US012454547B2

(12) United States Patent
Feula et al.

(10) Patent No.: US 12,454,547 B2
(45) Date of Patent: Oct. 28, 2025

(54) STEROIDAL COMPOSITIONS AND METHODS OF TREATING LIPOGENIC CANCERS

(71) Applicant: Asteroid Therapeutics, Indianapolis, IN (US)

(72) Inventors: Antonio Feula, San Mateo, CA (US); Francesco G Salituro, Marlborough, MA (US); Ryan Edward Stites, Indianapolis, IN (US)

(73) Assignee: Asteroid Therapeutics, Indianapolis, IN (US)

( * ) Notice: Subject to any disclaimer, the term of this patent is extended or adjusted under 35 U.S.C. 154(b) by 0 days.

(21) Appl. No.: 18/305,332

(22) Filed: Apr. 22, 2023

(65) Prior Publication Data

US 2023/0340011 A1 Oct. 26, 2023

Related U.S. Application Data

(60) Provisional application No. 63/486,681, filed on Feb. 24, 2023, provisional application No. 63/363,399, filed on Apr. 22, 2022.

(51) Int. Cl.

| | |
|---|---|
| ***C07J 41/00*** | (2006.01) |
| ***A61P 35/00*** | (2006.01) |
| ***C07J 9/00*** | (2006.01) |
| ***C07J 43/00*** | (2006.01) |

(52) U.S. Cl.

CPC ........... *C07J 41/0061* (2013.01); *A61P 35/00* (2018.01); *C07J 9/00* (2013.01); *C07J 43/003* (2013.01)

(58) Field of Classification Search

CPC ........ C07J 41/0061; C07J 9/00; C07J 43/003; A61P 35/00

See application file for complete search history.

(56) References Cited

U.S. PATENT DOCUMENTS

| | | | |
|---|---|---|---|
| 5,541,322 A | 7/1996 | Fang et al. | |
| 7,012,069 B2 | 3/2006 | Song et al. | |
| 7,235,552 B1 | 6/2007 | Hesse et al. | |
| 7,825,269 B2 | 11/2010 | Mangelsdorf | |
| 9,370,504 B2 * | 6/2016 | Kim | A61P 43/00 |
| 10,117,878 B2 | 11/2018 | Mangelsdorf et al. | |
| 2002/0013302 A1 | 1/2002 | Gronvald et al. | |
| 2003/0153541 A1 | 8/2003 | Dudley et al. | |
| 2006/0025393 A1 | 2/2006 | Liao et al. | |
| 2007/0032464 A1 | 2/2007 | Liao | |
| 2012/0040916 A1 | 2/2012 | Moon et al. | |
| 2015/0158903 A1 | 6/2015 | Upasani et al. | |
| 2015/0376225 A1 | 12/2015 | Dugar et al. | |
| 2019/0125745 A1 | 5/2019 | Martinez et al. | |
| 2022/0402965 A1 * | 12/2022 | Benenato | C07J 21/005 |
| 2023/0112857 A1 * | 4/2023 | Huang | A61K 48/0033 424/450 |

FOREIGN PATENT DOCUMENTS

| | | |
|---|---|---|
| EP | 0 105 404 A1 | 4/1984 |
| EP | 0 562 849 A2 | 9/1993 |
| GB | 2321244 A | 7/1998 |
| WO | 02/14342 A1 | 2/2002 |
| WO | 03/082893 A2 | 10/2003 |

OTHER PUBLICATIONS

Dormer et al. (J. Org. Chem. 2003, 68, 2, 467-477 (Year: 2003).*
Li, W. et al., A Bacterial Bile Acid Metabolite Modulates Treg Activity through the Nuclear Hormone Receptor NR4A 1, Cell Host Microbe. Sep. 8, 2021; 29(9): 1366-1377.
PCT/US/2023/066095 Invitation to Pay Additional Fees and, where, Applicable, Protest Fee, Aug. 15, 2023.

* cited by examiner

*Primary Examiner* — Joseph K McKane
*Assistant Examiner* — Quincy McKoy
(74) *Attorney, Agent, or Firm* — Vance Intellectual Property, PC

(57) ABSTRACT

The invention describes novel steroidal compounds, compositions containing the same, and methods of using the same as SREBP inhibitors, as LXR agonists, or as dual modulators of SREBP and LXR, to treat SREBP and/or LXR mediated diseases.

6 Claims, No Drawings

STEROIDAL COMPOSITIONS AND METHODS OF TREATING LIPOGENIC CANCERS

CROSS REFERENCE TO RELATED APPLICATIONS

This application is entitled to priority pursuant to 35 U.S.C. § 119(e) to U.S. provisional patent application No. 63/363,399, filed on 22 Apr. 2022 and to U.S. provisional patent application No. 63/486,681, filed on 24 Feb. 2023. The contents of which are incorporated herein by reference in their entirety.

BACKGROUND OF THE INVENTION

Malignant brain tumors are among the most devastating types of cancer. Glioblastoma multiforme (GBM) is the most common and serious form of brain cancer. GBM is generally located in the supratentorial region and rapidly infiltrates the brain parenchyma, sometimes becoming very large before producing any symptoms. GBM is characterized by the presence of hyperplastic blood vessels that present with disrupted morphology and functionality, with small areas of necrotic tissue surrounded by anaplastic cells. The increased hypoxia within glioblastoma leads to cancer progression by promoting processes such as immunosuppression.

Most GBMs are surgically unresectable and are typically diagnosed at an advanced stage. The high level of resistance to chemotherapy, radiotherapy and immunotherapy makes GBM one of the most difficult cancers to treat. In brain tumors, the challenges of targeted therapy also include the blood-brain barrier, which often contributes to treatment failure. Therefore, the discovery of novel therapeutic agents that possess the capability to pass through the blood brain barrier are desired for the effective management of GBM.

Sterol regulatory element-binding proteins (SREBPs) are key transcription factors involved in the regulation of lipogenesis through regulating gene expression of proteins involved in fatty acid biosynthesis. In lipogenic cancers such as brain (GBM), breast, lung, melanoma, hepatocellular carcinoma (HCC), colon, prostate, and ovarian, overexpression of SREBP has been found to be associated with its aggressive pathological features. The inhibition of SREBPs therefore serves as a potential therapeutic treatment for lipogenic cancers, leading to the reduction in tumor viability, cell growth, cell size and migration.

The liver x receptor (LXR), a nuclear receptor transcription factor, is known to be an important regulator of lipid homeostasis. 22(R)-hydroxycholesterol, and 24(S)-hydroxycholesterol, both LXR agonists, have been shown to suppress the proliferation of glioblastoma, prostate cancer, and breast cancer cells as well as to delay progression of prostate cancer to androgen-independent status. So, the agonism of LXR serves as a potential therapeutic treatment for lipogenic cancers, leading to the reduction in tumor viability, cell growth, cell size and migration.

The LXR receptor is also known to be involved in numerous other disease-related pathways. Examples of such diseases include Alzheimer's, atherosclerosis, type II diabetes, skin aging, etc. (see, for example, US Patent Publication No. 20220363662A1 and U.S. Pat. No. 9,751,869B2). So, the agonism of the LXR also serves as a potential therapeutic treatment for these diseases.

The novel, steroidal compounds and methods described herein provide effective approaches to the treatment of lipogenic cancers and their respective symptoms through the inhibition of SREBP and its associated pathways. In addition, at least some of the steroidal compounds described herein function as LXR agonists, thereby providing an additional mechanism for the treatment of lipogenic cancers as well as other SREBP and LXR agonist-mediated diseases.

SUMMARY OF THE INVENTION

In an aspect, there are described steroidal compounds.

In another aspect, there are described steroidal compounds that are inhibitors of sterol regulatory element-binding protein (SREBP)(e.g., SREBP-1 and/or SREBP-2).

In another aspect, there are described steroidal compounds that are inhibitors of SREBP and agonists of the liver x receptors (LXR).

In another aspect, there are described steroidal compounds that are agonists of the liver X receptors (LXR).

In another aspect, there are described pharmaceutical compositions, comprising steroidal compounds.

In another aspect, there are describe methods of treating an SREBP-mediated disease using steroidal compounds.

In another aspect, there are describe methods of treating an LXR-mediated disease using steroidal compounds.

In another aspect, there are describe methods of treating an SREBP- and LXR-mediated disease using steroidal compounds.

In another aspect, there are described steroidal compounds and/or compositions for use in medical therapy.

In another aspect, there are described the use of steroidal compounds for the manufacture of a medicament for the treatment of an indication described herein (e.g., glioblastoma).

These and other aspects, which will become apparent during the following detailed description, have been achieved by the inventors' discovery of novel, steroidal compounds.

DETAILED DESCRIPTION OF THE INVENTION

Exemplary aspects of the invention are described herein. Although the following detailed description contains many specifics for purposes of illustration, a person of ordinary skill in the art will appreciate that variations and alterations to the following details are within the scope of the invention. Accordingly, the following aspects of the invention are set forth without any loss of generality to, and without imposing limitations upon, the claimed invention.

An aspect of the invention involves novel steroids that are inhibitors of sterol regulatory element-binding protein (SREBP), including, for example, SREBP-1 and SREBP-2.

Another aspect of the invention involves novel steroids that are inhibitors of sterol regulatory element-binding protein (SREBP) and agonists of liver x receptor (LXR).

Another aspect of the invention involves novel steroids that are agonists of the liver X receptors (LXR).

Another aspect of the invention involves a compound of Formula I or a stereoisomer or pharmaceutically acceptable salt thereof.

I

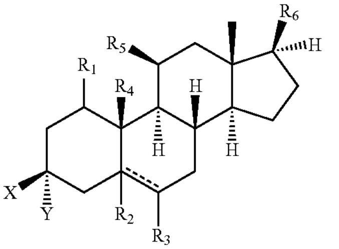

wherein:

“ ═══ ” represents a single bond or a double bond, provided that in formula I, $R_2$ is absent and $R_3$ is H when “ ═══ ” is a double bond;

X is selected from H, OH, and F;

Y is selected from H, OH, $CH_3$, $CH_2CH_3$, —$CH_2$—O—$C_{1-3}$ alkyl, F, and $CF_3$, provided that only one of X and Y is H;

$R_1$ is selected from H and OH;

$R_2$, when present, is H, provided that when $R_2$ is a beta-H (cis to $R_4$), then $R_3$ is a beta-OH;

$R_3$ is selected from H and OH;

$R_4$ is selected from H and $CH_3$;

$R_5$ is selected from H and OH;

$R_6$ is selected from $R_{6A}$-$R_{6F}$(wherein * is the point of attachment to formula I):

$R_{6A}$

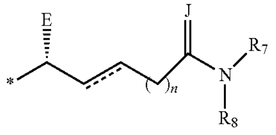

$R_{6B}$

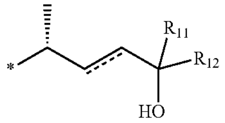

$R_{6C}$

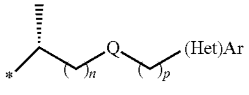

$R_{6D}$

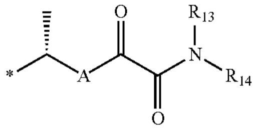

$R_{6E}$

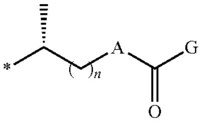

$R_{6F}$

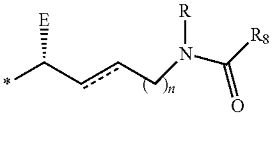

“ ═══ ” represents a single bond or a double bond;

A is selected from O, NR, and $CH_2$;

E is selected from H and $CH_3$;

G is selected from OR, $NR_{15}R_{16}$, and $R_8$;

J is O or S;

Q is absent or is O;

n is selected from 0, 1, 2, and 3;

p is selected from 0, 1, 2, and 3, provided that in $R_{6C}$, when Q is absent, then n+p total at least 2;

$R_7$ is selected from H, $C_{1-6}$ alkyl, and $C_{3-6}$ cycloalkyl;

alternatively, $R_7$ is $OR_{10}$;

$R_8$ is selected from $C_{1-6}$ alkyl, —$C_{0-4}$ alkylene-$C_{3-6}$ cycloalkyl, —$C_{0-4}$ alkylene-aryl, —$C_{0-4}$ alkylene-$C_{4-6}$ membered cyclic amine, —$C_{0-4}$ alkylene-heteroaryl, —$C_{1-4}$ alkylene-OR, —$C_{1-4}$ alkylene-$NR^aR^b$, —$C_{1-4}$ alkylene-$CF_3$, and —$C_{1-4}$ alkylene-C(O)OR, wherein each cycloalkyl, cyclic amine, aryl, and heteroaryl is optionally substituted with $C_{0-4}$ alkylene-OR, —$C_{0-4}$ alkylene-C(O)$R^a$, —$C_{0-4}$ alkylene-C(O)$OR^a$, —$C_{0-4}$ alkylene-C(O)$NR^aR^b$, —$C_{0-4}$ alkylene-OC(O)$NR^aR^b$, —$C_{0-4}$ alkylene-$NR^a$C(O)$NR^aR^b$, —$C_{0-4}$ alkylene-S(O)$_2NR^aR^b$, —$C_{0-4}$ alkylene-$NR^a$C(O)$R^a$, —$C_{0-4}$ alkylene-$NR^a$S(O)$_2$—$C_{1-4}$ alkyl, and —$C_{0-4}$ alkylene-S(O)$_2$—$C_{1-4}$ alkyl;

alternatively, $NR_7R_8$ forms a 4-10 membered mono-, bi-, or tricyclic amine or a 7-11 membered spirocyclic amine, wherein:

(a) 0-2 ring $CH_2$ are replaced by a group selected from O, S, S(O), $SO_2$, $SO_2NR$, C(O)NR, and NR;

(b) 0-1 ring double bond is present;

(c) the cyclic amine is optionally substituted at a $CH_2$ and/or NH position with 1-2 groups selected from $C_{1-6}$ alkyl, —$C_{0-4}$ alkylene-$C_{3-6}$ cycloalkyl, halo, $CH_2CF_3$, $CHF_2$, $CF_3$, $CH_2CHF_2$, —CN, $OCH_2CF_3$, $OCHF_2$, $OCF_3$, $OCH_2CHF_2$, CH(OR)($CF_3$), C(OR)($CF_3$)$_2$, $C_{2-6}$ alkenyl, $C_{2-6}$ alkynyl, —$C_{0-4}$ alkylene-OR, O—$C_{2-4}$ alkylene-OR, —$C_{0-4}$ alkylene-C(O)$R^a$, —$C_{0-4}$ alkylene-C(N)—$C_{1-4}$ alkyl, —$C_{0-4}$ alkylene-C(N)NRR, —$C_{0-4}$ alkylene-C(O)$OR^a$, —$C_{0-4}$ alkylene-C(O)SR, —$C_0$-4 alkylene-C(S)$OR^a$, —$C_{0-4}$ alkylene-C(O)$NR^aR^b$, —$C_{0-4}$ alkylene-OC(O)$NR^aR^b$, —$C_{0-4}$ alkylene-$NR^a$C(O)OR, —$C_{0-4}$ alkylene-$NR^a$C(O)$NR^aR^b$, —$C_{0-4}$ alkylene-S(O)$_2NR^aR^b$, —$C_{0-4}$ alkylene-$NR^a$C(O)$R^a$, —CH($CF_3$)$NR^a$C(O)$R^a$—$C_{1-4}$ alkyl, —$C_{0-4}$ alkylene-$NR^a$S(O)$_2$—$C_{1-4}$ alkyl, —CH($CF_3$)$NR^a$S(O)$_2$—$C_{1-4}$ alkyl, —$C_{0-4}$ alkylene-$NR^a$S(O)$_2$—$CF_3$, —$C_{0-4}$ alkylene-S(O)$_2$—$C_{1-4}$ alkyl, —$C_{0-4}$ alkylene-aryl, —($CH_2$)$_{0-4}$—N-morpholin-3-one, —($CH_2$)$_{0-4}$—N-2,2-dimethyl-morpholin-3-one, —$C_{0-4}$ alkylene-heteroaryl, —O—($CH_2$)$_{0-4}$-aryl, —O—($CH_2$)$_{0-4}$-heteroaryl, —C(O)-aryl, and —C(O)-heteroaryl, provided that only one substituent on the monocyclic amine is alkyl; and, (d) wherein each aryl or heteroaryl in (c) is optionally substituted with 1-2 groups selected from $C_{1-6}$ alkyl, —$C_{0-4}$ alkylene-$C_{3-6}$ cycloalkyl, —O—$C_{3-6}$ cycloalkyl, halo, $CH_2CF_3$, $CHF_2$, $CF_3$, $CH_2CHF_2$, C(OR)($CF_3$)$_2$, $C_{2-6}$ alkenyl, $C_{2-6}$ alkynyl, —$C_{0-4}$ alkylene-OR, —O—$C_{2-4}$ alkylene-OR, —$C_{0-4}$ alkylene-C(O)R, —$C_{0-4}$ alkylene-C(O)OR, —$C_{0-4}$ alkylene-NRR, —$C_{0-4}$ alkylene-C(O)NRR, —$C_{0-4}$ alkylene-S(O)$_2$NRR, —$C_{0-4}$ alkylene-NRC(O)—$C_{1-4}$ alkyl, —$C_{0-4}$ alkylene-NRS(O)$_2$—$C_{1-4}$ alkyl, —$C_{0-4}$ alkylene-S(O)$_2$—$C_{1-4}$ alkyl, and —$C_{0-4}$ alkylene-aryl, and $C_{0-4}$ alkylene-heteroaryl;

R, at each occurrence, is selected from H and $C_{1-6}$ alkyl;

$R^a$, at each occurrence, is selected from H, $C_{1-6}$ alkyl, —$C_{0-4}$ alkylene-$C_{3-6}$ cycloalkyl, —$C_{0-4}$ alkylene-$C_{4-6}$ cyclic ether, —$C_{0-4}$ alkylene-$C_{4-6}$ cyclic amine, —$C_{2-4}$ alkylene-OR, —$C_{0-4}$ alkylene-C(O)R, —$C_{0-4}$ alkylene-C(O)OR, —$C_{0-4}$ alkylene-C(O)NRR, —$C_{0-4}$ alkylene-$S(O)_2$NRR, —$C_{0-4}$ alkylene-NRC(O)—$C_{1-4}$ alkyl, —$C_{0-4}$ alkylene-NR$S(O)_2$—$C_{1-4}$ alkyl, —$C_{0-4}$ alkylene-$S(O)_2$—$C_{1-4}$ alkyl, —$C_{0-4}$ alkylene-aryl, and —$C_{0-4}$ alkylene-heteroaryl, wherein each cycloalkyl, cyclic ether, cyclic amine, aryl, and heteroaryl is optionally substituted with $C_{1-6}$ alkyl and $C_{0-4}$ alkylene-OR;

$R^b$, at each occurrence, is selected from H and $C_{1-6}$ alkyl;

alternatively, $NR^aR^b$ forms a 4-6 membered cyclic amine substituted with 0-1 groups selected from $C_{1-6}$ alkyl, OR, halo, and $CF_3$;

$R_{10}$ is selected from $C_{1-6}$ alkyl, $C_{3-6}$ cycloalkyl, —$C_{1-4}$ alkylene-$C_{3-6}$ cycloalkyl, —$C_{1-4}$ alkylene-OR, —$C_{1-4}$ alkylene-$NR^aR^b$, and —$C_{1-4}$ alkylene-$CF_3$;

$R_{11}$ is selected from isopropyl and $CF_3$; $R_{12}$ is selected from H, $CF_3$, $C_{1-6}$ alkyl, $C_{2-6}$ alkenyl, $C_{2-6}$ alkynyl, and $C_{3-6}$ cycloalkyl;

$R_{13}$ is selected from H and $C_{1-6}$ alkyl;

$R_{14}$ is selected from H and $C_{1-6}$ alkyl;

alternatively, $NR_{13}R_{14}$ forms a 4-8 membered cyclic amine, wherein:

(a) 0-2 ring $CH_2$ are replaced by a group selected from O, S, S(O), $SO_2$, $SO_2$NR, C(O)NR, and NR;

(b) 0-1 ring double bond is present;

(c) the cyclic amine is optionally substituted at a $CH_2$ and/or NH position with 1-2 groups selected from $C_{1-6}$ alkyl, —$C_{0-4}$ alkylene-$C_{3-6}$ cycloalkyl, halo, $CH_2CF_3$, $CHF_2$, $CF_3$, $CH_2CHF_2$, —CN, $OCH_2CF_3$, $OCHF_2$, $OCF_3$, $OCH_2CHF_2$, CH(OR)($CF_3$), C(OR)$(CF_3)_2$, $C_{2-6}$ alkenyl, $C_{2-6}$ alkynyl, —$C_{0-4}$ alkylene-OR, O—$C_{2-4}$ alkylene-OR, —$C_{0-4}$ alkylene-C(O)$R^a$, —$C_{0-4}$ alkylene-C(N)—$C_{1-4}$ alkyl, —$C_{0-4}$ alkylene-C(N)NRR, —$C_{0-4}$ alkylene-C(O)$OR^a$, —$C_{0-4}$ alkylene-C(O)SR, —$C_{0-4}$ alkylene-C(S)$OR^a$, —$C_{0-4}$ alkylene-C(O)$NR^aR^b$, —$C_{0-4}$ alkylene-OC(O)$NR^aR^b$, —$C_{0-4}$ alkylene-$NR^a$C(O)OR, —$C_{0-4}$ alkylene-$NR^a$C(O)$NR^aR^b$, —$C_{0-4}$ alkylene-$S(O)_2NR^aR^b$, —$C_{0-4}$ alkylene-$NR^a$C(O)$R^a$, —CH($CF_3$)$NR^a$C(O)$R^a$—$C_{1-4}$ alkyl, —$C_{0-4}$ alkylene-$NR^aS(O)_2$—$C_{1-4}$ alkyl, —CH($CF_3$)$NR^aS(O)_2$—$C_{1-4}$ alkyl, —$C_{0-4}$ alkylene-$NR^aS(O)_2$—$CF_3$, —$C_{0-4}$ alkylene-$S(O)_2$—$C_{1-4}$ alkyl, —$C_{0-4}$ alkylene-aryl, —$(CH_2)_{0-4}$—N-morpholin-3-one, —$(CH_2)_{0-4}$—N-2,2-dimethyl-morpholin-3-one, —$C_{0-4}$ alkylene-heteroaryl, —O—$(CH_2)_{0-4}$-aryl, —O—$(CH_2)_{0-4}$-heteroaryl, —C(O)-aryl, and —C(O)-heteroaryl, provided that only one substituent on the monocyclic amine is alkyl; and, (d) wherein each aryl or heteroaryl in (c) is optionally substituted with 1-2 groups selected from $C_{1-6}$ alkyl, —$C_{0-4}$ alkylene-$C_{3-6}$ cycloalkyl, —O—$C_{3-6}$ cycloalkyl, halo, $CH_2CF_3$, $CHF_2$, $CF_3$, $CH_2CHF_2$, C(OR)$(CF_3)_2$, $C_{2-6}$ alkenyl, $C_{2-6}$ alkynyl, —$C_{0-4}$ alkylene-OR, —O—$C_{2-4}$ alkylene-OR, —$C_{0-4}$ alkylene-C(O)R, —$C_{0-4}$ alkylene-C(O)OR, —$C_{0-4}$ alkylene-NRR, —$C_{0-4}$ alkylene-C(O)NRR, —$C_{0-4}$ alkylene-$S(O)_2$NRR, —$C_{0-4}$ alkylene-NRC(O)—$C_{1-4}$ alkyl, —$C_{0-4}$ alkylene-NR$S(O)_2$—$C_{1-4}$ alkyl, —$C_{0-4}$ alkylene-$S(O)_2$—$C_{1-4}$ alkyl, and —$C_{0-4}$ alkylene-aryl, and $C_{0-4}$ alkylene-heteroaryl;

$R_{15}$ is selected from H, $C_{1-6}$ alkyl, and —$C_{1-4}$ alkylene-OR;

$R_{16}$ is selected from H and $C_{1-6}$ alkyl;

alternatively, $NR_{15}R_{16}$ forms a 4-8 membered cyclic amine, wherein:

(a) 0-2 ring $CH_2$ are replaced by a group selected from O, S, S(O), $SO_2$, $SO_2$NR, C(O)NR, and NR;

(b) 0-1 ring double bond is present;

(c) the cyclic amine is optionally substituted at a $CH_2$ and/or NH position with 1-2 groups selected from $C_{1-6}$ alkyl, —$C_{0-4}$ alkylene-$C_{3-6}$ cycloalkyl, halo, $CH_2CF_3$, $CHF_2$, $CF_3$, $CH_2CHF_2$, —CN, $OCH_2CF_3$, $OCHF_2$, $OCF_3$, $OCH_2CHF_2$, CH(OR)($CF_3$), C(OR)$(CF_3)_2$, $C_{2-6}$ alkenyl, $C_{2-6}$ alkynyl, —$C_{0-4}$ alkylene-OR, —O—$C_{2-4}$ alkylene-OR, —$C_{0-4}$ alkylene-C(O)$R^a$, —$C_{0-4}$ alkylene-C(N)—$C_{1-4}$ alkyl, —$C_{0-4}$ alkylene-C(N)NRR, —$C_{0-4}$ alkylene-C(O)$OR^a$, —$C_{0-4}$ alkylene-C(O)SR, —$C_{0-4}$ alkylene-C(S)$OR^a$, —$C_{0-4}$ alkylene-C(O)$NR^aR^b$, —$C_{0-4}$ alkylene-OC(O)$NR^aR^b$, —$C_{0-4}$ alkylene-$NR^a$C(O)OR, —$C_{0-4}$ alkylene-$NR^a$C(O)$NR^aR^b$, —$C_{0-4}$ alkylene-$S(O)_2NR^aR^b$, —$C_{0-4}$ alkylene-$NR^a$C(O)$R^a$, —CH($CF_3$)$NR^a$C(O)$R^a$—$C_{1-4}$ alkyl, —$C_{0-4}$ alkylene-$NR^aS(O)_2$—$C_{1-4}$ alkyl, —CH($CF_3$)$NR^aS(O)_2$—$C_{1-4}$ alkyl, —$C_{0-4}$ alkylene-$NR^aS(O)_2$—$CF_3$, —$C_{0-4}$ alkylene-$S(O)_2$—$C_{1-4}$ alkyl, —$C_{0-4}$ alkylene-aryl, —$(CH_2)_{0-4}$—N-morpholin-3-one, —$(CH_2)_{0-4}$—N-2,2-dimethyl-morpholin-3-one, —$C_{0-4}$ alkylene-heteroaryl, —O—$(CH_2)_{0-4}$-aryl, —O—$(CH_2)_{0-4}$-heteroaryl, —C(O)-aryl, and —C(O)-heteroaryl, provided that only one substituent on the monocyclic amine is alkyl; and, (d) wherein each aryl or heteroaryl in (c) is optionally substituted with 1-2 groups selected from $C_{1-6}$ alkyl, —$C_{0-4}$ alkylene-$C_{3-6}$ cycloalkyl, —O—$C_{3-6}$ cycloalkyl, halo, $CH_2CF_3$, $CHF_2$, $CF_3$, $CH_2CHF_2$, C(OR)$(CF_3)_2$, $C_{2-6}$ alkenyl, $C_{2-6}$ alkynyl, —$C_{0-4}$ alkylene-OR, —O—$C_{2-4}$ alkylene-OR, —$C_{0-4}$ alkylene-C(O)R, —$C_{0-4}$ alkylene-C(O)OR, —$C_{0-4}$ alkylene-NRR, —$C_{0-4}$ alkylene-C(O)NRR, —$C_{0-4}$ alkylene-$S(O)_2$NRR, —$C_{0-4}$ alkylene-NRC(O)—$C_{1-4}$ alkyl, —$C_{0-4}$ alkylene-NR$S(O)_2$—$C_{1-4}$ alkyl, —$C_{0-4}$ alkylene-$S(O)_2$—$C_{1-4}$ alkyl, and —$C_{0-4}$ alkylene-aryl, and $C_{0-4}$ alkylene-heteroaryl;

Het(Ar) is an aryl or a heteroaryl, wherein (a) the Het(Ar) ring is optionally substituted with 1-2 groups selected from —NC, $C_{1-6}$ alkyl, —$C_{0-4}$ alkylene-$C_{3-6}$ cycloalkyl, halo, $CH_2CF_3$, $CHF_2$, $CF_3$, $CH_2CHF_2$, C(OR)$(CF_3)_2$, $C_{2-6}$ alkenyl, $C_{2-6}$ alkynyl, —$C_{0-4}$ alkylene-OR, —O—$C_{2-4}$ alkylene-OR, —$C_{0-4}$ alkylene-C(O)R, —$C_{0-4}$ alkylene-C(O)OR, —$C_{0-4}$ alkylene-C(O)$NR^aR^b$, —$C_{0-4}$ alkylene-$S(O)_2NR^aR^b$, —$C_{0-4}$ alkylene-$NR^a$C(O)—$C_{1-4}$ alkyl, —$C_{0-4}$ alkylene-$NR^aS(O)_2$—$C_{1-4}$ alkyl, and —$C_{0-4}$ alkylene-$S(O)_2$—$C_{1-4}$ alkyl; and, (b) 0-1 ring $CH_2$ present in each ring is replaced by a group selected from C═O and C═S;

provided that the following compounds are excluded:
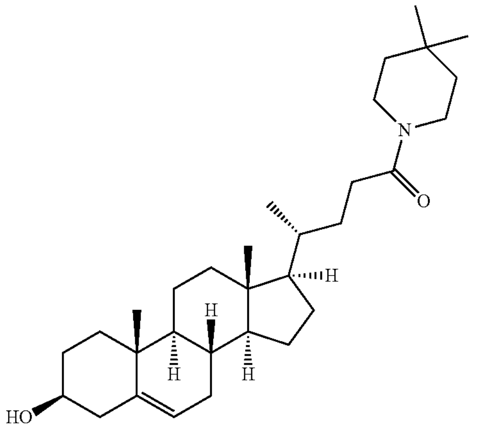
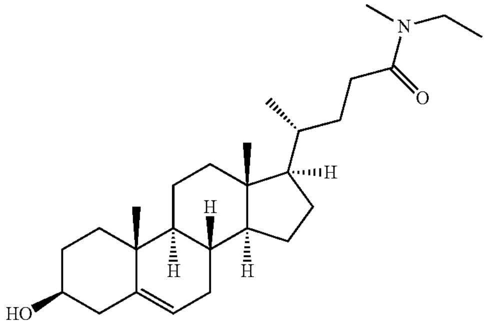
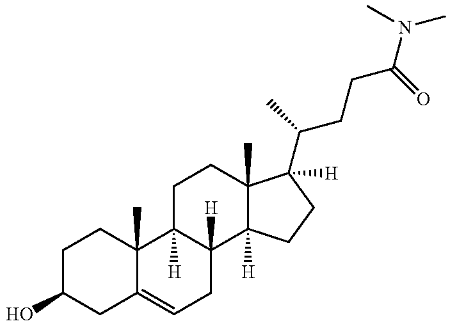
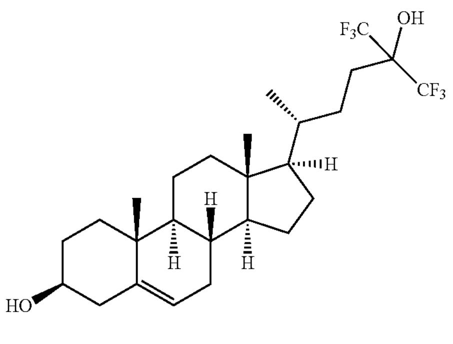
-continued
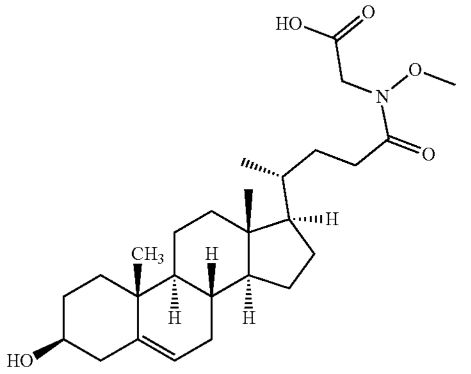
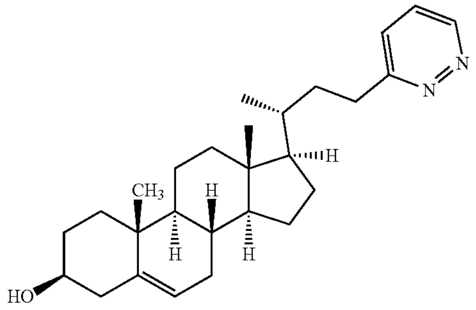
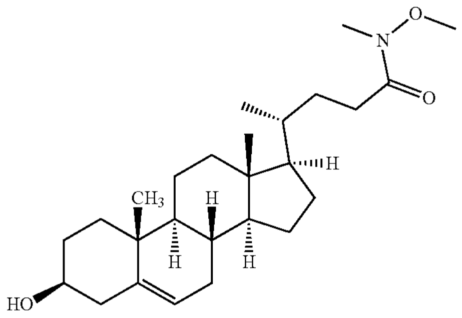
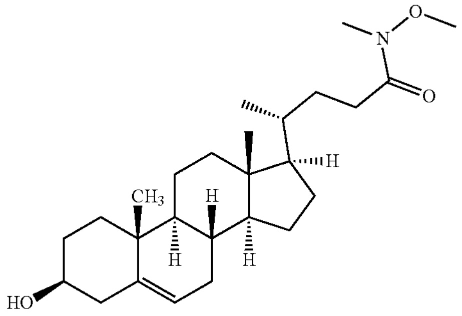
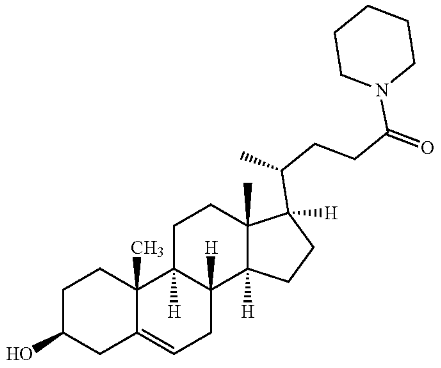

-continued
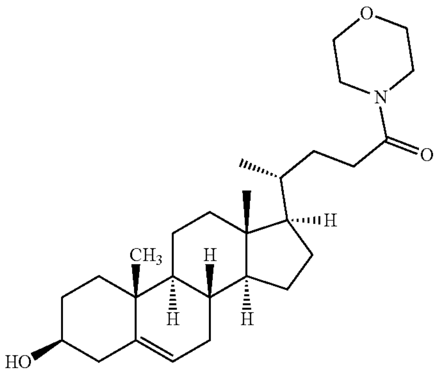
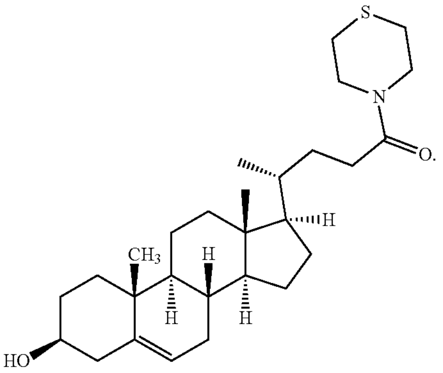
Another aspect of the invention involves a compound of formula II, III, or IV or a stereoisomer or pharmaceutically acceptable salt thereof:
II
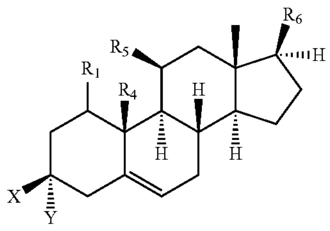
III
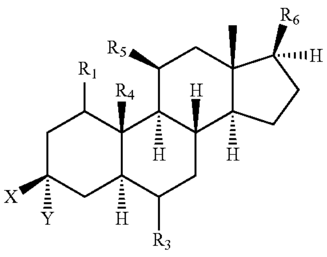
VI
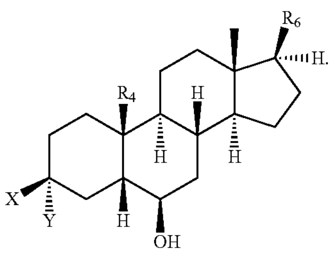
Another aspect of the invention involves a compound of formula IIa-1 or a stereoisomer or pharmaceutically acceptable salt thereof:
IIa
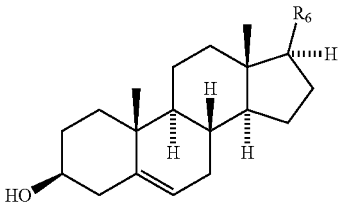
IIb
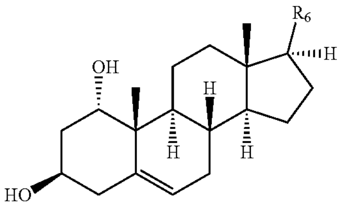
IIc
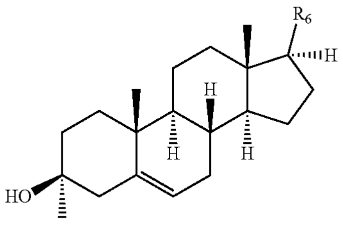
IId
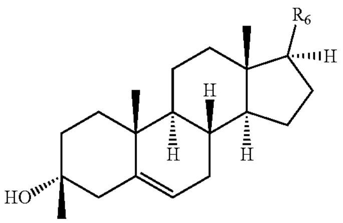
IIe
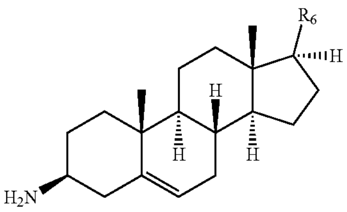
IIf
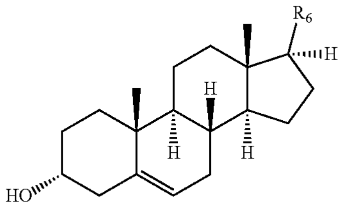
IIg
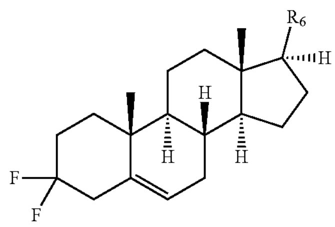

-continued
IIh
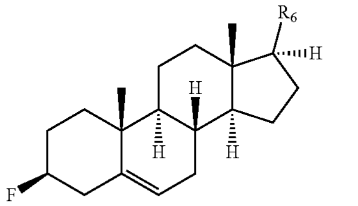
IIi
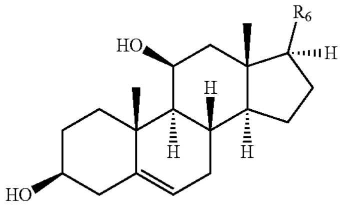
IIj
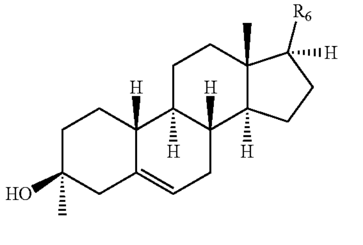
IIk
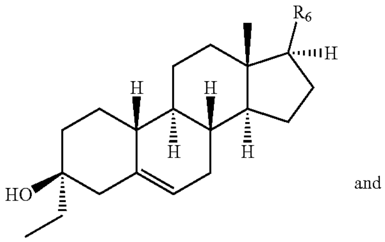
and
IIl
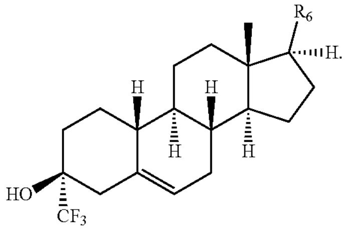
Another aspect of the invention involves a compound of formula IIIa-g or a stereoisomer or pharmaceutically acceptable salt thereof:
IIIa
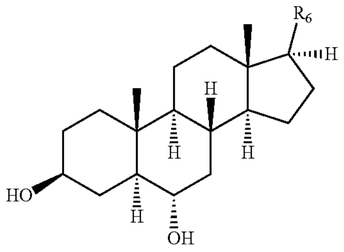
-continued
IIIb
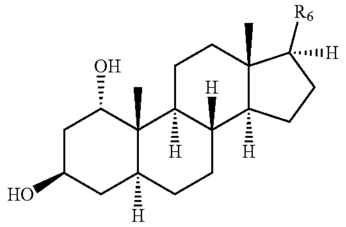
IIIc
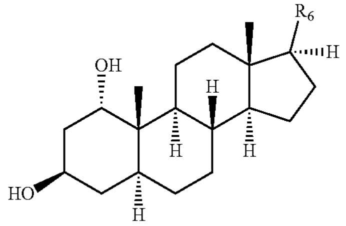
IIId
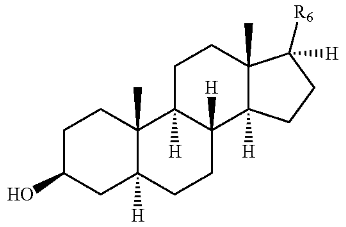
IIIe
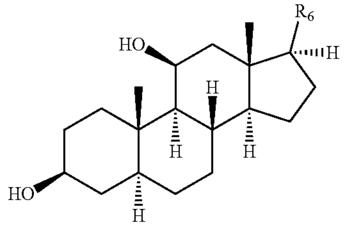
IIIf
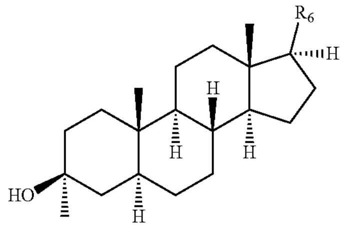
IIIg
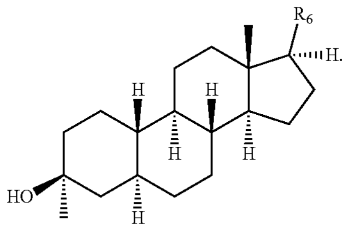
Another aspect of the invention involves a compound of formula IVa or a stereoisomer or pharmaceutically acceptable salt thereof:

IVa

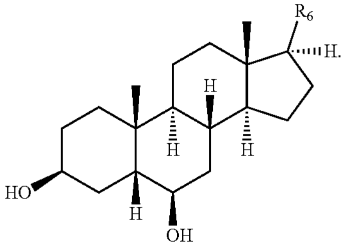

Another aspect of the invention involves a compound of Formula I (or one of Formula II-IVa) or a stereoisomer or pharmaceutically acceptable salt thereof:

I

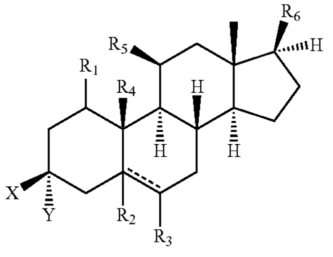

wherein:

“ ═══ ” represents a single bond or a double bond, provided that in formula I, $R_2$ is absent and $R_3$ is H when “ ═══ ” is a double bond;

X is OH;

Y is H;

$R_1$ is H;

$R_2$, when present, is H, provided that when $R_2$ is a beta-H (cis to $R_4$), then $R_3$ is a beta-OH;

$R_3$ is selected from H and OH;

$R_4$ is $CH_3$;

$R_5$ is H;

$R_6$ is selected from $R_{6A}$-$R_{6E}$ (wherein * is the point of attachment to formula I (or one of Formula II-IVa)):

$R_{6A}$

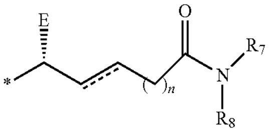

$R_{6B}$

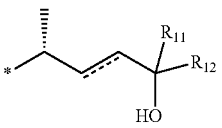

$R_{6C}$

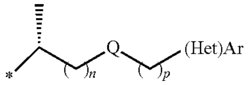

$R_{6D}$

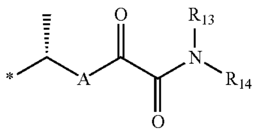

-continued $R_{6E}$

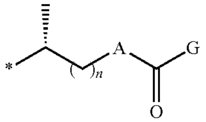

$R_{6F}$

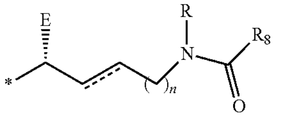

“ ═══ ” represents a single bond or a double bond

A is selected from 0, NR, and $CH_2$;

E is selected from H and $CH_3$;

G is selected from OR and $NR_{15}R_{16}$;

Q is absent or is selected from O;

n is selected from 0 and 1;

p is selected from 0, 1, 2, and 3, provided that in $R_{6C}$, when Q is absent, then n+p total at least 2 and further provided that in $R_{6C}$, n+p is at least 1;

$R_7$ is selected from H, $C_{1-6}$ alkyl, and $C_{3-6}$ cycloalkyl; alternatively, $R_7$ is $OR_{10}$;

$R_8$ is selected from $C_{1-6}$ alkyl, —$C_{0-4}$ alkylene-$C_{3-6}$ cycloalkyl, —$C_{0-4}$ alkylene-aryl, —$C_{0-4}$ alkylene-$C_{4-6}$ membered cyclic amine, —$C_{0-4}$ alkylene-heteroaryl, —$C_{1-4}$ alkylene-OR, —$C_{1-4}$ alkylene-$NR^aR^b$, —$C_{1-4}$ alkylene-$CF_3$, and —$C_{1-4}$ alkylene-C(O)OR, wherein each cycloalkyl, cyclic amine, aryl, and heteroaryl is optionally substituted with $C_{0-4}$ alkylene-OR, —$C_{0-4}$ alkylene-C(O)$R^a$, —$C_{0-4}$ alkylene-C(O)$OR^a$, —$C_{0-4}$ alkylene-C(O)$NR^aR^b$, —$C_{0-4}$ alkylene-OC(O)$NR^aR^b$, —$C_{0-4}$ alkylene-$NR^a$C(O)$NR^aR^b$, —$C_{0-4}$ alkylene-S(O)$_2NR^aR^b$, —$C_{0-4}$ alkylene-$NR^a$C(O)$R^a$, —$C_{0-4}$ alkylene-$NR^a$S(O)$_2$—$C_{1-4}$ alkyl, and —$C_{0-4}$ alkylene-S(O)$_2$—$C_{1-4}$ alkyl;

alternatively, $NR_7R_8$ forms a 4-10 membered mono-, bi-, or tricyclic amine or a 7-11 membered spirocyclic amine, wherein:

(a) 0-2 ring $CH_2$ are replaced by a group selected from O, S, S(O), $SO_2$, $SO_2NR$, C(O)NR, and NR;

(b) 0-1 ring double bond is present;

(c) the cyclic amine is optionally substituted at a $CH_2$ and/or NH position with 1-2 groups selected from $C_{1-6}$ alkyl, —$C_{0-4}$ alkylene-$C_{3-6}$ cycloalkyl, halo, $CH_2CF_3$, $CHF_2$, $CF_3$, $CH_2CHF_2$, —CN, $OCH_2CF_3$, $OCHF_2$, $OCF_3$, $OCH_2CHF_2$, CH(OR)($CF_3$), C(OR)($CF_3$)$_2$, $C_{2-6}$ alkenyl, $C_{2-6}$ alkynyl, —$C_{0-4}$ alkylene-OR, O—$C_{2-4}$ alkylene-OR, —$C_{0-4}$ alkylene-C(O)$R^a$, —$C_{0-4}$ alkylene-C(N)—$C_{1-4}$ alkyl, —$C_{0-4}$ alkylene-C(N)NRR, —$C_{0-4}$ alkylene-C(O)$OR^a$, —$C_{0-4}$ alkylene-C(O)SR, —$C_{0-4}$ alkylene-C(S)$OR^a$, —$C_{0-4}$ alkylene-C(O)$NR^aR^b$, —$C_{0-4}$ alkylene-OC(O)$NR^aR^b$, —$C_{0-4}$ alkylene-$NR^a$C(O)OR, —$C_{0-4}$ alkylene-$NR^a$C(O)$NR^aR^b$, —$C_{0-4}$ alkylene-S(O)$_2NR^aR^b$, —$C_{0-4}$ alkylene-$NR^a$C(O)$R^a$, —CH($CF_3$)$NR^a$C(O)$R^a$—$C_{1-4}$ alkyl, —$C_{0-4}$ alkylene-$NR^a$S(O)$_2$—$C_{1-4}$ alkyl, —CH($CF_3$)$NR^a$S(O)$_2$—$C_{1-4}$ alkyl, —$C_{0-4}$ alkylene-$NR^a$S(O)$_2$—$CF_3$, —$C_{0-4}$ alkylene-S(O)$_2$—$C_{1-4}$ alkyl, —$C_{0-4}$ alkylene-aryl, —($CH_2$)$_{0-4}$—N-morpholin-3-one, —($CH_2$)$_{0-4}$—N-2,2-dimethyl-morpholin-3-one, —$C_{0-4}$ alkylene-heteroaryl, —O—($CH_2$)$_{0-4}$-aryl, —O—($CH_2$)$_{0-4}$-heteroaryl, —C(O)-aryl, and —C(O)-heteroaryl, provided that only one substituent on the monocyclic amine is alkyl; and, (d) wherein each aryl or heteroaryl in (c) is optionally substituted with 1-2 groups selected from $C_{1-6}$ alkyl, —$C_{0-4}$ alkylene-$C_{3-6}$ cycloalkyl, —O—$C_{3-6}$ cycloalkyl, halo, $CH_2CF_3$, $CHF_2$, $CF_3$, $CH_2CHF_2$, C(OR)$(CF_3)_2$, $C_{2-6}$ alkenyl, $C_{2-6}$ alkynyl, $C_{0-4}$ alkylene-OR, —O—$C_{2-4}$ alkylene-OR, —$C_{0-4}$ alkylene-C(O)R, —$C_{0-4}$ alkylene-C(O)OR, —$C_{0-4}$ alkylene-NRR, —$C_{0-4}$ alkylene-C(O)NRR, —$C_{0-4}$ alkylene-$S(O)_2$NRR, —$C_{0-4}$ alkylene-NRC(O)—$C_{1-4}$ alkyl, —$C_{0-4}$ alkylene-NRS$(O)_2$—$C_{1-4}$ alkyl, —$C_{0-4}$ alkylene-$S(O)_2$—$C_{1-4}$ alkyl, and —$C_{0-4}$ alkylene-aryl, and $C_{0-4}$ alkylene-heteroaryl;

R, at each occurrence, is selected from H and $C_{1-6}$ alkyl;

$R^a$, at each occurrence, is selected from H, $C_{1-6}$ alkyl, —$C_{0-4}$ alkylene-$C_{3-6}$ cycloalkyl, —$C_{0-4}$ alkylene-$C_{4-6}$ cyclic ether, —$C_{0-4}$ alkylene-$C_{4-6}$ cyclic amine, —$C_{2-4}$ alkylene-OR, —$C_{0-4}$ alkylene-C(O)R, —$C_{0-4}$ alkylene-C(O)OR, —$C_{0-4}$ alkylene-C(O)NRR, —$C_{0-4}$ alkylene-$S(O)_2$NRR, —$C_{0-4}$ alkylene-NRC(O)—$C_{1-4}$ alkyl, —$C_{0-4}$ alkylene-NRS$(O)_2$—$C_{1-4}$ alkyl, —$C_{0-4}$ alkylene-$S(O)_2$—$C_{1-4}$ alkyl, —$C_{0-4}$ alkylene-aryl, and —$C_{0-4}$ alkylene-heteroaryl, wherein each cycloalkyl, cyclic ether, cyclic amine, aryl, and heteroaryl is optionally substituted with $C_{1-6}$ alkyl and $C_{0-4}$ alkylene-OR;

$R^b$, at each occurrence, is selected from H and $C_{1-6}$ alkyl;

alternatively, $NR^aR^b$ forms a 4-6 membered cyclic amine substituted with 0-1 groups selected from $C_{1-6}$ alkyl, OR, halo, and $CF_3$;

$R_{10}$ is selected from $C_{1-6}$ alkyl, $C_{3-6}$ cycloalkyl, —$C_{1-4}$ alkylene-$C_{3-6}$ cycloalkyl, —$C_{1-4}$ alkylene-OR, —$C_{1-4}$ alkylene-$NR^aR^b$, and —$C_{1-4}$ alkylene-$CF_3$;

$R_{11}$ is selected from isopropyl and $CF_3$;

$R_{12}$ is selected from H, $CF_3$, $C_{1-6}$ alkyl, $C_{2-6}$ alkenyl, $C_{2-6}$ alkynyl, and $C_{3-6}$ cycloalkyl;

$R_{13}$ is selected from H and $C_{1-6}$ alkyl;

$R_{14}$ is selected from H and $C_{1-6}$ alkyl;

alternatively, $NR_{13}R_{14}$ forms a 4-8 membered cyclic amine, wherein:

(a) 0-2 ring $CH_2$ are replaced by a group selected from O, S, S(O), $SO_2$, $SO_2$NR, C(O)NR, and NR;

(b) 0-1 ring double bond is present;

(c) the cyclic amine is optionally substituted at a $CH_2$ and/or NH position with 1-2 groups selected from $C_{1-6}$ alkyl, —$C_{0-4}$ alkylene-$C_{3-6}$ cycloalkyl, halo, $CH_2CF_3$, $CHF_2$, $CF_3$, $CH_2CHF_2$, —CN, $OCH_2CF_3$, $OCHF_2$, $OCF_3$, $OCH_2CHF_2$, CH(OR)$(CF_3)$, C(OR)$(CF_3)_2$, $C_{2-6}$ alkenyl, $C_{2-6}$ alkynyl, —$C_{0-4}$ alkylene-OR, O—$C_{2-4}$ alkylene-OR, —$C_{0-4}$ alkylene-C(O)$R^a$, —$C_{0-4}$ alkylene-C(N)—$C_{1-4}$ alkyl, —$C_{0-4}$ alkylene-C(N)NRR, —$C_{0-4}$ alkylene-C(O)$OR^a$, —$C_{0-4}$ alkylene-C(O)SR, —$C_{0-4}$ alkylene-C(S)$OR^a$, —$C_{0-4}$ alkylene-C(O)$NR^aR^b$, —$C_{0-4}$ alkylene-OC(O)$NR^aR^b$, —$C_{0-4}$ alkylene-$NR^a$C(O)OR, —$C_{0-4}$ alkylene-$NR^a$C(O)$NR^aR^b$, —$C_{0-4}$ alkylene-$S(O)_2NR^aR^b$, —$C_{0-4}$ alkylene-$NR^a$C(O)$R^a$, —CH$(CF_3)NR^a$C(O)$R^a$—$C_{1-4}$ alkyl, —$C_{0-4}$ alkylene-$NR^aS(O)_2$—$C_{1-4}$ alkyl, —CH$(CF_3)NR^aS(O)_2$—$C_{1-4}$ alkyl, —$C_{0-4}$ alkylene-$NR^aS(O)_2$—$CF_3$, —$C_{0-4}$ alkylene-$S(O)_2$—$C_{1-4}$ alkyl, —$C_{0-4}$ alkylene-aryl, —$(CH_2)_{0-4}$—N-morpholin-3-one, —$(CH_2)_{0-4}$—N-2,2-dimethyl-morpholin-3-one, —$C_{0-4}$ alkylene-heteroaryl, —O—$(CH_2)_{0-4}$-aryl, —O—$(CH_2)_{0-4}$-heteroaryl, —C(O)-aryl, and —C(O)-heteroaryl, provided that only one substituent on the monocyclic amine is alkyl; and, (d) wherein each aryl or heteroaryl in (c) is optionally substituted with 1-2 groups selected from $C_{1-6}$ alkyl, —$C_{0-4}$ alkylene-$C_{3-6}$ cycloalkyl, —O—$C_{3-6}$ cycloalkyl, halo, $CH_2CF_3$, $CHF_2$, $CF_3$, $CH_2CHF_2$, C(OR)$(CF_3)_2$, $C_{2-6}$ alkenyl, $C_{2-6}$ alkynyl, —$C_{0-4}$ alkylene-OR, —O—$C_{2-4}$ alkylene-OR, —$C_{0-4}$ alkylene-C(O)R, —$C_{0-4}$ alkylene-C(O)OR, —$C_{0-4}$ alkylene-NRR, —$C_{0-4}$ alkylene-C(O)NRR, —$C_{0-4}$ alkylene-$S(O)_2$NRR, —$C_{0-4}$ alkylene-NRC(O)—$C_{1-4}$ alkyl, —$C_{0-4}$ alkylene-NRS$(O)_2$—$C_{1-4}$ alkyl, —$C_{0-4}$ alkylene-$S(O)_2$—$C_{1-4}$ alkyl, and —$C_{0-4}$ alkylene-aryl, and $C_{0-4}$ alkylene-heteroaryl;

$R_{15}$ is selected from H, $C_{1-6}$ alkyl, and —$C_{1-4}$ alkylene-OR;

$R_{16}$ is selected from H and $C_{1-6}$ alkyl;

alternatively, $NR_{15}R_{16}$ forms a 4-8 membered cyclic amine, wherein:

(a) 0-2 ring $CH_2$ are replaced by a group selected from O, S, S(O), $SO_2$, $SO_2$NR, C(O)NR, and NR;

(b) 0-1 ring double bond is present;

(c) the cyclic amine is optionally substituted at a $CH_2$ and/or NH position with 1-2 groups selected from $C_{1-6}$ alkyl, —$C_{0-4}$ alkylene-$C_{3-6}$ cycloalkyl, halo, $CH_2CF_3$, $CHF_2$, $CF_3$, $CH_2CHF_2$, —CN, $OCH_2CF_3$, $OCHF_2$, $OCF_3$, $OCH_2CHF_2$, CH(OR)$(CF_3)$, C(OR)$(CF_3)_2$, $C_{2-6}$ alkenyl, $C_{2-6}$ alkynyl, —$C_{0-4}$ alkylene-OR, —O—$C_{2-4}$ alkylene-OR, —$C_{0-4}$ alkylene-C(O)$R^a$, —$C_{0-4}$ alkylene-C(N)—$C_{1-4}$ alkyl, —$C_{0-4}$ alkylene-C(N)NRR, —$C_{0-4}$ alkylene-C(O)$OR^a$, —$C_{0-4}$ alkylene-C(O)SR, —$C_{0-4}$ alkylene-C(S)$OR^a$, —$C_{0-4}$ alkylene-C(O)$NR^aR^b$, —$C_{0-4}$ alkylene-OC(O)$NR^aR^b$, —$C_{0-4}$ alkylene-$NR^a$C(O)OR, —$C_{0-4}$ alkylene-$NR^a$C(O)$NR^aR^b$, —$C_{0-4}$ alkylene-$S(O)_2NR^aR^b$, —$C_{0-4}$ alkylene-$NR^a$C(O)$R^a$, —CH$(CF_3)NR^a$C(O)$R^a$—$C_{1-4}$ alkyl, —$C_{0-4}$ alkylene-$NR^aS(O)_2$—$C_{1-4}$ alkyl, —CH$(CF_3)NR^aS(O)_2$—$C_{1-4}$ alkyl, —$C_{0-4}$ alkylene-$NR^aS(O)_2$—$CF_3$, —$C_{0-4}$ alkylene-$S(O)_2$—$C_{1-4}$ alkyl, —$C_{0-4}$ alkylene-aryl, —$(CH_2)_{0-4}$—N-morpholin-3-one, —$(CH_2)_{0-4}$—N-2,2-dimethyl-morpholin-3-one, —$C_{0-4}$ alkylene-heteroaryl, —O—$(CH_2)_{0-4}$-aryl, —O—$(CH_2)_{0-4}$-heteroaryl, —C(O)-aryl, and —C(O)-heteroaryl, provided that only one substituent on the monocyclic amine is alkyl; and, (d) wherein each aryl or heteroaryl in (c) is optionally substituted with 1-2 groups selected from $C_{1-6}$ alkyl, —$C_{0-4}$ alkylene-$C_{3-6}$ cycloalkyl, —O—$C_{3-6}$ cycloalkyl, halo, $CH_2CF_3$, $CHF_2$, $CF_3$, $CH_2CHF_2$, C(OR)$(CF_3)_2$, $C_{2-6}$ alkenyl, $C_{2-6}$ alkynyl, —$C_{0-4}$ alkylene-OR, —O—$C_{2-4}$ alkylene-OR, —$C_{0-4}$ alkylene-C(O)R, —$C_{0-4}$ alkylene-C(O)OR, —$C_{0-4}$ alkylene-NRR, —$C_{0-4}$ alkylene-C(O)NRR, —$C_{0-4}$ alkylene-$S(O)_2$NRR, —$C_{0-4}$ alkylene-NRC(O)—$C_{1-4}$ alkyl, —$C_{0-4}$ alkylene-NRS$(O)_2$—$C_{1-4}$ alkyl, —$C_{0-4}$ alkylene-$S(O)_2$—$C_{1-4}$ alkyl, and —$C_{0-4}$ alkylene-aryl, and $C_{0-4}$ alkylene-heteroaryl;

Het(Ar) is an aryl or a heteroaryl, wherein (a) the Het(Ar) ring is optionally substituted with 1-2 groups selected from —NC, $C_{1-6}$ alkyl, —$C_{0-4}$ alkylene-$C_{3-6}$ cycloalkyl, halo, $CH_2CF_3$, $CHF_2$, $CF_3$, $CH_2CHF_2$, C(OR)$(CF_3)_2$, $C_{2-6}$ alkenyl, $C_{2-6}$ alkynyl, —$C_{0-4}$ alkylene-OR, —O—$C_2$-4 alkylene-OR, —$C_{0-4}$ alkylene-C(O)R, —$C_{0-4}$ alkylene-C(O)OR, —$C_{0-4}$ alkylene-C(O)$NR^aR^b$, —$C_{0-4}$ alkylene-$S(O)_2NR^aR^b$, —$C_{0-4}$ alkylene-$NR^a$C(O)—$C_{1-4}$ alkyl, $C_{0-4}$ alkylene-$NR^aS(O)_2$—$C_{1-4}$ alkyl, and —$C_{0-4}$ alkylene-$S(O)_2$—$C_{1-4}$ alkyl; and, (b) 0-1 ring $CH_2$ present in each ring is replaced by a group selected from C═0 and C═S.

Another aspect of the invention involves a compound of Formula I (or one of Formula II-IVa), or a stereoisomer or pharmaceutically acceptable salt thereof, wherein:

$R_6$ is $R_{6A}1$ or $R_{6A}2$ wherein * is the point of attachment to formula I (or one of Formula II-IVa):

$R_{6A1}$

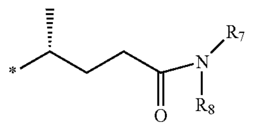

$R_{6A2}$

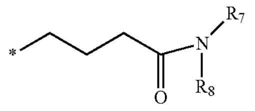

$R_7$ is selected from $C_{1-4}$ alkyl, alternatively, $R_7$ is $OR_{10}$;

$R_8$ is selected from $C_{1-6}$ alkyl, —$C_{0-4}$ alkylene-$C_{3-6}$ cycloalkyl, —$C_{0-4}$ alkylene-aryl, —$C_{0-4}$ alkylene-$C_{4-6}$ membered cyclic amine, —$C_{0-4}$ alkylene-heteroaryl, —$C_{1-4}$ alkylene-OR, —$C_{1-4}$ alkylene-$NR^aR^b$, —$C_{1-4}$ alkylene-$CF_3$, and —$C_{1-4}$ alkylene-C(O)OR, wherein each cycloalkyl, cyclic amine, aryl, and heteroaryl is optionally substituted with $C_{0-4}$ alkylene-OR, —$C_{0-4}$ alkylene-C(O)$R^a$, —$C_{0-4}$ alkylene-C(O)O$R^a$, —$C_{0-4}$ alkylene-C(O)$NR^aR^b$, —$C_{0-4}$ alkylene-OC(O)$NR^aR^b$, —$C_{0-4}$ alkylene-$NR^a$C(O)$NR^aR^b$, —$C_{0-4}$ alkylene-S(O)$_2NR^aR^b$, —$C_{0-4}$ alkylene-$NR^a$C(O)$R^a$, $C_{0-4}$ alkylene-$NR^aS(O)_2$—$C_{1-4}$ alkyl, and —$C_{0-4}$ alkylene-$S(O)_2$—$C_{1-4}$ alkyl;

alternatively, $NR_7R_8$ forms a 4-10 membered mono-, bi-, or tricyclic amine or a 7-11 membered spirocyclic amine, wherein:

(a) 0-2 ring $CH_2$ are replaced by a group selected from O, S, S(O), $SO_2$, $SO_2NR$, C(O)NR, and NR;

(b) 0-1 ring double bond is present;

(c) the cyclic amine is optionally substituted at a $CH_2$ and/or NH position with 1-2 groups selected from $C_{1-6}$ alkyl, —$C_{0-4}$ alkylene-$C_{3-6}$ cycloalkyl, halo, $CH_2CF_3$, $CHF_2$, $CF_3$, $CH_2CHF_2$, —CN, $OCH_2CF_3$, $OCHF_2$, $OCF_3$, $OCH_2CHF_2$, CH(OR)($CF_3$), C(OR)($CF_3$)$_2$, $C_{2-6}$ alkenyl, $C_{2-6}$ alkynyl, —$C_{0-4}$ alkylene-OR, —O—$C_{2-4}$ alkylene-OR, —$C_{0-4}$ alkylene-C(O)$R^a$, —$C_{0-4}$ alkylene-C(N)—$C_{1-4}$ alkyl, —$C_{0-4}$ alkylene-C(N)NRR, —$C_{0-4}$ alkylene-C(O)O$R^a$, —$C_{0-4}$ alkylene-C(O)SR, —$C_{0-4}$ alkylene-C(S)O$R^a$, —$C_{0-4}$ alkylene-C(O)$NR^aR^b$, —$C_{0-4}$ alkylene-OC(O)$NR^aR^b$, $C_{0-4}$ alkylene-$NR^a$C(O)OR, —$C_{0-4}$ alkylene-$NR^a$C(O)$NR^aR^b$, —$C_{0-4}$ alkylene-$S(O)_2NR^aR^b$, —$C_{0-4}$ alkylene-$NR^a$C(O)$R^a$, —CH($CF_3$)$NR^a$C(O)$R^a$—$C_{1-4}$ alkyl, —$C_{0-4}$ alkylene-$NR^aS(O)_2$—$C_{1-4}$ alkyl, —CH($CF_3$)$NR^aS(O)_2$—$C_{1-4}$ alkyl, —$C_{0-4}$ alkylene-$NR^aS(O)_2$—$CF_3$, —$C_{0-4}$ alkylene-$S(O)_2$—$C_{1-4}$ alkyl, —$C_{0-4}$ alkylene-aryl, —$(CH_2)_{0-4}$—N-morpholin-3-one, —$(CH_2)_{0-4}$—N-2,2-dimethyl-morpholin-3-one, —$C_{0-4}$ alkylene-heteroaryl, —O—$(CH_2)_{0-4}$-aryl, —O—$(CH_2)_{0-4}$-heteroaryl, —C(O)-aryl, and —C(O)-heteroaryl, provided that only one substituent on the monocyclic amine is alkyl; and, (d) wherein each aryl or heteroaryl in (c) is optionally substituted with 1-2 groups selected from $C_{1-6}$ alkyl, —$C_{0-4}$ alkylene-$C_{3-6}$ cycloalkyl, —O—$C_{3-6}$ cycloalkyl, halo, $CH_2CF_3$, $CHF_2$, $CF_3$, $CH_2CHF_2$, C(OR)($CF_3$)$_2$, $C_{2-6}$ alkenyl, $C_{2-6}$ alkynyl, —$C_{0-4}$ alkylene-OR, —O—$C_{2-4}$ alkylene-OR, —$C_{0-4}$ alkylene-C(O)R, —$C_{0-4}$ alkylene-C(O)OR, —$C_{0-4}$ alkylene-NRR, —$C_{0-4}$ alkylene-C(O)NRR, —$C_{0-4}$ alkylene-$S(O)_2$NRR, —$C_{0-4}$ alkylene-NRC(O)—$C_{1-4}$ alkyl, —$C_{0-4}$ alkylene-NRS(O)$_2$—$C_{1-4}$ alkyl, —$C_{0-4}$ alkylene-$S(O)_2$—$C_{1-4}$ alkyl, and —$C_{0-4}$ alkylene-aryl, and $C_{0-4}$ alkylene-heteroaryl;

R, at each occurrence, is selected from H and $C_{1-6}$ alkyl;

$R^a$, at each occurrence, is selected from H, $C_{1-6}$ alkyl, —$C_{0-4}$ alkylene-$C_{3-6}$ cycloalkyl, —$C_{0-4}$ alkylene-$C_{4-6}$ cyclic ether, —$C_{0-4}$ alkylene-$C_{4-6}$ cyclic amine, —$C_{2-4}$ alkylene-OR (if this is subst. off O, then require alkylene or different substituent? Ex. 280)), —$C_{0-4}$ alkylene-C(O)R, —$C_{0-4}$ alkylene-C(O)OR, —$C_{0-4}$ alkylene-C(O)NRR, —$C_{0-4}$ alkylene-$S(O)_2$NRR, —$C_{0-4}$ alkylene-NRC(O)—$C_{1-4}$ alkyl, —$C_{0-4}$ alkylene-NRS(O)$_2$—$C_{1-4}$ alkyl, —$C_{0-4}$ alkylene-$S(O)_2$—$C_{1-4}$ alkyl, —$C_{0-4}$ alkylene-aryl, and —$C_{0-4}$ alkylene-heteroaryl, $R^b$, at each occurrence, is selected from H and $C_{1-6}$ alkyl; and, alternatively, $NR^aR^b$ forms a 4-6 membered cyclic amine substituted with 0-1 groups selected from $C_{1-6}$ alkyl, OR, halo, and $CF_3$.

Another aspect of the invention involves a compound of Formula I (or one of Formula II-IVa), or a stereoisomer or pharmaceutically acceptable salt thereof, wherein:

$R_6$ is $R_{6B1}$, wherein * is the point of attachment to formula I (or one of Formula II-IVa):

$R_{6B1}$

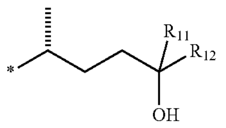

$R_{11}$ is $CF_3$; and, $R_{12}$ is selected from $CF_3$, ethyl, ethenyl, cyclopropyl, and cyclobutyl.

Another aspect of the invention involves a compound of Formula I (or one of Formula II-IVa), or a stereoisomer or pharmaceutically acceptable salt thereof, wherein:

$R_6$ is $R_{6C1}$ or $R_{6C2}$ wherein * is the point of attachment to formula I (or one of Formula II-IVa):

$R_{6C1}$

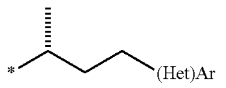

$R_{6C2}$

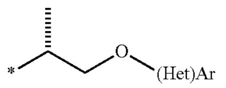

Het(Ar) is selected from the group phenyl, pyridyl, pyrimidyl, quinolinyl, 1,2-thiazolyl, 1,3-thiazolyl, and 1,3-oxazolyl, wherein the Het(Ar) ring is optionally substituted with 1-2 groups selected from $C_{1-6}$ alkyl, OR, Cl, F, and $CF_3$; and, R is $C_{1-4}$ alkyl;

Another aspect of the invention involves a compound of Formula I (or one of Formula II-IVa), or a stereoisomer or pharmaceutically acceptable salt thereof, wherein:

$R_6$ is $R_{6D1}$, wherein * is the point of attachment to formula I (or one of Formula II-IVa):

$R_{6D1}$

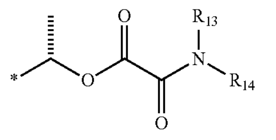

R, at each occurrence, is selected from H and $C_{1-4}$ alkyl;

$R^a$, at each occurrence, is selected from H, $C_{1-6}$ alkyl, —$C_{0-4}$ alkylene-$C_{3-6}$ cycloalkyl, —$C_{0-4}$ alkylene-$C_{4-6}$ cyclic ether, —$C_{0-4}$ alkylene-$C_{4-6}$ cyclic amine, —$C_{2-4}$ alkylene-OR, —$C_{0-4}$ alkylene-C(O)R, —$C_{0-4}$ alkylene-C(O)OR, —$C_{0-4}$ alkylene-C(O)NRR, —$C_{0-4}$ alkylene-$S(O)_2$NRR, —$C_{0-4}$ alkylene-NRC(O)—$C_{1-4}$ alkyl, —$C_{0-4}$ alkylene-NRS$(O)_2$—$C_{1-4}$ alkyl, —$C_{0-4}$ alkylene-S$(O)_2$—$C_{1-4}$ alkyl, —$C_{0-4}$ alkylene-aryl, and —$C_{0-4}$ alkylene-heteroaryl, wherein each cycloalkyl, cyclic ether, cyclic amine, aryl, and heteroaryl is optionally substituted with $C_{1-6}$ alkyl and $C_{0-4}$ alkylene-OR;

$R^b$, at each occurrence, is selected from H and $C_{1-6}$ alkyl;

alternatively, $NR^aR^b$ forms a 4-6 membered cyclic amine substituted with 0-1 groups selected from $C_{1-6}$ alkyl, OR, halo, and $CF_3$;

$R_{13}$ is selected from $C_{1-4}$ alkyl;

$R_{14}$ is selected from $C_{1-4}$ alkyl;

alternatively, $NR_{13}R_{14}$ forms a 4-8 membered cyclic amine, wherein:

(a) 0-2 ring $CH_2$ are replaced by a group selected from O, S, S(O), $SO_2$, $SO_2$NR, C(O)NR, and NR;

(b) 0-1 ring double bond is present;

(c) the cyclic amine is optionally substituted at a $CH_2$ and/or NH position with 1-2 groups selected from $C_{1-6}$ alkyl, —$C_{0-4}$ alkylene-$C_{3-6}$ cycloalkyl, halo, $CH_2CF_3$, $CHF_2$, $CF_3$, $CH_2CHF_2$, —CN, $OCH_2CF_3$, $OCHF_2$, $OCF_3$, $OCH_2CHF_2$, CH(OR)$(CF_3)$, C(OR)$(CF_3)_2$, $C_{2-6}$ alkenyl, $C_{2-6}$ alkynyl, —$C_{0-4}$ alkylene-OR, O—$C_{2-4}$ alkylene-OR, —$C_{0-4}$ alkylene-C(O)$R^a$, —$C_{0-4}$ alkylene-C(N)—$C_{1-4}$ alkyl, $C_{0-4}$ alkylene-C(N)NRR, —$C_{0-4}$ alkylene-C(O)O$R^a$, —$C_{0-4}$ alkylene-C(O)SR, —$C_{0-4}$ alkylene-C(S)O$R^a$, —$C_{0-4}$ alkylene-C(O)$NR^aR^b$, —$C_{0-4}$ alkylene-OC(O)$NR^aR^b$, —$C_{0-4}$ alkylene-$NR^a$C(O)OR, —$C_{0-4}$ alkylene-$NR^a$C(O)$NR^aR^b$, —$C_{0-4}$ alkylene-$S(O)_2NR^aR^b$, —$C_{0-4}$ alkylene-$NR^a$C(O)$R^a$, —CH$(CF_3)NR^a$C(O)$R^a$—$C_{1-4}$ alkyl, —$C_{0-4}$ alkylene-$NR^aS(O)_2$—$C_{1-4}$ alkyl, —CH$(CF_3)NR^aS(O)_2$—$C_{1-4}$ alkyl, —$C_{0-4}$ alkylene-$NR^aS(O)_2$—$CF_3$, —$C_{0-4}$ alkylene-$S(O)_2$—$C_{1-4}$ alkyl, —$C_{0-4}$ alkylene-aryl, —$(CH_2)_{0-4}$—N-morpholin-3-one, —$(CH_2)_{0-4}$—N-2,2-dimethyl-morpholin-3-one, —$C_{0-4}$ alkylene-heteroaryl, —O—$(CH_2)_{0-4}$-aryl, —O—$(CH_2)_{0-4}$-heteroaryl, —C(O)-aryl, and —C(O)-heteroaryl, provided that only one substituent on the monocyclic amine is alkyl; and, (d) wherein each aryl or heteroaryl in (c) is optionally substituted with 1-2 groups selected from $C_{1-6}$ alkyl, —$C_{0-4}$ alkylene-$C_{3-6}$ cycloalkyl, —O—$C_{3-6}$ cycloalkyl, halo, $CH_2CF_3$, $CHF_2$, $CF_3$, $CH_2CHF_2$, C(OR)$(CF_3)_2$, $C_{2-6}$ alkenyl, $C_{2-6}$ alkynyl, —$C_{0-4}$ alkylene-OR, —O—$C_{2-4}$ alkylene-OR, —$C_{0-4}$ alkylene-C(O)R, —$C_{0-4}$ alkylene-C(O)OR, —$C_{0-4}$ alkylene-NRR, —$C_{0-4}$ alkylene-C(O)NRR, —$C_{0-4}$ alkylene-$S(O)_2$NRR, —$C_{0-4}$ alkylene-NRC(O)—$C_{1-4}$ alkyl, —$C_{0-4}$ alkylene-NRS$(O)_2$—$C_{1-4}$ alkyl, —$C_{0-4}$ alkylene-$S(O)_2$—$C_{1-4}$ alkyl, and —$C_{0-4}$ alkylene-aryl, and $C_{0-4}$ alkylene-heteroaryl.

Another aspect of the invention involves a compound of Formula I (or one of Formula II-IVa), or a stereoisomer or pharmaceutically acceptable salt thereof, wherein:

$R_6$ is $R_{6D2}$, wherein * is the point of attachment to formula I (or one of Formula II-IVa):

$R_{6D2}$

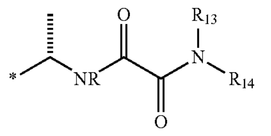

$R^a$, at each occurrence, is selected from H, $C_{1-6}$ alkyl, —$C_{0-4}$ alkylene-$C_{3-6}$ cycloalkyl, —$C_{0-4}$ alkylene-$C_{4-6}$ cyclic ether, —$C_{0-4}$ alkylene-$C_{4-6}$ cyclic amine, —$C_{2-4}$ alkylene-OR, —$C_{0-4}$ alkylene-C(O)R, —$C_{0-4}$ alkylene-C(O)OR, —$C_{0-4}$ alkylene-C(O)NRR, —$C_{0-4}$ alkylene-$S(O)_2$NRR, —$C_{0-4}$ alkylene-NRC(O)—$C_{1-4}$ alkyl, —$C_{0-4}$ alkylene-NRS$(O)_2$—$C_{1-4}$ alkyl, —$C_{0-4}$ alkylene-S$(O)_2$—$C_{1-4}$ alkyl, —$C_{0-4}$ alkylene-aryl, and —$C_{0-4}$ alkylene-heteroaryl, wherein each cycloalkyl, cyclic ether, cyclic amine, aryl, and heteroaryl is optionally substituted with $C_{1-6}$ alkyl and $C_{0-4}$ alkylene-OR;

$R^b$, at each occurrence, is selected from H and $C_{1-6}$ alkyl;

alternatively, $NR^aR^b$ forms a 4-6 membered cyclic amine substituted with 0-1 groups selected from $C_{1-6}$ alkyl, OR, halo, and $CF_3$;

$R_{13}$ is selected from $C_{1-4}$ alkyl;

$R_{14}$ is selected from $C_{1-4}$ alkyl;

alternatively, $NR_{13}R_{14}$ forms a 4-8 membered cyclic amine, wherein:

(a) 0-2 ring $CH_2$ are replaced by a group selected from O, S, S(O), $SO_2$, $SO_2$NR, C(O)NR, and NR;

(b) 0-1 ring double bond is present;

(c) the cyclic amine is optionally substituted at a $CH_2$ and/or NH position with 1-2 groups selected from $C_{1-6}$ alkyl, —$C_{0-4}$ alkylene-$C_{3-6}$ cycloalkyl, halo, $CH_2CF_3$, $CHF_2$, $CF_3$, $CH_2CHF_2$, —CN, $OCH_2CF_3$, $OCHF_2$, $OCF_3$, $OCH_2CHF_2$, CH(OR)$(CF_3)$, C(OR)$(CF_3)_2$, $C_{2-6}$ alkenyl, $C_{2-6}$ alkynyl, —$C_{0-4}$ alkylene-OR, O—$C_{2-4}$ alkylene-OR, —$C_{0-4}$ alkylene-C(O)$R^a$, —$C_{0-4}$ alkylene-C(N)—$C_{1-4}$ alkyl, $C_{0-4}$ alkylene-C(N)NRR, —$C_{0-4}$ alkylene-C(O)O$R^a$, —$C_{0-4}$ alkylene-C(O)SR, —$C_{0-4}$ alkylene-C(S)O$R^a$, —$C_{0-4}$ alkylene-C(O)$NR^aR^b$, —$C_{0-4}$ alkylene-OC(O)$NR^aR^b$, $C_{0-4}$ alkylene-$NR^a$C(O)OR, —$C_{0-4}$ alkylene-$NR^a$C(O)$NR^aR^b$, —$C_{0-4}$ alkylene-$S(O)_2NR^aR^b$, —$C_{0-4}$ alkylene-$NR^a$C(O)$R^a$, —CH $(CF_3)NR^aC(O)R^a$—$C_{1-4}$ alkyl, —$C_{0-4}$ alkylene-$NR^aS(O)_2$—$C_{1-4}$ alkyl, —$CH(CF_3)NR^aS(O)_2$—$C_{1-4}$ alkyl, —$C_{0-4}$ alkylene-$NR^aS(O)_2$—$CF_3$, —$C_{0-4}$ alkylene-$S(O)_2$—$C_{1-4}$ alkyl, —$C_{0-4}$ alkylene-aryl, —$(CH_2)_{0-4}$—N-morpholin-3-one, —$(CH_2)_{0-4}$—N-2,2-dimethyl-morpholin-3-one, —$C_{0-4}$ alkylene-heteroaryl, —O—$(CH_2)_{0-4}$-aryl, —O—$(CH_2)_{0-4}$-heteroaryl, —C(O)-aryl, and —C(O)-heteroaryl, provided that only one substituent on the monocyclic amine is alkyl; and, (d) wherein each aryl or heteroaryl in (c) is optionally substituted with 1-2 groups selected from $C_{1-6}$ alkyl, —$C_{0-4}$ alkylene-$C_{3-6}$ cycloalkyl, —O—$C_{3-6}$ cycloalkyl, halo, $CH_2CF_3$, $CHF_2$, $CF_3$, $CH_2CHF_2$, $C(OR)(CF_3)_2$, $C_{2-6}$ alkenyl, $C_{2-6}$ alkynyl, —$C_{0-4}$ alkylene-OR, —O—$C_{2-4}$ alkylene-OR, —$C_{0-4}$ alkylene-C(O)R, —$C_{0-4}$ alkylene-C(O)OR, —$C_{0-4}$ alkylene-NRR, —$C_{0-4}$ alkylene-C(O)NRR, —$C_{0-4}$ alkylene-$S(O)_2NRR$, —$C_{0-4}$ alkylene-NRC(O)—$C_{1-4}$ alkyl, —$C_{0-4}$ alkylene-$NRS(O)_2$—$C_{1-4}$ alkyl, —$C_{0-4}$ alkylene-$S(O)_2$—$C_{1-4}$ alkyl, and —$C_{0-4}$ alkylene-aryl, and $C_{0-4}$ alkylene-heteroaryl.

Another aspect of the invention involves a compound of Formula I (or one of Formula II-IVa), or a stereoisomer or pharmaceutically acceptable salt thereof, wherein:

$R_6$ is $R_{6E1}$, wherein * is the point of attachment to formula I (or one of Formula II-IVa):

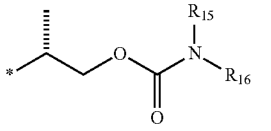

$R_{6E1}$

R, at each occurrence, is selected from H and $C_{1-4}$ alkyl;

$R^a$, at each occurrence, is selected from H, $C_{1-6}$ alkyl, —$C_{0-4}$ alkylene-$C_{3-6}$ cycloalkyl, —$C_{0-4}$ alkylene-$C_{4-6}$ cyclic ether, —$C_{0-4}$ alkylene-$C_{4-6}$ cyclic amine, —$C_{2-4}$ alkylene-OR, —$C_{0-4}$ alkylene-C(O)R, —$C_{0-4}$ alkylene-C(O)OR, —$C_{0-4}$ alkylene-C(O)NRR, —$C_{0-4}$ alkylene-$S(O)_2NRR$, —$C_{0-4}$ alkylene-NRC(O)—$C_{1-4}$ alkyl, —$C_{0-4}$ alkylene-$NRS(O)_2$—$C_{1-4}$ alkyl, —$C_{0-4}$ alkylene-$S(O)_2$—$C_{1-4}$ alkyl, —$C_{0-4}$ alkylene-aryl, and —$C_{0-4}$ alkylene-heteroaryl, wherein each cycloalkyl, cyclic ether, cyclic amine, aryl, and heteroaryl is optionally substituted with $C_{1-6}$ alkyl and $C_{0-4}$ alkylene-OR;

$R^b$, at each occurrence, is selected from H and $C_{1-6}$ alkyl;

alternatively, $NR^aR^b$ forms a 4-6 membered cyclic amine substituted with 0-1 groups selected from $C_{1-6}$ alkyl, OR, halo, and $CF_3$;

$R_{15}$ is selected from $C_{1-6}$ alkyl and —$C_{1-4}$ alkylene-OR;

$R_{16}$ is selected from $C_{1-6}$ alkyl;

alternatively, $NR_{15}R_{16}$ forms a 4-8 membered cyclic amine, wherein:

(a) 0-2 ring $CH_2$ are replaced by a group selected from O, S, S(O), $SO_2$, $SO_2NR$, C(O)NR, and NR;

(b) 0-1 ring double bond is present;

(c) the cyclic amine is optionally substituted at a $CH_2$ and/or NH position with 1-2 groups selected from $C_{1-6}$ alkyl, —$C_{0-4}$ alkylene-$C_{3-6}$ cycloalkyl, halo, $CH_2CF_3$, $CHF_2$, $CF_3$, $CH_2CHF_2$, —CN, $OCH_2CF_3$, $OCHF_2$, $OCF_3$, $OCH_2CHF_2$, $CH(OR)(CF_3)$, $C(OR)(CF_3)_2$, $C_{2-6}$ alkenyl, $C_{2-6}$ alkynyl, —$C_{0-4}$ alkylene-OR, O—$C_{2-4}$ alkylene-OR, —$C_{0-4}$ alkylene-$C(O)R^a$, —$C_{0-4}$ alkylene-C(N)—$C_{1-4}$ alkyl, $C_{0-4}$ alkylene-C(N)NRR, —$C_{0-4}$ alkylene-$C(O)OR^a$, —$C_{0-4}$ alkylene-C(O)SR, —$C_{0-4}$ alkylene-$C(S)OR^a$, —$C_{0-4}$ alkylene-$C(O)NR^aR^b$, —$C_{0-4}$ alkylene-$OC(O)NR^aR^b$, —$C_{0-4}$ alkylene-$NR^aC(O)OR$, —$C_{0-4}$ alkylene-$NR^aC(O)NR^aR^b$, —$C_{0-4}$ alkylene-$S(O)_2NR^aR^b$, —$C_{0-4}$ alkylene-$NR^aC(O)R^a$, —$CH(CF_3)NR^aC(O)R^a$—$C_{1-4}$ alkyl, —$C_{0-4}$ alkylene-$NR^aS(O)_2$—$C_{1-4}$ alkyl, —$CH(CF_3)NR^aS(O)_2$—$C_{1-4}$ alkyl, —$C_{0-4}$ alkylene-$NR^aS(O)_2$—$CF_3$, —$C_{0-4}$ alkylene-$S(O)_2$—$C_{1-4}$ alkyl, —$C_{0-4}$ alkylene-aryl, —$(CH_2)_{0-4}$—N-morpholin-3-one, —$(CH_2)_{0-4}$—N-2,2-dimethyl-morpholin-3-one, —$C_{0-4}$ alkylene-heteroaryl, —O—$(CH_2)_{0-4}$-aryl, —O—$(CH_2)_{0-4}$-heteroaryl, —C(O)-aryl, and —C(O)-heteroaryl, provided that only one substituent on the monocyclic amine is alkyl; and, (d) wherein each aryl or heteroaryl in (c) is optionally substituted with 1-2 groups selected from $C_{1-6}$ alkyl, —$C_{0-4}$ alkylene-$C_{3-6}$ cycloalkyl, —O—$C_{3-6}$ cycloalkyl, halo, $CH_2CF_3$, $CHF_2$, $CF_3$, $CH_2CHF_2$, $C(OR)(CF_3)_2$, $C_{2-6}$ alkenyl, $C_{2-6}$ alkynyl, —$C_{0-4}$ alkylene-OR, —O—$C_{2-4}$ alkylene-OR, —$C_{0-4}$ alkylene-C(O)R, —$C_{0-4}$ alkylene-C(O)OR, —$C_{0-4}$ alkylene-NRR, —$C_{0-4}$ alkylene-C(O)NRR, —$C_{0-4}$ alkylene-$S(O)_2NRR$, —$C_{0-4}$ alkylene-NRC(O)—$C_{1-4}$ alkyl, —$C_{0-4}$ alkylene-$NRS(O)_2$—$C_{1-4}$ alkyl, —$C_{0-4}$ alkylene-$S(O)_2$—$C_{1-4}$ alkyl, and —$C_{0-4}$ alkylene-aryl, and $C_{0-4}$ alkylene-heteroaryl.

Another aspect of the invention involves a compound of Formula I (or one of Formula II-IVa), or a stereoisomer or pharmaceutically acceptable salt thereof, wherein:

$R_6$ is $R_{6F1}$, wherein * is the point of attachment to formula I:

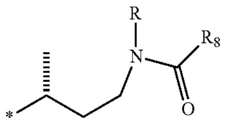

$R_{6F1}$

R, at each occurrence, is selected from H and $C_{1-6}$ alkyl;

$R_8$ is selected from —$C_{0-4}$ alkylene-$C_{4-6}$ membered cyclic amine optionally substituted with $C_{0-4}$ alkylene-OR, —$C_{0-4}$ alkylene-$C(O)R^a$, —$C_{0-4}$ alkylene-$C(O)OR^a$, —$C_{0-4}$ alkylene-$C(O)NR^aR^b$, —$C_{0-4}$ alkylene-$OC(O)NR^aR^b$, —$C_{0-4}$ alkylene-$NRC(O)NR^aR^b$, —$C_{0-4}$ alkylene-$S(O)_2NR^aR^b$, —$C_{0-4}$ alkylene-$NR^aC(O)R^a$, —$C_{0-4}$ alkylene-$NR^aS(O)_2$—$C_{1-4}$ alkyl, and —$C_{0-4}$ alkylene-$S(O)_2$—$C_{1-4}$ alkyl;

$R^a$, at each occurrence, is selected from H, $C_{1-6}$ alkyl, —$C_{0-4}$ alkylene-$C_{3-6}$ cycloalkyl, —$C_{0-4}$ alkylene-$C_{4-6}$ cyclic ether, —$C_{0-4}$ alkylene-$C_{4-6}$ cyclic amine, —$C_{2-4}$ alkylene-OR, —$C_{0-4}$ alkylene-C(O)R, —$C_{0-4}$ alkylene-C(O)OR, —$C_{0-4}$ alkylene-C(O)NRR, —$C_{0-4}$ alkylene-$S(O)_2NRR$, —$C_{0-4}$ alkylene-NRC(O)—$C_{1-4}$ alkyl, —$C_{0-4}$ alkylene-$NRS(O)_2$—$C_{1-4}$ alkyl, —$C_{0-4}$ alkylene-$S(O)_2$—$C_{1-4}$ alkyl, —$C_{0-4}$ alkylene-aryl, and —$C_{0-4}$ alkylene-heteroaryl, wherein each cycloalkyl, cyclic ether, cyclic amine, aryl, and heteroaryl is optionally substituted with $C_{1-6}$ alkyl and $C_{0-4}$ alkylene-OR;

$R^b$, at each occurrence, is selected from H and $C_{1-6}$ alkyl;
alternatively, $NR^aR^b$ forms a 4-6 membered cyclic amine substituted with 0-1 groups selected from $C_{1-6}$ alkyl, OR, halo, and $CF_3$.

Another aspect of the invention involves a compound of Table 1, or a stereoisomer or pharmaceutically acceptable salt thereof:

Another aspect of the invention involves a compound of Table 2, or a stereoisomer or pharmaceutically acceptable salt thereof:

Another aspect of the invention involves a compound of Table 3, or a stereoisomer or pharmaceutically acceptable salt thereof:

Another aspect of the invention involves a compound of Table 1, or a stereoisomer or pharmaceutically acceptable salt thereof, wherein the compound has a category A SREBP-2 IC50.

Another aspect of the invention involves a compound of Table 1, or a stereoisomer or pharmaceutically acceptable salt thereof, wherein the compound has a category A SREBP-2 IC50 and a category A or B LXRβ PPI.

Another aspect of the invention involves a compound of Table 1, or a stereoisomer or pharmaceutically acceptable salt thereof, wherein the compound has a category A SREBP-2 IC50 and a category C or D LXRβ PPI.

Another aspect of the invention involves a compound of Table 1, or a stereoisomer or pharmaceutically acceptable salt thereof, wherein the compound has a category A SREBP-2 IC50 and a category D LXRβ PPI.

Another aspect of the invention involves a compound of Table 1, or a stereoisomer or pharmaceutically acceptable salt thereof, wherein the compound has a category A or B LXRβPPI.

Another aspect of the invention involves a compound of Table 1, or a stereoisomer or pharmaceutically acceptable salt thereof, wherein the compound has a category A LXRβ PPI.

Another aspect of the invention involves a compound of Table 1, or a stereoisomer or pharmaceutically acceptable salt thereof, wherein the compound has a category A or B LXRβPPI and a category C or D SREBP-2 IC50.

Another aspect of the invention involves a compound of Table 1, or a stereoisomer or pharmaceutically acceptable salt thereof, wherein the compound has a category A LXRβ PPI and a category C or D SREBP-2 IC50.

Another aspect of the invention involves a compound of Table 1, or a stereoisomer or pharmaceutically acceptable salt thereof, wherein the compound has a category A LXRβ PPI and a category D SREBP-2 IC50.

Another aspect of the invention involves a compound of Table 3, or a stereoisomer or pharmaceutically acceptable salt thereof, wherein the compound has a category A SREBP-2 IC50.

Another aspect of the invention involves a compound of Table 3, or a stereoisomer or pharmaceutically acceptable salt thereof, wherein the compound has a category A SREBP-2 IC50 and a category A or B LXRβ PPI.

Another aspect of the invention involves a compound of Table 3, or a stereoisomer or pharmaceutically acceptable salt thereof, wherein the compound has a category A SREBP-2 IC50 and a category C or D LXRβ PPI.

Another aspect of the invention involves a compound of Table 3, or a stereoisomer or pharmaceutically acceptable salt thereof, wherein the compound has a category A SREBP-2 IC50 and a category D LXRβ PPI.

Another aspect of the invention involves a compound of Table 3, or a stereoisomer or pharmaceutically acceptable salt thereof, wherein the compound has a category A or B LXRβPPI.

Another aspect of the invention involves a compound of Table 3, or a stereoisomer or pharmaceutically acceptable salt thereof, wherein the compound has a category A LXRβ PPI.

Another aspect of the invention involves a compound of Table 3, or a stereoisomer or pharmaceutically acceptable salt thereof, wherein the compound has a category A or B LXRβPPI and a category C or D SREBP-2 IC50.

Another aspect of the invention involves a compound of Table 3, or a stereoisomer or pharmaceutically acceptable salt thereof, wherein the compound has a category A LXRβ PPI and a category C or D SREBP-2 IC50.

Another aspect of the invention involves a compound of Table 3, or a stereoisomer or pharmaceutically acceptable salt thereof, wherein the compound has a category A LXRβ PPI and a category D SREBP-2 IC50.

Another aspect of the invention involves a pharmaceutical composition, comprising: a pharmaceutically acceptable carrier and a therapeutically effective amount of a steroidal compound described herein or a stereoisomer or pharmaceutically acceptable salt thereof.

Another aspect of the invention involves a method for treating a disease, comprising: administering to a patient in need thereof a therapeutically effective amount of a steroidal compound described herein or a stereoisomer or pharmaceutically acceptable salt thereof, wherein the disease is mediated by antagonism of SREBP (e.g., lipogenic cancers such as GBM).

Another aspect of the invention involves a method for treating a disease, comprising: administering to a patient in need thereof a therapeutically effective amount of a steroidal compound described herein or a stereoisomer or pharmaceutically acceptable salt thereof, wherein the disease is mediated by antagonism of SREBP and agonism of LXR (dual SREBP and LXR modulation)(e.g., lipogenic cancers such as prostate and breast).

Another aspect of the invention involves a method for treating a disease, comprising: administering to a patient in need thereof a therapeutically effective amount of a steroidal compound described herein or a stereoisomer or pharmaceutically acceptable salt thereof, wherein the disease is mediated by agonism of LXR.

Another aspect of the invention involves a steroidal compound described herein for use in therapy.

Another aspect of the invention involves the use of a steroidal compound described herein for the manufacture of a medicament, wherein the medicament is useful as an antagonist of SREBP (e.g., SREBP-1 and/or SREBP-2).

Another aspect of the invention involves the use of a steroidal compound described herein for the manufacture of a medicament, wherein the medicament is useful as an antagonist of SREBP (e.g., SREBP-1 and/or SREBP-2) and an agonist of LXR.

Another aspect of the invention involves the use of a steroidal compound described herein for the manufacture of a medicament, wherein the medicament is useful as an agonist of LXR.

Another aspect of the invention involves the treatment of an LXR-mediated disease selected from age and UV exposure-dependent skin wrinkling, Alzheimer's disease, amyotrophic lateral sclerosis, asthma, atherosclerosis, atopic dermatitis, cardiac steatosis, coronary artery disease, dementia with Lewy bodies, dyslipidemia, familial hypercholesterolemia, fronto-temporal dementias, glioblastoma (GBM), hepatitis C virus infection or its complications, Huntington's disease, hypercholesterolemia in nephrotic syndrome, hyperglycemia, hyperlipidemia, hypertension, inflammation, inflammatory bowel disease, insulin resistance, liver fibrosis, liver inflammation, macular degeneration, metabolic syndrome, multiple sclerosis, non-alcoholic fatty liver disease (NAFLD), non-alcoholic steatohepatitis (NASH), obesity, osteoporosis, osteoarthritis, Parkinson's disease, peripheral neuropathy, psoriasis, rheumatoid arthritis, stroke, type II diabetes, viral myocarditis, and unwanted side-effects of long-term glucocorticoid treatment in diseases such as rheumatoid arthritis.

Another aspect of the invention involves the treatment of lipogenic cancers or the alleviation of associated symptoms thereof through the administration of one or more of the steroidal compounds described herein.

Another aspect of the invention involves the treatment of lipogenic cancers, wherein the treatment leads to the reduction in tumor viability, cell growth, cell size, and/or metastasis.

Lipogenic cancers include brain (e.g., GBM), breast, lung (including, for example, non-small cell lung cancer (NSCLC) and small cell lung cancer (SCLC)), melanoma (including, for example, BRAF wild type and BRAF positive melanomas), hepatocellular carcinoma (HCC), colon, prostate, and ovarian.

Another aspect of the invention involves the treatment of GBM or the alleviation of associated symptoms thereof through the administration of one or more of the compounds described herein.

Another aspect of the invention involves the treatment of breast cancer or the alleviation of associated symptoms thereof through the administration of one or more of the compounds described herein.

Another aspect of the invention involves the treatment of lung cancer or the alleviation of associated symptoms thereof through the administration of one or more of the compounds described herein.

Another aspect of the invention involves the treatment of melanoma cancer or the alleviation of associated symptoms thereof through the administration of one or more of the compounds described herein.

Another aspect of the invention involves the treatment of hepatocellular (HCC) cancer or the alleviation of associated symptoms thereof through the administration of one or more of the compounds described herein.

Another aspect of the invention involves the treatment of colon cancer or the alleviation of associated symptoms thereof through the administration of one or more of the compounds described herein.

Another aspect of the invention involves the treatment of prostate cancer or the alleviation of associated symptoms thereof through the administration of one or more of the compounds described herein.

Another aspect of the invention involves the treatment of ovarian cancer or the alleviation of associated symptoms thereof through the administration of one or more of the compounds described herein.

Another aspect of the invention involves treatment of a lipogenic cancer through the administration of one or more of the steroidal compounds described herein in combination with one or more additional therapeutic agents or treatments. This involves exploiting unique drug combinations that may provide additive, more than additive, or synergistic improvement in efficacy or side-effect management.

Additional agents or combination of agents include:

a. BRAF inhibitors (e.g., agents for BRAF positive melanoma);
b. BRAF inhibitors and MEK inhibitors;
c. PD1 blockers (programmed cell death protein 1 receptor);
d. PD-LI blockers;
e. K-ras inhibitors (Kirsten rat sarcoma viral oncogene homolog);
f. EGFR inhibitors (epidermal growth factor receptor);
g. CTLA4 blockers (cytotoxic T-lymphocyte-associated protein 4) and,
h. chemotherapies.

BRAF inhibitors are typically indicated for patients that have a BRAF positive (BRAF+) mutation (e.g., BRAF+ melanoma). Examples of BRAF inhibitors include vemurafenib (Zelboraf), dabrafenib (Tafinlar), encorafenib (Braftovi), and, sorafenib (Nexavar.

Examples of MEK inhibitors include binimetinib (Mektovi), cobimetinib (Cotellic), selumetinib, trametinib (Mekinist), PD035901, and TAK-733.

Examples of PD1 blockers include pembrolizumab (Keytruda), nivolumab (Opdivo), cempilimab (Liptayo), dostarlimab, JTX-4014, spartalizumab, camrelizumab, sintilimab, tislelizumab, toripalimab, INCMGA00012, AMP-224, and AMP-514.

Examples of PD-L1 blockers include atezolizumab (Tecentriq), avelumab (Bavencio), durvalumab (Imfinzi), KN035, CK-301, AUNP12, CA170, and BMS-986189.

Examples of K-ras inhibitors include Sotorasib (AMG510) and Adagrasib (MRTX849).

EGFR inhibitors include erlotinib, osimertinib, neratinib, geftinib, cetuximab, panitumumab, dacomitinib, lapatinib, necitumumab, mobocertinib, and vandetanib.

Examples of CTLA4 blockers include ipilimumab (Yervoy) and tremelimumab.

Examples of chemotherapies include dacarbazine and temozolomide.

Another aspect of the invention involves modifications to the time that the compounds are administered, the use of dose-modifying agents that control the rate of metabolism of the compound, normal tissue protective agents, and other alterations. Specific examples include: variations of infusion schedules (e.g., bolus IV (intravenous) versus continuous infusion), the use of lymphokines (e.g., G-CSF, GM-CSF, EPO) to increase leukocyte count for improved immune response or for preventing anemia caused by myelosuppressive agents, or the use of rescue agents such as leucovorin for 5-FU or thiosulfate for cisplatin treatment. Other examples include: continuous IV infusion for hours to days; biweekly administration; doses greater than 5 mg/m2/day; progressive escalation of dosing from 1 mg/m2/day based on patient tolerance; doses less than 1 mg/m2 for greater than 14 days; use of caffeine to modulate metabolism; use of isoniazid to modulate metabolism; single and multiple doses escalating from 5 mg/m2/day via bolus; oral doses below 30 or above 130 mg/m2; oral dosages up to 40 mg/m2 for 3 days and then a nadir/recovery period of 18-21 days; dosing at a lower level for an extended period (e.g., 21 days); dosing at a higher level; dosing with a nadir/recovery period longer than 21 days; dosing at a level to achieve a concentration in the cerebrospinal fluid (CSF) of equal to or greater than 5 μM; dosing at a level to achieve a cytotoxic concentration in the CSF; or the use as a single cytotoxic agent.

Another aspect of the invention involves modifications in the timing of administration, or route by which the compounds are administered, or a combination thereof. General examples include: daily administration; weekly administration; weekly administration for three weeks; biweekly administration; weekly administration with rest periods; intermittent boost dose administration; or daily administration for one week for multiple weeks or for months; changing route from oral to intravenous administration and vice versa; or the use of specialized routes such as subcutaneous, intramuscular, intraarterial, intraperitoneal, intralesional, intralymphatic, intratumoral, intrathecal, intravesicular, and intracranial.

Another aspect of the invention involves modifications in the stage of disease at diagnosis/progression that the compounds are administered. General examples include: the use of chemotherapy for non-resectable local disease, prophylactic use to prevent metastatic spread or inhibit disease progression or conversion to more malignant stages. Specific inventive examples include: use with angiogenesis inhibitors such as Avastin, a VEGF inhibitor, to prevent or limit metastatic spread, especially in the central nervous system; use for newly diagnosed disease; use for recurrent disease; use for resistant or refractory disease; or use for childhood glioblastoma.

Another aspect of the invention involves modifications to the type of patient that would best tolerate or benefit from the use of the compounds. General examples include: use of pediatric doses for elderly patients, altered doses for obese patients; exploitation of co-morbid disease conditions such as diabetes, cirrhosis, or other conditions that may uniquely exploit a feature of the compound. Specific examples include: patients with a disease condition characterized by a high level of a metabolic enzyme selected from the group consisting of histone deacetylase and ornithine decarboxylase; patients with a low or high susceptibility to a condition selected from the group consisting of thrombocytopenia and neutropenia; patients intolerant of GI toxicities; patients characterized by over- or under-expression of a gene selected from the group consisting of c-Jun, a GPCR, a signal transduction protein, VEGF, a prostate-specific gene, and a protein kinase; prostate-specific gene, and a protein kinase; patients characterized by carrying extra copies of the EGFR gene for GBM; patients characterized by mutations in at least one gene selected from the group consisting of TP53, $PDGFR^{A}$, IDH1, and NF1 for GBM; patients characterized by methylation or lack of methylation of the promoter of the MGMT gene; patients characterized by one or more deletions of the distal part of chromosome 17, distal to the p53 gene for medulloblastoma; patients characterized by a particular cytogenic subgroup selected from the group consisting of: (i) a gain of 6 q or amplification of MYC or MYCN; (ii) gain of 17 q or an i(17 q) without gain of 6 q or amplification of MYC or MYCN; and (iii) 6 q and 17 q balanced or 6 q deletion for medulloblastoma; patients characterized by the existence of an IDH1 mutation; patients characterized by the presence of IDH1 wild-type gene; patients characterized by the presence of 1p/19 q co-deletion; patients characterized by a high expression of MGMT; patients characterized by a low expression of MGMT; or patients characterized by a mutation in EGFR including, but not limited to, EGFR Variant III.

Another aspect of the invention involves more precise identification of a patient's ability to tolerate, metabolize, and exploit the use of the compound as associated with a particular phenotype of the patient. General examples include: use of diagnostic tools and kits to better characterize a patient's ability to process/metabolize a chemotherapeutic agent or the susceptibility of the patient to toxicity caused by potential specialized cellular, metabolic, or organ system phenotypes. Specific examples include: use of a diagnostic tool, a diagnostic technique, a diagnostic kit, or a diagnostic assay to confirm a patient's particular phenotype; use of a method for measurement of a marker selected from the group consisting of histone deacetylase, ornithine decarboxylase, VEGF, a protein that is a gene product of jun, and a protein kinase; surrogate compound testing; or low dose pre-testing for enzymatic status.

Another aspect of the invention involves more precise identification of a patient's ability to tolerate, metabolize and exploit the use of the compound as associated with a particular genotype of the patient. General examples include: biopsy samples of tumors or normal tissues (e.g., glial cells or other cells of the central nervous system) that may also be taken and analyzed to specifically tailor or monitor the use of a particular drug against a gene target; studies of unique tumor gene expression patterns; or analysis of SNP (single nucleotide polymorphisms), to enhance efficacy or to avoid drug-sensitive normal tissue toxicities. Specific examples include: diagnostic tools, techniques, kits, and assays to confirm a patient's particular genotype; gene/protein expression chips and analysis; SNP assessment; SNP's for histone deacetylase, ornithine decarboxylase, GPCR's, protein kinases, telomerase, or jun; identification and measurement of metabolism enzymes and metabolites; determination of mutation of the TP53 gene; determination of mutation of PDGFRA gene; determination of mutation of IDH1 gene; determination of mutation of NF1 gene; determination of copy number of the EGFR gene; determination of status of methylation of promoter of MGMT gene; determination of cytogenic subgroup classification (for medulloblastoma); use for disease characterized by an IDH1 mutation; use for disease characterized by IDH1 wild-type; use for disease characterized by 1p/19 q co-deletion; use for disease where the 1p/19 q co-deletion is not present; use for disease characterized by an unmethylated promoter region of the MGMT gene; use for disease characterized by a methylated promoter region of the MGMT gene; use for disease characterized by high expression of MGMT; or use for disease characterized by low expression of MGMT.

Another aspect of the invention involves specialized preparation of a patient prior to or after the use of a chemotherapeutic agent. General examples include: induction or inhibition of metabolizing enzymes, specific protection of sensitive normal tissues or organ systems. Specific inventive examples for a substituted hexitol derivative such as dianhydrogalactitol for treatment include: the use of colchicine or analogs; use of diuretics such as probenecid; use of uricase; non-oral use of nicotinamide; sustained release forms of nicotinamide; use of inhibitors of poly (ADP ribose) polymerase; use of caffeine; leucovorin rescue; infection control; antihypertensives.

Another aspect of the invention involves the use of additional drugs or procedures to prevent or reduce potential side-effects or toxicities. General examples include: the use of anti-emetics, anti-nausea, hematological support agents to limit or prevent neutropenia, anemia, thrombocytopenia, vitamins, antidepressants, treatments for sexual dysfunction, and other supportive techniques. Specific examples include: the use of colchicine or analogs; use of diuretics such as probenecid; use of uricase; non-oral use of nicotinamide; sustained release forms of nicotinamide; use of inhibitors of poly ADP-ribose polymerase; use of caffeine; leucovorin rescue; use of sustained release allopurinol; non-oral use of allopurinol; bone marrow transplant stimulants, blood, platelet infusions, Neupogen, G-CSF; GM-CSF; pain management; anti-inflammatories; fluids; corticosteroids; insulin control medications; anti-pyretics; anti-nausea treatments; anti-diarrhea treatment; N-acetylcysteine; or antihistamines.

Another aspect of the invention involves monitoring drug levels after dosing to maximize a patient's drug plasma level, to monitor the generation of toxic metabolites, monitoring of ancillary medicines that could be beneficial or harmful in terms of drug-drug interactions. Specific examples include: the monitoring of drug plasma protein binding, and monitoring of other pharmacokinetic or pharmacodynamic variables.

Another aspect of the invention involves exploiting unique drug combinations that may provide additive, more than additive, or synergistic improvement in efficacy or side-effect management. Specific examples include: use with topoisomerase inhibitors; use with fraudulent nucleosides; use with fraudulent nucleotides; use with thymidylate synthetase inhibitors; use with signal transduction inhibitors; use with cisplatin or platinum analogs; use with alkylating agents such as the nitrosoureas (BCNU, Gliadel wafers, CCNU, nimustine (ACNU), bendamustine (Treanda)); use with alkylating agents that damage DNA at a different place than does DAG (TMZ, BCNU, CCNU, and other alkylating agents all damage DNA at 06 of guanine, whereas DAG cross-links at N7); use with a monofunctional alkylating agent; use with a bifunctional alkylating agent; use with anti-tubulin agents; use with antimetabolites; use with berberine; use with apigenin; use with amonafide; use with colchicine and analogs; use with genistein; use with etoposide; use with cytarabine; use with campothecins; use with *vinca* alkaloids; use with topoisomerase inhibitors; use with 5-fluorouracil; use with curcumin; use with NF-κB inhibitors; use with rosmarinic acid; use with mitoguazone; use with tetrandrine; use with TMZ; use with biological therapies such as antibodies such as Avastin (a VEGF inhibitor), Rituxan, Herceptin, Erbitux; use with epidermal growth factor receptor (EGFR) inhibitors; use with tyrosine kinase inhibitors; use with poly (ADP-ribose) polymerase (PARP) inhibitors; or use with cancer vaccine therapy.

Another aspect of the invention involves exploiting the compounds as a chemosensitizer where no measurable activity is observed when used alone but in combination with other therapeutics an additive, more than additive, or synergistic improvement in efficacy is observed. Specific examples include: as a chemosensitizer in combination with topoisomerase inhibitors; as a chemosensitizer in combination with fraudulent nucleosides; as a chemosensitizer in combination with fraudulent nucleotides; as a chemo sensitizer in combination with thymidylate synthetase inhibitors; as a chemosensitizer in combination with signal transduction inhibitors; as a chemosensitizer in combination with cisplatin or platinum analogs; as a chemosensitizer in combination with alkylating agents such as BCNU, BCNU wafers, Gliadel, CCNU, bendamustine (Treanda), or Temozolomide (Temodar); as a chemosensitizer in combination with anti-tubulin agents; as a chemosensitizer in combination with antimetabolites; as a chemosensitizer in combination with berberine; as a chemosensitizer in combination with h apigenin; as a chemosensitizer in combination with amonafide; as a chemosensitizer in combination with colchicine and analogs; as a chemosensitizer in combination with genistein; as a chemosensitizer in combination with etoposide; as a chemosensitizer in combination with cytarabine; as a chemosensitizer in combination with camptothecins; as a chemosensitizer in combination with *vinca* alkaloids; as a chemosensitizer in combination with topoisomerase inhibitors; as a chemosensitizer in combination with 5-fluorouracil; as a chemosensitizer in combination with curcumin; as a chemosensitizer in combination with NF-κB inhibitors; as a chemosensitizer in combination with rosmarinic acid; as a chemosensitizer in combination with mitoguazone; as a chemosensitizer in combination with tetrandrine; as a chemosensitizer in combination with a tyrosine kinase inhibitor; as a chemosensitizer in combination with an EGFR inhibitor; or as a chemosensitizer in combination with an inhibitor of poly (ADP-ribose) polymerase (PARP).

Another aspect of the invention involves exploiting the compounds as a chemopotentiator where minimal therapeutic activity is observed alone but in combination with other therapeutics unique drug an additive, more than additive, or synergistic improvement in efficacy is observed. Specific examples include: as a chemopotentiator in combination with topoisomerase inhibitors; as a chemopotentiator in combination with fraudulent nucleosides; as a chemopotentiator in combination with thymidylate synthetase inhibitors; as a chemopotentiator in combination with signal transduction inhibitors; as a chemopotentiator in combination with cisplatin or platinum analogs; as a chemopotentiator in combination with use with alkylating agents such as BCNU, BCNU wafers, Gliadel, or bendamustine (Treanda); as a chemopotentiator in combination with anti-tubulin agents; as a chemopotentiator in combination with antimetabolites; as a chemopotentiator in combination with berberine; as a chemopotentiator in combination with apigenin; as a chemopotentiator in combination with amonafide; as a chemopotentiator in combination with colchicine and analogs; as a chemopotentiator in combination with genistein; as a chemopotentiator in combination with etoposide; as a chemopotentiator in combination with cytarabine; as a chemopotentiator in combination with camptothecins; as a chemopotentiator in combination with *vinca* alkaloids; as a chemopotentiator in combination with topoisomerase inhibitors; as a chemopotentiator in combination with 5-fluorouracil; as a chemopotentiator in combination with curcumin; as a chemopotentiator in combination with NF-κB inhibitors; as a chemopotentiator in combination with rosmarinic acid; as a chemopotentiator in combination with mitoguazone; as a chemopotentiator in combination with tetrandrine; as a chemopotentiator in combination with a tyrosine kinase inhibitor; as a chemopotentiator in combination with an EGFR inhibitor; or as a chemopotentiator in combination with an inhibitor of poly (ADP-ribose) polymerase (PARP).

Another aspect of the invention involves the use of the compounds for the maximum benefit to the patients treated. General examples include: pain management, nutritional support, anti-emetics, anti-nausea therapies, anti-anemia therapy, anti-inflammatories, antipyretics, and immune stimulants.

Another aspect of the invention involves the use of complementary therapeutics or methods to enhance effectiveness or reduce side effects of the compounds. Specific examples include: hypnosis; acupuncture; meditation; herbal medications created either synthetically or through extraction including NF-κB inhibitors (such as parthenolide, curcumin, rosmarinic acid); natural anti-inflammatories (including rhein, parthenolide); immunostimulants (such as those found in *Echinacea*); antimicrobials (such as berberine); flavonoids; isoflavones; and flavones (such as apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin); or applied kinesiology.

Another aspect of the invention involves modifications in the pharmaceutical bulk substance. General examples include: salt formation; homogeneous crystalline structure;

pure isomers; increased purity; lower residual solvents; lower heavy metals; or polymorphic forms.

Another aspect of the invention involves modifications to the solvents or diluents used to solubilize, deliver, or present the compound for administration. Specific examples include Cremophor-EL, cyclodextrins, emulsions, dimethyl sulfoxide (DMSO), N-methylformamide (NMF), dimethylformamide (DMF), dimethylacetamide (DMA), ethanol, benzyl alcohol, dextrose containing water, Cremophor, and PEG.

Another aspect of the invention involves modifications in the materials/excipients, buffering agents, or preservatives required to stabilize and present the compounds for proper administration. Specific examples include: mannitol, albumin, EDTA, sodium bisulfite, benzyl alcohol, carbonate buffers, and phosphate buffers.

Another aspect of the invention involves modifications in the potential dosage forms of the compound, depending on the route of administration, duration of effect, plasma levels required, exposure to side-effect normal tissues and metabolizing enzymes. Specific examples include: tablets, capsules, powders, topical gels, creams, patches, suppositories, and lyophilized fills.

Another aspect of the invention involves modification in the dosage forms, container/closure systems, accuracy of mixing and dosage preparation and presentation. Specific examples include: amber vials to protect from light and stoppers with coatings to improve stability.

Another aspect of the invention involves the use of delivery systems to improve the potential attributes of the compounds such as convenience, duration, effect, or reduction of toxicities. Specific examples include: nanocrystals, bioerodible polymers, liposomes, slow release injectable gels, and microspheres.

Another aspect of the invention involves modifications to the compounds with covalent, ionic, or hydrogen bonded moieties to alter the efficacy, toxicity, pharmacokinetics, metabolism, or route of administration. Specific examples include: polymer systems such as polyethylene glycols, polylactides, polyglycolides, amino acids, peptides, and multivalent linkers.

Another aspect of the invention involves modifications to the compound such that improved pharmaceutical performance is gained with a variant of the active molecule in that after introduction into the body a portion of the molecule is cleaved to reveal the active molecule (e.g., prodrugs). Specific examples include: enzyme sensitive esters, dimers, Schiff bases, pyridoxal complexes, and caffeine complexes.

Another aspect of the invention involves the use of additional biological agents that, when administered, a unique and beneficial effect can be realized. Specific examples include: inhibitors of multi-drug resistance, specific drug resistance inhibitors, specific inhibitors of selective enzymes, signal transduction inhibitors, repair inhibition, and topoisomerase inhibitors with non-overlapping side effects.

Another aspect of the invention involves use in combination of sensitizers/potentiators with biological response modifiers. Specific examples include: use in combination as sensitizers/potentiators with biological response modifiers, cytokines, lymphokines, therapeutic antibodies, antisense therapies, gene therapies, ribozymes, RNA interference, and vaccines.

Another aspect of the invention involves exploiting the selective use of a compound to overcome developing or complete resistance to the efficient use of biotherapeutics. Specific examples include: tumors resistant to the effects of biological response modifiers, cytokines, lymphokines, therapeutic antibodies, antisense therapies, gene therapies, ribozymes, RNA interference, and vaccines.

Another aspect of the invention involves exploiting the use in combination with ionizing radiation, phototherapies, heat therapies, or radio-frequency generated therapies. Specific examples include: hypoxic cell sensitizers, radiation sensitizers/protectors, photosensitizers, radiation repair inhibitors, use in combination with thiol depletion, use in combination with vaso-targeted agents, use in combination with use with radioactive seeds, use in combination with radionuclides, use in combination with radiolabeled antibodies, and use in combination with brachytherapy.

Another aspect of the invention involves optimizing utility by determining the various mechanisms of action, biological targets of a compound for greater understanding and precision to better exploit the utility of the molecule. Specific examples include: the use with inhibitors of poly-ADP ribose polymerase, agents that effect vasculature, vasodilation, oncogenic targeted agents, signal transduction inhibitors, EGFR inhibition, Protein Kinase C inhibition, Phospholipase C down-regulation, jun down-regulation, histone genes, VEGF, ornithine decarboxylase, jun D, v-jun, GPCRs, protein kinase A, telomerase, prostate specific genes, protein kinases, histone deacetylase, and tyrosine kinase inhibitors.

Another aspect of the invention involves more precise identification and exposure of the compounds to those select cell populations where the effect can be maximally exploited, particularly GBM and medulloblastoma tumor cells. Specific examples include: use against radiation sensitive cells; use against radiation resistant cells; or use against energy depleted cells.

Another aspect of the invention involves a method of treating a malignancy (see the lipogenic cancers described herein), comprising the step of administering a therapeutically effective quantity of one or more of the compounds described herein to a patient suffering from the malignancy.

The method can further comprise the step of administering a therapeutically effective dose of ionizing radiation. If the malignancy to be treated is GBM, the method can further comprise the step of administering a therapeutically effective quantity of temozolomide, bevacizumab, or a corticosteroid.

Typically, the compound suppresses the growth of cancer stem cells (CSCs). Typically, the suppression of the growth of cancer stem cells is at least 50%. Examples include the suppression of the growth of cancer stem cells of at least 99%. Typically, the compound is effective in suppressing the growth of cancer cells possessing $O^6$-methylguanine-DNA methyltransferase (MGMT)-driven drug resistance. Typically, the compound is also effective in suppressing the growth of cancer cells resistant to temozolomide. The method can further comprise the administration of a therapeutically effective quantity of a tyrosine kinase inhibitor as described above. The method can further comprise the administration of a therapeutically effective quantity of an epidermal growth factor receptor (EGFR) inhibitor. The EGFR inhibitor can affect either wild-type binding sites or mutated binding sites, including EGFR Variant III, as described above.

The invention may be embodied in other specific forms without departing from the spirit or essential attributes thereof. This invention encompasses all combinations of aspects of the invention noted herein. It is understood that any and all embodiments of the invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

Formulation and Dosage

Formulation of pharmaceutical compositions in tablets, capsules, and topical gels, topical creams or suppositories is well known in the art and is described, for example, in United States Patent Application Publication No. 2004/0023290 by Griffin et al. Formulation of pharmaceutical compositions as patches such as transdermal patches is well known in the art and is described, for example, in U.S. Pat. No. 7,728,042 to Eros et al. Lyophilized dosage fills are also well known in the art.

The use of prodrug systems is described in T. Jarvinen et al., "Design and Pharmaceutical Applications of Prodrugs" in Drug Discovery Handbook (S. C. Gad, ed., Wiley-Interscience, Hoboken, N.J., 2005), ch. 17, pp. 733-796; U.S. Pat. No. 7,879,896 to Allegretti et al.' S. Prasad et al., "Delivering Multiple Anticancer Peptides as a Single Prodrug Using Lysyl-Lysine as a Facile Linker," J. Peptide Sci. 13: 458-467 (2007); U.S. Pat. No. 7,619,005 to Epstein et al.; U.S. Pat. No. 6,443,898 to Unger et al.

Prodrugs and active metabolites of a compound may be identified using routine techniques known in the art. See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992).

When the pharmacologically active compound in a pharmaceutical composition possesses a sufficiently acidic, a sufficiently basic, or both a sufficiently acidic and a sufficiently basic functional group, these group or groups can accordingly react with any of several inorganic or organic bases, and inorganic and organic acids, to form a pharmaceutically acceptable salt. Exemplary pharmaceutically acceptable salts include those salts prepared by reaction of the pharmacologically active compound with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, .beta.-hydroxybutyrates, glycolates, tartrates, methane-sulfonates, propanesulfonates, naphthalene-1-sulfonates, naphthalene-2-sulfonates, and mandelates.

If the pharmacologically active compound has one or more basic functional groups, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the pharmacologically active compound has one or more acidic functional groups, the desired pharmaceutically acceptable salt may be prepared by any suitable method available in the art, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the compounds and salts may exist in different crystal or polymorphic forms, all of which are intended to be within the scope of the invention and specified formulas.

The amount of a given pharmacologically active agent in a unit dose of a pharmaceutical composition will vary depending upon factors such as the particular compound, disease condition and its severity, the identity (e.g., weight) of the subject in need of treatment, but can nevertheless be routinely determined by one skilled in the art. Typically, such pharmaceutical compositions include a therapeutically effective quantity of the pharmacologically active agent and an inert pharmaceutically acceptable carrier or diluent. Typically, these compositions are prepared in unit dosage form appropriate for the chosen route of administration, such as oral administration or parenteral administration. A pharmacologically active agent as described above can be administered in conventional dosage form prepared by combining a therapeutically effective amount of such a pharmacologically active agent as an active ingredient with appropriate pharmaceutical carriers or diluents according to conventional procedures. These procedures may involve mixing, granulating, and compressing or dissolving the ingredients as appropriate to the desired preparation. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of a pharmacologically active agent as described above is dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0-60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the complex being used, the composition formulated, the mode of administration and the site, host, disease, and/or condition being treated. Actual dosage levels of the active ingredients in the pharmaceutical compositions of the invention can be varied so as to obtain an amount of the active ingredient which is effective to achieve the desired therapeutic response for a particular subject, composition, and mode of administration, without being toxic to the subject. The selected dosage level depends upon a variety of pharmacokinetic factors including the activity of the therapeutic agent, the route of administration, the time of administration, the rate of excretion of the compound being employed, the severity of the condition, other health considerations affecting the subject, and the status of liver and kidney function of the subject. It also depends on the duration of the treatment, other drugs, compounds and/or materials used in combination with the therapeutic agent employed, as well as the age, weight, condition, general health and prior medical history of the subject being treated, and like factors. Methods for determining optimal dosages are described in the art, e.g., Remington: The Science and Practice of Pharmacy, Mack Publishing Co., 20.sup.th ed., 2000. Optimal dosages for a given set of conditions can be ascertained by those skilled in the art using conventional dosage-determination tests in view of the experimental data for an agent.

For oral administration, an exemplary daily dose generally employed is from about 0.001 to about 3000 mg/kg of body weight, with courses of treatment repeated at appropriate intervals. In some embodiments, the daily dose is from about 1 to 3000 mg/kg of body weight. Typical daily doses in a patient may be anywhere between about 500 mg to about 3000 mg, given once or twice daily, e.g., 3000 mg can be given twice daily for a total dose of 6000 mg. In one embodiment, the dose is between about 1000 to about 3000 mg. In another embodiment, the dose is between about 1500 to about 2800 mg. In other embodiments, the dose is between about 2000 to about 3000 mg. Typically, doses are from about 1 $mg/m^2$ to about 40 $mg/m^2$. Further examples include doses that are from about 5 $mg/m^2$ to about 25 $mg/m^2$.

Plasma concentrations in the subjects may be between about 100 μM to about 1000 μM. In some embodiments, the plasma concentration may be between about 200 μM to about 800 μM. In other embodiments, the concentration is about 300 μM to about 600 μM. In still other embodiments the plasma concentration may be between about 400 μM to about 800 μM. In another alternative, the plasma concentration can be between about 0.5 μM to about 20 μM, typically 1 μM to about 10 μM. Administration of prodrugs is typically dosed at weight levels, which are chemically equivalent to the weight levels of the fully active form.

The compositions of the invention may be manufactured using techniques generally known for preparing pharmaceutical compositions, e.g., by conventional techniques such as mixing, dissolving, granulating, dragee-making, levitating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations, which can be used pharmaceutically.

Proper formulation is dependent upon the route of administration chosen. For injection, the agents of the invention may be formulated into aqueous solutions, e.g., in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, solutions, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Pharmaceutical formulations for parenteral administration can include aqueous solutions or suspensions. Suitable lipophilic solvents or vehicles include fatty oils such as sesame oil or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or modulators which increase the solubility or dispersibility of the composition to allow for the preparation of highly concentrated solutions or can contain suspending or dispersing agents. Pharmaceutical preparations for oral use can be obtained by combining the pharmacologically active agent with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating modulators may be added, such as the cross-linked polyvinyl pyrrolidone, agar, or alginic acid or a salt thereof such as sodium alginate.

Other ingredients such as stabilizers, for example, antioxidants such as sodium citrate, ascorbyl palmitate, propyl gallate, reducing agents, ascorbic acid, vitamin E, sodium bisulfite, butylated hydroxytoluene, BHA, acetylcysteine, monothioglycerol, phenyl-.alpha.-naphthylamine, or lecithin can be used. Also, chelators such as EDTA can be used.

Other ingredients that are conventional in pharmaceutical compositions and formulations, such as lubricants in tablets or pills, coloring agents, or flavoring agents, can be used. Also, conventional pharmaceutical excipients or carriers can be used. The pharmaceutical excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agents, and/or the like. The use of such media and/or agents for pharmaceutically active substances is well known in the art. Except insofar as any conventional medium, carrier, or agent is incompatible with the active ingredient or ingredients, its use in a composition according to the invention is contemplated. Supplementary active ingredients can also be incorporated into the compositions, particularly as described above.

For administration intranasally or by inhalation, the compounds for use according to the invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days; in other alternatives, depending on the therapeutic agent and the formulation employed, release may occur over hours, days, weeks, or months. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

A pharmaceutical composition can be administered by a variety of methods known in the art. The routes and/or modes of administration vary depending upon the desired results. Depending on the route of administration, the pharmacologically active agent may be coated in a material to protect the targeting composition or other therapeutic agent from the action of acids and other compounds that may inactivate the agent. Conventional pharmaceutical practice can be employed to provide suitable formulations or compositions for the administration of such pharmaceutical compositions to subjects. Any appropriate route of administration can be employed, for example, but not limited to, intravenous, parenteral, intraperitoneal, intravenous, transcutaneous, subcutaneous, intramuscular, intraurethral, or oral administration. Depending on the severity of the malignancy or other disease, disorder, or condition to be treated, as well as other conditions affecting the subject to be treated, either systemic or localized delivery of the pharmaceutical composition can be used in the course of treatment. The pharmaceutical composition as described above can be administered together with additional therapeutic agents intended to treat a particular disease or condition, which may be the same disease or condition that the pharmaceutical composition is intended to treat, which may be a related disease or condition, or which even may be an unrelated disease or condition.

Pharmaceutical compositions according to the invention can be prepared in accordance with methods well known and routinely practiced in the art. See, e.g., Remington: The Science and Practice of Pharmacy, Mack Publishing Co., 20.sup.th ed., 2000; and Sustained and Controlled Release Drug Delivery Systems, J. R. Robinson, ed., Marcel Dekker, Inc., New York, 1978. Pharmaceutical compositions are typically manufactured under GMP conditions. Formulations for parenteral administration may, for example, contain excipients, sterile water, or saline, polyalkylene glycols such as polyethylene glycol, oils of vegetable origin, or hydrogenated naphthalenes. Biocompatible, biodegradable lactide polymers, lactide/glycolide copolymers, or polyoxyethylene-polyoxypropylene copolymers may be used to control the release of the compounds. Other potentially useful parenteral delivery systems for molecules of the invention include ethylene-vinyl acetate copolymer particles, osmotic pumps, and implantable infusion systems. Formulations for inhalation may contain excipients, for example, lactose, or may be aqueous solutions containing, e.g., polyoxyethylene-9-lauryl ether, glycocholate and deoxycholate, or can be oily solutions for administration or gels.

Pharmaceutical compositions in aspects of the invention are typically administered to the subjects on multiple occasions. Intervals between single dosages can be weekly, monthly or yearly. Intervals can also be irregular as indicated by therapeutic response or other parameters well known in the art. Alternatively, the pharmaceutical composition can be administered as a sustained release formulation, in which case less frequent administration is required. Dosage and frequency vary depending on the half-life in the subject of the pharmacologically active agent included in a pharmaceutical composition. The dosage and frequency of administration can vary depending on whether the treatment is prophylactic or therapeutic. In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and typically until the subject shows partial or complete amelioration of symptoms of disease. Thereafter, the subject can be administered a prophylactic regime.

For the purposes of the present application, treatment can be monitored by observing one or more of the improving symptoms associated with the disease, disorder, or condition being treated, or by observing one or more of the improving clinical parameters associated with the disease, disorder, or condition being treated. In the case of glioblastoma multiforme and medulloblastoma, the clinical parameters can include, but are not limited to, reduction in tumor burden, reduction in pain, reduction in edema of the brain, reduction in frequency or severity of seizures, reduction in frequency or severity of vomiting, reduction of frequency or severity of headache, reduction in memory deficit, reduction in neurological deficit, and reduction in occurrence of tumor spread or metastasis. As used herein, the terms "treatment," "treating," or equivalent terminology are not intended to imply a permanent cure for the disease, disorder, or condition being treated. Compositions and methods according to the invention are not limited to treatment of humans but are applicable to treatment of socially or economically important animals, such as dogs, cats, horses, cows, sheep, goats, pigs, and other animal species of social or economic importance. Unless specifically stated, compositions and methods according to the invention are not limited to the treatment of humans.

Sustained-release formulations or controlled-release formulations are well-known in the art. For example, the sustained-release or controlled-release formulation can be (1) an oral matrix sustained-release or controlled-release formulation; (2) an oral multilayered sustained-release or controlled-release tablet formulation; (3) an oral multiparticulate sustained-release or controlled-release formulation; (4) an oral osmotic sustained-release or controlled-release formulation; (5) an oral chewable sustained-release or controlled-release formulation; or (6) a dermal sustained-release or controlled-release patch formulation.

The pharmacokinetic principles of controlled drug delivery are described, for example, in B. M. Silber et al., "Pharmacokinetic/Pharmacodynamic Basis of Controlled Drug Delivery" in Controlled Drug Delivery: Fundamentals and Applications (J. R. Robinson & V. H. L. Lee, eds, 2d ed., Marcel Dekker, New York, 1987), ch. 5, pp. 213-251. One of ordinary skill in the art can readily prepare formulations for controlled release or sustained release comprising a pharmacologically active agent according to the invention by modifying the formulations described above, such as according to principles disclosed in V. H. K. Li et al, "Influence of Drug Properties and Routes of Drug Administration on the Design of Sustained and Controlled Release Systems" in Controlled Drug Delivery: Fundamentals and Applications (J. R. Robinson & V. H. L. Lee, eds, 2d ed., Marcel Dekker, New York, 1987), ch. 1, pp. 3-94. This process of preparation typically considers physicochemical properties of the pharmacologically active agent, such as aqueous solubility, partition coefficient, molecular size, stability, and nonspecific binding to proteins and other biological macromolecules. This process of preparation also takes into account biological factors, such as absorption, distribution, metabolism, duration of action, the possible existence of side effects, and margin of safety, for the pharmacologically active agent. Accordingly, one of ordinary skill in the art could modify the formulations into a formulation having the desirable properties described above for a particular application.

U.S. Pat. No. 6,573,292 by Nardella, U.S. Pat. No. 6,921,722 by Nardella, U.S. Pat. No. 7,314,886 by Chao et al., and U.S. Pat. No. 7,446,122 by Chao et al., which disclose methods of use of various pharmacologically active agents and pharmaceutical compositions in treating a number of diseases and conditions, including cancer, and methods of determining the therapeutic effectiveness of such pharmacologically active agents and pharmaceutical compositions.

Definitions

The examples provided in the definitions present in this application are non-inclusive unless otherwise stated. They include but are not limited to the recited examples.

When introducing elements of the present disclosure or an aspect thereof, the articles “a”, “an”, “the” and “said” are intended to mean that there are one or more of the elements. The terms “comprising”, “including” and “having” are intended to be inclusive and mean that there may be additional elements other than the listed elements.

The term “and/or” when used in a list of two or more items, means that any one of the listed items can be employed by itself or in combination with any one or more of the listed items. For example, the expression “A and/or B” is intended to mean either or both of A and B, i.e. A alone, B alone or A and B in combination. The expression “A, B and/or C” is intended to mean A alone, B alone, C alone, A and B in combination, A and C in combination, B and C in combination or A, B, and C in combination.

The terms “treatment,” “treating” or “treat,” when referring to a condition, and as understood in the art, are defined to mean an approach for obtaining beneficial or desired results, including clinical results. Beneficial or desired clinical results can include alleviation of one or more symptoms of the condition, diminishment of extent of disease or condition, stabilize (i.e., not worsening) the state of disease or condition, preventing spread of disease, delay or slowing of disease progression, palliation of the disease state, and remission (whether partial or total), whether detectable or undetectable.

The terms “subject” or “patient” are used interchangeably and mean all members of the animal kingdom (e.g., humans).

The term “effective amount” or “pharmaceutically effective amount” are used interchangeably and are defined to mean the amount or quantity of steroidal compound, which is sufficient to elicit an appreciable biological response when administered to a patient. It will be appreciated that the precise therapeutic dose will depend on the age and condition of the patient and the nature of the condition to be treated and will be at the ultimate discretion of the attendant physician.

A compound or compounds of the invention, as used herein, includes, where appropriate, stereoisomers (enantiomers and/or diastereomers) and/or pharmaceutically acceptable salts thereof.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C═N double bonds, or other types of double bonds may be present in the compounds described herein, and all such stable isomers are included in the invention. Specifically, cis and trans geometric isomers of the compounds of the invention may also exist and may be isolated as a mixture of isomers or as separated isomeric forms. All processes used to prepare compounds of the invention and intermediates made therein are part of the invention. All tautomers of shown or described compounds are also considered to be part of the invention.

The invention includes all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The term “substituted” means that any one or more hydrogens on the designated atom is replaced with a selection from the indicated group, provided that the designated atom’s normal valency is not exceeded, and that the substitution results in a stable compound. When a substituent is keto (i.e., ═O), then 2 hydrogens on the atom are replaced. Keto substituents are not present on aromatic moieties.

“Stable” means that the compound is suitable for pharmaceutical use.

The invention includes stable compounds and thus avoids, unless otherwise specified, the following bond types: heteroatom-halogen, N—S, O—S, 0-0, and S—S.

“Halo” includes Cl, F, Br, and I.

“Alkyl” includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl.

“Alkenyl” includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups.

“Alkynyl” includes the specified number of hydrocarbon atoms in either straight or branched configuration with one or more triple carbon-carbon bonds that may occur in any stable point along the chain, such as ethynyl and propynyl. $C_{2-6}$ Alkynyl includes $C_2$, $C_3$, $C_4$, $C_5$, and $C_6$ alkynyl groups.

When an “ene” terminates a group it indicates the group is attached to two other groups. For example, methylene refers to a —$CH_2$-moiety.

“Cycloalkyl” includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups.

“Cyclic amine” refers to any stable 4, 5, 6, 7, 8, 9, 10, or 10 membered mono-, bi-, or tri cyclic or 7-11 spirocyclic heterocyclic ring that contains a ring nitrogen and is attached via the ring nitrogen. The cyclic amine consists of the ring nitrogen, carbon atoms and 0, 1, or 2 additional heteroatoms independently selected from the group consisting of N, O, and S. One or two double bonds can be present in the ring containing the amine. If the cyclic amine is bicyclic then the non-amine containing ring can be aromatic (e.g., benzo, pyrimido, or other heteroaryl). An additional N group, if present, may be N, NH, or N-substituent, depending on the chosen ring and if substituents are recited. The nitrogen and sulfur heteroatoms may optionally be oxidized (e.g., S, S(O), $S(O)_2$, and N—O). The cyclic amines described herein may be substituted on carbon or on a nitrogen atom if the resulting compound is stable.

"Spirocyclic" refers to two rings that have only one carbon atom in common. An example of a spirocyclic amine

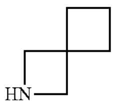

(2-azaspiro[3.3]heptane).

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, adamantyl, and tetrahydronaphthyl.

"Heteroaryl" refers to any stable 5, 6, 7, 8, 9, or 10 membered monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), $S(O)_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heteroaryl includes acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, 2H-pyrrolyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Mammal" and "patient" cover warm blooded mammals that are typically under medical care (e.g., humans and domesticated animals). Examples include feline, canine, equine, bovine, non-human primate, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting its development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof.

"Therapeutically effective amount" includes an amount of a compound of the invention that is effective when administered alone or in combination to an indication listed herein. "Therapeutically effective amount" also includes an amount of the combination of compounds claimed that is effective to treat the desired indication. The combination of compounds can be a synergistic combination. Synergy, as described, for example, by Chou and Talalay, *Adv. Enzyme Regul.* 1984, 22: 27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Synthesis

The compounds of the invention can be prepared in several ways known to one skilled in the art of organic synthesis. The compounds of the invention can be synthesized using the methods described below, together with synthetic methods known in the art of synthetic organic chemistry, or by variations thereon as appreciated by those skilled in the art. Useful methods include, but are not limited to, those described below. The reactions are performed in a solvent appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one process scheme over another to obtain a desired compound of the invention. It will also be recognized that another major consideration in the planning of any synthetic route in the is field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991).

One stereoisomer of a compound of the invention may be a more potent than its counterpart(s). Thus, stereoisomers are included in the invention. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of the invention may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis.

Other features of the invention will become apparent during the following descriptions of exemplary embodiments that are given for illustration of the invention and are not intended to be limiting thereof.

EXAMPLES

Abbreviations:

a. ACN: acetonitrile
b. $BF_3.Et_2O$: boron trifluoride diethyl etherate
c. $(Boc)_2O$: Di-tert-butyl decarbonate
d. nBuLi: n-butyllithium
e. nBuMgBr: n-butylmagnesium bromide
f. tBuOH: tertiary butyl alcohol
g. tBuOK: potassium tert-butoxide
h. CDI: carbodiimide
i. mCPB A: meta-chloroperbenzoic acid
j. DAST: diethylaminosulfur trifluoride
k. DBU: 1,8-diazabicyclo(5.4.0)undec-7-ene
l. DCC: N,N'-dicyclohexylcarbodiimide
m. DCM: dichloromethane
n. DDQ: 2,3-dichloro-5,6-dicyanobenzoquinone
o. DEAD: diethyl azodicarboxylate
P. DIAD: diisopropyl azodicarboxylate
q. DIBAL-H: diisobutylaluminum hydride
r. DIEA: diisopropylethylamine
s. DIPEA: diisopropylethylamine
t. DMAP: 4-(dimethylamino)pyridine
u. DME: dimethoxyethane
v. DMF: dimethylformamie
w. DMSO: dimethylsulfoxide
x. EDC-HCl: N-ethyl-N'-(3-dimethylaminopropyl)carbodiimide hydrochloride
y. EDCI:1-ethyl-3-(3-dimethylaminopropyl)carbodiimide
z. $Et_2AlCl$: diethylaluminum chloride
aa. EtMgBr: ethylmagnesium bromide
bb. EtOH: ethanol
cc. $Et_2O$: diethyl ether
dd. FA: formic acid
ee. HATU: 1-[bis(dimethylamino)methylene]-1H-1,2,3-triazolo[4,5-b]pyridinium 3-oxid hexafluorophosphate
ff. HOBT: 1-hydroxybenzotriazole hydrate
gg. HPLC: high performance liquid chromatography
hh. LAH: lithium aluminum hydride
ii. MeMgBr: methylmagnesium bromide
jj. MeOH: methanol
kk. $NaBH_4$: sodium borohydride
ll. $NaBH(OAc)_3$: sodium triacetoxyborohydride
mm. $NaCNBH_4$: sodium cyanoborohydride
nn. NaOAc: sodium acetate
oo. NBS: N-bromosuccinimide
pp. NCS: N-chlorosuccinimide
qq. Pd/C: palladium on carbon
rr. $Pd(dppf)C_{12}$: (1,1'-Bis(diphenylphosphino)ferrocene) palladium(II) dichloride
ss. $PPh_3$: triphenylphosphine
tt. $TMSCF_3$: trimethyl(trifluoromethyl)silane
uu. TBACl: tertrabutylammonium chloride
vv. TBAF: tetrabutylammonium fluoride
ww. TBSCl: tert-butyldimethylsilyl chloride
xx. TBDMSCl: tert-butyldimethylchlorosilane
yy. TBSOTf: trifluoromethanesulfonic acid tert-butyldimethylsilylester
zz. TEA: triethylamine
aaa. TEMPO: (2,2,6,6-Tetramethylpiperidin-1-yl)oxyl or (2,2,6,6-tetramethylpiperidin-1-yl)oxidanyl
bbb. TFA: trifluoroacetic acid
ccc. THF: tetrahydrofuran
ddd. T3P: Propylphosphonic anhydride
eee. AND 1: both stereochemical configurations present
fff. $OR_1$: single unknown stereochemical configuration
ggg. SM: starting material General Procedure A: Synthesis of Sterol Amides Using HATU and DIPEA To a solution of 3β-hydroxy-5-cholenic acid (1 equiv.) in DMF or THF were added HATU (2-5 equiv.) and DIPEA (2-5 equiv.) at 0° C. under nitrogen atmosphere and allowed to stir for 15 minutes at same temperature. Then was added the required hydroxylamine or amine derivative (1-3 equiv.) at 0° C. and the resulting mixture stirred at room temperature for 16 h. Upon completion, the reaction mixture was diluted with water and extracted with ethyl acetate (2×). The combined organic layer was dried over sodium sulfate, filtered, concentrated in vacuo, and purified by column chromatography.

General Procedure B: Synthesis of Sterol Amides Using EDC.HCl and HOBt

To a stirred solution of 3β-hydroxy-5-cholenic acid (1 equiv.) in THF or DMF or DCM were added EDC.HCl (1-5 equiv.), HOBt (1-5 equiv.), DIPEA (2-5 equiv.), and the required hydroxylamine or amine derivative (1-3 equiv.) sequentially at 0° C. under nitrogen atmosphere. The resulting mixture was stirred at room temperature for 16 h. Upon completion, the reaction mixture was quenched with water and extracted with DCM (2×). The combined organic layer was washed with brine, dried over sodium sulfate, filtered, concentrated in vacuo, and purified by column chromatography.

General Procedure C: Silyl Group Deprotection by TBAF

To a stirred solution of silyl protected sterol (1 equiv.) in THF or DCM was added 1M TBAF in THF (2-5 equiv.) at 0° C. and the resultant reaction mixture was stirred at room temperature until completion of starting material. Upon completion, the reaction mixture was diluted with water, extracted with organic solvent (2×). The combined organic layer was washed with water, brine, dried over sodium sulfate, filtered, concentrated in vacuo, and purified by column chromatography.

Example 1: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methoxy-N-methylpentanamide

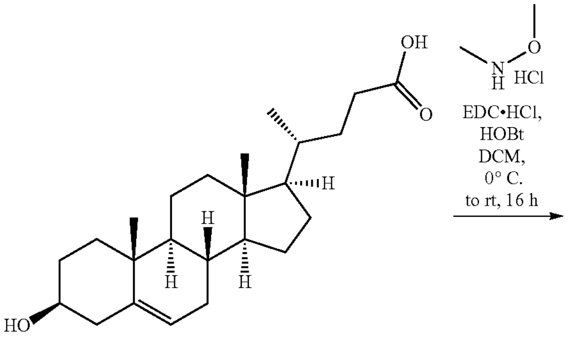

3β-hydroxy-5-cholenic acid

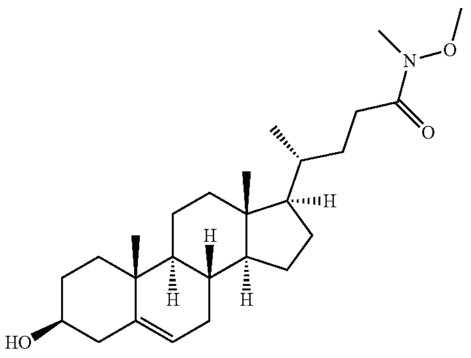

1

Synthesized compound 1 according to the general procedure B using 3β-hydroxy-5-cholenic acid (500 mg, 1.33 mmol), EDC.HCl (382 mg, 2.0 mmol), HOBt (198 mg, 1.47 mmol), DIPEA (0.68 mL, 3.98 mmol), N, O-dimethylhydroxylamine hydrochloride (156 mg, 1.6 mmol) and DCM (15 mL) were used. The obtained crude material was purified by column chromatography over silica gel (100-200 mesh) with 0-50% gradient elution of ethyl acetate in hexanes to afford compound 1 as an off-white solid (30 mg, 46%). ELSD LC-MS (ESI) m/z: 417.9 $[M+H]^+$; $^1H$ NMR (400 MHz, $CDCl_3$) δ 5.36-5.34 (m, 1H), 3.69 (s, 3H), 3.58-3.46 (m, 1H), 3.19 (s, 3H), 2.49-2.19 (m, 3H), 2.04-1.93 (m, 2H), 1.89-1.74 (m, 4H), 1.69-1.40 (m, 9H), 1.39-1.25 (m, 2H), 1.21-1.02 (m, 5H), 1.0 (s, 3H), 0.98-0.90 (m, 4H), 0.68 (s, 3H).

Example 2: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(piperazin-1-yl) pentan-1-one

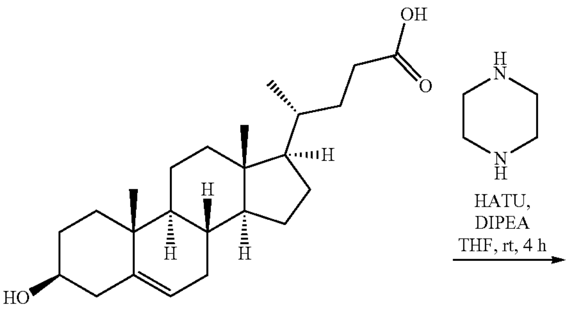

3β-hydroxy-5-cholenic acid

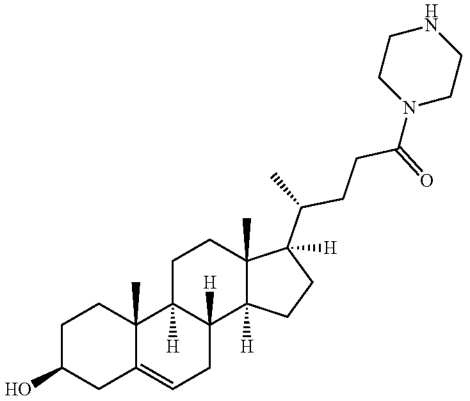

2

Compound 2 was synthesized according to the general procedure A using 3β-hydroxy-5-cholenic acid (150 mg, 0.40 mmol), HATU (288 mg, 0.600 mmol), DIPEA (103.5 mg, 0.80 mmol), piperazine (68.9 mg, 0.8 mmol) and THE (1.5 mL). The reaction time was 4 h. The obtained crude material was further purified by preparative HPLC [Column: Gemini 5 µm NX—$C_{18}$ $_{110}$A 50*2 mm Mobile Phase-A: 0.01% FA in water, Mobile phase-B: 100% ACN, program (Time/% B): 0/40,13/45,15/95, @ 13.mL/minn] to afford compound 2 (12.3 mg, 6.6%) as an off-white solid. LC-MS (ESI) m/z: 442.8 $[M+H]^+$; $^1H$ NMR (400 MHz, DMSO-$d_6$): δ 8.26 (s, 1H), 5.27-5.25 (m, 1H), 4.62-4.58 (m, 1H), 2.68-2.59 (m, 3H), 2.33-2.25 (m, 1H), 2.21-2.05 (m, 4H), 1.98-1.85 (m, 2H), 1.84-1.59 (m, 5H), 1.58-1.43 (m, 3H), 1.42-1.32 (m, 4H), 1.31-1.21 (m, 2H), 1.19-1.03 (m, 4H), 1.02-0.96 (m, 2H), 0.94 (s, 3H) 0.91-0.83 (m, 4H), 0.64 (s, 3H).

Example 3: (R)-1-(4-acetylpiperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

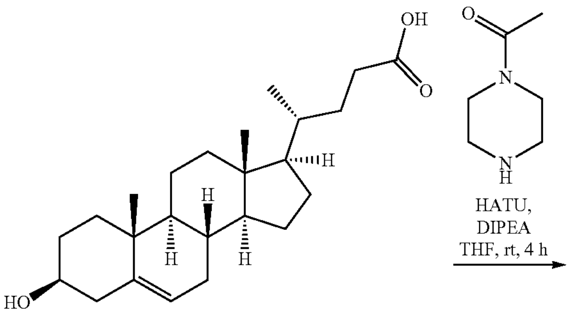

3β-hydroxy-5-cholenic acid

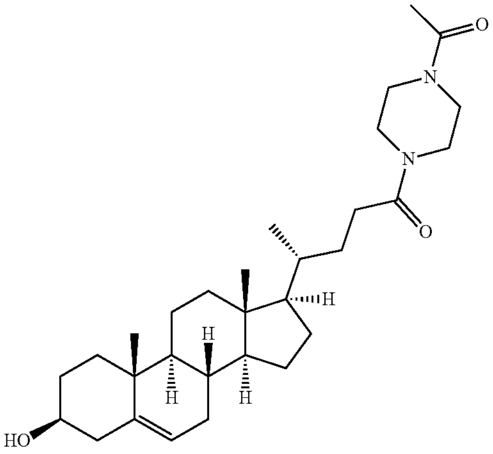

3

Compound 3 was synthesized according to the general procedure A using 3β-hydroxy-5-cholenic acid (200 mg, 0.53 mmol), HATU (304 mg, 0.80 mmol), DIPEA (138 mg, 1.07 mmol), 1-piperazin-1-ylethanone (136.88 mg, 1.07 mmol) and THF (2 mL). The reaction time was 4 h. The obtained crude material was purified by column chromatography over silica gel (100-200 mesh) with 0-3% gradient elution of MeOH in DCM to afford compound 3 (55.1 mg, 21%) as an off-white solid. LC-MS (ESI) m/z: 484.9 $[M+H]^+$; $^1$H NMR (400 MHz, $CDCl_3$): δ 5.36-5.34 (m, 1H), 3.68-3.60 (m, 4H), 3.55-3.45 (m, 5H), 2.46-2.36 (m, 1H), 2.32-2.19 (m, 3H), 2.13 (s, 3H), 2.05-1.95 (m, 2H), 1.90-1.81 (m, 3H), 1.80-1.73 (m, 1H), 1.62-1.28 (m, 10H), 1.25-1.03 (m, 6H), 1.04 (s, 3H), 1.00-0.90 (m, 4H), 0.68 (s, 3H).

Example 4: 4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperazine-1-carboxamide

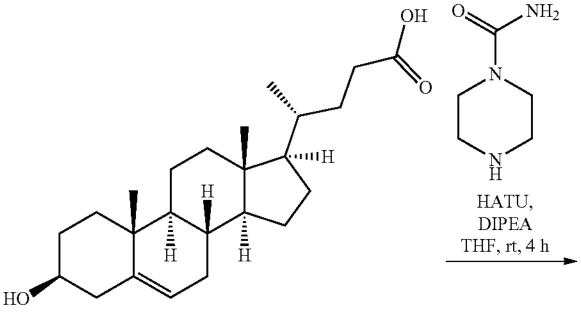

3β-hydroxy-5-cholenic acid

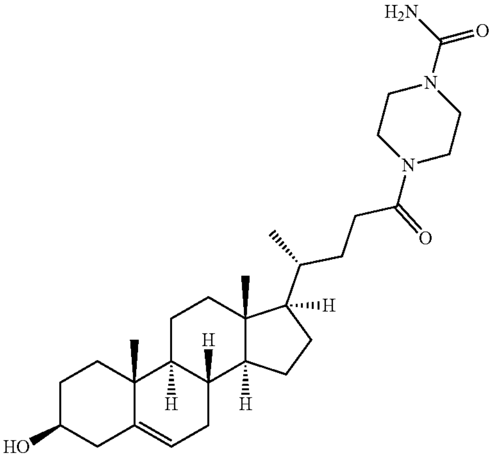

4

Compound 4 was synthesized according to the general procedure A using 3β-hydroxy-5-cholenic acid (120 mg, 0.32 mmol), HATU (243.6 mg, 0.64 mmol), DIPEA (124 mg, 0.96 mmol), piperazine-1-carboxamide (82.7 mg, 0.64 mmol), and THE (1.5 mL). The reaction time was 4 h. The obtained crude material was purified by column chromatography over silica gel (100-200 mesh) with 0-3% gradient elution of MeOH in DCM to afford compound 4 (31.1 mg, 20%) as an off-white solid. LC-MS (ESI) m/z: 486.4 $[M+H]^+$; $^1$H NMR (400 MHz, DMSO-$d_6$): δ 6.05 (s, 2H), 5.27-5.25 (m, 1H), 4.61 (d, J=4.4 Hz, 1H), 3.42-3.17 (m, 8H), 2.33-2.28 (m, 1H), 2.25-2.05 (m, 3H), 2.00-1.86 (m, 2H), 1.85-1.72 (m, 2H), 1.69-1.43 (m, 5H), 1.42-1.32 (m, 4H), 1.31-1.22 (m, 2H), 1.19-1.08 (m, 3H), 1.07-0.96 (m, 3H), 0.94 (s, 3H) 0.93-0.86 (m, 4H), 0.64 (s, 3H).

Example 5: (R)-1-(4,4-dimethylpiperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl) pentan-1-one

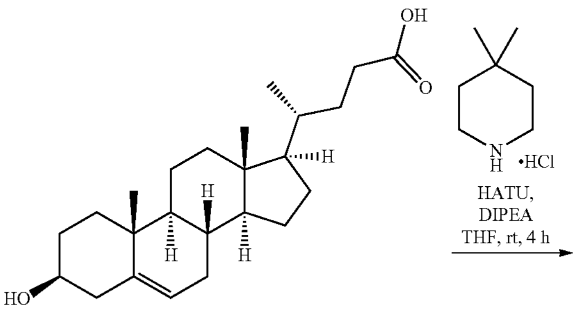

3β-hydroxy-5-cholenic acid

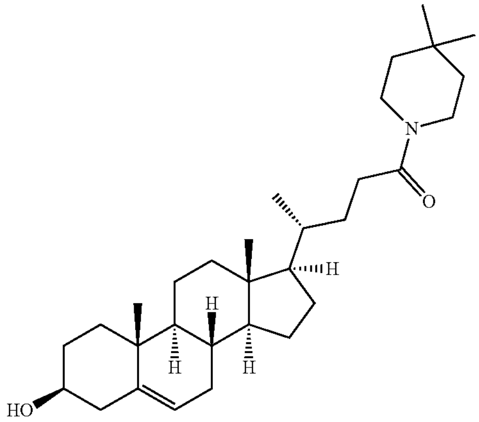

5

Compound 5 was synthesized according to the general procedure A using 3β-hydroxy-5-cholenic acid (200 mg, 0.533 mmol), HATU (406 mg, 1.07 mmol), DIPEA (207 mg, 1.6 mmol), 4,4-di(methyl)piperidine hydrochloride (159.83 mg, 1.07 mmol), and THE (2 mL). The reaction time was 4 h. The reaction mixture was poured into the ice and the solid formed was filtered to afford compound 5 (155 mg, 60%) as an off-white solid which have enough purity. LC-MS (ESI) m/z: 469.9 $[M+H]^+$; $^1H$ NMR (400 MHz, DMSO-$d_6$) δ 5.27-5.25 (m, 1H), 4.60 (d, J=4.4 Hz, 1H), 3.43-3.22 (m, 5H), 2.31-2.25 (m, 1H), 2.21-2.05 (m, 4H), 1.98-1.72 (m, 4H), 1.70-1.59 (m, 2H), 1.57-1.43 (m, 3H), 1.42-1.25 (m, 7H), 1.24-1.03 (m, 6H), 1.02-0.87 (m, 14H), 0.64 (s, 3H).

Example 6: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-hydroxy-4-methylpiperidin-1-yl)pentan-1-one

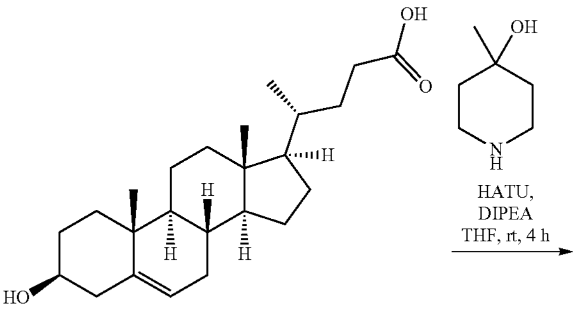

3β-hydroxy-5-cholenic acid

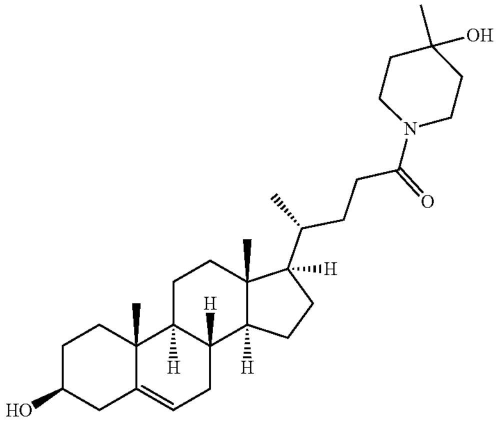

6

Compound 6 was synthesized according to the general procedure A using 3β-hydroxy-5-cholenic acid (100 mg, 0.26 mmol), HATU (152 mg, 0.40 mmol), DIPEA (69 mg, 0.53 mmol), 4-methylpiperidin-4-ol (61.5 mg, 0.53 mmol) and THF (1 mL). The reaction time was 4 h. The obtained crude material was purified by column chromatography over silica gel (100-200 mesh) with 0-3% gradient elution of MeOH in DCM to afford compound 6 (103.9 mg, 82.5%) as an off-white solid. ELSD-MS (ESI) m/z: 471.9 $[M+H]^+$; $^1H$ NMR (400 MHz, DMSO-$d_6$): δ 5.27 5.23 (m, 1H), 4.60 (d, J=4.4 Hz, 1H), 4.36 (s, 1H), 3.93-3.85 (m, 1H), 3.53-3.46 (m, 1H), 3.31-3.24 (m, 2H), 3.03-2.96 (m, 1H), 2.31-2.24 (m, 1H), 2.22-2.02 (m, 4H), 1.98-1.84 (m, 2H), 1.82-1.71 (m, 2H), 1.70-1.58 (m, 2H), 1.57-1.22 (m, 11H), 1.20-1.02 (m, 7H), 1.01-0.93 (m, 5H), 0.92-0.83 (m, 4H), 0.64 (s, 3H).

Example 7: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-morpholinopentan-1-one

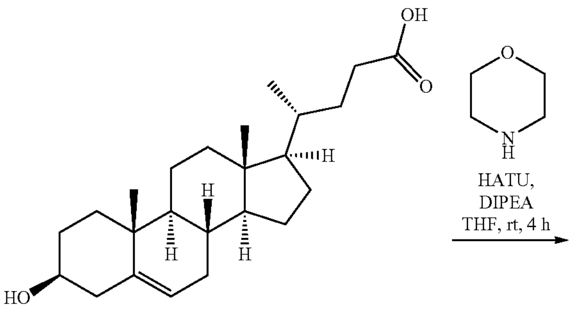

3β-hydroxy-5-cholenic acid

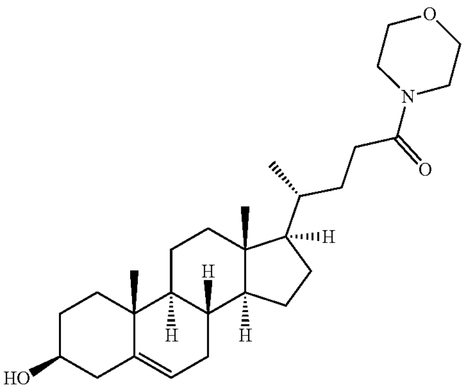

7

Compound 7 was synthesized according to the general procedure A using 3β-hydroxy-5-cholenic acid (100 mg, 0.26 mmol), HATU (152 mg, 0.40 mmol), DIPEA (102 mg, 0.8 mmol), morpholine (34.8 mg, 0.4 mmol) and THF (1.5 mL). The reaction time was 4 h. The reaction mixture was poured into ice cold water and the precipitated formed was filtered off to afford compound 7 (104 mg, 87%) as an off-white solid. ELSD-MS (ESI) m/z: 443.9 $[M+H]^+$; $^1H$ NMR (400 MHz, DMSO-$d_6$): δ 5.28-5.25 (m, 1H), 4.60 (d, J=4.4 Hz, 1H), 3.57-3.50 (m, 4H), 3.45-3.39 (m, 4H), 3.28-3.21 (m, 1H), 2.36-2.27 (m, 1H), 2.23-2.03 (m, 3H), 1.98-1.85 (m, 2H), 1.84-1.73 (m, 2H), 1.71-1.61 (m, 2H), 1.58-1.45 (m, 3H), 1.44-1.32 (m, 4H), 1.31-1.05 (m, 5H), 1.04-0.98 (m, 2H), 0.94 (s, 3H) 0.92-0.83 (m, 4H), 0.65 (s, 3H).

Example 8: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-thiomorpholinopentan-1-one

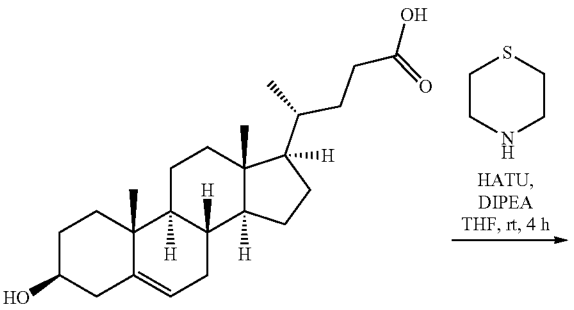

3β-hydroxy-5-cholenic acid

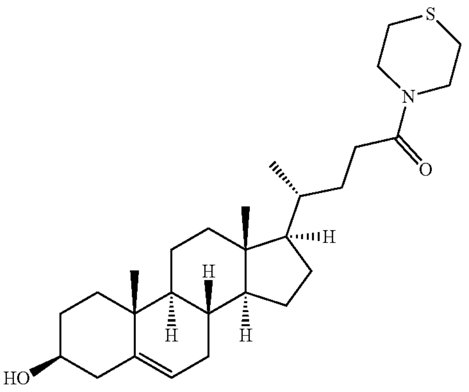

8

Compound 8 was synthesized according to the general procedure A using 3β-hydroxy-5-cholenic acid (100 mg, 0.26 mmol), HATU (152 mg, 0.40 mmol), DIPEA (69 mL, 0.53 mmol), thiomorpholine (55 mg, 0.53 mmol) and THE (1 mL). The reaction time was 4 h. The obtained crude material was purified by column chromatography over silica gel (100-200 mesh) with 0-3% gradient elution of MeOH in DCM to afford compound 8 (57 mg, 46%) as an off-white solid. ELSD-MS (ESI) m/z: 459.9 $[M+H]^+$; $^1H$ NMR (400 MHz, McOD): δ 5.27-5.23 (m, 1H), 3.74-3.68 (m, 4H), 3.34-3.25 (m, 1H), 2.58-2.54 (m, 2H), 2.52-2.47 (m, 2H), 2.38-2.30 (m, 1H), 2.23-2.07 (m, 3H), 1.98-1.83 (m, 3H), 1.82-1.75 (m, 2H), 1.73-1.60 (m, 2H), 1.59-1.32 (m, 7H), 1.29-1.15 (m, 3H), 1.14-1.00 (m, 3H), 0.99-0.83 (m, 9H) 0.64 (s, 3H).

Example 9: (R)-1-(1,1-dioxidothiomorpholino)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl) pentan-1-one

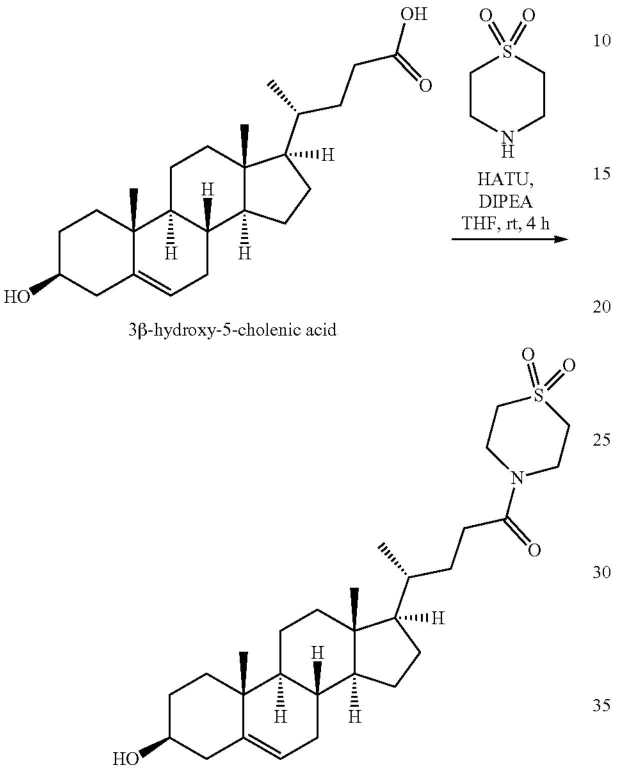

3β-hydroxy-5-cholenic acid

9

Compound 9 was synthesized according to the general procedure A using 3β-hydroxy-5-cholenic acid (100 mg, 0.26 mmol), HATU (101 mg, 0.26 mmol), DIPEA (34 mg 0.26 mmol), thiomorpholine 1,1-dioxide (36 mg, 0.26 mmol) and THE (1 mL). The reaction time was 4 h. The reaction mixture was poured into ice-cold water and the precipitated formed was filtered off, washed with water, and dried to get compound 9 (87.9 mg, 66%) as an off-white solid. ELSD-MS (ESI) m/z: 491.9 $[M+H]^+$; $^1H$ NMR (400 MHz, DMSO-$d_6$): δ 5.28-5.25 (m, 1H), 4.60 (d, J=4.4 Hz, 1H), 3.89-3.82 (m, 4H), 3.28-3.06 (m, 5H), 2.47-3.37 (m, 1H), 2.35-2.23 (m, 1H), 2.18-2.03 (m, 2H), 2.00-1.88 (m, 2H), 1.87-1.72 (m, 2H), 1.71-1.60 (m, 2H), 1.59-1.42 (m, 3H), 1.41-1.32 (m, 4H), 1.31-1.10 (m, 4H), 1.09-0.96 (m, 3H), 0.94 (s, 3H), 0.93-0.83 (m, 4H), 0.65 (s, 3H).

Example 10: (R)—N-ethoxy-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methylpentanamide

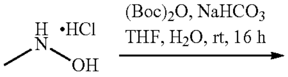

-continued

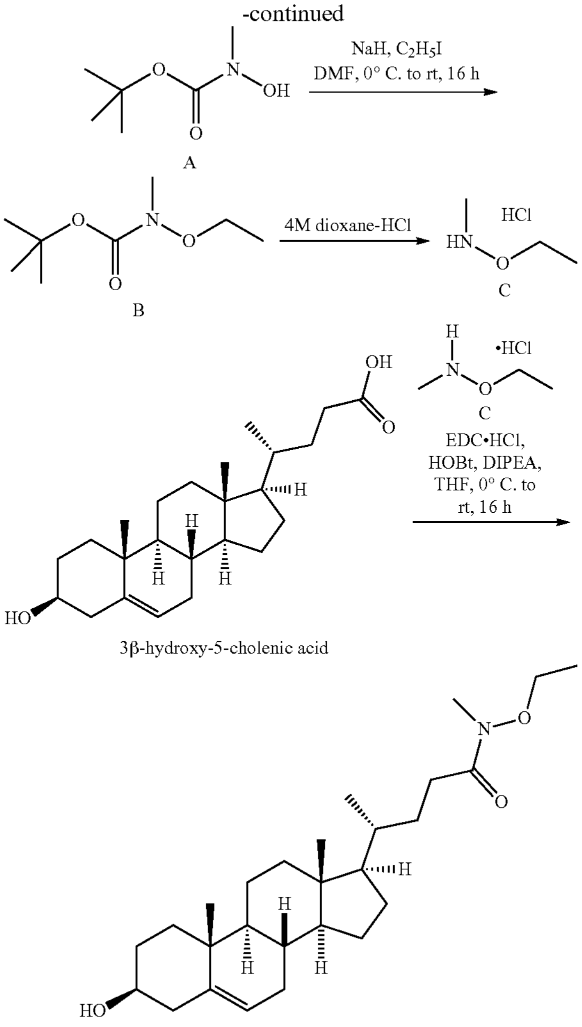

A

B

C

3β-hydroxy-5-cholenic acid

10

To a stirred solution of N-methylhydroxylamine hydrochloride (5 g, 59.8 mmol) in a mixture of THF (100 mL) and $H_2O$ (10 mL) were added $NaHCO_3$ (15.09 mg, 179.60 mmol) and $(Boc)_2O$ (13.07 g, 59.87 mmol) at 0° C. The resulting reaction mixture was stirred at room temperature for 16 h. Upon completion, the reaction mixture was diluted with water (20 mL) and extracted with DCM (50 mL×3). The combined organic layer was dried over sodium sulfate, filtered, concentrated in vacuo, and purified by column chromatography over silica gel (100-200 mesh) with 0-50% gradient elution of ethyl acetate in hexanes to afford the compound A as a colorless liquid. (5 g, 56%).

To a stirred solution of compound A (0.5 g, 3.40 mmol) in THF (5 mL) at 0° C. was added NaH, (60% dispersed in mineral oil, 122 mg, 5.1 mmol), and allowed to stir for 15 minutes. Ethyl iodide (1.59 ml, 10.19 mmol) was added at 0° C., and the resulting mixture was allowed to stir at room temperature for 16 h. Upon completion, the reaction mixture was quenched ice-water (20 mL) and extracted with ethyl acetate (30 mL×2). The combined organic layer was dried over sodium sulfate, filtered, concentrated in vacuo to afford compound B as a pale brown liquid (300 mg). The crude compound was used for the next step without further purification.

To a stirred solution of compound B (300 mg, 1.71 mmol) in 1,4-dioxane (3 mL) at 0° C. was added HCl solution (4M in 1,4-dioxane, 5 mL) under nitrogen atmosphere. The resulting reaction mixture was stirred at room temperature for 2 h. Upon completion, the reaction mixture was concentrated in vacuo and triturated with n-pentane to afford compound C as an off-white solid (100 mg, 77%). The crude compound was subjected to the next step without further purification.

Compound 10 was synthesized according to the general procedure B using 3β-hydroxy-5-cholenic acid (150 mg, 0.40 mmol), EDC.HCl (115 mg, 0.60 mmol), HOBt (59.5 mg, 0.44 mmol) DIPEA (0.2 mL, 1.2 mmol), crude compound C (49 mg, 0.44 mmol) and THE (5 mL). The resulting crude material was purified by column chromatography over silica gel (100-200 mesh) with 0-50% gradient elution of ethyl acetate in hexanes to afford the compound 10 (50 mg, 28%) as an off-white solid. ELSD-MS (ESI) m/z: 431.7 $[M+H]^+$; $^1H$ NMR (400 MHz, $CDCl_3$): δ 5.35-5.34 (m, 1H), 3.90 (q, J=6.8 Hz, 1H), 3.56-3.48 (m, 1H), 3.18 (s, 3H), 2.49-2.40 (m, 1H), 2.38-2.22 (m, 3H), 2.04-1.93 (m, 2H), 1.91-1.81 (m, 4H), 1.62-1.41 (m, 7H), 1.38-1.24 (m, 5H), 1.21-1.03 (m, 5H), 1.01 (s, 3H), 0.97-0.88 (m, 5H), 0.68 (s, 3H).

Example 11: (R)—N-ethyl-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methoxypentanamide

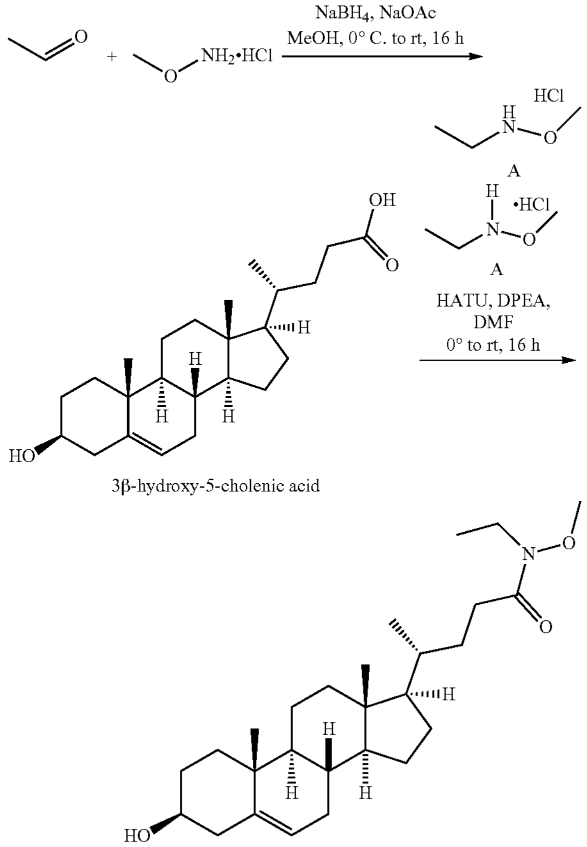

A
3β-hydroxy-5-cholenic acid
11

To a stirred solution of O-methylhydroxylamine hydrochloride (500 mg, 5.99 mmol) in MeOH (100 mL) at 0° C. were added NaOAc (491 mg, 5.99 mmol) and acetaldehyde (791 mg, 17.96 mmol). After stirring the mixture at 0° C. for 2 h, sodium borohydride (679 mg, 17.96 mmol) was added, and the resultant reaction mixture was stirred at room temperature for 16 h. Upon completion, the reaction mixture was quenched with ice-water (20 mL) and extracted with DCM (20 mL×3). The combined organic layer was dried over sodium sulfate, filtered, the filtrate was treated with HCl solution (4M HCl in 1,4-dioxane, 10 mL), concentrated, and triturated with n-pentane to afford compound A as an off-white solid. (150 mg, 22%). The crude compound was directly subjected to the next step without further purification.

Compound 11 was synthesized according to the general procedure A using 3β-hydroxy-5-cholenic acid (150 mg, 0.40 mmol), crude compound A (49 mg, 0.44 mmol), HATU (182 mg, 0.48 mmol), DIPEA (0.2 mL, 1.2 mmol), and DMF (5 mL). The crude material was purified by column chromatography over silica gel (100-200 mesh) with 0-50% gradient elution of ethyl acetate in hexanes to afford the title compound 11 (60 mg, 33%) as an off-white solid. ELSD-MS (ESI) m/z: 432.4 $[M+H]^+$; $^1H$ NMR (400 MHz, $CDCl_3$): δ 5.36-5.34 (m, 1H), 3.68 (s, 3H), 3.67-3.60 (m, 2H), 3.58-3.48 (m, 1H), 2.48-2.39 (m, 1H), 2.38-2.21 (m, 3H), 2.05-1.93 (m, 2H), 1.92-1.75 (m, 4H), 1.63-1.40 (m, 8H), 1.38-1.23 (m, 2H), 1.21-1.02 (m, 7H), 1.01 (s, 3H), 0.99-0.88 (m, 4H), 0.68 (s, 3H).

Example 12: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methyl-N-propoxypentanamide

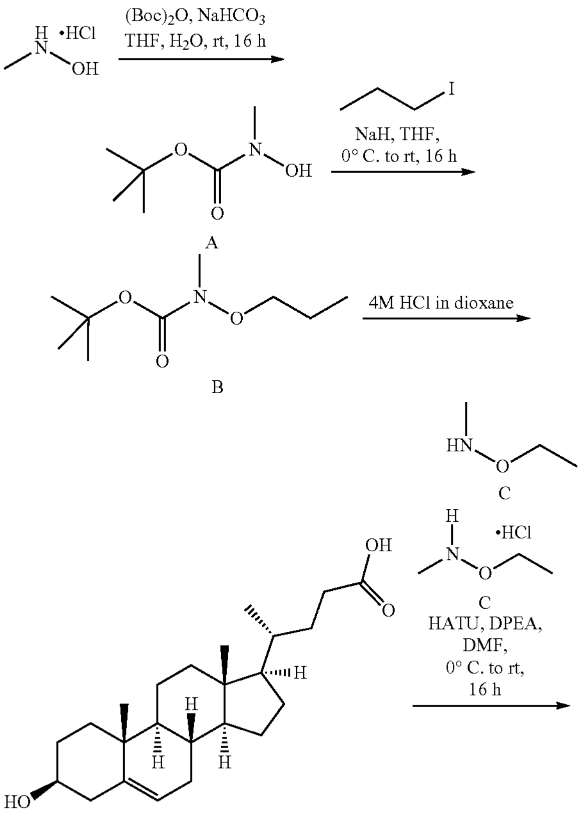

A
B
C
3β-hydroxy-5-cholenic acid

-continued

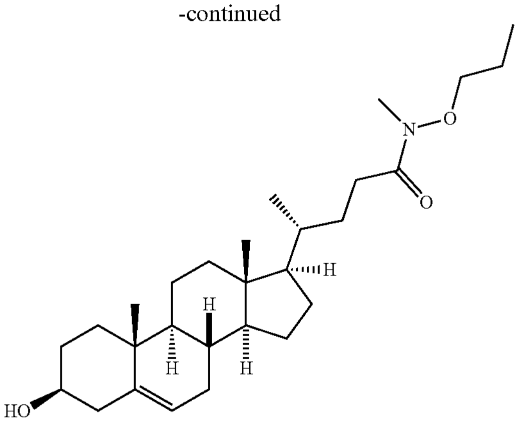

12

To a stirred solution of compound A (see Example 10)(0.5 g, 3.40 mmol) in THF (10 PGP-55,$C_3$ mL) at 0° C. was added NaH (60% dispersed in mineral oil, 122 mg, 5.1 mmol) under nitrogen atmosphere, and after stirring the mixture for 15 min at 0° C. was added ethyl 1-iodopropane (1.73 g, 10.19 mmol). The mixture was allowed to stir at room temperature for 16 h. Upon completion, the reaction mixture was quenched with ice-water (20 mL) and extracted with ethyl acetate (30 mL×2). The combined organic layer was dried over sodium sulfate, filtered, and concentrated in vacuo to afford compound B as a pale brown liquid (300 mg). The crude compound was subjected to the next step without further purification.

To a stirred solution of compound B (300 mg, 1.59 mmol) in 1,4-dioxane (3 mL) at 0° C. was added HCl solution (4M in 1,4-dioxane, 5 mL) under nitrogen atmosphere. The resultant reaction mixture was stirred at room temperature for 2 h. Upon completion, the reaction mixture was concentrated in vacuo and triturated with n-pentane to afford compound C as an off-white solid (100 mg, 70%).

Compound 12 was synthesized according to the general procedure A using 3β-hydroxy-5-cholenic acid (150 mg, 0.40 mmol), HATU (305 mg, 0.80 mmol), DIPEA (0.21 mL, 1.2 mmol), compound C (50 mg, 0.40 mmol) and THE (5 mL) were used. The crude material was purified by column chromatography over silica gel (100-200 mesh) with 0-50% gradient elution of ethyl acetate in hexanes to afford the compound 12 (50 mg, 27%) as an off-white solid. ELSD-MS (ESI) m/z: 445.8 $[M+H]^+$; $^1H$ NMR (400 MHz, $CDCl_3$): δ 5.35-5.34 (m, 1H), 3.79 (q, J=6.4 Hz, 2H), 3.55-3.49 (m, 1H), 3.18 (s, 3H), 2.50-2.40 (m, 1H), 2.38-2.19 (m, 3H), 2.03-1.93 (m, 2H), 1.92-1.75 (m, 4H), 1.72-1.61 (m, 4H), 1.60-1.41 (m, 6H), 1.38-1.24 (m, 3H), 1.21-1.06 (m, 4H), 1.04-0.98 (m, 6H), 0.97-0.88 (m, 4H), 0.68 (s, 3H).

Example 13: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methoxy-N-propylpentanamide

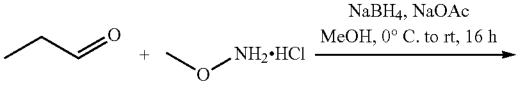

-continued

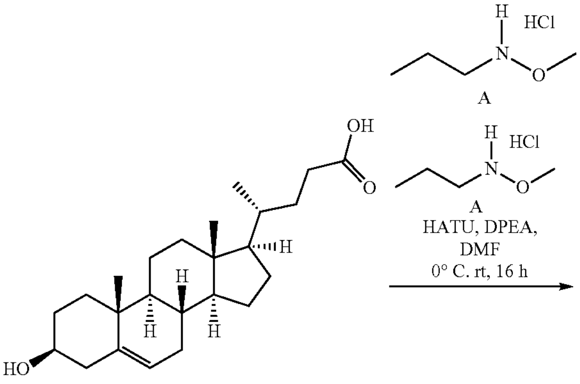

3β-hydroxy-5-cholenic acid

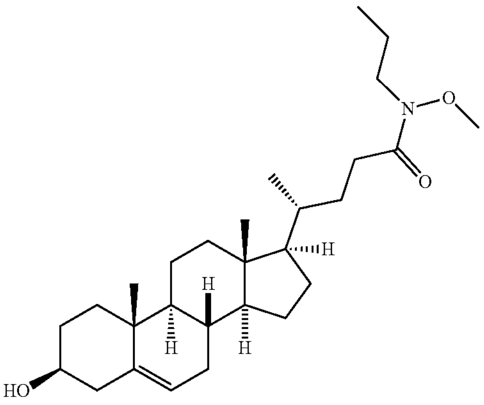

13

To a stirred solution of O-methyl hydroxylamine hydrochloride (1 g, 11.97 mmol) in MeOH (20 mL) at 0° C. were added NaOAc (983 mg, 11.97 mmol) and propanal (2.09 g, 35.92 mmol). After stirring the mixture at 0° C. for 1 h, sodium borohydride (1.36 g, 35.92 mmol) was added and the resultant reaction mixture was stirred at room temperature for 16 h. Upon completion, the reaction mixture was quenched with ice-cold water (20 mL) and extracted with DCM (20 mL×3). The combined organic layer was dried over sodium sulfate, filtered, the filtrate was treated with 4M HCl in 1,4-dioxane (10 mL), concentrated, and triturated with n-pentane to afford compound A as light brown liquid (200 mg, 13%). The crude compound was used for the next step without further purification.

Compound 13 was synthesized according to the general procedure A using 3β-hydroxy-5-cholenic acid (150 mg, 0.40 mmol), crude compound A (202 mg, 1.60 mmol), HATU (304 mg, 0.80 mmol), DIPEA (0.47 mL, 2.8 mmol), and DMF (5 mL). The obtained crude material was purified by column chromatography over silica gel (100-200 mesh) with 0-50% gradient elution of ethyl acetate in hexanes to afford the compound 13 (54 mg, 30.1%) as an off-white solid. ELSD-MS (ESI) m/z: 445.9 $[M+H]^+$; $^1H$ NMR (400 MHz, $CDCl_3$): δ 5.36-5.34 (m, 1H), 3.67 (s, 3H), 3.59-3.49 (m, 3H), 2.48-2.40 (m, 1H), 2.39-2.22 (m, 3H), 2.03-1.93 (m, 2H), 1.88-1.76 (m, 4H), 1.67-1.60 (m, 2H), 1.56-1.40 (m, 8H), 1.39-1.29 (m, 2H), 1.21-1.01 (m, 5H), 1.00 (s, 3H), 0.96 (d, J=6.8 Hz, 3H), 0.91 (t, J=7.2 Hz, 3H), 0.68 (s, 3H).

Example 14: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-isopropoxy-N-methylpentanamide
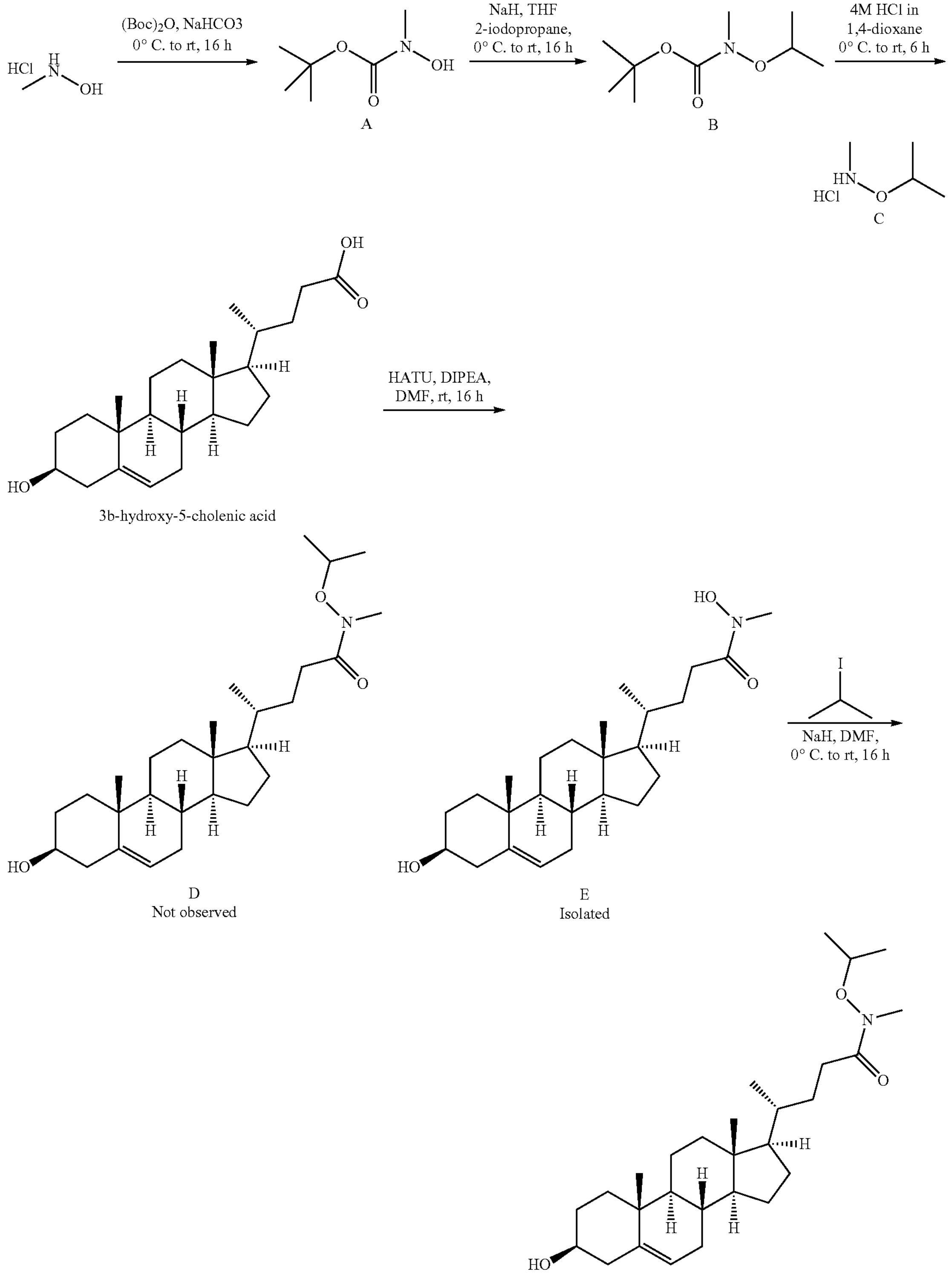
A
B
C
3b-hydroxy-5-cholenic acid
D
Not observed
E
Isolated
14

To a stirred solution of N-methylhydroxylamine hydrochloride (5 g, 59.87 mmol) in mixture of THF (100 mL) and water (10 mL) were added $NaHCO_3$ (15.09 g, 179.60 mmol) and di-tert-butyl dicarbonate (13.07 g, 59.87 mmol, 13.74 mL) at 0° C. The resultant mixture was stirred at room temperature for 16 h. Upon completion, the reaction mixture was diluted with water (10 mL) and extracted with DCM (3×50 mL). The combined organic layer was washed with brine (50 mL), dried over anhydrous sodium sulfate, filtered, and concentrated to obtain crude. The crude material was purified by column chromatography over silica gel (100-200 mesh) with a gradient elution of 0-50% ethyl acetate in hexane to afford compound A as a colorless liquid (5 g).

To a stirred solution of compound A (500 mg, 3.40 mmol, 1 eq.) in THF (5 mL), was added NaH (60% dispersion in mineral oil, 163 mg, 6.79 mmol) portion wise over a period of 5 min at 0° C. After stirring the mixture for 1 h at 0° C., 2-iodopropane (693.03 mg, 4.08 mmol, 0.4 mL) was added and the resultant mixture was allowed to stir at room temperature for 16 h. Upon completion, the reaction mixture was quenched with ice water (20 mL) and extracted with ethyl acetate (3×20 mL). The combined organic layer was washed with water (10 mL), brine (10 mL), dried over anhydrous sodium sulfate, filtered, and concentrated. The crude material was purified by column chromatography over silica gel (100-200 mesh) by gradient elution of 0-50% ethyl acetate in pet ether to afford compound B as a yellow liquid (400 mg, Yield: 62%).

To a stirred solution of compound B (400.00 mg, 2.11 mmol) in 1,4-dioxane (5 mL) was added HCl solution (4M in 1,4-dioxane, 3 mL) at 0° C. and the resultant mixture was stirred at room temperature for 6 h. Upon completion, the reaction mixture was concentrated and dried under vacuo to afford compound C as a gummy liquid (200 mg, Yield:75%) which was used for the next step without further purification.

Compound E was synthesized according to the general procedure A using 3β-hydroxy-5-cholenic acid (150 mg, 0.401 mmol), crude compound C (50.30 mg, 0.401 mmol), HATU (304 mg, 0.802 mmol) and DIPEA (0.210 mL, 1.20 mmol) and DMF (5 mL) were reacted for 16 h. The obtained crude compound was purified by column chromatography over silica gel (100-200 mesh) by gradient elution of 0-70% ethyl acetate in pet ether to afford compound E as an off-white solid (80 mg, Yield:45%). Formation of compound D was not observed under this condition.

To a stirred solution of compound E (80 mg, 0.198 mmol) in DMF (5 mL) at 0° C. were added NaH (60% dispersion in mineral oil, 9.5 mg, 0.396 mmol), 2-iodopropane (0.018 mL, 0.198 mmol). The resultant reaction mixture was allowed to warm to room temperature and stirred for 16 h. Upon completion, the reaction mixture was quenched with ice water (20 mL) and extracted with ethyl acetate (2×20 mL). The combined organic layer was washed with brine (10 mL), dried over anhydrous sodium sulfate, filtered, and concentrated in vacuo to obtain crude compound. Crude compound was purified by column chromatography over silica gel (100-200 mesh) by gradient elution of 0-50% ethyl acetate in pet ether to afford the title compound 14 as an off-white solid (26 mg, Yield: 29.1%). LC-MS (ESI) m/z: 446.4 $(M+H)^+$; $^1H$ NMR (400 MHz, DMSO-$d_6$): δ 5.26 (brd, J=4.8 Hz, 1H), 4.62 (d, J=4.8 Hz, 1H), 4.15-4.12 (m, 1H), 3.30-3.21 (m, 1H), 3.06 (s, 3H), 2.40-2.25 (m, 2H), 2.18-2.03 (m, 2H), 1.98-1.87 (m, 2H), 1.85-1.71 (m, 2H), 1.68-1.60 (m, 2H), 1.59-1.45 (m, 3H), 1.41-1.32 (m, 4H), 1.30-1.20 (m, 2H), 1.18 (d, J=6 Hz, 6H), 1.15-0.96 (m, 5H), 0.94 (s, 3H), 0.92-0.88 (m, 4H), 0.64 (s, 3H).

Example 15: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-isopropyl-N-methoxypentanamide

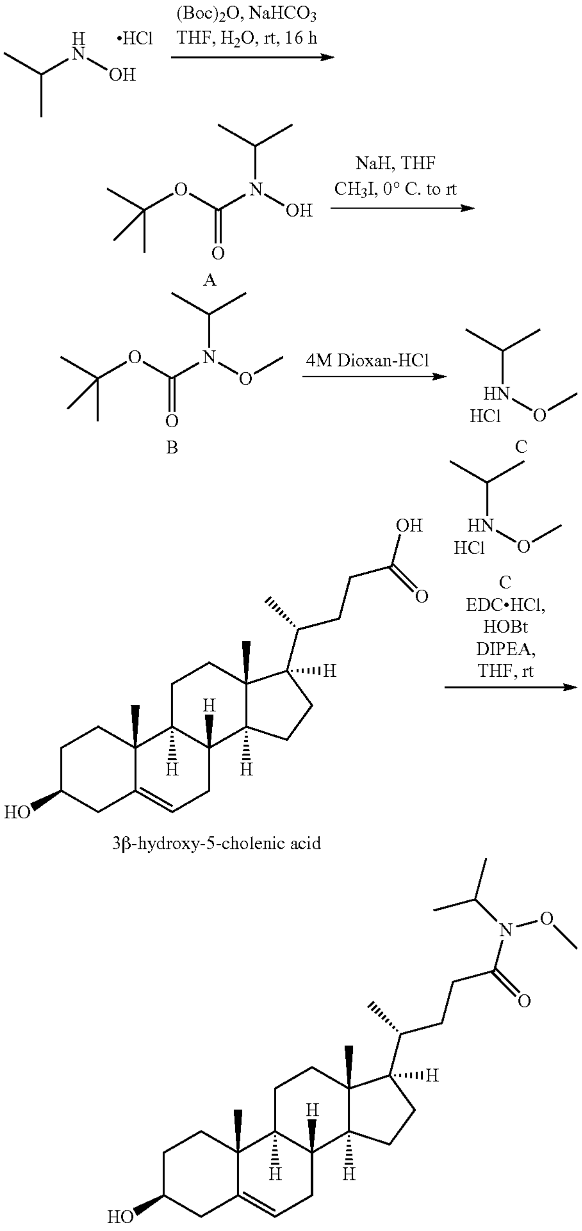

15

To a stirred solution of N-isopropylhydroxylamine hydrochloride (500 mg, 4.48 mmol) in a mixture of THF (9 mL) and $H_2O$ (2 mL) at 0° C. were added $NaHCO_3$ (1.13 g, 13.44 mmol) and $(Boc)_{2O}$ (1.17 g, 5.38 mmol). The resultant reaction mixture was stirred at room temperature for 2 h. Upon completion, the reaction mixture was diluted with water (20 mL) and extracted with DCM (30 mL×3). The combined organic layer was dried over sodium sulfate, filtered, concentrated in vacuo, and purified by column chromatography over silica gel (100-200 mesh) with 0-50% gradient elution of ethyl acetate in hexanes to afford the compound A (400 mg, 50%).

To a stirred solution of compound A (1 g, 5.71 mmol) in THF (10 mL) at 0° C. was added NaH (60% dispersed in mineral oil, 262 mg, 11.4 mmol) under nitrogen atmosphere, after stirring the mixture for 10 min at 0° C. was added methyl iodide (0.426 mL, 6.85 mmol) and the mixture was allowed to stir at room temperature for 16 h. Upon completion, the reaction mixture was quenched with ice-water (20 mL) and extracted with ethyl acetate (50 mL×3). The combined organic layer was dried over sodium sulfate, filtered, concentrated in vacuo, and purified by column chromatography over silica gel (100-200 mesh) with 0-50% gradient elution of ethyl acetate in hexanes to afford compound B (800 mg, 74%).

To a stirred solution of compound B (400 mg, 2.11 mmol) in 1,4-dioxane (5 mL) at 0° C. was added 4M HCl in 1,4-dioxane (5 mL) under nitrogen atmosphere. The resultant reaction mixture was stirred at room temperature for 6 h. Upon completion, the reaction mixture was concentrated in vacuo to afford compound C (200 mg). The crude compound was directly subjected to the next step without further purification.

Compound 15 was synthesized according to the general procedure B using 3β-hydroxy-5-cholenic acid (150 mg, 0.40 mmol), EDC.HCl (115 mg, 0.60 mmol), HOBt (59 mg, 0.44 mmol), DIPEA (0.21 mL, 1.2 mmol), crude compound C (60 mg, 0.48 mmol), and THF (5 mL). The obtained crude material was purified by column chromatography over silica gel (100-200 mesh) with 0-50% gradient elution of ethyl acetate in hexanes to afford the compound 15 (60 mg, 33%) as an off-white solid. ELSD-MS (ESI) m/z: 445.9 $[M+H]^+$; $^1H$ NMR (400 MHz, $CDCl_3$): δ 5.35-5.34 (m, 1H), 4.57 (brs, 1H), 3.76 (s, 3H), 3.58-3.47 (m, 1H), 2.48-2.38 (m, 1H), 2.37-2.20 (m, 3H), 2.03-1.92 (m, 2H), 1.91-1.73 (m, 4H), 1.63-1.39 (m, 8H), 1.38-1.22 (m, 2H), 1.21-0.88 (m, 17H), 0.68 (s, 3H).

Example 16: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methyl-N-propoxypentanamide

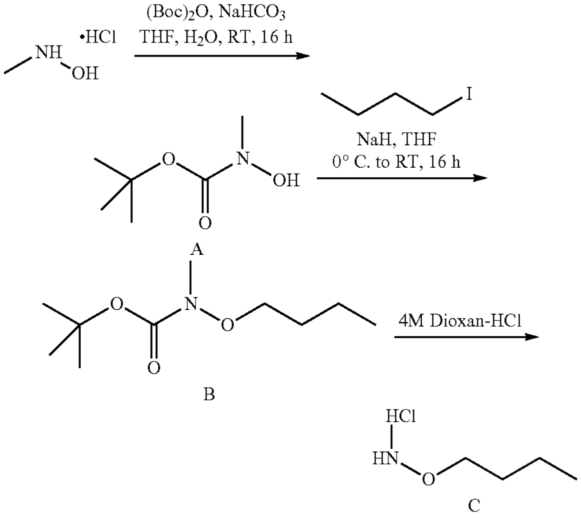

A
B
C

-continued

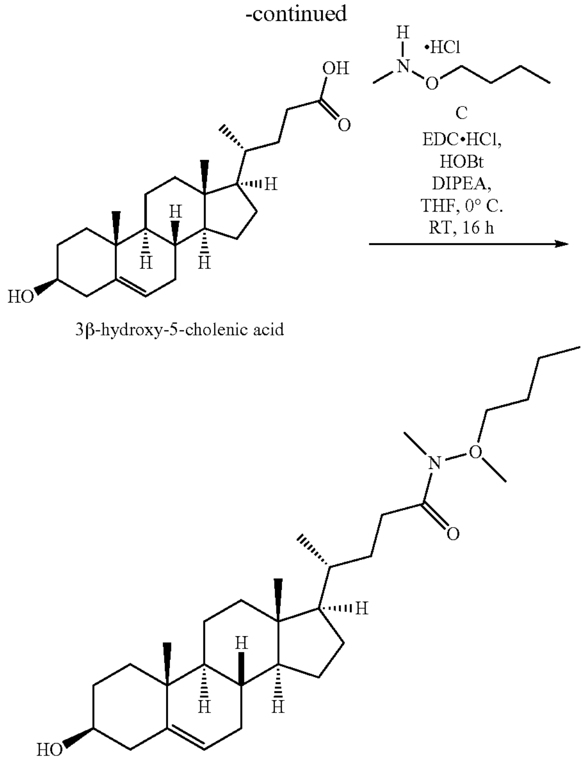

3β-hydroxy-5-cholenic acid

To a stirred solution of compound A (see Example 10)(0.5 g, 3.40 mmol) in THF (5 mL) at 0° C. was added NaH (60% dispersed in mineral oil, 163 mg, 6.79 mmol) under nitrogen atmosphere. After stirring the mixture for 15 min at 0° C. was added 1-iodobutane (1.88 g, 10.19 mmol) and the resultant mixture was allowed to stir at room temperature for 16 h. Upon completion, the reaction mixture was quenched with ice-water (20 mL) and extracted with ethyl acetate (30 mL×2). The combined organic layer was dried over sodium sulfate, filtered, and concentrated in vacuo to afford compound B as a pale brown liquid (400 mg). The crude compound was subjected to the next step reaction without further purification.

To a stirred solution of compound B (400 mg, 1.97 mmol) in 1,4-dioxane (3 mL) at 0° C. was added 4M HCl in 1,4-dioxane (5 mL) under nitrogen atmosphere. The resultant reaction mixture was stirred at room temperature for 2 h. Upon completion, the reaction mixture was concentrated in vacuo and triturated with n-pentane to afford compound C as an off-white solid (120 mg, 59%).

Compound 16 was synthesized according to the general procedure B using 3β-hydroxy-5-cholenic acid (150 mg, 0.40 mmol), EDC.HCl (84 mg, 0.44 mmol), HOBt (81 mg, 0.6 mmol), DIPEA (0.21 mL, 1.2 mmol), compound C (61 mg, 0.44 mmol), and THE (5 mL). The crude material was purified by column chromatography over silica gel (100-200 mesh) with 0-50% gradient elution of ethyl acetate in hexanes to afford the title compound 16 (50 mg, 26%) as an off-white solid. ELSD-MS (ESI) m/z: 460.4 $[M+H]^+$; $^1H$ NMR (400 MHz, $CDCl_3$): δ 5.35-5.34 (m, 1H), 3.83 (t, J=6.4 Hz, 2H), 3.55-3.49 (m, 1H), 3.18 (s, 3H), 2.50-2.40 (m, 1H), 2.39-2.19 (m, 3H), 2.04-1.93 (m, 2H), 1.92-1.76 (m, 4H), 1.66-1.58 (m, 3H), 1.57-1.39 (m, 8H), 1.38-1.23 (m, 3H), 1.21-1.06 (m, 4H), 1.04-0.89 (m, 11H), 0.68 (s, 3H).

Example 17: (R)—N-butyl-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methoxypentanamide

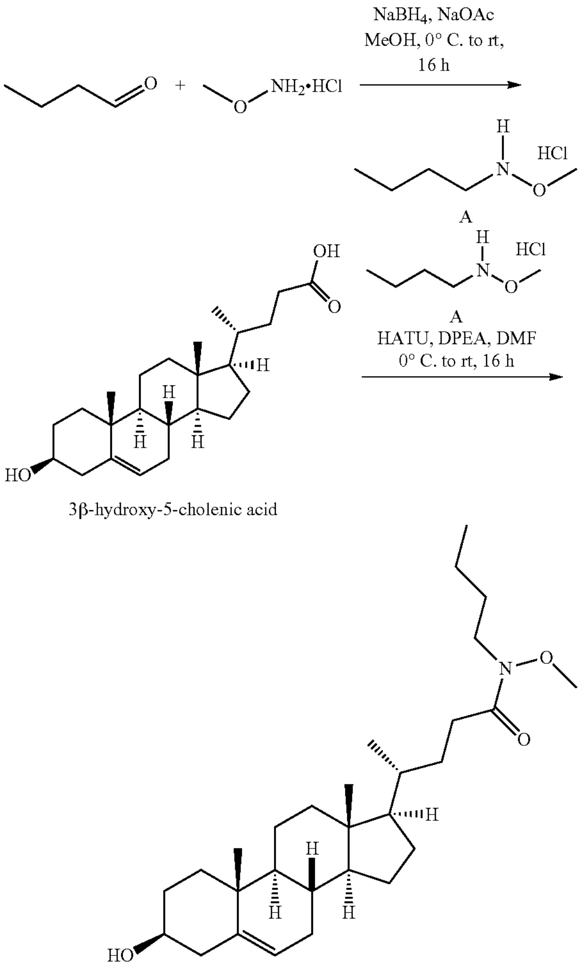

A

A

3β-hydroxy-5-cholenic acid

17

To a stirred solution of O-methyl hydroxylamine hydrochloride (1 g, 11.97 mmol) in MeOH (10 mL) at 0° C. were added NaOAc (983 mg, 11.97 mmol) and butanal (2.59 g, 35.92 mmol). After stirring the mixture at 0° C. for 1 h, sodium borohydride (1.36 g, 35.92 mmol) was added and the resultant reaction mixture was stirred at room temperature for 16 h. Upon completion, the reaction mixture was quenched with ice-water (20 mL) and extracted with DCM (20 mL×3). The combined organic layer was dried over sodium sulfate, filtered, the filtrate was treated with HCl solution (4M in 1,4-dioxane, 10 mL), concentrated, and triturated with n-pentane to afford crude compound A as light brown liquid (200 mg, 12%). The crude compound was directly subjected to the next step without further purification.

Compound 17 was synthesized according to the general procedure A using 3β-hydroxy-5-cholenic acid (150 mg, 0.40 mmol), crude compound A (224 mg, 1.60 mmol), HATU (305 mg, 0.80 mmol), DIPEA (0.47 mL, 2.8 mmol), and THF (3 mL). The crude material was purified by column chromatography over silica gel (100-200 mesh) with 0-50% gradient elution of ethyl acetate in hexanes to afford the compound 17 (40 mg, 21%) as an off-white solid. ELSD-MS (ESI) m/z: 459.9 $[M+H]^+$; $^1H$ NMR (400 MHz, $CDCl_3$): δ 5.36-5.34 (m, 1H), 3.67 (s, 3H), 3.60-3.49 (m, 3H), 2.50-2.20 (m, 4H), 2.01-1.92 (m, 2H), 1.91-1.75 (m, 4H), 1.54-1.40 (m, 9H), 1.39-1.24 (m, 4H), 1.22-1.02 (m, 4H), 1.00 (s, 3H), 0.98-0.90 (m, 8H), 0.68 (s, 3H).

Example 18: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(1-oxidothiomorpholino)pentan-1-one

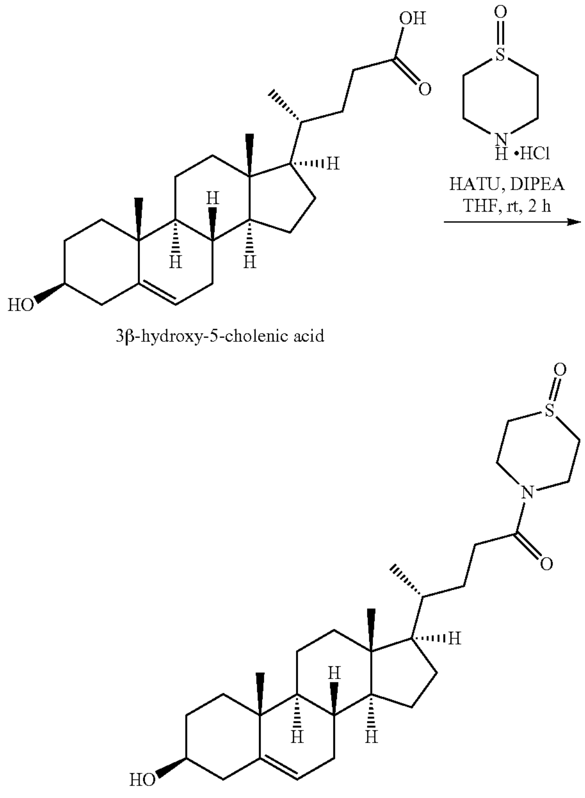

3β-hydroxy-5-cholenic acid

18

Compound 18 was synthesized according to the general procedure A using 3β-hydroxy-5-cholenic acid (100 mg, 0.26 mmol), HATU (203 mg, 0.53 mmol), DIPEA (103 mg, 0.80 mmol), 1,4-thiazinane 1-oxide hydrochloride (83 mg, 0.53 mmol) and THF (1 mL). The reaction time was 2 h. The reaction mixture was poured into ice-cold water and the precipitated formed was filtered off, washed with water and dried to get compound 18 (74 mg, 58%) as an off-white solid. ELSD-MS (ESI) m/z: 475.9 $[M+H]^+$; $^1H$ NMR (400 MHz, $CDCl_3$): δ 5.37-5.34 (m, 1H), 4.52-4.48 (m, 1H), 4.16-4.10 (m, 1H), 3.82-3.71 (m, 2H), 3.53-3.49 (m, 1H), 2.90-2.80 (m, 2H), 2.71-2.68 (m, 2H), 2.43-2.22 (m, 3H), 2.01-1.91 (m, 2H), 1.90-1.72 (m, 4H), 1.58-1.42 (m, 10H), 1.40-1.22 (m, 2H), 1.20-1.01 (m, 4H), 1.00 (s, 3H) 0.96-0.90 (m, 4H), 0.68 (s, 3H).

Examples 19 and 20

Example 19: (3S,8S,9S,10R,13R,14S,17R)-17-((2R,5S)-5-hydroxy-5-(trifluoromethyl)hept-6-en-2-yl)-10,13-dimethyl2,3,4,7,8,9,10,11,12,13,14,15,16,17-tetradecahydro-1H-cyclopenta[a]phenanthren-3-ol Example 20: (3S,8S,9S,10R,13R,14S,17R)-17-((2R,5R)-5-hydroxy-5-(trifluoromethyl)hept-6-en-2-yl)-10,13-dimethyl-2,3,4,7,8,9,10,11,12,13,14,15,16,17-tetradecahydro-1H-cyclopenta[a]phenanthren-3-ol

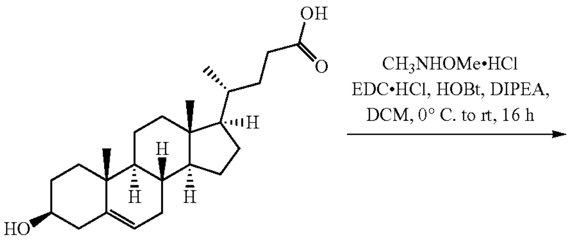

3b-hydroxy-5-cholenic acid

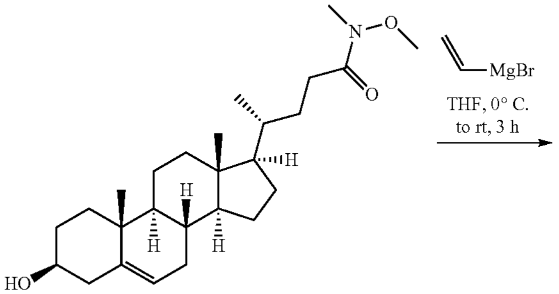

A

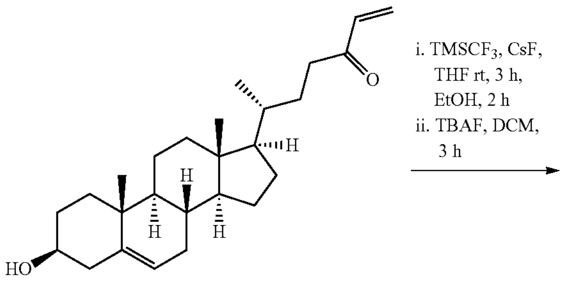

B

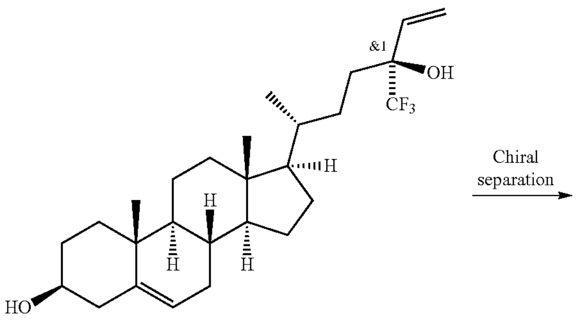

C
(mixture of distereomers)

-continued

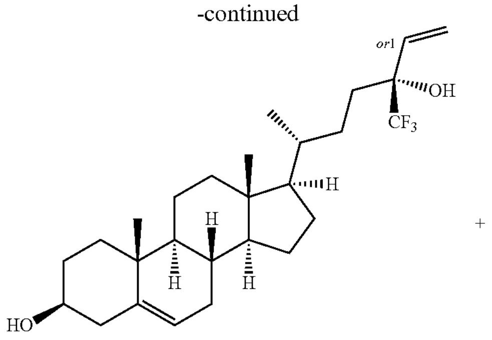

20

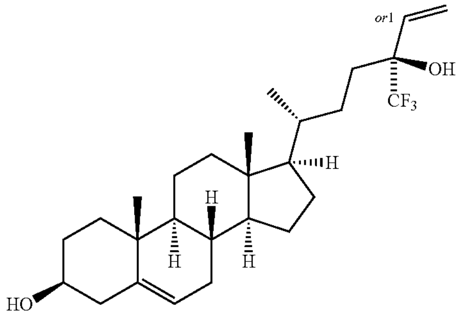

19

Compound A was synthesized according to the general procedure B. 3β-hydroxy-5-cholenic acid (2.5 g, 6.67 mmol), EDC.HCl (1.91 g, 10 mmol), HOBt (992 mg, 7.34 mmol), DIPEA (2.33 mL, 13.3 mmol), N,O-dimethyl hydroxylamine (781 mg, 8.01 mmol) and DCM (30 mL). The obtained crude material was purified by column chromatography over silica gel (100-200 mesh) with 0-50% gradient elution of ethyl acetate in hexanes to afford compound A as an off-white solid (1.9 g, 68%). LC-MS (ESI) m/z: 418.5 $[M+H]^+$.

To a stirred solution of A (1.8 g, 4.31 mmol) in THF (40 mL) at 0° C. was added vinyl magnesium bromide (1M in THF, 6.55 g, 50 mL, 50 mmol) under nitrogen atmosphere. The resultant reaction mixture was stirred at room temperature for 3 h. Upon completion, the reaction mixture was quenched with saturated aqueous $NH_4Cl$ (50 mL) and extracted with ethyl acetate (100 mL×3). The combined organic layer was dried over sodium sulfate, filtered, concentrated in vacuo, and purified by column chromatography over silica gel (100-200 mesh) with 0-50% gradient elution of ethyl acetate in hexanes to afford compound B as an off-white solid (1.2 g, 72%). LC-MS (ESI) m/z: 367.4 $[M-H_2O]^+$.

To a stirred solution of B (1.2 g, 3.12 mmol) in THF (20 mL) were added CsF (94.8 mg, 0.624 mmol) and $TMSCF_3$ (1.33 g, 9.36 mmol) sequentially at room temperature. The resulting mixture was stirred at room temperature for 3 h. EtOH (20 mL) was added, and the mixture was stirred at room temperature for 2 h. Upon completion, the reaction mixture was concentrated in vacuo, diluted with water (10 mL) and extracted with ethyl acetate (30 mL×3). The combined organic layer was dried over anhydrous sodium sulfate and concentrated in vacuo. The obtained crude compound was dissolved in DCM (30 mL), added TBAF (1M in THF, 30 mL) at 0° C. and allowed to stir at room temperature for 3 h. Upon completion, the reaction mixture was quenched with saturated aqueous $NH_4C_1$ (100 mL) and extracted with DCM (100 mL×3). The combined organic layer was dried over sodium sulfate, filtered, concentrated in vacuo and purified by column chromatography over silica gel (100-200 mesh) using 0-50% gradient elution of ethyl acetate in hexanes to afford compound C as an off-white solid (1 g, diastereomeric mixture). The diastereomers were separated by chiral prep HPLC [column: CHIRALPAK-IA (250*4.6 mm), 5 μm; mobile phase: hexanes/IPA 90/10; flow rate: 1 mL/min.] to afford compound 19 (peak-1, 155 mg, 15%) and compound 20 (peak-2, 356 mg, 34%) as an off-white solid.

19 (peak-1): LC-MS (ESI) m/z: 437 $[M-H_2O]^+$; $^1H$ NMR (400 MHz, DMSO-$d_6$) δ 5.93 (s, 1H), 5.76 (dd, J=10.8, 17.2 Hz, 1H), 5.47 (dd, J=1.6, 17.2 Hz, 1H), 5.37 (dd, J=1.6, 10.8 Hz, 1H), 5.26-5.25 (m, 1H), 4.58 (d, J=4.8 Hz, 1H), 3.30-3.21 (m, 1H), 2.17-2.03 (m, 2H), 1.98-1.87 (m, 2H), 1.79-1.60 (m, 4H), 1.58-1.30 (m, 9H), 1.29-0.97 (m, 6H), 0.96-0.83 (m, 8H), 0.64 (s, 3H); $^{19}F$ NMR (376 MHz, DMSO-$d_6$): δ-79.56 (s, $CF_3$).

20 (peak-2): LC-MS (ESI) m/z: 436.9 $[M-H_2O]^+$; $^1H$ NMR (400 MHz, DMSO-$d_6$) δ 5.93 (s, 1H), 5.76 (dd, J=10.8, 17.2 Hz, 1H), 5.47 (dd, J=1.6, 17.2 Hz, 1H), 5.38 (dd, J=1.6, 10.8 Hz, 1H), 5.26-5.25 (m, 1H), 4.59 (d, J=4.8 Hz, 1H), 3.30-3.24 (m, 1H), 2.17-2.03 (m, 2H), 1.98-1.87 (m, 2H), 1.81-1.61 (m, 4H), 1.58-1.29 (m, 9H), 1.27-0.97 (m, 7H), 0.93 (s, 3H), 0.91-0.83 (m, 4H), 0.64 (s, 3H); $^{19}F$ NMR (376 MHz, DMSO-$d_6$): δ-79.34 (s, $CF_3$).

Examples 21 and 22

Example 21: (3S,8S,9S,10R,13R,14S,17R)-17-((2R,5R)-5-hydroxy-5-(trifluoromethyl)heptan-2-yl)-10,13-dimethyl-2,3,4,7,8,9,10,11,12,13,14,15,16,17-tetradecahydro-1H-cyclopenta(a)phenanthren-3-ol

Example 22: (3S,8S,9S,10R,13R,14S,17R)-17-((2R,5S)-5-hydroxy-5-(trifluoromethyl)heptan-2-yl)-10,13-dimethyl-2,3,4,7,8,9,10,11,12,13,14,15,16,17-tetradecahydro-1H-cyclopenta(a)phenanthren-3-ol

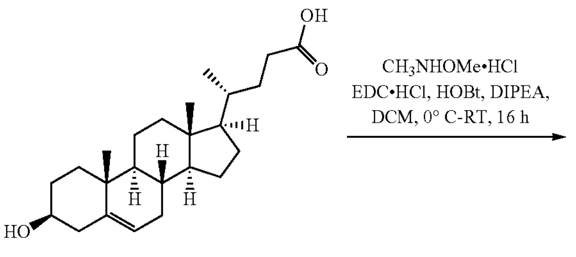

3β-hydroxy-5-cholenic acid

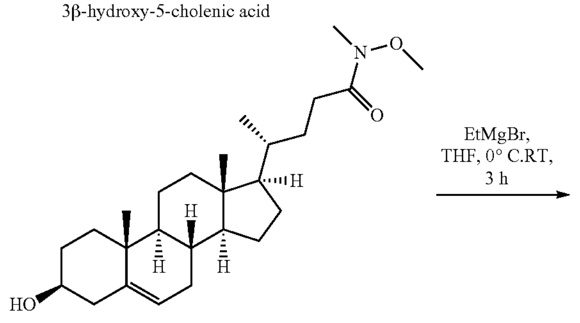

A

-continued

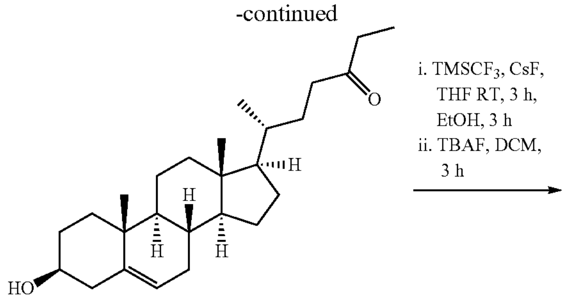

B

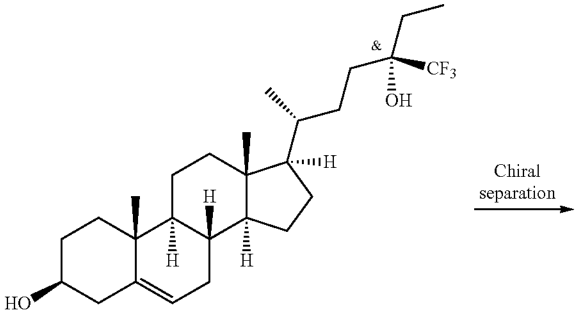

C

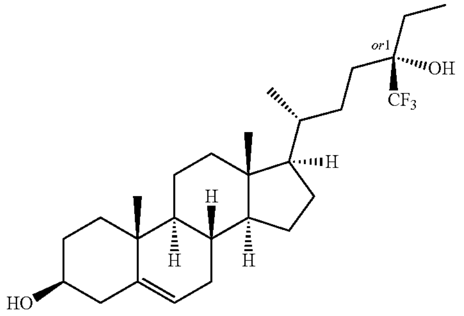

22

+

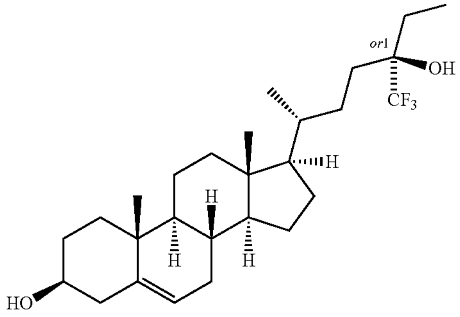

21

Compound A was synthesized according to general procedure B as described in the example 19 and 20. To a stirred solution of A (300 mg, 0.718 mmol) in THF (6 mL) at room temperature was added ethyl magnesium bromide (1M in THF, 10 mL, 0.239 mmol) under nitrogen atmosphere. The resultant reaction mixture was stirred at room temperature for 3 h. Upon completion, the reaction mixture was quenched with saturated aqueous $NH_4C_1$ (50 mL) and extracted with ethyl acetate (50 mL×2). The combined organic layer was dried over sodium sulfate, filtered, concentrated in vacuo, and purified by column chromatography over silica gel (100-200 mesh) using 0-7% gradient elution of ethyl acetate in hexanes to afford compound B as an off-white solid (0.2 g, 72%). LC-MS m/z: 369 $(M-H_2O+1)^+$.

To a stirred solution of B (0.2 g, 0.517 mmol) in THF (4 mL) were added CsF (16 mg, 0.103 mmol) and $TMSCF_3$ (221 mg, 1.554 mmol) sequentially at room temperature and stirred for 3 h. EtOH (4 mL) was then added, and the mixture was stirred at room temperature for 2 h. Upon completion, the reaction mixture was concentrated in vacuo, diluted with water (30 mL) and extracted with ethyl acetate (25 mL×2). The combined organic layer was dried over anhydrous sodium sulfate and concentrated in vacuo. The obtained crude compound was dissolved in DCM (4 mL), added TBAF (1M in THF, 0.2 mL) at 0° C. and allowed to stir at room temperature for 2 h. Upon completion, the reaction mixture was quenched with water (50 mL) and extracted with DCM (20 mL×3). The combined organic layer was dried over sodium sulfate, filtered, concentrated in vacuo, and purified by column chromatography over silica gel (100-200 mesh) with 0-10% gradient elution of ethyl acetate in hexanes to afford compound C as an off-white solid (0.11 g, diastereomeric mixture). The diastereomers were separated by chiral preparative HPLC (column: Chiralpak IG 250*4.6 mm, 5μ; mobile phase: hexanes/0.1% TFA in methanol 90/10; flow rate: 0.5 mL/min.) to afford compound 21 (peak-1, 16 mg, 7%) and compound 22 (peak-2, 25 mg, 11%) as an off-white solid.

21 (peak-1): MS (APCI) m/z: 439 $(M-H_2O)^+$; $^1H$ NMR (400 MHz, DMSO-$d_6$) δ 5.51 (s, 1H), 5.26-5.25 (m, 1H), 4.58 (d, J=4.8 Hz, 1H), 3.28-3.21 (m, 1H), 2.18-2.04 (m, 2H), 1.97-1.85 (m, 2H), 1.84-1.73 (m, 2H), 1.70-1.31 (m, 12H), 1.28-1.19 (m, 3H), 1.18-0.94 (m, 6H), 0.93 (s, 3H), 0.91-0.84 (m, 6H), 0.65 (s, 3H). $^{19}F$ NMR (376 MHz, DMSO-$d_6$): δ-79.56 (s, $CF_3$).

22 (peak-2): MS (APCI) m/z: 439 $(M-H_2O)^+$; $^1H$ NMR (400 MHz, DMSO-$d_6$) δ 5.52 (s, 1H), 5.27-5.25 (m, 1H), 4.58 (d, J=4.4 Hz, 1H), 3.28-3.21 (m, 1H), 2.17-2.05 (m, 2H), 1.96-1.85 (m, 2H), 1.83-1.72 (m, 2H), 1.70-1.32 (m, 14H), 1.31-1.21 (m, 1H), 1.17-0.96 (m, 6H), 0.94 (s, 3H), 0.91-0.83 (m, 6H), 0.65 (s, 3H). $^{19}F$ NMR (376 MHz, DMSO-$d_6$): δ-77.91 (s, $CF_3$).

Examples 23 and 24

Example 23: (3S,8S,9S,10R,13R,14S,17R)-17-((2R,5s)-5-cyclopropyl-6,6,6-trifluoro-5-hydroxyhexan-2-yl)-10,13-dimethyl-2,3,4,7,8,9,10,11,12,13,14,15,16,17-tetradecahydro-1H-cyclopenta(a)phenanthren-3-ol Example 24: (3S,8S,9S,10R,13R,14S,17R)-17-((2R,5R)-5-cyclopropyl-6,6,6-trifluoro-5-hydroxyhexan-2-yl)-10,13-dimethyl-2,3,4,7,8,9,10,11,12,13,14,15,16,17-tetradecahydro-1H-cyclopenta(a)phenanthren-3-ol

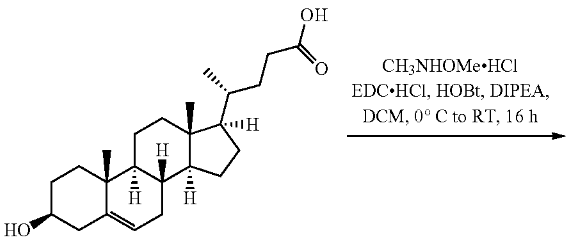

3β-hydroxy-5-cholenic acid

-continued

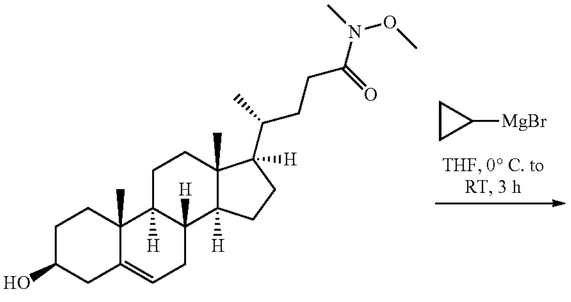

A

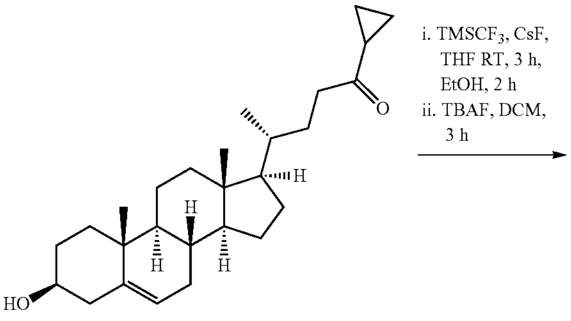

B

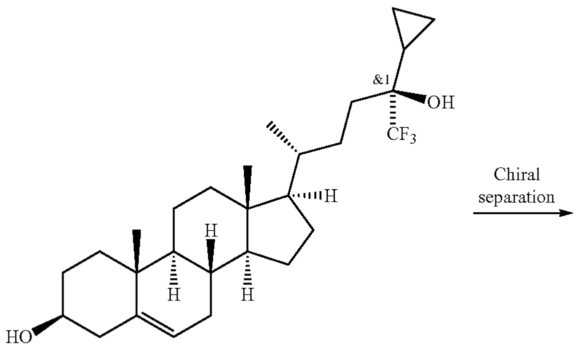

C

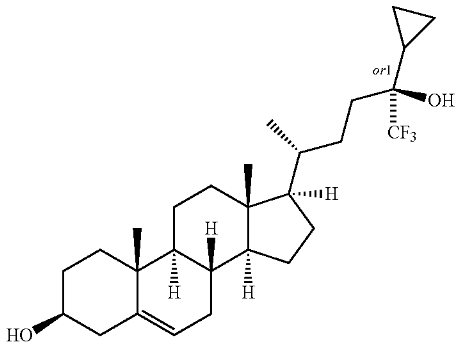

23

+

-continued

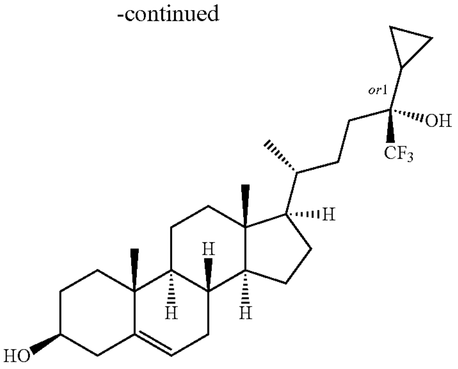

24

Compound A was synthesized according to the general procedure B as described in the example 19 and 20.

To a stirred solution of A (1.8 g, 4.31 mmol) in THF (36 mL) at 0° C. was added cyclopropyl magnesium bromide (1M, in THF, 54 mL, 30 vol) under nitrogen atmosphere. The resultant reaction mixture was stirred at room temperature for 3 h. Upon completion, the reaction mixture was quenched with saturated aqueous $NH_4C_1$ (200 mL) and extracted with ethyl acetate (60 mL×3). The combined organic layer was dried over sodium sulfate, filtered, concentrated in vacuo and purified by column chromatography over silica gel (100-200 mesh) with 0-10% gradient elution of ethyl acetate in hexanes to afford compound B as an off-white solid (1.2 g, 70.17%). LC-MS (ESI) m/z: 399 $(M+H)^+$.

To a stirred solution of B (0.5 g, 1.25 mmol) in dry THF (10 mL) were added CsF (38.1 mg, 0.251 mmol) and $TMSCF_3$ (535 mg, 3.76 mmol) sequentially at room temperature. The resulting mixture was stirred at room temperature for 3 h. Followed by EtOH (5 mL) was added and stirred at room temperature for 2 h. Upon completion, the reaction mixture was concentrated in vacuo, diluted with water (60 mL) and extracted with ethyl acetate (30 mL×3). The combined organic layer was dried over anhydrous sodium sulfate and concentrated in vacuo. The obtained crude compound was dissolved in DCM (10 mL), added TBAF (1M in THF, 0.5 mL) at 0° C. and allowed to stir at room temperature for 3 h. Upon completion, the reaction mixture was diluted with water (50 mL) and extracted with DCM (50 mL×2). The combined organic layer was dried over sodium sulfate, filtered, concentrated in vacuo and purified by column chromatography over silica gel (100-200 mesh) using 0-10% gradient elution of ethyl acetate in hexanes to afford compound C as an off-white solid (0.6 g, diastereomeric mixture). The diastereomers were separated by chiral prep HPLC (column: Chiralpak IG (4.6×250) 5 μm; mobile phase-A: 0.1% TFA in acetonitrile; mobile phase-B: 0.1% TFA in Methanol, elution 80/20; flow rate: 0.8 mL/min.) to afford compound 23 (peak-1, 125 mg, 21%) and compound 24 (peak-2, 75 mg, 13%) as an off-white solid.

23 (peak-1): ELSD-MS m/z:450 $(M-H_2O)^+$; $^1H$ NMR (400 MHz, DMSO-$d_6$) δ 5.28 (s, 1H), 5.27-5.25 (m, 1H), 4.60 (brs, 1H), 3.27-3.21 (m, 1H), 2.17-2.03 (m, 2H), 1.98-1.85 (m, 2H), 1.84-1.60 (m, 5H), 1.58-1.43 (m, 4H), 1.42-1.32 (m, 4H), 1.31-1.03 (m, 5H), 1.02-0.96 (m, 2H), 0.94 (s, 3H), 0.92-0.84 (m, 5H), 0.65 (s, 3H), 0.56-0.48 (m, 1H), 0.38-0.32 (m, 3H), $^{19}F$ NMR (376 MHz, DMSO-$d_6$): δ-78.71 (s, $CF_3$).

24 (peak-2): ELSD-MS m/z:450 $(M-H_2O)^+$; $^1H$ NMR (400 MHz, DMSO-$d_6$) δ 5.32 (s, 1H), 5.27-5.25 (m, 1H), 4.56 (brs, 1H), 3.29-3.22 (m, 1H), 2.18-2.04 (m, 2H), 1.98-1.85 (m, 2H), 1.82-1.62 (m, 4H), 1.61-1.44 (m, 5H), 1.43-1.22 (m, 6H), 1.18-0.96 (m, 4H), 0.94 (s, 3H), 0.91-0.84 (m, 5H), 0.65 (s, 3H), 0.52-0.45 (m, 1H), 0.41-0.31 (m, 3H), $^{19}F$ NMR (376 MHz, DMSO-$d_6$): δ-79.14 (s, $CF_3$).

Examples 25 and 26

Example 25: (3S,8S,9S,10R,13R,14S,17R)-17-((2R,5S)-5-cyclobutyl-6,6,6-trifluoro-5-hydroxyhexan-2-yl)-10,13-dimethyl-2,3,4,7,8,9,10,11,12,13,14,15,16,17-tetradecahydro-1H-cyclopenta[a]phenanthren-3-ol Example 26: (3S,8S,9S,10R,13R,14S,17R)-17-((2R,5R)-5-cyclobutyl-6,6,6-trifluoro-5-hydroxyhexan-2-yl)-10,13-dimethyl-2,3,4,7,8,9,10,11,12,13,14,15,16,17-tetradecahydro-1H-cyclopenta[a]phenanthren-3-ol

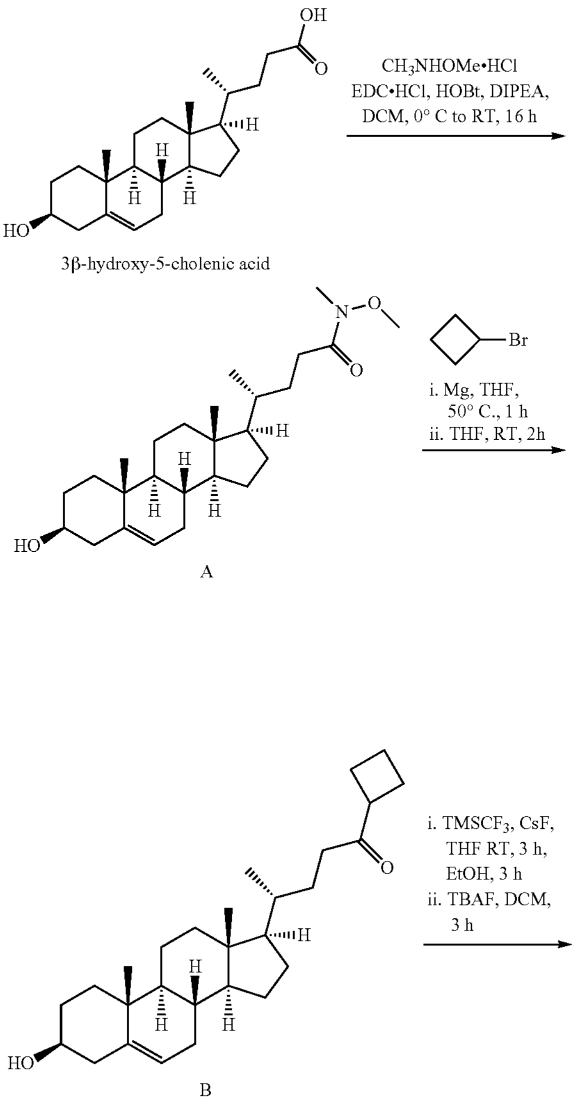

3β-hydroxy-5-cholenic acid

A

B

-continued

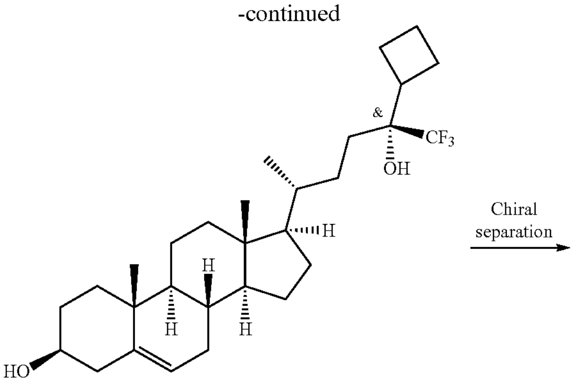

C

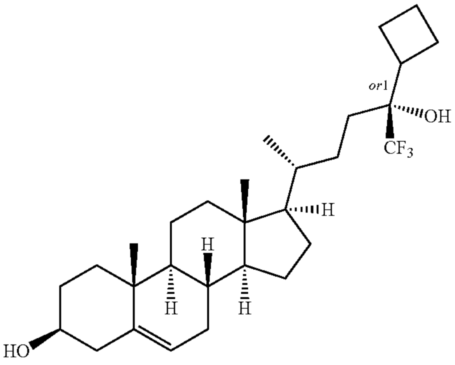

+

25

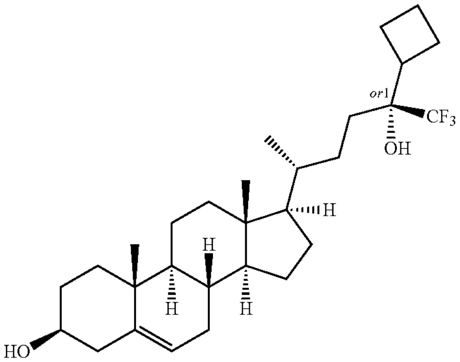

26

Compound A was synthesized according to the general procedure B as described in the example 19 and 20. To a stirred solution of Mg (104.76 mg, 4.31 mmol) in THF (3 mL) at 50° C. was added bromocyclobutane (290.94 mg, 2.16 mmol) drop wise under nitrogen atmosphere. The resultant reaction mixture was stirred at 50° C. for 1 h. The reaction mixture was allowed to ambient temperature and added to a solution of compound A (300 mg, 0.718 mmol) in THF (3 mL) slowly drop wise. The resultant reaction mixture was stirred at ambient temperature for 3 h. Upon completion, the reaction mixture was quenched with saturated aqueous $NH_4Cl$ (50 mL) and extracted with ethyl acetate (45 mL×2). The combined organic layer was dried over sodium sulfate, filtered, concentrated in vacuo, and purified by column chromatography over silica gel (100-200 mesh) with 0-10% gradient elution of ethyl acetate in hexanes to afford compound B as an off-white solid (250 mg, 84% yield). MS (APCI) m/z: 413 $[M+H]^+$.

To a stirred solution of B (350 mg, 0.848 mmol) in THF (6 mL) were added CsF (25.77 mg, 0.169 mmol) and $TMSCF_3$ (361.82 mg, 2.54 mmol) sequentially at room temperature. The resulting mixture was stirred at room temperature for 2 h. Followed by EtOH (6 mL) was added and the mixture was stirred at room temperature for 2 h. Upon completion, the reaction mixture was concentrated in vacuo, diluted with water (10 mL) and extracted with ethyl acetate (30 mL×2). The combined organic layer was dried over anhydrous sodium sulfate and concentrated in vacuo. The obtained crude compound was dissolved in DCM (6 mL), and to it was added 1M TBAF in THF (0.6 mL) at 0° C. and the mixture allowed to stir at room temperature for 3 h. Upon completion, the reaction mixture was quenched with water (50 mL) and extracted with DCM (50 mL×2). The combined organic layer was dried over sodium sulfate, filtered, concentrated in vacuo and purified by column chromatography over silica gel (100-200 mesh) with 0-8% gradient elution of ethyl acetate in hexanes to afford compound C as an off-white solid (110 mg, diastereomeric mixture). The diastereomers were separated by chiral preparative HPLC [column: Chiralpak IE,250*4.6 mm, Sum; mobile phase: hexanes/EtOH 95/05; flow rate: 1 mL/min. Retention time of peak-1 10.77 min. and peak-2 13.75 min.] to afford compound 25 (peak-1, 9 mg, 2%) and compound 26 (peak-2, 18.5 mg, 5%) as an off-white solid.

25 (peak-1): MASS (ESI) m/z: 465 $[M-H_2O]^+$; $^1H$ NMR (400 MHz, DMSO-$d_6$)) δ 5.51 (s, 1H), 5.26-5.25 (m, 1H) 4.58 (d, J=4.4 Hz, 1H), 3.30-3.22 (m, 1H), 2.63-2.55 (m, 1H), 2.24 2.00 (m, 4H), 1.98-1.85 (m, 2H), 1.82-1.62 (m, 6H), 1.61-1.29 (m, 11H), 1.28-0.96 (m, 8H), 0.94 (s, 3H), 0.87-0.85 (m, 4H), 0.64 (s, 3H), $^{19}F$ NMR (376 MHz, DMSO-$d_6$): δ-75.62 (s, $CF_3$).

26 (peak-2): MASS (ESI) m/z: 465 $[M-H_2O]^+$; $^1H$ NMR (400 MHz, DMSO-$d_6$) δ 5.52 (s, 1H), 5.26-5.25 (m, 1H) 4.58 (d, J=4.4 Hz, 1H), 3.32-3.22 (m, 1H), 2.63-2.55 (m, 1H), 2.24 1.85 (m, 6H), 1.83-1.44 (m, 11H), 1.41-1.16 (m, 7H), 1.15-0.96 (m, 6H), 0.94 (s, 3H), 0.88-0.86 (m, 4H), 0.63 (s, 3H), $^{19}F$ NMR (376 MHz, DMSO-$d_6$): δ-75.95 (s, $CF_3$).

Example 27: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-(2-methoxyethoxy)-N-methylpentanamide

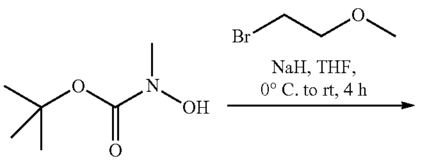

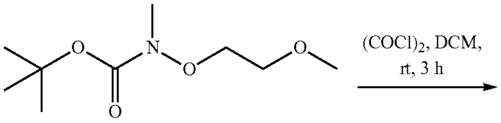

A

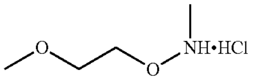

B

-continued

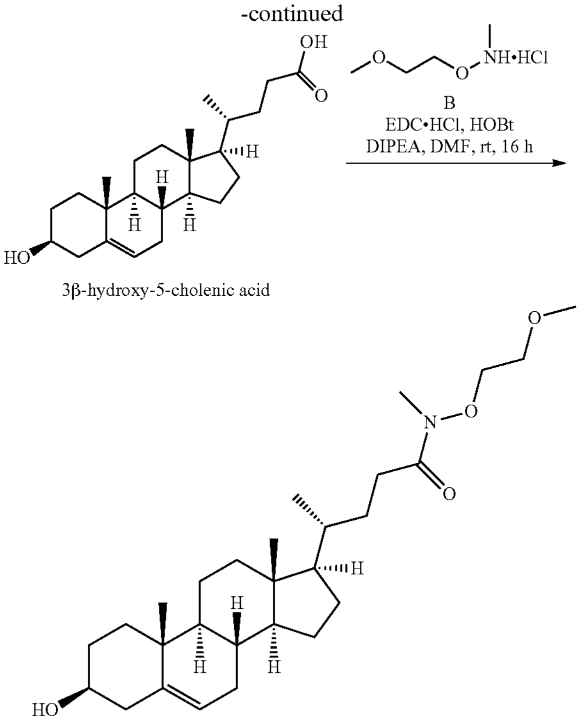

3β-hydroxy-5-cholenic acid

27

To a stirred solution of tert-butyl hydroxy(methyl)carbamate (700 mg, 4.76 mmol) in THF (10 mL) at 0° C. was added NaH (60% dispersion in mineral oil, 218 mg, 9.51 mmol). After stirring the reaction mixture for 30 min at room temperature was added 1-bromo-2-methoxyethane (793.3 mg, 5.71 mmol) and the resulting reaction mixture was stirred at room temperature for 4 h. Upon completion, the reaction mixture was quenched with ice-cooled water (20 mL) and concentrated in vacuo to obtain crude material that was purified by column chromatography over silica gel (100-200 mesh) with 0-10% gradient elution of ethyl acetate in hexane to afford compound A (300 mg, 32.9%) as pale-yellow liquid.

To a stirred solution of compound A (50 mg, 0.24 mmol) in MeOH (5 mL) at 0° C. was added oxalyl chloride (92.7 mg, 0.73 mmol) drop wise. The resulting reaction mixture was stirred at room temperature for 3 h. Upon completion, the reaction mixture was concentrated in vacuo to afford crude compound B (20 mg, crude) as yellow semi solid which was used for the next step without further purification.

Compound 27 was synthesized according to the general procedure B. 3β-hydroxy-5-cholenic acid (150 mg, 0.40 mmol), EDC-HCl (115 mg, 0.60 mmol), DIPEA (517 mg, 0.40 mmol), crude compound B (134.7 mg, 1.28 mmol), DMF (1.5 mL). The reaction time was 16 h. The obtained crude material was purified by column chromatography over silica gel (100-200 mesh) with 0-10% gradient elution of ethyl acetate in hexane to afford compound 27 (50 mg, 26.4%) as an off-white solid. LC-MS (ESI) m/z: 462 $[M+H]^+$; $^1H$ NMR (400 MHz, $CDCl_3$): δ 5.36-5.34 (m, 1H), 4.00 (t, J=4.4 Hz, 2H), 3.60 (t, J=2.8 Hz, 2H), 3.58-3.50 (m, 1H), 3.40 (s, 3H), 3.20 (s, 3H), 2.55-2.43 (m, 1H), 2.41-2.20 (m, 3H), 2.02-1.92 (m, 2H), 1.90-1.70 (m, 4H), 1.53-1.41 (m, 6H), 1.39-1.22 (m, 3H), 1.20-1.02 (m, 5H), 1.01 (s, 3H), 0.94-0.91 (m, 4H), 0.68 (s, 3H).

Example 28: (R)—N-(2-aminoethoxy)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methylpentanamide hydrochloride

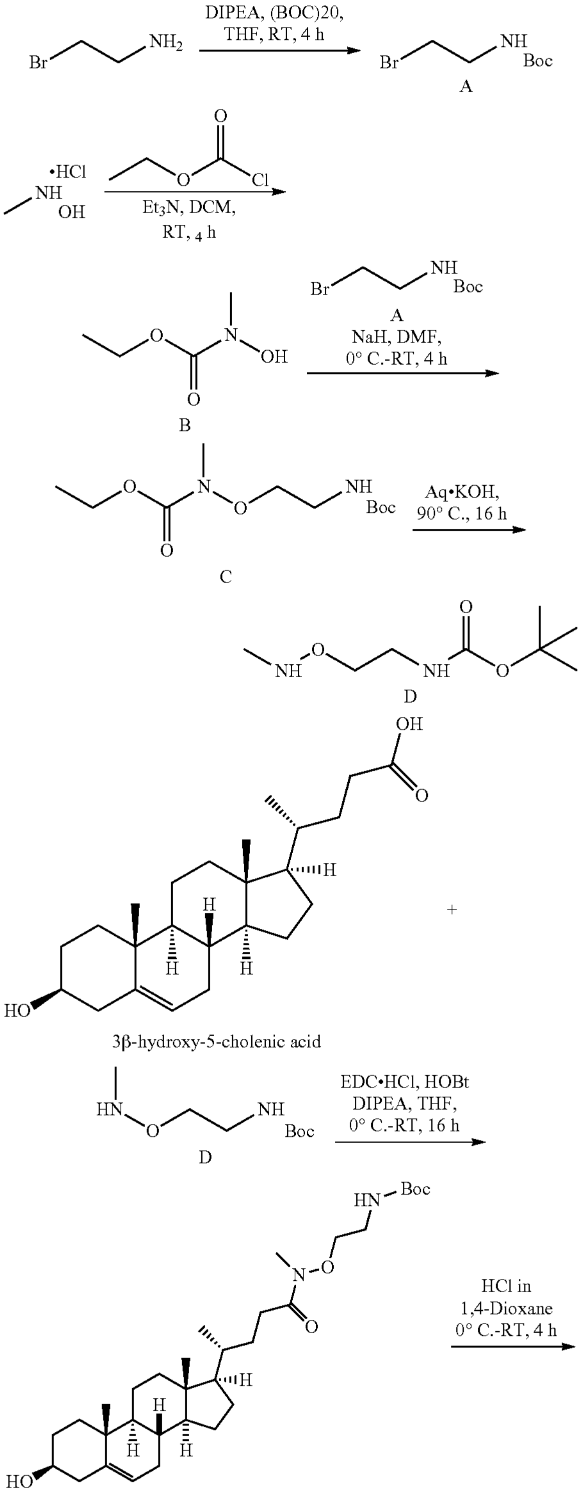

A

B

C

D

3β-hydroxy-5-cholenic acid

E

-continued

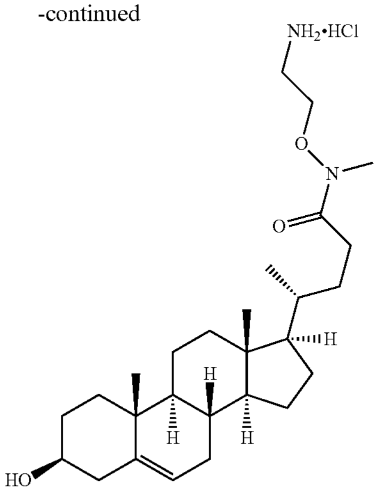

28

To a stirred solution of 2-bromanylethanamine (500 mg, 4.03 mmol) in THF (5 mL) was added di-tert-butyl dicarbonate (967.28 mg, 4.43 mmol) followed by DIPEA (1.04 g, 8.06 mmol) at room temperature and allowed to stir at room temperature for 4 h. Upon completion, the reaction mixture was diluted with water (100 mL) and extracted with ethyl acetate (50 mL×2). The combined organic layer was dried over sodium sulfate, filtered, and concentrated in vacuo to afford crude compound. The obtained crude material was purified by column chromatography over silica gel (60-120 mesh) with 0-10% gradient elution of ethyl acetate in hexanes to afford compound A as an off-white solid (421 mg, 46.2%).

To a stirred solution of N-methylhydroxylamine (1 g, 21.25 mmol) in THF (10 mL) at 0° C. were added $Et_3N$ (4.30 g, 42.50 mmol, 5.92 mL) and ethyl chloroformate (2.54 g, 23.38 mmol, 2.23 mL). The resultant reaction mixture was allowed to stir at room temperature for 16 h. Upon completion, the reaction mixture was diluted with water (100 mL) and extracted with DCM (50 mL×2). The combined organic layer was dried over sodium sulfate, filtered, and concentrated in vacuo to afford crude compound. The obtained crude material was purified by column chromatography over silica gel (60-120 mesh) with 0-10% gradient elution of ethyl acetate in hexanes to afford compound B (1.1 g, 43%) as a liquid compound.

To a stirred solution of compound B (640 mg, 5.37 mmol) in THF (5 mL) at 0° C. was added NaH (60% dispersion in mineral oil, 247.04 mg, 10.75 mmol) and stirred for 30 min at room temperature. Compound A (1.20 g, 5.37 mmol) in THF was added drop wise and the resulting reaction mixture was stirred at room temperature for 4 h. Upon completion, the reaction mixture was diluted with water (100 mL) and extracted with DCM (50 mL×2). The combined organic layer was dried over sodium sulfate, filtered, and concentrated in vacuo to afford crude compound. The obtained crude material was purified by column chromatography over silica gel (60-120 mesh) with 0-10% gradient elution of ethyl acetate in hexanes to afford compound C (210 mg, 14.9%) as a pale-yellow viscus compound.

To a stirred solution of compound C (826 mg, 3.15 mmol) in $H_2O$ (10 mL) at 0° C. was added aq. KOH (176 mg, 3.15 mmol, 15 mL). The resultant reaction mixture was stirred at room temperature for 18 h. The reaction mixture was diluted with water (100 mL) and extracted with DCM (20 mL×2). The combined organic layer was dried over sodium sulfate, filtered, and concentrated in vacuo to afford crude compound. The obtained crude material was purified by column chromatography over silica gel (60-120 mesh) with 0-30% gradient elution of ethyl acetate in hexanes to afford compound D (241 mg, 40.2%).

Compound E was synthesized according to the general procedure B. 3β-hydroxy-5-cholenic acid (100 mg, 0.26 mmol.), EDC.HCl (513 mg, 0.33 mmol.), HOBt (54 mg, 0.40 mmol.), DIPEA (172 mg, 1.33 mmol), compound D (76 mg, 0.4 mmol) and THE (1 mL). The reaction time was 4 h. The obtained crude material was purified by column chromatography over silica gel (60-120 mesh) with 0-50% gradient elution of ethyl acetate in hexanes to afford compound E (98 mg, 67.1%) as a gummy liquid. LC-MS (ESI) m/z: 547 $[M+H]^+$.

To a stirred solution of compound E (170 mg, 0.31 mmol) in 1,4-dioxane (1.7 mL) at 0° C. was added HCl solution (4 N HCl in 1,4-dioxane, 1.7 mL). The resultant reaction mixture was stirred at room temperature for 2 h. Upon completion, the reaction mixture was concentrated in vacuo to get crude material that was triturated with diethyl ether (2×5 mL) to afford the title compound 28 (40.3 mg, 29%) as an off-white solid. LC-MS (ESI) m/z: 447 $[M+H]^+$; $^1H$ NMR (400 MHz, DMSO-$d_6$): δ 8.05 (brs, 3H), 5.27-5.25 (m, 1H), 4.05-4.03 (m, 2H), 3.30-3.01 (m, 6H), 2.41-2.39 (m, 1H), 2.19-2.03 (m, 2H), 2.00-1.88 (m, 2H), 1.83-1.72 (m, 2H), 1.71-1.61 (m, 2H), 1.60-1.42 (m, 3H), 1.41-1.21 (m, 6H), 1.20-1.12 (m, 2H), 1.11-0.96 (m, 4H), 0.94 (s, 3H), 0.91-0.83 (m, 4H), 0.65 (s, 3H).

Example 29: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methyl-N-(3,3,3-trifluoropropoxy)pentanamide

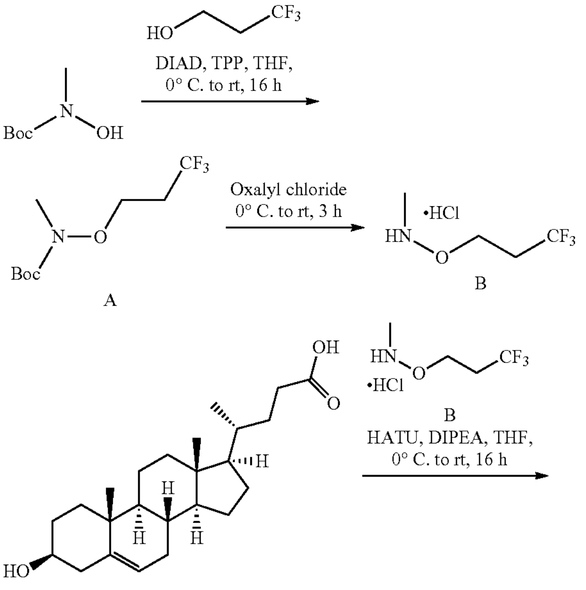

-continued

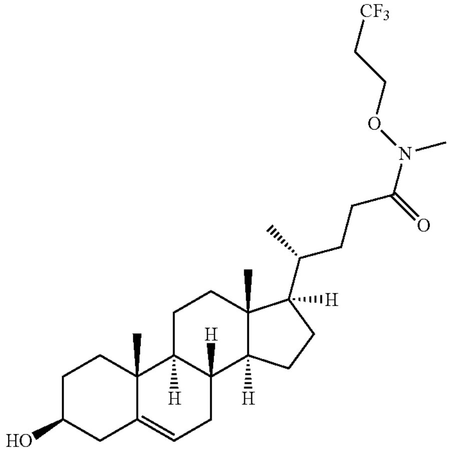

29

To a stirred solution of tert-butyl N-hydroxy-N-methylcarbamate (900 mg, 6.12 mmol) in THF (30 mL) were added triphenylphosphine (2.08 g, 7.95 mmol), DIAD (1.7 g, 9.78 mmol) and 3,3,3-tris(fluoranyl)propan-1-ol (837 mg, 7.35 mmol) sequentially at 0° C. The resulting reaction mixture was stirred at room temperature for 16 h. Upon completion, the reaction mixture was concentrated to obtain crude material that was purified by column chromatography over silica gel (100-200 mesh) with 0-3% gradient elution of MeOH in DCM to afford compound A (270 mg, 49%) as pale-yellow liquid.

To a stirred solution of 1,1-di(methyl)ethyl N-methyl-N-[3,3,3-tris(fluoranyl)propoxy]carbamate (150 mg, 0.61 mmol) in methanol (1.5 mL) was added oxalyl chloride (78.28 mg, 0.612 mmol) at 0° C. drop wise. The resulting reaction mixture was stirred at room temperature for 3 h. Upon completion, the reaction mixture was concentrated in vacuo to afford crude compound B (80 mg, crude) as yellow semi solid which was used for the next step without further purification.

Compound 29 was synthesized according to the general procedure A using 3β-hydroxy-5-cholenic acid (150 mg, 0.40 mmol), HATU (305 mg, 0.80 mmol), DIPEA (0.67 mL, 0.40 mmol), crude compound B (113 mg, 1.20 mmol), THF (1.5 mL). The reaction time was 16 h. The obtained crude material was purified by preparative HPLC [column: Agilent prep (50*30 mm)5μ; mobile phase A: 0.1% FA in water, mobile phase B: ACN, 0/40, 3/40, 15/85, 25/95; flow rate: 15 mL/min.] to afford compound 29 (23 mg, 11%) as an off-white solid. LC-MS (ESI) m/z: 500 $[M+H]^+$; $^1H$ NMR (400 MHz, DMSO-$d_6$): δ 5.37-5.34 (m, 1H), 4.06 (t, J=6.4 Hz, 2H), 3.56-3.45 (m, 1H), 3.19 (s, 3H), 2.55-2.41 (m, 3H), 2.33-2.20 (m, 3H), 2.02-1.92 (m, 2H), 1.90-1.80 (m, 3H), 1.50-1.41 (m, 8H), 1.38-1.22 (m, 3H), 1.20-1.02 (m, 5H), 1.01 (s, 3H) 0.94 0.91 (m, 4H), 0.68 (s, 3H). $^{19}F$ NMR (376 MHz, $CDCl_3$): δ 64.62 (s, $CF_3$).

Example 30: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-(3-hydroxypropoxy)-N-methylpentanamide

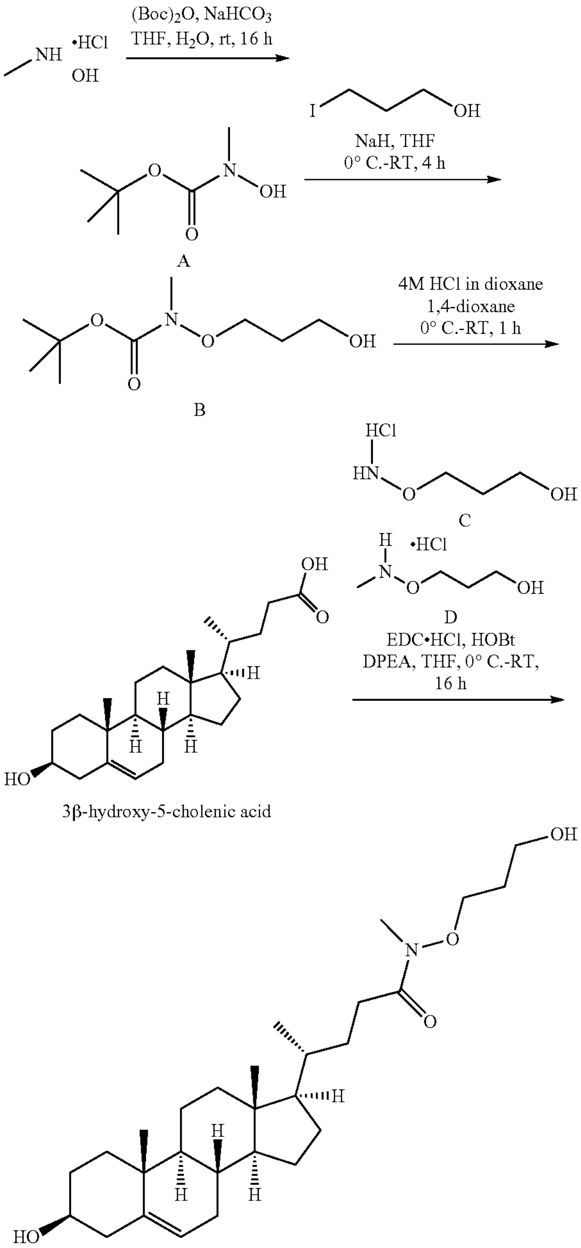

30

To the stirred solution of compound A (see Example 31)(400 mg, 2.72 mmol) in THF (10 mL) was added NaH (60% dispersion in mineral oil, 163 mg, 4.08 mmol) slowly at 0° C. under nitrogen atmosphere. After 20 min, was added 3-iodanylpropan-1-ol (1 g, 5.37 mmol) and the mixture was stirred at room temperature for 2 h. Upon completion, the reaction mixture was quenched with ice water and extracted with ethyl acetate. The combined organic layer was dried over anhydrous sodium sulfate, concentrated in vacuo to obtained crude compound B (300 mg) that was used for the next step without further purification.

To the stirred solution of compound B (280 mg, 1.31 mmol) in 1,4-dioxane (5 mL) was added HCl solution (4N in 1,4-dioxane, 8 mL) slowly at 0° C. The resultant reaction mixture was stirred at room temperature for 2 h then concentrated in vacuo to obtain crude compound C (120 mg) that was used without further purification.

Compound 30 was synthesized according to the general procedure B using 3β-hydroxy-5-cholenic acid (100 mg, 0.27 mmol), DIPEA (0.5 mL, 2.7 mmol), EDC.HCl (77 mg, 0.40 mmol), HOBt (43 mg, 0.32 mmol), crude compound C (121 mg, 0.86 mmol), and THF (5 mL). The crude compound was purified by column chromatography over 100-200 silica gel mesh by eluting 50% ethyl acetate in hexane to afford the title compound 30 (45 mg, 35%) as an off white solid. LC-MS (ESI) m/z: 462 $[M+H]^+$; $^1$H-NMR (400 MHz, $CDCl_3$): δ 5.36-5.34 (m, 1H), 4.00 (t, J=5.6 Hz, 2H), 3.81 (q, J=6.0 Hz, 2H), 3.58-3.48 (m, 1H), 3.30-3.13 (m, 3H), 2.50-2.19 (m, 4H), 2.04-1.74 (m, 8H), 1.53-1.41 (m, 7H), 1.39-1.02 (m, 9H), 1.03 (s, 3H), 0.97-0.90 (m, 4H), 0.69 (s, 3H).

Example 31: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-(3-methoxypropoxy)-N-methylpentanamide

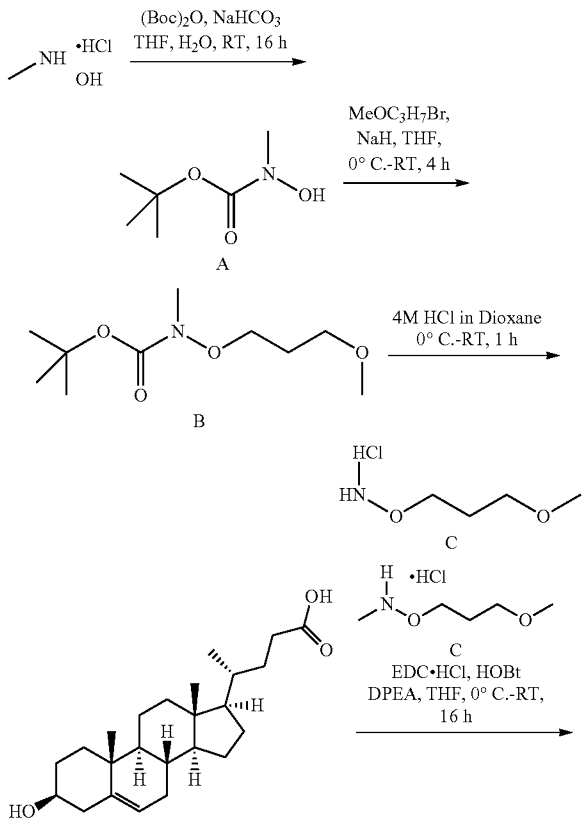

3β-hydroxy-5-cholenic acid

-continued

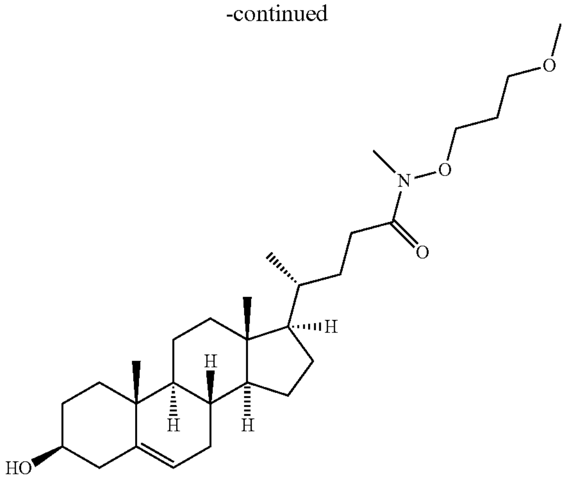

To the stirred solution of N-methyl-hydroxylamine hydrochloride (3 g, 35.19 mmol) in THF (60 mL) were added $NaHCO_3$ (6 g, 71.8 mmol), water (6 mL), and BOC anhydride (9.9 mL, 43.10 mmol) at 0° C. The reaction mixture was stirred at room temperature for 3 h. Upon completion, the reaction mixture was diluted with water and extracted with ethyl acetate. The organic layer dried over anhydrous sodium sulfate, concentrated in vacuo to obtain crude compound A. The crude compound was purified by column chromatography over 100-200 silica gel to obtain compound A (3.8 g, 74%) as colorless oil.

To the stirred solution of compound A (200 mg, 1.360 mmol) in THF (5 mL) was added NaH (60% dispersion in mineral oil, 62 mg, 2.72 mmol) slowly at 0° C. under nitrogen atmosphere and allowed to stir for 20 min at 0° C. Then was added 1-bromanyl-3-methoxy-propane (416 mg, 2.72 mmol) and the resultant mixture allowed to stir at room temperature for 4 h. Upon completion, the reaction mixture was quenched with ice water and extracted with ethyl acetate. The combined organic layer was dried over anhydrous sodium sulfate and concentrated in vacuo to obtain crude compound B (260 mg), which was used without further purification.

To the stirred solution of compound B (300 mg, 1.36 mmol) in 1,4-dioxane (5 mL) was added HCl solution (4M HCl in 1,4-dioxane, 3 mL) slowly at 0° C. The resultant reaction mixture was stirred at room temperature for 2 h. Upon completion, the reaction mixture was concentrated to obtain the crude compound C (150 mg) which was used for the next step without further purification.

Compound 31 was synthesized according to the general procedure B using 3β-hydroxy-5-cholenic acid (100 mg, 0.27 mmol), DIPEA (0.5 mL, 2.7 mmol), EDC.HCl (77 mg, 0.40 mmol), HOBt (43 mg, 0.32 mmol), crude compound C (132 mg, 0.86 mmol), and THE (5 mL). The crude compound was purified by column chromatography over 100-200 silica gel mesh with eluting 40% ethyl acetate in hexane to afford the compound 31 (42 mg, 33%) as an off white solid. LC-MS (ESI) m/z: 476 $[M+H]^+$; $^1$H-NMR (400 MHz, $CDCl_3$): δ 5.38-5.33 (m, 1H), 3.93 (t, J=6.4 Hz, 2H), 3.58-3.47 (m, 3H), 3.36 (s, 3H), 3.18 (s, 3H), 2.50-2.20 (m, 4H), 2.04-1.76 (m, 8H), 1.60-1.40 (m, 8H), 1.38-1.26 (m, 2H), 1.20-1.01 (m, 5H), 1.00 (s, 3H), 0.97-0.90 (m, 4H), 0.69 (s, 3H).

Example 32: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methyl-N-(4,4,4-trifluorobutoxy)pentanamide

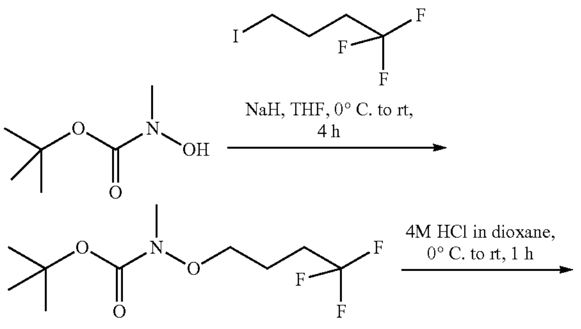

A

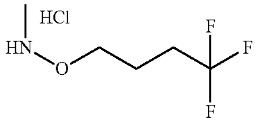

B

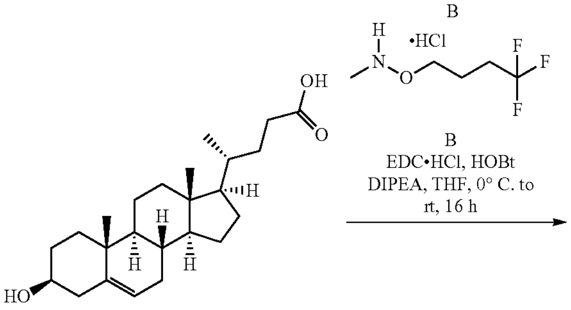

3β-hydroxy-5-cholenic acid

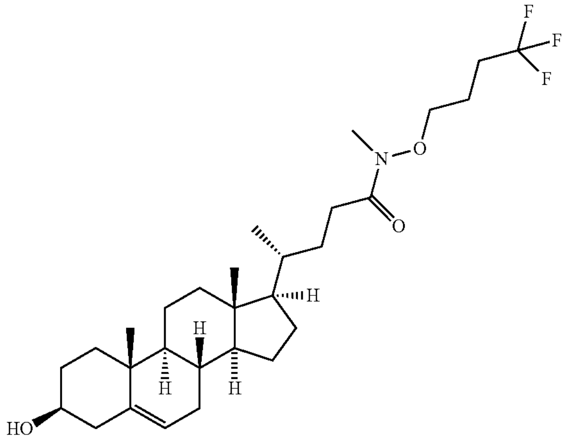

32

To a stirred solution of 1,1-di(methyl)ethyl N-methyl-N-oxidanyl-carbamate (400 mg, 2.72 mmol) in THF (8 mL) at 0° C. was added NaH (60% dispersion in mineral oil, 62.48 mg, 2.72 mmol) portion wise and the heterogeneous mixture was stirred at 0° C. for 10 minutes. To this was added 1,1,1-trifluoro-4-iodobutane (646.83 mg, 2.72 mmol) and the reaction mixture was allowed to stir at room temperature for 4 h. Upon completion, the reaction mixture was diluted with water (10 mL) and extracted with ethyl acetate (30 mL×3). The combined organic layer was dried over anhydrous sodium sulfate and concentrated in vacuo. The obtained crude compound was and purified by column chromatography over silica gel (60-120 mesh) using 0-5% gradient elution of ethyl acetate in hexanes to afford compound A (320 mg, 45%) as a colorless liquid.

To a stirred solution of compound A (700 mg, 2.72 mmol) in 1,4-dioxane (2 mL) at 0° C. was added HCl solution (4M HCl in 1,4-dioxane, 2.72 mmol, 5 mL) drop wise. The resulting reaction mixture was stirred at room temperature for 1 h. Upon completion, the reaction mixture was concentrated in vacuo to afford crude compound B (500 mg, crude) as yellow semi solid which was used for the next step without further purification.

Compound 32 was synthesized according to the general procedure B using 3β-hydroxy-5-cholenic acid (100 mg, 0.26 mmol), crude compound B (41.95 mg, 0.26 mmol), EDC HCl (76.77 mg, 0.40 mmol), HOBt (36.07 mg, 0.26 mmol), and THF (1 mL). The reaction time was 4 h. The obtained crude material was purified by column chromatography over silica gel (100-200 mesh) with 0-5% gradient elution of MeOH in DCM to afford compound 32 (59 mg, 43%) as an off white solid. LC-MS (ESI) m/z: 514.4 $[M+H]^+$; $^1H$ NMR (400 MHz, DMSO-$d_6$): 5.27-5.25 (m, 1H), 4.61 (d, J=4.4 Hz, 1H), 3.91 (t, J=6 Hz, 2H), 3.28-3.21 (m, 1H), 3.08 (s, 3H), 2.43-2.32 (m, 3H), 2.30-2.21 (m, 1H), 2.20-1.85 (m, 5H), 1.83-1.71 (m, 4H), 1.70-1.60 (m, 2H), 1.60-1.32 (m, 7H), 1.31-0.98 (m, 7H), 0.97-0.82 (m, 7H), 0.64 (s, 3H).

Example 33: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(isoxazolidin-2-yl)pentan-1-one

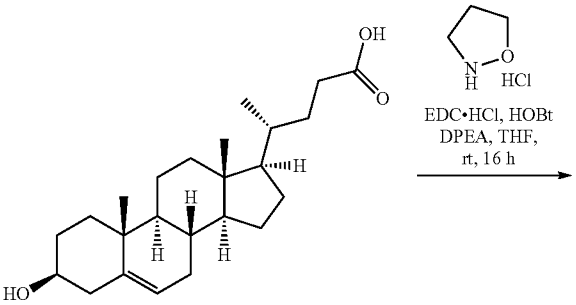

3β-hydroxy-5-cholenic acid

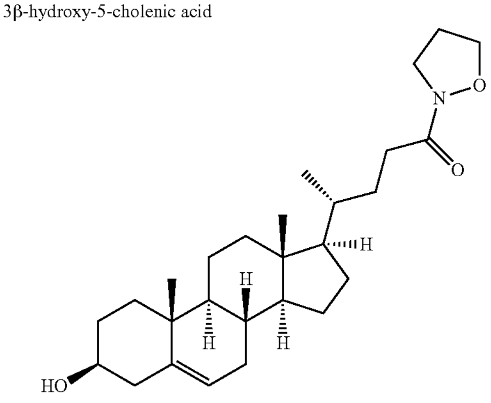

33

Compound 33 was synthesized according to the general procedure B using 3β-hydroxy-5-cholenic acid (150 mg, 0.40 mmol), EDC.HCl (115 mg, 0.60 mmol), HOBt (59 mg, 0.44 mmol), DIPEA (0.21 mL, 1.2 mmol), isoxazolidine hydrochloride (48 mg, 0.44 mmol) and THF (5 mL). The crude material was purified by column chromatography over silica gel (100-200 mesh) with 0-50% gradient elution of ethyl acetate in hexanes to afford the title compound 33 (40 mg, 23%) as an off-white solid. ELSD-MS (ESI) m/z: 429.9 $[M+H]^+$; $^1H$ NMR (400 MHz, $CDCl_3$) δ 5.35 5.34 (m, 1H), 3.95 (t, J=6.8 Hz, 2H), 3.70 (t, J=7.2 Hz, 2H), 3.55-3.49 (m, 1H), 2.50-2.40 (m, 1H), 2.39-2.19 (m, 5H), 2.04-1.93 (m, 2H), 1.92-1.74 (m, 4H), 1.63-1.41 (m, 8H), 1.39-1.22 (m, 2H), 1.21-1.02 (m, 5H), 1.01 (s, 3H), 0.98-0.88 (m, 4H), 0.68 (s, 3H).

Example 34: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(1,2-oxazinan-2-yl)pentan-1-one

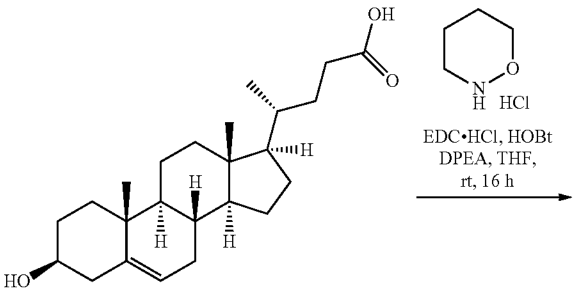

3β-hydroxy-5-cholenic acid

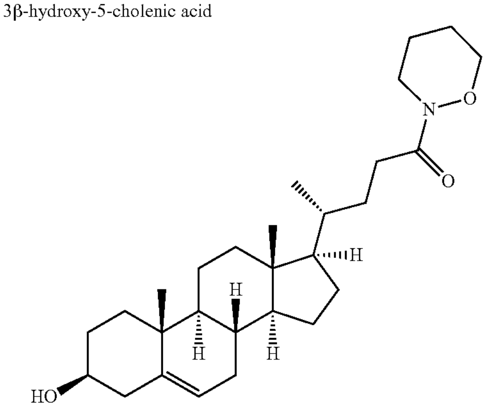

34

Compound 34 was synthesized according to the general procedure B using 3β-hydroxy-5-cholenic acid (150 mg, 0.40 mmol), EDC.HCl (115 mg, 0.60 mmol), HOBt (59 mg, 0.44 mmol), DIPEA (0.21 mL, 1.2 mmol), 1,2-oxazinane hydrochloride (54 mg, 0.44 mmol), and THE (5 mL). The crude material was purified by column chromatography over silica gel (100-200 mesh) with 0-50% gradient elution of ethyl acetate in hexanes to afford the title compound 34 (65 mg, 36%) as an off-white solid. ELSD-MS (ESI) m/z: 443.9 $[M+H]^+$; $^1H$ NMR (400 MHz, $CDCl_3$) δ 5.36-5.34 (m, 1H), 3.96 (t, J=4.8 Hz, 2H), 3.82-3.75 (m, 2H), 3.53-3.51 (m, 1H), 2.49-2.39 (m, 1H), 2.38-2.20 (m, 3H), 2.03-1.92 (m, 2H), 1.92-1.77 (m, 5H), 1.76-1.62 (m, 4H), 1.61-1.40 (m, 8H), 1.39-1.22 (m, 2H), 1.21-1.02 (m, 4H), 1.01 (s, 3H), 0.99-0.89 (m, 4H), 0.68 (s, 3H).

Example 35: (S)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethyl 2-(dimethylamino)-2-oxoacetate

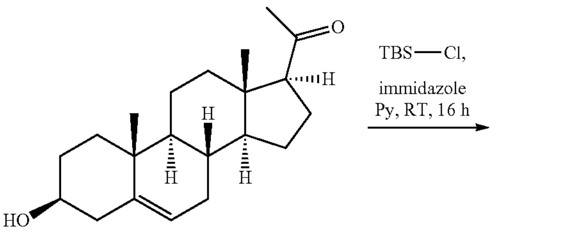

Pregnenolone

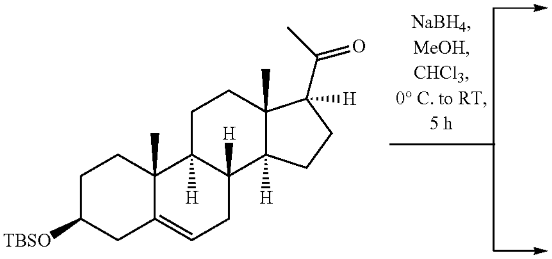

A

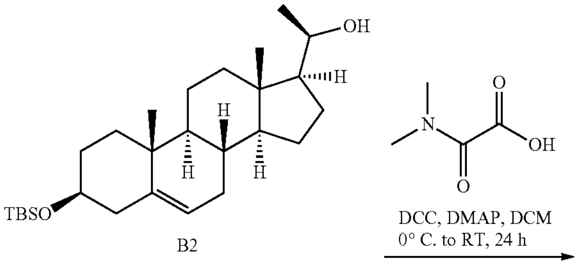

B2

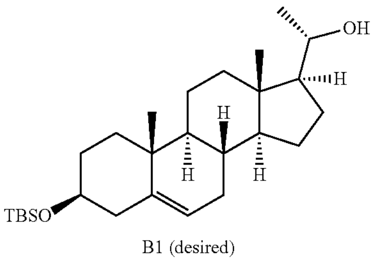

B1 (desired)

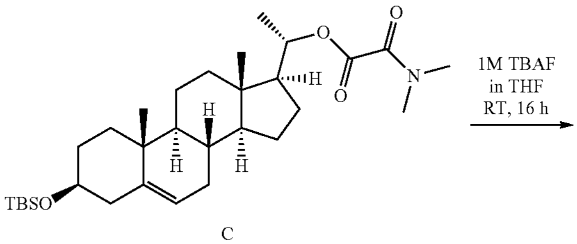

C

-continued

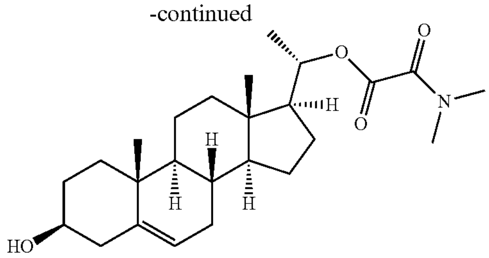

35

To a stirred solution of pregnenolone (5 g, 15.8 mmol, 1 eq.) in DMF (70 mL) were added imidazole (13.98 g, 205.35 mmol, 13 eq.), pyridine (5.62 g, 71.10 mmol, 5.75 mL, 4.5 eq.) and TBDMS-Cl (7.86 g, 52.14 mmol, 9.70 mL, 3.3 eq.) at 0° C. The resultant mixture was stirred at room temperature for 16 h. Upon completion, reaction mass was quenched with ice water (20 mL) and solid generated was filtered and dried in vacuo to afford compound A as an off-white solid (6.5 g, 95.5%).

To a stirred solution of compound A (15 g, 34.82 mmol) in mixture of methanol (40 mL) and chloroform (100 mL) was added sodium borohydride (2.63 g, 69.65 mmol, 2.45 mL) portion wise over a period of 10 min at 0° C. The resultant mixture was allowed to room temperature and stirred for 5 h. Upon completion, reaction mass was quenched with ice water (70 mL) and extracted with DCM (2×100 mL). The combined organic layer was washed with water (100 mL) followed by brine (75 mL), dried over sodium sulfate, filtered, and concentrated to obtain crude compound. The crude compound was purified by column chromatography using 100-200 silica gel with a gradient elution of 0-20% ethyl acetate in pet ether to obtain compound B2 (diastereomer-I, 5 g, 33%) and compound B1 (diastereomer-II, 850 mg, 5.6%) as white solids.

To a stirred solution of compound B1 (400.00 mg, 0.924 mmol) and 2-[di(methyl)amino]-2-oxidanylidene-acetic acid (216.48 mg, 1.85 mmol.) in DCM (10 mL) was added N,N'-dicyclohexylcarbodiimide (381.43 mg, 1.85 mmol), followed by 4-dimethylaminopyridine (11.2 mg, 0.0916 mmol) at 0° C. and the resultant mixture was allowed to stir at room temperature for 24 h. Upon completion, the reaction mixture was diluted with DCM (25 mL) and filtered through a pad of Celite. The filtrate was washed with water (10 mL), brine (5 mL), dried over anhydrous sodium sulfate, filtered, and concentrated to obtained crude compound. The crude compound was purified by column chromatography over silica gel (100 200 mesh) with a gradient elution of 0-15% ethyl acetate in hexane to afford compound C as a gummy liquid (250 mg, 50.8%).

To a stirred solution of compound C (250 mg, 0.47 mmol) in THF (5 mL) was added tetrabutylammonium fluoride (1.2 mL (1 M in THF), 1.22 mmol, 2.6 eq.) The resultant mixture was stirred at room temperature for 16 h. Upon completion, the reaction mixture was quenched with water (10 mL) and extracted with ethyl acetate (2×10 mL). The combined organic layer was washed with brine (5 mL), dried over anhydrous sodium sulfate, filtered, and concentrated in vacuo to obtain crude compound. The compound was purified by column chromatography over silica gel (100-200 mesh) with a gradient elution of 0-25% ethyl acetate in pet ether to afford the title compound 35 as an off-white solid (50 mg, 24.6%). $^1H$ NMR (400 MHz, $CDCl_3$): δ 5.35 (brt, 1H), 5.16-5.09 (m, 1H), 3.55-3.49 (m, 1H), 3.00 (s 3H), 2.97 (s, 3H), 2.35-2.19 (m, 2H), 2.03-1.83 (m, 5H), 1.67-1.43 (m, 8H), 1.35 (d, J=6.4 Hz, 3H), 1.28-1.04 (m, 5H), 1.03 (s, 3H), 0.99-0.92 (m, 1H), 0.73 (s, 3H).

Example 36: (R)—N-cyclopropyl-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methoxypentanamide

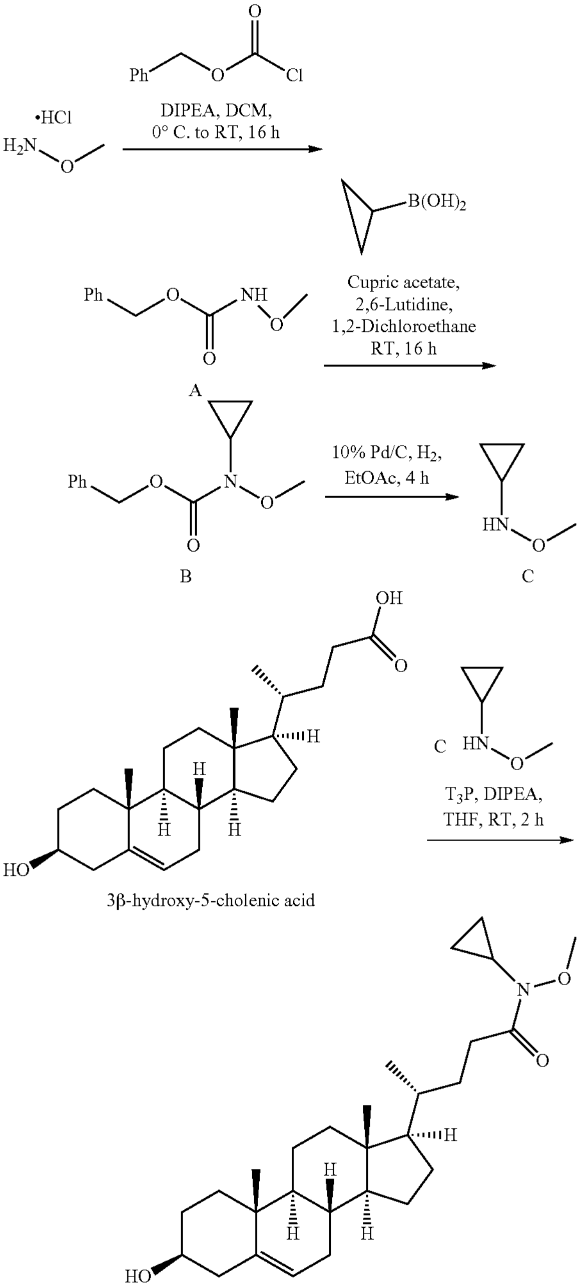

36

To a stirred solution of O-methylhydroxylamine hydrochloride (3.55 g, 42.5 mmol) in DCM (20 mL) at 0° C. were added benzyl chloroformate (7.25 g, 42.5 mmol) and DIPEA (13.7 g, 106 mmol). The resulting mixture was stirred at room temperature for 16 h. Upon completion, the reaction mixture was concentrated in vacuo, diluted with water (100 mL), and extracted with ethyl acetate (30 mL×3). The combined organic layer was dried over anhydrous sodium sulfate and concentrated in vacuo. The obtained crude compound was purified by column chromatography over silica gel (60-120 mesh) using 0-30% gradient elution of ethyl acetate in hexanes to afford compound A (1.6 g, 20%) as an off-white solid.

To a stirred solution of compound A (1 g, 5.52 mmol) in EDC (20 mL) at 0° C. were added cyclopropylboronic acid (569 mg, 6.62 mmol), copper (II) diacetate (501 mg, 2.76 mmol), and 2,6-dimethylpyridine (1.77 g, 16.6 mmol). The resulting mixture was stirred at room temperature for 16 h. Upon completion, the reaction mixture was concentrated in vacuo, diluted with water (100 mL), and extracted with ethyl acetate (30 mL×3). The combined organic layer was dried over anhydrous sodium sulfate and concentrated in vacuo. The obtained crude compound was purified by column chromatography over silica gel (60-120 mesh) with 0-10% gradient elution of ethyl acetate in hexanes to afford compound B (440 mg, 36%) as a color less liquid.

To a stirred solution of compound B (0.3 g, 1.5 eq, 1.36 mmol) in ethyl acetate (3 mL, 30.4 mmol) was added 10% Pd/C (30 mg, 0.282 mmol) at room temperature. The resulting reaction mixture was degassed with $H_2$ gas and stirred at room temperature for 4 h under $H_2$ atmosphere (balloon). Upon completion, the reaction mixture was filtered through a Celite pad, washed with ethyl acetate (3 mL), and concentrated in vacuo to afford crude compound C (123 mg, crude), which was used next step without further purification.

Compound 36 was synthesized according to the general procedure A using 3β-hydroxy-5-cholenic acid (100 mg, 0.26 mmol), T3P (255 mg, 50% w/w in ethyl acetate, 0.80 mmol), DIPEA (0.34 mL, 1.95 mmol), crude compound C (46 mg, 0.53 mmol), and THE (1 mL). The reaction time was 2 h. The obtained crude material was purified by preparative HPLC [column: Agilent prep (50*30 mm)$_5$μ; mobile phase A: 0.1% FA in water, mobile phase B: ACN, 0/40, 3/40, 15/85, 25/95; flow rate: 15 mL/min.] to afford compound 36 (5.6 mg, 4.7%) as an off-white solid. LC-MS (ESI) m/z: 444 $[M+H]^+$; $^1H$ NMR (400 MHz, DMSO-$d_6$): δ 5.27-5.25 (m, 1H), 4.58 (d, J=4.4 Hz, 1H), 3.63 (s, 3H), 3.28-3.22 (m, 1H), 2.90-2.87 (m, 1H), 2.41-2.21 (m, 2H), 2.18-2.08 (m, 2H) 1.98-1.87 (m, 2H), 1.84-1.73 (m, 2H), 1.71-1.60 (m, 2H), 1.58-1.43 (m, 2H), 1.42-1.15 (m, 7H), 1.14-0.96 (m, 4H), 0.93 (s, 3H), 0.91-0.83 (m, 6H), 0.78-0.73 (m, 2H), 0.64 (s, 3H).

Example 37: (R)—N-cyclopropoxy-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methylpentanamide

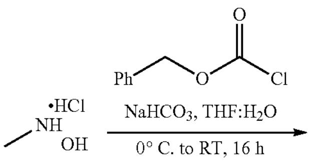

-continued

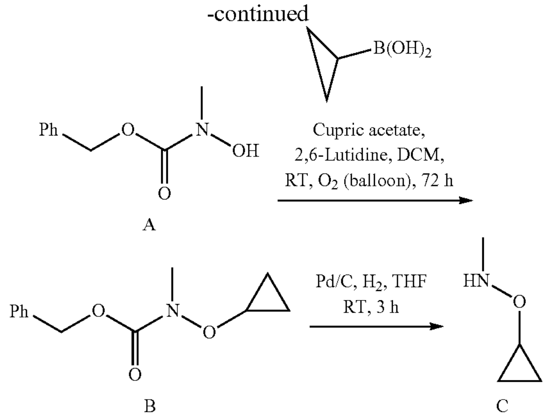

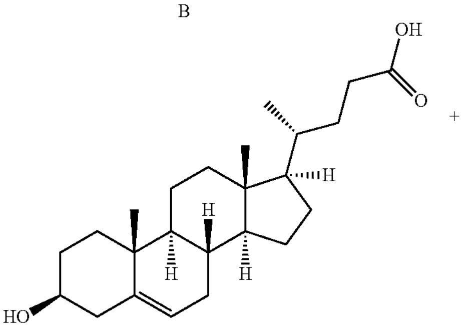

3β-hydroxy-5-cholenic acid

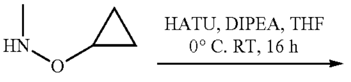

C

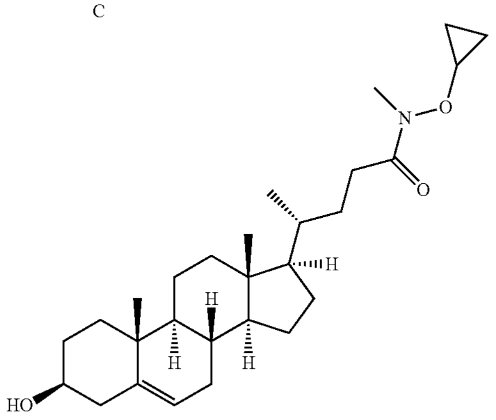

37

To a stirred solution of N-methyl hydroxylamine hydrochloride (2 g, 23.9 mmol) in THF (30 mL) at room temperature were added $NaHCO_3$ (4.02 g, 47.9 mmol) and water (4 mL, 222 mmol) followed by benzyl chloroformate (4.09 g, 23.9 mmol). The resultant reaction mixture was allowed to stir for 16 h at room temperature. Upon completion, the reaction was quenched with water and extracted with ethyl acetate (20 mL×2). The combined organic layer was washed with brine (20 mL), dried over anhydrous sodium sulfate, and concentrated in vacuo to afford crude compound. The crude compound was purified by column chromatography over 100-200 silica gel mesh by eluting with 10% ethyl acetate in hexane. The pure fractions were concentrated in vacuo to afford compound A (2.7 g, 62%) as a colorless liquid.

To a stirred solution of compound A (2 g, 11 mmol) and cyclopropylboronic acid (1.42 g, 16.6 mmol) in anhydrous DCM (50 mL, 221 mmol) was added dried 4A molecular sieves at room temperature and purged with 02 for 15 min. Then, were added 2,6-Lutidine (3.55 g, 33.1 mmol) and cupric acetate (677 mg, 5.52 mmol) and the resulting mixture was stirred for 72 h under 02 atmosphere. Upon completion, the reaction was quenched with water and extracted with DCM (50 mL×2). The combined organic layer was washed with brine (10 mL), dried over anhydrous sodium sulfate and concentrated in vacuo to obtain the crude compound. The crude compound was purified by column chromatography over 100-200 silica gel mesh by eluting with 3% ethyl acetate in hexane. The pure fractions were concentrated in vacuo to afford compound B (0.3 g, 12%) as an off-white solid.

To a stirred solution of compound B (0.5 g, 2.26 mmol) in THF (5 mL) at room temperature was added 10% Pd on carbon (50 mg). The reaction mixture was degassed with hydrogen gas and stirred under hydrogen pressure (balloon) at room temperature for 2 h. Upon completion, the reaction mixture was filtered through a pad of celite, washed with THF (5 mL). The filtrate was used for the next step without further concentration and purification.

Compound 37 was synthesized according to the general procedure A using 3β-hydroxy-5-cholenic acid (0.1 g, 0.267 mol), DIPEA (233 μL, 1.33 mmol), HATU (203 mg, 0.534 mmol) crude compound C (69.8 mg, 0.801 mmol), and THF (5 mL). The crude compound was purified by preparative HPLC [Column: Gemini C18 2.0*50 mm, 3 μm; mobile phase-A 0.01% FA in water, mobile phase-B: ACN; flow: 0.6 ml/min; program (Time/% B): 0.01/5, 2.0/90, 3.50/90, 3.51/5] to afford the title compound 37 (50 mg, 42%) as an off white solid. LC-MS (ESI) m/z: 444 $[M+H]^+$; $^1$H-NMR (400 MHz, $CDCl_3$): δ 5.35 (t, J=3.2 Hz, 1H), 3.79-3.72 (m, 1H), 3.59 3.47 (m, 1H), 3.25 (s, 3H), 2.50-2.41 (m, 1H), 2.39-2.21 (m, 3H), 2.05-1.75 (m, 6H), 1.56-1.40 (m, 7H), 1.37-1.25 (m, 2H), 1.20-1.02 (m, 5H), 1.01 (s, 3H), 0.98-0.89 (m, 4H), 0.85-0.81 (m, 2H), 0.68 (s, 3H), 0.67-0.64 (m, 2H).

Example 38: (R)—N-cyclobutyl-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methoxypentanamide

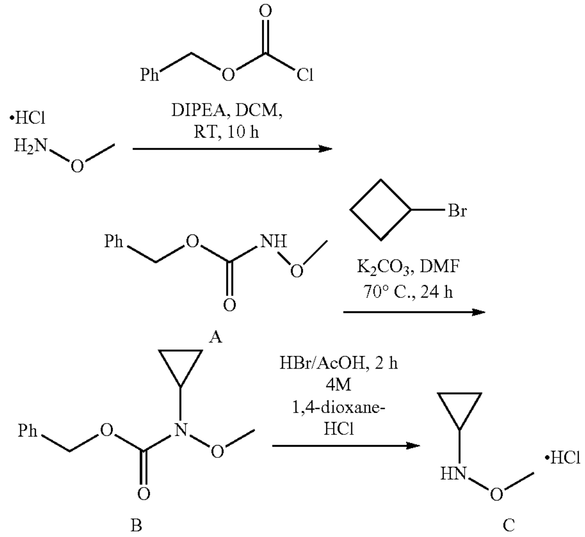

-continued

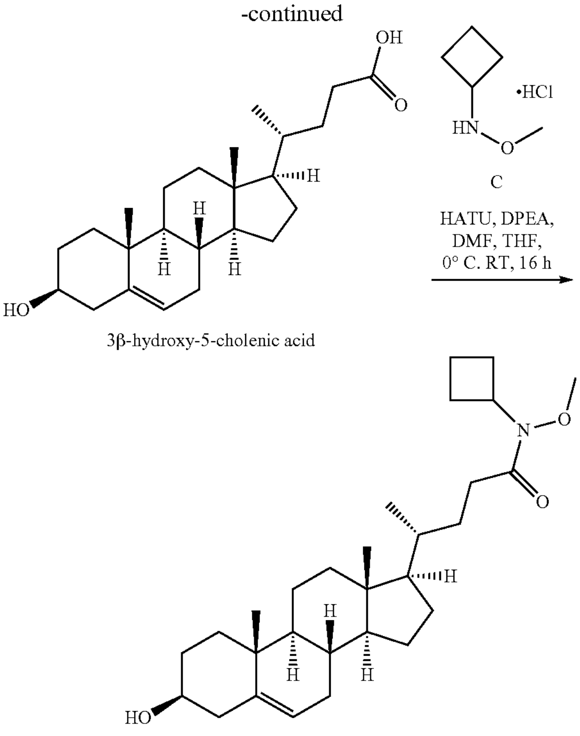

3β-hydroxy-5-cholenic acid

38

To a stirred solution of O-methylhydroxylamine hydrochloride (500 mg, 5.99 mmol) in DCM (5 mL) at 0° C. were added N, N-Diisopropylethylamine (1.93 g, 14.97 mmol, 2.61 mL) and benzyl chloroformate (1.02 g, 5.99 mmol). The resulting reaction mixture was stirred at room temperature for 10 h. Upon completion, the reaction mixture was diluted with DCM (20 mL) and washed with $NaHCO_3$ solution (30 mL×3). The combined organic layer was dried over sodium sulfate, filtered, concentrated in vacuo and purified by column chromatography over silica gel (100-200 mesh) with 0-50% gradient elution of ethyl acetate in hexanes to afford compound A as a brown liquid (400 mg, 36%).

To a stirred solution of compound A (200 mg, 1.10 mmol) in DMF (8 mL) at ambient temperature were added $K_2CO_3$ (229 mg, 1.66 mmol) and bromocyclobutane (670 mg, 4.97 mmol). The resultant reaction mixture was stirred at 70° C. for 24 h. Upon completion, the reaction mixture was diluted with water and extracted with DCM (30 mL×3). The combined organic layer was dried over sodium sulfate, filtered, concentrated in vacuo, and purified by column chromatography over silica gel (100-200 mesh) with 0-30% gradient elution of ethyl acetate in hexanes to afford compound B as a pale brown liquid (80 mg, 30%).

A mixture of compound B (80 mg, 0.34 mmol) and HBr solution (33 wt % in acetic acid, 1 mL, 0.34 mmol) was stirred at room temperature for 2 h. Upon completion, the reaction mixture was quenched with saturated $NaHCO_3$ solution (20 mL) and extracted with DCM (30 mL×3). The combined organic layer was dried over sodium sulfate, filtered, treated with 4M HCl in 1,4-dioxane and concentrated in vacuo. The obtained residue was triturated with n-pentane to afford compound C as an off-white solid (30 mg, 87%). The crude compound was directly used for the next step without further purification.

Compound 38 was synthesized according to the general procedure A using 3β-hydroxy-5-cholenic acid (150 mg, 0.40 mmol), HATU (304 mg, 0.80 mmol), DIPEA (258 mg, 2.00 mmol, 0.348 mL), compound C (66 mg, 0.480 mmol) and DMF (4 mL). The obtained crude material was purified by column chromatography over silica gel (100-200 mesh) with 0-50% gradient elution of ethyl acetate in hexanes to afford the title compound 38 as an off-white solid (50 mg, 25%). ELSD-MS (ESI) m/z: 458.4 $[M+H]^+$; $^1H$ NMR (400 MHz, $CDCl_3$): δ 5.37-5.35 (m, 1H), 4.75 (brs, 1H), 3.74 (s, 3H), 3.53-3.49 (m, 1H), 2.47-2.37 (m, 1H), 2.36-2.21 (m, 5H), 2.20-2.11 (m, 2H), 2.03-1.93 (m, 2H), 1.91-1.76 (m, 4H), 1.74-1.61 (m, 2H), 1.56-1.40 (m, 8H), 1.39-1.24 (m, 2H), 1.22-1.02 (m, 5H), 1.01 (s, 3H), 0.99-0.84 (m, 4H), 0.68 (s, 3H).

Example 39: (R)—N-cyclobutoxy-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methylpentanamide

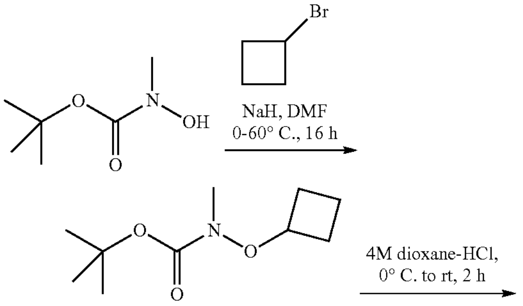

A

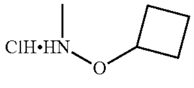

B

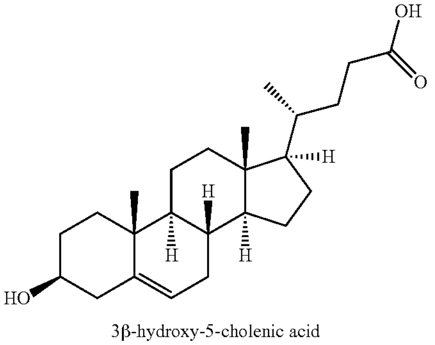

3β-hydroxy-5-cholenic acid

+

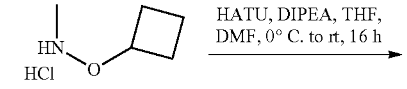

B

-continued

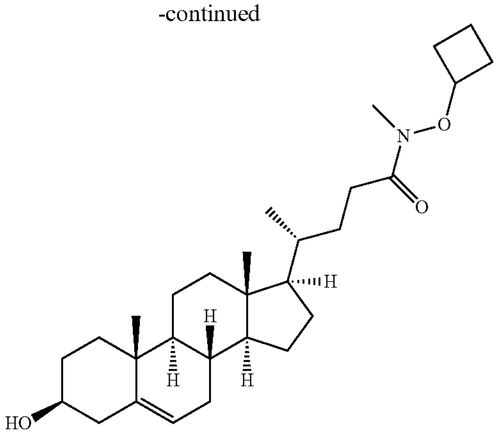

39

To a stirred solution of tert-butyl hydroxy(methyl)carbamate (see Example 14)(200 mg, 1.36 mmol) in DMF (10 mL) at 0° C. were added sodium hydride (60% dispersion in paraffin oil, 55 mg, 1.36 mmol, 1 eq.) and bromocyclobutane (183.46 mg, 1.36 mmol). The resultant reaction mixture was stirred at 60° C. for 16 h. Upon completion, reaction mixture was quenched with ice water (10 mL) and extracted with ethyl acetate (3x20 mL). The combined organic layer was dried over sodium sulfate and concentrated in vacuo to afford crude compound A as a pale-yellow gummy liquid (80 mg, 29% yield.

To a stirred solution of crude compound A (100 mg, 0.496 mmol) in 1,4-dioxane (5 mL) at 0° C. was added HCl solution (4M in 1,4-dioxane, 5 mL). The resultant reaction mixture was stirred at ambient temperature for 2 h. Upon completion, reaction mixture was concentrated, and triturated with n-pentane to get compound B as an off white solid (35 mg, 70% yield).

Compound 39 was synthesized according to the general procedure A using 3β-hydroxy-5-cholenic acid (150 mg, 0.400 mmol), crude compound B (66 mg, 0.480 mmol) in DMF (3 mL), N,N-Diisopropylethylamine (155 mg, 1.20 mmol, 209.27 μL), HATU (305 mg, 0.800 mmol) and THF (5 mL). The reaction time was 16 h. The obtained crude was purified by column chromatography over silica gel (100-200 mesh) by gradient elution of 0-50% of ethyl acetate in hexane to obtain the title compound 39 as an off white solid (25 mg, 13%). $^1H$ NMR (400 MHz, $CDCl_3$): δ 5.35 (d, J=5.2 Hz, 1H), 4.38-4.30 (m, 1H), 3.54-3.51 (m, 1H), 3.18 (s, 3H), 2.50-2.40 (m, 1H), 2.36-2.23 (m, 5H), 2.16-2.13 (m, 2H), 2.03-1.93 (m, 2H), 1.87-1.73 (m, 5H), 1.54-1.41 (m, 8H), 1.33-1.25 (m, 3H), 1.21-1.04 (m, 5H), 1.02 (s, 3H), 0.98-0.93 (m, 4H), 0.68 (s, 3H).

Example 40: (R)—N-(cyclopropylmethyl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methoxypentanamide

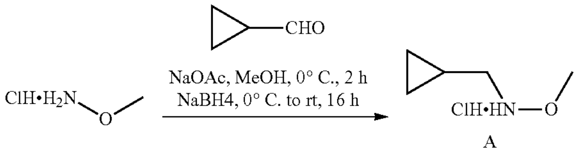

A

-continued

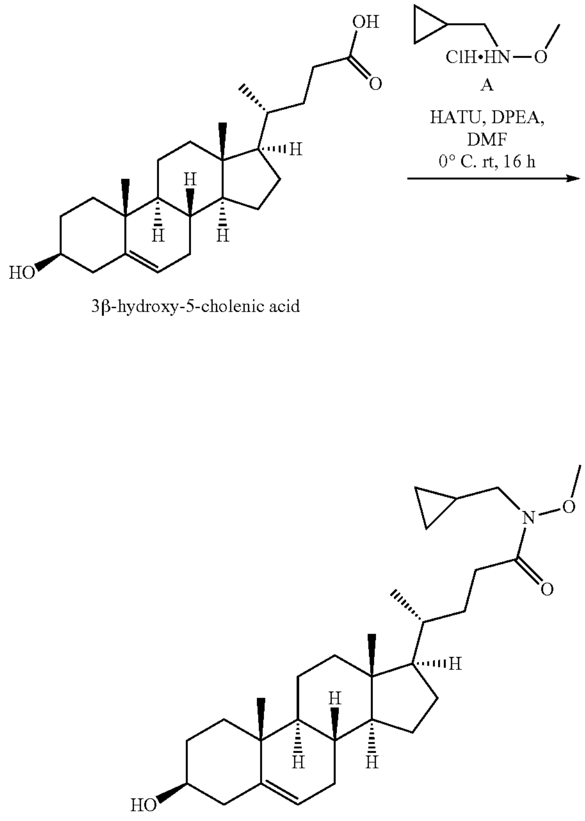

A

3β-hydroxy-5-cholenic acid

40

To a stirred solution of O-methylhydroxylamine hydrochloride (200 mg, 4.25 mmol) in methanol (5 mL) at 0° C. were added NaOAc (348 mg, 4.25 mmol) and cyclopropane carbaldehyde (893 mg, 12.75 mmol). After stirring the mixture at 0° C. for 2 h, $NaBH_4$ (482 mg, 12.75 mmol) was added, and the resultant mixture was stirred at room temperature for 16 h.

Upon completion, the reaction mixture was quenched with ice-water (20 mL), extracted with DCM (30 mL×3) and washed with saturated aqueous $NaHCO_3$ (30 mL×3). The combined organic layer was dried over sodium sulfate, filtered, treated with 4M HCl in 1,4-dioxane (2 mL), and concentrated in vacuo. The obtained residue was triturated with n-pentane to afford crude compound A as an off-white solid (50 mg).

Compound 40 was synthesized according to the general procedure A using 3β-hydroxy-5-cholenic acid (150 mg, 0.40 mmol), HATU (304 mg, 0.80 mmol), DIPEA (0.2 mL 1.2 mmol), crude compound A (60 mg, 0.44 mmol) and DMF (3 mL). The obtained crude material was purified by column chromatography over silica gel (100-200 mesh) with 0-50% gradient elution of ethyl acetate in hexanes to afford compound 40 as an off-white solid (50 mg, 27%). ELSD-MS (ESI) m/z: 458.4 $[M+H]^+$; $^1H$ NMR (400 MHz, $CDCl_3$) δ 5.37-5.35 (m, 1H), 3.73 (s, 3H), 3.58-3.49 (m, 1H), 3.47 (d, J=6.8 Hz, 2H), 2.51-2.42 (m, 1H), 2.39-2.3 (m, 1H), 2.29-2.22 (m, 2H), 2.04-1.94 (m, 2H), 1.92-1.77 (m, 4H), 1.56-1.40 (m, 8H), 1.39-1.27 (m, 2H), 1.21-1.02 (m, 6H), 1.0 (s, 3H), 0.98-0.85 (m, 4H), 0.68 (s, 3H), 0.53-0.49 (m, 2H), 0.29-0.26 (m, 2H).

Example 41: (R)—N-(cyclopropylmethoxy)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methylpentanamide

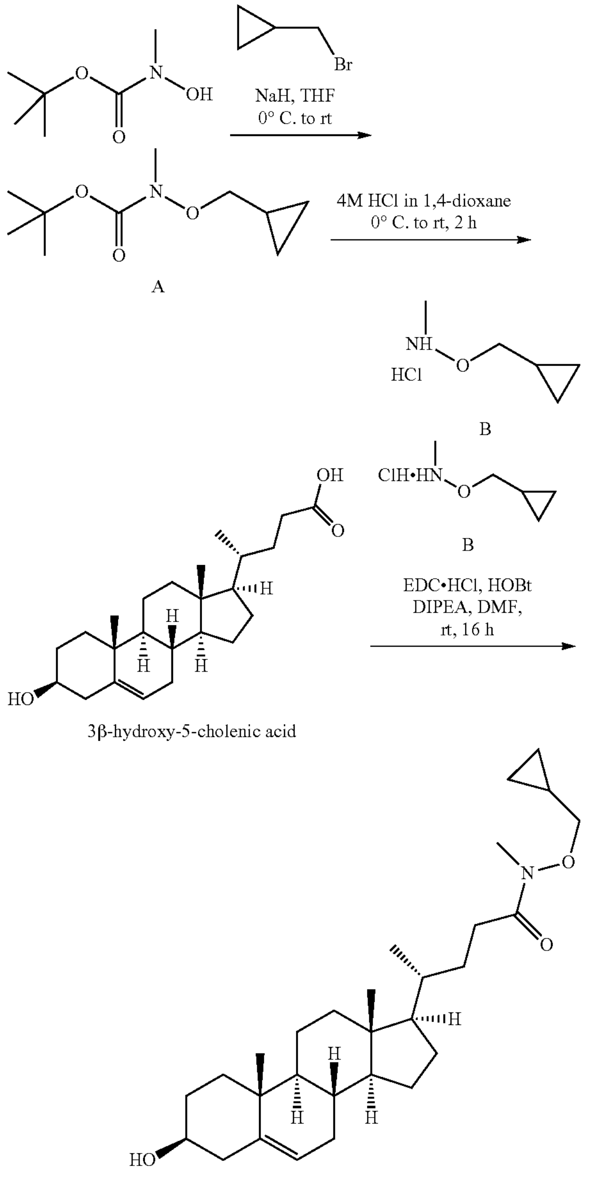

A

B

B

3β-hydroxy-5-cholenic acid

41

To a stirred solution of tert-butyl hydroxy(methyl)carbamate (0.5 g, 3.40 mmol) in THF (10 mL), were added NaH (60% dispersion in mineral oil, 163.07 mg, 6.79 mmol) and cyclopropylmethyl bromide (550 mg, 4.08 mmol). The resultant reaction mixture was stirred at room temperature for 16 h. Upon completion, the reaction mixture was diluted with water (50 mL) and extracted with ethyl acetate (20 mL×2). The combined organic layer was dried over sodium sulfate, filtered, and concentrated in vacuo to afford crude material that was purified by column chromatography over silica gel (100-200 mesh) with 0-10% gradient elution of ethyl acetate in hexane to afford compound A (350 mg, 51.19%) as light-yellow liquid.

To a stirred solution of compound A (100 mg, 0.49 mmol) in 1,4-dioxane (2 mL) at 0° C. was added HCl solution (4M HCl in 1,4-dioxane, 0.49 mmol, 2 mL) and the resulting reaction mixture was stirred at room temperature for 2 h. Upon completion, the reaction mixture was concentrated in vacuo to afford crude. The crude material was triturated with hexane (0.5 mL) to afford compound B (45 mg, 0.44 mmol, 89.54%) as light brown solid.

Compound 41 was synthesized according to the general procedure B using 3β-hydroxy-5-cholenic acid (150 mg, 0.40 mmol), compound B (176.35 mg, 0.12 mmol), EDC.HCl (176.35 mg, 0.12 mmol), DIPEA (517.57 mg, 0.40 mmol), HOBt (64.93 mg, 0.48 mmol) and DMF (2.35 mL) The reaction time was 16 h. The obtained crude material was purified by column chromatography over silica gel (100-200 mesh) with 0-5% gradient elution of MeOH in DCM to afford compound 41 (104 mg, 58%) as an off-white solid. LC-MS (ESI) m/z: 458.5 $[M+H]^+$; $^1H$ NMR (400 MHz, DMSO-$d_6$) δ 5.36-5.34 (m, 1H), 3.66 (d, J=7.2 Hz, 1H), 3.60-3.49 (m, 1H), 3.31 (s, 3H), 2.52-2.49 (m, 1H), 2.41-2.13 (m, 3H), 2.03-1.91 (m, 2H), 1.90-1.73 (m, 4H), 1.70 1.40 (m, 8H), 1.40-1.25 (m, 3H), 1.20-1.10 (m, 5H), 1.01 (s, 4H) 1.00-0.91 (m, 4H), 0.64 (s, 3H), 0.65-0.63 (m, 2H), 0.31-0.29 (m, 2H).

Example 42: Synthesis of (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]-phenanthren-17-yl)-1-((S)-5-(hydroxymethyl) isoxazolidin-2-yl) pentan-1-one

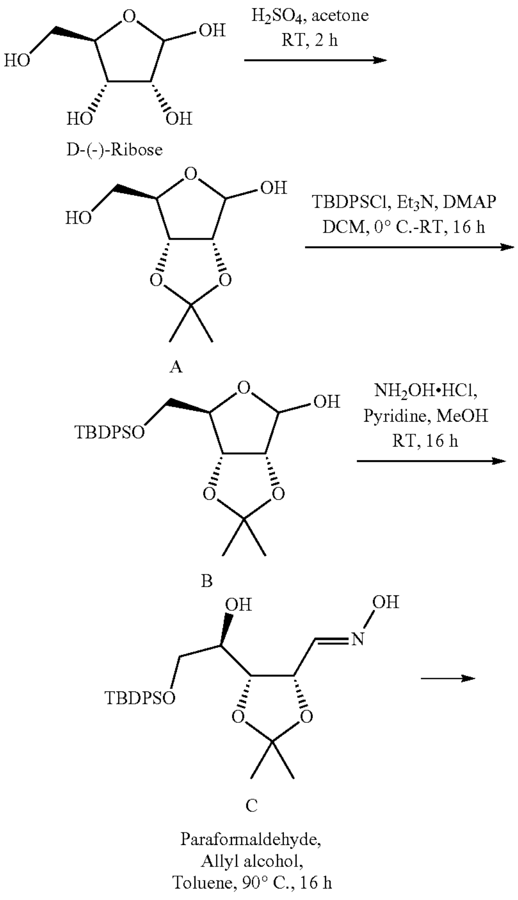

-continued

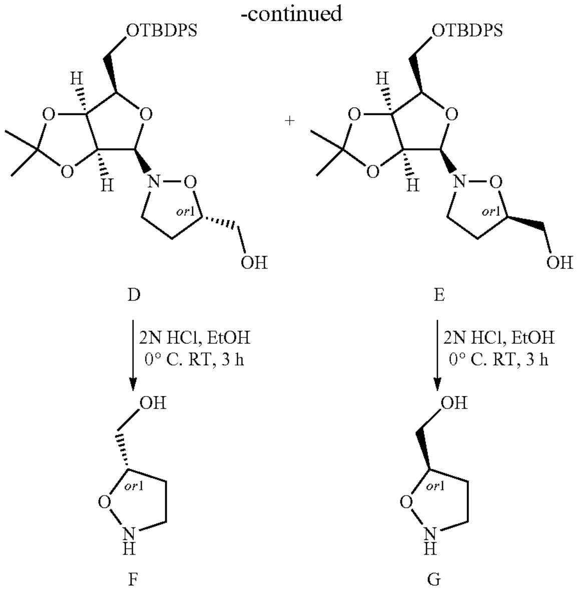

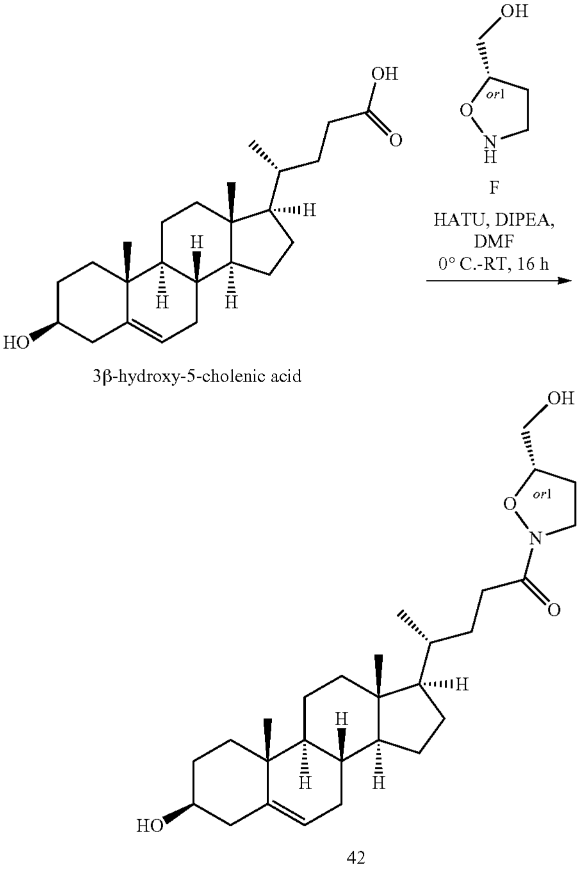

To a stirred solution of D-(−)-ribose (5.00 g, 33.30 mmol) in acetone (50 mL) was added $H_2SO_4$ (catalytic amount) dropwise at room temperature. The resultant mixture was stirred at room temperature for 2 h. Upon completion, the reaction mixture was quenched with solid sodium bicarbonate (50 mg), filtered, and concentrated in vacuo. The crude compound was purified by column chromatography over silica gel (100-200 mesh) with 0-35% gradient elution of EtOAc in hexanes to afford the compound A (2.5 g, 39%) as a gummy liquid. $^1H$ NMR (400 MHz, $CDCl_3$): δ 5.43-5.40

(m, 1H), 4.85 (d, J=6.0, 1H), 4.59 (d, J=5.6, 1H), 4.42 (t, J=2.4, 1H), 4.28-4.26 (m, 1H), 3.79-3.70 (m, 2H), 3.24-3.23 (m, 1H), 1.49 (s, 3H), 1.33 (s, 3H).

To a stirred solution of compound A (2.5 g, 13.14 mmol) in DCM (20 mL) were added $Et_3N$ (1.33 g, 13.14 mmol), 1.83 mL), TBDPSCl (3.61 g, 13.14 mmol) and DMAP (160 mg, 1.34 mmol) at 0° C. The resultant reaction mixture was stirred at room temperature for 16 h. Upon completion, the reaction mixture was diluted with water (10 mL) and extracted with DCM (20 mL×2). The combined organic layer was washed with water (10 mL), brine (10 mL), dried over anhydrous sodium sulphate, filtered, and concentrated in vacuo. The crude compound was purified by column chromatography over silica gel (100-200 mesh) with 0-20% gradient elution of EtOAc in hexanes to afford compound B (4.0 g, 71%) as a gummy liquid. ELSD-MS (ESI) m/z: 427 $[M-H]^+$; $^1H$ NMR (400 MHz, $CDCl_3$):Major isomer δ 7.68-7.62 (m, 4H), 7.48-7.38 (m, 6H), 5.35 (d, J=10.4, 1H), 4.72 (d, J=6.0, 1H), 4.60 (d, J=6.0, 1H), 4.50 (d, J=10.4, 1H), 4.28 (t, J=2.4, 1H), 3.85-3.79 (m, 1H), 3.68-3.64 (m, 1H), 1.47 (s, 3H), 1.32 (s, 3H), 1.09 (s, 9H).

To a stirred solution of $NH_2OH \cdot HCl$ (1.30 g, 18.67 mmol) in methanol (20 mL) was added pyridine (1.48 g, 18.67 mmol) at ambient temperature and stirred for 10 minutes. Compound B (4.0 g, 9.33 mmol) in methanol (5 mL) was added and the resultant mixture was stirred at room temperature 16 h. Upon completion, the reaction mixture was diluted with water (10 mL) and extracted with DCM (20 mL×2). The combined organic layer was washed with water (10 mL), brine (10 mL), dried over anhydrous sodium sulphate, filtered, and concentrated in vacuo. The crude compound was purified by column chromatography over silica gel (100-200 mesh) with 0-50% gradient elution of EtOAc in hexanes to afford compound C (E and Z isomers) (2.5 g, 60%) as a gummy liquid. LC-MS (ESI) m/z: 444 $[M+H]^+$; $^1H$ NMR (400 MHz, $CDCl_3$):Major isomer δ 10.93 (s, 1H), 7.69-7.62 (m, 4H), 7.48-7.40 (m, 6H), 7.35 (d, 1H), 5.10 (d, J=6 Hz, 1H), 4.66-4.62 (m, 1H), 4.28-4.21 (m, 1H), 3.73-3.60 (m, 3H), 1.33 (s, 3H), 1.28 (s, 3H), 0.99 (s, 9H).

To a stirred solution of compound C (2.5 g, 5.65 mmol) in toluene (25 mL) were added para formaldehyde (338 mg, 11.3 mmol) and allyl alcohol (655 mg, 11.3 mmol) at room temperature. The resultant mixture was stirred at 90° C. for 16 h. Upon completion, the reaction mixture was filtered, and the filtrate was concentrated in vacuo. The crude compound was purified by column chromatography over silica gel (100-200 mesh) with 0-50% gradient elution of EtOAc in hexanes to afford compound D (diastereomer-I, 600 mg) & compound E (diastereomer-II, 300 mg,) diastereomers.

Compound D (diastereomer-I): ELSD-MS (ESI) m/z: 514.3 $[M+H]^+$; $^1H$ NMR (400 MHz, $CDCl_3$): δ 7.67-7.65 (m, 4H), 7.45-7.35 (m, 6H), 4.76-4.74 (m, 1H), 4.65-4.63 (m, 1H), 4.53 (s, 1H), 4.30-4.22 (m, 2H), 3.72-3.64 (m, 3H), 3.51-3.45 (m, 1H), 3.18-3.13 (m, 1H), 3.02 2.95 (m, 1H), 2.30-2.11 (m, 1H), 2.04-1.97 (m, 1H), 1.93 (brs, 1H), 1.51 (s, 3H), 1.33 (s, 3H), 1.06 (s, 9H).

Compound E (diastereomer-II): ELSD-MS (ESI) m/z: 514.3 $[M+H]^+$; $^1H$ NMR (400 MHz, $CDCl_3$): δ 7.68-7.65 (m, 4H), 7.43-7.35 (m, 6H), 4.76-4.73 (m, 1H), 4.64-4.62 (m, 1H), 4.61-4.60 (m, 1H), 4.21-4.18 (m, 1H), 4.11-4.06 (m, 1H), 3.76-3.70 (m, 2H), 3.68-3.61 (m, 1H), 3.47-3.41 (m, 1H), 3.11-3.09 (t, J=7.6 Hz, 2H), 2.21-2.0 (m, 3H), 1.51 (s, 3H), 1.33 (s, 3H), 1.06 (s, 9H).

To a stirred solution of compound D (600 mg, 1.16 mmol) in ethanol (6 mL) was added aqueous 2N HCl (5 mL) at 0° C., the resultant mixture was allowed to stir at room temperature for 3 h. Upon completion, the reaction mixture was basified with saturated aqueous $Na_2CO_3$ and extracted with 10% MeOH in DCM (20 mL×3). The combined organic layer was dried over sodium sulfate, filtered, and concentrated. The obtained crude compound was purified by column chromatography over silica gel (100-200 mesh) with 0-10% gradient elution of MeOH in DCM to afford compound F (50 mg, 41%) as a pale-yellow liquid. $^1H$ NMR (400 MHz, $CDCl_3$): δ 4.19-4.14 (m, 1H), 3.79-3.75 (m, 1H), 3.60-3.56 (m, 1H), 3.18 (t, J=7.2, 2H), 2.30-2.21 (m, 1H), 2.05-1.97 (m, 1H).

To a stirring solution of compound E (300 mg, 0.58 mmol) in ethanol (3 mL) was added aqueous 2N HCl (2.5 mL) at 0° C., the resultant mixture was allowed to stir at room temperature for 3 h. Upon completion, the reaction mixture was basified with saturated aqueous $Na_2CO_3$ and extracted with 10% MeOH in DCM (20 mL×3). The combined organic layer was dried over sodium sulfate, filtered, and concentrated. The obtained crude compound was purified by column chromatography over silica gel (100-200 mesh) with 0-10% gradient elution of MeOH in DCM to afford compound G (30 mg, 50%) as a pale-brown liquid. NMR (400 MHz, $CDCl_3$): δ 4.19 4.14 (m, 1H), 3.79-3.75 (m, 1H), 3.61-3.56 (m, 1H), 3.18 (t, J=7.2, 2H), 2.30-2.21 (m, 1H), 2.05-1.97 (m, 1H).

Compound 42 was synthesized according to the general procedure A using 3β-hydroxy-5-cholenic acid (100 mg, 0.266 mmol), DIPEA (0.14 mL, 0.800 mmol), HATU (203 mg, 0.532 mmol), compound F (27.53 mg, 0.266 mmol), and DMF (2 mL). The obtained crude compound was purified by preparative HPLC (Column: KINETIX C18 (250*21.2 mm); 5 μm, solubility: ACN+$H_2O$+THF; mobile phase A: 0.01% FA in $H_2O$, mobile phase B: 0.1% FA in acetonitrile; flow rate: 13 mL/min, 0/25, 10/95) to afford the title compound 42 (10 mg, 8%) as pale-yellow solid. LC-MS (ESI) m/z: 460.4 $[M+H]^+$; $^1H$ NMR (400 MHz, DMSO-$d_6$): δ 5.27-5.25 (m, 1H), 4.92 (t, J=5.6 Hz, 1H), 4.58 (d, J=4.8 Hz, 1H), 4.14-4.08 (m, 1H), 3.65-3.58 (m, 1H), 3.57-3.46 (m, 2H), 3.41-3.35 (m, 1H), 3.28-3.20 (m, 1H), 2.28-2.19 (m, 1H), 2.18-2.05 (m, 2H), 2.00-1.86 (m, 3H), 1.85-1.71 (m, 2H), 1.70-1.61 (m, 2H), 1.59-1.43 (m, 3H), 1.42-1.31 (m, 4H), 1.30-1.16 (m, 3H), 1.15-1.05 (m, 2H), 1.04-0.96 (m, 3H), 0.94 (s, 3H), 0.92-0.82 (m, 4H), 0.64 (s, 3H).

Example 43: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-5-(hydroxymethyl)isoxazolidin-2-yl)pentan-1-one

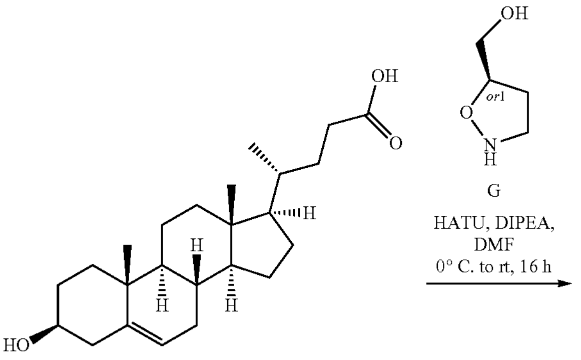

3β-hydroxy-5-cholenic acid

-continued

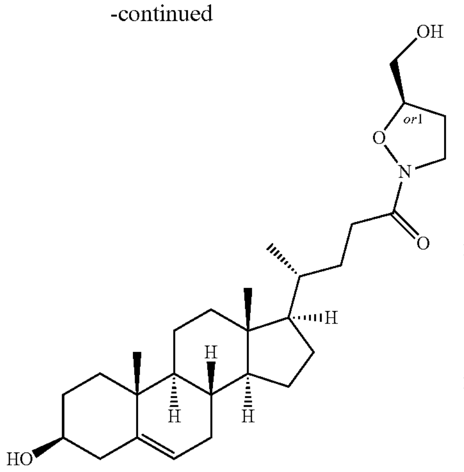

43

Compound 43 was synthesized according to the general procedure A using 3β-hydroxy-5-cholenic acid (100 mg, 0.266 mmol), DIPEA (0.14 mL, 0.800 mmol), HATU (203 mg, 0.532 mmol), compound G (27.53 mg, 0.266 mmol), and DMF (2 mL). The crude compound was purified by preparative HPLC (Column: KINETIX $C_{18}$ (250*21.2 mm); 5 μm, solubility: ACN+$H_2O$+THF, mobile phase A: 0.01% FA in $H_2O$, mobile phase B: 0.1% FA in acetonitrile; flow rate: 14 mL/min, 0/25, 10/95) to afford compound 43 (12 mg, 9%) as a pale brown solid. LC-MS (ESI) m/z: 460.4 $[M+H]^+$. $^1H$ NMR (400 MHz, DMSO-$d_6$) δ 5.27-5.25 (m, 1H), 4.92 (t, J=5.2 Hz, 1H), 4.58 (d, J=4.8 Hz, 1H), 4.16-4.09 (m, 1H), 3.63-3.46 (m, 3H), 3.41-3.35 (m, 1H), 3.28-3.10 (m, 1H), 2.27-2.18 (m, 1H), 2.15-2.05 (m, 2H), 2.01-1.86 (m, 4H), 1.85-1.72 (m, 2H), 1.70-1.59 (m, 2H), 1.60-1.43 (m, 4H), 1.42-1.31 (m, 3H), 1.30-1.20 (m, 2H), 1.18-1.01 (m, 4H), 1.0-0.97 (m, 2H), 0.94 (s, 3H), 0.92-0.82 (m, 4H), 0.64 (s, 3H).

Examples 44-46

Example 44: (R)-1-((3aR,6aR)-5-allylhexahydro-1H-pyrrolo[3,4-c]isoxazol-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one Example 45: (R)-1-((3aR,6aR)-5-allylhexahydro-1H-pyrrolo[3,4-c]isoxazol-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one Example 46: (R)-1-((3aS,6aS)-5-allylhexahydro-1H-pyrrolo[3,4-c]isoxazol-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

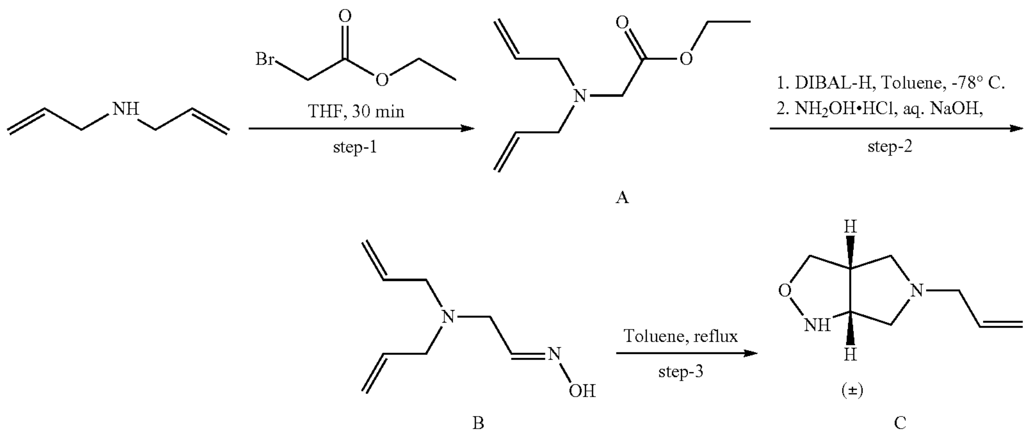

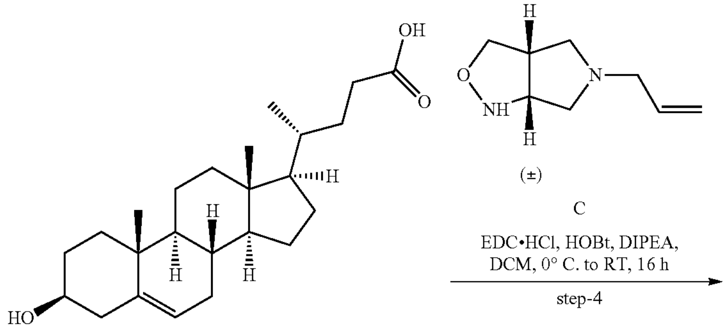

3β-hydroxy-5-cholenic acid

-continued

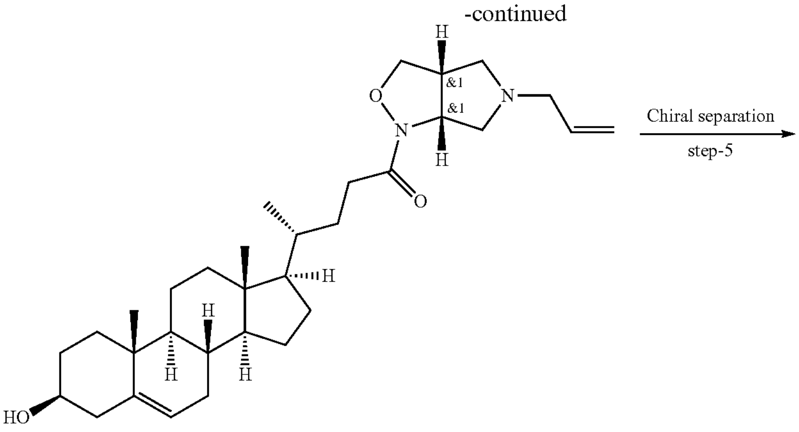

44

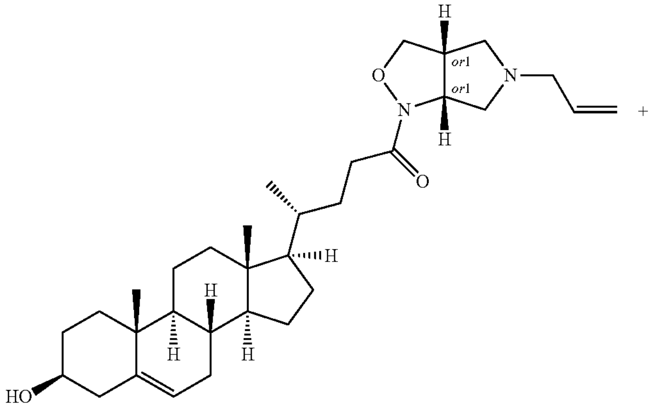

45

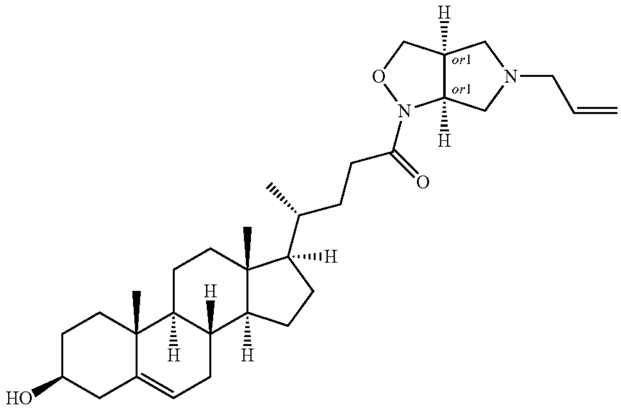

46

To a stirred solution of diallyl amine (5 g, 51.5 mmol) in benzene (200 mL) was added ethyl 2-bromoacetate (17.2 g, 103 mmol) in benzene (50 mL) at 0° C. under nitrogen atmosphere. The resulting reaction mixture was stirred at room temperature for 10 h. Upon completion, the reaction mixture was washed with water (50 mL×2), dried over anhydrous sodium sulfate, filtered, concentrated in vacuo, and purified by column chromatography over silica gel (100-200 mesh) using 0-20% gradient elution of ethyl acetate in hexanes to afford compound A as a colorless liquid (2.5 g, 26.5%).

To a stirred solution of A (2.8 g, 15.3 mmol) in toluene (28 mL) at −78° C. was added 1M DIBAL-H in hexane (16.8 mL, 16.8 mmol) under nitrogen atmosphere and the resulting mixture was stirred at same temperature for 4 h. Upon completion, the reaction mixture was quenched with aqueous NaOH (611 mg, 15.3 mmol) and the mixture was allowed to warm 0° C. Then, hydroxylamine hydrochloride (1.06 g, 15.3 mmol) was added, and the reaction mixture was allowed to stir at room temperature for 10 h. Upon completion, the reaction mixture was concentrated, the obtained residue was diluted with water (10 mL) and extracted with diethyl ether (20 mL×2). The combined organic layer was dried over sodium sulfate, filtered, concentrated in vacuo, and purified by column chromatography over silica gel (100-200 mesh) using 0-50% gradient elution of ethyl acetate in hexanes to afford compound B (mixture of E & Z) as a colorless liquid (1.4 g, 59.4%);

A solution of compound B (1.4 g, 9.08 mmol) in toluene (100 mL) was refluxed for 18 h. Upon completion, the reaction mixture was concentrated in vacuo to afford compound C as an oily compound (1.3 g, 92%).

Compound 44 was synthesized according to the general procedure B using 3β-hydroxy-5-cholenic acid (1.5 g, 4 mmol), compound C (679 mg, 4.41 mmol) EDC.HCl (1.15 g, 6.01 mmol), HOBt (595 mg, 4.41 mmol) and THE (45 mL). The crude compound was purified by column chromatography over silica gel (100-200 mesh) with 0-50% gradient elution of ethyl acetate in hexanes to afford compound 44 as an off-white solid (950 mg, 46.3%). LC-MS (ESI) m/z: 510.9 $[M+H]^+$; $^1H$ NMR (400 MHz, DMSO-$d_6$): δ 5.85-5.75 (m, 1H), 5.26 (brs, 1H), 5.19-5.06 (m, 2H), 4.64-4.58 (m, 2H), 3.88 (d, J=8.4 Hz, 1H), 3.78 (t, J=7.2 Hz, 1H), 3.31-3.21 (m, 1H), 3.19 3.11 (m, 1H), 2.97 (d, J=6 Hz, 2H), 2.67-2.56 (m, 2H), 2.50-2.45 (m, 2H), 2.33-2.25 (m, 1H), 2.22-2.03 (m, 2H), 1.98-1.86 (m, 2H), 1.85-1.72 (m, 2H), 1.71-1.59 (m, 2H), 1.58-1.44 (m, 3H), 1.42-1.31 (m, 3H), 1.30-1.15 (m, 3H), 1.13-0.97 (m, 5H), 0.93 (s, 3H), 0.92-0.83 (m, 4H), 0.64 (s, 3H).

The mixture of diastereomers 44 (800 mg) were separated by chiral prep-HPLC purification [column: CHIRALPAK IG (4.6×250) 5 μm), 5 μm; mobile phase: n-hexane: ethanol: DCM (40:50:10); flow rate: 1 mL/min, solubility: EtOH] to afford compound 45 (peak-1, 180 mg) and compound 46 (peak-2, 230 mg) as off-white solids. 45 (peak-1): LC-MS (ESI) m/z: 510.9 $[M+H]^+$; $^1H$ NMR (400 MHz, DMSO-$d_6$): δ 5.85-5.77 (m, 1H), 5.26 (brs, 1H), 5.19 (dd, J=1.6, 17.2 Hz, 1H), 5.06 (dd, J=10, 12 Hz, 1H), 4.64-4.60 (m, 1H), 4.59 (d, J=4.8 Hz, 1H), 3.90-3.87 (m, 1H), 3.78 (t, J=8 Hz, 1H), 3.30-3.21 (m, 1H), 3.19-3.10 (m, 1H), 2.98 (d, J=6 Hz, 2H), 2.63-2.58 (m, 1H), 2.48-2.41 (m, 2H), 2.31-2.25 (m, 2H), 2.19-2.05 (m, 2H), 1.98-1.86 (m, 2H), 1.82-1.72 (m, 2H), 1.71-1.59 (m, 2H), 1.58-1.32 (m, 7H), 1.31-1.03 (m, 6H), 1.01-0.96 (m, 2H), 0.93 (s, 3H), 0.91-0.83 (m, 4H), 0.64 (s, 3H). 46 (peak-2): LC-MS (ESI) m/z: 510.9 $[M+H]^+$; $^1H$ NMR (400 MHz, DMSO-$d_6$): δ 5.85-5.77 (m, 1H), 5.26 (brs, 1H), 5.19 (dd, J=2, 17.2 Hz, 1H), 5.07 (d, J=10 Hz, 1H), 4.65-4.58 (m, 2H), 3.90-3.87 (m, 1H), 3.79-3.76 (m, 1H), 3.32-3.22 (m, 1H), 3.19-3.11 (m, 1H), 2.98 (d, J=6 Hz, 2H), 2.65-2.56 (m, 2H), 2.47-2.35 (m, 3H), 2.21-2.03 (m, 3H), 1.98-1.86 (m, 2H), 1.85-1.72 (m, 2H), 1.70-1.59 (m, 2H), 1.58-1.43 (m, 3H), 1.42-1.32 (m, 4H), 1.30-1.13 (m, 3H), 1.12-0.96 (m, 4H), 0.94 (s, 3H), 0.89-0.88 (m, 4H), 0.64 (s, 3H).

Example 47: (R)-1-((3aS,6R,6aS)-6-ethylhexahydro-1H-pyrrolo[3,4-c]isoxazol-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

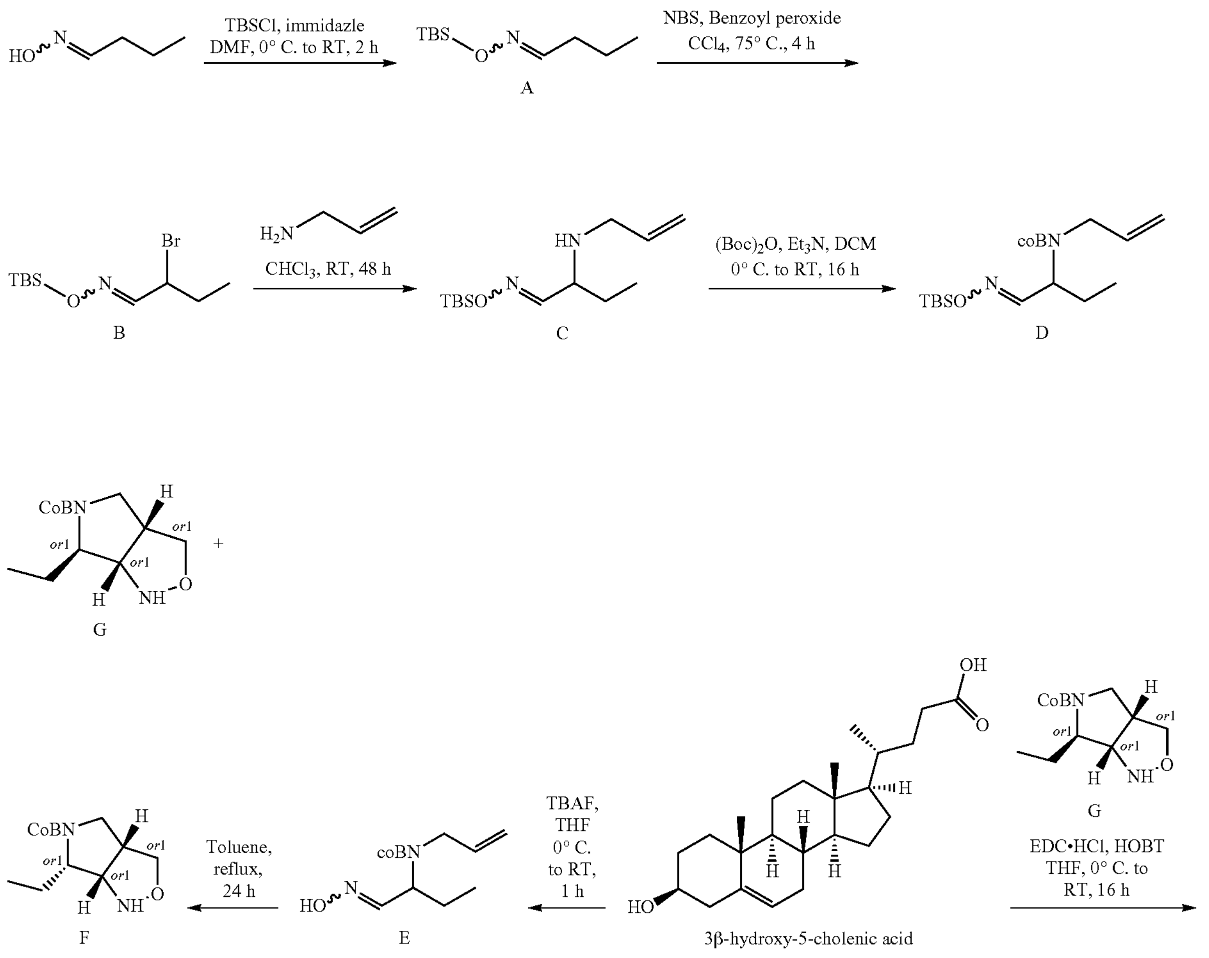

-continued

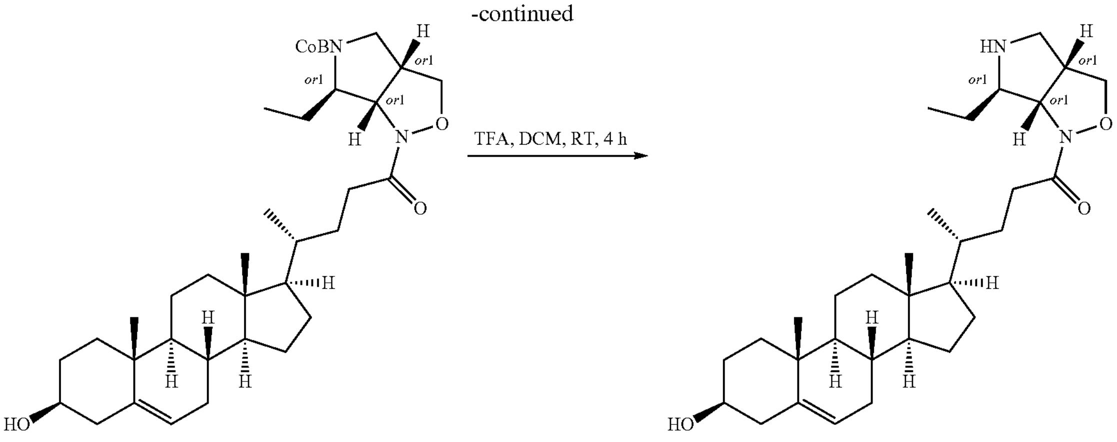

H

47

To a stirred solution of butyraldehyde oxime (500 mg, 5.74 mmol) in DMF (5 mL) at 0° C. were added imidazole (1.95 g, 28.67 mmol) and TBSC1 (1.73 g, 11.47 mmol). The resultant reaction mixture was stirred at room temperature for 2 h. Upon completion, the reaction mixture was diluted with water (30 mL) and extracted with diethyl ether (20 mL×2). The combined organic layer was dried over sodium sulfate, filtered, and concentrated in vacuo to afford compound A (E&Z isomers) as a pale brown liquid (800 mg, 69%).

To a stirred solution of crude compound A (7 g, 34.7 mmol) in $CCl_4$ (10 mL) at room temperature were added NBS (6.19 g, 34.76 mmol) and benzoyl peroxide (421 mg, 1.74 mmol). The resultant reaction mixture was stirred at 75° C. for 4 h. Upon completion, the reaction mixture was quenched with water (100 mL) and extracted with DCM (200 mL×3). The combined organic layer was dried over sodium sulfate, filtered, and concentrated in vacuo to afford compound B (E & Z isomers) as a pale brown liquid (6 g, 61%).

To a stirred solution of crude compound B (6 g, 21.41 mmol) in $CHCl_3$ (150 mL) was added allylamine (8.56 g, 149.85 mmol) at room temperature. The resultant reaction mixture was stirred at room temperature for 48 h. Upon completion, the reaction mixture was diluted with water (100 mL) and extracted with DCM (200 mL×3). The combined organic layer was dried over sodium sulfate, filtered, and concentrated in vacuo and purified by column chromatography over silica gel (100-200 mesh) with 0-50% gradient elution of ethyl acetate in hexanes to afford compound C as a brown solid (E and Z mixture, 3 g, 54%).

To a stirred solution of compound C (2 g, 7.8 mmol) in DCM (10 mL) were added $Et_3N$ (1.58 g, 15.60 mmol) and $(Boc)_2O$ (2.04 g, 9.36 mmol, 2.15 mL) at room temperature. The resultant reaction mixture was stirred at room temperature for 16 h. Upon completion, the reaction mixture was diluted with water (20 mL) and extracted with DCM (30 mL×3). The combined organic layer was dried over sodium sulfate, filtered, concentrated in vacuo, and purified by column chromatography over silica gel (100-200 mesh) with 0-50% gradient elution of ethyl acetate in hexanes to afford compound D as a brown solid (E and Z mixture, 1.2 g, 43%).

To a stirred solution of compound D (600 mg, 1.68 mmol) in THF (10 mL) was added TBAF solution 1.0 M in THF (1.68 mmol, 1.68 mL) at 0° C. The resultant reaction mixture was stirred at room temperature for 1 h. Upon completion, the reaction mixture was diluted with water (10 mL) and extracted with ethyl acetate (20 mL×3). The combined organic layer was dried over sodium sulfate, filtered, concentrated in vacuo, and purified by column chromatography over silica gel (100-200 mesh) with 0-50% gradient elution of ethyl acetate in hexanes to afford compound E as a yellow solid (200 mg, 49%).

A solution of compound E (1.2 g, 4.95 mmol) in toluene (60 mL) was stirred at 120° C. for 24 h. Upon completion, the reaction mixture was concentrated and dried in vacuo to obtain crude compound (mixture of diastereomers). Diastereomers were separated by column chromatography over silica gel (100-200 mesh) with 0-50% gradient elution of ethyl acetate in hexanes to afford compound F (isomer-I, 100 mg, 8%) and compound G (isomer-II, 500 mg, 41%) as a pale-yellow solid. These two isomers were confirmed by 2D NMR analysis.

Compound H was synthesized according to the general procedure B using 3β-hydroxy-5-cholenic acid (130 mg, 0.347 mmol), EDC.HCl (115 mg, 0.60 mmol), HOBt (60 mg, 0.44 mmol) DIPEA (0.21 mL, 1.2 mmol), compound G (107 mg, 0.44 mmol) and THE (5 mL). The crude material was purified over silica gel chromatography (100-200 mesh) by gradient elution of 0-50% ethyl acetate in hexanes to afford the compound H (100 mg, 41%) as an off-white solid. ELSD-MS (ESI) m/z: 599.5 $[M+H]^+$.

To a stirred solution of compound H (100 mg, 0.167 mmol) in DCM (5 mL) at 0° C. was added TFA (1 mL, 12.98 mmol) under nitrogen atmosphere. The resultant reaction mixture was stirred at room temperature for 4 h. Upon completion, the reaction mixture was concentrated, basified with saturated aqueous $NaHCO_3$ (10 mL), and extracted with ethyl acetate (20 mL×3). The combined organic layer was dried over sodium sulfate, filtered, and concentrated in vacuo to obtain crude material that was triturated with n-pentane and dried to afford compound 47 as an off-white solid (50 mg, 57%). ELSD-MS (ESI) m/z: 499.1 $[M+H]^+$; $^1H$ NMR (400 MHz, $CDCl_3$): δ 5.36-5.34 (m, 1H), 4.68-4.63 (m, 1H), 3.95 (d, J=8.8 Hz, 1H), 3.73-3.68 (m, 1H), 3.57-3.45 (m, 2H), 3.37-3.28 (m, 1H), 3.10-3.01 (m, 1H), 2.96-2.89 (m, 1H), 2.59-2.49 (m, 1H), 2.42-2.35 (m, 1H), 2.31-2.18 (m, 3H), 2.04-1.93 (m, 3H), 1.92-1.80 (m, 4H), 1.79-1.66 (m, 2H), 1.63-1.41 (m, 7H), 1.39-1.22 (m, 3H), 1.20-1.02 (m, 6H), 1.00 (s, 3H), 0.98-0.92 (m, 5H), 0.68 (s, 3H).

Example 48: (R)-1-((3aS,6S,6aS)-6-ethylhexahydro-1H-pyrrolo[3,4-c]isoxazol-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

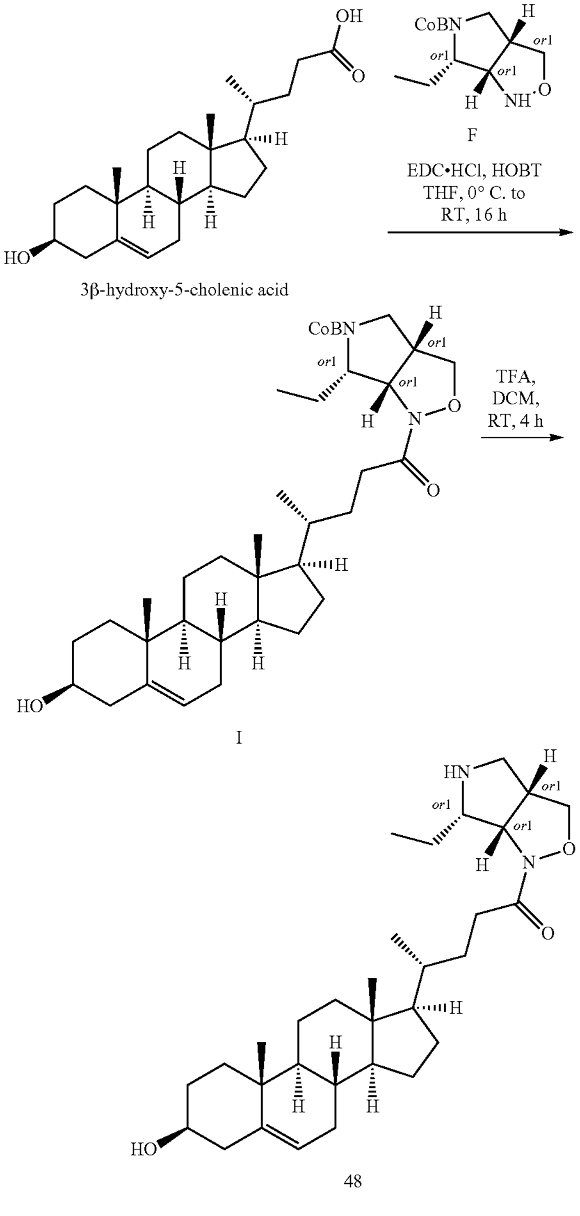

3β-hydroxy-5-cholenic acid

F

I

48

Compound I was synthesized according to the general procedure B using 3β-hydroxy-5-cholenic acid (150 mg, 0.40 mmol), EDC.HCl (115 mg, 0.60 mmol), HOBt (60 mg, 0.44 mmol) DIPEA (0.21 mL, 1.2 mmol), compound F (see Example 47)(Isomer-1, 97 mg, 0.40 mmol) and THF (5 mL). The crude material was purified over silica gel chromatography (100-200 mesh) by gradient elution of 0-50% ethyl acetate in hexanes to afford the compound I (50 mg, 20%) as an off-white solid. ELSD-MS (ESI) m/z: 599.5 $[M+H]^+$.

To a stirred solution of compound I (100 mg, 0.167 mmol) in DCM (5 mL) at 0° C. was added TFA (1 mL, 12.98 mmol) under nitrogen atmosphere. The resultant reaction mixture was stirred at room temperature for 4 h. Upon completion, the reaction mixture was concentrated, basified with saturated aqueous $NaHCO_3$ (10 mL), and extracted with ethyl acetate (20 mL×3). The combined organic layer was dried over sodium sulfate, filtered, and concentrated in vacuo to obtain the crude material, which was triturated with n-pentane and dried to afford compound 48 as an off-white solid (20 mg, 22%). ELSD-MS (ESI) m/z: 499.5 $[M+H]^+$; $^1H$ NMR (400 MHz, DMSO-$d_6$): δ 5.27-5.25 (m, 1H), 4.70 (t, J=6 Hz, 1H), 4.59 (d, J=4.8 Hz, 1H), 3.97-3.92 (m, 1H), 3.76-3.70 (m, 1H), 3.30-3.21 (m, 1H), 3.19-3.11 (m, 1H), 2.98-2.94 (m, 1H), 2.88-2.79 (m, 2H), 2.30-2.05 (m, 3H), 1.99-1.86 (m, 2H), 1.85-1.72 (m, 2H), 1.7-1.61 (m, 2H), 1.59-1.43 (m, 4H), 1.42-1.32 (m, 5H), 1.28-1.19 (m, 3H), 1.18-1.04 (m, 3H), 1.02-0.96 (m, 2H), 0.94 (s, 3H), 0.92-0.82 (m, 8H), 0.64 (s, 3H).

Example 49: (R)-1-((3aR,6aS)-3,3-dimethyltetrahydro-1H,3H-furo[3,4-c]isoxazol-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

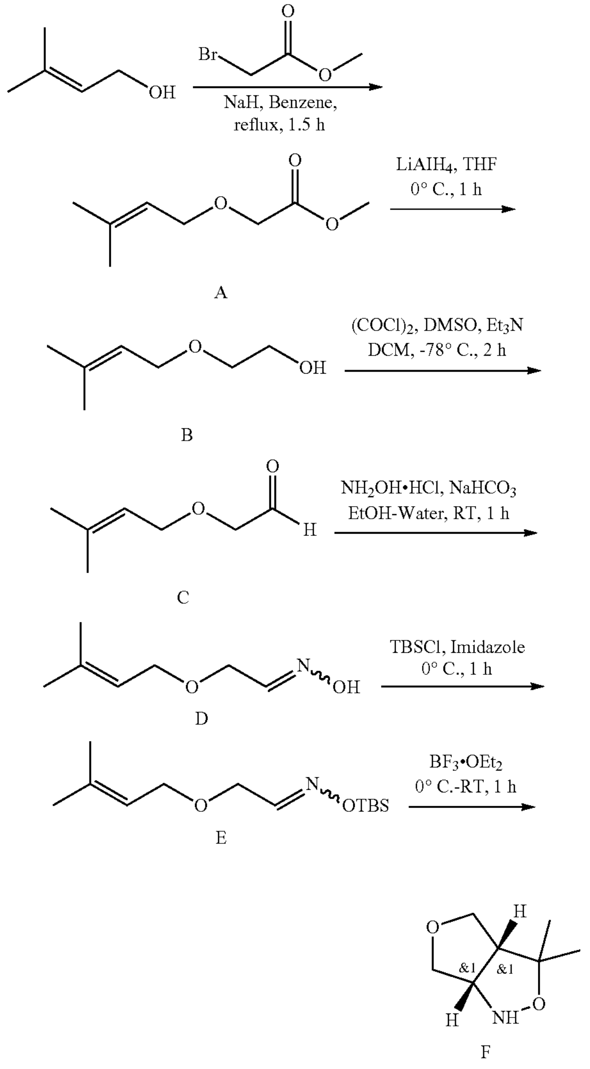

A

B

C

D

E

F

-continued

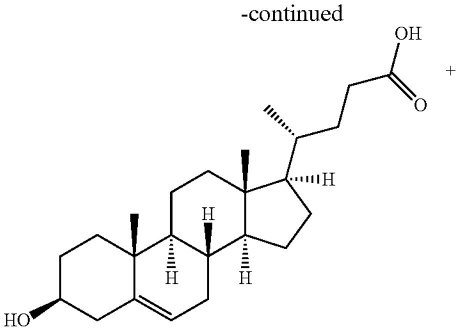

3β-hydroxy-5-cholenic acid

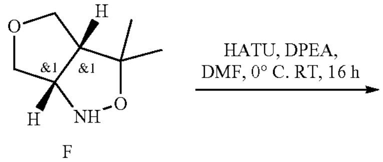

F

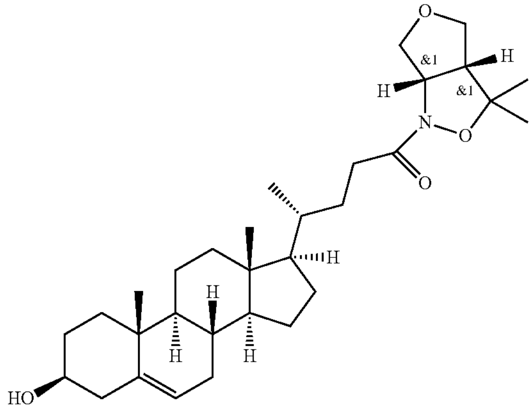

49

To a suspension of NaH (60% dispersed in mineral oil, 334 mg, 13.93 mmol) in dry benzene (20 mL) was added 3-methylbut-2-en-1-ol (1 g, 11.61 mmol) in benzene (5 mL) at ambient temperature and the resultant mixture was refluxed for 15 minutes. Methyl 2-bromoacetate (1.78 g, 11.61 mmol, 1.07 mL) was then added and the resultant reaction mixture was refluxed for an additional 1 h. Upon completion, the reaction mixture was quenched with saturated aqueous $NH_4C_1$ (30 mL) and extracted with ethyl acetate (50 mL×2). The combined organic layer was washed with water (50 mL), brine (50 ml), dried over sodium sulfate, filtered, and concentrated in vacuo to afford compound A as a pale-yellow liquid (1.2 g).

To a stirred solution of crude compound A (1.5 g, 9.48 mmol) in dry THE (20 mL) at 0° C. was added LAH (223 mg, 5.88 mmol) and stirred for 1 h at the same temperature. Upon completion, the reaction mixture was carefully quenched by addition of ethyl acetate (20 mL), MeOH (10 mL) and saturated aqueous $NaHCO_3$ (10 mL) at 0° C., then the resultant suspension was allowed to stir at room temperature for 16 h. The suspension was diluted with ethyl acetate (20 mL), filtered through a pad of Celite and the filtrate was concentrated in vacuo. The crude material was purified by column chromatography over silica gel (100-200 mesh) with 0-20% gradient elution of ethyl acetate in hexanes to afford compound B as a colorless liquid (300 mg, 24%).

To a stirred solution of oxalyl chloride (0.174 mL, 2.00 mmol) in dry DCM (10 mL) was added DMSO (192 mg, 2.46 mmol) at −78° C. and the mixture was further stirred for 30 min at same temperature. A solution of compound B (200 mg, 1.54 mmol) in dry DCM (5 mL) at −78° C. was then added and after stirring the reaction mixture for 30 minutes was added triethyl amine (1.07 mL, 7.68 mmol), allowed to warm to 0° C., and stirred for 1 h. Upon completion, the reaction mixture was diluted with water (100 mL) and extracted with $Et_2O$ (30 mL×2). The combined organic layer was dried over sodium sulfate, filtered, and concentrated in vacuo to afford compound C as a yellow liquid (190 mg).

To a stirred solution of hydroxylamine hydrochloride (3.58 g, 51.49 mmol, 2.14 mL) in $H_2O$ (30 mL) at room temperature was added $NaHCO_3$ (4.33 g, 51.49 mmol) followed by a solution of crude compound C (2.2 g, 17.16 mmol) in ethanol (15 mL) and stirred for 1 h. Upon completion, the reaction mixture was concentrated, obtained residue was diluted with water (20 mL) and extracted with ethyl acetate (30 mL×2). The combined organic layer was washed with water (20 mL), brine (20 mL), dried over sodium sulfate, filtered, and concentrated in vacuo. The crude compound was purified by column chromatography over silica gel (100-200 mesh) with 0-20% gradient elution of ethyl acetate in hexanes to afford compound D (E & Z isomers) as a colorless liquid (1.39 g, 56%). LC-MS (ESI) m/z: 144 $[M+H]^+$.

To a stirred solution of compound D (1.39 g, 9.71 mmol) in dry DMF (15 mL) was added TBDMSCl (2.93 g, 19.42 mmol) and imidazole (3.30 g, 48.54 mmol) at 0° C. The resultant reaction mixture was stirred for 1 h at same temperature. Upon completion, the reaction mixture was diluted with water (10 mL) and extracted with ethyl acetate (20 mL×3). The combined organic layer was dried over sodium sulfate, filtered, and concentrated in vacuo. The crude compound was purified by column chromatography over silica gel (100-200 mesh) with 0-10% gradient elution of ethyl acetate in hexanes to afford compound E (E & Z isomers) as a yellow solid (2.2 g, 86%). LC-MS (ESI) m/z: 258 $[M+H]^+$.

To a stirred solution of compound E (1.1 g, 4.27 mmol) in dry DCM (10 mL) was added $BF_3.Et_2O$ (1.27 g, 8.97 mmol) at 0° C. and the resultant reaction stirred at room temperature for 1 h. Upon completion, the reaction mixture was diluted with saturated aqueous $NaHCO_3$ (30 mL) and extracted with ethyl acetate (30×2 mL). The combined organic layer was washed with water (20 mL), brine (20 mL), dried over sodium sulfate, filtered, and concentrated in vacuo. The crude compound was purified by column chromatography over silica gel (100-200 mesh) with 0-3% gradient elution of MeOH in DCM to afford compound F (300 mg, 49%) as a colorless liquid.

Compound 49 was synthesized according to the general procedure A using 3β-hydroxy-5-cholenic acid (200 mg, 0.53 mmol), HATU (400 mg, 1.06 mmol) DIPEA (0.27 mL, 1.59 mmol), compound F (98 mg, 0.68 mmol), and DMF (5 mL). The crude material was purified by column chromatography over silica gel (100-200 mesh) with gradient elution of 0-50% ethyl acetate in hexanes to afford the title compound 49 (180 mg, 67%) as an off-white solid. ELSD-MS (ESI) m/z: 500.4 $[M+H]^+$; $^1H$ NMR (400 MHz, DMSO-$d_6$): δ 5.26-5.25 (m, 1H), 4.86-4.82 (m, 1H), 4.58 (d, J=4.4 Hz, 1H), 3.83-3.80 (m, 1H), 3.75-3.71 (m, 1H), 3.64-3.56 (m, 2H), 3.28-3.20 (m, 1H), 2.95-2.87 (m, 1H), 2.37-2.21 (m, 2H), 2.20-2.03 (m, 2H), 1.99-1.85 (m, 2H), 1.84-1.72 (m, 2H), 1.70-1.61 (m, 2H), 1.60-1.43 (m, 3H), 1.42-1.32 (m, 4H), 1.30 (s, 3H), 1.29-1.19 (m, 2H), 1.19-1.12 (m, 4H), 1.11-1.02 (m, 2H), 1.01-096 (m, 2H), 0.94 (s, 3H), 0.92-0.83 (m, 4H), 0.64 (s, 3H).

Example 50: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((3S,3aR,6aS)-3-phenylhexahydro-1H-cyclopenta[c]isoxazol-1-yl)pentan-1-one

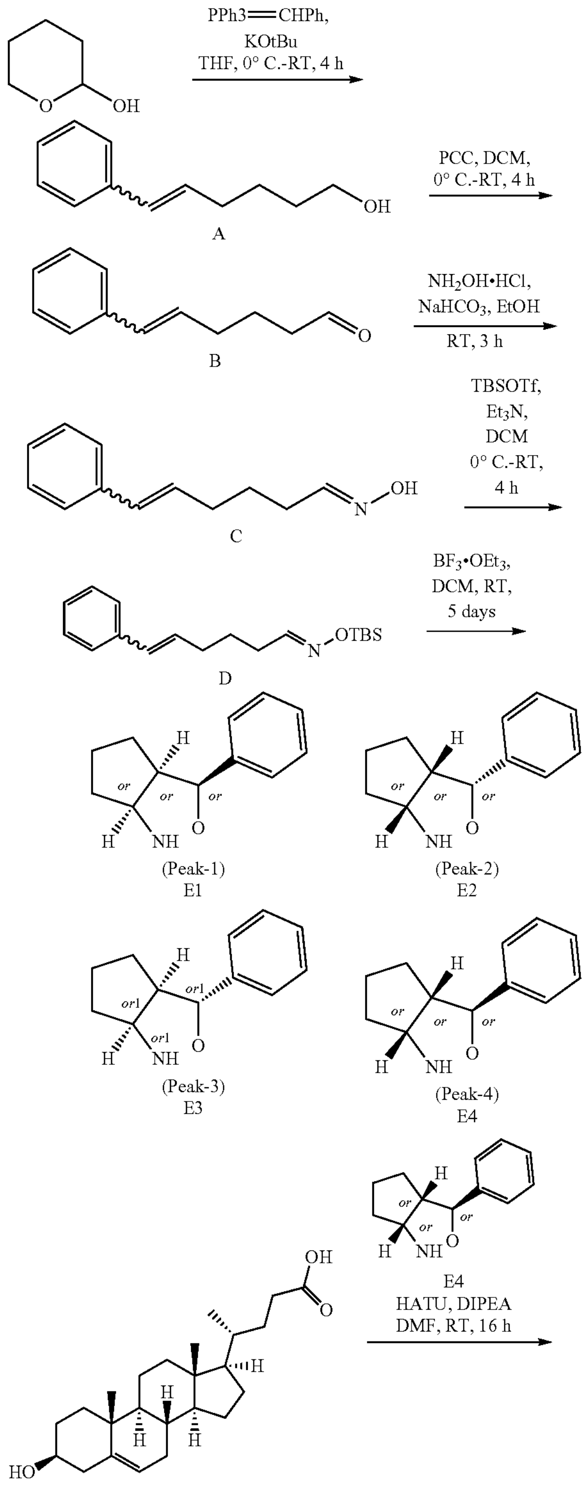

3β-hydroxy-5-cholenic acid

-continued

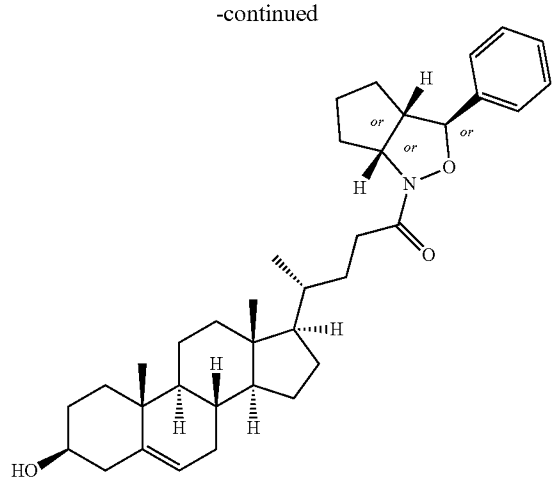

50

To a stirred suspension of benzyl(triphenyl)phosphonium chloride (9.14 g, 23.50 mmol) in dry THE (30 mL) was added potassium tert-butoxide (3.30 g, 29.37 mmol) at 0° C. and which was then stirred for ten minutes at room temperature. Tetrahydropyran-2-ol (2 g, 19.58 mmol) was then added dropwise at 0° C. and the resulting mixture was stirred at room temperature for 4 h. Upon completion the reaction mass was quenched with water (20 mL) and extracted with ethyl acetate (2×30 mL). The combined organic layer was dried over sodium sulphate, filtered, and concentrated to obtained crude compound that was purified by column chromatography over silica gel (100-200 mesh) with 10-15% gradient elution of ethyl acetate in hexane to afford compound A (E and Z mixture, 1.4 g, 41%) as a gummy liquid.

To a stirred solution of compound A (1.4 g, 7.94 mmol) in anhydrous DCM (20 mL), was added pyridinium chlorochromate (1.71 g, 7.94 mmol) in one portion at 0° C. and the resulting reaction mixture was stirred at room temperature for 4 h. Upon completion, the reaction mixture was diluted with water (10 mL) and extracted with DCM (2×30 mL). The combined organic layer was washed with water (10 mL) and brine (10 mL), dried over anhydrous sodium sulfate, filtered, and concentrated in vacuo to get crude compound. The crude material was purified by column chromatography over silica gel (100-200 mesh) with 0-20% gradient elution of ethyl acetate in hexane to afford compound B (E and Z mixture, 0.8 g, 58%) as a gummy liquid.

To a stirred solution of hydroxylamine hydrochloride (638.12 mg, 9.18 mmol,) in ethanol (5 mL) was added $NaHCO_3$ (771.42 mg, 9.18 mmol) followed by compound B (800 mg, 4.59 mmol) dissolved in ethanol (30 mL) at ambient temperature and stirred for 3 h at same temperature. Upon completion, the reaction mixture was extracted with DCM (2×50 mL). The combined organic layer was washed with water (10 mL), brine (10 mL), dried over anhydrous sodium sulphate, filtered, and concentrated in vacuo to get crude compound. The crude material was purified by column chromatography over silica gel (100-200 mesh) with 0-20% gradient elution of ethyl acetate in hexane to afford compound C (E and Z mixture, 600 mg, 65%) as a gummy liquid. LC-MS (ESI) m/z: 190 $[M+H]^+$.

To a stirring solution of compound C (600 mg, 3.17 mmol) in anhydrous DCM (10 mL), was added TBSOTF (403.81 mg, 4.76 mmol) and triethyl amine (641.62 mg, 6.34 mmol) at 0° C., and the resulting reaction mixture was allowed to stir at same temperature for 4 h. Upon completion, the reaction mixture was diluted with water (5 mL) and extracted with DCM (2×20 mL). The combined organic layer was washed with water (5 mL), brine (5 mL), dried over anhydrous sodium sulphate, filtered, and concentrated in vacuo to obtain crude compound. The crude material was purified by column chromatography over silica gel (100-200 mesh) with 0-20% gradient elution of ethyl acetate in hexane to afford compound D (E and Z mixture, 600 mg, 1.98 mmol, 62%) as a gummy liquid.

To a stirred solution of compound D (600 mg, 1.98 mmol) in anhydrous DCM (7 mL), was added $BF_3 \cdot OEt_2$ (0.702 g, 4.15 mmol) at 0° C., and the resulting reaction mixture was allowed to stir at ambient temperature for 5 days. Upon completion, the reaction mixture was diluted with saturated aqueous $NaHCO_3$ (5 mL) and extracted with ethyl acetate (2×10 mL). The combined organic layer was washed with water (5 mL), brine (5 mL), dried over anhydrous sodium sulphate, filtered, and concentrated in vacuo to get crude compound. The crude material was purified by column chromatography over silica gel (100-200 mesh) with gradient elution of 15-25% ethyl acetate in hexane to afford mixture of diastereomers (420 mg). The diastereomers are separated by chiral preparative HPLC (Column: Chiralpak IG (250*4.6)$_5$μ; Mobile phase: n-Hexane:IPA(70:30); Flow 1.0 mL/Min) to obtained compound E1 (peak-1.40 mg), compound E2 (peak-2, 40 mg) compound E3 (peak-3, 50 mg) compound E4 (peak-4, 50 mg) as colorless liquids.

Compound 50 was synthesized according to the general procedure A using 3β-Hydroxy-5-cholenic acid (100 mg, 0.266 mmol), compound E4 (peak-4, 50.53 mg, 0.266 mmol), DIPEA (104 mg, 0.800 mmol,), HATU (203 mg, 0.533 mmol), and DMF (5 mL). The reaction time was 16 h. The obtained crude compound was purified by column chromatography over silica gel (100-200 mesh) with a gradient elution of 0-20% ethyl acetate in hexane to afford the title compound 50 (19.0 mg,. 94%) as an off-white solid. LC-MS (ESI) m/z: 546.4 $[M+H]^+$; $^1$H NMR (400 MHz, $CDCl_3$) δ 7.36-7.35 (m, 5H), 5.35-5.34 (m, 1H), 4.85-4.81 (m, 2H), 3.60-3.51 (m, 1H), 3.20-3.10 (m, 1H), 2.40-2.20 (m, 2H), 2.19-2.10 (m, 1H), 1.90-1.80 (m, 5H), 1.79-1.70 (m, 5H), 1.69-1.60 (m, 2H), 1.50-1.40 (m, 7H), 1.39-1.35 (m, 2H), 1.34-1.22 (m, 5H), 0.99 (s, 3H), 0.96-0.94 (m, 3H), 0.77 (d, J=6.4, 3H), 0.66 (s, 3H).

Example 51: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((3R,3aS,6aR)-3-phenylhexahydro-1H-cyclopenta[c]isoxazol-1-yl)pentan-1-one

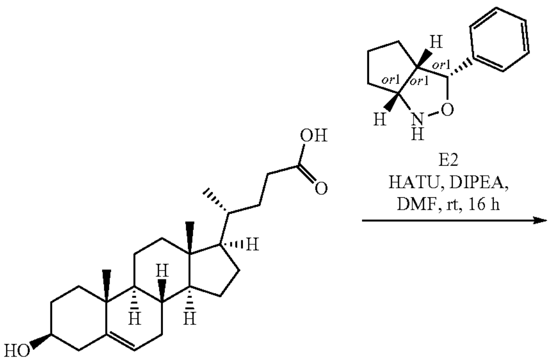

3β-hydroxy-5-cholenic acid

-continued

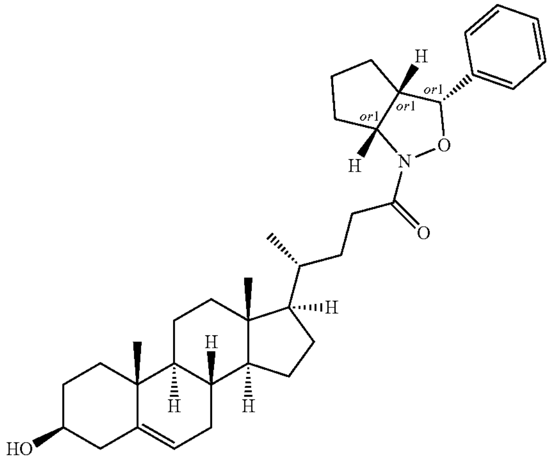

51

Compound 51 was synthesized according to the general procedure A using 3β-Hydroxy-5-cholenic acid (90 mg, 0.240 mmol), compound E2 (45.47 mg, 0.240 mmol), DIPEA (93 mg, 0.720 mmol), HATU (183 mg, 0.480 mmol), and dry DMF (5 mL). The reaction time was 16 h. The obtained crude compound was purified by column chromatography over silica gel (100-200 mesh) with a gradient elution of 0-20% ethyl acetate in hexane to afford the title compound 51 (29.5 mg, 22%) as an off-white solid. LC-MS (ESI) m/z: 546.5 $[M+H]^+$; $^1$H NMR (400 MHz, $CDCl_3$) δ 7.38-7.26 (m, 5H), 5.34 (d, J=5.2 Hz, 1H), 5.02 (d, J=5.6, 1H), 4.99-4.90 (m, 1H), 3.52-3.49 (m, 1H), 3.25-3.15 (m, 1H), 2.60-2.50 (m, 1H), 2.33-2.10 (m, 3H), 1.90-1.82 (m, 8H), 1.55-1.47 (m, 10H), 1.46-1.44 (m, 3H), 1.40-1.25 (m, 2H), 1.23-1.14 (m, 4H), 0.99 (s, 3H), 0.98 91 (m, 4H), 0.67 (s, 3H).

Example 52: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((3R,3aR,6aS)-3-phenylhexahydro-1H-cyclopenta[c]isoxazol-1-yl)pentan-1-one

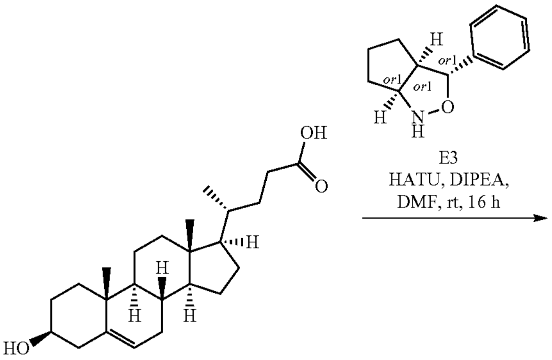

3β-hydroxy-5-cholenic acid

-continued

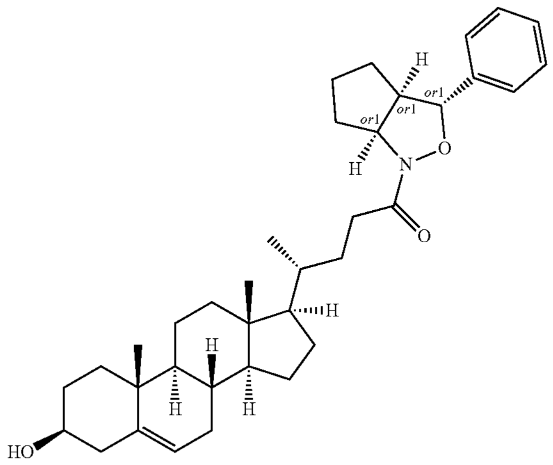

52

Compound 52 was synthesized according to the general procedure A using 3β-Hydroxy-5-cholenic acid (100 mg, 0.266 mmol) compound E3 (50.53 mg, 0.266 mmol), DIPEA (104 mg, 0.800 mmol), HATU (203 mg, 0.533 mmol), and dry DMF (5 mL). The reaction time was 16 h. The obtained crude compound was purified by column chromatography over silica gel (100-200 mesh) with a gradient elution of 0-20% ethyl acetate in hexane to afford the title compound 52 (60 mg, 40%) as an off-white solid. LC-MS (ESI) m/z: 546.5 $[M+H]^+$; $^1H$ NMR (400 MHz, $CDCl_3$) δ 7.37-7.31 (m, 5H), 5.26-5.24 (m, 1H), 4.99 (d, J=3.2 Hz, 1H), 4.82-4.76 (m, 1H), 4.58 (d, J=4.8 Hz, 1H), 3.36-3.18 (m, 2H), 2.18-2.00 (m, 3H), 1.98-1.80 (m, 4H), 1.79-1.59 (m, 8H), 1.56-1.42 (m, 3H), 1.40-1.23 (m, 4H), 1.20-1.02 (m, 6H), 0.99-0.92 (m, 4H), 0.88-0.84 (m, 2H), 0.69-0.62 (m, 3H), 0.58 (s, 3H).

Example 53: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((3S,3aR,6aS)-3-phenylhexahydro-1H-cyclopenta[c]isoxazol-1-yl)pentan-1-one

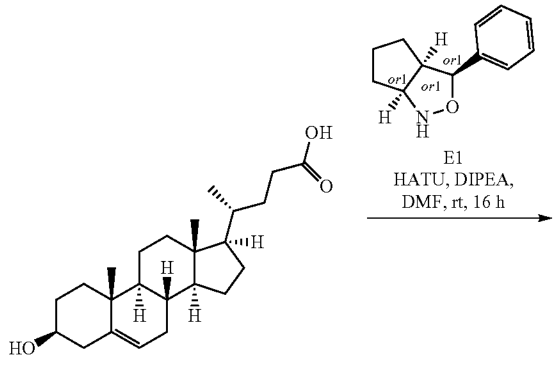

3β-hydroxy-5-cholenic acid

-continued

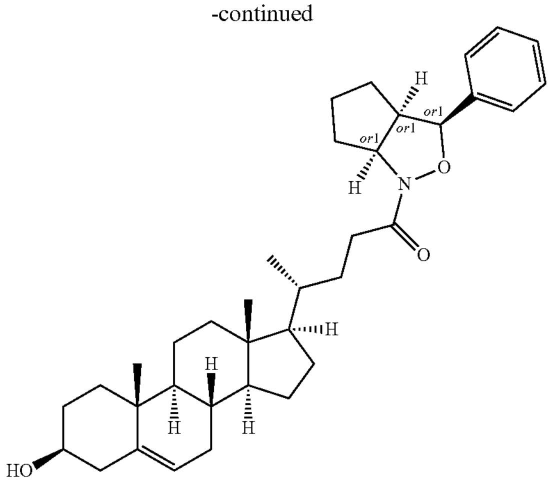

53

Compound 53 was synthesized according to the general procedure A using 3β-Hydroxy-5-cholenic acid (90 mg, 0.240 mmol), compound E2 (45.47 mg, 0.240 mmol), DIPEA (93 mg, 0.720 mmol), HATU (183 mg, 0.480 mmol), and dry DMF (5 mL). The reaction time was 16 h. The obtained crude compound was purified by column chromatography over silica gel (100-200 mesh) with a gradient elution of 0-20% ethyl acetate in hexane to afford the title compound 53 (31.0 mg, 0.053 mmol, 23%) as an off-white solid. LC-MS (ESI) m/z: 546.5 $[M+H]^+$; $^1H$ NMR (400 MHz, $CDCl_3$) δ 7.40-7.26 (m, 5H), 5.35-5.30 (m, 1H), 5.03 (d, J=6.0, 1H), 4.99-4.92 (m, 1H), 3.60-3.51 (m, 1H), 3.28-3.21 (m, 1H), 2.48-2.41 (m, 2H), 2.32-2.20 (m, 2H), 1.97-1.80 (m, 9H), 1.55-1.40 (m, 7H), 1.38-1.28 (m, 4H), 1.27-1.01 (m, 6H), 1.00-0.90 (m, 8H), 0.66 (s, 3H).

Example 54: (R)-1-((1S,4R,5S,6S)-5,6-dihydroxy-2-oxa-3-azabicyclo [2.2.1]heptan-3-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl) pentan-1-one

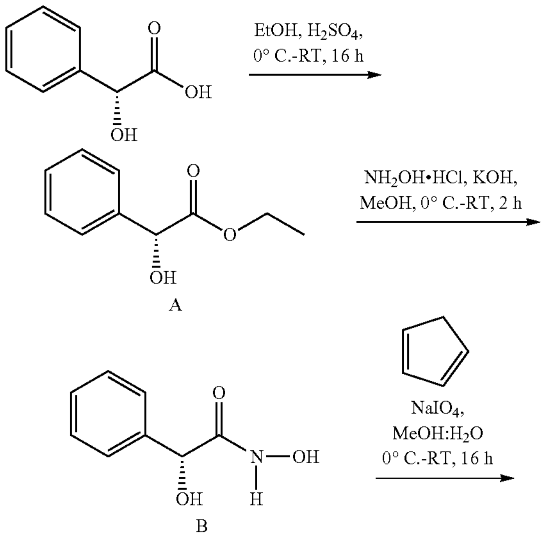

-continued

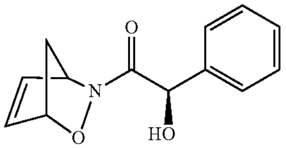

+

C1 (Peak-1)
Major diastereomer

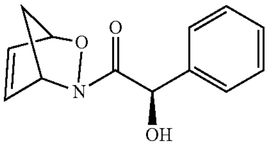

C2 (Peak-2)
Minor diastereomer

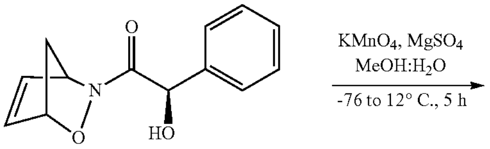

C1 (Peak-1)

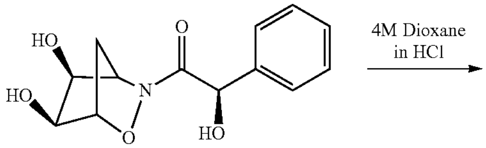

D

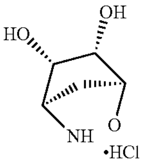

E

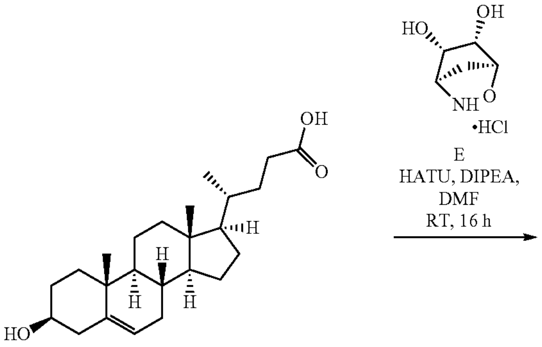

3β-hydroxy-5-cholenic acid

-continued

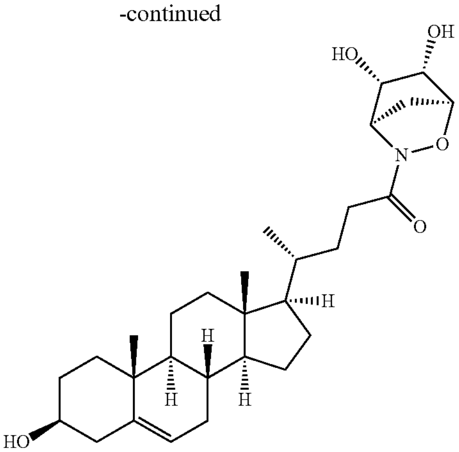

54

To the stirred solution of (2R)-2-hydroxy-2-phenylacetic acid (3 g, 19.7 mmol) in ethanol (30 mL, 514 mmol) at 0° C. was added sulfuric acid (2 mL) dropwise. The resultant reaction mixture was allowed to warm to room temperature and stirred for 16 h. Upon completion, the reaction mixture was quenched with ice cold water (20 mL) and extracted with ethyl acetate (2×30 mL). The combined organic layer was washed with brine (30 mL), dried over anhydrous sodium sulfate, and concentrated in vacuo to afford crude compound A (3.2 g, 91%) which was used for the next step without further purification.

To a stirred solution of hydroxylamine hydrochloride (4.63 g, 66.6 mmol) in methanol (50 mL, 1.23 mol) at 0° C. was added potassium hydroxide (5.6 g, 99.9 mmol) dissolved in methanol. The reaction mixture was stirred at room temperature for 20 minutes, then filtered and washed with methanol. The filtrate was transferred into a round bottom flask followed by addition of compound A (6 g, 33.3 mmol) dissolved in methanol. The resultant reaction mixture was allowed to stir at room temperature for 1 h. Upon completion, the reaction mixture was acidified with 2N acetic acid and extracted with ethyl acetate (8×10 mL). The combined organic layer was dried over anhydrous sodium sulfate and concentrated in vacuo to afford crude compound. The crude compound was purified by trituration with ethyl acetate to obtain compound B (4 g, 72%) as an off-white solid which was used for the next step without further purification.

To a stirred solution of cyclopenta-1,3-diene (297 mg, 4.49 mmol) in methanol (10 mL, 247 mmol) at room temperature were added compound B (0.5 g, 2.99 mmol) and sodium periodate (768 mg, 3.59 mmol) under nitrogen atmosphere. The resultant reaction mixture was allowed to stir at room temperature for 4 h. Upon completion, the reaction mixture was diluted with water (5 mL) and extracted with DCM (2×10 mL). The combined organic layer was washed with brine (10 mL), dried over anhydrous sodium sulfate, and concentrated in vacuo to afford crude compound. The crude compound was purified by column chromatography over 100-200 silica gel mesh by eluting 15% ethyl acetate in hexane to afford mixture of compounds $C_1$ and $C_2$ (220 mg, 951 mol). The diastereomers were separated by chiral prep HPLC [column: CHIRAL PAK IG (4.6×250) 5u; mobile phase-A: n-Hexane, mobile phase-B: ethanol; Flow:1.0 mL/Min; ISOCRATIC:(A:B):70:30, diluent: ethanol] to afford compound C1 (peak-1) (150 mg, 21%) and compound C2 (peak-2) (50 mg, 7%) as an off-white solids.

To the stirred solution of compound C1 (0.4 g, 1.73 mmol) in methanol (10 mL, 247 mmol) at −76° C. was added $MgSO_4$ (271 mg, 2.25 mmol) and followed by $KMnO_4$ (355 mg, 2.25 mmol) dissolved in water (3 mL) under nitrogen atmosphere. The resultant reaction mixture was allowed to warm to −12° C. and stirred for 5 h. Upon completion, saturated aqueous $Na_2SO_3$ (2 mL) was added to the reaction mixture followed by extraction with ethyl acetate (2×10 mL). The combined organic layer was dried over anhydrous sodium sulfate and concentrated in vacuo to afford crude compound. The crude material was purified by column chromatography over 100-200 silica gel mesh with elution of 35% ethyl acetate in hexane. Required fractions were concentrated in vacuo to afford compound D (0.2 g, 43%) as a gummy yellow liquid. LC-MS indicated 98% of desired compound mass peak, m/z 266 $[M+H]^+$.

To the stirred solution of compound D (0.2 g, 0.754 mmol) in 1,4-dioxane (4 mL, 46.9 mmol) at 0° C. was added 4M HCl in 1,4-dioxane (185 μL, 2.26 mmol) and allowed to stir at room temperature for 4 h. Upon completion, the reaction mixture was concentrated to afford crude compound E (90 mg, 71%) as a yellow liquid.

Compound 54 was synthesized according to the general procedure A using 3β-hydroxy-5-cholenic acid (0.1 g, 0.267 mmol), DIPEA (0.2 L, 1.15 mol), HATU (203 mg, 0.534 mmol) crude compound E (105 mg, 0.801 mmol), and dry THE (5 mL). The obtained crude compound was purified by preparative HPLC [column: Gemini® 3 μm NX—C18 110 Å LC column 50*2 mm; mobile phase-A: 0.01% FA in water, mobile phase-B: 100% ACN; flow rate: 0.6 ml/min; program (Time/% B): 0.01/5,6.0/90,8.00/90,10.01/05] to afford compound 54 (47 mg, 36%). LC-MS (ESI) m/z: 488 $[M+H]^+$; $^1H$ NMR (400 MHz, DMSO-$d_6$): δ 5.29-5.25 (m, 1H), 5.16 (brs, 1H), 4.96 (brs, 1H), 4.58 (brs, 1H), 4.44 (s, 1H), 4.41 (s, 1H), 3.78-3.73 (m, 2H), 3.26-3.22 (m, 1H), 2.33-2.22 (m, 1H), 2.18-2.08 (m, 4H), 1.98-1.85 (m, 2H), 1.82-1.72 (m, 2H), 1.70-1.58 (m, 3H), 1.57-1.28 (m, 7H), 1.26-0.95 (m, 7H), 0.94 (s, 3H), 0.90-0.82 (m, 4H), 0.64 (s, 3H).

Example 55: (R)-1-((1R,4S,5R,6R)-5,6-dihydroxy-2-oxa-3-azabicyclo[2.2.1]heptan-3-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

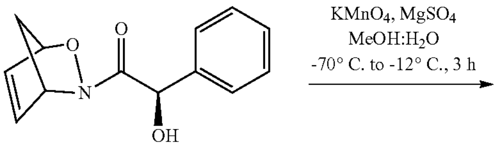

C2 (Peak-2)

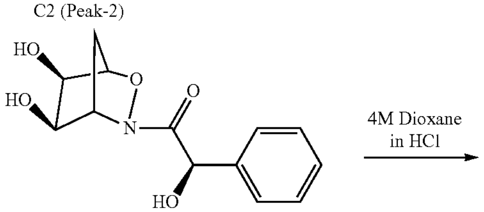

D

-continued

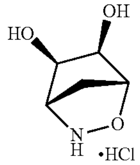

E

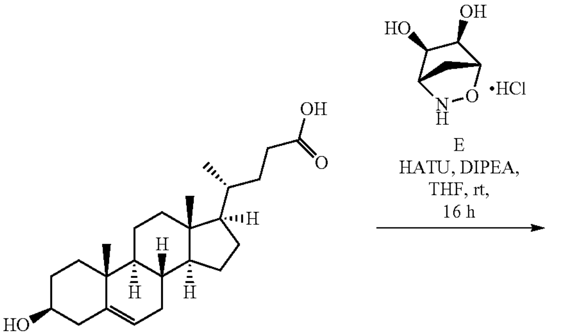

E

3β-hydroxy-5-cholenic acid

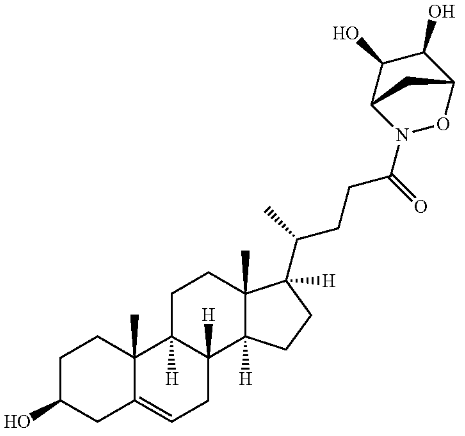

55

To a stirred solution of $C_2$ (Example 53) (180 mg, 0.778 mmol) in methanol (5 mL) at −78° C. were added $MgSO_4$ (271 mg, 2.25 mmol) and $KMnO_4$ (355 mg, 2.25 mmol) dissolved in water (3 mL). The resultant reaction mixture was allowed to warm to −12° C. and stirred for 3 h. Upon completion, the reaction mixture was diluted with water (10 mL) and extracted with ethyl acetate (2×10 mL). The combined organic layer was dried over anhydrous sodium sulfate and concentrated in vacuo to afford crude compound D (150 mg, 72%) as a gummy liquid. LC-MS analysis of crude compound indicated 86% peak of desired m/z-266 $[M+H]^+$.

To a stirred solution of crude compound D (120 mg, 0.452 mmol) in 1,4-dioxane (5 mL) at 0° C. was added 4M HCl in dioxane (340 μL, 1.36 mmol). The resultant reaction mixture was allowed to stir at room temperature for 6 h. Upon completion, the reaction mixture was concentrated in vacuo to afford crude compound E (70 mg, 92%) as a light-yellow oil.

Compound 55 was synthesized according to the general procedure A using 3β-hydroxy-5-cholenic acid (60 mg, 0.160 mmol), DIPEA (140 μL, 0.801 mmol), HATU (122 mg, 0.320 mmol), crude compound E (42 mg, 0.320 mmol) and dry THF (5 mL). The obtained crude compound was purified by preparative HPLC purification [column: Gemini 3 μm NX-C18 110A LC Column 50*2 mm; mobile phase-A:

0.01% FA in water, mobile phase-B: 100% ACN; flow rate: 0.6 ml/min; program (Time/% B): 0.01/5,6.0/90,8.00/90, 10.01/05] to afford compound 55 (40 mg, 51%) as an off-white solid. LC-MS (ESI) m/z: 488 $[M+H]^+$; $^1H$ NMR (400 MHz, DMSO-$d_6$): δ 5.26 (d, J=5.2 Hz, 1H), 5.19-5.14 (m, 1H), 4.98-4.92 (m, 1H), 4.58 (d, J=4.4 Hz, 1H), 4.45-4.39 (m, 2H), 3.78-3.73 (m, 2H), 3.25-3.20 (m, 1H), 2.29-2.05 (m, 5H), 1.99-1.85 (m, 2H), 1.82-1.72 (m, 2H), 1.70-1.58 (m, 3H), 1.57-1.42 (m, 3H), 1.42-1.31 (m, 4H), 1.30-0.95 (m, 7H), 0.94 (s, 3H), 0.90-0.83 (m, 4H), 0.64 (s, 3H).

Example 56: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(1,2-oxazepan-2-yl)pentan-1-one

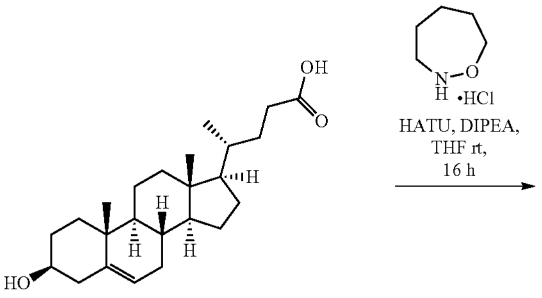

3β-hydroxy-5-cholenic acid

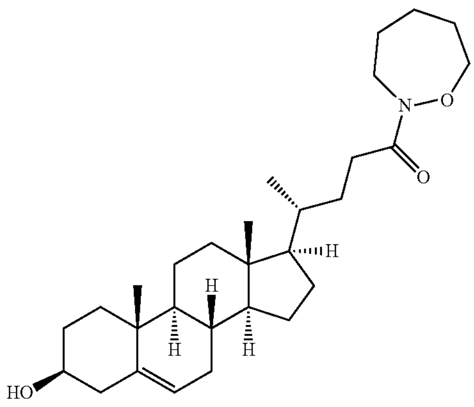

56

Compound 56 was synthesized according to the general procedure A using 3β-hydroxy-5-cholenic acid (120 mg, 0.32 mmol), HATU (244 mg, 0.64 mmol), DIPEA (207 mg, 1.6 mmol), 1,2-oxazepane hydrochloride (88.2 mg, 0.64 mmol), and THF (1.2 mL). The reaction time was 16 h. The obtained crude material was purified by column chromatography over silica gel (100-200 mesh) with 0-30% gradient elution of ethyl acetate in hexane to afford compound 56 (59 mg, 40%) as an off-white solid. LC-MS (ESI) m/z: 458 $[M+H]^+$; $^1H$ NMR (400 MHz, $CDCl_3$): δ 5.37-5.34 (m, 1H), 4.00 (t, J=5.2 Hz, 2H), 3.74-3.67 (m, 2H), 3.53-3.49 (m, 1H), 2.51-2.41 (m, 1H), 2.40-2.22 (m, 4H), 2.03-1.92 (m, 2H), 1.90-1.72 (m, 9H), 1.52-1.41 (m, 7H), 1.40-1.21 (m, 3H), 1.20-1.02 (m, 5H), 1.01 (s, 3H) 0.98-0.91 (m, 4H), 0.68 (s, 3H).

Example 57: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-methylisoxazolidin-2-yl)pentan-1-one

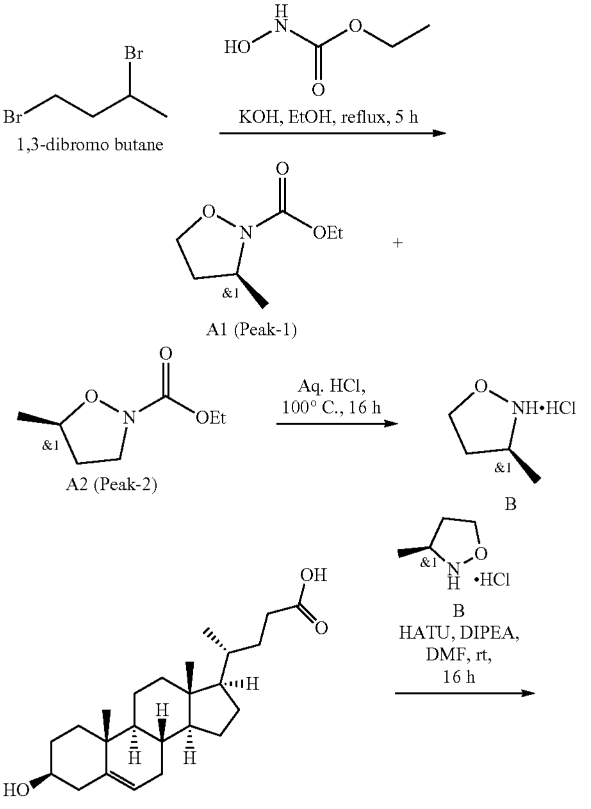

1,3-dibromo butane

A1 (Peak-1)

A2 (Peak-2)

B

B

3β-hydroxy-5-cholenic acid

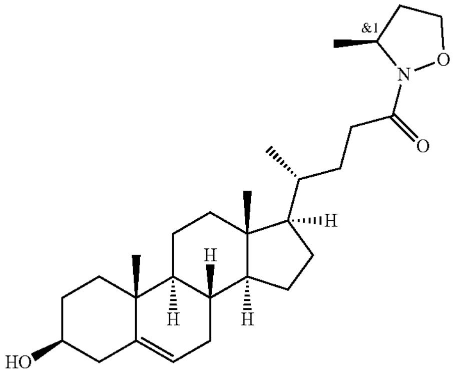

57

To a stirred solution of 1,3-dibromobutane (1 g, 4.63 mmol) in ethanol (20 mL, 343 mmol) were added ethyl N-hydroxycarbamate (487 mg, 4.63 mmol) and potassium hydroxide (520 mg, 9.26 mmol) at room temperature under nitrogen atmosphere. The resulting reaction mixture was stirred at 80° C. for 5 h. Upon completion, the reaction mixture was concentrated in vacuo to get crude compound. It was diluted with water (50 mL) and extracted with ethyl acetate (50 mL×3). The combined organic layer was dried over sodium sulfate and filtered, concentrated in vacuo and purified by column chromatography over silica gel (100-200 mesh) with 0-5% gradient elution of ethyl acetate in hexanes to afford mixture of regioisomers A1 and A2 as an off-white solid (400 mg). The regioisomers were separated by chiral prep HPLC [column: Lux amylose-1 (4.6×250) 5 μm; mobile phase: hexanes/IPA 90/10; flow rate: 1 mL/min.] to afford compound A1 (peak-1, 70 mg, 9.51%) and compound A2 (peak-2, 8 mg, 1.08%) as colorless liquid. Both compounds were characterized by 2D NMR analysis.

To a stirred solution of compound A1 (70 mg, 0.44 mmol) in water (1 mL) at ambient temperature was added 6N HCl (1 mL). The resultant reaction mixture was stirred at 100° C. for 16 h. Upon completion, the reaction mixture was concentrated to afford HCl salt of crude compound B as a brown liquid (40 mg, 72%). LC-MS m/z: 88 [M+H]$^+$.

Compound 57 was synthesized according to the general procedure A using 3β-hydroxy-5-cholenic acid (120 mg, 0.32 mmol), HATU (244 mg, 0.641 mmol), DIPEA (0.16 mL, 0.96 mmol), Compound B (41.9 mg, 0.481 mmol), and DMF (4 mL). The crude material was purified by preparative HPLC [column: Agilent prep (50*30 mm);5 μm; mobile phase: A: 0.1% FA in water, B: Acetonitrile; flow rate: 20 mL/min.] to afford the title compound 57 (55 mg, 39%). LC-MS (ESI) m/z: 444 [M+H]$^+$; $^1$H NMR (400 MHz, DMSO-$d_6$) δ 5.28-5.25 (m, 1H), 4.58 (d, J=4.4 Hz, 1H), 4.28-4.23 (m, 1H), 4.11-4.07 (m, 1H), 3.74-3.68 (m, 1H), 3.27-3.24 (m, 1H), 2.57-2.55 (m, 1H), 2.43-2.23 (m, 3H), 2.22-2.03 (m, 3H), 1.98-1.61 (m, 8H), 1.58-1.31 (m, 5H), 1.30-1.17 (m, 5H), 1.14-0.96 (m, 4H), 0.94 (s, 3H), 0.90-0.88 (m, 3H), 0.64 (s, 3H).

Example 58: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-4-methylisoxazolidin-2-yl)pentan-1-one

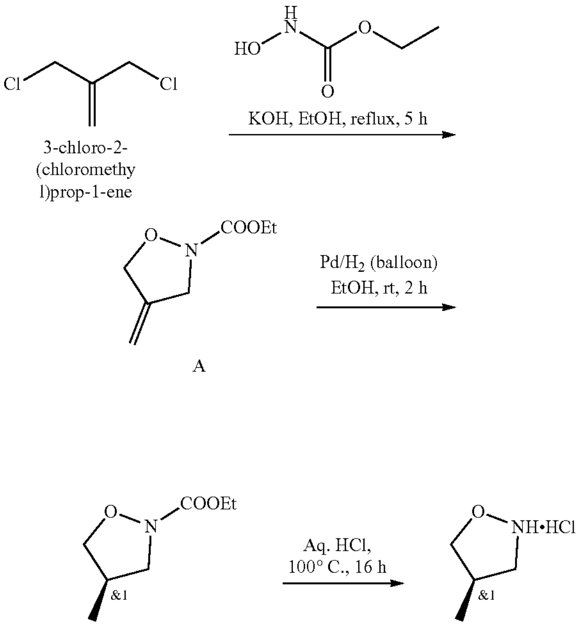

3-chloro-2-(chloromethyl)prop-1-ene

A

B

C

-continued

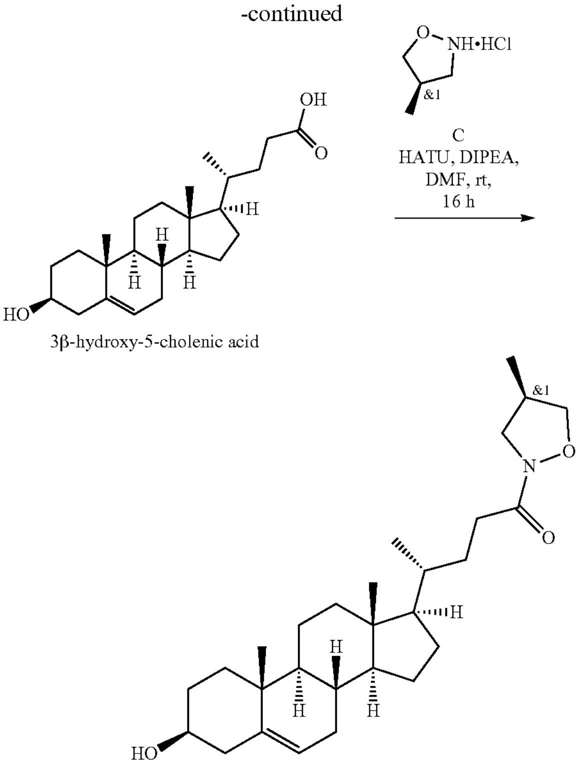

3β-hydroxy-5-cholenic acid

C

58

To a stirred solution of 3-chloro-2-(chloromethyl)prop-1-ene (1 g, 8 mmol) in ethanol (20 mL) were added ethyl N-hydroxycarbamate (841 mg, 8 mmol) and potassium hydroxide (898 mg, 16 mmol) at room temperature under nitrogen atmosphere. The resulting reaction mixture was stirred at 80° C. for 5 h. Upon completion, the reaction mixture was concentrated in vacuo to obtain crude compound which was diluted with water (50 mL) and extracted with ethyl acetate (50 mL×3). The combined organic layer was dried over sodium sulfate, filtered, concentrated in vacuo, and purified by column chromatography over silica gel (100-200 mesh) with 0-5% gradient elution of ethyl acetate in hexanes to afford compound A as a colorless liquid (300 mg, 23.69%).

To a stirred solution of compound A (300 mg, 1.91 mmol) in ethanol (6 mL) at ambient temperature was added 10% Pd/C (60 mg). The resultant reaction mixture was degassed with hydrogen gas and stirred at ambient temperature for 2 h under the hydrogen atmosphere (balloons). Upon completion, the reaction mixture was filtered through pad of Celite and the filtrate was concentrated in vacuo and purified by column chromatography over silica gel (100-200 mesh) with 0-5% gradient elution of ethyl acetate in hexanes to afford compound B as a colorless liquid (180 mg, 59.40%). LC-MS m/z: 160 [M+H]$^+$.

To a stirred solution of compound B (130 mg, 0.817 mmol) in water (1.5 mL) was added 6N HCl (2 mL) at ambient temperature. The resultant reaction mixture was stirred at 100° C. for 16 h. Upon completion, the reaction mixture was concentrated to afford HCl salt of crude compound C as a brown liquid (100 mg, 72%) which was used for the next step without further purification. LC-MS m/z: 88 [M+H]$^+$.

Compound 58 was synthesized according to the general procedure A using 3β-hydroxy-5-cholenic acid (150 mg, 0.4 mmol), HATU (305 mg, 0.8 mmol), DIPEA (0.21 mL, 1.2 mmol), Compound C (53 mg, 0.601 mmol) and DMF (5 mL). The crude material was purified by preparative HPLC [column: Agilent prep (50*30 mm);5 μm; mobile phase: A: 0.1% FA in water, B: acetonitrile; flow rate: 25 mL/min.] to afford the title compound 58 (40 mg, 12.7%). LC-MS (ELSD) m/z: 443.9 $[M+H]^+$; $^1H$ NMR (400 MHz, DMSO-$d_6$): δ 5.27-5.25 (m, 1H), 4.58 (d, J=4.4 Hz, 1H), 4.04-4.00 (m, 1H), 3.77-3.68 (m, 1H), 3.51-3.47 (m, 1H), 3.28-3.12 (m, 2H), 2.67-2.63 (m, 1H), 2.28-2.06 (m, 3H), 1.96-1.72 (m, 4H), 1.70-1.43 (m, 5H), 1.42-1.31 (m, 4H), 1.30-1.02 (m, 9H), 1.01-0.96 (m, 2H), 0.93 (s, 3H), 0.89 (d, J=6.4 Hz, 4H), 0.64 (s, 3H).

Example 59: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-5-methylisoxazolidin-2-yl)pentan-1-one

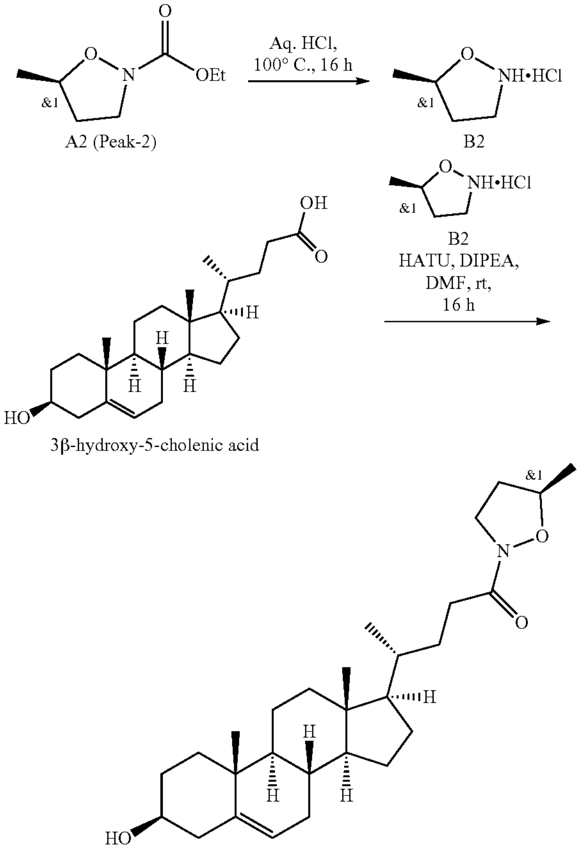

A2 (Peak-2)

B2

B2

3β-hydroxy-5-cholenic acid

59

To a stirred solution of A2 (Example 57) (120 mg, 0.754 mmol) in water (1 mL) at ambient temperature was added 6N HCl (1.5 mL). The resultant reaction mixture was stirred at 100° C. for 16 h. Upon completion, the reaction mixture was concentrated to afford HCl salt of crude compound B2 as a brown liquid (60 mg, 64.63%) which was used for the next step without further purification. LC-MS m/z: 88 $[M+H]^+$.

Compound 59 was synthesized according to the general procedure A using 3β-hydroxy-5-cholenic acid (100 mg, 0.267 mmol), HATU (203 mg, 0.534 mmol), DIPEA (0.14 mL, 0.801 mmol), compound B2 (46.5 mg, 0.534 mmol) and DMF (4 mL). The crude material was purified by preparative HPLC [column: Agilent prep (50*30 mm);5 μm; mobile phase: A: 0.1% FA in water, B: Acetonitrile+MeOH (9:10); flow rate: 25 mL/min.] to afford the title compound 59 (15 mg, 12.7%). LC-MS (ELSD) m/z: 443.9 $[M+H]^+$; $^1H$ NMR (400 MHz, DMSO-$d_6$): δ 5.26-5.25 (m, 1H), 4.65 (bs, 1H), 4.17-4.09 (m, 1H), 3.72-3.65 (m, 1H), 3.54-3.45 (m, 1H), 3.26-3.22 (m, 1H), 2.38-2.12 (m, 4H), 1.98-1.72 (m, 5H), 1.70-1.61 (m 2H), 1.59-1.32 (m, 7H), 1.31-1.13 (m, 6H), 1.12-0.96 (m, 4H), 0.93 (s, 3H), 0.90-0.85 (m, 4H), 0.64 (s, 3H).

Example 60: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-6-methyl-1,2-oxazinan-2-yl)pentan-1-one

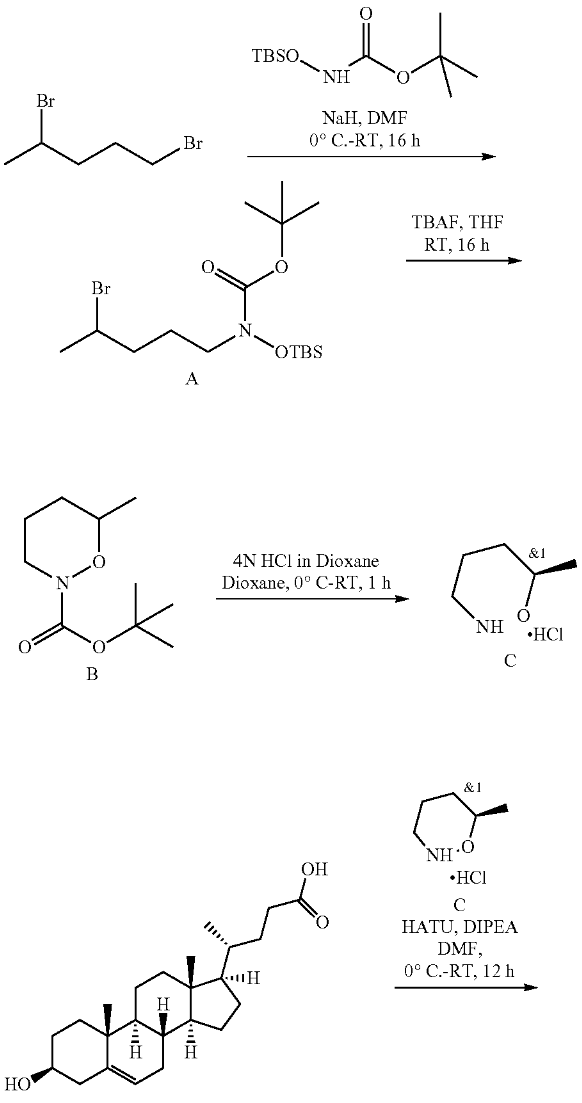

A

B

C

C

3β-hydroxy-5-cholenic acid

-continued

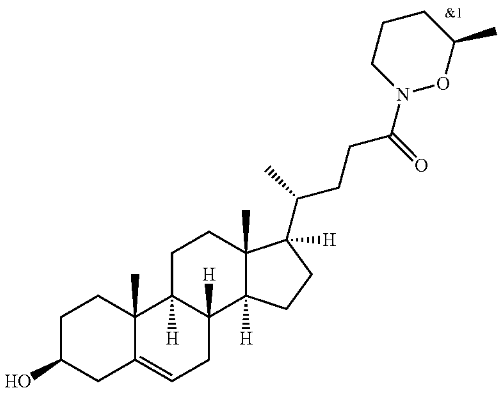

60

To the stirred solution of tert-butyl ((tert-butyldimethylsilyl)oxy)carbamate (Example 68)(1 g, 4.04 mmol) in DMF (10 mL) at 0° C. was added NaH (60% dispersion in mineral oil, 194 mg, 8.08 mmol) portion wise under nitrogen atmosphere. The resultant reaction mixture was stirred at room temperature for 30 min. Followed by added 1,4-dibromopentane (929 mg, 4.04 mmol) at 0° C. The resultant reaction mixture was stirred at room temperature for 16 h. Upon completion, reaction mixture was quenched with ice-water and extracted with ethyl acetate (2×10 mL). The combined organic layer was dried over anhydrous sodium sulfate and concentrated in vacuo to afford crude compound A. The crude compound was purified by column chromatography over 100-200 silica gel mesh to afford compound A (fraction-1, 600 mg, 37%) and compound B (400 mg, 49%) as a colorless oily compound.

To the stirred solution of crude compound A (0.6 g, 1.51 mmol) in THF (6 mL) at 0° C. under nitrogen atmosphere was added TBAF (396 mg, 1.51 mmol). The resultant reaction mixture was allowed to stir at room temperature for 2 h. Upon completion, diluted with water and extracted with ethyl acetate (2×10 mL). The combined organic layer was dried over anhydrous sodium sulfate and concentrated in vacuo to afford crude compound B. The crude compound was purified by column chromatography over 100-200 silica gel mesh with elution of 3% ethyl acetate in hexane to obtain compound B (0.2 g, 66%) as a colorless oily compound. compound B was further confirmed by 2D NMR (HSQC).

To the stirred solution of compound B (0.4 g, 1.99 mmol) in 1,4-dioxane (4 mL) at 0° C. was added HCl solution (4M in 1,4-dioxane, 390 mg, 4.37 mmol) and the resultant reaction mixture was allowed to stir at room temperature for 2 h. Upon completion, the reaction mixture was concentrated in vacuo to obtain a residue which was triturated with diethyl ether to afford crude compound C (190 mg) as a yellow solid.

Compound 60 was synthesized according to the general procedure A using 3β-hydroxy-5-cholenic acid (0.1 g, 0.26 mmol), DIPEA (233 μL, 1.33 mmol), HATU (203 mg, 0.53 mmol), compound C (81 mg, 0.801 mmol), and THF (3 mL). The obtained crude material was purified by column chromatography over 100-200 silica gel mesh by eluting at 35% ethyl acetate in hexane. The combined pure fractions were concentrated under reduced to afford compound 60 (80 mg, 67%) as an off-white solid. LC-MS (ESI) m/z: 458 $[M+H]^+$; $^1H$ NMR (400 MHz, DMSO-$d_6$): δ 5.29-5.24 (m, 1H), 4.58 (d, J=4.8 Hz, 1H), 4.26-4.19 (m, 1H), 3.85-3.76 (m, 1H), 3.28-3.20 (m, 1H), 2.94-2.83 (m, 1H), 2.37-2.03 (m, 5H), 2.00-1.60 (m, 8H), 1.58-1.12 (m, 15H), 1.11-0.83 (m, 11H), 0.65 (s, 3H).

Example 61: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-(methyl)-N-cyclopentoxypentanamide

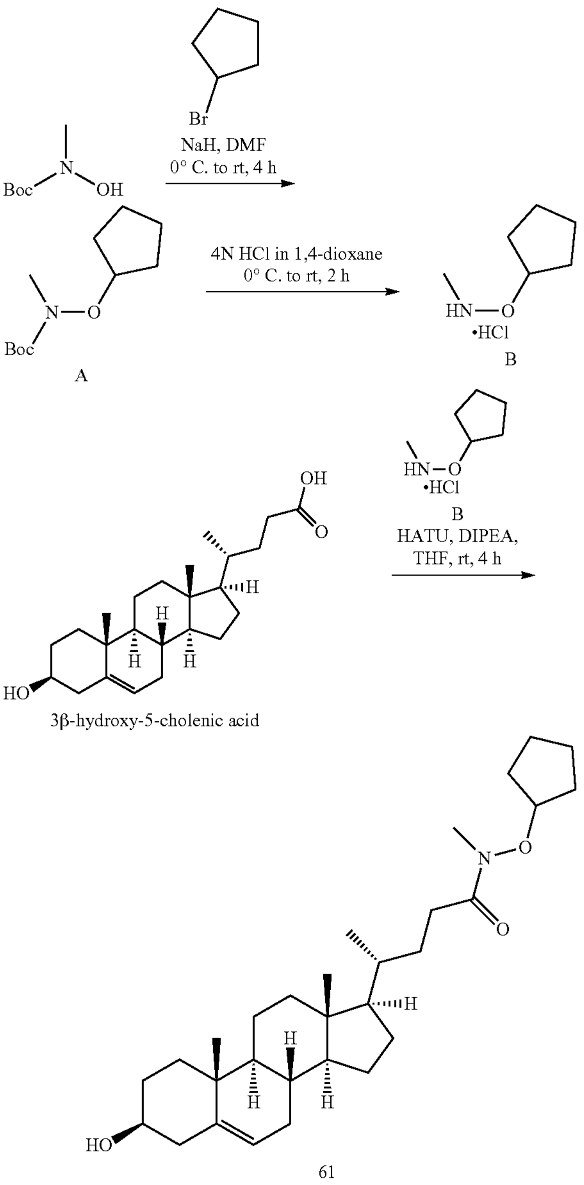

3β-hydroxy-5-cholenic acid

61

To a stirred solution of tert-butyl hydroxy(methyl)carbamate (500 mg, 3.40 mmol) in DMF (10 mL) at 0° C. was added NaH (60% dispersion in mineral oil, 195.26 mg, 8.49 mmol) and stirred for 30 min. following by addition of bromocyclopentane (759.46 mg, 5.10 mmol). The resulting reaction mixture was stirred at room temperature for 4 h. Upon completion, the reaction mixture was concentrated in vacuo, diluted with water (10 mL), and extracted with ethyl acetate (30 mL×3). The combined organic layer was dried over anhydrous sodium sulfate and concentrated in vacuo. The obtained crude compound was and purified by column chromatography over silica gel (60-120 mesh) with 0-5% gradient elution of ethyl acetate in hexanes to afford compound A (350 mg, 47.8%) as a colorless liquid.

To a stirred solution of Compound A (350 mg, 1.63 mmol) in 1,4-dioxane at 0° C. was added HCl (4N HCl in 1,4-dioxane, 4 mL, 4.88 mmol) and the resulting reaction mixture was stirred at room temperature for 2 h. Upon completion, the reaction mixture was concentrated in vacuo. The obtained crude compound was triturated with diethyl ether to afford crude compound B (152 mg, 81%) as a colorless liquid.

Compound 61 was synthesized according to the general procedure A using 3β-hydroxy-5-cholenic acid (150 mg, 0.40 mmol), HATU (152 mg, 0.40 mmol), DIPEA (258 mg, 2.0 mmol), crude compound B (92.25 mg, 0.80 mmol), and THE (1.5 mL). The reaction time was 4 h. The obtained crude material was purified by column chromatography over silica gel (100-200 mesh) with 0-3% gradient elution of MeOH in DCM to afford compound 61 (91 mg, 48%) as an off-white solid. LC-MS (ESI) m/z: 472 $[M+H]^+$; $^1H$ NMR (400 MHz, $CDCl_3$): δ 5.36-5.34 (m, 1H), 4.48-4.44 (m, 1H), 3.55-3.48 (m, 1H), 3.18 (s, 3H), 2.49-2.40 (m, 1H), 2.35-2.22 (m, 3H), 2.03-1.92 (m, 2H), 1.91-1.71 (m, 10H), 1.65-1.58 (m, 2H), 1.52-1.41 (m, 8H), 1.39-1.25 (m, 2H), 1.20-1.01 (m, 5H), 1.00 (s, 3H), 0.99-0.90 (m, 4H), 0.68 (s, 3H).

Example 62: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-(2-hydroxyethyl)-N-methoxypentanamide

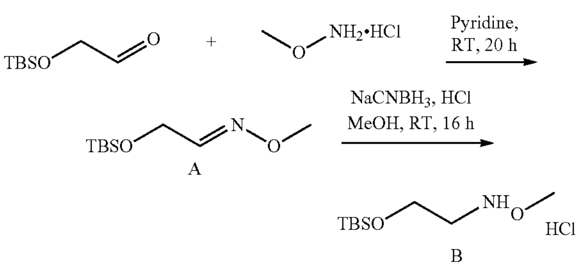

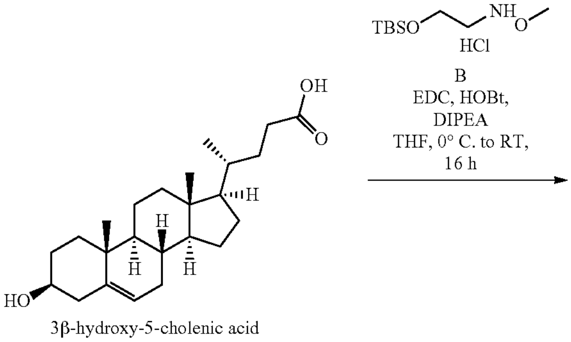

3β-hydroxy-5-cholenic acid

-continued

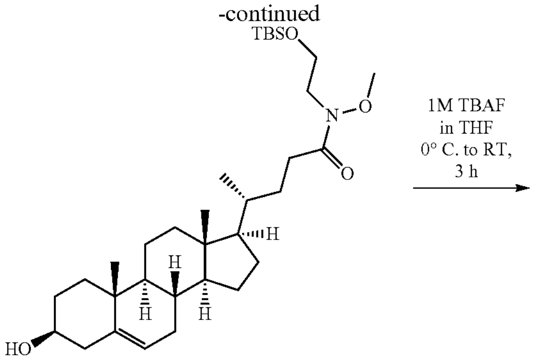

C

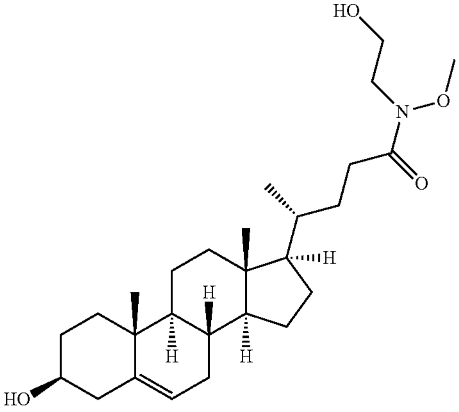

62

To a stirred solution of 2-((tert-butyldimethylsilyl)oxy) acetaldehyde (0.8 g, 4.59 mmol) in pyridine (2 mL, 2.5 vol) was added O-methyl hydroxylamine hydrochloride (1.52 g, 18.36) at room temperature. The resultant reaction mixture was stirred at room temperature for 20 h. Upon completion, the reaction mixture was diluted with water (100 mL) and extracted with $Et_2O$ (30 mL×2). The combined organic layer was dried over sodium sulfate, filtered, and concentrated in vacuo to afford Compound A (E & Z isomers) as an oily liquid (800 mg).

To a stirred solution of crude Compound A (800 mg, 3.93 mmol) in MeOH (5 mL) at 0° C. was added $NaCNBH_3$ (1.48 g, 23.6 mmol) and HCl solution (4M in MeOH, 8 mL) at room temperature. The resultant reaction mixture was stirred at room temperature for 16 h. Upon completion, the reaction mixture was poured into saturated aqueous $NaHCO_3$ (10 ml) and extracted with $Et_2O$ (30 mL×2). The combined organic layer was dried over sodium sulfate, filtered, concentrated in vacuo, and purified by column chromatography over silica gel (100-200 mesh) with 0-20% gradient elution of ethyl acetate in hexanes to afford compound B as a colorless liquid (180 mg, 35%).

Compound C was synthesized according to the general procedure A using 3 (3-hydroxy-5-cholenic acid (150 mg, 0.534 mmol), HATU (305 mg, 0.80 mmol), DIPEA (0.21 mL, 1.2 mmol), compound B (140 mg, 0.681 mmol) and THF (3 mL). After concentration, obtained crude compound C as a gummy liquid (180 mg).

Compound 62 was synthesized according to the general procedure C using Compound D (180 mg, 0.32 mmol), TBAF (1M in THF, 0.96 mL, 0.961 mmol), and THF (4 mL). The reaction time was 4 h. The obtained crude material was purified by column chromatography over silica gel (100-200 mesh) with 0-50% gradient elution of ethyl acetate in hexanes to afford compound 62 as an off-white solid (87 mg, 34%). LC-MS (ESI) m/z: 448.1 $[M+H]^+$; $^1H$ NMR (400 MHz, DMSO-$d_6$): δ 5.27-5.25 (m, 1H), 4.72 (brs, 1H), 4.59 (d, J=4.8 Hz, 1H), 3.64 (s, 3H), 3.57 (t, J=5.6 Hz, 2H), 3.48 (q, J=5.6 Hz, 2H), 3.26-3.22 (m, 1H), 2.37-2.22 (m, 2H), 2.18-2.02 (m, 2H), 1.99-1.86 (m, 2H), 1.85-1.72 (m, 2H), 1.71-1.61 (m, 2H), 1.59-1.44 (m, 3H), 1.43-1.31 (m, 4H), 1.30-1.18 (m, 2H), 1.17-1.03 (m, 3H), 1.02-0.96 (2H), 0.94 (s, 3H), 0.93-0.83 (m, 4H), 0.64 (s, 3H).

Example 63: N—((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N-methoxyglycine

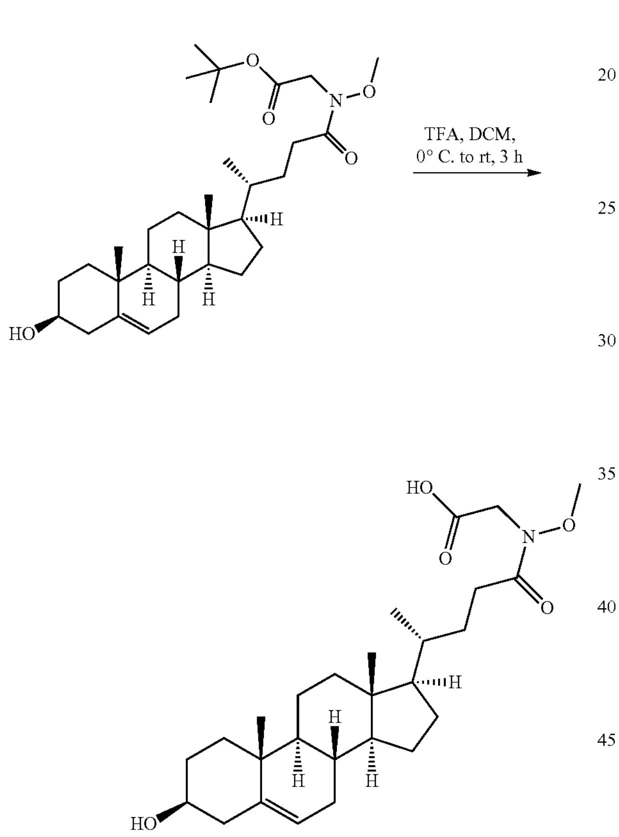

63

To a stirred solution of Example 75 (0.1 g, 0.193 mmol) in DCM (5 mL) was added trifluoroacetic acid (1 mL) at 0° C. The resultant reaction mixture was allowed to stir at room temperature for 3 h. Upon completion, the reaction mixture was concentrated in vacuo to get crude compound that was triturated with diethyl ether to afford Compound 63 (27 mg, 30%) as a light brown solid. LC-MS (ESI) m/z: 461.8 $[M+H]^+$; $^1H$ NMR (400 MHz, DMSO-$d_6$) δ 12.81 (bs, 1H), 5.28-5.25 (m, 1H), 4.62-4.53 (m, 1H), 4.18 (brs, 2H), 3.64 (s, 3H), 3.28-3.20 (m, 1H), 2.16-2.07 (m, 2H), 2.00-1.86 (m, 2H), 1.85-1.64 (m, 4H), 1.62-1.37 (m, 6H), 1.35-1.15 (m, 4H), 1.14-0.96 (m, 5H), 0.95 (s, 3H), 0.94-0.86 (m, 4H), 0.65 (s, 3H).

Example 64: (R)—N-(2-aminoethyl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methoxypentanamide

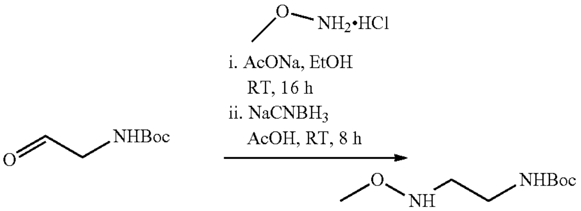

A

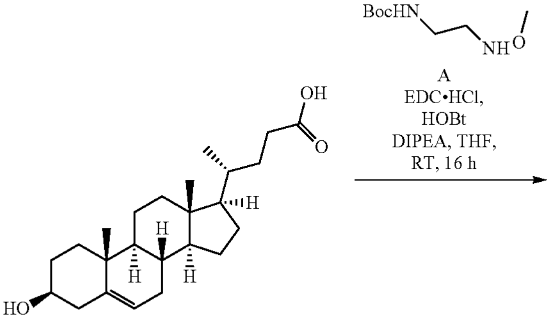

3β-hydroxy-5-cholenic acid

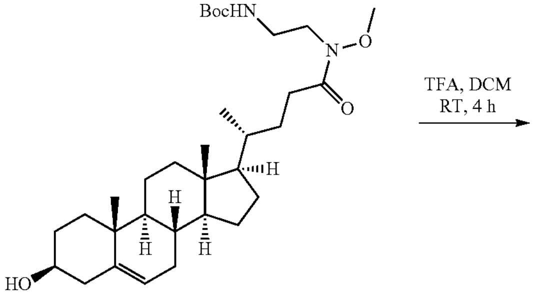

B

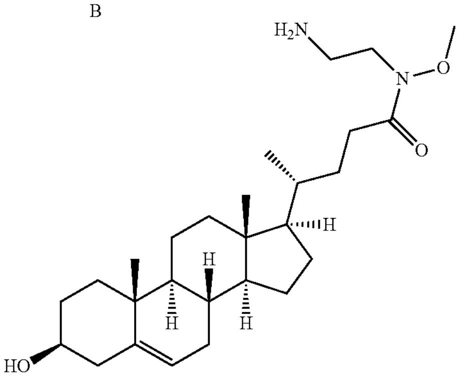

64

To a stirred solution of tert-butyl (2-oxoethyl)carbamate (0.5 g, 3.14 mmol) in ethanol (5 mL) at 0° C. were added compound O-methylhydroxylamine hydrochloride (126 mg, 1.51 mmol) and sodium acetate (206 mg, 2.5 mmol) at 0° C. under nitrogen atmosphere. The resultant reaction mixture was stirred at room temperature for 16 h. $NaCNBH_3$ (233 mg, 3.72 mmol) and acetic acid (188 mg, 3.14 mmol) were added at room temperature and the resulting reaction mixture was stirred at room temperature for 8 h. Upon completion, the reaction mixture was quenched with $NaHCO_3$ solution (20 mL) and extracted with ethyl acetate (30 mL×3). The combined organic layer was dried over sodium sulfate, filtered, concentrated in vacuo, and purified by column chromatography over silica gel (100-200 mesh) with 0-50% gradient elution of ethyl acetate in hexanes to afford compound A as an off-white solid (150 mg, 25%).

Compound B was synthesized according to the general procedure B using 3β-hydroxy-5-cholenic acid (130 mg, 0.347 mmol) EDC.HCl (99 mg, 0.521 mmol), HOBt (51.6 mg, 0.382 mmol) DIPEA (0.184 mL, 1.042 mmol), compound A (79.2 mg, 0.417 mmol), and THE (10 mL). The crude material was purified by silica gel chromatography (0-50% ethyl acetate:hexanes) to afford the compound B (50 mg, 22.8%) as an off-white solid. ELSD-MS (ESI) m/z: 446.7 $[M-100+H]^+$.

To a stirred solution of compound B (150 mg, 0.274 mmol) in DCM (5 mL) at 0° C. was added TFA (0.5 mL) under nitrogen atmosphere. The resultant reaction mixture was stirred at room temperature for 4 h. Upon completion, the reaction mixture was concentrated and basified with saturated aqueous $NaHCO_3$ (10 mL) and extracted with ethyl acetate (20 mL×3). The combined organic layer was dried over sodium sulfate, filtered, concentrated in vacuo, and purified by column chromatography over silica gel (100-200 mesh) with 0-50% gradient elution of ethyl acetate in hexanes to afford compound 64 as an off-white solid (41 mg, 33%). ELSD-MS (ESI) m/z: 446.9 $[M+H]^+$; $^1H$ NMR (400 MHz, $CDCl_3$): δ 7.70 (t, J=5.6 Hz, 1H), 6.54 (t, J=6 Hz, 1H), 5.27-5.25 (m, 1H), 4.59 (d, J=4.4 Hz, 1H), 3.37 (s, 3H), 3.31-3.10 (m, 3H), 2.81-2.75 (m, 2H), 2.17-2.02 (m, 3H), 2.01-1.87 (m, 3H), 1.86-1.72 (m, 2H), 1.71-1.59 (m, 2H), 1.58-1.43 (m, 3H), 1.41-1.27 (m, 4H), 1.26-0.96 (m, 7H), 0.93 (s, 3H), 0.91-0.82 (m, 4H), 0.64 (s, 3H).

Example 65: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methoxy-N-(3,3,3-trifluoropropyl) pentalamide

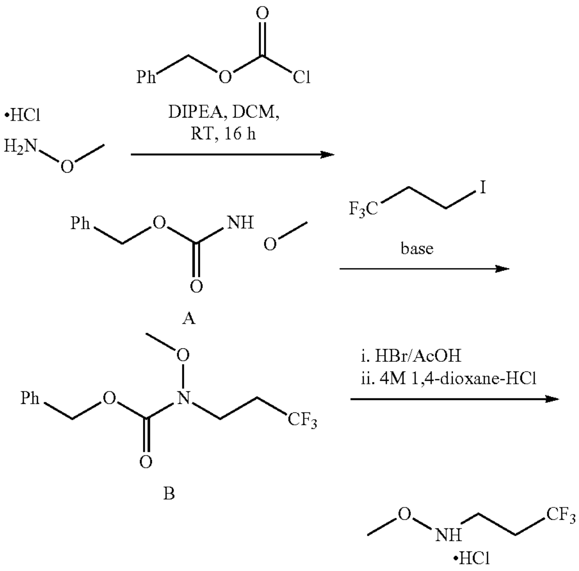

A

B

C

-continued

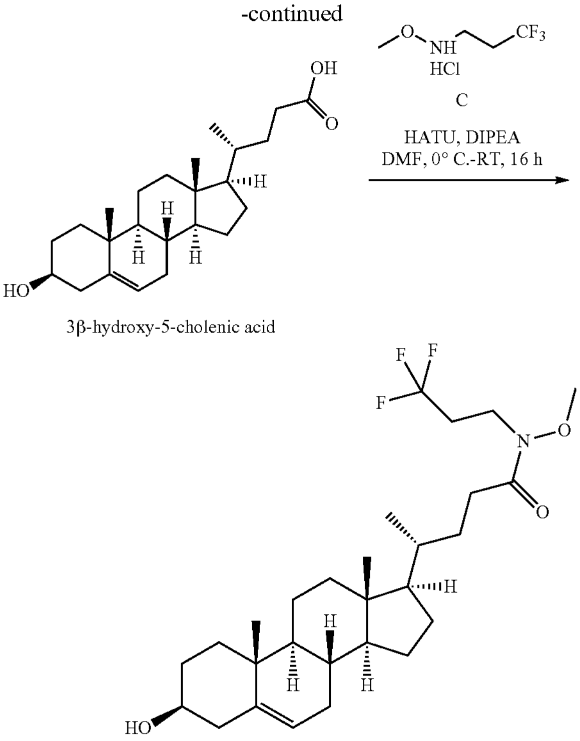

C

3β-hydroxy-5-cholenic acid

65

To a stirred solution of O-methyl hydroxylamine hydrochloride (1 g, 12 mmol) in DCM (10 mL) was added DIPEA (4.64 g, 35.9 mmol) followed by benzyl chloroformate (2.04 g, 12 mmol) at 0° C. under argon atmosphere. The resultant reaction mixture was stirred at room temperature for 16 h. Upon completion, the reaction mixture was poured into ice water (10 mL) and extracted with ethyl acetate (3×20 mL). The combined organic layer was washed with brine (10 mL), dried over anhydrous sodium sulphate, and concentrated under high vacuum to afford crude material. The crude material was purified by column chromatography over silica gel (100-200 mesh) with gradient elution of 0-30% of ethyl acetate in hexane to afford compound A (1 g, 46.09%) as a brown gummy liquid.

To a stirred solution of compound A (0.8 g, 4.42 mmol) in DMF (3 mL) was added NaH (60% dispersion in mineral oil, 212 mg, 8.83 mmol) at 0° C. under argon atmosphere, followed by addition of 1,1,1-trifluoro-3-iodopropane (1.98 g, 8.83 mmol). The resultant reaction mixture was stirred at room temperature for 4 h. Upon completion, the reaction mixture was poured into ice-cold water (5 mL) and extracted with ethyl acetate (3×20 mL). The combined organic layer was washed with brine (10 mL), dried over anhydrous sodium sulphate, and concentrated in vacuo to afford crude material. The crude material was purified by column chromatography over silica gel (100-200 mesh) using gradient elution of 0-20% ethyl acetate in hexane to afford pure compound B (0.2 g, 16.34%) as a brown gummy liquid.

Compound B (0.1 g, 0.36 mmol) was charged into a round bottom flask followed by 33% HBr in acetic acid (1 mL, 1.08 mmol) at 0° C. under argon atmosphere. The resulting reaction mixture was stirred at room temperature for 4 h. Upon completion, the reaction mixture was poured into saturated aqueous sodium bicarbonate (5 mL) and extracted with DCM (2×10 mL). The combined organic layer was cooled to 0° C., then was added HCl solution (4M in 1,4 dioxane, 1 mL, 0.72 mmol) drop wise and stirred for ten minutes at the same temperature. The reaction mixture was concentrated and co-distilled with toluene to get crude compound which was triturated with diethyl ether to get pure compound C (50 mg, 77.2%) an off-white solid.

Compound 65 was synthesized according to the general procedure A using 3-β-hydroxy-5-cholenoic acid (150 mg, 0.4 mmol), DIPEA (259 mg, 2.01 mmol), HATU (382 mg, 1 mmol) compound C (79 mg, 0.552 mmol), and DMF (3 mL). The reaction time was 16 h. The obtained crude compound was purified by column chromatography over silica gel (100-200 mesh) with gradient elution of 40-60% ethyl acetate in hexane to afford the title compound 65 (58.8 mg, 23.45%) as an off-white solid. LC-MS (ESI) m/z: 478.0 $[M+H]^+$; $^1H$ NMR (400 MHz, $CDCl_3$): δ 5.36-5.34 (m, 1H), 3.86-3.81 (m, 2H), 3.71 (s, 3H), 3.55-3.49 (m, 1H), 2.50-2.20 (m, 5H), 2.02-1.92 (m, 2H), 1.90-1.75 (m, 4H), 1.64-1.41 (m, 9H), 1.40-1.24 (m, 2H), 1.22-1.02 (m, 5H), 1.01 (s, 3H), 0.99-0.92 (m, 4H), 0.68 (s, 3H). $^{19}F$ NMR (376 MHz, $CDCl_3$) δ-65.50 (s, $-CF_3$).

Example 66: (4R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-(1-hydroxypropan-2-yl)-N-methoxypentanamide

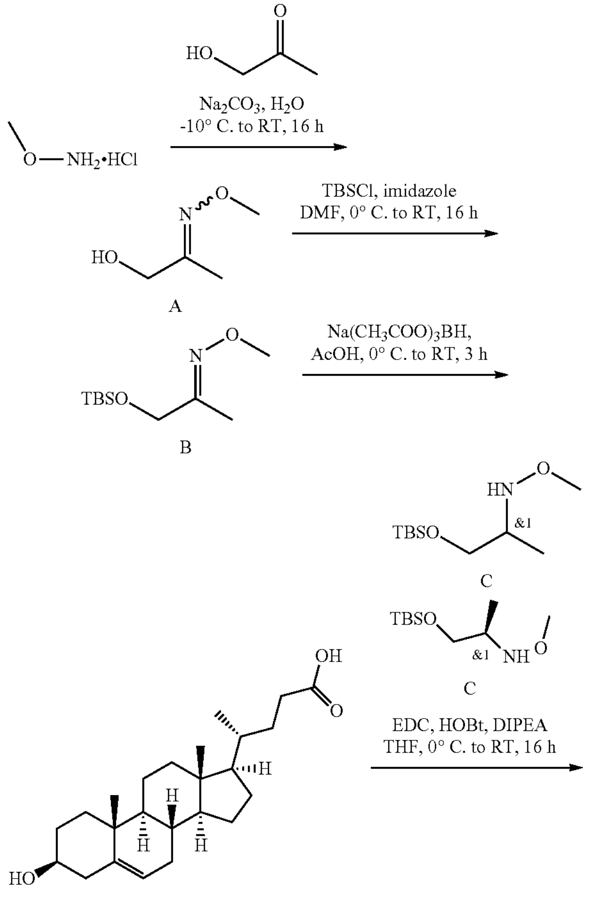

A

B

C

C

3β-hydroxy-5-cholenic acid

-continued

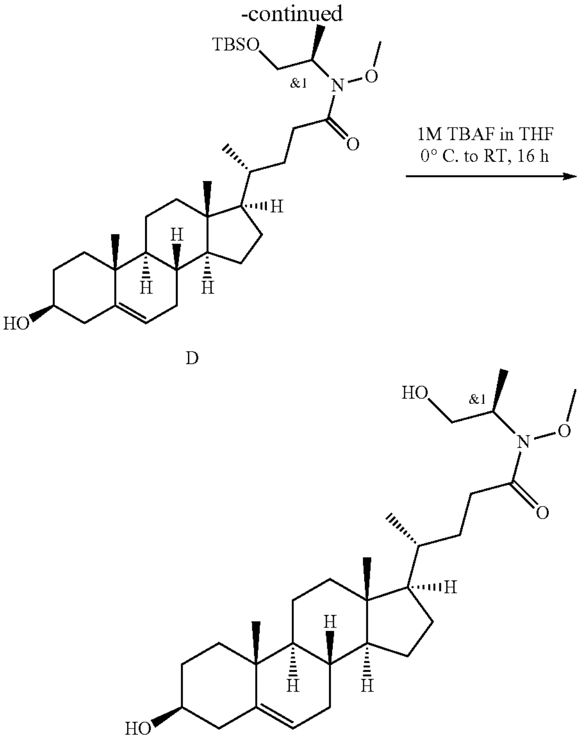

D

66

To a stirred solution of O-methyl hydroxylamine hydrochloride (1 g, 13.5 mmol) in $H_2O$ (15 mL) at 0° C. was added hydroxyacetone (1.13 g, 13.5 mmol) and $Na_2CO_3$ (1.7 g, 20.2 mmol). The resultant reaction mixture was stirred at room temperature for 16 h. Upon completion, the reaction mixture was diluted with water (100 mL) and extracted with ethyl acetate (500 mL×3). The combined organic layer was dried over sodium sulfate, filtered, and concentrated in vacuo to afford compound A as an oily liquid (2 g).

To a stirred solution of compound A (2 g, 19.6 mmol) in DCM (5 mL) at 0° C. was added imidazole (2.67 g, 39.2 mmol) and TBDMSCl (3.24 g, 21.5 mmol). The resultant reaction mixture was stirred at room temperature for 16 h. Upon completion, the reaction mixture was diluted with water (100 mL) and extracted with ethyl acetate (200 mL×3). The combined organic layer was washed with brine (100 mL), dried over sodium sulfate, filtered, concentrated in vacuo, and purified by column chromatography over silica gel (100-200 mesh) with 0-20% gradient elution of ethyl acetate in hexanes to afford compound B as a yellow liquid (1 g, 23%).

To a stirred solution of compound B (200 mg, 0.92 mmol) in AcOH (5 mL) at 0° C. was added $NaBH(OAc)_3$ (487 mg, 2.3 mmol). The resulting reaction mixture was stirred at room temperature for 3 h. Upon completion, the reaction mixture was basified with saturated aqueous $NaHCO_3$ (20 mL) and extracted with ethyl acetate (50 mL×2). The combined organic layer was dried over sodium sulfate, filtered, concentrated in vacuo, and purified by column chromatography over silica gel (100-200 mesh) with 0-70% gradient elution of ethyl acetate in hexanes to afford compound C as a yellow liquid (180 mg, 35%).

Compound D was synthesized according to the general procedure B using 3β-hydroxy-5-cholenic acid (200 mg, 0.534 mmol), EDC.HCl (154 mg, 0.80 mmol), HOBt (108 mg, 0.80 mmol), DIPEA (0.28 mL, 1.6 mmol), compound C (141 mg, 0.641 mmol), and THF (5 mL). The obtained crude material was purified by column chromatography over silica gel (100-200 mesh) with 0-50% gradient elution of ethyl acetate in hexanes to afford compound D as an off-white solid (180 mg, 58%).

Compound 66 was synthesized according to the general procedure C using Compound D (180 mg, 0.313 mmol), TBAF (1M in THF, 0.62 mL, 0.625 mmol), and THF (5 mL). The reaction time was 16 h. The obtained crude material was purified by column chromatography over silica gel (100-200 mesh) with 0-5% gradient elution of MeOH in DCM to afford the title compound 66 as an off-white solid (60 mg, 41%). ELSD-MS (ESI) m/z: 461.9 $[M+H]^+$; $^1H$ NMR (400 MHz, DMSO-$d_6$) δ 5.26-5.25 (m, 1H), 4.76 (brs, 1H), 4.58 (brs, 1H), 4.25 (brs, 1H), 3.69 (s, 3H), 3.50-3.42 (m, 1H), 3.25-3.20 (m, 1H), 3.02-2.98 (m, 1H), 2.33-2.25 (m, 1H), 2.17-2.05 (m, 2H), 1.99-1.86 (m, 2H), 1.84-1.73 (m, 2H), 1.72-1.61 (m, 3H), 1.59-1.45 (m, 3H), 1.43-1.33 (m, 4H), 1.31-1.21 (m, 2H), 1.19-1.10 (m, 2H), 1.09-1.05 (m, 4H), 1.02-0.96 (2H), 0.94 (s, 3H), 0.93-0.83 (m, 5H), 0.64 (s, 3H).

Example 67: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-isobutyl-N-methoxypentanamide

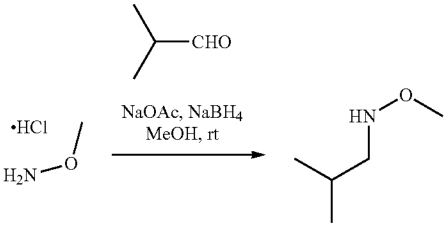

A

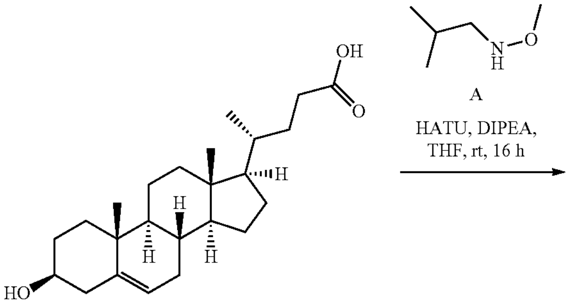

3β-hydroxy-5-cholenic acid

-continued

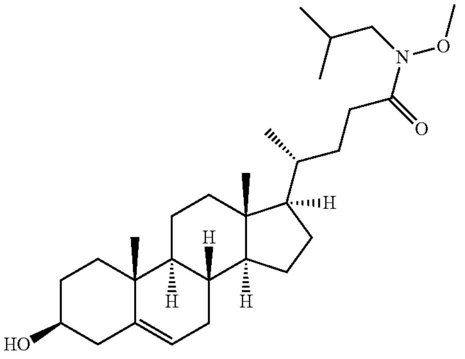

67

To a stirred solution of O-methylhydroxylamine hydrochloride (1 g, 12 mmol) in methanol (10 mL) at 0° C. were added 2-methylpropanal (2.59 g, 35.9 mmol) and sodium acetate (982 mg, 12 mmol). The reaction mixture was stirred at 0° C. for 2 h and followed by addition of sodium borohydride (906 mg, 23.9 mmol) portion wise. The resultant reaction mixture was allowed stir at room temperature for 16 h. Upon completion, the reaction mixture was quenched with water (20 mL) and extracted with DCM (50 mL×3). The combined organic layer was dried over sodium sulfate, filtered, and the solvent evaporated by purging with $N_2$ gas to afford crude compound A (1.2 g) as a pale-yellow liquid.

Compound 67 was synthesized according to the general procedure A using 3β-hydroxy-5-cholenic acid (100 mg, 0.26 mmol), HATU (203 mg, 0.54 mmol), DIPEA (173 mg, 1.33 mmol), crude compound A (55 mg, 0.53 mmol), and THE (2 mL). The reaction time was 4 h. The obtained crude material was purified by column chromatography over silica gel (100-200 mesh) with 0-60% gradient elution of MeOH in DCM to afford semi pure compound, which was further purified by preparative HPLC [Column: Gemini 3 μm NX-C18 110A 50*2 mm; mobile phase-A:0.01% FA in water, mobile phase-B:100% ACN, program (Time/% B):0.01/5, 6.0/90, 8.00/90, 10.01/05, flow: 0.6 ml/min] to afford compound 67 (8.6 mg, 7%) as a light pink solid. LC-MS (ESI) m/z: 460 $[M+H]^+$; $^1H$ NMR (400 MHz, DMSO-$d_6$): δ 5.27-5.25 (m, 1H), 4.58 (d, J=4.4 Hz, 1H), 3.63 (s, 3H), 3.40-3.32 (m, 2H), 2.50-2.41 (m, 4H), 2.18-2.02 (m, 3H), 1.98-1.85 (m, 3H), 1.84-1.62 (m, 4H), 1.60-1.30 (m, 7H), 1.29-0.96 (m, 6H), 0.94 (s, 3H) 0.93-0.82 (m, 9H), 0.64 (s, 3H).

Example 68: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-5-hydroxy-5-methyl-1,2-oxazinan-2-yl)pentan-1-one

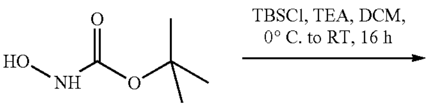

-continued

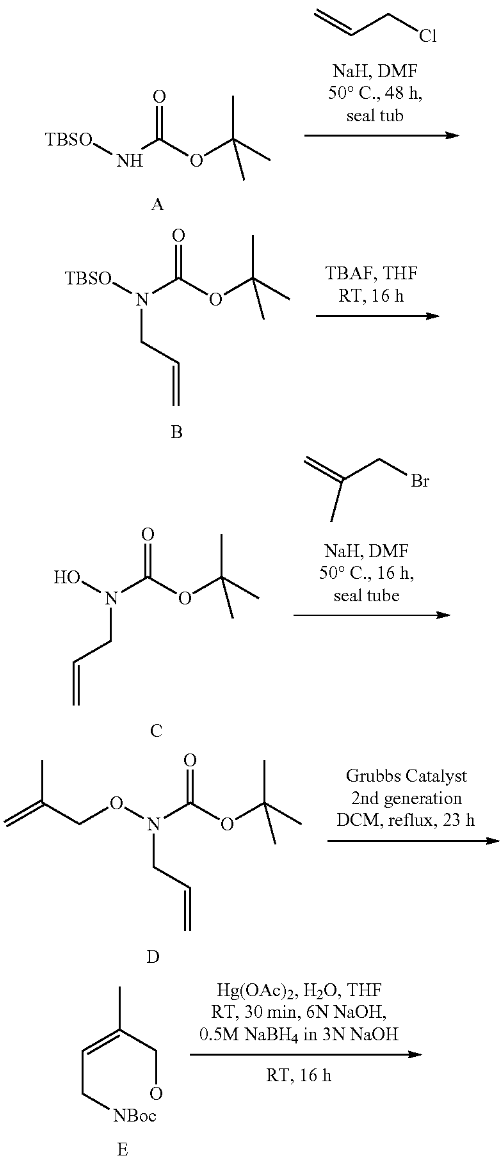

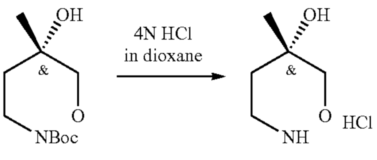

F G

3β-hydroxy-5-cholenic acid

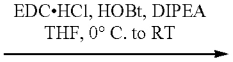

-continued

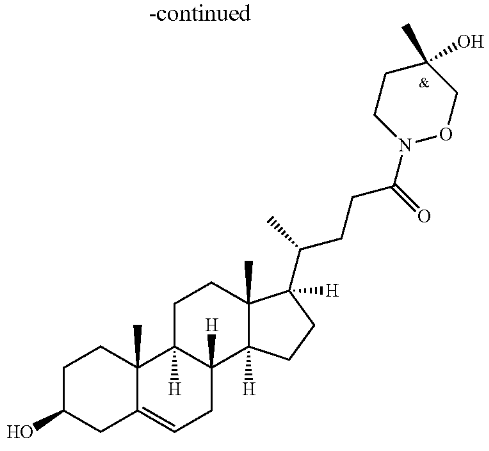

68

To a stirred solution of tert-butyl N-hydroxy carbamate (5 g, 37.6 mmol) in anhydrous DCM (20 mL, 312 mmol) at 0° C. was added triethylamine (16 mL, 113 mmol) followed by tert-butyl(chloro) dimethyl silane (11.3 g, 75.1 mmol) and the resulting reaction mixture was stirred at room temperature for 16 h. Upon completion, the reaction mixture was diluted with water and extracted with DCM (2×100 mL), and the combined organic layers was dried over anhydrous sodium sulfate and concentrated in vacuo to get a crude compound A (7 g, 28.3 mmol) as a yellow liquid.

To a stirred solution of crude compound A (2 g, 8.08 mmol) in dimethylformamide (60 mL, 775 mmol) at 0° C. was added NaH (60% dispersion in mineral oil, 356 mg, 8.89 mmol), followed by 3-chloroprop-1-ene (1.86 g, 24.3 mmol). The reaction mixture was stirred at 50° C. for 48 h. The reaction was monitored by TLC. Upon completion, the reaction mixture was then diluted with water and extracted with ethyl acetate (2×200 mL), and the combined organic layers was dried over anhydrous sodium sulfate, filtered, concentrated in vacuo, and purified by column chromatography over silica gel (100-200 mesh) using 0-10% gradient elution of ethyl acetate in hexanes to afford compound B as a yellow liquid (1.2 g, 51%).

To a stirred solution of compound B (1.2 g, 4.17 mmol) in THF (15 mL, 184 mmol) at 0° C. was added tetrabutylammonium fluoride solution (1M in THF, 1.2 mL) and the resultant reaction mixture was stirred at ambient temperature for 16 h. Upon completion, the reaction mixture was quenched with water and extracted with ethyl acetate (2×100 mL), the combined organic layer was dried over anhydrous sodium sulfate, filtered, concentrated in vacuo and purified by column chromatography over silica gel (100-200 mesh) with 0-20% gradient elution of ethyl acetate in hexanes to afford compound C as a yellow liquid (0.3 g, 41%).

To a stirred solution of compound C (0.4 g, 2.31 mmol) in DMF (4 mL, 51.7 mmol) at 0° C. was added NaH (60% dispersion in mineral oil, 50.8 mg, 1.27 mmol) followed by 3-bromo-2-methylprop-1-ene (468 mg, 3.46 mmol). The resultant reaction mixture was stirred at 50° C. for 16 h. Upon completion, the reaction mixture was diluted with water and extracted with ethyl acetate (2×50 mL), and the combined organic layer was dried over anhydrous sodium sulfate, filtered, concentrated in vacuo, and purified by column chromatography over silica gel (100-200 mesh) with 1-10% gradient elution of ethyl acetate in hexanes to afford compound D as a yellow liquid (250 mg, 95%).

To a stirred solution of compound D (250 mg, 1.1 mmol) in dichloromethane (25 mL, 390 mmol) at ambient temperature was added Grubbs $2^{nd}$ generation catalyst (25 mg) and the resultant reaction mixture was stirred at reflux for 23 h. Upon completion, the reaction mixture was concentrated to get a crude product (350 mg), that was purified by column chromatography over silica gel (100-200 mesh) with 1-5% gradient elution of ethyl acetate in hexanes to afford compound E as a brown liquid (130 mg, 59%).

To a ten minute stirred solution of (acetyloxy)mercuric acetate (446 mg, 1.4 mmol) in water (4 mL, 222 mmol) and THF (4 mL, 49.1 mmol) was added compound E (0.2 g, 933 μmol) at ambient temperature and the resultant reaction mixture was stirred at same temperature for 16 h. 6N sodium hydroxide (1.2 mL) and 0.5M sodium borohydride in NaOH (3N, 2.4 mL) were then added. The reaction mixture was stirred at ambient temperature for another 4 h. Upon completion, the reaction mixture filtered through pad of Celite and washed with ethyl acetate (50 mL). The collected filtrate was dried over anhydrous sodium sulfate, filtered, concentrated in vacuo, and purified by column chromatography over silica gel (100-200 mesh) with 20-40% gradient elution of ethyl acetate in hexanes to afford compound F as a brown liquid (100 mg, 46%).

To a stirred solution of compound F (0.2 g, 861 μmol) in 1,4-dioxane (4 mL, 46.9 mmol) at 0° C. was added 4M HCl in dioxane (1 mL) and the resultant reaction mixture was stirred at room temperature for 3 h. Upon completion, the reaction mixture was concentrated in vacuo to afford crude compound G as a brown liquid (150 mg, 60%).

Compound 68 was synthesized according to the general procedure B using 3β-hydroxy-5-cholenic acid (200 mg, 133 μmol), DIPEA (0.6 mL, 0.8 mmol), EDC.HCl (124 mg, 801 μmol), HOBt (79 mg, 587 μmol), crude compound G (crude) (130 mg, 1.6 mmol), and THF (6 mL). The reaction time was 16 h. The obtained crude compound was purified by preparative HPLC [column: Kinetix C18 2.0*50 mm, 3 μm; mobile phase A: 0.01% FA in water; mobile phase B: 100% acetonitrile; flow rate: 0.5 ml/min; program (Time/% B): 0.05/5, 2.0/60, 5.50/75, 5.0/85] to afford compound 68 (30 mg, 11%) as an off-white solid. LC-MS (ESI) m/z 473.9 $(M+H)^+$; $^1H$ NMR (400 MHz, DMSO-$d_6$): δ 5.27-5.26 (m., 1H), 4.78 (s, 1H), 4.58 (d, J=4.8 Hz, 1H), 3.82-3.74 (m, 1H), 3.67-3.58 (m, 3H), 3.28-3.23 (m, 1H), 2.31-2.20 (m, 2H), 2.19-2.03 (m, 2H), 1.98-1.72 (m, 4H), 1.69-1.61 (m, 2H), 1.59-1.30 (m, 9H), 1.29-1.04 (m, 8H), 1.02-0.96 (m, 2H), 0.94 (s, 3H), 0.90-0.88 (m, 4H), 0.64 (s, 3H).

Example 69: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N—((S)-2-hydroxypropyl)-N-methoxypentanamide

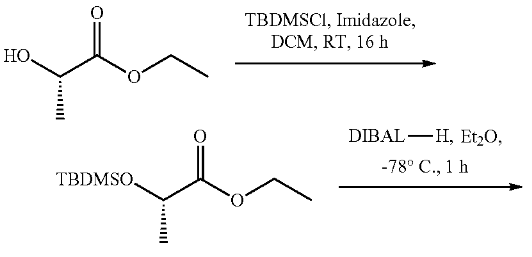

A

-continued

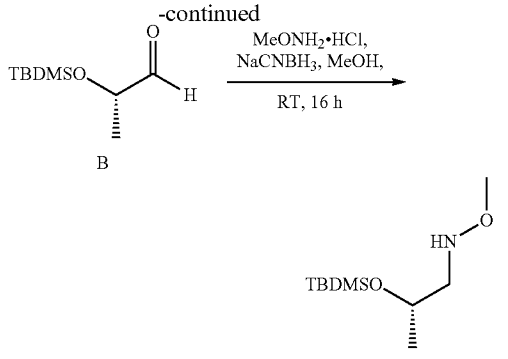

B

C

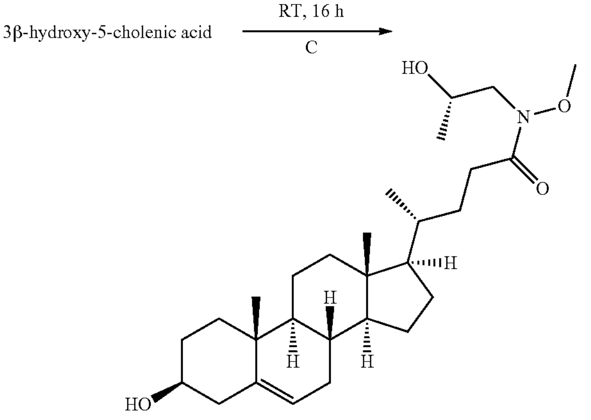

69

To a stirred solution of ethyl (S)-2-hydroxypropanoate (2 g, 16.9 mmol) in anhydrous DCM (20 mL, 312 mmol) at 0° C. were added imidazole (1.73 g, 25.4 mmol) and TBDMSCl (3.06 g, 20.3 mmol). The resultant reaction mixture was allowed to stir at room temperature for 16 h. Upon completion, the reaction mixture was quenched with water and extracted with DCM (2×10 mL). The combined organic layer was washed with brine, dried over anhydrous sodium sulfate, and concentrated in vacuo to obtained crude compound. The crude compound was purified by column chromatography over 100-200 silica gel mesh by eluting 2% ethyl acetate in hexane to afford compound A (2.5 g, 64%) as a colorless liquid.

To a stirred solution of compound A (1 g, 4.3 mmol) in diethyl ether (10 mL) at −78° C. was added DIBAL-H (1M in hexane, 2.4 mL, 4.3 mmol) dropwise. The resultant reaction mixture was allowed to stir at −78° C. for 1 h. Upon completion, the reaction mixture was quenched with saturated aqueous sodium potassium tartrate and extracted with DCM (2×10 mL). The combined organic layer was dried over anhydrous sodium sulfate and concentrated in vacuo to afford crude compound B (650 mg, 80%) as colorless liquid. The crude compound was used in the next step without further purification.

To a stirred solution of compound B (0.2 g, 1.06 mmol) in methanol (3.55 mL) at 0° C. were added O-methyl hydroxylamine hydrochloride (177 mg, 2.12 mmol) and acetic acid (0.1 mL, 1.75 mmol). The reaction mixture was allowed to warm up to room temperature and stirred for 2 h, followed by added $NaCNBH_3$ (133 mg, 2.12 mmol) portion wise at 0° C. The resultant reaction mixture was stirred at room temperature for 16 h. Upon completion, the reaction mixture was diluted with ice cold water and extracted with DCM (2×5 mL). The combined organic layer was dried over anhydrous sodium sulfate and concentrated in vacuo to afford crude compound C (120 mg, 51%) as a colorless liquid.

Compound 69 was synthesized according to the general procedure A using 3β-hydroxy-5-cholenic acid (70 mg, 0.187 mmol), DIPEA (163 μL, 0.934 mmol), HATU (142 mg, 0.374 mmol), compound C (120 mg, 0.548 mmol), and THF (2 mL). The crude compound was purified by preparative HPLC [Column: Kinetix C18 (250*21.2 mm), 5μ; Mobile Phase-A: 0.1% FA in water, Mobile Phase-B: 100% ACN; Flow rate: 13 ml/min; program (Time/% B): 0/30,15/80,25/95; Solubility: ACN+$H_2O$+THF] to afford the title compound 69 (15 mg, 32.5 μmol) as an off-white solid. LC-MS (ESI) m/z: 462 $[M+H]^+$; $^1H$ NMR (400 MHz, DMSO-$d_6$): δ 5.26 (brs, 1H), 4.70 (brs, 1H), 4.59 (d, J=4.8 Hz, 1H), 3.83-3.80 (m, 1H), 3.64 (s, 3H), 3.53-3.48 (m, 1H), 3.42-3.39 (m, 1H), 3.26-3.19 (m, 2H), 2.60-2.55 (m, 2H), 2.19-2.06 (m, 2H), 1.98-1.89 (m, 2H), 1.82-1.72 (m, 2H), 1.69-1.62 (m, 2H), 1.58-1.43 (m, 3H), 1.42-1.31 (m, 4H), 1.30-0.95 (m, 9H), 0.94 (s, 3H), 0.92-0.85 (m, 4H), 0.65 (s, 3H).

Example 70: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N—((R)-2-hydroxypropyl)-N-methoxypentanamide

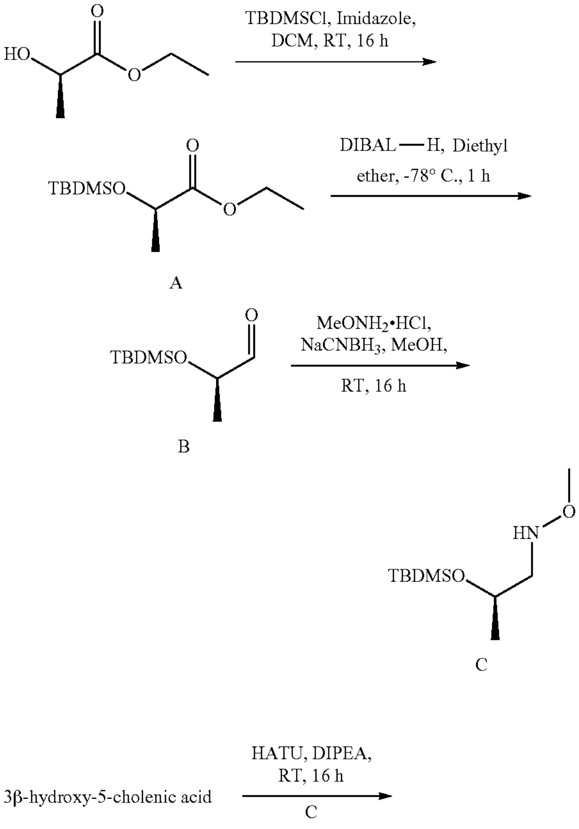

-continued

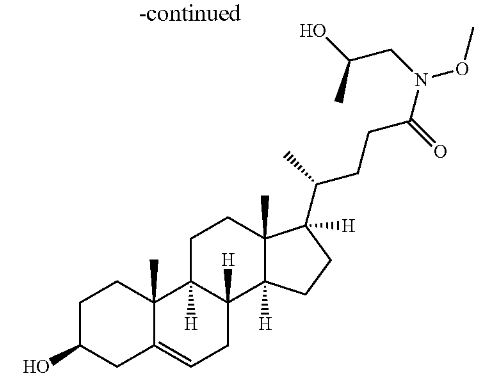

70

To a stirred solution of ethyl (2R)-2-hydroxypropanoate (2 g, 16.9 mmol) in dichloromethane (20 mL, 312 mmol) at 0° C. were added 1H-imidazole (1.73 g, 25.4 mmol) and TBDMSCl (3.06 g, 20.3 mmol). The resultant reaction mixture was allowed to stir at room temperature for 16 h. Upon completion, the reaction mixture was diluted with water and extracted with DCM (2×20 mL). The combined organic layer was washed with brine, dried over anhydrous sodium sulfate, and concentrated in vacuo to afford crude. The crude compound was purified by column chromatography over 100-200 silica gel mesh with elution of 2% ethyl acetate in hexane to afford compound A (2.5 g, 64%) as a colorless liquid.

To a stirred solution of compound A (2 g, 8.61 mmol) in diethyl ether (15 mL, 144 mmol) at −78° C. was added DIBAL-H (1M in hexane, 1.22 g, 8.61 mmol) dropwise. The resultant reaction mixture was stirred at −78° C. for 1 h. Upon completion, the reaction mixture was quenched with saturated aqueous sodium potassium tartrate (5 mL) and extracted with DCM (2×10 mL). The combined organic layer was dried over anhydrous sodium sulfate and concentrated in vacuo to afford crude compound B (1 g, 62%) as a colorless liquid. The crude compound was used for next step without further purification.

To a stirred solution of crude compound B (1 g, 5.31 mmol) in methanol (8.33 mL, 206 mmol) at 0° C. were added O-methylhydroxylamine (750 mg, 15.9 mmol) and acetic acid (0.1 mL, 1.75 mmol). The resultant reaction mixture was allowed to stir at room temperature for 2 h. Then, was added $NaCNBH_3$ (667 mg, 10.6 mmol) portion wise at 0° C. and the reaction mixture was stirred at room temperature for 16 h. Upon completion, ice-water was added to the reaction mixture, and it was extracted with 10% methanol in DCM (2×10 mL). The combined organic layer was dried over anhydrous sodium sulfate and concentrated in vacuo to afford crude compound C (350 mg, 30%) as a colorless liquid.

Compound 70 was synthesized according to the general procedure A using 3β-hydroxy-5-cholenic acid (0.1 g, 0.267 mol), DIPEA (173 mg, 1.33 mmol), HATU (203 mg, 534 mol), crude compound C (176 mg, 801 μmol) and dry THE (5 mL). The obtained crude material was purified by preparative HPLC [Column: Gemini 3 μm NX-C18 110A LC column 50*2 mm; mobile phase:(A): 0.01% FA in water, mobile phase:(B): 100% ACN; flow: 0.6 ml/min; program (time % B): 0.01/5,6.0/90,8.00/90,10.01/05] to afford compound 70 (22 mg, 18%) as an off-white solid. LC-MS (ESI) m/z: 462 $[M+H]^+$; $^1H$ NMR (400 MHz, DMSO-$d_6$): δ 5.28-5.22 (m, 1H), 4.70 (brs, 1H), 4.59 (d, J=4.8 Hz, 1H), 3.86-3.79 (m, 1H), 3.64 (s, 3H), 3.50 (dd, J=6.8, 14.2 Hz, 1H), 3.41 (d, J=6.0 Hz, 1H), 3.26-3.22 (m, 1H), 2.30-2.25 (m, 1H), 2.18-2.06 (m, 2H), 1.99-1.86 (m, 2H), 1.81-1.61 (m, 4H), 1.58-1.31 (m, 8H), 1.30-1.05 (m, 5H), 1.04-0.95 (m, 5H), 0.94 (s, 3H), 0.93-0.85 (m, 4H), 0.65 (s, 3H).

Examples-71 and 72: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N—((R)-1-hydroxypropan-2-yl)-N-methoxypentanamide (71) and (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N—((S)-1-hydroxypropan-2-yl)-N-methoxypentanamide

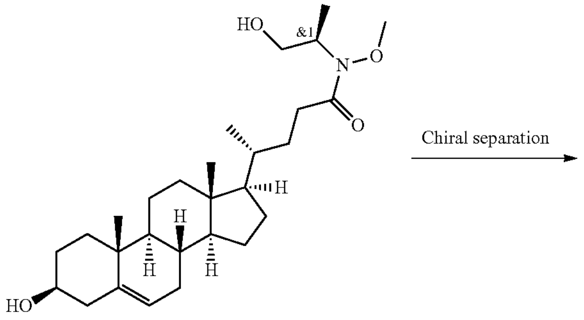

66

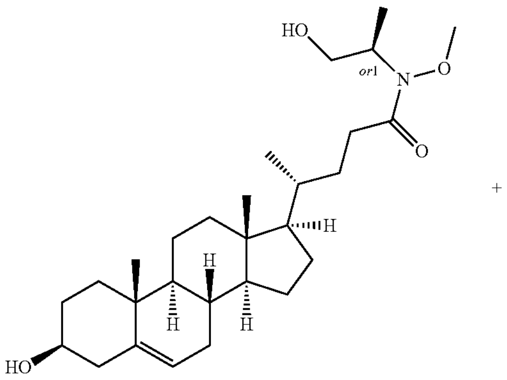

71

-continued

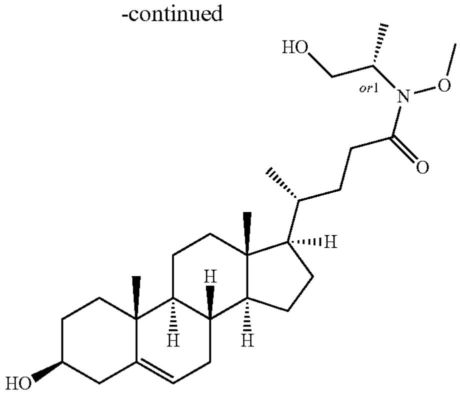

72

The diastereomers 66 (150 mg) were separated by chiral prep HPLC (Column: Chiralpak IG (4.6×250 mm) 5 μm; mobile phase-A: n-hexane, mobile phase-B: IPA; Flow rate:1.0 mL/min, Isocratic: (% A:B) 80:20) to afford compound 71 (peak-1, 23 mg, 13.76%) and compound 72 (peak-2, 25 mg, 25.26%) as an off-white solid.

71 (Peak-1): ELSD-MS (ESI) m/z: 461.9 $[M+H]^+$; $^1H$ NMR (400 MHz, DMSO-$d_6$): δ 5.26-5.25 (m, 1H), 4.78-4.73 (m, 1H), 4.59 (d, J=4.8 Hz, 1H), 4.24 (brs, 1H), 3.69 (s, 3H), 3.50-3.43 (m, 1H), 3.38-3.33 (m, 1H), 3.28-3.22 (m, 1H), 2.32-2.23 (m, 1H), 2.17-2.05 (m, 2H), 1.99-1.86 (m, 2H), 1.84-1.73 (m, 2H), 1.72-1.61 (m, 2H), 1.59-1.44 (m, 3H), 1.42-1.32 (m, 4H), 1.31-1.09 (m, 5H), 1.07-1.03 (m, 4H), 1.02-0.96 (2H), 0.94 (s, 3H), 0.93-0.83 (m, 4H), 0.64 (s, 3H).

72 (Peak-2): ELSD-MS (ESI) m/z: 462 $[M+H]^+$; $^1H$ NMR (400 MHz, DMSO-$d_6$): δ 5.26-5.25 (m, 1H), 4.77-4.76 (m, 1H), 4.59 (d, J=4.8 Hz, 1H), 4.24 (brs, 1H), 3.69 (s, 3H), 3.49-3.43 (m, 1H), 3.38-3.33 (m, 1H), 3.28-3.21 (m, 1H), 2.40-2.33 (m, 1H), 2.31-2.20 (m, 1H), 2.17-2.04 (m, 2H), 1.99-1.86 (m, 2H), 1.84-1.73 (m, 2H), 1.72-1.61 (m, 2H), 1.59-1.44 (m, 3H), 1.42-1.32 (m, 4H), 1.31-1.17 (m, 2H), 1.16-1.09 (m, 2H), 1.07-1.03 (m, 4H), 1.02-0.96 (2H), 0.94 (s, 3H), 0.93-0.83 (m, 4H), 0.65 (s, 3H).

Examples-73 & 74: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-3-methyl-1,2-oxazinan-2-yl)pentan-1-one (73) and (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-methyl-1,2-oxazinan-2-yl)pentan-1-one

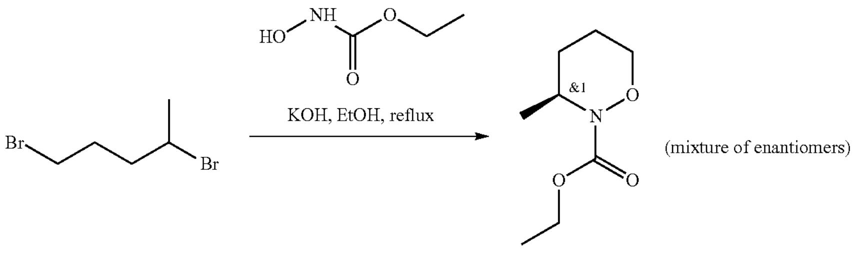

A

-continued

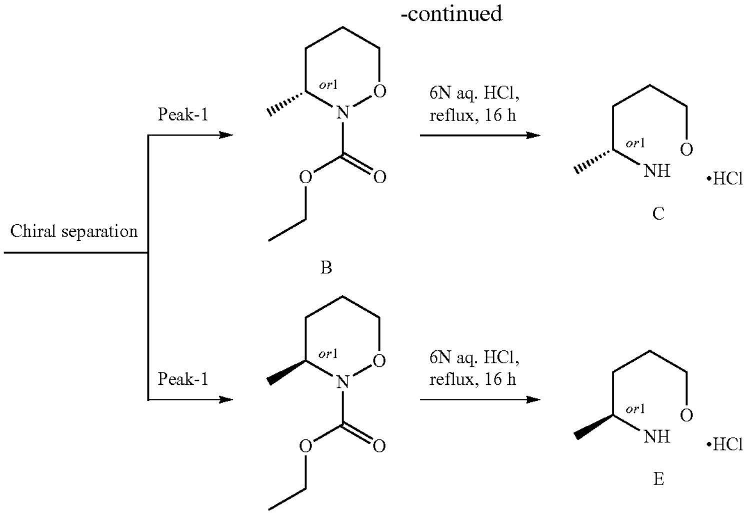

B C D E

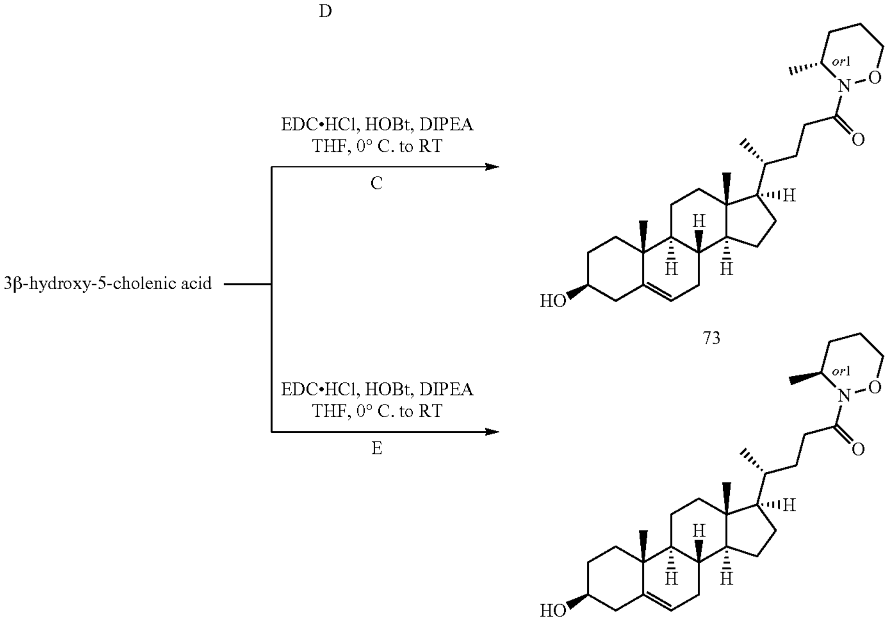

73

74

To a stirred solution of ethyl N-hydroxy carbamate (920 mg, 8.75 mmol) in ethanol (10 mL, 171 mmol) at room temperature was added potassium hydroxide (484 mg, 8.63 mmol) followed by 1,4-dibromopentane-(1 g, 4.35 mmol). The reaction mixture was stirred at 80° C. for 6 h. The progress of the reaction was monitored by TLC. Upon completion, the reaction mixture was concentrated, diluted with MTBE and then filtered. The filtrate was concentrated to get a crude compound A as a mixture of enantiomers (1 g, crude). The enantiomers were separated by chiral preparative HPLC [column: Chiralpak-IA (250*4.6 mm), 5 μm; mobile phase: hexanes/IPA 85/15; flow rate: 0.5 mL/min.] to afford compound B (peak-1, 100 mg, 13%) and compound D (peak-2, 70 mg, 9%) as off-white solids.

To a stirred solution of compound B (50 mg, 289 μmol) in 1,4-dioxane (1 mL) at room temperature was added 6N HCl (1 mL) and stirred at 100° C. for 16 h. Upon completion, the reaction mixture was concentrated to get a crude compound C (20 mg, 68%) as a brown liquid.

To a stirred solution of crude compound D (100 mg, 0.577 mmol) in 1,4-dioxane (2 mL) at room temperature was added 6N HCl (2 mL) and stirred at 100° C. for 16 h. Upon completion, the reaction mixture was concentrated to get crude compound E (58 mg, 100%) as a brown liquid.

Compound 73 was synthesized according to the general procedure B using 3β-hydroxy-5-cholenic acid (50 mg, 0.133 mmol), DIPEA (0.1 mL, 0.4 mmol), EDC.HCl (38 mg, 0.2 mmol), HOBt (20 mg, 0.147 mmol), crude compound C (33 mg, 334 mmol), and THF (2.5 mL). The reaction time was 16. The obtained crude compound was purified by preparative HPLC [column: Gemini C18 2.0*50 mm, 3 μm; mobile phase: A 0.01% FA in water; flow rate: 0.5 ml/min, Program (Time/% B): 0.05/5, 2.0/60, 5.50/75, 5.0/85] to afford compound 73 (30 mg, 32%) as an off-white solid. LC-MS(ESI) m/z 457.9 $(M+H)^+$; $^1H$ NMR (400 MHz, DMSO-$d_6$): δ 5.27-5.25 (m, 1H), 4.6-4.53 (m, 2H), 4.13-4.08 (m, 1H), 3.76-3.69 (m, 1H), 3.26-3.20 (m, 1H), 2.28-2.23 (m, 1H), 2.18-2.05 (m, 2H), 2.04-1.83 (m, 3H), 1.82-

1.60 (m, 5H), 1.58-1.32 (m, 8H), 1.31-1.20 (m, 2H), 1.18-0.97 (m, 10H), 0.94 (s, 3H), 0.91-0.88 (m, 4H),), 0.64 (s, 3H).

Compound 74 was synthesized according to the general procedure B using 3β-hydroxy-5-cholenic acid (50 mg, 133 μmol), DIPEA (0.1 mL, 0.4 mmol), EDC.HCl (38 mg, 0.2 mmol), HOBt (20 mg, 147 μmol), crude compound E (33 mg, 334 mmol), and THF (2.5 mL). The reaction time was 16 h. The obtained crude compound was purified by prep HPLC purification [column: Gemini C18 2.0*50 mm, 3 μm; mobile phase: A 0.01% FA in water; flow rate: 0.5 ml/min, program (Time/% B): 0.05/5, 2.0/60, 5.50/75, 5.0/85] to afford compound 74 (14 mg, 14.9%) as an off-white solid. LC-MS(ESI) m/z 458.4 $(M+H)^+$; $^1H$ NMR (400 MHz, DMSO-$d_6$): δ 5.27-5.25 (m, 1H), 4.61-4.52 (m, 2H), 4.12-4.08 (m, 1H), 3.75-3.68 (m, 1H), 3.33-3.21 (m, 1H), 2.38-2.30 (m, 2H), 2.22-2.01 (m, 3H), 2.00-2.85 (m, 3H), 1.83-1.62 (m, 4H), 1.54-1.31 (m, 9H), 1.30-0.96 (m, 10), 0.94 (s, 3H), 0.90-0.86 (m, 4H), 0.64 (s, 3H).

Example 75: tert-butyl N—((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N-methoxyglycinate

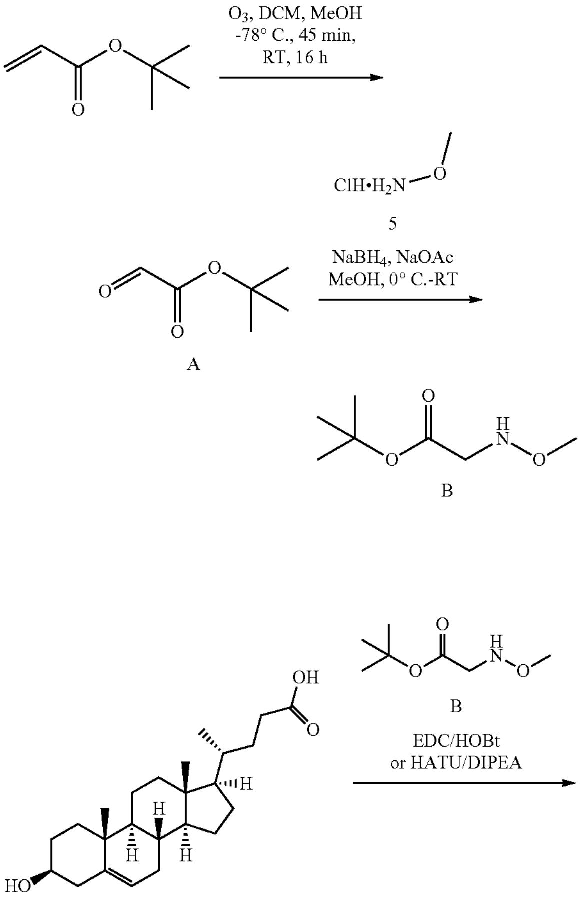

5

A

B

B

3β-hydroxy-5-cholenic acid

-continued

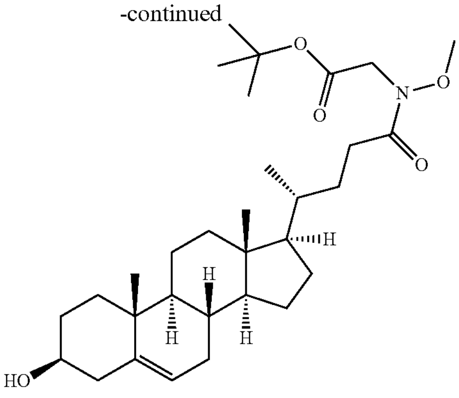

75

A solution of tert-butyl prop-2-enoate (2 g, 15.6 mmol) in a mixture of DCM (46.7 mL), methanol (13.3 mL) was ozonized by bubbling with ozone gas over the period of 45 minutes at −78° C. Upon completion, the reaction mixture was quenched with dimethyl sulfide (10 mL) at −78° C., and the resultant reaction mixture was stirred for 16 h at room temperature. The reaction mixture was diluted with water (50 ml) and extracted with DCM (2×20 mL) and the organic layer was dried over sodium sulfate and concentrated in vacuo to obtain crude compound. The crude material was purified by column chromatography over silica gel (100-200 mesh) with gradient elution of 10-15% ethyl acetate in hexane to afford compound A (0.7 g, 5.38 mmol) as a colorless liquid.

To a stirred solution of compound A (0.4 g, 3.07 mmol), O-methyl hydroxylamine hydrochloride (257 mg, 3.07 mmol) in methanol (5 mL, 123 mmol) was added sodium acetate (504 mg, 6.15 mmol) at 0° C. The resulting reaction mixture was stirred for 4 h at room temperature. Followed by added $NaCNBH_3$ (579 mg, 9.22 mmol) at 0° C. and the reaction mixture was stirred at room temperature for 16 h. Upon completion, the reaction mixture was diluted with water (5 mL) and extracted with DCM (3×10 mL). The combined organic layer was dried over anhydrous sodium sulfate and concentrated in vacuo to afford crude material. The crude material was purified by column chromatography over silica gel (100-200 mesh) by gradient elution of 10-15% ethyl acetate in hexane to obtain compound B (150 mg) as a colorless liquid.

Compound 75 was synthesized according to the general procedure A using 3β-hydroxy-5-cholenic acid (50 mg, 0.133 mmol), compound B (23.7 mg, 0.147 mmol), HATU (102 mg, 0.267 mmol), DIPEA (51.8 mg, 0.4 mmol), and DMF (3 mL) at room temperature. The resultant reaction mixture was stirred for 16 h at room temperature. Upon completion, the reaction mixture was diluted with water (10 mL) and extracted with ethyl acetate (2×10 mL). The combined organic layer was dried over sodium sulfate, concentrated in vacuo to get crude compound. The crude product was purified by flash chromatography over silica gel (100-200 mesh) with gradient elution of 10-30% ethyl acetate in hexane to obtain the compound 75 (25 mg, yield 28%) as gummy liquid. LC-MS (ESI) m/z: 461.8 $[M+H-56]^+$; $^1H$ NMR (400 MHz, $CDCl_3$): δ 5.36-5.34 (m, 1H), 4.21 (d, J=2.8, 2H), 3.71 (s, 3H), 3.53-3.48 (m, 1H), 2.62-2.52 (m, 1H), 2.50-2.40 (m, 1H), 2.32-2.21 (m, 2H), 2.05-1.93 (m, 2H), 1.90-1.79 (m, 4H), 1.53-1.42 (m, 15H), 1.41-1.24 (m, 3H), 1.20-1.02 (m, 6H), 1.01 (s, 3H), 0.98-0.92 (m, 4H), 0.69 (s, 3H).

Example 76: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-phenylpiperidin-1-yl)pentan-1-one (76) and Example 77: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-3-phenylpiperidin-1-yl)pentan-1-one

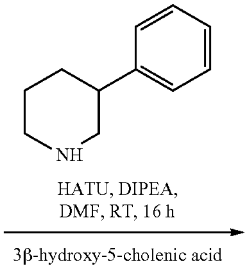

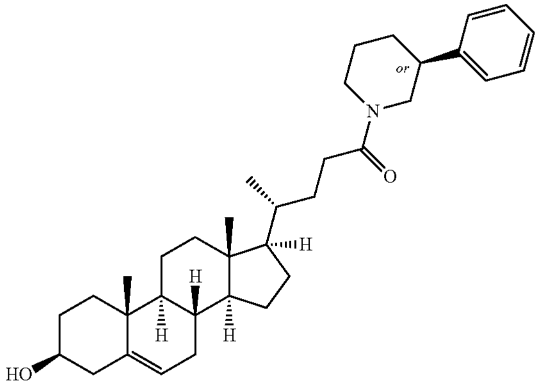

76

+

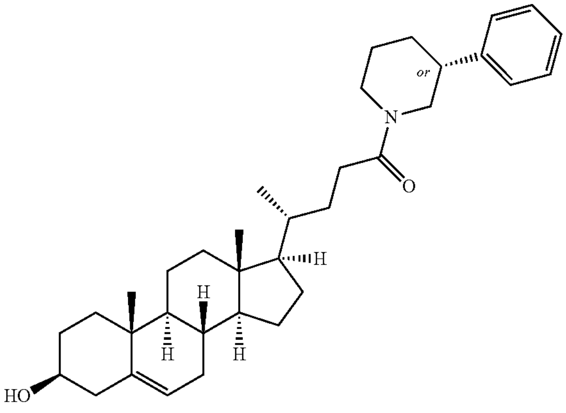

77

Compounds 76 and 77 were synthesized according to the general procedure A using 3β-hydroxy-5-cholenic acid (350 mg, 0.93 mmol), HATU (711 mg, 1.87 mmol), DIPEA (242 mg, 1.87 mmol), 3-phenylpiperidine (151 mg, 0.93 mmol), and DMF (3.5 mL). The reaction time was 16 h. Upon completion, the reaction mixture was diluted with water (100 mL) and extracted with ethyl acetate (50 mL×2). The combined organic layer was dried over sodium sulfate, filtered, and concentrated in vacuo to afford crude diastereomeric mixture (300 mg). The diastereomers were separated by chiral prep HPLC [column: Chiralpack-IG (4.6× 250) mobile phase-A: n-hexane, mobile phase-B: ethanol, Flow: 1.0 mL/Min.] to afford compound 76 (peak-1, 64.8 mg, 13.4%) and compound 77 (peak-2, 77.5 mg, 16%) as an off-white solid.

76 (peak-1): ELSD-MS (ESI) m/z: 517.9 $[M+H]^+$; $^1H$ NMR (400 MHz, DMSO-$d_6$): δ 7.30-7.19 (m, 5H), 5.27-5.25 (m, 1H), 4.59 (brs, 1H) 4.47-4.40 (m, 1H), 3.90-3.81 (m, 1H), 3.30-3.00 (m, 2H), 2.63-2.58 (m, 1H), 2.42-2.35 (m, 1H), 2.28-2.05 (m, 3H), 1.99-1.85 (m, 3H), 1.84-1.60 (m, 6H), 1.58-1.32 (m, 8H), 1.31-1.05 (m, 5H), 1.03-0.82 (m, 10H), 0.66 (d, J=12 Hz, 3H).

77 (peak-2): ELSD-MS (ESI) m/z: 517.9 $[M+H]^+$; $^1H$ NMR (400 MHz, DMSO-$d_6$): δ 7.32-7.19 (m, 5H), 5.27-5.25 (m, 1H), 4.59 (brs, 1H) 4.47-4.40 (m, 1H), 3.90-3.81 (m, 1H), 3.32-3.20 (m, 1H), 3.12-3.00 (m, 1H), 2.63-2.56 (m, 1H), 2.31-2.20 (m, 2H), 2.19-2.02 (m, 2H), 2.00-1.85 (m, 3H), 1.82-1.60 (m, 6H), 1.59-1.31 (m, 8H), 1.30-1.05 (m, 5H), 1.04-0.82 (m, 10H), 0.66 (d, J=9.6 1 Hz, 3H).

Example 78: (4R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(1-phenyl-3-azabicyclo[3.1.0]hexan-3-yl)pentan-1-one

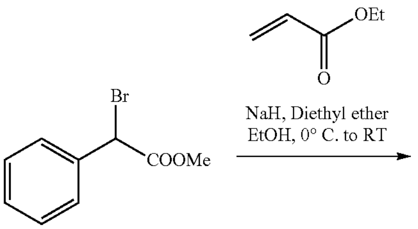

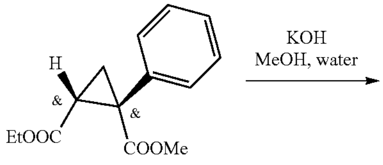

A

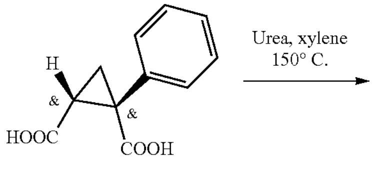

B

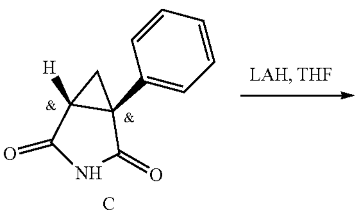

C

-continued

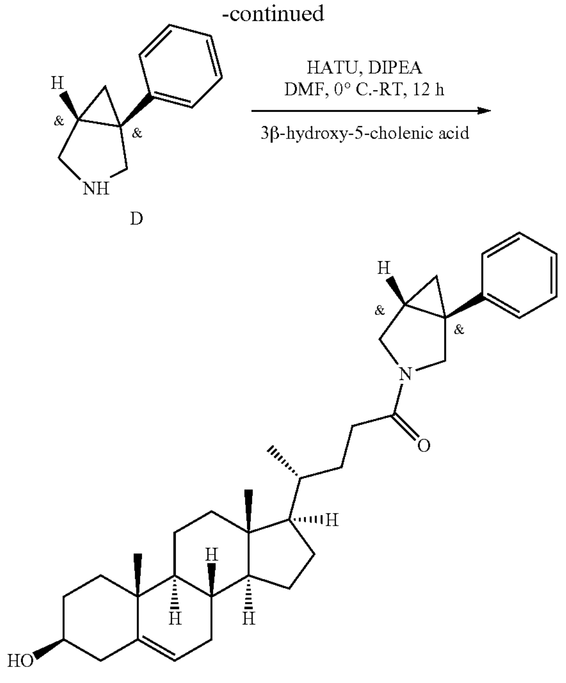

D

78

To the stirred slurry of NaH (60% dispersion in mineral oil, 175 mg, 4.37 mmol) in diethyl ether (10 mL, 96.2 mmol) was added methanol (0.2 mL, 4.94 mmol) followed by methyl 2-bromo-2-phenylacetate (1 g, 4.37 mmol) and ethyl prop-2-enoate (874 mg, 2 eq, 8.73 mmol). The resultant reaction mixture was allowed to stir at room temperature for 16 h. Upon completion, the mixture was diluted with ice-water and extracted with ethyl acetate (2×10 mL). The combined organic layer was dried over anhydrous sodium sulfate and concentrated in vacuo to afford crude compound A (1 g) as a gummy liquid.

To the stirred solution of crude compound A (0.9 g, 3.62 mmol) in a mixture of ethanol (5 mL, 85.6 mmol) and water (5 mL, 278 mmol) was added potassium hydroxide (549 mg, 9.79 mmol). The resultant reaction mixture was allowed to stir at 90° C. for 6 h. Upon completion, the reaction mixture was diluted with water, acidified with HCl, and extracted with ethyl acetate (2×10 mL). The combined organic layer was dried over anhydrous sodium sulfate and concentrated in vacuo to afford crude compound B (1 g) as gummy liquid.

To the stirred solution of crude compound B (1 g, 4.85 mmol) in xylene (10 mL) at room temperature was added urea (583 mg, 2 eq, 9.7 mmol) and the resultant reaction mixture was allowed to stir at 150° C. for 5 h. Upon completion, the reaction mixture was diluted with water and extracted with ethyl acetate (2×10 mL). The combined organic layer was dried over anhydrous sodium sulfate and concentrated in vacuo to afford crude compound. The crude compound was purified by column chromatography over 100-200 silica gel mesh by eluting 1% methanol in DCM to afford pure compound C (450 mg, 66% for two steps) as a colorless oil. LC-MS (ESI) m/z: 188 $[M+H]^+$.

To the stirred solution of compound C (0.4 g, 2.14 mmol) in tetrahydrofuran (4 mL, 49.1 mmol) at 0° C. was added $LiAlH_4$ (2M in THF, 270 μL, 6.41 mmol) slowly drop wise and allowed to stir for 15 min. at room temperature and then heated at 80° C. for 3 h. Upon completion, the reaction mixture was quenched with saturated sodium sulphate, filtered, and washed with ethyl acetate. The filtrate was concentrated in vacuo to afford crude compound of compound D (0.3 g, 88%) as a yellow oil. LC-MS (ESI) m/z: 160 $[M+H]^+$.

Compound 78 was synthesized accordingly general procedure A using 3β-Hydroxy-5-cholenic acid (320 mg, 0.854 mmol), DIPEA (552 mg, 4.27 mmol), HATU (650 mg, 1.71 mmol), compound D (272 mg, 1.71 mmol), and dry THF (4 mL). The crude compound was purified by column chromatography over 100-200 silica gel mesh by eluting 35% ethyl acetate in hexane to afford compound 78 (350 mg, 79%) as an off-white solid. LC-MS (ESI) m/z: 516 $[M+H]^+$; $^1$H-NMR (400 MHz, DMSO-$d_6$): δ 7.35-7.28 (m, 2H), 7.27-7.18 (m, 3H), 5.30-5.25 (m, 1H), 4.59 (d, J=4.4 Hz, 1H), 4.05-3.98 (m, 1H), 3.78-3.68 (m, 2H), 3.48-3.37 (m, 1H), 3.28-3.21 (m, 1H), 2.30-2.01 (m, 4H), 2.00-1.60 (m, 6H), 1.59-0.96 (m, 16H), 0.95-0.82 (m, 7H), 0.76-0.72 (m, 1H), 0.65 (s, 3H).

Example 79: (R)-1-(4,4-difluoropiperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

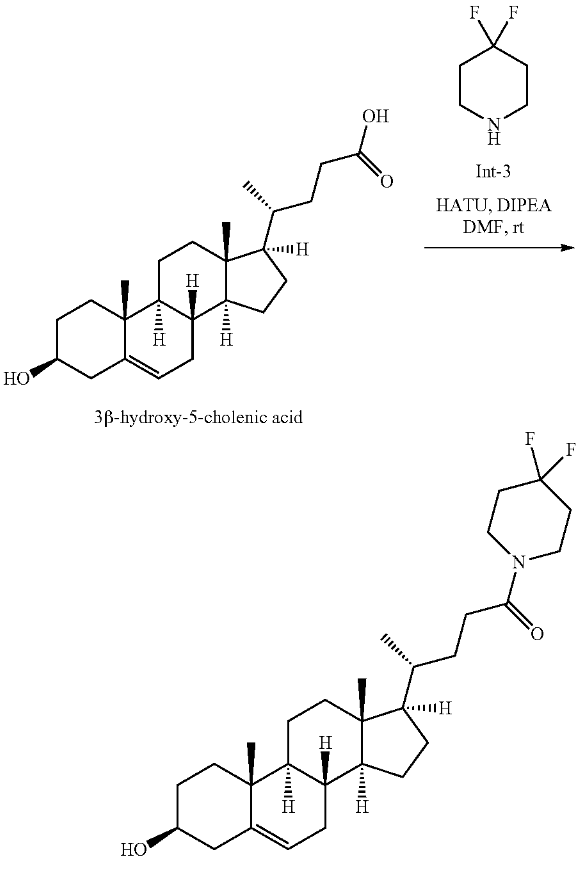

79

Compound 79 was synthesized according to the general procedure A using 3β-hydroxy-5-cholenic acid (50 mg, 0.133 mmol), HATU (102 mg, 0.267 mmol), DIPEA (0.07 mL, 0.40 mmol), 4,4-difluoropiperidine_(19.4 mg, 0.033 mmol), and DMF (2 mL). The reaction time was 16 h. The obtained crude compound was purified by column chromatography over silica gel (100-200 mesh) using 0-80% gradient elution of ethyl acetate in hexanes to afford the title compound 79 as an off-white solid (42 mg, 65.87%). LC-MS (ESI) m/z: 478.0 $[M+H]^+$; $^1H$ NMR (400 MHz, $CDCl_3$): δ 5.36-5.34 (m, 1H), 3.72 (brt, J=5.6 Hz, 2H), 3.56 (brt, J=5.2 Hz, 2H), 3.55-3.48 (m, 1H), 2.46-2.36 (m, 1H), 2.34-1.91 (m, 3H), 2.03-1.6-90 (m, 6H), 1.89-1.74 (m, 4H), 1.52-1.41 (m, 5H), 1.40-1.22 (m, 4H), 1.20-1.02 (m, 6H), 1.01 (s, 3H), 0.99-0.92 (m, 4H), 0.68 (s, 3H). $^{19}F$ NMR (376 MHz, $CDCl_3$) δ−97.92 (s, $CF_2$).

Example 80: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(2-oxa-7-azaspiro[3.5]nonan-7-yl)pentan-1-one

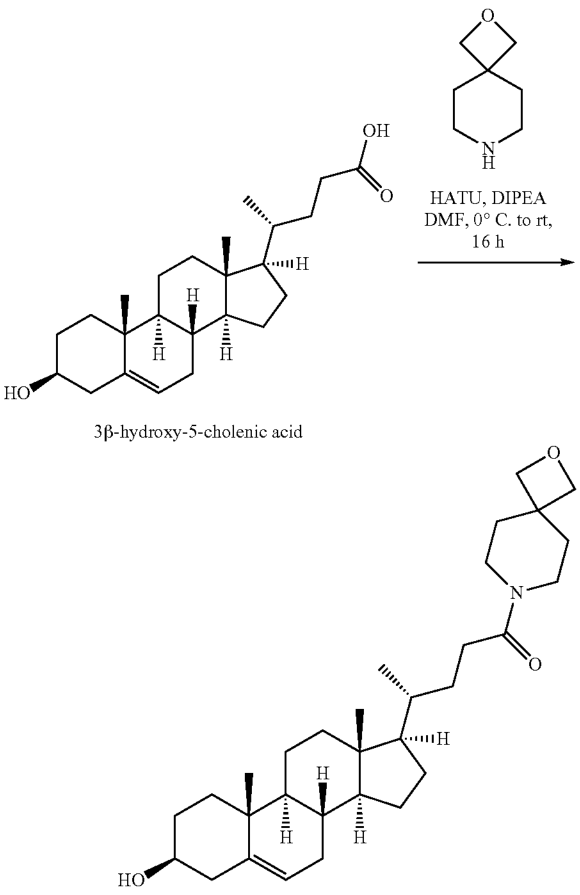

3β-hydroxy-5-cholenic acid

80

Compound 80 was synthesized according to the general procedure A using 3β-hydroxy-5-cholenic acid (100 mg, 0.267 mmol), HATU (0.203 mg, 0.534 mmol), DIPEA (0.138 mL, 0.8 mmol), 2-oxa-7-azaspiro[3.5]nonane (37 mg, 0.29 mmol), and DMF (3 mL). The obtained crude material was purified by column chromatography over silica gel (100-200 mesh) with 0-50% gradient elution of ethyl acetate in hexanes to afford compound 80 as an off-white solid (30 mg, 46%). ELSD-MS (ESI) m/z: 483.9 $[M+H]^+$;

$^1H$ NMR (400 MHz, DMSO-$d_6$): δ 5.26-5.25 (m, 1H), 4.59 (d, J=4.4 Hz, 1H), 4.31 (s, 4H), 3.38-3.30 (m, 4H, merged with moisture peak), 3.28-3.21 (m, 1H), 2.32-2.25 (m, 1H), 2.23-2.05 (m, 3H), 1.99-1.86 (m, 2H), 1.85-1.72 (m, 4H), 1.71-1.64 (m, 3H), 1.60-1.43 (m, 4H), 1.42-1.32 (m, 4H), 1.31-1.22 (m, 1H), 1.19-1.05 (m, 4H), 1.02-0.94 (m, 2H), 0.95 (s, 3H), 0.92-0.82 (m, 4H), 0.64 (s, 3H).

Example 81: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(1,4-oxazepan-4-yl)pentan-1-one

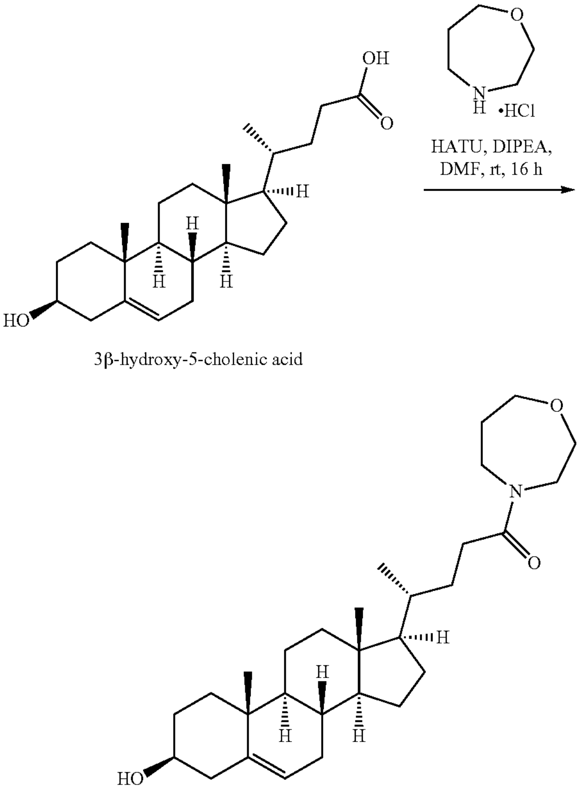

3β-hydroxy-5-cholenic acid

81

Compound 81 was synthesized according to the general procedure A using 3β-hydroxy-5-cholenic acid (100 mg, 0.26 mmol), HATU (203 mg, 0.54 mmol), DIPEA (69 mg, 0.53 mmol), 1,4-oxazepane hydrochloride (55 mg, 0.4 mmol) and DMF (1 mL). The reaction time was 16 h. The obtained crude material was purified by preparative HPLC [Column: Acquity BEH C18 (2.1*50*1.7u, Mobile phase-A: 0.01% FA in water, mobile phase-B: 100% ACN, program (Time/% B): 0/3,4/95, 6/95, 6.01/3, 6.50/3 flow:0.4 ml/min] to afford compound 81 (8.6 mg, 7%) as a light pink solid. LC-MS (ESI) m/z: 457.8 $[M+H]^+$; $^1H$ NMR (400 MHz, DMSO-$d_6$) δ 5.27-5.25 (m, 1H), 4.58 (d, J=4.8 Hz, 1H), 3.68-3.59 (m, 8H), 3.25-3.20 (m, 1H), 2.25-2.21 (m, 2H), 2.20-2.05 (m, 2H), 2.00-1.85 (m, 2H), 1.84-1.60 (m, 6H), 1.59-1.32 (m, 7H), 1.31-0.96 (m, 7H), 0.94 (s, 3H) 0.93-0.83 (m, 4H), 0.64 (s, 3H).

Example 82: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(trifluoromethyl)piperidin-1-yl)pentan-1-one

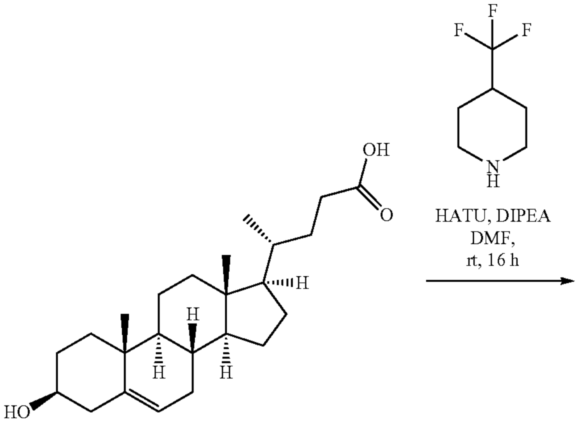

3β-hydroxy-5-cholenic acid

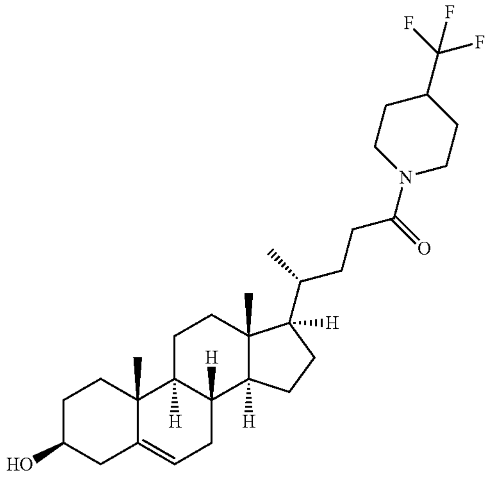

82

Compound 82 was synthesized according to the general procedure A using 3β-hydroxy-5-cholenic acid (100 mg, 0.267 mmol), HATU (203 mg, 0.534 mmol), DIPEA (0.18 mL, 1.07 mmol), 4-(trifluoromethyl)piperidine (61.3 mg, 0.4 mmol), and DMF (3 mL). The crude material was purified by column chromatography over silica gel (100-200 mesh) using 0-7% gradient elution of ethyl acetate in hexanes to afford the title compound 82 (130 mg, 95.5%). LC-MS (ELSD) m/z: 510[M+H]$^+$; $^1$H NMR (400 MHz, DMSO-$d_6$): δ 5.27-5.25 (m, 1H), 4.59 (d, J=4.8 Hz, 1H), 4.49 (brd, J=13.2 Hz, 1H), 3.96 (brd, J=14 Hz, 1H), 3.28-3.21 (m, 1H), 3.02 (t, J=12.8 Hz, 1H), 2.63-2.55 (m, 1H), 2.36-2.04 (m, 4H), 2.01-1.73 (m, 6H), 1.71-1.45 (m, 5H), 1.42-1.32 (m, 4H), 1.29-1.14 (m, 5H), 1.13-0.97 (m, 5H), 0.93 (s, 3H), 0.91-0.84 (m, 4H), 0.64 (s, 3H).

Example 83: N-(1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-4-methylpiperidin-4-yl)acetamide

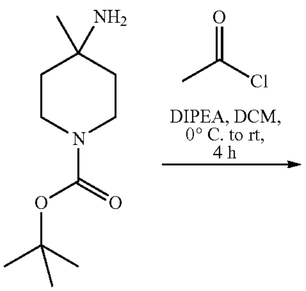

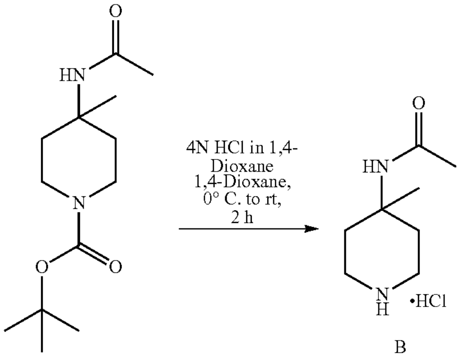

A

B

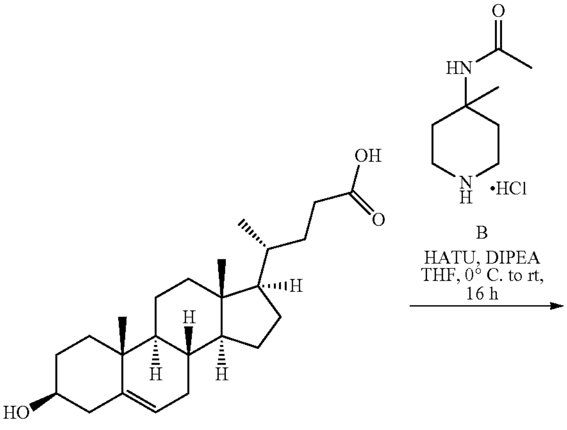

3β-hydroxy-5-cholenic acid

-continued

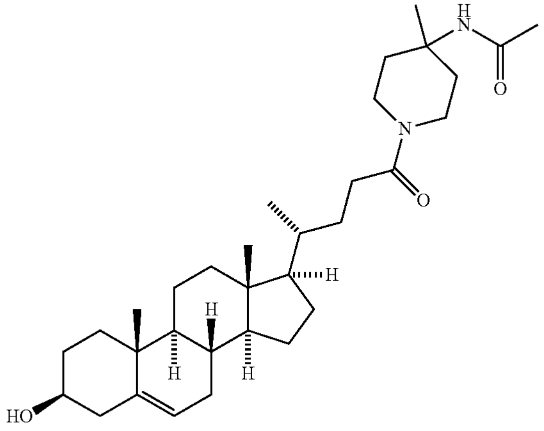

83

To a stirred solution of tert-butyl 4-amino-4-methylpiperidine-1-carboxylate (0.2 g, 0.93 mmol) in DCM (16 mL) at 0° C. were added DIPEA (634 mg, 4.91 mmol) and acetyl chloride (143 mg, 1.83 mmol). The resultant reaction mixture was allowed to stir at room temperature for 16 h. Upon completion, the reaction mixture was concentrated in vacuo, diluted with water (10 mL), and extracted with DCM (30 mL×3). The combined organic layer was dried over anhydrous sodium sulfate and concentrated in vacuo. The obtained crude compound was purified by column chromatography over silica gel (60-120 mesh) with 0-3% gradient elution of MeOH in DCM to afford compound A (240 mg, 82%) as a pale-yellow solid.

To the stirred solution of compound A (240 mg, 1.12 mmol) in 1,4-dioxane (5 mL, 58.6 mmol) at 0° C., was added HCl solution (4M in 1,4-dioxane, 0.1 mL) and the resultant reaction mixture was stirred at room temperature for 4 h. Upon completion, the reaction mixture was concentrated in vacuo to obtain crude compound. The crude compound was triturated with hexane to get pure compound B as a brown solid.

Compound 83 was synthesized according to the general procedure A using 3β-hydroxy-5-cholenic acid (100 mg, 0.26 mmol), HATU (203 mg, 0.54 mmol), DIPEA (104 mg, 0.80 mmol), compound B (62.8 mg, 0.4 mmol), and THE (1 mL). The reaction time was 1 h. The obtained crude material was purified by column chromatography over silica gel (100-200 mesh) with 0-5% gradient elution of MeOH in DCM to afford compound 83 (75.3 mg, 55%) as an off-white solid. LC-MS (ESI) m/z: 513 $[M+H]^+$; $^1H$ NMR (400 MHz, DMSO-$d_6$): δ 7.39 (s, 1H), 5.27-5.25 (m, 1H), 4.58 (d, J=4.4 Hz, 1H), 3.88-3.83 (m, 1H), 3.54-3.50 (m, 1H), 3.28-3.24 (m, 2H), 3.00-2.91 (m, 1H), 2.31-2.22 (m, 1H), 2.21-2.08 (m, 4H), 2.00-1.87 (m, 3H), 1.81 (s, 3H), 1.80-1.72 (m, 2H), 1.70-1.61 (m, 2H), 1.60-1.42 (m, 3H), 1.40-1.31 (m, 5H), 1.30-1.21 (m, 6H), 1.20-0.96 (m, 5H) 0.94 (s, 3H) 0.91-0.83 (m, 4H), 0.64 (s, 3H).

Example 84: N-(1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-4-methylpiperidin-4-yl)methanesulfonamide

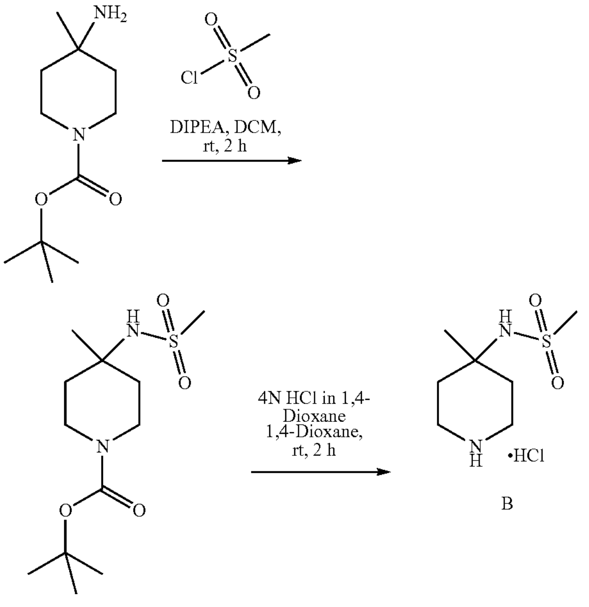

A

B

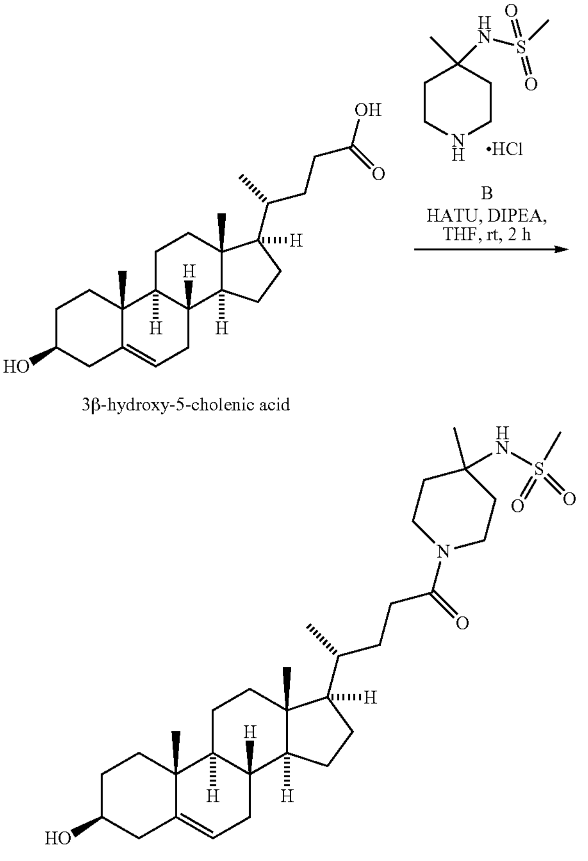

B

3β-hydroxy-5-cholenic acid

84

To a stirred solution of tert-butyl 4-amino-4-methylpiperidine-1-carboxylate (0.5 g, 2.33 mmol) in DCM (5 mL), at 0° C. were added DIPEA (995 mg, 7.7 mmol) and mesyl chloride (267 mg, 2.33 mmol) under nitrogen atmosphere. The resultant reaction mixture was stirred at room temperature for 2 h. Upon completion, the reaction mixture was quenched with water (40 mL) and extracted with ethyl acetate (60 mL×3). The combined organic layer was dried over sodium sulfate, filtered, concentrated in vacuo, and purified by column chromatography over silica gel (100-200 mesh) with 0-2% gradient elution of MeOH in DCM to afford compound A as a yellow liquid (450 mg, 65%).

To a stirred solution of compound A (450 mg, 1.54 mmol) in 1,4 dioxane (4.5 mL) at 0° C. was added HCl solution (4M in 1,4-dioxane, 4.5 mL) under nitrogen atmosphere. The resultant reaction mixture was stirred at room temperature for 2 h. Upon completion, the reaction mixture was concentrated in vacuo and the resultant crude material was triturated with n-pentane (5 mL) to afford compound B as a pale-yellow solid (300 mg, 85%).

Compound 84 was synthesized according to the general procedure A using 3β-hydroxy-5-cholenic acid (120 mg, 0.32 mmol), HATU (291 mg, 0.76 mmol), DIPEA (0.33 mL, 1.9 mmol), crude compound B (334 mg, 1.9 mmol) and THE (1.5 mL). The reaction time was 2 h. The obtained crude material was purified by column chromatography over silica gel (100-200 mesh) with 0-3% gradient elution of MeOH in DCM to afford compound 84 (77.2 mg, 44%) as an off-white solid. LC-MS (ESI) m/z: 548.8 $[M+H]^+$; $^1H$ NMR (400 MHz, DMSO-$d_6$): δ 6.83 (s, 1H), 5.27-5.25 (m, 1H), 4.58 (d, J=4.8 Hz, 1H), 3.71-3.63 (m, 1H), 3.47-3.35 (m, 2H), 3.28-3.20 (m, 2H), 2.96 (s, 3H), 2.31-2.25 (m, 1H), 2.24-2.00 (m, 4H), 1.98-1.85 (m, 3H), 1.84-1.72 (m, 2H), 1.70-1.60 (m, 2H), 1.59-1.42 (m, 4H), 1.42-1.33 (m, 7H), 1.31-1.22 (m, 2H), 1.21-0.96 (m, 6H), 0.94 (s, 3H) 0.93-0.83 (m, 4H), 0.64 (s, 3H).

Example 85: 1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-4-methylpiperidine-4-carboxamide

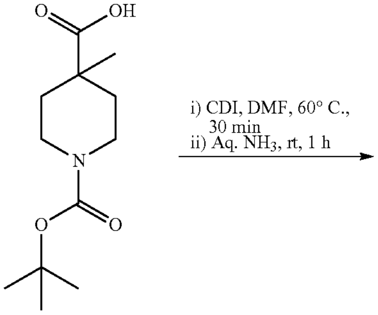

-continued

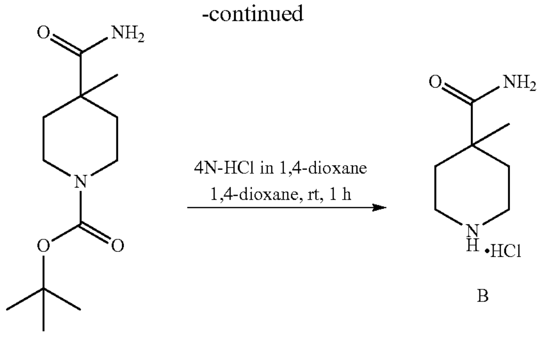

A B

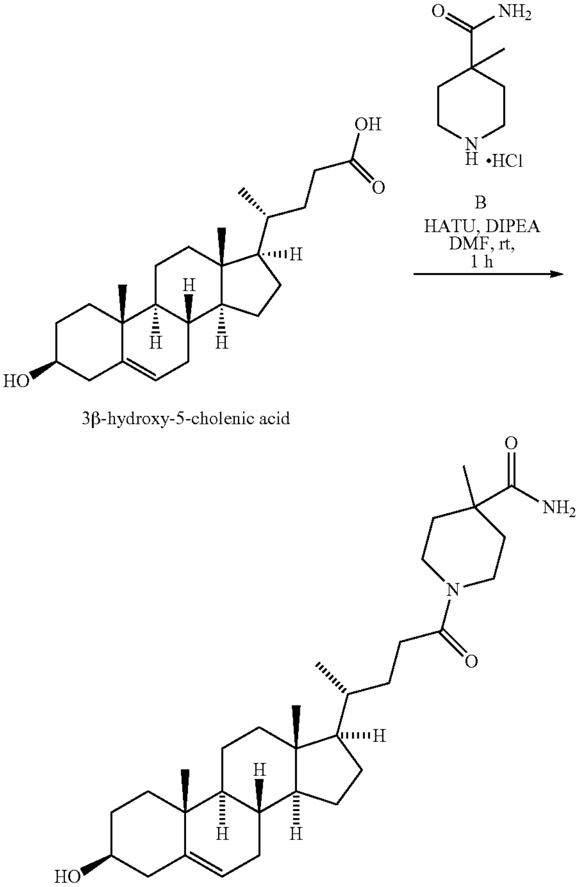

B

3β-hydroxy-5-cholenic acid

85

To a stirred solution of 1-[(tert-butoxy)carbonyl]-4-methylpiperidine-4-carboxylic acid (500 mg, 2.06 mmol) in dry DMF (10 mL) at 0° C. was added CDI (400 mg, 2.47 mmol) and the resulting reaction mixture was stirred at 60° C. for 1 h. Then, the reaction mixture was cooled to room temperature and 33% aqueous ammonia (3.2 mL, 3.29 mmol) was added. The resultant reaction mixture was allowed stir at room temperature for 1 h. Upon completion, the reaction mixture was quenched with water (30 mL) and extracted with ethyl acetate (50 mL×3). The combined organic layer was dried over sodium sulfate, filtered, concentrated to afford compound A (150 mg, crude) as a pale-yellow liquid.

To a stirred solution of crude compound A (90 mg, 0.37 mmol) in 1,4-dioxane (1 mL) at 0° C. was added HCl solution (4M in 1,4-dioxane, 3 mL) under nitrogen atmosphere. The resultant reaction mixture was stirred at room temperature for 1 h. Upon completion, the reaction mixture was concentrated in vacuo and crude was triturated with n-pentane (5 mL) to afford crude compound B as a pale-yellow solid (56 mg).

Compound 85 was synthesized according to the general procedure A using 3β-hydroxy-5-cholenic acid (90 mg, 0.24 mmol), HATU (183 mg, 0.48 mmol), DIPEA (0.085 mL, 0.48 mmol), crude compound B (51.3 mg, 0.36 mmol), and DMF (1 mL). The reaction time was 1 h. The obtained crude material was purified by purified by preparative HPLC [column: Kinetex EVO, C18 (50×3 mm, 2.60; mobile phase A: 0.01% FA in water, mobile phase B: 100% ACN; program (time % B): 0.01/5, 3/95, 6/95, 6.01/5. flow: 0.6 mL/min] to afford compound 85 (60 mg, 50%) as an off-white solid. LC-MS (ESI) m/z: 499 $[M+H]^+$; $^1H$ NMR (400 MHz, DMSO-$d_6$): δ 7.19 (s, 1H), 6.90 (s, 1H), 5.27-5.25 (m, 1H), 4.6 (d, J=4.4 Hz, 1H), 3.84-3.76 (m, 1H), 3.60-3.50 (m, 1H), 3.30-3.12 (m, 2H), 2.99-2.91 (m, 1H), 2.31-2.05 (m, 4H), 2.01-1.87 (m, 4H), 1.85-1.70 (m, 2H), 1.69-1.44 (m, 5H), 1.41-1.31 (m, 4H), 1.30-1.11 (m, 6H), 1.05 (s, 3H), 1.02-0.97 (m, 3H), 0.94 (s, 3H) 0.91-0.83 (m, 4H), 0.64 (s, 3H).

Example 86: 1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N,4-dimethylpiperidine-4-carboxamide

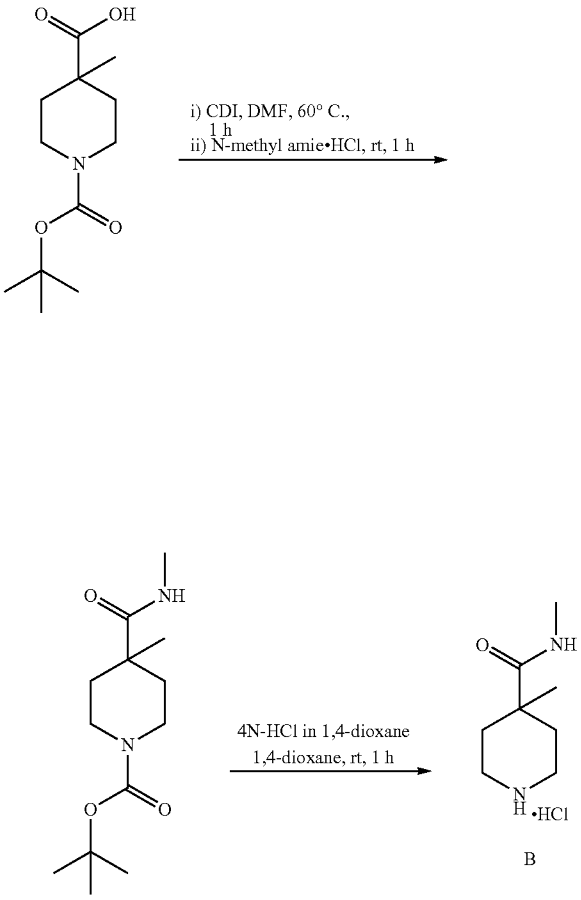

-continued

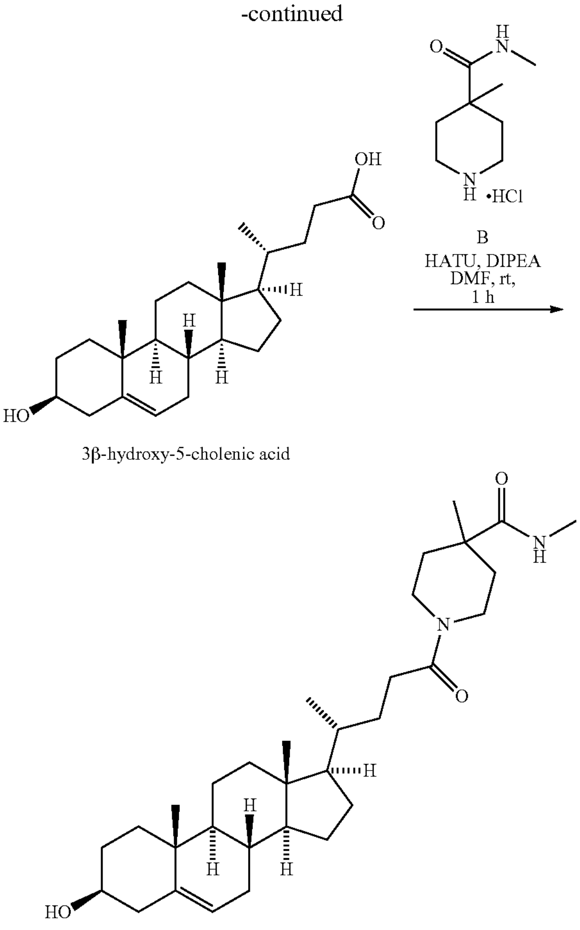

3β-hydroxy-5-cholenic acid

86

To a stirred solution of 1-[(tert-butoxy)carbonyl]-4-methylpiperidine-4-carboxylic acid (750 mg, 0.30 mmol) in dry DMF (7 mL) at 0° C. was added CDI (600 mg, 0.37 mmol). The reaction mixture was stirred at 60° C. for 1 h. The reaction mixture was cooled to room temperature, triethylamine (0.45 mL, 3.29 mmol) added followed by N-methylamine hydrochloride (416 mg, 0.67 mmol). The resultant reaction mixture was allowed stir at room temperature for 1 h. Upon completion, the reaction mixture was quenched with water (30 mL) and extracted with ethyl acetate (15 mL×2). The combined organic layer was dried over sodium sulfate, filtered, concentrated to afford compound A (195 mg, crude) as a pale-yellow liquid.

To a stirred solution of crude compound A (190 mg, 0.74 mmol) in 1,4-dioxane (2 mL) at 0° C. was added HCl (4M in 1,4-dioxane, 2 mL) under nitrogen atmosphere. The resultant reaction mixture was stirred at room temperature for 2 h. Upon completion, the reaction mixture was concentrated in vacuo and the resultant crude material was triturated with n-Pentane (5 mL) to afford compound B as a pale-yellow solid (143 mg, crude).

Compound 86 was synthesized according to the general procedure A using 3β-hydroxy-5-cholenic acid (220 mg, 0.58 mmol), HATU (447 mg, 1.17 mmol), DIPEA (0.33 mL, 1.9 mmol), crude compound B (184 mg, 1.1 mmol), and DMF (2 mL). The reaction time was 1 h. The obtained crude material was purified by column chromatography over silica gel (100-200 mesh) with 0-5% gradient elution of MeOH in DCM to afford compound 86 (196 mg, 65%) as an off-white solid. LC-MS (ESI) m/z: 513.4 [M+H]$^+$.

Example 87: 1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N,N,4-trimethylpiperidine-4-carboxamide

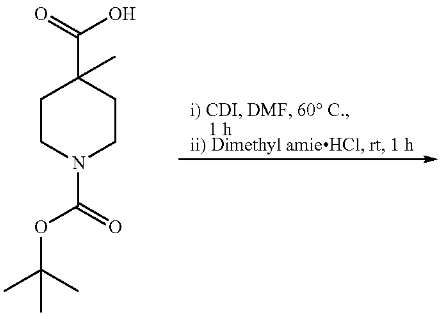

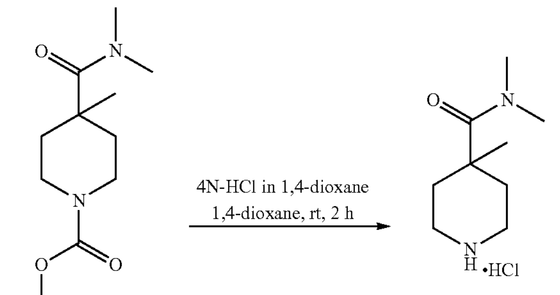

B

A

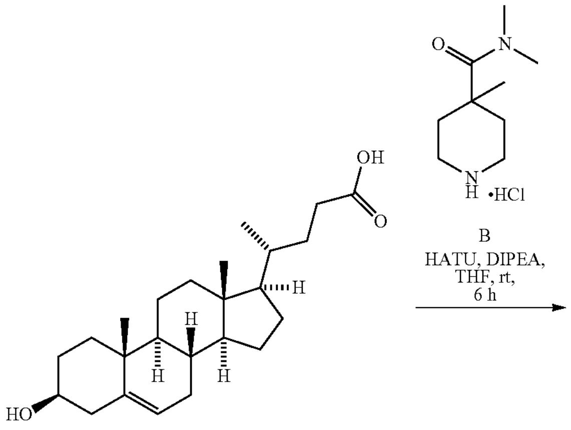

3β-hydroxy-5-cholenic acid

-continued

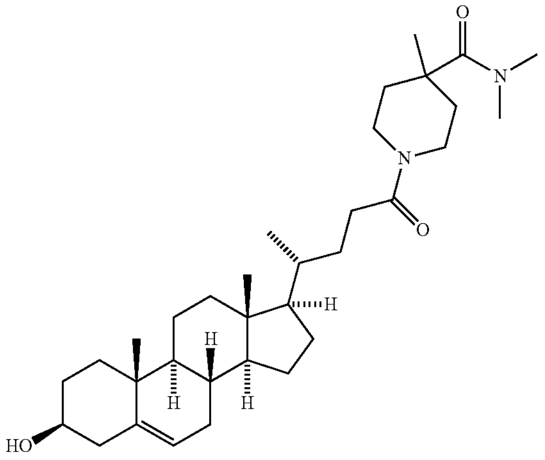

87

To a stirred solution of 1-[(tert-butoxy)carbonyl]-4-methylpiperidine-4-carboxylic acid (100 mg, 0.41 mmol) in dry dimethylformamide (1 mL) at 0° C. was added CDI (80 mg, 0.49 mmol). The reaction mixture was stirred at 60° C. for 1 h. The reaction mixture was cooled to room temperature followed by added triethylamine (0.45 mL, 3.29 mmol) and dimethylamine hydrochloride (134 mg, 1.64 mmol). The resultant reaction mixture was allowed stir at room temperature for 1 h. Upon completion, the reaction mixture was quenched with water (30 mL) and extracted with ethyl acetate (50 mL×3). The combined organic layer was dried over sodium sulfate, filtered, and concentrated to afford compound A (30 mg, crude) as a pale-yellow liquid.

To a stirred solution of crude compound A (200 mg, 0.74 mmol) in 1,4-dioxane (2 mL) at 0° C. was added HCl solution (4M in 14-Dioxane, 2 mL) under nitrogen atmosphere. The resultant reaction mixture was stirred at room temperature for 2 h. Upon completion, the reaction mixture was concentrated in vacuo and the resultant crude material was triturated with n-pentane (5 mL) to afford crude compound B as a pale-yellow solid (140 mg).

Compound 87 was synthesized according to the general procedure A using 3β-hydroxy-5-cholenic acid (120 mg, 0.32 mmol), HATU (291 mg, 0.76 mmol), DIPEA (0.33 mL, 1.9 mmol), crude compound B (334 mg, 1.9 mmol), and THE (1.5 mL). The reaction time was 6 h. The obtained crude material was purified by column chromatography over silica gel (100-200 mesh) with 0-5% gradient elution of MeOH in DCM to afford semi pure compound, which was further purified by preparative HPLC [column: Kinetex EVO, C18 (50×3 mm, 2.60; mobile phase A: 0.01% FA in water, mobile phase B: 100% ACN; program (time % B): 0.01/5, 3/95, 6/95, 6.01/5. flow: 0.6 mL/min] to afford compound 87 (65.9 mg, 39%) as an off-white solid. ELSD-MS (ESI) m/z: 526.9 [M+H]$^+$; $^1$H NMR (400 MHz, DMSO-$d_6$): δ 5.27-5.25 (m, 1H), 3.76-3.69 (m, 1H), 3.58-3.48 (m, 1H), 3.28-3.22 (m, 3H), 3.10-3.00 (m, 1H), 2.94 (s, 6H), 2.45-2.40 (m, 1H), 2.30-2.22 (m, 1H), 2.20-1.85 (m, 7H), 1.82-1.72 (m, 2H), 1.71-1.45 (m, 5H), 1.44-1.32 (m, 6H), 1.31-1.21 (m, 4H), 1.99-0.96 (m, 5H), 0.94 (s, 3H) 0.93-0.83 (m, 4H), 0.64 (s, 3H).

Example 88: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(1-oxa-δ-azaspiro[4.5]decan-δ-yl)pentan-1-one

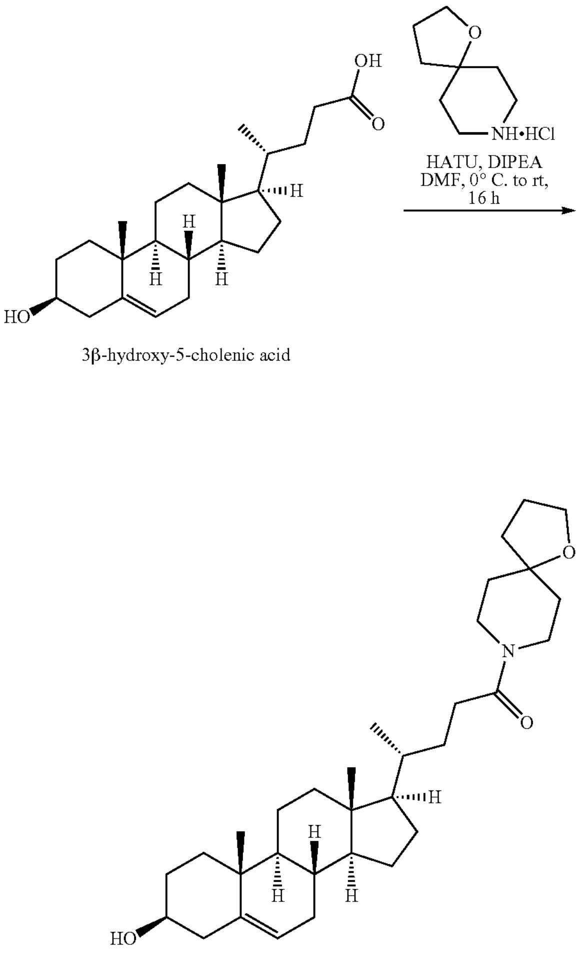

3β-hydroxy-5-cholenic acid

88

Compound 88 was synthesized according to the general procedure A using 3β-hydroxy-5-cholenic acid (100 mg, 0.267 mmol), 1-oxa-δ-azaspiro[4.5]decane hydrochloride (71 mg, 0.4 mmol), HATU (230 mg, 0.534 mmol), DIPEA (138 μL, 0.801 mmol), and DMF (2 mL). The crude material was purified by column chromatography over silica gel (100-200 mesh) with gradient elution of 50-70% ethyl acetate in hexanes to afford the title compound 88 (30 mg, 22.5%) as an off white solid. ELSD-MS (ESI) m/z: 497.9 $[M+H]^+$; $^1H$ NMR (400 MHz, DMSO-$D_6$) 8 5.26-5.25 (m, 1H), 4.58 (d, J=4.8 Hz, 1H), 3.72 (t, J=6.8 Hz, 2H), 3.68-3.67 (m, 1H), 3.48-3.45 (m, 1H), 3.39-3.36 (m, 1H), 3.28-3.17 (m, 2H), 2.31-2.26 (m, 1H), 2.23-2.06 (m, 3H), 1.98-1.93 (m, 1H), 1.91-1.83 (m, 3H), 1.81-1.72 (m, 2H), 1.70-1.59 (m, 4H), 1.57-1.32 (m, 10H), 1.31-1.21 (m, 2H), 1.20-0.96 (m, 6H), 0.94 (s, 3H), 0.91-0.83 (m, 4H), 0.64 (s, 3H).

Example 89: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(2-oxa-δ-azaspiro[4.5]decan-δ-yl)pentan-1-one

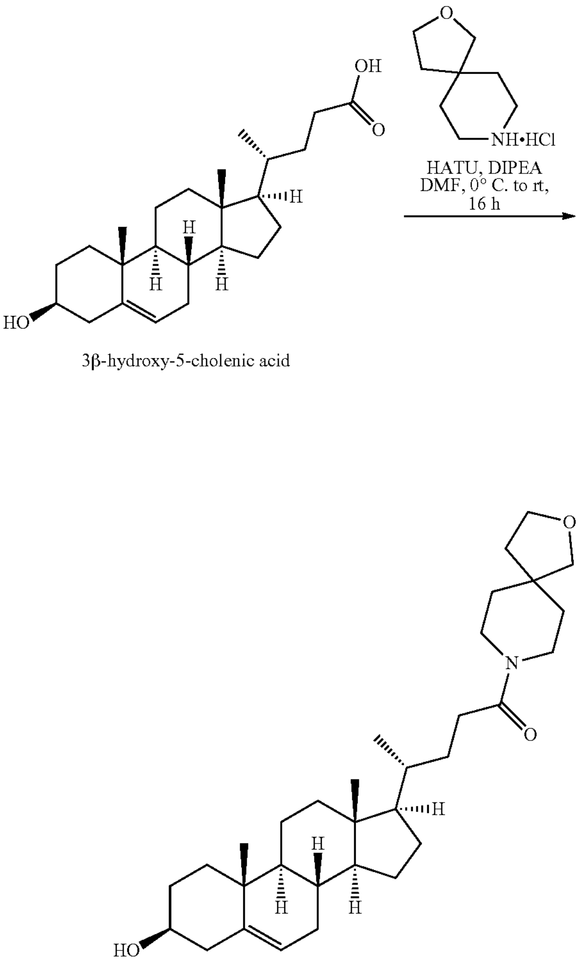

3β-hydroxy-5-cholenic acid

89

Compound 89 was synthesized according to the general procedure A using 3β-hydroxy-5-cholenic acid (100 mg, 0.267 mmol), 2-oxa-δ-azaspiro[4.5]decane hydrochloride (71.2 mg, 1.5 eq, 0.4 mmol), HATU (230 mg, 0.534 mmol), DIPEA (138 μL, 0.801 mmol), and DMF (2 mL). The crude material was purified by column chromatography over silica gel (100-200 mesh) with gradient elution of 50-70% ethyl acetate in hexanes to afford the title compound 89 (87 mg, 65%) as an off white solid. ELSD-MS (ESI) m/z: 497.7 $[M+H]^+$; $^1H$ NMR (400 MHz, $CDCl_3$) δ 5.35-5.34 (m, 1H), 3.88 (t, J=7.2 Hz, 2H), 3.68-3.41 (m, 7H), 2.42-2.31 (m, 1H), 2.29-2.15 (m, 3H), 2.04-1.93 (m, 2H), 1.89-1.75 (m, 6H), 1.55-1.41 (m, 8H), 1.39-1.22 (m, 3H), 1.2-1.03 (m, 5H), 1.0 (s, 3H), 0.97-0.93 (m, 4H), 0.68 (s, 3H).

Example 90: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-hydroxy-4-(prop-1-yn-1-yl)piperidin-1-yl)pentan-1-one

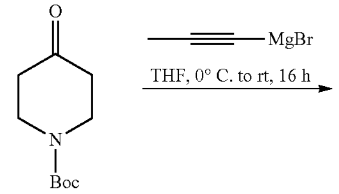

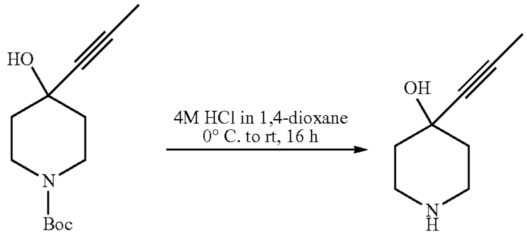

A

B

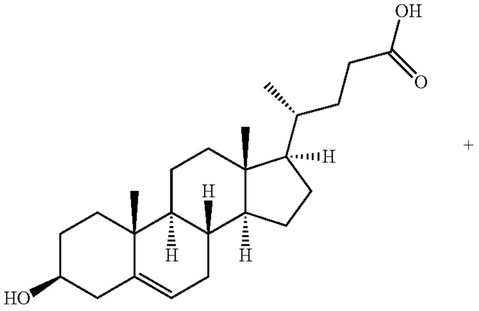

3β-hydroxy-5-cholenic acid

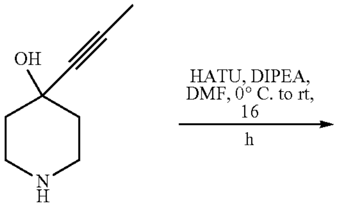

B

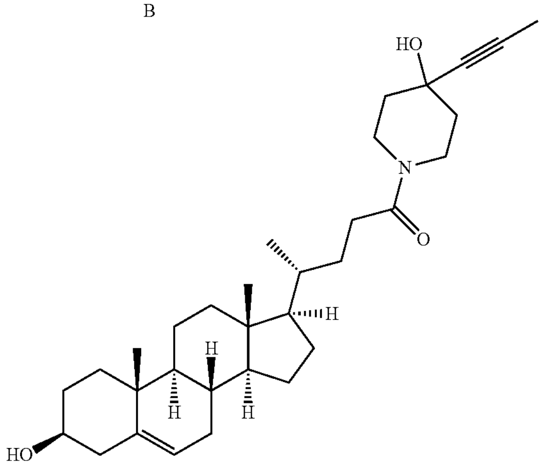

90

To a stirred solution of tert-butyl 4-oxopiperidine-1-carboxylate (0.3 g, 1.51 mmol) in dry THF (6 mL, 73.7 mmol) at 0° C. was added 1-propynylmagnesium bromide (0.5 M in THF, 9 mL, 4.52 mmol). The reaction mixture was stirred at ambient temperature for 3 h. Upon completion, the reaction mixture was quenched with saturated $NH_4Cl$ (20 mL), extracted with ethyl acetate (2×50 mL), and the combined organic layer was washed with water (50 mL) and brine (50 mL). The separated organic layer was dried over anhydrous sodium sulfate, filtered, and concentrated in vacuo to afford compound A (300 mg, 55%) as a brown liquid.

To a stirred solution of crude compound A (0.3 g, 1.25 mmol) in 1,4-dioxane (3 mL, 46.9 mmol) at 0° C. was added 4 M HCl in 1,4-dioxane (0.6 mL) and allowed to stir the reaction mixture at room temperature for 3 h. Upon completion, the reaction mixture was concentrated to afford the crude compound B (130 mg, 36%) as an off white solid.

Compound 90 was synthesized according to general procedure A using 3β-hydroxy-5-cholenic acid (70 mg, 187 μmol), DIPEA (1.2 mL, 1.6 mmol), HATU (203 mg, 0.267 mmol), crude compound B (111 mg, 0.801 mmol), and DMF (3 mL). The crude compound was purified by preparative HPLC [column: Gemini C18 2.0*50 mm, 3 μm; mobile phase: A 0.01% FA in water; flow rate: 0.5 ml/min, program (Time/% B): 0.02/40, 2.0/60, 3.50/70, 3.52/80] to afford the title compound 90 (15 mg, 11.3%) as an off-white solid. LC-MS (ESI) m/z 495.9 $(M+H)^+$; $^1H$ NMR (400 MHz, DMSO-$d_6$): δ 5.42 (s, 1H), 5.26-5.25 (d, J=5.2 Hz, 1H), 4.59-4.57 (d, J=4.4 Hz, 1H), 3.68-3.67 (m, 1H), 3.59-3.54 (m, 1H), 3.26-3.22 (m, 2H), 2.34-2.31 (m, 1H), 2.22-2.05 (m, 3H), 1.98-1.85 (m, 2H), 1.81 (s, 3H), 1.79-1.51 (m, 8H), 1.52-1.32 (m, 7H), 1.31-0.96 (m, 8H), 0.93 (s, 3H), 0.90 (d, J=2.4 Hz, 3H), 0.89-0.83 (m, 1H), 0.64 (s, 3H).

Example 91: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-hydroxy-4-phenylpiperidin-1-yl) pentan-1-one

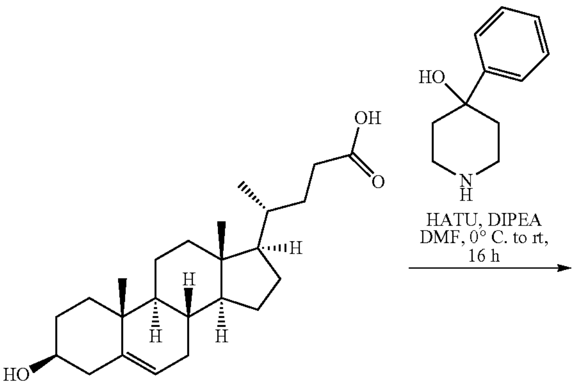

3β-hydroxy-5-cholenic acid

-continued

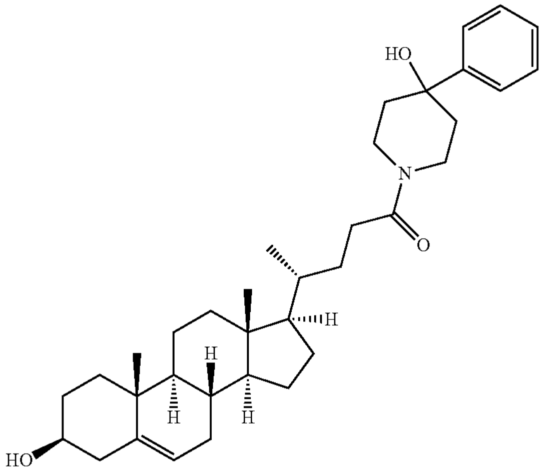

91

Compound 91 was synthesized according to the general procedure A using 3β-hydroxy-5-cholenic acid (100 mg, 0.267 mmol), HATU (203 mg, 0.534 mmol), DIPEA (0.138 mL, 0.8 mmol), 4-phenylpiperidin-4-ol (71 mg, 0.4 mmol), and DMF (2 mL). The crude material was purified by column chromatography over silica gel (100-200 mesh) with 0-5% gradient elution of MeOH in DCM to afford the title compound 91 (55 mg, 39%) as an off-white solid. LC-MS (ESI) m/z: 534 $[M+H]^+$; $^1H$ NMR (400 MHz, $CDCl_3$) δ 7.48 (d, J=1.6 Hz, 2H), 7.38 (t, J=7.2 Hz, 2H), 7.29 (d, J=7.2 Hz, 1H), 5.36-5.34 (m, 1H), 4.65-4.55 (m, 1H), 3.79-3.73 (m, 1H), 3.62-3.48 (m, 2H), 3.13-3.04 (m, 1H), 2.49-2.38 (m, 1H), 2.32-2.19 (m, 3H), 2.09-1.91 (m, 5H), 1.89-1.75 (m, 6H), 1.63-1.55 (m, 1H), 1.51-1.41 (m, 7H), 1.39-1.25 (m, 3H), 1.21-1.02 (m, 4H), 1.00 (s, 3H), 0.98-0.92 (m, 4H), 0.69 (s, 3H).

Example 92: (R)-1-(4-butyl-4-hydroxypiperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

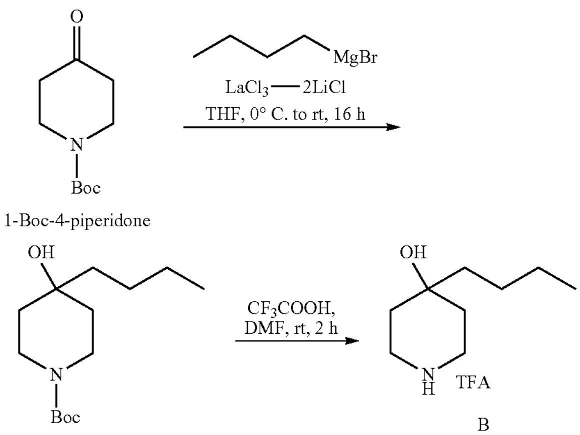

1-Boc-4-piperidone

A

B

-continued

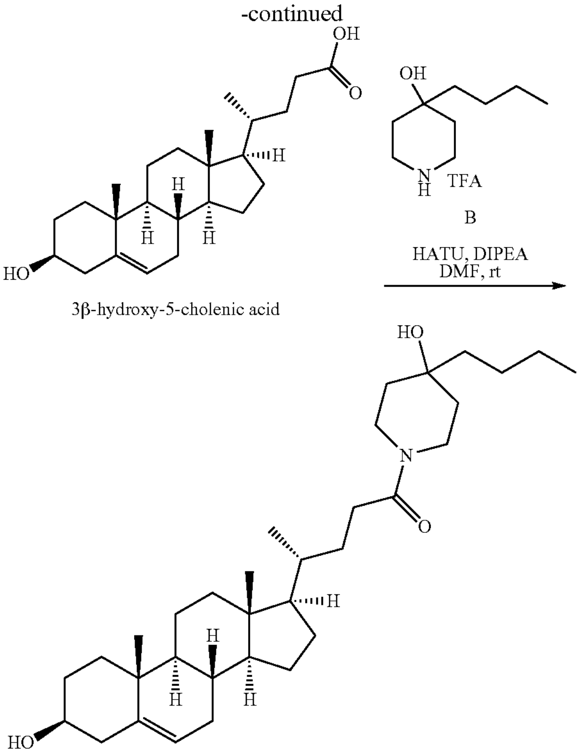

3β-hydroxy-5-cholenic acid

B

92

To a stirred solution of $LaCl_3\cdot 2LiCl$ (0.6 M in THF,1.25 mL, 0.75 mmol) at 0° C. was added n-BuMgBr (1M in THF, 0.75 mL, 0.75 mmol) under nitrogen atmosphere, and after stirring the reaction mixture at 0° C. for 1 h was added 1-Boc-4-piperidone (100 mg, 0.50 mmol) in THF (5 mL) drop wise at 0° C. The resultant reaction mixture was stirred at room temperature for 16 h. Upon completion, the reaction mixture was quenched with sat.aq. $NH_4Cl$ (10 mL) and extracted with ethyl acetate (10 mL×3). The combined organic layer was washed with brine (10 mL), dried over anhydrous sodium sulfate, filtered, and concentrated in vacuo to afford compound A as an oily compound (80 mg).

To a stirred solution of crude compound A (80 mg, 0.31 mmol) in DCM (5 mL) was added TFA (0.2 mL, 2.48 mmol) at 0° C. under nitrogen atmosphere. The resultant reaction mixture was stirred at room temperature for 2 h. Upon completion, the reaction mixture was concentrated and co-distilled with toluene in vacuo to afford compound B as a brown color gummy liquid (40 mg).

Compound 92 was synthesized according to the general procedure A using 3β-hydroxy-5-cholenic acid (50 mg, 0.133 mmol), HATU (102 mg, 0.267 mmol), DIPEA (0.08 mL, 0.4 mmol), crude compound B (40 mg, 0.16 mmol), and DMF (2.5 mL). The obtained crude material was purified by column chromatography over silica gel (100-200 mesh) with 0-5% gradient elution of MeOH in DCM to afford compound 92 as an off-white solid (49 mg, 71%). ELSD-MS (ESI) m/z: 513.6 $[M+H]^+$; $^1H$ NMR (400 MHz, DMSO-$D_6$) δ 5.27-5.25 (m, 1H), 4.59 (d, J=4.4 Hz, 1H), 4.16 (s, 1H), 4.05-3.96 (m, 1H), 3.59-3.50 (m, 1H), 3.30-3.21 (m, 2H), 2.93-2.85 (m, 1H), 2.32-2.25 (m, 1H), 2.21-2.05 (m, 3H), 2.00-1.87 (m, 2H), 1.83-1.72 (m, 2H), 1.71-1.61 (m, 2H), 1.55-1.32 (m, 13H), 1.30-1.19 (m, 6H), 1.18-1.03 (m, 4H), 1.01-0.97 (m, 1H), 0.94 (s, 3H), 0.91-0.82 (m, 7H), 0.64 (s, 3H).

Example 93: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-hydroxy-4-isobutylpiperidin-1-yl) pentan-1-one

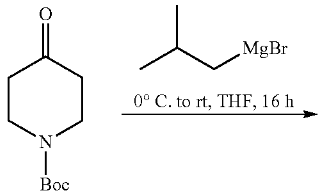

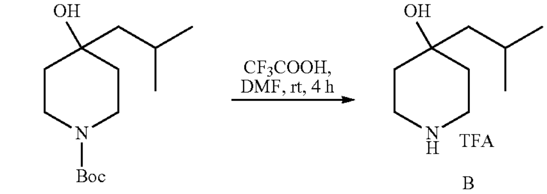

A

B

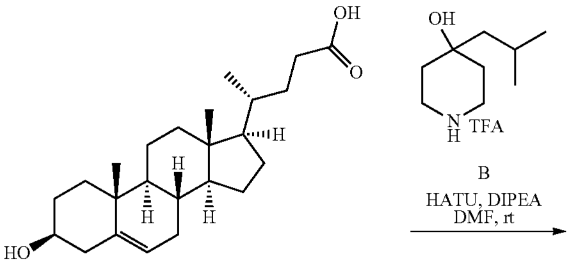

B

3β-hydroxy-5-cholenic acid

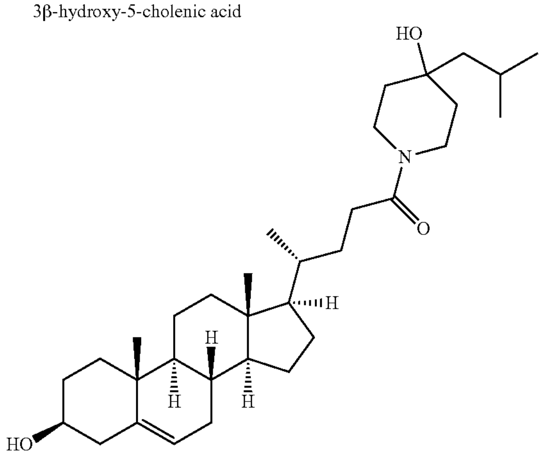

93

To a stirred solution of LaCl3·2LiCl (0.6 M in THF, 1.24 g, 3.76 mmol) in THF (5 mL) under nitrogen atmosphere, was added isobutylmagnesium chloride (1.0 M in THF, 573 mg, 3.76 mmol) slowly through syringe at 0° C. After stirring at room temperature for 3 h, a solution of tert-butyl 4-oxopiperidine-1-carboxylate (0.5 g, 2.51 mmol) in THE (5.0 mL) was added to the mixture. The resultant reaction mixture was allowed to stir at room temperature for 16 h. Upon completion, the reaction mixture was cooled to 0° C., quenched with acetic acid (5 mL), and extracted with ethyl acetate (3×20 mL). The combined organic layer was washed with brine (5 mL), dried over anhydrous sodium sulfate, and concentrated under high vacuum to afford crude compound A (0.5 g, 1.94 mmol) as a pale yellow liquid.

To a stirred solution of crude compound A (0.5 g, 1.94 mmol) in DCM (10 mL, 156 mmol) was added trifluoroacetic acid (443 mg, 3.89 mmol) at 0° C. under argon atmosphere. The reaction mixture was stirred at room temperature for 4 h. Upon completion, the reaction mixture was concentrated and co-distilled with toluene to get crude compound B (0.3 g, 1.18 mmol) as brown gummy liquid.

Compound 93 was synthesized according to the general procedure A using 3β-hydroxy-5-cholenic acid (150 mg, 0.4 mmol), HATU (305 mg, 0.801 mmol) DIPEA (207 mg, 1.6 mmol), crude compound B, 440750 (94.5 mg, 1.5 eq, 601 μmol), and DMF (3 mL). The reaction time was 16 h. The obtained crude material was purified by column chromatography over silica gel (100-200 mesh) with gradient elution of 50-70% ethyl acetate in hexanes to afford compound 93 (34.3 mg) as an off white solid. LC-MS (ESI) m/z: 534 $[M+H]^+$; $^1H$ NMR (400 MHz, DMSO-$d_6$): δ 5.27-5.25 (m, 1H), 4.59 (d, J=4.8 Hz, 1H), 4.13 (s, 1H), 4.02-3.99 (m, 1H), 3.56-3.53 (m, 1H), 3.28-3.20 (m, 2H), 2.93-2.86 (m, 1H), 2.30-2.23 (m, 1H), 2.21-2.05 (m, 3H), 1.98-1.86 (m, 2H), 1.84-1.72 (m, 3H), 1.70-1.45 (m, 6H), 1.44-1.32 (m, 6H), 1.31-1.21 (m, 4H), 1.20-0.96 (m, 6H), 0.94 (s, 3H), 0.91-0.82 (m, 10H), 0.64 (s, 3H).

Example 94: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-methoxypiperidin-1-yl) pentan-1-one

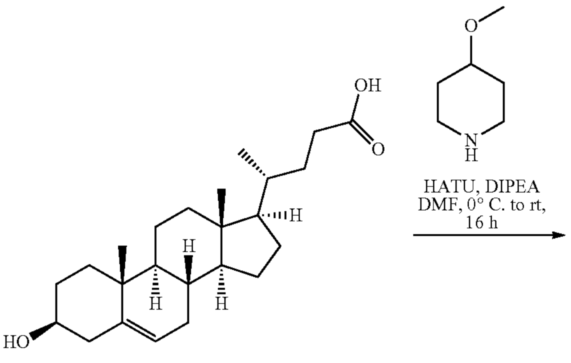

3β-hydroxy-5-cholenic acid

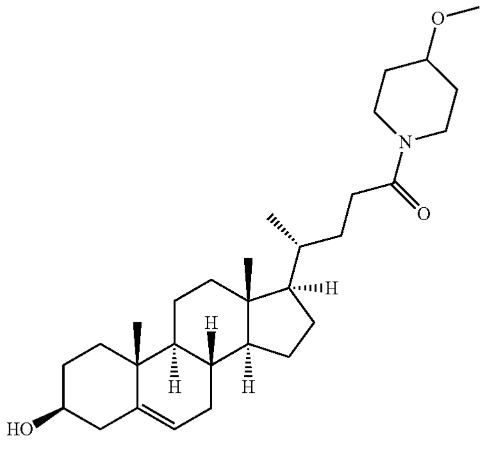

94

Compound 94 was synthesized according to the general procedure A using 3β-hydroxy-5-cholenic acid (100 mg, 0.267 mmol), HATU (203 mg, 0.534 mmol), DIPEA (0.138 mL, 0.8 mmol), 4-methoxypiperidine (36.9 mg, 0.32 mmol), and DMF (3 mL). The obtained crude material was purified by column chromatography over silica gel (100-200 mesh) with 0-50% gradient elution of ethyl acetate in hexanes to afford compound 94 as an off-white solid (180 mg, 58%). ELSD-MS (ESI) m/z: 471.9 $[M+H]^+$; $^1H$ NMR (400 MHz, DMSO-$d_6$): δ 5.27-5.25 (m, 1H), 4.59 (d, J=4.4 Hz, 1H), 3.84-379 (m, 1H), 3.66-3.60 (m, 1H), 3.39-3.37 (m, 1H), 3.25-3.21 (s, 3H & m, 1H), 3.20-3.14 (m, 1H), 3.08-3.00 (m, 1H), 2.32-2.25 (m, 1H), 2.23-2.05 (m, 3H), 1.99-1.89 (m, 2H), 1.86-1.71 (m, 4H), 1.69-1.60 (m, 2H), 1.58-1.45 (m, 3H), 1.43-1.32 (m, 5H), 1.31-1.22 (m, 2H), 1.21-1.03 (m, 4H), 1.02-0.97 (m, 2H), 0.94 (s, 3H), 0.91-0.82 (m, 4H), 0.64 (s, 3H).

Example 95: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-7-methyl-1,4-oxazepan-4-yl)pentan-1-one

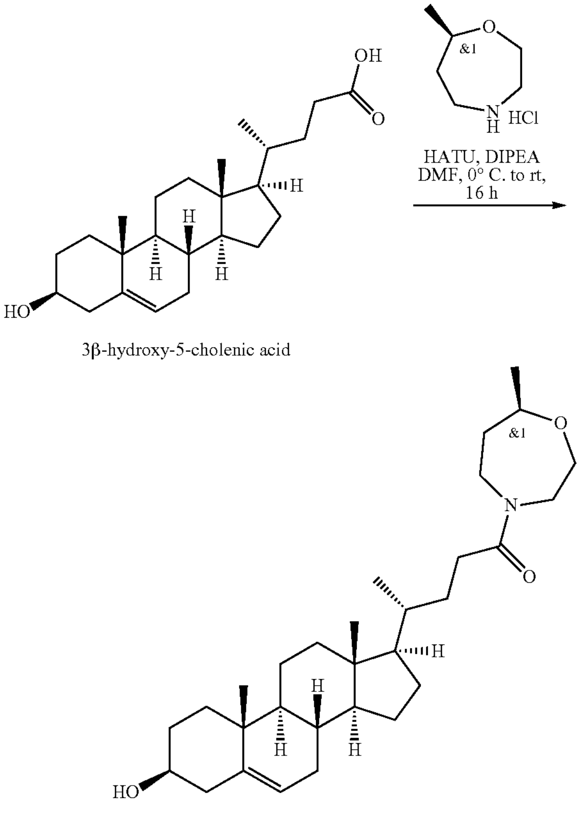

3β-hydroxy-5-cholenic acid

95

Compound 95 was synthesized according to the general procedure A using 3β-hydroxy-5-cholenic acid (100 mg, 0.267 mmol), HATU (203 mg, 0.534 mmol), DIPEA (0.138 mL, 0.8 mmol), racemic 7-methyl-1,4-oxazepane hydrochloride (60.7 mg, 0.4 mmol) and DMF (2 mL). The crude material was purified by silica gel (100-200 mesh) chromatography with 0-70% gradient elution of ethyl acetate in hexanes to afford the title compound 95 (60 mg, 48%) as an off-white solid. ELSD-MS (ESI) m/z: 471.8 $[M+H]^+$; $^1H$ NMR (400 MHz, DMSO-$D_6$) δ 5.28-5.25 (m, 1H), 4.59 (d, J=4.4 Hz, 1H), 3.92-3.79 (m, 1H), 3.71-3.59 (m, 1H), 3.58-3.49 (m, 3H), 3.43-3.19 (m, 3H), 2.30-2.25 (m, 1H), 2.23-2.05 (m, 4H), 1.99-1.88 (m, 3H), 1.86-1.72 (m, 3H), 1.71-1.61 (m, 2H), 1.59-1.43 (m, 3H), 1.42-1.35 (m, 4H), 1.32-1.11 (m, 4H), 1.11-1.06 (m, 4H), 1.02-0.98 (m, 2H), 0.94 (s, 3H), 0.92-0.82 (m, 3H), 0.64 (s, 3H).

Example 96: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-2-methyl-1,4-oxazepan-4-yl)pentan-1-one

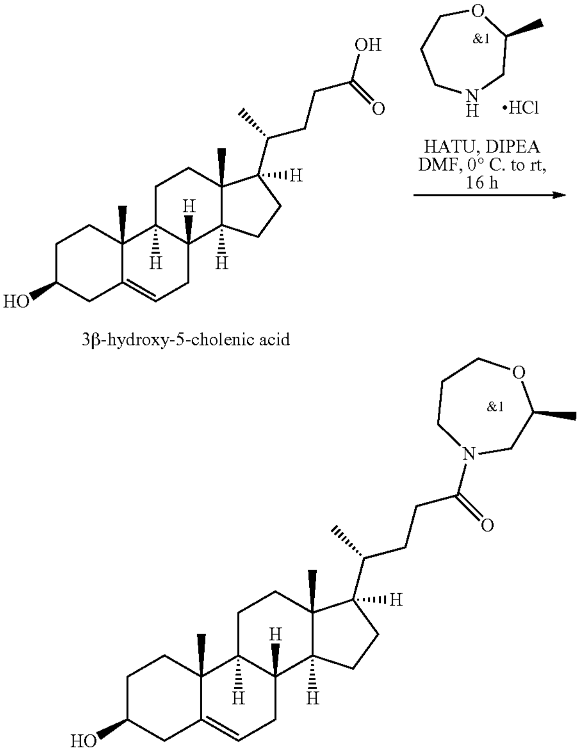

3β-hydroxy-5-cholenic acid

96

Compound 96 was synthesized according to the general procedure A using 3β-hydroxy-5-cholenic acid (100 mg, 0.267 mmol), HATU (203 mg, 0.534 mmol), DIPEA (0.138 mL, 0.8 mmol), racemic 2-methyl-1,4-oxazepane (46 mg, 0.4 mmol) and DMF (2 mL). The crude material was purified over silica gel chromatography (100-200 mesh) with 0-70% gradient elution of ethyl acetate in hexanes to afford compound 96 (61 mg, 48%) as an off-white solid. ELSD-MS (ESI) m/z: 471.9 $[M+H]^+$; $^1H$ NMR (400 MHz, DMSO-$D_6$) δ 5.27-5.25 (m, 1H), 4.59 (d, J=4.4 Hz, 1H), 4.02-3.83 (m, 2H), 3.78-3.65 (m, 1H), 3.62-3.48 (m, 1H), 3.40-3.21 (m, 2H), 3.18-3.10 (m, 1H), 3.03-2.85 (m, 1H), 2.79-2.7 (m, 1H), 2.29-2.21 (m, 1H), 2.20-2.05 (m, 3H), 1.99-1.85 (m, 2H), 1.84-1.73 (m, 4H), 1.71-1.62 (m, 2H), 1.60-1.45 (m, 4H), 1.42-1.31 (m, 4H), 1.30-1.12 (m, 3H), 1.11-1.03 (m, 3H), 1.01-0.96 (m, 2H), 0.96 (s, 3H), 0.94-0.85 (m, 4H), 0.64 (s, 3H).

Example 97: (R)-1-(3-(1,1,1,3,3,3-hexafluoro-2-hydroxypropan-2-yl) azetidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl) pentan-1-one

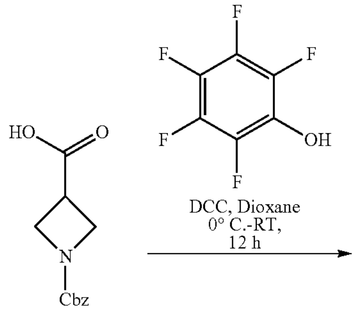

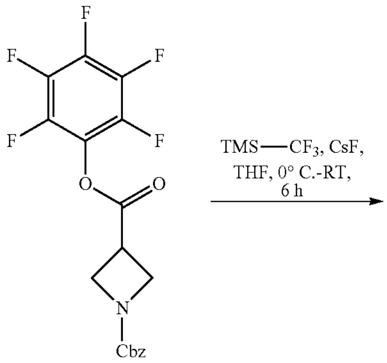

A

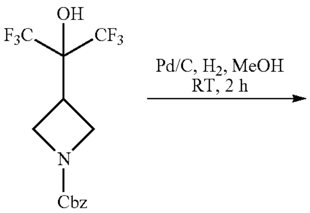

B

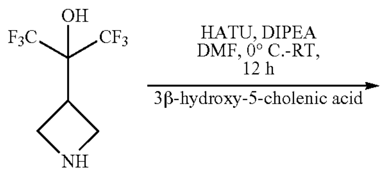

C

-continued

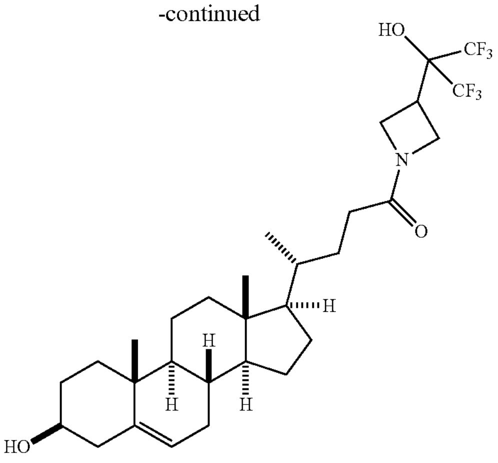

97

To a stirred solution of 1-[(benzyloxy)carbonyl]azetidine-3-carboxylic acid (0.5 g, 2.13 mmol) in 1,4-dioxane (5 mL) at 0° C. under nitrogen atmosphere were added pentafluorophenol (430 mg, 2.34 mmol) and DCC (482 mg, 2.34 mmol). The resultant reaction mixture was stirred at room temperature for 16 h. Upon completion, the reaction mixture was filtered through pad of Celite and washed with ethyl acetate. The obtained filtrate was concentrated in vacuo to afford crude compound A that was purified by column chromatography over 100-200 silica gel mesh by eluting 10% ethyl acetate in hexane to afford compound A (410 mg, 48%) as a yellow oil.

To the stirred solution of compound A (990 mg, 2.47 mmol) in THF 10 mL) at 0° C. were added trimethyl (trifluoromethyl)silane (1.05 g, 7.40 mmol) and CsF (187 mg, 1.23 mmol) under nitrogen atmosphere. The resultant reaction mixture was allowed to stir at room temperature for 16 h. Upon completion, the resultant reaction mixture was concentrated in vacuo to afford crude compound B. The crude compound was purified by column chromatography over 100-200 silica gel mesh by eluting 4% MeOH in DCM to afford compound B (550 mg, 62%) as a colorless oil To the stirred solution of compound B (0.5 g, 1.4 mmol) in methanol (5 mL) at room temperature was added 10% Pd/C (53 mg). The resultant reaction mixture was degassed with $H_2$ gas and allowed to stir at room temperature for 2 h under hydrogen atmosphere (bladder). Upon completion, the resultant reaction mixture was filtered through pad of Celite and washed with methanol. The collected filtrate was concentrated in vacuo to afford crude compound C (250 mg) as a white solid.

Compound 97 was synthesized according to general procedure A using 3β-hydroxy-5-cholenic acid (0.1 g, 0.27 mmol), DIPEA (173 mg, 1.33 mmol), HATU (203 mg, 0.53 mmol), crude compound C (238 mg, 1.07 mmol), and THE (3 mL). The reaction time was 16 h. The obtained crude compound was purified by column chromatography over 100-200 silica gel mesh by eluting 40% ethyl acetate in hexane to afford compound 97 (115 mg, 70%) as an off-white solid. LC-MS (ELSD) m/z: 579.7; $^1$H NMR (400 MHz, DMSO-$d_6$): δ 8.49 (s, 1H), 5.28-5.25 (m, 1H), 4.59 (d, J=4.0 Hz, 1H), 4.26-4.13 (m, 2H), 4.00-3.95 (m, 1H), 3.85 (t, J=9.2 Hz, 1H), 3.45-3.38 (m, 1H), 3.26-3.20 (m, 1H), 2.18-1.87 (m, 6H), 1.82-1.31 (m, 11H), 1.30-0.96 (m, 7H), 0.95-0.82 (m, 8H), 0.64 (s, 3H).$^{19}$F NMR (376 MHz, DMSO-$d_6$): δ–74.75–-74.82 (d, 2×$CF_3$).

Example 98: (R)-1-((R)-3-(1,1,1,3,3,3-hexafluoro-2-hydroxypropan-2-yl)pyrrolidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

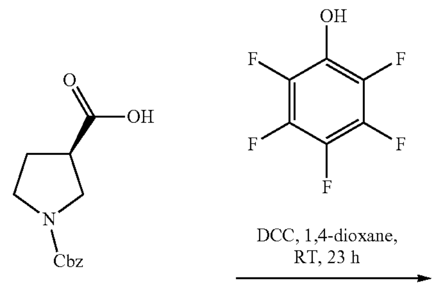

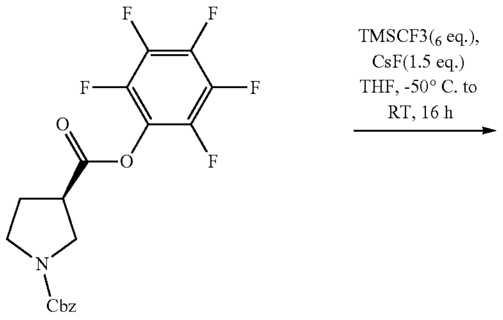

A

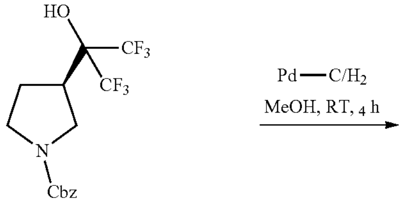

B

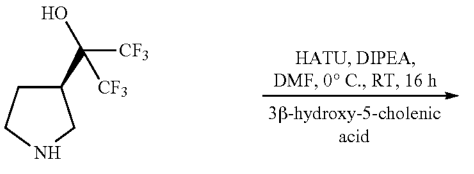

C

-continued

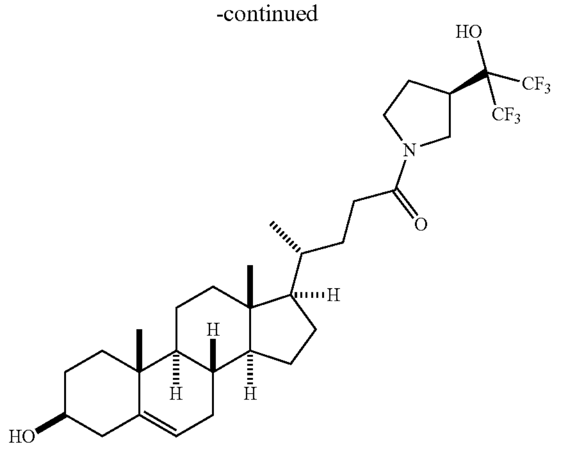

98

To a stirred solution of 1-[(benzyloxy)carbonyl]pyrrolidine-3-carboxylic acid (0.7 g, 2.81 mmol) in 1,4-dioxane (14 mL) at 0° C. were added pentafluorophenol (569 mg, 3.09 mmol) and N,N-dicyclohexylmethanediimine (637 mg, 3.09 mmol) under nitrogen atmosphere. The resultant reaction mixture was stirred at room temperature for 16 h. Upon completion, the reaction mixture was filtered through pad of Celite and washed with ethyl acetate. The filtrate was concentrated in vacuo to afford crude material that was purified by column chromatography over 100-200 silica gel mesh with eluting 10% ethyl acetate in hexane to afford compound A (610 mg, 52%) as yellow liquid.

To a stirred solution of compound A (0.4 g, 963 μmol) in dry THF (8 mL, 98.3 mmol) at −50° C. were added trimethyl (trifluoromethyl)silane (822 mg, 5.78 mmol) and CsF (219 mg, 1.44 mmol). The resultant reaction mixture was stirred at room temperature for 16 h. Upon completion, the reaction mixture was concentrated in vacuo to afford crude material that was purified by preparative HPLC [column: Kinetex EVO,C18 (50×3 mm, 2.41.); mobile phase: A 0.01% formic acid in water; flow rate: 0.5 ml/min, program (Time/% B): 0.01/5,4/95,7/95,7.01/5] to afford compound B (130 mg, 36%) as an off-white solid.

To a stirred solution of compound B (0.1 g, 269 μmol) in methanol (5 mL, 123 mmol) at room temperature was added 10% Pd/C (20 mg, 20% wt/wtQ. The resultant reaction mixture was degassed with hydrogen gas and stirred at room temperature for 4 h under hydrogen atmosphere (hydrogen bladder). Upon completion, the reaction mixture was filtered through pad of Celite and washed with methanol. The filtrate was concentrated in vacuo to afford crude compound C (50 mg, 78%) as an off-white solid.

Compound 98 was synthesized according to the general procedure A using 3β-hydroxy-5-cholenic acid (70 mg, 0.187 mmol), DIPEA (0.6 mL, 0.561 mmol), HATU (142 mg, 0.187 mmol) crude compound B (66 mg, 0.280 mmol), and in DMF (2 mL). The crude compound was purified by prep HPLC [column: Gemini C18 2.0*50 mm, 3 μm; mobile phase: A 0.01% FA in water; flow rate: 0.5 ml/min, program (Time/% B): 0.02/6, 2.0/70, 3.50/80, 3.52/90., 5.0/100] to afford compound 98 (8 mg, 11%) as an off-white solid. LC-MS (ESI) m/z 591.7 $(M+H)^+$; 1H NMR (400 MHz, DMSO-$d_6$): δ 8.15 (s, 1H), 5.26 (d, J=4.40 Hz, 1H), 4.59 (d, J=4.80 Hz, 1H), 3.62 (m, 2H), 3.32-3.37 (m, 1H), 3.23 (m, 1H), 2.67-2.67 (m, 1H), 2.32-2.33 (m, 1H), 2.08-2.14 (m, 4H), 1.74-1.97 (m, 4H), 1.65-1.68 (m, 2H), 1.50-1.53 (m, 2H), 1.46-1.49 (m, 1H), 1.41-1.49 (m, 4H).$^{19}$F NMR (376 MHz, DMSO-$d_6$): δ-72.95--73.03 (m, $CF_3$), -73.12--73.20 (m, $CF_3$), 73.99--74.02 (m, $CF_3$).

Example 99: (R)-1-(4-(1,1,1,3,3,3-hexafluoro-2-hydroxypropan-2-yl) piperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

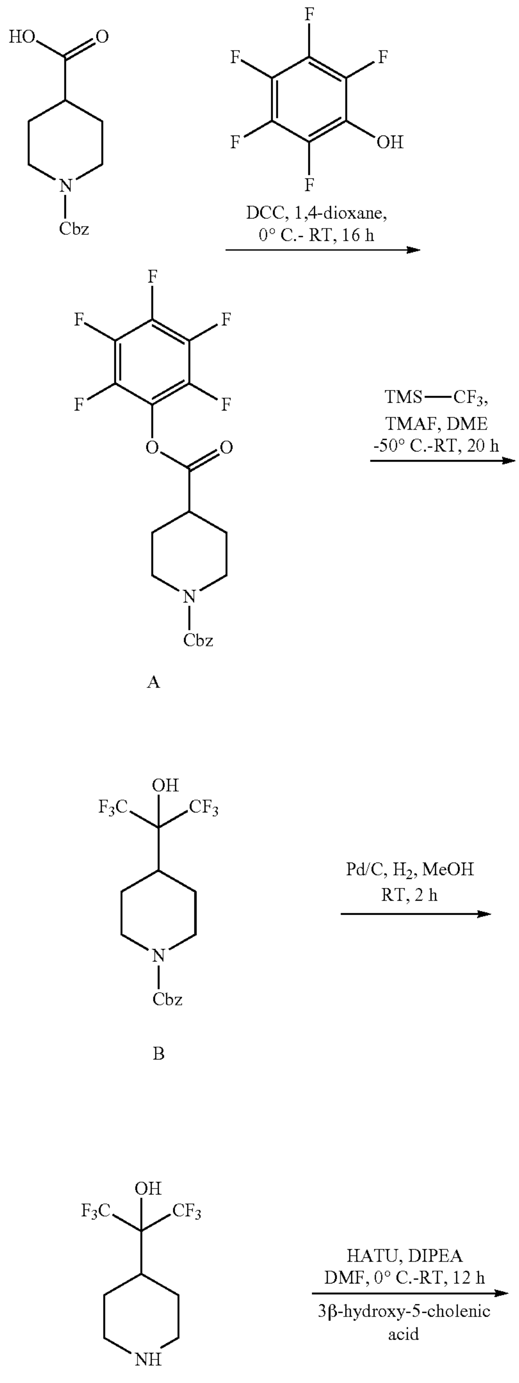

A

B

C

-continued

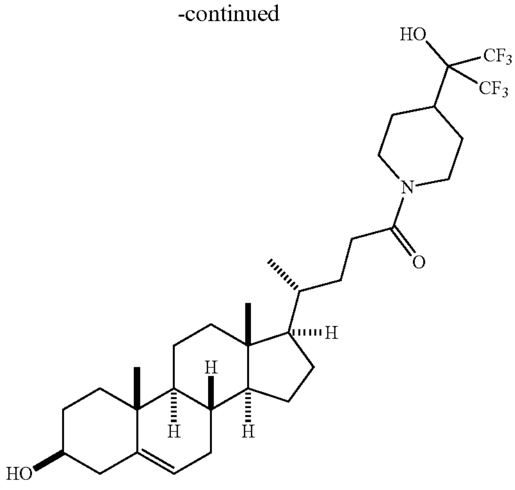

99

To the stirred solution of 1-[(benzyloxy)carbonyl]piperidine-4-carboxylic acid (1 g, 3.8 mmol) in 1,4-dioxane (10 mL) at 0° C. were added pentafluorophenol (769 mg, 4.18 mmol) and DCC (862 mg, 4.18 mmol) under nitrogen atmosphere. The resultant reaction mixture was stirred at room temperature for 16 h. Upon completion, the reaction mixture was filtered through pad of celite, washed with ethyl acetate. The filtrate was concentrated in vacuo to afford crude. The crude compound was purified by column chromatography over 100-200 silica gel mesh by eluting 10% ethyl acetate in hexane to obtain compound A (1.5 g, 92%) as a light yellow solid.

To the stirred solution of compound A (0.8 g, 1.86 mmol) in THE (8 mL, 98.3 mmol) at 0° C. were added trimethyl (trifluoromethyl)silane (795 mg, 5.59 mmol) and CsF (142 mg, 0.93 mmol) under nitrogen atmosphere. The resultant reaction mixture was allowed to stir at room temperature for 16 h. Upon completion, reaction mixture was concentrated in vacuo to afford crude compound. The crude compound was purified by preparative HPLC [column: KINETEX EVO,C18 (50x3 mm, 2.41.; mobile phase A: 0.01% FA in water; mobile Phase B: 100% ACN; flow rate: 0.6 mL/min; program (T/% B):0.01/5,4/95,7/95,7.01/5] to afford compound B (260 mg, 36%) as a colorless oil. LC-MS (ESI) m/z: 386 $[M+H]^+$.

To the stirred solution of compound B (0.2 g, 0.52 mmol) in methanol (2 mL) at room temperature was added 10% Pd/C (67 mg) and the resultant reaction mixture was degassed with hydrogen gas and allowed to stir at room temperature for 2 h under hydrogen atmosphere (bladder). Upon completion, the resultant reaction mixture was filtered through pad of Celite and washed with methanol. The collected filtrate was concentrated in vacuo to afford crude compound C (105 mg) as a white solid.

Compound 99 was synthesized according to the general procedure A using 3β-hydroxy-5-cholenic acid (0.1 g, 0.27 mmol), DIPEA (173 mg, 1.33 mmol), HATU (203 mg, 0.53 mmol), compound C (101 mg, 0.4 mmol), and THE (2 mL). The obtained crude material was purified by column chromatography over 100-200 silica gel mesh by eluting 65% ethyl acetate in hexane to afford compound 99 (85 mg, 52%) as an off-white solid. LC-MS (ESI) m/z: 608 $[M+H]^+$; 1H NMR (400 MHz, DMSO-$d_6$): δ 7.80 (s, 1H), 5.29-5.24 (m, 1H), 4.59 (d, J=4.4 Hz, 1H), 4.50 (d, J=12.4 Hz, 1H), 3.98 (d, J=13.2 Hz, 1H), 3.25-3.20 (m, 1H), 3.00-2.90 (m, 1H), 2.45-2.37 (m, 2H), 2.25-2.02 (m, 5H), 2.00-1.85 (m, 4H), 1.80-1.32 (m, 11H), 1.30-0.96 (m, 8H), 0.94 (s, 3H), 0.92-0.83 (m, 4H), 0.64 (s, 3H); $^{19}F$ NMR (376 MHz, DMSO-$d_6$): δ-71.74 (s, 2×$CF_3$).

Example 100: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(6-hydroxy-2-azaspiro[3.3]heptan-2-yl)pentan-1-one

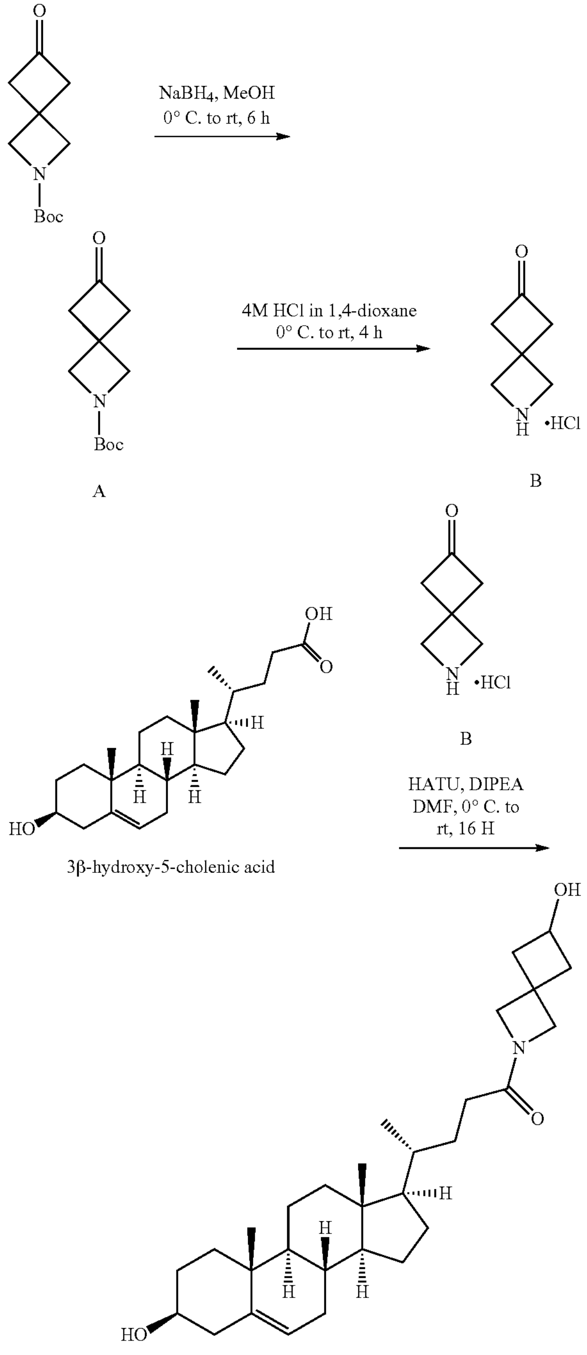

A

B

B

3β-hydroxy-5-cholenic acid

100

To a stirred solution of tert-butyl 6-oxo-2-azaspiro[3.3]heptane-2-carboxylate (500 mg, 2.37 mmol) in MeOH (10 mL) was added $NaBH_4$ (107 mg, 2.83 mmol) at 0° C. under nitrogen atmosphere. The resulting reaction mixture was stirred at room temperature for 6 h. Upon completion, the reaction mixture was quenched with ice water (20 mL) and extracted with ethyl acetate (30 mL×3). The combined organic layer was washed with brine (10 mL), dried over anhydrous sodium sulfate, filtered, and concentrated in vacuo to afford compound A as a pale-yellow oil (250 mg).

To a stirred solution of crude compound A (100 mg, 0.469 mmol) in 1,4-dioxane (3 mL) was added solution of HCl (4M in 1,4-dioxane, 0.7 mL, 1.88 mmol) at 0° C. under nitrogen atmosphere. The resulting reaction mixture was stirred at room temperature for 4 h. Upon completion, the reaction mixture was concentrated to afford compound B as a brown color liquid (50 mg).

Compound 100 was synthesized according to the general procedure A using 3β-hydroxy-5-cholenic acid (50 mg, 0.133 mmol), HATU (101 mg, 0.267 mmol), DIPEA (0.07 mL, 0.4 mmol), crude compound B (24 mg, 0.16 mmol), and DMF (3 mL). The obtained crude material was purified by column chromatography over silica gel (100-200 mesh) with 0-5% gradient elution of MeOH in DCM to afford compound 100 as an off-white solid (43 mg, 68%). LC-MS (ESI) m/z: 469.9 $[M+H]^+$; $^1H$ NMR (400 MHz, DMSO-$d_6$): δ 5.27-5.25 (m, 1H), 5.02 (d, J=6 Hz, 1H), 4.59 (d, J=4.4 Hz, 1H), 4.04 (s, 1H), 3.99 (s, 1H), 3.97-3.92 (m, 1H), 3.75 (s, 1H), 3.71 (s, 1H), 3.28-3.22 (m, 1H), 2.41-2.32 (m, 2H), 2.18-2.05 (m, 2H), 2.03-1.83 (m, 6H), 1.82-1.72 (m, 2H), 1.71-1.62 (m, 1H), 1.61-1.42 (m, 4H), 1.41-1.31 (m, 4H), 1.36-1.20 (m, 1H), 1.19-1.11 (m, 2H), 1.0-1.03 (m, 2H), 1.02-0.97 (m, 2H), 0.94 (s, 3H), 0.91-0.82 (m, 4H), 0.63 (s, 3H).

Example 101: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(6-hydroxy-6-methyl-2-azaspiro[3.3]heptan-2-yl)pentan-1-one

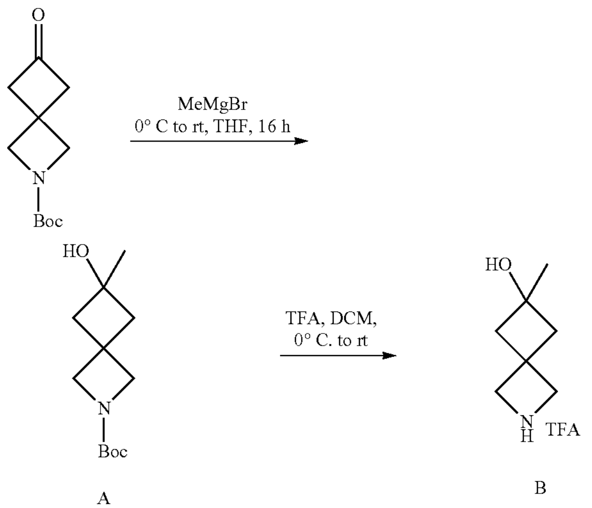

A

B

-continued

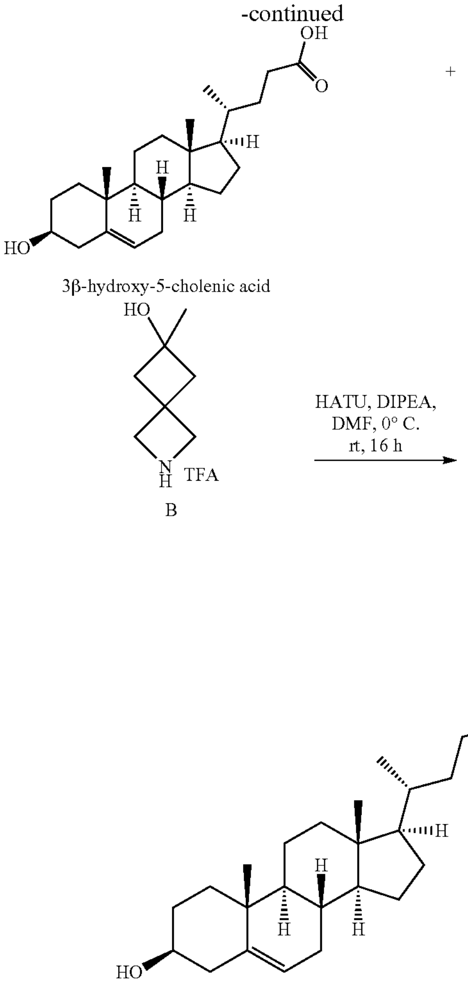

3β-hydroxy-5-cholenic acid

B

101

To a stirred solution of tert-butyl 6-oxo-2-azaspiro[3.3]heptane-2-carboxylate (250 mg, 1.18 mmol) in dry THE (5 mL) at 0° C. was added methylmagnesium bromide (1M in $Et_2O$, 4.5 mL, 4.73 mmol) and the resulting reaction mixture was stirred at ambient temperature for 16 h. Upon completion, the reaction mixture was quenched with saturated aqueous $NH_4Cl$ (20 mL) and extracted with ethyl acetate (2×50 mL). The combined organic layer was washed with water (50 mL), brine (50 mL), dried over anhydrous sodium sulfate, filtered, and concentrated in vacuo to afford crude compound A (160 mg, 59%) as a yellow liquid.

To a stirred solution of crude compound A (0.3 g, 0.7 mmol) in DCM (3 mL) at 0° C. was added TFA (321 mg, 2.82 mmol) and the resulting reaction mixture was stirred at room temperature for 3 h. Upon completion, the reaction mixture was concentrated in vacuo to obtain the TFA salt of crude compound B as a yellow gummy liquid.

Compound 101 was synthesized according to the general procedure A using 3β-hydroxy-5-cholenic acid (0.1 g, 0.267 mmol), DIPEA (1.2 mL, 1.6 mmol), HATU (203 mg, 0.534 mmol) TFA salt of crude compound B (68 mg, 0.534 mmol) and DMF (5 mL). The crude compound was purified by preparative HPLC [column: Gemini C18 2.0*50 mm, 3 μm; mobile phase: A 0.01% formic acid in water; flow rate: 0.6 ml/min, program (Time/% B): 0.01/5, 2.0/90, 3.50/90, 3.51/5] to afford compound 101 (20 mg, 15%) as an off-white solid. LC-MS (ESI) m/z 484 $(M+H)^+$; $^1H$ NMR (400 MHz, DMSO-$d_6$): δ 5.28-2.24 (m, 1H), 4.88 (s, 1H), 4.58 (s, 1H), 4.08 (s, 1H), 4.02 (s, 1H), 3.79 (s, 1H), 3.73 (s, 1H), 3.28-3.23 (m, 1H), 2.17-1.88 (m, 10H), 1.79-1.63 (m, 3H), 1.62-1.30 (m, 8H), 1.28-1.22 (m, 2H), 1.17 (s, 3H), 1.15-0.96 (m, 5H), 0.94 (s, 3H), 0.93-0.88 (m, 4H), 0.64 (s, 3H).

Example 102: (R)-1-(6-ethyl-6-hydroxy-2-azaspiro[3.3]heptan-2-yl)-4-((3S,8S,9S,10R,13R,14S,17R)-3-hydroxy-10,13-dimethyl2,3,4,7,8,9,10,11,12,13,14,15,16,17-tetradecahydro-1H-cyclopenta[a]phenanthren-17-yl)pentan-1-one

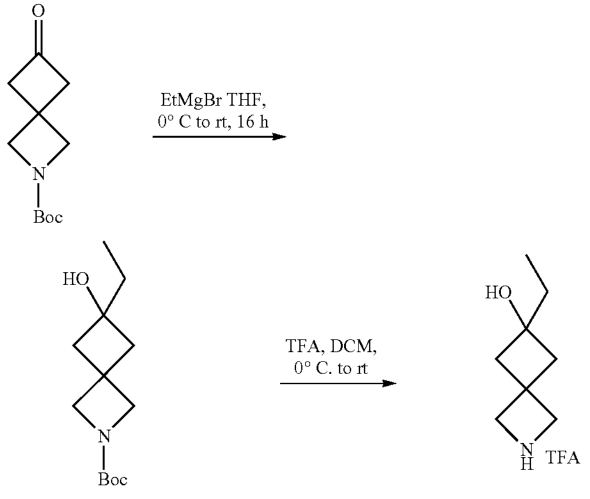

A

B

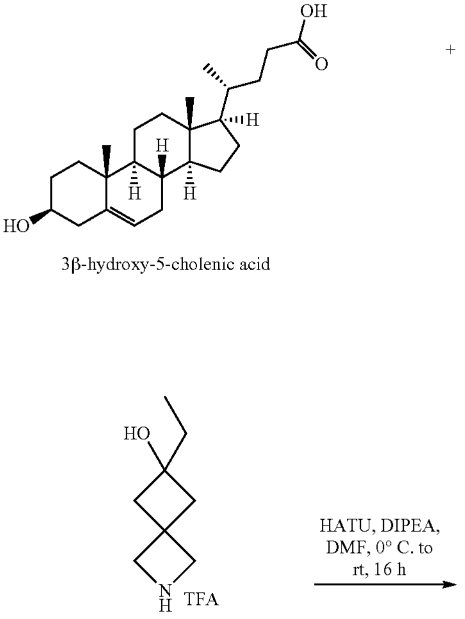

3β-hydroxy-5-cholenic acid

B

-continued

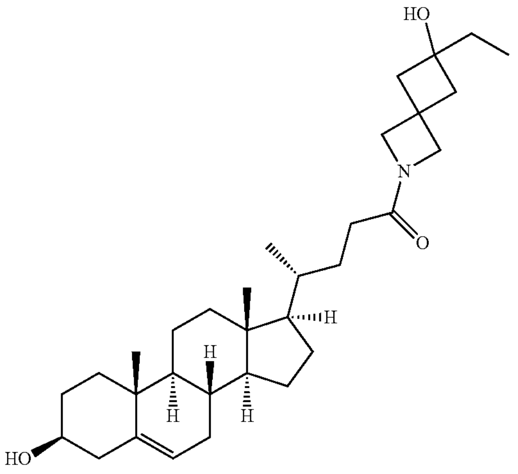

102

To a stirred solution of compound tert-butyl 6-oxo-2-azaspiro[3.3]heptane-2-carboxylate (250 mg, 1.18 mmol) in dry THE (5 mL) at 0° C. was added ethylmagnesium bromide (1M in $Et_{20}$, 4.5 mL, 4.53 mmol) and the reaction mixture was allowed to stir at ambient temperature for 16 h. Upon completion, the reaction mixture was quenched with saturated aqueous $NH_4Cl$ (20 mL) and extracted with ethyl acetate (2×50 mL). The combined organic layer was washed with water (50 mL), brine (50 mL), dried over anhydrous sodium sulfate, filtered, and concentrated in vacuo to afford crude compound A (180 mg, 63%) as a yellow liquid.

To a stirred solution of crude compound A (180 mg, 0.74 mmol) in anhydrous DCM (3 mL) at 0° C. was added TFA (340 mg, 2.98 mmol) and the resultant reaction mixture was stirred at room temperature for 3 h. Upon completion, the reaction mixture was concentrated in vacuo to afford TFA salt of crude compound B (80 mg, 75%) as a yellow gummy liquid. The crude product was used to next step without further purification.

Compound 102 was synthesized according to the general procedure A using 3β-hydroxy-5-cholenic acid (0.1 g, 267 μmol), DIPEA (1.2 mL, 1.6 mmol), HATU (203 mg, 0.534 mmol) TFA salt of crude compound B (75 mg, 0.534 mmol) and DMF (5 mL). The crude compound was purified by preparative HPLC [column: Gemini C18 2.0*50 mm, 3 μm; mobile phase: A 0.01% formic acid in water; flow rate: 0.5 ml/min, program (Time/% B): 0.02/5, 2.0/80, 3.50/70, 3.52/7] to afford compound 102 (18 mg, 15%) as an off-white solid. LC-MS (ESI) m/z 497.8 $(M+H)^+$; $^1H$ NMR (400 MHz, DMSO-$d_6$): δ 5.26 (d, J=4.80 Hz, 1H), 4.72 (d, J=6.00 Hz, 1H), 4.58 (d, J=4.40 Hz, 1H), 4.04 (s, 2H), 3.75 (s, 2H), 3.28-3.20 (m, 1H), 2.19-2.04 (m, 6H), 2.02-1.85 (m, 4H), 1.80-1.63 (m, 3H), 1.62-1.44 (m, 4H), 1.43-1.22 (m, 7H), 1.18-0.96 (m, 6H), 0.94 (s, 3H), 0.92-0.85 (m, 4H), 0.83-0.77 (m, 3H), 0.64 (s, 3H).

Example 103: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-hydroxypiperidin-1-yl)pentan-1-one

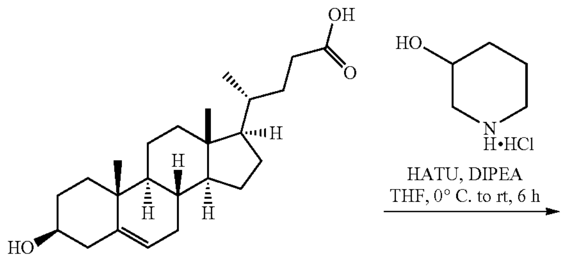

3β-hydroxy-5-cholenic acid

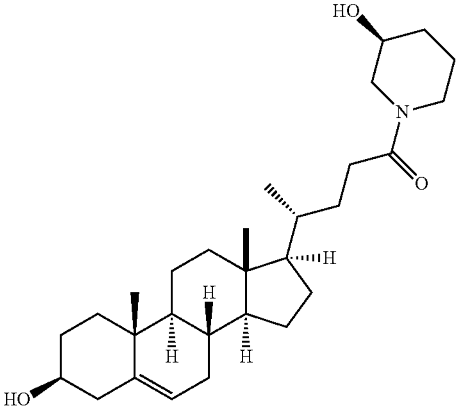

103

Compound 103 was synthesized according to the general procedure A using 3β-hydroxy-5-cholenic acid (150 mg, 0.40 mmol), HATU (305 mg, 0.80 mmol), DIPEA (0.35 mL, 2.0 mmol), (3S)-piperidin-3-ol hydrochloride (81 mg, 0.80 mmol) and THE (1.5 mL). The reaction time was 6 h. The obtained crude material was purified by column chromatography over silica gel (100-200 mesh) with 0-5% gradient elution of MeOH in DCM to afford compound 103 (42.1 mg, 23%) as an off-white solid. LC-MS (ESI) m/z: 458.4 $[M+H]^+$; $^1H$ NMR (400 MHz, DMSO-$d_6$): δ 5.27-5.25 (m, 1H), 4.83 (d, J=4.0 Hz, 1H), 4.58 (d, J=4.4 Hz, 1H), 4.13-4.10 (m, 0.5H), 3.63-3.45 (m, 2.5H), 3.27-3.21 (m, 1H), 3.08-2.95 (m, 2H), 2.32-2.22 (m, 1H), 2.20-2.02 (m, 3H), 2.00-1.85 (m, 2H), 1.82-1.72 (m, 3H), 1.69-1.43 (m, 7H), 1.42-1.21 (m, 7H), 1.20-0.96 (m, 5H), 0.94 (s, 3H) 0.92-0.85 (m, 4H), 0.64 (s, 3H).

Example 104: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-3-hydroxypiperidin-1-yl) pentan-1-one

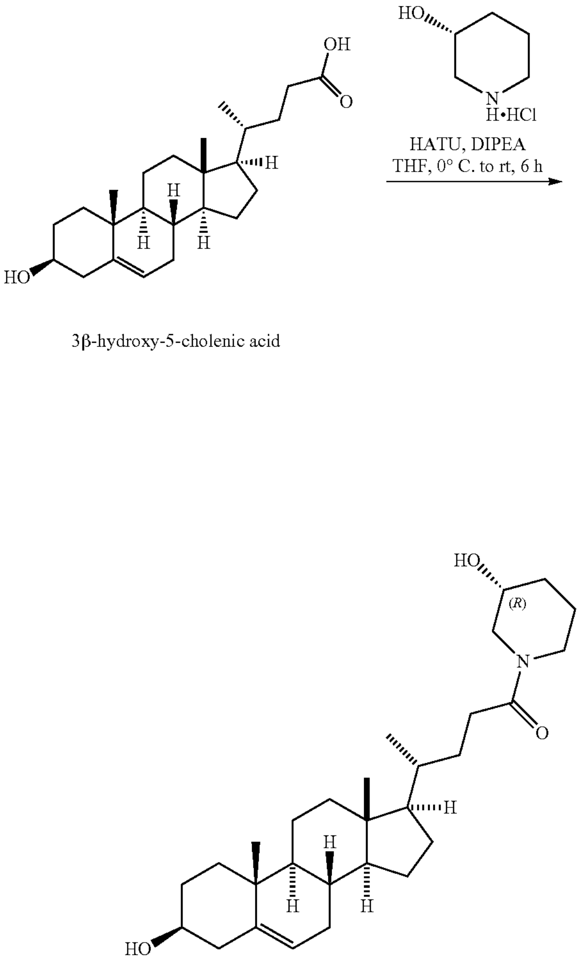

3β-hydroxy-5-cholenic acid

104

Compound 104 was synthesized according to the general procedure A using 3β-hydroxy-5-cholenic acid (150 mg, 0.40 mmol), HATU (305 mg, 0.80 mmol), DIPEA (0.35 mL, 2.0 mmol), (3R)-piperidin-3-ol hydrochloride(122 mg, 1.2 mmol), and THE (1.5 mL). Reaction time 6 h. The obtained crude material was purified by column chromatography over silica gel (100-200 mesh) with 0-5% gradient elution of MeOH in DCM to afford compound 104 (85 mg, 46%) as an off-white solid. LC-MS (ESI) m/z: 458.4 $[M+H]^+$; $^1H$ NMR (400 MHz, DMSO-$d_6$): δ 5.27-5.25 (m, 1H), 4.84-4.82 (m, 1H), 4.58 (d, J=4.4 Hz, 1H), 4.14-4.09 (m, 0.5H), 3.61-3.48 (m, 2.5H), 3.28-3.21 (m, 1H), 3.08-2.95 (m, 1H), 2.33-2.25 (m, 1H), 2.22-2.02 (m, 3H), 2.00-1.72 (m, 5H), 1.70-1.44 (m, 7H), 1.43-1.20 (m, 8H), 1.19-0.96 (m, 6H), 0.94 (s, 3H) 0.91-0.83 (m, 4H), 0.64 (s, 3H).

Example 105: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-3-hydroxy-3-methylpiperidin-1-yl) pentan-1-one

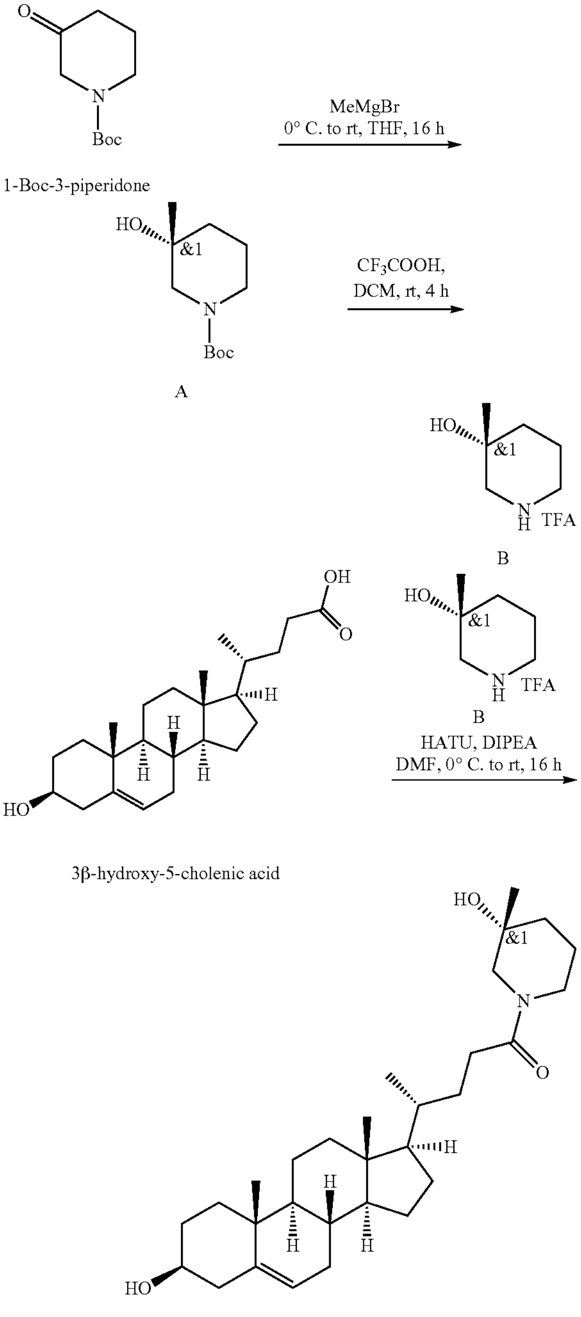

1-Boc-3-piperidone

A

B

3β-hydroxy-5-cholenic acid

105

To a stirred solution of 1-Boc-3-piperidone (500 mg, 2.51 mmol) in dry THF (5 mL) was added MeMgBr (1M in THF, 10 mL, 10 mmol) drop wise at 0° C. under nitrogen atmosphere. The resulting reaction mixture was stirred at room temperature for 16 h. Upon completion, the reaction mixture was quenched with saturated aqueous $NH_4Cl$ (10 mL) and extracted with ethyl acetate (20 mL×3). The combined organic layer was washed with brine (10 mL), dried over anhydrous sodium sulfate, filtered, and concentrated in vacuo to afford compound A as an oily compound (500 mg, 92%).

To a stirred solution of crude compound-A (500 mg, 2.32 mmol) in DCM (5 mL) was added TFA (1 mL, 13 mmol) at 0° C. under nitrogen atmosphere. The resulting reaction mixture was stirred at room temperature for 4 h. Upon completion, the reaction mixture was concentrated and co-distilled with toluene in vacuo to afford compound B as a brown gummy liquid (300 mg, 61%).

Compound 105 was synthesized according to the general procedure A using 3β-hydroxy-5-cholenic acid (100 mg, 0.267 mmol), HATU (203 mg, 0.534 mmol), DIPEA (0.276 mL, 1.6 mmol), crude compound B (226 mg, 1.07 mmol), and DMF (2 mL). The reaction time was 16 h. The crude material was purified by column chromatography over silica gel (100-200 mesh) with 0-70% gradient elution of ethyl acetate in hexanes to afford the desired compound 105 (40 mg, 31%) as an off-white solid. LC-MS (ESI) m/z: 534 $[M+H]^+$; $^1H$ NMR (400 MHz, DMSO-$D_6$) δ 5.26-5.25 (m, 1H), 4.59 (d, J=4.4 Hz, 1H), 4.44 (d, J=19.2, 1 H, OH) 3.82 (brs, 1H, OH), 3.28-3.22 (m, 2H), 3.09-2.85 (m, 1H), 2.33-2.25 (m, 1H), 2.22-2.05 (m, 3H), 2.00-1.87 (m, 2H), 1.83-1.72 (m, 2H), 1.71-1.61 (m, 3H), 1.59-1.44 (m, 6H), 1.42-1.36 (m, 4H), 1.35-1.21 (m, 3H), 1.20-1.08 (m, 5H), 1.06-1.0 (m, 2H), 0.99-0.82 (m, 9H), 0.65 (s, 3H).

Example 106: (4R)-1-(3-ethyl-3-hydroxypiperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl) pentan-1-one

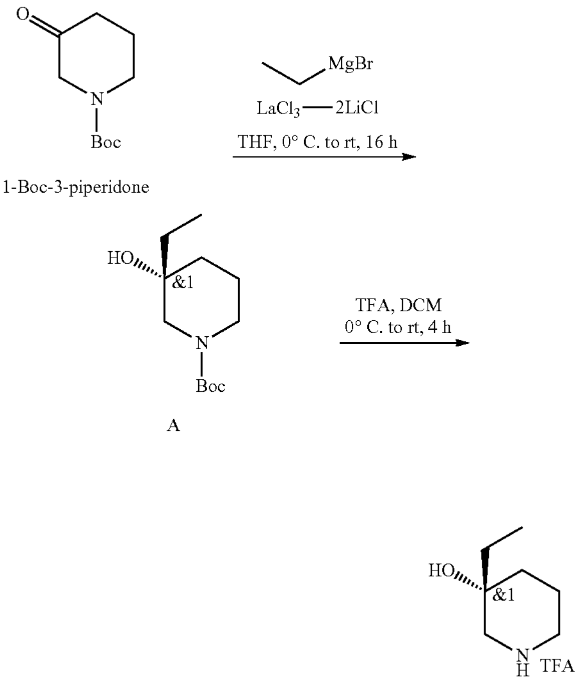

1-Boc-3-piperidone

A

B

-continued

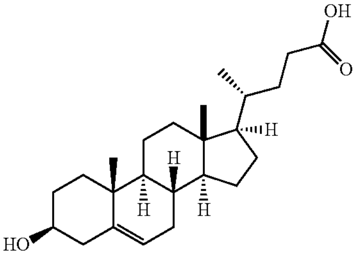

3β-hydroxy-5-cholenic acid

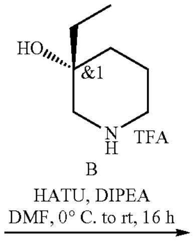

B

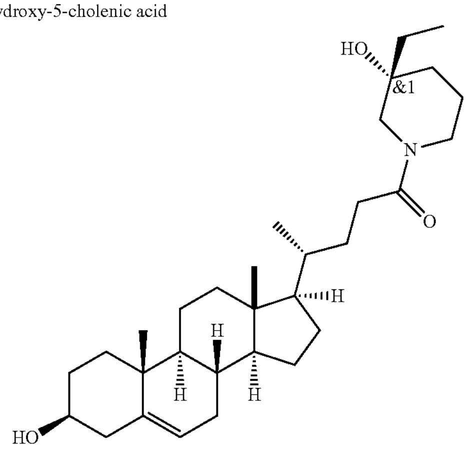

106

To a stirred solution of $LaCl_3$.2LiCl (0.6M in THF, 6 mL, 0.75 mmol) at 0° C. was added EtMgBr (2M in $Et_{20}$, 2.5 mL, 5.0 mmol) under nitrogen atmosphere and after stirring the reaction mixture for 3 h at 0° C., was added 1-boc-3-piperidone (500 mg, 2.5 mmol) in THF (5 mL) drop wise. The resultant reaction mixture was stirred at room temperature for 16 h. Upon completion, the reaction mixture was quenched with acetic acid (5 mL), diluted with ethyl acetate (10 mL), and extracted into ethyl acetate (20 mL×3). The combined organic layer was washed with brine, dried over anhydrous sodium sulfate, filtered, and concentrated in vacuo to afford compound A as a pale-yellow oil (500 mg).

To a stirred solution of crude compound A (500 mg, 2.18 mmol) in DCM (5 mL) was added TFA (1 mL, 26.54 mmol) at 0° C. under nitrogen atmosphere. The resultant reaction mixture was stirred at room temperature for 4 h. Upon completion, the reaction mixture was concentrated in vacuo to afford compound B as a brown gummy liquid (250 mg).

Compound 106 was synthesized according to the general procedure A using 3β-hydroxy-5-cholenic acid (100 mg, 0.267 mmol), HATU (203 mg, 0.532 mmol), DIPEA (0.14 mL, 0.80 mmol), crude compound B (66 mg, 0.4 mmol), and DMF (5 mL). The obtained crude material was purified by column chromatography over silica gel (100-200 mesh) with 0-5% gradient elution of MeOH in DCM to afford compound 106 as an off-white solid (35 mg, 27%). ELSD-MS (ESI) m/z: 486 $[M+H]^+$; $^1H$ NMR (400 MHz, DMSO-$d_6$): δ 5.27-5.25 (m, 1H), 4.61 (d, J=4.4 Hz, 1H), 4.22-4.17 (m, 1H), 3.97-3.94 (m, 1H), 3.28-3.22 (m, 2H), 3.01-2.96 (m, 0.5H), 2.78-2.71 (m, 0.5H), 2.32-2.25 (m, 1H), 2.23-2.06 (m, 3H), 1.99-1.87 (m, 2H), 1.83-1.73 (m, 2H), 1.71-1.46 (m, 7H), 1.44-1.23 (m, 9H), 1.19-1.05 (m, 4H), 1.03-0.97 (m, 2H), 0.95 (s, 3H), 0.92-0.78 (m, 8H), 0.64 (s, 3H).

Example 107: ((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)glycine

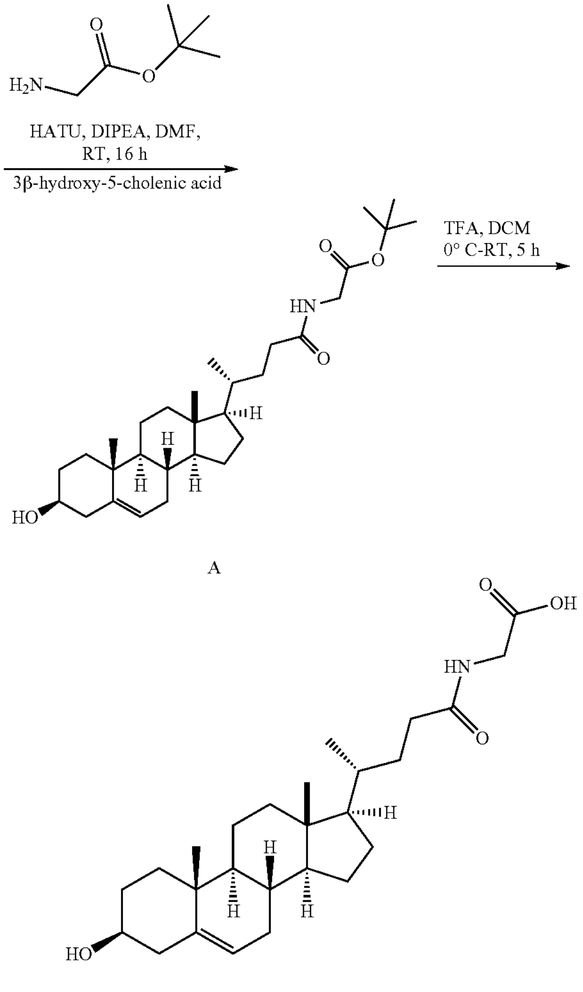

A

107

Compound 107 was synthesized according to the general procedure A using 3β-hydroxy-5-cholenic acid (100 mg, 0.267 mmol), HATU (203 mg, 0.534 mmol), DIPEA (0.18 mL, 1.07 mmol), tert-butyl glycinate (80.6 mg, 0.481 mmol), and DMF (4 mL). The crude material was purified by column chromatography over silica gel (100-200 mesh) using 0-7% gradient elution of ethyl acetate in hexanes to afford the title compound A (90 mg, 69.2%).

To a stirred solution of compound A (100 mg, 0.44 mmol) in DCM (4 mL) at 0° C. was added TFA (1 mL). The resultant reaction mixture was stirred at ambient temperature for 5 h. Upon completion, the reaction mixture was concentrated to afford crude compound. The crude compound was diluted with water (20 mL) and extracted with ethyl acetate (20 mL×2). The organic layer was washed with 1N NaOH (20 mL) solution. The combined organic layer was dried over sodium sulfate, filtered, and concentrated in vacuo to obtain the crude material that was purified by preparative HPLC [column: Kinetex EVO, C18 (50×3 mm, 2.60; mobile phase-A: 0.1% FA in water, mobile phase-B: acetonitrile; flow rate: 06 mL/min.] to afford the title compound 107 (45 mg, 51%). LC-MS (ESI) m/z: 431.8 $[M+H]^+$; $^1H$ NMR (400 MHz, DMSO-$d_6$): δ 12.56 (brs, 1H), 8.05 (t, J=5.6 Hz, 1H), 5.25 (s, 1H), 4.58 (brs, 1H), 3.69 (d, J=5.6 Hz, 2H), 3.26-3.22 (m, 1H), 2.19-1.88 (m, 6H), 1.86-1.61 (m, 4H), 1.59-1.32 (m, 7H), 1.31-1.11 (m, 3H), 1.10-0.96 (m, 4H), 0.93 (s, 3H), 0.89-0.86 (m, 4H), 0.64 (s, 3H).

Example 108: N—((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N-methylglycine

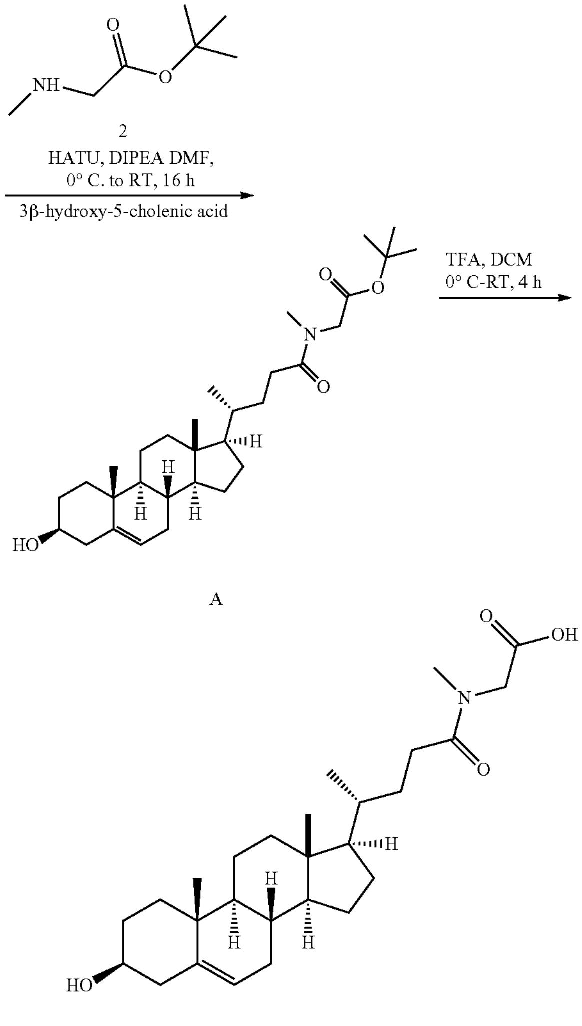

2

A

108

Compound 108 was synthesized according to the general procedure A using 3β-hydroxy-5-cholenic acid (150 mg, 0.4 mmol), HATU (305 mg, 0.801 mmol), DIPEA (0.276 mL, 1.6 mmol), tert-butyl methylglycinate (226 mg, 1.07 mmol), and DMF (3 mL). The crude material was purified by silica gel chromatography (0-70% ethyl acetate:hexanes) to afford the desired compound A (120 mg, 59%). LC-MS (ESI) m/z: 502 $[M+H]^+$.

To a stirred solution of compound A (100 mg, 62.5 mmol) in DCM (4 mL) was added TFA (0.12 mL, 1.59 mmol) at 0° C. under nitrogen atmosphere. The resulting reaction mixture was stirred at room temperature for 4 h. Upon completion, the reaction mixture was concentrated and co-distilled with toluene in vacuo and obtained crude compound that was purified by preparative HPLC (Column: X-BRIDGE C18 (250*19 mm; mobile phase-A:0.1% TFA in water, mobile phase-B: acetonitrile; flow rate: 13 mL/min, Gradient: 0/35,10/70, 25/90.) to afford compound 108 (60 mg, 67%). ELSD-MS (ESI) m/z: 445.9 $[M+H]^+$; $^1H$ NMR (400 MHz, DMSO-$d_6$): δ 12.8 (brs, 1H), 5.27-5.25 (m, 1H), 4.59 (brs, 1H), 4.05 (s, 0.5H), 3.95 (s, 1.5H), 3.30-3.20 (m, 1H), 2.99 (s, 2H), 2.78 (s, 1H), 2.39-2.29 (m, 1H), 2.28-2.03 (m, 4H), 2-01-1.87 (m, 2H), 1.85-1.72 (m, 2H), 1.71-1.59 (m, 2H), 1.58-1.44 (m, 3H), 1.42-1.33 (m, 3H), 1.31-1.21 (m, 1H), 1.21-1.05 (m, 3H), 1.03-0.83 (m, 10H), 0.65 (s, 3H).

Example 109: N-ethyl-N—((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl) pentanoyl)glycine

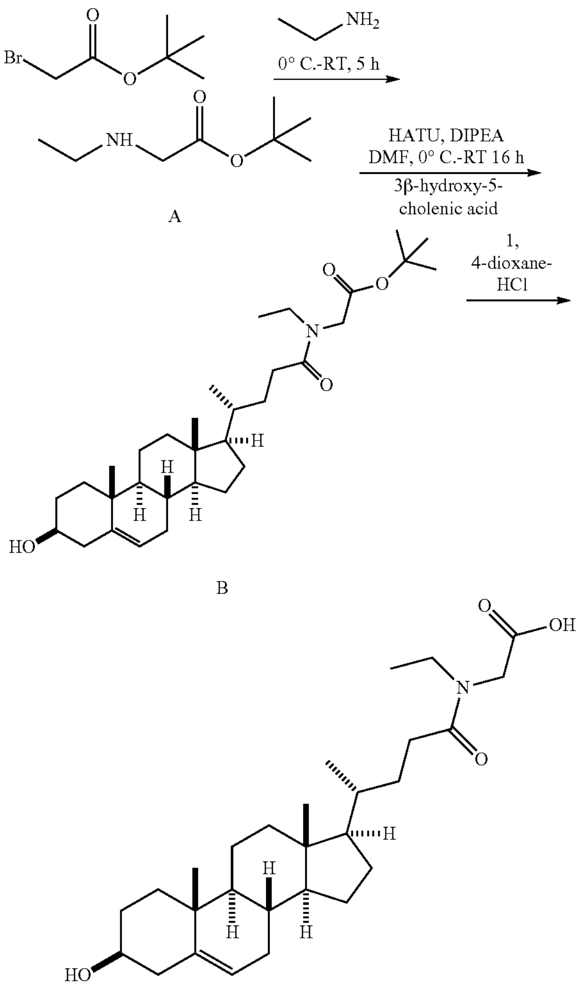

A

B

109

To a stirred solution of ethyl amine (2.0 M in THF, 1.16 g, 25.6 mmol) in tetrahydrofuran (5 mL) was added tert-butyl 2-bromoacetate (0.5 g, 2.56 mmol) at 0° C. After stirring the reaction mixture for 15 minutes, it was allowed to warm to room temperature and stirred for 5 h. Upon completion, the reaction mixture was concentrated, diluted with ethyl acetate (20 mL) and washed with saturated sodium bicarbonate (5 mL). The organic layer was dried over sodium sulfate and concentrated in vacuo to obtain crude compound A (150 mg, 942 μmol) as gummy liquid.

Compound B was synthesized according to the general procedure A using 3β-hydroxy-5-cholenic acid (100 mg, 0.267 mmol), HATU (203 mg, 0.534 mmol), DIPEA (0.276 mL, 1.6 mmol), crude compound A (226 mg, 1.07 mmol), and DMF (2 mL). The reaction time was 16 h. The crude material was purified by column chromatography over silica gel (100-200 mesh) with gradient elution of 0-70% ethyl acetate in hexanes to afford the compound B (11 mg, 10%) as gummy liquid.

To a stirred solution of compound B (120 mg, 0.233 mmol) in DCM (5 mL) was added trifluoroacetic acid (1 mL) 0° C. and stirred for 15 minutes. Then, it was allowed to room temperature and stirred for 3 h. Upon completion, the reaction mixture was concentrated in vacuo to get crude compound. The crude compound was triturated with diethyl ether to afford the title compound 109 (11 mg) as an off white solid. LC-MS (ESI) m/z: 459.8 $[M+H]^+$; $^1H$ NMR (400 MHz, DMSO-$d_6$): δ 12.50 (bs, 1H), 5.27-5.25 (m, 1H), 4.58 (brs, 1H), 4.04 (s, 1H), 3.88 (s, 1H), 3.37-3.24 (m, 3H), 2.30-2.02 (m, 4H), 2.00-1.86 (m, 2H), 1.85-1.72 (m, 2H), 1.71-1.60 (m, 2H), 1.59-1.22 (m, 8H), 1.20-1.03 (m, 5H), 1.02-0.83 (m, 11H), 0.64 (d, J=4.8, 3H).

Example 110: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-methylpiperidin-1-yl)pentan-1-one

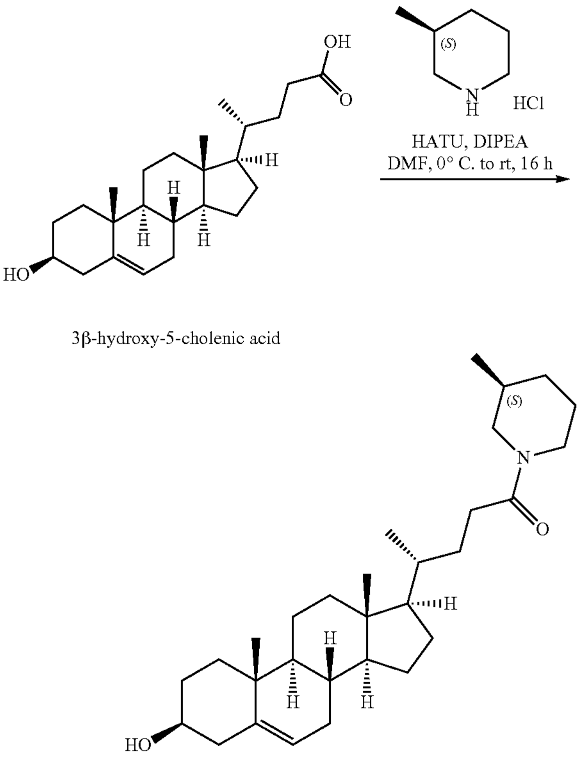

3β-hydroxy-5-cholenic acid

110

Compound 110 was synthesized according to the general procedure A using 3β-hydroxy-5-cholenic acid (100 mg, 0.266 mmol), HATU (203 mg, 0.534 mmol), DIPEA (0.143 mL, 0.801 mmol), (3S)-methyl piperidine hydrochloride (39.7 mg, 0.4 mmol), and DMF (3 mL). The reaction time was 16 h. The obtained crude material was purified by column chromatography over silica gel (100-200 mesh) with gradient elution of 0-80% ethyl acetate in hexanes to afford compound 110 as an off-white solid (51 mg, 42%). LC-MS (ESI) m/z: 455.9 $[M+H]^+$; $^1H$ NMR (400 MHz, DMSO-$d_6$): δ 5.27-5.26 (m, 1H), 4.58 (d, J=4.8 Hz, 1H), 4.22-4.16 (m, 1H), 3.76-3.66 (m, 1H), 3.28-3.21 (m, 1H), 2.95-2.89 (m, 1H), 2.69-2.61 (m, 1H), 2.35-2.05 (m, 4H), 2.00-1.85 (m, 2H), 1.84-1.70 (m, 3H), 1.69-1.45 (m, 7H), 1.44-1.32 (m, 5H), 1.31-1.20 (m, 2H), 1.19-1.04 (m, 5H), 1.03-0.81 (m, 12H), 0.64 (s, 3H).

Example 111:(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-3-methylpiperidin-1-yl)pentan-1-one

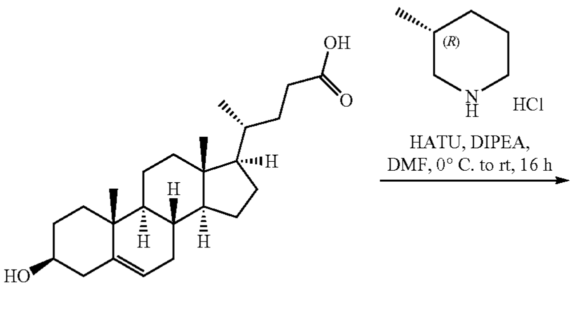

3β-hydroxy-5-cholenic acid

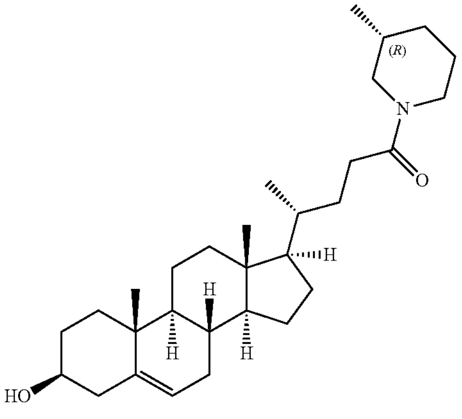

111

Compound 111 was synthesized according to the general procedure A using 3β-hydroxy-5-cholenic acid (100 mg, 0.266 mmol), HATU (203 mg, 0.534 mmol), DIPEA (0.143 mL, 0.801 mmol), (3R)-methyl piperidine hydrochloride (39.7 mg, 0.4 mmol), and DMF (3 mL). The reaction time was 16 h. The obtained crude material was purified by column chromatography over silica gel (100-200 mesh) with 0-80% gradient elution of ethyl acetate in hexanes to afford compound 111 as an off-white solid (25.8 mg, 21%). LC-MS (ESI) m/z: 456.9 $[M+H]^+$; $^1H$ NMR (400 MHz, DMSO-$d_6$): δ 5.27-5.25 (m, 1H), 4.58 (d, J=4.8 Hz, 1H), 4.23-4.14 (m, 1H), 3.78-3.65 (m, 1H), 3.30-3.21 (m, 1H), 2.98-2.60 (m, 1H), 2.65-2.61 (m, 1H), 2.31-2.02 (m, 4H), 1.99-1.85 (m, 2H), 1.84-1.70 (m, 3H), 1.69-1.43 (m, 7H), 1.42-1.21 (m, 7H), 1.20-0.95 (m, 7H), 0.94 (s, 3H), 0.93-0.81 (m, 7H), 0.64 (s, 3H).

Example 112: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-2-methylpyrrolidin-1-yl)pentan-1-one

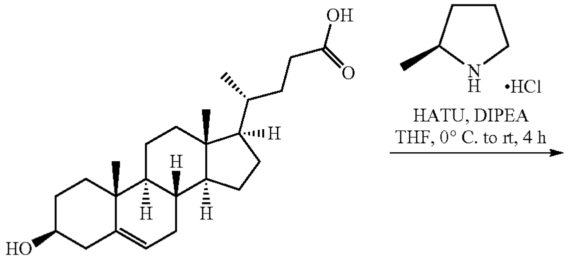

3β-hydroxy-5-cholenic acid

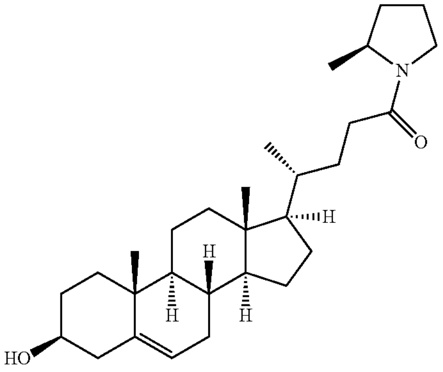

112

Compound 112 was synthesized according to the general procedure A using 3β-hydroxy-5-cholenic acid (150 mg, 0.40 mmol), HATU (305 mg, 0.80 mmol), DIPEA (0.34 mL, 1.95 mmol), (S)-2-Methyl-pyridine hydrochloride (96.9 mg, 0.80 mmol), and THE (1.5 mL). The reaction time was 4 h. The obtained crude material was purified by column chromatography over silica gel (100-200 mesh) with 0-3% gradient elution of MeOH in DCM to afford compound 112 (104 mg, 58%) as an off-white solid. LC-MS (ESI) m/z: 442 $[M+H]^+$; $^1H$ NMR (400 MHz, DMSO-$d_6$): δ 5.27-5.25 (m, 1H), 4.59 (d, J=4.4 Hz, 1H), 4.03-3.97 (m, 1H), 3.46-3.41 (m, 1H), 3.28-3.22 (m, 2H), 2.25-2.18 (m, 1H), 2.13-2.12 (m, 3H), 2.00-1.71 (m, 7H), 1.70-1.61 (m, 2H), 1.59-1.32 (m, 7H), 1.30-1.21 (m, 2H), 1.20-1.10 (m, 4H), 1.08-0.96 (m, 5H), 0.94 (s, 3H), 0.91-0.83 (m, 4H), 0.64 (s, 3H).

Example 113: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-2-methylpyrrolidin-1-yl)pentan-1-one

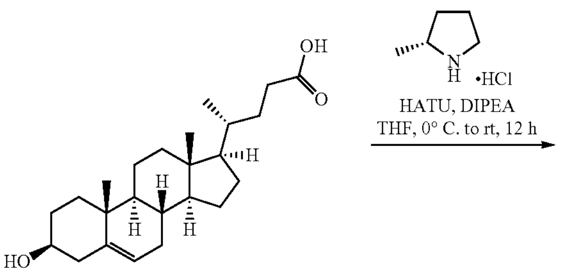

3β-hydroxy-5-cholenic acid

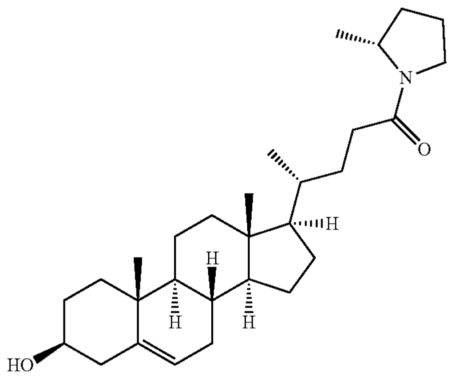

113

Compound 113 was synthesized according to the general procedure A using 3β-hydroxy-5-cholenic acid (150 mg, 0.40 mmol), HATU (305 mg, 0.80 mmol), DIPEA (0.34 mL, 1.95 mmol), (R)-2-Methyl-pyrrolidine hydrochloride (96.9 mg, 0.80 mmol), and THF (1.5 mL). The reaction time was 12 h. The obtained crude material was purified by preparative HPLC [Column: Gemini C18 (250*21.2 mm) 5μ, mobile phase-A: 0.01% FA in water, mobile phase-B: 100% ACN, program (Time/% B): 0/70,10/95, flow 15.0 ml/min] to afforded compound 113 (30 mg, 17%) as an off-white solid. LC-MS (ESI) m/z: 442 $[M+H]^+$; $^1H$ NMR (400 MHz, DMSO-$d_6$): δ 5.27-5.25 (m, 1H), 4.59 (d, J=4.8 Hz, 1H), 4.03-3.97 (m, 1H), 3.47-3.41 (m, 2H), 3.28-3.22 (m, 1H), 2.22-2.15 (m, 2H), 2.13-2.05 (m, 3H), 2.01-1.72 (m, 7H), 1.70-1.61 (m, 2H), 1.57-1.33 (m, 7H), 1.32-1.11 (m, 5H), 1.09-0.96 (m, 5H), 0.93 (s, 3H), 0.91-0.85 (m, 4H), 0.64 (s, 3H).

Example 114: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-methylpyrrolidin-1-yl)pentan-1-one

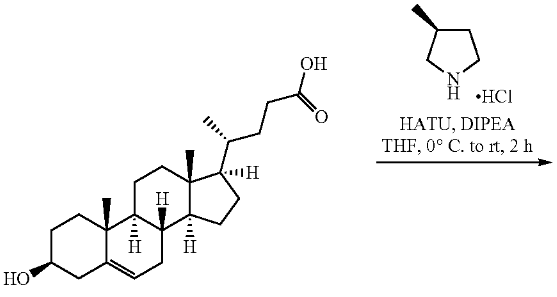

3β-hydroxy-5-cholenic acid

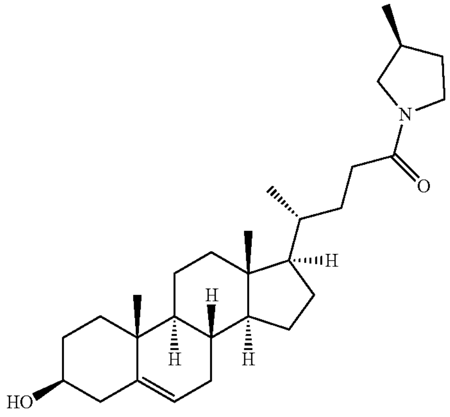

114

Compound 114 was synthesized according to the general procedure A using 3β-hydroxy-5-cholenic acid (150 mg, 0.40 mmol), HATU (305 mg, 0.80 mmol), DIPEA (0.35 mL, 2.0 mmol), (S)-3-Methyl-pyridine hydrochloride (96.9 mg, 0.80 mmol), and THF (1.5 mL). The reaction time was 2 h. The obtained crude material was purified by column chromatography over silica gel (100-200 mesh) with 0-3% gradient elution of MeOH in DCM to afford compound 114 (116.7 mg, 66%) as an off-white solid. LC-MS (ESI) m/z: 442.4 $[M+H]^+$; $^1H$ NMR (400 MHz, DMSO-$d_6$): δ 5.27-5.25 (m, 1H), 4.58 (d, J=4.4 Hz, 1H), 3.59-3.42 (m, 2H), 3.22-3.14 (m, 1H), 2.93-2.72 (m, 1H), 2.27-2.20 (m, 2H), 2.18-2.02 (m, 4H), 2.00-1.87 (m, 3H), 1.85-1.72 (m, 2H), 1.71-1.60 (m, 2H), 1.56-1.43 (m, 3H), 1.42-1.31 (m, 4H), 1.30-1.03 (m, 5H), 1.02-0.93 (m, 5H), 0.94 (s, 3H) 0.91-0.83 (m, 4H), 0.64 (s, 3H).

Example 115: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-3-methylpyrrolidin-1-yl)pentan-1-one

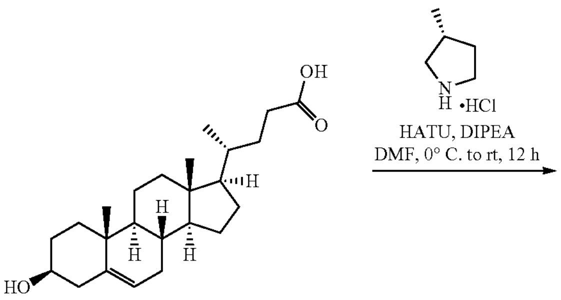

3β-hydroxy-5-cholenic acid

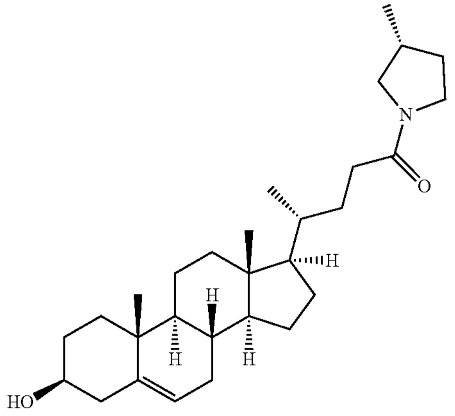

115

Compound 115 was synthesized according to the general procedure A using 3β-hydroxy-5-cholenic acid (150 mg, 0.40 mmol), HATU (305 mg, 0.80 mmol), DIPEA (0.35 mL, 2.0 mmol), (R)-3-Methyl-pyrrolidine hydrochloride (96.9 mg, 0. 80 mmol), and DMF (2 mL). The reaction time was 12 h. The obtained crude material was purified by preparative HPLC [Column: Gemini C18 (250*21.2 mm) 5μ, mobile phase-A: 0.01% FA in water, mobile phase-B: 100% ACN, program (Time/% B): 0/70,10/95, flow 15.0 ml/min] to afford compound 115 (68 mg, 38%) as an off-white solid. LC-MS (ESI) m/z: 442 $[M+H]^+$; $^1H$ NMR (400 MHz, DMSO-$d_6$): δ 5.27-5.25 (m, 1H), 4.58 (d, J=4.8 Hz, 1H), 3.59-3.39 (m, 2H), 3.30-3.12 (m, 2H), 2.93-2.71 (m, 1H), 2.28-2.04 (m, 5H), 2.03-1.87 (m, 3H), 1.86-1.72 (m, 2H), 1.70-1.60 (m, 2H), 1.59-1.43 (m, 4H), 1.41-1.31 (m, 4H), 1.30-1.21 (m, 1H), 1.20-1.02 (m, 4H), 1.01-0.95 (m, 5H), 0.94 (s, 3H), 0.91-0.83 (m, 4H), 0.64 (s, 3H).

Example 116: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-phenylpyrrolidin-1-yl)pentan-1-one

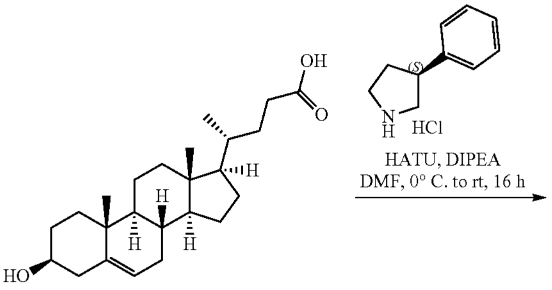

3β-hydroxy-5-cholenic acid

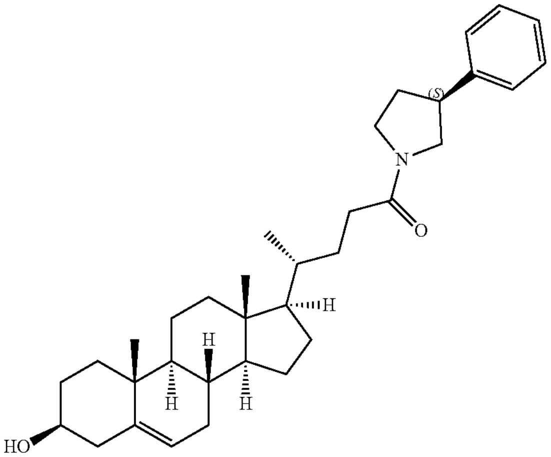

116

Compound 116 was synthesized according to the general procedure A using 3β-hydroxy-5-cholenic acid (100 mg, 0.267 mmol), HATU (0.203 mg, 0.534 mmol), DIPEA (0.143 mL, 0.8 mmol), (S)-3-phenylpyrrolidine hydrochloride (73 mg, 0.4 mmol), and DMF (3 mL). The obtained crude material was purified by column chromatography over silica gel (100-200 mesh) with 0-50% gradient elution of ethyl acetate in hexanes to afford compound 116 as an off-white solid (60 mg, 44%). LC-MS (ESI) m/z: 504 $[M+H]^+$; $^1H$ NMR (400 MHz, DMSO-$d_6$): δ 7.33-7.21 (m, 5H), 5.27-5.25 (m, 1H), 4.59-4.57 (m, 1H), 3.93-3.78 (m, 1H), 3.69-3.47 (m, 2H), 3.21-3.15 (m, 1H), 2.31-2.22 (m, 2H), 2.21-2.04 (m, 4H), 2.03-1.72 (m, 5H), 1.70-1.63 (m, 2H), 1.59-1.43 (m, 3H), 1.42-1.32 (m, 4H), 1.30-1.19 (m, 2H), 1.18-1.05 (m, 3H), 1.03-0.97 (m, 2H), 0.96-0.83 (m, 8H), 0.65-0.64 (d, J=5.2 Hz, 3H).

Example 117: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-3-phenylpyrrolidin-1-yl)pentan-1-one

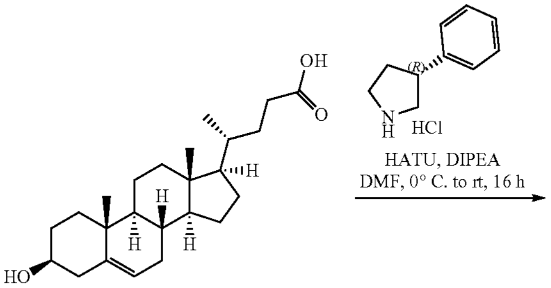

3β-hydroxy-5-cholenic acid

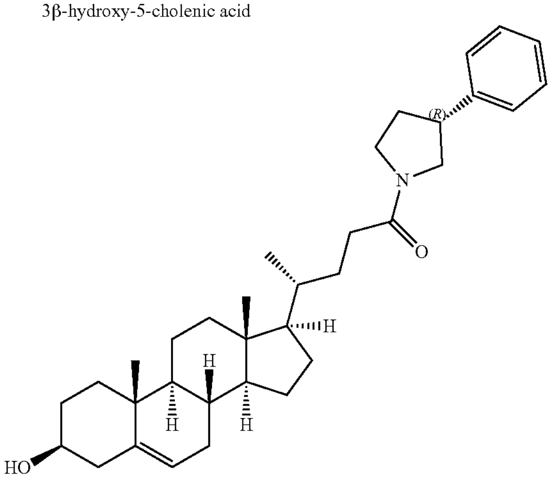

117

Compound 117 was synthesized according to the general procedure A using 3β-hydroxy-5-cholenic acid (100 mg, 0.267 mmol), HATU (0.203 mg, 0.534 mmol), DIPEA (0.143 mL, 0.8 mmol), (R)-3-phenylpyrrolidine hydrochloride (73 mg, 0.4 mmol), and DMF (3 mL). The obtained crude material was purified by column chromatography over silica gel (100-200 mesh) with 0-50% gradient elution of ethyl acetate in hexanes to afford compound 117 as an off-white solid (60 mg, 44%). LC-MS (ESI) m/z: 504 $[M+H]^+$; $^1H$ NMR (400 MHz, DMSO-$d_6$): δ 7.35-7.21 (m, 5H), 5.27-5.25 (m, 1H), 4.59-4.57 (m, 1H), 3.92-3.78 (m, 1H), 3.60-3.50 (m, 2H), 3.42-3.15 (m, 3H), 2.31-2.22 (m, 1H), 2.21-2.04 (m, 4H), 2.03-1.86 (m, 3H), 1.85-1.72 (m, 2H), 1.70-1.62 (m, 2H), 1.59-1.43 (m, 3H), 1.42-1.29 (m, 5H), 1.27-1.20 (m, 1H), 1.19-0.97 (m, 5H), 0.96-0.83 (m, 7H), 0.65 (d, J=5.2 Hz, 3H).

Examples 118 and 119

Example 118: N1-((R)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethyl)-N2,N2-dimethyloxalamide Example 119: N1-((R)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethyl)-N2,N2-dimethyloxalamide

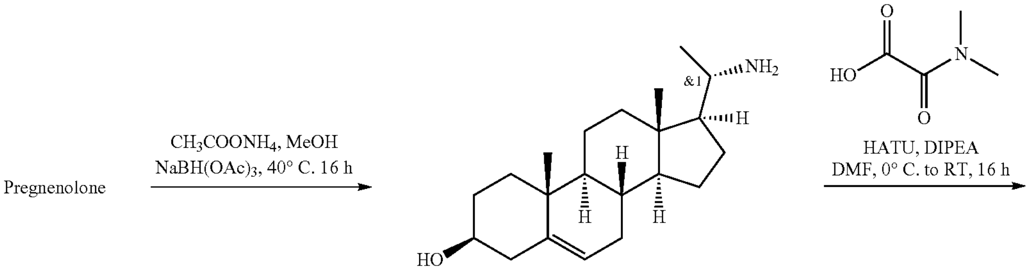

A

-continued

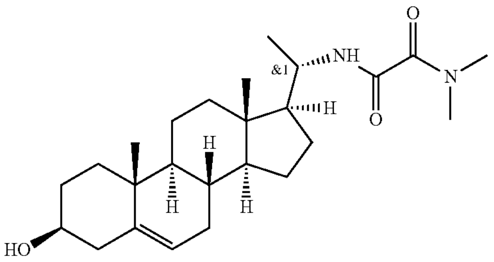

B (diastereomeric mixture)

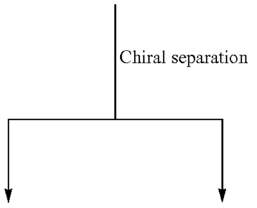

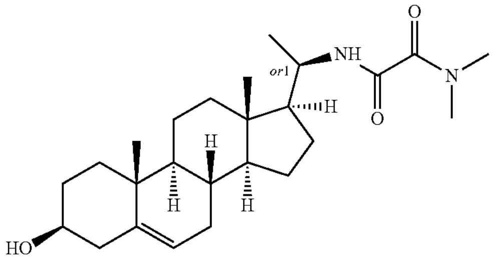

Peak-1
118

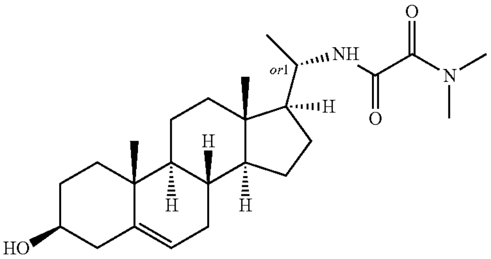

Peak-2
119

To a stirred solution of pregnenolone (1 g, 3.16 mmol) in MeOH (10 mL) at 0° C. was added $CH_3COONH_4$ (4.38 g, 56.9 mmol). The resultant mixture was stirred at 40° C. for 2 h, then was added $NaBH(OAc)_3$ (12.1 g, 56.9 mmol) under nitrogen atmosphere and stirred at same temperature for 16 h. Upon completion, the reaction mixture was quenched with saturated aqueous $NaHCO_3$ (50 mL) and extracted with ethyl acetate (100 mL×3). The combined organic layer was washed with brine (10 mL), dried over anhydrous sodium sulfate, filtered, and concentrated in vacuo to obtain crude material which was triturated with diethyl ether to afford compound A as an off-white solid (500 mg, 49%).

Compound B was synthesized according to the general procedure A using 2-(dimethylamino)-2-oxoacetic acid (277 mg, 2.36 mmol), HATU (1.2 g, 3.15 mmol), DIPEA (0.81 mL, 4.72 mmol), compound A (500 mg, 1.57 mmol), THE (5 mL), and DMF (1 mL). The obtained crude material was purified by column chromatography over silica gel (100-200 mesh) with 0-50% gradient elution of ethyl acetate in hexanes to afford compound B (500 mg, diastereomeric mixture). The diastereomers were separated by preparative HPLC (Column: KINETEX EVO, C18 (50×3 mm, 2.611; mobile phase A: 0.01% FA in water, mobile phase B: 100% CAN; flow rate: 0.6 mL/min, (T/% B): 0.01/5,4/95,7/95, 7.01/5) to afford the title compounds 118 (peak-1, 21 mg, 3%) and 119 (peak-2, 85 mg, 12%) as an off-white solid.

118 (peak-1): LC-MS (ESI) m/z: 416.9$[M+H]^+$; $^1H$ NMR (400 MHz, DMSO-$d_6$): δ 8.46 (d, J=8.8 Hz, 1H), 5.27-5.25 (m, 1H), 4.59 (d, J=4.4 Hz, 1H), 3.84-3.78 (m, 1H), 3.31-3.23 (m, 1H), 2.93 (s, 3H), 2.83 (s, 3H), 2.19-2.05 (m, 2H), 1.95-1.87 (m, 2H), 1.79-1.72 (m, 2H), 1.71-1.65 (m, 1H), 1.57-1.47 (m, 3H), 1.45-1.36 (m, 3H), 1.35-1.27 (m, 2H), 1.17-1.12 (m, 1H), 1.11-1.06 (m, 4H), 1.05-0.97 (m, 2H), 0.96 (s, 3H), 0.92-0.85 (m, 1H), 0.68 (s, 3H).

119 (peak-2): LC-MS (ESI) m/z: 416.8$[M+H]^+$; $^1H$ NMR (400 MHz, DMSO-$d_6$): δ 8.36 (d, J=9.2 Hz, 1H), 5.28-5.25 (m, 1H), 4.58 (d, J=4.8 Hz, 1H), 3.83-3.76 (m, 1H), 3.31-3.23 (m, 1H), 2.97 (s, 3H), 2.84 (s, 3H), 2.19-2.05 (m, 2H), 1.95-1.87 (m, 2H), 1.79-1.72 (m, 1H), 1.71-1.63 (m, 2H), 1.59-1.49 (m, 2H), 1.48-1.41 (m, 2H), 1.39-1.19 (m, 4H), 1.15-1.03 (m, 2H), 1.01-0.96 (m, 5H), 0.93 (s, 3H), 0.89-0.82 (m, 1H), 0.61 (s, 3H).

Examples 120 and 121

Example 120: (R)-4-((3S,8S,9S,10R,13R,14S,17R)-3-hydroxy-3,10,13-trimethyl-2,3,4,7,8,9,10,11,12,13,14,15,16,17-tetradecahydro-1H-cyclopenta[a]phenanthren-17-yl)-N,N-dimethylpentanamide Example 121: (R)-4-((3R,8S,9S,10R,13R,14S,17R)-3-hydroxy-3,10,13-trimethyl-2,3,4,7,8,9,10,11,12,13,14,15,16,17-tetradecahydro-1H-cyclopenta[a]phenanthren-17-yl)-N,N-dimethylpentanamide

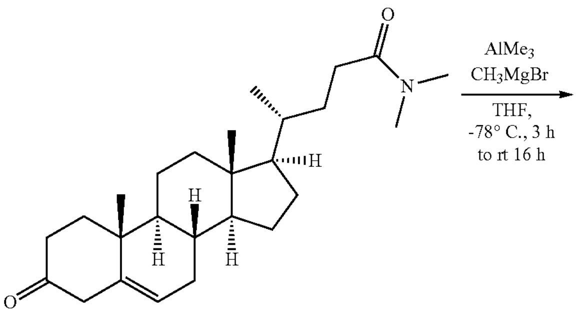

A

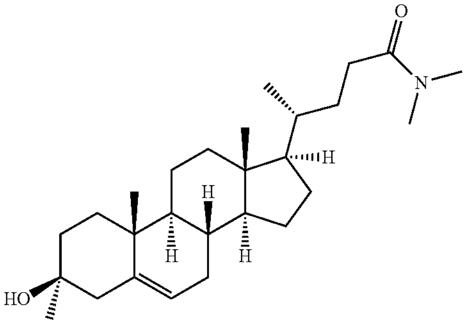

120

-continued

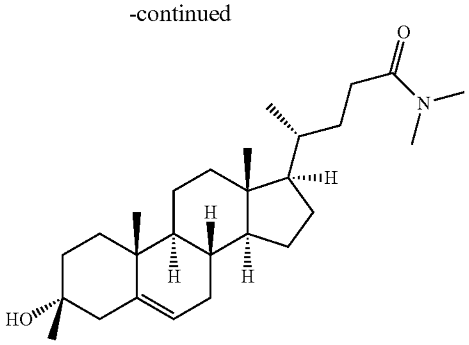

121

A solution of methylmagnesium bromide (6.0 mL, 6.0 mmol, 3 eq. 1M in THF) and trimethylaluminum (2.0 mL, 4.0 mmol, 2 eq. 2M in toluene) in dry toluene (5 mL) was stirred at −78° C. under N2 for 1 h, then compound A (800 mg, 2.0 mmol) was added. The mixture was warmed to room temperature and stirred for 16 h. After completion, the mixture was diluted with water (50 mL) and extracted with DCM (200 mL×3). The combined organic layers were washed with brine (100 mL), dried over sodium sulfate, and concentrated in vacuo to give the crude product that was purified by silica gel chromatography to afford compounds 120 (233 mg, 561 μmol, 29%) and 121 (80 mg, 193 μmol, 10%) as white solids.

Compound 120: $^1$H NMR (400 MHz, $CDCl_3$) δ5.30 (d, J=5.1 Hz, 1H), 3.01 (s, 3H), 2.93 (s, 3H), 2.49-2.28 (m, 2H), 2.28-2.13 (m, 1H), 2.05-1.92 (m, 3H), 1.94-1.66 (m, 4H), 1.57-1.13 (m, 13H), 1.11 (s, 3H), 1.01 (s, 3H), 0.95 (d, J=6.5 Hz, 3H), 0.68 (s, 3H).LCMS: [M+H$^+$]=416.3.

Compound 121: $^1$H NMR (400 MHz, $CDCl_3$) δ 5.44 (d, J=5.1 Hz, 1H), 3.05 (s, 3H), 2.97 (s, 3H), 2.49-2.34 (m, 2H), 2.31-2.18 (m, 1H), 2.12-1.68 (m, 8H), 1.62-1.28 (m, 10H), 1.26 (d, J=1.2 Hz, 3H), 1.23-1.04 (m, 5H), 1.02 (s, 3H), 0.99 (d, J=6.5 Hz, 3H), 0.72 (s, 3H).LCMS: [M+H$^+$]=416.4.

Example 122 (R)-4-((3R,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N,N-dimethylpentanamide

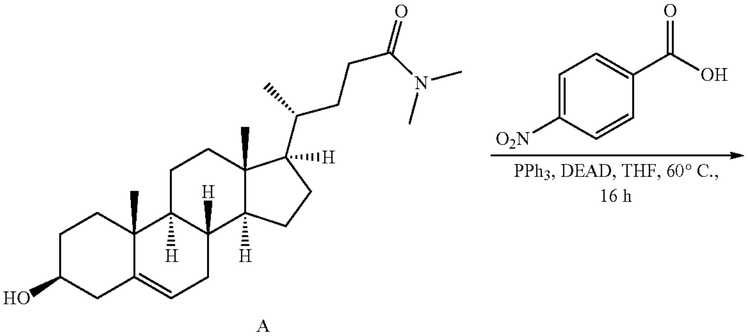

A

-continued

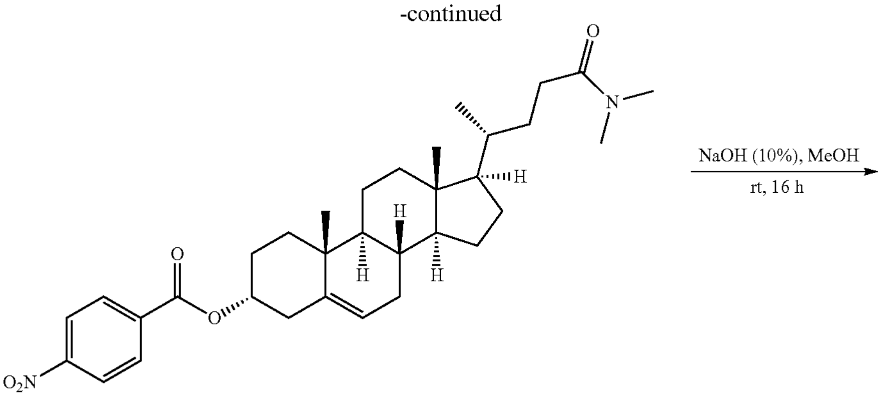

B

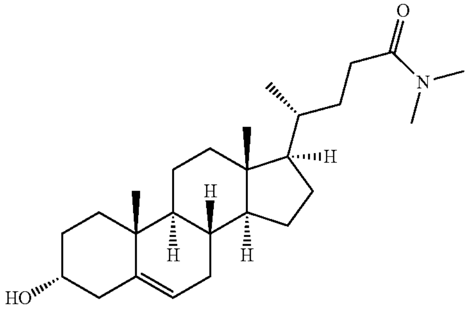

122

To a stirring solution of compound A (300 mg, 747 μmol), 4-nitrobenzoic acid (150 mg, 1.2 eq, 896 μmol) and triphenylphosphine (588 mg, 3 eq, 2.24 mmol) in dry THF (8 mL) at room temperature under $N_2$ atmosphere was added DEAD (156 mg, 1.2 eq, 896 μmol). The mixture was heated to 60° C. and stirred 16 hrs. After completion, the mixture was concentrated in vacuo and the residue was extracted between ethyl acetate and $NaHCO_3$. The organic layer was concentrated in vacuo and the residue was purified by silica gel chromatography (ethyl acetate/petroleum ether=1/50-1:1) to give compound B (310 mg).

To a solution of compound B (108 mg, 196 μmol) in methanol (5 mL) was added NaOH (aq., 10%, 1 mL) at room temperature and stirred for 16 h. After completion, the mixture was diluted with water and extracted with ethyl acetate. The organic layer was washed with aqueous $NaHCO_3$ (100 mL×2) and concentrated to give the crude product that was purified by silica gel chromatography to give compound 122 (36 mg, 89.6 μmol) as an off-white solid. $^1H$ NMR (400 MHz, $CDCl_3$) δ 5.48-5.41 (m, 1H), 4.05 (t, J=3.0 Hz, 1H), 3.05 (s, 3H), 2.98 (s, 3H), 2.61 (d, J=15.4 Hz, 1H), 2.40 (ddd, J=15.7, 11.1, 5.1 Hz, 1H), 2.24 (ddd, J=15.1, 10.4, 5.4 Hz, 1H), 2.14-1.68 (m, 9H), 1.58-1.07 (m, 14H), 1.05 (s, 3H), 0.99 (d, J=6.5 Hz, 3H), 0.72 (s, 3H). LCMS: $[M+H^+]$=402.3.

Example 123: (R)-4-((1S,3R,8S,9S,10R,13R,14S,17R)-1,3-dihydroxy-10,13-dimethyl-2,3,4,7,8,9,10,11,12,13,14,15,16,17-tetradecahydro-1H-cyclopenta[a]phenanthren-17-yl)-N,N-dimethylpentanamide

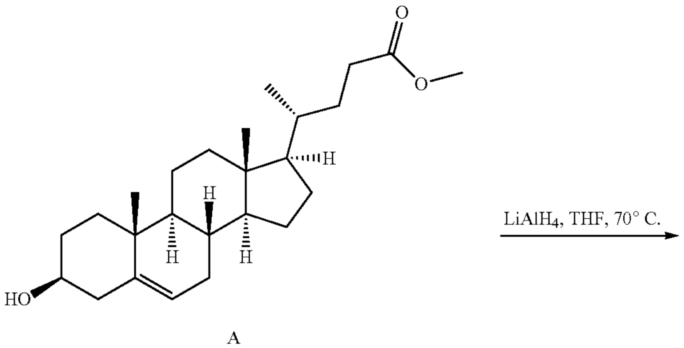

A

-continued
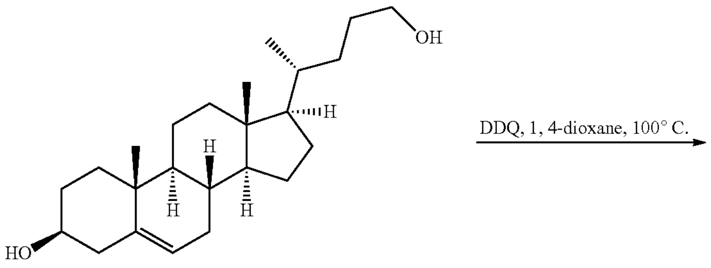
B
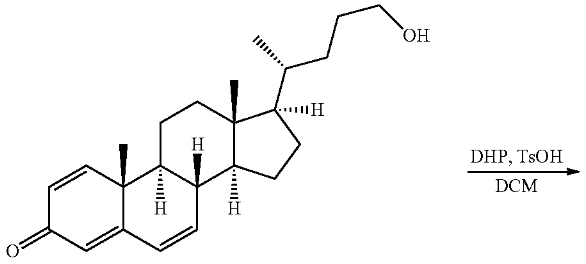
C
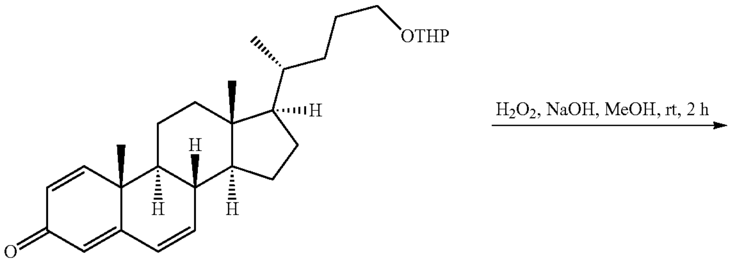
D
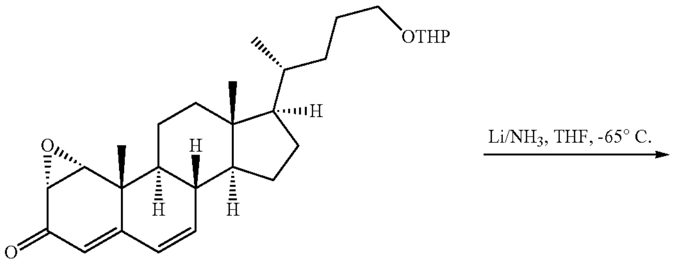
E
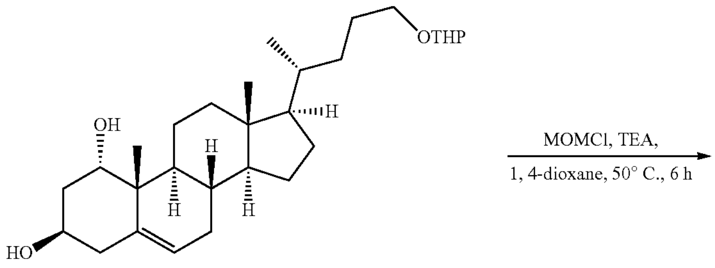
F -continued
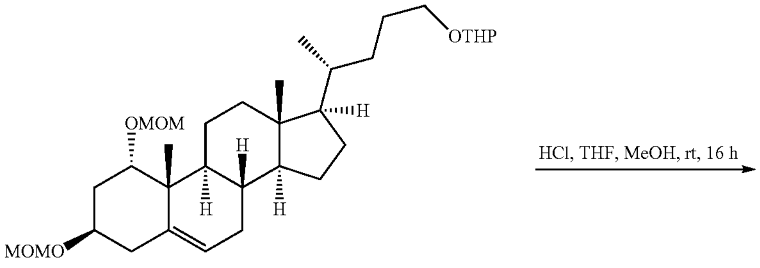
G
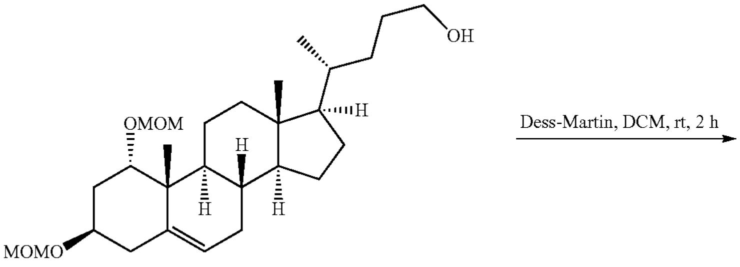
H
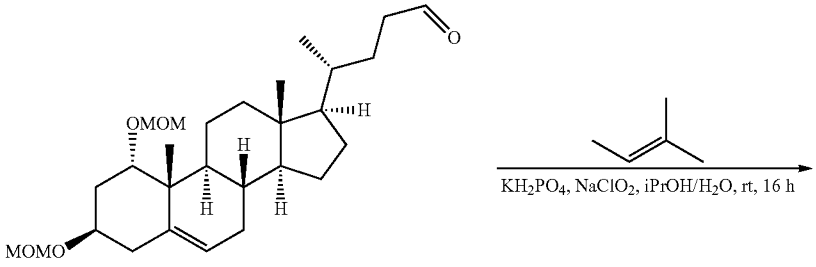
I
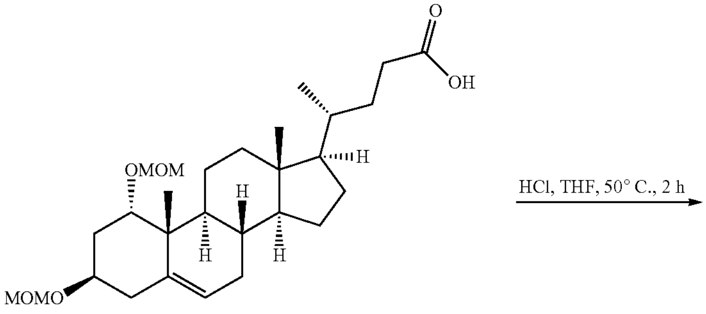
J
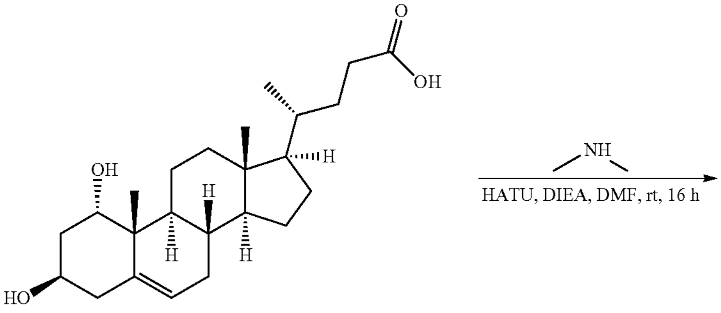
K -continued

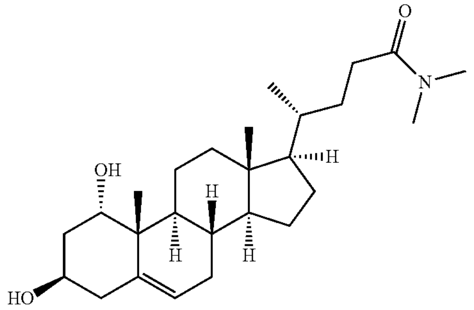

123

To a suspension of $LiAlH_4$ (1.5 g, 38.6 mmol) in THF (200 mL) was drop-wise added compound A (10.0 g, 25.7 mmol) in THF (40 mL) at room temperature. The mixture was stirred at 70° C. for 5 h. After completion, the reaction mixture was quenched by addition of saturated aqueous potassium sodium tartrate and extracted with DCM. The combined organic layers were dried over sodium sulfate and concentrated to give the crude product that was purified by silica gel chromatography to afford compound B (8.0 g, 86%).

To a solution of compound B (8.0 g, 23.1 mmol) in 1,4-dioxane (300 mL) was added DDQ (26.2 g, 115 mmol) at room temperature. The mixture was stirred at 100° C. for 16 h. After completion, the solution was cooled to room temperature. The mixture was filtered and washed with 1,4-dioxane, and the filtrate was concentrated to give crude product that was purified by silica gel chromatography to afford compound C (4.5 g, 57%).

To a solution of compound C (4.0 g, 11.3 mmol) in DCM (80 mL) was added 3,4-dihydro-2H-pyran (2.9 g, 33.8 mmol) and 4-methylbenzene-1-sulfonic acid (194.0 mg, 1.1 mmol). The mixture was stirred at room temperature for 2 h. After completion, the reaction was quenched by the addition of saturated aqueous $NaHCO_3$, and the aqueous layer was extracted with ethyl acetate. The combined organic layers were dried over sodium sulfate and concentrated to give crude product that was purified by silica gel chromatography to afford compound D (4.5 g, 91%).

To the solution of compound D (4.8 g, 11 mmol) in methanol (113 mL) was added 10% sodium hydroxide (0.1 mL, 1.1 mmol) and $H_2O_2$ (0.6 mL, 30% w/w, 27.6 mmol) at room temperature. The mixture was stirred at room temperature for 2 h. After completion, the reaction was quenched by the addition of saturated aqueous $Na_2SO_3$ at 0-5° C. and extracted with DCM. The combined organic layers were dried over sodium sulfate, filtered, and concentrated. The residue was purified by silica gel chromatography to give compound E (1.42 g, 28%).

A four-necked flask was equipped with a sealed mechanical stirrer, a dropping funnel, a cold-finger filled with solid $CO_2$, and an inlet connected to an anhydrous ammonia source. Nitrogen was swept through the system for 10 min, and then ammonia (30 mL) was trapped in the flask. Lithium wire (700 mg) was cut into short pieces and added to the reaction mixture. After stirring for 1 h, compound E (1.0 g, 2.2 mmol) in THF (40 mL) was added dropwise over an hour. The mixture was stirred for another hour before quenched with anhydrous ammonium chloride (40 g). The mixture was diluted with $H_2O$ and extracted with $Et_2O$. The organic layer was concentrated, and the residue was purified by silica gel chromatography to give compound F (420 mg, 42%).

A solution of compound F (420.0 mg, 0.91 mmol) in 1,4-dioxane (5 mL) was added chloro(methoxy)methane (732.6 mg, 9.13 mmol) and ethylbis(propan-2-yl)amine (1.2 g, 9.13 mmol). The mixture was stirred at 50° C. for 6 h. After completion, the mixture was extracted between ethyl acetate and water. The combined organic layer was concentrated, and the residue was purified by silica gel chromatography (ethyl acetate: petroleum ether=1:15) to afford compound G (370.0 mg, 74%) as an oil.

To a solution of compound G (370.0 mg, 0.67 mmol) in THF (4 mL) was added methanol (4 mL) and aqueous HCl (1 mL). The mixture was stirred at room temperature for 16 h under nitrogen. After completion, the mixture was filtered, diluted with water, and extracted with ethyl acetate. The organic layer was concentrated and the residue was purified by silica gel chromatography (ethyl acetate: petroleum ether=1/10) to give compound H (230.0 mg,74%).

To a solution of compound H (230.0 mg, 0.49 mmol) in DCM (6 mL) was added Dess-Martin oxidant (623.4 mg, 1.47 mmol) at 0° C. The mixture was stirred at room temperature for 2 h under nitrogen. After completion, the mixture was filtered, diluted with water, and extracted with ethyl acetate. The organic layer was concentrated to give crude compound I, which was used in the next step directly without further purification.

To a mixture of compound I in isopropyl alcohol (3 mL) and water (1 mL) was added 2-methylbut-2-ene (68.3 mg, 0.97 mmol), potassium dihydrogen phosphate (106.0 mg, 0.78 mmol) and sodium chlorite (70.4 mg, 0.78 mmol) added at 0° C. The mixture was stirred at room temperature for 16 h. After completion, the mixture was diluted with water and extracted with ethyl acetate. The organic layer was concentrated, and the residue was purified by silica gel chromatography to afford compound J (130.0 mg, 54%).

To a solution of compound J (130.0 mg, 0.27 mmol) in THE (10 mL) was added HCl (2.6 mL, 6M). The mixture was stirred at 50° C. for 2 h. After completion, the mixture was diluted with water and extracted with ethyl acetate. The organic layer was concentrated, and the residue was purified by silica gel chromatography to afford compound K (54.0 mg, 51%).

To a solution of compound K (20.0 mg, 51.2 μmol) in DMF (0.4 mL) was added dimethylamine (2.3 mg, 51.2 μmol), HATU (38.9 mg, 102 μmol), and DIEA (33.1 mg, 256 μmol). The mixture was stirred at room temperature for 16 h. After completion, the mixture was diluted with water and extracted with ethyl acetate. The organic layer was concentrated and the residue was purified by C-18 column to give compound 123 (2.4 mg, 11%)$^1$H NMR (400 MHz, $CDCl_3$) δ 5.60 (s, 1H), 4.05-3.93 (m, 1H), 3.85 (s, 1H), 3.01 (s, 3H), 2.94 (s, 3H), 2.46-2.17 (m, 5H), 2.17-1.67 (m, 10H), 1.47 (s, 6H), 1.43-1.06 (m, 13H), 1.03 (s, 3H), 0.95 (d, J=6.4 Hz, 3H), 0.91-0.79 (m, 1H), 0.69 (s, 3H).

Example 124: (3S,8S,9S,10R,13R,14S,17R)-10,13-dimethyl-17-((R)-4-(pyridin-2-yl)butan-2-yl)-2,3,4,7,8,9,10,11,12,13,14,15,16,17-tetradecahydro-1H-cyclopenta[a]phenanthren-3-ol

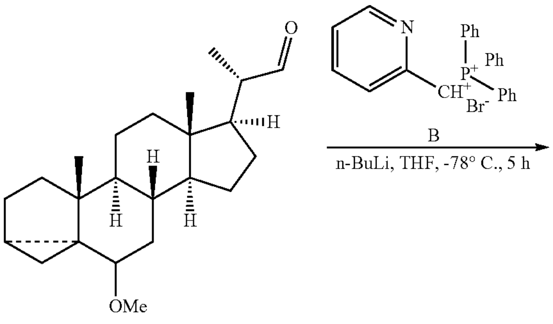

A

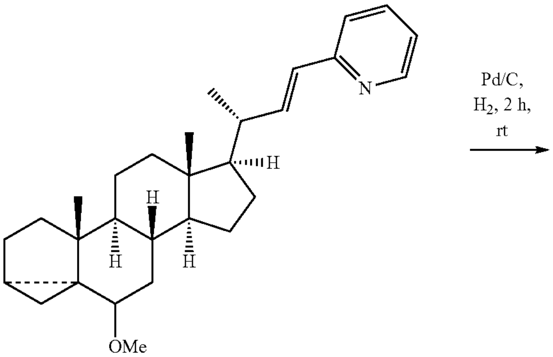

C

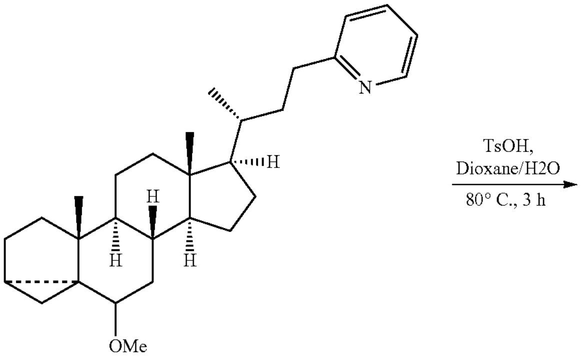

D

-continued

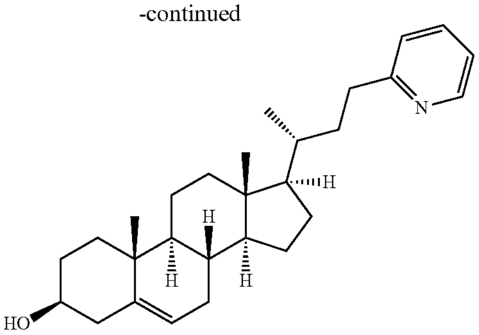

124

To a solution of compound B (26.5 g, 3 eq, 61 mmol) in tetrahydrofuran (151 mL) was added nBuLi (24. 4 mL, 61 mmol, 2.5M in hexanes) at −78° C. under $N_2$. After stirring at this temperature for 1 h, compound A (7.0 g, 20.3 mmol) in THF (20 mL) was added at −78° C. Then the reaction was warmed to room temperature and stirred for 5 h. The reaction was quenched with $NH_4Cl$ (aq) (50 mL) and extracted with ethyl acetate. The combined organic phase was washed with brine and concentrated in vacuo, and the residue was purified by silica gel column to afford compound C (8.0 g, 19.1 mmol) as a white solid.

The solution of compound C (8.0 g, 19.1 mmol) in methanol (86 mL) was added Pd/C (800 mg, 10%) and stirred under 1 atm of $H_2$ at room temperature for 2 h. After completion, the mixture was filtered through Celite and the solvent was concentrated in vacuo to afford compound D (7.0 g, 87%) as a white solid. LCMS: $[M+H]^+$=408.25

To a solution of compound D (7.0 g, 16.6 mmol) in 1,4-dioxane (77.8 mL) and water (13 mL) was added 4-methylbenzene-1-sulfonic acid (1.14 g, 0.4 eq, 6.64 mmol) at room temperature. After stirring at 80° C. for 16 h, the reaction was quenched with water (50 mL) and extracted with ethyl acetate. The combined organic phase was washed with brine and concentrated in vacuo, and the residue was purified by silica gel column to afford compound 124 (3.05 g, 7.48 mmol, 45.07%) as a white solid. $^1$H NMR (400 MHz, $CDCl_3$) δ 8.51 (d, J=4.8 Hz, 1H), 7.62-7.53 (m, 1H), 7.13 (d, J=7.8 Hz, 1H), 7.08 (dd, J=7.4, 5.1 Hz, 1H), 5.34 (d, J=5.1 Hz, 1H), 3.52 (d, J=4.9 Hz, 1H), 2.92-2.80 (m, 1H), 2.67 (dd, J=6.5, 3.9 Hz, 1H), 2.33-2.17 (m, 2H), 2.07-1.79 (m, 6H), 1.62-1.42 (m, 9H), 1.35-1.10 (m, 3H), 1.12-0.99 (m, 9H), 0.98-0.85 (m, 1H), 0.68 (s, 3H).

Example 125: (1R,3aS,3bS,7S,9aR,9bS,11aR)-1-[(2R)-5-hydroxy-5-(propan-2-yl)hept-6-en-2-yl]-9a,11a-dimethyl-1H,2H,3H,3aH,3bH,4H,6H,7H,8H,9H,9aH,9bH,10H,11H,11aH-cyclopenta[a]phenanthren-7-ol

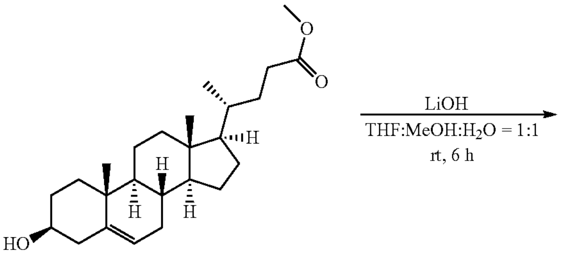

A

-continued

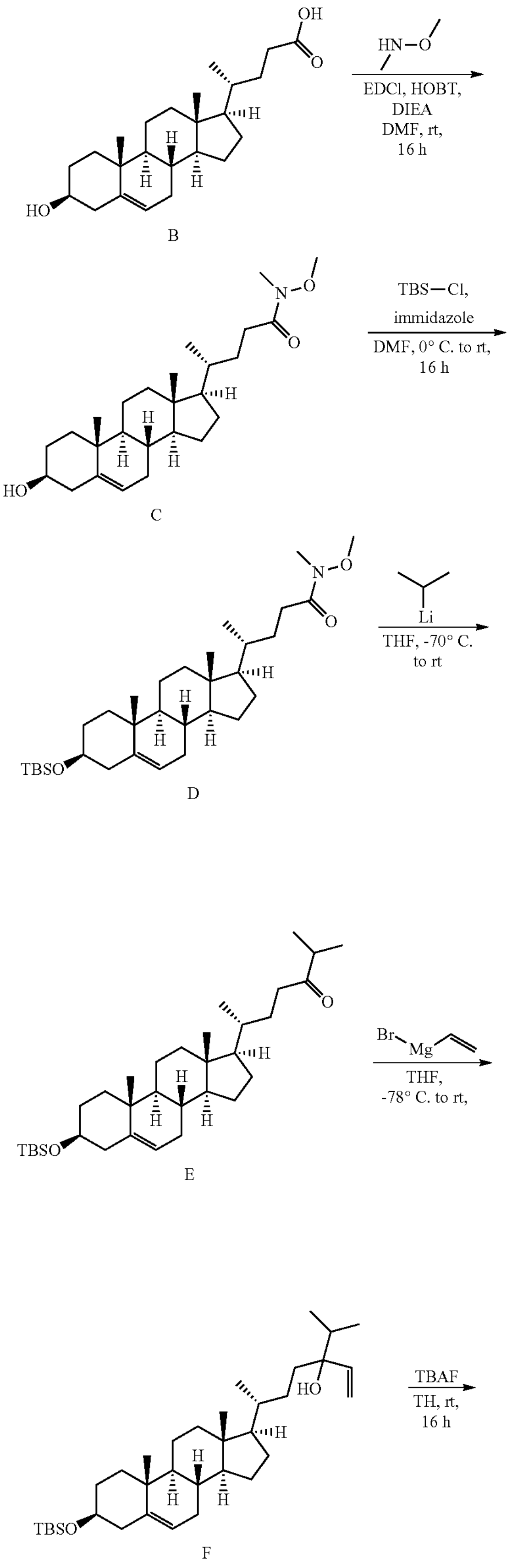

-continued

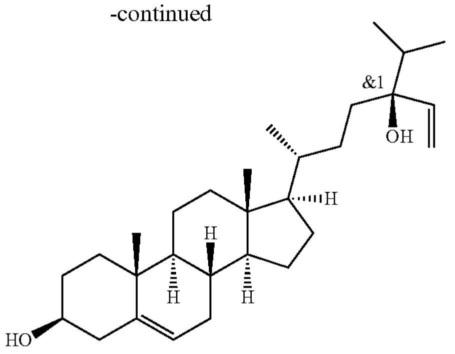

125

To a solution of compound A (13.0 g, 33.5 mmol) in THF (100 mL), methanol (100 mL), and water (100 mL) was added lithium hydroxide (1.33 g, 4 eq, 55.6 mmol). The reaction was stirred at room temperature for 6 h. After completion, the pH of the mixture was adjusted to 3 with HCl (1M), the suspension was filtered and the filter cake was concentrated in vacuo to afford compound B (11.5 g, 91%).

To a solution of crude compound B (11.0 g, 29.4 mmol) in DMF (200 mL), HOBT (6.7 g, 1.5 eq, 44.1 mmol), EDCI (8.44 g, 1.5 eq, 44.1 mmol), Weinreb amine (2.87 g, 29.4 mmol), and ethylbis(propan-2-yl)amine (11.4 g, 3 eq, 88.1 mmol) was added. The reaction mixture was stirred at room temperature for 16 h. After completion, the mixture was diluted with water and extracted with ethyl acetate. The organic layer was concentrated in vacuo and the residue was purified by silica gel chromatography to afford compound C (9.62 g, 78%).

To a solution of compound C (6.0 g, 0.49 eq, 14.4 mmol) in DMF (150 mL) was added 1H-imidazole (6.04 g, 3 eq, 88.7 mmol) and tert-butyl(chloro)dimethylsilane (11.1 g, 2.5 eq, 73.9 mmol) under 0° C. The mixture was warmed to room temperature and stirred for 16 h. After completion, the mixture was diluted with water and extracted with ethyl acetate. The organic layer was concentrated in vacuo and the residue was purified by silica gel chromatography to afford compound D (7.0 g, 44%).

To a solution of crude compound D (3.0 g, 1.7 eq, 940 μmol) in THF (10 mL) was added lithium propan-2-ide (30 mL, 30 mmol, 1M in THF) under $N_2$ at −70° C. After warming to room temperature, the reaction was quenched with water and extracted with ethyl acetate. The organic phase was concentrated in vacuo and the residue was purified by silica gel chromatography to afford compound E (2.07 g, 71%).

To a solution of compound E (2.0 g, 3.88 mmol) in THF (40 mL) at −78° C. under $N_2$ atmosphere was added vinyl magnesium bromide (14.6 mL, 14.6 mmol, 1M in THF) dropwise. The reaction was warmed to room temperature. After completion, the reaction was quenched with water and extracted with ethyl acetate. The organic layer was concentrated in vacuo and the residue was purified by silica gel chromatography to afford compound F (1.73 g, 82%).

To a solution of compound F (1.63 g, 3 mmol) in THF (30 mL) was added TBAF (30 mL mL, 10 eq, 30 mmol, 1M in THF). The reaction was stirred at room temperature for 16 h. After completion, the reaction mixture was diluted with water and extracted with ethyl acetate. The organic layer was concentrated in vacuo and the residue was purified by silica gel chromatography to afford compound 125 (1.19 g, 98%). $^1H$ NMR (400 MHz, $CDCl_3$) δ 5.80 (ddd, J=16.8, 10.9, 5.5

Hz, 1H), 5.35 (d, J=5.1 Hz, 1H), 5.22-5.11 (m, 2H), 3.52 (d, J=4.7 Hz, 1H), 2.33-2.19 (m, 2H), 2.03-1.92 (m, 2H), 1.89-1.78 (m, 3H), 1.77-1.69 (m, 1H), 1.54-1.35 (m, 9H), 1.33-1.05 (m, 7H), 1.01 (s, 3H), 0.94-0.85 (m, 10H), 0.67 (s, 3H).

Example 126: (R)-4-((3S,8S,9S,10R,13R,14S,17R)-3-fluoro-10,13-dimethyl-2,3,4,7,8,9,10,11,12,13,14,15,16,17-tetradecahydro-1H-cyclopenta[a]phenanthren-17-yl)-N,N-dimethylpentanamide

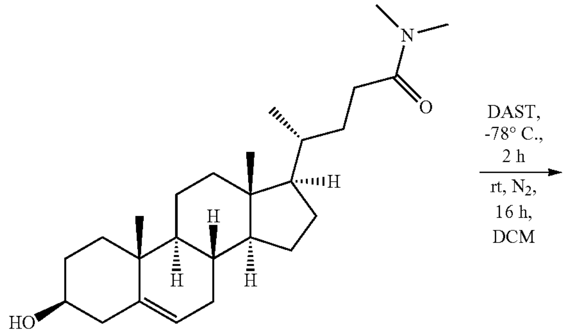

A

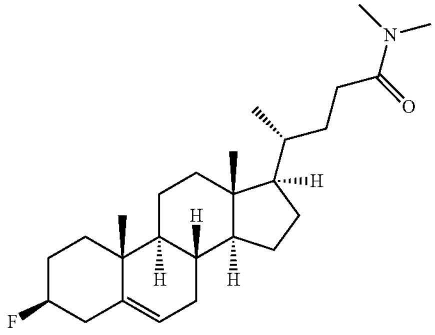

126

To a stirring solution of compound A (500 mg, 1.24 mmol) in dichloromethane (15 mL) was added DAST (803 mg, 4 eq, 4.98 mmol) at −78° C. under $N_2$. The reaction was warmed to room temperature and stirred for 16 h. After completion, a saturated solution of $NH_4Cl$ (100 mL) was added to the reaction mixture. The organic layer was separated, and the aqueous layer was extracted with DCM (30 mL×2). The combined organic layer was concentrated in vacuo and the residue was purified by silica gel chromatography (petroleum ether: ethyl acetate=100:13:1) to give compound 126 (39 mg, 8%). $^1H$ NMR (400 MHz, $CDCl_3$) δ 5.45-5.32 (m, 1H), 4.52-4.25 (m, 1H), 3.01 (s, 3H), 2.94 (s, 3H), 2.49-2.30 (m, 3H), 2.21 (ddd, J=15.3, 10.5, 5.6 Hz, 1H), 2.06-1.64 (m, 7H), 1.54-1.39 (m, 5H), 1.40-1.06 (m, 6H), 1.02 (s, 3H), 0.95 (d, J=6.5 Hz, 3H), 0.69 (s, 3H). $^{19}F$ NMR (376 MHz, $CDCl_3$) δ-167.83 (d, J=48 Hz).

Example 127: (R)-4-((8S,9S,10R,13R,14S,17R)-3,3-difluoro-10,13-dimethyl-2,3,4,7,8,9,10,11,12,13,14,15,16,17-tetradecahydro-1H-cyclopenta[a]phenanthren-17-yl)-N,N-dimethylpentanamide

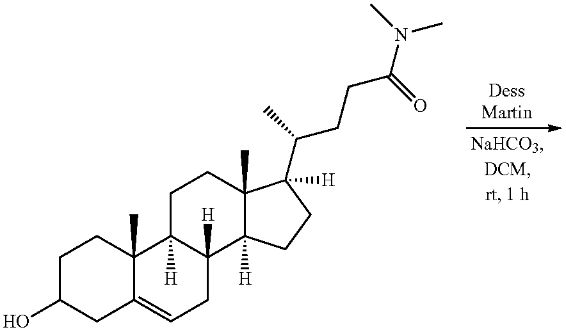

A

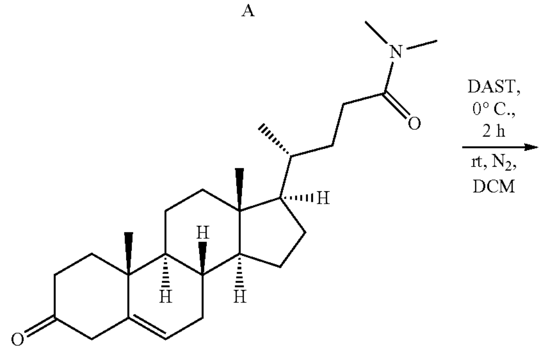

B

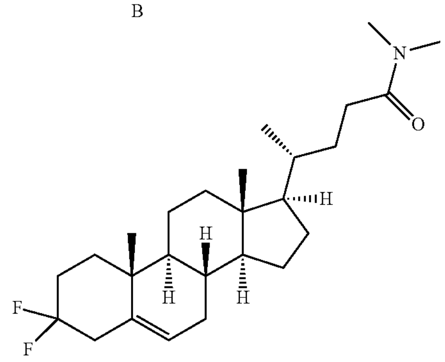

127

To a stirring solution of compound A (500 mg, 1.24 mmol) in dichloromethane (30 mL), Dess-Martin oxidant (1.06 g, 2 eq, 2.49 mmol) and $NaHCO_3$ (523 mg, 5 eq, 6.22 mmol) were added, and the mixture was stirred at room temperature under $N_2$ atmosphere for 1 h. After this period, saturated $Na_2SO_3$ (100 mL) was added. The organic layer was separated, and the aqueous layer was extracted with DCM (50 mL×2). The combined organic layer was concentrated in vacuo and the residue was purified by silica gel column to afford compound B as yellow oil (305 mg, 763 mol, 61%).

To a stirred solution of compound B (305 mg, 0.001 eq, 763 μmol) in DCM (30 mL) at −78° C. under $N_2$ atmosphere, diethyl(trifluoro-λ$^4$-sulfanyl)amine (369 g, 3 eq, 2.29 mol) was added. The mixture was warmed to room temperature and stirred for 2 h. After this period, saturated $NH_4Cl$ (100 mL) was added. The organic layer was separated, and the aqueous layer was extracted with DCM (50 mL×2). The combined organic layer was concentrated in vacuo and the residue was purified by Prep-HPLC to afford compound 127 (14 mg). $^1H$ NMR (400 MHz, $CDCl_3$) δ 5.53 (s, 1H), 3.12 (s, 3H), 3.05 (s, 3H), 2.79 (d, J=15.2 Hz, 1H), 2.63-2.41 (m, 2H), 2.32 (td, J=15.1, 12.8, 5.6 Hz, 1H), 2.19-1.84 (m, 7H), 1.64-1.51 (m, 4H), 1.51-1.17 (m, 8H), 1.14 (s, 3H), 1.06 (d, J=6.5 Hz, 3H), 0.80 (s, 3H). $^{19}F$ NMR (400 MHz, $CDCl_3$) δ-90.94 (d, J=240 Hz), −101.66 (m).

Example 128: (R)-1-(4-(difluoromethyl)-4-hydroxypiperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

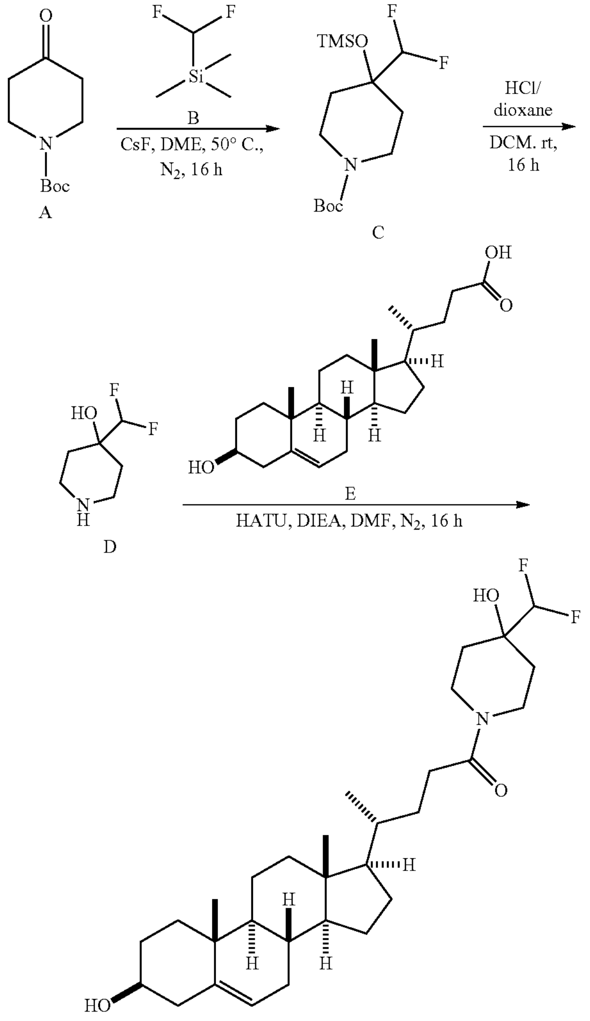

128

A solution of compound A (10.0 g, 50.2 mmol), compound B (18.7 g, 3 eq, 151 mmol) and cesium fluoride (1.52 g, 0.2 eq, 10 mmol) in DME (0.2 L) was stirred at 50° C. under $N_2$ for 16 h. The reaction mixture was diluted with water, extracted with ethyl acetate. The organic layer was washed by brine, dried over sodium sulfate, filtered, and concentrated to afford compound C (17.0 g) as yellow oil.

To a solution of crude compound C (17.0 g, 67.7 mmol) in DCM (170 mL) was added hydrogen chloride (169 mL, 10 eq, 677 mmol, 4M in dixoane) and stirred at room temperature for 16 h. The reaction mixture was concentrated to afford the compound D (9.0 g) as a yellow solid.

To a solution of crude compound D (2.1 g, 13.9 mmol) in dimethylformamide (105 mL) was added compound E (5.2 g, 13.9 mmol), HATU (10.6 g, 2 eq, 27.8 mmol), and DIEA (10.8 g, 6 eq, 83.4 mmol). The mixture was stirred at room temperature under $N_2$ for 16 h. TLC showed SM disappeared, a major new spot was found. The reaction mixture was diluted with water and extracted with ethyl acetate. The organic layer was washed with brine, dried over sodium sulfate, filtered, and concentrated to afford the crude product that was purified by silica gel chromatography to afford compound 128 (3.09 g, yield: 43.8%) as a white solid. $^1H$ NMR (400 MHz, DMSO-$d_6$) δ 5.70 (t, J=56.0 Hz, 1H), 5.32 (s, 1H), 5.26 (d, J=4.0 Hz, 1H), 4.57 (d, J=4.0 Hz, 1H), 4.28 (d, J=12.0 Hz, 1H), 3.74 (d, J=8.0 Hz, 1H), 3.29-3.18 (m, 2H), 2.82-2.69 (m, 1H), 2.39-0.82 (m, 37H), 0.64 (s, 3H).

Example 129: (R)-1-(4-ethyl-4-hydroxypiperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

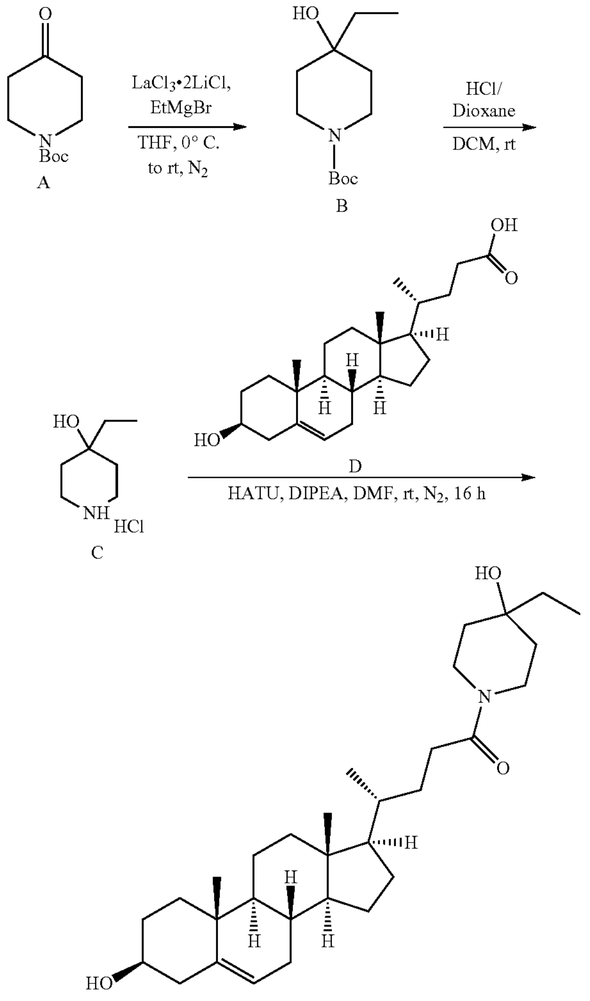

129

A solution of ethylmagnesium bromide (100 mL, 2 eq, 0.1 mol, 1M in THF) and lanthanum trichloride lithium chloride complex (166 mL, 2 eq, 0.1 mol, 1M in THF) in THF (200 mL) was stirred at 0° C. under $N_2$ atmosphere for 2 h. Then compound A (10.0 g, 50.2 mmol) was added, and stirred for 4 h. After completion, the reaction was quenched with saturated $NH_4Cl$ and extracted with ethyl acetate. The combined organic layer was concentrated in vacuo and the residue was purified with silica gel chromatography to give compound B (10.9 g, 47.5 mmol, 95%) (petroleum ether: ethyl acetate=100: 1-1:1) as yellow oil.

To a stirring solution of B (10.9 g, 47.5 mmol) in dichloromethane (200 mL) was added 4N HCl in dioxane (36.3 mL, 149 mmol) and stirred for 3 h. After this period, the mixture was concentrated in vacuo and washed with DCM to give compound C (7.1 g, 42.9 mmol, 90%).

The solution of crude compound D (2.83 g, 1.0 eq, 7.55 mmol), C (1.25 g, 1.0 eq, 7.55 mmol), HATU (4.3 g, 1.5 eq, 11.3 mmol) and DIPEA (3.9 g, 4 eq, 30.2 mmol) in DMF (30 mL) was stirred at room temperature under $N_2$ atmosphere for 16 h. After completion, the reaction mixture was diluted with ethyl acetate and washed with saturated $NH_4C1$, water, and brine. The organic layer was concentrated in vacuo and the residue was purified by silica gel chromatography (DCM:MeOH=100:110:1) to afford compound 129 (2.2 g, 4.53 mmol, 60%).$^1$H NMR (400 MHz, DMSO-$d_6$) δ 5.26 (d, J=4.9 Hz, 1H), 4.58 (s, 1H), 4.14 (s, 1H), 4.11-3.95 (m, 1H), 3.56 (d, J=13.4 Hz, 1H), 3.27 (d, J=13.8 Hz, 3H), 2.96-2.82 (m, 1H), 2.35-2.02 (m, 4H), 2.02-1.60 (m, 6H), 1.60-0.96 (m, 22H), 0.94 (s, 3H), 0.90 (d, J=6.4 Hz, 3H), 0.82 (t, J=7.4 Hz, 3H), 0.65 (s, 3H).

Example 130: (3S,8S,9S,10R,13R,14S,17R)-10,13-dimethyl-17-((R)-4-(3-methylpyridin-2-yl)butan-2-yl)-2,3,4,7,8,9,10,11,12,13,14,15,16,17-tetradecahydro-1H-cyclopenta[a]phenanthren-3-ol

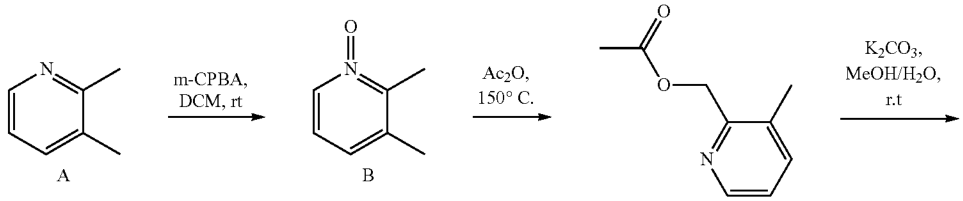

A B C

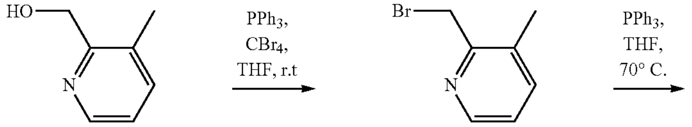

D E

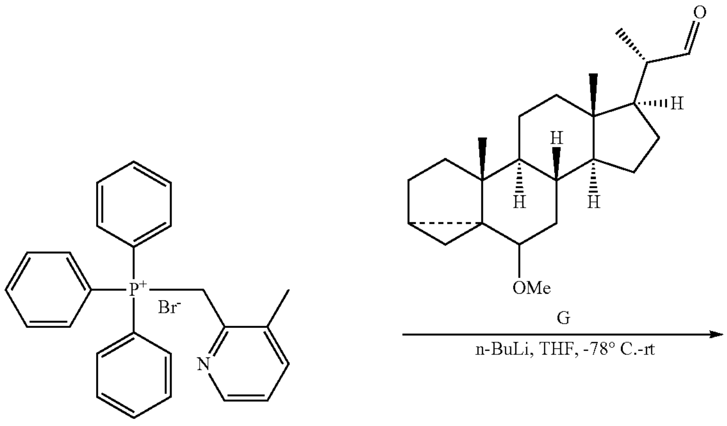

G

F

-continued

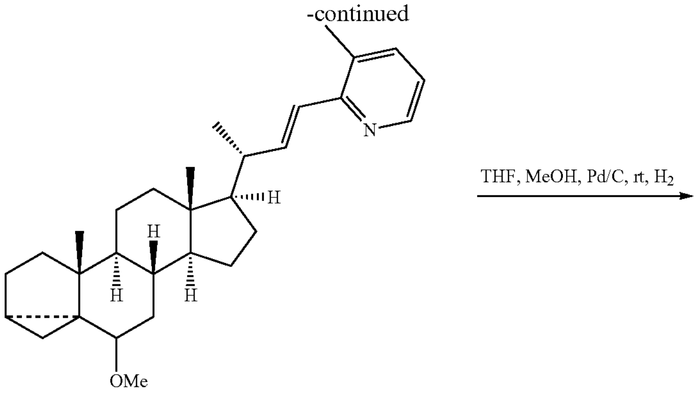

H

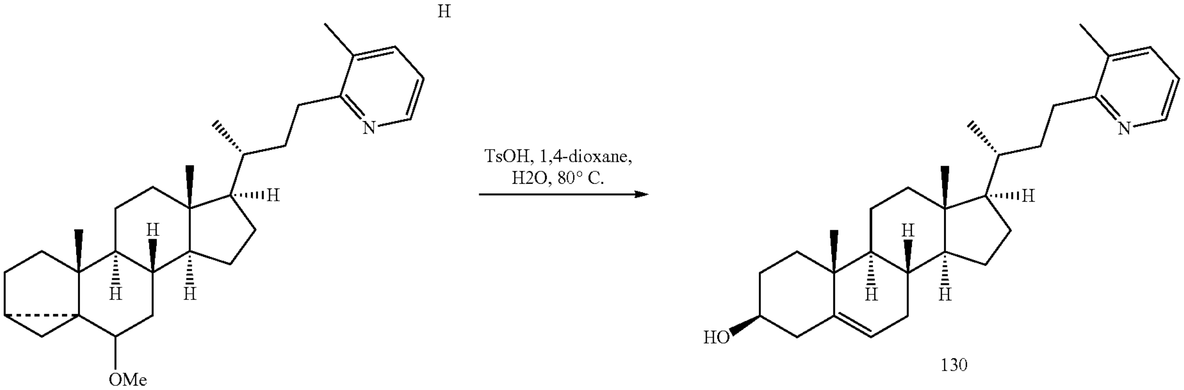

I

130

To a stirring solution of compound A (5.0 g, 46.7 mmol) in DCM (100 mL) at 0° C. was added 3-chlorobenzene-1-carboperoxoic acid (12.1 g, 70 mmol). The mixture was stirred for an additional 30 min at 0° C. and then allowed to warm to room temperature. After completion, the reaction mixture was concentrated to dryness, water (20 mL) was added, and the pH of the mixture was adjusted to 8 by saturated $NaHCO_3$. The mixture was concentrated, and the residue was treated with dichloromethane/methanol (4: 1). The mixture was filtered, and the clear solution was concentrated. The residue was purified by column chromatography to give compound B (4.8 g, 83%).

A solution of compound B (4.8 g, 39 mmol) in acetic anhydride (30 mL) was stirred at 150° C. for 1 h. The mixture was concentrated to give compound C.

To a solution of crude compound C (5.0 g, 30.3 mmol) in methanol (50 mL) and water (25 mL) was added $K_2CO_3$ (7.53 g, 54.5 mmol). The mixture was stirred at room temperature for 1 h. After completion, the solvent was evaporated, and the residue was extracted with DCM. The combined organic phase was concentrated to give crude compound that was purified by column chromatography to give compound D (2.4 g, 64%).

To a solution of compound D (500 mg, 4.06 mmol) in THF (10 mL) at 0° C., triphenylphosphine (1.28 g, 4.87 mmol) and tetrabromomethane (2.69 g, 8.12 mmol) were added, and the mixture was stirred for 4 h at room temperature. After completion, the mixture was diluted with $H_2O$ and extracted with DCM. The organic phase was concentrated to give the crude compound that was purified by column chromatography on silica to give compound E (680 mg, 90%).

To a solution of compound E (480 mg, 2.58 mmol) in THF (10 mL) was added triphenylphosphine (2.1 g, 7.74 mmol). The mixture was stirred at 70° C. for 1 h. After completion, the mixture was filtered to give compound F (500 mg, 43%). LCMS: $[M+H]^+$=369.17.

A solution of crude compound F (1.17 g, 2.61 mmol) in THF (6 mL) was added n-BuLi (1.1 mL, 2.75 mmol, 1.05 eq, 2.5M in hexanes) at −78° C. After stirring at −78° C. for 1 h, compound G (300 mg, 871 μmol) was added and the mixture was warmed to room temperature and stirred for 16 h. The reaction was quenched with saturated $NH_4Cl$ and extracted with DCM. The organic phase was concentrated to give the crude compound that was purified by column chromatography to give compound H (370 mg, 98%).

A mixture of compound H (300 mg, 692 μmol) and Pd/C (60 mg, 20% weight) in methanol (8.6 mL) and THF (8.6 mL) was stirred at room temperature for 16 h under 1 atm of $H_2$. After completion, the mixture was filtered and concentrated to give compound I (280 mg, 643 μmol).

A solution of crude compound I (140 mg, 321 μmol) and 4-methylbenzene-1-sulfonic acid hydrate (12.2 mg, 64.3 μmol) in 1,4-dioxane (4 mL) and water (1 mL) was heated at reflux for 3 h under an atmosphere of $N_2$. The reaction was quenched with saturated $NaHCO_3$ and extracted with ethyl acetate. The organic phase was washed with water and brine, dried with sodium sulfate, and concentrated in vacuo to give crude product that was purified by column chromatography to give compound 130 (11.3 mg, 8%). $^1H$ NMR (400 MHz, $CDCl_3$) δ 8.38 (d, J=4.9 Hz, 1H), 7.50 (d, J=8.3 Hz, 1H), 7.10 (s, 1H), 5.35 (d, J=5.0 Hz, 1H), 3.52 (d, J=10.3 Hz, 1H), 2.91 (d, J=13.4 Hz, 1H), 2.73 (d, J=13.1 Hz, 1H), 2.34 (s, 3H), 2.30-2.18 (m, 2H), 2.03 (dt, J=12.9, 3.6 Hz, 1H), 2.00-1.92 (m, 1H), 1.91-1.80 (m, 3H), 1.79-1.71 (m, 1H), 1.64-1.54 (m, 3H), 1.53-1.48 (m, 3H), 1.36-1.24 (m, 3H), 1.23-11.4 (m, 2H), 1.08 (d, J=6.3 Hz, 3H), 1.01 (s, 3H), 0.98-0.83 (m, 3H), 0.70 (s, 3H).

Example 131: (3S,8S,9S,10R,13R,14S,17R)-10,13-dimethyl-17-((R)-4-(5-methylpyridin-2-yl)butan-2-yl)-2,3,4,7,8,9,10,11,12,13,14,15,16,17-tetradecahydro-1H-cyclopenta[a]phenanthren-3-ol

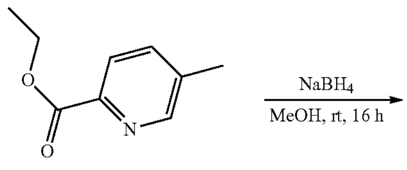

A

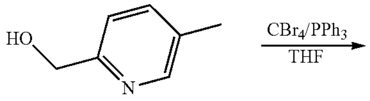

B

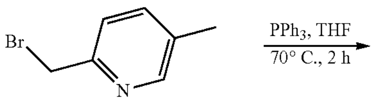

C

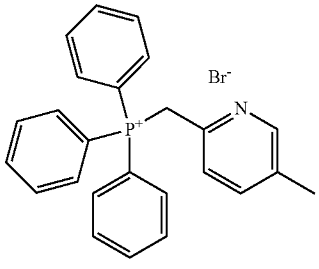

D

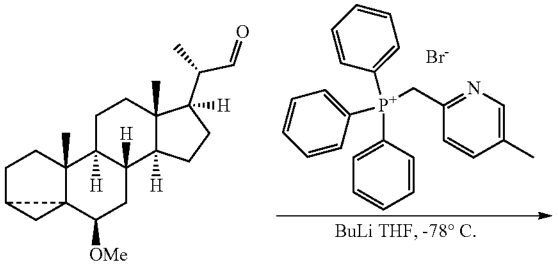

E

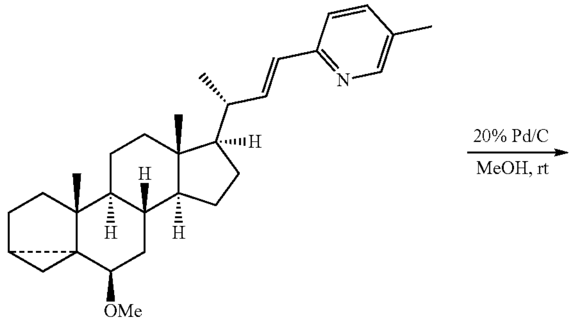

F

-continued

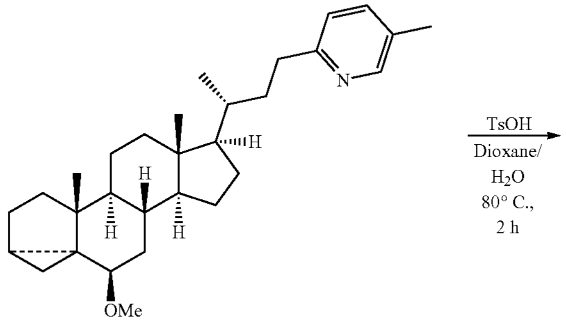

G

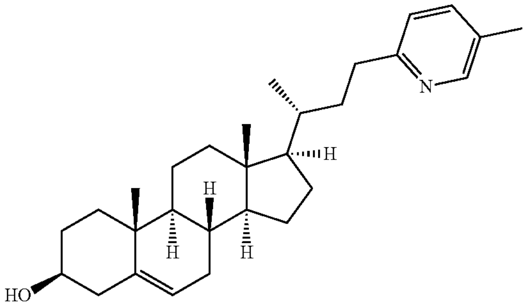

131

To the solution of compound A (2.0 g, 12.1 mmol) in MeOH (20 mL) was added $NaBH_4$ (4.12 g, 109.0 mmol) at 0° C. The mixture was stirred at room temperature for 16 h. After completion, the mixture was filtered through Celite and the solvent was concentrated in vacuo to afford the crude compound that was purified by column chromatography to give compound B (1.0 g, 77%) as a white solid.

To a solution of compound B (1.0 g, 8.12 mmol) in THF (50 mL) was added triphenylphosphine (2.56 g, 9.74 mmol) at 0° C. Then tetrabromomethane (5.39 g, 16.2 mmol) was added in portions. The mixture was allowed to warm to room temperature and stirred for 16 h. The reaction was quenched by the addition of water and extracted with DCM (50 mL×3). The organic layer was washed by brine, dried over sodium sulfate, filtered, and concentrated to afford crude product that was purified by column chromatography to give compound C (1.0 g, 66%) as light yellow oil.

To the solution of compound C (1.0 g, 5.37 mmol) in THF (25 mL) was added triphenylphosphine (4.2 g, 16.1 mmol). The mixture was stirred at 70° C. for 2 h. After completion, the mixture was filtered, and the filter cake was washed with diethyl ether (50 mL×3) to give compound D (1.1 g, 45%) as a white solid.

To a solution of crude compound D (1.05 g, 2.35 mmol) in THF (13.5 mL) at −78° C. was added nBuLi (0.94 mL, 2.35 mmol, 2.5M in hexanes) drop wise. The mixture was stirred at −78° C. for 1 h, then compound E (270 mg, 784 μmol) was added, and the mixture was allowed to warm up to room temperature stirred for 16 h. The reaction was quenched by water and extracted with DCM. The combined organic layers were dried over sodium sulfate and concentrated to afford crude product that was purified by column chromatography to give compound F as a white solid (170 mg, 50%).

To a solution of compound F (170 mg, 0.392 mmol) in MeOH (3 mL) was added Pd/C (35 mg, 20% weight) at room temperature. The mixture was stirred for 16 h under 1 atm $H_2$. After completion, the mixture was filtered through Celite, and the solvent was concentrated in vacuo to afford crude product that was purified by column chromatography to give compound G as a white solid. (90.0 mg, 53%).

To a solution of compound G (90 mg, 0.207 mmol) in 1,4-dioxane (2 mL) and water (0.5 mL) was added 4-methylbenzene-1-sulfonic acid (7.11 mg, 0.041 mmol). The mixture was stirred at 80° C. for 2 h. The reaction was quenched with saturated $NaHCO_3$ and extracted with DCM (50 mL×3). The combined organic layer was dried over sodium sulfate and concentrated to give crude product that was purified by column chromatography to yield compound 131 (13.1 mg, 15%). $^1H$ NMR (400 MHz, $CDCl_3$) δ 8.34 (d, J=2.2 Hz, 1H), 7.42 (dd, J=8.0, 2.2 Hz, 1H), 7.05 (d, J=8.0 Hz, 1H), 5.34 (dd, J=5.0, 2.6 Hz, 1H), 3.52 (dt, J=11.4, 6.2 Hz, 1H), 2.90-2.78 (m, 1H), 2.70-2.59 (m, 1H), 2.35-2.16 (m, 5H), 2.06-1.97 (m, 2H), 1.91-1.77 (m, 4H), 1.54-1.39 (m, 7H), 1.30-1.23 (m, 2H), 1.22-1.11 (m, 3H), 1.09-0.86 (m, 10H), 0.67 (s, 3H). LCMS: $[M+H]^+$=422.30.

Example 132: (3S,8S,9S,10R,13R,14S,17R)-10,13-dimethyl-17-((R)-4-(6-methylpyridin-2-yl)butan-2-yl)-2,3,4,7,8,9,10,11,12,13,14,15,16,17-tetradecahydro-1H-cyclopenta[a]phenanthren-3-ol

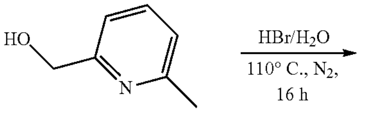

A

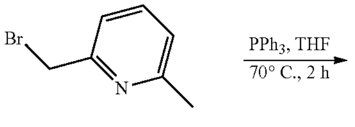

B

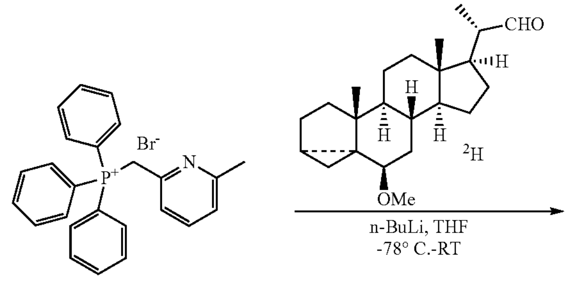

C

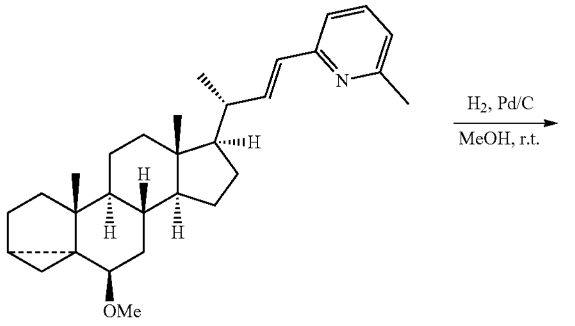

E

-continued

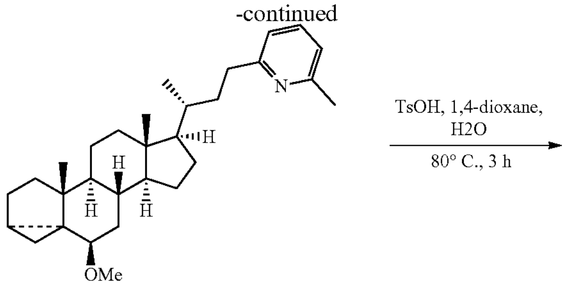

F

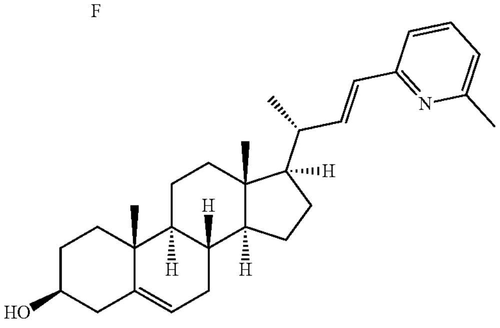

132

Compound A (500 mg, 4.06 mmol) was added to hydrogen bromide solution (10 mL) and refluxed under nitrogen for 16 h. The mixture was quenched with saturated aqueous $NaHCO_3$ and extracted with ethyl acetate. The organic layer was concentrated in vacuo to give the crude product that was triturated with ether to afford compound B (690 mg, 91%).

To a solution of compound B (690 mg, 3.70 mmol) in tetrahydrofuran (10.1 mL) was added triphenylphosphine (972.5 mg, 3.70 mmol), and the mixture was stirred at 70° C. for 2 h. The mixture was filtered to afford compound C (1.34 g, 81%) as pink solid.

To a solution of compound C (1.34 g, 3.64 mmol) in THE (15 mL) was added nBuLi (4.4 mL, 10.92 mmol, 3 eq. 2.5 M in hexanes) at −78° C. under nitrogen followed by stirring at this temperature for 1 h. Then compound D (417.6 mg, 1.21 mmol) was added at the same temperature. The mixture was warmed to room temperature and stirred for 4 h. After completion, the mixture was quenched with water and extracted with ethyl acetate (10 mL×3). The organic layer was washed with brine, dried over sodium sulfate, filtered, and concentrated to give the crude product that was purified by column chromatography to afford compound E (360 mg, 74%). LCMS: $[M+H]^+$=433.73.

To a solution of compound E (360 mg, 0.83 mmol) in methanol (4 mL) was added Pd/C (36 mg, 10% weight). The mixture was stirred at room temperature for 3 h under 1 atm of hydrogen. After completion, the mixture was filtered, the solvent was removed in vacuo and the residue was purified by prep-TLC to afford compound F (200 mg, 56%) as a solid. LCMS: $[M+H]^+$=435.73.

To a solution of compound F (200 mg 0.46 mmol) in 1,4-dioxane (4 mL) and water (0.5 ml) was added 4-methylbenzene-1-sulfonic acid (15.9 mg, 0.092 mmol). The mixture was stirred at 80° C. for 3 h. After completion, the mixture was washed with $NaHCO_3$ and extracted with ethyl acetate (10 mL×3). The organic layer was washed with brine, dried over sodium sulfate, filtered, and concentrated to give the crude product that was purified by column chromatography to yield compound 132 (67 mg, 23%) as white solid. $^1H$ NMR (400 MHz, $CDCl_3$) δ 7.45 (s, 1H), 6.91

(dd, J=7.8, 3.1 Hz, 2H), 5.30 (d, J=4.6 Hz, 1H), 3.47 (t, J=5.1 Hz, 1H), 2.86-2.77 (m, 1H), 2.59 (dt, J=13.2, 6.5 Hz, 1H), 2.49 (s, 3H), 2.23 (dd, J=5.7, 2.1 Hz, 2H), 2.14 (s, 1H), 1.95-1.22 (m, 20H), 1.05-0.95 (m, 9H), 0.64 (s, 1H).

Example 133: (1R,3aS,3bS,7S,9aR,9bS,11aR)-9a,11a-dimethyl-1-[(2R)-4-(pyrimidin-2-yl)butan-2-yl]-1H,2H,3H,3aH,3bH,4H,6H,7H,8H,9H,9aH,9bH,10H,11H,11aH-cyclopenta[a]phenanthren-7-ol

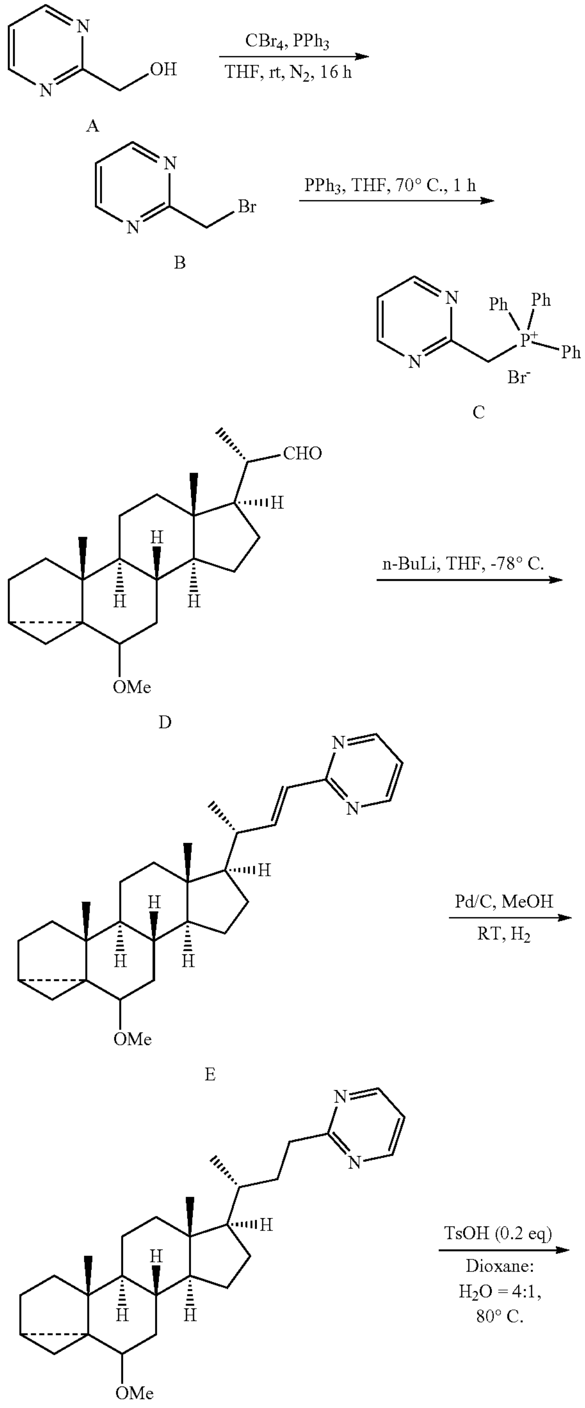

A
B
C
D
E
F

-continued

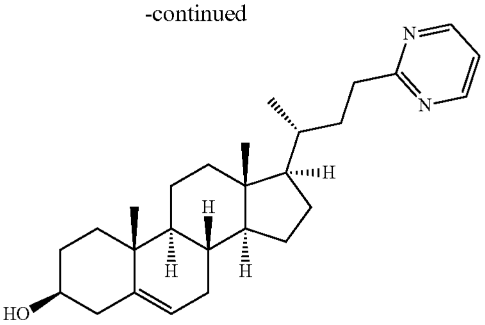

133

To a solution of compound A (500 mg, 4.54 mmol) in THF (10 mL) was added triphenylphosphine (1.43 g, 5.45 mmol) and tetrabromomethane (3.01 g, 9.08 mmol) at 0° C. The mixture was stirred at room temperature for 16 h. After completion, the solvent was removed in vacuo and the residue was purified by silica gel chromatography (eluting with 1/1 ethyl acetate/petroleum ether) to afford compound B (340 mg, 43.3%).

To a solution of compound B (340 mg, 1.97 mmol) in THF (3 mL) was added triphenylphosphine (1.55 g, 5.9 mmol) at 0° C. The mixture was stirred at 70° C. for 1 h. After completion, the solvent was removed in vacuo and the residue was purified by silica gel chromatography (eluting with 50/1 DCM/Methyl alcohol) to afford compound C (410 mg, 47.9%).

To a solution of compound C (379 mg, 871 μmol) in THF (5 mL) at −78° C. was slowly added nBuLi (0.35 mL, 870 μmol, 1 eq. 2.5M in hexanes). The mixture was warmed to room temperature and stirred at room temperature for 1 h before cooling to −78° C. again. Compound D (100 mg, 290 μmol) in THE was added dropwise. The mixture was warmed to room temperature and stirred for 16 h before being quenched with saturated $NH_4Cl$ solution and extracted with ethyl acetate. The organic phase was washed with water and brine, dried with sodium sulfate, and concentrated in vacuo. The residue was purified by silica gel chromatography (eluting with 1/20 ethyl acetate/PE) to afford compound E (90 mg, 73.7%).

To a solution of compound E (90 mg, 214 μmol) in methanol (3 mL) was added Pd/C (9 mg, 10% weight). The mixture was purged with hydrogen three times and then charged with 1 atm of hydrogen. The resulting mixture was stirred for 16 h at room temperature. After completion, the mixture was filtered through Celite, and the filtrate was concentrated in vacuo. The residue was purified by silica gel chromatography (eluting with 1/20 ethyl acetate/petroleum ether) to afford compound F (40 mg, 44.2%).

A mixture of compound F (40 mg, 94.6 μmol) and 4-methylbenzene-1-sulfonic acid hydrate (3.6 mg, 0.2 eq, 18.9 μmol) in 1,4-dioxane (2 mL) and water (0.5 mL) was heated at 80° C.; for 4 h under atmosphere of $N_2$. The reaction was quenched with saturated $NaHCO_3$ solution and extracted with ethyl acetate. The organic phase was washed with water and brine, dried with sodium sulfate, and concentrated in vacuo to give the crude product that was purified by silica gel chromatography (eluting with 1/10 ethyl acetate/petroleum ether) to afford compound 133 (23.4 mg, 60.5%). $^1H$ NMR (400 MHz, $CDCl_3$) δ 8.68 (d, J=5.0 Hz, 2H), 7.14 (t, J=5.0 Hz, 1H), 5.35 (d, J=5.0 Hz, 1H), 3.52 (t, J=5.4 Hz, 1H), 3.10-3.00 (m, 1H), 2.88 (d, J=10.2 Hz, 1H), 2.32-2.20 (m, 2H), 1.97 (d, J=22.2 Hz, 3H), 1.84 (d, J=10.2

Hz, 2H), 1.57 (s, 3H), 1.52-1.47 (m, 4H), 1.45 (s, 1H), 1.35-1.25 (m, 4H), 1.22-1.15 (m, 2H), 1.10 (d, J=12.0 Hz, 1H), 1.04 (d, J=6.2 Hz, 3H), 1.01 (s, 3H), 0.95-0.88 (m, 1H), 0.68 (s, 3H).LCMS: $[M+H]^+$=409.35.

Example 134: (1R,3aS,3bS,7S,9aR,9bS,11aR)-9a,11a-dimethyl-1-[(2R)-4-(pyridazin-3-yl)butan-2-yl]-1H,2H,3H,3aH,3bH,4H,6H,7H,8H,9H,9aH,9bH,10H,11H,11aH-cyclopenta[a]phenanthren-7-ol

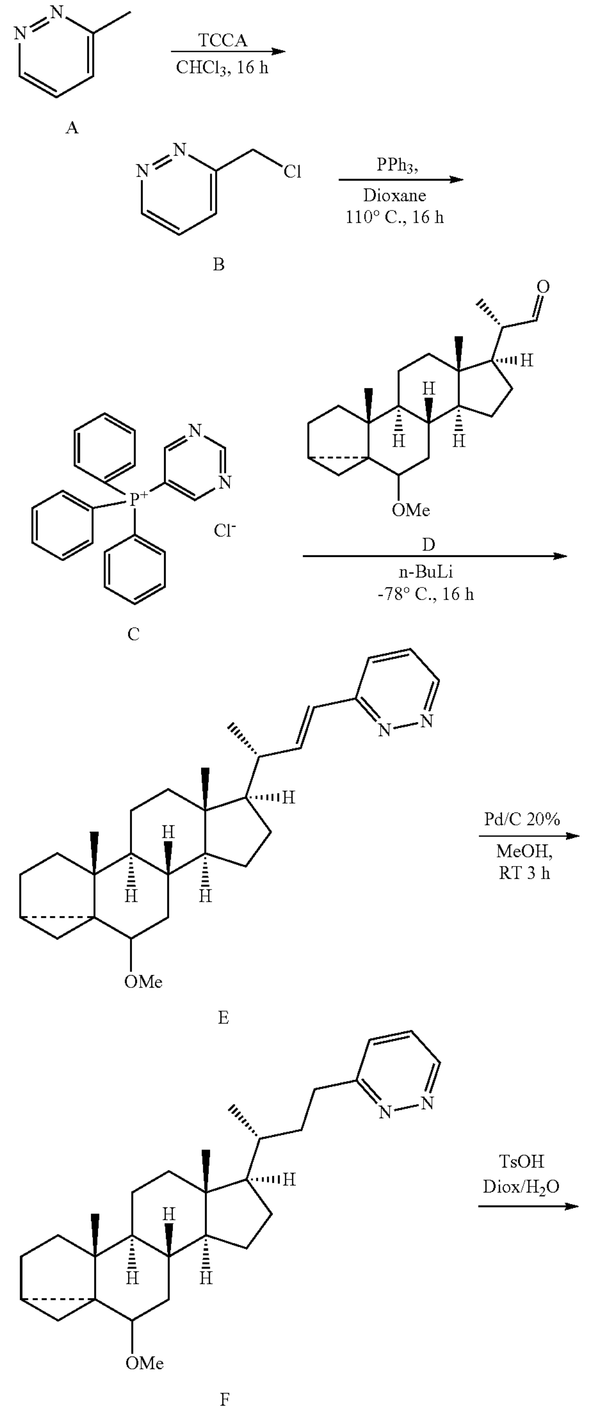

-continued

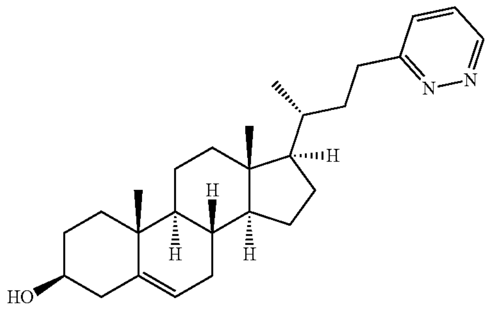

134

To a solution of compound A (1.0 g, 10.6 mmol) in chloroform (20 mL) was added trichloro-1,3,5-triazinane-2,4,6-trione (988 mg, 4.25 mmol). The reaction solution was refluxed 16 h. After completion, the mixture was quenched with water and extracted with DCM. The combined organic layer was dried over sodium sulfate and concentrated to give compound B (600 mg, 44%) as a yellow solid.

To a solution of crude compound B (600 mg, 4.67 mmol) in 1,4-dioxane (20 mL) was added $PPh_3$ (1.47 g, 5.6 mmol) at room temperature. The mixture was stirred at 110° C. for 16 h. After completion, the solvent was evaporated in vacuo and the residue was washed with $Et_2O$ to give compound C (400 mg, 22%).

To a solution of crude compound C (340 mg, 871 μmol) in THE (5 mL) was added nBuLi (0.35 mL, 870 μmol, 1 eq. 2.5 M in hexanes) dropwise at −78° C. After stirring for 1 h at −78° C., compound D (100 mg, 290 μmol) was added. The reaction was slowly warmed to room temperature and stirred for 16 h. After completion, the reaction was quenched by addition of water and extracted with DCM. The combined organic layers were dried over sodium sulfate and concentrated to give the crude compound that was purified by column chromatography to give compound E (35 mg, 29%).

A mixture of compound E (35 mg, 83.2 μmol) and Pd/C (7 mg, 20% weight) in ethyl acetate (2 mL) was purged with $H_2$ for 3 times. The mixture was stirred at room temperature for 3 h under 1 atm of $H_2$. After completion, the mixture was filtered through Celite and the solvent was concentrated in vacuo to afford compound F (30 mg, 85%) as a white solid.

A mixture of crude compound F (30 mg, 71 μmol) and 4-methylbenzene-1-sulfonic acid hydrate (2.7 mg, 4.2 μmol) in 1,4-dioxane (2 mL) and water (0.5 mL) was heated at 80° C.; for 3 h under $N_2$ atmosphere. The reaction was quenched with saturated $NaHCO_3$ solution and extracted with ethyl acetate. The organic phase was washed with water and brine, dried with sodium sulfate, and concentrated in vacuo to give crude product that was purified by silica gel chromatography (eluting with 1/1 ethyl acetate/petroleum ether) to afford compound 134 (11.8 mg, 40.7%). $^1H$ NMR (400 MHz, $CDCl_3$) δ 9.08 (s, 1H), 7.47 (s, 1H), 7.42 (s, 1H), 5.34 (s, 1H), 3.52 (dt, J=12.7, 6.8 Hz, 1H), 3.17-3.02 (m, 1H), 2.99-2.86 (m, 1H), 2.34-2.19 (m, 2H), 2.06-1.94 (m, 3H), 1.92-1.81 (m, 6H), 1.45-1.39 (m, 2H), 1.35-1.12 (m, 4H), 1.20 (s, 3H), 1.07 (d, J=5.9 Hz, 6H), 1.01 (s, 3H), 0.68 (s, 3H). LCMS: $[M+H]^+$=409.30.

Example 135: (3S,8S,9S,10R,13R,14S,17R)-10,13-dimethyl-17-((R)-4-(pyrimidin-4-yl)butan-2-yl)-2,3,4,7,8,9,10,11,12,13,14,15,16,17-tetradecahydro-1H-cyclopenta[a]phenanthren-3-ol

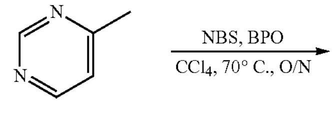

A

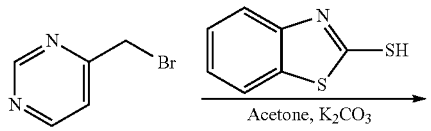

B

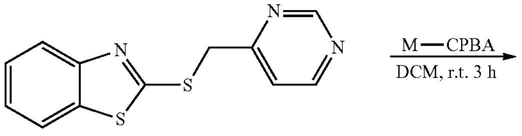

C

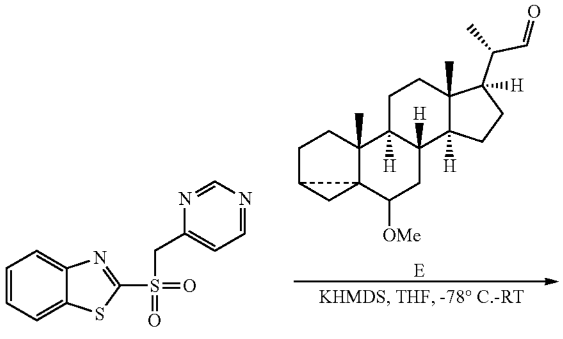

D

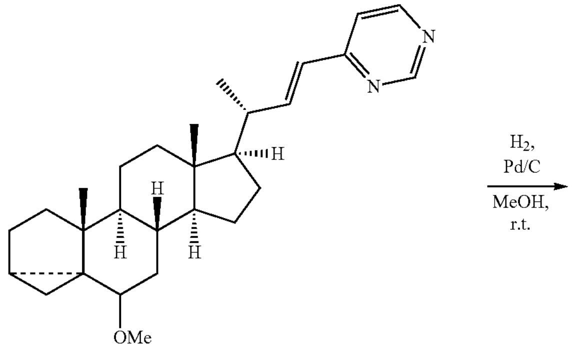

F

-continued

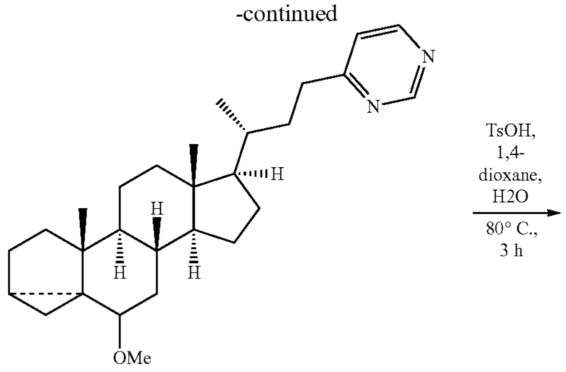

G

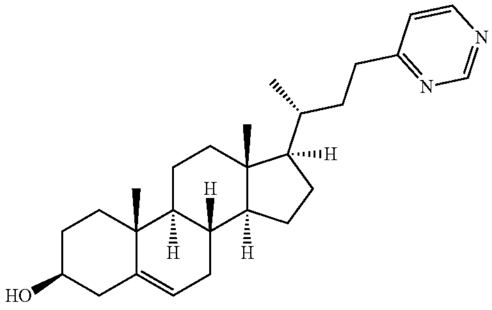

135

To a solution of compound A (3.0 g, 31.9 mmol) in carbon tetrachloride (130 mL) was added benzoylbenzenecarbop-eroxoate (772 mg, 3.19 mmol) and 1-bromopyrrolidine-2,5-dione (6.24 g, 35.1 mmol) at 0° C. under nitrogen. The mixture was stirred for 30 minutes and heated to 70° C. for 16 h. The reaction mixture was quenched by adding saturated $NaHCO_3$ (50 mL) and extracted with DCM (50 mL×3). The organic layer was washed with brine, dried over sodium sulfate, filtered, and concentrated to give the crude product that was purified by column chromatography to afford compound B (580 mg, 10%) as red-brown oil.

To a solution of compound B (580 mg, 3.35 mmol) and 1,3-benzothiazole-2-thiol (1.45 g, 8.65 mmol) in acetone (12 mL) was added potassium carbonate (2.17 g, 15.7 mmol). The mixture was stirred at 55° C. for 2 h. After completion, the mixture was diluted with water (15 mL) and extracted with ethyl acetate (15 mL×3). The organic layer was washed with brine, dried over sodium sulfate, filtered, and concentrated to give the crude product that was purified by column chromatography to afford compound C (580 mg, 66%).

To the solution of compound C (580 mg, 2.23 mmol) in DCM (14.5 mL) at 0° C. 3-chlorobenzene-1-carboperoxoic acid (1.93 g, 11.2 mmol) was added. The mixture was stirred for 3 h, then quenched with 1M sodium thiosulfate solution (20 mL) and extracted with ethyl ether. The combined organic layer was washed with saturated $NaHCO_3$, brine, dried over sodium sulfate, filtered, and concentrated to give the crude product that was purified by column chromatography to afford compound D (120 mg, 18%). LCMS: $[M+H]^+=292.02$.

To a solution of compound E (66.7 mg, 193 μmol) and compound D (120 mg, 412 μmol) in tetrahydrofuran (4 mL) was added KHMDS (0.41 mL, 410 μmol, 2.1 eq. 1M in THF) at −78° C. The mixture was warmed to room temperature and stirred for 16 h. The mixture was quenched with saturated ammonium chloride solution and extracted with ethyl acetate. The organic layer was washed with brine, dried over sodium sulfate, filtered, and concentrated to give the crude product that was purified by column chromatography to afford compound F (40 mg, 47%). LCMS: $[M+H]^+$ =421.3.

To a solution of compound F (40 mg, 95.1 μmol) in methanol (4 mL) was added Pd/C (4 mg, 10% weight). The mixture was stirred at room temperature for 3 h under 1 atm of hydrogen. After completion, the mixture was filtered and concentrated in vacuo to afford the crude product that was purified by prep-TLC to afford compound G (35 mg, 87%) as oil. LCMS: $[M+H]^+$=423.3.

To a solution of compound G (35 mg, 82.8 μmol) in 1,4-dioxane (1 mL) and water (0.25 mL) was added 4-methylbenzene-1-sulfonic acid (3.2 mg, 18.6 μmol). The mixture was stirred at 80° C. for 3 h. After completion, the reaction was quenched by adding saturated $NaHCO_3$ (3 mL) and extracted with ethyl acetate (3 mL×3). The organic layer was washed with brine, dried over sodium sulfate, filtered, and concentrated to give the crude product that was purified by column chromatography to yield compound 135 (18 mg, 53%) as white solid. LCMS: $[M+H]^+$=409.3. $^1$H NMR (400 MHz, $CDCl_3$) δ 9.12 (s, 1H), 8.61 (d, J=4.6 Hz, 1H), 7.24-7.15 (m, 1H), 5.35 (d, J=4.8 Hz, 1H), 3.52 (td, J=11.1, 5.6 Hz, 1H), 2.90-2.80 (m, 1H), 2.73-2.59 (m, 1H), 2.41-2.17 (m, 3H), 2.11-1.94 (m, 3H), 1.91-1.78 (m, 6H), 1.35-1.14 (m, 8H), 1.07-1.00 (m, 7H), 0.98-0.83 (m, 2H), 0.68 (s, 3H).

Example 136: (3S,8S,9S,10R,13R,14S,17R)-10,13-dimethyl-17-((R)-4-(pyrazin-2-yl)butan-2-yl)-2,3,4,7,8,9,10,11,12,13,14,15,16,17-tetradecahydro-1H-cyclopenta[a]phenanthren-3-ol

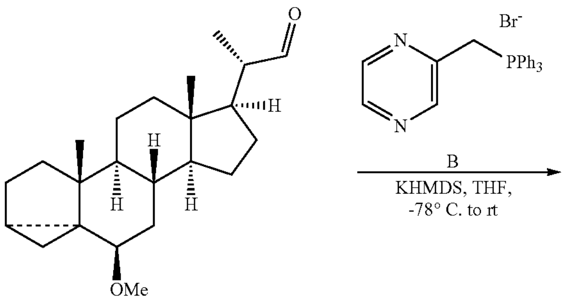

A

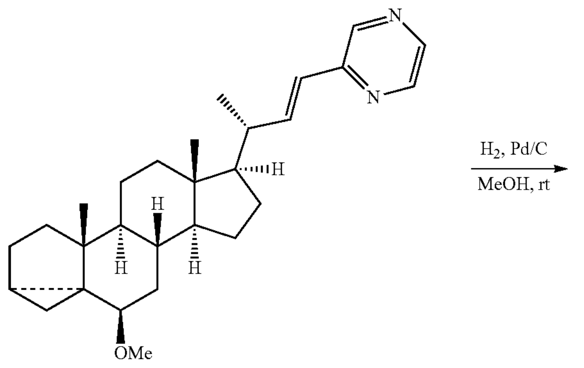

C

-continued

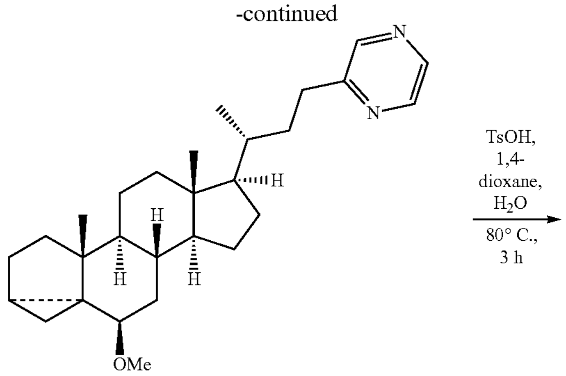

D

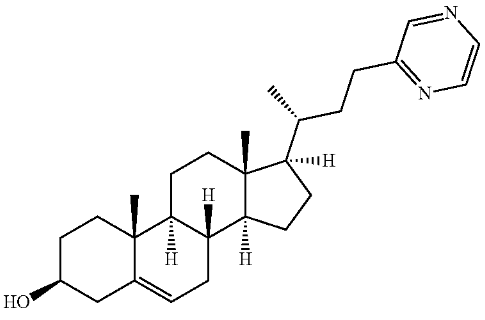

136

To a solution o compound B (758 mg, 1.74 mmol) in tetrahydrofuran (5 mL) was added KHMDS (1.75 mL, 1.75 mmol, 1 M in THF) at −78° C. under nitrogen. After stirring for 1 h, compound A (200 mg, 580 μmol) was added. The reaction was warmed to room temperature and stirred for 4 h. After completion, the mixture was quenched with water and extracted with ethyl acetate (5 mL×3). The organic layer was washed with brine, dried over sodium sulfate, filtered, and concentrated to give the crude product that was purified by column chromatography to afford compound C (220 mg, 90%).

To a solution of compound C (220 mg, 523 μmol) in methanol (4 mL) was added Pd/C (44 mg, 20% weight). The reaction was stirred at room temperature for 4 h under 1 atm of hydrogen. After completion, the mixture was filtered and concentrated to afford the crude product that was purified by prep-TLC to afford compound D. (166 mg, 75%). LCMS: $[M+H]^+$=423.3.

To a solution of compound D (166 mg, 393 μmol) in 1,4-dioxane (4 mL) and water (0.5 ml) was added 4-methylbenzene-1-sulfonic acid (13.5 mg, 78.6 μmol). The mixture was stirred at 80° C. for 3 h. After completion, the reaction was quenched with saturated $NaHCO_3$ and extracted with ethyl acetate (10 mL×3). The organic layer was washed with brine, dried over sodium sulfate, filtered, and concentrated to give the crude product that was purified by column chromatography to yield compound 132 (134 mg, 83%) as white solid. $^1$H NMR (400 MHz, $CDCl_3$) δ 8.56-8.42 (m, 2H), 8.39 (d, J=2.6 Hz, 1H), 5.35 (d, J=4.7 Hz, 1H), 3.52 (tq, J=9.5, 4.7 Hz, 1H), 2.89 (ddd, J=14.9, 11.1, 4.2 Hz, 1H), 2.70 (ddd, J=13.8, 10.1, 5.9 Hz, 1H), 2.33-2.18 (m, 2H), 2.07-1.93 (m, 2H), 1.92-1.78 (m, 4H), 1.77-1.62 (m, 2H), 1.63-1.54 (m, 2H), 1.48-1.39 (m, 3H), 1.36-1.13 (m, 4H), 1.12-1.07 (m, 1H), 1.05 (d, J=6.0 Hz, 3H), 1.01 (s, 3H), 0.68 (s, 3H).

Example 137: (3S,8S,9S,10R,13R,14S,17R)-10,13-dimethyl-17-((R)-4-(oxazol-2-yl)butan-2-yl)-2,3,4,7,8,9,10,11,12,13,14,15,16,17-tetradecahydro-1H-cyclopenta[a]phenanthren-3-ol

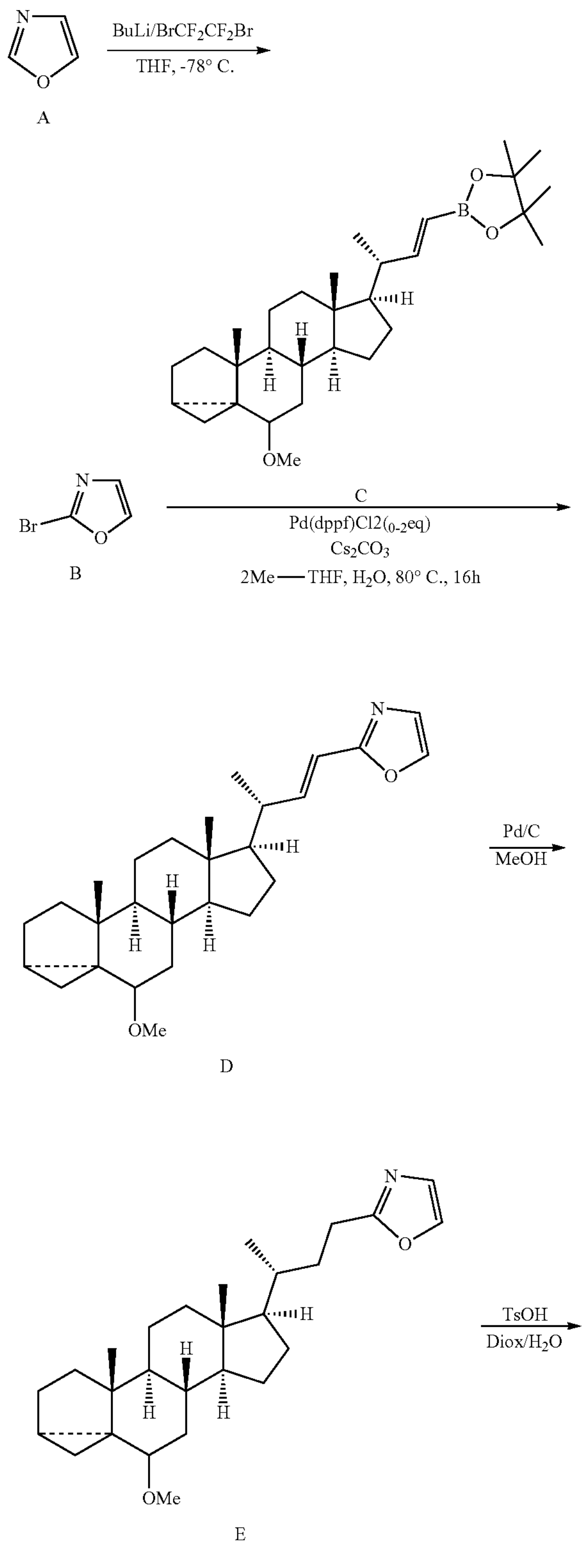

-continued

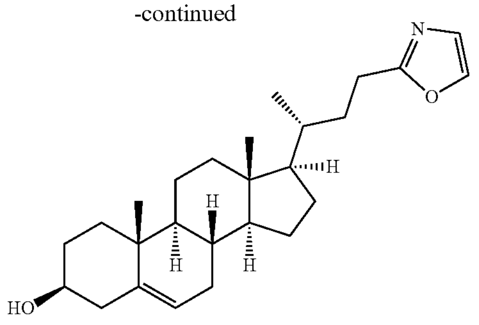

137

To the solution of compound A (2.0 g, 29 mmol) in THE (60 mL) was added dropwise nBuLi (12.7 mL, 31.9 mmol, 2.5 M in hexanes) at −78° C. The mixture was stirred at −78° C. for 40 minutes and then was added 1,2-dibromo-1,1,2,2-tetrafluoroethane (3.46 mL, 29 mmol). The mixture was stirred and allowed to warm to room temperature for 16 h. After completion, the reaction solution was quenched by the addition of saturated $NH_4Cl$ and extracted with DCM. The combined organic layer was dried over sodium sulfate and evaporated in vacuum to give crude 1.5 g of compound B as light yellow oil.

To a solution of compound C (150 mg, 0.32 mmol) in 2-methyloxolane (2 mL) and water (250 μL) was added Pd(dppf)$Cl_2$ (98.9 mg, 135 μmol), cesium carbonate (551 mg, 1.69 mmol) and crude compound B (50 mg, 0.32 mmol) at room temperature. The mixture was stirred at 80° C. for 16 h. After completion, the reaction was quenched by water and extracted with DCM (30 mL×3). The combined organic layer was dried over sodium sulfate and concentrated to give crude product that was purified by column chromatography to give compound D (65 mg, 50%) as a white solid.

To a solution of compound D (65 mg, 159 μmol) in MeOH (2 mL) was added Pd/C (13 mg, 20% weight) at room temperature. The mixture was stirred for 16 h under 1 atm $H_2$. After completion, the mixture was filtered through Celite and the solvent was concentrated in vacuo to afford the crude product that was purified by column chromatography to give compound E (50 mg, 76%) as a white solid.

To a solution of compound E (50 mg, 121 μmol) in 1,4-dioxane (500 μL) and water (125 μL) was added 4-methylbenzene-1-sulfonic acid (4.18 mg, 24.3 μmol). The mixture was stirred at 85° C. 3 h. After completion, the result mixture was quenched by the added $NaHCO_{3(aq)}$ and extracted with DCM (50 mL×3). The combined organic layer was dried over sodium sulfate and concentrated to give crude product that was purified by column chromatography to yield compound 137 (6.7 mg, 14%). $^{1}H$ NMR (400 MHz, $CDCl_3$) δ 7.55 (s, 1H), 7.01 (s, 1H), 5.35 (d, J=5.2 Hz, 1H), 3.52 (tt, J=10.8, 4.8 Hz, 1H), 2.87-2.78 (m, 1H), 2.68 (dt, J=15.6, 8.4 Hz, 1H), 2.32-2.20 (m, 2H), 2.02-1.82 (m, 6H), 1.62-1.45 (m, 8H), 1.29 (dd, J=20.0, 8.6 Hz, 2H), 1.21-1.06 (m, 4H), 1.02-0.93 (m, 7H), 0.68 (s, 3H). LCMS: $[M+H]^+$=398.60.

Example 138: (4R)-1-(3,3-dimethylhexahydro-1H-furo[3,4-b]pyrrol-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

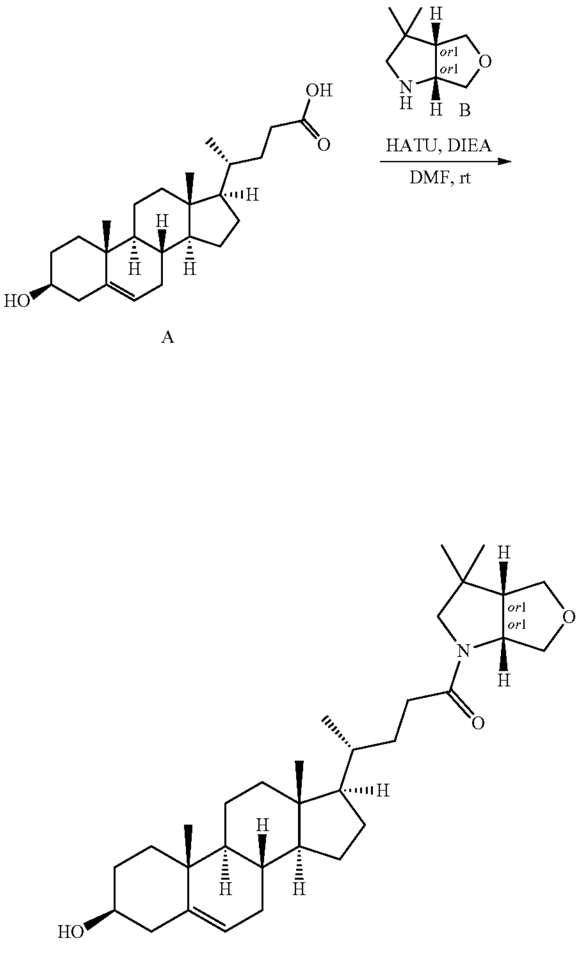

138

To a solution of compound A (100 mg, 267 μmol) in dimethylformamide (4 mL) was added HATU (203 mg, 2 eq., 534 μmol), compound B (37.7 mg, 267 μmol) and ethylbis(propan-2-yl)amine (173 mg, 5 eq., 1.33 mmol). The mixture was stirred at room temperature for 16 h. The reaction was quenched with water and extracted with ethyl acetate (10 mL×4). The combined organic layer was concentrated to give the crude product that was purified by silica gel column to yield compound 138 (30 mg, 22%). $^1H$ NMR (400 MHz, $CDCl_3$) δ 5.36 (d, J=5.0 Hz, 1H), 4.58 (s, 1H), 3.94-3.84 (m, 2H), 3.82-3.66 (m, 2H), 3.52 (dt, J=11.2, 6.2 Hz, 1H), 3.28 (q, J=10.3 Hz, 2H), 2.42 (q, J=7.2 Hz, 1H), 2.28 (ddd, J=16.3, 15.3, 8.4 Hz, 3H), 2.20-2.10 (m, 1H), 1.98 (t, J=12.7 Hz, 2H), 1.84 (d, J=9.6 Hz, 3H), 1.62-1.44 (m, 13H), 1.35-1.24 (m, 5H), 1.18-1.08 (m, 8H), 1.02 (d, J=13.0 Hz, 3H), 0.94 (d, J=6.5 Hz, 3H).

Example 139: (R)-1-((3aS,6aS)-5-allylhexahydropyrrolo[3,4-b]pyrrol-1 (2H)-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

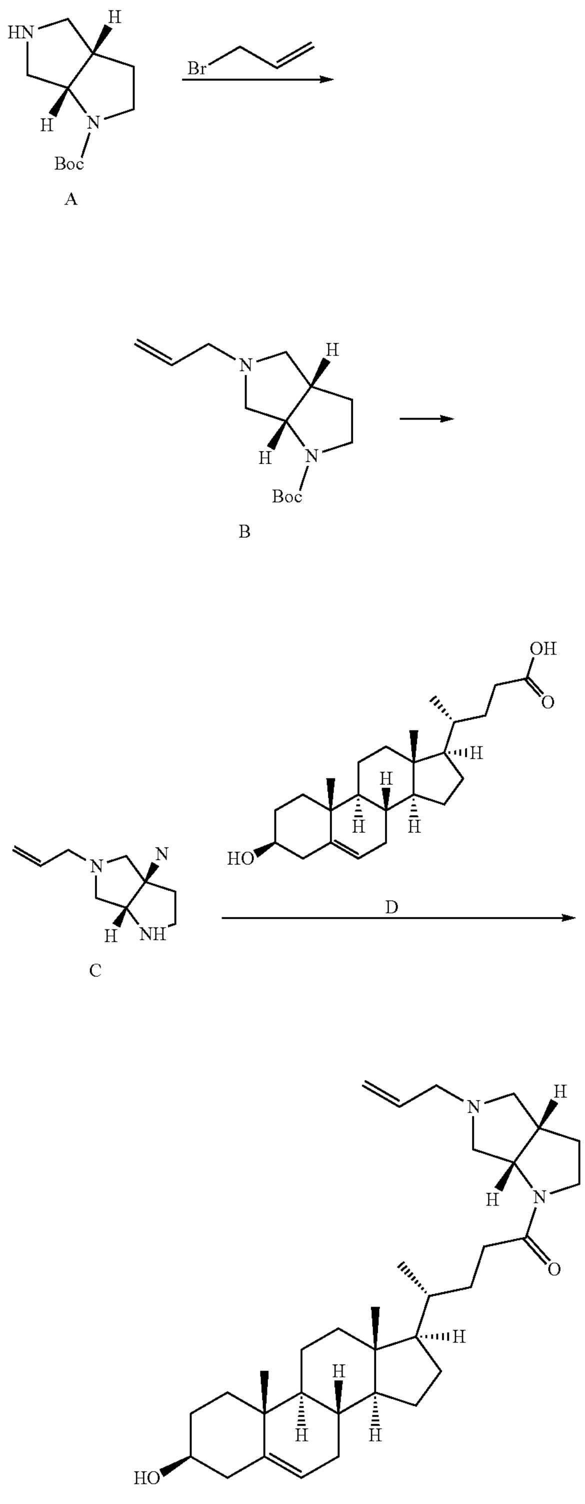

139

To a solution of compound A (120 mg, 565 μmol) in tetrahydrofuran (12 mL) were added allyl bromide (205 mg, 1.7 mmol) and $K_2CO_3$ (312 mg, 2.26 mmol) at room temperature. After the mixture was stirred at room temperature for 16 h. The mixture was diluted with water and extracted with ethyl acetate (20 mL×3). The combined organic phase was washed with brine, dried over sodium sulfate, and concentrated in vacuo to afford compound B (90 mg, 357 μmol) as yellow oil.

To a solution of compound B (90 mg, 357 μmol) in dichloromethane (4.5 mL) was added 4 M HCl in dioxane (2.25 mL) at room temperature After the mixture was stirred for 4 h. The mixture was concentrated in vacuo to afford compound C (60 mg, 355 μmol) as yellow oil.

To a solution of compound D (0.1 g, 267 μmol) and crude compound C (40.6 mg, 267 μmol) in dichloromethane (3.37 mL) were added ethylbis(propan-2-yl)amine (173 mg, 1.33 mmol), EDCI (77.6 mg, 0.4 mmol), and HOBT (60.9 mg, 0.4 mmol) at room temperature. After stirring at room temperature for 16 h, the mixture was concentrated in vacuo and the residue was purified by silica gel column (DCM/MeOH=30/1, v/v) and prep-HPLC to afford the title compound 139 (60 mg, 114 μmol, 43%) as a yellow solid. $^1H$ NMR (400 MHz, $CDCl_3$) δ 5.94-5.78 (m, 1H), 5.38-5.33 (m, 1H), 5.23-5.06 (m, 2H), 4.47-4.24 (m, 1H), 3.60-3.47 (m, 2H), 3.14-2.91 (m, 3H), 2.88-2.68 (m, 2H), 2.52 (s, 1H), 2.40-1.78 (m, 13H), 1.63-0.88 (m, 24H), 0.68 (s, 3H).

-continued

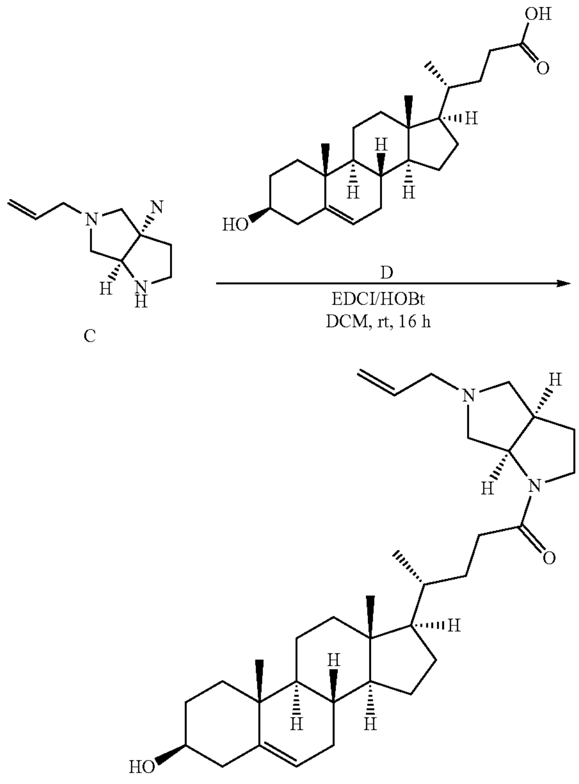

140

Example 140: (R)-1-((3aR,6aR)-5-allylhexahydropyrrolo[3,4-b]pyrrol-1 (2H)-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

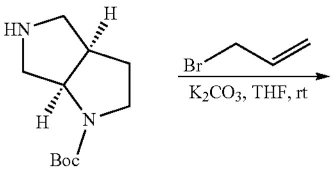

A

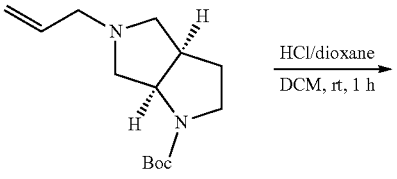

B

To the mixture of A (80 mg, 1.0 eq, 377 μmol) and $K_2CO_3$ (78.1 mg, 2 eq, 565 μmol) in tetrahydrofuran (8 mL, 98.3 mmol) was added allyl bromide (91.2 mg, 2 eq, 755 μmol) at room temperature under $N_2$ atmosphere and stirred for 16 h. The mixture was diluted with water (50 mL) and extracted with ethyl acetate (20 mL×3). The combined organic layers were washed with brine (20 mL), dried over sodium sulfate, and concentrated in vacuo to give the crude product that was purified by chromatography (DCM:MeOH=10:010:1, v/v) to give compound B (100 mg, 396 μmol, 100%).

To a stirred solution of B (100 mg, 396 μmol) in DCM (7 mL) was added hydrogen chloride (1.0 mL, 4.0 mmol, 4M in dioxane) at room temperature under $N_2$ atmosphere and stirred 1 h. The mixture was concentrated in vacuo to give the crude compound C (80 mg, 525 μmol, 100%).

A solution of crude compound C (50 mg, 1.0 eq, 328 μmol), D (123 mg, 1.0 eq, 328 μmol), EDCI (76.5 mg, 1.5 eq, 493 μmol), HOBT (66.6 mg, 1.5 eq, 493 μmol) and ethylbis(propan-2-yl)amine (424 mg, 10 eq, 3.28 mmol) in dichloromethane (8 mL, 125 mmol) was stirred at room temperature under $N_2$ atmosphere 16 h. The mixture was diluted with water (20 mL) and extracted with DCM (20 mL×3). The combined organic layers were washed with brine (50 mL), dried over sodium sulfate, and concentrated in vacuo to give the crude product that was purified by chromatography (DCM:MeOH=10:010:1, v/v) to give compound 140 (42 mg, 82.5 μmol, 25%) as a white solid. $^1H$ NMR (400 MHz, $CDCl_3$) δ 5.86 (dd, J=19.7, 12.4 Hz, 1H), 5.35 (d, J=5.2 Hz, 1H), 5.32-5.07 (m, 2H), 4.51-4.24 (m, 1H), 3.71-3.41 (m, 2H), 3.19-2.52 (m, 5H), 2.41-1.74 (m, 13H), 1.56-1.24 (m, 13H), 1.21-0.82 (m, 14H), 0.70 (s, 3H).

Example 141: (2R,4R)-4-[(1R,3aS,3bS,7S,9aR,9bS,11aR)-7-hydroxy-9a,11a-dimethyl-2,3,3a,3b,4,6,7,8,9,9a,9b,10,11,11a-tetradecahydro-1H-cyclopenta[a]phenanthren-1-yl]-N-methoxy-N,2-dimethylpentanamide
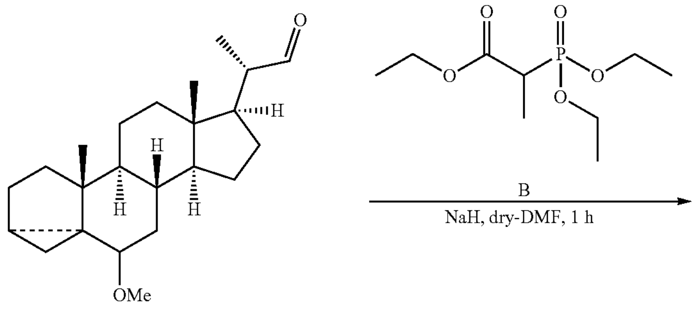
A
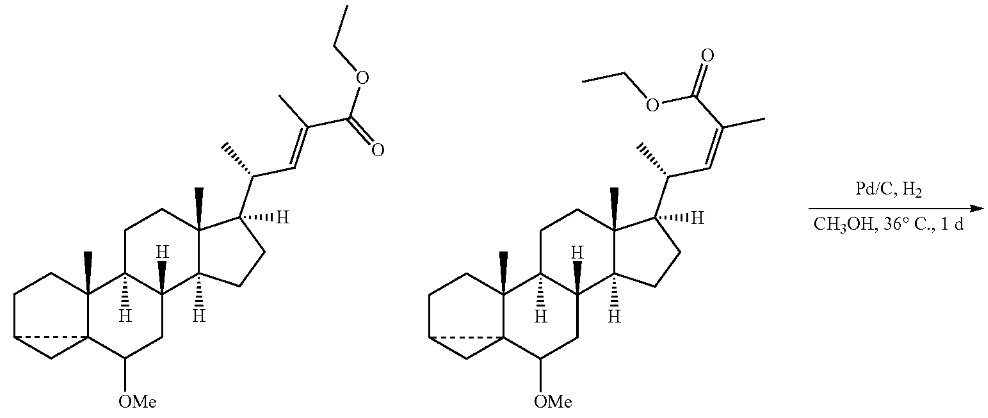
C C1
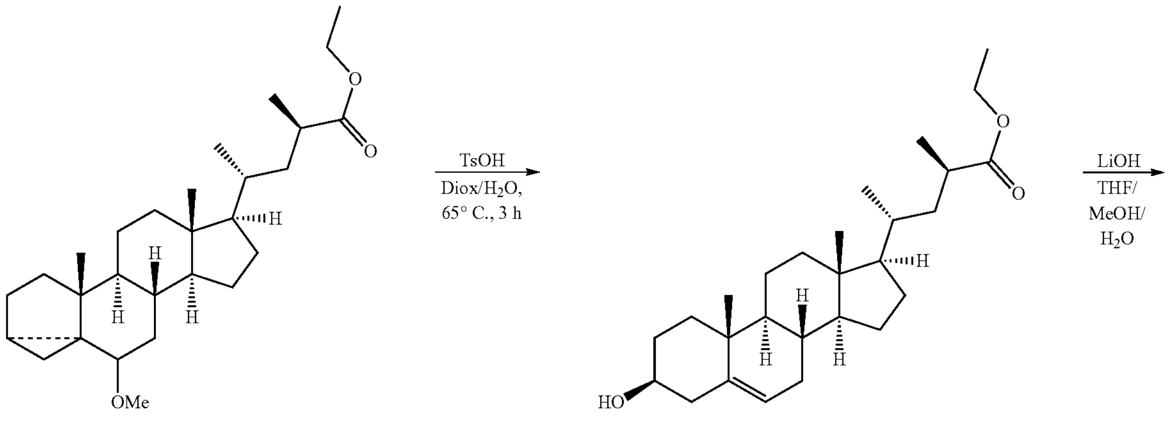
D E -continued

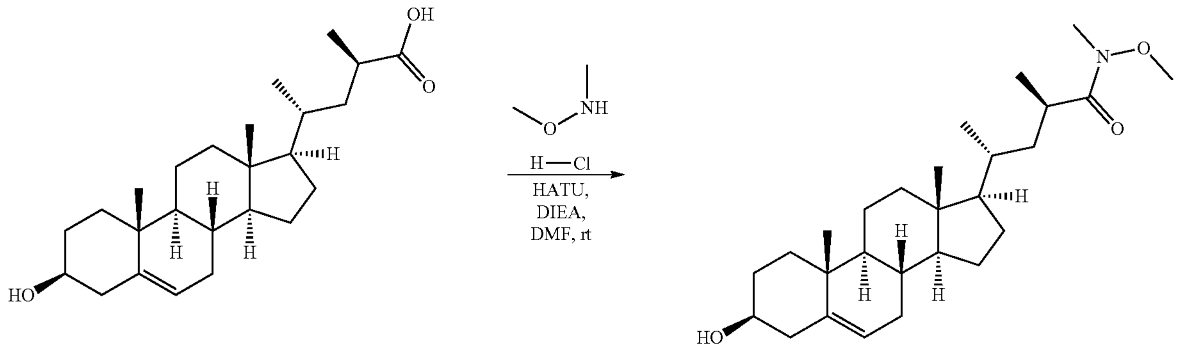

F

141

To a solution of compound B (1.66 g, 6.97 mmol) in DMF (5 mL) at −78° C. under $N_2$ atmosphere was NaH (200 mg, 8.71 mmol). The reaction mixture was stirred at −78° C. for 1 hour. Then compound A (2.0 g, 5.8 mmol) in DMF (5 mL) was added to the mixture at −78° C. After stirring at −78° C. for another hour, the reaction was quenched with water and extracted with EA. The organic phase was concentrated in vacuo and the residue was purified by column chromatography to afford the compound C (800 mg, 32%) and C1 (420 mg, 17%) as a white solid. $^1$H NMR (400 MHz, $CDCl_3$) δ 6.72-6.61 (m, 1H), 4.25-4.12 (m, 2H), 3.32 (s, 3H), 2.77 (s, 1H), 2.46-2.31 (m, 1H), 1.93-1.82 (m, 5H), 1.76-1.67 (m, 3H), 1.54-1.46 (m, 2H), 1.43-1.24 (m, 10H) 1.20-1.15 (m, 1H), 1.08-0.97 (m, 6H), 0.92-0.81 (m, 5H), 0.70-0.62 (m, 4H), 0.50-0.43 (m, 1H).

The solution of compound C (700 mg, 1.63 mmol) in methanol (7 mL) was added Pd/C (140 mg, 20% weight). The mixture was stirred at 35° C. for 24 hours under 1 atm of hydrogen. After completion, the mixture was filtered and concentrated to give the crude which was purified by column chromatography to compound D (150 mg, 21%).

The solution of compound D (150 mg, 348 μmol) in 1,4-dioxane (0.7 mL) and water (0.1 mL) was added TsOH (5.2 mg, 0.03 mmol). The mixture was stirred at 65° C. for 3 hours. After completion, the mixture was washed with $NaHCO_3$ and extracted with ethyl acetate. The organic layer was washed with brine, dried over sodium sulfate, filtered, and concentrated to give the crude which was purified by column chromatography to yield the title compound E (120 mg, 85%).

To a solution of compound E (120 mg, 298 μmol) in THE (2 mL), methanol (2 mL) and water (2 mL) was added LiOH (21.4 mg, 894 μmol). The mixture was stirred for 16 h. After completion, the solvent was removed under vacuum. The residue was diluted with water, acidified with 1N HCl to pH~3 and extracted with DCM. The organic layer was washed by brine, dried over sodium sulfate, filtered, concentrated and the residue was purified by column chromatography to afford compound F (108 mg, 278 μmol) as a white solid.

To a solution of compound F (108 mg, 278 μmol) and hydrogen N,N-dimethylhydroxylamine chloride (54.2 mg, 556 μmol) in DMF was added DIEA (453 mg, 834 μmol) and HATU (159 mg, 417 μmol). The mixture was stirred for 16 h. The reaction was diluted with water, extracted with ethyl acetate. The organic layer was washed by brine, dried over sodium sulfate, filtered, and concentrated. The mixture was purified by column chromatography to afford compound 141 (40 mg, 33%) as a white solid. $^1$H NMR (400 MHz, $CDCl_3$) δ 5.39-5.28 (m, 1H), 3.70 (s, 4H), 3.51 (dt, J=11.1, 5.9 Hz, 1H), 3.18 (s, 3H), 3.07 (d, J=19.1 Hz, 2H), 2.29-2.13 (m, 5H), 2.04-1.67 (m, 5H), 1.62-1.38 (m, 10H), 1.42-1.23 (m, 3H), 1.19-1.08 (m, 9H), 1.08-0.96 (m, 7H), 0.83 (d, J=6.4 Hz, 3H), 0.70 (s, 3H).

Example 142: (4R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methoxy-N,2-dimethylpentanamide

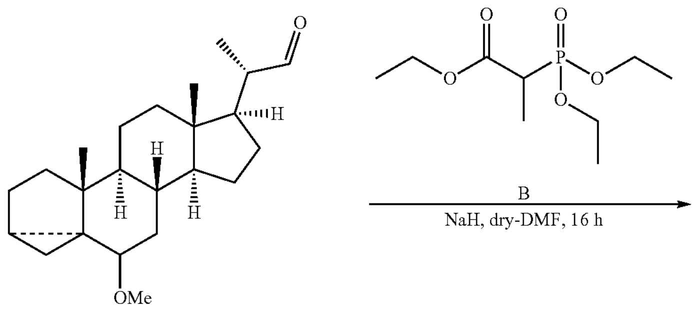

A

-continued

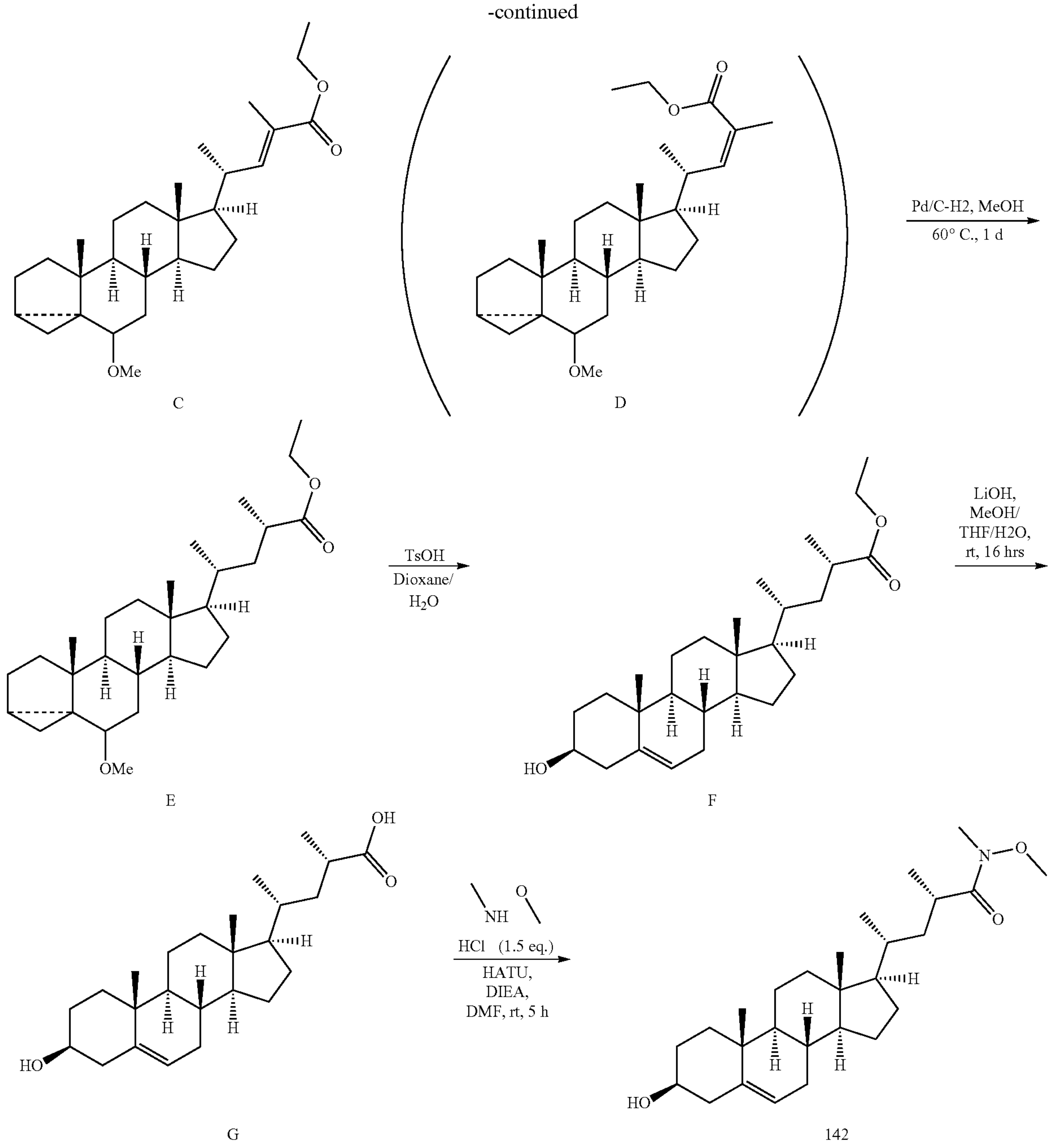

To a stirring solution of ethyl 2-(diethoxyphosphoryl) propanoate (1.66 g, 1.2 eq., 6.93 mmol) and NaH (200 mg, 1.5 eq., 8.73 mmol) in DMF (10 mL, 129 mmol) at 0° C., A (2.00 g, 8.81 mmol) was added. The mixture was warmed to room temperature and stirred for 16 hrs. The reaction was quenched with water and concentrated in vacuo. The residue was purified by column chromatography (EtOAc/petroleum ether=1/5) to afford the compound C (800 mg, 32%) and D (420 mg, 17%) as a white solid. HNMR of C: $^1H$ NMR (400 MHz, $CDCl_3$) δ 6.72-6.61 (m, 1H), 4.25-4.12 (m, 2H), 3.32 (s, 3H), 2.77 (s, 1H), 2.46-2.31 (m, 1H), 1.93-1.82 (m, 5H), 1.76-1.67 (m, 3H), 1.54-1.46 (m, 2H), 1.43-1.24 (m, 10H) 1.20-1.15 (m, 1H), 1.08-0.97 (m, 6H), 0.92-0.81 (m, 5H), 0.70-0.62 (m, 4H), 0.50-0.43 (m, 1H). HNMR of D: $^1H$ NMR (400 MHz, $CDCl_3$) δ 6.59-6.52 (m, 1H), 4.25-4.12 (q, J=8.0 Hz, 2H), 3.32 (s, 3H), 2.77 (s, 1H), 2.61-2.52 (m, 1H), 2.01-1.94 (m, 1H), 1.91-1.83 (m, 4H), 1.79-1.66 (m, 3H), 1.54-1.48 (m, 2H), 1.52-1.42 (m, 2H), 1.32-1.25 (m, 5H), 1.19-1.09 (m, 3H), 1.05-1.00 (m, 7H), 0.92-0.81 (m, 4H), 0.78-0.74 (m, 3H), 0.65 (t, J=4.0 Hz, 1H), 0.43 (dd, J=7.9, 5.0 Hz, 1H).

To a solution of D (420 mg, 981 μmol) in methanol (10 mL) was added Pd/C (40 mg, 10% weight) and stirred under 1 atm of $H_2$ at 60° C. for 24 h. The mixture was filtered and concentrated under vacuum to give the crude which was purified by silica gel chromatograph (petroleum ether/EtOAc=5/1-petroleum ether/EtOAc=1/1, v/v) to give E (210 mg, 488 μmol, 50%).

The solution of E (210 mg, 488 μmol) and 4-methylbenzene-1-sulfonic acid (16.8 mg, 0.2 eq., 97.5 μmol) in 1,4-dioxane (8 mL) and water (2 mL) was stirred at 65° C. under $N_2$ atmosphere for 16 h. After completion, the reaction mixture was diluted with EA, washed with $NaHCO_{3(aq.)}$ and brine. The organic layer was concentrated under vacuum and the residue was purified by column chromatography (DCM: MeOH=100:110:1) to afford F (158 mg, 379 μmol, 78%).

The solution of F (110 mg, 264 μmol) and LiOH (19 mg, 3 eq., 792 μmol) in the mixture of methanol (3 mL), THE (3 mL) and water (3 mL) was stirred at room temperature under $N_2$ atmosphere for 16 h. After completion, the mixture was concentrated under vacuum, the residue was diluted with water and adjusted pH to 2-3 with 1N HCl. The suspension was filtered to give compound G (89 mg, 221 μmol, 84%).

To the solution of G (89 mg, 1.0 eq., 229 μmol) in DMF (3 mL) was added methoxy(methyl)amine hydrochloride (33.5 mg, 1.5 eq., 344 μmol), HATU (131 mg, 1.5 eq., 344 μmol) and DIPEA (148 mg, 5 eq., 1.15 mmol) and stirred at room temperature under $N_2$ atmosphere for 5 h. After completion, the mixture was diluted with ethyl acetate and washed with $NH_4Cl_{(aq)}$, water and brine. The organic layer was concentrated and the residue was purified by column chromatography (DCM:MeOH=100:110:1) to afford 142 (35 mg, 81.1 μmol). $^1$H NMR (400 MHz, $CDCl_3$) δ 5.43-5.28 (m, 1H), 3.70 (s, 3H), 3.58-3.43 (m, 1H), 3.18 (s, 3H), 3.12-2.98 (m, 1H), 2.33-2.10 (m, 4H), 2.00-1.71 (m, 4H), 1.64-1.42 (m, 5H), 1.40-1.18 (m, 3H), 1.19-1.04 (m, 6H), 1.00 (s, 3H), 0.96-0.88 (m, 2H), 0.83 (d, J=6.0 Hz, 3H), 0.70 (s, 3H). LCMS: $t_R$=1.802 min, $[M+H]^+$=432.3.

Example 143: (S)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethyl dimethylglycinate

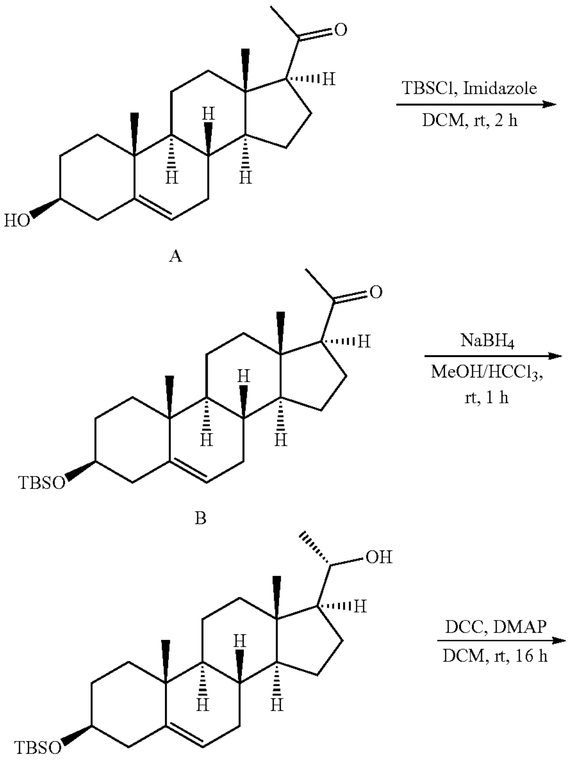

A

B

C

-continued

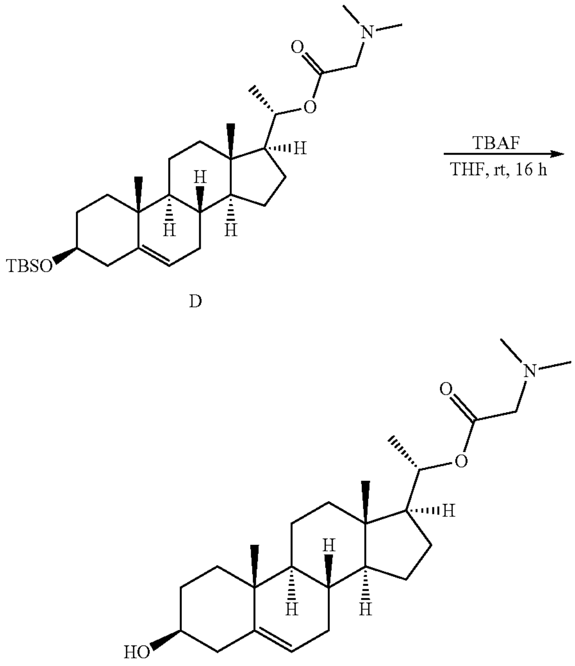

D

143

To the solution of compound A (25.0 g, 79 mmol) in DCM (250 mL) was added 1H-imidazole (8.07 g, 118 mmol) and tert-butyl(chloro)dimethylsilane (17.9 g, 118 mmol) at 0° C. The mixture was stirred at room temperature for 2 h. After completion, the solution was evaporated to give the crude product that was purified by column chromatography to give compound B as a white solid (30 g, 88%).

To a solution of compound B (5.0 g, 11.6 mmol) in methanol (25 mL) and CHC13 (25 mL) was added $NaBH_4$ (2.2 g, 58 mmol) at 0° C. The mixture was stirred at room temperature for 1 h. After completion, the solvent was evaporated to give the crude product that was purified by column chromatography to give compound C as a white solid (723 mg, 14%).

To a solution of compound C (200 mg, 462 μmol) in DCM (5 mL) was added 2-(dimethylamino) acetic acid (52.4 mg, 508 μmol) and 4-(dimethylamino)pyridine (5.69 mg, 46.2 μmol) at room temperature. Then to the mixture was added N, N'-dicyclohexylmethanediimine (105 mg, 508 μmol). The reaction was stirred at room temperature for 16 h. After completion, the solvent was evaporated to give crude product that was purified by column chromatography to give compound D as a white solid (100 mg, 42%).

To a solution of compound D (100 mg, 193 μmol) in THF (2 mL) was added tetrabutylammonium fluoride (500 uL, 500 μmol, 1 M in THF). The mixture was stirred at room temperature for 16 h. After completion, the solvent was evaporated to give crude product that was purified by column chromatography to give compound 143 as a white solid (42 mg, 54%). $^1$H NMR (400 MHz, $CDCl_3$) δ 5.33 (dt, J=4.4, 1.8 Hz, 1H), 5.00 (dq, J=8.8, 6.4 Hz, 1H), 3.55-3.45 (m, 1H), 3.10 (d, J=3.0 Hz, 2H), 2.33 (s, 6H), 2.26 (dt, J=5.4, 2.6 Hz, 2H), 2.04-1.88 (m, 2H), 1.85-1.77 (m, 4H), 1.69-1.41 (m, 8H), 1.24 (d, J=6.2 Hz, 3H), 1.23-0.90 (m, 8H), 0.68 (s, 3H). LCMS: $[M+H]^+$=404.25.

Example 144: (S)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethyl 2-amino-2-oxoacetate

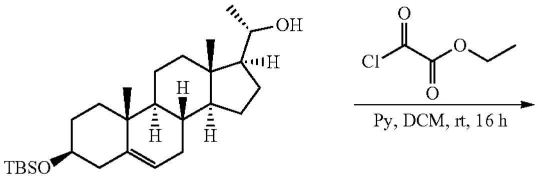

A

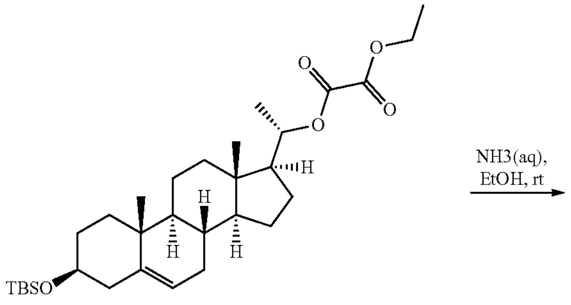

B

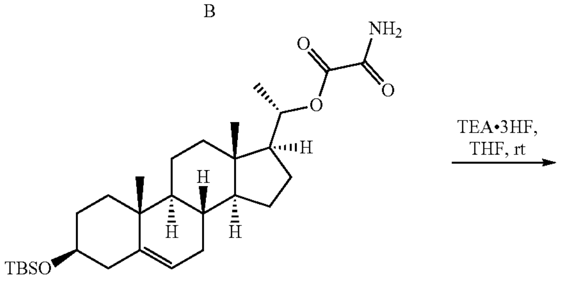

C

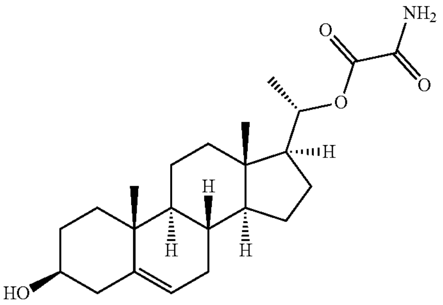

144

A solution of compound A (200 mg, 462 μmol) and pyridine (40.2 mg, 508 μmol) in dichloromethane (4 mL) was cooled in an ice bath and ethyl oxalyl monochloride (69.4 mg, 508 μmol) was added over 5 mins. The mixture was stirred at room temperature for 16 h. The mixture was concentrated, and the residue was purified by column chromatography to give compound B (150 mg, 61%).

A solution of compound B (100 mg, 187.6 μmol) in ethanol (2 mL) was added ammonium hydroxide (0.2 mL) and stirred at room temperature for 16 h. The mixture was concentrated, and the residue was purified by column chromatography to give compound C (90 mg, 95%).

A solution of compound C (40 mg, 79.4 μmol) and triethylamine trihydrofluoride (0.5 mL) in tetrahydrofuran (2 mL) was stirred at room temperature for 8 h. To the mixture was added $H_2O$, and it was extracted with DCM. The organic phase was concentrated, and the residue was purified by column chromatography to give compound 144 (21 mg, 68%). $^1H$ NMR (400 MHz, $CDCl_3$) δ 6.90 (s, 1H), 5.71 (s, 1H), 5.35 (s, 1H), 5.08 (t, J=7.6 Hz, 1H), 3.59-3.48 (m, 1H), 2.33-2.21 (m, 2H), 2.04-1.79 (m, 6H), 1.78-1.60 (m, 3H), 1.46 (d, J=13.6 Hz, 3H), 1.36 (d, J=6.2 Hz, 3H), 1.28-1.03 (m, 4H), 1.01 (s, 3H), 0.97 (s, 1H), 0.72 (s, 3H).

Example 145: (S)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethyl 2-(methylamino)-2-oxoacetate

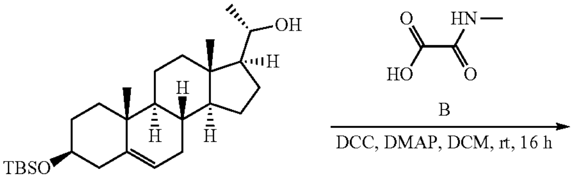

A

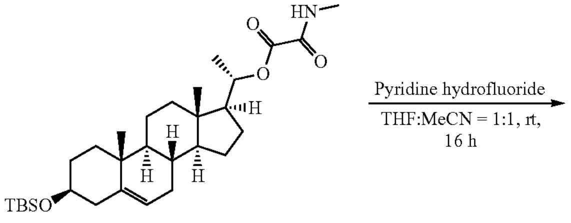

C

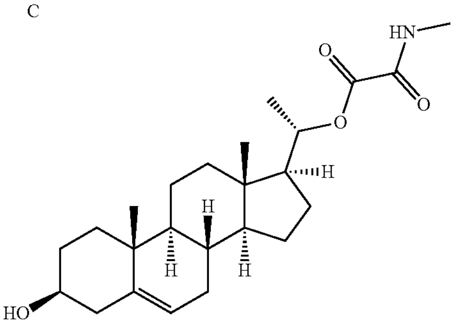

145

To a solution of compound A (200 mg, 462 μmol) in DCM (5 mL) was added compound B (47.6 mg, 462 μmol), DCC (105 mg, 508 μmol), and DMAP (5.7 mg, 46 μmol). The mixture was stirred at room temperature for 16 h. After completion, the mixture was diluted with water and extracted with DCM, dried over sodium sulfate, and concentrated to give the crude product that was purified by column chromatography to afford compound C (85 mg, 35%).

To a solution of compound C (90 mg, 174 μmol) in THF (1 mL) and acetonitrile (1 mL) was added pyridine hydrofluoride (0.1 mL). The solution was stirred at room temperature for 16 h. After completion, the reaction was diluted with water, extracted with DCM. The combined organic phase was dried over sodium sulfate and concentrated to give the crude product that was purified by column chromatography to afford compound 145 (30 mg, 42%). $^1H$ NMR (400 MHz, $CDCl_3$) δ 7.06 (s, 1H), 5.35 (d, J=5.1 Hz, 1H), 5.13-5.02 (m, 1H), 3.59-3.45 (m, 1H), 2.92 (d, J=5.1 Hz, 3H), 2.32-2.21 (m, 2H), 2.01-1.82 (m, 5H), 1.67-1.60 (m, 1H), 1.49-1.43 (m, 3H), 1.34 (d, J=6.2 Hz, 3H), 1.26 (s, 3H), 1.23-1.03 (m, 4H), 1.01 (s, 3H), 0.99-0.85 (m, 2H), 0.72 (s, 3H).

Example 146: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-hydroxy-4-vinylpiperidin-1-yl) pentan-1-one

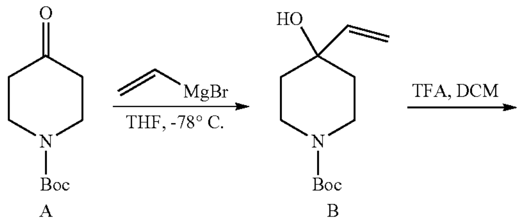

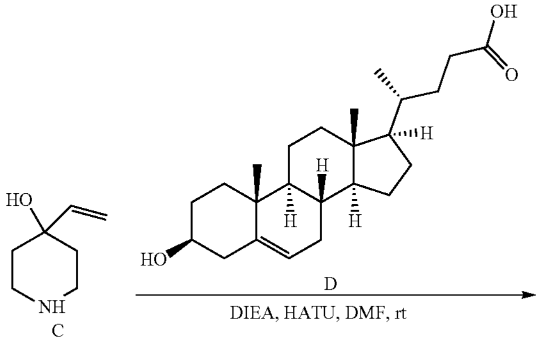

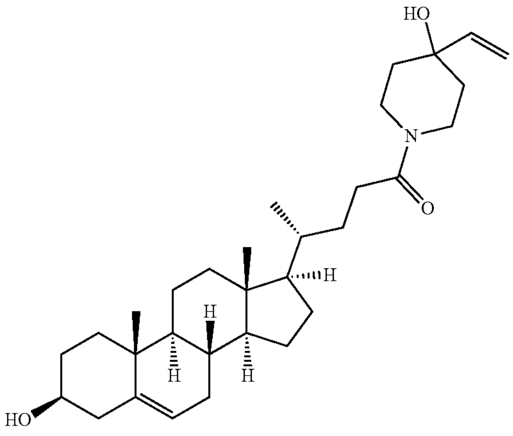

146

To a solution of compound A (1.0 g, 5.02 mmol) in tetrahydrofuran (20 mL) was added vinylmagnesium bromide (6.5 mL, 6.5 mmol, 1M in THF) at −78° C., then the mixture was warmed to room temperature and stirred for 16 h. After completion, to the mixture was added potassium sodium tartrate tetrahydrate solution and extracted with ethyl acetate (30 mL×3). The organic layer was washed with brine, dried over sodium sulfate, filtered, and concentrated to give the crude product that was purified by column chromatography to afford compound B (380 mg, 26%).

To a solution of compound B (380 mg, 1.67 mmol) in DCM (10 mL) was added TFA (2 mL) at room temperature. After stirring at room temperature for 30 minutes, the mixture was concentrated to afford compound C (120 mg, 56%).

To a solution of compound D (290 mg, 774 μmol) and compound C (120 mg, 943 μmol) in DMF (8 mL) was added HATU (735 mg, 1.93 mmol) and DIEA (1.25 g, 10 eq, 9.67 mmol) at room temperature and stirred for 16 h. The mixture was diluted with water and extracted with ethyl acetate (50 ml×3). The combined organic layer was washed with brine, dried over sodium sulfate, filtered, and concentrated to give the crude product that was purified by column chromatography to afford compound 146 as white solid (145 mg, 31%). $^1$H NMR (400 MHz, DMSO-$d_6$) δ 5.90 (dd, J=17.3, 10.7 Hz, 1H), 5.26 (d, J=4.9 Hz, 1H), 5.19 (dd, J=17.3, 1.8 Hz, 1H), 4.97 (dd, J=10.7, 1.8 Hz, 1H), 4.66 (s, 1H), 4.58 (d, J=4.6 Hz, 1H), 4.07 (d, J=12.8 Hz, 1H), 3.60 (d, J=13.4 Hz, 1H), 3.34 (s, 3H), 3.24 (p, J=5.2 Hz, 1H), 3.00-2.82 (m, 1H), 2.31 (ddd, J=15.4, 10.2, 5.6 Hz, 1H), 2.21-2.15 (m, 3H), 2.02-1.86 (m, 2H), 1.85-0.97 (m, 24H), 0.94 (s, 3H), 0.90 (d, J=6.4 Hz, 3H), 0.64 (s, 3H).

Example 147: (R)-1-(4-ethynyl-4-hydroxypiperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl) pentan-1-one

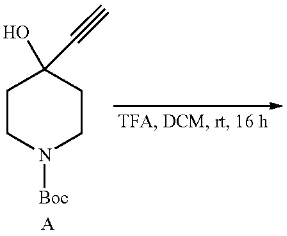

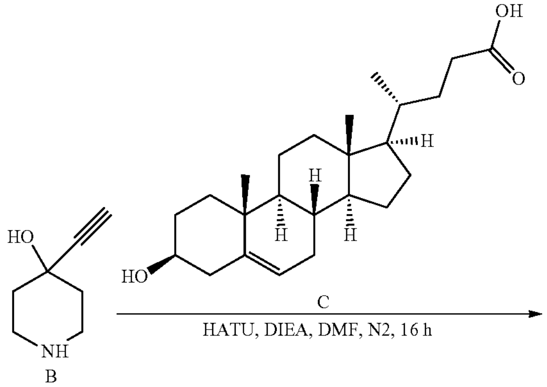

-continued

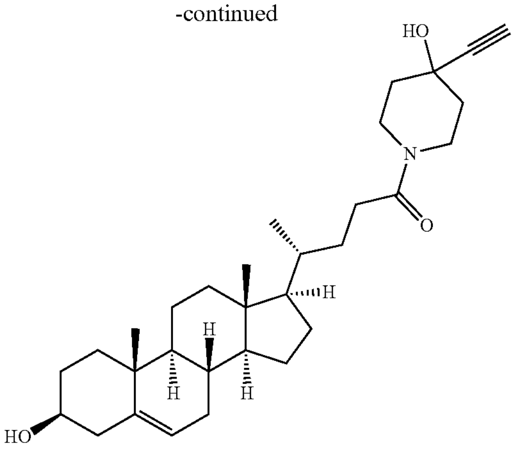

147

To a solution of A (50 mg, 222 μmol) in DCM (2 mL) was added TFA (0.2 mL). The mixture was stirred at room temperature for 16 h. TLC showed a major new spot was found. The mixture was concentrated to afford the compound B (40 mg) as a white solid.

To a solution of crude compound B (26.2 mg, 209 μmol) in DMF (3 mL) were added C (78.5 mg, 209 μmol), HATU (159 mg, 2 eq, 419 μmol) and DIEA (162 mg, 6 eq, 1.26 mmol). The mixture was stirred at room temperature under $N_2$ for 16 h. TLC showed SM disappeared, a major new spot was found. The reaction mixture was diluted with water (40 mL) and extracted with ethyl acetate (50 mL). The organic layer was washed by brine, dried over sodium sulfate, filtered, and concentrated. The residue was purified by column chromatography to afford compound 147 (55 mg, yield: 54.5%) as a white solid. $^1$H NMR (400 MHz, $CDCl_3$) δ 5.35 (d, J=4.9 Hz, 1H), 4.08-3.95 (m, 1H), 3.73-3.63 (m, 1H), 3.58-3.48 (m, 1H), 3.40 (t, J=11.5 Hz, 2H), 2.56 (s, 1H), 2.43-2.33 (m, 1H), 2.33-2.15 (m, 3H), 2.05-1.02 (m, 29H), 1.01 (s, 3H), 0.95 (d, J=6.5 Hz, 3H), 0.68 (s, 3H).

Example 148: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-hydroxy-4-propylpiperidin-1-yl) pentan-1-one

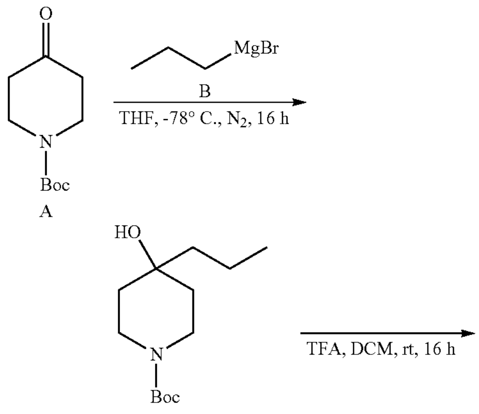

A

C

-continued

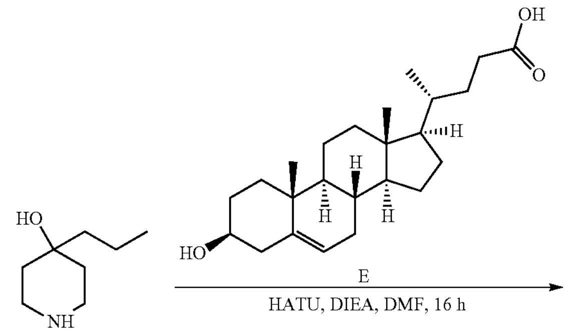

D

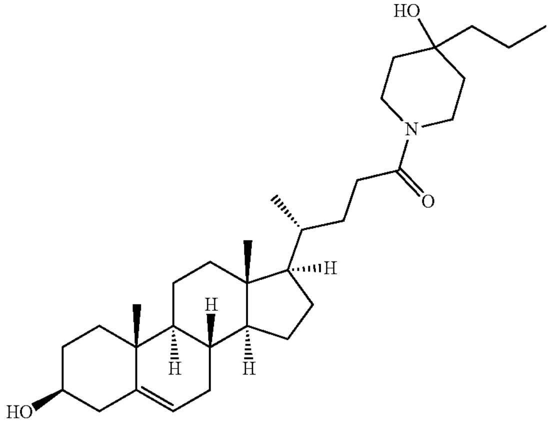

148

To a solution of A (300 mg, 1.51 mmol) in tetrahydrofuran (5 mL) at −78° C. under $N_2$ was added B (4.5 mL, 4.5 mmol, 3 eq. 1M in THF). The mixture was stirred at room temperature under $N_2$ for 16 h. The reaction was quenched with $NH_4Cl_{aq}$ (200 mL) and extracted with ethyl acetate (100 mL). The organic layer was washed by brine, dried over sodium sulfate, filtered, and concentrated. The residue was purified by column chromatography to afford compound C (100 mg, yield: 27.3%) as a yellow oil.

To a solution of compound C (50 mg, 205 μmol) in DCM (2 mL) was added TFA (0.2 mL). The mixture was stirred at room temperature for 16 h. The reaction mixture was concentrated to afford the compound D (40 mg) as a yellow solid.

To a solution of crude compound D (40 mg, 279 μmol) in DMF (4 mL) were added E (126 mg, 1.2 eq, 335 μmol), HATU (212 mg, 2 eq, 559 μmol), and DIEA (217 mg, 6 eq, 1.68 mmol), the mixture was stirred at room temperature under $N_2$ for 16 h. The reaction mixture was diluted with water (40 mL) and extracted with ethyl acetate (50 mL). The organic layer was washed by brine, dried over sodium sulfate, filtered, and concentrated. The mixture was purified by column chromatography to afford compound 148 (65 mg, yield: 38.6%) as a white solid. $^1$H NMR (400 MHz, $CDCl_3$) δ 5.35 (s, 1H), 4.31 (s, 1H), 3.68-3.34 (m, 3H), 3.03 (s, 1H), 2.44-2.16 (m, 5H), 1.98 (t, J=7.6 Hz, 2H), 1.91-1.70 (m, 5H), 1.65-1.23 (m, 23H), 1.21-0.88 (m, 16H), 0.68 (s, 3H).

Example 149: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-hydroxy-4-isopropylpiperidin-1-yl) pentan-1-one

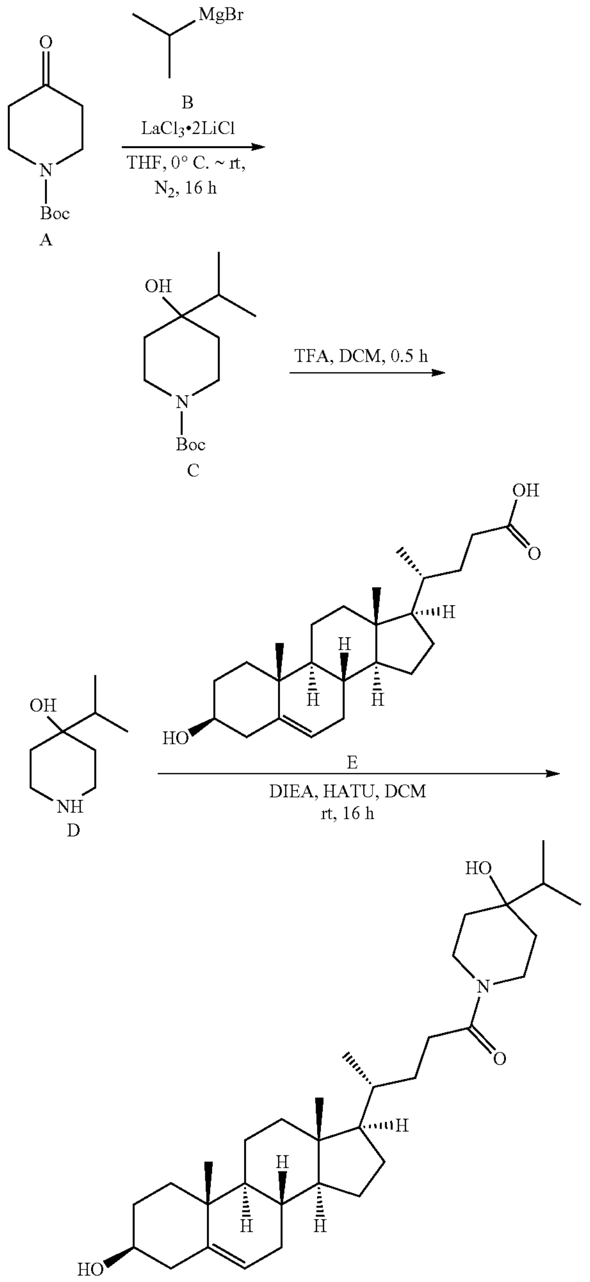

149

Lanthanum trichloride lithium chloride complex (12.5 mL, 3 eq, 7.5 mmol, 0.6 M in THF) was placed in a 100 mL 3-neck round bottom flask under $N_2$, then compound B (7.53 mL, 7.53 mmol, 1 M in THF) was added slowly at 0° C. After stirring at room temperature for 3 h, a solution of compound A (500 mg, 2.51 mmol) in tetrahydrofuran (5 mL) was added. The mixture was stirred at room temperature for 16 h. After completion, the reaction was quenched with acetic acid (0.3 mL), diluted with $H_2O$ (30 mL), and extracted with ethyl acetate (20 mL×3). The combined organic phases were washed with brine, dried over sodium sulfate, filtered, and concentrated in vacuo and the residue was purified by silica gel chromatography to compound afford C (520 mg 85%) as a brown solid.

To a solution of compound C (50 mg, 205 μmol) in dichloromethane (2 mL) was added TFA (0.2 mL). The solution was stirred at room temperature for 30 mins. After completion, the reaction mixture was concentrated to afford compound D (28 mg, 95%).

To a solution of compound D (60 mg, 419 μmol) in dichloromethane (4 mL) was added DIEA (108 mg, 2 eq, 838 μmol), HATU (478 mg, 3 eq, 1.26 mmol), and compound E (157 mg, 419 μmol). After stirring at room temperature for 16 h, the reaction mixture was diluted with water (10 mL) and extracted with ethyl acetate (10 mL×3). The combined organic phases were washed with brine, dried over sodium sulfate, filtered, concentrated in vacuo, and the residue was purified by column chromatography to afford compound 149 (40 mg, 20%) as a white solid. 1H NMR (400 MHz, $CDCl_3$) δ 5.35 (d, J=4.5 Hz, 1H), 4.47 (d, J=13.0 Hz, 1H), 3.67 (d, J=13.4 Hz, 1H), 3.51 (q, J=9.9, 7.8 Hz, 1H), 3.40 (s, 1H), 2.94 (d, J=15.4 Hz, 1H), 2.50-2.14 (m, 5H), 2.08-1.04 (m, 33H), 1.01 (s, 3H), 0.96 (d, J=6.3 Hz, 4H), 0.92 (d, J=6.9 Hz, 6H), 0.68 (s, 3H).

Example 150: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-hydroxy-4-(hydroxymethyl)piperidin-1-yl)pentan-1-one

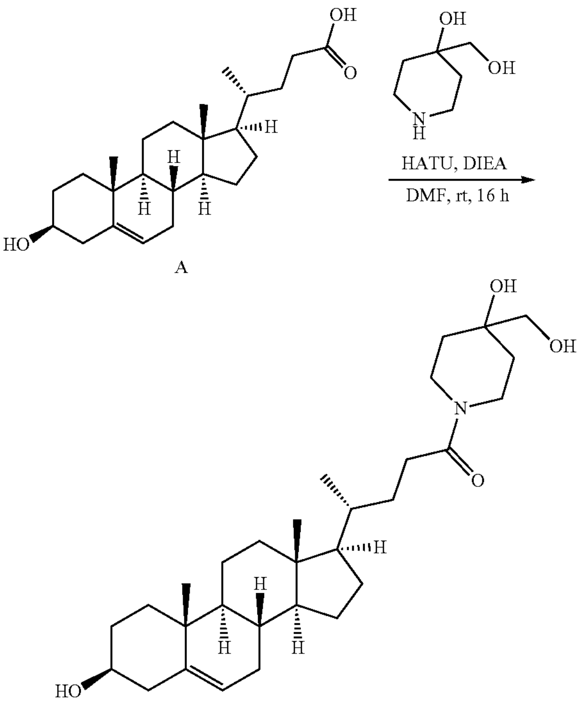

150

To a solution of compound A (100 mg, 0.27 mmol) in dimethylformamide (2 mL) was added 4-(hydroxymethyl)piperidin-4-ol (35 mg, 0.27 mmol), DIEA (174.8 mg, 1.35 mmol), and HATU (205.4 mg, 0.54 mmol). The mixture was stirred at room temperature for 16 h. The reaction was quenched with water and extracted with ethyl acetate. The organic layer was concentrated to give crude product that was purified by column chromatography to yield compound 150 (30 mg, 26.9%). $^1$H NMR (400 MHz, DMSO-$d_6$) δ 5.26 (d, J=4.8 Hz, 1H), 4.58 (d, J=5.0 Hz, 2H), 4.24 (s, 1H), 4.10 (d, J=12.9 Hz, 1H), 3.60 (d, J=13.2 Hz, 1H), 3.18 (d, J=5.6 Hz, 4H), 2.90-2.80 (m, 1H), 2.34-2.24 (m, 1H), 2.22-2.16 (m, 1H), 2.14-2.04 (m, 2H), 1.96 (d, J=13.5 Hz, 2H), 1.76 (dd, J=9.8, 6.5 Hz, 2H), 1.66 (s, 2H), 1.56-1.44 (m, 4H), 1.38-0.96 (m, 13H), 0.94 (s, 3H), 0.90 (d, J=6.4 Hz, 3H), 0.66 (s, 3H).

Example 151: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(2,2-difluoroethyl)-4-hydroxypiperidin-1-yl]pentan-1-one

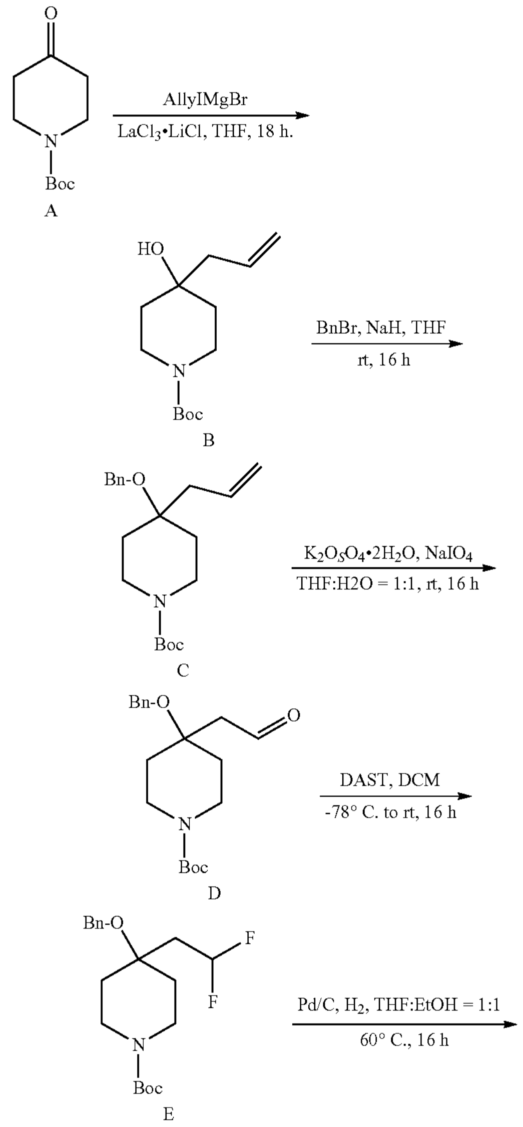

-continued

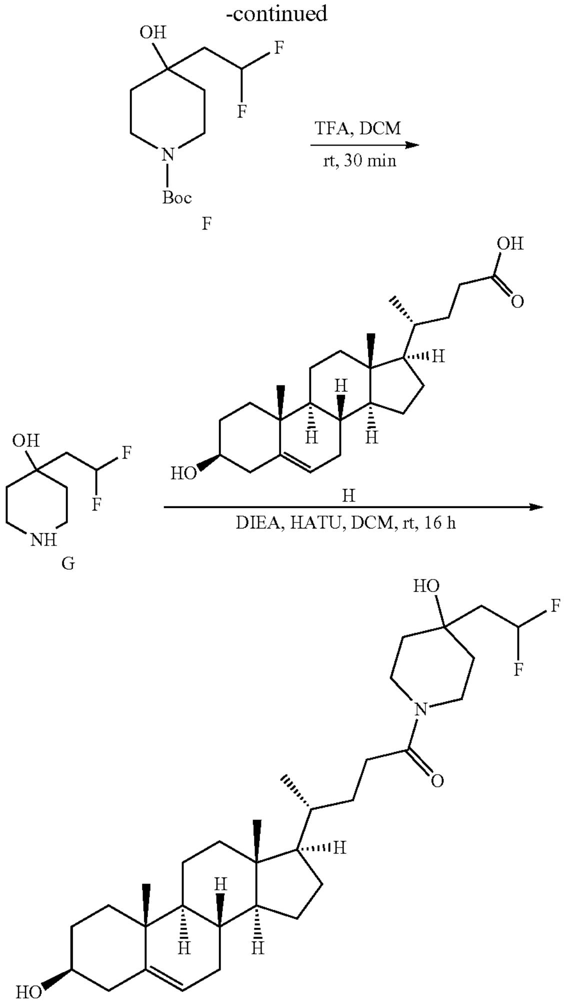

151

To a solution of compound A (1.5 g, 2.51 mmol) in THF (15 mL) was added lanthanum trichloride lithium chloride complex (8.4 mL, 2 eq, 5.0 mmol, 0.6 M in THF) and allylmagnesium bromide (5 mL, 2 eq, 5.0 mmol, 1 M in THF) at 0° C. After stirring at room temperature for 18 h, the mixture was quenched with water and extracted with ethyl acetate. The combined organic phases were washed with brine, dried over sodium sulfate, filtered, and concentrated in vacuo to afford compound B (1.9 g, 78%).

To a solution of compound B (1.5 g, 0.96 eq, 6.22 mmol) in THF (40 mL) were added benzyl bromide (3.33 g, 3 eq, 19.5 mmol) and sodium hydride (747 mg, 3 eq, 19.5 mmol) at −78° C. under $N_2$ atmosphere. The mixture was warmed to room temperature and stirred 16 h. After completion, the reaction solution was quenched with water and extracted with ethyl acetate. The organic phase was concentrated in vacuo to afford the crude product that was purified by column chromatography to give compound C (1.54 g, 71%).

To a solution of compound C (1.3 g, 3.92 mmol) in THF (5 mL) and water (5 mL) were added $K_2OsO_4 \cdot 2H_2O$ (143 mg, 0.39 mmol) and NaIO4 (516 mg, 4 eq, 2.41 mmol) at 0° C. The mixture was stirred at room temperature under $N_2$ atmosphere 16 h. After completion, the reaction was quenched with water and extracted with ethyl acetate. The organic phase was concentrated in vacuo to afford the crude product that was purified by column chromatography to give compound D (1.1 g, 84%).

To a solution of compound D (1.06 g, 3.18 mmol) in DCM (10 mL) was added diethyl(trifluoro-$\lambda^4$-sulfanyl)amine (840 μL, 2 eq, 6.36 mmol) at −78° C. under $N_2$ atmosphere. The mixture was stirred at room temperature for 16 h under $N_2$ atmosphere. After completion, the solvent was concentrated in vacuo and the residue was purified by column chromatography to give compound E (419 mg, 37%).

To a solution of compound E (419 mg, 1.18 mmol) in THF (2 mL) and ethanol (2 mL) was added Pd/C (41.9 mg, 10% weight) at room temperature. Then the mixture was stirred at 60° C. for 16 h under 1 atm of $H_2$. After completion, the mixture was filtered and the solvent was concentrated in vacuo to afford the crude product that was purified by column chromatography to give compound F (277 mg, 88%).

To a solution of compound F (60 mg, 226 μmol) in DCM (10 mL) was added trifluoroacetic acid (1 mL). Then the reaction mixture was stirred at room temperature for 30 mins. After completion, the solvent was concentrated in vacuo to afford crude compound G (80 mg).

To a solution of crude compound G (80 mg, 238 μmol) and compound H (44.6 mg, 0.5 eq, 119 μmol) in DCM (3 mL) were added HATU (271 mg, 3 eq, 714 μmol) and DIEA (184 mg, 6 eq, 1.43 mmol). The reaction mixture was stirred at room temperature for 16 h. After completion, the reaction mixture was diluted with water and extracted with ethyl acetate. The organic phase was concentrated in vacuo to afford the crude product that was purified by column chromatography to give compound 151 (57 mg, 45%). $^1$H NMR (400 MHz, $CDCl_3$) δ 6.12 (tt, J=55.8, 4.6 Hz, 1H), 5.45-5.35 (m, 1H), 4.33 (d, J=13.4 Hz, 1H), 3.64 (d, J=13.7 Hz, 1H), 3.60-3.40 (m, 2H), 3.11 (t, J=11.6 Hz, 1H), 2.49-1.05 (m, 38H), 1.04 (s, 3H), 0.98 (d, J=6.5 Hz, 4H), 0.71 (s, 3H).

Example 152: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-hydroxy-4-(2,2,2-trifluoroethyl) piperidin-1-yl) pentan-1-one

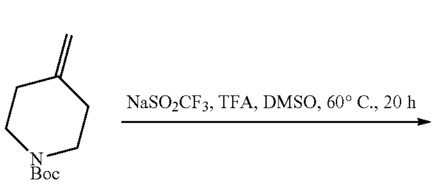

A

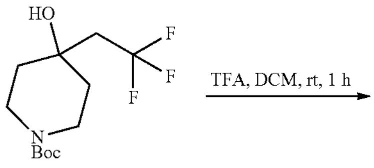

B

-continued

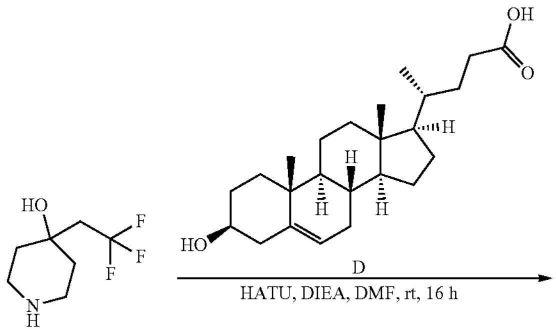

C D

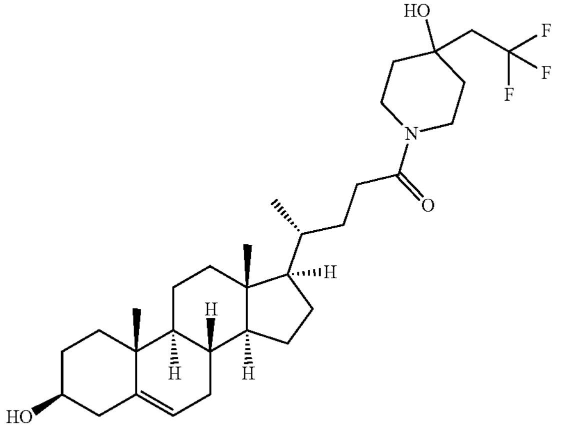

152

To a solution of compound A (2.0 g, 10.1 mmol) in DMSO (50 mL) were added sodium trifluoromethanesulfinate (3.16 g, 20.3 mmol) and trifluoroacetic acid (2.31 g, 20.3 mmol). The mixture was stirred at 60° C. for 20 h. After completion, to the mixture was added $H_2O$ and it was extracted with ethyl acetate. The organic phase was concentrated to give the crude product that was purified by silica gel chromatography to give compound B (270 mg, 953 μmol).

To a solution of compound B (100 mg, 353 μmol) in dichloromethane (1 mL) was added trifluoroacetic acid (250 μL). The mixture was stirred at room temperature for 1 h then concentrated to give compound C (50 mg, 77%).

A solution of crude compound C (50 mg, 273 μmol), compound D (92 mg, 246 μmol), HATU (311 mg, 819 μmol), and DIPEA (106 mg, 819 μmol) in DMF (4 mL) was stirred at room temperature for 16 h. The mixture was diluted with $H_2O$ and extracted with ethyl acetate. The organic phase was concentrated to give the crude product that was purified by silica gel chromatography to give compound 152 (30 mg, 55.6 μmol). $^1$H NMR (400 MHz, $CDCl_3$) δ 5.35 (d, J=5.0 Hz, 1H), 4.40 (d, J=13.7 Hz, 1H), 3.65 (d, J=13.6 Hz, 1H), 3.58-3.39 (m, 2H), 3.01 (t, J=12.7 Hz, 1H), 2.44-2.17 (m, 6H), 2.08-1.70 (m, 10H), 1.70-1.04 (m, 22H), 1.01 (s, 3H), 0.95 (d, J=6.6 Hz, 3H), 0.68 (s, 3H).

Example 153: (S)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethyl 2-(ethyl(methyl)amino)-2-oxoacetate

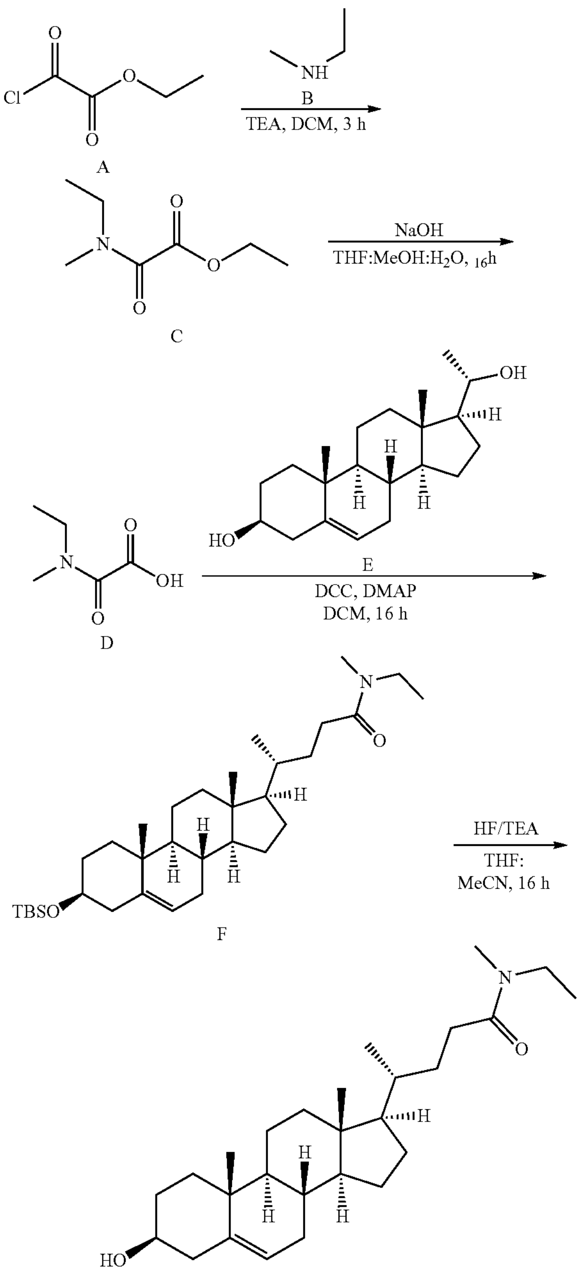

153

To a solution of compound B (727 μL, 8.46 mmol) in DCM (5 mL) were added TEA (2.35 mL, 16.9 mmol) and compound A (1.04 mL, 9.3 mmol) at 0° C. The mixture was stirred at 0° C. for 3 h. After completion, the reaction was quenched by the addition of water and extracted with DCM. The combined organic layers were dried over sodium sulfate and concentrated to give the crude product that was purified by column chromatography to give compound C (1.2 g, 89%) as colorless oil.

To a solution of compound C (1.2 g, 7.54 mmol) in the mixture of THE (5 mL), methanol (5 mL) and water (5 mL) was added sodium hydroxide (905 mg, 22.6 mmol) at room temperature. The mixture was stirred for 16 h. After completion, the reaction was quenched by the addition of water, then adjusted to pH 3 with HCl (1M) and extracted with DCM. The combined organic layers were dried over sodium sulfate and concentrated to give compound D (800 mg, 81%) as a white solid.

To a solution of compound E (250 mg, 578 μmol) in DCM (5 mL) were added compound D (227 mg, 1.73 mmol), DMAP (14.2 mg, 116 μmol), and DCC (596 mg, 2.89 mmol) at room temperature. The mixture was stirred for 16 h. After completion, the solvent was evaporated to give the crude product that was purified by column chromatography to give compound F as a white solid (300 mg, 95%).

To a solution of compound F (100 mg, 183 μmol) in THF (5 mL) and MeCN (5 mL) was added trihydrogen triethylamine trifluoride (0.3 mL). The mixture was stirred at room temperature for 16 h. After completion, the reaction was quenched by the addition of water and extracted with DCM. The combined organic layers were dried over sodium sulfate and concentrated to give the crude product that was purified by column chromatography to afford compound 153 (50.1 mg, 53%) as a white solid. $^1$H NMR (400 MHz, $CDCl_3$) δ 5.35 (d, J=5.2 Hz, 1H), 5.19-5.06 (m, 1H), 3.58-3.39 (m, 2H), 3.37-3.23 (m, 1H), 2.95 (d, J=8.4 Hz, 3H), 2.37-2.16 (m, 2H), 2.04-1.78 (m, 6H), 1.78-1.39 (m, 14H), 1.35 (dd, J=6.3, 2.2 Hz, 4H), 1.32-1.03 (m, 13H), 1.01 (s, 3H), 0.98-0.79 (m, 3H), 0.73 (s, 3H).

Example 154: (1S)-1-[(1S,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]ethyl (diethylcarbamoyl)formate

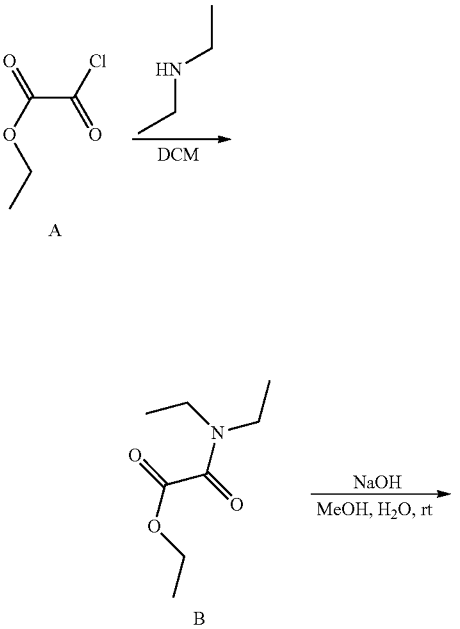

-continued

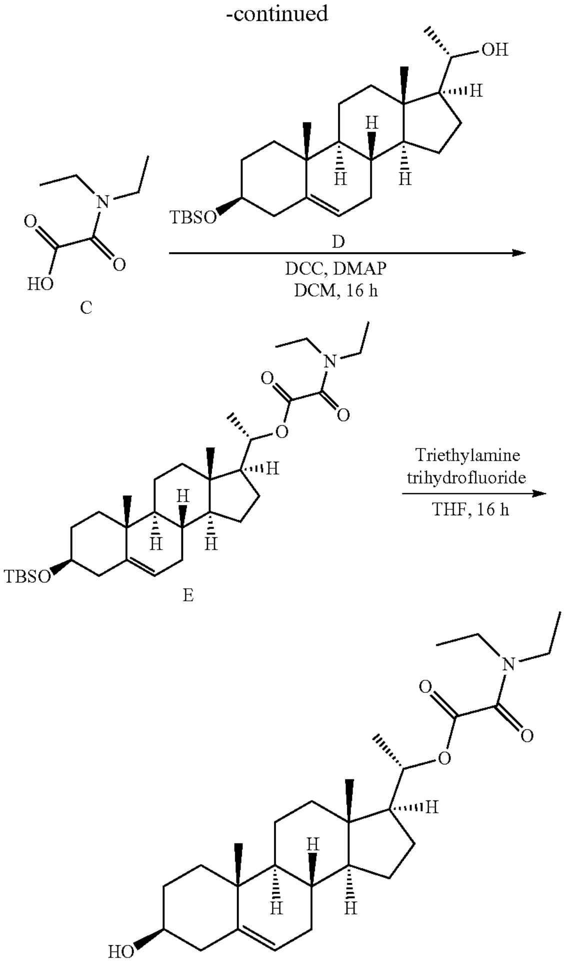

C
D
E
154

To a solution of compound A (1.2 g, 8.94 mmol) in dichloromethane (35 mL) was added diethylamine (654 mg, 8.94 mmol) dropwise at 0° C. The mixture was stirred at room temperature for 3 h. After completion, the mixture was diluted with water and extracted with ethyl acetate. The organic phase was dried with sodium sulfate, filtered, and concentrated in vacuo to give compound B (950 mg, 61.4%).

A mixture of compound B (950 mg, 5.48 mmol) and sodium hydroxide (877 mg, 21.9 mmol) in methanol (20 mL) and water (5 mL) was stirred at room temperature for 3 h. After completion, the pH was adjusted to 2 with 1 M HCl. The resulting mixture was extracted with ethyl acetate. The combined organic phase was dried with sodium sulfate, filtered, and concentrated in vacuo to give compound C (800 mg, 100 mmol).

To a solution of compound D (200 mg, 462 μmol) in dichloromethane (10 mL) were added 4-(dimethylamino) pyridin-1-ium (11.4 mg, 92.4 μmol), compound C (201 mg, 1.39 mmol), and N,N'-dicyclohexylmethanediimine (210 mg, 1.02 mmol) at room temperature. The mixture was stirred at room temperature for 16 h. After completion, the solvent was removed under vacuum, and the crude product was purified by column chromatography (eluting with 1/3/0.1 ethyl acetate/petroleum ether/MeOH) to give compound E (130 mg, 50.2%).

To a solution of compound E (100 mg, 179 μmol) in THE (2.5 mL) was added trihydrogen trifluoride triethylamine (250 μL). The mixture was stirred for 16 h at room temperature. After completion, the reaction was diluted with water and extracted with ethyl acetate. The organic phase was washed with water and brine, dried with sodium sulfate, and concentrated in vacuo. The residue was purified by column chromatography (eluting with 1/4 ethyl acetate/petroleum ether) to give compound 154 (25.2 mg, 31.6%). $^1H$ NMR (400 MHz, $CDCl_3$) δ 5.35 (s, 1H), 5.11 (d, J=7.4 Hz, 1H), 3.52 (s, 1H), 3.47-3.37 (m, 2H), 3.28 (d, J=7.2 Hz, 2H), 2.33-2.22 (m, 2H), 1.96 (s, 1H), 1.94-1.85 (m, 3H), 1.83 (s, 1H), 1.65 (d, J=9.2 Hz, 3H), 1.47 (d, J=12.8 Hz, 3H), 1.35 (d, J=6.4 Hz, 4H), 1.30-1.13 (m, 12H), 1.01 (s, 3H), 0.73 (s, 3H). LCMS: $[M+H]^+$=446.30.

Example 155: (1S)-1-[(1S,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]ethyl 2-(azetidin-1-yl)-2-oxoacetate

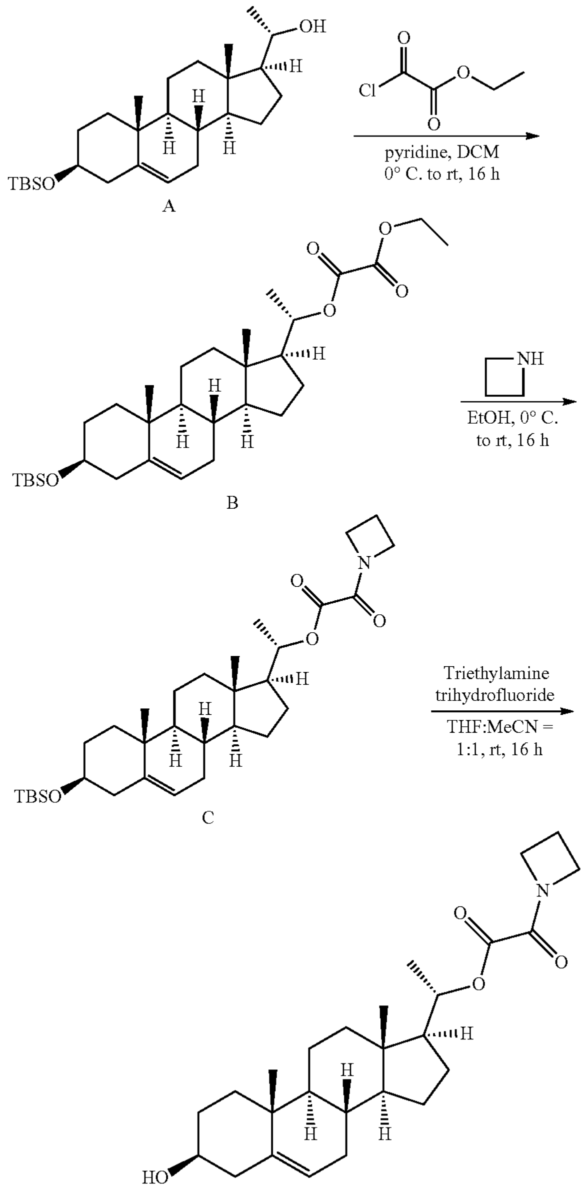

A
B
C
155

To a solution of compound A (500 mg, 1.16 mmol) in dichloromethane (5 mL) was added pyridine (101 mg, 1.1 eq, 1.27 mmol) and ethyl oxalochloridate (174 mg, 1.1 eq, 1.27 mmol) under 0° C. The reaction was stirred at room temperature for 16 h. After completion, the mixture was diluted with water and extracted with ethyl acetate. The organic phase was concentrated in vacuo and the residue was purified by column chromatography (petroleum ether/ethyl acetate=80/1) to afford compound B (550 mg, 97.3%).

To a solution of compound B (200 mg, 0.35 mmol) in ethanol (2 mL) was added azetidine (5.36 mg, 93.8 μmol). The mixture was stirred at room temperature for 16 h. After completion, the solvent was concentrated in vacuo to afford the crude product that was purified by column chromatography to give compound C (163 mg, 84.8%) as a white solid.

To a solution of compound C (80 mg, 147 μmol) in THE (0.5 mL) and acetonitrile (0.5 mL) was added trihydrogen triethylamine trifluoride (0.1 mL). The mixture was stirred at room temperature overnight. After completion, the mixture was diluted with water and extracted with ethyl acetate. The organic layer was concentrated in vacuo and the residue was purified by column chromatography to yield compound 155 (39 mg, 61.9%).$^{1}$H NMR (400 MHz, $CDCl_3$) δ 5.35 (d, J=4.9 Hz, 1H), 5.06 (dq, J=9.3, 6.3 Hz, 1H), 4.49 (td, J=7.6, 4.0 Hz, 2H), 4.13 (t, J=7.9 Hz, 2H), 3.51 (ddd, J=10.7, 5.5, 4.6 Hz, 1H), 2.39-2.17 (m, 4H), 2.04-1.80 (m, 5H), 1.74-1.61 (m, 2H), 1.55-1.38 (m, 6H), 1.32 (d, J=6.2 Hz, 3H), 1.26-1.03 (m, 5H), 1.00 (s, 3H), 0.95 (dt, J=11.4, 5.8 Hz, 1H), 0.71 (s, 3H).

Example 156: (R)-4-((1S,3R,8S,9S,10R,13R,14S,17R)-1,3-dihydroxy-10,13-dimethyl-2,3,4,7,8,9,10,11,12,13,14,15,16,17-tetradecahydro-1H-cyclopenta[a]phenanthren-17-yl)-1-(4-ethyl-4-hydroxypiperidin-1-yl)pentan-1-one

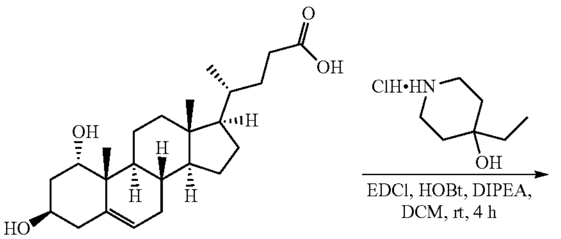

A

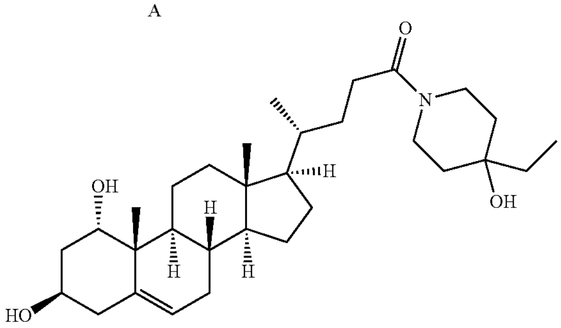

156

A solution of compound A (50 mg, 128 μmol), 4-ethylpiperidin-4-ol hydrochloride (31.8 mg, 1.5 eq, 192 μmol), EDCI (37.2 mg, 1.5 eq, 192 μmol), HOBT (29.2 mg, 1.5 eq, 192 μmol), and ethylbis(propan-2-yl)amine (82.7 mg, 5 eq, 640 μmol) in dichloromethane (5 mL) was stirred at room temperature under $N_2$ atmosphere 4 h. After completion, the mixture was diluted with water (20 mL) and extracted with DCM (300 mL×3). The combined organic layers were washed with brine (10 mL), dried over sodium sulfate, and concentrated in vacuo to give the crude product that was purified by column chromatography (DCM:MeOH=20:1) to give compound 156 (11.5 mg, 22.9 μcool, 18%).1H NMR (400 MHz, $CDCl_3$) δ 5.63 (d, J=5.3 Hz, 1H), 4.48-4.31 (m, 1H), 4.02 (tt, J=10.9, 5.0 Hz, 1H), 3.88 (d, J=3.0 Hz, 1H), 3.74-2.96 (m, 5H), 2.53-2.18 (m, 6H), 2.18-1.73 (m, 9H), 1.57-1.43 (m, 16H), 1.42-1.09 (m, 13H), 1.07 (s, 3H), 1.01-0.90 (m, 7H), 0.72 (s, 3H).

Examples 157 and T5

Example 157: (R)-4-((3S,8S,9S,10R,11S,13R,14S,17R)-3,11-dihydroxy-10,13-dimethyl-2,3,4,7,8,9,10,11,12,13,14,15,16,17-tetradecahydro-1H-cyclopenta[a]phenanthren-17-yl)-N, N-dimethylpentanamide Example T5: (R)-4-((3S,5S,8S,9S,10S,11S,13R,14S,17R)-3,11-dihydroxy-10,13-dimethylhexadecahydro-1H-cyclopenta[a]phenanthren-17-yl)-N, N-dimethylpentanamide

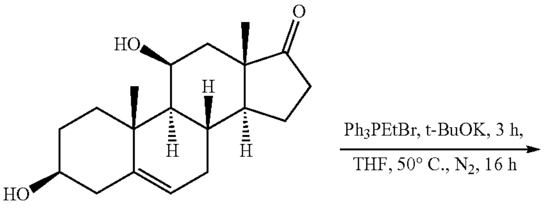

A

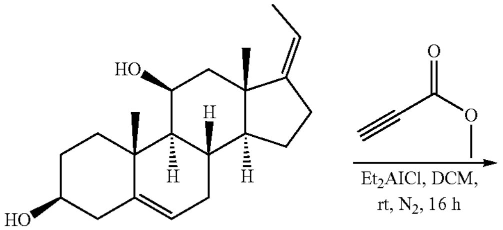

B

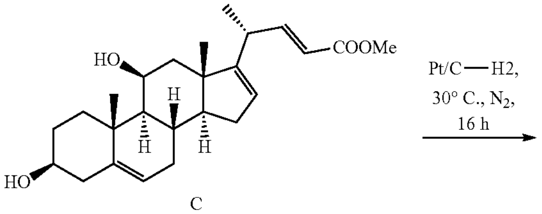

C

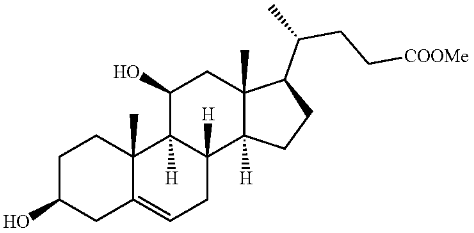

D1

-continued

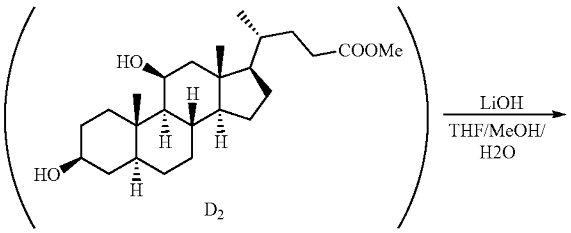

D2

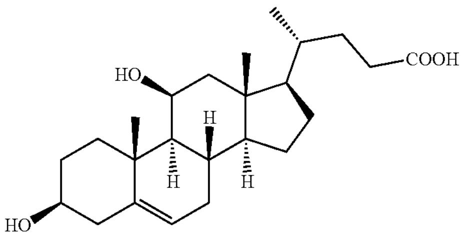

E1

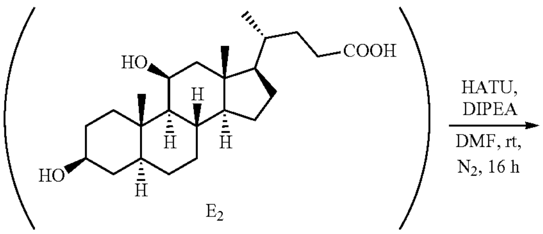

E2

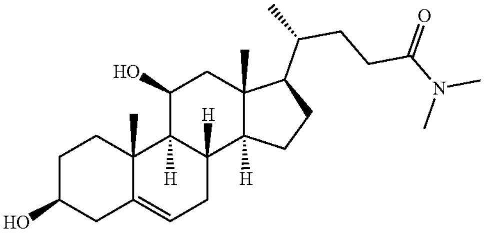

157

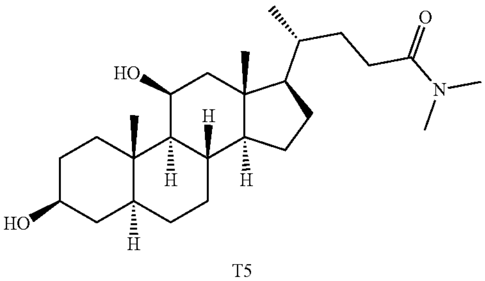

T5

The solution of bromo(ethyl)triphenyl-%$^{5}$-phosphane (61 g, 10 eq, 164 mmol) and tBuOK (18.4 g, 10 eq, 164 mmol) in THF (200 mL) was stirred at 50° C. under $N_2$ atmosphere for 3 h, then compound A (5.0 g, 1.0 eq, 16.4 mmol) was added and the mixture was stirred for 16 h. After completion, the reaction was quenched with saturated solution of $NH_4Cl$ (aq.) and extracted with ethyl acetate. The combined organic layers were washed with brine, dried over sodium sulfate, concentrated in vacuo, and the residue was purified column chromatography (petroleum ether/ethyl acetate=100/1-petroleum ether/ethyl acetate=3/1, v/v) to give compound B (2.56 g, 8.09 mmol, 50%) as a white solid.

To a stirred solution of compound B (2.46 g, 1.0 eq, 7.77 mmol) and methyl prop-2-ynoate (1.96 g, 3 eq, 23.3 mmol) in dichloromethane (30 mL) under $N_2$ at 0° C. was added $Et_2AlCl$ (23.3 mL, 23.3 mmol, 3 eq. 1M in hexanes). The mixture was stirred at room temperature for 16 h. After completion, the reaction was quenched with $NH_4Cl$ (aq.) and extracted with DCM. The organic layer was concentrated in vacuo and the residue was purified by column chromatography with ethyl acetate/petroleum ether=1/10 to give compound C (1.7 g, 4.24 mmol, 55%) as an off-white solid.

A mixture of compound C (200 mg, 3.37 mmol) and Pt/C (20 mg, 10% weight) in ethyl acetate (2 mL) and methanol (4 mL) was stirred under 1 atm of $H_2$ atmosphere at 30° C. for 16 h. After completion, the mixture was filtered and concentrated in vacuo to give the mixture of compounds D1 and D2 (180 mg, D1:D2=3:2, 90% in total).

A solution of D1 and D2 (50 mg, D1:D2=3:2, 124 μmol) and LiOH (8.9 mg, 3 eq, 371 μmol) in tetrahydrofuran (1 mL), methanol (1 mL), and water (1 mL) was stirred at room temperature 16 h. After completion, the mixture was concentrated in vacuo, the residue was treated with HCl (1M, 100 ml) and filtered to give compounds E1 and E2 (30 mg, E1:E2=3:2, 77 μmol, 62% in total).

To a stirred solution of compounds E1 and E2 (30 mg, E1:E2=3:2, 77 μmol) and DIPEA (65.8 mg, 4 eq, 309 μmol) in DMF (2 mL) were added dimethyl amine (13.9 mg, 4 eq. 0.309 mmol), and HATU (44 mg, 1.5 eq, 116 μmol) at room temperature under $N_2$ atmosphere. The mixture was stirred for 16 h. After completion, the reaction was diluted with ethyl acetate and washed with $NH_4C1$, water and brine. The organic layer was concentrated in vacuo and the residue was purified by Prep-HPLC to give compound 157 (12 mg, 28.7 μmol, 37%) and the title compound T5 (9.6 mg, 22.9 μmol, 30%).

157: $^1$H NMR (400 MHz, $CDCl_3$) δ 5.24 (s, 1H), 4.34 (d, J=3.5 Hz, 1H), 3.61-3.46 (m, 1H), 3.01 (s, 3H), 2.94 (s, 3H), 2.47-2.08 (m, 7H), 2.01 (d, J=13.0 Hz, 1H), 1.93-1.72 (m, 5H), 1.55 (s, 1H), 1.50-1.41 (m, 2H), 1.33 (t, J=9.9 Hz, 3H), 1.27 (s, 5H), 1.23-1.01 (m, 5H), 0.96 (d, J=6.5 Hz, 3H), 0.92 (s, 3H).LCMS: [M+Na]=440.3.

T5: $^1$H NMR (400 MHz, DMSO-$d_6$) δ 4.37 (d, J=4.7 Hz, 1H), 4.07 (s, 1H), 3.89 (d, J=3.0 Hz, 1H), 3.29 (s, 1H), 2.94 (s, 3H), 2.78 (s, 3H), 2.33-2.01 (m, 3H), 1.85-1.43 (m, 7H), 1.34 (s, 13H), 0.95 (s, 3H), 0.90 (d, J=6.5 Hz, 3H), 0.82 (s, 3H), 0.54 (dd, J=10.7, 3.3 Hz, 1H). LCMS: [M+Na]=442.4.

Examples 158 and T7

Example 158: (R)-4-((3S,8S,9S,10R,11S,13R,14S,17R)-3,11-dihydroxy-10,13-dimethyl-2,3,4,7,8,9,10,11,12,13,14,15,16,17-tetradecahydro-1H-cyclopenta[a]phenanthren-17-yl)-1-(4-ethyl-4-hydroxypiperidin-1-yl)pentan-1-one Example T7: (R)-4-((3S,5S,8S,9S,10S,11S,13R,14S,17R)-3,11-dihydroxy-10,13-dimethylhexadecahydro-1H-cyclopenta[a]phenanthren-17-yl)-1-(4-ethyl-4-hydroxypiperidin-1-yl)pentan-1-one To a stirred solution of compounds E1 and E2 (see Example 157) (200 mg, 0.51 mmol, 1 eq.), 4-ethylpiperidin-4-ol hydrochloride (127 mg, 1.5 eq, 0.768 mmol) and ethylbis(propan-2-yl)amine (265 mg, 4 eq, 2.05 mmol) in DMF (5 mL) was added HATU (292 mg, 1.5 eq, 0.768 mmol) under $N_2$ atmosphere. After stirring for 16 h, the mixture was diluted with ethyl acetate and washed with saturated $NH_4Cl$, water, and brine. The organic layer was concentrated in vacuo and the residue was purified by Prep-HPLC to afford compounds 158 (17 mg, 34 μmol, 7%) as an off-white solid and T7 (96 mg, 191 μmol, 37.5%) as white solid.

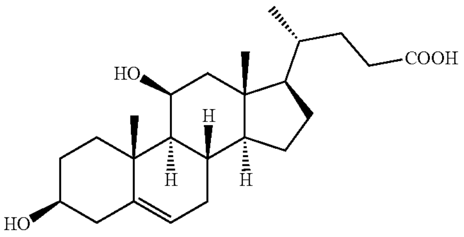

E1

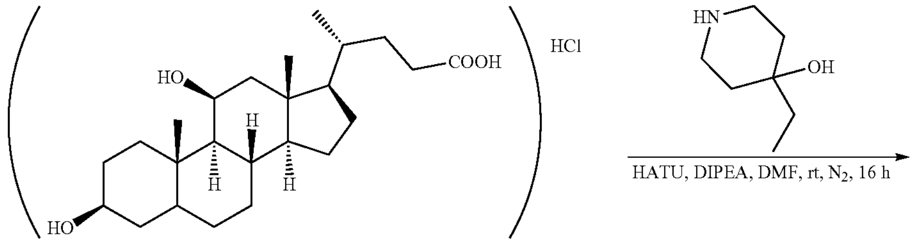

E2

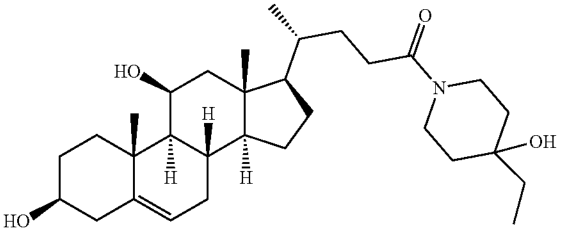

158

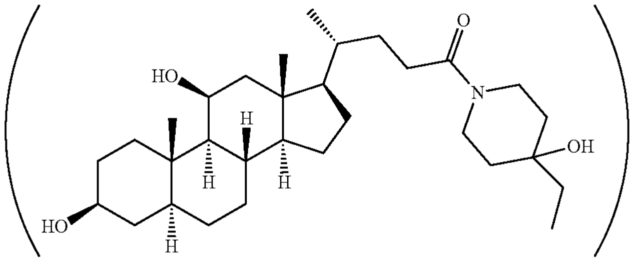

T7

158: $^{1}H$ NMR (400 MHz, $CDCl_3$) δ 5.24 (s, 1H), 4.34 (d, J=3.8 Hz, 2H), 3.69-3.36 (m, 3H), 3.02 (s, 1H), 2.43-2.33 (m, 1H), 2.29 (d, J=8.0 Hz, 2H), 2.23-2.09 (m, 3H), 2.03-1.98 (m, 1H), 1.87 (dt, J=10.4, 4.6 Hz, 3H), 1.77 (s, 1H), 1.56-1.42 (m, 11H), 1.35-1.21 (m, 9H), 1.18-1.03 (m, 4H), 0.99-0.87 (m, 11H).

T7: $^{1}H$ NMR (400 MHz, $CDCl_3$) δ 4.33 (s, 1H), 4.26 (d, J=3.3 Hz, 1H), 3.58 (tt, J=10.7, 4.9 Hz, 2H), 3.41 (s, 1H), 3.02 (s, 1H), 2.35 (d, J=12.9 Hz, 1H), 2.22 (s, 1H), 2.13 (dd, J=14.1, 2.7 Hz, 1H), 1.94-1.68 (m, 6H), 1.68-1.20 (m, 19H), 1.17-1.05 (m, 4H), 1.04 (s, 3H), 1.02-0.90 (m, 7H), 0.89 (s, 3H), 0.68 (dd, J=11.2, 3.3 Hz, 1H).

Example 159: (3S,8S,9S,10R,13R,14S,17R)-10,13-dimethyl-17-((R)-4-(pyridin-3-yl)butan-2-yl)-2,3,4,7,8,9,10,11,12,13,14,15,16,17-tetradecahydro-1H-cyclopenta[a]phenanthren-3-ol

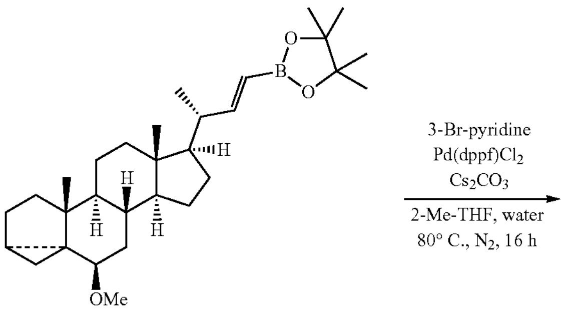

A

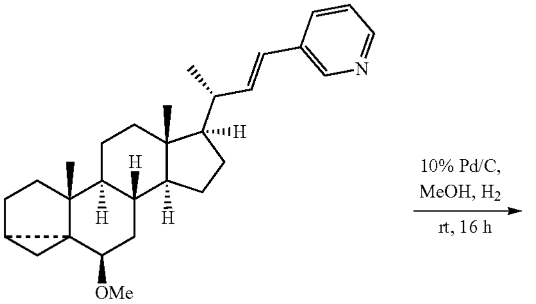

B

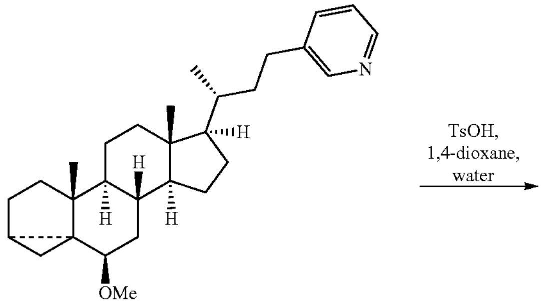

C

-continued

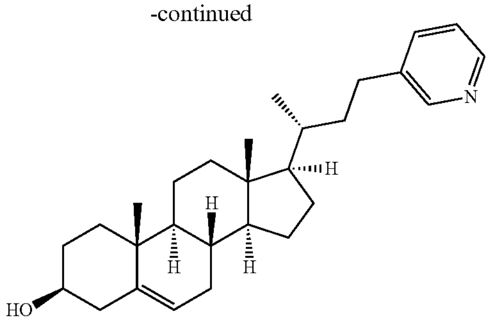

159

To a solution of compound A (100 mg, 213 μmol) in 2-methyltetrahydrofuran (2 mL) and water (0.3 mL) were added 3-bromopyridine (43.8 mg, 277 μmol), $Cs_2CO_3$ (174 mg, 534 μmol), and Pd(dppf)$Cl_2$ (31.2 mg, 42.7 μmol). After stirring at 80° C. for 16 h under nitrogen, the reaction was quenched with water and extracted with ethyl acetate. The organic layer was dried over sodium sulfate, filtered, and concentrated to give the crude product that was purified by column chromatography to give compound B (67 mg 74.8%) as white solid. LCMS:$[M+H]^+$=419.77.

To a solution of compound B (60 mg, 143 μmol) in methanol (8.57 mL) was added Pd/C (6 mg, 10% weight). The mixture was stirred at room temperature for 16 h under 1 atm of hydrogen. After completion, the mixture was filtered and concentrated to give compound C (54 mg, 89.57%). LCMS:$[M+H]^+$=421.77.

To a solution of compound C (54 mg, 135 μmol) in 1,4-dioxane (0.5 mL) and water (0.1 mL) was added 4-methylbenzene-1-sulfonic acid (4.66 mg, 27 μmol). The mixture was stirred at 80° C. for 16 h under nitrogen. After completion, the mixture was washed with $NaHCO_3$ and extracted with ethyl acetate. The organic layer was dried over sodium sulfate, filtered, and concentrated to give the crude product that was purified by column chromatography on to yield compound 159 (39 mg, 70.78%) as a white solid. $^{1}H$ NMR (400 MHz, $CDCl_3$) δ 8.52-8.42 (m, 2H), 7.68 (d, J=7.9 Hz, 1H), 7.38 (dd, J=7.9, 5.1 Hz, 1H), 5.36 (d, J=5.1 Hz, 1H), 3.50 (d, J=13.7 Hz, 1H), 2.78-2.69 (m, 1H), 2.54 (dt, J=8.1, 5.2 Hz, 1H), 2.32-2.20 (m, 2H), 2.00 (t, J=3.6 Hz, 2H), 1.88-1.80 (m, 3H), 1.78-1.66 (m, 2H), 1.54 (s, 2H), 1.48 (dd, J=11.8, 4.7 Hz, 4H), 1.42 (d, J=6.1 Hz, 3H), 1.28-1.11 (m, 5H), 1.06-1.02 (m, 6H), 0.94 (dt, J=11.3, 5.8 Hz, 1H), 0.68 (s, 3H). LCMS:$[M+H]^+$=408.20.

Example 160: (3S,8S,9S,10R,13R,14S,17R)-10,13-dimethyl-17-((R)-4-(pyridin-4-yl)butan-2-yl)-2,3,4,7,8,9,10,11,12,13,14,15,16,17-tetradecahydro-1H-cyclopenta[a]phenanthren-3-ol

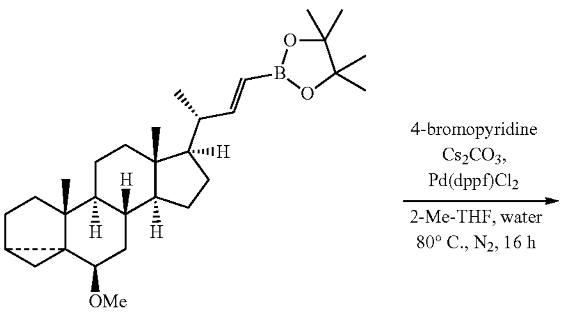

A

-continued

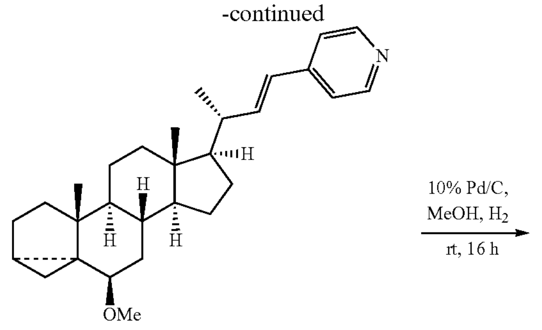

B

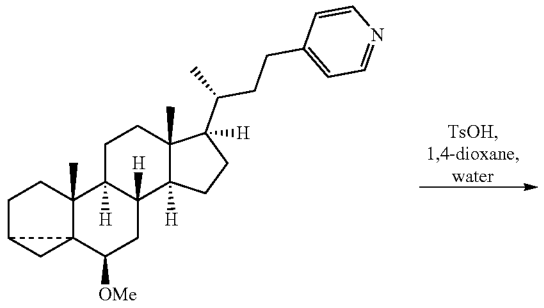

C

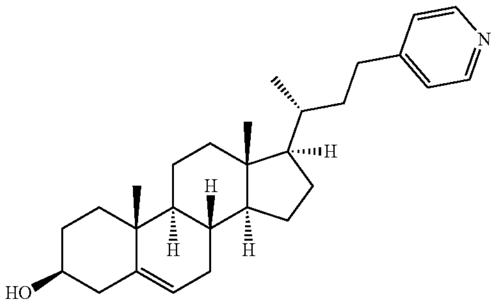

160

To a solution of compound A (100 mg, 213 μmol) in 2-methyltetrahydrofuran (2 mL) and water (0.3 mL) were added 4-bromopyridine (43.8 mg, 277 μmol), cesium carbonate (174 mg, 534 μmol), and Pd(dppf)$Cl_2$ (31.2 mg, 42.7 μmol). The mixture was stirred at 80° C. for 16 h under nitrogen. After completion, the mixture was diluted with water and extracted with ethyl acetate. The combined organic layer was dried over sodium sulfate, filtered, and concentrated to give the crude product that was purified by column chromatography to give compound B (75 mg, 83.7%). LCMS: $[M+H]^+$=419.77.

To a solution of compound B (75 mg, 179 μmol) in methanol (5 mL) was added Pd/C (7.5 mg, 10% weight). The mixture was stirred at room temperature for 16 h under 1 atm of hydrogen. After completion, the mixture was filtered and concentrated in vacuo to afford compound C (54 mg, 71%) as a white solid. LCMS:$[M+H]^+$=421.77.

To a solution of compound C (54 mg, 135 μmol) in 1,4-dioxane (0.5 mL) and water (0.1 mL) was added 4-methylbenzene-1-sulfonic acid (4.66 mg, 27 μmol). The mixture was stirred at 80° C. for 3 h under nitrogen. After completion, the reaction was quenched with saturated $NaHCO_3$ and extracted with ethyl acetate. The organic layer was dried over sodium sulfate, filtered, and concentrated to give the crude product that was purified by column chromatography to yield compound 160 (32 mg, 61%) as a white solid. $^1H$ NMR (400 MHz, $CDCl_3$) δ 8.48 (s, 2H), 7.12 (d, J=4.8 Hz, 2H), 5.35 (s, 1H), 3.53 (s, 1H), 2.74-2.65 (m, 1H), 2.48 (dd, J=19.8, 10.4 Hz, 1H), 2.33-2.19 (m, 3H), 2.00 (t, J=15.8 Hz, 3H), 1.85 (d, J=11.4 Hz, 3H), 1.48-1.41 (m, 4H), 1.35-0.99 (m, 12H), 0.67 (s, 3H).

Example 161: (3S,8S,9S,10R,13R,14S,17R)-17-((R)-4-(6-fluoropyridin-2-yl)butan-2-yl)-10,13-dimethyl-2,3,4,7,8,9,10,11,12,13,14,15,16,17-tetradecahydro-1H-cyclopenta[a]phenanthren-3-ol

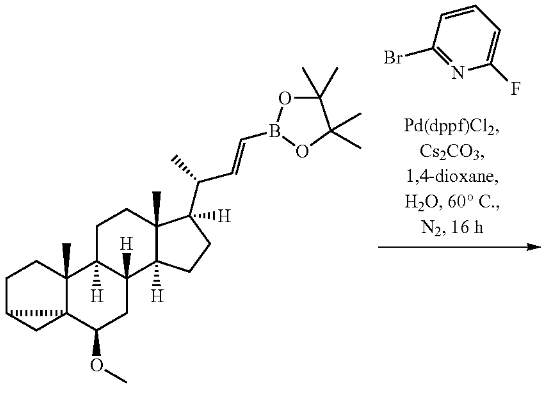

A

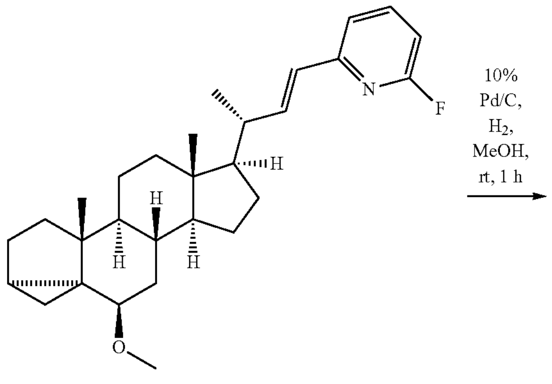

B

-continued

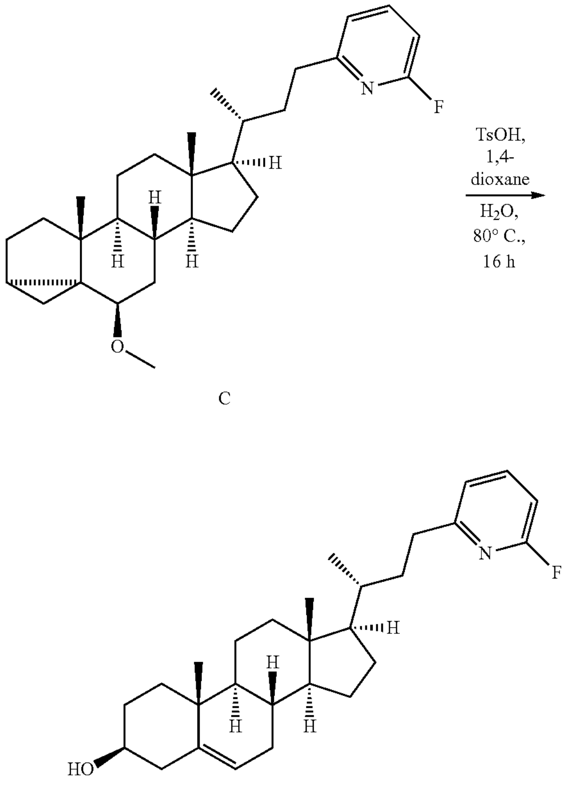

C

161

To a solution of compound A (180 mg, 384 μmol) in 1,4-dioxane (7 mL) and water (1 PGP-193,C3 mL) were added 2-bromo-6-fluoropyridine (67.6 mg, 384 μmol), cesium carbonate (313 mg, 960 μmol), and $Pd(dppf)Cl_2$ (28 mg, 0.1 eq, 38 umol). The mixture was stirred at 60° C. for 16 h under $N_2$. The mixture was diluted $H_2O$ (20 mL) and extracted with ethyl acetate (15 mL×3). The combined organic phases were washed with brine, dried over sodium sulfate, concentrated in vacuo, and the residue was purified by column chromatography to afford compound B (120 mg, 71%).

To a solution of compound B (100 mg, 228 μmol) in methanol (4 mL) was added Pd/C (10 mg, 10% weight). The mixture was stirred at room temperature for 1 h under 1 atm of $H_2$. After completion, the reaction solution was filtered and concentrated in vacuo to afford compound C (80 mg, 80%).

To a solution of compound C (80 mg, 182 μmol) in 1,4-dioxane (4 mL) and water (1 mL) was added 4-methylbenzene-1-sulfonic acid (6.27 mg, 0.2 eq, 36.4 μmol). After stirring at 80° C. for 16 h under $N_2$, the mixture concentrated in vacuo and the residue was purified by column chromatography to afford compound 161 (10 mg, 13%) as a white solid. $^1H$ NMR (400 MHz, $CDCl_3$) δ 7.66 (q, J=8.0 Hz, 1H), 7.00 (dd, J=7.4, 2.4 Hz, 1H), 6.72 (dd, J=8.1, 2.8 Hz, 1H), 5.35 (d, J=5.2 Hz, 1H), 3.52 (tt, J=10.7, 4.7 Hz, 1H), 2.80 (ddd, J=13.1, 11.1, 4.4 Hz, 1H), 2.60 (ddd, J=13.5, 10.4, 5.9 Hz, 1H), 2.37-2.20 (m, 2H), 2.12-1.75 (m, 7H), 1.63-1.53 (m, 3H), 1.45 (dt, J=12.7, 6.4 Hz, 3H), 1.34-0.88 (m, 17H), 0.68 (s, 3H). $^{19}F$ NMR (376 MHz, $CDCl_3$) δ -67.80.

Example 162: (1R,3aS,3bS,7S,9aR,9bS,11aR)-1-[(2R)-4-(5-fluoropyridin-2-yl)butan-2-yl]-9a,11a-dimethyl-1H,2H,3H,3aH,3bH,4H,6H,7H,8H,9H,9aH,9bH,10H,11H,11aH-cyclopenta[a]phenanthren-7-ol

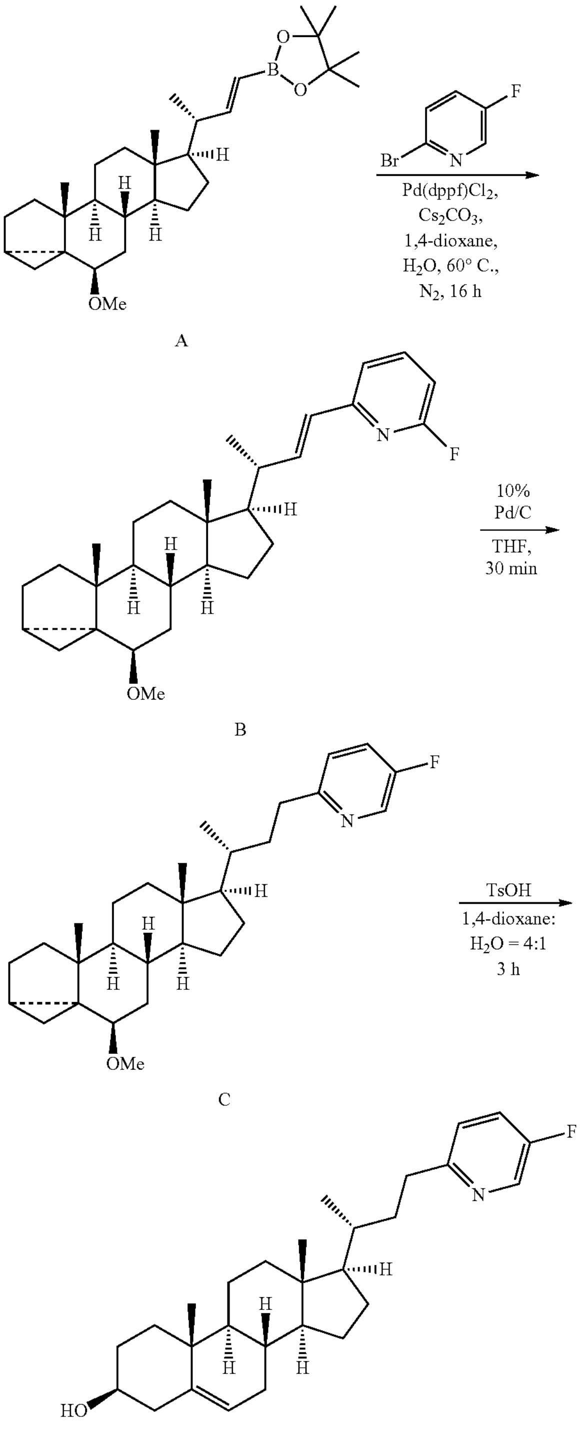

A

B

C

162

To a solution of compound A (200 mg, 427 μmol) in the mixture of 1,4-dioxane (7.5 mL) and water (1.5 mL) were added sodium carbonate (113 mg, 1.07 mmol), 2-bromo-5-fluoropyridine (82.6 mg, 470 µmol), and Pd(dppf)$Cl_2$ (31 mg, 42.7 µmol). The mixture was heated at 90° C.; for 2 h under $N_2$ and then cooled to ambient temperature. The mixture was filtered through Celite, and the filtrate was concentrated in vacuo. Then residue was purified by column chromatography (eluting with 1/20 ethyl acetate/petroleum ether) to give compound B (80 mg, 42.8%).

To a solution of compound B (80 mg, 183 µmol) in THE (2 mL) was added Pd/C (8 mg, 10% weight). The mixture was purged with hydrogen three times and stirred for 30 mins at room temperature under 1 atm of $H_2$. After completion, the mixture was filtered through Celite and concentrated in vacuo to give compound C (51 mg, 63.5%).

A mixture of compound C (51 mg, 116 µmol) and 4-methylbenzene-1-sulfonic acid hydrate (4.41 mg, 23.2 µmol) in 1,4-dioxane (2 mL) and water (0.5 mL) was heated at reflux for 3 h under an atmosphere of $N_2$. After completion, the mixture was adjusted pH to 7 with saturated $NaHCO_3$ solution and extracted with ethyl acetate. The organic phase was dried over anhydrous sodium sulfate and concentrated in vacuo to give the crude product that was purified by column chromatography (eluting with 1/15 ethyl acetate/petroleum ether) to afford the title compound 162 (25.2 mg, 31.6%).$^1$H NMR (400 MHz, $CDCl_3$) δ 8.36 (d, J=2.8 Hz, 1H), 7.32 (d, J=3.4 Hz, 1H), 7.13 (d, J=6.0 Hz, 1H), 5.34 (d, J=4.8 Hz, 1H), 3.52 (d, J=3.8 Hz, 1H), 2.91-2.80 (m, 1H), 2.73-2.60 (m, 1H), 2.34-2.17 (m, 2H), 2.05-1.78 (m, 9H), 1.62-1.45 (m, 5H), 1.30-1.05 (m, 7H), 1.00 (d, J=2.8 Hz, 8H), 0.67 (d, J=2.6 Hz, 3H). $^{19}$F NMR (376 MHz, $CDCl_3$) δ−131.82. LCMS: $[M+H]^+$=426.25.

Example 163: (3S,8S,9S,10R,13R,14S,17R)-17-((R)-4-(4-fluoropyridin-2-yl)butan-2-yl)-10,13-dimethyl-2,3,4,7,8,9,10,11,12,13,14,15,16,17-tetradecahydro-1H-cyclopenta[a]phenanthren-3-ol

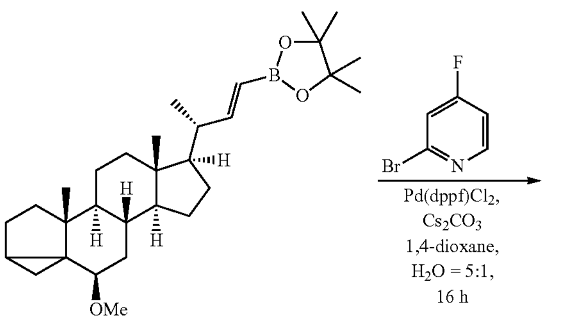

A

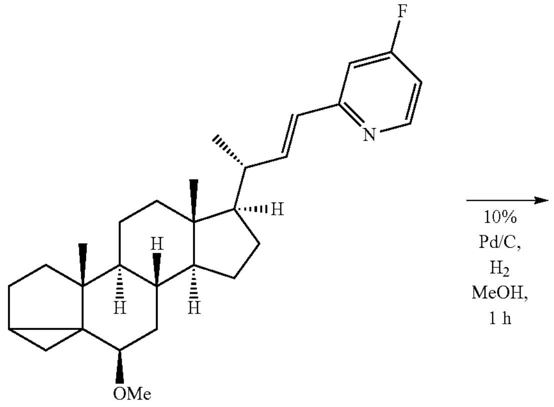

C

-continued

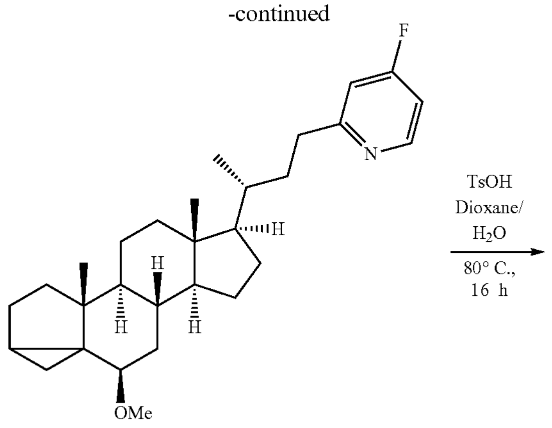

D

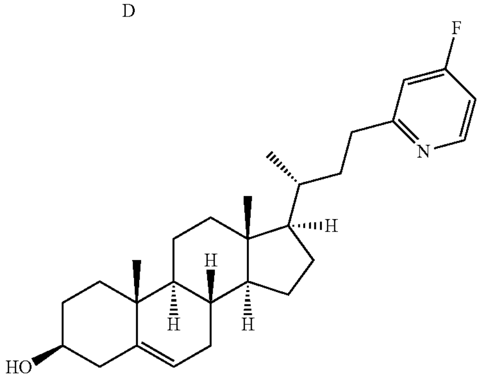

163

To a solution of compound A (180 mg, 384 µmol) and compound B (67.6 mg, 384 µmol) in 1,4-dioxane (5 mL) and water (1 mL) were added Pd(dppf)$Cl_2$ (27.9 mg, 0.1 eq, 38.4 µmol) and cesium carbonate (376 mg, 3 eq, 1.15 mmol) at room temperature. After stirring at 65° C. for 16 h under $N_2$, the mixture was diluted with water and extracted with ethyl acetate. The combined organic phase was washed with brine, dried over sodium sulfate, and concentrated in vacuo. The residue was purified by silica gel chromatography (petroleum ether/ethyl acetate=50/1, v/v) to afford compound C (100 mg, 228 µmol) as a yellow solid.

To a solution of compound C (90 mg, 206 µmol) in methanol (4 mL) was added Pd/C (9.0 mg, 10% weight) at room temperature After stirring for 1 h under 1 atm of $H_2$, the mixture was filtered, and the filtrate was concentrated in vacuo to afford compound D (85 mg, 193 µmol) as a yellow solid.

To a solution of compound D (85 mg, 197 µmol) in 1,4-dioxane (4 mL) and water (1 mL) was added 4-methylbenzene-1-sulfonic acid (9.4 mg, 0.2 eq, 54.6 µmol) at room temperature After stirring at 80° C. for 16 h, the mixture was diluted with water and extracted with ethyl acetate. The combined organic phases were washed with brine, dried over sodium sulfate, and concentrated in vacuo. The residue was purified by column chromatography (DCM/MeOH=50/1, v/v) to afford compound 163 (15.4 mg, 36.2 µmol) as a yellow solid. $^1$H NMR (400 MHz, $CDCl_3$) δ 8.51 (dd, J=8.8, 5.7 Hz, 1H), 6.89 (td, J=9.3, 8.2, 5.1 Hz, 2H), 5.38 (d, J=5.1 Hz, 1H), 3.57 (d, J=13.9 Hz, 1H), 2.96-2.84 (m, 1H), 2.78-2.64 (m, 1H), 2.43-2.21 (m, 2H), 2.14-1.80 (m, 7H), 1.63 (t, J=9.7 Hz, 2H), 1.47 (d, J=5.2 Hz, 2H), 1.42-0.89 (m, 17H), 0.71 (s, 3H).$^{19}$F NMR (376 MHz, $CDCl_3$) δ−103.47.

Example 164: (3S,8S,9S,10R,13R,14S,17R)-17-((R)-4-(3-fluoropyridin-2-yl)butan-2-yl)-10,13-dimethyl-2,3,4,7,8,9,10,11,12,13,14,15,16,17-tetradecahydro-1H-cyclopenta[a]phenanthren-3-ol

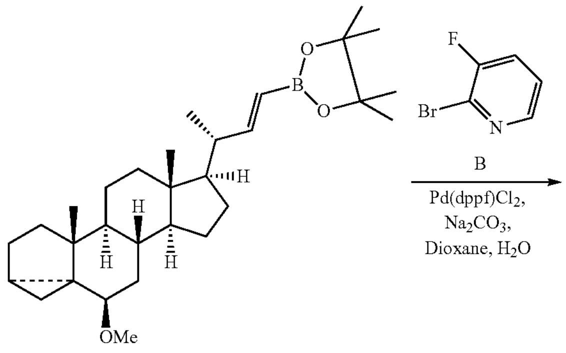

A

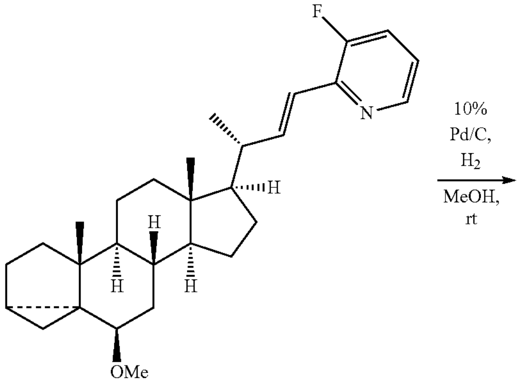

C

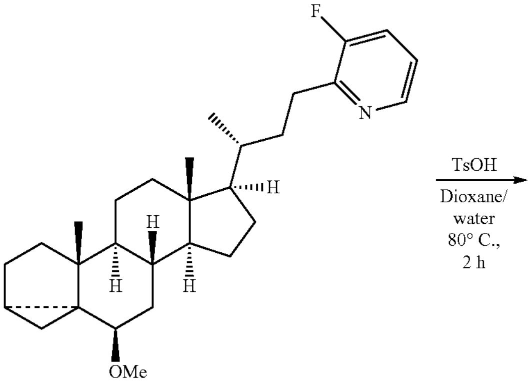

D

-continued

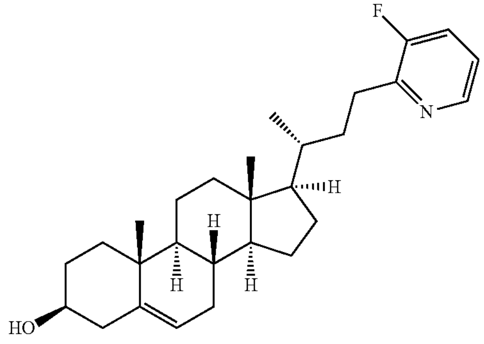

164

To a solution of compound A (150 mg, 320 μmol) in 1,4-dioxane (5 mL) and water (1 mL) were added compound B (67.6 mg, 384 μmol), Pd(dppf)$Cl_2$ (23.2 mg, 32 μmol) and sodium carbonate (84.8 mg, 0.8 mmol) at room temperature. The mixture was stirred at 60° C. for 4 h. The resultant solution was evaporated to afford the crude product that was purified by column chromatography to give compound C (100 mg, 71%) as a white solid.

To a solution of compound C (100 mg, 228 μmol) in MeOH (3 mL) was added Pd/C (10 mg, 10% weight) at room temperature. The mixture was stirred for 16 h under 1 atm of $H_2$. After completion, the solvent was evaporated to afford the crude product that was purified by column chromatography to give compound D (70 mg, 50%) as a white solid.

To a solution of compound D (70 mg, 159 μmol) in 1,4-dioxane (3.0 mL) and water (1.0 mL) was added 4-methylbenzene-1-sulfonic acid (5.48 mg, 31.8 μmol) at room temperature. The mixture was stirred at 80° C. for 2 h. The reaction was quenched by the addition of $NaHCO_3$ and extracted with DCM (50 mL×3). The combined organic layer was dried over sodium sulfate and concentrated to give the crude product that was purified by column chromatography to yield compound 164 (7.8 mg, 12%). $^1$H NMR (400 MHz, $CDCl_3$) δ 8.33 (d, J=4.8 Hz, 1H), 7.32 (t, J=9.0 Hz, 1H), 7.13 (dt, J=8.4, 4.4 Hz, 1H), 5.35 (d, J=5.2 Hz, 1H), 3.52 (dt, J=11.6, 6.2 Hz, 1H), 2.92 (td, J=12.4, 7.0 Hz, 1H), 2.76 (m, 1H), 2.36-2.14 (m, 2H), 2.00 (m, 2H), 1.85 (m, 4H), 1.53-1.40 (m, 8H), 1.34-1.24 (m, 4H), 1.23-1.10 (m, 3H), 1.01 (s, 3H), 0.98-0.83 (m, 2H), 0.68 (s, 3H). $^{19}$F NMR (376 MHz, $CDCl_3$) δ −125.73. LCMS: $[M+H]^+$=426.25.

Example 165: (3S,8S,9S,10R,13R,14S,17R)-17-((R)-4-(6-chloropyridin-2-yl)butan-2-yl)-10,13-dimethyl-2,3,4,7,8,9,10,11,12,13,14,15,16,17-tetradecahydro-1H-cyclopenta[a]phenanthren-3-ol

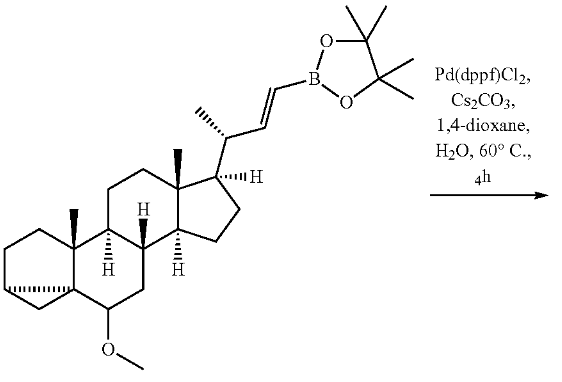

A

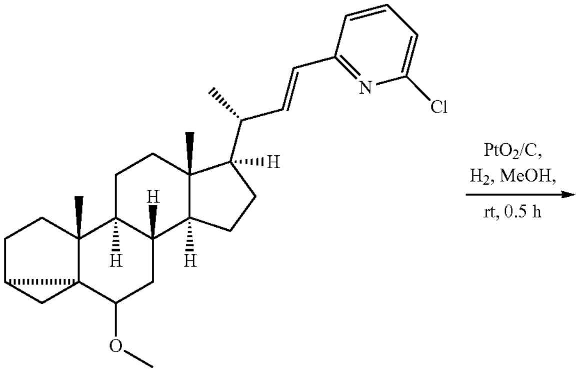

B

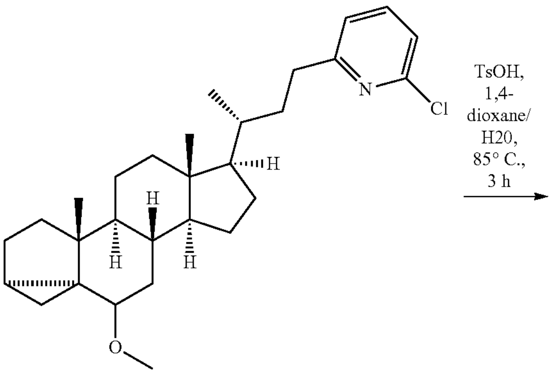

C

-continued

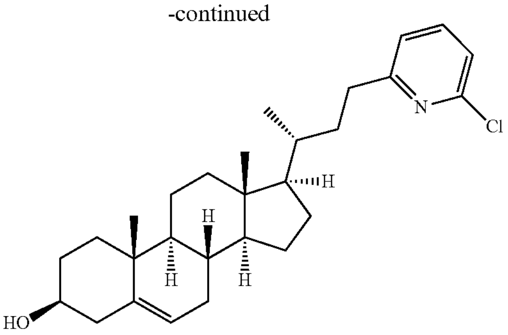

165

A solution of compound A (100 mg, 213 μmol), 2-bromo-6-chloropyridine (45.2 mg, 235 μmol), $Pd(dppf)Cl_2$ (15.5 mg, 21.3 μmol) and $Cs_2CO_3$ (104 mg, 320 μmol) in 1,4-dioxane (5 mL) and water (1 mL) was stirred at 60° C. for 4 h under an inert atmosphere. After completion, the mixture was concentrated to give the crude product that was purified by silica gel chromatography to give compound B (90 mg, 93%).

A mixture of compound B (90 mg, 198 μmol) and $PtO_2$ (18 mg, 20% weight) in methanol (3 mL) was stirred at room temperature for 30 mins under 1 atm of $H_2$ atmosphere. The mixture was filtered and concentrated to give the crude product that was purified by column chromatography to give compound C (26 mg, 29%).

To a solution of compound C (26 mg, 57 μmol) in 1,4-dioxane (1 mL) and water (0.2 mL) was added 4-methylbenzene-1-sulfonic acid (1.96 mg, 11.4 μmol). The mixture was stirred at 85° C. for 3 h. After completion, the mixture was concentrated to give the crude product that was purified by Prep-HPLC to afford compound 165 (3.5 mg, 14%) as a white solid. $^1H$ NMR (400 MHz, $CDCl_3$) δ 7.53 (t, J=7.6 Hz, 1H), 7.13 (d, J=7.8 Hz, 1H), 7.05 (d, J=7.6 Hz, 1H), 5.35 (d, J=5.0 Hz, 1H), 3.58-3.45 (m, 1H), 2.90-2.79 (m, 1H), 2.71-2.57 (m, 1H), 2.33-2.20 (m, 2H), 2.02 (d, J=13.6 Hz, 2H), 1.84 (d, J=12.6 Hz, 4H), 1.51-1.42 (m, 5H), 1.26 (s, 3H), 1.17 (s, 1H), 1.13-1.04 (m, 2H), 1.02-0.98 (m, 6H), 0.95-0.89 (m, 1H), 0.68 (s, 3H).

Example 166: (3S,8S,9S,10R,13R,14S,17R)-10,13-dimethyl-17-((R)-4-(6-(trifluoromethyl)pyridin-2-yl)butan-2-yl)-2,3,4,7,8,9,10,11,12,13,14,15,16,17-tetradecahydro-1H-cyclopenta[a]phenanthren-3-ol

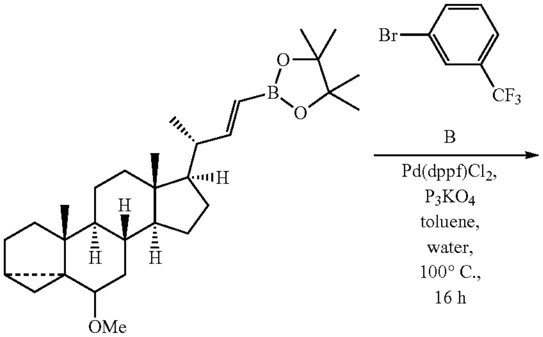

A

-continued

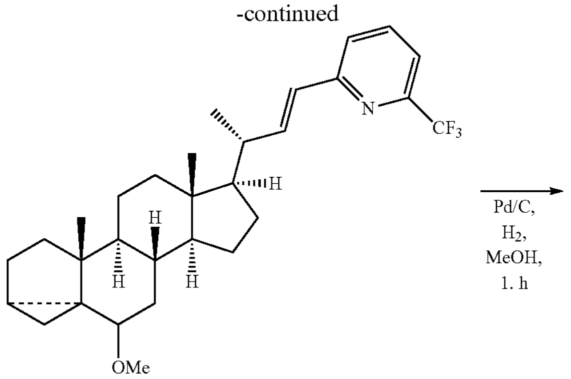

C

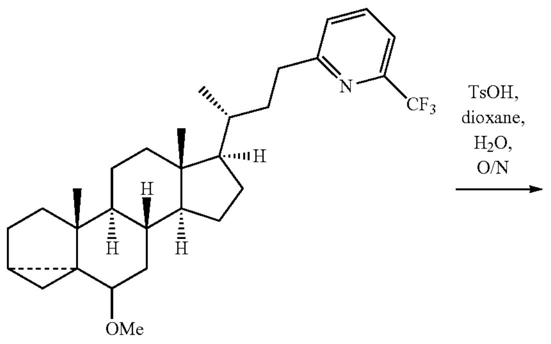

D

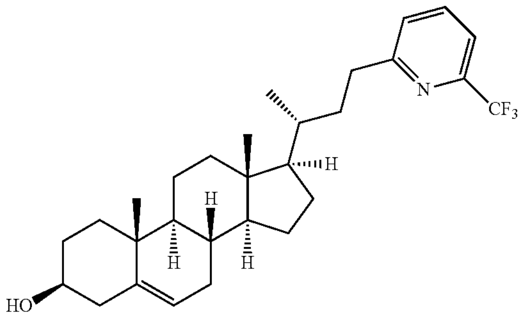

166

A solution of compound A (150 mg, 320 μmol), compound B (72.4 mg, 320 μmol), tripotassium phosphate (204 mg, 3 eq, 960 μmol), and 1,1'-Bis(diphenylphosphino)ferrocene palladium(II)dichloride (0.1 eq, 32 μmol) in toluene (4.5 mL) and water (0.3 mL) was stirred at 100° C. under $N_2$ for 16 h. The reaction mixture was diluted with water and extracted with ethyl acetate. The organic layer was washed with brine, dried over sodium sulfate, filtered, and concentrated. The residue was purified by column chromatography to afford compound C (120 mg, 76.9%).

To a solution of compound C (120 mg, 246 μmol) in MeOH (3 mL) and tetrahydrofuran (3 mL) was added Pd/C (12 mg, 10% weight). The mixture was stirred at room temperature under 1 atm of $H_2$ for 1 h. The reaction mixture was filtered and concentrated in vacuo to afford compound D (120 mg, 100% yield).

To a solution of compound D (60 mg, 123 μmol) in 1,4-dioxane (2 mL) and water (0.5 mL) was added 4-methylbenzene-1-sulfonic acid (4.22 mg, 0.2 eq, 24.5 μmol). The mixture was stirred at 80° C. under $N_2$ for 16 h. The reaction mixture was diluted with water and extracted with ethyl acetate. The organic layer was washed with brine, dried over sodium sulfate, filtered, and concentrated. The residue was purified by column chromatography to afford compound 166 (15.5 mg, 27.0%). $^1H$ NMR (400 MHz, $CDCl_3$) δ 7.74 (t, J=7.8 Hz, 1H), 7.47 (d, J=7.7 Hz, 1H), 7.32 (d, J=7.9 Hz, 1H), 5.34 (d, J=5.2 Hz, 1H), 3.52 (tt, J=10.7, 4.7 Hz, 1H), 2.94 (ddd, J=14.9, 11.0, 4.3 Hz, 1H), 2.75 (ddd, J=13.9, 10.2, 6.0 Hz, 1H), 2.35-2.18 (m, 2H), 2.08-1.92 (m, 2H), 1.92-1.79 (m, 4H), 1.71-1.39 (m, 10H), 1.27 (qd, J=9.8, 4.9 Hz, 2H), 1.22-0.83 (m, 13H), 0.67 (s, 3H).

Example 167: (3S,8S,9S,10R,13R,14S,17R)-17-((R)-4-(6-ethylpyridin-2-yl)butan-2-yl)-10,13-dimethyl-2,3,4,7,8,9,10,11,12,13,14,15,16,17-tetradecahydro-1H-cyclopenta[a]phenanthren-3-ol

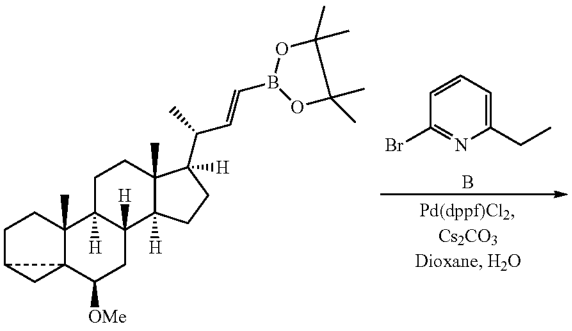

A

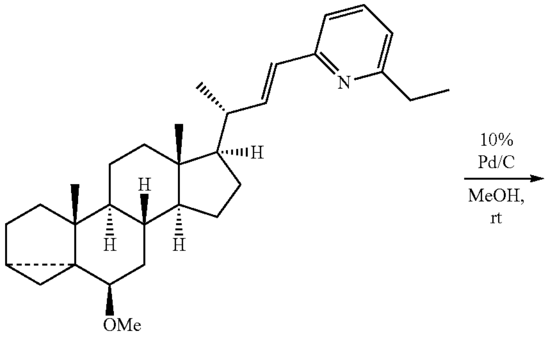

C

-continued

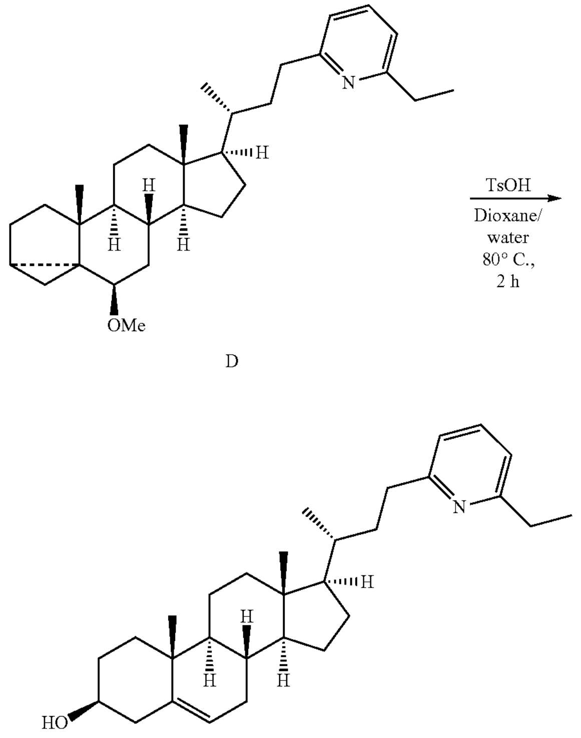

D

167

To a solution of compound A (150 mg, 320 μmol) in 1,4-dioxane (5 mL) and water (1 mL) were added compound B (71.5 mg, 384 μmol), Pd(dppf)$Cl_2$ (23.2 mg, 32 μmol), and cesium carbonate (156 mg, 480 μmol) at room temperature. The mixture was stirred at 60° C. for 8 h. After completion, the solvent was evaporated to afford the crude product that was purified by column chromatography to give compound C (79 mg, 55%) as a white solid.

To a solution of compound C (79 mg, 176 μmol) in MeOH (3 mL) was added Pd/C (8 g, 1% weight) at room temperature. The mixture was stirred for 16 h under 1 atm of $H_2$. After completion, the mixture was filtered and the solvent was evaporated to afford the crude product that was purified by column chromatography to give compound D (70 mg, 88%) as a white solid.

To a solution of compound D (70 mg, 156 μmol) in 1,4-dioxane (4.0 mL) and water (1.0 mL) was added 4-methylbenzene-1-sulfonic acid (5.36 mg, 31.1 μmol) at room temperature. The mixture was stirred at 80° C. for 2 h. After completion, the reaction was quenched by the addition of $NaHCO_3$ and extracted with DCM (50 mL×3). The combined organic layer was dried over sodium sulfate and concentrated to give crude product that was purified by column chromatography to yield compound 167 (17 mg, 25%). $^1$H NMR (400 MHz, $CDCl_3$) δ 7.52 (t, J=7.8 Hz, 1H), 6.97 (t, J=6.6 Hz, 2H), 5.34 (d, J=5.2 Hz, 1H), 3.52 (s, 1H), 2.97-2.80 (m, 3H), 2.67 (s, 1H), 2.26 (dd, J=13.6, 8.6 Hz, 2H), 2.04-1.94 (m, 2H), 1.85 (dt, J=14.6, 4.6 Hz, 4H), 1.62-1.51 (m, 4H), 1.47-1.39 (m, 3H), 1.29 (s, 3H), 1.26 (s, 1H), 1.17 (d, J=9.4 Hz, 2H), 1.08 (d, J=4.6 Hz, 2H), 1.03 (d, J=6.4 Hz, 3H), 1.01 (s, 3H), 0.85 (s, 3H), 0.67 (s, 3H).LCMS: $[M+H]^+$=436.25.

Example 168: (3S,8S,9S,10R,13R,14S,17R)-17-((R)-4-(6-methoxypyridin-2-yl)butan-2-yl)-10,13-dim ethyl-2, 3,4, 7,8,9,10,11,12,13,14,15,16,17-tetradecahydro-1H-cyclopenta[a]phenanthren-3-ol

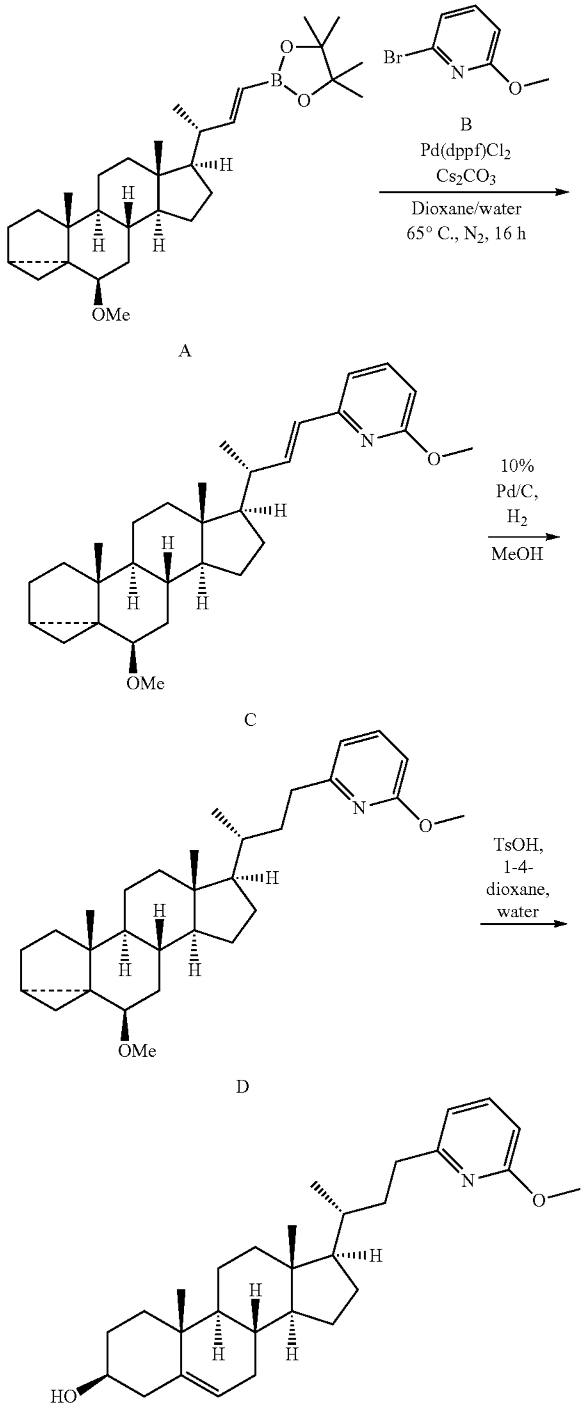

A

B

C

D

168

The solution of compound A (150 mg, 0.32 mmol) in 1.4-dioxane (0.7 mL) and water (0.1 mL) were added compound B (120 mg, 0.64 mmol), Pd(dppf)$Cl_2$ (46.2 mg, 0.064 mmol), and $Cs_2CO_3$ (312 mg, 0.96 mmol). The mixture was stirred at 65° C. for 16 h. After completion, the mixture was washed with water and extracted with ethyl acetate (10 mL×3). The organic layer was washed with brine, dried over sodium sulfate, filtered, and concentrated to give the crude product that was purified by column chromatography to afford compound C (85 mg, 59%) LCMS: $[M+H]^+$=450.35

To a solution of compound C (85 mg, 0.19 mmol) in methanol (2 mL) was added Pd/C (8.5 mg, 10% weight). The mixture was stirred at room temperature for 3 h under 1 atm of hydrogen. After completion, the mixture was filtered and concentrated to give the crude product that was purified by column chromatography to give compound D (66 mg, 77%). LCMS: $[M+H]^+$=452.35.

To a solution of compound D (66 mg, 0.15 mmol) in 1.4-dioxane (0.7 mL) and water (0.1 mL) was added TsOH (5.2 mg, 0.03 mmol). The mixture was stirred at 80° C. for 3 h. After completion, the mixture was washed with $NaHCO_3$ and extracted with ethyl acetate (10 mL×3). The organic layer was washed with brine, dried over sodium sulfate, filtered, and concentrated to give the crude product that was purified by column chromatography to yield compound 168 (30 mg, 46%) as a white solid. $^1$H NMR (400 MHz, $CDCl_3$) δ 7.51 (t, J=7.7 Hz, 1H), 6.72 (d, J=7.3 Hz, 1H), 6.56 (d, J=8.1 Hz, 1H), 5.35 (s, 1H), 3.94 (s, 3H), 3.58-3.46 (m, 1H), 2.86-2.74 (m, 1H), 2.71-2.58 (m, 1H), 2.35-2.15 (m, 2H), 2.10-1.75 (m, 7H), 1.63-1.52 (m, 4H), 1.46-1.40 (m, 3H), 1.37-0.82 (m, 19H), 0.68 (s, 3H).

Example 170: (1R,3aS,3bS,7S,9aR,9bS,11aR)-9a,11a-dimethyl-1-[(2R)-4-(pyridazin-4-yl)butan-2-yl]-1H,2H,3H,3aH,3bH,4H,6H,7H,8H,9H,9aH,9bH,10H,11H,11aH-cyclopenta[a]phenanthren-7-ol

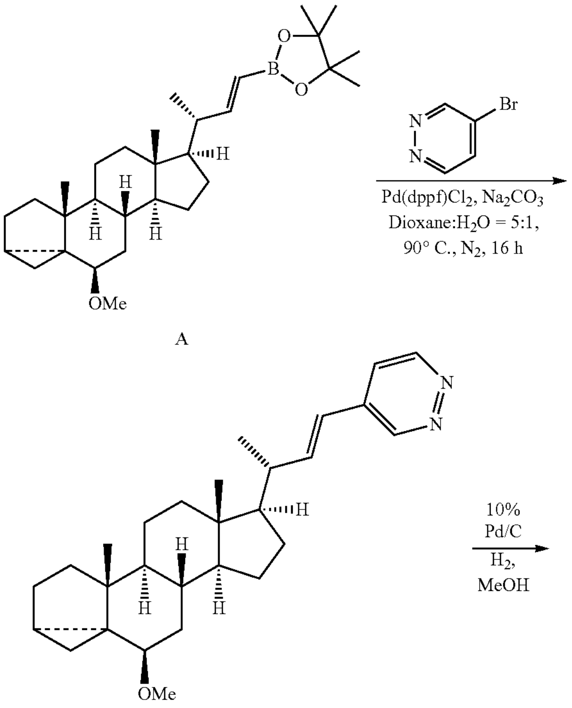

A

B

-continued

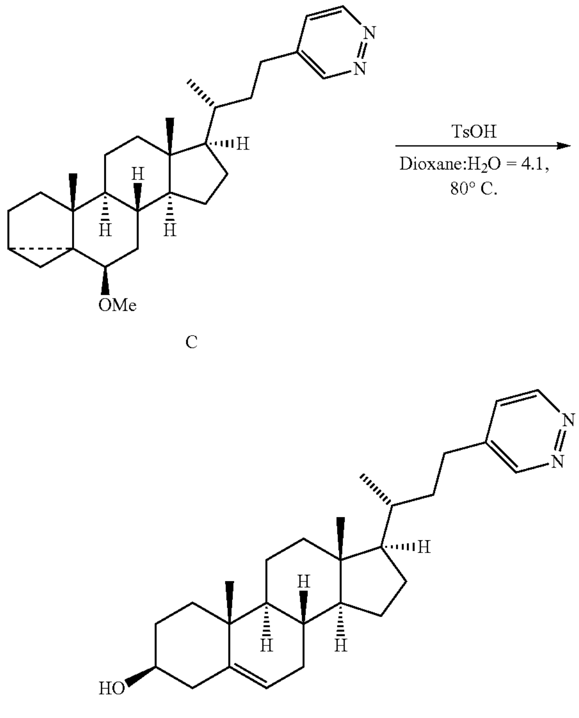

C

170

To a solution of compound A (250 mg, 534 μmol) in a mixture of 1,4-dioxane (10 mL) and water (2 mL) were added sodium carbonate (141 mg, 1.33 mmol), 4-bromopyridazine (110 mg, 694 μmol), and Pd(dppf)$Cl_2$ (38.7 mg, 53.4 μmol). The mixture was heated at 90° C.; for 16 h under nitrogen and then cooled to ambient temperature. The mixture was filtered through Celite, and the filtrate was concentrated in vacuo. The residue was purified by column chromatography (eluting with 1/3 ethyl acetate/petroleum ether) to afford compound B (240 mg, 53.4%).

To a solution of compound B (240 mg, 571 μmol) in methanol (5 mL) was added Pd/C (24 mg, 10% weight). The mixture was purged with hydrogen three times, then charged with 1 atm of hydrogen and stirred for 2 h at room temperature. After completion, the mixture was filtered through Celite and concentrated in vacuo to give compound C (200 mg, 82.9%).

A mixture of crude compound C (240 mg, 568 μmol) and 4-methylbenzene-1-sulfonic acid hydrate (21.6 mg, 114 μmol) in 1,4-dioxane (8 mL) and water (2 mL) was heated at 80° C. for 4 h under an atmosphere of nitrogen. After completion, the pH of the mixture was adjusted to 7 with saturated $NaHCO_3$ solution and extracted with ethyl acetate. The organic layer was dried over anhydrous sodium sulfate and concentrated in vacuo to give the crude product that was purified by column chromatography (eluting with 1/1 ethyl acetate/petroleum ether) to afford compound 170 (87.5 mg, 37.7%). $^1$H NMR (400 MHz, $CDCl_3$) δ 9.07 (d, J=5.4 Hz, 2H), 7.37-7.30 (m, 1H), 5.35 (d, J=5.0 Hz, 1H), 3.52 (d, J=4.6 Hz, 1H), 2.73 (d, J=4.2 Hz, 1H), 2.53 (dd, J=7.0, 3.6 Hz, 1H), 2.34-2.18 (m, 3H), 2.05-1.94 (m, 2H), 1.88-1.70 (m, 4H), 1.65-1.34 (m, 9H), 1.26 (d, J=2.8 Hz, 2H), 1.20-1.06 (m, 4H), 1.06-0.94 (m, 8H), 0.94-0.81 (m, 1H). LCMS: $[M+H]^+$=409.25.

Example 171: (3S,8S,9S,10R,13R,14S,17R)-10,13-dimethyl-17-((R)-4-(pyrimidin-5-yl)butan-2-yl)-2,3,4,7,8,9,10,11,12,13,14,15,16,17-tetradecahydro-1H-cyclopenta[a]phenanthren-3-ol

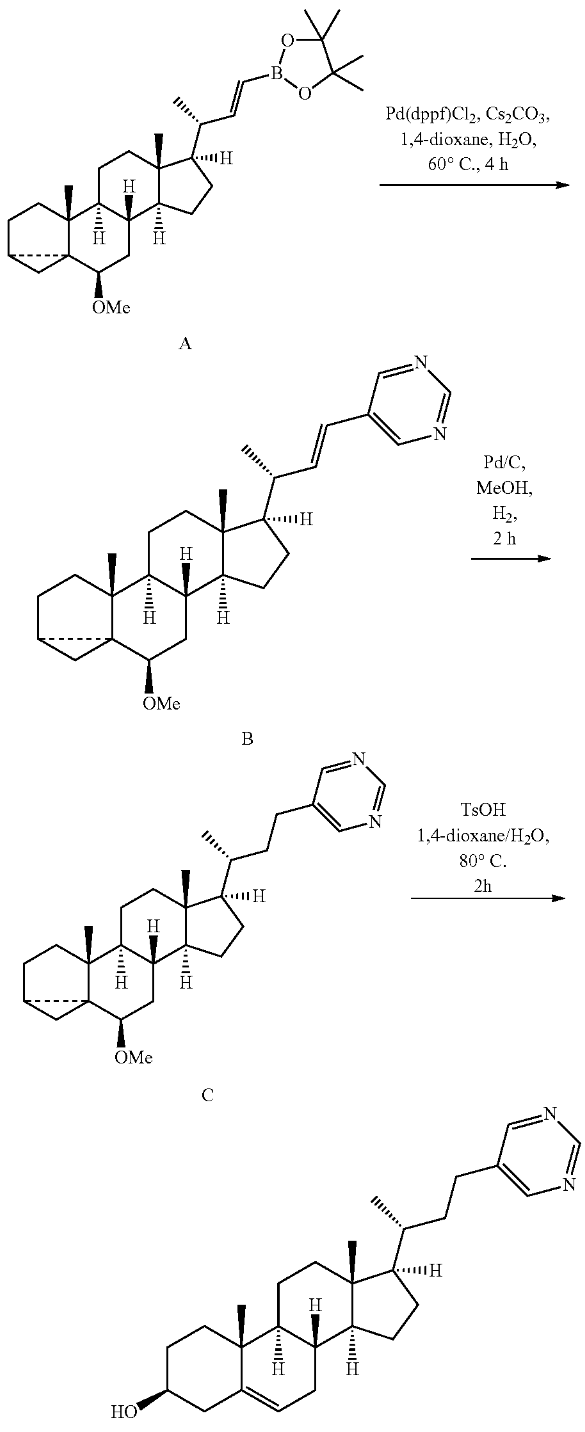

A

B

C

171

A solution of compound A (500 mg, 1.07 mmol), 5-bromopyrimidine (254 mg, 1.6 mmol), Pd(dppf)$Cl_2$ (77.4 mg, 107 μmol), and $Cs_2CO_3$ (695 mg, 2.13 mmol) in 1,4-dioxane (20 mL) and water (3 mL) was stirred at 100° C. for 16 h. After completion, the mixture was concentrated to give the crude product that was purified by column chromatography to give compound B (450 mg, 100%).

A mixture of compound B (380 mg, 903 μmol) and Pd/C (76 mg, 20% weight) in methanol (19 mL) was stirred at room temperature for 2 h under 1 atm of $H_2$. After completion, the mixture was filtered and the solvent was evaporated to give the crude product that was purified by silica gel chromatography to give compound C (280 mg, 73%).

A solution of compound C (200 mg, 473 μmol) and 4-methylbenzene-1-sulfonic acid hydrate (18 mg, 94.6 μmol) in 1,4-dioxane (4 mL) and water (1 mL) was stirred at 80° C. for 2 h. The reaction was quenched with $H_2O$ and extracted with DCM. The organic layer was concentrated to give the crude product that was purified by column chromatography to give compound 171 (120 mg, 62%). $^1$H NMR (400 MHz, $CDCl_3$) δ 9.07 (s, 1H), 8.59 (s, 2H), 5.38-5.31 (m, 1H), 3.52-3.46 (m, 1H), 2.77-2.65 (m, 1H), 2.53-2.45 (m, 1H), 2.27 (t, J=15.2 Hz, 2H), 2.05-1.95 (m, 2H), 1.90-1.80 (m, 3H), 1.71 (dd, J=11.4, 5.8 Hz, 1H), 1.65-1.35 (m, 9H), 1.29-1.15 (m, 4H), 1.10 (d, J=11.2 Hz, 2H), 1.05 (s, 3H), 1.01 (s, 3H), 0.99-0.80 (m, 2H), 0.68 (s, 3H).

Example 172: (1R,3aS,3bS,7S,9aR,9bS,11aR)-9a,11a-dimethyl-1-[(2R)-4-(1,3-thiazol-2-yl)butan-2-yl]-1H,2H,3H,3aH,3bH,4H,6H,7H,8H,9H,9aH,9bH,10H,11H,11aH-cyclopenta[a]phenanthren-7-ol

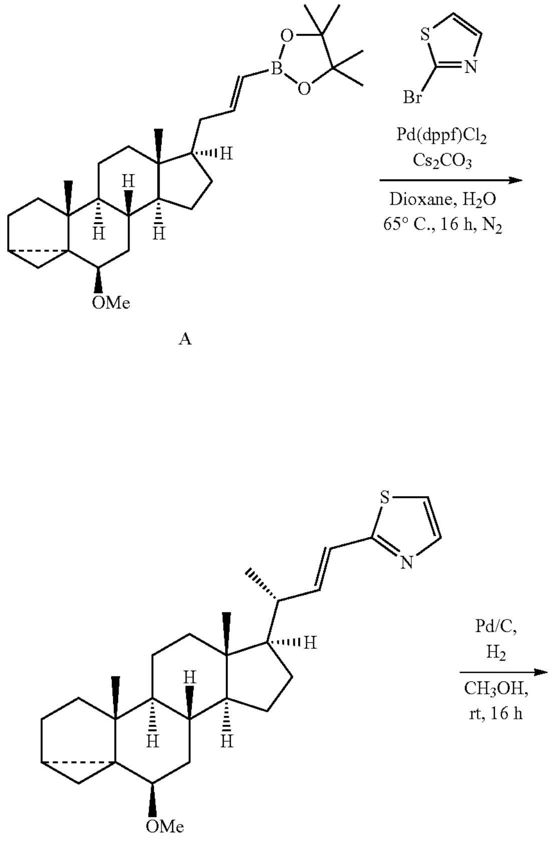

A

B

-continued

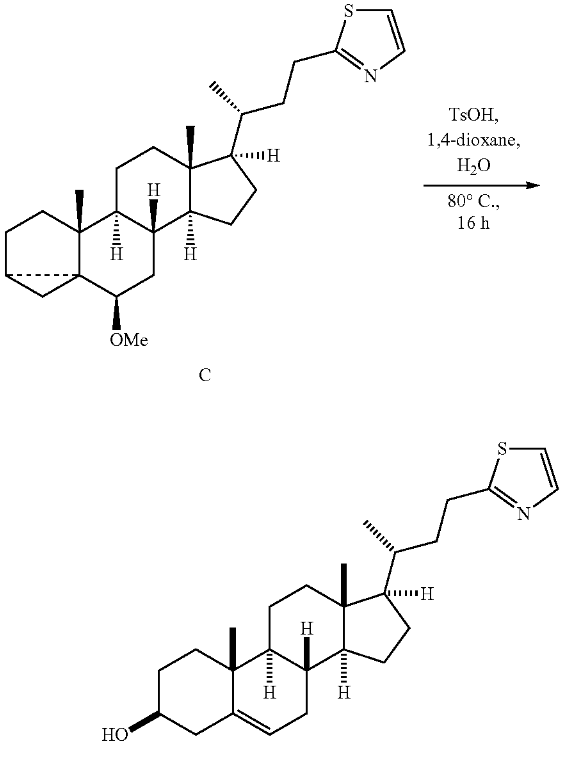

C

172

To a solution of compound A (500 mg, 1.07 mmol) in 1.4-dioxane (30 mL) and water (5 mL) were added 2-bromothiazole (175 mg, 1.07 mmol), cesium carbonate (59 mg, 427 μmol), and Pd(dppf)$Cl_2$ (31.2 mg, 42.7 μmol). The mixture was stirred at 65° C. for 16 h under $N_2$. After completion, the mixture was washed with water and extracted with ethyl acetate (30 mL×3). The organic layer was washed with brine, dried over sodium sulfate, filtered, and concentrated to give the crude product that was purified by column chromatography on to afford compound B (250 mg, 55%).

To a solution of compound B (250 mg, 585 μmol) in methanol (20 mL) was added Pd/C (500 mg, 200% weight). The mixture was stirred at room temperature for 16 h under 1 atm of hydrogen. After completion, the mixture was filtered and concentrated to give the crude product that was purified by column chromatography to give compound C (200 mg, 80%) as a white solid.

To a solution of compound C (200 mg, 468 μmol) in 1,4-dioxane (14 mL) and water (2 mL) at room temperature was added TsOH (40 mg, 232 μmol). The mixture was warmed to 80° C. and stirred 16 h. The solvent was removed in vacuo. The residue was diluted with water, basified with saturated $NaHCO_3$ to pH~7 and extracted with ethyl acetate (10 mL×3). The organic layer was washed by brine, dried over sodium sulfate, filtered, and concentrated. The residue was purified by column chromatography to afford compound 172 (19 mg, 10%) as a white solid. $^1H$ NMR (400 MHz, $CDCl_3$) δ 7.66 (d, J=3.3 Hz, 1H), 7.18 (d, J=3.3 Hz, 1H), 5.36 (s, 1H), 3.84-3.67 (m, 1H), 3.16-3.04 (m, 1H), 2.94 (dt, J=15.1, 8.2 Hz, 1H), 2.62-2.43 (m, 2H), 3.13-1.78 (m, 7H), 1.67-1.42 (m, 9H), 1.34-0.87 (m, 14H), 0.68 (s, 3H).

Example:173: (3S,8S,9S,10R,13R,14S,17R)-10,13-dimethyl-17-((R)-4-(thiazol-5-yl)butan-2-yl)-2,3,4,7,8,9,10,11,12,13,14,15,16,17-tetradecahydro-1H-cyclopenta[a]phenanthren-3-ol

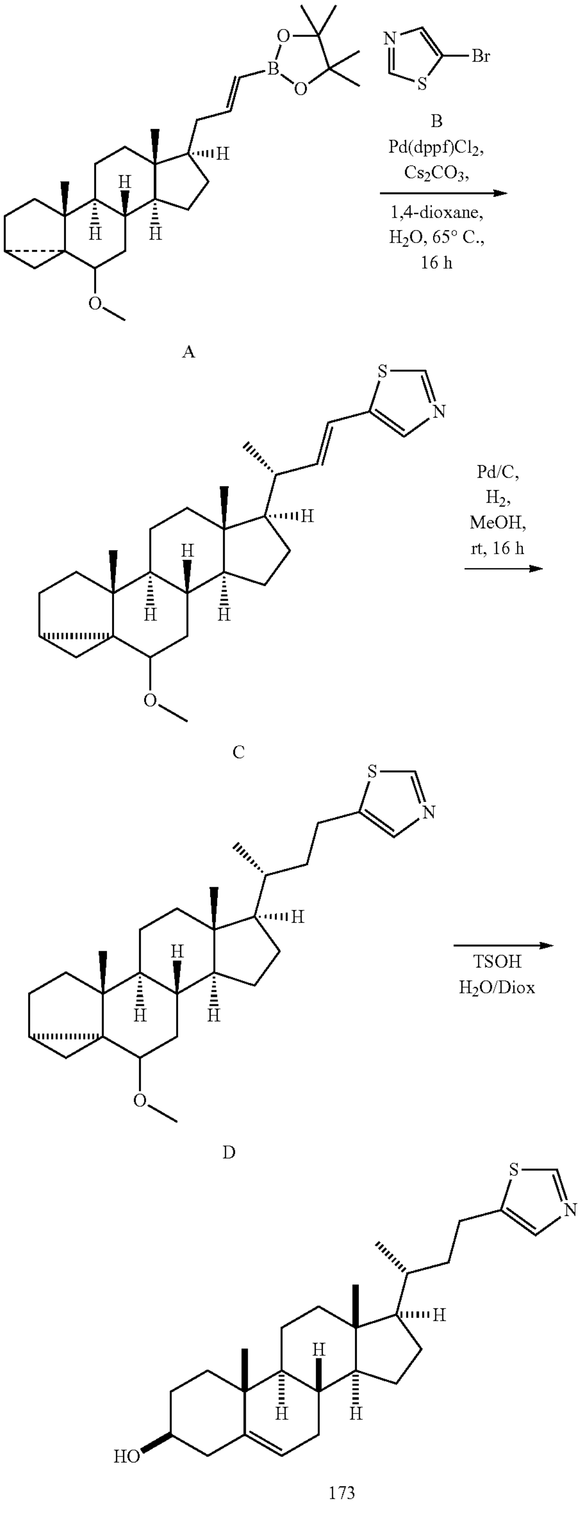

A

C

D

173

To a solution of compound A (400 mg, 854 μmol) in 1,4-dioxane (7 mL) and water (1 mL) were added compound B (140 mg, 854 μmol), cesium carbonate (695 mg, 2.13 mmol), and Pd(dppf)$Cl_2$ (62.4 mg, 0.1 eq. 85 μmol). The reaction was stirred for 16 h at 65° C. under $N_2$. After completion, the reaction was diluted with $H_2O$ (30 mL) and extracted with ethyl acetate (15 mL×3). The combined organic phases were washed with brine, dried over sodium sulfate, concentrated in vacuo, and the residue was purified by column chromatography to afford compound C (315 mg, 86%).

To a solution of compound C (280 mg, 658 μmol) in methanol (4 mL) was added Pd/C (560 mg, 200% weight). The reaction was stirred for 16 h at room temperature under 1 atm of $H_2$. After completion, the reaction solution was filtered and concentrated to afford compound D (200 mg, 71%).

To a solution of compound D (180 mg, 421 μmol) in 1,4-dioxane (4 mL) and water (1 mL) was added 4-methylbenzene-1-sulfonic acid (14.5 mg, 0.2 eq, 84.2 μmol). After being stirred at 80° C. for 16 h, to the mixture was added saturated $NH_4Cl$ (10 mL) and it was extracted with ethyl acetate (10 mL×3). The combined organic phases were washed with brine, dried over sodium sulfate, concentrated in vacuo, and the residue was purified by column chromatography to afford compound 173 (16.5 mg, 10%) as white solid. $^1$H NMR (400 MHz, $CDCl_3$) δ 8.71 (s, 1H), 7.63 (s, 1H), 5.39 (d, J=5.1 Hz, 1H), 3.55 (dq, J=10.7, 5.4, 4.8 Hz, 1H), 2.96 (ddd, J=14.7, 10.3,4.2 Hz, 1H), 2.80 (dt, J=15.5, 7.8 Hz, 1H), 2.41-2.20 (m, 2H), 2.14-1.77 (m, 8H), 1.72-1.60 (m, 2H), 1.51-1.43 (m, 3H), 1.35-0.89 (m, 18H), 0.71 (s, 3H).

Example 174: (1R,3aS,3bS,7S,9aR,9bS,11aR)-9a,11a-dimethyl-1-[(2R)-4-(1,2,4-thiadiazol-5-yl)butan-2-yl]-1H,2H,3H,3aH,3bH,4H,6H,7H,8H,9H,9aH,9bH,10H,11H,11aH-cyclopenta[a]phenanthren-7-ol -continued

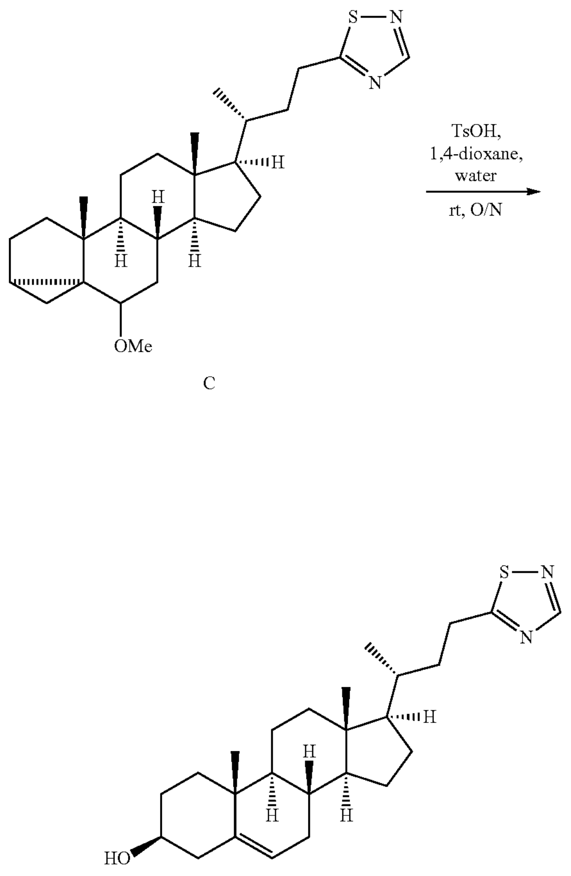

C

174

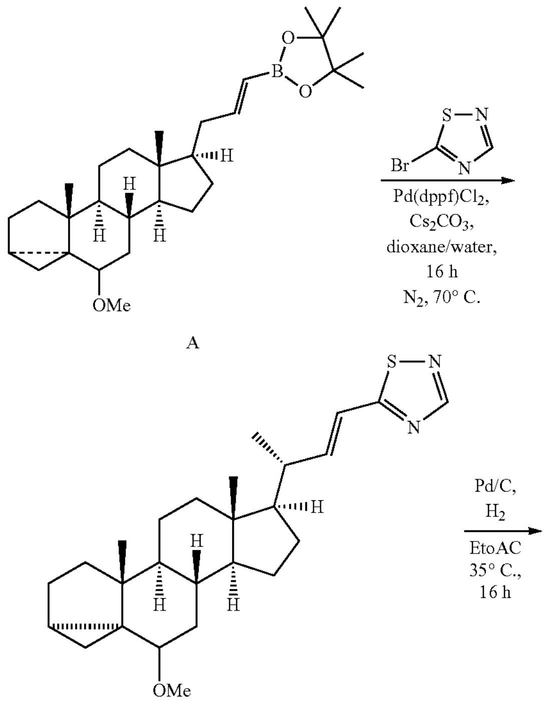

A

B

A solution of compound A (450 mg, 960 mol), $Cs_2CO_3$ (785 mg, 2.5 eq, 2.4 mol), 5-bromo-1,2,4-thiadiazole (158 mg, 960 mol), and Pd(dppf)$Cl_2$ (69.7 mg, 0.1 eq, 96 μmol) in 1,4-dioxane (10 mL) and water (1.5 mL) was heated at 70° C. under $N_2$ atmosphere for 16 h. After completion, the solvent was concentrated in vacuo and the residue was purified by silica gel column to give compound B (330 mg, 73%) as white solid.

A mixture of compound B (330 mg, 773 μmol) and Pd/C (33 mg, 10% weight) in ethyl acetate (5 mL) was stirred at 35° C. for 16 h under 1 atm of $H_2$. The mixture was filtered and concentrated to afford compound C (288 mg, 96%).

A solution of compound C (270 mg, 630 μmol) and 4-methylbenzene-1-sulfonic acid hydrate (24 mg, 0.2 eq, 126 μmol) in 1,4-dioxane (14 mL) and water (2 mL) was stirred at 80° C. for 3 h. After completion, the mixture was diluted with water and extracted with ethyl acetate. The combined organic layer was washed with brine, dried over sodium sulfate, concentrated in vacuo, and the residue was purified by column chromatography to yield compound 174 (160 mg, 61%) as a white solid. $^1$H NMR (400 MHz, $CDCl_3$) δ 8.58 (s, 1H), 5.35 (d, J=5.1 Hz, 1H), 3.52 (tt, J=10.6, 4.7 Hz, 1H), 3.19 (ddd, J=15.4, 10.7, 4.2 Hz, 1H), 3.05 (ddd, J=15.7, 9.8, 6.3 Hz, 1H), 2.36-2.18 (m, 2H), 2.05-1.92 (m, 3H), 1.89-1.80 (m, 3H), 1.66-1.39 (m, 11H), 1.36-1.12 (m, 4H), 1.10-0.93 (m, 10H), 0.69 (s, 3H).

Example 175: (1R,3aS,3bS,7S,9aR,9bS,11aR)-9a,11a-dimethyl-1-[(2R)-4-(1,3-thiazol-4-yl)butan-2-yl]-1H,2H,3H,3aH,3bH,4H,6H,7H,8H,9H,9aH,9bH,10H,11H,11aH-cyclopenta[a]phenanthren-7-ol

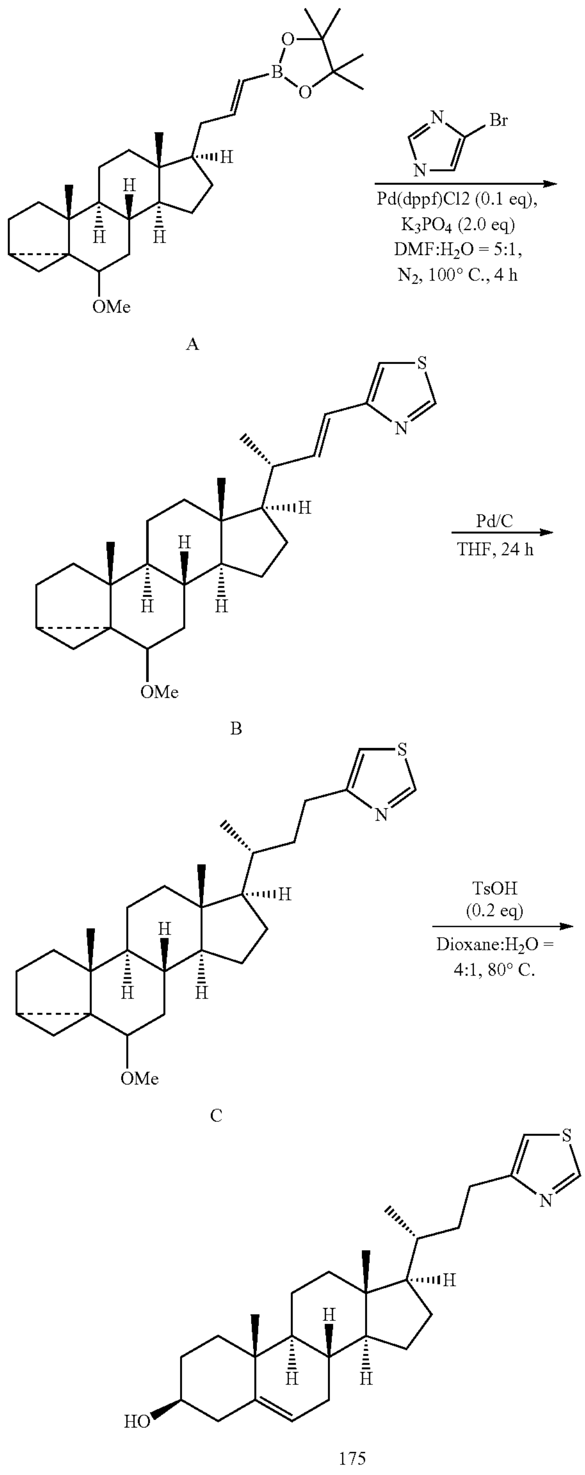

A

B

C

175

To a solution of compound A (500 mg, 1.07 mmol) in a mixture of DMF (12.5 mL) and water (2.5 mL) were added potassium phosphate tribasic (453 mg, 2.13 mmol), 4-bromo-1,3-thiazole (350 mg, 2.13 mmol) and Pd(dppf)$Cl_2$ (77.4 mg, 107 μmol). The mixture was heated at 100° C. for 48 h under $N_2$. After being cooled to ambient temperature, the mixture was filtered through Celite, and the filtrate concentrated in vacuo. The residue was purified by column chromatography (eluting with 1/40 ethyl acetate/petroleum ether) to give compound B (207 mg, 45.6%) as a white solid.

To a solution of compound B (207 mg, 486 μmol) in THF (5 mL) was added Pd/C (41 mg, 20% weight). The mixture was purged with hydrogen three times and stirred for 2 h under 1 atm of $H_2$. The mixture was filtered through Celite, and the filtrate was concentrated in vacuo. The residue was purified by column chromatography (eluting with 1/20 ethyl acetate/petroleum ether) to give compound C (103 mg, 49.5%).

A mixture of compound C (103 mg, 241 μmol) and 4-methylbenzene-1-sulfonic acid hydrate (9.16 mg, 48.2 μmol) in 1,4-dioxane (4 mL) and water (1 mL) was heated at 80° C. for 4 h. The pH of the mixture was adjusted to 7 with saturated $NaHCO_3$ solution and extracted with ethyl acetate. The organic layer was dried over anhydrous sodium sulfate and concentrated in vacuo to give the crude product that was purified by column chromatography (eluting with 1/10 ethyl acetate/petroleum ether) to afford compound 175 (90.7 mg, 91.0%). $^1H$ NMR (400 MHz, $CDCl_3$) δ 8.78 (d, J=1.8 Hz, 1H), 6.94 (d, J=1.8 Hz, 1H), 5.35 (d, J=5.0 Hz, 1H), 3.58-3.47 (m, 1H), 2.98-2.85 (m, 1H), 2.79-2.68 (m, 1H), 2.35-2.19 (m, 2H), 2.09-1.90 (m, 3H), 1.90-1.79 (m, 4H), 1.63-1.41 (m, 9H), 1.27 (s, 2H), 1.18-1.08 (m, 4H), 1.05-1.01 (m, 6H), 1.00-0.82 (m, 2H). LCMS: $[M+H]^+$ =414.20.

Example 176: (3S,8S,9S,10R,13R,14S,17R)-17-((R)-4-(isothiazol-4-yl)butan-2-yl)-10,13-dimethyl-2,3,4,7,8,9,10,11,12,13,14,15,16,17-tetradecahydro-1H-cyclopenta[a]phenanthren-3-ol

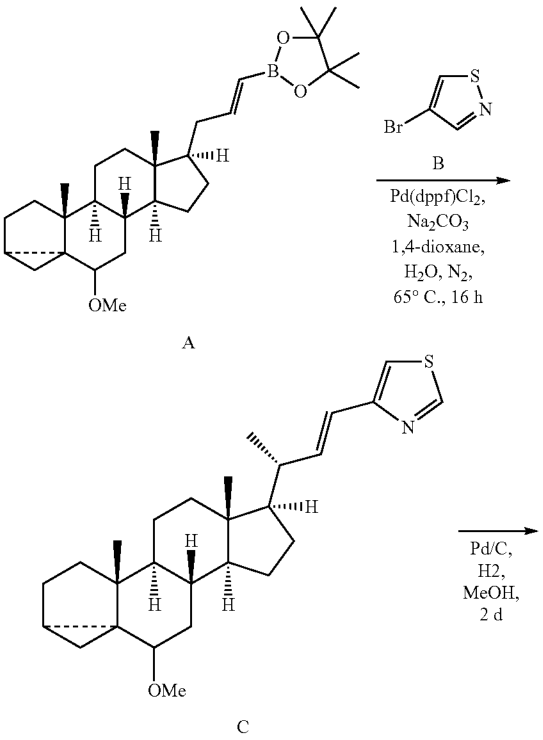

A

C

-continued

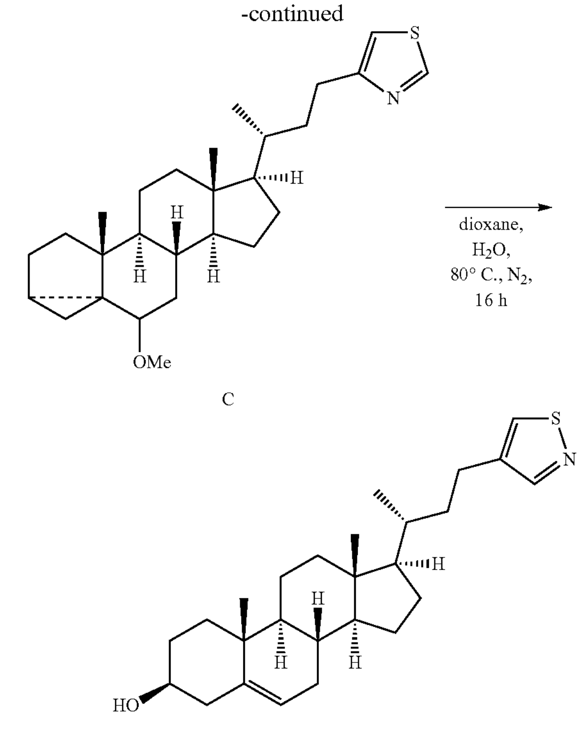

C

176

A mixture of compound A (400 mg, 0.85 mmol), compound B (139 mg, 0.85 mmol), $Na_2CO_3$ (226.3 mg, 2.5 eq, 2.13 mmol) and $Pd(dppf)Cl_2$ (61 mg, 0.1 eq, 0.085 mmol) in 1,4-dioxane (14 mL) and water (2 mL) was stirred at 65° C. under $N_2$ for 16 h. The reaction mixture was diluted with water and extracted with ethyl acetate. The organic layer was washed by brine, dried over sodium sulfate, filtered, and concentrated. The residue was purified by column chromatography to afford compound C (300 mg, 82.6% yield) as a white solid.

A solution of compound C (280 mg) in methanol (10 mL) was added Pd/C (560 mg, 200% weight) and stirred at room temperature under 1 atm of $H_2$ for 2 days. After completion, the mixture was filtered through Celite, and the solvent was concentrated in vacuo to afford compound D (90 mg, 32% yield) as a white solid.

To a solution of compound D (90 mg, 210 μmol) in 1,4-dioxane (8.4 mL, 98.5 mmol) and water (1.2 mL, 66.6 mmol) was added 4-methylbenzene-1-sulfonic acid (7.25 mg, 0.2 eq, 42.1 μmol). The mixture was stirred at 80° C. for 16 h. The reaction mixture was diluted with water and extracted with ethyl acetate. The organic layer was washed by brine, dried over sodium sulfate, filtered, and concentrated to afford the crude product that was purified by column chromatography to afford compound 176 (20.7 mg, 23.7% yield) as a white solid. $^1H$ NMR (400 MHz, $CDCl_3$) δ 8.34 (s, 1H), 8.23 (s, 1H), 5.35 (d, J=8.0 Hz, 1H), 3.58-3.47 (m, 1H), 2.82-2.72 (m, 1H), 2.66-2.56 (m, 1H), 2.34-2.17 (m, 2H), 2.06-1.92 (m, 2H), 1.91-1.71 (m, 4H), 1.65-1.36 (m, 11H), 1.33-0.89 (m, 13H), 0.68 (s, 3H).

Example 178: (3S,8S,9S,10R,13R,14S,17R)-10,13-dimethyl-17-((R)-4-(quinolin-2-yl)butan-2-yl)-2,3,4,7,8,9,10,11,12,13,14,15,16,17-tetradecahydro-1H-cyclopenta[a]phenanthren-3-ol

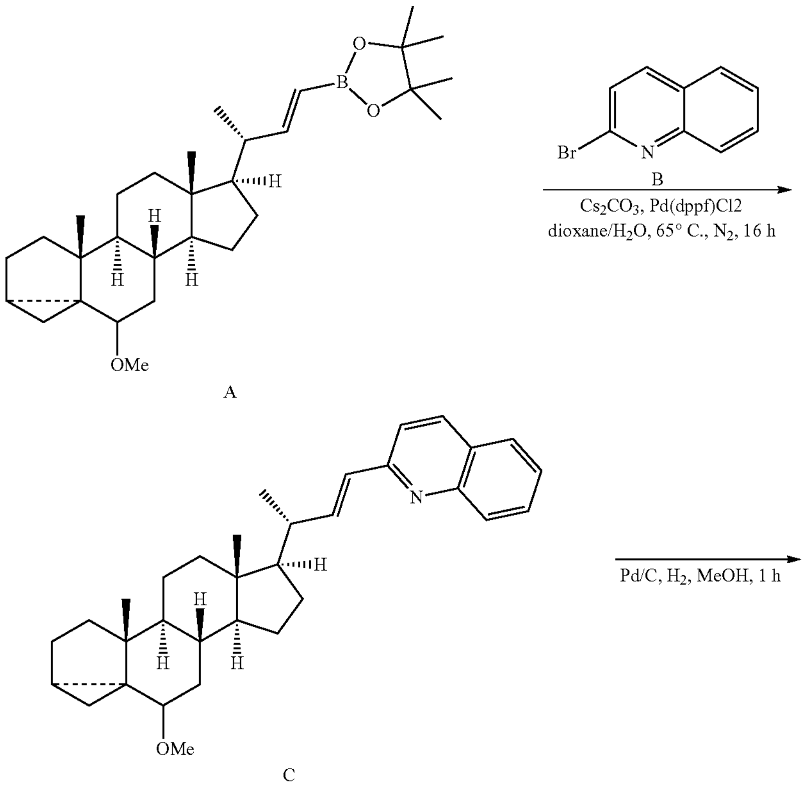

A

B

C

-continued

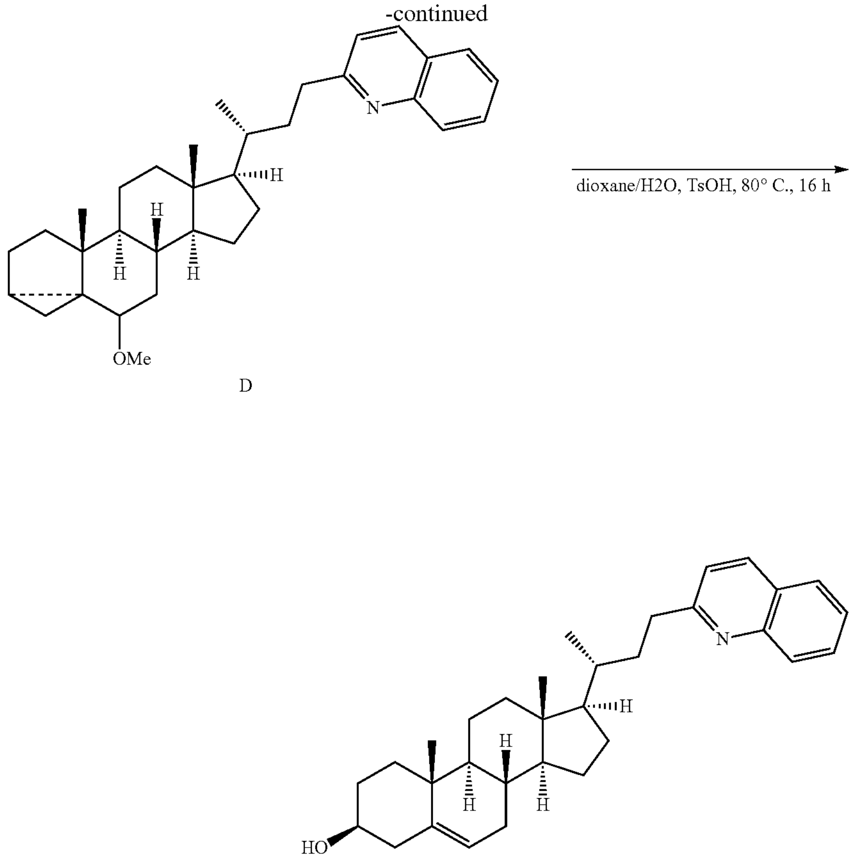

D

178

A mixture of compound A (500 mg, 1.07 mmol), compound B (222 mg, 1.07 mmol), cesium carbonate (1.22 g, 3.5 eq, 3.74 mmol), and Pd(dppf)$Cl_2$ (0.1 eq, 107 μmol) in 1,4-dioxane (42 mL) and water (6 mL) was stirred at 65° C. under $N_2$ for 16 h. The reaction mixture was diluted with water and extracted with ethyl acetate. The organic layer was washed by brine, dried over sodium sulfate, filtered, and concentrated. The residue was purified by column chromatography to afford compound C (360 mg, 71.8%).

To a solution of compound C (340 mg, 724 μmol) in methanol (13.6 mL) was added Pd/C (34 mg, 10% weight), the mixture was stirred under 1 atm of $H_2$ for 1 h. The reaction mixture was filtered and concentrated to afford compound D (300 mg).

To a solution of D (300 mg, 636 μmol) in 1,4-dioxane (7 mL) and water (1 mL) was added 4-methylbenzene-1-sulfonic acid (21.9 mg, 0.2 eq, 127 μmol). The mixture was stirred at 80° C. for 16 h. The reaction mixture was diluted with water (200 mL) and extracted with ethyl acetate (200 mL). The organic layer was washed by brine, dried over sodium sulfate, filtered, and concentrated. The residue was purified by column chromatography to afford compound 178 (138 mg, yield: 47.4%) as a white solid. $^1$H NMR (400 MHz, $CDCl_3$) δ 8.06 (d, J=12.0 Hz, 2H), 7.77 (d, J=8.0 Hz, 1H), 7.68 (t, J=8.0 Hz, 1H), 7.48 (t, J=8.0 Hz, 1H), 7.29 (d, J=12.0 Hz, 1H), 5.35 (d, J=4.0 Hz, 1H), 3.58-3.47 (m, 1H), 3.06 (ddd, J=12.6, 11.4, 4.0 Hz, 1H), 2.85 (d, J=12.2 Hz, 1H), 2.35-2.15 (m, 2H), 2.11-1.77 (m, 6H), 1.74-1.38 (m, 11H), 1.38-1.14 (m, 4H), 1.14-0.85 (m, 11H), 0.69 (s, 3H).

Example 179: (3S,8S,9S,10R,13S,14S,17R)-10,13-dimethyl-17-((S)-1-(pyridin-2-yloxy)propan-2-yl)-2,3,4,7,8,9,10,11,12,13,14,15,16,17-tetradecahydro-1H-cyclopenta[a]phenanthren-3-ol

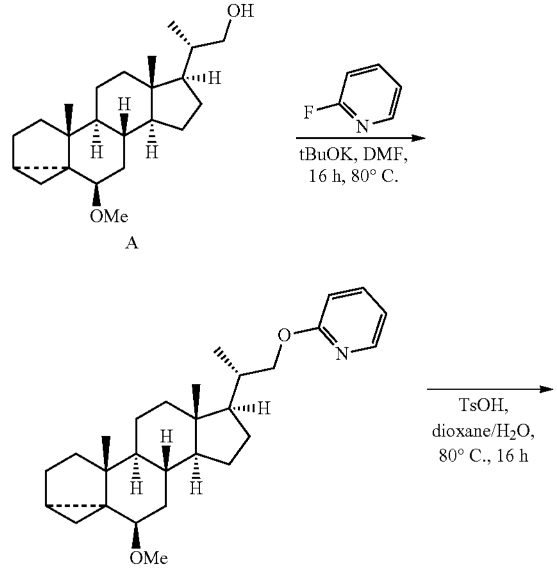

A

B

-continued

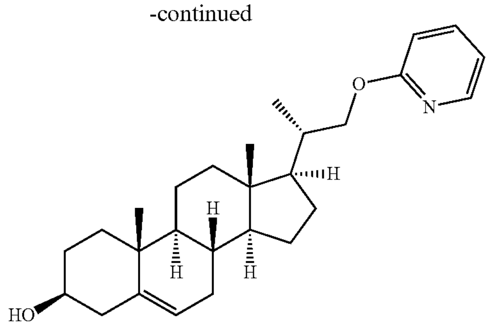

179

To a solution of compound A (50 mg, 144 μmol) and 2-fluoropyridine (21 mg, 1.5 eq, 216 μmol) in dimethylformamide (5 mL) was added tBuOK (48.6 mg, 3 eq, 433 μmol) at room temperature. The mixture was stirred at 80° C. for 16 h. After completion, the mixture was concentrated in vacuo and the residue was purified by column chromatography (petroleum ether/ethyl acetate=10/1, v/v) to afford compound B (60 mg, 142 μmol) as a white solid.

To a solution of compound B (60 mg, 144 μmol) in 1,4-dioxane (3 mL) and water (1 mL) was added 4-methylbenzene-1-sulfonic acid (4.97 mg, 0.2 eq, 28.9 μmol) at room temperature. After being stirred at 80° C. for 16 h, the reaction was concentrated in vacuo and the residue was purified by column chromatography (petroleum ether/ethyl acetate=3/1, v/v) to afford compound 179 (8 mg, 19.5 μmol) as a white solid. $^1$H NMR (400 MHz, $CDCl_3$) δ 8.14 (dd, J=5.2, 1.9 Hz, 1H), 7.62-7.49 (m, 1H), 6.83 (dd, J=7.0, 5.1 Hz, 1H), 6.73 (d, J=8.4 Hz, 1H), 5.35 (d, J=5.2 Hz, 1H), 4.25 (dd, J=10.1, 3.3 Hz, 1H), 4.00 (dd, J=10.1, 7.4 Hz, 1H), 3.53 (tt, J=10.9, 4.8 Hz, 1H), 2.36-2.16 (m, 2H), 2.12-1.79 (m, 7H), 1.61-1.55 (m, 2H), 1.49-1.19 (m, 7H), 1.12 (d, J=6.5 Hz, 3H), 1.11-1.03 (m, 2H), 1.02 (s, 3H), 0.99-0.85 (m, 2H), 0.74 (s, 3H).

Example 180: (3S,8S,9S,10R,13S,14S,17R)-10,13-dimethyl-17-((S)-1-(pyridin-3-yloxy)propan-2-yl)-2,3,4,7,8,9,10,11,12,13,14,15,16,17-tetradecahydro-1H-cyclopenta[a]phenanthren-3-ol

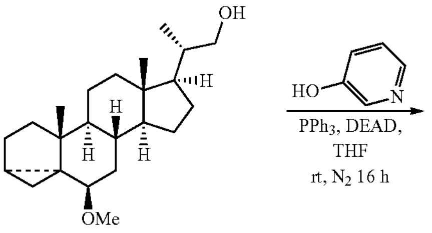

A

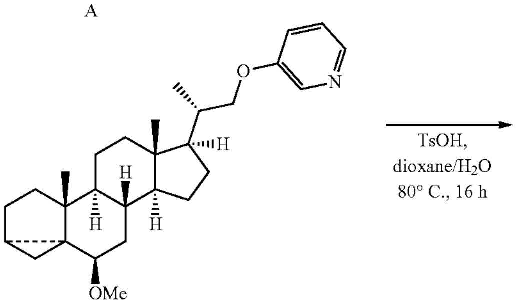

B

-continued

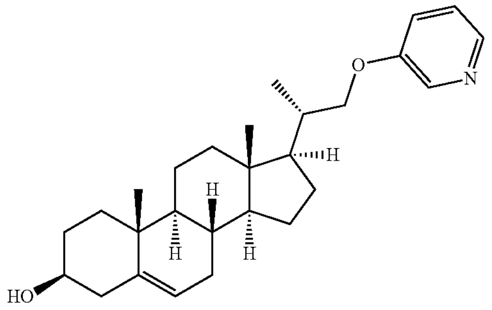

180

To a solution of compound A (50 mg, 144 μmol) and pyridin-3-ol (16.5 mg, 1.2 eq, 173 μmol) in tetrahydrofuran (5 mL) were added triphenylphosphine (114 mg, 3 eq, 433 μmol) and DEAD (75.4 mg, 3 eq, 433 μmol) at 0° C. under $N_2$. After being stirred at room temperature for 16 h, the reaction was concentrated in vacuo and the residue was purified by column chromatography (petroleum ether/ethyl acetate=10/1, v/v) to afford compound B (25 mg, 59 μmol, 41%) as a white solid.

To a solution of compound B (60 mg, 144 μmol) in 1,4-dioxane (3 mL) and water (1 mL) was added 4-methylbenzene-1-sulfonic acid (4.97 mg, 0.2 eq, 28.9 μmol) at room temperature. After being stirred at 80° C. for 16 h, the reaction was concentrated in vacuo and the residue was purified by column chromatography (petroleum ether/ethyl acetate=3/1, v/v) to afford compound 180 (7.9 mg, 19.5 μmol, 14%) as a white solid. $^1$H NMR (400 MHz, $CDCl_3$) δ 8.31 (s, 1H), 8.20 (s, 1H), 7.22 (d, J=6.4 Hz, 2H), 5.36 (d, J=5.1 Hz, 1H), 3.96 (dd, J=8.9, 3.2 Hz, 1H), 3.73 (t, J=8.0 Hz, 1H), 3.52 (dq, J=11.1, 5.8, 5.1 Hz, 1H), 2.33-2.20 (m, 2H), 2.08-1.97 (m, 2H), 1.91-1.80 (m, 4H), 1.68-1.61 (m, 1H), 1.56-1.46 (m, 5H), 1.41-1.32 (m, 3H), 1.15 (d, J=6.6 Hz, 3H), 1.09 (d, J=4.0 Hz, 2H), 1.02 (s, 3H), 0.98-0.92 (m, 1H), 0.91-0.80 (m, 2H), 0.74 (s, 3H).

Example 181: (8S,9S,10R,13S,14S,17R)-10,13-dimethyl-17-((S)-1-(pyridin-4-yloxy)propan-2-yl)-2,3,4,7,8,9,10,11,12,13,14,15,16,17-tetradecahydro-1H-cyclopenta[a]phenanthren-3-ol

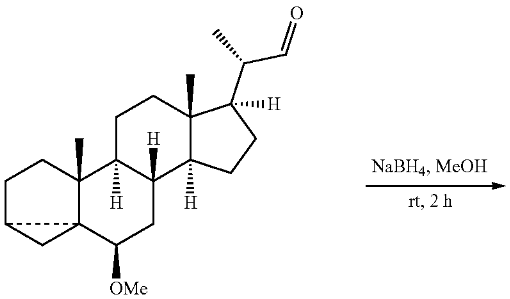

A

-continued

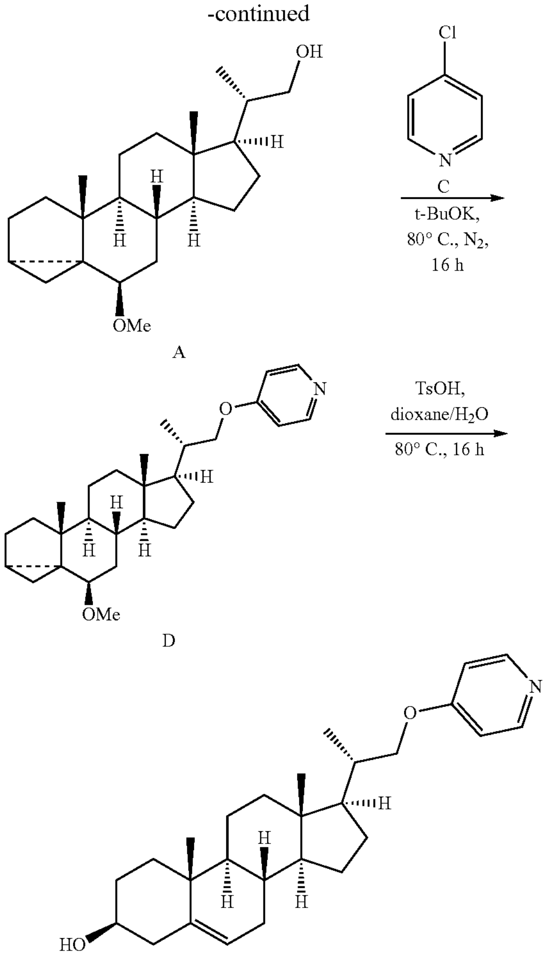

A

D

181

To a solution of compound A (1.0 g, 2.9 mmol) in methanol (10 mL) was added $NaBH_4$ (110 mg, 2.9 mmol). The mixture was stirred at room temperature for 2 h. After completion, the mixture was diluted with water and adjusted pH with HCl (1M) to ~3. After extraction with ethyl acetate (15 mL×3), the combined organic phases were washed with brine, dried over sodium sulfate, filtered, and concentrated in vacuo to afford compound B (950 mg, 94%).

To a solution of compound B (500 mg, 1.44 mmol) in dimethylformamide (10 mL) was added C (216 mg, 1.44 mmol) and tBuOK (648 mg, 4 eq, 5.77 mmol). The mixture was stirred 16 h at 80° C. under $N_2$. The mixture was diluted with $H_2O$ (15 mL) and extracted with ethyl acetate (10 mL×3). The combined organic phases were washed with brine, dried over sodium sulfate, filtered, and concentrated in vacuo to afford compound D (600 mg, 98%).

To a solution of compound D (200 mg, 472 μmol) in 1,4-dioxane (8 mL) and water (2 mL) was added 4-methylbenzene-1-sulfonic acid (16.3 mg, 0.2 eq, 94.4 μmol). After being stirred at 80° C. for 16 h, the mixture was concentrated in vacuo and the residue was purified by column chromatography to afford compound 181 (26.4 mg, 14%).$^1$H NMR (400 MHz, $CDCl_3$) δ 8.48 (d, J=5.3 Hz, 2H), 6.95 (d, J=5.8 Hz, 2H), 5.39 (s, 1H), 4.06 (d, J=8.7 Hz, 1H), 3.85 (t, J=8.1 Hz, 1H), 3.61-3.48 (m, 1H), 2.44-2.26 (m, 2H), 2.18-1.80 (m, 7H), 1.73-1.33 (m, 12H), 1.18 (d, J=6.7 Hz, 4H), 1.06 (s, 3H), 0.78 (s, 3H).

Example 182: (1R,3aS,3bS,7S,9aR,9bS,11aS)-9a,11a-dimethyl-1-[(2S)-1-phenoxypropan-2-yl]-1H,2H,3H,3aH,3bH,4H,6H,7H,8H,9H,9aH,9bH,10H,11H,11aH-cyclopenta[a]phenanthren-7-ol

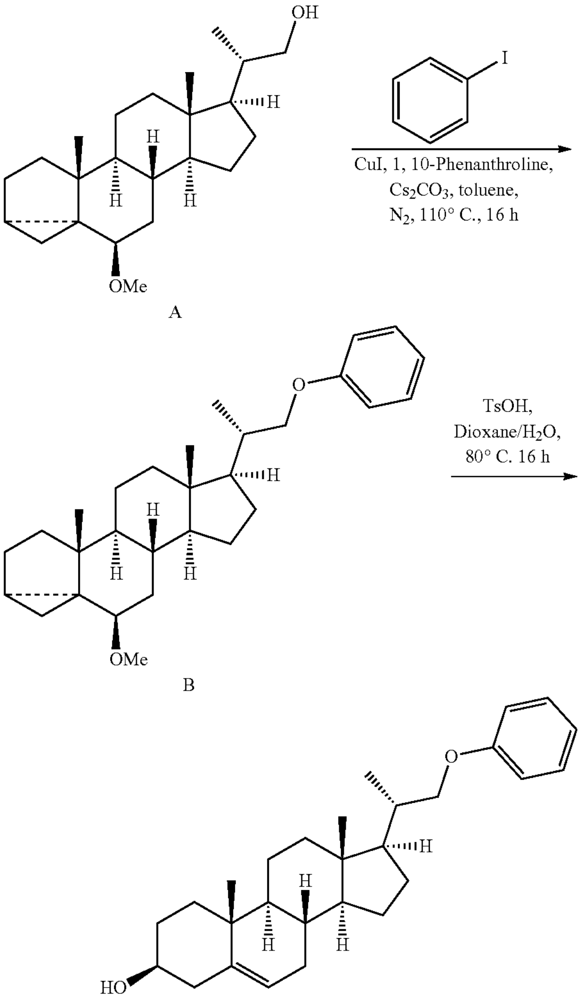

A

B

182

A mixture of compound A (150 mg, 433 μmol), iodobenzene (88.3 mg, 433 μmol), CuI (8.24 mg, 0.1 eq, 43.3 μmol), 1,10-phenanthroline (17.2 mg, 0.2 eq, 86.6 μmol) and cesium carbonate (282 mg, 2 eq, 866 μmol) in toluene (5 mL) was stirred at 110° C. for 16 h under $N_2$. After completion, the mixture was diluted with water and extracted with ethyl acetate. The combined organic phase was concentrated, and the residue was purified by column chromatography to afford compound B (20 mg, 10%).

To a solution of compound B (20 mg, 47.3 μmol) in 1,4-dioxane (7 mL) and water (1 mL) was added 4-methylbenzene-1-sulfonic acid (6.11 mg, 0.2 eq, 35.5 μmol) at room temperature. After being stirred at 80° C. for 16 h, the mixture was diluted with water and extracted with ethyl acetate. The combined organic layer was dried in vacuo and the residue was purified by column chromatography to afford compound 182 (6 mg, 31%). $^1$H NMR (400 MHz, $CDCl_3$) δ 7.25-7.20 (m, 2H), 6.93-6.80 (m, 3H), 5.33 (d, J=5.1 Hz, 1H), 3.90 (dd, J=8.9, 3.2 Hz, 1H), 3.64 (t, J=8.1 Hz, 1H), 3.50 (tt, J=10.7, 4.5 Hz, 1H), 2.33-2.14 (m, 2H), 2.06-1.91 (m, 2H), 1.90-1.74 (m, 4H), 1.54-1.39 (m, 7H), 1.36-1.20 (m, 5H), 1.11 (d, J=6.7 Hz, 3H), 0.99 (s, 3H), 0.71 (s, 3H).

Example 183: (3S,8S,9S,10R,13R,14S,17R)-17-((R)-4-(isothiazol-5-yl)butan-2-yl)-10,13-dimethyl-2,3,4,7,8,9,10,11,12,13,14,15,16,17-tetradecahydro-1H-cyclopenta[a]phenanthren-3-ol

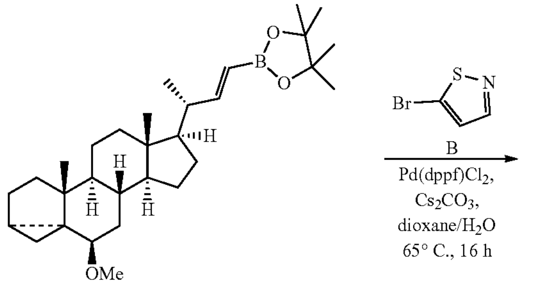

A

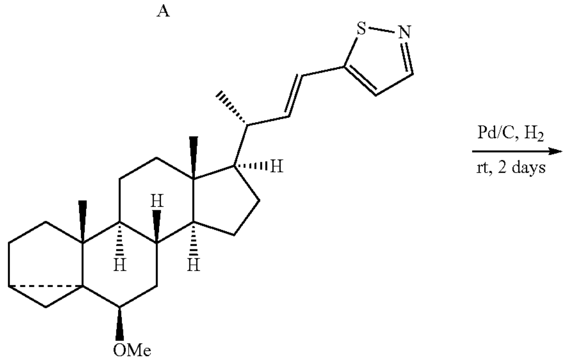

C

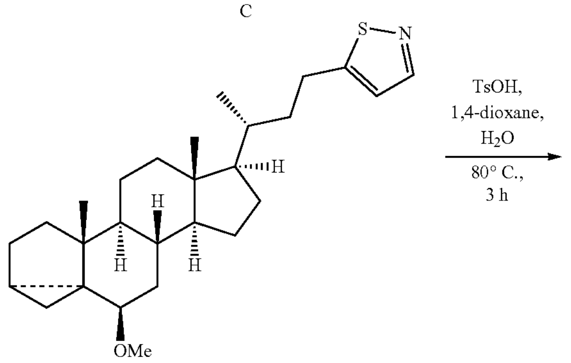

D

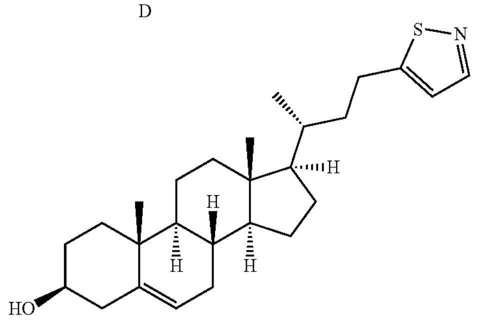

183

To a solution of compound A (470 mg, 1.0 mmol) in 1,4-dioxane(14 mL) and water (2 mL) were added compound B (165 mg, 1.0 mmol), $Cs_2CO_3$ (820 mg, 2.51 mmol) and Pd(dppf)$Cl_2$ (72.8 mg, 0.1 mmol). The mixture was stirred at 65° C. for 16 h under nitrogen. After completion, the mixture was extracted with water and ethyl acetate. The combined organic layer was dried over sodium sulfate, filtered, and concentrated to give the crude product that was purified by column chromatography to give compound C (410 mg, 96%).

To a solution of compound C (410 mg, 963 μmol) in methanol (10 mL) was added Pd/C (82 mg, 20% weight). The mixture was stirred at room temperature for 2 days under 1 atm of hydrogen. After completion, the mixture was filtered and concentrated to give compound D (330 mg, 80%). LCMS: $[M+H]^+$=428.7.

To a solution of compound D (330 mg, 772 μmol) in 1,4-dioxane (8 mL) and water (2 mL) was added 4-methylbenzene-1-sulfonic acid (26 mg, 154 μmol). The mixture was stirred at 80° C. for 3 h. After completion, the mixture was washed with $NaHCO_3$ and extracted with ethyl acetate. The organic layer was dried over sodium sulfate, filtered, and concentrated to give the crude product that was purified by column chromatography to yield compound 183 (200 mg, 63%) as a white solid. $^1$H NMR (400 MHz, $CDCl_3$) δ 8.35 (s, 1H), 6.97 (s, 1H), 5.35 (s, 1H), 3.64-3.44 (m, 1H), 2.99 (d, J=10.8 Hz, 1H), 2.85 (d, J=6.8 Hz, 1H), 2.35-2.16 (m, 2H), 2.08-1.92 (m, 2H), 1.91-1.77 (m, 4H), 1.66-1.38 (m, 9H), 1.27 (d, J=11.2 Hz, 1H), 1.17 (t, J=8.0 Hz, 2H), 1.08 (s, 1H), 1.01 (d, J=4.8 Hz, 8H), 0.68 (s, 3H).

Example 184: bis((1R,3aS,3bS,7S,9aR,9bS,11aR)-1-[(2R)-4-(3-chloropyridin-2-yl)butan-2-yl]-9a,11a-dimethyl-1H,2H,3H,3aH,3bH,4H,6H,7H,8H,9H,9aH,9bH,10H,11H,11aH-cyclopenta[a]phenanthren-7-ol)

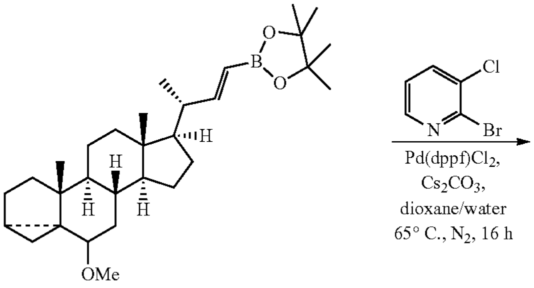

A

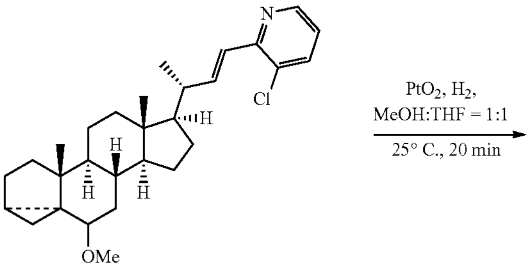

B

-continued

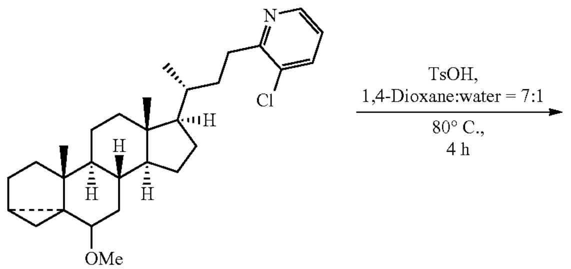

C

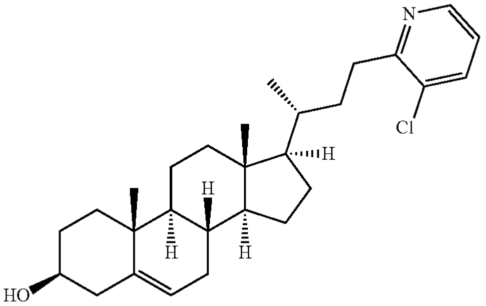

184

To a solution of compound A (500 mg, 1.07 mmol) in 1,4-dioxane (14 mL) and water (2 mL) was added 2-bromo-3-chloropyridine (205 mg, 1.07 mmol), cesium carbonate (869 mg, 2.5 eq, 2.67 mmol) and Pd(dppf)$Cl_2$ (77.4 mg, 0.1 eq, 107 μmol). The reaction was stirred at 65° C. for 16 h under $N_2$ atmosphere. After completion, the mixture was diluted with water and extracted with ethyl acetate. The combined organic phase was washed with brine, dried with sodium sulfate, and filtered. The solvent was evaporated in vacuo to afford the crude product that was purified by column chromatography to give compound B (450 mg, 92%).

To a mixture of compound B (295 mg, 162 μmol) and $PtO_2$ (29.5 mg, 10% weight) in methanol (2 mL) and THE (2 mL) was stirred at 25° C. for 20 mins under 1 atm of $H_2$. After completion, the mixture was filtered, and the solvent was concentrated to afford the crude product that was purified by column chromatography to afford compound C (65 mg, 21%).

To a solution of compound C (65 mg, 71.3 μmol) in 1,4-dioxane (7 mL) and water (1 mL) was added 4-methylbenzene-1-sulfonic acid (2.45 mg, 0.2 eq, 14.3 μmol). The reaction was stirred at 80° C. for 4 h. The mixture was extracted with ethyl acetate and the organic phase was washed with brine, dried with sodium sulfate, and filtered. The solvent was evaporated in vacuo to afford crude product that was purified by column chromatography to afford compound 184 (13 mg, 20%). $^1H$ NMR (400 MHz, $CDCl_3$) δ 8.42 (dd, J=4.8, 1.6 Hz, 1H), 7.62 (dd, J=8.1, 1.6 Hz, 1H), 7.08 (dd, J=8.0, 4.8 Hz, 1H), 5.35 (d, J=5.1 Hz, 1H), 3.52 (tt, J=10.6, 4.5 Hz, 1H), 3.01 (td, J=12.4, 4.7 Hz, 1H), 2.82 (td, J=12.4, 5.1 Hz, 1H), 2.34-2.16 (m, 2H), 2.07-1.76 (m, 6H), 1.62-1.41 (m, 10H), 1.35-1.15 (m, 4H), 1.12-0.90 (m, 10H), 0.69 (s, 3H).

Example 185: (1R,3aS,3bS,7S,9aR,9bS,11aR)-9a, 11a-dimethyl-1-[(2R)-4-[3-(trifluoromethyl)pyridin-2-yl]butan-2-yl]-1H,2H,3H,3aH,3bH,4H,6H,7H,8H, 9H,9aH,9bH,10H,11H, 11 aH-cyclopenta[a] phenanthren-7-ol

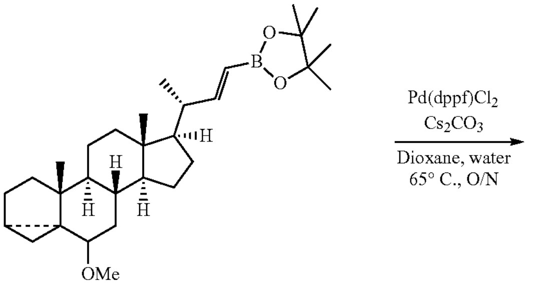

A

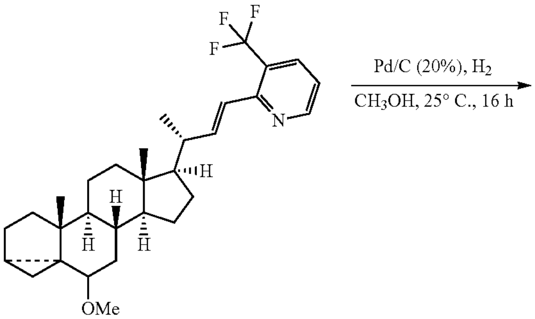

B

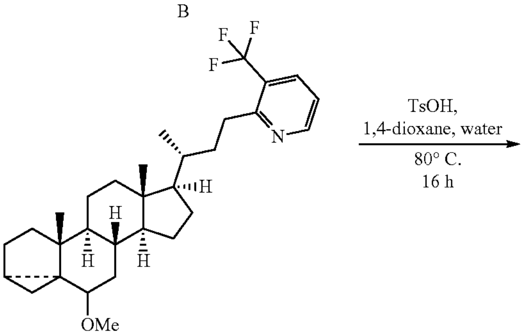

C

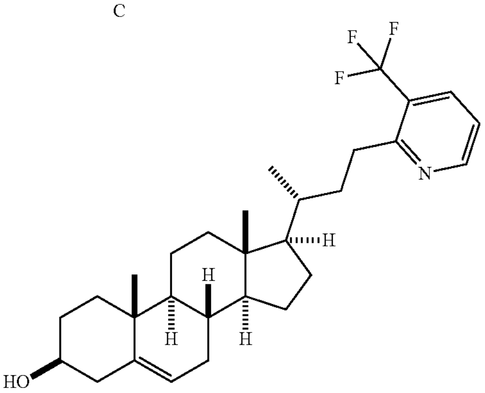

185

To a solution of compound A (300 mg, 0.66 mmol) in 1.4-dioxane (6 mL) and water (1 mL) were added 2-bromo-3-(trifluoromethyl)pyridine (149 mg, 660 mmol), cesium carbonate (538 mg, 1.65 mmol), and Pd(dppf)$Cl_2$ (47.9 mg, 66 μmol). The mixture was stirred at 65° C. for 16 h under nitrogen. After completion, the mixture was diluted with water and extracted with ethyl acetate. The organic layer was washed with brine, dried over sodium sulfate, filtered, and concentrated to give the crude product that was purified by column chromatography to afford compound B (210 mg, 65%).

To a solution of compound B (170 mg, μmol) in methanol (5 mL) was added Pd/C (34 mg, 20% weight). The mixture was stirred at room temperature for 16 h under 1 atm of hydrogen. The mixture was filtered and concentrated to give the crude product that was purified by column chromatography to compound C (160 mg, 94%).

To a solution of compound C (160 mg, 327 μmol) in 1,4-dioxane (5 mL) and water (1 mL) at room temperature was added TsOH (11.4 mg, 65.4 μmol). The mixture was warmed to 80° C. and stirred for 16 h. After completion, the solvent was removed in vacuo. The residue was diluted with water; the pH was adjusted with saturated $NaHCO_3$ to ~7 and extracted with ethyl acetate. The organic layer was washed with brine, dried over sodium sulfate, filtered, and concentrated. The residue was purified by column chromatography to afford compound 185 (80 mg, 168 μmol) as a white solid. $^1$H NMR (400 MHz, $CDCl_3$) δ 8.70 (d, J=4.8 Hz, 1H), 7.90 (d, J=7.9 Hz, 1H), 7.25-7.18 (m, 1H), 5.47-5.25 (m, 1H), 3.53 (dq, J=11.3, 6.0, 5.2 Hz, 1H), 3.03 (td, J=12.6, 4.7 Hz, 1H), 2.90-2.71 (m, 1H), 2.36-2.15 (m, 2H), 2.09-1.77 (m, 6H), 1.66-1.39 (m, 11H), 1.37-0.85 (m, 13H), 0.70 (s, 3H).

Example 186: (1R,3aS,3bS,7S,9aR,9bS,11aR)-1-[(2R)-4-(3-methoxypyridin-2-yl)butan-2-yl]-9a,11a-dimethyl-1H,2H,3H,3aH,3bH,4H,6H,7H,8H,9H,9aH,9bH,10H,11H,11aH-cyclopenta[a]phenanthren-7-ol

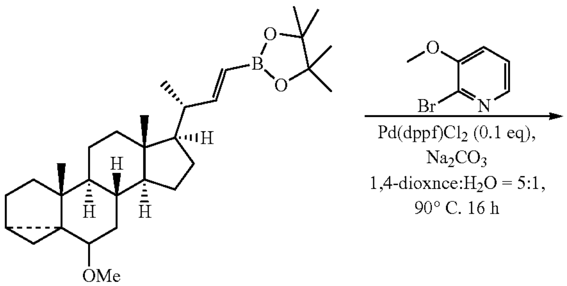

A

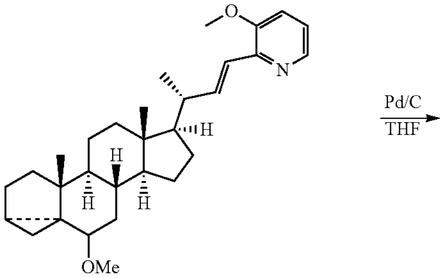

B

-continued

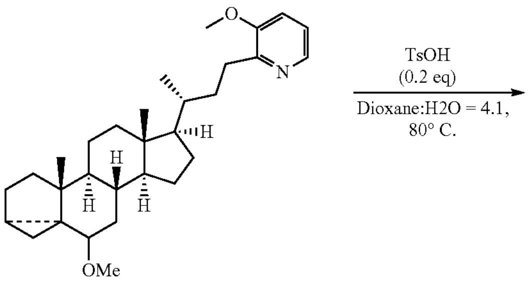

C

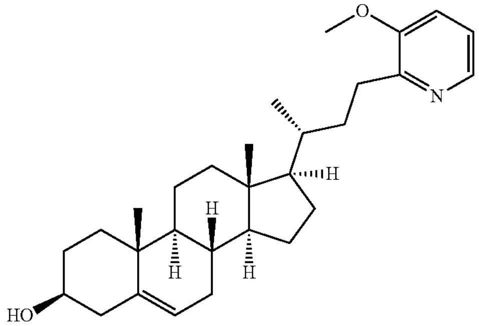

186

To a solution of compound A (200 mg, 427 μmol) in a mixture of 1,4-dioxane (5 mL) and water (1 mL) were added sodium carbonate (113 mg, 1.07 mmol), 2-bromo-3-methoxypyridine (161 mg, 854 μmol), and Pd(dppf)$Cl_2$ (31 mg, 42.7 μmol). The mixture was heated at 90° C. for 2 h under nitrogen. After being cooled to ambient temperature, the mixture was filtered through Celite, and the filtrate was concentrated in vacuo. Then residue was purified by column chromatography (eluting with 1/20 ethyl acetate/petroleum ether) to afford compound B (75 mg, 39.1%).

To a solution of compound B (75 mg, 167 μmol) in THE (3 mL) was added Pd/C (15 mg, 20% weight). The mixture purged with hydrogen three times and stirred for 2 h under 1 atm of $H_2$ at room temperature. After completion, the mixture was filtered through Celite and concentrated in vacuo to give compound C (70 mg, 92.9%).

A mixture of crude compound C (70 mg, 155 μmol) and 4-methylbenzene-1-sulfonic acid hydrate (5.9 mg, 31 μmol) in 1,4-dioxane (2 mL) and water (1 mL) was heated at 80° C. for 3 h under an atmosphere of nitrogen. After completion, the pH of the mixture was adjusted to 7 with saturated $NaHCO_3$ solution and extracted with ethyl acetate. The organic layer was dried over anhydrous sodium sulfate and concentrated in vacuo to give the crude product that was purified by column chromatography (eluting with 1/5 ethyl acetate/petroleum ether) to afford compound 186 (34.7 mg, 51.2%). $^1$H NMR (400 MHz, $CDCl_3$) δ 8.11 (t, J=3.0 Hz, 1H), 7.10 (d, J=3.0 Hz, 2H), 5.35 (d, J=5.0 Hz, 1H), 3.84 (s, 3H), 3.52 (s, 1H), 2.90 (d, J=4.8 Hz, 1H), 2.72 (d, J=5.4 Hz, 1H), 2.34-2.16 (m, 2H), 2.07-1.94 (m, 2H), 1.90-1.74 (m, 4H), 1.65-1.50 (m, 8H), 1.43 (s, 1H), 1.36-1.24 (m, 2H), 1.23-1.14 (m, 2H), 1.05 (d, J=6.4 Hz, 4H), 1.01 (s, 3H), 0.92 (tt, J=12.4, 5.6 Hz, 1H), 0.69 (s, 3H). LCMS: $[M+H]^+$=438.25.

Example 187: (3S,8S,9S,10R,13R,14S,17R)-17-((R)-4-(3-ethylpyridin-2-yl)butan-2-yl)-10,13-dimethyl-2,3,4,7,8,9,10,11,12,13,14,15,16,17-tetradecahydro-1H-cyclopenta[a]phenanthren-3-ol

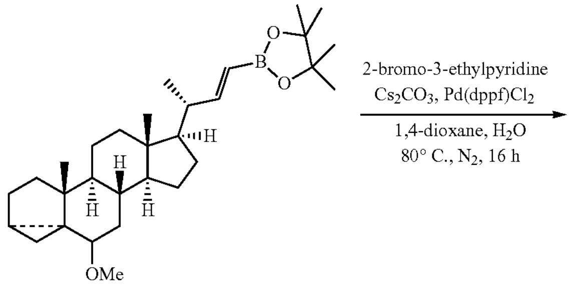

A

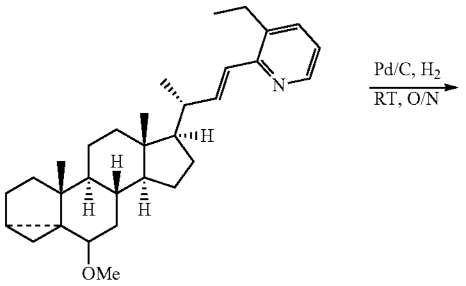

B

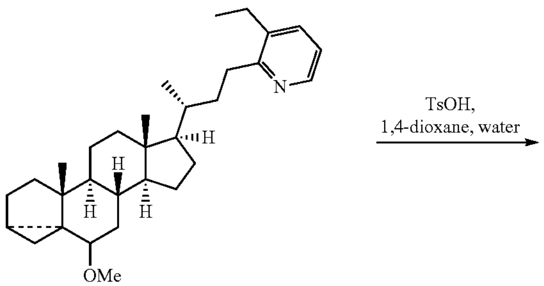

C

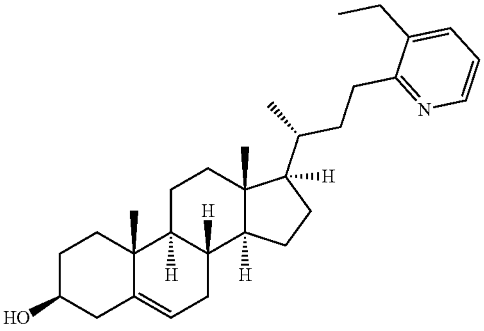

185

To a solution of compound A (100 mg, 213 μmol) in 1,4-dioxane (2 mL) and water (0.3 mL) were added 2-bromo-3-ethylpyridine (51.6 mg, 277 μmol), $Cs_2CO_3$ (174 mg, 534 μmol), and Pd(dppf)$Cl_2$ (31.2 mg, 42.7 μmol). The mixture was stirred at 80° C. for 16 h under nitrogen. After completion, the mixture was diluted with water and extracted with ethyl acetate. The combined organic layer was dried over sodium sulfate, filtered, and concentrated to give the crude product that was purified by column chromatography to give compound B (64 mg, 67%).

To a solution of compound B (64 mg, 143 μmol) in methanol (5 mL) was added Pd/C (13 mg, 20% weight). The mixture was stirred at room temperature for 4 h under 1 atm of hydrogen. After completion, the mixture was filtered and concentrated to give compound C (54 mg, 84%).

To a solution of compound C (54 mg, 120 μmol) in 1,4-dioxane (2.8 mL) and water (0.7 mL) was added 4-methylbenzene-1-sulfonic acid (4.58 mg, 24 μmol). The mixture was stirred at 80° C. for 3 h. After completion, the mixture was quenched with $NaHCO_3$ and extracted with ethyl acetate. The organic layer was dried over sodium sulfate, filtered, and concentrated to give the crude product that was purified by column chromatography to yield compound 187 (45 mg, 86%) as white solid. $^1H$ NMR (400 MHz, $CDCl_3$) δ 8.44-8.39 (m, 1H), 7.52 (s, 1H), 7.13 (s, 1H), 5.39 (d, J=5.0 Hz, 1H), 3.56 (d, J=4.8 Hz, 1H), 2.93 (d, J=13.2 Hz, 1H), 2.71 (s, 3H), 2.32 (d, J=6.0 Hz, 2H), 2.11-1.96 (m, 3H), 1.88 (d, J=9.4 Hz, 5H), 1.64-1.52 (m, 7H), 1.36-1.32 (m, 1H), 1.28 (s, 3H), 1.26 (s, 1H), 1.21 (d, J=10.0 Hz, 1H), 1.13-1.02 (m, 9H), 0.74 (s, 3H).

Example 188: (3S,8S,9S,10R,13R,14S,17R)-10,13-dimethyl-17-((R)-4-(4-methylpyrimidin-5-yl)butan-2-yl)-2,3,4,7,8,9,10,11,12,13,14,15,16,17-tetradecahydro-1H-cyclopenta[a]phenanthren-3-ol

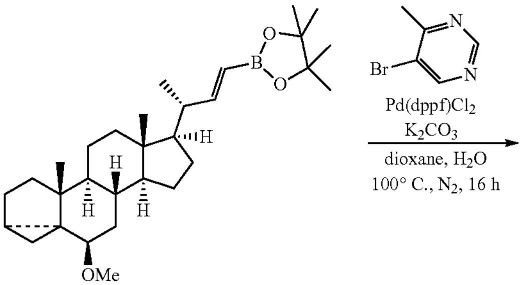

A

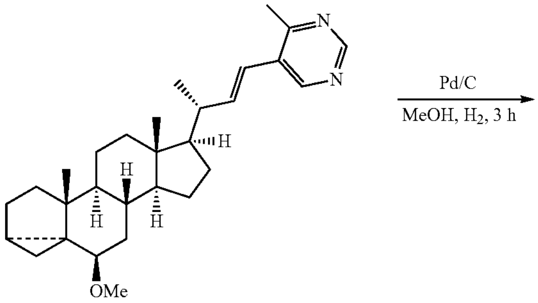

B

-continued

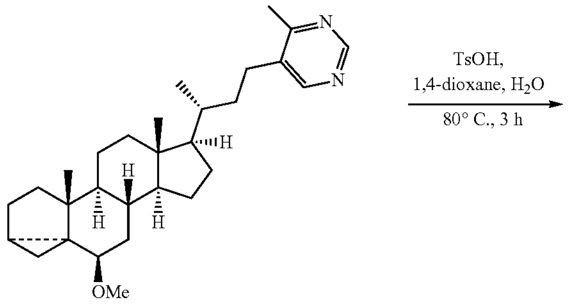

C

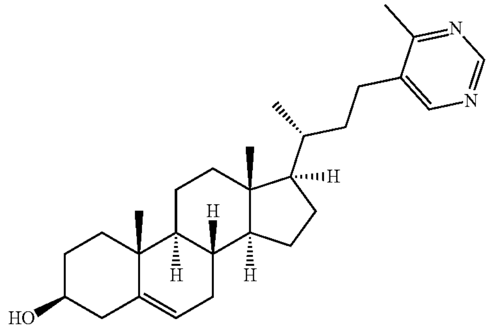

188

The solution of compound A (100 mg, 0.21 mmol) in 1.4-dioxane (0.8 mL) and water (0.1 mL) were added 4-chloro-5-methylpyrimidine (82.3 mg, 640 μmol), $K_2CO_3$ (59 mg, 427 μmol), and Pd(dppf)$Cl_2$ (31.2 mg, 42.7 μmol). The mixture was stirred at 100° C. for 16 h under nitrogen. After completion, the mixture was washed with water and extracted with ethyl acetate (10 mL×3). The organic layer was washed with brine, dried over sodium sulfate, filtered, and concentrated to give the crude product that was purified by column chromatography to afford compound B (72 mg, 77%). LCMS: $[M+H]^+$=435.33.

The solution of compound B (72 mg, 0.16 mmol) in methanol (2 mL) was added Pd/C (14 mg, 20% weight). The reaction was stirred at room temperature for 3 h under 1 atm of hydrogen. After completion, the mixture was filtered and concentrated to give the crude product that was purified by column chromatography to give compound C (54 mg, 75%) LCMS: $[M+H]^+$=437.33.

To a solution of compound C (54 mg, 0.12 mmol) in 1.4-dioxane (0.7 mL) and water (0.1 mL) was added TsOH (5.2 mg, 0.03 mmol). The mixture was stirred at 80° C. for 3 h. After completion, the mixture was washed with $NaHCO_3$ and extracted with ethyl acetate (10 mL×3). The organic layer was washed with brine, dried over sodium sulfate, filtered, and concentrated to give the crude product that was purified by column chromatography to yield compound 188 (37 mg, 74%). $^1H$ NMR (400 MHz, $CDCl_3$) δ 9.02 (s, 1H), 8.48 (s, 1H), 5.36 (d, J=5.1 Hz, 1H), 3.56-3.48 (m, 1H), 2.90 (dt, J=11.9, 6.4 Hz, 1H), 2.72 (d, J=4.0 Hz, 1H), 2.34 (s, 3H), 2.30-2.20 (m, 2H), 2.04 (d, J=14.0 Hz, 2H), 1.92-1.78 (m, 5H), 1.58 (s, 1H), 1.52-1.46 (m, 6H), 1.38 (d, J=5.5 Hz, 1H), 1.30-1.20 (m, 6H), 1.08 (d, J=6.5 Hz, 4H), 1.02 (s, 3H), 0.98-0.94 (m, 1H), 0.86 (t, J=9.5 Hz, 3H), 0.70 (s, 3H).

Example 189: (1R,3aS,3bS,7S,9aR,9bS,11aR)-9a, 11a-dimethyl-1-[(2R)-4-(6-methylpyrimidin-4-yl) butan-2-yl]-1H,2H,3H,3aH,3bH,4H,6H,7H,8H,9H, 9aH,9bH,10H,11H,11aH-cyclopenta[a]phenanthren-7-ol

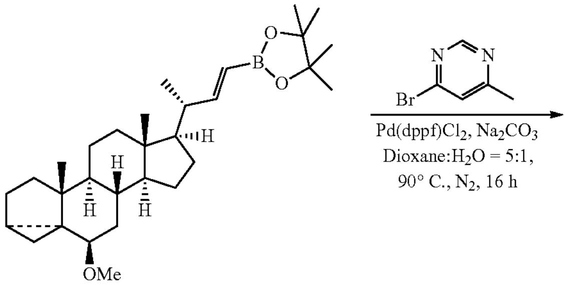

A

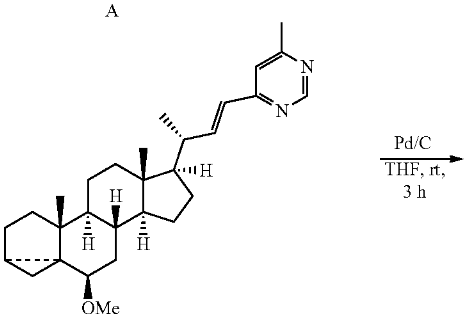

B

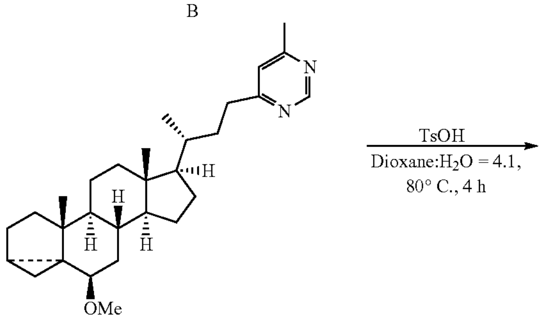

C

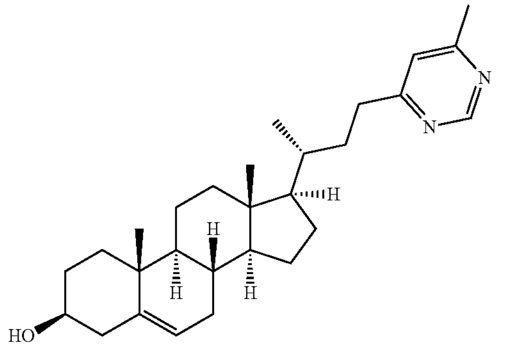

189

To a solution of compound A (100 mg, 213 μmol) in a mixture of 1,4-dioxane (2.5 mL) and water (0.5 mL) were added sodium carbonate (56.6 mg, 534 μmol), 4-bromo-6-methylpyrimidine (48 mg, 277 μmol), and Pd(dppf)$Cl_2$ (15.5 mg, 21.3 μmol). The mixture was heated for 16 h at 90° C. under nitrogen. After being cooled to ambient temperature, the mixture was filtered through Celite, and the filtrate was concentrated in vacuo. The residue was purified by column chromatography (eluting with 1/20 ethyl acetate/petroleum ether) to afford compound B (80 mg, 86.2%).

To a solution of compound B (80 mg, 184 μmol) in THE (3 mL) was added Pd/C (16 mg, 20% weight). The mixture was purged with hydrogen three times and stirred under 1 atm of $H_2$ for 3 h at room temperature. After completion, the mixture was filtered through Celite and concentrated in vacuo to give compound C (50 mg, 62.2%).

A mixture of crude compound C (50 mg, 114 μmol) and 4-methylbenzene-1-sulfonic acid hydrate (4.36 mg, 22.9 μmol) in 1,4-dioxane (2 mL) and water (0.5 mL) was heated at 80° C. for 4 h under. The pH of the mixture was adjusted to 7 with saturated $NaHCO_3$ solution, and the mixture was extracted with ethyl acetate. The organic layer was dried over anhydrous sodium sulfate, filtered, and concentrated in vacuo to give the crude product that was purified by column chromatography (eluting with 1/1 ethyl acetate/petroleum ether) to afford compound 189 (15.3 mg, 31.6%). $^1$H NMR (400 MHz, $CDCl_3$) δ 8.98 (s, 1H), 7.04 (s, 1H), 5.35 (d, J=5.0 Hz, 1H), 3.52 (d, J=5.6 Hz, 1H), 2.79 (t, J=11.4 Hz, 1H), 2.65-2.54 (m, 1H), 2.51 (s, 3H), 2.33-2.19 (m, 2H), 2.05-1.94 (m, 2H), 1.85 (d, J=12.2 Hz, 4H), 1.65-1.52 (m, 6H), 1.28 (d, J=16.6 Hz, 4H), 1.22-1.06 (m, 4H), 1.03 (d, J=6.2 Hz, 3H), 1.01 (s, 3H), 0.98-0.85 (m, 2H), 0.68 (s, 3H). LCMS: $[M+H]^+$=423.30.

Example 190: (3S,8S,9S,10R,13R,14S,17R)-10,13-dimethyl-17-((R)-4-(2-methylpyrimidin-4-yl)butan-2-yl)-2,3,4,7,8,9,10,11,12,13,14,15,16,17-tetradecahydro-1H-cyclopenta[a]phenanthren-3-ol

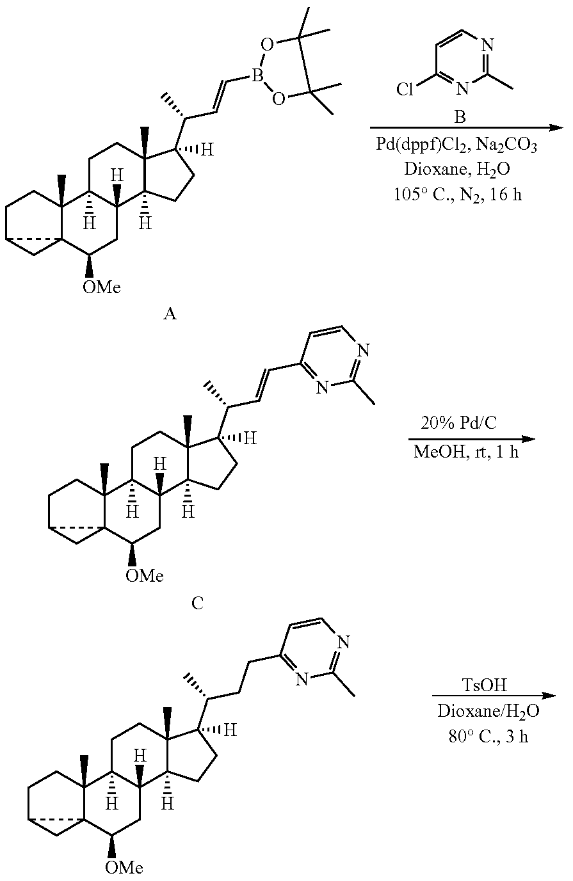

A

C

D

-continued

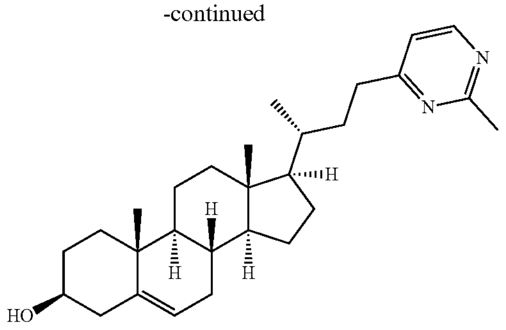

190

To a solution of compound A (500 mg, 1.07 mmol) in 1,4-dioxane (9 mL) and wate (1 mL) were added compound B (412 mg, 3.2 mmol), Pd(dppf)C12 (123 mg, 107 μmol) and sodium carbonate (295 mg, 2.13 mmol) at room temperature. The mixture was stirred at 105° C. for 16 h under $N_2$. The solvent was evaporated to afford the crude product that was purified by column chromatography to give compound C (300 mg, 65%) as a white solid.

To a solution of compound C (150 mg, 345 μmol) in MeOH (5 mL) was added Pd/C (30 mg, 20% weight) at room temperature. The mixture was stirred at room temperature under 1 atm of $H_2$ for 1 h. After completion, the mixture was filtered and evaporated to afford compound D (150 mg, 99%) as a white solid.

To a solution of compound D (150 mg, 345 μmol) in 1,4-dioxane (4.0 mL) and water (1.0 mL) was added 4-methylbenzene-1-sulfonic acid (11.9 mg, 69 μmol) at room temperature. The mixture was stirred at 80° C. for 3 h. The result solution was quenched by the addition of $NaHCO_3$ and then extracted with DCM (50 mL×3). The combined organic layers were dried over sodium sulfate and concentrated to give crude product that was purified by column chromatography to compound 190 (24.3 mg, 17%) as a white solid. $^1$H NMR (400 MHz, $CDCl_3$) δ 8.49 (d, J=5.2 Hz, 1H), 6.97 (d, J=5.2 Hz, 1H), 5.35 (d, J=5.2 Hz, 1H), 3.52 (tt, J=10.8, 4.8 Hz, 1H), 2.80 (m, 1H), 2.71 (s, 3H), 2.64-2.54 (m, 1H), 2.33-2.18 (m, 2H), 2.04-1.94 (m, 2H), 1.90-1.79 (m, 4H), 1.61-1.40 (m, 9H), 1.28 (d, J=11.4 Hz, 1H), 1.22-1.05 (m, 4H), 1.02 (d, J=8.6 Hz, 6H), 0.94 (dt, J=11.2, 5.2 Hz, 1H), 0.68 (s, 3H). LCMS: $[M+H]^+$=423.25.

Example 191: (3S,8S,9S,10R,13R,14S,17R)-10,13-dimethyl-17-((R)-4-(4-methylpyrimidin-2-yl)butan-2-yl)-2,3,4,7,8,9,10,11,12,13,14,15,16,17-tetradecahydro-1H-cyclopenta[a]phenanthren-3-ol

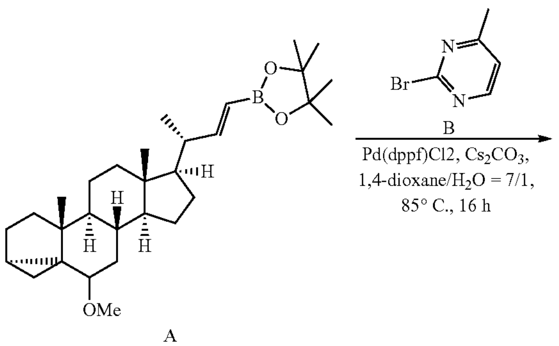

A

-continued

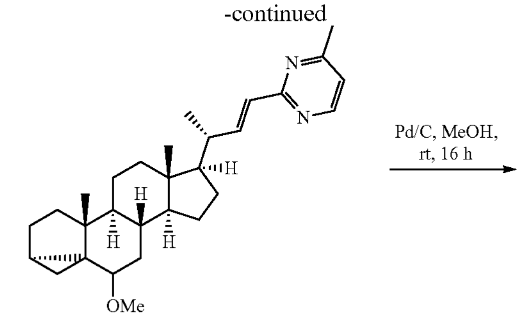

C

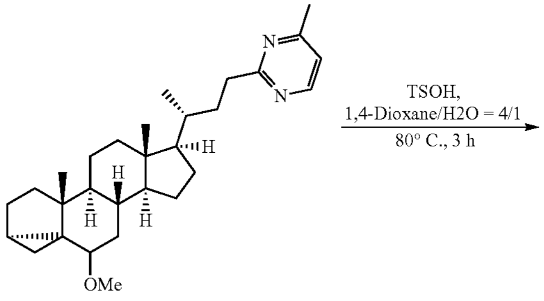

D

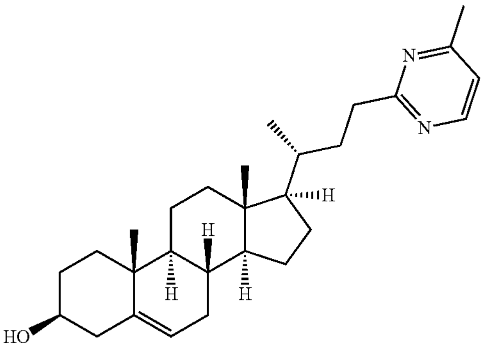

191

A solution of compound A (500 mg, 1.1 mmol) in 1,4-dioxane (9.1 mL) and $H_2O$ (1.3 mL) were added cesium carbonate (540 mg, 1.66 mmol), compound B (956 mg, 5.52 mmol), and Pd(dppf)$Cl_2$ (160 mg, 0.22 mmol), then heated at 85° C. for 16 h under $N_2$. After completion, the mixture diluted with water and extracted with ethyl acetate (100 mL×3). The organic layer was washed by brine, dried over sodium sulfate, filtered, and concentrated to give the crude product that was purified by column chromatography to yield the compound C (333 mg, 72%) as a white solid.

A mixture of compound C (333 mg, 760 μmol) and Pd/C (66.5 mg, 20% weight) in methanol (33.3 mL) was purged with $H_2$ for 3 times and stirred 16 h under 1 atm of $H_2$. After completion, the mixture was filtered through Celite and the solvent was concentrated in vacuo to afford compound D (133 mg, 35%) as a white solid.

To a solution of D (133 mg, 315 μmol) in 1,4-dioxane (4 mL) and $H_2O$ (1 mL) was added 4-methylbenzene-1-sulfonic acid (10.9 mg, 63 μmol). The mixture was stirred at 80° C. for 3 h. After completion, the mixture was washed with water and extracted with ethyl acetate (30 mL×3). The organic layer was washed with brine, dried over sodium sulfate, filtered, and concentrated to give the crude product that was purified by column chromatography to afford compound 191 (58.7 mg, 44%). $^1$H NMR (400 MHz, $CDCl_3$) δ 8.49 (d, J=5.0 Hz, 1H), 6.96 (d, J=5.0 Hz, 1H), 5.35 (d, J=5.0 Hz, 1H), 3.52 (s, 1H), 3.03-2.94 (m, 1H), 2.83-2.74 (m, 1H), 2.50 (s, 3H), 2.32-2.19 (m, 2H), 2.04-1.81 (m, 6H), 1.55-1.42 (m, 8H), 1.33-1.26 (m, 1H), 1.22-1.13 (m, 2H), 1.08 (t, J=11.8 Hz, 2H), 1.03 (d, J=5.8 Hz, 3H), 1.01 (s, 3H), 0.93 (td, J=11.2, 5.2 Hz, 1H), 0.68 (s, 3H). LCMS: $[M+H]^+$ =423.25.

Example 192: (3S,8S,9S,10R,13R,14S,17R)-10,13-dimethyl-17-((R)-4-(5-methylpyrimidin-2-yl)butan-2-yl)-2,3,4,7,8,9,10,11,12,13,14,15,16,17-tetradecahydro-1H-cyclopenta[a]phenanthren-3-ol

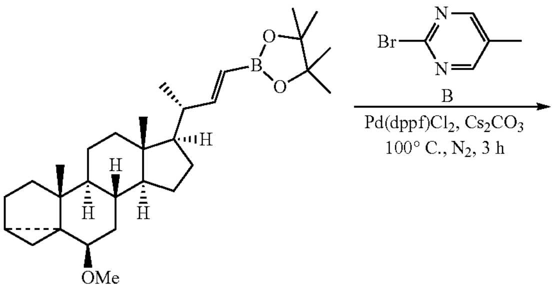

A

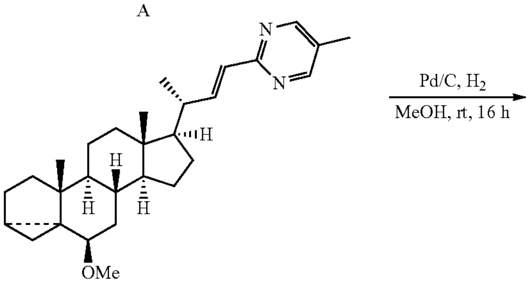

C

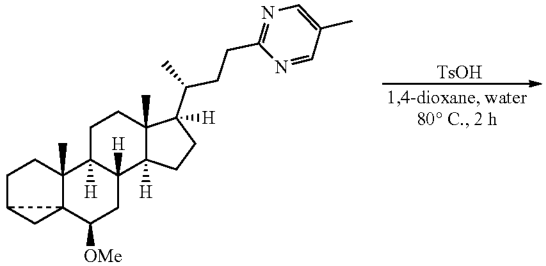

D

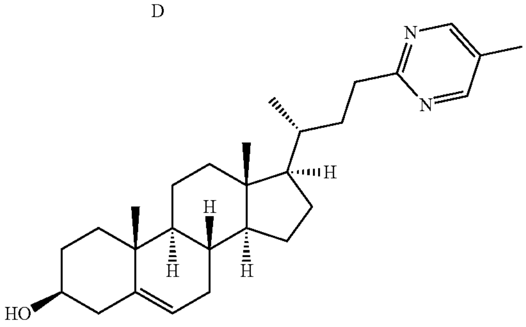

192

To a solution of compound A (300 mg, 0.64 mmol) in 1,4-dioxane (6.6 mL) and water (1.0 mL) were added compound B (554 mg, 3.2 mmol), cesium carbonate (625 mg, 1.92 mmol) and Pd(dppf)$Cl_2$ (92.9 mg, 0.128 mmol). The mixture was stirred at 100° C. under $N_2$ for 3 h. After completion, the mixture was extracted with ethyl acetate. The organic layer was dried over sodium sulfate and concentrated to afford the crude product that was purified by column chromatography to afford compound C (240 mg, 86%).

A mixture of compound C (100 mg, 0.23 mmol) and Pd/C (20 mg, 20% weight) in methanol (3 mL) was purged with $H_2$ for 3 times and stirred at room temperature 16 h under 1 atm of $H_2$. After completion, the mixture was filtered and the solvent was concentrated to afford compound D (90 mg, 90%).

To a solution of compound D (90 mg, 0.206 mmol) in 1,4-dioxane (2 mL) and water (0.5 mL) was added TsOH (7.8 mg, 0.041 mmol). The mixture was stirred at 80° C. for 2 h. After completion, the mixture was extracted with ethyl acetate. The organic layer was dried over sodium sulfate and concentrated to afford the crude product that was purified by column chromatography to afford compound 192 (42.4 mg, 49%). $^1$H NMR (400 MHz, $CDCl_3$) δ 8.50 (s, 2H), 5.34 (d, J=4.9 Hz, 1H), 3.52 (t, J=5.0 Hz, 1H), 2.99 (d, J=3.1 Hz, 1H), 2.83 (d, J=4.2 Hz, 1H), 2.35-2.18 (m, 5H), 2.04-1.81 (m, 6H), 1.59-1.42 (m, 8H), 1.35-0.78 (m, 15H), 0.68 (s, 3H).

Examples 193 and 193A

Example 193: (R)-1-(4-cyclopropyl-4-hydroxypiperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one Example 193A: (R)-1-(4-cyclopropyl-3,6-dihydropyridin-1 (2H)-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

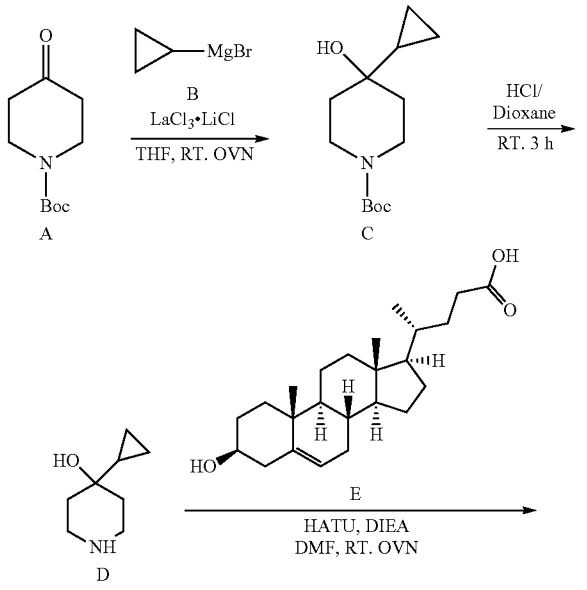

-continued

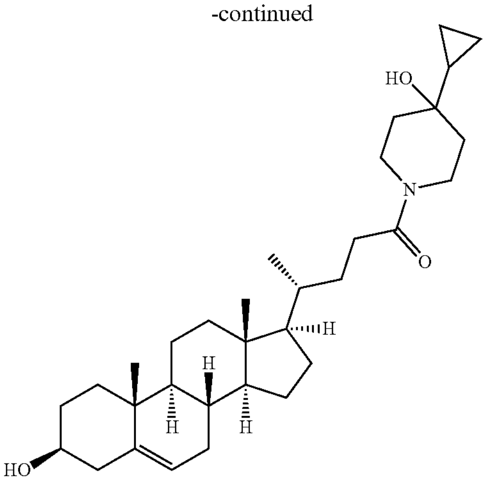

&

193

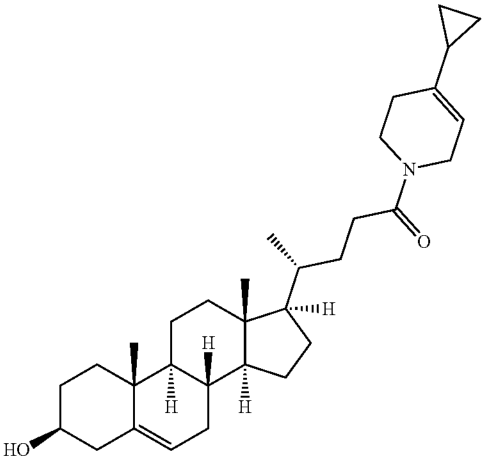

193A

To a solution of lanthanum trichloride lithium chloride complex (8.36 mL, 5.02 mmol, 0.6 M in THF) in THF (5 mL) was added compound B (10 mL, 5.0 mmol, 0.5 M in THF) at −78° C. and stirred for 1 h and then compound A (500 mg, 2.51 mmol) was added. The mixture was warmed to room temperature and stirred for 16 h. After completion, the reaction solution was quenched by the addition of water and extracted with DCM. The organic layer was washed with brine, dried over sodium sulfate, filtered, and concentrated to afford the crude product that was purified by column chromatography to give compound C (350 mg, 58%) as a white solid.

Compound C (300 mg, 1.24 mmol) was dissolved in the HCl solution in dioxane (3.1 mL, 12.4 mmol) at room temperature. The mixture was stirred for 3 h. After completion, the solvent was evaporated to give compound D (160 mg, 91%) as a white solid.

To a solution of compound E (150 mg, 0.4 mmol) in DMF (5 mL) were added compound D (84.8 mg, 601 μmol), HATU (167 mg, μmol) and DIEA (259 mg, 2 mmol) at room temperature. The mixture was stirred for 16 h. After completion, the reaction was quenched by the addition of water and extracted with ethyl acetate. The organic layer was washed by brine, dried over sodium sulfate, filtered, and concentrated to afford the crude product that was purified by column chromatography to give compounds 193 (21.5 mg, 11%) as a white solid and 201 (4.6 mg, 2%) as a white solid.

193: $^1$H NMR (400 MHz, $CDCl_3$) δ 5.35 (d, J=5.2 Hz, 1H), 4.39 (d, J=13.4 Hz, 1H), 3.64 (d, J=13.8 Hz, 1H), 3.52 (m, 1H), 3.44-3.35 (m, 1H), 3.02-2.93 (m, 1H), 2.37 (d, J=11.8 Hz, 1H), 2.30-2.19 (m, 3H), 2.03-1.94 (m, 2H), 1.84 (d, J=10.0 Hz, 3H), 1.58-1.43 (m, 12H), 1.32 (s, 3H), 1.19-1.02 (m, 5H), 0.96 (d, J=6.6 Hz, 6H), 0.68 (s, 3H), 0.44-0.33 (m, 4H). LCMS: $[M+H]^+$=498.30.

201: $^1$H NMR (400 MHz, $CDCl_3$) δ 5.43-5.31 (m, 2H), 3.99-3.92 (m, 2H), 3.69-3.46 (m, 3H), 2.40-2.17 (m, 4H), 2.05-1.92 (m, 4H), 1.88-1.70 (m, 4H), 1.53-1.41 (m, 6H), 1.30 (m, 4H), 1.18-0.82 (m, 13H), 0.68 (s, 3H), 0.60 (d, J=8.2 Hz, 2H), 0.45 (d, J=6.2 Hz, 2H). LCMS: $[M+H]^+$ =480.30.

Example:194: (R)-1-(4-cyclobutyl-4-hydroxypiperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

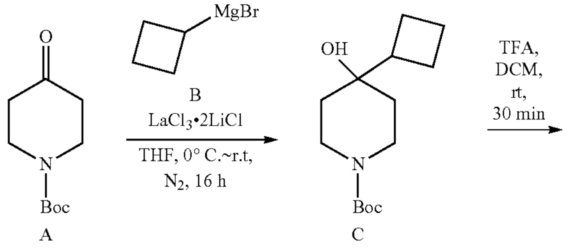

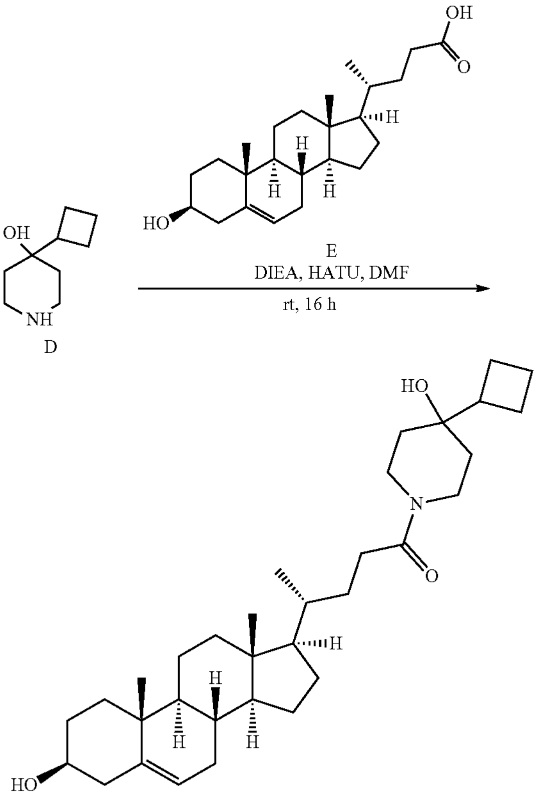

194

Lanthanum trichloride lithium chloride complex (12.5 mL, 3 eq, 7.53 mmol, 0.6 M in THF) was placed in a 100 mL 3-neck round bottom flask under $N_2$, then compound B (7.53 mL, 3 eq, 7.53 mmol, 1M in THF) was added slowly at 0° C. After stirring at room temperature for 3 h, a solution of compound A (500 mg, 2.51 mmol) in tetrahydrofuran (5 mL) was added and stirred for 16 h. The reaction was quenched by adding acetic acid (0.5 mL), then diluted with $H_2O$ (10 mL) and extracted with ethyl acetate (10 mL×3). The combined organic phases were washed with brine, dried over sodium sulfate, concentrated in vacuo. The residue was purified by column chromatography to afford compound C (520 mg, 80%) as a brown solid.

To a solution of compound C (400 mg, 1.57 mmol) in dichloromethane (5 mL) was added trifluoroacetic acid (1.6 mL). The solution was stirred at room temperature for 30 mins. After completion, the reaction mixture was concentrated in vacuo to afford compound D (200 mg, 82%).

To a solution of compound D (99.5 mg, 2 eq, 641 μmol) in dimethylformamide (10 mL) were added DIEA (290 mg, 7 eq, 2.24 mmol), HATU (365 mg, 3 eq, 961 μmol), and compound E (120 mg, 320 μmol). The solution was stirred at room temperature for 16 h. After completion, the reaction mixture was diluted with water (20 mL) and extracted with ethyl acetate (15 mL×3). The combined organic phases were washed with brine, dried over sodium sulfate, and concentrated in vacuo. The residue was purified by column chromatography to afford compound 194 (32.6 mg, 20%) as a white solid. $^1$H NMR (400 MHz, $CDCl_3$) δ 5.35 (d, J=5.1 Hz, 1H), 4.35 (d, J=13.1 Hz, 1H), 3.61 (d, J=13.4 Hz, 1H), 3.52 (tt, J=10.5, 4.5 Hz, 1H), 3.40 (d, J=13.2 Hz, 1H), 2.98 (s, 1H), 2.45-2.15 (m, 5H), 2.07-1.69 (m, 13H), 1.46-1.03 (m, 19H), 1.00 (s, 3H), 0.95 (d, J=6.5 Hz, 3H), 0.87 (dq, J=13.6, 7.7, 6.5 Hz, 2H), 0.68 (s, 3H).

Example: 195: (1S)-1-[(1S,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]ethyl

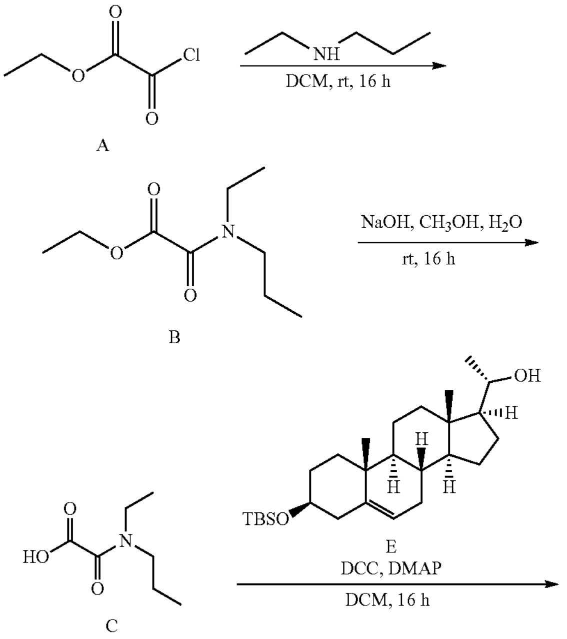

-continued

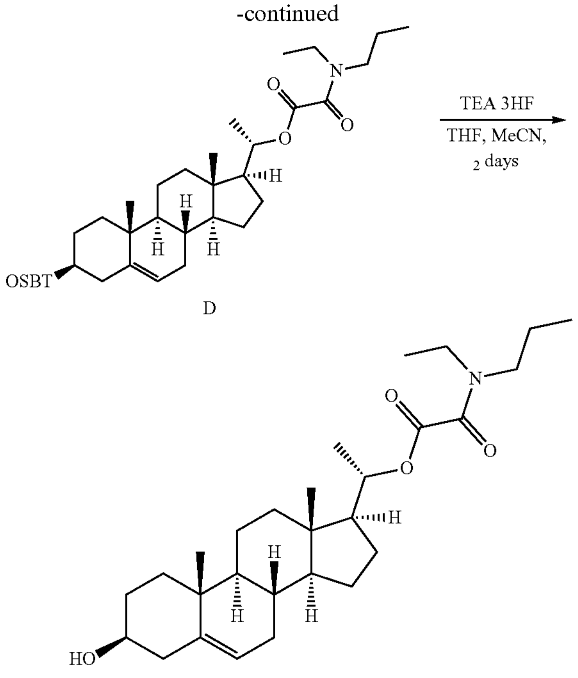

D

195

To a solution of compound A (500 mg, 3.66 mmol) in DCM (5 mL) at room temperature was added ethyl (propyl) amine (319 mg, 3.66 mmol). The mixture was stirred for 16 h. After completion, the solvent was removed in vacuo. The residue was diluted with water, extracted with ethyl acetate. The organic layer was washed by brine, dried over sodium sulfate, filtered, and concentrated. The residue was purified by column chromatography to afford compound B (300 mg, 44%) as colorless oil.

To a solution of compound B (300 mg, 1.6 mmol) in methanol (16 mL) and water (4 mL) at room temperature was added sodium hydroxide (256 mg, 6.41 mmol). The mixture was stirred for 16 h. After completion, the solvent was removed in vacuo. The residue was diluted with water, acidified with 1N HCl to pH~3 and extracted with DCM. The organic layer was washed by brine, dried over sodium sulfate, filtered, and concentrated to afford compound C (140 mg, 55%) as a colorless oil. $^1$H NMR (400 MHz, DMSO-$d_6$) δ 3.34-3.23 (m, 2H), 3.22-3.11 (m, 2H), 1.51 (m, 2H), 1.08 (m, 3H), 0.82 (m, 3H).

To a solution of compound C (140 mg, 879 μmol) and E (354 mg, 879 μmol) in DCM (10 mL) at room temperature were added N,N'-dicyclohexylmethanediimine (272 mg, 1.32 mmol) and N,N-dimethylpyridin-4-amine (10.7 mg, 87.9 μmol). The mixture was stirred for 16 h. After completion, the solvent was removed in vacuo and the crude was extracted between water and ethyl acetate. The organic layer was washed by brine, dried over sodium sulfate, filtered, and concentrated. The residue was purified by column chromatography to afford compound D (50 mg, 10%) as a yellow solid.

To a solution of compound D (50 mg, 89.6 μmol) in acetonitrile (2.5 mL) and tetrahydrofuran (2.5 mL) at room temperature was added trihydrogen fluoride triethylamine (144 mg, 896 μmol). The mixture was stirred for 2 days. After completion, the solvent was removed in vacuo. The mixture was extracted between water and ethyl acetate. The organic layer was washed by brine, dried over sodium sulfate, filtered, and concentrated. The residue was purified by column chromatography to afford compound 195 (16 mg, 38%) as a white solid. $^1$H NMR (400 MHz, $CDCl_3$) δ 5.38-5.31 (m, 1H), 5.16-5.07 (m, 1H), 3.57-3.48 (m, 1H), 3.47-3.35 (m, 1H), 3.34-3.23 (m, 2H), 3.21-3.13 (m, 1H), 2.36-2.18 (m, 2H), 2.03-1.79 (m, 5H), 1.68-1.57 (m, 6H), 1.55-1.41 (m, 6H), 1.35 (m, 3H), 1.32-1.28 (m, 1H), 1.19 (m, 5H), 1.01 (s, 3H), 0.91 (m, 4H), 0.73 (s, 3H).

Example 196: (S)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethyl 2-(dipropylamino)-2-oxoacetate

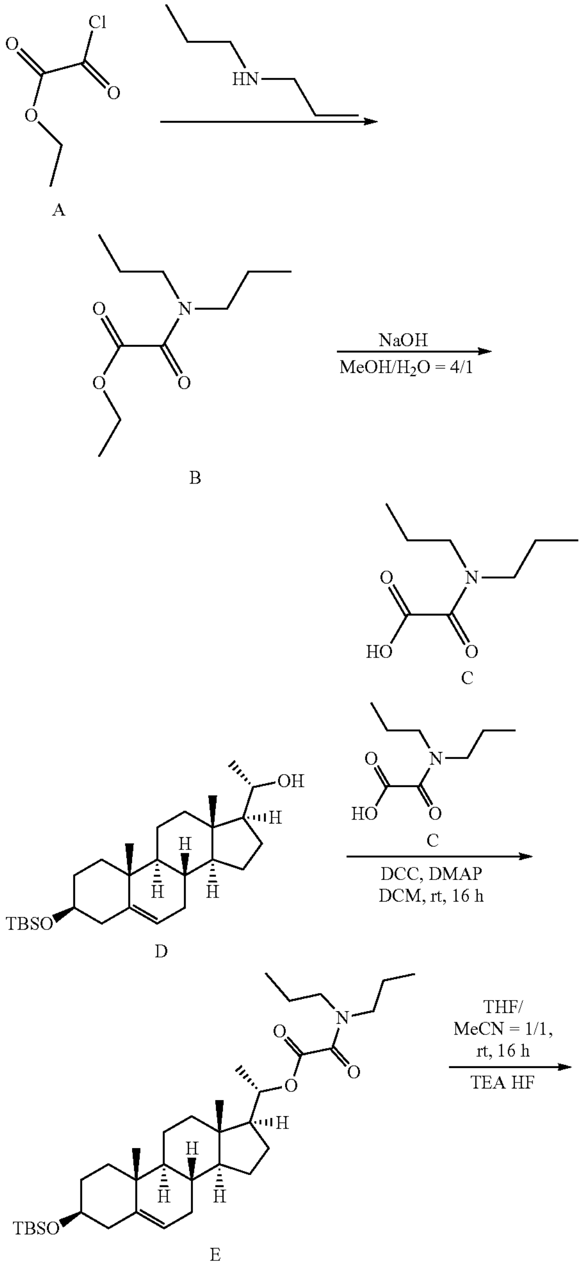

A

B

C

D

E

-continued

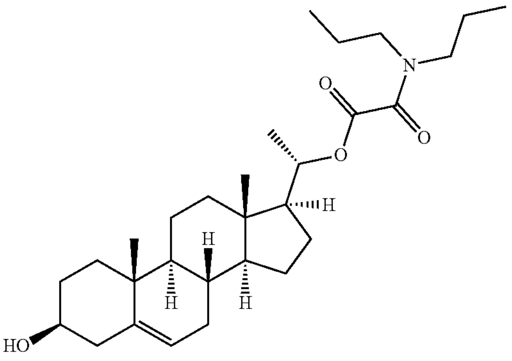

196

To a solution of dipropylamine (303 μL, 3.66 mmol) in dichloromethane (5 mL) was added ethyl oxalochloridate (500 mg, 3.66 mmol) at 0° C. The mixture was stirred at room temperature for 3 h. The mixture was poured into water and extracted with DCM. The combined organic layer was dried over sodium sulfate and concentrated to give the crude which was purified by column chromatography (petroleum ether/ethyl acetate=30/1) to give compound B (360 mg, yield: 48.8%).

To a solution of compound B (360 mg, 1.79 mmol) in methanol (4 mL) was added sodium hydroxide (286 mg, 7.15 mmol) in water (1 mL). The mixture was stirred at room temperature for 16 h. After completion, the mixture was adjusted with 1N HCl to pH ~1 and extracted with EA. The combined organic phase was dried over sodium sulfate and concentrated to give the compound C (300 mg, yield: 96.8%).

To a solution of compound C (48 mg, 277 μmol) in dry dichloromethane (2 mL) was added D (100 mg, 231 μmol) and 4-(dimethylamino)pyridin-1-ium (2.85 mg, 23.1 μmol) and N,N'-dicyclohexylmethanediimine (71.5 mg, 347 μmol). The mixture was stirred at room temperature for 16 h. The mixture was poured into water and extracted with DCM. The combined organic layer was dried over sodium sulfate and concentrated to give the crude which was purified by column chromatography (petroleum ether/ethyl acetate=300/7) to give compound E (130 mg, yield: 95.75%).

To a solution of compound E (140 mg, 238 μmol) in tetrahydrofuran (1 mL) and acetonitrile (1 mL) was added trihydrogen triethylamine trifluoride (230 mg, 1.43 mmol). The mixture was stirred at room temperature for 16 h. After completion, the mixture was poured into water and extracted with ethyl acetate. The organic layer were dried over sodium sulfate and concentrated to give the crude which was purified by column chromatography (petroleum ether/ethyl acetate=3/1) to give compound 196 (90 mg, yield: 79.8%). $^1$H NMR (400 MHz, $CDCl_3$) δ 5.35 (d, J=5.1 Hz, 1H), 5.21-5.11 (m, 1H), 3.62-3.52 (m, 1H), 3.44-3.15 (m, 4H), 2.35-2.18 (m, 2H), 1.98 (d, J=19.4 Hz, 1H), 1.87 (dd, J=23.6, 11.3 Hz, 4H), 1.74-1.45 (m, 14H), 1.34 (d, J=6.2 Hz, 3H), 1.28-1.07 (m, 4H), 1.01 (s, 3H), 1.00-0.88 (m, 6H), 0.73 (s, 3H).

Example 197: (S)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethyl 2-(ethyl(isopropyl)amino)-2-oxoacetate

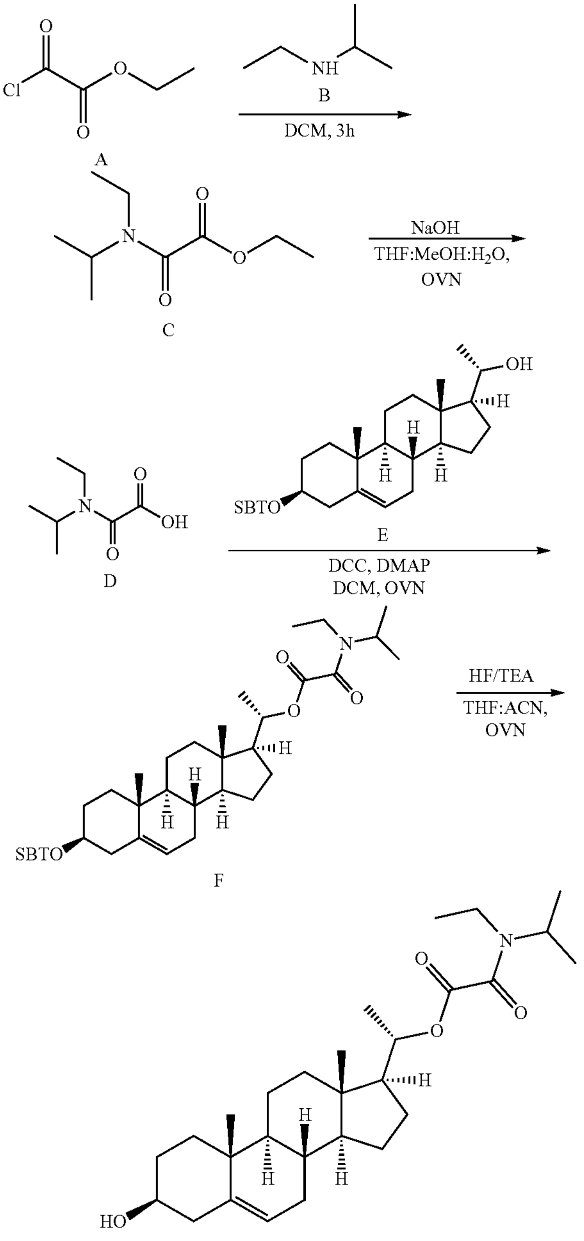

197

To a solution of compound B (887 μL, 7.32 mmol) in DCM (5 mL) was added compound A (409 μL, 3.66 mmol) at 0° C. The mixture was stirred at 0° C. for 3 h. After completion, the reaction was quenched by the addition of water and extracted with DCM. The combined organic layers were dried over sodium sulfate and concentrated to give the crude product that was purified by column chromatography to give compound C as colorless oil (450 mg, 66%).

To a solution of compound C (450 mg, 2.4 mmol) in THE (2 mL), methanol (2 mL) and water (2 mL) at room temperature was added sodium hydroxide (288 mg, 7.21 mmol). The mixture was stirred for 16 h. After completion, the reaction was quenched by the addition of water, then adjusted to pH 3 with HCl (1M) and filtered, the filter cake was dried in vacuo to afford compound D as a white solid (300 mg, 78%).

To a solution of compound E (300 mg, 693 μmol) in DCM (10 mL) were added compound D (166 mg, 1.04 mmol), DMAP (16.9 mg, 139 μmol) and DCC (429 mg, 2.08 mmol) at room temperature. The mixture was stirred for 16 h. After completion, the solvent was evaporated to give the crude product that was purified by column chromatography to give compound F as a white solid (170 mg, 43%).

To a solution of compound F (170 mg, 296 μmol) in acetonitrile (2 mL) and tetrahydrofuran (2 mL) was added trihydrogen triethylamine trifluoride (483 μL, 2.96 mmol) at room temperature. After being stirred for 16 h, the solution was concentrated in vacuo to afford the crude product that was purified by column chromatography to give compound 197 as a white solid (53.7 mg, 40%). $^1H$ NMR (400 MHz, $CDCl_3$) δ 5.35 (d, J=5.2 Hz, 1H), 5.11 (dd, J=9.2, 6.0 Hz, 1H), 3.86-3.74 (m, 1H), 3.51 (dd, J=10.8, 5.6 Hz, 1H), 3.27 (dq, J=14.8, 7.2 Hz, 2H), 2.34-2.15 (m,, 2H), 2.04-1.95 (m, 1H), 1.93-1.81 (m, 4H), 1.64 (qd, J=9.0, 2.8 Hz, 2H), 1.56 (d, J=12.2 Hz, 3H), 1.50 (dt, J=12.8, 3.4 Hz, 4H), 1.42 (dd, J=13.6, 4.0 Hz, 1H), 1.34 (d, J=6.2 Hz, 3H), 1.27-1.23 (m, 5H), 1.21 (t, J=5.8 Hz, 4H), 1.17-1.13 (m, 1H), 1.12-1.06 (m, 1H), 1.01 (s, 3H), 0.95 (dt, J=11.4, 5.8 Hz, 1H), 0.73 (s, 3H). LCMS: $[M+H]^+$=460.25.

Example 198: (S)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethyl 2-oxo-2-(pyrrolidin-1-yl) acetate

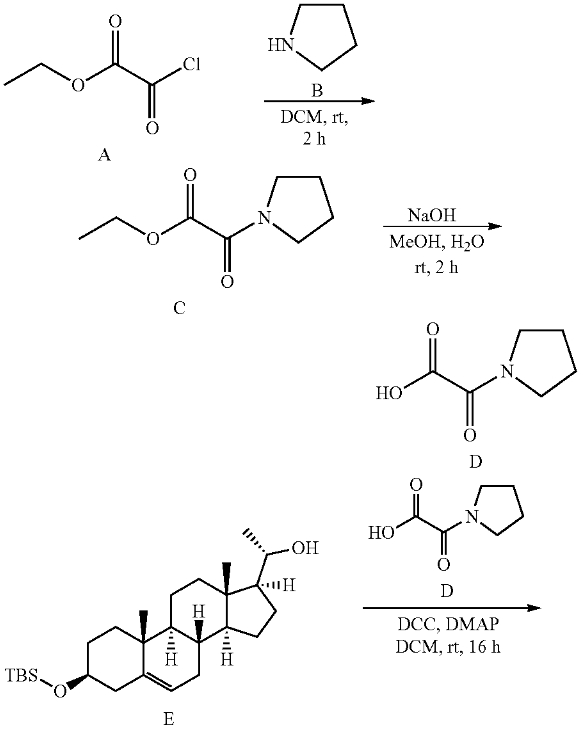

A
C
D
D
E

-continued

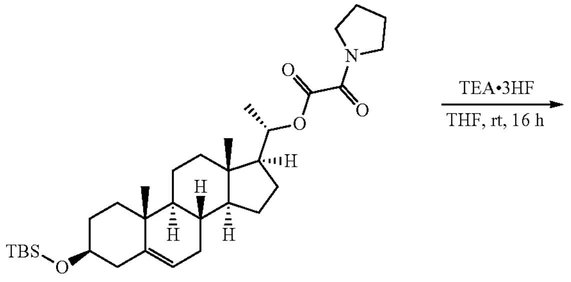

F

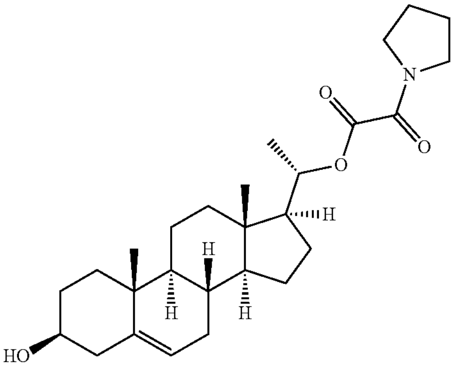
198

To a solution of compound B (260 mg, 3.66 mmol) in dry DCM (9 mL) was added compound A (500 mg, 3.66 mmol) at 0° C. The mixture was stirred at room temperature for 2 h. After completion, the mixture was concentrated, and the residue was purified by column chromatography to afford compound C (330 mg, 95% yield).

To a solution of compound C (330 mg, 1.93 mmol) in methanol (4 mL) and water (1 mL) was added NaOH (308 mg, 7.71 mmol). The mixture was stirred at room temperature for 2 h. After completion, the mixture was diluted with water and extracted with ethyl acetate. The organic layer was dried over sodium sulfate and concentrated to afford compound D (280 mg, 95% yield).

To a solution of compound E (100 mg, 0.231 mmol) in DCM (3 mL) was added D (33.1 mg, 0.231 mmol), DCC (52.4 mg, 0.254 mmol) and DMAP (2.82 mg, 0.023 mmol). The mixture was stirred at room temperature for 16 h. After completion, the mixture was extracted with ethyl acetate. The organic layer was dried over sodium sulfate and concentrated to afford the crude product that was purified by column chromatography to give compound F (70 mg, 54% yield).

To a solution of compound F (70 mg, 0.129 mmol) in THE (2.6 mL) was added TEA·3HF (0.4 mL). The mixture was stirred at room temperature for 16 h. After completion, the mixture was diluted with water and extracted with DCM. The organic layer was dried over sodium sulfate and concentrated to afford the crude product that was purified by column chromatography to afford compound 198 (17 mg, 31%) as a white solid. $^1H$ NMR (400 MHz, $CDCl_3$) δ 5.35 (d, J=5.1 Hz, 1H), 5.11 (dd, J=9.1, 6.2 Hz, 1H), 3.55 (dd, J=18.3, 7.3 Hz, 5H), 2.32-2.17 (m, 2H), 2.02-1.81 (m, 9H), 1.69-1.42 (m, 10H), 1.35 (d, J=6.2 Hz, 3H), 1.26-0.87 (m, 9H), 0.73 (s, 3H).

Example 199: (1S)-1-[(1S,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]ethyl2-oxo-2-(piperidin-1-yl)acetate

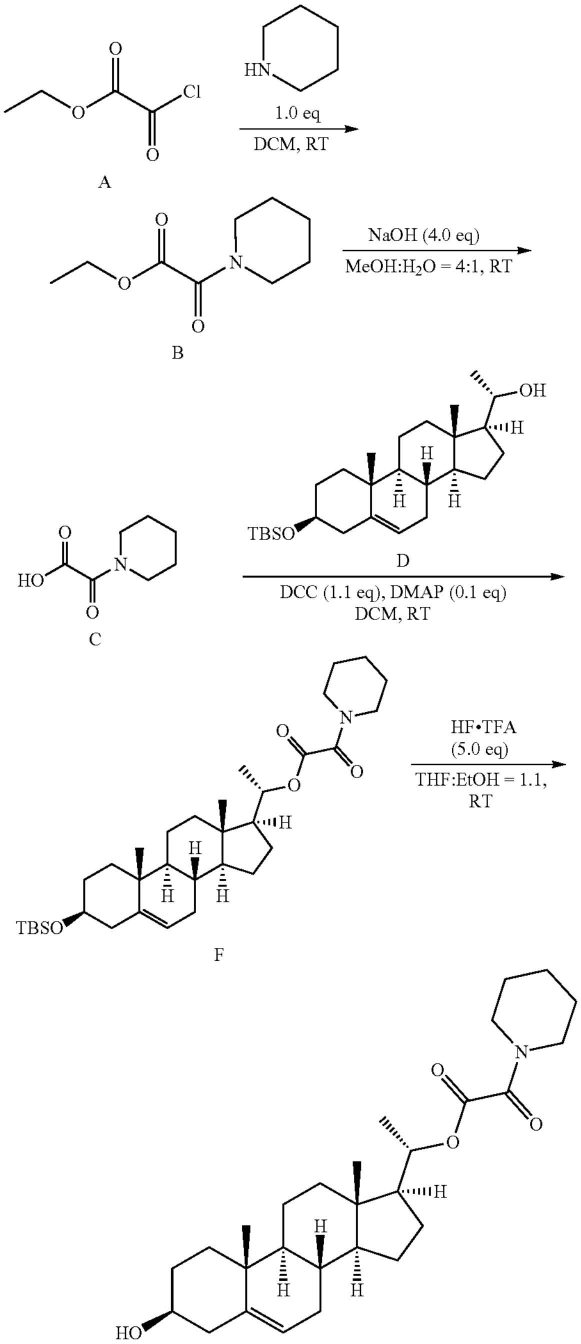

A
B
D
C
F
199

To a solution of compound A (1.2 g, 8.79 mmol) in DCM (20 mL) was added piperidine (748 mg, 8.79 mmol) dropwise at 0° C. The reaction was stirred at room temperature for 2 h. After completion, the mixture diluted with water and extracted with ethyl acetate. The organic layer was dried with sodium sulfate and concentrated in vacuo to give compound B (1.32 g, 81.1%).

A mixture of compound B (500 mg, 2.7 mmol) and sodium hydroxide (432 mg, 10.8 mmol) in methanol (32 mL) and water (8 mL) was stirred at room temperature for 4 h. After completion, the pH of the mixture was adjusted to 2 with 1 M HCl and extracted with ethyl acetate. The organic layer was dried with sodium sulfate and concentrated in vacuo to give compound C (300 mg, 70.7%).

To a solution of compound C (36.3 mg, 231 μmol) in DCM (5 mL) were added 4-(dimethylamino)pyridin-1-ium (2.85 mg, 23.1 μmol), compound D (100 mg, 231 μmol) and N,N'-dicyclohexylmethanediimine (52.4 mg, 254 μmol) at room temperature. The mixture was heated at 30° C. and stirred for 16 h. The reaction was diluted with ethyl acetate, washed with water and brine. The organic layer was dried with sodium sulfate and concentrated in vacuo to give the crude product that was purified by column chromatography (eluting with 1/10 ethyl acetate/petroleum ether) to afford compound E (111 mg, 84.0%).

To a solution of compound E (111 mg, 194 μmol) in THE (3 mL) and EtOH (3 mL) was added trihydrogen triethylamine trifluoride (156 mg, 970 μmol) at room temperature. The reaction was stirred for 16 h at room temperature. After completion, the mixture was diluted with ethyl acetate, washed with water and brine. The organic layer was dried with sodium sulfate and concentrated in vacuo to give the crude product which was purified by column chromatography (eluting with 1/3 ethyl acetate/petroleum ether) to afford compound 199 (33.2 mg, 37.4%). $^1H$ NMR (400 MHz, $CDCl_3$) δ 5.35 (d, J=5.2 Hz, 1H), 5.11 (dd, J=9.0, 6.0 Hz, 1H), 3.64-3.46 (m, 3H), 3.32 (t, J=5.4 Hz, 2H), 2.33-2.20 (m, 2H), 1.98 (d, J=17.0 Hz, 1H), 1.93-1.79 (m, 4H), 1.69-1.58 (m, 8H), 1.58-1.39 (m, 8H), 1.35 (d, J=6.2 Hz, 3H), 1.27-1.11 (m, 3H), 1.01 (s, 3H), 0.98-0.85 (m, 1H), 0.73 (s, 3H). LCMS: $[M+H]^+$=458.25.

Example 200: (S)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethyl 2-(4-ethyl-4-hydroxypiperidin-1-yl)-2-oxoacetate

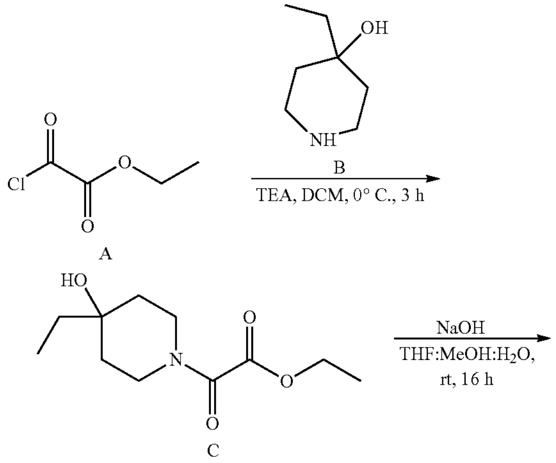

A
B
C

-continued

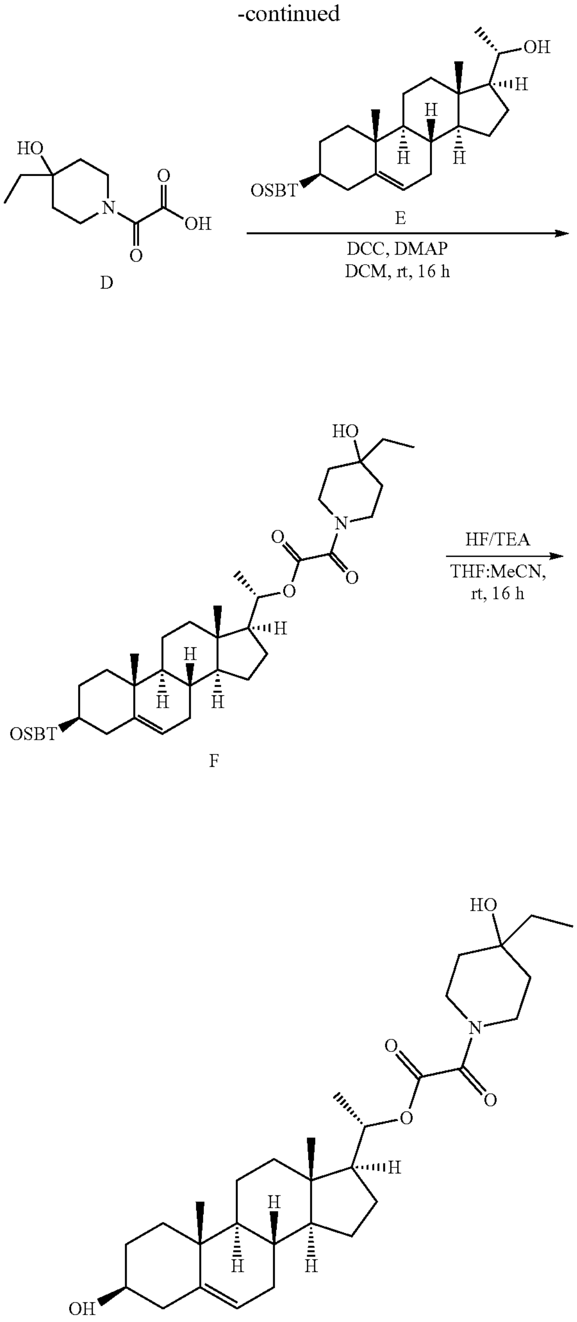

200

To a solution of compound B (315 mg, 1.9 mmol) in DCM (5 mL) was added TEA (611 μL) and compound A (164 μL, 1.46 mmol) at 0° C. The mixture was stirred at 0° C. for 3 h. After completion, the solution was quenched by the addition of water and extracted with DCM. The combined organic layers were dried over sodium sulfate and concentrated to give crude product that was purified by column chromatography to give compound C as colorless oil (180 mg, 54%).

To a solution of compound C (180 mg, 785 μmol) in THE (2 mL), methanol (2 mL) and water (2 mL) at room temperature was added sodium hydroxide (94.2 mg, 2.36 mmol). The mixture was stirred for 16 h. After completion, the result solution was quenched by the addition of water, then adjusted to pH 3 with HCl (1M) and extracted with DCM. The combined organic layer was dried over sodium sulfate and concentrated to afford compound D as a white solid (46 mg, 30%).

To a solution of compound E (100 mg, 231 μmol) in DCM (5 mL) was added compound D (46 mg, 231 μmol), DMAP (5.65 mg, 46.2 μmol) and DCC (143 mg, 639 μmol) at room temperature. The mixture was stirred for 16 h. After completion the solvent was evaporated to give the crude product that was purified by column chromatography to give compound F as a white solid (100 mg, 70%).

To a solution of compound F (80 mg, 130 μmol) in acetonitrile (1.1 mL) and tetrahydrofuran (1.1 mL) was added trihydrogen triethylamine trifluoride (105 μL, 649 μmol) at room temperature and stirred for 16 h. After completion, the solvent was concentrated in vacuo to afford the crude product that was purified by column chromatography to give compound 200 as a white solid (10 mg, 15%). $^1$H NMR (400 MHz, $CDCl_3$)$^1$H NMR (400 MHz, $CDCl_3$) δ 5.35 (d, J=5.2 Hz, 1H), 5.12 (m, 1H), 4.26 (s, 1H), 3.58-3.35 (m, 3H), 3.13 (dt, J=12.0, 6.0 Hz, 1H), 2.34-2.18 (m, 2H), 2.03-1.81 (m, 5H), 1.65 (t, J=9.3 Hz, 3H), 1.57-1.43 (m, 12H), 1.35 (d, J=6.2 Hz, 3H), 1.28-1.15 (m, 2H), 1.12-1.07 (m, 2H), 1.03 (s, 3H), 0.94 (t, J=7.6 Hz, 3H), 0.73 (s, 3H). LCMS: $[M+H]^+$=502.25.

Example 201: (R)-1-((R)-3-ethyl-3-methoxypiperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

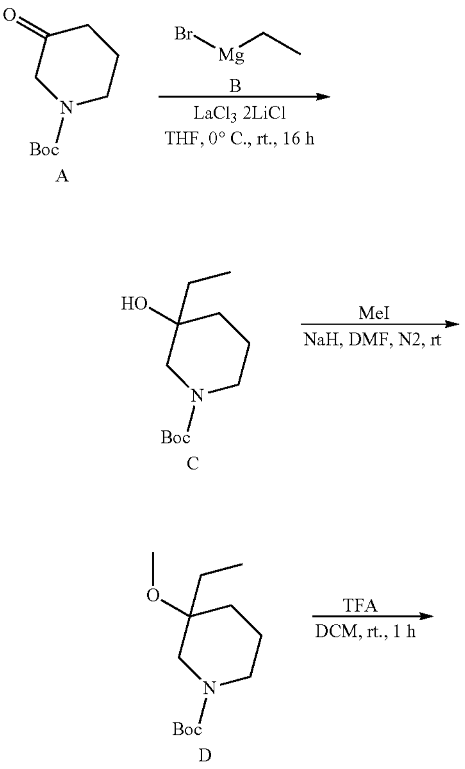

-continued

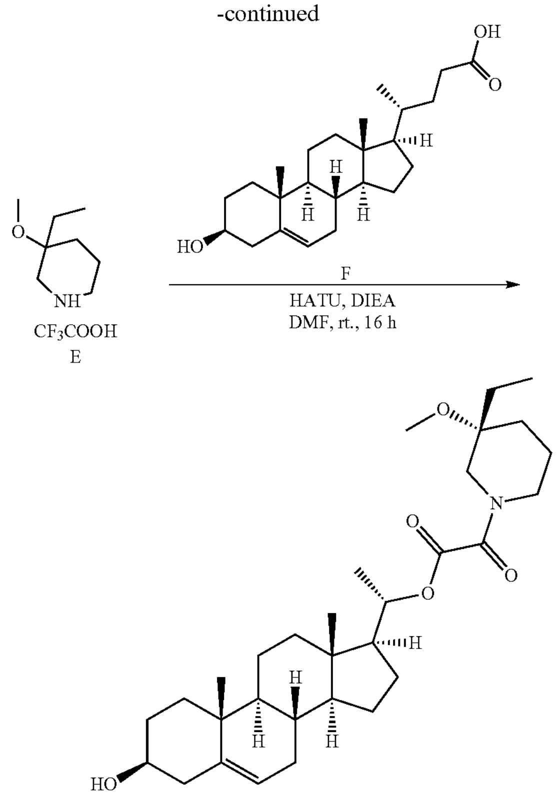

201

To a solution of compound B (1070 mg, 8.03 mmol) in THF (2 mL) was added $LaCl_3 \cdot 2LiCl$ (8.1 mL, 1M in THF, 8.1 mmol) at 0° C. After stirring at 0° C. under $N_2$ for 2 h, to the mixture was added compound A (400 mg, 2.01 mmol) at 0° C. Then the reaction was stirred at room temperature under $N_2$ for 16 h. The mixture was added $NH_4Cl$ and extracted with EA. The organic layer was dried over sodium sulfate and concentrated. The residue was purified by silica gel chromatography to afford compound C (200 mg, 43.4%).

To a solution of compound C (200 mg, 872 μmol) in DMF (2 mL) was added NaH (60.2 mg, 1.5 mmol, 60% dispersion in oil) at 0° C. under $N_2$. After stirring at room temperature for 0.5 h, to the mixture was added $CH_3I$ (186 mg, 1.31 mmol) and stirred at room temperature for 3 h. The mixture was added water and extracted with EA. The organic layer was washed with brine, dried over sodium sulfate and concentrated to afford compound D (180 mg, 84.5%).

To a solution of compound D (180 mg, 740 μmol) in DCM (2 mL) was added TFA (0.5 mL). The mixture was stirred at room temperature for 1 h. The mixture was concentrated to afford compound E and was used directly in the next step.

To a solution of compound F (150 mg, 0.4 mmol) in DMF (2 mL, 25.8 mmol) was added compound E (190 mg, 740 μmol), DIEA (259 mg, 2 mmol) and HATU (228 mg, 601 μmol). The mixture was stirred at room temperature for 16 h. The mixture was added water and extracted with EA. The organic layer was washed with brine, dried over sodium sulfate and concentrated. The residue was purified by silica gel chromatography to afford compound 201 (110 mg, 55%). LCMS [M+1]=500.25. $^1$HNMR (400 MHz, Chloroform-d) δ 5.34 (dd, J=4.8, 2.6 Hz, 1H), 4.28-4.05 (m, 1H), 3.69-3.45 (m, 2H), 3.15-3.11 (m, 3H), 3.10-2.71 (m, 2H), 2.44-2.16 (m, 4H), 2.04-1.93 (m, 2H), 1.93-1.70 (m, 6H), 1.66-1.56 (m, 5H), 1.55-1.40 (m, 8H), 1.38-1.25 (m, 4H), 1.20-1.02 (m, 4H), 1.00 (s, 3H), 0.95 (t, J=5.8 Hz, 5H), 0.90-0.84 (m, 3H), 0.68 (s, 3H).

Example 202: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(2-methoxypyrimidin-4-yl)piperazin-1-yl) pentan-1-one

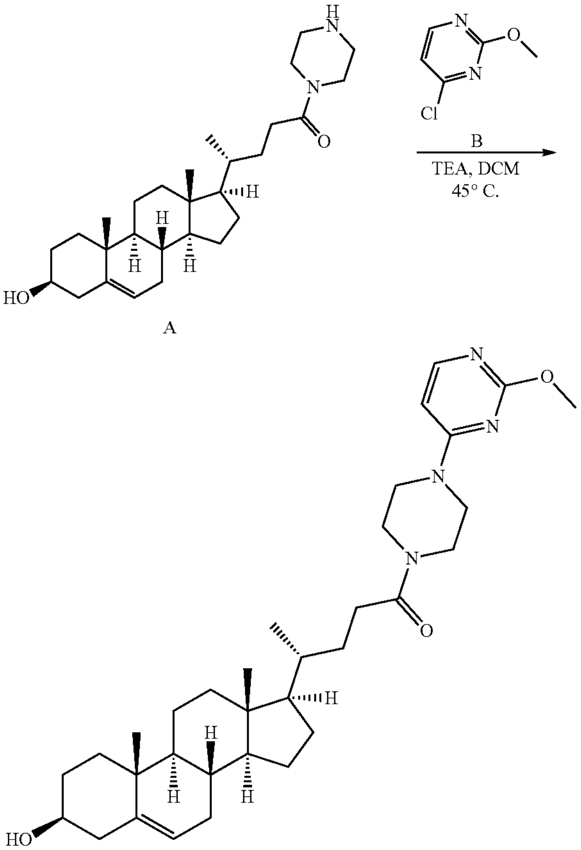

202

To a solution of compound A (200 mg, 452 μmol) and compound B (65.3 mg, 452 μmol) in dichloromethane (10 mL) was added triethylamine (274 mg, 2.71 mmol) and the reaction mixture was stirred at 45° C. under nitrogen for 16 hours. After completion, the mixture was quenched by adding water (10 mL) and extracted with dichloromethane (10 mL×3). The organic layer was washed with brine, dried over sodium sulfate, filtered, and concentrated to give the crude which was purified by column chromatography on silica gel to yield the title compound 202 (85.7 mg, 20%) as a white solid. LCMS: $[M+H]^+$=551.25. $^1$H NMR (400 MHz, Chloroform-d) δ 8.07 (d, J=6.0 Hz, 1H), 6.18 (d, J=6.1 Hz, 1H), 5.35 (d, J=5.2 Hz, 1H), 3.94 (s, 3H), 3.73 (dd, J=13.6, 5.9 Hz, 4H), 3.63-3.49 (m, 5H), 2.41 (ddd, J=15.5, 10.9, 5.1 Hz, 1H), 2.31-2.18 (m, 3H), 2.03-1.94 (m, 2H), 1.88-1.76 (m, 4H), 1.69 (s, 2H), 1.63-1.55 (m, 2H), 1.47-1.42 (m, 2H), 1.39-1.25 (m, 3H), 1.22-1.03 (m, 5H), 1.00 (s, 3H), 0.96 (d, J=6.5 Hz, 3H), 0.92 (dd, J=11.3, 5.5 Hz, 1H), 0.69 (s, 3H).

Example 203: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(6-methoxypyrimidin-4-yl)piperazin-1-yl]pentan-1-one

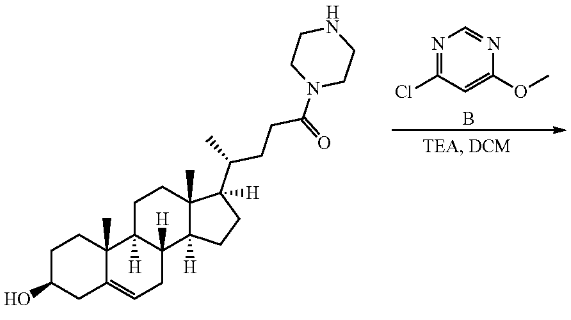

A

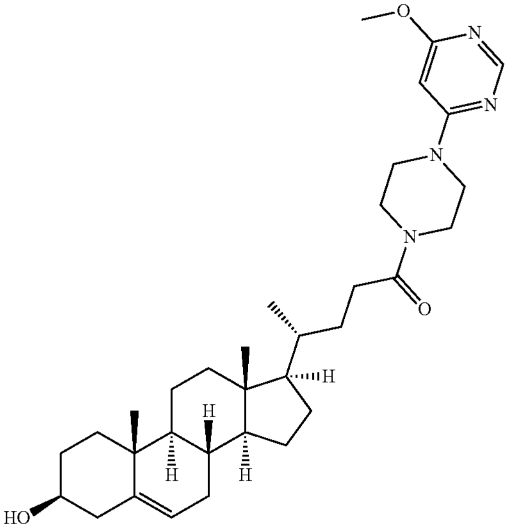

203

To a solution of compound A (200 mg, 452 μmol) in dichloromethane (8 mL) was added triethylamine (274 mg, 2.71 mmol) at room temperature. After addition, the solution was cooled to 0° C., and 4-chloro-6-methoxypyrimidine (52.2 mg, 361 μmol) was added. The mixture was heated at reflux for 16 h under nitrogen. The resulting mixture was extracted with DCM/water, the organic layer was dried with sodium sulfate and concentrated under vacuum to give crude product which was purified by silica gel chromatography (eluting with 1/30 MeOH/DCM) to give the title compound 203 (62.2 mg, 25.0%). $^1H$ NMR (400 MHz, $CDCl_3$) δ 8.34 (s, 1H), 5.82 (s, 1H), 5.35 (d, J=5.0 Hz, 1H), 3.93 (s, 3H), 3.74-3.67 (m, 4H), 3.59-3.49 (m, 5H), 2.46-2.19 (m, 4H), 2.05-1.75 (m, 6H), 1.55-1.05 (m, 15H), 1.01 (s, 3H), 0.96 (d, J=6.4 Hz, 3H), 0.91 (dd, J=17.4, 6.2 Hz, 1H), 0.69 (s, 3H). LCMS: $[M+H]^+$=551.25.

Example 204: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(5-methoxypyrimidin-4-yl)piperazin-1-yl]pentan-1-one

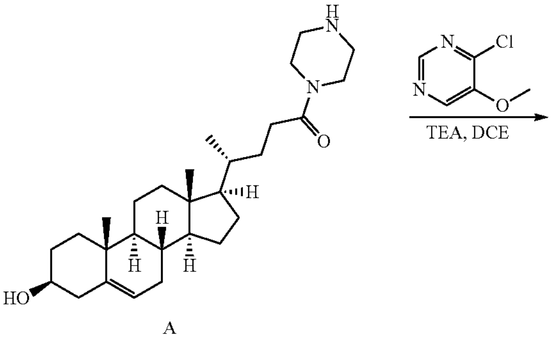

A

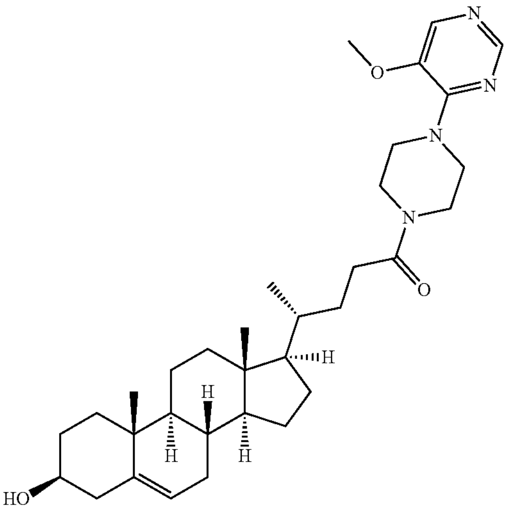

204

To a solution of compound A (150 mg, 339 μmol) in 1,2-dichloroethane (5 mL) was added triethylamine (283 μL, 2.03 mmol) at room temperature. After addition, the solution was cooled to 0° C., and 4-chloro-5-methoxypyrimidine (39.2 mg, 271 μmol) was added. The mixture was heated at 60° C.; for 16 h under nitrogen. The resulting mixture was diluted with water and extracted with DCM. The organic layer was dried with sodium sulfate and concentrated under vacuum to give crude product which was purified by silica gel chromatography (eluting with 1/30 MeOH/DCM) to give compound 204 (25.0 mg, 13.4%). $^1H$ NMR (400 MHz, $CDCl_3$) δ 8.36 (s, 1H), 7.96 (bs, 1H), 5.37-5.33 (m, 1H), 3.89 (s, 3H), 3.80-3.67 (m, 6H), 3.61-3.47 (m, 3H), 2.47-2.35 (m, 1H), 2.32-2.21 (m, 3H), 2.04-1.75 (m, 6H), 1.64-1.06 (m, 16H), 1.01 (s, 3H), 0.97 (d, J=6.4 Hz, 3H), 0.69 (s, 3H). LCMS: $[M+H]^+$=551.25.

Example 205: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(2-methylpyrimidin-4-yl)piperazin-1-yl)pentan-1-one

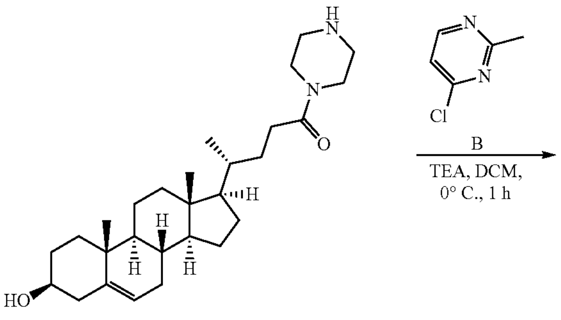

A

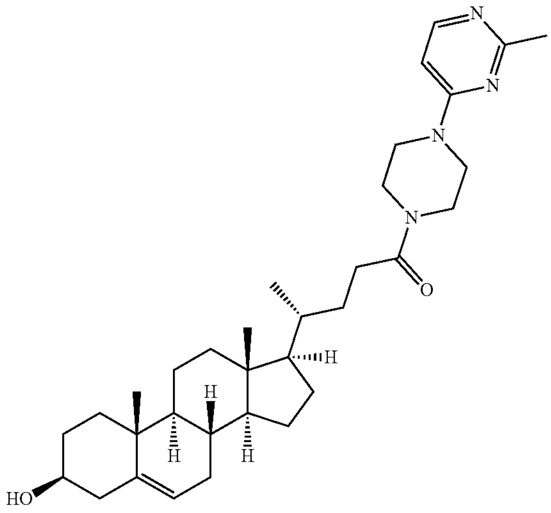

205

To a solution of compound A (100 mg, 226 μmol) in dichloromethane (3 mL) was added triethylamine (137 mg, 1.36 mmol) and 4-chloro-2-methylpyrimidine (26.1 mg, 203 μmol) at 0° C. The reaction mixture was stirred for 1 hour. After completion, the mixture was quenched by adding water (10 mL) and extracted with DCM (10 mL×3). The organic layer was washed with brine, dried over sodium sulfate, filtered, and concentrated to give the crude which was purified by column chromatography on silica gel to yield the title compound 205 (24.6 mg, 20.4%) as a white solid. LCMS: $[M+H]^+$=535.25. $^1H$ NMR (400 MHz, Chloroform-d) δ 8.17 (d, J=6.2 Hz, 1H), 6.33 (d, J=6.2 Hz, 1H), 5.35 (d, J=5.0 Hz, 1H), 3.79-3.67 (m, 4H), 3.63-3.46 (m, 5H), 2.52 (s, 3H), 2.46-2.36 (m, 1H), 2.32-2.19 (m, 3H), 2.03-1.95 (m, 2H), 1.91-1.75 (m, 6H), 1.64-1.04 (m, 15H), 1.01 (s, 3H), 0.97 (d, J=6.4 Hz, 3H), 0.69 (s, 3H).

Example 206: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(6-methylpyrimidin-4-yl)piperazin-1-yl]pentan-1-one

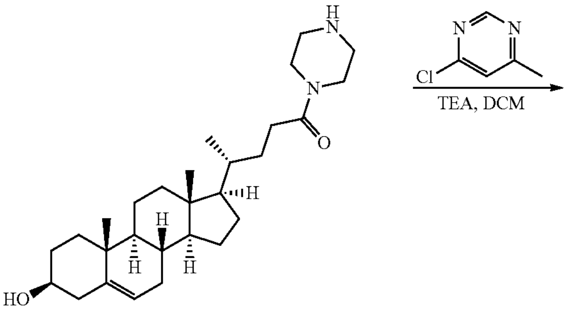

A

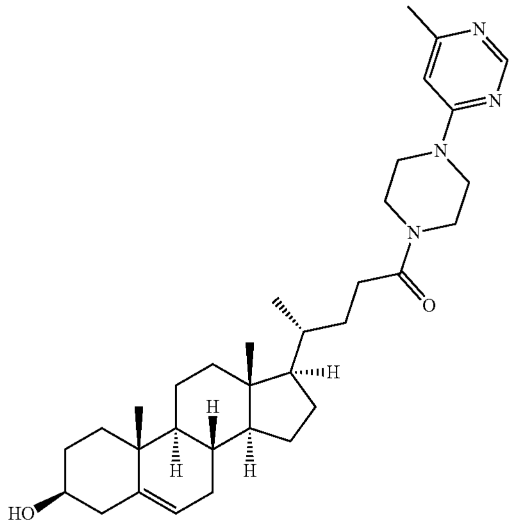

206

To a solution of compound A (150 mg, 339 μmol) in dichloromethane (20 mL) was added triethylamine (283 μL, 2.03 mmol) at room temperature. After addition, the solution was stirred at 0° C.; for 10 min. 4-chloro-6-methylpyrimidine (34.8 mg, 271 μmol) was added. The mixture was heated at reflux for 16 h under nitrogen. The resulting mixture was diluted with water and extracted with DCM. The organic layer was dried with sodium sulfate and concentrated under vacuum to give crude product which was purified by silica gel chromatography (eluting with 1/30 MeOH/DCM) to give the title compound 206 (74.2 mg, 41.0%). $^1H$ NMR (400 MHz, $CDCl_3$) δ 8.54 (s, 1H), 6.39 (s, 1H), 5.35 (d, J=5.0 Hz, 1H), 3.76 (d, J=19.4 Hz, 4H), 3.65-3.46 (m, 5H), 2.45-2.36 (m, 4H), 2.31-2.20 (m, 3H), 2.05-1.77 (m, 8H), 1.53-1.43 (m, 6H), 1.35-1.23 (m, 4H), 1.22-1.07 (m, 4H), 1.01 (s, 3H), 0.97 (d, J=6.4 Hz, 3H), 0.69 (s, 3H). LCMS: $[M+H]^+$=535.25.

Example: 207: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyrrolidine-1-carbonyl)piperazin-1-yl) pentan-1-one

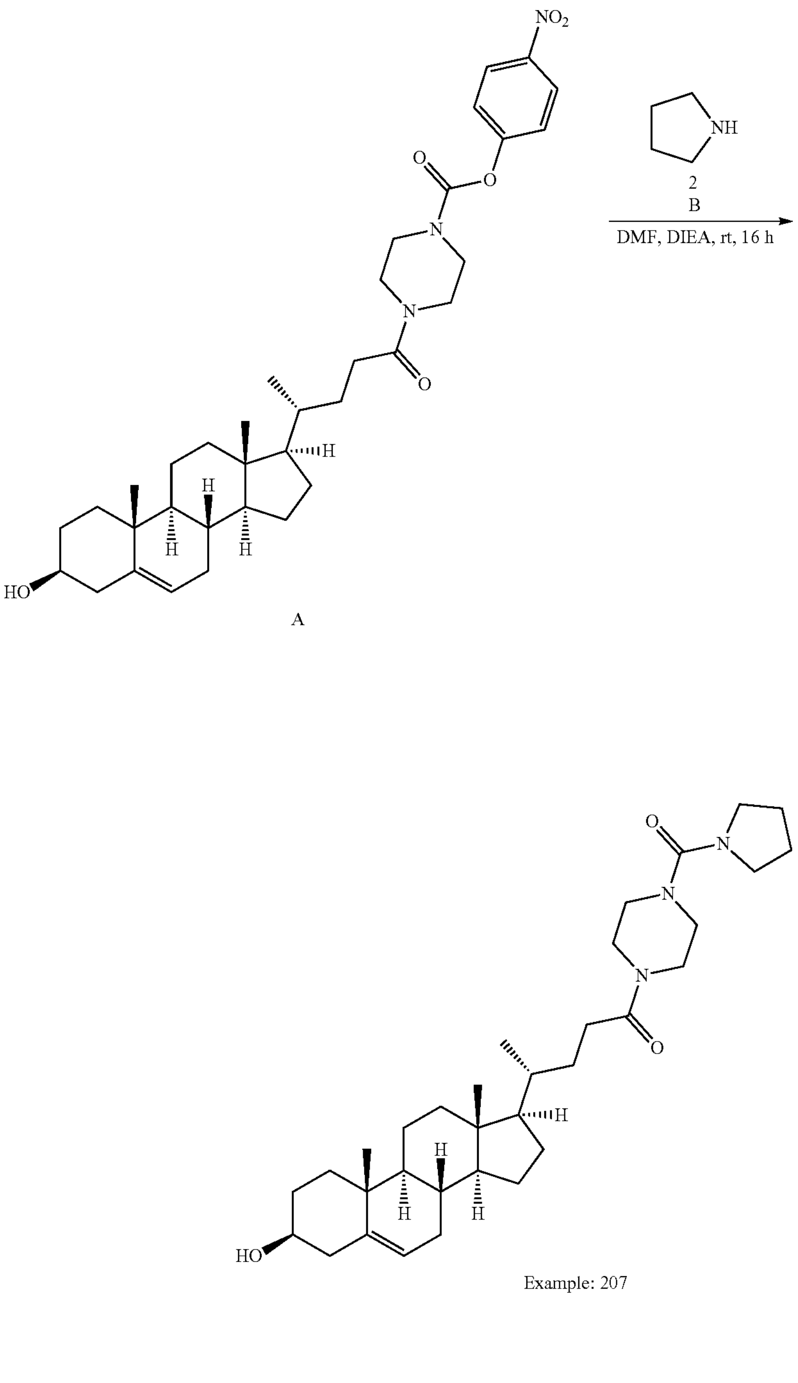

A

Example: 207

To a solution of compound A (100 mg, 165 μmol) in DMF (3 mL) was added DIEA (63.8 mg, 494 μmol) and compound B (58.5 mg, 823 μmol). The mixture was stirred at room temperature for 16 hours. After completion, the mixture was quenched by adding saturated ammonium chloride solution (20 mL) and extracted with ethyl acetate (15 mL×3). The organic layer was washed with brine, dried over sodium sulfate, filtered, and concentrated to give the crude which was purified by column chromatography on silica gel to yield the title compound 207 (30 mg, 33.78%) as a white solid. $^1$HNMR (400 MHz, Chloroform-d) δ 5.35 (d, J=5.0 Hz, 1H), 3.67-3.21 (m, 13H), 2.39 (bs, 1H), 2.34-2.16 (m 3H), 2.05-1.05 (m, 22H), 1.01 (s, 3H), 0.96 (d, J=6.0 Hz, 3H), 0.93-0.85 (m, 1H), 0.68 (s, 3H). LCMS: $[M+1]^+$=540.25.

Example: 208: (R)-1-(4-(azetidine-1-carbonyl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

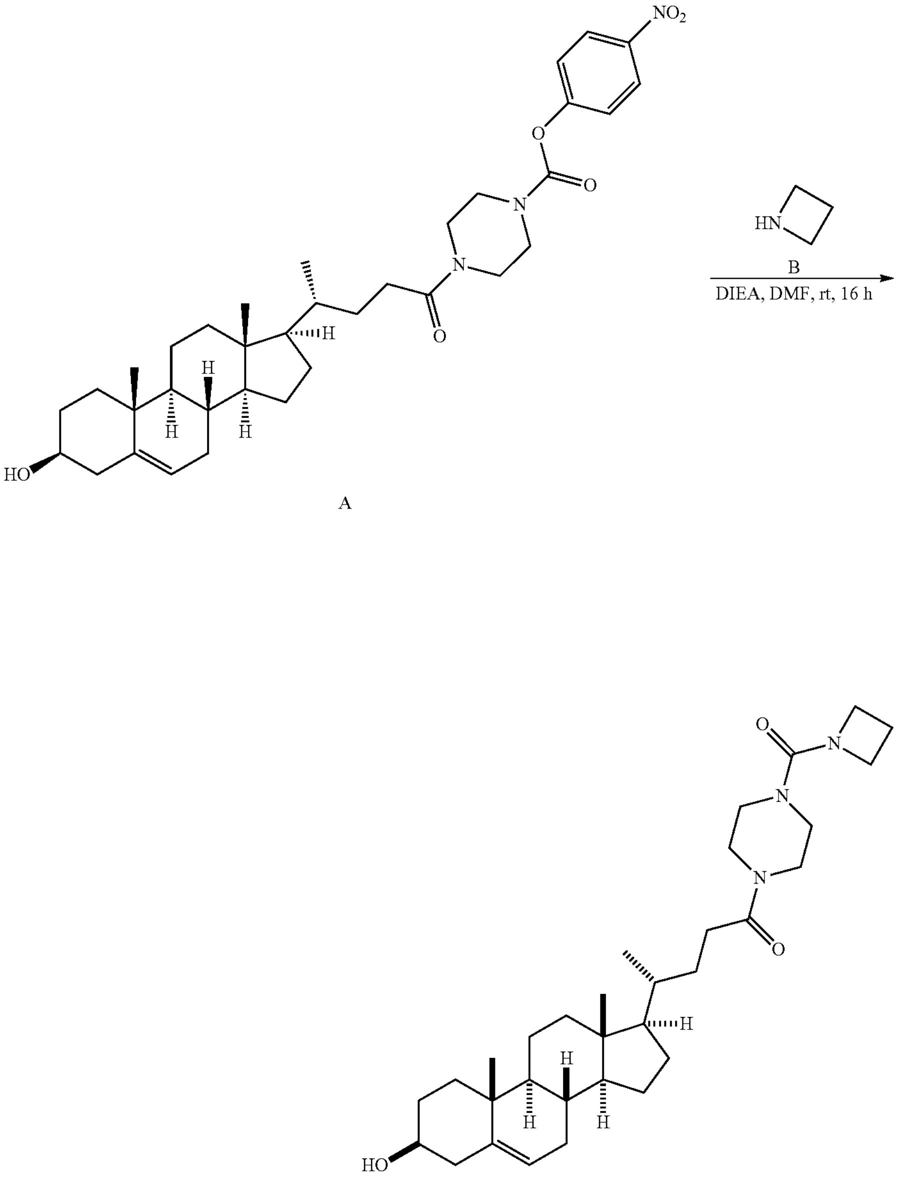

A

Example: 208

To a solution of compound A (100 mg, 165 μmol) in DMF (3 mL) was added DIEA (128 mg, 987 μmol) and compound B (9.4 mg, 165 μmol). The mixture was stirred at room temperature for 16 hours. After completion, the mixture was quenched by adding saturated ammonium chloride solution (20 mL) and extracted with ethyl acetate (10 mL×3). The organic layer was washed with brine, dried over sodium sulfate, filtered, and concentrated to give the crude which was purified by column chromatography on silica gel to yield the title compound 208 (40 mg, 46.3%) as a white solid. $^1$H NMR (400 MHz, Chloroform-d) δ 5.38-5.32 (m, 1H), 4.01 (t, J=7.7 Hz, 4H), 3.65-3.22 (m, 9H), 2.43-2.17 (m, 6H), 2.01-1.93 (m, 2H), 1.91-1.72 (m, 4H), 1.58-1.42 (m, 7H), 1.39-1.28 (m, 3H), 1.20-1.02 (m, 5H), 1.00 (s, 3H), 0.95 (d, J=6.5 Hz, 3H), 0.88 (q, J=7.1, 6.2 Hz, 1H), 0.68 (s, 3H). LCMS: $[M+1]^+$=526.25.

Example 209: 4—((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N-(2-methoxyethyl)-N-methylpiperazine-1-carboxamide
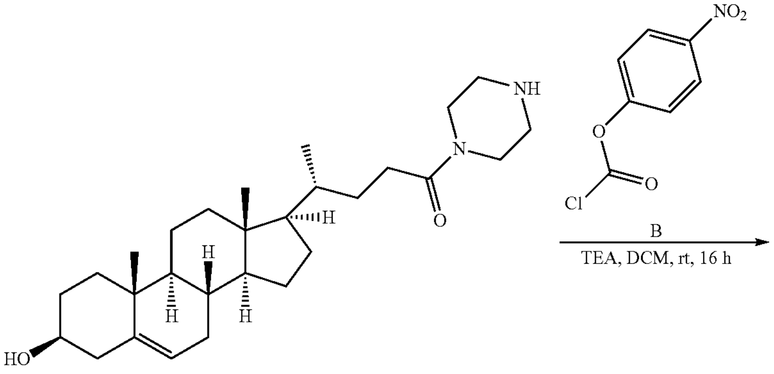
A
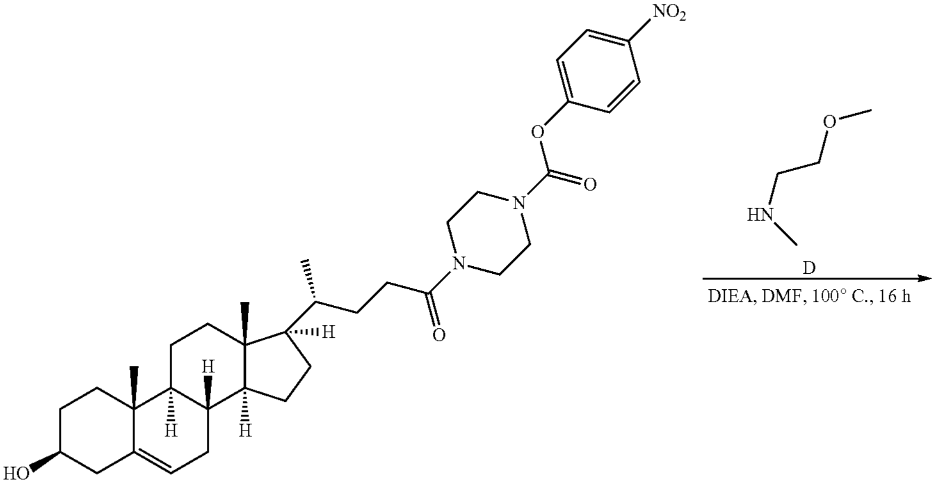
C
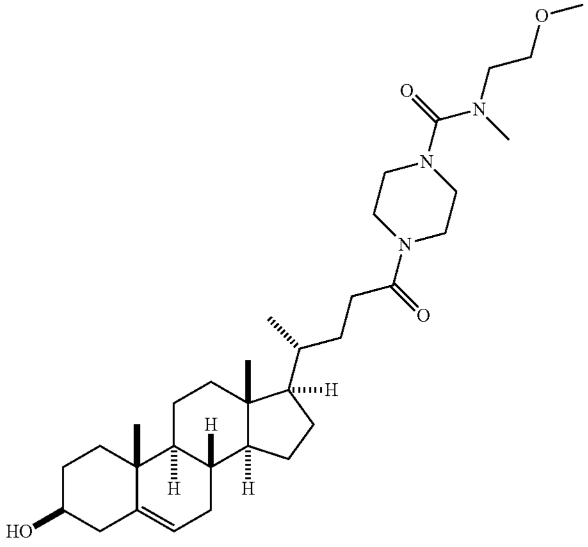
209

To a solution of compound A (3.0 g, 6.78 mmol) in dichloromethane (40 mL) was added triethylamine (1.03 g, 10.17 mmol) and compound B (1.23 g, 6.1 μmol) at 0° C. The mixture was stirred at room temperature for 16 hours. After completion, the mixture was quenched by adding saturated ammonium chloride solution (200 mL) and extracted with ethyl acetate (80 mL×3). The organic layer was washed with brine, dried over sodium sulfate, filtered, and concentrated to give the crude which was purified by column chromatography on silica gel to yield the title compound C (1.1 g, 26.7%) as a white solid.

To a solution of compound D (147 mg, 10 eq., 1.65 mmol) in DMF (2 mL) was added compound C (100 mg, 165 μmol) and DIEA (63.8 mg, 494 μmol). The solution was stirred at 100° C.; for 16 h under $N_2$. After completion, the mixture was quenched by adding saturated ammonium chloride solution (20 mL) and extracted with ethyl acetate (10 mL×3). The organic layer was washed with brine, dried over sodium sulfate, filtered, and concentrated to give the crude which was purified by column chromatography on silica gel to yield the title compound 209 (50 mg, 54%) as a white solid. $^1H$ NMR (400 MHz, Chloroform-d) δ 5.35 (d, J=5.0 Hz, 1H), 3.68-3.44 (m, 7H), 3.40 (t, J=5.5 Hz, 2H), 3.34 (s, 3H), 3.22 (bs, 4H), 2.93 (s, 3H), 2.43-2.18 (m, 4H), 2.07-1.72 (m, 7H), 1.59-1.04 (m, 16H), 1.00 (s, 3H), 0.95 (d, J=6.4 Hz, 3H), 0.93-0.82 (m, 1H), 0.68 (s, 3H). LCMS: $[M+1]^+$=558.25.

Example 210: N-(cyclopropylmethyl)-4-((R)-4-((3S, 8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl) pentanoyl)-N-methylpiperazine-1-carboxamide

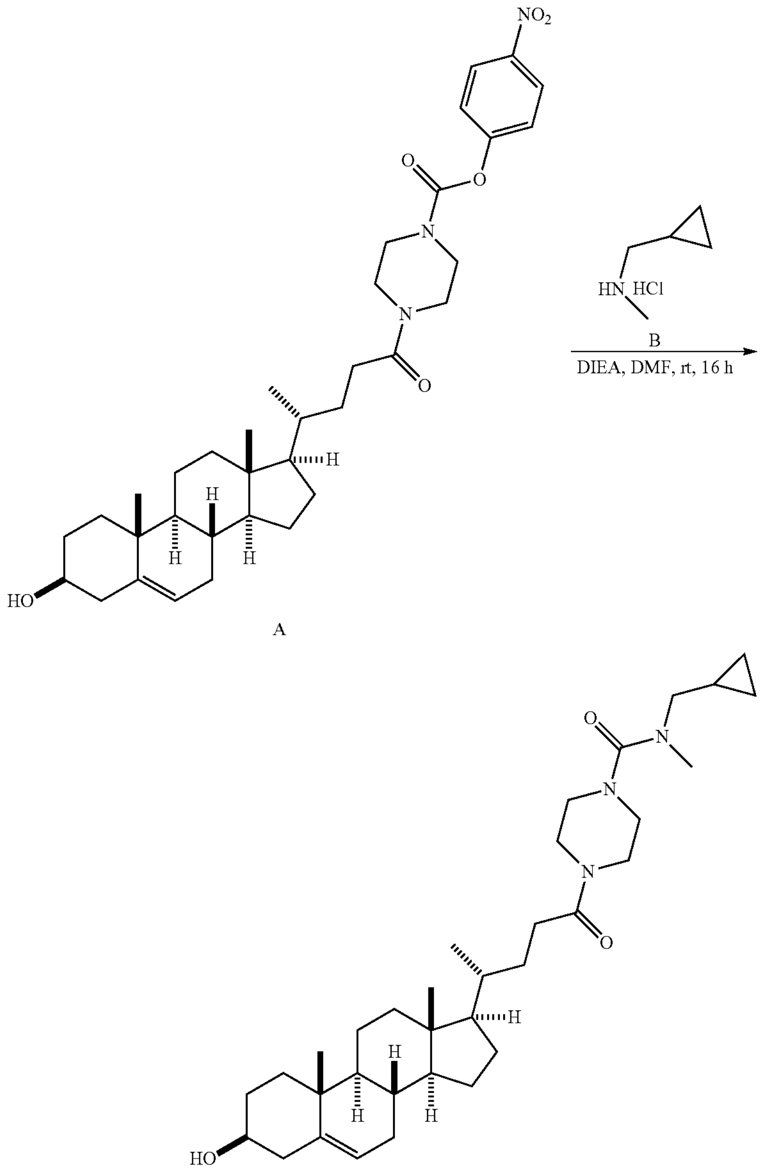

A

210

To a solution of compound A (100 mg, 0.16 mmol) and compound B (100 mg, 0.82 mmol) in DMF (3 mL) was added DIEA (170 mg, 1.32 mmol). The reaction mixture was stirred at 100° C. under $N_2$ for 16 h. The reaction mixture was diluted with water and extracted with EtOAc. The organic layer was washed by brine, dried over sodium sulfate, filtered, and concentrated. The mixture was purified by column chromatography on silica gel to afford the title compound 210 (41.2 mg, 45.2%) as a white solid. LCMS: [M+1]=554.30. $^1$H NMR (400 MHz, Chloroform-d) δ 5.35 (d, J=5.2 Hz, 1H), 3.70-3.43 (m, 5H), 3.23 (bs, 2H), 3.19 (bs, 2H), 3.07 (d, J=6.8 Hz, 2H), 2.93 (s, 3H), 2.43-2.18 (m, 4H), 2.07-1.72 (m, 6H), 1.59-1.41 (m, 8H), 1.36-1.27 (m, 3H), 1.21-1.05 (m, 4H), 1.00 (s, 3H), 0.97-0.85 (m, 5H), 0.68 (s, 3H), 0.57-0.49 (m, 2H), 0.19 (d, J=5.2 Hz, 2H).

Example 211: N-cyclopropyl-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N-methylpiperazine-1-carboxamide

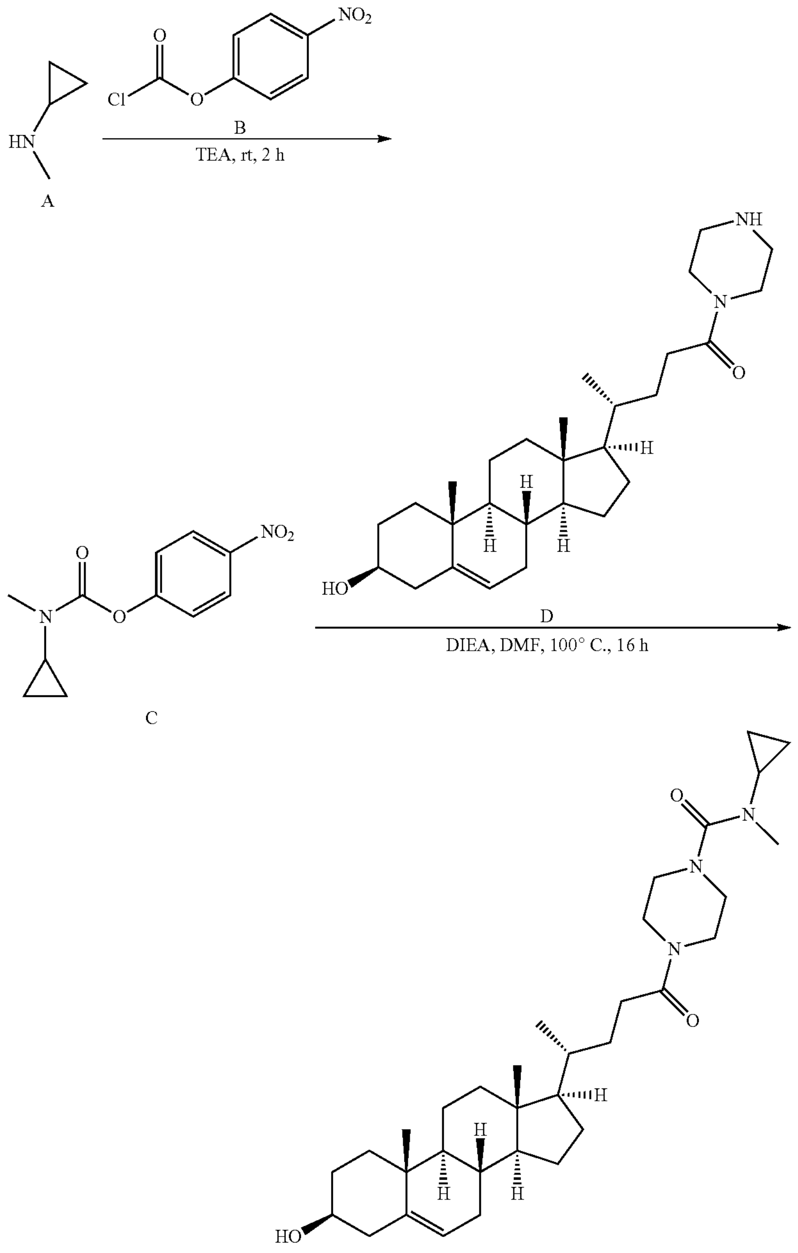

211

To a solution of compound A (90 mg, 1.27 mmol) and triethylamine (192 mg, 1.9 mmol) in dichloromethane (5 mL) was added compound B (255 mg, 1.27 mmol) at 0° C. under $N_2$ and stirred for 2 hours. The mixture was concentrated in vacuum to give the crude which was purified by Prep-TLC to give compound C (285 mg, 1.21 mmol).

To a solution of compound D (337 mg, 762 μmol) and compound C (150 mg, 635 μmol) in DMF (4 mL) was added DIEA (246 mg, 1.9 mmol) and heated at 100° C. under $N_2$ for 16 h. The mixture was diluted with HCl (20 mL, 1 M water solution) and extracted with EA (50 mL). The organic layer was washed with $NaHCO_3$ (20 mL), water (20 mL*2) and brine (20 mL), dried over sodium sulfate and concentrated in vacuum to give the crude which was purified by silica gel chromatography (EtOAc/Pet.ether=1/10) to give the title compound 211 (32 mg, 59.3 μmol) as a white solid. LCMS: $[M+H^+]$=540.5. $^1$H NMR (400 MHz, Chloroform-d) δ 5.37-5.33 (m, 1H), 3.66-3.42 (m, 6H), 3.34 (bs, 4H), 2.85 (s, 3H), 2.63-2.59 (m, 1H), 2.43-2.20 (m, 4H), 2.02-1.95 (m, 2H), 1.89-1.74 (m, 4H), 1.54-1.43 (m, 6H), 1.37-1.24 (m, 3H), 1.20-1.06 (m, 4H), 1.00 (s, 3H), 0.95 (d, J=6.5 Hz, 3H), 0.75-0.73 (m, 2H), 0.68 (s, 3H), 0.65-0.58 (m, 2H).

Example 212: N,N-diethyl-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperazine-1-carboxamide

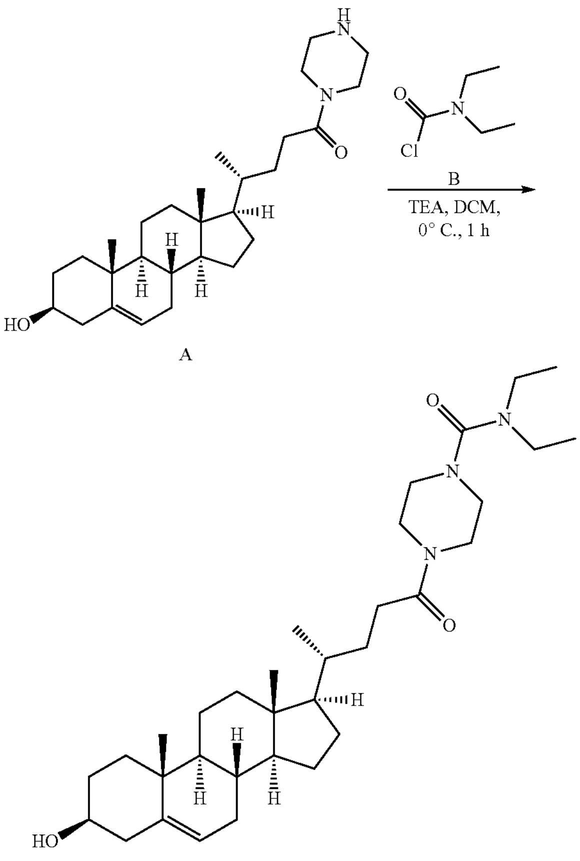

A

212

To a solution of compound A (300 mg, 678 μmol) in dichloromethane (3 mL) was added triethylamine (343 mg, 3.39 mmol) and N,N-diethylcarbamoyl chloride (73.5 mg, 542 μmol) at 0° C. The reaction mixture was stirred for 1 hour. After completion, the mixture was quenched by adding water (10 mL) and extracted with ethyl acetate (10 mL×3). The organic layer was washed with brine, dried over sodium sulfate, filtered, and concentrated to give the crude which was purified by column chromatography on silica gel to yield the title compound 212 (290 mg, 78.98%) as a white solid. LCMS: $[M+H]^+$=542.30. $^1$H NMR (400 MHz, Chloroform-d) δ 5.37-5.32 (m, 1H), 3.69-3.40 (m, 5H), 3.27-3.14 (m, 8H), 2.44-2.17 (m, 4H), 2.02-1.72 (m, 6H), 1.66 (s, 3H), 1.62-1.02 (m, 19H), 1.00 (s, 3H), 0.95 (d, J=6.4 Hz, 3H), 0.68 (s, 3H).

Example 213: N-ethyl-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N-methylpiperazine-1-carboxamide

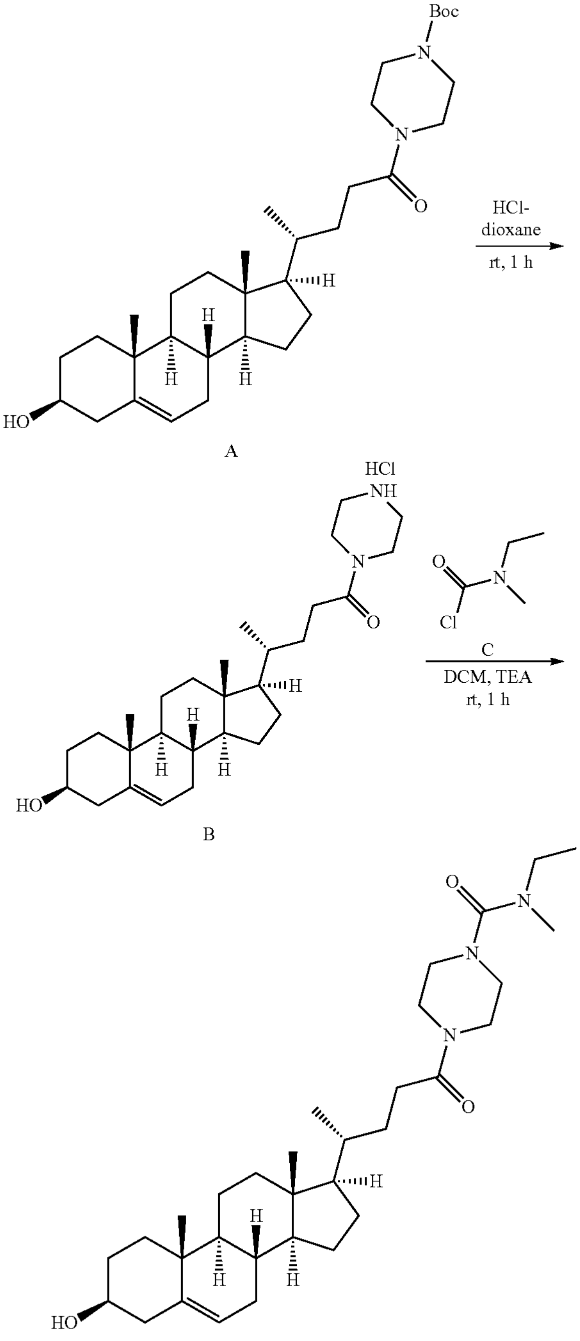

A

B

213

HCl (120 mL, 480 mmol, 4 M in dioxane) was added slowly to the solution of compound A (9.6 g, 17.71 mmol) in dioxane (100 mL) at room temperature and stirred for 1 hour. After completion, to the reaction mixture was concentrated under vacuum to give the title compound B (7.2 g, 85%) as a white solid.

To a solution of compound B (200 mg, 418 μmol) in dichloromethane (5 mL) was added triethylamine (183 mg, 1.81 mmol) and compound C (49.4 mg, 408 μmol) at 0° C. and stirred for 1 hour. After completion, the mixture was quenched by water (10 mL) and extracted with dichloromethane (10 mL×3). The organic layer was washed with brine, dried over sodium sulfate, filtered, and concentrated to give the crude which was purified by column chromatography on silica gel to yield the title compound 213 (88 mg, 37%) as a white solid. LCMS: $[M+H]^+$=528.2. $^1$H NMR (400 MHz, Chloroform-d) δ 5.34 (d, J=5.0 Hz, 1H), 3.65-3.56 (m, 2H), 3.55-3.42 (m, 3H), 3.27-3.14 (m, 6H), 2.82 (s, 3H), 2.45-2.33 (m, 1H), 2.33-2.18 (m, 3H), 2.04-1.93 (m, 2H), 1.89-1.73 (m, 4H), 1.66 (br, 1H), 1.56-1.40 (m, 6H), 1.39-1.23 (m, 3H), 1.13-1.05 (m, 7H), 1.00 (s, 3H), 0.95 (d, J=6.6 Hz, 3H), 0.68 (s, 3H).

Example 214: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(1-methyl-1H-pyrazol-4-yl)piperazin-1-yl)pentan-1-one

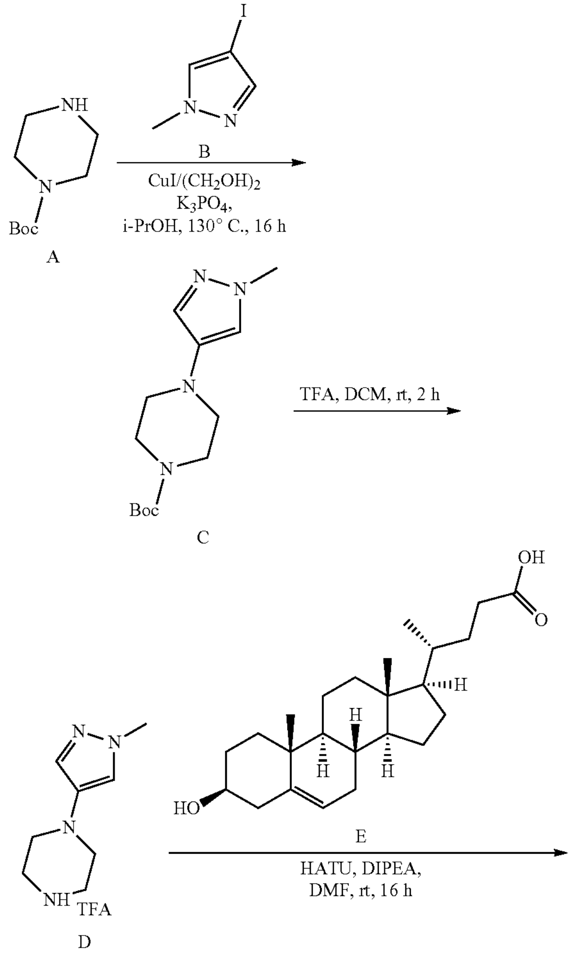

-continued

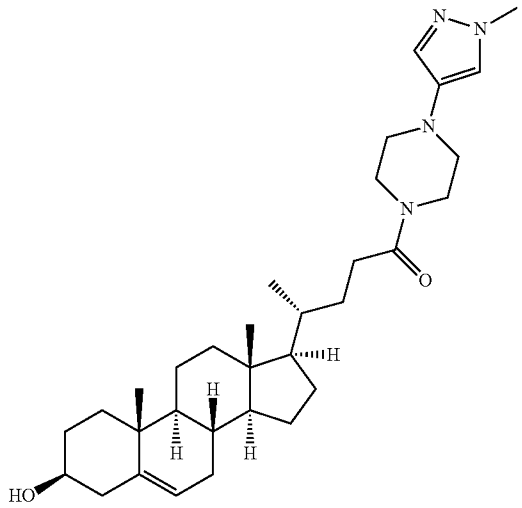

214

To a solution of compound A (500 mg, 2.68 mmol) in isopropanol (10 mL), compound B (1.12 g, 5.37 mmol), CuI (341 mg, 1.07 mmol), potassium phosphate (2.28 g, 10.7 mmol) and ethane-1,2-diol (333 mg, 5.37 mmol) were added and heated at 130° C. under $N_2$ for 16 h. The mixture was concentrated in vacuum to give the crude which was purified by silica gel chromatography (EtOAc/Pet.ether=1/10-1:3) to give compound C (150 mg, 563 μmol).

To a solution of compound C (150 mg, 563 μmol) in dichloromethane (6 mL) was added TFA (2 mL) at room temperature under $N_2$ and stirred for 2 h. The mixture was concentrated in vacuum to give compound D (181 mg).

To a solution of compound E (272 mg, 726 μmol), compound D (181 mg, ca 563 μmol) and DIPEA (469 mg, 3.63 mmol) in DMF (5 mL) was added HATU (414 mg, 1.09 mmol) at room temperature under $N_2$ and stirred for 16 h. The mixture was diluted with $NH_4Cl$ (aq., 30 mL) and extracted with EA (50 mL). The organic layer was washed with $NaHCO_3$ (20 mL), water (20 mL*3) and brine (20 mL), dried over sodium sulfate and concentrated in vacuum. The residue was purified by silica gel chromatography (DCM: MeOH=100: 0-100:2) to give the title compound 214 (271 mg) as a white solid. LCMS: $[M+H^+]$=523.5. $^1$H NMR (400 MHz, DMSO-$d_6$) δ 7.29 (s, 1H), 7.17 (s, 1H), 5.28 (d, J=4.9 Hz, 1H), 4.60 (d, J=4.6 Hz, 1H), 3.74 (s, 3H), 3.55 (t, J=5.1 Hz, 4H), 3.33 (s, 3H), 3.26 (dq, J=10.0, 5.1, 4.7 Hz, 1H), 2.84 (d, J=5.8 Hz, 2H), 2.78 (d, J=5.1 Hz, 2H), 2.36 (ddd, J=15.5, 10.3, 5.3 Hz, 1H), 2.31-2.05 (m, 3H), 2.02-1.63 (m, 6H), 1.61-1.34 (m, 7H), 1.33-0.97 (m, 8H), 0.96 (s, 3H), 0.93 (d, J=6.5 Hz, 3H), 0.88 (dd, J=11.5, 4.7 Hz, 1H), 0.67 (s, 3H).

Example 215: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-3-(pyrimidin-4-yloxy)pyrrolidin-1-yl)pentan-1-one

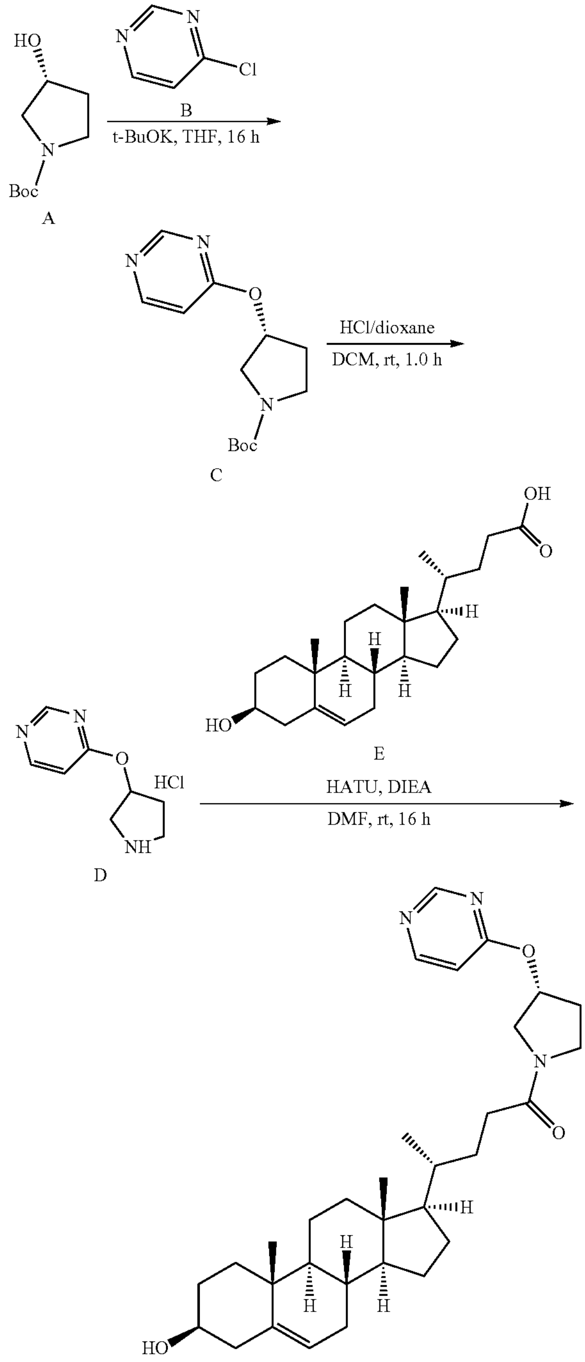

215

To a solution of compound A (245 mg, 1.31 mmol) and 4-chloropyrimidine (200 mg, 1.75 mmol) in tetrahydrofuran (3 mL) was added tBuOK (392 mg, 3.49 mmol). The reaction mixture was stirred at room temperature under $N_2$ for 16 h. The reaction was quenched with saturated $NH_4Cl$ and extracted with EtOAc. The organic layer was washed by brine, dried over sodium sulfate, filtered, and concentrated. The mixture was purified by column chromatography on silica gel to afford compound C (150 mg) as a white solid.

To a solution of compound C (150 mg, 565 μmol) in dichloromethane (2 mL) was added HCl (0.5 mL, 4M in dioxane, 2 mmol). The reaction mixture was stirred at room temperature for 1 h. The mixture was concentrated to afford the compound D (120 mg) as a solid.

To a solution of compound E (204 mg, 0.5 mmol) and compound D (120 mg, ca 0.565 mmol) in DMF (5 mL) was added DIEA (469 mg, 3.63 mmol) and HATU (460 mg, 1.21 mmol). The reaction mixture was stirred at room temperature under $N_2$ for 16 h. The reaction was quenched with saturated $NH_4Cl$ and extracted with EtOAc. The organic layer was washed by brine, dried over sodium sulfate, filtered, and concentrated. The mixture was purified by pre-HPLC to afford compound 215 (18.1 mg) as a white solid. $^1$H NMR (400 MHz, Chloroform-d) δ 8.77 (d, J=6.8 Hz, 1H), 8.45 (dd, J=9.8, 5.8 Hz, 1H), 6.76-6.68 (m, 1H), 5.68 (d, J=14.8 Hz, 1H), 5.34 (s, 1H), 3.85-3.46 (m, 5H), 2.37-2.10 (m, 6H), 2.04-1.94 (m, 2H), 1.89-1.74 (m, 4H), 1.64-1.41 (m, 11H), 1.32-1.07 (m, 5H), 1.00 (d, J=2.0 Hz, 3H), 0.98-0.90 (m, 4H), 0.68 (d, J=5.6 Hz, 3H). LCMS: [M+1]=522.25.

Example 216: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3S)-3-(pyrimidin-4-yloxy)pyrrolidin-1-yl]pentan-1-one

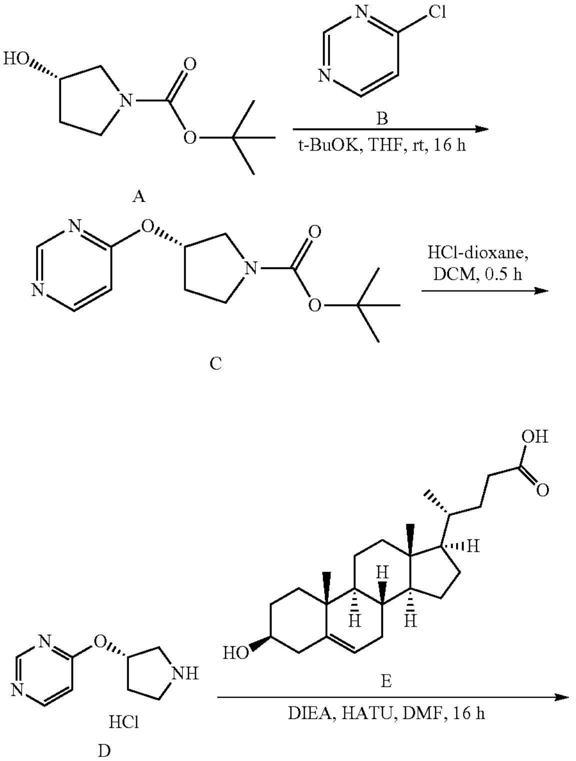

-continued

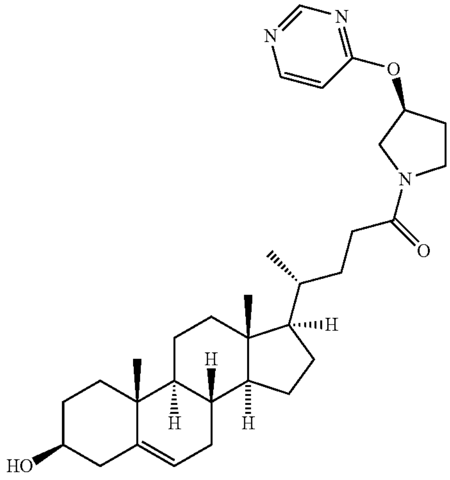

Example 216

To a solution of compound A (200 mg, 1.07 mmol) in tetrahydrofuran (2 mL) was added compound B (147 mg, 1.2 eq., 1.28 mmol) and tBuOK (479 mg, 4 eq., 4.27 mmol). The mixture was stirred at room temperature for 16 hours. The reaction was quenched with water and extracted with ethyl acetate (10 mL×4). The combined organic layer was concentrated to give the crude which was purified by silica gel chromatograph to yield the title compound C (200 mg, 70%).

To a solution of compound C (260 mg, 980 μmol) in dichloromethane (2 mL) was added hydrogen chloride (1 mL, 4 mmol, 4M in dioxane,). The mixture was stirred at room temperature for 30 mins. The reaction was quenched with water and extracted with ethyl acetate (10 mL×4). The combined organic layer was concentrated to give the crude compound D (150 mg, 76%).

To a solution of compound D (80 mg, 398 μmol) in DMF (2 mL) was added compound E (145 mg, 0.8 eq., 387 μmol), DIEA (376 mg, 6 eq., 2.91 mmol) and HATU (228 mg, 2 eq., 969 μmol). After stirring at room temperature for 16 hours, the reaction was quenched with water and extracted with ethyl acetate (10 mL×4). The combined organic layer was concentrated to give the crude which was purified by silica gel chromatograph to yield the title compound 216 (67.7 mg, 26%). $^{1}$H NMR (400 MHz, Chloroform-d) δ 8.86 (s, 1H), 8.51 (d, J=5.8 Hz, 1H), 6.82 (d, J=5.4 Hz, 1H), 5.73 (s, 1H), 5.35 (s, 1H), 3.99-3.44 (m, 5H), 2.49 (b, 2H), 2.36-2.12 (m, 6H), 1.99-1.85 (m, 5H), 163-1.37 (m, 7H), 1.37-1.21 (m, 3H), 1.21-1.02 (m, 4H), 1.00 (s, 3H), 0.97-0.85 (m, 5H), 0.67 (d, J=9.4 Hz, 3H). LCMS: [M+1]=522.25.

Examples 217: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3R)-3-(pyrimidin-4-yloxy)piperidin-1-yl]pentan-1-one

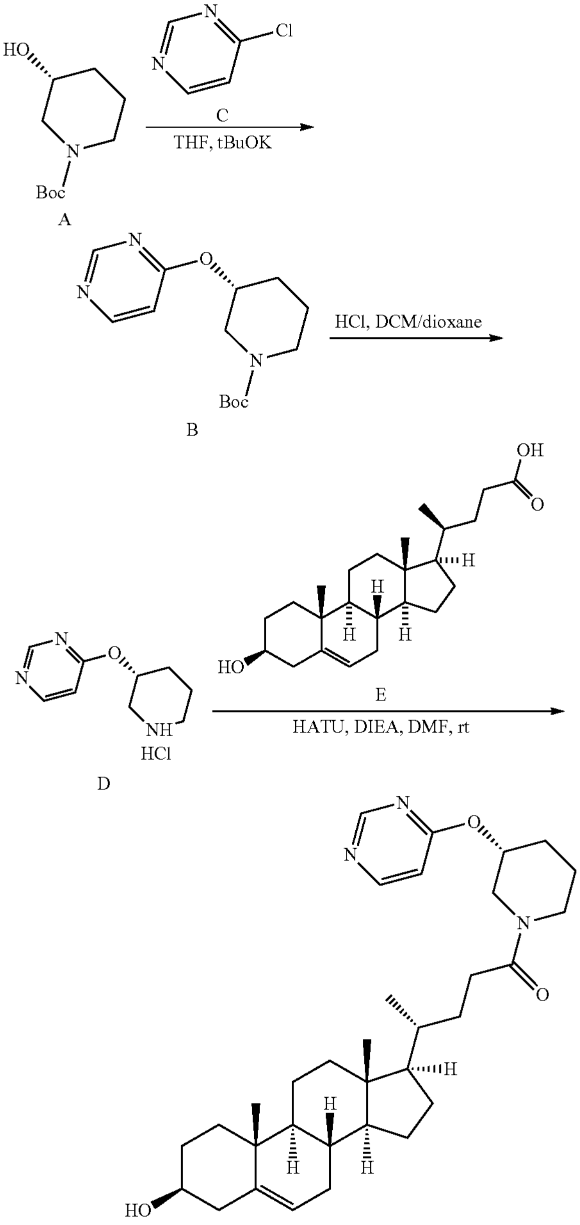

217

To a solution of compound A (200 mg, 994 μmol) and compound C (137 mg, 1.19 mmol) in tetrahydrofuran (4 mL) at room temperature was added followed by t-BuOK (335 mg, 2.98 mmol). The mixture was stirred for 16 hours. The solvent was removed under vacuum. The residue was diluted with water, extracted with EA. The organic layer was washed by brine, dried over sodium sulfate, filtered, and concentrated. The mixture was purified by column chromatography on silica gel to afford compound B (140 mg, 50%) as a white solid.

HCl (1 mL, 4 mmol, 4M in dioxane) was added slowly to the compound B (140 mg, 502 μmol) in a DCM (3 mL) at room temperature and stirred for 1 hour. After completion, the reaction mixture was added dichloromethane (10 mL) and concentrated three times to give the title compound D (90 mg, 84%) as a solid.

To a solution of compound D (90 mg, 418 μmol) and compound E (150 mg, 402 μmol) in DMF (8 mL) was added HATU (382 mg, 1 mmol) and DIEA (402 mg, 3 mmol). The mixture was stirred at room temperature for 3 hours. After completion, the mixture was quenched by adding saturated ammonium chloride solution (30 mL) and extracted with ethyl acetate (10 mL×3). The organic layer was washed with brine, dried over sodium sulfate, filtered, and concentrated to give the crude which was purified by column chromatography on silica gel to yield the title compound 217 (80 mg, 30%) as a white solid. $^1$H NMR (400 MHz, Chloroform-d) δ 8.78-8.72 (m 1H), 8.47-8.39 (m, 1H), 6.73-6.65 (m, 1H), 5.37-5.32 (m, 1H), 5.22-5.11 (m, 1H), 4.06-3.32 (m, 5H), 2.47-2.14 (m, 4H), 2.06-1.74 (m, 9H), 1.57-1.30 (m, 9H), 1.22-1.06 (m, 3H), 1.05-0.83 (m, 10H), 0.71-0.61 (m, 3H). LCMS: [M+1]=536.35.

Example 218: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-(pyrimidin-4-yloxy)piperidin-1-yl)pentan-1-one

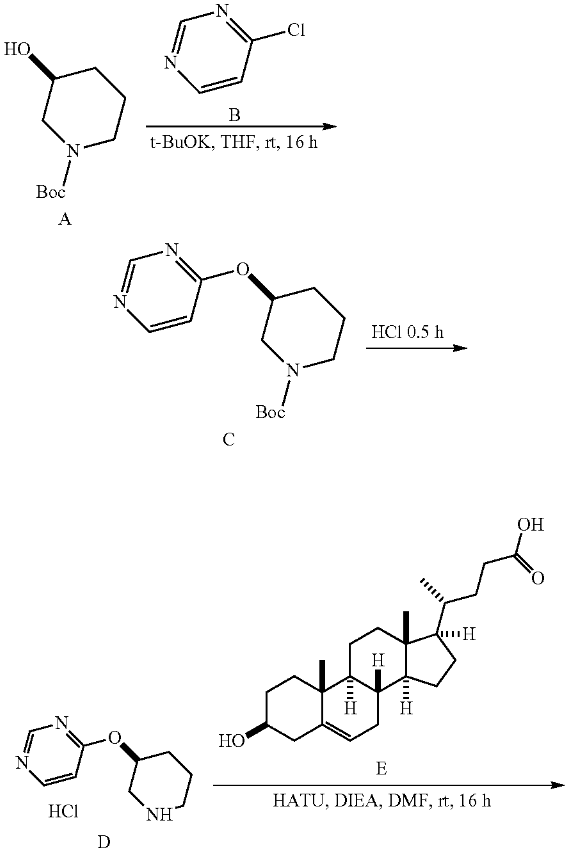

-continued

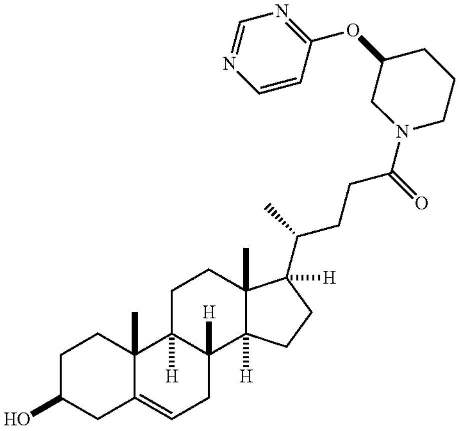

218

To a solution of compound A (200 mg, 994 μmol) in tetrahydrofuran (4 mL) was added compound B (137 mg, 1.19 mmol) and tBuOK (335 mg, 2.98 mmol). The mixture was stirred at room temperature for 16 hours. After completion, the mixture was quenched by adding saturated ammonium chloride solution (30 mL) and extracted with ethyl acetate (15 mL×3). The organic layer was washed with brine, dried over sodium sulfate, filtered, and concentrated to give compound C (240 mg 84%).

HCl (0.5 mL, 2 mmol, 4M in dioxane) was added slowly to the solution of compound C (100 mg, 358 μmol) in DCM (2 mL) at room temperature and stirred for 0.5 hour. After completion, the reaction mixture was concentrated to give the title compound D (72 mg, 93.52%) as a solid.

To a solution of compound D (72 mg, 335 μmol) in DMF (3 mL) was added compound E (113 mg, 301 μmol), DIEA (260 mg, 2.01 mmol) and HATU (229 mg, 670 μmol). The mixture was stirred at room temperature for 16 hours. After completion, the mixture was quenched by adding saturated ammonium chloride solution (30 mL) and extracted with ethyl acetate (15 mL×3). The organic layer was washed with brine, dried over sodium sulfate, filtered, and concentrated to give the crude which was purified by column chromatography on silica gel to yield the title compound 218 (40 mg, 22.3%) as a white solid. $^1$H NMR (400 MHz, Chloroform-d) δ 8.83 (d, J=23.1 Hz, 1H), 8.47 (d, J=5.9 Hz, 1H), 6.79 (dd, J=18.4, 5.9 Hz, 1H), 5.44-5.13 (m, 2H), 3.96-3.39 (m, 5H), 2.41-2.20 (m, 5H), 2.15-1.71 (m, 11H), 1.67-1.25 (m, 12H), 1.12 (dd, J=18.5, 7.7 Hz, 4H), 1.00 (d, J=2.2 Hz, 3H), 0.97-0.83 (m, 5H), 0.67 (d, J=12.3 Hz, 3H). LCMS: $[M+1]^+$=536.20.

Example 219: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyridin-3-yloxy)piperidin-1-yl)pentan-1-one

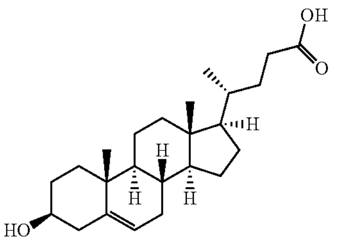

A

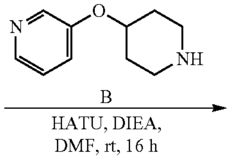

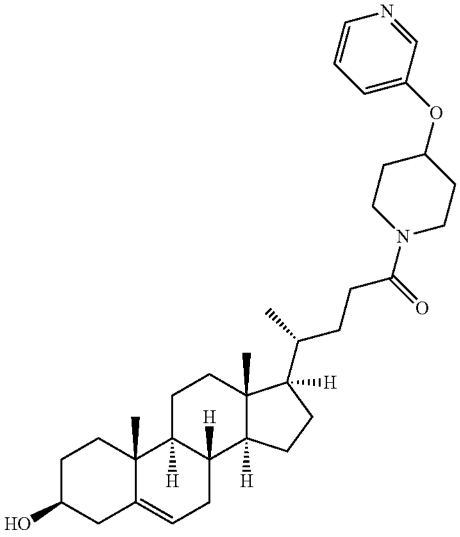

219

To a solution of compound A (300 mg, 801 μmol) and compound B (143 mg, 801 μmol) in DMF (5 mL) was added HATU (457 mg, 1.2 mmol) and DIEA (311 mg, 2.4 mmol). The mixture was stirred at room temperature for 16 hours. After completion, the mixture was quenched by adding saturated ammonium chloride solution (20 mL) and extracted with ethyl acetate (20 mL×3). The organic layer was washed with brine, dried over sodium sulfate, filtered, and concentrated to give the crude which was purified by column chromatography on silica gel to yield the title compound 219 (290 mg, 67.7%) as a white solid. LCMS: $[M+H]^+$=535.20. $^1H$ NMR (400 MHz, Chloroform-d) δ 8.33 (t, J=1.6 Hz, 1H), 8.26-8.20 (m, 1H), 7.25-7.21 (m, 2H), 5.39-5.30 (m, 1H), 4.62-4.54 (m, 1H), 3.85-3.38 (m, 5H), 2.46-2.19 (m, 4H), 2.05-1.74 (m, 10H), 1.64-1.05 (m, 13H), 1.00 (s, 3H), 0.96 (d, J=6.4 Hz, 3H), 0.94-0.88 (m, 1H), 0.69 (s, 3H).

Example 220: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyrazin-2-yloxy)piperidin-1-yl)pentan-1-one

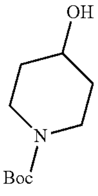

A

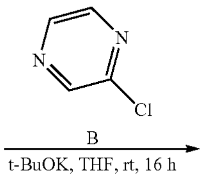

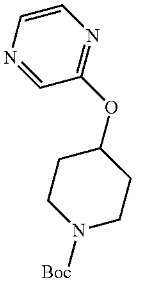

C

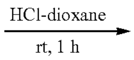

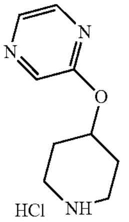

HCl

D

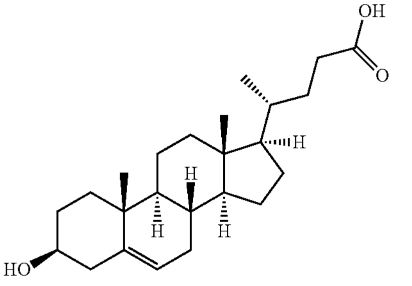

E

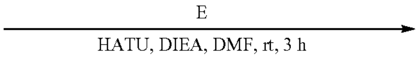

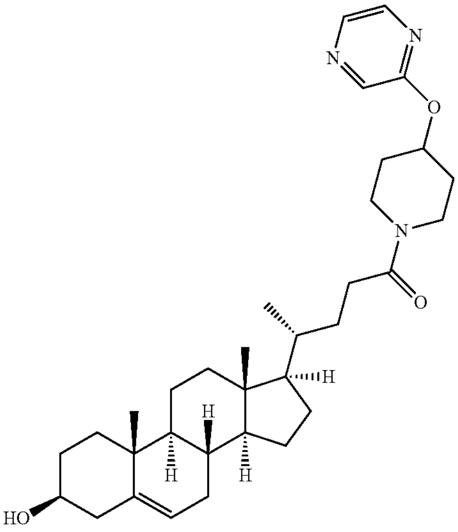

220

To a solution of compound A (600 mg, 2.98 mmol) in tetrahydrofuran (20 mL) was added tBuOK (1.34 g, 11.9 mmol) and compound B (410 mg, 3.58 mmol), then the reaction mixture was stirred at room temperature under nitrogen for 16 hours. After completion, the mixture was quenched by adding water (20 mL) and extracted with ethyl acetate (20 mL×3). The organic layer was washed with brine, dried over sodium sulfate, filtered, and concentrated to give the title compound C (650 mg, 78%) as a white solid.

HCl (2 mL, 8 mmol, 4 M in dioxane) was added slowly to the solution of compound C (350 mg, 1.25 mmol) in dioxane (3 mL) at room temperature and stirred for 1 hour. After completion, the reaction mixture was concentrated to give the title compound D (220 mg, 82%).

To a solution of compound D (144 mg, 667 μmol) and compound E (0.2 g, 534 μmol) in DMF (5 mL) was added HATU (251 mg, 1.07 mmol) and DIEA (345 mg, 2.67 mmol). The mixture was stirred at room temperature for 3 hours. After completion, the mixture was quenched by adding saturated ammonium chloride solution (50 mL) and extracted with ethyl acetate (50 mL×3). The organic layer was washed with brine, dried over sodium sulfate, filtered, and concentrated to give the crude which was purified by column chromatography on silica gel to yield the title compound 220 (166 mg, 58%) as a white solid. LCMS: $[M+H]^+=536.2$. $^1H$ NMR (400 MHz, Chloroform-d) δ 8.21 (d, J=1.4 Hz, 1H), 8.12 (d, J=2.8 Hz, 1H), 8.06 (m, 1.4 Hz, 1H), 5.35 (d, J=5.2 Hz, 1H), 5.30-5.22 (m, 1H), 3.99-3.89 (m, 1H), 3.78-3.68 (m, 1H), 3.56-3.44 (m, 2H), 3.45-3.35 (m, 1H), 2.45-2.35 (m, 1H), 2.32-2.18 (m, 3H), 2.08-1.94 (m, 4H), 1.93-172 (m, 6H), 1.70-1.54 (m, 4H), 1.53 (d, J=9.4 Hz, 1H), 1.47-1.43 (m, 2H), 1.38-1.25 (m, 2H), 1.20-1.03 (m, 4H), 1.01 (s, 3H), 0.99-0.88 (m, 4H), 0.69 (s, 3H).

Example 221: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(pyrimidin-4-yloxy)piperidin-1-yl]pentan-1-one

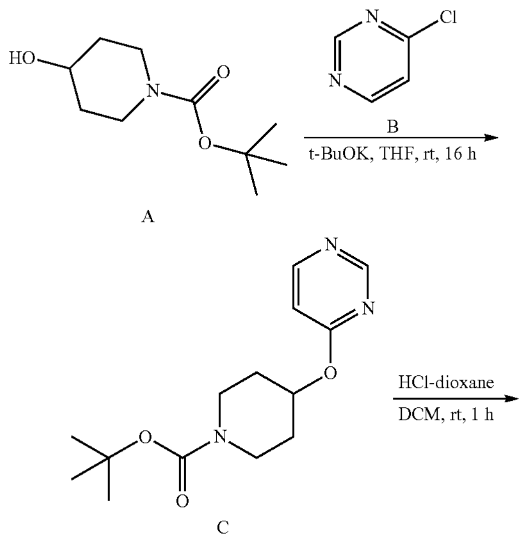

A B C

-continued

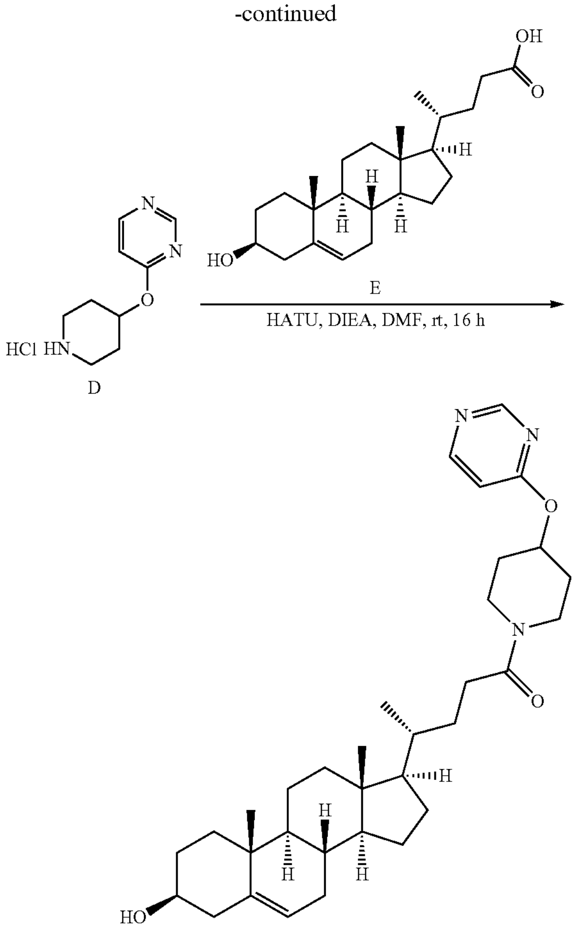

D E

Example 221

To a solution of compound A (0.2 g, 994 μmol) in tetrahydrofuran (2 mL) was added compound B (137 mg, 1.2 eq., 1.19 mmol) and tBuOK (446 mg, 4 eq., 3.97 mmol). The mixture was stirred at room temperature for 16 hours. The reaction was quenched with water and extracted with ethyl acetate (10 mL×4). The combined organic layer was concentrated to give the crude compound C (270 mg, 97%).

To a solution of compound C (280 mg, 1 mmol) in dichloromethane (2 mL) was added hydrogen chloride (2 mL, 8 mmol, 4M in dioxane). Then the mixture was stirred at room temperature for 1 hour. The reaction was diluted with water and extracted with DCM (10 mL×4). The combined organic layer was concentrated to give the crude compound D (128 mg, 59%).

To a solution of compound D (128 mg, 593 μmol) in DMF (2 mL) was added compound E (161 mg, 0.6 eq., 429 μmol), DIEA (554 mg, 6 eq., 4.29 mmol) and HATU (543 mg, 2 eq., 1.43 mmol). The mixture was stirred at room temperature for 16 hours. The reaction was quenched with water and extracted with ethyl acetate (10 mL×4). The combined organic layer was concentrated to give the crude which was purified by silica gel chromatograph to yield the title compound 221 (55 mg, 23%). $^1$HNMR (400 MHz, Chloroform-d) δ 8.75 (s, 1H), 8.43 (d, J=5.8 Hz, 1H), 6.76-6.66 (m, 1H), 5.45-5.31 (m, 2H), 4.01-3.91 (m, 1H), 3.77-3.67 (m, 1H), 3.58-3.34 (m, 3H), 2.40 (t, J=10.6 Hz, 1H), 2.33-2.18 (m, 3H), 2.09-1.94 (m, 4H), 1.88-1.74 (m, 5H), 1.65 (s, 3H), 1.60-1.43 (m, 8H), 1.37-1.24 (m, 4H), 1.21-1.03 (m, 4H), 1.00 (s, 3H), 0.99-0.87 (m, 4H), 0.68 (s, 3H). LCMS: [M+1]=536.10.

Example 222: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyrimidin-5-yl)piperazin-1-yl)pentan-1-one

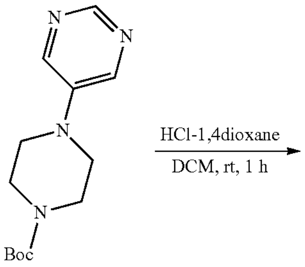

A

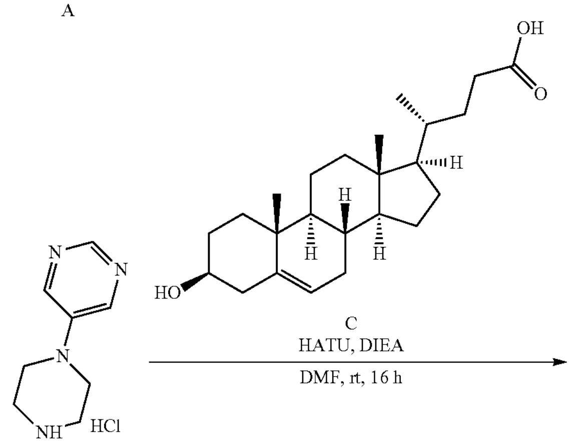

B

C

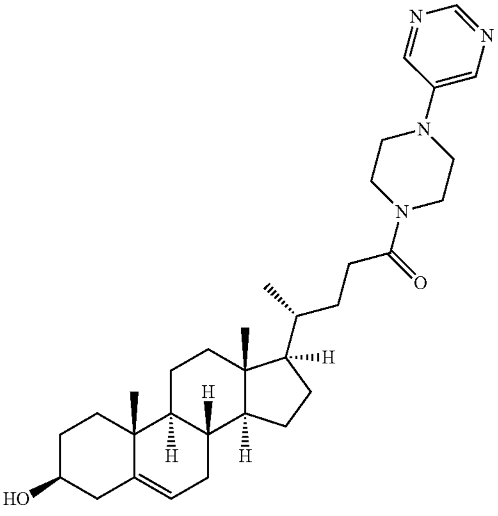

222

HCl (0.5 mL, 4 mmol, 4M in dioxane) was added slowly to a solution of the compound A (100 mg, 378 μmol) in DCM (2 mL) at room temperature and stirred for 1 hour. After completion, the reaction mixture was concentrated to give the title compound B (76 mg) as a solid.

To a solution of compound C (200 mg, 534 μmol) and compound B (76 mg, 380 μmol) in DMF (3 mL) was added HATU (305 mg, 801 μmol) and DIEA (207 mg, 1.6 mmol). The mixture was stirred at room temperature for 16 hours. After completion, the mixture was quenched by adding saturated ammonium chloride solution (20 mL) and extracted with ethyl acetate (20 mL×3). The organic layer was washed with brine, dried over sodium sulfate, filtered, and concentrated to give the crude which was purified by column chromatography on silica gel to yield the title compound 222 (95 mg, 34.2%) as a white solid. LCMS: $[M+H]^+$=521.25. 1H NMR (400 MHz, Chloroform-d) δ 8.74 (s, 1H), 8.39 (s, 2H), 5.36-5.33 (m, 1H), 3.81 (t, J=5.2 Hz, 2H), 3.67 (t, J=5.0 Hz, 2H), 3.56-3.48 (m, 1H), 3.29-3.20 (m, 4H), 2.47-2.23 (m, 4H), 2.03-1.78 (m, 7H), 1.69 (bs, 3H), 1.63-1.32 (m, 8H), 1.17-1.03 (m, 4H), 1.00 (s, 3H), 0.97 (d, J=6.4 Hz, 3H), 0.68 (s, 3H).

Example 223: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-((1-methyl-1H-pyrazol-4-yl)methyl)piperazin-1-yl)pentan-1-one

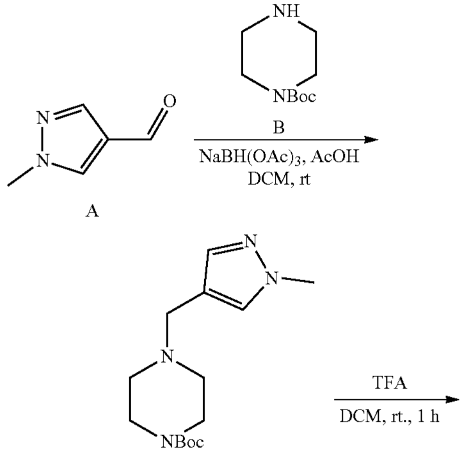

A

B

C

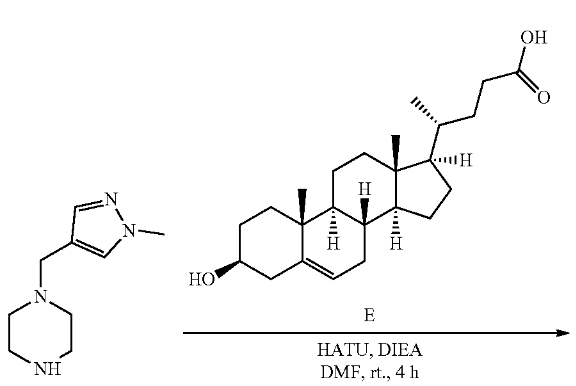

$CF_3COOH$

D

E

-continued

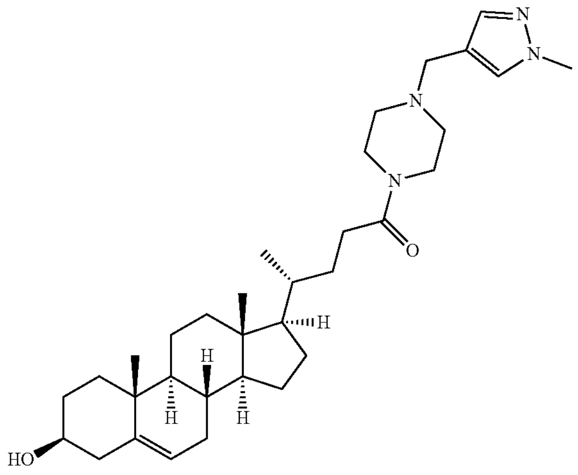

223

To a solution of compound A (200 mg, 1.82 mmol) in DCM (5 mL) was added compound B (338 mg, 1.82 mmol), AcOH (109 mg, 1.82 mmol) and $NaBH(OAc)_3$ (462 mg, 2.18 mmol). The mixture was stirred at room temperature under $N_2$ for 2 h. The mixture was added $NaHCO_3$ and extracted with EA. The organic layer was dried over sodium sulfate and concentrated. The residue was purified by silica gel chromatography to afford compound C (120 mg, 23.6%).

To a solution of compound C (120 mg, 428 μmol) in DCM (2 mL) was added TFA (0.5 mL). The mixture was stirred at room temperature for 1 h. The mixture was concentrated to afford compound D which was used directly in the next step.

To a solution of compound E (100 mg, 267 μmol) in DMF (2 mL) was added compound D (96.2 mg, 327 μmol), DIEA (173 mg, 1.33 mmol) and HATU (152 mg, 0.4 mmol). The mixture was stirred at room temperature for 4 h. The mixture was added water and extracted with EA. The organic layer was washed with brine, dried over sodium sulfate, and concentrated. The crude was purified by silica gel chromatography to afford compound 223 (134.3 mg, 93.7%). LCMS [M+1]=537.20. $^1$HNMR (400 MHz, Chloroform-d) δ 7.39 (s, 1H), 7.28 (s, 1H), 5.34 (d, J=5.0 Hz, 1H), 3.88 (s, 3H), 3.64-3.58 (m, 2H), 3.55-3.48 (m, 1H), 3.47-3.41 (m, 4H), 2.44-2.14 (m, 8H), 2.02-1.79 (m, 5H), 1.79-1.40 (m, 12H), 1.37-1.24 (m, 4H), 1.20-1.02 (m, 5H), 1.00 (s, 3H), 0.97 (d, J=5.7 Hz, 1H), 0.94 (d, J=6.5 Hz, 3H), 0.92-0.85 (m, 1H), 0.67 (s, 3H).

Example 224: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-{4-[(pyrimidin-5-yl)methyl]piperazin-1-yl}pentan-1-one

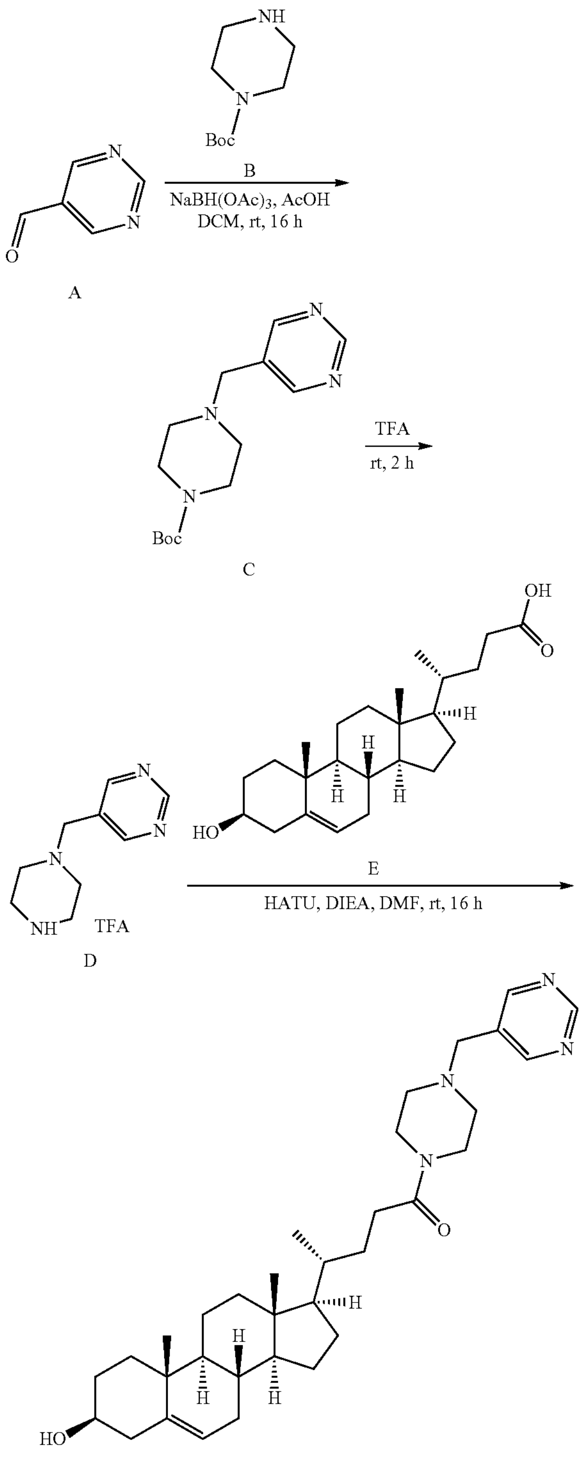

224

To a solution of compound A (500 mg, 4.63 mmol) in DCM (5 mL) was added compound B (861 mg, 4.63 mmol)

and $NaBH(OAc)_3$ (1.96 g, 9.25 mmol) and AcOH (27.8 mg, 463 μmol) at room temperature and stirred for 16 h. The mixture was concentrated to give crude which was purified by silica gel chromatography to give compound C (200 mg).

To a solution of compound C (200 mg, 719 μmol) in DCM (5 mL) was added TFA (2 mL) at room temperature and stirred for 2 h. The mixture was concentrated to give compound D (120 mg).

To a solution of compound D (150 mg, 543 μmol) in DMF (5 mL) was added compound E (284 mg, 757 μmol), HATU (480 mg, 1.26 mmol) and DIEA (435 mg, 3.37 mmol) at room temperature and stirred for 16 h. The mixture was extracted with EA/water. The organic layer was concentrated to give the crude which was purified by silica gel chromatograph to give the title compound 224 (60 mg). $^1H$ NMR (400 MHz, Chloroform-d) δ 9.14 (s, 1H), 8.70 (s, 2H), 5.34 (d, J=4.8 Hz, 1H), 3.63 (t, J=5.0 Hz, 2H), 3.55-3.45 (m, 5H), 2.44 (t, J=5.0 Hz, 4H), 2.39-2.19 (m, 4H), 2.01-1.78 (m, 5H), 1.61-1.03 (m, 15H), 1.00 (s, 3H), 0.94 (d, J=6.6 Hz, 3H), 0.90-0.82 (m, 1H), 0.68 (s, 3H). M+1=535.20.

Example 225: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(5-methyl-1,3,4-thiadiazol-2-yl)piperazin-1-yl)pentan-1-one

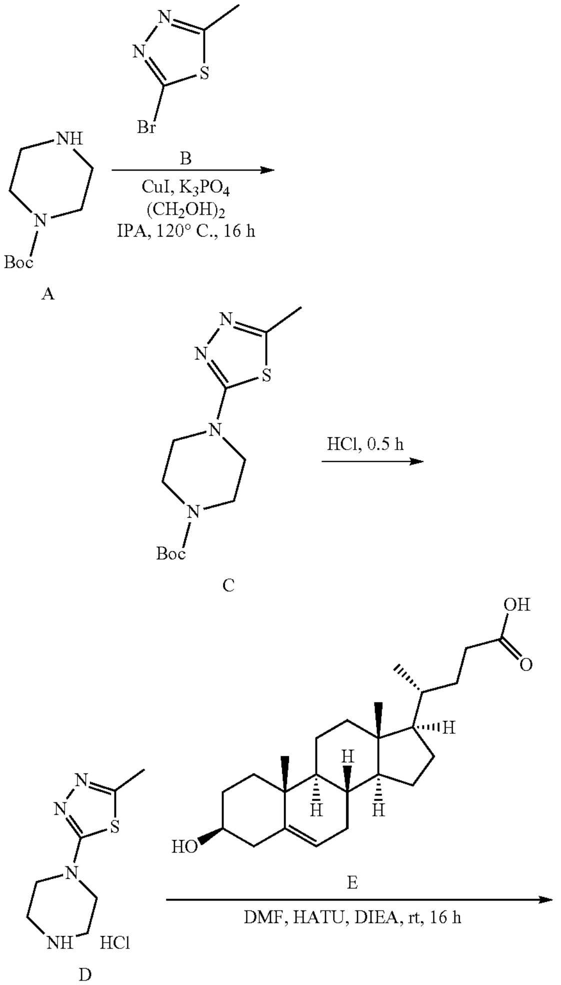

B
A
C
E
D

-continued

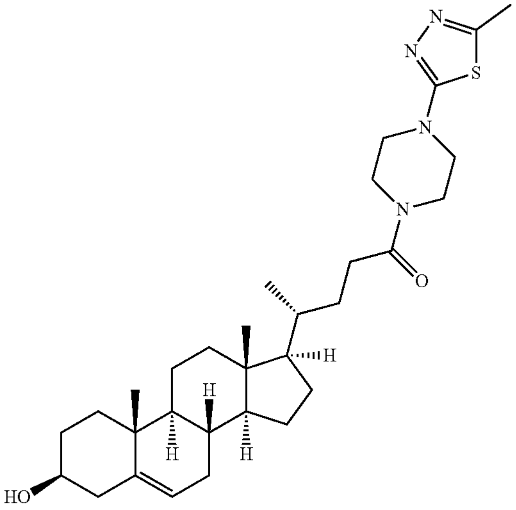

225

To a solution of compound A (100 mg, 537 μmol) in isopropanol (3 mL) was added compound B (192 mg, 1.07 mmol), K3PO4 (456 mg, 2.15 mmol), CuI (20.5 mg, 107 μmol) and ethane-1,2-diol (33.3 mg, 537 μmol) under $N_2$. The mixture was stirred at 120° C. for 16 hours. After completion, the mixture was quenched by adding saturated ammonium chloride solution (30 mL) and extracted with ethyl acetate (15 mL×3). The organic layer was washed with brine, dried over sodium sulfate, filtered, and concentrated to give compound C (70 mg, 45.8%).

HCl (2 mL, 4M in dioxane, 8 mmol) was added slowly to the solution of compound C (70 mg, 246 μmol) in DCM (2 mL) at room temperature and stirred for 0.5 hour. After completion, the reaction mixture was concentrated to give the title compound D (59 mg) as a solid.

To a solution of compound D (59 mg, 268 μmol) in DMF (3 mL) was added compound E (91.5 mg, 244 μmol), DIEA (210 mg, 1.63 mmol) and HATU (176 mg, 543 μmol). The mixture was stirred at room temperature for 16 hours. After completion, the mixture was quenched by adding saturated ammonium chloride solution (30 mL) and extracted with ethyl acetate (15 mL×3). The organic layer was washed with brine, dried over sodium sulfate, filtered, and concentrated to give the crude which was purified by column chromatography on silica gel to yield the title compound 225 (40 mg, 30.3%) as a white solid. $^1H$ NMR (400 MHz, Chloroform-d) δ 5.35 (d, J=4.8 Hz, 1H), 3.84-3.57 (m, 6H), 3.56-3.50 (m, 1H), 3.48 (s, 1H), 3.46 (bs, 1H), 2.61 (s, 3H), 2.45-2.18 (m, 4H), 2.03-1.94 (m, 2H), 1.90-1.74 (m, 4H), 1.64-1.27 (m, 10H), 1.21-0.98 (m, 8H), 0.98-0.88 (m, 4H), 0.69 (s, 3H). LCMS: $[M+1]^+$=541.15.

Example 226: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(1-methyl-1H-pyrazol-5-yl)piperazin-1-yl)pentan-1-one

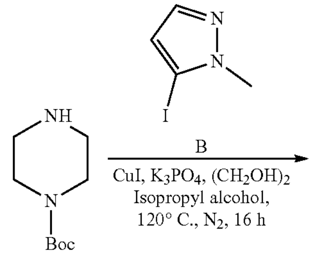

A

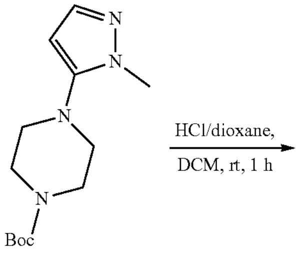

C

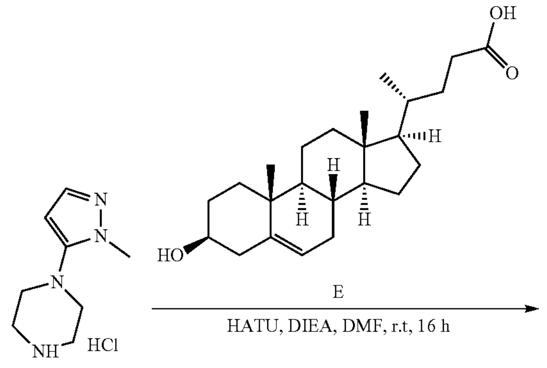

D

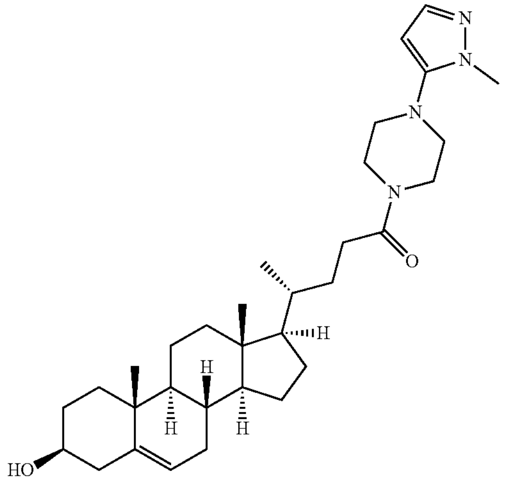

226

To a solution of compound A (100 mg, 0.54 mmol) and compound B (223 mg, 1.07 mmol) in isopropyl alcohol (1.5 mL) was added CuI (20.5 mg, 0.1 mmol), $K_3PO4$ (456 mg, 2.15 mmol) and ethane-1,2-diol (33.3 mg, 0.5 mmol). The reaction mixture was stirred at 120° C. under $N_2$ for 16 h in a sealed tube. After cooled to room temperature, the reaction was quenched with water and extracted with EtOAc. The organic layer was washed by brine, dried over sodium sulfate, filtered, and concentrated. The mixture was purified by column chromatography on silica gel to afford compound C (50 mg) as a solid.

To a solution of compound C (50 mg, 0.2 mmol) in dichloromethane (2 mL) was added HCl (0.1 mL, 4M in dioxane, 0.4 mmol). The reaction mixture was stirred at room temperature for 1 h. The reaction was concentrated to afford the compound D (30 mg) as a solid.

To a solution of compound E (60.8 mg, 0.16 mmol) and compound D (100 mg, 0.5 mmol) in DMF (3 mL) was added DIEA (140 mg, 1.08 mmol) and HATU (137 mg, 0.36 mmol). The reaction mixture was stirred at room temperature under $N_2$ for 16 h. The reaction was quenched with saturated $NH_4Cl$ and extracted with EtOAc. The organic layer was washed by brine, dried over sodium sulfate, filtered, and concentrated. The mixture was purified by column chromatography on silica gel to afford compound 226 (15.9 mg) as a white solid. $^1H$ NMR (400 MHz, Chloroform-d) δ 7.37 (s, 1H), 5.81 (s, 1H), 5.35 (d, J=4.8 Hz, 1H), 3.79-3.72 (m, 5H), 3.64-3.58 (m, 2H), 3.56-3.48 (m, 1H), 2.92-2.93 (m, 4H), 2.46-2.37 (m, 1H), 2.33-2.19 (m, 3H), 2.03-1.95 (m, 2H), 1.92-1.78 (m, 4H), 1.56-1.44 (m, 7H), 1.40-1.24 (m, 5H), 1.22-1.06 (m, 4H), 1.01 (s, 3H), 0.96 (d, J=6.4 Hz, 4H), 0.69 (s, 3H). LCMS: [M+H]=523.30.

Example 227: 2-hydroxy-N-(1-(1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)ethyl)-2-methylpropanamide

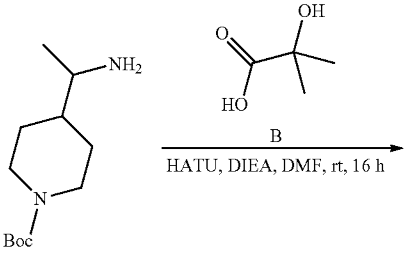

A

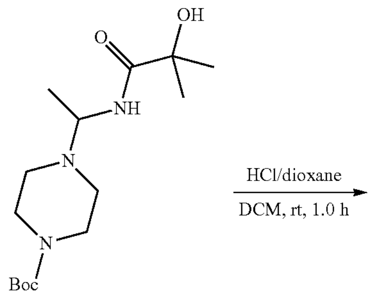

C

-continued

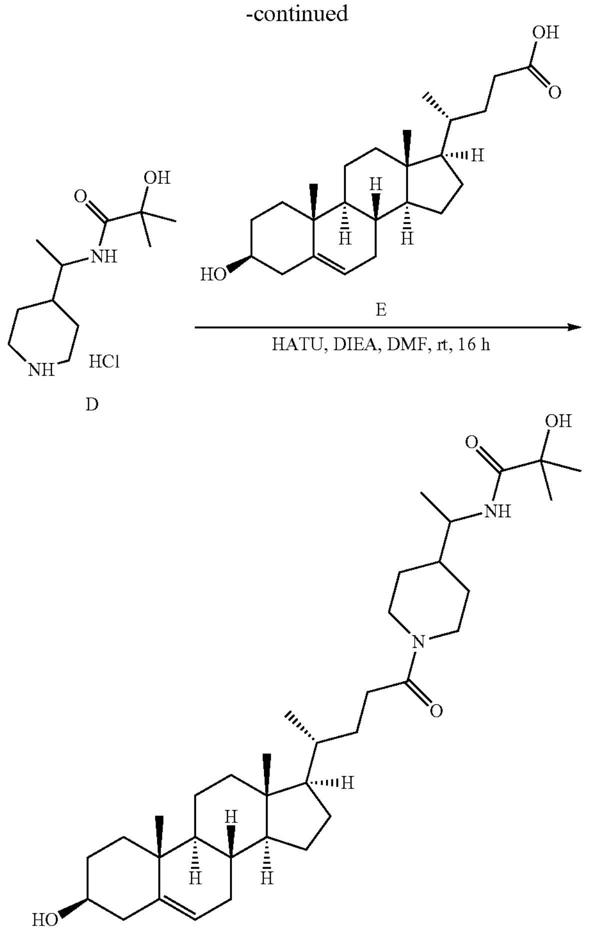

227

To a solution of compound A (500 mg, 2.19 mmol) and compound B (253 mg, 2.43 mmol) in DMF (10 mL) was added DIEA (1.89 g, 14.6 mmol) and HATU (1.85 g, 4.87 mmol). The reaction mixture was stirred at room temperature under $N_2$ for 16 h. The reaction was quenched with saturated $NH_4Cl$ and extracted with EtOAc. The organic layer was washed by brine, dried over sodium sulfate, filtered, and concentrated. The mixture was purified by column chromatography on silica gel to afford compound C (120 mg).

To a solution of compound C (120 mg, 382 μmol) in dichloromethane (2.0 mL) was added hydrogen chloride (0.2 mL, 4M in dioxane, 0.8 mmol). The reaction was stirred at room temperature for 1 hour. The mixture was concentrated to afford the compound D (85 mg) as a solid.

To a solution of compound E (134 mg, 357 μmol) and compound D (85 mg, 0.34 mmol) in DMF (3 mL) was added DIEA (308 mg, 2.38 mmol) and HATU (302 mg, 0.8 mmol). The mixture was stirred at room temperature under $N_2$ for 16 h. The reaction was quenched with saturated $NH_4Cl$ and extracted with EtOAc. The organic layer was washed by brine, dried over sodium sulfate, filtrated and concentrated. The mixture was purified by column chromatography on silica gel to afford compound 227 (40 mg) as a white solid. $^1H$ NMR (400 MHz, Chloroform-d) δ 6.56 (bs, 1H), 5.37-5.33 (m, 1H), 4.67 (bs, 1H), 3.97-3.78 (m, 2H), 3.57-3.48 (m, 1H), 3.03-2.90 (m, 1H), 2.53-2.15 (m, 6H), 2.05-1.92 (m, 2H), 1.88-1.80 (m, 3H), 1.79-1.68 (m, 3H), 1.54-1.41 (m, 13H), 1.33-1.24 (m, 5H), 1.21-1.06 (m, 8H), 1.00 (s, 3H), 0.94 (d, J=6.8 Hz, 4H), 0.68 (s, 3H). LCMS: [M+H]=571.30.

Example 228: 2-hydroxy-N-((1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)methyl)-2-methylpropanamide

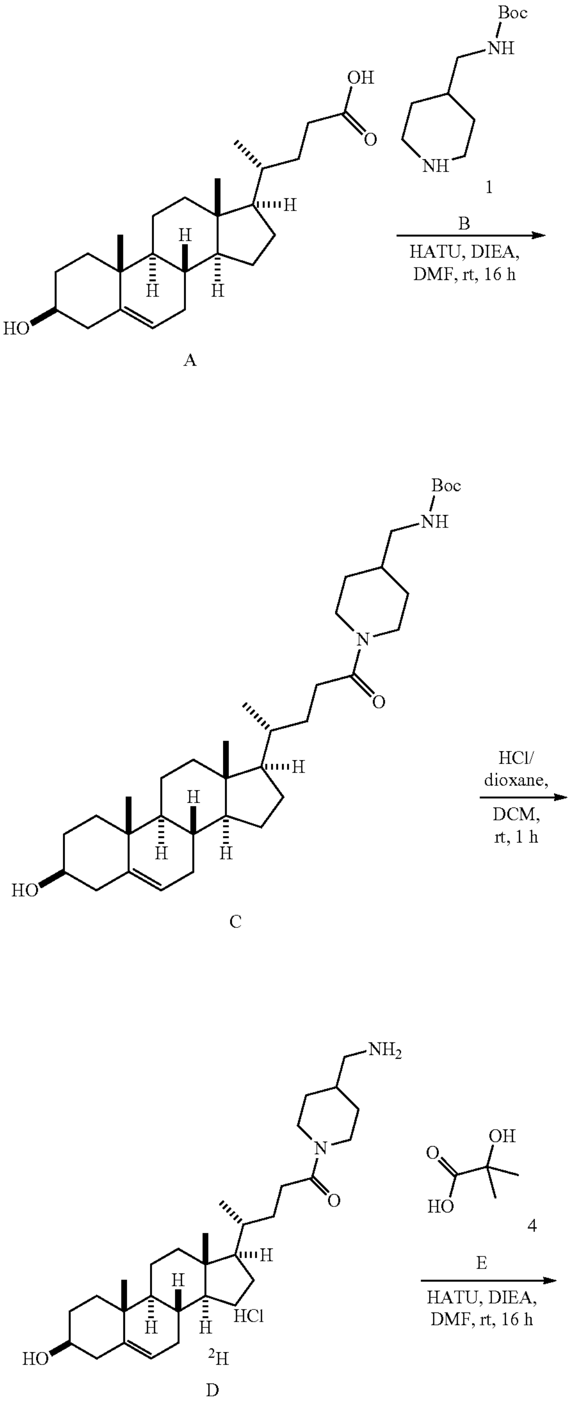

-continued

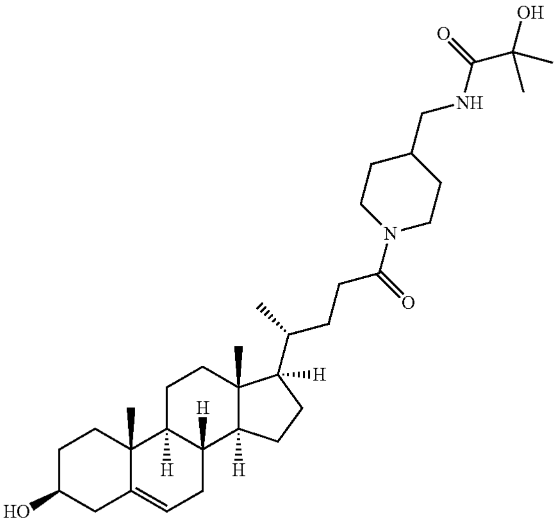

F

228

Example 229: N-(1-(1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)ethyl)methanesulfonamide

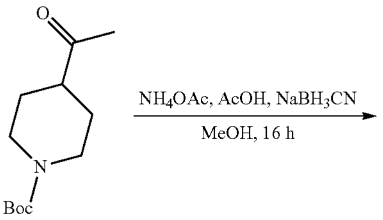

A

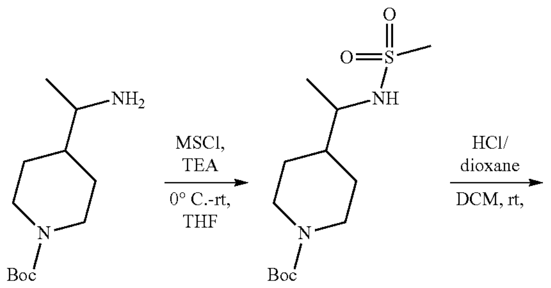

B C

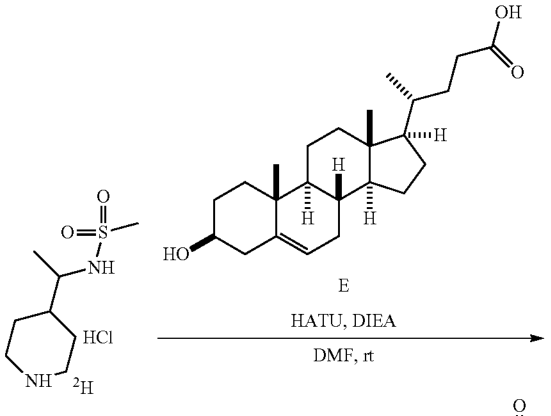

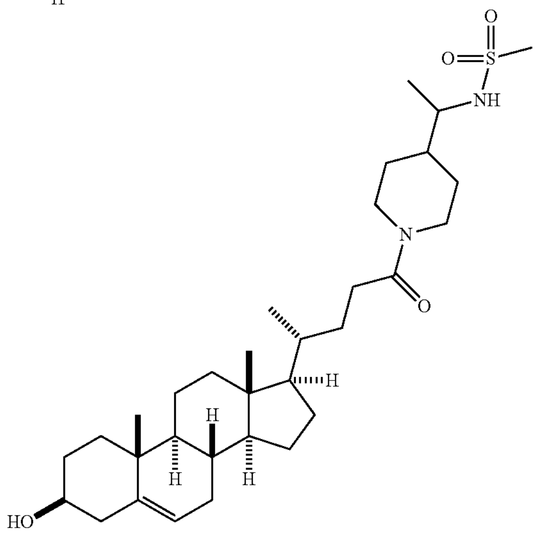

229

To a solution of compound A (500 mg, 1.33 mmol) and compound B (318 mg, 1.48 mmol) in DMF (15 mL) was added DIEA (1.15 g, 8.9 mmol) and HATU (1.13 g, 2.97 mmol). The reaction mixture was stirred at room temperature under $N_2$ for 16 h. The reaction was quenched with saturated $NH_4Cl$ and extracted with EtOAc. The organic layer was washed by brine, dried over sodium sulfate, filtered, and concentrated. The mixture was purified by column chromatography on silica gel to afford compound C (450 mg) as a solid.

To a solution of compound C (250 mg, 0.44 mmol) in dichloromethane (3 mL) was added hydrogen chloride (0.2 mL 4M in dioxane, 0.8 mmol). The reaction mixture was stirred at room temperature for 1 hour. The reaction was concentrated to afford the compound D (220 mg) as a solid.

To a solution of compound D (220 mg, 0.43 mmol) and compound E (43.8 mg, 0.42 mmol) in DMF (5 mL) was added DIEA (362 mg, 2.8 mmol) and HATU (355 mg, 0.93 mmol). The reaction mixture was stirred at room temperature under $N_2$ for 16 h. The reaction was quenched with saturated $NH_4Cl$ and extracted with EtOAc. The organic layer was washed by brine, dried over sodium sulfate, filtered, and concentrated. The mixture was purified by column chromatography on silica gel to afford compound 228 (70 mg) as a white solid. $^1H$ NMR (400 MHz, Chloroform-d) δ 6.84 (t, J=5.6 Hz, 1H), 5.35 (d, J=5.1 Hz, 1H), 4.62 (d, J=13.4 Hz, 1H), 3.85 (d, J=13.5 Hz, 1H), 3.52 (dt, J=11.4, 6.2 Hz, 1H), 3.17 (ddt, J=50.6, 13.3, 6.4 Hz, 2H), 2.99 (t, J=12.9 Hz, 1H), 2.53 (t, J=12.7 Hz, 1H), 2.42-2.16 (m, 5H), 2.05-1.68 (m, 10H), 1.46 (s, 12H), 1.30 (d, J=10.6 Hz, 3H), 1.22-1.02 (m, 7H), 1.01 (s, 3H), 0.95 (d, J=6.5 Hz, 3H), 0.92-0.85 (m, 1H), 0.68 (s, 3H). LCMS: [M+H]=557.30.

To a solution of compound A (500 mg, 2.2 mmol) in methanol (6 mL) was added ammonium acetate (678 mg, 8.8 mmol) and AcOH (0.1 mL), the reaction mixture was stirred at room temperature after 2 hours was added $NaCNBH_3$ (166 mg, 2.64 mmol) and stirred for 16 h. The reaction was quenched with saturated NaOH and extracted with DCM. The organic layer was washed by brine, dried over sodium sulfate, filtered, and concentrated to afford compound B (400 mg).

To a solution of compound B (440 mg, 1.93 mmol) in tetrahydrofuran (5 mL) at 0° C. was added TEA (385 mg) and methanesulfonyl chloride (331 mg, 2.89 mmol). The reaction mixture was stirred at room temperature under $N_2$ for 16 h. The reaction was quenched with saturated $NH_4Cl$ and extracted with EtOAc. The organic layer was washed by brine, dried over sodium sulfate, filtered, and concentrated. The mixture was purified by column chromatography on silica gel to afford compound C (290 mg) as a solid.

To a solution of compound C (150 mg, 0.49 mmol) in dichloromethane (2 mL) was added hydrochloric acid (0.3 mL, 4M in dioxane, 1.2 mmol). The reaction mixture was stirred at room temperature under $N_2$ for 0.5 h. The reaction was concentrated to afford the compound D (110 mg) as a solid.

To a solution of compound E (180 mg, 0.48 mmol) and compound D (110 mg, 0.45 mmol) in DMF (3 mL) was added DIEA (413 mg, 3.2 mmol) and HATU (405 mg, 1.07 mmol). The reaction mixture was stirred at room temperature under $N_2$ for 16 h. The reaction was quenched with saturated $NH_4Cl$ and extracted with EtOAc. The organic layer was washed by brine, dried over sodium sulfate, filtered, and concentrated. The mixture was purified by column chromatography on silica gel to afford compound 229 (80 mg) as a white solid. $^1H$ NMR (400 MHz, Chloroform-d) δ 5.35 (d, J=5.0 Hz, 1H), 4.71 (t, J=12.4 Hz, 1H), 4.08 (t, J=8.0 Hz, 1H), 3.91 (d, J=13.5 Hz, 1H), 3.53 (td, J=11.6, 10.6, 4.9 Hz, 1H), 3.44-3.26 (m, 1H), 2.97 (s, 3H), 2.55-2.17 (m, 5H), 2.06-1.68 (m, 8H), 1.55-1.40 (m, 7H), 1.37-1.05 (m, 13H), 1.01 (s, 4H), 0.95 (d, J=6.6 Hz, 3H), 0.89 (q, J=7.0, 6.2 Hz, 1H), 0.68 (s, 3H). LCMS: [M+H]=563.25.

Example 230: N-((1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)methyl)-N-methylmethanesulfonamide

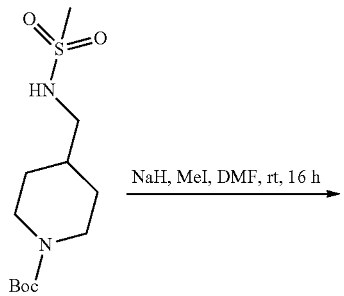

A

-continued

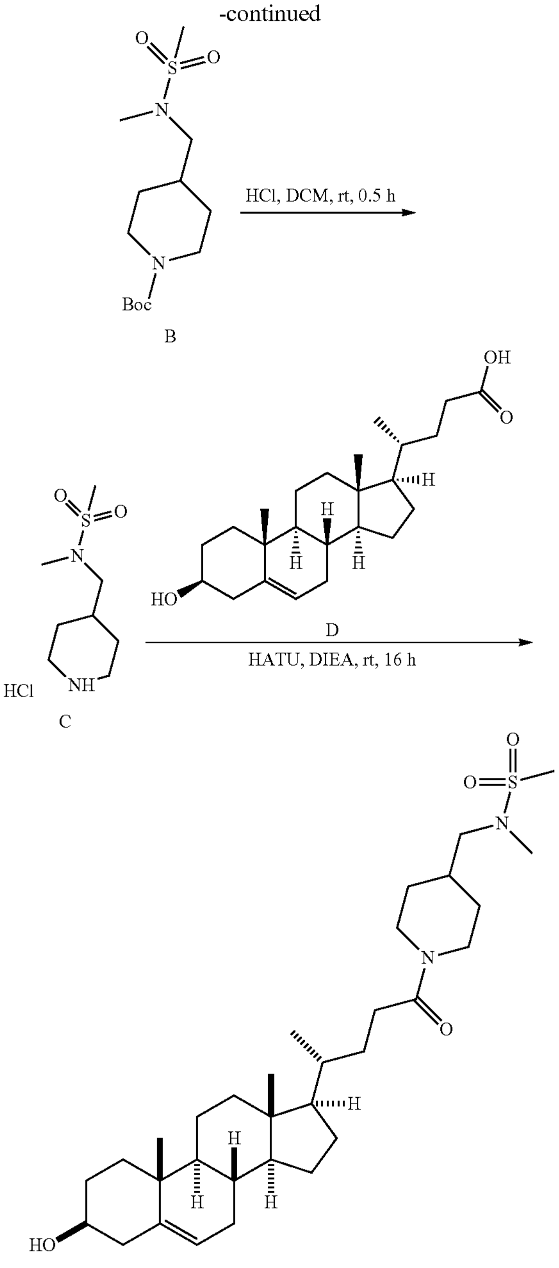

B

C

D

230

To a solution of compound A (500 mg, 1.71 mmol) in DMF (5 mL) was added NaH (78.6 mg, 3.42 mmol, 60% dispersion in oil) at 0° C.; and stirred for 30 mins. To the mixture was added iodomethane (364 mg, 2.57 mmol). The reaction was stirred at room temperature for 16 hours. The mixture was diluted with $H_2O$ and extracted with ethyl acetate. The combined organic layer was concentrated to give crude which was purified by silica gel chromatography to give compound B (500 mg, 95.4%) as light a yellow solid.

To a solution of compound B (200 mg, 635 μmol) in dichloromethane (2 mL) was added HCl (1 mL, 4M in dioxane, 4 mmol). The reaction was stirred at room temperature for 30 mins. The mixture was concentrated to afford compound C (152 mg, 96%) which was used in next step directly.

To a solution of compound C (152 mg, 630 μmol) in DMF (5 mL) was added compound D (212 mg, 567 μmol), DIEA (489 mg, 3.78 mmol) and HATU (408 mg, 1.26 mmol). The mixture was stirred at room temperature for 16 hours. The mixture was diluted with $H_2O$ and extracted with ethyl acetate. The combined organic layer was concentrated to give crude which was purified by silica gel chromatography to give the title compound 230 (140 mg, 39%) as a solid. $^1H$ NMR (400 MHz, Chloroform-d) δ 5.35 (d, J=5.1 Hz, 1H), 4.62 (d, J=13.4 Hz, 1H), 3.87 (d, J=13.6 Hz, 1H), 3.52 (tt, J=10.7, 4.6 Hz, 1H), 3.10-2.89 (m, 3H), 2.87 (s, 3H), 2.79 (s, 3H), 2.62-2.52 (m, 1H), 2.42-2.16 (m, 4H), 2.03-1.70 (m, 9H), 1.55-1.39 (m, 7H), 1.37-1.26 (m, 3H), 1.20-1.10 (m, 4H), 1.09-1.03 (m, 2H), 1.01 (s, 3H), 0.95 (d, J=6.5 Hz, 3H), 0.68 (s, 3H). LCMS: $[M+1]^+$=563.20.

Example 231: 1,1,1-trifluoro-N-((1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)methyl)methanesulfonamide

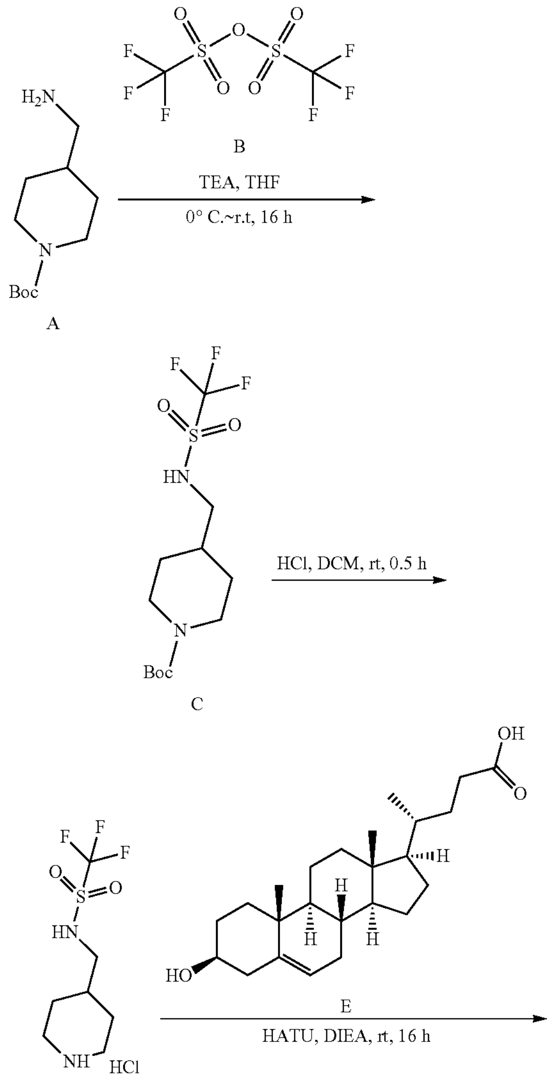

A B C D E

-continued

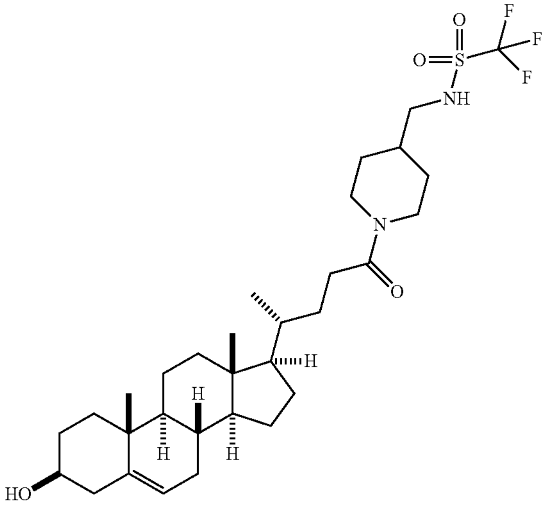

231

To a solution of compound A (1.0 g, 4.67 mmol) in tetrahydrofuran (15 mL) was added triethylamine (1.41 g, 14 mmol) and compound B (1.97 g, 7 mmol) at 0° C.; under $N_2$. The mixture was stirred at room temperature for 16 hours. After completion, the mixture was quenched by adding saturated ammonium chloride solution (100 mL) and extracted with ethyl acetate (30 mL×3). The organic layer was washed with brine, dried over sodium sulfate, filtered, and concentrated to give the crude which was purified by column chromatography on silica gel to yield the title compound C (380 mg, 23.51%).

HCl (1 mL, 4M in dioxane, 4 mmol) was added slowly to the solution of compound C (200 mg, 577 μmol) in DCM (3 mL) at room temperature and stirred for 0.5 hour. After completion, the reaction mixture was concentrated to give the title compound D (149 mg, 91%) as a solid.

To a solution of compound D (149 mg, 528 μmol) in DMF (5 mL) was added compound E (178 mg, 475 μmol), DIEA (409 mg, 3.17 mmol) and HATU (380 mg, 1.06 mmol). The mixture was stirred at room temperature for 16 hours. After completion, the mixture was quenched by adding saturated ammonium chloride solution (50 mL) and extracted with ethyl acetate (20 mL×3). The organic layer was washed with brine, dried over sodium sulfate, filtered, and concentrated to give the crude which was purified by column chromatography on silica gel to yield the title compound 231 (170 mg, 53.4%) as a solid. $^1H$ NMR (400 MHz, Chloroform-d) δ 5.68 (t, J=6.2 Hz, 1H), 5.35 (d, J=5.1 Hz, 1H), 4.66 (d, J=13.4 Hz, 1H), 3.90 (d, J=13.6 Hz, 1H), 3.52 (dq, J=10.5, 5.2, 4.2 Hz, 1H), 3.26-3.12 (m, 2H), 3.02 (t, J=12.9 Hz, 1H), 2.53 (t, J=12.8 Hz, 1H), 2.39-2.17 (m, 4H), 2.03-1.95 (m, 2H), 1.90-1.72 (m, 7H), 1.64-1.59 (m, 1H), 1.54-1.42 (m, 7H), 1.34-1.25 (m, 3H), 1.21-1.03 (m, 6H), 1.01 (s, 3H), 0.95 (d, J=6.6 Hz, 3H), 0.93-0.84 (m, 1H), 0.68 (s, 3H). $^{19}F$NMR (376 MHz, Chloroform-d) δ−77.15. LCMS: $[M+1]^+$=603.20.

Example 232: N-((1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)methyl)methanesulfonamide

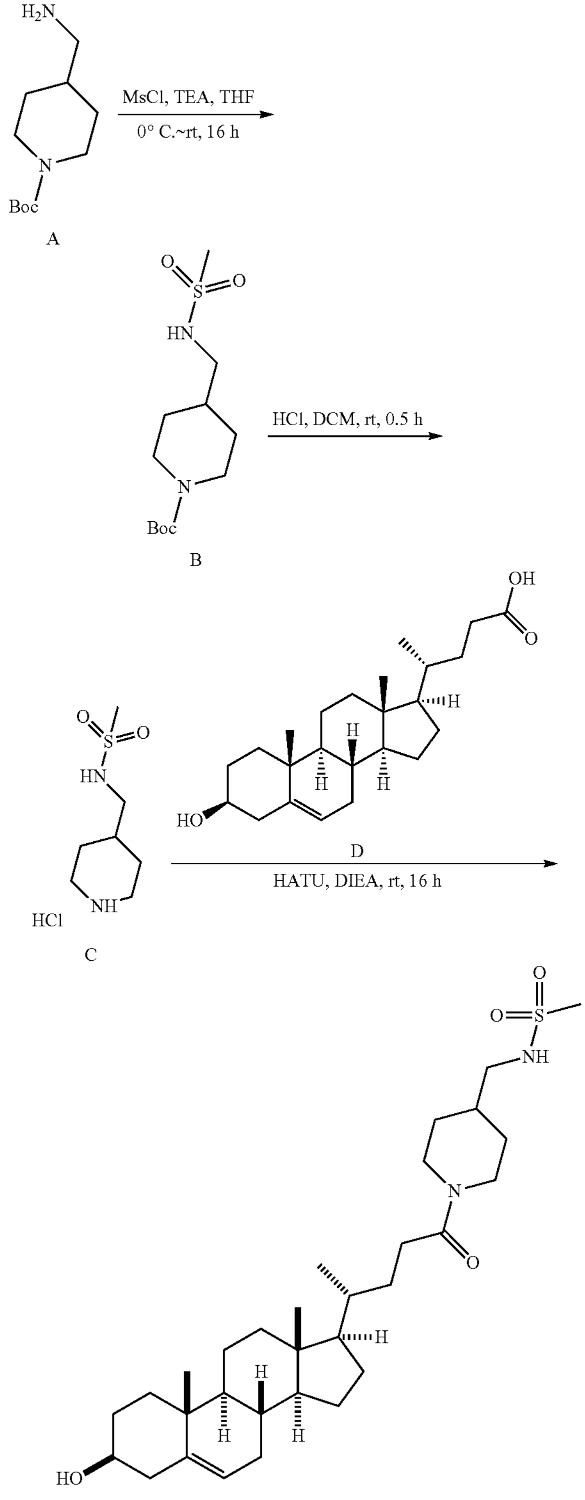

232

To a solution of compound A (2.0 g, 9.33 mmol) in tetrahydrofuran (30 mL) was added triethylamine (2.83 g, 28 mmol) and methanesulfonyl chloride (1.6 g, 14 mmol) at 0° C.; under $N_2$. The mixture was stirred at room temperature for 16 hours. After completion, the mixture was quenched by adding saturated ammonium chloride solution (100 mL) and extracted with ethyl acetate (30 mL×3). The organic layer was washed with brine, dried over sodium sulfate, filtered, and concentrated to give the crude which was purified by column chromatography on silica gel to yield the title compound B (2.0 g, 73.3%). HCl (1 mL, 4M in dioxane, 4 mmol) was added slowly to the solution of compound B (200 mg, 684 μmol) in DCM (3 mL) at room temperature and stirred for 0.5 hour. After completion, the reaction mixture was concentrated to give the title compound C (154 mg, 98%) as a solid.

To a solution of compound C (154 mg, 676 μmol) in DMF (5 mL) was added compound D (228 mg, 608 μmol), DIEA (524 mg, 4.06 mmol) and HATU (318 mg, 1.35 mmol). The mixture was stirred at room temperature for 16 hours. After completion, the mixture was quenched by adding saturated ammonium chloride solution (50 mL) and extracted with ethyl acetate (20 mL×3). The organic layer was washed with brine, dried over sodium sulfate, filtered, and concentrated to give the crude which was purified by column chromatography on silica gel to yield the title compound 232 (180 mg, 48.5%) as a white solid. $^1H$ NMR (400 MHz, Chloroform-d) δ 5.35 (d, J=4.9 Hz, 1H), 4.66 (d, J=12.8 Hz, 1H), 4.44 (t, J=6.1 Hz, 1H), 3.97-3.85 (m, 1H), 3.52 (dt, J=11.2, 6.5 Hz, 1H), 3.08-2.94 (m, 6H), 2.53 (t, J=13.0 Hz, 1H), 2.41-2.17 (m, 4H), 2.06-1.95 (m, 2H), 1.90-1.71 (m, 7H), 1.63-1.41 (m, 9H), 1.35-1.28 (m, 2H), 1.22-1.05 (m, 6H), 1.04-0.92 (m, 8H), 0.68 (s, 3H). LCMS: $[M+1]^+$=549.30.

Example 233: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3S)-3-(hydroxymethyl)pyrrolidin-1-yl]pentan-1-one

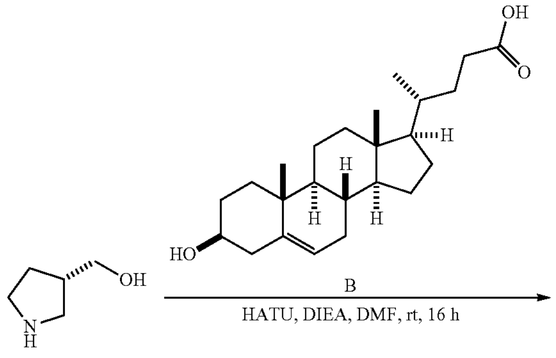

A

-continued

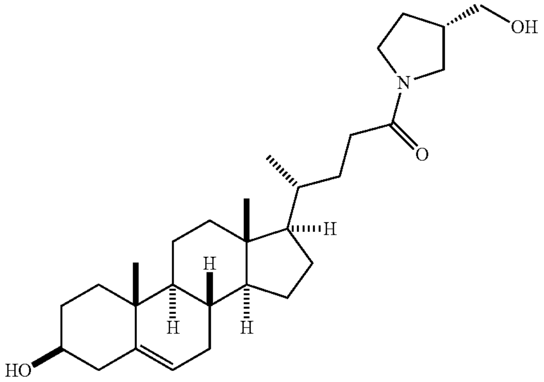

233

To a solution of compound A (100 mg, 989 μmol) in DMF (4 mL) was added compound B (333 mg, 890 μmol), HATU (564 mg, 1.48 mmol) and DIEA (511 mg, 3.95 mmol) at room temperature. The mixture was stirred at room temperature for 16 hours. The mixture was quenched with saturated $NH_4Cl$ and extracted with ethyl acetate. The organic layer was concentrated to give crude which was purified by silica gel chromatography to give the title compound 233 (80 mg). $^1H$ NMR (400 MHz, Chloroform-d) δ 5.35 (dt, J=4.3, 1.8 Hz, 1H), 3.79-3.37 (m, 6H), 3.33-3.15 (m, 1H), 2.52-2.07 (m, 5H), 2.04-1.89 (m, 3H), 1.88-1.72 (m, 7H), 1.70-1.55 (m, 2H), 1.52-1.40 (m, 5H), 1.37-1.25 (m, 2H), 1.21-1.04 (m, 4H), 1.00 (s, 3H), 0.94 (d, J=6.5 Hz, 3H), 0.68 (s, 3H). LCMS: M+1=458.4.

Example 234: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-3-(hydroxymethyl)pyrrolidin-1-yl)pentan-1-one

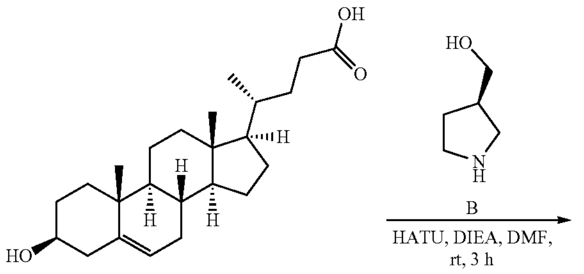

A

-continued

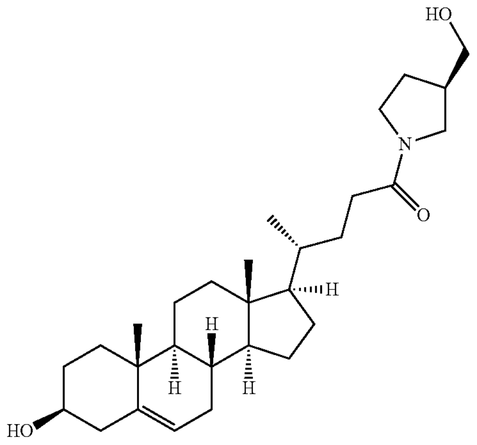

234

To a solution of compound A (300 mg, 801 μmol) and compound B (81 mg, 801 μmol) in DMF (5 mL) was added HATU (457 mg, 1.2 mmol) and DIEA (311 mg, 2.4 mmol). The mixture was stirred at room temperature for 3 hours. After completion, the mixture was quenched by adding saturated ammonium chloride solution (20 mL) and extracted with ethyl acetate (20 mL×3). The organic layer was washed with brine, dried over sodium sulfate, filtered, and concentrated to give the crude which was purified by column chromatography on silica gel to yield the title compound 234 (105 mg, 28.6%) as a white solid. LCMS: $[M+H]^+$=458.25. $^1H$ NMR (400 MHz, Chloroform-d) δ 5.35 (d, J=5.0 Hz, 1H), 3.74-3.18 (m, 7H), 2.46-1.90 (m, 8H), 1.89-1.03 (m, 20H), 1.00 (s, 3H), 0.94 (d, J=6.4 Hz, 3H), 0.68 (s, 3H).

Example 235: (4R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(1-methoxyethyl)piperidin-1-yl)pentan-1-one

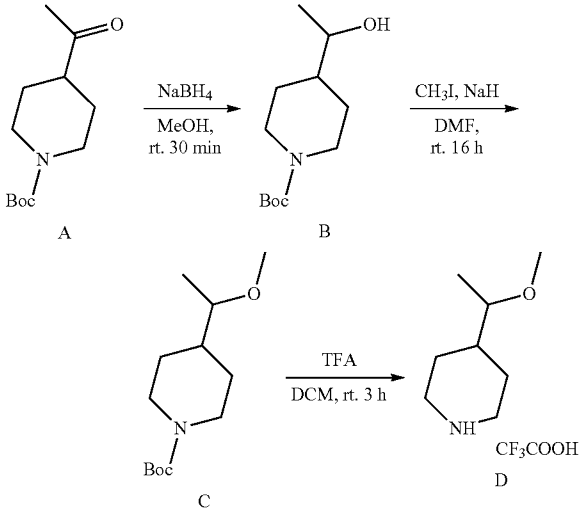

-continued

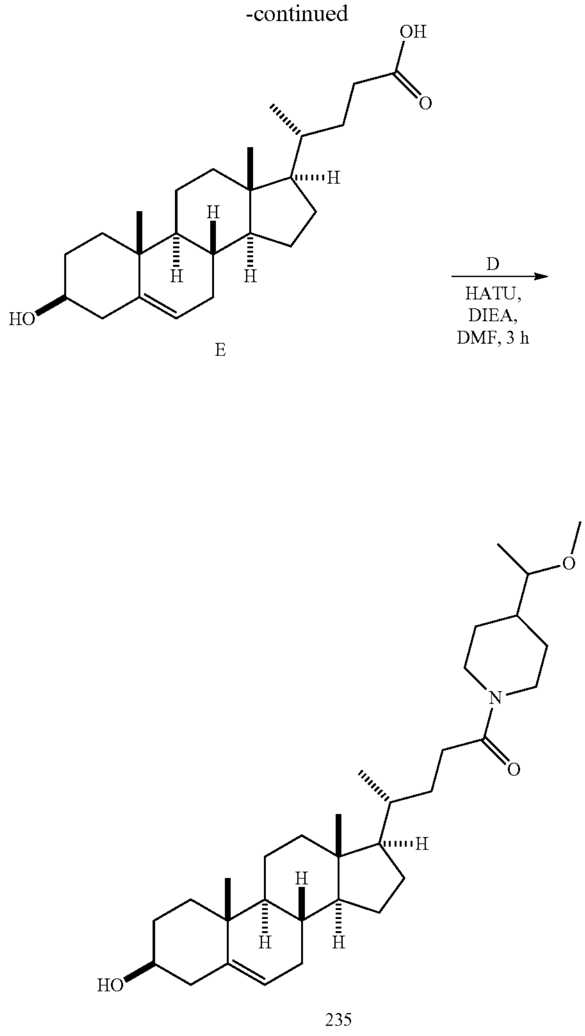

E

235

To a solution of compound A (1.0 g, 4.4 mmol) in methanol (10 mL) was added $NaBH_4$ (166 mg, 4.4 mmol) at room temperature, the mixture was stirred for 30 minutes. The reaction was quenched by $H_2O$ and extracted with ethyl acetate. The organic layer was concentrated to give crude which was purified by silica gel chromatography to give compound B (860 mg, 85%).

To a solution of compound B (500 mg, 2.18 mmol) in DMF (5 mL) was added $CH_3I$ (1.55 g, 10.9 mmol) and NaH (436 mg, 10.9 mmol, 60% dispersion in oil) at 0° C. under $N_2$, the mixture was stirred for 16 hours. The reaction was quenched by $H_2O$ and extracted with ethyl acetate. The organic layer was concentrated to give compound C (500 mg, 85%) which was used directly in the next step.

To a solution of compound C (200 mg, 822 μmol) in DCM (2 mL) was added TFA (0.6 mL) at room temperature, the mixture was stirred at room temperature for 3 hours. The mixture was concentrated to give compound D (110 mg, 52%).

To a solution of compound E (180 mg, 481 μmol) in DMF (4 mL) was added compound D (52.6 mg, 218 μmol), HATU (170 mg, 721 μmol) and DIEA (251 μL, 1.44 mmol). After stirring at room temperature for 3 hours, the reaction was quenched by $H_2O$ and extracted with ethyl acetate. The organic layer was concentrated, and the residue was purified by silica gel chromatography to give the title compound 235 (40 mg, 17%). $^1H$ NMR (400 MHz, Chloroform-d) δ 5.35 (d, J=5.2 Hz, 1H), 3.48-3.54 (m, 1H), 3.32 (s, 3H), 3.07 (t, J=6.2 Hz, 1H), 2.46-2.36 (m, 1H), 2.22-2.28 (m, 3H), 2.02-1.74 (m, 11H), 1.69-1.43 (m, 9H), 1.34-1.23 (m, 4H), 1.21-1.13 (m, 3H), 1.10 (d, J=6.2 Hz, 3H), 1.01 (s, 3H), 0.96 (d, J=6.4 Hz, 3H), 0.94-0.84 (m, 1H), 0.68 (s, 3H). LCMS: M+1=500.25.

Example 236: Methyl 4-(((S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propyl)carbamoyl)piperazine-1-carboxylate

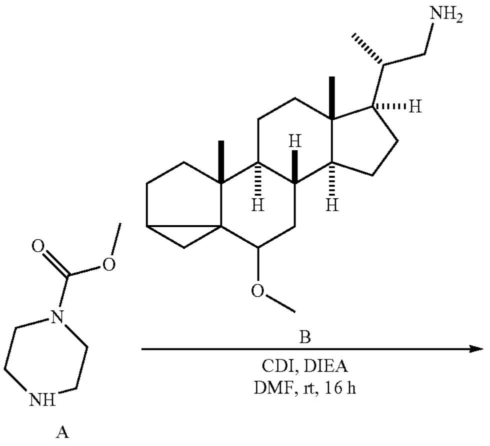

A

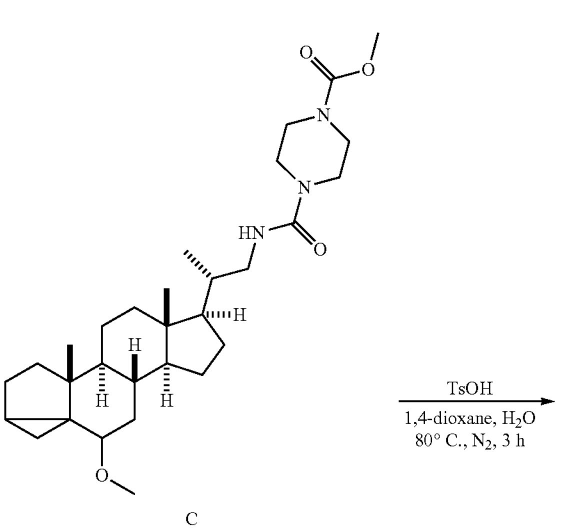

C

-continued

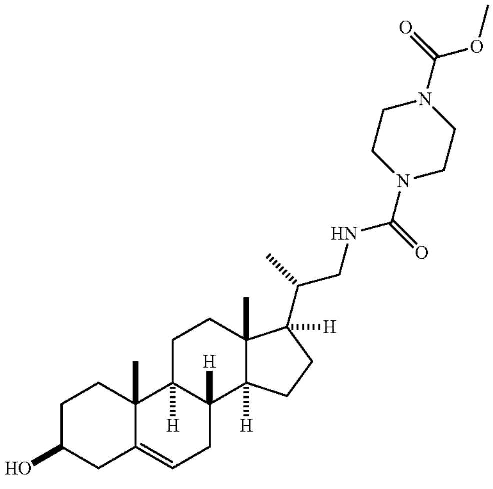

236

To a solution of compound B (100 mg, 0.29 mmol) in dimethylformamide (2 mL) was added compound A (41.7 mg, 289 μmol), CDI (61 mg, 376 μmol) and DIEA (112 mg, 868 μmol). The mixture was stirred at room temperature under $N_2$ for 16 h. The reaction was diluted with water, extracted with EA. The organic layer was washed by brine, dried over sodium sulfate, filtered, and concentrated. The mixture was purified by column chromatography on silica gel to afford compound C (50 mg) as a white solid.

To a solution of compound C (50 mg, 0.1 mmol) in 1,4-dioxane (2.1 mL) and water (0.3 mL) was added 4-methylbenzene-1-sulfonic acid (16.7 mg, 0.1 mmol). The mixture was stirred at 80° C. under $N_2$ for 3 h. The reaction was quenched with saturated $NH_4Cl$. extracted with EA. The organic layer was washed by brine, dried over sodium sulfate, filtered, and concentrated. The mixture was purified by column chromatography on silica gel to afford the title compound 236 (15 mg) as a white solid. $^1H$ NMR (400 MHz, Chloroform-d) δ 5.34 (d, J=3.6 Hz, 1H), 4.45 (t, J=5.6 Hz, 1H), 3.72 (s, 3H), 3.56-3.44 (m, 5H), 3.43-3.32 (m, 5H), 2.93-2.81 (m, 1H), 2.35-2.16 (m, 2H), 2.04-1.79 (m, 6H), 1.55-1.37 (m, 8H), 1.22-1.03 (m, 6H), 1.02-0.96 (m, 7H), 0.94-0.82 (m, 3H), 0.70 (s, 3H).

Example 237: 1-(1S)-1-[(1S,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]ethyl 4-methyl piperazine-1,4-dicarboxylate

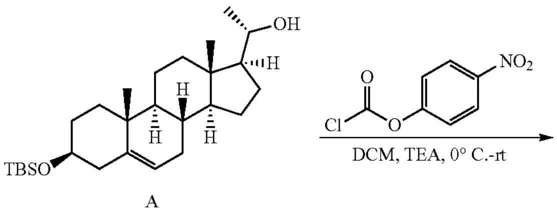

A

-continued

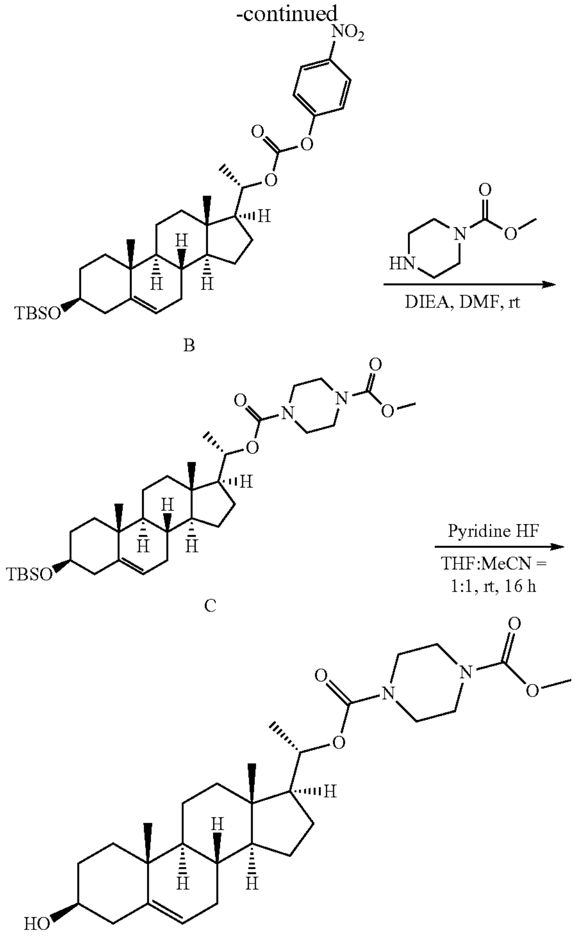

B

C

237

To a solution of compound A (450 mg, 1.04 mmol) in dichloromethane (10 mL) was added triethylamine (434 μL, 3.12 mmol) and 4-nitrophenyl carbonochloridate (314 mg, 1.56 mmol) at 0° C. The resulting mixture was stirred at room temperature for 3 h. The resulting mixture was extracted with water and ethyl acetate. The organic layer was dried with sodium sulfate and concentrated under vacuum to give crude product which was purified by silica gel chromatography (eluting with 1/30 ethyl acetate/PE) to give compound B (280 mg, 45.0%).

To a solution of compound B (140 mg, 234 μmol) in DMF (4.67 mL) was added DIEA (90.8 mg, 702 μmol) and methyl piperazine-1-carboxylate (92.2 μL, 702 μmol) at room temperature. The resulting mixture was stirred at room temperature for 16 h. The mixture was diluted water and extracted with ethyl acetate. The organic layer was washed with water and brine, dried with sodium sulfate, and concentrated under vacuum to give crude product which was purified by silica gel chromatography (eluting with 1/5 ethyl acetate/PE) to give compound C (100 mg, 70.8%).

A mixture of compound C (80 mg, 133 μmol) and HF pyridine (71.7 μL, 796 μmol) in tetrahydrofuran (8 mL) and acetonitrile (8 mL) was stirred at room temperature for 16 h. The pH of the resulting mixture was adjusted to 7 with saturated $NaHCO_3$ solution, extracted with ethyl acetate. The organic layer was dried over anhydrous sodium sulfate and concentrated under vacuum to give crude product which was purified by silica gel chromatography (eluting with 1/5 ethyl acetate/PE) to give the title compound 237 (44.9 mg, 69.2%). $^1$H NMR (400 MHz, Chloroform-d) δ 5.35 (d, J=5.1 Hz, 1H), 4.90-4.79 (m, 1H), 3.71 (s, 3H), 3.57-3.37 (m, 9H), 2.32-2.20 (m, 2H), 2.05-1.74 (m, 6H), 1.69-1.38 (m, 13H), 1.26 (d, J=6.0 Hz, 3H), 1.21-1.03 (m, 4H), 1.01 (s, 3H), 0.94 (dt, J=11.1, 5.7 Hz, 1H), 0.69 (s, 3H).

Example 238: 1-(2S)-2-[(1R,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]propyl 4-methyl piperazine-1,4-dicarboxylate To a solution of compound A (200 mg, 577 μmol) in dichloromethane (5 mL) was added triethylamine (241 μL, 1.73 mmol) and 4-nitrophenyl chloroformate (174 mg, 866 μmol) at 0° C. The resulting mixture was stirred at room temperature for 3 h. The resulting mixture was extracted with water and DCM. The organic layer was dried with sodium sulfate and concentrated under vacuum to give crude product which was purified by silica gel chromatography (eluting with 1/30 ethyl acetate/PE) to give compound B (150 mg, 50.8%).

To a solution of compound B (150 mg, 293 μmol) in DMF (3 mL) was added DIEA (114 mg, 879 μmol) and methyl piperazine-1-carboxylate (115 μL, 879 μmol) at room tem-

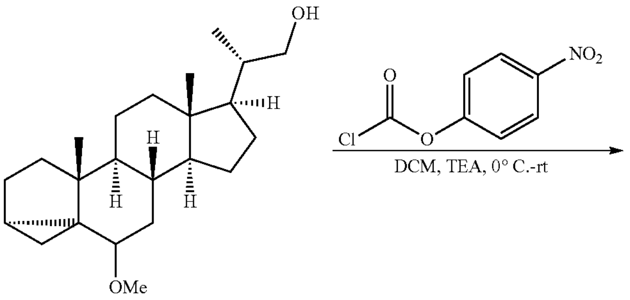

A

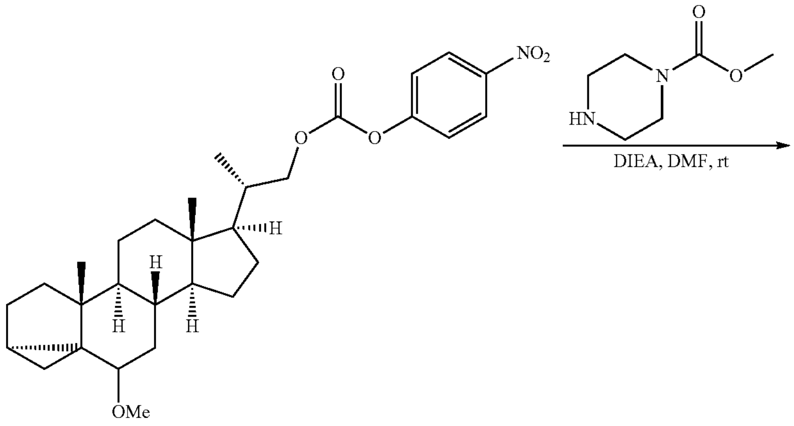

B

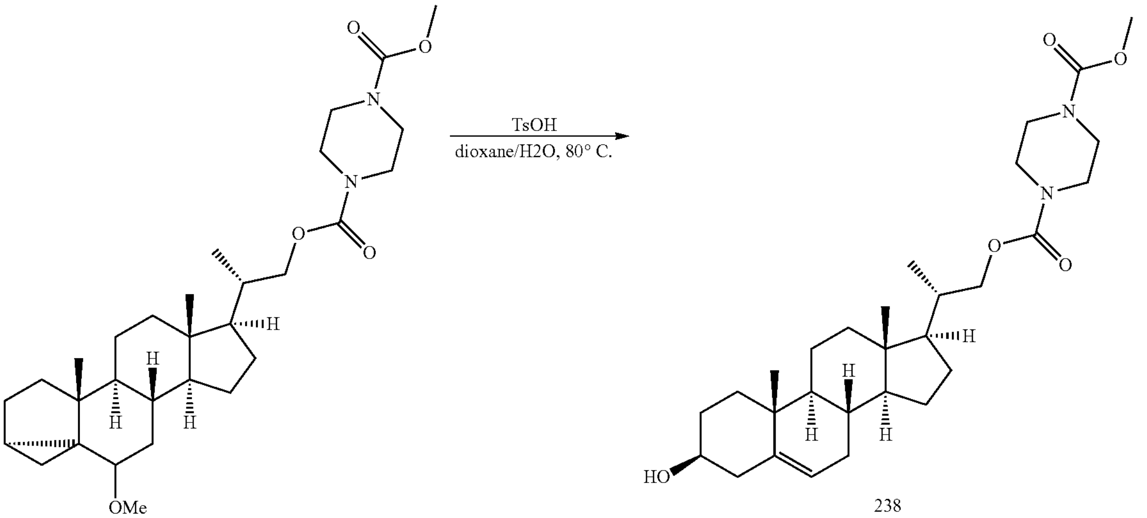

C

238 perature. The resulting mixture was stirred at room temperature for 16 h. The mixture was extracted with water and ethyl acetate. The organic layer was dried with sodium sulfate and concentrated under vacuum to give crude product which was purified by silica gel chromatography (eluting with 1/30 ethyl acetate/PE) to give compound C (50 mg, 33.0%).

A mixture of compound C (50 mg, 96.8 μmol) and 4-methylbenzene-1-sulfonic acid hydrate (14.7 mg, 77.4 μmol) in 1,4-dioxane (4 mL) and water (1 mL) was heated at 80° C.; for 3 h under an atmosphere of nitrogen. The pH of the resulting mixture was adjusted to 7 with saturated $NaHCO_3$ solution, extracted with ethyl acetate. The organic layer was dried over anhydrous sodium sulfate and concentrated under vacuum to give crude product which was purified by silica gel chromatography (eluting with 1/3 ethyl acetate/PE) to give the title compound 238 (17.2 mg, 35.4%). $^1H$ NMR (400 MHz, $CDCl_3$) δ 5.35 (d, J=5.0 Hz, 1H), 4.13 (dd, J=10.4, 3.4 Hz, 1H), 3.79 (dd, J=10.4, 7.4 Hz, 1H), 3.72 (s, 3H), 3.57-3.41 (m, 9H), 2.30-2.21 (m, 2H), 2.04-1.68 (m, 7H), 1.53-1.41 (m, 6H), 1.33-1.23 (m, 4H), 1.04-1.00 (m, 6H), 0.99-0.83 (m, 3H), 0.71 (s, 3H). LCMS: $[M+Na]^+$=525.20.

Example 239: 1—((S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propyl)-3-methylurea

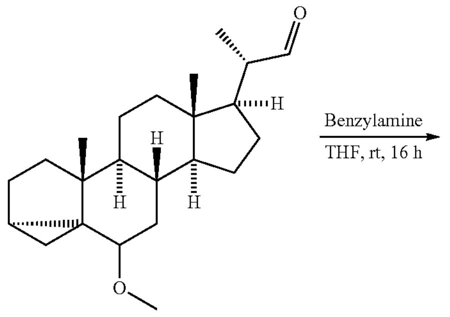

A

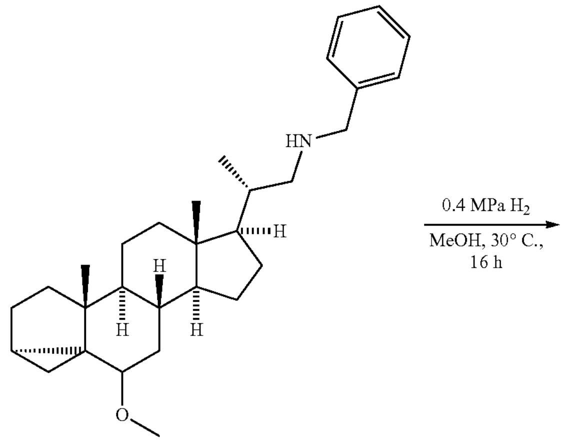

B

-continued

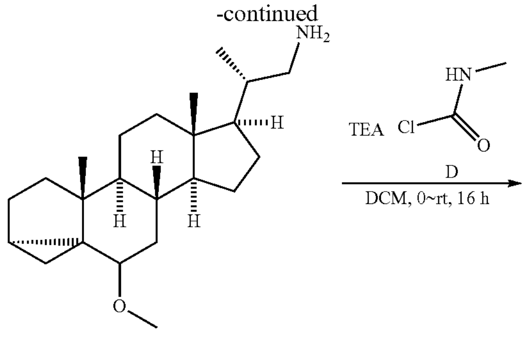

C

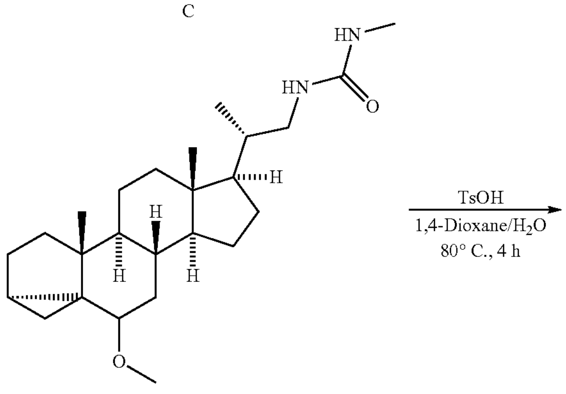

E

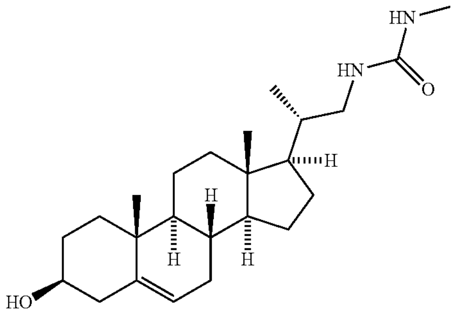

Example 239

To a solution of compound A (3.0 g, 8.71 mmol) in THE (60 mL) was added 1-phenylmethanamine (1.4 g, 13.1 mmol) and 10% Pd/C (400 mg). The mixture was stirred at room temperature under 1 atm of $H_2$ for 16 hours. The mixture was filtered and concentrated to give the crude which was purified by silica gel chromatography to afford compound B (3.0 g, 79%).

To a solution of compound B (3.0 g, 6.89 mmol) in MeOH (30 mL) was added 10% Pd/C (300 mg). The mixture was stirred at 30° C. for 16 hours under 4 atm of hydrogen. After completion, the mixture was concentrated, and the crude was purified by silica gel chromatography to afford compound C (1.2 g, 52%).

To a solution of compound C (200 mg, 579 μmol) in DCM (6 mL) was added TEA (293 mg, 2.89 mmol) then compound D (81.2 mg, 868 μmol) at 0° C. After stirring at room temperature for 16 hours, the mixture was diluted with water and extracted with ethyl acetate. The organic layer was concentrated to give the crude which was purified by silica gel chromatography to afford compound E (180 mg, 77%).

To a solution of compound E (180 mg, 447 μmol) in 1,4-dioxane (2.1 mL) and water (0.3 mL) was added 4-methylbenzene-1-sulfonic acid (15.4 mg, 89.4 μmol). After stirring at 80° C.; for 4 hours, the mixture was adjusted pH to 7 by $NaHCO_3$ and extracted with ethyl acetate. The organic layer was concentrated to give the crude which was purified by silica gel chromatography to afford the title compound 239 (57 mg, 32%). LCMS: $[M+1]^+$=389.20. $^1H$ NMR (400 MHz, Chloroform-d) δ 5.35 (d, J=5.2 Hz, 1H), 4.29-4.09 (m, 2H), 3.59-3.48 (m, 1H), 3.27 (dt, J=13.0, 4.8 Hz, 1H), 2.85 (dt, J=13.4, 7.2 Hz, 1H), 2.79 (d, J=4.8 Hz, 3H), 2.30-2.26 (m, 1H), 2.23 (d, J=6.8 Hz, 1H), 2.09-1.79 (m, 6H), 1.53-1.05 (m, 14H), 1.01 (s, 3H), 0.98 (d, J=6.6 Hz, 3H), 0.89 (d, J=7.4 Hz, 1H), 0.70 (s, 3H).

Example 240: Methyl ((S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propyl)carbamate

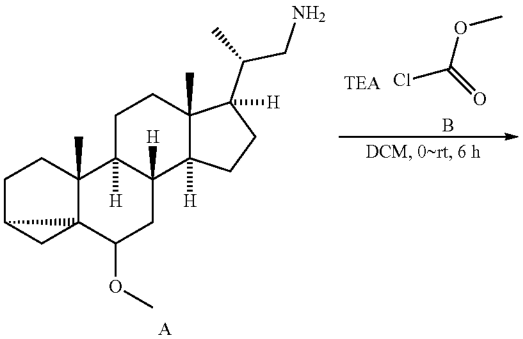

A

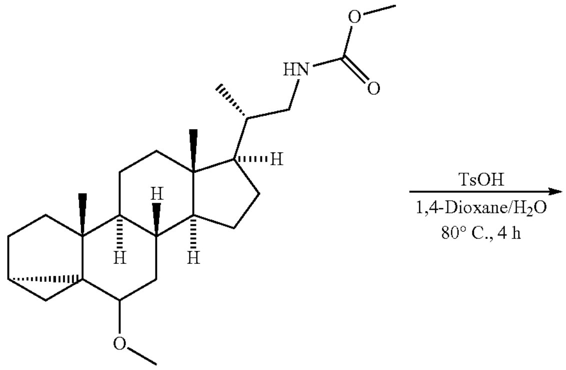

C

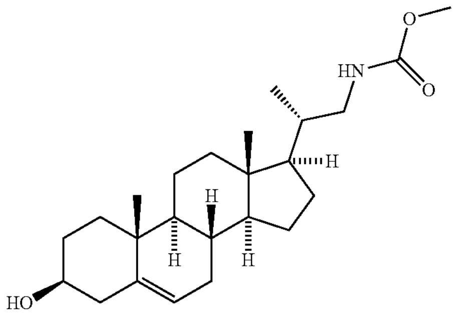

Example 240

To a solution of compound A (200 mg, 579 μmol) in DCM (10 mL) was added TEA (293 mg, 2.89 mmol) and compound B (82 mg, 868 μmol) at 0° C. After stirring at room temperature for 6 hours, the mixture was diluted with water and extracted with ethyl acetate. The organic layer was concentrated to give the crude and was purified by silica gel chromatography to afford compound C (180 mg, 77%).

To a solution of compound C (180 mg, 447 μmol) in 1,4-dioxane (2.5 mL) and water (360 μL) was added 4-methylbenzene-1-sulfonic acid (15.4 mg, 0.2 eq., 89.4 μmol). After stirring at 80° C.; for 4 hours, the mixture was adjusted pH to 7 by $NaHCO_3$, and extracted with ethyl acetate. The organic layer was concentrated to give the crude which was purified by Prep-HPLC to afford the title compound 240 (26 mg, 15%). LCMS: $[M+1]^+$=390.20. $^1H$ NMR (400 MHz, Chloroform-d) δ 5.35 (d, J=5.0 Hz, 1H), 4.64 (bs, 1H), 3.66 (s, 3H), 3.57-3.48 (m, 1H), 3.34-3.22 (m, 1H), 2.93-2.83 (m, 1H), 2.30-2.21 (m, 2H), 2.05-1.93 (m, 2H), 1.88-1.77 (m, 2H), 1.47-1.42 (m, 3H), 1.29-1.22 (m, 6H), 1.21-1.06 (m, 5H), 1.01 (s, 3H), 0.97 (d, J=6.6 Hz, 3H), 0.92-0.85 (m, 2H), 0.69 (s, 3H).

Example 241: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3R)-3-(pyrimidin-4-yloxy)piperidin-1-yl]pentan-1-one

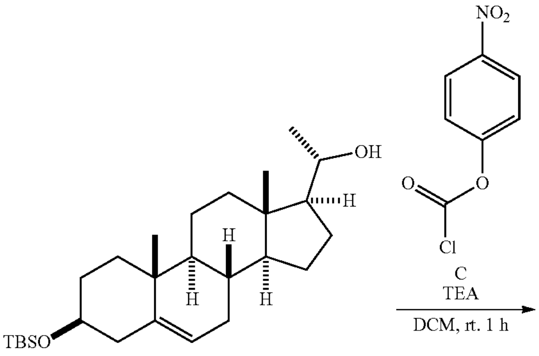

A

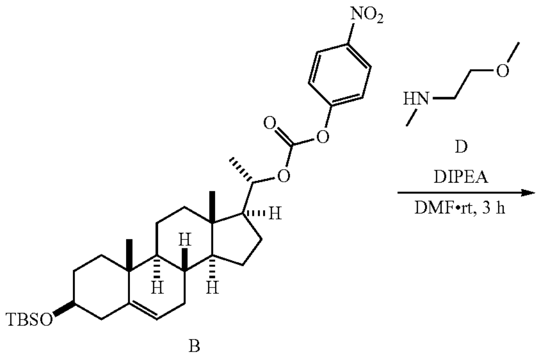

B

-continued

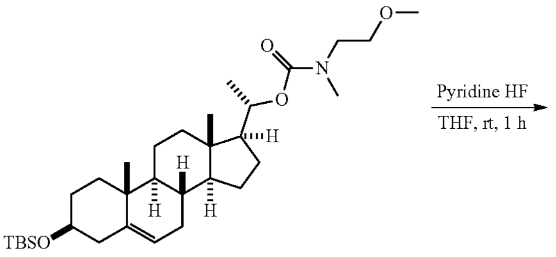

E

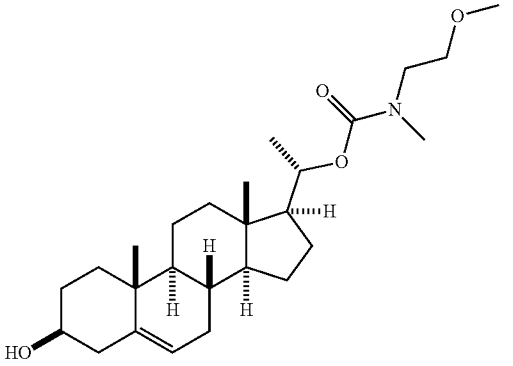

241

To a solution of compound A (400 mg, 960 μmol) in dichloromethane (10 mL) was added TEA (146 mg, 1.44 mmol) and compound C (213 mg, 1.06 mmol) at 0° C. The reaction mixture was stirred for 1 hour. After completion, the mixture was quenched by adding water (100 mL) and extracted with ethyl acetate (30 mL×3). The organic layer was washed with brine, dried over sodium sulfate, filtered, and concentrated to give the crude which was purified by column chromatography on silica gel to yield the title compound B (240 mg, 43%) as a white solid.

To a solution of compound B (240 mg, 412 μmol) and compound D (36.8 mg, 412 μmol) in DMF (10 mL) was added DIEA (160 mg, 1.24 mmol). The mixture was stirred at room temperature for 3 hours. After completion, the mixture was quenched by adding saturated ammonium chloride solution (30 mL) and extracted with ethyl acetate (10 mL×3). The organic layer was washed with brine, dried over sodium sulfate, filtered, and concentrated to give the crude which was purified by column chromatography on silica gel to yield the title compound E (120 mg, 68%) as a white solid.

Pyridine HF (2 mL) was added slowly to the compound E (120 mg, 219 μmol) in THE (5 mL) at room temperature and stirred for 16 h. After completion, the mixture was diluted with water and extracted with ethyl acetate. The organic layer was concentrated. The residue was purified by column chromatography on silica gel to give Example 241 (38 mg, 40%) as a solid. LCMS:$[M+Na]^+$=456.20. $^1$H NMR (400 MHz, Chloroform-d) δ 5.35 (d, J=5.1 Hz, 1H), 4.82 (t, J=6.8 Hz, 1H), 3.65-3.25 (m, 9H), 2.93 (bs, 3H), 2.37-2.17 (m, 2H), 2.04-1.76 (m, 5H), 1.56-1.39 (m, 8H), 1.30-0.89 (m, 11H), 0.69 (s, 3H).

Example 242: (1S)-1-[(1S,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]ethyl N,N-dimethylcarbamate

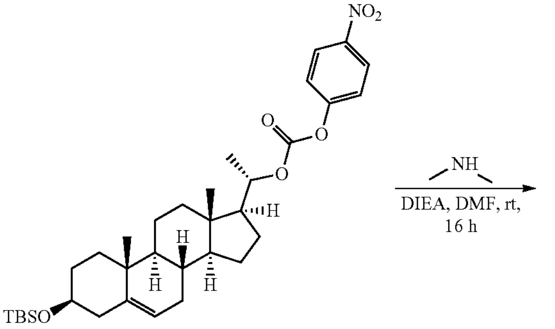

A

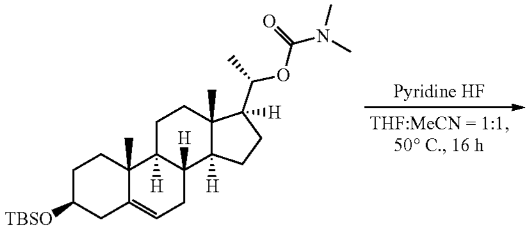

B

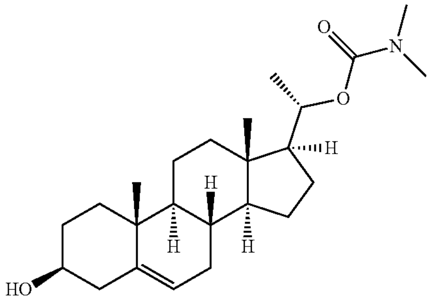

242

To a solution of compound A (140 mg, 234 μmol) in DMF (5 mL) was added DIEA (60.5 mg, 468 μmol) and dimethylamine (2 M in THF,0.35 mL, 702 μmol) at 0° C. The resulting mixture was stirred at room temperature for 16 h. The resulting mixture was extracted with water and ethyl acetate. The organic layer was dried with sodium sulfate and concentrated under vacuum to give crude product which was purified by silica gel chromatography (eluting with 1/30 ethyl acetate/PE) to give compound B (90.0 mg, 76.3%).

A mixture of compound B (70 mg, 139 μmol) and hydrogen pyridine fluoride (212 mg, 1.39 mmol) in tetrahydrofuran (5 mL) and acetonitrile (5 mL) was heated at 50° C.; for 16 h. The pH of the resulting mixture was adjusted to 7 with saturated $NaHCO_3$ solution and extracted with ethyl acetate. The organic layer was dried over anhydrous sodium sulfate and concentrated under vacuum to give crude product which was purified by silica gel chromatography (eluting with 1/10 ethyl acetate/PE) to give the title compound 242 (41.0 mg, 75.8%). $^1$H NMR (400 MHz, Chloroform-d) δ 5.35 (dd, J=5.3, 2.3 Hz, 1H), 4.84-4.74 (m, 1H), 3.56-3.47 (m, 1H), 2.88 (s, 6H), 2.30-2.19 (m, 2H), 2.04-

1.78 (m, 6H), 1.67-1.57 (m, 2H), 1.52-1.40 (m, 6H), 1.29-1.21 (m, 4H), 1.23 (d, J=1.7 Hz, 2H), 1.01 (s, 3H), 0.97-0.84 (m, 2H), 0.69 (s, 3H).

Example 243: (1S)-1-[(1S,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]ethyl N-methylcarbamate

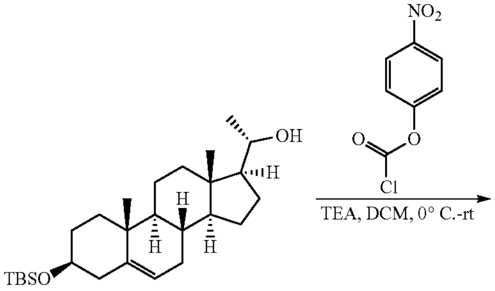

A

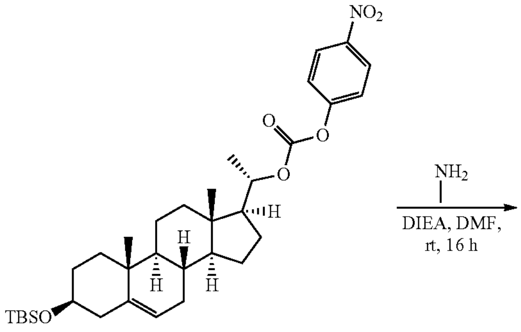

B

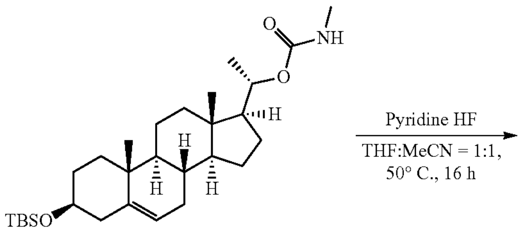

C

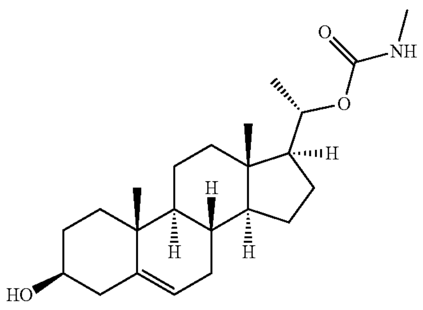

243

To a solution of compound A (300 mg, 693 μmol) in dichloromethane (6 mL) was added triethylamine (289 μL, 2.08 mmol) and 4-nitrophenyl carbonochloridate (210 mg, 1.04 mmol) at 0° C. The reaction was stirred at room temperature for 3 h. The mixture was extracted with water and ethyl acetate. The organic layer was dried with sodium sulfate and concentrated under vacuum to give crude product which was purified by silica gel chromatography (eluting with 1/30 ethyl acetate/PE) to give compound B (140 mg, 33.8%).

To a solution of compound B (140 mg, 234 μmol) in DMF (5 mL) was added DIEA (60.5 mg, 468 μmol) and methylamine (0.7 mL, 700 umol, 1M in THF) at room temperature. The resulting mixture was stirred at room temperature for 16 h. The mixture was diluted with water and extracted with ethyl acetate. The organic layer was washed with water and brine, dried with sodium sulfate and concentrated under vacuum to give crude product which was purified by silica gel chromatography (eluting with 1/5 ethyl acetate/PE) to give compound C (50 mg, 43.6%).

The mixture of compound C (30 mg, 61.2 μmol) and hydrogen pyridine fluoride (60.7 mg, 612 μmol) in tetrahydrofuran (0.5 mL) and acetonitrile (0.5 mL) was heated at 50° C.; for 16 h. The pH of the mixture was adjusted to 7 with saturated $NaHCO_3$ solution and extracted with ethyl acetate. The organic layer was dried over anhydrous sodium sulfate and concentrated under vacuum to give crude product which was purified by silica gel chromatography (eluting with 1/10 ethyl acetate/PE) to give the title compound 243 (24.8 mg, 99.2%). $^1$H NMR (400 MHz, $CDCl_3$) δ 5.35 (dt, J=4.2, 1.8 Hz, 1H), 4.81 (dt, J=12.4, 6.0 Hz, 1H), 4.48 (bs, 1H), 3.52 (tt, J=11.0, 4.4 Hz, 1H), 2.77 (d, J=4.6 Hz, 3H), 2.32-2.20 (m, 2H), 2.02-1.95 (m, 1H), 1.93-1.77 (m, 4H), 1.67-1.58 (m, 2H), 1.54-1.39 (m, 6H), 1.28-1.20 (m, 4H), 1.20-1.01 (m, 4H), 1.00 (s, 3H), 0.95 (dt, J=11.2, 5.8 Hz, 1H), 0.69 (s, 3H).

Example 244: (2S)-2-[(1R,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]propyl N-(2-methoxyethyl)carbamate

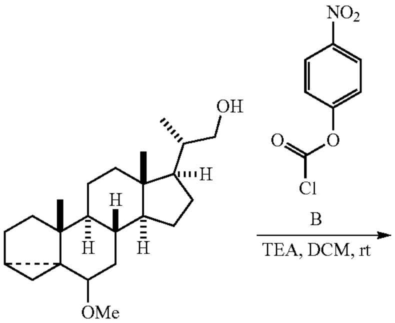

A

-continued

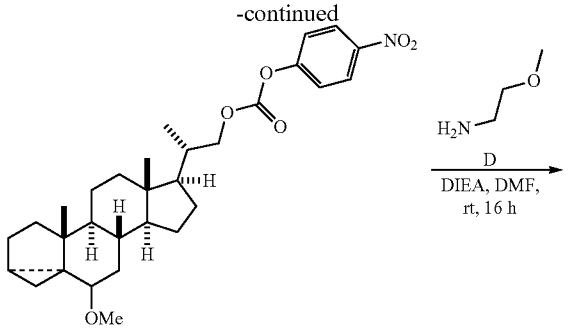

C

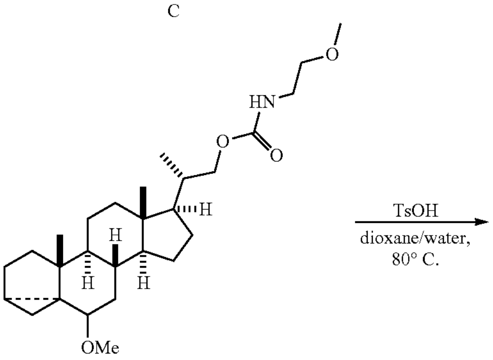

E

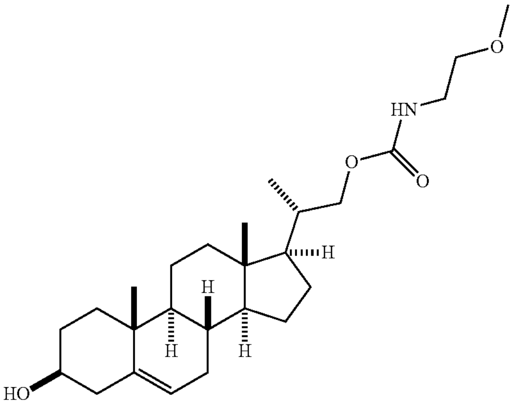

244

To a solution of compound A (500 mg, 1.44 mmol) in dichloromethane (10 mL) was added TEA (323 mg, 2.16 mmol) and compound B (320 mg, 1.59 mmol) at 0° C. The reaction mixture was stirred for 1 hour. After completion, the mixture was quenched by adding water (50 mL) and extracted with ethyl acetate (15 mL×3). The organic layer was washed with brine, dried over sodium sulfate, filtered, and concentrated to give the crude which was purified by column chromatography on silica gel to yield the title compound C (400 mg, 54%) as a white solid.

To a solution of compound C (200 mg, 412 μmol) in DMF (4 mL) was added compound D (31 mg, 412 μmol) and DIEA (160 mg, 1.24 mmol). The mixture was stirred at room temperature for 16 hours. The mixture was diluted with water and extracted with ethyl acetate. The organic layer was concentrated. The residue was purified by column chromatography on silica gel to give compound E (150 mg, 36%).

To a solution of compound E (150 mg, 335 μmol) in 1,4-dioxane (4 mL) and water (1 mL) was added 4-methylbenzene-1-sulfonic acid (11.5 mg, 67 μmol). The mixture was stirred at 80° C. for 3 hours. After completion, the mixture was quenched by adding $NaHCO_3$ (30 mL) and extracted with ethyl acetate (10 mL×3). The organic layer was washed with brine, dried over sodium sulfate, filtered, and concentrated to give the crude which was purified by column chromatography on silica gel to yield the title compound 244 (70 mg, 48%) as a white solid. LCMS:[M+Na]$^+$=456.20. $^1$H NMR (400 MHz, Chloroform-d) δ 5.35 (d, J=5.2 Hz, 1H), 5.00 (bs, 1H), 4.09 (dd, J=10.4, 3.4 Hz, 1H), 3.82-3.72 (m, 1H), 3.57-3.49 (m, 1H), 3.46 (t, J=5.1 Hz, 2H), 3.38-3.31 (m, 5H), 2.33-2.19 (m, 2H), 2.04-1.92 (m, 2H), 1.90-1.78 (m, 3H), 1.76-1.63 (m, 1H), 1.56-1.41 (m, 6H), 1.39-1.29 (m, 2H), 1.23-1.00 (m, 11H), 0.94 (dt, J=11.2, 5.6 Hz, 1H), 0.70 (s, 3H).

Example 245: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(1-iminoethyl)piperazin-1-yl)pentan-1-one

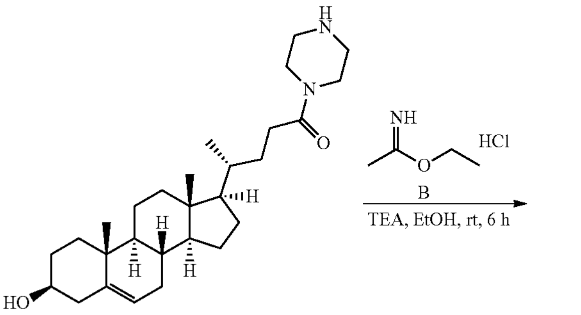

A

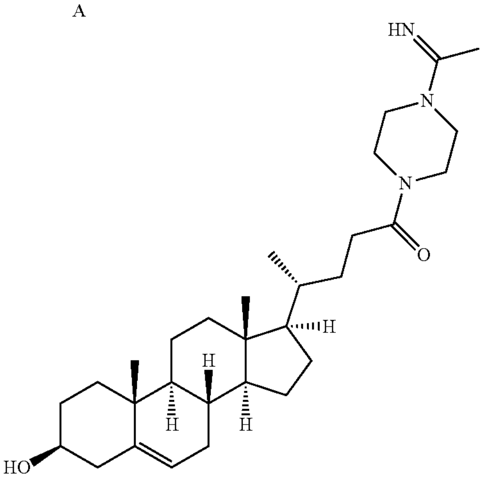

245

To a solution of compound A (300 mg, 678 μmol) and compound B (83.7 mg, 678 μmol) in ethanol (5 mL, 85.6 mmol) was added TEA (206 mg, 2.03 mmol). The mixture was stirred at room temperature for 6 hours. The mixture was diluted with water and extracted with ethyl acetate. The organic layer was concentrated, and the residue was purified by silica gel chromatography to give the title compound 245 (40 mg, 12.2%). $^1$H NMR (400 MHz, DMSO-$d_6$) δ 5.34 (d, J=5.1 Hz, 1H), 3.83-3.56 (m, 8H), 3.39 (td, J=12.4, 11.7, 6.5 Hz, 1H), 2.55-2.15 (m, 7H), 2.09-1.74 (m, 6H), 1.67-1.45 (m, 7H), 1.40-1.29 (m, 2H), 1.27-1.04 (m, 5H), 1.03 (s, 3H), 1.00 (d, J=6.6 Hz, 3H), 0.97-0.89 (m, 1H), 0.74 (s, 3H). LCMS: M+1=484.25.

Example 246: bis((1R,3aS,3bS,7S,9aR,9bS,11aR)-1-[(2R)-4-[3-(2-hydroxyethoxy) pyridin-2-yl]butan-2-yl]-9a,11a-dimethyl-1H,2H,3H,3aH,3bH,4H,6H,7H,8H,9H,9aH,9bH,10H,11H,11aH-cyclopenta[a]phenanthren-7-ol

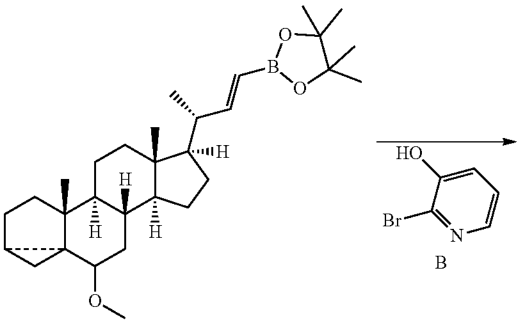

A

B

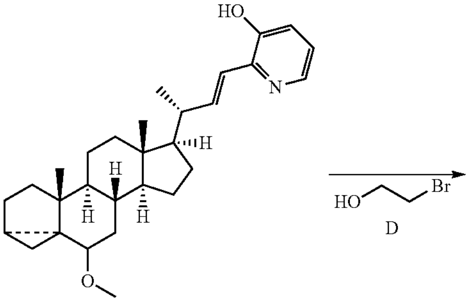

C

D

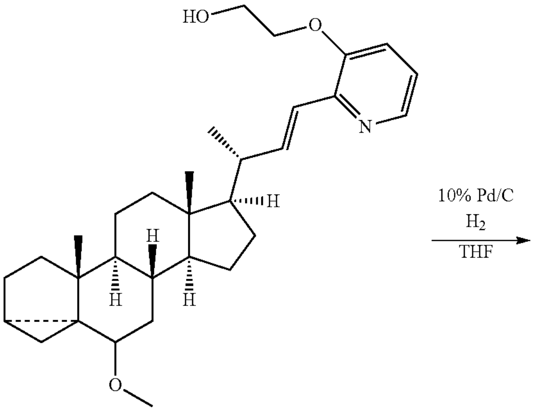

E

-continued

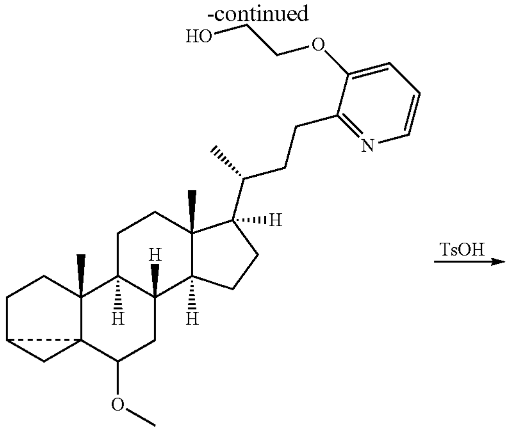

F

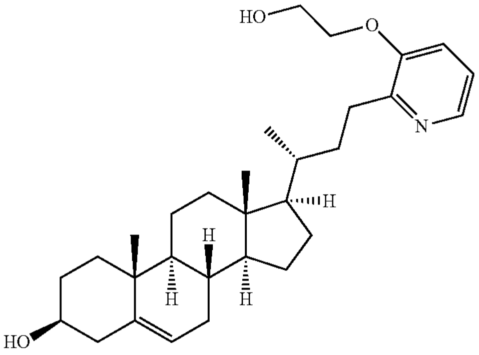

246

To a solution of compound A (500 mg, 1.07 mmol) in 1,4-dioxane (5 mL) and $H_2O$ (1 mL) was added compound B (167 mg, 960 μmol) and $Pd(PPh_3)_4$ (123 mg, 107 μmol) and $K_2CO_3$ (442 mg, 3.2 mmol) at room temperature. The mixture was stirred at 65° C.; for 16 hours. The reaction was quenched by adding saturated $NaHCO_3$ and extracted with ethyl acetate. The organic layer was concentrated, and the residue was purified by silica gel chromatography to give compound C (220 mg). To a solution of compound C (120 mg, 275 μmol) in DMF (2 mL) was added $K_2CO_3$ (228 mg, 1.65 mmol) at 50° C.; and the mixture was stirred at 50° C.; for 1 hour. Compound D (41.3 mg, 331 μmol) was added, and the reaction was heated to 120° C. for 6 h. The mixture was concentrated, and the residue was purified by silica gel chromatography to give compound E (80 mg, 60%). To a solution of compound E (160 mg, 334 μmol) in THF (4 mL) was added 10% Pd/C (50 mg) at room temperature, the mixture was stirred for 16 hours under $H_2$ atmosphere. The mixture was filtered and concentrated. The residue was purified by silica gel chromatography to give compound F (130 mg).

To a solution of compound F (130 mg, 271 μmol) in water (0.2 mL) and 1,4-dioxane (1 mL) was added TsOH (9.33 mg, 54.2 μmol). The mixture was stirred at 80° C.; for 2 hours. The reaction was quenched by adding saturated $NaHCO_3$ and extracted with ethyl acetate. The organic layer was concentrated, and the residue was purified by silica gel chromatography to give compound 246 (60 mg, 47%). $^1H$ NMR (400 MHz, Chloroform-d) δ 8.15 (dd, J=4.8, 1.4 Hz, 1H), 7.25-7.11 (m, 2H), 5.34 (d, J=4.9 Hz, 1H), 4.13 (t, J=4.5 Hz, 2H), 4.07-3.95 (m, 2H), 3.60-3.45 (m, 1H), 3.08-2.69 (m, 2H), 2.36-2.16 (m, 2H), 2.13-1.73 (m, 8H), 1.53-1.36 (m, 7H), 1.33-1.12 (m, 4H), 1.07 (d, J=6.4 Hz, 3H), 1.01 (s, 3H), 0.92 (dd, J=11.2, 5.5 Hz, 1H), 0.68 (s, 3H). LCMS: M+1=468.4.

Example 247: (1R,3aS,3bS,7S,9aR,9bS,11aR)-1-[(2R)-4-(3-ethoxypyridin-2-yl)butan-2-yl]-9a,11a-dimethyl-1H,2H,3H,3aH,3bH,4H,6H,7H,8H,9H,9aH,9bH,10H,11H,11aH-cyclopenta[a]phenanthren-7-ol

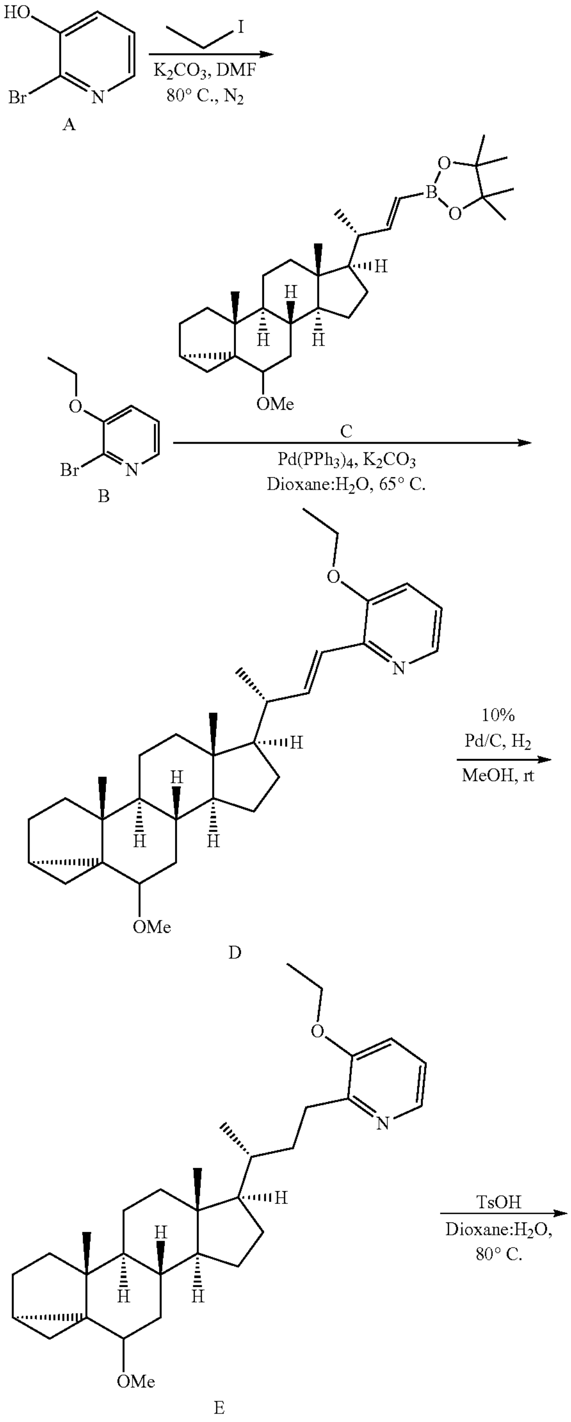

-continued

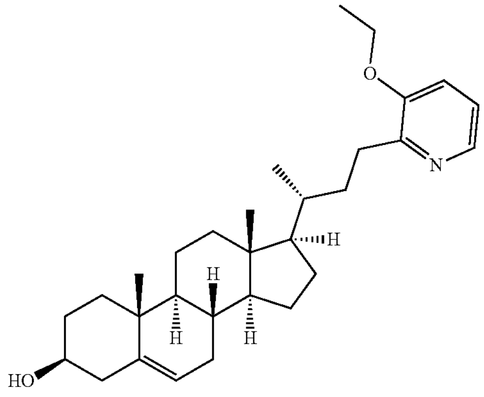

247

To a solution of compound A (2.0 g, 11.5 mmol) in DMF (20 mL) was added $K_2CO_3$ (2.54 g, 18.4 mmol) and iodoethane (1.56 mL, 19.5 mmol) at room temperature. The mixture was heated at 80° C.; for 16 h. The mixture was diluted with water and extracted with ethyl acetate. The organic layer was washed with water and brine, dried with sodium sulfate and concentrated under vacuum to give compound B (2.30 g, 99.2%).

To a solution of compound C (200 mg, 427 μmol) in a mixture of 1,4-dioxane (5 mL) and water (1 mL) was added $K_2CO_3$ (177 mg, 1.28 mmol), compound B (86.2 mg, 427 μmol) and tetrakis(triphenylphosphane) palladium (49.3 mg, 42.7 μmol). The mixture was heated at 65° C.; for 16 h under nitrogen. After cooling to ambient temperature, the mixture was filtered through Celite, and the filtrate was concentrated under vacuum. The residue was purified by silica gel chromatography (eluting with 1/20 ethyl acetate/PE) to give compound D (100 mg, 50.5%). To a solution of compound D (100 mg, 216 μmol) in methanol (6 mL) was added 10% Pd/C (5 mg). The reaction was stirred for 1 h at room temperature under 1 atm of $H_2$. Then the mixture was filtered through Celite and concentrated under vacuum to give compound D (80 mg, 79.6%).

A mixture of compound D (100 mg, 215 μmol) and 4-methylbenzene-1-sulfonic acid hydrate (8.17 mg, 0.2 eq., 42.9 μmol) in 1,4-dioxane (8 mL) and water (2 mL) was heated at 80° C.; for 4 h under nitrogen. The pH of the mixture was adjusted to 7 with saturated $NaHCO_3$ solution, extracted with ethyl acetate. The organic layer was dried over anhydrous sodium sulfate and concentrated under vacuum to give crude product which was purified by silica gel chromatography (eluting with 1/10 ethyl acetate/PE) to give compound 247 (48.4 mg, 49.9%). $^1H$ NMR (400 MHz, Chloroform-d) δ 8.13-8.04 (m, 1H), 7.09 (d, J=3.2 Hz, 2H), 5.35 (d, J=5.1 Hz, 1H), 4.04 (q, J=7.0 Hz, 2H), 3.51 (dd, J=14.3, 4.5 Hz, 2H), 2.92 (td, J=12.1, 4.5 Hz, 1H), 2.74 (td, J=11.7, 5.1 Hz, 1H), 2.31-2.19 (m, 2H), 2.07-1.73 (m, 7H), 1.45 (t, J=6.9 Hz, 6H), 1.31-1.10 (m, 6H), 1.06 (d, J=6.6 Hz, 3H), 1.01 (s, 3H), 0.98-0.82 (m, 2H), 0.69 (s, 3H). LCMS: $[M+H]^+$=452.20.

Example 248: (3S,8S,9S,10R,13R,14S,17R)-17-((R)-4-(3-(2-hydroxypropan-2-yl)pyridin-2-yl)butan-2-yl)-10,13-dimethyl-2,3,4,7,8,9,10,11,12,13,14,15,16,17-tetradecahydro-1H-cyclopenta[a]phenanthren-3-ol

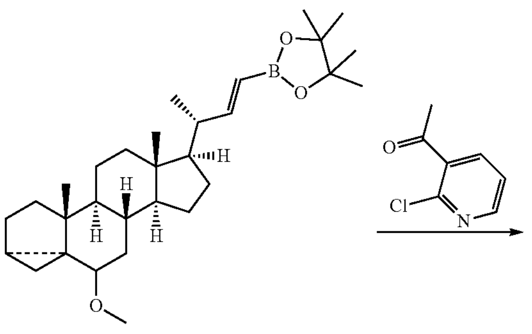

A

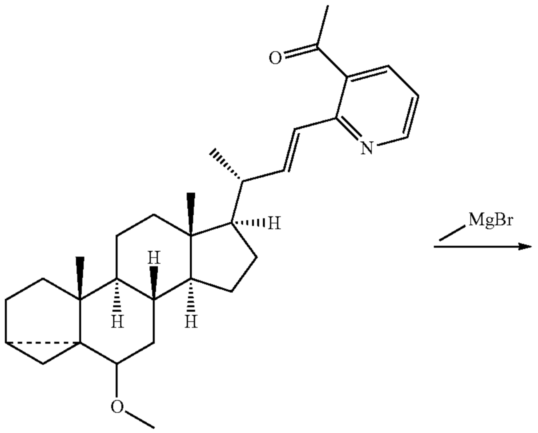

B

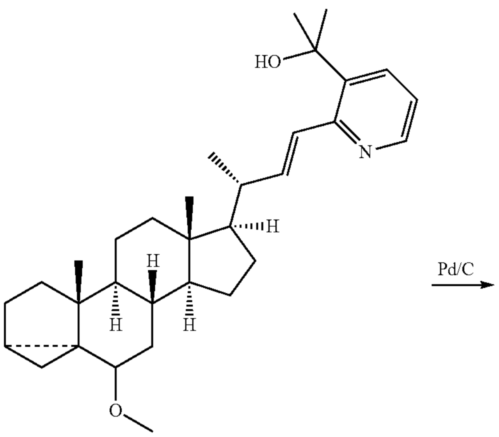

C

-continued

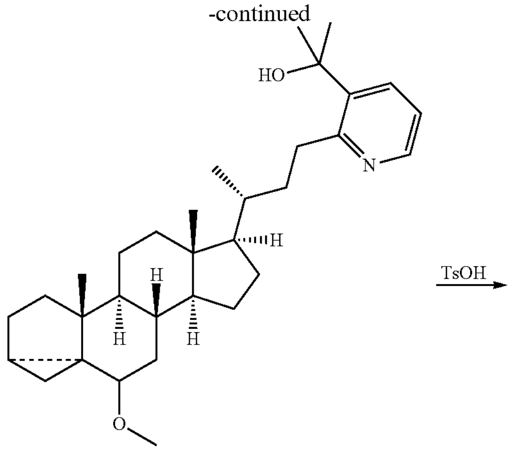

D

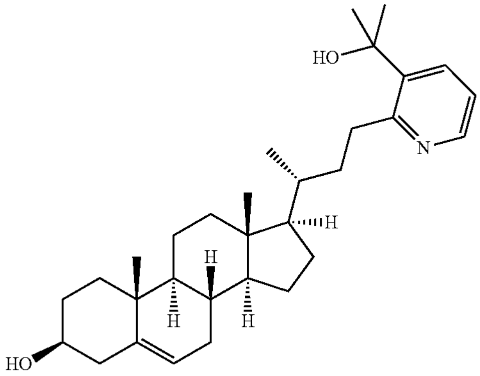

Example 248

To a solution of compound A (200 mg, 426 μmol) in 1,4-dioxane (5 mL) and water (1 mL) was added $Pd(PPh_3)_4$ (24.6 mg, 21.4 μmol), 1-(2-chloropyridin-3-yl)ethan-1-one (79.6 mg, 512 μmol) and $K_2CO_3$ (177.6 mg, 1.28 mmol) at room temperature. The mixture was stirred at 65° C. for 16 hours under an $N_2$ atmosphere. The result solution was quenched by the addition of water and extracted with DCM. The combined organic layers were dried over sodium sulfate and concentrated to give crude product. The crude product was purified by silica gel chromatography to give compound B (120 mg, 61%). To a solution of compound B (100 mg, 217 μmol) in THF (3 mL) at −78° C., was added $CH_3MgBr$ (1.08 mL, 1.08 mmol, 1M in THF) and stirred at room temperature for 16 h. The mixture was added $NH_4Cl$ (aq) and extracted with DCM. The organic phase was concentrated to give crude which was purified by silica gel chromatography to give compound C (60 mg, 58%). A solution of compound C (60 mg, 126 μmol) and 10% Pd/C (30 mg) in methanol (2 mL) was stirred at room temperature for 16 h under 1 atm $H_2$. The mixture was filtered and concentrated to give compound D (50 mg, 83%).

A solution of compound D (50 mg, 104 μmol) and 4-methylbenzene-1-sulfonic acid (3.59 mg, 20.8 μmol) in 1,4-dioxane (3 mL)/water (0.5 mL) was stirred at 80° C. for 2 h. The mixture was added $NaHCO_3$ (aq) and extracted with DCM. The organic phase was concentrated to give crude which was purified by silica gel chromatography to give the title compound 248 (20 mg, 41%). $^1H$ NMR (400 MHz, Chloroform-d) δ 8.51 (d, J=4.8 Hz, 1H), 7.82 (s, 1H), 7.13 (s, 1H), 5.39 (s, 1H), 3.61-3.49 (m, 1H), 3.30-3.13 (m, 1H), 3.00 (t, J=12.1 Hz, 1H), 2.36-2.24 (m, 2H), 2.14-2.01 (m, 2H), 1.98-1.84 (m, 4H), 1.77 (s, 1H), 1.72 (s, 6H), 1.42-1.29

(m, 5H), 1.27-1.19 (m, 2H), 1.17-1.10 (m, 4H), 1.09 (d, J=7.8 Hz, 1H), 1.06 (s, 3H), 1.02-0.88 (m, 2H), 0.75 (s, 3H).

Example 249: (3S,8S,9S,10R,13R,14S,17R)-17-((2R)-4-(3-(1-hydroxyethyl)pyridin-2-yl)butan-2-yl)-10,13-dimethyl-2,3,4,7,8,9,10,11,12,13,14,15,16,17-tetradecahydro-1H-cyclopenta[a]phenanthren-3-ol

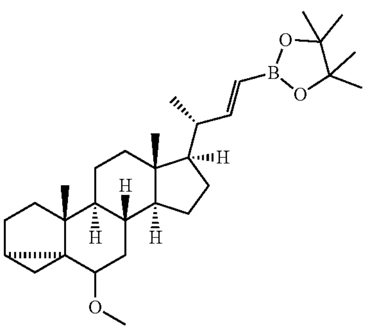

A

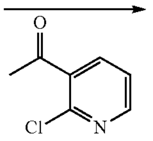

B

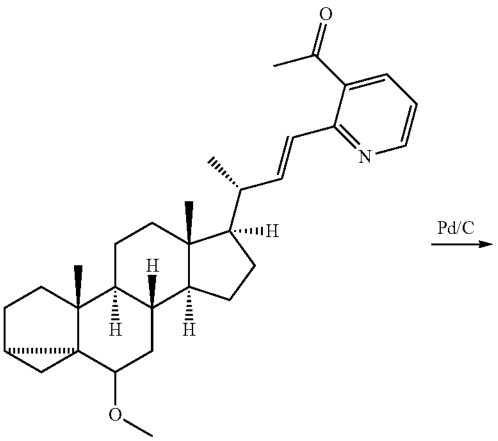

C

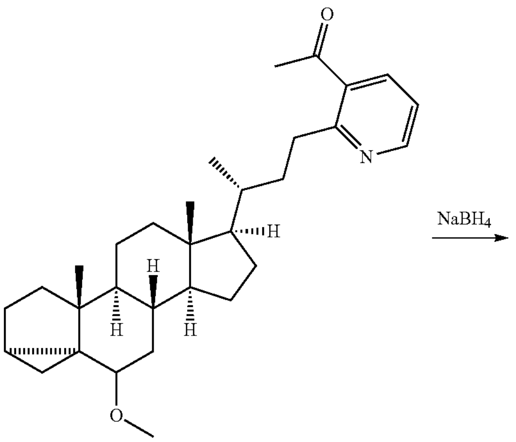

D

-continued

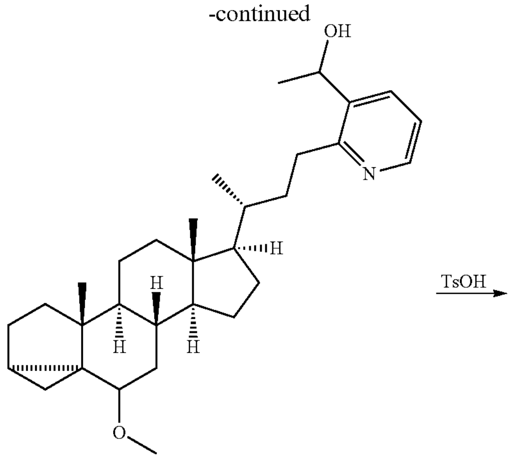

E

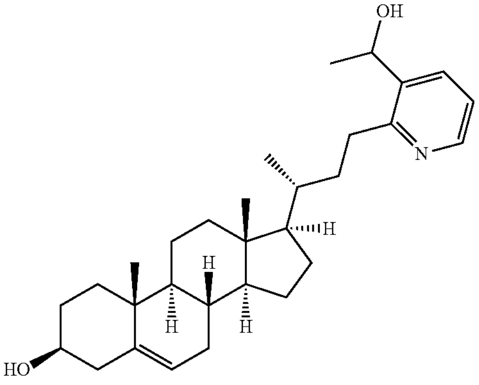

249

To a solution of compound A (500 mg, 1.07 mmol) in 1,4-dioxane (20 mL) and water (4 mL) was added compound B (149 mg, 960 μmol), $Pd(PPh_3)_4$ (123 mg, 107 μmol) and $K_2CO_3$ (442 mg, 3.2 mmol), the mixture was stirred at 65° C. for 16 hours under $N_2$. After completion, the result solution was quenched by the addition of water and extracted with DCM. The combined organic layers were dried over sodium sulfate and concentrated to give the crude product which was purified by silica gel chromatography to give compound C (320 mg, 65%).

To a solution of compound C (320 mg, 693 μmol) in methanol (10 mL) was added 10% Pd/C (32 mg) and stirred for 2 hours under 1 atm of $H_2$. After completion, the mixture was filtered through Celite and concentrated under vacuum to afford compound D (320 mg, 99%).

To a solution of compound D (200 mg, 417 μmol) in methanol (6 mL) was added $NaBH_4$ (15.8 mg, 417 μmol) at 0° C. The mixture was stirred at 0° C. for 30 minutes. After completion, the solution was concentrated to give crude which was purified by silica gel chromatography to give compound E (140 mg, 72%).

To a solution of compound E (70 mg, 150 μmol) in 1,4-dioxane (5 mL) and water (1 mL) was added 4-methylbenzene-1-sulfonic acid (5.18 mg, 30.1 μmol) at room temperature, the mixture was stirred at 80° C. for 2 hours. The result solution was quenched by the addition of saturated $NaHCO_3$ and extracted with DCM. The combined organic layers were dried over sodium sulfate and concentrated to give crude product which was purified by silica gel chromatography to give the title compound 249 (20 mg, 24%). $^1H$ NMR (400 MHz, Chloroform-d) δ 8.50-8.41 (m, 1H), 7.93 (s, 1H), 5.35 (d, J=5.2 Hz, 1H), 5.18 (d, J=6.8 Hz, 1H), 3.58-3.46 (m, 1H), 3.01-2.88 (m, 1H), 2.81-2.65 (m, 1H), 2.34-2.19 (m, 2H), 2.05-1.79 (m, 7H), 1.60-1.43 (m, 12H), 1.36-1.24 (m, 2H), 1.24-1.08 (m, 3H), 1.08 (d, J=6.2 Hz, 3H), 1.01 (s, 3H), 0.94 (td, J=11.2, 5.3 Hz, 1H), 0.70 (s, 3H). LCMS: M+1=452.20.

Example 250: (3S,8S,9S,10R,13R,14S,17R)-17-((R)-4-(3-(hydroxymethyl)pyridin-2-yl)butan-2-yl)-10,13-dimethyl-2,3,4,7,8,9,10,11,12,13,14,15,16,17-tetradecahydro-1H-cyclopenta[a]phenanthren-3-ol

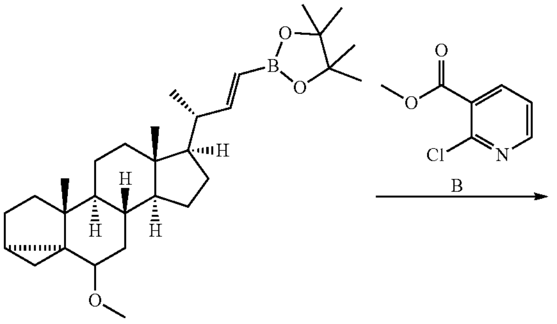

B

A

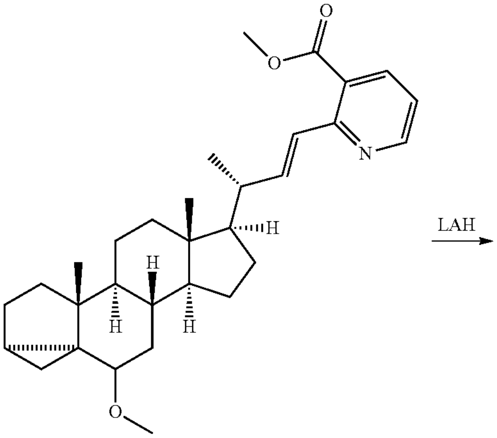

C

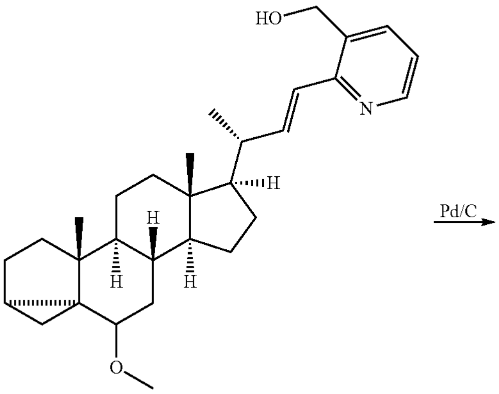

D

-continued

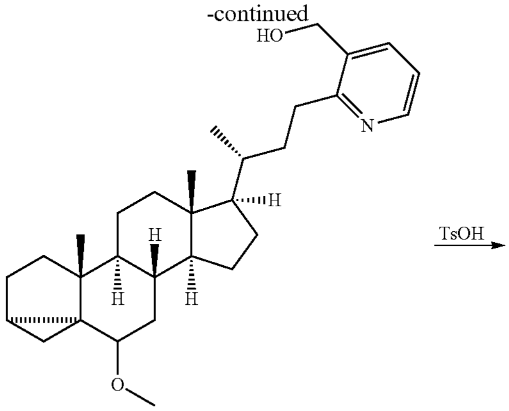

E

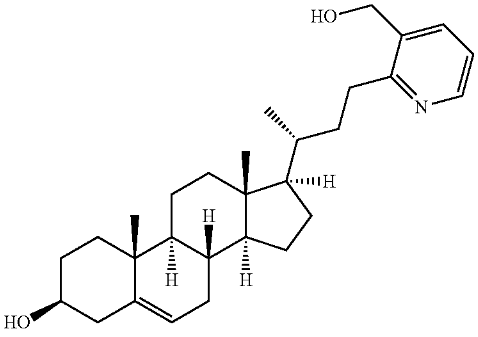

250

To a solution of compound A (200 mg, 427 μmol) in 1,4-dioxane (5 mL) and water (1 mL) was added compound B (65.9 mg, 384 μmol), $K_3CO_3$ (177 mg, 1.28 mmol) and $Pd(PPh_3)_4$ (49.3 mg, μmol). The mixture was stirred at 65° C. for 16 h under nitrogen. After completion, the mixture was quenched by adding $H_2O$ (20 mL) and extracted with ethyl acetate (15 mL×3). The organic layer was washed with brine, dried over sodium sulfate, filtered, and concentrated to give the crude which was purified by column chromatography on silica gel to yield the title compound C (160 mg, 78.47%) as a solid. To a solution of compound C (160 mg, 335 μmol) in tetrahydrofuran (3 mL) was added LAH (50.8 mg, 1.34 mmol) at 0° C. The mixture was stirred at room temperature for 30 mins under nitrogen. After completion, the mixture was quenched by adding methanol (10 mL) and concentrated to give the crude which was purified by column chromatography on silica gel to yield the title compound D (150 mg, 99.6%) as a white solid. To a solution of compound D (50 mg, 111 μmol) in methanol (3 mL) was added 10% Pd/C (10 mg). The mixture was stirred at room temperature for 3 hours under 1 atm of hydrogen. The mixture was filtered and concentrated under reduced pressure to afford the crude product which was purified by prep-TLC to afford compound E (50 mg, 99.6%) as oil.

To a solution of compound E (50 mg, 111 μmol) in 1,4-dioxane (4 mL) and water (1 mL) was added 4-methylbenzene-1-sulfonic acid (4.21 mg, 22.1 μmol). The mixture was stirred at 80° C. for 3 hours. After completion, the mixture was quenched by adding $NaHCO_3$ (5 mL) and extracted with ethyl acetate (10 mL×3). The organic layer was washed with brine, dried over sodium sulfate, filtered, and concentrated to give the crude which was purified by column chromatography on silica gel to yield the title compound 250 (12 mg, 24.8%) as a white solid. LCMS: $[M+H]^+$=438.20. $^1H$ NMR (400 MHz, Methanol-$d_4$) δ 8.46

(d, J=5.2 Hz, 1H), 8.20 (d, J=7.8 Hz, 1H), 7.56 (dd, J=7.8, 5.4 Hz, 1H), 5.34 (d, J=5.0 Hz, 1H), 4.75 (s, 2H), 3.44-3.33 (m, 1H), 3.02 (td, J=12.8, 5.1 Hz, 1H), 2.82-2.75 (m, 1H), 2.24-2.17 (m, 2H), 2.06-1.85 (m, 4H), 1.83-1.74 (m, 2H), 1.68-1.57 (m, 3H), 1.51 (s, 1H), 1.49-1.38 (m, 3H), 1.30-1.17 (m, 7H), 1.12 (d, J=6.4 Hz, 3H), 1.08 (d, J=4.8 Hz, 1H), 1.03 (s, 3H), 0.96 (q, J=6.2, 5.0 Hz, 1H), 0.90 (t, J=6.8 Hz, 1H), 0.75 (s, 3H).

Example 251: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(trifluoromethoxy)piperidin-1-yl]pentan-1-one

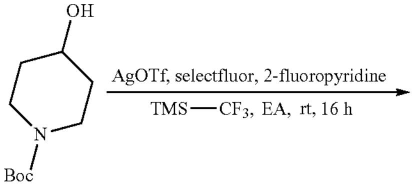

A

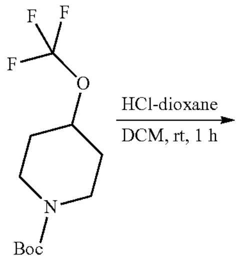

B

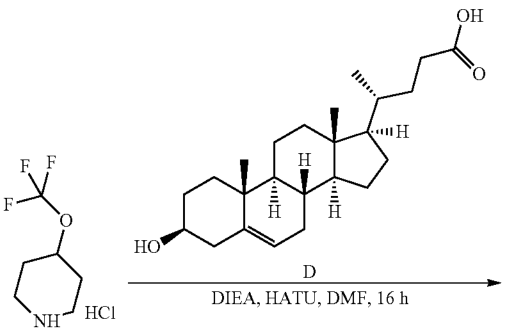

C

-continued

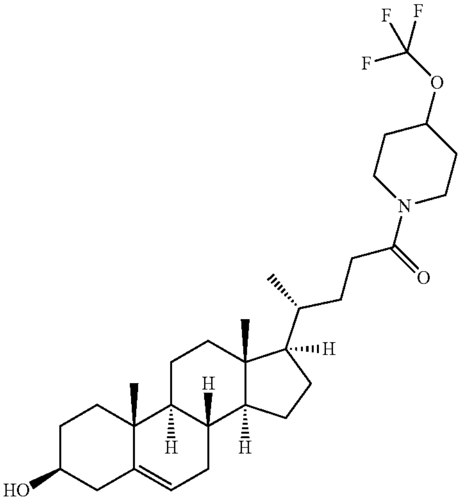

251

To a reaction tube that was equipped with a stirring bar, AgOTf (5.74 g, 22.4 mmol), 1-(Chloromethyl)-4-fluoro-1,4-diazabicyclo[2.2.2]octane-1,4-diium ditetrafluoroborate (3.96 g, 11.2 mmol), potassium fluoride (1.73 g, 29.8 mmol), compound A (1.5 g, 7.45 mmol) were added successively under $N_2$. Then ethyl acetate (37.5 mL, 380 mmol), 2-fluoropyridine (2.17 g, 22.4 mmol) and tert-butyl (trifluoromethyl) silane (3.49 g, 22.4 mmol) were added successively. After stirring at room temperature for 16 hours, the reaction was quenched with water and extracted with ethyl acetate (20 mL×4). The combined organic layer was concentrated to give the crude which was purified by silica gel chromatography to yield the title compound C (200 mg, 7.2%). To a solution of compound C (150 mg, 557 μmol) in DCM (2 mL) was added hydrogen chloride (2 mL, 8 mmol, 4 M in dioxane). After stirring at room temperature for 1 hour, the reaction was quenched with water and extracted with ethyl acetate. The combined organic layer was concentrated to give the crude compound C (73 mg, 53%).

To a solution of compound C (73 mg, 355 μmol) in DMF (2 mL) was added compound D (106 mg, 284 μmol), DIEA (275 mg, 2.13 mmol) and HATU (250 mg, 1.06 mmol). The mixture was stirred at room temperature for 16 hours. The reaction was quenched with water and extracted with ethyl acetate. The combined organic layer was concentrated to give the crude which was purified by silica gel chromatography to yield the title compound 251 (25.2 mg, 13%). LCMS:$[M+1]^+$=526.25. $^1H$ NMR (400 MHz, Chloroform-d) δ 5.35 (s, 1H), 4.48 (s, 1H), 3.81 (bs, 1H), 3.66 (bs, 1H), 3.57-3.47 (m, 2H), 3.38 (bs, 1H), 2.47-2.13 (m, 4H), 2.06-1.70 (m, 10H), 1.66-1.40 (m, 10H), 1.39-1.23 (m, 3H), 1.21-1.03 (m, 4H), 1.02-0.99 (m, 3H), 0.95 (d, J=6.6 Hz, 4H), 0.69 (s, 3H). F NMR (400 MHz, Chloroform-d) δ−58.02.

Example 252: (R)-1-(4-(difluoromethoxy)piperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

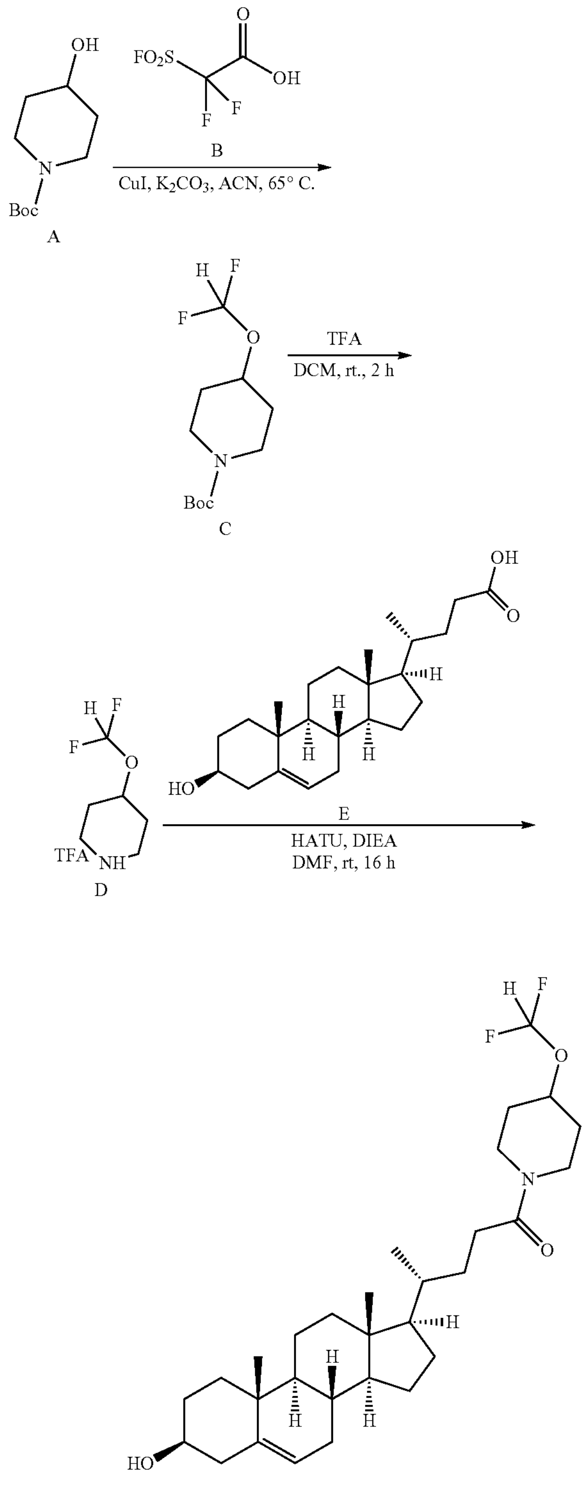

252

To a solution of compound A (2.01 g, 10 mmol) in ACN (20 mL) was added compound B (3.56 g, 20 mmol), CuI (570 mg, 3 mmol) and $K_2CO_3$ (4.14 g, 30 mmol). After stirring at 65° C. for 16 h, the reaction was quenched with water and extracted with EA. The organic layer was dried under vacuum and the residue was purified with silica gel chromatography to afford compound C (740 mg, 29%). To a solution of compound C (100 mg, 398 μmol) in DCM (2 mL) was added TFA (0.5 mL). The mixture was stirred at room temperature for 2 h. The mixture was concentrated to afford compound D and used directly into the next step.

To a solution of E (100 mg, 267 μmol) in DMF (2 mL) was added D (133.1 mg, 534 μmol), DIEA (173 mg, 1.33 mmol) and HATU (152 mg, 0.4 mmol). The mixture was stirred at room temperature for 3 h. The mixture was added water and extracted with EA. The organic layer was washed with brine, dried over sodium sulfate, and concentrated to afford the crude which was purified by silica gel chromatography to afford the title compound 252 (50 mg, 36.9%). LCMS [M+1]=508.20. $^1$HNMR (400 MHz, Chloroform-d) δ 6.27 (t, J=74.5 Hz, 1H), 5.35 (d, J=5.2 Hz, 1H), 4.44 (s, 1H), 3.75 (bs, 2H), 3.55-3.35 (m, 3H), 2.40 (bs, 1H), 2.30-2.18 (m, 3H), 2.02-1.68 (m, 13H), 1.62-1.37 (m, 8H), 1.36-1.26 (m, 3H), 1.21-1.02 (m, 5H), 1.01 (s, 3H), 0.96 (d, J=6.3 Hz, 3H), 0.90 (dt, J=18.6, 6.1 Hz, 1H), 0.68 (s, 3H). $^{19}$FNMR (376 MHz, Chloroform-d) δ−81.29 (d, J=74.8 Hz).

Example 253: 2-((S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propoxy)-N-methylnicotinamide

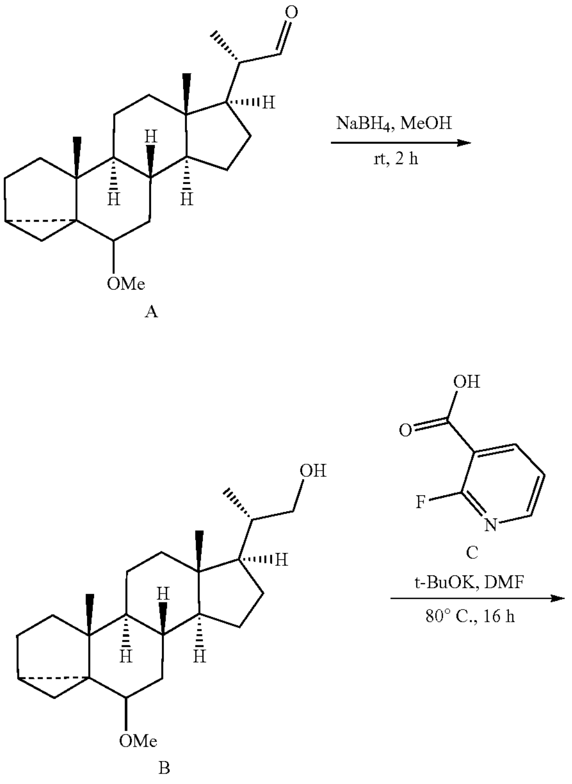

-continued

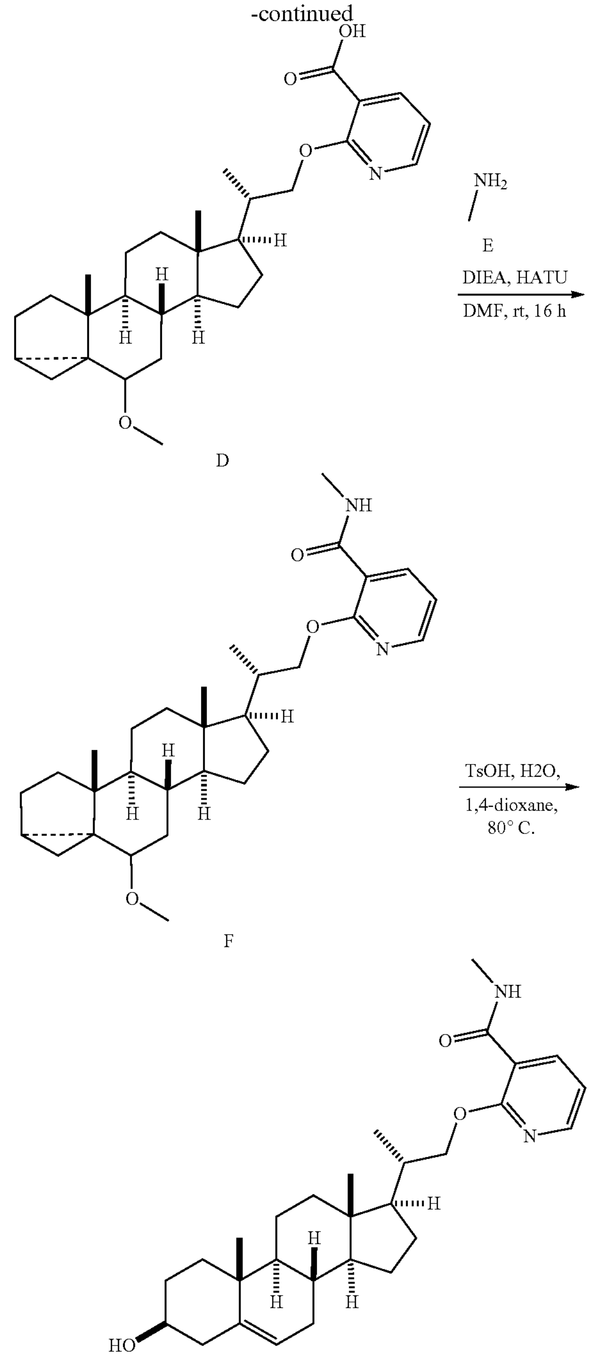

D

F

253

To a solution of compound A (6.0 g, 17.4 mmol) in methanol (40 mL) was added $NaBH_4$ (660 mg, 17.4 mmol). The mixture was stirred at room temperature for 2 hours. The resulting solution was added HCl (1M) to adjust pH to 3 then extracted with EtOAc (40 mL×3). The combined organic phases were washed with brine, dried over sodium sulfate, and concentrated under vacuum to afford B (6.0 g, 99.4%). To a solution of compound B (1.0 g, 2.89 mmol) in DMF (15 mL) was added compound C (407 mg, 2.89 mmol) and tBuOK (1.3 g, 11.5 mmol). The mixture was stirred at 80° C.; for 16 hours. The mixture was diluted $H_2O$ with and extracted with ethyl acetate. The combined organic layer was concentrated to give crude which was purified by silica gel chromatography to give compound D (300 mg, 22.2%) as a solid. To a solution of compound D (100 mg, 214 μmol) in DMF (3 mL) was added compound E (0.17 mL, 2M in THF, 314 umol), DIEA (166 mg, 1.28 mmol) and HATU (162 mg, 428 mmol). The mixture was stirred at room temperature for 16 hours. The mixture was diluted with $H_2O$ and extracted with ethyl acetate. The combined organic layer was concentrated to give crude which was purified by silica gel chromatography to give compound F (40 mg, 38.9%) as a white solid.

To a solution of compound F (40 mg, 83.2 μmol) in 1,4-dioxane (1.4 mL) and water (0.2 mL) was added 4-methylbenzene-1-sulfonic acid (2.8 mg, 16.6 μmol). The reaction was stirred at 80° C. for 3 hours. The mixture was diluted with $NaHCO_3$ (15 mL) and extracted with ethyl acetate. The combined organic layer was concentrated to give crude which was purified by silica gel chromatography to give the title compound 253 (15 mg, 38.6%) as a white solid. $^1H$ NMR (400 MHz, Chloroform-d) δ 8.52 (dd, J=7.6, 2.0 Hz, 1H), 8.23 (dd, J=4.9, 2.0 Hz, 1H), 8.04 (s, 1H), 7.03 (dd, J=7.6, 4.9 Hz, 1H), 5.36 (d, J=5.1 Hz, 1H), 4.47 (dd, J=10.4, 3.1 Hz, 1H), 4.28 (dd, J=10.4, 6.3 Hz, 1H), 3.53 (tt, J=10.0, 4.3 Hz, 1H), 3.03 (d, J=4.8 Hz, 3H), 2.34-2.19 (m, 2H), 2.11-1.78 (m, 7H), 1.68-1.62 (m, 1H), 1.56-1.39 (m, 7H), 1.36-1.29 (m, 2H), 1.17 (d, J=6.7 Hz, 4H), 1.15-1.05 (m, 3H), 1.03 (s, 3H), 1.01-0.94 (m, 1H), 0.77 (s, 3H). LCMS: $[M+1]^+$=467.20.

Example 254: 2—((S)-2-((3S,8S,9S,10R,13S,14S, 17R)-3-hydroxy-10,13-dimethyl-2,3,4,7,8,9,10,11, 12,13,14,15,16,17-tetradecahydro-1H-cyclopenta[a] phenanthren-17-yl)propoxy)-N-methylisonicotinamide

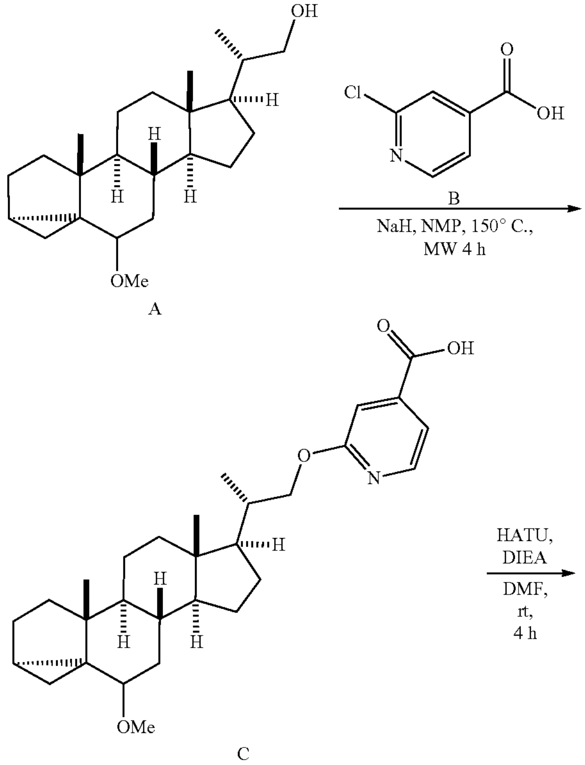

A

B

C

-continued

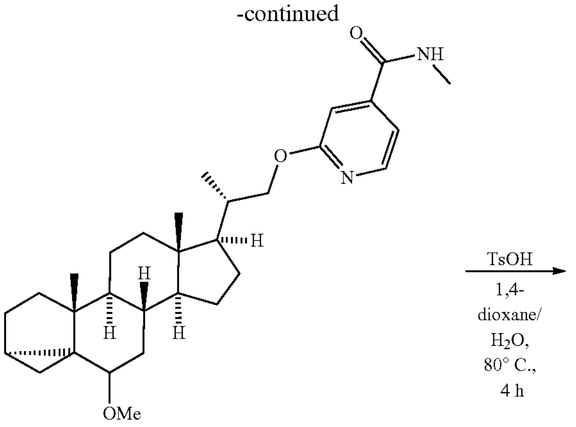

D

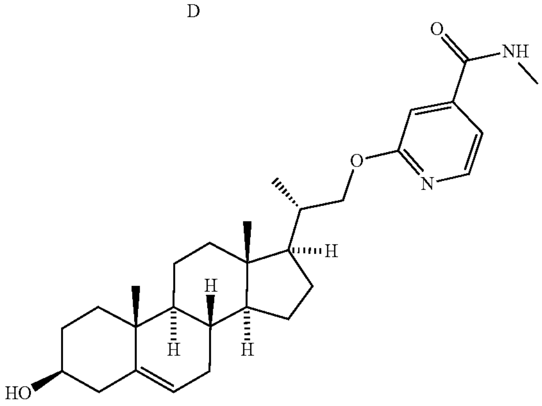

Example 254

To a solution of compound A (600 mg, 1.82 mmol) in NMP (6 mL) was added compound B (286 mg, 1.82 mmol) and NaH (417 mg, 10.4 mmol, 60% dispersion in oil). The mixture was heated at 150° C.; for 4 h using microwave irradiation. The mixture was diluted with water and extracted with ethyl acetate. The organic layer was concentrated to give crude which was purified by prep-TLC to give compound C (520 mg, 64%).

To a solution of compound C (270 mg, 577 μmol) in DMF (6 mL) was added methyl amine (26.9 mg, 866 μmol), DIEA (373 mg, 2.89 mmol) and HATU (272 mg, 1.15 mmol). After stirring at room temperature for 4 hours, the mixture was diluted with water and extracted with ethyl acetate. The organic layer was concentrated to give crude which was purified by silica gel chromatography to give compound D (60 mg, 21%).

To a solution of compound D (60 mg, 125 μmol) in 1,4-dioxane (1.4 mL) and water (0.2 mL) was added 4-methylbenzene-1-sulfonic acid (4.3 mg, 25 μmol). The mixture was stirred at 80° C.; for 4 h. The mixture was adjusted pH to 7 with $NaHCO_3$ and extracted with DCM. The organic layer was dried over anhydrous sodium sulfate and concentrated to give the crude which was purified by silica gel chromatography to give the title compound 254 (26 mg, 44%). $^1H$ NMR (400 MHz, Chloroform-d) δ 8.22 (d, J=5.3 Hz, 1H), 7.12 (dd, J=5.3, 1.4 Hz, 1H), 7.03 (d, J=1.1 Hz, 1H), 6.12 (s, 1H), 5.35 (d, J=5.2 Hz, 1H), 4.28 (dd, J=10.2, 3.3 Hz, 1H), 4.04 (dd, J=10.1, 7.1 Hz, 1H), 3.56-3.47 (m, 1H), 3.01 (d, J=4.9 Hz, 3H), 2.32-2.21 (m, 2H), 2.09-1.93 (m, 3H), 1.91-1.78 (m, 4H), 1.67-1.60 (m, 1H), 1.54-1.48 (m, 3H), 1.48-1.41 (m, 2H), 1.41-1.32 (m, 2H), 1.26 (s, 3H), 1.24-1.14 (m, 2H), 1.12 (d, J=6.6 Hz, 3H), 1.10-1.04 (m, 2H), 1.02 (s, 3H), 0.96 (td, J=11.3, 5.4 Hz, 1H), 0.74 (s, 3H). LCMS: $[M+1]^+$=467.20.

Example 255: 6—((S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propoxy)-N-methylnicotinamide

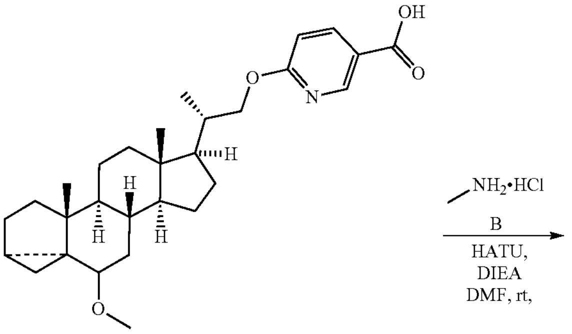

A

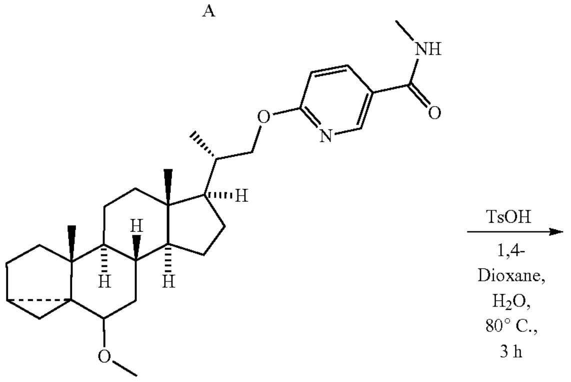

C

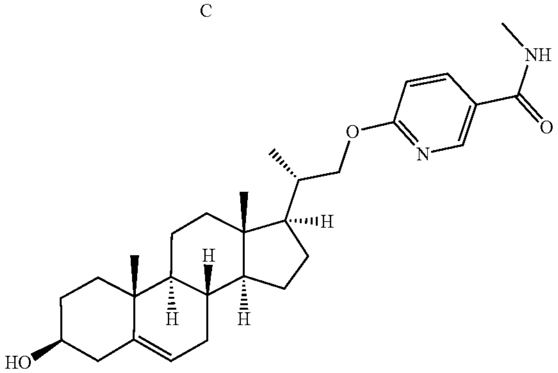

255

To a solution of compound A (220 mg, 470 μmol) in DMF (3 mL) was added compound B (43.8 mg, 1.41 mmol, HCl salt), DIEA (304 mg, 2.35 mmol) and HATU (268 mg, 706 μmol). The mixture was stirred at room temperature for 16 h. The mixture was added water and extracted with EA. The organic layer was washed with brine, dried over sodium sulfate, and concentrated. The residue was purified by silica gel chromatography to afford compound C (100 mg, 40.02%).

To a solution of compound C (100 mg, 208 μmol) in 1,4-dioxane (2 mL) and water (0.5 mL) was added TsOH (7.92 mg, 41.6 μmol). The mixture was stirred at 80° C.

under $N_2$ for 3 h. The mixture was adjusted to pH=7 by $NaHCO_3$ and extracted with EA. The organic layer was dried over sodium sulfate and concentrated to afford the crude which was purified by Prep-TLC to afford the title compound 255 (38.4 mg, 39.5%). LCMS [M+1]=467.20. $^1$HNMR (400 MHz, Chloroform-d) δ 8.72 (d, J=2.3 Hz, 1H), 8.16 (dd, J=8.8, 2.3 Hz, 1H), 6.85 (d, J=8.7 Hz, 1H), 6.58 (s, 1H), 5.35 (d, J=5.1 Hz, 1H), 4.37 (dd, J=10.0, 3.3 Hz, 1H), 4.11 (dd, J=10.0, 7.3 Hz, 1H), 3.53 (tt, J=11.1, 4.7 Hz, 1H), 3.01 (d, J=4.4 Hz, 3H), 2.34-2.19 (m, 3H), 2.06-1.81 (m, 7H), 1.67-1.27 (m, 11H), 1.24-1.16 (m, 1H), 1.13 (d, J=6.6 Hz, 3H), 1.11-1.03 (m, 2H), 1.02 (s, 3H), 0.96 (td, J=11.2, 5.1 Hz, 1H), 0.74 (s, 3H).

Example 256: 6—((S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propoxy)-N-methylpicolinamide

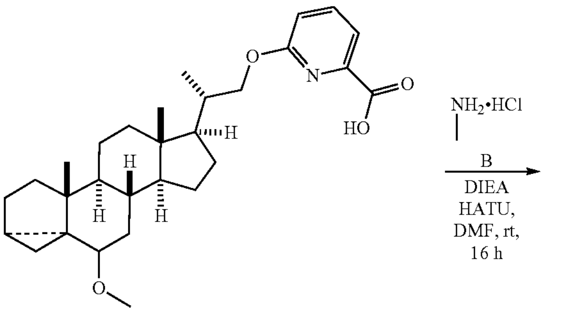

A

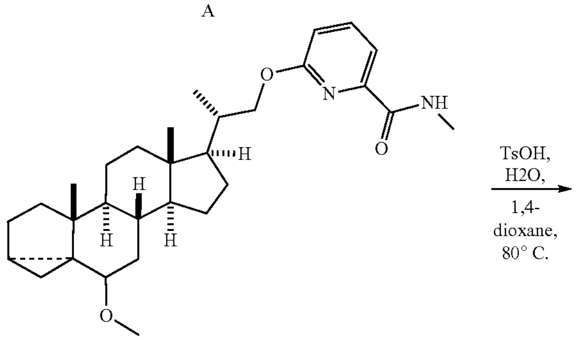

C

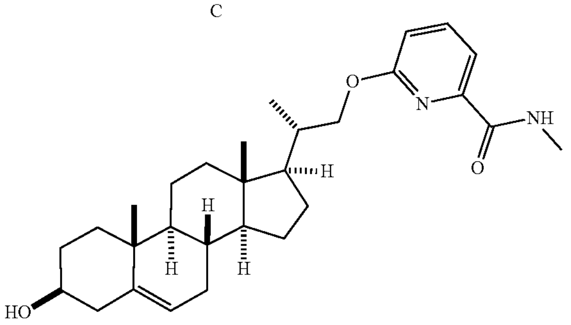

256

To a solution of compound A (400 mg, 0.85 mmol) and compound B (31.9 mg, 1.03 mmol, HCl salt) in DMF (7 mL, 90.4 mmol) was added HATU (650 mg, 1.71 mmol) and DIEA (663 mg, 5.13 mmol). The reaction mixture was stirred at room temperature under $N_2$ for 16 h. The reaction was quenched with saturated $NH_4Cl$ and extracted with EtOAc. The organic layer was washed with brine, dried over sodium sulfate, filtered, and concentrated. The mixture was purified by column chromatography on silica gel to afford compound C (120 mg) as a white solid.

To a solution of compound C (120 mg, 0.25 mmol) in water (0.3 mL) and 1,4-dioxane (2.1 mL) was added 4-methylbenzene-1-sulfonic acid (8.6 mg, 0.5 mmol). The reaction mixture was stirred at 80° C. under $N_2$ for 2 hours. The reaction was quenched with saturated $NaHCO_3$ and extracted with EtOAc. The organic layer was washed by brine, dried over sodium sulfate, filtered, and concentrated. The mixture was purified by column chromatography on silica gel to afford compound 256 (44.6 mg). $^1$H NMR (400 MHz, Chloroform-d) δ 7.80-7.72 (m, 2H), 7.69 (t, J=7.7 Hz, 1H), 6.87 (d, J=8.2 Hz, 1H), 5.36 (d, J=5.0 Hz, 1H), 4.29 (dd, J=10.2, 3.3 Hz, 1H), 4.01 (dd, J=10.2, 7.2 Hz, 1H), 3.62-3.50 (m, 1H), 3.03 (d, J=5.0 Hz, 3H), 2.34-2.21 (m, 2H), 2.08-1.96 (m, 2H), 1.93-1.82 (m, 4H), 1.69-1.61 (m, 2H), 1.54-1.46 (m, 4H), 1.45-1.41 (m, 2H), 1.39-1.34 (m, 1H), 1.31-1.27 (m, 2H), 1.24-1.16 (m, 1H), 1.13 (d, J=6.6 Hz, 3H), 1.08 (dd, J=10.5, 3.6 Hz, 1H), 1.02 (s, 3H), 0.96 (td, J=11.3, 5.4 Hz, 1H), 0.75 (s, 3H). LCMS: [M+Na]=489.20.

Example 257: (3S,8S,9S,10R,13S,14S,17R)-17-((S)-1-((3-(hydroxymethyl)pyridin-2-yl)oxy)propan-2-yl)-10,13-dimethyl-2,3,4,7,8,9,10,11,12,13,14,15,16,17-tetradecahydro-1H-cyclopenta[a]phenanthren-3-ol

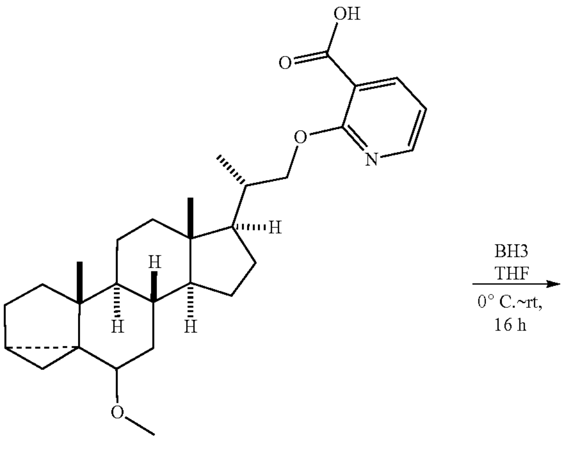

A

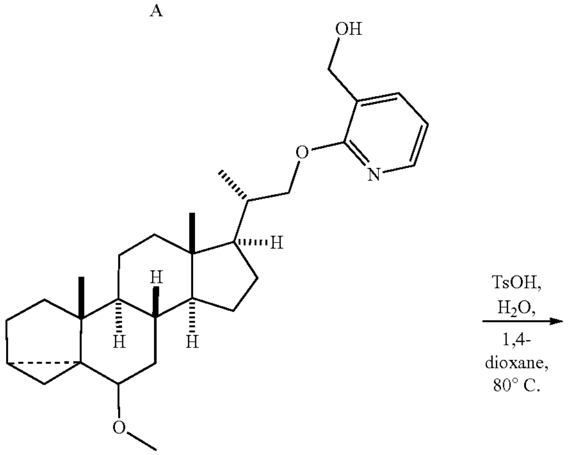

B

-continued

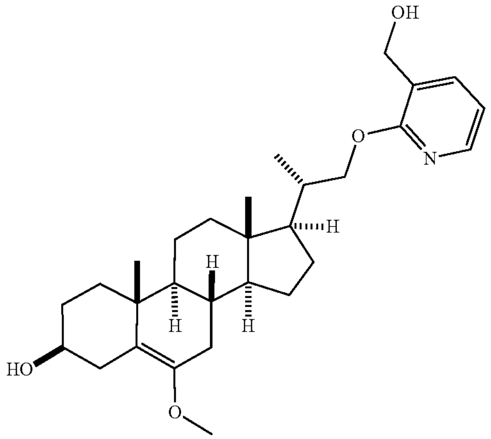

257

To a solution of compound A (50 mg, 107 μmol) in THF (3 mL) was added $BH_3$ (0.32 mL, 1M in THF, 0.32 mmol) at 0° C. under $N_2$. The mixture stirred at room temperature for 16 hours. After quenched with MeOH (5 mL), the mixture was concentrated under vacuum to afford compound B (48 mg,).

To a solution of compound B (50 mg, 110 μmol) in 1,4-dioxane (1.4 mL) and water (0.2 mL) was added 4-methylbenzene-1-sulfonic acid (3.8 mg, 22 μmol). The mixture was stirred at 80° C. for 3 hours. After completion, the mixture was quenched by adding $NaHCO_3$ (20 mL) and extracted with ethyl acetate. The combined organic layer was concentrated to give crude which was purified by silica gel chromatography to give the title compound 257 (15 mg, 31%). $^1$H NMR (400 MHz, Chloroform-d) δ 8.07 (dd, J=5.1, 1.8 Hz, 1H), 7.57 (d, J=7.1 Hz, 1H), 6.86 (dd, J=7.1, 5.0 Hz, 1H), 5.35 (d, J=5.1 Hz, 1H), 4.67 (s, 2H), 4.35 (dd, J=10.3, 3.2 Hz, 1H), 4.10 (dd, J=10.5, 7.0 Hz, 1H), 3.52 (td, J=10.9, 5.5 Hz, 1H), 2.34-2.19 (m, 3H), 2.07-1.80 (m, 7H), 1.55-1.41 (m, 7H), 1.38-1.29 (m, 2H), 1.24-1.20 (m, 1H), 1.13 (d, J=6.7 Hz, 3H), 1.11-1.04 (m, 2H), 1.02 (s, 3H), 0.99-0.93 (m, 1H), 0.74 (s, 3H). LCMS: $[M+1]^+$=440.20.

Example 258: (3S,8S,9S,10R,13S,14S,17R)-17-((S)-1-((4-(hydroxymethyl)pyridin-2-yl)oxy)propan-2-yl)-10,13-dimethyl-2,3,4,7,8,9,10,11,12,13,14,15,16,17-tetradecahydro-1H-cyclopenta[a]phenanthren-3-ol

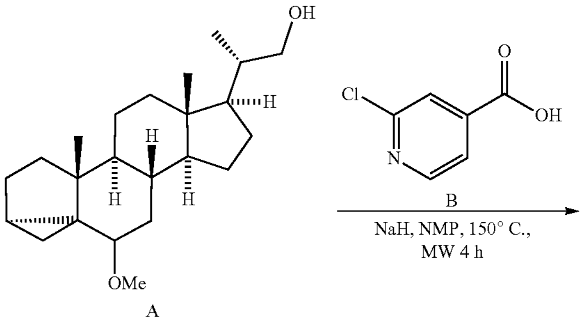

-continued

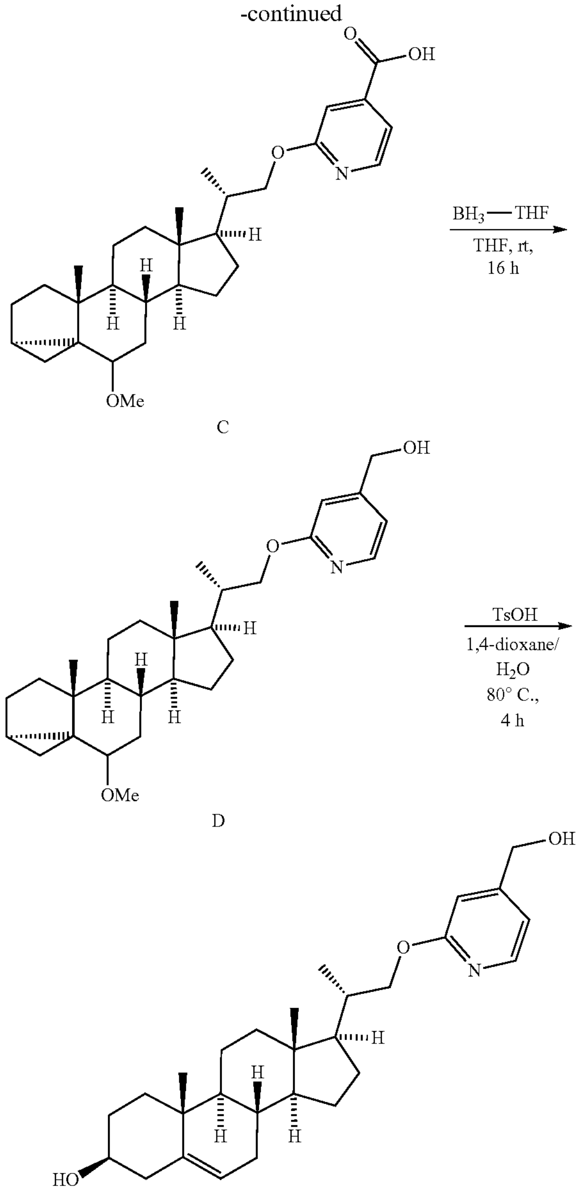

Example 258

To a solution of compound A (600 mg, 1.82 mmol) in NMP (6 mL) was added compound B (286 mg, 1.82 mmol) and NaH (728 mg, 18.2 mmol, 60% dispersion in oil). The mixture was heated at 150° C.; for 4 h under microwave irradiation. The mixture was diluted with water and extracted with ethyl acetate. The organic layer was concentrated to give the crude which was purified by prep-TLC to give compound C (520 mg, 64%).

To a solution of compound C (200 mg, 428 μmol) in THF (6 mL) was added $BH_3$THF (1.3 mL, 1.3 mmol, 1M in THF) at 0° C. After stirring at room temperature for 16 hours under nitrogen, the mixture was quenched with MeOH, and concentrated. The residue was diluted with water and extracted with ethyl acetate. The organic layer was concentrated to give crude which was purified by Prep-TLC to give compound D (120 mg, 62%).

To a solution of compound D (120 mg, 265 μmol) in 1,4-dioxane (1.4 mL) and water (300 μL,) was added 4-methylbenzene-1-sulfonic acid (9.1 mg, 52.9 μmol) and stirred at 80° C. for 4 hours. The mixture was adjusted pH to 7 with $NaHCO_3$ and extracted with DCM. The organic layer was dried over by sodium sulfate and concentrated under vacuum to give crude product which was purified by prep-TLC to give the title compound 258 (26 mg, 22%). LCMS: [M+1]+=440.20. $^1$H NMR (400 MHz, Chloroform-d) δ 8.10 (d, J=5.3 Hz, 1H), 6.82 (dd, J=5.3, 1.3 Hz, 1H), 6.75 (s, 1H), 5.35 (d, J=5.2 Hz, 1H), 4.68 (d, J=5.5 Hz, 2H), 4.25 (dd, J=10.1, 3.3 Hz, 1H), 4.01 (dd, J=10.1, 7.2 Hz, 1H), 3.53 (s, 1H), 2.32-2.22 (m, 2H), 2.07-2.02 (m, 1H), 1.96 (bs, 1H), 1.90-1.86 (m, 2H), 1.84 (s, 1H), 1.75 (t, J=6.0 Hz, 1H), 1.66-1.59 (m, 1H), 1.54-1.22 (m, 10H), 1.12 (d, J=6.6 Hz, 3H), 1.07 (d, J=14.2, 5.0 Hz, 2H), 1.02 (s, 3H), 0.74 (s, 3H).

Example 259: (3S,8S,9S,10R,13S,14S,17R)-17-((S)-1-((5-(hydroxymethyl)pyridin-2-yl)oxy)propan-2-yl)-10,13-dimethyl-2,3,4,7,8,9,10,11,12,13,14,15,16,17-tetradecahydro-1H-cyclopenta[a]phenanthren-3-ol

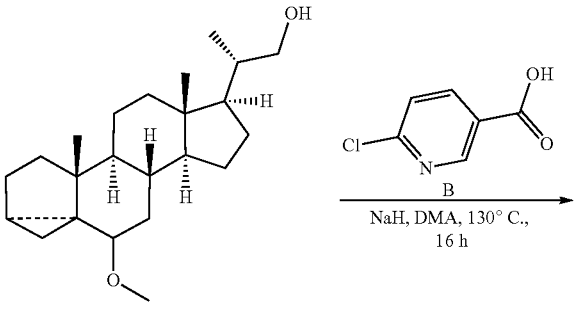

A

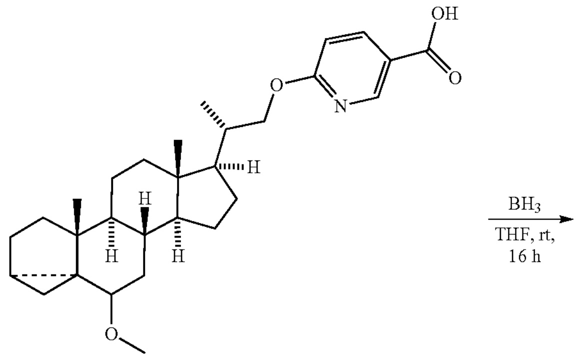

C

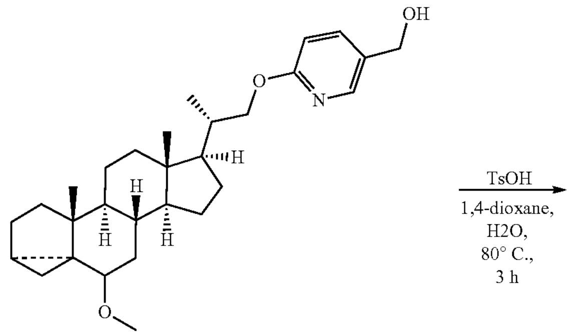

D

-continued

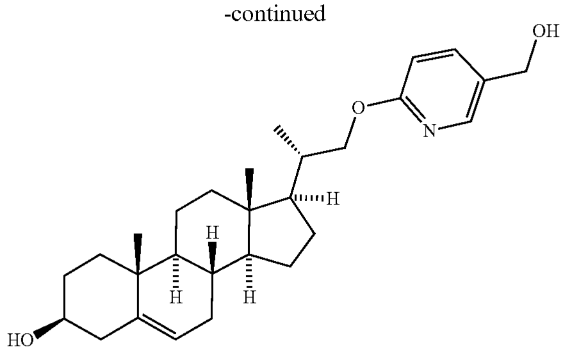

Example 259

To a solution of compound A (500 mg, 1.44 mmol) in DMF (5 mL) was added NaH (288 mg, 7.21 mmol, 60% dispersion in oil) and compound B (455 mg, 2.89 mmol). The mixture was stirred at 130° C. under $N_2$ for 16 h. The mixture was added water, adjusted pH=1-2 by HCl (1M) and extracted with EA. The organic layer was washed with brine, dried over sodium sulfate, and concentrated to afford the crude which was purified by Prep-TLC to afford compound C (380 mg, 56.5%).

To a solution of compound C (140 mg, 299 μmol) in THF (2.8 mL) was added $BH_3$ (0.9 mL, 900 μmol, 1M in THF) at 0° C. The mixture was stirred at room temperature under $N_2$ for 15 h. After completion, the mixture was concentrated to afford the crude which was purified by Prep-TLC to afford compound D (50 mg, 36.8%).

To a solution of compound D (50 mg, 110 μmol) in 1,4-dioxane (0.8 mL) and water (0.2 mL) was added TsOH (4.2 mg, 22 μmol). The mixture was stirred at 80° C.; for 3 h. The mixture was concentrated to afford the crude which was purified by silica gel chromatography to afford the title compound 259 (10.7 mg, 22.1%). LCMS [M+1]=440.20. $^1$HNMR (400 MHz, Chloroform-d) δ 8.12 (d, J=2.3 Hz, 1H), 7.63 (dd, J=8.5, 2.4 Hz, 1H), 6.75 (d, J=8.5 Hz, 1H), 5.35 (d, J=5.1 Hz, 1H), 4.62 (s, 2H), 4.27 (dd, J=10.1, 3.4 Hz, 1H), 4.02 (dd, J=10.1, 7.3 Hz, 1H), 3.59-3.48 (m, 1H), 2.34-2.19 (m, 2H), 2.08-1.80 (m, 7H), 1.67-1.46 (m, 14H), 1.41-1.28 (m, 6H), 1.24-1.15 (m, 2H), 1.12 (d, J=6.5 Hz, 3H), 1.07 (dd, J=12.4, 6.1 Hz, 2H), 1.02 (s, 3H), 0.99-0.87 (m, 2H), 0.74 (s, 3H).

Example 260: (3S,8S,9S,10R,13S,14S,17R)-17-((S)-1-((6-(hydroxymethyl)pyridin-2-yl)oxy)propan-2-yl)-10,13-dimethyl-2,3,4,7,8,9,10,11,12,13,14,15,16,17-tetradecahydro-1H-cyclopenta[a]phenanthren-3-ol

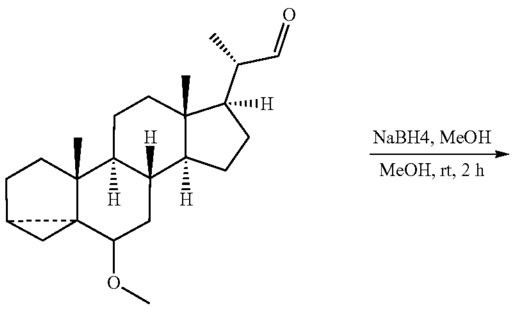

A

-continued

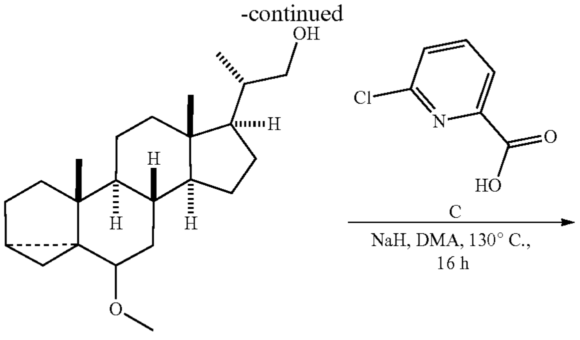

B

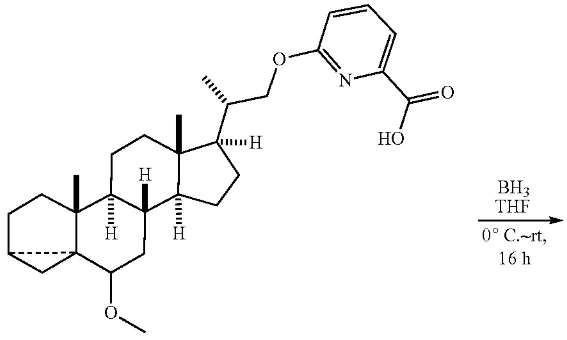

D

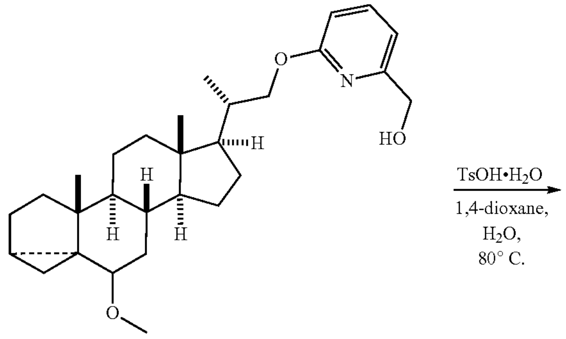

E

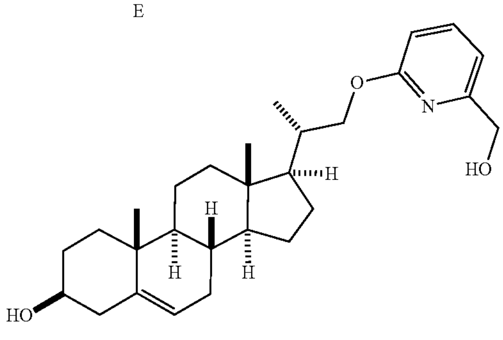

260

To a solution of compound A (3.0 g, 8.71 mmol) in methanol (20 mL) was added $NaBH_4$. The reaction mixture was stirred at room temperature under $N_2$ for 2 h. The reaction was quenched with saturated $NH_4Cl$ and extracted with EtOAc. The organic layer was washed by brine, dried over sodium sulfate, filtered, and concentrated. The residue was purified by column chromatography on silica gel to afford compound B (3.0 g) as a white solid.

To a solution of compound B (1.0 g, 2.89 mmol) and compound C (1.36 g, 8.66 mmol) in DMF (20 mL) was added NaH (576 mg, 14.4 mmol, 60% dispersion in oil). The mixture was stirred at 130° C. under $N_2$ for 16 h. The reaction was quenched with saturated $NH_4Cl$ and extracted with EtOAc. The organic layer was washed by brine, dried over sodium sulfate, filtered, and concentrated. The mixture was purified by column chromatography on silica gel to afford compound D (1.3 g).

To a solution of compound D (200 mg, 0.42 mmol) in tetrahydrofuran (3 mL) at 0° C. was added $BH_3$ (1.28 mL, 1.28 mmol, 1M in THF). The reaction mixture was stirred at room temperature under $N_2$ for 16 h. After quenched with methanol, the solvent was removed under vacuum. The residue was purified by column chromatography on silica gel to afford compound E (80 mg).

To a solution of compound E (60 mg, 0.13 mmol) in water (0.2 mL) and 1,4-dioxane (1.4 mL) was added 4-methylbenzene-1-sulfonic acid (4.55 mg, 0.026 mmol). The reaction mixture was stirred at 80° C. under $N_2$ for 2 hours. The reaction was quenched with saturated $NaHCO_3$ and extracted with EtOAc. The organic layer was washed by brine, dried over sodium sulfate, filtered, and concentrated. The mixture was purified by column chromatography on silica gel to afford the title compound 260 (29.9 mg). $^1H$ NMR (400 MHz, DMSO-$d_6$) δ 7.72-7.64 (m, 1H), 7.03 (d, J=7.3 Hz, 1H), 6.64 (d, J=8.2 Hz, 1H), 5.33 (t, J=5.9 Hz, 1H), 5.28 (d, J=5.0 Hz, 1H), 4.62 (d, J=4.6 Hz, 1H), 4.45 (d, J=5.9 Hz, 2H), 4.22 (dd, J=10.4, 3.3 Hz, 1H), 3.94 (dd, J=10.4, 7.2 Hz, 1H), 3.27 (dt, J=10.8, 5.1 Hz, 2H), 2.21-1.76 (m, 8H), 1.73-1.48 (m, 5H), 1.47-1.29 (m, 7H), 1.24-1.09 (m, 3H), 1.07 (d, J=6.6 Hz, 3H), 1.05-0.99 (m, 2H), 0.97 (s, 3H), 0.94-0.83 (m, 2H), 0.71 (s, 3H). LCMS: [M+H]=440.20.

Example 261: (3S,8S,9S,10R,13S,14S,17R)-10,13-dimethyl-17-((S)-1-((3-methylpyridin-2-yl)oxy) propan-2-yl)-2,3,4,7,8,9,10,11,12,13,14,15,16,17-tetradecahydro-1H-cyclopenta[a]phenanthren-3-ol

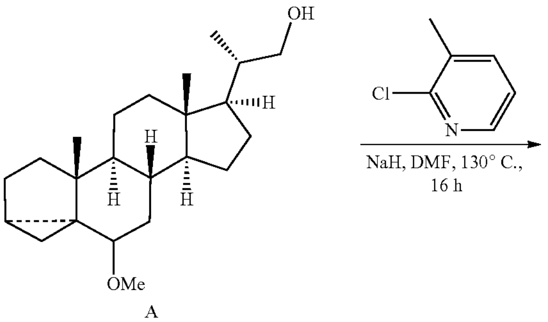

A

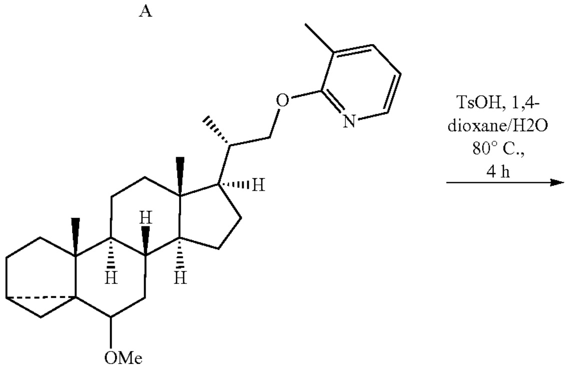

B

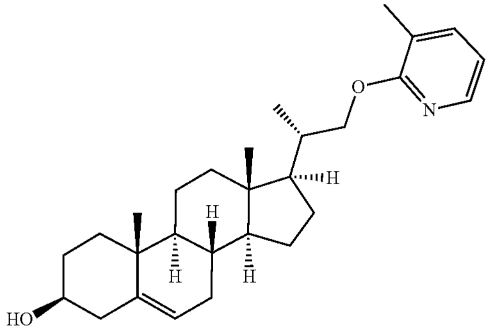

Example 261

A solution of compound A (200 mg, 577 μcool), NaH (111 mg, 2.89 mmol, 60% dispersion in oil) and 2-chloro-3-methylpyridine (147 mg, 1.15 mmol) in dry-DMF (4 mL) was stirred at 130° C. for 16 h under $N_2$ atmosphere. The mixture was added $H_2O$ and extracted with EtOAc. The organic phase was concentrated to give crude which was purified by silica gel chromatography to give compound B (170 mg, 67%).

A solution of compound B (170 mg, 388 μmol) and 4-methylbenzene-1-sulfonic acid (13.4 mg, 77.7 μmol) in 1,4-dioxane (4 mL)/water (1 mL) was stirred at 80° C. for 3 h. The mixture was concentrated to give crude which was purified by silica gel chromatography to give Example 261 (80 mg, 49%). $^1H$ NMR (400 MHz, Chloroform-d) δ 8.02-7.92 (m, 1H), 7.36 (d, J=7.2 Hz, 1H), 6.75 (dd, J=7.2, 5.2 Hz, 1H), 5.36 (d, J=5.2 Hz, 1H), 4.28 (dd, J=10.2, 3.4 Hz, 1H), 4.02 (dd, J=10.2, 7.2 Hz, 1H), 3.58-3.48 (m, 1H), 2.36-2.21 (m, 2H), 2.20 (s, 3H), 2.09-2.03 (m, 1H), 2.01-1.94 (m, 1H), 1.94-1.78 (m, 4H), 1.66-1.58 (m, 2H), 1.52-1.46 (m, 4H), 1.43-1.33 (m, 2H), 1.32-1.16 (m, 3H), 1.14 (d, J=6.6 Hz, 3H), 1.12-1.05 (m, 2H), 1.02 (s, 3H), 1.00-0.93 (m, 1H), 0.75 (s, 3H).

Example 262: (1R,3aS,3bS,7S,9aR,9bS,11aS)-9a,11a-dimethyl-1-[(2S)-1-[(4-methylpyridin-2-yl)oxy]propan-2-yl]-1H,2H,3H,3aH,3bH,4H,6H,7H,8H,9H,9aH,9bH,10H,11H,11aH-cyclopenta[a]phenanthren-7-ol

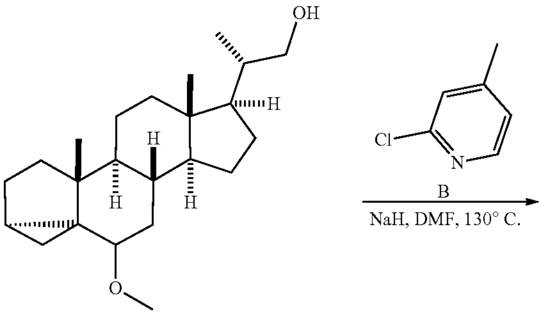

A

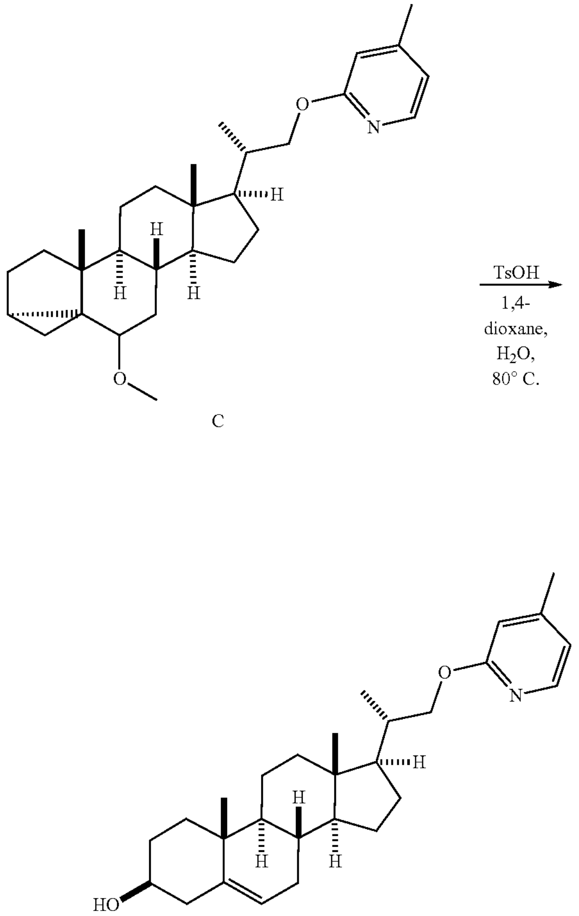

C

262

To a solution of compound A (300 mg, 866 μmol) in DMF (5 mL) was added NaH (138 mg, 3.46 mmol, 60% dispersion in oil) at 0° C. The mixture was stirred at room temperature for 0.5 hour. Then compound B (221 mg, 1.73 mmol) was added, and the mixture was stirred at 130° C.; for 16 hours. The reaction was quenched by $NaHCO_3$ and extracted with ethyl acetate. The organic layer was concentrated, and the residue was purified by silica gel chromatography to give compound C (140 mg, 37%).

To a solution of compound C (140 mg, 320 μmol) in 1,4-dioxane (2 mL) and $H_2O$ (0.4 mL) was added TsOH (11 mg, 64 μmol). The mixture was stirred at 80° C.; for 2 hours. The reaction was quenched by $NaHCO_3$ and extracted with ethyl acetate. The organic layer was concentrated to give the crude which was purified by silica gel chromatography to give the title compound 262 (50 mg). $^1H$ NMR (400 MHz, Chloroform-d) δ 7.99 (d, J=5.2 Hz, 1H), 6.72-6.62 (m, 1H), 6.55 (s, 1H), 5.35 (d, J=5.1 Hz, 1H), 4.22 (dd, J=10.0, 3.3 Hz, 1H), 3.99 (dd, J=10.0, 7.3 Hz, 1H), 3.58-3.47 (m, 1H), 2.39-2.16 (m, 5H), 2.08-1.94 (m, 2H), 1.90-1.79 (m, 4H), 1.56-1.38 (m, 7H), 1.37-1.19 (m, 3H), 1.16-1.06 (m, 5H), 1.02 (s, 3H), 0.98-0.83 (m, 2H), 0.73 (s, 3H). LCMS:M+1=424.3.

Example 263: (3S,8S,9S,10R,13S,14S,17R)-10,13-dimethyl-17-((S)-1-((5-methylpyridin-2-yl)oxy) propan-2-yl)-2,3,4,7,8,9,10,11,12,13,14,15,16,17-tetradecahydro-1H-cyclopenta[a]phenanthren-3-ol

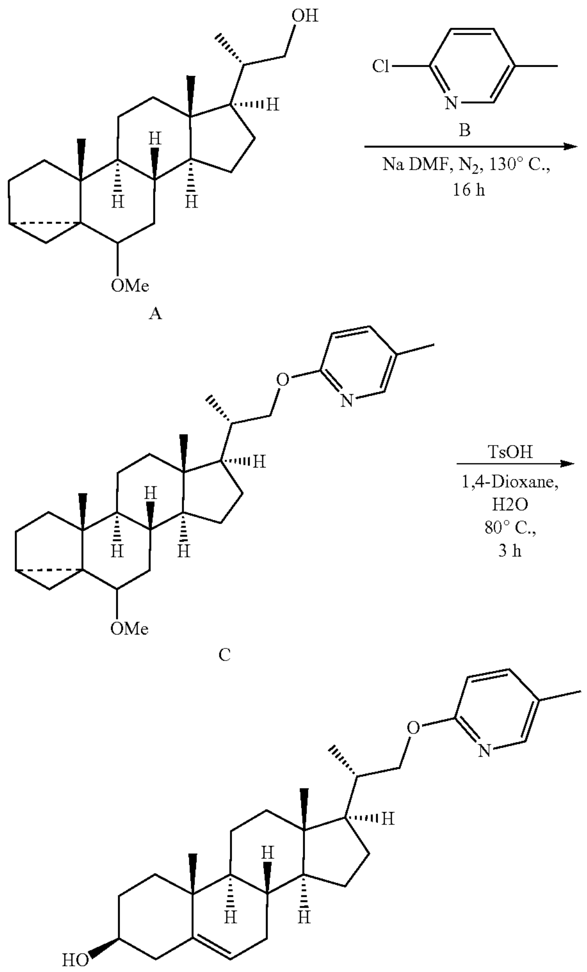

A

C

263

To a solution of compound A (100 mg, 289 μmol) in DMF (2 mL) was added NaH (57.6 mg, 1.44 mmol, 60% dispersion in oil) and compound B (73.6 mg, 577 μmol). The mixture was stirred at 130° C.; under $N_2$ for 16 h. The mixture was added water and extracted with EA. The organic layer was washed with brine, dried over sodium sulfate, and concentrated to afford the crude which was purified by silica gel chromatography to afford compound C (100 mg, 79%).

To a solution of compound C (100 mg, 228 μmol) in 1,4-dioxane (2 mL) and water (0.5 mL) was added TsOH (8.69 mg, 45.7 μmol). The mixture was stirred at 80° C.; for 3 h. The mixture was added water and extracted with EA. The organic layer was washed with brine, dried over sodium sulfate, and concentrated to afford the crude which was purified by silica gel chromatography to afford the title compound 263 (25 mg, 25.8%). LCMS [M+1]=424.20. $^1$HNMR (400 MHz, Chloroform-d) δ 8.18 (bs, 1H), 7.84 (d, J=8.7 Hz, 1H), 7.00 (d, J=8.7 Hz, 1H), 5.38 (d, J=5.1 Hz, 1H), 4.53 (d, J=9.2 Hz, 1H), 4.30 (t, J=8.4 Hz, 1H), 3.61-3.50 (m, 1H), 2.39 (s, 3H), 2.35-2.25 (m, 2H), 2.08-1.85 (m, 7H), 1.71-1.59 (m, 2H), 1.59-1.47 (m, 5H), 1.47-1.36 (m, 3H), 1.34-1.23 (m, 4H), 1.19 (d, J=6.6 Hz, 3H), 1.14 (dd, J=13.2, 4.2 Hz, 2H), 1.10-1.06 (m, 1H), 1.05 (s, 3H), 1.02-0.87 (m, 2H), 0.77 (s, 3H).

Example 264: (1R,3aS,3bS,7S,9aR,9bS,11aS)-9a,11a-dimethyl-1-[(2S)-1-[(6-methylpyridin-2-yl)oxy]propan-2-yl]-1H,2H,3H,3aH,3bH,4H,6H,7H,8H,9H,9aH,9bH,10H,11H,11aH-cyclopenta[a]phenanthren-7-ol

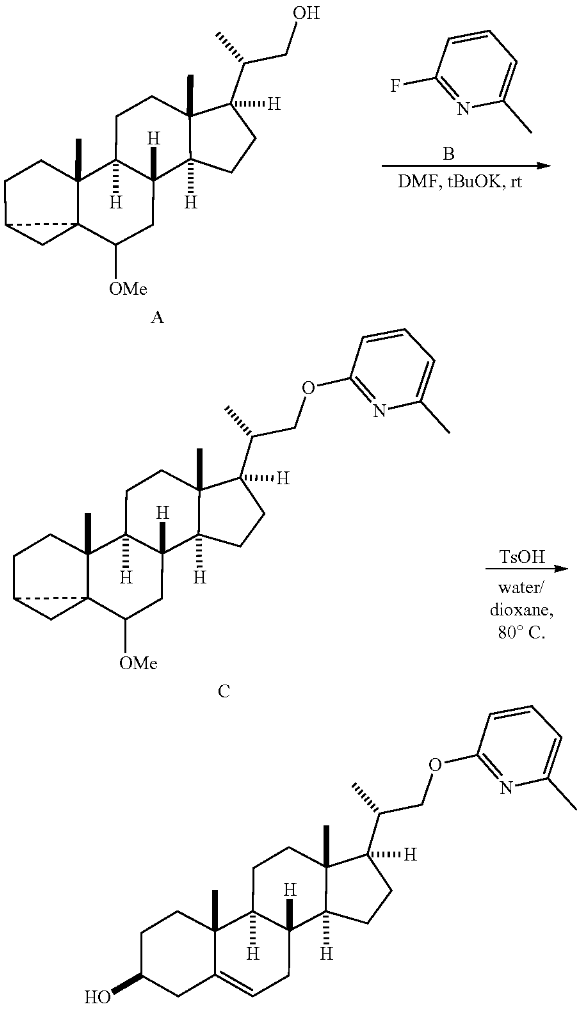

A

C

264

To a solution of compound A (300 mg, 866 μmol) in DMF (4 mL) was added compound B (96.2 mg, 866 μmol) and t-BuOK (389 mg, 3.46 mmol). The reaction was stirred at room temperature for 4 hours. The mixture was diluted with water and extracted with ethyl acetate. The organic layer was concentrated, and the residue was purified by silica gel chromatography to give compound C (150 mg, 41%).

To a solution of compound C (150 mg, 343 μmol) in 1,4-dioxane (4 mL) and water (1 mL) was added 4-methylbenzene-1-sulfonic acid (11.8 mg, 68.5 μmol). The mixture was stirred at 80° C. for 3 hours. After completion, the mixture was quenched by adding $NaHCO_3$ (30 mL) and extracted with ethyl acetate (10 mL×3). The organic layer was washed with brine, dried over sodium sulfate, filtered, and concentrated to give the crude which was purified by column chromatography on silica gel to yield the title compound 264 (34 mg, 23%) as a white solid. LCMS: $[M+1]^+$=424.25. $^1$H NMR (400 MHz, Chloroform-d) δ 7.43 (t, J=7.8 Hz, 1H), 6.68 (d, J=7.2 Hz, 1H), 6.50 (d, J=8.3 Hz, 1H), 5.35 (d, J=4.9 Hz, 1H), 4.24 (d, J=9.4 Hz, 1H), 3.96 (t, J=8.7 Hz, 1H), 3.60-3.46 (m, 1H), 2.43 (s, 3H), 2.34-2.19 (m, 2H), 2.10-1.78 (m, 6H), 1.60-1.39 (m, 10H), 1.38-1.20 (m, 4H), 1.16-1.06 (m, 5H), 1.02 (s, 3H), 0.73 (s, 3H).

Example 265: 3—((S)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethoxy)-N-methylisonicotinamide

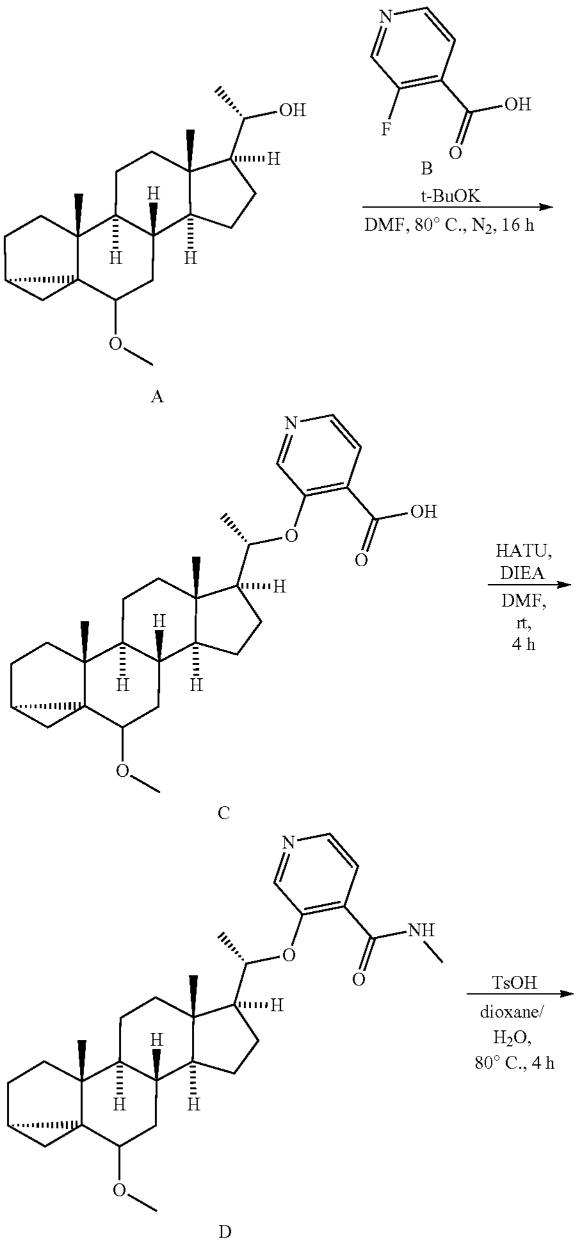

-continued

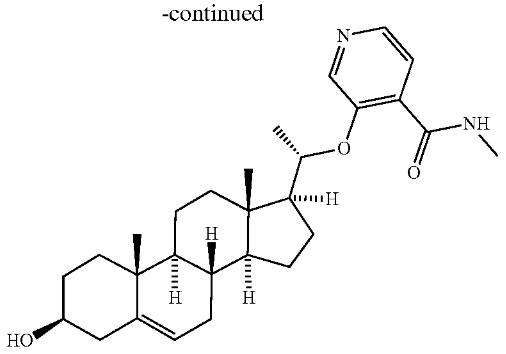

Example 265

To a solution of compound A (500 mg, 1.5 mmol) in DMF (30 mL) was added compound B (318 mg, 2.26 mmol) and tBuOK (506 mg, 4.51 mmol). After stirring 80° C.; for 16 hours under $N_2$, the mixture was extracted with ethyl acetate/water. The organic layer was concentrated to give the crude which was purified by prep-TLC to give compound C (500 mg, 73%).

To a solution of compound C (200 mg, 441 μmol) in DMF (6 mL) was added methylamine (0.90 mL, 900 μmol, 1M in THF), DIEA (284 mg, 2.21 mmol) and HATU (334 mg, 0.88 mmol) and stirred at room temperature for 4 hours. The mixture was extracted with ethyl acetate/water. The organic layer was concentrated to give the crude which was purified by silica gel chromatography to give compound D (100 mg, 50%).

To a solution of compound D (100 mg, 214 μmol) in 1,4-dioxane (0.7 mL) and water (0.1 mL) was added 4-methylbenzene-1-sulfonic acid (7.3 mg, 42.9 μmol). The mixture was stirred at 80° C.; for 4 h. The mixture was adjusted pH to 7 with $NaHCO_3$ and extracted with DCM. The organic layer was dried over anhydrous sodium sulfate and concentrated to give the crude which was purified by silica gel chromatography to give the title compound 265 (26 mg, 26%). LCMS: [M+1]+=453.20. $^1$H NMR (400 MHz, Chloroform-d) δ 8.42 (s, 1H), 8.34 (d, J=4.8 Hz, 1H), 8.01 (d, J=4.8 Hz, 1H), 7.91 (s, 1H), 5.37 (d, J=5.0 Hz, 1H), 4.68-4.55 (m, 1H), 3.54 (s, 1H), 3.02 (d, J=4.8 Hz, 3H), 2.32-2.20 (m, 2H), 2.06-1.92 (m, 4H), 1.89-1.82 (m, 2H), 1.80-1.45 (m, 12H), 1.44 (d, J=6.0 Hz, 3H), 1.33-1.06 (m, 7H), 1.03 (s, 3H), 0.76 (s, 3H).

Example 266: 5—((S)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethoxy)-N-methylnicotinamide

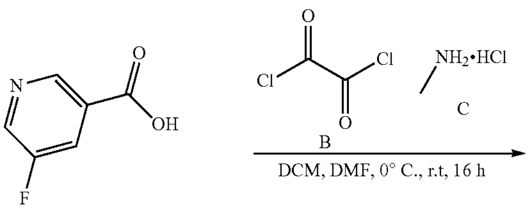

A

-continued

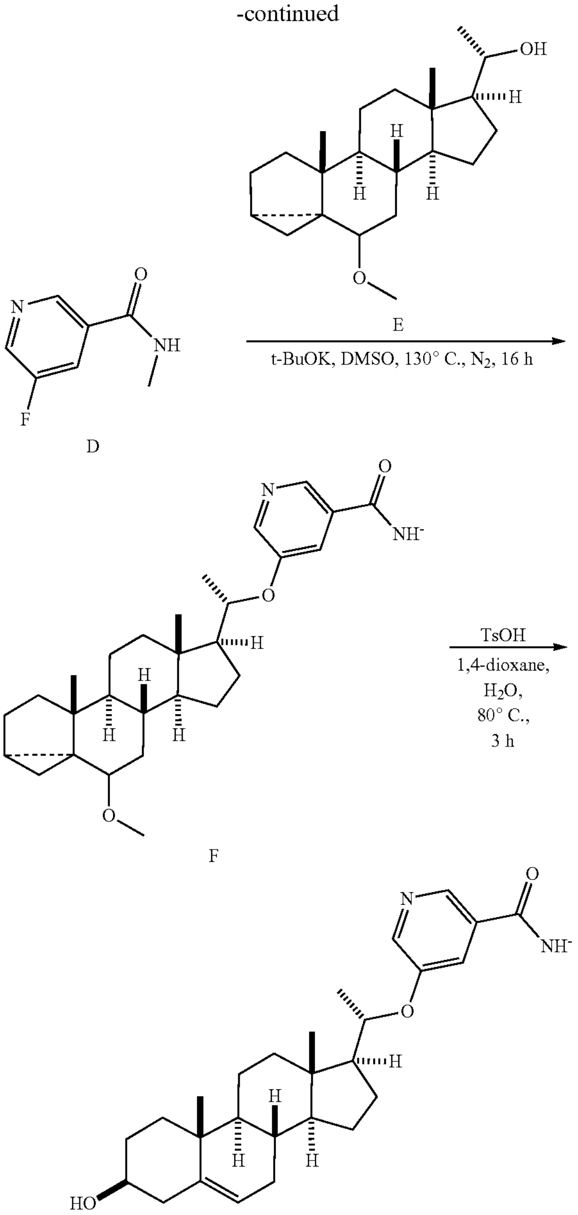

266

To a solution of compound A (1.8 g, 12.8 mmol) in DCM (30 mL) was added compound B (4.05 g, 31.9 mmol) and 1 drop of DMF. The mixture was stirred at 0° C. for 2 hours. Then compound C (1.19 g, 38.3 mmol, HCl salt) was added to the solution. After stirring at room temperature under $N_2$ for 16 h, the reaction was quenched with saturated $NH_4Cl$. extracted with EA. The organic layer was washed with brine, dried over sodium sulfate, filtered, and concentrated. The residue was purified by column chromatography on silica gel to afford the compound D (500 mg) as a white solid.

To a solution of compound D (487 mg, 3.16 mmol) in dimethyl sulfoxide (10.4 mL) was added compound E (350 mg, 1.05 mmol) and tBuOK (472 mg, 4.21 mmol). The mixture was stirred at 130° C. under $N_2$ for 16 h. The reaction was quenched with saturated $NH_4Cl$. extracted with EA. The organic layer was washed by brine, dried over sodium sulfate, filtered, and concentrated. The residue was purified by column chromatography on silica gel to afford compound F (280 mg) as a white solid.

To a solution of compound F (280 mg, 0.6 mmol) in 1,4-dioxane (10 mL) and water (1.4 mL) was added 4-methylbenzene-1-sulfonic acid (103 mg, 0.6 mmol). The mixture was stirred at 80° C. under $N_2$ for 3 h. The reaction was quenched with saturated $NH_4Cl$ and extracted with EA. The organic layer was washed by brine, dried over sodium sulfate, filtered, and concentrated. The mixture was purified by column chromatography on silica gel to afford the title compound 266 (38.9 mg) as a white solid. $^1H$ NMR (400 MHz, Chloroform-d) δ 8.39 (d, J=35.2 Hz, 2H), 7.62 (t, J=2.0 Hz, 1H), 6.17 (s, 1H), 5.36 (s, 1H), 4.42-4.33 (m, 1H), 3.58-3.48 (m, 1H), 3.04 (d, J=4.8 Hz, 3H), 2.36-2.19 (m, 2H), 2.05-1.80 (m, 6H), 1.72-1.63 (m, 2H), 1.57-1.40 (m, 6H), 1.33 (d, J=6.0 Hz, 3H), 1.24-1.04 (m, 4H), 1.01 (s, 3H), 0.99-0.81 (m, 2H), 0.72 (s, 3H).

Example 267: 3—((S)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethoxy)-N-methylpicolinamide

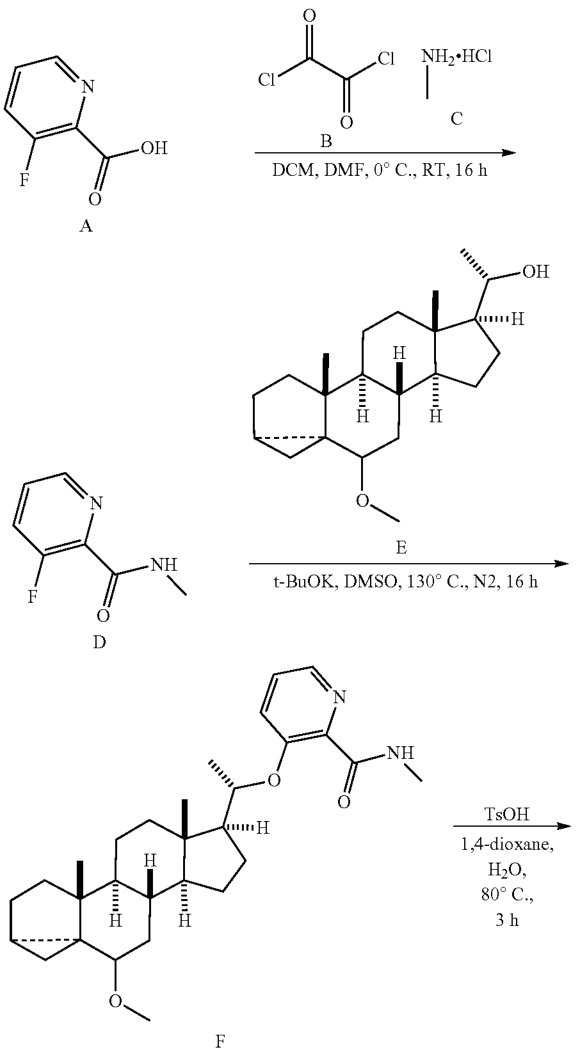

-continued

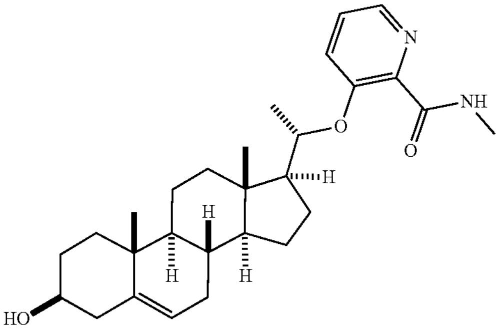

267

To a solution of compound A (1.8 g, 12.8 mmol) in DCM (10 mL) at 0° C. under $N_2$ was added compound B (1.35 g, 10.6 mmol) and 1 drop of DMF. After stirring at room temperature for 2 h, compound C (396 mg, 12.8 mmol, HCl salt) was added to the solution. The mixture was stirred at room temperature under $N_2$ for 16 h. The reaction was diluted with water, extracted with EA. The organic layer was washed by brine, dried over sodium sulfate, filtered, and concentrated. The residue was purified by column chromatography on silica gel to afford compound D (500 mg) as a white solid.

To a solution of compound D (487 mg, 3.16 mmol) in dimethyl sulfoxide (10 mL) was added compound E (350 mg, 1.05 mmol) and tBuOK (591 mg, 5.26 mmol). The mixture was stirred at 130° C. under $N_2$ for 16 h. The reaction was diluted with water, and extracted with EA. The organic layer was washed by brine, dried over sodium sulfate, filtered, and concentrated. The mixture was purified by column chromatography on silica gel to afford compound F (350 mg) as a brown solid.

To a solution of compound F (150 mg, 0.3 mmol) in 1,4-dioxane (4.2 mL) and water (0.6 mL) was added 4-methylbenzene-1-sulfonic acid (27.7 mg, 161 μmol). The mixture was stirred at 80° C. under $N_2$ for 3 h. The reaction was quenched with $NH_4Cl$ solution, and extracted with EA. The organic layer was washed with brine, dried over sodium sulfate, filtered, and concentrated. The mixture was purified by column chromatography on silica gel to afford the title compound 267 (80 mg) as a white solid. $^1H$ NMR (400 MHz, Chloroform-d) δ 8.24 (d, J=3.2 Hz, 1H), 7.67 (s, 1H), 7.42-7.33 (m, 2H), 5.36 (d, J=5.2 Hz, 1H), 4.45-4.35 (m, 1H), 3.59-3.47 (m, 1H), 3.01 (d, J=5.2 Hz, 3H), 2.34-2.19 (m, 2H), 2.15-1.82 (m, 7H), 1.74-1.40 (m, 8H), 1.38 (d, J=6.0 Hz, 3H), 1.31-1.06 (m, 6H), 1.01 (s, 3H), 0.73 (s, 3H).

Example 268: (3S,8S,9S,10R,13S,14S,17S)-17-((S)-1-((4-(hydroxymethyl)pyridin-3-yl) oxy)ethyl)-10,13-dim ethyl-2, 3,4, 7,8,9,10,11,12,13,14,15,16,17-tetradecahydro-1H-cyclopenta[a]phenanthren-3-ol

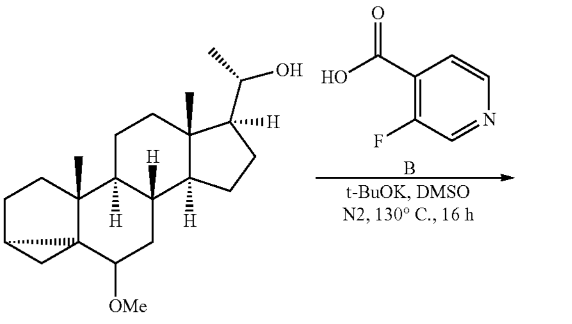

A

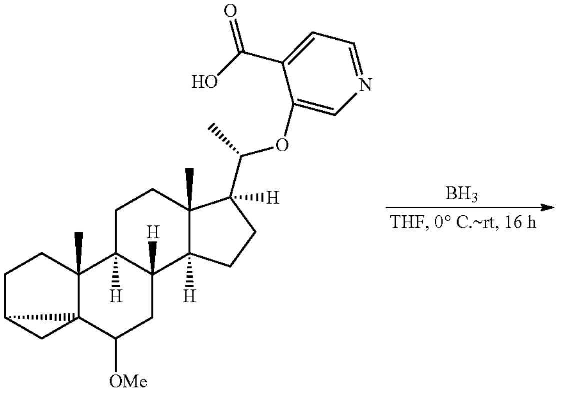

C

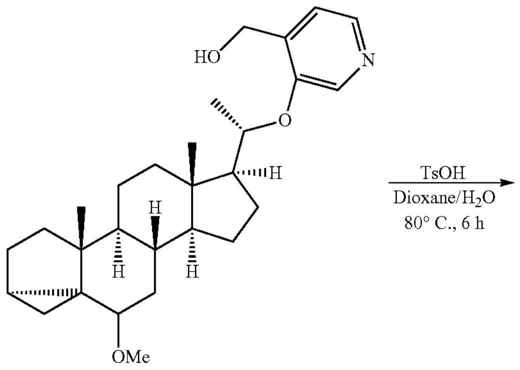

D

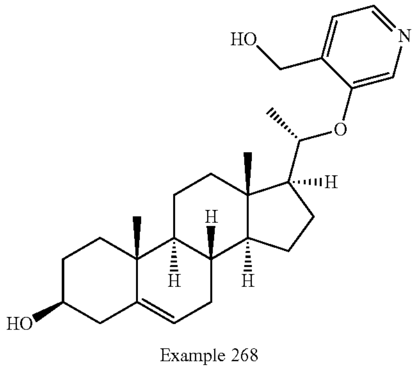

Example 268

To a solution of compound A (600 mg, 1.8 mmol) in DMSO (30 mL) was added compound B (382 mg, 2.71 mmol) and tBuOK (607 mg, 5.41 mmol). After stirring 130° C.; for 16 hours under nitrogen, the mixture was diluted with water and extracted with ethyl acetate. The organic layer was concentrated to give crude which was purified by prep-TLC to give compound C (800 mg, 97%).

To a solution of compound C (200 mg, 428 μmol) in THF (6 mL) was added $BH_3THF$ (1.3 mL, 1.3 mmol, 1M in THF) at 0° C. The mixture was stirred at room temperature for 16 hours under nitrogen then quenched with MeOH and concentrated. The mixture was extracted with ethyl acetate and water. The organic layer was concentrated to give the crude which was purified by Prep-TLC to give compound D (90 mg, 50%).

To a solution of compound D (90 mg, 205 μmol) in 1,4-dioxane (0.7 mL) and water (0.1 mL) was added 4-methylbenzene-1-sulfonic acid (10.6 mg, 61.4 μmol). The mixture was stirred at 80° C.; for 6 hours. The mixture was adjusted pH to 7 by $NaHCO_3$ and extracted with DCM. The organic layer was dried over by sodium sulfate and concentrated under vacuum to give the crude which was purified by prep-TLC to give the title compound 268 (70 mg, 80%)..LCMS: $[M+1]^+$=426.20. $^1H$ NMR (400 MHz, Chloroform-d) δ 8.16 (d, J=4.0 Hz, 2H), 7.39 (d, J=4.8 Hz, 1H), 5.34 (s, 1H), 4.70 (s, 2H), 4.47-4.39 (m, 1H), 3.57-3.35 (m, 2H), 2.33-2.20 (m, 2H), 2.03-1.41 (m, 13H), 1.34 (d, J=6.0 Hz, 3H), 1.26-1.02 (m, 5H), 1.00 (s, 3H), 0.96 (d, J=4.6 Hz, 1H), 0.70 (s, 3H).

Example 269: (3S,8S,9S,10R,13S,14S,17S)-17-((S)-1-((5-(hydroxymethyl)pyridin-3-yl) oxy)ethyl)-10, 13-dim ethyl-2, 3,4, 7,8,9,10,11,12,13,14,15,16,17-tetradecahydro-1H-cyclopenta[a]phenanthren-3-ol

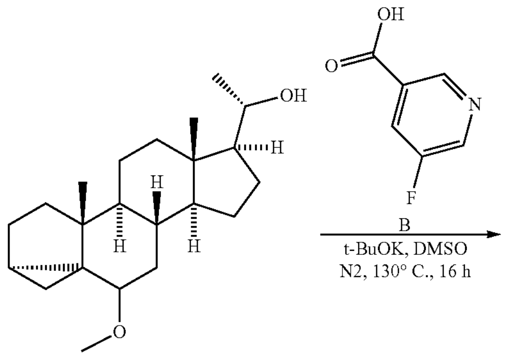

A

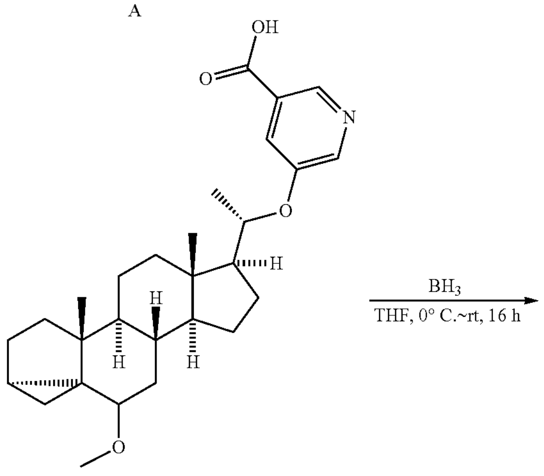

C

-continued

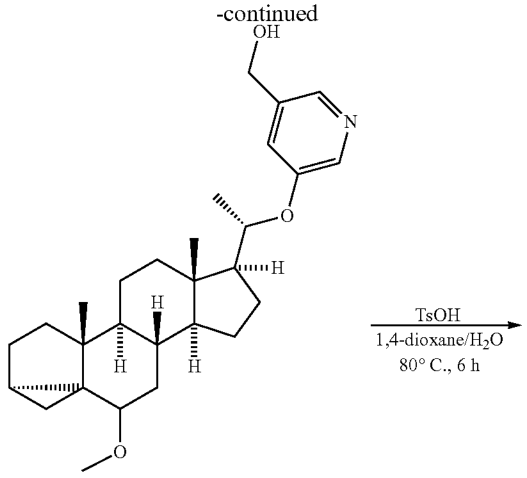

D

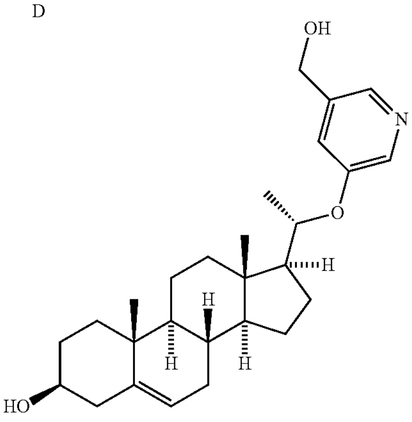

Example 269

To a solution of compound A (200 mg, 601 μmol) in DMSO (8 mL) was added compound B (127 mg, 902 μmol) and tBuOK (202 mg, 1.8 mmol). After stirring 130° C.; for 16 hours under nitrogen, the mixture was diluted with water and extracted with ethyl acetate. The organic layer was concentrated to give the crude which was purified by prep-TLC to give compound C (150 mg, 56%).

To a solution of compound C (150 mg, 331 μmol) in THF (6 mL) was added $BH_3THF$ (1 mL, 1 mmol, 1M in THF) at 0° C. After stirring at room temperature for 16 hours under nitrogen, the mixture was quenched with MeOH, and concentrated. The residue was diluted with water and extracted with ethyl acetate. The organic layer was concentrated to give the crude which was purified by Prep-TLC to give compound D (110 mg, 76%).

To a solution of compound D (110 mg, 250 μmol) in 1,4-dioxane (2.1 mL) and water (0.3 mL) was added 4-methylbenzene-1-sulfonic acid (8.62 mg, 50 μmol). The mixture was stirred at 80° C.; for 6 hours. The mixture was adjusted pH to 7 by $NaHCO_3$ and extracted with DCM. The organic layer was dried over by sodium sulfate and concentrated under vacuum to give the crude which was purified by prep-TLC to give the title compound 269 (25 mg, 23%). LCMS: [M+1]+=426.20. $^1H$ NMR (400 MHz, Chloroform-d) δ 8.31 (s, 1H), 8.14 (s, 1H), 7.49 (s, 1H), 5.36 (d, J=5.1 Hz, 1H), 4.81 (s, 2H), 4.36 (t, J=6.9 Hz, 1H), 3.59-3.46 (m, 1H), 2.33-2.19 (m, 3H), 2.05-1.83 (m, 6H), 1.70-1.44 (m, 8H), 1.35 (d, J=6.0 Hz, 3H), 1.29-1.04 (m, 7H), (s, 3H), 0.72 (s, 3H).

Example 270: (3S,8S,9S,10R,13S,14S,17S)-17-((S)-1-((2-(hydroxymethyl)pyridin-3-yl) oxy)ethyl)-10, 13-dim ethyl-2, 3,4, 7,8,9,10,11,12,13,14,15,16,17-tetradecahydro-1H-cyclopenta[a]phenanthren-3-ol

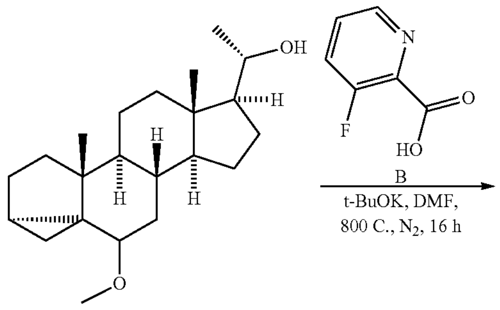

A

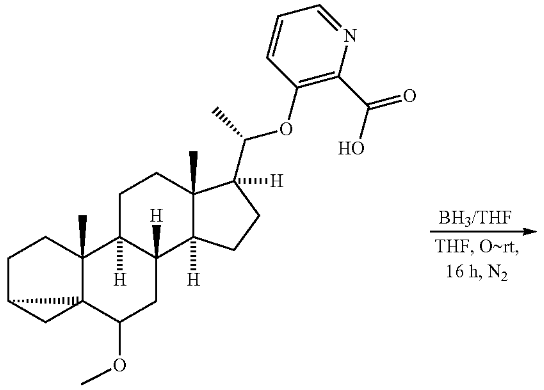

C

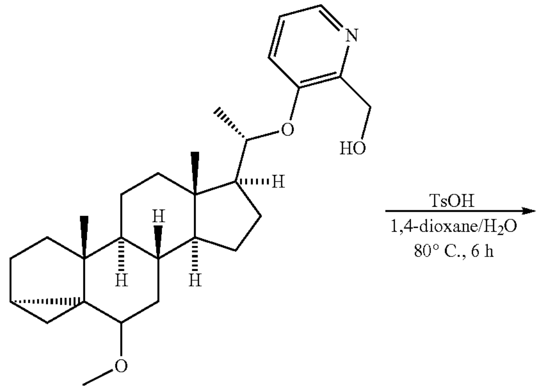

D

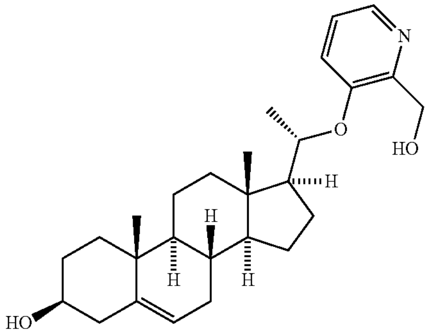

Example 270

To a solution of compound A (200 mg, 601 μmol) in DMF (8 mL) was added compound B (127 mg, 902 μmol) and t-BuOK (202 mg, 1.8 mmol). After stirring at 130° C.; for 16 hours, the mixture was diluted with water and extracted with ethyl acetate. The combined organic layer was concentrated to give crude which was purified by prep-TLC to give compound C (150 mg, 56%).

To a solution of compound C (150 mg, 331 μmol) in THF (6 mL) was added $BH_3$ (1 mL, 1 mmol, 1M in THF) at 0° C. After stirring at room temperature for 16 hours, the mixture was quenched with MeOH and concentrated to give the crude which was purified by prep-TLC to give compound D (110 mg, 76%).

To a solution of compound D (110 mg, 250 μmol) in 1,4-dioxane (2.1 mL) and water (0.3 mL) was added 4-methylbenzene-1-sulfonic acid (8.62 mg, 50 μmol). After stirring at 80° C. for 6 hours, the mixture was adjusted pH to 7 by $NaHCO_3$ and extracted with DCM. The organic layer was concentrated to give crude which was purified by silica gel chromatography to give the title compound 270 (25 mg, 23%). $^1$H NMR (400 MHz, Chloroform-d) δ 8.10 (dd, J=4.7, 1.3 Hz, 1H), 7.16 (dd, J=8.3,4.7 Hz, 1H), 7.10 (d, J=8.1 Hz, 1H), 5.36 (d, J=5.1 Hz, 1H), 4.70 (d, J=4.5 Hz, 2H), 4.32 (t, J=6.8 Hz, 2H), 3.58-3.49 (m, 1H), 2.34-2.21 (m, 2H), 2.07-1.83 (m, 5H), 1.74-1.66 (m, 2H), 1.53-1.41 (m, 4H), 1.31 (d, J=6.0 Hz, 3H), 1.28-1.04 (m, 6H), 1.01 (s, 3H), 0.97 (dd, J=11.4, 4.8 Hz, 1H), 0.71 (s, 3H). .LCMS: M+1=426.20.

Example 271: (3S,8S,9S,10R,13S,14S,17S)-10,13-dimethyl-17-((S)-1-((4-methylpyridin-3-yl)oxy) ethyl)-2,3,4,7,8,9,10,11,12,13,14,15,16,17-tetradeca-hydro-1H-cyclopenta[a]phenanthren-3-ol

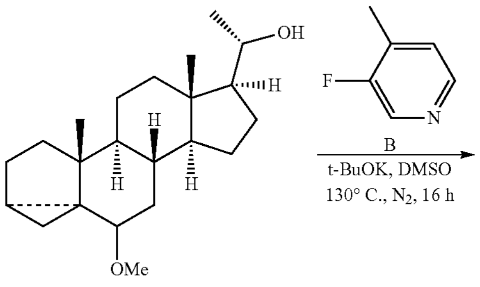

A

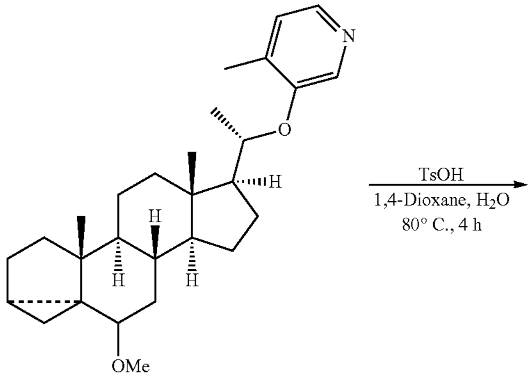

C

-continued

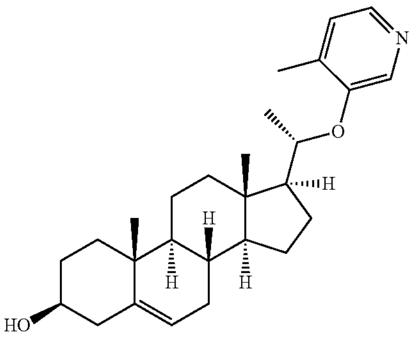

271

To a solution of compound A (300 mg, 902 μmol) in DMSO (5 mL) was added compound B (200 mg, 1.8 mmol) and t-BuOK (506 mg, 4.51 mmol). The mixture was stirred at 130° C. under $N_2$ for 16 h. The mixture was added water and extracted with EA. The organic layer was washed with brine, dried over sodium sulfate, and concentrated to afford the crude which was purified by silica gel chromatography to afford compound C (130 mg, 34%).

To a solution of compound C (130 mg, 307 μmol) in 1,4-dioxane (1.6 mL) and water (0.4 mL) was added TsOH (42.3 mg, 245 μmol). The mixture was stirred at 80° C. for 4 h. The mixture was added $NaHCO_3$ to adjust pH=7 and extracted with EA. The organic layer was dried over sodium sulfate and concentrated to afford the crude was purified by silica gel chromatography to afford the title compound 271 (39.3 mg, 31.3%). LCMS [M+1]=410.15. $^1$HNMR (400 MHz, Chloroform-d) δ 8.15 (s, 1H), 8.06 (d, J=4.7 Hz, 1H), 7.06 (d, J=4.6 Hz, 1H), 5.36 (dd, J=4.8, 2.5 Hz, 1H), 4.43-4.36 (m, 1H), 3.58-3.46 (m, 1H), 2.33-2.21 (m, 2H), 2.20 (s, 3H), 2.06-1.79 (m, 7H), 1.73-1.63 (m, 3H), 1.62-1.44 (m, 6H), 1.34 (d, J=6.0 Hz, 3H), 1.32-1.05 (m, 6H), 1.02 (s, 3H), 0.97 (dt, J=11.9, 5.7 Hz, 1H), 0.72 (s, 3H).

Example 272: (3S,8S,9S,10R,13S,14S,17S)-10,13-dimethyl-17-((S)-1-((5-methylpyridin-3-yl)oxy)ethyl)-2,3,4,7,8,9,10,11,12,13,14,15,16,17-tetradecahydro-1H-cyclopenta[a]phenanthren-3-ol

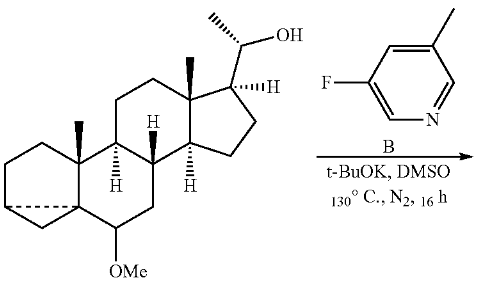

A

-continued

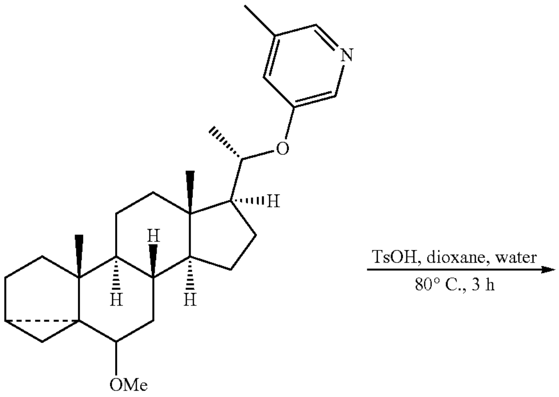

C

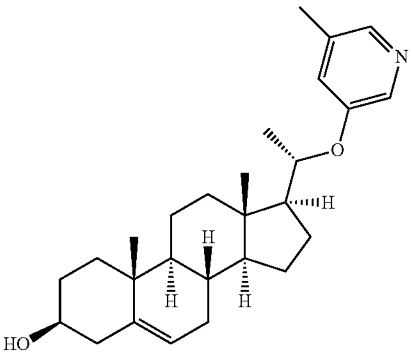

272

To a solution of compound A (200 mg, 601 μmol) in dimethyl sulfoxide (5 mL) was added compound B (200 mg, 902 μmol) and the reaction mixture was stirred at 130° C. under nitrogen for 16 hours. After completion, the mixture was quenched by adding water (10 mL) and extracted with ethyl acetate (10 mL×3). The organic layer was washed with brine, dried over sodium sulfate, filtered, and concentrated to give the crude which was purified by column chromatography on silica gel to yield the title compound C (140 mg, 55%) as a white solid.

To a solution of compound C (140 mg, 330 μmol) in 1,4-dioxane (3.2 mL) and water (0.8 mL) was added 4-methylbenzene-1-sulfonic acid (28.5 mg, 165 μmol). The mixture was stirred at 80° C. for 3 hours. After completion, the mixture was quenched by adding $NaHCO_3$ (5 mL) and extracted with ethyl acetate (5 mL×3). The organic layer was washed with brine, dried over sodium sulfate, filtered, and concentrated to give the crude which was purified by column chromatography on silica gel to yield the title compound 272 (50 mg, 37%) as a white solid. LCMS: [M+H]+=410.15. $^1$H NMR (400 MHz, Chloroform-d) δ 8.06 (d, J=2.6 Hz, 1H), 8.00 (s, 1H), 6.97 (t, J=2.1 Hz, 1H), 5.36 (dd, J=5.0, 2.3 Hz, 1H), 4.28 (dd, J=7.4, 5.8 Hz, 1H), 3.59-3.46 (m, 1H), 2.34-2.19 (m, 5H), 2.06-1.75 (m, 6H), 1.70-1.61 (m, 3H), 1.59-1.51 (m, 3H), 1.47 (dt, J=11.0, 4.5 Hz, 2H), 1.31 (d, J=6.0 Hz, 3H), 1.26-1.04 (m, 5H), 1.01 (s, 3H), 0.96 (dd, J=11.5, 4.9 Hz, 1H), 0.72 (s, 3H).

Example 273: (1S,3aS,3bS,7S,9aR,9bS,11aS)-9a, 11a-dimethyl-1-[(1S)-1-[(6-methylpyridin-3-yl)oxy] ethyl]-1H,2H,3H,3aH,3bH,4H,6H,7H,8H,9H,9aH, 9bH,10H,11H,11aH-cyclopenta[a]phenanthren-7-ol

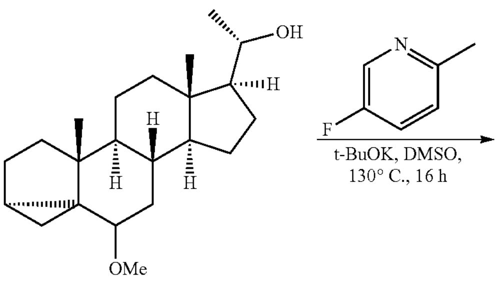

A

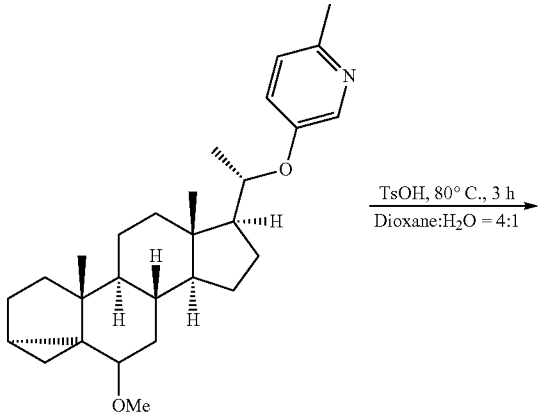

B

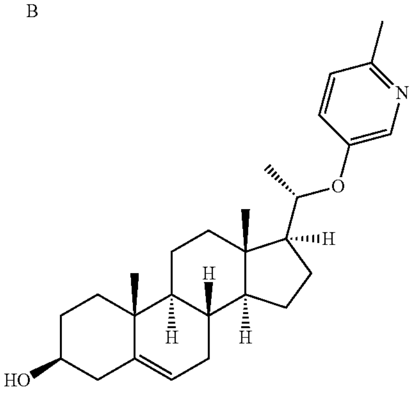

273

To a solution of compound A (150 mg, 451 μmol) in dimethyl sulfoxide (3.75 mL) was added 5-fluoro-2-methylpyridine (75.2 mg, 677 μmol) and tBuOK (253 mg, 2.26 mmol) at room temperature. The mixture was heated at 130° C. for 16 h under nitrogen. The mixture was diluted with water and extracted with ethyl acetate. The organic layer was washed with water and brine, dried with sodium sulfate and concentrated under vacuum to give crude product which was purified by silica gel chromatography (eluting with 1/20 ethyl acetate/PE) to give compound B (90 mg, 47.1%).

A mixture of compound B (70 mg, 165 μmol) and 4-methylbenzene-1-sulfonic acid hydrate (25.1 mg, 132 μmol) in 1,4-dioxane (2 mL) and water (0.5 mL) was heated at 80° C. for 3 h under an atmosphere of nitrogen. The pH of the resulting mixture was adjusted to 7 with saturated $NaHCO_3$ solution and extracted with ethyl acetate. The organic layer was dried over anhydrous sodium sulfate and concentrated under vacuum to give crude product which was purified by silica gel chromatography (eluting with 1/5 ethyl acetate/PE) to give the title compound 273 (39.1 mg, 57.8%). $^1H$ NMR (400 MHz, $CDCl_3$) δ 8.14 (d, J=2.8 Hz, 1H), 7.15-7.00 (m, 2H), 5.36 (d, J=5.0 Hz, 1H), 4.29-4.19 (m, 1H), 3.58-3.46 (m, 1H), 2.49 (s, 3H), 2.33-2.21 (m, 2H), 2.04-1.61 (m, 12H), 1.50-1.43 (m, 2H), 1.30 (d, J=6.0 Hz, 3H), 1.27-1.08 (m, 5H), 1.01 (s, 3H), 0.71 (s, 3H). LCMS: $[M+H]^+$=410.20.

Example 274: (1S,3aS,3bS,7S,9aR,9bS,11aS)-9a, 11a-dimethyl-1-[(1S)-1-[(2-methylpyridin-3-yl)oxy] ethyl]-1H,2H,3H,3aH,3bH,4H,6H,7H,8H,9H,9aH, 9bH,10H,11H,11aH-cyclopenta[a]phenanthren-7-ol

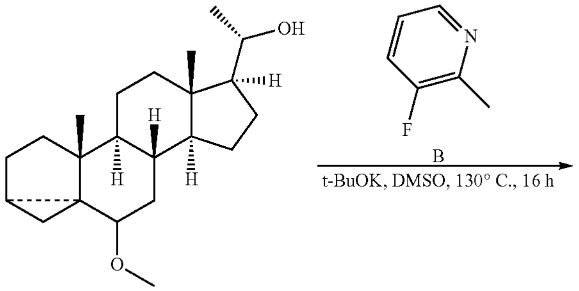

A

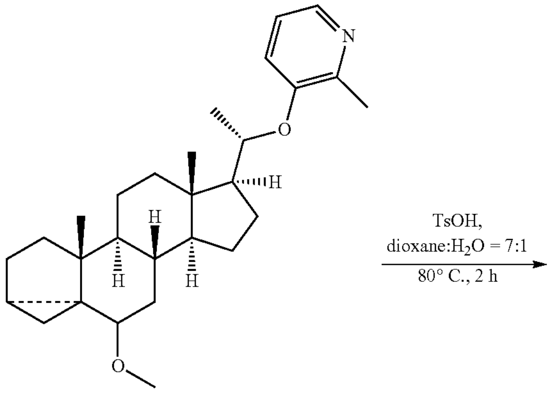

C

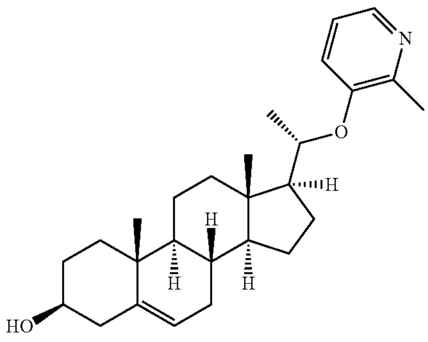

274

To a solution of compound A (200 mg, 601 µmol) in dimethyl sulfide (3 mL) was added compound B (100 mg, 902 µmol) and tBuOK (202 mg, 3 eq., 1.8 mmol). The mixture was stirred at 130° C. for 16 hours. The reaction was diluted with water and extracted with ethyl acetate (10 mL×4). The combined organic layer was concentrated to give the crude compound C (200 mg, 78%).

To a solution of compound C (100 mg, 236 µmol) in dioxane (3.5 mL) and water (0.5 mL) was added 4-methylbenzene-1-sulfonic acid (24.4 mg, 142 µmol). Then the reaction was stirred for 2 hours at 80° C. The reaction was quenched with water and extracted with ethyl acetate (10 mL×4). The combined organic layer was concentrated to give the crude which was purified by silica gel chromatography to yield the title compound 274 (14.6 mg, 15%). LCMS:$[M+1]^+$=410.20. $^1H$ NMR (400 MHz, Chloroform-d) δ 8.07-7.96 (m, 1H), 7.07 (d, J=3.2 Hz, 2H), 5.42-5.32 (m, 1H), 4.35-4.21 (m, 1H), 3.59-3.46 (m, 1H), 2.45 (s, 3H), 2.35-2.18 (m, 2H), 2.10-1.79 (m, 7H), 1.76-1.37 (m, 9H), 1.30 (d, J=6.2 Hz, 3H), 1.28-1.04 (m, 6H), 1.01 (s, 3H), 0.98 (s, 1H), 0.71 (s, 3H).

Example 275: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(2R)-4-acetyl-2-methylpiperazin-1-yl]pentan-1-one

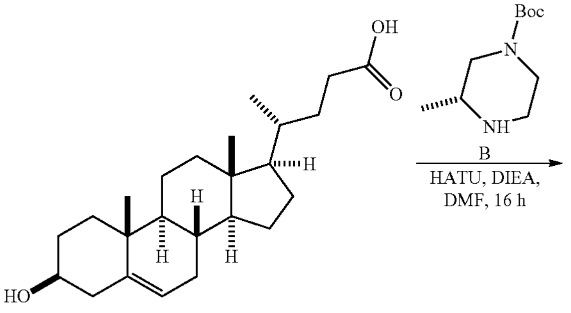

A

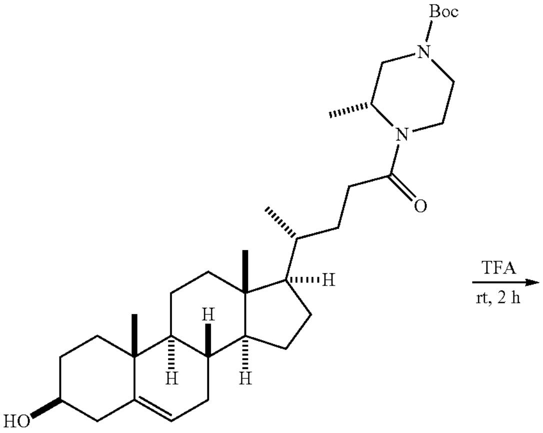

C

-continued

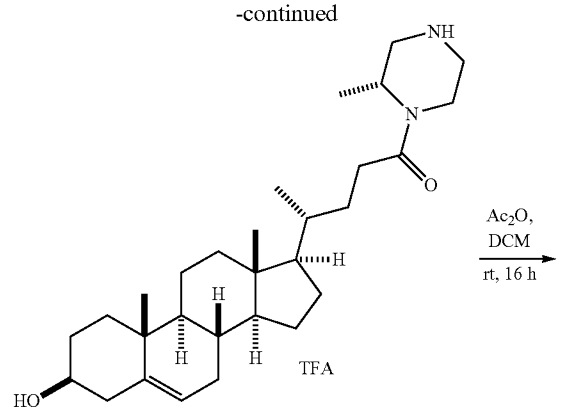

D

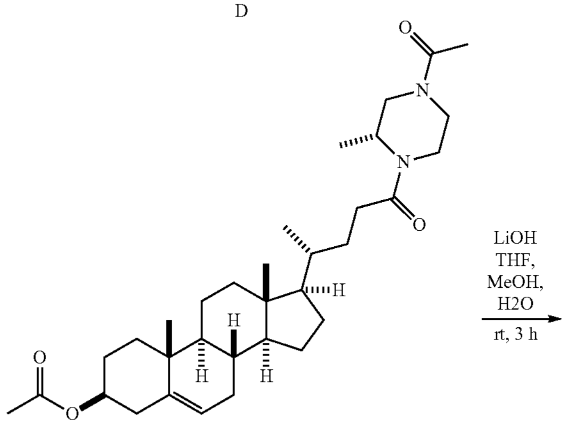

E

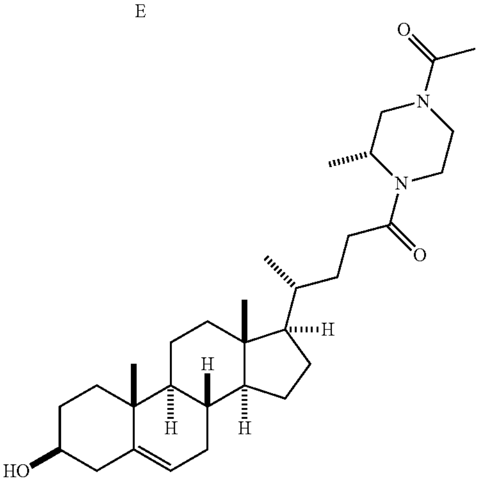

275

To a solution of compound A (300 mg, 801 µmol) in DMF (5 mL) was added compound B (192 mg, 961 µmol), HATU (457 mg, 1.2 mmol) and DIEA (414 mg, 3.2 mmol). The mixture was stirred at room temperature for 16 hours. The mixture was quenched by $NH_4Cl$ and extracted with ethyl acetate. The organic layer was concentrated, and the residue was purified by silica gel chromatography to give compound C (350 mg). To a solution of compound C (350 mg, 629 µmol) in DCM (4 mL) was added TFA (1 mL). After stirring at room temperature for 2 hours, the mixture was concentrated to give compound D (258 mg). To a solution of compound D (118 mg, 213 µmol) in DCM (3 mL) was added acetic anhydride (39.6 mg, 388 µmol). The mixture was stirred at room temperature for 16 hours. The reaction was quenched by $NaHCO_3$ and extracted with ethyl acetate. The organic layer was concentrated, and the residue was purified by silica gel chromatography to give compound E (40 mg).

To a solution of compound E (40 mg, 74 μmol) in mixture of THE (1 mL), MeOH (1 mL) and water (1 mL) was added LiOH (5.31 mg, 222 μmol). The solution was stirred at room temperature for 3 h. The mixture was diluted with water and extracted with ethyl acetate. The organic layer was concentrated, and the residue was purified by silica gel chromatography to give the title compound 275 (21 mg). $^1$H NMR (400 MHz, Chloroform-d) δ 5.35 (d, J=5.0 Hz, 1H), 4.89-4.01 (m, 2H), 3.80-2.63 (m, 5H), 2.45-1.77 (m, 12H), 1.57-1.39 (m, 8H), 1.18-1.04 (m, 7H), 1.02-0.91 (m, 8H), 0.92-0.87 (m, 1H), 0.68 (s, 3H). LCMS:M+1=498.4

Example 276: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(2S)-4-acetyl-2-methylpiperazin-1-yl]pentan-1-one

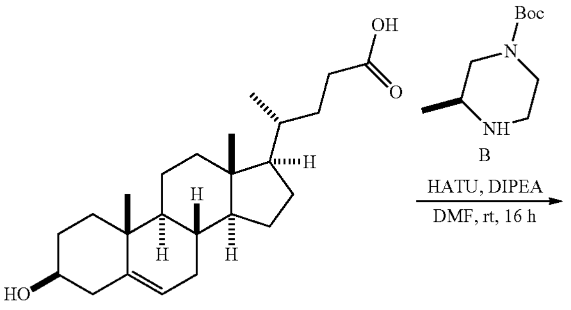

A

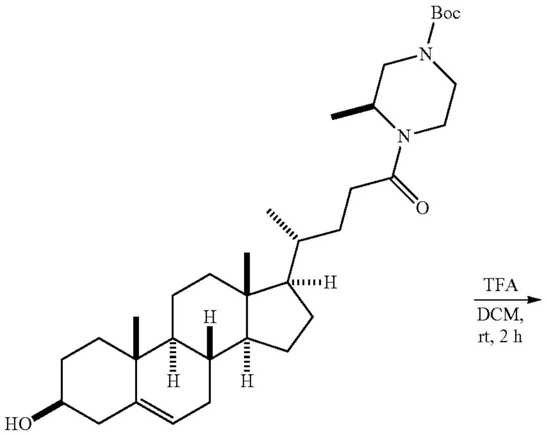

C

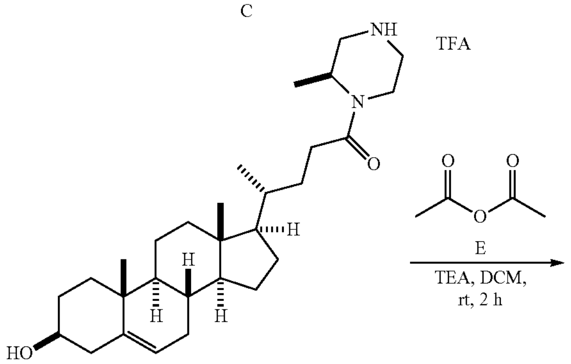

D

-continued

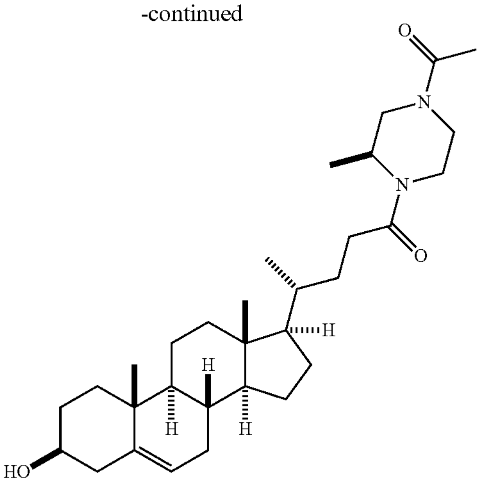
276

To a solution of compound A (500 mg, 1.33 mmol) in DMF (10 mL) was added compound B (334 mg, 1.67 mmol), DIEA (1.27 g, 3.34 mmol) and HATU (1.29 mg, 10 mmol). The mixture was stirred at room temperature for 16 hours. The mixture was diluted with water and extracted with ethyl acetate. The organic layer was concentrated to give the crude which was purified by silica gel chromatography to give compound C (300 mg, 32%). To a solution of compound C (200 mg, 359 μmol) in dichloromethane (2 mL) was added TFA (0.5 mL). The mixture was stirred at room temperature for 2 hours. The mixture was concentrated to afford compound D (162 mg) which was used in next step directly.

To a solution of compound D (162 mg, 285 μmol) in dichloromethane (5 mL) was added TEA (127 mg, 854 μmol) and E (29.1 mg, 285 μmol) at 0° C. The reaction mixture was stirred at room temperature for 2 hours. After completion, the mixture was quenched by adding water (30 mL) and extracted with ethyl acetate (10 mL×3). The organic layer was washed with brine, dried over sodium sulfate, filtered, and concentrated to give the crude which was purified by column chromatography on silica gel to yield the title compound 276 (40 mg, 28%) as white solid. LCMS: $[M+1]^+$=499.20. $^1$H NMR (400 MHz, Chloroform-d) δ 5.34 (s, 1H), 4.91-4.30 (m, 2H), 4.12-3.44 (m, 3H), 3.38-2.58 (m, 3H), 2.49-1.78 (m, 13H), 1.56-0.84 (m, 25H), 0.68 (s, 3H).

Example 277: (R)-1-((S)-4-acetyl-3-methylpiperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

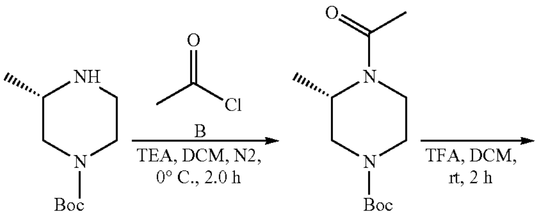

A C

-continued

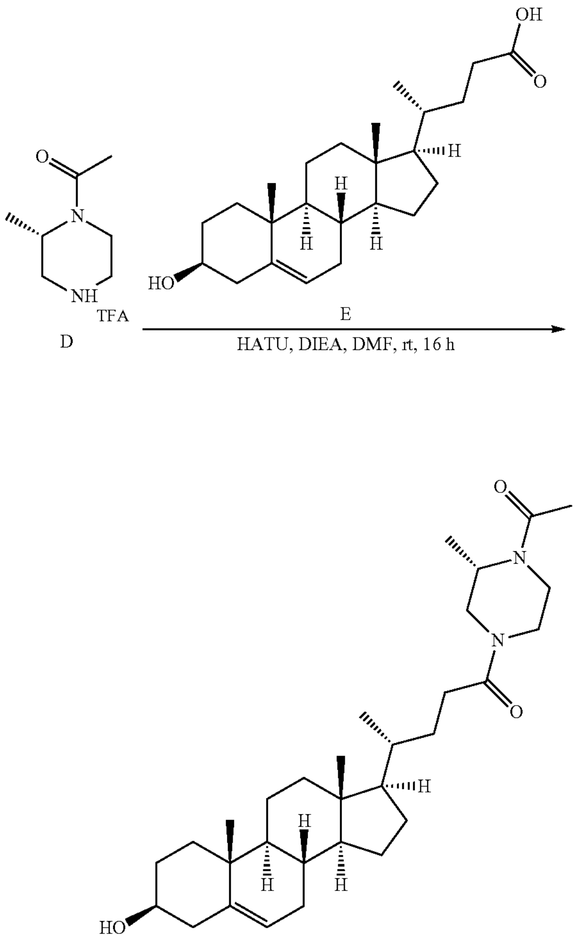

277

To a solution of compound A (500 mg, 2.5 mmol) and TEA (700 mg, 6.9 mmol) in DCM (10 mL) at 0° C. was added compound B (235 mg, 3 mmol). The mixture was stirred at 0° C. under $N_2$ for 2 h. The reaction was diluted with water, extracted with EA. The organic layer was washed by brine, dried over sodium sulfate, filtered, and concentrated to afford the compound C (400 mg) as white oil. To a solution of compound C (200 mg, 0.82 mmol) in DCM (3 mL) was added TFA (1 mL). The mixture was stirred at room temperature under $N_2$ for 2 h. The reaction was concentrated to afford compound D (170 mg) as yellow oil. To a solution of compound D (170 mg, 0.70 mmol) in DMF (6 mL) was added compound E (300 mg, 0.82 mmol), HATU (626 mg, 1.65 mmol) and DIEA (640 mg, 4.95 mmol). The mixture was stirred at room temperature under $N_2$ for 16 h. The reaction mixture was diluted with water and extracted with EtOAc. The organic layer was washed by brine, dried over sodium sulfate, filtered, and concentrated. The mixture was purified by column chromatography on silica gel to afford the title compound 277 (55.3 mg) as a white solid. $^1H$ NMR (400 MHz, Chloroform-d) δ 5.35 (d, J=5.2 Hz, 1H), 4.88-4.33 (m, 2H), 4.10-3.48 (m, 3H), 3.44-2.56 (m, 3H), 2.44-2.18 (m, 4H), 2.15-2.07 (m, 3H), 1.99 (m, 2H), 1.91-1.75 (m, 4H), 1.58-1.40 (m, 7H), 1.38-1.25 (m, 4H), 1.23-1.05 (m, 6H), 1.00 (s, 3H), 0.95 (t, J=6.8 Hz, 4H), 0.68 (s, 3H). LCMS: [M+H]=499.25.

Example 278: (R)-1-((R)-4-acetyl-3-methylpiperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

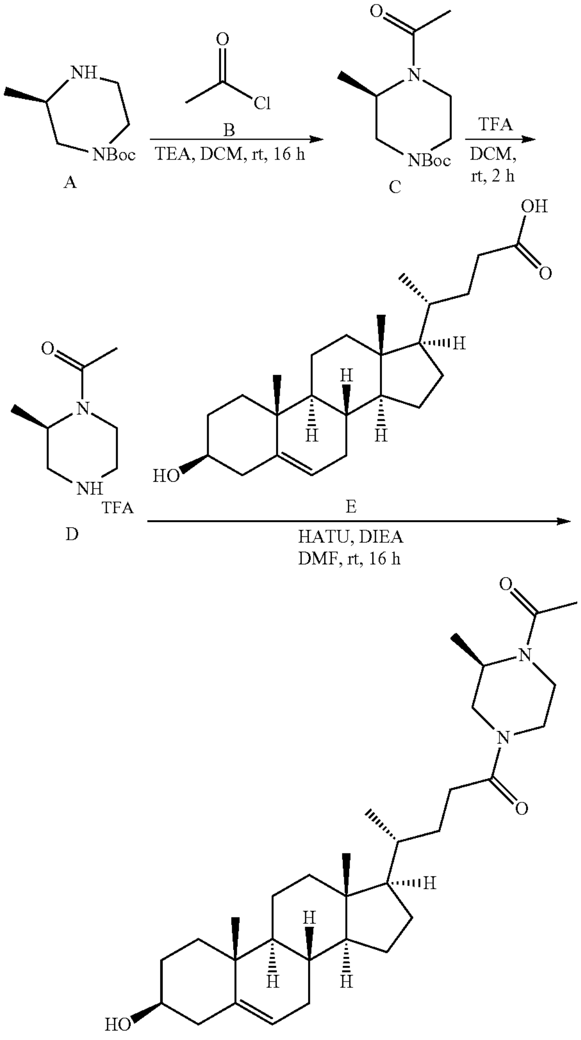

278

To a solution of compound A (200 mg, 999 μmol) in DCM (3 mL) was added TEA (298 mg, 2 mmol). The mixture was cooled to 0° C. and added compound B (86.2 mg, 1.1 mmol). After stirring at room temperature under $N_2$ for 16 h, the mixture was quenched with water and extracted with DCM. The organic layer was dried over sodium sulfate and concentrated to afford compound C (100 mg, 41.3%). To a solution of compound C (100 mg, 413 μmol) in DCM (2 mL) was added TFA (0.5 mL). After stirring at room temperature for 2 h, the mixture was concentrated to afford compound D and used directly into the next step.

To a solution of compound E (120 mg, 320 μmol) in DMF (2 mL) was added compound D (77.1 mg, 320 μmol), DIEA (207 mg, 1.6 mmol) and HATU (183 mg, 481 μmol). After stirring at room temperature for 16 h, the mixture was added water and extracted with EA. The organic layer was washed with brine, dried over sodium sulfate, and concentrated to afford the crude which was purified by silica gel chromatography to afford the title compound 278 (81.3 mg, 50.9%). LCMS [M+1]=499.30. $^{1}H$ NMR (400 MHz, Chloroform-d) δ 5.34 (dd, J=4.8, 2.6 Hz, 1H), 4.87-4.32 (m, 2H), 4.09-3.44 (m, 3H), 3.40-2.58 (m, 3H), 2.44-1.64 (m, 16H), 1.63-1.03 (m, 20H), 1.00 (s, 3H), 0.99-0.85 (m, 5H), 0.68 (s, 3H).

Example 279: 4—((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperazine-1-carboxylate

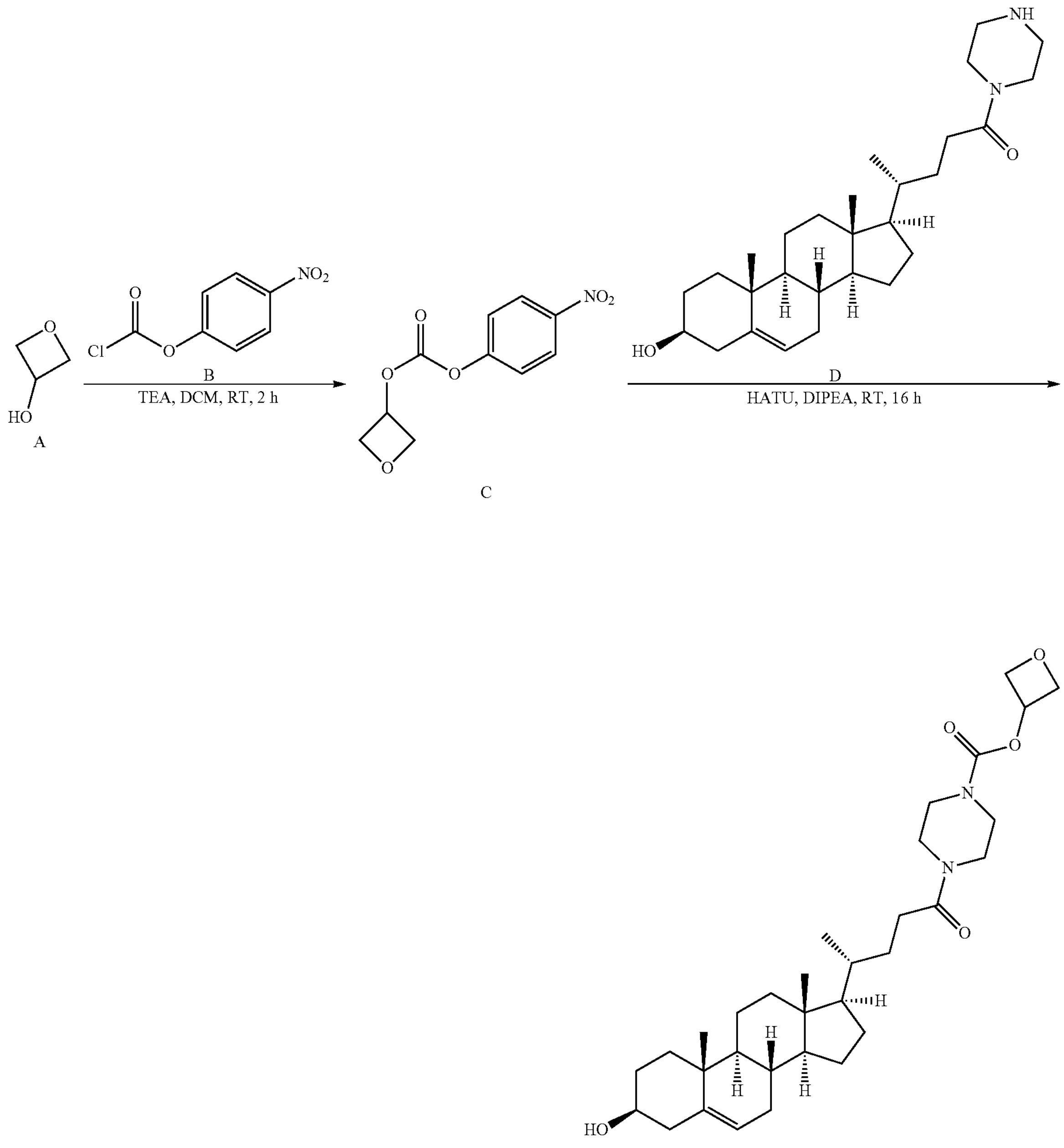

279

To a solution of compound A (100 mg, 1.35 mmol) and compound B (272 mg, 1.35 mmol) in dichloromethane (5 mL) was added triethylamine (205 mg, 2.02 mmol) at 0° C. under $N_2$ and stirred at room temperature for 2 hours. The mixture was concentrated in vacuum to give the crude compound C (520 mg).

To a solution of compound D (157 mg, 354 μmol), compound C (102 mg, 425 μmol) and DIEA (137 mg, 1.06 mmol) in DMF (1.5 mL) was added HATU (201 mg, 531 umol) at room temperature under $N_2$ and stirred for 16 h. The mixture was diluted with HCl (aq, 1M, 10 mL) and extracted with EA (50 mL). The organic layer was washed with $NaHCO_3$ (20 mL), water (20 mL*3) and brine (20 mL), dried over sodium sulfate and concentrated in vacuum to give the crude which was purified by silica gel chromatography (DCM:MeOH=100:0100:2) to give the title compound 279 (110 mg, 41%) as a white solid. LCMS: [M+H$^{+}$]

=543-25. $^{1}$H NMR (400 MHz, Chloroform-d) δ 5.45-5.38 (m, 1H), 5.36-5.33 (m, 1H), 4.89 (t, J=8.0 Hz, 2H), 4.69-4.63 (m, 2H), 3.65-3.59 (m, 2H), 3.56-3.41 (m, 7H), 2.42-2.34 (m, 1H), 2.32-2.15 (m, 3H), 2.05-1.92 (m, 2H), 1.91-1.72 (m, 4H), 1.64-1.60 (m, 1H), 1.52-1.41 (m, 6H), 1.37-1.25 (m, 3H), 1.22-1.04 (m, 4H), 1.01 (s, 3H), 0.97-0.91 (m, 4H), 0.69 (s, 3H).

Example 280: 2-hydroxyethyl 4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]piperazine-1-carboxylate

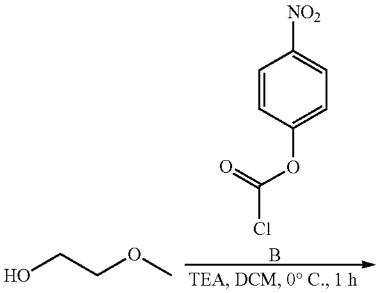

A

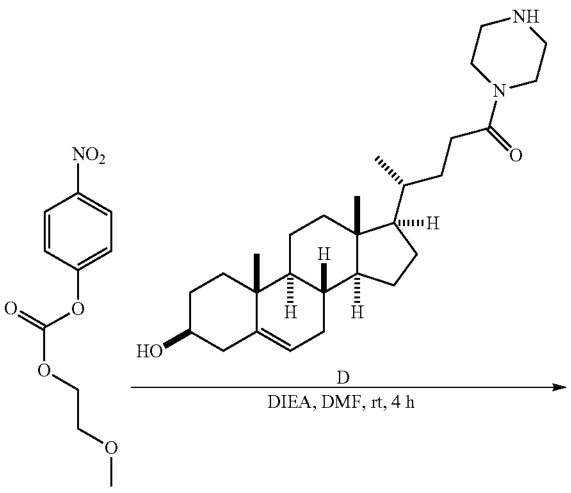

C

-continued

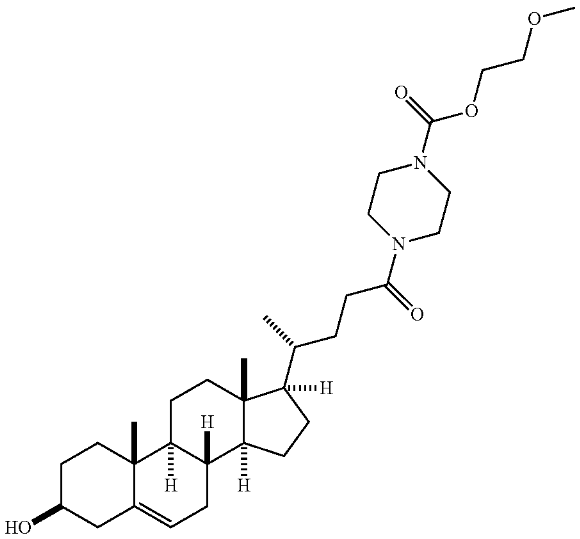

280

To a solution of compound A (100 mg, 1.31 mmol) in dichloromethane (5 mL) was added TEA (294 mg, 1.97 mmol) and compound B (291 mg, 1.45 mmol) at 0° C. The reaction mixture was stirred for 1 hour. After completion, the mixture was quenched by adding water (30 mL) and extracted with ethyl acetate (10 mL×3). The organic layer was washed with brine, dried over sodium sulfate, filtered, and concentrated to give the crude which was purified by column chromatography on silica gel to yield compound C (200 mg, 61%) as a white solid.

To a solution of compound C (200 mg, 829 μmol) in DMF (4 mL) was added compound D (367 mg, 829 μmol) and DIEA (322 mg, 2.49 mmol). The mixture was stirred at room temperature for 4 hours. The mixture was diluted with water and extracted with ethyl acetate. The organic layer was concentrated to give the crude which was purified by column chromatography on silica gel to give the title compound 280 (80 mg, 18%). LCMS: $[M+1]^{+}$=545.25. $^{1}$H NMR (400 MHz, Chloroform-d) δ 5.37-5.31 (m, 1H), 4.29-4.21 (m, 2H), 3.63-3.58 (m, 4H), 3.56-3.41 (m, 7H), 3.38 (s, 3H), 2.43-2.17 (m, 4H), 2.04-1.91 (m, 2H), 1.90-1.72 (m, 4H), 1.59-1.40 (m, 7H), 1.37-1.23 (m, 3H), 1.19-1.03 (m, 4H), 1.00 (s, 3H), 0.95 (d, J=6.6 Hz, 3H), 0.90 (dd, J=11.7, 6.4 Hz, 1H), 0.68 (s, 3H).

Example 281: 2-hydroxyethyl 4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]piperazine-1-carboxyla

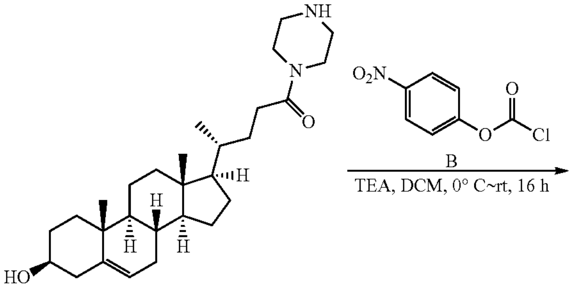

A

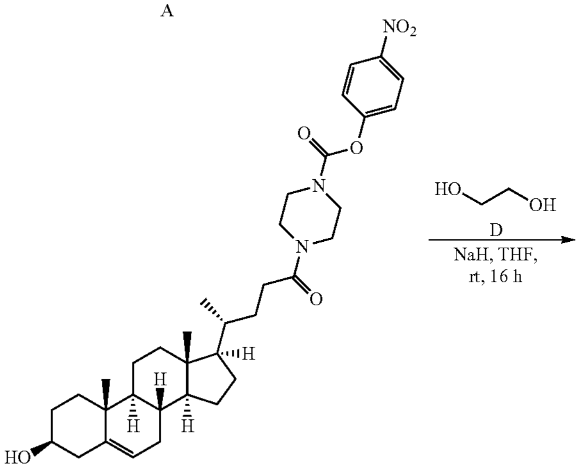

C

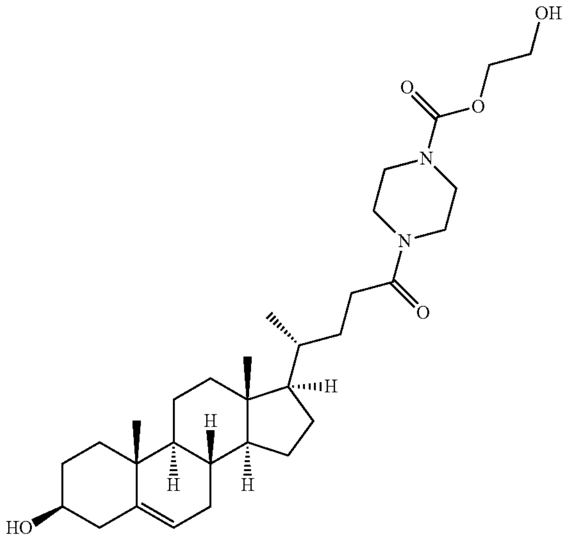

Example 281

To a solution of compound A (1.0 g, 2.26 mmol) in dichloromethane (10 mL) was added triethylamine (343 mg, 3.39 mmol) and compound B (462 mg, 2.03 mmol) at 0° C. The mixture was stirred at room temperature for 16 hours. The reaction was quenched with water and extracted with ethyl acetate (30 mL×4). The combined organic layer was concentrated to give the crude which was purified by silica gel chromatography to yield the title compound C (500 mg, 36%).

To a solution of compound D (408 mg, 6.58 mmol) in tetrahydrofuran (5 mL) was added NaH (131 mg, 3.29 mmol, 60% dispersion) at 0° C. After 30 min, compound D (400 mg, 658 μmol) was in THE and added to the mixture. The reaction was stirred at room temperature for 16 hours. The reaction was quenched with water and extracted with ethyl acetate (10 mL×4). The combined organic layer was concentrated to give the crude which was purified by silica gel chromatography to yield the title compound 281 (76.7 mg, 21%). LCMS:$[M+1]^+$=531.20. $^1H$ NMR (400 MHz, Chloroform-d) δ 5.34 (d, J=5.2 Hz, 1H), 4.30-4.21 (m, 2H), 3.87-3.80 (m, 2H), 3.61 (s, 2H), 3.54-3.44 (m, 7H), 2.42-2.33 (m, 1H), 2.32-2.19 (m, 3H), 2.02-1.93 (m, 2H), 1.91-1.75 (m, 8H), 1.63-1.55 (m, 2H), 1.54-1.41 (m, 6H), 1.36-1.24 (m, 3H), 1.21-1.03 (m, 5H), 1.00 (s, 3H), 0.97-0.87 (m, 4H), 0.68 (s, 3H).

Example 282: 4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]piperazine-1-carboxylate

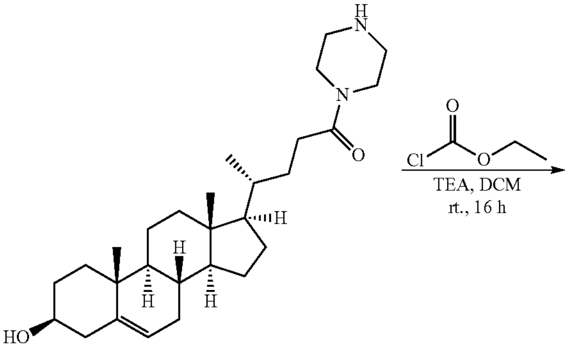

A

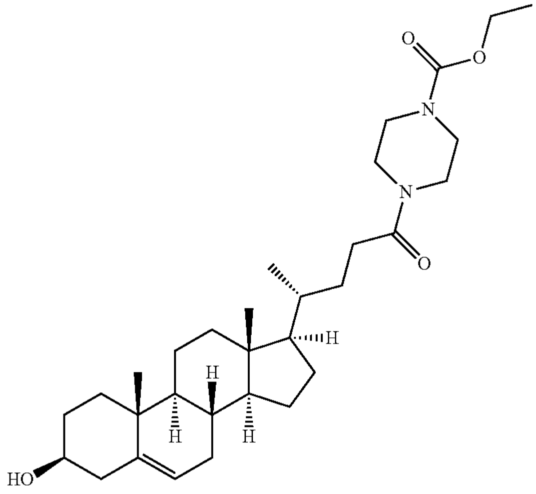

282

To a solution of compound A (200 mg, 452 μmol) in dichloromethane (5 mL) at room temperature was added triethylamine (229 mg, 2.26 mmol) and the reaction was cooled to 0° C. then ethyl chloroformate (39.2 mg, 361

μmol) was added. The resulting mixture was stirred for 16 h. The mixture was extracted with water and ethyl acetate. The organic layer was dried with sodium sulfate and concentrated under vacuum to give crude product which was purified by silica gel chromatography (eluting with 1/30 MeOH/DCM) to give the title compound 282 (56.0 mg, 24.1%). $^1$H NMR (400 MHz, $CDCl_3$) δ 5.38-5.31 (m, 1H), 4.16 (q, J=7.0 Hz, 2H), 3.70-3.33 (m, 9H), 2.43-2.19 (m, 4H), 2.04-1.72 (m, 6H), 1.53-1.28 (m, 6H), 1.27 (d, J=7.0 Hz, 6H), 1.12-1.02 (m, 4H), 1.01 (s, 3H), 0.95 (d, J=6.4 Hz, 3H), 0.93-0.84 (m, 3H), 0.68 (s, 3H). LCMS: $[M+H]^+$=515.25.

Example 283: Methyl-4-(4-((3S,5S,8S,9S,10S,13R,14S,17S)-3-hydroxy-10,13-dimethylhexadecahydro-1H-cyclopenta[a]phenanthren-17-yl)butanoyl)piperazine-1-carboxylate

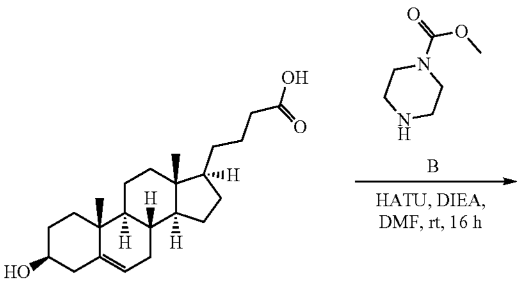

A

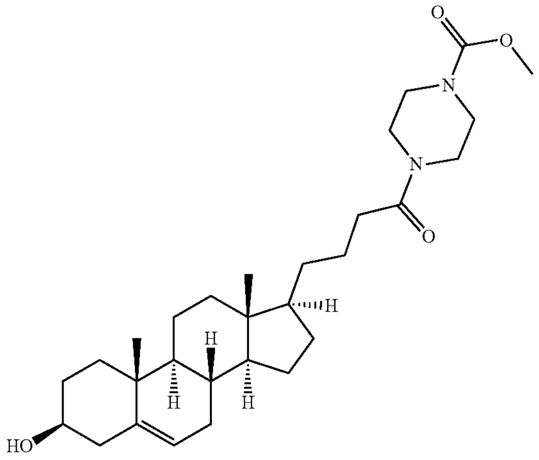

283

To a solution of compound A (200 mg, 555 μmol) and compound B (88 mg, 610 μmol) in DMF (3 mL) was added HATU (316 mg, 832 μmol) and DIEA (215 mg, 1.66 mmol). The mixture was stirred at room temperature for 16 hours. After completion, the mixture was quenched by adding saturated ammonium chloride solution (10 mL) and extracted with ethyl acetate (10 mL×3). The organic layer was washed with brine, dried over sodium sulfate, filtered, and concentrated to give the crude which was purified by column chromatography on silica gel to yield the title compound 283 (50 mg, 18.5%) as a white solid. LCMS: $[M+H]^+$=487.25. $^1$H NMR (400 MHz, Chloroform-d) δ 5.35 (d, J=5.0 Hz, 1H), 3.72 (s, 3H), 3.62-3.43 (m, 9H), 2.35-2.30 (m, 2H), 2.29-2.17 (m, 2H), 2.03-1.93 (m, 1H), 1.89-1.80 (m, 3H), 1.78-1.72 (m, 1H), 1.67-1.40 (m, 10H), 1.32-1.19 (m, 3H), 1.13 (m, 2H), 1.09-1.05 (m, 1H), 1.01 (s, 3H), 0.96 (t, J=5.6 Hz, 2H), 0.58 (s, 3H).

Example 284: methyl 4-[(4R)-4-[(1R,3aS,3bS,7S,9aR,9bS,11aR)-7-ethyl-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]piperazine-1-carboxylate

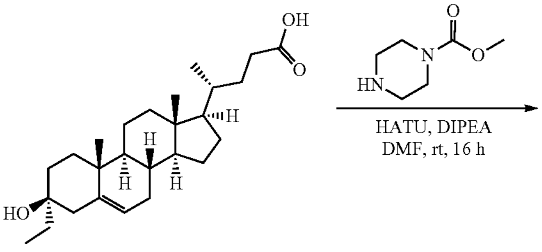

A

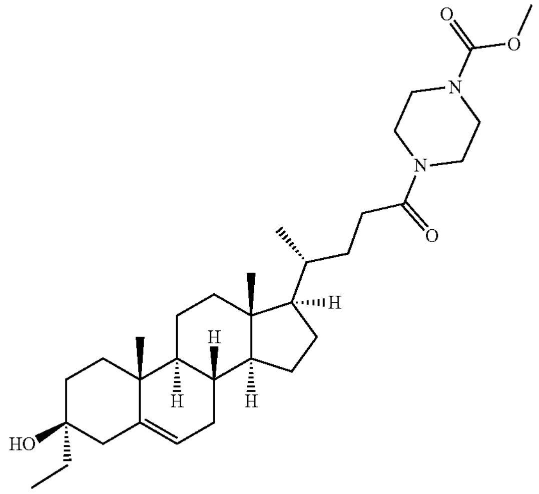

284

To a solution of compound A (150 mg, 373 μmol) in DMF (3 mL) was added DIEA (144 mg, 1.12 mmol), methyl piperazine-1-carboxylate (48.9 μL, 373 μmol) and HATU (283 mg, 2 eq., 745 μmol) at room temperature. The resulting mixture was stirred at room temperature for 16 h. The mixture was diluted with water and extracted with ethyl acetate. The organic layer was washed with water and brine, dried with sodium sulfate, and concentrated under vacuum to give crude product which was purified by silica gel chromatography (eluting with 1/30 MeOH/DCM) to give the title compound 284 (27.6 mg, 14.0%). $^1$H NMR (400 MHz, $CDCl_3$) δ 5.31-5.24 (m, 1H), 3.72 (s, 3H), 3.60 (bs, 2H), 3.54-3.40 (m, 6H), 2.44-2.18 (m, 3H), 2.07-1.96 (m, 3H), 1.96-1.68 (m, 4H), 1.65-1.55 (m, 4H), 1.51-1.36 (m, 8H), 1.27-1.05 (m, 6H), 1.03 (s, 3H), 0.95 (d, J=6.4 Hz, 3H), 0.85 (t, J=7.4 Hz, 3H), 0.68 (s, 3H). LCMS: $[M+H]^+$=529.25.

Example 285: methyl 4-((R)-4-((3S,8S,9S,10R,13R,14S,17R)-3-hydroxy-10,13-dimethyl-3-(trifluoromethyl)-2,3,4,7,8,9,10,11,12,13,14,15,16,17-tetradecahydro-1H-cyclopenta[a]phenanthren-17-yl)pentanoyl)piperazine-1-carboxylate

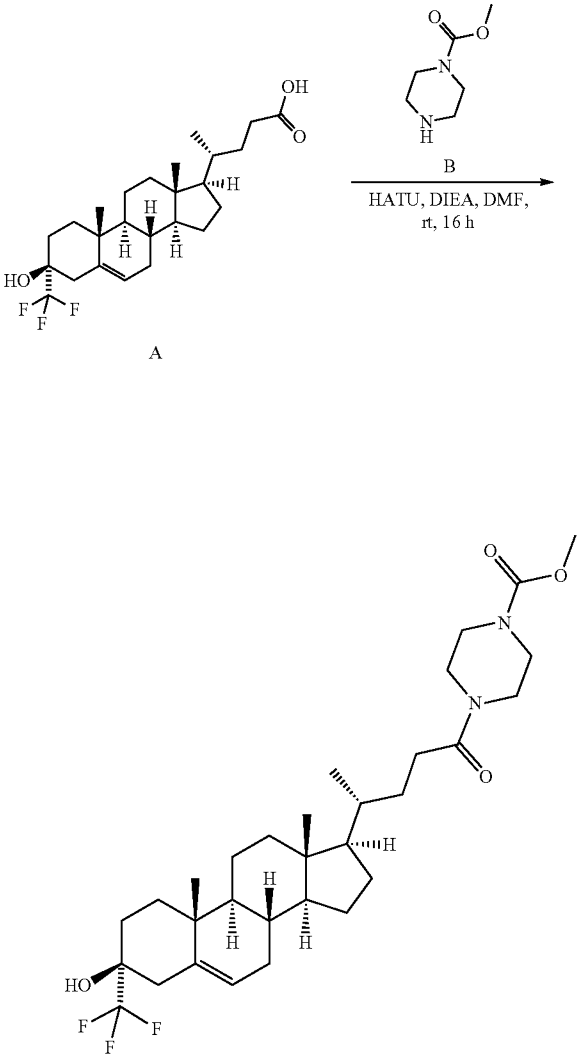

Example 285

To a solution of compound A (150 mg, 339 μmol) in DMF (5 mL) was added compound B (48.9 mg, 339 μmol) and HATU (159 mg, 678 μmol) and DIEA (219 mg, 1.69 mmol). The mixture was stirred at room temperature for 16 hours. The mixture was diluted with water and extracted with ethyl acetate. The organic layer was concentrated to give crude which was purified by silica gel chromatography to give the title compound 285 (123 mg, 64%). $^1H$ NMR (400 MHz, Chloroform-d) δ 5.39-5.35 (m, 1H), 3.73 (s, 3H), 3.59-3.42 (m, 8H), 2.49 (s, 2H), 2.46-2.34 (m, 1H), 2.31-2.22 (m, 1H), 2.10-1.09 (m, 21H), 1.06 (s, 3H), 1.03-1.00 (m, 1H), 0.96 (d, J=6.4 Hz, 3H), 0.69 (s, 3H). 19F NMR (376 MHz, Chloroform-d) δ-78.59. LCMS: [M+1]=569.25.

Example 286: 1—((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl dimethylcarbamate

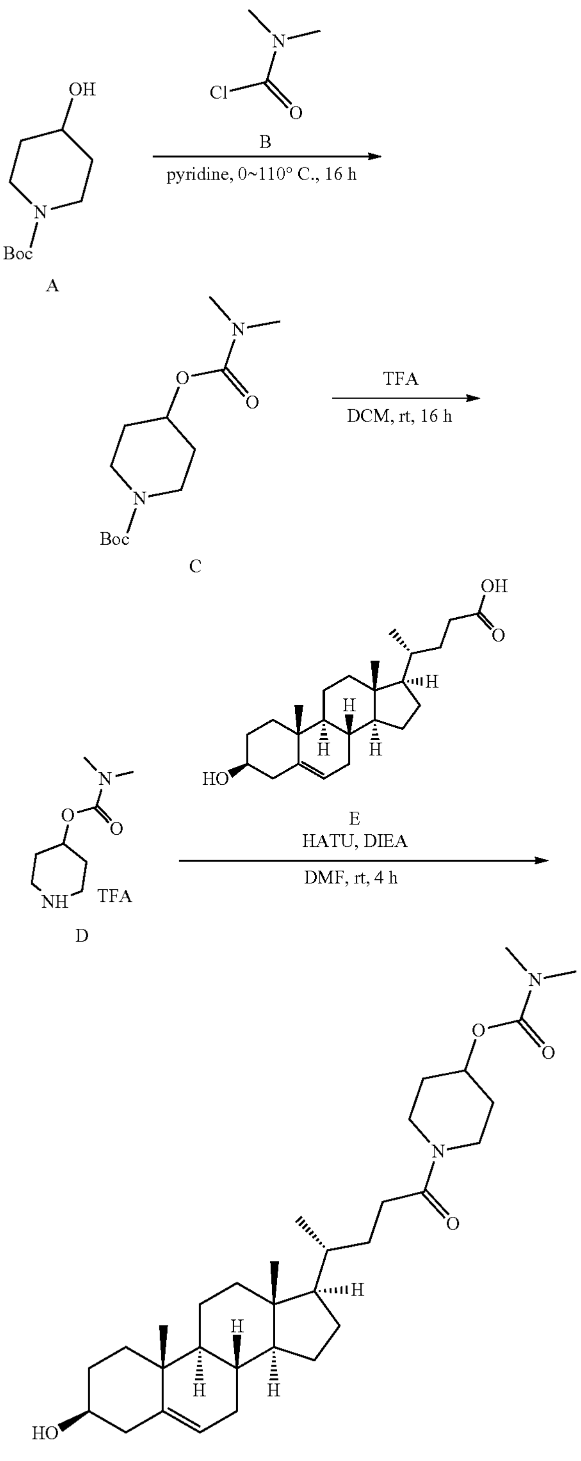

Example 286

To a solution of compound A (500 mg, 2.48 mmol) in pyridine (10 mL) was added compound B (2.67 g, 24.8 mmol) at 0° C. The reaction was heated to 110° C.; for 16 hours and then quenched with saturated aq. $NaHCO_3$ and extracted with ethyl acetate. The organic layer was concentrated to give crude which was purified by silica gel chromatography to give compound C (230 mg, 34%). To a solution of compound C (230 mg, 845 μmol) in dichloromethane (2 mL) was added TFA (289 mg, 2.53 mmol) and the mixture was stirred at room temperature for 16 hours. The mixture was concentrated to afford compound D (140 mg) used in next step directly.

To a solution of compound E (304 mg, 813 μmol) in DMF (4 mL) was added compound D (220 mg, 813 μmol), DIEA (1.05 g, 8.13 mmol) and HATU (765 mg, 3.25 mmol). After stirring at room temperature for 4 hours, the mixture was diluted with water and extracted with ethyl acetate. The combined organic layer was concentrated to give crude which was purified by silica gel chromatography to give the title compound 286 (250 mg, 58%). LCMS: $[M+1]^+$ =529.25. $^1H$ NMR (400 MHz, Chloroform-d) δ 5.37-5.33 (m, 1H), 4.93-4.84 (m, 1H), 3.91-3.33 (m, 5H), 2.91 (s, 6H), 2.44-2.18 (m, 4H), 2.04-1.88 (m, 3H), 1.88-1.81 (m, 3H), 1.80-1.59 (m, 9H), 1.53-1.03 (m, 12H), 1.00 (s, 3H), 0.95 (d, J=6.4 Hz, 3H), 0.68 (s, 3H).

Example 287: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(pyridin-4-yl)piperidin-1-yl]pentan-1-one

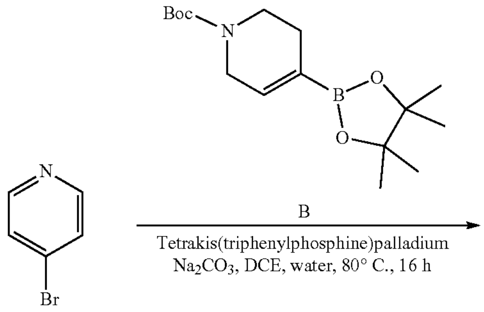

A

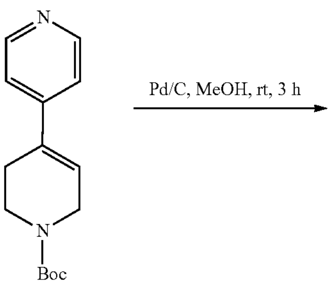

C

-continued

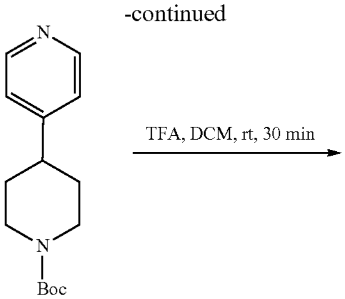

D

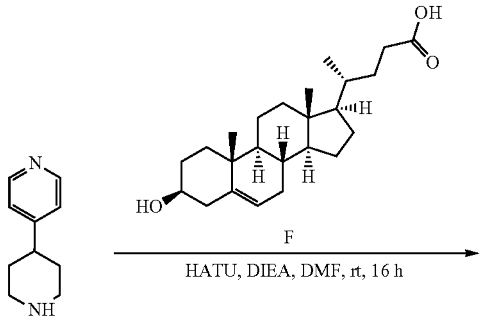

TFA

E

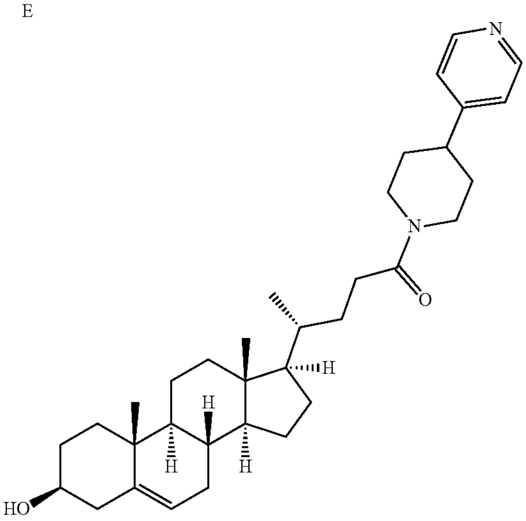

287

To a solution of compound A (200 mg, 1.27 mmol) in 1,2-dichloroethane (5 mL) was added sodium carbonate (1.89 mL, 3.78 mmol, 2M in water), compound B (470 mg, 1.52 mmol) and tetrakis(triphenylphosphane) palladium (43.9 mg, 38 μmol). The mixture was stirred at 80° C. for 16 hours under $N_2$. The reaction was quenched with water and extracted with ethyl acetate (10 mL×4). The combined organic layer was concentrated to give the crude which was purified by silica gel chromatography to yield the compound C (300 mg, 91%). To a solution of compound C (100 mg, 384 μmol) in methanol (8.2 mL) was added 10% Pd/C (10 mg). Then the mixture was stirred at room temperature for 3 h under 1 atm $H_2$ atmosphere. The mixture was filtered and concentrated to give the crude compound D (87 mg, 86%). To a solution of compound D (87 mg, 332 μmol) in dichloromethane (2 mL) was added trifluoroacetic acid (1 mL). After stirring at room temperature for 30 mins, the mixture was concentrated to give the crude compound E (92 mg, 98%).

To a solution of compound E (92 mg, 333 μmol) in DMF (3 mL) was added compound F (112 mg, 0.3 mmol), DIEA (258 mg, 2 mmol) and HATU (253 mg, 666 μmol). The mixture was stirred at room temperature for 16 hours. The reaction was quenched with water and extracted with ethyl acetate (10 mL×4). The combined organic layer was concentrated to give the crude which was purified by silica gel chromatography to yield the title compound 287 (68.5 mg, 39%). LCMS:$[M+1]^+$=519.30. $^1H$ NMR (400 MHz, Chloroform-d) δ 8.53 (d, J=6.2 Hz, 2H), 7.17-7.09 (m, 2H), 5.35 (d, J=4.8 Hz, 1H), 4.81 (d, J=13.2 Hz, 1H), 4.00 (d, J=13.4 Hz, 1H), 3.52-3.45 (m, 1H), 3. 21-3.06 (m, 1H), 2.81-2.69 (m, 1H), 2.67-2.58 (m, 1H), 2.48-2.35 (m, 1H), 2.33-2.18 (m, 3H), 2.09-1.74 (m, 12H), 1.54-1.22 (m, 13H), 1.21-1.03 (m, 4H), 1.00 (s, 3H), 0.97 (d, J=6.4 Hz, 3H), 0.94-0.84 (m, 1H), 0.69 (s, 3H).

Example 288: N-(1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)-N-methylisonicotinamide

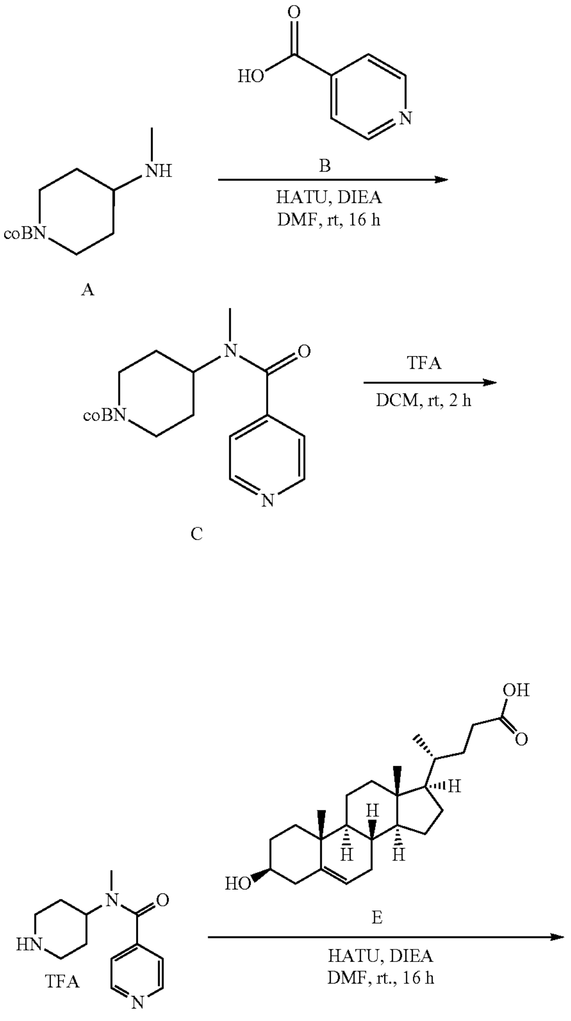

A

C

D

-continued

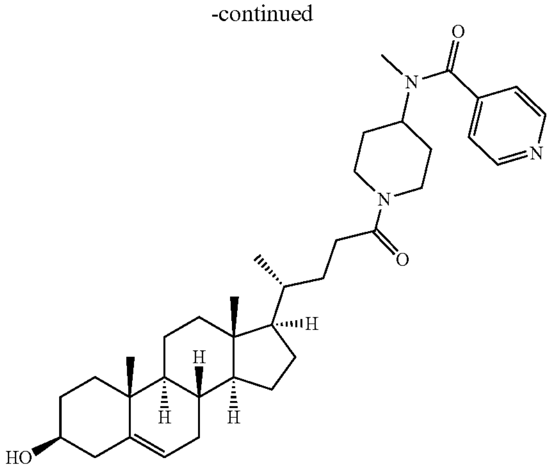

288

To a solution of compound A (200 mg, 933 μmol) in DMF (3 mL) was added compound B (115 mg, 933 μmol), DIEA (603 mg, 4.67 mmol) and HATU (532 mg, 1.4 mmol). The mixture was stirred at room temperature for 16 h. The mixture was diluted with water and extracted with EA. The organic layer was washed with brine, dried over sodium sulfate, and concentrated to afford 500 mg crude. The crude was purified by silica gel chromatography to afford compound C (290 mg, 97%). To a solution of compound C (150 mg, 470 μmol) in DCM (2 mL) was added TFA (0.5 mL). The mixture was stirred at room temperature for 2 h. The mixture was concentrated to afford compound D and which was used directly into the next step.

To a solution of compound E (170 mg, 454 μmol) in DMF (2 mL) was added compound D (144 mg, 454 μmol), DIEA (293 mg, 2.27 mmol) and HATU (259 mg, 681 μmol). After stirring at room temperature for 16 h, the mixture was diluted with water and extracted with EA. The organic layer was washed with brine, dried over sodium sulfate, and concentrated to afford the crude which was purified by silica gel chromatography to afford the title compound 288 (62.0 mg, 23.7%). LCMS [M+1]=576.30. $^1H$ NMR (400 MHz, Chloroform-d) δ 8.82-8.69 (m, 2H), 7.50-7.37 (m, 2H), 5.39-5.32 (m, 1H), 4.92-4.62 (m, 2H), 4.05-3.83 (m, 1H), 3.52 (dt, J=11.1, 6.2 Hz, 1H), 3.20 (t, J=13.1 Hz, 1H), 2.98 (s, 1H), 2.78 (s, 3H), 2.65 (t, J=13.2 Hz, 1H), 2.45-2.18 (m, 5H), 2.03-1.77 (m, 8H), 1.72-1.41 (m, 10H), 1.30 (s, 3H), 1.20-1.01 (m, 5H), 1.00 (s, 3H), 0.98-0.84 (m, 5H), 0.68 (s, 3H).

Example 289: N-{1-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]piperidin-4-yl}-N-methylmethanesulfonamide

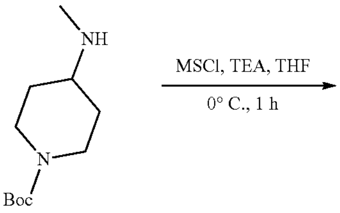

A

-continued

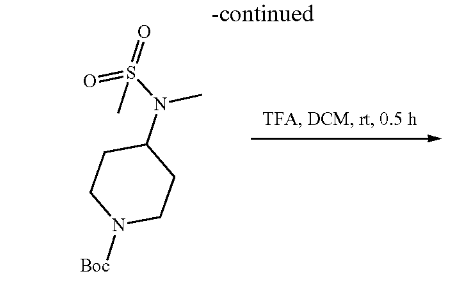

B

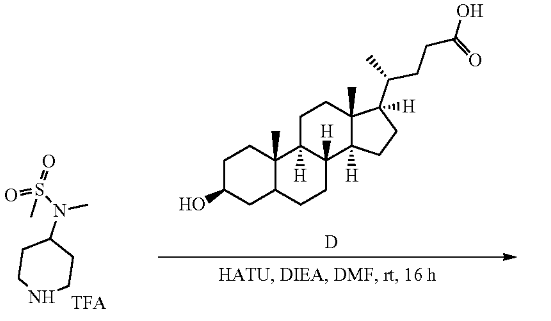

C

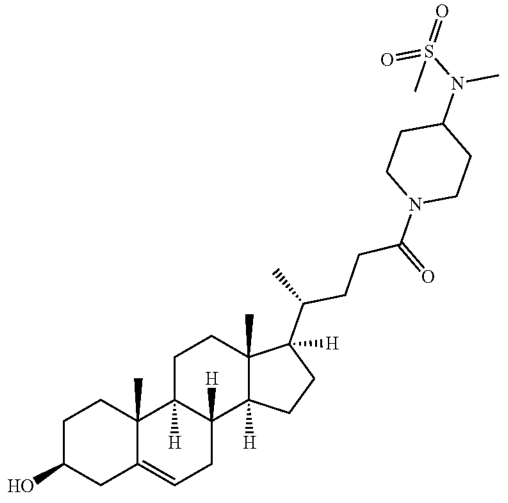

289

To a solution of compound A (1.0 g, 4.67 mmol) in tetrahydrofuran (5 mL) was added triethylamine (1.42 g, 14 mmol) and methanesulfonyl chloride (802 mg, 7 mmol) at 0° C. under $N_2$ atmosphere. The mixture was stirred at the same temperature for 1 hour. The reaction was quenched with water and extracted with ethyl acetate (30 mL×4). The combined organic layer was concentrated to give the crude compound B (1.2 g, 87%). To a solution of compound B (400 mg, 1.37 mmol) in dichloromethane (4 mL) was added TFA (2 mL). The mixture was stirred at room temperature for 30 mins. The reaction was quenched with water and extracted with DCM (10 mL×4). The combined organic layer was concentrated to give the crude compound C (159 mg, 40%).

To a solution of compound C (159 mg, 520 μmol) in DMF (3 mL) was added compound D (176 mg, 468 μmol), DIEA (403 mg, 6 eq., 3.12 mmol) and HATU (396 mg, 1.04 mmol). The mixture was stirred at room temperature for 16 hours. The reaction was quenched with water and extracted with ethyl acetate (10 mL×4). The combined organic layer was concentrated to give the crude which was purified by silica gel chromatography to yield the title compound 289 (164 mg, 57%). LCMS:$[M+Na]^+$=571.25. $^1H$ NMR (400 MHz, Chloroform-d) δ 5.34 (d, J=5.2 Hz, 1H), 4.77 (d, J=13.4 Hz, 1H), 4.01-3.87 (m, 2H), 3.57-3.45 (m, 1H), 3.14-3.02 (m, 1H), 2.86 (s, 3H), 2.77 (s, 3H), 2.60-2.49 (m, 1H), 2.43-2.15 (m, 4H), 2.05-1.93 (m, 2H), 1.89-1.77 (m, 4H), 1.76-1.69 (m, 2H), 1.68-1.56 (m, 5H), 1.54-1.40 (m, 7H), 1.37-1.24 (m, 3H), 1.21-1.03 (m, 5H), 1.00 (s, 3H), 0.95 (d, J=6.8 Hz, 4H), 0.68 (s, 3H).

Example 290: 1—((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N,N-dimethylpiperidine-4-sulfonamide

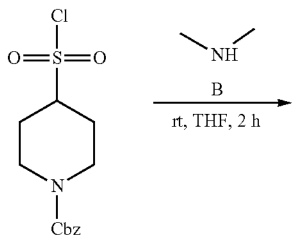

A

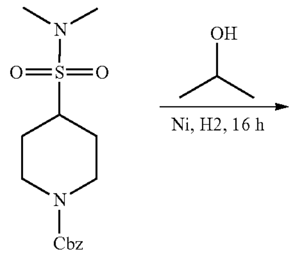

C

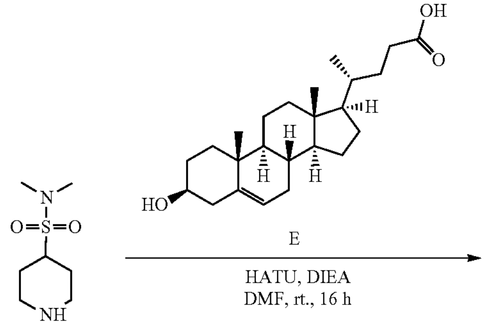

D

-continued

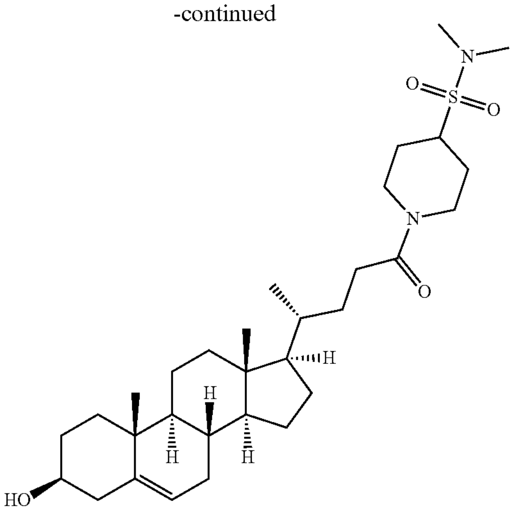

290

To a solution of compound A (1.0 g, 3.15 mmol) in THF (30 mL) was added compound B (16 mL, 2 M in THF). The mixture was stirred at room temperature for 2 hours. The mixture was concentrated under reduced pressure to afford the compound C (1.1 g) as oil. To a solution of compound C (300 mg, 919 μmol) in isopropyl alcohol (5 mL) was added Raney Ni (30 mg). The mixture was stirred at room temperature for 16 hours under 1 atm of hydrogen. The mixture was filtered and concentrated under reduced pressure to afford compound D (90 mg, 50.9%) as oil.

To a solution of compound D (90 mg, 468 μmol) and compound E (175 mg, 468 μmol) in DMF (3 mL) was added HATU (267 mg, 702 μmol) and DIEA (181 mg, 1.4 mmol). The mixture was stirred at room temperature for 16 hours. After completion, the mixture was quenched by adding saturated ammonium chloride solution (20 mL) and extracted with ethyl acetate (20 mL×3). The organic layer was washed with brine, dried over sodium sulfate, filtered, and concentrated to give the crude which was purified by column chromatography on silica gel to yield the title compound 290 (93 mg, 36.2%) as a white solid. LCMS: $[M+H]^+$=549.25. $^1H$ NMR (400 MHz, Chloroform-d) δ 5.35 (d, J=5.2 Hz, 1H), 4.74 (bs, 1H), 3.99 (bs, 1H), 3.57-3.46 (m, 1H), 3.23-2.97 (m, 2H), 2.93 (s, 6H), 2.55 (bs, 1H), 2.42-2.18 (m, 4H), 2.15-1.93 (m, 4H), 1.91-1.68 (m, 6H), 1.63 (s, 2H), 1.52-1.41 (m, 5H), 1.36-1.25 (m, 3H), 1.17-1.10 (m, 2H), 1.09-1.01 (m, 2H), 1.00 (s, 3H), 0.95 (d, J=6.4 Hz, 3H), 0.93-0.83 (m, 1H), 0.68 (s, 3H).

Example 291: 1-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]-N-methylpiperidine-4-sulfonamide

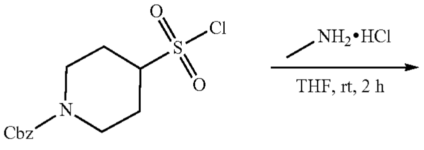

A

-continued

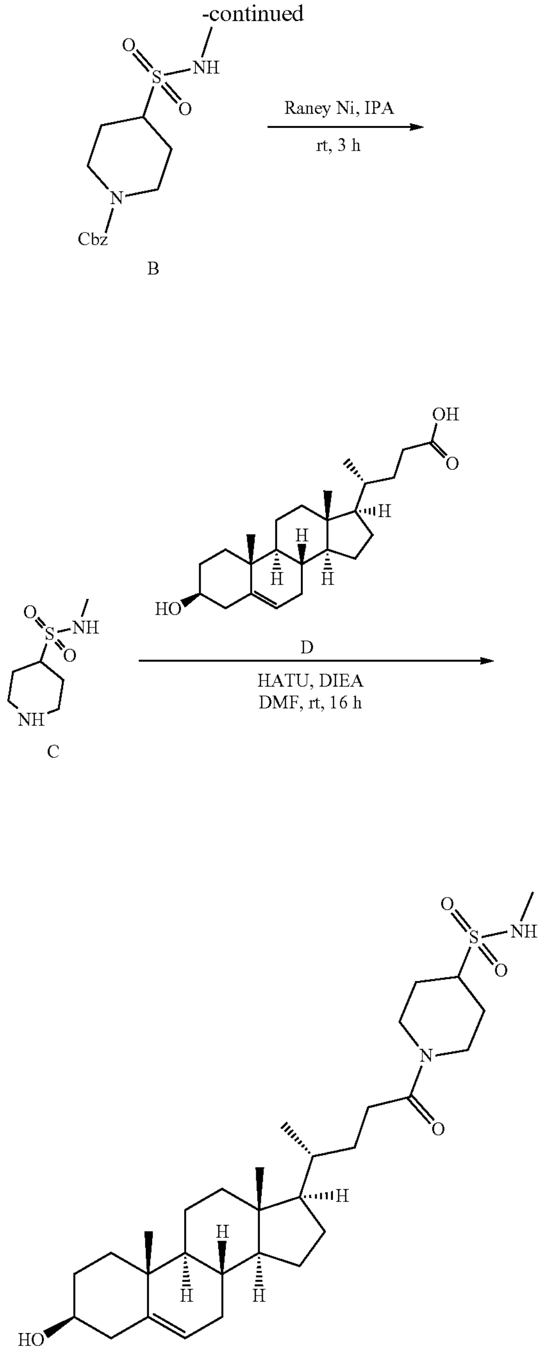

291

To a solution of compound A (1.0 g, 3.15 mmol) in tetrahydrofuran (30 mL) was added methylamine (977 mg, 31.5 mmol, HCl salt) at room temperature. After stirring at room temperature for 2 h, the solvent was removed under vacuum to give compound B (800 mg, 81.4%). To a solution of compound B (200 mg, 640 μmol) in propan-2-ol (10 mL) was added Raney Ni (20 mg). The reaction was stirred for 3 h at room temperature under 1 atm of $H_2$. The mixture was filtered through Celite and concentrated under vacuum to give crude compound C (77 mg, 67.5%).

To a solution of compound D (150 mg, 0.4 mmol) in DMF (5 mL) was added DIEA (155 mg, 1.2 mmol), compound C (71.4 mg, 0.4 mmol) and HATU (305 mg, 2 eq., 801 μmol) at room temperature. After stirring at room temperature for 16 h, the mixture was diluted with water and extracted with ethyl acetate. The organic layer was washed with water and brine, dried with sodium sulfate, and concentrated under vacuum to give crude product which was purified by silica gel chromatography (eluting with 1/30 MeOH/DCM) to give the title compound 291 (84.0 mg, 39.2%). $^1$H NMR (400 MHz, $CDCl_3$) δ 5.35 (d, J=5.0 Hz, 1H), 4.78 (d, J=13.2 Hz, 1H), 4.09-3.94 (m, 2H), 3.52 (dt, J=11.0, 6.2 Hz, 1H), 3.17-2.9 (m, 2H), 2.84 (d, J=4.8 Hz, 3H), 2.57 (t, J=12.6 Hz, 1H), 2.42-2.09 (m, 6H), 1.99 (tt, J=12.2, 3.4 Hz, 2H), 1.91-1.68 (m, 6H), 1.56-1.39 (m, 8H), 1.37-1.24 (m, 3H), 1.22-1.03 (m, 4H), 1.01 (s, 3H), 0.95 (d, J=6.4 Hz, 3H), 0.94-0.84 (m, 1H), 0.69 (s, 3H). LCMS: $[M+H]^+$=535.25.

Example 292: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(3-methyl-1,2,4-oxadiazole-5-carbonyl)piperazin-1-yl)pentan-1-one

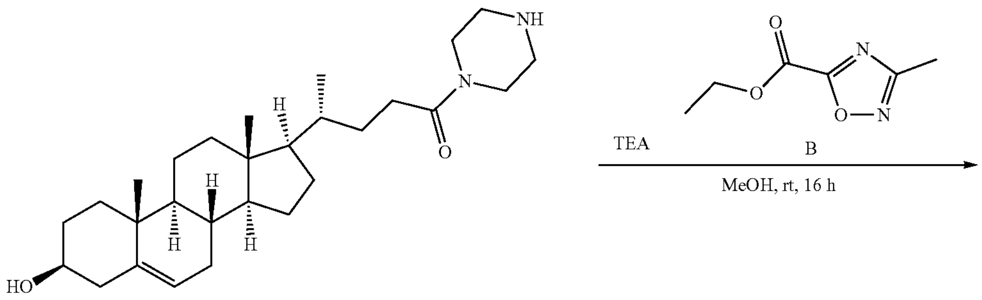

A

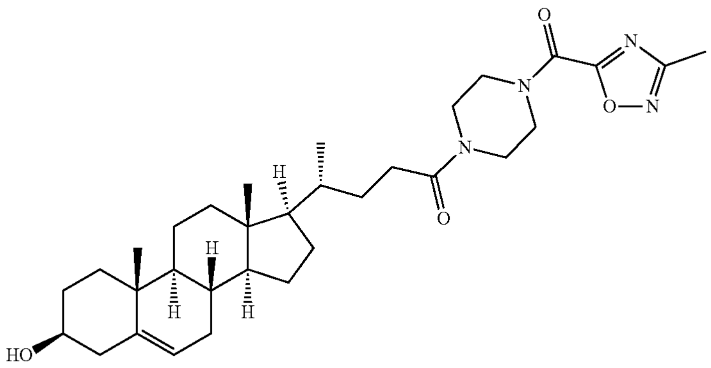

292

To a solution of compound A (129 mg, 291 μmol) in methanol (2 mL) was added compound B (50 mg, 320 μmol), triethylamine (405 μL, 2.91 mmol) at room temperature. The mixture was stirred for 16 hours. After completion, the result solution was quenched by the addition of water and extracted with dichloromethane. The combined organic layers were dried over sodium sulfate and concentrated to give crude product which was purified by column chromatography on silica to yield the title compound 292 (10.0 mg, 6.2%) as a white solid. $^1$H NMR (400 MHz, Chloroform-d) δ 5.35 (d, J=5.0 Hz, 1H), 3.90-3.46 (m, 9H), 2.49 (s, 3H), 2.44-2.19 (m, 4H), 2.04-1.78 (m, 6H), 1.51-1.23 (m, 10H), 1.18-0.84 (m, 12H), 0.69 (s, 3H).

Example 293: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-N-methyl-N-[2-(pyridin-2-yl)ethyl]pentanamide

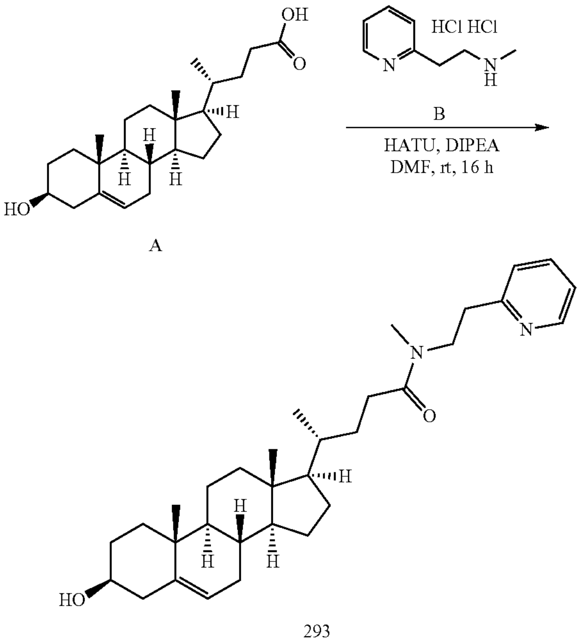

A

293

To a solution of compound A (200 mg, 534 μmol) in DMF (5 mL) was added DIEA (350 mg, 2.67 mmol), compound B (112 mg, 534 μmol) and HATU (406 mg, 1.07 mmol) at room temperature. The resulting mixture was stirred at room temperature for 16 h. The mixture was diluted with water and extracted with ethyl acetate. The organic layer was washed with water and brine, dried with sodium sulfate, and concentrated under vacuum to give crude product which was purified by silica gel chromatography (eluting with 1/30 MeOH/DCM) to give the title compound Example 293 (136 mg, 51.7%). $^1$H NMR (400 MHz, $CDCl_3$) δ 8.59-8.49 (m, 1H), 7.70-7.58 (m, 1H), 7.29-7.06 (m, 2H), 5.35 (d, J=5.0 Hz, 1H), 3.76-3.70 (m, 2H), 3.52 (dt, J=11.4, 6.2 Hz, 1H), 3.04 (dt, J=14.2, 7.2 Hz, 2H), 2.94 (d, J=7.4 Hz, 3H), 2.36-1.79 (m, 10H), 1.56-1.48 (m, 4H), 1.47-1.38 (m, 3H), 1.35-1.25 (m, 3H), 1.23-1.11 (m, 2H), 1.07 (td, J=10.4, 9.6, 4.6 Hz, 3H), 1.00 (s, 3H), 0.93 (d, J=6.4 Hz, 2H), 0.87 (d, J=6.4 Hz, 2H), 0.67 (d, J=5.8 Hz, 3H). LCMS: $[M+H]^+$=493.30.

Example 294: 1-acetyl-N—((R)-3-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)butyl)-N-methylpiperidine-4-carboxamide

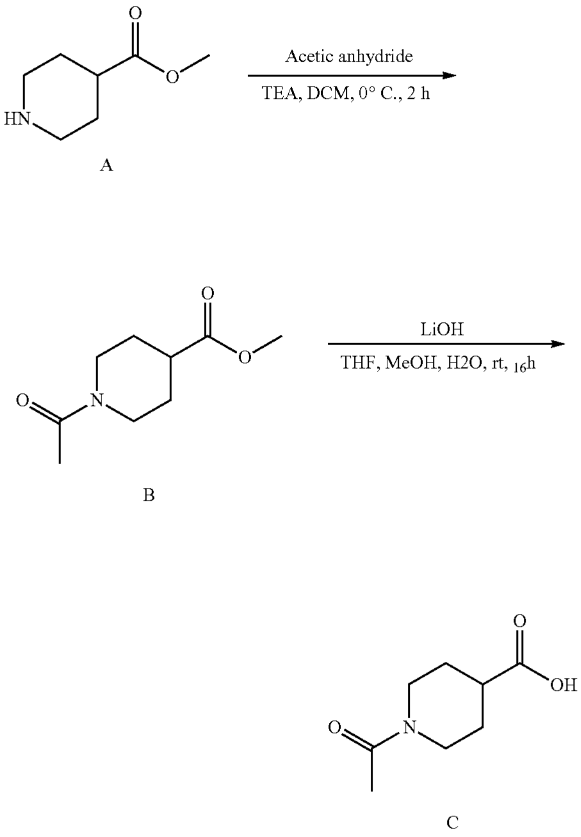

A

B

C

-continued
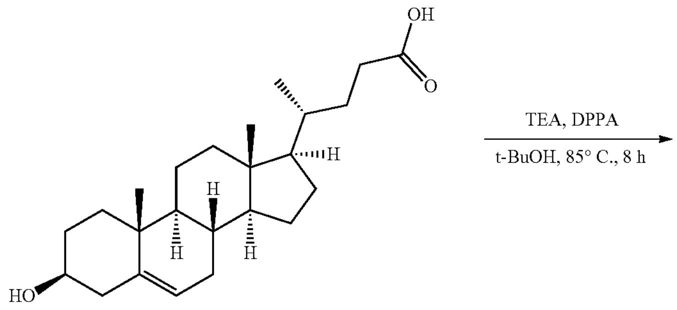
D
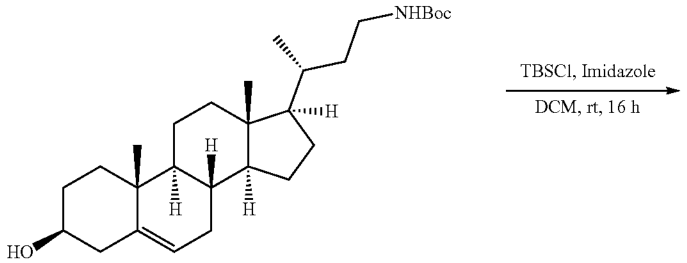
E
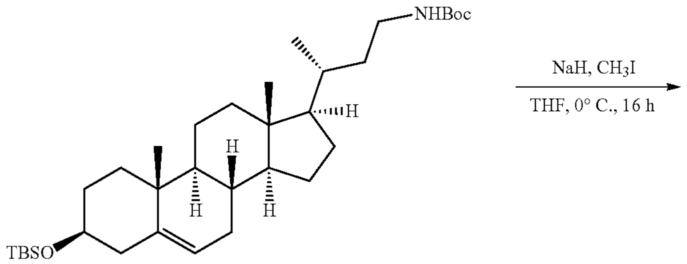
F
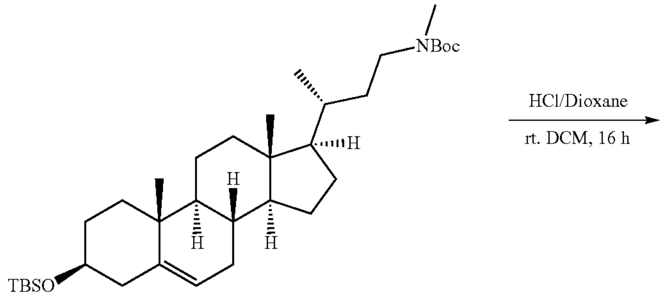
G
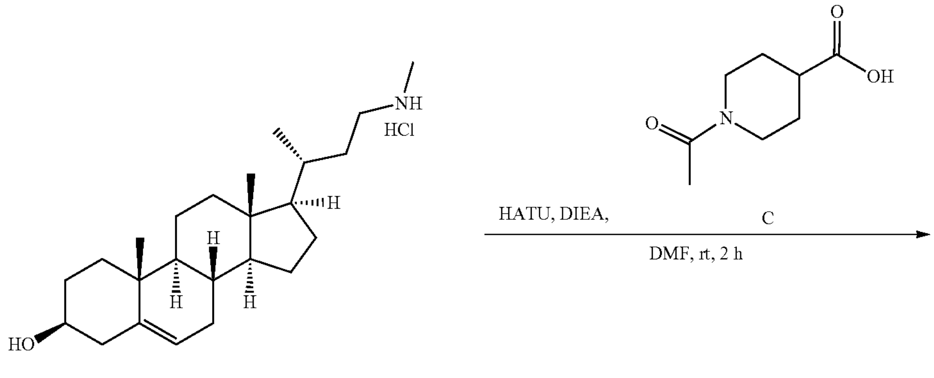
H -continued

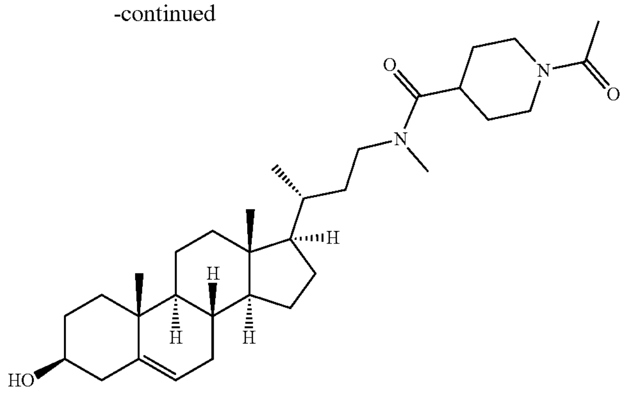

294

To a solution of compound A (1.0 g, 6.98 mmol) in DCM (10 mL) was added TEA (2.91 mL, 21 mmol) and acetic anhydride (984 μL, 10.5 mmol) at 0° C. The mixture was stirred at 0° C. for 2 hours. After completion, the result solution was quenched by the addition of water and extracted with DCM. The combined organic layers were dried over sodium sulfate and concentrated to give crude which was purified by silica gel chromatography to give the compound B (1.2 g, 92.8%) as a white solid.

To a solution of compound B (600 mg, 3.24 mmol) in methanol (1 mL), THE (1 mL) and water (1 mL) was added LiOH (233 mg, 9.72 mmol) at room temperature. The mixture was stirred for 16 hours. After completion, the resulting solution was quenched by water and adjusted pH to 2, then the mixture was concentrated to give crude compound C (500 mg, 90.2%).

To a solution of compound D (5.0 g, 12.9 mmol) in t-BuOH (50 mL) was added DPPA (3.54 mg, 12.9 mmol) and TEA (1.8 mL, 12.9 mmol). The mixture was stirred at 85° C. for 8 hours under $N_2$. After completion, the result solution was concentrated to give crude which was purified by silica gel chromatography to give the compound E (2.7 g, 46.1%) as a white solid.

To a solution of compound E (1.5 g, 3.37 mmol) in DCM (15 mL) was added imidazole (458 mg, 6.73 mmol) and TBSCl (761 mg, 5.05 mmol) at 0° C. and stirred for 16 hours. The result solution was quenched by the addition of water and extracted with DCM. The combined organic layers were dried over sodium sulfate and concentrated to give crude product which was purified by column chromatography on silica gel to give compound F (1.2 g, 63.7%) as a white solid.

To a solution of compound F (800 mg, 1.43 mmol) in DMF (40 mL) was added NaH (60% w/w, 286 mg, 7.41 mmol) and $CH_3I$ (608 mg, 4.29 mmol) at 0° C. The mixture was stirred for 16 hours. After completion, the resulting solution was quenched by the addition of water and extracted with DCM. The combined organic layers were dried over sodium sulfate and concentrated to give crude product which was purified by column chromatography on silica gel to give compound G (500 mg, 61.0%) as a white solid.

To a solution of compound G (300 mg, 523 μmol) in DCM (12 mL) was added HCl (1.31 mL, 5.23 mmol, 4M in dioxane) at room temperature and a mixture was stirred at room temperature for 16 hours. After completion, the resulting solution was concentrated to give crude compound H (188 mg, ca 100%) which was used in the next step directly.

To a solution of compound H (180 mg, 454 μmol) in DMF (10 mL) was added compound C (129 mg, 751 μmol), HATU (236 mg, 1 mmol) and DIEA (872 μL, 5.01 mmol) at room temperature. The mixture was stirred at room temperature for 2 hours. After completion, the resulting solution was quenched by the addition of water and extracted with ethyl acetate. The combined organic layers were dried over sodium sulfate, and concentrated to give crude product which was purified by column chromatography on silica gel to yield the title compound Example 294 (84.4 mg, 32.9%) as a white solid. $^1$H NMR (400 MHz, Chloroform-d) δ 5.35 (s, 1H), 4.68-4.52 (m, 1H), 3.89 (d, J=13.4 Hz, 1H), 3.56-3.46 (m, 1H), 3.39-3.23 (m, 2H), 3.16-2.89 (m, 4H), 2.74-2.63 (m, 2H), 2.34-2.20 (m, 2H), 2.09 (s, 3H), 2.03-1.68 (m, 10H), 1.53-1.07 (m, 13H), 1.05-0.96 (m, 7H), 0.68 (d, J=10.4 Hz, 3H). LCMS (M+H)+=[513.30].

Example 295: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-N-(1-acetylpiperidin-4-yl)-N-methylpentanamide

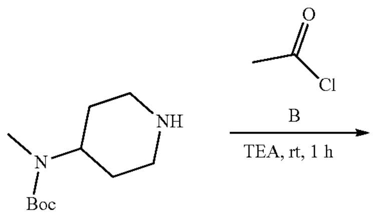

A

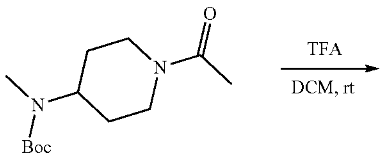

C

-continued

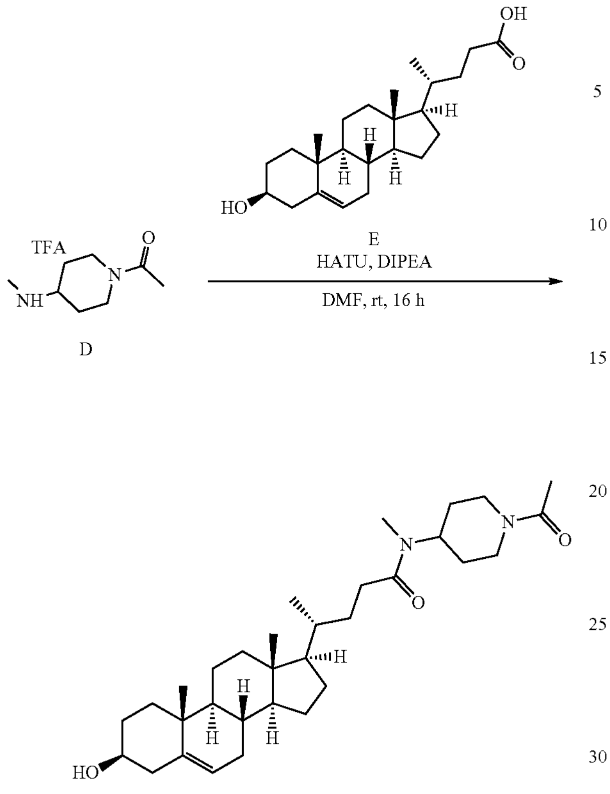

295

To a solution of compound A (100 mg, 467 μmol) in dichloromethane (4 mL) was added TEA (142 mg, 1.4 mmol) and compound B (44 mg, 560 μmol) at 0° C. The reaction mixture was stirred for 1 hour. After completion, the mixture was quenched by adding water (30 mL) and extracted with ethyl acetate (10 mL×3). The organic layer was washed with brine, dried over sodium sulfate, filtered, and concentrated to give the crude which was purified by column chromatography on silica gel to yield the title compound C (120 mg, 89%) as a white solid.

To a solution of compound C (120 mg, 507 μmol) in dichloromethane (2 mL) was added TFA (0.5 mL). The mixture was stirred at room temperature for 16 hours. The mixture was concentrated to afford compound D (121 mg) which was used in next step directly.

To a solution of compound D (121 mg, 448 μmol) in DMF (4 mL) was added compound E (134 mg, 358 μmol) and DIEA (347 mg, 2.69 mmol) and HATU (341 mg, 896 μmol). The mixture was stirred at room temperature for 16 hours. The mixture was diluted with water and extracted with ethyl acetate. The organic layer was concentrated to give the crude which was purified by column chromatography on silica gel to give the title compound 295 (70 mg, 30%). LCMS: $[M+1]^+$=545.25. $^1$H NMR (400 MHz, Chloroform-d) δ 5.35 (d, J=5.1 Hz, 1H), 4.72 (t, J=12.9 Hz, 2H), 3.97-3.76 (m, 1H), 3.52 (dq, J=10.6, 5.5, 4.6 Hz, 1H), 3.15 (t, J=13.1 Hz, 1H), 2.86-2.75 (m, 3H), 2.59 (t, J=12.8 Hz, 1H), 2.38-2.18 (m, 4H), 2.16-2.08 (m, 3H), 1.99 (t, J=13.0 Hz, 2H), 1.89-1.64 (m, 6H), 1.45-1.32 (m, 9H), 1.23-1.03 (m, 5H), 1.01 (s, 3H), 0.95 (d, J=6.6 Hz, 3H), 0.93-0.81 (m, 2H), 0.69 (s, 3H).

Example 296: (1R,4r)-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methylpentanamido)-N,N-dimethylcyclohexane-1-carboxamide

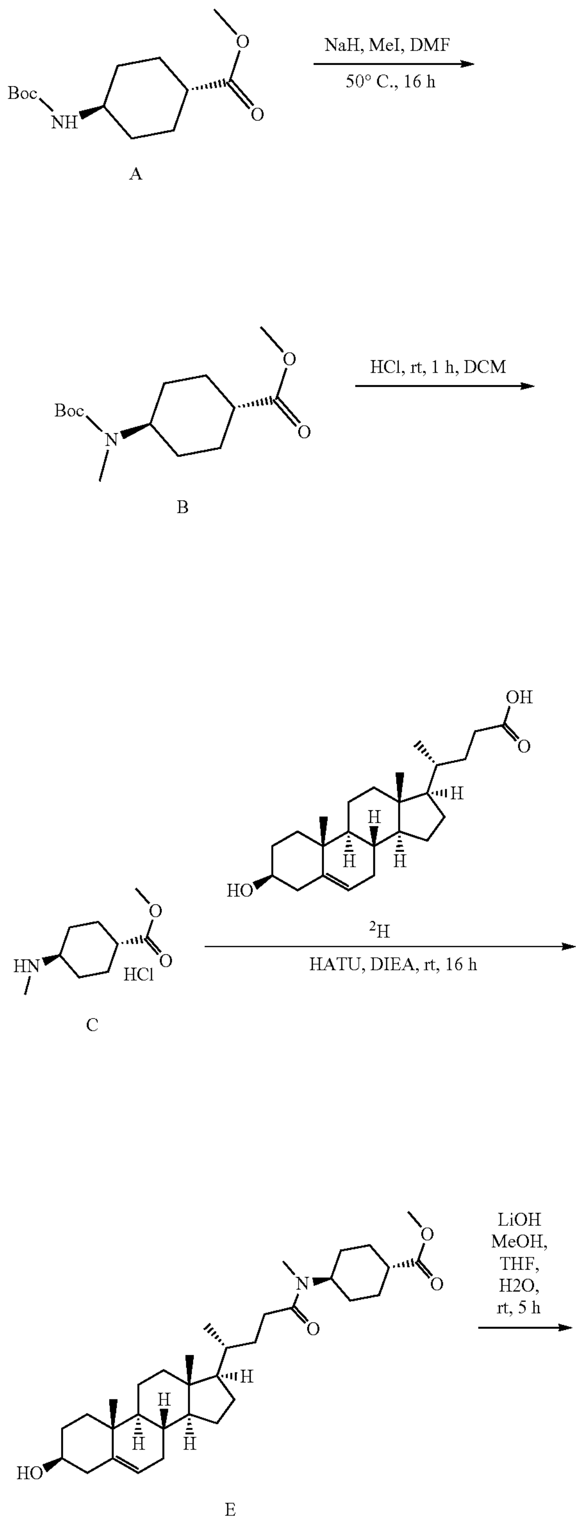

-continued

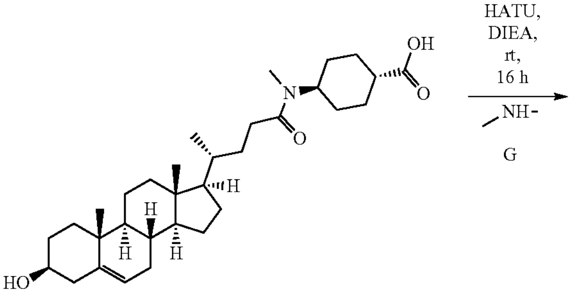

F

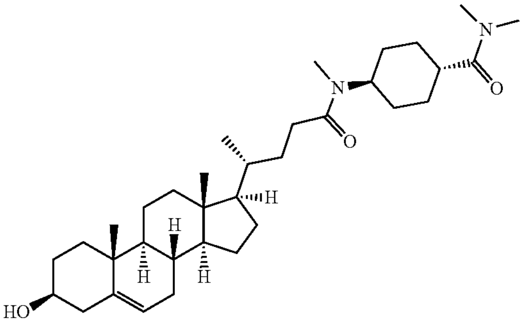

296

To a solution of compound A (500 mg, 1.94 mmol) in DMF (5 mL) was added NaH (155 mg 3.89 mmol, 60% dispersion in oil) at 0° C. and stirred for 0.5 h. MeI (1.1 g, 7.77 mmol) was added and the reaction stirred at 50° C. for 16 hours. The mixture was diluted with water and extracted with ethyl acetate. The organic layer was concentrated to give crude which was purified by silica gel chromatography to give compound B (450 mg, 85.3%). To a solution of compound B (450 mg, 845 μmol) in dichloromethane (4 mL) was added HCl (1 mL, 4 mmol, 4 M in dioxane). The mixture was stirred at room temperature for 1 hour. The mixture was concentrated to afford compound C (387 mg, ca 845 μmol) which was used in next the step directly. To a solution of compound C (240 mg, 509 mmol) in DMF (5 mL) was added compound D (394 mg, 1.05 mmol), DIEA (748 mg, 7.01 mmol) and HATU (732 mg, 2.34 mmol). After stirring at room temperature for 16 hours, the mixture was diluted with water and extracted with ethyl acetate. The organic layer was concentrated to give crude which was purified by silica gel chromatography to give compound E (250 mg, 93.0%).

To a solution of compound E (150 mg, 284 μmol) in methanol (1 mL), water (1 mL) and THF (1 mL) was added LiOH (20.4 mg, 853 μmol). The solution was stirred at room temperature for 5 hours. The mixture was adjusted to pH=3-4 with 1 M HCl and extracted with ethyl acetate (10 mL×3). The combined organic phases were washed with brine, dried over sodium sulfate, concentrated under vacuum to afford compound F (130 mg, 89%).

To a solution of compound F (130 mg, 253 μmol) in DMF (3 mL) was added compound G (0.28 mL, 0.56 mmol, 2M in THF), DIEA (196, 1.52 mmol) and HATU (190 mg, 506 mmol). After stirring at room temperature for 16 hours, the mixture was diluted with $H_2O$ and extracted with ethyl acetate. The combined organic layer was concentrated to give the crude which was purified by silica gel chromatography to give the title compound 296 (55 mg, 40%). $^1H$ NMR (400 MHz, Chloroform-d) δ 5.34 (s, 1H), 4.51-3.47 (m, 2H), 3.11-2.75 (m, 9H), 2.46-2.16 (m, 5H), 2.04-1.68 (m, 12H), 1.54-1.22 (m, 12H), 1.19-1.04 (s, 3H), 1.00 (m, 3H), 0.9-0.82 (m, 5H), 0.68 (s, 3H). LCMS: $[M+1]^+$=541.30.

Example 297: (1S,4s)-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methylpentanamido)-N,N-dimethylcyclohexane-1-carboxamide

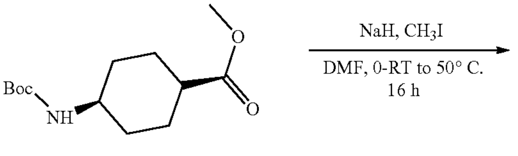

A

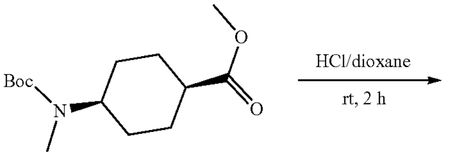

B

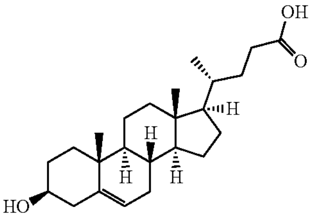

D

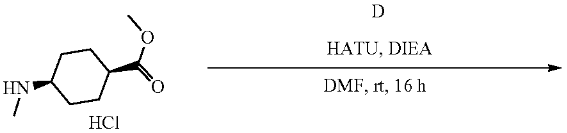

C

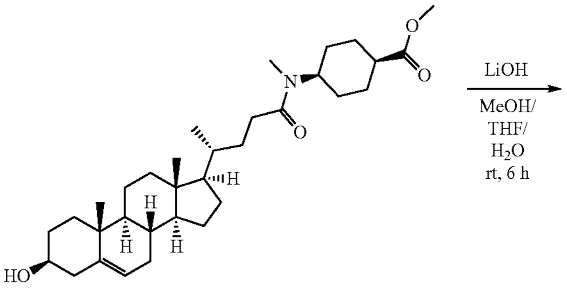

E

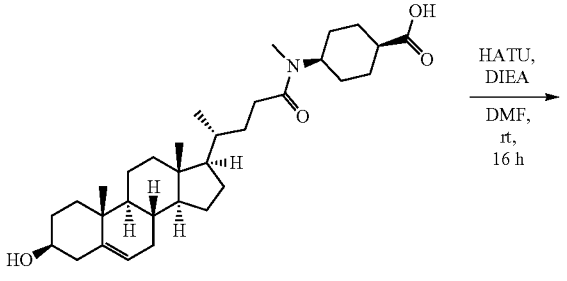

F

-continued

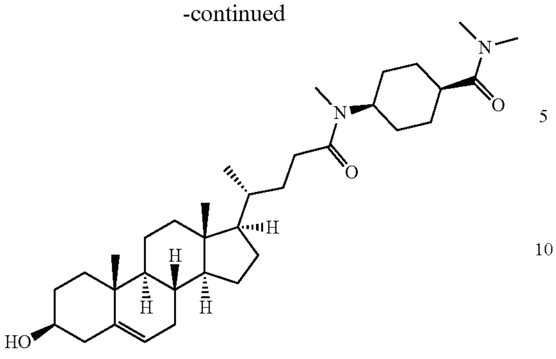

Example-297

To a solution of compound F (600 mg, 976 μmol) in DMF (20 mL) was added dimethylamine (0.6 mL, 2 M in THF), HATU (891 mg, 2.34 mmol) and DIEA (754 mg, 5.85 mmol). After stirring at room temperature for 16 hours, the mixture was diluted with water and extracted with ethyl acetate. The organic layer was concentrated to give crude which was purified by prep-HPLC to give the title compound 297 (35.9 mg, 6.8%). LCMS: [M+1]+=541.30. $^1$H NMR (400 MHz, Chloroform-d) δ 5.35 (d, J=5.1 Hz, 1H), 3.58-3.47 (m, 1H), 3.04-2.96 (m, 7H), 2.94 (s, 3H), 2.90-2.55 (m, 4H), 2.34-2.19 (m, 3H), 2.00-1.03 (m, 25H), 1.00 (d, J=5.6 Hz, 6H), 0.98-0.80 (m, 2H), 0.69 (s, 3H).

To a solution of NaH (468 mg, 11.7 mmol, 60% dispersion in oil) in DMF (20 mL) was added compound A (1.0 g, 3.89 mmol) at 0° C. The mixture was stirred at this temperature for 1 h, then added $CH_3I$ (1.65 g, 11.7 mmol). After stirring at 50° C.; for 16 hours under nitrogen, the mixture was diluted with water extracted with ethyl acetate. The organic layer was concentrated to give crude which was purified by silica gel chromatography to give compound B (1.0 g, 95%).

To a solution of compound B (1.0 g, 3.68 mmol) in dioxane (10 mL) was added hydrogen chloride (2.5 mL, 10 mmol, 4M in dioxane). After stirring at room temperature for 2 hours, the mixture was concentrated to give compound C (656 mg) used in next step directly.

To a solution of compound D (656 mg, 3.13 mmol) in DMF (12.9 mL) was added compound C (1.16 g, 3.10 mmol), HATU (824 mg, 3.5 mmol) and DIEA (1.13 g, 8.76 mmol). After stirring at room temperature for 16 hours, the mixture was diluted with water and extracted with ethyl acetate. The organic layer was concentrated to give crude which was purified by silica gel chromatography to give compound E (515 mg, 31%).

To a solution of compound E (515 mg, 976 μmol) in methanol (2 mL), THF (2 mL) and water (2 mL) was added LiOH (117 mg, 1.95 mmol). After stirring at room temperature for 6 hours, the mixture was adjusted pH to 1-2 then extracted with DCM. The organic layer was concentrated to give compound F (600 mg, ca 976 μmol) which was used in next step directly.

Example 298: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methyl-N-((1r,4R)-4-(N-methylacetamido)cyclohexyl)pentanamide

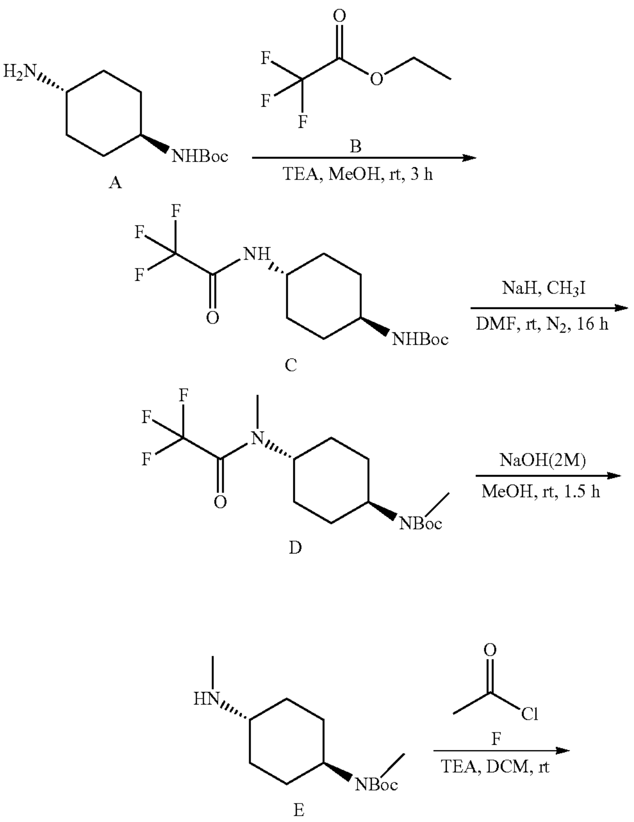

-continued

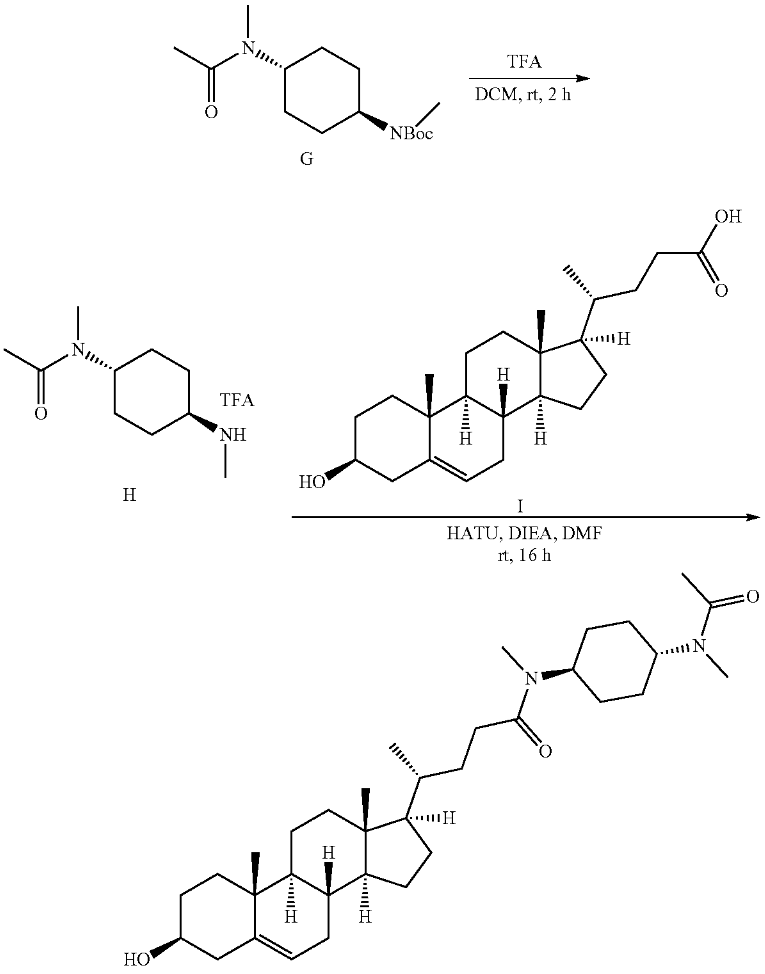

G

H

I

298

To a solution of compound A (700 mg, 3.27 mmol) in methanol (10 mL) was cooled to 0° C., then added compound B (2.32 g, 16.3 mmol) and TEA (2 mL). The mixture was stirred at room temperature for 3 h. The mixture was concentrated to afford the crude which was purified by silica gel chromatography to afford compound C (800 mg, 78.9%).

To a solution of compound C (800 mg, 2.58 mmol) in dry DMF (8 mL) was cooled to 0° C., and added NaH (309 mg, 7.73 mmol, 60% dispersion in oil). The mixture was stirred 20 minutes, followed by the addition of $CH_3I$ (805 mg, 5.67 mmol). After stirring at room temperature under $N_2$ for 16 h, the mixture was quenched with ice cold water, neutralized with citric acid and extracted with EA. The organic layer was washed with brine, dried over sodium sulfate, and concentrated to afford compound D (800 mg, 91.5%).

To the solution of compound D (700 mg, 2.07 mmol) in methanol (8 mL), NaOH (4 mL, 2M) was added. The mixture was stirred at room temperature for 1.5 h. The mixture was concentrated and to the residue was added 1 N citric acid and extracted with DCM/MeOH=9/1. The aqueous phase was basified with 2 N NaOH solution and extracted with DCM/MeOH=9/1. The organic layer was dried over sodium sulfate and concentrated to afford compound E (400 mg, 80%).

To a solution of compound E (150 mg, 619 μmol) in DCM (2 mL) was added TEA (185 mg, 1.24 mmol). The mixture was cooled to 0° C. and added compound F (58.3 mg, 743 μmol). After stirring at room temperature under $N_2$ for 2 h, the mixture was extracted with EA and water. The organic layer was dried over sodium sulfate and concentrated to afford compound G (140 mg, 79.5%). To a solution of compound G (120 mg, 422 μmol) in DCM (1 mL) was added TFA (0.2 mL). The mixture was stirred at room temperature for 2 h. The mixture was concentrated to afford crude compound H.

To a solution of compound I (100 mg, 267 μmol) in DMF (2 mL) was added compound H (124 mg, 442 μmol), DIEA (173 mg, 1.33 mmol) and HATU (152 mg, 0.4 mmol). The mixture was stirred at room temperature for 16 h. The mixture was diluted with water and extracted with EA. The organic layer was washed with brine, dried over sodium sulfate, and concentrated to afford the crude which was purified by silica gel chromatography to afford the title compound 298 (50 mg, 34.6%). LCMS [M+1]=541.30. $^1H$ NMR (400 MHz, Chloroform-d) δ 5.35 (d, J=4.2 Hz, 1H), 4.46 (bs, 1H), 3.57-3.48 (m, 1H), 2.86 (s, 3H), 2.85 (s, 3H), 2.44-2.11 (m, 12H), 2.05-1.80 (m, 7H), 1.79-1.03 (m, 26H), 1.01 (s, 3H), 0.97 (d, J=6.4 Hz, 3H), 0.93-0.85 (m, 1H), 0.69 (s, 3H).

Example 299: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methyl-N-((1s,4S)-4-(N-methylacetamido)cyclohexyl)pentanamide
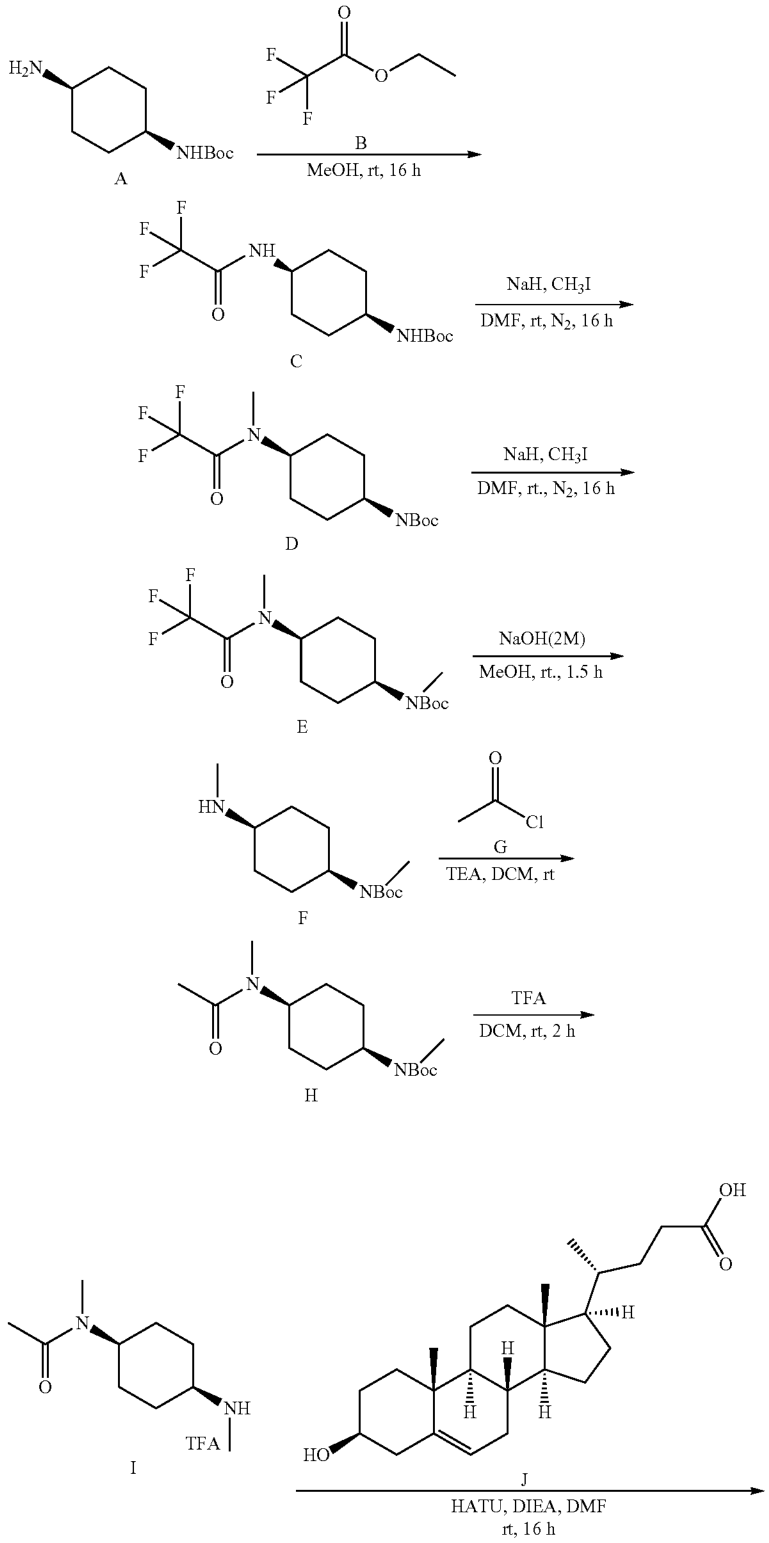

-continued

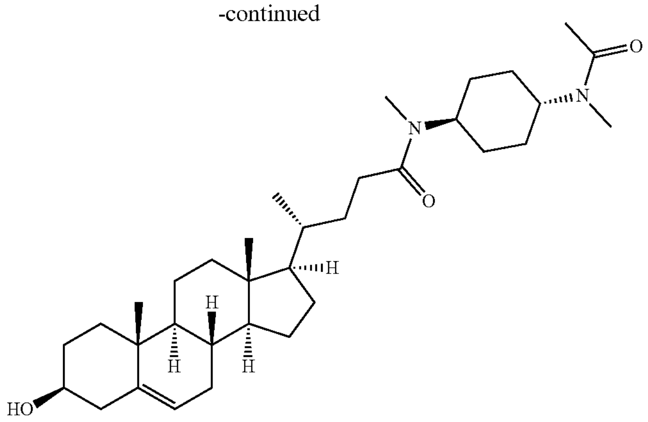

299

To a solution of compound A (1.0 g, 4.67 mmol) in MeOH (10 mL) was added compound B (1.7 mL, 14.29 mmol). The mixture was stirred at room temperature for 16 h. The reaction was quenched by $NaHCO_3$ and extracted with ethyl acetate. The organic layer was concentrated to give crude which was purified by silica gel chromatography to give compound C (1.0 g, 69%). To a solution of compound C (1.35 g, 4.35 mmol) in DMF (10 mL) was added NaH (696 mg, 17.4 mmol, 60% dispersion in oil) at 0° C. and stirred for 30 min. Then iodomethane (1.23 g, 8.7 mmol) was added at room temperature and stirred for 16 hours. The mixture was quenched by $NaHCO_3$ and extracted with ethyl acetate. The organic layer was concentrated to give crude which was purified by silica gel chromatography to give compound D (1.0 g, 70%).

To a solution of compound D (800 mg, 2.47 mmol) in DMF (10 mL) was added NaH (394 mg, 9.87 mmol, 60% dispersion in oil) at 0° C. and stirred for 30 min. Then iodomethane (0.7 g, 4.93 mmol) was added at room temperature and stirred for 16 hours. The mixture was quenched by saturated aqueous $NaHCO_3$ and extracted with ethyl acetate. The organic layer was concentrated to give crude which was purified by silica gel chromatography to give compound E (600 mg, 71%). To a solution of compound E (600 mg, 1.77 mmol) in methanol (6 mL) was added NaOH (2 mL, 4 mmol, 2 M in water). The mixture was stirred at room temperature for 1.5 hours. The mixture was diluted with water and extracted with EA. The organic layer was concentrated under vacuum to afford the crude compound F (400 mg, 93%).

To a solution of compound F (100 mg, 413 μmol) in DCM (2 mL) was added compound G (48.6 mg, 619 μmol) and triethylamine (125 mg, 1.24 mmol). After stirring at room temperature for 16 h, the mixture was diluted with water and extracted with EA. The organic layer was concentrated under vacuum and the residue was purified by silica gel chromatography to give compound H (39 mg, 33%). The solution of compound H (78 mg, 274 μmol) in TFA (1 mL) and DCM (2 mL) was stirred at room temperature for 2 h. The mixture was concentrated to afford compound I (60 mg, 95%).

To a solution of compound I (46 mg, 163 μmol) in DMF (1 mL) was added compound J (54.9 mg, 147 μmol), HATU (92.8 mg, 244 μmol) and DIEA (84.2 mg, 651 μmol). After stirring at room temperature for 16 h, the mixture was diluted with water and extracted with ethyl acetate. The organic layer was concentrated to give the crude which was purified by silica gel chromatography to give the title compound 299 (28 mg, 31%). $^1$H NMR (400 MHz, Chloroform-d) δ 5.36-5.33 (m, 1H), 3.56-3.48 (m, 1H), 3.01 (s, 3H), 2.98 (s, 3H), 2.49-2.19 (m, 8H), 2.16 (s, 3H), 2.04-1.65 (m, 15H), 1.64-1.37 (m, 10H), 1.36-1.26 (m, 5H), 1.21-1.10 (m, 3H), 1.09-1.02 (m, 2H), 1.00 (s, 3H), 0.96 (d, J=6.5 Hz, 3H), 0.91 (dd, J=17.3, 5.9 Hz, 1H), 0.68 (s, 3H). LCMS: M+1=541.4

Example 300: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-methoxypiperidin-1-yl)pentan-1-one

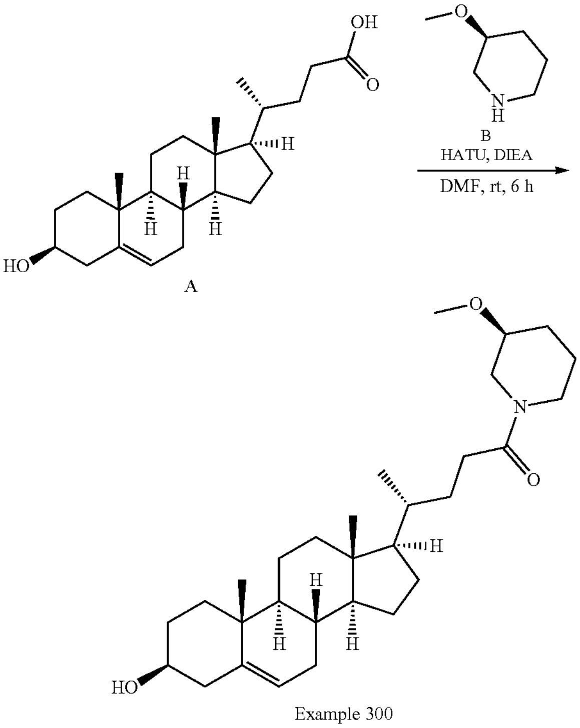

Example 300

To a solution of compound A (163 mg, 434 μmol) in DMF (4 mL) was added compound B (50 mg, 434 μmol), HATU (204 mg, 868 μmol) and DIEA (281 mg, 2.17 mmol). The mixture was stirred at room temperature for 6 hours. The mixture was diluted with water and extracted with ethyl acetate. The organic layer was concentrated to give crude which was purified by silica gel chromatography to the title compound 300 (60 mg, 29%). LCMS: [M+1]+=472.30. $^1$H NMR (400 MHz, Chloroform-d) δ 5.35 (d, J=5.0 Hz, 1H), 4.11-3.41 (m, 6H), 3.38 (s, 3H), 3.26-3.10 (m, 3H), 2.42-2.19 (m, 4H), 2.04-1.94 (m, 3H), 1.88-1.77 (m, 4H), 1.61-1.51 (m, 5H), 1.49-1.04 (m, 15H), 1.01 (s, 3H), 0.95 (d, J=6.6 Hz, 4H), 0.68 (s, 3H).

Example 301: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(pyridin-4-yloxy)piperidin-1-yl]pentan-1-one

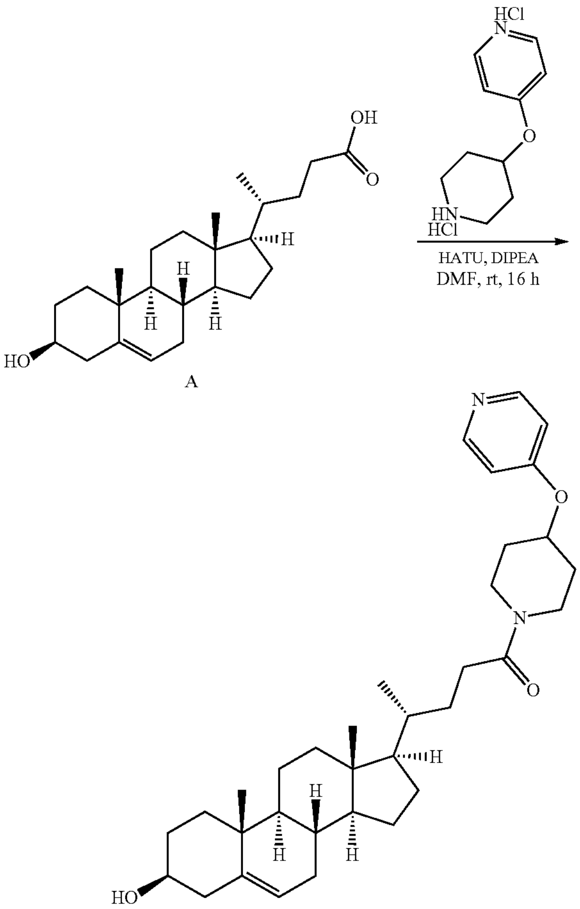

A

301

To a solution of compound A (74.6 mg, 199 μmol) in DMF (3 mL) was added DIEA (129 mg, 995 μmol), 4-(piperidin-4-yloxy)pyridine dihydrochloride (50 mg, 199 μmol) and HATU (151 mg, 398 μmol) at room temperature. The resulting mixture was stirred at room temperature for 16 h. The mixture was diluted with water and extracted with ethyl acetate. The organic layer was washed with water and brine, dried with sodium sulfate, and concentrated under vacuum to give crude product which was purified by silica gel chromatography (eluting with 20/1 DCM/MeOH) to give the title compound 301 (34.1 mg, 32.0%). $^1$H NMR (400 MHz, $CDCl_3$) δ 8.46 (d, J=5.6 Hz, 2H), 6.93 (d, J=5.6 Hz, 2H), 5.35 (d, J=5.0 Hz, 1H), 4.74-4.66 (m, 1H), 3.85-3.39 (m, 5H), 2.47-2.19 (m, 7H), 2.05-1.76 (m, 10H), 1.51-1.44 (m, 4H), 1.40-1.24 (m, 6H), 1.22-1.06 (m, 4H), 1.01 (s, 3H), 0.96 (d, J=6.4 Hz, 3H), 0.69 (s, 3H). LCMS: $[M+H]^+$=535.25.

Example 302: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyrimidin-4-yl)piperazin-1-yl)pentan-1-one

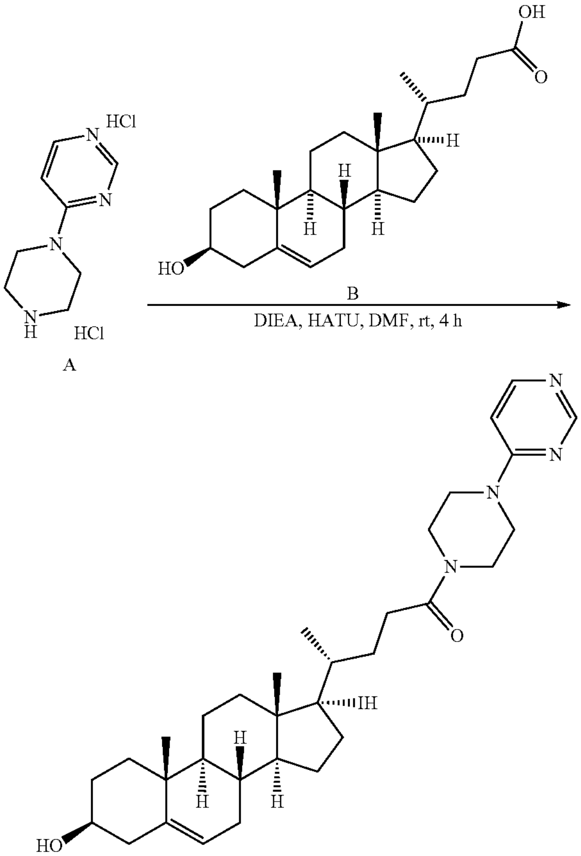

A

302

To a solution of compound A (200 mg, 843 μmol) in DMF (5 mL) was added compound B (284 mg, 759 μmol), DIEA (654 mg, 5.06 mmol) and HATU (641 mg, 1.69 mmol). After stirring at room temperature for 4 hours, the mixture was diluted with water and extracted with ethyl acetate. The organic layer was concentrated to give crude which was purified by silica gel chromatography to give the title compound 302 (80 mg, 18%). $^1$H NMR (400 MHz, Chloroform-d) δ 8.63 (s, 1H), 8.24 (d, J=6.3 Hz, 1H), 6.55 (dd, J=6.4, 1.2 Hz, 1H), 5.34 (dd, J=4.9, 2.6 Hz, 1H), 3.84-3.47 (m, 9H), 2.41 (td, J=10.5, 5.4 Hz, 1H), 2.34-2.17 (m, 3H), 2.03-1.94 (m, 2H), 1.90-1.76 (m, 4H), 1.61-1.43 (m, 7H), 1.41-1.25 (m, 3H), 1.22-1.03 (m, 5H), 1.01 (s, 3H), 0.97 (d, J=6.5 Hz, 3H), 0.95-0.86 (m, 1H), 0.69 (s, 3H). LCMS: $[M+1]^+$=521.30.

Example 303: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(pyridazin-3-yl)piperazin-1-yl]pentan-1-one

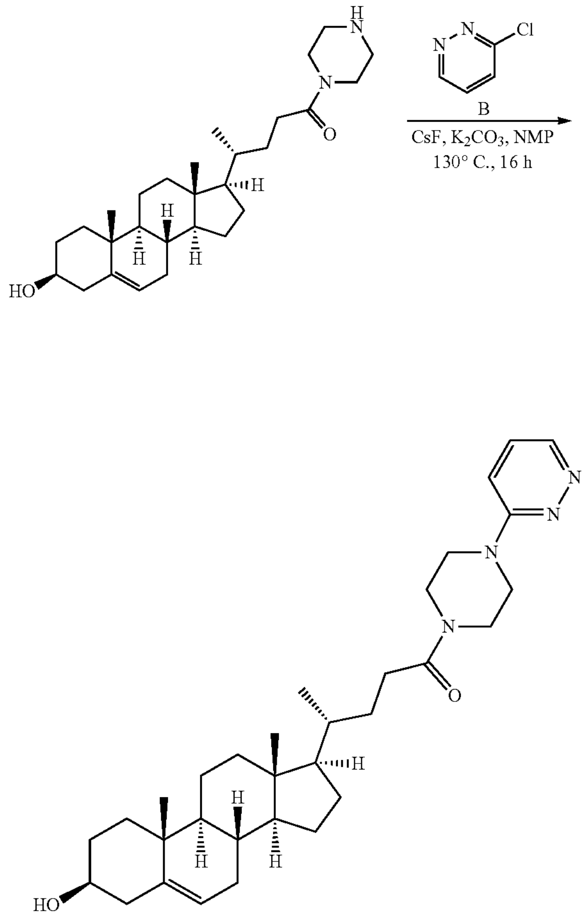

303

To a solution of compound A (100 mg, 226 μmol) in NMP (2 mL) was added compound B (25.9 mg, 226 μmol), cesium fluoride (103 mg, 678 μmol) and $K_2CO_3$ (156 mg, 1.13 mmol). The reaction mixture was stirred at 130° C. for 16 hours. The reaction was quenched with water and extracted with ethyl acetate (10 mL×4). The combined organic layer was concentrated to give the crude which was purified by silica gel chromatography to yield the title compound 303 (10 mg, 8.5%). LCMS:[M+Na]$^+$=521.25. $^1$H NMR (400 MHz, Methanol-$d_4$) δ 8.52 (d, J=4.4 Hz, 1H), 7.45 (dd, J=9.3,4.4 Hz, 1H), 7.31 (dd, J=9.4, 1.2 Hz, 1H), 5.34 (d, J=5.1 Hz, 1H), 3.73 (d, J=6.1 Hz, 6H), 3.65 (d, J=5.4 Hz, 2H), 3.40 (dq, J=10.9, 5.2 Hz, 1H), 2.51 (ddd, J=15.5, 10.6, 5.2 Hz, 1H), 2.37 (ddd, J=15.2, 10.3, 5.9 Hz, 1H), 2.26-2.18 (m, 2H), 2.08-1.85 (m, 4H), 1.83-1.74 (m, 2H), 1.69-1.43 (m, 7H), 1.41-1.26 (m, 6H), 1.22-1.07 (m, 4H), 1.02 (d, J=8.1 Hz, 6H), 0.92 (dt, J=18.2, 6.4 Hz, 2H), 0.74 (s, 3H).

Example 304: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyrazin-2-yl)piperazin-1-yl)pentan-1-one

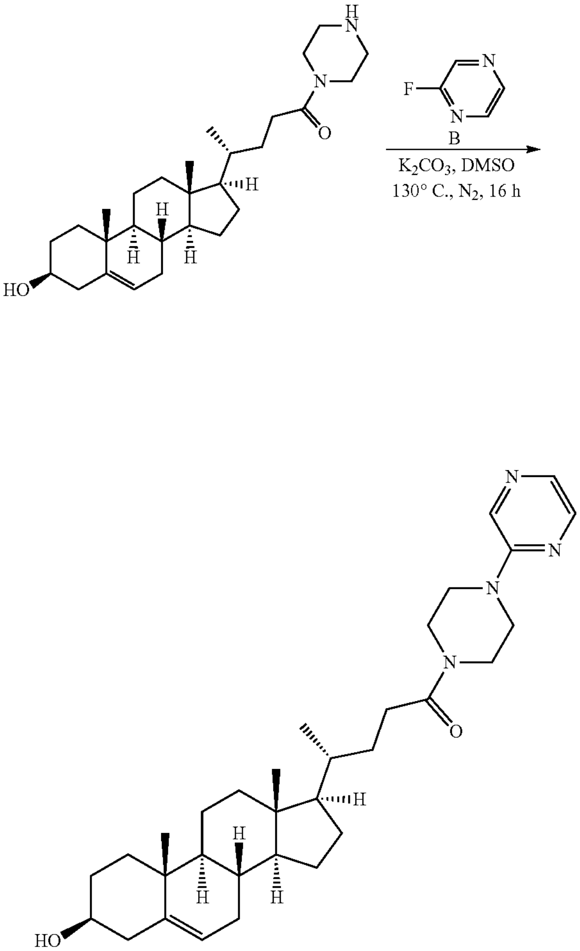

304

To a solution of compound A (190 mg, 429 μmol) in DMSO (3 mL) was added compound B (42.1 mg, 429 μmol) and K2CO3 (178 mg, 1.29 mmol). The mixture was stirred at 130° C. under $N_2$ for 16 h. The mixture was diluted with water and extracted with EA. The organic layer was washed with brine, dried over sodium sulfate, and concentrated to afford the crude which was purified by silica gel chromatography to afford the title compound 304 (20 mg, 10%). LCMS [M+1]=521.25. 1H NMR (400 MHz, Chloroform-d) δ 8.16 (s, 1H), 8.10 (s, 1H), 7.90 (d, J=2.6 Hz, 1H), 5.35 (d, J=5.1 Hz, 1H), 3.76 (bs, 2H), 3.66 (bs, 2H), 3.61 (bs, 4H), 3.56-3.48 (m, 1H), 2.47-2.18 (m, 4H), 2.04-1.03 (m, 28H), 1.01 (s, 3H), 0.97 (d, J=6.4 Hz, 3H), 0.96-0.84 (m, 2H), 0.69 (s, 3H).

Example 305: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyrimidin-2-yl)piperazin-1-yl)pentan-1-one

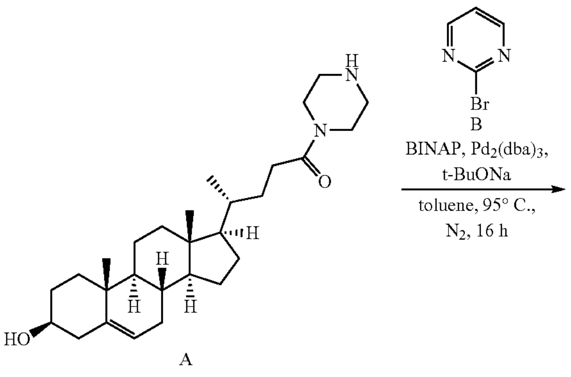

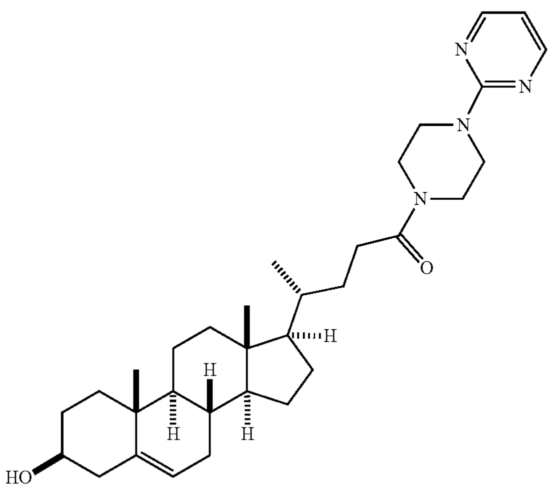

305

To a solution of compound A (300 mg, 0.67 mmol) in toluene (6 mL) was add 2-bromopyrimidine (108 mg, 0.67 mmol), BINAP (127 mg, 203 μmol), t-BuONa (65.1 mg, 0.67 mmol) and $Pd_2(dba)_3$ (124 mg, 0.136 mmol). The mixture was stirred at 95° C. under $N_2$ for 16 h. The reaction was quenched with saturated $NH_4Cl$ and extracted with EtOAc. The organic layer was washed with brine, dried over sodium sulfate, filtered, and concentrated. The mixture was purified by column chromatography on silica gel to afford the title compound 305 (14 mg, 4%) as a white solid. $^1H$ NMR (400 MHz, Methanol-$d_4$) δ 8.35 (d, J=4.8 Hz, 2H), 6.63 (t, J=4.8 Hz, 1H), 5.34 (d, J=5.2 Hz, 1H), 3.83 (dt, J=24.5, 5.4 Hz, 4H), 3.69-3.60 (m, 4H), 3.39 (dq, J=10.5, 5.5 Hz, 1H), 2.56-2.45 (m, 1H), 2.41-2.31 (m, 1H), 2.27-2.15 (m, 2H), 2.11-1.74 (m, 7H), 1.69-1.43 (m, 8H), 1.42-0.87 (m, 18H), 0.74 (s, 3H). LCMS: [M+H]=521.30.

Example 306: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(pyridin-3-yl)piperazin-1-yl]pentan-1-one

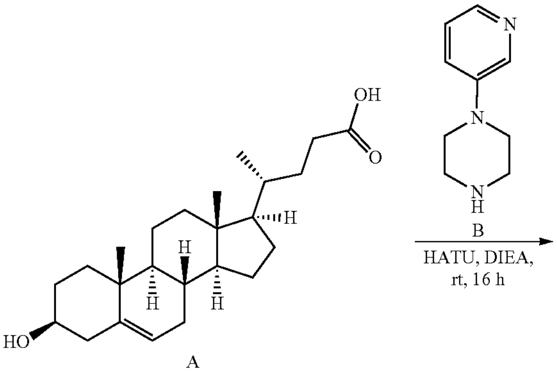

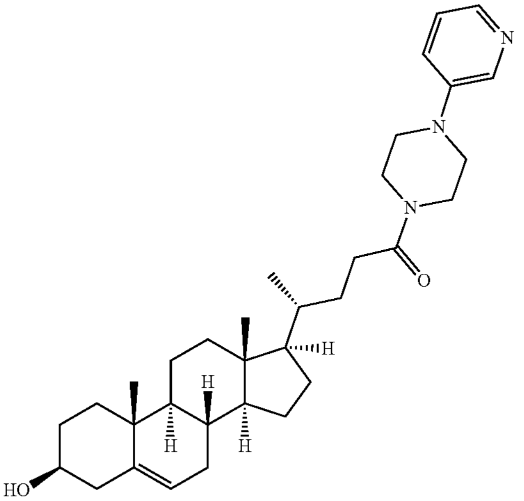

306

To a solution of compound A (500 mg, 1.33 mmol) in DMF (5 mL) was added compound B (242 mg, 1.48 mmol), DIEA (1.15 g, 8.9 mmol) and HATU (1.12 g, 2.97 mmol). The mixture was stirred at room temperature for 16 hours. The reaction was quenched with water and extracted with ethyl acetate (10 mL×4). The combined organic layer was concentrated to give the crude which was purified by silica gel chromatography to yield the title compound 306 (116 mg, 15%). LCMS:$[M+1]^+$=520.30. $^1H$ NMR (400 MHz, Chloroform-d) δ 8.31 (s, 1H), 8.17-8.10 (m, 1H), 7.24-7.17 (m, 2H), 5.34 (d, J=5.2 Hz, 1H), 3.87-3.72 (m, 2H), 3.70-3.59 (m, 2H), 3.58-3.45 (m, 1H), 3.30-3.12 (m, 4H), 2.49-2.36 (m, 1H), 2.32-2.18 (m, 3H), 2.08-1.93 (m, 4H), 1.90-1.76 (m, 4H), 1.63-1.40 (m, 7H), 1.38-1.24 (m, 3H), 1.21-1.03 (m, 5H), 1.00 (s, 3H), 0.97 (d, J=6.4 Hz, 3H), 0.93-0.89 (m, 1H), 0.69 (s, 3H).

Example 307: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyridin-2-yl)piperazin-1-yl)pentan-1-one

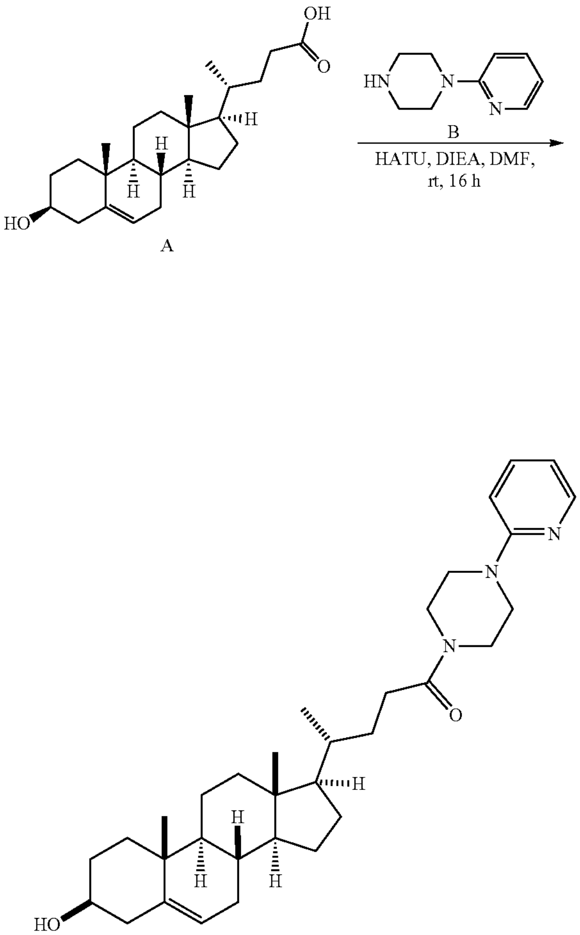

307

To a solution of compound A (300 mg, 0.8 mmol) in DMF (20 mL) was added compound B (145 mg, 0.89 mmol), DIEA (677 mg, 5.24 mmol) and HATU (677 mg, 1.78 mmol). The mixture was stirred at room temperature under $N_2$ for 16 h. The reaction was quenched with saturated $NH_4Cl$ and extracted with EtOAc. The organic layer was washed by brine, dried over sodium sulfate, filtered, and concentrated. The mixture was purified by column chromatography on silica gel to afford the title compound 307 (100 mg, 24%). $^1H$ NMR (400 MHz, Chloroform-d) δ 8.20 (d, J=4.7 Hz, 1H), 7.52-7.50 (m, 1H), 6.72-6.63 (m, 2H), 5.35 (d, J=5.2 Hz, 1H), 3.74 (t, J=5.4 Hz, 2H), 3.65-3.56 (m, 4H), 3.49 (t, J=5.5 Hz, 2H), 2.49-2.38 (m, 1H), 2.34-2.19 (m, 3H), 2.05-1.73 (m, 6H), 1.64-1.03 (m, 17H), 1.01 (s, 3H), 0.97 (d, J=6.5 Hz, 3H), 0.92 (dd, J=11.0, 5.3 Hz, 1H), 0.69 (s, 3H). LCMS: [M+H]=520.30.

Example 308: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(1-methyl-1H-1,2,3-triazole-4-carbonyl)piperazin-1-yl)pentan-1-one

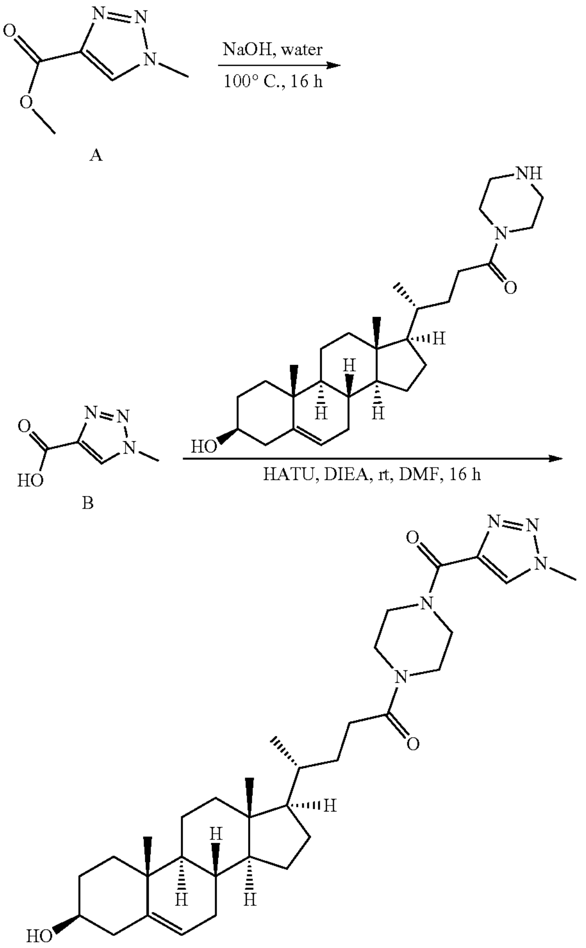

308

To a solution of compound A (100 mg, 0.71 mmol) in MeOH (3 mL) and water (1 mL) was added NaOH (85 mg, 2.1 mmol). The mixture was stirred at 100° C. for 16 h. The mixture was cooled down to rt and adjusted to pH=6-7 with 1M HCl, extracted with EA. The organic layer was concentrated to afford compound B (45 mg, 44%).

To a solution of compound B (45 mg, 0.3 mmol) in DMF (4 mL) was added C (157 mg, 354 μmol), HATU (269 mg, 0.7 mol) and DIEA (275 mg, 2.12 mmol). The mixture was stirred at room temperature under $N_2$ for 16 h. The reaction was diluted with water, extracted with EA. The organic layer was washed by brine, dried over sodium sulfate, filtered, and concentrated to afford the crude which was purified with silica gel chromatography to afford the title compound 308 (20 mg, 10%) as a white solid. $^1H$ NMR (400 MHz, Chloroform-d) δ 8.08 (d, J=9.6 Hz, 1H), 5.35 (d, J=4.8 Hz, 1H), 4.33 (d, J=33.6 Hz, 2H), 4.15 (s, 3H), 3.83-3.68 (m, 4H), 3.63-3.47 (m, 3H), 2.48-2.34 (m, 1H), 2.34-2.20 (m, 3H), 2.04-1.94 (m, 2H), 1.92-1.70 (m, 7H), 1.64-1.42 (m, 8H), 1.41-1.24 (m, 3H), 1.21-1.04 (m, 4H), 1.01 (s, 3H), 0.96 (d, J=6.4 Hz, 3H), 0.69 (s, 3H).

Example 309: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(1-methyl-1H-pyrazole-4-carbonyl)piperazin-1-yl]pentan-1-one

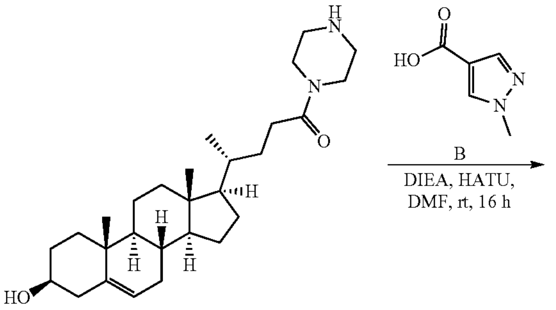

A

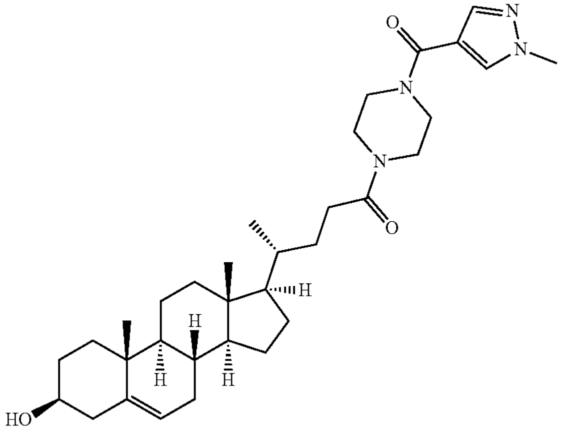

309

To a solution of compound A (200 mg, 452 μmol) in DMF (5 mL) was added compound B (38 mg, 301 μmol), DIEA (234 mg, 1.81 mmol) and HATU (229 mg, 904 μmol). The mixture was stirred at room temperature for 16 hours. The reaction was quenched with water and extracted with ethyl acetate (10 mL×4). The combined organic layer was concentrated to give the crude which was purified by silica gel chromatography to yield the title compound 309 (30 mg, 18%). LCMS:$[M+1]^+$=551.30. $^1H$ NMR (400 MHz, Methanol-$d_4$) δ 7.98 (s, 1H), 7.74 (s, 1H), 5.34 (d, J=5.2 Hz, 1H), 3.93 (s, 3H), 3.82-3.59 (m, 8H), 3.44-3.36 (m, 1H), 2.54-2.43 (m, 1H), 2.40-2.30 (m, 1H), 2.28-2.17 (m, 2H), 2.08-1.98 (m, 2H), 1.97-1.84 (m, 3H), 1.81-1.75 (m, 2H), 1.68-1.60 (m, 1H), 1.58-1.44 (m, 6H), 1.38-1.28 (m, 3H), 1.25-1.10 (m, 3H), 1.08-1.06 (m, 1H), 1.04-0.98 (m, 7H), 1.04-0.97 (m, 1H), 0.73 (s, 3H).

Example 310: (R)-1-(4-(1H-pyrazole-4-carbonyl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

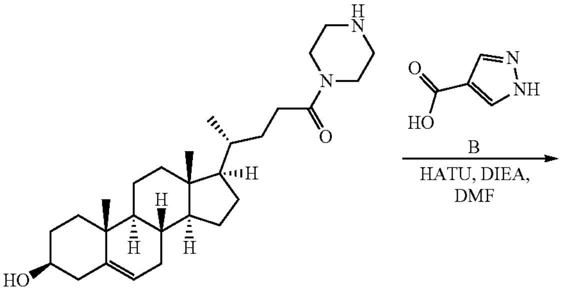

A

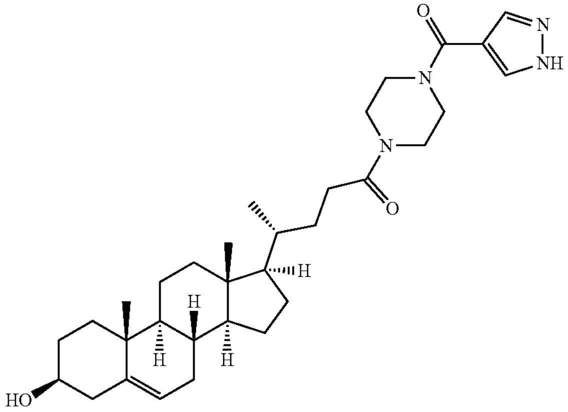

Example 310

To a mixture of compound A (235 mg, 491 μmol), compound B (50 mg, 446 μmol) and HATU (254 mg, 669 μmol) in DMF (2 mL) was added DIEA (173 mg, 1.34 mmol). The mixture was stirred at room temperature for 1 h. Water (10 mL) was added to the mixture and extracted with EtOAc (10 mL×3). The combined organic phase was washed by brine, dried over sodium sulfate, and concentrated under vacuum. The residue was purified by Prep-HPLC to afford the title compound 310 (36.3 mg, 15%) as a white solid. $^1H$ NMR (400 MHz, DMSO-$d_6$) δ 13.21 (s, 1H), 8.09 (s, 1H), 7.73 (s, 1H), 5.26 (d, J=4.8 Hz, 1H), 4.58 (d, J=4.4 Hz, 1H), 3.61 (bs, 2H), 3.56 (bs, 2H), 3.49 (bs, 4H), 3.28-3.21 (m, 1H), 2.38-2.31 (m, 1H), 2.27-2.06 (m, 3H), 1.99-1.61 (m, 6H), 1.56-0.97 (m, 14H), 0.94 (s, 3H), 0.91 (d, J=6.4 Hz, 3H), 0.86 (dd, J=11.4, 4.8 Hz, 1H), 0.65 (s, 3H).

Example 311: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(isothiazole-5-carbonyl)piperazin-1-yl)pentan-1-one

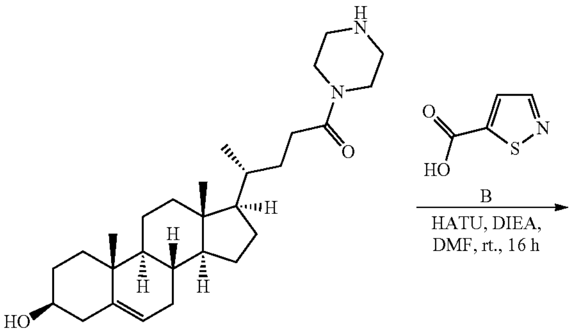

A

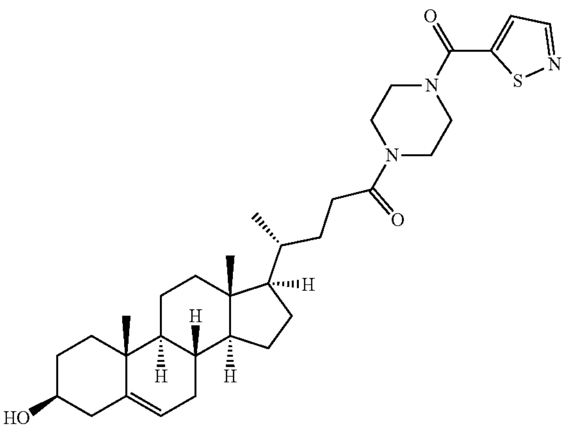

311

To a solution of compound A (500 mg, 1.13 mmol) and compound B (146 mg, 1.13 mmol) in DMF (6 mL) was added HATU (644 mg, 1.69 mmol) and DIEA (438 mg, 3.39 mmol). The mixture was stirred at room temperature for 16 hours. After completion, the mixture was quenched by adding saturated ammonium chloride solution (20 mL) and extracted with ethyl acetate (20 mL×3). The combined organic layer was washed with brine, dried over sodium sulfate, filtered, and concentrated to give the crude which was purified by column chromatography on silica gel to yield the title compound 311 (171 mg, 27.3%) as a white solid. LCMS: $[M+H]^+$=554.25. $^1$H NMR (400 MHz, Chloroform-d) δ 8.49 (d, J=1.6 Hz, 1H), 7.38 (d, J=1.6 Hz, 1H), 5.35 (d, J=5.0 Hz, 1H), 3.81-3.47 (m, 9H), 2.45-2.36 (m, 1H), 2.32-2.20 (m, 3H), 2.03-1.95 (m, 2H), 1.91-1.74 (m, 4H), 1.57-1.44 (m, 6H), 1.42-1.24 (m, 4H), 1.21-1.06 (m, 4H), 1.01 (s, 3H), 0.96 (d, J=6.4 Hz, 3H), 0.93-0.86 (m, 1H), 0.69 (s, 3H).

Example 312: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyridazine-4-carbonyl)piperazin-1-yl) pentan-1-one

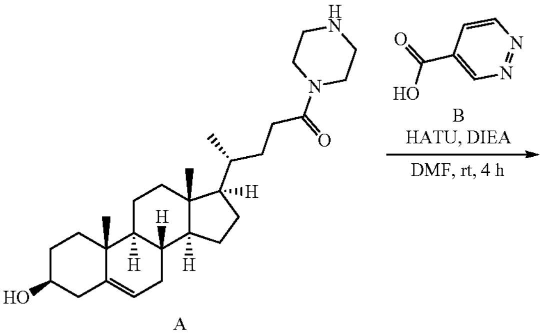

A

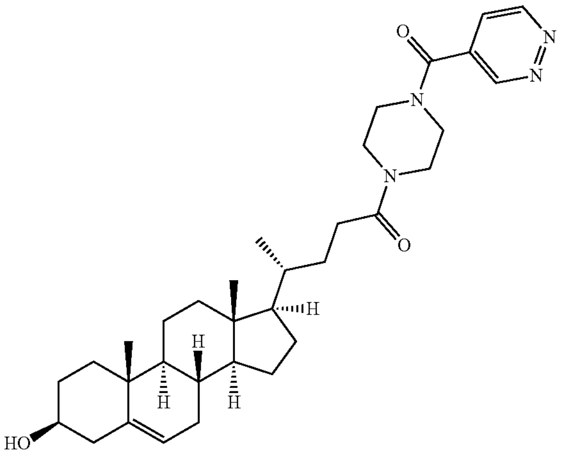

Example 312

To a solution of compound A (357 mg, 806 μmol) in DMF (6 mL) was added compound B (100 mg, 806 μmol), HATU (379 mg, 1.61 mmol) and DIEA (521 mg, 4.03 mmol). After stirring at room temperature for 4 hours, the mixture was diluted with water and was extracted with ethyl acetate. The organic layer was concentrated to give crude which was purified by silica gel chromatography to give the title compound 312 (56 mg, 13%). LCMS: [M+1]+=531.30. $^1$H NMR (400 MHz, Chloroform-d) δ9.35 (dd, J=5.2, 1.2 Hz, 1H), 9.23 (dd, J=2.2, 1.2 Hz, 1H), 7.50 (d, J=5.0 Hz, 1H), 5.35 (d, J=5.0 Hz, 1H), 3.87-3.29 (m, 9H), 2.50-2.16 (m, 4H), 2.04-1.74 (m, 6H), 1.64-1.04 (m, 16H), 1.01 (s, 3H), 0.97-0.93 (m, 3H), 0.69 (s, 3H).

Example 313: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(pyridine-3-carbonyl)piperazin-1-yl]pentan-1-one

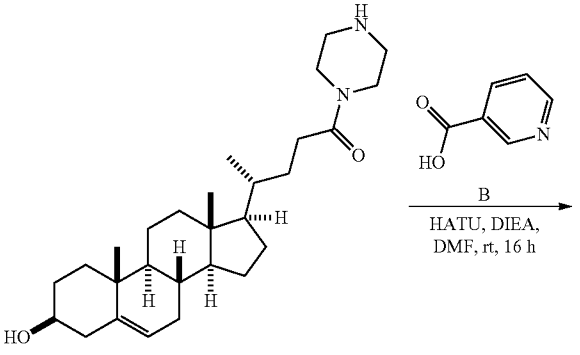

A

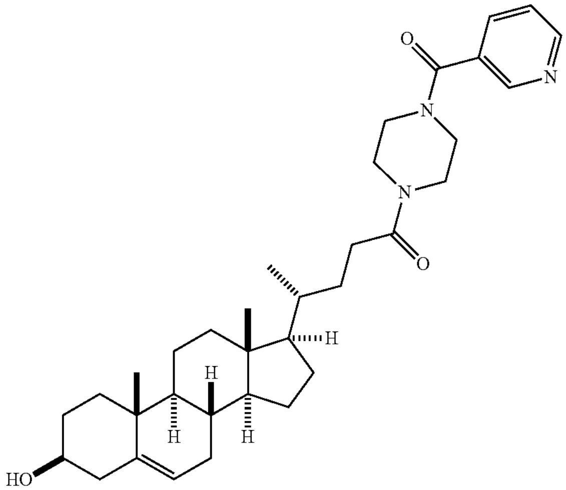

313

To a solution of compound A (100 mg, 226 μmol) in DMF (2 mL) was added compound B (33.4 mg, 271 μmol), HATU (129 mg, 339 μmol) and DIEA(0.4 mL, 2.26 mmol) at room temperature and stirred for 16 h. The mixture was diluted with water and extracted with ethyl acetate. The organic layer was concentrated, and the residue was purified by silica gel chromatography to give example 313 (20 mg, 16%). $^1$H NMR (400 MHz, Chloroform-d) δ 8.70 (s, 2H), 7.81 (d, J=7.8 Hz, 1H), 7.55-7.37 (m, 1H), 5.35 (d, J=5.1 Hz, 1H), 3.90-3.36 (m, 9H), 2.49-2.14 (m, 5H), 2.06-1.92 (m, 3H), 1.91-1.72 (m, 6H), 1.65-1.54 (m, 2H), 1.48-1.43 (m, 2H), 1.39-1.23 (m, 4H), 1.22-1.04 (m, 4H), 1.01 (s, 3H), 0.96 (d, J=6.4 Hz, 3H), 0.69 (s, 3H). LCMS:M+1=548.4.

Example 314: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-(4-cyclopropanecarbonylpiperazin-1-yl)pentan-1-one

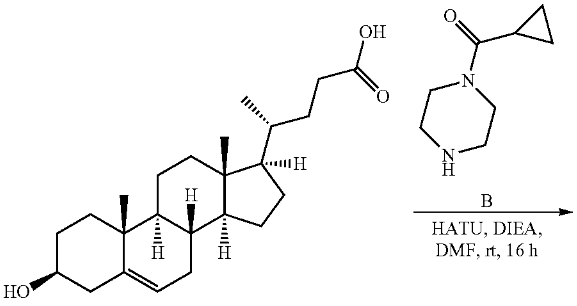

A

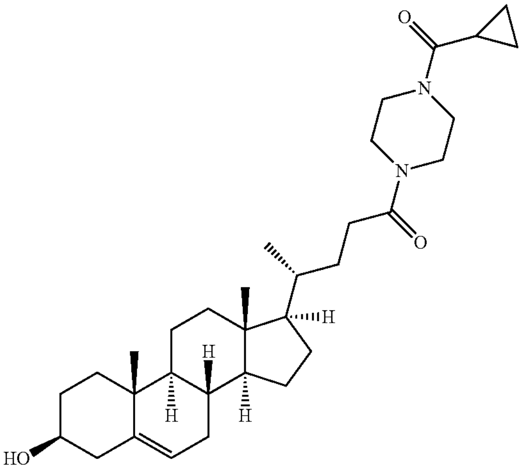

314

To a solution of compound A (300 mg, 0.801 mmol) and compound B (185 mg, 1.2 mmol) in DMF (8 mL) was added HATU (457 mg, 1.2 mmol) and DIEA (270 mg, 2.4 mmol). The mixture was stirred at room temperature for 16 hours. After completion, the mixture was quenched by adding saturated ammonium chloride solution (30 mL) and extracted with ethyl acetate (10 mL×3). The combined organic layer was washed with brine, dried over sodium sulfate, filtered, and concentrated to give the crude which was purified by column chromatography on silica gel to yield the title compound 314 (250 mg, 61%) as a white solid. LCMS: $[M+1]^+$=511.30. $^1$H NMR (400 MHz, Chloroform-d) δ 5.37-5.32 (m, 1H), 3.74-3.41 (m, 9H), 2.45-2.17 (m, 4H), 2.06-1.93 (m, 2H), 1.90-1.69 (m, 5H), 1.55-1.42 (m, 6H), 1.40-1.24 (m, 3H), 1.20-1.04 (m, 4H), 1.01 (s, 6H), 0.96 (d, J=6.4 Hz, 3H), 0.83-0.76 (m, 2H), 0.69 (s, 3H).

Example 315: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-isobutyrylpiperazin-1-yl)pentan-1-one

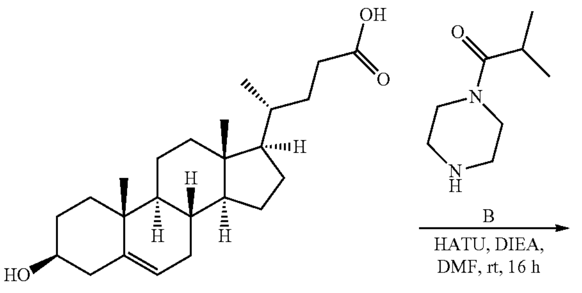

A

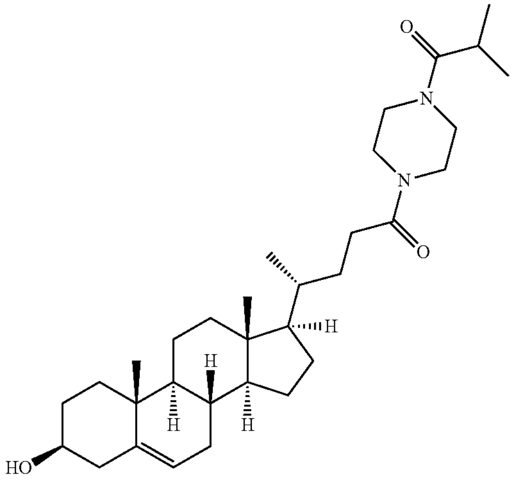

315

To a solution of compound A (109 mg, 291 μmol) and compound B (50 mg, 320 μmol) in DMF (3 mL) was added HATU (137 mg, 582 μmol) and DIEA (188 mg, 1.45 mmol). The mixture was stirred at room temperature for 16 hours. After completion, the mixture was quenched by adding saturated ammonium chloride solution (20 mL) and extracted with ethyl acetate (20 mL×3). The combined organic layer was washed with brine, dried over sodium sulfate, filtered, and concentrated to give the crude which was purified by column chromatography on silica gel to yield the title compound 315 (94 mg, 63%) as a white solid. LCMS: $[M+H]^+$=513.30. $^1H$ NMR (400 MHz, Chloroform-d) δ 5.35 (d, J=5.0 Hz, 1H), 3.71-3.40 (m, 9H), 2.85-2.74 (m, 1H), 2.47-2.35 (m, 1H), 2.33-2.20 (m, 3H), 2.03-1.94 (m, 2H), 1.92-1.68 (m, 9H), 1.64-1.41 (m, 6H), 1.36-1.29 (m, 2H), 1.27-1.25 (m, 1H), 1.14 (d, J=6.8 Hz, 6H), 1.12-1.06 (m, 2H), 1.01 (s, 3H), 0.96 (d, J=6.4 Hz, 3H), 0.69 (s, 3H).

Example 316: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-isopropylpiperazin-1-yl)pentan-1-one

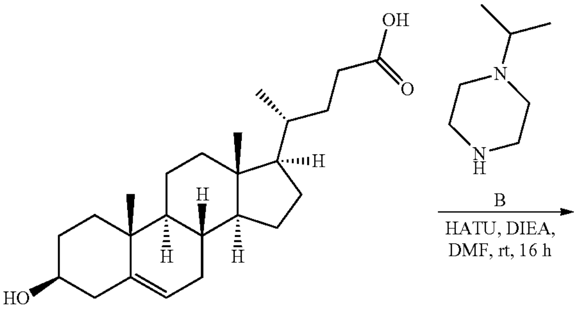

A

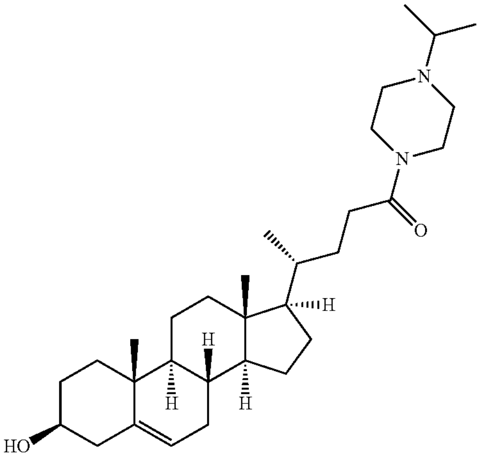

316

To a solution of compound A (300 mg, 801 μmol) and compound B (123 mg, 961 μmol) in DMF (6 mL) was added HATU (377 mg, 1.6 mmol) and DIEA (518 mg, 4 mmol). The mixture was stirred at room temperature for 16 hours. After completion, the mixture was quenched by adding saturated ammonium chloride solution (20 mL) and extracted with ethyl acetate (20 mL×3). The organic layer was washed with brine, dried over sodium sulfate, filtered, and concentrated to give the crude which was purified by column chromatography on silica gel to yield the title compound 316 (80 mg, 20.6%) as a white solid. LCMS: $[M+H]^+$=485.30. 1H NMR (400 MHz, Chloroform-d) δ 5.35 (d, J=5.0 Hz, 1H), 3.67 (bs, 2H), 3.57-3.47 (m, 3H), 2.86-2.75 (m, 1H), 2.63-2.49 (m, 4H), 2.52-2.17 (m, 4H), 2.04-1.12 (m, 21H), 1.09 (d, J=6.6 Hz, 6H), 1.01 (s, 3H), 0.95 (d, J=6.4 Hz, 3H), 0.68 (s, 3H).

Example 317: (R)-1-(4-acetyl-1,4-diazepan-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

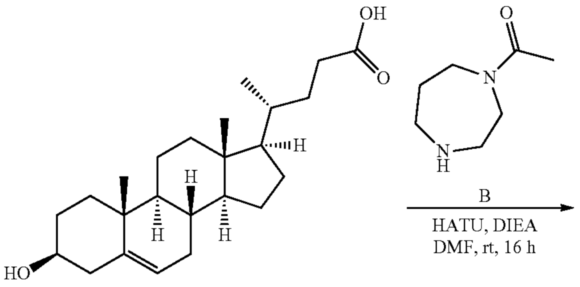

A

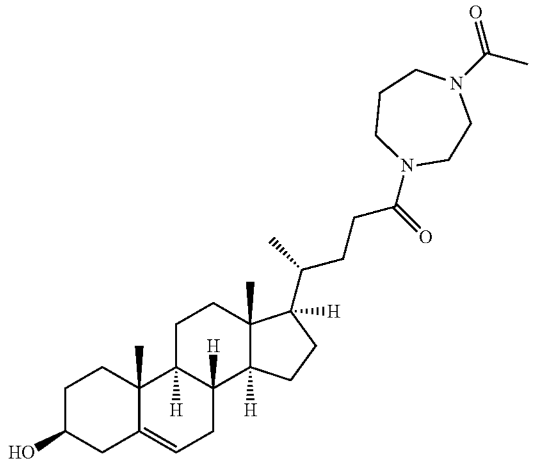

317

To a solution of compound A (200 mg, 534 μmol) in DMF (3 mL) was added compound B (75.9 mg, 534 μmol), DIEA (345 mg, 2.67 mmol) and HATU (305 mg, 801 μmol). The mixture was stirred at room temperature 16 h. The mixture was added water and extracted with EA. The organic layer was washed with brine, dried over sodium sulfate, and concentrated to afford the crude was purified by silica gel chromatography to afford the title compound 317 (176.5 mg, 66.3%). LCMS [M+1]=499.30. $^1$H NMR (400 MHz, Chloroform-d) δ 5.35 (d, J=5.1 Hz, 1H), 3.70-3.44 (m, 9H), 2.38-2.17 (m, 4H), 2.13-2.07 (m, 3H), 2.04-1.90 (m, 3H), 1.89-1.54 (m, 10H), 1.54-1.28 (m, 10H), 1.25 (s, 2H), 1.21-1.03 (m, 5H), 1.00 (s, 3H), 0.94-0.84 (m, 5H), 0.73-0.65 (m, 3H).

Example 318: (4R)-1-[(3aR,6aS)-5-acetyl-octahydropyrrolo[3,4-c]pyrrol-2-yl]-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentan-1-one

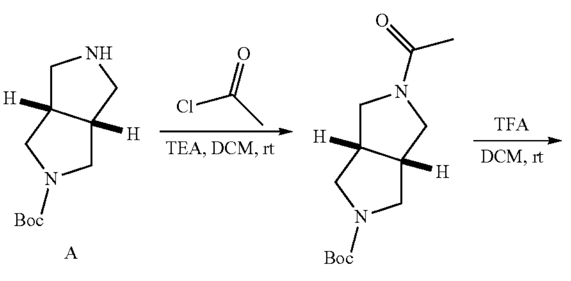

A B

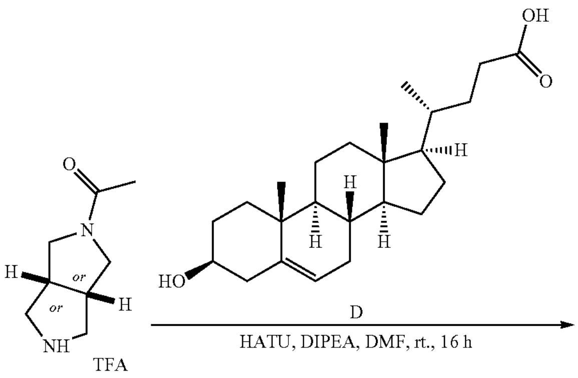

C

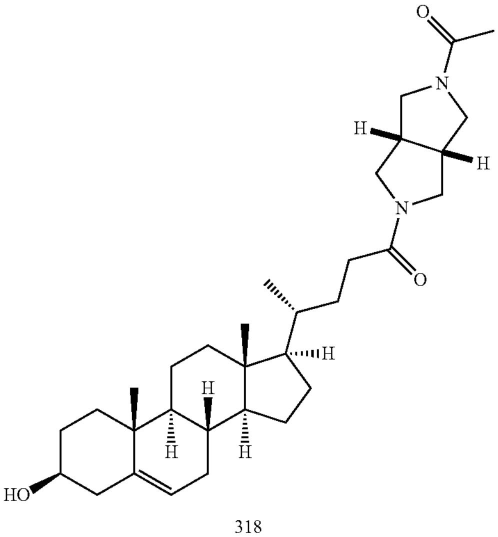

318

To a solution of compound A (500 mg, 2.36 mmol) in dichloromethane (7 mL) was added triethylamine (358 mg, 3.53 mmol) and acetyl chloride (222 mg, 2.83 mmol) at −10° C. The resulting mixture was stirred at room temperature for 3 h. Then reaction was the quenched with a saturated aqueous $NaHCO_3$ solution and extracted with DCM. The organic layer was dried with sodium sulfate and concentrated under vacuum to give compound B (600 mg, 90.1%).

To a solution of compound B (300 mg, 1.06 mmol) in dichloromethane (4.5 mL) was added trifluoroacetic acid (1.5 mL) at room temperature and stirred for 3 h. The mixture was concentrated under vacuum to give crude compound C (333 mg, 91.5%).

To a solution of compound D (350 mg, 934 μmol) in DMF (11.9 mL) was added DIEA (604 mg, 4.67 mmol), compound C (236 mg, 934 μmol) and HATU (711 mg, 1.87 mmol) at room temperature. The resulting mixture was stirred at room temperature for 16 h. The mixture was diluted with water and extracted with ethyl acetate. The organic layer was washed with water and brine, dried with sodium sulfate, and concentrated under vacuum to give crude product which was purified by silica gel chromatography (eluting with 1/20 MeOH/DCM) to give the title compound 318 (136 mg, 28.5%). $^1H$ NMR (400 MHz, $CDCl_3$) δ 5.35 (s, 1H), 3.77-3.67 (m, 4H), 3.56-3.29 (m, 5H), 3.09-2.82 (m, 2H), 2.40-2.08 (m, 5H), 2.05 (s, 3H), 2.03-1.77 (m, 6H), 1.52-1.06 (m, 15H), 1.00 (s, 3H), 0.94 (d, J=6.4 Hz, 3H), 0.68 (s, 3H).

Example 319: N-(1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)-N-methylacetamide

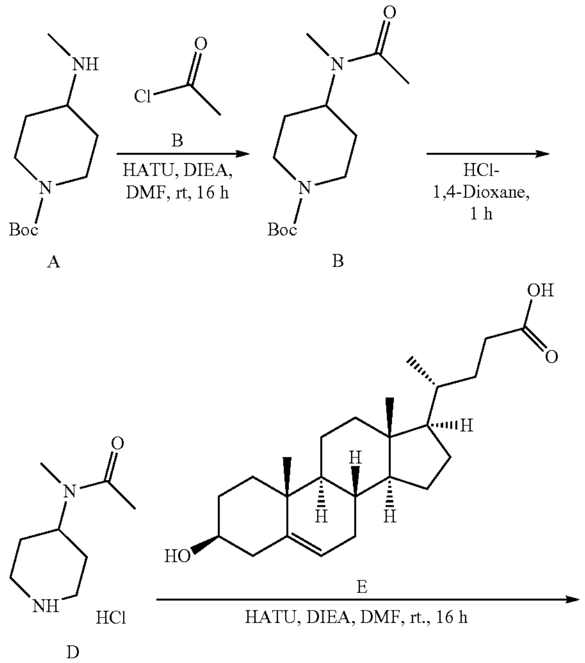

-continued

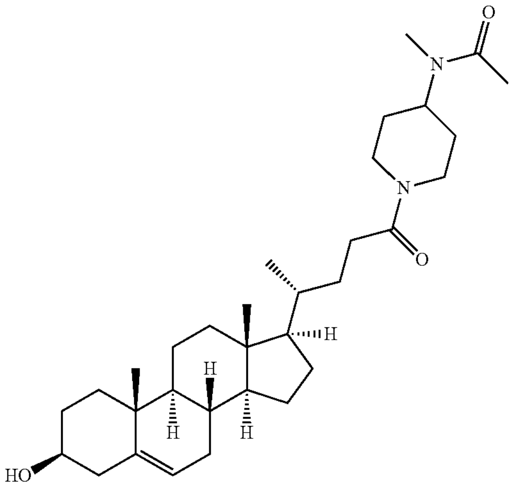

319

To a solution of compound A (500 mg, 2.33 mmol) in dichloromethane (5 mL) was added triethylamine (708 mg, 7 mmol) and compound B (201 mg, 2.57 mmol) at 0° C. The reaction mixture was stirred at room temperature for 16 hours. After completion, the mixture was quenched by adding water (15 mL) and extracted with DCM (10 mL×3). The organic layer was washed with brine, dried over sodium sulfate, filtered, and concentrated to give the crude which was purified by column chromatography on silica gel to yield the title compound C (300 mg, 50.2%) as a white solid.

HCl (0.5 mL, 2 mmol, 4M in dioxane) was added slowly to the compound C (100 mg, 390 μmol) in DCM (3 mL) at room temperature and stirred for 1 hour. After completion, the reaction mixture was concentrated to give the title compound D (80 mg) as a solid.

To a solution of compound E (77.8 mg, 208 μmol) and compound D (80 mg, 415 μmol) in DMF (2 mL) was added HATU (147 mg, 624 μmol) and DIEA (202 mg, 1.56 mmol). The mixture was stirred at room temperature for 16 hours. After completion, the mixture was quenched by adding saturated ammonium chloride solution (20 mL) and extracted with ethyl acetate (20 mL×3). The organic layer was washed with brine, dried over sodium sulfate, filtered, and concentrated to give the crude which was purified by column chromatography on silica gel to yield the title compound 319 (70.5 mg, 44%) as a white solid. LCMS: $[M+H]^+$=513.30. $^1H$ NMR (400 MHz, Chloroform-d) δ 5.35 (d, J=5.1 Hz, 1H), 4.87-4.63 (m, 2H), 4.01-3.88 (m, 1H), 3.57-3.46 (m, 1H), 3.12 (t, J=13.4 Hz, 1H), 2.82-2.78 (m, 3H), 2.58 (t, J=12.9 Hz, 1H), 2.46-1.66 (m, 14H), 1.58-1.05 (m, 17H), 1.00 (s, 3H), 0.95 (d, J=6.6 Hz, 3H), 0.94-0.84 (m, 1H), 0.68 (s, 3H).

Example 320: N-(1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)acetamide

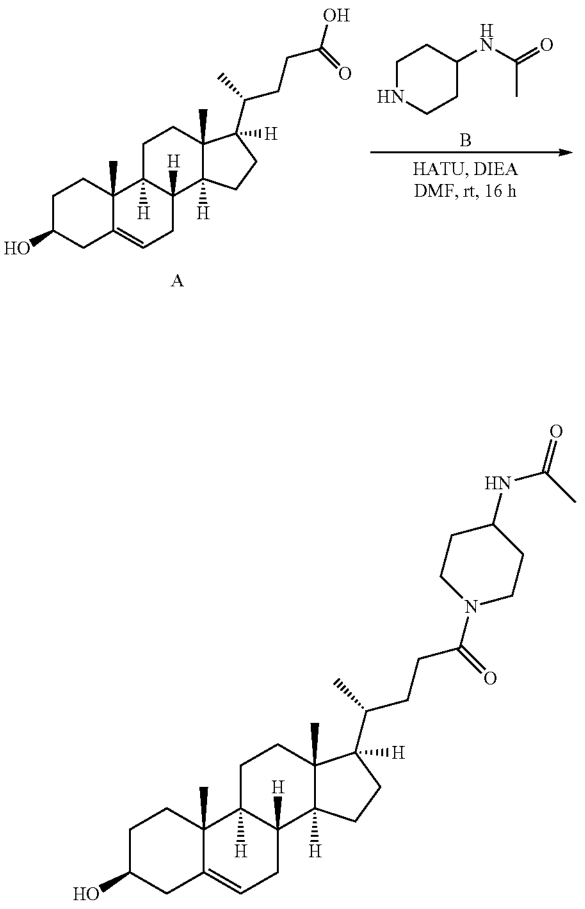

A

320

To a solution of compound A (200 mg, 534 μmol) in DMF (3 mL) was added compound B (75.9 mg, 534 μmol), DIEA (345 mg, 2.67 mmol) and HATU (305 mg, 801 μmol). The mixture was stirred at room temperature for 16 h. The reaction was quenched with water and extracted with EA. The organic layer was washed with brine, dried over sodium sulfate, and concentrated to afford the crude which was purified by silica gel chromatography to afford the title compound 320 (167.9 mg, 63%). LCMS [M+1]=499.25. $^1$H NMR (400 MHz, Chloroform-d) δ 5.39 (d, J=8.0 Hz, 1H), 5.35 (d, J=5.6 Hz, 1H), 4.56 (d, J=13.7 Hz, 1H), 4.04-3.93 (m, 1H), 3.81 (d, J=13.8 Hz, 1H), 3.57-3.46 (m, 1H), 3.12 (t, J=12.9 Hz, 1H), 2.69 (t, J=12.7 Hz, 1H), 2.41-2.27 (m, 2H), 2.26-2.17 (m, 2H), 2.07-2.01 (m, 2H), 1.98 (s, 3H), 1.96-1.72 (m, 7H), 1.67-1.53 (m, 5H), 1.52-1.40 (m, 6H), 1.36-1.18 (m, 7H), 1.17-1.02 (m, 5H), 1.00 (s, 3H), 0.95 (d, J=6.6 Hz, 4H), 0.68 (s, 3H).

Example 321: N—((S)-1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)pyrrolidin-3-yl)-N-methylacetamide

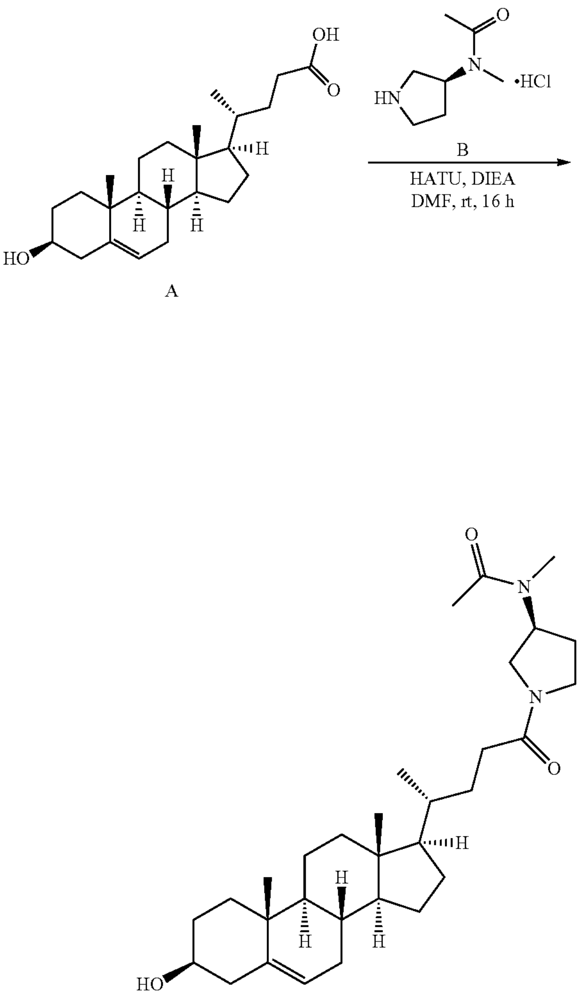

A

321

To a solution of compound A (200 mg, 534 μmol) in DMF (3 mL) was added compound B (75.9 mg, 534 μmol), DIEA (345 mg, 2.67 mmol) and HATU (305 mg, 801 μmol). The mixture was stirred at room temperature for 16 h. The reaction was quenched with water and extracted with EA. The organic layer was washed with brine, dried over sodium sulfate, and concentrated. The crude was purified by silica gel chromatography to afford the title compound 321 (176.8 mg, 66.4%). LCMS [M+1]=499.30. $^1$H NMR (400 MHz, Chloroform-d) δ 5.35 (d, J=4.3 Hz, 1H), 5.27-5.16 (m, 1H), 3.80-3.19 (m, 5H), 2.95-2.83 (m, 3H), 2.34-1.92 (m, 11H), 1.88-1.02 (m, 27H), 1.00 (s, 3H), 0.94 (t, J=5.9 Hz, 3H), 0.68 (s, 3H).

Example 322: N—((S)-1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)pyrrolidin-3-yl)acetamide

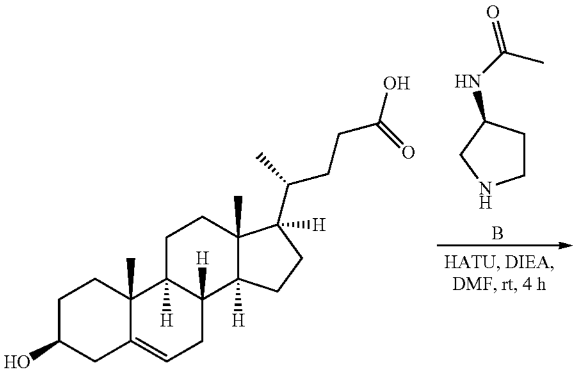

A

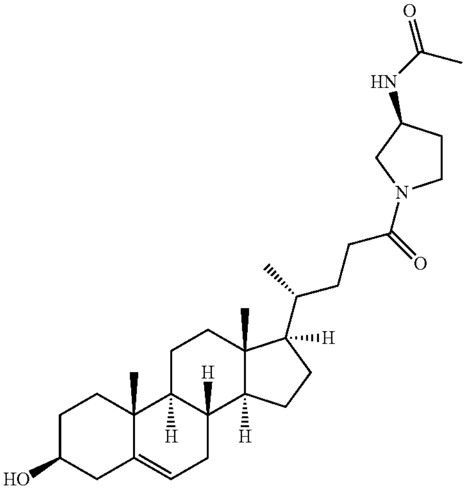

Example 322

To a solution of compound A (292 mg, 780 μmol) in DMF (6 mL) was added compound B (100 mg, 780 μmol), HATU (367 mg, 1.56 mmol) and DIEA (504 mg, 3.9 mmol). After stirring at room temperature for 4 hours, the mixture was diluted with water and extracted with ethyl acetate. The organic layer was concentrated to give crude which was purified by silica gel chromatography to give the title compound 322 (186 mg, 49%). LCMS: [M+1]+=485.30. $^1$H NMR (400 MHz, Chloroform-d) δ 5.67 (bs, 1H), 5.35 (d, J=5.2 Hz, 1H), 4.55-4.41 (m, 1H), 3.78-3.27 (m, 5H), 2.36-2.06 (m, 4H), 2.04-1.93 (m, 5H), 1.88-1.78 (m, 3H), 1.62-1.02 (m, 18H), 1.01 (s, 3H), 0.95 (d, J=6.4 Hz, 3H), 0.68 (d, J=2.8 Hz, 3H).

Example 323: N—((R)-1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)pyrrolidin-3-yl)-N-methylacetamide

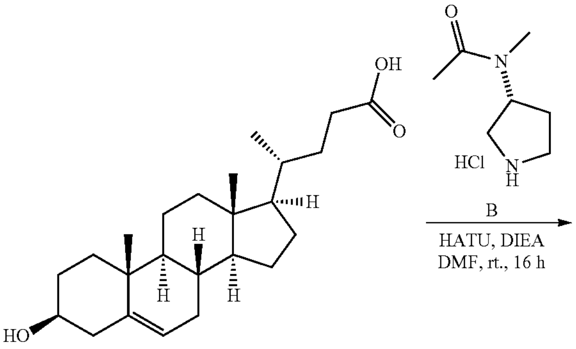

A

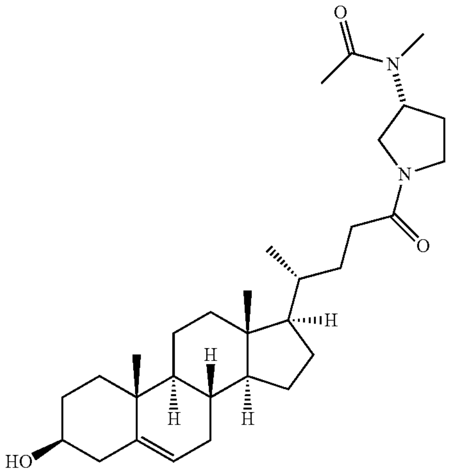

323

To a mixture of compound B (49.8 mg, 279 μmol), compound A (95 mg, 254 μmol) and HATU (145 mg, 380 μmol) in DMF (1.81 mL) was added DIEA (82.9 μL, 475 μmol). The mixture was stirred at room temperature for 16 h. The reaction was quenched with water and extracted with EA. The organic layer was washed with brine, dried over sodium sulfate, and concentrated to afford the crude which was purified by Prep-HPLC to afford the title compound 323 (20.4 mg, 16%). LCMS [M+1]=499.25. $^1$H NMR (400 MHz, Chloroform-d) δ 5.35 (s, 1H), 5.27-5.15 (m, 1H), 3.81-3.17 (m, 5H), 2.96-2.82 (m, 3H), 2.35-1.73 (m, 15H), 1.58-1.03 (m, 14H), 1.00 (s, 3H), 0.94 (d, J=6.2 Hz, 3H), 0.92-0.86 (m, 1H), 0.68 (s, 3H).

Example 324: N-[(3R)-1-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]pyrrolidin-3-yl]acetamide

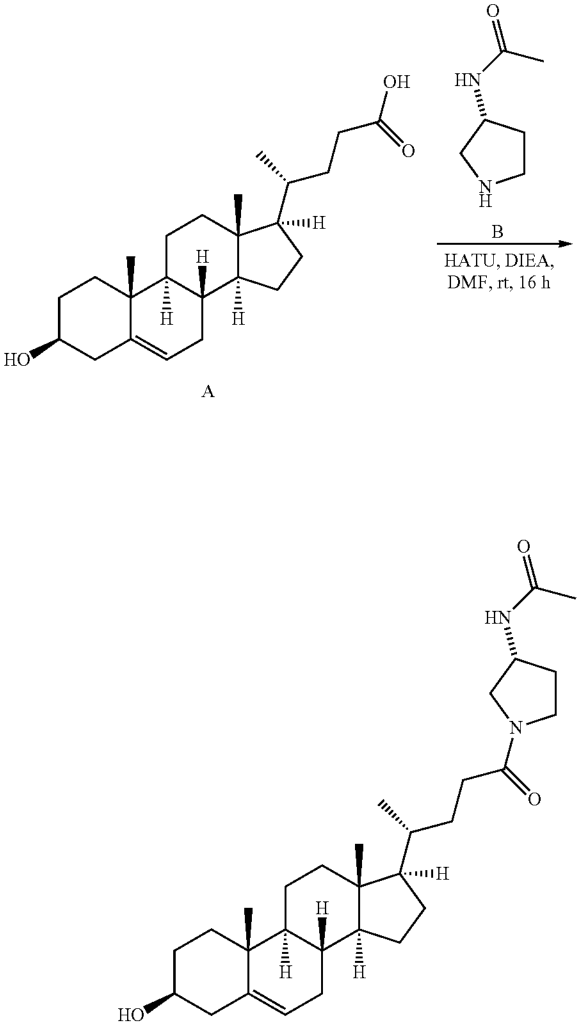

324

To a solution of compound A (100 mg, 267 μmol) in DMF (2 mL) was added compound B (41.1 mg, 320 μmol), HATU (152 mg, 0.4 mmol) and DIEA (138 mg, 1.07 mmol). After stirring at room temperature for 16 hours, the mixture was diluted with water and extracted with ethyl acetate. The organic layer was concentrated, and the residue was purified by silica gel chromatography to give the title compound 324 (20 mg, 15%). $^1$H NMR (400 MHz, Chloroform-d) δ 5.89 (dd, J=23.5, 5.6 Hz, 1H), 5.34 (d, J=5.1 Hz, 1H), 4.47 (dd, J=21.7, 5.3 Hz, 1H), 3.85-3.16 (m, 5H), 2.36-2.09 (m, 5H), 2.04-1.92 (m, 6H), 1.91-1.71 (m, 6H), 1.63-1.54 (m, 2H), 1.49-1.39 (m, 3H), 1.38-1.24 (m, 2H), 1.22-1.03 (m, 4H), 1.00 (s, 3H), 0.95-0.89 (m, 4H), 0.68 (s, 3H). LCMS:M+1=485.4.

Example 325: N-(1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)azetidin-3-yl)-N-methylacetamide

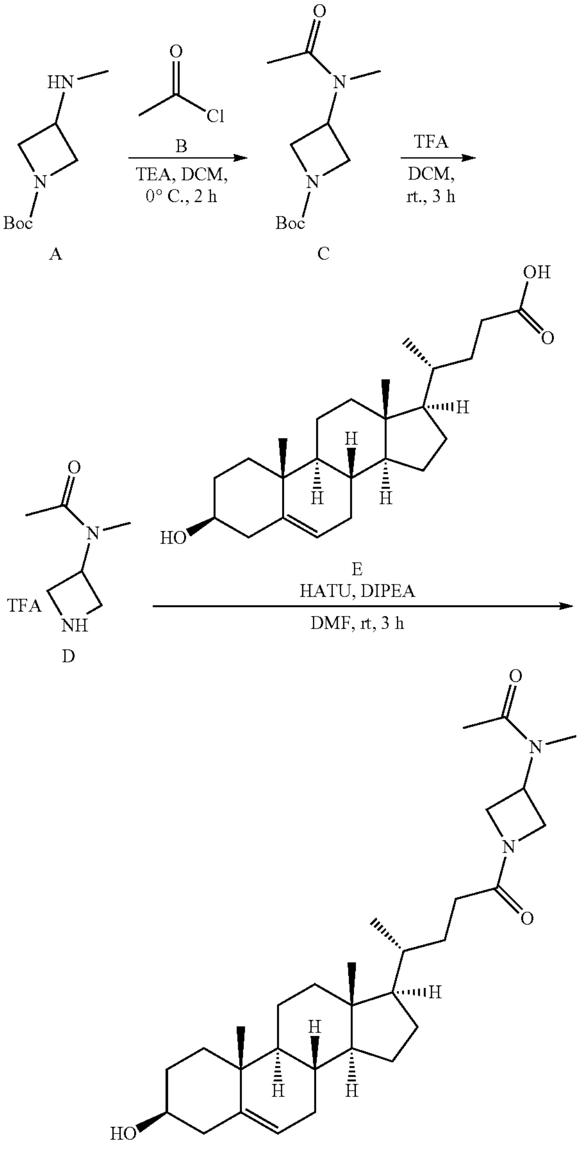

325

To a solution of compound A (500 mg, 2.68 mmol) in dichloromethane (5 mL) was added triethylamine (896 μL, 6.44 mmol) and compound B (229 μL, 3.22 mmol) at 0° C. The mixture was stirred for 2 hours. After completion, the result solution was quenched by the addition of water and extracted with dichloromethane. The organic layer was dried over sodium sulfate and concentrated to give crude product which was purified by column chromatography on silica gel to give compound C (500 mg, 81.6%) as a white solid. To a solution of compound C (500 mg, 2.19 mmol) in dichloromethane (8 mL) was added TFA (1 mL) at room temperature. The mixture was stirred at room temperature for 3 hours. After completion, the result solution was concentrated to give compound D (494 mg, 100%).

To a solution of compound E (147 mg, 393 μmol) in DMF (3 mL) was added compound D (63 mg, 279 μmol), HATU (173 mg, 737 μmol) and DIEA (171 μL, 983 μmol) at room temperature. The mixture was stirred for 3 hours. After completion, the result solution was quenched by the addition of $NH_4Cl$ and extracted with ethyl acetate. The combined organic layers were dried over sodium sulfate and concentrated to give crude product which was purified by prep-HPLC to yield the title compound 325 (11.2 mg, 4.7%) as a white solid. $^1$H NMR (400 MHz, Chloroform-d) δ 5.37-5.25 (m, 2H), 4.36 (t, J=8.8 Hz, 1H), 4.22 (t, J=9.2 Hz, 1H), 4.16-3.99 (m, 2H), 3.56-3.49 (m, 1H), 3.09-3.00 (m, 3H), 2.34-2.24 (m, 5H), 2.13 (s, 3H), 2.05-1.73 (m, 6H), 1.60-1.41 (m, 7H), 1.33-1.25 (m, 3H), 1.20-1.03 (m, 3H) 1.01 (s, 3H), 0.93 (d, J=6.6 Hz, 4H), 0.68 (s, 3H). LCMS[M+H]$^+$ =485.30.

Example 326: N-{1-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]azetidin-3-yl}acetamide

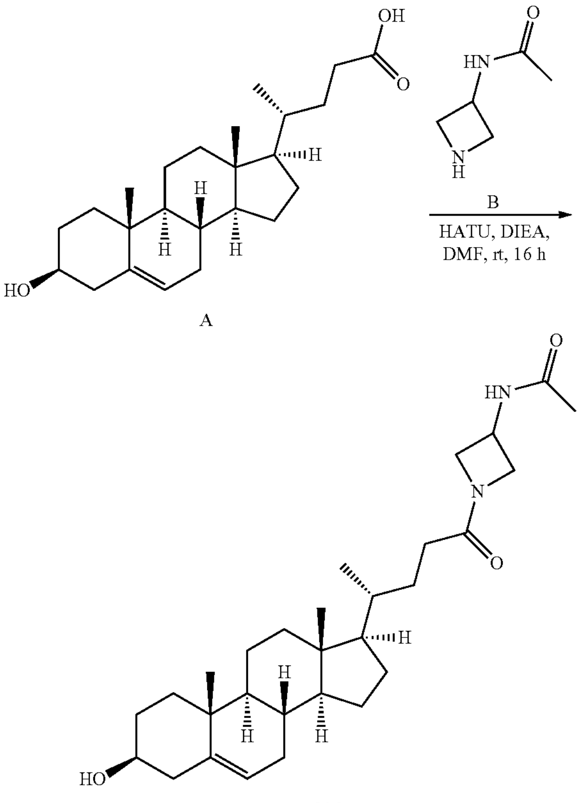

A B

326

To a solution of compound A (100 mg, 267 μmol) in DMF (2 mL) was added compound B (36.6 mg, 320 μmol), HATU (152 mg, 0.4 mmol) and DIEA (138 mg, 1.07 mmol). After stirring at room temperature for 16 hours, the mixture was diluted with water and extracted with ethyl acetate. The organic layer was concentrated, and the residue was purified by silica gel chromatography to give the title compound 326 (78 mg, 62%). $^1$H NMR (400 MHz, Chloroform-d) δ 6.30 (s, 1H), 5.34 (d, J=5.0 Hz, 1H), 4.71-4.60 (m, 1H), 4.43 (bs, 1H), 4.31 (bs, 1H), 4.91 (bs, 1H), 3.84 (bs, 1H), 3.56-3.47 (m, 1H), 2.44-2.06 (m, 3H), 2.03-1.70 (m, 12H), 1.63-1.53 (m, 2H), 1.47-1.39 (m, 3H), 1.34-1.23 (m, 3H), 1.19-1.02 (m, 4H), 1.00 (s, 3H), 0.98-0.86 (m, 5H), 0.67 (s, 3H). LCMS:[M+1]=471.4.

Example 327: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-{6-acetyl-2,6-diazaspiro[3.4]octan-2-yl}pentan-1-one

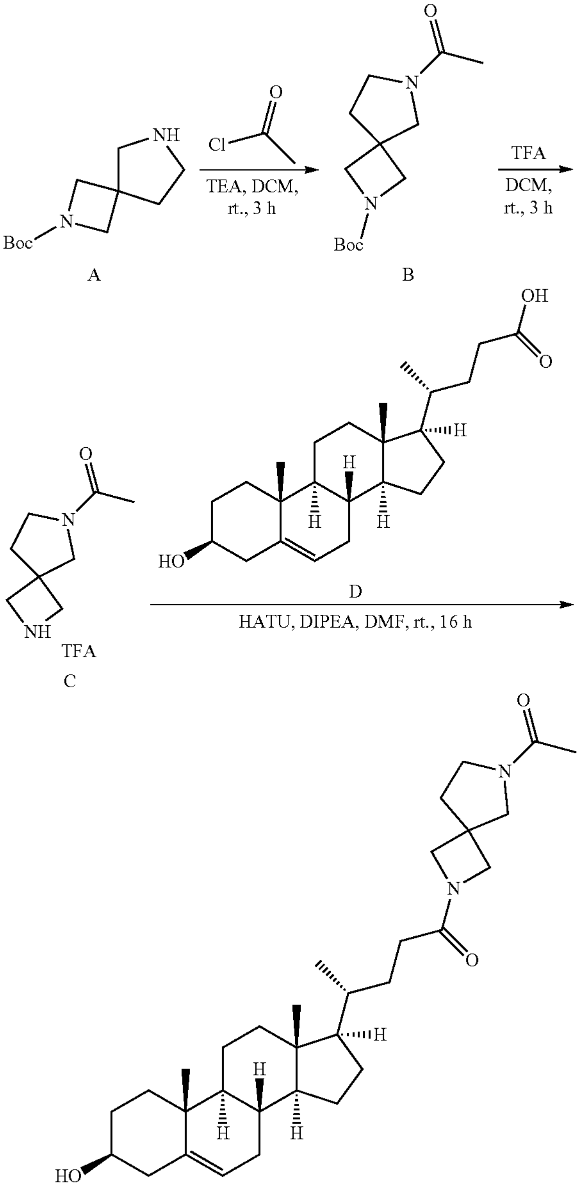

A B C D

327

To a solution of compound A (100 mg, 471 μmol) in dichloromethane (2.5 mL) was added triethylamine (95.3 mg, 942 μmol) and acetyl chloride (44.4 mg, 565 μmol) at −10° C. The resulting mixture was stirred at room temperature for 3 h. Then the reaction was the quenched with saturated aqueous $NaHCO_3$ solution and extracted with ethyl acetate. The organic layer was dried with sodium sulfate and concentrated under vacuum to give compound B (132 mg, 99.2%).

To a solution of compound B (132 mg, 519 μmol) in dichloromethane (2 mL) was added TFA (0.5 mL) at room temperature. After stirring for 3 h, the mixture was concentrated under vacuum to give crude compound C (190 mg, 95%).

To a solution of compound D (185 mg, 494 μmol) in DMF (5 mL) was added DIEA (319 mg, 2.47 mmol), compound C (124 mg, 494 μmol) and HATU (376 mg, 988 μmol) at room temperature. The resulting mixture was stirred at room temperature for 16 h. The reaction was quenched with water and extracted with ethyl acetate. The organic layer was washed with water and brine, dried with sodium sulfate, and concentrated under vacuum to give crude product which was purified by silica gel chromatography (eluting with 1/20 MeOH/DCM) to give the title compound 327 (88 mg, 34.9%). $^1$H NMR (400 MHz, $CDCl_3$) δ 5.34 (d, J=5.0 Hz, 1H), 4.08-3.87 (m, 4H), 3.68-3.46 (m, 5H), 2.32-2.07 (m, 5H), 2.05 (s, 3H), 2.01-1.77 (m, 6H), 1.72 (s, 3H), 1.63-1.06 (m, 12H), 1.00 (s, 3H), 0.92 (d, J=6.4 Hz, 3H), 0.68 (s, 3H). LCMS: $[M+Na]^+$=523.25.

Example 328: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-{6-acetyl-2,6-diazaspiro[3.3]heptan-2-yl}pentan-1-one

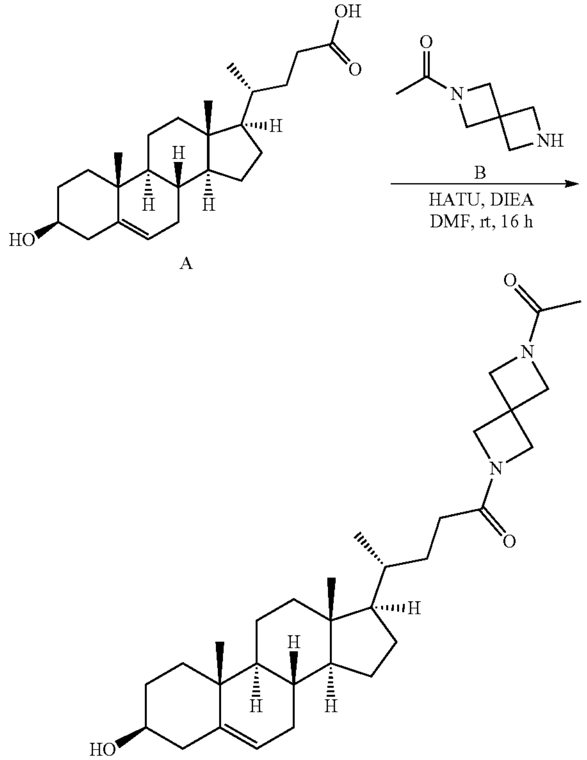

328

To a solution of compound A (50.6 mg, 135 μmol) in DMF (3 mL) was added DIEA (52.3 mg, 405 μmol), compound B (18.9 mg, 135 umol) and HATU (103 mg, 270 μmol) at room temperature. The resulting mixture was stirred at room temperature for 16 h. The mixture was diluted with water and extracted with ethyl acetate. The organic layer was washed with water and brine, dried with sodium sulfate, and concentrated under vacuum to give crude product which was purified by silica gel chromatography (eluting with 1/20 MeOH/DCM) to give the title compound 328 (22.7 mg, 33.8%). $^1$H NMR (400 MHz, $CDCl_3$) δ 5.35 (d, J=5.0 Hz, 1H), 4.25 (bs, 4H), 4.12 (bs, 4H), 3.52 (dt, J=11.6, 6.4 Hz, 1H), 2.33-1.92 (m, 8H), 1.87 (s, 3H), 1.85-1.70 (m, 3H), 1.53-1.04 (m, 15H), 1.01 (s, 3H), 0.93 (d, J=6.4 Hz, 3H), 0.68 (s, 3H). LCMS: $[M+H]^+$=497.25.

Example 329: [(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-ethynyl-4-(propan-2-yloxy)piperidin-1-yl]pentan-1-one

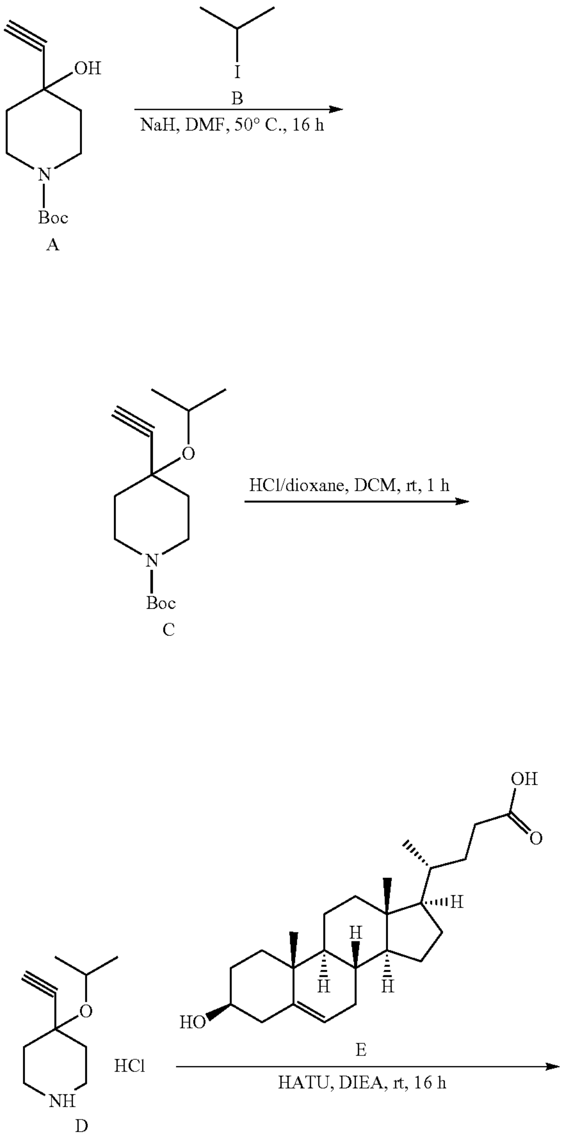

-continued

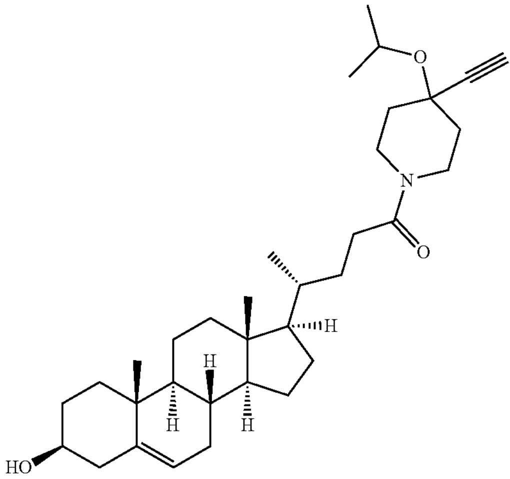

329

Example 330: (R)-1-(4-ethynyl-4-methoxypiperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

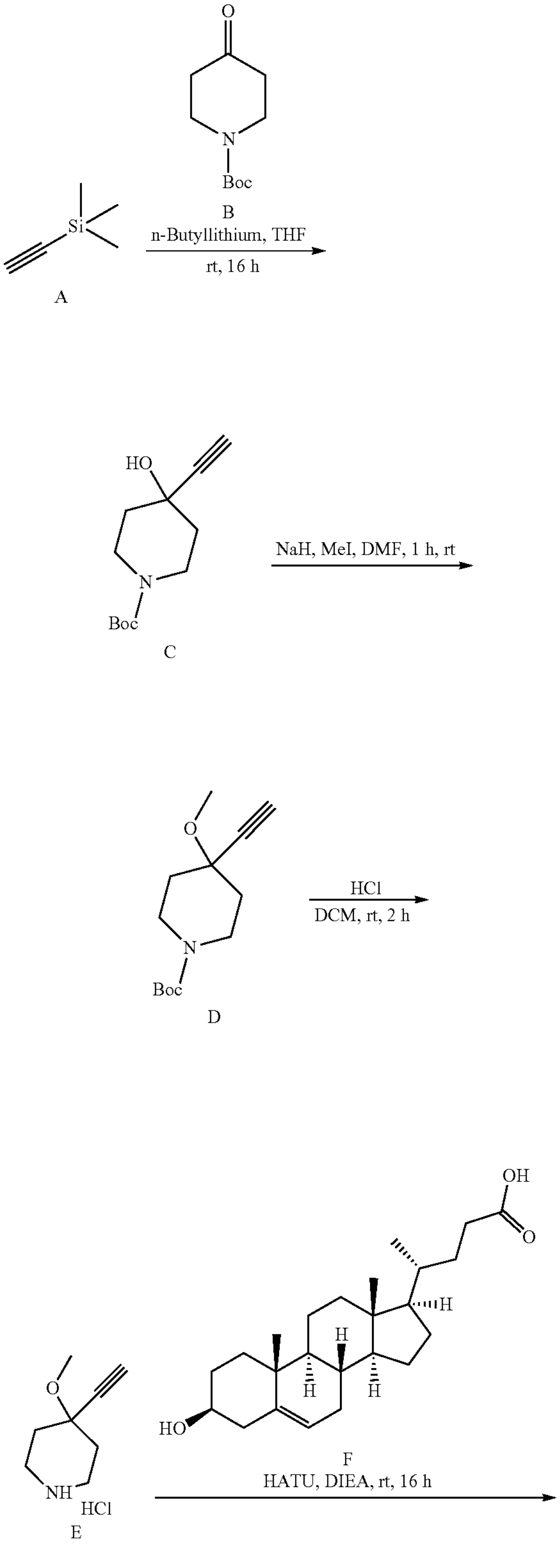

To a solution of compound A (2.0 g, 8.88 mmol) in DMF (10 mL) was added NaH (1.06 g, 26.6 mmol, 60% dispersion in oil) at 0° C. After stirring for 30 mins, to the reaction mixture was added compound B (22.6 g, 133 mmol) and stirred for 16 hours at 50° C. The reaction was quenched with water and extracted with ethyl acetate (30 mL×4). The combined organic layer was concentrated to give the crude which was purified by silica gel chromatography to yield compound C (80 mg, 3%).

To a solution of compound C (80 mg, 299 μmol) in dichloromethane (2 mL) was added hydrogen chloride (0.5 mL, 2 mmol, 4M in dioxane). After stirring at room temperature for 1 hour, the reaction mixture was concentrated under vacuum to afford compound D (77 mg, 91%).

To a solution of compound D (77 mg, 275 μmol) in dimethylformamide (2 mL) was added compound E (82.4 mg, 220 μmol), DIEA (213 mg, 1.65 mmol) and HATU (209 mg, 550 μmol). The mixture was stirred at room temperature for 16 hours. The reaction was quenched with water and extracted with ethyl acetate (10 mL×4). The combined organic layer was concentrated to give the crude which was purified by silica gel chromatography to yield the title compound 329 (24 mg, 20%). LCMS:$[M+1]^+$=520.30. $^1H$ NMR (400 MHz, Chloroform-d) δ 5.35 (d, J=5.2 Hz, 1H), 4.19-4.07 (m, 1H), 4.06-3.97 (m, 1H), 3. 72-3.60 (m, 1H), 3.59-3.45 (m, 1H), 3.44-3.27 (m, 2H), 2.50 (s, 1H), 2.41-2.16 (m, 4H), 2.04-1.81 (m, 7H), 1.77-1.66 (m, 3H), 1.54-1.42 (m, 7H), 1.37-1.24 (m, 3H), 1.22-1.17 (m, 7H), 1.15-1.03 (m, 4H), 1.00 (s, 3H), 0.95 (d, J=6.4 Hz, 4H), 0.68 (s, 3H).

-continued

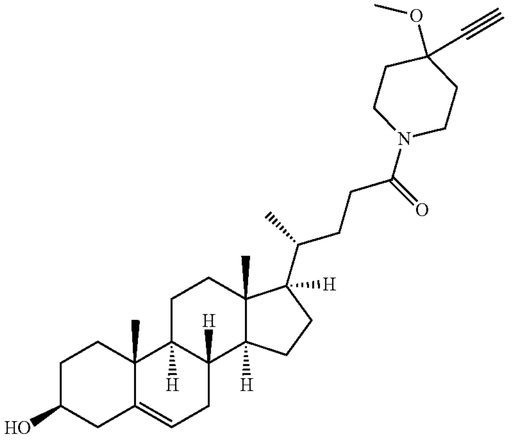

330

To a solution of compound A (10 g, 102 mmol) in THF (200 mL) was added BuLi (63 mL, 101 mmol, 1.6M in hexane) slowly at −78° C.; under $N_2$. After stirring at −78° C. for 0.5 hours, compound B (17 g, 85.5 mmol) in tetrahydrofuran (80 mL, 983 mmol) was added. The mixture stirred at room temperature for 16 hours. To this mixture was added methanol (100 mL) and $K_2CO_3$ (12.9 g, 93.7 mmol) and stirred at room temperature for another 5 hours. The mixture was extracted with $H_2O$ and diethyl ether. The organic layer was concentrated to give crude which was purified by silica gel chromatography to give compound C (19.0 g, 82%).

To a solution of C (500 mg, 2.22 mmol) in DMF (8 mL) was added NaH (176 mg, 4.44 mmol, 60% dispersion in oil) at 0° C. After stirring at 0° C. for 0.5 hours, the solution was added MeI (473 mg, 3.33 mmol). The reaction stirred at room temperature for 1 hour. The mixture was diluted with water and extracted with EtOAc. The organic phase was washed with brine, dried over sodium sulfate, and concentrated under vacuum to afford compound D (520 mg, 97.9%).

To a solution of compound D (80 mg, 334 μmol) in dichloromethane (2 mL) was added HCl (0.5 mL, 2 mmol, 4M in dioxane). After stirring at room temperature for 2 hours, the mixture was concentrated to afford compound E (58 mg) which was used in next step directly.

To a solution of compound E (58 mg, 331 μmol) in DMF (4 mL) was added compound F (100 mg, 265 μmol), DIEA (256 mg, 1.98 mmol) and HATU (251 mg, 662 μmol). After stirring at room temperature for 4 hours, the mixture was diluted with $H_2O$ and extracted with ethyl acetate. The organic layer was concentrated to give crude which was purified by silica gel chromatography to give example 330 (62 mg, 29%). $^1H$ NMR (400 MHz, Chloroform-d) δ 5.35 (d, J=5.1 Hz, 1H), 3.97-3.88 (m, 1H), 3.68-3.58 (m, 1H), 3.56-3.47 (m, 1H), 3.46-3.37 (m, 5H), 2.55 (s, 1H), 2.38 (ddd, J=15.6, 10.9, 5.0 Hz, 1H), 2.32-2.17 (m, 3H), 2.02-1.70 (m, 10H), 1.52-1.41 (m, 6H), 1.38-1.28 (m, 3H), 1.20-1.05 (m, 4H), 1.01 (s, 3H), 0.95 (d, J=6.6 Hz, 3H), 0.93-0.82 (m, 1H), 0.68 (s, 3H). LCMS: $[M+1]^+$=496.25.

Example 331: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3R)-3-(1,1,1,3,3,3-hexafluoro-2-methoxypropan-2-yl)pyrrolidin-1-yl]pentan-1-one

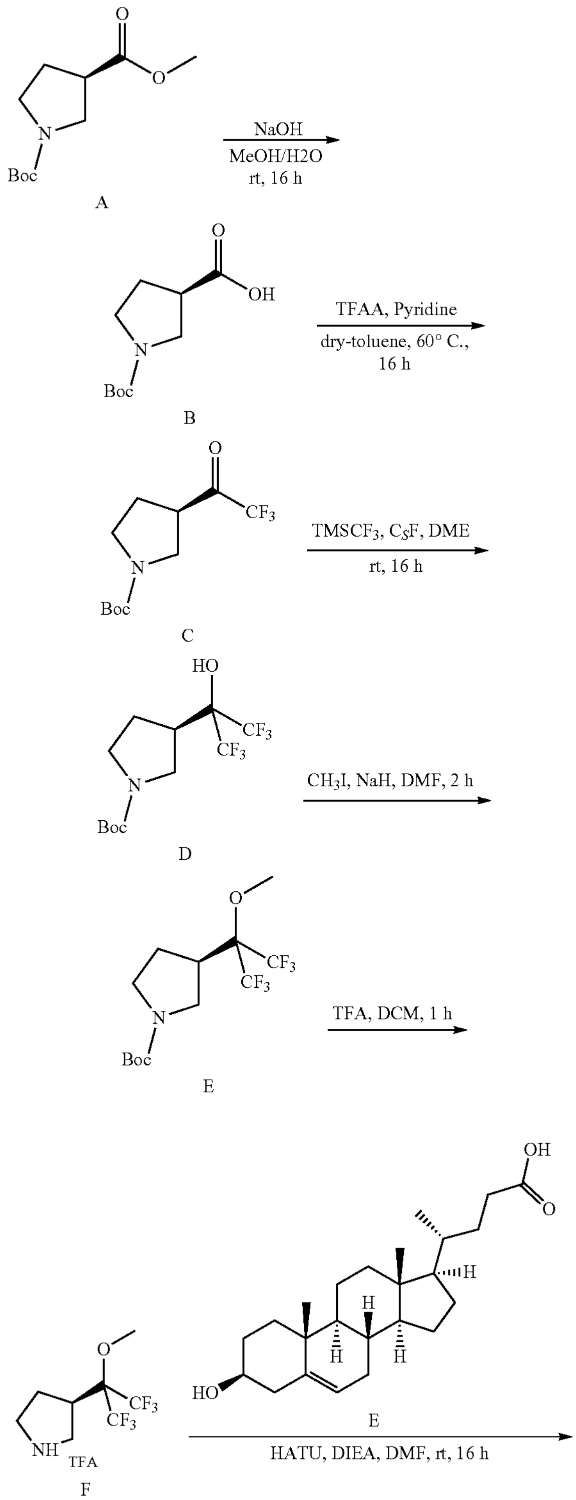

-continued

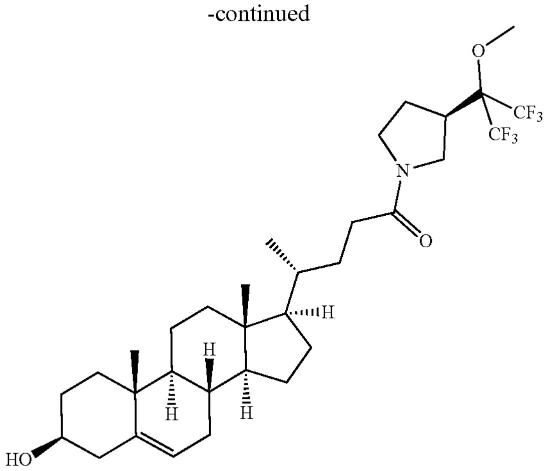

331

To a solution of compound A (1.0 g, 4.36 mmol) in methanol (15 mL) and water (15 mL) was added sodium hydroxide (523 mg, 13.1 mmol). The reaction mixture was stirred at room temperature for 16 hours under $N_2$ atmosphere. The reaction was quenched with saturated $NH_4Cl$ and extracted with ethyl acetate (10 mL×4). The combined organic layer was concentrated to give the crude compound B (900 mg, 95%).

To a solution of compound B (650 mg, 3.02 mmol) in toluene (5 mL) was added TFAA (4.2 mL, 30.2 mmol) and pyridine (3 mL, 36.2 mmol) at 0° C. After stirring at 60° C. for 16 hours under $N_2$ atmosphere, the reaction was quenched with water and extracted with ethyl acetate (10 mL×4). The combined organic layer was concentrated to give the crude which was purified by silica gel chromatography to yield the title compound C (600 mg, 74%).

To a solution of compound C (0.6 g, 2.25 mmol) in 1,2-dichloroethane (5 mL) was added tert-butyl(trifluoromethyl)silane (1.05 g, 6.74 mmol) and cesium fluoride (68.2 mg, 449 μmol). After stirring at room temperature for 16 hours, the reaction was quenched with water and extracted with ethyl acetate (10 mL×4). The combined organic layer was concentrated to give the crude which was purified by silica gel chromatography to yield the title compound D (400 mg, 54%).

To a solution of compound D (360 mg, 1.07 mmol) in DMF (4 mL) was added NaH (64 mg, 1.6 mmol, 60% dispersion in oil) at 0° C. After stirring for 30 mins, the reaction mixture was added iodomethane (455 mg, 3.2 mmol) and stirred for additional 2 hour at room temperature. The reaction was then quenched with water and extracted with ethyl acetate (10 mL×4). The combined organic layer was concentrated to give the crude compound E (370 mg, 98%).

To a solution of compound E (200 mg, 569 μmol) in dichloromethane (2 mL) was added TFA (1 mL). The mixture was stirred at room temperature for 1 hour. The mixture was concentrated to give the crude compound F (206 mg, 99%).

To a solution of compound F (206 mg, 569 μmol) in DMF (3 mL) was added compound G (171 mg, 455 μmol), DIEA (442 mg, 3.42 mmol) and HATU (430 mg, 1.14 mmol). The mixture was stirred at room temperature for 16 hours. The reaction was quenched with water and extracted with ethyl acetate (10 mL×4). The combined organic layer was concentrated to give the crude which was purified by silica gel chromatography to yield the title compound 331 (24 mg, 6%). LCMS:$[M+1]^+$=608.20. $^1H$ NMR (400 MHz, Chloroform-d) δ 5.35 (d, J=5.2 Hz, 1H), 3.85-3.72 (m, 1H), 3.72-3.12 (m, 7H), 2.85-2.60 (m, 1H), 2.35-1.74 (m, 14H), 1.65-1.39 (m, 7H), 1.39-1.23 (m, 3H), 1.21-1.02 (m, 5H), 1.00 (s, 3H), 0.98-0.87 (m, 4H), 0.68 (s, 3H). $^{19}F$ NMR (400 MHz, Chloroform-d) δ−67.45 (q, J=10.8 Hz), −67.83 (q, J=10.5 Hz), −68.66 (q, J=10.8 Hz), −68.85 (q, J=10.8 Hz).

Example 332: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyrimidine-2-carbonyl)piperazin-1-yl)pentan-1-one

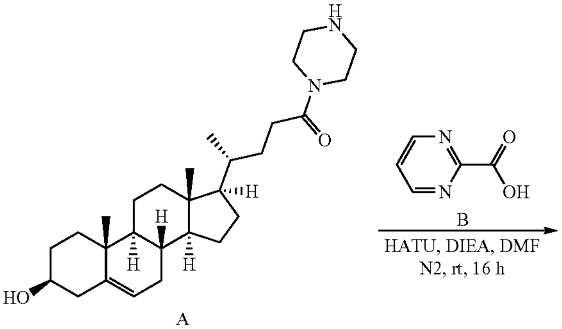

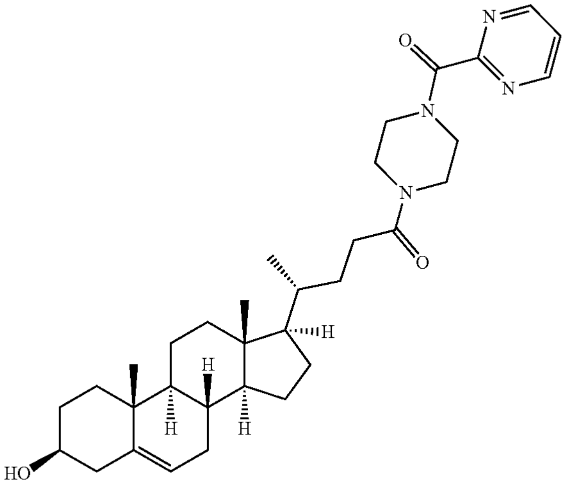

332

To a solution of compound A (100 mg, 0.226 mmol) and compound B (28 mg, 0.226 mmol) in DMF (2 mL) was added HATU (170 mg, 0.452 mmol) and DIEA (170 mg, 1.356 mmol). The mixture was stirred at room temperature under $N_2$ for 16 h. The reaction mixture was diluted with water and extracted with EtOAc. The organic layer was washed by brine, dried over sodium sulfate, filtered, and concentrated. The mixture was purified by column chromatography on silica gel to afford compound 332 (25 mg) as a white solid. $^1H$ NMR (400 MHz, Chloroform-d) δ 8.84 (d, J=4.8 Hz, 2H), 7.38 (t, J=5.2 Hz, 1H), 5.34 (d, J=4.0 Hz, 1H), 3.90-3.35 (m, 10H), 2.48-2.15 (m, 5H), 2.05-1.75 (m, 7H), 1.69-1.22 (m, 19H), 1.21-0.82 (m, 14H), 0.68 (d, J=7.2 Hz, 3H). LCMS: [M+H]=549.25.

Example 333: (4R)-4-[(1R,3aS,3bR,5aS,7S,9aS,9bS,11aR)-7-hydroxy-9a,11a-dimethyl-hexadecahydro-1H-cyclopenta[a]phenanthren-1-yl]-1-[(3S)-3-methoxypiperidin-1-yl]pentan-1-one

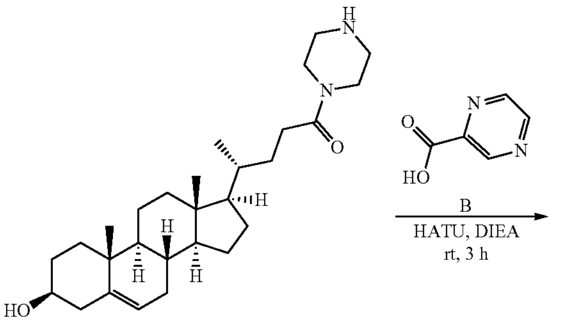

A

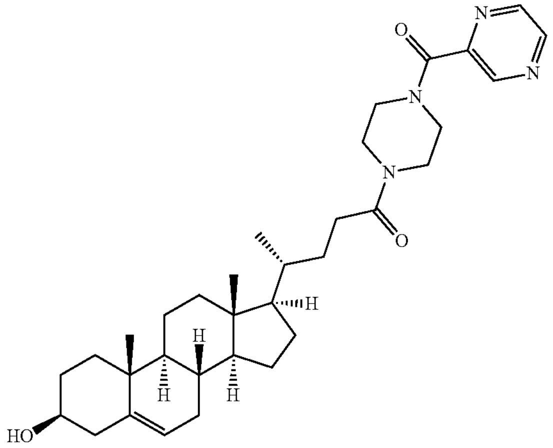

333

To a solution of compound A (150 mg, 398 μmol) and compound B (45.9 mg, 398 μmol) in DMF (5 mL) was added HATU (303 mg, 797 mmol) and DIEA (309 mg, 2.39 μmol). The mixture was stirred at room temperature for 3 hours. After completion, the mixture was quenched by adding saturated ammonium chloride solution (30 mL) and extracted with ethyl acetate (10 mL×3). The organic layer was washed with brine, dried over sodium sulfate, filtered, and concentrated to give the crude which was purified by column chromatography on silica gel to yield the title compound Example 333 (100 mg, 53%) as a white solid. LCMS: $[M+Na]^+$=571.30. $^1H$ NMR (400 MHz, Chloroform-d) δ 9.00 (d, J=9.6 Hz, 1H), 8.67 (d, J=2.5 Hz, 1H), 8.55 (d, J=5.2 Hz, 1H), 5.35 (d, J=5.1 Hz, 1H), 3.86-3.50 (m, 9H), 2.48-2.18 (m, 4H), 2.06-1.79 (m, 6H), 1.49 (d, J=7.4 Hz, 6H), 1.38-1.28 (m, 2H), 1.18-1.05 (m, 4H), 1.01 (s, 3H), 0.99-0.86 (m, 4H), 0.69 (s, 3H).

Example 334: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyrimidine-4-carbonyl)piperazin-1-yl)pentan-1-one

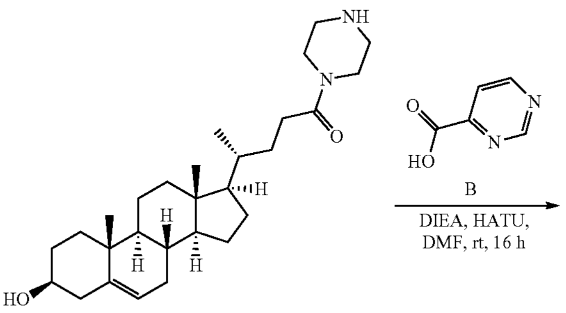

A

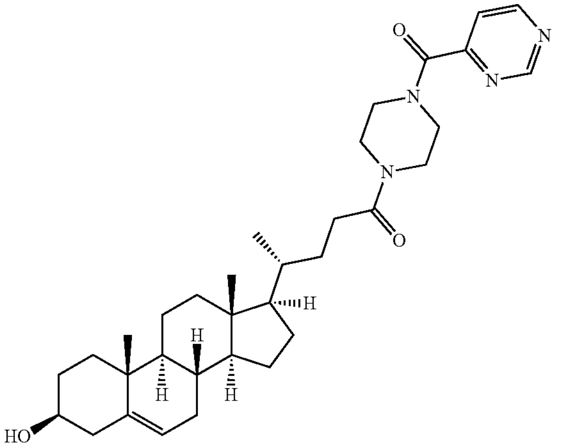

334

To a solution of compound A (100 mg, 226 μmol) in DMF (4 mL) was added compound B (18.7 mg, 151 μmol), DIEA (117 mg, 904 μmol) and HATU (158 mg, 452 μmol). After stirring at room temperature for 16 hours, the mixture was diluted with water and extracted with ethyl acetate. The organic layer was concentrated to give crude which was purified by silica gel chromatography to give the title compound 334 (30 mg, 36%). $^1H$ NMR (400 MHz, Chloroform-d) δ 9.26 (s, 1H), 8.92 (d, J=5.2 Hz, 1H), 7.73-7.62 (m, 1H), 5.35 (d, J=5.1 Hz, 1H), 3.85-3.73 (m, 3H), 3.69 (s, 2H), 3.62 (s, 2H), 3.59-3.48 (m, 2H), 2.47-2.32 (m, 1H), 2.32-2.18 (m, 3H), 2.03-1.76 (m, 6H), 1.52-1.28 (m, 9H), 1.22-1.06 (m, 4H), 1.05-0.89 (m, 9H), 0.69 (s, 3H). LCMS: $[M+1]^+$=549.30.

Example 335: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(pyridine-2-carbonyl)piperazin-1-yl]pentan-1-one

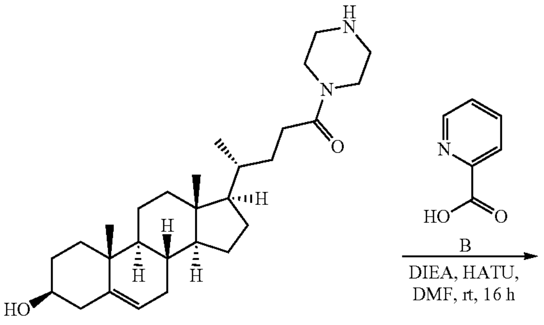

A

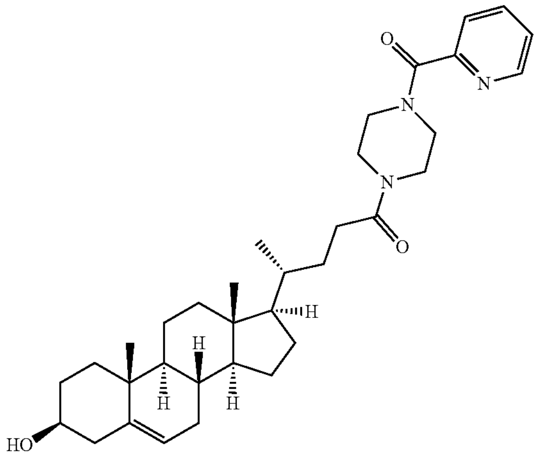

335

To a solution of compound A (100 mg, 226 μmol) in DMF (2 mL) was added compound B (18.5 mg, 151 μmol), DIEA (117 mg, 904 μmol) and HATU (114 mg, 452 μmol). After stirring at room temperature for 16 hours, the reaction was quenched with water and extracted with ethyl acetate (10 mL×4). The combined organic layer was concentrated to give the crude which was purified by silica gel chromatography to yield the title compound 335 (20 mg, 24%). LCMS:$[M+1]^+$=548.25. $^1H$ NMR (400 MHz, Chloroform-d) δ 8.59 (s, 1H), 7.87-7.85 (m, 1H), 7.76-7.65 (m, 1H), 7.41-7.34 (m, 1H), 5.35 (d, J=5.2 Hz, 1H), 3.85-3.47 (m, 9H), 2.49-2.35 (m, 1H), 2.32-2.17 (m, 3H), 2.04-1.93 (m, 2H), 1.91-1.75 (m, 4H), 1.69-1.41 (m, 10H), 1.38-1.24 (m, 3H), 1.19-1.06 (m, 3H), 1.00 (s, 3H), 0.99-0.92 (m, 4H), 0.69 (s, 3H).

Example 336: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(2-hydroxy-2-methylpropanoyl)piperazin-1-yl)pentan-1-one

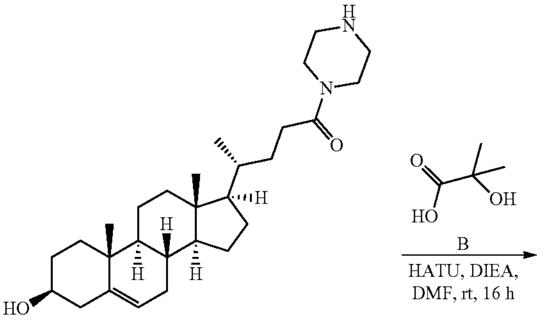

A

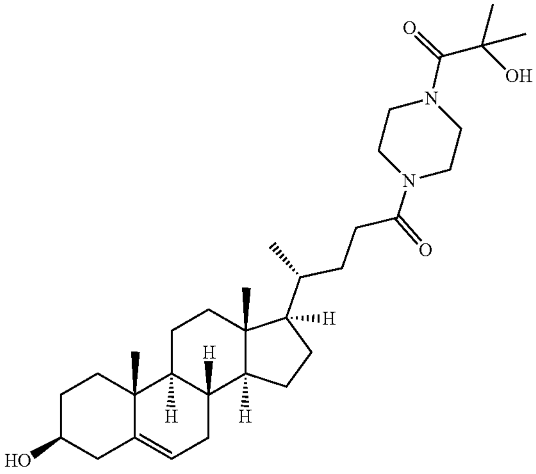

336

To a solution of compound A (500 mg, 1.13 mmol) and compound B (118 mg, 1.13 mmol) in DMF (6 mL) was added HATU (644 mg, 1.69 mmol) and DIEA (438 mg, 3.39 mmol). The mixture was stirred at room temperature for 16 hours. After completion, the mixture was quenched by adding saturated ammonium chloride solution (50 mL) and extracted with ethyl acetate (50 mL×3). The combined organic extracts were washed with brine, dried over sodium sulfate, filtered, and concentrated to give the crude which was purified by column chromatography on silica gel to yield the title compound 336 (148 mg, 24.8%) as a white solid. LCMS: $[M+H]^+$=529.20. $^1H$ NMR (400 MHz, Chloroform-d) δ 5.35 (d, J=5.0 Hz, 1H), 3.79-3.44 (m, 9H), 2.45-2.21 (m, 4H), 2.14-1.95 (m, 6H), 1.87-1.72 (m, 3H), 1.63-1.57 (m, 1H), 1.51 (s, 6H), 1.49-1.43 (m, 3H), 1.36-1.25 (m, 3H), 1.21-1.03 (m, 5H), 1.01 (s, 3H), 0.96 (d, J=6.4 Hz, 3H), 0.69 (s, 3H).

Example 337: 4[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]-N-methylpiperazine-1-carboxamide

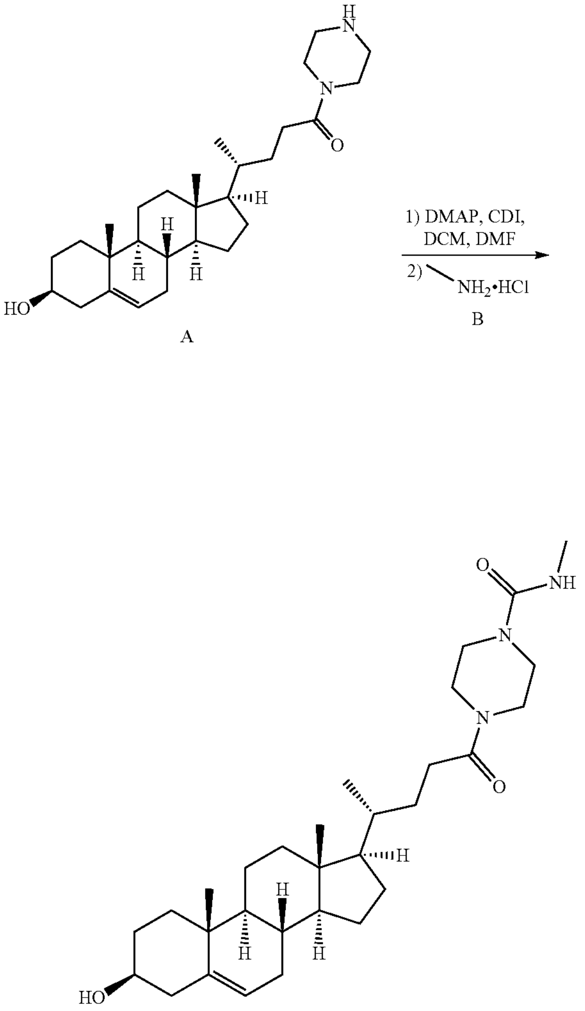

337

To a solution of compound A (200 mg, 452 μmol) in dichloromethane (1.5 mL) and DMF (0.2 mL) at room temperature was added DMAP (82.8 mg, 678 μmol) and CDI (237 mg, 678 μmol). After stirring for 4 hours, compound B HCl salt (20 mg, 645 μmol) was added. The mixture was stirred for 16 hours. The solvent was removed under vacuum. The residue was diluted with water, acidified with 1N HCl to pH~3 and extracted with EA. The organic layer was washed by brine, dried over sodium sulfate, filtered, concentrated. The residue was purified by pre-HPLC to afford the title compound 337 (20 mg, 8.9%) as a white solid. LCMS: $[M+1]^+$=500.30. $^1H$ NMR (400 MHz, Chloroform-d) δ 5.35 (d, J=5.2 Hz, 1H), 4.44 (bs, 1H), 3.64 (t, J=5.3 Hz, 2H), 3.56-3.42 (m, 5H), 3.30 (t, J=5.4 Hz, 2H), 2.83 (d, J=4.1 Hz, 3H), 2.45-2.16 (m, 4H), 2.05-1.74 (m, 6H), 1.55-1.40 (m, 6H), 1.38-1.22 (m, 3H), 1.22-1.04 (m, 4H), 1.00 (s, 4H), 0.95 (d, J=6.5 Hz, 4H), 0.68 (s, 3H).

Example 338: 4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]-N-cyclopropylpiperazine-1-carboxamide

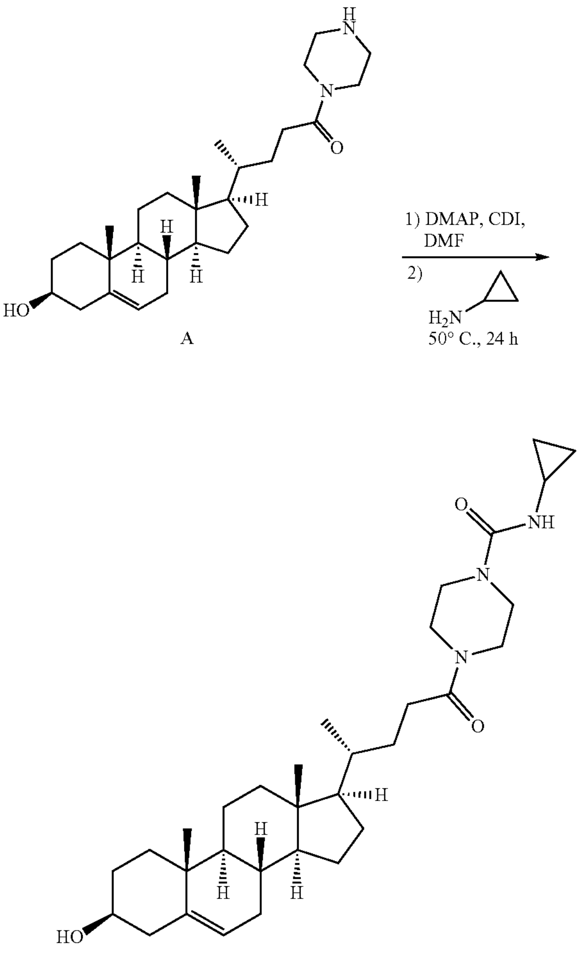

338

To a solution of compound A (200 mg, 452 μmol) in DMF (1.5 mL) at room temperature was added DMAP (83.5 mg, 678 μmol) and CDI (110 mg, 678 μmol). After stirring at room temperature for 1 h, cyclopropylamine (157 μL, 2.26 mmol) was added. The resulting mixture was allowed to warm to 50° C.; and stirred for 24 h. The mixture was diluted with water and extracted with ethyl acetate. The organic layer was washed with water and brine, dried with sodium sulfate, and concentrated under vacuum to give crude product which was purified by silica gel chromatography (eluting with 1/20 ethyl acetate/PE) to give the title compound 338 (45.3 mg, 19.1%). $^1H$ NMR (400 MHz, $CDCl_3$) δ 5.35 (d, J=5.2 Hz, 1H), 4.70 (s, 1H), 3.62 (t, J=5.4 Hz, 2H), 3.56-3.49 (m, 1H), 3.47 (s, 3H), 3.27 (t, J=5.2 Hz, 2H), 2.70-2.62 (m, 1H), 2.42-2.16 (m, 4H), 2.02-1.94 (m, 2H), 1.91-1.75 (m, 4H), 1.70 (s, 3H), 1.55-1.40 (m, 6H), 1.34-1.24 (m, 4H), 1.17-1.03 (m, 4H), 1.00 (s, 3H), 0.95 (d, J=6.4 Hz, 3H), 0.77-0.71 (m, 2H), 0.68 (s, 3H), 0.51-0.45 (m, 2H). LCMS: $[M+H]^+$=526.30.

Example 339: 4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]-N,N-dimethylpiperazine-1-carboxamide

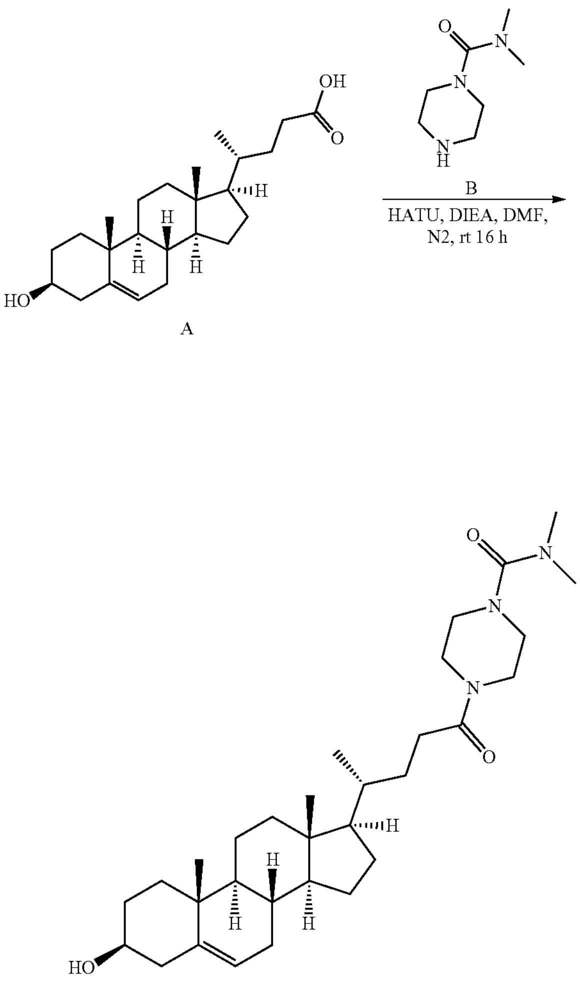

A

339

To a solution of compound A (100 mg, 267 μmol) in DMF (2 mL) was added compound B (50.4 mg, 320 μmol), HATU (152 mg, 0.4 mmol) and DIEA(138 mg, 1.07 mmol). After stirring at room temperature for 16 hours, the mixture was diluted with water and extracted with ethyl acetate. The organic layer was concentrated to give crude which was purified by silica gel chromatography to give the title compound 339 (25 mg, 18%). $^{1}$H NMR (400 MHz, Chloroform-d) δ 5.35 (d, J=4.8 Hz, 1H), 3.61 (bs, 2H), 3.56-3.41 (m, 3H), 3.24 (bs, 2H), 3.20 (bs, 2H), 2.85 (s, 6H), 2.43-2.17 (m, 4H), 2.05-1.92 (m, 2H), 1.92-1.74 (m, 4H), 1.55-1.40 (m, 6H), 1.38-1.23 (m, 4H), 1.21-1.04 (m, 4H), 1.00 (s, 3H), 0.95 (d, J=6.5 Hz, 3H), 0.68 (s, 3H). LCMS:[M+1]=514.4.

Example 340: cyclopropyl4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]piperazine-1-carboxylate

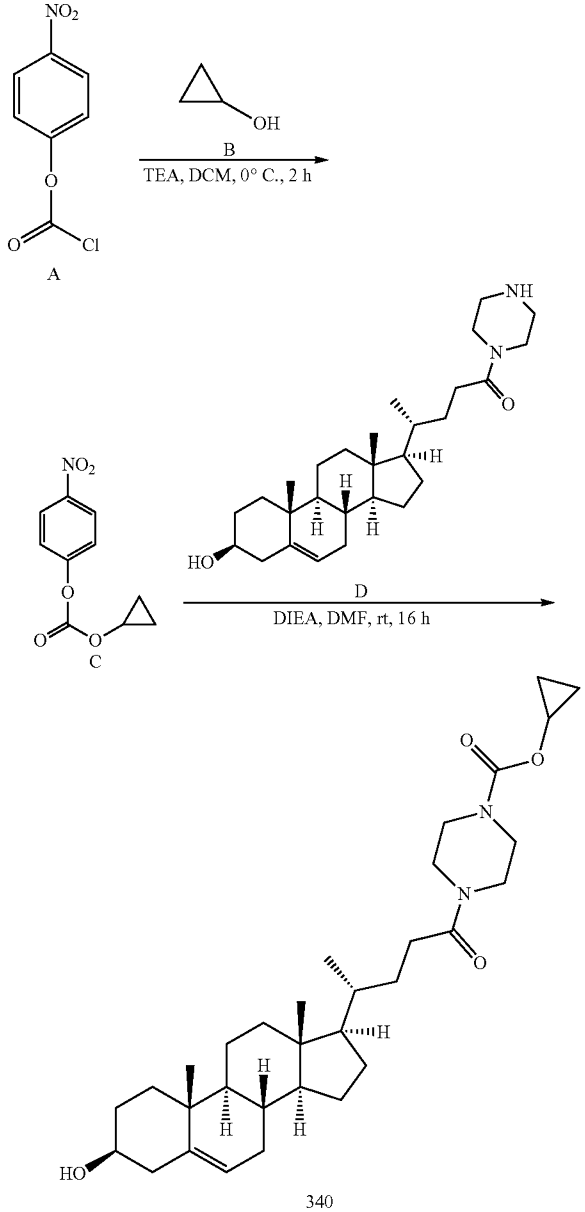

A

C

340

To a solution of compound A (1.0 g, 4.96 mmol) in dichloromethane (10 mL) was added compound B (346 mg, 5.95 mmol) and triethylamine (602 mg, 5.95 mmol) at 0° C. under $N_2$ atmosphere. The mixture was stirred at the same temperature for 2 hours. The reaction was quenched with water and extracted with DCM (10 mL×4). The combined organic layer was concentrated to give the crude which was purified by silica gel chromatography to yield the title compound C (1.0 g, 90%).

To a solution of compound C (298 mg, 672 μmol) in DMF (3 mL) was added compound D (0.1 g, 448 μmol), DIEA (174 mg, 1.34 mmol) and HATU (158 mg, 672 μmol). The mixture was stirred at room temperature for 16 hours. The reaction was quenched with water and extracted with ethyl acetate (10 mL×4). The combined organic layer was concentrated to give the crude which was purified by silica gel chromatography to yield the title compound 340 (97 mg, 41%). LCMS:$[M+1]^+$=548.25. $^1H$ NMR (400 MHz, Chloroform-d) δ 5.35 (s, 1H), 4.16-4.03 (m, 1H), 3.61-3.35 (m, 10H), 2.43-2.17 (m, 5H), 2.04-1.93 (m, 2H), 1.89-1.73 (m, 4H), 1.54-1.39 (m, 6H), 1.38-1.24 (m, 3H), 1.20-1.02 (m, 5H), 1.00 (s, 3H), 0.95 (d, J=6.4 Hz, 3H), 0.72-0.66 (m, 7H).

Example 341: isopropyl4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperazine-1-carboxylate

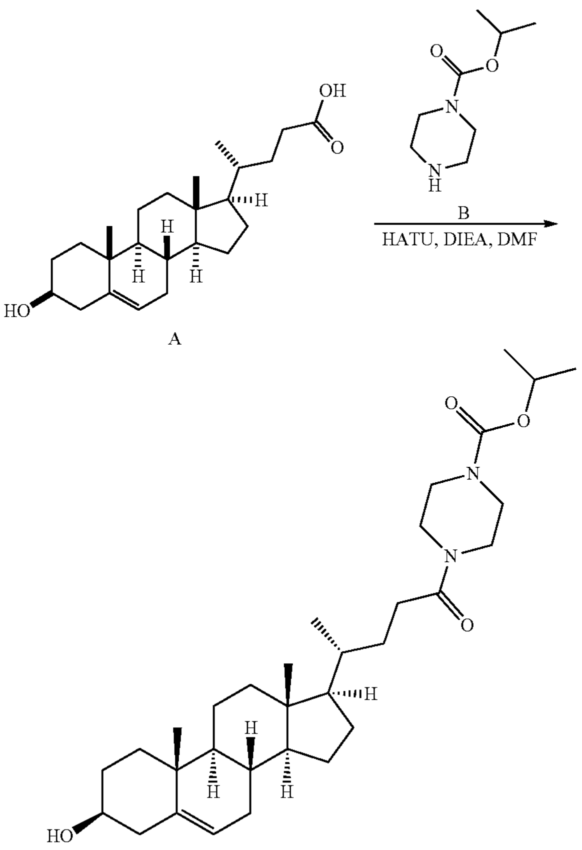

A
B
Example 341

To a mixture of compound B (50.6 mg, 294 μmol), compound A (100 mg, 267 μmol) and HATU (152 mg, 0.4 mmol) in DMF (2 mL) was added DIEA (104 mg, 801 μmol). The mixture was stirred at room temperature for 16 h. The reaction was quenched with water (20 mL) and extracted with EtOAc (20 mL×3). The combined organic phase was washed by brine (50 mL), dried over sodium sulfate, and concentrated under vacuum. The residue was purified by Prep-HPLC to afford the title compound 341 (92.3 mg, 65%) as a white solid. $^1H$ NMR (400 MHz, Chloroform-d) δ 5.35 (d, J=5.2 Hz, 1H), 4.98-4.89 (m, 1H), 3.64-3.39 (m, 9H), 2.43-2.32 (m, 1H), 2.32-2.17 (m, 3H), 2.05-1.92 (m, 2H), 1.94-1.79 (m, 3H), 1.81-1.71 (m, 1H), 1.70-1.53 (m, 4H), 1.54-1.41 (m, 4H), 1.38-1.28 (m, 2H), 1.25 (d, J=6.2 Hz, 6H), 1.23-1.02 (m, 5H), 1.00 (s, 3H), 0.95 (d, J=6.5 Hz, 3H), 0.90 (dd, J=11.4, 6.2 Hz, 1H), 0.68 (s, 3H).

Example 342: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(2-methyl-2H-tetrazole-5-carbonyl)piperazin-1-yl)pentan-1-one

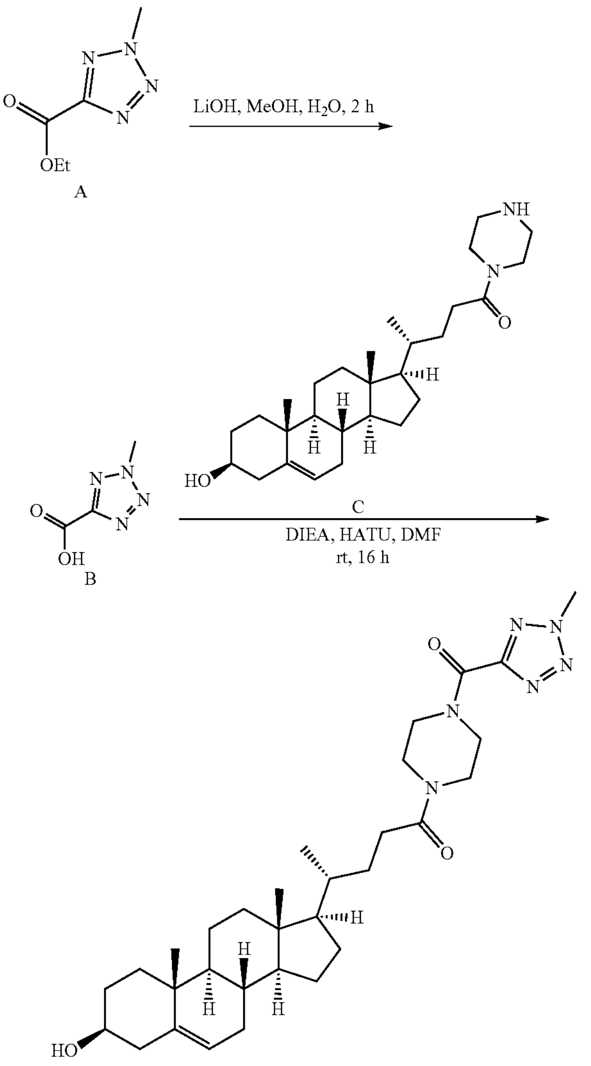

A
B
C
342

To a solution of compound A (120 mg, 769 μmol) in methanol (3 mL) and water (2 mL) was added LiOH (36.8 mg, 1.54 mmol). The reaction mixture was stirred at room temperature for 2 h. The mixture was quenched with 1 N HCl and extracted with ethyl acetate. The organic layer was concentrated to give compound B (95 mg, 98%).

To a solution compound B (100 mg, 781 μmol) in DMF (5 mL) was added compound C (346 mg, 781 μmol), DIEA (303 mg, 2.34 mmol) and HATU (594 mg, 1.56 mmol). After stirring at room temperature for 16 hours, the mixture was diluted with water and extracted with ethyl acetate. The organic layer was concentrated to give crude which was purified by silica gel chromatography to give the title compound 342 (37.2 mg, 8.6%). $^{1}H$ NMR (400 MHz, Chloroform-d) 65.35 (d, J=5.2 Hz, 1H), 4.44 (s, 3H), 3.98-3.81 (m, 4H), 3.78-3.68 (m, 2H), 3.64-3.47 (m, 3H), 2.48-2.19 (m, 4H), 2.05-1.73 (m, 7H), 1.56-1.28 (m, 10H), 1.22-0.88 (m, 13H), 0.69 (s, 3H). LCMS: M+1=553.25.

Example 343: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-hydroxy-4-(pyridazin-4-yl)piperidin-1-yl) pentan-1-one

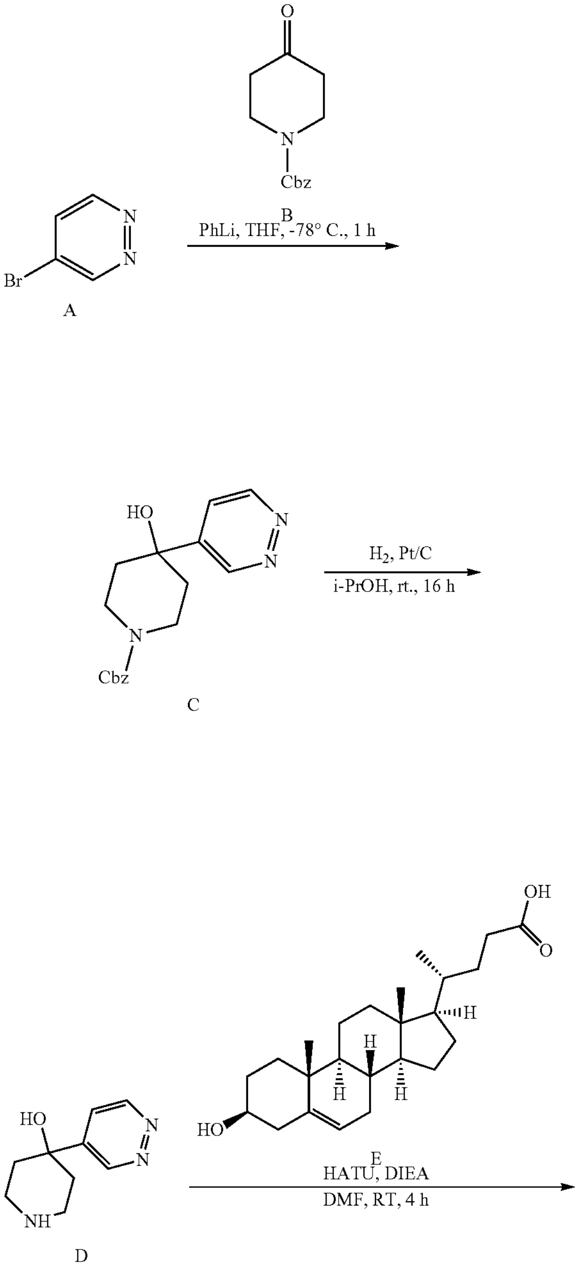

-continued

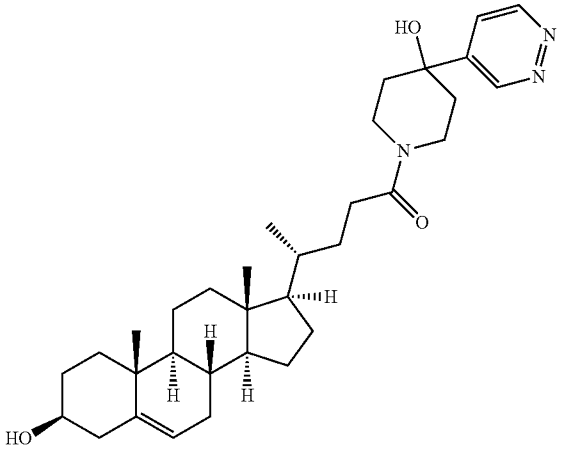

343

To a stirring solution of compound A (200 mg, 1.26 mmol) in tetrahydrofuran (8 mL) was added PhLi (3.1 mL, 1M in THF, 3.1 mmol) at −78° C. under $N_2$ atmosphere, then compound B (440 mg, 1.89 mmol) in THF (10 mL) was added and stirred for 1 h. The mixture was quenched with water (50 mL) and extracted with DCM (30 mL×2). The combined organic layers were washed with brine (50 mL), dried over sodium sulfate, and concentrated in vacuum to give the crude which purified by silica gel chromatography (EtOAc/petroleum ether=1/10-1/3) to give compound C (35 mg, 8.8%).

To a stirring solution of compound C (35 mg, 112 μmol) in isopropanol (2 mL) was added 10% Pt/C (35 mg) at room temperature and stirred under 1 atm of $H_2$ for 16 h. The mixture was filtered and concentrated in vacuum to give the crude which was purified by silica gel chromatography (DCM/MeOH=100/1) to give compound D (14 mg, 22%).

To a solution of compound D (14 mg, 78.1 μmol) in DMF (2 mL) was added compound E (29.3 mg, 78.1 μmol), DIPEA (50.5 mg, 391 μmol) and HATU (36.8 mg, 156 μmol). After stirring at room temperature for 4 h, the mixture was diluted with $NH_4Cl$ (20 mL) and extracted with EA (30 mL×2). The combined organic layers were washed with saturated aqueous $NaHCO_3$ (20 mL), water (20 mL×2), brine (50 mL), dried over sodium sulfate and concentrated in vacuum to give the crude which was purified by silica gel chromatography (DCM/MeOH=100/0-100/2) to give the title compound 343 (7 mg, 17%). LCMS: $[M+H^+]$=536.25. $^{1}H$ NMR (400 MHz, Chloroform-d) δ 9.39 (s, 1H), 9.21-9.16 (m, 1H), 7.62 (d, J=6.0 Hz, 1H), 5.37 (d, J=6.0 Hz, 1H), 4.68 (d, J=12.0 Hz, 1H), 3.85 (d, J=12.0 Hz, 1H), 3.68-3.49 (m, 2H), 3.07 (t, J=12.0 Hz, 1H), 2.50-2.39 (m, 1H), 2.34-2.22 (m, 3H), 2.06-1.71 (m, 8H), 1.68-1.60 (m, 1H), 1.55-1.50 (m, 3H), 1.48-1.42 (m, 2H), 1.38-1.31 (m, 2H), 1.28 (s, 3H), 1.24-1.17 (m, 2H), 1.16-1.06 (m, 3H), 1.03 (s, 3H), 0.99 (d, J=8.0 Hz, 3H), 0.71 (s, 3H).

Example 344: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-hydroxy-4-(pyridin-4-yl)piperidin-1-yl)pentan-1-one

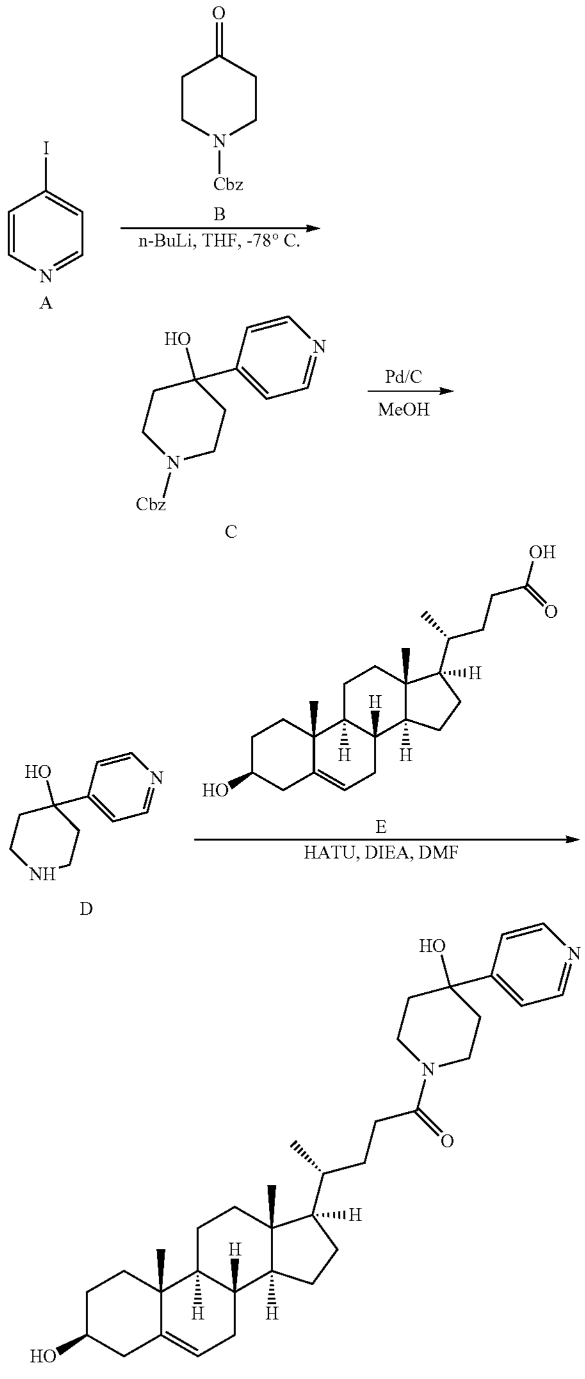

Example 344

A solution of compound A (1.5 g, 7.32 mmol) in THF (15 mL) was cooled to −78° C. n-BuLi (3.5 mL, 8.78 mmol, 2.5M in THF) was added dropwise and the resulting mixture was stirred at −78° C. for 30 min. A solution of compound B (2.39 g, 10.2 mmol) in THF (5 mL) was added and stirred for another 30 min. The reaction was quenched by water (30 mL) and extracted with EtOAc (20 mL×3). The combined organic phase was washed by brine, dried over sodium sulfate, concentrated in vacuum and the residue was purified by silica gel chromatography to afford compound C (1.1 g, 48%) as yellow oil.

To a solution of compound C (1.0 g, 3.2 mmol) in MeOH (20 mL) was added 10% Pd/C (100 mg). The mixture was stirred at room temperature under 1 atm of $H_2$ for 2 h. The mixture was filtered, and the filtrate was concentrated under vacuum to afford compound D (550 mg, 96%) as a white solid.

To a mixture of compound D (114 mg, 641 μmol), compound E (200 mg, 534 μmol) and HATU (305 mg, 801 μmol) in DMF (2 mL) was added DIEA (138 mg 1.07 mmol). The mixture was stirred at room temperature for 1 h. To the mixture, water (10 mL) was added and extracted with EtOAc (10 mL×3). The combined organic phase was washed with brine, dried over sodium sulfate, concentrated in vacuum and the residue was purified by Prep-HPLC to afford the title compound 344 (142 mg, 49%) as a white solid. $^1H$ NMR (400 MHz, Chloroform-d) δ 8.57 (d, J=5.6 Hz, 2H), 7.41-7.33 (m, 2H), 5.34 (d, J=5.2 Hz, 1H), 4.62 (d, J=13.8 Hz, 1H), 3.78 (d, J=13.4 Hz, 1H), 3.61-3.47 (m, 2H), 3.04 (dd, J=14.2, 11.4 Hz, 1H), 2.47-2.37 (m, 1H), 2.31-2.21 (m, 3H), 2.04-1.95 (m, 4H), 1.91-1.80 (m, 6H), 1.78-1.68 (m, 2H), 1.64-1.53 (m, 2H), 1.50-1.42 (m, 4H), 1.36-1.27 (m, 2H), 1.21-1.04 (m, 4H), 1.00 (s, 3H), 0.96 (d, J=6.4 Hz, 3H), 0.91 (dd, J=11.2, 5.4 Hz, 1H), 0.69 (s, 3H).

Example 345: (4R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(3-(pyridazin-4-yl)piperidin-1-yl)pentan-1-one

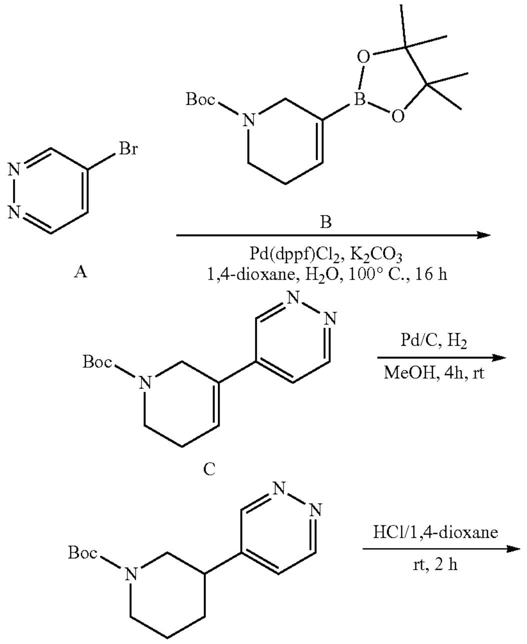

-continued

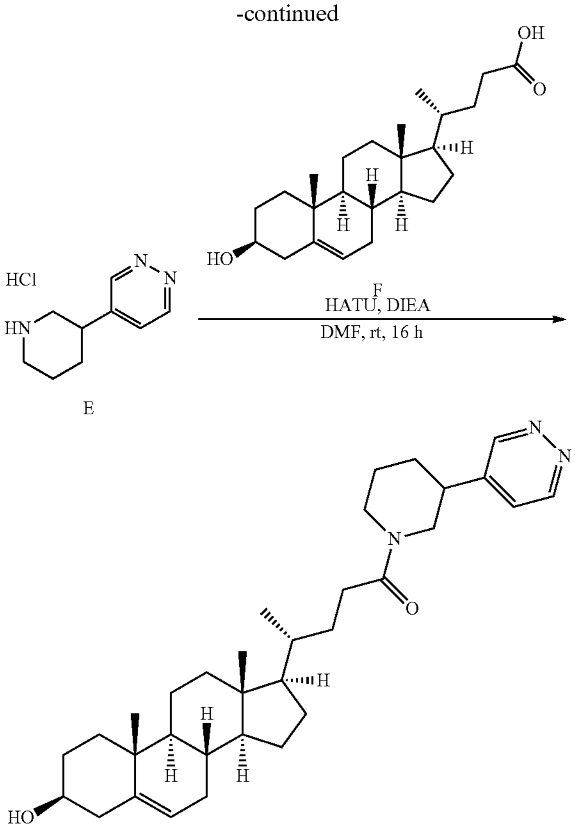

345

To a solution of compound A (100 mg, 629 μmol) in 1,4-dioxane (4 mL) and water (0.6 mL) was added compound B (292 mg, 943 μmol), $Pd(dppf)Cl_2$ (91.3 mg, 126 μmol) and $K_2CO_3$ (261 mg, 1.89 mmol). The mixture was stirred at 100° C. for 16 hours under $N_2$. After completion, the result solution was quenched by the addition of $NH_4Cl$ and extracted with ethyl acetate. The combined organic layers were dried over sodium sulfate and concentrated to give crude product which was purified by silica gel chromatography to give compound C (120 mg, 73.0%) as a white solid. To a solution of compound C (110 mg, 421 μmol) in methanol (8.57 mL) was added 10% Pd/C (22 mg), the mixture was stirred for 4 hours under 1 atm of $H_2$. After completion, the mixture was filtered through Celite and concentrated under vacuum to afford the crude which was purified by silica gel chromatography to give compound D (75 mg, 67.7%) as a white solid.

The Compound D (75 mg, 285 μmol) was added to a solution of HCl (1 mL, 4 mmol, 4 M in dioxane), the mixture was stirred at room temperature for 2 hours. After completion, the mixture was concentrated to give compound E (56.6 mg, 100%) which was used in next step directly.

To a solution of compound F (55.1 mg, 147 μmol) in DMF (1.5 mL) was added Compound E (30 mg, 150 μmol), HATU (86.5 mg, 368 μmol) and DIEA (128 μL, 735 μmol) at room temperature and stirred for 16 h. After completion, the result solution was quenched by the addition of $NH_4Cl$ and extracted with ethyl acetate. The combined organic layers were dried over sodium sulfate and concentrated to give crude product which was purified by column chromatography on silica gel to yield the title compound 345 (17.1 mg, 17.9%) as a white solid. $^1H$ NMR (400 MHz, DMSO-$d_6$) δ 9.22 (d, J=17.4 Hz, 1H), 9.14 (dd, J=8.4, 5.4 Hz, 1H), 7.61 (m, 1H), 5.26 (d, J=3.6 Hz, 1H), 4.39 (dd, J=36.4, 12.8 Hz, 1H), 3.89 (dd, J=34.0, 13.4 Hz, 1H), 3.26-3.04 (m, 3H), 2.89-2.60 (m, 2H), 2.40-2.02 (m, 5H), 1.94-1.29 (m, 17H), 1.22-0.84 (m, 13H), 0.64 (d, J=9.7 Hz, 3H). LCMS: [M+1]=520.30.

Example 346: (4R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(3-(pyridin-4-yl)piperidin-1-yl)pentan-1-one

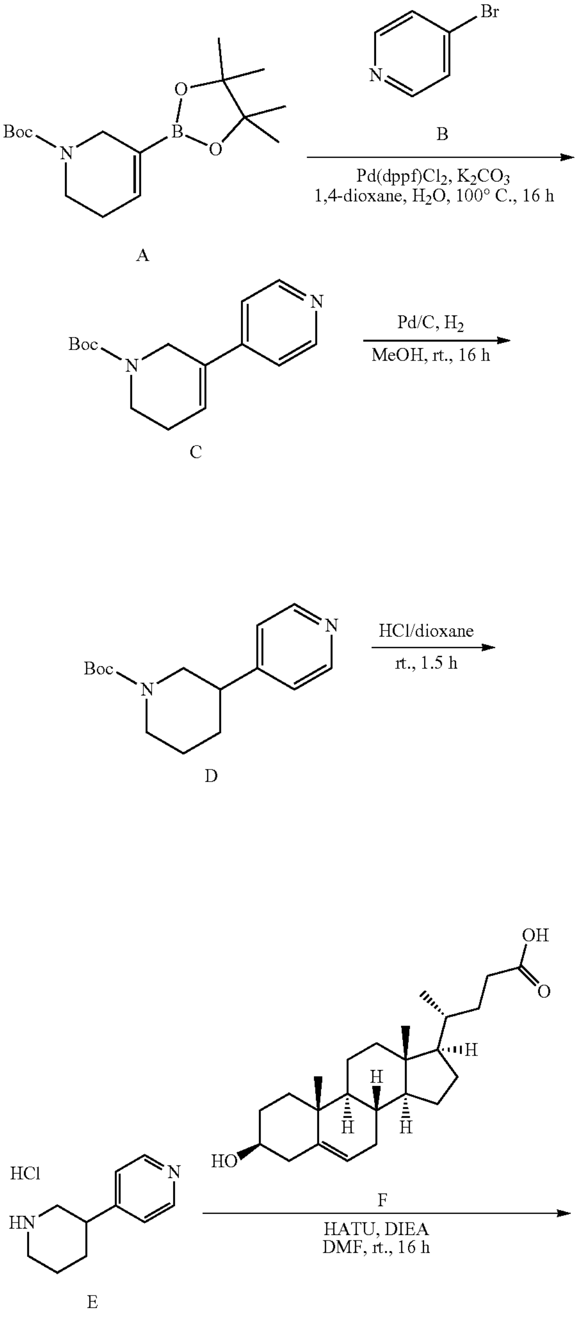

-continued

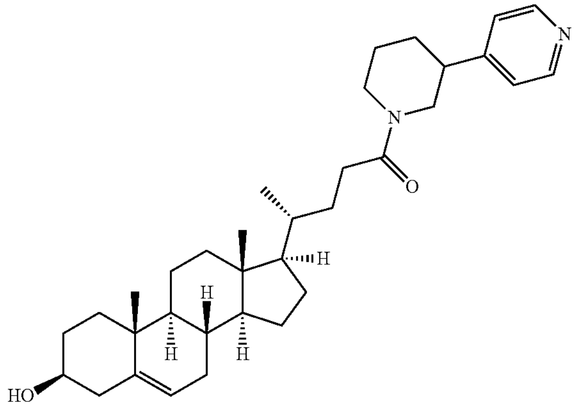

346

To a solution of compound A (200 mg, 647 μmol) in 1,4-dioxane (4 mL) and water (0.4 mL) was added $K_2CO_3$ (268 mg, 1.94 mmol), compound B (307 mg, 1.94 mmol) and Pd(dppf)$Cl_2$ (20 mg). The mixture was stirred at 100° C. under $N_2$ for 16 h. The mixture was extracted with EA and the organic layer was dried over sodium sulfate and concentrated to afford the crude which was purified by silica gel chromatography to afford compound C (160 mg, 95%).

To a solution of compound C (120 mg, 461 μmol) in methanol (2.5 mL) was added 10% Pd/C (24 mg). The mixture was stirred at room temperature under 1 atm of $H_2$ for 16 h. After completion, the mixture was purified by silica gel chromatography to afford compound D (80 mg, 91.6%).

HCl (0.5 mL, 2 mmol, 4 M, 26 eq.) was added to the solution of compound D (80 mg, 305 μmol) in DCM (2 mL). After stirring at room temperature for 1.5 h, the solvent was removed under vacuum to afford crude compound E.

To a solution of compound F (100 mg, 267 μmol) in DMF (2 mL) was added compound E (105.8 mg, 534 μmol), DIEA (173 mg, 1.33 mmol) and HATU (152 mg, 0.4 mmol). The mixture was stirred at room temperature for 16 h. The mixture was diluted with water and extracted with EA. The organic layer was washed with brine, dried over sodium sulfate, and concentrated to afford the crude which was purified by Prep-HPLC to afford the title compound 346 (21.4 mg, 15.5%). LCMS [M+1]=519.25. $^1$H NMR (400 MHz, Chloroform-d) δ 8.58 (s, 2H), 7.37 (s, 1H), 5.35 (d, J=4.9 Hz, 1H), 4.70 (t, J=12.3 Hz, 1H), 3.91 (t, J=14.9 Hz, 1H), 3.57-3.47 (m, 1H), 3.10 (q, J=12.2 Hz, 1H), 2.83-2.52 (m, 2H), 2.48-2.05 (m, 11H), 2.04-1.64 (m, 10H), 1.64-1.41 (m, 9H), 1.37-1.25 (m, 4H), 1.22-1.03 (m, 5H), 1.03-0.87 (m, 9H), 0.68 (d, J=8.2 Hz, 3H).

Example 347: 3—((S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propyl)-1,1-dimethylurea

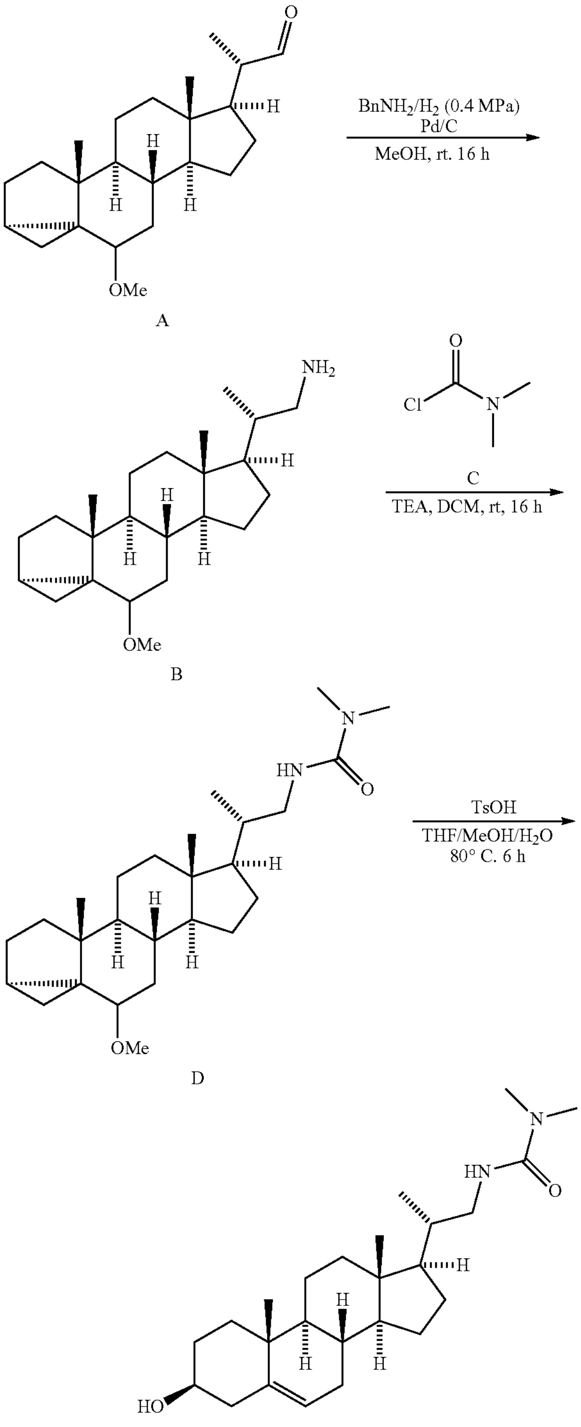

Example 347

To a solution of compound A (5.0 g, 14.5 mmol) in MeOH (100 mL) was added 1-phenylmethanamine (2.33 g, 21.8 mmol) and 10% Pd/C (400 mg) The mixture was stirred at room temperature for 16 hours under 0.4 MPa hydrogen.

The mixture was filtered and concentrated to give the crude which was purified by silica gel chromatography to give compound B (3.0 g, 60%).

To a solution of compound B (500 mg, 1.45 mmol) in dichloromethane (20 mL) was added TEA (732 mg, 7.23 mmol) and compound C (233 mg, 2.17 mmol) at 0° C. The mixture was stirred at room temperature for 16 hours. After completion, the mixture was concentrated to give the crude which was purified by silica gel chromatography to give compound D (590 mg, 97%).

To a solution of compound D (200 mg, 499 μmol) in 1,4-dioxane (2.8 mL) and water (0.4 mL) was added 4-methylbenzene-1-sulfonic acid (17.2 mg, 99.8 μmol). The mixture was stirred at 80° C. for 6 hours. After completion, the mixture was washed with $NaHCO_3$ and extracted with DCM (10 mL×3). The organic layer was washed with brine, dried over sodium sulfate, filtered, and concentrated to give the crude which was purified by silica gel chromatography to give the title compound 347 (34 mg, 16%). $^1$H NMR (400 MHz, Chloroform-d) δ 5.35 (s, 1H), 4.38 (bs, 1H), 3.65 (bs, 1H), 3.55-3.47 (m, 1H), 2.90 (s, 6H), 2.81 (t, J=6.6 Hz, 1H), 2.32-2.21 (m, 2H), 2.06-1.93 (m, 2H), 1.88-1.05 (m, 17H), 1.00 (s, 3H), 0.97-0.91 (m, 1H), 0.89 (s, 1H), 0.87 (s, 1H), 0.75 (s, 3H). LCMS: M+1=403.25.

Example 348: (S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propyl 4-ethyl-4-hydroxypiperidine-1-carboxylate

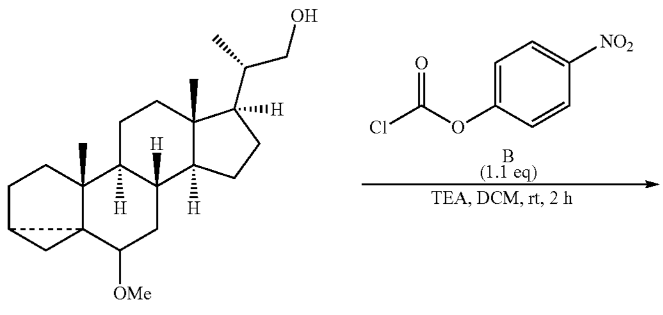

A

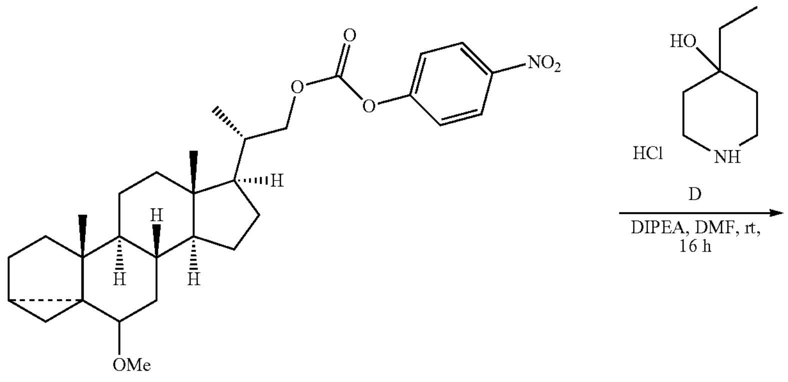

C

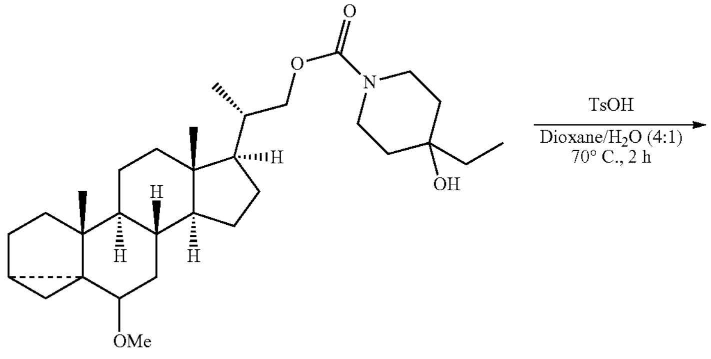

E

-continued

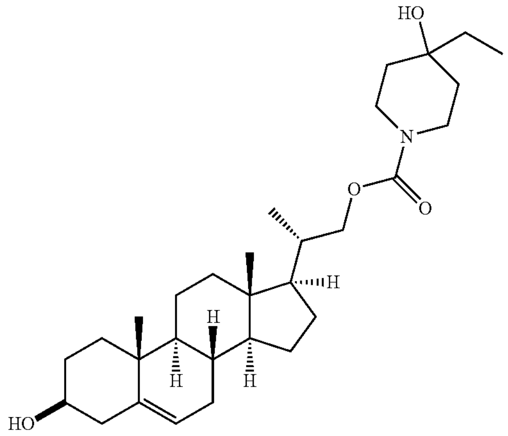

348

To a stirring solution of compound A (500 mg, 1.44 mmol) in dichloromethane (10 mL), compound B (291 mg, 1.44 mmol) and triethylamine (219 mg, 2.16 mmol) was added at 0° C. and stirred at room temperature under $N_2$ atmosphere for 2 h. The mixture was concentrated in vacuum to give the crude which was purified by silica gel chromatography (EtOAc/petroleum ether=1: 20-1/5) to give compound C (750 mg, 99%).

To a stirring solution of compound C (150 mg, 293 μmol) in DMF (5 mL) was added compound D (48.6 mg, 293 μmol) and DIPEA (75.8 mg, 586 μmol) at room temperature and stirred under $N_2$ atmosphere for 16 h. The mixture was diluted with 1N HCl (50 mL) and extracted with EA (30 mL×2), then washed with saturated aqueous $NaHCO_3$ (30 mL) and water (20 mL×2). The combined organic layers were washed with brine (50 mL), dried over sodium sulfate and concentrated in vacuum to give the crude which was purified by silica gel chromatography (DCM: MeOH=100/0100/2) to give compound E (130 mg, 88%) as an off-white solid.

The stirring solution of compound E (30 mg, 59.8 μmol) and 4-methylbenzene-1-sulfonic acid (10.3 mg, 59.8 μmol) in 1,4-dioxane (2 mL) and water (0.5 mL) was heated at 70° C. under $N_2$ atmosphere for 2 h. The mixture was concentrated in vacuum to give the crude which was purified silica gel chromatography (DCM:MeOH=0/100-2/100) to give the title compound 348 (6.8 mg, 23%) as a white solid. LCMS: $[M+H^+]$=488.4. $^1H$ NMR (400 MHz, Chloroform-d) δ 5.26 (d, J=4.0 Hz, 1H), 4.58 (d, J=4.0 Hz, 1H), 4.13 (s, 1H), 3.97 (dd, J=12.0, 4.0 Hz, 1H), 3.74-3.62 (m, 3H), 3.28-3.21 (m, 1H), 3.17-3.06 (m, 2H), 2.20-2.02 (m, 2H), 1.98-1.86 (m, 2H), 1.81-1.61 (m, 4H), 1.60-1.46 (m, 3H), 1.43-1.22 (m, 11H), 1.19-1.04 (m, 3H), 1.00-0.90 (m, 8H), 0.82 (t, J=8.0 Hz, 3H), 0.66 (s, 3H).

Example 349: (S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propyl (2-methoxyethyl)(methyl)carbamate

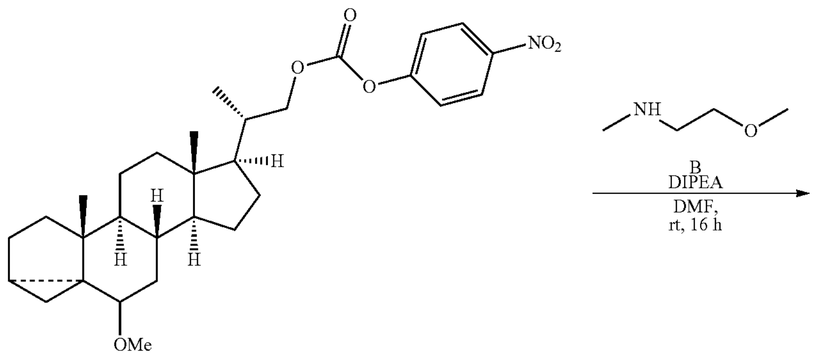

A

-continued

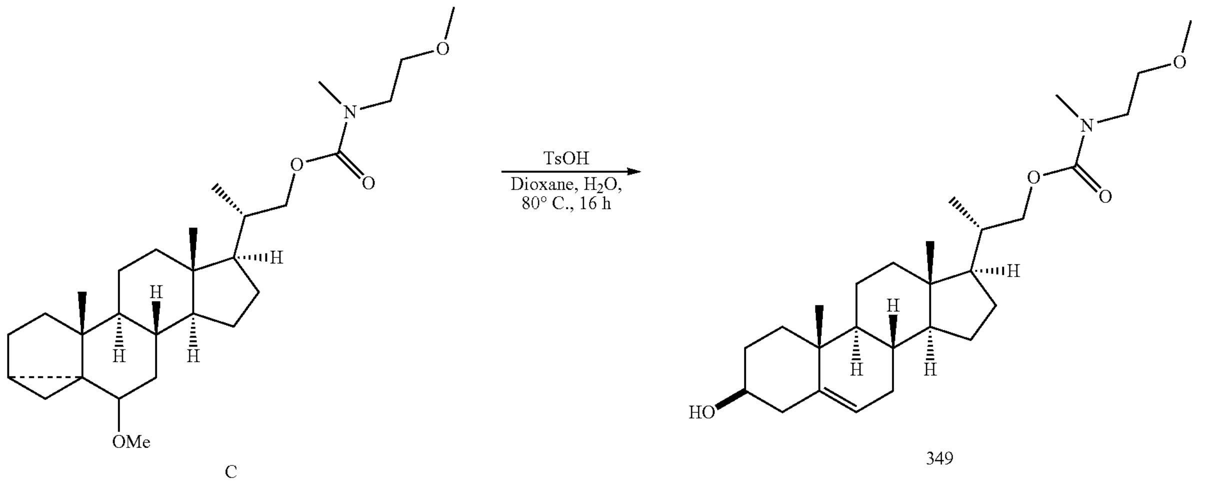

C

349

To a solution of compound A (200 mg, 391 μmol) in DMF (4 mL) was added compound B (34.8 mg, 391 μmol), DIEA (637 mg, 1.17 mmol). After stirring at room temperature for 16 hours, the mixture was diluted with and extracted with ethyl acetate. The combined organic layer was concentrated to give crude which was purified by silica gel chromatography to give compound C (250 mg, 58%).

To a solution of compound C (90 mg, 195 μmol) in 1,4-dioxane (4 mL) and water (1 mL) was added 4-methylbenzene-1-sulfonic acid (6.17 mg, 39 μmol). The mixture was stirred at 80° C. for 16 hours. After completion, the mixture was quenched by adding $NaHCO_3$ (30 mL) and extracted with ethyl acetate (10 mL×3). The organic layer was washed with brine, dried over sodium sulfate, filtered, and concentrated to give the crude which was purified by column chromatography on silica gel to yield the title compound 349 (40 mg, 45%) as a white solid. LCMS: $[M+1]^+$=448.25. $^1H$ NMR (400 MHz, Chloroform-d) δ 5.34 (dt, J=4.2, 1.8 Hz, 1H), 4.10 (dd, J=10.4, 3.4 Hz, 1H), 3.77 (t, J=9.0 Hz, 1H), 3.58-3.38 (m, 5H), 3.35 (s, 3H), 2.96 (s, 3H), 2.35-2.18 (m, 2H), 2.06-1.93 (m, 2H), 1.88-1.80 (m, 3H), 1.72 (dtd, J=10.3, 6.8, 3.4 Hz, 1H), 1.65-1.57 (m, 2H), 1.54-1.43 (m, 4H), 1.39-1.27 (m, 1H), 1.22-1.14 (m, 2H), 1.12-1.06 (m, 1H), 1.03 (d, J=6.6 Hz, 3H), 1.01 (s, 4H), 0.96-086 (m, 1H), 0.70 (s, 3H).

Example 350: (2S)-2-[(1R,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]propyl N-(2-hydroxyethyl)-N-methylcarbamate

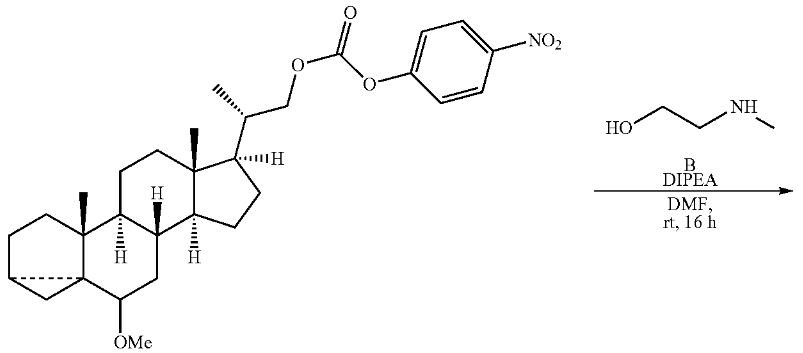

A

-continued

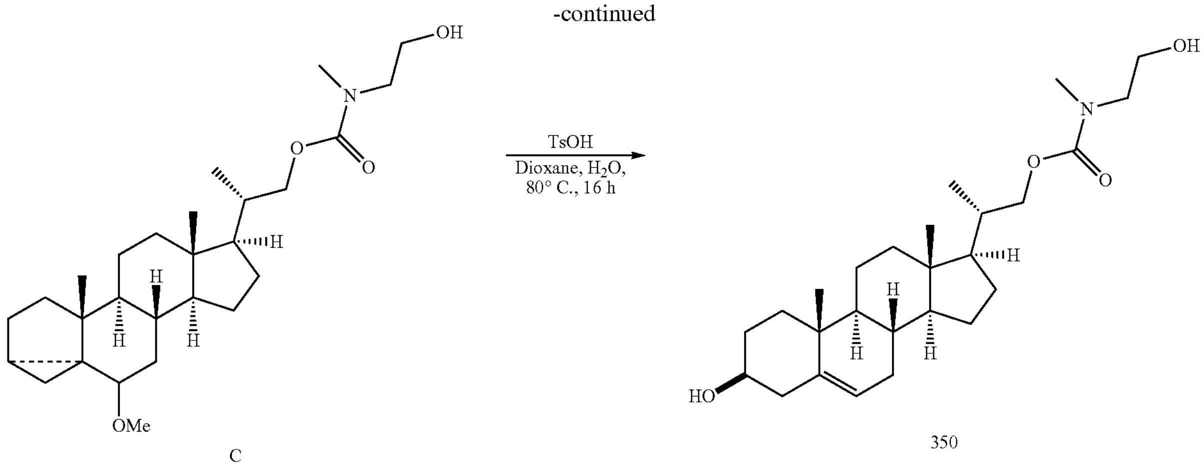

C

350

To a solution of compound A (200 mg, 391 μmol) in DMF (4 mL) was added compound B (29.4 mg, 391 μmol), DIEA (637 mg, 1.17 mmol). After stirring at room temperature for 16 hours, the mixture was diluted with and extracted with ethyl acetate. The organic layers were concentrated to give crude which was purified by silica gel chromatograph to give compound C (71 mg, 40%).

To a solution of compound C (70 mg, 156 μmol) in 1,4-dioxane (4 mL) and water (1 mL) was added 4-methylbenzene-1-sulfonic acid (5.39 mg, 31.3 μmol). The mixture was stirred at 80° C. for 16 hours. After completion, the mixture was quenched by adding $NaHCO_3$ (30 mL) and extracted with ethyl acetate (10 mL×3). The combined organic layers were washed with brine, dried over sodium sulfate, filtered, and concentrated to give the crude which was purified by column chromatography on silica gel to yield the title compound 350 (10 mg, 15%) as a white solid. LCMS: $[M+1]^+$=434.20. $^1H$ NMR (400 MHz, Chloroform-d) δ 5.35 (dd, J=5.3, 2.5 Hz, 1H), 4.11 (dd, J=10.4, 3.4 Hz, 1H), 3.81-3.75 (m, 3H), 3.58-3.48 (m, 1H), 3.44 (t, J=5.0 Hz, 2H), 2.98 (s, 3H), 2.33-2.21 (m, 2H), 2.04-1.93 (m, 2H), 1.88-1.80 (m, 3H), 1.78-1.70 (m, 3H), 1.65-1.59 (m, 1H), 1.54-1.43 (m, 4H), 1.38-1.30 (m, 2H), 1.22-1.16 (m, 2H), 1.13-1.07 (m, 2H), 1.04 (d, J=6.6 Hz, 3H), 1.01 (s, 3H), 0.99-0.84 (m, 2H), 0.71 (s, 3H).

Example 351: (S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propyl methylcarbamate

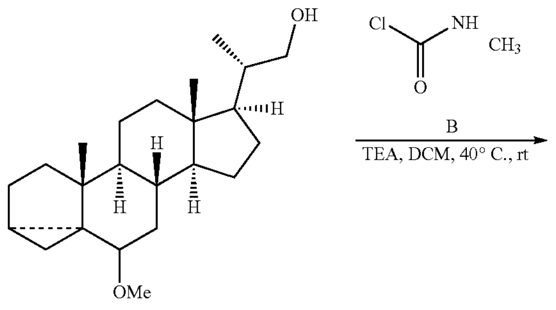

A

-continued

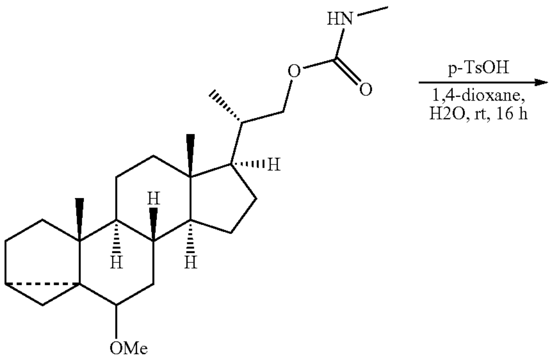

C

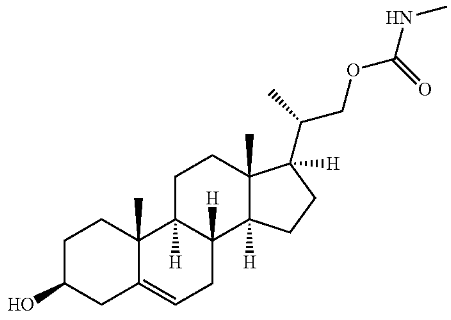

351

To a solution of compound A (100 mg, 289 μmol) in dichloromethane (5 mL) was added triethylamine (234 mg, 2.31 mmol) and compound B (162 mg, 1.73 mmol). The solution was stirred at 40° C. for 16 hours under $N_2$. After completion, the mixture was quenched by adding saturated aqueous ammonium chloride (30 mL) and extracted with ethyl acetate (15 mL×3). The combined organic layers were washed with brine, dried over sodium sulfate, filtered, and concentrated to give the crude which was purified by column chromatography on silica gel to yield the title compound C (110 mg, 94%).

To a solution of compound C (100 mg, 248 μmol) in 1,4-dioxane (2.1 mL) and water (0.3 mL) was added 4-methylbenzene-1-sulfonic acid (8.5 mg, 49 μmol). The mixture was stirred at 80° C. for 16 hours. After completion, the mixture was quenched by adding saturated aqueous $NaHCO_3$ (15 mL) and extracted with ethyl acetate (10 mL×3). The combined organic layers were washed with brine, dried over sodium sulfate, filtered, and concentrated to give the crude which was purified by prep-HPLC to give the title compound 351 (30 mg, 31%) as a white solid. $^1H$ NMR (400 MHz, Chloroform-d) δ 5.35 (d, J=5.1 Hz, 1H), 4.57 (s, 1H), 4.09 (d, J=10.4 Hz, 1H), 3.76 (t, J=9.0 Hz, 1H), 3.56-3.41 (m, 1H), 2.79 (d, J=4.7 Hz, 3H), 2.32-2.19 (m, 2H), 2.02-1.94 (m, 2H), 1.90-1.59 (m, 6H), 1.51-1.43 (m, 4H), 1.34 (t, J=11.5 Hz, 1H), 1.22-1.07 (m, 4H), 1.01 (s, 6H), 0.93 (dt, J=11.3, 5.7 Hz, 1H), 0.70 (s, 3H). LCMS: $[M+1]^+$=390.25.

Example 352: (2S)-2-[(1R,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]propyl N-ethyl-N-methylcarbamate

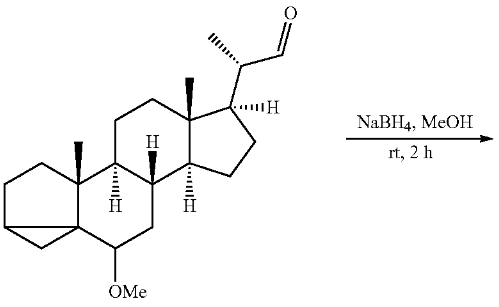

A

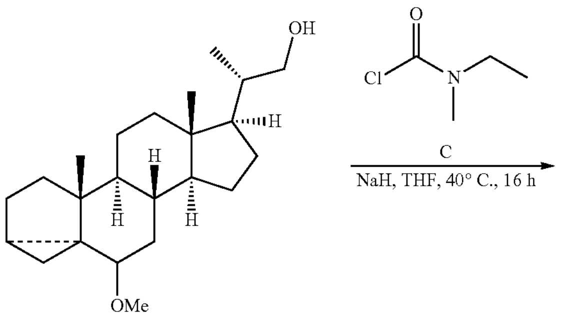

B

C

-continued

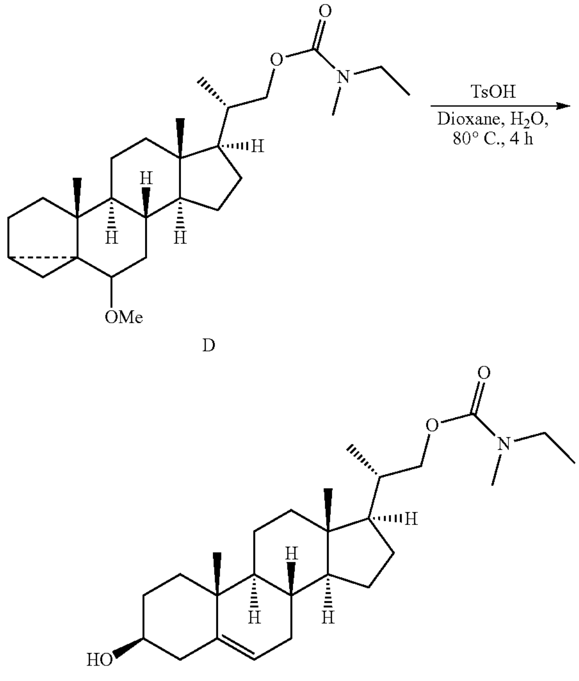

D

352

To a solution of compound A (2.0 g, 5.8 mmol) in MeOH (15 mL) was added $NaBH_4$ (438 mg, 11.3 mmol). The mixture was stirred at room temperature for 2 hours. The mixture was with diluted with water and extracted with ethyl acetate. The organic layer was concentrated to give the crude which was purified by silica gel chromatography to give compound B (1.0 g, 50%).

To a solution of compound B (500 mg, 1.44 mmol) in THE (10 mL) was added NaH (140 mg, 3.5 mmol, 60% dispersion in oil). After stirring at room temperature for 30 mins, to the mixture was added compound C. The reaction was warmed to 40° C. and stirred for 16 hours. The mixture was diluted with water and extracted with ethyl acetate. The organic layer was concentrated to give the crude which was purified by silica gel chromatography to give compound D (350 mg, 56%).

To a solution of compound D (200 mg, 436 μmol) in 1,4-dioxane (4 mL) and water (1 mL) was added 4-methylbenzene-1-sulfonic acid (16 mg, 92 μmol). The mixture was stirred at 80° C. for 4 hours. After completion, the mixture was quenched by adding saturated aqueous $NaHCO_3$ (30 mL) and extracted with ethyl acetate (10 mL×3). The combined organic layers were washed with brine, dried over sodium sulfate, filtered, and concentrated to give the crude which was purified by column chromatography on silica gel to yield the title compound 352 (100 mg, 52%) as a white solid. LCMS: $[M+1]^+$=418.25. $^1H$ NMR (400 MHz, Chloroform-d) δ 5.35 (d, J=5.1 Hz, 1H), 4.09 (dd, J=10.5, 3.4 Hz, 1H), 3.76 (t, J=8.8 Hz, 1H), 3.52 (dt, J=11.2, 6.1 Hz, 1H), 3.30 (bs, 2H), 2.88 (s, 3H), 2.33-2.18 (m, 2H), 2.05-1.93 (m, 2H), 1.88-1.79 (m, 3H), 1.77-1.69 (m, 1H), 1.65-1.56 (m, 3H), 1.52-1.46 (m, 3H), 1.39-1.30 (m, 1H), 1.23-1.17 (m, 2H), 1.13-1.07 (m, 5H), 1.03 (d, J=6.7 Hz, 3H), 1.01 (s, 3H), 0.97-0.81 (m, 2H), 0.71 (s, 3H).

Example 353: 4-ethyl-5-((R)-3-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)butyl)-2,4-dihydro-3H-1,2,4-triazole-3-thione

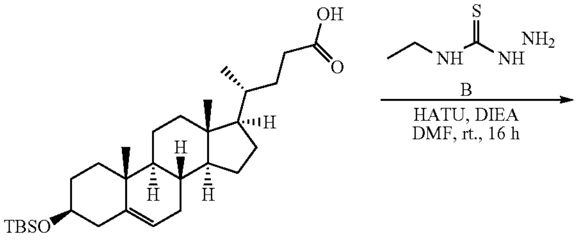

A

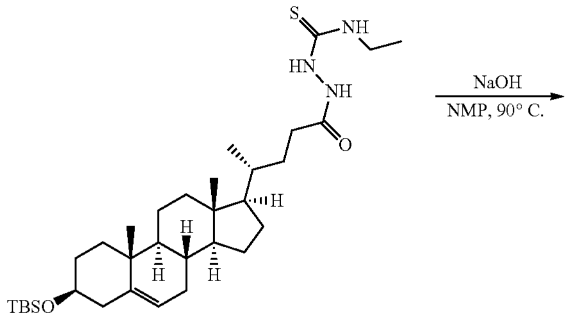

C

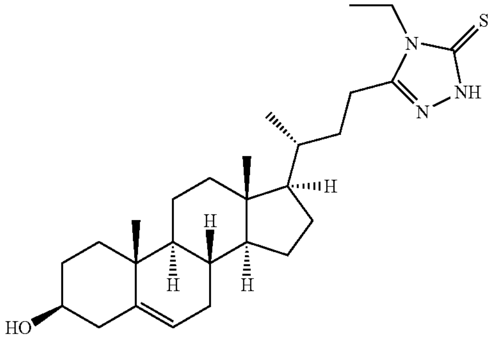

353

To a solution of A (2.05 g, 4.19 mmol) in dry DMF (20 mL) was added compound B (500 mg, 4.19 mmol), DIEA (2.71 g, 21 mmol) and HATU (2.39 g, 6.29 mmol). The mixture was stirred at room temperature for 16 h. The mixture was added water and extracted with EA. The organic layer was washed with brine, dried over sodium sulfate, and concentrated. The crude was purified by silica gel chromatography to afford compound C (160 mg, 7%).

To a solution of C (160 mg, 271 μmol) in NMP (5.33 mL) was added solution of sodium hydroxide (21.7 mg, 542 μmol) in water (1 mL). The mixture was stirred at 90° C. under $N_2$ for 16 h. The mixture was adjusted pH=3 with 1N HCl and extracted with EA. The organic layer was washed with brine, dried over sodium sulfate, and concentrated to afford the crude which was purified by silica gel chromatography to afford compound 353 (15.1 mg, 12%). LCMS $[M+1]^+$=458.25. $^1$H NMR (400 MHz, Chloroform-d) δ 5.35 (d, J=5.1 Hz, 1H), 4.05 (q, J=7.2 Hz, 2H), 3.53 (dt, J=13.8, 7.2 Hz, 1H), 2.75-2.61 (m, 1H), 2.54 (dt, J=15.0, 7.9 Hz, 1H), 2.30-2.22 (m, 3H), 2.06-1.81 (m, 8H), 1.77-1.41 (m, 17H), 1.40-1.29 (m, 8H), 1.23-1.00 (m, 14H), 0.98-0.80 (m, 5H), 0.70 (s, 3H).

Example 354: 5-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]-1λ$^6$,2,5-thiadiazepane-1,1-dione

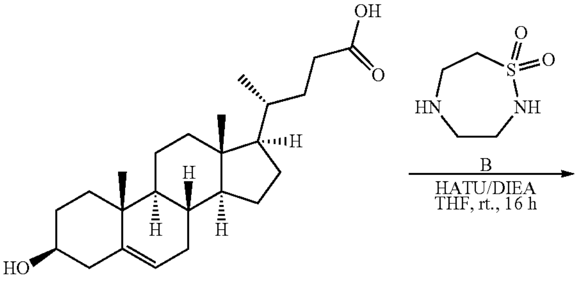

A

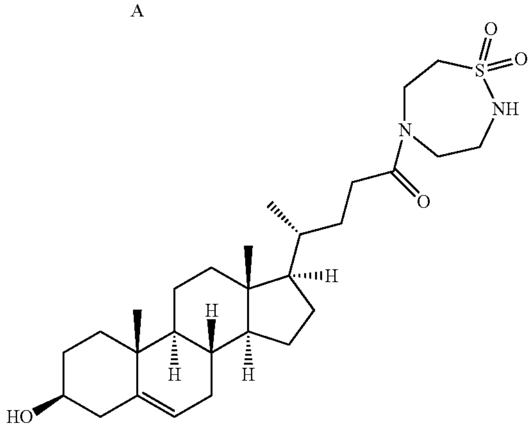

354

To a solution of compound A (50 mg, 133 μmol) in DMF (5 mL) was added DIEA (51.8 mg, 0.4 mmol), compound B (40.1 mg, 267 μmol) and HATU (62.8 mg, 267 μmol) at room temperature. The resulting mixture was stirred at room temperature for 16 h. The mixture was diluted with water and ethyl acetate. The organic layer was washed with water and brine, dried with sodium sulfate and concentrated under vacuum. The residue was purified by a Biotage (C18 column, eluting with 10% to 95% Acetonitrile/$H_2O$, containing 0.1% formic acid) to give the title compound 354 (24.0 mg, 35.5%). LCMS: $[M+H]^+$=507.20. $^1$H NMR (400 MHz, Chloroform-d) δ 5.35 (d, J=4.1 Hz, 1H), 4.64 (dt, J=27.7, 5.8 Hz, 1H), 3.89-3.76 (m, 4H), 3.58-3.46 (m, 1H), 3.42-3.26 (m, 4H), 2.39-2.31 (m, 1H), 2.30-2.17 (m, 3H), 2.02-1.94 (m, 2H), 1.91-1.78 (m, 4H), 1.63-1.42 (m, 6H), 1.40-1.29 (m, 3H), 1.25 (s, 2H), 1.14 (dd, J=16.4, 7.5 Hz, 3H), 1.01 (s, 3H), 0.97-0.91 (m, 4H), 0.69 (s, 3H).

Example 355: {[(1R,3aS,3bS,5S,5aR,7R,9aR,9bS,11aR)-7-[(tert-butyldimethylsilyl)oxy]-9a,11a-dimethyl-1-[(2R,3E)-6-methyl-5-(trifluoromethyl)-5-[(trimethylsilyl)oxy]hept-3-en-2-yl]-hexadecahydro-1H-cyclopenta[a]phenanthren-5-yl]oxy}(tert-butyl)dimethylsilane

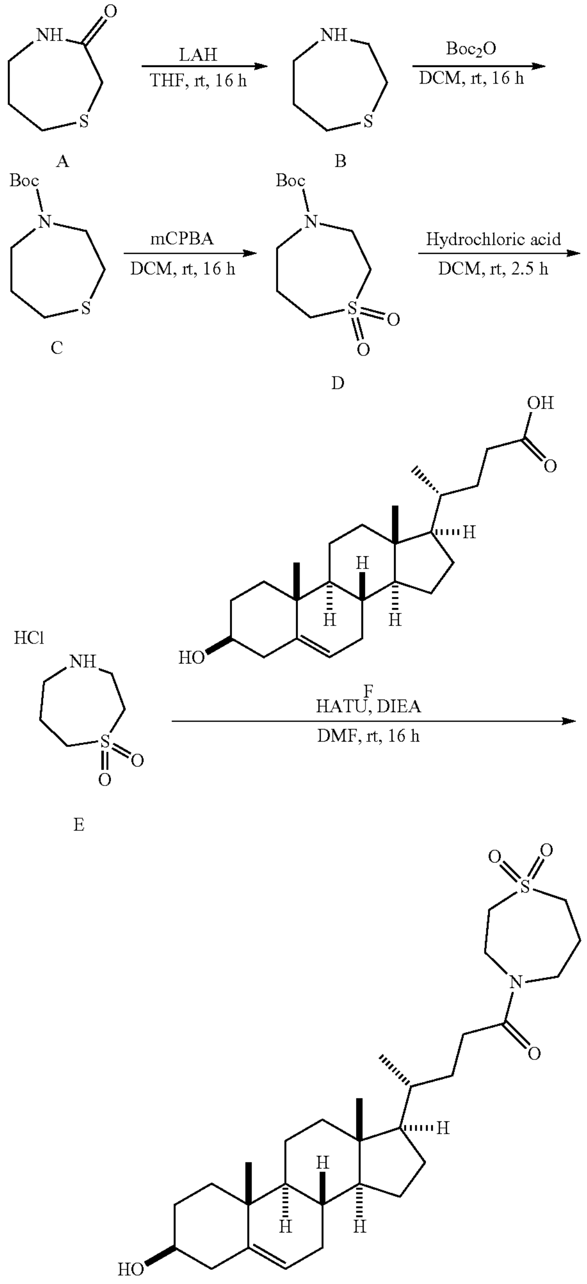

355

To a solution of compound A (700 mg, 5.34 mmol) in THF (10 mL) was added LAH (506 mg, 13.3 mmol). The mixture was stirred at room temperature for 16 hours. The mixture was diluted with water and extracted with ethyl acetate. The organic layer was concentrated to give the crude which was purified by silica gel chromatography to give compound B (580 mg, 92%). To a solution of compound B (580 mg, 4.95 mmol) in DCM (10 mL) was added $Boc_2O$ (580 mg, 4.95 mmol). The mixture was stirred at room temperature for 16 hours. The mixture was diluted with water and extracted with DCM. The organic layer was concentrated to give the crude which was purified by silica gel chromatography to give compound C (850 mg, 79%).

To a solution of compound C (200 mg, 920 μmol) in DCM (10 mL) was added mCPBA (397 mg, 2.3 mmol). The mixture was stirred at room temperature for 16 hours. The mixture was diluted with water extracted with DCM. The organic layer was concentrated to give the crude which was purified by silica gel chromatography to give compound D (150 mg, 60%).

To a solution of compound D (300 mg, 1.2 mmol) in dichloromethane (4 mL) was added HCl (0.6 mL, 2.4 mmol, 4M in dioxane). The mixture was stirred at room temperature for 16 hours. The mixture was concentrated to afford compound E (187.3 mg) which was used in next step directly.

To a solution of compound E (187.3 mg, 1.01 mmol) in DMF (4 mL) was added compound F (188 mg, 503 μmol), DIEA (290 mg, 2.2 mmol) and HATU (287 mg, 754 μmol). The mixture was stirred at room temperature for 16 hours. The mixture was diluted with water and extracted with ethyl acetate. The organic layer was concentrated to give the crude which was purified by silica gel chromatography to give the title compound 355 (80 mg, 31%). LCMS: $[M+1]^+$=506.25. $^1H$ NMR (400 MHz, Chloroform-d) δ 5.35 (d, J=5.0 Hz, 1H), 3.83-3.68 (m, 4H), 3.52 (dt, J=11.2, 6.4 Hz, 1H), 3.28 (t, J=5.5 Hz, 2H), 3.16-3.08 (m, 2H), 2.48-2.07 (m, 7H), 2.03-1.80 (m, 6H), 1.55-1.24 (m, 10H), 1.20-1.07 (m, 3H), 1.01 (s, 3H), 0.95 (d, J=6.5 Hz, 3H), 0.93-0.81 (m, 1H), 0.69 (s, 3H).

Example 356: (2R)-4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]-2-methyl-1λ$^6$-thiomorpholine-1,1-dione

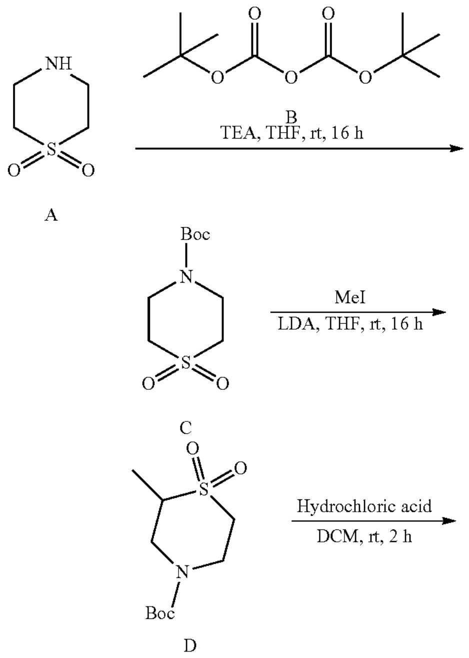

-continued

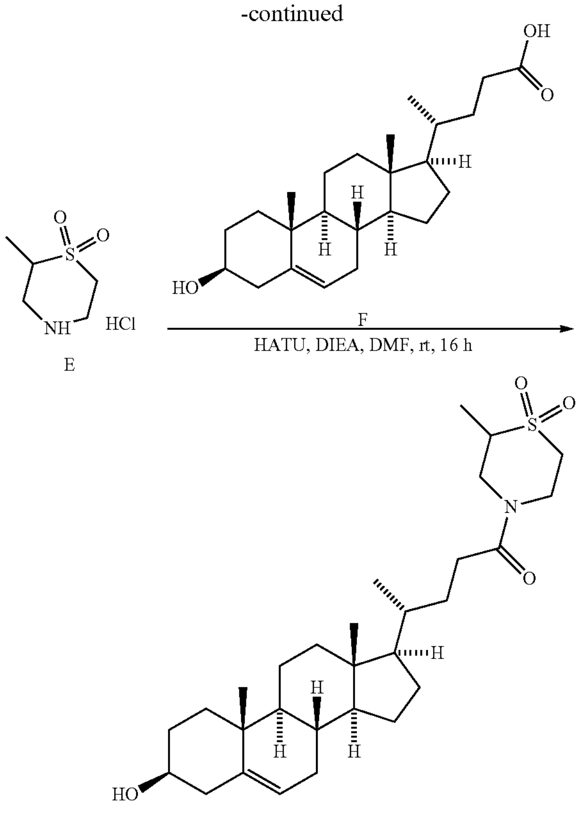

356

To a solution of compound A (750 mg, 5.55 mmol) in tetrahydrofuran (10 mL) was added compound B (1.1 g, 4.67 mmol) and triethylamine (1.12 g, 2 eq., 11.1 mmol). The mixture was stirred at room temperature for 16 hours. After completion, the mixture was quenched by adding $H_2O$ (30 mL) and extracted with ethyl acetate (15 mL×3). The organic layer was washed with brine, dried over sodium sulfate, filtered, and concentrated to give the crude which was purified by column chromatography on silica gel to yield the title compound C (1.1 g, 84%) as a white solid.

To a solution of compound C (300 mg, 1.27 mmol) in tetrahydrofuran (3 mL) was added LDA (0.65 mL, 1.3 mmol) at −78° C.; and stirred for 0.5 h under $N_2$. Then, to the solution was added iodomethane (271 mg, 1.91 mmol) and stirred at room temperature for 16 h. After completion, the mixture was quenched by adding $H_2O$ (50 mL) and extracted with ethyl acetate (15 mL×3). The organic layer was washed with brine, dried over sodium sulfate, filtered, and concentrated to give the crude which was purified by column chromatography on silica gel to yield the title compound D (200 mg, 63%) as a white solid.

HCl (0.5 mL, 2 mmol, 4M in dioxane) was added slowly to the solution of compound D (50 mg, 201 μmol) in DCM (2 mL) at room temperature and stirred for 2 h. After completion, the reaction mixture was concentrated to give the title compound E (37 mg, 100%) as a solid.

To a solution of compound E (100 mg, 536 μmol) in DMF (3 mL) was added compound F (181 mg, 483 μmol), DIEA (416 mg, 3.22 mmol) and HATU (288 mg, 1.07 mmol). The mixture was stirred at room temperature for 16 hours. After completion, the mixture was quenched by adding saturated ammonium chloride solution (30 mL) and extracted with ethyl acetate (15 mL×3). The organic layer was washed with brine, dried over sodium sulfate, filtered, and concentrated to give the crude which was purified by prep-HPLC to give the title compound 356 (30 mg, 11%) as a white solid. $^1$H NMR (400 MHz, Chloroform-d) δ 5.35 (d, J=5.0 Hz, 1H), 4.64 (dd, J=31.7, 12.7 Hz, 1H), 4.19-2.89 (m, 7H), 2.46-2.19 (m, 4H), 2.07-1.75 (m, 6H), 1.53-1.43 (m, 6H), 1.41-1.25 (m, 6H), 1.22-1.06 (m, 4H), 1.01 (s, 3H), 0.95 (d, J=6.5 Hz, 3H), 0.93-0.80 (m, 1H), 0.69 (s, 3H). LCMS: $[M+1]^+$=506.25.

Example 357: (R)-1-(1,1-dioxidothiazolidin-3-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl) pentan-1-one

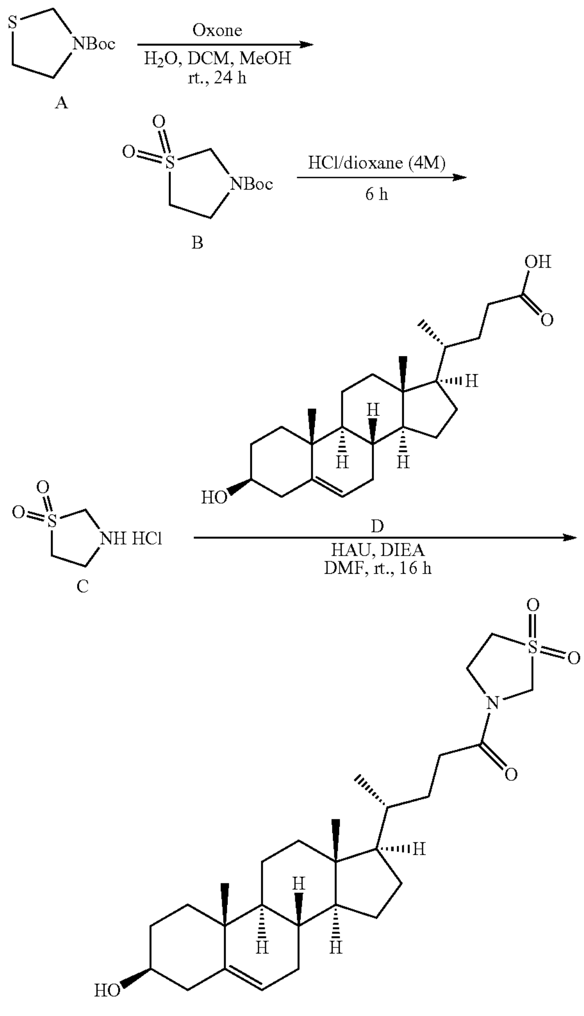

357

The solution of Oxone (929 mg, 1.51 mmol) in water (10 mL) was added into a solution PGP-387,C3 of compound A (220 mg, 1.16 mmol) in dichloromethane (3.33 mL) and methanol (6.67 mL) at room temperature. The mixture was stirred at room temperature for 24 hours. After completion, the mixture was added 8 mL water and extracted with DCM. The organic layer was dried over sodium sulfate and concentrated. The residue was purified by silica gel chromatography to afford compound B (210 mg, 82%).

To a solution of HCl (0.9 mL, 3.6 mmol, 4M in dioxane) was added B (100 mg, 452 μmol). The mixture was stirred at room temperature for 6 h. The mixture was concatenated to afford compound C (80 mg) which was used directly in the next step.

To a solution of compound D (150 mg, 0.4 mmol) in DMF (3 mL) was added compound C (125.9 mg, 801 μmol), DIEA (259 mg, 2 mmol) and HATU (228 mg, 601 μmol). The mixture was stirred at room temperature for 16 h. The mixture was added water and extracted with EA. The organic layer was washed with brine, dried over sodium sulfate, and concentrated. The residue was purified by Prep-HPLC to afford compound 357 (6 mg, 3.2%). LCMS $[M+1]^+$=478.20. $^1$H NMR (400 MHz, Chloroform-d) δ 5.35 (d, J=4.9 Hz, 1H), 4.53 (bs, 1H), 4.44 (bs, 1H), 4.16-4.01 (m, 2H), 3.57-3.47 (m, 1H), 3.38-3.20 (m, 2H), 2.39-1.75 (m, 10H), 1.65-1.27 (m, 12H), 1.21-0.81 (m, 14H), 0.69 (s, 3H).

Example 358: 4—((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N,N-dimethylpiperazine-1-sulfonamide

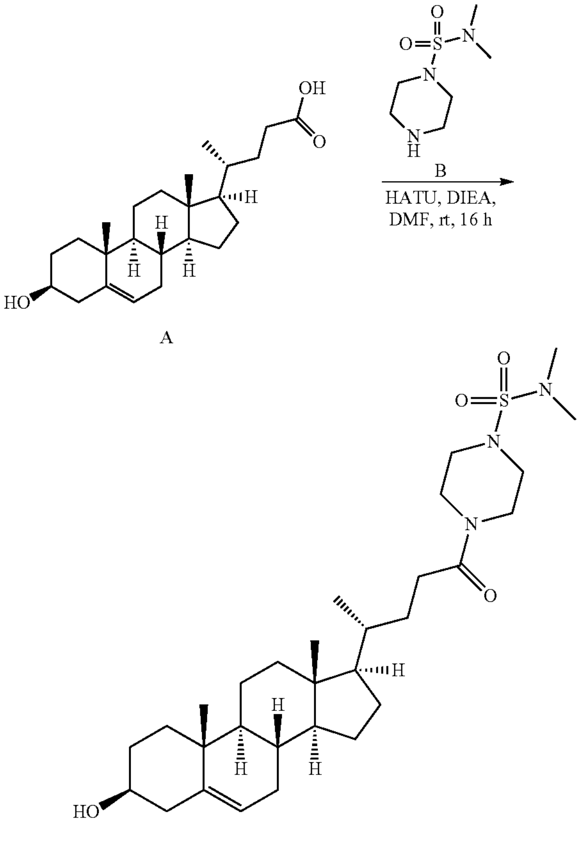

Example 358

To a solution of compound A (100 mg, 267 μmol) in DMF (2 mL) was added compoundB (61.9 mg, 320 μmol), HATU (126 mg, 534 μmol) DIEA (173 mg, 1.33 mmol). The mixture was stirred at room temperature for 16 hours. After completion, the mixture was diluted with water and extracted with ethyl acetate. The organic layer was concentrated to give crude which was purified by prep-HPLC to give the title compound 358 (119 mg, 80%). $^1$H NMR (400 MHz, Chloroform-d) δ 5.35 (d, J=5.0 Hz, 1H), 3.72-3.65 (m, 2H), 3.58-3.49 (m, 3H), 3.29-3.15 (m, 4H), 2.84 (s, 6H), 2.43-2.16 (m, 4H), 2.07-1.71 (m, 6H), 1.65-1.02 (m, 18H), 1.01 (s, 3H), 0.95 (d, J=6.6 Hz, 3H), 0.90-0.83 (m, 1H), 0.68 (s, 3H). LCMS: [M+1]=550.30.

Example 359: 4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]piperazine-1-sulfonamide

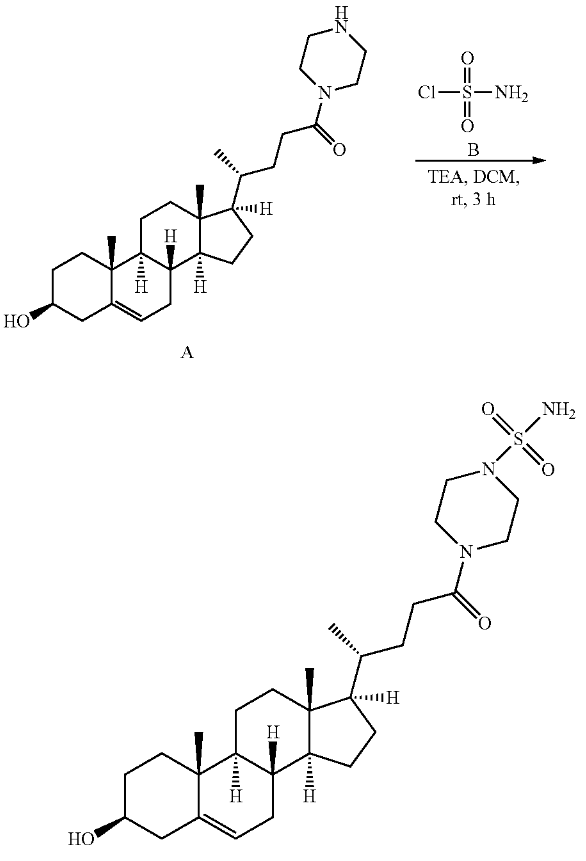

359

To a solution of compound A (271 mg, 612 μmol) and triethylamine (124 mg, 1.22 mmol) in dichloromethane (16.3 mL) was added compound B (70.7 mg, 612 μmol) at 0° C. After stirring at room temperature for 3 h, the mixture was diluted with water and extracted with ethyl acetate. The organic layer was dried with sodium sulfate and concentrated under vacuum. The residue was purified by silica gel chromatography (eluting with 1/1 ethyl acetate/PE) to give the title compound 359 (7.2 mg, 2.25%). LCMS: $[M+H]^+$=522.25. $^1$H NMR (400 MHz, Chloroform-d) δ 5.35 (d, J=4.2 Hz, 1H), 4.39 (s, 2H), 3.74 (bs, 2H), 3.63-3.45 (m, 3H), 3.18 (bs, 4H), 2.47-2.21 (m, 4H), 2.03-1.81 (m, 6H), 1.51-1.07 (m, 17H), 1.01 (s, 3H), 0.96 (d, J=6.5 Hz, 3H), 0.69 (s, 3H).

Example 360: methyl 4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperazine-1-carboxylate

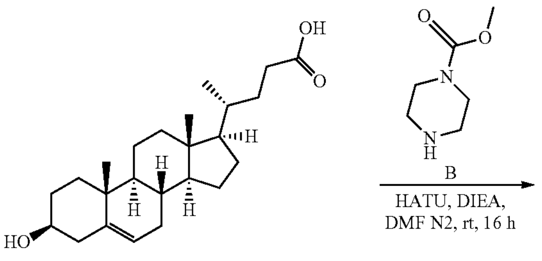

A

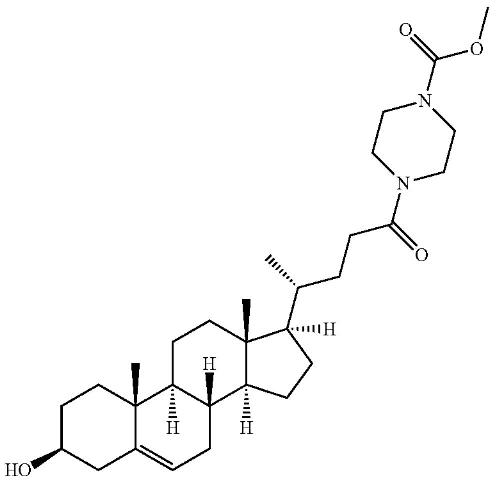

360

To a solution of compound A (100 mg, 0.27 mmol) in DMF (3 mL) was added compound B (38.5 mg, 0.27 mmol), HATU (200 mg, 0.534 mmol) and DIEA (200 mg, 1.6 mmol). The mixture was stirred at room temperature under $N_2$ for 16 h. The reaction was quenched with saturated $NH_4Cl$ and extracted with EtOAc. The organic layer was washed by brine, dried over sodium sulfate, filtered, and concentrated. The mixture was purified by column chromatography on silica gel to afford the title compound 360 (21 mg) as a white solid. $^1H$ NMR (400 MHz, Chloroform-d) δ 5.35 (s, 1H), 3.72 (s, 3H), 3.65-3.38 (m, 9H), 2.42-2.17 (M, 4H), 2.05-1.73 (m, 6H), 1.67-0.82 (m, 29H), 0.68 (s, 3H). LCMS: [M+H]=501.25.

Example 361: 4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]-1-methylpiperazin-2-one

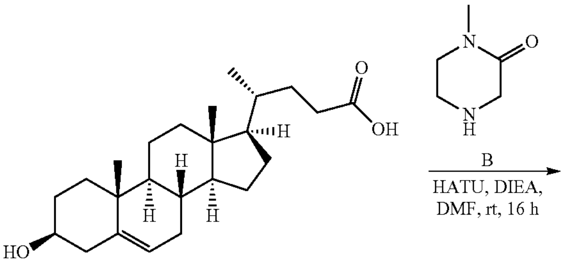

A

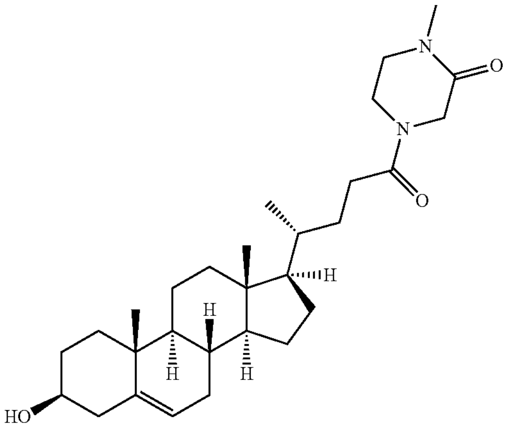

361

To a solution of compound A (100 mg, 267 μmol) in DMF (2 mL) was added compound B (30.5 mg, 267 μmol), DIEA (207 mg, 6 eq., 1.6 mmol) and HATU (203 mg, 2 eq., 534 μmol). The mixture was stirred at room temperature for 16 hours. After completion, the reaction was quenched with water and extracted with ethyl acetate (10 mL×4). The combined organic layer was concentrated to give the crude which was purified by silica gel chromatography to yield the title compound 361 (20 mg, 15%). LCMS:$[M+1]^+$=471.20. $^1H$ NMR (400 MHz, Chloroform-d) δ 5.38-5.32 (m, 1H), 4.26-4.09 (m, 2H), 3.91-3.66 (m, 2H), 3.58-3.48 (m, 1H), 3.90-3.66 (m, 2H), 3.01 (s, 3H), 2.43-2.15 (m, 5H), 2.04-1.92 (m, 2H), 1.89-1.72 (m, 5H), 1.52-1.39 (m, 6H), 1.36-1.23 (m, 3H), 1.21-1.05 (m, 4H), 1.00 (s, 3H), 0.94 (d, J=6.4 Hz, 3H), 0.68 (s, 3H).

Example 362: 4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]piperazin-2-one

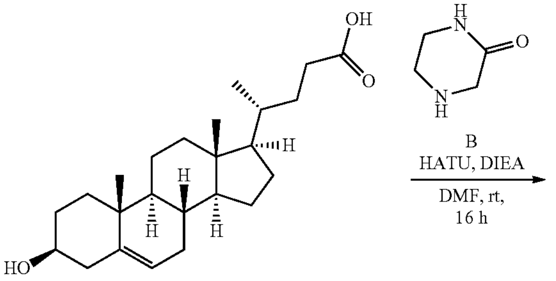

A

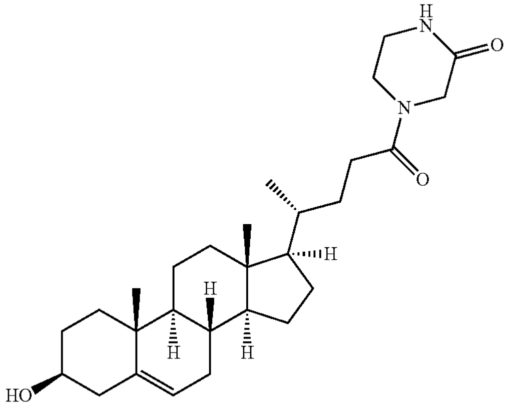

362

To a solution of compound A (100 mg, 267 μmol) in DMF (4 mL) was added HATU (203 mg, 534 μmol), compound B ((53.5 mg, 534 μmol)) and DIEA (173 mg, 1.33 mmol). The mixture was stirred at room temperature for 16 hours. The reaction was quenched with water and extracted with ethyl acetate (10 mL×4). The combined organic layer was concentrated to give the crude which was purified by silica gel chromatography to yield the title compound 362 (20 mg, 16%). LCMS: $[M+1]^+$=487.25. $^1H$ NMR (400 MHz, Chloroform-d) δ 6.13-6.00 (m, 1H), 5.40-5.33 (m, 1H), 4.26 (s, 1H), 4.14 (s, 1H), 3.90-3.64 (m, 2H), 3.53-3.35 (m, 3H), 2.29-2.20 (m, 2H), 2.03-1.95 (m, 2H), 1.89-1.77 (m, 3H), 1.56-1.44 (m, 8H), 1.32-1.22 (m, 5H), 1.16-1.07 (m, 3H), 1.02-0.92 (m, 7H), 0.69 (s, 3H).

Example 363: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(1-methyl-1H-tetrazole-5-carbonyl)piperazin-1-yl)pentan-1-one

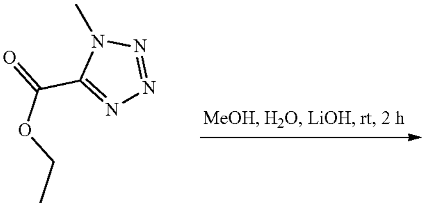

A

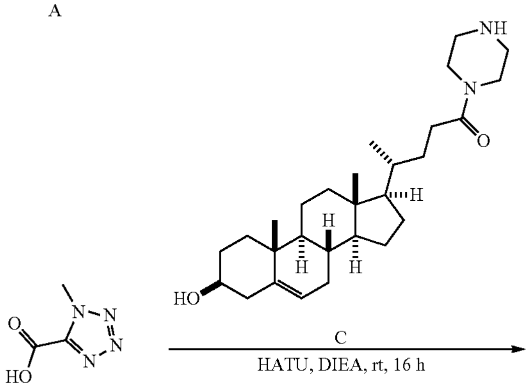

B

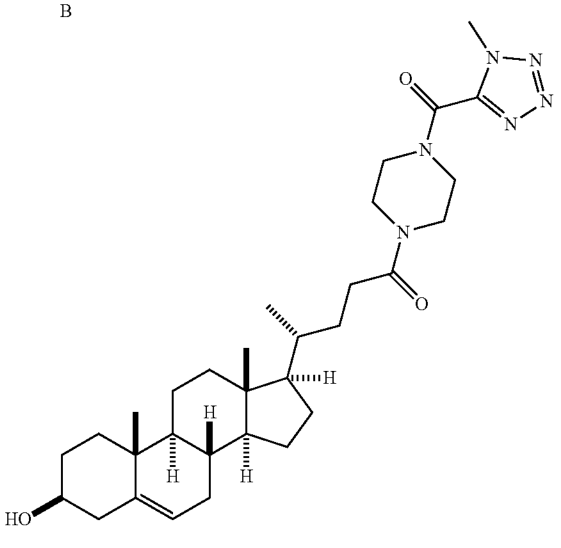

363

To a solution of compound A (40 mg, 0.25 mmol) in MeOH (2 mL) and water (2 mL) was added LiOH (18.4 mg, 0.77 mmol). The mixture was stirred at room temperature for 2 h. The mixture was adjusted to pH 6-7 and concentrated to afford compound B (35 mg) as a colorless oil.

To a solution of compound B (29 mg, 226 μmol) in DMF (2 mL) was added compound C (100 mg, 226 μmol), HATU (160 mg, 679 μmol) and DIEA (176 mg, 1.36 mmol). The mixture was stirred at room temperature under $N_2$ for 16 h. The reaction was quenched with saturated $NH_4Cl$. and extracted with ethyl acetate. The organic layer was washed with brine, dried over sodium sulfate, and concentrated under vacuo. The residue was purified by column chroma tography on silica gel to afford the title compound 363 (18.9 mg) as a white solid. $^1$H NMR (400 MHz, Chloroform-d) δ 5.35 (d, J=5.2 Hz, 1H), 4.30 (s, 3H), 4.10 (d, J=28 Hz, 2H), 3.86-3.45 (m, 7H), 2.47-2.38 (m, 1H), 2.34-2.18 (m, 3H), 2.04-1.28 (m, 19H), 1.22-1.04 (m, 5H), 1.01 (s, 3H), 0.99-0.80 (m, 6H), 0.69 (s, 3H).
Example 364: 1-((1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-4-methylpiperidin-4-yl)methyl)-3-methylurea
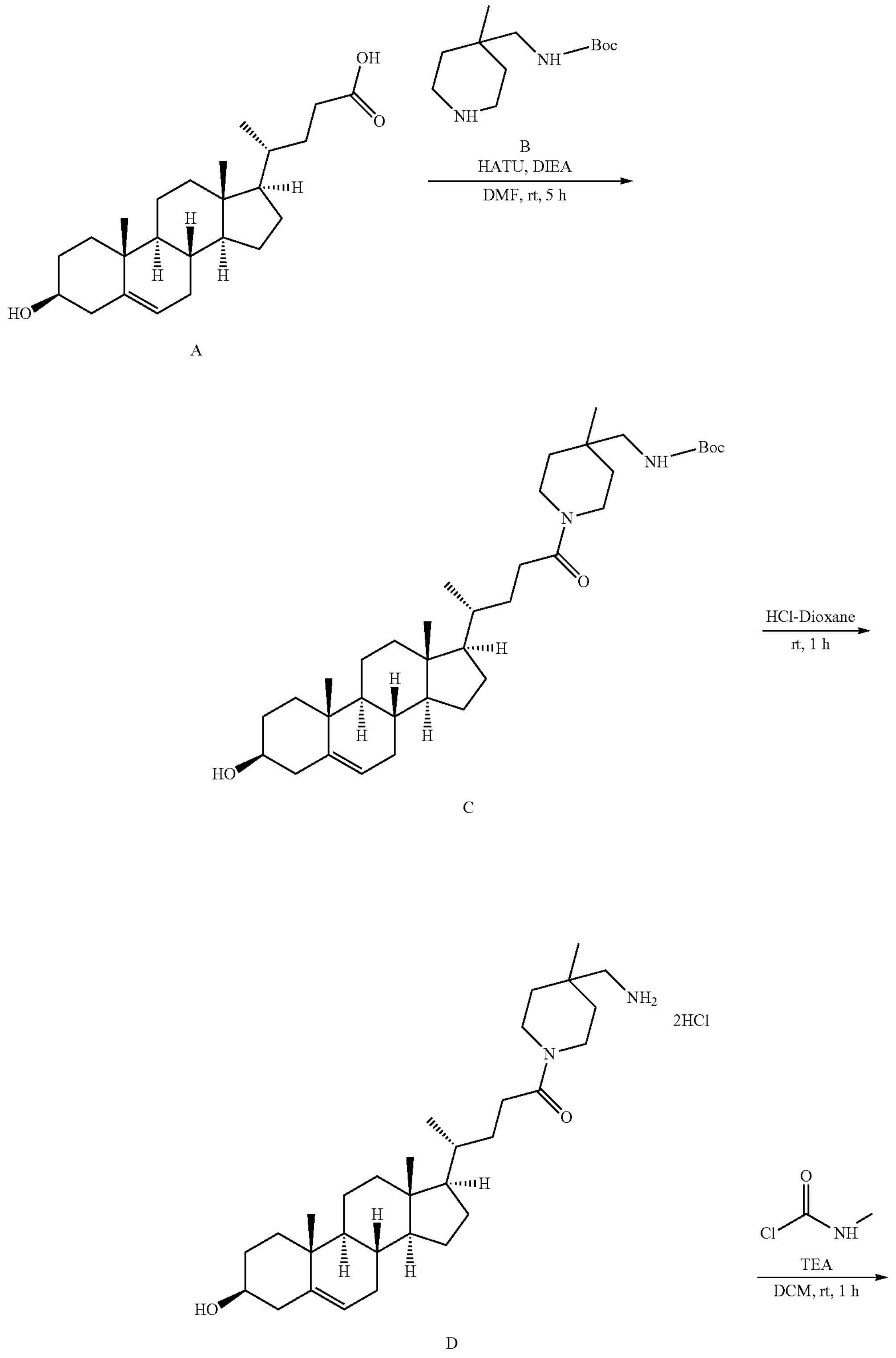

-continued

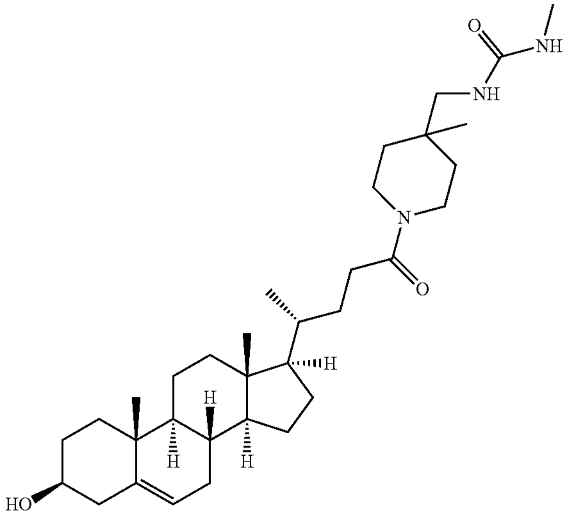

364

To a solution of compound A (1.23 g, 3.28 mmol) and compound B (1.12 g, 4.93 mmol) in DMF (20 mL) was added HATU (1.55 g, 6.57 mmol) and DIEA (2.12 g, 16.4 mmol). The mixture was stirred at room temperature for 5 hours. After completion, the mixture was quenched by adding saturated ammonium chloride solution (200 mL) and extracted with ethyl acetate (200 mL×3). The organic layer was washed with brine, dried over sodium sulfate, filtered, and concentrated to give the crude which was purified by column chromatography on silica gel to yield compound C (1.7 g, 92%) as a white solid.

HCl (2 mL, 8 mmol, 4 M in dioxane) was added slowly to the solution of compound C (1.0 g, 1.71 mmol) in dioxane (10 mL) and stirred for 1 hour. After completion, the reaction mixture was concentrated to give compound D (950 mg, 99%) as a solid.

To a solution of compound D (200 mg, 413 μmol) in dichloromethane (5 mL) was slowly added triethylamine (104 mg, 1.03 mmol) and N-methylcarbamoyl chloride (34.7 mg, 371 μmol) at 0° C. The reaction mixture was stirred for 1 hour. After completion, the mixture was quenched by adding water (10 mL) and extracted with ethyl acetate (10 mL×3). The organic layer was washed with brine, dried over sodium sulfate, filtered, and concentrated to give the crude which was purified by column chromatography on silica gel to yield the title compound 364 (70 mg, 31%) as a white solid. LCMS: $[M+H]^+$=542.4. $^1H$ NMR (400 MHz, DMSO-$d_6$) δ 5.90 (t, J=6.2 Hz, 1H), 5.62 (d, J=4.8 Hz, 1H), 5.26 (d, J=4.8 Hz, 1H), 4.59 (d, J=4.4 Hz, 1H), 3.67 (d, J=12.2 Hz, 1H), 3.50 (d, J=13.4 Hz, 1H), 3.30-3.20 (m, 2H), 3.14 (t, J=10.8 Hz, 1H), 2.92 (bs, 2H), 2.53 (d, J=4.6 Hz, 3H), 2.32-2.04 (m, 4H), 2.00-0.96 (m, 25H) 0.93 (s, 3H), 0.88 (d, J=21.4 Hz, 7H), 0.64 (s, 3H).

Example 365: 2-hydroxy-N-((1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-4-methylpiperidin-4-yl)methyl)-2-methylpropanamide

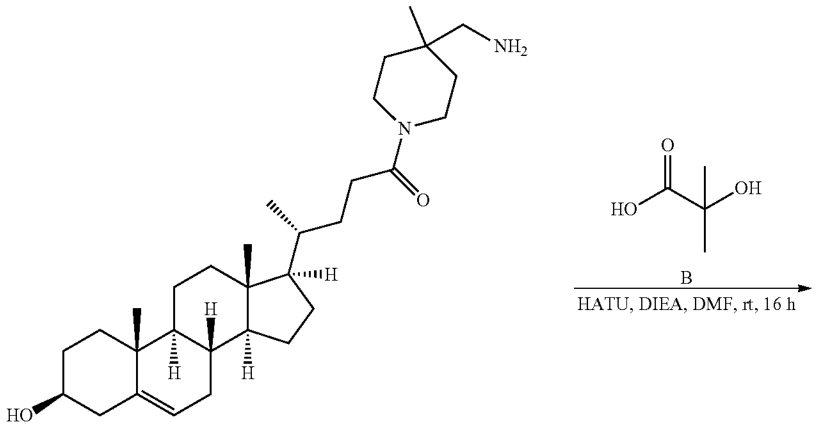

A

-continued

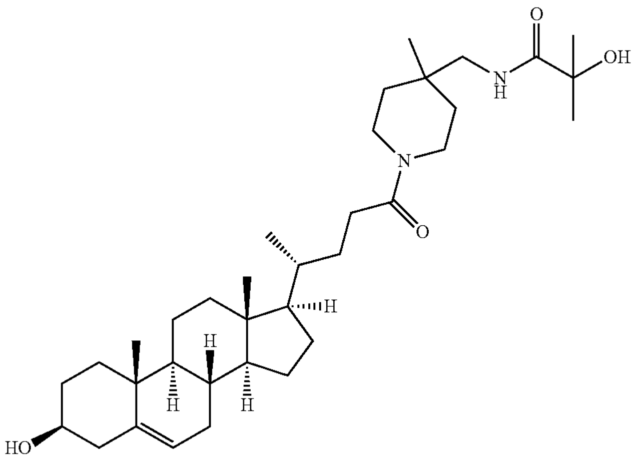

365

To a solution of compound A (100 mg, 206 μmol) and compound B (21.5 mg, 206 μmol) in DMF (5 mL) was added HATU (97.1 mg, 413 μmol) and DIEA (133 mg, 1.03 mmol). The mixture was stirred at room temperature for 16 hours. After completion, the mixture was quenched by adding saturated ammonium chloride solution (20 mL) and extracted with ethyl acetate (20 mL×3). The organic layer was washed with brine, dried over sodium sulfate, filtered, and concentrated to give the crude which was purified by column chromatography on silica gel to yield the title compound 365 (36.6 mg, 31%) as a white solid. LCMS: $[M+H]^+$=571.35. $^1H$ NMR (400 MHz, Chloroform-d) δ 6.90 (s, 1H), 5.35 (d, J=3.4 Hz, 1H), 3.93-3.83 (m, 1H), 3.63-3.47 (m, 2H), 3.38-3.27 (m, 3H), 3.12-3.03 (m, 1H), 2.43-2.18 (m, 10H), 2.03-1.69 (m, 6H), 1.63-1.49 (m, 4H), 1.47 (s, 6H), 1.45-1.06 (m, 11H), 1.00 (d, J=3.8 Hz, 6H), 0.94 (d, J=6.4 Hz, 3H), 0.68 (s, 3H).

Example 366: 2—((S)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethoxy)-1-(4-(hydroxymethyl)-4-methylpiperidin-1-yl)ethan-1-one

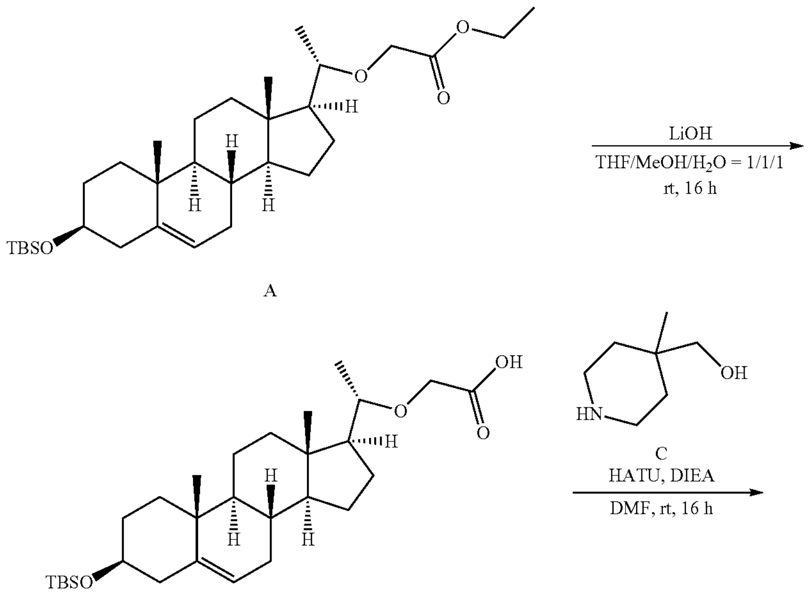

A

B

-continued

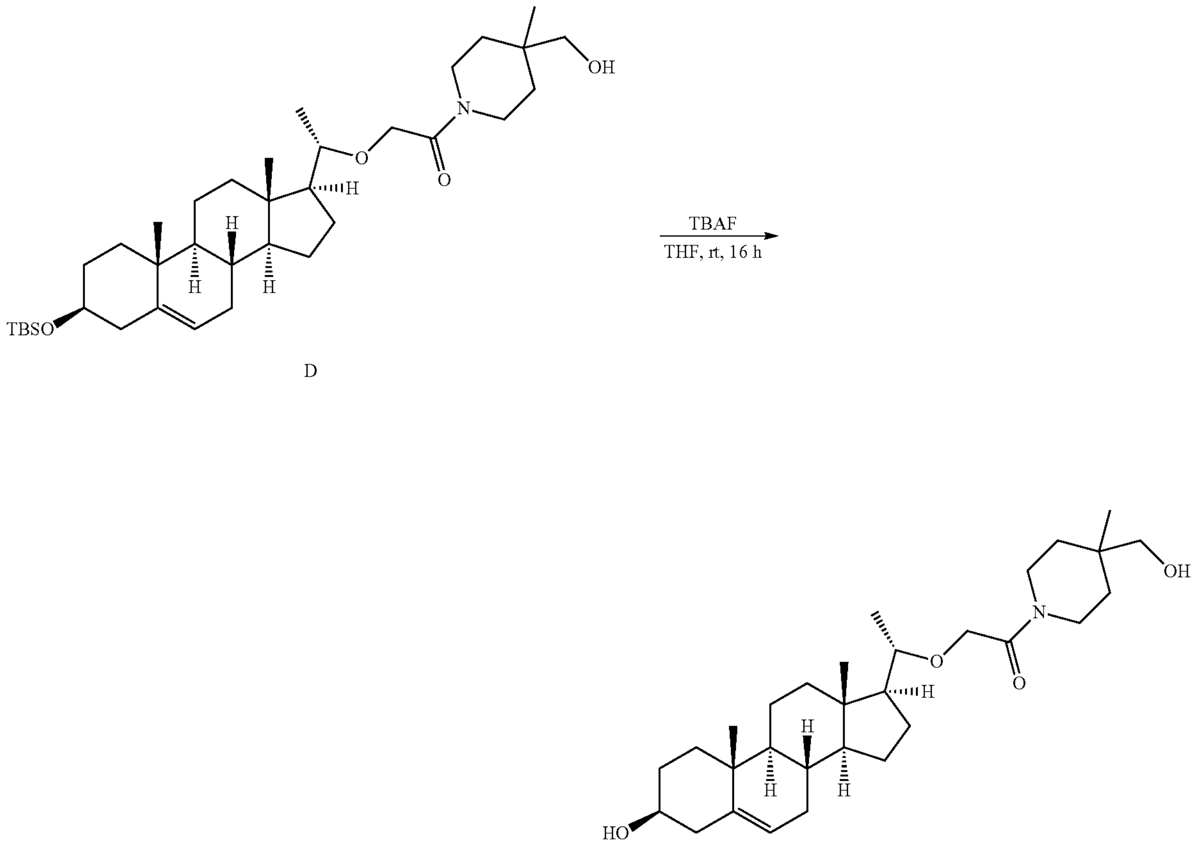

D

366

To a solution of compound A (200 mg, 375 μmol) in THF (1 mL) and methanol (1 mL) and water (1 mL) was added LiOH (44.9 mg, 1.88 mmol). The mixture was stirred at room temperature for 16 hours. After completion, the mixture was adjusted to pH=1 and extracted with DCM. The organic layer was concentrated to give compound B (200 mg) which was used in the next step directly.

To a solution of compound B (200 mg, 396 μmol) in DMF (4 mL) was added compound C (76.8 mg, 594 μmol), HATU (301 mg, 792 μmol) and DIEA (256 mg, 1.98 mmol). The mixture was stirred at room temperature for 16 hours. After completion, the mixture was diluted with water and extracted with ethyl acetate. The organic layer was concentrated to give the crude which was purified by silica gel chromatography to give compound D (110 mg, 46%).

To a solution of compound D (110 mg, 183 μmol) in THF (3 mL) was added TBAF (0.91 mL, 0.91 mmol, 1M in THF). The mixture was stirred at room temperature for 16 hours. After completion, the mixture was concentrated to give the crude which was purified by silica gel chromatography to give the title compound 366 (27 mg, 30%). $^1$H NMR (400 MHz, Chloroform-d) δ 5.34 (d, J=5.0 Hz, 1H), 4.14 (d, J=12.6 Hz, 1H), 4.02 (d, J=12.4 Hz, 2H), 4.19-3.07 (m, 10H), 2.36-2.18 (m, 2H), 2.01-1.80 (m, 5H), 1.69-1.22 (m, 16H), 1.17-1.05 (m, 3H), 1.02 (s, 3H), 1.00 (s, 3H), 0.98-0.90 (m, 1H), 0.65 (s, 3H). LCMS: $[M+1]^+$=488.40.

Example 367: N-({1-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]-4-methylpiperidin-4-yl}methyl)methanesulfonamide

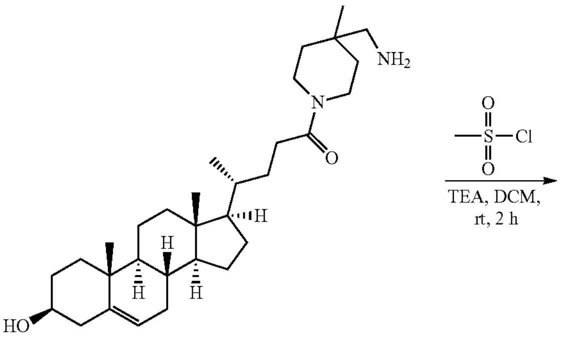

A

-continued

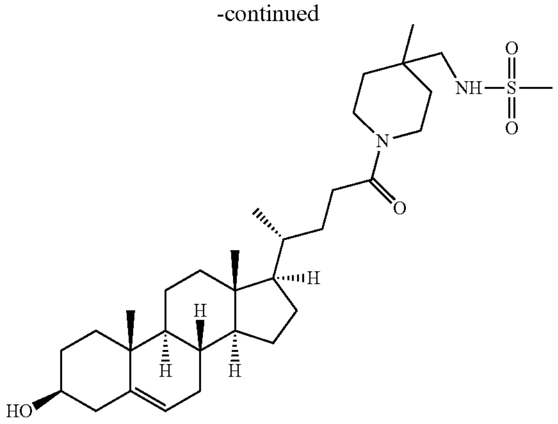

367

To a solution of compound A (200 mg, 413 μmol) and triethylamine (83.5 mg, 825 μmol) in dichloromethane (20 mL) was added methanesulfonyl chloride (42.5 mg, 371 μmol) at 0° C. The resulting mixture was stirred at room temperature for 2 h after which it was diluted with water and extracted with DCM. The organic layer was dried with sodium sulfate and concentrated under vacuum. The residue was purified by silica gel chromatography (eluting with 1/1 ethyl acetate/PE) to give the title compound 367 (7.0 mg, 3.01%). LCMS: $[M+H]^+=563.25$. $^1H$ NMR (400 MHz, Chloroform-d) δ 5.35 (d, J=5.1 Hz, 1H), 4.37 (t, J=7.1 Hz, 1H), 3.98 (d, J=13.3 Hz, 1H), 3.61-3.47 (m, 2H), 3.35-3.16 (m, 2H), 3.07-3.00 (m, 1H), 2.97 (s, 3H), 2.40-2.17 (m, 5H), 2.04-1.73 (m, 7H), 1.52-1.25 (m, 14H), 1.17-1.06 (m, 4H), 1.02 (d, J=10.6 Hz, 6H), 0.95 (d, J=6.6 Hz, 4H), 0.68 (s, 3H).

Example 368: (3S,8S,9S,10R,13R,14S,17R)-17-((2R,5S)-5-cyclopropyl-6,6,6-trifluoro-5-hydroxyhexan-2-yl)-3,10,13-trimethyl-2,3,4,7,8,9,10,11,12,13,14,15,16,17-tetradecahydro-1H-cyclopenta[a]phenanthren-3-ol

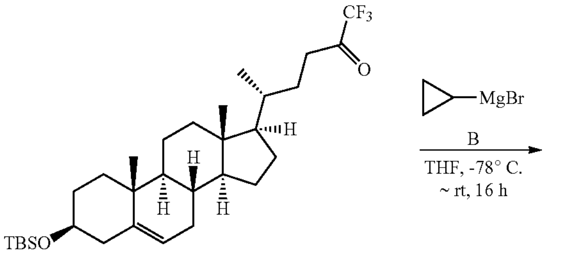

A

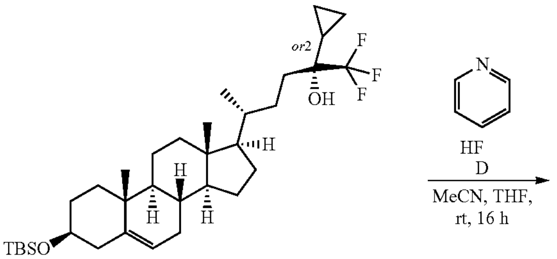

C

-continued

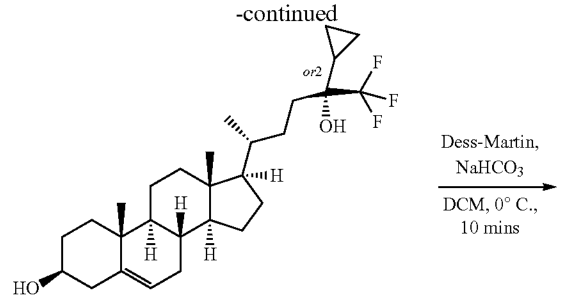

E

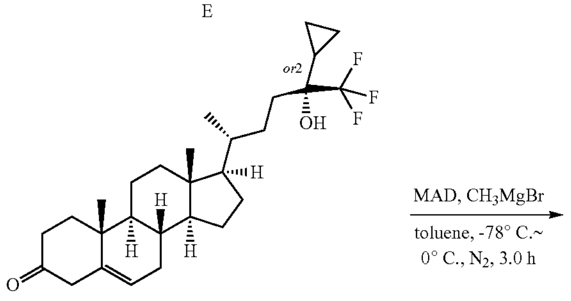

F

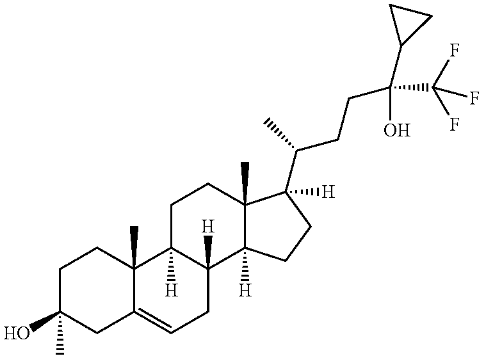

368

To a solution of compound A (1.0 g, 1.85 mmol) in THF (30 mL) at −78° C. under $N_2$ was added compound B (0.9 mL, 2M in THF, 1.8 mmol). The mixture was stirred at room temperature under $N_2$ for 16 h. The reaction was quenched with saturated $NH_4Cl$ and extracted with ethyl acetate. The organic layer was washed with brine, dried over sodium sulfate and concentrated under vacuum. The residue was purified by column chromatography on silica gel to afford compound C (750 mg) as a white solid. To a solution of compound C (750 mg, 1.29 mmol) and acetonitrile (20 mL) in THF (20 mL) was added compound D (5 mL). The mixture was stirred at room temperature for 16 h. The reaction was quenched with saturated $NH_4Cl$ and extracted with ethyl acetate. The organic layer was washed by brine, dried over sodium sulfate and concentrated under vacuum. The residue was purified by column chromatography on silica gel to afford compound E (350 mg) as a white solid.

To a solution of compound E (350 mg, 0.75 mmol) in DCM (10 mL) was added DMP acetate (634 mg, 1.49 mmol) and sodium hydrogen carbonate (314 mg, 3.73 mmol). The mixture was stirred at 0° C. under $N_2$ for 10 minutes. The reaction was quenched with saturated $NH_4Cl$ and extracted with ethyl acetate. The organic layer was washed with brine, dried over sodium sulfate, filtered, and concentrated to afford compound F (350 mg) as a white solid.

The solution of 2,6-di-tert-butyl-4-methylphenol (1.69 g, 7.66 mmol) and trimethylalumane (255 mg, 3.54 mmol) in toluene (22 mL) was stirred at 0° C. for 30 mins under $N_2$. After cooled to −78° C., compound F (550 mg, 1.18 mmol) was added, followed by MeMgBr (3.5 mL, 1 M in THF, 3.5 mmol). The mixture was stirred at −78° C. under $N_2$ for 3 h. The reaction was quenched with saturated $NH_4Cl$ and extracted with EA. The organic layer was washed by brine, dried over sodium sulfate, and concentrated. The residue was purified by column chromatography on silica gel to afford the title compound 368 (100 mg) as a white solid. $^1H$ NMR (400 MHz, Chloroform-d) δ 5.33-5.28 (m, 1H), 2.42 (d, J=13.2 Hz, 1H), 2.04-1.93 (m, 3H), 1.91-1.37 (m, 19H), 1.36-0.82 (m, 22H), 0.69 (s, 3H), 0.60-0.39 (m, 4H).

Example 369: (3S,8S,9S,10R,13R,14S,17R)-3,10,13-trimethyl-17-((R)-4-(pyridin-2-yl)butan-2-yl)-2,3,4,7,8,9,10,11,12,13,14,15,16,17-tetradecahydro-1H-cyclopenta[a]phenanthren-3-ol

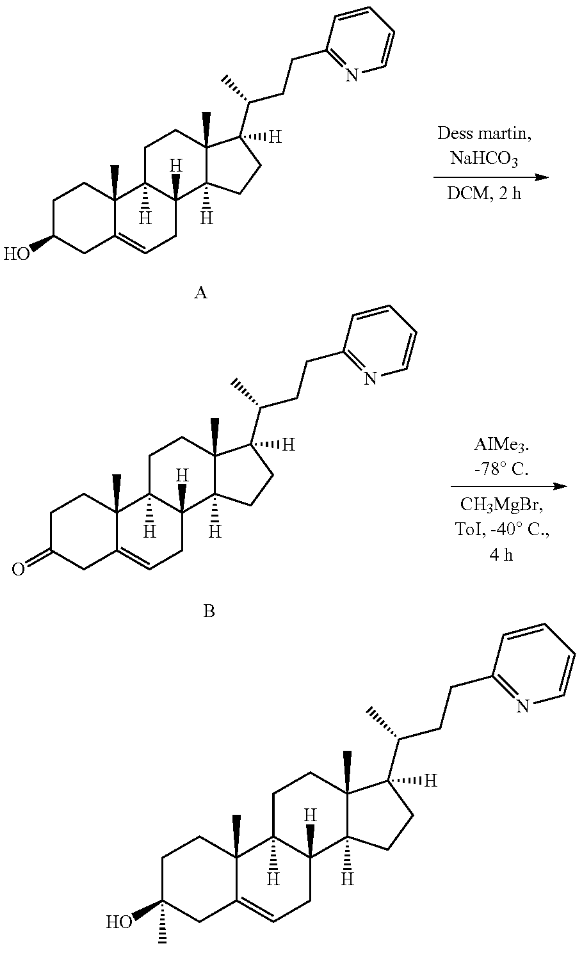

369

To a stirring mixture of compound A (200 mg, 491 μmol) and sodium hydrogen carbonate (206 mg, 981 μmol) in DCM (10 mL), DMP (416 mg, 982 μmol) was added at 0° C. After stirring for 2 h, the mixture was quenched with $Na_2SO_3$ (30 mL) and extracted with ethyl acetate (30 mL×2). The combined organic layers were washed with brine (20 mL), dried over sodium sulfate and concentrated in vacuum to give the crude which was purified by silica gel chromatography to afford compound B (150 mg, 75%).

To a stirring solution of trimethylaluminium (53.3 mg, 740 μmol) in toluene (5 mL) at −78° C. under $N_2$, $CH_3MgBr$ (1.11 mL, 1.11 mmol, 1M in THF) was added and stirred for 2 h. Compound B (150 mg, 370 μmol) was added at −40° C. under $N_2$ atmosphere and stirred for 4 h. The mixture was quenched with water (30 mL) and extracted with ethyl acetate (30 mL×2). The combined organic layers were washed with brine (30 mL), dried over sodium sulfate, and concentrated in vacuum to give the crude which was purified by silica gel chromatography (DCM/MeOH=100:0100:3) to give the title compound 369 (40 mg, 26%) as an off-white solid. LCMS:[M+H$^+$]=422.4. $^1H$ NMR (400 MHz, Chloroform-d) δ 8.57-8.45 (m, 1H), 7.59 (td, J=8.0, 2.0 Hz, 1H), 7.17-7.05 (m, 2H), 5.32-5.28 (m, 1H), 2.92-2.82 (m, 1H), 2.71-2.61 (m, 1H), 2.42 (d, J=12.0 Hz, 1H), 2.04-1.94 (m, 3H), 1.91-1.82 (m, 2H), 1.80-1.66 (m, 3H), 1.58 (s, 2H), 1.52-1.45 (m, 4H), 1.30 (s, 2H), 1.20-1.13 (m, 3H), 1.11 (s, 3H), 1.04 (d, J=6.4 Hz, 3H), 1.01 (s, 3H), 0.96-0.80 (m, 3H), 0.68 (s, 3H).

Example 370: 1-(4-ethyl-4-hydroxypiperidin-1-yl)-4-((3S,8S,9S,10R,13R,14S,17S)-3-hydroxy-10,13-dimethyl-2,3,4,7,8,9,10,11,12,13,14,15,16,17-tetradecahydro-1H-cyclopenta[a]phenanthren-17-yl)butan-1-one

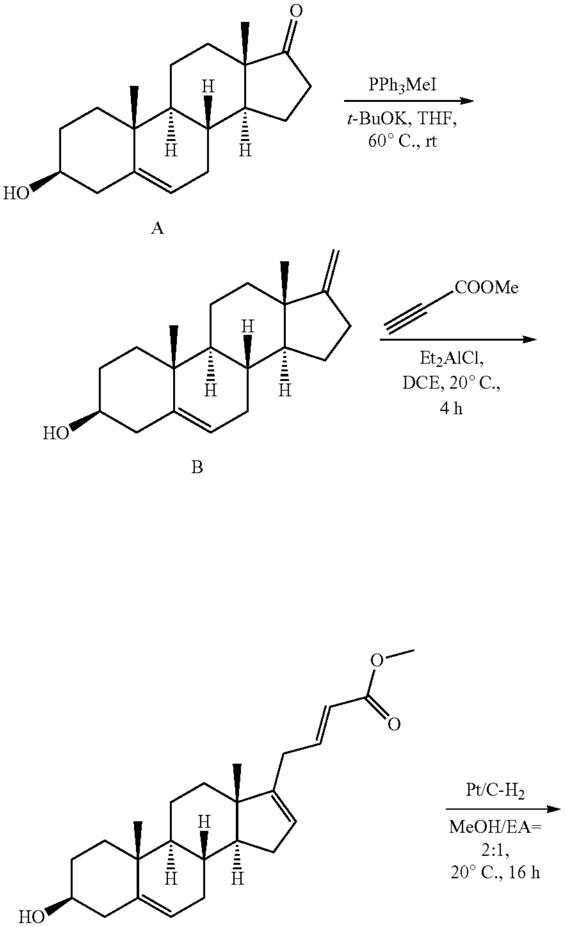

C

-continued

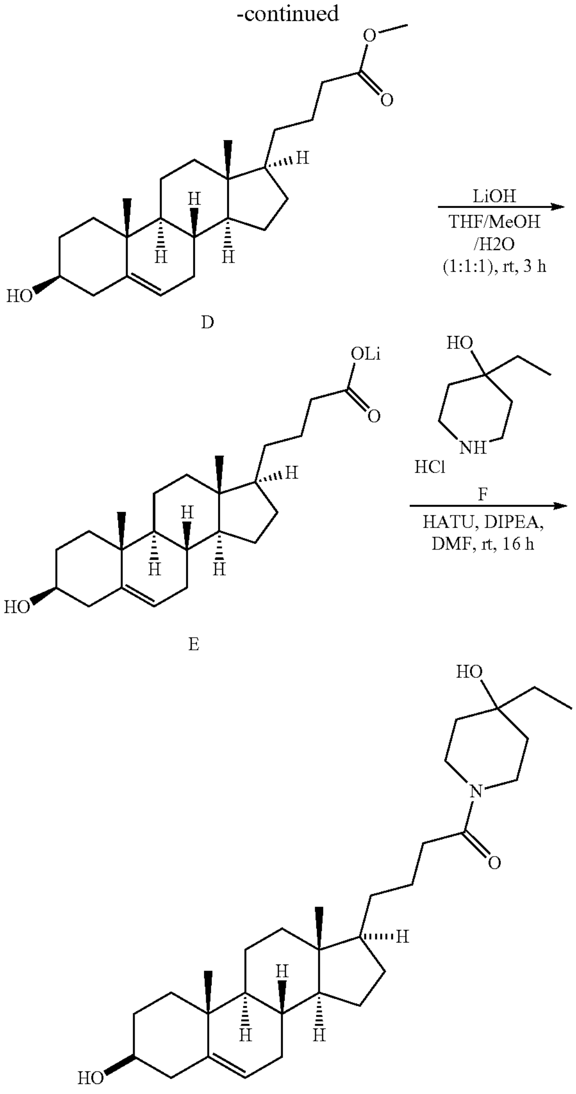

D

E

370

The mixture of $PPh_3MeI$ (70 g, 173 mmol) and tBuOK (19.5 g, 173 mmol) in tetrahydrofuran (0.5 L) was stirred at 60° C. under $N_2$ atmosphere for 1 h. Then compound A (10 g, 34.7 mmol) was added and stirred for 16 h. The mixture was diluted with water (500 mL) and extracted with ethyl acetate (500 mL×2). The combined organic layers were washed with brine (500 mL), dried over sodium sulfate, and concentrated in vacuum to give the crude which was purified by silica gel chromatography (EtOAc/Petroleum ether=1/10-1:3) to give crude compound B (12.6 g) which was used directly in the next step without further purification.

The mixture of compound B (12.6 g, 44 mmol), chlorodiethylalumane (132 mL, 132 mmol, 1M in THF) and methyl prop-2-ynoate (11.1 g, 132 mmol) in DCE (40 mL) was stirred at 20° C. under $N_2$ atmosphere for 4 h. The mixture was quenched with water (100 mL) and extracted with DCM (100 mL×2). The combined organic layers were washed with brine (100 mL), dried over sodium sulfate and concentrated in vacuum to give the crude which was purified by silica gel chromatography (EtOAc/Petroleum ether=1/10-1:3) to give compound C (9.5 g, 58%).

The mixture of compound C (2.0 g, 5.40 mmol) and 10% Pt/C (200 mg) in methanol (10 mL) and ethyl acetate (5 mL) was stirred at 20° C. under 1 atm of $H_2$ for 16 h. The mixture was filtered and concentrated in vacuum to give compound D (1.86 g, 92%) as a white solid.

Compound D (1.86 g, 4.97 mmol) and LiOH (357 mg, 3 eq., 14.9 mmol) in methanol (3 mL), tetrahydrofuran (3 mL) and water (3 mL) were stirred at room temperature under $N_2$ atmosphere for 3 h. The mixture was concentrated in vacuum to give crude compound E (1.57 g, 88%).

To a stirring solution of compound E (102 mg, 277 μmol) in DMF (4 mL) was added compound F (50.5 mg, 305 μmol), HATU (158 mg, 416 μmol) and DIPEA (143 mg, 1.11 mmol) at room temperature and the mixture was stirred for 16 h after which it was diluted with water and extracted with ethyl acetate (80 mL). The organic layer was washed with HCl (aq., 1M, 30 ml), $NaHCO_3$ (aq, 30 mL), water (30 mL*2), and brine (30 mL), dried over sodium sulfate and concentrated in vacuum to give the crude which was concentrated in vacuum and purified by silica gel chromatography (DCM/MeOH=100/0100:3) to give the title compound 370 (118 mg, 90%). LCMS:[M+H$^+$]=472.40. $^1$H NMR (400 MHz, DMSO-d6) δ 5.26 (d, J=4.0 Hz, 1H), 4.59 (d, J=4.0 Hz, 1H), 4.15 (s, 1H), 4.03 (d, J=12.0 Hz, 1H), 3.56 (d, J=12.0 Hz, 1H), 3.30-3.16 (m, 2H), 2.89 (t, J=12.0 Hz, 1H), 2.37-2.07 (m, 4H), 1.95-1.89 (m, 1H), 1.84-1.64 (m, 4H), 1.59-1.30 (m, 15H), 1.26-1.17 (m, 3H), 1.12-1.01 (m, 3H), 0.97-0.89 (m, 6H), 0.82 (t, J=8.0 Hz, 3H), 0.55 (s, 3H).

Example 371: (R)-1-(4-ethyl-4-hydroxypiperidin-1-yl)-4-((3S,8S,9S,10R,13R,14S,17R)-3-hydroxy-3,10,13-trimethyl-2,3,4,7,8,9,10,11,12,13,14,15,16,17-tetradecahydro-1H-cyclopenta[a]phenanthren-17-yl)pentan-1-one

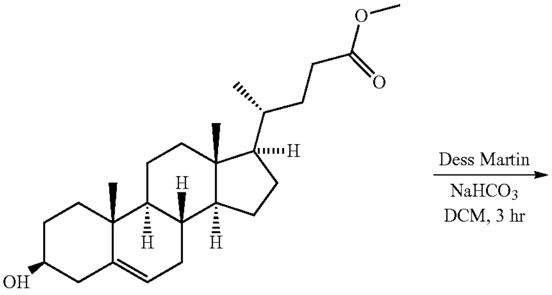

A

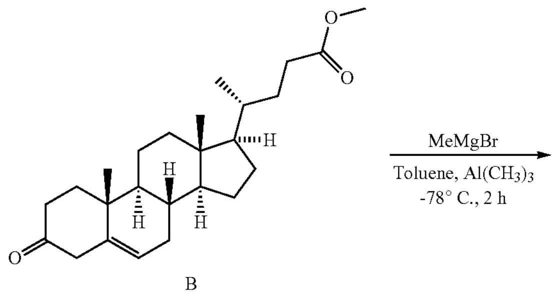

B

-continued

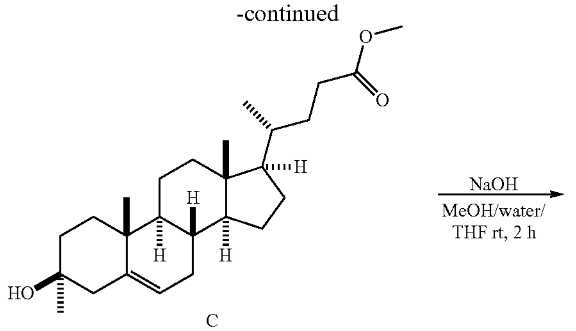

C

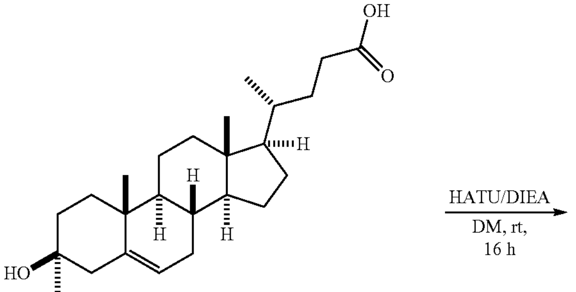

D

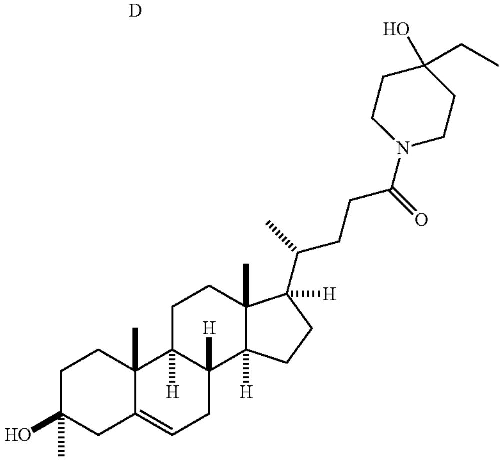

371

To a solution of compound A (5.0 g, 12.9 mmol) and $NaHCO_3$ (10.8 g, 129 mmol) in DCM (60 mL) was added Dess-Martin periodinane (8.19 g, 19.3 mmol) at 0° C. and the mixture was stirred for 3 hours. The reaction was then diluted with saturated $Na_2SO_3$ aqueous solution (150 mL) and extracted with ethyl acetate (150 mL×3). The combined organic layers were dried over sodium sulfate and concentrated under reduced pressure. The residue was purified by silica gel chromatograph to afford compound B (3.5 g, 70%) as a white solid.

To a solution of BHT (18.5 g, 84.1 mmol) in toluene (25 mL) was added A1 $(CH_3)_3$ (38.8 mol, 38.8 mmol, 1M in toluene) at 0° C. After stirring for 1 hour, the mixture was cooled to −78° C., compound B (5 g, 12.9 mmol) was added and the reaction was stirred for 1 hour. MeMgBr (19.4 mL, 19.4 mmol, 1 M in THF) was added in the mixture at −78° C. and stirred for 2 hours. The mixture was quenched with water (50 mL) and extracted with ethyl acetate (50 mL×3). The organic layer was washed with brine, dried over sodium sulfate, filtered, and concentrated to give the crude which was purified by column chromatography on silica gel to afford compound C (3.0 g, 57%). To a solution of compound C (3.0 g, 7.45 mmol) in methanol (60 mL) and tetrahydrofuran (60 mL) was added a solution of LiOH (892 mg, 37.3 mmol) in water (60 mL) at room temperature and the reaction was stirred for 2 hours. After completion, the solution was adjusted to pH 2-3 with hydrochloric acid and extracted with dichloromethane/methanol=10/1 (50 mL×3). The organic layer was washed with brine, dried over sodium sulfate, filtered, and concentrated to give compound D (2.5 g, 86%) as a white solid.

To a solution of compound D (5.0 g, 12.9 mmol) and 4-ethylpiperidin-4-ol (2.49 g, 19.3 mmol) in DMF (50 mL) was added HATU (6.05 g, 25.7 mmol) and DIEA (8.32 g, 64.3 mmol). The mixture was stirred at room temperature for 16 hours. After completion, the reaction was quenched by adding saturated ammonium chloride solution (500 mL) and extracted with ethyl acetate (500 mL×3). The organic layer was washed with brine, dried over sodium sulfate, filtered, and concentrated to give the crude which was purified by column chromatography on silica gel to yield the title compound 371 (4.09 g, 63%) as a white solid. LCMS: $[M+H]^+$=500.35. $^1H$ NMR (400 MHz, Chloroform-d) δ 5.29 (dd, J=5.0, 2.6 Hz, 1H), 4.32 (d, J=13.3 Hz, 1H), 3.60 (d, J=13.6 Hz, 1H), 3.42 (td, J=13.3, 12.6, 3.1 Hz, 1H), 3.02 (td, J=13.8, 12.5, 4.1 Hz, 1H), 2.46-2.31 (m, 2H), 2.21 (ddt, J=15.6, 11.1, 5.8 Hz, 1H), 2.04-1.83 (m, 4H), 1.81-1.69 (m, 3H), 1.66-1.39 (m, 16H), 1.38-1.12 (m, 5H), 1.10 (s, 3H), 1.00 (s, 3H), 0.95-0.85 (m, 6H), 0.67 (s, 3H).

Example 372: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(6-(hydroxymethyl)-6-methyl-2-azaspiro[3.3]heptan-2-yl)pentan-1-one

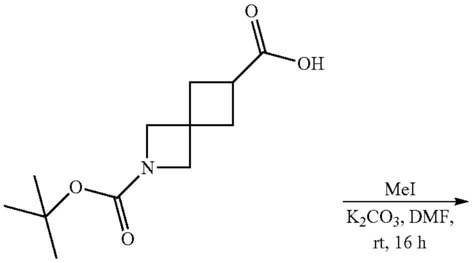

A

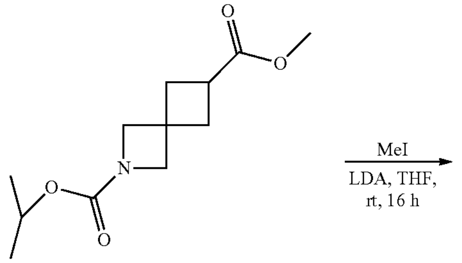

B

-continued

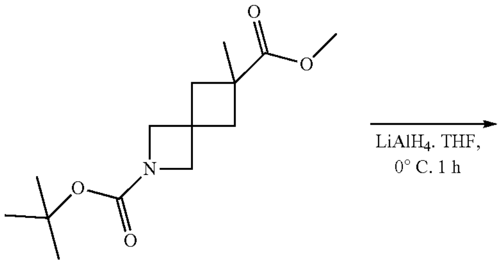

C

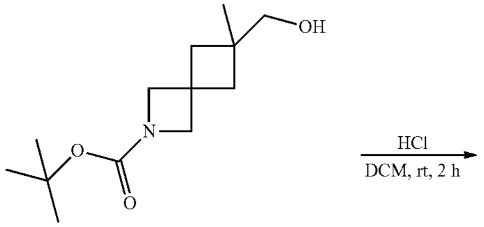

D

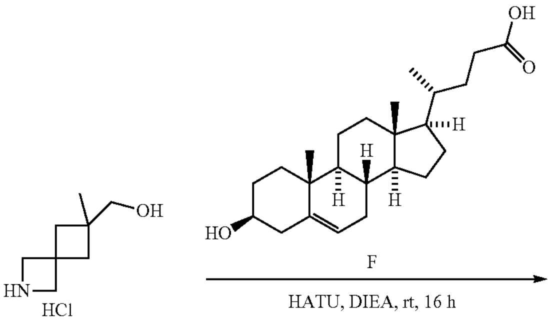

F

E

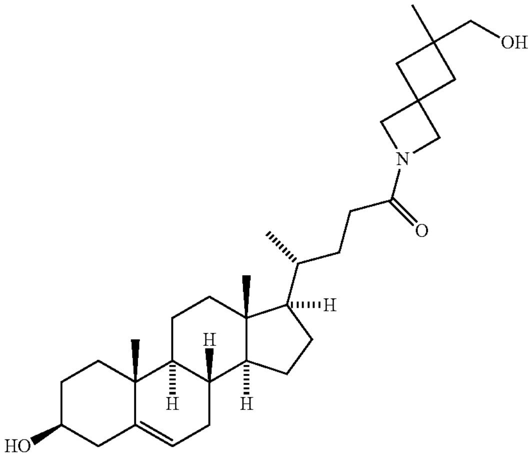

372

To a solution of A (100 mg, 414 μmol) in DMF (3 mL) was added potassium carbonate (85.9 mg, 622 μmol) and iodomethane (64.7 mg, 456 μmol). The mixture was stirred at room temperature for 16 hours. After completion, the mixture was quenched with $H_2O$ (20 mL) and extracted with ethyl acetate (10 mL×3). The organic layer was washed with brine, dried over sodium sulfate, filtered, and concentrated to give compound B (90 mg, 85%) as a yellow solid.

To a solution of B (90 mg, 353 μmol) in THF (3 mL) was added LDA (0.36 mL, 0.72 mmol, 2M in THF) at −78° C. under $N_2$. The solution was stirred at −78° C. for 0.5 h. Iodomethane (150 mg, 1.06 mmol) was added to the solution and the mixture was stirred at room temperature for 16 hours. After completion, the mixture was quenched with $H_2O$ (20 mL) and extracted with ethyl acetate (10 mL×3). The organic layer was washed with brine, dried over sodium sulfate, filtered, and concentrated to give compound C (80 mg, 84%) as a yellow solid.

To a solution of C (80 mg, 297 μmol) in THE (2 mL) was added LAH (12.4 mg, 1.1 eq., 327 μmol) at 0° C. and the mixture was stirred at 0° C. for 1 h. The reaction was then quenched with NaOH (3 mL, 1M solution) and extracted with water (10 mL) and EtOAc (10 mL×3). The organic layer was washed with brine, dried over sodium sulfate, and concentrated. The mixture was purified by column chromatography on silica gel to afford compound D (60 mg, 83%).

HCl (1 mL, 4 mmol, 4M in dioxane) was added slowly to a solution of compound D (50 mg, 507 μmol) in DCM (2 mL) at room temperature and the reaction was stirred for 2 hours. After completion, the reaction mixture was concentrated to give compound E (35 mg, 95%) as a solid.

To a solution of compound E (105 mg, 602 μmol) in DMF (3 mL) was added compound F (203 mg, 542 μmol), DIEA (467 mg, 3.61 mmol) and HATU (385 mg, 1.2 mmol). The mixture was stirred at room temperature for 16 hours. After completion, the mixture was quenched by adding saturated ammonium chloride solution (30 mL) and extracted with ethyl acetate (15 mL×3). The organic layer was washed with brine, dried over sodium sulfate, filtered, and concentrated to give the crude which was purified by column chromatography on silica gel to yield the title compound 372 (29.3 mg, 10%) as a white solid. $^1H$ NMR (400 MHz, Chloroform-d) δ 5.35 (d, J=5.2 Hz, 1H), 5.33-5.28 (m, 1H), 3.71 (s, 2H), 3.64 (s, 2H), 3.51 (dq, J=10.7, 5.4, 4.7 Hz, 1H), 3.15 (d, J=6.2 Hz, 2H), 2.33-2.16 (m, 3H), 2.10-1.94 (m, 3H), 1.90-1.77 (m, 4H), 1.63 (dt, J=7.7, 3.8 Hz, 3H), 1.53-1.40 (m, 8H), 1.38-1.26 (m, 3H), 1.20-1.05 (m, 4H), 1.01 (s, 3H), 0.97 (s, 3H), 0.94 (d, J=6.5 Hz, 3H), 0.92-0.83 (m, 1H), 0.68 (s, 3H). LCMS: $[M+1]^+$=498.30.

Example 555: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(3-(hydroxymethyl)-3-methylazetidin-1-yl)pentan-1-one

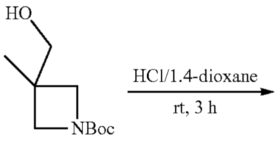

A

-continued

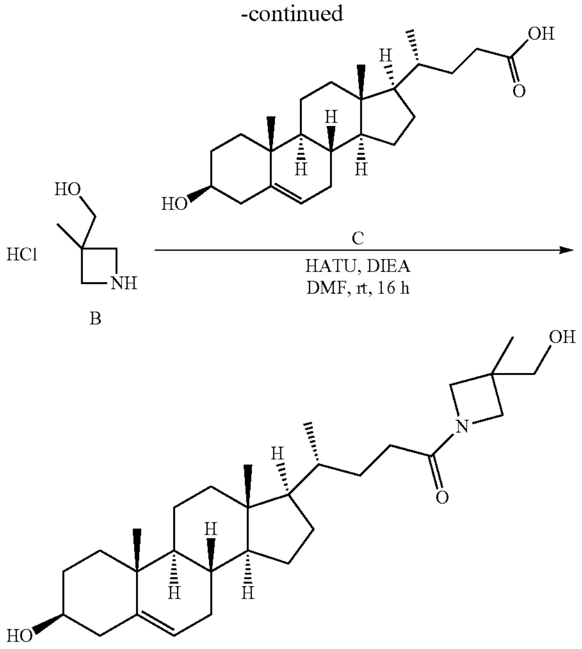

373

HCl (0.5 mL, 2 mmol, 4 M in dioxane) was added to solution of compound A (100 mg, 497 μmol) in DCM (2 mL). The mixture was stirred at room temperature for 3 h after which it was concentrated to give compound B (55 mg, 97%).

To a solution of compound B (50 mg, 365 μmol) in DMF (2 mL) was added compound C (185 mg, 494 μmol), DIEA (319 mg, 2.47 mmol) and HATU (282 mg, 741 μmol). The mixture was stirred at room temperature for 16 h after which water was added and the reaction was extracted with ethyl acetate. The organic layer was washed with brine, dried over sodium sulfate, and concentrated and the residue was purified by silica gel chromatography to afford compound 555 (50.6 mg, 22.4%). LCMS $[M+1]^+$=458.35. $^1$H NMR (400 MHz, Chloroform-d) δ 5.35 (d, J=5.0 Hz, 1H), 3.99 (bs, 1H), 3.86 (bs, 1H), 3.76-3.46 (m, 5H), 2.33-1.92 (m, 7H), 1.90-1.72 (m, 7H), 1.62-1.38 (m, 8H), 1.29 (s, 5H), 1.20-0.98 (m, 8H), 0.98-0.81 (m, 5H), 0.68 (s, 3H).

Example 374: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3R)-3-(hydroxymethyl)-3-methylpyrrolidin-1-yl]pentan-1-one

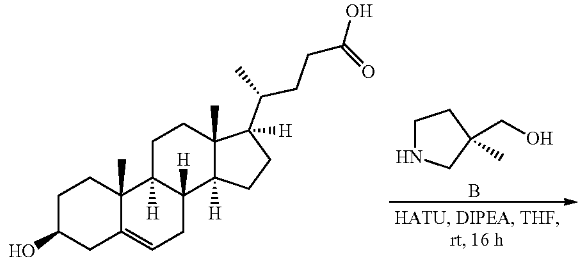

A

-continued

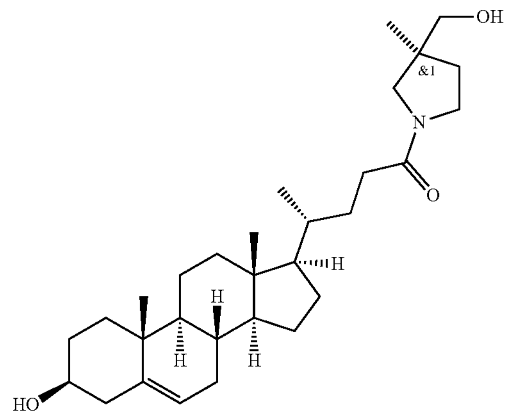

374

To a solution of compound A (150 mg, 0.4 mmol) in DMF (5 mL) was added DIEA (155 mg, 1.2 mmol), compound B (92.2 mg, 801 μmol) and HATU (188 mg, 801 μmol) at room temperature. The resulting mixture was stirred at room temperature for 16 h. The mixture was diluted with water and extracted with ethyl acetate. The organic layer was washed with water and brine, dried with sodium sulfate, and concentrated under vacuum. The residue was purified by Biotage (C18 column, eluting with 10% to 95% Acetonitrile/$H_2O$, containing 0.1% formic acid) to give compound 374 (10.0 mg, 0.01%). $^1$H NMR (400 MHz, $CDCl_3$) δ 5.35 (d, J=5.0 Hz, 1H), 3.58-3.47 (m, 5H), 3.43 (t, J=10.8 Hz, 1H), 3.16 (dd, J=30.2, 11.0 Hz, 1H), 2.34-1.78 (m, 12H), 1.74-1.26 (m, 13H), 1.21-1.06 (m, 6H), 1.01 (s, 3H), 0.94 (d, J=6.2 Hz, 3H), 0.68 (s, 3H). LCMS: $[M+H]^+$=472.40.

Example 375: (4R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(hydroxymethyl)-4-methylazepan-1-yl)pentan-1-one

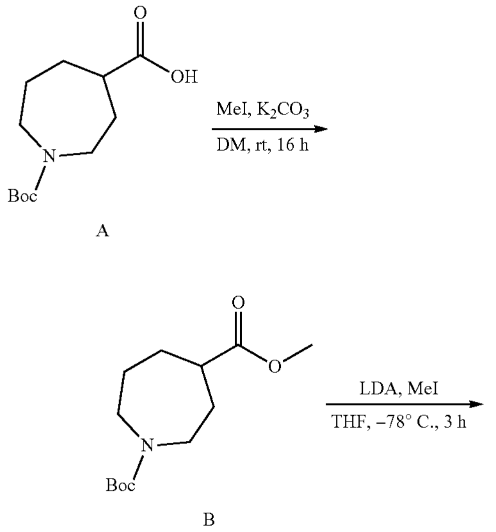

-continued

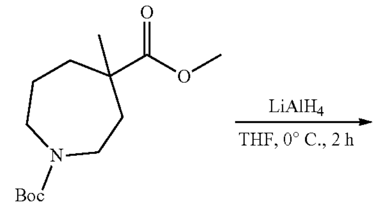

C

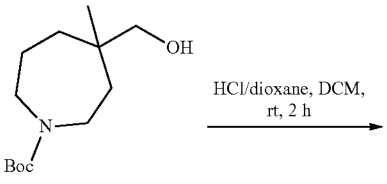

D

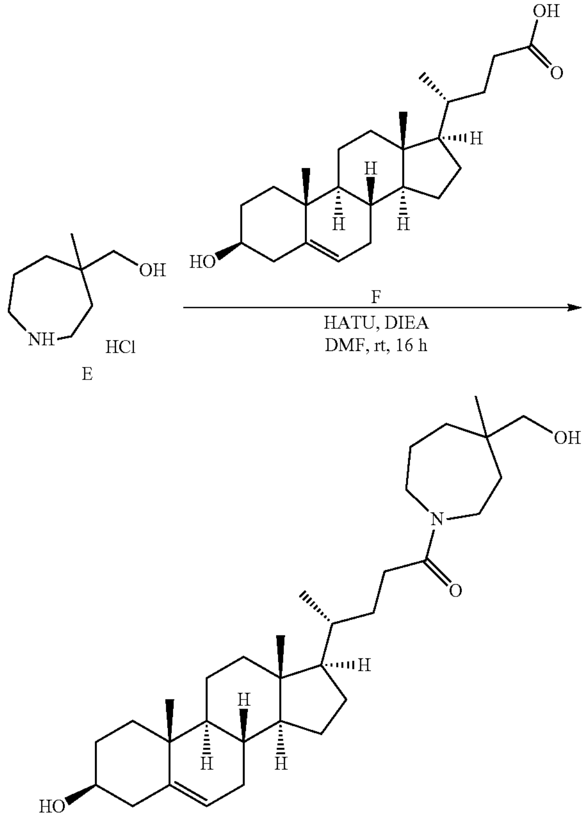

F

E

375

To a solution of compound A (800 mg, 3.29 mmol) in DMF (10 mL) was added $K_2CO_3$ (682 mg, 4.93 mmol) and iodomethane (513 mg, 3.62 mmol) at 0° C. The mixture was stirred at room temperature for 16 h after which it was diluted with water and extracted with ethyl acetate. The organic layer was washed with brine, dried over sodium sulfate, and concentrated to afford the crude which was purified by silica gel chromatography to afford compound B (800 mg, 94.5%). To compound B (800 mg, 3.11 mmol) in THF (10 mL) was added LDA (6.22 mL, 6.22 mmol, 1M in THF) at −78° C. and the solution was stirred for 30 mins. Iodomethane (1.32 g, 9.33 mmol) was added, and the mixture was stirred at −78° C. for 1 hr. The reaction was quenched with water and extracted with ethyl acetate and the organic layer was concentrated to give the crude which was purified by silica gel chromatography to give compound C (800 mg, 94.8%).

To a solution of compound C (800 mg, 2.95 mmol) in THF (10 mL) was added $LiAlH_4$ (123 mg, 3.24 mmol) at 0° C. The mixture was stirred at 0° C. for 1 hr after which was quenched with 1N NaOH and water and extracted with ethyl acetate. The organic layer was concentrated to give the crude which was purified by silica gel chromatography to give compound D (600 mg, 83.6%). To a solution of compound D (60 mg, 247 μmol) in dichloromethane (2 mL) was added HCl (0.5 mL, 2 mmol, 4M in dioxane). The mixture was stirred at room temperature for 2 h after which it was concentrated to afford compound E (40 mg) which was directly used in the next step.

To a solution of compound E (250.6 mg, 1.4 mmol) in DMF (4 mL) was added compound F (418 mg, 1.12 mmol), DIEA (902 mg, 6.98 mmol) and HATU (657 mg, 2.79 mmol). After stirring at room temperature for 16 hours, the mixture was diluted and extracted with ethyl acetate. The combined organic layer was concentrated to give a crude which was purified by silica gel chromatography to give the title compound 375 (100 mg, 14.33%). LCMS: $[M+1]^+$ =500.35. $^1H$ NMR (400 MHz, Chloroform-d) δ 5.41-5.30 (m, 1H), 3.69-3.59 (m, 1H), 3.56-3.32 (m, 6H), 2.41-2.19 (m, 4H), 2.05-1.69 (m, 8H), 1.64-1.59 (m, 2H), 1.52-1.40 (m, 8H), 1.38-1.05 (m, 7H), 1.04-0.88 (m, 11H), 0.69 (s, 3H).

Example 376: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(hydroxymethyl)piperidin-1-yl]pentan-1-one

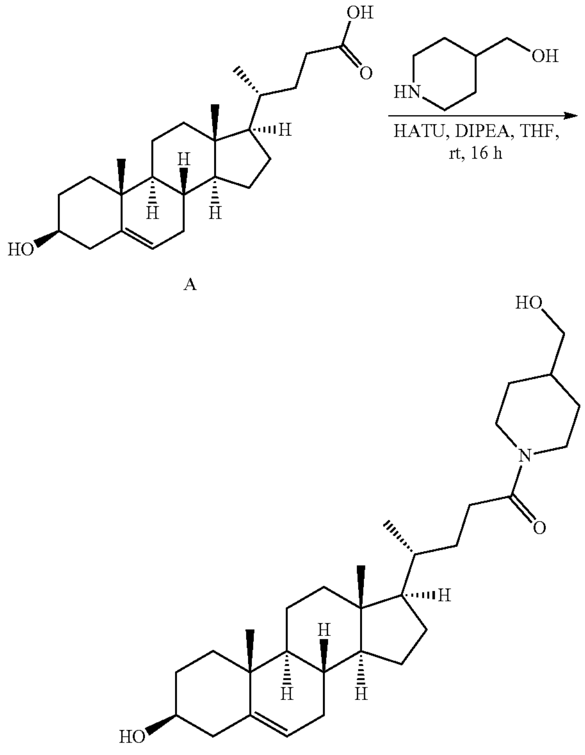

A

376

To a solution of compound A (200 mg, 534 μmol) in tetrahydrofuran (10 mL) was added DIEA (207 mg, 1.6 mmol), (piperidin-4-yl) methanol (123 mg, 1.07 mmol) and HATU (251 mg, 1.07 mmol) at room temperature. The resulting mixture was stirred for 16 h after which it was diluted with water and extracted with ethyl acetate. The organic layer was washed with water and brine, dried with sodium sulfate and concentrated under vacuum. The residue was purified by Biotage (C18 column, eluting with 10% to 95% Acetonitrile/$H_2O$, containing 0.1% formic acid) to give the title compound 376 (75.1 mg, 29.8%). $^1$H NMR (400 MHz, $CDCl_3$) δ 5.35 (d, J=5.0 Hz, 1H), 4.66 (d, J=13.6 Hz, 1H), 3.88 (d, J=13.4 Hz, 1H), 3.57-3.46 (m, 3H), 3.01 (t, J=12.6 Hz, 1H), 2.54 (t, J=12.6 Hz, 1H), 2.43-2.33 (m, 1H), 2.33-2.17 (m, 3H), 2.03-1.93 (m, 2H), 1.88-1.70 (m, 7H), 1.60-1.04 (m, 14H), 1.00 (s, 3H), 0.95 (d, J=6.4 Hz, 4H), 0.91-0.82 (m, 1H), 0.68 (s, 3H). LCMS: $[M+H]^+$=472.30.

Example 377: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(1-hydroxyethyl)piperidin-1-yl]pentan-1-one

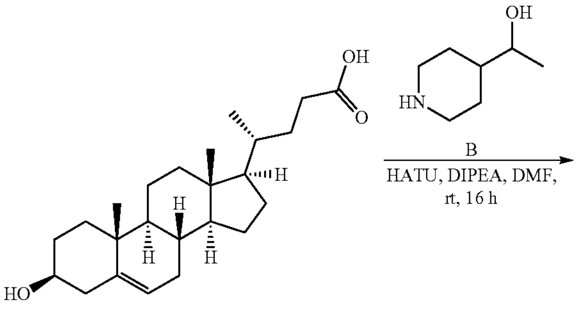

A

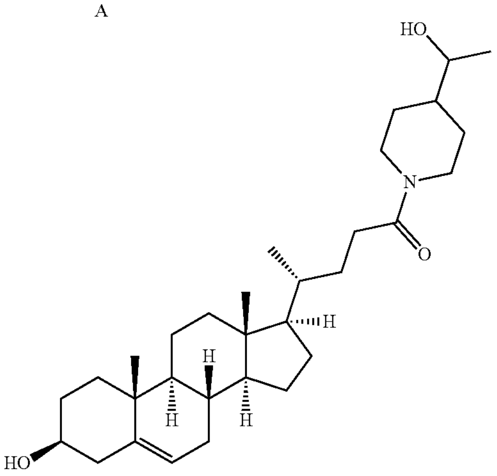

377

To a solution of compound A (200 mg, 534 μmol) in DMF (10 mL) was added DIPEA (207 mg, 1.6 mmol), compound B (138 mg, 1.07 mmol) and HATU (251 mg, 1.07 mmol) at room temperature. The resulting mixture was stirred for 16 h after which it was diluted with water and extracted with ethyl acetate. The organic layer was washed with water and brine, dried with sodium sulfate, and concentrated under vacuum. The residue was purified by Biotage (C18 column, eluting with 10% to 95% Acetonitrile/$H_2O$, containing 0.1% formic acid) to give the title compound 377 (72.0 mg, 27.8%). $^1$H NMR (400 MHz, $CDCl_3$) δ 5.35 (d, J=5.0 Hz, 1H), 4.69 (s, 1H), 3.89 (d, J=13.2 Hz, 1H), 3.65-3.47 (m, 2H), 2.98 (t, J=13.0 Hz, 1H), 2.48 (s, 1H), 2.40-2.32 (m, 1H), 2.30-2.17 (m, 3H), 2.04-1.91 (m, 3H), 1.88-1.53 (m, 9H), 1.45-1.26 (m, 7H), 1.19 (d, J=6.2 Hz, 6H), 1.14-1.06 (m, 3H), 1.01 (s, 3H), 0.95 (d, J=6.6 Hz, 3H), 0.89 (d, J=6.0 Hz, 1H), 0.68 (s, 3H). LCMS: $[M+H]^+$=486.30.

Example 378: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(2-hydroxypropan-2-yl)piperidin-1-yl)pentan-1-one

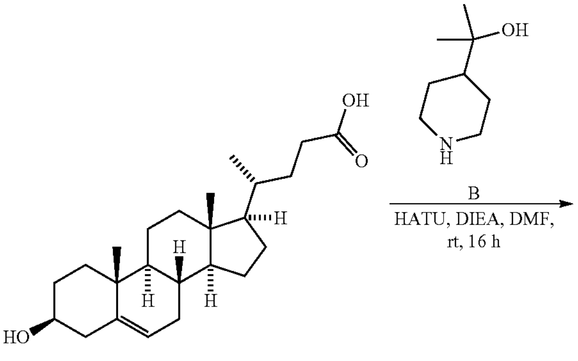

A

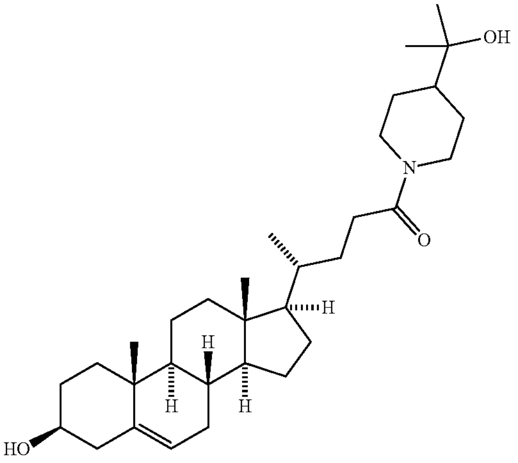

378

To a solution of compound A (200 mg, 534 μmol) in DMF (4 mL) was added compoundB (76.5 mg, 534 μmol), HATU (251 mg, 1.07 mmol) and DIEA (345 mg, 2.67 mmol). After stirring at room temperature for 16 hours, the mixture was diluted with water and extracted with ethyl acetate. The organic layer was concentrated to give a crude which was purified by prep-HPLC to give compound 378 (129 mg, 48%). $^1$H NMR (400 MHz, Chloroform-d) δ 5.34 (d, J=5.1 Hz, 1H), 4.73 (d, J=13.2 Hz, 1H), 3.92 (dd, J=13.0, 3.5 Hz, 1H), 3.52 (tt, J=10.6, 4.5 Hz, 1H), 2.96 (dd, J=14.2, 11.6 Hz, 1H), 2.49-2.33 (m, 2H), 2.34-2.15 (m, 3H), 2.04-1.38 (m, 18H), 1.37-1.21 (m, 4H), 1.19 (s, 3H), 1.17 (s, 3H), 1.14-1.03 (m, 3H), 1.00 (s, 3H), 0.95 (d, J=6.4 Hz, 3H), 0.91-0.82 (m, 1H), 0.68 (s, 3H). LCMS: $[M+1]^+$=500.30.

Example 379: (1S,3aS,3bS,7S,9aR,9bS,11aS)-9a,11a-dimethyl-1-[(1S)-1-(pyridin-4-yloxy)ethyl]-1H,2H,3H,3aH,3bH,4H,6H,7H,8H,9H,9aH,9bH,10H,11H,11aH-cyclopenta[a]phenanthren-7-ol

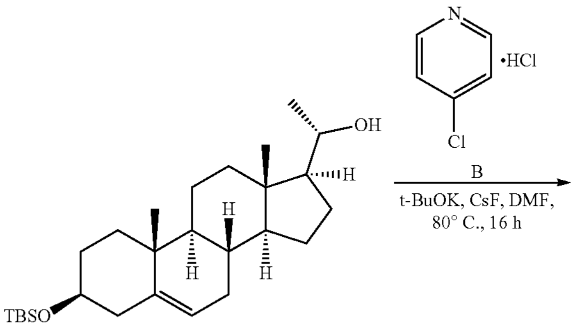

A

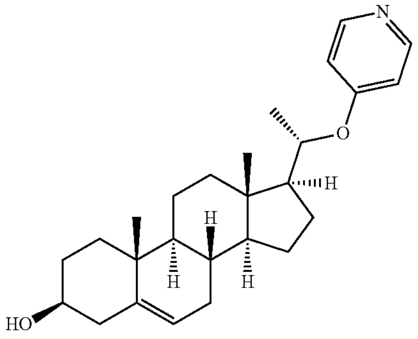

379

To a solution of compound A (1 g, 2.31 mmol) in dimethylformamide (10 mL) was added compound B (262 mg, 2.31 mmol), tBuOK (778 mg, 6.93 mmol) and cesium fluoride (702 mg, 4.62 mmol). The mixture was stirred at 80° C. for 16 hours after which it was quenched with water and extracted with ethyl acetate (10 mL×4). The combined organic layer was concentrated to give a crude which was purified by silica gel chromatography to give the title compound 379 (70 mg, 7%). LCMS:$[M+1]^+$=396.20. $^1H$ NMR (400 MHz, Chloroform-d) δ 8.39 (d, J=5.6 Hz, 2H), 6.78 (d, J=5.6 Hz, 2H), 5.41-5.32 (m, 1H), 4.44-4.34 (m, 1H), 3.59-3.46 (m, 1H), 2.36-2.17 (m, 2H), 2.05-1.79 (m, 5H), 1.73-1.63 (m, 2H), 1.62-1.40 (m, 6H), 1.33 (d, J=6.4 Hz, 3H), 1.30-1.04 (m, 5H), 1.02-0.93 (m, 4H), 0.71 (s, 3H).

Example 380: (3S,8S,9S,10R,13S,14S,17S)-10,13-dimethyl-17-((S)-1-(pyridin-3-yloxy)ethyl)-2,3,4,7,8,9,10,11,12,13,14,15,16,17-tetradecahydro-1H-cyclopenta[a]phenanthren-3-ol

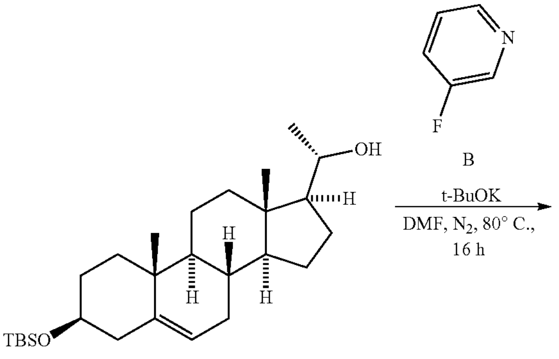

A

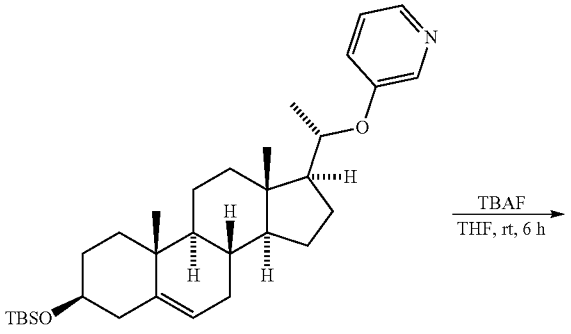

C

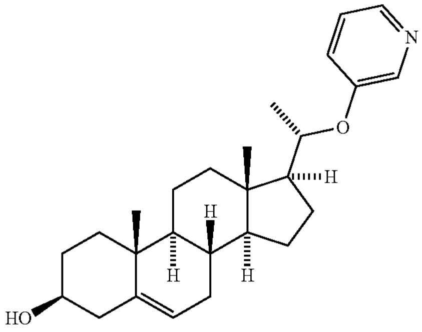

380

To a solution of compound A (400 mg, 924 μmol) in DMF (8 mL) was added compound B (89.7 mg, 924 μmol) and tBuOK (311 mg, 2.77 mmol). The mixture was stirred at 80° C. for 16 hours under nitrogen after which it was diluted with water and extracted with ethyl acetate. The organic layer was concentrated to give a crude which was purified by silica gel chromatography to give compound C (220 mg, 47%).

To a solution of compound C (220 mg, 0.431 mmol) in THF (6 mL) was added TBAF (1.27 mL, 1.27 mmol, 1M in THF). The mixture was stirred at room temperature for 6 hours after which it was diluted with water and extracted with ethyl acetate. The organic layer was concentrated to give a crude which was purified by silica gel chromatography to give the title compound 380 (36 mg, 36%). $^1H$ NMR (400 MHz, Chloroform-d) δ 8.27 (s, 1H), 8.20-8.16 (m, 1H), 7.23-7.17 (m, 2H), 5.38-5.34 (m, 1H), 4.36-4.27 (m, 1H), 3.59-3.48 (m, 1H), 2.32-2.21 (m, 2H), 2.06-1.79 (m, 5H), 1.72-1.42 (m, 8H), 1.33 (d, J=6.0 Hz, 3H), 1.28-1.04 (m, 5H), 1.02 (s, 3H), 0.99-0.95 (m, 1H), 0.72 (s, 3H). LCMS: $[M+1]^+$=396.20.

Example 381: (3S,8S,9S,10R,13S,14S,17S)-10,13-dimethyl-17-((S)-1-(pyridin-2-yloxy)ethyl)-2,3,4,7,8,9,10,11,12,13,14,15,16,17-tetradecahydro-1H-cyclopenta[a]phenanthren-3-ol

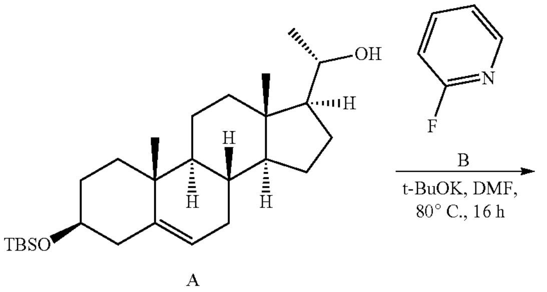

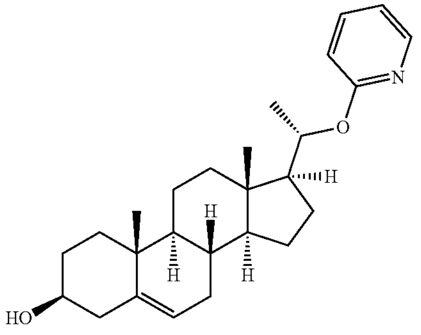

381

To a solution of compound A (400 mg, 924 μmol) and compound B (134.8 mg, 1.38 mmol) in DMF (8.01 mL), t-BuOK (233.4 mg, 2.77 mmol) was added at room temperature. The mixture was stirred at 80° C. under $N_2$ for 16 h after which water was added water and the solution was extracted with ethyl acetate. The organic layer was washed with brine, dried over sodium sulfate, and concentrated to afford a crude which was purified by silica gel chromatography and prep-HPLC to afford compound 381 (15 mg, 4%). LCMS $[M+1]^+$=396.25. $^1$HNMR (400 MHz, Chloroform-d) 8.22 (s, 1H), 7.64 (bs, 1H), 6.89 (s, 1H), 6.73 (d, J=8.0 Hz, 1H), 5.38-5.31 (m, 1H), 5.11 (t, J=6.8 Hz, 1H), 3.59-3.45 (m, 1H), 2.35-2.19 (m, 2H), 2.03-1.81 (m, 5H), 1.73-1.42 (m, 9H), 1.36 (d, J=5.6 Hz, 3H), 1.30-1.06 (m, 6H), 1.01 (s, 3H), 0.74 (s, 3H).

Example 382: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(1-methyl-1H-1,2,4-triazole-5-carbonyl)piperazin-1-yl)pentan-1-one

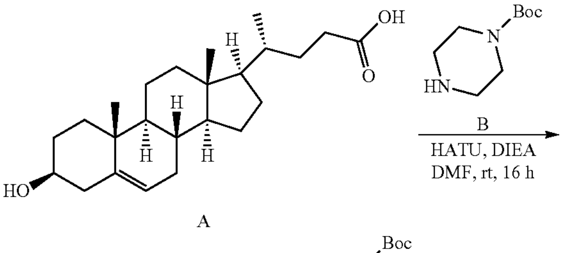

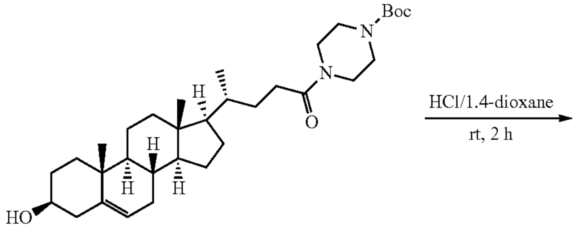

C

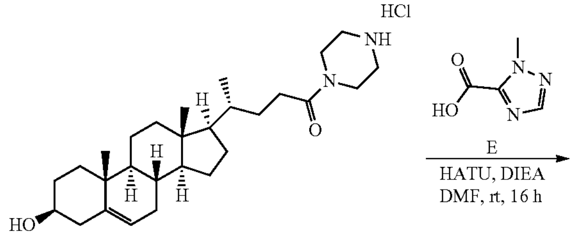

D

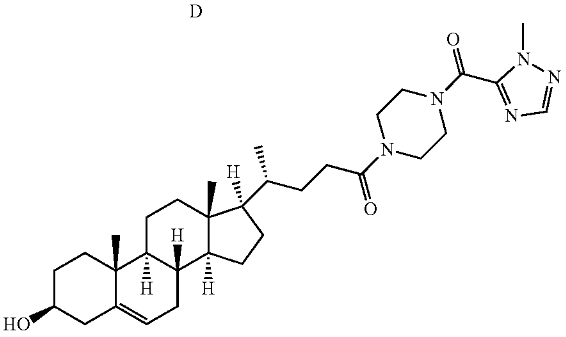

382

To a solution of compound A (150 mg, 267 μmol) in dry DMF (2 mL) was added HATU (203 mg, 534 μmol), DIEA (173 mg, 1.33 mmol) and compound B (59.7 mg, 320 μmol). The mixture was stirred at room temperature for 16 h. After completion, the mixture was poured into water and extracted with ethyl acetate, the organic layer was washed with brine, dried over sodium sulfate, and concentrated. The residue was purified by silica gel chromatography to afford compound C (180 mg, 82.8%).

To a solution of compound C (180 mg, 332 μmol) in DCM (3 mL) was added HCl (0.5 mL, 2 mmol, 4 M in dioxane). The mixture was stirred at room temperature for 2 h after which it was concentrated to afford compound D (130 mg, 88.6%).

To a solution of compound D (130 mg, 279 μmol) in DMF (4 mL) was added compound E (37.3 mg, 294 μmol), DIEA (190 mg, 1.47 mmol) and HATU (167 mg, 440 μmol). The mixture was stirred at room temperature for 16 h. After completion, water was added to the reaction which was then extracted with ethyl acetate. The organic layer was washed with brine, dried over sodium sulfate, and concentrated. The residue was purified by silica gel chromatography to afford the title compound 382 (30 mg, 18.5%). LCMS $[M+1]^+$ =552.30. $^1$H NMR (400 MHz, Chloroform-d) δ 7.89 (s, 1H), 5.35 (d, J=5.1 Hz, 1H), 4.11 (s, 3H), 4.05 (bs, 1H), 3.98 (bs, 1H), 3.82-3.67 (m, 4H), 3.65-3.47 (m, 3H), 2.47-2.18 (m, 4H), 2.03-1.75 (m, 8H), 1.64-1.06 (m, 16H), 1.01 (s, 3H), 0.98-0.91 (m, 4H), 0.69 (s, 3H).

Example 383: (R)-1-(4-cyclohexyl-4-hydroxypiperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

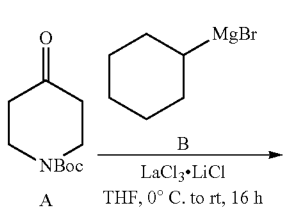

A

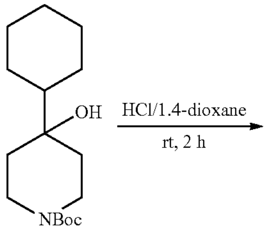

C

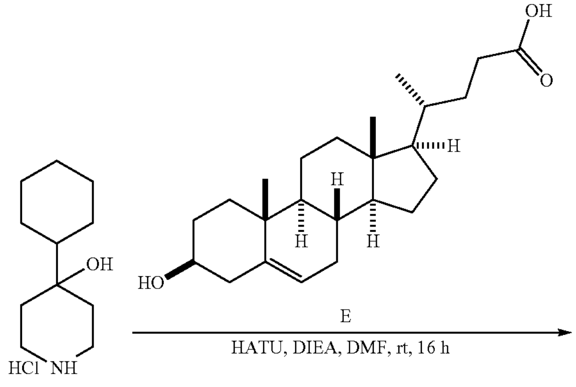

D

-continued

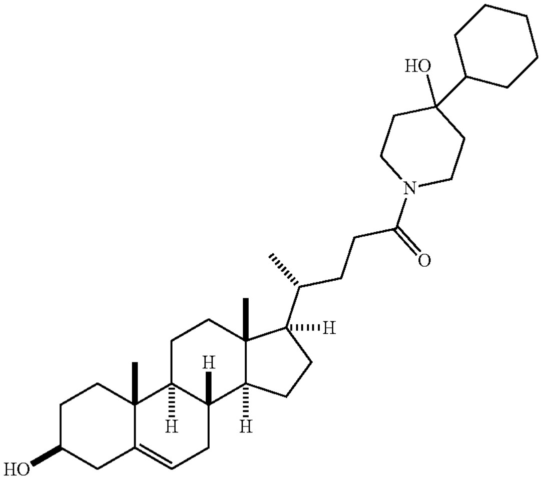

383

To a solution of $LaCl_3LiCl$ (10 mL, 10 mmol, 1M in THF,) was added compound B (1.88 g, 10 mmol) at 0° C. under nitrogen. The mixture was stirred at 0° C. for 2 h, compound A (1.0 g, 5.02 mmol) was added, and the solution was stirred at room temperature for 16 hours. The reaction was quenched with water and extracted with DCM. The organic layer was concentrated to give a crude which was purified by silica gel chromatography to afford compound C (570 mg, 40%).

To a solution of compound C (200 mg, 708 μmol) in DCM (3 mL) was added hydrogen chloride (0.5 mL, 2 mmol, 4 M in dioxane). The mixture was stirred at room temperature for 2 hours. After completion, the solution was concentrated to afford compound D (130 mg) which was directly used in the next step.

To a solution of compound D (130 mg, 594 μmol) in DMF (4 mL) was added compound E (265 mg, 709 μmol), DIEA (635 mg, 4.91 mmol) and HATU (747 mg, 1.96 mmol). The mixture was stirred at room temperature for 16 hours after which it was diluted with water and extracted with ethyl acetate. The organic layer was concentrated to give a crude which was purified by silica gel chromatography to afford the title compound 383 (70 mg, 13%). $^1$H NMR (400 MHz, Chloroform-d) δ 5.38 (d, J=5.0 Hz, 1H), 4.49 (bs, 1H), 3.68 (bs, 1H), 3.61-3.49 (m, 1H), 3.48-3.36 (m, 1H), 2.99-2.89 (m, 1H), 2.46-2.19 (m, 4H), 2.12-1.05 (m, 40H), 1.02 (s, 3H), 0.98 (d, J=6.4 Hz, 3H), 0.95-0.85 (m, 1H), 0.71 (s, 3H). LCMS: $[M+1]^+$=540.35.

Example 384: 1-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]-4-hydroxypiperidine-4-carbonitrile

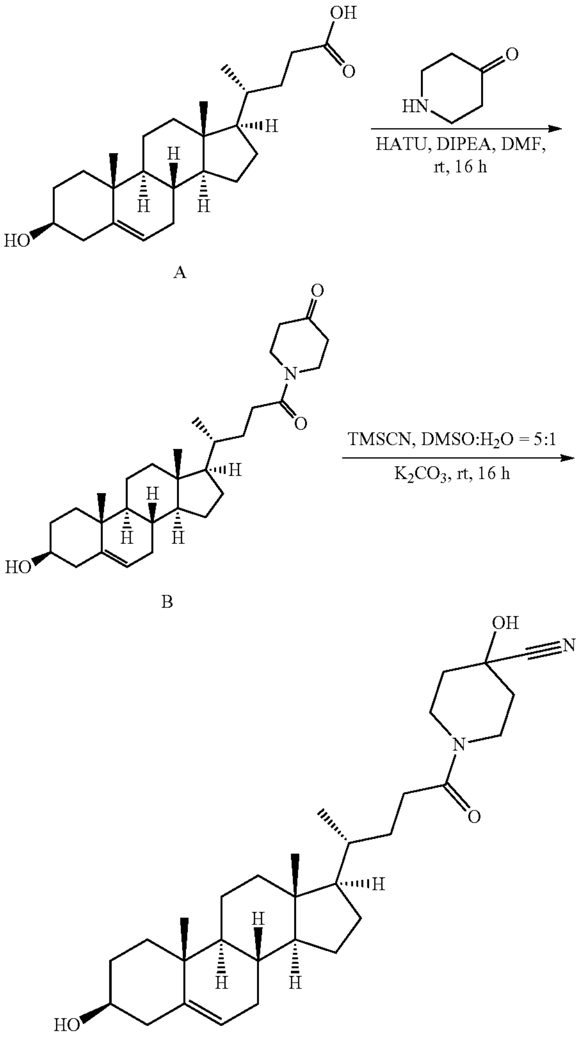

384

To a solution of compound A (500 mg, 1.33 mmol) in tetrahydrofuran (10 mL) was added DIEA (518 mg, 4 mmol), piperidin-4-one (397 mg, 4 mmol) and HATU (1.02 g, 2.67 mmol) at room temperature. The resulting mixture was stirred for 16 h after which it was diluted with water and extracted with ethyl acetate. The organic layer was washed with water and brine, dried with sodium sulfate, and concentrated under vacuum. The residue was purified by silica gel chromatography (eluting with 1/3 ethyl acetate/petroleum ether) to give compound B (150 mg, 24.7%).

To a solution of compound B (150 mg, 329 mmol) and $K_2CO_3$ (91 mg, 658 mmol) in DMSO (2.5 mL) and water (0.5 mL) was added TMSCN (98 mg, 988 mmol) at 0° C. After stirring for 16 h at room temperature, the mixture was diluted with water (20 mL) and extracted with ethyl acetate (20 mL×3). The combined organic phases were washed with brine, dried over sodium sulfate, concentrated under vacuum and the residue was purified by prep-HPLC (eluting with 10% to 95% Acetonitrile/$H_2O$, containing 0.1% formic acid) to give the title compound 384 (10.0 mg, 0.01%). $^1$H NMR (400 MHz, $CDCl_3$) δ 5.35 (d, J=5.0 Hz, 1H), 4.01 (d, J=10.9 Hz, 1H), 3.74 (dd, J=13.2, 6.2 Hz, 1H), 3.58-3.40 (m, 4H), 2.72 (s, 1H), 2.42-1.17 (m, 13H), 1.52-1.04 (m, 13H), 1.01 (s, 3H), 0.95 (d, J=6.6 Hz, 3H), 0.89 (d, J=6.4 Hz, 1H), 0.69 (s, 3H). LCMS: $[M+H]^+$=483.40.

Example 385: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-propionylpiperazin-1-yl)pentan-1-one

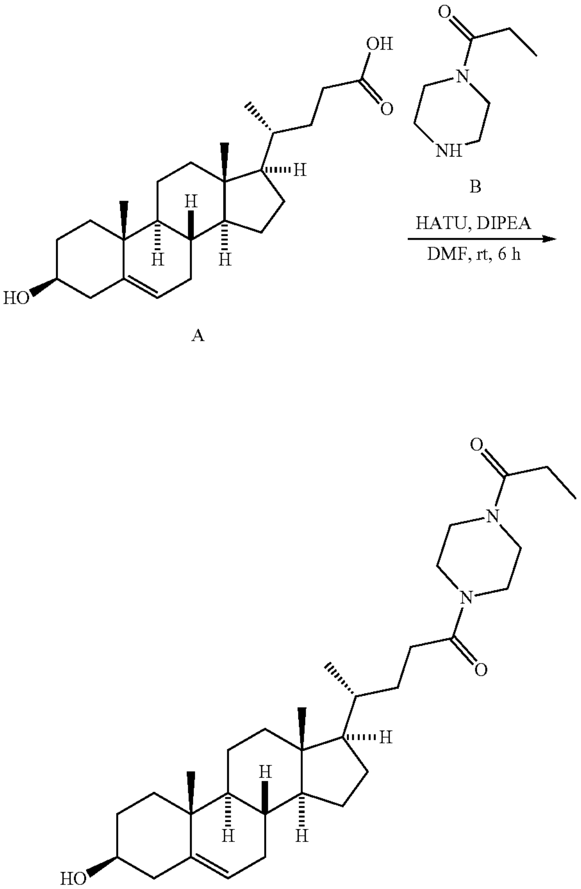

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (200 mg, 534 μmol) and (S)-4-(piperidin-3-yloxy)pyridine hydrochloride (75.9 mg, 534 μmol) were reacted according to the method of Example 536 to afford the title compound 385 (86 mg, 33%) as a white solid. LCMS: [M+1]+=499.30. $^1$H NMR (400 MHz, Chloroform-d) δ 5.35 (d, J=5.0 Hz, 1H), 3.69-3.40 (m, 9H), 2.37 (q, J=7.2 Hz, 3H), 2.30-2.18 (m, 3H), 2.03-1.95 (m, 2H), 1.91-1.73 (m, 3H), 1.67-1.40 (m, 8H) 1.37-1.24 (m, 3H), 1.16 (q, J=7.2 Hz, 4H), 1.11 (s, 1H), 1.06-1.04 (m, 2H), 1.01 (s, 3H), 0.96 (d, J=6.4 Hz, 4H), 0.69 (s, 3H).

Example 386: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-isobutyrylpiperazin-1-yl)pentan-1-one

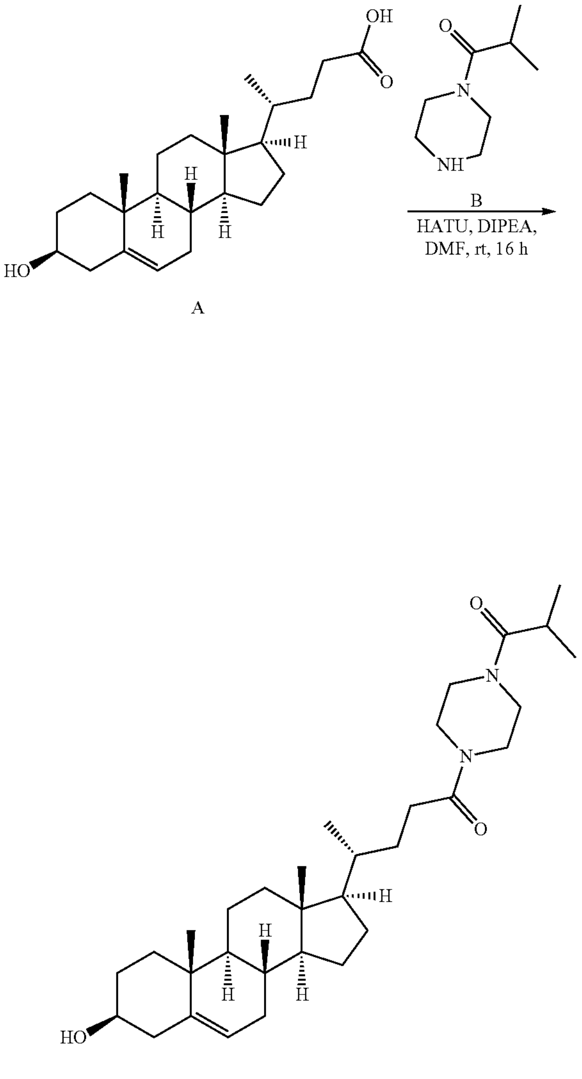

2-methyl-1-(piperazin-1-yl)propan-1-one (50 mg, 320 μmol) and (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (109 mg, 291 μmol) were reacted according to the method of Example 536 to afford the title compound 386 (94 mg, 63%) as a white solid. LCMS: $[M+1]^+$=513.30. $^1$H NMR (400 MHz, Chloroform-d) δ 5.35 (d, J=5.2 Hz, 1H), 3.71-3.40 (m, 9H), 2.85-2.74 (m, 1H), 2.47-2.35 (m, 1H), 2.33-2.20 (m, 3H), 2.03-1.94 (m, 2H), 1.92-1.68 (m, 9H), 1.64-1.41 (m, 6H), 1.36-1.29 (m, 2H), 1.27-1.25 (m, 1H), 1.14 (d, J=6.8 Hz, 6H), 1.12-1.06 (m, 2H), 1.01 (s, 3H), 0.96 (d, J=6.4 Hz, 3H), 0.69 (s, 3H).

Example 387: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-(4-cyclopropanecarbonylpiperazin-1-yl)pentan-1-one

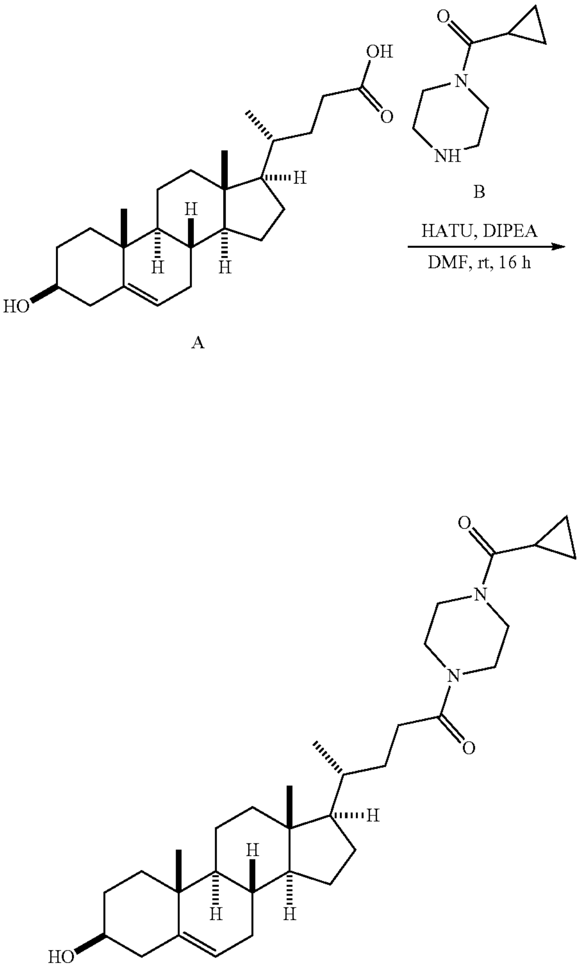

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (185 mg, 1.2 mmol) and cyclopropyl(piperazin-1-yl)methanone (300 mg, 801 μmol) were reacted according to the method of Example 536 to afford the title compound 387 (250 mg, 61%) as a white solid. LCMS: $[M+1]^+$=511.30. $^1$H NMR (400 MHz, Chloroform-d) δ 5.35 (d, J=5.2 Hz, 1H), 3.67 (s, 6H), 3.57-3.42 (m, 3H), 2.45-2.34 (m, 1H), 2.23-2.16 (m, 3H), 2.06-1.93 (m, 2H), 1.90-1.69 (m, 5H), 1.55-1.42 (m, 6H), 1.40-1.24 (m, 3H), 1.20-1.04 (m, 4H), 1.01-0.99 (m, 6H), 0.96 (d, J=6.4 Hz, 3H), 0.83-0.76 (m, 2H), 0.69 (s, 3H).

Example 388: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(pyridine-3-carbonyl)piperazin-1-yl]pentan-1-one

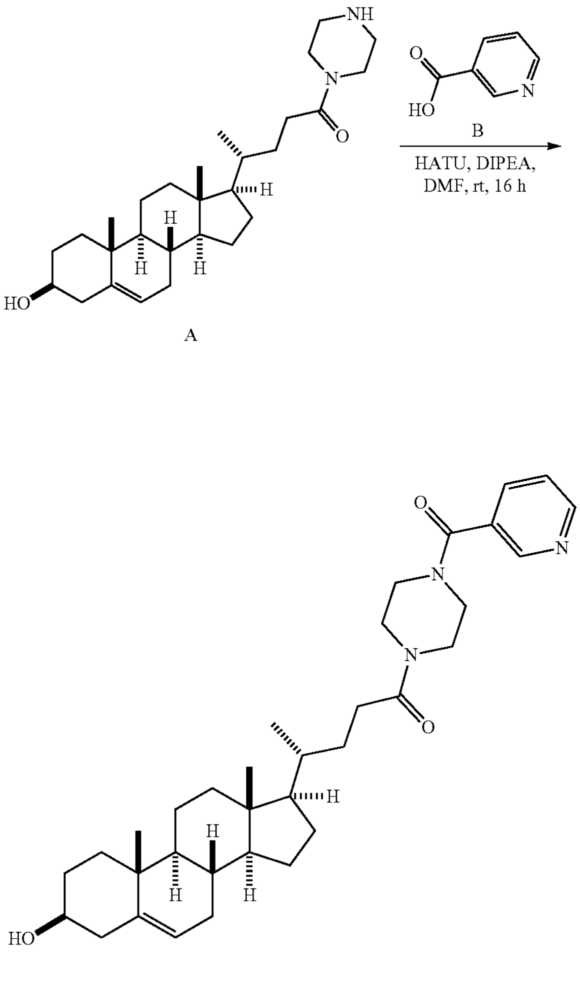

To a solution of compound A (100 mg, 226 μmol) in DMF (2 mL) at room temperature was added compound B (33 mg, 271 μmol), HATU (129 mg, 339 μmol) and DIPEA (60 mg, 452 μmol). The reaction was stirred at room temperature for 16 hours. Water (20 mL) was added, and the reaction was extracted with EtOAc (20 mL*3). The combined organic phase was washed with water (20 mL*2), brine (20 mL), dried over sodium sulfate, and concentrated under reduced pressure. The residue was purified by silica gel chromatography to afford the title compound 388 (20 mg, 16%) as a white solid. $^1$H NMR (400 MHz, Chloroform-d) δ 8.70 (s, 2H), 7.81 (d, J=7.6 Hz, 1H), 7.55-7.37 (m, 1H), 5.35 (d, J=5.2 Hz, 1H), 3.90-3.36 (m, 9H), 2.49-2.14 (m, 5H), 2.06-1.92 (m, 3H), 1.84-1.80 (m, 6H), 1.65-1.54 (m, 2H), 1.46 (dd, J=11.2, 4.4 Hz, 2H), 1.39-1.23 (m, 4H), 1.13-1.10 (m, 4H), 1.01 (s, 3H), 0.96 (d, J=6.4 Hz, 4H), 0.69 (s, 3H). LCMS: $[M+H]^+$=548.4.

Example 389: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyridazine-4-carbonyl)piperazin-1-yl) pentan-1-one

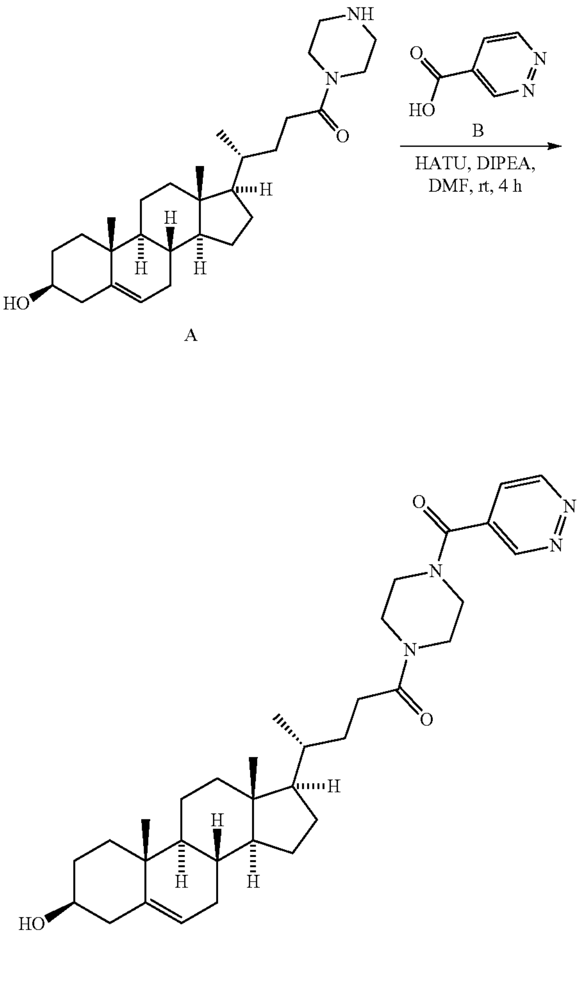

To a solution of compound A (357 mg, 806 μmol) in DMF (6 mL) was added compound B (100 mg, 806 μmol), HATU (379 mg, 1.61 mmol), DIPEA (521 mg, 4.03 mmol) and stirred at room temperature for 4 hours. The reaction was diluted with water (5 mL) and extracted with ethyl acetate (15 mL). The organic layer was concentrated under reduced pressure. The crude product was purified by silica gel chromatography to afford the title compound 389 (86 mg, 33%) as a white solid. LCMS: [M+1]+=531.25. $^1$H NMR (400 MHz, Chloroform-d) δ 9.35 (dd, J=5.2, 1.2 Hz, 1H), 9.23 (dd, J=2.2, 1.2 Hz, 1H), 7.50 (d, J=5.0 Hz, 1H), 5.35 (d, J=5.0 Hz, 1H), 3.81 (s, 3H), 3.65-3.50 (m, 4H), 3.39 (s, 2H), 2.40 (s, 1H), 2.27 (dt, J=17.3, 9.1 Hz, 3H), 1.97 (d, J=15.8 Hz, 2H), 1.84 (d, J=12.4 Hz, 3H), 1.57 (s, 3H), 1.51 (dd, J=7.2, 3.6 Hz, 3H), 1.44 (d, J=6.4 Hz, 2H), 1.26 (s, 5H), 1.16 (s, 1H), 1.10 (s, 1H), 1.08 (s, 1H), 1.01 (s, 3H), 0.97-0.93 (m, 3H), 0.69 (s, 3H).

Example 390: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(isothiazole-5-carbonyl)piperazin-1-yl)pentan-1-one

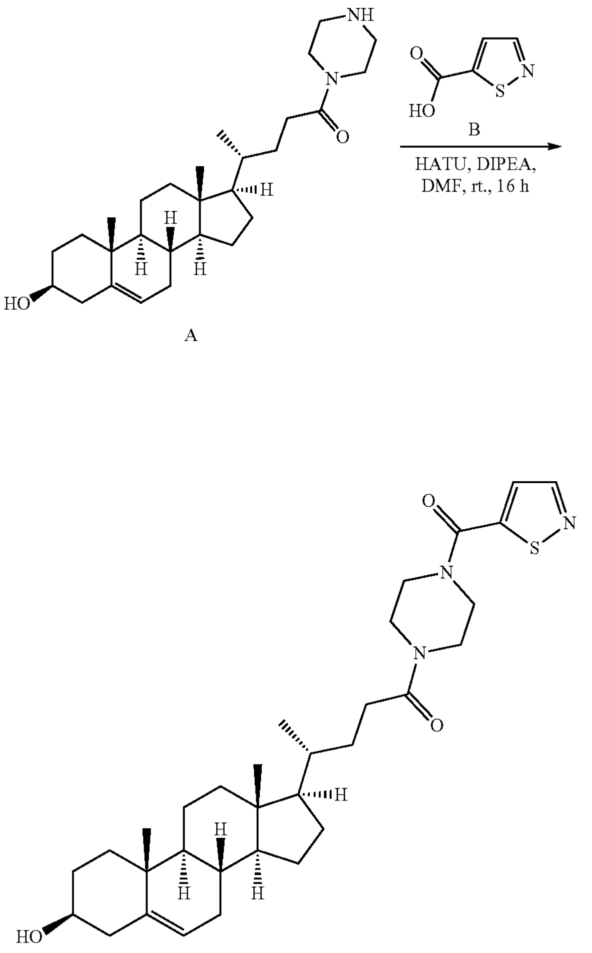

To a solution of compound A (500 mg, 1.13 mmol) and compound B (146 mg, 1.13 mmol) in DMF (6 mL) was added HATU (644 mg, 1.69 mmol), DIPEA (438 mg, 3.39 mmol) and the reaction was stirred at room temperature for 16 hours. Upon completion, the reaction was quenched with saturated ammonium chloride (15 mL) and extracted with ethyl acetate (15 mL*3). The combined organic layers were washed with brine, dried over sodium sulfate, filtered, and concentrated under reduced pressure. The crude product was purified by silica gel chromatography to afford the title compound 390 (171 mg, 27.3%) as a white solid. LCMS: $[M+1]^+$=554.25. $^1$H NMR (400 MHz, Chloroform-d) δ 8.49 (d, J=1.6 Hz, 1H), 7.38 (d, J=1.6 Hz, 1H), 5.35 (d, J=5.0 Hz, 1H), 3.81-3.47 (m, 9H), 2.45-2.36 (m, 1H), 2.32-2.20 (m, 3H), 2.03-1.95 (m, 2H), 1.91-1.74 (m, 4H), 1.57-1.44 (m, 6H), 1.42-1.24 (m, 4H), 1.21-1.06 (m, 4H), 1.01 (s, 3H), 0.96 (d, J=6.4 Hz, 3H), 0.93-0.86 (m, 1H), 0.69 (s, 3H).

Example 391: (R)-1-(4-(1H-pyrazole-4-carbonyl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

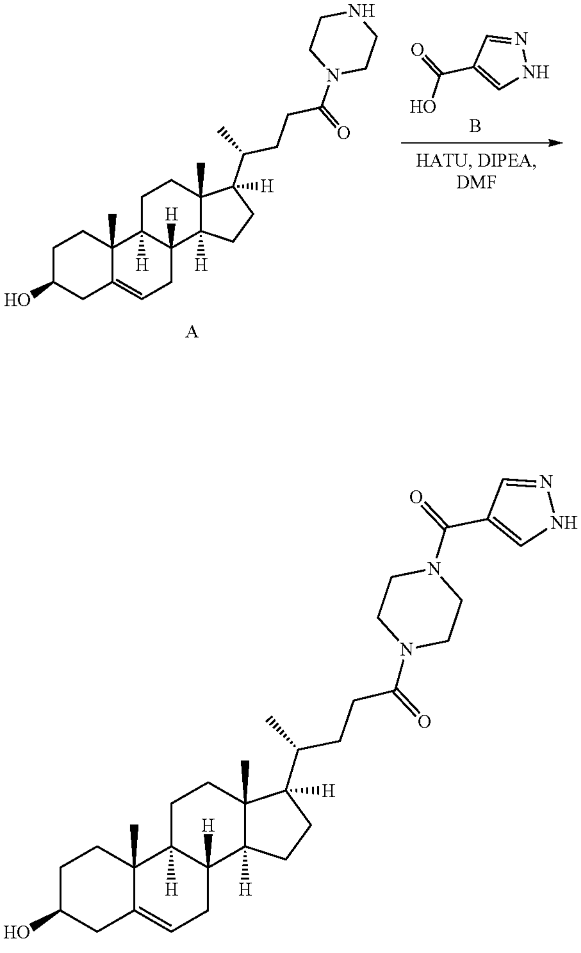

To a solution of compound A (235 mg, 491 μmol), compound B (50 mg, 446 μmol) and HATU (254 mg, 669 μmol) in DMF (2 mL) was added DIPEA (173 mg, 1.34 mmol) and the reaction was stirred at room temperature for 1 h. Water (10 mL) was added to the reaction and extracted with EtOAc (10 mL*3). The combined organic phase was washed with brine, dried over sodium sulfate, and concentrated under vacuum. The residue was purified by Prep-HPLC to afford the title compound 391 (36.3 mg, 15%) as a white solid. LCMS: $[M+1]^+$=537.30. $^1$H NMR (400 MHz, DMSO-d6) δ 13.21 (s, 1H), 8.09 (s, 1H), 7.73 (s, 1H), 5.26 (d, J=4.8 Hz, 1H), 4.58 (d, J=4.4 Hz, 1H), 3.61 (s, 2H), 3.56 (s, 2H), 3.49-3.45 (m, 4H), 3.28-3.21 (m, 1H), 2.38-2.31 (m, 1H), 2.27-2.06 (m, 3H), 1.99-1.61 (m, 6H), 1.56-0.97 (m, 14H), 0.94 (s, 3H), 0.91 (d, J=6.4 Hz, 3H), 0.86 (dd, J=11.4, 4.8 Hz, 1H), 0.65 (s, 3H).

Example 392: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(1-methyl-1H-pyrazole-4-carbonyl)piperazin-1-yl]pentan-1-one

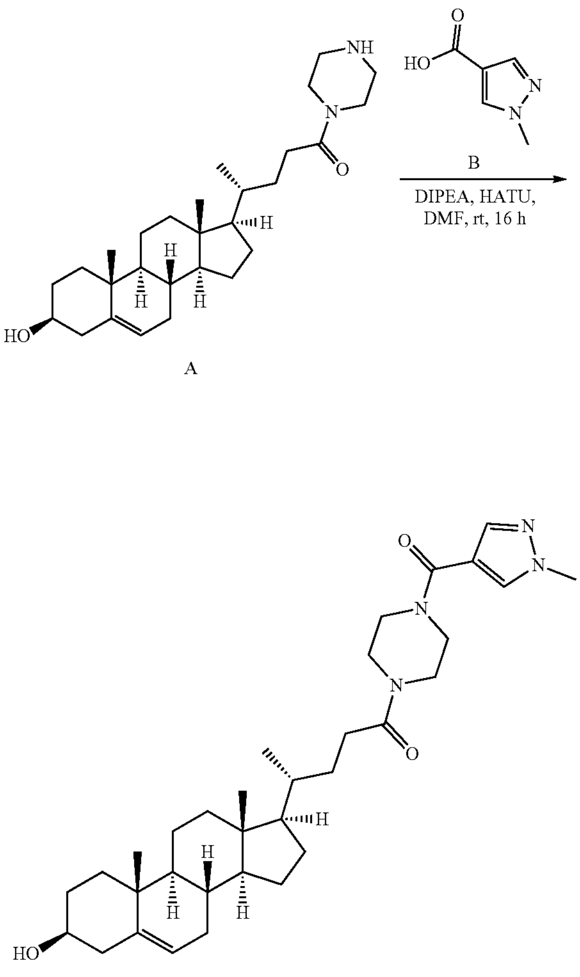

To a solution of compound A (0.2, 452 μmol) in DMF (5 mL) was added compound B (38 mg, 301 mot), DIPEA (234 mg, 1.81 mmol) and HATU (229 mg, 904 μmol). The reaction was stirred at room temperature for 16 hours. The reaction was diluted with saturated aqueous $NH_4Cl$ (30 mL) and extracted with EtOAc (10 mL*2). The combined organic layers were washed with saturated $NaHCO_3$ (20 mL), water (20 mL), brine (20 mL), dried over sodium sulfate and concentrated under reduced pressure. The residue was purified by silica gel chromatography to afford the title compound 392 (30 mg, 18%). LCMS: $[M+1]^+$=551.30. $^1H$ NMR (400 MHz, Methanol-d4) δ 7.98 (s, 1H), 7.74 (s, 1H), 5.34 (d, J=5.2 Hz, 1H), 3.93 (s, 3H), 3.82-3.59 (m, 8H), 3.44-3.36 (m, 1H), 2.54-2.43 (m, 1H), 2.40-2.30 (m, 1H), 2.28-2.17 (m, 2H), 2.08-1.98 (m, 2H), 1.97-1.84 (m, 3H), 1.81-1.75 (m, 2H), 1.68-1.60 (m, 1H), 1.58-1.44 (m, 6H), 1.38-1.28 (m, 3H), 1.25-1.10 (m, 3H), 1.08-1.06 (m, 1H), 1.04-0.98 (m, 7H), 1.04-0.97 (m, 1H), 0.73 (s, 3H).

Example 393: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(1-methyl-1H-1,2,3-triazole-4-carbonyl)piperazin-1-yl)pentan-1-one

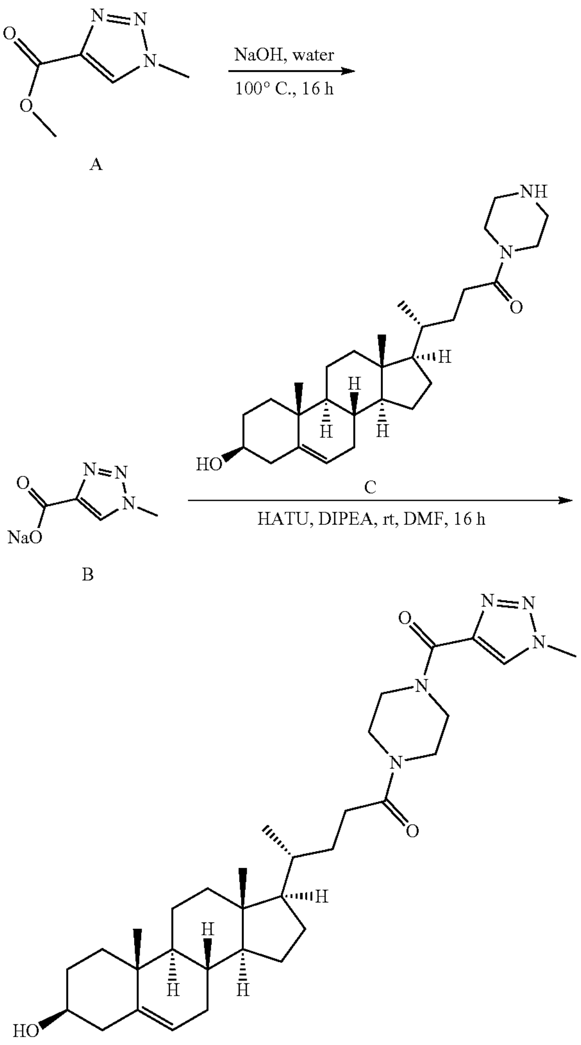

To a solution of compound A (100 mg, 0.71 mmol) in MeOH (3 mL) and water (1 mL) was added NaOH (85 mg, 2.1 mmol). The reaction was stirred at 100° C. for 16 h. The reaction was concentrated to afford the compound B (45 mg, 50%) as colorless oil. To a solution of compound B (45 mg, 0.3 mmol) in DMF (4 mL) was added compound C (157 mg, 354 μmol), HATU (269 mg, 0.7 mol), DIPEA (275 mg, 2.12 mmol) and the reaction was stirred at room temperature for 16 h. The reaction was diluted with water (5 mL) extracted with EtOAc (10 mL). The organic layer was washed with brine (5 mL), dried over sodium sulfate and concentrated. The residue was purified by silica gel chromatography to afford the title compound 393 (20 mg, 10.2%) as a white solid. LCMS: $[M+1]^+$=552.30. $^1H$ NMR (400 MHz, Chloroform-d) δ 8.08 (d, J=9.6 Hz, 1H), 5.35 (d, J=4.8 Hz, 1H), 4.33-4.31 (m, 2H), 4.15 (s, 3H), 3.83-3.68 (m, 4H), 3.63-3.47 (m, 3H), 2.48-2.34 (m, 1H), 2.34-2.20 (m, 3H), 2.04-

1.94 (m, 2H), 1.92-1.70 (m, 7H), 1.64-1.42 (m, 8H), 1.41-1.24 (m, 3H), 1.21-1.04 (m, 4H), 1.01 (s, 3H), 0.96 (d, J=6.4 Hz, 3H), 0.69 (s, 3H).

Example 394: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyridin-2-yl)piperazin-1-yl)pentan-1-one

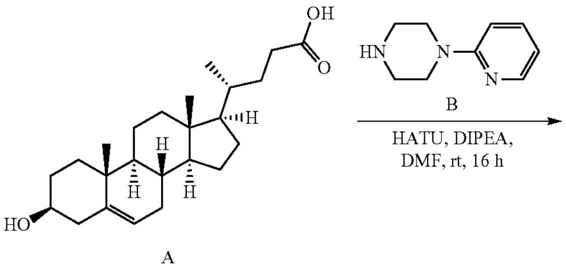

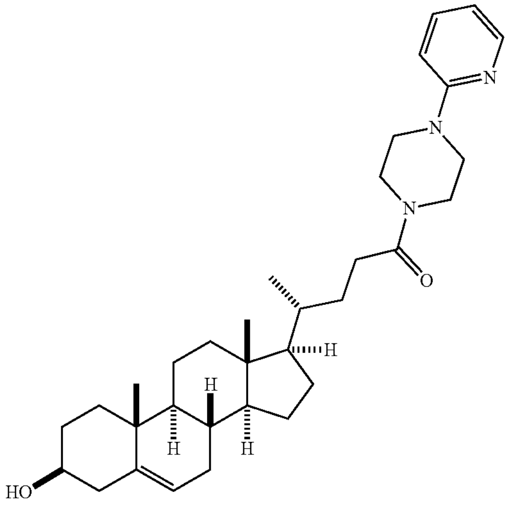

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (300 mg, 0.8 mmol) and 1-(pyridin-2-yl)piperazine (145 mg, 0.89 mmol) were reacted according to the method of Example 536 to afford the title compound 394 (100 mg, 24%) as a white solid. LCMS: $[M+1]^+$=520.30. $^1$H NMR (400 MHz, Chloroform-d) δ 8.20 (d, J=4.8 Hz, 1H), 7.51 (td, J=8.4, 2.0 Hz, 1H), 6.72-6.63 (m, 2H), 5.35 (d, J=5.2 Hz, 1H), 3.74 (t, J=5.2 Hz, 2H), 3.65-3.56 (m, 4H), 3.49 (t, J=5.6 Hz, 2H), 2.49-2.38 (m, 1H), 2.34-2.19 (m, 3H), 2.05-1.73 (m, 6H), 1.64-1.03 (m, 17H), 1.01 (s, 3H), 0.97 (d, J=6.4 Hz, 3H), 0.92 (dd, J=11.2, 5.4 Hz, 1H), 0.69 (s, 3H).

Example 395: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(pyridin-3-yl)piperazin-1-yl]pentan-1-one

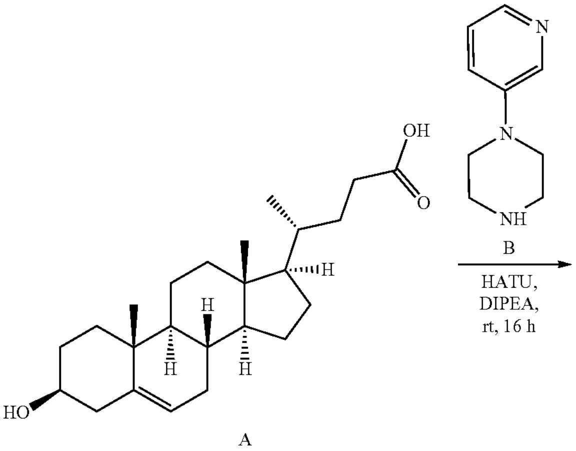

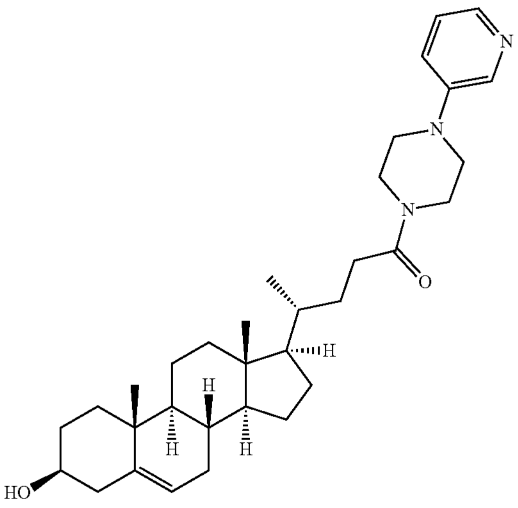

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (0.5 g, 1.33 mmol) and 1-(pyridin-3-yl)piperazine (242 mg, 1.48 mmol) were reacted according to the method of Example 536 to afford the title compound 395 (116 mg, 15%) as a white solid. LCMS: $[M+1]^+$=520.30. $^1$H NMR (400 MHz, Chloroform-d) δ 8.31 (s, 1H), 8.17-8.10 (m, 1H), 7.24-7.17 (m, 2H), 5.34 (d, J=5.2 Hz, 1H), 3.87-3.72 (m, 2H), 3.70-3.59 (m, 2H), 3.58-3.45 (m, 1H), 3.30-3.12 (m, 4H), 2.49-2.36 (m, 1H), 2.32-2.18 (m, 3H), 2.08-1.93 (m, 4H), 1.90-1.76 (m, 4H), 1.63-1.40 (m, 7H), 1.38-1.24 (m, 3H), 1.21-1.03 (m, 5H), 1.00 (s, 3H), 0.97 (d, J=6.4 Hz, 3H), 0.93-0.89 (m, 1H), 0.69 (s, 3H).

Example 396: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyridin-4-yl)piperazin-1-yl)pentan-1-one

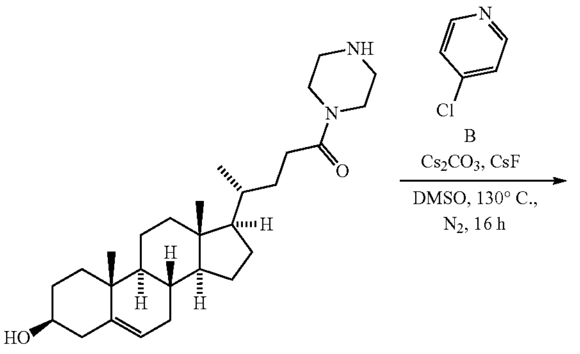

A

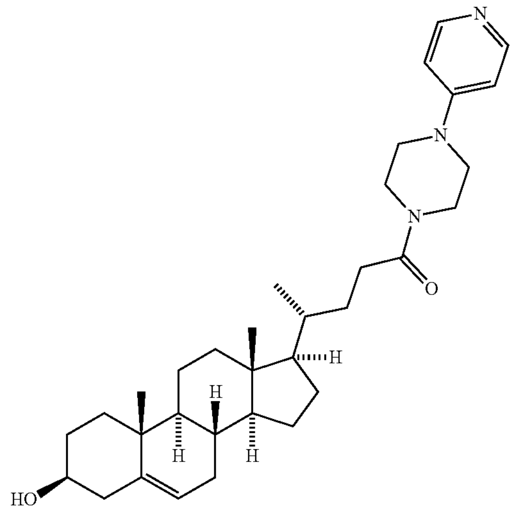

To a solution of compound A (390 mg, 881 μmol) in DMSO (6 mL) was added compound B (0.1 g, 881 μmol), CsF (401 mg, 2.64 mmol) and $Cs_2CO_3$ (861 mg, 2.64 mmol). The reaction was stirred at 130° C.; for 16 hours under $N_2$ atmosphere. Upon completion, the reaction was diluted with water and extracted with ethyl acetate. The organic layer was concentrated under reduced pressure. The crude product was purified by silica gel chromatography to afford the title compound 396 (100 mg, 22%) as a white solid. LCMS: $[M+1]^+$=, 520.30. $^1$H NMR (400 MHz, Chloroform-d) δ 8.35 (d, J=6.6 Hz, 2H), 6.87 (d, J=6.8 Hz, 2H), 5.35 (d, J=5.2 Hz, 1H), 3.87 (bs, 2H), 3.71-3.60 (m, 6H), 3.58-3.48 (m, 1H), 2.34-1.94 (m, 10H), 1.89-1.80 (m, 2H), 1.52-1.42 (m, 4H), 1.35-1.29 (m, 2H), 1.26 (s, 3H), 1.19-1.03 (m, 3H), 1.01 (s, 3H), 0.97 (d, J=6.4 Hz, 3H), 0.69 (s, 3H).

Example 397: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyrimidin-2-yl)piperazin-1-yl)pentan-1-one

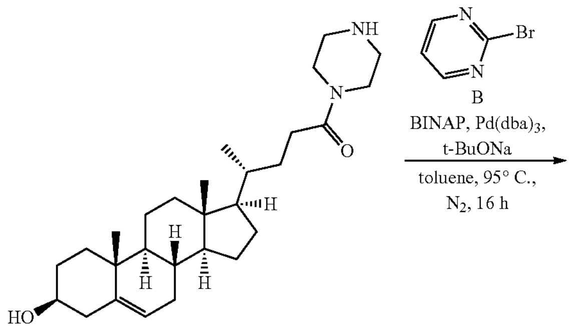

A

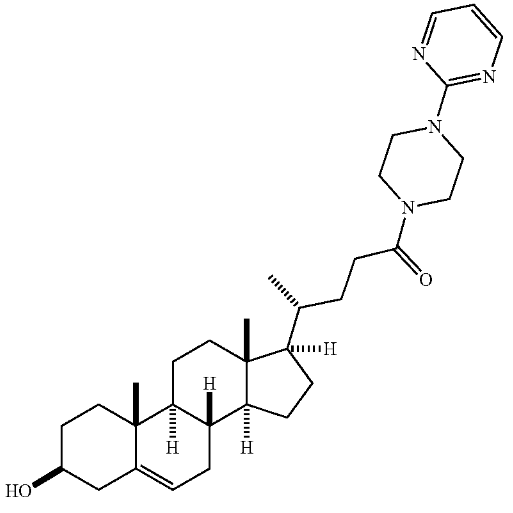

To a solution of compound A (300 mg, 0.67 mmol) in toluene (6 mL) was added compound B (108 mg, 0.67 mmol), BINAP (127 mg, 203 μmol), t-BuONa (65.1 mg, 0.67 mmol) and $Pd_2(dba)_3$ (124 mg, 0.136 mmol). The reaction was stirred at 95° C. under $N_2$ for 16 h. The reaction was quenched with saturated aqueous $NH_4Cl$ (5 mL) and extracted with EtOAc (10 mL). The organic layer was washed with brine, dried over sodium sulfate, filtered, and concentrated. The residue was purified by silica gel chromatography to afford the title compound 397 (14 mg, 3.9%) as a white solid. LCMS: $[M+1]^+$=521.30. $^1$H NMR (400 MHz, Methanol-$d_4$) δ 8.35 (d, J=4.8 Hz, 2H), 6.63 (t, J=4.8 Hz, 1H), 5.34 (d, J=5.2 Hz, 1H), 3.83 (dt, J=24.5, 5.4 Hz, 4H), 3.69-3.60 (m, 4H), 3.39 (dq, J=10.5, 5.5 Hz, 1H), 2.56-2.45 (m, 1H), 2.41-2.31 (m, 1H), 2.27-2.15 (m, 2H), 2.11-1.74 (m, 7H), 1.69-1.43 (m, 8H), 1.42-0.87 (m, 18H), 0.74 (s, 3H).

Example 398: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyrazin-2-yl)piperazin-1-yl)pentan-1-one

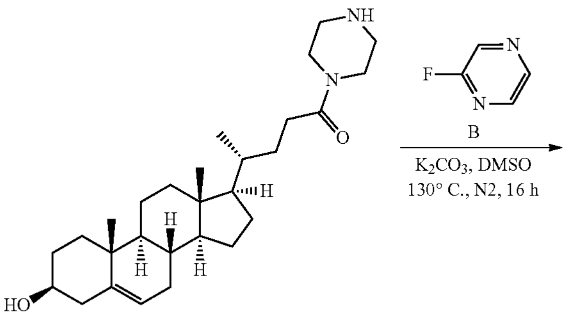

A

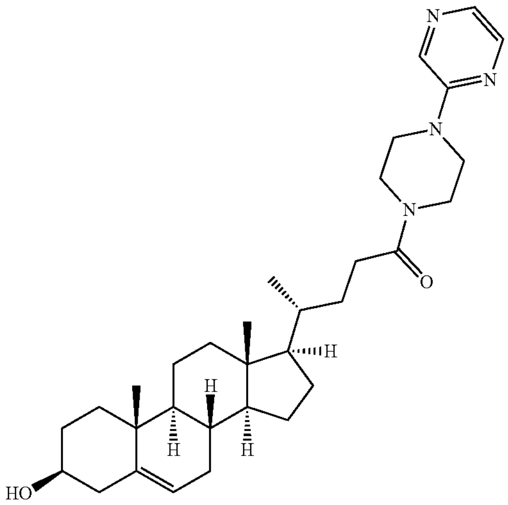

To a solution of compound A (190 mg, 429 μmol) in DMSO (3 mL) was added compound B (42.1 mg, 429 μmol) and $K_2CO_3$ (178 mg, 1.29 mmol). The reaction was stirred at 130° C. under $N_2$ for 16 h. The reaction was diluted with water (5 mL) and extracted with EtOAc (15 mL). The organic layer was washed with brine, dried over sodium sulfate, and concentrated under reduced pressure. The crude product was purified by silica gel chromatography to afford the title compound 398 (20 mg, 10%) as a white solid. LCMS: $[M+1]^+$=521.25. $^1$H NMR (400 MHz, Chloroform-d) δ 8.16 (s, 1H), 8.10 (s, 1H), 7.90 (d, J=2.4 Hz, 1H), 5.35 (d, J=5.2 Hz, 1H), 3.76 (s, 2H), 3.66 (s, 2H), 3.61-3.57 (m, 4H), 3.56-3.48 (m, 1H), 2.47-2.18 (m, 4H), 2.04-1.03 (m, 28H), 1.01 (s, 3H), 0.97 (d, J=6.4 Hz, 3H), 0.96-0.84 (m, 2H), 0.69 (s, 3H).

Example 399: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(pyridazin-3-yl)piperazin-1-yl]pentan-1-one

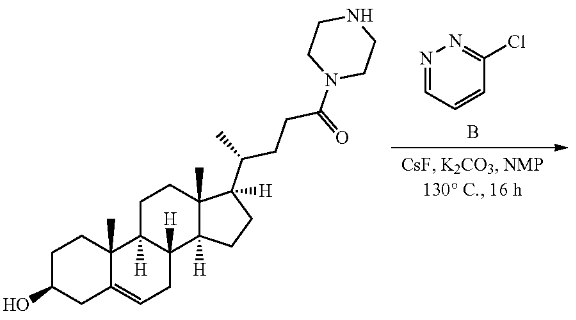

A

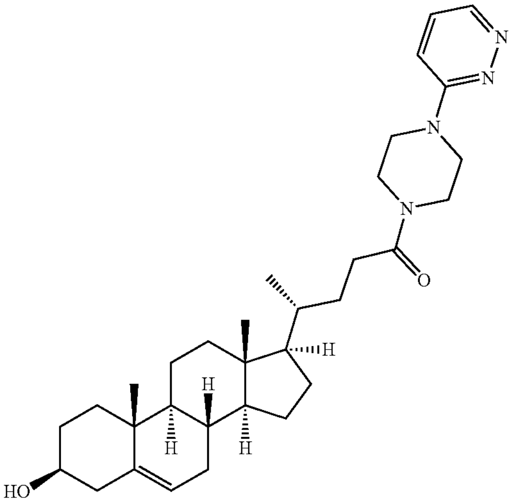

To a solution of compound A (0.1 g, 226 μmol) in NMP (2 mL) was added compound B (25.9 mg, 226 μmol), CsF (103 mg, 678 μmol) and $K_2CO_3$ (156 mg, 1.13 mmol). The reaction was stirred at 130° C. for 16 hours. The reaction was cooled to room temperature. The reaction was quenched with saturated aqueous $NH_4Cl$ (5 mL) and extracted with EtOAc (10 mL). The organic layer was washed with brine, dried over sodium sulfate, filtered, and concentrated. The residue was purified by silica gel chromatography to afford the title compound 399 (10 mg, 8.5%) as a white solid. LCMS: $[M+1]^+$=521.25. $^1$H NMR (400 MHz, Methanol-$d_4$) δ 8.52 (d, J=4.4 Hz, 1H), 7.48-7.42 (m, 1H), 7.34-7.28 (m, 1H), 5.04-5.27 (m, 1H), 3.79-3.68 (m, 6H), 3.65 (s, 2H), 3.45-3.35 (m, 1H), 2.56-2.47 (m, 1H), 2.41-2.32 (m, 1H), 2.26-2.18 (m, 2H), 2.08-1.85 (m, 4H), 1.82-1.75 (m, 2H), 1.68-1.60 (m, 1H), 1.57-1.46 (m, 6H), 1.29-1.27 (m, 6H), 1.22-1.06 (m, 4H), 1.04-0.99 (m, 6H), 0.96-0.88 (m, 2H), 0.74 (s, 3H).

Example 400: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyrimidin-4-yl)piperazin-1-yl)pentan-1-one

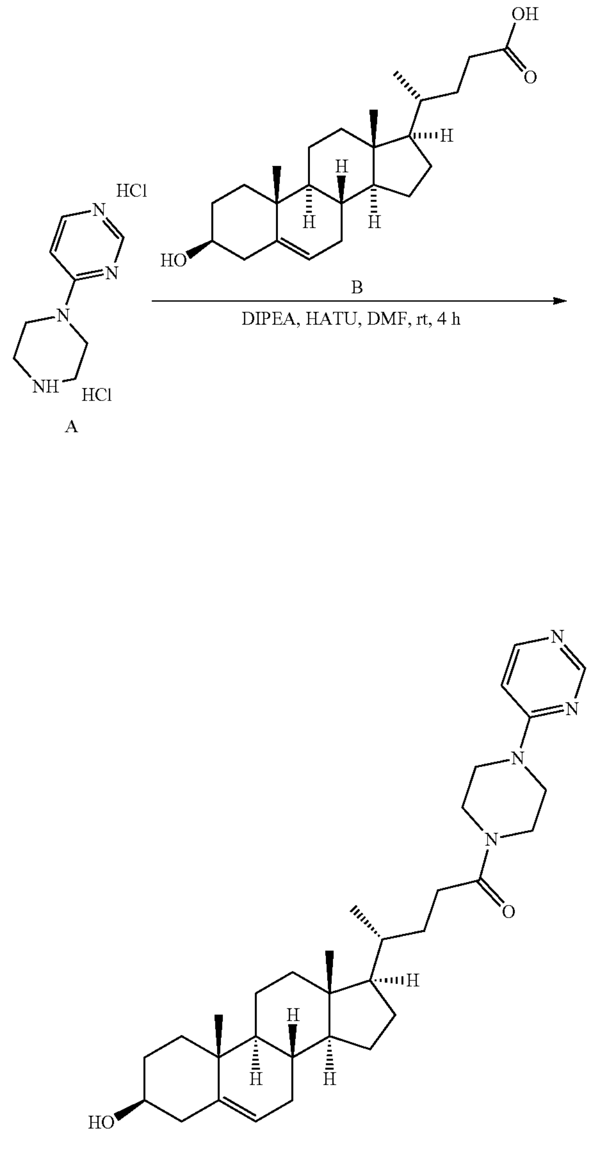

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (284 mg, 759 μmol) and 4-(piperazin-1-yl)pyrimidine dihydrochloride (108 mg, 505 μmol) was reacted according to the method of Example 536 to afford the title compound 400 (80 mg, 18%) as a white solid. LCMS: $[M+1]^+$=521.30. $^1$H NMR (400 MHz, Chloroform-d) δ 8.63 (s, 1H), 8.24 (d, J=6.4 Hz, 1H), 6.55 (dd, J=6.4, 1.2 Hz, 1H), 5.34 (dd, J=4.8, 2.4 Hz, 1H), 3.84-3.47 (m, 9H), 2.41 (td, J=10.4, 5.2 Hz, 1H), 2.34-2.17 (m, 3H), 2.03-1.94 (m, 2H), 1.90-1.76 (m, 4H), 1.61-1.43 (m, 7H), 1.41-1.25 (m, 3H), 1.22-1.03 (m, 5H), 1.01 (s, 3H), 0.97 (d, J=6.4 Hz, 3H), 0.95-0.86 (m, 1H), 0.69 (s, 3H).

Example 401: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(pyridin-4-yloxy)piperidin-1-yl]pentan-1-one

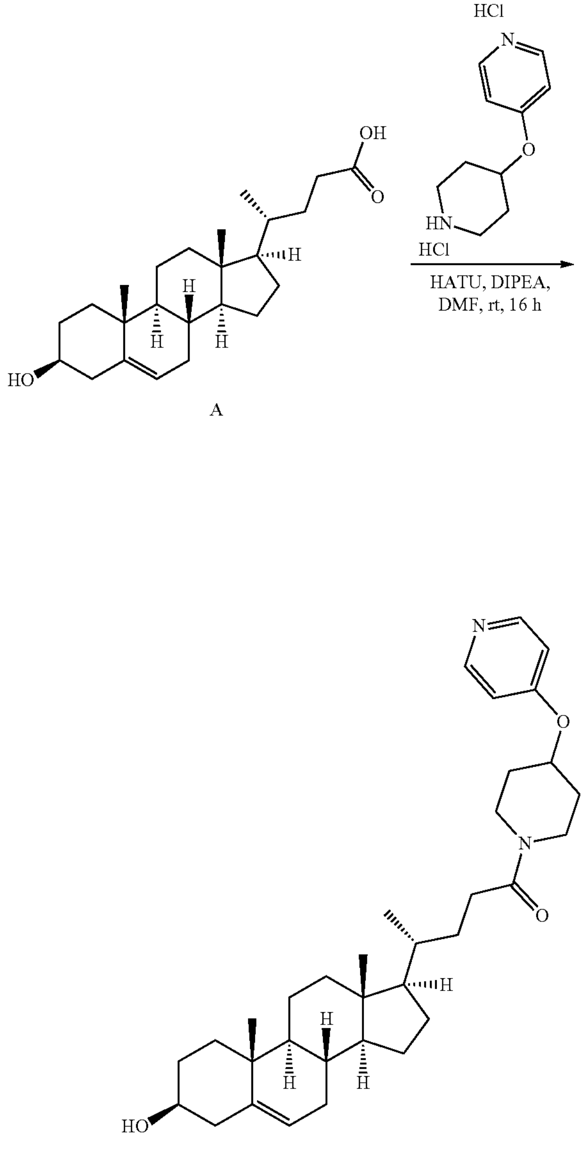

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (74.6 mg, 199 μmol) and 4-(piperidin-4-yloxy)pyridine dihydrochloride (50 mg, 199 μmol) was reacted according to the method of Example 536 to afford the title compound 401 (34.1 mg, 32.0%) as a white solid. LCMS: $[M+1]^+$=535.25. $^1$H NMR (400 MHz, $CDCl_3$) δ 8.46 (d, J=5.6 Hz, 2H), 6.93 (d, J=5.6 Hz, 2H), 5.35 (d, J=5.0 Hz, 1H), 4.74-4.66 (m, 1H), 3.85-3.39 (m, 5H), 2.47-2.19 (m, 7H), 2.05-1.76 (m, 10H), 1.51-1.44 (m, 4H), 1.40-1.24 (m, 6H), 1.22-1.06 (m, 4H), 1.01 (s, 3H), 0.96 (d, J=6.4 Hz, 3H), 0.69 (s, 3H).

Example 402: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-methoxypiperidin-1-yl)pentan-1-one

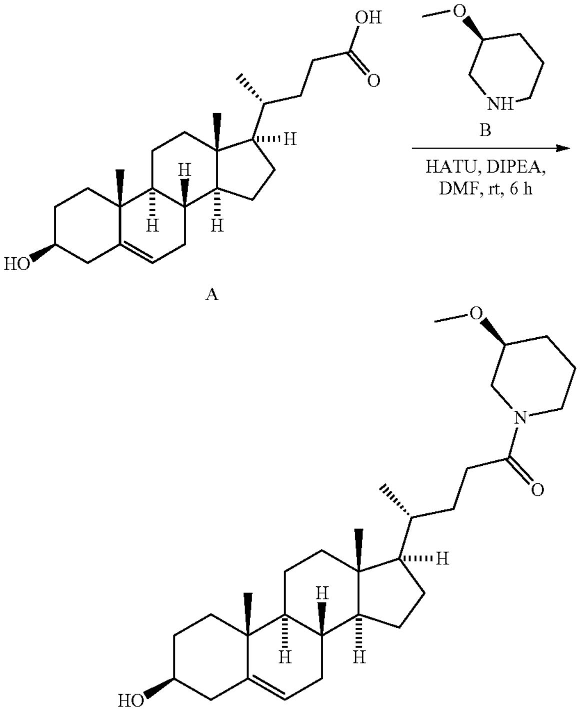

A (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (163 mg, 434 μmol) and (S)-3-methoxypiperidine (50 mg, 434 μmol) was reacted according to the method of Example 536 to afford the title compound 402 (60 mg, 29%) as a white solid. LCMS: $[M+1]^+=472.30$. $^1H$ NMR (400 MHz, Chloroform-d) δ 5.35 (d, J=5.2 Hz, 1H), 4.11-3.41 (m, 6H), 3.38 (s, 3H), 3.26-3.10 (m, 3H), 2.42-2.19 (m, 4H), 2.04-1.94 (m, 3H), 1.88-1.77 (m, 4H), 1.61-1.51 (m, 5H), 1.49-1.04 (m, 15H), 1.01 (s, 3H), 0.95 (d, J=6.4 Hz, 4H), 0.68 (s, 3H).

Example 403: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methyl-N-((1s, 4S)-4-(N-methylacetamido)cyclohexyl)pentanamide

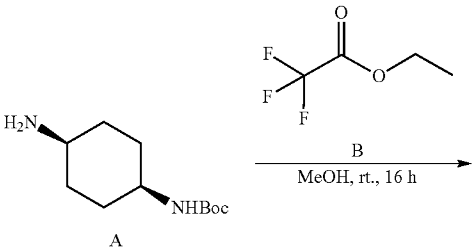

A

-continued

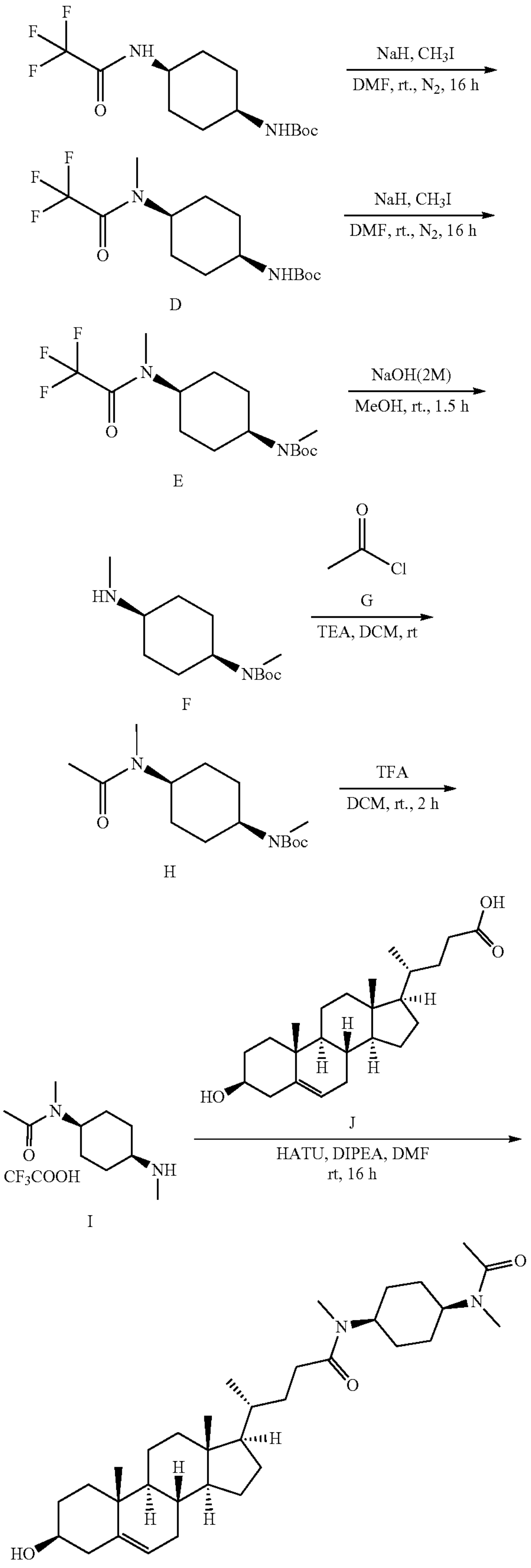

To a solution of compound A (1.0 g, 4.67 mmol) in MeOH (10 mL) was added compound B (1.7 mL). The reaction was stirred at room temperature for 16 h. The reaction was quenched with saturated $NaHCO_3$ (10 mL) and extracted with EtOAc (50 mL). The organic layer was concentrated under reduced pressure. The crude product was purified by silica gel chromatography to give compound C (1.0 g, 69%) as a yellow oil. To a solution of compound C (1.35 g, 4.35 mmol) in DMF (10 mL) was added NaH (400 mg, 10.0 mmol, 60% dispersion in mineral oil) at 0° C. and stirred for 30 min. MeI (1.23 g, 8.7 mmol) was added at room temperature and stirred for 16 hours. The reaction was quenched with $NaHCO_3$ (10 mL) and extracted with ethyl acetate (50 mL). The organic layer was concentrated, and the crude product was purified by silica gel chromatograph to give compound D (1.0 g, 70%) as a yellow oil.

To a solution of compound D (800 mg, 2.47 mmol) in DMF (10 mL) was added NaH (0.22 g, 5.50 mmol, 60% dispersion in mineral oil) at 0° C. and stirred for 30 min. MeI (0.7 g, 4.93 mmol) was added at room temperature and stirred for 16 hours. The reaction was quenched with $NaHCO_3$ (10 mL) and extracted with ethyl acetate (50 mL). The organic layer was concentrated. The crude product was purified by silica gel chromatograph to give compound E (600 mg, 71%) as a yellow oil. To a solution of compound E (600 mg, 1.77 mmol) in methanol (6 mL) was added NaOH (2 mL, 4 mmol, 2 M in water). The reaction was stirred at room temperature for 1.5 hours. The reaction was diluted with water (10 mL) and extracted with EtOAc (30 mL). The organic layer was concentrated under vacuum to afford the crude compound F (400 mg, 93%) as a yellow oil. To a solution of compound F (100 mg, 413 μmol) in DCM (2 mL) was added compound G (48.6 mg, 619 μmol), triethylamine (125 mg, 1.24 mmol) and stirred at room temperature for 16 h. The reaction was diluted with water (5 mL) and extracted with ethyl acetate (10 mL). The organic layer was concentrated under vacuum and the residue was purified by silica gel chromatograph to afford compound H (39 mg, 33%) as a yellow oil. The solution of compound H (78 mg, 274 μmol) in TFA (1 mL) and DCM (2 mL) was stirred at room temperature for 2 h. The reaction concentrated under reduced pressure to give compound I (60 mg) as the TFA salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (54.9 mg, 404 μmol) and N-methyl-N-((1s,4s)-4-(methylamino)cyclohexyl)acetamide (60 mg, 270 μmol) was reacted according to the method of Example 536 to afford the title compound 403 (28 mg, 31%) as a white solid. LCMS: $[M+1]^+$=541.4. $^1H$ NMR (400 MHz, Chloroform-d) δ 5.36-5.33 (m, 1H), 3.56-3.48 (m,, 1H), 3.01 (s, 3H), 2.98 (s, 3H), 2.49-2.19 (m, 8H), 2.16 (s, 3H), 2.04-1.65 (m, 15H), 1.64-1.37 (m, 10H), 1.36-1.26 (m, 5H), 1.21-1.10 (m, 3H), 1.09-1.02 (m, 2H), 1.00 (s, 3H), 0.96 (d, J=6.4 Hz, 3H), 0.91-0.88 (m, 1H), 0.68 (s, 3H).

Example 404: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methyl-N-((1r,4R)-4-(N-methylacetamido)cyclohexyl)pentanamide

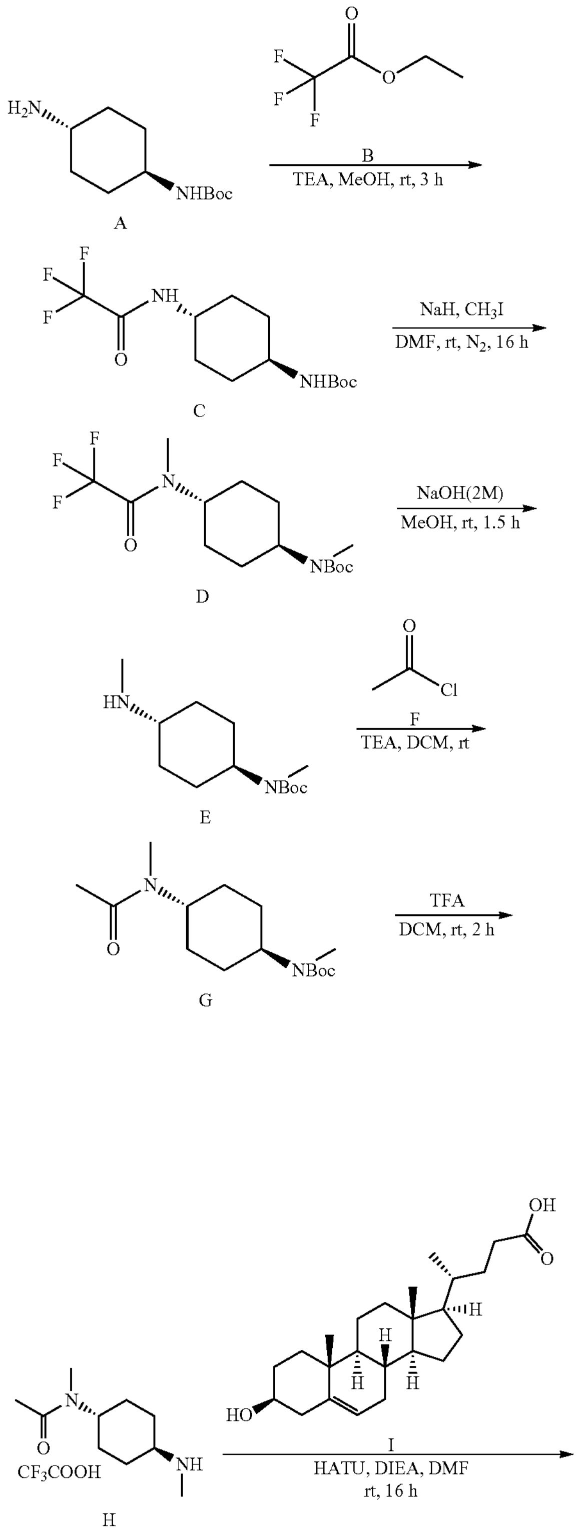

-continued

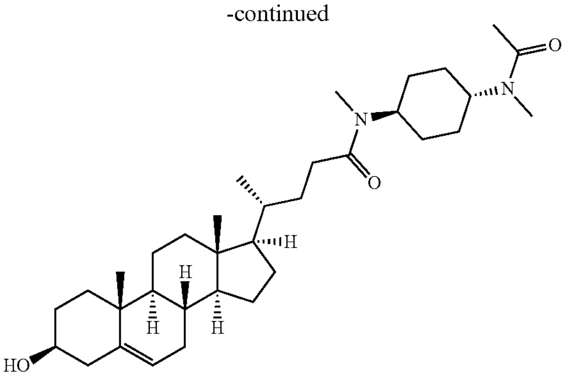

A solution of compound A (700 mg, 3.27 mmol) in methanol (10 mL) was cooled to 0° C., and compound B (2.32 g, 16.3 mmol), triethylamine (2 mL) was added. The reaction was stirred at room temperature for 3 h. The reaction concentrated under reduced pressure. The crude product was purified by silica gel chromatography to afford compound C (800 mg, 78.9%) as a yellow oil. A solution of compound C (800 mg, 2.58 mmol) in dry DMF (8 mL) was cooled to 0° C. and NaH (296 mg, 7.40 mmol, 60% dispersion in mineral oil) was added. The reaction was stirred for 20 minutes, followed by the addition of $CH_3I$ (805 mg, 5.67 mmol) then stirred at room temperature under $N_2$ for 16 h. The reaction was quenched with ice cold water (5 mL), citric acid solution (10 mL, 1 N in water) and extracted with EtOAc (20 mL). The organic layer was washed with brine, dried over sodium sulfate and concentrated to afford compound D (800 mg, 91.5%) as a yellow oil.

To the solution of compound D (700 mg, 2.07 mmol) in methanol (8 mL), NaOH (4 mL, 2N in water) was added. The reaction was stirred at room temperature for 1.5 h. The reaction concentrated. Citric acid solution (10 mL, 1 N in water) was added to the residue. The reaction was extracted with DCM/MeOH=9/1 (20 mL). The aqueous phase was basified with NaOH (2N in water) and extracted with DCM/MeOH=9/1 (20 mL). The organic layer was dried over sodium sulfate and concentrated to afford compound E (400 mg, 80%) as a yellow oil. To a solution of compound E (150 mg, 619 μmol) in DCM (2 mL) was added triethylamine (185 mg, 1.24 mmol). The reaction was cooled to 0° C. and added compound F (58.3 mg, 743 μmol). After stirring at room temperature under $N_2$ for 2 h, the reaction was extracted with EtOAc (10 mL) and water (5 mL). The organic layer was dried over sodium sulfate and concentrated to afford compound G (140 mg, 79.5%) as a yellow oil. To a solution of compound G (120 mg, 422 μmol) in DCM (1 mL) was added TFA (0.2 mL). The reaction was stirred at room temperature for 2 h. The reaction concentrated under reduced pressure to afford compound H (124.8 mg) as the TFA salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (100 mg, 404 μmol) and N-methyl-N-((1r,4r)-4-(methylamino)cyclohexyl)acetamide 2,2,2-trifluoroacetate (124.8 mg, 420 μmol) was reacted according to the method of Example 536 to afford the title compound 404 (70 mg, 25%) as a white solid. LCMS: $[M+1]^+$=541.30. $^1H$ NMR (400 MHz, Chloroform-d) δ 5.35 (d, J=4.4 Hz, 1H), 4.46 (bs, 1H), 3.57-3.48 (m, 1H), 2.86 (s, 3H), 2.85 (s, 3H), 2.44-2.11 (m, 12H), 2.05-1.80 (m, 7H), 1.79-1.03 (m, 26H), 1.01 (s, 3H), 0.97 (d, J=6.4 Hz, 3H), 0.93-0.85 (m, 1H), 0.69 (s, 3H).

Example 405: (1S,4s)-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methylpentanamido)-N,N-dimethylcyclohexane-1-carboxamide

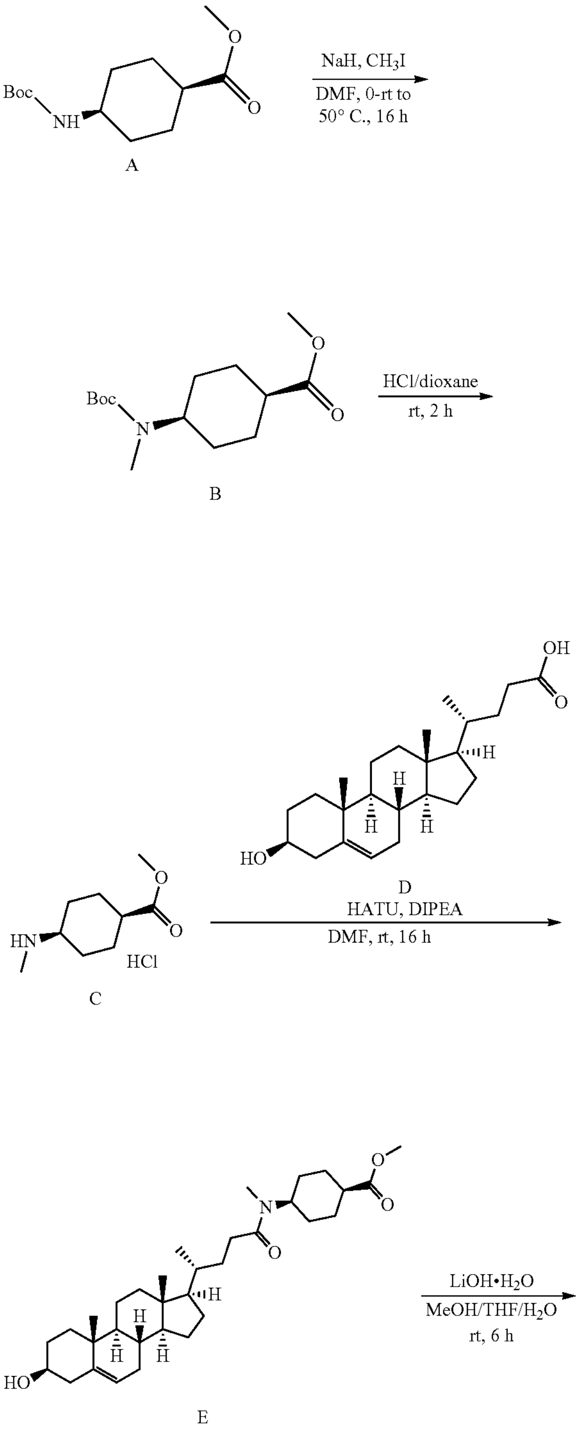

-continued

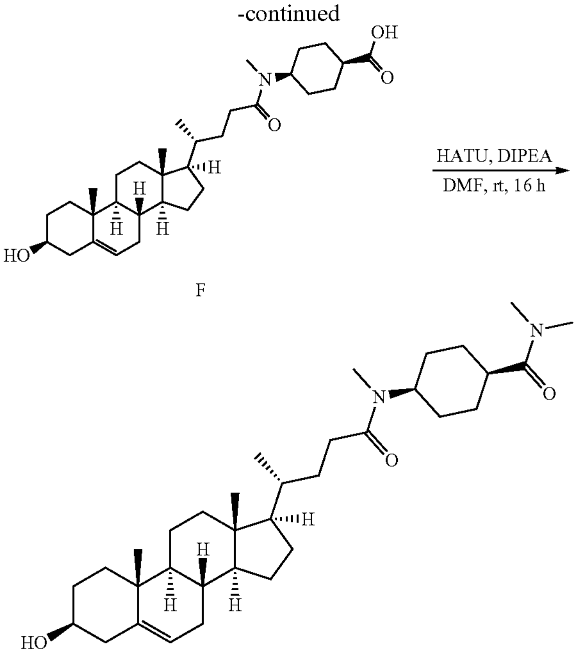

To a 0° C. solution of NaH (268 mg, 6.7 mmol, 60% dispersion in mineral oil) in DMF (20 mL) was added compound A (1.0 g, 3.89 mmol) and the reaction was stirred for 1 h. $CH_3I$ (1.65 g, 11.7 mmol) was added and heated to 50° C.; for 16 hours under nitrogen. The reaction was diluted with water and extracted with ethyl acetate. The organic layer was concentrated. The crude product was purified by silica gel chromatography to give compound B (1.0 g, 95%) as a yellow oil. To a solution of compound B (1.0 g, 3.68 mmol) in 1,4-dioxane (10 mL) was added 4N HCl in 1,4-dioxane (2.5 mL, 10 mmol). After stirring at room temperature for 2 hours, the reaction concentrated to give compound C (650 mg) as the HCl salt. To a solution of compound D (656 mg, 1.44 mmol) in DMF (12.9 mL, 166 mmol) was added compound C (300 mg, 1.44 mmol), HATU (824 mg, 3.5 mmol), DIPEA (1.13 g, 8.76 mmol) and stirred at room temperature for 16 hours. The reaction was diluted with water and extracted with ethyl acetate. The organic layer was concentrated. The crude product was purified by silica gel chromatography to afford compound E (515 mg, 56%) as a yellow oil. To a solution of compound E (515 mg, 976 μmol) in methanol (2 mL), THE (2 mL) and water (2 mL) was added LiOH (117 mg, 1.95 mmol) and stirred at room temperature for 6 hours. The reaction was adjusted pH to 1-2 with HCl 1N and extracted with DCM. The organic layer was concentrated to afford compound F (500 mg, 99%).

To a solution of compound F (500 mg, 0.97 mmol) in DMF (20 mL) was added dimethylamine (52.7 mg, 1.17 mmol), HATU (891 mg, 2.34 mmol), DIPEA (754 mg, 5.85 mmol) and stirred at room temperature for 16 hours. The reaction was diluted with water and extracted with ethyl acetate. The organic layer was concentrated. The crude product was purified by prep-HPLC to afford the title compound 405 (35.9 mg, 5.8%) as a white solid. LCMS: $[M+1]^+$=541.30. $^1$H NMR (400 MHz, Chloroform-d) δ 5.35 (d, J=5.2 Hz, 1H), 3.58-3.47 (m, 1H), 3.04-2.96 (m, 7H), 2.94 (s, 3H), 2.90-2.55 (m, 4H), 2.34-2.19 (m, 3H), 2.00-1.03 (m, 25H), 1.00 (d, J=5.6 Hz, 6H), 0.98-0.80 (m, 2H), 0.69 (s, 3H).

Example 406: (1R,4r)-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methylpentanamido)-N,N-dimethylcyclohexane-1-carboxamide

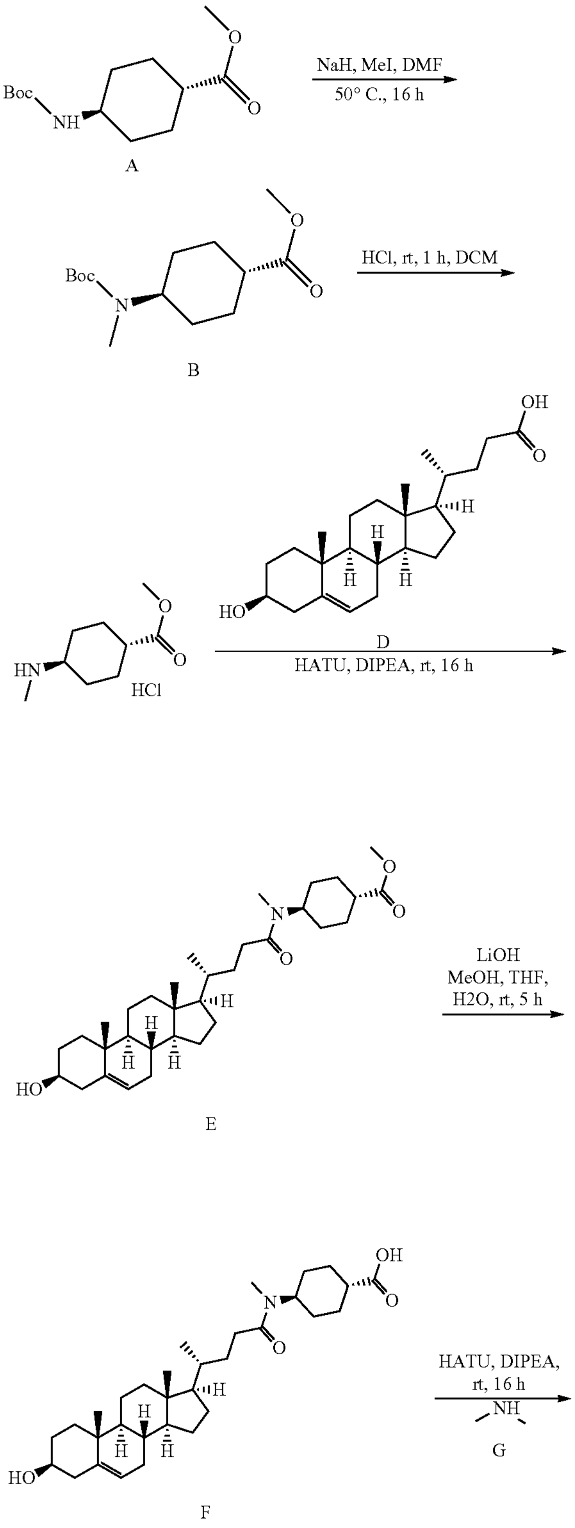

-continued

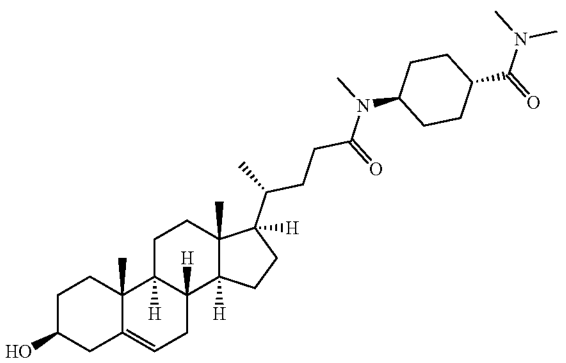

To a 0° C. solution of compound A (500 mg, 1.94 mmol) in DMF (5 mL) was added NaH (89.3 mg, 2.23 mmol, 60% dispersion in mineral oil) and stirred for 0.5 h. MeI (1.1 g, 7.77 mmol) was added and warmed to 50° C. for 16 hours. The reaction was diluted with water and extracted with ethyl acetate. The organic layer was concentrated. The crude product was purified by silica gel chromatograph to afford compound B (450 mg, 85.3%) as a white solid. To a solution of compound B (450 mg, 1.66 mmol) in DCM (4 mL) was added HCl (3 mL, 12 mmol, 4 M in 1,4-dioxane). The reaction was stirred at room temperature for 1 hour. The reaction concentrated to afford compound C (320 mg, 1.54 mmol) as the HCl salt. To a solution of compound C (240 mg, 1.17 mmol) in DMF (5 mL) was added compound D (394 mg, 1.05 mmol), DIPEA (748 mg, 7.01 mmol) and HATU (732 mg, 2.34 mmol). The reaction was stirred at room temperature for 16 hours. The reaction was diluted with water and extracted with ethyl acetate. The organic layer was concentrated. The crude product was purified by silica gel chromatography to afford compound E (250 mg, 40.56%) as a white solid. To a solution of compound E (150 mg, 284 μmol) in methanol (1 mL), water (1 mL) and THF (1 mL) was added LiOH (20.4 mg, 853 μmol). The solution was stirred at room temperature for 5 hours. The reaction was diluted with $H_2O$ (10 mL) and extracted with ethyl acetate (10 mL*3). The combined organic phase was washed with brine, dried over sodium sulfate, concentrated under vacuum to afford compound F (130 mg, 89%) as a white solid.

To a solution of compound F (130 mg, 253 μmol) in DMF (3 mL) was added compound G (0.28 mL, 0.56 mmol, 2M in THF), DIPEA (196, 1.52 mmol), HATU (190 mg, 506 mmol) and the reaction stirred at room temperature for 16 hours. The reaction was diluted with $H_2O$ and extracted with ethyl acetate. The organic layer was concentrated under reduced pressure. The crude product was purified by silica gel chromatography to afford the title compound 406 (55 mg, 40%) as a white solid. LCMS: $[M+1]^+$=541.30. $^1H$ NMR (400 MHz, Chloroform-d) δ 5.34 (s, 1H), 4.51-3.47 (m, 2H), 3.11-2.75 (m, 9H), 2.46-2.16 (m, 5H), 2.04-1.68 (m, 12H), 1.54-1.22 (m, 12H), 1.19-1.04 (s, 3H), 1.00 (m, 3H), 0.9-0.82 (m, 5H), 0.68 (s, 3H).

Example 407: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-N-(1-acetylpiperidin-4-yl)-N-methylpentanamide

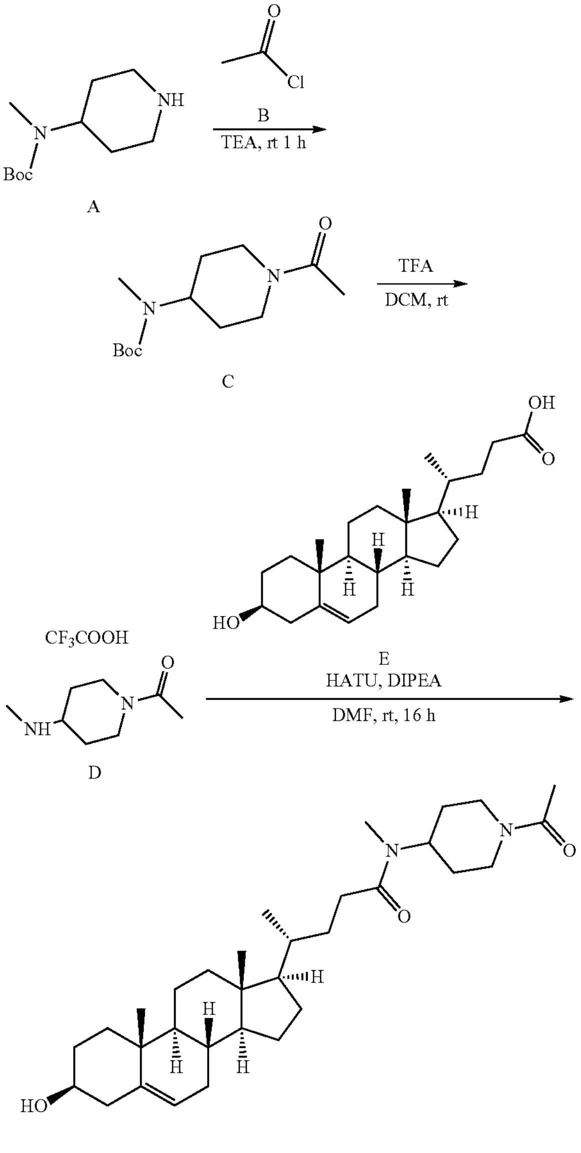

To a 0° C. solution of compound A (100 mg, 467 μmol) in dichloromethane (4 mL) was added TEA (142 mg, 1.4 mmol), compound B (44 mg, 560 μmol) and the reaction was stirred for 1 hour. Upon completion, the reaction was quenched with water (30 mL) and extracted with ethyl acetate (10 mL*3). The combined organic layers were washed with brine, dried over sodium sulfate, filtered, and concentrated under reduced pressure. The crude product was purified by column chromatography on silica gel to yield the title compound C (120 mg, 89%) as a white solid. To a solution of compound C (120 mg, 507 μmol) in DCM (6 mL) was added trifluoroacetic acid (2 mL) at room temperature and the reaction was stirred for 2 h. The reaction concentrated under reduced pressure to afford compound D as the TFA salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (134 mg, 358 μmo) and 1-(4-(methylamino)piperidin-1-yl) ethan-1-one 2,2,2-trifluoroacetate (70 mg, 448 μmol), to afford the title compound 407 (70 mg, 30%) as a white solid. LCMS: $[M+1]^+$=513.30. $^1H$ NMR (400 MHz, Chloroform-d) δ 5.35 (m, 1H), 4.74 (m, 2H), 3.86 (m, 1H), 3.52 (m, 1H), 3.15 (m, 1H), 2.80 (m, 3H), 2.59 (m, 1H), 2.38-2.18 (m, 4H), 2.11 (m, 3H), 1.99 (m, 2H), 1.91-1.77 (m, 4H), 1.68 (m, 3H), 1.47 (m, 7H), 1.32 (m, 3H), 1.23-1.03 (m, 5H), 1.01 (s, 3H), 0.95 (m, 4H), 0.89 (m, 1H), 0.69 (s, 3H).

Example 408: 1-acetyl-N—((R)-3-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)butyl)-N-methylpiperidine-4-carboxamide

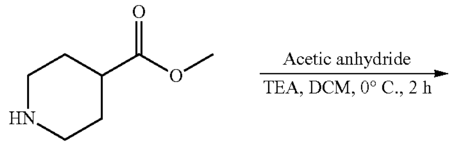

A

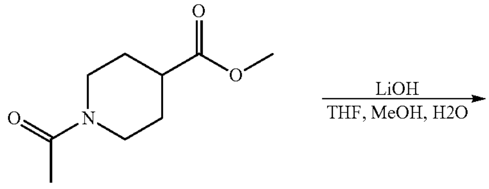

B

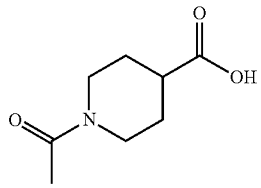

C

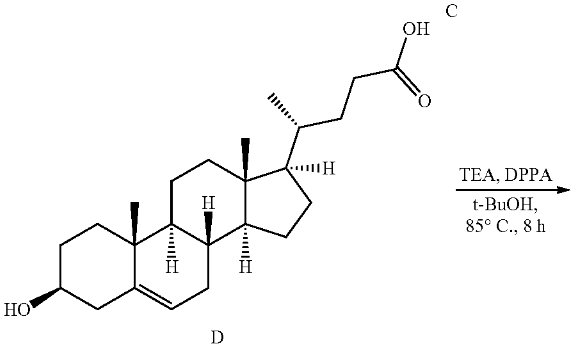

D

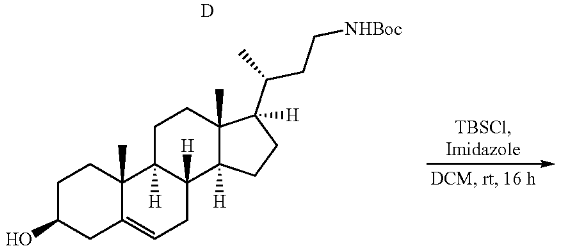

E

-continued

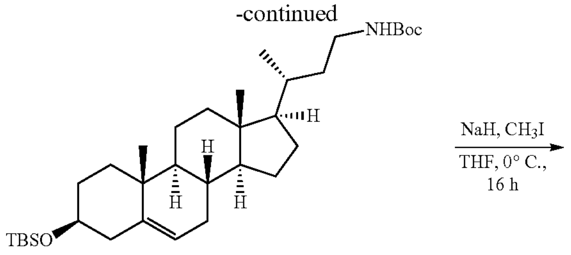

F

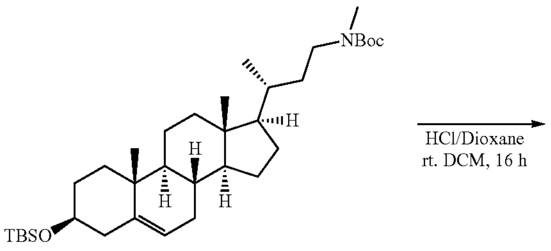

G

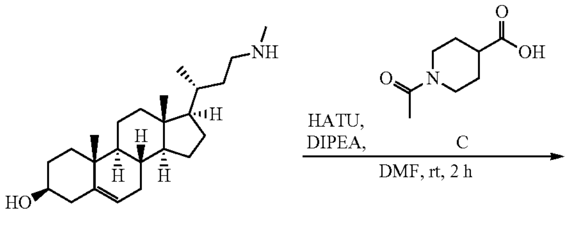

H

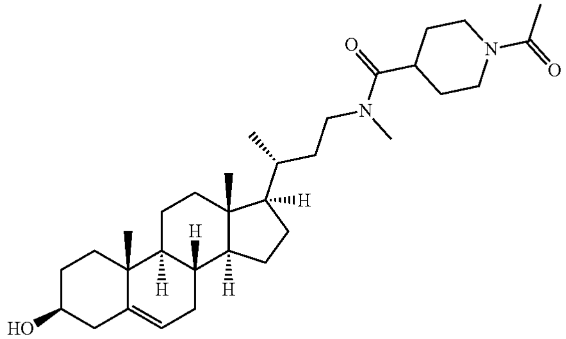

To a 0° C. solution of compound A (1.0 g, 6.98 mmol) in DCM (10 mL) was added TEA (2.91 mL, 21 mmol) and acetic anhydride (984 μL, 10.5 mmol) at 0° C. The reaction was stirred at 0° C. for 2 hours. Upon completion, the solution was quenched with water and extracted with DCM. The organic layer was dried over sodium sulfate and concentrated under reduced pressure. The crude product was purified by silica gel chromatography to afford compound B (1.2 g, 92.8%) as a white solid. To a solution of compound B (600 mg, 3.24 mmol) in methanol (1 mL), THE (1 mL) and water (1 mL) was added LiOH (233 mg, 9.72 mmol) at room temperature. The reaction was stirred for 16 hours. Upon completion, the solution was quenched with water and adjusted to pH=2 with 1N HCl and concentrated to afford crude compound C (500 mg, 90.2%).

To a solution of compound D (5.0 g, 12.9 mmol) in t-BuOH (50 mL) was added DPPA (3.54 mg, 12.9 mmol) and TEA (1.8 mL, 12.9 mmol). The reaction was stirred at 85° C. for 8 hours under $N_2$. Upon completion, the solution concentrated under reduced pressure. The crude product was purified by silica gel chromatography to afford the compound E (2.7 g, 46.1%) as a white solid. To a 0° C. solution of compound E (1.5 g, 3.37 mmol) in DCM (15 mL) was added imidazole (458 mg, 6.73 mmol), TBSCl (761 mg, 5.05 mmol) and stirred for 16 hours. The solution was quenched with water and extracted with DCM. The organic layer was dried over sodium sulfate and concentrated under reduced pressure. The crude product was purified by column chromatography on silica gel to afford compound F (1.2 g, 63.7%) as a white solid.

To a 0° C. solution of compound F (800 mg, 1.43 mmol) in DMF (40 mL) was added NaH (286 mg, 7.15 mmol, 60% dispersion in mineral oil) and $CH_3I$ (608 mg, 4.29 mmol) and the reaction was stirred for 16 hours. Upon completion, the solution was quenched with water and extracted with DCM. The organic layer was dried over sodium sulfate and concentrated under reduced pressure. The crude product was purified by column chromatography on silica gel to afford compound G (500 mg, 61.0%) as a white solid. To a solution of compound G (300 mg, 523 μmol) in DCM (12 mL) was added HCl (1.31 mL, 5.23 mmol, 4M in 1,4-dioxane) and a reaction was stirred at room temperature for 16 hours. Upon completion, the solution concentrated to afford crude compound H (188 mg) as the HCl salt.

To a solution of compound H (180 mg, 454 μmol) in DMF (10 mL) was added compound C (129 mg, 751 μmol), HATU (236 mg, 1 mmol) and DIPEA (872 μL, 5.01 mmol). The reaction was stirred at room temperature for 2 hours. Upon completion, the solution was quenched with water and extracted with ethyl acetate. The organic layer was dried over sodium sulfate and concentrated under reduced pressure. The crude product was purified by column chromatography on silica gel to yield the title compound 408 (84.4 mg, 32.9%) as a white solid. LCMS: $[M+1]^+$=513.30. $^1H$ NMR (400 MHz, Chloroform-d) δ 5.35 (s, 1H), 4.68-4.52 (m, 1H), 3.89 (d, J=13.2 Hz, 1H), 3.56-3.46 (m, 1H), 3.39-3.23 (m, 2H), 3.16-2.89 (m, 4H), 2.74-2.63 (m, 2H), 2.34-2.20 (m, 2H), 2.09 (s, 3H), 2.03-1.68 (m, 10H), 1.53-1.07 (m, 13H), 1.05-0.96 (m, 7H), 0.68 (d, J=10.4 Hz, 3H).

Example 409: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-N-methyl-N-[2-pyridin-2-yl)ethyl]pentanamide

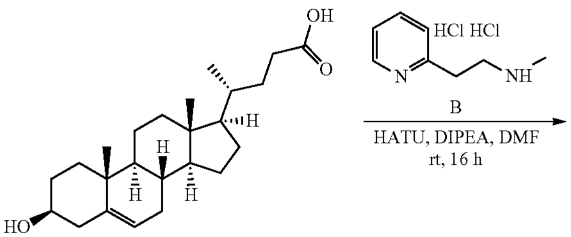

A

-continued

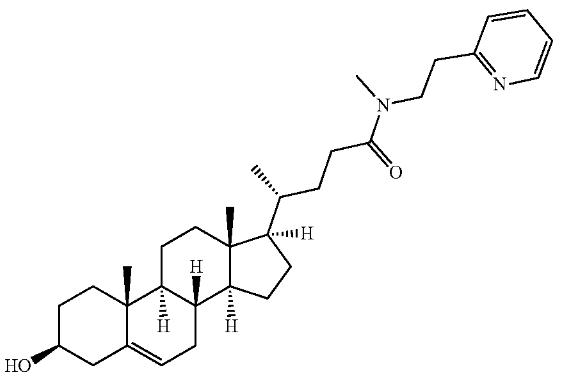

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (200 mg, 534 μmol) and N-methyl-2-(pyridin-2-yl)ethan-1-amine dihydrochloride (112 mg, 534 μmol) was reacted according to the method of Example 536 to afford the title compound 409 (136 mg, 51.7%) as a white solid. LCMS: $[M+1]^+$=493.30. $^1H$ NMR (400 MHz, $CDCl_3$) δ 8.59-8.49 (m, 1H), 7.70-7.58 (m, 1H), 7.29-7.06 (m, 2H), 5.35 (d, J=5.2 Hz, 1H), 3.76-3.70 (m, 2H), 3.52 (dt, J=11.2, 6.2 Hz, 1H), 3.04 (dt, J=14.0, 7.2 Hz, 2H), 2.94 (d, J=7.2 Hz, 3H), 2.36-1.79 (m, 10H), 1.56-1.48 (m, 4H), 1.47-1.38 (m, 3H), 1.35-1.25 (m, 3H), 1.23-1.11 (m, 2H), 1.07 (td, J=10.4, 9.6, 4.4 Hz, 3H), 1.00 (s, 3H), 0.93 (d, J=6.4 Hz, 2H), 0.87 (d, J=6.4 Hz, 2H), 0.67 (d, J=5.6 Hz, 3H).

Example 410: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-{δ-acetyl-5-oxa-2,8-diazaspiro[3.4]octan-2-yl}pentan-1-one

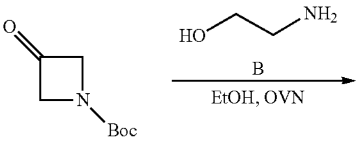

A

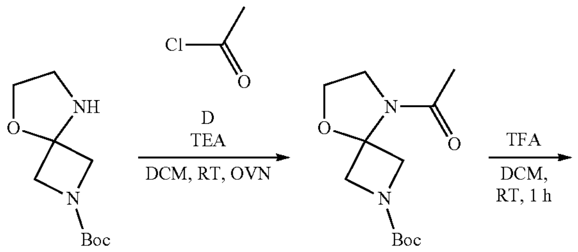

C

E

-continued

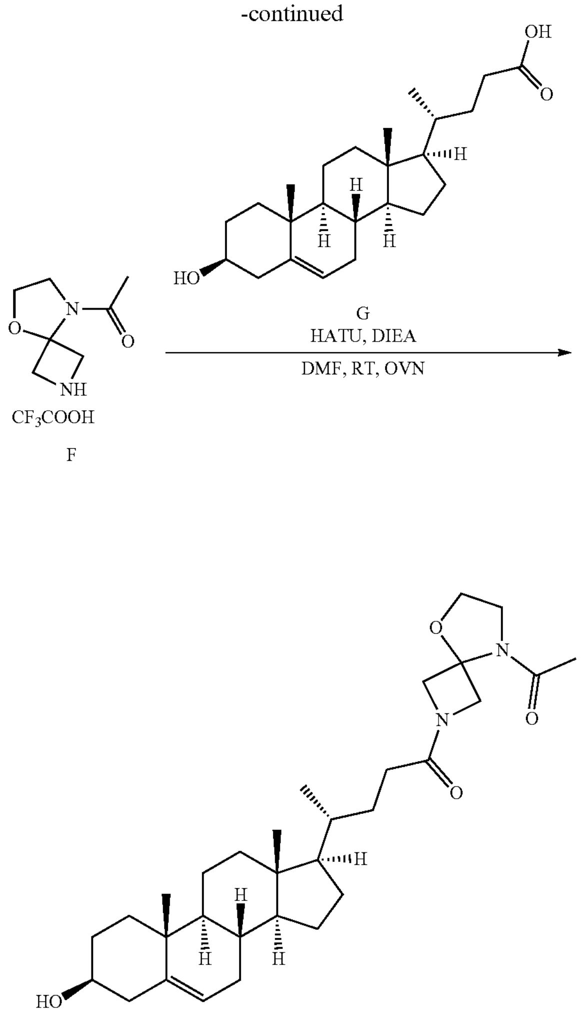

A solution of compound A (1 g, 11.8 mmol) and compound B (1 g, 1.4 eq., 16.4 mmol) in ethanol (10 mL) was stirred for 16 hours at room temperature. The solvent was removed under vacuum. The residue was diluted with water (40 mL), extracted with EtOAc (40 mL). The organic layer was washed by brine (40 mL), dried over sodium sulfate, filtered, and concentrated. The reaction was purified by column chromatography on silica gel to afford compound C (1 g, 39%) as a white solid. To a solution of compound C (200 mg, 933 μmol) and TEA (189 mg, 1.87 mmol) in DCM (5 mL) at 0° C. was added compound D (73.3 mg, 933 μmol). The reaction was warmed to room temperature and stirred for 16 hours. The reaction was diluted with saturated aqueous $NH_4Cl$ (30 mL) and extracted with EtOAc (10 mL*2). The combined organic layer was washed with water (20 mL), brine (20 mL), dried over sodium sulfate and concentrated under reduced pressure. The residue was purified by silica gel chromatography to afford compound E (100 mg, 41%) as a white solid. To a solution of compound E (200 mg, 933 μmol) in DCM (6 mL) was added TFA (2 mL) at room temperature and the reaction was stirred for 2 h. The reaction was concentrated under reduced pressure to afford compound F as the TFA salt (170 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (192 mg, 512 μmol) and 1-(5-oxa-2,8-diazaspiro[3.4]octan-8-yl)ethan-1-one 2,2,2-trifluoroacetate (170 mg, 746 μmol) were reacted according to Example 536 to give the title compound 410 (50 mg, 15%) as a white solid. LCMS: $[M+1]^+$=513.40. $^1$H NMR (400 MHz, Chloroform-d) δ 5.34 (dd, J=4.8, 2.4 hz, 1H), 4.84 (dd, J=8.8, 1.4 hz, 1H), 4.59 (dd, J=10.4, 1.6 hz, 1H), 4.04 (t, J=6.4 hz, 3H), 3.99-3.93 (m, 1H), 3.65-3.58 (m, 2H), 3.57-3.47 (m, 1H), 2.33-2.16 (m, 3H), 2.13 (s, 3H), 1.99-2.98 (m, 3H), 1.89-1.77 (m, 4H), 1.62-1.39 (m, 8H), 1.38-1.27 (m, 3H), 1.18-1.03 (m, 4H), 1.00-0.98 (m, 4H), 0.96-0.83 (m, 5H), 0.67 (d, J=1.2 hz, 3H).

Example 411: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(3-methyl-1,2,4-oxadiazole-5-carbonyl)piperazin-1-yl)pentan-1-one

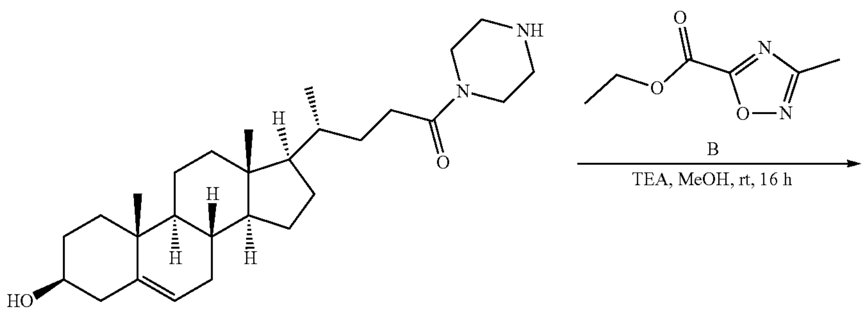

A

-continued

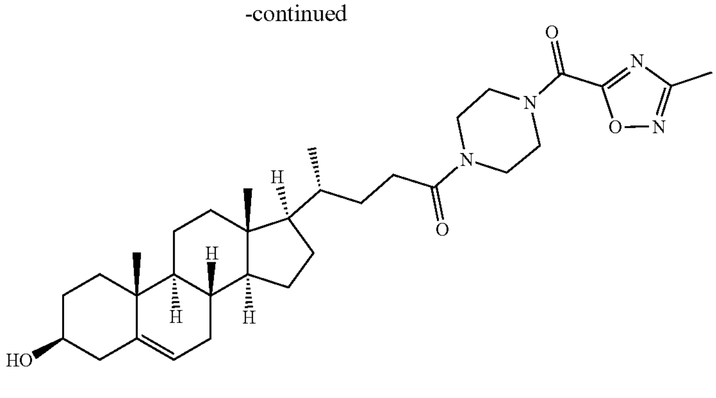

To a solution of compound A (129 mg, 291 μmol) in methanol (2 mL) was added compound B (50 mg, 320 μmol), TEA (405 μL, 2.91 mmol) and the reaction was stirred for 16 hours. Upon completion, the solution was quenched with water and extracted with dichloromethane. The organic layer was dried over sodium sulfate and concentrated under reduced pressure. The crude product was purified by column chromatography on silica to yield the title compound 411 (10.0 mg, 6.2%) as a white solid. $^1$H NMR (400 MHz, Chloroform-d) δ 5.35 (d, J=5.2 Hz, 1H), 3.90-3.46 (m, 9H), 2.49 (s, 3H), 2.44-2.19 (m, 4H), 2.04-1.78 (m, 6H), 1.51-1.23 (m, 10H), 1.18-0.84 (m, 12H), 0.69 (s, 3H).

Example 412: 1-[(4R)-4-[(1R,3aS,3bS,7S,9aR,9bS,11aR) dimethyl-1H,2H,3H,3aH,3bH,4H,6H,7H,8H,9H,9aH,9bH,10H,1 cyclopenta[a]phenanthren-1-yl]pentanoyl]-N-methylpiperidine-4-sulfonamide

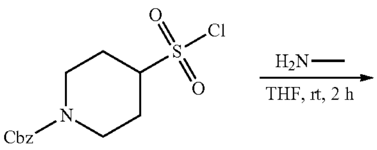

A

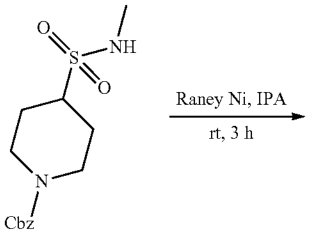

B

-continued

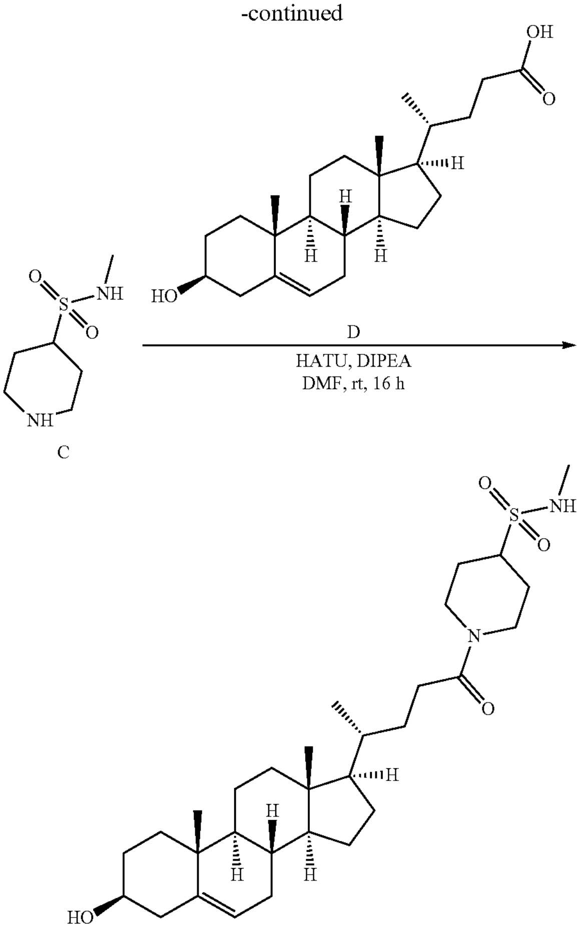

To a solution of compound A (1.0 g, 3.15 mmol) in THF (30 mL) was added methylamine (15.7 mL, 31.5 mmol, 2M in THF) and stirred at room temperature for 2 h, the solvent was concentrated under reduced pressure to give compound B (800 mg, 81.4%). To a solution of compound B (200 mg, 640 μmol) in iPrOH (10 mL) was added Raney Ni (20 mg). The reaction was stirred for 3 h at room temperature under 1 atm of $H_2$. The reaction was filtered through Celite and concentrated under vacuum to give crude compound C (77 mg, 67.5%).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (150 mg, 0.4 mmol) and N-methylpiperidine-4-sulfonamide (71.4 mg, 0.4 mmol) was reacted according to the method of Example 536 to afford the title compound 412 (84.0 mg, 39.2%) as a white solid. LCMS: $[M+1]^+$=535.25. $^1$H NMR (400 MHz, $CDCl_3$) δ 5.35 (d, J=5.2 Hz, 1H), 4.78 (d, J=13.2 Hz, 1H), 4.09-3.94 (m, 2H), 3.52 (dt, J=11.2, 6.4 Hz, 1H), 3.17-2.9 (m, 2H), 2.84 (d, J=4.8 Hz, 3H), 2.57 (t, J=12.8 Hz, 1H), 2.42-2.09 (m, 6H), 1.99 (tt, J=12.4, 3.2 Hz, 2H), 1.91-1.68 (m, 6H), 1.56-1.39 (m, 8H), 1.37-1.24 (m, 3H), 1.22-1.03 (m, 4H), 1.01 (s, 3H), 0.95 (d, J=6.4 Hz, 3H), 0.94-0.84 (m, 1H), 0.69 (s, 3H).

Example 413: 1—((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N,N-dimethylpiperidine-4-sulfonamide

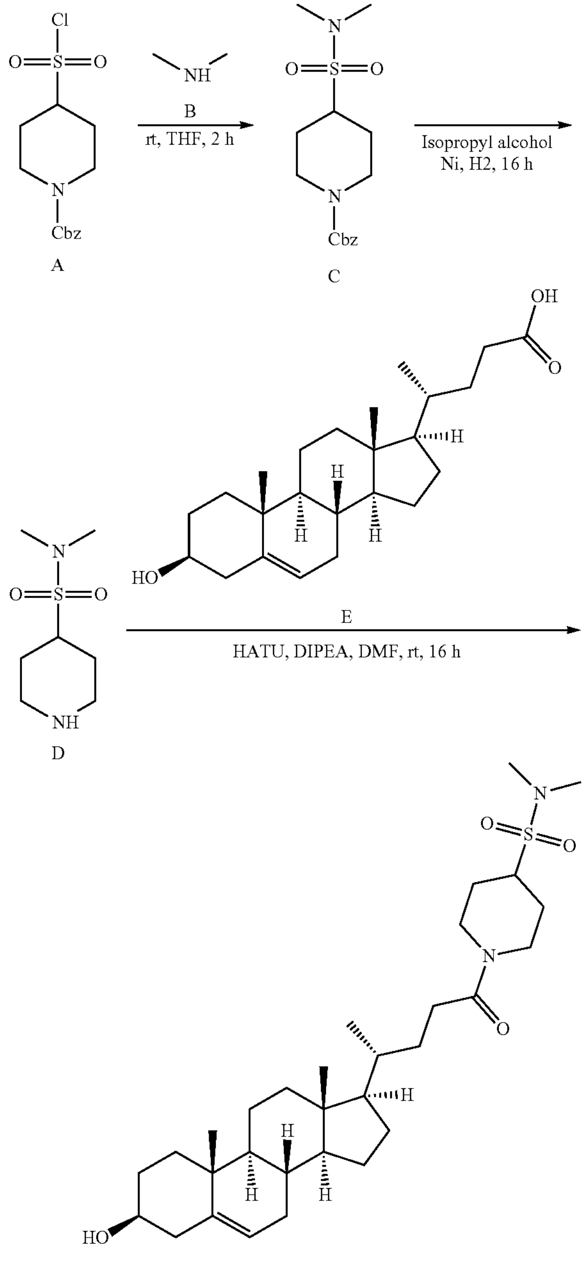

To a solution of compound A (1.0 g, 3.15 mmol) in THF (30 mL) was added compound B (1.42 g, 31.5 mmol). The reaction was stirred at room temperature for 2 hours. The reaction concentrated to afford the compound C (1.02 g, 100%) as oil. To a solution of compound C (300 mg, 919 μmol) in isopropyl alcohol (5 mL) was added Raney Ni (30 mg). The reaction was stirred at room temperature for 16 hours under 1 atm of hydrogen. The reaction was filtered and concentrated to afford compound D (90 mg, 50.9%) as oil.

N,N-dimethylpiperidine-4-sulfonamide (90 mg, 468 μmol) and (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (175 mg, 468 μmol) was reacted according to the method of Example 536 to afford the title compound 413 (93 mg, 36.2%) as a white solid. LCMS: $[M+1]^+$=549.25. $^1$H NMR (400 MHz, Chloroform-d) δ 5.35 (d, J=5.2 Hz, 1H), 4.74 (bs, 1H), 3.99 (bs, 1H), 3.57-3.46 (m, 1H), 3.23-2.97 (m, 2H), 2.93 (s, 6H), 2.55 (bs, 1H), 2.42-2.18 (m, 4H), 2.15-1.93 (m, 4H), 1.91-1.68 (m, 6H), 1.63 (s, 2H), 1.52-1.41 (m, 5H), 1.36-1.25 (m, 3H), 1.17-1.10 (m, 2H), 1.09-1.01 (m, 2H), 1.00 (s, 3H), 0.95 (d, J=6.0 Hz, 3H), 0.93-0.83 (m, 1H), 0.68 (s, 3H).

Example 414: N-(1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)methanesulfonamide

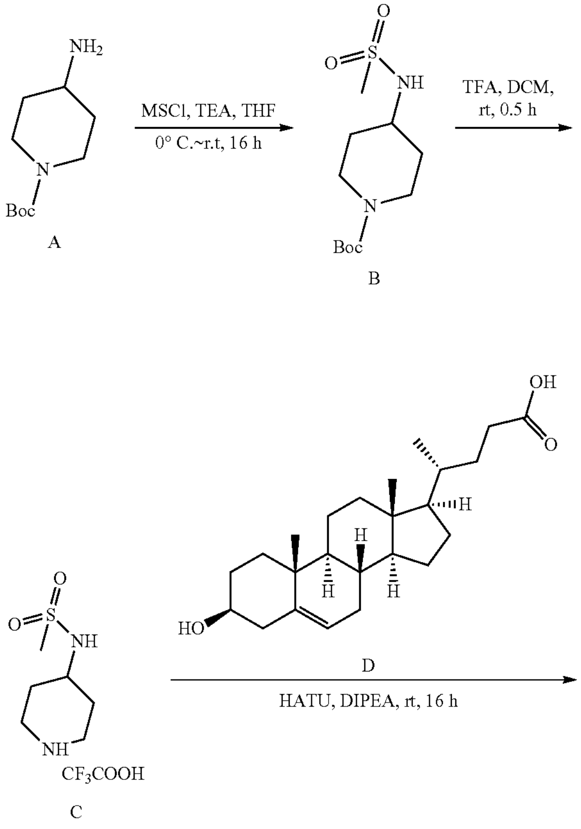

-continued

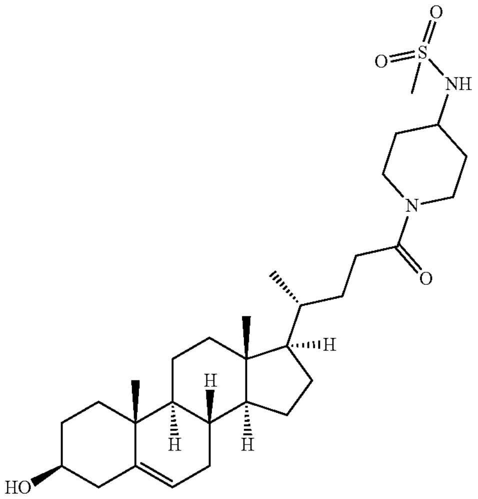

To a 0° C. solution of compound A (1.0 g, 4.99 mmol) in THF (15 mL) was added triethylamine (1.52 g, 15 mmol) and MsCl (858 mg, 7.49 mmol) under $N_2$. The reaction was stirred at room temperature for 16 hours. The reaction was diluted with saturated aqueous $NH_4Cl$ (30 mL) and extracted with EtOAc (20 mL*2). The combined organic layers were washed with brine (20 mL), dried over sodium sulfate, and concentrated under reduced pressure. The residue was purified by silica gel chromatography to afford compound B (1.1 g, 80%) as a yellow oil. To a solution of compound B (300 mg, 1.08 mmol) in DCM (3 mL) was added trifluoroacetic acid (3 mL) at room temperature and the reaction was stirred for 0.5 h. The reaction concentrated under reduced pressure to give compound C (212 mg) as the TFA salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (216 mg, 580 µmol) and N-(piperidin-4-yl)methanesulfonamide 2,2,2-trifluoroacetate (108 mg, 505 µmol) was reacted according to the method of Example 536 to afford the title compound 414 (110 mg, 20%) as a white solid. LCMS: $[M+1]^+$=535.20. $^1H$ NMR (400 MHz, DMSO-d6) δ 7.11 (d, J=7.2 Hz, 1H), 5.26-5.25 (m, 1H), 4.58 (d, J=4.4 Hz, 1H), 4.18 (d, J=13.6 Hz, 1H), 3.77 (d, J=13.6 Hz, 1H), 3.39-3.22 (m, 3H), 3.08 (t, J=12.4 Hz, 1H), 2.93 (s, 3H), 2.70 (t, J=12.4 Hz, 1H), 2.30-2.27 (m, 1H), 2.23-2.04 (m, 3H), 2.00-1.73 (m, 6H), 1.70-1.59 (m, 2H), 1.57-1.45 (m, 3H), 1.43-1.30 (m, 5H), 1.29-1.04 (m, 6H), 1.01-0.84 (m, 9H), 0.65 (s, 3H).

Example 415: N-{1-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]piperidin-4-yl}-N-methylmethanesulfonamide

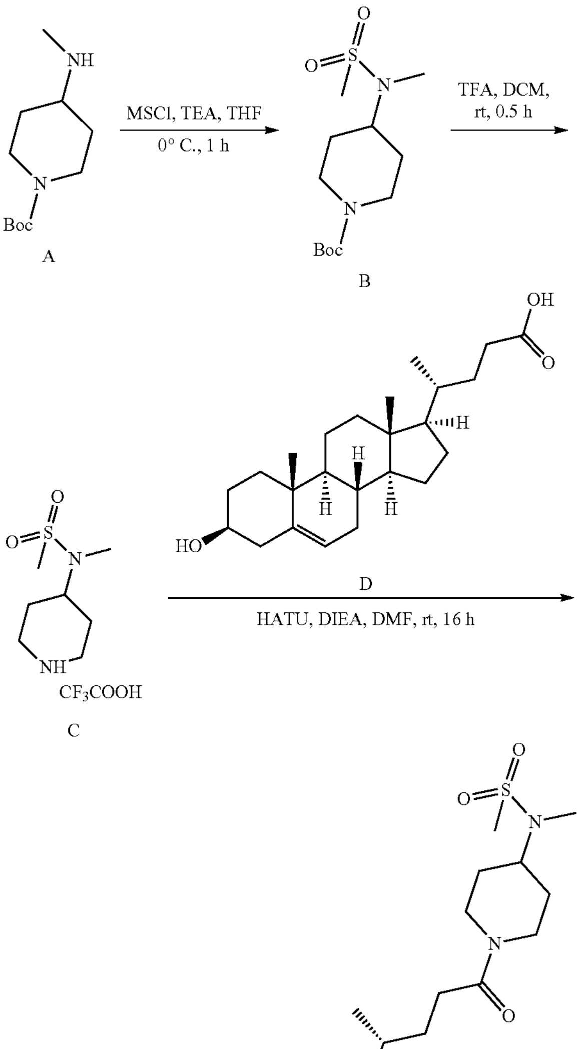

To a 0° C. solution of compound A (1 g, 4.67 mmol) in THE (5 mL) was added triethylamine (1.42 g, 14 mmol) and MsCl (802 mg, 7 mmol) under $N_2$. The reaction was stirred at room temperature for 1 hour. The reaction was quenched with water and extracted with ethyl acetate (30 mL*4). The combined organic layers were concentrated to give the crude compound B (1.2 g, 87%). To a solution of compound B (0.4 g, 1.37 mmol) in DCM (6 mL) was added trifluoroacetic acid (2 mL) at room temperature and the reaction was stirred for 2 h. The reaction was concentrated under reduced pressure to give compound C as the TFA salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (176 mg, 468 μmol) and N-methyl-N-(piperidin-4-yl)methanesulfonamide 2,2,2-trifluoroacetate (100 mg, 330 μmol) was reacted according to the method of Example 536 to afford the title compound 415 (164 mg, 299 μmol, 57%) as a white solid. LCMS: $[M+23]^+$=571.25. $^1$H NMR (400 MHz, Chloroform-d) δ 5.34 (d, J=5.2 Hz, 1H), 4.77 (d, J=13.4 Hz, 1H), 4.01-3.87 (m, 2H), 3.57-3.45 (m, 1H), 3.14-3.02 (m, 1H), 2.86 (s, 3H), 2.77 (s, 3H), 2.60-2.49 (m, 1H), 2.43-2.15 (m, 4H), 2.05-1.93 (m, 2H), 1.89-1.77 (m, 4H), 1.76-1.69 (m, 2H), 1.68-1.56 (m, 5H), 1.54-1.40 (m, 7H), 1.37-1.24 (m, 3H), 1.21-1.03 (m, 5H), 1.00 (s, 3H), 0.95 (d, J=6.8 Hz, 4H), 0.68 (s, 3H).

Example 416: N-(1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)-N-methylisonicotinamide

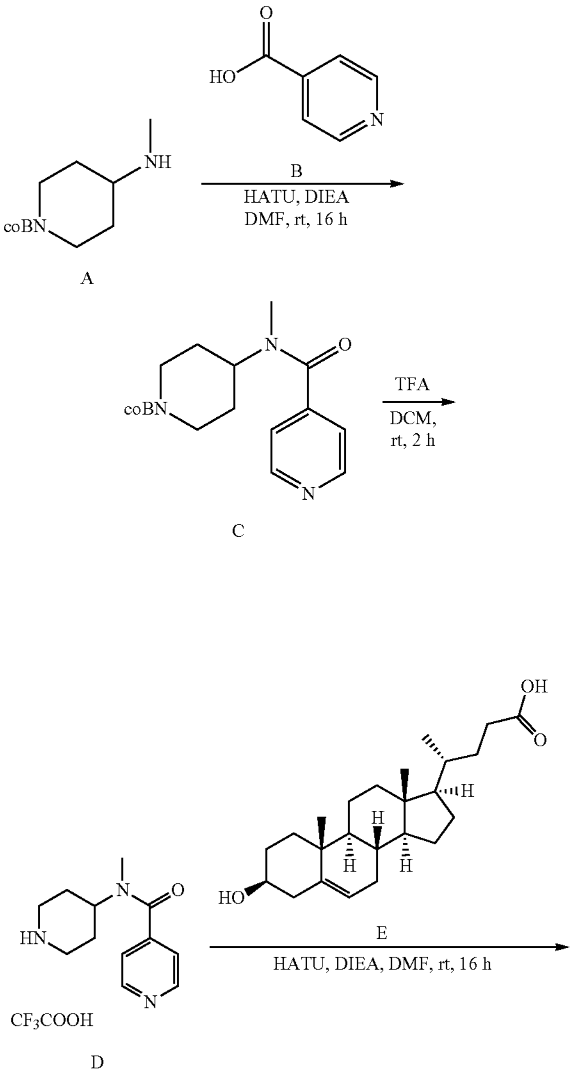

-continued

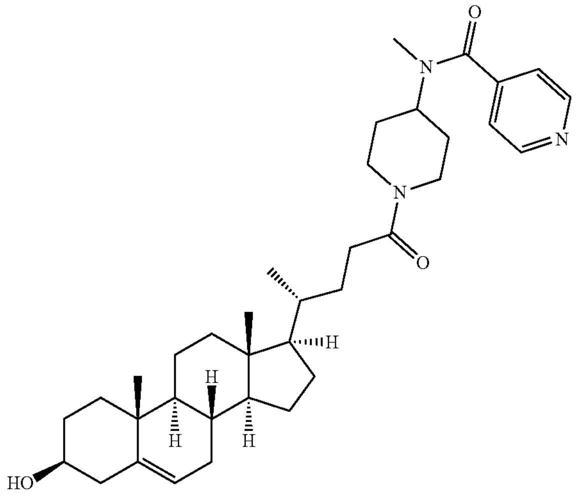

To a solution of compound A (200 mg, 933 μmol) in DMF (3 mL) was added compound B (115 mg, 933 μmol), DIPEA (603 mg, 4.67 mmol) and HATU (532 mg, 1.4 mmol). The reaction was stirred at room temperature for 16 h. The reaction was diluted with water and extracted with EtOAc. The organic layer was washed with brine, dried over sodium sulfate, and concentrated under reduced pressure. The residue was purified by silica gel chromatography to afford compound C (290 mg, 97%) as a yellow oil. To a solution of compound C (150 mg, 470 μmol) in DCM (2 mL) was added TFA (0.5 mL). The reaction was stirred at room temperature for 2 h. The reaction concentrated under reduced pressure to give compound D (99.5 mg) as the TFA salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (170 mg, 404 μmol) and N-methyl-N-(piperidin-4-yl)isonicotinamide (99.5 mg, 454 μmol) was reacted according to the method of Example 430 to afford the title compound 416 (62.0 mg, 23.7%) as a white solid. LCMS: $[M+1]^+$=576.30. $^1$H NMR (400 MHz, Chloroform-d) δ 8.82-8.69 (m, 2H), 7.50-7.37 (m, 2H), 5.39-5.32 (m, 1H), 4.92-4.62 (m, 2H), 4.05-3.83 (m, 1H), 3.52 (dt, J=11.2, 6.2 Hz, 1H), 3.20 (t, J=13.0 Hz, 1H), 2.98 (s, 1H), 2.78 (s, 3H), 2.65 (t, J=13.2 Hz, 1H), 2.45-2.18 (m, 5H), 2.03-1.77 (m, 8H), 1.72-1.41 (m, 10H), 1.30 (s, 3H), 1.20-1.01 (m, 5H), 1.00 (s, 3H), 0.98-0.84 (m, 5H), 0.68 (s, 3H).

Example 417: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(pyridin-4-yl)piperidin-1-yl]pentan-1-one

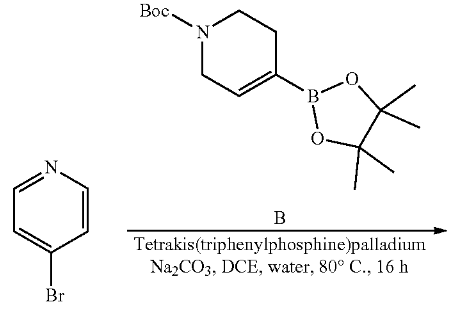

A

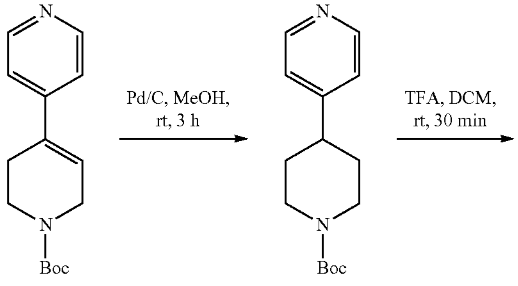

C D

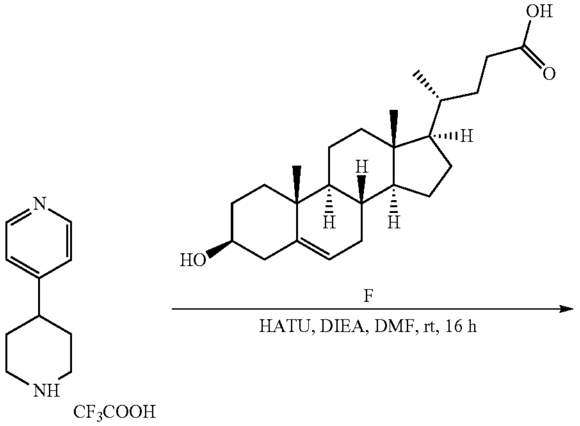

$CF_3COOH$

E

-continued

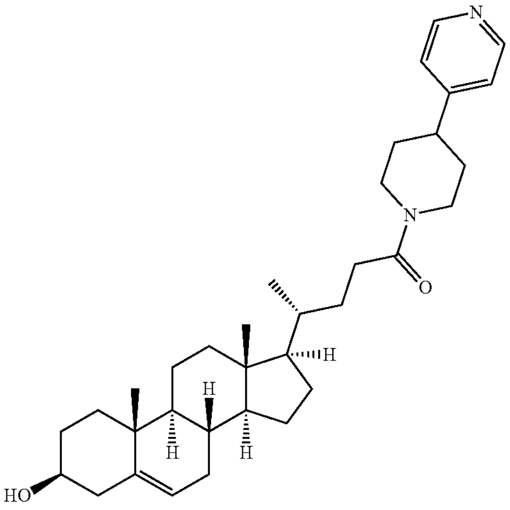

To a solution of compound A (200 mg, 1.27 mmol) in DCE (5 mL) was added (2 mol/L) sodium carbonate (1.89 mL), compound B (470 mg, 1.52 mmol) and $Pd(PPh_3)_4$ (43.9 mg, 38 μmol). The reaction was stirred at 80° C. for 16 hours. The reaction was cooled to room temperature and concentrated under reduced pressure. The residue was purified by silica gel chromatography to afford compound C (300 mg, 91%) as a white solid, To a solution of compound C (0.1 g, 384 μmol) in methanol (8.18 mL) was added 10% Pd/C (10 mg). The reaction was stirred at room temperature for 3 h under $H_2$ atmosphere. The reaction was filtered and concentrated to give the crude compound D (87 mg, 86%) as a white solid. To a solution of compound D (87 mg, 332 μmol) in DCM (6 mL) was added trifluoroacetic acid (2 mL) at room temperature and the reaction was stirred for 2 h. The reaction concentrated under reduced pressure to give compound E (54 mg) as the TFA salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (112 mg, 0.3 mmol) and 4-(piperidin-4-yl)pyridine 2,2,2-trifluoroacetate (54 mg, 196 μmol) was reacted according to the method of Example 536 to afford the title compound 417 (68.5 mg, 39%) as a white solid. LCMS: $[M+1]^+$=519.30. $^1H$ NMR (400 MHz, Chloroform-d) δ 8.53 (d, J=6.2 Hz, 2H), 7.17-7.09 (m, 2H), 5.35 (d, J=4.8 Hz, 1H), 4.81 (d, J=13.2 Hz, 1H), 4.00 (d, J=13.4 Hz, 1H), 3.52-3.45 (m, 1H), 3.21-3.06 (m, 1H), 2.81-2.69 (m, 1H), 2.67-2.58 (m, 1H), 2.48-2.35 (m, 1H), 2.33-2.18 (m, 3H), 2.09-1.74 (m, 12H), 1.49 (d, J=7.6 Hz, 9H), 1.25 (s, 4H), 1.21-1.03 (m, 4H), 1.00 (s, 3H), 0.97 (d, J=6.4 Hz, 3H), 0.94-0.84 (m, 1H), 0.69 (s, 3H).

Example 418: 1—((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl dimethylcarbamate

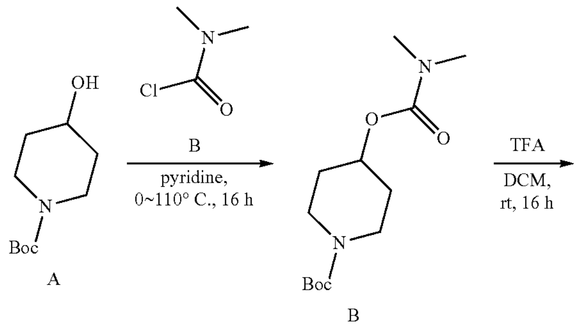

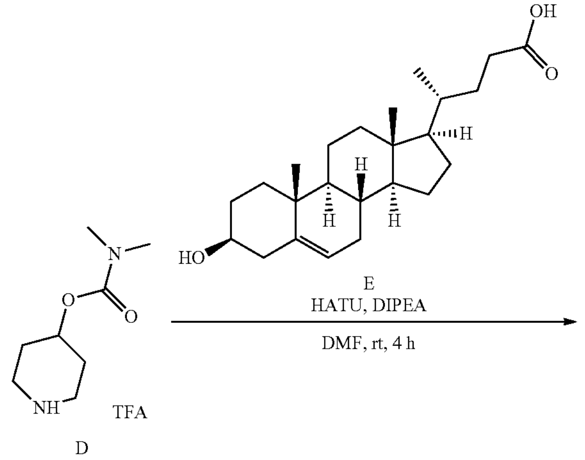

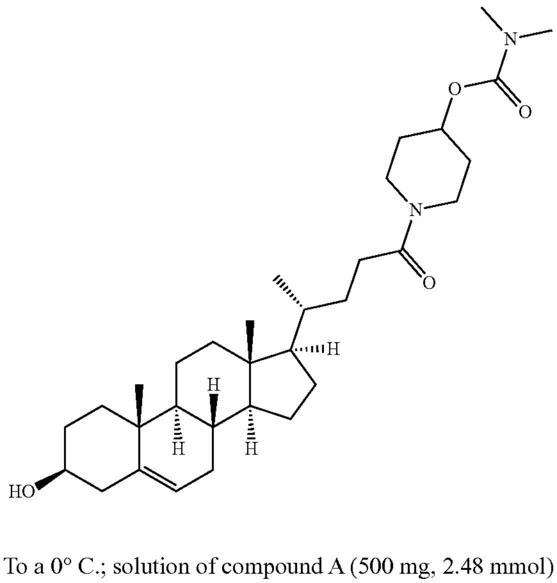

To a 0° C.; solution of compound A (500 mg, 2.48 mmol) in pyridine (10 mL) was added compound B (2.67 g, 24.8 mmol) and stirred at 110° C.; for 16 hours. The reaction was quenched with $NaHCO_3$ and extracted with ethyl acetate. The organic layer was concentrated under reduced pressure. The crude product was purified by silica gel chromatography to give compound C (230 mg, 34%) as a yellow oil. To a solution of compound C (230 mg, 845 μmol) in DCM (2 mL) was added TFA (289 mg, 2.53 mmol), the reaction was stirred at room temperature for 16 hours. The reaction concentrated to afford compound D (140 mg) as the TFA salt used in next step directly.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (304 mg, 813 μmol) and piperidin-4-yl dimethylcarbamate (140 mg, 490 μmol) was reacted according to the method of Example 536 to afford the title compound 418 (250 mg, 58%). LCMS: $[M+1]^+$=529.25 $^1H$ NMR (400 MHz, Chloroform-d) δ 5.37-5.33 (m, 1H), 4.93-4.84 (m, 1H), 3.91-3.33 (m, 5H), 2.91 (s, 6H), 2.44-2.18 (m, 4H), 2.04-1.88 (m, 3H), 1.88-1.81 (m, 3H), 1.80-1.59 (m, 9H), 1.53-1.03 (m, 12H), 1.00 (s, 3H), 0.95 (d, J=6.4 Hz, 3H), 0.68 (s, 3H).

Example 419: Methyl 4-((R)-4-((3S,8S,9S,10R,13R,14S,17R)-3-hydroxy-10,13-dimethyl-3-(trifluoromethyl)-2,3,4,7,8,9,10,11,12,13,14,15,16,17-tetradecahydro-1H-cyclopenta[a]phenanthren-17-yl)pentanoyl)piperazine-1-carboxylate

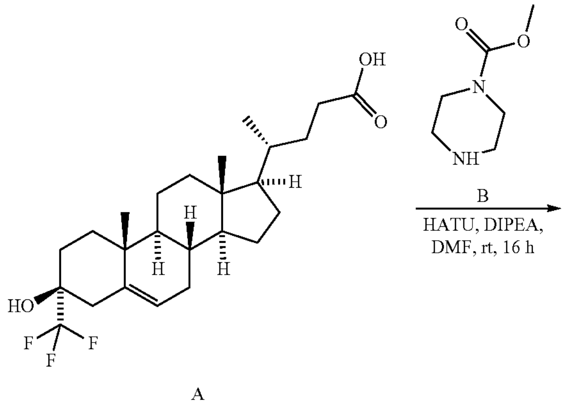

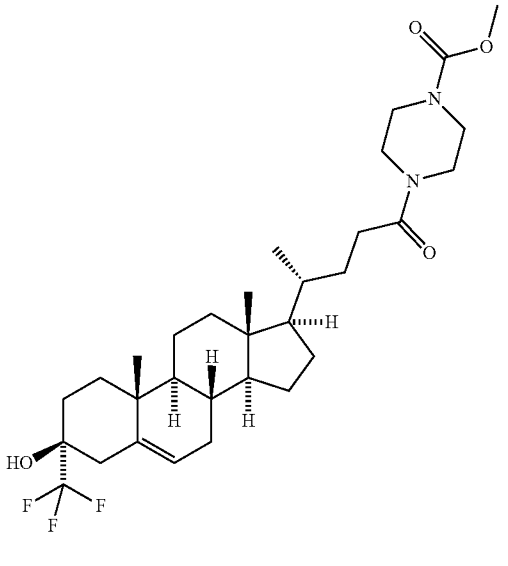

To a solution of compound A (150 mg, 339 μmol) in DMF (5 mL) was added compound B (48.9 mg, 339 μmol), HATU (159 mg, 678 μmol), DIPEA (219 mg, 1.69 mmol) and the reaction was stirred at room temperature for 16 hours. The reaction was diluted with water and extracted with ethyl acetate. The organic layer was concentrated under reduced pressure. The crude product was purified by silica gel chromatography to afford the title compound 419 (123 mg, 64%) as a white solid. LCMS: $[M+1]^+$=569.25. $^1H$ NMR (400 MHz, Chloroform-d) δ 5.39-5.35 (m, 1H), 3.73 (s, 3H), 3.59-3.42 (m, 8H), 2.49 (s, 2H), 2.46-2.34 (m, 1H), 2.31-2.22 (m, 1H), 2.10-1.09 (m, 21H), 1.06 (s, 3H), 1.03-1.00 (m, 1H), 0.96 (d, J=6.4 Hz, 3H), 0.69 (s, 3H). $^{19}F$ NMR (376 MHz, Chloroform-d) δ-78.59 (s).

Example 420: Methyl 4-[(4R)-4-[(1R,3aS,3bS,7S,9aR,9bS,11aR)-7-ethyl-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]piperazine-1-carboxylate

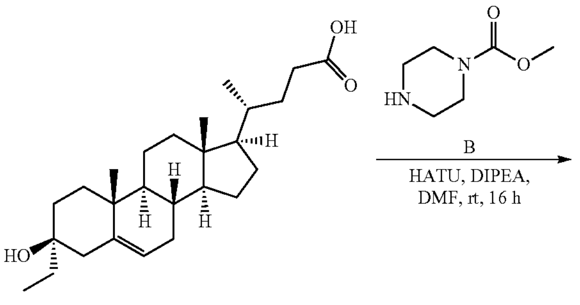

A

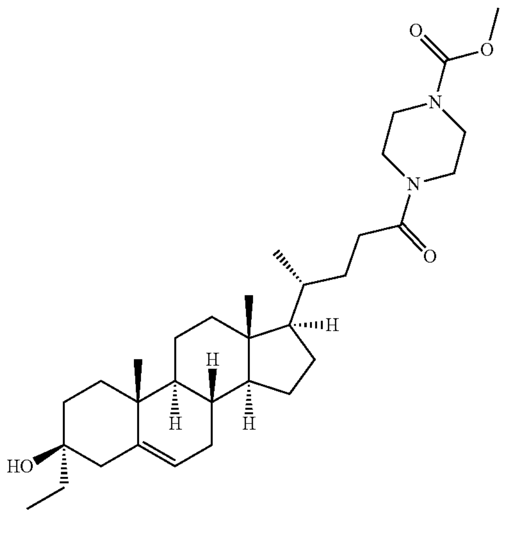

To a solution of compound A (150 mg, 373 μmol) in DMF (3 mL) was added DIPEA (144 mg, 1.12 mmol), compound B (53.7 mg, 373 μmol), HATU (283 mg, 745 μmol) and the reaction was stirred at room temperature for 16 h. The reaction was diluted with water and extracted with ethyl acetate. The organic layer was washed with water and brine, dried with sodium sulfate and concentrated under reduced pressure. The crude product was purified by silica gel chromatography to give the title compound 420 (27.6 mg, 14.0%) as a white solid. LCMS: 1.76, 529.25[M+H]. $^1H$ NMR (400 MHz, $CDCl_3$) δ 5.31-5.24 (m, 1H), 3.72 (s, 3H), 3.60 (bs, 2H), 3.54-3.40 (m, 6H), 2.44-2.18 (m, 3H), 2.07-1.96 (m, 3H), 1.96-1.68 (m, 4H), 1.65-1.55 (m, 4H), 1.51-1.36 (m, 8H), 1.27-1.05 (m, 6H), 1.03 (s, 3H), 0.95 (d, J=6.4 Hz, 3H), 0.85 (t, J=7.4 Hz, 3H), 0.68 (s, 3H).

Example 421: Methyl-4-(4-((3S,5S,8S,9S,10S,13R,14S,17S)-3-hydroxy-10,13-dimethylhexadecahydro-1H-cyclopenta[a]phenanthren-17-yl)butanoyl)piperazine-1-carboxylate

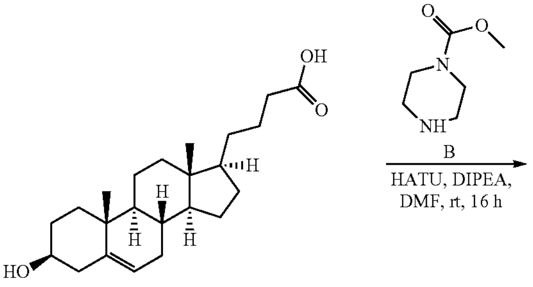

A

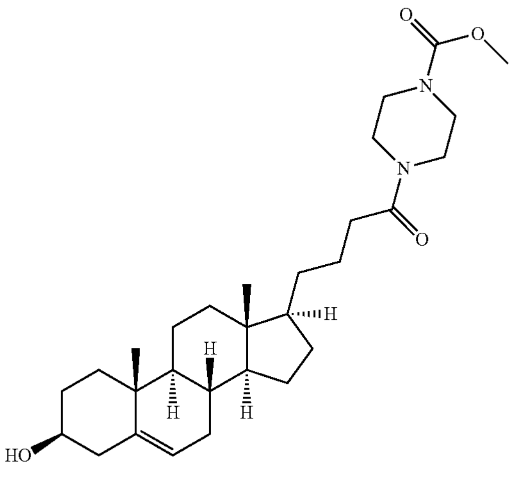

Methyl piperazine-1-carboxylate (88 mg, 610 μmol) and (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (200 mg, 555 μmol) was reacted according to the method of Example 536 to afford the title compound 421 (50 mg, 18.5%) as a white solid. LCMS: $[M+1]^+$=487.25. $^1H$ NMR (400 MHz, Chloroform-d) δ 5.35 (d, J=5.0 Hz, 1H), 3.72 (s, 3H), 3.62-3.43 (m, 9H), 2.35-2.30 (m, 2H), 2.29-2.17 (m, 2H), 2.03-1.93 (m, 1H), 1.89-1.80 (m, 3H), 1.78-1.72 (m, 1H), 1.67-1.40 (m, 10H), 1.32-1.19 (m, 3H), 1.10-1.17 (m, 2H), 1.09-1.05 (m, 1H), 1.01 (s, 3H), 0.96 (t, J=5.6 Hz, 2H), 0.58 (s, 3H).

Example 422: 4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]piperazine-1-carboxylate

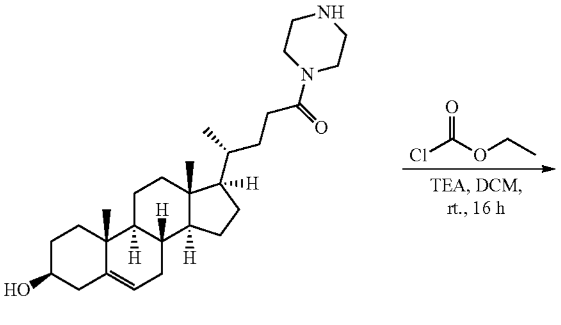

A

-continued

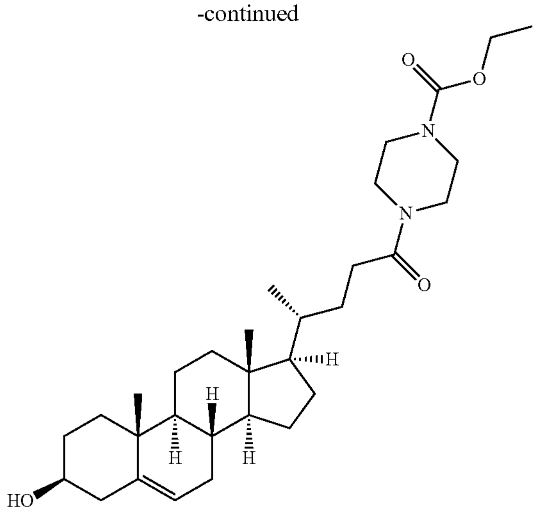

To a 0° C.; solution of compound A (200 mg, 452 μmol) in DCM (5 mL) was added triethylamine (229 mg, 2.26 mmol) and ethyl carbonochloridate (39.2 mg, 361 μmol) and the reaction was stirred for 16 h. The reaction was diluted with water and extracted with ethyl acetate. The organic layer was dried with sodium sulfate and concentrated under reduced pressure. The crude product was purified by silica gel chromatography to give the title compound 422 (56.0 mg, 24.1%) as a white solid. LCMS: [M+1]+=515.25. $^1H$ NMR (400 MHz, $CDCl_3$) δ 5.38-5.31 (m, 1H), 4.16 (q, J=7.0 Hz, 2H), 3.70-3.33 (m, 9H), 2.43-2.19 (m, 4H), 2.04-1.72 (m, 6H), 1.53-1.28 (m, 6H), 1.27 (d, J=7.2 Hz, 6H), 1.12-1.02 (m, 4H), 1.01 (s, 3H), 0.95 (d, J=6.4 Hz, 3H), 0.93-0.84 (m, 3H), 0.68 (s, 3H).

Example 423: 2-hydroxyethyl 4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]piperazine-1-carboxyla

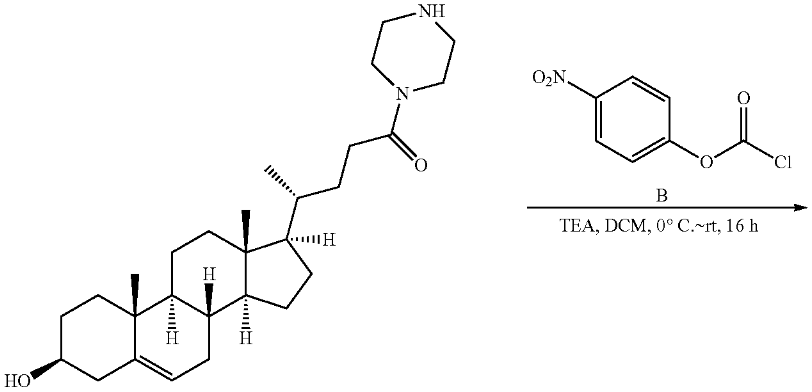

A

-continued

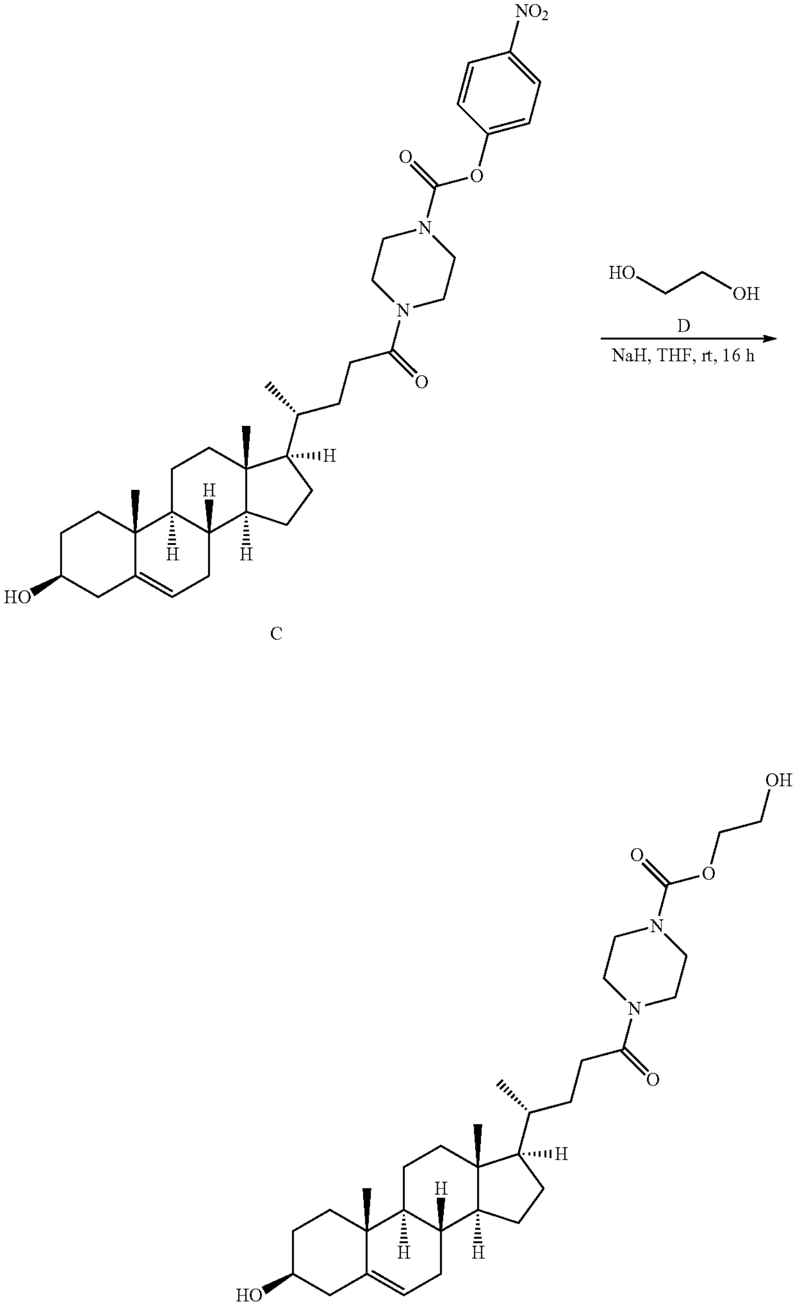

C

To a 0° C.; solution of compound A (1 g, 2.26 mmol) in DCM (10 mL) was added triethylamine (343 mg, 3.39 mmol) and compound B (462 mg, 2.03 mmol) and the reaction was stirred at room temperature for 16 hours. The reaction was quenched with water and extracted with ethyl acetate (30 mL*4). The combined organic layers were concentrated under reduced pressure. The crude product was purified by silica gel column to afford compound C (408 mg, 36%).

To a 0° C.; solution of compound C (408 mg, 6.58 mmol) in THF (5 mL) was added NaH (75.7 mg, 1.89 mmol, 60% dispersion in mineral oil) and stirred for 30 min at 0° C. A solution of Compound D (0.4 g, 658 μmol) in THF (4 mL) was added and the reaction warmed to room temperature for 16 hours. The reaction was quenched with water and extracted with ethyl acetate (10 mL*4). The combined organic layers were concentrated under reduced pressure. The residue was purified by silica gel chromatography to afford the title compound 423 (76.7 mg, 21%). LCMS: $[M+1]^+$=533.20. $^1H$ NMR (400 MHz, Chloroform-d) δ 5.34 (d, J=5.2 Hz, 1H), 4.30-4.21 (m, 2H), 3.87-3.80 (m, 2H), 3.61 (s, 2H), 3.54-3.44 (m, 7H), 2.42-2.33 (m, 1H), 2.32-2.19 (m, 3H), 2.02-1.93 (m, 2H), 1.91-1.75 (m, 8H), 1.63-1.55 (m, 2H), 1.54-1.41 (m, 6H), 1.36-1.24 (m, 3H), 1.21-1.03 (m, 5H), 1.00 (s, 3H), 0.97-0.87 (m, 4H), 0.68 (s, 3H).

Example 424: 2-hydroxyethyl 4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]piperazine-1-carboxylate

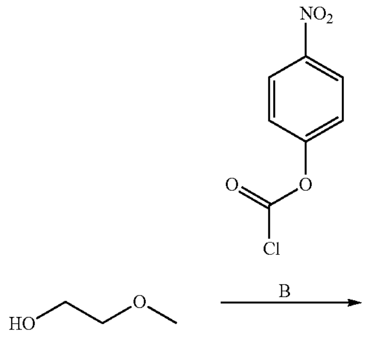

A

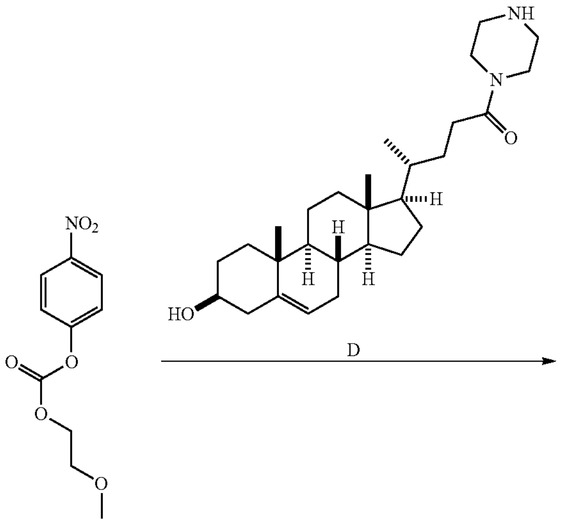

B

-continued

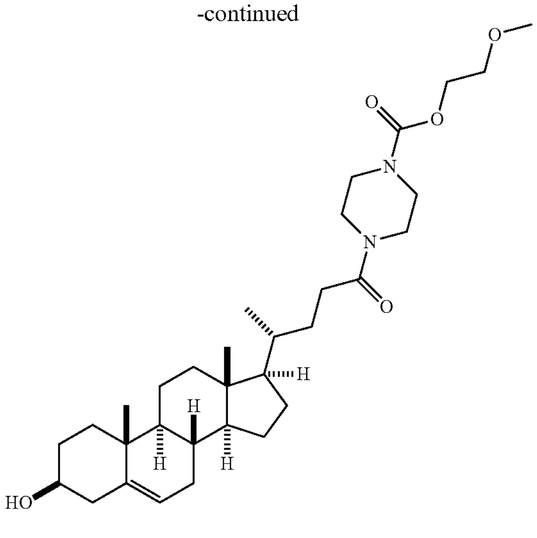

To a 0° C.; solution of compound A (100 mg, 1.31 mmol) in DCM (5 mL) was added TEA (294 mg, 1.97 mmol) and compound B (291 mg, 1.45 mmol) and the reaction stirred at 0° C. for 1 hour. Upon completion, the reaction was quenched with water (30 mL) and extracted with ethyl acetate (10 mL*3). The combined organic layers were washed with brine, dried over sodium sulfate, filtered concentrated under reduced pressure. The crude product was purified by column chromatography on silica gel to afford compound C (200 mg, 61%) as a white solid.

To a solution of compound C (200 mg, 829 μmol) in DMF (4 mL) was added compound D (367 mg, 829 μmol), DIEA (322 mg, 2.49 mmol) and the reaction was stirred at room temperature for 4 hours. The reaction was added water (40 mL) and extracted with ethyl acetate (20 mL*2). The combined organic layer was concentrated to give crude. The crude was purified by column to afford the title compound 424 (80 mg, 18%) as a white solid. LCMS: $[M+H]^+$=545.25. $^1H$ NMR (400 MHz, Chloroform-d) δ 5.37-5.31 (m, 1H), 4.29-4.21 (m, 2H), 3.64-3.41 (m, 11H), 3.38 (s, 3H), 2.43-2.17 (m, 4H), 2.04-1.91 (m, 2H), 1.90-1.72 (m, 4H), 1.59-1.40 (m, 7H), 1.37-1.23 (m, 3H), 1.19-1.03 (m, 4H), 1.00 (s, 3H), 0.95 (d, J=6.6 Hz, 4H), 0.68 (s, 3H).

Example 425: oxetan-3-yl4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperazine-1-carboxylate

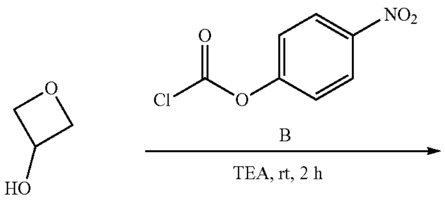

A

-continued

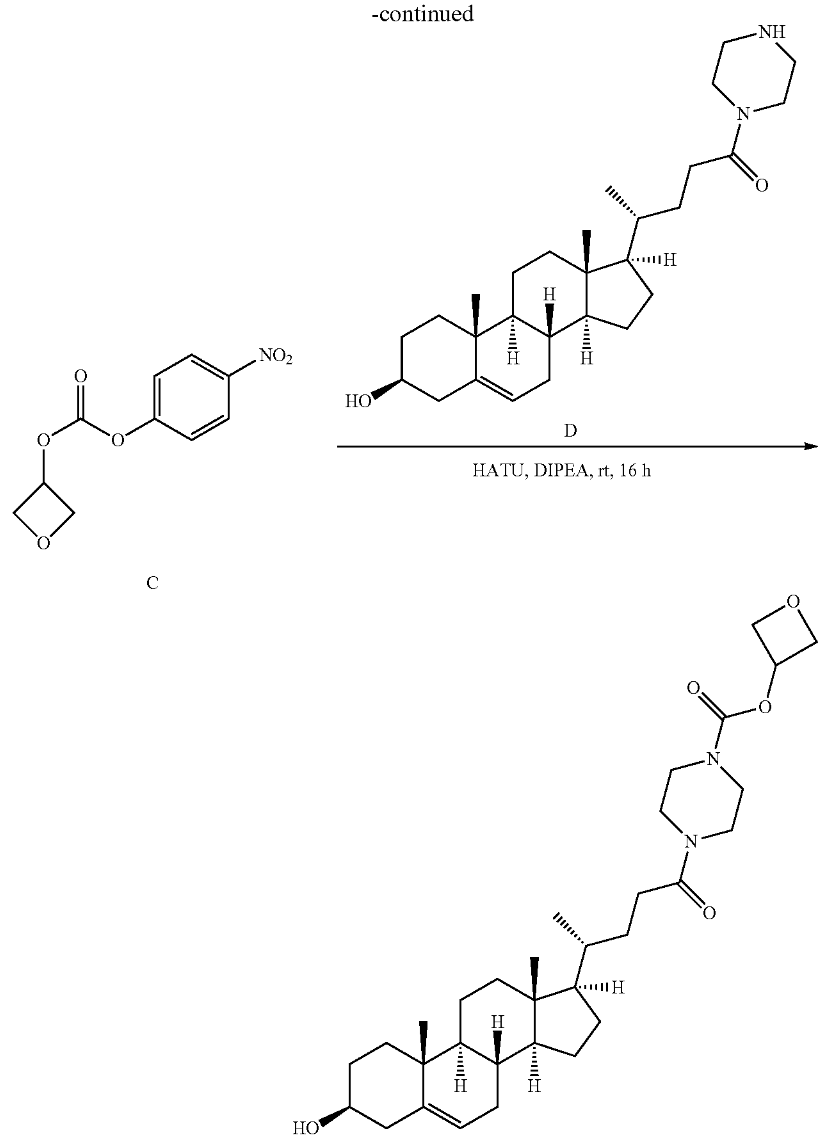

To a 0° C.; solution of compound A (100 mg, 1.35 mmol) and compound B (272 mg, 1.35 mmol) in dichloromethane (5 mL, 78.1 mmol) under $N_2$ was added triethylamine (205 mg, 1.5 eq, 2.02 mmol) and the reaction was warmed to room temperature for 2 hours. The reaction concentrated under reduced pressure to afford the crude C (520 mg, 2.17 mmol). To a room temperature solution of compound D (157 mg, 354 μmol) and compound C (102 mg, 425 μmol) in DMF (1.5 mL) under $N_2$ was added DIPEA (137 mg, 1.06 mmol) and the reaction was stirred at room temperature for 16 hours. The reaction was diluted with water (10 mL) and extracted with EtOAc (20 ml*3). The combined organic layers were washed with brine (20 mL), dried over sodium sulfate and concentrated under reduced pressure. The crude product was purified by silica gel chromatography to afford the title compound 425 (110 mg, 57%) as a white solid. LCMS: $[M+1]^+$=543.25. $^1$H NMR (400 MHz, Chloroform-d) δ 5.45-5.38 (m, 1H), 5.36-5.33 (m, 1H), 4.89 (t, J=8.0 Hz, 2H), 4.69-4.63 (m, 2H), 3.65-3.59 (m, 2H), 3.56-3.41 (m, 7H), 2.42-2.34 (m, 1H), 2.32-2.15 (m, 3H), 2.05-1.92 (m, 2H), 1.91-1.72 (m, 4H), 1.64-1.60 (m, 1H), 1.52-1.41 (m, 6H), 1.37-1.25 (m, 3H), 1.22-1.04 (m, 4H), 1.01 (s, 3H), 0.97-0.91 (m, 4H), 0.69 (s, 3H).

Example 426: (R)-1-((R)-4-acetyl-3-methylpiperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

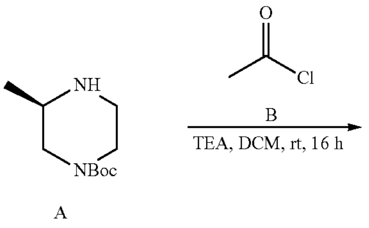

-continued

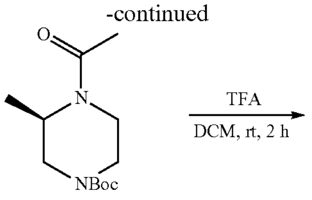

C

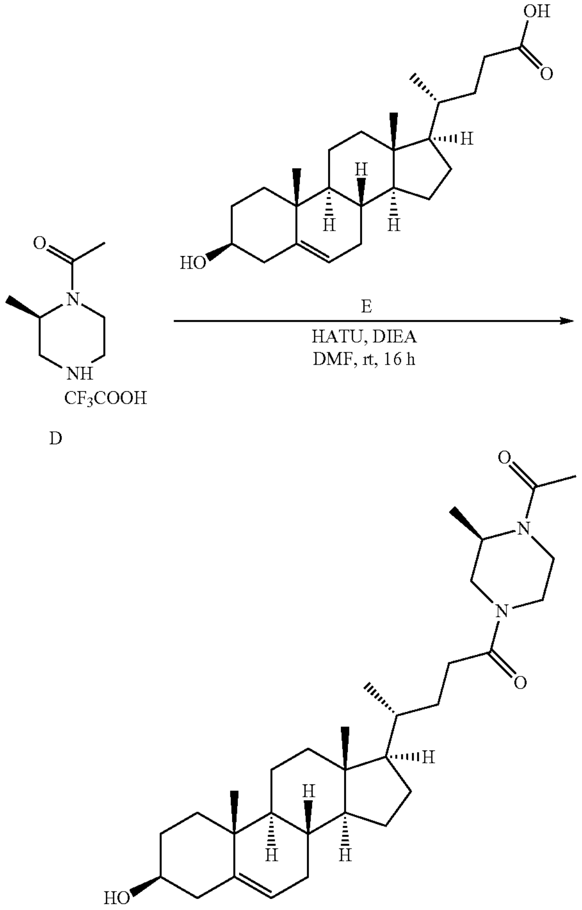

To a solution of compound A (200 mg, 999 μmol) in DCM (3 mL) was added triethylamine (298 mg, 2 mmol). The reaction was cooled to 0° C. and added compound B (86.2 mg, 1.1 mmol) and stirred at room temperature under $N_2$ for 16 h. The reaction was quenched with water and extracted with DCM. The organic layer was dried over sodium sulfate and concentrated to afford compound C (100 mg, 413 μmol, 41.3% yield) as a yellow oil. To a solution of compound C (100 mg, 413 μmol) in DCM (2 mL) was added TFA (0.5 mL) and stirred at room temperature for 2 h. The reaction was concentrated under reduced pressure to give compound D as the TFA salt (77.1 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (120 mg, 404 μmol) and (R)-1-(2-methylpiperazin-1-yl)ethan-1-one (77.1 mg, 320 μmol) was reacted according to the method of Example 536 to afford the title compound 426 (81.3 mg, 50.9%) as a white solid. LCMS: $[M+1]^+$=499.30. $^1H$ NMR (400 MHz, Chloroform-d) δ 5.34 (dd, J=4.8, 2.4 Hz, 1H), 4.87-4.32 (m, 2H), 4.09-3.44 (m, 3H), 3.40-2.58

(m, 3H), 2.44-1.64 (m, 16H), 1.63-1.03 (m, 20H), 1.00 (s, 3H), 0.99-0.85 (m, 5H), 0.68 (s, 3H).

Example 427: (R)-1-((S)-4-acetyl-3-methylpiperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

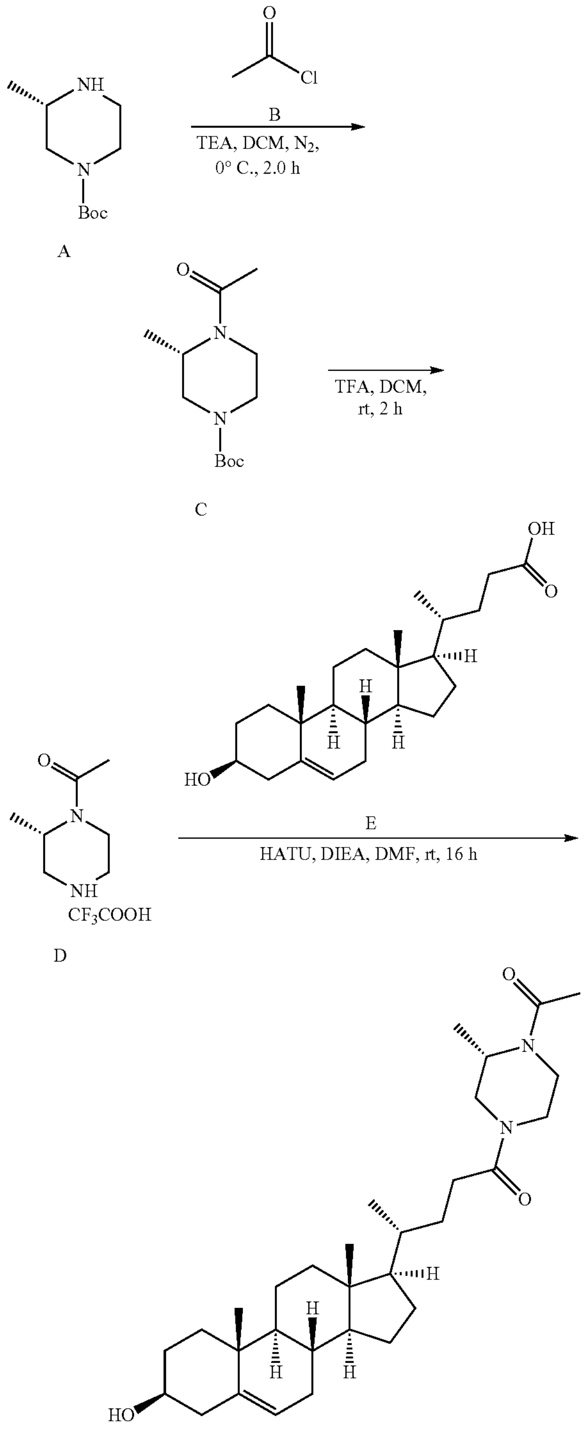

To a solution of compound A (500 mg, 2.5 mmol) and TEA (700 mg, 6.9 mmol) in DCM (10 mL) at 0° C. was added compound B (235 mg, 3 mmol). The reaction was stirred at 0° C. under $N_2$ for 2 h. The reaction was diluted with water and extracted with EtOAc. The organic layer was washed with brine, dried over sodium sulfate, filtered, and concentrated to afford the compound C (400 mg, 66.1%) as white oil. To a solution of compound C (200 mg, 0.82 mmol) in DCM (3 mL) was added TFA (1 mL). The reaction was stirred at room temperature under $N_2$ for 2 h. The reaction concentrated to afford compound D as the TFA salt (170 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (300 mg, 0.82 mmol) and (S)-1-(2-methylpiperazin-1-yl)ethan-1-one 2,2,2-trifluoroacetate (170 mg, 0.66 mmol) was reacted according to the method of Example 536 to afford the title compound 427 (55.3 mg, 13.4%) as a white solid. LCMS: $[M+1]^+$=499.25. $^1H$ NMR (400 MHz, Chloroform-d) δ 5.35 (d, J=5.2 Hz, 1H), 4.88-4.33 (m, 2H), 4.10-3.48 (m, 3H), 3.44-2.56 (m, 3H), 2.44-2.18 (m, 4H), 2.15-2.07 (m, 3H), 1.99 (m, 2H), 1.91-1.75 (m, 4H), 1.58-1.40 (m, 7H), 1.38-1.25 (m, 4H), 1.23-1.05 (m, 6H), 1.00 (s, 3H), 0.95 (t, J=6.8 Hz, 4H), 0.68 (s, 3H).

Example 428: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(2S)-4-acetyl-2-methylpiperazin-1-yl]pentan-1-one

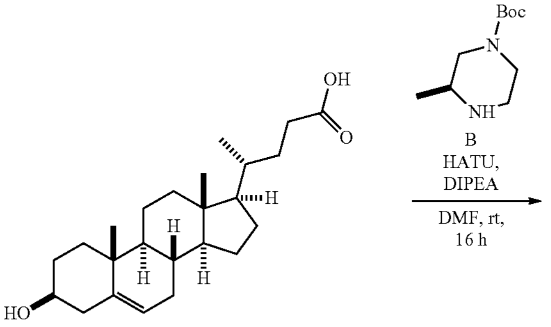

A

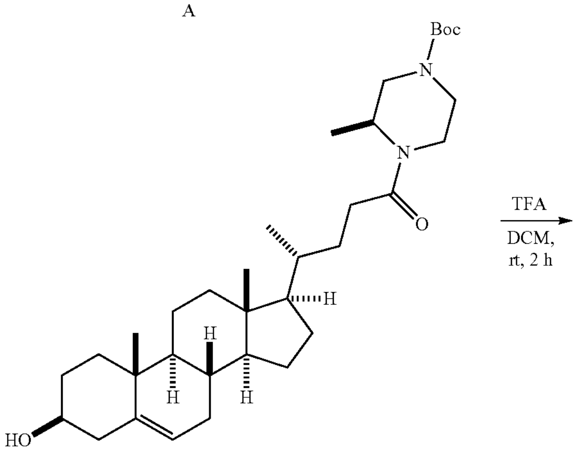

C

-continued

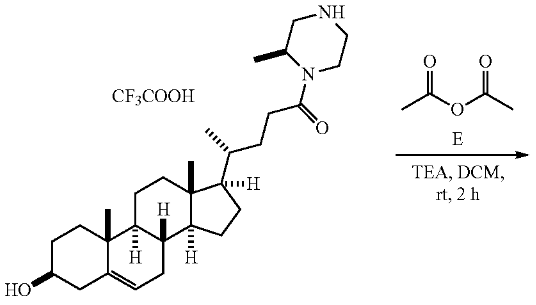

D

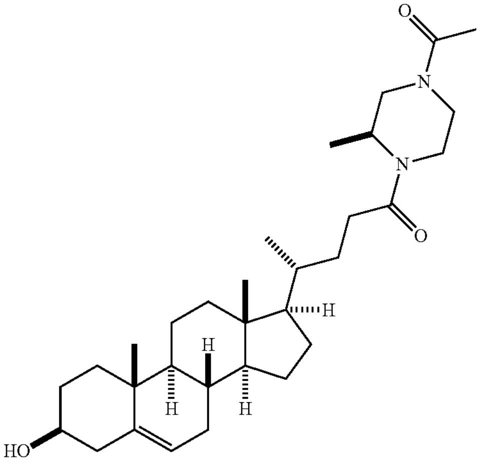

To a solution of compound A (500 mg, 1.33 mmol) in DMF (10 mL) was added compound B (334 mg, 1.67 mmol), DIEA (1.27 g, 3.34 mmol) and HATU (1.29 mg, 10 mmol) and the reaction was stirred at room temperature for 4 hours. The reaction was quenched with water and extracted with ethyl acetate. The organic layer was concentrated under reduced pressure. The crude product was purified by silica gel chromatography to afford compound C (300 mg, 32%) To a solution of compound C (200 mg, 359 μmol) in DCM (6 mL) was added TFA (2 mL) at room temperature and the reaction was stirred for 2 h. The reaction concentrated under reduced pressure to afford compound D as the TFA salt.

To a 0° C. solution of compound D (130 mg, 285 μmol) in DCM (5 mL) was added TEA (127 mg, 854 μmol) and compound E (29.1 mg, 285 μmol) and the reaction was stirred for 1 hour. Upon completion, the reaction was quenched with water (30 mL) and extracted with ethyl acetate (10 mL*3). The combined organic layers were washed with brine, dried over sodium sulfate, filtered, and concentrated under reduced pressure. The crude product was purified by silica gel chromatography to yield the title compound 428 (40 mg, 28%) as a white solid. LCMS: $[M+H]^+$=499.20. $^1H$ NMR (400 MHz, Chloroform-d) δ 5.34 (s, 1H), 4.60-4.30 (m, 1H), 3.82-3.44 (m, 3H), 3.23 (m, 2H), 2.87-2.68 (m, 1H), 2.27-2.19 (m, 3H), 2.14-2.09 (m, 3H), 2.01-1.94 (m, 2H), 1.91-1.78 (m, 3H), 1.56-1.39 (m, 7H), 1.31 (s, 4H), 1.20-1.05 (m, 6H), 1.00 (d, J=3.6 Hz, 4H), 0.95 (s, 4H), 0.68 (s, 3H).

Example 429: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(2R)-4-acetyl-2-methylpiperazin-1-yl]pentan-1-one

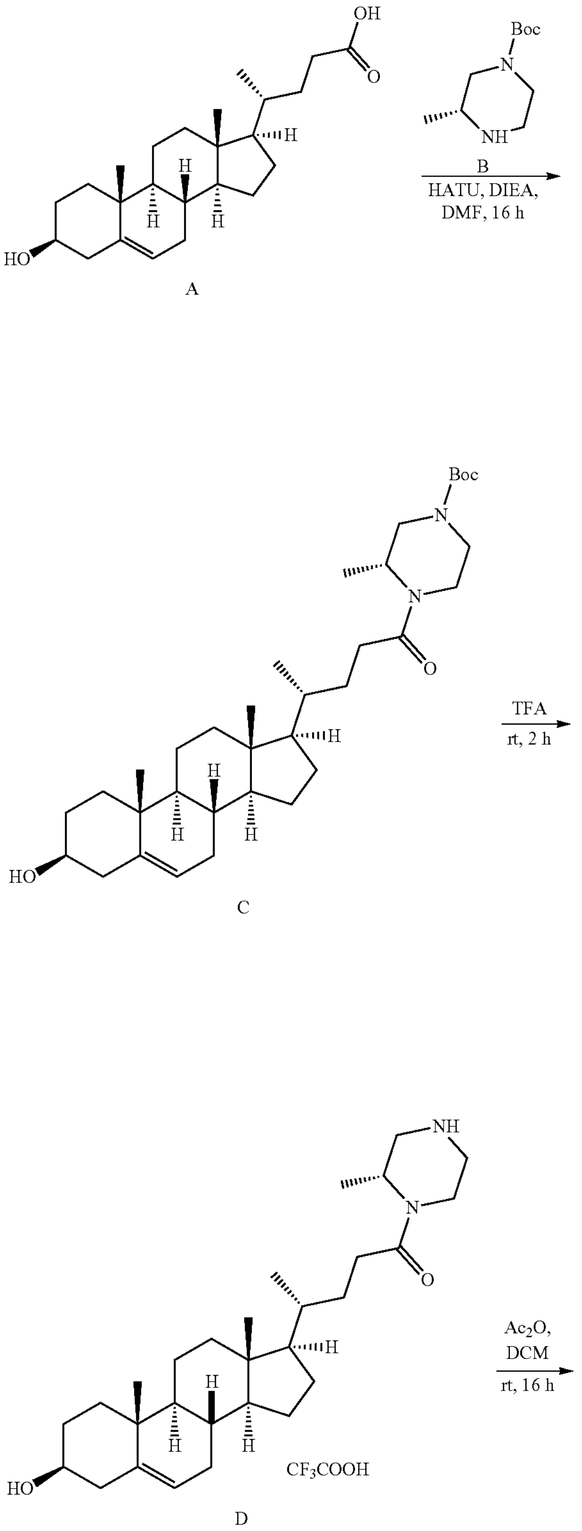

-continued

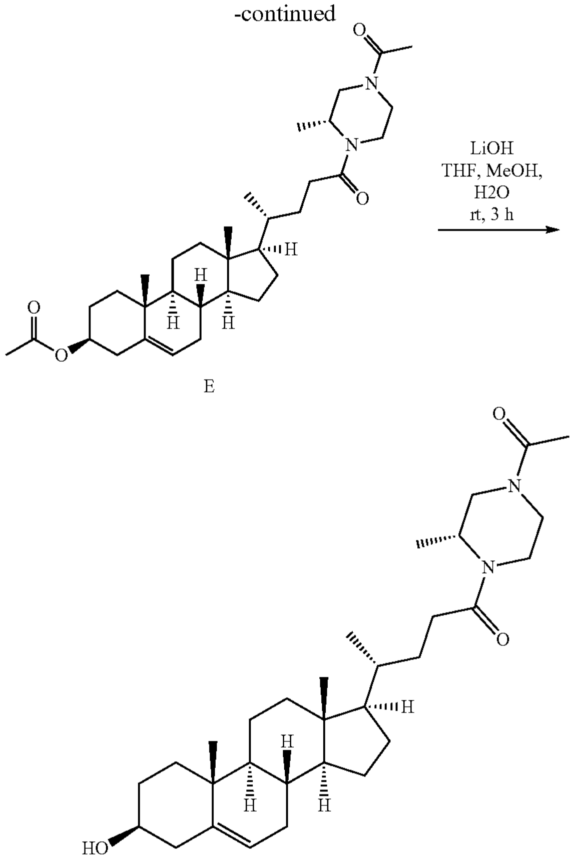

To a solution of compound A (300 mg, 801 μmol) in DMF (5 mL) was added compound B (192 mg, 961 μmol), HATU (457 mg, 1.2 mmol) and DIPEA (414 mg, 3.2 mmol). The reaction was stirred at room temperature for 16 hours. The reaction was quenched with saturated $NH_4Cl$ and extracted with ethyl acetate. The organic layer was concentrated, and the residue was purified by silica gel chromatography to afford compound C (350 mg, 78%) as a white solid.

To a solution of compound C (350 mg, 629 μmol) in DCM (6 mL) was added trifluoroacetic acid (2 mL) at room temperature and the reaction was stirred for 2 h. The reaction concentrated under reduced pressure to give compound D as the TFA salt (342 mg). To a solution of compound D (118 mg, 258 μmol) in DCM (3 mL) was added acetic anhydride (39.6 mg, 388 μmol). The reaction was stirred at room temperature for 16 hours. The reaction was quenched with saturated $NaHCO_3$ and extracted with ethyl acetate. The organic layer was concentrated, and the residue was purified by silica gel chromatography to give compound E (40 mg, 29%) as a yellow solid.

To a solution of compound E (40 mg, 74 μmol) in THE (1 mL), MeOH (1 mL) and water (1 mL) was added LiOH (5.31 mg, 222 μmol). The solution was stirred at room temperature for 3 h. The reaction was diluted with water and extracted with ethyl acetate. The organic layer was concentrated, and the residue was purified by silica gel chromatography to give the title compound 429 (21 mg, 56%) as a white solid. LCMS: $[M+1]^+$=498.40. $^1H$ NMR (400 MHz, Chloroform-d) δ 5.35 (d, J=5.2 Hz, 1H), 4.89-4.01 (m, 2H), 3.80-2.63 (m, 5H), 2.45-1.77 (m, 12H), 1.57-1.39 (m, 8H), 1.18-1.04 (m, 7H), 1.02-0.91 (m, 8H), 0.92-0.87 (m, 1H), 0.68 (s, 3H).

Example 430: (1S,3aS,3bS,7S,9aR,9bS,11aS)-9a,11a-dimethyl-1-[(1S)-1-[(2-methylpyridin-3-yl)oxy]ethyl]-1H,2H,3H,3aH,3bH,4H,6H,7H,8H,9H,9aH,9bH,10H,11H,11aH-cyclopenta[a]phenanthren-7-ol

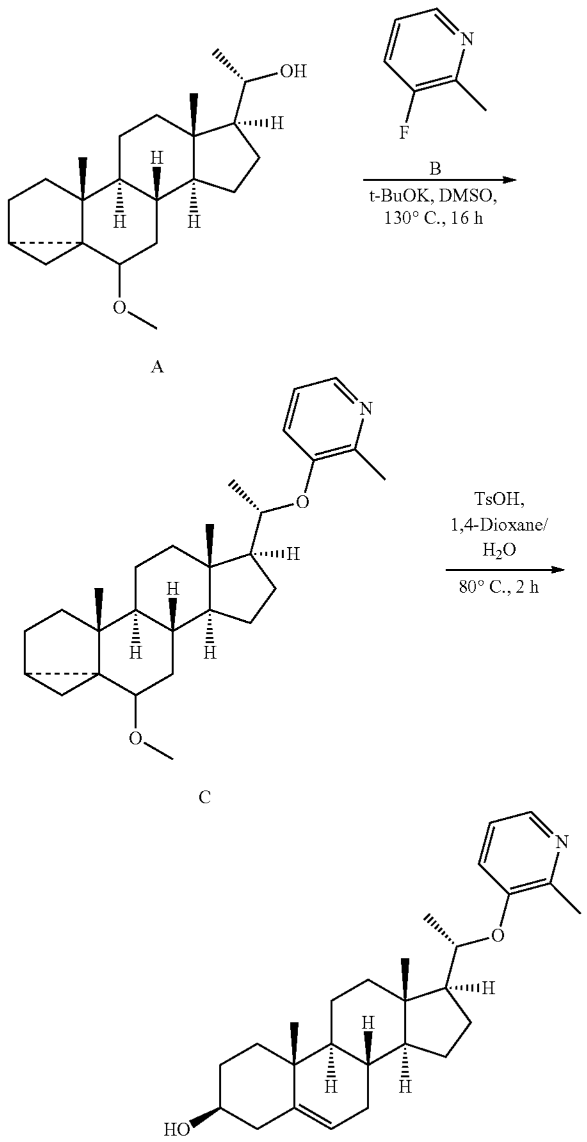

To a solution of compound A (200 mg, 601 μmol) in DMSO (3 mL) was added compound B (100 mg, 902 μmol) and t-BuOK (202 mg, 1.8 mmol). The reaction was stirred at 130° C. for 16 hours. The reaction was cooled to room temperature. The reaction was quenched with water (30 mL) and extracted with ethyl acetate (15 mL*3). The combined organic layers were concentrated under reduced pressure. The crude product was purified by silica gel chromatography to afford compound C (200 mg, 78%) as a white solid.

To a solution of compound C (100 mg, 236 μmol) in 1,4-dioxane (3.5 mL) and water (0.5 mL) was added TsOH (24.4 mg, 142 μmol). The reaction was stirred at 80° C. for 2 hours. The reaction was quenched with water (5 mL) and extracted with ethyl acetate (10 mL). The organic layer was concentrated under reduced pressure. The crude product was purified by silica gel chromatography to afford the title compound 430 (14.6 mg, 15%) as a white solid. LCMS: $[M+H]^+$=410.20. $^1H$ NMR (400 MHz, Chloroform-d) δ 8.07-7.96 (m, 1H), 7.07 (d, J=3.2 Hz, 2H), 5.42-5.32 (m, 1H), 4.35-4.21 (m, 1H), 3.59-3.46 (m, 1H), 2.45 (s, 3H), 2.35-2.18 (m, 2H), 2.10-1.79 (m, 7H), 1.76-1.37 (m, 9H), 1.30 (d, J=6.0 Hz, 3H), 1.28-1.04 (m, 6H), 1.01 (s, 3H), 0.99-0.85 (m, 1H), 0.71 (s, 3H).

Example 431: (1S,3aS,3bS,7S,9aR,9bS,11aS)-9a,11a-dimethyl-1-[(1S)-1-[(6-methylpyridin-3-yl)oxy]ethyl]—H,2H,3H,3aH,3bH,4H,6H,7H,8H,9H,9aH,9bH,10H,11H,11aH-cyclopenta[a]phenanthren-7-ol

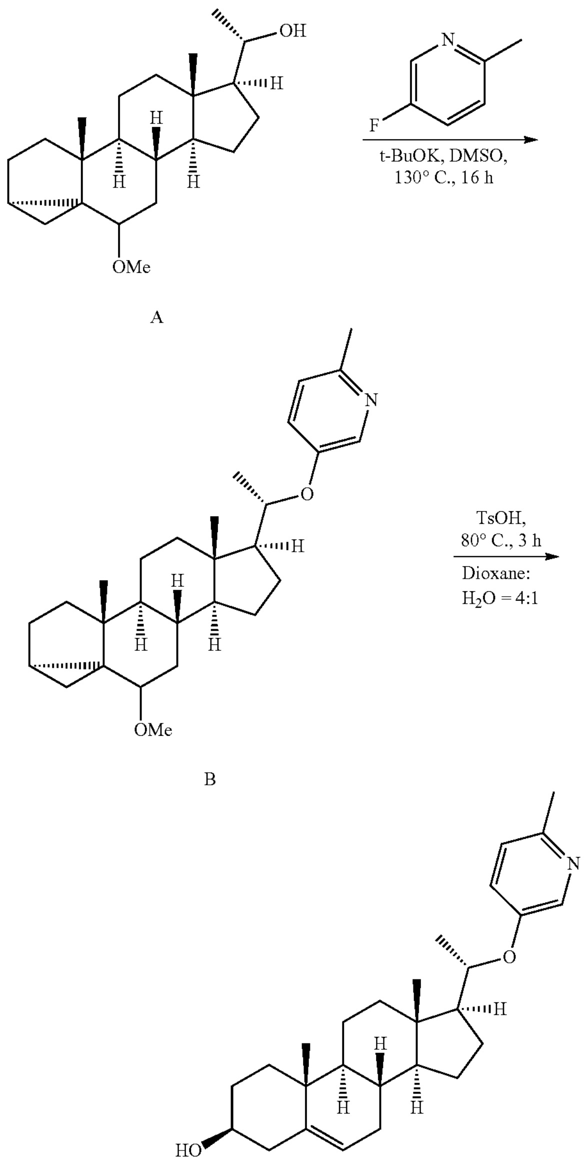

To a solution of compound A (150 mg, 451 μmol) in DMSO (3.75 mL) was added 5-fluoro-2-methylpyridine (75.2 mg, 677 μmol) and t-BuOK (253 mg, 2.26 mmol) at room temperature. The reaction was stirred at 130° C. for 16 h under nitrogen. The reaction was diluted with water and extracted with ethyl acetate. The organic layer was washed with water and brine, dried with sodium sulfate and concentrated under reduced pressure. The crude product was purified by silica gel chromatography to give compound B (90 mg, 47.1%).

5-((1S)-1-((1aR,3aR,3bS,5aS,6S,8aS,8bS,10aS)-10-methoxy-3a,5a-dimethylhexadecahydrocyclopenta[a]cyclopropa[2,3]cyclopenta[1,2-f]naphthalen-6-yl)ethoxy)-2-methylpyridine(70 mg, 165 μmol) was reacted according to the method of Example 430 to afford the title compound 431 (39.1 mg, 57.8%) as a white solid. LCMS: $[M+H]^+$=410.20. $^1$H NMR (400 MHz, $CDCl_3$) δ 8.14 (d, J=2.8 Hz, 1H), 7.15-7.00 (m, 2H), 5.36 (d, J=5.2 Hz, 1H), 4.29-4.19 (m, 1H), 3.58-3.46 (m, 1H), 2.49 (s, 3H), 2.33-2.21 (m, 2H), 2.04-1.61 (m, 12H), 1.50-1.43 (m, 2H), 1.30 (d, J=6.0 Hz, 3H), 1.27-1.08 (m, 5H), 1.01 (s, 3H), 0.71 (s, 3H).

Example 432: (3S,8S,9S,10R,13S,14S,17S)-10,13-dimethyl-17-((S)-1-((5-methylpyridin-3-yl)oxy)ethyl)-2,3,4,7,8,9,10,11,12,13,14,15,16,17-tetradecahydro-1H-cyclopenta[a]phenanthren-3-ol

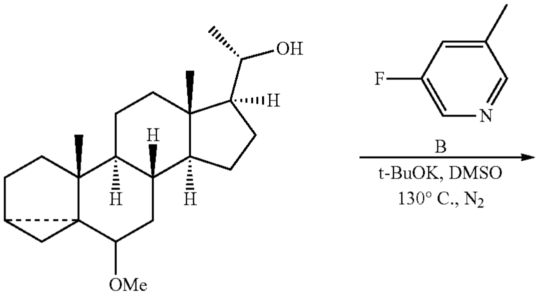

A

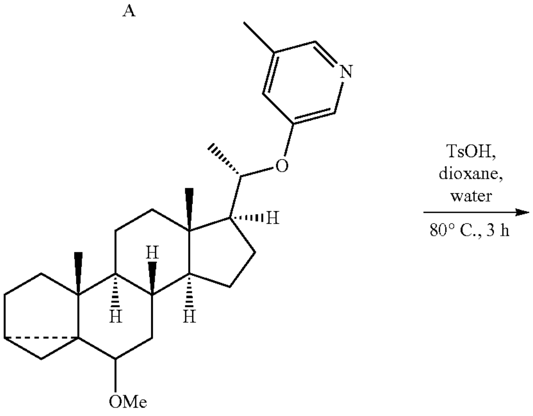

C

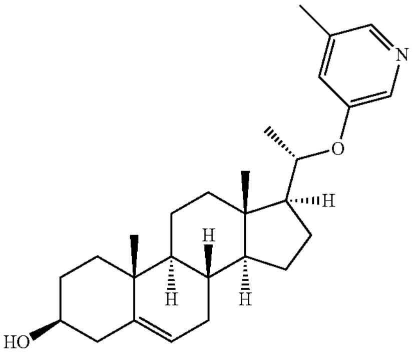

To a solution of compound A (200 mg, 601 μmol) in DMSO (5 mL) was added compound B (200 mg, 902 μmol), t-BuOK (202 mg, 1.8 mmol) and the reaction was stirred at 130° C. under nitrogen for 16 hours. Upon completion, the reaction was quenched with water (10 mL) and extracted with ethyl acetate (10 mL*3). The organic layer was washed with brine, dried over sodium sulfate, filtered, and concentrated under reduced pressure. The crude product was purified by column chromatography on silica gel to afford compound C (140 mg, 55%) as a white solid.

3-((1S)-1-((1aR,3aR,3bS,5aS,6S,8aS,8bS,10aR)-10-methoxy-3a,5a-dimethylhexadecahydrocyclopenta[a]cyclopropa[2,3]cyclopenta[1,2-f]naphthalen-6-yl)ethoxy)-5-methylpyridine (140 mg, 330 μmol) was reacted according to the method of Example 430 to afford the title compound 432 (50 mg, 37%) as a white solid. LCMS: $[M+1]^+$=410.15. $^1$H NMR (400 MHz, Chloroform-d) δ 8.06 (d, J=2.4 Hz, 1H), 8.00 (s, 1H), 6.97 (t, J=2.0 Hz, 1H), 5.36 (dd, J=5.2, 2.4 Hz, 1H), 4.28 (dd, J=7.2, 5.6 Hz, 1H), 3.59-3.46 (m, 1H), 2.34-2.19 (m, 5H), 2.06-1.75 (m, 6H), 1.70-1.61 (m, 3H), 1.59-1.51 (m, 3H), 1.47 (dt, J=11.2, 4.4 Hz, 2H), 1.31 (d, J=6.0 Hz, 3H), 1.26-1.04 (m, 5H), 1.01 (s, 3H), 0.96 (dd, J=11.6, 5.2 Hz, 1H), 0.72 (s, 3H).

Example 433: (3S,8S,9S,10R,13S,14S,17S)-10,13-dimethyl-17-((S)-1-((4-methylpyridin-3-yl)oxy)ethyl)-2,3,4,7,8,9,10,11,12,13,14,15,16,17-tetradecahydro-1H-cyclopenta[a]phenanthren-3-ol

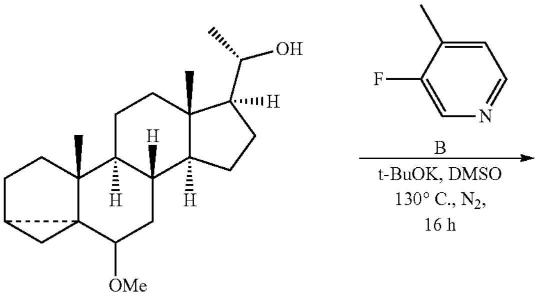

A

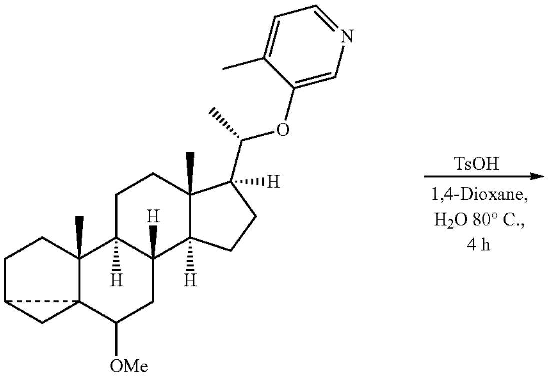

C

-continued

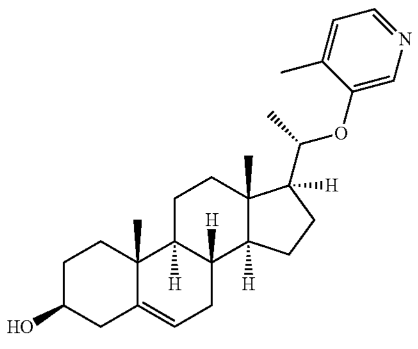

To a solution of compound A (300 mg, 902 μmol) in DMSO (5 mL) was added compound B (200 mg, 1.8 mmol) and t-BuOK (506 mg, 4.51 mmol). The reaction was stirred at 130° C. under $N_2$ for 16 h. The reaction was quenched with water and extracted with EA. The organic layer was washed with brine, dried over sodium sulfate and concentrated under reduced pressure. The crude product was purified by silica gel chromatography to afford compound C (130 mg, 34%) as a yellow oil.

3-((1S)-1-((1aR,3aR,3bS,5aS,6S,8aS,8bS,10aR)-10-methoxy-3a,5a-dimethylhexadecahydrocyclopenta[a]cyclopropa[2,3]cyclopenta[1,2-f]naphthalen-6-yl)ethoxy)-4-methylpyridine (130 mg, 307 μmol) was reacted according to the method of Example 430 to afford the title compound 433 (39.3 mg, 31.3%) as a white solid. LCMS: $[M+1]^+$=410.15. $^1$H NMR (400 MHz, Chloroform-d) δ 8.15 (s, 1H), 8.06 (d, J=4.4 Hz, 1H), 7.06 (d, J=4.4 Hz, 1H), 5.36 (dd, J=4.8, 2.4 Hz, 1H), 4.43-4.36 (m, 1H), 3.58-3.46 (m, 1H), 2.33-2.21 (m, 2H), 2.20 (s, 3H), 2.06-1.79 (m, 7H), 1.73-1.63 (m, 3H), 1.62-1.44 (m, 6H), 1.34 (d, J=6.0 Hz, 3H), 1.32-1.05 (m, 6H), 1.02 (s, 3H), 0.97 (dt, J=11.6, 5.6 Hz, 1H), 0.72 (s, 3H).

Example 434: (3S,8S,9S,10R,13S,14S,17S)-17-((S)-1-((2-(hydroxymethyl)pyridin-3-yl) oxy)ethyl)-10,13-dim ethyl-2, 3,4, 7,8, 9,10,11,12,13,14,15,16,17-tetradecahydro-1H-cyclopenta[a]phenanthren-3-ol

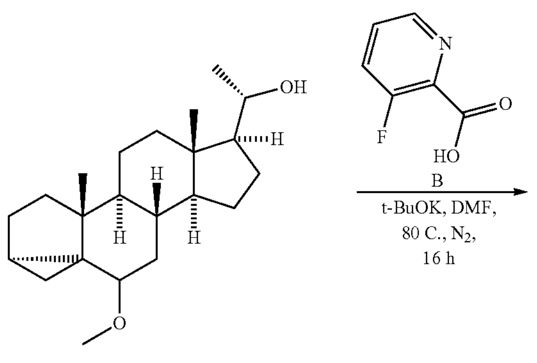

A

-continued

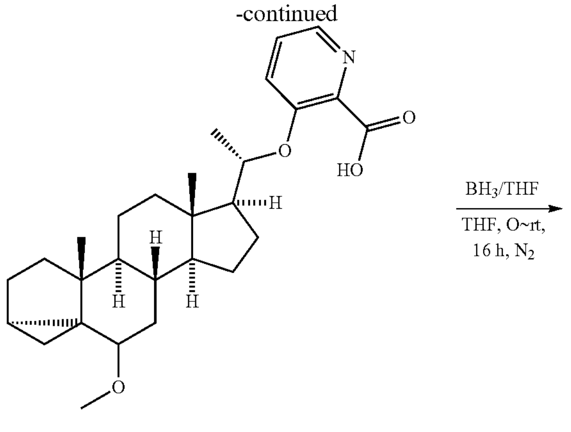

C

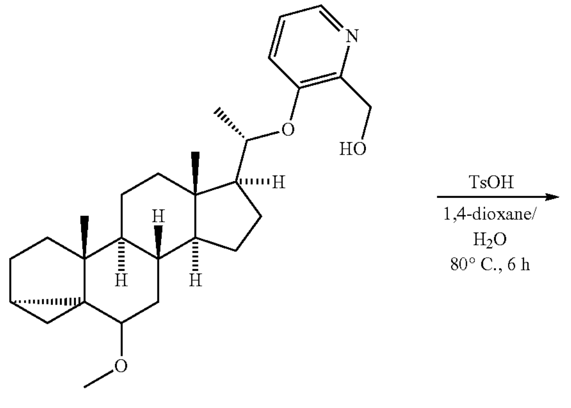

D

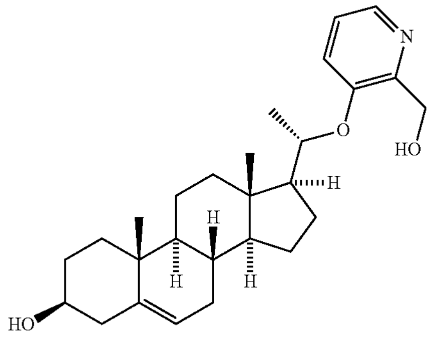

To a solution of compound A (200 mg, 601 μmol) in DMF (8 mL) was added compound B (127 mg, 902 μmol) and t-BuOK (202 mg, 1.8 mmol) and the reaction was stirred at 130° C. for 16 hours. The reaction was diluted with water and extracted with ethyl acetate. The organic layer was concentrated under reduced pressure. The crude product was purified by prep-TLC to give compound C (150 mg, 56%) To a 0° C. solution of compound C (150 mg, 331 μmol) in THF (6 mL) was added $BH_3$/THF (1 mL, 1 mmol, 1M in THF) and the reaction was warmed to room temperature for 16 hours. The reaction was quenched with MeOH and concentrated under reduced pressure. The crude product was purified by prep-TLC to give compound D (110 mg, 76%)

5-((1S)-1-(3-((1S)-1-((1aR,3aR,3bS,5aS,6S,8aS,8bS,10aS)-10-methoxy-3a,5a-dimethylhexadecahydrocyclopenta[a]cyclopropa[2,3]cyclopenta[1,2-f]naphthalen-6-yl) ethoxy)pyridin-2-yl)methanol (110 mg, 250 μmol) was reacted according to the method of Example 430 to afford the title compound 434 (25 mg, 23%) as a white solid.

LCMS: $[M+1]^+$=426.20. $^1H$ NMR (400 MHz, Chloroform-d) δ 8.10 (dd, J=4.8, 1.2 Hz, 1H), 7.16 (dd, J=8.4, 4.8 Hz, 1H), 7.10 (d, J=8.0 Hz, 1H), 5.36 (d, J=5.2 Hz, 1H), 4.70 (d, J=4.4 Hz, 2H), 4.32 (t, J=6.8 Hz, 2H), 3.58-3.49 (m, 1H), 2.34-2.21 (m, 2H), 2.07-1.83 (m, 5H), 1.74-1.66 (m, 2H), 1.53-1.41 (m, 4H), 1.31 (d, J=6.0 Hz, 3H), 1.28-1.04 (m, 6H), 1.01 (s, 3H), 0.97 (dd, J=11.2, 4.8 Hz, 1H), 0.71 (s, 3H).

Example 435: (3S,8S,9S,10R,13S,14S,17S)-17-((S)-1-((6-(hydroxymethyl)pyridin-3-yl) oxy)ethyl)-10,13-dim ethyl-2, 3,4, 7,8, 9,10,11,12,13,14,15,16,17-tetradecahydro-1H-cyclopenta[a]phenanthren-3-ol

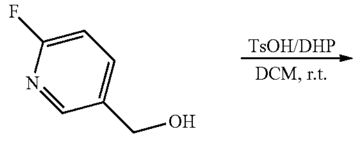

A

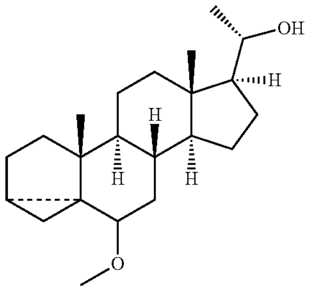

C

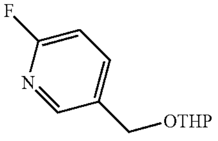

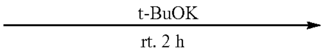

B

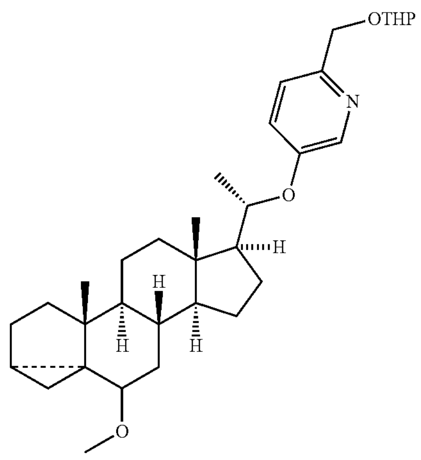

D

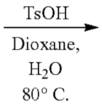

-continued

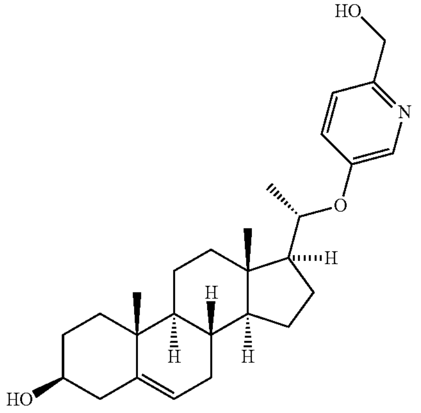

To a solution of compound A (200 mg, 1.57 mmol) in DCM (4 mL) was added DHP (397 mg, 4.72 mmol), 4-methylbenzene-1-sulfonic acid (27.1 mg, 157 μmol) and the reaction was stirred at room temperature for 1 hour under nitrogen. Upon completion, the solution was quenched with water and extracted with ethyl acetate. The organic layer was dried over sodium sulfate and concentrated under reduced pressure. The crude product was purified by silica gel chromatography to afford the compound B (290 mg, 87.3%) as a white solid.

To a solution of compound C (150 mg, 451 μmol) in DMSO (3 mL) was added compound B (143 mg, 677 μmol) and t-BuOK (253 mg, 2.26 mmol) and the reaction was stirred for 2 hours. Upon completion, the solution was quenched with water and extracted with DCM. The organic layer was dried over sodium sulfate and concentrated under reduced pressure. The crude product was purified by silica gel chromatography to afford the compound D (120 mg, 50.8%) as a white solid.

5-((1S)-1-((1aR,3aR,3bS,5aS,6S,8aS,8bS,10aR)-10-methoxy-3a,5a-dimethylhexadecahydrocyclopenta[a]cyclopropa[2,3]cyclopenta[1,2-f]naphthalen-6-yl)ethoxy)-2-(((tetrahydro-2H-pyran-2-yl)oxy)methyl)pyridine (100 mg, 191 μmol) was reacted according to the method of Example 430 to afford the title compound 435 (21.7 mg, 26.7%) as a white solid. LCMS: $[M+H]^+$=426.20. $^1H$ NMR (400 MHz, Chloroform-d) δ 8.20 (d, J=2.5 Hz, 1H), 7.23-7.12 (m, 2H), 5.36 (d, J=5.2 Hz, 1H), 4.69 (s, 2H), 4.32-4.24 (m, 1H), 3.52 (td, J=11.2, 5.8 Hz, 1H), 2.34-2.20 (m, 2H), 2.04-1.97 (m, 2H), 1.91 (dd, J=12.4, 3.2 Hz, 1H), 1.87-1.82 (m, 2H), 1.69-1.47 (m, 12H), 1.32 (d, J=6.0 Hz, 3H), 1.23-1.09 (m, 3H), 1.01 (s, 3H), 0.72 (s, 3H).

Example 436: (3S,8S,9S,10R,13S,14S,17S)-17-((S)-1-((5-(hydroxymethyl)pyridin-3-yl) oxy)ethyl)-10, 13-dim ethyl-2, 3,4, 7,8, 9,10,11,12,13,14,15,16,17-tetradecahydro-1H-cyclopenta[a]phenanthren-3-ol

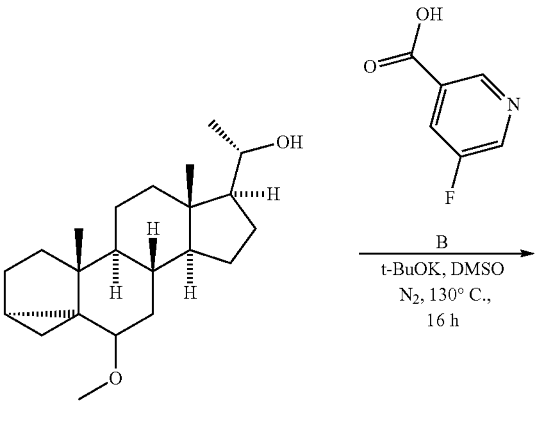

A

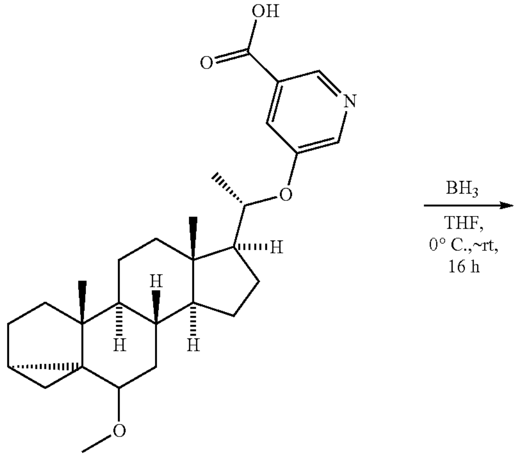

C

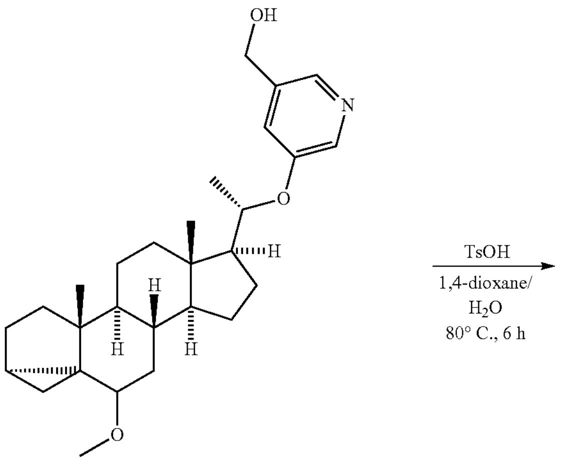

D

-continued

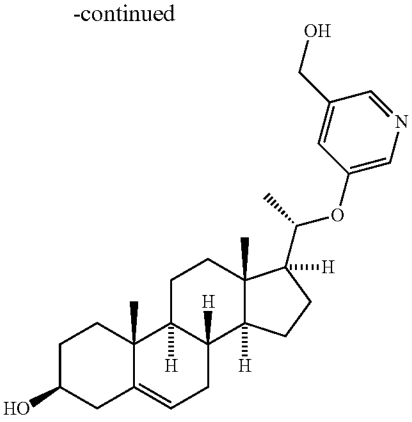

To a solution of compound A (200 mg, 601 μmol) in DMSO (8 mL) was added compound B (127 mg, 902 μmol) and t-BuOK (202 mg, 1.8 mmol) and the reaction was heated to 130° C. for 16 hours under nitrogen. The reaction was diluted with water and extracted with ethyl acetate. The organic layer was concentrated under reduced pressure. The crude product was purified by prep-TLC to give compound C (150 mg, 56%) as a white solid. To a 0° C. solution of compound C (150 mg, 331 μmol) in THF (6 mL) was added $BH_3$-THF (1 mL, 1 mmol, 1M in THF) and the reaction stirred at room temperature for 16 hours under nitrogen. The reaction was quenched with MeOH and concentrated. The residue was diluted with water and extracted with ethyl acetate. The organic layer was concentrated under reduced pressure. The crude product was purified by Prep-TLC to give compound D (110 mg, 76%) as a white solid.

(5-((1S)-1-((1aR,3aR,3bS,5aS,6S,8aS,8bS,10aS)-10-methoxy-3a,5a-dimethylhexadecahydrocyclopenta[a]cyclopropa[2,3]cyclopenta[1,2-f]naphthalen-6-yl)ethoxy)pyridin-3-yl)methanol (110 mg, 250 μmol) was reacted according to the method of Example 430 to afford the title compound 436 (25 mg, 23%) as a white solid LCMS: $[M+H]^+$=426.20 $^1$H NMR (400 MHz, Chloroform-d) δ 8.31 (s, 1H), 8.14 (s, 1H), 7.49 (s, 1H), 5.36 (d, J=5.2 Hz, 1H), 4.81 (s, 2H), 4.36 (t, J=6.8 Hz, 1H), 3.59-3.46 (m, 1H), 2.33-2.19 (m, 3H), 2.05-1.83 (m, 6H), 1.70-1.44 (m, 8H), 1.35 (d, J=6.0 Hz, 3H), 1.29-1.04 (m, 7H), (s, 3H), 0.72 (s, 3H).

Example 437: (3S,8S,9S,10R,13S,14S,17S)-17-((S)-1-((4-(hydroxymethyl)pyridin-3-yl) oxy)ethyl)-10, 13-dim ethyl-2, 3,4, 7,8, 9,10,11,12,13,14,15,16,17-tetradecahydro-1H-cyclopenta[a]phenanthren-3-ol

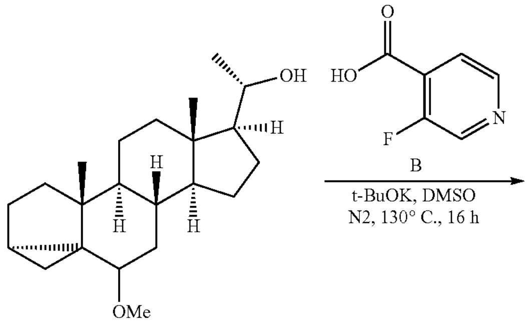

A

-continued

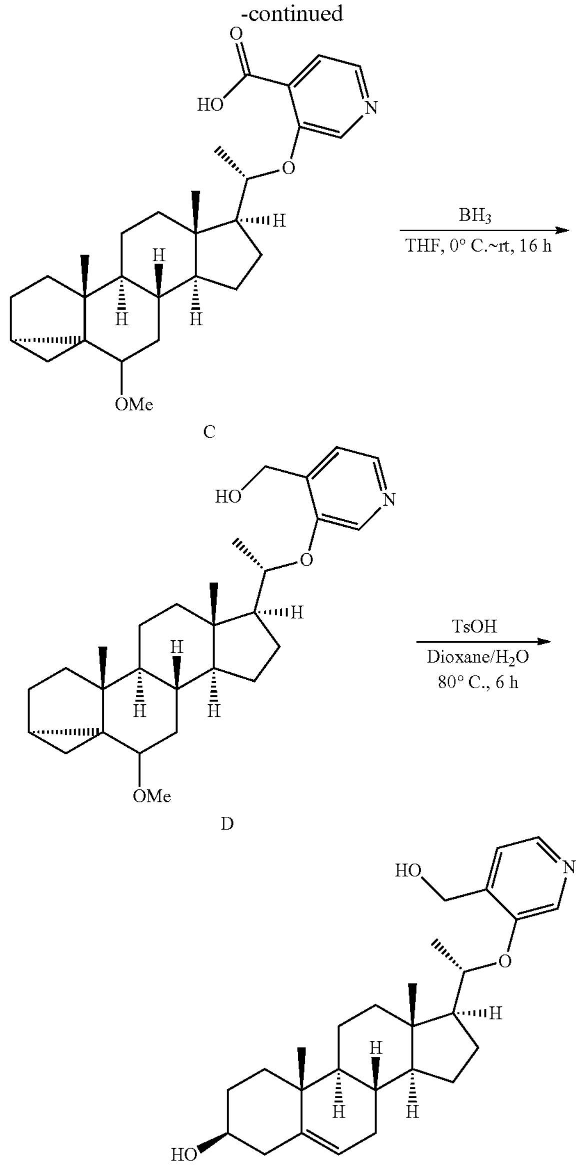

To a solution of compound A (600 mg, 1.8 mmol) in DMSO (30 mL) was added compound B (382 mg, 2.71 mmol) and tBuOK (607 mg, 5.41 mmol) and the reaction was heated to 130° C. for 16 hours under nitrogen. The reaction was diluted with water and extracted with ethyl acetate. The organic layer was concentrated under reduced pressure. The crude product was purified by prep-TLC to give compound C (800 mg, 97%). To a 0° C. solution of compound C (200 mg, 428 μmol) in THF (6 mL) was added BH3-THF (1.3 mL, 1.3 mmol, 1M in THF) and the reaction was warmed to room temperature for 16 hours under nitrogen. The reaction was quenched with MeOH and concentrated. The reaction was diluted with water and extracted with ethyl acetate. The organic layer was concentrated under reduced pressure. The crude product was purified by Prep-TLC to give compound D (90 mg, 50%).

(3-((1S)-1-((1aR,3aR,3bS,5aS,6S,8aS,8bS,10aS)-10-methoxy-3a,5a-dimethylhexadecahydrocyclopenta[a]cyclopropa[2,3]cyclopenta[1,2-f]naphthalen-6-yl)ethoxy)pyridin-4-yl)methanol (90 mg, 205 μmol) was reacted according to the method of Example 430 to afford the title compound 437 (70 mg, 80%) as a white solid. LCMS: $[M+1]^+$=426.20. $^1$H NMR (400 MHz, Chloroform-d) δ 8.16 (d, J=4.0 Hz, 2H), 7.39 (d, J=4.8 Hz, 1H), 5.34 (s, 1H), 4.70 (s, 2H), 4.47-4.39 (m, 1H), 3.57-3.35 (m, 2H), 2.33-2.20 (m, 2H), 2.03-1.41 (m, 13H), 1.34 (d, J=6.0 Hz, 3H), 1.26-1.02 (m, 5H), 1.00 (s, 3H), 0.96 (d, J=4.4 Hz, 1H), 0.70 (s, 3H).

Example 438: 5-((S)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethoxy)-N-methylpicolinamide

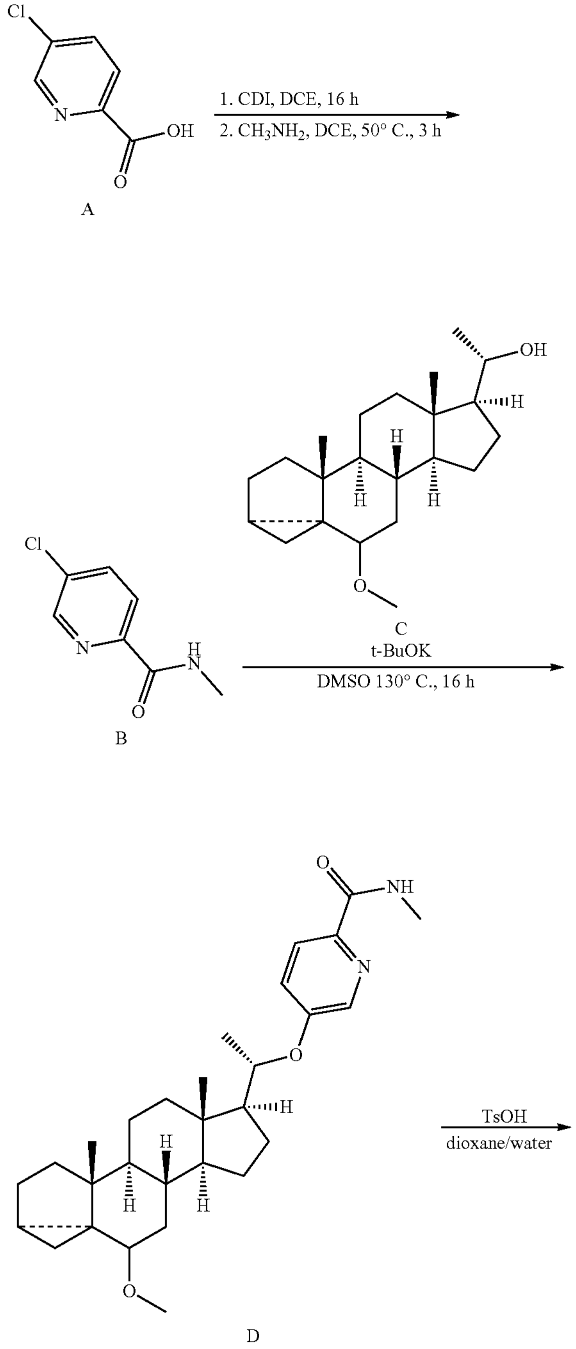

-continued

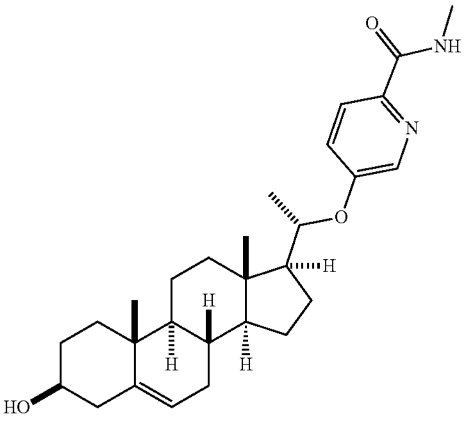

To a solution of compound A (1.5 g, 9.52 mmol) in 1, 2-dichloroethane (10 mL) was added 1-(1H-imidazole-1-carbonyl)-1H-imidazole (3.1 g, 19.11 mmol) and the reaction was stirred at room temperature for 16 hours. Methylamine (2 M in solution of THF, 28.5 ml, 57.1 mmol) was added to the solution, the reaction was stirred at 50° C. for 3 hours. The solution was quenched with water and extracted with DCM. The organic layer was dried over sodium sulfate and concentrated under reduced pressure. The crude product was purified by column chromatography on silica gel to compound B (880 mg, 27%). To a solution of compound C (0.3 g, 902 μmol) in DMSO (6 mL) was added compound B (308 mg, 1.8 mmol) and t-BuOK (506 mg, 4.51 mmol) and the reaction was warmed to 130° C. under $N_2$ for 16 hours. Upon completion, the reaction was quenched with water and extracted with ethyl acetate. The organic layer was washed with brine, dried over sodium sulfate, filtered, and concentrated under reduced pressure. The crude product was purified by column chromatography on silica gel to afford compound D (50 mg, 12%).

5-((S)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethoxy)-N-methylpicolinamide (50 mg, 107 μmol) was reacted according to the method of Example 430 to afford the title compound 438 (39.1 mg, 57.8%) as a white solid. LCMS: $[M+H]^+$=453.20. $^1H$ NMR (400 MHz, Chloroform-d) δ 8.13-8.08 (m, 2H), 7.81 (d, J=6.0 Hz, 1H), 7.23 (dd, J=8.8, 2.8 Hz, 1H), 5.36 (dd, J=4.8, 2.4 Hz, 1H), 4.41-4.30 (m, 1H), 3.53 (dt, J=11.6, 6.4 Hz, 1H), 3.01 (d, J=5.2 Hz, 3H), 2.34-2.19 (m, 2H), 2.04-1.82 (m, 5H), 1.69 (q, J=8.8 Hz, 2H), 1.61-1.43 (m, 13H), 1.34 (d, J=6.0 Hz, 3H), 1.29-0.92 (m, 10H), 0.85 (dt, J=16.4, 7.2 Hz, 1H), 0.72 (s, 3H).

Example 439: 5—((S)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethoxy)-N-methylnicotinamide

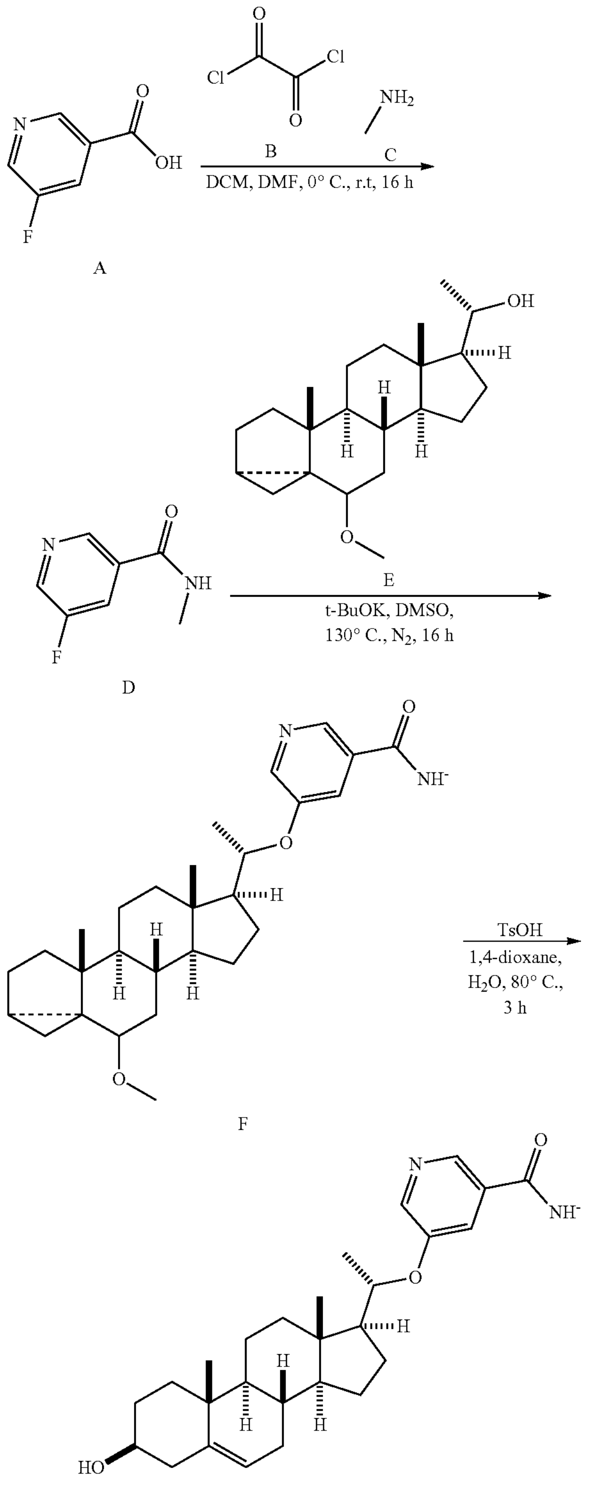

To a 0° C. solution of compound A (1.8 g, 12.8 mmol) in DCM (30 mL) was added compound B (4.05 g, 31.9 mmol) and 1 drop of DMF and the reaction was stirred at 0° C. for 2 hours. Compound C (1.19 g, 38.3 mmol) was added to the solution and the reaction stirred at room temperature under $N_2$ for 16 h. The reaction was quenched with saturated aqueous $NH_4Cl$ and extracted with EtOAc. The organic layer was washed with brine, dried over sodium sulfate, filtered, and concentrated. The residue was purified by silica gel chromatography to afford compound D (500 mg, 25.4%) as a white solid. To a solution of compound D (487 mg, 3.16 mmol) in dimethyl sulfoxide (10.4 mL) was added compound E (350 mg, 1.05 mmol) and tBuOK (472 mg, 4.21 mmol) and the reaction was stirred at 130° C. under $N_2$ for 16 h. The reaction was quenched with saturated aqueous $NH_4Cl$ and extracted with EA. The organic layer was washed with brine, dried over sodium sulfate, filtered, and concentrated. The residue was purified by column chromatography on silica gel to afford compound F (280 mg, 19%) as a white solid.

5-((1S)-1-((1aR,3aR,3bS,5aS,6S,8aS,8bS,10aR)-10-methoxy-3a,5a-dimethylhexadecahydrocyclopenta[a]cyclopropa[2,3]cyclopenta[1,2-f]naphthalen-6-yl)ethoxy)-N-methylnicotinamide (280 mg, 0.6 mmol) was reacted according to the method of Example 430 to afford the title compound 439 (38.9 mg, 14.3%) as a white solid. LCMS: $[M+1]^+$=453.20. $^1H$ NMR (400 MHz, Chloroform-d) δ 8.39 (d, J=35.2 Hz, 2H), 7.62 (t, J=2.0 Hz, 1H), 6.17 (s, 1H), 5.36 (s, 1H), 4.42-4.33 (m, 1H), 3.58-3.48 (m, 1H), 3.04 (d, J=4.8 Hz, 3H), 2.36-2.19 (m, 2H), 2.05-1.80 (m, 6H), 1.72-1.63 (m, 2H), 1.57-1.40 (m, 6H), 1.33 (d, J=6.0 Hz, 3H), 1.24-1.04 (m, 4H), 1.01 (s, 3H), 0.99-0.81 (m, 2H), 0.72 (s, 3H).

Example 440: (1R,3aS,3bS,7S,9aR,9bS,11aS)-9a,11a-dimethyl-1-[(2S)-1-[(6-methylpyridin-2-yl)oxy]propan-2-yl]-1H,2H,3H,3aH,3bH,4H,6H,7H,8H,9H,9aH,9bH,10H,11H,11aH-cyclopenta[a]phenanthren-7-ol

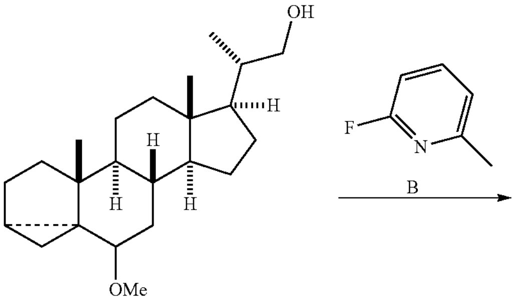

A

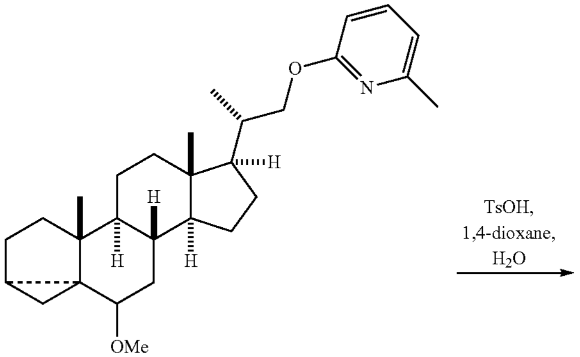

C

-continued

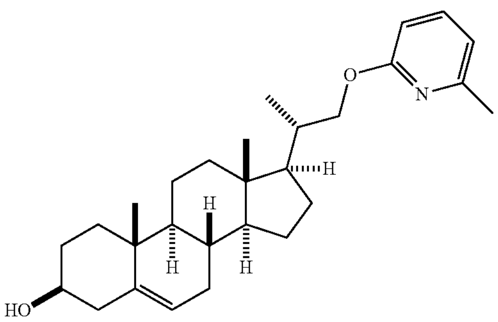

To a solution of compound A (300 mg, 866 μmol) in DMF (4 mL) was added compound B (96.2 mg, 866 μmol) and t-BuOK (389 mg, 3.46 mmol). The reaction was stirred at room temperature for 4 hours. The reaction was added water (40 mL) and extracted with ethyl acetate (20 mL*2). The combined organic layer was concentrated to give crude. The crude was purified by column to give compound C (150 mg, 41%).

2-((2S)-2-((1aR,3 aR,3bS,5aS,6R,8aS,8bS,10aR)-10-methoxy-3a,5a-dimethylhexadecahydrocyclopenta[a]cyclopropa[2,3]cyclopenta[1,2-f]naphthalen-6-yl)propoxy)-6-methylpyridine (150 mg, 343 μmol) was reacted according to the method of Example 430 to afford the title compound 440 (34 mg, 23%) as a white solid. LCMS: $[M+H]^+$=424.25. $^1H$ NMR (400 MHz, Chloroform-d) δ 8.02 (t, J=3.1 Hz, 1H), 7.07 (d, J=3.1 Hz, 2H), 5.36 (dd, J=5.0, 2.2 Hz, 1H), 4.35-4.21 (m, 1H), 3.58-3.50 (m, J=10.8, 4.6 Hz, 1H), 2.45 (s, 3H), 2.35-2.18 (m, 2H), 2.10-1.79 (m, 7H), 1.76-1.37 (m, 9H), 1.30 (d, J=6.1 Hz, 3H), 1.28-1.04 (m, 6H), 1.01 (s, 3H), 0.99-0.85 (m, 1H), 0.71 (s, 3H).

Example 441: (3S,8S,9S,10R,13S,14S,17R)-10,13-dimethyl-17-((S)-1-((5-methylpyridin-2-yl)oxy) propan-2-yl)-2,3,4,7,8,9,10,11,12,13,14,15,16,17-tetradecahydro-1H-cyclopenta[a]phenanthren-3-ol

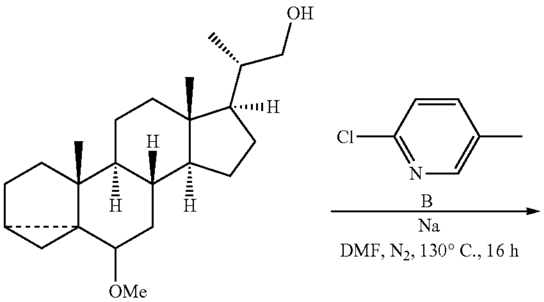

A

-continued

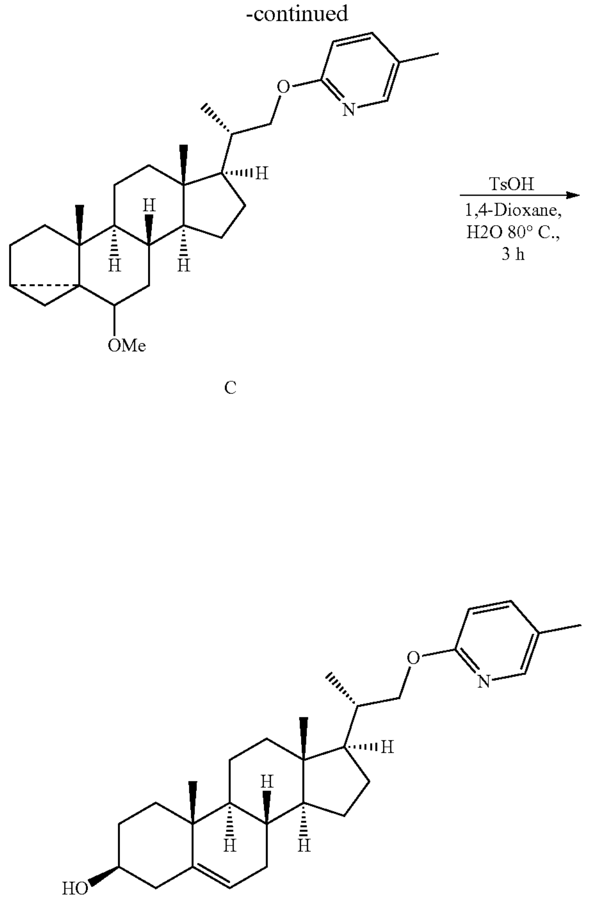

C

To a solution of compound A (100 mg, 289 μmol) in DMF (2 mL) was added NaH (33.2 mg, 0.83 mmol, 60% dispersion in mineral oil) and then compound B (73.6 mg, 577 μmol). The reaction was stirred at 130° C. under $N_2$ for 16 h. The reaction was quenched with water and extracted with EtOAc. The organic layer was washed with brine, dried over sodium sulfate, and concentrated under reduced pressure. The crude product was purified by silica gel chromatography to afford compound C (100 mg, 79%) as a yellow oil.

To a solution of compound C (100 mg, 228 μmol) in 1, 4-dioxane (2 mL) and water (0.5 mL) was added TsOH·$H_2O$ (8.69 mg, 45.7 μmol). The reaction was stirred at 80° C. for 3 h. The reaction was quenched with water and extracted with EtOAc. The organic layer was washed with brine, dried over sodium sulfate, and concentrated under reduced pressure. The crude product was purified by silica gel chromatography to afford the title compound 441 (25 mg, 25.8%) as a white solid. LCMS: $[M+1]^+$=424.20. $^1H$ NMR (400 MHz, Chloroform-d) δ 8.18 (bs, 1H), 7.84 (d, J=8.6 Hz, 1H), 7.00 (d, J=8.8 Hz, 1H), 5.38 (d, J=5.2 Hz, 1H), 4.53 (d, J=9.2 Hz, 1H), 4.30 (t, J=8.4 Hz, 1H), 3.61-3.50 (m, 1H), 2.39 (s, 3H), 2.35-2.25 (m, 2H), 2.08-1.85 (m, 7H), 1.71-1.59 (m, 2H), 1.59-1.47 (m, 5H), 1.47-1.36 (m, 3H), 1.34-1.23 (m, 4H), 1.19 (d, J=6.6 Hz, 3H), 1.14 (dd, J=13.2, 4.2 Hz, 2H), 1.10-1.06 (m, 1H), 1.05 (s, 3H), 1.02-0.87 (m, 2H), 0.77 (s, 3H).

Example 442: (1R,3aS,3bS,7S,9aR,9bS,11aS)-9a, 11a-dimethyl-1-[(2S)-1-[(4-methylpyridin-2-yl)oxy]propan-2-yl]-1H,2H,3H,3aH,3bH,4H,6H,7H,8H,9H, 9aH,9bH,10H,11H,11aH-cyclopenta[a]phenanthren-7-ol

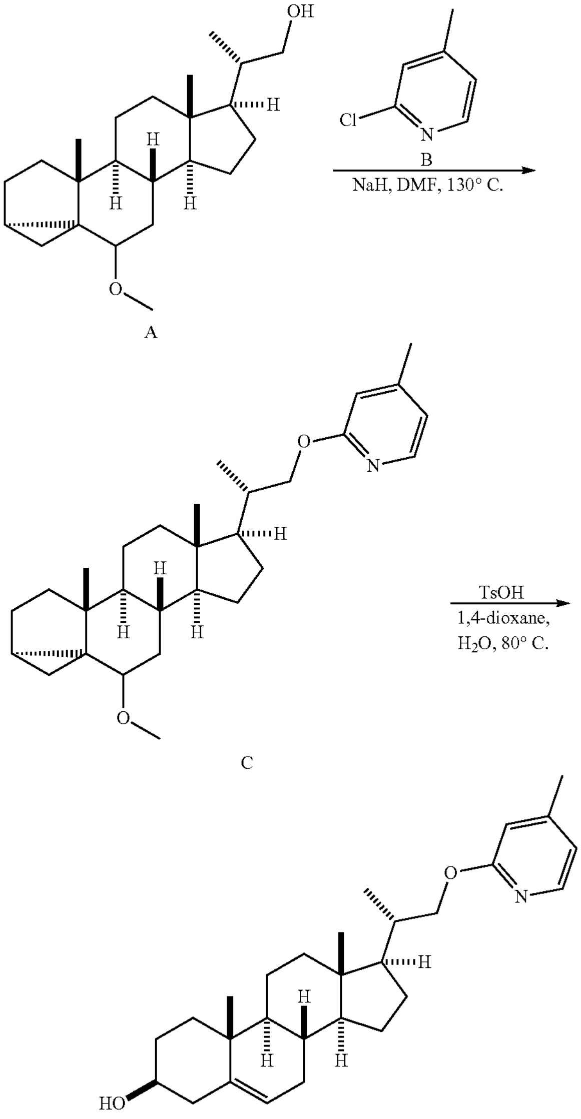

A B C

To a 0° C. solution of compound A (300 mg, 866 μmol) in DMF (5 mL) was added NaH (83 mg, 2.07 mmol, 60% dispersion in mineral oil) and the reaction was warmed to room temperature for 0.5 hour. Compound B (221 mg, 1.73 mmol) was added and the reaction was heated to 130° C. for 16 hours. The reaction was cooled to room temperature. Water (40 mL) was added, and the reaction was extracted with EtOAc (30 mL*3). The combined organic phase was washed with water (50 mL*2), brine (50 mL), dried over sodium sulfate and concentrated under reduced pressure. The residue was purified by silica gel chromatography to afford compound C (140 mg, 37%) as a white solid.

2-((2S)-2-((1aR,3 aR,3bS,5aS,6R,8aS,8bS,10aS)-10-methoxy-3a,5a-dimethylhexadecahydrocyclopenta[a]cyclopropa[2,3]cyclopenta[1,2-f]naphthalen-6-yl)propoxy)-4-methylpyridine (140 mg, 320 μmol) was reacted according to the method of Example 430 to afford the title compound 442 (50 mg, 37%) as a white solid. LCMS: $[M+H]^+$=424.3. $^1$H NMR (400 MHz, Chloroform-d) δ 7.99 (d, J=5.2 Hz, 1H), 6.66 (d, J=5.2 Hz 1H), 6.55 (s, 1H), 5.35 (d, J=7.6 Hz, 1H), 4.22 (dd, J=10.0, 3.2 Hz, 1H), 3.99 (dd, J=10.0, 3.2 Hz, 1H), 3.53 (s, 1H), 2.39-2.16 (m, 5H), 2.08-1.94 (m, 2H), 1.91-1.82 (m, 4H), 1.56-1.38 (m, 7H), 1.37-1.19 (m, 3H), 1.16-1.06 (m, 5H), 1.02 (s, 4H), 0.98-0.83 (m, 2H), 0.73 (s, 3H).

Example 443: (3S,8S,9S,10R,13S,14S,17R)-10,13-dimethyl-17-((S)-1-((3-methylpyridin-2-yl)oxy) propan-2-yl)-2,3,4,7,8,9,10,11,12,13,14,15,16,17-tetradecahydro-1H-cyclopenta[a]phenanthren-3-ol

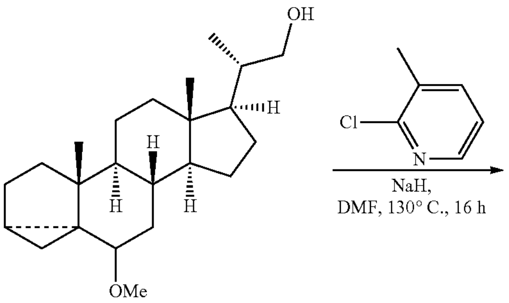

A

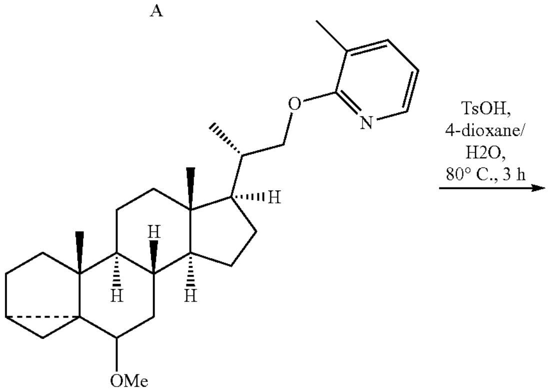

B

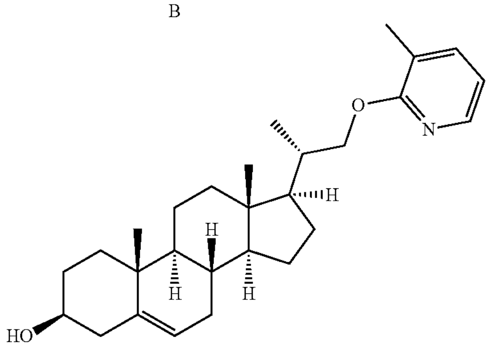

A solution of compound A (200 mg, 577 μmol), NaH (111 mg, 2.77 mmol, 60% dispersion in mineral oil) and 2-chloro-3-methylpyridine (147 mg, 1.15 mmol) in dry DMF (4 mL) was stirred at 130° C. for 16 h under $N_2$ atmosphere. The reaction was quenched with water (5 mL) and extracted with EtOAc (10 mL). The organic phase concentrated under reduced pressure. The crude product was purified by silica gel chromatography to give compound B (170 mg, 67%).

2-((2S)-2-((1aR,3 aR,3bS,5aS,6R,8aS,8bS,10aR)-10-methoxy-3a,5a-dimethylhexadecahydrocyclopenta[a]cyclopropa[2,3]cyclopenta[1,2-f]naphthalen-6-yl)propoxy)-3-methylpyridine (170 mg, 388 μmol) was reacted according to the method of Example 430 to afford the title compound 443 (80 mg, 49%) as a white solid. $^1$H NMR (400 MHz, Chloroform-d) δ 8.02-7.92 (m, 1H), 7.36 (d, J=7.2 Hz, 1H), 6.75 (dd, J=7.2, 5.2 Hz, 1H), 5.36 (d, J=5.2 Hz, 1H), 4.28 (dd, J=10.0, 3.2 Hz, 1H), 4.02 (dd, J=10.2, 7.2 Hz, 1H), 3.58-3.48 (m, 1H), 2.36-2.21 (m, 2H), 2.20 (s, 3H), 2.09-2.03 (m, 1H), 2.01-1.94 (m, 1H), 1.94-1.78 (m, 4H), 1.66-1.58 (m, 2H), 1.52-1.46 (m, 4H), 1.43-1.33 (m, 2H), 1.32-1.16 (m, 3H), 1.14 (d, J=6.6 Hz, 3H), 1.12-1.05 (m, 2H), 1.02 (s, 3H), 1.00-0.93 (m, 1H), 0.75 (s, 3H).

Example 444: (3S,8S,9S,10R,13S,14S,17R)-17-((S)-1-((6-(hydroxymethyl)pyridin-2-yl)oxy)propan-2-yl)-10,13-dimethyl-2,3,4,7,8,9,10,11,12,13,14,15,16,17-tetradecahydro-1H-cyclopenta[a]phenanthren-3-ol

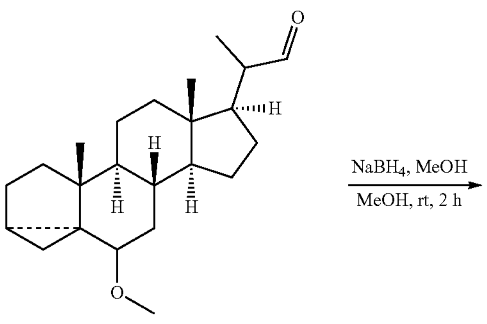

A

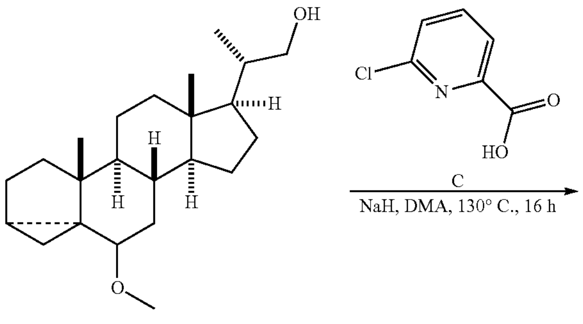

B

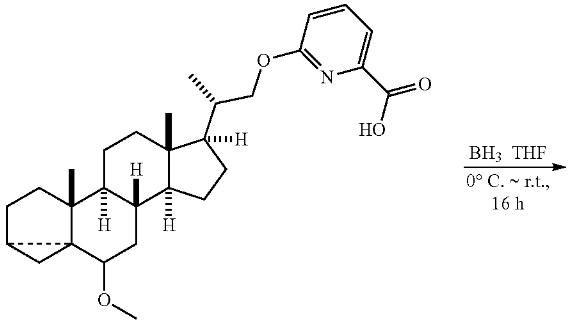

D

-continued

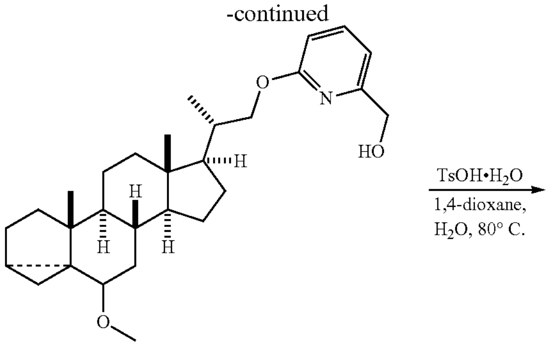

E

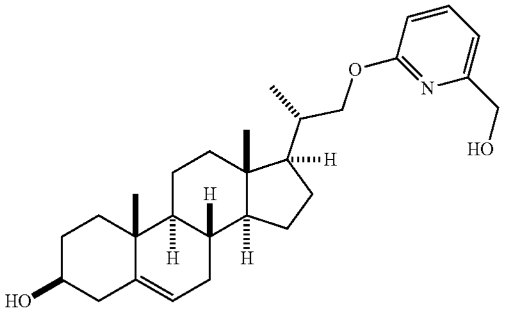

To a solution of compound A (3.0 g, 8.71 mmol) in methanol (20 mL) was added $NaBH_4$ and the reaction was stirred at room temperature under $N_2$ for 2 h. The reaction was quenched with saturated aqueous $NH_4Cl$ (10 mL) and extracted with EtOAc (40 mL). The organic layer was washed with brine (10 mL), dried over sodium sulfate, filtered, and concentrated under reduced pressure. The residue was purified by silica gel chromatography to afford compound B (3.0 g) as a white solid. To a solution of compound B (1.0 g, 2.89 mmol) and compound C (1.36 g, 8.66 mmol) in DMF (20 mL) was added NaH (332 mg, 8.3 mmol, 60% dispersion in mineral oil) and the reaction was stirred at 130° C. under $N_2$ for 16 h. The reaction was quenched with saturated aqueous $NH_4Cl$ (5 mL) and extracted with EtOAc (30 mL). The organic layer was washed with brine, dried over sodium sulfate, filtered, and concentrated. The residue was purified by silica gel chromatography to afford compound D (1.3 g, 96%). To a 0° C. solution of compound D (200 mg, 0.42 mmol) in tetrahydrofuran (3 mL) was added $BH_3$ (1.28 mL, 1M in THF, 1.28 mmol) and the reaction was warmed to room temperature under $N_2$ for 16 h. The reaction was quenched with methanol (2 mL) and the solvent was concentrated under reduced pressure. The residue was purified by silica gel chromatography to afford compound E (80 mg, 41.2%).

(6-((2S)-2-((1aR,3aR,3bS,5aS,6R,8aS,8bS,10aR)-10-methoxy-3a,5a-dimethylhexadecahydrocyclopenta[a]cyclopropa[2,3]cyclopenta[1,2-f]naphthalen-6-yl)propoxy)pyridin-2-yl)methanol (60 mg, 0.13 mmol) was reacted according to the method of Example 430 to afford the title compound 444 (29.9 mg, 34.48%) as a white solid. LCMS: $[M+1]^+$=440.20. $^1H$ NMR (400 MHz, DMSO-$d_6$) δ 7.72-7.64 (m, 1H), 7.03 (d, J=7.2 Hz, 1H), 6.64 (d, J=8.2 Hz, 1H), 5.33 (t, J=5.6 Hz, 1H), 5.28 (d, J=5.2 Hz, 1H), 4.62 (d, J=4.4 Hz, 1H), 4.45 (d, J=5.6 Hz, 2H), 4.22 (dd, J=10.4, 3.2 Hz, 1H), 3.94 (dd, J=10.4, 7.2 Hz, 1H), 3.27 (dt, J=10.8, 5.2 Hz, 2H), 2.21-1.76 (m, 8H), 1.73-1.48 (m, 5H), 1.47-1.29 (m, 7H), 1.24-1.09 (m, 3H), 1.07 (d, J=6.4 Hz, 3H), 1.05-0.99 (m, 2H), 0.97 (s, 3H), 0.94-0.83 (m, 2H), 0.71 (s, 3H).

Example 445: (3S,8S,9S,10R,13S,14S,17R)-17-((S)-1-((5-(hydroxymethyl)pyridin-2-yl)oxy)propan-2-yl)-10,13-dimethyl-2,3,4,7,8,9,10,11,12,13,14,15,16,17-tetradecahydro-1H-cyclopenta[a]phenanthren-3-ol

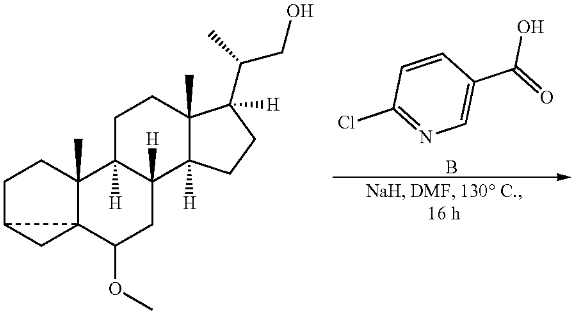

A

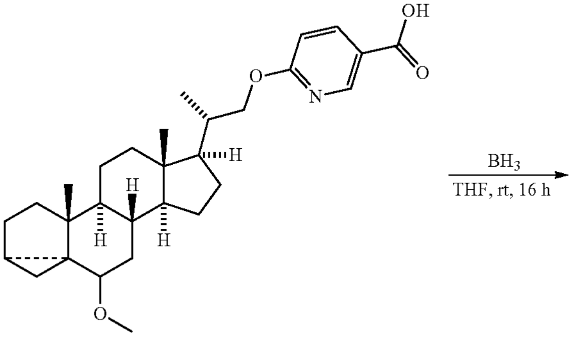

C

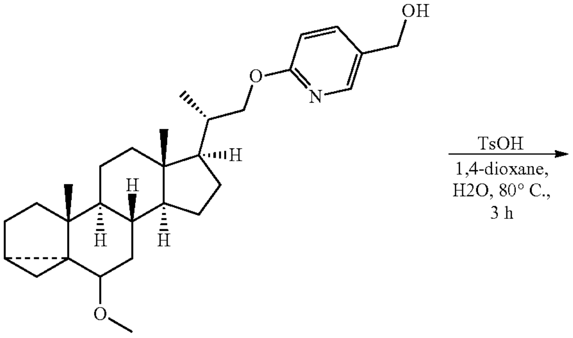

D

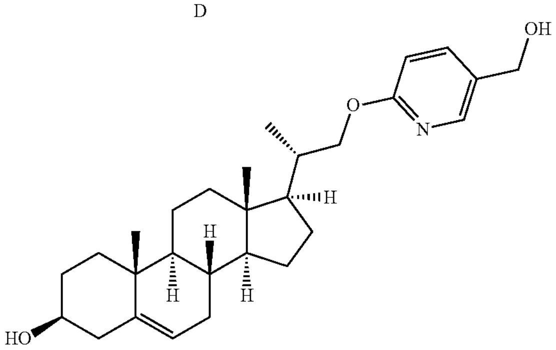

To a solution of compound A (500 mg, 1.44 mmol) in DMF (5 mL) was added NaH (166 mg, 4.15 mmol, 60% dispersion in mineral oil) and compound B (455 mg, 2.89 mmol) and the reaction was heated to 130° C. under $N_2$ for 16 h. The reaction was quenched with water, adjusted pH=1~2 with HCl (1M) and extracted with Ethyl Acetate (20 mL). The organic layer was washed with brine (5 mL), dried over sodium sulfate and concentrated under reduced pressure. The crude product was purified by Prep-TLC to afford compound C (380 mg, 56.5%) as a yellow oil. To a 0° C. solution of compound C (140 mg, 299 μmol) in THF (2.8 mL) was added $BH_3$ (0.9 mL, 1M in THF, 900 μmol) and the reaction was warmed to room temperature under $N_2$ for 15 h. Upon completion, the reaction concentrated under reduced pressure. The crude product was purified by Prep-TLC to afford compound D (50 mg, 36.8%) as a yellow oil.

To a solution of compound D (50 mg, 110 μmol) in 1,4-dioxane (0.8 mL) and water (0.2 mL) was added TsOH (4.2 mg, 22 μmol). The reaction was stirred at 80° C. for 3 h. The reaction concentrated under reduced pressure. The crude product was purified by silica gel chromatography to afford the title compound 445 (10.7 mg, 22.1%) as a white solid. LCMS: $[M+1]^+$=440.20. $^1$H NMR (400 MHz, Chloroform-d) δ 8.12 (d, J=2.4 Hz, 1H), 7.63 (dd, J=8.6, 2.4 Hz, 1H), 6.75 (d, J=8.4 Hz, 1H), 5.35 (d, J=5.2 Hz, 1H), 4.62 (s, 2H), 4.27 (dd, J=10.2, 3.2 Hz, 1H), 4.02 (dd, J=10.0, 7.6 Hz, 1H), 3.59-3.48 (m, 1H), 2.34-2.19 (m, 2H), 2.08-1.80 (m, 7H), 1.67-1.46 (m, 14H), 1.41-1.28 (m, 6H), 1.24-1.15 (m, 2H), 1.12 (d, J=6.4 Hz, 3H), 1.07 (dd, J=12.4, 6.4 Hz, 2H), 1.02 (s, 3H), 0.99-0.87 (m, 2H), 0.74 (s, 3H).

Example 446: (3S,8S,9S,10R,13S,14S,17R)-17-((S)-1-((4-(hydroxymethyl)pyridin-2-yl)oxy)propan-2-yl)-10,13-dimethyl-2,3,4,7,8,9,10,11,12,13,14,15,16,17-tetradecahydro-1H-cyclopenta[a]phenanthren-3-ol

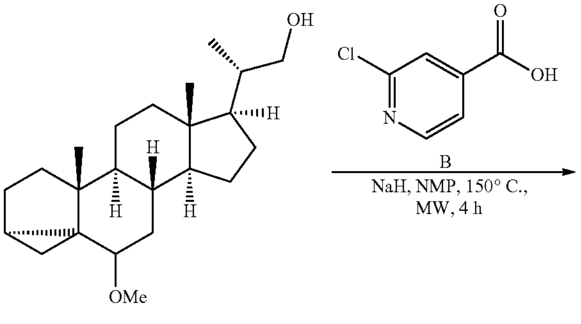

A

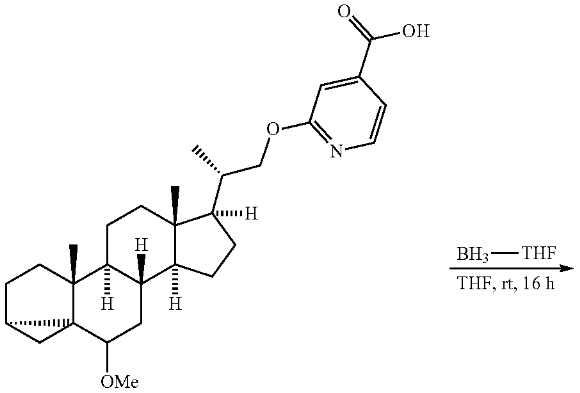

C

-continued

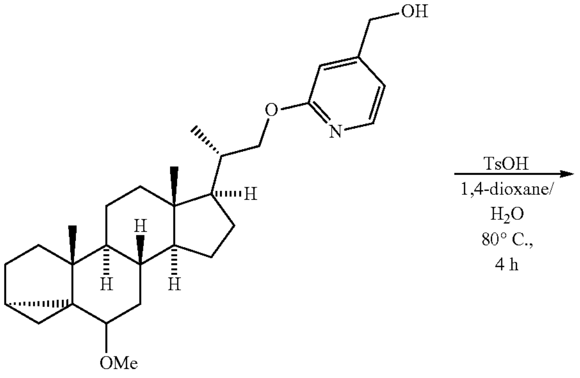

D

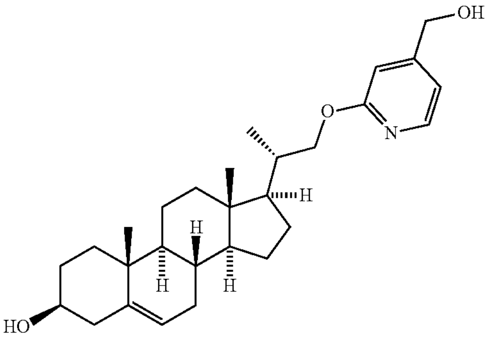

To a solution of compound A (600 mg, 1.82 mmol) in NMP (6 mL) was added compound B (286 mg, 1.82 mmol) and NaH (417 mg, 10.4 mmol, 60% dispersion in mineral oil) and the reaction was heated at 150° C.; for 4 h under microwave irradiation. The reaction was diluted with water (10 mL) and extracted with ethyl acetate (30 mL). The organic layer was concentrated under reduced pressure. The crude product was purified by prep-TLC to give compound C (520 mg, 64%) as solid. To a 0° C. solution of compound C (200 mg, 428 μmol) in THF (6 mL) was added $BH_3$-THF (1.3 mL, 1.3 mmol, 1M in THF) and the reaction was warmed to room temperature for 16 hours under nitrogen. The reaction was quenched with MeOH (4 mL) and concentrated. The residue was diluted with water (5 mL) and extracted with ethyl acetate (20 mL). The organic layer was concentrated under reduced pressure. The crude product was purified by Prep-TLC to give compound D (120 mg, 62%) as solid.

(2-((2S)-2-((1aR,3aR,3bS,5aS,6R,8aS,8bS,10aS)-10-methoxy-3a,5a-dimethylhexadecahydrocyclopenta[a]cyclopropa[2,3]cyclopenta[1,2-f]naphthalen-6-yl)propoxy)pyridin-4-yl)methanol (120 mg, 265 μmol) was reacted according to the method of Example 430 to afford the title compound 446 (26 mg, 22%) as a white solid. LCMS: $[M+H]^+$=440.20. $^1$H NMR (400 MHz, Chloroform-d) δ 8.10 (d, J=5.2 Hz, 1H), 6.82 (dd, J=5.2, 1.2 Hz, 1H), 6.75 (s, 1H), 5.35 (d, J=5.2 Hz, 1H), 4.68 (d, J=5.2 Hz, 2H), 4.25 (dd, J=10.0, 3.2 Hz, 1H), 4.01 (dd, J=10.0, 7.2 Hz, 1H), 3.53 (s, 1H), 2.32-2.22 (m, 2H), 2.07-2.02 (m, 1H), 1.96 (bs, 1H), 1.90-1.86 (m, 2H), 1.84 (s, 1H), 1.75 (t, J=6.0 Hz, 1H), 1.66-1.59 (m, 1H), 1.54-1.22 (m, 10H), 1.12 (d, J=6.4 Hz, 3H), 1.07 (d, J=14.4, 5.2 Hz, 2H), 1.02 (s, 3H), 0.74 (s, 3H).

Example 447: (3S,8S,9S,10R,13S,14S,17R)-17-((S)-1-((3-(hydroxymethyl)pyridin-2-yl)oxy)propan-2-yl)-10,13-dimethyl-2,3,4,7,8,9,10,11,12,13,14,15,16,17-tetradecahydro-1H-cyclopenta[a]phenanthren-3-ol

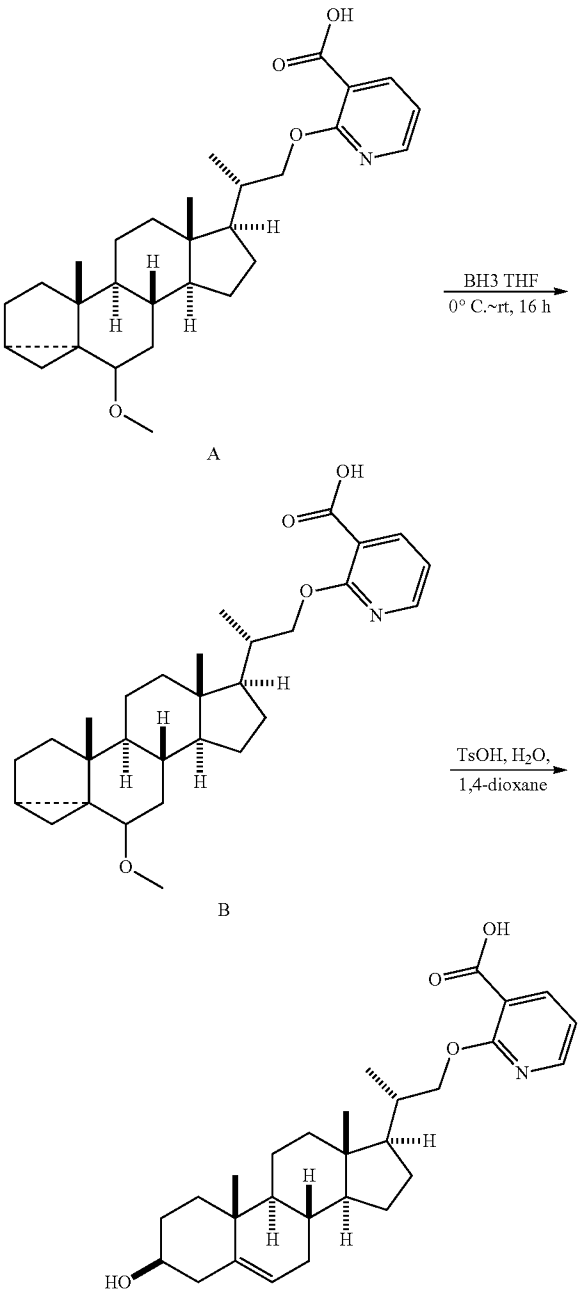

To a 0° C. solution of compound A (50 mg, 107 μmol) in THF (3 mL) was added $BH_3$ (0.32 mL, 1M in THF, 0.32 mmol) and the reaction was warmed to room temperature for 16 hours under $N_2$. The reaction was quenched with MeOH (5 mL), the reaction concentrated under vacuum to afford compound B (48 mg, 98%) as a yellow solid.

(2-((2S)-2-((1aR,3aR,3bS,5aS,6R,8aS,8bS,10aR)-10-methoxy-3a,5a-dimethylhexadecahydrocyclopenta[a]cyclopropa[2,3]cyclopenta[1,2-f]naphthalen-6-yl)propoxy)pyridin-3-yl)methanol(50 mg, 110 μmol) was reacted according to the method of Example 430 to afford the title compound 447 (15 mg, 31%) as a white solid. LCMS: $[M+H]^+$=440.20. $^1$H NMR (400 MHz, Chloroform-d) δ 8.07 (dd, J=5.2, 1.6 Hz, 1H), 7.57 (d, J=7.2 Hz, 1H), 6.86 (dd, J=7.2, 5.2 Hz, 1H), 5.35 (d, J=5.2 Hz, 1H), 4.67 (s, 2H), 4.35 (dd, J=10.4, 3.2 Hz, 1H), 4.10 (dd, J=10.6, 7.0 Hz, 1H), 3.52 (td, J=11.2, 5.6 Hz, 1H), 2.34-2.19 (m, 3H), 2.07-1.80 (m, 7H), 1.55-1.41 (m, 7H), 1.38-1.29 (m, 2H), 1.24-1.20 (m, 1H), 1.13 (d, J=6.8 Hz, 3H), 1.11-1.04 (m, 2H), 1.02 (s, 3H), 0.99-0.93 (m, 1H), 0.74 (s, 3H).

Example 448: 6—((S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propoxy)-N-methylpicolinamide

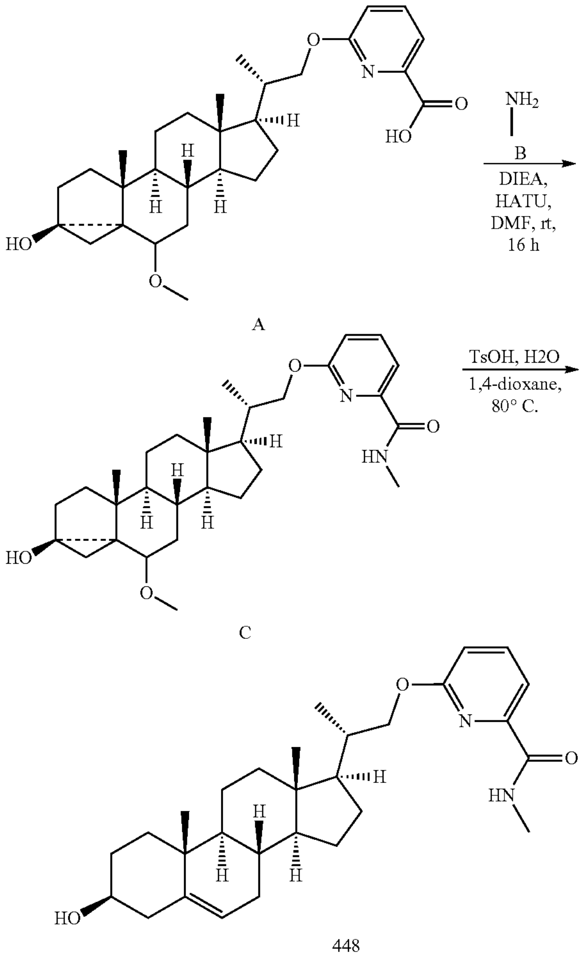

To a solution of compound A (400 mg, 0.85 mmol) and compound B (31.9 mg, 1.03 mmol) in DMF (7 mL) was added HATU (650 mg, 1.71 mmol), DIEA (663 mg, 5.13 mmol) and the reaction was stirred at room temperature under $N_2$ for 16 h. The reaction was quenched with saturated aqueous $NH_4Cl$ (5 mL) and extracted with EtOAc (15 mL). The organic layer was washed with brine (5 mL), dried over sodium sulfate, filtered, and concentrated. The residue was purified by silica gel chromatography to afford compound C (120 mg, 29.2%) as a white solid.

6-((2S)-2-((1aR,3 aR,3bS,5aS,6R,8aS,8bS,10aR)-10-methoxy-3a,5a-dimethylhexadecahydrocyclopenta[a]cyclopropa[2,3]cyclopenta[1,2-f]naphthalen-6-yl)propoxy)-N-methylpicolinamide (120 mg, 0.25 mmol) was reacted according to the method of Example 430 to afford the title compound 448 (44.6 mg, 38.4%) as a white solid. LCMS: $[M+23]^+$=489.20. $^1$H NMR (400 MHz, Chloroform-d) δ 7.80-7.72 (m, 2H), 7.69 (t, J=7.6 Hz, 1H), 6.87 (d, J=8.0 Hz, 1H), 5.36 (d, J=5.2 Hz, 1H), 4.29 (dd, J=10.0, 3.2 Hz, 1H), 4.01 (dd, J=10.0, 7.2 Hz, 1H), 3.62-3.50 (m, 1H), 3.03 (d, J=5.2 Hz, 3H), 2.34-2.21 (m, 2H), 2.08-1.96 (m, 2H), 1.93-1.82 (m, 4H), 1.69-1.61 (m, 2H), 1.54-1.46 (m, 4H), 1.45-1.41 (m, 2H), 1.39-1.34 (m, 1H), 1.31-1.27 (m, 2H), 1.24-1.16 (m, 1H), 1.13 (d, J=6.4 Hz, 3H), 1.08 (dd, J=10.4, 3.6 Hz, 1H), 1.02 (s, 3H), 0.96 (td, J=11.2, 5.6 Hz, 1H), 0.75 (s, 3H).

Example 449: 6—((S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propoxy)-N-methylnicotinamide

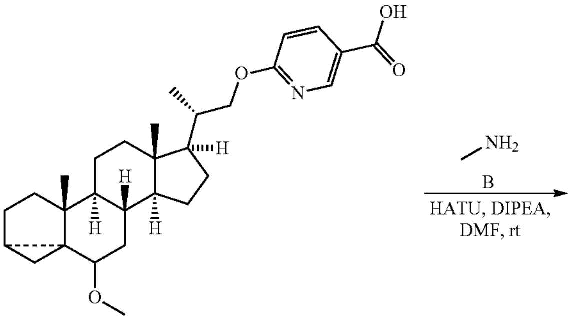

A

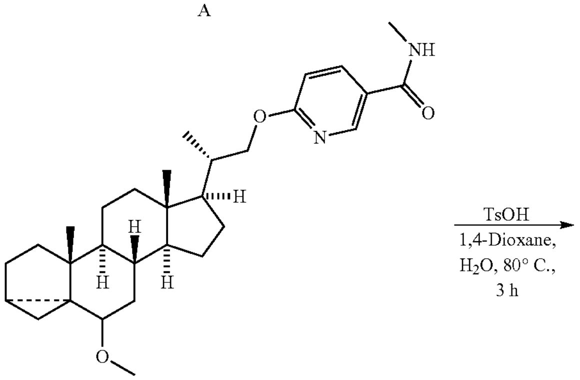

C

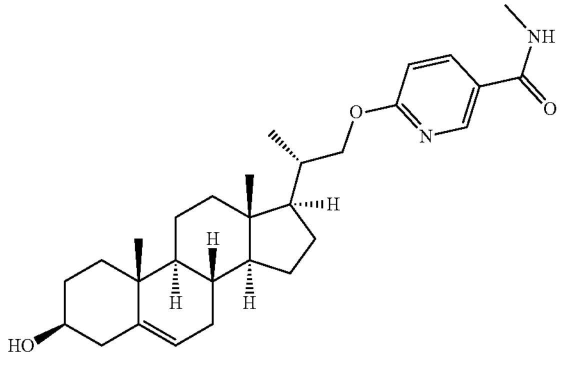

To a solution of compound A (220 mg, 470 μmol) in DMF (3 mL) was added compound B (43.8 mg, 1.41 mmol), DIPEA (304 mg, 2.35 mmol), HATU (268 mg, 706 μmol) and the reaction was stirred at room temperature for 16 h. The reaction was quenched with water (5 mL) and extracted with EtOAc (10 mL). The organic layer was washed with brine, dried over sodium sulfate, and concentrated. The residue was purified by silica gel chromatography to afford compound C (100 mg, 40.02%) as a yellow oil.

6-((2S)-2-((1aR,3aR,3bS,5aS,6R,8aS,8bS,10aR)-10-methoxy-3a,5a-dimethylhexadecahydrocyclopenta[a]cyclopropa[2,3]cyclopenta[1,2-f]naphthalen-6-yl)propoxy)-N-methylnicotinamide(100 mg, 208 μmol) was reacted according to the method of Example 430 to afford the title compound 449 (38.4 mg, 39.5%) as a white solid. LCMS: $[M+1]^+$=467.20. $^1$H NMR (400 MHz, Chloroform-d) δ 8.72 (d, J=2.4 Hz, 1H), 8.16 (dd, J=8.8, 2.4 Hz, 1H), 6.85 (d, J=8.4 Hz, 1H), 6.58 (s, 1H), 5.35 (d, J=5.2 Hz, 1H), 4.37 (dd, J=10.0, 3.2 Hz, 1H), 4.11 (dd, J=10.0, 7.2 Hz, 1H), 3.53 (tt, J=11.0, 4.8 Hz, 1H), 3.01 (d, J=4.4 Hz, 3H), 2.34-2.19 (m, 3H), 2.06-1.81 (m, 7H), 1.67-1.27 (m, 11H), 1.24-1.16 (m, 1H), 1.13 (d, J=6.6 Hz, 3H), 1.11-1.03 (m, 2H), 1.02 (s, 3H), 0.96 (td, J=11.2, 5.2 Hz, 1H), 0.74 (s, 3H).

Example 450: 2—((S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propoxy)-N-methylisonicotinamide

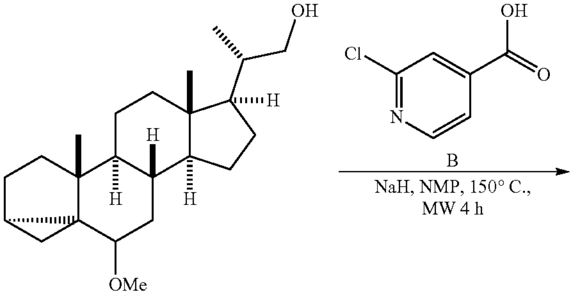

A

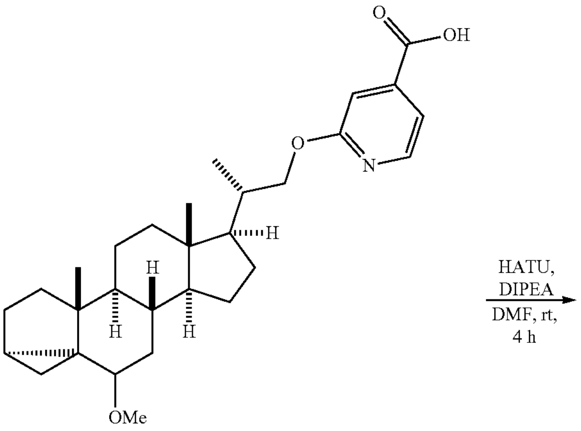

C

-continued

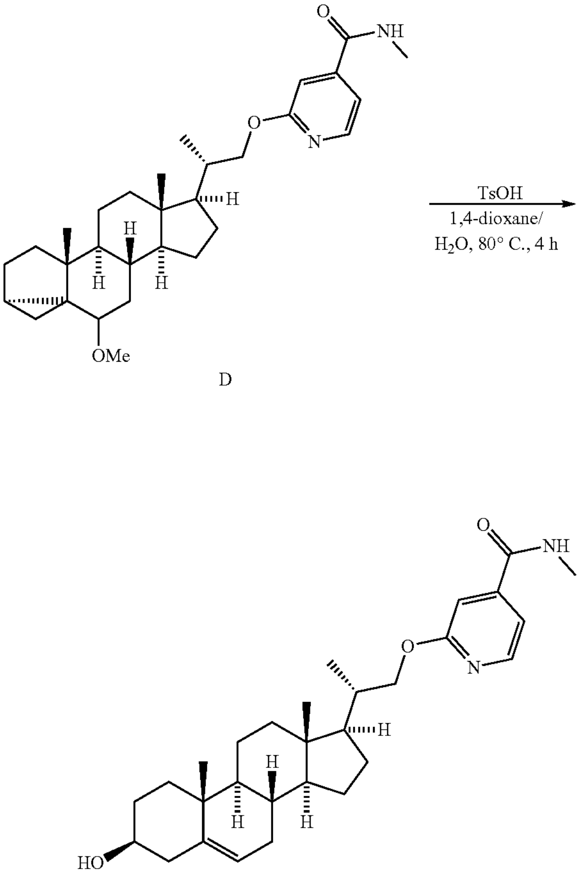

D

To a solution of compound A (600 mg, 1.82 mmol) in NMP (6 mL) was added compound B (286 mg, 1.82 mmol) and NaH (417 mg, 10.4 mmol, 60% dispersion in mineral oil) and the reaction was heated at 150° C. for 4 h in microwave irradiation. The reaction was diluted with water (5 mL) and extracted with ethyl acetate (20 mL). The organic layer was concentrated under reduced pressure. The crude product was purified by prep-TLC to give compound C (520 mg, 64%) as a white solid. To a solution of compound C (270 mg, 577 μmol) in DMF (6 mL) was added methyl amine (26.9 mg, 866 μmol), DIPEA (373 mg, 2.89 mmol), HATU (272 mg, 1.15 mmol) and the reaction was stirred at room temperature for 4 hours. The reaction was diluted with water (5 mL) and extracted with ethyl acetate (15 mL). The organic layer was concentrated under reduced pressure. The crude product was purified by silica gel chromatography to give compound D (60 mg, 21%) as a white solid.

2-((2S)-2-((1aR,3aR,3bS,5aS,6R,8aS,8bS,10aS)-10-methoxy-3a,5a-dimethylhexadecahydrocyclopenta[a]cyclopropa[2,3]cyclopenta[1,2-f]naphthalen-6-yl)propoxy)-N-methylisonicotinamide (60 mg, 125 μmol) was reacted according to the method of Example 430 to afford the title compound 450 (26 mg, 44%) as a white solid. LCMS: $[M+1]^+$=467.20. $^1H$ NMR (400 MHz, Chloroform-d) δ 8.22 (d, J=5.2 Hz, 1H), 7.12 (dd, J=5.2, 1.2 Hz, 1H), 7.03 (bs, 1H), 6.12 (s, 1H), 5.35 (d, J=5.2 Hz, 1H), 4.28 (dd, J=10.0, 3.2 Hz, 1H), 4.04 (dd, J=10.0, 7.2 Hz, 1H), 3.57-3.48 (m, 1H), 3.01 (d, J=4.8 Hz, 3H), 2.32-2.21 (m, 2H), 2.09-1.93 (m, 3H), 1.91-1.78 (m, 4H), 1.67-1.60 (m, 1H), 1.54-1.48 (m, 3H), 1.48-1.41 (m, 2H), 1.41-1.32 (m, 2H), 1.26 (s, 3H), 1.24-1.14 (m, 2H), 1.12 (d, J=6.4 Hz, 3H), 1.10-1.04 (m, 2H), 1.02 (s, 3H), 0.74 (s, 3H).

Example 451: 2—((S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propoxy)-N-methylnicotinamide

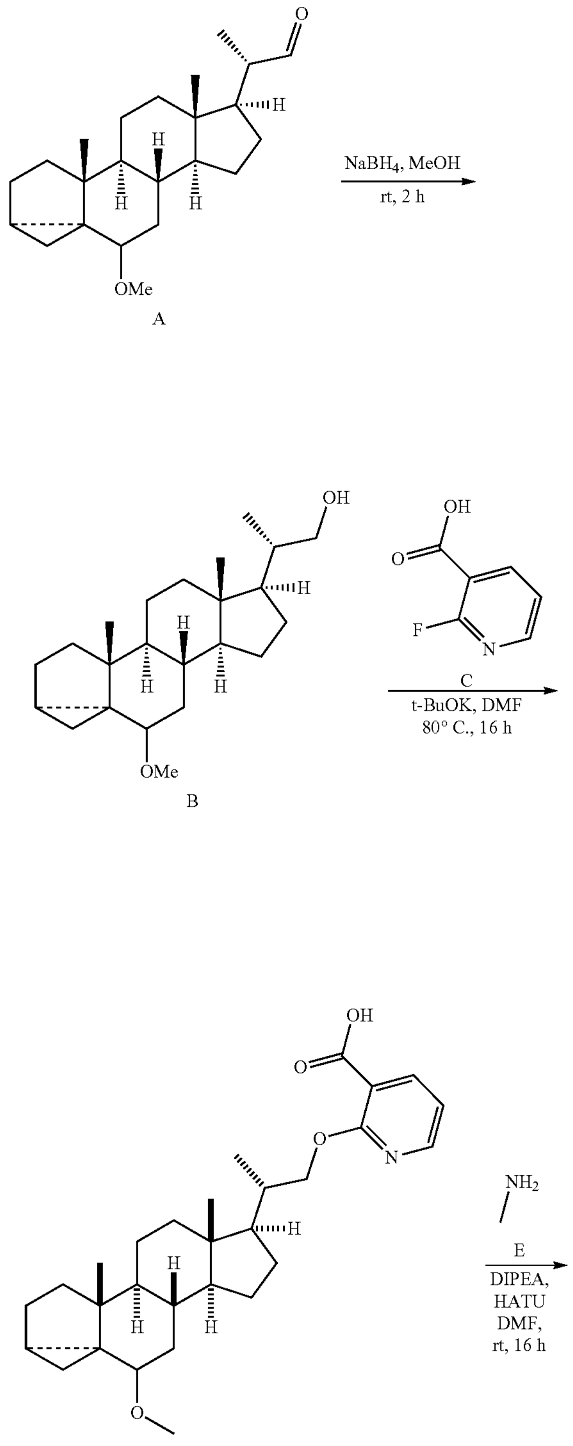

A

B

D

-continued

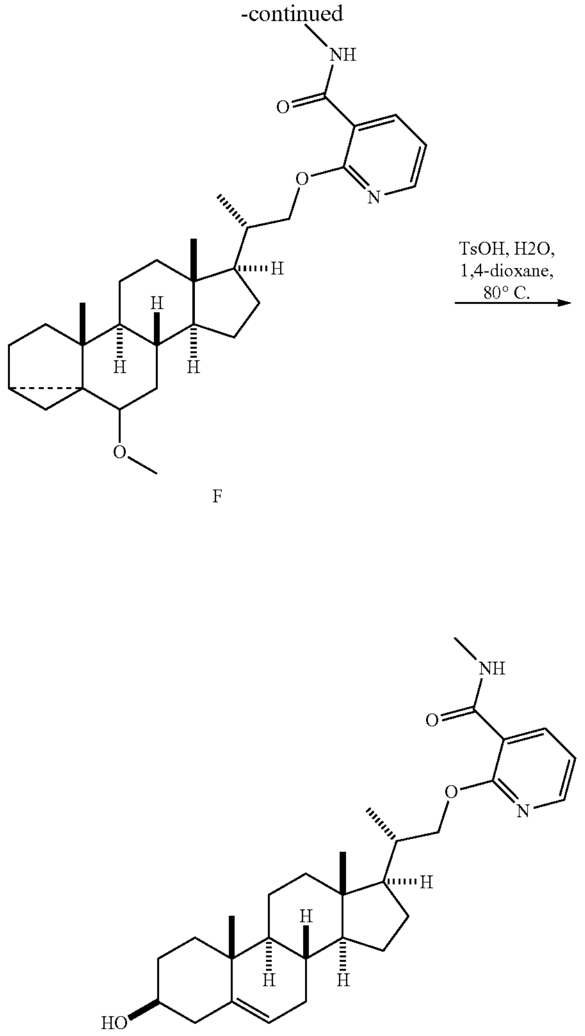

F

To a solution of compound A (6.0 g, 17.4 mmol) in methanol (40 mL) was added $NaBH_4$ (660 mg, 17.4 mmol) and the reaction was stirred at room temperature for 2 hours. The reaction was quenched with water (20 mL) and extracted with EtOAc (40 mL*3). The combined organic phase was washed with brine (10 mL), dried over sodium sulfate, and concentrated under vacuum to afford compound B (6.0 g, 99.4%) as a white solid. To a solution of compound B (1.0 g, 2.89 mmol) in DMF (15 mL) was added compound C (407 mg, 2.89 mmol) and t-BuOK (1.3 g, 11.5 mmol) and the reaction was stirred at 80° C. for 16 hours. The reaction was diluted with water (10 mL) and extracted with ethyl acetate (20 mL). The organic layer was concentrated under reduced pressure. The crude product was purified by silica gel chromatography to give compound D (300 mg, 22.2%) as a white solid. To a solution of compound D (100 mg, 214 μmol) in DMF (3 mL) was added compound E (0.17 mL, 2M in THF, 314 μmol), DIPEA (166 mg, 1.28 mmol), HATU (162 mg, 428 mmol) and the reaction was stirred at room temperature for 16 hours. The reaction was diluted with water (5 mL) and extracted with ethyl acetate (10 mL). The organic layer was concentrated under reduced pressure. The crude product was purified by silica gel chromatography to give compound F (40 mg, 38.9%) as a white solid.

2-((S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propoxy)-N-methylnicotinamide (40 mg, 83 μmol) was reacted according to the method of Example 430 to afford the title compound 451 (15 mg, 38%) as a white solid. LCMS: $[M+1]^+$=467.20. $^1H$ NMR (400 MHz, Chloroform-d) δ 8.52 (dd, J=7.6, 2.0 Hz, 1H), 8.23 (dd, J=4.8, 2.0 Hz, 1H), 8.04 (s, 1H), 7.03 (dd, J=7.6, 4.8 Hz, 1H), 5.36 (d, J=5.2 Hz, 1H), 4.47 (dd, J=10.4, 3.2 Hz, 1H), 4.28 (dd, J=10.4, 6.4 Hz, 1H), 3.53 (tt, J=10.0, 4.2 Hz, 1H), 3.03 (d, J=4.8 Hz, 3H), 2.34-2.19 (m, 2H), 2.11-1.78 (m, 7H), 1.68-1.62 (m, 1H), 1.56-1.39 (m, 7H), 1.36-1.29 (m, 2H), 1.17 (d, J=6.8 Hz, 4H), 1.15-1.05 (m, 3H), 1.03 (s, 3H), 1.01-0.94 (m, 1H), 0.77 (s, 3H).

Example 452: (R)-1-(4-(difluoromethoxy)piperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

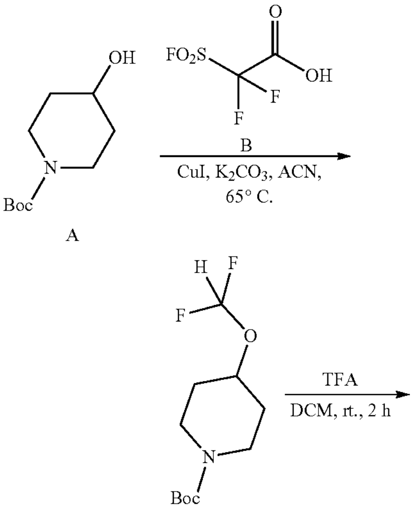

A

C

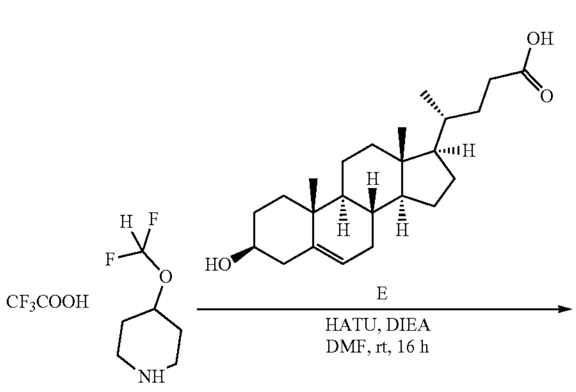

D

-continued

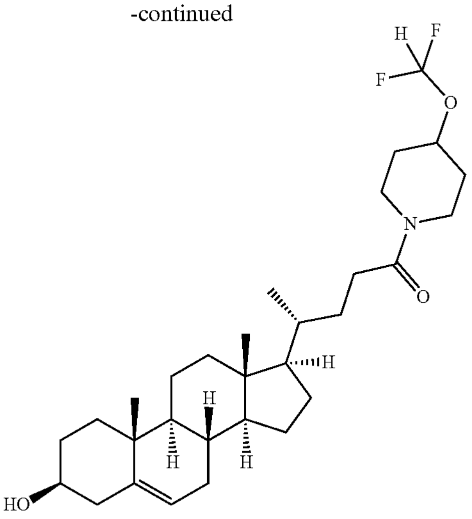

To a solution of compound A (2.01 g, 10 mmol) in ACN (20 mL) was added compound B (3.56 g, 20 mmol), CuI (570 mg, 3 mmol) and $K_2CO_3$ (4.14 g, 30 mmol) and the reaction was heated to 65° C. for 16 h. The reaction was quenched with water (10 mL) and extracted with EtOAc (40 mL). The organic layer was concentrated under reduced pressure and the residue was purified with silica gel chromatograph to afford compound C (740 mg, 29%) as a yellow oil. To a solution of compound C (100 mg, 398 μmol) in DCM (2 mL) was added TFA (0.5 mL). The reaction was stirred at room temperature for 2 h. The reaction concentrated under reduced pressure to give compound D (100.1 mg) as the TFA salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (100 mg, 404 μmol),4-(difluoromethoxy)piperidine (100.1 mg, 380 μmol) was reacted according to the method of Example 536 to afford the title compound 452 (50 mg, 36.9%) as a white solid. LCMS: $[M+1]^+$=508.20. $^1H$ NMR (400 MHz, Chloroform-d) δ 6.27 (t, J=74.6 Hz, 1H), 5.35 (d, J=5.2 Hz, 1H), 4.44 (s, 1H), 3.75 (bs, 2H), 3.55-3.35 (m, 3H), 2.40 (bs, 1H), 2.30-2.18 (m, 3H), 2.02-1.68 (m, 13H), 1.62-1.37 (m, 8H), 1.36-1.26 (m, 3H), 1.21-1.02 (m, 5H), 1.01 (s, 3H), 0.96 (d, J=6.4 Hz, 3H), 0.90-0,86 (m, 1H), 0.68 (s, 3H). $^{19}F$ NMR (376 MHz, Chloroform-d) δ–81.39 (d, J=74.6 Hz).

Example 453: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(trifluoromethoxy)piperidin-1-yl]pentan-1-one

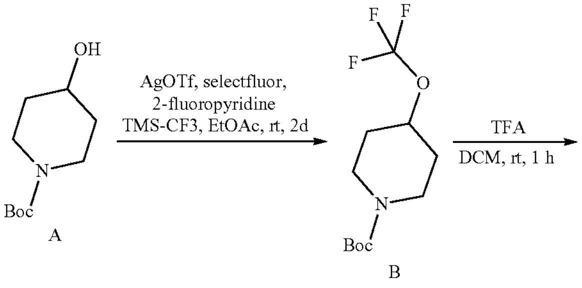

-continued

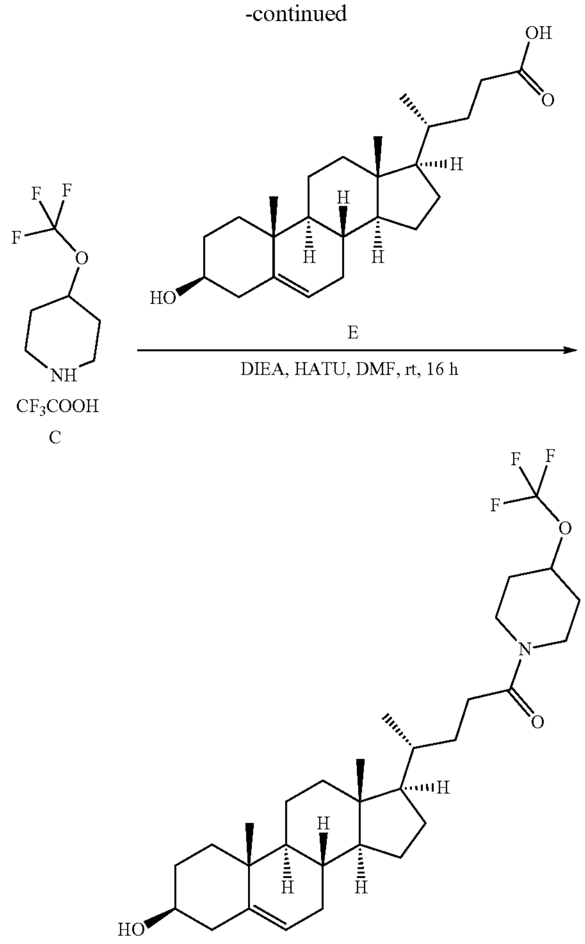

AgOTf (5.74 g, 22.4 mmol), selectfluor (3.96 g, 11.2 mmol), potassium fluoride (1.73 g, 29.8 mmol), compound A (1.5 g, 7.45 mmol) was added successively under $N_2$ atmosphere. Ethyl acetate (37.5 mL), 2-fluoropyridine (2.17 g, 22.4 mmol) and tert-butyl (trifluoromethyl) silane (3.49 g, 22.4 mmol) was added successively under $N_2$ atmosphere. The reaction was stirred at room temperature for 16 hours. The reaction was quenched with water (20 mL) and extracted with ethyl acetate (20 mL*4). The combined organic layers were concentrated under reduced pressure. The residue was purified by silica gel chromatography to afford compound B (200 mg, 7.2%) as a white solid. To a solution of compound B (150 mg, 557 μmol) in DCM (6 mL) was added trifluoroacetic acid (2 mL) at room temperature and the reaction was stirred for 2 h. The reaction concentrated under reduced pressure to give compound C (60 mg) as the TFA salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (106 mg, 284 μmol), 4-(trifluoromethoxy)piperidine 2,2,2-trifluoroacetate (60 mg, 211 μmol) was reacted according to the method of Example 536 to afford the title compound 453 (25.2 mg, 13%) as a white solid. LCMS: $[M+1]^+$=526.25. $^1H$ NMR (400 MHz, Chloroform-d) δ 5.35 (s, 1H), 4.48 (s, 1H), 3.81 (s, 1H), 3.66 (s, 1H), 3.52 (s, 2H), 3.38 (s, 1H), 2.47-2.13 (m, 4H), 2.06-1.70 (m, 10H), 1.66-1.40 (m, 10H), 1.39-1.23 (m, 3H), 1.21-1.03 (m, 4H), 1.02-0.99 (m, 3H), 0.95 (d, J=6.4 Hz, 4H), 0.69 (s, 3H). $^{19}F$ NMR (376 MHz, Chloroform-d) δ–58.02 (s).

Example 454: (3S,8S,9S,10R,13R,14S,17R)-17-((R)-4-(3-(hydroxymethyl)pyridin-2-yl)butan-2-yl)-10,13-dimethyl-2,3,4,7,8,9,10,11,12,13,14,15,16,17-tetradecahydro-1H-cyclopenta[a]phenanthren-3-ol

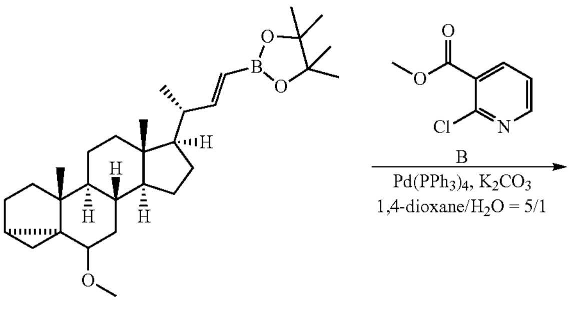

A

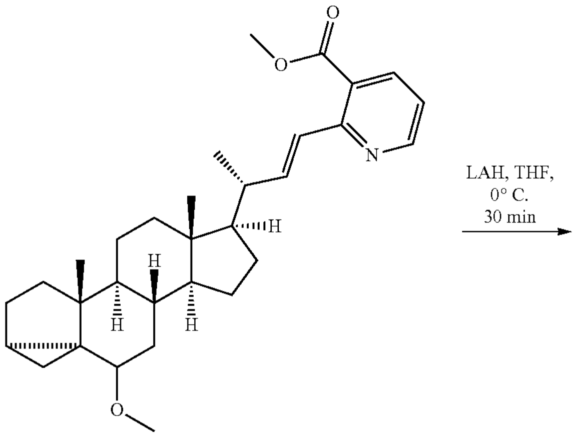

C

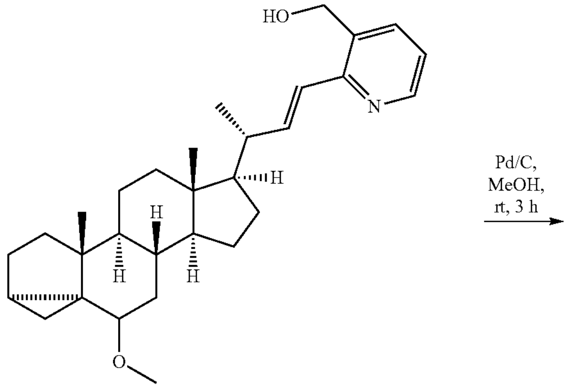

D

-continued

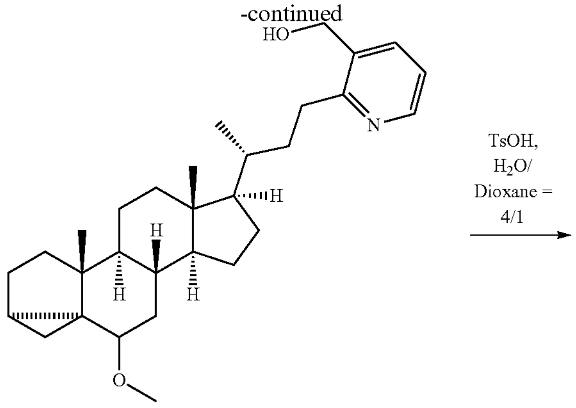

E

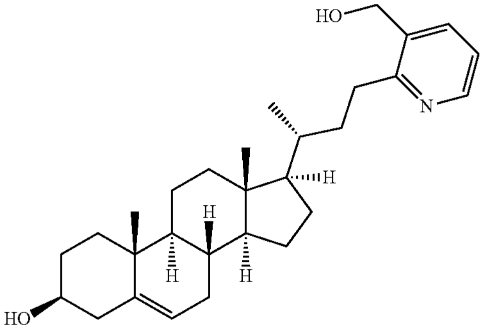

To a solution of compound A (200 mg, 427 μmol) in 1,4-dioxane (5 mL) and water (1 mL) was added compound B (65.9 mg, 384 μmol), $K_2CO_3$ (177 mg, 1.28 mmol) and $Pd(PPh_3)_4$ (49.3 mg, μmol). The reaction was heated to 65° C. for 16 h under nitrogen. Upon completion, the reaction was quenched with water (20 mL) and extracted with ethyl acetate (15 mL×3). The organic layer was washed with brine, dried over sodium sulfate, filtered, and concentrated under reduced pressure. The crude product was purified by silica gel chromatography to afford the title compound C (160 mg, 78.47%) as a white solid. To a 0° C. solution of compound C (160 mg, 335 μmol) in THE (3 mL) was added LAH (50.8 mg, 1.34 mmol) and the reaction was stirred at room temperature for 30 min under nitrogen. Upon completion, the reaction was quenched with methanol (10 mL) and concentrated under reduced pressure. The crude product was purified by silica gel chromatography to afford the title compound D (150 mg, 99.6%) as a white solid. To a solution of compound D (50 mg, 111 μmol) in methanol (3 mL) was added 10% Pd/C (10 mg). The reaction was stirred at room temperature for 3 hours under $H_2$. The reaction was filtered and concentrated to afford compound E (50 mg, 99.6%) as oil.

(2-((3R)-3-((1aR,3aR,3bS,5aR,6R,8aS,8bS,10aR)-10-methoxy-3a,5a-dimethylhexadecahydrocyclopenta[a]cyclopropa[2,3]cyclopenta[1,2-f]naphthalen-6-yl)butyl)pyridin-3-yl)methanol (50 mg, 111 μmol) was reacted according to the method of Example 430 to afford the title compound 454 (12 mg, 24.8%) as a white solid. LCMS: $[M+1]^+$=438.20. $^1H$ NMR (400 MHz, Methanol-d4) δ 8.46 (d, J=5.2 Hz, 1H), 8.20 (d, J=7.6 Hz, 1H), 7.56 (dd, J=7.6, 5.2 Hz, 1H), 5.34 (d, J=5.2 Hz, 1H), 4.75 (s, 2H), 3.44-3.33 (m, 1H), 3.02 (td, J=12.8, 5.2 Hz, 1H), 2.79 (td, J=12.8, 12.4, 4.8 Hz, 1H), 2.24-2.17 (m, 2H), 2.06-1.85 (m, 4H), 1.83-1.74 (m, 2H), 1.68-1.57 (m, 3H), 1.51 (s, 1H), 1.49-1.38 (m, 3H), 1.30-

1.17 (m, 7H), 1.12 (d, J=6.4 Hz, 3H), 1.08 (d, J=4.8 Hz, 1H), 1.03 (s, 3H), 0.96 (q, J=6.4, 5.2 Hz, 1H), 0.90 (t, J=6.8 Hz, 1H), 0.75 (s, 3H).

Example 455: (3S,8S,9S,10R,13R,14S,17R)-17-((2R)-4-(3-(1-hydroxyethyl)pyridin-2-yl)butan-2-yl)-10,13-dimethyl-2,3,4,7,8,9,10,11,12,13,14,15,16,17-tetradecahydro-1H-cyclopenta[a]phenanthren-3-ol

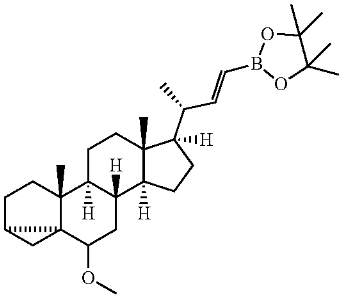

A

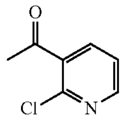

B $Pd(PPh_3)_4$, $K_2CO_3$,
1,4-dioxane, $H_2O$

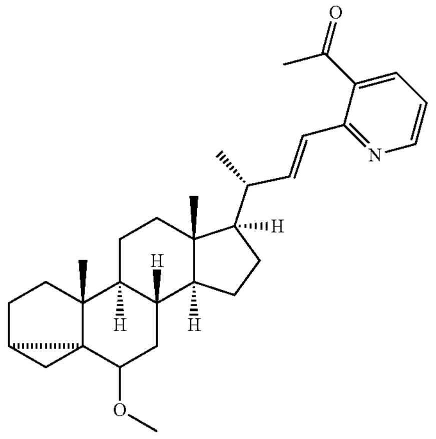

C

Pd/C
MeOH, rt.
2 h

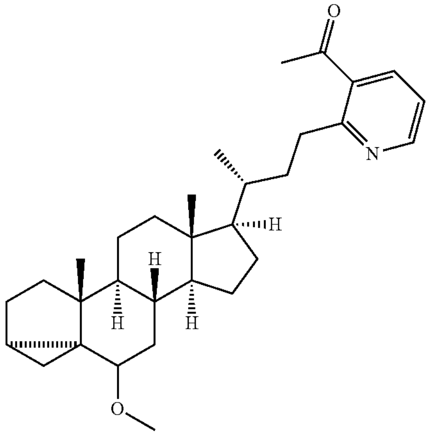

D $NaBH_4$
MeOH,
0° C.
30 min

-continued

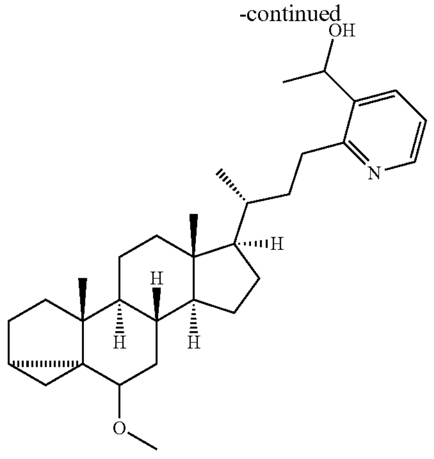

E

TsOH
$H_2O$/
Dioxane,
80° C.

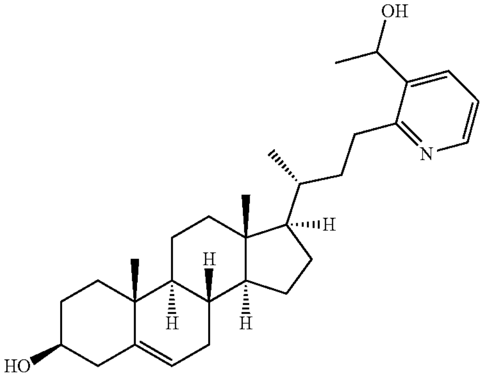

To a room temperature solution of compound A (500 mg, 1.07 mmol) in 1, 4-dioxane (20 mL) and water (4 mL) was added compound B (149 mg, 960 μmol), $Pd(PPh_3)_4$ (123 mg, 107 μmol), $K_2CO_3$ (442 mg, 3.2 mmol) and the reaction was heated to 65° C. for 16 hours under $N_2$. Upon completion, the solution was quenched with water (10 mL) and extracted with DCM (30 mL). The organic layer was dried over sodium sulfate and concentrated under reduced pressure. The crude product was purified by silica gel chromatography to afford compound C (320 mg, 65%).To a solution of compound C (320 mg, 693 μmol) in methanol (10 mL) was added 10% Pd/C (32 mg) and stirred for 2 hours under 1 atm of $H_2$. Upon completion, the reaction was filtered through celite and concentrated under vacuum to afford compound D (320 mg, 99%). To a solution of compound D (200 mg, 417 μmol) in methanol (6 mL) was added $NaBH_4$ (15.8 mg, 417 μmol) at 0° C. The reaction was stirred at 0° C. for 30 minutes. Upon completion, the solution concentrated under reduced pressure. The crude product was purified by silica gel chromatography to afford compound E (140 mg, 72%).

(3S,8S,9S,10R,13R,14S,17R)-17-((2R)-4-(3-(1-hydroxyethyl)pyridin-2-yl)butan-2-yl)-10,13-dimethyl-2,3,4,7,8,9,10,11,12,13,14,15,16,17-tetradecahydro-1H-cyclopenta[a]phenanthren-3-ol (70 mg, 150 μmol) was reacted according to the method of Example 430 to afford the title compound 455 (20.0 mg, 24%) as a white solid. LCMS: $[M+H]^+$ =452.20. $^1H$ NMR (400 MHz, Chloroform-d) δ 8.50-8.41 (m, 1H), 7.93 (s, 1H), 5.35 (d, J=5.2 Hz, 1H), 5.18 (d, J=6.8 Hz, 1H), 3.58-3.46 (m, 1H), 3.01-2.88 (m, 1H), 2.81-2.65 (m, 1H), 2.34-2.19 (m, 2H), 2.05-1.79 (m, 7H), 1.60-1.43 (m, 12H), 1.36-1.24 (m, 2H), 1.24-1.08 (m, 3H), 1.08 (d, J=6.0 Hz, 3H), 1.01 (s, 3H), 0.94 (td, J=11.2, 5.2 Hz, 1H), 0.70 (s, 3H).

Example 456: (3S,8S,9S,10R,13R,14S,17R)-17-((R)-4-(3-(2-hydroxypropan-2-yl)pyridin-2-yl)butan-2-yl)-10,13-dimethyl-2,3,4,7,8,9,10,11,12,13,14,15,16,17-tetradecahydro-1H-cyclopenta[a]phenanthren-3-ol

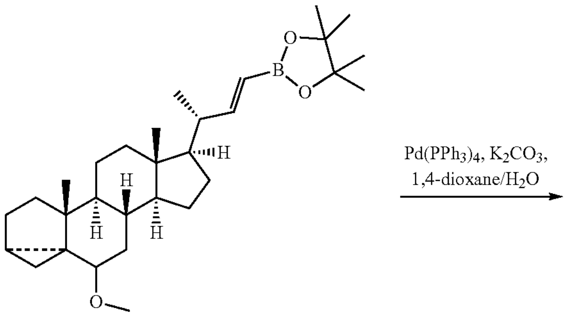

A

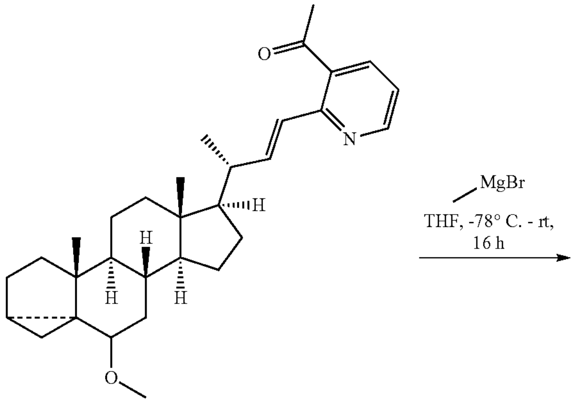

B

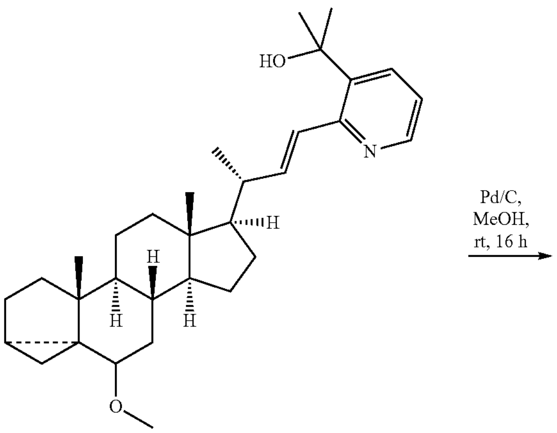

C

-continued

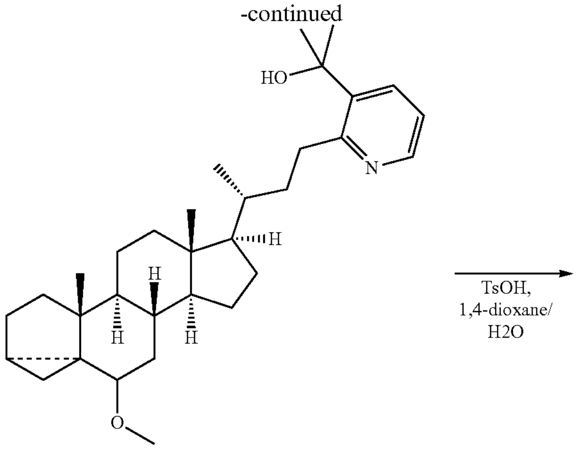

D

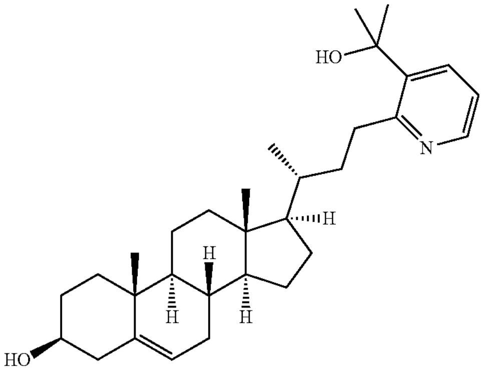

To a room temperature solution of compound A (200 mg, 426 μmol) in 1,4-dioxane (5 mL) and water (1 mL) was added $Pd(PPh_3)_4$ (24.6 mg, 21.4 μmol), 1-(2-chloropyridin-3-yl)ethan-1-one (79.6 mg, 512 μmol) and $K_2CO_3$ (177.6 mg, 1.28 mmol). The reaction was heated to 65° C. for 16 hours under a $N_2$ atmosphere. The solution was quenched with water (5 mL) and extracted with DCM (15 mL). The organic layer was dried over sodium sulfate and concentrated under reduced pressure. The crude product was purified by silica gel chromatography to give compound B (120 mg, 61%). To a solution of compound B (100 mg, 217 μmol) in THF (3 mL) at −78° C., was added $CH_3MgBr$ (1.08 mL, 1.08 mmol, 1M in THF) and stirred at room temperature for 16 h. The reaction was quenched with saturated aqueous $NH_4Cl$ (10 mL) and extracted with DCM (20 mL). The organic phase was concentrated under reduced pressure. The crude product was purified by silica gel chromatography to give compound C (60 mg, 58%). A solution of compound C (60 mg, 126 μmol) and 10% Pd/C (30 mg) in methanol (2 mL) was stirred at room temperature for 16 h under 1 atm $H_2$. The reaction was filtered and concentrated to give compound D (50 mg, 83%).

2-(2-((3R)-3-((1aR,3aR,3bS,5aR,6R,8aS,8bS,10aR)-10-methoxy-3a,5a-dimethylhexadecahydrocyclopenta[a]cyclopropa[2,3]cyclopenta[1,2-f]naphthalen-6-yl)butyl)pyridin-3-yl)propan-2-ol (50 mg, 104 μmol) was reacted according to the method of Example 430 to afford the title compound 456 (20 mg, 41%) as a white solid. LCMS: $[M+1]^+$=466.20. $^1H$ NMR (400 MHz, Chloroform-d) δ 8.51 (d, J=4.8 Hz, 1H), 7.82 (s, 1H), 7.13 (s, 1H), 5.39 (s, 1H), 3.61-3.49 (m, 1H), 3.30-3.13 (m, 1H), 3.00 (t, J=12.0 Hz, 1H), 2.36-2.24 (m, 2H), 2.14-2.01 (m, 2H), 1.98-1.84 (m, 4H), 1.77 (s, 1H), 1.72 (s, 6H), 1.42-1.29 (m, 5H), 1.27-1.19 (m, 2H), 1.17-1.10 (m, 4H), 1.09 (d, J=7.6 Hz, 1H), 1.06 (s, 3H), 1.02-0.88 (m, 2H), 0.75 (s, 3H).

Example 457: (1R,3aS,3bS,7S,9aR,9bS,11aR)-1-[(2R)-4-(3-ethoxypyridin-2-yl)butan-2-yl]-9a,11a-dimethyl-1H,2H,3H,3aH,3bH,4H,6H,7H,8H,9H,9aH,9bH,10H,11H,11aH-cyclopenta[a]phenanthren-7-ol

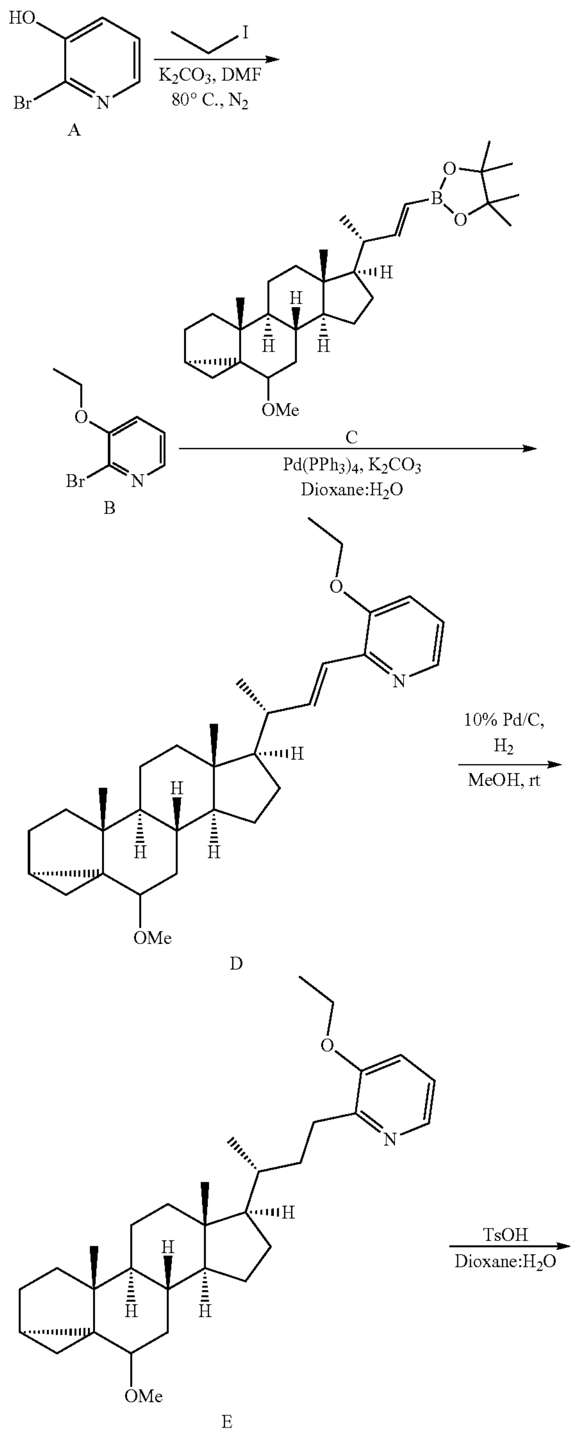

-continued

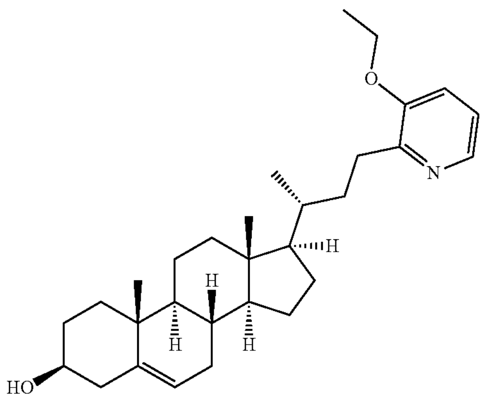

To a room temperature solution of compound A (2.0 g, 11.5 mmol) in DMF (20 mL) was added $K_2CO_3$ (2.54 g, 18.4 mmol) and iodoethane (1.56 mL, 19.5 mmol) and the reaction was heated to 80° C.; for 16 h. The reaction was diluted with water (10 mL) and extracted with ethyl acetate (50 mL). The organic layer was washed with water and brine (5 mL), dried with sodium sulfate, and concentrated under vacuum to give compound B (2.30 g, 99.2%). To a solution of compound C (200 mg, 427 μmol) in 1,4-dioxane (5 mL) and water (1 mL) was added $K_2CO_3$ (177 mg, 1.28 mmol), compound B (86.2 mg, 427 μmol) and $Pd(PPh_3)_4$ (49.3 mg, 42.7 μmol). The reaction was heated at 65° C. for 16 h under nitrogen. After cooling to room temperature, the reaction was filtered and concentrated under vacuum. The residue was purified by silica gel chromatography to give compound D (100 mg, 50.5%). To a solution of compound D (100 mg, 216 μmol) in methanol (6 mL) was added 10% Pd/C (5 mg), the reaction was stirred for 1 h at room temperature under 1 atm of $H_2$. The reaction was filtered through Celite and concentrated under vacuum to give compound E (80 mg, 79.6%).

3-ethoxy-2-((3R)-3-((1aR,3aR,3bS,5aR,6R,8aS,8bS,10aS)-10-methoxy-3a,5a-dimethylhexadecahydrocyclopenta[a]cyclopropa[2,3]cyclopenta[1,2-f]naphthalen-6-yl)butyl)pyridine (80 mg, 172 μmol) was reacted according to the method of Example 430 to afford the title compound 457 (48.4 mg, 49.9%) as a white solid. LCMS: $[M+H]^+$=452.20. $^1H$ NMR (400 MHz, Chloroform-d) δ 8.13-8.04 (m, 1H), 7.09 (d, J=3.2 Hz, 2H), 5.35 (d, J=5.2 Hz, 1H), 4.04 (q, J=7.2 Hz, 2H), 3.51 (dd, J=14.4, 4.4 Hz, 2H), 2.92 (td, J=12.0, 4.4 Hz, 1H), 2.74 (td, J=11.6, 5.2 Hz, 1H), 2.31-2.19 (m, 2H), 2.07-1.73 (m, 7H), 1.45 (t, J=6.8 Hz, 6H), 1.31-1.10 (m, 6H), 1.06 (d, J=6.4 Hz, 3H), 1.01 (s, 3H), 0.98-0.82 (m, 2H), 0.69 (s, 3H).

Example 458: bis((1R,3aS,3bS,7S,9aR,9bS,11aR)-1-[(2R)-4-[3-(2-hydroxyethoxy) pyridin-2-yl]butan-2-yl]-9a,11a-dimethyl-1H,2H,3H,3aH,3bH,4H,6H,7H,8H,9H,9aH,9bH,10H,11H,11aH-cyclopenta[a]phenanthren-7-ol)

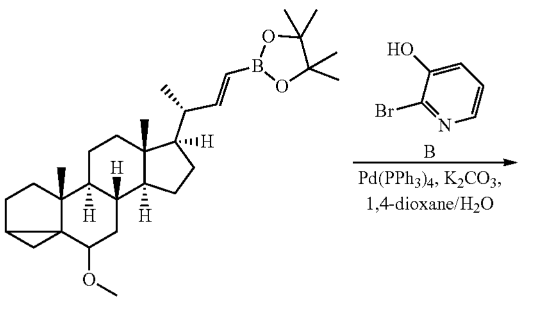

A

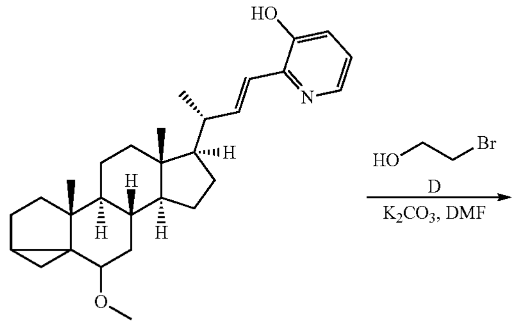

C

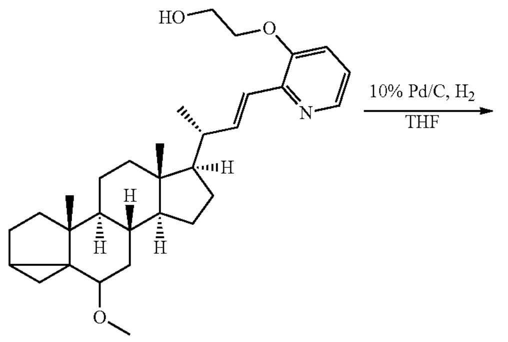

E

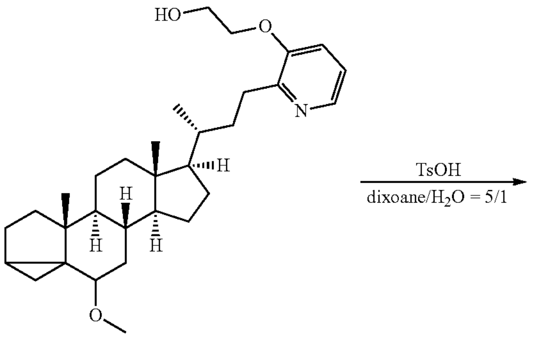

F

-continued

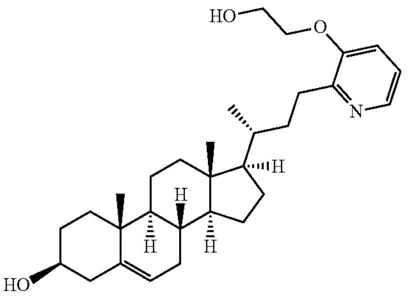

To a room temperature solution of compound A (500 mg, 1.07 mmol) in 1, 4-dioxane (5 mL) and $H_2O$ (1 mL) was added compound B (167 mg, 960 μmol), $Pd(PPh_3)_4$ (123 mg, 107 μmol) and $K_2CO_3$ (442 mg, 3.2 mmol) and the reaction was heated to 65° C. for 16 hours. The reaction was filtered through Celite, water (20 mL) was added and extracted with ethyl acetate (20 mL*2). The combined organic layers were dried over sodium sulfate and concentrated under reduced pressure. The residue was purified by silica gel chromatography to afford compound C (220 mg, 48%) as a yellow oil. To a solution of compound C (120 mg, 275 μmol) in DMF (2 mL) was added $K_2CO_3$ (228 mg, 1.65 mmol). The reaction was stirred at 50° C. for 1 hour and compound D (41 mg, 331 μmol) was added. The reaction was stirred at 120° C. for 6 h. The reaction was cooled to room temperature quenched with water (30 mL) and extracted with EtOAc (20 mL*3). The combined organic phase was washed with water (30 mL*2), brine (30 mL), dried over sodium sulfate, concentrated under reduced pressure, and purified by silica gel chromatography to afford compound E (80 mg, 60%). To a solution of compound E (160 mg, 334 μmol) in THE (4 mL) was added 10% Pd/C (50 mg) under $H_2$ atmosphere at room temperature. The reaction was stirred at room temperature for 16 hours. The reaction was filtered through celite and the filtrate concentrated under reduced pressure. The residue was purified by silica gel chromatography to afford compound F (130 mg, 81%) as a yellow oil.

2-((2-((3R)-3-((1aR,3aR,3bS,5aR,6R,8aS,8bS,10aR)-10-methoxy-3a,5a-dimethylhexadecahydrocyclopenta[a]cyclopropa[2,3]cyclopenta[1,2-f]naphthalen-6-yl)butyl)pyridin-3-yl)oxy)ethan-1-ol (130 mg, 271 μmol) was reacted according to the method of Example 430 to afford the title compound 458 (60 mg, 47%) as a white solid. LCMS: $[M+H]^+$=468.4 $^1H$ NMR (400 MHz, Chloroform-d) δ 8.15 (dd, J=4.8, 1.6 Hz, 1H), 7.22-7.07 (m, 1H), 5.35-5.34 (m, 1H), 4.13 (t, J=4.4 Hz, 2H), 4.02 (s, 2H), 3.55-3.51 (m, 1H), 3.01-2.77 (m, 2H), 2.36-2.16 (m, 2H), 2.13-1.73 (m, 8H), 1.54-1.36 (m, 7H), 1.36-1.12 (m, 4H), 1.09-0.98 (m, 8H), 0.97-0.90 (m, 1H), 0.68 (s, 3H).

Example 459: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(1-iminoethyl)piperazin-1-yl)pentan-1-one

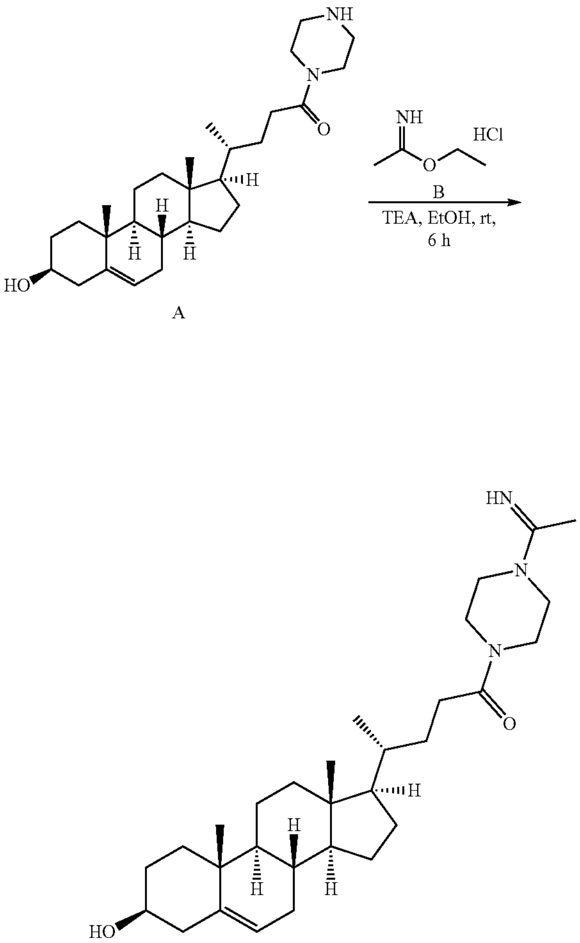

To a solution of compound A (300 mg, 678 μmol) and compound B (83.7 mg, 678 μmol) in ethanol (5 mL, 85.6 mmol) was added TEA (206 mg, 2.03 mmol). The reaction was stirred at room temperature for 6 hours. The reaction was diluted with water (20 mL) and extracted with ethyl acetate (10 mL*2). The combined organic layers were washed with water (20 mL), brine (20 mL), dried over sodium sulfate and concentrated under reduced pressure. The residue was purified by silica gel chromatography to afford the title compound 459 (40 mg, 12.2%) as a white solid. LCMS: $[M+1]^+$=484.25. $^1H$ NMR (400 MHz, DMSO-$d_6$) δ 5.34 (d, J=5.2 Hz, 1H), 3.83-3.56 (m, 8H), 3.39 (td, J=12.4, 11.6, 6.5 Hz, 1H), 2.55-2.15 (m, 7H), 2.09-1.74 (m, 6H), 1.67-1.45 (m, 7H), 1.40-1.29 (m, 2H), 1.27-1.04 (m, 5H), 1.03 (s, 3H), 1.00 (d, J=6.4 Hz, 3H), 0.97-0.89 (m, 1H), 0.74 (s, 3H).

Example 460: (2S)-2-[(1R,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]propyl N-(2-methoxyethyl)carbamate

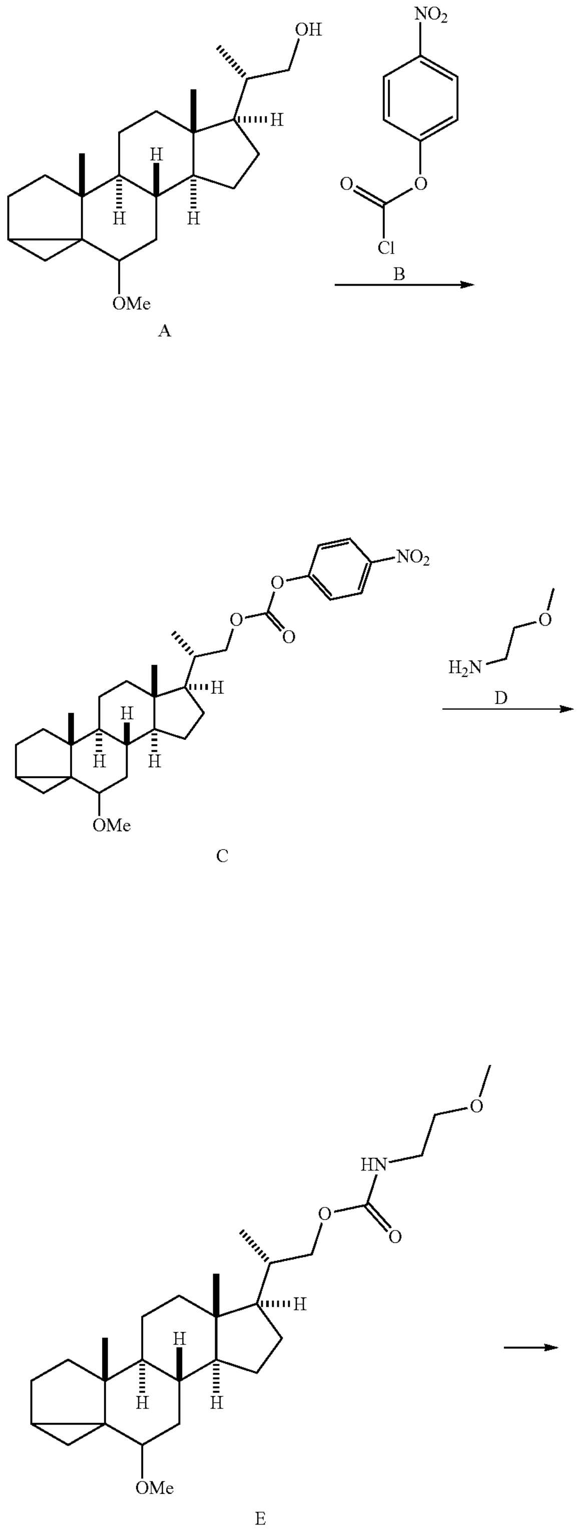

-continued

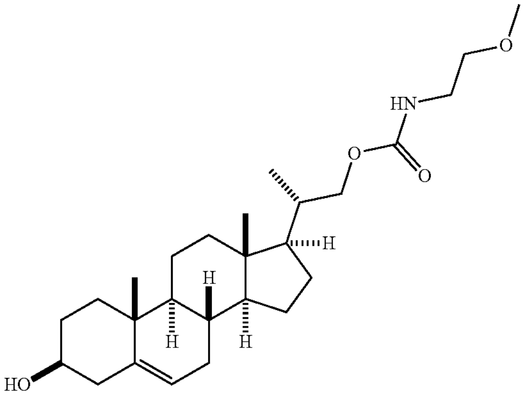

To a 0° C. solution of compound A (500 mg, 1.44 mmol) in DCM (10 mL) was added TEA (323 mg, 2.16 mmol) and compound B (320 mg, 1.59 mmol). The reaction was stirred for 1 hour. Upon completion, the reaction was quenched with water (50 mL) and extracted with ethyl acetate (15 mL*3). The combined organic layers were washed with brine, dried over sodium sulfate, filtered, and concentrated under reduced pressure. The crude product was purified by column chromatography on silica gel to yield the title compound C (400 mg, 54%) as a white solid. To a solution of compound C (200 mg, 412 μmol) in DMF (4 mL) was added compound D (31 mg, 412 μmol) and DIEA (160 mg, 1.24 mmol) and the reaction was stirred at room temperature for 16 hours. The reaction was quenched with water and extracted with ethyl acetate. The organic layer was concentrated under reduced pressure and the crude was purified by column to give compound E (150 mg, 36%).

(2S)-2-((1aR,3aR,3bS,5aS,6R,8aS,8bS,10aR)-10-methoxy-3a,5a-dimethylhexadecahydrocyclopenta[a]cyclopropa[2,3]cyclopenta[1,2-f]naphthalen-6-yl)propyl (2-methoxyethyl)carbamate (150 mg, 335 μmol) was reacted according to the method of Example 430 to afford the title compound 460 (70 mg, 48%) as a white solid. LCMS: $[M+1]^+$=456.20. $^1H$ NMR (400 MHz, Chloroform-d) δ 5.35-5.34 (m, 1H), 5.00 (bs, 1H), 4.09 (dd, J=10.4, 3.4 Hz, 1H), 3.78-3.76 (m, 1H), 3.57-3.49 (m, 1H), 3.46-3.44 (m, 2H), 3.36 (s, 5H), 2.33-2.19 (m, 2H), 1.98 (m, 2H), 1.90-1.78 (m, 3H), 1.72-1.67 (m, 1H), 1.56-1.41 (m, 6H), 1.39-1.29 (m, 2H), 1.22-1.07 (m, 4H), 1.01-0.99 (m, 7H), 0.97-0.94 (m, 1H), 0.70 (s, 3H).

Example 461: (1S)-1-[(1S,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]ethyl N,N-dimethylcarbamate

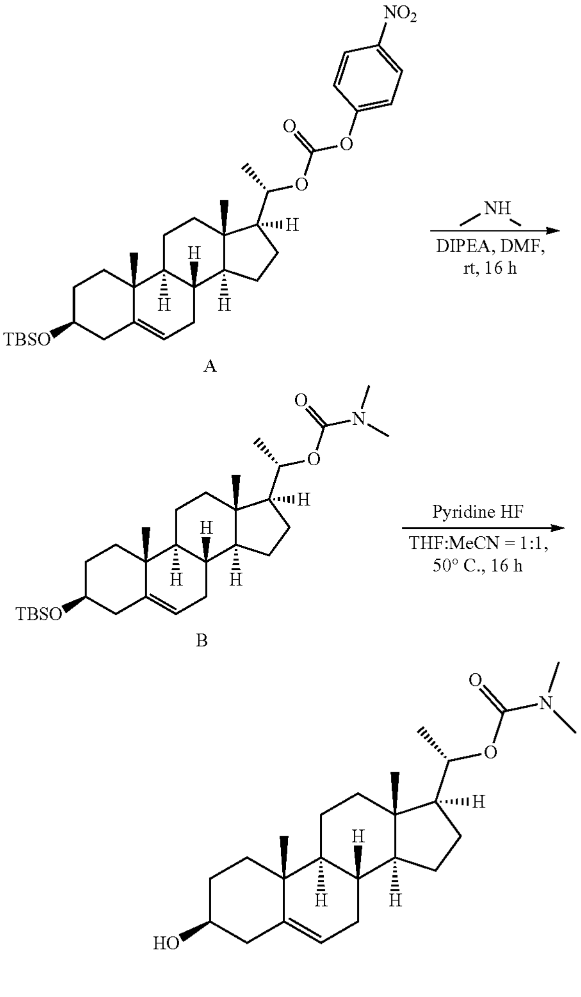

To a 0° C. solution of compound A (140 mg, 234 μmol) in DMF (5 mL) was added DIPEA (60.5 mg, 468 μmol) and dimethylamine (31.7 mg, 702 μmol) and the reaction was warmed to room temperature for 16 h. The reaction was quenched with water (10 mL) and extracted with ethyl acetate (30 mL). The organic layer was dried with sodium sulfate and concentrated under reduced pressure. The crude product was purified by silica gel chromatography to give compound B (90.0 mg, 76.3%). To a reaction of compound B (70 mg, 139 μmol) and hydrogen pyridine fluoride (212 mg, 1.39 mmol) in tetrahydrofuran (5 mL) and acetonitrile (5 mL) was heated at 50° C. for 16 h. The pH of the reaction was adjusted to pH 7 with saturated aqueous $NaHCO_3$ and extracted with ethyl acetate (20 mL). The organic layer was dried over anhydrous sodium sulfate and concentrated under reduced pressure. The crude product was purified by silica gel chromatography to give the title compound 461 (41.0 mg, 75.8%) as a white solid. $^1H$ NMR (400 MHz, Chloroform-d) δ 5.35 (dd, J=5.2, 2.4 Hz, 1H), 4.84-4.74 (m, 1H), 3.56-3.47 (m, 1H), 2.88 (s, 6H), 2.30-2.19 (m, 2H), 2.04-

1.78 (m, 6H), 1.67-1.57 (m, 2H), 1.52-1.40 (m, 6H), 1.29-1.21 (m, 4H), 1.23 (d, J=1.6 Hz, 2H), 1.01 (s, 3H), 0.97-0.84 (m, 2H), 0.69 (s, 3H).

Example 462: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3R)-3-(pyrimidin-4-yloxy)piperidin-1-yl]pentan-1-one

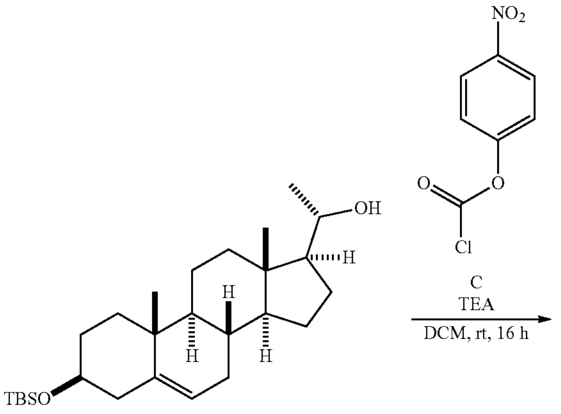

A

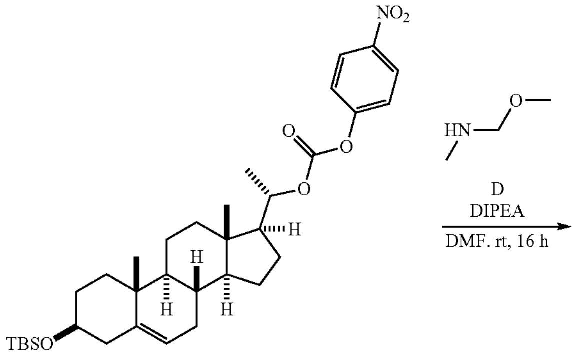

B

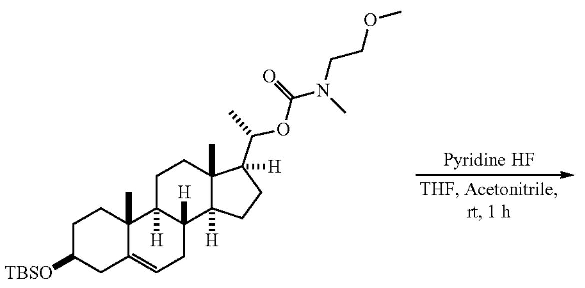

E

-continued

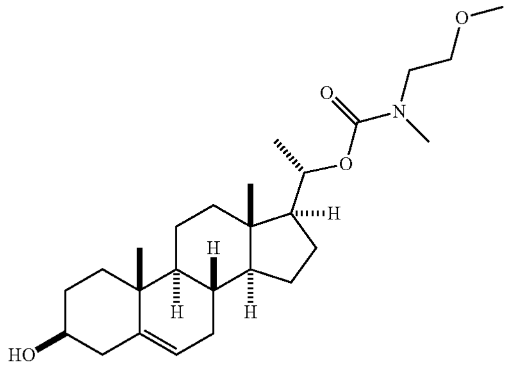

To a 0° C. solution of compound A (400 mg, 960 μmol) in dichloromethane (10 mL) was added TEA (146 mg, 1.44 mmol) and compound C (213 mg, 1.06 mmol) and the reaction was stirred for 1 hour. Upon completion, the reaction was quenched with water (100 mL) and extracted with ethyl acetate (30 mL*3). The combined organic layers were washed with brine (20 mL), dried over sodium sulfate, filtered, and concentrated under reduced pressure. The crude product was purified by silica gel chromatography to afford compound B (240 mg, 43%) as a white solid. To a solution of compound B (240 mg, 412 μmol) and compound D (36.8 mg, 412 μmol) in DMF (10 mL) was added DIEA (160 mg, 1.24 mmol) and the reaction was stirred at room temperature for 3 hours. Upon completion, the reaction was quenched with saturated aqueous ammonium chloride (30 mL) and extracted with ethyl acetate (10 mL*3). The combined organic layers were washed with brine (10 mL), dried over sodium sulfate, filtered, and concentrated under reduced pressure. The crude product was purified by silica gel chromatography to afford compound E (120 mg, 68%) as a white solid.

Pyridine HF (2 mL, 65-70%) was added slowly to the compound E (120 mg, 219 μmol) in a single-neck flask at room temperature and stirred for 16 hours. Upon completion, the reaction was extracted with ethyl acetate (2*10 mL). The combined organic layers were concentrated under reduced pressure. The crude product was purified by silica gel chromatography to afford the title compound 462 (38 mg, 40%) as a white solid. LCMS: $[M+23]^+$=456.20. $^1H$ NMR (400 MHz, Chloroform-d) δ 5.35 (m, 1H), 4.82 (m, 1H), 3.65-3.25 (m, 9H), 2.93-2.90 (m, 3H), 2.26-2.24 (m, 2H), 2.04-1.76 (m, 5H), 1.56-1.39 (m, 8H), 1.30 (s, 1H), 1.23 (s, 1H), 1.11-1.00 (m, 4H), 1.00-0.98 (m, 5H), 0.69 (s, 3H).

Example 463: methyl ((S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propyl)carbamate

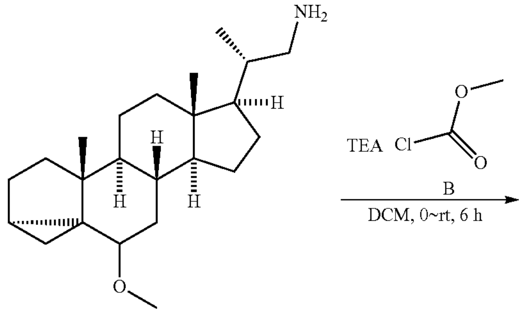

A

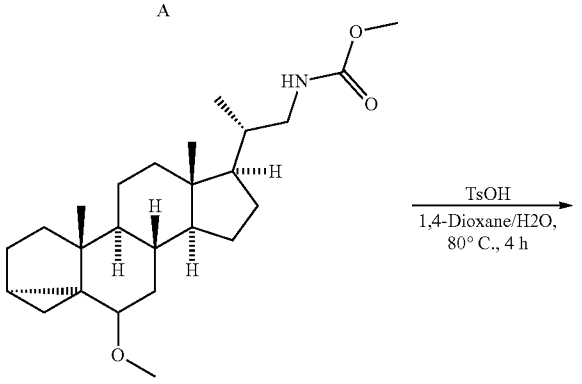

C

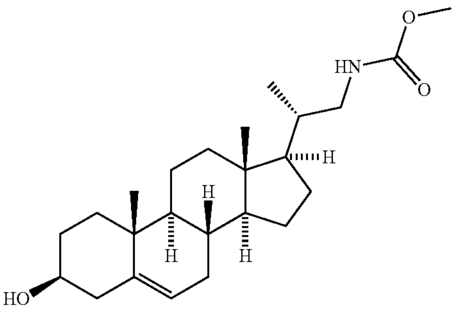

To a 0° C. solution of compound A (200 mg, 579 μmol) in DCM (10 mL) was added TEA (293 mg, 2.89 mmol) and compound B (82 mg, 868 μmol) and the reaction was warmed to room temperature for 6 hours. The reaction was diluted with water (5 mL) and extracted with ethyl acetate (10 mL). The organic layer was concentrated under reduced pressure. The crude product was purified by silica gel chromatography to afford compound C (180 mg, 77%) as a yellow oil.

Methyl ((2S)-2-((1aR,3aR,3bS,5aS,6R,8aS,8bS,10aS)-10-methoxy-3a,5a-dimethylhexadecahydrocyclopenta[a]cyclopropa[2,3]cyclopenta[1,2-f]naphthalen-6-yl)propyl)carbamate (180 mg, 447 μmol) was reacted according to the method of Example 430 to afford the title compound 463 (26 mg, 15%) as a white solid LCMS: $[M+1]^+=390.20$. $^1H$ NMR (400 MHz, Chloroform-d) δ 5.35 (d, J=5.2 Hz, 1H), 4.64 (bs, 1H), 3.66 (s, 3H), 3.57-3.48 (m, 1H), 3.34-3.22 (m, 1H), 2.93-2.83 (m, 1H), 2.30-2.21 (m, 2H), 2.05-1.93 (m, 2H), 1.88-1.77 (m, 2H), 1.47-1.42 (m, 3H), 1.29-1.22 (m, 6H), 1.21-1.06 (m, 5H), 1.01 (s, 3H), 0.97 (d, J=6.4 Hz, 3H), 0.92-0.85 (m, 2H), 0.69 (s, 3H).

Example 464: 1—((S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propyl)-3-methylurea

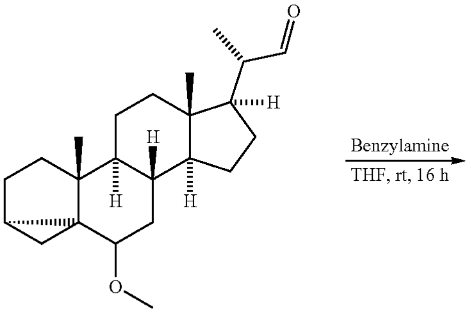

A

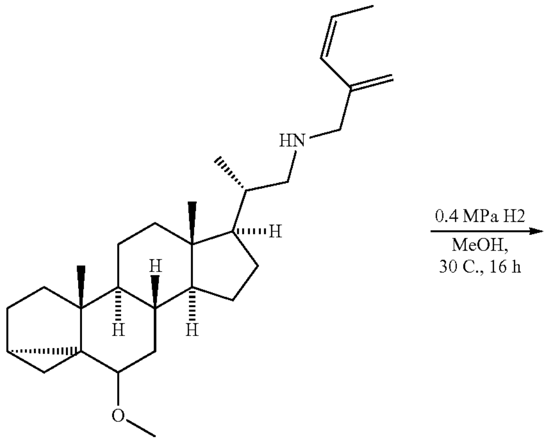

B

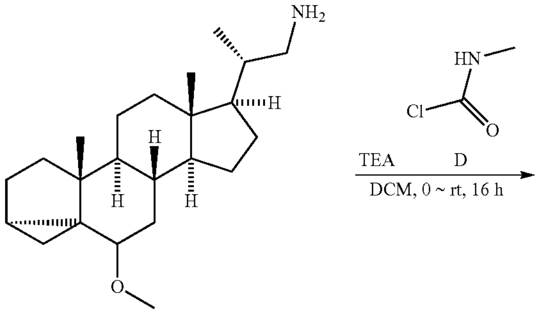

C

-continued

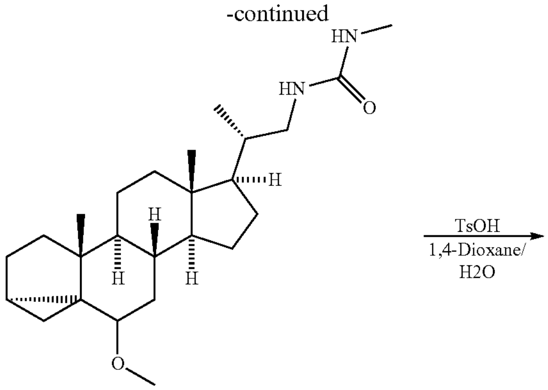

E

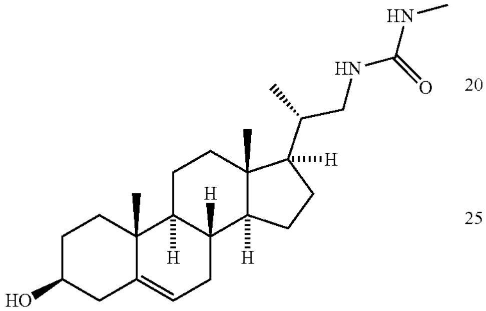

To a solution of compound A (3.0 g, 8.71 mmol) in THF (60 mL) was added 1-phenylmethanamine (1.4 g, 13.1 mmol) and 10% Pd/C (400 mg). The reaction was stirred at room temperature under 1 atm of $H_2$ for 16 hours. The reaction was filtered and concentrated under reduced pressure. The crude product was purified by silica gel chromatography to afford compound B (3.0 g, 79%). To a solution of compound B (3.0 g, 6.89 mmol) in MeOH (30 mL) was added 10% Pd/C (300 mg). The reaction was stirred at 30° C. for 16 hours under 4 atm of hydrogen. Upon completion, the reaction was concentrated, and the crude was purified by silica gel chromatography to afford compound C (1.2 g, 52%). To a 0° C. solution of compound C (200 mg, 579 μmol) in DCM (6 mL) was added TEA (293 mg, 2.89 mmol), compound D (81.2 mg, 868 μmol) and the solution was warmed to room temperature for 16 hours. The reaction was diluted with water (5 mL) and extracted with ethyl acetate (15 mL). The organic layer was concentrated under reduced pressure. The crude product was purified by silica gel chromatography to afford compound E (180 mg, 77%).

1-((2S)-2-((1aR,3 aR,3bS,5aS,6R,8aS,8bS,10aS)-10-methoxy-3a,5a-dimethylhexadecahydrocyclopenta[a]cyclopropa[2,3]cyclopenta[1,2-f]naphthalen-6-yl)propyl)-3-methylurea (180 mg, 447 μmol) was reacted according to the method of Example 430 to afford the title compound 464 (57 mg, 32%) as a white solid. LCMS: $[M+1]^+$=389.20. $^1H$ NMR (400 MHz, Chloroform-d) δ 5.35 (d, J=5.2 Hz, 1H), 4.29-4.09 (m, 2H), 3.59-3.48 (m, 1H), 3.27 (dt, J=13.2, 4.8 Hz, 1H), 2.85 (dt, J=13.2, 7.2 Hz, 1H), 2.79 (d, J=4.8 Hz, 3H), 2.30-2.26 (m, 1H), 2.23 (d, J=6.8 Hz, 1H), 2.09-1.79 (m, 6H), 1.53-1.05 (m, 14H), 1.01 (s, 3H), 0.98 (d, J=6.8 Hz, 3H), 0.89 (d, J=7.2 Hz, 1H), 0.70 (s, 3H).

Example 465: 1-(2S)-2-[(1R,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]propyl 4-methyl piperazine-1,4-dicarboxylate

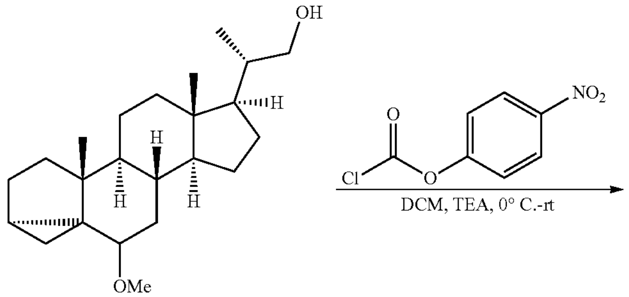

A

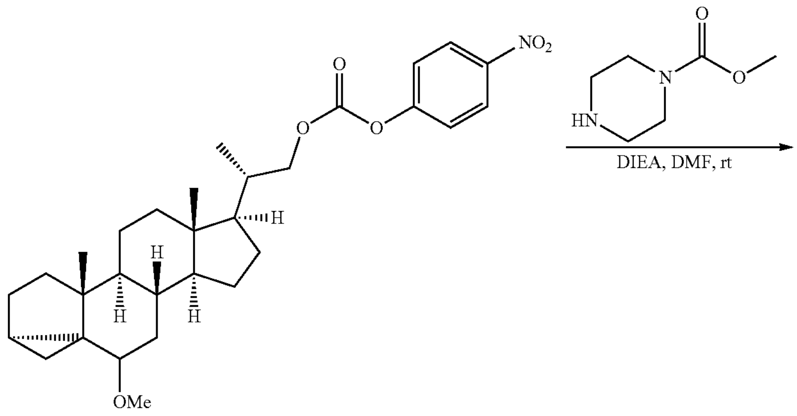

B

-continued

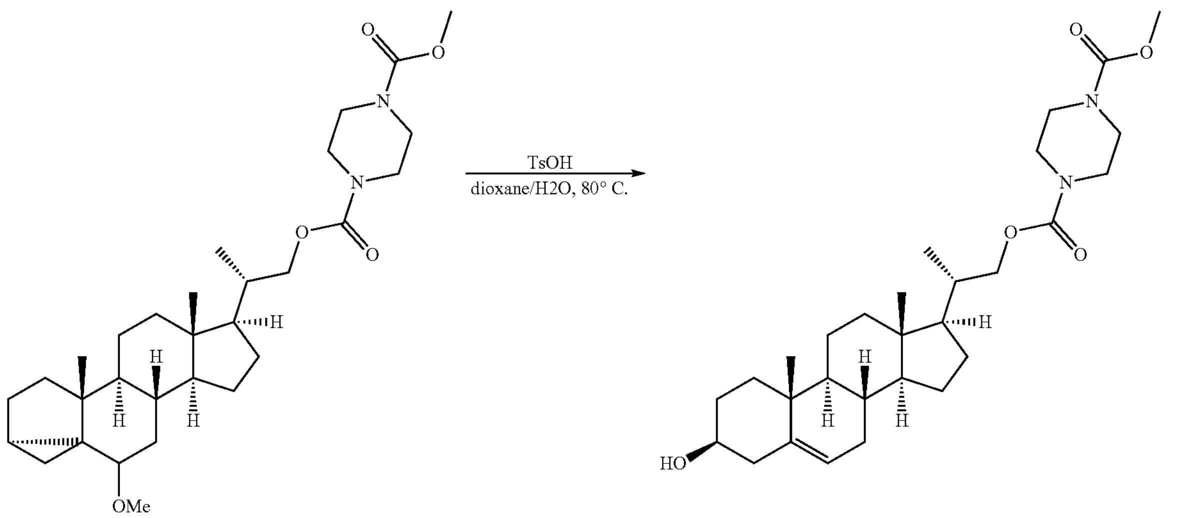

C

To a 0° C. solution of compound A (200 mg, 577 μmol) in dichloromethane (5 mL) was added triethylamine (241 μL, 1.73 mmol), 4-nitrophenyl carbonochloridate (174 mg, 866 μmol) and the reaction was stirred at room temperature for 3 h. The reaction was quenched with water (5 mL) and extracted with DCM (10 mL). The organic layer was dried with sodium sulfate and concentrated under reduced pressure. The crude product was purified by silica gel chromatography to give compound B (150 mg, 50.8%). To a solution of compound B (150 mg, 293 μmol) in DMF (3 mL) was added DIEA (114 mg, 879 μmol) and methyl piperazine-1-carboxylate (115 μL, 879 μmol) at room temperature. The reaction was stirred at room temperature for 16 h. The reaction was quenched with water (10 mL) and extracted with ethyl acetate (20 mL). The organic layer was dried with sodium sulfate and concentrated under reduced pressure. The crude product was purified by silica gel chromatography to give compound C (50 mg, 33.0%).

1-((2S)-2-((1aR,3 aR,3bS,5aS,6R,8aS,8bS,10aS)-10-methoxy-3a,5a-dimethylhexadecahydrocyclopenta[a]cyclopropa[2,3]cyclopenta[1,2-f]naphthalen-6-yl)propyl) 4-methyl piperazine-1,4-dicarboxylate (50 mg, 96.8 μmol) was reacted according to the method of Example 430 to afford the title compound 465 (17.2 mg, 35.4%) as a white solid. LCMS: $[M+23]^+=525.20$. $^1H$ NMR (400 MHz, $CDCl_3$) δ 5.35 (d, J=5.2 Hz, 1H), 4.13 (dd, J=10.4, 3.2 Hz, 1H), 3.79 (dd, J=10.4, 7.2 Hz, 1H), 3.72 (s, 3H), 3.57-3.41 (m, 9H), 2.30-2.21 (m, 2H), 2.04-1.68 (m, 7H), 1.53-1.41 (m, 6H), 1.33-1.23 (m, 4H), 1.04-1.00 (m, 6H), 0.99-0.83 (m, 3H), 0.71 (s, 3H).

Example 466: 1-(1S)-1-[(1S,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]ethyl 4-methyl piperazine-1,4-dicarboxylate

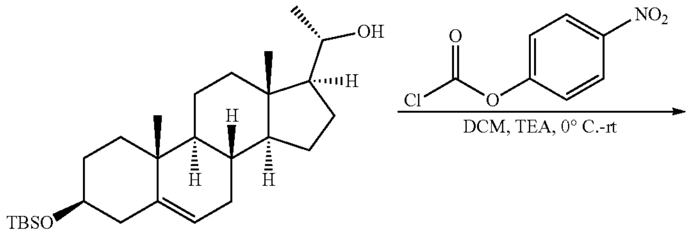

A

-continued

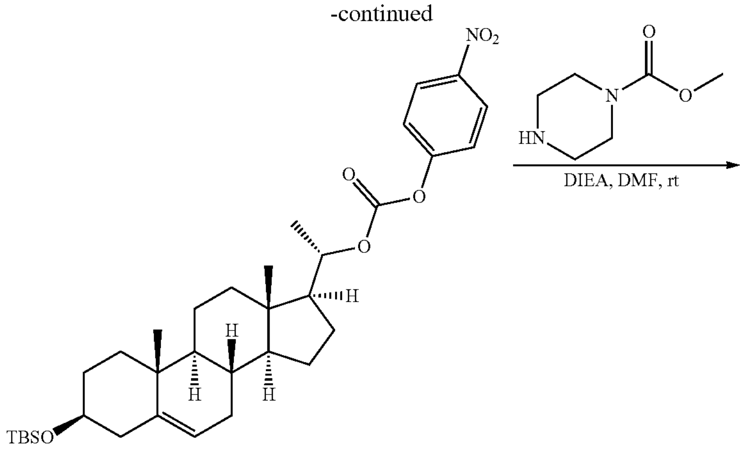

B

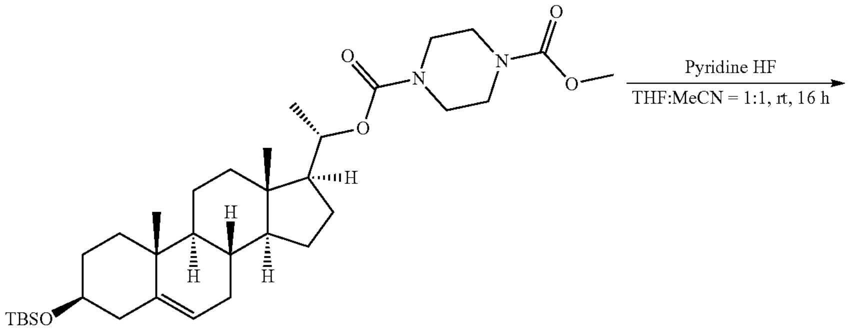

C

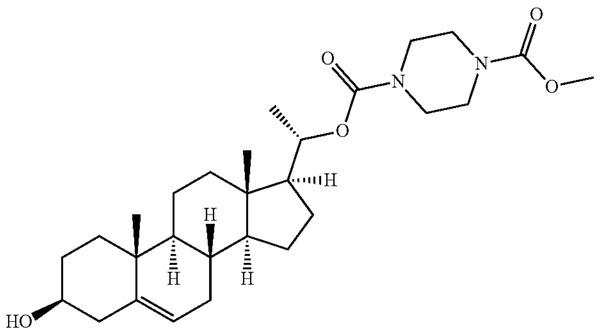

To a 0° C.; solution of compound A (450 mg, 1.04 mmol) in dichloromethane (10 mL) was added triethylamine (434 μL, 3.12 mmol) and 4-nitrophenyl carbonochloridate (314 mg, 1.56 mmol) and the reaction was stirred at room temperature for 3 h. The reaction was quenched with water (5 mL) and extracted with ethyl acetate (20 mL). The organic layer was dried with sodium sulfate and concentrated under reduced pressure. The crude product was purified by silica gel chromatography to give compound B (280 mg, 45.0%). To a solution of compound B (140 mg, 234 μmol) in DMF (4.67 mL) was added DIEA (90.8 mg, 702 μmol) and methyl piperazine-1-carboxylate (92.2 μL, 702 μmol) at room temperature. The reaction was stirred at room temperature for 16 h. The reaction was diluted water (5 mL) and extracted with ethyl acetate (15 mL). The organic layer was washed with water and brine (5 mL), dried with sodium sulfate, and concentrated under reduced pressure. The crude product was purified by silica gel chromatography to give compound C (100 mg, 70.8%). A reaction of compound C (80 mg, 133 μmol) and HF pyridine (71.7 μL, 796 μmol) in tetrahydrofuran (8 mL) and acetonitrile (8 mL) was stirred at room temperature for 16 h. The pH of the reaction was adjusted to pH 7 with saturated $NaHCO_3$ solution, extracted with ethyl acetate (15 mL). The organic layer was dried over anhydrous sodium sulfate and concentrated under reduced pressure. The crude product was purified by silica gel chromatography to give the title compound 466 (44.9 mg, 69.2%) as a white solid. $^1H$ NMR (400 MHz, Chloroform-d) δ 5.35 (d, J=5.2 Hz, 1H), 4.90-4.79 (m, 1H), 3.71 (s, 3H), 3.57-3.37 (m, 9H), 2.32-2.20 (m, 2H), 2.05-1.74 (m, 6H), 1.69-1.38 (m, 13H), 1.26 (d, J=6.0 Hz, 3H), 1.21-1.03 (m, 4H), 1.01 (s, 3H), 0.94 (dt, J=11.2, 5.6 Hz, 1H), 0.69 (s, 3H).

Example 467: Methyl 4-(((S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propyl)carbamoyl)piperazine-1-carboxylate

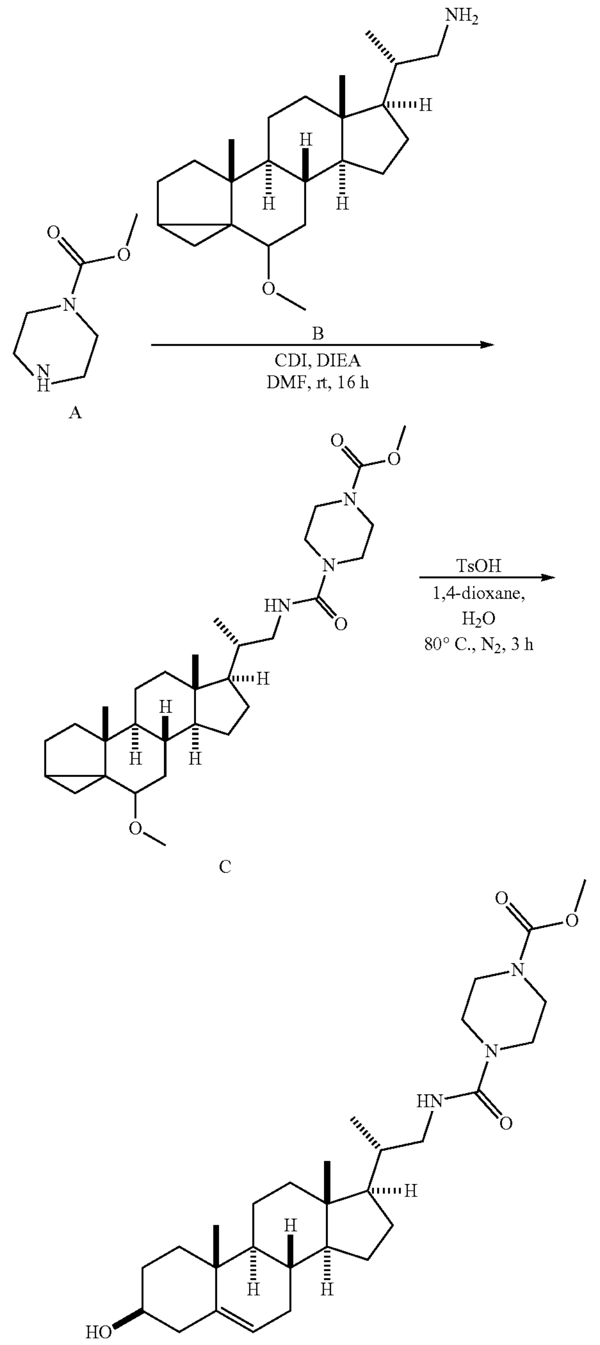

To a solution of compound B (100 mg, 0.29 mmol) in DMF (2 mL) was added compound A (41.7 mg, 289 μmol), CDI (61 mg, 376 μmol) and DIEA (112 mg, 868 μmol). The reaction was stirred at room temperature under $N_2$ for 16 h. The reaction was diluted with water (5 mL) and extracted with Ethyl Acetate (10 mL). The organic layer was washed with brine, dried over sodium sulfate, filtered, and concentrated. The reaction was purified by silica gel chromatography to afford compound C (50 mg) as a white solid.

Methyl-4-(((2S)-2-((1aR,3aR,3bS,5aS,6R,8aS,8bS,10aR)-10-methoxy-3a,5a-dimethylhexadecahydrocyclopenta[a]cyclopropa[2,3]cyclopenta[1,2-f]naphthalen-6-yl)propyl)carbamoyl)piperazine-1-carboxylate (50 mg, 0.1 mmol) was reacted according to the method of Example 430 to afford the title compound 467 (15 mg, 30.8%) as a white solid. $^1$H NMR (400 MHz, Chloroform-d) δ 5.34 (d, J=3.6 Hz, 1H), 4.45 (t, J=5.6 Hz, 1H), 3.72 (s, 3H), 3.56-3.44 (m, 5H), 3.43-3.32 (m, 5H), 2.93-2.81 (m, 1H), 2.35-2.16 (m, 2H), 2.04-1.79 (m, 6H), 1.55-1.37 (m, 8H), 1.22-1.03 (m, 6H), 1.02-0.96 (m, 7H), 0.94-0.82 (m, 3H), 0.70 (s, 3H).

Example 468: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-{4-[(1 S)-2,2,2-trifluoro-1-hydroxyethyl]piperidin-1-yl}pentan-1-one

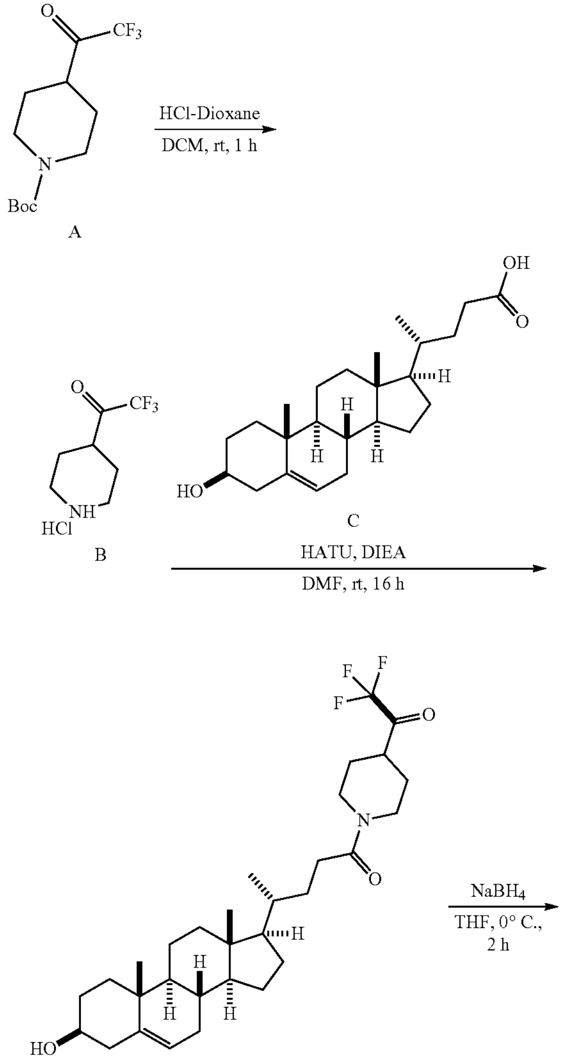

-continued

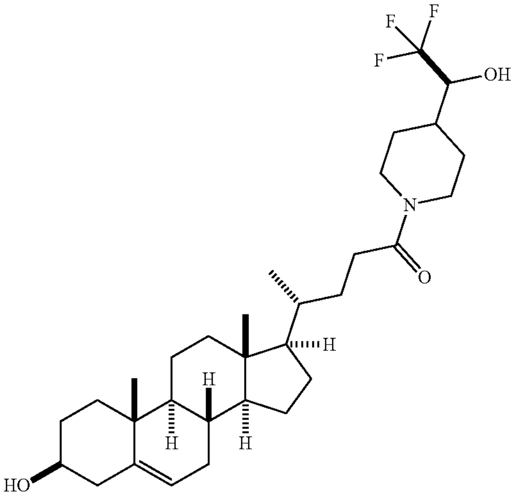

To a solution of compound A (200 mg, 711 μmol) in DCM (4 mL) was added hydrochloric acid (2 mL) at room temperature and the reaction was stirred for 2 h. The reaction concentrated under reduced pressure to afford compound B (140 mg) as the HCl salt. To a solution of compound B (140 mg, 645 μmol), compound C (232 mg, 618 μmol) and DIPEA (599 mg, 4.64 mmol) in DMF (5 mL) was added HATU (588 mg, 1.55 mmol) at room temperature under $N_2$ and stirred for 16 h. The reaction was diluted with saturated $NH_4Cl$ (30 mL) and extracted with EtOAc (10 mL*2). The combined organic layers were washed with saturated $NaHCO_3$ (20 mL), water (20 mL), brine (20 mL), dried over sodium sulfate and concentrated under reduced pressure. The residue was purified by silica gel chromatography to afford compound D (100 mg, 24%) as a white solid.

To a solution of compound D (100 mg, 186 μmol) in THF (4 mL) was added $NaBH_4$ (14.07 mg, 372 μmol) at 0° C. The reaction was stirred for 2 hours at room temperature. The solvent was concentrated under reduced pressure. The residue was diluted with water, extracted with Ethyl Acetate (10 mL*2), dried over sodium sulfate, and concentrated under reduced pressure. The residue was purified by silica gel chromatography to afford the title compound 468 (10.3 mg, 13%) as a white solid. LCMS: $[M+1]^+$=540.20. $^1H$ NMR (400 MHz, Chloroform-d) δ 5.39-5.32 (m, 1H), 4.70 (d, J=13.2 Hz, 1H), 3.97-3.72 (m, 2H), 3.52 (td, J=10.0, 8.8, 4.4 Hz, 1H), 3.02 (s, 1H), 2.52 (s, 1H), 2.29-3.10 (m,, 4H), 2.03-1.90 (m, 4H), 1.88-1.80 (m, 3H), 1.76 (s, 2H), 1.65-1.52 (m, 5H), 1.44 (dt, J=13.2, 4.8 Hz, 4H), 1.38-1.28 (m, 4H), 1.21-1.05 (m, 4H), 1.01 (s, 3H), 0.95 (d, J=6.4 Hz, 3H), 0.91-0.81 (m, 2H), 0.68 (s, 3H). $^{19}F$ NMR (376 MHz, Chloroform-d) δ−75.81 (d, J=68.5 Hz).

Example 469: (4R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(1-methoxyethyl)piperidin-1-yl)pentan-1-one

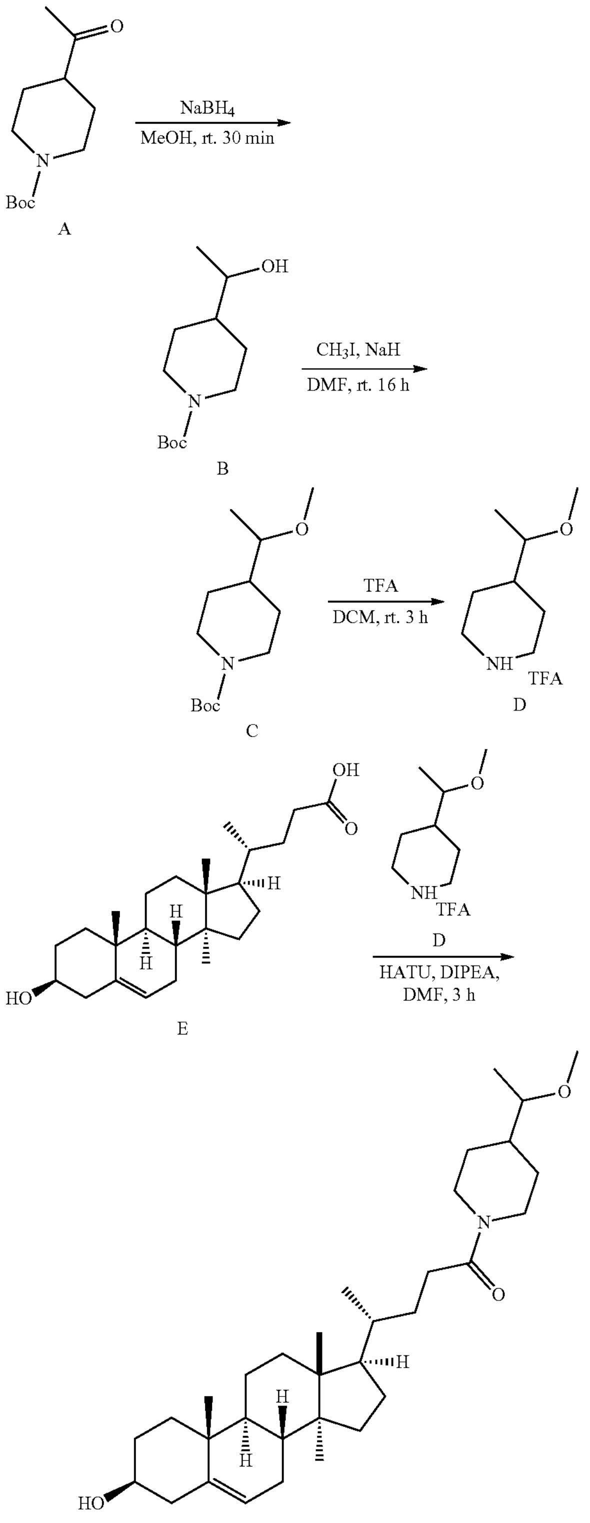

To a solution of compound A (1.0 g, 4.4 mmol) in methanol (10 mL) was added $NaBH_4$ (166 mg, 4.4 mmol) at room temperature, the reaction was stirred for 30 minutes. The reaction was quenched with $H_2O$ (20 mL) and extracted with ethyl acetate (50 mL). The organic layer was concentrated under reduced pressure. The crude product was purified by silica gel chromatography to afford compound B (860 mg, 85%). To a solution of compound B (500 mg, 2.18 mmol) in DMF (5 mL) was added $CH_3I$ (1.55 g, 10.9 mmol) and NaH (436 mg, 10.9 mmol, 60% dispersion in mineral oil) at 0° C. under $N_2$, the reaction was stirred for 16 hours. The reaction was quenched with $H_2O$ (10 mL) and extracted with ethyl acetate (20 mL). The organic layer was concentrated to afford compound C (500 mg, 85%). To a solution of compound C (200 mg, 822 μmol) in DCM (2 mL) was added TFA (0.6 mL) at room temperature, the reaction was stirred at room temperature for 3 hours. The reaction concentrated to afford compound D (110 mg) as the TFA salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (180 mg, 481 μmol) and 4-(1-methoxyethyl)piperidine TFA salt (52.6 mg, 218 μmol) were reacted according to the method of Example 526 to afford the title compound 469 (40 mg, 17%) as a white solid. LCMS: $[M+1]^+$=500.25. $^1H$ NMR (400 MHz, Chloroform-d) δ 5.35 (d, J=5.2 Hz, 1H), 3.48-3.54 (m, 1H), 3.32 (s, 3H), 3.07 (t, J=6.4 Hz, 1H), 2.46-2.36 (m, 1H), 2.22-2.28 (m, 3H), 2.02-1.74 (m, 11H), 1.69-1.43 (m, 9H), 1.34-1.23 (m, 4H), 1.21-1.13 (m, 3H), 1.10 (d, J=6.0 Hz, 3H), 1.01 (s, 3H), 0.96 (d, J=6.4 Hz, 3H), 0.94-0.84 (m, 1H), 0.68 (s, 3H).

Example 470: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-3-(hydroxymethyl)pyrrolidin-1-yl)pentan-1-one

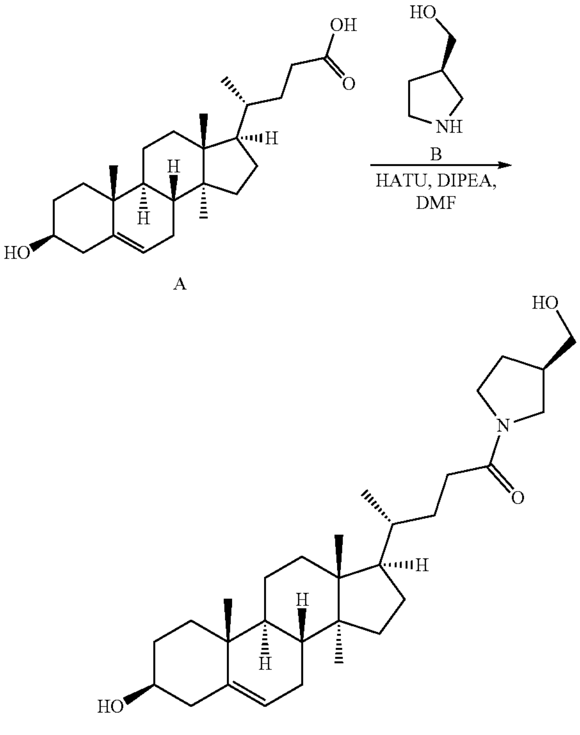

(R)-pyrrolidin-3-ylmethanol (81 mg, 801 μmol), (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (300 mg, 801 μmol) was reacted according to the method of Example 536 to afford the title compound 470 (105 mg, 28.6%) as a white solid. LCMS: $[M+1]^+$=457.36 $^1H$ NMR (400 MHz, Chloroform-d) δ 5.35 (d, J=5.2 Hz, 1H), 3.74-3.18 (m, 7H), 2.46-1.90 (m, 8H), 1.89-1.03 (m, 20H), 1.00 (s, 3H), 0.94 (d, J=6.4 Hz, 3H), 0.68 (s, 3H).

Example 471: 233: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3S)-3-(hydroxymethyl)pyrrolidin-1-yl]pentan-1-one

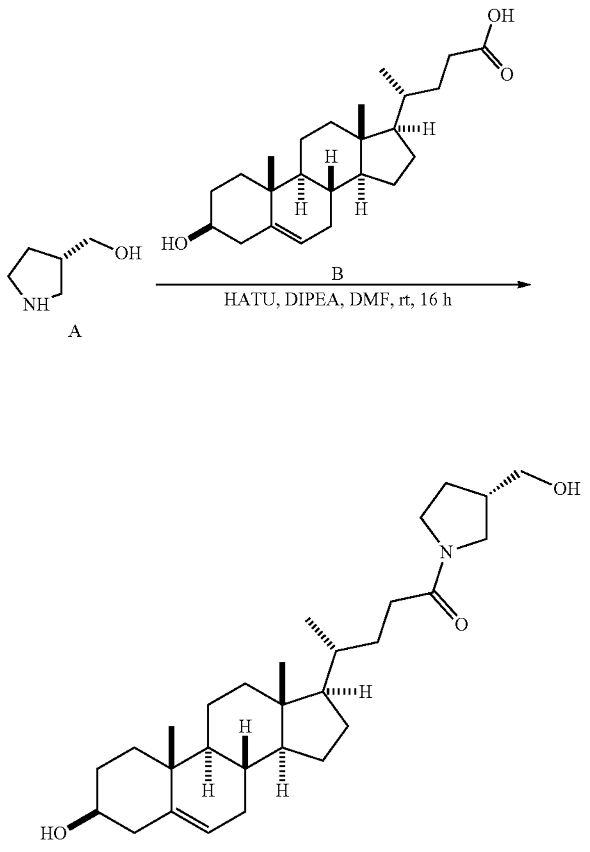

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (333 mg, 890 μmol), (S)-pyrrolidin-3-ylmethanol (100 mg, 989 μmol) was reacted according to the method of Example 536 to afford the title compound 471 (80 mg, 19%) as a white solid. LCMS: [M+H]+=458.4 $^1H$ NMR (400 MHz, Chloroform-d) δ 5.36-5.33 (m, 1H), 3.79-3.37 (m, 6H), 3.33-3.15 (m, 1H), 2.54-2.46 (m, 1H), 2.34-2.25 (m, 2H), 2.24-2.07 (m, 2H), 2.04-1.89 (m, 3H), 1.88-1.72 (m, 7H), 1.70-1.55 (m, 2H), 1.51-1.41 (m, 5H), 1.37-1.25 (m, 2H), 1.21-1.04 (m, 4H), 1.00 (s, 4H), 0.94 (d, J=6.4 Hz, 4H), 0.68 (s, 3H).

Example 472: N-((1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)methyl)methanesulfonamide

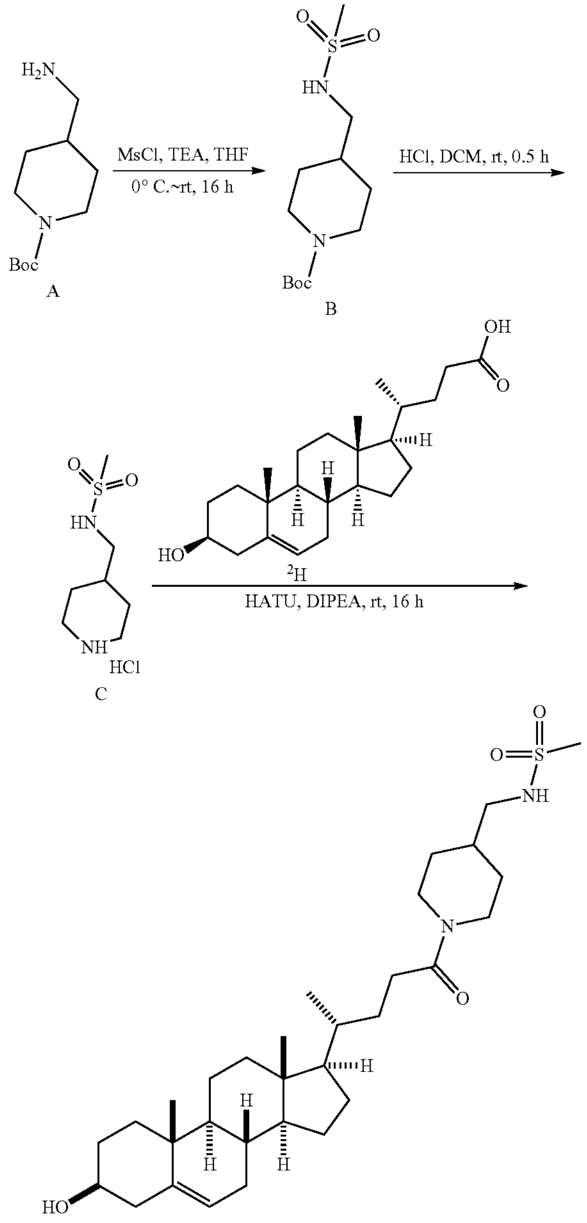

To a 0° C. solution of compound A (2.0 g, 9.33 mmol) in tetrahydrofuran (30 mL) under $N_2$ was added triethylamine (2.83 g, 28 mmol) and methanesulfonyl chloride (1.6 g, 14 mmol) and the reaction was warmed to room temperature for 16 hours. Upon completion, the reaction was quenched with saturated ammonium chloride (100 mL) and extracted with ethyl acetate (30 mL*3). The combined organic layers were washed with brine (5 mL), dried over sodium sulfate, filtered, and concentrated under reduced pressure. The crude product was purified by silica gel chromatography to afford compound B (2.0 g, 73.3%) as a yellow oil. To a solution of compound B (200 mg, 684 μmol) in DCM (6 mL) was added hydrogen chloride (1 mL, 4 mmol, 4M in 1,4-dioxane) at room temperature and the reaction was stirred for 0.5 h. The reaction concentrated under reduced pressure to give compound C as the HCl salt (154 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (228 mg, 608 μmol), N-(piperidin-4-ylmethyl)methanesulfonamide hydrochloride (108 mg, 474 μmol) was reacted according to the method of Example 436 to afford the title compound 472 (180 mg, 48%) as a white solid. LCMS: $[M+1]^+$=549.30. $^1H$ NMR (400 MHz, Chloroform-d) δ 5.35 (d, J=4.8 Hz, 1H), 4.66 (d, J=12.8 Hz, 1H), 4.44 (t, J=6.0 Hz, 1H), 3.97-3.85 (m, 1H), 3.52 (dt, J=11.2, 6.4 Hz, 1H), 3.08-2.94 (m, 6H), 2.53 (t, J=13.2 Hz, 1H), 2.41-2.17 (m, 4H), 2.06-1.95 (m, 2H), 1.90-1.71 (m, 7H), 1.63-1.41 (m, 9H), 1.35-1.28 (m, 2H), 1.22-1.05 (m, 6H), 1.04-0.92 (m, 8H), 0.68 (s, 3H).

Example 473: 1,1,1-trifluoro-N-((1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)methyl)methanesulfonamide

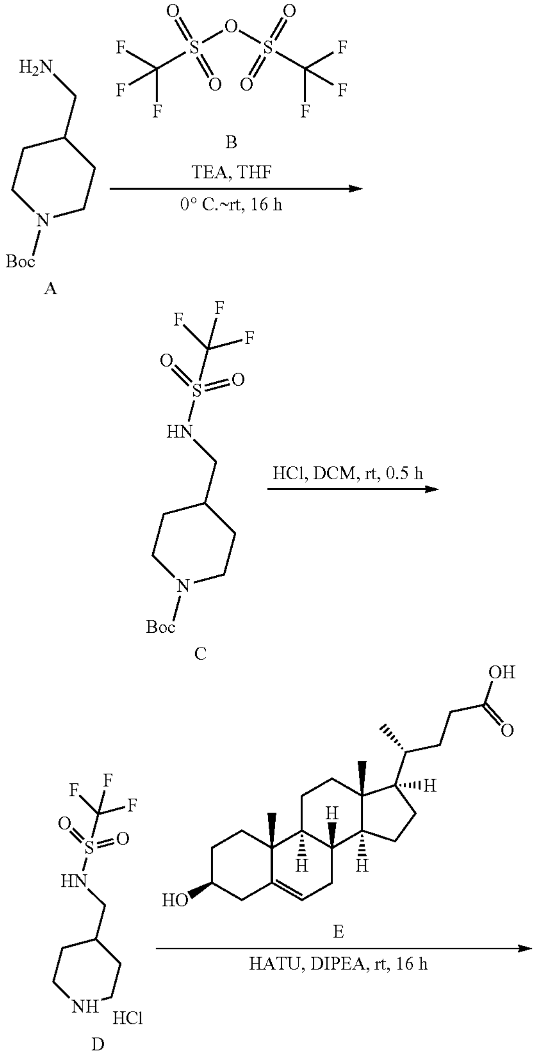

-continued

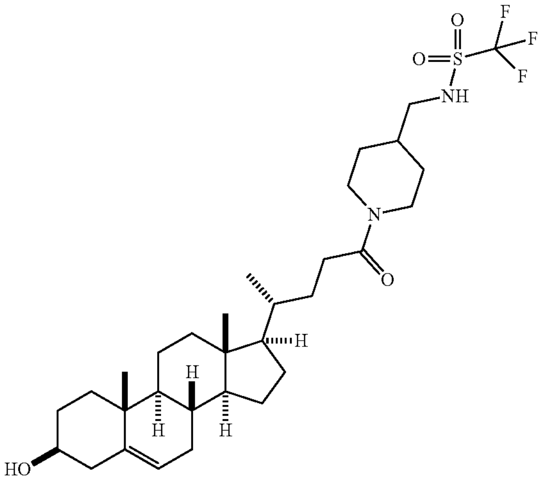

To a 0° C. solution of compound A (1.0 g, 4.67 mmol) in tetrahydrofuran (15 mL) under $N_2$ was added triethylamine (1.41 g, 14 mmol) and compound B (1.97 g, 7 mmol) and the reaction was warmed to room temperature for 16 hours. Upon completion, the reaction was quenched with saturated ammonium chloride (100 mL) and extracted with ethyl acetate (30 mL*3). The combined organic layers were washed with brine, dried over sodium sulfate, filtered, and concentrated under reduced pressure. The crude product was purified by silica gel chromatography to afford compound C (380 mg, 23.51%) as a yellow oil. To a solution of compound C (200 mg, 577 μmol) in DCM (6 mL) was added hydrogen chloride (3 mL, 12 mmol, 4M in 1, 4-dioxane) at room temperature and the reaction was stirred for 0.5 h. The reaction concentrated under reduced pressure to give compound C as the HCl salt (149 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (178 mg, 475 μmol) and 1,1,1-trifluoro-N-(piperidin-4-ylmethyl)methanesulfonamide hydrochloride (149 mg, 528 μmol) were reacted according to the method of Example 536 to afford the title compound 473 (70 mg, 25%) as a white solid. LCMS: $[M+1]^+$=603.20. $^{1}$H NMR (400 MHz, Chloroform-d) δ 5.68 (t, J=6.0 Hz, 1H), 5.35 (d, J=5.2 Hz, 1H), 4.66 (d, J=13.2 Hz, 1H), 3.90 (d, J=13.6 Hz, 1H), 3.52 (dq, J=10.4, 5.2 Hz, 1H), 3.26-3.12 (m, 2H), 3.02 (t, J=12.8 Hz, 1H), 2.53 (t, J=12.8 Hz, 1H), 2.39-2.17 (m, 4H), 2.03-1.95 (m, 2H), 1.90-1.72 (m, 7H), 1.64-1.59 (m, 1H), 1.54-1.42 (m, 7H), 1.34-1.25 (m, 3H), 1.21-1.03 (m, 6H), 1.01 (s, 3H), 0.95 (d, J=6.4 Hz, 3H), 0.93-0.84 (m, 1H), 0.68 (s, 3H). $^{19}$FNMR (376 MHz, Chloroform-d) δ−77.15 (s).

Example 474: N-((1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)methyl)-N-methylmethanesulfonamide

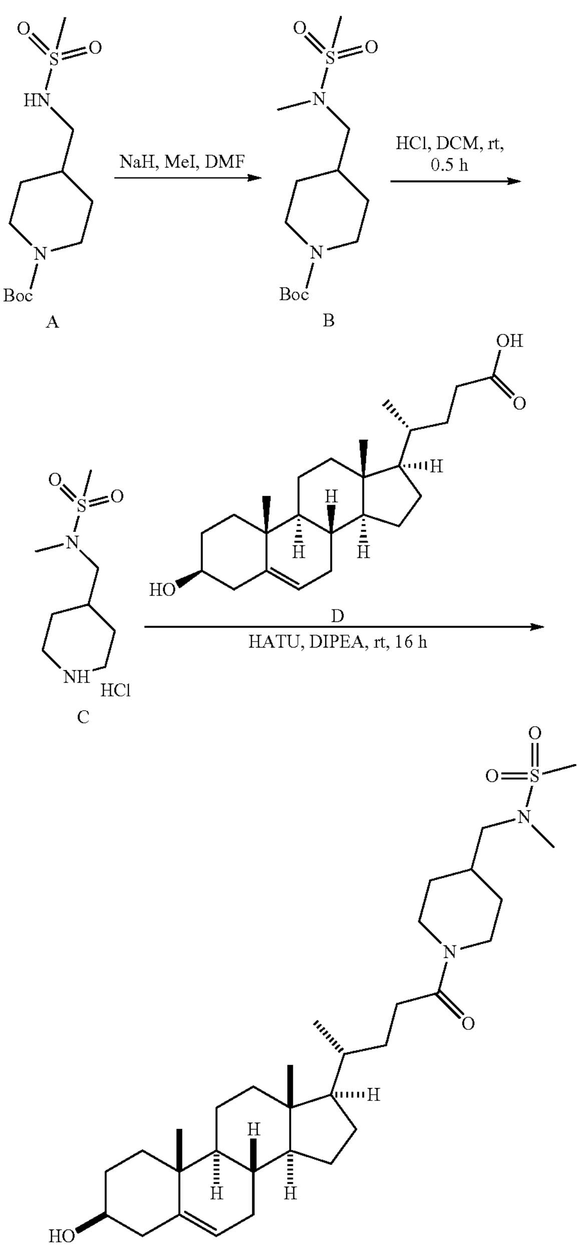

To a solution of compound A (500 mg, 1.71 mmol) in DMF (5 mL) was added NaH (78.6 mg, 1.97 mmol, 60% dispersion in mineral oil) at 0° C. and stirred for 30 mins. To the reaction was added iodomethane (364 mg, 2.57 mmol) and the reaction was warmed to room temperature for 16 hours. The reaction was diluted with $H_2O$ (5 mL) and extracted with ethyl acetate (20 mL). The organic layer was concentrated under reduced pressure. The crude product was purified by silica gel chromatography to afford compound B (500 mg, 95.4%) as a light yellow solid. To a solution of compound B (200 mg, 635 umol) in dichloromethane (2 mL)

was added HCl (1 mL, 4M in dioxane, 4 mmol). The reaction was stirred at room temperature for 0.5 h. The reaction concentrated to afford compound C as the HCl salt (152 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (212 mg, 567 μmol) and N-methyl-N-(piperidin-4-ylmethyl) methanesulfonamide hydrochloride (152 mg, 630 μmol) were reacted according to the method of Example 536 to afford the title compound 474 (70 mg, 25%) as a white solid. LCMS: $[M+1]^+$=563.20. $^1$H NMR (400 MHz, Chloroform-d) δ 5.35 (d, J=5.2 Hz, 1H), 4.62 (d, J=13.2 Hz, 1H), 3.87 (d, J=13.6 Hz, 1H), 3.52 (tt, J=10.8, 4.4 Hz, 1H), 3.10-2.89 (m, 3H), 2.87 (s, 3H), 2.79 (s, 3H), 2.62-2.52 (m, 1H), 2.42-2.16 (m, 4H), 2.03-1.70 (m, 9H), 1.55-1.39 (m, 7H), 1.37-1.26 (m, 3H), 1.20-1.10 (m, 4H), 1.09-1.03 (m, 2H), 1.01 (s, 3H), 0.95 (d, J=6.4 Hz, 3H), 0.68 (s, 3H).

Example 475: N-(1-(1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)ethyl) methanesulfonamide

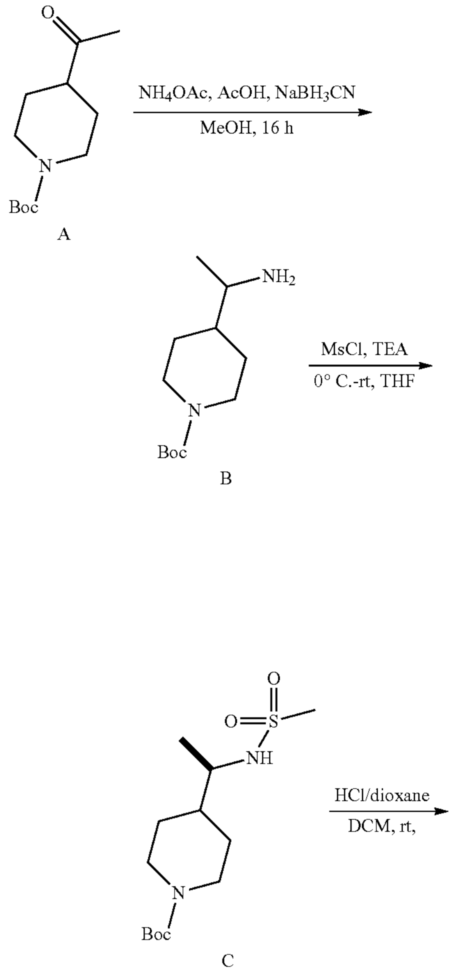

-continued

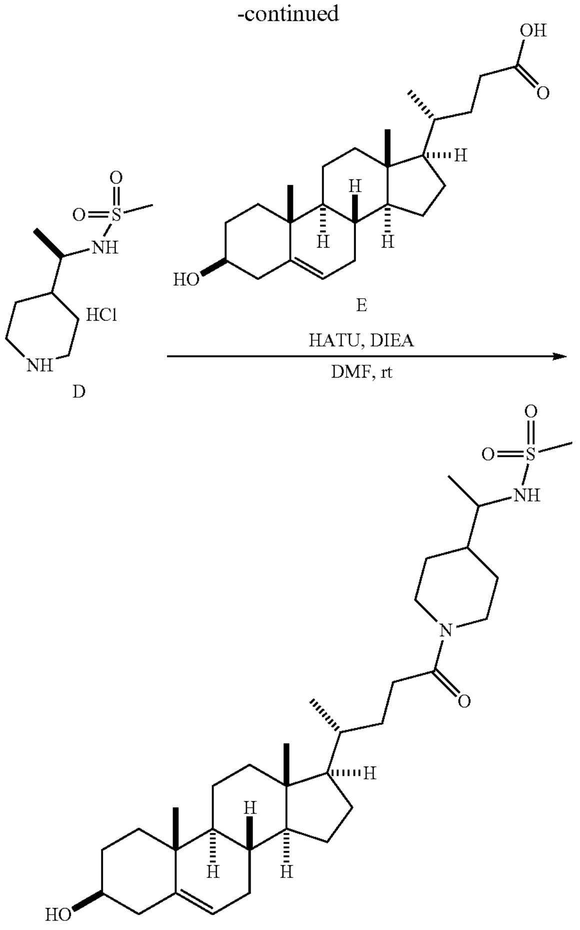

To a solution of compound A (500 mg, 2.2 mmol) in methanol (6 mL) was added ammonium acetate (678 mg, 8.8 mmol) and AcOH (0.1 mL), the reaction was stirred at room temperature after 2 hours was added $NaCNBH_3$ (166 mg, 2.64 mmol) and stirred for 16 h. The reaction was quenched with saturated aqueous NaOH (5 mL) and extracted with DCM (20 mL). The organic layer was washed with brine (5 mL), dried over sodium sulfate, filtered, and concentrated to afford compound B (400 mg). To a solution of compound B (440 mg, 1.93 mmol) in tetrahydrofuran (5 mL) at 0° C. was added TEA (385 mg) and methanesulfonyl chloride (331 mg, 2.89 mmol). The reaction was stirred at room temperature under $N_2$ for 16 h. The reaction was quenched with saturated aqueous $NH_4Cl$ (5 mL) and extracted with EtOAc (15 mL). The organic layer was washed with brine, dried over sodium sulfate, filtered, and concentrated. The reaction was purified by column chromatography on silica gel to afford compound C (290 mg, 48.5%) as a solid. To a solution of compound C (150 mg, 0.49 mmol) in dichloromethane (2 mL) was added HCl (0.3 mL, 1.2 mmol, 4M in 1, 4-dioxane). The reaction was stirred at room temperature under $N_2$ for 0.5 h. The reaction concentrated to afford the compound D (110 mg) as the HCl salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (180 mg, 0.48 mmol) and (R)—N-(1-(piperidin-4-yl)ethyl) methanesulfonamide (110 mg, 0.49 mmol) was reacted according to the method of Example 536 to afford the title compound 475 (80 mg, 16.3%) as a white solid. LCMS:

$[M+1]^+$=563.25. $^1$H NMR (400 MHz, Chloroform-d) δ 5.35 (d, J=5.2 Hz, 1H), 4.71 (t, J=12.4 Hz, 1H), 4.08 (t, J=8.0 Hz, 1H), 3.91 (d, J=13.6 Hz, 1H), 3.53 (td, J=11.6, 4.8 Hz, 1H), 3.44-3.26 (m, 1H), 2.97 (s, 3H), 2.55-2.17 (m, 5H), 2.06-1.68 (m, 8H), 1.55-1.40 (m, 7H), 1.37-1.05 (m, 13H), 1.01 (s, 4H), 0.95 (d, J=6.4 Hz, 3H), 0.89 (q, J=7.2 Hz, 1H), 0.68 (s, 3H).

Example 476: N-(2,2,2-trifluoro-1-(1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)ethyl)methanesulfonamide

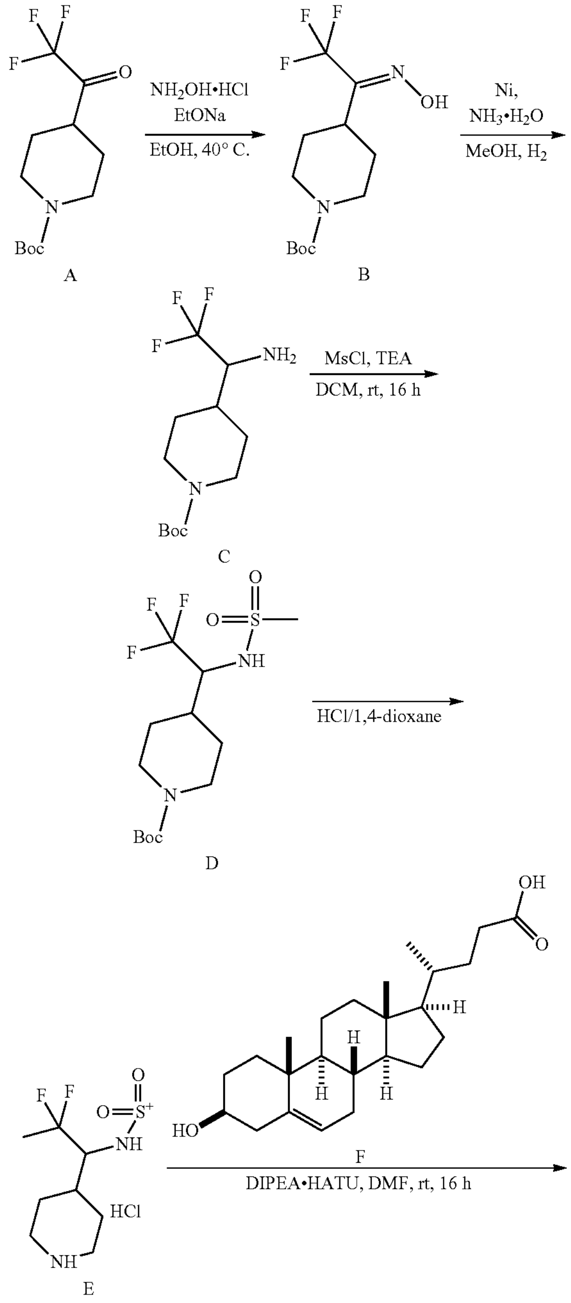

-continued

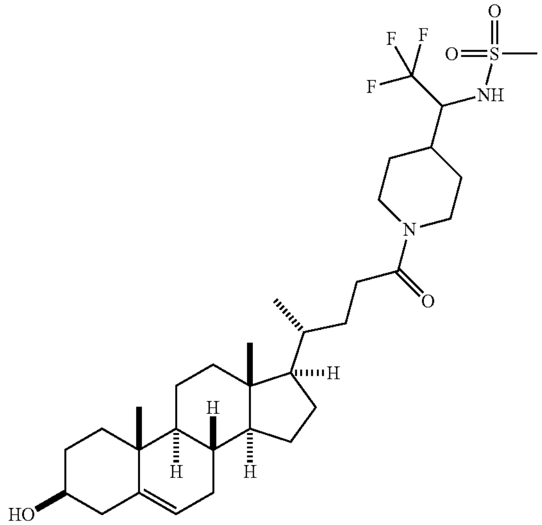

To a solution of compound A (0.7 g, 2.49 mmol) in ethanol (21 mL, 360 mmol) was added hydrogen hydroxylamine chloride (346 mg, 4.98 mmol) and sodium ethanolate (508 mg, 7.47 mmol). The reaction was stirred at 40° C. under $N_2$ for 16 h. The reaction was quenched with water (10 mL) extracted with ethyl acetate (30 mL). The organic layer was washed with brine (10 mL), dried over sodium sulfate, filtered, and concentrated. The residue was purified by silica gel chromatography to afford compound B (320 mg, 43.4%) as a white solid. To a solution of compound B (170 mg, 574 μmol) in MeOH (3 mL) was added Raney nickel (20 mg, 341 μmol) and ammonium hydroxide (0.2 mL). The reaction was stirred at rt under $H_2$ for 16 h. The reaction was filtered and concentrated to afford compound C (130 mg, 80.7%) as a yellow oil.

To a solution of compound C (90 mg, 319 μmol) in DCM (2.77 mL) at 0° C. under $N_2$ was added triethylamine (96.8 mg, 956 μmol) and methanesulfonyl chloride (54.8 mg, 478 μmol). The reaction was warmed to room temperature under $N_2$ for 3 h. The reaction was quenched with water (5 mL) and extracted with EtOAc (10 mL). The organic layer was washed with brine (5 mL), dried over sodium sulfate, filtered, and concentrated. The residue was purified by silica gel chromatography to afford the compound D (50 mg, 43.8%) as a white solid. To a solution of compound D (50 mg, 138 μmol) in DCM (3 mL) was added HCl/dioxane (0.5 mL, 4M in 1,4-dioxane). The reaction was stirred at room temperature under $N_2$ for 1 h. The reaction concentrated to afford compound E (30 mg) as the HCl salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (37.7 mg, 101 μmol) and N-(2,2,2-trifluoro-1-(piperidin-4-yl)ethyl)methanesulfonamide (30 mg, 112 μmol) were reacted according to the method of Example 430 to afford the title compound 476 (30 mg, 42.2%) as a white solid. LCMS: $[M+1]^+$=617.15. $^1$H NMR (400 MHz, Chloroform-d) δ 5.35 (d, J=4.8 Hz, 1H), 5.20 (d, J=10.0 Hz, 1H), 4.90-4.60 (m, 1H), 3.94 (d, J=15.2 Hz, 2H), 3.55-3.48 (m, 1H), 3.05 (s, 4H), 2.56-2.44 (m, 1H), 2.43-2.16 (m, 4H), 2.12-1.69 (m, 10H), 1.50-1.42 (m, 7H), 1.36-1.28 (m, 3H), 0.95-0.84 (m, 4H), 1.00 (s, 4H), 0.97-0.87 (m, 4H), 0.68 (s, 3H).

Example 477: 2-hydroxy-N-((1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)methyl)-2-methylpropanamide

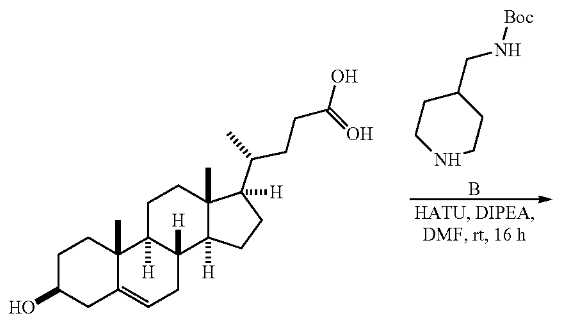

A

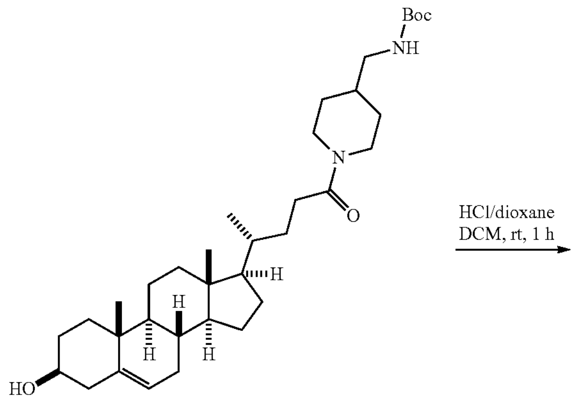

C

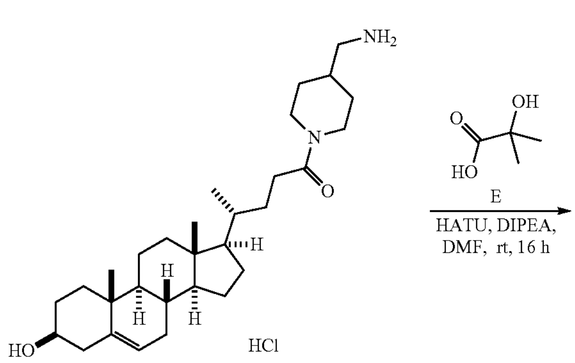

HCl

D

-continued

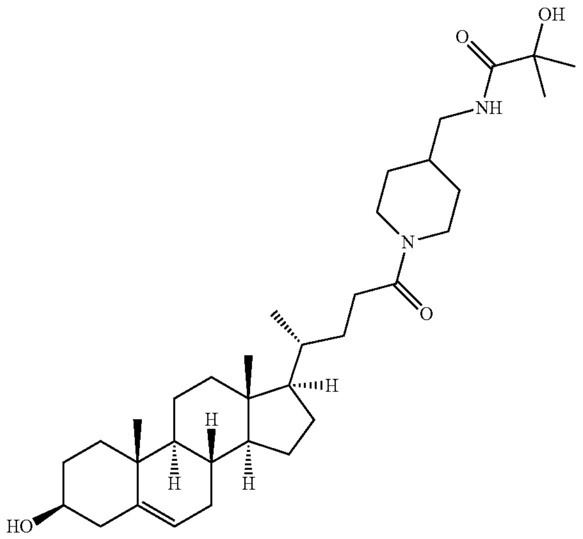

To a solution of compound A (500 mg, 1.33 mmol) and compound B (318 mg, 1.48 mmol) in DMF (15 mL) was added DIPEA (1.15 g, 8.9 mmol), HATU (1.13 g, 2.97 mmol) and the reaction was stirred at room temperature under $N_2$ for 16 h. The reaction was quenched with saturated aqueous $NH_4Cl$ (5 mL) and extracted with EtOAc (15 mL). The organic layer was washed with brine (5 mL), dried over sodium sulfate, filtered, and concentrated. The reaction was purified by silica gel chromatography to afford compound C (450 mg) as a solid. To a solution of compound C (250 mg, 0.44 mmol) in dichloromethane (3 mL) was added hydrogen chloride (0.2 mL 4M in 1,4-dioxane, 0.8 mmol). The reaction was stirred at room temperature for 1 hour. The reaction concentrated to afford the compound D (220 mg) as the HCl salt.

To a solution of compound D (220 mg, 0.44 mmol) and compound E (43.8 mg, 0.42 mmol) in DMF (5 mL) was added DIPEA (362 mg, 2.8 mmol), HATU (355 mg, 0.93 mmol) and the reaction was stirred at room temperature under $N_2$ for 16 h. The reaction was quenched with saturated aqueous $NH_4Cl$ (5 mL) and extracted with EtOAc (15 mL). The organic layer was washed with brine (5 mL), dried over sodium sulfate, filtered, and concentrated. The reaction was purified by silica gel chromatography to afford compound 477 (70 mg, 26.9%) as a white solid. LCMS: $[M+1]^+$ =557.30. $^1H$ NMR (400 MHz, Chloroform-d) δ 6.84 (t, J=5.6 Hz, 1H), 5.35 (d, J=5.2 Hz, 1H), 4.62 (d, J=13.2 Hz, 1H), 3.85 (d, J=13.6 Hz, 1H), 3.52 (dt, J=11.2, 6.0 Hz, 1H), 3.17-3.15 (m, 2H), 2.99 (t, J=12.8 Hz, 1H), 2.53 (t, J=12.8 Hz, 1H), 2.42-2.16 (m, 5H), 2.05-1.68 (m, 10H), 1.46 (s, 12H), 1.30 (d, J=10.4 Hz, 3H), 1.22-1.02 (m, 7H), 1.01 (s, 3H), 0.95 (d, J=6.4 Hz, 3H), 0.92-0.85 (m, 1H), 0.68 (s, 3H).

Example 478: 2-hydroxy-N-(1-(1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)ethyl)-2-methylpropanamide

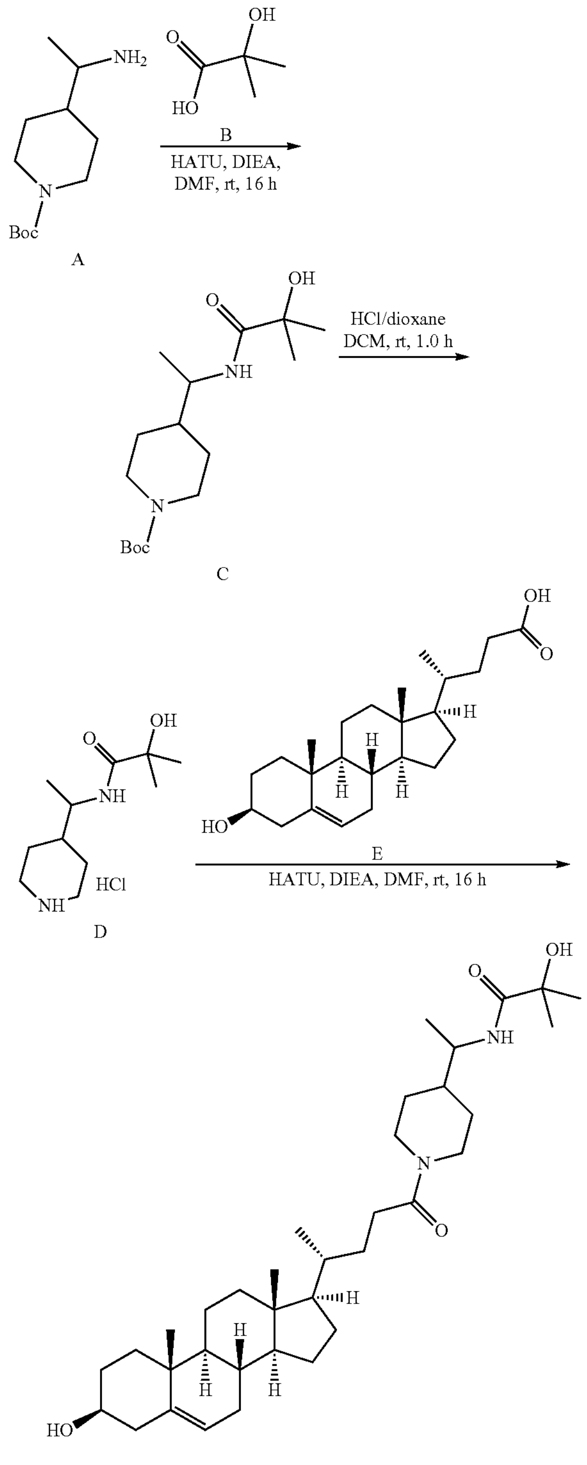

To a solution of compound A (500 mg, 2.19 mmol) and compound B (253 mg, 2.43 mmol) in DMF (10 mL) was added DIEA (1.89 g, 14.6 mmol) and HATU (1.85 g, 4.87 mmol). The reaction was stirred at room temperature under $N_2$ for 16 h. The reaction was quenched with saturated aqueous $NH_4Cl$ (5 mL) and extracted with EtOAc (15 mL). The organic layer was washed with brine (5 mL), dried over sodium sulfate, filtered, and concentrated. The residue was purified by silica gel chromatography to afford compound C (120 mg, 17.4%) as a white solid. To a solution of compound C (120 mg, 382 μmol) in DCM (2.0 mL) was added hydrogen chloride (0.2 mL, 4M in 1,4-dioxane, 0.8 mmol). The reaction was stirred at room temperature for 1 hour. The reaction concentrated to afford the compound D (85 mg) as the HCl salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (134 mg, 357 μmol) and 2-hydroxy-2-methyl-N-(1-(piperidin-4-yl)ethyl)propanamide (85 mg, 0.38 mmol) was reacted according to the method of Example 536 to afford the title compound 478 (40 mg, 11.2%) as a white solid. LCMS: $[M+1]^+$=571.30. $^1$H NMR (400 MHz, Chloroform-d) δ 6.56 (bs, 1H), 5.37-5.33 (m, 1H), 4.67 (bs, 1H), 3.97-3.78 (m, 2H), 3.57-3.48 (m, 1H), 3.03-2.90 (m, 1H), 2.53-2.15 (m, 6H), 2.05-1.92 (m, 2H), 1.88-1.80 (m, 3H), 1.79-1.68 (m, 3H), 1.54-1.41 (m, 13H), 1.33-1.24 (m, 5H), 1.21-1.06 (m, 8H), 1.00 (s, 3H), 0.94 (d, J=6.8 Hz, 4H), 0.68 (s, 3H).

Example 479: 2-hydroxy-2-methyl-N-(2,2,2-trifluoro-1-(1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)ethyl)propanamide

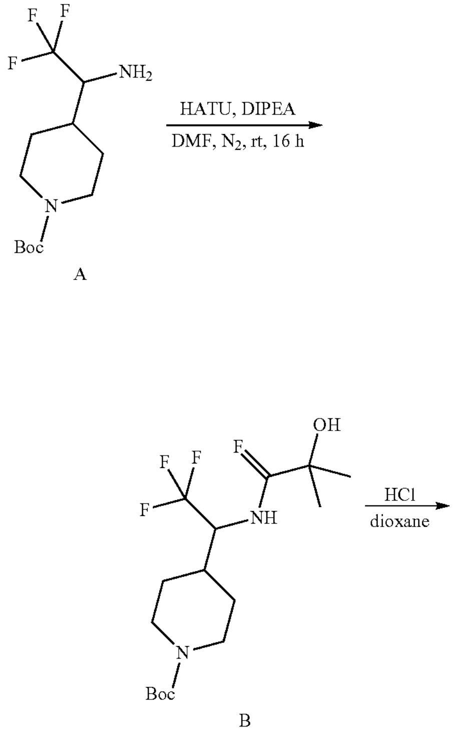

-continued

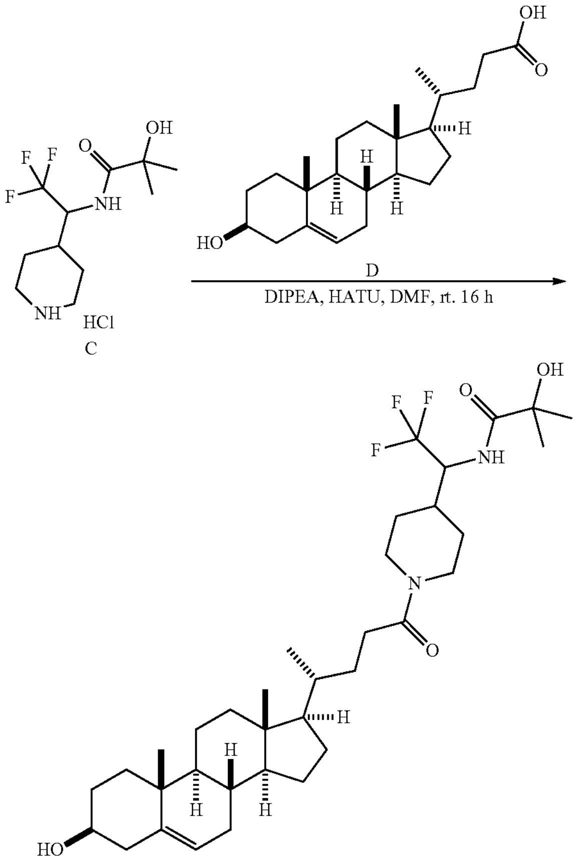

To a solution of compound A (65 mg, 230 μmol) in DMF (2 mL) was added 2-hydroxy-2-methylpropanoic acid (24 mg, 230 μmol), HATU (175 mg, 460 μmol), DIPEA (179 mg, 1.38 mmol) and the was stirred at room temperature under $N_2$ for 16 h. The reaction was quenched with saturated aqueous $NH_4Cl$ (5 mL), extracted with EtOAc (10 mL). The organic layer was washed with brine (5 mL), dried over sodium sulfate, filtered, and concentrated. The residue was purified by silica gel chromatography to afford the compound B (30 mg, 35.3%) as a white solid. To a solution of compound B (30 mg, 81.4 mmol) in DCM (1 mL) was added HCl (0.1 mL, 4M in 1,4-dioxane). The reaction was stirred at room temperature under $N_2$ for 16 h. The reaction concentrated to afford compound C (20 mg) as the HCl salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (25.1 mg, 67.1 μmol) and 2-hydroxy-2-methyl-N-(2,2,2-trifluoro-1-(piperidin-4-yl)ethyl)propanamide hydrochloride (20 mg, 74.5 μmol) were reacted according to the method of Example 536 to afford the title compound 479 (20 mg, 43.4%) as a white solid. LCMS: $[M+1]^+$=625.20. $^1$H NMR (400 MHz, Chloroform-d) δ 7.05 (t, J=11.2 Hz, 1H), 5.35 (d, J=5.2 Hz, 1H), 4.69 (s, 1H), 4.53 (s, 1H), 3.90 (t, J=12.4 Hz, 1H), 3.55-3.49 (m, 1H), 3.07-2.97 (m, 1H), 2.56-2.47 (m, 1H), 2.38-2.19 (m, 5H), 2.09-1.95 (m, 4H), 1.91-1.70 (m, 7H), 1.53-1.43 (m, 12H), 1.37-1.28 (m, 4H), 1.21-1.02 (m, 5H), 1.01 (s, 3H), 0.94 (d, J=6.8 Hz, 4H), 0.89 (m, 1H), 0.68 (s, 3H). $^{19}$F NMR (376 MHz, Chloroform-d) δ−71.84, −72.10

Example 480: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(1-methyl-1H-pyrazol-5-yl)piperazin-1-yl)pentan-1-one

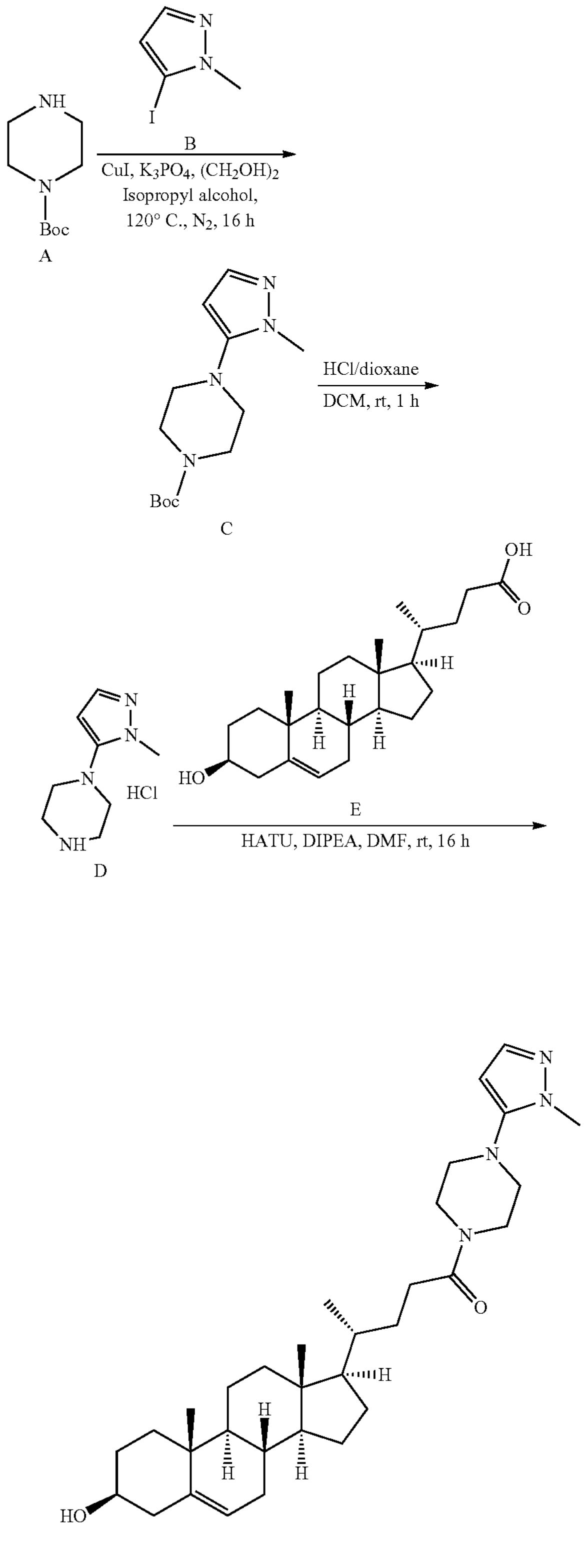

To a solution of compound A (100 mg, 0.54 mmol) and compound B (223 mg, 1.07 mmol) in isopropyl alcohol (1.5 mL) was added CuI (20.5 mg, 0.1 mmol), $K_3PO_4$ (456 mg, 2.15 mmol) and ethylene glycol (33.3 mg, 0.5 mmol). The reaction was stirred at 120° C. under $N_2$ for 16 h in a sealed tube. The reaction was cooled to room temperature and quenched with water (5 mL) and extracted with EtOAc (15 mL). The organic layer was washed with brine (5 mL), dried over sodium sulfate, filtered, and concentrated. The residue was purified by silica gel chromatography to afford compound C (50 mg, 34.9%) as a light yellow solid. To a solution of compound C (50 mg, 0.2 mmol) in dichloromethane (2 mL) was added HCl (0.1 mL, 4M in 1, 4-dioxane, 0.4 mmol). The reaction was stirred at room temperature for 1 h. The reaction concentrated to afford the compound D (30 mg) as the HCl salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (100 mg, 0.6 mmol) and 1-(1-methyl-1H-pyrazol-5-yl)piperazine hydrochloride (30 mg, 0.16 mmol) were reacted according to the method of Example 536 to afford the title compound 480 (15.9 mg, 18.6%) as a white solid. LCMS: $[M+1]^+=523.30$. $^1H$ NMR (400 MHz, Chloroform-d) δ 7.37 (s, 1H), 5.81 (s, 1H), 5.35 (d, J=4.8 Hz, 1H), 3.79-3.72 (m, 5H), 3.64-3.58 (m, 2H), 3.56-3.48 (m, 1H), 2.92-2.93 (m, 4H), 2.46-2.37 (m, 1H), 2.33-2.19 (m, 3H), 2.03-1.95 (m, 2H), 1.92-1.78 (m, 4H), 1.56-1.44 (m, 7H), 1.40-1.24 (m, 5H), 1.22-1.06 (m, 4H), 1.01 (s, 3H), 0.96 (d, J=6.4 Hz, 4H), 0.69 (s, 3H).

Example 481: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(1-methyl-1H-imidazol-5-yl)piperazin-1-yl]pentan-1-one

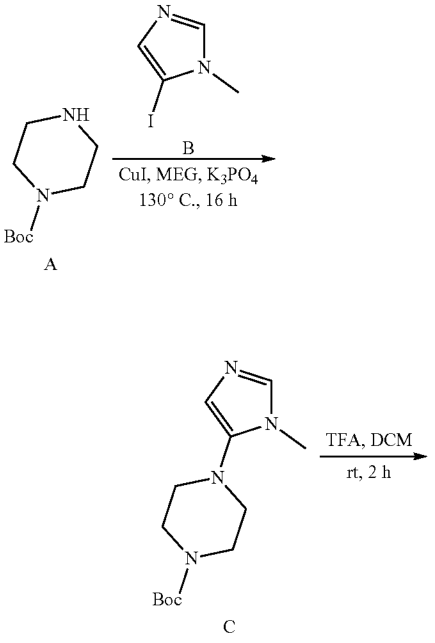

-continued

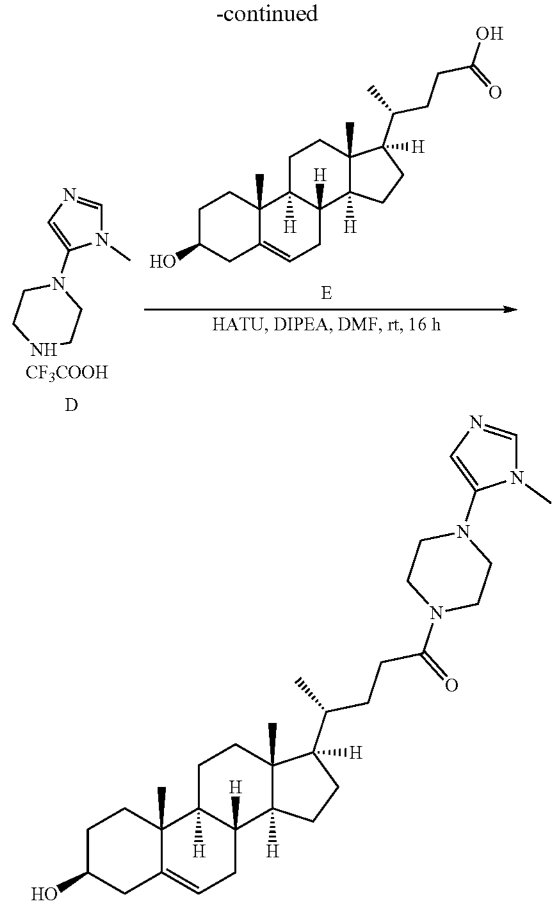

To a solution of compound A (100 mg, 0.54 mol) in isopropanol (3 mL) was added compound B (223 mg, 1.07 mmol), CuI (41 mg, 215 mol), MEG (67 mg, 1.07 mmol) and $K_3PO_4$ (456 mg, 2.15 mmol). The reaction was stirred at 130° C.; for 16 hours. The reaction was cooled to room temperature. Water (30 mL) was added, and the reaction was extracted with EtOAc (20 mL*2). The combined organic layers were dried over sodium sulfate concentrated under reduced pressure. The residue was purified by silica gel chromatography to afford compound C (45 mg, 32%) as a yellow solid. To a solution of C (130 mg, 488 μmol) in DCM (3 mL) at room temperature was added TFA (1 mL). The reaction was stirred at room temperature for 2 hours. The reaction concentrated under reduced pressure to afford D (135 mg, 98%) as the TFA salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (180 mg, 481 μmol) and 1-(1-methyl-1H-imidazol-5-yl) piperazine 2,2,2-trifluoroacetate (100 mg, 357 μmol) were reacted according to the method of Example 536 to afford the title compound 481 (10 mg, 4%) as a white solid. LCMS: [M+1]+=523.25 $^1H$ NMR (400 MHz, DMSO-$d_6$) δ 8.39 (s, 1H), 7.06 (s, 1H), 5.27 (d, J=4.8 Hz, 1H), 4.59 (s, 1H), 3.63 (s, 3H), 3.59 (t, J=4.8 Hz, 4H), 3.24 (s, 1H), 2.91-2.80 (m, 4H), 2.41-2.33 (m, 1H), 2.29-2.22 (m, 1H), 2.18-2.09 (m, 2H), 2.05-1.90 (m, 2H), 1.84-1.72 (m, 2H), 1.67 (t, J=8.0 Hz, 2H), 1.57-1.34 (m, 7H), 1.26 (d, J=12.4 Hz, 4H), 1.15-1.08 (m, 2H), 1.02-0.97 (m, 2H), 0.96-0.91 (m, 6H), 0.88-0.83 (m, 1H), 0.66 (s, 3H).

Example 402: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(5-methyl-1,3,4-oxadiazol-2-yl)piperazin-1-yl)pentan-1-one

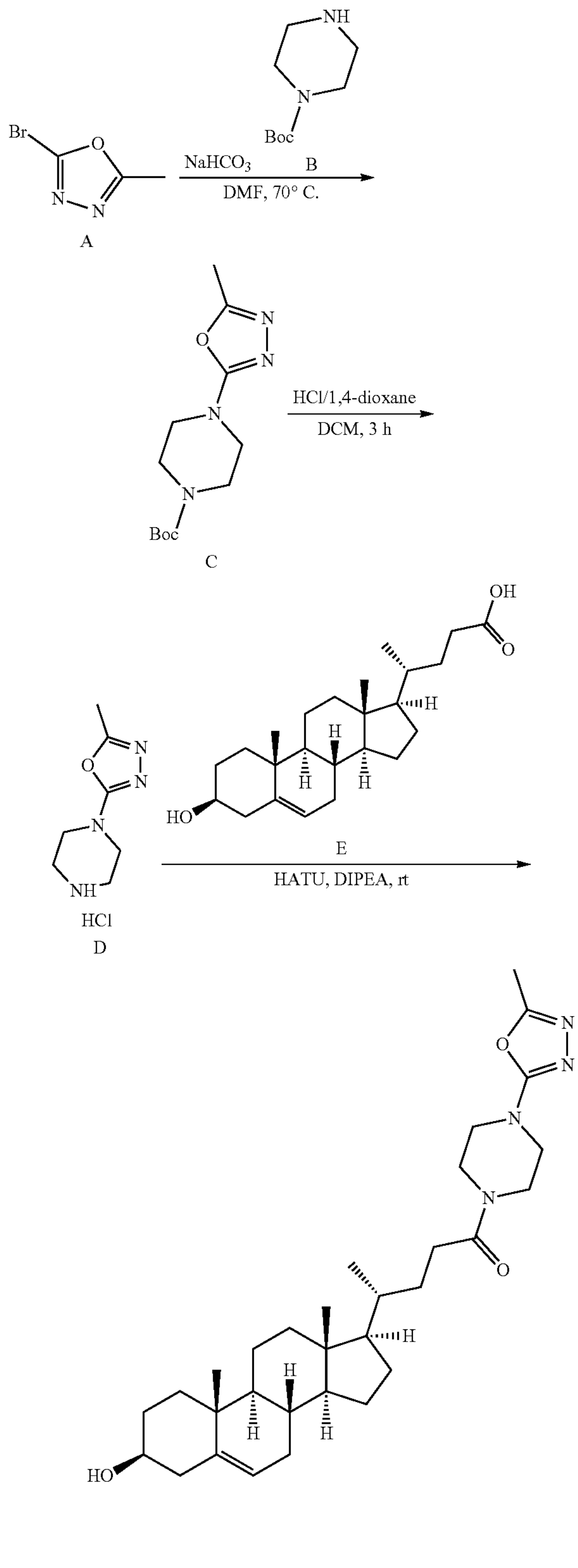

To a solution of compound B (250 mg, 1.34 mmol) in DMF (10 mL) was added compound A (284 mg, 1.74 mmol) and $NaHCO_3$ at room temperature, the reaction was stirred at 70° C. for 16 hours. The reaction was quenched with $H_2O$ (5 mL) and extracted with ethyl acetate (15 mL). The combined organic layers were dried over sodium sulfate and concentrated under reduced pressure. The crude product was purified by silica gel chromatography to afford compound C (350 mg, 97%). To a solution of compound C (300 mg, 1.12 mmol) in DCM (5 mL) was added HCl (4 M in solution of 1, 4-dioxane, 2.8 mL, 11.2 mmol), the reaction was stirred at room temperature for 3 hours. The solution concentrated to afford compound D (200 mg) as the HCl salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (100 mg, 267 μmol) and 2-methyl-5-(piperazin-1-yl)-1,3,4-oxadiazole HCl salt (71 mg, 347 μmol) were reacted according to the method of Example 536 to afford the title compound 482 (59.3 mg, 42%) as a white solid. LCMS: $[M+1]^+$=525.20. $^1H$ NMR (400 MHz, Chloroform-d) δ 5.35 (d, J=4.8 Hz, 1H), 3.73 (t, J=5.2 Hz, 2H), 3.61-3.42-3.39 (m, 7H), 2.41 (s, 4H), 2.33-2.19 (m, 3H), 2.04-1.93 (m, 2H), 1.91-1.75 (m, 4H), 1.55-1.42 (m, 8H), 1.38-1.25 (m, 3H), 1.21-1.05 (m, 4H), 1.02-0.93 (m, 7H), 0.69 (s, 3H).

Example 483: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(5-methyl-1,3,4-thiadiazol-2-yl)piperazin-1-yl)pentan-1-one

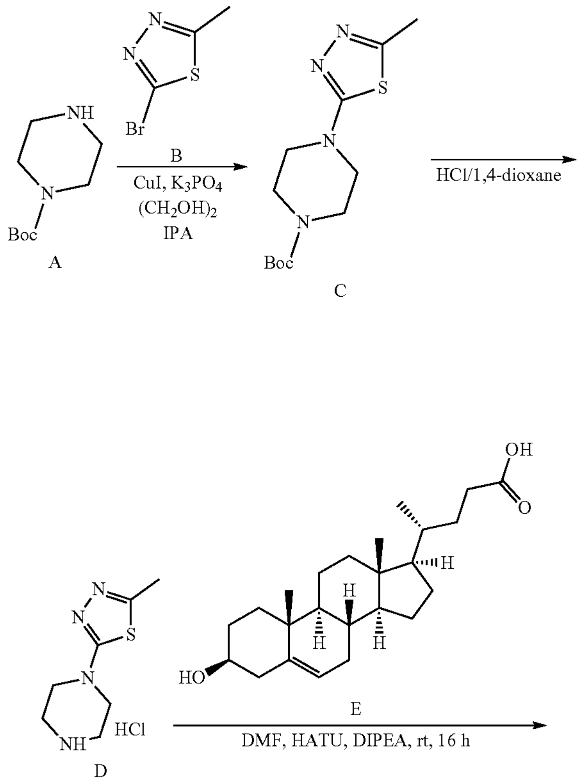

-continued

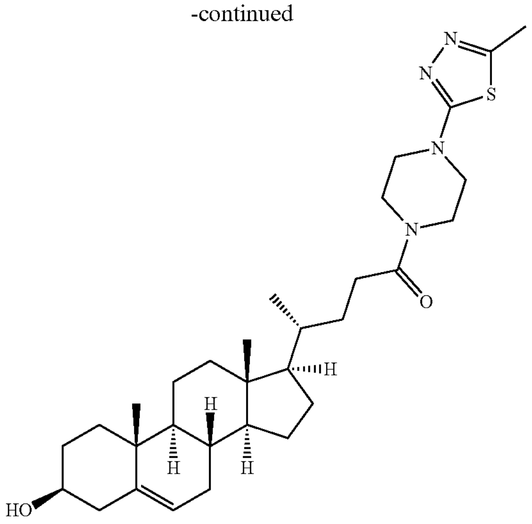

To a solution of compound A (100 mg g, 537 μmol) in isopropanol (3 mL) was added compound B (192 mg, 1.07 mmol), $K_3PO_4$ (456 mg, 2.15 mmol), CuI (20.5 mg, 107 μmol) and ethylene glycol (33.3 mg, 537 μmol) under $N_2$. The reaction was stirred at 120° C. for 16 hours. Upon completion, the reaction was quenched with saturated ammonium chloride (30 mL) and extracted with ethyl acetate (15 mL*3). The combined organic layers were washed with brine, dried over sodium sulfate, filtered, and concentrated to afford compound C (70 mg, 45.8%) as a white solid. To a solution of compound C (70 mg, 246 μmol) in DCM (6 mL) was added hydrogen chloride (1 mL, 4 mmol, 4M in dioxane) at room temperature and the reaction was stirred for 2 h. The reaction concentrated under reduced pressure to give compound D as the HCl salt (50 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (68 mg, 181 μmol) and 2-methyl-5-(piperazin-1-yl)-1,3,4-thiadiazole hydrochloride (50 mg, 227 μmol) were reacted according to the method of Example 536 to afford the title compound 483 (40 mg, 27.26%) as a white solid. LCMS: $[M+1]^+$=541.15 $^1$H NMR (400 MHz, Chloroform-d) δ 5.35 (d, J=4.8 Hz, 1H), 3.84-3.57 (m, 6H), 3.56-3.50 (m, 1H), 3.48 (s, 1H), 3.46 (bs, 1H), 2.61 (s, 3H), 2.45-2.18 (m, 4H), 2.03-1.94 (m, 2H), 1.90-1.74 (m, 4H), 1.64-1.27 (m, 10H), 1.21-0.98 (m, 8H), 0.98-0.88 (m, 4H), 0.69 (s, 3H).

Example 484: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-{4-[(pyrimidin-5-yl)methyl]piperazin-1-yl}pentan-1-one

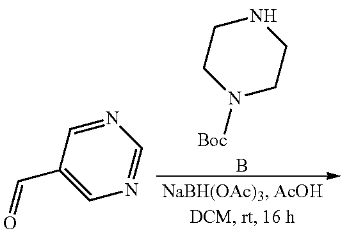

A

-continued

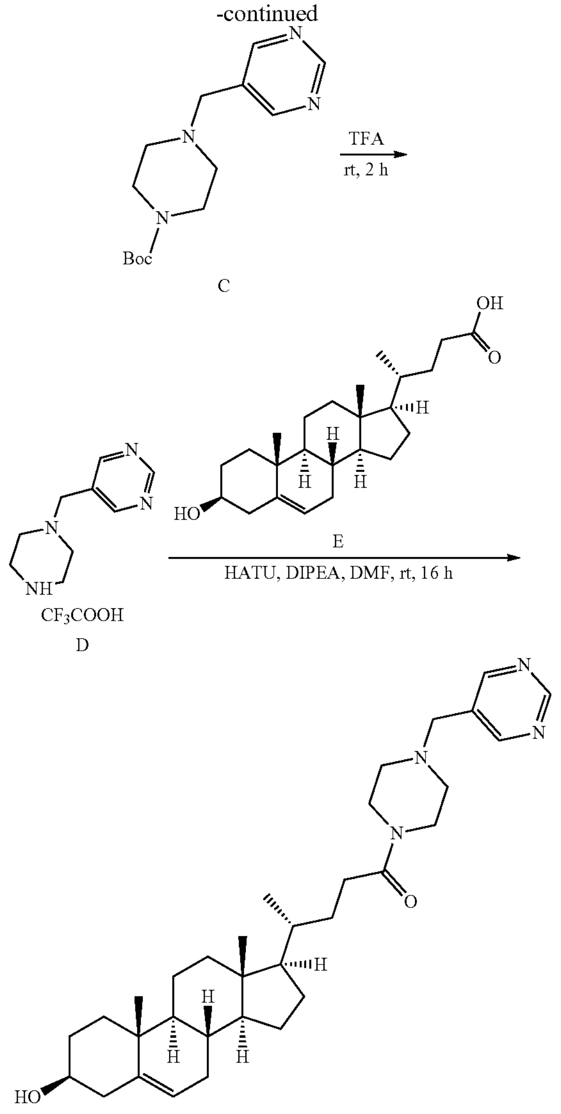

To a solution of compound A (500 mg, 4.63 mmol) in DCM (5 mL) was added compound B (861 mg, 4.63 mmol), $NaBH(OAc)_3$ (1.96 g, 9.25 mmol) and AcOH (28 mg, 463 μmol). The reaction was stirred at room temperature for 16 h. Water (20 mL) was added and extracted with DCM (20 mL*2). The combined organic layers were dried over sodium sulfate and concentrated under reduced pressure. The residue was purified by silica gel chromatography to afford compound C (200 mg, 15%) as a yellow solid. A solution of compound C (200 mg, 719 μmol) in TFA (5 mL) was stirred at room temperature for 2 h. The reaction concentrated under reduced pressure to give compound D (200 mg) as the TFA salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (284 mg, 757 μmol) and 5-(piperazin-1-ylmethyl)pyrimidine 2,2,2-trifluoroacetate (150 mg, 513 μmol) were reacted according to the method of Example 536 to afford the title compound 484 (60 mg, 14%) as a white solid. $^1$H NMR (400 MHz, Chloroform-d) δ 9.14 (s, 1H), 8.70 (s, 2H), 5.34 (d, J=4.8 Hz, 1H), 3.63 (t, J=5.2 Hz, 2H), 3.55-3.45 (m, 5H), 2.44 (t, J=5.2 Hz, 4H), 2.39-2.19 (m, 4H), 2.02-1.94 (m, 2H), 1.89-1.80 (m, 3H), 1.62-1.57 (m, 2H), 1.52-1.40 (m, 6H), 1.36-1.22 (m, 3H), 1.19-1.06 (m, 4H), 1.00 (s, 4H), 0.94 (d, J=6.4 Hz, 4H), 0.68 (s, 3H).

Example 485: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-((1-methyl-1H-pyrazol-4-yl)methyl)piperazin-1-yl)pentan-1-one

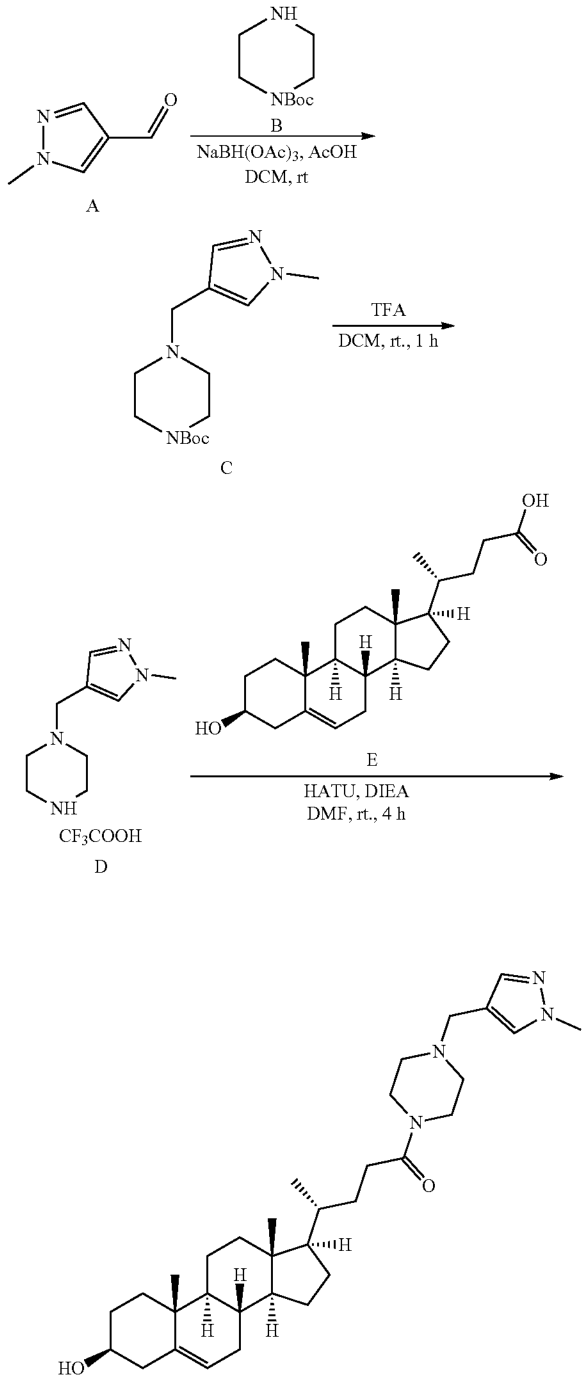

To a solution of compound A (200 mg, 1.82 mmol) in DCM (5 mL) was added compound B (338 mg, 1.82 mmol), AcOH (109 mg, 1.82 mmol) and $NaBH(OAc)_3$ (462 mg, 2.18 mmol). The reaction was stirred at room temperature under $N_2$ for 2 h. Saturated aqueous $NaHCO_3$ (5 mL) was added and extracted with EtOAc (10 mL). The organic layer was dried over sodium sulfate and concentrated. The residue was purified by silica gel chromatography to afford compound C (120 mg, 23.6%) as a yellow oil. To a solution of compound C (120 mg, 428 μmol) in DCM (2 mL) was added TFA (0.5 mL). The reaction was stirred at room temperature for 1 h. The reaction concentrated under reduced pressure to give compound D as the TFA salt (121 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (100 mg, 404 μmol) and 1-((1-methyl-1H-pyrazol-4-yl)methyl)piperazine (148.6 mg, 411 μmol) were reacted according to the method of Example 536 to afford the title compound 485 (134.3 mg, 93.7%) as a white solid. LCMS: $[M+1]^+$=537.20. $^1H$ NMR (400 MHz, Chloroform-d) δ 7.39 (s, 1H), 7.28 (s, 1H), 5.34 (d, J=5.2 Hz, 1H), 3.88 (s, 3H), 3.64-3.58 (m, 2H), 3.55-3.48 (m, 1H), 3.47-3.41 (m, 4H), 2.44-2.14 (m, 8H), 2.02-1.79 (m, 5H), 1.79-1.40 (m, 12H), 1.37-1.24 (m, 4H), 1.20-1.02 (m, 5H), 1.00 (s, 3H), 0.97 (d, J=5.8 Hz, 1H), 0.94 (d, J=6.4 Hz, 3H), 0.92-0.85 (m, 1H), 0.67 (s, 3H).

Example 486: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyrimidin-5-yl)piperazin-1-yl)pentan-1-one

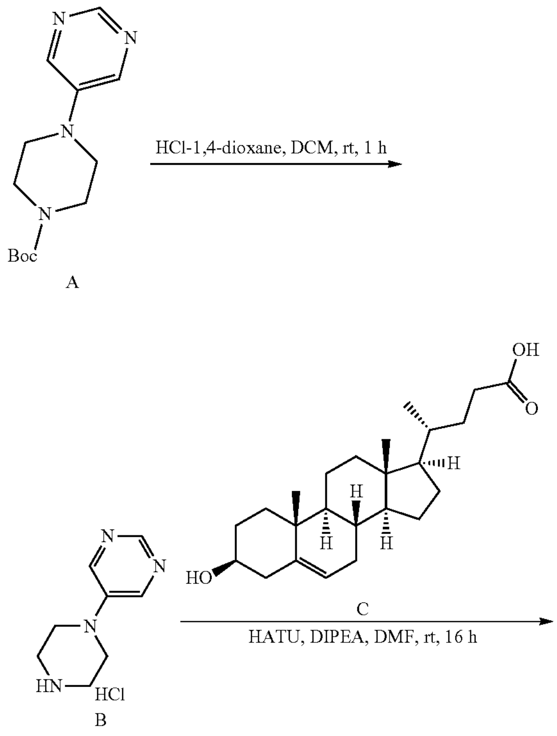

-continued

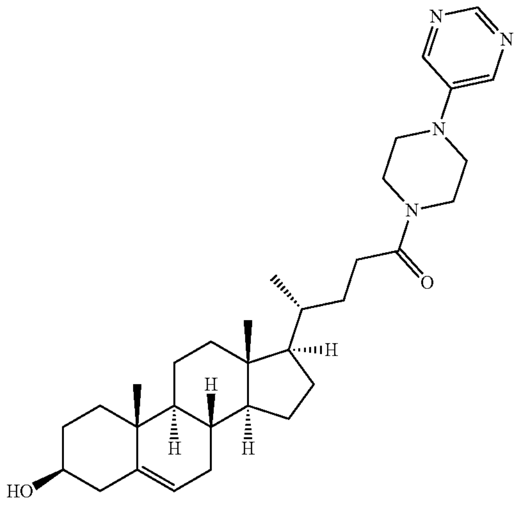

Hydrochloride in 1,4-dioxane (1 mL, 4 mmol) was added slowly to a solution of the compound A (100 mg, 378 μmol) in DCM (2 mL) at room temperature and stirred for 1 hour. Upon completion, the reaction was added dichloromethane (5 mL) and concentrated in vacuo three times to afford the title compound B (75.9 mg) as the HCl salt. 5-(piperazin-1-yl)pyrimidine hydrochloride (75.9 mg, 378 μmol) and (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (200 mg, 534 μmol) was reacted according to the method of Example 536 to afford the title compound 486 (95 mg, 34.2%) as a white solid. LCMS: $[M+1]^+$=520.38 $^1$H NMR (400 MHz, Chloroform-d) δ 8.74 (s, 1H), 8.39 (s, 2H), 5.36-5.33 (m, 1H), 3.81 (t, J=5.2 Hz, 2H), 3.67 (t, J=5.2 Hz, 2H), 3.56-3.48 (m, 1H), 3.29-3.20 (m, 4H), 2.47-2.23 (m, 4H), 2.03-1.78 (m, 7H), 1.69 (bs, 3H), 1.63-1.32 (m, 8H), 1.17-1.03 (m, 4H), 1.00 (s, 3H), 0.97 (d, J=6.4 Hz, 3H), 0.68 (s, 3H).

Example 487: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyridazin-4-yl)piperazin-1-yl)pentan-1-one

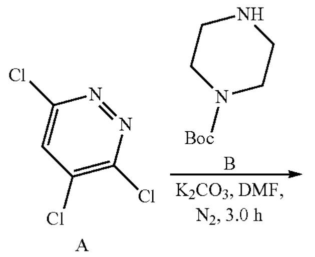

-continued

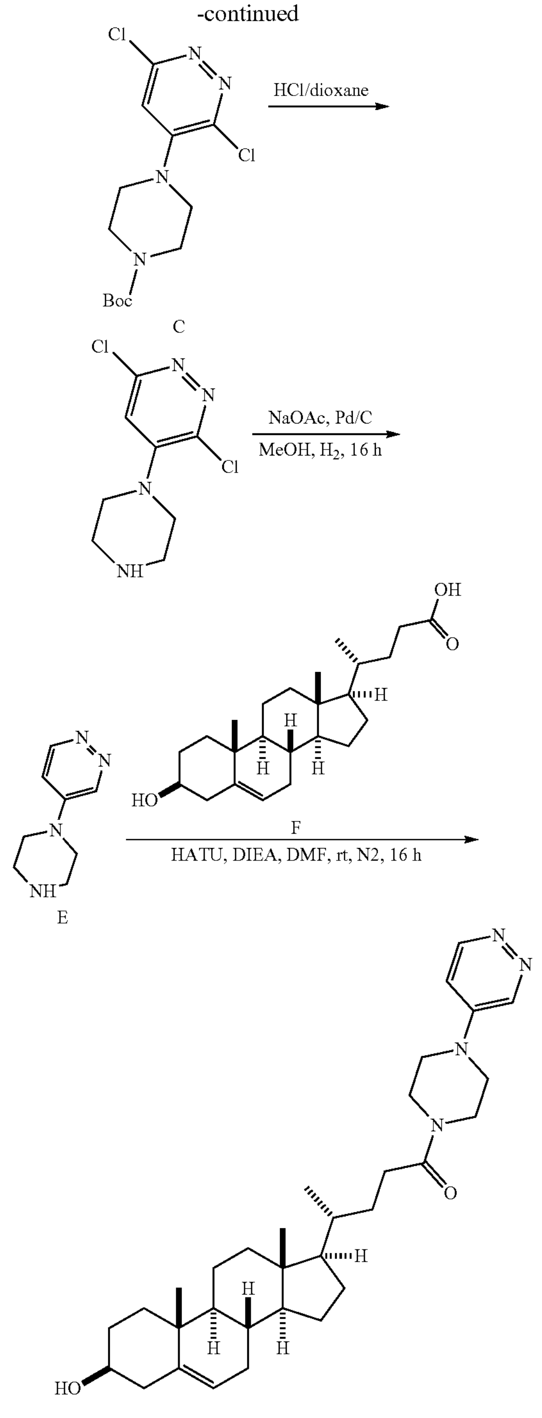

To a solution of compound A (1.5 g, 8.18 mmol) in DMF (30 mL) was added compound B (1.68 g, 9 mmol) and $K_2CO_3$ (2.26 g, 16.4 mmol). The reaction was stirred at room temperature under $N_2$ for 16.0 h. The reaction was quenched with water (10 mL) extracted with EtOAc (25 mL). The organic layer was washed with brine, dried over sodium sulfate, filtered, and concentrated. The residue was purified by silica gel chromatography to afford the compound C (1.5 g, 54.8%) as a white solid. To a solution of compound C (1.5 g, 4.5 mmol) in DCM (6.0 mL) was added 4N HCl/dioxane (1 mL). The reaction was stirred at room temperature under $N_2$ for 2.0 h. The reaction concentrated to afford compound D (1.0 g) as the HCl salt. To a solution of compound D (1.0 g) in MeOH (10 mL) was added NaOAc (500 mg) and 10% Pd/C (100 mg). The reaction was stirred at room temperature under a 1 atm $H_2$ atmosphere for 16 h. The reaction concentrated to afford the compound E (700 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (719 mg, 1.92 mmol) and 4-(piperazin-1-yl)pyridazine (350 mg, 2.13 mmol) were reacted according to the method of Example 536 to afford the title compound 487 (181 mg, 16.3%) as a white solid. LCMS: $[M+1]^+$=521.25. $^1H$ NMR (400 MHz, Chloroform-d) δ 8.86 (d, J=3.2 Hz, 1H), 8.74 (d, J=6.2 Hz, 1H), 6.68 (dd, J=6.3, 3.3 Hz, 1H), 5.34 (dd, J=4.9, 2.8 Hz, 1H), 3.74-3.72 (m, 4H), 3.56-3.39 (m, 5H), 2.45-2.37 (m, 1H), 2.31-2.19 (m, 3H), 2.04-1.76 (m, 7H), 1.65-0.85 (m, 25H), 0.69 (s, 3H).

Example 488: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(pyrimidin-4-yloxy)piperidin-1-yl]pentan-1-one

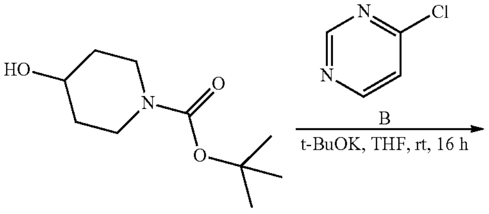

A

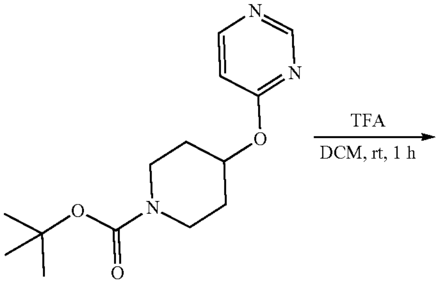

C

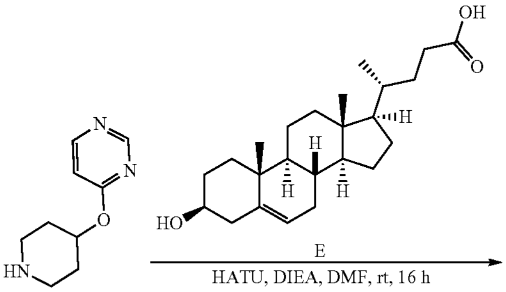

$CH_3COOH$

D

-continued

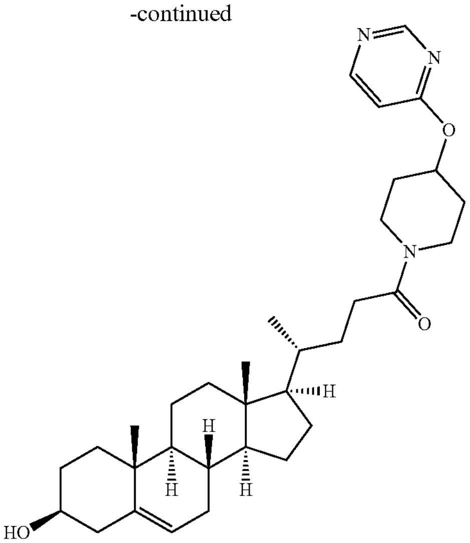

To a solution of compound A (0.2 g, 994 μmol) in THF (2 mL) was added compound B (137 mg, 1.19 mmol) and t-BuOK (446 mg, 3.97 mmol). The reaction was stirred at room temperature for 16 hours. The reaction was quenched with water (10 mL) and extracted with ethyl acetate (10 mL*4). The combined organic layers were concentrated to give the crude compound C (270 mg, 97%) as a white solid. To a solution of compound C (270 mg, 1 mmol) in DCM (6 mL) was added TFA (2 mL) at room temperature and the reaction was stirred for 2 h. The reaction concentrated under reduced pressure to give compound D (128 mg) as the TFA salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (161 mg, 429 μmol) and 4-(piperidin-4-yloxy)pyrimidine acetate (128 mg, 450 μmol) was reacted according to the method of Example 536 to afford the title compound 488 (55 mg, 23%) as a white solid. LCMS: $[M+1]^+$=536.10. $^1H$ NMR (400 MHz, Chloroform-d) δ 8.75 (s, 1H), 8.43 (d, J=5.6 Hz, 1H), 6.76-6.66 (m, 1H), 5.45-5.31 (m, 2H), 3.99 (s, 1H), 3.69 (s, 1H), 3.58-3.34 (m, 3H), 2.40 (t, J=10.4 Hz, 1H), 2.33-2.18 (m, 3H), 2.09-1.94 (m, 4H), 1.88-1.74 (m, 5H), 1.65 (s, 3H), 1.60-1.43 (m, 8H), 1.37-1.24 (m, 4H), 1.21-1.03 (m, 4H), 1.00 (s, 3H), 0.96 (d, J=6.4 Hz, 4H), 0.68 (s, 3H).

Example 489: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyrazin-2-yloxy)piperidin-1-yl)pentan-1-one

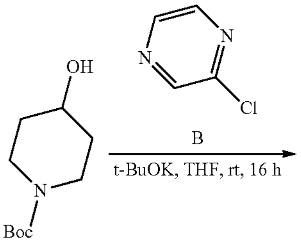

A

-continued

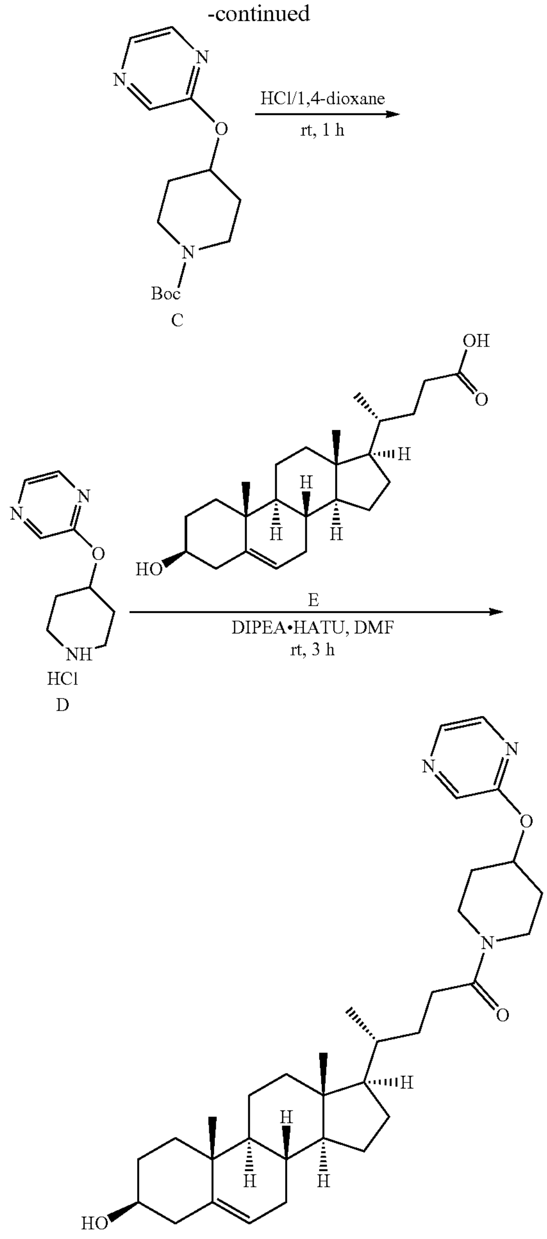

To a solution of compound A (600 mg, 2.98 mmol) in THF (20 mL) was added t-BuOK (1.34 g, 11.9 mmol) and compound B (410 mg, 3.58 mmol). The reaction was stirred at room temperature under nitrogen for 16 hours. Upon completion, the reaction was quenched with water (20 mL) and extracted with ethyl acetate (20 mL*3). The combined organic layers were washed with brine, dried over sodium sulfate, filtered, and concentrated to afford compound C (650 mg, 78%) as a white solid. To a solution of compound C (350 mg, 1.25 mmol) in DCM (3 mL) was added HCl (2 mL, 8 mmol, 4 M in 1,4-dioxane) slowly at room temperature and stirred for 1 hour. Upon completion, the reaction concentrated to give compound D (220 mg) as the HCl salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (200 mg, 534 μmol) and 2-(piperidin-4-yloxy)pyrazine hydrochloride (220 mg, 801 μmol) was reacted according to the method of Example 536 to afford the title compound 489 (166 mg, 58%) as a white solid. LCMS: $[M+1]^+$=536.20. $^1$H NMR (400 MHz, Chloroform-d) δ 8.21 (d, J=1.2 Hz, 1H), 8.12 (d, J=2.8 Hz, 1H), 8.06 (m, 1.4 Hz, 1H), 5.35 (d, J=5.2 Hz, 1H), 5.30-5.22 (m, 1H), 3.99-3.89 (m, 1H), 3.78-3.68 (m, 1H), 3.56-3.44 (m, 2H), 3.45-3.35 (m, 1H), 2.45-2.35 (m, 1H), 2.32-2.18 (m, 3H), 2.08-1.94 (m, 4H), 1.93-172 (m, 6H), 1.70-1.54 (m, 4H), 1.53 (d, J=9.6 Hz, 1H), 1.47-1.43 (m, 2H), 1.38-1.25 (m, 2H), 1.20-1.03 (m, 4H), 1.01 (s, 3H), 0.99-0.88 (m, 4H), 0.69 (s, 3H).

Example 490: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyridin-3-yloxy)piperidin-1-yl)pentan-1-one

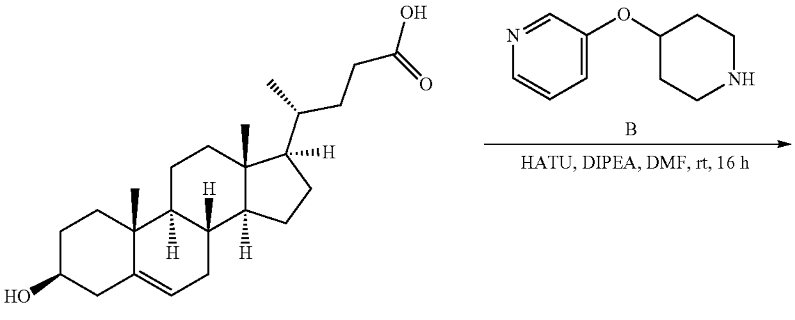

A

-continued

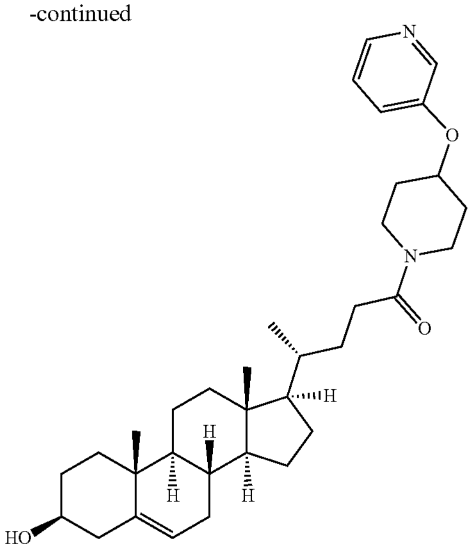

3-(piperidin-4-yloxy)pyridine (143 mg, 801 μmol) and (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (300 mg, 801 μmol) were reacted according to the method of Example 536 to afford the title compound 490 (290 mg, 67.7%) as a white solid. LCMS: $[M+1]^+$=534.38 $^1$H NMR (400 MHz, Chloroform-d) δ 8.33 (t, J=1.6 Hz, 1H), 8.26-8.20 (m, 1H), 7.25-7.21 (m, 2H), 5.39-5.30 (m, 1H), 4.62-4.54 (m, 1H), 3.85-3.38 (m, 5H), 2.46-2.19 (m, 4H), 2.05-1.74 (m, 10H), 1.64-1.05 (m, 13H), 1.00 (s, 3H), 0.96 (d, J=6.4 Hz, 3H), 0.94-0.88 (m, 1H), 0.69 (s, 3H).

Example 491: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-(pyrimidin-4-yloxy)piperidin-1-yl)pentan-1-one

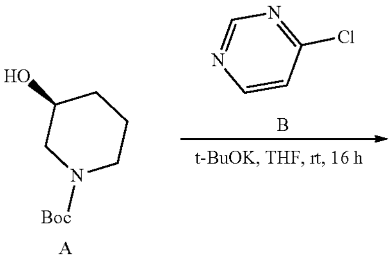

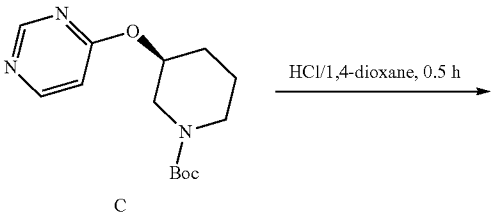

-continued

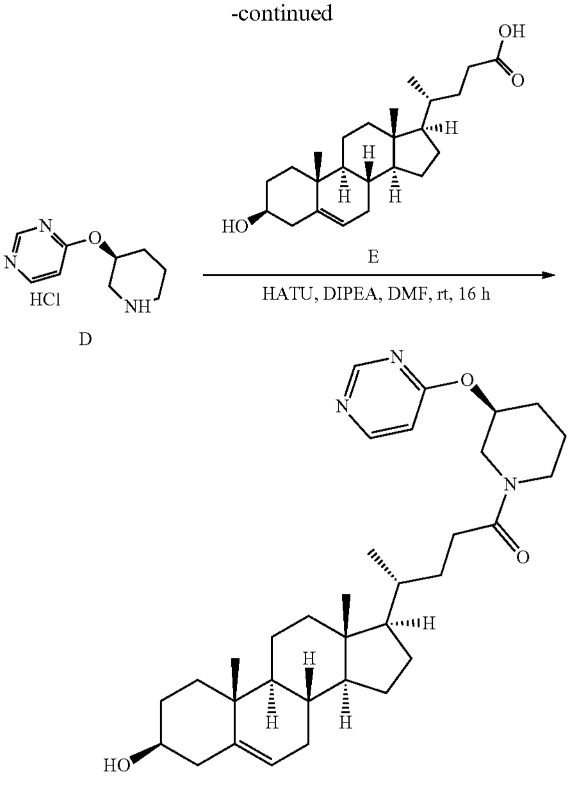

To a solution of compound A (200 mg, 994 μmol) in THF (4 mL) was added compound B (137 mg, 1.19 mmol) and t-BuOK (335 mg, 2.98 mmol). The reaction was stirred at room temperature for 16 hours. Upon completion, the reaction was quenched with saturated ammonium chloride (30 mL) and extracted with ethyl acetate (15 mL*3). The combined organic layers were washed with brine, dried over sodium sulfate, filtered, and concentrated to afford compound C (240 mg, 835 μmol, 84%) as a white solid. To a solution of compound C (100 mg, 358 μmol) in DCM (6 mL) was added hydrogen chloride (2 mL, 8 mmol, 4M in 1,4-dioxane) at room temperature and the reaction was stirred for 2 h. The reaction concentrated under reduced pressure to give compound D (72 mg) as the HCl salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (113 mg, 301 μmol, (S)-4-(piperidin-3-yloxy)pyrimidine hydrochloride (72 mg, 335 μmol) was reacted according to the method of Example 536 to afford the title compound 491 (40 mg, 22%) as a white solid. LCMS: $[M+1]^+$=536.20. $^1H$ NMR (400 MHz, Chloroform-d) δ 8.83-8.80 (m, 1H), 8.47 (d, J=5.6 Hz, 1H), 6.79-6.76 (m, 1H), 5.44-5.13 (m, 2H), 3.96-3.39 (m, 5H), 2.41-2.20 (m, 5H), 2.15-1.71 (m, 11H), 1.67-1.25 (m, 12H), 1.12-1.10 (m, 4H), 1.00 (d, J=2.0 Hz, 3H), 0.97-0.83 (m, 5H), 0.67 (d, J=12.4 Hz, 3H).

Example 492: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3R)-3-(pyrimidin-4-yloxy)piperidin-1-yl]pentan-1-one

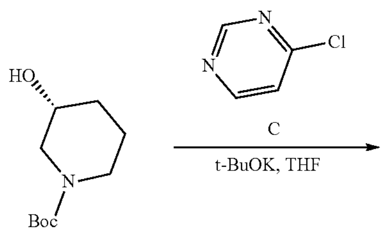

A

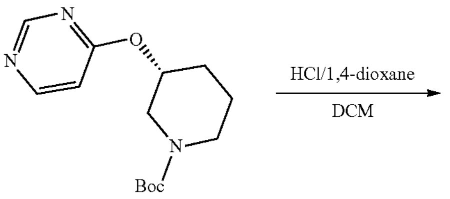

B

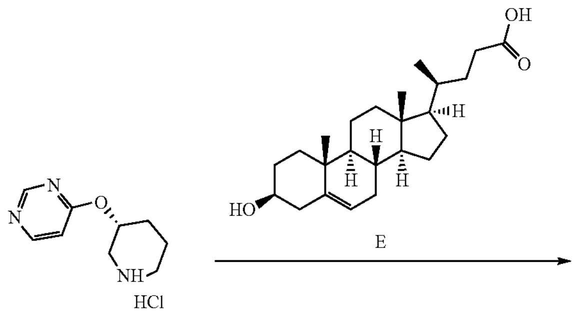

D

-continued

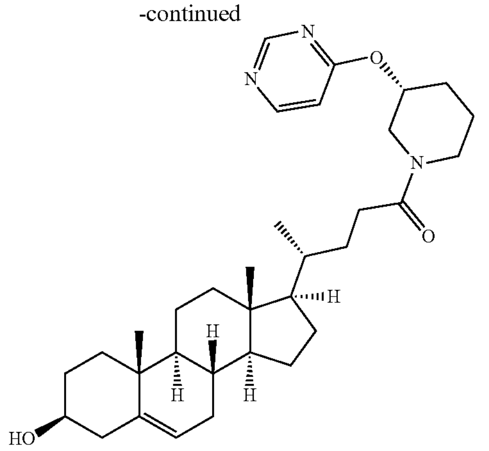

To a room temperature solution of compound A (0.2 g, 994 μmol) and compound C (137 mg, 1.19 mmol) in tetrahydrofuran (4 mL was added t-BuOK (335 mg, 2.98 mmol) and the reaction was stirred for 16 hours. The solvent was concentrated under reduced pressure. The residue was diluted with water (5 mL), extracted with EtOAc (20 mL). The organic layer was washed with brine, dried over sodium sulfate, filtered, and concentrated. The reaction was purified by column chromatography on silica gel to afford compound B (140 mg, 50%) as a white solid. To a solution of compound B (140 mg, 502 μmol) in DCM (6 mL) was added HCl/1,4-dioxane (1.5 mL) at room temperature and the reaction was stirred for 2 h. The reaction concentrated under reduced pressure to afford compound D (90 mg) as the HCl salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (150 mg, 402 μmol) and (R)-4-(piperidin-3-yloxy)pyrimidine hydrochloride (90 mg, 502 μmol) was reacted according to the method of Example 536 to afford the title compound 492 (80 mg, 30%) as a white solid. LCMS: $[M+1]^+$=536.65. $^1H$ NMR (400 MHz, Chloroform-d) δ 5.63 (s, 1H), 5.35 (d, J=5.0 Hz, 1H), 3.76 (q, J=10.7 Hz, 1H), 3.70-3.61 (m, 2H), 3.57-3.37 (m, 3H), 2.95-2.88 (m, 1H), 2.82 (td, J=11.4, 6.1 Hz, 4H), 2.36-2.05 (m, 7H), 1.92-1.88 (m, 7H), 1.61 (s, 4H), 1.58-1.40 (m, 8H), 1.32 (d, J=9.3 Hz, 4H), 1.20-1.02 (m, 5H).

Example 493: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3S)-3-(pyrimidin-4-yloxy)pyrrolidin-1-yl]pentan-1-one

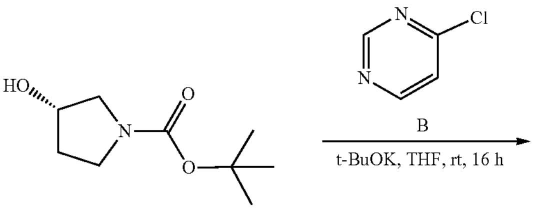

A

-continued

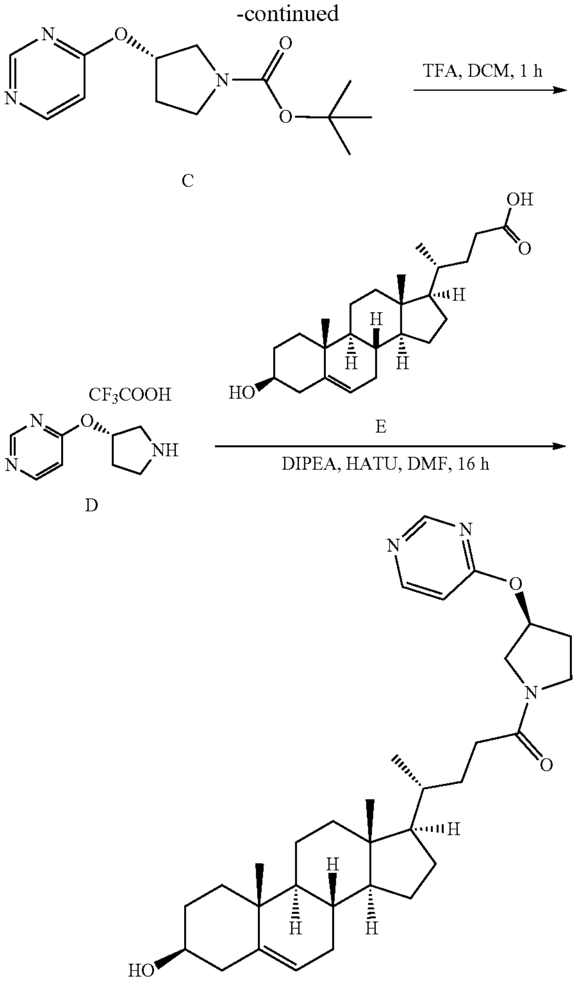

To a solution of compound A (200 mg, 1.07 mmol) in THE (2 mL) was added compound B (147 mg, 1.28 mmol) and t-BuOK (479 mg, 4.27 mmol). The reaction was stirred at room temperature for 16 hours. The reaction was quenched with water (5 mL) and extracted with ethyl acetate (10 mL*4). The combined organic layers were concentrated under reduced pressure. The crude product was purified by silica gel chromatography to afford compound C (260 mg, 70%) as a white solid. To a solution of compound C (260 mg, 980 μmol) in DCM (6 mL) was added TFA (2 mL) at room temperature and the reaction was stirred for 2 h. The reaction concentrated under reduced pressure to give compound D as the TFA salt (270 mg, 92%).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (145 mg, 387 μmol) and (S)-4-(pyrrolidin-3-yloxy)pyrimidine 2,2,2-trifluoroacetate (135 mg, 484 μmol) was reacted according to the method of Example 536 to afford the title compound 493 (67.7 mg, 26%) as a white solid. LCMS: $[M+1]^+$=522.25. $^1$H NMR (400 MHz, Chloroform-d) δ 8.86 (s, 1H), 8.51 (d, J=5.8 Hz, 1H), 6.82 (d, J=5.4 Hz, 1H), 5.76-5.70 (m, 1H), 5.35-5.32 (m, 1H), 3.99-3.44 (m, 5H), 2.58-2.43 (m, 2H), 2.36-2.12 (m, 6H), 2.01-1.93 (m, 2H), 1.85-1.82 (m, 4H), 1.63-1.40 (m, 7H), 1.37-1.25 (m, 3H), 1.21-1.02 (m, 4H), 1.01-0.98 (m, 3H), 0.97-0.85 (m, 5H), 0.67 (d, J=9.4 Hz, 3H).

Example 494: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-3-(pyrimidin-4-yloxy)pyrrolidin-1-yl)pentan-1-one

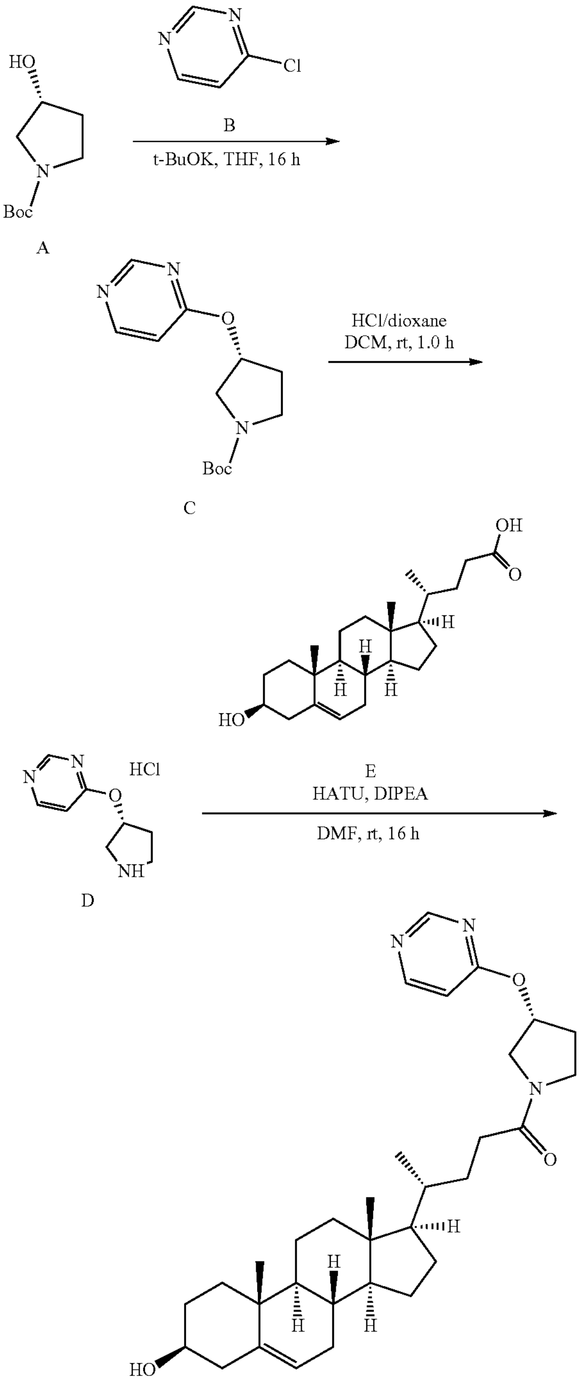

To a solution of compound A (245 mg, 1.31 mmol) and compound B (200 mg, 1.75 mmol) in THF (3 mL) was added t-BuOK (392 mg, 3.49 mmol) and the reaction was stirred at room temperature under $N_2$ for 16 h. The reaction was diluted with saturated aqueous $NH_4Cl$ (30 mL) and extracted with EtOAc (10 mL*2). The combined organic layers were washed with saturated aqueous $NaHCO_3$ (20 mL), water (20 mL), brine (20 mL), dried over sodium sulfate and concentrated under reduced pressure. The residue was purified by silica gel chromatography to afford compound C (150 mg, 43% yield) as a white solid. To a solution of compound C (150 mg, 565 umol) in DCM (2 mL) was added HCl (0.5 mL, 4M in dioxane, 2 mmol). The reaction was stirred at room temperature for 1 h. The reaction concentrated to afford the compound D as the HCl salt (100 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (204 mg, 0.5 mmol) and (R)-4-(pyrrolidin-3-yloxy)pyrimidine (100 mg, 497 umol) were reacted according to the method of Example 536 to afford the title compound 494 (18.1 mg, 7%) as a white solid. LCMS: $[M+1]^+$=522.25. $^1H$ NMR (400 MHz, Chloroform-d) δ 8.77 (d, J=6.8 Hz, 1H), 8.45 (dd, J=9.8, 5.8 Hz, 1H), 6.76-6.68 (m, 1H), 5.68 (d, J=14.8 Hz, 1H), 5.34 (s, 1H), 3.85-3.46 (m, 5H), 2.37-2.10 (m, 6H), 2.04-1.94 (m, 2H), 1.89-1.74 (m, 4H), 1.64-1.41 (m, 11H), 1.32-1.07 (m, 5H), 1.00 (d, J=2.0 Hz, 3H), 0.98-0.90 (m, 4H), 0.68 (d, J=5.6 Hz, 3H).

Example 495: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(3-methyl-1,2,4-oxadiazol-5-yl)piperazin-1-yl)pentan-1-one

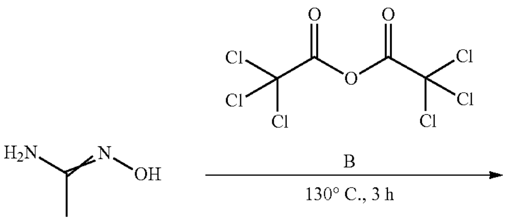

A

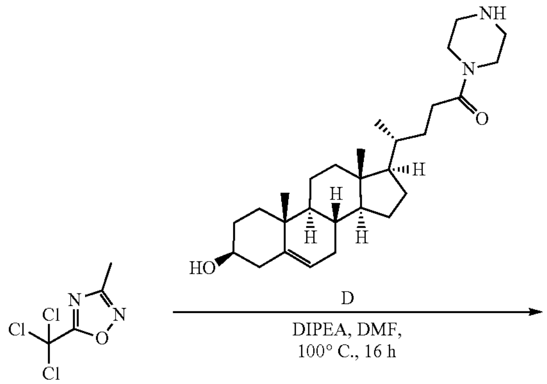

C

-continued

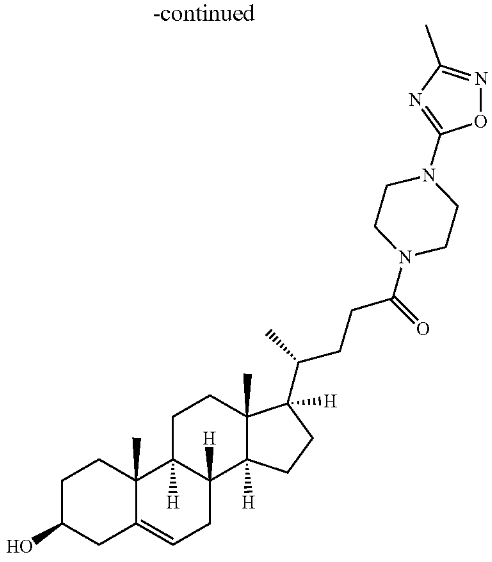

To a solution of compound A (1.00 g, 13.5 mmol) was added compound B (8.33 g, 27 mmol) and the reaction was heated to 130° C. under $N_2$ for 2 hours. The reaction was diluted with Saturated aqueous $NaHCO_3$ (20 mL) and extracted with EtOAc (20 mL*2). The combined organic layers were washed with brine (20 mL), dried over sodium sulfate, and concentrated under reduced pressure. The crude product was purified by silica gel chromatography to afford compound C (1.60 g, 59%) as oily liquid. To a solution of compound D (151 mg, 331 μmol) in DMF (2 mL) was added DIPEA (128 mg, 993 μmol) at room temperature under $N_2$ for 1 hour. Compound C (100 mg, 496 μmol) was added at 80° C. under $N_2$ and the reaction was stirred for 3 hours. The reaction was diluted with HCl (1M, 10 mL) and extracted with EtOAc (50 mL). The organic layer was washed with $NaHCO_3$ (20 mL), water (20 ml*3), brine (20 mL), dried over sodium sulfate and concentrated under reduced pressure. The crude product was purified by silica gel chromatography to afford the title compound 495 (38 mg, 22%) as a white solid. $^1H$ NMR (400 MHz, Chloroform-d) δ 5.35 (d, J=6.0 Hz, 1H), 3.91-3.64 (m, 6H), 3.62-3.55 (m, 2H), 3.54-3.48 (m, 1H), 2.49 (s, 3H), 2.42-2.17 (m, 4H), 2.03-1.94 (m, 2H), 1.91-1.74 (m, 4H), 1.52-1.42 (m, 5H), 1.39-1.24 (m, 5H), 1.21-1.07 (m, 4H), 1.01 (s, 3H), 0.96 (d, J=6.2 Hz, 4H), 0.89-0.77 (m, 2H), 0.69 (s, 3H).

Example 496: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(1-methyl-1H-pyrazol-4-yl)piperazin-1-yl)pentan-1-one

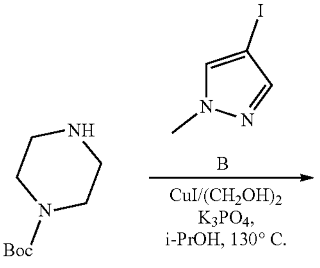

A

-continued

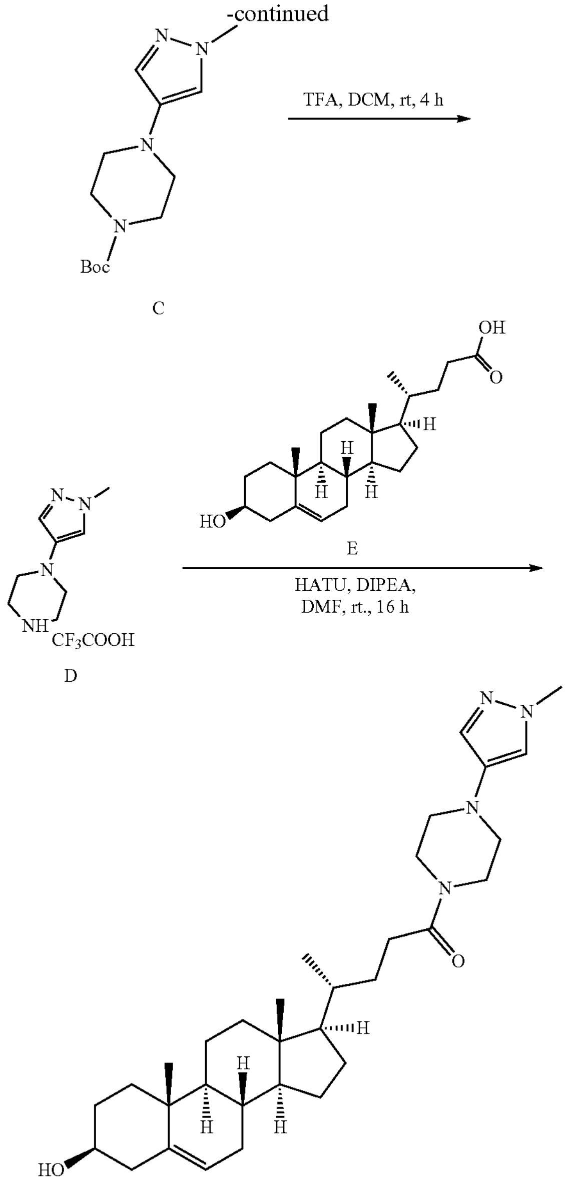

To a solution of compound A (500 mg, 2.68 mmol), compound B (1.12 g, 5.37 mmol), CuI (341 mg, 1.07 mmol), $K_3PO_4$ (2.28 g, 10.7 mmol) and ethylene glycol (333 mg, 5.37 mmol) in isopropanol (10 mL) was added at 120° C. under $N_2$ for 16 hours. The reaction was concentrated under reduced pressure. The crude product was purified by silica gel chromatography to afford compound C (150 mg, 21%) as brown solid. To a solution of compound C (150 mg, 563 μmol) in DCM (6 mL) was added TFA (2 mL) at room temperature under $N_2$ for 2 hours. The reaction concentrated under reduced pressure to afford compound D as the TFA salt (155 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (272 mg, 726 μmol) and 1-(1-methyl-1H-pyrazol-4-yl)piperazine 2,2,2-trifluoroacetate (162 mg, 553 μmol) were reacted according to the method of Example 536 to afford the title compound 496 (271 mg, 72%) as a white solid. LCMS: $[M+1]^+$=523.50. $^1$H NMR (400 MHz, DMSO-$d_6$) δ 7.27 (s, 1H), 7.15 (s, 1H), 5.26 (d, J=4.8 Hz, 1H), 4.58 (d, J=4.8 Hz, 1H), 3.72 (s, 3H), 3.59-3.48 (m, 4H), 3.29-3.21 (m, 1H), 2.79 (d, J=16.0 Hz, 4H), 2.40-2.30 (m, 1H), 2.25-2.18 (m, 1H), 2.17-2.05 (m, 2H), 1.98-1.86 (m, 2H), 1.76 (d, J=12.0 Hz, 2H), 1.66 (d, J=12.0 Hz, 2H), 1.58-1.30 (m, 8H), 1.25-1.16 (m, 2H), 1.14-1.06 (m, 2H), 1.02-0.96 (m, 2H), 0.94 (s, 3H), 0.92-0.83 (m, 4H), 0.65 (s, 3H).

Example 497: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(3-methylisothiazol-5-yl)piperazin-1-yl)pentan-1-one

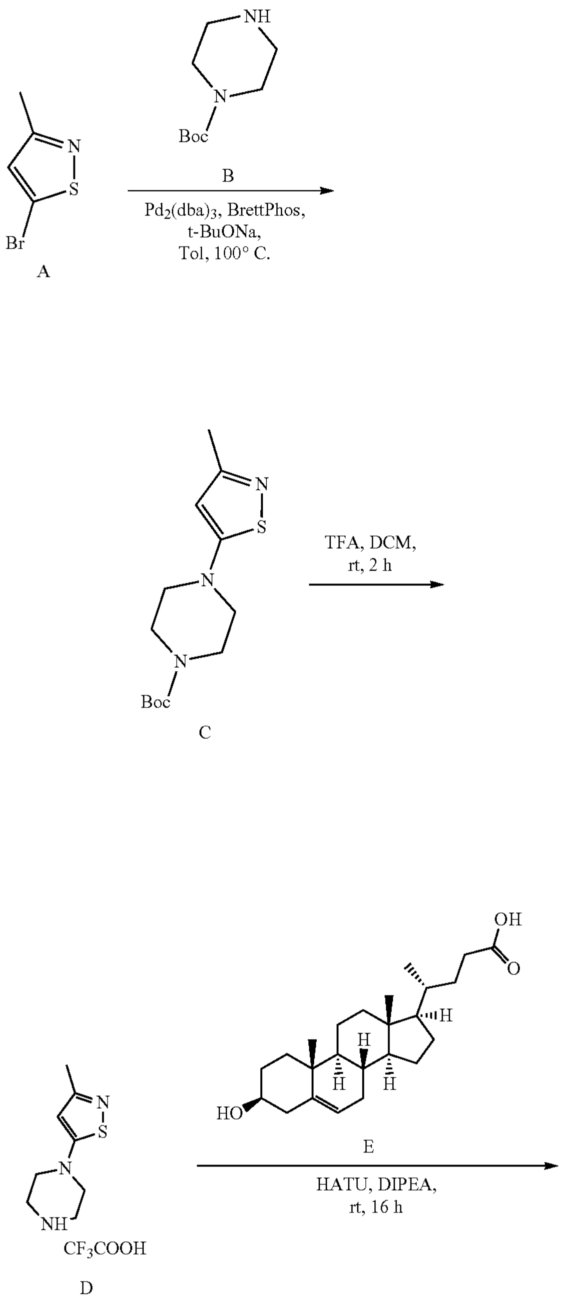

-continued

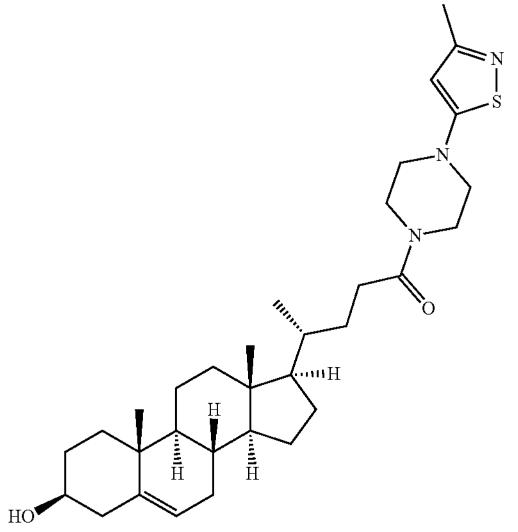

To a solution of compound A (100 mg, 562 μmol), compound B (115 mg, 618 μmol), $Pd_2(dba)_3$ (51.4 mg, 56.2 μmol) and Brett-Phos (60.3 mg, 112 μmol) in toluene (4 mL) was added t-BuONa (108 mg, 1.12 mmol) at 100° C. under $N_2$ for 16 hours. The reaction was concentrated under reduced pressure and purified by silica gel chromatography to afford compound C (80 mg, 50%) as off-white solid. To a solution of compound C (80 mg, 282 μmol) in DCM (4 mL) was added TFA (2 mL) at room temperature under $N_2$ for 2 hours. The reaction concentrated under reduced pressure to afford compound D as the TFA salt (85 mg, 286 μmol).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (81.8 mg, 218 μmol) and 3-methyl-5-(piperazin-1-yl)isothiazole 2,2,2-trifluoroacetate (85 mg, 286 μmol) were reacted according to the method of Example 536 to afford the title compound 497 (66 mg, 56%) as a white solid. LCMS: $[M+1]^+$=540.40. $^1H$ NMR (400 MHz, Chloroform-d) δ 6.06 (s, 1H), 5.35 (d, J=6.0 Hz, 1H), 3.76 (t, J=6.0 Hz, 2H), 3.61 (d, J=6.0 Hz, 2H), 3.56-3.47 (m, 1H), 3.22-3.15 (m, 4H), 2.45-2.36 (m, 1H), 2.34 (s, 3H), 2.31-2.15 (m, 3H), 2.04-1.92 (m, 2H), 1.91-1.73 (m, 4H), 1.56-1.41 (m, 7H), 1.40-1.23 (m, 3H), 1.21-1.05 (m, 4H), 1.01 (s, 3H), 0.96 (d, J=6.4 Hz, 4H), 0.69 (s, 3H).

Example 498: N-ethyl-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N-methylpiperazine-1-carboxamide

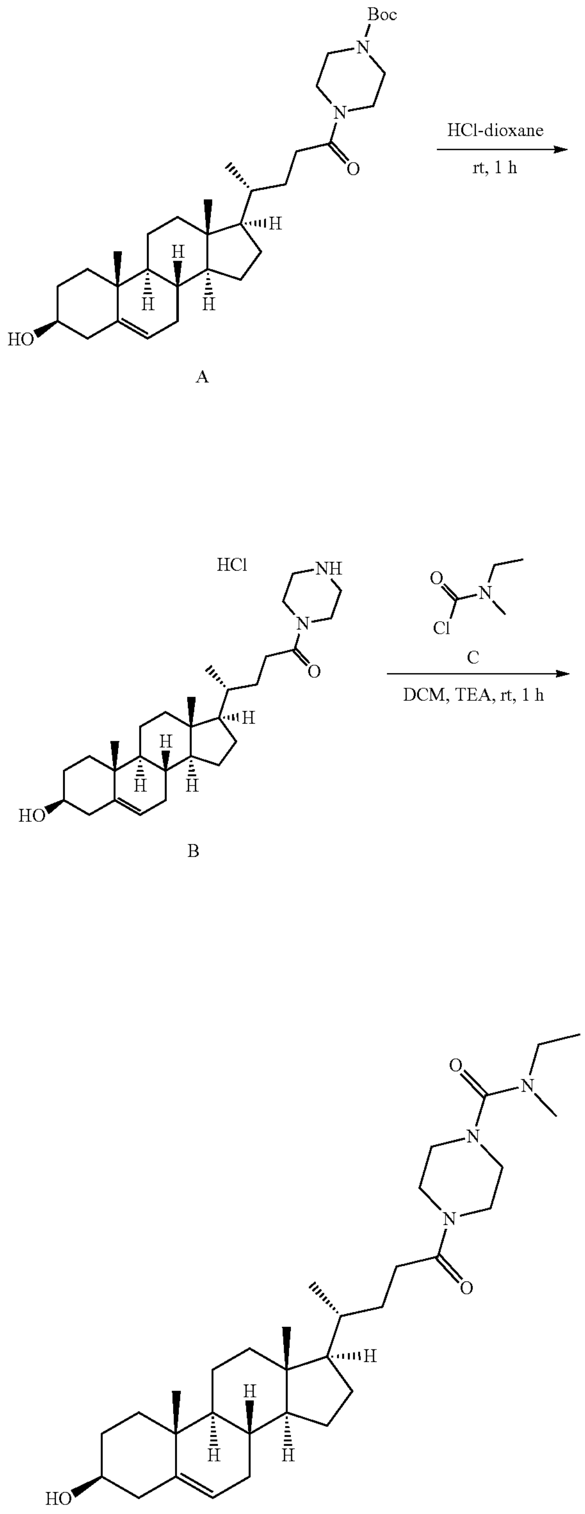

A

B

HCl (120 mL, 480 mmol, 4 M in 1.4-dioxane) was added slowly to the solution of compound A (9.6 g, 17.71 mmol) in 1.4-dioxane (100 mL) at room temperature and stirred for 1 hour. Upon completion, the reaction concentrated under vacuum to afford compound B as the HCl salt (7.2 g). To a solution of compound B (216 mg, 452 μmol) in DCM (5 mL) was added TEA (183 mg, 1.81 mmol) and compound C (49.4 mg, 408 μmol) at 0° C. and stirred for 1 hour. Upon completion, the reaction was quenched with water (10 mL) and extracted with DCM (10 mL*3). The organic layer was washed with brine (5 mL), dried over sodium sulfate, filtered, and concentrated under reduced pressure. The crude product was purified by column chromatography to afford the title compound 498 (88 mg, 40%) as a white solid. LCMS: $[M+1]^+$=528.20. $^1$H NMR (400 MHz, Chloroform-d) δ 5.36-5.32 (m, 1H), 3.65-3.56 (m, 2H), 3.55-3.42 (m, 3H), 3.27-3.14 (m, 6H), 2.82 (s, 3H), 2.45-2.33 (m, 1H), 2.33-2.18 (m, 3H), 2.04-1.93 (m, 2H), 1.89-1.73 (m, 4H), 1.66 (bs, 1H), 1.56-1.40 (m, 6H), 1.39-1.23 (m, 3H), 1.13-1.05 (m, 7H), 1.00 (s, 3H), 0.95-0.89 (m, 4H), 0.68 (s, 3H).

Example 499: N,N-diethyl-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperazine-1-carboxamide

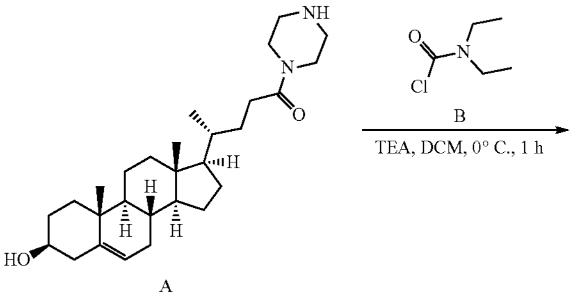

-continued

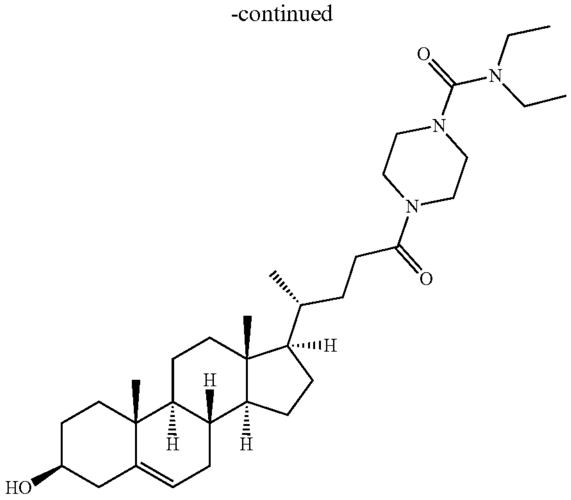

To a 0° C. solution of compound A (300 mg, 678 μmol) in DCM (3 mL) was added TEA (343 mg, 3.39 mmol), compound B (73.5 mg, 542 μmol) and the reaction was stirred for 1 hour. Upon completion, the reaction was quenched with water (10 mL) and extracted with ethyl acetate (10 mL*3). The combined organic layers were washed with brine (10 mL), dried over sodium sulfate, concentrated under reduced pressure. The crude product was purified by silica gel chromatography to afford the title compound 499 (290 mg, 79%) as a white solid. LCMS: $[M+1]^+$=542.30. $^1$H NMR (400 MHz, Chloroform-d) δ 5.37-5.32 (m, 1H), 3.69-3.40 (m, 5H), 3.27-3.14 (m, 8H), 2.44-2.17 (m, 4H), 2.02-1.72 (m, 6H), 1.66 (s, 3H), 1.62-1.02 (m, 19H), 1.00 (s, 3H), 0.95 (d, J=6.4 Hz, 3H), 0.68 (s, 3H).

Example 500: N-cyclopropyl-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N-methylpiperazine-1-carboxamide

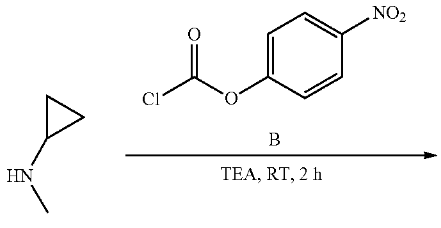

-continued

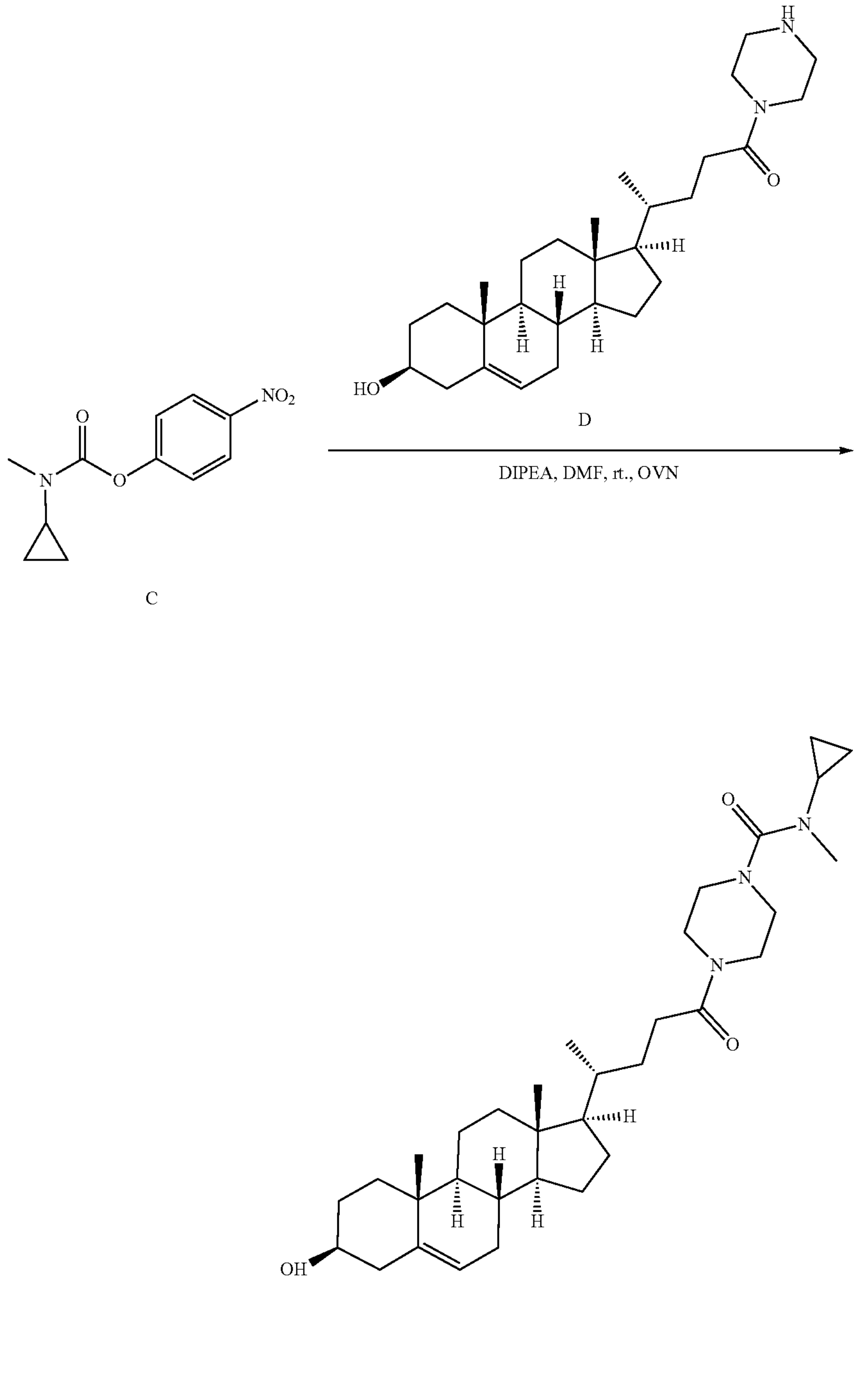

To a 0° C. solution of compound A (90 mg, 1.27 mmol) and TEA (192 mg, 1.9 mmol) in DCM (5 mL) was added compound B (255 mg, 1.27 mmol) and the reaction was stirred under $N_2$ for 2 hours. The reaction was concentrated under reduced pressure. The crude product was purified by Prep-TLC to afford compound C (285 mg, 95%) as off-white solid. To a solution of compound D (337 mg, 762 μmol) and compound C (150 mg, 635 μmol) in DMF (4 mL) was added DIPEA (246 mg, 1.9 mmol) at 100° C. under $N_2$ for 16 hours. The reaction was diluted with HCl (1N, 20 mL) and extracted with EtOAc (50 mL). The combined organic layers were washed with $NaHCO_3$ (20 mL) and water (20 mL*2), brine (20 mL), dried over sodium sulfate and concentrated under reduced pressure. The crude product was purified by silica gel chromatography to afford the title compound 500 (32 mg, 9.4%) as a white solid. LCMS: $[M+1]^+$=540.50. $^1$H NMR (400 MHz, Chloroform-d) δ 5.37-5.33 (m, 1H), 3.66-3.42 (m, 6H), 3.34 (s, 4H), 2.85 (s, 3H), 2.64-2.58 (m, 1H), 2.43-2.20 (m, 4H), 2.04-1.93 (m, 2H), 1.89-1.74 (m, 4H), 1.54-1.43 (m, 6H), 1.37-1.24 (m, 3H), 1.20-1.06 (m, 4H), 1.00 (s, 3H), 0.95 (d, J=6.4 Hz, 3H), 0.76-0.71 (m, 2H), 0.68 (s, 3H), 0.65-0.58 (m, 2H).

Example 501: N-(cyclopropylmethyl)-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N-methylpiperazine-1-carboxamide

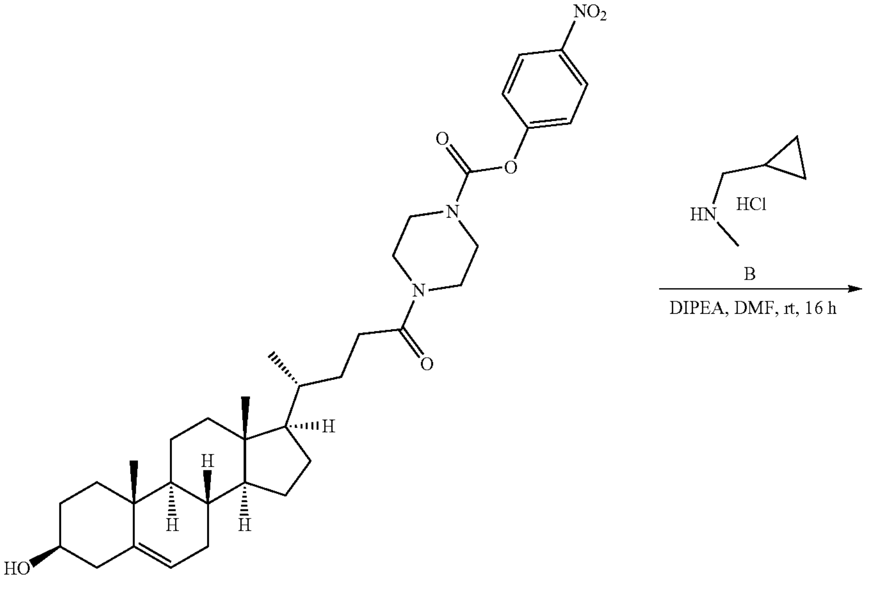

A

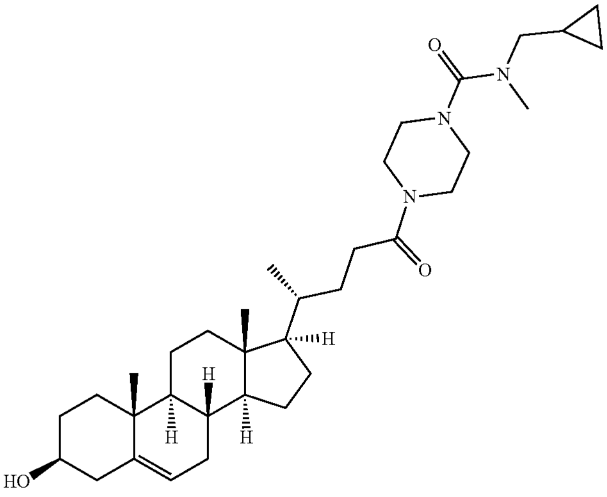

To a solution of compound A (100 mg, 0.16 mmol) and compound B (100 mg, 0.82 mmol) in DMF (3 mL) was added DIPEA (170 mg, 1.32 mmol). The reaction was stirred at 100° C. under $N_2$ for 16 h. The reaction was diluted with water (5 mL) and extracted with EtOAc (10 mL). The organic layer was washed with brine, dried over sodium sulfate, filtered, and concentrated. The residue was purified by silica gel chromatography to afford example 501 (41.2 mg, 45%) as a white solid. LCMS: $[M+1]^+$=554.30. $^1H$ NMR (400 MHz, Chloroform-d) δ 5.35 (d, J=5.2 Hz, 1H), 3.70-3.43 (m, 5H), 3.23 (bs, 2H), 3.19 (bs, 2H), 3.07 (d, J=6.8 Hz, 2H), 2.93 (s, 3H), 2.43-2.18 (m, 4H), 2.07-1.72 (m, 6H), 1.59-1.41 (m, 8H), 1.36-1.27 (m, 3H), 1.21-1.05 (m, 4H), 1.00 (s, 3H), 0.97-0.85 (m, 5H), 0.68 (s, 3H), 0.57-0.49 (m, 2H), 0.19 (d, J=5.2 Hz, 2H).

Example 502: 4—((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N-(2-methoxyethyl)-N-methylpiperazine-1-carboxamide

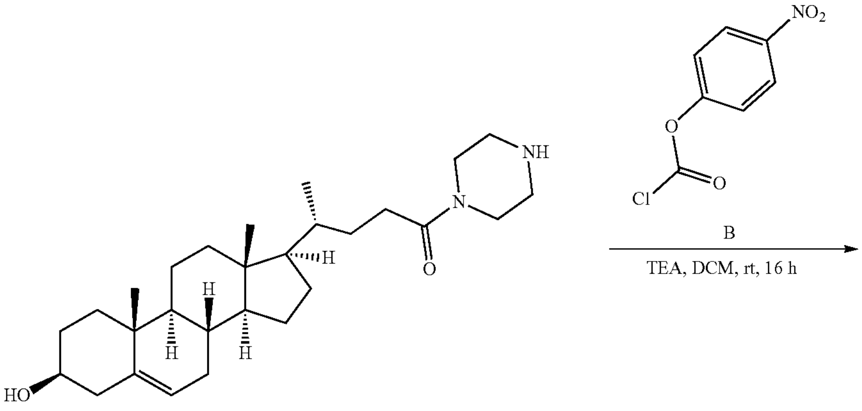

A

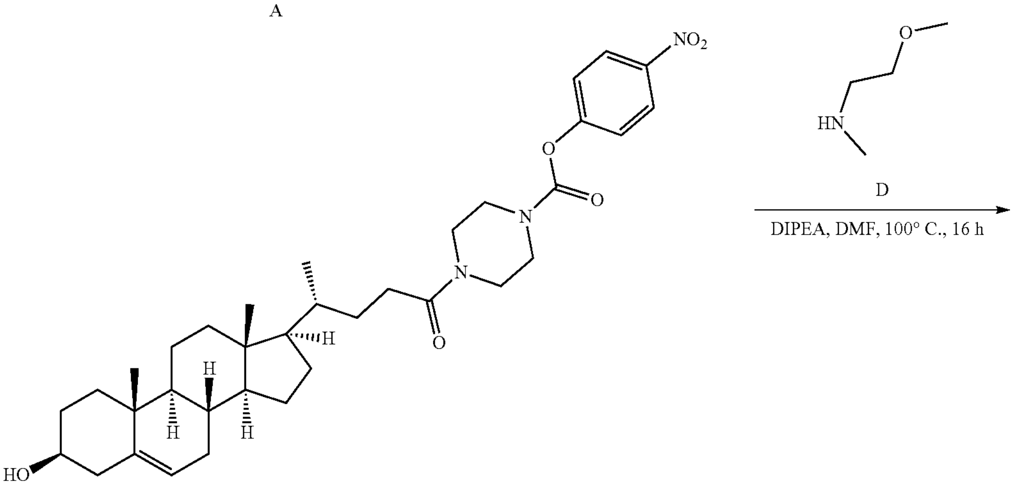

C

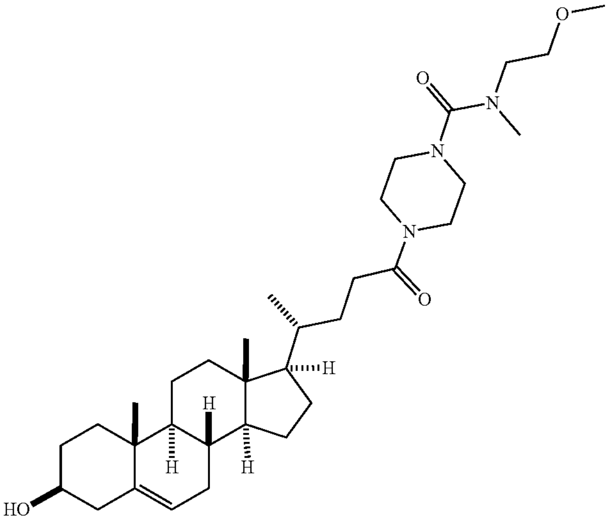

To a solution of compound A (3.0 g, 6.78 mmol) in DCM (40 mL) was added TEA (1.03 g, 10.17 mmol) and compound B (1.23 g, 6.1 μmol) at 0° C. The reaction was stirred at room temperature for 16 hours. Upon completion, the reaction was quenched with saturated ammonium chloride (200 mL) and extracted with ethyl acetate (80 mL*3). The combined organic layers were washed with brine (50 mL), dried over sodium sulfate, filtered, and concentrated under reduced pressure. The crude product was purified by silica gel chromatography to afford compound C (1.1 g, 26.7%) as a white solid. To a solution of compound D (147 mg, 1.65 mmol) in DMF (2 mL) was added compound C (100 mg, 165 μmol) and DIPEA (63.8 mg, 494 μmol). The solution was heated to 100° C. for 16 h under $N_2$. Upon completion, the reaction was quenched with saturated ammonium chloride (20 mL) and extracted with ethyl acetate (10 mL*3). The organic layers were washed with brine (10 mL), dried over sodium sulfate, filtered, and concentrated under reduced pressure. The crude product was purified by silica gel chromatography to afford the title compound 502 (50 mg, 54%) as a white solid. LCMS: rt: 1.97, 558.25 [M+1]. $^1$H NMR (400 MHz, Chloroform-d) δ 5.35 (d, J=5.2 Hz, 1H), 3.68-3.44 (m, 7H), 3.40 (t, J=5.6 Hz, 2H), 3.34 (s, 3H), 3.22 (bs, 4H), 2.93 (s, 3H), 2.43-2.18 (m, 4H), 2.07-1.72 (m, 7H), 1.59-1.04 (m, 16H), 1.00 (s, 3H), 0.95 (d, J=6.4 Hz, 3H), 0.93-0.82 (m, 1H), 0.68 (s, 3H).

Example 503: (R)-1-(4-(azetidine-1-carbonyl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one To a solution of compound A (100 mg, 165 μmol) in DMF (3 mL) was added DIPEA (128 mg, 987 μmol) and compound B (9.4 mg, 165 μmol). The reaction was stirred at room temperature for 16 hours. Upon completion, the reaction was quenched with saturated ammonium chloride (20 mL) and extracted with ethyl acetate (10 mL*3). The combined organic layers were washed with brine (5 mL), dried over sodium sulfate, filtered, and concentrated under reduced pressure. The crude product was purified by silica gel chromatography to afford the title compound 503 (40 mg, 46.3%) as a white solid. LCMS: rt: 1.35, 526.25 [M+1]. $^1$H NMR (400 MHz, Chloroform-d) δ 5.38-5.32 (m, 1H), 4.01 (t, J=7.6 Hz, 4H), 3.65-3.22 (m, 9H), 2.43-2.17 (m, 6H), 1.98 (ddt, J=13.6, 10.4, 3.2 Hz, 2H), 1.91-1.72 (m, 4H), 1.58-1.42 (m, 7H), 1.39-1.28 (m, 3H), 1.20-1.02 (m, 5H), 1.00 (s, 3H), 0.95 (d, J=6.4 Hz, 3H), 0.88 (q, J=7.2, 6.4 Hz, 1H), 0.68 (s, 3H).

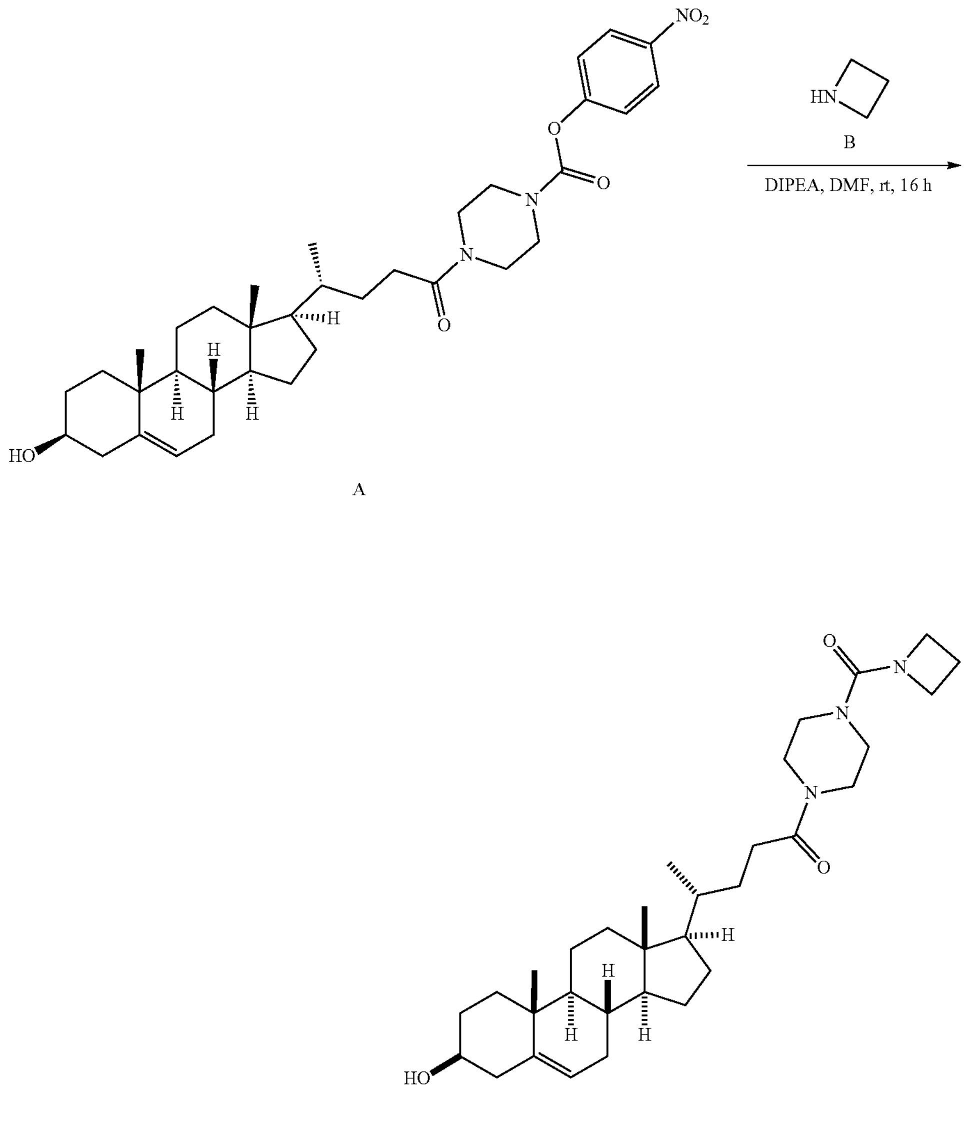

Example 504: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyrrolidine-1-carbonyl)piperazin-1-yl)pentan-1-one

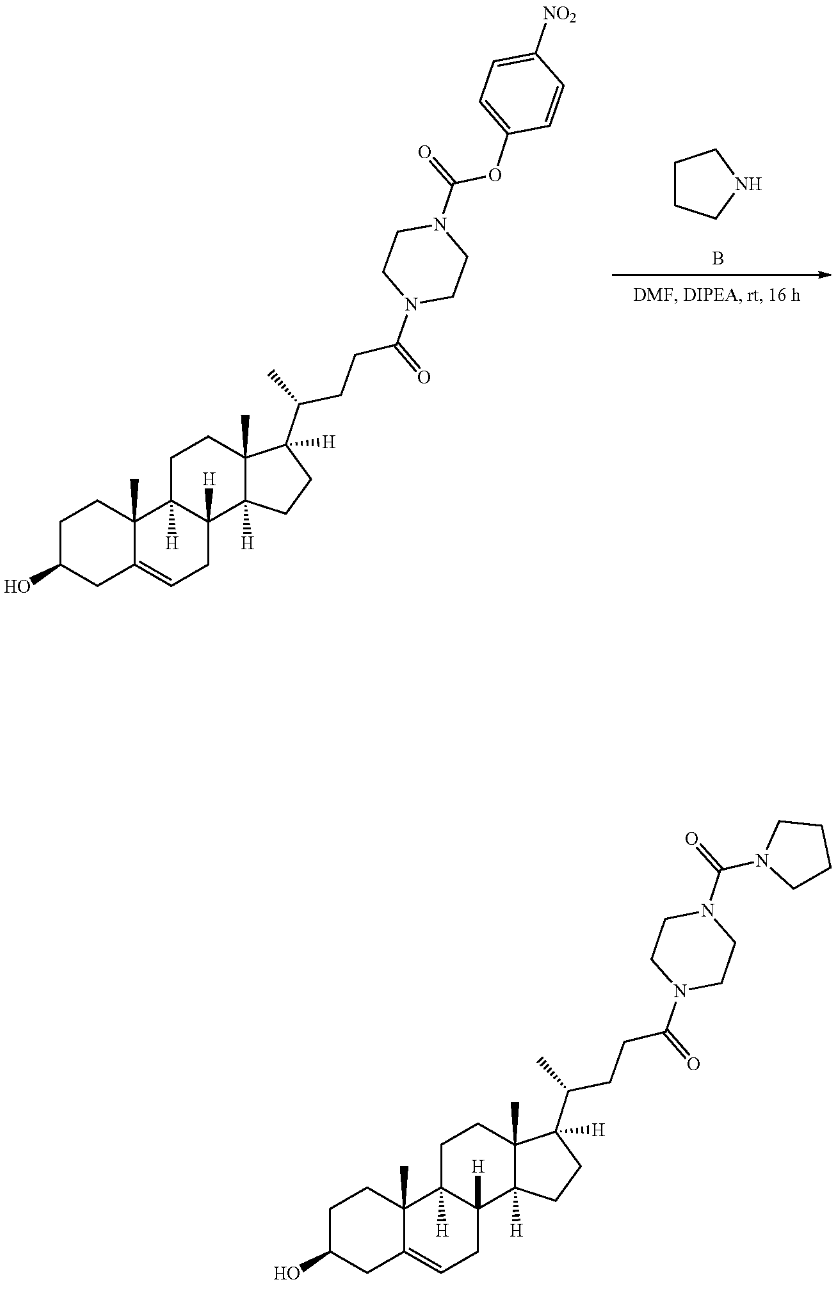

To a solution of compound A (100 mg, 165 μmol) in DMF (3 mL) was added DIPEA (63.8 mg, 494 μmol), compound B (58.5 mg, 823 μmol) and the reaction was stirred at room temperature for 16 hours. Upon completion, the reaction was quenched with saturated ammonium chloride (20 mL) and extracted with ethyl acetate (15 mL*3). The organic layer was washed with brine (15 mL), dried over sodium sulfate, filtered, and concentrated under reduced pressure. The crude product was purified by silica gel chromatography to afford the title compound 504 (30 mg, 33%) as a white solid. LCMS: rt: 1.14, 540.25 [M+1]. $^1$H NMR (400 MHz, Chloroform-d) δ 5.35 (d, J=5.2 Hz, 1H), 3.67-3.21 (m, 13H), 2.39 (bs, 1H), 2.34-2.16 (m 3H), 2.05-1.05 (m, 22H), 1.01 (s, 3H), 0.96 (d, J=6.0 Hz, 3H), 0.93-0.85 (m, 1H), 0.68 (s, 3H).

Example 505: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(3-methyl-1,2,4-oxadiazol-5-yl)piperidin-1-yl)pentan-1-one

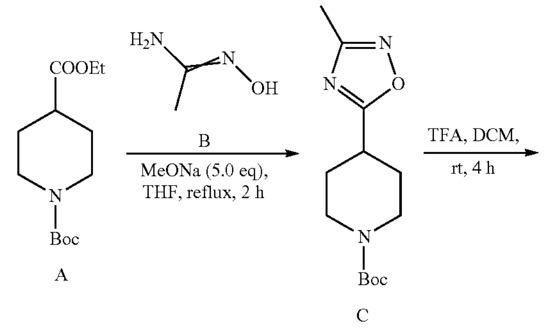

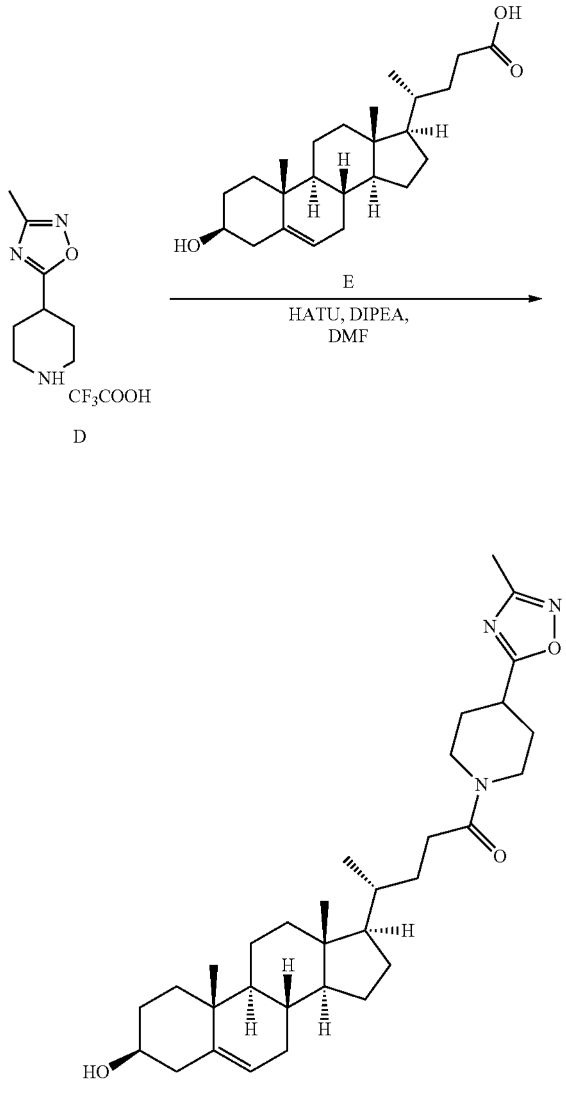

To a room temperature solution of compound A (300 mg, 1.17 mmol) and compound B (216 mg, 2.91 mmol) in THF (8 mL) was added MeONa (315 mg, 5.83 mmol) and the reaction was heated to 70° C. under $N_2$ for 2 hours. The reaction was quenched with $NaHCO_3$ (ice, 20 mL) and extracted with EtOAc (50 mL). The organic layer was washed with brine (20 mL), dried over sodium sulfate and concentrated under reduced pressure silica gel chromatography to afford compound C (220 mg, 70%) as light yellow solid. To a solution of compound C (220 mg, 823 μmol) in DCM (5 mL) was added TFA (2 mL) at room temperature under $N_2$ for 2 hours. The reaction concentrated under reduced pressure to give compound D as the TFA salt (230 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (257 mg, 609 μmol) and 3-methyl-5-(piperidin-4-yl)-1,2,4-oxadiazole 2,2,2-trifluoroacetate (173 mg, 615 μmol) were reacted according to the method of Example 536 to afford the title compound 505 (185 mg, 51%) as a white solid. LCMS: $[M+1]^+$=524.40. $^1H$ NMR (400 MHz, Chloroform-d) δ 5.34 (d, J=6.0 Hz, 1H), 4.49 (d, J=12.0 Hz, 1H), 3.89 (d, J=12.0 Hz, 1H), 3.54-3.48 (m, 1H), 3.33-3.04 (m, 2H), 2.90 (t, J=12.0 Hz, 1H), 2.38 (s, 3H), 2.32-2.19 (m, 3H), 2.11 (s, 2H), 2.02-1.93 (m, 2H), 1.91-1.71 (m, 6H), 1.61-1.41 (m, 7H), 1.30-1.28 (m, 3H), 1.20-1.03 (m, 4H), 1.00 (s, 3H), 0.96-0.89 (m, 4H), 0.68 (s, 3H).

Example 506: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-((3-methyl-1,2,4-oxadiazol-5-yl)oxy)piperidin-1-yl)pentan-1-one

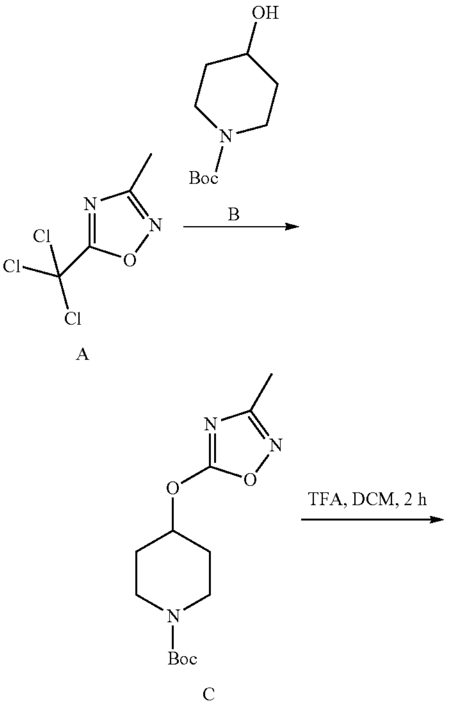

-continued

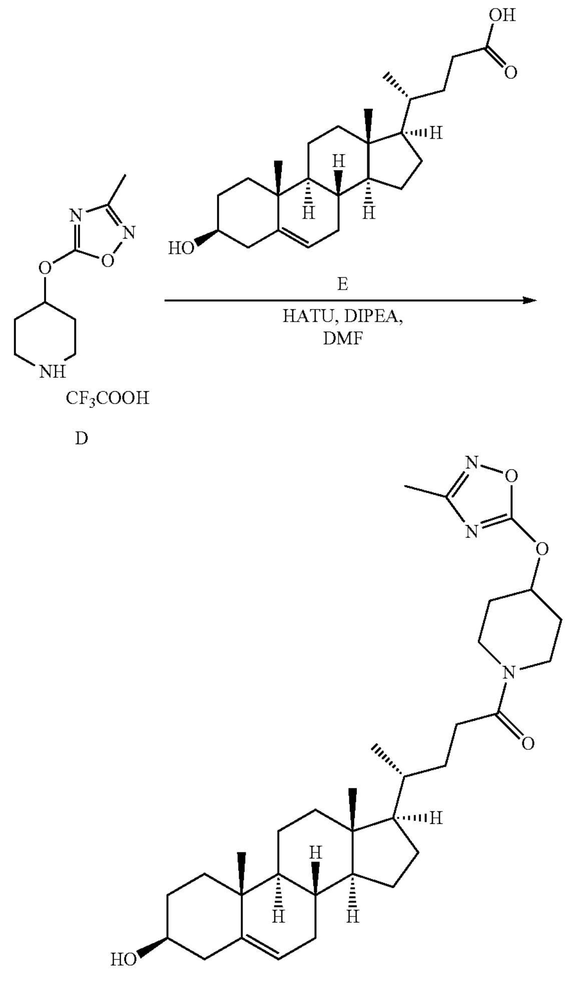

To a solution of compound B (0.2 g, 993 μmol) in DMF (1 mL) was added NaH (28.5 mg, 0.71 mmol, 60% dispersion in mineral oil) at room temperature under $N_2$ for 1 hour. Compound A (0.1 g, 496 μmol) was added at 60° C. under $N_2$ and the reaction was stirred for 3 hours. The reaction was diluted with HCl (1M, 10 mL) and extracted with EtOAc (50 mL). The organic layer was washed with $NaHCO_3$ (20 mL), water (20 ml*3), brine (20 mL), dried over sodium sulfate and concentrated under reduced pressure. The crude product was purified by silica gel chromatography to afford compound C (50 mg, 34%) as brown solid. To a solution of compound C (50 mg, 176 μmol) in DCM (1 mL) was at room temperature under $N_2$ was added TFA (0.5 mL). The reaction was stirred at room temperature for 3 hours. The reaction concentrated under reduced pressure to afford compound D as the TFA salt (51.4 mg, 173 μmol).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (54 mg, 144 μmol) and 3-methyl-5-(piperidin-4-yloxy)-1,2,4-oxadiazole 2,2,2-trifluoroacetate (51.4 mg, 173 μmol) were reacted according to the method of Example 430 to afford the title compound 506 (60 mg, 77%) as off-white solid. $^1H$ NMR (400 MHz, Chloroform-d) δ 5.35 (d, J=6.0 Hz, 1H), 5.15-5.03 (m, 1H), 3.90-3.79 (m, 1H), 3.72-3.66 (m, 1H), 3.62-3.39 (m, 3H), 2.45-2.34 (m, 1H), 2.31-2.21 (m, 6H), 2.09-1.75 (m, 10H), 1.53-1.43 (m, 6H), 1.35-1.26 (m, 4H), 1.21-1.06 (m, 4H), 1.01 (s, 3H), 0.97-0.88 (m, 4H), 0.68 (s, 3H).

Example 507: (R)-1-(4-cyclohexyl-4-hydroxypiperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

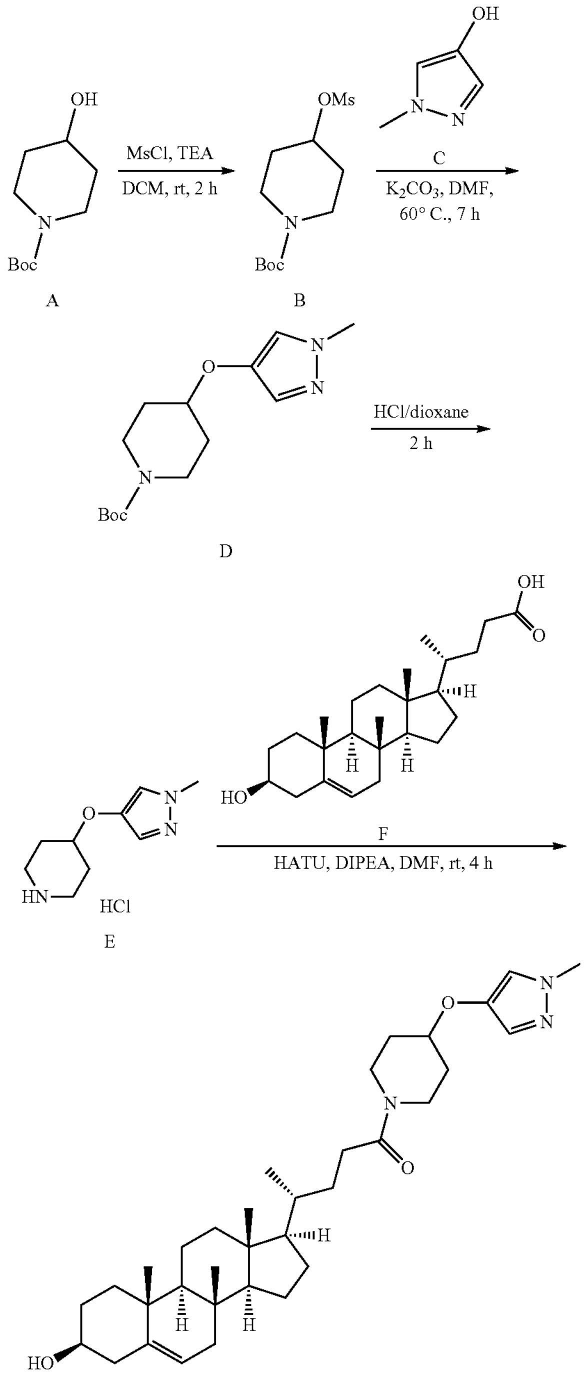

To a solution of compound A (500 mg, 2.48 mmol) in DCM (10 mL) was added TEA (1.26 g, 12.4 mmol) and MsCl (569 mg, 4.97 mmol) at 0° C. The reaction was stirred at room temperature for 2 hours. The reaction was quenched with water (10 mL) and extracted with DCM (20 mL). The organic layer was concentrated under reduced pressure. The crude product was purified by silica gel chromatography to afford compound B (200 mg, 29%). To a solution of compound B (200 mg, 716 μmol) in DMF (4 mL) was added $K_2CO_3$ (297 mg, 32.15 mmol) and compound C (105 mg, 716 μmol). The reaction was stirred at 60° C. for 7 hours under $N_2$. The reaction was quenched with water (5 mL) and extracted with ethyl acetate (15 mL). The organic layer was concentrated under reduced pressure. The crude product was purified by silica gel chromatography to afford compound D (60 mg, 30%). To a solution of compound D (60 mg, 213 μmol) in DCM was added 4N hydrogen chloride in dioxane (1 mL), the reaction was stirred at room temperature for 2 h. Upon completion, the reaction concentrated to afford compound E as the HCl salt (39 mg, 210 μmol).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (78.5 mg, 210 μmol) and 4-((1-methyl-1H-pyrazol-4-yl)oxy)piperidine hydrochloride(39 mg, 210 μmol) was reacted according to the method of Example 536 to afford the title compound 507 (50 mg, 44%) as a white solid. LCMS: $[M+1]^+$=538.30 $^1$H NMR (400 MHz, Chloroform-d) δ 7.18 (s, 1H), 7.04 (s, 1H), 5.33 (d, J=5.2 Hz, 1H), 4.08 (dt, J=6.8, 3.4 Hz, 1H), 3.79 (s, 3H), 3.68 (s, 1H), 3.49 (dd, J=10.4, 5.2 Hz, 2H), 3.34 (s, 1H), 2.38-2.18 (m, 4H), 2.02-1.98 (m, 2H), 1.87 (dt, J=13.2, 4.0 Hz, 3H), 1.81 (s, 3H), 1.78-1.73 (m, 2H), 1.63-1.56 (m, 1H), 1.53 (d, J=2.4 Hz, 1H), 1.52-1.48 (m, 2H), 1.48-1.46 (m, 1H), 1.44 (d, J=4.4 Hz, 1H), 1.38-1.32 (m, 1H), 1.31-1.24 (m, 1H), 1.21-1.14 (m, 1H), 1.14-1.04 (m, 3H), 1.00 (s, 3H), 0.95 (d, J=6.4 Hz, 3H), 0.68 (s, 3H).

Example 508: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(5-methylpyrimidin-4-yl)piperazin-1-yl)pentan-1-one

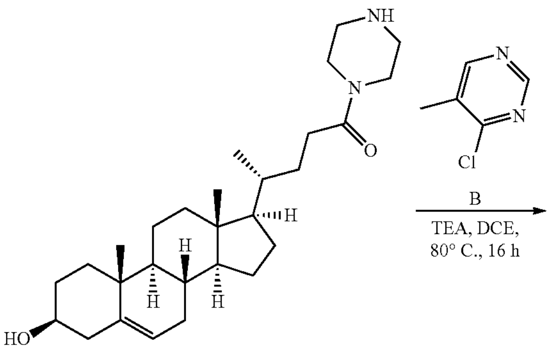

A

-continued

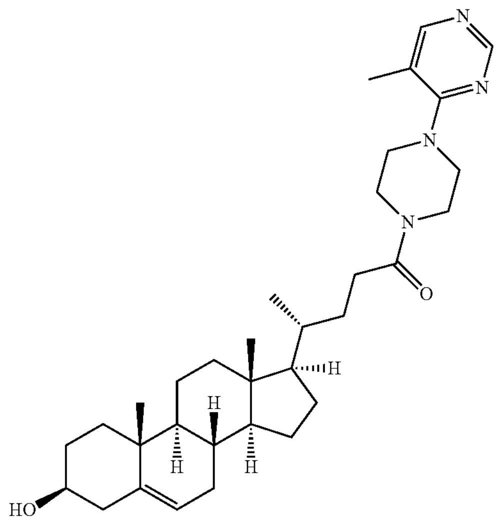

A solution of compound A (0.2 g, 452 μmol), compound B (52.3 mg, 407 μmol) and triethylamine (137 mg, 1.36 mmol) in 1,2-dichloroethane (4 mL) was stirred at 80° C. for 16 h. The reaction concentrated under reduced pressure. The crude product was purified by RP-column to afford the title compound 508 (13 mg, 5.4%). .LCMS: [M+1]+=535.20. $^1$H NMR (400 MHz, Chloroform-d) δ 8.62 (s, 1H), 8.19 (s, 1H), 5.35 (d, J=5.2 Hz, 1H), 3.73 (s, 2H), 3.63 (d, J=16.7 Hz, 2H), 3.52 (dd, J=11.0, 5.6 Hz, 3H), 3.41 (s, 2H), 2.48-2.37 (m, 1H), 2.26 (d, J=13.2 Hz, 6H), 1.99 (t, J=12.8 Hz, 2H), 1.85 (d, J=10.0 Hz, 4H), 1.47-0.89 (m, 20H), 0.69 (s, 3H).

Example 509: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(6-methylpyrimidin-4-yl)piperazin-1-yl]pentan-1-one

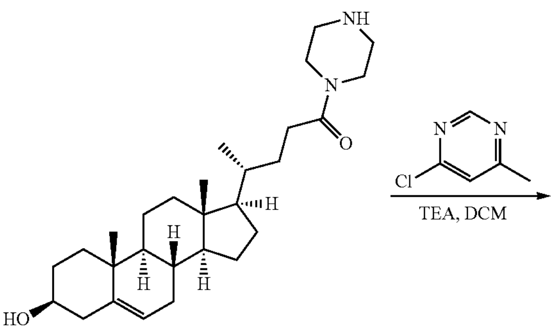

A

-continued

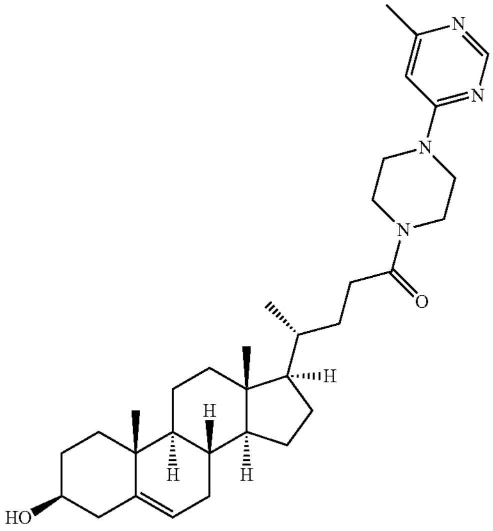

To a solution of compound A (150 mg, 339 μmol) in DCM (20 mL) was added TEA (283 μL, 2.03 mmol) and the reaction was cooled to 0° C. for 10 min. 4-chloro-6-methylpyrimidine (34.8 mg, 271 μmol) was added. The reaction was heated at reflux for 16 h under nitrogen. The reaction was diluted with water (10 mL) and extracted with DCM (20 mL). The organic layer was dried with sodium sulfate and concentrated under reduced pressure. The crude product was purified by silica gel chromatography to afford the title compound 509 (74.2 mg, 41.0%) as a white solid. LCMS: $[M+1]^+$=535.25. $^1$H NMR (400 MHz, $CDCl_3$) δ 8.54 (s, 1H), 6.39 (s, 1H), 5.35 (d, J=5.2 Hz, 1H), 3.76 (d, J=19.2 Hz, 4H), 3.65-3.46 (m, 5H), 2.45-2.36 (m, 4H), 2.31-2.20 (m, 3H), 2.05-1.77 (m, 8H), 1.53-1.43 (m, 6H), 1.35-1.23 (m, 4H), 1.22-1.07 (m, 4H), 1.01 (s, 3H), 0.97 (d, J=6.4 Hz, 3H), 0.69 (s, 3H).

Example 510: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(2-methylpyrimidin-4-yl)piperazin-1-yl)pentan-1-one

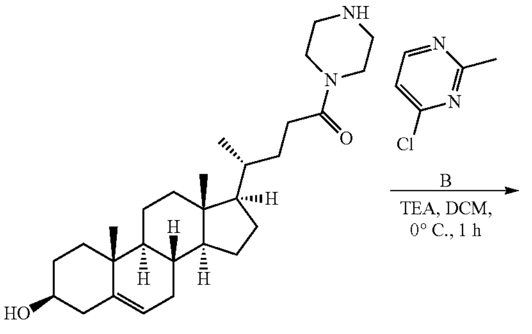

A

-continued

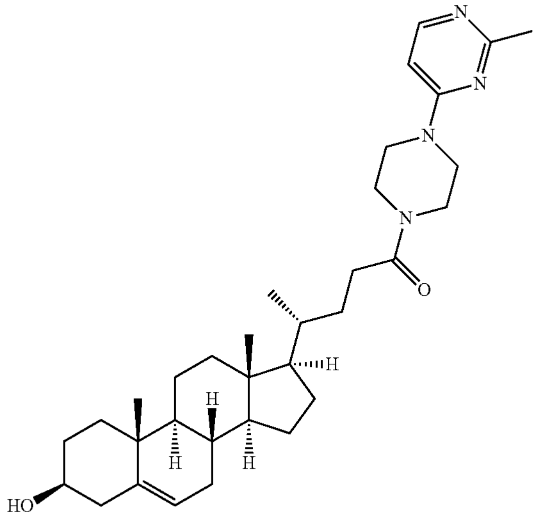

To a 0° C. solution of compound A (100 mg, 226 μmol) in dichloromethane (3 mL) was added triethylamine (137 mg, 1.36 mmol), 4-chloro-2-methylpyrimidine (26.1 mg, 203 μmol) and the reaction was stirred at 0° C. for 1 hour. Upon completion, the reaction was quenched with water (10 mL) and extracted with DCM (10 mL*3). The combined organic layers were washed with brine (10 mL) dried over sodium sulfate, filtered, and concentrated under reduced pressure. The crude product was purified by silica gel chromatography to afford the title compound 510 (24.6 mg, 20.4%) as a white solid. LCMS: $[M+1]^+$=534.39 $^1$H NMR (400 MHz, Chloroform-d) δ 8.17 (d, J=6.4 Hz, 1H), 6.33 (d, J=6.4 Hz, 1H), 5.35 (d, J=5.2 Hz, 1H), 3.79-3.67 (m, 4H), 3.63-3.46 (m, 5H), 2.52 (s, 3H), 2.46-2.36 (m, 1H), 2.32-2.19 (m, 3H), 2.03-1.95 (m, 2H), 1.91-1.75 (m, 6H), 1.64-1.04 (m, 15H), 1.01 (s, 3H), 0.97 (d, J=6.4 Hz, 3H), 0.69 (s, 3H).

Example 511: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(5-methoxypyrimidin-4-yl)piperazin-1-yl]pentan-1-one

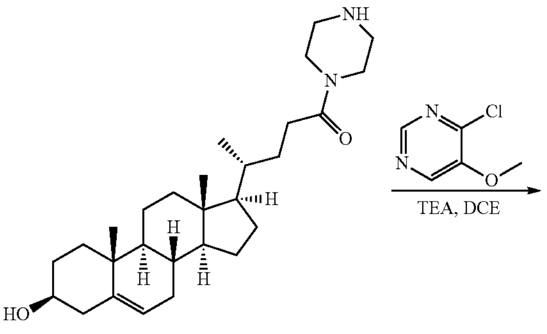

A

-continued

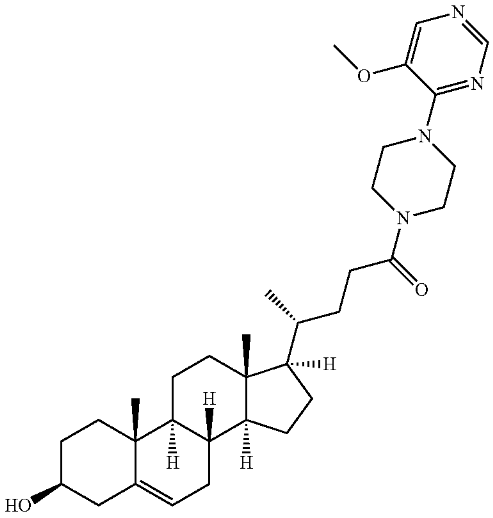

To a solution of compound A (150 mg, 339 μmol) in 1,2-dichloroethane (5 mL) was added triethylamine (283 μL, 2.03 mmol) at room temperature. After addition, the solution was cooled to 0° C. and 4-chloro-5-methoxypyrimidine (39.2 mg, 271 μmol) was added. The reaction was heated at 60° C. for 16 h under nitrogen. The reaction was diluted with water (10 mL) and extracted with DCM (10 mL). The organic layer was dried with sodium sulfate and concentrated under reduced pressure. The crude product was purified by silica gel chromatography to afford the title compound 511 (25.0 mg, 13.4%) as a white solid. LCMS: $[M+1]^+$=551.25. $^1H$ NMR (400 MHz, $CDCl_3$) δ 8.36 (s, 1H), 7.96 (bs, 1H), 5.37-5.33 (m, 1H), 3.89 (s, 3H), 3.80-3.67 (m, 6H), 3.61-3.47 (m, 3H), 2.47-2.35 (m, 1H), 2.32-2.21 (m, 3H), 2.04-1.75 (m, 6H), 1.64-1.06 (m, 16H), 1.01 (s, 3H), 0.97 (d, J=6.4 Hz, 3H), 0.69 (s, 3H).

Example 512: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(6-methoxypyrimidin-4-yl)piperazin-1-yl]pentan-1-one

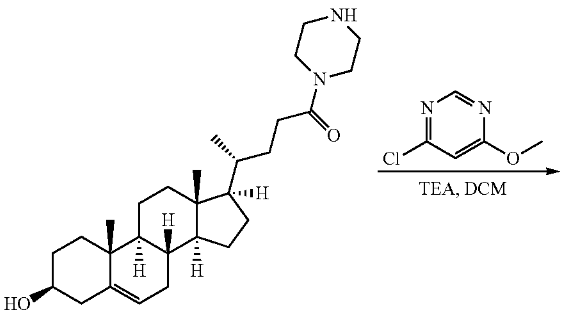

A

-continued

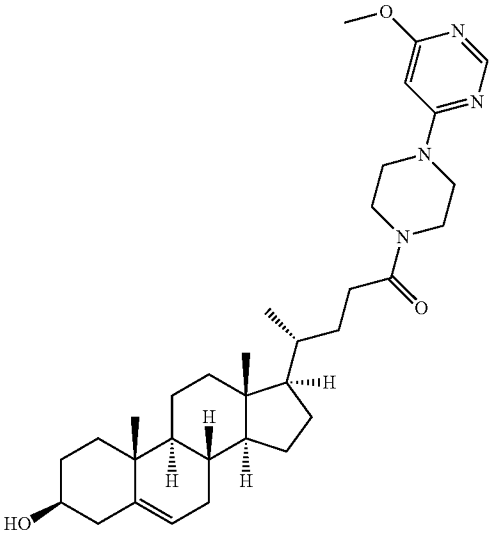

To a room temperature solution of compound A (200 mg, 452 μmol) in dichloromethane (8 mL) was added triethylamine (274 mg, 2.71 mmol) and the reaction was cooled to 0° C. 4-chloro-6-methoxypyrimidine (52.2 mg, 361 μmol) was added and the reaction was heated at reflux for 16 h under nitrogen. The reaction was diluted with water (10 mL) and extracted with DCM (10 mL). The organic layer was dried with sodium sulfate and concentrated under reduced pressure. The crude product was purified by silica gel chromatography to give the title compound 512 (62.2 mg, 25.0%). LCMS: $[M+1]^+$=551.25. $^1H$ NMR (400 MHz, $CDCl_3$) δ 8.34 (s, 1H), 5.82 (s, 1H), 5.35 (d, J=5.2 Hz, 1H), 3.93 (s, 3H), 3.74-3.67 (m, 4H), 3.59-3.49 (m, 5H), 2.46-2.19 (m, 4H), 2.05-1.75 (m, 6H), 1.55-1.05 (m, 15H), 1.01 (s, 3H), 0.96 (d, J=6.4 Hz, 3H), 0.91-0.87 (m, 1H), 0.69 (s, 3H).

Example 513: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(2-methoxypyrimidin-4-yl)piperazin-1-yl) pentan-1-one

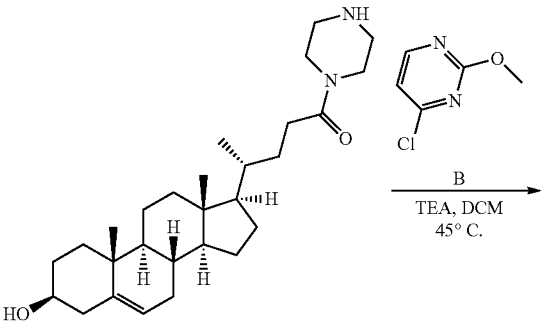

A

-continued

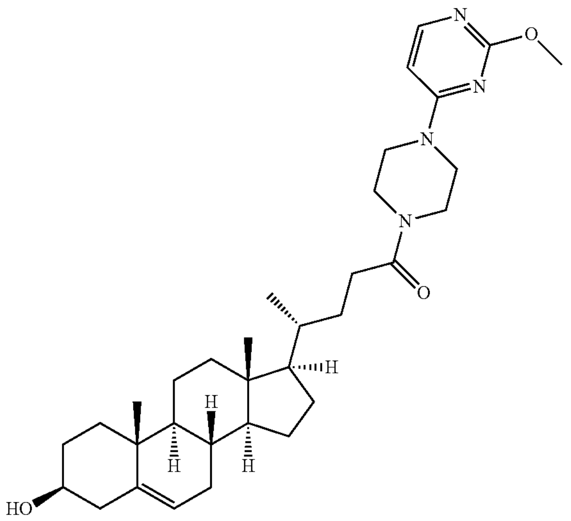

To a solution of compound A (200 mg, 452 μmol) and compound B (65.3 mg, 452 μmol) in dichloromethane (10 mL) was added TEA (274 mg, 2.71 mmol) and the reaction was stirred at 45° C. under nitrogen for 16 hours. Upon completion, the reaction was quenched with water (10 mL) and extracted with dichloromethane (10 mL*3). The combined organic layers were washed with brine (10 mL), dried over sodium sulfate, filtered, and concentrated under reduced pressure. The crude product was purified by silica gel chromatography to afford the title compound 513 (85.7 mg, 20%) as a white solid. LCMS: $[M+1]^+$=551.25. $^1H$ NMR (400 MHz, Chloroform-d) δ 8.07 (d, J=6.0 Hz, 1H), 6.18 (d, J=6.0 Hz, 1H), 5.35 (d, J=5.2 Hz, 1H), 3.94 (s, 3H), 3.73 (dd, J=13.6, 6.0 Hz, 4H), 3.63-3.49 (m, 5H), 2.43-2.40 (m, 1H), 2.31-2.18 (m, 3H), 2.03-1.94 (m, 2H), 1.88-1.76 (m, 4H), 1.69 (s, 2H), 1.63-1.55 (m, 2H), 1.47-1.42 (m, 2H), 1.39-1.25 (m, 3H), 1.22-1.03 (m, 5H), 1.00 (s, 3H), 0.96 (d, J=6.6 Hz, 3H), 0.92 (dd, J=11.2, 5.6 Hz, 1H), 0.69 (s, 3H).

Example 514: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(1-methyl-1H-1,2,3-triazol-4-yl)piperazin-1-yl)pentan-1-one

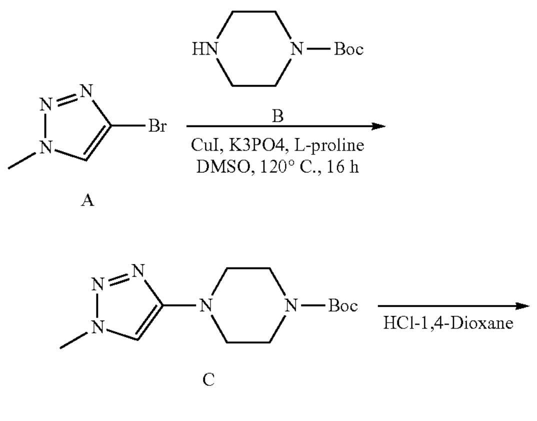

-continued

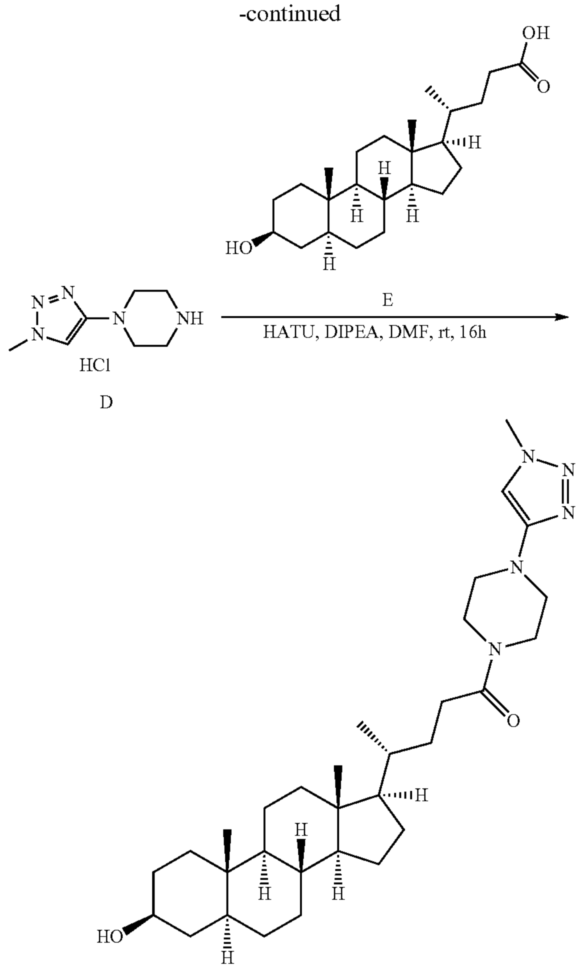

To a solution of compound A (500 mg, 3.09 mmol) in DMSO (7.5 mL) was added compound B (690 mg, 3.7 mmol), CuI (176 mg, 9.26 mmol), $K_3PO_4$ (1.97 g, 9.26 mmol) and L-proline (213 mg, 1.85 mmol). The reaction was stirred at 120° C. for 16 hours under nitrogen. The reaction was diluted with water (15 mL) and extracted with ethyl acetate (30 mL). The organic layer was dried over sodium sulfate, filtered, and concentrated under reduced pressure. The crude product was purified by silica gel chromatography to compound B (20 mg, 2.42%). 4N HCl in 1,4-dioxane (3 mL) was added slowly to the compound B (15 mg, 56.1 μcool) in a single-neck flask at room temperature and stirred for 1 hour. Upon completion, the reaction was added DCM (10 mL) and concentrated under reduced pressure to afford the compound C as the HCl salt (11.4 mg).

(R)-4-((3S,5S,8R,9S,10S,13R,14S,17R)-3-hydroxy-10,13-dimethylhexadecahydro-1H-cyclopenta[a]phenanthren-17-yl)pentanoic acid (40 mg, 107 μmol) and 1-(1-methyl-1H-1,2,3-triazol-4-yl)piperazine hydrochloride (11.4 mg, 56 μmol) were reacted according to the method of Example 536 to afford the title compound 514 (10 mg, 18%) as a white solid. LCMS: $[M+1]^+$=526.40. $^1H$ NMR (400 MHz, Chloroform-d) δ 6.85 (s, 1H), 5.35 (d, J=5.2 Hz, 1H), 4.01 (s, 3H), 3.78-3.48 (m, 5H), 3.20 (d, J=70.4 Hz, 4H), 2.45-2.37 (m, 1H), 2.32-2.22 (m, 3H), 2.06-1.90 (m, 3H), 1.89-1.78 (m, 4H), 1.53-1.04 (m, 14H), 1.02 (s, 3H), 0.98 (d, J=6.4 Hz, 3H), 0.70 (s, 3H).

Example 515: (R)-1-(4-(cyclopentanecarbonyl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

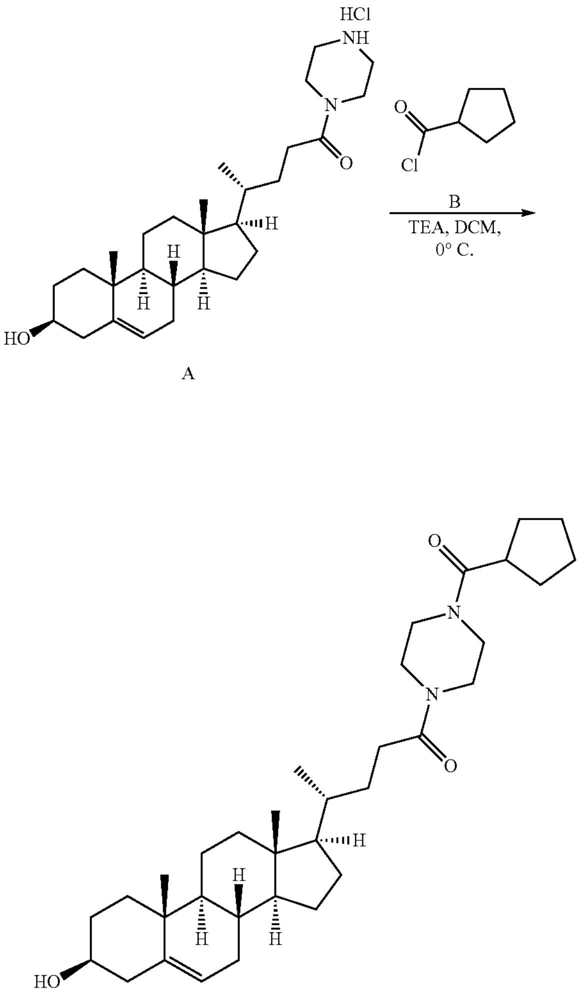

To a solution of compound A (200 mg, 417 μmol) in dichloromethane (6 mL) under 0° C. was added TEA (169 mg, 1.67 mmol) and compound B (49.8 mg, 376 μmol). The reaction was stirred for 16 h. Upon completion, the reaction was diluted with water (10 mL) and extracted with DCM (15 mL*3). The organic layer was washed with brine (10 mL), dried over sodium sulfate, filtered, and concentrated under reduced pressure. The crude product was purified by silica gel chromatography to afford the title compound 515 (36 mg, 16%). LCMS: $[M+1]^+=539.40$. $^1H$ NMR (400 MHz, Chloroform-d) δ 5.35-5.33 (m, 1H), 3.70-3.39 (m, 9H), 2.89 (t, J=7.6 Hz, 1H), 2.39 (ddd, J=15.6, 10.8, 5.2 Hz, 1H), 2.33-2.16 (m, 3H), 2.04-1.94 (m, 2H), 1.79-1.75 (m, 9H), 1.62 (d, J=11.2 Hz, 4H), 1.48-1.45 (m, 5H), 1.38-1.23 (m, 3H), 1.10 (m, 4H), 1.00 (s, 3H), 0.97-0.88 (m, 4H), 0.68 (s, 3H).

Example 516: (R)-1-(4-(1-cyclopropyl-1H-pyrrol-3-yl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

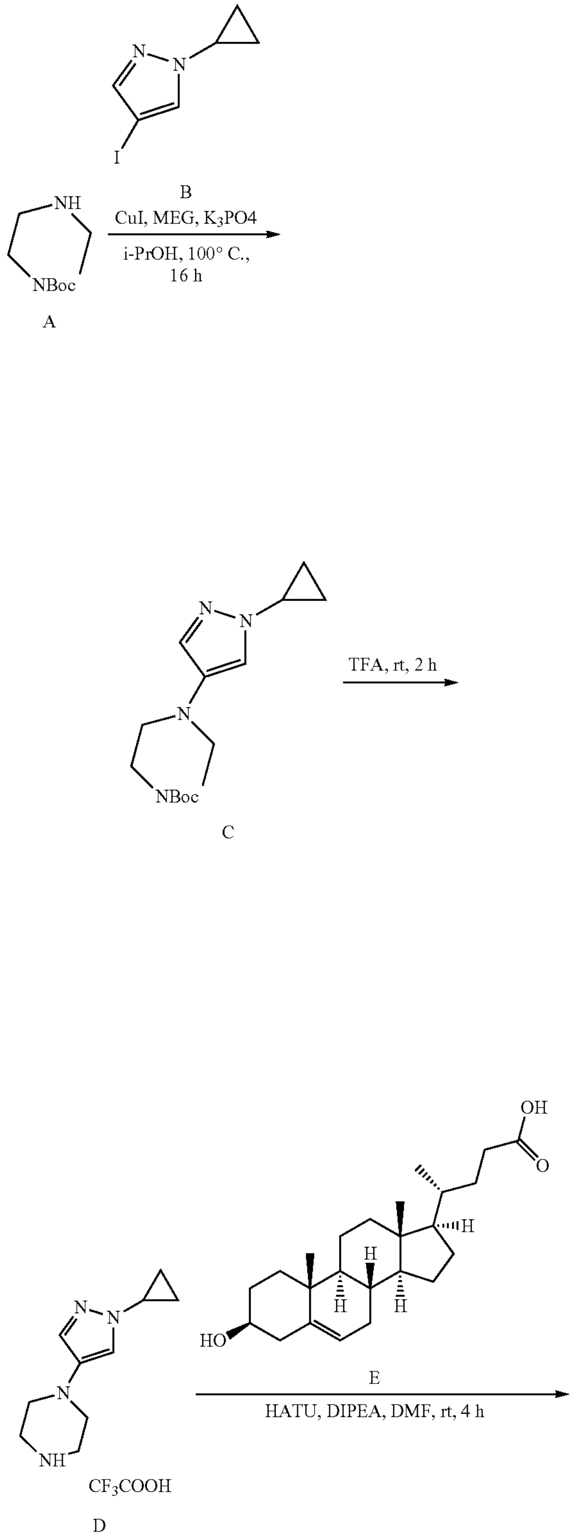

-continued

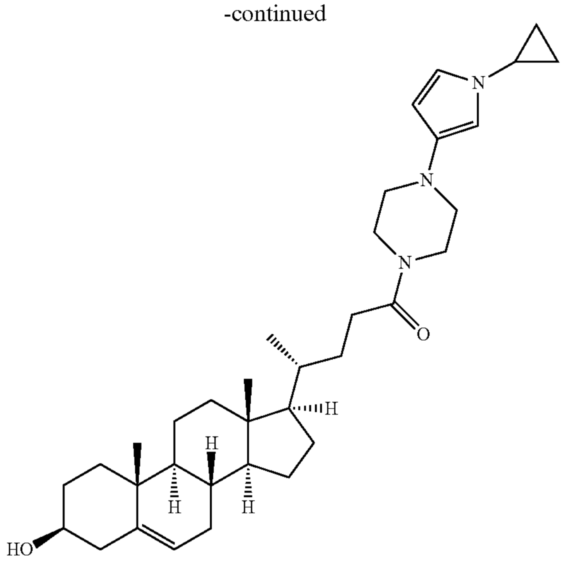

To a solution of compound A (300 mg, 1.61 mmol) in i-PrOH (6 mL) was added compound B (377 mg, 1.61 mmol), CuI (61.4 mg, 322 μmol), $K_3PO_4$ (1.37 g, 6.44 mmol) and ethane-1,2-diol (0.1 g, 1.61 mmol). The reaction was stirred at 100° C. for 16 h under $N_2$. Upon completion, the reaction was diluted with water (10 mL) and extracted with ethyl acetate (20 mL). The organic layer was concentrated under reduced pressure and the crude product was purified by Prep-TLC to afford the title compound C (250 mg, 53%). To a solution of compound C (250 mg, 855 μmol) in DCM was added TFA (2 mL). The reaction was stirred at room temperature for 2 h. Upon completion, the reaction concentrated to afford compound D as the TFA salt (109 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (97.4 mg, 260 μmol) and 1-(1-cyclopropyl-1H-pyrazol-4-yl) piperazine 2,2,2-trifluoroacetate (50 mg, 163 μmol) were reacted according to the method of Example 430 to afford the title compound 516 (125 mg, 87%) as a white solid. LCMS: $[M+1]^+$=549.25 $^1H$ NMR (400 MHz, Chloroform-d) δ 7.20 (s, 1H), 7.06 (s, 1H), 5.35 (d, J=5.2 Hz, 1H), 3.74 (s, 2H), 3.60 (s, 2H), 3.54-3.48 (m, 2H), 2.95-2.86 (m, 4H), 2.40-2.36 (m, 1H), 2.33-2.19 (m, 3H), 2.05-1.95 (m, 3H), 1.90-1.75 (m, 4H), 1.57-1.52 (m, 2H), 1.52-1.48 (m, 3H), 1.47-1.43 (m, 2H), 1.42-1.37 (m, 1H), 1.35-1.29 (m, 2H), 1.26 (s, 2H), 1.20-1.94 (m, 14H), 0.69 (s, 3H).

Example 517: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3S)-3-[(1-methyl-1H-pyrazol-4-yl)oxy]piperidin-1-yl]pentan-1-one

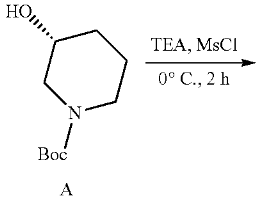

A

-continued

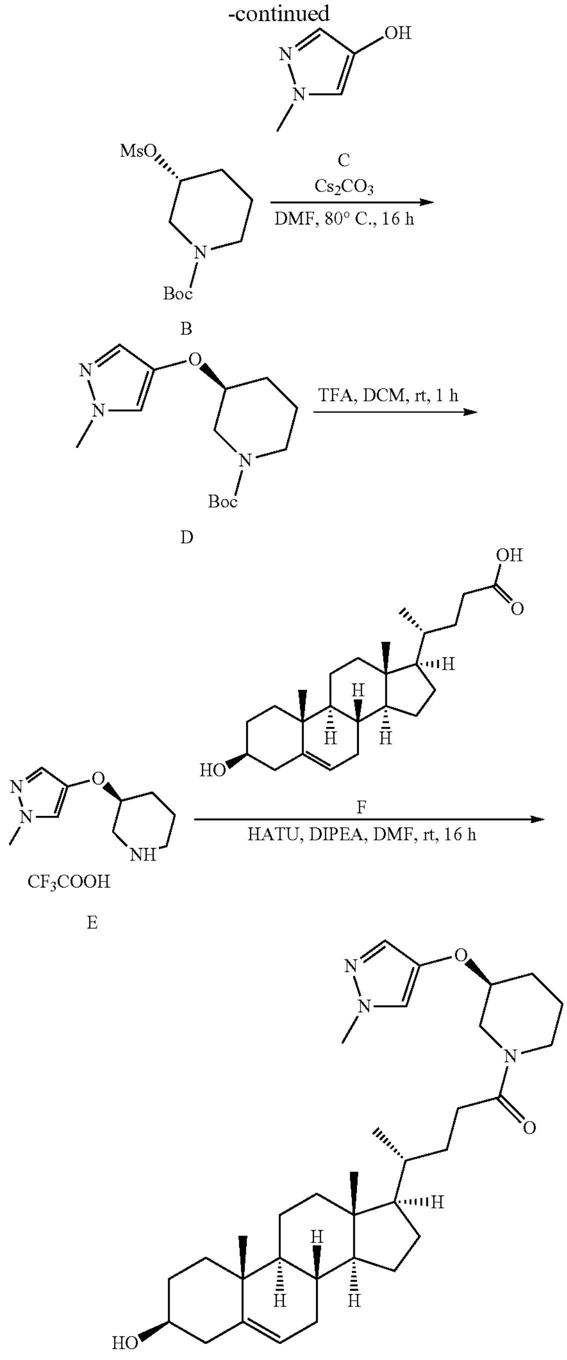

To a solution of compound A (500 mg, 2.48 mmol) in THF (10 mL) was added TEA (754 mg, 745 mmol) and MsCl (424 mg, 3.72 mmol) at 0° C. slowly. The reaction was stirred for 2 hours. Upon completion, the reaction was quenched with water (20 mL) and extracted with ethyl acetate (20 mL*3). The combined organic layers were washed with brine (5 mL), dried over sodium sulfate, filtered, and concentrated under reduced pressure. The residue was purified by silica gel chromatography to afford compound B (460 mg, 66%) as a white solid. To a solution of compound B (460 mg, 1.65 mmol, 66%) in DMF (10 mL), was added compound C (232 mg, 2.36 mmol), $Cs_2CO_3$ (2.31 g, 7.09 mmol) and the reaction was heated to 80° C. under $N_2$ for 16 h. The reaction was cooled to room temperature and concentrated under reduced pressure. The residue was purified by silica gel chromatography to afford compound D (120 mg, 18%) as a yellow solid. To a solution of compound D (120 mg, 427 μmol) in DCM (6 mL) was added TFA (2 mL) at room temperature and the reaction was stirred for 2 h. The reaction concentrated under reduced pressure to afford compound E as the TFA salt (130 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (132 mg, 353 μmol) and (S)-3-((1-methyl-1H-pyrazol-4-yl)oxy)piperidine 2,2,2-trifluoroacetate (130 mg, 427 μmol) were reacted according to the method of Example 536 to afford the title compound 517 (60 mg, 25%) as a white solid. LCMS: $[M+1]^+=538.20$. $^1H$ NMR (400 MHz, Chloroform-d) δ 7.29 (d, J=8.6 Hz, 1H), 5.35 (d, J=5.2 Hz, 1H), 4.10 (d, J=13.4 Hz, 1H), 3.87-3.84 (m, 4H), 3.67-3.46 (m, 4H), 3.32 (s, 1H), 2.40 (d, J=11.0 Hz, 1H), 2.35-2.06 (m, 7H), 1.97 (d, J=15.0 Hz, 3H), 1.89-1.71 (m, 6H), 1.61-1.52 (m, 3H), 1.47-1.40 (m, 3H), 1.36-1.28 (m, 2H), 1.23-1.03 (m, 4H), 1.00 (s, 3H), 0.98-0.86 (m, 4H), 0.68 (s, 3H).

Example 518: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3R)-3-[(1-methyl-1H-pyrazol-4-yl)oxy]piperidin-1-yl]pentan-1-one

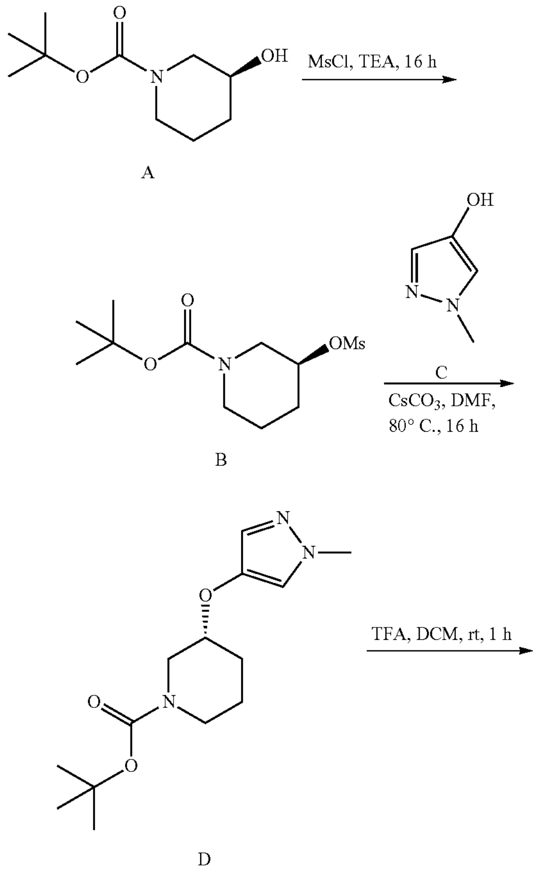

-continued

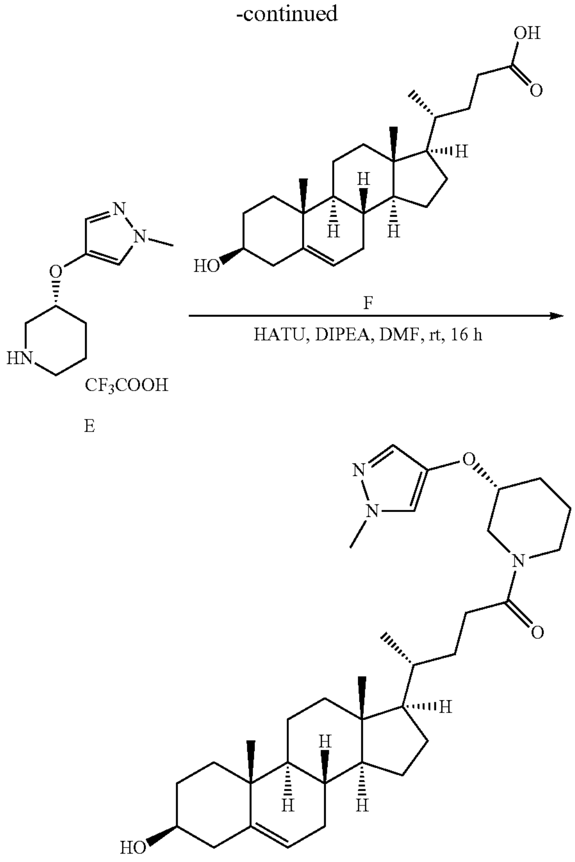

To a 0° C. solution of compound A (1 g, 4.97 mmol) in THE (6 mL) was added triethylamine (1.51 g, 14.9 mmol), methanesulfonyl chloride (854 mg, 7.45 mmol) and the reaction was stirred for 16 hours. The reaction was quenched with water (10 mL) and extracted with ethyl acetate (30 mL*4). The combined organic layers were concentrated under reduced pressure. The crude product was purified by silica gel chromatography to afford the compound B (1.1 g, 79%) as a white solid. To a solution of compound B (700 mg, 2.51 mmol) in DMF (4 mL) was added compound C (246 mg, 2.51 mmol), $Cs_2CO_3$ (2.45 g, 7.52 mmol) and the reaction was stirred at 80° C. for 16 hours. The reaction was quenched with water (15 mL) and extracted with ethyl acetate (10 mL*4). The combined organic layers were concentrated under reduced pressure. The crude product was purified by silica gel chromatography to afford compound D (177 mg, 25%) as a white solid. To a solution of compound D (100 mg, 355 μmol) in DCM (6 mL) was added TFA (2 mL) at room temperature and the reaction was stirred for 2 h. The reaction concentrated under reduced pressure to give compound E as the TFA salt (64.4 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (106 mg, 284 μmol) and (R)-3-((1-methyl-1H-pyrazol-4-yl)oxy)piperidine 2,2,2-trifluoroacetate (64.4 mg, 218 μmol) was reacted according to the method of Example 536 to afford the title compound 518 (83.5 mg, 43%) as a white solid. LCMS: $[M+1]^+=538.25$. $^1H$ NMR (400 MHz, Chloroform-d) δ 7.23-7.14 (m, 1H), 5.34 (s, 1H), 3.81 (d, J=5.2 Hz, 3H), 3.52 (t, J=13.4 Hz, 3H), 3.33-3.14 (m, 1H), 2.42-2.12 (m, 4H), 2.04-1.91 (m, 3H), 1.81 (t, J=15.6 Hz, 5H), 1.48-1.45 (m, 8H), 1.38-1.24 (m, 3H), 1.21-1.02 (m, 4H), 1.00 (s, 4H), 0.95 (d, J=6.4 Hz, 2H), 0.88 (d, J=6.0 Hz, 2H), 0.67 (d, J=6.4 Hz, 3H).

Example 519: (R)-1-((R)-3-ethyl-3-methoxypiperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

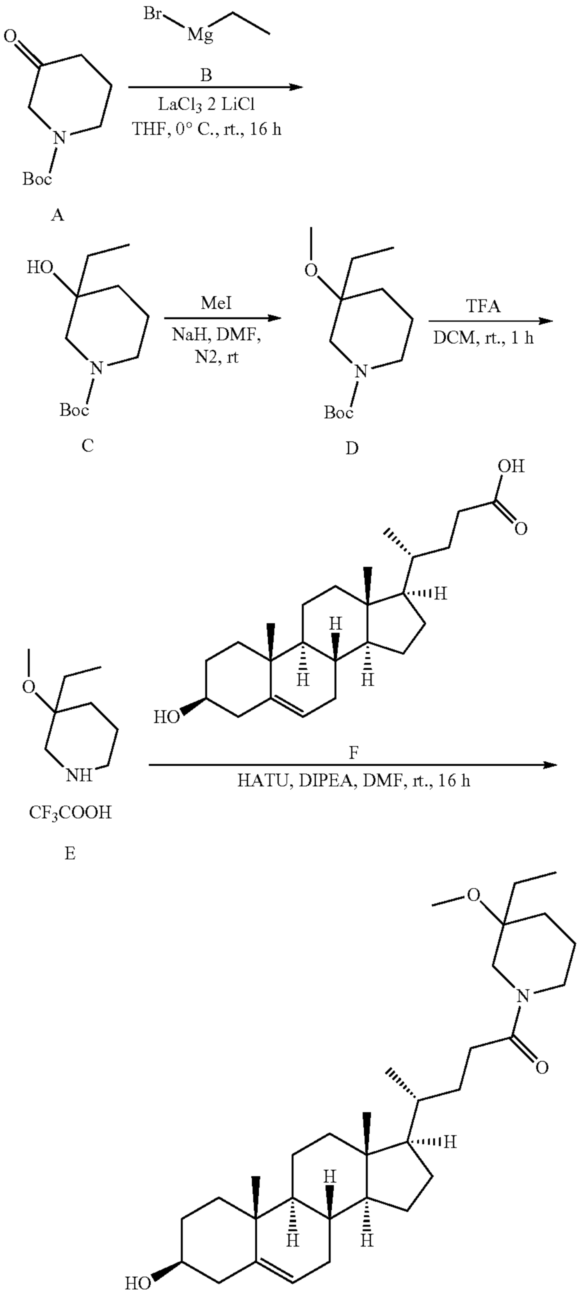

To a 0° C. solution of compound B (1.07 g, 8.03 mmol) in THF (2 mL) was added $LaCl_3 \cdot 2LiCl$ (8.1 mL, 1M in THF, 8.1 mmol) and the reaction stirred at 0° C. under $N_2$ for 2 h. Compound A (400 mg, 2.01 mmol) was added at 0° C. The reaction was stirred at room temperature under $N_2$ for 16 h. The reaction was added saturated aqueous $NH_4Cl$ (5 mL) and extracted with EtOAc (20 mL). The organic layer was dried over sodium sulfate and concentrated. The residue was purified by silica gel chromatography to afford compound C (200 mg, 43.4% yield) as a yellow oil. To a 0° C. solution of compound C (200 mg, 872 μmol) in DMF (2 mL) was added NaH (60.2 mg, 1.51 mmol, 60% dispersion in mineral oil) under $N_2$ and the reaction was warmed to room temperature for 0.5 h. $CH_3I$ (186 mg, 1.31 mmol) was added and the reaction was stirred at room temperature for 3 h. The reaction was quenched with water (10 mL) and extracted with EtOAc (30 mL). The organic layer was washed with brine (5 mL), dried over sodium sulfate, and concentrated to afford compound D (180 mg, 84.5% yield) as a yellow oil. To a solution of compound D (180 mg, 740 μmol) in DCM (2 mL) was added TFA (0.5 mL). The reaction was stirred at room temperature for 1 h. The reaction concentrated under reduced pressure to give compound E as the TFA salt (188 mg, 720 μmol).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (150 mg, 404 μmol) and 3-ethyl-3-methoxypiperidine(188 mg, 720 μmol) were reacted according to the method of Example 536 to afford the title compound 519 (110 mg, 55%) as a white solid. LCMS: $[M+1]^+$=500.25 $^1$H NMR (400 MHz, Chloroform-d) δ 5.34 (dd, J=4.8, 2.6 Hz, 1H), 4.28-4.05 (m, 1H), 3.69-3.45 (m, 2H), 3.15-3.11 (m, 3H), 3.10-2.71 (m, 2H), 2.44-2.16 (m, 4H), 2.04-1.93 (m, 2H), 1.93-1.70 (m, 6H), 1.66-1.56 (m, 5H), 1.55-1.40 (m, 8H), 1.38-1.25 (m, 4H), 1.20-1.02 (m, 4H), 1.00 (s, 3H), 0.95-0.93 (m, 5H), 0.90-0.84 (m, 3H), 0.68 (s, 3H).

Example 520: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-(pyridin-4-yloxy)piperidin-1-yl)pentan-1-one

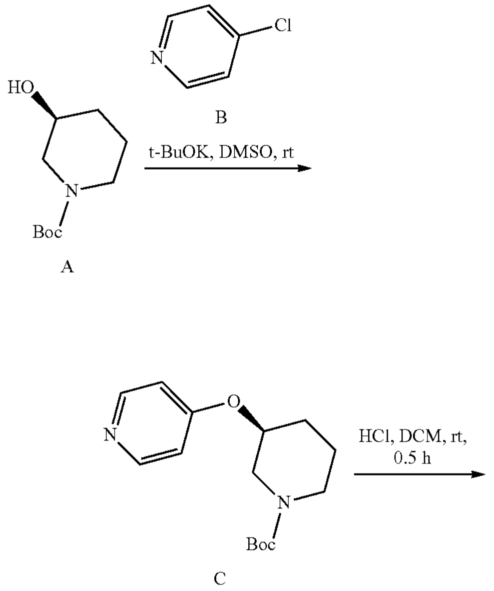

-continued

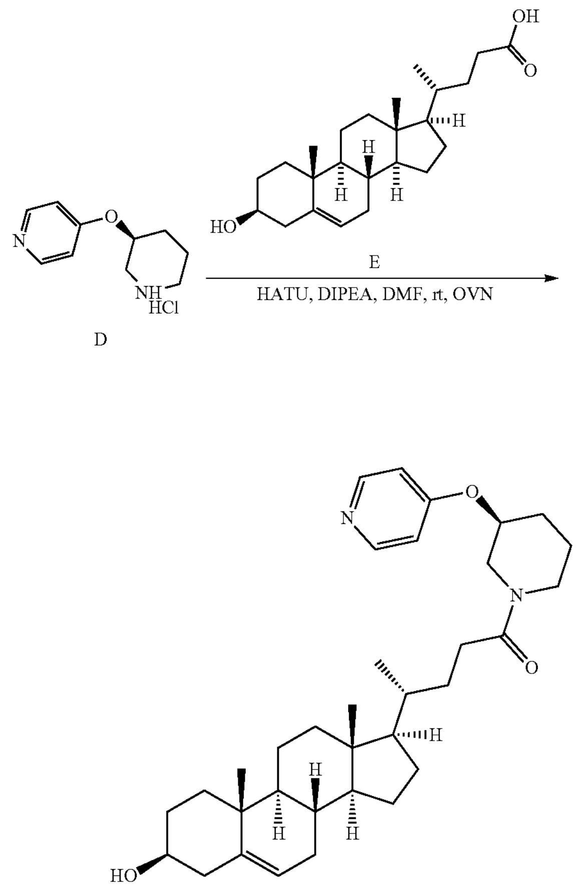

To a solution of compound A (360 mg, 1.79 mmol) in DMSO (5 mL) was added compound B (169 mg, 1.49 mmol) and t-BuOK (669 mg, 5.96 mmol) at room temperature under $N_2$ and stirred for 16 h. The reaction was diluted with saturated aqueous $NH_4Cl$ (30 mL) and extracted with EtOAc (10 mL*2). The combined organic layers were washed with water (20 mL), brine (20 mL), dried over sodium sulfate and concentrated under reduced pressure to afford compound C (350 mg, 85%) as a yellow oil. To a solution of compound C (150 mg, 539 μmol) in DCM (3 mL) was added HCl (2 mL, 8 mmol, 4M in 1,4-dioxane) at room temperature and the reaction was stirred for 0.5 h. The reaction concentrated under reduced pressure to give compound D as the HCl salt (108 mg) as a white solid.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (151 mg, 404 μmol) and (S)-4-(piperidin-3-yloxy)pyridine hydrochloride (108 mg, 505 μmol) were reacted according to the method of Example 536 to afford the title compound 520 (70 mg, 25%) as a white solid. LCMS: $[M+1]^+$=535.20. $^1H$ NMR (400 MHz, Chloroform-d) δ 8.43 (dd, J=12.8, 5.4 Hz, 2H), 6.89-6.75 (m, 2H), 5.35-5.33 (m, 1H), 4.54-4.20 (m, 2H), 3.83-3.16 (m, 4H), 3.05 (dd, J=13.2, 8.4 Hz, 1H), 2.46-2.39 (m, 1H), 2.33-2.11 (m, 4H), 2.04-1.92 (m, 3H), 1.90-1.79 (m, 4H), 1.76-1.69 (m, 3H), 1.59-1.38 (m, 9H), 1.36-1.26 (m, 2H), 1.17-1.04 (m, 4H), 1.00-0.99 (m, 3H), 0.97 (d, J=6.4 Hz, 2H), 0.93-0.89 (m, 1H), 0.85 (d, J=6.4 Hz, 1H), 0.67 (d, J=14.4 Hz, 3H).

Example 521: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((R)-3-(pyridin-4-yloxy)piperidin-1-yl)pentan-1-one

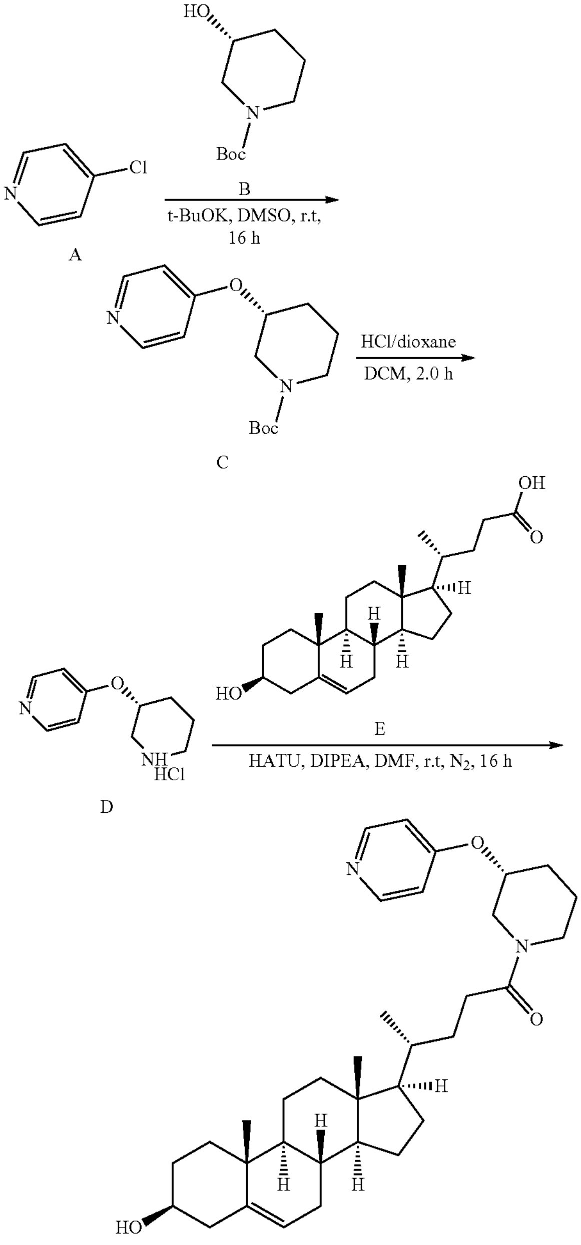

To a solution of compound A (250 mg, 2.21 mmol) in DMSO (10 mL) was added compound B (440 mg, 2.21 mmol), t-BuOK (500 mg, 4.42 mmol) and the reaction was stirred at room temperature for 16 h. The reaction was quenched with water (20 mL) and extracted with EtOAc (40 mL). The organic layer was washed with brine, dried over sodium sulfate, filtered, and concentrated. The residue was purified by silica gel chromatography to afford the compound C (400 mg, 65%) as a white solid. To a solution of compound C (200 mg, 0.719 mmol) in DCM (2 mL) was added 4N HCl in 1,4-dioxane (0.2 mL). The reaction was stirred at room temperature for 1.0 h. The reaction concentrated to afford compound D as the HCl salt (170 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (215 mg, 575 μmol) and (R)-4-(piperidin-3-yloxy)pyridine hydrochloride (128 mg, 719 μmol) was reacted according to the method of Example 536 to afford the title compound 521 (90.8 mg, 23.4%) as a white solid. LCMS: $[M+1]^+$=535.20. $^1H$ NMR (400 MHz, Chloroform-d) δ 8.48-8.35 (m, 2H), 6.88-6.73 (m, 2H), 5.37-5.31 (m, 1H), 4.46 (m, 1H), 4.30 (m, 1H), 3.71-3.61 (m, 1H), 3.57-3.39 (m, 2H), 3.22-3.20 (m, 1H), 3.05-3.02 (m, 1H), 2.44-2.33 (m, 1H), 2.33-2.08 (m, 4H), 2.05-1.72 (m, 9H), 1.62-1.28 (m, 11H), 1.22-0.80 (m, 13H), 0.67 (d, J=16.4 Hz, 3H).

Example 522: 4-({1-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]piperidin-4-yl}methyl)-2,2-dimethylmorpholin-3-one

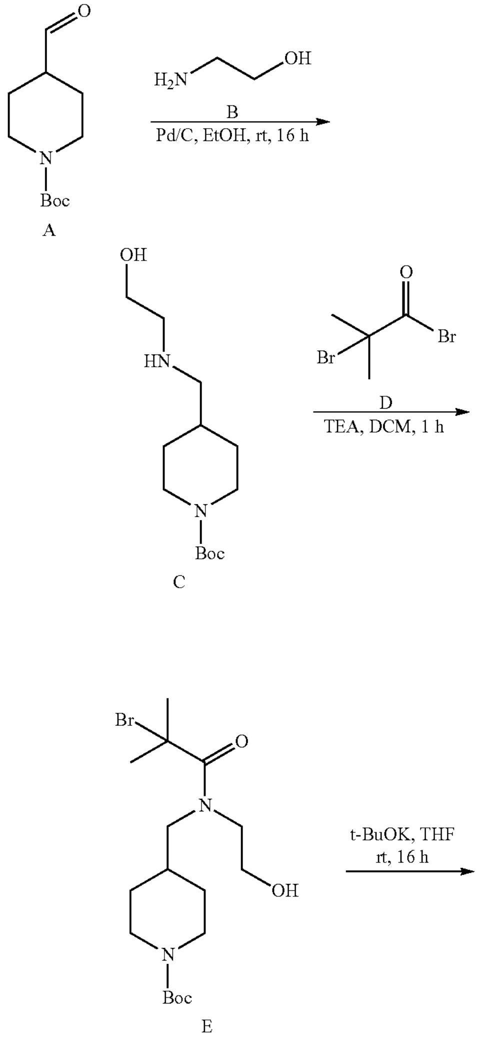

-continued

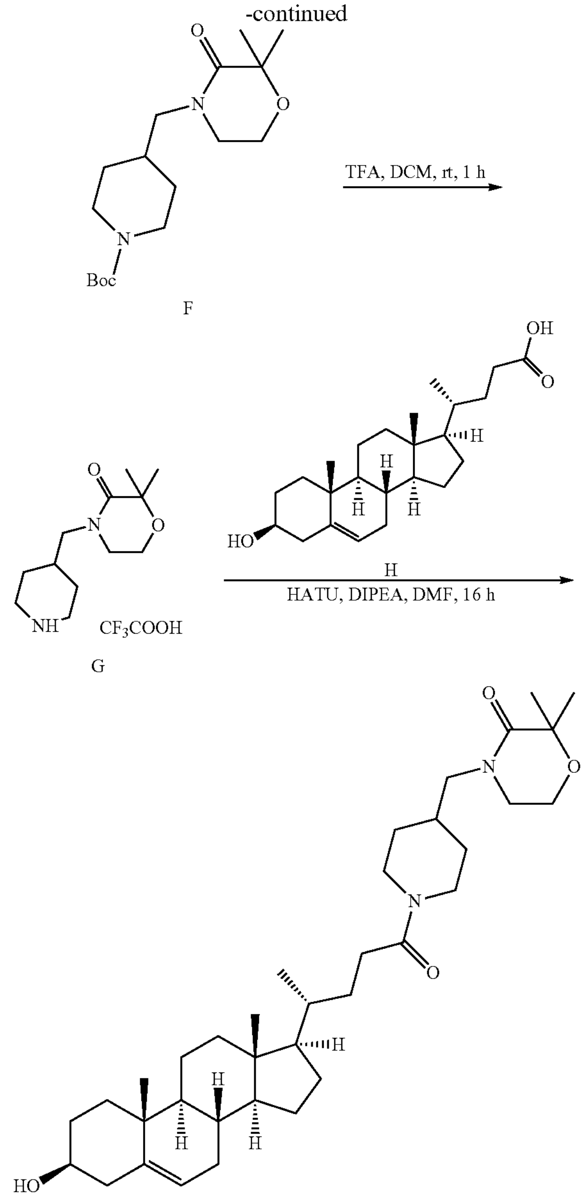

To a solution of compound A (2 g, 9.38 mmol) in ethanol (4 mL) was added compound B (687 mg, 11.3 mmol) and 10% Pd/C (20 mg). The reaction was stirred at room temperature for 16 hours under a $H_2$ atmosphere. The reaction was filtered and concentrated to afford compound C (2.4 g, 99%) as a white solid. To a 0° C. solution of compound C (1 g, 3.87 mmol) in dichloromethane (10 mL) was added TEA (783 mg, 7.74 mmol), compound D (890 mg, 3.87 mmol) and the reaction was stirred at 0° C. for 1 hour. The reaction was quenched with water (20 mL) and extracted with ethyl acetate (30 mL*4). The combined organic layers were concentrated under reduced pressure. The crude product was purified by silica gel chromatography to afford compound E (1 g, 63%) as a white solid. To a solution of compound E (200 mg, 491 μmol) in THE (2 mL) was t-BuOK (110 mg, 982 μmol). The reaction was stirred at room temperature for 16 hours. The reaction was quenched with water (10 mL) and extracted with ethyl acetate (10 mL*4). The combined organic layers were concentrated to give the crude compound F (150 mg, 93%)

as a white solid. To a solution of compound F (100 mg, 306 μmol) in DCM (6 mL) was added TFA (2 mL) at room temperature and the reaction was stirred for 2 h. The reaction concentrated under reduced pressure to give compound G as a TFA salt (60 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (89.8 mg, 240 μmol) and 2,2-dimethyl-4-(piperidin-4-ylmethyl)morpholin-3-one 2,2,2-trifluoroacetate (60 mg, 178 μmol) were reacted according to the method of Example 536 to afford the title compound 522 (54.5 mg, 31%) as a white solid. LCMS: $[M+1]^+$=583.30. $^1H$ NMR (400 MHz, Chloroform-d) δ 5.35 (s, 1H), 4.58 (d, J=13.2 Hz, 1H), 3.92-3.80 (m, 3H), 3.59-3.29 (m, 4H), 3.13-2.91 (m, 2H), 2.56 (t, J=12.4 Hz, 1H), 2.43-2.14 (m, 4H), 2.06-1.91 (m, 3H), 1.84 (d, J=13.0 Hz, 3H), 1.74 (s, 2H), 1.44 (s, 15H), 1.37-1.24 (m, 3H), 1.22-1.02 (m, 6H), 1.00 (s, 3H), 0.94 (d, J=6.6 Hz, 4H), 0.73-0.64 (m, 3H).

Example 523: 4-((1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-4-methylpiperidin-4-yl)methyl)-2,2-dimethylmorpholin-3-one

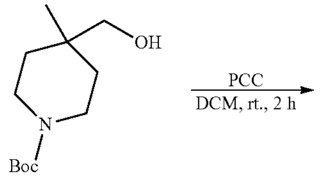

A

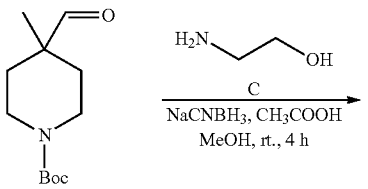

B

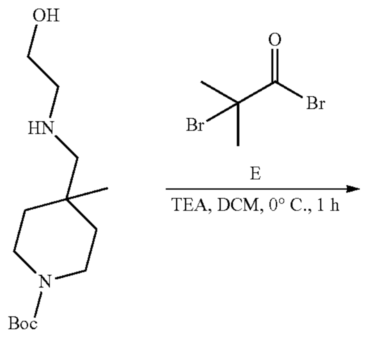

D

-continued

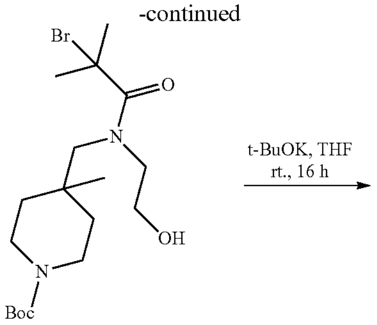

F

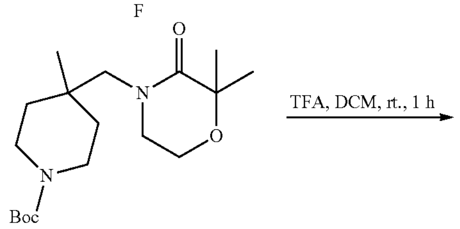

G

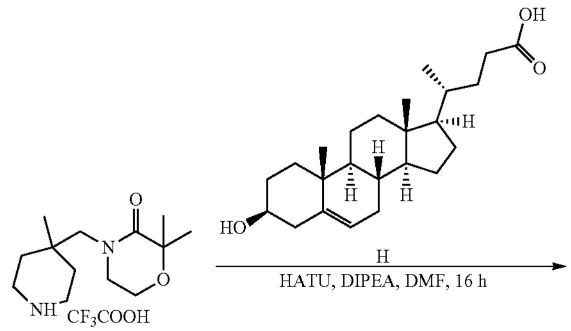

H

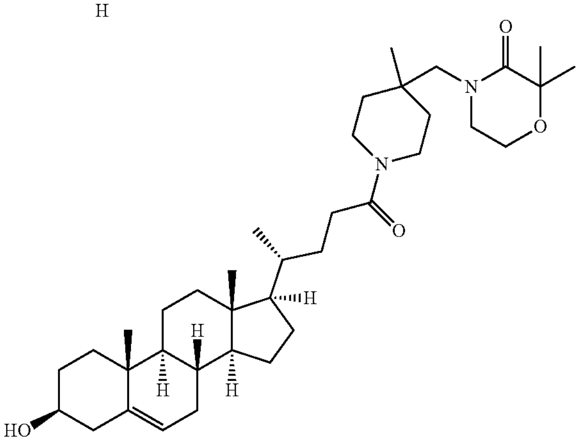

To a solution of compound A (500 mg, 2.18 mmol) in DCM (5 mL) was added PCC (1.41 g, 6.54 mmol). The reaction was stirred at room temperature for 2 h. The reaction was quenched with saturated aqueous sodium thiosulfate (10 mL) and extracted with EtOAc (20 mL). The organic layer was concentrated under reduced pressure and the residue was purified by silica gel chromatography to afford compound B (430 mg, 86.9% yield) as a yellow oil. To a solution of compound B (430 mg, 1.89 mmol) in methanol (1.72 mL) was added compound C (231 mg, 3.78 mmol), $NaCNBH_3$ (357 mg, 5.68 mmol) and AcOH (11.4 mg, 189 μmol). The reaction was stirred at room temperature for 4 hours. The reaction was quenched with water (10 mL)

and extracted with ethyl acetate (20 mL). The organic layer was concentrated under reduced pressure. The crude product was purified by Prep-TLC to afford compound D (440 mg, 85.4% yield) as a yellow oil. To a 0° C. solution of compound D (440 mg, 1.62 mmol) in DCM (17.6 mL) was added compound E (371 mg, 1.62 mmol), TEA (490 mg, 4.85 mmol) and the reaction was stirred at 0° C. for 1 hour. The reaction was quenched with water (10 mL) and extracted with EtOAc (20 mL). The organic layer was concentrated under reduced pressure. The crude product was purified by Prep-TLC to afford compound F (120 mg, 17.7% yield) as a yellow oil. To a solution of compound F (120 mg, 285 μmol) in THE (12 mL) was added t-BuOK (63.9 mg, 570 μmol). The reaction was stirred at room temperature for 16 hours. The reaction was quenched with water (5 mL) and extracted with EtOAc (15 mL). The reaction was cooled to room temperature and concentrated under reduced pressure. The residue was purified by silica gel chromatography to afford compound G (88 mg, 90% yield) as a yellow oil. To a solution of compound G (40 mg, 117 μmol) in DCM (2 mL) was added TFA (0.5 mL). The reaction was stirred at room temperature for 1 hour. The reaction concentrated under reduced pressure to afford compound H as the TFA salt (39 mg, 93.4 μmol).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (22.5 mg, 404 μmol) and 2,2-dimethyl-4-((4-methylpiperidin-4-yl)methyl)morpholin-3-one (35 mg, 93.4 μmol) were reacted according to the method of Example 536 to afford the title compound 523 (13.1 mg, 36.5%) as a white solid. LCMS: $[M+1]^+$=597.45. $^1H$ NMR (400 MHz, Chloroform-d) δ 5.35 (d, J=3.6 Hz, 1H), 3.84 (t, J=4.8 Hz, 2H), 3.67-3.38 (m, 5H), 3.29 (s, 2H), 3.06 (d, J=13.6 Hz, 1H), 2.42-2.13 (m, 4H), 1.98-1.96 (m, 2H), 1.90-1.71 (m, 4H), 1.66-1.47 (m, 11H), 1.45 (s, 6H), 1.43-1.40 (m, 1H), 1.39-1.26 (m, 6H), 1.21-1.06 (m, 4H), 1.04 (s, 3H), 1.00 (s, 3H), 0.99-0.95 (m, 1H), 0.94 (d, J=6.4 Hz, 3H), 0.92-0.86 (m, 1H), 0.68 (s, 3H).

Example 524: 4-(1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)-2,2-dimethylmorpholin-3-one

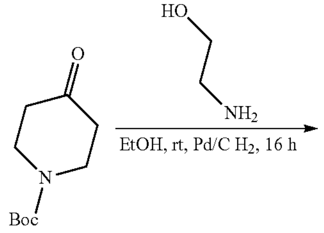

A

-continued

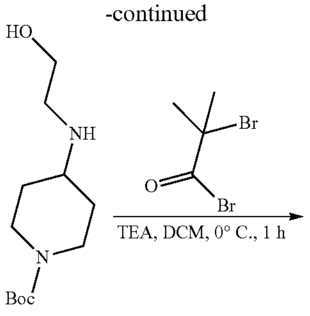

B

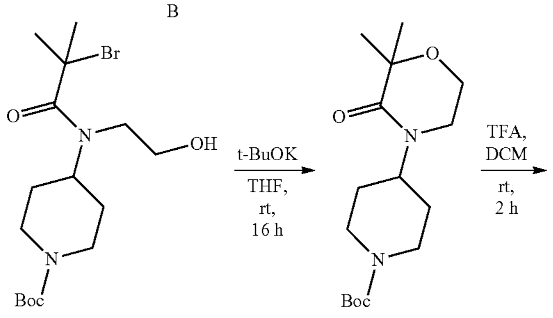

C

D

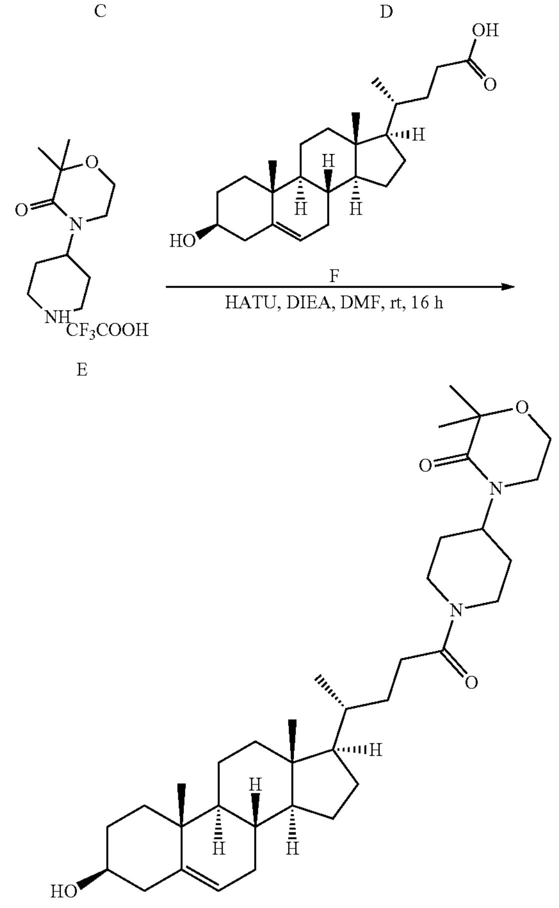

E

F

To a solution of compound A (3 g, 15.1 mmol) and 2-aminoethan-1-ol (1.84 g, 30.1 mmol) in ethanol (50 mL) was added 10% Pd/C (320 mg) and the reaction was stirred at room temperature for 16 h under 1 atm $H_2$. The reaction was filtered, and the filtrate concentrated under reduced pressure to afford compound B (3.6 g, 98%) as a white solid. To a 0° C. solution of compound B (1 g, 4.09 mmol) in DCM (10 mL) was added TEA (828 mg, 8.19 mmol) and 2-bromo-2-methylpropanoyl bromide (941 mg, 4.09 mmol) and the reaction was warmed to room temperature for 1 h. The reaction was diluted with water (30 mL) and extracted with EtOAc (10 mL*2). The combined organic layers were washed with water (20 mL), brine (20 mL), dried over sodium sulfate and concentrated under reduced pressure. The residue was purified by silica gel chromatography to afford compound C (200 mg, 12%) as a white solid. To a solution of compound C (100 mg, 254 μmol) in THE (3 mL) was added t-BuOK (57.1 mg, 508 μmol) and the reaction stirred at room temperature for 16 h. The reaction was concentrated under reduced pressure. The residue was purified by silica gel chromatography to afford compound D (30 mg, 37%) as a white solid. To a solution of compound D (30 mg, 96 μmol) in DCM (2 mL) was added TFA (1 mL) at room temperature and the reaction was stirred for 2 h. The reaction concentrated under reduced pressure to give compound E as the TFA salt (32 mg, 96 μmol).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (36 mg, 96 μmol) and 2,2-dimethyl-4-(piperidin-4-yl)morpholin-3-one 2,2,2-trifluoroacetate (32 mg, 96 μmol) were reacted according to the method of Example 536 to afford the title compound 524 (20 mg, 36%) as a white solid. LCMS: $[M+1]^+$=569.25. $^1H$ NMR (400 MHz, Chloroform-d) δ 5.35-5.34 (m, 1H), 4.79-4.74 (m, 1H), 4.67-4.61 (m, 1H), 3.98-3.80 (m, 3H), 3.56-3.47 (m, 1H), 3.29-3.01 (m, 3H), 2.61-2.54 (m, 1H), 2.42-2.17 (m, 4H), 2.02-1.65 (m, 8H), 1.56-1.27 (m, 19H), 1.18-0.89 (m, 13H), 0.68 (s, 3H).

Example 525: 4-(1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperidin-4-yl)morpholin-3-one

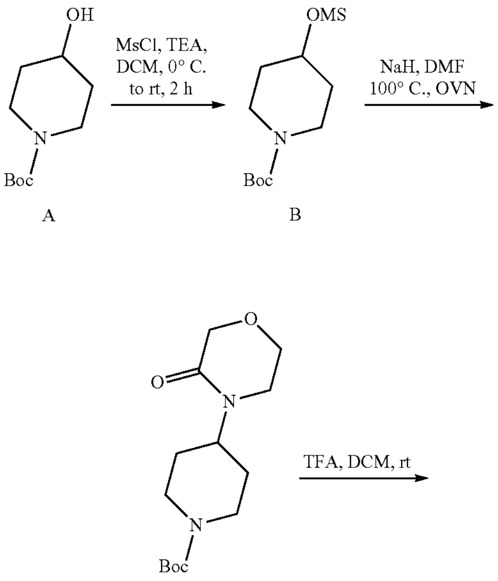

A B C

-continued

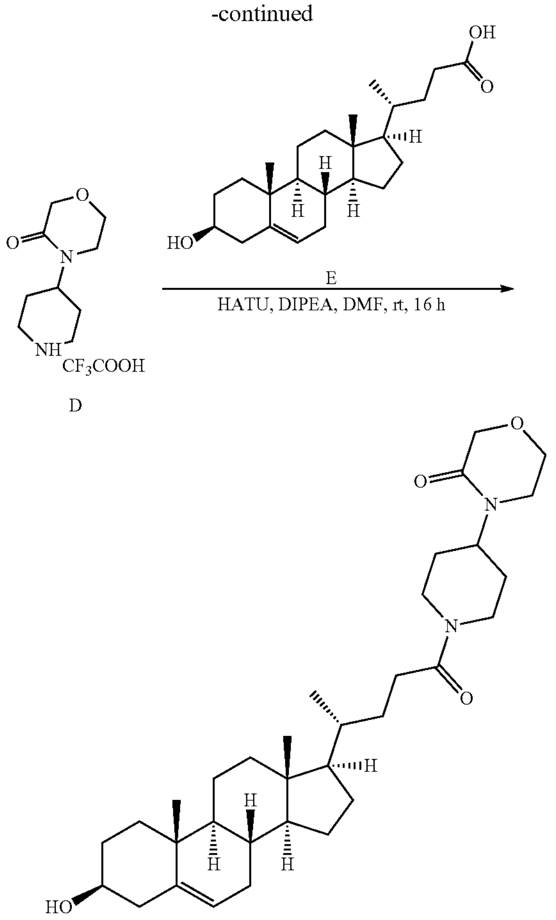

D E

To a 0° C. solution of compound A (400 mg, 1.99 mmol) and TEA (302 mg, 2.98 mmol) in DCM (5 mL) was added MsCl (273 mg, 2.38 mmol) under $N_2$ for 2 hours. The reaction was warmed to room temperature for 16 hours. The reaction was diluted with saturated aqueous $NaHCO_3$ (20 mL) and extracted with EtOAc (50 mL). The organic layer was washed with brine (20 mL), dried over sodium sulfate, concentrated under reduced pressure and purified by silica gel chromatography to afford compound B (660 mg, 98%) as brown liquid. To a solution of morpholin-3-one (181 mg, 1.79 mmol) and NaH (61.8 mg, 1.55 mmol, 60% dispersion in mineral oil) in DMF (5 mL) was added compound B (500 mg, 1.79 μmol) at 80° C. under $N_2$ for 16 hours. The reaction was diluted with 1N HCl (20 mL) and extracted with EtOAc (50 mL). The organic layer was washed with $NaHCO_3$ (20 mL), water (20 mL*3), brine (20 mL), dried over sodium sulfate and concentrated under reduced pressure. The crude product was purified by silica gel chromatography to afford compound C (460 mg, 90%). To a solution of compound C (211 mg, 743 μmol) in dichloromethane (3 mL) was added TFA (1 mL) at room temperature under $N_2$ for 2 hours. The reaction was concentrated under reduced pressure to afford compound D as the TFA salt (220 mg, 0.743 μmol).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (224 mg, 597 μmol) and 4-(piperidin-4-yl)morpholin-3-one 2,2,2-trifluoroacetate (220 mg, 0.743 μmol) were reacted according to the method of Example 536 to afford the title compound 525 (15 mg, 5.0%) as a white solid. LCMS:

[M+1]$^+$=541.40. $^1$H NMR (400 MHz, Chloroform-d) δ 5.35 (d, J=6.0 Hz, 1H), 4.85-4.64 (m, 2H), 4.19 (s, 2H), 4.03-3.81 (m, 3H), 3.55-3.47 (m, 1H), 3.24 (q, J=4.4 Hz, 2H), 3.14 (t, J=12.0 Hz, 1H), 2.69-2.50 (m, 1H), 2.43-2.16 (m, 4H), 2.02-1.93 (m, 2H), 1.89-1.73 (m, 5H), 1.56-1.43 (m, 7H), 1.37-1.23 (m, 5H), 1.18-1.03 (m, 4H), 1.00 (s, 3H), 0.96-0.83 (m, 4H), 0.68 (s, 3H).

Example 526: N-[(3S)-1-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]pyrrolidin-3-yl]-1-methyl-1H-pyrazole-4-carboxamide

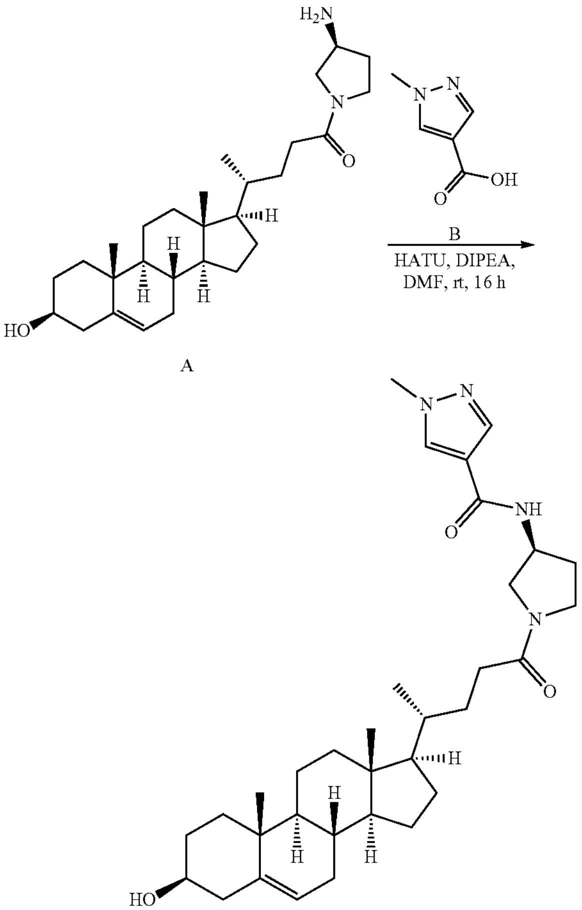

To a solution of compound A (0.2 g, 452 μmol) in DMF (3 mL) was added compound B (57 mg, 452 μmol), HATU (131 mg, 678 μmol), DIPEA (234 mg, 1.81 mmol) and the reaction was stirred at room temperature for 16 hours. Water (20 mL) was added and the reaction was extracted with EtOAc (30 mL*2). The combined organic layers were washed with water (20 mL*2), brine (20 mL), dried over sodium sulfate and concentrated under reduced pressure. The residue was purified by silica gel chromatography to afford the title compound 526 (25 mg, 10%) as a white solid. LCMS: [M+H]+=551.25 $^1$H NMR (400 MHz, Chloroform-d) δ 7.95-7.90 (m, 2H), 6.77 (s, 1H), 5.34 (d, J=4.8 Hz, 1H), 4.67 (s, 1H), 3.92 (s, 3H), 3.83-3.42 (m, 5H), 2.30-2.10 (m, 8H), 1.99-1.94 (m, 2H), 1.83 (d, J=12.2 Hz, 4H), 1.59-1.41 (m, 7H), 1.27 (d, J=12.2 Hz, 2H), 1.19-1.04 (m, 4H), 1.00 (s, 3H), 0.93 (d, J=6.0 Hz, 4H), 0.67 (s, 3H).

Example 527: N—((S)-1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)pyrrolidin-3-yl)-3-methyl-1,2,4-oxadiazole-5-carboxamide

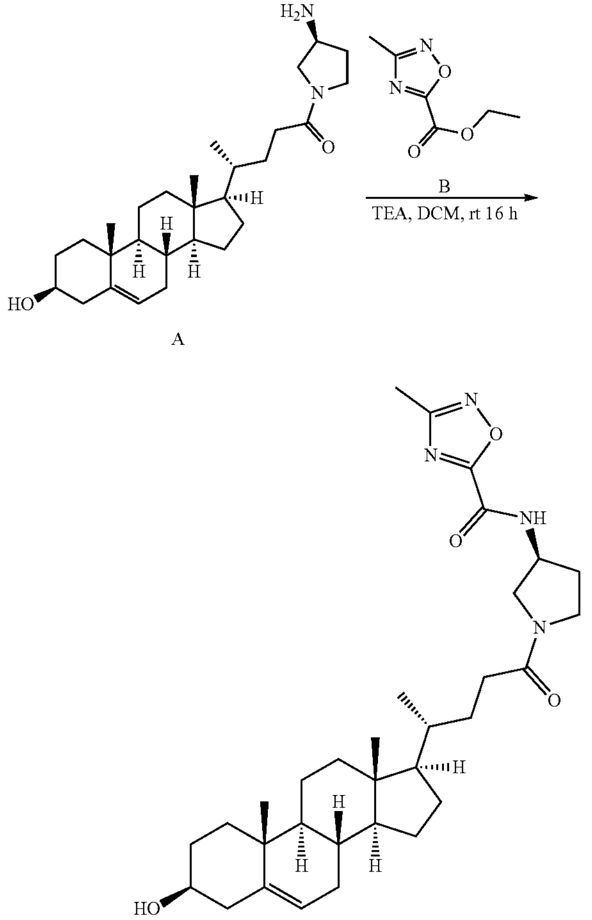

To a 0° C. solution of compound A (200 mg, 452 μmol) and TEA (457 mg, 4.52 mmol) in DCM (3 mL) was added compound B (77.6 mg, 497 μmol) and the reaction was warmed to room temperature for 2 hours. Upon completion, the reaction was quenched with saturated ammonium chloride (10 mL) and extracted with ethyl acetate (10 mL*3). The organic layer was washed with brine (5 mL), dried over sodium sulfate, filtered, and concentrated under reduced pressure. The crude product was purified by silica gel chromatography to afford the title compound 527 (15 mg, 6.0%) as a white solid. LCMS: [M+1]$^+$=553.30. $^1$H NMR (400 MHz, Chloroform-d) δ 7.24-7.16 (m, 1H), 5.34 (d, J=5.2 Hz, 1H), 4.72-4.57 (m, 1H), 3.73-3.89 (m, 1H), 3.71-3.42 (m, 4H), 2.47 (d, J=2.0 Hz, 3H), 2.38-2.25 (m, 3H), 2.23-2.11 (m, 2H), 1.99 (d, J=8.2 Hz, 3H), 1.86-1.80 (m, 3H), 1.69 (s, 4H), 1.52-1.42 (m, 5H), 1.41-1.24 (m, 3H), 1.17-1.13 (m, 1H), 1.11-1.06 (m, 2H), 1.00 (s, 3H), 0.94 (dd, J=8.8, 6.4 Hz, 4H), 0.68 (d, J=6.8 Hz, 3H).

Example 528: N—((S)-1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)pyrrolidin-3-yl)pyrimidine-4-carboxamide

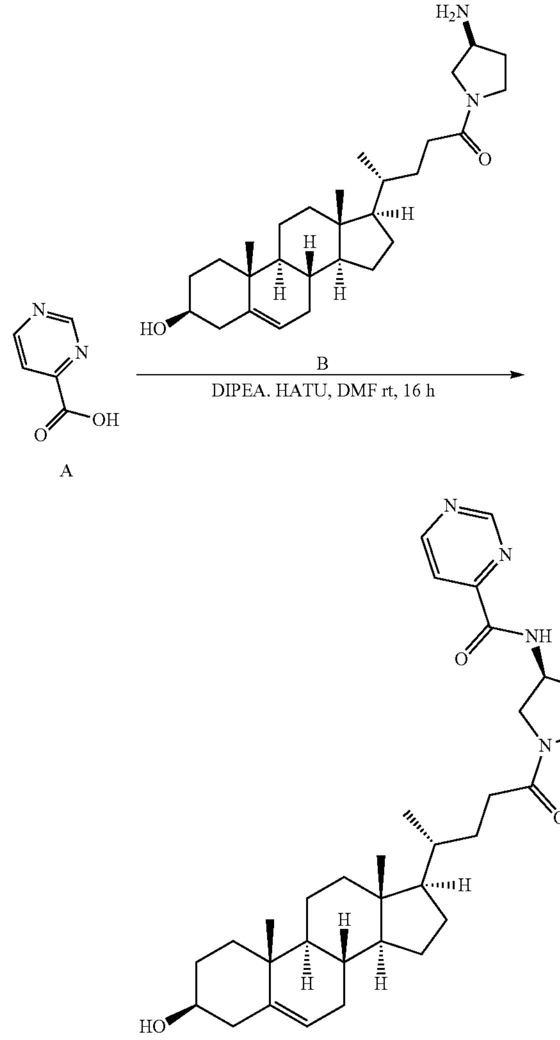

A

To a solution of compound A (67.3 mg, 542 μmol) in DMF (5 mL) was added compound B (216 mg, 452 μmol), HATU (344 mg, 904 μmol), DIPEA (350 mg, 2.71 mmol) and the reaction was stirred at room temperature for 16 h. The reaction was quenched with saturated aqueous $NaHCO_3$ (20 mL) and extracted with EtOAc (60 mL). The organic layer was washed with brine $NaHCO_3$ (50 mL), dried over sodium sulfate, filtered, and concentrated under reduced pressure. The residue was purified by silica gel chromatography to afford the title compound 528 (21.3 mg, Yield: 9%) as a white solid. LCMS: [M+1]=549.20. $^1H$ NMR (400 MHz, $CDCl_3$): 9.28 (dd, J=3.6, 1.6 Hz, 1H), 9.03 (t, J=5.2 Hz, 1H), 8.18-8.02 (m, 2H), 5.39 (dd, J=5.2, 2.4 Hz, 1H), 4.72 (dq, J=18.8, 6.0 Hz, 1H), 3.98-3.40 (m, 5H), 2.50-2.13 (m, 6H), 2.04-2.01 (m, 3H), 1.94-1.77 (m, 7H), 1.67-1.56 (m, 2H), 1.51-1.27 (m, 6H), 1.24-0.93 (m, 12H), 0.72 (d, J=11.2 Hz, 3H).

Example 529: N—((S)-1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)pyrrolidin-3-yl)pyrazine-2-carboxamide

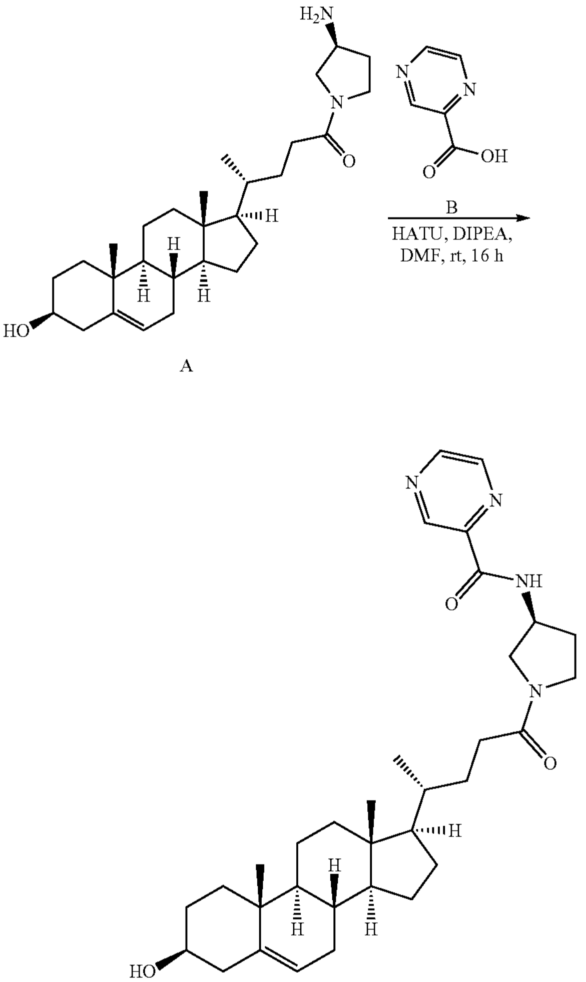

A

To a solution of compound A (200 mg, 452 μmol) and compound B (56.1 mg, 452 μmol) in DMF (3 mL) was added HATU (258 mg, 678 μmol), DIPEA (175 mg, 1.36 mmol) and the reaction was stirred at room temperature for 3 hours. Upon completion, the reaction was quenched with saturated ammonium chloride (10 mL) and extracted with ethyl acetate (10 mL*3). The combined organic layers were washed with brine (10 mL), dried over sodium sulfate, filtered, and concentrated under reduced pressure. The crude product was purified by silica gel chromatography to afford the title compound 529 (22 mg, 9%) as a white solid. LCMS: $[M+1]^+$=549.20. $^1H$ NMR (400 MHz, Chloroform-d) δ 9.40 (s, 1H), 8.77 (dd, J=5.6, 2.4 Hz, 1H), 8.52 (d, J=3.6 Hz, 1H), 7.86-7.83 (m, 1H), 5.39-5.32 (m, 1H), 4.70 (dq, J=18.0, 6.0 Hz, 1H), 3.91-3.78 (m, 1H), 3.73-3.44 (m, 4H), 2.46-2.10 (m, 6H), 1.99 (t, J=11.4 Hz, 3H), 1.89-1.68 (m, 4H), 1.47 (d, J=14.3 Hz, 6H), 1.41-1.23 (m, 4H), 1.11-1.08 (m, 4H), 1.00 (d, J=3.2 Hz, 3H), 0.94 (dd, J=13.2, 6.4 Hz, 4H), 0.68 (d, J=12.0 Hz, 3H).

Example 530: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3S)-3-[(pyridin-4-yl)amino]pyrrolidin-1-yl]pentan-1-one

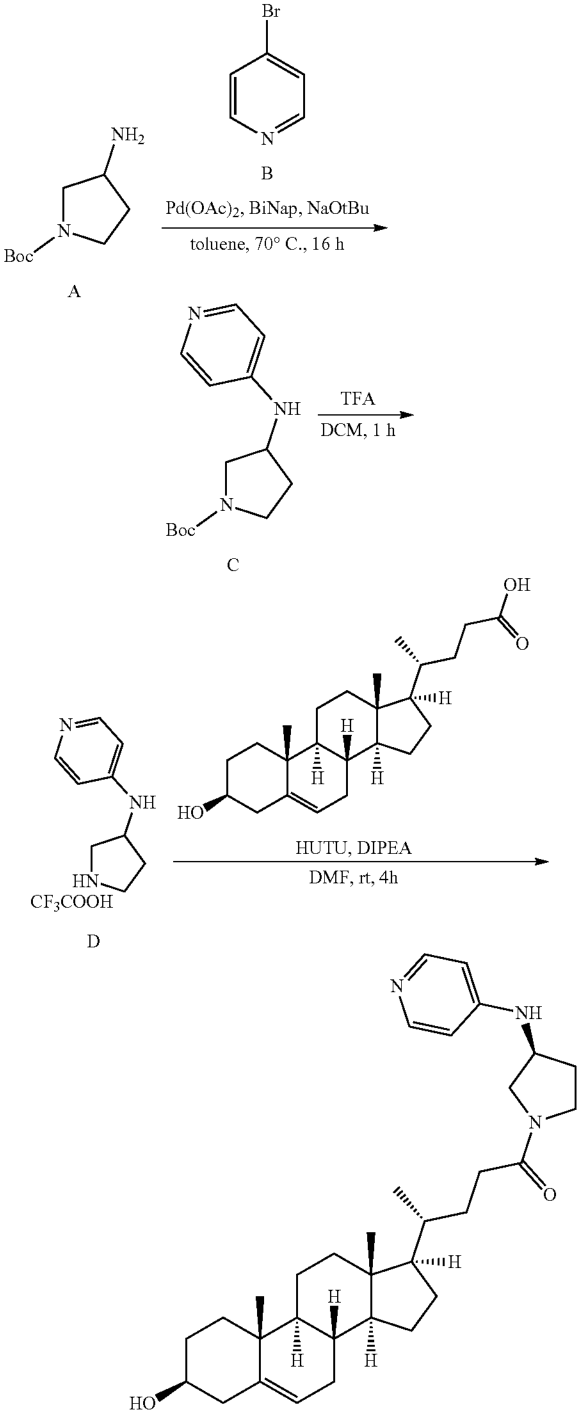

To a solution of compound A (100 mg, 537 μmol) in toluene (4 mL), was added compound B (926.5 mg, 586 μmol), BINAP (15.2 mg, 24.4 μmol), NaOtBu (141 mg, 1.46 mmol), $Pd(OAc)_2$ (5.48 mg, 24.4 μmol) and the reaction was heated to 70° C. under $N_2$ for 16 h. The reaction was cooled to room temperature and concentrated under reduced pressure, the residue was purified by silica gel chromatography to afford compound C (120 mg, 454 μmol, 92%) as a yellow solid. To a solution of compound C (120 mg, 454 μmol,) in DCM (4 mL) was added TFA (2 mL) at room temperature and the reaction was stirred for 2 h. The reaction concentrated under reduced pressure to afford compound D as the TFA salt (125 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (184 mg, 490 μmol) and N-(pyrrolidin-3-yl)pyridin-4-amine 2,2,2-trifluoroacetate (100 mg, 361 μmol) were reacted according to the method of Example 430 to afford the title compound 530 (11.4 mg, 3.58%) as a white solid. LCMS: $[M+1]^+$=520.20. $^1$H NMR (400 MHz, Chloroform-d) δ 8.19-8.15 (m, 2H), 6.53 (t, J=5.4 Hz, 2H), 5.48 (s, 1H), 5.35 (s, 1H), 4.14-4.10 (m, 1H), 3.78 (dt, J=11.6, 6.8 Hz, 1H), 3.68-3.47 (m, 4H), 2.17-2.10 (m, 3H), 2.06-1.93 (m, 3H), 1.84 (d, J=11.2 Hz, 4H), 1.46-1.40 (m, 7H), 1.40-1.30 (m, 2H), 1.20-1.02 (m, 5H), 1.00 (d, J=2.4 Hz, 3H), 0.93 (dd, J=13.2, 6.4 Hz, 4H), 0.67 (d, J=9.2 Hz, 3H).

Example 531: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-(pyrimidin-4-ylamino)pyrrolidin-1-yl)pentan-1-one

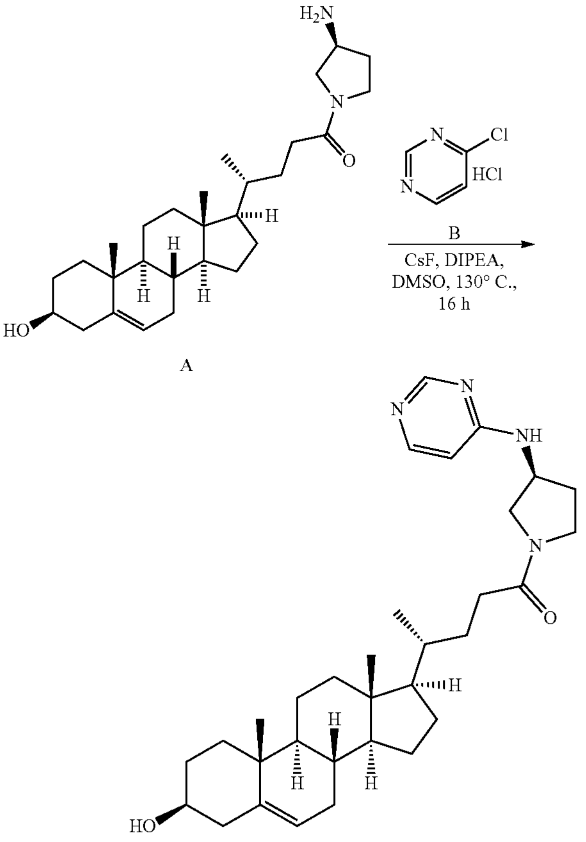

To a solution of compound B (150 mg, 993 μmol) and compound A (440 mg, 993 μmol) in DMSO (5 mL) was added CsF (151 mg, 993 umol), DIPEA (385 mg, 2.98 mmol) and the reaction was stirred at 90° C. for 16 hours. The reaction was diluted with water (20 mL) and extracted with ethyl acetate (10 mL*2). The combined organic layers were washed with water (20 mL), brine (20 mL), dried over sodium sulfate and concentrated under reduced pressure. The residue was purified by silica gel chromatography to afford the title compound 531 (60 mg, 11.6%) as a white solid. LCMS: $[M+1]^+$=521.25. $^1H$ NMR (400 MHz, Chloroform-d) δ 8.58 (d, J=11.2 Hz, 1H), 8.19 (d, J=6.0 Hz, 1H), 6.40 (t, J=5.2 Hz, 1H), 5.67-5.60 (m, 1H), 5.38-5.29 (m, 1H), 4.48-4.45 (m, 1H), 3.80-3.74 (m, 1H), 3.69-3.34 (m, 4H), 2.37-1.72 (m, 13H), 1.62-0.86 (m, 23H), 0.67 (d, J=10.3 Hz, 3H).

Example 532: (R)-1-(4-cyclohexyl-4-hydroxypiperidin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

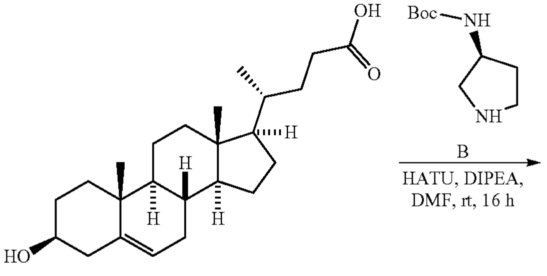

A

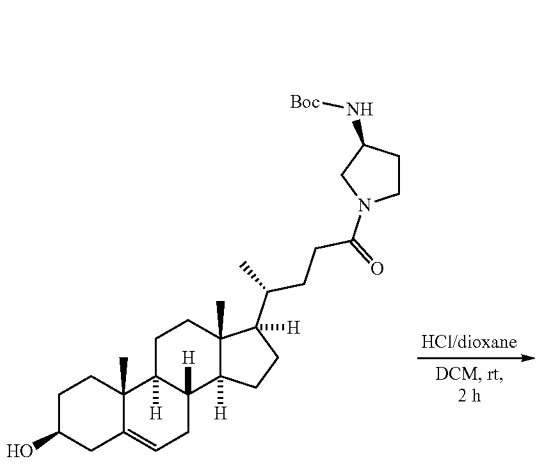

C

-continued

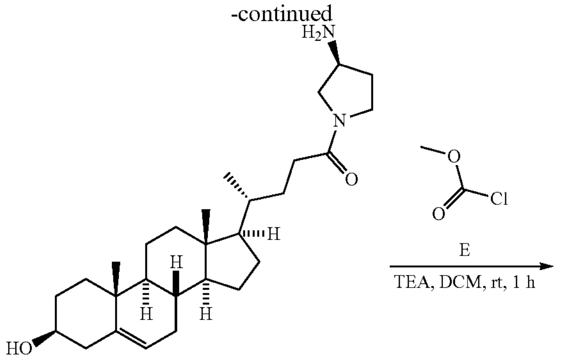

D

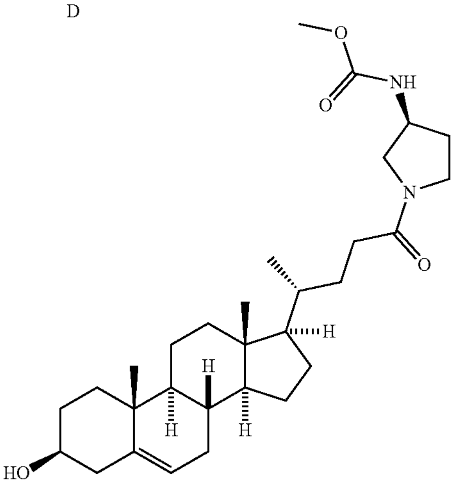

To a solution of compound A (2 g, 5.34 mmol) in DMF (50 mL, 646 mmol) was added compound B (1.49 g, 1.5 eq., 8.01 mmol), DIPEA (3.45 g, 26.7 mmol), HATU (2.51 g, 10.7 mmol) and the reaction was stirred at room temperature for 16 h. The reaction was quenched with water (100 mL) and extracted with ethyl acetate (4*50 mL). The combined organic layers were concentrated under reduced pressure. The crude product was purified by silica gel chromatography to afford compound C (2.8 g, 97%). To a solution of compound C (2.8 g, 5.34 mmol) in DCM was added 4N HCl in 1,4-dioxane (20 mL, 80 mmol) and the reaction was stirred at room temperature for 2 h. Upon completion, the reaction concentrated to afford compound D as the HCl salt (2.4 g).

To a 0° C. solution of compound D (0.1 g, 217 μmol) in DCM (4 mL, 62.5 mmol) was added TEA (114 mg, 1.13 mmol), compound E (17.1 mg, 181 μmol) and the reaction was warmed to room temperature for 1 h. Upon completion, the reaction was diluted with water (10 mL) and extracted with ethyl acetate (20 mL). The organic layer was concentrated under reduced pressure. The crude product was purified by silica gel chromatography to afford the title compound 532 (50 mg, 44%). LCMS: $[M+1]^+$=501.30 $^1H$ NMR (400 MHz, Chloroform-d) δ 5.35 (d, J=5.2 Hz, 1H), 4.76-4.70 (m, 1H), 4.28 (s, 1H), 3.74 (dd, J=11.0, 6.4 Hz, 1H), 3.68 (s, 3H), 3.54 (td, J=11.8, 6.8 Hz, 3H), 3.41-3.28 (m, 1H), 2.33-2.11 (m, 5H), 2.03-1.93 (m, 3H), 1.86 (s, 1H), 1.82 (t, J=3.2 Hz, 3H), 1.61 (d, J=10.4 Hz, 3H), 1.56 (d, J=6.4 Hz, 2H), 1.50 (d, J=3.8 Hz, 2H), 1.48-1.44 (m, 2H), 1.33 (t, J=9.8 Hz, 2H), 1.25 (s, 1H), 1.20-1.05 (m, 4H), 1.01 (s, 3H), 0.94 (dd, J=6.4, 4.0 Hz, 3H), 0.68 (d, J=1.4 Hz, 3H).

Example 533: 1—((S)-1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)pyrrolidin-3-yl)-3-methylurea

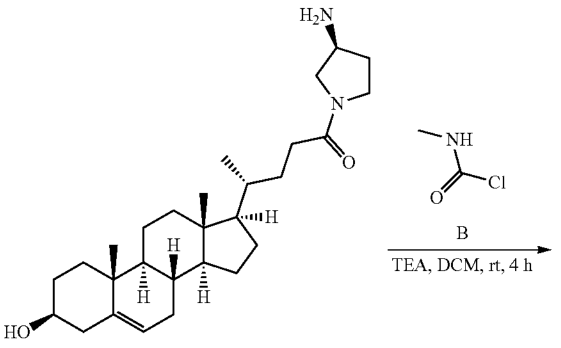

A

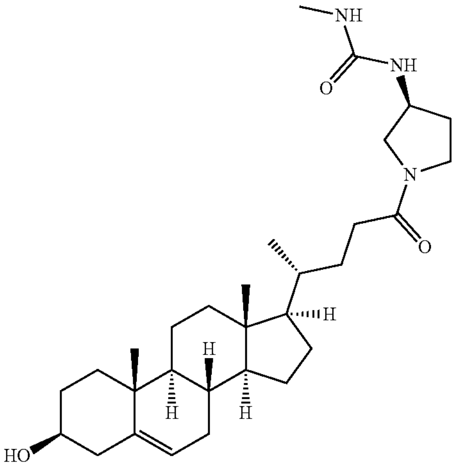

To a 0° C. solution of compound A (200 mg, 452 μmol) and TEA (183 mg, 1.81 mmol) in DCM (5 mL) was added compound B (42.2 mg, 452 μmol) and the reaction was warmed to room temperature for 2 hours. Upon completion, the reaction was quenched with saturated ammonium chloride (10 mL) and extracted with ethyl acetate (10 mL*3). The organic layer was washed with brine (10 mL), dried over sodium sulfate, filtered, and concentrated under reduced pressure. The crude product was purified by silica gel chromatography to afford the title compound 533 (30 mg, 13.29%) as a white solid. LCMS: $[M+1]^+$=500.25 $^1$H NMR (400 MHz, DMSO-$d_6$) δ 6.14-6.11 (m, 1H), 5.63 (dt, J=14.4, 4.8 Hz, 1H), 5.26 (d, J=4.8 Hz, 1H), 4.58 (d, J=4.4 Hz, 1H), 4.06-4.00 (m, 1H), 3.59 (dd, J=10.4, 6.0 Hz, 1H), 3.43 (tt, J=12.0, 5.4 Hz, 2H), 3.25 (td, J=10.8, 5.6 Hz, 2H), 3.03-3.17 (m, 1H), 2.53 (dd, J=4.8, 2.4 Hz, 3H), 2.22-2.16 (m, 1H), 2.14-2.03 (m, 3H), 1.93 (t, J=16.4 Hz, 3H), 1.82-1.60 (m, 5H), 1.56-1.45 (m, 3H), 1.37 (dd, J=16.4, 11.2 Hz, 4H), 1.32-1.21 (m, 2H), 1.02-1.21 (m, 4H), 1.02-0.96 (m, 2H), 0.94 (s, 3H), 0.89 (dd, J=6.6, 3.7 Hz, 3H), 0.65 (d, J=1.6 Hz, 3H).

Example 534: 3—((S)-1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)pyrrolidin-3-yl)-1,1-dimethylurea

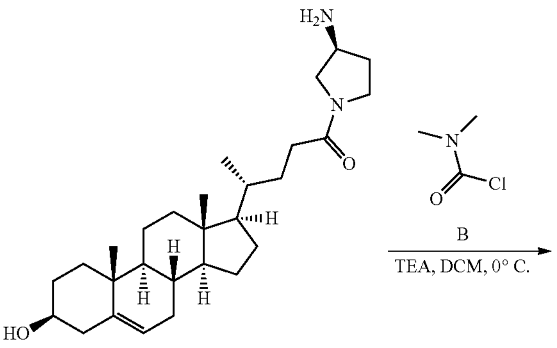

A

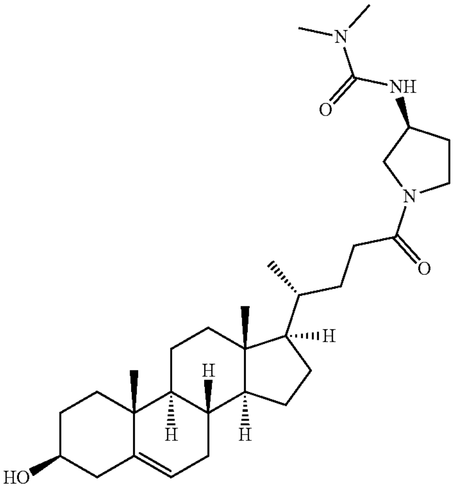

To a 0° C. solution of compound A (200 mg, 452 μmol) in dichloromethane (5 mL) was added TEA (183 mg, 1.81 mmol), compound A (43.7 mg, 407 μmol) slowly and the reaction was stirred for 1 hour. Upon completion, the reaction was quenched with water (10 mL) and extracted with DCM (10 mL*3). The combined organic layers were washed with brine (10 mL), dried over sodium sulfate, filtered, and concentrated under reduced pressure. The crude product was purified by silica gel chromatography to afford the title compound 534 (128 mg, 55%) as a white solid. LCMS: $[M+1]^+$=514.35. $^1$H NMR (400 MHz, Chloroform-d) δ 5.34 (d, J=5.2 Hz, 1H), 4.38 (dt, J=14.8, 4.8 Hz, 2H), 3.75-3.70 (m, 1H), 3.62-3.43 (m, 3H), 3.34 (d, J=10.4 Hz, 1H), 2.89 (d, J=5.6 Hz, 6H), 2.34-2.07 (m, 5H), 1.99 (m, 2H), 1.89-1.73 (m, 5H), 1.67 (s, 3H), 1.54-1.39 (m, 6H), 1.36-1.25 (m, 2H), 1.12-1.09 (m, 4H), 1.00 (s, 3H), 0.93 (dd, J=8.0, 6.4 Hz, 4H), 0.68 (d, J=3.6 Hz, 3H).

Example 535: N—((S)-1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)pyrrolidin-3-yl)methanesulfonamide

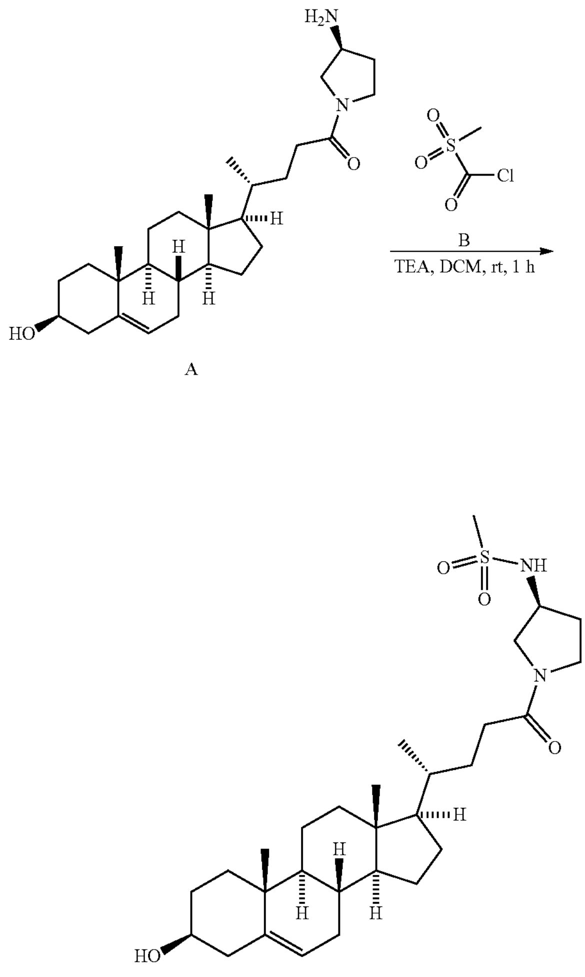

To a 0° C. solution of compound A (0.2 g, 452 μmol) in DCM (4 mL) was added TEA (229 mg, 2.26 mmol), compound B (25.9 mg, 226 μmol) and the reaction was warmed to room temperature for 4 h. Upon completion, the reaction was diluted with water (10 mL) and extracted with ethyl acetate (20 mL). The organic layer was concentrated under reduced pressure. The crude product was purified by silica gel chromatography to afford the title compound 535 (30 mg, 13%). LCMS: $[M+1]^+$=521.25 $^1$H NMR (400 MHz, Chloroform-d) δ 5.34 (d, J=4.8 Hz, 1H), 5.12 (t, J=6.8 Hz, 1H), 4.12-4.01 (m, 1H), 3.80-3.69 (m, 1H), 3.65-3.59 (m, 1H), 3.55-3.47 (m, 2H), 3.45-3.38 (m, 1H), 3.00 (d, J=7.0 Hz, 3H), 2.34-2.25 (m, 3H), 2.23-2.18 (m, 1H), 2.16-2.10 (m, 1H), 2.02-1.99 (m, 1H), 1.97 (s, 1H), 1.87-1.80 (m, 3H), 1.70 (s, 4H), 1.52-1.47 (m, 4H), 1.48-1.41 (m, 3H), 1.36-1.24 (m, 4H), 1.20-1.09 (m, 3H), 1.07 (s, 1H), 1.00 (s, 3H), 0.94 (d, J=6.4 Hz, 3H), 0.68 (s, 3H).

Example 536: (S)-1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N-methylpyrrolidine-3-carboxamide

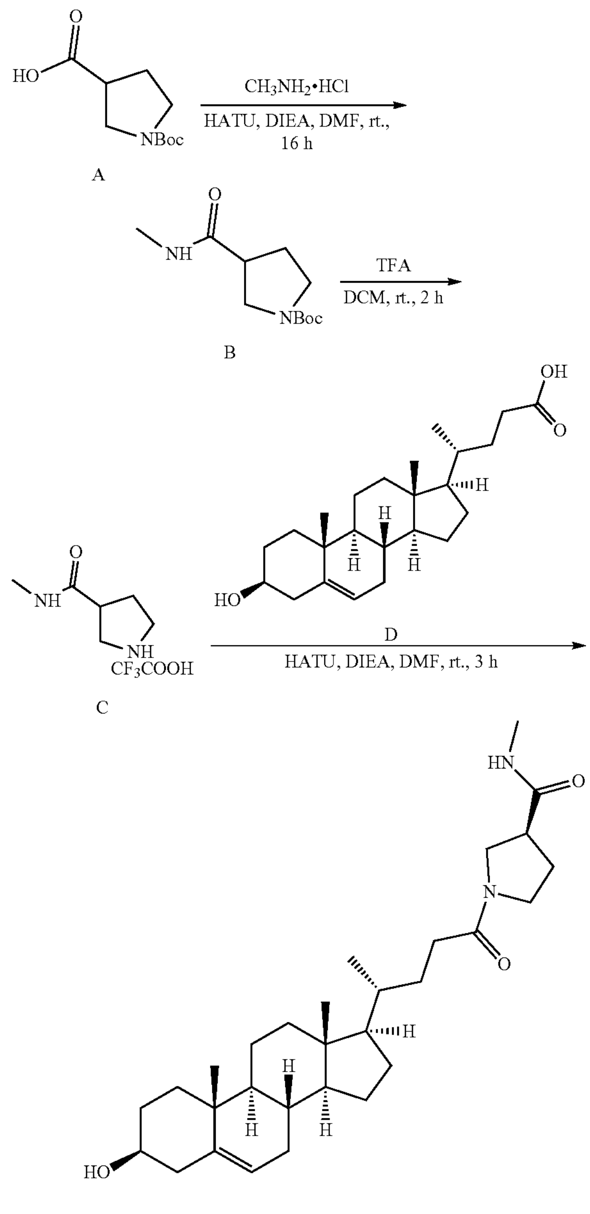

To a solution of compound A (200 mg, 929 μmol) in DMF (3 mL) was added $CH_3NH_2$ HCl (62.7 mg, 929 μmol), DIPEA (600 mg, 4.65 mmol) and HATU (530 mg, 1.39 mmol). The reaction was stirred at room temperature for 16 h. The reaction was quenched with water (5 mL) and extracted with EtOAc (15 mL). The organic layer was washed with brine, dried over sodium sulfate and concentrated to afford 250 mg crude. The crude was purified by silica gel chromatography to afford compound B (140 mg, 66%) as a yellow oil. To a solution of compound B (140 mg, 613 μmol) in DCM (1.5 mL) was added TFA (0.3 mL). The reaction was stirred at room temperature for 2 h. The reaction concentrated under reduced pressure to give compound C as the TFA salt (135 mg, 534 μmol).

To a solution of (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (100 mg, 267 μmol) in DMF (2 mL) was added N-methylpyrrolidine-3-carboxamide 2,2,2-trifluoroacetate (135 mg, 534 μmol), DIPEA (173 mg, 1.33 mmol) and HATU (152 mg, 0.4 mmol). The reaction was stirred at room temperature for 3 h. The reaction was quenched with water (5 mL) and extracted with EtOAc (10 mL). The organic layer was washed with brine, dried over sodium sulfate, and concentrated. The crude was purified by silica gel chromatography to afford the title compound 536 (69.5 mg, 53.7%) as a white solid. LCMS: $[M+1]^+$=485.25. $^1H$ NMR (400 MHz, Chloroform-d) δ 5.63 (s, 1H), 5.35 (d, J=5.0 Hz, 1H), 3.76 (q, J=9.4 Hz, 1H), 3.70-3.61 (m, 2H), 3.57-3.37 (m, 3H), 2.95-2.88 (m, 1H), 2.82 (td, J=11.4, 10.6 Hz, 4H), 2.36-2.05 (m, 7H), 1.92-1.83 (m, 7H), 1.61 (s, 4H), 1.58-1.40 (m, 8H), 1.32 (d, J=9.4 Hz, 4H), 1.20-1.02 (m, 5H), 1.00 (s, 3H), 0.93 (dd, J=6.4, 2.0 Hz, 4H), 0.68 (s, 3H).

Example 537: (S)-1-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N,N-dimethylpyrrolidine-3-carboxamide

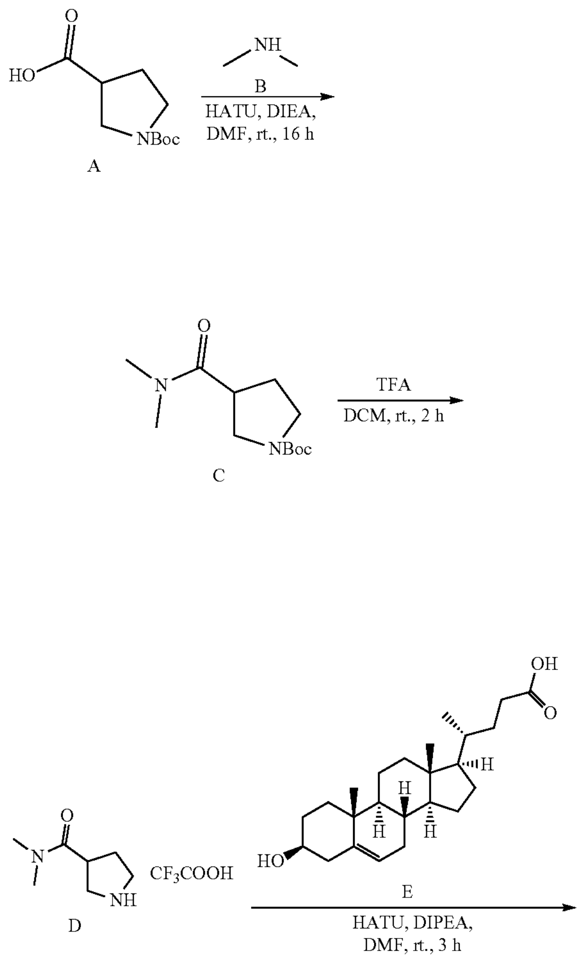

-continued

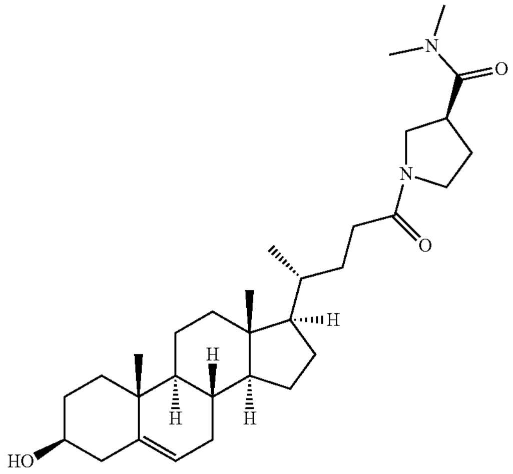

To a solution of compound A (200 mg, 929 μmol) in DMF (3 mL) was added compound B (41.9 mg, 929 μmol), DIPEA (600 mg, 4.65 mmol) and HATU (530 mg, 1.39 mmol). The reaction was stirred at room temperature for 16 h. The reaction was quenched with water (10 mL) and extracted with EtOAc (20 mL). The organic layer was washed with brine (10 mL), dried over sodium sulfate, and concentrated under reduced pressure. The crude product was purified by silica gel chromatography to afford compound C (200 mg, 88.9% yield) as a yellow oil. To a solution of compound C (200 mg, 825 μmol) in DCM (2 mL) was added TFA (0.5 mL). The reaction was stirred at room temperature for 2 h. The reaction concentrated under reduced pressure to give compound D as the TFA salt (195 mg, 762 μmol).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (100 mg, 404 μmol) and N,N-dimethylpyrrolidine-3-carboxamide (195 mg, 762 μmol) was reacted according to the method of Example 430 to afford the title compound 537 (117 mg, 87.9%) as a white solid. LCMS: $[M+1]^+$=499.20. $^1H$ NMR (400 MHz, Chloroform-d) δ 5.35 (d, J=4.4 Hz, 1H), 3.85-3.17 (m, 6H), 3.08 (d, J=16.6 Hz, 3H), 2.97 (d, J=10.4 Hz, 3H), 2.43-2.03 (m, 6H), 2.02-1.87 (m, 3H), 1.86-1.75 (m, 3H), 1.63 (d, J=2.6 Hz, 3H), 1.59-1.39 (m, 8H), 1.29-1.20 (m, 3H), 1.10-1.06 (m, 4H), 1.00 (s, 3H), 0.94 (d, J=6.6 Hz, 3H), 0.88 (d, J=6.2 Hz, 1H), 0.68 (s, 3H).

Example 538: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(1-methyl-1H-imidazole-4-carbonyl)piperazin-1-yl]pentan-1-one

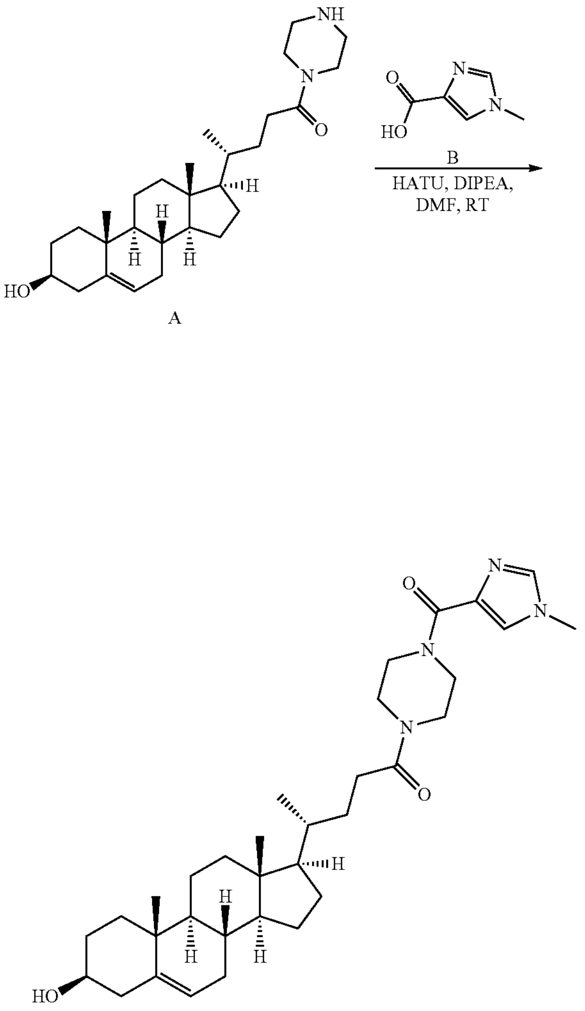

To a solution of compound A (100 mg, 226 μmol) in DMF (3 mL) was added compound B (28.5 mg, 226 μmol), DIPEA (175 mg, 1.36 mmol) and HATU (106 mg, 2 eq., 452 μmol). Upon completion, the reaction was diluted with saturated aqueous $NH_4Cl$ (30 mL) and extracted with EtOAc (10 mL*2). The combined organic layers were washed with saturated $NaHCO_3$ (20 mL), water (20 mL), brine (20 mL), dried over sodium sulfate and concentrated under reduced pressure. The residue was purified by silica gel chromatography to afford the title compound 538 (50 mg, 40%) as a white solid. LCMS: $[M+1]^+$=551.25 $^1H$ NMR (400 MHz, Chloroform-d) δ 7.55 (s, 1H), 7.38 (s, 1H), 5.35 (s, 1H), 4.26 (s, 2H), 3.81-3.62 (m, 7H), 3.54 (s, 3H), 2.48-2.35 (m, 1H), 2.33-2.16 (m, 3H), 2.05-1.91 (m, 2H), 1.91-1.74 (m, 4H), 1.62-1.41 (m, 8H), 1.40-1.27 (m, 3H), 1.21-1.02 (m, 5H), 1.00 (s, 3H), 0.98-0.86 (m, 5H), 0.68 (s, 3H).

Example 539: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(1-methyl-1H-pyrazole-3-carbonyl)piperazin-1-yl]pentan-1-one

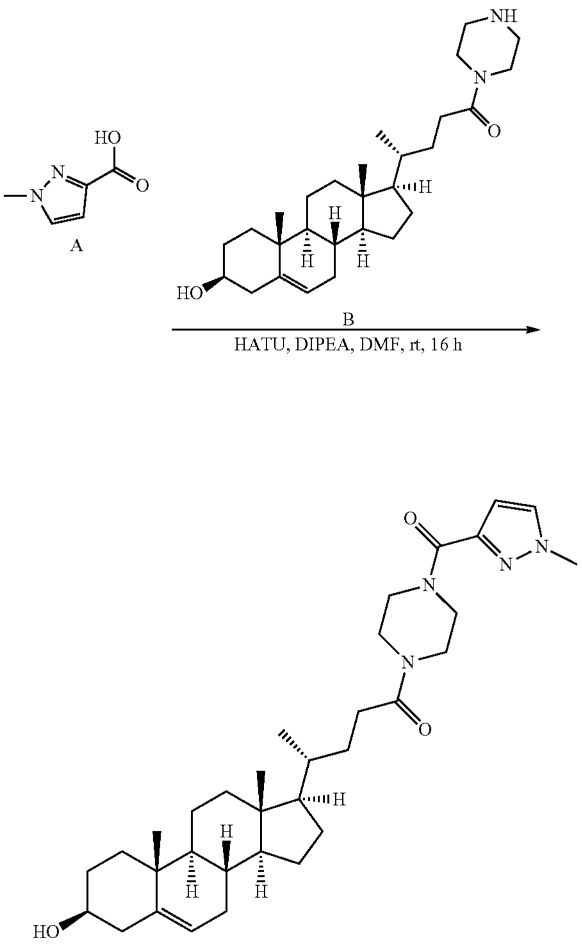

To a solution of compound A (100 mg, 793 μmol) in DMF (2 mL) was added compound B (351 mg, 793 μmol), HATU (452 mg, 1.19 mmol), DIPEA (410 mg, 3.17 mmol) and the reaction was stirred at room temperature for 16 hours. Water (20 mL) was added and extracted with EtOAc (20 mL*2). The combined organic layers were washed with water (20 mL), brine (20 mL), dried over sodium sulfate and concentrated under reduced pressure. The organic layer was concentrated, and the residue was purified by silica gel chromatography to afford the title compound 539 (100 mg, 25%) as a white solid. LCMS: [M+H]+=551.35 $^1H$ NMR (400 MHz, Chloroform-d) δ 7.40 (d, J=2.0 Hz, 1H), 6.74 (s, 1H), 5.38 (d, J=5.2 Hz, 1H), 4.17 (s, 1H), 4.08(s 1H), 3.97 (s, 3H), 3.82-3.71 (m, 4H), 3.59-3.53 (m, 3H), 2.48-2.41 (m, 1H), 2.37-2.21 (m, 3H), 2.02-1.99 (m, 2H), 1.94-1.81 (m, 4H), 1.57-1.46 (m, 8H), 1.41-1.29 (m, 3H), 1.17-1.07 (m, 3H), 1.04 (s, 3H), 1.00 (d, J=6.4 Hz, 3H), 0.72 (s, 3H).

Example 540: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(5-methyl-1,3,4-oxadiazole-2-carbonyl)piperazin-1-yl)pentan-1-one

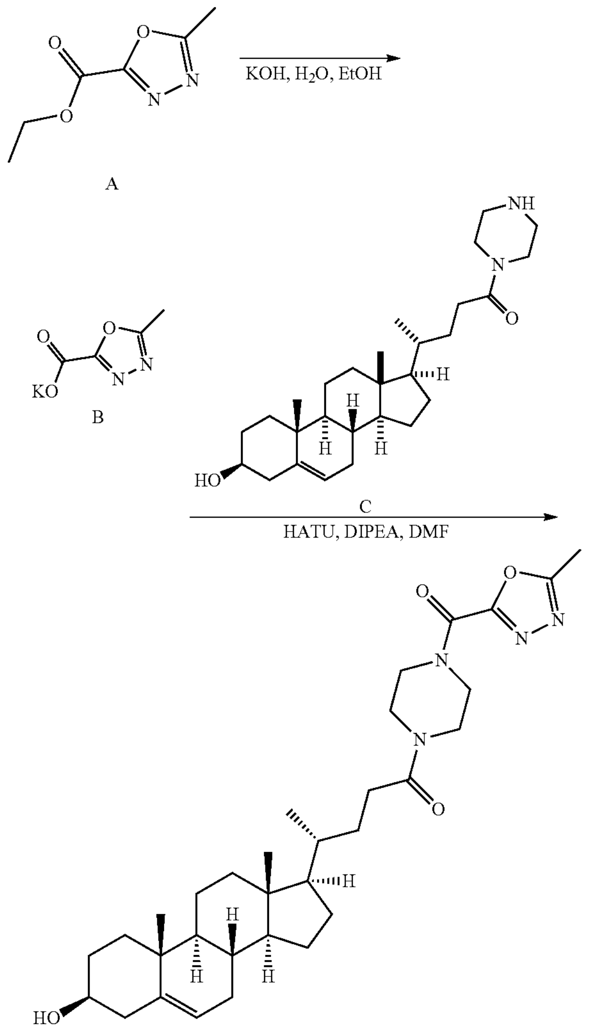

To a 0° C. solution of compound A (200 mg, 1.28 mmol) in ethanol (4 mL) was added KOH (160 mg, 2.85 mmol) and the reaction was warmed to room temperature for 40 min. The reaction was filtered, and the filter cake was washed with 4 mL of ethanol and washed with 4 mL of diethyl ether. The solid was dried under reduced pressure to afford compound B (180 mg, 84%) as a white solid. To a solution of compound B (150 mg, 339 µmol) and compound C (84.5 mg, 508 µmol) in DMF (5 mL) was added HATU (159 mg, 678 µmol) and DIPEA (219 mg, 1.69 mmol). The reaction was stirred at room temperature for 3 hours. Upon completion, the reaction was quenched with saturated ammonium chloride (50 mL) and extracted with ethyl acetate (50 mL*3). The combined organic layers were washed with brine (10 mL), dried over sodium sulfate, filtered, and concentrated under reduced pressure. The crude product was purified by column chromatography on silica gel to afford the title compound 540 (80 mg, 43%) as a white solid. LCMS: $[M+1]^+$=553.30. $^1$H NMR (400 MHz, Chloroform-d) δ 5.35 (d, J=5.0 Hz, 1H), 4.22-4.10 (m, 2H), 3.87-3.69 (m, 4H), 3.56-3.53 (m, 3H), 2.63 (s, 3H), 2.40 (d, J=10.6 Hz, 1H), 2.28 (td, J=16.8, 14.8, 8.0 Hz, 3H), 1.99 (dt, J=16.8, 8.8 Hz, 2H), 1.90-1.75 (m, 4H), 1.48-1.42 (m, 7H), 1.39-1.24 (m, 3H), 1.13-1.07 (m, 4H), 1.00 (s, 4H), 0.96 (d, J=6.4 Hz, 3H), 0.69 (s, 3H).

Example 541: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-N-ethyl-N-[2-(pyridin-2-yl) ethyl]pentanamide

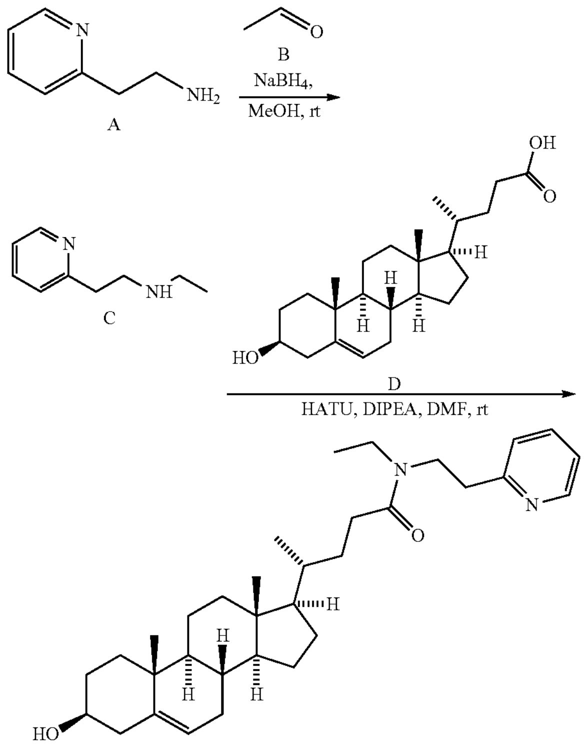

To a solution of compound A (0.3 g, 2.46 mmol) in methanol (3 mL) was added compound B (130 mg, 2.95 mmol) and $NaBH_4$ (111 mg, 2.95 mmol). The reaction was stirred at room temperature for 16 hours. The reaction was quenched with water (10 mL) and extracted with ethyl acetate (15 mL*4). The combined organic layers were concentrated under reduced pressure. The crude product was purified by silica gel chromatography to afford compound C (200 mg, 54%) as a white solid. (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (99.7 mg, 266 mol 1) and N-ethyl-2-(pyridin-2-yl)ethan-1-amine (50 mg, 333 µmol) were reacted according to the method of Example 536 to afford the title compound 541 (68.4 mg, 40%) as a white solid. LCMS: $[M+1]^+$=507.20. $^1$H NMR (400 MHz, Chloroform-d) δ 8.61-8.49 (m, 1H), 7.67-7.53 (m, 1H), 7.24-7.06 (m, 2H), 5.34 (s, 1H), 3.77-3.61 (m, 2H), 3.53 (t, J=13.2 Hz, 1H), 3.37 (d, J=16.4 Hz, 1H), 3.28-3.16 (m, 1H), 3.11-2.94 (m, 2H), 2.41-2.12 (m, 4H), 1.98-1.90 (m, 2H), 1.91-1.71 (m, 4H), 1.49-1.40 (m, 8H), 1.37-1.22 (m, 3H), 1.22-1.03 (m, 7H), 1.01 (s, 4H), 0.97-0.84 (m, 4H), 0.68 (d, J=7.2 Hz, 3H).

Example 542: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-N-methyl-N-[(pyridin-2-yl) methyl]pentanamide

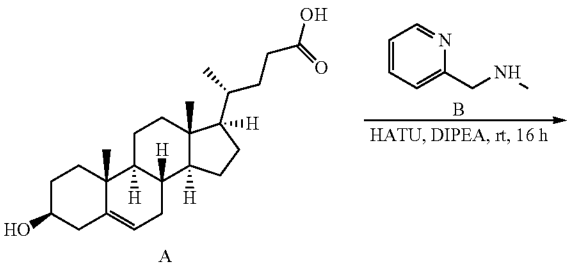

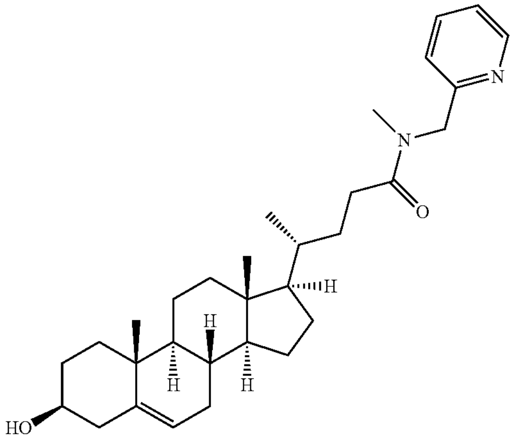

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (200 mg, 534 μmol) and N-methyl-1-(pyridin-2-yl)methanamine (65.2 mg, 534 μmol) were reacted according to the method of Example 536 to afford the title compound 542 (124.0 mg, 48.5%) as a white solid. LCMS: $[M+1]^+$=479.30. $^1H$ NMR (400 MHz, $CDCl_3$) δ 8.61-8.49 (m, 1H), 7.72-7.61 (m, 1H), 7.26-7.11 (m, 2H), 5.34 (dd, J=5.4, 2.8 Hz, 1H), 4.77-4.61 (m, 2H), 3.52 (s, 1H), 3.03 (d, J=21.6 Hz, 3H), 2.48-2.36 (m, 1H), 2.33-2.19 (m, 3H), 2.03-1.93 (m, 2H), 1.90-1.75 (m, 4H), 1.62 (s, 2H), 1.55-1.46 (m, 5H), 1.45-1.25 (m, 5H), 1.18-1.03 (m, 4H), 1.00 (d, J=5.4 Hz, 3H), 0.97 (d, J=6.4 Hz, 2H), 0.86 (d, J=6.2 Hz, 1H), 0.67-0.65 (m, 3H).

Example 543: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methyl-N-(2-(pyridin-3-yl)ethyl)pentanamide

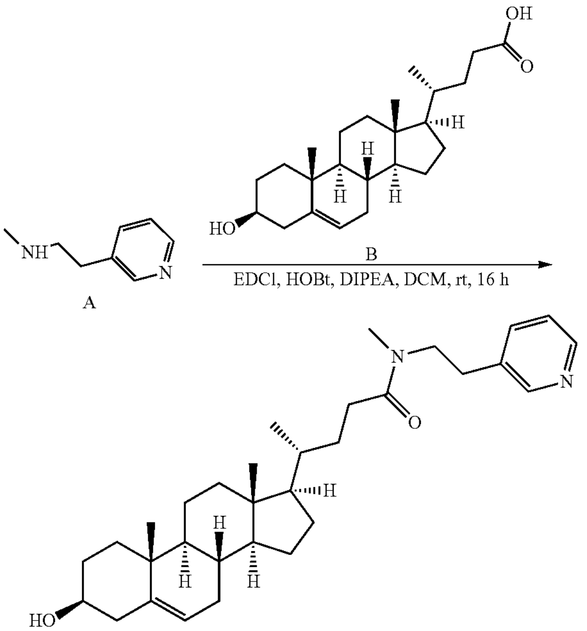

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (220 mg, 587 μmol) and N-methyl-2-(pyridin-3-yl)ethan-1-amine (80 mg, 587 μmol) were reacted according to the method of Example 444 to afford the title compound 543 (65.9 mg, 23%) as a white solid. LCMS: $[M+1]^+$=493.20. $^1H$ NMR (400 MHz, $CDCl_3$): δ 8.47 (s, 2H), 7.64-7.43 (m, 1H), 7.24 (d, J=5.2 Hz, 1H), 5.34 (d, J=5.2 Hz, 1H), 3.62-3.46 (m, 3H), 2.93 (d, J=16.8 Hz, 3H), 2.85 (q, J=7.2 Hz, 2H), 2.36-2.07 (m, 6H), 2.02-1.92 (m, 2H), 1.90-1.66 (m, 4H), 1.64-1.38 (m, 7H), 1.36-1.23 (m, 2H), 1.21-0.98 (m, 8H), 0.93 (d, J=6.4 Hz, 3H), 0.85 (d, J=6.4 Hz, 1H), 0.66 (d, J=7.2 Hz, 3H).

Example 544: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methyl-N-(2-(pyridin-4-yl)ethyl)pentanamide

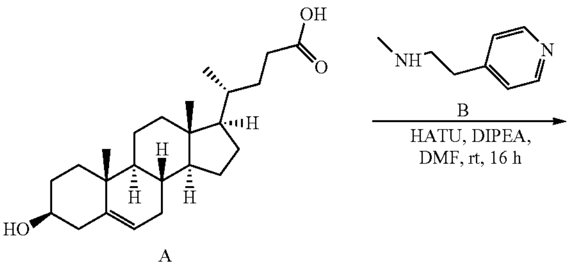

-continued

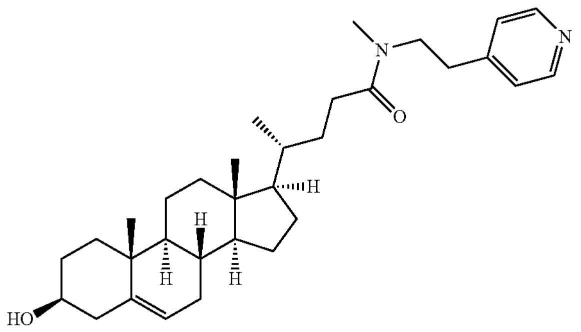

N-methyl-2-(pyridin-4-yl)ethan-1-amine (72.7 mg, 534 μmol) and (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (200 mg, 534 μmol) were reacted according to the method of Example 536 to afford the title compound 544 (193 mg, 73.51%) as a white solid. LCMS: $[M+1]^+$=493.30. $^1H$ NMR (400 MHz, Chloroform-d) δ 8.58-8.47 (m, 2H), 7.08-7.23 (m, 2H), 5.34 (d, J=5.2 Hz, 1H), 3.66-3.46 (m, 3H), 2.93 (d, J=12.8 Hz, 3H), 2.86 (t, J=7.6 Hz, 2H), 2.39-2.06 (m, 4H), 2.05-1.99 (m, 2H), 1.91 (s, 3H), 1.89-1.80 (m, 3H), 1.78-1.68 (m, 1H), 1.58 (dd, J=12.0, 5.8 Hz, 1H), 1.55-1.37 (m, 6H), 1.33-1.25 (m, 2H), 1.15 (dd, J=8.8, 3.6 Hz, 1H), 1.12-1.09 (m, 1H), 1.09-1.02 (m, 2H), 1.00 (s, 3H), 0.94 (d, J=6.4 Hz, 3H), 0.86 (d, J=6.4 Hz, 1H), 0.67 (d, J=6.8 Hz, 3H).

Example 545: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methyl-N-(2-(thiazol-2-yl)ethyl)pentanamide

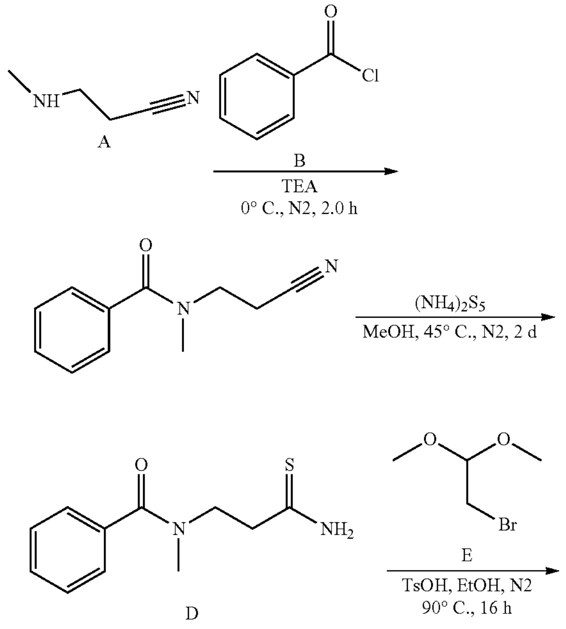

-continued

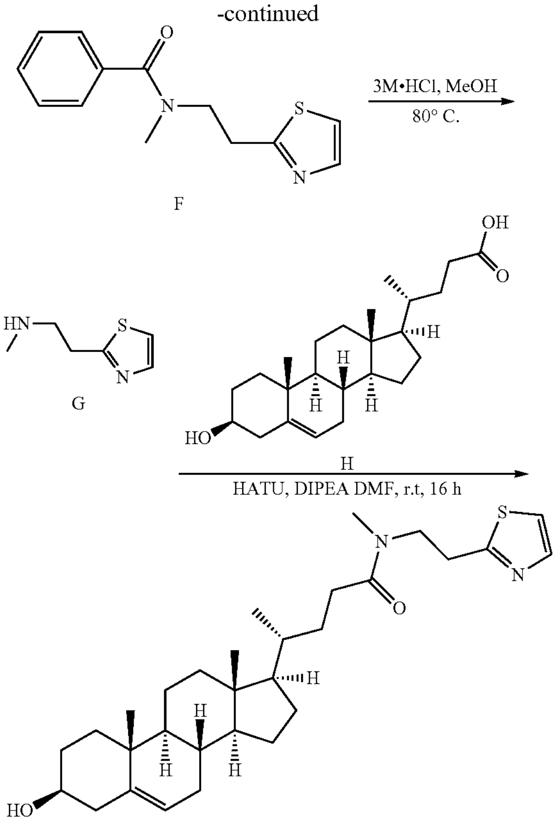

To a 0° C. solution of compound A (3 g, 35.7 mmol) in THF (60 mL, 737 mmol) under $N_2$ was added TEA (7.22 g, 71.3 mmol), compound B (5.01 g, 35.7 mmol) and the reaction was warmed to room temperature under $N_2$ for 16.0 h. The reaction was quenched with water (20 mL) and extracted with EtOAc (60 mL). The organic layer was washed with brine (20 mL), dried over sodium sulfate, filtered, and concentrated. The residue was purified by silica gel chromatography to afford the compound C (6.5 g, 97%). To a solution of compound C (6 g, 31.9 mmol) in methanol (240 mL) was added $(NH_4)_2S_5$ (56.8 g, 319 mmol). The reaction was stirred at 85° C. under $N_2$ for 2.0 days. The reaction was quenched with water (200 mL) and extracted with EtOAc (5*100 mL). The combined organic layers were washed with brine, dried over sodium sulfate, filtered, and concentrated. The residue was purified by silica gel chromatography to afford compound D (1.92 g, 27.1%). To a solution of compound D (0.2 g, 0.9 mmol) in ethanol (6 mL) was added compound E (228 mg, 1.35 mmol) and TsOH (232 mg, 1.35 mmol). The reaction was stirred at 90° C. under $N_2$ for 16.0 h. The reaction was quenched with saturated aqueous $NH_4Cl$ (10 mL) and extracted with EtOAc (20 mL). The organic layer was washed with brine (10 mL), dried over sodium sulfate, filtered, and concentrated. The residue was purified by silica gel chromatography to afford the title compound F (40 mg, 18%). To a solution of compound F (40 mg, 162 μmol) in methanol (1.33 mL) was added 4N hydrogen chloride in 1,4-dioxane (0.5 mL). The reaction was stirred at 80° C. under $N_2$ for 16.0 h. The reaction was quenched with saturated aqueous $NH_4Cl$ and extracted with EA. The organic layer was washed with brine, dried over sodium sulfate, filtered, and concentrated. The residue was purified by silica gel chromatography to afford the compound G (15 mg, 65.2%).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (52.7 mg, 141 μmol) and N-methyl-2-(thiazol-2-yl)ethan-1-amine (20 mg, 141 μmol) were reacted according to the method of Example 536 to afford the title compound 545 (7.6 mg, 10.8%) as a white solid. LCMS: $[M+1]^+$=499.45. $^1H$ NMR (400 MHz, Chloroform-d) δ7.71-7.69 (m, 1H), 7.22 (dd, J=11.8, 3.4 Hz, 1H), 5.34 (d, J=5.0 Hz, 1H), 3.76 (t, J=7.0 Hz, 2H), 3.52 (tt, J=10.7, 4.6 Hz, 1H), 3.27 (t, J=7.1 Hz, 2H), 2.94 (d, J=10.9 Hz, 3H), 2.38-2.17 (m, 4H), 2.04-1.93 (m, 2H), 1.89-1.80 (m, 3H), 1.63-1.28 (m, 11H), 1.21-0.85 (m, 14H), 0.67 (d, J=5.4 Hz, 3H).

Example 546: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyridin-4-ylmethoxy)piperidin-1-yl)pentan-1-one

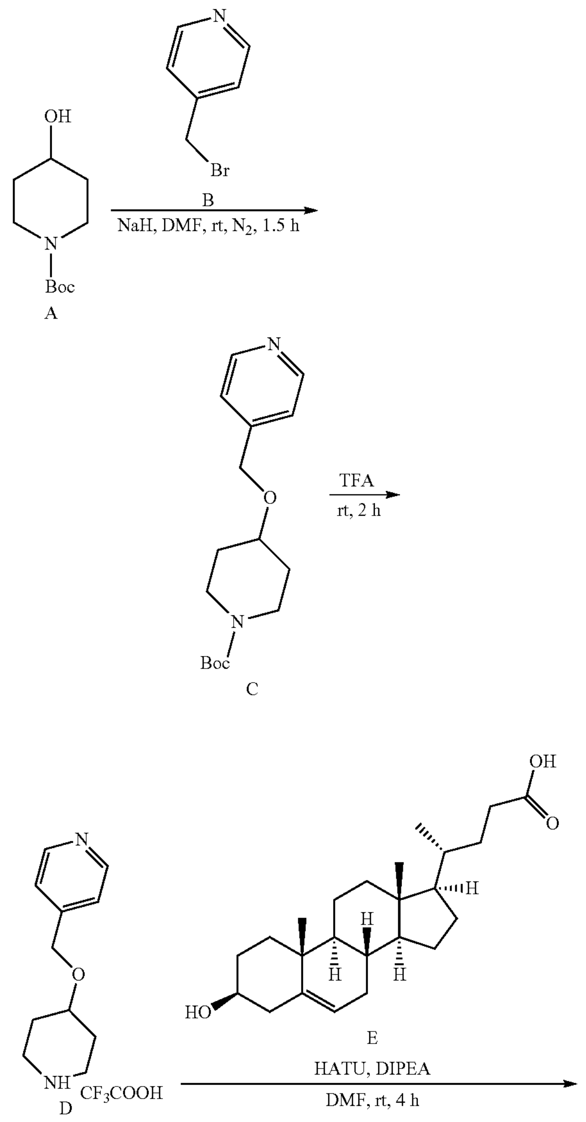

-continued

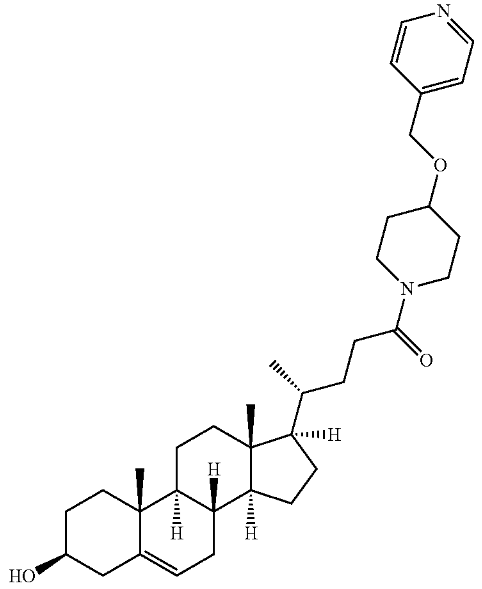

To a solution of compound A (200 mg, 994 μmol) in DMF (4 mL) was added compound B (180 mg, 1.05 mmol) and NaH (96 mg, 2.40 mmol, 60% dispersion in mineral oil) and the reaction was stirred at room temperature for 1.5 h under $N_2$. Upon completion, the reaction was diluted with water (10 mL) and extracted with ethyl acetate (20 mL). The organic layer was concentrated under reduced pressure. The crude product was purified by Prep-TLC to afford the compound C (100 mg, 34%). To a solution of compound C (100 mg, 342 μmol) in DCM was added TFA (1 mL), the reaction was stirred at room temperature for 2 h. Upon completion, the reaction was concentrated to afford compound D as the TFA salt (65 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (127 mg, 338 μmol) and 4-((piperidin-4-yloxy)methyl)pyridine 2,2,2-trifluoroacetate (65 mg, 212 μmol) were reacted according to the method of Example 536 to afford the title compound 546 (67 mg, 36%). LCMS: $[M+1]^+$=549.25 $^1H$ NMR (400 MHz, DMSO-$d_6$) δ 8.79 (d, J=5.8 Hz, 2H), 7.93 (d, J=5.8 Hz, 2H), 5.24 (d, J=4.6 Hz, 1H), 4.83 (s, 2H), 3.83 (s, 1H), 3.70 (s, 2H), 3.28-3.18 (m, 2H), 3.10 (d, J=11.0 Hz, 1H), 2.31 (s, 1H), 2.21 (s, 1H), 2.14-2.04 (m, 2H), 1.92 (s, 2H), 1.87 (s, 1H), 1.84-1.69 (m, 3H), 1.66 (d, J=12.2 Hz, 1H), 1.51 (s, 2H), 1.44 (s, 2H), 1.38 (s, 2H), 1.34 (d, J=12.0 Hz, 2H), 1.21 (s, 3H), 1.16-1.05 (m, 3H), 0.96 (d, J=12.8 Hz, 3H), 0.92 (s, 3H), 0.89 (d, J=6.4 Hz, 3H), 0.84 (s, 1H), 0.63 (s, 3H).

Example 547: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-N-(pyridin-4-yl)pentanamide

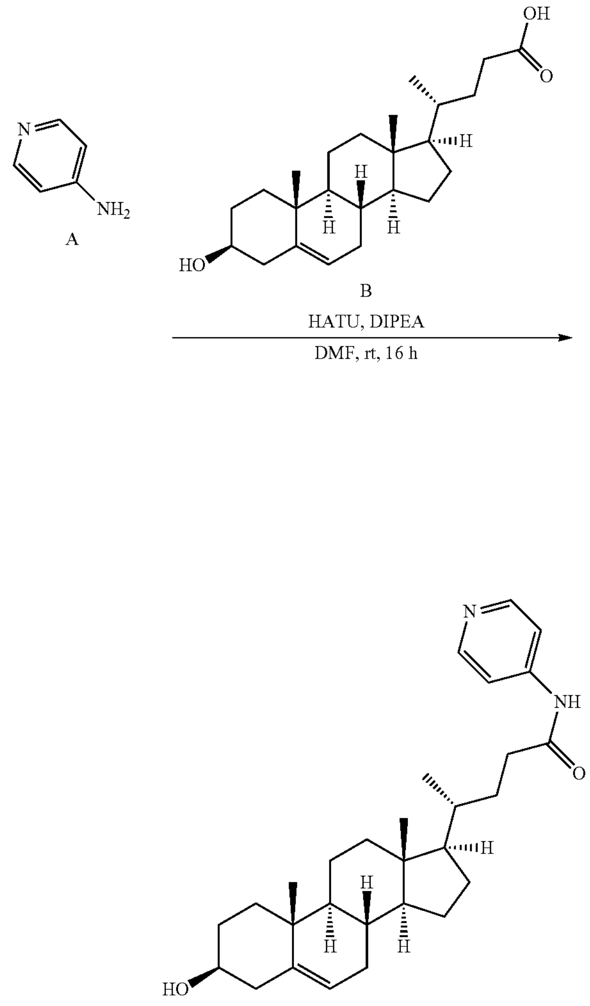

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (100 mg, 1.06 mmol) and pyridin-4-amine (318 mg, 850 μmol) were reacted according to the method of Example 536 to afford the title compound 547 (212 mg, 44%) as a white solid. LCMS: $[M+1]^+$=451.20. $^1H$ NMR (400 MHz, DMSO-$d_6$) δ 10.23 (s, 1H), 8.43-8.33 (m, 2H), 7.60-7.48 (m, 2H), 5.26 (d, J=5.2 Hz, 1H), 4.58 (d, J=4.6 Hz, 1H), 3.24 (dt, J=10.8, 5.2 Hz, 1H), 2.34-2.42 (m, 1H), 2.25-2.29 (m, 1H), 2.19-2.01 (m, 2H), 1.93-1.98 (m, 2H), 1.86-1.71 (m, 3H), 1.70-1.63 (m, 1H), 1.61-1.44 (m, 3H), 1.43-1.35 (m, 3H), 1.27-1.32 (m, 3H), 1.20-1.04 (m, 3H), 1.04-0.96 (m, 2H), 0.95-0.81 (m, 7H), 0.65 (s, 3H).

Example 548: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-N-cyclopropyl-N-(pyridin-4-yl)pentanamide

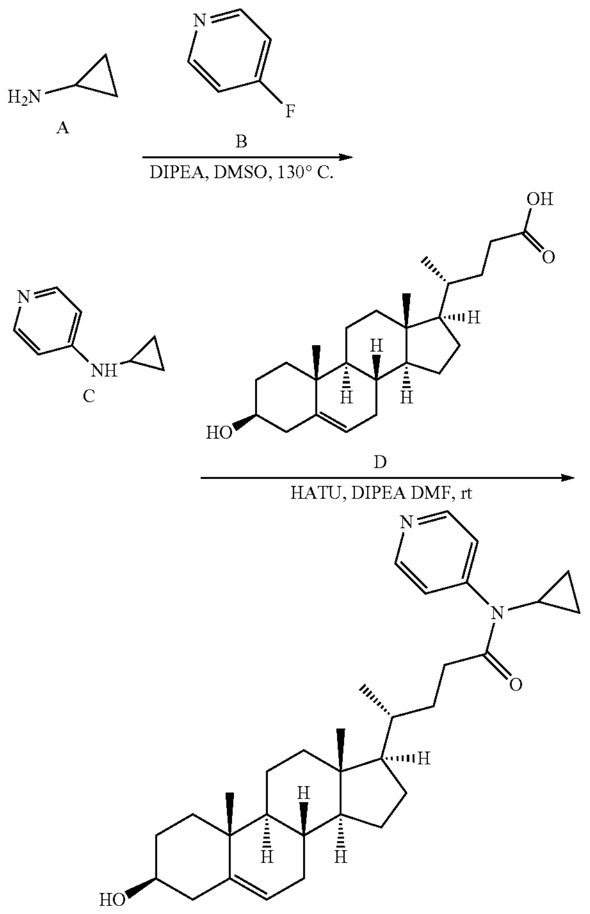

To a room temperature solution of compound B (200 mg, 2.06 mmol) and compound A (353 mg, 6.18 mmol) in DMSO (5 mL) was added DIPEA (1.1 g, 8.24 mmol) and the reaction was stirred at 130° C.; for 16 hours. Water (30 mL) was added, and the reaction was extracted with EtOAc (30 mL*3). The combined organic layers were washed with water (20 mL), dried over sodium sulfate, and concentrated under reduced pressure. The crude product was purified by silica gel chromatography to afford compound C (15 mg, 6%) as a yellow oil.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (28 mg, 74.5 μmol) and N-cyclopropylpyridin-4-amine (10 mg, 74.5 μmol) were reacted according to the method of Example 536 to afford the title compound 548 (12 mg, 32.7%) as a white solid LCMS: [M+H]+=491.40. $^1H$ NMR (400 MHz, Chloroform-d) δ 8.56 (d, J=5.2 Hz, 2H), 7.24 (d, J=5.6 Hz, 2H), 5.34 (dd, J=4.8, 2.4 Hz, 1H), 3.55-3.48 (m, 1H), 3.08-3.03 (m, 1H), 2.66-2.47 (m, 2H), 2.32-2.20 (m, 2H), 2.07-1.92 (m, 3H), 1.90-1.79 (m, 7H), 1.59-1.40 (m, 7H), 1.35-1.25 (m, 4H), 1.14-1.02 (m, 5H), 1.00 (s, 3H), 0.92 (d, J=6.4 Hz, 3H), 0.68 (s, 3H).

Example 549: O-methyl4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)piperazine-1-carbothioate

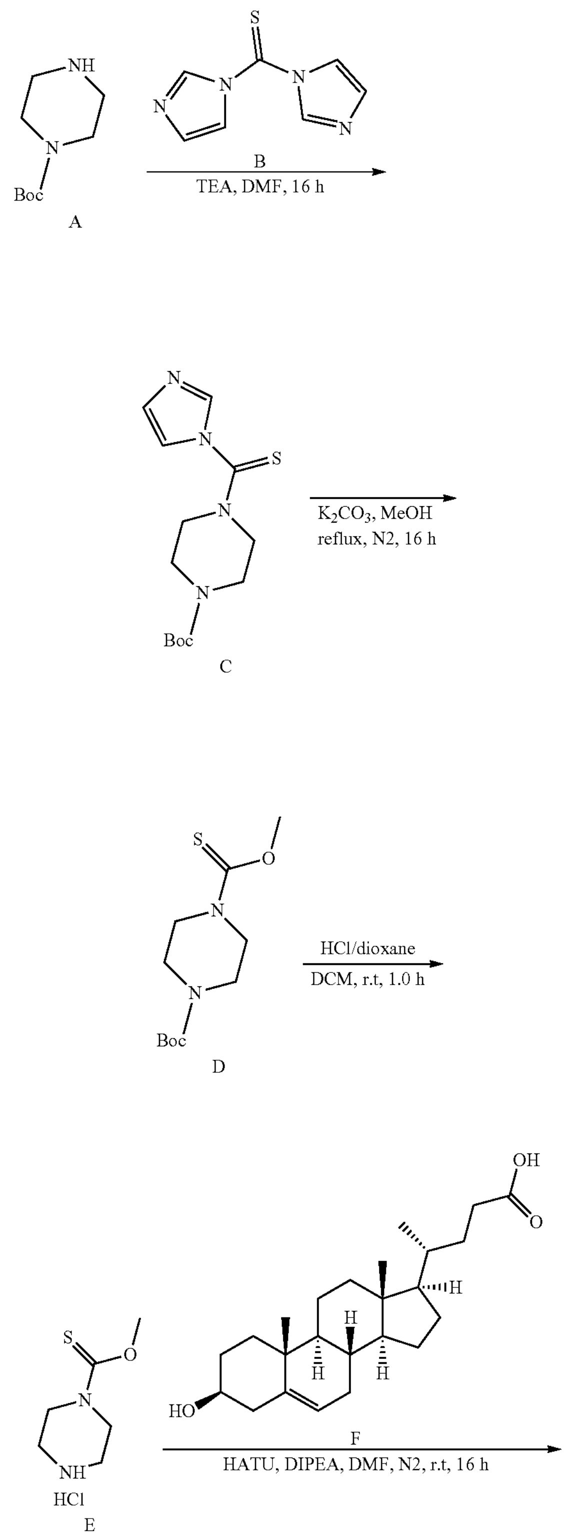

-continued

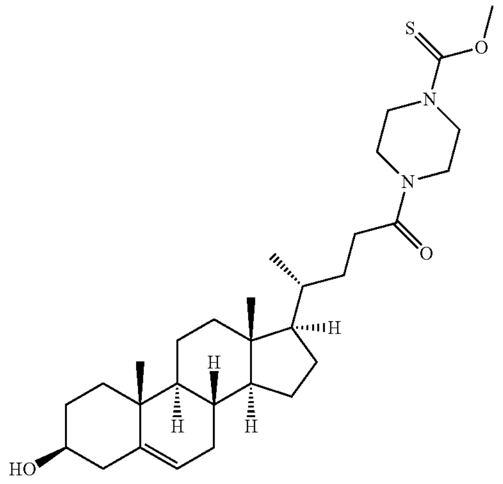

To a solution of compound A (200 mg, 1.07 mmol) in DMF (5 mL, 64.6 mmol) was added compound B (574 mg, 3.22 mmol), TEA (326 mg, 3.22 mmol) and the reaction was stirred at room temperature under $N_2$ for 16.0 h. The reaction was quenched with saturated aqueous $NH_4Cl$ (10 mL) and extracted with EtOAc (20 mL). The organic layer was washed with brine (5 mL), dried over sodium sulfate, filtered, and concentrated under reduced pressure. The residue was purified by silica gel chromatography to afford the compound C (300 mg, 94.3%). To a solution of C (200 mg, 675 μmol) in methanol (3.0 mL) was added $K_2CO_3$ (0.1 g, 384 μmol). The reaction was stirred at 85° C. under $N_2$ for 16 h. The reaction was quenched with saturated aqueous $NH_4Cl$ (10 mL) and extracted with EtOAc (20 mL). The organic layer was washed with brine (5 mL), dried over sodium sulfate, filtered, and concentrated. The residue was purified by silica gel chromatography to afford compound D (100 mg, 57.1%) as a white solid. To a solution of D (0.1 g, 384 μmol) in DCM (2.0 mL) was added 4N HCl in 1,4-dioxane (0.2 mL). The reaction was stirred at room temperature for 2.0 h. The reaction concentrated under reduced pressure to afford the title compound E as the HCl salt (70 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (115 mg, 307 μmol) and O-methyl piperazine-1-carbothioate (61.5 mg, 312 μmol) were reacted according to the method of Example 536 to afford the title compound 549 (88.1 mg, 44.5%) as a white solid. LCMS: $[M+1]^+$=517.20. $^1H$ NMR (400 MHz, Chloroform-d) δ 5.39-5.32 (m, 1H), 4.06 (s, 5H), 3.82-3.43 (m, 7H), 2.45-2.18 (m, 4H), 2.05-1.93 (m, 2H), 1.92-1.73 (m, 4H), 1.56-1.40 (m, 7H), 1.37-1.24 (m, 4H), 1.22-0.86 (m, 13H), 0.68 (s, 3H).

Example 550: methyl4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanethioyl]piperazine-1-carboxylate

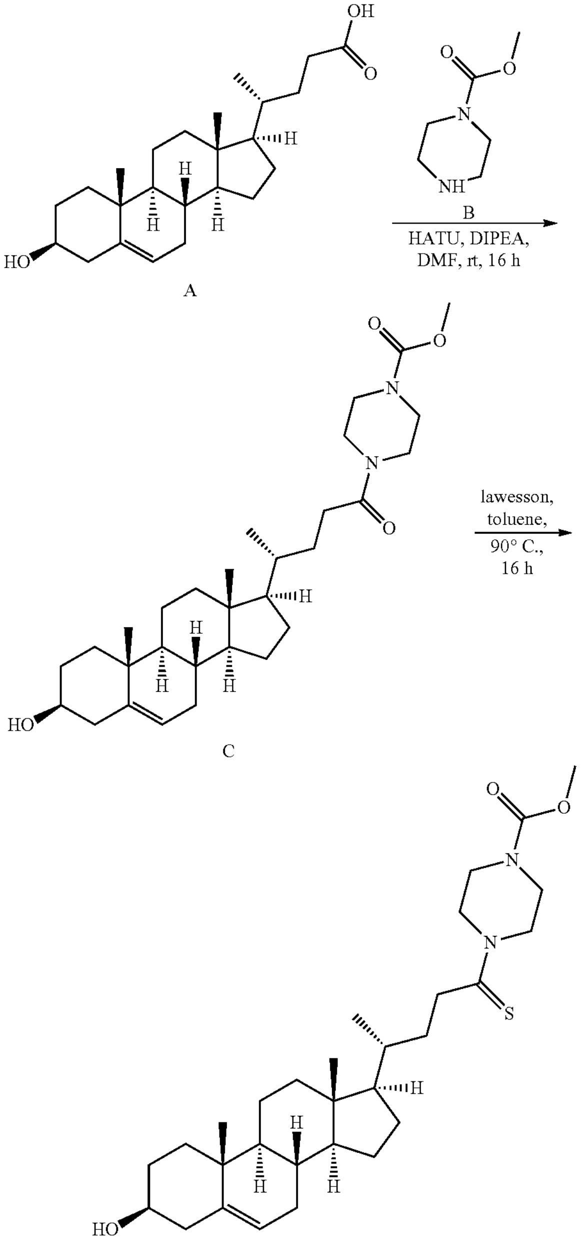

To a solution of compound A (250 mg, 667 μmol) in dimethylformamide (10 mL) was added DIPEA (173 mg, 1.33 mmol), compound B (96.2 mg, 667 μmol) and HATU (761 mg, 2 mmol) and the reaction was stirred at room temperature for 16 h. The reaction was diluted with ethyl acetate (30 mL), washed with water (20 mL), brine (10 mL), dried with sodium sulfate and concentrated under reduced pressure. The crude product was purified by silica gel chromatography to give compound C (300 mg, 89.7%) as a white solid.

To a solution of compound C (200 mg, 399 μmol) in toluene (8 mL) was added bis(4-methoxyphenyl)-1,3,2$\lambda^5$,4$\lambda^5$-dithiadiphosphetane-2,4-dithione (194 mg, 479 μmol) at room temperature. The reaction was evacuated and back filled with nitrogen three times and charged with nitrogen. The reaction was heated at 90° C. for 1 h. The reaction was diluted with ethyl acetate (20 mL) washed with water (10 mL), brine (5 mL), dried with sodium sulfate and concentrated under reduced pressure. The crude product was purified by silica gel chromatography to give the title compound 550 (12.8 mg, 6.2%) as a white solid. LCMS: rt: 4.36, 517.40 [M+1]. $^1$H NMR (400 MHz, $CDCl_3$) δ 5.35 (d, J=4.8 Hz, 1H), 4.31 (d, J=3.6 Hz, 2H), 3.83-3.63 (m, 5H), 3.56-3.50 (m, 5H), 2.97 (td, J=12.4, 4.8 Hz, 1H), 2.79 (dt, J=12.6, 6.5 Hz, 1H), 2.32-2.19 (m, 3H), 2.03-1.95 (m, 3H), 1.84 (d, J=11.8 Hz, 3H), 1.76 (s, 2H), 1.51-1.45 (m, 5H), 1.30 (s, 4H), 1.18-1.06 (m, 4H), 1.00 (d, J=8.6 Hz, 6H), 0.69 (s, 3H).

Example 551: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-{4-[(methylsulfanyl)carbonyl]piperazin-1-yl}pentan-1-one

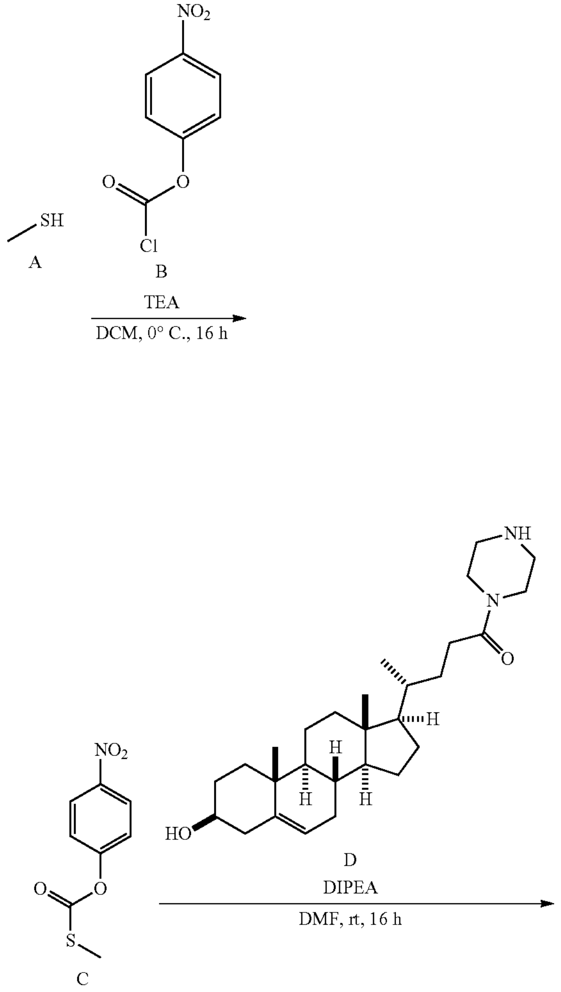

-continued

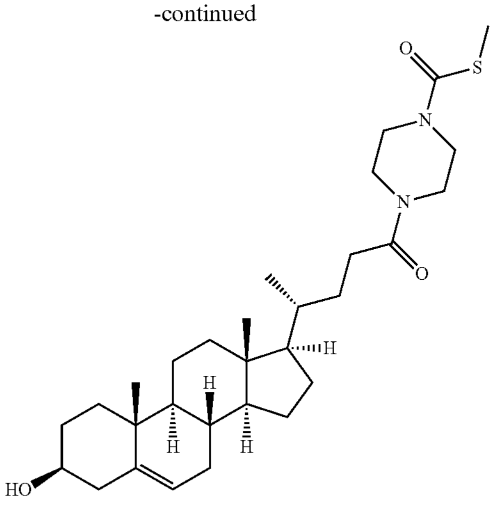

To a solution of compound A (500 mg, 10.4 mmol) in dichloromethane (10 mL, 156 mmol) was added TEA (0.3 g, 2.01 mmol) and compound B (0.3 g, 1.49 mmol) at 0° C. slowly. The reaction was stirred for 1 hour. Upon completion, the reaction was quenched with water (90 mL) and extracted with ethyl acetate (30 mL*3). The combined organic layers were washed with brine (10 mL), dried over sodium sulfate, filtered, and concentrated under reduced pressure. The residue was purified by silica gel chromatography to afford compound C (120 mg, 5%) as a white solid. To a solution of compound C (120 mg, 563 μmol), compound D (249 mg, 563 μmol) in DMF (5 mL) was added DIPEA (109 mg, 844 μmol) at room temperature under $N_2$ and stirred for 16 h.

The reaction was diluted with saturated $NH_4Cl$ (30 mL) and extracted with EtOAc (10 mL*2). The combined organic layers were washed with saturated aqueous $NaHCO_3$ (20 mL), water (20 mL), brine (20 mL), dried over sodium sulfate and concentrated under reduced pressure. The residue was purified by silica gel chromatography to afford the title compound 551 (80 mg, 27%) as a white solid. LCMS: $[M+1]^+$=517.20. $^1$H NMR (400 MHz, Chloroform-d) δ 5.35 (d, J=5.2 Hz, 1H), 3.68-3.44 (m, 9H), 2.36 (s, 4H), 2.25 (dt, J=14.4, 5.6 Hz, 3H), 2.06-1.93 (m, 2H), 1.90-1.73 (m, 4H), 1.55-1.39 (m, 7H), 1.37-1.28 (m, 3H), 1.23-1.06 (m, 4H), 1.05-0.87 (m, 9H), 0.68 (s, 3H).

Example 552: methyl6-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-1,6-diazaspiro[3.3]heptane-1-carboxylate

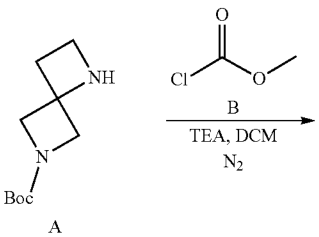

A

-continued

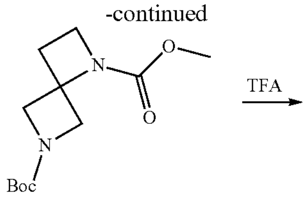

C

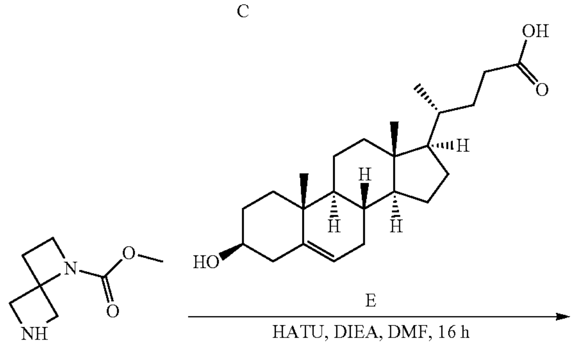

D $CH_3COOH$

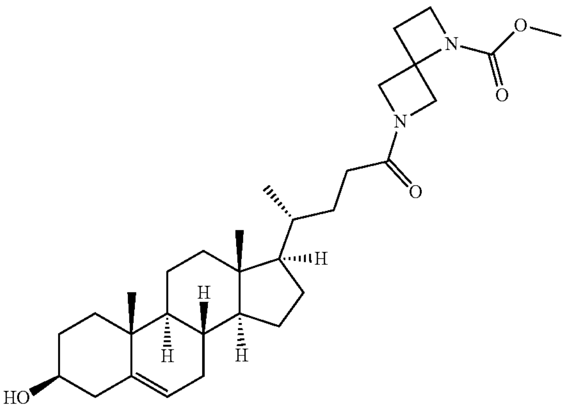

To a solution of compound A (80 mg, 403 μmol) in DCM (3 mL) was added TEA (122 mg, 1.21 mmol) and compound B (38.1 mg, 403 μmol). The reaction was stirred at room temperature under $N_2$ for 16.0 h. The reaction was quenched with water (10 mL) and extracted with EtOAc (20 mL). The organic layer was washed with brine (5 mL), dried over sodium sulfate, filtered, and concentrated under reduced pressure, and the residue was purified by silica gel chromatography to afford the compound C (50 mg, 48.5%) as a white solid. To a solution of C (56 mg, 218 μmol) in DCM (4.0 mL) was added TFA (0.1 mL). The reaction was stirred at room temperature for 16.0 h. The reaction concentrated to afford compound D as the TFA salt (34 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (81.5 mg, 218 μmol) and methyl 1,6-diazaspiro[3.3]heptane-1-carboxylate acetate TFA salt (34 mg, 125 μmol) were reacted according to the method of Example 536 to afford the title compound 552 (34.2 mg, 30.6%) as a white solid. LCMS: $[M+1]^+$=513.40. $^1$H NMR (400 MHz, Chloroform-d) δ 5.35-5.33 (m, 1H), 4.86-4.38 (m, 2H), 4.10-4.06 (m, 1H), 4.02-4.00 (m, 1H), 3.85-3.81 (m, 2H), 3.71-3.58 (m, 3H), 3.57-3.46 (m, 1H), 2.45 (t, J=7.6 Hz, 2H), 2.33-2.20 (m, 2H), 2.14 (m, 1H), 2.05-1.92 (m, 3H), 1.89-1.79 (m, 4H), 1.62-1.38 (m, 9H), 1.36-1.27 (m, 3H), 1.18-0.83 (m, 13H), 0.67 (s, 3H).

Example 553: Methyl 2-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-5-thia-2,8-diazaspiro[3.4]octane-δ-carboxylate

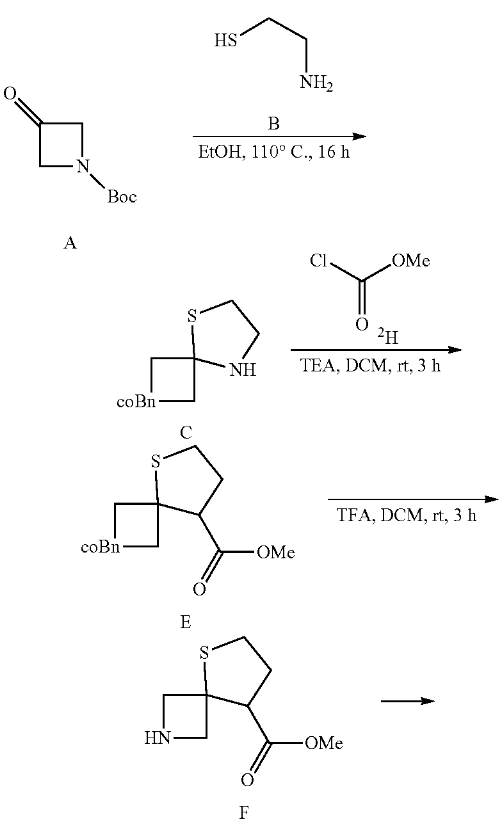

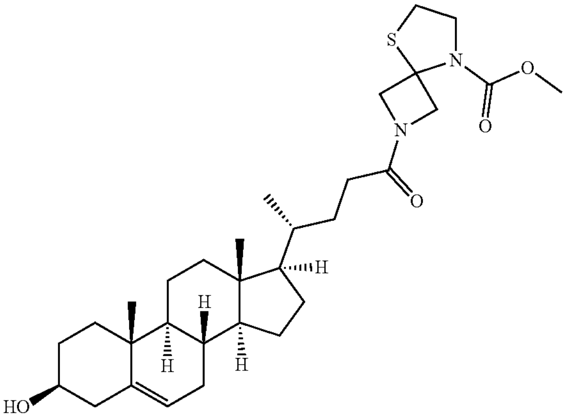

To a solution of compound A (3 g, 17.5 mmol) in EtOH (60 mL) was added compound B (2 g, 8.68 mmol) and the reaction was stirred at 110° C. for 16 h. The reaction was quenched with water (150 mL) and extracted with EtOAc (300 mL). The organic layer was washed with brine (200 mL), dried over sodium sulfate, filtered, and concentrated under reduced pressure. The residue was purified by silica gel chromatography to afford compound C (2 g, 50%) as a light yellow solid. To a solution of compound C (300 mg, 1.3 mmol) in DCM (5 mL) was added compound D (185 mg, 1.95 mmol) and the reaction was stirred at room temperature for 3 h. TEA (395 mg, 3.91 mmol) was added, and the reaction was stirred at room temperature for 3 h. The reaction was quenched with water (20 mL) and extracted with EtOAc (80 mL). The organic layer was washed with brine (50 mL), dried over sodium sulfate, filtered, and concentrated under reduced pressure. The residue was purified by silica gel chromatography to afford compound E (130 mg, 27%) as a light yellow solid. To a solution of compound E (130 mg, 451 μmol) in DCM (5 mL) was added TFA (1 mL), the reaction was stirred at room temperature for 3 h. The reaction concentrated under reduced pressure to afford compound F (135 mg) as the TFA salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (127 mg, 340 μmol) and methyl 5-thia-2,8-diazaspiro[3.4]octane-δ-carboxylate TFA salt (135 mg, 447 μmol) were reacted according to the method of Example 444 to afford the title compound 553 (24.7 mg, 11%) as a white solid. LCMS: $[M+1]^+$=545.35 $^1H$ NMR (400 MHz, $CDCl_3$): 5.35 (s, 1H), 4.97 (s, 1H), 4.77 (d, J=10.4 Hz, 1H), 4.19 (d, J=8.4 Hz, 1H), 4.10 (d, J=10.4 Hz, 1H), 3.87 (t, J=6.2 Hz, 2H), 3.75 (s, 3H), 3.52 (dt, J=11.2, 6.2 Hz, 1H), 2.95 (t, J=6.2 Hz, 2H), 2.36-2.09 (m, 3H), 1.99 (d, J=11.6 Hz, 3H), 1.84 (d, J=12.0 Hz, 4H), 1.60-1.40 (m, 8H), 1.37-1.25 (m, 3H), 1.22-1.03 (m, 4H), 1.00 (s, 3H), 0.93 (d, J=6.4 Hz, 3H), 0.68 (s, 3H).

Example 554: Methyl 7-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-2,7-diazaspiro[4.4]nonane-2-carboxylate

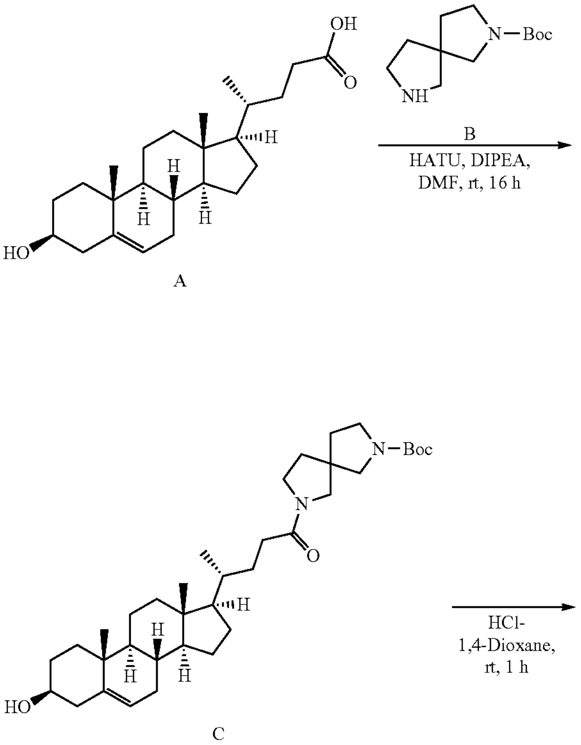

-continued

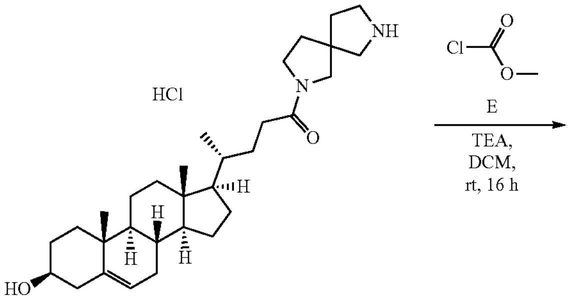

D

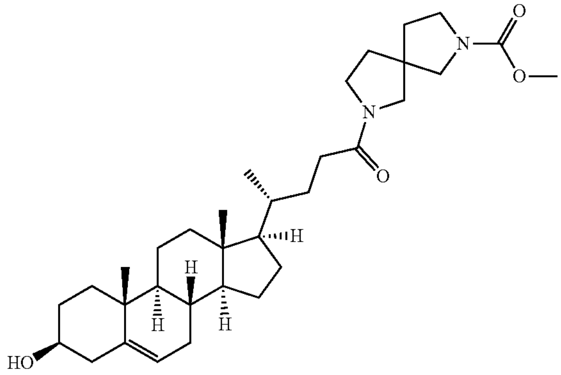

To a solution of compound A (500 mg, 1.33 mmol) and compound B (302 mg, 1.33 mmol) in DMF (5 mL) was added HATU (761 mg, 2 mmol) and DIPEA (518 mg, 4 mmol). The reaction was stirred at room temperature for 16 hours. Upon completion, the reaction was quenched with saturated ammonium chloride solution (15 mL) and extracted with ethyl acetate (15 mL*3). The organic layer was washed with brine (5 mL), dried over sodium sulfate, filtered, and concentrated under reduced pressure. The crude product was purified by silica gel chromatography to afford the title compound C (300 mg, 38.6%).

HCl/1,4-dioxane (5 mL, 4M) was added slowly to the compound C (300 mg, 515 μmol) in a single-neck flask at room temperature and stirred for 1 hour. Upon completion, the crude material was slurried in DCM (10 mL) and concentrated under reduced pressure three times to afford the title compound D as an HCl salt (267.2 mg).

To a solution of compound D (100 mg, 192 μmol) in DCM (3 mL) was added TEA (105 mg, 1.04 mmol) and compound E (15.7 mg, 166 μmol). The reaction was stirred at room temperature for 3 hours. Upon completion, the reaction was quenched with saturated ammonium chloride solution (10 mL) and extracted with ethyl acetate (10 ml*3). The organic layer was washed with brine (10 mL), dried over sodium sulfate, filtered, and was concentrated under reduced pressure. The crude product was purified by silica gel chromatography to afford the title compound 554 (37.7 mg, 33.7%) as a white solid. LCMS: $[M+1]^+=541.30$. $^1H$ NMR (400 MHz, Chloroform-d) δ 5.35 (d, J=5.1 hz, 1H), 3.74-3.65 (m, 3H), 3.64-3.22 (m, 9H), 2.32-2.19 (m, 3H), 2.13 (d, J=12.4 hz, 1H), 2.02-1.93 (m, 3H), 1.85 (dq, J=14.2, 4.9 Hz, 6H), 1.62-1.58 (m, 5H), 1.47 (dt, J=16.1, 4.4 hz, 5H), 1.29-1.27 (m, 3H), 1.18 (dd, J=12.4, 4.6 hz, 1H), 1.13-1.03 (m, 3H), 1.00 (s, 3H), 0.94 (dd, J=6.5, 2.3 hz, 3H), 0.68 (s, 3H).

Example 555: (R)—N-(4-acetamidophenyl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanamide

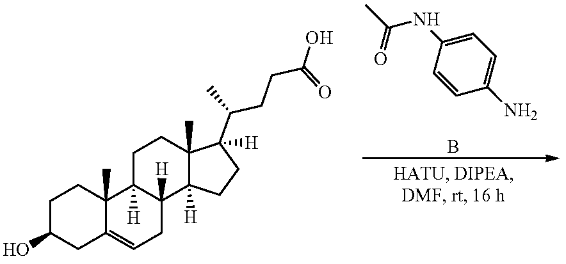

A

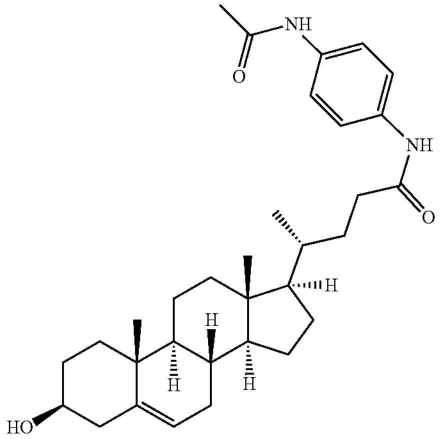

N-(4-aminophenyl)acetamide (80.2 mg, 534 μmol) and (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (200 mg, 534 μmol) were reacted according to Example 536 to give the title compound 555 (70 mg, 25%) as a white solid. $^1H$ NMR (400 MHz, DMSO-$d_6$) δ 9.85 (s, 1H), 9.78 (s, 1H), 7.46-7.43 (m, 3H), 5.26 (d, J=4.8 hz, 1H), 3.50 (s, 1H), 3.24 (dt, J=11.2, 6.0 hz, 1H), 2.33-2.26 (m, 1H), 2.21-2.07 (m, 3H), 2.00 (s, 3H), 1.97-1.81 (m, 3H), 1.78-1.64 (m, 3H), 1.55-1.45 (m, 3H), 1.43-1.32 (m, 4H), 1.30-1.25 (m, 2H), 1.23-1.19 (m, 2H), 1.17-1.04 (m, 3H), 1.01-0.95 (m, 2H), 0.92 (d, J=7.4 hz, 5H), 0.87 (dd, J=10.8, 6.8 hz, 1H), 0.64 (s, 3H).

Example 556: 4—((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanamido)benzamide

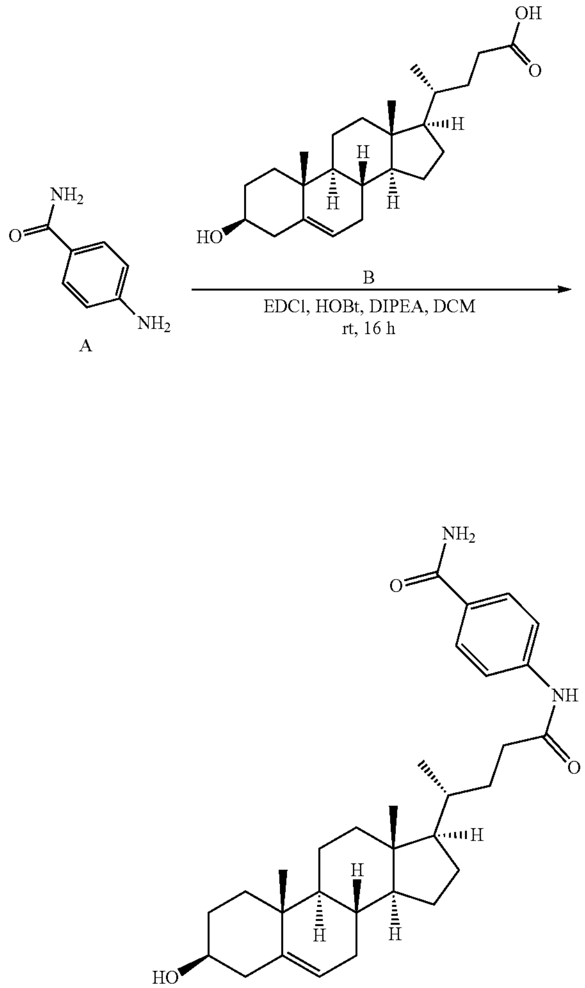

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (275 mg, 734 μmol) and 4-aminobenzamide (100 mg, 734 μmol) were reacted according to the method of Example 626 to give the title compound 556 (13 mg, 4%) as a white solid. LCMS: [M+23]=515.15. $^1$H NMR (400 MHz, DMSO-$d_6$): δ 10.05 (s, 1H), 7.80 (d, J=8.4 hz, 3H), 7.63 (d, J=8.4 hz, 2H), 7.19 (s, 1H), 5.26 (d, J=4.8 hz, 1H), 4.58 (d, J=4.8 hz, 1H), 3.24 (dd, J=10.4, 4.8 hz, 1H), 2.36 (ddd, J=14.8, 9.6, 5.2 hz, 1H), 2.29-2.20 (m, 1H), 2.19-2.03 (m, 2H), 2.01-1.81 (m, 3H), 1.76 (d, J=12.4 hz, 2H), 1.67 (d, J=12.4 hz, 1H), 1.51-1.36 (m, 5H), 1.34-1.22 (m, 4H), 1.19-1.03 (m, 3H), 1.03-0.96 (m, 2H), 0.93-0.89 (m, 6H), 0.89-0.83 (m, 1H), 0.65 (s, 3H).

Example 557: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-(4-tert-butylpiperazin-1-yl)pentan-1-one

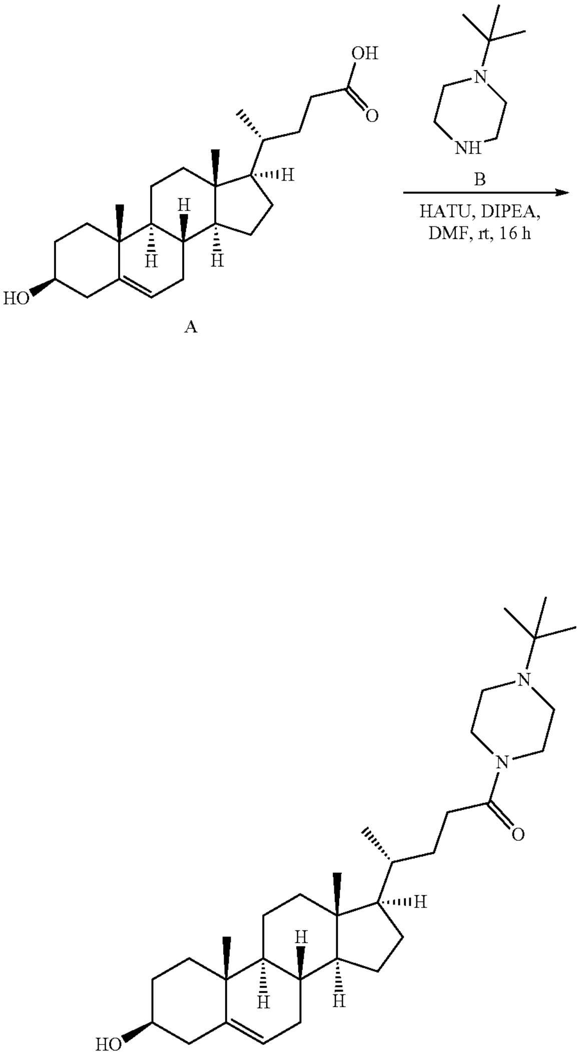

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (200 mg, 534 μmol) and 1-(tert-butyl)piperazine (76 mg, 534 μmol) were reacted according to Example 536 to give the title compound 557 (180 mg, 67%) as white solid. LCMS: $[M+1]^+$=499.25 $^1$H NMR (400 MHz, Chloroform-d) δ 5.35 (d, J=5.2 hz, 1H), 3.91 (s, 2H), 3.80 (d, J=5.6 hz, 2H), 3.59-3.31 (m, 6H), 2.95 (d, J=16.6 hz, 4H), 2.37-2.19 (m, 4H), 2.02-1.94 (m, 2H), 1.88-1.81 (m, 3H), 1.56-1.42 (m, 7H), 1.33 (s, 9H), 1.16-1.06 (m, 3H), 1.00-0.87 (m, 4H), 0.94 (d, J=6.4 hz, 4H), 0.68 (s, 3H).

Example 558: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-(4-cyclopropylpiperazin-1-yl)pentan-1-one

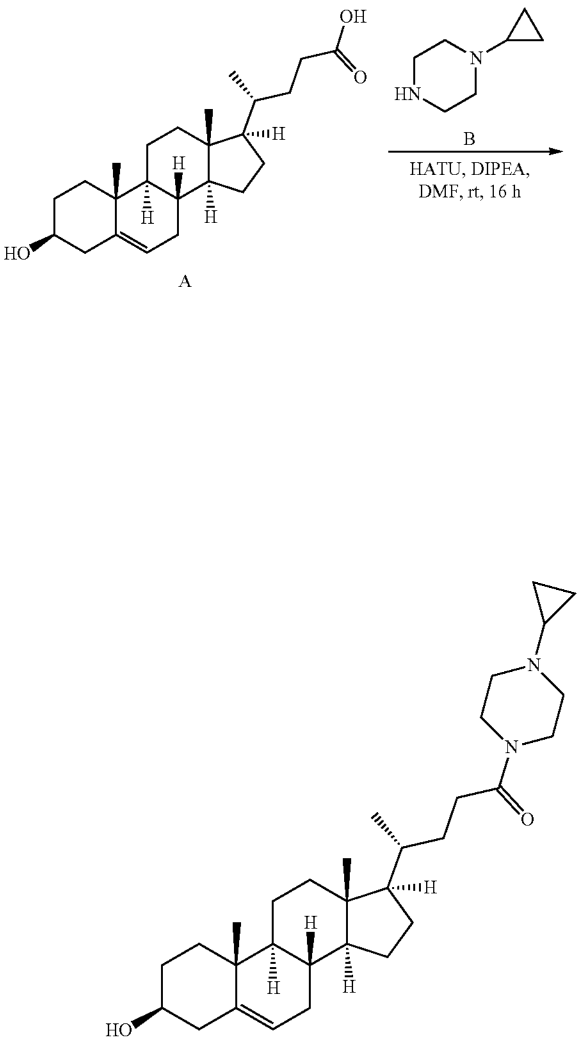

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (200 mg, 534 μmol) and 1-cyclopropylpiperazine (67.4 mg, 534 μmol) were reacted according to Example 536 to give the title compound 558 (186.0 mg, 72.2%) as a white solid. LCMS: $[M+1]^+$=483.30. $^1H$ NMR (400 MHz, $CDCl_3$) δ 5.35 (d, J=5.0 hz, 1H), 3.76-3.33 (m, 5H), 2.62 (s, 3H), 2.41-2.18 (m, 4H), 2.03-1.94 (m, 2H), 1.88-1.73 (m, 4H), 1.61 (d, J=9.4 hz, 5H), 1.54-1.41 (m, 7H), 1.36-1.25 (m, 3H), 1.17-1.03 (m, 4H), 1.00 (s, 3H), 0.95 (d, J=6.4 hz, 3H), 0.68 (s, 3H), 0.50 (d, J=6.2 hz, 3H).

Example 559: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(2-hydroxypyrimidin-4-yl)piperazin-1-yl)pentan-1-one

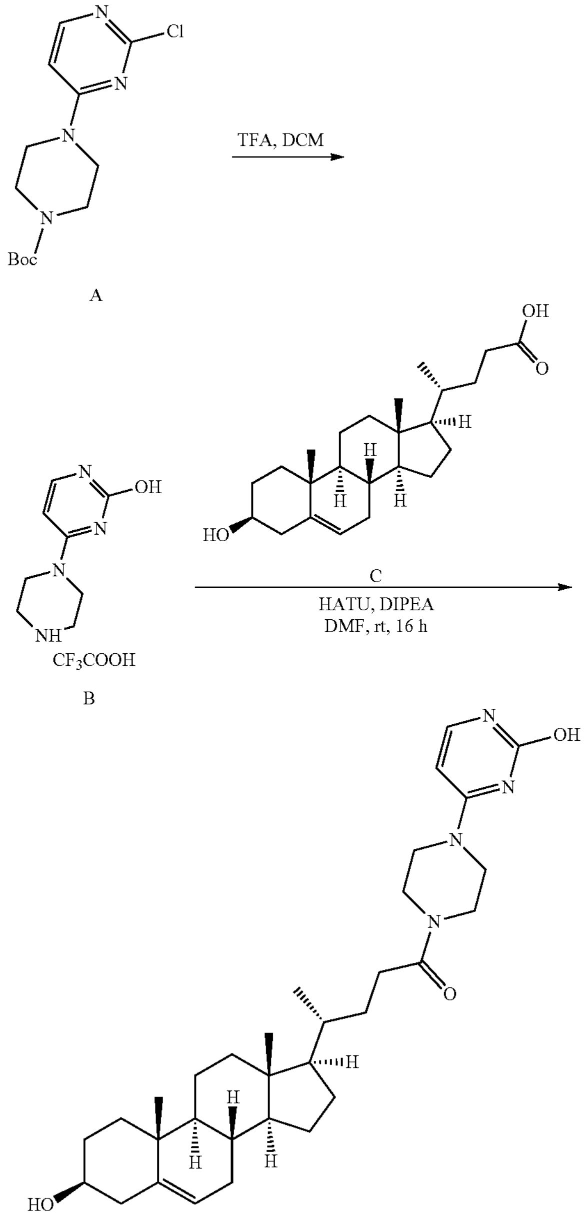

To a solution of compound A (200 mg, 669 μmol) in DCM (5 mL) was added TFA (2 mL) at room temperature and the reaction was stirred for 2 h. The reaction was concentrated under reduced pressure to give compound B as the TFA salt (196 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (250 mg, 669 μmol) and 4-(piperazin-1-yl)pyrimidin-2-ol 2,2,2-trifluoroacetate (196 mg, 626 μmol) were reacted according to Example 536 to give the title compound 559 (30 mg, 8%) as a white solid. LCMS: $[M+1]^+$=537.35. $^1H$ NMR (400 MHz, DMSO-$d_6$) δ 10.52 (bs, 1H), 7.46 (d, J=7.2 hz, 1H), 6.00 (d, J=7.2 hz, 1H), 5.28-5.22 (m, 1H), 4.58 (d, J=4.4 hz, 1H), 3.62-3.56 (m, 3H), 3.50-3.46 (m, 4H), 3.41-3.37 (m, 1H), 3.27-3.20 (m, 1H), 2.40-1.61 (m, 11H), 1.57-0.83 (m, 23H), 0.65 (s, 3H).

Example 560: (R)-1-(4-(2-aminopyrimidin-4-yl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

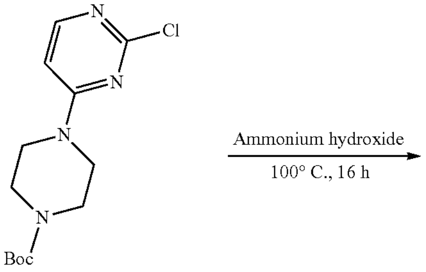

A

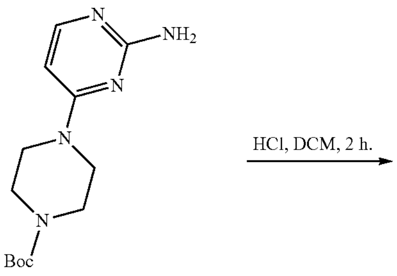

B

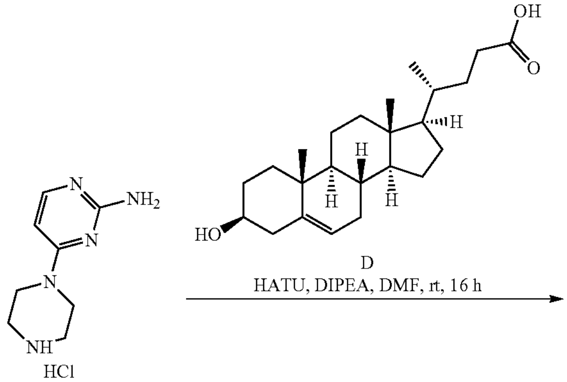

C D

-continued

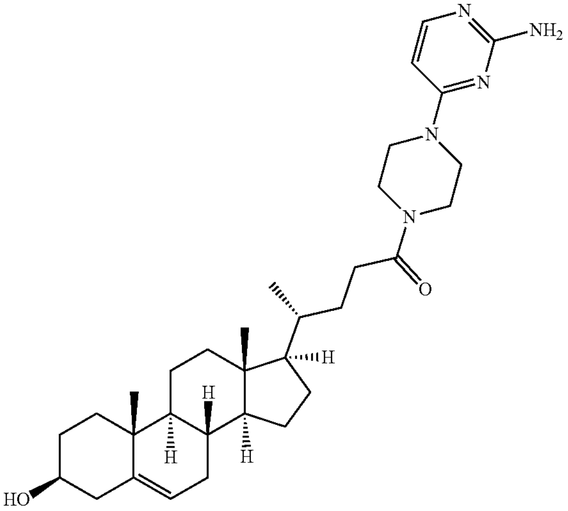

To a solution of compound A (500 mg, 1.68 mmol) in ammonium hydroxide (10 mL), the reaction was heated to reflux under $N_2$ for 16 h. The reaction was cooled to room temperature and was diluted with $H_2O$ (30 mL) and extracted with EtOAc (10 mL*2). The combined organic layer was washed with water (20 mL), brine (20 mL), dried over sodium sulfate and concentrated under reduced pressure to afford compound B (80 mg, 17% yield) as yellow oil.

To a solution of compound B (80 mg, 286 μmol) in DCM (6 mL) was added hydrogen chloride (1 mL, 4 mmol, 4M in 1,4-dioxane) at room temperature and the reaction was stirred for 2 h. The reaction was concentrated under reduced pressure to give compound C as an HCl salt (60 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (83 mg, 224 μmol) and 4-(piperazin-1-yl)pyrimidin-2-aminehydrochloride (60 mg, 280 μmol) was reacted according to Example 536 to give the title compound 560 (30 mg, 20%) as a white solid. LCMS: $[M+1]^+$=536.60. $^1$H NMR (400 MHz, Chloroform-d) δ 7.90 (d, J=6.0 hz, 1H), 5.94 (d, J=6.0 hz, 1H), 5.35 (d, J=5.2 hz, 1H), 4.77 (s, 2H), 3.67 (t, J=5.8 hz, 4H), 3.60-3.47 (m, 5H), 2.44-2.36 (m, 1H), 2.31-2.19 (m, 3H), 2.05-1.94 (m, 2H), 1.88-1.81 (m, 4H), 1.60-1.41 (m, 7H), 1.39-1.26 (m, 3H), 1.20-1.13 (m, 1H), 1.14-1.04 (m, 3H), 1.01 (s, 3H), 0.96 (d, J=6.4 hz, 4H), 0.69 (s, 3H).

Example 561: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(2-(methylamino)pyrimidin-4-yl)piperazin-1-yl)pentan-1-one

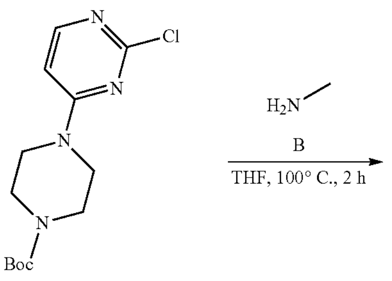

A

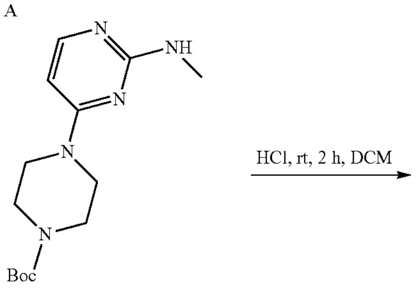

C

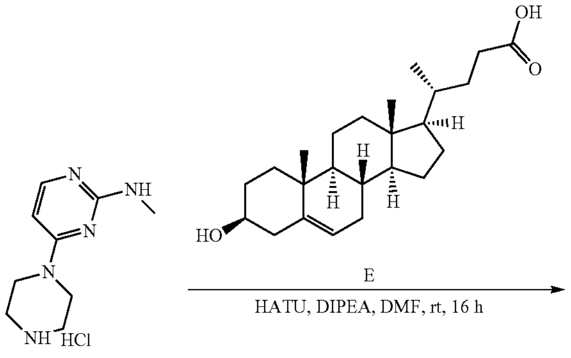

D

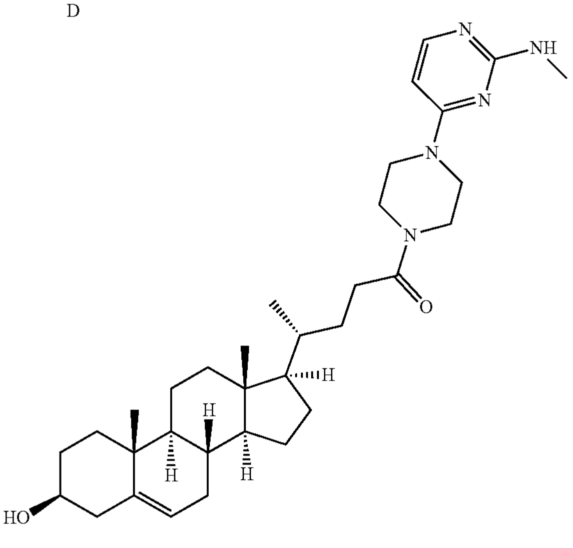

To a solution of compound A (50 mg, 167 μmol) in THF (1 mL) was added compound B (52 mg, 1.67 mmol). The reaction vessel was sealed and heated in microwave at 110° C. for 2 h. The reaction was cooled to room temperature, diluted with saturated aqueous $NH_4Cl$ (aq, 30 mL) and extracted with EtOAc (10 mL*2). The combined organic layers were washed with water (20 mL), brine (20 mL), dried over sodium sulfate and concentrated under reduced pressure to afford compound C (45 mg, 91% yield) as a white solid.

To a solution of compound C (45 mg, 153 μmol) in DCM (6 mL) was added hydrogen chloride (1 mL, 4 mmol, 4M in dioxane) at room temperature and the reaction was stirred for 2 h. The reaction was concentrated under reduced pressure to afford compound D as an HCl salt (30 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (39 mg, 104 μmol) and N-methyl-4-(piperazin-1-yl)pyrimidin-2-aminehydrochloride (30 mg, 131 μmol) were reacted according to Example 536 to give the title compound 561 (12.9 mg, 15%) as a white solid. LCMS: $[M+1]^+$=550.25. $^1H$ NMR (400 MHz, Chloroform-d) δ 7.91 (d, J=6.0 hz, 1H), 5.87 (d, J=6.0 hz, 1H), 5.35 (d, J=5.2 hz, 1H), 4.87 (s, 1H), 3.69 (dd, J=7.3,4.0 hz, 4H), 3.56-3.52 (m, 5H), 2.94 (d, J=5.0 hz, 3H), 2.44-2.37 (m, 1H), 2.31-2.19 (m, 3H), 2.00 (dt, J=12.6, 3.6 hz, 2H), 1.84-1.80 (m, 4H), 1.49-1.39 (m, 7H), 1.38-1.27 (m, 4H), 1.20-1.05 (m, 4H), 1.01 (s, 3H), 0.96 (d, J=6.4 hz, 4H), 0.69 (s, 3H).

Example 562: (R)-1-(4-(2-(dimethylamino)pyrimidin-4-yl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

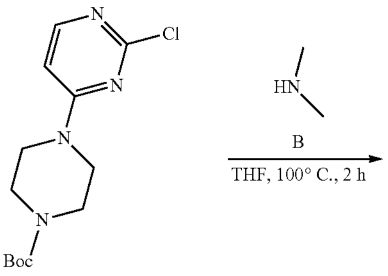

A

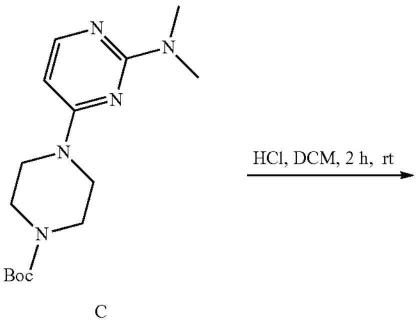

C

-continued

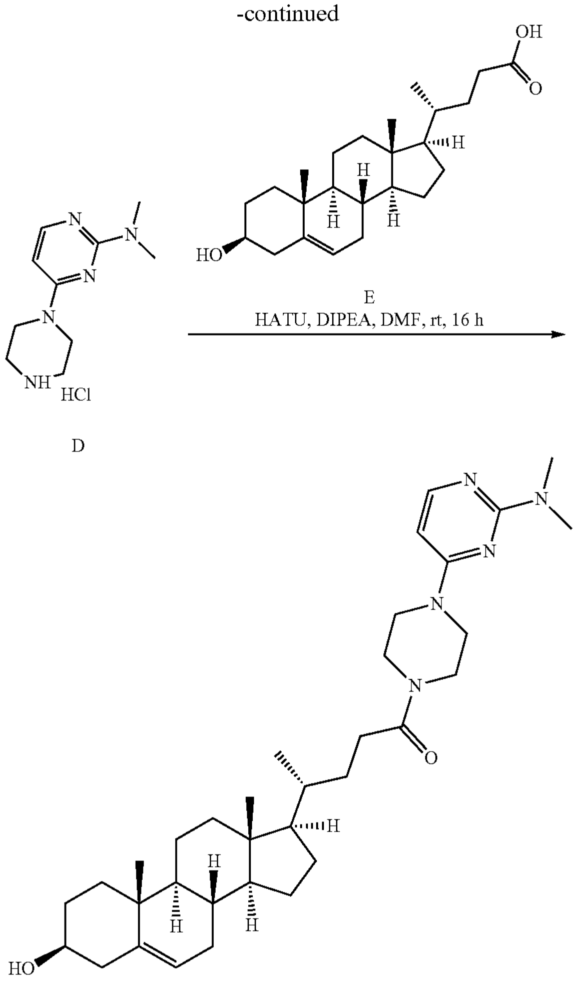

To a solution of compound A (50 mg, 167 μmol) in THF (2 mL) was added compound B (2 M in THF, 0.65 mL). The reaction vessel was sealed and heated in microwave at 100° C. for 2 h. The reaction was cooled to room temperature, diluted with saturated aqueous $NH_4Cl$ (aq, 30 mL) and extracted with EtOAc (10 mL*2). The combined organic layers were washed with water (20 mL), brine (20 mL), dried over sodium sulfate and concentrated under reduced pressure to afford compound C (45 mg, 87%) as a yellow solid.

To a solution of compound C (45 mg, 146 μmol) in DCM (2 mL) was added hydrogen chloride (2 mL, 8 mmol, 4M in dioxane) at room temperature and the reaction was stirred for 2 h. The reaction was concentrated under reduced pressure to afford compound D as an HCl salt (32 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (39 mg, 104 μmol), N,N-dimethyl-4-(piperazin-1-yl)pyrimidin-2-aminehydrochloride (32 mg, 131 μmol), to give the title compound 562 (9 mg, 12%) as a white solid. LCMS: $[M+1]^+$=564.30. $^1H$ NMR (400 MHz, Chloroform-d) δ 7.97 (d, J=5.8 hz, 1H), 5.82 (d, J=5.6 hz, 1H), 5.34 (d, J=4.8 hz, 1H), 3.67 (s, 4H), 3.59-3.46 (m, 5H), 3.13 (s, 6H), 2.44-2.36 (m, 1H), 2.32-2.20 (m, 3H), 1.99 (t, J=13.4 hz, 2H), 1.87-1.69 (m, 7H), 1.60-1.44 (m, 7H), 1.37-1.27 (m, 3H), 1.11-1.02 (m, 4H), 1.01 (s, 3H), 0.97 (d, J=6.2 hz, 3H), 0.69 (s, 3H).

Example 563: (R)-1-(4-(2-ethoxypyrimidin-4-yl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

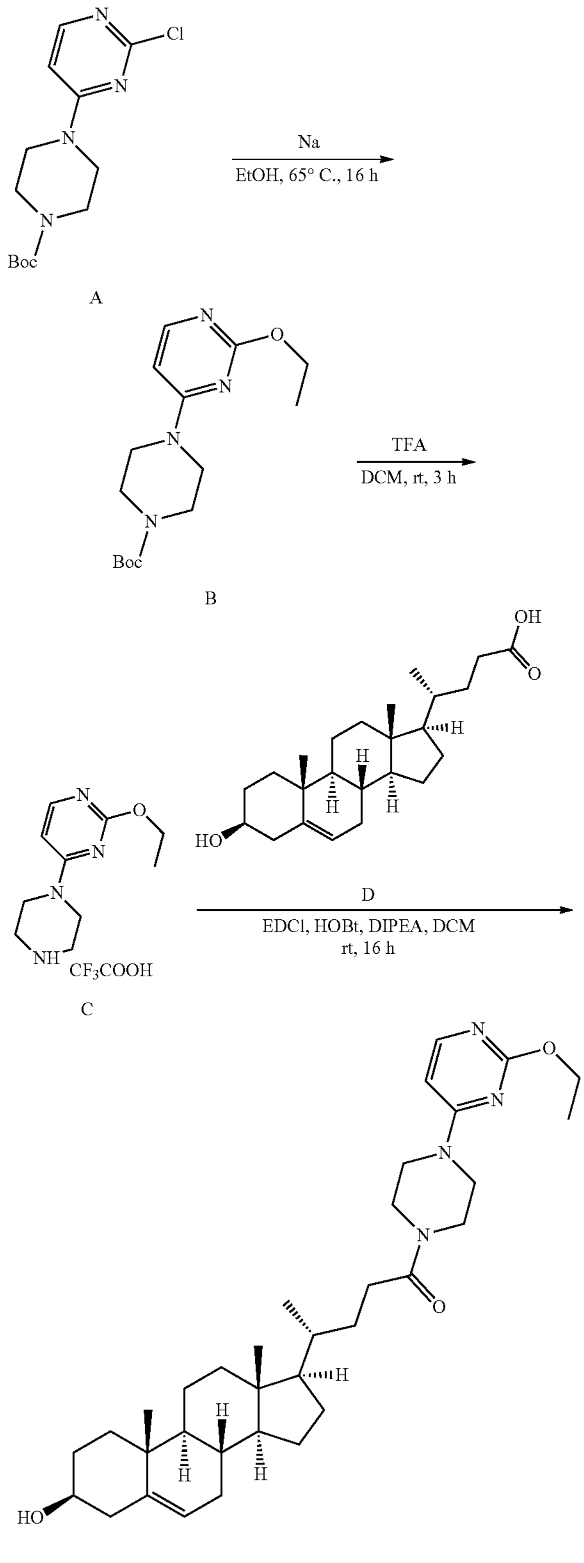

To a solution of compound A (200 mg, 66.9 umol) in EtOH (4 mL) was added NaH (268 mg, 6.69 mmol, 60% dispersion in mineral oil) and the reaction was stirred at 65° C. for 16 h. The reaction was quenched with water (20 mL) and extracted with EtOAc (60 mL). The organic layer was washed by brine (50 mL), dried over sodium sulfate, filtered, and concentrated under reduced pressure. The residue was purified by silica gel chromatography to afford compound B (200 mg, 97%) as a light yellow solid.

To a solution of compound B (200 mg, 649 μmol) in DCM (5 mL) was added TFA (1 mL). The reaction was stirred at room temperature for 3 h. The reaction was concentrated under reduced pressure to afford compound C as the TFA salt (250 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (187 mg, 499 μmol) and 2-ethoxy-4-(piperazin-1-yl)pyrimidine 2,2,2-trifluoroacetate (250 mg, 649 μmol) were reacted according to the method of Example 626 to give the title compound 563 (45.8 mg, 10%) as a white solid. LCMS: [M+1]=565.60. $^1$H NMR (400 MHz, $CDCl_3$): 8.06 (d, J=6.0 hz, 1H), 6.17 (d, J=6.0 hz, 1H), 5.35 (d, J=5.2 hz, 1H), 4.35 (q, J=7.2 hz, 2H), 3.72 (dd, J=13.2, 6.2 hz, 4H), 3.55-3.51 (m, 5H), 2.39 (d, J=10.6 hz, 1H), 2.26-2.21 (m, 3H), 1.99 (t, J=13.8 hz, 2H), 1.89-1.79 (m, 4H), 1.55-1.45 (m, 6H), 1.41 (q, J=7.2, 4H), 1.34-1.25 (m, 2H), 1.20-1.06 (m, 4H), 1.03-0.89 (m, 9H), 0.69 (s, 3H).

Example 564 (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-{4-[2-(2-hydroxyethoxy)pyrimidin-4-yl]piperazin-1-yl}pentan-1-one

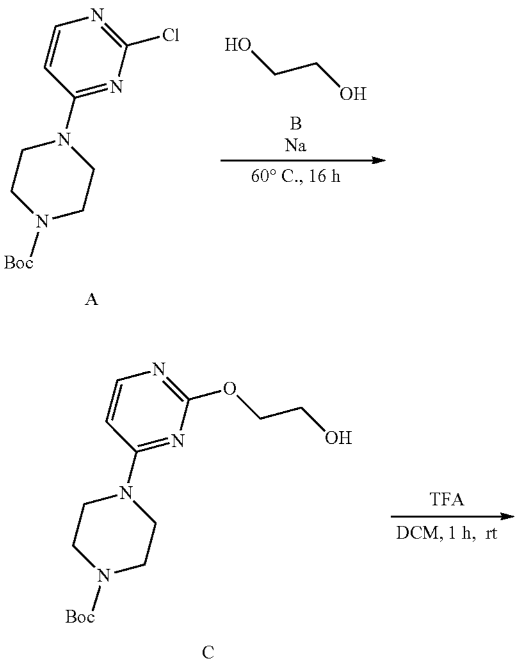

-continued

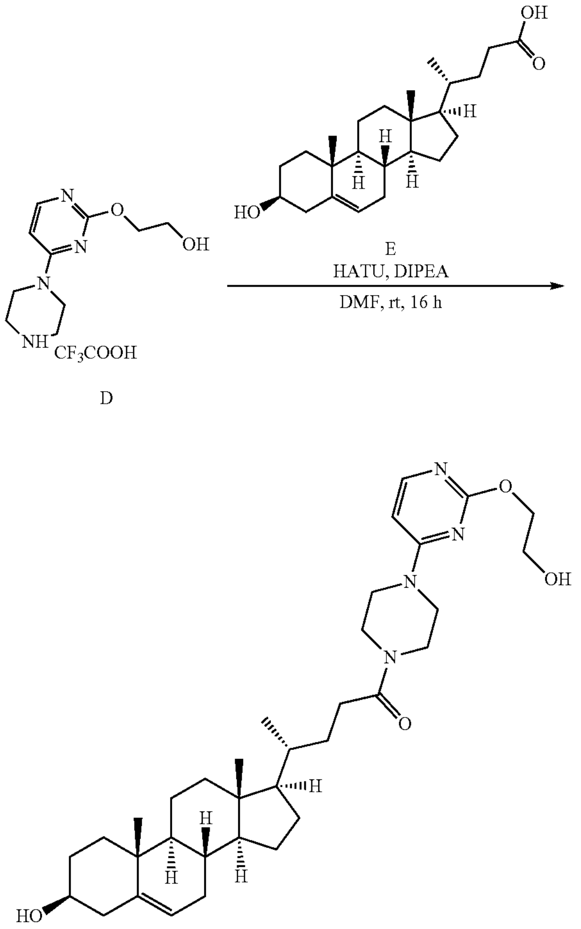

To a solution of compound A (50 mg, 167 μmol) in neat compound B (10 mL), was added NaH (24.1 mg, 0.60 mmol, 60% dispersion in mineral oil) at 0° C. The reaction was heated to 60° C. under $N_2$ for 16 h. The reaction was cooled to room temperature and concentrated under reduced pressure. The residue was purified by silica gel chromatography to afford compound C (30 mg, 55%) as white solid.

To a solution of compound C (30 mg, 92.5 μmol) in DCM (6 mL) was added TFA (2 mL) at room temperature and the reaction was stirred for 2 h. The reaction was concentrated under reduced pressure to afford compound D as the TFA salt (34 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (30 mg, 89.2 μmol) and 2-((4-(piperazin-1-yl)pyrimidin-2-yl)oxy)ethan-1-ol 2,2,2-trifluoroacetate (26 mg, 71.3 μmol) were reacted according to Example 536 to give the title compound 564 (14.9 mg, 36%) as a white solid. LCMS: $[M+1]^+$=581.35. $^1$H NMR (400 MHz, Chloroform-d) δ 8.03 (d, J=6.0 hz, 1H), 6.21 (d, J=6.0 hz, 1H), 5.35 (d, J=5.2 hz, 1H), 4.58-4.37 (m, 2H), 3.94 (t, J=4.4 hz, 2H), 3.73 (t, J=9.2 hz, 4H), 3.64-3.47 (m, 5H), 2.49-2.37 (m, 1H), 2.33-2.14 (m, 3H), 1.98 (t, J=12.8 hz, 3H), 1.84 (d, J=12.4 hz, 4H), 1.78-1.59 (m, 7H), 1.46-1.40 (m, 2H), 1.32 (d, J=21.6 hz, 3H), 1.13 (tt, J=16.0, 8.0 hz, 4H), 1.00 (s, 3H), 0.96 (d, J=6.4 hz, 4H), 0.88 (t, J=6.8 hz, 1H), 0.69 (s, 3H).

Examples 565: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3S)-3-methyl-4-(1-methyl-1H-pyrazole-4-carbonyl)piperazin-1-yl]pentan-1-one

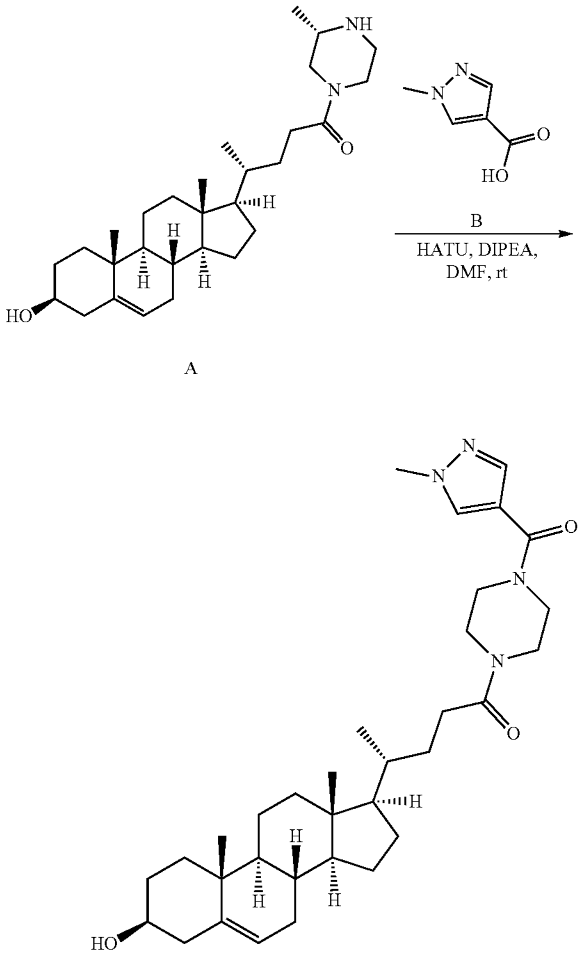

To a solution of compound A (0.1 g, 219 μmol) in DMF (2 mL) was added compound B (27.6 mg, 219 μmol), DIPEA (170 mg, 1.31 mmol) and HATU (167 mg, 438 μmol). The reaction was stirred at room temperature for 16 hours. The reaction was diluted with saturated aqueous $NH_4Cl$ (30 mL) and extracted with EtOAc (10 mL*2). The combined organic layers were washed with saturated $NaHCO_3$ (20 mL), water (20 mL), brine (20 mL), dried over sodium sulfate and concentrated under reduced pressure. The residue was purified by silica gel chromatography to give the title compound 565 (40.1 mg, 32%) as white solid. LCMS: $[M+1]^+$=565.25. $^1H$ NMR (400 MHz, Chloroform-d) δ 7.70 (s, 1H), 7.59 (s, 1H), 5.35 (s, 1H), 4.73 (s, 1H), 4.59 (s, 1H), 4.41-4.39 (m, 1H), 4.17-4.13 (m, 1H), 3.92 (s, 3H), 3.63 (s, 1H), 3.57-3.46 (m, 1H), 3.40-3.11 (m, 2H), 2.93-2.82 (m, 1H), 2.78-2.64 (m, 1H), 2.43-2.19 (m, 4H), 1.98 (t, J=12.3 hz, 2H), 1.90-1.79 (m, 4H), 1.62 (d, J=9.9 hz, 2H), 1.54-1.42 (m, 7H), 1.34-1.23 (m, 5H), 1.22-1.02 (m, 5H), 1.00 (s, 3H), 0.95 (t, J=7.4 hz, 4H), 0.68 (s, 3H).

Example 566: Methyl (2S)-4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]-2-methylpiperazine-1-carboxylate

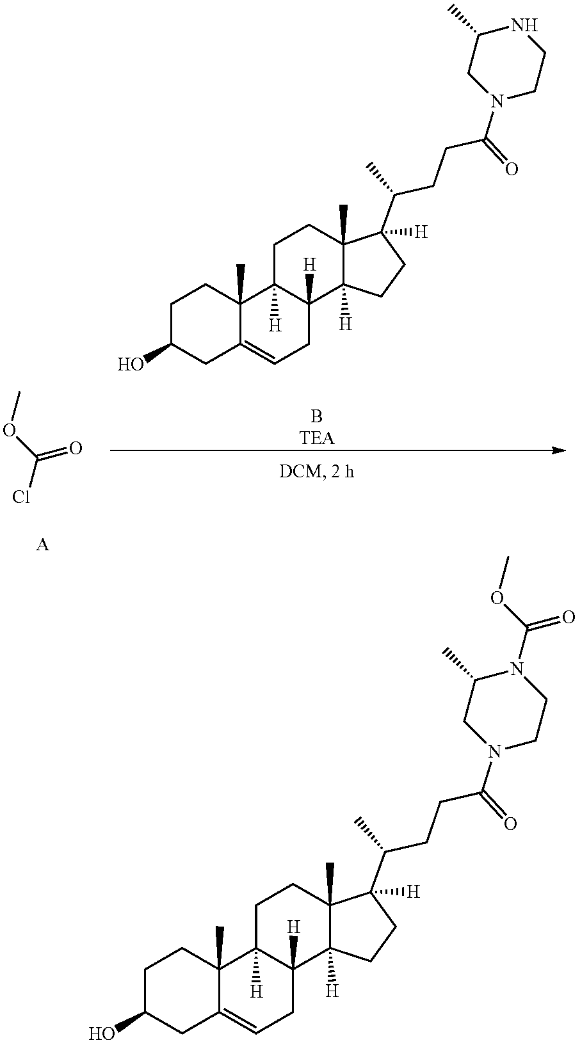

To a solution of compound A (200 mg, 2.13 mmol) and DIPEA (411 mg, 3.19 mmol) in DCM (5 mL) was slowly added compound B (971 mg, 2.13 mmol) at 0° C. The reaction was warmed to room temperature under $N_2$ and stirred for 2 h. The reaction was diluted with saturated aqueous $NH_4Cl$ (30 mL) and extracted with EtOAc (10 mL*2). The combined organic layer was washed with saturated $NaHCO_3$ (20 mL), water (20 mL), brine (20 mL), dried over sodium sulfate and concentrated under reduced pressure. The residue was purified by silica gel chromatography to give the title compound 566 (51 mg, 4.6%) as a white solid. LCMS: $[M+1]^+$=515.25. $^1H$ NMR (400 MHz, Chloroform-d) δ 5.35 (d, J=5.2 hz, 1H), 4.32 (d, J=13.2 hz, 1H), 3.93-3.87 (m, 1H), 3.72 (s, 3H), 3.64-3.48 (m, 2H), 3.31 (dd, J=13.6, 3.6 hz, 1H), 3.21-3.01 (m, 1H), 2.44-2.14 (m, 4H), 2.05-1.92 (m, 2H), 1.90-1.73 (m, 4H), 1.56-1.40 (m, 7H), 1.37-1.23 (m, 3H), 1.21-1.03 (m, 7H), 1.00 (s, 4H), 0.95 (t, J=6.4 hz, 4H), 0.68 (s, 3H).

Example 567: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-methyl-4-(pyridin-4-yl)piperazin-1-yl)pentan-1-one

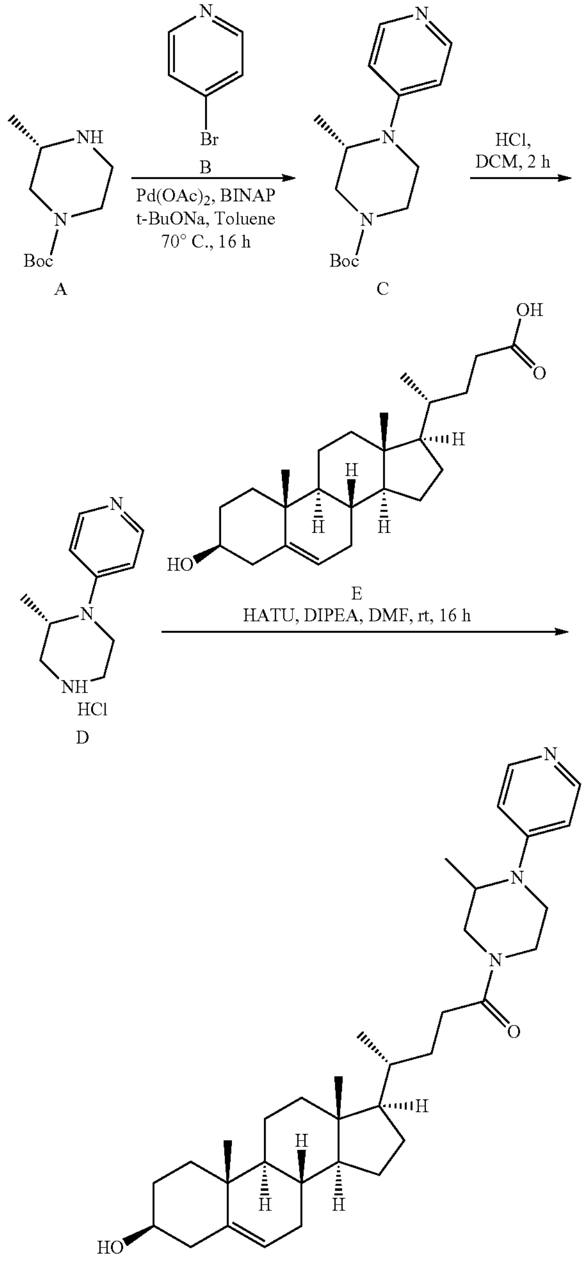

To a solution of compound A (100 mg, 499 μmol) in toluene (2 mL) was added compound B (95 mg, 599 μmol), t-BuONa (144 mg, 1.5 mmol), BINAP (15.5 mg, 25 μmol), $Pd(OAc)_2$ (5.6 mg, 25 μmol) and the reaction was heated to 70° C. under $N_2$ for 16 h. The reaction was cooled to room temperature, diluted with saturated aqueous $NH_4Cl$ (30 mL) and extracted with EtOAc (10 mL*2). The combined organic layers were washed with water (20 mL), brine (20 mL), dried over sodium sulfate and concentrated under reduced pressure to afford compound C (50 mg, 36%) as yellow oil.

To a solution of compound C (50 mg, 180 μmol) in DCM (2 mL) was added hydrogen chloride (1 mL, 4 mmol, 4M in dioxane) at room temperature and the reaction was stirred for 2 h. The reaction was concentrated under reduced pressure to afford compound D as an HCl salt (30 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (43 mg, 113 μmol) and(S)-2-methyl-1-(pyridin-4-yl)piperazinehydrochloride (30 mg, 141 μmol) were reacted according to Example 536 to give the title compound 567 (13 mg, 17%) as a white solid. LCMS: $[M+1]^+$=534.20. $^1$H NMR (400 MHz, Chloroform-d) δ 8.31 (d, J=5.6 hz, 2H), 6.67 (d, J=5.6 hz, 2H), 5.39 (d, J=4.8 hz, 1H), 4.52-4.37 (m, 1H), 4.16 (d, J=6.4 hz, 1H), 3.94 (d, J=13.0 hz, 1H), 3.81-3.68 (m, 1H), 3.66-3.52 (m, 3H), 3.43 (t, J=11.1 hz, 1H), 3.20-3.12 (m, 2H), 3.03 (t, J=12.4 hz, 1H), 2.46-2.25 (m, 4H), 2.07-1.99 (m, 2H), 1.88 (d, J=12.2 hz, 4H), 1.66-1.47 (m, 7H), 1.34 (s, 3H), 1.19-1.11 (m, 5H), 1.11 (d, J=4.8 hz, 1H), 1.04 (s, 4H), 1.00 (q, J=6.0 hz, 4H), 0.73 (s, 3H).

Example 568: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-methyl-4-(pyrazine-2-carbonyl)piperazin-1-yl)pentan-1-one

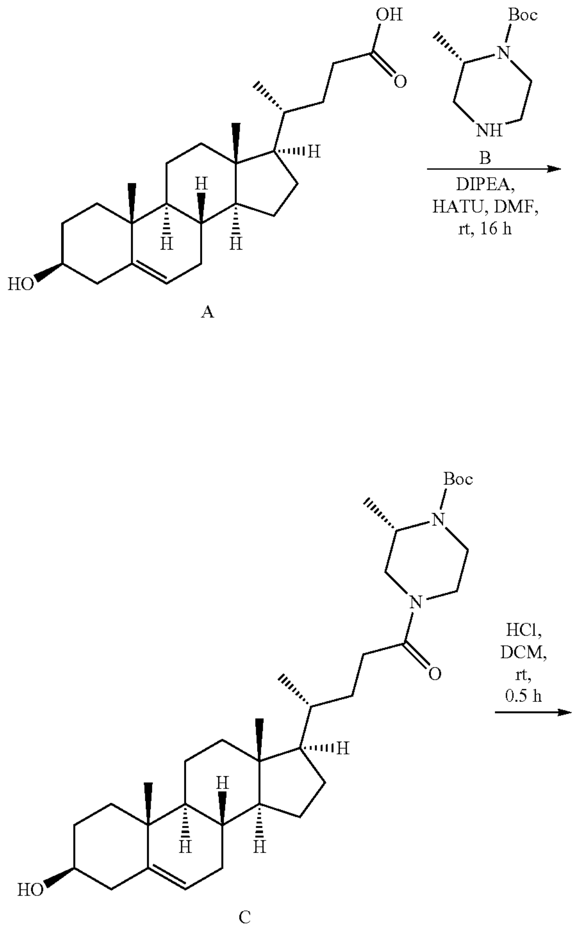

-continued

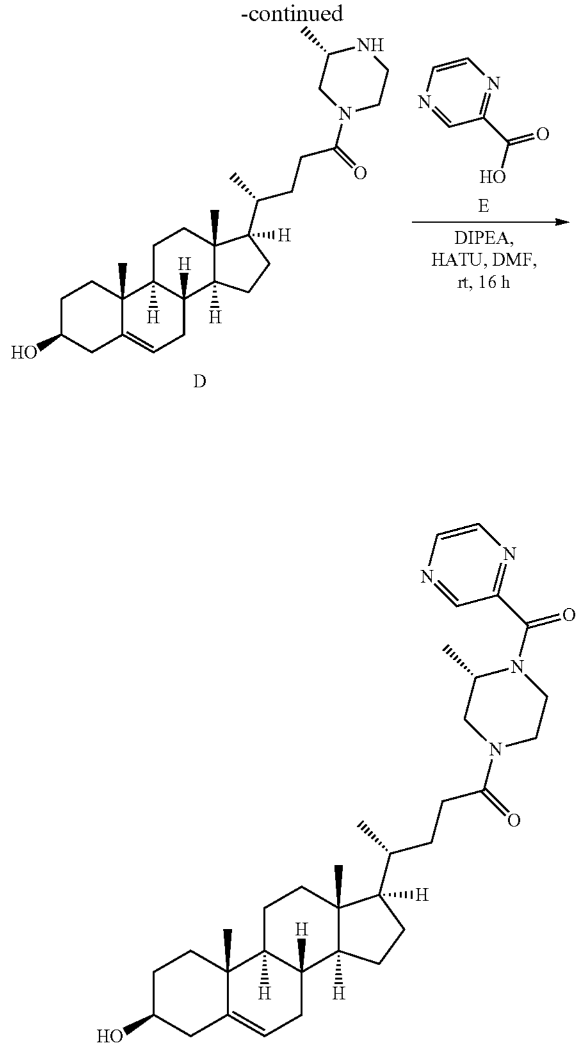

To a solution of compound A (3.0 g, 8.01 mmol), compound B (1.6 g, 8.01 mmol) and DIPEA (6.2 g, 48 mmol) in DMF (30 mL) was added HATU (6.1 g, 16 mmol) at room temperature under $N_2$ and stirred for 16 h. The reaction was diluted with saturated aqueous $NH_4Cl$ (150 mL) and extracted with EtOAc (50 mL*2). The combined organic layers were washed with water (50 mL), brine (100 mL), dried over sodium sulfate and concentrated under reduced pressure. The residue was purified by silica gel chromatography to afford compound C (3.5 g, 78.5%) as a white solid.

To a solution of compound C (2 g, 3.59 mmol) in DCM (20 mL) was added hydrogen chloride (10 mL, 40 mmol, 4M in dioxane) at room temperature and the reaction was stirred for 0.5 h. The reaction was concentrated under reduced pressure to afford compound D as an HCl salt (1.7 g).

To a solution of compound D (150 mg, 304 μmol), compound E (45 mg, 361 μmol) and DIPEA (254 mg, 1.97 mmol) in DMF (3 mL) was added HATU (250 mg, 656 μmol) at room temperature under $N_2$ and stirred for 16 h. The reaction was diluted with saturated aqueous $NH_4Cl$ (20 mL) and extracted with EtOAc (10 mL*2). The combined organic layers were washed with water (15 mL), brine (20 mL), dried over sodium sulfate and concentrated under reduced pressure. The residue was purified by silica gel chromatography to afford compound 568 (110 mg, 60%) as a white solid. LCMS: rt: 1.37, 563.20 [M+1]. $^1$H NMR (400 MHz, Chloroform-d) δ 8.94 (s, 1H), 8.65 (d, J=2.4 hz, 1H), 8.54 (s, 1H), 5.34 (d, J=5.0 hz, 1H), 4.72-4.26 (m, 2H), 3.99-3.67 (m, 1H), 3.55-3.28 (m, 2H), 3.18-2.75 (m, 2H), 2.41-2.18 (m, 4H), 1.98 (t, J=12.4 hz, 2H), 1.90-1.77 (m, 4H), 1.50-1.48 (m, 8H), 1.30-1.33 (m, 6H), 1.11-1.05 (m, 4H), 1.00-0.87 (m, 4H), 0.96-0.91 (m, 3H), 0.68 (s, 3H).

Example 569: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-methyl-4-propionylpiperazin-1-yl)pentan-1-one

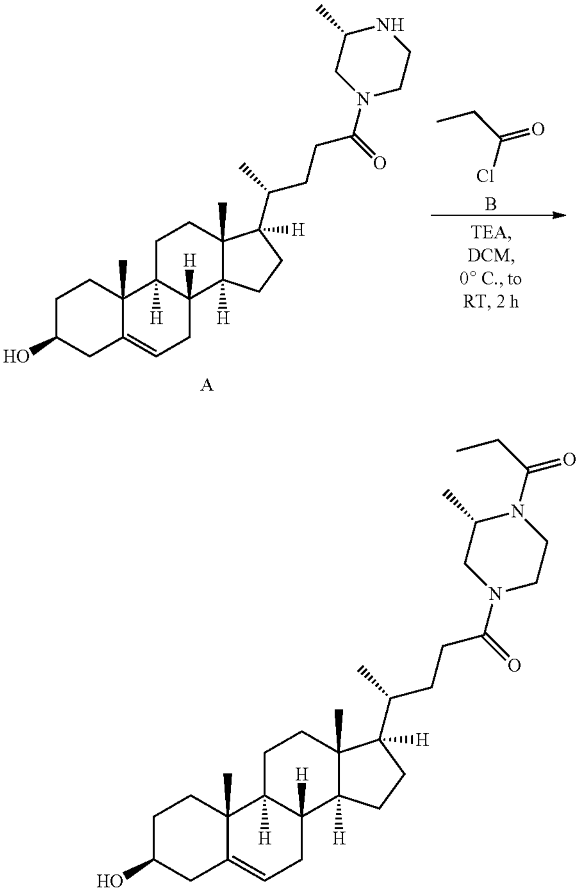

To a solution of compound A (100 mg, 219 μmol) and TEA (33.2 mg, 328 μmol) in dichloromethane (2 mL) was added compound B (20.3 mg, 219 μmol) at 0° C. and stirred under $N_2$ for 2 hours. The reaction was diluted with cold $NaHCO_3$ (20 mL) and extracted with EtOAc (50 mL). The organic layer was washed with brine (20 mL), dried over sodium sulfate and concentrated under reduced pressure. The crude material was purified by silica gel chromatography to give the title compound 569 (40 mg, 36%) as white solid. LCMS: $[M+1]^+$=513.25. $^1$H NMR (400 MHz, Chloroform-d) δ 5.42-5.29 (m, 1H), 4.93-3.75 (m, 3H), 3.62 (d, J=12.0 hz, 1H), 3.55-3.48 (m, 1H), 3.35-2.55 (m, 3H), 2.44-2.15 (m, 6H), 1.98 (t, J=12.0 hz, 2H), 1.89-1.76 (m, 4H), 1.58-1.38 (m, 7H), 1.38-1.24 (m, 3H), 1.23-1.03 (m, 10H), 1.00 (s, 3H), 0.97-0.88 (m, 4H), 0.68 (s, 3H).

Example 570: Cyclopropyl(S)-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-2-methylpiperazine-1-carboxylate

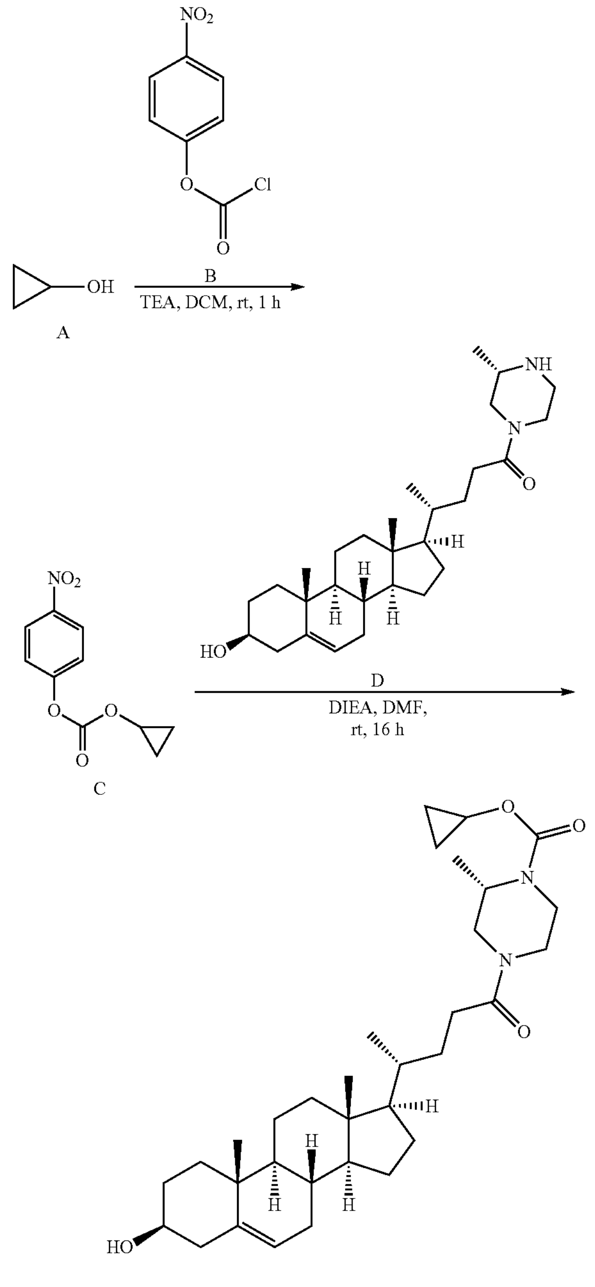

To a solution of compound A (200 mg, 3.44 mmol) and TEA (523 mg, 5.17 mmol) in DCM (10 mL) was added compound B (694 mg, 3.44 mmol) at 0° C. and stirred under $N_2$ for 2 hours. The reaction was concentrated under reduced pressure and purified by silica gel chromatography to afford compound C (0.6 g, 2.69 mmol) as an off-white solid.

To a solution of compound D (100 mg, 219 μmol) and DIPEA (84.9 mg, 657 μmol) in DMF (2 mL) was added compound C (73.3 mg, 328 μmol) at room temperature under $N_2$ for 2 hours. The reaction was stirred at room temperature for 16 hours. The reaction was diluted with HCl (1M, 20 mL) and extracted with EtOAc (50 mL), washed with $NaHCO_3$ (20 mL) and water (20 mL*3). The combined organic layer was washed with brine (20 mL), dried over sodium sulfate and concentrated under reduced pressure to give the crude and purified by silica gel chromatography to give the title compound 570 (45 mg, 38%) as a colorless solid. LCMS: $[M+1]^+$=541.25. $^1$HNMR (400 MHz, Chloroform-d) δ 5.44-5.30 (m, 1H), 4.53-4.21 (m, 2H), 4.09 (s, 1H), 4.00-3.41 (m, 3H), 3.35-2.59 (m, 3H), 2.44-2.14 (m, 4H), 2.02-1.93 (m, 2H), 1.89-1.74 (m, 4H), 1.57-1.39 (m, 7H), 1.35-1.24 (m, 4H), 1.19-1.02 (m, 7H), 1.00 (s, 3H), 0.94 (t, J=6.4 hz, 4H), 0.73-0.65 (m, 6H).

Example 571: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((3S,4S)-3-methyl-4-(pyridin-4-yloxy)piperidin-1-yl)pentan-1-one

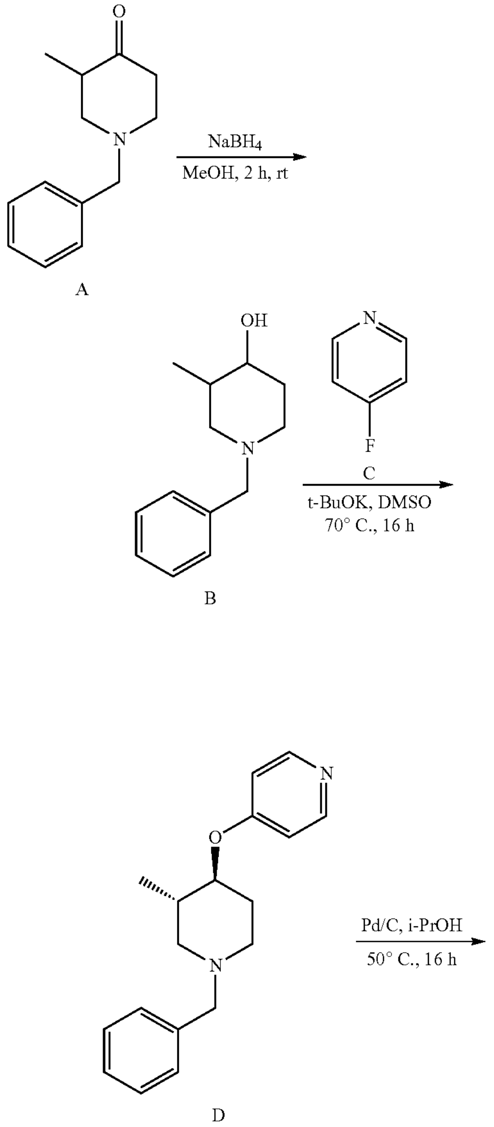

-continued

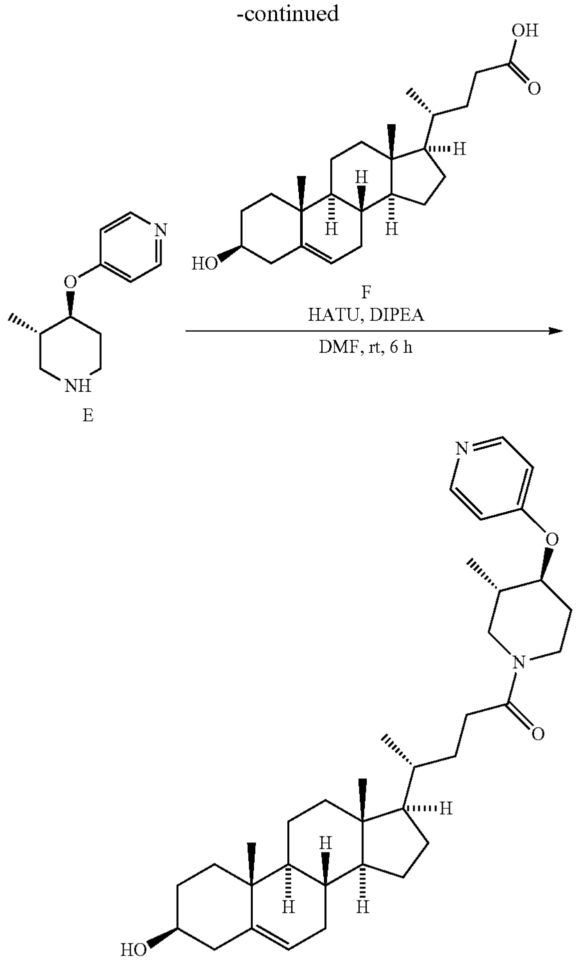

To a solution of compound A (2 g, 9.84 mmol) in methanol (40 mL) was added $NaBH_4$ (1.86 g, 49.2 mmol) at 0° C., the reaction was warmed to room temperature and stirred for 2 hours under $N_2$. The reaction was quenched with water (10 mL) and extracted with DCM (100 mL). The organic layer was concentrated under reduced pressure. The crude product was purified by silica gel chromatography to afford compound B (1.8 g, 89%).

To a solution of compound B (1.5 g, 7.31 mmol) in DMSO (25.7 mL) was added compound C (709 mg, 7.31 mmol), t-BuOK (2.46 g, 21.9 mmol) and the reaction was stirred at 70° C. for 16 hours. Upon completion, the reaction was diluted with water (50 mL) and extracted with ethyl acetate (200 mL). The organic layer was concentrated under reduced pressure. The crude product was purified by silica gel chromatography to afford compound D (1.8 g, 88%).

To a solution of compound D (1.8 g, 6.37 mmol) in propan-2-ol (20 mL) was added 10% Pd/C (180 mg), the reaction was stirred at 50° C. for 16 hours underh$_2$. Upon completion the reaction was filtered. The organic layer was concentrated under reduced pressure. The crude product was purified by silica gel chromatography to afford compound E (800 mg, 65%).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (200 mg, 534 μmol) and 4-(((3S,4S)-3-methylpiperidin-4-yl)oxy)pyridine (103 mg, 534 μmol) were reacted according to Example 536 to give the title compound 571 (200 mg, 68%) as white solid. LCMS: $[M+1]^+$=549.45. $^1$H NMR (400 MHz, Chloroform-d) δ 8.45-8.38 (m, 2H), 6.84 (s, 2H), 5.35 (s, 1H), 4.17 (s, 1H), 3.78 (d, J=15.2 hz, 1H), 3.51 (td, J=10.2, 4.8 hz, 1H), 3.32-3.16 (m, 1H), 3.01 (s, 1H), 2.84-2.74 (m, 1H), 2.39 (s, 1H), 2.26-2.21 (m, 3H), 2.03-1.97 (m, 2H), 1.92-1.87 (m, 4H), 1.84 (d, J=11.8 hz, 3H), 1.60 (s, 2H), 1.54-1.50 (m, 2H), 1.50-1.48 (m, 2H), 1.44 (s, 3H), 1.31 (d, J=12.4 hz, 2H), 1.25-1.12 (d, 4H), 1.07-0.89 (s, 7H), 0.96 (dd, J=6.4, 4.2 hz, 4H), 0.69 (d, J=2.8 hz, 3H).

Example 572: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((3S,4R)-3-methyl-4-(pyridin-4-yloxy)piperidin-1-yl)pentan-1-one

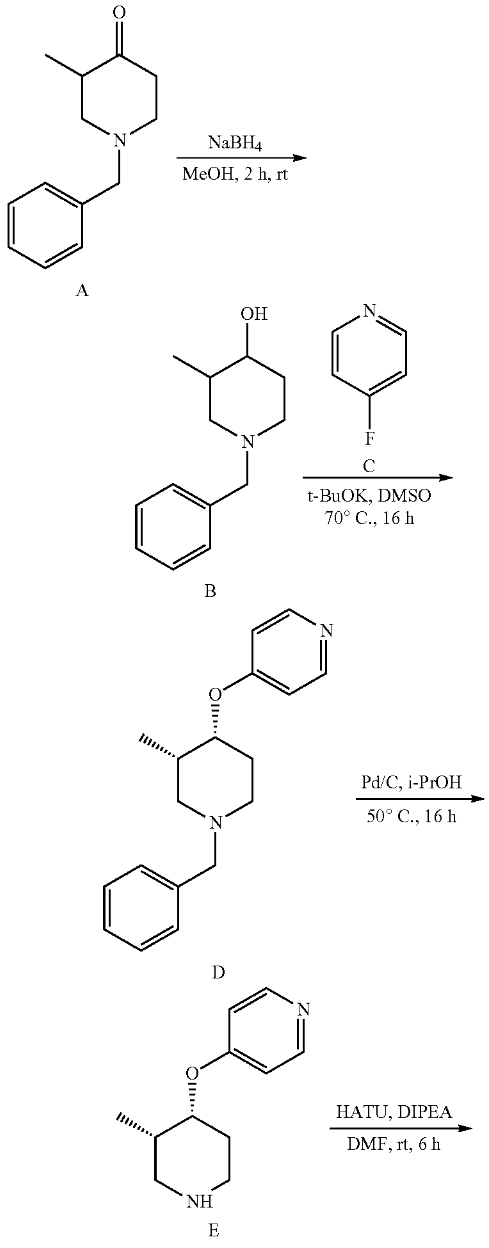

-continued

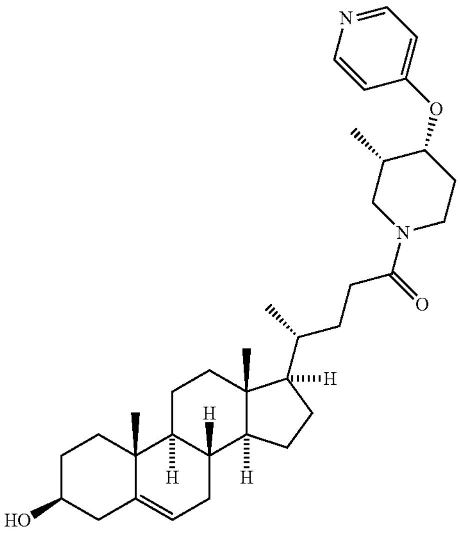

To a solution of compound A (2 g, 9.84 mmol) in methanol (40 mL) was added $NaBH_4$ (1.86 g, 49.2 mmol) at 0° C. and the reaction was stirred at room temperature for 2 hours under $N_2$. The reaction was quenched with water (10 mL) and extracted with DCM (100 mL). The organic layer was concentrated under reduced pressure. The crude product was purified by silica gel chromatography to afford compound B (1.8 g, 89%).

To a solution of compound B (1.5 g, 7.31 mmol) in DMSO (25.7 mL) was added compound C (709 mg, 7.31 mmol), t-BuOK(2.46 g, 21.9 mmol) and the reaction was stirred at 70° C. for 16 hours. Upon completion the reaction was diluted with water (50 mL) and extracted with ethyl acetate (200 mL). The organic layer was concentrated under reduced pressure. The crude product was purified by silica gel chromatography to afford compound D (1.8 g, 88%).

To a solution of compound D (1.8 g, 6.37 mmol) in propan-2-ol (20 mL) was added 10% Pd/C (180 mg), the reaction was stirred at 50° C. for 16 hours underh$_2$. Upon completion the reaction was filtered and concentrated under reduced pressure. The crude product was purified by silica gel chromatography to afford compound E (800 mg, 65%).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (200 mg, 534 μmol) and 4-(((3S,4R)-3-methylpiperidin-4-yl)oxy)pyridine (103 mg, 534 μmol) were reacted according to Example 536 to give the title compound 572 (200 mg, 68%) as white solid. LCMS: $[M+1]^+$=549.45. $^1$H NMR (400 MHz, Chloroform-d) δ 8.48 (s, 2H), 6.93-6.88 (m, 2H), 5.35 (s, 1H), 4.62 (s, 1H), 4.24-4.13 (m, 1H), 3.62-3.33 (m, 4H), 3.11-2.88 (m, 3H), 2.43-2.20 (m, 5H), 2.00 (d, J=11.6 hz, 4H), 1.84-1.85 (m, 5H), 1.47-1.38 (m, 5H), 1.29-1.22 (m, 6H), 1.17-1.01 (s, 7H), 0.96 (t, J=6.8 hz, 4H), 0.69 (d, J=3.6 hz, 3H).

Examples 573: (2S)-4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoyl]-N,N,2-trimethylpiperazine-1-carboxamide

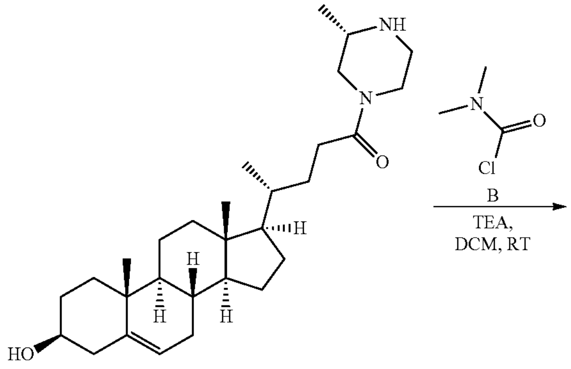

A

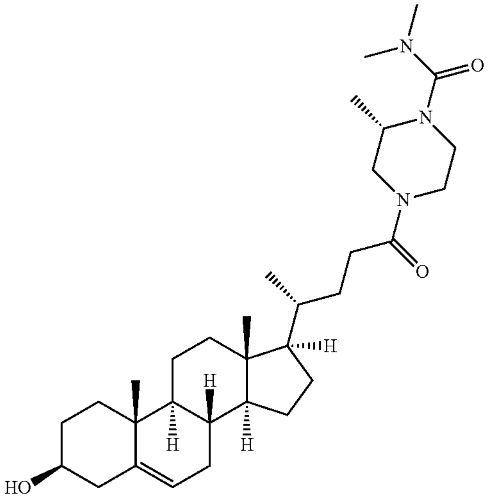

To a solution of compound A (100 mg, 219 μmol) in DCM (2 mL) was added TEA (33.2 mg, 328 μmol) and compound B (23.5 mg, 219 μmol) at 0° C. The reaction was warmed to room temperature and stirred for 2 hours. The reaction was extracted with EtOAc (10 mL*2). The combined organic layers were washed with saturated $NaHCO_3$ (20 mL), water (20 mL), brine (20 mL), dried over sodium sulfate and concentrated under reduced pressure. The residue was purified by silica gel chromatography to give the title compound 573 (37.9 mg, 32%) as white solid. LCMS: $[M+1]^+$=551.25. $^1$H NMR (400 MHz, Chloroform-d) δ 5.41-5.23 (m, 1H), 4.44-4.16 (m, 1H), 4.00-3.77 (m, 1H), 3.52 (t, J=12.8 hz, 1H), 3.46-3.35 (m, 1H), 3.34-3.21 (m, 1H), 3.20-3.06 (m, 1H), 3.00-2.91 (m, 1H), 2.83-2.75 (m, 6H), 2.45-2.15 (m, 4H), 1.98 (t, J=12.3 hz, 2H), 1.90-1.70 (m, 4H), 1.49-1.37 (m, 8H), 1.38-1.24 (m, 3H), 1.20 (d, J=6.8 hz, 2H), 1.18-1.03 (m, 5H), 1.00 (s, 3H), 0.95 (t, J=6.4 hz, 4H), 0.68 (s, 3H).

Example 574: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-methyl-4-(1-methyl-1H-1,2,3-triazole-4-carbonyl)piperazin-1-yl)pentan-1-one

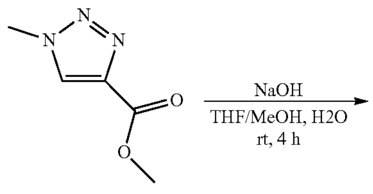

A

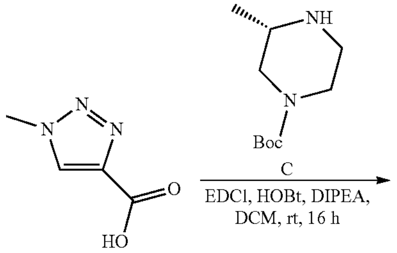

B

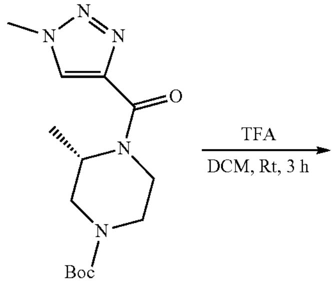

D

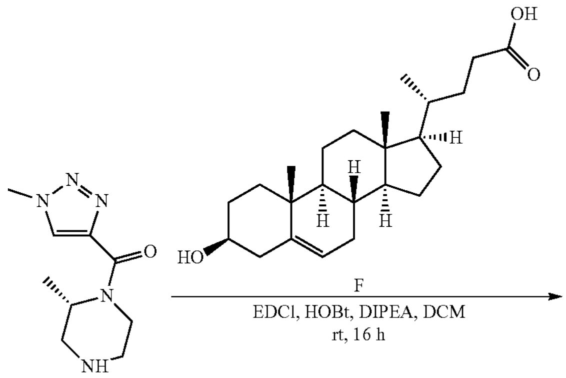

E

-continued

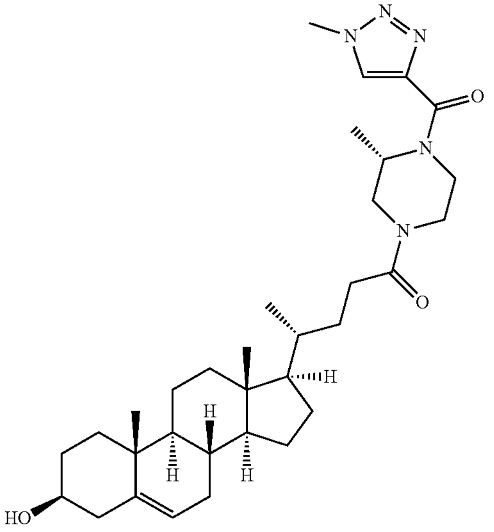

To a solution of compound A (160 mg, 1.13 μmol) in THE (1.6 mL, 19.7 mmol), water (1.6 mL, 88.8 mmol) and methanol (1.6 mL, 39.5 mmol) was added sodiumhydroxide (90.7 mg, 2.27 mmol). The reaction was stirred at room temperature for 4 h. The reaction was quenched with 1MhCl (15 mL) and extracted with EtOAc (30 mL). The organic layer was washed by brine (20 mL), dried over sodium sulfate, filtered, and concentrated under reduced pressure to afford compound B (140 mg, 97%) as a white solid.

To a solution of compound B (70 mg, 551 μmol) in dichloromethane (3 mL) was added compound C (110 mg, 551 μmol), EDCI (213 mg, 1.1 mmol),hOBt (168 mg, 1.1 mmol) and DIPEA (427 mg, 3.3 mmol), the reaction was stirred at room temperature for 16 h. The reaction was quenched with saturated aqueous $NaHCO_3$ (15 mL) and extracted with EtOAc (45 mL). The organic layer was washed by brine, $NaHCO_3$ (30 mL), dried over sodium sulfate, filtered, and concentrated under reduced pressure. The residue was purified by silica gel chromatography to afford compound D (100 mg, 59%) as a white solid.

To a solution of compound D (100 mg, 324 μmol) in dichloromethane (2 mL) was added TFA (0.5 mL), the reaction was stirred at room temperature for 3 h. The reaction was concentrated under reduced pressure to afford compound E (130 mg) as the TFA salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (134 mg, 358 μmol) and (S)-(1-methyl-1H-1,2,3-triazol-4-yl)(2-methylpiperazin-1-yl)methanone (130 mg, 324 μmol) were reacted according to the method of Example 626 to give the title compound 574 (21.8 mg, 11%) as a white solid. LCMS: $[M+1]^+$=566.35. $^1H$ NMR (400 MHz, $CDCl_3$): 8.07 (s, 1H), 5.37-5.32 (m, 1H), 4.91 (s, 1H), 4.47 (d, J=57.8 hz, 2H), 4.14 (s, 3H), 3.68 (d, J=13.6 hz, 1H), 3.56-3.50 (m, 2H), 3.19-3.00 (m, 1H), 2.81-2.79 (m, 1H), 2.46-2.19 (m, 5H), 2.03-1.95 (m, 2H), 1.88-1.78 (m, 4H), 1.49-1.44 (m, 9H), 1.35-1.24 (m, 7H), 1.21-1.07 (m, 4H), 1.00-0.88 (m, 8H), 0.69 (s, 3H)

Example 575: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3S)-3-methyl-4-(pyrimidin-4-yl)piperazin-1-yl]pentan-1-one

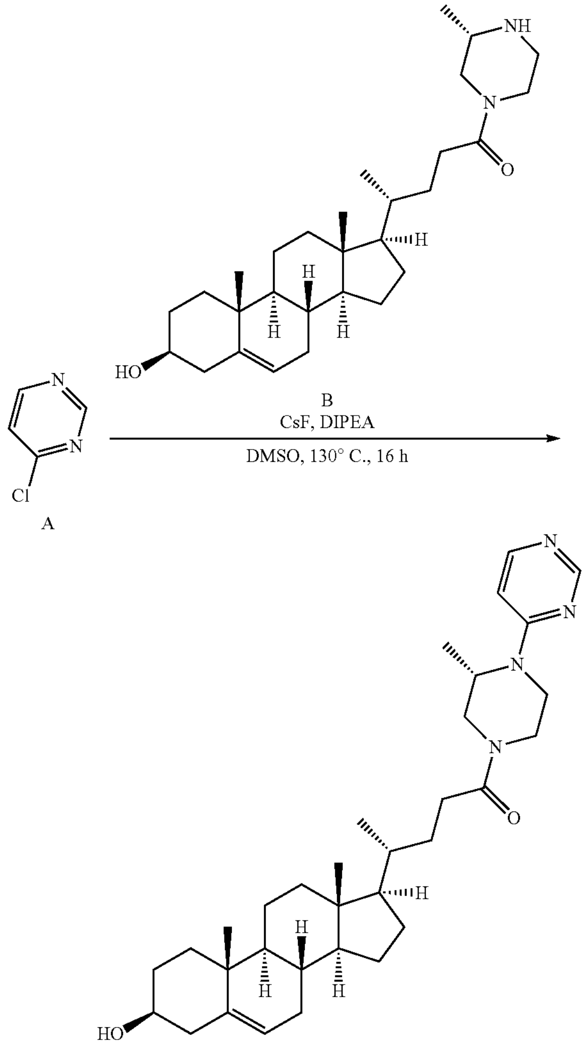

To a solution of compound A (100 mg, 873 μmol) in DMSO (4 mL) was added compound B (399 g, 873 μmol), CsF (398 mg, 2.62 mmol) and DIPEA (677 mg, 5.24 mmol), the reaction was heated to 130° C. under $N_2$ for 16 h. The reaction was cooled to room temperature and concentrated under reduced pressure. The residue was purified by silica gel chromatography to give the title compound 575 (12.4 mg, 2.6%) as yellow solid. LCMS: $[M+1]^+$=535.25. $^1H$ NMR (400 MHz, Chloroform-d) δ 8.63 (s, 1H), 8.24 (s, 1H), 6.51 (d, J=6.0 hz, 1H), 5.35 (d, J=5.2 hz, 1H), 4.57 (d, J=13.4 hz, 1H), 4.37 (d, J=14.4 hz, 2H), 4.04 (d, J=13.2 hz, 1H), 3.87 (d, J=12.4 hz, 1H), 3.73 (d, J=13.2 hz, 1H), 3.58-3.42 (m, 2H), 3.39-3.18 (m, 2H), 3.17-3.07 (m, 1H), 2.91 (t, J=12.0 hz, 1H), 2.44-2.20 (m, 5H), 2.05-1.78 (m, 11H), 1.65-1.53 (m, 3H), 1.48-1.39 (m, 3H), 1.24-1.17 (m, 3H), 1.09-1.01 (m, 4H), 1.01 (s, 3H), 0.96-0.84 (m, 5H), 0.69 (s, 3H).

Example 576: isopropyl(S)-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-2-methylpiperazine-1-carboxylate

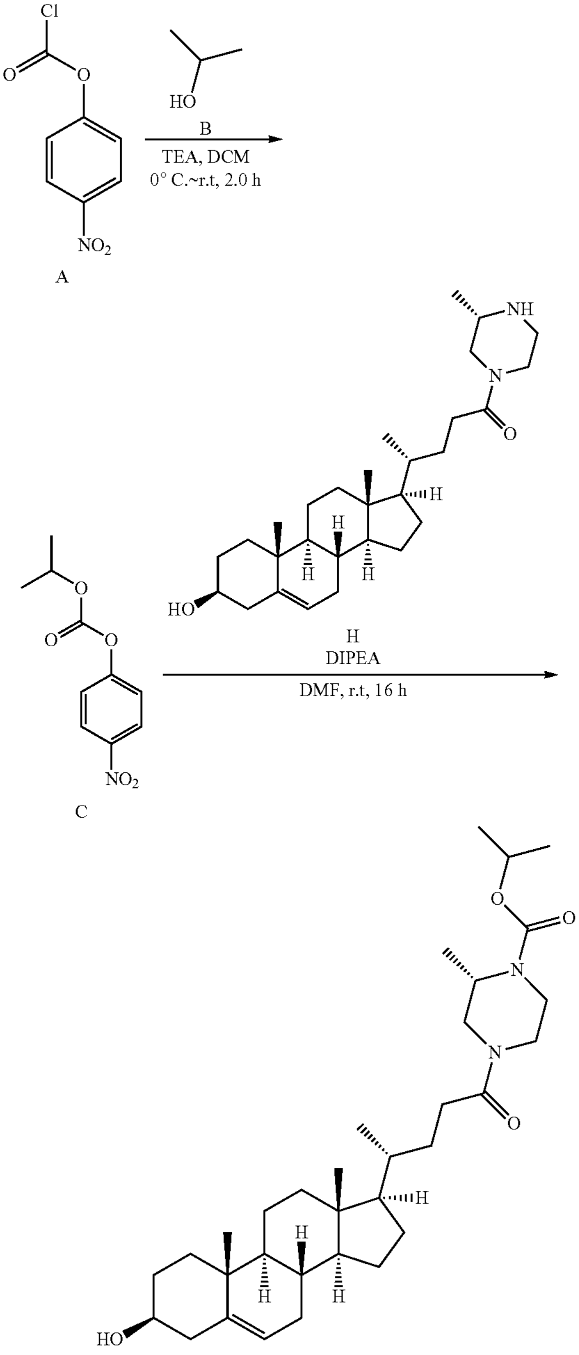

To a solution of A (100 mg, 496 μmol) in DCM (2 mL) was added TEA (75.3 mg, 744 μmol) and B (29.8 mg, 496 μmol). The reaction was stirred at room temperature under $N_2$ for 16 h. The reaction was quenched with water (5 mL) and extracted with EtOAc (20 mL). The organic layer was washed with brine (5 mL), dried over sodium sulfate, filtered, and concentrated under reduced pressure. The residue was purified by silica gel chromatography to afford the compound C (37 mg, 33%).

To a solution of C (37 mg, 164 μmol) in DMF (2 mL) was added D (75 mg, 164 μmol) and DIPEA (127 mg, 986 μmol) and the reaction was stirred at room temperature under $N_2$ for 16 h. The reaction was quenched with saturated aq. $NH_4Cl$ (5 mL) and extracted with EtOAc (20 mL). The organic layer was washed with brine (5 mL), dried over sodium sulfate, filtered, and concentrated under reduced pressure. The residue was purified by silica gel chromatography to give the title compound 576 (42.7 mg, 47.9%) as a white solid. LCMS: $[M+1]^+$=543.45. $^1$H NMR (400 MHz, Chloroform-d) δ 5.34 (d, J=4.8 hz, 1H), 4.94-4.89 (m, 1H), 4.49 (d, J=13.6 hz, 1H), 4.30-4.28 (m, 2H), 3.92-3.87 (m, 1H), 3.61-3.45 (m, 2H), 3.31-3.29 (m, 1H), 3.08-2.88 (m, 3H), 2.41-2.15 (m, 4H), 2.04-1.93 (m, 2H), 1.91-1.73 (m, 4H), 1.61-1.35 (m, 9H), 1.25-1.20 (m, 8H), 1.19-1.05 (m, 7H), 1.00-0.94 (m, 8H), 0.68 (s, 3H).

Example 577: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-4-isonicotinoyl-3-methylpiperazin-1-yl)pentan-1-one

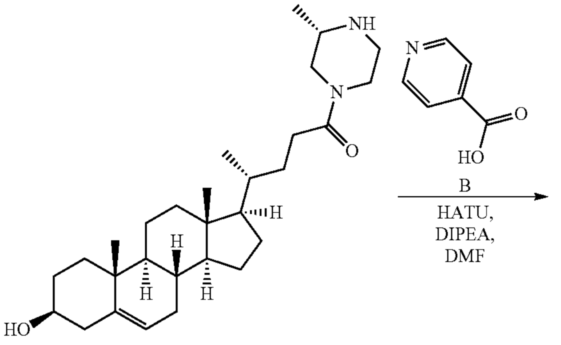

A

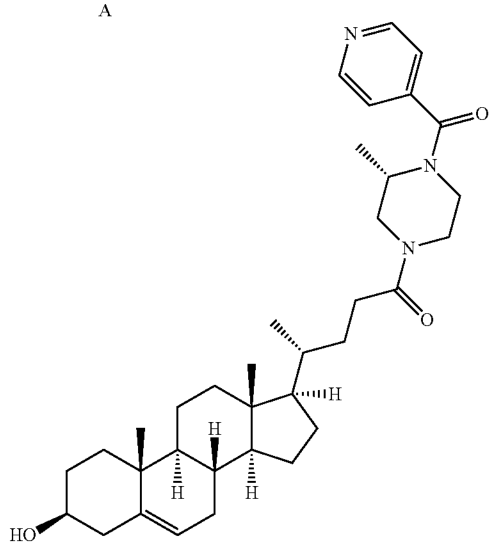

To a solution of B (73 mg, 593 μmol) in DMF (4 mL) was added A (226 mg, 494 μmol), HATU (376 mg, 988 μmol) and DIPEA (383 mg, 2.96 mmol). The reaction was stirred at room temperature under $N_2$ for 16 h. The reaction was quenched with saturated aq. $NH_4Cl$ (5 mL) and extracted with EtOAc (30 mL). The organic layer was washed with brine, dried over sodium sulfate, filtered, and concentrated. The residue was purified by silica gel chromatography to give the title compound 577 (13.9 mg, 15.4%) as a white solid. LCMS: $[M+1]^+$=562.20. $^1$H NMR (400 MHz, Chloroform-d) δ 8.72 (d, J=4.8 hz, 2H), 7.27 (s, 2H), 5.34 (d, J=5.2 hz, 1H), 5.02-4.37 (m, 2H), 3.77-3.65 (m, 1H), 3.51-3.46 (m, 1H), 3.37-3.18 (m, 2H), 2.82-2.63 (m, 1H), 2.50-2.16 (m, 4H), 2.01-1.98 (m, 2H), 1.91-1.77 (m, 4H), 1.56-1.03 (m, 20H), 1.00-0.84 (m, 8H), 0.68 (s, 3H).

Example 578: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-2-methyl-4-(1-methyl-1H-pyrazole-4-carbonyl)piperazin-1-yl)pentan-1-one

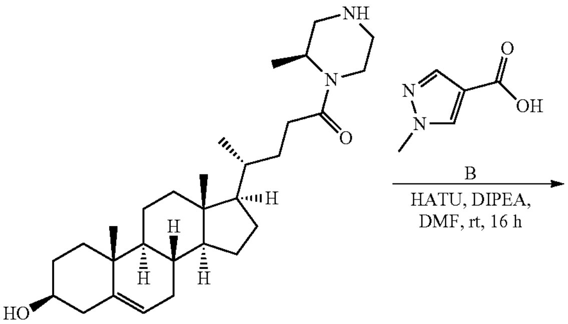

A

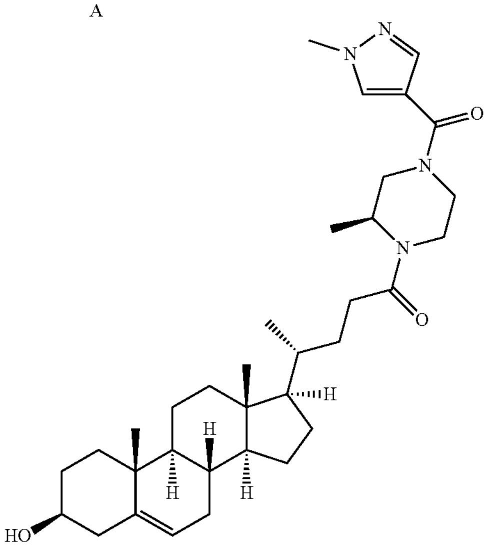

To a solution of compound A (100 mg, 219 μmol) and compound B (27.6 mg, 219 μmol) in DMF (3 mL) was added HATU (125 mg, 328 μmol) and DIPEA (84.9 mg, 657 mmol). The reaction was stirred at room temperature for 3 hours. Upon completion the reaction was quenched with saturated ammonium chloride solution (10 mL) and extracted with ethyl acetate (10 mL*3). The combined organic layers were washed with brine (10 mL), dried over sodium sulfate, filtered, and concentrated under reduced pressure. The crude product was purified by silica gel chromatography to afford the title compound 578 (10 mg, 8.09%) as a white solid. LCMS: $[M+H]^+$=565.30. $^1$H NMR (400 MHz, Chloroform-d) δ 7.72 (s, 1H), 7.61 (s, 1H), 5.34 (dd, J=4.8, 2.6 hz, 1H), 4.90-3.95 (m, 3H), 3.92 (s, 3H), 3.70-2.95 (m, 4H), 2.47-2.18 (m, 4H), 2.03-1.94 (m, 2H), 1.87-1.80 (m, 3H), 1.72 (s, 5H), 1.63-1.57 (m, 1H), 1.48-1.40 (m, 6H), 1.38-1.24 (m, 5H), 1.13-1.10 (m, 6H), 1.00 (s, 3H), 0.95 (d, J=6.4 hz, 3H), 0.68 (s, 3H).

Example 579: Methyl(S)-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-3-methylpiperazine-1-carboxylate

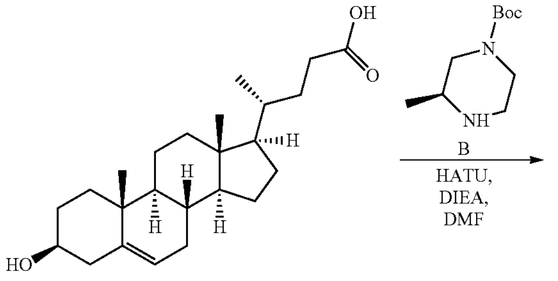

A

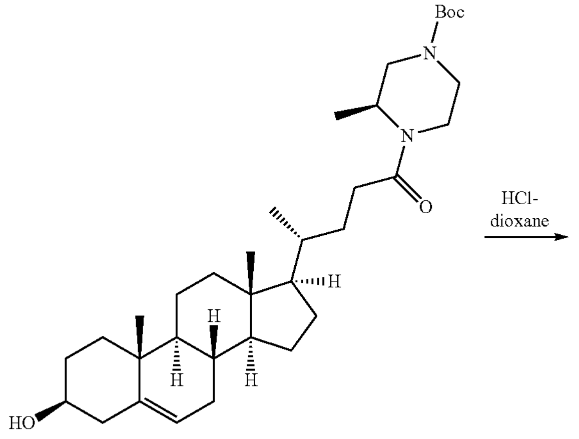

C

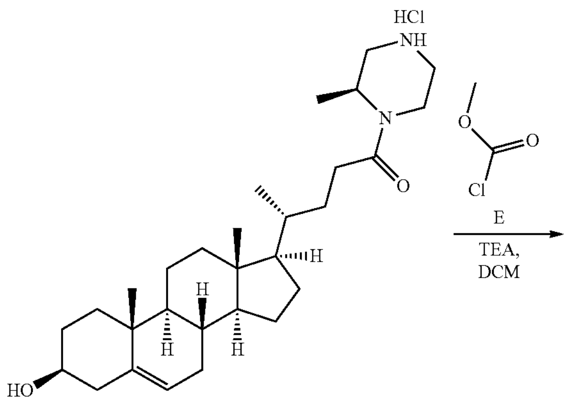

D

-continued

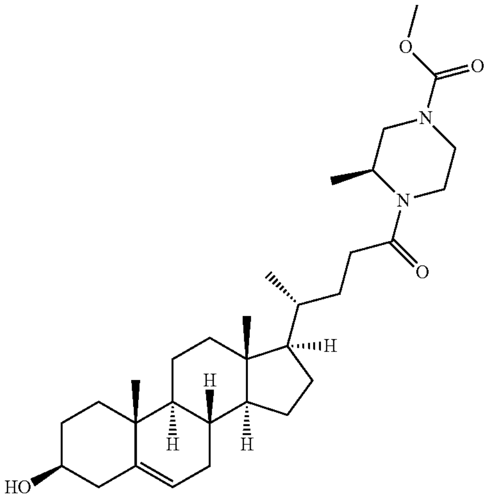

To a solution of compound A (1.8 g, 4.81 mmol) and compound B (1.44 g, 7.21 mmol) in DMF (20 mL) was added HATU (2.26 g, 9.61 mmol) and DIPEA (3.11 g, 24 mmol). The reaction stirred at room temperature for 3 hours. Upon completion the reaction was quenched with saturated ammonium chloride solution (200 mL) and extracted with ethyl acetate (200 mL*3). The combined organic layers were washed with brine (20 mL), dried over sodium sulfate, filtered, and concentrated under reduced pressure. The crude product was purified by column chromatography on silica gel to afford compound C (1.9 g, 71%) as a white solid.

4 M HCl in 1.4-dioxane (30 mL) was added slowly to the compound C (1.9 g, 3.41 mmol) in a single-neck flask at room temperature and stirred for 1 hour. Upon completion, DCM (50 mL) was added to the reaction and concentrated (3×) to give compound D as an HCl salt (1.6 g).

To a solution of compound D (108 mg, 219 μmol) in dichloromethane (5 mL) was added TEA (88.6 mg, 876 μmol) and methyl chloroformate (18.6 mg, 197 μmol) at 0° C. and the reaction was stirred for 1 h. Upon completion, the reaction was quenched with water (10 mL) and extracted with ethyl acetate (10 mL*3). The combined organic layers were washed with brine, dried over sodium sulfate, filtered, and concentrated under reduced pressure. The crude product was purified by silica gel chromatography to give the title compound 579 (100 mg, 88%) as a white solid. LCMS: $[M+1]^+$=515.30. $^1$H NMR (400 MHz, Chloroform-d) δ 5.35 (d, J=5.2 hz, 1H), 3.97-3.90 (m, 2H), 3.73 (s, 3H), 3.55-3.48 (m, 1H), 3.04-2.87 (m, 2H), 2.34-2.23 (m, 2H), 2.21 (d, J=12.2 hz, 2H), 1.98 (t, J=13.0 hz, 2H), 1.88-1.79 (m, 3H), 1.54-1.45 (m, 5H), 1.43-1.28 (d, J=23.8 hz, 7H), 1.20-1.06 (m, 6H), 1.01 (s, 3H), 0.95 (d, J=6.6 hz, 4H), 0.86 (d, J=12.0 hz, 1H), 0.68 (s, 3H).

Example 580: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-2-methyl-4-(pyridin-4-yl)piperazin-1-yl)pentan-1-one

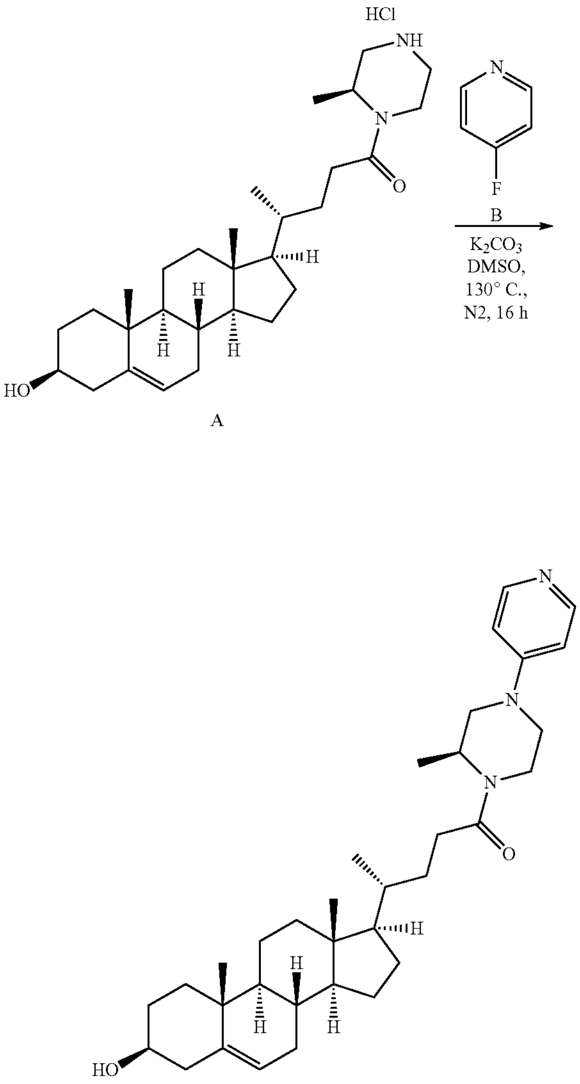

To a solution of compound A (300 mg, 657 μmol) in DMSO (2 mL) was added compound B (105 mg, 788 μmol), $K_2CO_3$ (90.8 mg, 657 μmol) and the reaction was stirred at 130° C. for 16 h. Water (5 mL) was added to the reaction and extracted with EtOAc (20 mL). The organic layer was washed with brine (5 mL), dried over sodium sulfate and concentrated. The crude product was purified by Prep-HPLC to give the title compound 580 (20.3 mg, 6.2%) as a white solid. LCMS: $[M+1]^+$=534.50. $^1$HNMR (400 MHz, Chloroform-d) δ 8.32 (s, 2H), 6.71 (s, 2H), 5.38 (d, J=5.0 hz, 1H), 3.86-3.50 (m, 4H), 3.31-2.99 (m, 2H), 2.53-2.20 (m, 4H), 2.06-1.88 (m, 5H), 1.67-1.43 (m, 8H), 1.42-1.30 (m, 6H), 1.26-1.06 (m, 6H), 1.04 (s, 3H), 1.00 (d, J=6.6 hz, 3H), 0.93-0.72 (s, 5H).

Example 581: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-2-methyl-4-(pyrazine-2-carbonyl)piperazin-1-yl)pentan-1-one

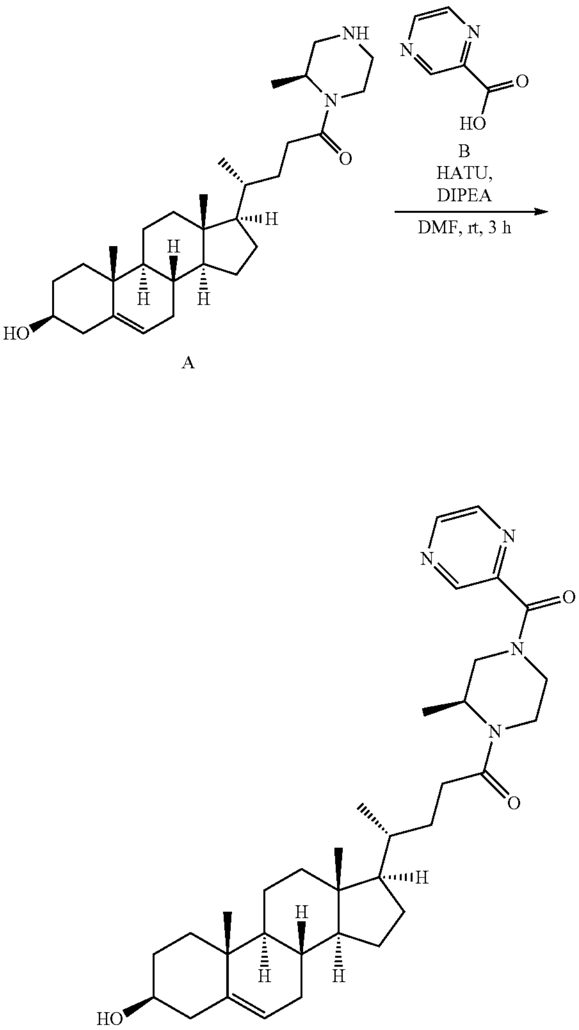

To a solution of compound A (100 mg, 219 μmol) in DMF (2 mL) was added compound B (32.6 mg, 263 μmol), HATU (103 mg, 438 μmol), DIPEA (191 μL, 1.09 mmol) and stirred at room temperature for 3 h. The reaction was quenched with $h_2O$ (5 mL) and extracted with ethyl acetate (20 mL). The organic layer was concentrated, and the residue was purified by silica gel chromatography to give the title compound 581 (56.8 mg, 46%) as a white solid. LCMS: $[M+1]^+$=563.25. $^1$H NMR (400 MHz, Chloroform-d) δ 9.01 (s, 1H), 8.67 (s, 1H), 8.55 (s, 1H), 5.35 (d, J=5.2 hz, 1H), 5.03-4.40 (m, 2H), 4.21-3.92 (m, 1H), 3.56-3.32 (m, 2H), 3.11-2.98 (m, 2H), 2.33-2.17 (m, 4H), 1.91-1.87 (m, 6H), 1.53-1.39 (m, 6H), 1.37-1.21 (m, 5H), 1.18-1.06 (m, 5H), 0.99-0.96 (m, 9H), 0.69 (s, 3H).

Example 582: (S)-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N,N,3-trimethylpiperazine-1-carboxamide

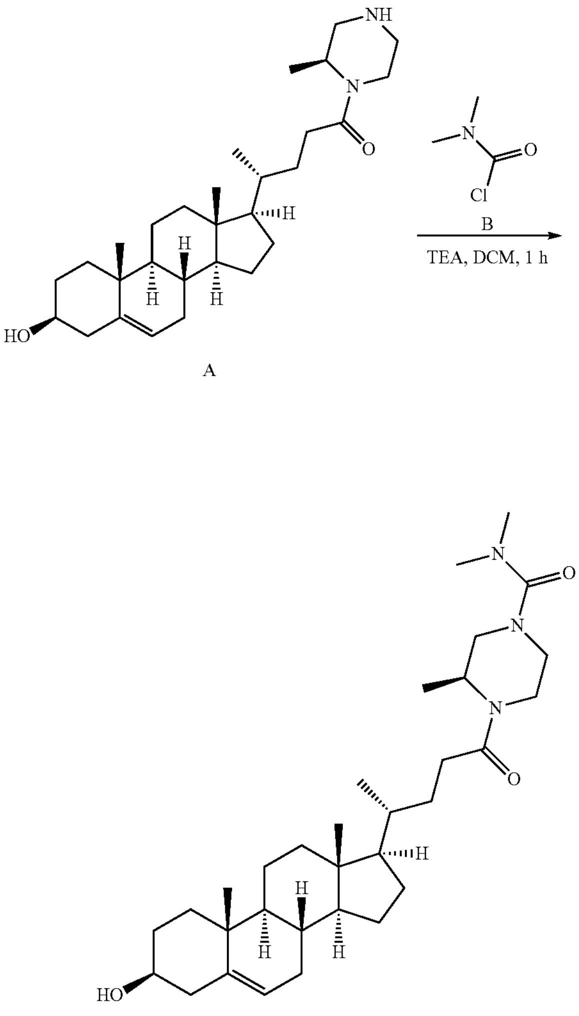

To a solution of compound A (100 mg, 219 μmol) in DCM (3 mL) was added TEA (91.3 μL, 657 μmol) and compound B (17.1 μL, 186 μmol) at 0° C. The reaction was stirred at 0° C. for 2 hours. The reaction was quenched by the addition of water (10 mL) and extracted with DCM (20 mL). The organic layer was dried over sodium sulfate and concentrated under reduced pressure. The crude product was purified by silica gel chromatography to give the title compound 582 (56.1 mg, 49%) as a white solid. LCMS: $[M+1]^+$=528.25. $^1$H NMR (400 MHz, Chloroform-d) δ 5.35 (d, J=5.2 hz, 1H), 4.77 (s, 1H), 4.41 (d, J=13.2 hz, 1H), 4.06 (s, 1H), 3.76-3.35 (m, 5H), 3.01 (d, J=13.6 hz, 1H), 2.86 (s, 6H), 2.79 (td, J=12.4, 3.6 hz, 1H), 2.32-2.19 (m, 3H), 2.02-1.93 (m, 2H), 1.85 (dd, J=10.2, 7.2 hz, 3H), 1.61-1.55 (m, 7H), 1.51-1.43 (m, 4H), 1.30 (d, J=9.6 hz, 3H), 1.18 (dd, J=12.6, 5.6 hz, 2H), 1.13-1.05 (m, 3H), 1.00 (s, 3H), 0.95-0.93 (m, 4H), 0.68 (s, 3H).

Example 583: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(2S)-2-methyl-4-propanoylpiperazin-1-yl]pentan-1-one

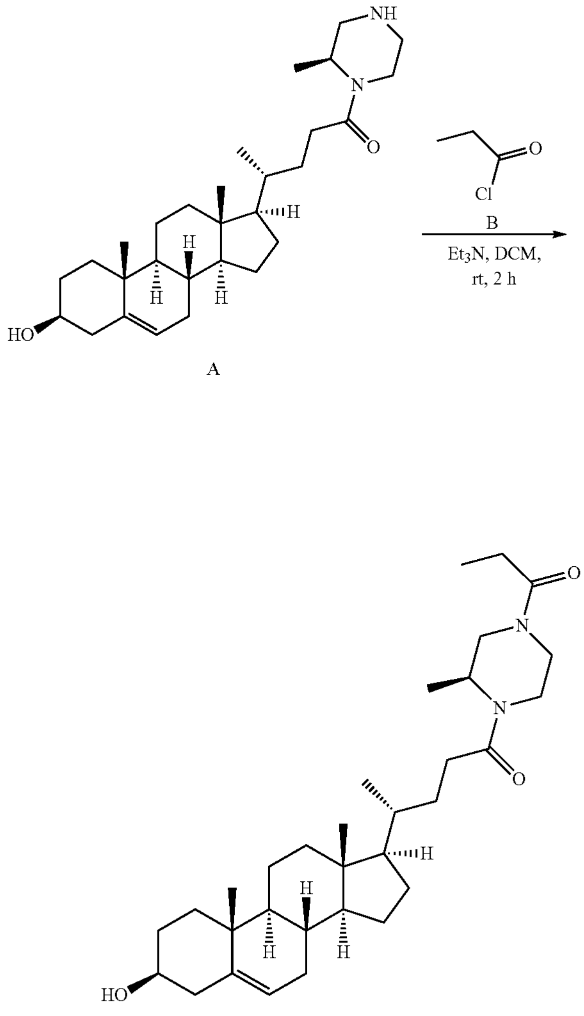

To a solution of compound A (100 mg, 219 μmol) in DCM (2 mL) was added compound B (16 mg, 175 μmol) and $Et_3N$ (98 mg, 657 μmol) at 0° C. The reaction was stirred at room temperature for 2 h. Water (30 mL) was added, and the reaction was extracted with DCM (30 mL*2). The combined organic layers were dried over sodium sulfate and concentrated under reduced pressure. The residue was purified by silica gel chromatography to give the title compound 583 (12 mg, 11%) as white solid. LCMS: $[M+1]^+$=513.25. $^1$H NMR (400 MHz, Chloroform-d) δ 5.35-5.33 (m, 1H), 4.61-4.29 (m, 1H), 3.79 (d, J=12.4 hz, 1H), 3.72-3.45 (m, 2H), 3.30-2.72 (m, 3H), 2.49-2.12 (m, 9H), 1.88-1.76 (m, 2H), 1.84 (dt, J=10.4, 3.6 hz, 3H), 1.59-1.39 (m, 7H), 1.28-1.22 (m, 4H), 1.20-1.12 (m, 6H), 1.00-0.88 (m, 8H), 0.68 (s, 3H).

Example 584: Cyclopentyl4-[(4R)-4-[(1R,3aS,3bR,5aS,7S,9aS,9bS,11aR)-7-hydroxy-9a,11a-dimethyl-hexadecahydro-1H-cyclopenta[a]phenanthren-1-yl]pentanoyl]piperazine-1-carboxylate

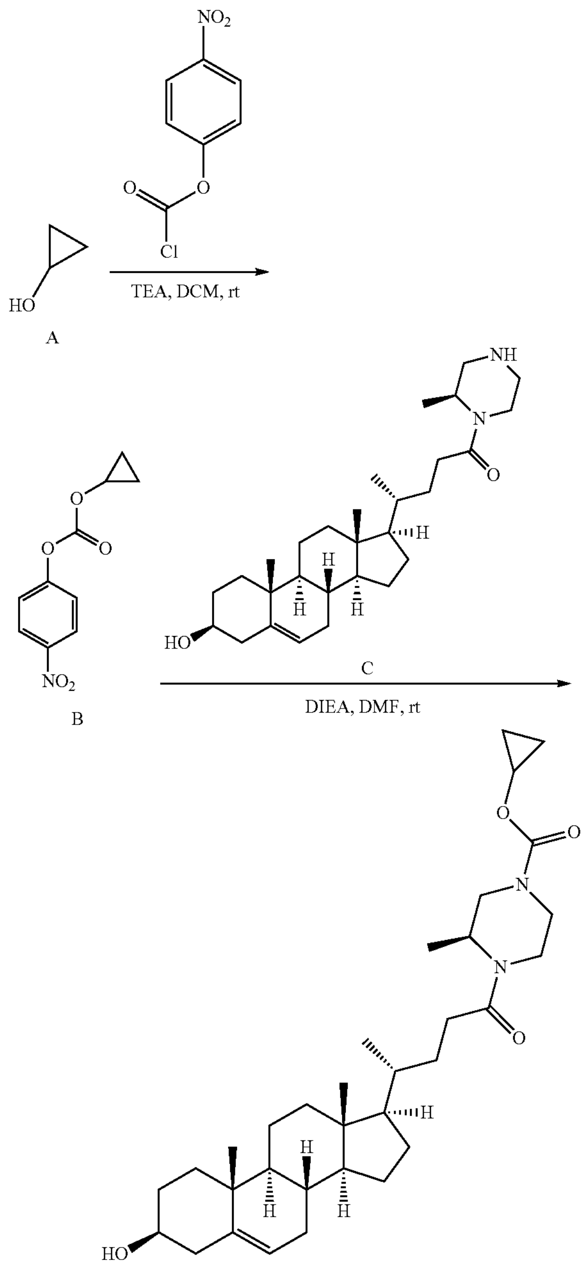

To a solution of compound A (173 mg, 2.98 mmol) in DCM (5 mL) was added TEA (301 mg, 2.98 mmol) drop-wise at room temperature. After addition, the reaction was cooled to 0° C. for 10 min. 4-nitrophenyl carbonochloridate (200 mg, 992 μmol) in DCM (5 mL) was added at 0° C. The reaction was stirred at room temperature for 3 h. The reaction was concentrated to afford crude compound B (210 mg, 95.0%) used directly to the next step.

To a solution of compound C (150 mg, 328 μmol) in dichloromethane (5 mL) was added DIPEA (127 mg, 985 μmol) and compound B (66 mg, 296 μmol) at room temperature. The reaction was stirred at room temperature for 16 h. The reaction was diluted with ethyl acetate (30 mL), washed with water (10 mL), brine (10 mL), dried with sodium sulfate and concentrated under reduced pressure. The crude product was purified by silica gel chromatography to give the title compound 584 (41.9 mg, 23.5%) as white solid. LCMS: $[M+1]^{+}=541.40$. $^{1}H$ NMR (400 MHz, $CDCl_3$) δ 5.37-5.32 (m, 1H), 4.19-3.96 (m, 2H), 3.92-3.70 (m, 1H), 3.68-3.48 (m, 1H), 3.00 (d, J=13.2 hz, 1H), 2.84 (bs, 1H), 2.47-2.14 (m, 4H), 2.02-1.94 (m, 2H), 1.89-1.81 (m, 3H), 1.63 (s, 3H), 1.54 (d, J=5.8 hz, 2H), 1.52-1.38 (m, 5H), 1.37-1.23 (m, 4H), 1.20-1.02 (m, 6H), 1.00 (s, 3H), 0.94 (d, J=6.6 hz, 3H), 0.93-0.81 (m, 1H), 0.72-0.66 (m, 6H).

Example 585: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((2S,4S)-2-methyl-4-(pyridin-4-yloxy)piperidin-1-yl)pentan-1-one

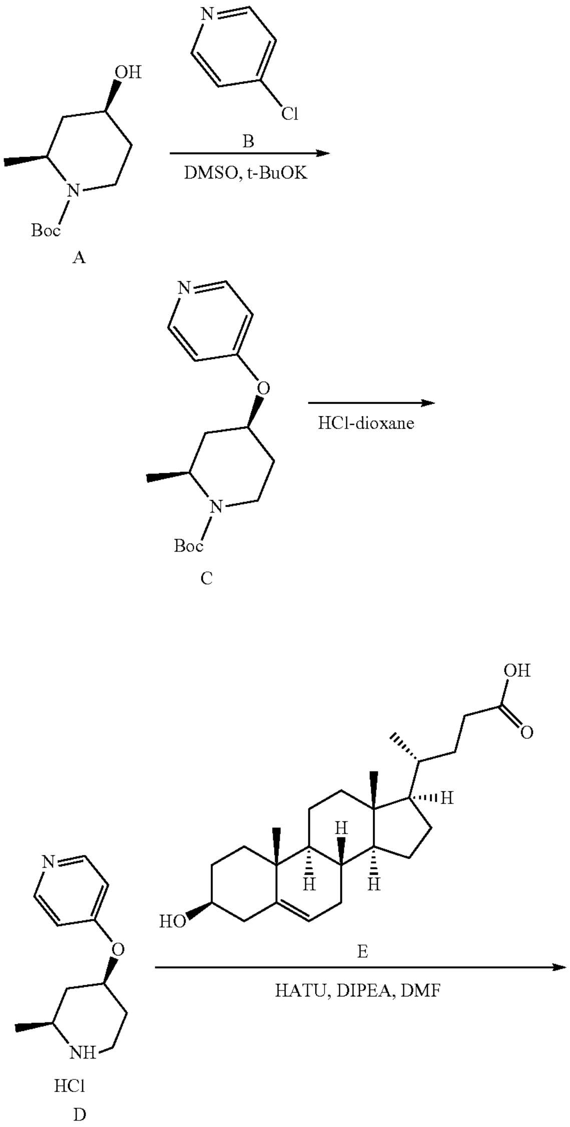

-continued

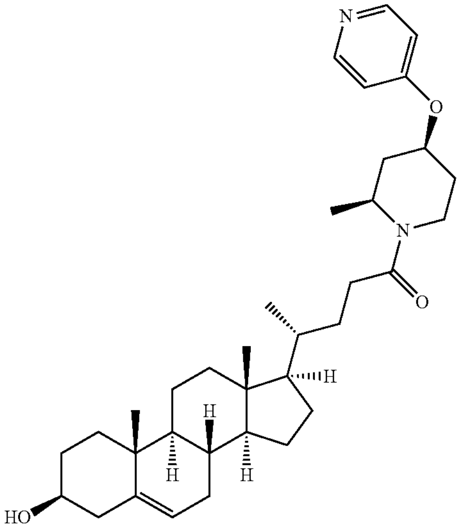

To a solution of compound A (100 mg, 881 μmol) and compound B (190 mg, 881 μmol) in DMSO (4 mL) was added t-BuOK (395 mg, 3.52 mmol) and the reaction was stirred at 70° C. under nitrogen for 16 h. Upon completion, the reaction was quenched with water (10 mL) and extracted with ethyl acetate (10 mL*3). The combined organic layers were washed with brine, dried over sodium sulfate, filtered, and concentrated under reduced pressure. The crude product was purified by silica gel chromatography to afford compound C (107 mg, 41%) as a white solid.

HCl in 1,4-dioxane (2 mL) was added slowly to the compound C (100 mg, 342 μmol) in a single-neck flask at room temperature and stirred for 1 hour. Upon completion, DCM (10 mL) was added to the reaction and concentrated (3×) to give compound D as an HCl salt (118 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (164 mg, 437 μmol) and 4-(((2S,4S)-2-methylpiperidin-4-yl)oxy)pyridine hydrochloride (118 mg, 342 μmol) were reacted according to Example 536 to give the title compound 585 (35 mg, 15%) as a white solid. LCMS: $[M+1]^+$=549.35. $^1$H NMR (400 MHz, Chloroform-d) δ 8.44 (d, J=5.6 hz, 2H), 6.81 (d, J=5.6 hz, 2H), 5.35 (d, J=5.2 hz, 1H), 4.80 (q, J=3.2 hz, 1H), 4.34-4.25 (m, 1H), 3.52 (tt, J=10.8, 4.6 hz, 2H), 2.41 (ddd, J=15.4, 11.0, 5.0 hz, 1H), 2.33-2.18 (m, 3H), 2.00 (dt, J=12.8, 3.6 hz, 3H), 1.94 (t, J=4.8 hz, 1H), 1.87-1.80 (m, 3H), 1.73-1.66 (m, 6H), 1.64-1.58 (m, 1H), 1.51-1.46 (m, 3H), 1.44 (d, J=4.8 hz, 1H), 1.39-1.35 (m, 1H), 1.34-1.28 (m, 3H), 1.26 (t, J=4.0 hz, 1H), 1.17 (d, J=5.8 hz, 1H), 1.14 (d, J=4.2 hz, 1H), 1.11 (bs, 1H), 1.07 (d, J=5.4 hz, 1H), 1.04 (d, J=4.4 hz, 1H), 1.01 (s, 3H), 0.96 (d, J=6.4 hz, 3H), 0.90 (dd, J=11.8, 6.4 hz, 1H), 0.69 (s, 3H).

Example 586: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((2S,4R)-2-methyl-4-(pyridin-4-yloxy)piperidin-1-yl)pentan-1-one

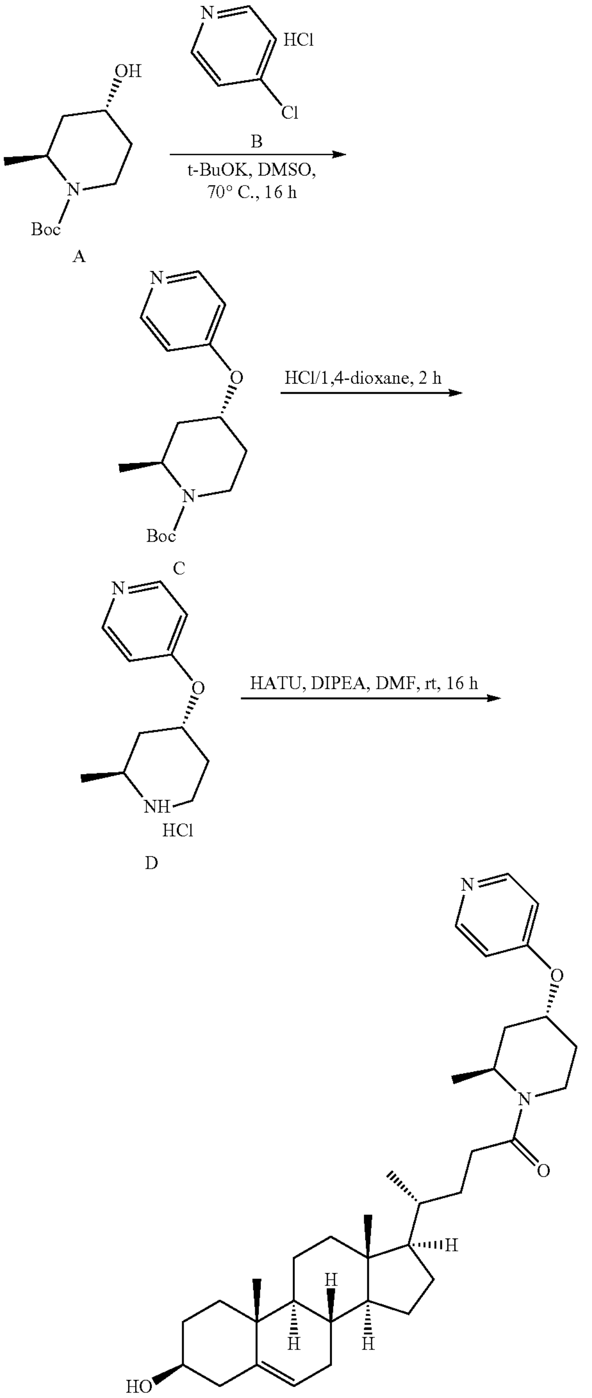

A solution of tert-butyl compound A (50 mg, 232 μmol), t-BuOK (104 mg, 929 μmol) and compound B (69.7 mg, 464 μmol) in DMSO (2 mL) was stirred at 70° C. for 16 h under $N_2$. The reaction was quenched with water (10 mL) and extracted with EtOAc (20 mL). The organic layer was concentrated under reduced pressure. The crude product was purified by silica gel chromatography to afford compound C (65 mg, 95.7%) as a white solid.

A solution of compound C (60 mg, 205 μmol) was added HCl (1 mL, 4M in 1,4-dioxane). The reaction was stirred at room temperature for 1 h. The reaction was concentrated to afford compound D (50 mg) as a white solid.

(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]pentanoic acid (50 mg, 133 μmol) and 4-{[(2S,4R)-2-methylpiperidin-4-yl]oxy}pyridine hydrochloride (36.6 mg, 160 μmol) were reacted according to Example 536 to give the title compound 586 (15 mg, 20.4%). LCMS: $[M+1]^+$ =549.25. $^1$H NMR (400 MHz, Chloroform-d) δ 8.47 (d, J=5.6 hz, 2H), 6.94 (d, J=6.0 hz, 2H), 5.35 (d, J=5.2 hz, 1H), 5.22-4.78 (m, 3H), 3.58-3.44 (m, 1H), 3.38-2.70 (m, 1H), 2.51-2.15 (m, 5H), 2.01-1.78 (m, 11H), 1.66-1.57 (m, 2H), 1.54-1.43 (m, 6H), 1.39-1.29 (m, 4H), 1.19-1.04 (m, 4H), 1.00 (s, 3H), 0.96 (d, J=6.4 hz, 3H), 0.92-0.83 (m, 1H), 0.69 (s, 3H).

Example 587: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-2-methyl-4-(1-methyl-1H-1,2,3-triazole-4-carbonyl)piperazin-1-yl)pentan-1-one

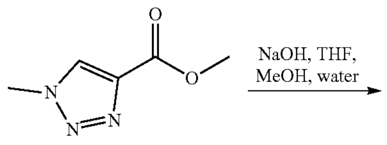

A

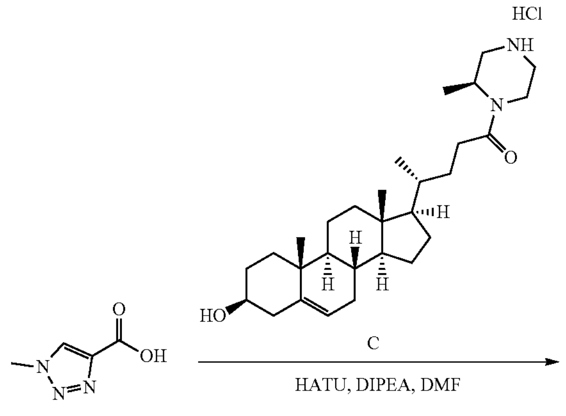

B C

-continued

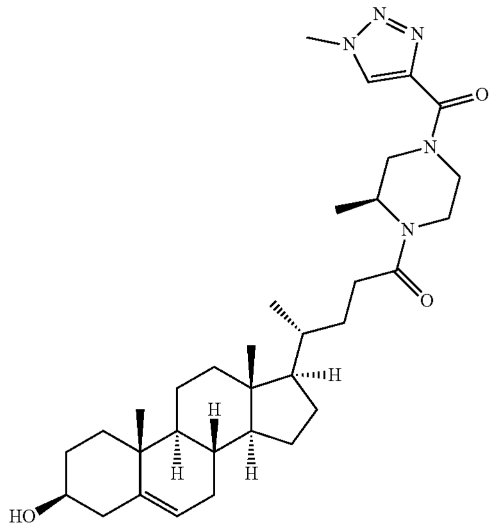

To a room temperature solution of compound A (100 mg, 709 μmol) in methanol (2 mL) and THF (4 mL) was added a solution of NaOH (142 mg, 3.54 mmol) in water (2 mL) and the reaction stirred for 2 hours. Upon completion, the reaction solution was adjusted to pH 2 to 3 with 1 N hydrochloric acid and extracted with dichloromethane (10 mL*3). The combined organic layers were washed with brine, dried over sodium sulfate, filtered, and concentrated to afford compound B (70 mg, 78%) as a white solid.

To a solution of compound B (70 mg, 550 μmol) and compound C (163 mg, 330 μmol) in DMF (5 mL) was added HATU (419 mg, 1.1 mmol) and DIPEA (427 mg, 3.3 mmol). The reaction was stirred at room temperature for 2 h. Upon completion, the reaction was quenched with saturated aqueous ammonium chloride (50 mL) and extracted with ethyl acetate (50 mL*3). The combined organic layers were washed with brine, dried over sodium sulfate, filtered, and concentrated under reduced pressure. The crude product was purified by silica gel chromatography to give the title compound 587 (37.9 mg, 20%) as a white solid. LCMS: $[M+1]^+$=566.40. $^1$H NMR (400 MHz, Chloroform-d) δ 8.09 (s, 1H), 5.48-5.20 (m, 2H), 4.90-4.87 (m, 1H), 4.62 (d, J=13.2 hz, 1H), 4.51 (bs, 1H), 4.14 (s, 3H), 3.69 (bs, 1H), 3.51 (td, J=12.8, 8.6 hz, 2H), 3.26 (s, 1H), 3.02 (s, 1H), 2.34-2.19 (m, 3H), 1.99 (tt, J=13.2, 3.4 hz, 2H), 1.88-1.85 (m, 1H), 1.82 (d, J=4.8 hz, 1H), 1.60-1.54 (m, 6H), 1.48-1.41 (m, 4H), 1.30 (dt, J=16.6, 7.6 hz, 4H), 1.22-1.07 (m, 5H), 1.01 (s, 3H), 0.96 (d, J=6.4 hz, 3H), 0.92 (dd, J=11.2, 5.6 hz, 1H), 0.69 (s, 3H).

Example 588: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(2S)-2-methyl-4-(pyrimidin-4-yl)piperazin-1-yl]pentan-1-one

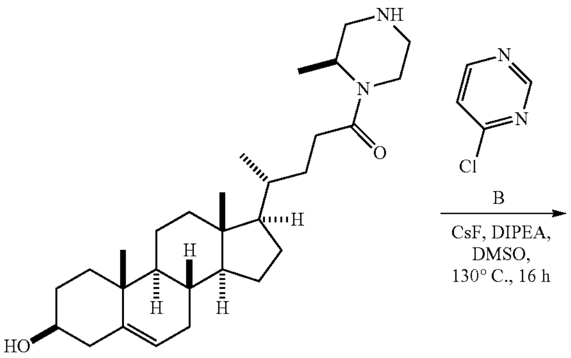

A

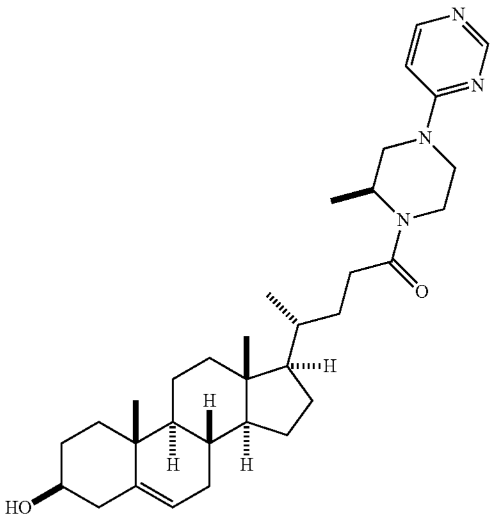

To a solution of compound A (100 mg, 219 μmol) in DMSO (2 mL) at room temperature was added compound B (25 mg, 219 μmol), CsF (99.8 mg, 657 μmol), DIPEA (113 mg, 876 μmol) and the reaction was stirred at 130° C. for 16 h. The reaction was diluted with saturated aqueous $NH_4Cl$ (30 mL) and extracted with EtOAc (20 mL*2). The combined organic layers were washed with water (20 mL), dried over sodium sulfate and concentrated under reduced pressure. The residue was purified by silica gel chromatography to give the title compound 588 (14 mg, 12%) as white solid. LCMS: [M+1]+=535.20. $^{1}H$ NMR (400 MHz, Chloroform-d) δ 8.60 (s, 1H), 8.23 (s, 1H), 6.50 (d, J=6.0 hz, 1H), 5.35 (d, J=5.2 hz, 1H), 4.57-3.95 (m, 3H), 3.72 (s, 1H), 3.60-3.44 (m, 2H), 3.30 (bs, 1H), 3.07 (bs, 2H), 2.31-2.20 (m, 3H), 2.03-1.97 (m, 2H), 1.91-1.88 (s, 6H), 1.86-1.79 (m, 3H), 1.55-1.42 (m, 6H), 1.31-1.23 (m, 3H), 1.19-1.05 (m, 5H), 1.01 (s, 3H), 0.96 (d, J=6.4 hz, 3H), 0.69 (s, 3H).

Example 589: Isopropyl(S)-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-3-methylpiperazine-1-carboxylate

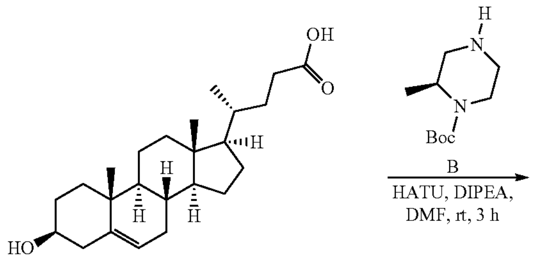

A

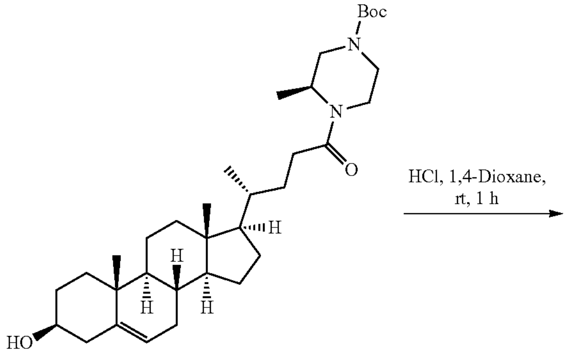

C

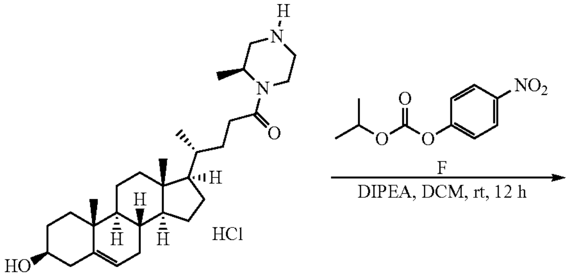

D

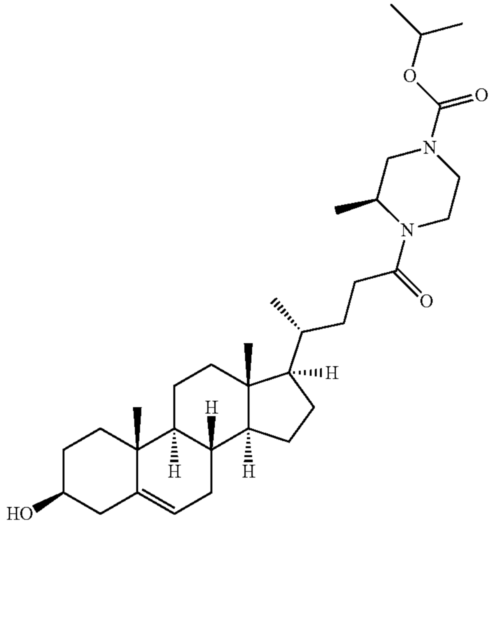

-continued

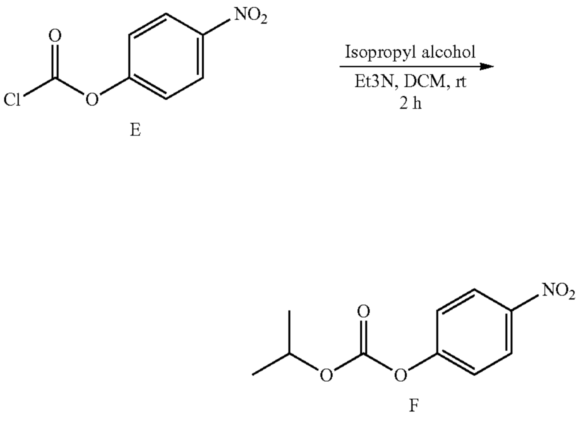

To a solution of compound A (5 g, 13.3 mmol), compound B (4 g, 20 mmol) and DIPEA (8.6 g, 66.7 mmol) in DMF (20 mL) was added HATU (10.2 g, 26.7 mmol) at room temperature under $N_2$ and stirred for 3 h. The reaction was diluted with saturated aqueous $NH_4Cl$ (60 mL) and extracted with EtOAc (20 mL*2). The combined organic layers were washed with saturated aqueous $NaHCO_3$ (40 mL), water (40 mL), brine (40 mL), dried over sodium sulfate and concentrated under reduced pressure. The residue was purified by silica gel chromatography to afford C (6.5 g, 86%) as a white solid.

To a solution of compound C (6.5 g, 11.7 mmol) in 1,4-dioxane (10 mL) was added hydrogen chloride (2.5 mL, 10 mmol, 4M in 1.4-dioxane) at room temperature and the reaction was stirred for 1 h. The reaction was concentrated under reduced pressure to give compound D as an HCl salt (5.6 g).

To a solution of compound E (5 g, 24.8 mmol) and $Et_3N$ (10 g, 99.2 mmol) in DCM (20 mL) was added isopropyl alcohol (3 g, 49.6 mmol) at 0° C. and the reaction was warmed to room temperature for 2 h. The reaction was concentrated under reduced pressure and the residue was purified by silica gel chromatography to afford F (5.4 g, 97%) as a white solid.

To a solution of compound D (5 g, 10.2 mmol) and compound F (2 g, 8.9 mmol) in DCM (10 mL) was added DIPEA (4.6 g, 35.5 mmol) at room temperature under $N_2$ and stirred for 12 h. The reaction was diluted with saturated aqueous $NH_4Cl$ (30 mL) and extracted with DCM (10 mL*2). The combined organic layers were washed with saturated aqueous $NaHCO_3$ (20 mL), water (20 mL), brine (20 mL), dried over sodium sulfate and concentrated under reduced pressure. The residue was purified by silica gel chromatography to give the title compound 589 (4.4 g, 91%) as a white solid. LCMS: $[M+H]^+$=543.40. $^1H$ NMR (400 MHz, Chloroform-d) δ 5.34 (d, J=5.2 hz, 1H), 5.03-4.80 (m, 1H), 4.78-4.38 (m, 1H), 4.08-4.00 (m, 2H), 3.54 (dd, J=10.8, 4.8 hz, 2H), 3.00 (d, J=13.0 hz, 1H), 2.85 (bs, 2H), 2.51-2.12 (m, 4H), 1.99 (dt, J=7.2, 3.6 hz, 2H), 1.89-1.75 (m, 4H), 1.55-1.39 (m, 8H), 1.37-1.20 (m, 11H), 1.19-1.05 (m, 5H), 1.00 (s, 3H), 0.95 (d, J=6.4 hz, 4H), 0.68 (s, 3H).

Example 590: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-4-isonicotinoyl-2-methylpiperazin-1-yl)pentan-1-one

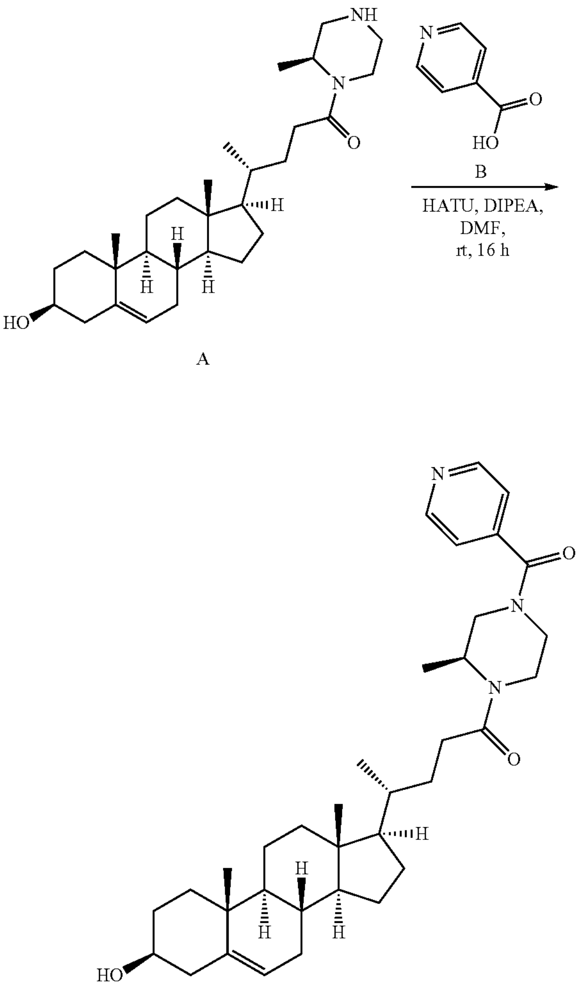

To a solution of compound A (100 mg, 219 μmol) and compound B (27 mg, 219 μmol) in DMF (3 mL) was added HATU (125 mg, 328 μmol) and DIPEA (84.9 mg, 657 μmol) and the reaction was stirred at room temperature for 3 h. Upon completion, the reaction was quenched with saturated aqueous ammonium chloride (10 mL) and extracted with ethyl acetate (10 mL*3). The combined organic layers were washed with brine (10 mL), dried over sodium sulfate, filtered, and concentrated under reduced pressure. The crude product was purified by silica gel chromatography to afford the title compound 590 (51.9 mg, 42.19%) as a white solid. LCMS: $[M+1]^+$=562.35. $^1H$ NMR (400 MHz, Chloroform-d) δ 8.73 (d, J=4.9 hz, 2H), 7.30 (d, J=4.7 hz, 2H), 5.36 (dd, J=4.9, 2.7 hz, 1H), 4.66-4.54 (m, 2H), 4.12-4.00 (m, 1H), 3.53-3.49 (m, 2H), 3.38 (bs, 2H), 3.01-2.95 (m, 2H), 2.34-2.22 (m, 3H), 2.05-1.83 (m, 6H), 1.64-1.53 (m, 6H), 1.48-1.42 (m, 5H), 1.37-1.26 (m, 5H), 1.22-1.10 (m, 4H), 1.09 (d, J=4.6 hz, 1H), 1.02 (s, 3H), 0.97 (d, J=5.5 hz, 3H), 0.70 (s, 3H).

Example 591: Methyl 4-{[(2S)-2-[(1R,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]propyl]carbamoyl}piperidine-1-carboxylate

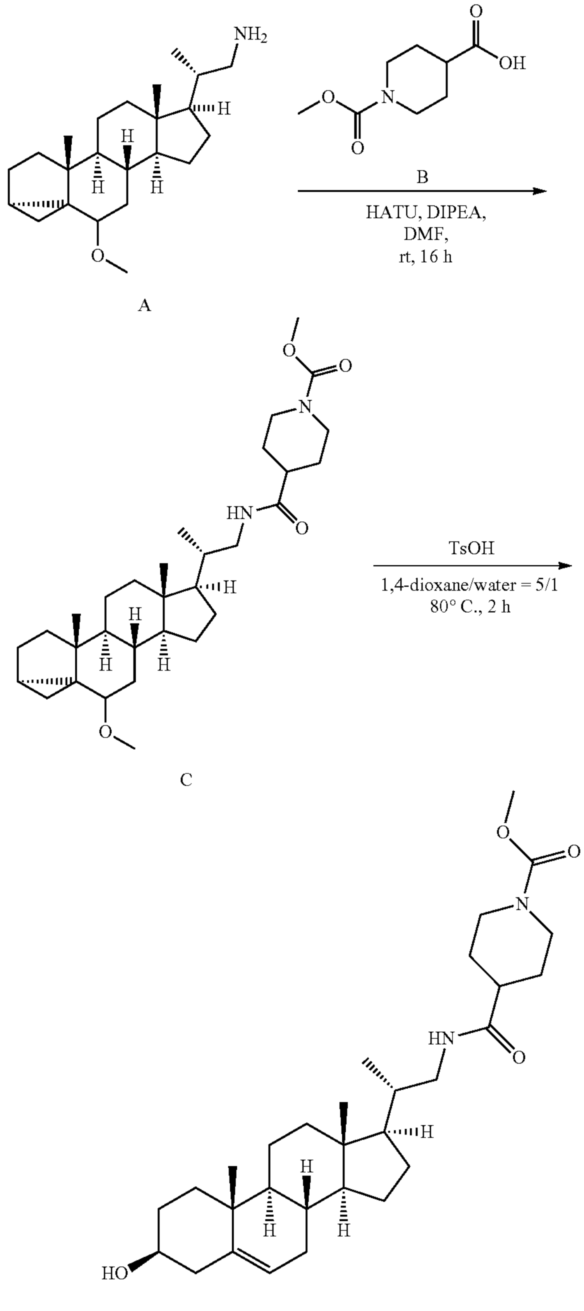

To a solution of compound A (100 mg, 289 μmol) in DMF (2 mL) was added compound B (54 mg, 289 μmol), HATU (165 mg, 434 μmol) and DIPEA (150 mg, 1.16 mmol). The reaction was stirred at room temperature for 16 h. Water (30 mL) was added, and the reaction was extracted with ethyl acetate (20 mL*2). The combined organic layers were washed with water (20 mL), brine (20 mL), dried over sodium sulfate and concentrated under reduced pressure. The residue was purified by silica gel chromatography to afford compound C (100 mg, 67%) as yellow oil.

Methyl-4-(((2S)-2-((1aR,3aR,3bS,5aS,6R,8aS,8bS,10aS)-10-methoxy-3a,5a-dimethylhexadecahydrocyclopenta[a]cyclopropa[2,3]cyclopenta[1,2-f]naphthalen-6-yl)propyl)carbamoyl)piperidine-1-carboxylate (80 mg, 155 μmol) were reacted according to Example 430 to give the title compound 591 (30 mg, 38%) as white solid. LCMS: $[M+1]^+$=501.25. $^1H$ NMR (400 MHz, Chloroform-d) δ 5.45-5.32 (m, 2H), 4.17 (s, 2H), 3.69 (s, 3H), 3.58-3.47 (m, 1H), 3.38-3.32 (m, 1H), 3.00-2.93 (m, 1H), 2.82 (t, J=12.4 hz, 2H), 2.32-2.20 (m, 3H), 2.02-1.94 (m, 2H), 1.91-1.78 (m, 5H), 1.70-1.62 (m, 3H), 1.54-1.42 (m, 6H), 1.26 (bs, 2H), 1.07-1.05 (m, 4H), 1.01 (s, 3H), 0.95 (d, J=6.6 hz, 4H), 0.69 (s, 3H).

Example 592: (R)-1-(4-ethyl-4-hydroxypiperidin-1-yl)-3-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)butan-1-one

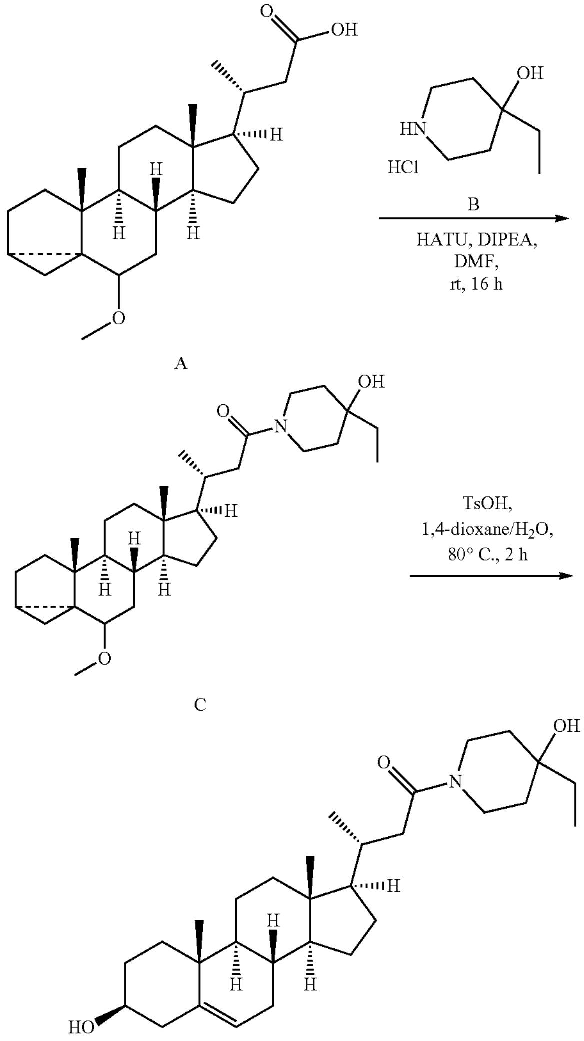

A solution of compound A (100 mg, 267 μmol), compound B (53.1 mg, 320 μmol), HATU (94.2 mg, 0.4 mmol) and DIPEA (104 mg, 801 μmol) in DMF (2 ml) was stirred at room temperature for 16 h.

The reaction was quenched with water (5 mL) and extracted with EtOAc (10 mL). The organic layer was concentrated under reduced pressure. The crude product was purified by silica gel chromatography to afford compound C (80 mg, 61.7%).

(3R)-1-(4-ethyl-4-hydroxypiperidin-1-yl)-3-((1aR,3aR,3bS,5aR,6R,8aS,8bS,10aR)-10-methoxy-3a,5a-dimethyl-hexadecahydrocyclopenta[a]cyclopropa[2,3]cyclopenta[1,2-f]naphthalen-6-yl)butan-1-one (80 mg, 165 μmol) to give the title compound 592 (15 mg, 19.3%). LCMS: $[M+1]^+$=472.20. $^1$H NMR (400 MHz, Chloroform-d) δ 5.35 (d, J=4.8 hz, 1H), 4.46-2.95 (m, 5H), 2.45-2.37 (m, 1H), 2.31-2.21 (m, 2H), 2.02-1.90 (m, 5H), 1.84 (d, J=12.4 hz, 3H), 1.51-1.45 (m, 10H), 1.35 (s, 3H), 1.19-1.06 (m, 4H), 1.01 (s, 3H), 0.98 (d, J=6.0 hz, 3H), 0.95-0.91 (m, 3H), 0.73 (s, 3H).

Example 593: Methyl 4-[(3R)-3-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]butanoyl]piperazine-1-carboxylate

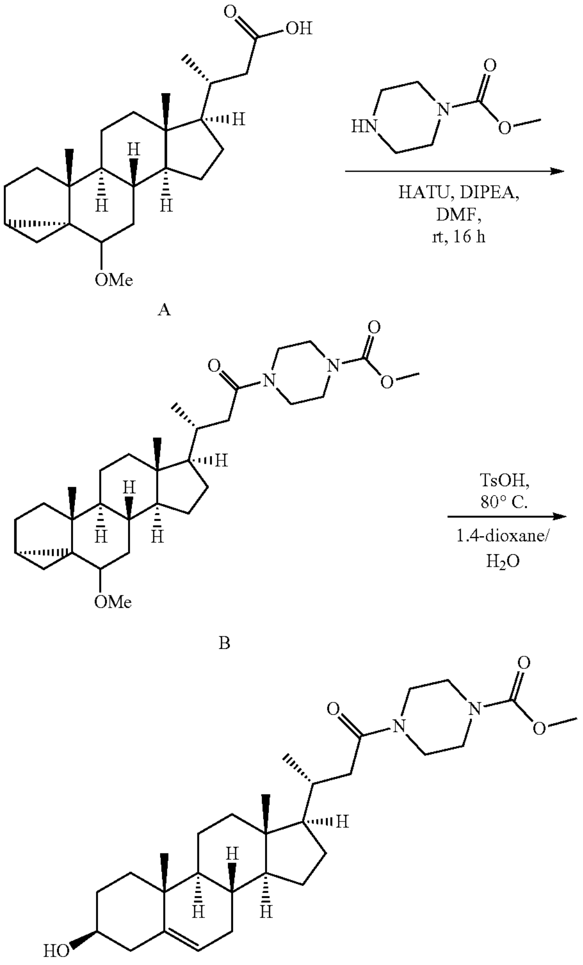

A

B

To a solution of compound A (150 mg, 0.4 mmol) in DMF (8 mL) was added DIEA (155 mg, 1.2 mmol), methyl piperazine-1-carboxylate (75.1 mg, 521 μmol) and HATU (305 mg, 801 μmol) at room temperature. After stirring at room temperature for 16 h, the reaction was diluted with water (5 mL) and extracted with ethyl acetate (10 mL). The organic layer was washed with water (5 mL), brine (5 mL), dried with sodium sulfate and concentrated under reduced pressure. The crude product was purified by silica gel chromatography to give the title compound B (60 mg, 29.9%).

Methyl 4-((R)-3-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)butanoyl)piperazine-1-carboxylate (60 mg, 120 μmol) were reacted according to Example 430 to give the title compound 593 (19.7 mg, 33.7%) as a white solid. LCMS: $[M+H]^+$=487.45. $^1$H NMR (400 MHz, $CDCl_3$) δ 5.35 (bs, 1H), 3.72-3.47 (m, 12H), 2.41 (d, J=13.4 hz, 1H), 2.32-2.22 (m, 2H), 2.09-1.92 (m, 5H), 1.84 (d, J=11.0 hz, 3H), 1.55-1.41 (m, 6H), 1.28-1.22 (m, 5H), 1.19-1.13 (m, 2H), 1.01-0.97 (m, 6H), 0.73 (s, 3H).

Example 594: (R)-3-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(1-methyl-1H-pyrazole-4-carbonyl)piperazin-1-yl)butan-1-one

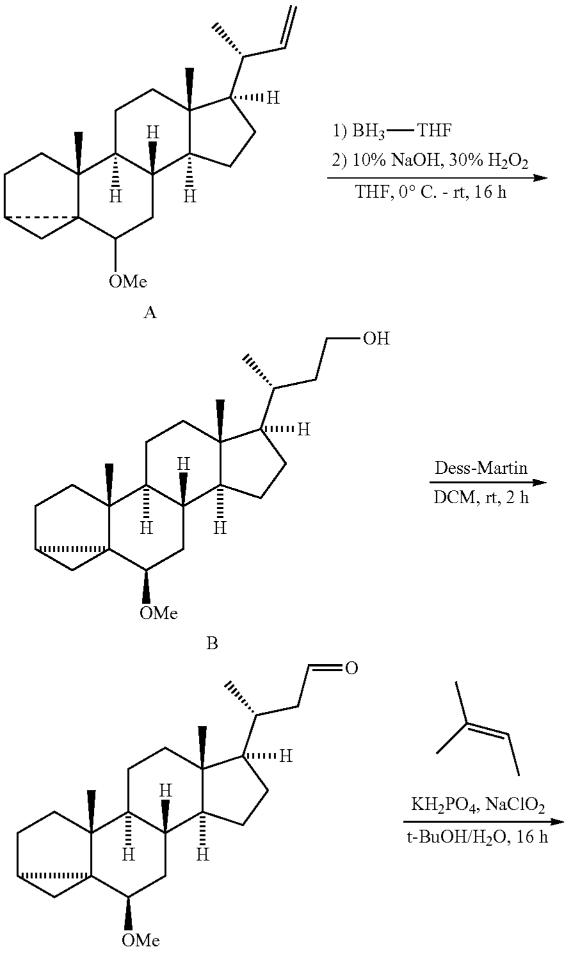

A

B

C

-continued

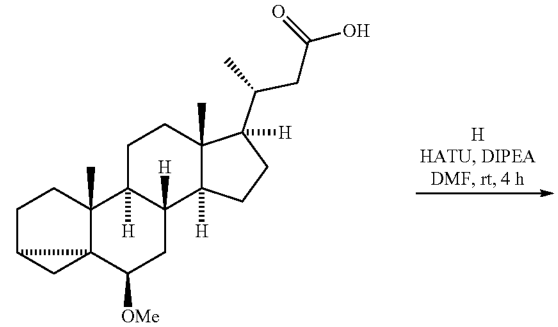

D

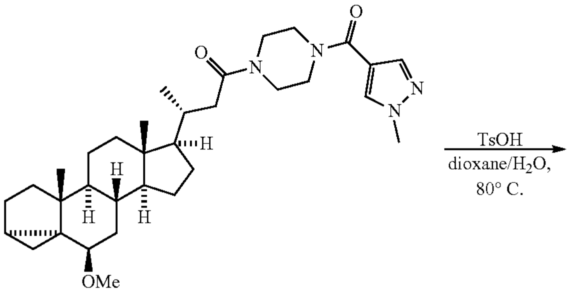

I

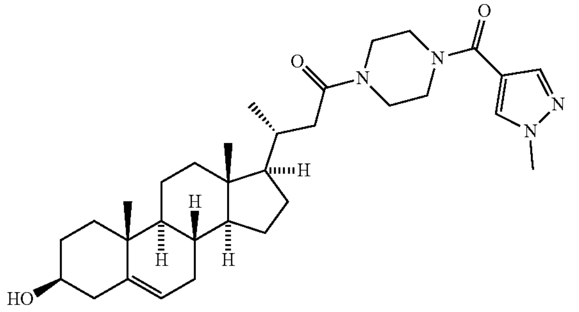

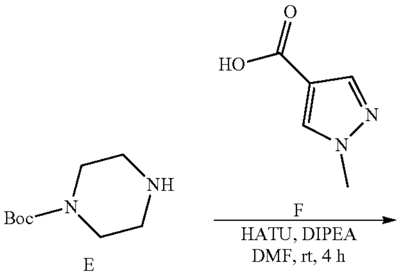

E

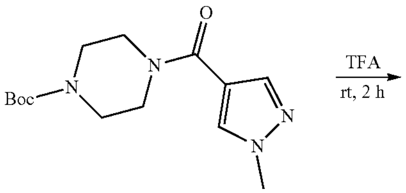

G

-continued

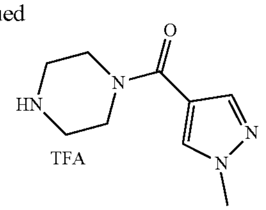

H

To a solution of compound A (1.5 g, 4.38 mmol) in THE (37.2 mL) was added $BH_3$-THF (11.6 mL, 8.32 mmol) at −5° C. The reaction stirred at 0° C. for 1 h under $N_2$, then warmed to room temperature for 16 h. Sodium hydroxide 10% w/w (8.3 mL) and $h_2O_2$ 30% w/w (2.7 mL) were added at −5° C. and the reaction stirred at room temperature for 1.5 h. The reaction was quenched with water (5 mL) and extracted with DCM (10 mL). The organic layer was concentrated under reduced pressure. The crude product was purified by silica gel chromatography to afford compound B (1.3 g, 82%).

To a solution of compound B (350 mg, 971 μmol) in DCM (6 mL) was added Dess-Martin periodinane (1.24 g, 2.91 mmol) at 0° C. The reaction stirred at room temperature for 2 h. Saturated aqueous $Na_2S_2O_3$ (10 mL) was added and diluted with water (9 mL) then extracted with ethyl acetate (20 mL). The organic layer was concentrated to give compound C (350 mg, 976 μmol) and was used as is in the next step.

To a solution of compound C (350 mg, 976 μmol) in t-BuOH (6 mL) and water (1.75 mL) was added $KH_2PO_4$ (159 mg, 1.17 mmol), 2-methylbut-2-ene (103 mg, 1.46 mmol) and $NaClO_2$ (106 mg, 1.17 mmol) at 0° C. The reaction was stirred at room temperature for 16 h. Upon completion, the reaction was diluted with water (10 mL) and extracted with ethyl acetate (30 mL). The organic layer was concentrated to give compound D (350 mg) and was used as is in the next step.

To a solution of compound F (135 mg, 1.07 mmol) in DMF (4 mL) was added compound E (0.2 g, 1.07 mmol), DIPEA (694 mg, 5.37 mmol),hATU (505 mg, 2.15 mmol) and the reaction stirred at room temperature for 4 h. Upon completion, the reaction was diluted with water (15 mL) and extracted with ethyl acetate (30 mL). The organic layer was concentrated under reduced pressure and purified by silica gel chromatography to afford compound G (200 mg, 63%).

To a solution of compound G (200 mg, 679 μmol) in DCM was added TFA (2 mL) and the reaction stirred at room temperature for 2 h. Upon completion, the reaction was concentrated to afford compound H (150 mg) and was used directly in the next step.

To a solution of compound D (150 mg, 0.4 mmol) in DMF (4 mL) was added compound H (150 mg, 486 μmol),hATU (188 mg, 801 μmol), DIPEA (259 mg, 2 mmol) and the reaction stirred at room temperature for 4 h. Upon completion, the reaction was diluted with water (10 mL) and extracted with ethyl acetate (20 mL). The organic layer was concentrated under reduced pressure and the crude product was purified by silica gel chromatography to afford compound I (100 mg, 45%).

(R)-3-((1aR,3aR,3bS,5aR,6R,8aS,8bS,10R,10aS)-10-methoxy-3a,5a-dimethylhexadecahydrocyclopenta[a]cyclopropa[2,3] cyclopenta[1,2-f]naphthalen-6-yl)-1-(4-(1-methyl-1H-pyrazole-4-carbonyl)piperazin-1-yl)butan-1-one (100 mg, 182 μmol) were reacted according to Example 430 to give the title compound 594 (30 mg, 31%). LCMS:

[M+1]$^+$=537.40. $^1$H NMR (400 MHz, Chloroform-d) δ 7.71 (s, 1H), 7.60 (s, 1H), 5.32 (d, J=5.0 hz, 1H), 3.91 (s, 3H), 3.75-3.63 (m, 6H), 3.56-3.45 (m, 3H), 2.41 (dd, J=14.2, 2.6 hz, 1H), 2.30-2.19 (m, 2H), 2.07 (d, J=10.2 hz, 1H), 2.02 (d, J=3.8 hz, 1H), 1.99 (d, J=3.4 hz, 1H), 1.96-1.92 (m, 1H), 1.85-1.77 (m, 3H), 1.63-1.57 (m, 1H), 1.51 (dd, J=9.6, 3.4 hz, 2H), 1.47-1.45 (m, 1H), 1.44-1.35 (m, 2H), 1.30 (d, J=10.8 hz, 1H), 1.25 (d, J=12.4 hz, 3H), 1.16 (dd, J=11.4, 8.0 hz, 2H), 1.10-1.02 (m, 2H), 0.98 (d, J=6.6 hz, 6H), 0.91 (d, J=1.8 hz, 1H), 0.71 (s, 3H).

Example 595: (R)-3-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(pyrimidin-4-yl)piperazin-1-yl)butan-1-one

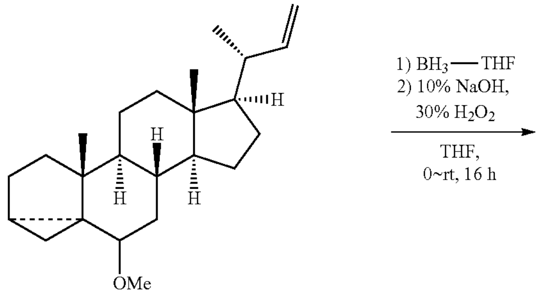

A

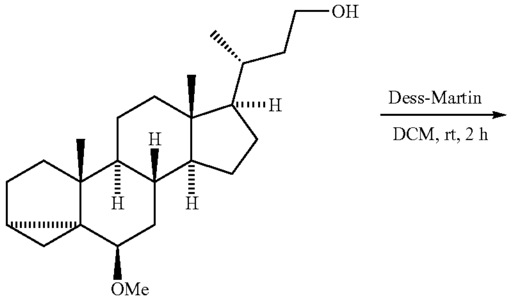

B

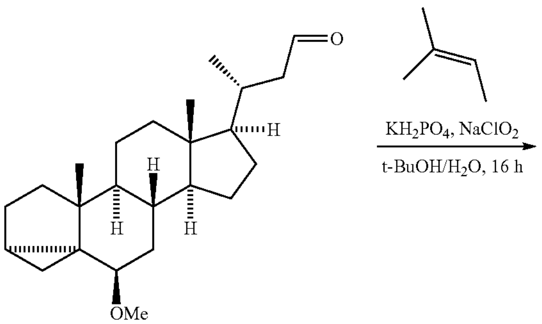

C

-continued

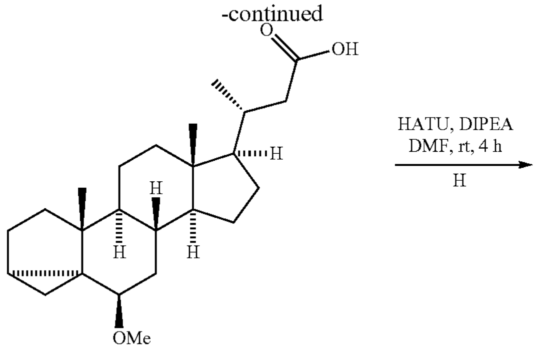

D

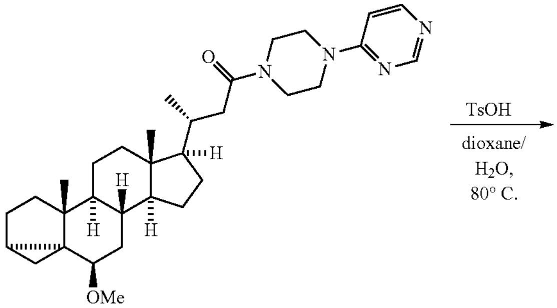

I

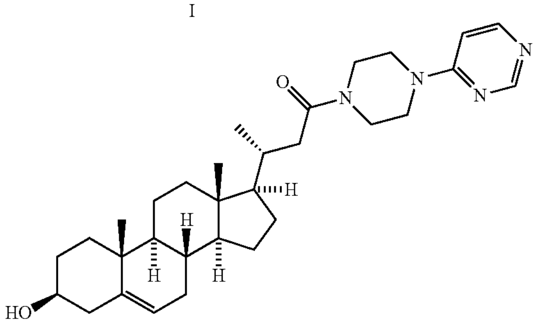

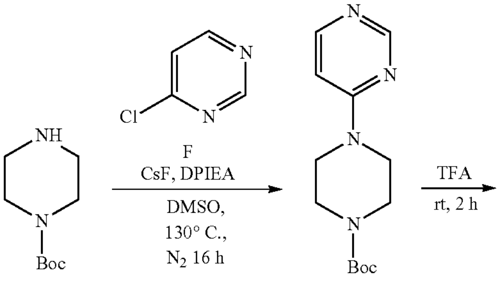

E F G

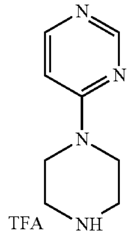

H

To a solution of compound F (184 mg, 1.61 mmol) in DMSO (4 mL) was added compound E (200 mg, 1.07 mmol), CsF (489 mg, 3.22 mmol), DIPEA (694 mg, 5.37 mmol) and the reaction stirred at 130° C. for 16 h under $N_2$. Upon completion, the reaction was diluted with water (10 mL) and extracted with ethyl acetate (20 mL). The organic layer was concentrated under reduced pressure and the crude product was purified by silica gel chromatography to afford compound G (80 mg, 28%).

To a solution of compound G (80 mg, 303 μmol) in DCM was added TFA (2 mL) and the reaction stirred at room temperature for 2 h. Upon completion, the reaction was concentrated to afford compound H (49 mg) and was used directly in the next step.

To a solution of compound D (112 mg, 298 μmol) in DMF (3 mL) was added compound H (49 mg, 176 μmol), DIPEA (193 mg, 5 eq., 1.49 mmol), HATU (140 mg, 2 eq., 597 μmol) and the reaction stirred at room temperature for 4 h. Upon completion, the reaction was diluted with water (5 mL) and extracted with ethyl acetate (15 mL). The organic layer was concentrated under reduced pressure and the crude product was purified by silica gel chromatography to afford compound I (55 mg, 35%).

(R)-3-((1aR,3aR,3bS,5aR,6R,8aS,8bS,10R,10aS)-10-methoxy-3a,5a-dimethylhexadecahydrocyclopenta[a]cyclopropa[2,3] cyclopenta[1,2-f]naphthalen-6-yl)-1-(4-(pyrimidin-4-yl)piperazin-1-yl)butan-1-one (55 mg, 106 μmol) were reacted according to Example 430 to give the title compound 595 (12 mg, 21%). LCMS: $[M+1]^+$=507.45. $^1H$ NMR (400 MHz, Chloroform-d) δ 8.62 (s, 1H), 8.25 (s, 1H), 6.53 (d, J=6.2 hz, 1H), 5.34 (d, J=5.0 hz, 1H), 3.80-3.72 (m, 4H), 3.65-3.58 (m, 4H), 3.54-3.48 (m, 1H), 2.44 (dd, J=14.0, 2.6 hz, 1H), 2.32-2.20 (m, 2H), 2.07 (d, J=13.8 hz, 1H), 2.02-1.98 (m, 2H), 1.95 (d, J=2.8 hz, 1H), 1.88-1.85 (m, 2H), 1.82 (d, J=4.2 hz, 2H), 1.67-1.56 (m, 2H), 1.55-1.49 (m, 3H), 1.43 (d, J=2.8 hz, 1H), 1.35 (d, J=9.2 hz, 1H), 1.30 (d, J=4.4 hz, 1H), 1.25 (s, 3H), 1.18-1.13 (m, 2H), 1.11 (d, J=5.8 hz, 1H), 1.08-1.05 (m, 1H), 1.00-0.88 (m, 6H), 0.73 (s, 3H).

Example 596: (S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propyl 4-(1-methyl-1H-pyrazole-4-carbonyl)piperazine-1-carboxylate

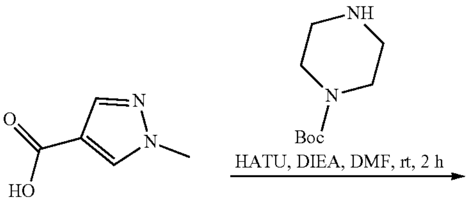

A

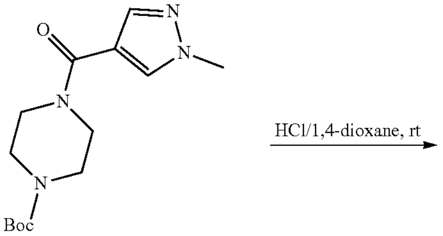

B

-continued

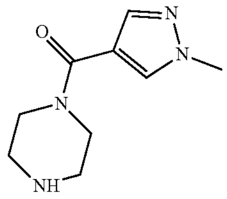

C

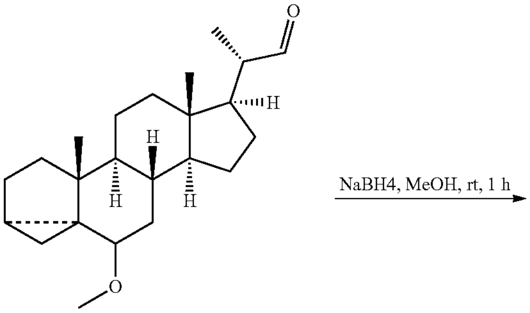

D

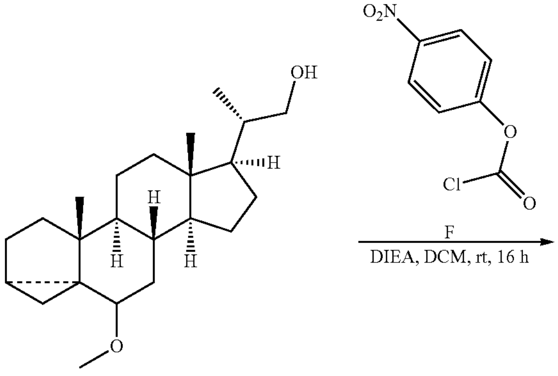

E

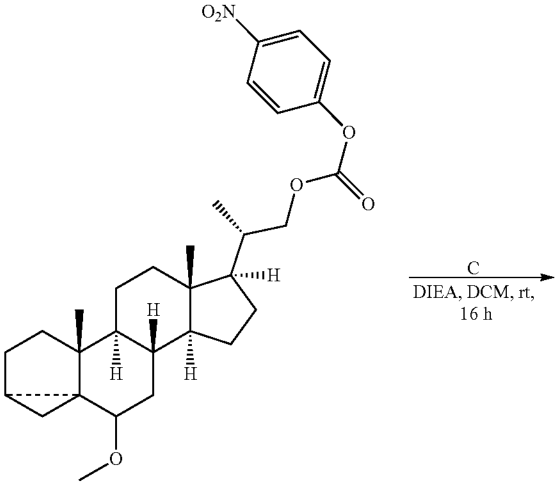

G

-continued

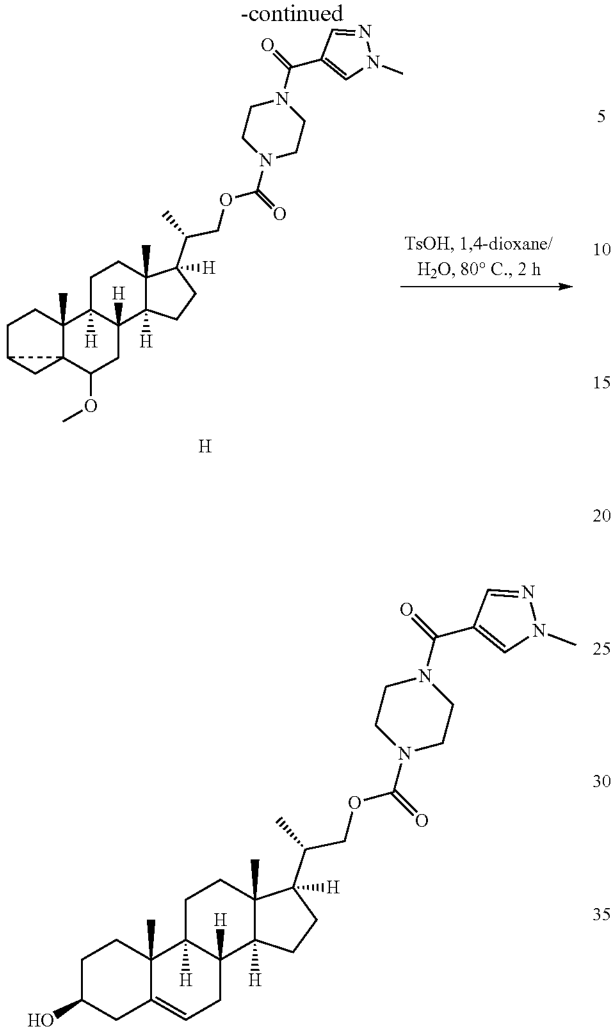

H

A solution of compound A (200 mg, 1.59 mmol), tert-butyl-piperazine-1-carboxylate (295 mg, 1.59 mmol), HATU (904 mg, 2.38 mmol) and DIPEA (615 mg, 4.76 mmol) in DMF (2 mL) was stirred at room temperature for 16 h. Water (10 mL) was added, and the reaction was extracted with EtOAc (20 mL). The organic phase was concentrated under reduced pressure and the crude product was purified by silica gel chromatography to afford compound B (200 mg, 42.8%).

A solution of compound B (467 mg, 1.59 mmol) in HCl (1 mL 4M in 1,4-dioxane) was stirred at room temperature for 2 h. The reaction was concentrated to afford compound C (0.4 g) as a white solid.

A solution of compound D (0.2 g, 580 μmol) in methanol (4 mL) was added $NaBH_4$ (43.9 mg, 1.16 mmol) and the reaction was stirred at room temperature for 1 h. Water (10 mL) was added, and the reaction was extracted with DCM (20 mL). The organic phase was concentrated to afford compound E (200 mg, 99.4%).

To a 0° C. solution of compound E (200 mg, 577 μmol) and DIPEA (373 mg, 2.89 mmol) in DCM (4 mL,) was added compound F (349 mg, 1.73 mmol) and the reaction stirred at room temperature for 16 h. The reaction was concentrated under reduced pressure and the crude product was purified by silica gel chromatography to afford compound G (200 mg, 67.7%).

A solution of compound G (50 mg, 97.7 μmol), compound C (19 mg, 82.6 μmol) and DIPEA (37.9 mg, 293 μmol) in DMF (2 mL) was stirred at room temperature for 16 h. The reaction was diluted with water (10 mL) and extracted with EtOAc (20 mL). The organic layer was concentrated, and the crude product was purified by silica gel chromatography to afford compound H (30 mg, 52.9 μmol).

(2S)-2-((1aR,3aR,3bS,5aS,6R,8aS,8bS,10aR)-10-methoxy-3a,5a-dimethylhexadecahydrocyclopenta[a]cyclopropa[2,3]cyclopenta[1,2-f]naphthalen-6-yl)propyl 4-(1-methyl-1H-pyrazole-4-carbonyl)piperazine-1-carboxylate (30 mg, 52.9 μmol) were reacted according to Example 430 to give the title compound 596 (10 mg, 34.2%) LCMS: $[M+1]^+$=553.35. $^1$H NMR (400 MHz, Chloroform-d) δ 7.71 (s, 1H), 7.60 (s, 1H), 5.35 (d, J=5.2 hz, 1H), 4.15 (dd, J=10.4, 3.6 hz, 1H), 3.93 (s, 3H), 3.81 (dd, J=10.4, 7.2 hz, 1H), 3.71-3.65 (m, 4H), 3.53-3.49 (m, 5H), 2.32-2.18 (m, 2H), 1.99 (dd, J=13.6, 10.4 hz, 2H), 1.88-1.71 (m, 4H), 1.65 (bs, 1H), 1.55-1.44 (m, 5H), 1.42-1.24 (m, 2H), 1.24-1.06 (m, 4H), 1.03 (d, J=6.8 hz, 3H), 1.01 (s, 3H), 0.98-0.89 (m, 1H), 0.71 (s, 3H).

Example 597: (2S)-2-[(1R,3aS,3bS,7S,9aR,9bS,11aS)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]propyl 4-(pyridin-4-yl)piperazine-1-carboxylate

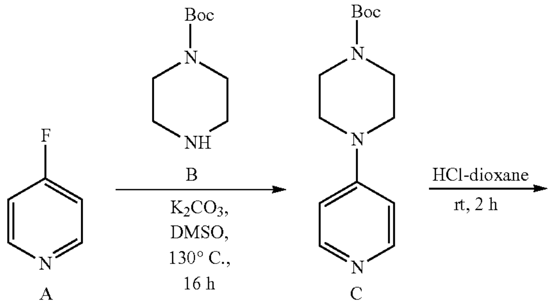

A B C

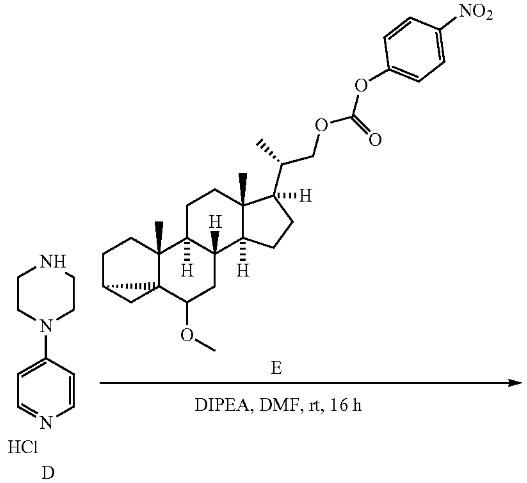

HCl
D E

-continued

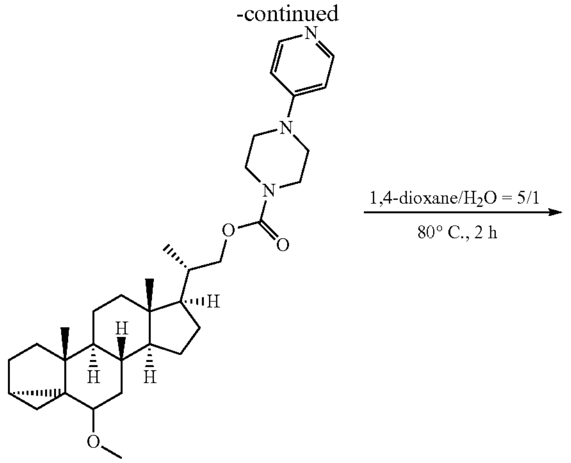

F

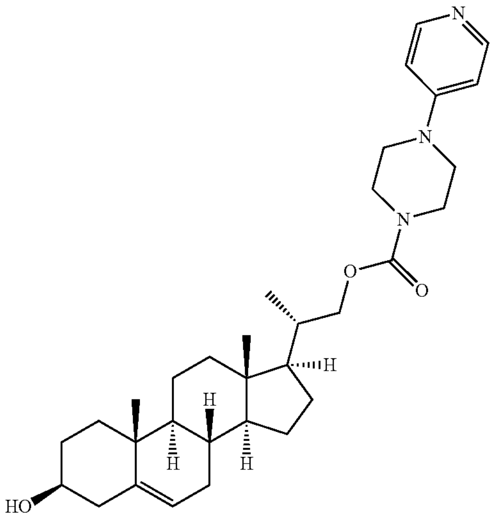

To a solution of compound A (500 mg, 5.15 mmol) and compound B (959 mg, 5.15 mmol) in DMSO (15 mL) was added $K_2CO_3$ (2.9 g, 20.6 mmol) an the reaction was stirred at 130° C. under $N_2$ atmosphere for 16. Upon completion, the reaction was cooled to room temperature. Water (30 mL) was added, and the reaction was extracted with ethyl acetate (50 mL*3). The combined organic layers were washed with water (50 mL*2), brine (40 mL), dried over sodium sulfate and concentrated under reduced pressure. The residue was purified by RP-C18 to afford compound C (700 mg, 52%) as yellow solid.

A reaction of compound C (150 mg, 570 μmol) in 4 M HCl/1, 4-dioxane (2 mL) was stirred at room temperature for 2 hours. The reaction was concentrated under reduced pressure to afford compound D as an HCl salt (113 mg).

To a solution of compound D (30 mg, 150 μmol) in DMF (2 mL) was added compound E (94 mg, 184 μmol) and DIPEA (95 mg, 735 μmol). The reaction was stirred at room temperature for 16 hours. The reaction was diluted with water (30 mL) and the reaction was extracted with ethyl acetate (20 mL*2). The combined organic layer was washed with water (20 mL*2) and brine (20 mL), dried over sodium sulfate and concentrated under reduced pressure. The residue was purified by silica gel chromatography to afford compound F (50 mg, 51%) as yellow solid.

(2S)-2-((1aR,3aR,3bS,5aS,6R,8aS,8bS,10aS)-10-methoxy-3a,5a-dimethylhexadecahydrocyclopenta[a]cyclopropa[2,3]cyclopenta[1,2-f]naphthalen-6-yl)propyl 4-(pyridin-4-yl)piperazine-1-carboxylate (50 mg, 93.3 μmol) were reacted according to Example 430 to give the title compound 597 (15 mg. 31%) as white solid. $^1$H NMR (400 MHz, Chloroform-d) δ 8.29 (d, J=5.6 hz, 2H), 6.68 (d, J=6.0 hz, 2H), 5.35 (d, J=5.2 hz, 1H), 4.16 (dd, J=10.4, 3.2 hz, 1H), 3.82 (dd, J=10.4, 7.6 hz, 1H), 3.63 (t, J=5.2 hz, 4H), 3.55-3.49 (m, 1H), 3.38-3.33 (m, 4H), 2.35-2.21 (m, 2H), 2.01-1.81 (m, 9H), 1.62 (d, J=9.0 hz, 1H), 1.56-1.43 (m, 5H), 1.23-1.10 (m, 4H), 1.07-0.99 (m, 7H), 0.98-0.91 (m, 1H), 0.72 (s, 3H).

Example 598: methyl 4-((S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)propanoyl)piperazine-1-carboxylate

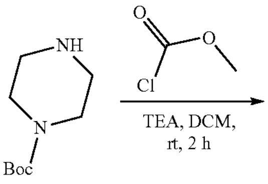

C

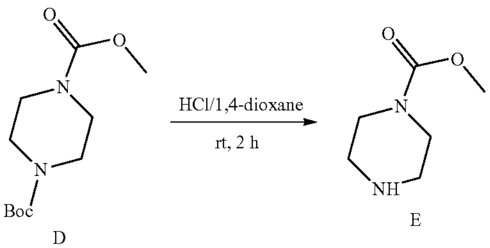

D

E

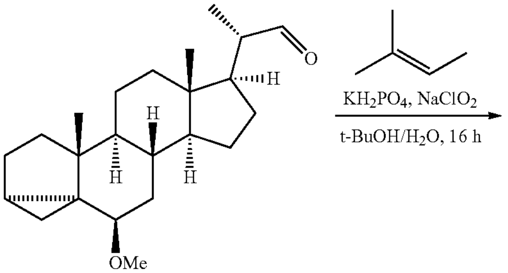

A

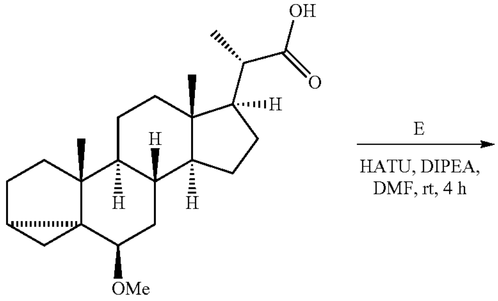

B

-continued

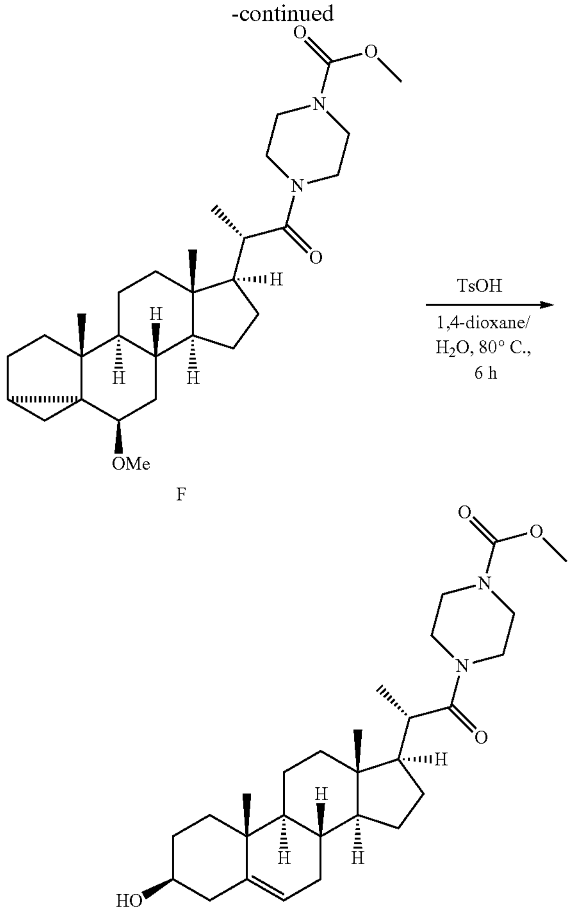

F

To a 0° C. solution of compound A (1 g, 2.9 mmol) in t-BuOH (12 mL) and water (4 mL) was added $KH_2PO_4$ (474 mg, 3.48 mmol), 2-methylbut-2-ene (305 mg, 4.35 mmol), $NaClO_2$ (315 mg, 3.48 mmol) and the reaction was warmed to room temperature for 16 h. The reaction was extracted with DCM (20 mL). The organic layer was concentrated to give compound B (1 g, 96%) which was used directly in the next step.

To a 0° C. solution of compound C (200 mg, 1.07 mmol) in DCM (6 mL) was added TEA (326 mg, 3.22 mmol) and methyl carbanochloridate (152 mg, 1.61 mmol) and the reaction was warmed to room temperature for 4 h. The reaction was diluted with water (5 mL) and extracted with DCM (10 mL). The organic layer was concentrated to give compound D (200 mg, 76%).

To a solution of compound D (200 mg, 819 μmol) in DCM (5 mL) was added hydrogen chloride (3 mL, 12N in water), the reaction was stirred at room temperature for 2 h. The reaction was concentrated to give compound E (126 mg) used in next step directly.

To a solution of compound B (0.2 g, 580 μmol) in DMF (5.33 mL) was added compound E (126 mg, 871 μmol), HATU (273 mg, 1.16 mmol), DIPEA (375 mg, 2.9 mmol) and stirred at room temperature for 4 h. The reaction was diluted with water (10 mL) and extracted with ethyl acetate (20 mL). The organic layer was concentrated under reduced pressure and the crude product was purified by silica gel chromatography to afford compound F (240 mg, 88%).

Methyl4-((S)-2-((1aR,3aR,3bS,5aS,6R,8aS,8bS,10R,10aR)-10-methoxy-3a,5a-dimethylhexadecahydrocyclopenta[a]cyclopropa[2,3]cyclopenta[1,2-f]naphthalen-6-yl)propanoyl)piperazine-1-carboxylate (240 mg, 510 μmol) were reacted according to Example 430 to give the title compound 598 (100 mg, 49%). LCMS: $[M+1]^+$=473.40. $^1H$ NMR (400 MHz, Chloroform-d) δ 5.34 (d, J=5.0 hz, 1H), 3.72 (s, 3H), 3.63-3.43 (m, 9H), 2.71 (t, J=8.0 hz, 1H), 2.32-2.20 (m, 2H), 2.00-1.93 (m, 2H), 1.87-1.78 (m, 4H), 1.58-1.52 (m, 6H), 1.51-1.47 (m, 2H), 1.45 (d, J=3.8 hz, 1H), 1.33 (bs, 1H), 1.29 (d, J=4.6 hz, 1H), 1.26 (bs, 1H), 1.15 (d, J=6.6 hz, 3H), 1.08-1.01 (m, 3H), 0.73 (s, 3H).

Example 599: (S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)-N-(pyridin-4-ylmethyl)propanamide

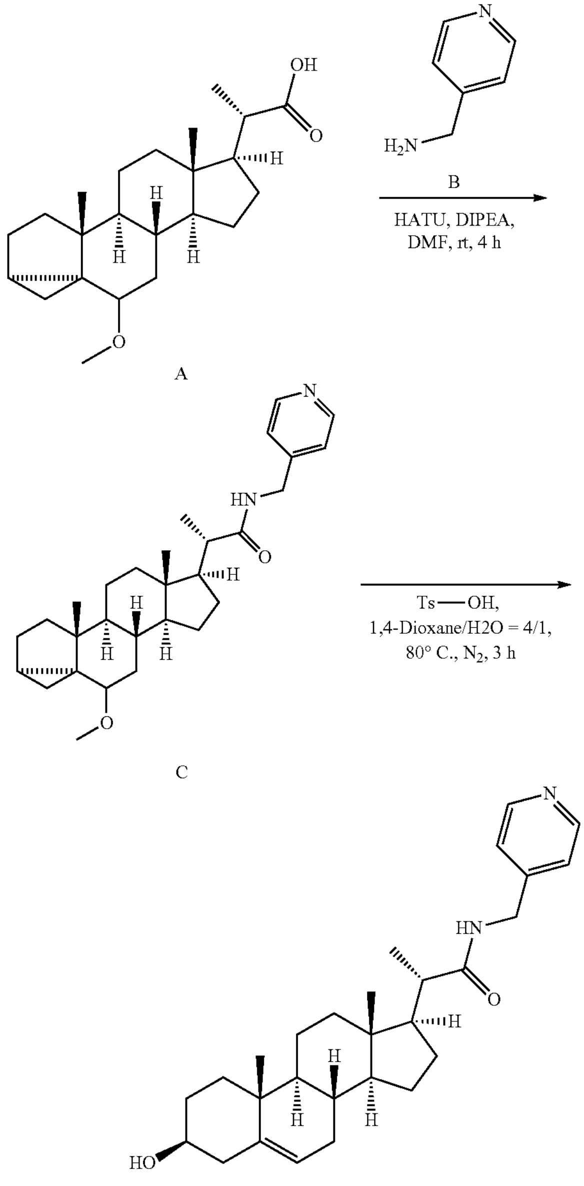

A

C

To a solution of compound A (100 mg, 277 μmol) and compound B (30 mg, 277 μmol) in DMF (3 mL) was added HATU (158 mg, 416 μmol), DIPEA (108 mg, 832 μmol) and the reaction was stirred at room temperature for 4 h. Upon completion, the reaction was quenched with saturated aqueous ammonium chloride (10 mL) and extracted with ethyl acetate (10 mL*3). The combined organic layers were washed with brine (5 mL), dried over sodium sulfate, filtered, and concentrated under reduced pressure. The crude product was purified by silica gel chromatography to afford the title compound C (70 mg, 56% yield) as a white solid.

(2S)-2-((1aR,3aR,3bS,5aS,6R,8aS,8bS,10aR)-10-methoxy-3a,5a-dimethylhexadecahydrocyclopenta[a]cyclopropa[2,3]cyclopenta[1,2-f]naphthalen-6-yl)-N-(pyridin-4-ylmethyl)propanamide (70 mg, 155 μmol) were reacted according to Example 430 to give the title compound 599 (24.2 mg, 35.68%) as white solid. LCMS: $[M+1]^+$=437.40. $^1H$ NMR (400 MHz, Chloroform-d) δ 8.55 (d, J=5.0 hz, 2H), 7.19 (d, J=5.0 hz, 2H), 5.82 (t, J=6.1 hz, 1H), 5.34 (d, J=5.1 hz, 1H), 4.52-4.36 (m, 2H), 3.52 (dt, J=11.3, 6.5 hz, 1H), 2.32-2.14 (m, 3H), 1.96 (dt, J=12.1, 3.9 hz, 2H), 1.84 (d, J=11.8 hz, 2H), 1.77 (dt, J=9.3,4.8 hz, 1H), 1.66-1.39 (m, 8H), 1.35-1.27 (m, 2H), 1.24 (d, J=7.0 hz, 3H), 1.17-1.05 (m, 3H), 1.01-0.88 (m, 4H), 0.70 (s, 3H).

Example 600: (S)-2-((3S,8S,9S,10R,13S,14S,17R)-3-hydroxy-10,13-dimethyl-2,3,4,7,8,9,10,11,12,13,14,15,16,17-tetradecahydro-1H-cyclopenta[a]phenanthren-17-yl)-N-(pyridin-4-yl)propanamide

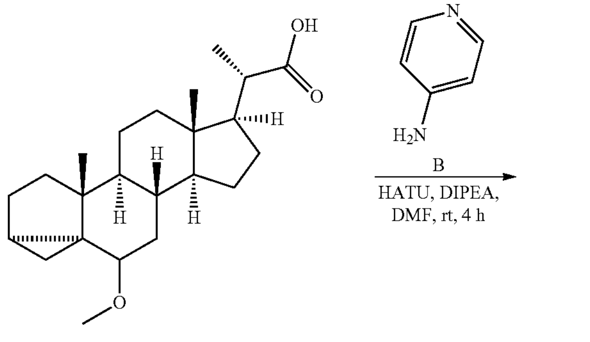

A

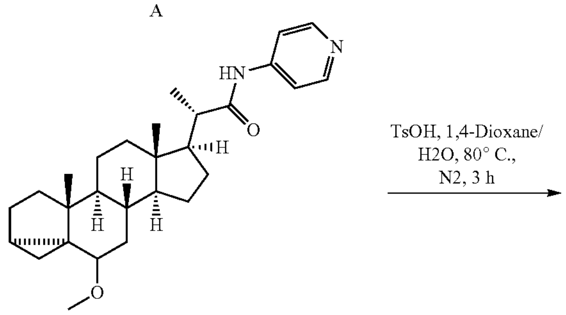

C

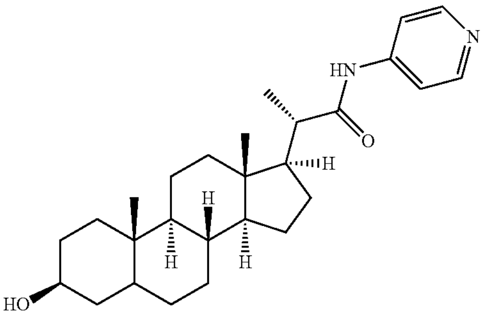

To a solution of compound A (100 mg, 277 μmol) and compound B (26.1 mg, 277 μmol) in DMF (3 mL) was added HATU (158 mg, 416 μmol), DIPEA (108 mg, 832 μmol) and the reaction was stirred at room temperature for 4 h. Upon completion, the reaction was quenched with saturated aqueous ammonium chloride (10 mL) and extracted with ethyl acetate (10 mL*3). The combined organic layers were washed with brine (10 mL), dried over sodium sulfate, filtered, and concentrated under reduced pressure. The crude product was purified by silica gel chromatography to afford compound C (50 mg, 41.29%) as white solid.

(2S)-2-((1aR,3aR,3bS,5aS,6R,8aS,8bS,10aR)-10-methoxy-3a,5a-dimethylhexadecahydrocyclopenta[a]cyclopropa[2,3]cyclopenta[1,2-f]naphthalen-6-yl)-N-(pyridin-4-yl)propanamide (50 mg, 115 μmol) were reacted according to Example 430 to give the title compound 600 (13.8 mg, 28.52%) as white solid. LCMS: $[M+1]^+$=423.40. $^1H$ NMR (400 MHz, Chloroform-d) δ 8.53-8.41 (m, 2H), 7.51-7.44 (m, 2H), 7.37 (s, 1H), 5.34 (d, J=5.2 hz, 1H), 3.56-3.50 (m, 1H), 2.18-2.34 (m, 3H), 2.01-1.92 (m, 2H), 1.84 (d, J=11.6 hz, 3H), 1.70 (d, J=9.6 hz, 2H), 1.55-1.43 (m, 4H), 1.34 (d, J=8.0 hz, 1H), 1.29 (d, J=6.4 hz, 3H), 1.26 (d, J=4.4 hz, 1H), 1.16-1.07 (m, 3H), 1.01-0.88 (s, 4H), 0.73 (s, 3H).

Example 601: (1R,3aS,3bS,7S,9aR,9bS,11aR)-1-[(2R)-4-(5-methoxypyridin-2-yl)butan-2-yl]-9a,11a-dimethyl-1H,2H,3H,3aH,3bH,4H,6H,7H,8H,9H,9aH,9bH,10H,11H,11aH-cyclopenta[a]phenanthren-7-ol

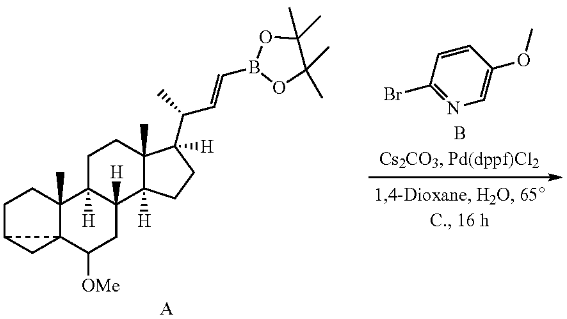

A

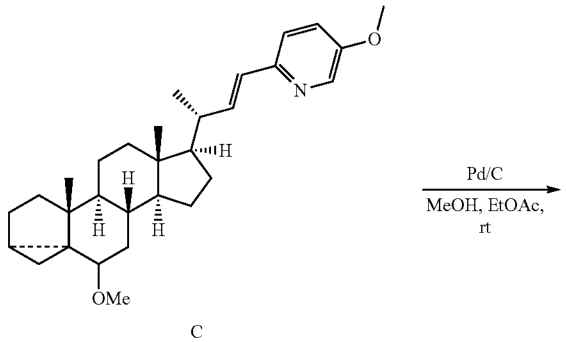

C

-continued

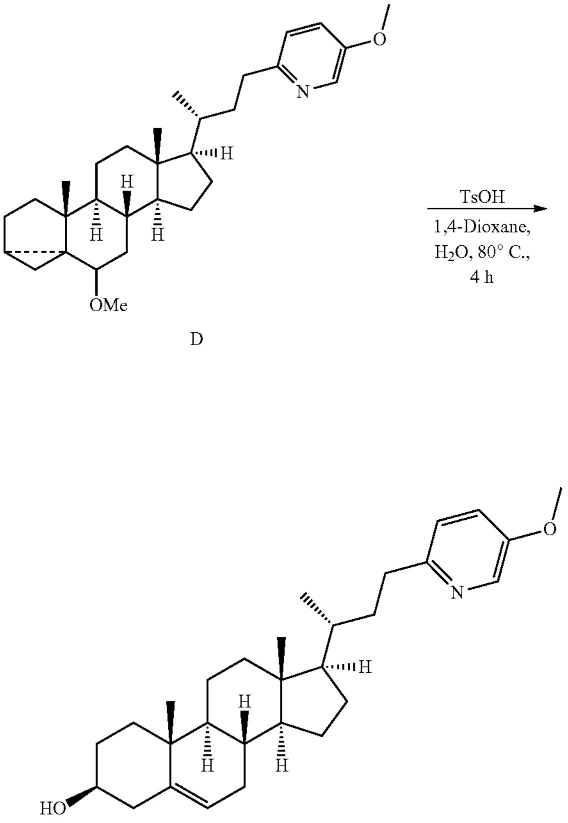

To a solution of compound A (380 mg, 811 μmol) in 1, 4-dioxane (7 mL) and water (1 mL) was added compound B (152 mg, 811 μmol), $Cs_2CO_3$ (611 mg, 2.03 mmol) and $Pd(dppf)Cl_2$ (58.9 mg, 81.1 μmol). The reaction was heated to 65° C. under $N_2$ for 16 h then cooled to room temperature and concentrated under reduced pressure. The residue was purified by silica gel chromatography to afford compound C (170 mg, 46%) as yellow solid.

To a solution of compound C (170 mg, 378 μmol) in ethyl acetate (0.5 mL) and methanol (0.5 mL) was added 10% Pd/C (35 mg). The reaction was stirred at room temperature for 5 h under hydrogen. The reaction was filtered and was concentrated under reduced pressure. The crude product was purified by prep-TLC to afford compound D (150 mg, 87%) as oil.

5-methoxy-2-((3R)-3-((1aR,3aR,3bS,5aR,6R,8aS,8bS, 10aR)-10-methoxy-3a,5a-dimethylhexadecahydrocyclopenta[a]cyclopropa[2,3]cyclopenta[1,2-f]naphthalen-6-yl) butyl)pyridine (150 mg, 332 μmol) were reacted according to Example 430 to give the title compound 601 (80 mg, 53%) as a white solid. LCMS: $[M+1]^+$=438.35. $^1H$ NMR (400 MHz, Chloroform-d) δ 8.23 (d, J=2.8 hz, 1H), 7.38 (dd, J=8.8, 2.8 hz, 1H), 7.23 (d, J=8.8 hz, 1H), 5.34 (dd, J=5.2, 2.8 hz, 1H), 3.88 (s, 3H), 3.52 (dt, J=11.2, 6.4 hz, 1H), 2.96 (td, J=12.4, 4.2 hz, 1H), 2.85-2.74 (m, 1H), 2.27-2.34 (m, 2H), 1.99-2.03 (m, 2H), 1.91-1.81 (m, 4H), 1.62-1.41 (m, 8H), 1.30 (d, J=19.2 hz, 1H), 1.22-1.11 (m, 2H), 1.06-1.01 (m, 5H), 1.00 (s, 3H), 0.93-0.88 (m, 1H), 0.67 (s, 3H).

Example 602: (3S,8S,9S,10R,13R,14S,17R)-17-((R)-4-(4-methoxypyridin-2-yl)butan-2-yl)-10,13-dim ethyl-2, 3,4, 7,8, 9,10,11,12,13,14,15,16,17-tetradecahydro-1H-cyclopenta[a]phenanthren-3-ol

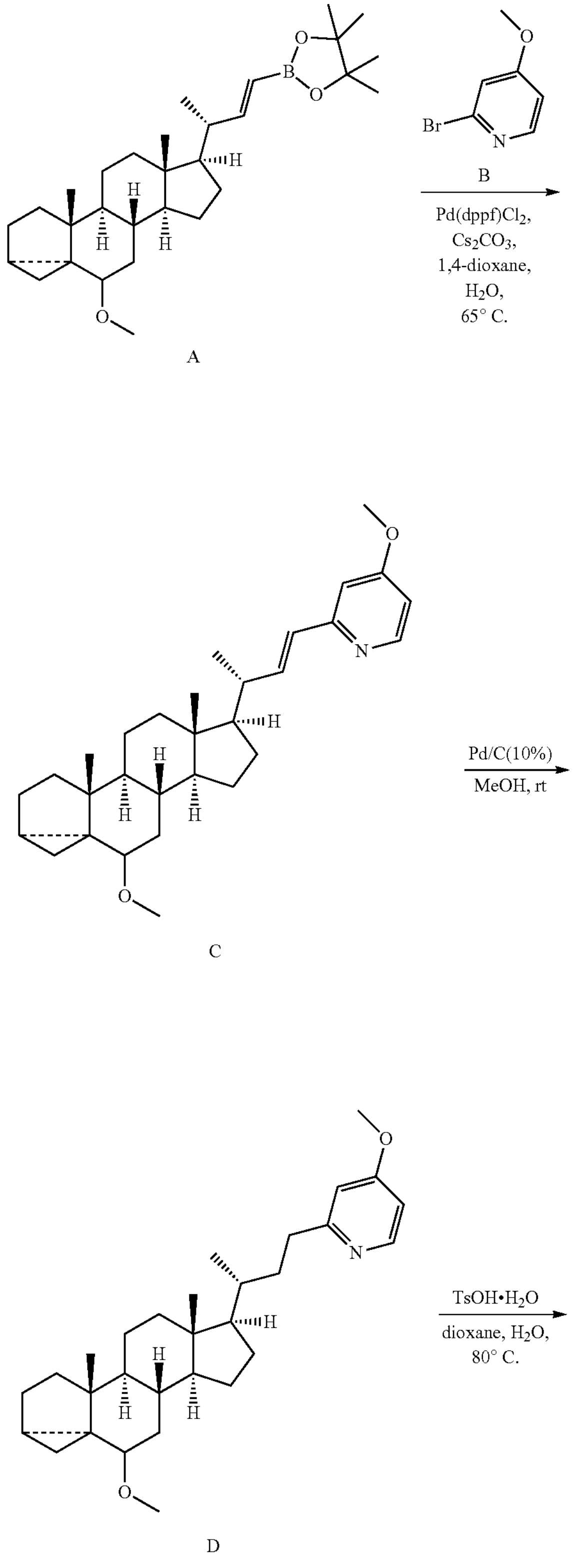

-continued

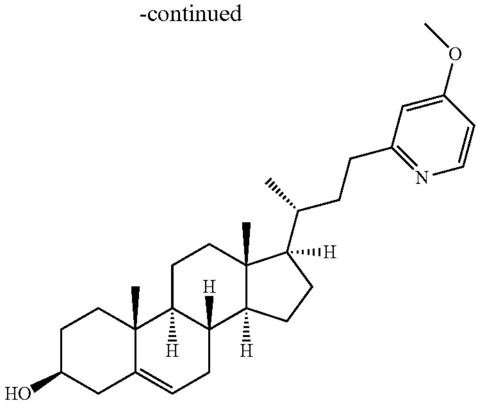

To a solution of compound A (500 mg, 1.07 mmol) in 1, 4-dioxane (9 mL) and $h_2O$ (1.3 mL) was added compound B (201.2 mg, 1.07 mmol), Pd(dppf)$Cl_2$ (80 mg, 0.11 mmol), $Cs_2CO_3$ (869 mg, 2.68 mmol) and the reaction was heated to 65° C. under $N_2$ for 16 h. The reaction was cooled to room temperature and concentrated under reduced pressure. The residue was purified by silica gel chromatography to afford compound C (218 mg, 45%) as a white solid.

To a solution of compound C (218 mg, 485 μmol) in methanol (20 mL) was added 10% Pd/C (103 mg) at room temperature. The reaction was evacuated and flushed 3 times with $h_2$ and stirred under 1 atm$h_2$ at room temperature for 2 h. The reaction was filtered and concentrated under reduced pressure to give compound D (207 mg, 94%) as a white solid.

4-methoxy-2-((3R)-3-((1aR,3aR,3bS,5aR,6R,8aS,8bS,10aR)-10-methoxy-3a,5a-dimethylhexadecahydrocyclopenta[a]cyclopropa[2,3]cyclopenta[1,2-f]naphthalen-6-yl)butyl)pyridine (70 mg, 165 μmol) were reacted according to Example 430 to give the title compound 602 (91 mg, 45%) as a white solid. LCMS: $[M+H]^+$=438.30. $^1H$ NMR (400 MHz, $CDCl_3$) δ 8.35 (d, J=6.4 hz, 1H), 6.66 (d, J=4.8 hz, 2H), 5.40-5.30 (m, 1H), 3.84 (s, 3H), 3.61-3.45 (m, 1H), 2.89-2.75 (m, 1H), 2.70-2.55 (m, 1H), 2.35-2.16 (m, 2H), 2.06-1.93 (m, 4H), 1.93-1.75 (m, 4H), 1.64-1.39 (m, 8H), 1.35-1.23 (m, 2H), 1.22-1.10 (m, 3H), 1.11-0.96 (m, 9H), 0.98-0.85 (m, 1H), 0.68 (s, 3H).

Example 603: (R)-1-(4-(1,5-dimethyl-1H-pyrazol-4-yl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

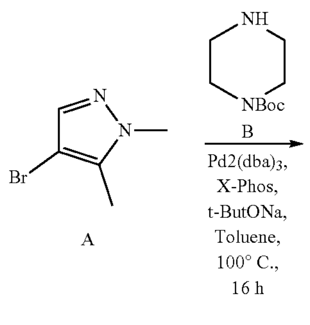

-continued

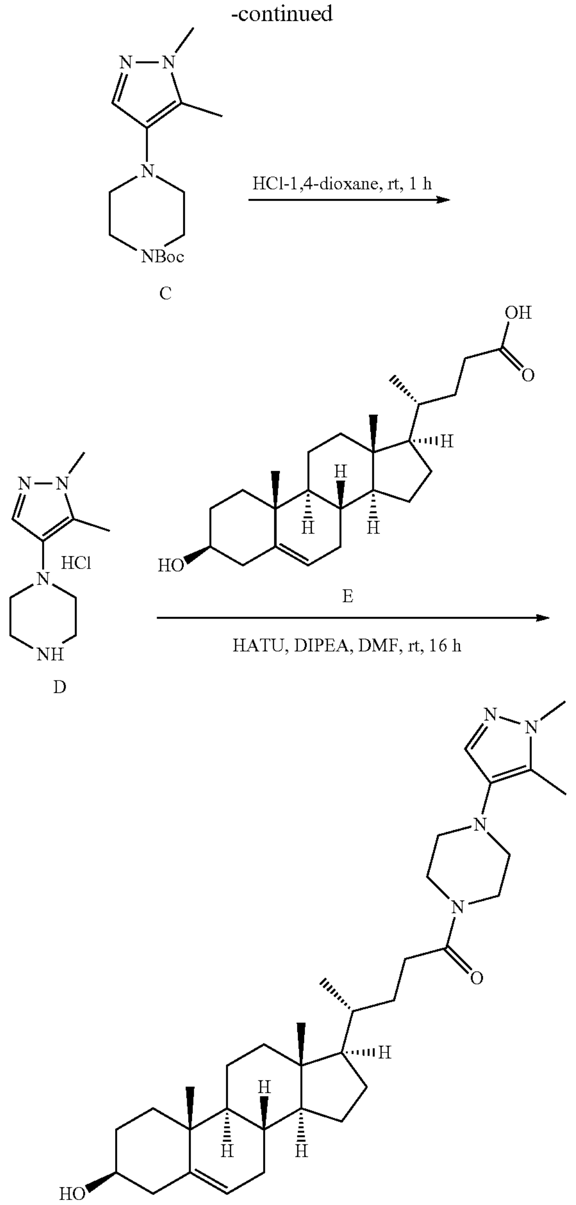

To a solution of compound A (500 mg, 2.86 mmol) and compound B (532 mg, 2.86 mmol) in toluene (10 mL) was added was added t-BuONa (824 mg, 8.57 mmol), X-phos (136 mg, 286 μmol), $Pd_2(dba)_3$ (261.5, 286 μmol) and the reaction was stirred at 100° C. for 16 h under nitrogen. Upon completion, the reaction was quenched with $h_2O$ (20 mL) and extracted with ethyl acetate (20 mL*3). The combined organic layers were washed with brine, dried over sodium sulfate, filtered, and concentrated under reduced pressure. The crude product was purified by silica gel chromatography to afford the title compound C (100 mg, 12.49%) as a white solid.

HCl in 1,4-dioxane (2 mL, 4M) was added slowly to compound C (150 mg, 357 μmol) in a single-neck flask at room temperature and stirred for 1 hour. Upon completion, the reaction was added dichloromethane (10 mL) and concentrated under reduced pressure to afford the title compound D as an HCl salt (115.9 mg).

1-(1,5-dimethyl-1H-pyrazol-4-yl)piperazine hydrochloride (111 mg, 311 μmol), (R)-4-((3S,8S,9S,10R,13R,14S, 17R)-3-hydroxy-10,13-dimethyl-2,3,4,7,8,9,10,11,12,13,14,15,16,17-tetradecahydro-1H-cyclopenta[a]phenanthren-17-yl)pentanoic acid (230 mg, 614 μmol) were reacted according to Example 536 to give the title compound 603 (26.3 mg, 7.98%) as a white solid. LCMS: $[M+1]^+$=537.45. $^1$H NMR (400 MHz, Chloroform-d) δ 7.24 (s, 1H), 5.35 (d, J=5.0 hz, 1H), 3.75 (s, 3H), 3.72 (s, 2H), 3.60-3.47 (m, 3H), 2.82-2.77 (m, 4H), 2.35-2.44 (m, 1H), 2.32-2.22 (m, 3H), 2.20 (s, 3H), 2.03-1.94 (m, 2H), 1.91-1.81 (m, 4H), 1.56-1.44 (m, 6H), 1.37-1.25 (m, 3H), 1.17 (dd, J=16.4, 11.2 hz, 2H), 1.07 (d, J=5.2 hz, 2H), 1.01 (s, 3H), 0.97-0.89 (m, 4H), 0.69 (s, 3H).

Example 604: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(1,3-dimethyl-1H-pyrazol-4-yl) piperazin-1-yl]pentan-1-one

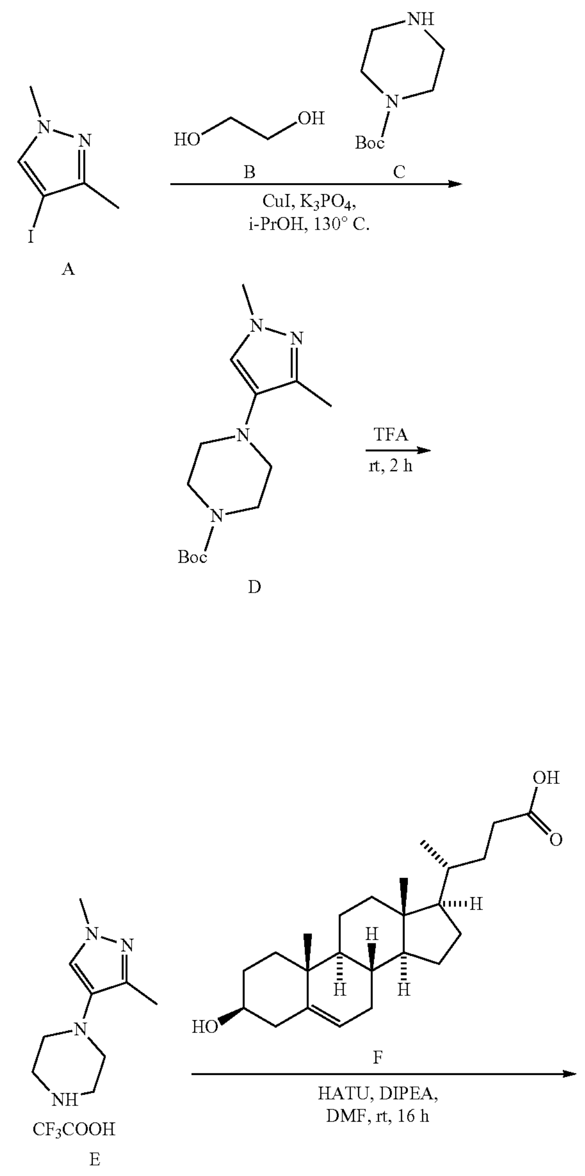

-continued

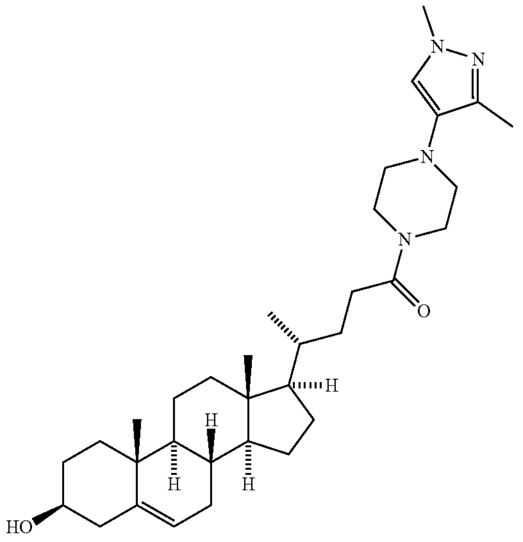

To a solution of compound A (200 mg, 901 μmol) in propan-2-ol (5 mL) at room temperature was added compound C (168 mg, 901 μmol), CuI (69 mg, 360 μmol), $K_3PO_4$ (765 mg, 3.6 mmol) and compound B (112 mg, 1.8 mmol). The reaction was stirred at 130° C. for 16 hours then the reaction was cooled to room temperature, filtered through Celite and concentrated under reduced pressure. The crude material was purified by reverse phase chromatography to afford compound D (70 mg, 28%) as yellow solid.

A solution of compound D (75 mg, 198 μmol) in TFA (2 mL) was stirred at room temperature for 2 hours. The reaction was concentrated under reduced pressure to afford E as the TFA salt (76 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (25 mg, 66.7 μmol) and 1-(1,3-dimethyl-1H-pyrazol-4-yl) piperazine 2,2,2-trifluoroacetate (60 mg, 153 μmol) were reacted according to Example 536 to give the title compound 604 (29 mg, 15%) as white solid. $^1$H NMR (400 MHz, Chloroform-d) δ 6.98 (s, 1H), 5.38-5.32 (m, 1H), 3.75-3.72 (m, 5H), 3.59-3.57 (m, 2H), 3.53-3.49 (m, 1H), 2.82-2.76 (m, 4H), 2.44-2.36 (m, 1H), 2.31-2.16 (m, 6H), 2.02-1.98 (m, 2H), 1.90-1.84 (m, 2H), 1.79-1.72 (m, 2H), 1.53-1.41 (m, 8H), 1.36-1.30 (m, 3H), 1.15-1.07 (m, 3H), 1.02-0.84 (m, 9H), 0.69 (s, 3H).

Example 605: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(1-methyl-1H-1,2,4-triazol-5-yl)piperazin-1-yl)pentan-1-one

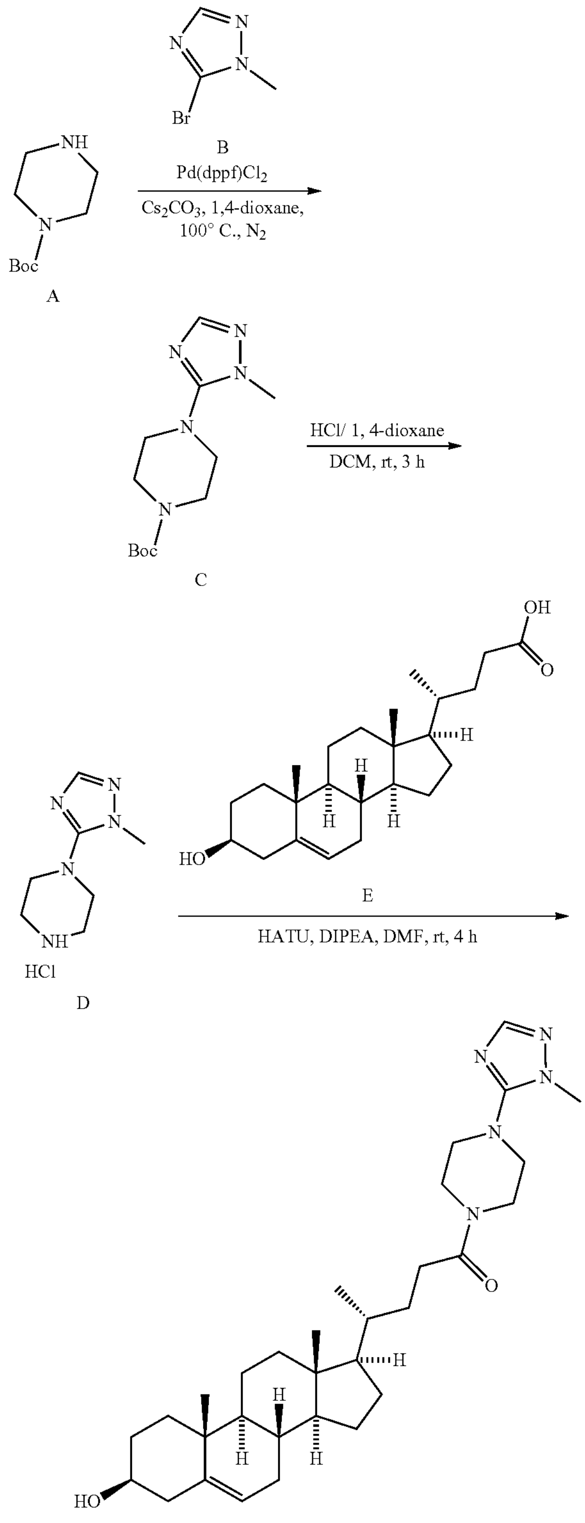

To a solution of compound B (261 mg, 1.61 mmol) in 1,4-dioxane (6 mL) was added compound A (0.2 g, 1.07 mmol), $CsCO_3$ (1.05 g, 3.22 mmol), Pd(dppf)$Cl_2$ (156 mg, 215 μmol) and stirred at 100° C. for 16 hours. The reaction was extracted with DCM (30 mL*2). The combined organic layers were concentrated under reduced pressure to afford compound C (200 mg, 70%) as yellow oil.

To a solution of compound C (0.2 g, 748 μmol) in DCM (2 mL) was added HCl/1, 4-dioxane (292 mg, 8 mmol) and stirred at room temperature for 2 hours. The reaction was concentrated to afford compound D as an HCl salt (125 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (280 mg, 748 μmol) and 1-(1-methyl-1H-1,2,4-triazol-5-yl)piperazine hydrochloride (125 mg, 613 μmol) were reacted according to Example 536 to give the title compound 605 (70 mg, 18%) as white solid. LCMS: $[M+1]^+$=524.45. $^1H$ NMR (400 MHz, Chloroform-d) δ 7.63 (s, 1H), 5.35 (d, J=5.0 hz, 1H), 3.74 (bs, 4H), 3.63 (d, J=5.6 hz, 2H), 3.52 (dt, J=11.2, 6.0 hz, 1H), 3.24-3.10 (m, 4H), 2.41 (s, 1H), 2.34-2.20 (m, 3H), 2.04-1.95 (m, 2H), 1.87-1.78 (m, 3H), 1.63 (s, 3H), 1.48-1.41 (m, 6H), 1.44 (d, J=6.4 hz, 3H), 1.36 (dd, J=9.2, 4.4 hz, 1H), 1.26-1.15 (m, 3H), 1.15-1.05 (m, 3H), 1.01 (s, 3H), 0.96 (d, J=6.4 hz, 3H), 0.69 (s, 3H).

Example 606: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(1-methyl-1H-tetrazol-5-yl)piperazin-1-yl)pentan-1-one

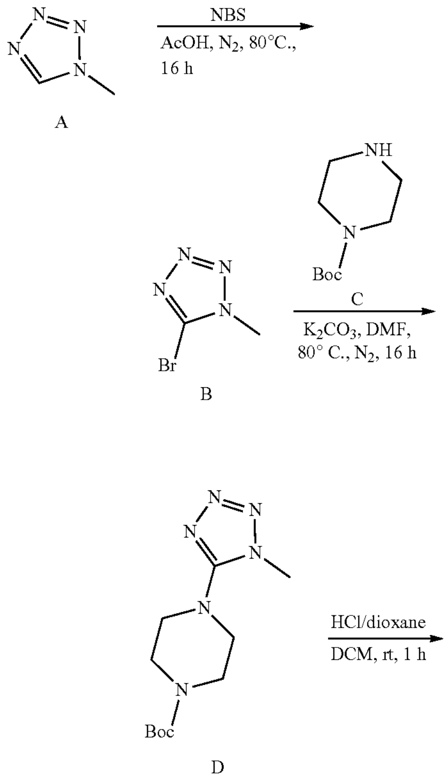

-continued

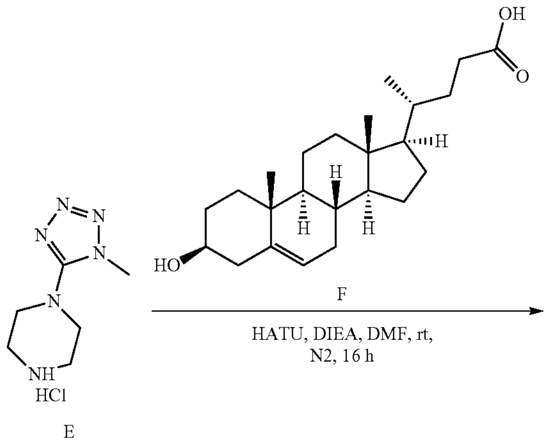

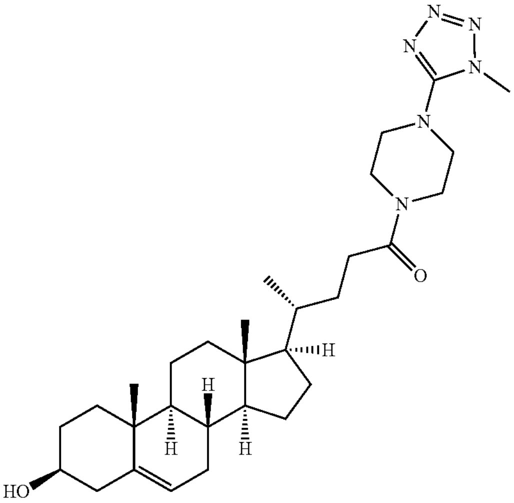

To a solution of compound A (500 mg, 5.95 mmol) in acetic acid (40 mL) was added NBS (1.27 g, 7.14 mmol) and the reaction was stirred at 80° C. under $N_2$ for 16 h. The reaction was quenched with water (80 mL) and extracted with EtOAc (200 mL). The organic layer was washed with brine (50 mL), dried over sodium sulfate, filtered, and concentrated. The residue was purified by silica gel chromatography to afford the compound B (750 mg, 78.2%) as yellow oil.

To a solution of compound B (150 mg, 920 μmol) in DMF (6 mL) was added compound C (206 mg, 1.1 mmol) and $K_2CO_3$ (382 mg, 2.76 mmol). The reaction was stirred at 80° C. under $N_2$ for 16 h. The reaction was quenched with water (10 mL) and extracted with EtOAc (40 mL). The organic layers were washed with brine, dried over sodium sulfate, filtered, and concentrated. The residue was purified by silica gel chromatography to afford compound D (150 mg, 60.4%) as a white solid.

To a solution of D (150 mg, 372 μmol) in DCM (2 mL) was added HCl in 1,4-dioxane (0.5 mL, 4M). The reaction was stirred at room temperature for 2.0 h. The reaction was concentrated to afford the compound E as an HCl salt (125 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (334 mg, 892 μmol) and 1-(1-methyl-1H-tetrazol-5-yl)piperazine HCl salt (125 mg, 372 μmol) were reacted according to Example 536 to give the title compound 606 (122 mg, 26%) as a white solid. LCMS: $[M+1]^+$=525.35. $^1H$ NMR (400 MHz, Chloroform-d) δ 5.35 (d, J=5.1 hz, 1H), 3.91 (s, 3H), 3.77 (d, J=5.2 hz, 2H), 3.67 (t, J=5.0 hz, 2H), 3.52 (dt, J=11.1, 6.2 hz, 1H), 3.37 (t, J=5.1 hz, 2H), 3.26 (d, J=5.7 hz, 2H), 2.42 (ddd, J=15.6, 10.9, 5.1 hz, 1H), 2.33-2.19 (m, 3H), 2.00-1.76 (m, 6H), 1.56-1.29 (m, 9H), 1.23-0.83 (m, 14H), 0.69 (s, 3H).

Example 607: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(4-methylthiazol-5-yl)piperazin-1-yl)pentan-1-one

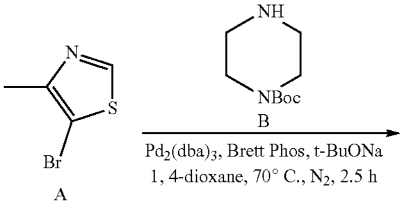

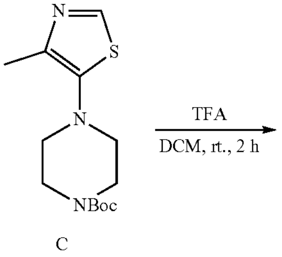

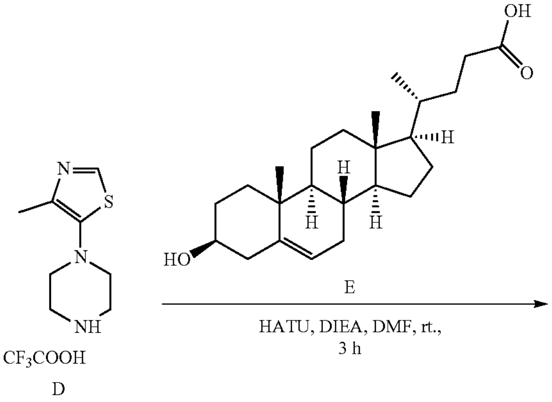

-continued

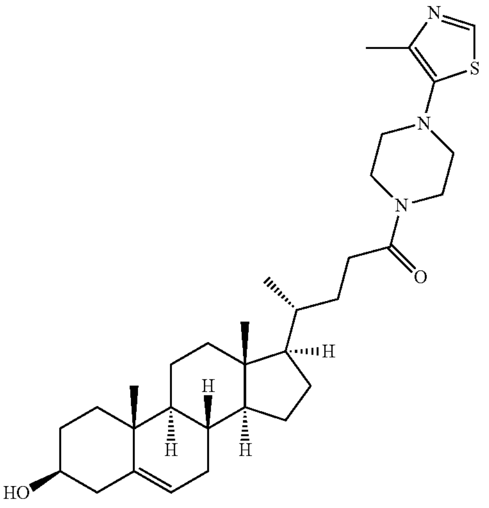

To a solution of compound A (200 mg, 1.12 mmol) in 1,4-dioxane (4 mL) was added compound B (418 mg, 2.25 mmol), BrettPhos (30.1 mg, 56.2 μmol), t-BuONa (216 mg, 2.25 mmol) and $Pd_2(dba)_3$ (41.4 mg, 56.2 μmol). The reaction was stirred at 70° C. for 2.5 h. The reaction was cooled to room temperature and filtered through Celite. The filtrate was concentrated under reduced pressure. The crude product was purified by silica gel chromatography to afford compound C (160 mg, 49.8%) as yellow oil.

To a solution of compound C (100 mg, 353 μmol) in DCM (2 mL) was added TFA (0.5 mL). The reaction was stirred at room temperature for 2 h. The reaction was concentrated under reduced pressure to afford compound D as the TFA salt (96 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (100 mg, 404 μmol) and 4-methyl-5-(piperazin-1-yl)thiazole (96 mg, 320 μmol) were reacted according to Example 536 to give the title compound 607 (9.6 mg, 6.7%) as a white solid. LCMS: $[M+1]^+$=540.40. $^1$HNMR (400 MHz, Chloroform-d) δ 8.47 (s, 1H), 5.35 (d, J=5.2 hz, 1H), 3.76 (bs, 2H), 3.61-3.52 (m, 3H), 2.86-2.79 (m, 4H), 2.44-2.39 (m, 1H), 2.37 (s, 3H), 2.29-2.20 (m, 3H), 1.99-1.84 (m, 8H), 1.57-1.39 (m, 9H), 1.31-1.03 (m, 9H), 1.01 (s, 3H), 0.96 (d, J=6.4 hz, 3H), 0.89 (d, J=7.2 hz, 1H), 0.69 (s, 3H).

Examples 608: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-methyl-4-(1-methyl-1H-pyrazol-5-yl)piperazin-1-yl)pentan-1-one

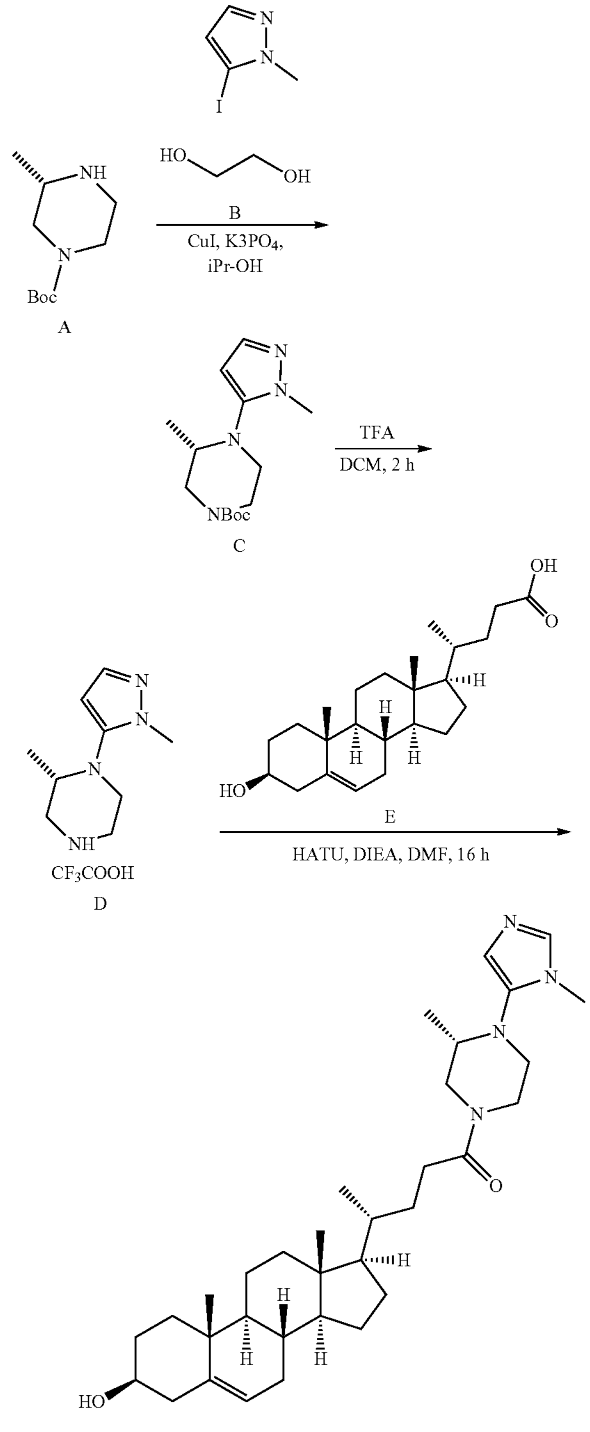

To a room temperature solution of compound B (415 mg, 2 mmol) in isopropanol (5 mL) was added compound A (200 mg, 999 μmol), CuI (38 mg, 0.2 mmol), ethane-1,2-diol (62 mg, 999 μmol) and $K_3PO_4$ (848 mg, 3.99 mmol). The reaction was stirred at 110° C. for 16 hours under $N_2$. Upon completion, the reaction was quenched by the addition of water (15 mL) and extracted with ethyl acetate (50 mL). The organic layer was dried over sodium sulfate and was concentrated under reduced pressure. The crude product was purified by silica gel chromatography to afford compound C (27 mg, 10%) as yellow solid.

To a solution of compound C (27 mg, 96.3 μmol) in DCM (3 mL) was added TFA (22 mg, 193 μmol). The reaction was stirred for 2 hours. Upon completion, the solution was concentrated to afford compound D as the TFA salt (15 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (24.9 mg, 66.6 μmol) and (S)-4-(piperidin-3-yloxy)pyridine hydrochloride (15 mg, 54 μmol) were reacted according to Example 536 to give the title compound 608 (9.7 mg, 22%) as a white solid. LCMS: $[M+1]^+$=537.40. $^1$H NMR (400 MHz, Chloroform-d) δ 7.17 (s, 1H), 5.61 (d, J=8.4 hz, 1H), 5.35 (d, J=5.2 hz, 1H), 3.75 (s, 3H), 3.63-3.29 (m, 4H), 3.17-2.97 (m, 2H), 2.45-2.19 (m, 4H), 2.05-1.93 (m, 2H), 1.89-1.80 (m, 3H), 1.50-1.43 (m, 5H), 1.25-1.20 (m, 7H), 1.19-0.87 (m, 15H), 0.69 (s, 3H).

Example 609: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-2-methyl-4-(1-methyl-1H-pyrazol-5-yl)piperazin-1-yl)pentan-1-one

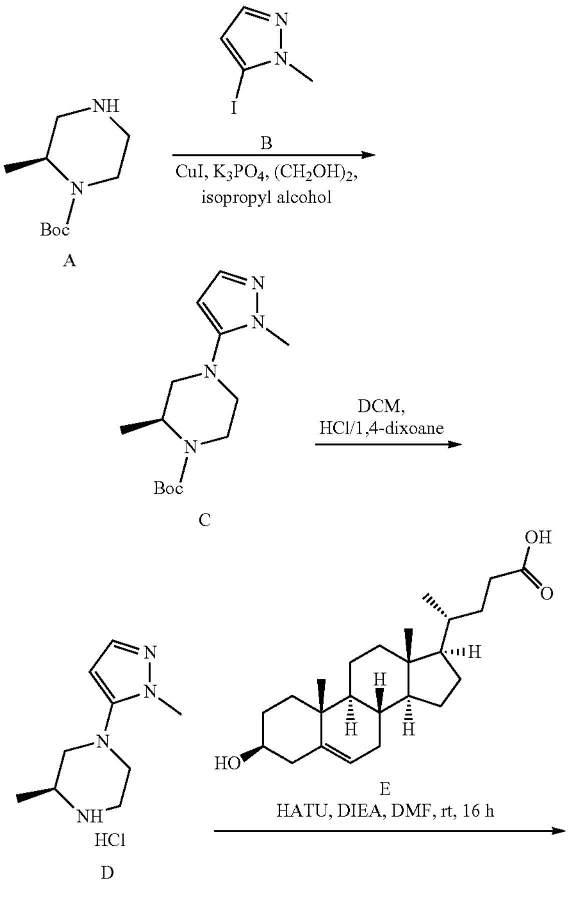

-continued

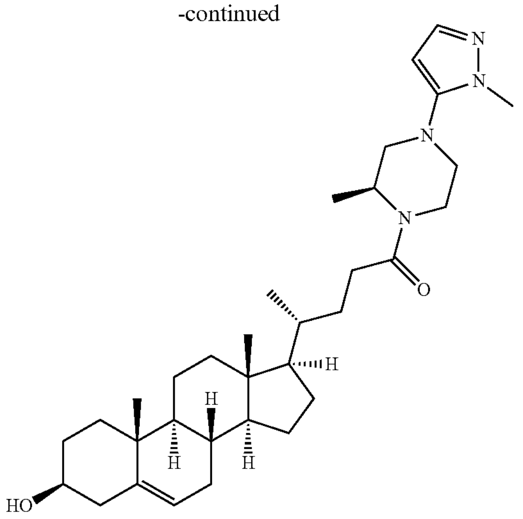

To a solution of compound A (200 mg, 1 mmol) in isopropanol (3 mL) was added compound B (415 mg, 2 mmol), CuI (38 mg, 200 μmol), $K_3PO_4$ (840 mg, 4 mmol) and ethane-1,2-diol (62 mg, 1 mmol). The reaction was heated to 130° C. under $N_2$ for 16 h. The reaction was cooled to room temperature and concentrated under reduced pressure. The residue was purified by silica gel chromatography to afford compound C (120 mg, 42%) as yellow oil.

To a solution of compound C (120 mg, 428 μmol) in DCM (3 mL) was added hydrogen chloride (2 mL, 4M in 1, 4-dioxane) at room temperature and the reaction was stirred for 2 h. The reaction was concentrated under reduced pressure to afford compound D as an HCl salt (83 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (116 mg, 311 μmol) and(S)-3-methyl-1-(1-methyl-1H-pyrazol-5-yl)piperazinehydrochloride (83 mg, 388 μmol) were reacted according to Example 536 to give the title compound 609 (80 mg, 38%) as a white solid. LCMS: $[M+1]^+$=537.40. $^1$H NMR (400 MHz, Chloroform-d) δ 7.16 (d, J=2.4 hz, 1H), 5.63 (d, J=2.4 hz, 1H), 5.35 (d, J=5.2 hz, 1H), 4.50 (d, J=13.8 hz, 1H), 4.11 (bs, 1H), 3.75 (s, 3H), 3.68-3.48 (m, 4H), 2.84-2.66 (m, 2H), 2.49-2.17 (m, 4H), 2.06-1.92 (m, 2H), 1.91-1.76 (m, 4H), 1.59-1.43 (m, 8H), 1.41-1.25 (m, 6H), 1.21-1.10 (m, 2H), 1.08-1.03 (m, 2H), 1.01 (s, 3H), 0.98-0.90 (m, 4H), 0.69 (s, 3H).

Example 610: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(3-methoxypyrazin-2-yl)piperazin-1-yl)pentan-1-one

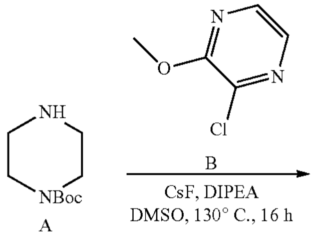

-continued

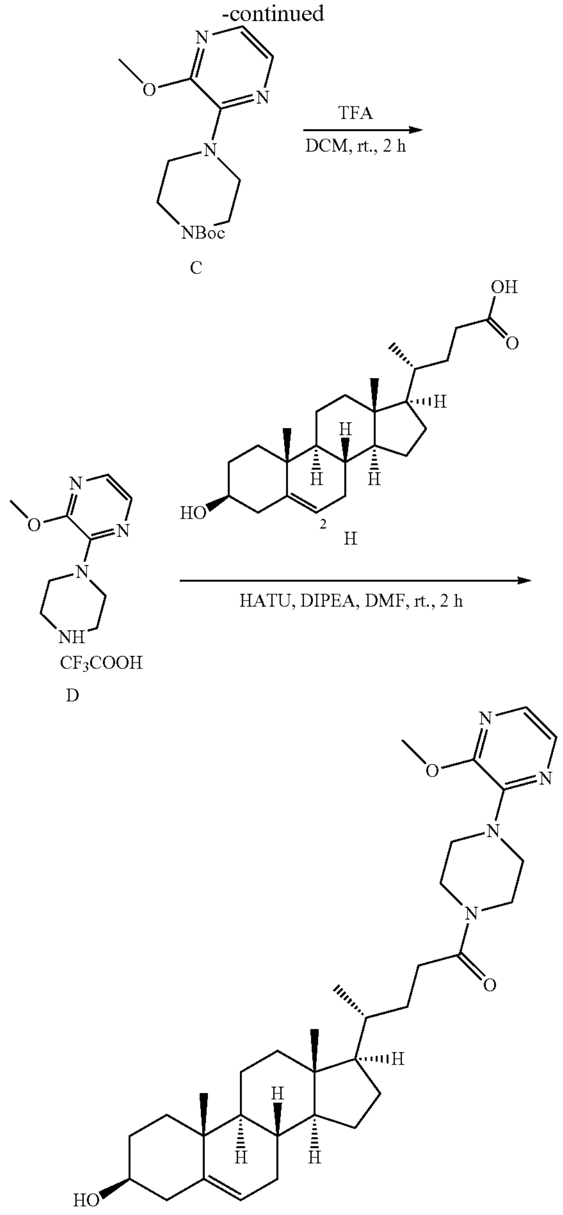

To a solution of compound A (200 mg, 1.07 mmol) in DMSO (3 mL) was added compound B (310 mg, 2.15 mmol), CsF (489 mg, 3.22 mmol) and DIPEA (694 mg, 5.37 mmol). The reaction was stirred at 130° C. under $N_2$ for 16 h. The reaction was quenched with water (10 mL) and extracted with EtOAc (30 mL). The organic layer was washed with brine, dried over sodium sulfate and concentrated under reduced pressure. The crude was purified by silica gel chromatography to afford compound C (200 mg, 679 μmol, 63.3%) as yellow oil.

To a solution of compound C (200 mg, 679 μmol) in DCM (2 mL) was added TFA (0.5 mL). The reaction was stirred at room temperature for 1 h. The reaction was concentrated under reduced pressure to afford compound D as the TFA salt (198 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (150 mg, 404 μmol) and 2-methoxy-3-(piperazin-1-yl)pyrazine (198 mg, 601 μmol) were reacted according to Example 536 to give the title compound 610 (152 mg, 68.9%) as a white solid. LCMS: $[M+1]^+$=551.45. $^1$HNMR (400 MHz, Chloroform-d) δ 7.73 (d, J=2.8 hz, 1H), 7.60 (d, J=2.8 hz, 1H), 5.35 (d, J=5.2 hz, 1H), 4.00 (s, 3H), 3.74 (t, J=5.2 hz, 2H), 3.60 (t, J=5.2 hz, 2H), 3.50-3.41 (m, 5H), 2.42 (ddd, J=15.6, 11.2, 5.2 hz, 1H), 2.33-2.18 (m, 3H), 1.99 (tt, J=14.0, 3.6 hz, 2H), 1.91-1.75 (m, 4H), 1.64-1.42 (m, 11H), 1.42-1.25 (m, 3H), 1.22-1.03 (m, 5H), 1.01 (s, 3H), 0.97 (d, J=6.4 hz, 3H), 0.95-0.86 (m, 1H), 0.69 (s, 3H).

Example 611: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(4-methoxypyridin-3-yl)piperazin-1-yl)pentan-1-one

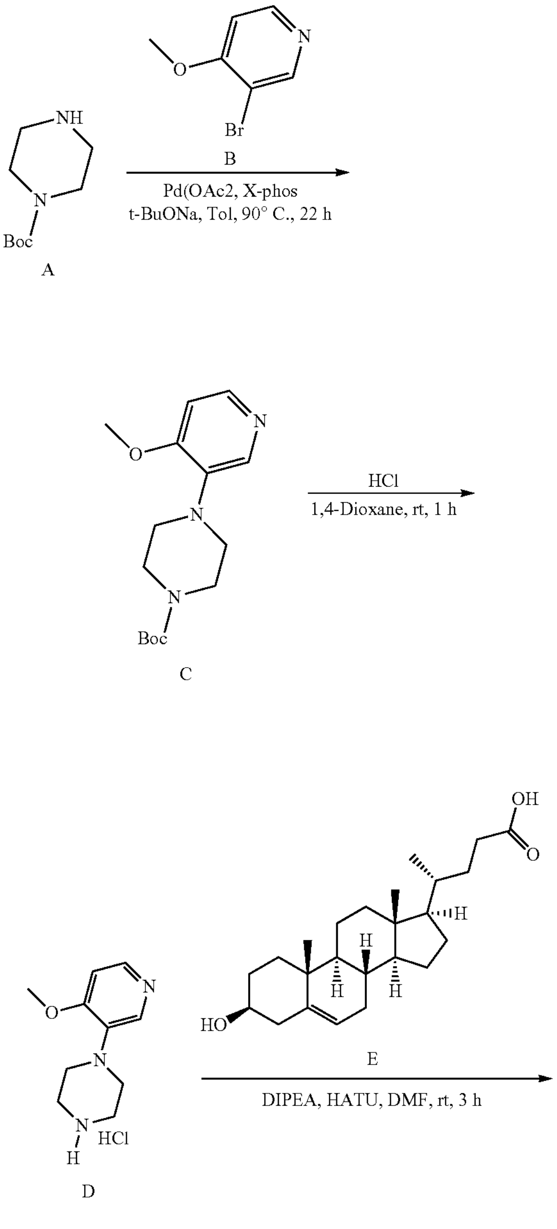

-continued

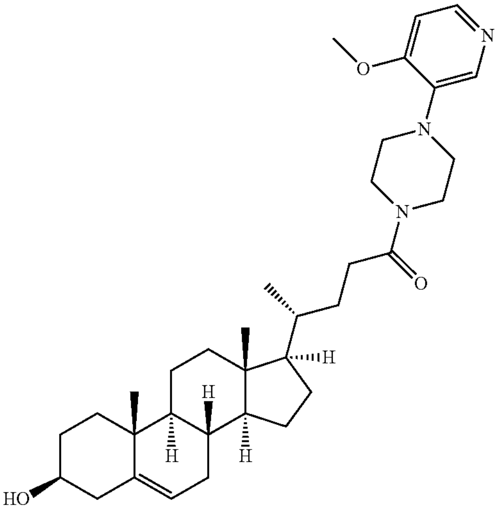

To a solution of compound A (466 mg, 2.50 mmol) in toluene (20 mL) was added compound B (470 mg, 2.5 mmol), $Pd(OAc)_2$ (56 mg, 250 μmol), t-BuONa (361 mg, 3.75 mmol) and X-phos (239 mg, 0.5 mmol). The reaction was heated to 90° C. under $N_2$ for 22 h. The reaction was cooled to room temperature and concentrated under reduced pressure. The residue was purified by silica gel chromatography to afford compound C (410 mg, 56%) as a yellow solid.

To a solution of compound C (300 mg, 1.02 mmol) in 1,4-dioxane (6 mL) was added hydrogen chloride (1.5 mL, 6 mmol, 4M in 1, 4-dioxane) at room temperature and the reaction was stirred for 1 h. The reaction was concentrated under reduced pressure to afford compound D as an HCl salt (200 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (78 mg, 207 μmol) and 1-(4-methoxypyridin-3-yl)piperazine hydrochloride (50 mg, 220 μmol) were reacted according to Example 536 to give the title compound 611 (99 mg, 70%) as a white solid. LCMS: $[M+1]^+$=550.35. $^1H$ NMR (400 MHz, DMSO-$d_6$) δ 8.24 (d, J=5.6 hz, 1H), 8.09 (s, 1H), 6.81 (d, J=5.6 hz, 1H), 5.35 (d, J=5.2 hz, 1H), 3.94 (s, 3H), 3.78 (t, J=5.2 hz, 2H), 3.64 (t, J=4.8 hz, 2H), 3.57-3.45 (m, 1H), 3.15-3.03 (m, 4H), 2.42 (td, J=10.4, 5.4 hz, 1H), 2.34-2.17 (m, 3H), 2.08-1.91 (m, 2H), 1.90-1.75 (m, 4H), 1.55-1.41 (m, 7H), 1.39-1.06 (m, 9H), 1.01 (s, 3H), 0.97 (d, J=6.4 hz, 3H), 0.69 (s, 3H).

Example 612: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(2-methoxypyridin-3-yl)piperazin-1-yl)pentan-1-one

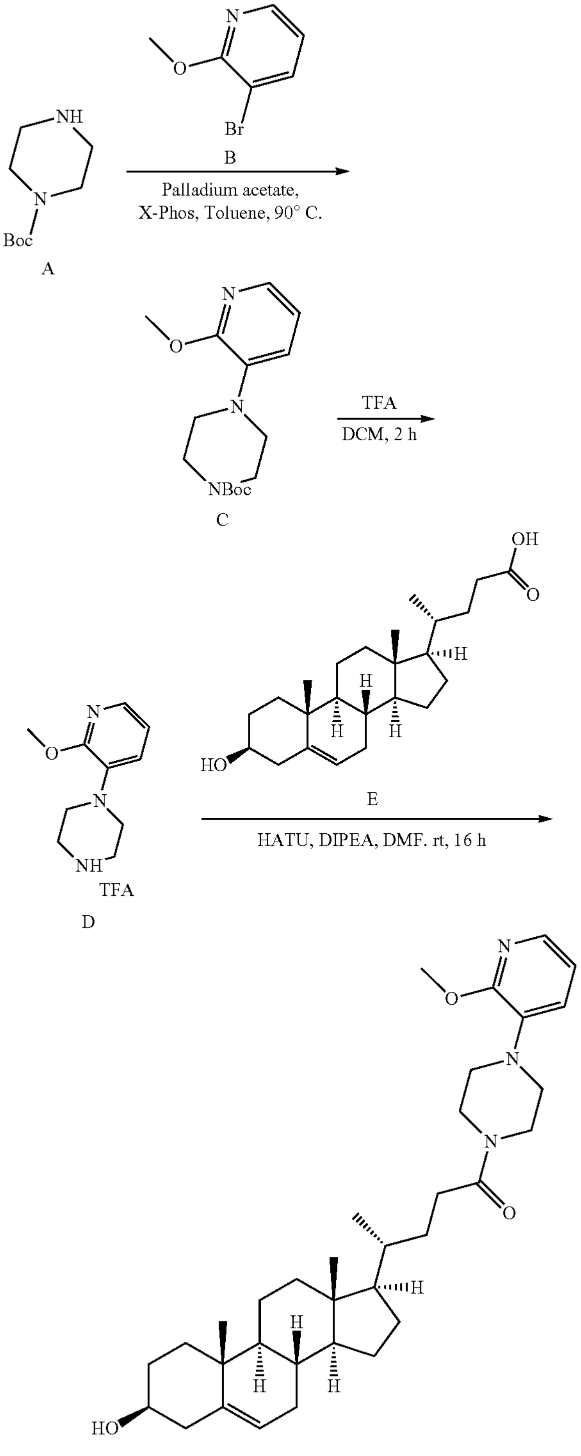

To a solution of compound B (200 mg, 1.07 mmol) in toluene (4 mL) was added compound A (242 mg, 1.29 mmol), palladium acetate (42.8 mg, 215 μmol), X-Phos (102 mg, 215 μmol) and t-BuONa (206 mg, 2.15 mmol). The reaction was stirred at 90° C. for 4 h under $N_2$.

The reaction was quenched by $h_2O$ (10 mL) and extracted with ethyl acetate (20 mL) and the organic layer was concentrated under reduced pressure. The crude product was purified by silica gel chromatography to afford compound C (200 mg, 63%) as yellow solid.

To a solution of compound C (150 mg, 511 μmol) in DCM (2 mL) was added TFA (0.4 mL, 5.12 mmol). The reaction was stirred at room temperature for 4 hours. The solution was concentrated to afford compound D as the TFA salt (95 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (93 mg, 248 μmol) and 1-(2-methoxypyridin-3-yl)piperazine TFA salt (80 mg, 260 μmol) were reacted according to Example 536 to give the title compound 612 (36.5 mg, 16%) as a white solid. LCMS: $[M+1]^+$=550.35. $^1$H NMR (400 MHz, Chloroform-d) δ 7.84 (dd, J=4.8, 1.6 hz, 1H), 7.08 (dd, J=7.6, 1.6 hz, 1H), 6.85 (dd, J=7.6, 5.2 hz, 1H), 5.35 (d, J=5.2 hz, 1H), 4.01 (s, 3H), 3.79 (d, J=5.6 hz, 2H), 3.65 (t, J=5.2 hz, 2H), 3.60-3.47 (m, 1H), 3.11-2.99 (m, 4H), 2.44-2.38 (m, 1H), 2.32-2.20 (m, 3H), 2.03-1.95 (m, 2H), 1.84-1.71 (m, 4H), 1.54-1.44 (m, 6H), 1.39-1.32 (m, 2H), 1.26 (bs, 2H), 1.21-1.05 (m, 4H), 1.01 (s, 3H), 0.97 (d, J=6.4 hz, 3H), 0.92-0.84 (m, 1H), 0.69 (s, 3H).

Example 613: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(3-methoxypyridin-2-yl)piperazin-1-yl)pentan-1-one

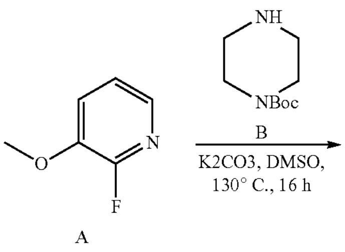

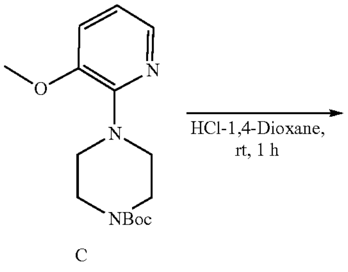

-continued

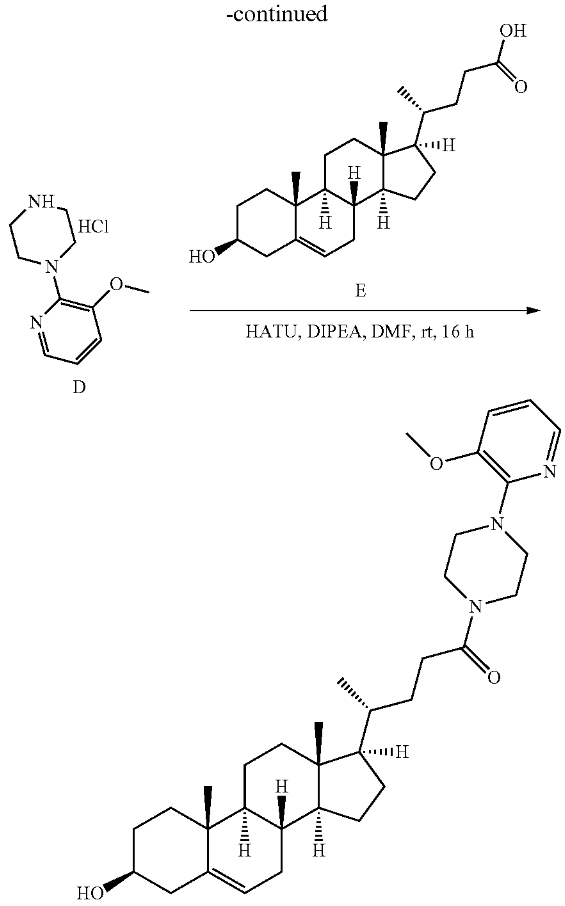

To a solution of compound A (100 mg, 787 μmol) and compound B (147 mg, 787 μmol) in DMSO (3 mL) was added $K_2CO_3$ (326 mg, 2.36 mmol). The reaction was stirred at 130° C. for 16 hours. Upon completion, the reaction was quenched with saturated aqueous ammonium chloride (10 mL) and extracted with ethyl acetate (10 mL*3). The combined organic layers were washed with brine, dried over sodium sulfate, filtered, and concentrated under reduced pressure. The crude product was purified by silica gel chromatography to afford compound C (45 mg, 19.5%) as yellow solid.

4N HCl and 1,4-dioxane (2 mL) was added slowly to compound C (45 mg, 153 μmol) in a single-neck flask at room temperature and stirred for 1 hour. Upon completion, the reaction was concentrated under reduced pressure to afford the title compound D as an HCl salt (35.2 mg).

1-(3-methoxypyridin-2-yl)piperazine hydrochloride (35.2 mg, 153 μmol) and (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (77.5 mg, 207 μmol) were reacted according to Example 536 to give the title compound 613 (14.7 mg, 12.92%) as a white solid. LCMS: $[M+1]^+$=550.50. $^1$H NMR (400 MHz, Chloroform-d) δ 7.87 (d, J=4.8 hz, 1H), 7.07 (d, J=8.0 hz, 1H), 6.88 (dd, J=7.6, 4.8 hz, 1H), 5.35 (s, 1H), 3.87-3.63 (m, 7H), 3.51 (d, J=13.6 hz, 1H), 3.38 (d, J=17.6 hz, 4H), 2.41 (d, J=11.2 hz, 1H), 2.27-2.01 (m, 5H), 1.85-1.47 (m, 10H), 1.32 (d, J=11.6 hz, 2H), 1.26 (s, 3H), 1.22-1.04 (m, 5H), 1.01 (s, 3H), 0.97 (d, J=6.4 hz, 3H), 0.69 (s, 3H).

Example 614: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(4-methoxypyrimidin-5-yl)piperazin-1-yl]pentan-1-one

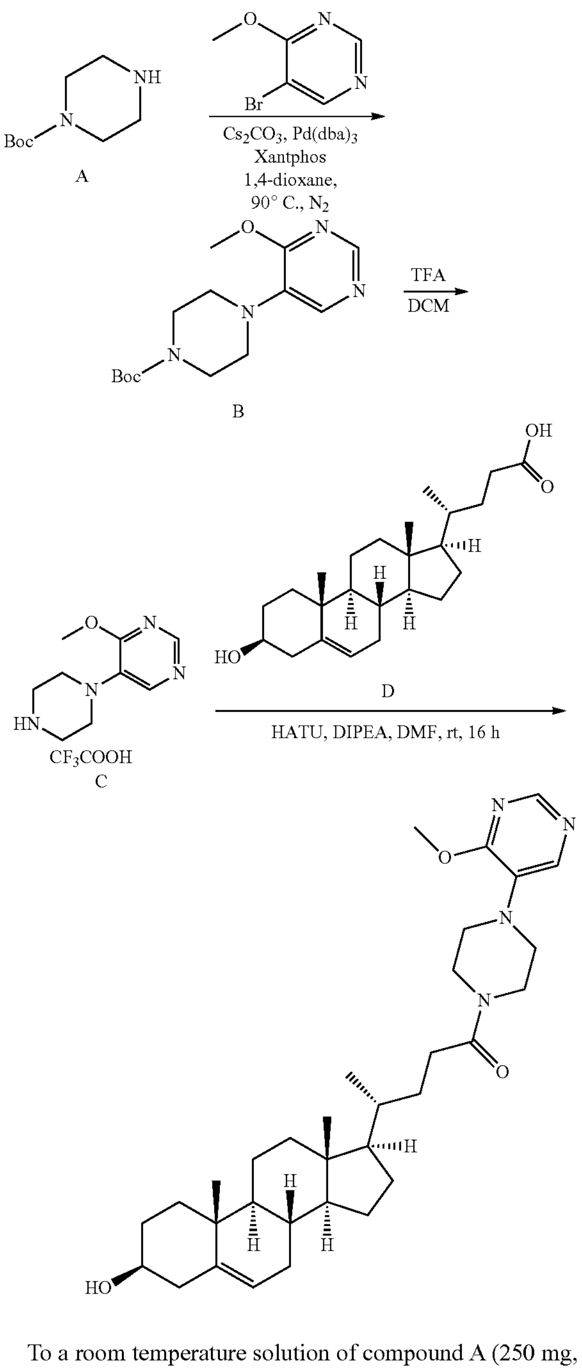

To a room temperature solution of compound A (250 mg, 1.34 mmol) in 1, 4-dioxane (10 mL) was added $Cs_2CO_3$ (875 mg, 2.68 mmol), 5-bromo-4-methoxypyrimidine (228 mg, 1.21 mmol), XantPhos (77.7 mg, 134 μmol) and $Pd_2(dba)_3$ (61.5 mg, 67.1 μmol). The reaction was heated to 90° C. for 16 h under nitrogen. The reaction was diluted with water (10 mL) and extracted with ethyl acetate (30 mL). The organic layer was washed with water and brine, dried over sodium sulfate, and was concentrated under reduced pressure. The crude product was purified by silica gel chromatography to afford compound B (150 mg, 37.9%) as white solid.

To a solution of compound B (50 mg, 170 μmol) in dichloromethane (3 mL) was added trifluoroacetic acid (0.5 mL) dropwise at room temperature. The reaction was stirred at room temperature for 2 h. The reaction was concentrated under reduced pressure to give compound C as the TFA salt (52 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (63.2 mg, 169 μmol) and 4-methoxy-5-(piperazin-1-yl)pyrimidine 2,2,2-trifluoroacetate (52 mg, 169 μmol) were reacted according to Example 536 to give the title compound 614 (11.2 mg, 12.0%) as a white solid. LCMS: $[M+1]^+$=551.50. $^1H$ NMR (400 MHz, $CDCl_3$) δ 8.47 (s, 1H), 8.00 (s, 1H), 5.35 (d, J=5.2 hz, 1H), 4.06 (s, 3H), 3.78 (t, J=5.2 hz, 2H), 3.64 (t, J=5.2 hz, 2H), 3.55-3.49 (m, 1H), 3.12-3.06 (m, 4H), 2.45-2.38 (m, 1H), 2.30-2.21 (m, 3H), 2.01-1.95 (m, 3H), 1.91-1.80 (m, 4H), 1.53-1.43 (m, 6H), 1.32 (d, J=10.8 hz, 2H), 1.26 (d, J=3.6 hz, 3H), 1.19-1.05 (m, 4H), 1.01 (s, 3H), 0.97 (d, J=6.4 hz, 3H), 0.69 (s, 3H).

Example 615: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-4-(5-methoxypyrimidin-4-yl)-3-methylpiperazin-1-yl)pentan-1-one

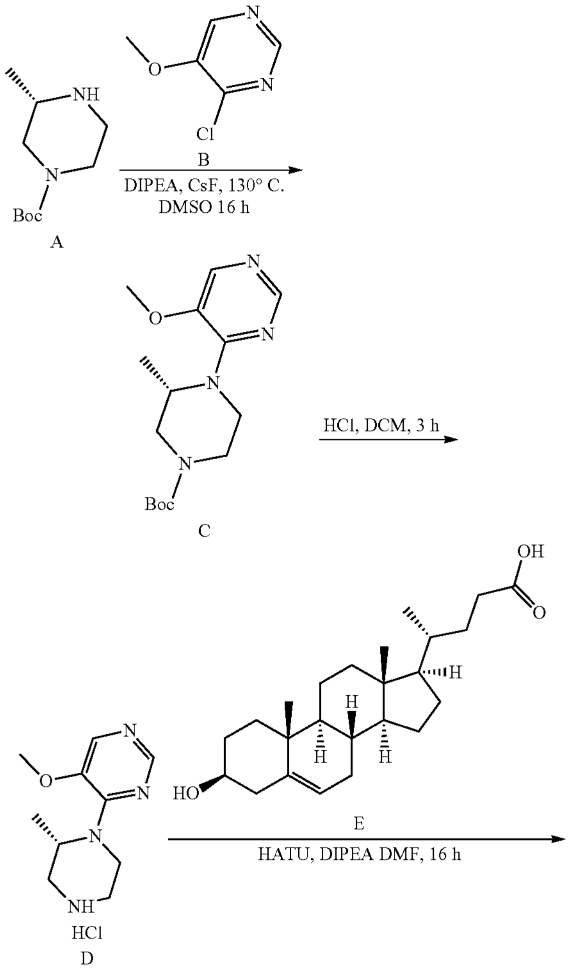

-continued

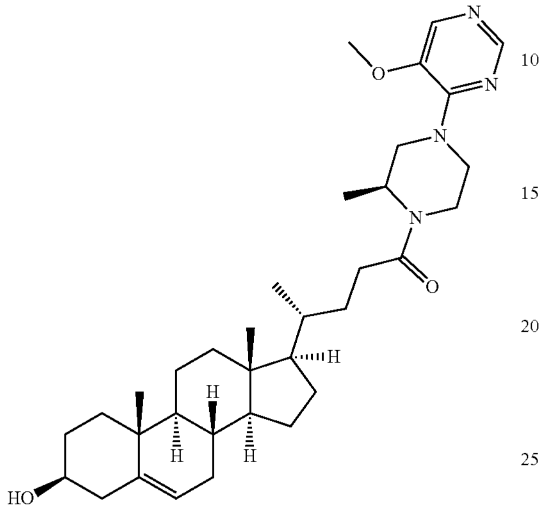

To a solution of compound A (100 mg, 499 μmol) in DMSO (3 mL), was added compound B (60 mg, 416 mmol), DIPEA (161 mg, 1.25 mmol) and CsF (126 mg, 832 μmol). The reaction was heated to 130° C. under $N_2$ for 16 h. The reaction was cooled to room temperature and water (30 mL) was added. The reaction was extracted with EtOAc (10 mL*2). The combined organic layers were washed with water (20 mL), brine (20 mL), dried over sodium sulfate and concentrated under reduced pressure. The residue was purified by silica gel chromatography to afford compound C (40 mg, 31%) as yellow oil.

To a solution of compound C (40 mg, 130 μmol) in DCM (2 mL) was added hydrogen chloride (1 mL, 4 mmol, 4M in dioxane) at room temperature and the reaction was stirred for 2 h. The reaction was concentrated under reduced pressure to afford compound D as an HCl salt (30 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (36 mg, 96 μmol and (S)-5-methoxy-4-(2-methylpiperazin-1-yl)pyrimidine hydrochloride (30 mg, 120 μmol), to give the title compound 615 (15.6 mg, 23%) as a white solid. LCMS: $[M+1]^+$=565.40. $^1$H NMR (400 MHz, Chloroform-d) δ 8.33 (s, 1H), 7.94 (s, 1H), 5.35 (d, J=5.2 hz, 1H), 4.88 (s, 1H), 4.53 (d, J=13.2 hz, 1H), 4.38 (s, 1H), 4.30 (d, J=13.2 hz, 1H), 3.88 (bs, 3H), 3.63 (d, J=9.6 hz, 1H), 3.54-3.43 (m, 1H), 3.37-3.23 (m, 1H), 2.30-2.15 (m, 4H), 1.99 (t, J=13.2 hz, 2H), 1.85-1.78 (m, 4H), 1.60-1.42 (m, 8H), 1.38-1.27 (m, 4H), 1.18 (d, J=6.8 hz, 2H), 1.15-1.06 (m, 3H), 1.01 (s, 4H), 0.98-0.90 (m, 4H), 0.69 (s, 3H).

Example 616: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-4-(5-methoxypyrimidin-4-yl)-2-methylpiperazin-1-yl)pentan-1-one

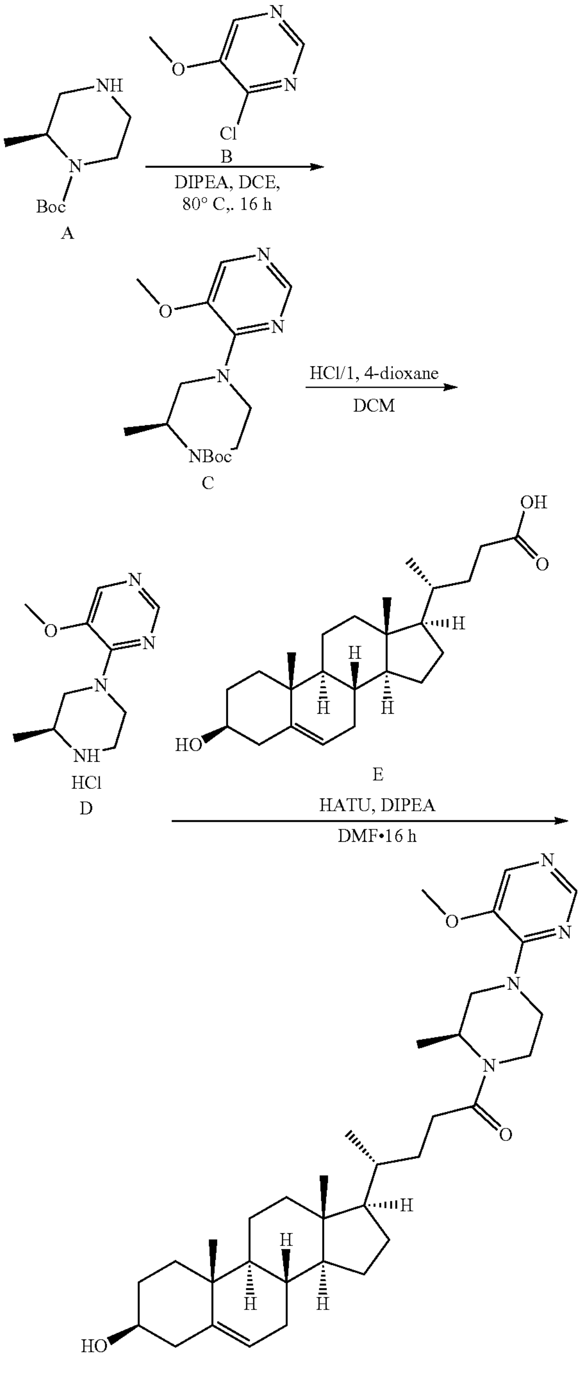

To a solution of compound B (100 mg, 692 μmol) in 1,2-dichloroethane (5 mL) was added compound A (166 mg, 830 μmol) and DIPEA (482 μL, 2.77 mmol). The reaction was stirred at 80° C. for 16 hours. The reaction was quenched by $h_2O$ (10 mL) and extracted with DCM (30 mL). The organic layer was dried over sodium sulfate and was concentrated under reduced pressure. The crude product was purified by silica gel chromatography to afford compound C (90 mg, 42%) as yellow solid.

To a solution of compound C (90 mg, 292 μmol) in DCM (3 mL) was added HCl (4 M in solution of 1,4-dioxane, 0.2 mL, 876 μmol). The reaction was stirred at room temperature for 4 hours. The solution was concentrated to afford compound D as an HCl salt (60 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (87.5 mg, 233 μmol) and (S)-5-methoxy-4-(3-methylpiperazin-1-yl)pyrimidinehCl salt (60 mg, 246 μmol) were reacted according to Example 536 to give the title compound 616 (32.1 mg, 19%) as a white solid. LCMS: $[M+1]^+$=565.30. $^1$H NMR (400 MHz, Chloroform-d) δ 8.31 (s, 1H), 7.91 (s, 1H), 5.34 (d, J=5.2 hz, 1H), 4.57 (dd, J=12.8, 2.8 hz, 1H), 4.47 (d, J=12.4 hz, 1H), 3.88 (s, 3H), 3.70 (dt, J=15.6, 8.0 hz, 1H), 3.56-3.47 (m, 1H), 3.18 (q, J=7.6 hz, 2H), 2.99 (s, 1H), 2.32-2.19 (m, 3H), 2.01-1.94 (m, 2H), 1.84-1.74 (m, 6H), 1.53-1.40 (m, 8H), 1.36-1.26 (m, 3H), 1.18-1.06 (m, 5H), 1.00 (s, 3H), 0.96 (d, J=6.4 hz, 4H), 0.68 (s, 3H).

Example 617: (R)-1-(4-(2,5-dimethoxypyrimidin-4-yl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

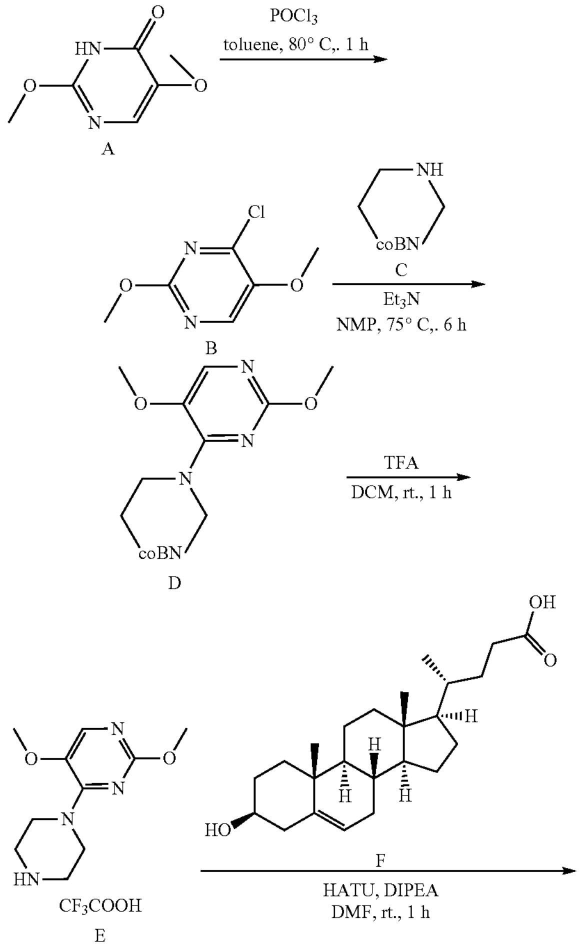

-continued

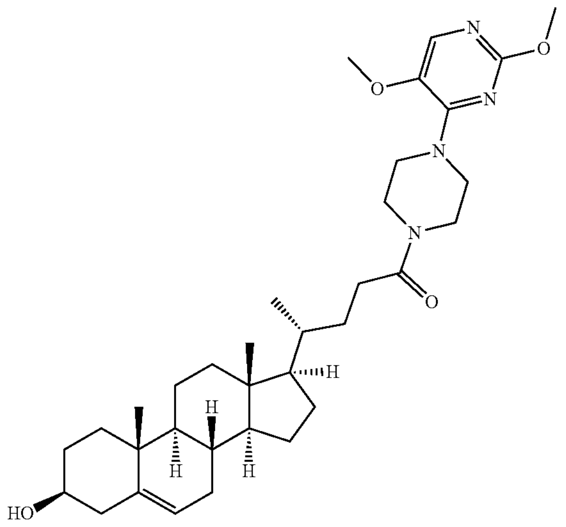

To a solution of compound A (600 mg, 3.84 mmol) in toluene (956 mg) was added $POCl_3$ (1.77 g, 11.5 mmol). The reaction was stirred at 80° C. under $N_2$ for 1 h then $Et_3N$ (803 mg, 5.38 mmol) was added, and the reaction stirred at 80° C. under $N_2$ for 0.5 h. The reaction was cooled and poured into ice water (20 mL) with stirring and warmed to room temperature. The quenched reaction was adjusted to pH=5 with aqueous NaOH (3N) and extracted with toluene (50 mL). The organic layer was dried over sodium sulfate and concentrated under reduced pressure. The residue was purified by silica gel chromatography to afford compound B (120 mg, 17.9%) as yellow oil.

To a solution of compound B (120 mg, 687 μmol) in NMP (3 mL) was added compound C (154 mg, 825 μmol) and $Et_3N$ (308 mg, 2.06 mmol). The reaction was stirred at 75° C. under $N_2$ for 6 h. The reaction was quenched with water (10 mL) and extracted with EtOAc (50 mL). The organic layer was washed with brine (10 mL), dried over sodium sulfate and concentrated. The crude was purified by silica gel chromatography to afford compound D (120 mg, 53.7%) as yellow oil.

To a solution of compound D (120 mg, 370 μmol) in DCM (2 mL) was added TFA (0.5 mL). The reaction was stirred at room temperature for 1 h. The reaction was concentrated under reduced pressure to afford compound E as the TFA salt (118 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (100 mg, 404 μmol) and 2,5-dimethoxy-4-(piperazin-1-yl)pyrimidine (118 mg, 320 μmol) were reacted according to Example 536 to give the title compound 617 (154.8 mg, 99.8%) as a white solid. LCMS: $[M+1]^+$=581.45. 1 HNMR (400 MHz, Chloroform-d) δ 7.74 (s, 1H), 5.35 (d, J=5.2 hz, 1H), 3.90 (s, 3H), 3.79 (d, J=7.6 hz, 7H), 3.69 (t, J=5.2 hz, 2H), 3.53-3.49 (m, 3H), 2.40-2.26 (m, 4H), 2.03-1.94 (m, 2H), 1.93-1.74 (m, 4H), 1.57-1.39 (m, 8H), 1.34-1.25 (m, 2H), 1.22-1.02 (m, 5H), 1.01 (s, 3H), 0.99-0.83 (m, 5H), 0.69 (s, 3H).

Example 618: (R)-1-(4-(5,6-dimethoxypyrimidin-4-yl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

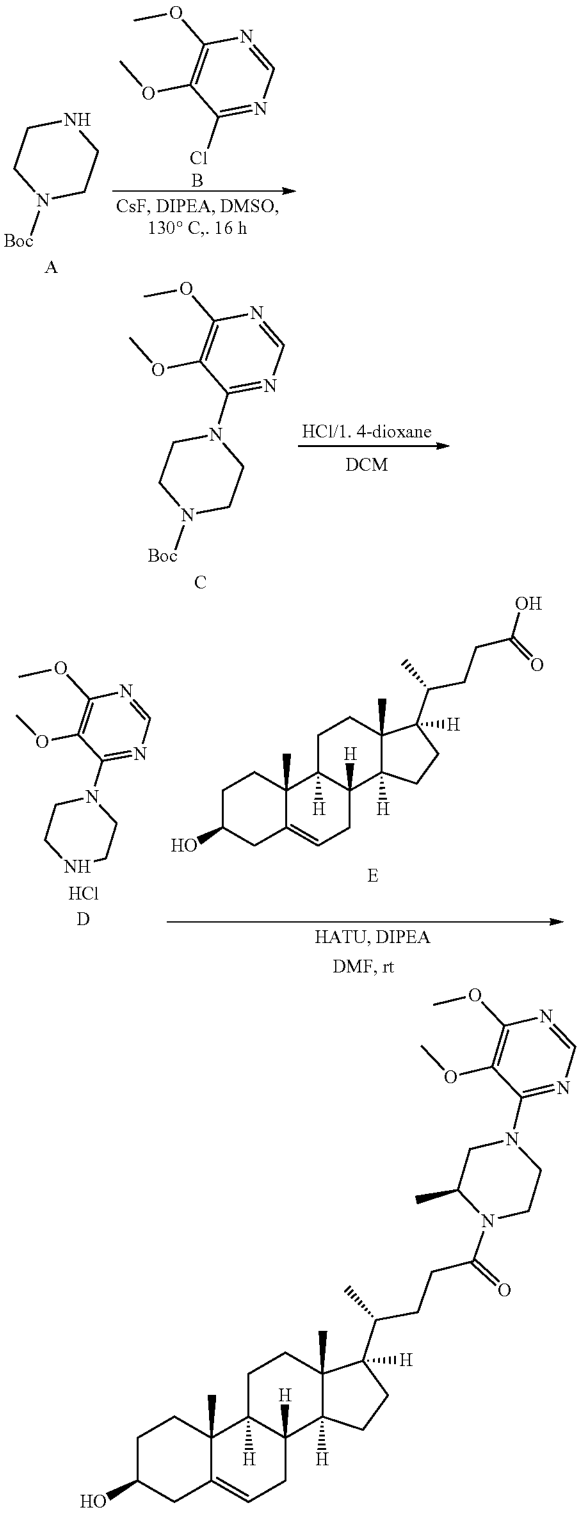

To a solution of compound B (261 mg, 1.61 mmol) in DMSO (6 mL) was added compound A (0.2 g, 1.07 mmol), CsF (326 mg, 2.15 mmol) and DIPEA (694 mg, 5.37 mmol). The reaction was stirred at 130° C. for 16 h. The reaction was cooled to room temperature and water (30 mL) was added. The reaction was extracted with ethyl acetate (50 mL). The organic layer was dried over sodium sulfate and concentrated under reduced pressure. The residue was purified by silica gel chromatography to afford compound C (250 mg, 72%) as white solid.

To a solution of compound C (250 mg, 772 μmol) in DCM was added HCl in 1,4-dioxane (2 mL, 4M), after stirred at room temperature for 2 hours, the reaction was concentrated to afford compound D as an HCl salt (200 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (200 mg, 534 μmol) and 4,5-dimethoxy-6-(piperazin-1-yl)pyrimidine hydrochloride (120 mg, 460 μmol) were reacted according to Example 536 to give the title compound 618 (150 mg, 48%) as white solid. LCMS: $[M+1]^+$=581.45. $^1H$ NMR (400 MHz, Chloroform-d) δ 8.10 (s, 1H), 5.34 (d, J=5.2 hz, 1H), 3.99 (s, 3H), 3.71-3.65 (m, 9H), 3.51-3.47 (m, 3H), 2.38 (dd, J=10.4, 4.8 hz, 1H), 2.32-2.19 (m, 3H), 1.98 (t, J=13.6 hz, 2H), 1.90-1.77 (m, 4H), 1.67 (bs, 2H), 1.59 (d, J=9.6 hz, 2H), 1.54 (bs, 2H), 1.48 (d, J=8.4 hz, 2H), 1.46-1.42 (m, 2H), 1.38 (d, J=18.6 hz, 1H), 1.32-1.25 (m, 2H), 1.18 (dd, J=13.2, 5.2 hz, 1H), 1.12 (d, J=9.6 hz, 2H), 1.05-1.03 (m, 2H), 1.00 (s, 3H), 0.96 (d, J=6.4 hz, 3H), 0.68 (s, 3H).

Example 619: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(5-(trifluoromethyl)pyrimidin-4-yl)piperazin-1-yl)pentan-1-one

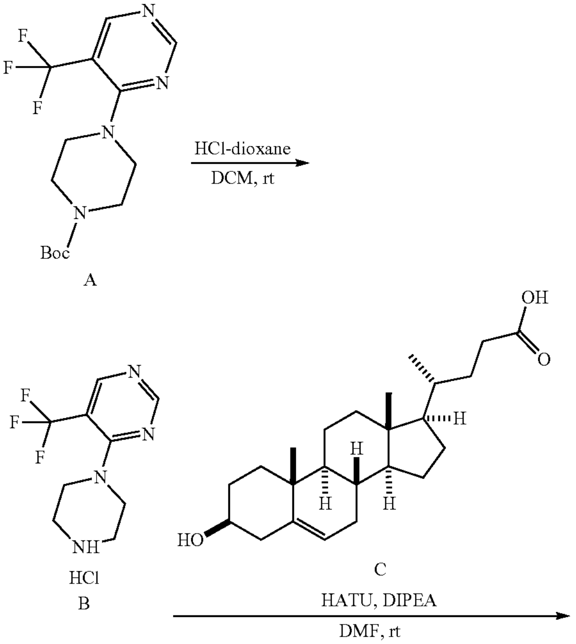

-continued

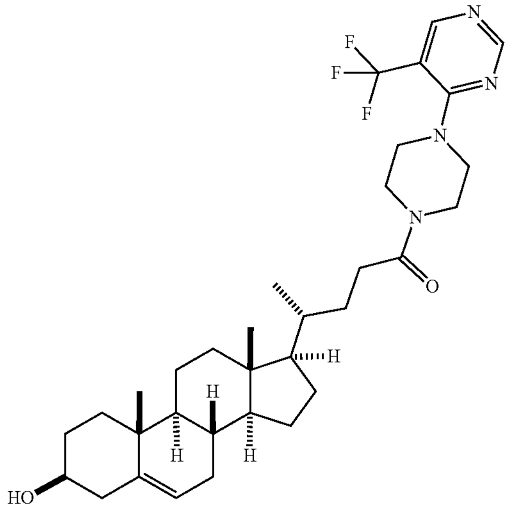

To a solution of compound A (100 mg, 301 μmol) in DCM (2 mL) was added 4NhCl/dioxane (2 mL) at room temperature and the reaction was stirred for 2 h. The reaction was concentrated under reduced pressure to afford compound B as an HCl salt (80.9 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (89.9 mg, 240 μmol) and 4-(piperazin-1-yl)-5-(trifluoromethyl)pyridine hydrochloride (80.9 mg, 0.30 mmol) were reacted according to Example 536 to give the title compound 619 (71 mg, 40%) as a white solid. LCMS: $[M+1]^+$=589.35. $^1H$ NMR (400 MHz, $CDCl_3$) δ 8.71 (s, 1H), 8.61 (s, 1H), 5.35 (d, J=4.8 hz, 1H), 3.78-3.65 (m, 6H), 3.65-3.57 (m, 2H), 3.57-3.47 (m, 1H), 2.46-2.36 (m, 1H), 2.33-2.18 (m, 3H), 2.06-1.93 (m, 2H), 1.93-1.75 (m, 4H), 1.57-1.28 (m, 11H), 1.22-1.02 (m, 6H), 1.01 (s, 3H), 0.96 (d, J=6.4 hz, 3H), 0.94-0.78 (m, 3H), 0.69 (s, 3H). $^{19}F$ NMR (376 MHz, $CDCl_3$) δ-57.37.

Example 620: (R)-1-(4-(5,6-dimethoxypyrimidin-4-yl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

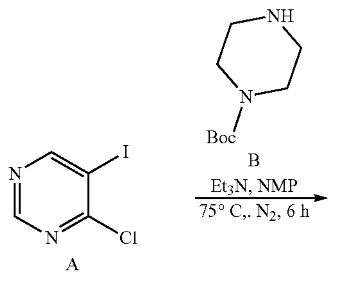

-continued

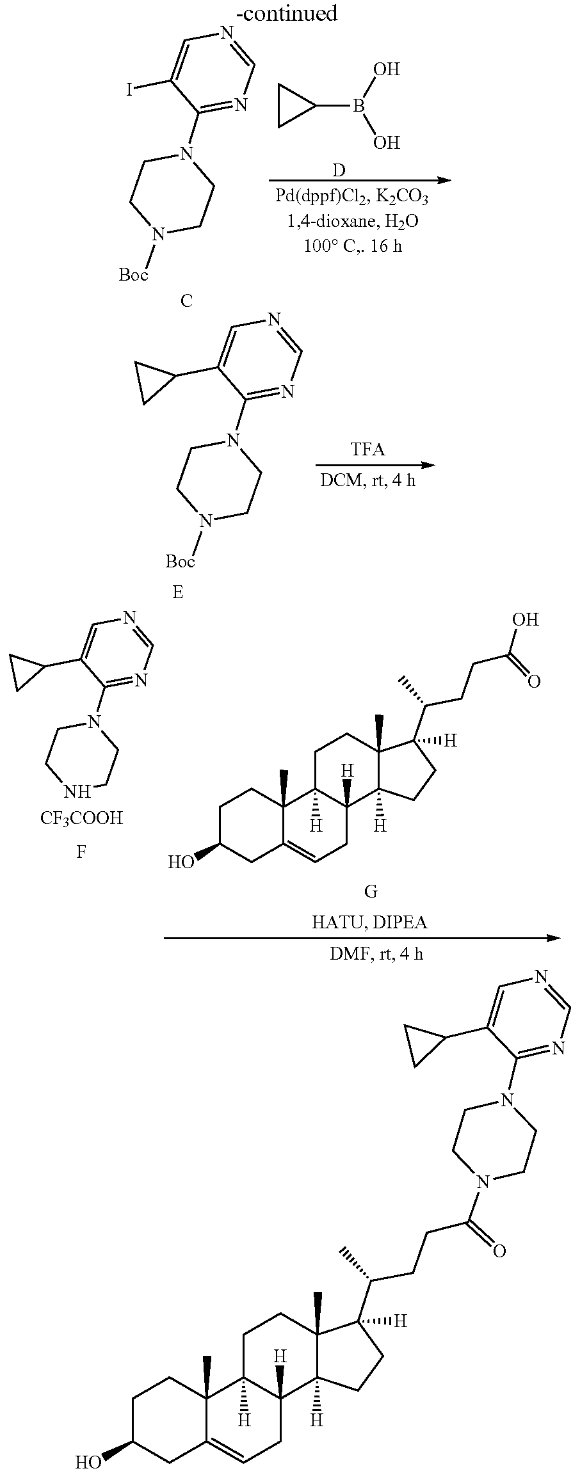

To a solution of compound A (1.0 g, 4.16 mmol) in NMP (6 mL) was added compound B (775 mg, 4.16 mmol) and $Et_3N$ (1.26 g, 12.5 mmol). The reaction was stirred at 75° C. for 6 hours under $N_2$. The reaction was diluted with water (10 mL) and extracted with ethyl acetate (30 mL). The organic layer was concentrated under reduced pressure and the residue was purified by silica gel chromatography to afford compound C (1.5 g, 92%) as yellow solid.

To a solution of compound C (200 mg, 513 mmol) in 1,4-dioxane (3 mL) and water (1 mL) was added $K_2CO_3$ (213 mg, 1.54 mmol), compound D (44 mg, 513 μmol) and Pd(dppf)C12 (37.2 mg, 51.3 μmol). The reaction was stirred at 100° C. for 16 hours. The reaction was cooled to room temperature and water (10 mL) was added then extracted with DCM (30 mL). The organic layer was concentrated under reduced pressure. The crude product was purified by silica gel chromatography to afford compound E (70 mg, 45%) as yellow solid.

To a solution of compound E (70 mg, 230 μmol) in DCM was added TFA (2 mL) and stirred at room temperature for 4 hours. The reaction was concentrated under reduced pressure to afford compound F as the TFA salt (47 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (86.2 mg, 230 μmol) and 5-cyclopropyl-4-(piperazin-1-yl) pyrimidine 2,2,2-trifluoroacetate (47 mg, 148 μmol) were reacted according to Example 536 to give the title compound 620 (70 mg, 54%) as white solid. LCMS: $[M+1]^+=561.45$. $^1H$ NMR (400 MHz, Chloroform-d) δ 8.57 (s, 1H), 8.15 (s, 1H), 5.35 (d, J=5.2 hz, 1H), 3.73-3.61 (m, 6H), 3.62 (d, J=5.6 hz, 2H), 3.52 (dt, J=11.2, 6.0 hz, 1H), 2.47-2.38 (m, 1H), 2.27-2.16 (m, 3H), 2.01 (d, J=12.0 hz, 2H), 1.87-1.78 (m, 5H), 1.70 (d, J=16.0 hz, 2H), 1.58 (d, J=8.4 hz, 1H), 1.49 (d, J=7.6 hz, 5H), 1.44-1.37 (m, 7H), 1.31-1.26 (s, 3H), 1.17 (dd, J=13.6, 8.4 hz, 2H), 1.12-1.07 (m, 2H), 1.06-1.03 (m, 2H), 1.01 (s, 3H), 0.97 (d, J=6.4 hz, 3H), 0.76-0.68 (m, 2H), 0.69 (s, 3H).

Example 621: (R)-1-(4-(3-cyclopropoxypyridin-2-yl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

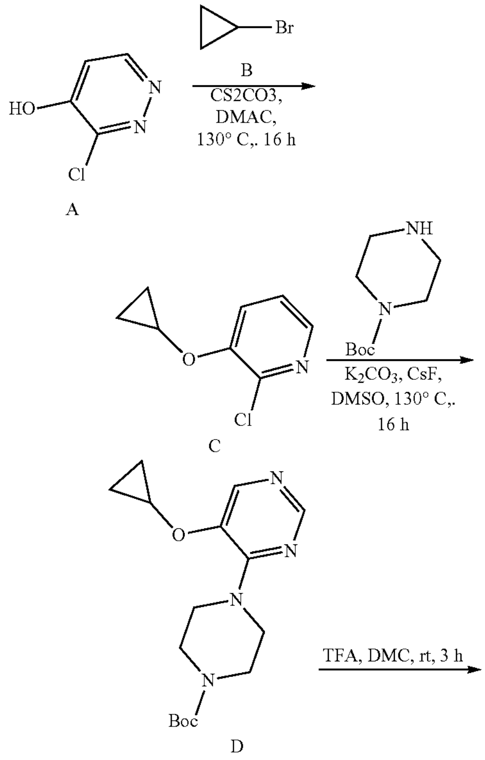

-continued

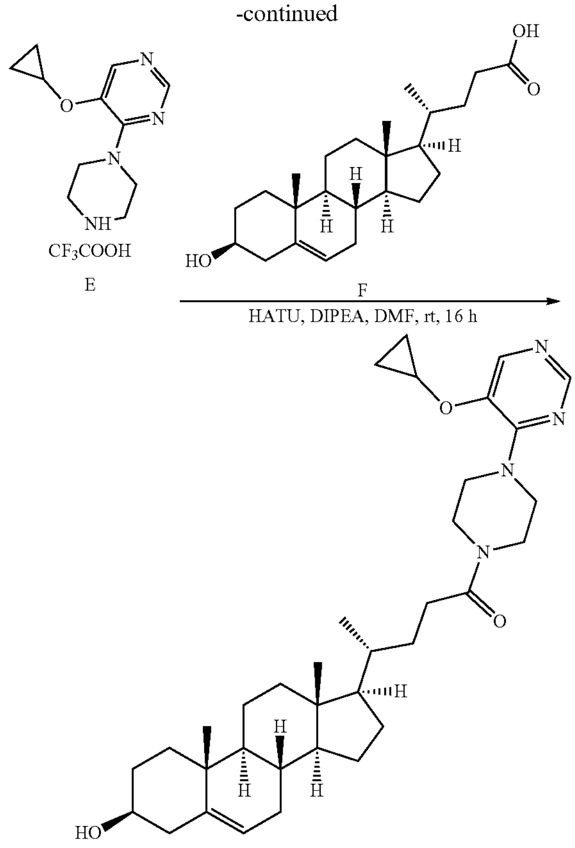

To a solution of compound A (1.00 g, 7.72 mmol) and $Cs_2CO_3$ (5.03 g, 15.4 mmol) in DMAC (25 mL) was added compound B (5.60 g, 46.3 mmol). The reaction was stirred at 130° C. for 2 hours. The reaction was cooled to room temperature. The reaction was diluted with water (20 mL), extracted with EtOAc (30 mL*2). The combined organic layers were concentrated under reduced pressure to afford compound C (300 mg, 23%) as yellow oily liquid.

To a solution of compound C (200 mg, 1.18 mmol), tert-butyl piperazine-1-carboxylate (439 mg, 2.36 mmol), CsF (358 mg, 2.36 mmol) and $K_2CO_3$ (489 mg, 3.54 mmol) in DMSO (5 mL) was heated to 130° C. under $N_2$ for 16 hours. The reaction was diluted with water (30 mL), extracted with EtOAc (30 mL*2). The combined organic phase was washed with brine (30 mL), dried over sodium sulfate, and concentrated under reduced pressure. The crude product was purified by silica gel chromatography to afford compound D (50 mg, 14%) as brown solid.

To a solution of compound D (50 mg, 157 μmol) in TFA (0.5 mL) and dichloromethane (2 mL) was added at room temperature under $N_2$ for 3 hours. The reaction was concentrated under reduced pressure to give compound E as the TFA salt (70 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (99.6 mg, 266 μmol) and 1-(3-cyclopropoxypyridin-2-yl) piperazine 2,2,2-trifluoroacetate (70 mg, 157 μmol) were reacted according to Example 536 to give the title compound 621 (52 mg, 34%). $^1H$ NMR (400 MHz, Chloroform-d) δ 7.88 (dd, J=4.8, 1.6 hz, 1H), 7.44 (dd, J=8.0, 1.6 hz, 1H), 6.87 (dd, J=8.0, 4.8 hz, 1H), 5.34 (dd, J=4.8, 2.4 hz, 1H), 3.79-3.67 (m, 3H), 3.63-3.57 (m, 2H), 3.55-3.48 (m, 1H), 3.39-3.28 (m, 4H), 2.46-2.37 (m, 1H), 2.31-2.19 (m, 3H), 2.03-1.93 (m, 2H), 1.91-1.78 (m, 4H), 1.57-1.43 (m, 6H), 1.36-1.24 (m, 4H), 1.20-1.05 (m, 4H), 1.00 (s, 3H), 0.96-0.90 (m, 4H), 0.86-0.78 (m, 4H), 0.68 (s, 3H).

Example 622: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(3-methoxypyridin-2-yl)piperidin-1-yl)pentan-1-one

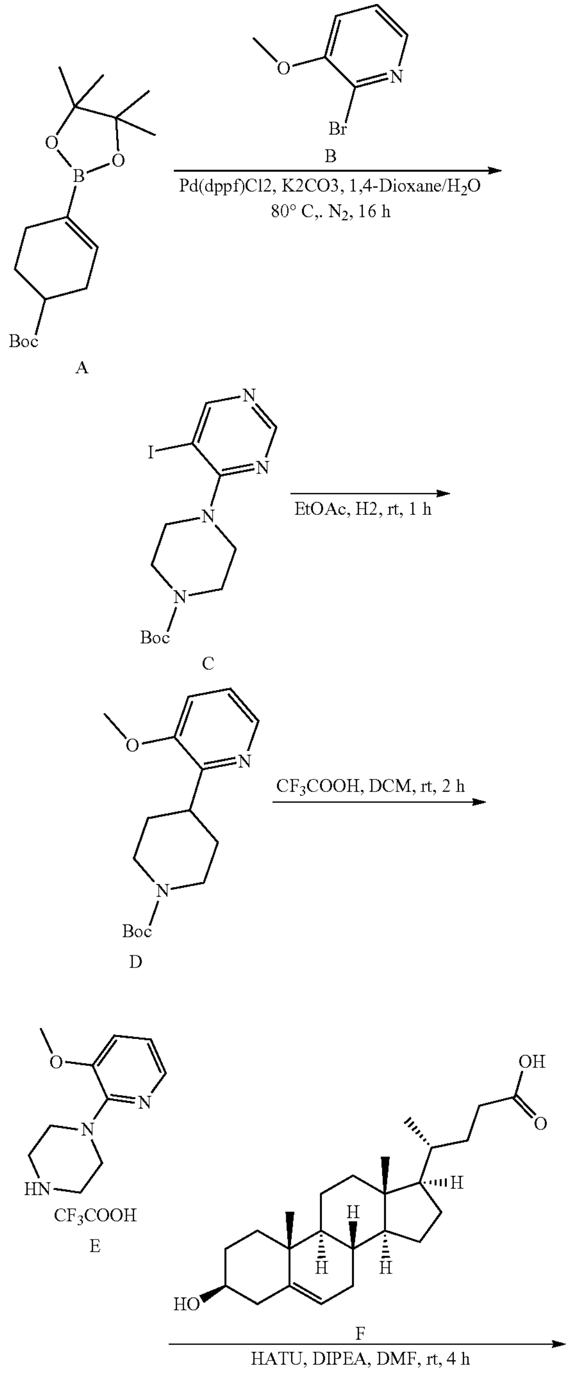

-continued

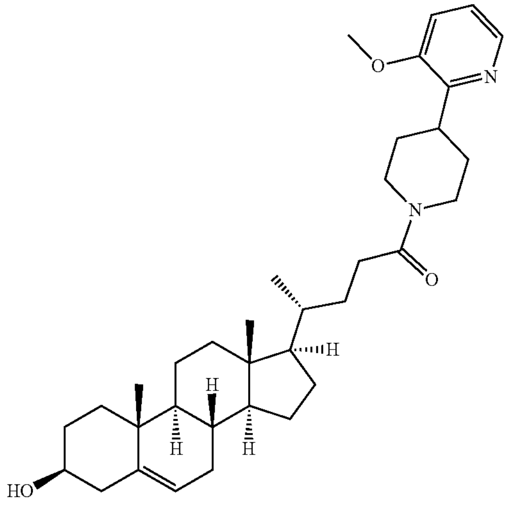

To a solution of compound A (200 mg, 647 μmol) and compound B (243 mg, 1.29 mmol) in 1,4-dioxane (3 mL) and $H_2O$ (1 ml) was added $K_2CO_3$ (358 mg, 2.59 mmol) and Pd(dppf)$Cl_2$ (46.9 mg, 64.7 μmol). The reaction was heated to 80° C. for 16 hours. Upon completion, the reaction was quenched with saturated aqueous ammonium chloride (10 mL) and extracted with ethyl acetate (10 mL*3). The combined organic layers were washed with brine (10 mL), dried over sodium sulfate, filtered, and concentrated under reduced pressure. The crude product was purified by silica gel chromatography to afford compound C (170 mg, 90.52%) as yellow solid.

To a solution of compound C (110 mg, 379 μmol) in EtOAc (3 mL) was added 10% Pd/C (11 mg). The reaction was stirred at room temperature for 1 hour under hydrogen. The reaction was filtered and was concentrated under reduced pressure. The crude product was purified by silica gel chromatography to afford compound E (90 mg, 81.25%) as yellow solid.

TFA (3 mL) was added slowly to the compound D (90 mg, 308 μmol) in a single-neck flask at room temperature and stirred for 2 hours. Upon completion, the reaction was concentrated under reduced pressure to afford compound E as the TFA salt (77.7 mg).

3-methoxy-2-(piperidin-4-yl)pyridine acetate TFA salt (67.4 mg, 220 μmol), (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (100 mg, 267 μmol) was reacted according to Example 536 to give the title compound 622 (45.5 mg, 31.05% yield) as white solid. LCMS: $[M+1]^+=549.50$. $^1H$ NMR (400 MHz, Chloroform-d) δ 8.13 (s, 1H), 7.12 (d, J=3.0 hz, 2H), 5.38-5.30 (m, 1H), 4.72 (dd, J=9.6, 6.8 hz, 1H), 3.98 (d, J=13.2 hz, 1H), 3.84 (s, 3H), 3.52 (tt, J=11.2, 4.8 hz, 1H), 3.35 (tt, J=11.6, 3.6 hz, 1H), 3.22-3.11 (m, 1H), 2.68 (td, J=12.8, 2.8 hz, 1H), 2.46-2.36 (m, 1H), 2.32-2.19 (m, 3H), 2.03-1.87 (m, 4H), 1.87-1.81 (m, 4H), 1.61-1.53 (m, 2H), 1.45-1.51 (m, 5H), 1.43 (dd, J=5.6, 2.8 hz, 2H), 1.39-1.24 (m, 3H), 1.16 (d, J=5.6 hz, 1H), 1.13-1.03 (m, 3H), 1.00 (s, 3H), 0.96 (d, J=6.4 hz, 4H), 0.68 (s, 3H).

Example 623: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(2-methoxyphenyl)piperidin-1-yl)pentan-1-one

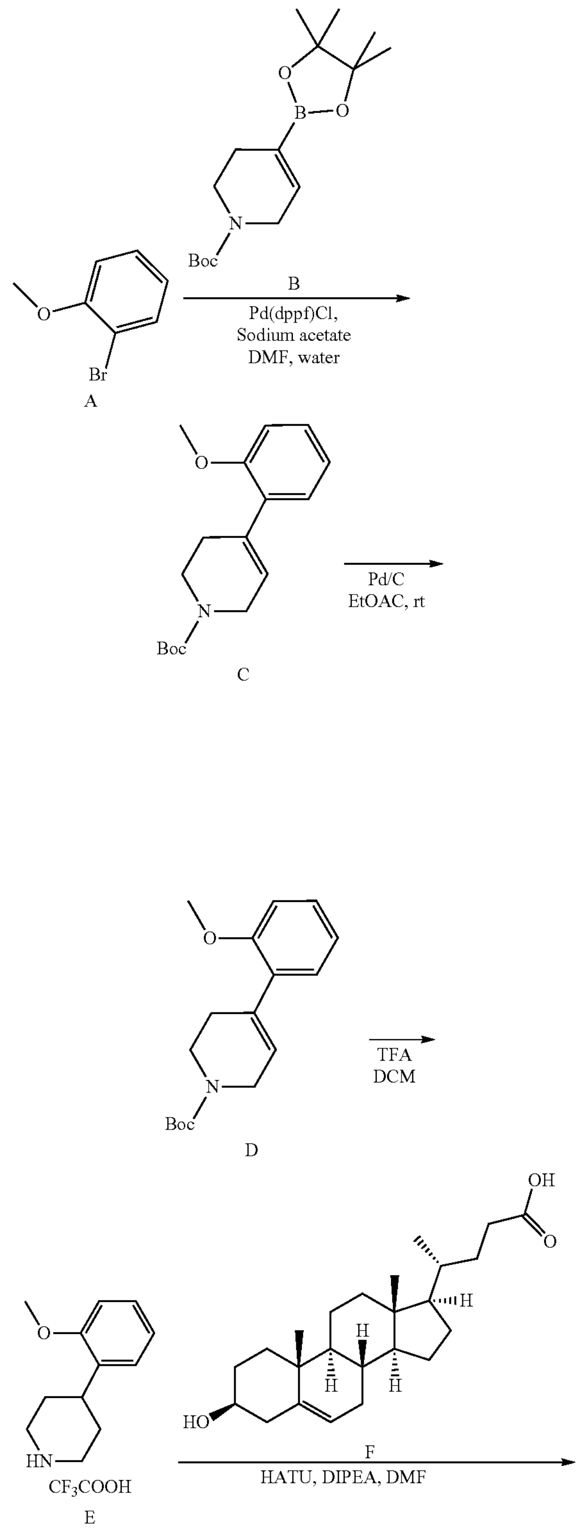

-continued

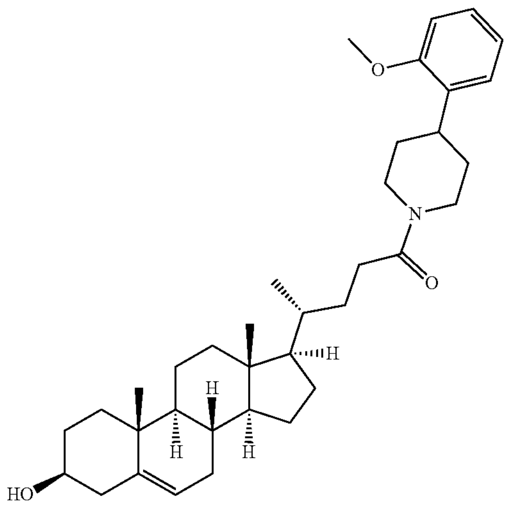

To a solution of compound A (907 mg, 4.85 mmol) in DMF (12 mL) and water (1 mL) was added compound B (500 mg, 1.62 mmol), Pd(dppf)$Cl_2$ (176 mg, 243 μmol) and sodium acetate (99 mg, 728 μmol). The reaction was stirred at 90° C. for 16 hours under $N_2$. The reaction was quenched by $H_2O$ (20 mL) and extracted with ethyl acetate (100 mL). The organic layer was concentrated under reduced pressure. The crude product was purified by silica gel chromatography to afford compound C (230 mg, 49%) as yellow solid.

To a solution of compound C (200 mg, 691 μmol) in ethyl acetate (2 mL) was added 10% Pd/C (20 mg) under 1 atm$h_2$. The reaction was stirred at room temperature for 16 hours. The solution was filtered and concentrated to afford compound D (150 mg, 74%) as yellow solid.

To a solution of compound D (150 mg, 515 μmol) in DCM (3 mL) was added TFA (0.4 mL, 48.5 mmol). The reaction was stirred at room temperature for 4 hours. The solution was concentrated to afford compound E as the TFA salt (98 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (141 mg, 376 μmol) and 4-(2-methoxyphenyl)piperidine 2,2,2-trifluoroacetate (90 mg, 295 μmol) to give the title compound 623 (20.0 mg, 8%) as a white solid. LCMS: $[M+1]^+$=548.40. $^1$H NMR (400 MHz, Chloroform-d) δ 7.22-7.16 (m, 1H), 7.12 (dd, J=7.2, 1.2 hz, 1H), 6.93 (t, J=7.6 hz, 1H), 6.87 (d, J=8.4 hz, 1H), 5.35 (d, J=5.2 hz, 1H), 4.79 (d, J=13.2 hz, 1H), 3.95 (d, J=13.2 hz, 1H), 3.83 (s, 3H), 3.55-3.48 (m, 1H), 3.18 (t, J=12.0 hz, 2H), 2.64 (s, 1H), 2.41 (d, J=11.2 hz, 1H), 2.33-2.19 (m, 3H), 2.04-1.77 (m, 9H), 1.55-0.87 (m, 23H), 0.69 (s, 3H).

Example 624: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(2-methoxyphenyl)piperazin-1-yl)pentan-1-one

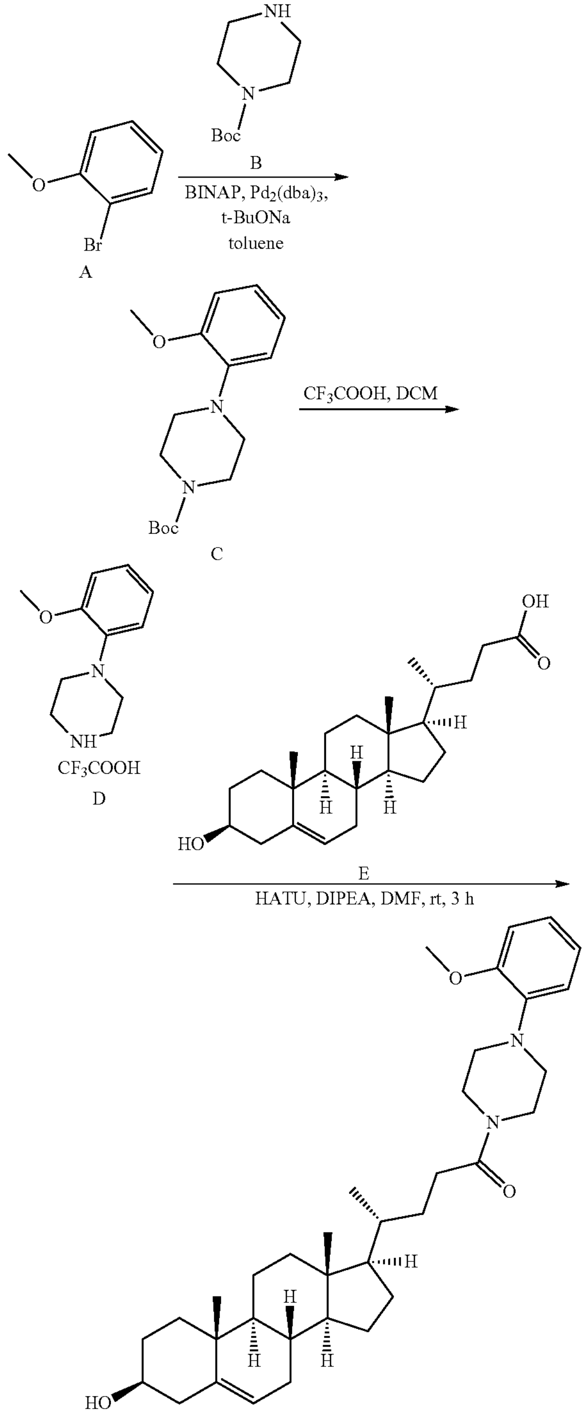

To a solution of compound A (300 mg, 1.6 mmol) in toluene (15 mL) was added BINAP (99.9 mg, 160 μmol), $Pd_2(dba)_3$ (29.4 mg, 32.1 μmol) and t-BuONa (308 mg, 21 mmol) the reaction was purged 3 times with nitrogen. Compound B (299 mg, 1.6 mmol) was added to the reaction and stirred at 100° C. for 16 h under nitrogen atmosphere. The reaction was quenched with water (10 mL) and extracted with ethyl acetate (10 mL*3). The combined organic layers were washed with brine (10 mL), dried over sodium sulfate, filtered, and concentrated under reduced pressure. The crude product was purified by silica gel chromatography to afford compound C (370 mg, 67%) as a white solid.

To a solution of compound C (300 mg, 1.03 mmol) in dichloromethane (5 mL) was added TFA (1 mL) at room temperature and was stirred for 1 hour and concentrated to afford compound D as the TFA salt (226 mg, 76%).

(4R)-4-((3S,8R,9S,13R,14S,17R)-3-hydroxy-13-methyl-2,3,4,7,8,9,10,11,12,13,14,15,16,17-tetradecahydro-1H-cyclopenta[a]phenanthren-17-yl)pentanoic acid (194 mg, 519 μmol) and 1-(2-methoxyphenyl)piperazine 2,2,2-trifluoroacetate (226 mg, 780 μmol) were reacted according to Example 536 to give the title compound 624 (200 mg, 70%) as a white solid. LCMS: $[M+H]^+$=549.45. $^1H$ NMR (400 MHz, Chloroform-d) δ 7.03 (m, 1H), 6.95-6.83 (m, 3H), 5.35 (d, J=5.2 hz, 1H), 3.88 (s, 3H), 3.79 (d, J=5.2 hz, 2H), 3.65 (t, J=5.2 hz, 2H), 3.51-3.45 (m, 1H), 3.04-2.97 (m, 4H), 2.42 (td, J=11.2, 5.2 hz, 1H), 2.26-2.15 (m, 3H), 2.03-1.95 (m, 2H), 1.90-1.77 (m, 4H), 1.53-1.47 (m, 4H), 1.46-1.39 (m, 2H), 1.38-1.30 (m, 2H), 1.29-1.20 (m, 2H), 1.17 (d, J=5.2 hz, 1H), 1.13-1.03 (m, 3H), 1.01 (s, 3H), 0.97 (d, J=6.4 hz, 3H), 0.94-0.87 (m, 1H), 0.69 (s, 3H).

Example 625: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-(3-methoxypyridin-2-yl)pentanamide

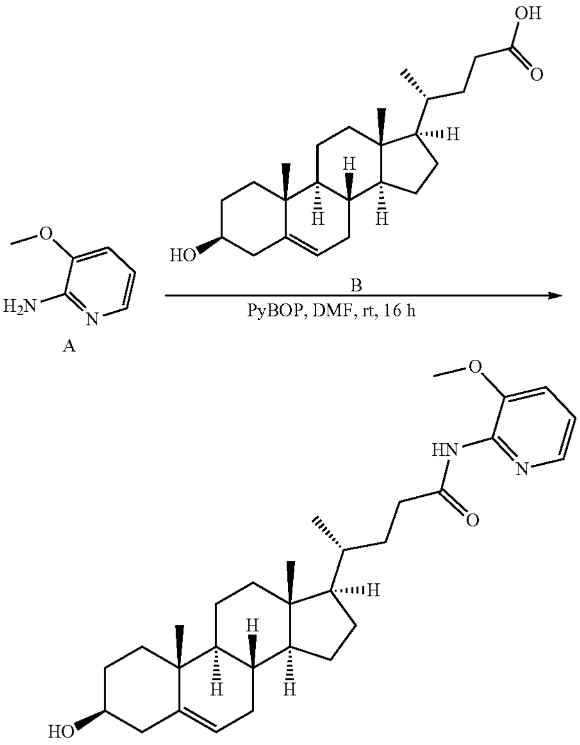

To a solution of compound A (0.5 g, 4.03 mmol) in DMF (10 mL) was added compound B (1.21 g, 3.22 mmol) and PyBOP (2.1 g, 4.03 mmol) at room temperature under $N_2$ and stirred for 16 h. The reaction was diluted with saturated aqueous $NH_4Cl$ (aq, 30 mL) and extracted with EtOAc (10 mL*2). The combined organic layers were washed with water (20 mL), brine (20 mL), dried over sodium sulfate and concentrated under reduced pressure. The residue was purified by prep-C18 to give the title compound 625 (8.8 mg, 0.5%) as a white solid. LCMS: $[M+1]^+$=481.30. $^1H$ NMR (400 MHz, Chloroform-d) δ 7.98 (d, J=4.8 hz, 1H), 7.86 (s, 1H), 7.11 (dd, J=8.4, 1.6 hz, 1H), 6.98 (dd, J=8.4, 4.8 hz, 1H), 5.35 (d, J=5.2 hz, 1H), 3.88 (s, 3H), 3.52 (tt, J=10.4, 4.8 hz, 1H), 2.88-2.51 (m, 2H), 2.32-2.20 (m, 2H), 2.02-1.81 (m, 6H), 1.60-1.52 (m, 4H), 1.48-1.40 (m, 4H), 1.37-1.26 (m, 3H), 1.23-1.03 (m, 5H), 1.01 (s, 3H), 0.99-0.88 (m, 5H), 0.69 (s, 3H).

Example 626: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-{2H,3H,4H-pyrido[3,2-b][1,4]oxazin-4-yl}pentan-1-one

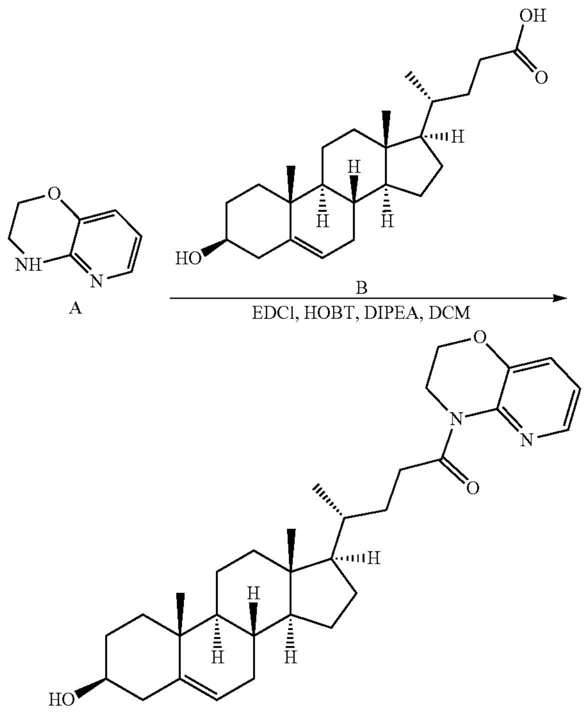

To a solution of compound A (100 mg, 734 μmol), compound B (150 mg, 402 μmol) and DIPEA (389 mg, 3.01 mmol) in DCM (5 mL) was added EDCI (195 mg, 1 mmol) and HOBT (153 mg, 1 mmol) at room temperature under $N_2$ and stirred for 16 h. The reaction was diluted with saturated $NH_4Cl$ (30 mL) and extracted with EtOAc (10 mL*2). The combined organic layers were washed with saturated $NaHCO_3$ (20 mL), water (20 mL), brine (20 mL), dried over $Na_2SO_4$ and concentrated under reduced pressure. The residue was purified by silica gel chromatography to afford the title compound 626 (130 mg, 52%) as a white solid. LCMS: $[M+1^+$=493.30. $^1H$ NMR (400 MHz, Chloroform-d) δ 7.98 (dd, J=4.8, 1.6 Hz, 1H), 7.22 (dd, J=8.0, 1.6 Hz, 1H), 7.03 (dd, J=8.0, 4.8 Hz, 1H), 5.36 (d, J=5.2 Hz, 1H), 4.31-4.22 (m, 2H), 4.11-4.04 (m, 2H), 3.61-3.48 (m, 1H), 3.07 (dd, J=10.4, 4.4 Hz, 1H), 2.95 (dd, J=9.6, 5.2 Hz, 1H), 2.34-2.16 (m, 2H), 2.00 (dd, J=14.0, 10.4 Hz, 2H), 1.86 (q, J=4.8 Hz, 4H), 1.55-1.38 (m, 7H), 1.29 (d, J=11.6 Hz, 3H), 1.21-1.06 (m, 4H), 1.02 (s, 4H), 0.95 (d, J=6.4 Hz, 4H), 0.70 (s, 3H).

Example 627: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(7-methoxyisoquinolin-1-yl)piperazin-1-yl)pentan-1-one

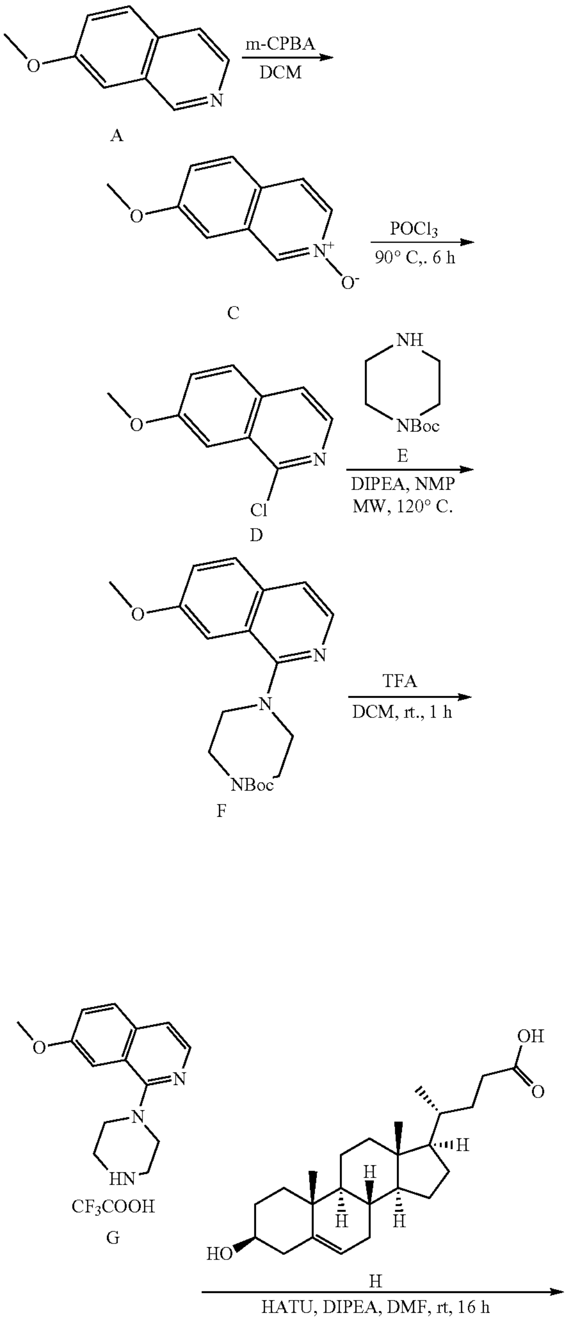

-continued

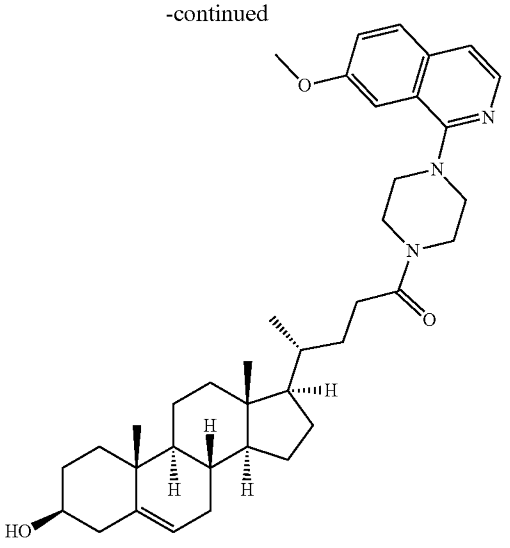

To a solution of compound A (1 g, 6.28 mmol) in DCM (14 mL) at 0° C. was added compound B (2.16 g, 12.5 mmol) in portions over approximately 15 min. The reaction was stirred at room temperature for 0.5 h. Ice-cold water (20 mL) was added, and the reaction was extracted with DCM (50 mL). The organic layer was washed by 10% aq. NaOH (10 mL), brine (10 mL), dried over sodium sulfate and concentrated under reduced pressure. The residue was purified by silica gel chromatography to afford compound C (870 mg, 79%) as yellow oil.

A reaction of compound C (400 mg, 2.28 mmol) and $POCl_3$ (2.5 mL, 26.8 mmol) was stirred at 90° C. under $N_2$ for 6 h. 10% aq. $NaHCO_3$ (20 mL) was added, and the reaction extracted with EtOAc (50 mL). The organic layer was dried over sodium sulfate and concentrated under reduced pressure. The crude was purified by silica gel chromatography to afford compound D (240 mg, 54.4%) as yellow oil.

To a solution of compound D (240 mg, 1.24 mmol) in NMP (1.5 mL) was added compound E (277.6 mg, 1.49 mmol) and DIPEA (320 mg, 2.48 mmol). The reaction was heated in a microwave reactor at 150° C. for 4 h. Water (10 mL) was added, and the reaction was extracted with EtOAc (30 mL). The organic layer was washed with brine, dried over sodium sulfate and concentrated under reduced pressure. The crude was purified by silica gel chromatography to afford compound F (180 mg, 42.2%) as yellow oil.

To a solution of compound F (180 mg, 524 μmol) in DCM (2 mL) was added TFA (0.3 mL). The reaction was stirred at room temperature for 1 h. The reaction was concentrated under reduced pressure to afford compound G as the TFA salt (127 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (130 mg, 404 μmol) and 7-methoxy-1-(piperazin-1-yl)isoquinoline TFA salt (127 mg, 356 μmol) were reacted according to Example 536 to give the title compound 627 (170 mg, 81.7%) as a white solid. LCMS: $[M+1]^+$=600.45. $^1$HNMR (400 MHz, Chloroform-d) δ 8.07 (d, J=5.6 hz, 1H), 7.71 (d, J=8.8 hz, 1H), 7.39 (d, J=2.4 hz, 1H), 7.31 (dd, J=8.8, 2.4 hz, 1H), 7.28 (s, 1H), 5.35 (d, J=5.2 hz, 1H), 3.94 (s, 3H), 3.88 (t, J=5.2 hz, 2H), 3.74 (t, J=5.2 hz, 2H), 3.51 (d, J=12.4 hz, 1H), 3.41 (t, J=5.2 hz, 2H), 3.32 (t, J=5.2 hz, 2H), 2.46-2.26 (m, 4H), 2.06-1.78 (m, 6H), 1.60-1.27 (m, 12H), 1.22-1.02 (m, 5H), 1.01 (s, 3H), 0.98 (d, J=6.4 hz, 3H), 0.96-0.84 (m, 1H), 0.70 (s, 3H).

Example 628: (R)-1-(4-(2,7-naphthyridin-1-yl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

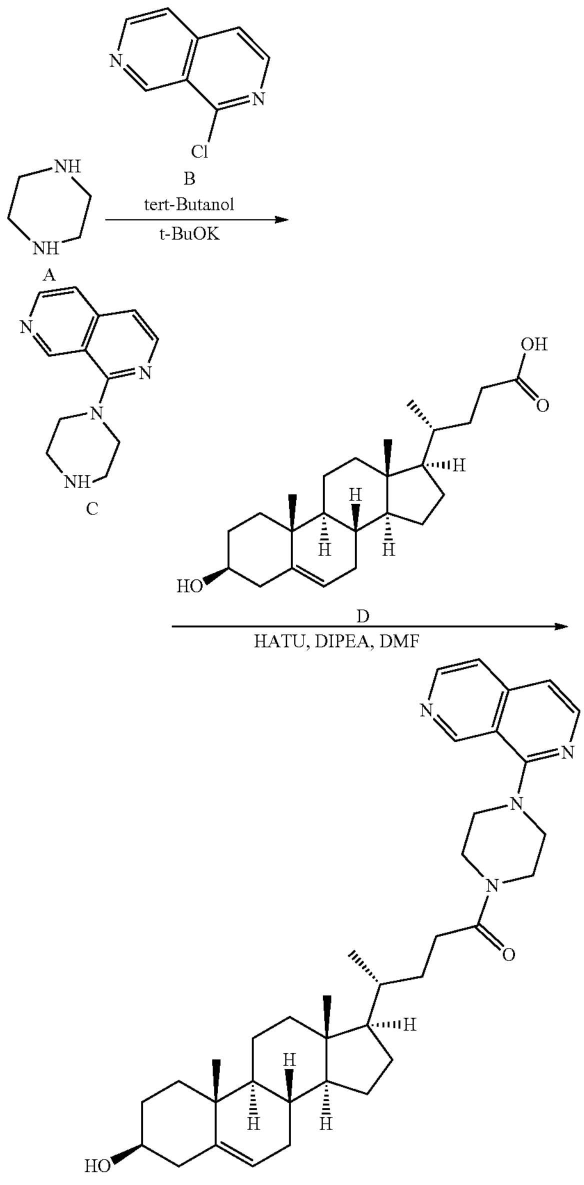

A solution of compound A (424 mg, 4.92 mmol) in t-butanol (10 mL) was treated with t-BuOK (92 mg, 820 μmol) in one portion. After stirring for 10 minutes at 40° C., a solution of compound B (90 mg, 547 μmol) in t-butanol (2 mL) was added. The reaction was stirred at 40° C. for 16 h. The solvent was removed under reduced pressure and the residue was purified by silica gel chromatography to afford compound C (80 mg, 68%) as a white solid.

(R)-4-((3S,8S,9S,10R,13R,14S,17R)-3-hydroxy-10,13-dimethyl-2,3,4,7,8,9,10,11,12,13,14,15,16,17-tetradeca-hydro-1H-cyclopenta[a]phenanthren-17-yl)pentanoic acid (62.9 mg, 168 μmol) and 1-(piperazin-1-yl)-2,7-naphthyridine (45 mg, 210 μmol) were reacted according to Example 536 to give the title compound 628 (40 mg, 33%) as a white solid. LCMS: $[M+H]^+$=574.50. $^1$H NMR (400 MHz, Chloroform-d) δ 9.47 (s, 1H), 8.64 (d, J=5.6 hz, 1H), 8.28 (d, J=5.6 hz, 1H), 7.56 (d, J=5.6 hz, 1H), 7.20 (d, J=5.6 hz, 1H), 5.35 (d, J=5.2 hz, 1H), 3.89 (t, J=5.2 hz, 2H), 3.79-3.70 (m, 2H), 3.53-3.42 (m, 5H), 2.46 (td, J=10.8, 5.6 hz, 1H), 2.28 (m, 3H), 2.04-1.89 (m, 3H), 1.88-1.81 (m, 3H), 1.60-1.56 (m, 1H), 1.49 (m, 6H), 1.37 (t, J=10.0 Hz, 1H), 1.31-1.20 (m, 2H), 1.19-1.05 (m, 4H), 1.01 (s, 3H), 0.98 (d, J=6.4 hz, 3H), 0.95-0.87 (m, 1H), 0.70 (s, 3H).

Example 629: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(3-methoxypyridazin-4-yl)piperazin-1-yl)pentan-1-one

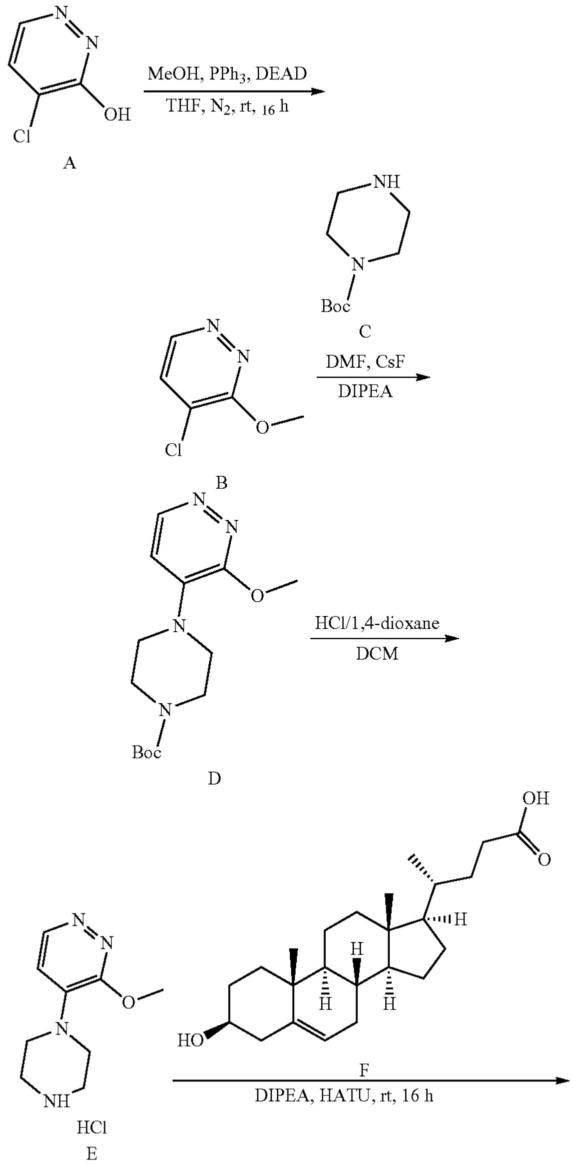

-continued

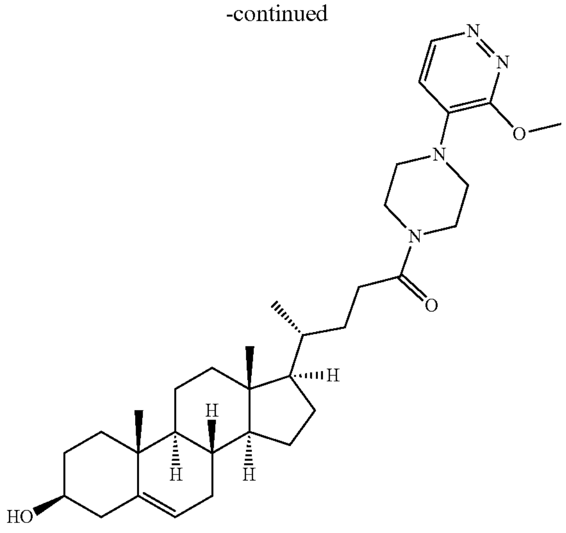

To a 0° C. solution of compound A (100 mg, 766 μmol) in THF (3 mL) was added methanol (36.8 mg, 1.15 mmol), $PPh_3$ (301 mg, 1.15 mmol) and DEAD (200 mg, 1.15 mmol) under $N_2$. The reaction was warmed to room temperature under $N_2$ for 16 h. The reaction was diluted with saturated aqueous $NH_4Cl$ (30 mL) and extracted with EtOAc (10 mL*2). The combined organic layers were washed with water (20 mL), brine (20 mL), dried over sodium sulfate and concentrated under reduced pressure. The residue was purified by silica gel chromatography to afford compound B (80 mg, 72%) as yellow oil.

To a solution of compound B (80 mg, 553 μmol) in DMF (3 mL) was added compound C (103 mg, 553 μmol), CsF (168 mg, 1.11 mmol) and DIPEA (215 mg, 1.66 mmol). The reaction was heated to 100° C. under $N_2$ for 16 h. The reaction was diluted with saturated aqueous $NH_4Cl$ (30 mL) and extracted with EtOAc (10 mL*2). The combined organic layers were washed with water (20 mL), brine (20 mL), dried over sodium sulfate and concentrated under reduced pressure. The residue was purified by silica gel chromatography to afford compound D (60 mg, 36%) as a white solid.

To a solution of compound D (60 mg, 204 μmol) in DCM (3 mL) was added hydrogen chloride (2 mL, 8 mmol, 4M in dioxane) at room temperature and the reaction was stirred for 2 h. The reaction was concentrated under reduced pressure to afford compound E as an HCl salt (42 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (54 mg, 144 μmol) and 3-methoxy-4-(piperazin-1-yl)pyridine hydrochloride (42 mg, 180 μmol), to give the title compound 629 (70 mg, 25%) as a white solid. LCMS: $[M+1]^+$=551.40. $^1$H NMR (400 MHz, Chloroform-d) δ 7.60 (d, J=4.8 hz, 1H), 6.27 (d, J=4.8 hz, 1H), 5.35 (d, J=5.2 hz, 1H), 3.77-3.65 (m, 5H), 3.56-3.45 (m, 5H), 3.32 (t, J=5.2 hz, 2H), 2.41 (ddd, J=15.6, 10.8, 5.2 hz, 1H), 2.26-2.17 (m, 3H), 1.99 (t, J=13.2 hz, 2H), 1.90-1.76 (m, 4H), 1.57-1.43 (m, 7H), 1.40-1.27 (m, 3H), 1.22-1.06 (m, 4H), 1.01 (s, 4H), 0.96 (d, J=6.4 hz, 4H), 0.69 (s, 3H).

Example 630: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(5-hydroxypyrimidin-4-yl)piperazin-1-yl)pentan-1-one

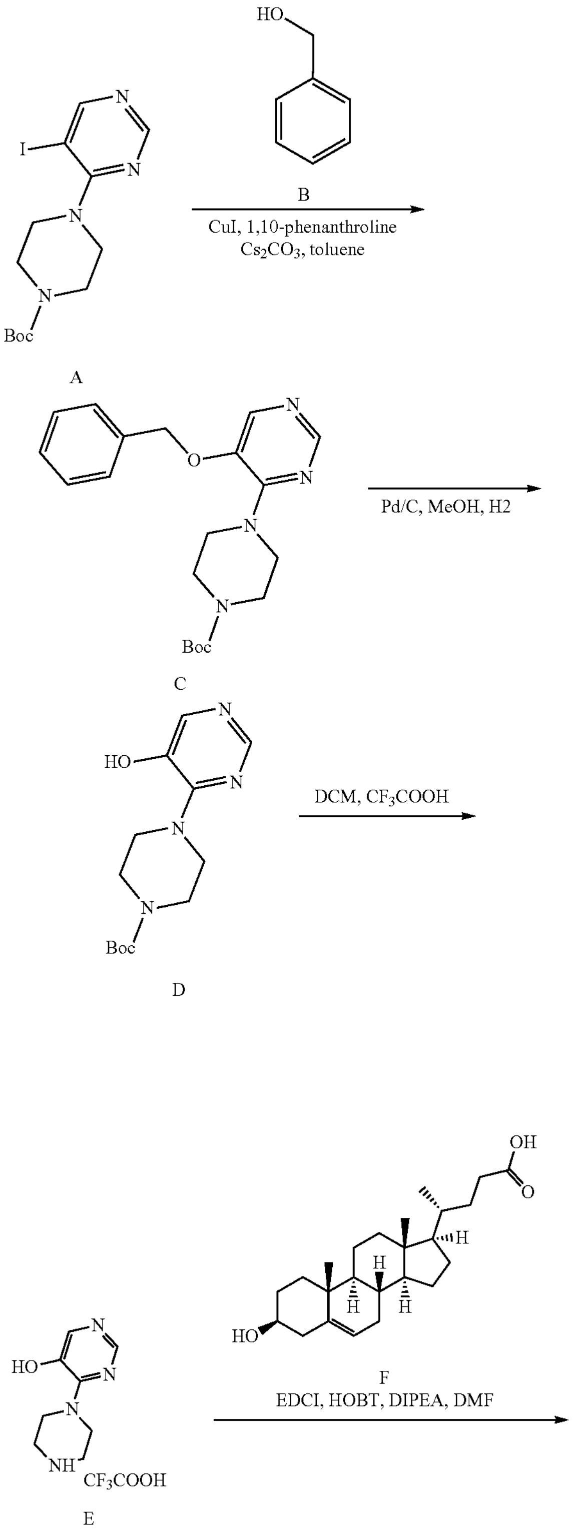

-continued

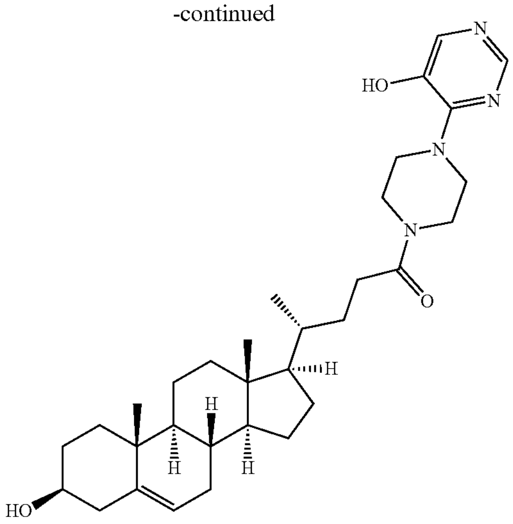

To a sealed tube was added compound A (370 mg, 948 μmol), CuI (18.1 mg, 94.8 μmol), 1,10-phenanthroline (34.2 mg, 190 μmol), $Cs_2CO_3$ (433 mg, 1.33 mmol), compound B (308 mg, 2.84 mmol), and toluene (6 mL). The reaction was stirred under nitrogen at 110° C. for 16 hours. The reaction was diluted with water (10 mL) and extracted with ethyl acetate (20 mL). The organic layer was dried over sodium sulfate, filtered, and concentrated under reduced pressure. The crude product was purified by silica gel chromatography to afford compound C (280 mg, 79%) as a white solid.

To a solution of compound C (100 mg, 270 μmol) in methanol (3 mL) was added 10% Pd/C (100 mg). The reaction was stirred at room temperature for 10 minutes under 1 atm hydrogen. The reaction was filtered and concentrated under reduced pressure to afford compound D (70 mg, 92%) as a white solid.

TFA (2 mL) was added slowly to a solution of compound D (70 mg, 250 μmol) in dichloromethane (3 mL) in a single-neck flask at room temperature and stirred for 1 hour. Upon completion, the reaction was added dichloromethane (10 mL) and concentrated to afford compound E as the TFA salt (40 mg, 89%).

To a solution of compound E (40 mg, 222 μmol) and compound F (100 mg, 267 μmol) in DMF (4 mL) was added EDCI (64.5 mg, 333 μmol),hOBT (50.7 mg, 333 μmol) and DIPEA (86.1 mg, 666 μmol). The reaction was stirred at room temperature for 2 hours. Upon completion, the reaction was quenched with saturated aqueous ammonium chloride (20 mL) and extracted with ethyl acetate (20 mL*3). The combined organic layers were washed with brine, dried over sodium sulfate, filtered, and concentrated under reduced pressure. The crude product was purified by silica gel chromatography to give the title compound 630 (30 mg, 25%) as a white solid. LCMS: $[M+1]^+$=537.50. $^1H$ NMR (400 MHz, DMSO-$d_6$) δ 10.04 (s, 1H), 8.15 (s, 1H), 7.84 (s, 1H), 5.26 (d, J=4.8 hz, 1H), 4.58 (s, 1H), 3.66-3.55 (m, 4H), 3.52 (d, J=5.6 hz, 4H), 3.27-3.22 (m, 1H), 2.36-2.12 (m, 4H), 1.99-1.88 (m, 2H), 1.78 (ddt, J=16.8, 12.8, 4.4 hz, 2H), 1.70-1.61 (m, 2H), 1.57-1.49 (m, 2H), 1.47-1.44 (m, 1H), 1.39 (d, J=9.2 hz, 2H), 1.35-1.26 (m, 2H), 1.24 (d, J=5.2 hz, 2H), 1.19-1.06 (m, 3H), 1.03-0.96 (m, 2H), 0.94 (s, 3H), 0.91 (d, J=6.4 hz, 3H), 0.86 (dd, J=11.2, 5.2 hz, 1H), 0.65 (s, 3H).

Example 631: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[4-(6-hydroxypyrimidin-4-yl)piperazin-1-yl]pentan-1-one

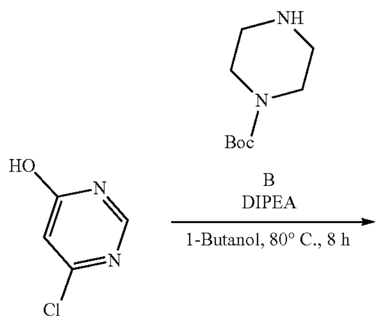

A

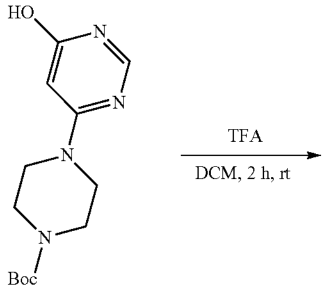

C

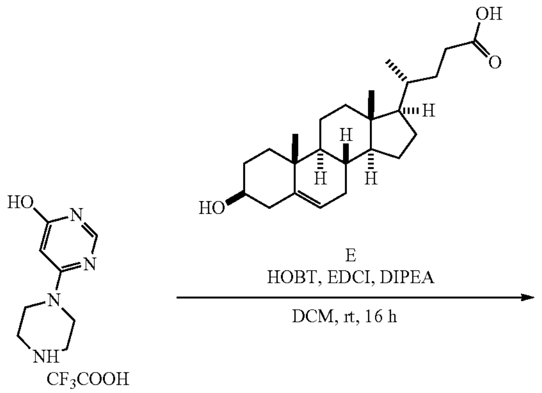

D

-continued

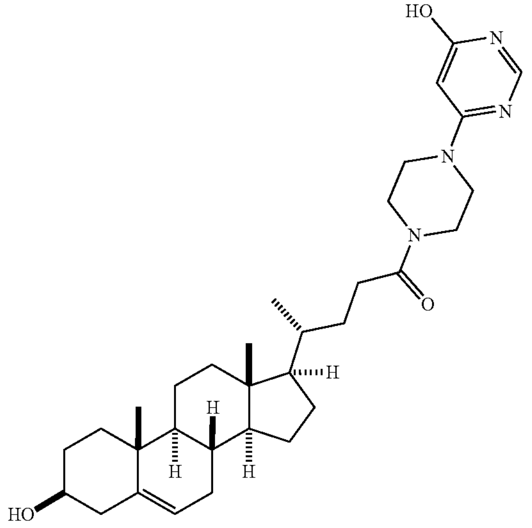

To a solution of compound A (500 mg, 3.83 mmol) in 1-butanol (10 mL) was added compound B (927 mg, 4.98 mmol) and DIPEA (644 mg, 4.98 mmol). The reaction was heated to 80° C. under $N_2$ for 16 h. The reaction was cooled to room temperature and concentrated under reduced pressure. The residue was purified by silica gel chromatography to afford compound C (920 mg, 85%) as white solid.

To a solution of compound C (920 mg, 3.28 mmol) in DCM (20 mL) was added TFA (8 mL) at room temperature and the reaction was stirred for 2 h. The reaction was concentrated under reduced pressure to afford compound D as the TFA salt (97.9 mg).

To a solution of compound E (99.8 mg, 266 μmol), compound D (97.9 mg, 333 μmol) and DIPEA (258 mg, 2 mmol) in DCM (5 mL) was added EDCI (129 mg, 666 μmol) and HOBT (101 mg, 666 μmol) at room temperature under $N_2$ and stirred for 16 h. The reaction was diluted with saturated aqueous $NH_4Cl$ (30 mL) and extracted with EtOAc (10 mL*2). The combined organic layers were washed with saturated $NaHCO_3$ (20 mL), water (20 mL), brine (20 mL), dried over sodium sulfate and concentrated under reduced pressure. The residue was purified by silica gel chromatography to give the title compound 631 (80 mg, 44%) as a white solid. LCMS: $[M+1]^+$=537.40. $^1H$ NMR (400 MHz, Chloroform-d) δ 7.87 (s, 1H), 5.40 (s, 1H), 5.35 (d, J=5.2 hz, 1H), 3.69 (dd, J=19.2, 5.6 Hz, 4H), 3.62-3.47 (m, 5H), 2.38 (dd, J=10.8, 4.8 hz, 1H), 2.31-2.20 (m, 3H), 2.04-1.93 (m, 2H), 1.92-1.78 (m, 4H), 1.49-1.53 (m, 7H), 1.36-1.29 (m, 2H), 1.21-1.04 (m, 5H), 1.01 (s, 3H), 0.99-0.87 (m, 5H), 0.69 (s, 3H).

Example 632: (R)-1-(4-(5-aminopyrimidin-4-yl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

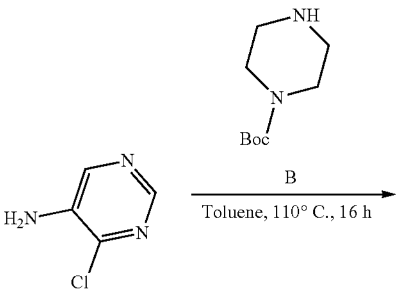

A

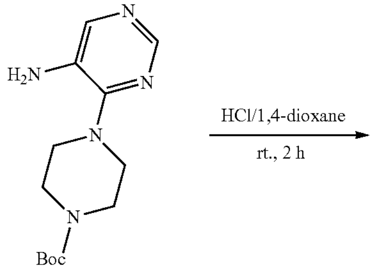

C

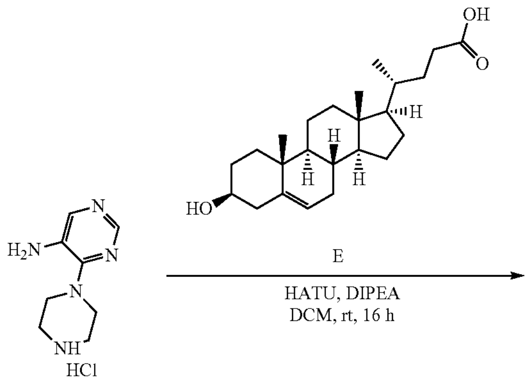

D

-continued

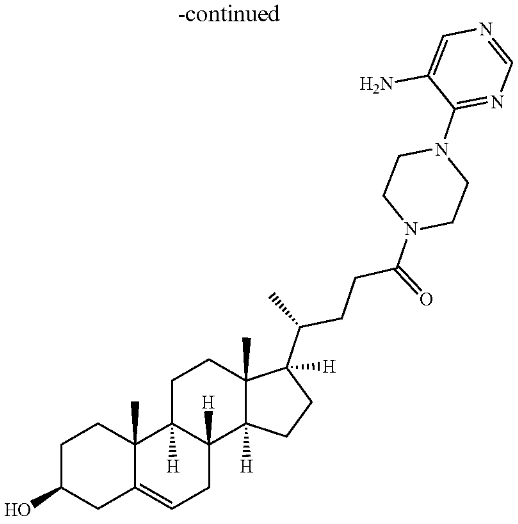

To a solution of compound A (300 mg, 2.32 mmol) in toluene (10 mL) was added compound B (1.08 g, 5.79 mmol). The reaction was stirred at 110° C. for 16 h. The reaction was concentrated under reduced pressure. The crude product was purified by silica gel chromatography to afford compound C (200 mg, 30.8%) as yellow oil.

A solution of compound C (200 mg, 716 μmol) in 4N HCl/1, 4-dioxane (4 mL) was stirred at room temperature for 2 h. The reaction was concentrated to afford compound D as an HCl salt (160 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (40 mg, 404 μmol) and 4-(piperazin-1-yl)pyrimidin-5-aminehCl salt (66.9 mg, 310 μmol) were reacted according to Example 536 to give the title compound 632 (22 mg, 23%) as a white solid. LCMS: $[M+1]^+$=536.50. $^1$HNMR (400 MHz, DMSO-$d_6$) δ 8.13 (s, 1H), 7.91 (s, 1H), 5.26 (d, J=4.8 hz, 1H), 4.93 (s, 2H), 4.58 (d, J=4.8 hz, 1H), 3.59 (t, J=4.8 hz, 4H), 3.23-3.15 (m, 2H), 2.41-2.31 (m, 1H), 2.24-2.20 (m, 1H), 2.18-1.61 (m, 10H), 1.58-1.27 (m, 10H), 1.08-1.01 (m, 7H), 0.94 (s, 3H), 0.92 (d, J=6.4 hz, 3H), 0.86 (q, J=6.4 hz, 2H), 0.65 (s, 3H).

Example 633: (R)-1-(4-(6-aminopyrimidin-4-yl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

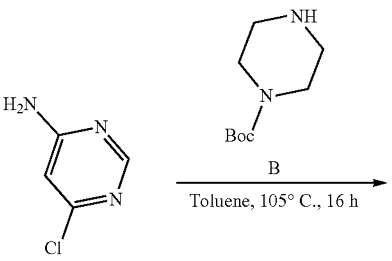

A

-continued

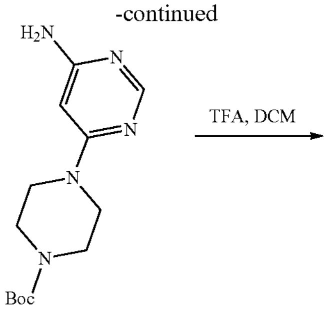

C

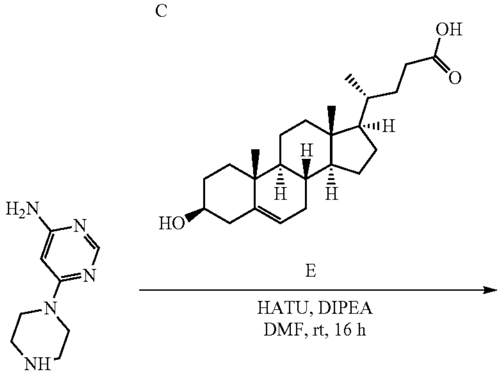

D

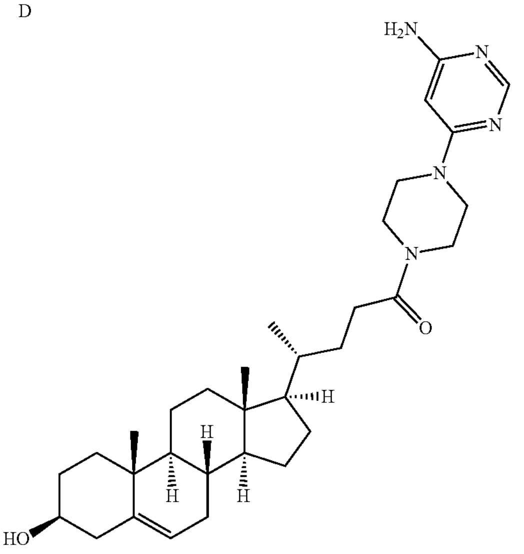

To a solution of compound A (1.80 g, 9.65 mmol) in toluene (22 mL) was added compound B (0.50 g, 3.86 mmol). The reaction was heated to 105° C. under $N_2$ for 16 h. The reaction was cooled to room temperature. The reaction was diluted with water (10 ml) and extracted with EtOAc (10 mL*2). The combined organic layers were washed with water (10 mL), brine (10 mL), dried over sodium sulfate and concentrated under reduced pressure. The residue was purified by silica gel chromatography to afford compound C (850 mg, 78%) as white solid.

To a solution of compound C (90 mg, 322 μmol) in DCM (4 mL) was added TFA (0.5 mL) at room temperature and the reaction was stirred for 2 h. The reaction was concentrated under reduced pressure to afford compound D as the TFA salt (57.7 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (55 mg, 307 μmol) and 6-(piperazin-1-yl)pyrimidin-4-amine (80 mg, 215 μmol) were reacted according to Example 536 to give the title compound 633 (97 mg, 59%) as a white solid. LCMS: $[M+1]^+=536.55$. $^1H$ NMR (400 MHz, Chloroform-d6) δ 8.19 (s, 1H), 5.57 (s, 1H), 5.35-5.34 (m, 1H), 4.62 (s, 2H), 3.72-3.68 (m, 3H), 3.56-3.47 (m, 5H), 2.41-2.37 (m, 1H), 2.29-2.21 (m, 3H), 2.03-1.95 (m, 2H), 1.88-1.79 (m, 4H), 1.61-1.27 (m, 11H), 1.22-1.04 (m, 5H), 1.00 (s, 3H), 0.97-0.92 (m, 4H), 0.69 (s, 3H).

Example 634: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3S)-3-methyl-4-(5-methyl-1,3,4-oxadiazol-2-yl)piperazin-1-yl]pentan-1-one

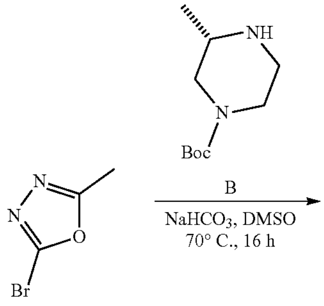

A

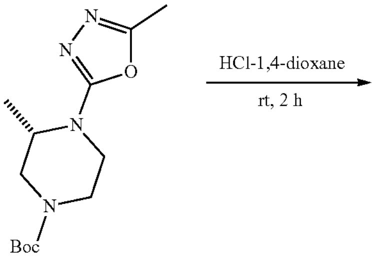

C

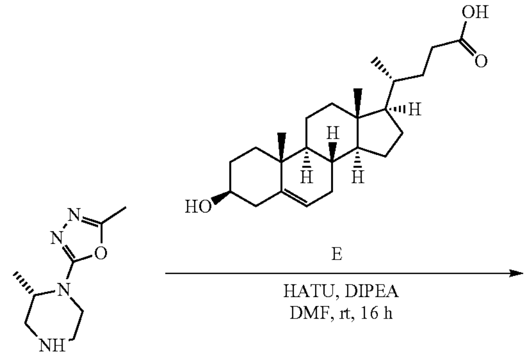

HCl

D

-continued

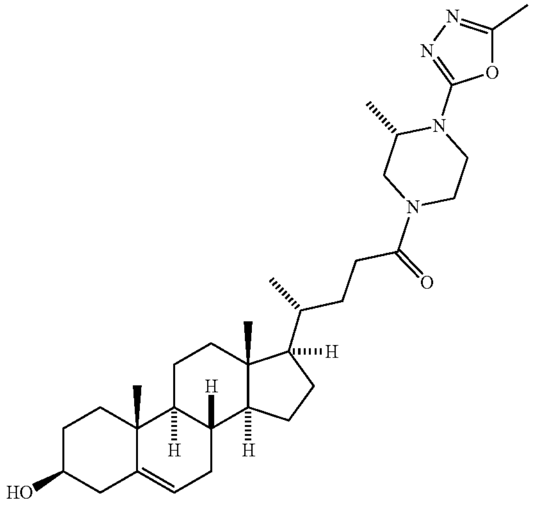

To a solution of compound A (100 mg, 614 μmol) in DMSO (2 mL) at room temperature was added compound B (147 mg, 736 μmol) and $NaHCO_3$ (103 mg, 1.23 mmol). The reaction was stirred at 70° C. for 16 hours. The reaction was cooled to room temperature. Water (30 mL) was added, and the reaction extracted with ethyl acetate (30 mL*3). The combined organic phase was washed with water (30 mL*2), brine (30 mL), dried over sodium sulfate, concentrated under reduced pressure and purified by silica gel chromatography to afford compound C (50 mg, 29%) as yellow solid.

A reaction of compound C (50 mg, 177 μmol) and 4NhCl in 1,4-dioxane (2 mL) was stirred at room temperature for 2 hours. The reaction was concentrated under reduced pressure to afford compound D as an HCl salt (38 mg) as yellow oil.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (58 mg, 154 μmol) and (S)-2-methyl-5-(2-methylpiperazin-1-yl)-1,3,4-oxadiazolehydrochloride (35 mg, 160 μmol) were reacted according to Example 536 to give the title compound 634 (60 mg, 58%) as white solid. $^1H$ NMR (400 MHz, Chloroform-d) δ 5.35 (d, J=4.8 hz, 1H), 4.67-4.42 (m, 1H), 4.25-4.13 (m, 1H), 3.86-3.78 (m, 1H), 3.71-3.67 (m, 1H), 3.56-3.45 (m, 2H), 3.34-3.26 (m, 2H), 3.02-2.78 (m, 1H), 2.40 (s, 4H), 2.35-2.17 (m, 4H), 2.02-1.95 (m, 2H), 1.90-1.83 (m, 4H), 1.54-1.44 (m, 6H), 1.33-1.23 (m, 4H), 1.21-1.08 (m, 5H), 1.04-0.88 (m, 7H), 0.69 (s, 3H).

Example 635: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-2-methyl-4-(5-methyl-1,3,4-oxadiazol-2-yl)piperazin-1-yl)pentan-1-one

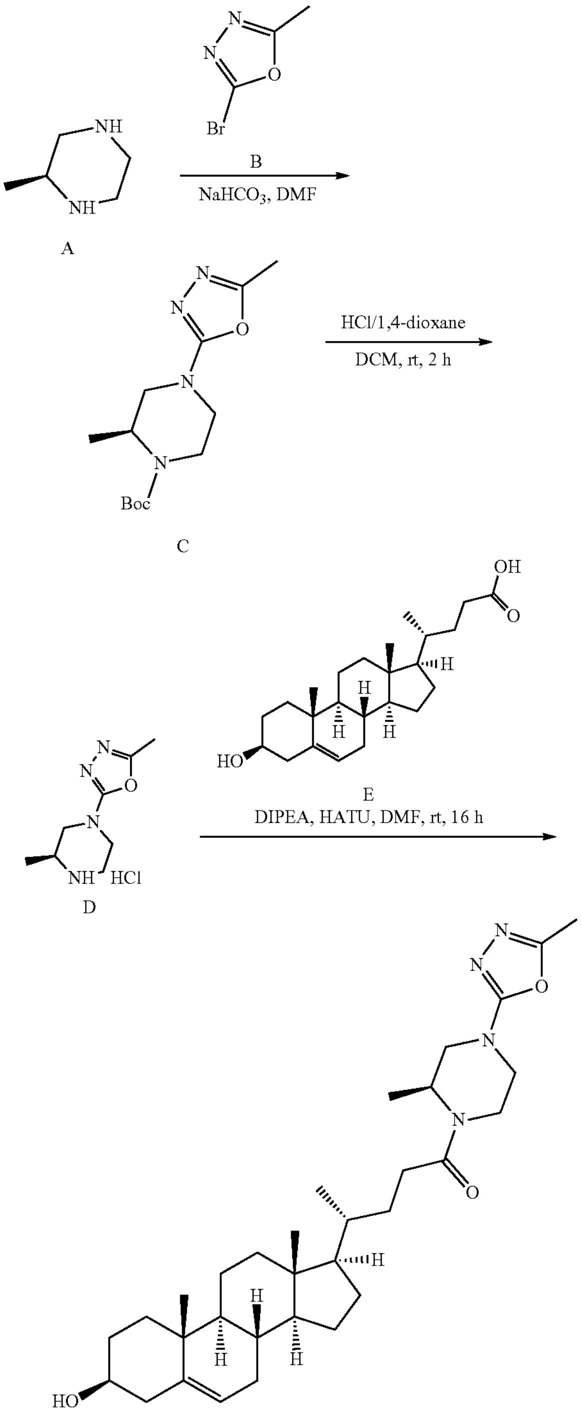

To a solution of compound A (100 mg, 499 μmol) in DMF (3 mL) was added compound B (81.4 mg, 499 μmol) and $NaHCO_3$ (84.9 mg, 999 μmol). The reaction was heated to 70° C. under $N_2$ for 16 h. The reaction was cooled to room temperature and diluted with $h_2O$ (30 mL) and extracted with EtOAc (10 mL*2). The combined organic layers were washed with water (20 mL), brine (20 mL), dried over sodium sulfate and concentrated under reduced pressure. The residue was purified by silica gel chromatography to afford compound C (80 mg, 56%) as a white solid.

To a solution of compound C (80 mg, 283 μmol) in DCM (3 mL) was added hydrogen chloride (2.5 mL, 10 mmol, 4M in dioxane) at room temperature and the reaction was stirred for 2 h. The reaction was concentrated under reduced pressure to afford compound D as an HCl salt (59 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (82 mg, 219 μmol) and (S)-2-methyl-5-(3-methylpiperazin-1-yl)-1,3,4-oxadiazolehydrochloride (59 mg, 274 μmol) were reacted according to Example 536 to give the title compound 635 (70 mg, 47%) as a white solid. LCMS: $[M+1]^+$=539.40. $^1H$ NMR (400 MHz, Chloroform-d) δ 5.35 (dt, J=4.8, 1.6 hz, 1H), 4.54 (bs, 1H), 3.93 (bs, 1H), 3.79-3.61 (m, 2H), 3.52 (ddd, J=11.2, 6.4, 4.8 hz, 1H), 3.20 (d, J=12.8 hz, 1H), 3.02 (s, 1H), 2.40-2.27 (m, 7H), 2.03-1.93 (m, 2H), 1.90-1.80 (m, 3H), 1.61-1.42 (m, 8H), 1.34-1.29 (m, 5H), 1.20-1.03 (m, 6H), 1.00 (s, 3H), 0.96 (d, J=6.4 hz, 3H), 0.68 (s, 3H).

Example 636: (S)—N-(cyclopropylmethyl)-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N,2-dimethylpiperazine-1-carboxamide

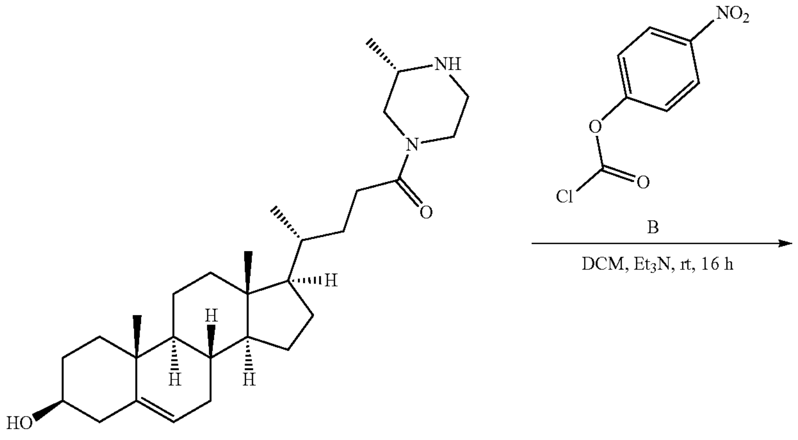

A

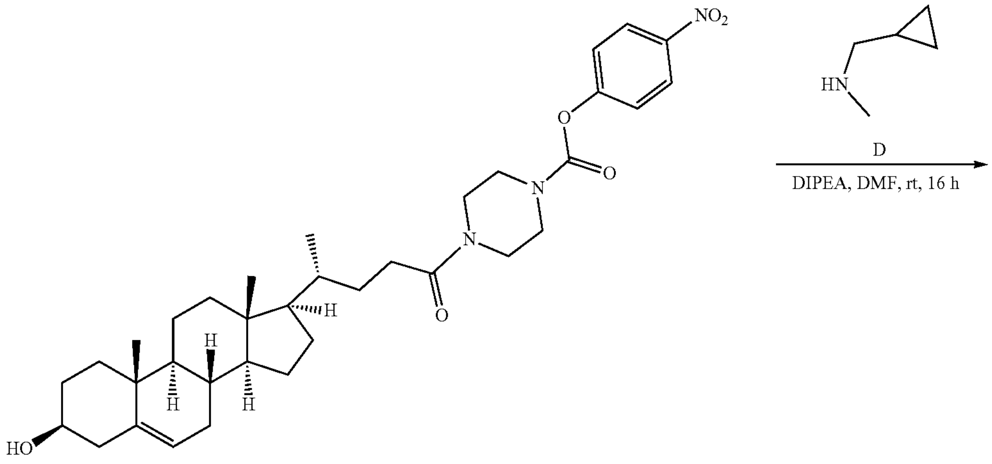

C

-continued

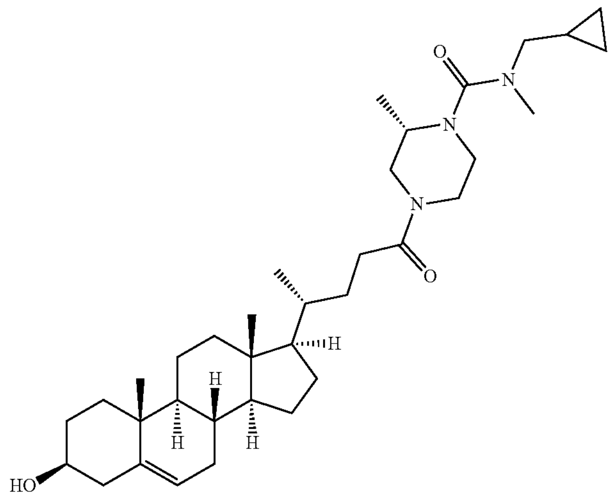

To a 0° C. solution of compound A (100 mg, 219 μmol) in DMF (5 mL) was added $Et_3N$ (33 mg, 328 μmol) and compound B (43 mg, 219 μmol) and stirred for 16 h under $N_2$. The reaction was diluted with saturated aqueous $NH_4Cl$ (30 mL) and extracted with DCM (10 mL*2). The combined organic layers were washed with water (20 mL), brine (20 mL), dried over sodium sulfate and concentrated under reduced pressure. The residue was purified by silica gel chromatography to afford compound C (40 mg, 30%) as a white solid.

To a room temperature solution of compound C (40 mg, 65 μmol), compound D (55 mg, 650 μmol) and DIPEA (26 mg, 197 μmol) in DMF (2 mL) and stirred for 16 h under $N_2$. The reaction was diluted with saturated aqueous $NH_4Cl$ (30 mL) and extracted with EtOAc (10 mL*2). The combined organic layers were washed with water (20 mL), brine (20 mL), dried over sodium sulfate and concentrated under reduced pressure. The residue was purified by silica gel chromatography to give the title compound 636 (15 mg, 40%) as a white solid. LCMS: $[M+1]^+$=568.40. $^1H$ NMR (400 MHz, Chloroform-d) δ 5.35 (d, J=5.2 hz, 1H), 4.37-4.15 (m, 1H), 3.96-3.77 (m, 1H), 3.68 (d, J=12.8 hz, 1H), 3.51 (ddd, J=16.8, 11.2, 4.4 hz, 1H), 3.44-3.36 (m, 1H), 3.33-3.22 (m, 1H), 3.17-2.95 (m, 3H), 2.91 (d, J=6.8 hz, 3H), 2.41-2.15 (m, 4H), 2.04-1.74 (m, 7H), 1.58-1.41 (m, 8H), 1.37-1.28 (m, 3H), 1.20 (d, J=6.4 hz, 2H), 1.16-1.12 (m, 3H), 1.11-1.03 (m, 3H), 1.00 (s, 3H), 0.97-0.87 (m, 5H), 0.68 (s, 3H), 0.53 (d, J=7.6 hz, 2H), 0.18 (d, J=4.8 hz, 2H).

Example 637: (S)—N-(cyclopropylmethyl)-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoyl)-N,3-dimethylpiperazine-1-carboxamide

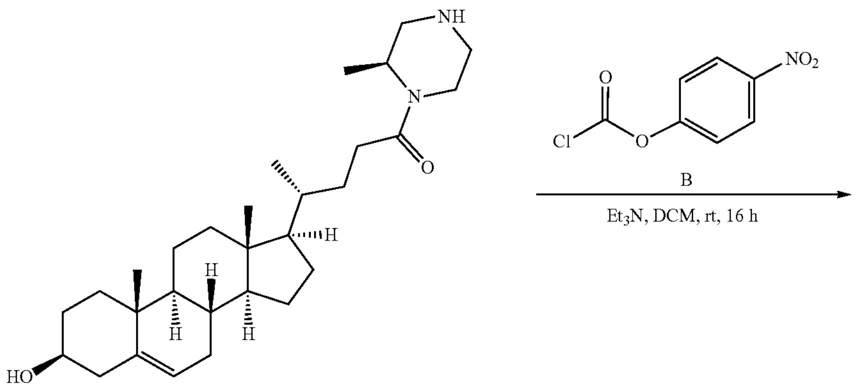

A

-continued

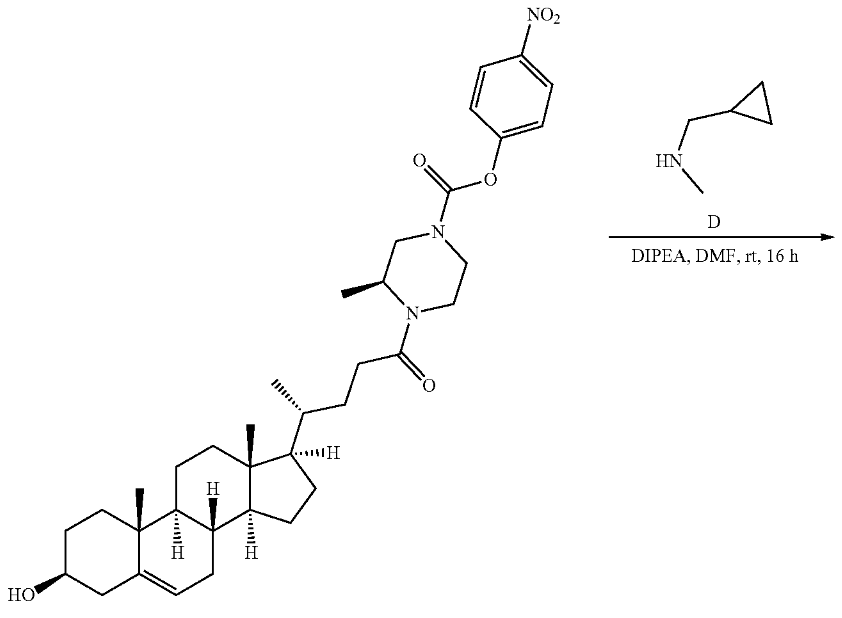

C

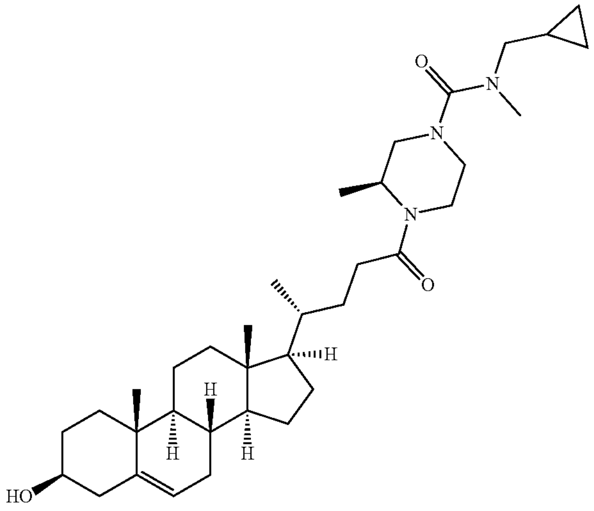

To a 0° C. solution of compound A (100 mg, 219 μmol) in DMF (2 mL) was added compound B (39.7 mg, 219 μmol) and $Et_3N$ (33.2 mg, 328 μmol) and the reaction was stirred at room temperature for 16 hours. Upon completion, the reaction was quenched with saturated aqueous ammonium chloride (10 mL) and extracted with ethyl acetate (10 mL*3). The combined organic layers were washed with brine (10 mL), dried over sodium sulfate, filtered, and concentrated under reduced pressure. The crude product was purified by silica gel chromatography to afford the title compound C (90 mg, 66.1%) as yellow solid.

To a solution of compound C (50 mg, 80.4 μmol) and compound D (342 mg, 4.02 mmol) in DMF (2 mL) was added DIPEA (93.5 mg, 724 μmol) and the reaction was stirred at room temperature for 72 hours. Upon completion, the reaction was quenched with saturated aqueous ammonium chloride (10 mL) and extracted with ethyl acetate (10 mL*3). The combined organic layers were washed with brine, dried over sodium sulfate, filtered, and concentrated under reduced pressure. The crude product was purified by silica gel chromatography to give the title compound 637 (10 mg, 21.9%) as a white solid. LCMS: $[M+1]^+$=568.55. $^1H$ NMR (400 MHz, Chloroform-d) δ 5.34 (dd, J=4.8, 2.8 hz, 1H), 3.73-3.35 (m, 4H), 3.13 (dd, J=14.0, 7.2 hz, 1H), 3.02 (dd, J=14.0, 6.4 hz, 2H), 2.93 (s, 3H), 2.79 (td, J=12.4, 3.2 hz, 1H), 2.46-2.16 (m, 4H), 2.03-1.95 (m, 2H), 1.85-1.79 (m, 4H), 1.54-1.40 (m, 6H), 1.38-1.28 (m, 4H), 1.26 (d, J=3.6 hz, 3H), 1.18 (dd, J=8.0, 4.8 hz, 2H), 1.03-1.13 (m, 3H), 1.00 (s, 3H), 0.96-0.85 (m, 5H), 0.68 (s, 3H), 0.53 (dd, J=7.6, 1.6 hz, 2H), 0.26-0.12 (m, 2H).

Example 638: (3S,8S,9S,10R,13R,14S,17R)-17-((R)-4-(3-isocyanopyridin-2-yl)butan-2-yl)-10,13-dim ethyl-2, 3,4, 7,8, 9,10,11,12,13,14,15,16,17-tetradecahydro-1H-cyclopenta[a]phenanthren-3-ol

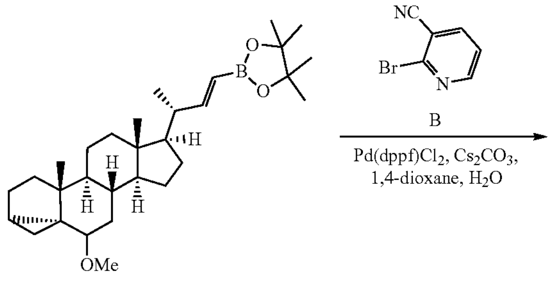

A

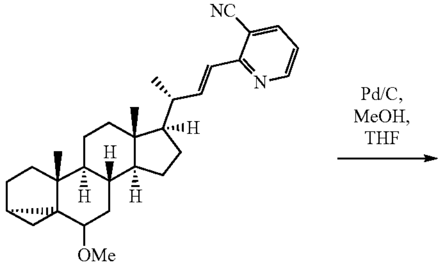

C

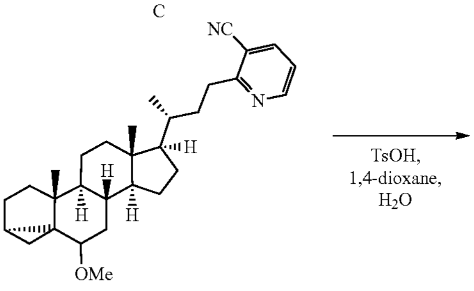

D

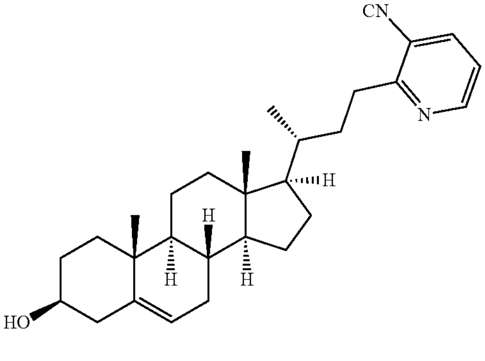

To a solution of compound A (200 mg, 427 μmol) in 1, 4-dioxane (7 mL) and water (1 mL) was added compound B (117 mg, 640 μmol), $Cs_2CO_3$ (348 mg, 1.07 mmol) and Pd(dppf)$Cl_2$ (31.2 mg, 42.7 μmol). The reaction was stirred at 80° C. for 16 hours under nitrogen. The reaction was diluted with water (10 mL) and extracted with ethyl acetate (10 mL*3). The combined organic layer were dried over sodium sulfate, filtered, and concentrated under reduced pressure. The crude product was purified by silica gel chromatography to afford compound C (143 mg, 75%) as oil.

To a solution of compound C (120 mg, 270 μmol) in methanol (7 mL) and THE (1.5 mL) was added 10% Pd/C (50 mg). The reaction was stirred at room temperature for 30 minutes under hydrogen. The reaction was filtered and was concentrated under reduced pressure. The crude product was purified by prep-TLC to afford compound D (83 mg, 68%) as oil.

2-((3R)-3-((1aR,3aR,3bS,5aR,6R,8aS,8bS,10aS)-10-methoxy-3a,5a-dimethylhexadecahydrocyclopenta[a]cyclopropa[2,3]cyclopenta[1,2-f]naphthalen-6-yl)butyl)nicotinonitrile (83 mg, 186 μmol) was reacted according to Example 430 to give the title compound 638 (40 mg, 50%) as a white solid. LCMS: $[M+1]^+$=433.40. $^1$H NMR (400 MHz, DMSO-$d_6$) δ 8.75 (dd, J=5.2, 1.6 hz, 1H), 8.23 (dd, J=7.6, 1.6 hz, 1H), 7.43 (dd, J=7.6, 4.8 hz, 1H), 5.26 (d, J=4.8 hz, 1H), 4.58 (d, J=4.4 hz, 1H), 3.25 (d, J=5.2 hz, 1H), 2.99 (t, J=11.2 hz, 1H), 2.86 (d, J=12.4 hz, 1H), 2.10 (d, J=18.0 hz, 2H), 1.94 (d, J=11.6 hz, 1H), 1.85-1.72 (m, 3H), 1.67 (d, J=12.0 hz, 1H), 1.53 (bs, 2H), 1.46 (s, 3H), 1.41-1.33 (m, 3H), 1.25 (d, J=9.2 hz, 3H), 1.17 (bs, 1H), 1.02-0.97 (s, 5H), 0.94 (s, 3H), 0.86 (d, J=8.4 hz, 1H), 0.64 (s, 3H).

Example 639: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methyl-N-(pyridin-4-yl)pentanamide

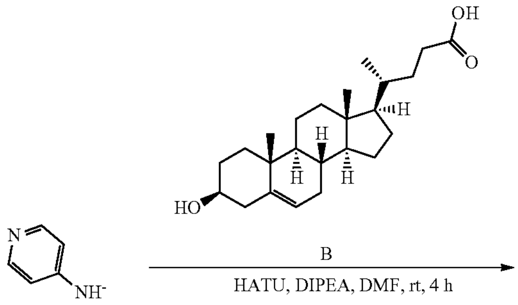

A

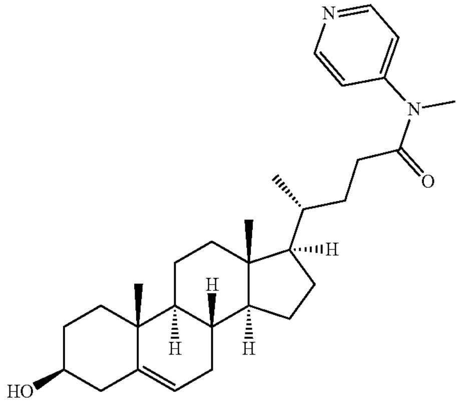

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (173 mg, 462 μmol) and N-methylpyridin-4-amine(50 mg, 462 μmol were reacted according to Example 536 to give the title compound 639 (150 mg, 70%) as white solid. LCMS: $[M+1]^+$=465.40. $^1$H NMR (400 MHz, Chloroform-d) δ 8.68-8.61 (m, 2H), 7.19-7.12 (m, 2H), 5.34 (dt, J=4.4, 2.0 hz, 1H), 3.56-3.46 (m, 1H), 3.30 (s, 3H), 2.32-2.22 (m, 3H), 2.14 (d, J=5.2 hz, 1H), 1.99-1.92 (m, 2H), 1.85-1.81 (m, 2H), 1.77 (q, J=2.8 hz, 1H), 1.62 (bs, 2H), 1.58-1.51 (m, 3H), 1.47 (d, J=3.6 hz, 2H), 1.43 (dd, J=9.6, 4.2 hz, 2H), 1.32 (t, J=4.4 hz, 2H), 1.29-1.21 (m, 3H), 1.12-1.09 (m, 1H), 1.07-1.02 (m, 2H), 1.00-0.95 (m, 4H), 0.79 (d, J=5.6 hz, 3H), 0.64 (s, 3H).

Example 640: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(2-hydroxypyridin-3-yl)piperazin-1-yl) pentan-1-one

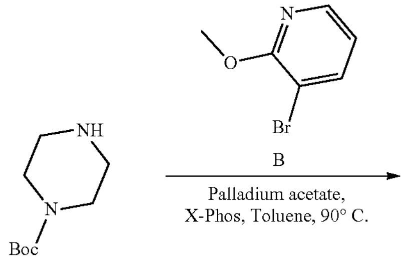

B
A

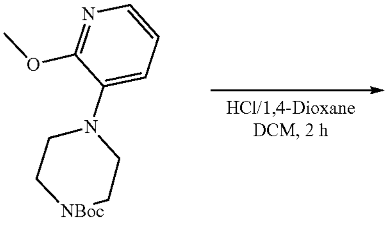

C

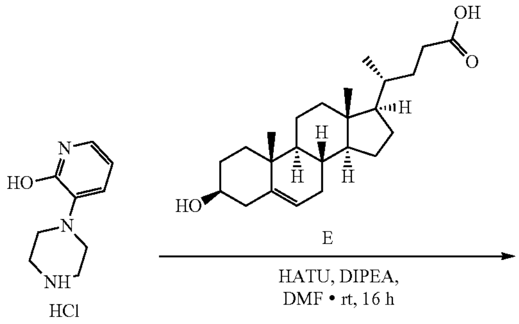

D
E

-continued

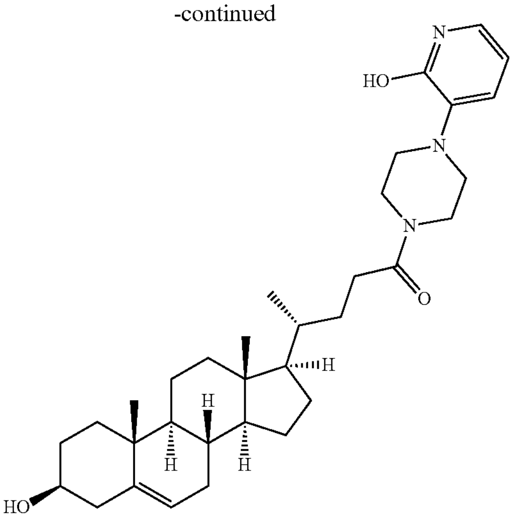

To a solution of compound B (121 mg, 644 μmol) in toluene (2 mL) was added compound A (100 mg, 537 μmol), palladium acetate (24.1 mg, 107 μmol), X-Phos (51.2 mg, 107 μmol) and t-BuONa (103 mg, 1.07 mmol). The reaction was stirred at 90° C. for 4 h under $N_2$. The reaction was quenched by $H_2O$ (5 mL) and extracted with ethyl acetate (20 mL). The organic layer was concentrated under reduced pressure. The crude product was purified by silica gel chromatography to afford compound C (86 mg, 55%).

To a solution of compound C (86 mg, 293 μmol) in DCM (2 mL) was added HCl (4 M in 1, 4-dioxane, 0.7 mL, 2.93 mmol). The reaction was stirred at room temperature for 2 hours. The solution was concentrated to afford compound D as an HCl salt (52.5 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (87.5 mg, 233 μmol) and 3-(piperazin-1-yl)pyridin-2-ol (52.5 mg, 228 μmol) were reacted according to Example 536 to give the title compound 640 (29.5 mg, 19%) as a white solid. LCMS: [M+1]+=536.35. $^1H$ NMR (400 MHz, Chloroform-d) δ 7.07 (d, J=6.4 hz, 1H), 6.79 (d, J=7.2 hz, 1H), 6.26 (t, J=6.8 hz, 1H), 5.38 (d, J=5.2 hz, 1H), 3.89-3.49 (m, 6H), 3.18-3.10 (m, 4H), 2.51-2.20 (m, 4H), 2.08-1.97 (m, 2H), 1.94-1.77 (m, 4H), 1.57-1.41 (m, 7H), 1.32-1.08 (m, 6H), 1.06-0.92 (m, 8H), 0.73 (s, 3H).

Example 641: (1S,4s)-4-((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanamido)-N,N-dimethylcyclohexane-1-carboxamide

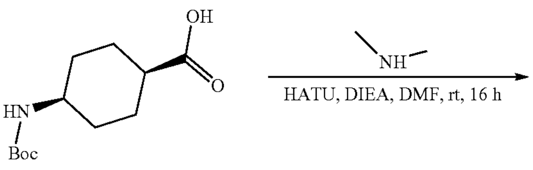

A

-continued

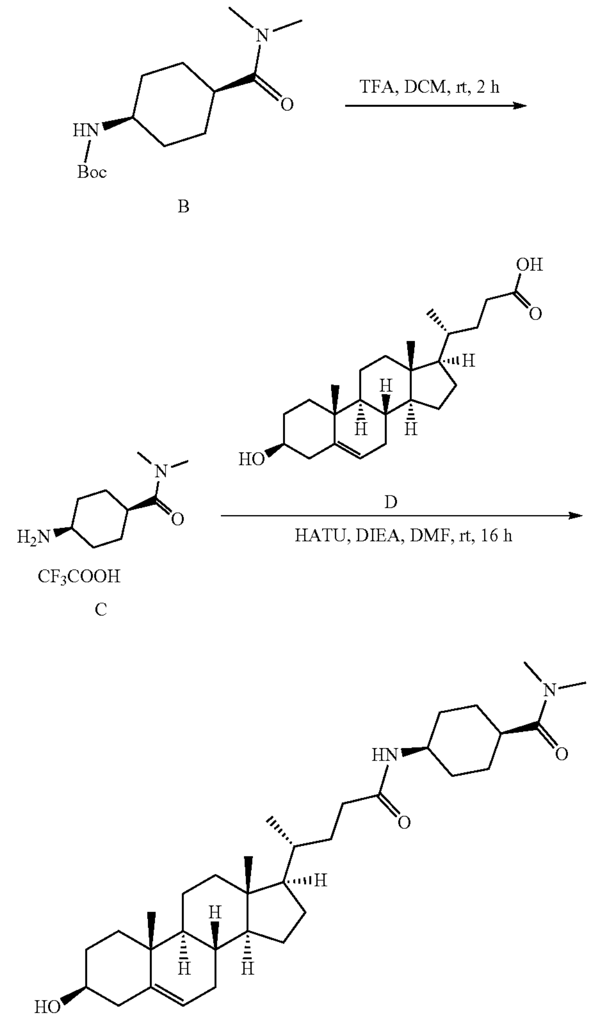

A solution of compound A (500 mg, 2.06 mmol), dimethylamine (1.23 mL, 2M in THF, 2.47 mmol), DIEA (797 mg, 6.17 mmol) and HATU (1.17 g, 3.08 mmol) in DMF (10 mL) was stirred at room temperature for 16 h. The reaction was purified by RP-column to afford compound B (330 mg, 59.4%).

A solution of compound B (100 mg, 370 μmol) in DCM (2 mL) was added TFA (84.3 mg, 740 μmol). The reaction was stirred at room temperature for 2 h and concentrated to afford compound C as the TFA salt (100 mg, 100% yield).

(1s,4s)-4-amino-N,N-dimethylcyclohexane-1-carboxamide trifluoroethanoic acid (113 mg, 399 μmol) and (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (130 mg, 333 μmol) were reacted according to Example 536 to give the title compound 641 (60 mg, 34.2%) as a white solid. LCMS: $[M+1]^+$=527.50. $^1H$ NMR (400 MHz, Chloroform-d) δ 5.74 (d, J=8.0 hz, 1H), 5.35 (d, J=5.2 hz, 1H), 4.13 (d, J=7.6 hz, 1H), 3.53 (td, J=11.4, 5.8 hz, 1H), 3.05 (s, 3H), 2.94 (s, 3H), 2.61 (dt, J=9.6, 5.2 hz, 1H), 2.31-2.18 (m, 3H), 2.08-1.94 (m, 3H), 1.91-1.77 (m, 6H), 1.75-1.63 (m, 5H), 1.55-1.41 (m, 7H), 1.37-1.03 (m, 10H), 1.00 (s, 3H), 0.94 (d, J=6.5 hz, 3H), 0.91-0.82 (m, 1H), 0.68 (s, 3H).

Example 642: (R)—N-(1-(cyclopropanecarbonyl)piperidin-4-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methylpentanamide

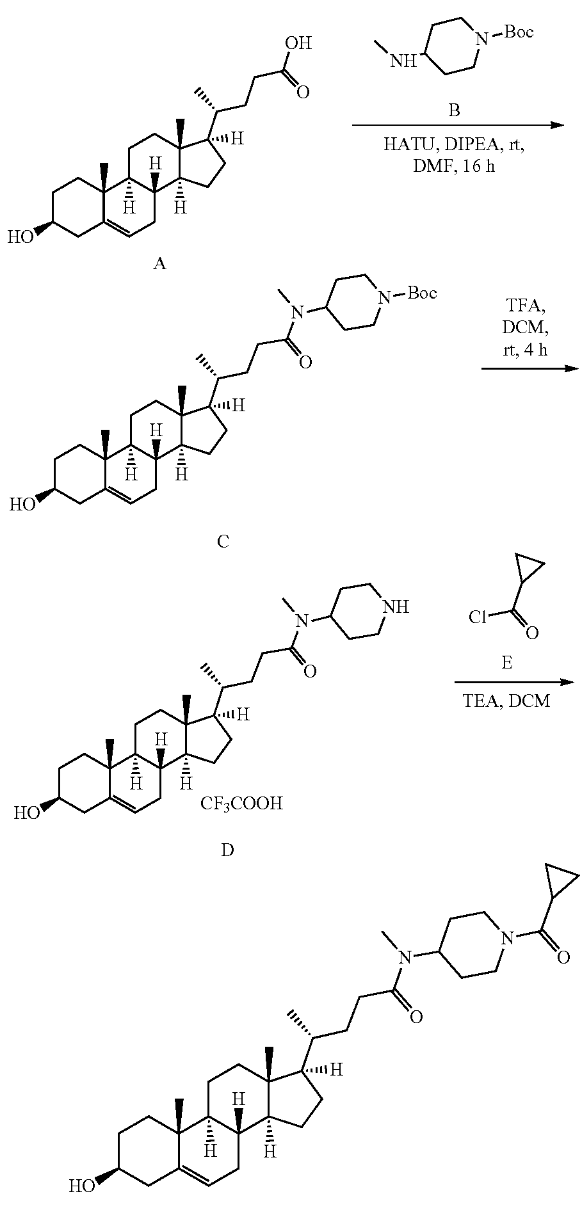

To a room temperature solution of compound A (2.0 g, 5.34 mmol), compound B (1.14 g, 5.34 mmol) and DIPEA (3.45 g, 26.7 mmol) in DMF (20 mL) was added HATU (3.05 g, 8.01 mmol) and stirred for 16 h. The reaction was diluted with water (10 mL) and extracted with EtOAc (10 mL*2). The combined organic layers were washed with water (20 mL), brine (20 mL), dried over sodium sulfate and concentrated under reduced pressure. The residue was purified by silica gel chromatography to afford compound C (2.8 g, 91%) as white solid.

To a solution of compound C (1.5 g, 2.63 mmol) in DCM (15 mL) was added TFA (5 mL) at room temperature and the reaction was stirred for 4 h. The reaction was concentrated under reduced pressure to afford compound D as a TFA salt (1.5 g).

To a room temperature solution of compound D (200 mg, 342 μmol), compound E (22.2 mg, 212 μmol) in DCM (4 mL) was added TEA (190 mg, 1.27 mmol) and the reaction was stirred for 16 h. The reaction was quenched with water, extracted with EtOAc (5 mL*2). The combined organic layers were washed with water (10 mL), brine (10 mL), dried over sodium sulfate and concentrated under reduced pressure. The residue was purified by silica gel chromatography to give the title compound 642 (57 mg, 50%) as a white solid. LCMS: $[M+1]^+$=539.45. $^1H$ NMR (400 MHz, Chloroform-d6) δ 5.35-5.34 (m, 1H), 4.79-4.68 (m, 2H), 4.30-4.27 (m, 1H), 3.56-3.48 (m, 1H), 3.18-3.15 (m, 1H), 2.83-2.78 (m, 3H), 2.66-2.63 (m, 1H), 2.35-2.17 (m, 4H), 2.04-1.69 (m, 10H), 1.54-1.41 (m, 7H), 1.36-1.25 (m, 4H), 1.21-1.03 (m, 5H), 1.01 (s, 3H), 0.98-0.93 (m, 5H), 0.91-0.84 (m, 1H), 0.79-0.74 (m, 2H), 0.69 (s, 3H).

Example 643: Methyl 4-[(4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-N-methylpentanamido]piperidine-1-carboxylate

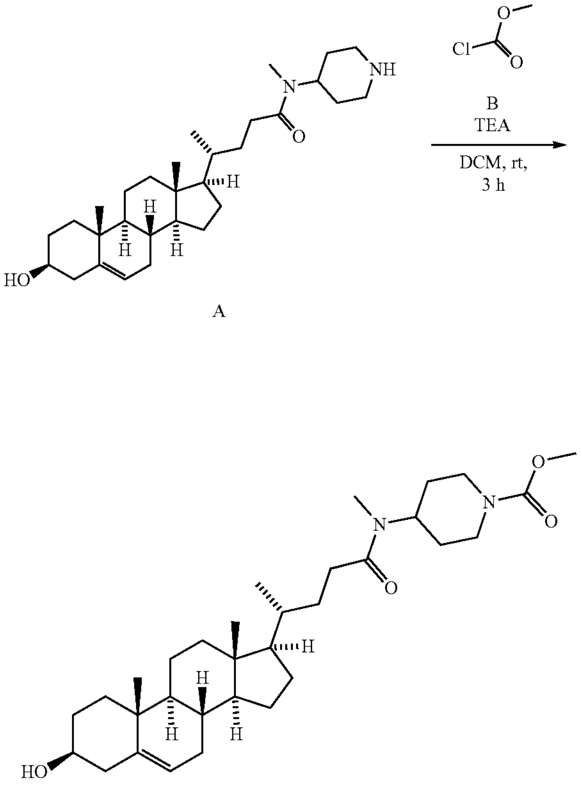

To a solution of compound A (200 mg, 425 μmol) and $Et_3N$ (64.5 mg, 637 μmol) in DCM (5 mL) was added compound B (40.1 mg, 425 μmol) at 0° C. under $N_2$ and stirred for 3 h. The reaction was diluted with saturated aqueous $NH_4Cl$ (30 mL) and extracted with EtOAc (10 mL*2). The combined organic layers were washed with saturated $NaHCO_3$ (20 mL), water (20 mL), brine (20 mL), dried over sodium sulfate and concentrated under reduced pressure. The residue was purified by silica gel chromatography to give the title compound 643 (18 mg, 8%) as a white solid. LCMS: $[M+1]^+$=529.40. $^1H$ NMR (400 MHz, Chloroform-d) δ 5.35 (d, J=5.2 hz, 1H), 4.66 (tt, J=10.4, 4.8 hz, 1H), 4.23 (bs, 2H), 3.70-3.67 (m, 3H), 3.52 (tt, J=10.8, 4.8 hz, 1H), 2.80-2.76 (m, 5H), 2.27-2.38 (m, 4H), 1.99-2.02 (m, 2H), 1.82-1.90 (m, 5H), 1.66 (bs, 1H), 1.58 (bs, 2H), 1.56-1.39 (m, 8H), 1.31-1.36 (m, 3H), 1.22-1.06 (m, 4H), 1.00-0.95 (m, 7H), 0.68 (s, 3H).

Example 644: 4—((R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-N-methylpentanamido)-N,N-dimethylpiperidine-1-carboxamide

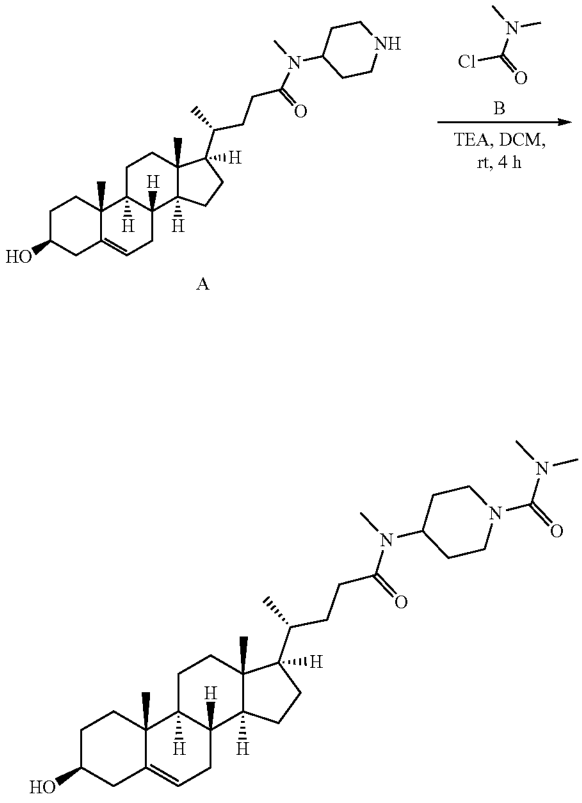

To a 0° C. solution of compound A (100 mg, 212 μmol) in DMF (3 mL) was added TEA (105 mg, 1.06 mmol) and compound B (22.8 mg, 212 μmol) and stirred for 4 h under $N_2$. The reaction was diluted with saturated aqueous $NH_4Cl$ (30 mL) and extracted with DCM (10 mL*2). The combined organic layers were washed with water (20 mL), brine (20 mL), dried over sodium sulfate and concentrated under reduced pressure. The residue was purified by silica gel chromatography to give the title compound 644 (15 mg, 13%) as a white solid. LCMS: $[M+1]^+$=542.40. $^1H$ NMR (400 MHz, Chloroform-d) δ 5.35 (d, J=5.2 hz, 1H), 4.65 (tt, J=11.2, 4.8 hz, 1H), 3.75 (d, J=12.8 hz, 2H), 3.52 (tt, J=10.8, 4.4 hz, 1H), 2.92-2.74 (m, 11H), 2.43-2.16 (m, 4H), 2.05-1.76 (m, 7H), 1.58-1.43 (m, 8H), 1.37-1.24 (m, 6H), 1.21-1.02 (m, 5H), 1.01 (s, 3H), 0.96-0.87 (m, 4H), 0.69 (s, 3H).

Example 645: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-N-methyl-N-[1-(pyrrolidine-1-carbonyl)piperidin-4-yl]pentanamide

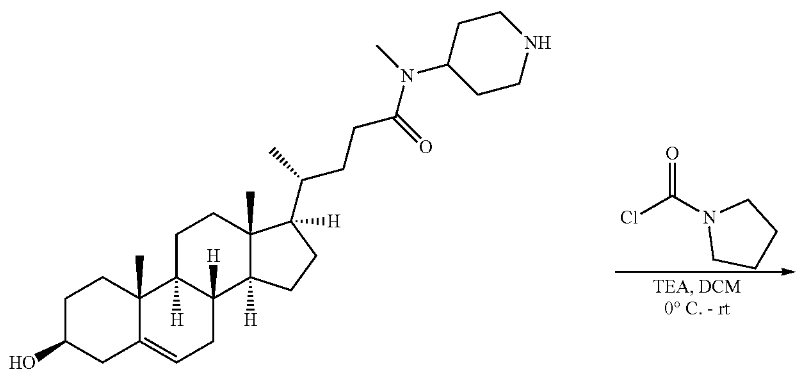

A

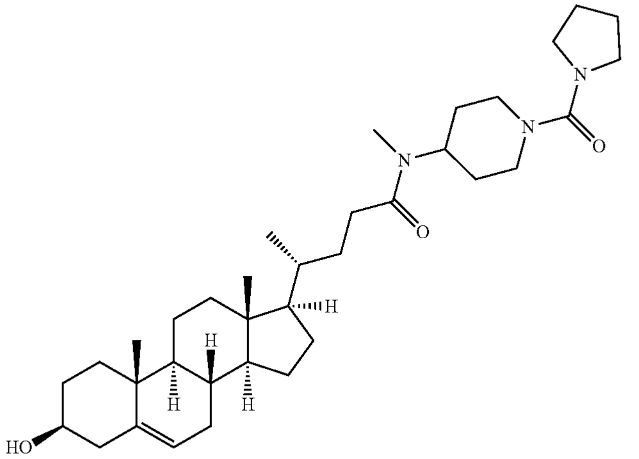

To a 0° C. solution of compound A (100 mg, 212 μmol) in DCM (5 mL) at room temperature was added TEA (107 mg, 1.06 mmol) and ethyl pyrrolidine-1-carbonyl chloride (28.4 mg, 212 μmol). The reaction was stirred for 16 h. Water (10 mL) was added and the reaction was extracted with ethyl acetate (20 mL). The organic layer was dried over sodium sulfate and was concentrated under reduced pressure. The crude product was purified by silica gel chromatography to give the title compound 645 (36.8 mg, 30.5%) as white solid. LCMS: $[M+1]^+$=568.55. $^1H$ NMR (400 MHz, $CDCl_3$) δ 5.34 (d, J=5.2 hz, 1H), 4.68-4.60 (m, 1H), 3.84 (d, J=13.2 hz, 2H), 3.54-3.48 (m, 1H), 3.36 (q, J=6.0 hz, 4H), 2.81-2.75 (m, 5H), 2.39-2.16 (m, 4H), 2.02-1.93 (m, 2H), 1.86-1.75 (m, 8H), 1.58-1.52 (m, 6H), 1.51-1.43 (m, 5H), 1.35-1.25 (m, 3H), 1.21-1.05 (m, 4H), 1.00 (s, 3H), 0.97 (bs, 1H), 0.95 (d, J=6.4 hz, 3H), 0.91-0.83 (m, 1H), 0.68 (s, 3H).

Example 646: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-4-(6-methoxypyrimidin-4-yl)-3-methylpiperazin-1-yl)pentan-1-one

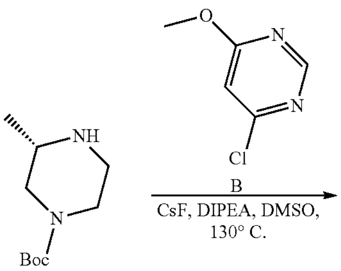

A

-continued

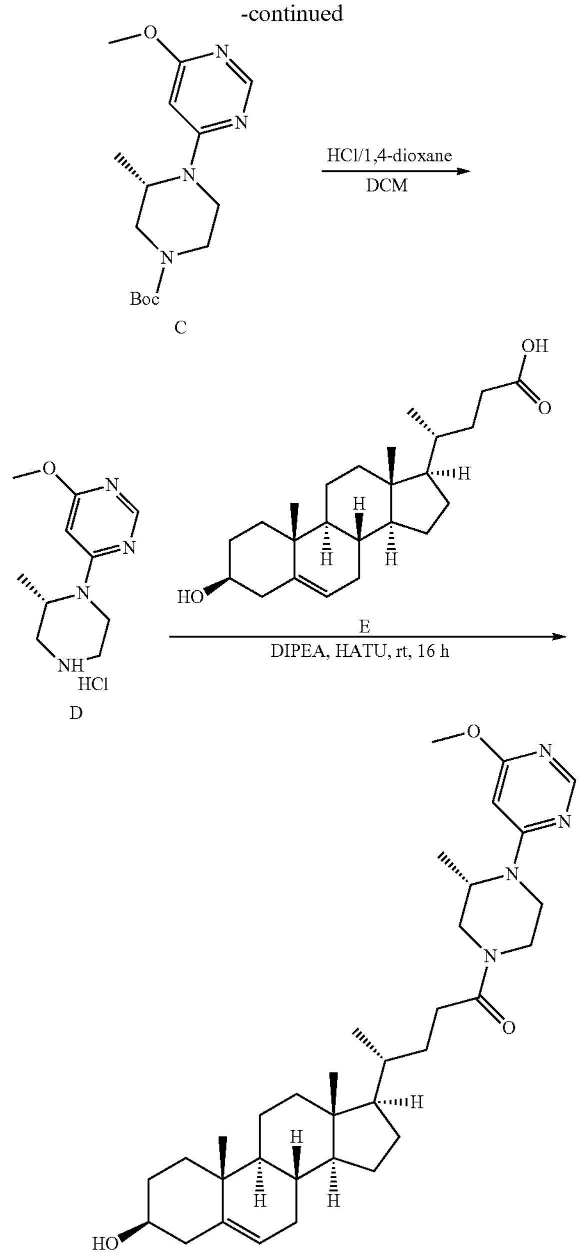

To a solution of compound A (100 mg, 499 μmol) in DMSO (3 mL) was added compound B (72 mg, 499 μmol), DIPEA (194 mg, 1.5 mmol) and CsF (75 mg, 499 μmol). The reaction was heated to 130° C. under $N_2$ for 16 h. The reaction was cooled to room temperature and diluted with $h_2O$ (30 mL) and extracted with EtOAc (10 mL*2). The combined organic layers were washed with water (20 mL), brine (20 mL), dried over sodium sulfate and concentrated under reduced pressure. The residue was purified by silica gel chromatography to afford compound C (120 mg, 78%) as yellow oil.

To a solution of compound C (120 mg, 389 μmol) in DCM (2 mL) was added hydrogen chloride (2 mL, 8 mmol, 4M in dioxane) at room temperature and the reaction was stirred for 2 h. The reaction was concentrated under reduced pressure to afford compound D as an HCl salt (70 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (87 mg, 230 μmol) and (S)-4-methoxy-6-(2-methylpiperazin-1-yl)pyrimidinehydrochloride(70 mg, 288 μmol) were reacted according to Example 536 to give the title compound 646 (40 mg, 24%) as a white solid. LCMS: $[M+1]^+$=565.40. $^1H$ NMR (400 MHz, Chloroform-d) δ 8.33 (d, J=2.0 hz, 1H), 5.78 (s, 1H), 5.36-5.34 (m, 1H), 4.64-4.48 (m, 1H), 4.35 (d, J=12.0 hz, 1H), 3.92 (bs, 4H), 3.69 (d, J=13.2 hz, 1H), 3.49-3.37 (m, 2H), 3.35-3.06 (m, 2H), 2.93-2.81 (m, 1H), 2.44-2.20 (m, 4H), 1.99 (ddt, J=14.4, 10.8, 5.2 hz, 2H), 1.85-1.67 (m, 4H), 1.49-1.45 (m, 8H), 1.40-1.26 (m, 3H), 1.19 (d, J=6.8 hz, 2H), 1.17-1.03 (m, 5H), 1.01 (s, 3H), 0.94-0.88 (m, 4H), 0.69 (s, 3H).

Example 647: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3S)-3-methyl-4-(2-methylpyrimidin-4-yl)piperazin-1-yl]pentan-1-one

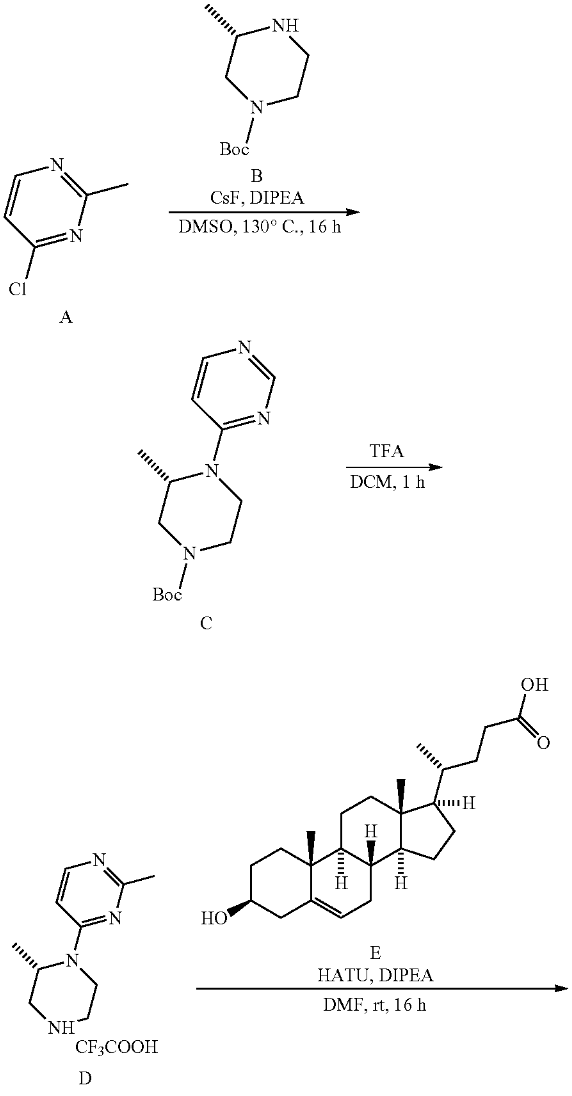

-continued

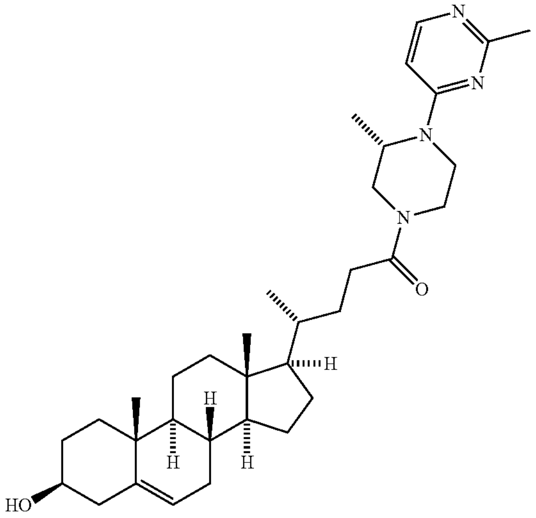

To a solution of compound A (100 mg, 778 μmol) in DMSO (10 mL) was added compound B (187 mg, 933 mmol), CsF (354 mg, 2.33 mmol) and DIPEA (503 mg, 3.89 mmol). The reaction was heated to 130° C. under $N_2$ for 16 h. The reaction was cooled to room temperature and concentrated under reduced pressure. The residue was purified by silica gel chromatography to afford compound C (70 mg, 30%) as yellow solid.

To a solution of compound C (70 mg, 239 μmol) in DCM (6 mL) was added TFA (2 mL) at room temperature and the reaction was stirred for 2 h. The reaction was concentrated under reduced pressure to afford compound D as the TFA salt (70 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (93.5 mg, 250 μmol) and (S)-2-methyl-4-(2-methylpiperazin-1-yl)pyrimidine 2,2,2-trifluoroacetate (70 mg, 228 μmol) were reacted according to Example 536 to give the title compound 647 (70 mg, 40%) as a white solid. LCMS: $[M+1]^+$=549.40. $^1$H NMR (400 MHz, Chloroform-d) δ 8.15 (d, J=5.6 hz, 1H), 6.29 (dd, J=6.4, 2.8 hz, 1H), 5.35 (d, J=5.2 hz, 1H), 4.38 (t, J=13.6 hz, 1H), 4.10 (dd, J=16.8, 10.4 hz, 1H), 3.57-3.40 (m, 1H), 3.37-3.06 (m, 2H), 2.51 (d, J=2.0 hz, 3H), 2.38 (dd, J=16.0, 11.2 hz, 1H), 2.32-2.20 (m, 3H), 1.99-2.04 (m, 3H), 1.84 (q, J=6.0, 4H), 1.74-1.56 (m, 4H), 1.49-1.40 (m, 3H), 1.37-1.29 (m, 2H), 1.14-2.16 (m, 7H), 1.01 (s, 3H), 0.96-0.89 (m, 4H), 0.90-0.82 (m, 2H), 0.69 (s, 3H).

Example 648: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-4-(6-methoxypyrimidin-4-yl)-2-methylpiperazin-1-yl)pentan-1-one

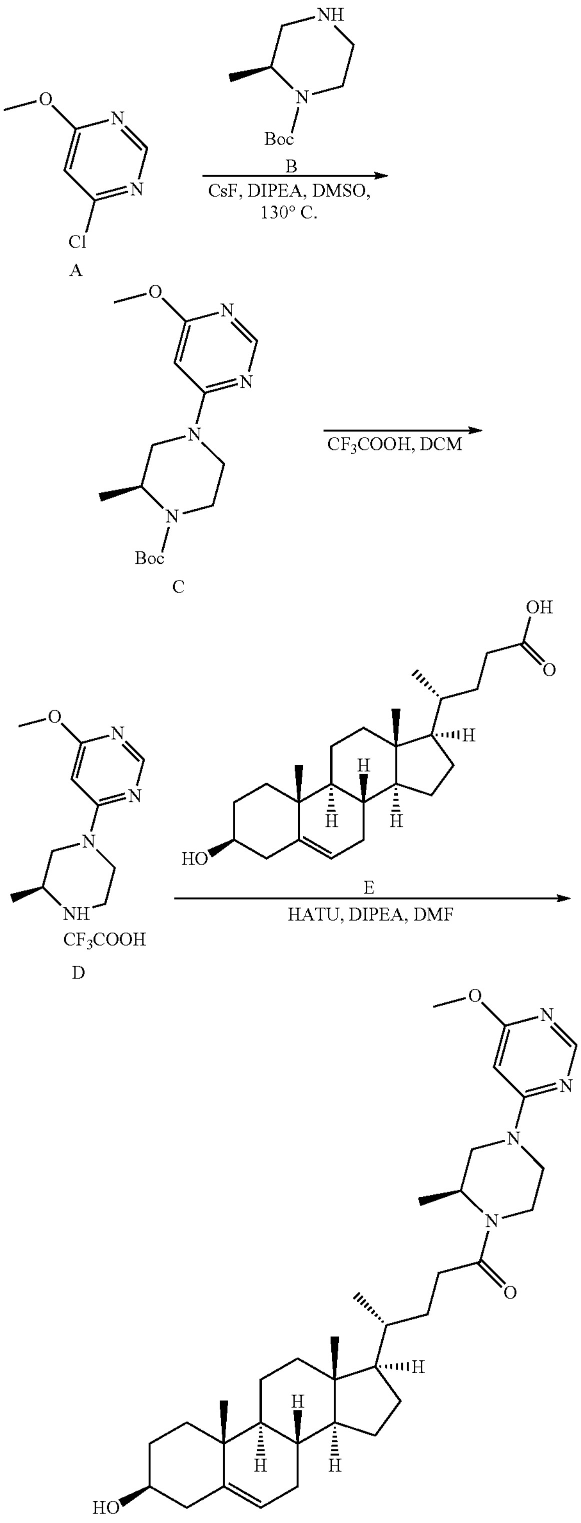

To a solution of compound A (86.6 mg, 599 μmol) and compound B (100 mg, 499 μmol) in DMF (3 mL) was added CsF (228 mg, 1.5 mmol) and DIPEA (323 mg, 2.5 mmol) and the reaction was stirred at 130° C. under nitrogen for 16 hours. Upon completion, the reaction was quenched with water (50 mL) and extracted with ethyl acetate (50 mL*3). The combined organic layers were washed with brine, dried over sodium sulfate, filtered, and concentrated under reduced pressure. The crude product was purified by silica gel chromatography to afford compound C (140 mg, 90%) as oil.

To a solution of compound C (148 mg, 479 μmol) in dichloromethane (3 mL) was added TFA (1 mL) at room temperature and was stirred for 1 hour. Upon completion, the reaction was added dichloromethane (10 mL) and concentrated under reduced pressure to afford compound D as the TFA salt (80 mg, 80% yield).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (100 mg, 267 μmol) and (S)-4-methoxy-6-(3-methylpiperazin-1-yl)pyrimidine 2,2,2-trifluoroacetate (83.4 mg, 400 μmol) were reacted according to Example 536 to give the title compound 648 (100 mg, 66%) as a white solid. LCMS: $[M+1]^+$=565.60. $^1$H NMR (400 MHz, Chloroform-d) δ 8.31 (s, 1H), 5.79 (s, 1H), 5.34 (dt, J=4.4, 1.6 hz, 1H), 4.13-4.10 (m, 1H), 3.91 (s, 3H), 3.76-3.65 (m, 1H), 3.55-3.48 (m, 1H), 3.31-3.19 (m, 1H), 3.03 (q, J=11.2 hz, 1H), 2.39 (d, J=13.6 hz, 1H), 2.31-2.18 (m, 3H), 2.02-1.93 (m, 2H), 1.91-1.77 (m, 4H), 1.70 (s, 2H), 1.59 (m, 1H), 1.47-1.36 (m, 4H), 1.37-1.29 (m, 2H), 1.28-1.22 (m, 2H), 1.13 (d, J=5.2 hz, 3H), 1.10 (bs, 1H), 1.08-1.02 (m, 2H), 1.00 (s, 3H), 0.96 (d, J=6.4 hz, 3H), 0.91-0.88 (m, 1H), 0.68 (s, 3H).

Example 649: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-2-methyl-4-(2-methylpyrimidin-4-yl)piperazin-1-yl)pentan-1-one

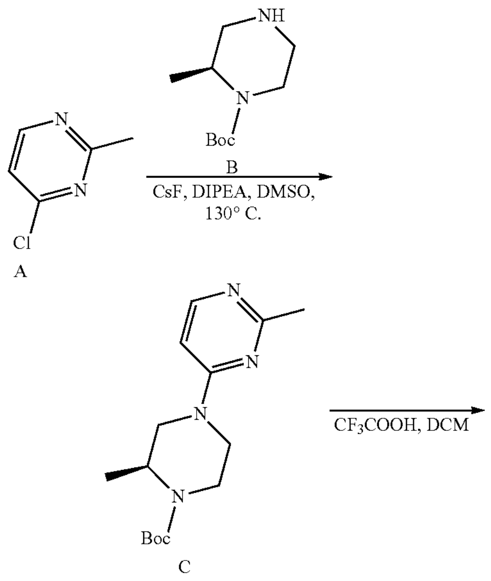

-continued

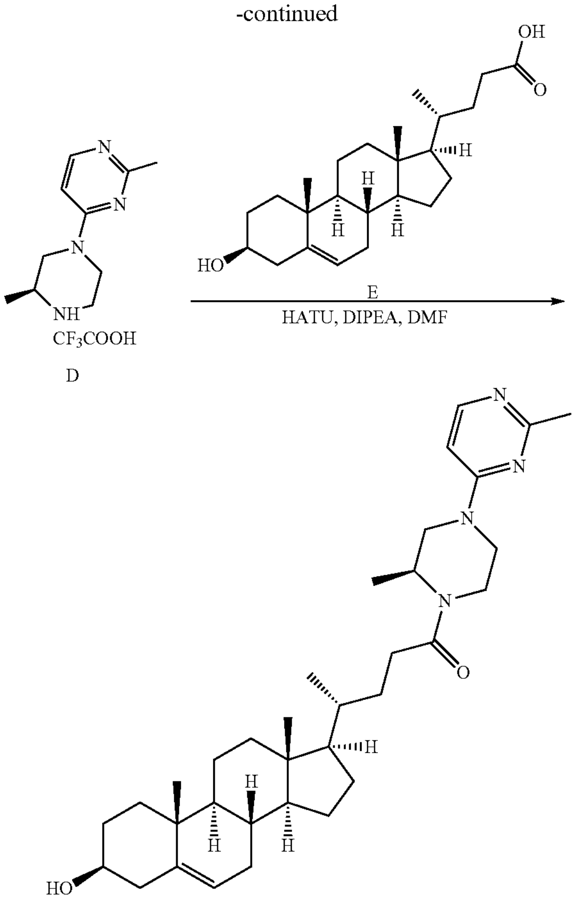

To a solution of compound A (70.6 mg, 549 μmol) in DMSO (3 mL) was added compound B (100 mg, 499 μmol), CsF (228 mg, 1.5 mmol) and DIPEA (323 mg, 2.5 mmol). The reaction was stirred at 130° C. under nitrogen for 16 hours. Upon completion, the reaction was quenched with water (50 mL) and extracted with ethyl acetate (50 mL*3). The combined organic layers were washed with brine, dried over sodium sulfate, filtered, and concentrated under reduced pressure. The crude product was purified by silica gel chromatography to afford compound B (140 mg, 96%) as oil.

To a solution of compound B (140 mg, 479 μmol) in dichloromethane (2 mL) was added TFA (0.5 mL) at room temperature and was stirred for 1 hour.

Upon completion, the reaction was added dichloromethane (10 mL) and concentrated three times to afford compound D as the TFA salt (85 mg, 92%).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (100 mg, 267 μmol) and (S)-2-methyl-4-(3-methylpiperazin-1-yl)pyrimidine 2,2,2-trifluoroacetate (77 mg, 400 μmol) were reacted according to Example 536 to give the title compound 649 (70 mg, 47%) as a white solid. LCMS: $[M+1]^+$=549.40. $^1$H NMR (400 MHz, Chloroform-d) δ 8.15 (d, J=6.4 hz, 1H), 6.33 (d, J=6.4 hz, 1H), 5.35 (d, J=5.2 hz, 1H), 4.54-4.10 (m, 2H), 3.71 (d, J=14.0 hz, 1H), 3.57-3.39 (m, 1H), 3.28 (s, 1H), 3.04 (bs, 1H), 2.52 (s, 3H), 2.47-2.34 (m, 1H), 2.31-2.19 (m, 3H), 2.03-1.95 (m, 4H), 1.85-1.77 (m, 4H), 1.64-1.57 (m, 1H), 1.48-1.41 (m, 3H), 1.36 (t, J=4.4 hz, 1H), 1.33 (d, J=3.2 hz, 1H), 1.29 (d, J=6.4 hz, 1H), 1.26

(d, J=5.2 hz, 3H), 1.22-1.18 (m, 1H), 1.17-1.13 (m, 2H), 1.12-1.06 (m, 2H), 1.01 (s, 3H), 0.97 (d, J=6.4 hz, 3H), 0.94-0.88 (m, 1H), 0.69 (s, 3H).

Example 650: (R)-1-((S)-4-(cyclopropanecarbonyl)-3-methylpiperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

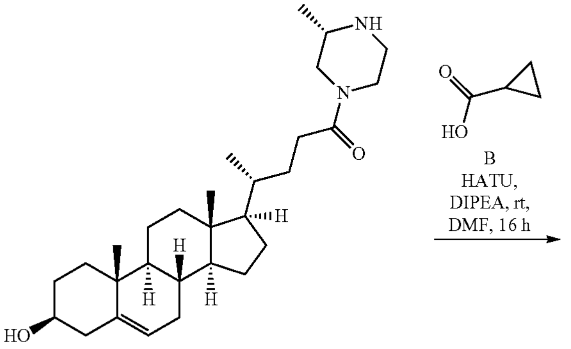

A

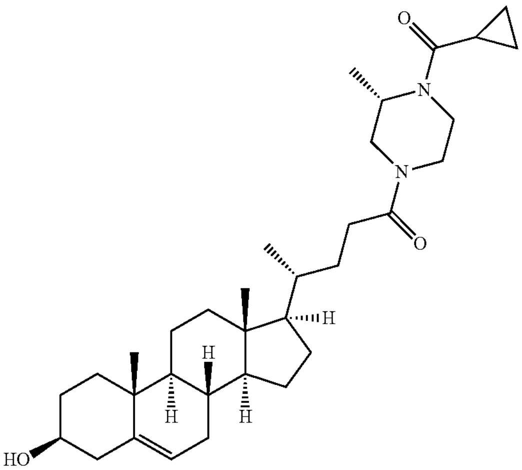

To a solution of compound A (100 mg, 219 μmol), compound B (18.8 mg, 219 μmol) and DIPEA (141 mg, 1.09 mmol) in DMF (2 mL) was added HATU (167 mg, 438 μmol) at room temperature and stirred for 16 h. The reaction was diluted with saturated aqueous $NH_4Cl$ (10 mL) and extracted with EtOAc (5 mL*2). The combined organic layers were washed with water (10 mL), brine (10 mL), dried over sodium sulfate and concentrated under reduced pressure. The residue was purified by silica gel chromatography to give the title compound 650 (50 mg, 43%) as a white solid. LCMS: $[M+1]^+$=525.40. $^1H$ NMR (400 MHz, Methanol-$d_4$) δ 5.35-5.34 (m, 1H), 4.65-4.56 (m, 1H), 4.30 (bs, 2H), 4.03-3.73 (m, 1H), 3.43-3.37 (m, 2H), 3.06-2.93 (m, 2H), 2.52-2.33 (m, 2H), 2.26-2.17 (m, 2H), 2.10-1.72 (m, 8H), 1.67-1.44 (m, 7H), 1.37-1.06 (m, 11H), 1.03-0.99 m, 6H), 0.93-0.81 (m, 4H), 0.74 (s, 3H).

Example 651: (R)-1-((S)-4-(cyclopropanecarbonyl)-2-methylpiperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

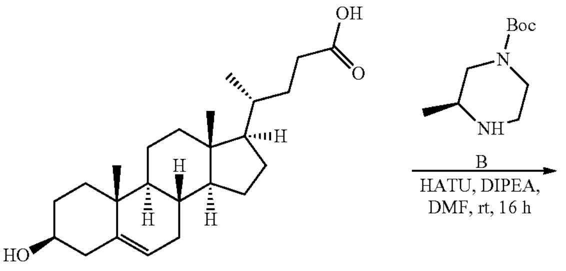

A

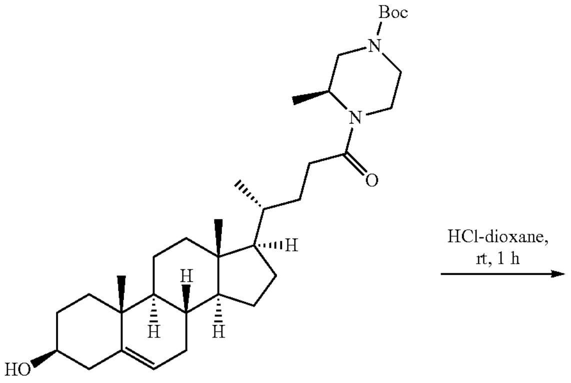

C

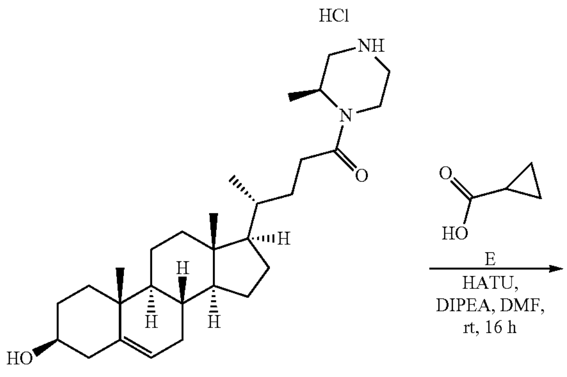

D

-continued

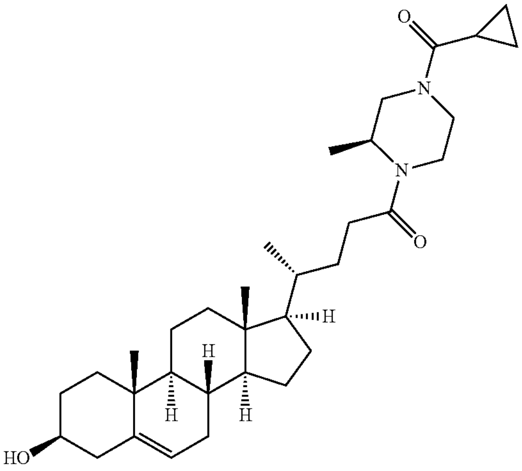

To a solution of compound A (2 g, 5.34 mmol) and compound B (1.6 g, 8.01 mmol) in DMF (20 mL) was added HATU (4.06 mg, 10.7 mmol) and DIPEA (3.45 g, 26.7 mmol). The reaction was stirred at room temperature for 16 hours. Upon completion, the reaction was quenched with saturated aqueous ammonium chloride (50 mL) and extracted with ethyl acetate (50 mL*3). The combined organic layers were washed with brine, dried over sodium sulfate, filtered, and concentrated under reduced pressure. The crude product was purified by silica gel chromatography to afford compound C (2.3 g, 77.36%) as a white solid.

4N hydrogen chloride in 1,4-dioxane (10 mL) was added slowly to the compound C (2.3 g, 4.13 mmol) in a flask at room temperature and stirred for 1 hour. Upon completion, the reaction was added dichloromethane (15 mL) and concentrated under reduced pressure three times to afford compound D (2.03 g) as an HCl salt.

To a solution of compound D (215 mg, 436 μmol) and compound E (37.5 mg, 436 μmol) in DMF (3 mL) was added HATU (332 mg, 872 μmol) and DIPEA (282 mg, 2.18 mmol). The reaction was stirred at room temperature for 3 hours. Upon completion, the reaction was quenched with saturated aqueous ammonium chloride (10 mL) and extracted with ethyl acetate (10 mL*3). The combined organic layers were washed with brine, dried over sodium sulfate, filtered, and concentrated under reduced pressure. The crude product was purified by silica gel chromatography to give the title compound 651 (50.5 mg, 21.97%) as a white solid. LCMS: $[M+1]^+$=525.50. $^1H$ NMR (400 MHz, Chloroform-d) δ 5.35 (d, J=5.2 hz, 1H), 4.23-4.15 (m, 3H), 3.67-3.47 (m, 2H), 3.36 (d, J=18.4 hz, 1H), 2.96 (bs, 1H), 2.79-2.19 (m, 5H), 2.04-1.80 (m, 6H), 1.57 (d, J=8.4 hz, 2H), 1.54-1.40 (m, 6H), 1.36-1.25 (m, 4H), 1.21-1.06 (m, 6H), 1.04 (d, J=4.8 hz, 1H), 1.01 (s, 3H), 0.96-0.89 (m, 4H), 0.80 (d, J=7.6 hz, 2H), 0.69 (s, 3H).

Example 652: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3 S)-4-(2-hydroxy-2-methylpropanoyl)-3-methylpiperazin-1-yl]pentan-1-one

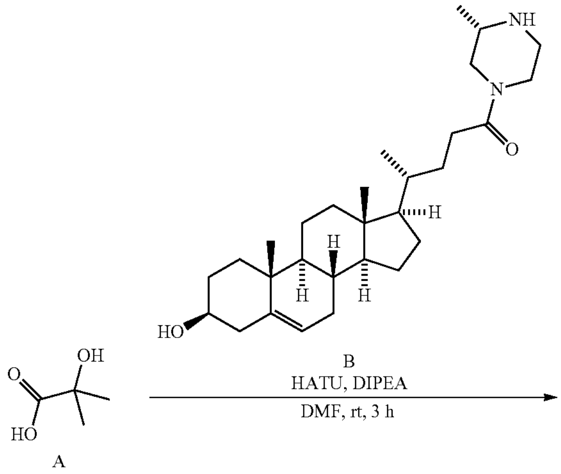

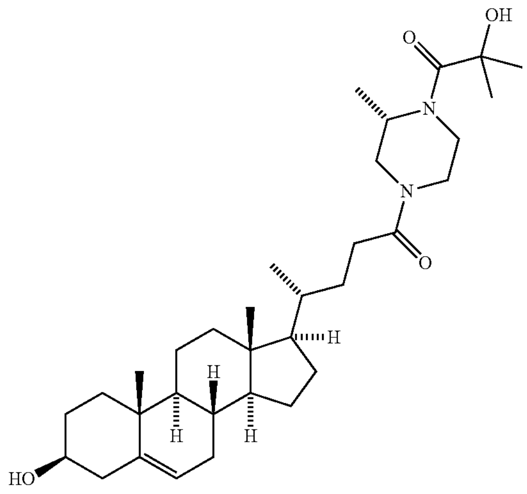

To a room temperature solution of compound A (100 mg, 961 μmol), compound B (351 mg, 768 μmol) and DIPEA (745 mg, 5.76 mmol) in DMF (5 mL) was added HATU (730 mg, 1.92 mmol) and stirred for 16 h under $N_2$. The reaction was diluted with saturated aqueous $NH_4Cl$ (30 mL) and extracted with EtOAc (10 mL*2). The combined organic layers were washed with saturated $NaHCO_3$ (20 mL), water (20 mL), brine (20 mL), dried over sodium sulfate and concentrated under reduced pressure. The residue was purified by silica gel chromatography to give the title compound 652 (271 mg, 64.8%) as a white solid. LCMS: $[M+1]^+$=543.40. $^1H$ NMR (400 MHz, DMSO-$d_6$) δ 5.42 (s, 1H), 5.26 (d, J=4.8 hz, 1H), 4.77-4.42 (m, 2H), 4.40-4.00 (m, 1H), 3.92-3.54 (m, 1H), 3.24 (dt, J=11.2, 6.0 hz, 2H), 3.17 (d, J=5.2 hz, 1H), 2.77-2.30 (m, 2H), 2.11 (p, J=12.4 Hz, 2H), 1.93 (t, J=17.6 hz, 2H), 1.76 (d, J=13.2 hz, 2H), 1.65 (bs, 2H), 1.58-1.45 (m, 3H), 1.39 (d, J=8.4 hz, 3H), 1.30-1.22 (m, 7H), 1.19-0.86 (m, 16H), 0.65 (s, 3H).

Example 653: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-4-(2-hydroxy-2-methylpropanoyl)-2-methylpiperazin-1-yl)pentan-1-one

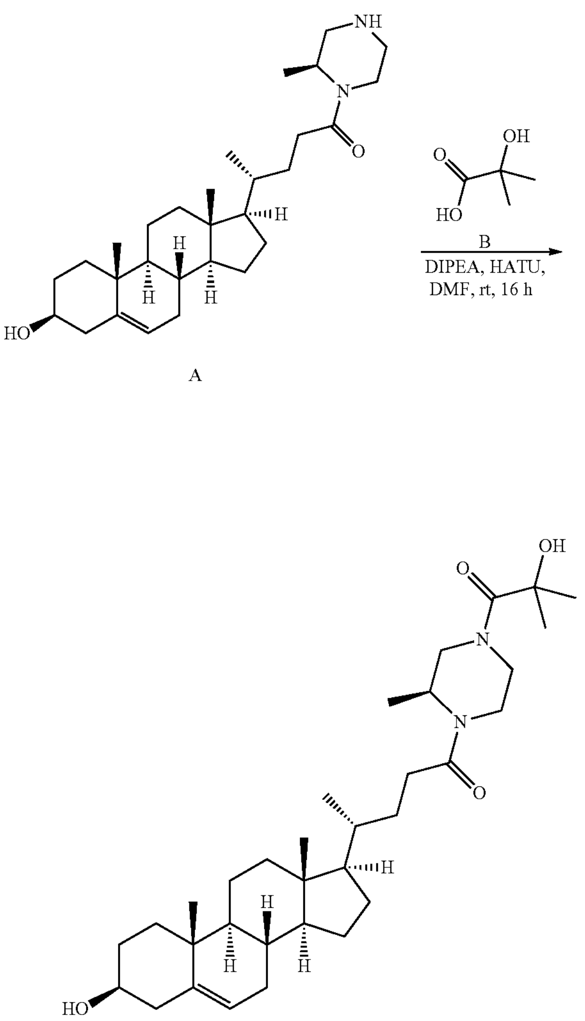

To a room temperature solution of compound A (0.1 g, 219 μmol), compound B (20.5 mg, 197 μmol) and DIPEA (978 mg, 2.19 mmol) in DMF (2 mL) was added HATU (125 mg, 328 μmol) and stirred for 16 h under $N_2$. The reaction was diluted with saturated aqueous $NH_4Cl$ (30 mL) and extracted with EtOAc (10 mL*2). The combined organic layers were washed with saturated $NaHCO_3$ (20 mL), water (20 mL), brine (20 mL), dried over sodium sulfate and concentrated under reduced pressure. The residue was purified by silica gel chromatography to give the title compound 653 (68 mg, 57%) as a white solid. LCMS: $[M+H]^+$=543.40. $^1$H NMR (400 MHz, Chloroform-d) δ 5.35 (d, J=5.2 hz, 1H), 4.83 (bs, 0.5H), 4.52-4.30 (m, 2H), 4.12 (bs, 0.5H), 3.66 (bs, 0.5H), 3.61-3.45 (m, 1H), 3.37 (bs, 0.5H), 3.02 (s, 2H), 2.52-2.11 (m, 5H), 2.07-1.92 (m, 2H), 1.94-1.74 (m, 4H), 1.71-1.40 (m, 15H), 1.25-1.21 (m, 5H), 1.20-1.05 (m, 5H), 1.01 (s, 3H), 0.96-0.89 (m, 4H), 0.69 (s, 3H).

Example 654: (4R)-4-[(1R,3aS,3bS,7S,9aR,9bS,11aR)-7-hydroxy-9a,11a-dimethyl-1H,2H,3H,3aH,3bH,4H,6H,7H,8H,9H,9aH,9bH,10H,11H,11aH-cyclopenta[a]phenanthren-1-yl]-1-[(3 S)-3-methyl-4-(pyrrolidine-1-carbonyl)piperazin-1-yl]pentan-1-one

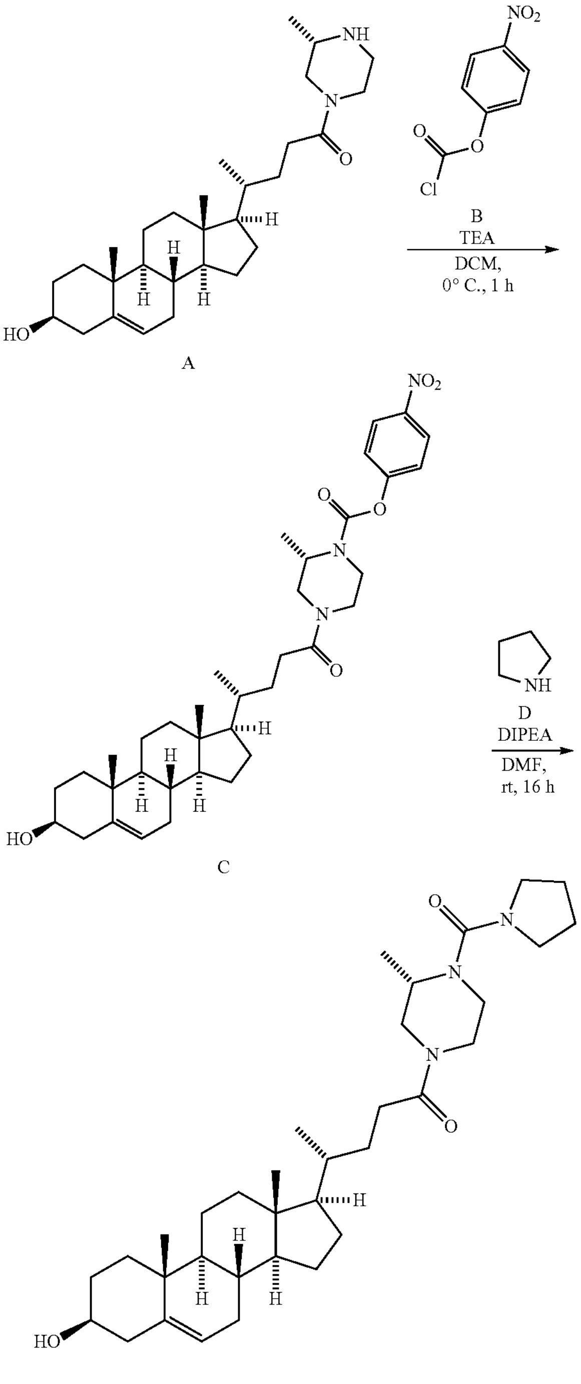

To a solution of compound A (200 mg, 438 mot) and TEA (66.5 mg, 657 mot) in DMF (5 mL) was added compound B (70.6 mg, 350 mot) at 0° C. under $N_2$ and stirred for 1 h. The reaction was diluted with saturated aqueous $NH_4Cl$ (30 mL) and extracted with EtOAc (10 mL*2). The combined organic layers were washed with saturated $NaHCO_3$ (20 mL), water (20 mL), brine (20 mL), dried over sodium sulfate and concentrated under reduced pressure. The residue was purified by silica gel chromatography to afford compound C (100 mg, 36%) as a white solid.

To a room temperature solution of compound C (100 mg, 161 mot) and compound D (11.4 mg, 161 mot) in DMF (5 mL) was added DIPEA (62.4 mg, 482 mot) and stirred for 16 h under $N_2$.

The reaction was diluted with saturated aqueous $NH_4Cl$ (30 mL) and extracted with EtOAc (10 mL*2). The combined organic layers were washed with saturated $NaHCO_3$ (20 mL), water (20 mL), brine (20 mL), dried over sodium sulfate and concentrated under reduced pressure. The residue was purified by silica gel chromatography to give the title compound 654 (30 mg, 33%) as a white solid. LCMS: $[M+1]^+$=554.40. $^1$H NMR (400 MHz, Chloroform-d) δ 5.34 (d, J=4.8 hz, 1H), 4.10-4.01 (m, 1H), 3.93 (d, J=7.2 hz, 1H), 3.60-3.41 (m, 3H), 3.36-3.30 (m, 4H), 3.17-3.04 (m, 1H), 2.91 (dd, J=13.2, 3.6 hz, 1H), 2.76 (d, J=3.6 hz, 1H), 2.44-2.15 (m, 4H), 1.98-2.01 (m, 2H), 1.89-1.77 (m, 8H), 1.67 (s, 2H), 1.58-1.42 (m, 6H), 1.37-1.27 (m, 3H), 1.22 (d, J=6.8 hz, 2H), 1.16 (d, J=6.8 hz, 2H), 1.13-1.03 (m, 3H), 1.00 (s, 3H), 0.94-0.88 (m, 4H), 0.68 (s, 3H).

Example 655: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-2-methyl-4-(pyrrolidine-1-carbonyl)piperazin-1-yl)pentan-1-one

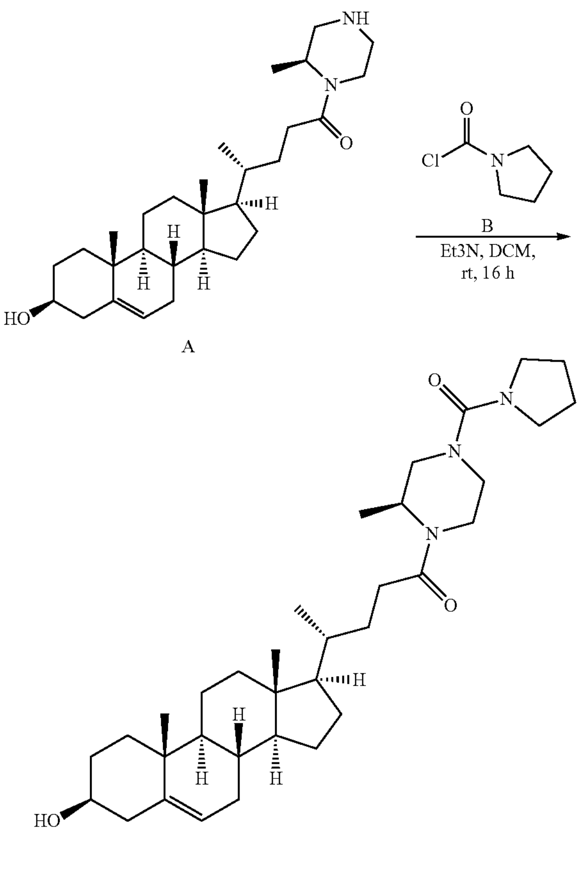

To a 0° C. solution of compound A (100 mg, 219 μmol) and $Et_3N$ (111 mg, 1.09 mmol) in DCM (2 mL) was added compound B (26.3 mg, 197 μmol) and the reaction was warmed to room temperature for 16 h. The reaction was concentrated under reduced pressure and the residue was purified by silica gel chromatography to give the title compound 655 (91.9 mg, 76%) as a white solid. LCMS: $[M+1]^+$=554.40. $^1$H NMR (400 MHz, Chloroform-d) δ 5.35 (d, J=5.2 hz, 1H), 4.77 (s, 0.5H), 4.40 (d, J=13.4 hz, 0.5H), 4.06 (s, 0.5H), 3.75 (d, J=12.8 hz, 0.5H), 3.64-3.29 (m, 8H), 3.10-2.92 (m, 1H), 2.87-2.74 (m, 1H), 2.37-2.14 (m, 4H), 2.05-1.93 (m, 3H), 1.84-1.76 (m, 8 h), 1.55-1.38 (m, 5H), 1.26-1.05 (m, 12H), 1.00 (s, 3H), 0.95-0.87 (m, 4H), 0.68 (s, 3H).

Example 656: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-((S)-3-methyl-4-(1-methyl-1H-pyrazol-4-yl)piperazin-1-yl)pentan-1-one

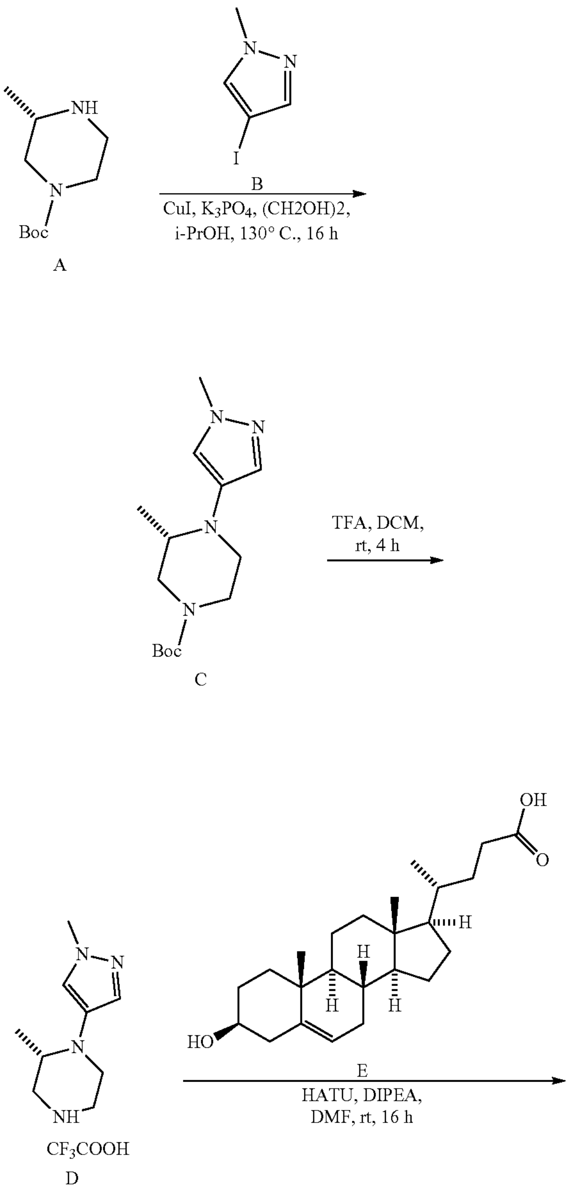

-continued

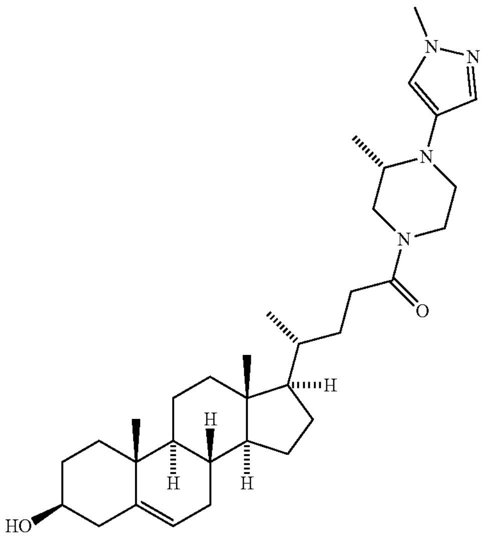

To a solution of compound A (100 mg, 499 μmol) in isopropanol (3 mL) was added compound B (208 mg, 999 μmol), CuI (19 mg, 99.9 μmol), $K_3PO_4$ (424 mg, 2 mmol) and ethane-1,2-diol (31 mg, 499 μmol). The reaction was stirred at 130° C. for 16 hours under $N_2$. The reaction was diluted with water (30 mL) and extracted with EtOAc (20 mL*2). The combined organic layers were washed with brine (30 mL), dried over sodium sulfate and concentrated under reduced pressure. The residue was purified by silica gel chromatography to afford compound C (50 mg, 36%) as off-white solid.

To a solution of compound C (50 mg, 178 μmol) in dichloromethane (3 mL) was added TFA (1 mL). The reaction was stirred at room temperature under $N_2$ for 3 hours. The reaction was concentrated under reduced pressure to afford compound D as the TFA salt (50 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (104 mg, 277 μmol) and (S)-2-methyl-1-(1-methyl-1H-pyrazol-4-yl)piperazine 2,2,2-trifluoroacetate (50 mg, 170 μmol) were reacted according to the method of Example 353 to give the title compound 656 (41 mg, 28%.) as off white solid. LCMS: $[M+1]^+$=537.50. $^1H$ NMR (400 MHz, Chloroform-d) δ 7.22 (d, J=4.0 hz, 1H), 7.01 (d, J=8.0 hz, 1H), 5.35 (d, J=5.2 hz, 1H), 3.84 (s, 3H), 3.78 (bs, 1H), 3.68-3.47 (m, 3H), 3.16-2.79 (m, 3H), 2.49-2.14 (m, 4H), 2.04-1.74 (m, 6H), 1.54-1.40 (m, 6H), 1.39-1.24 (m, 4H), 1.22-1.05 (m, 4H), 1.05-0.98 (m, 5H), 0.98-0.84 (m, 6H), 0.69 (s, 3H).

Example 657: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(4-methoxypyridin-2-yl)piperazin-1-yl)pentan-1-one

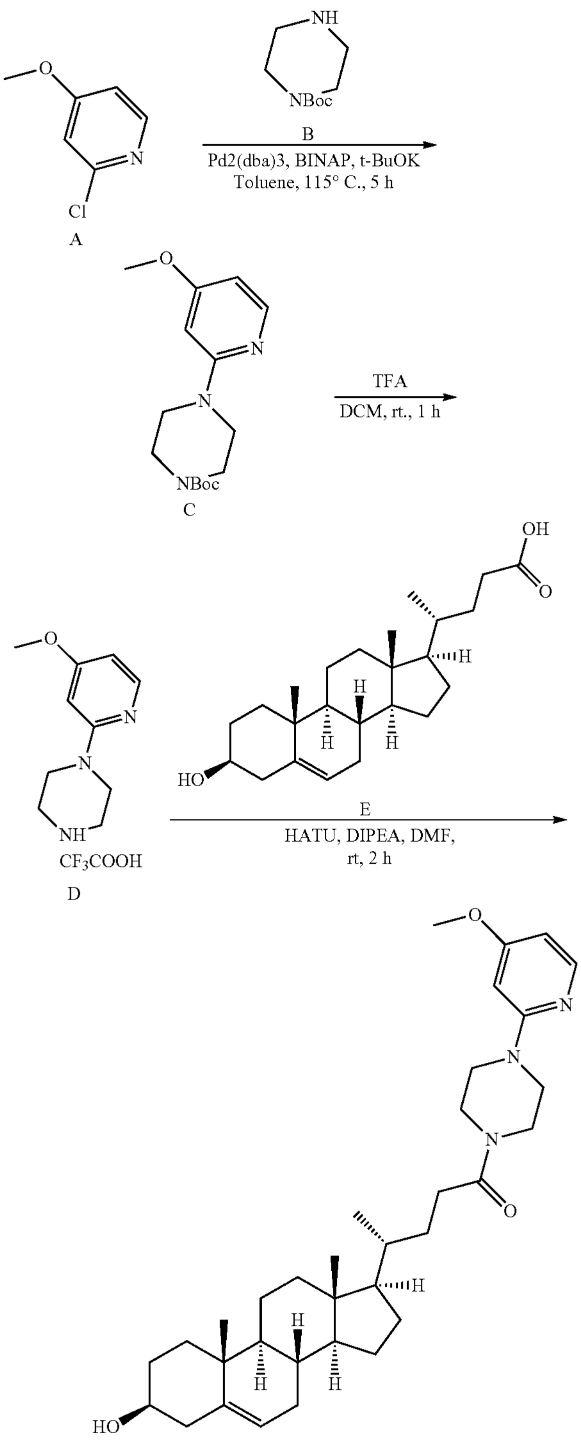

A solution of compound A (200 mg, 1.39 mmol), compound B (778 mg, 4.18 mmol) and t-BuOK (469 mg, 4.18 mmol) in toluene (12 mL) was heated to 80° C. under $N_2$. $Pd_2(dba)_3$ (15.3 mg, 16.7 μmol) and BINAP (23.4 mg, 37.6

μmol) were added into the reaction and stirred at 115° C. under $N_2$ for 3 h. Water (10 mL) was added to the reaction and extracted with EtOAc (30 mL). The organic layer was washed with brine (10 mL), dried over sodium sulfate and concentrated under reduced pressure. The crude was purified by silica gel chromatography to afford compound C (320 mg, 78.1%) as yellow oil.

To a solution of compound C (120 mg, 409 μmol) in DCM (1 mL) was added TFA (0.3 mL). The reaction was stirred at room temperature for 2 h. The reaction was concentrated under reduced pressure to afford compound D as the TFA salt (118 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (100 mg, 404 μmol) and 1-(4-methoxypyridin-2-yl)piperazine TFA salt (118 mg, 402 μmol) were reacted according to the method of Example 353 to give the title compound 657 (100 mg, 68.1%) as a white solid. LCMS: $[M+1]^+$=550.50. $^1$HNMR (400 MHz, Chloroform-d) δ 8.04 (d, J=5.6 hz, 1H), 6.29 (dd, J=5.6, 2.0 hz, 1H), 6.10 (d, J=2.0 hz, 1H), 5.35 (d, J=5.2 hz, 1H), 3.82 (s, 3H), 3.74 (t, J=5.2 hz, 2H), 3.60-3.45 (m, 4H), 3.48-3.40 (m, 3H), 2.42 (ddd, J=15.6, 11.0, 5.2 hz, 1H), 2.33-2.18 (m, 3H), 2.05-1.74 (m, 7H), 1.59-1.27 (m, 12H), 1.21-1.02 (m, 5H), 1.01 (s, 3H), 0.97-0.87 (m, 4H), 0.94-0.86 (m, 1H), 0.69 (s, 3H).

Example 658: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(4-methylpyridin-2-yl)piperazin-1-yl)pentan-1-one

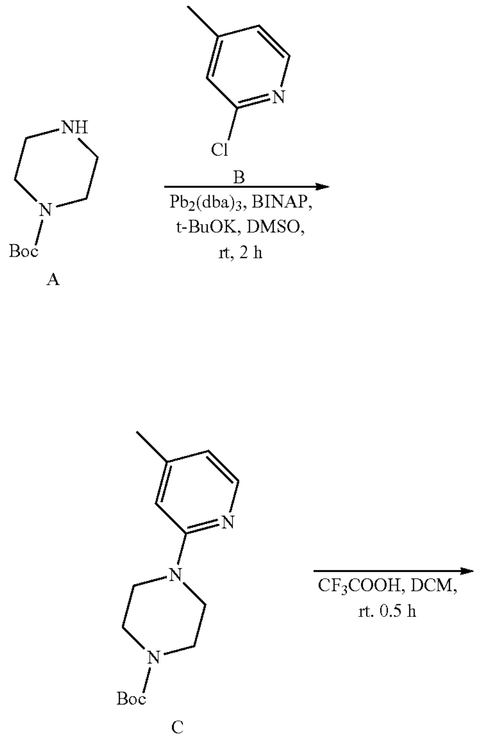

-continued

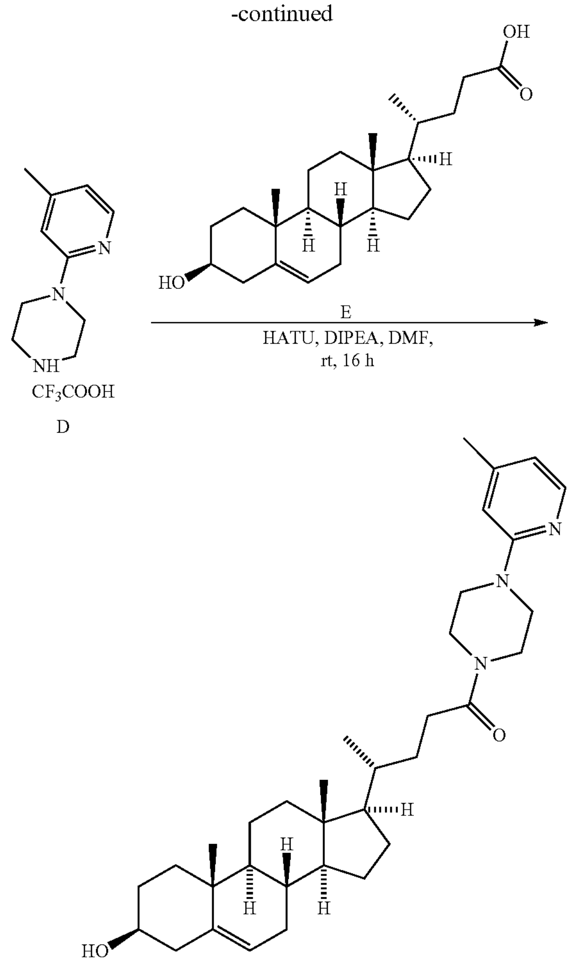

To a solution of compound A (300 mg, 1.61 mmol) in DMSO (6 mL) was added compound B (240 mg, 1.88 mmol), $Pb_2(dba)_3$ (85 mg, 0.07 mmol), BINAP (90 mg, 0.14 mmol) and t-BuOK (460 mg, 4.10 mmol). The reaction was heated to 100° C. under $N_2$ for 2 h. The reaction was cooled to room temperature and diluted with water (60 mL) and extracted with EtOAc (60 mL*2). The combined organic layers were washed with water (60 mL), dried over sodium sulfate and concentrated under reduced pressure. The residue was purified by silica gel chromatography to afford compound C (60 mg, 14.37%) as a white solid.

To a solution of compound C (60 mg, 0.22 mmol) in DCM (2 mL) was added TFA (0.5 mL) at room temperature and the reaction was stirred for 2 h. The reaction was concentrated under reduced pressure to afford compound D as the TFA salt (70 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (60 mg, 0.16 mmol) and 1-(4-methylpyridin-2-yl)piperazine 2,2,2-trifluoroacetate (70 mg, 0.22 mmol) were reacted according to the method of Example 353 to give the title compound 658 (48.5 mg, 46.01%) as a white solid. LCMS: $[M+1]^+$=534.50. $^1$H NMR (400 MHz, Chloroform-d) δ 8.05 (d, J=5.2 hz, 1H), 6.53 (d, J=5.2 hz, 1H), 6.50 (s, 1H), 5.35 (d, J=5.2 hz, 1H), 3.78-3.72 (m, 2H), 3.67-3.57 (m, 4H), 3.55-3.40 (m, 3H), 2.42 (ddd, J=15.6, 11.2, 5.2 hz, 1H), 2.29 (s, 3H), 2.21 (d, J=11.6 hz, 1H), 2.03-1.94 (m, 2H), 1.92-

1.75 (m, 4H), 1.62-1.55 (m, 2H), 1.54-1.43 (m, 6H), 1.40-1.25 (m, 4H), 1.01 (s, 3H), 0.97 (d, J=6.4 hz, 3H), 0.94-0.87 (m, 1H), 0.69 (s, 3H).

Example 659: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(6-methoxypyridin-2-yl)piperazin-1-yl)pentan-1-one

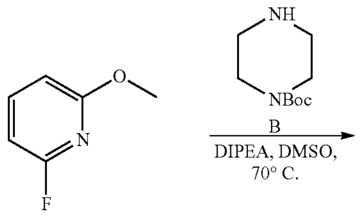

A

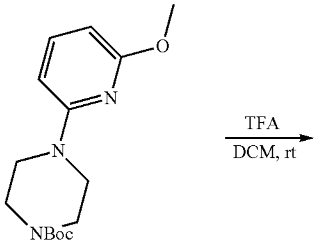

C

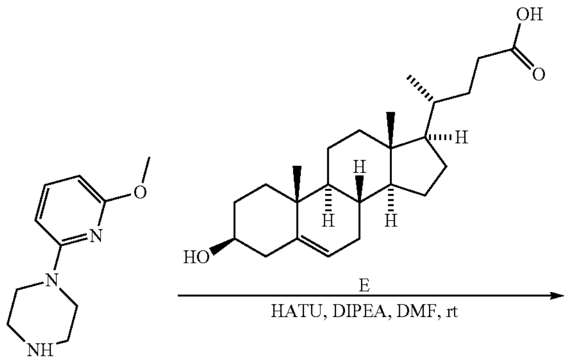

TFA
D

-continued

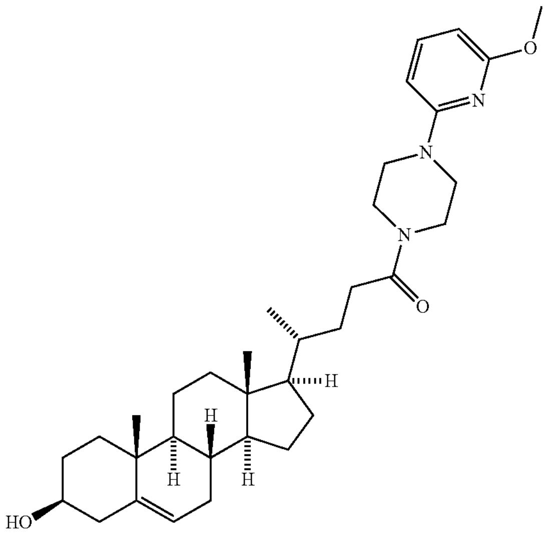

To a room temperature solution of compound A (200 mg, 1.57 mmol) under nitrogen was added compound B (322 mg, 1.73 mmol) in DMSO (10 mL) and DIPEA (244 mg, 1.89 mmol). The reaction was stirred at 70° C. for 16 h. The reaction was diluted with water (30 mL) and extracted with EtOAc (20 mL*2). The combined organic layers were washed with water (50 mL), brine (20 mL), dried over sodium sulfate and concentrated under reduced pressure. The residue was purified by silica gel chromatography to afford compound C (47 mg, 10%) as yellow oil.

To a solution of compound C (47 mg, 160 μmol) in DCM (2 mL) was added TFA (1 mL) at room temperature and the reaction was stirred for 2 h. The reaction was concentrated under reduced pressure to afford compound D as the TFA salt (49.0 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (53.6 mg, 143 μmol) and 2,2,2-trifluoroacetaldehyde compound with 1-(6-methoxypyridin-2-yl)piperazine TFA salt (49 mg, 160 μmol) were reacted according to the method of Example 353 to give the title compound 659 (60 mg, 61%) as a white solid. LCMS: $[M+1]^+$=550.40. $^1H$ NMR (400 MHz, $CDCl_3$) δ 7.42 (t, J=8.0 hz, 1H), 6.21-6.07 (m, 2H), 5.42-5.30 (m, 1H), 3.87 (s, 3H), 3.73 (t, J=4.8 hz, 2H), 3.59-3.52 (m, 4H), 3.53-3.43 (m, 4H), 2.49-2.38 (m, 1H), 2.34-2.17 (m, 3H), 2.06-1.92 (m, 2H), 1.94-1.75 (m, 4H), 1.57-1.39 (m, 9H), 1.43-1.27 (m, 4H), 1.26-1.01 (m, 10H), 1.01 (s, 4H), 1.00-0.81 (m, 5H), 0.69 (s, 3H).

Example 660: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(5-methoxypyridin-3-yl)piperazin-1-yl)pentan-1-one

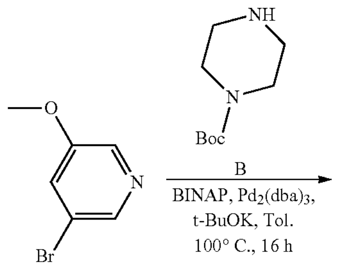

A

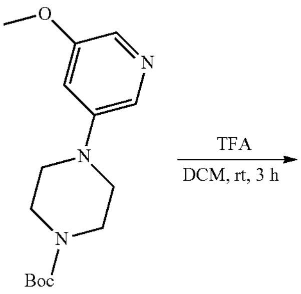

C

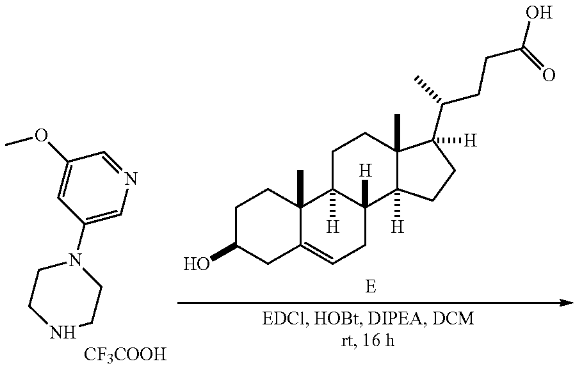

D

-continued

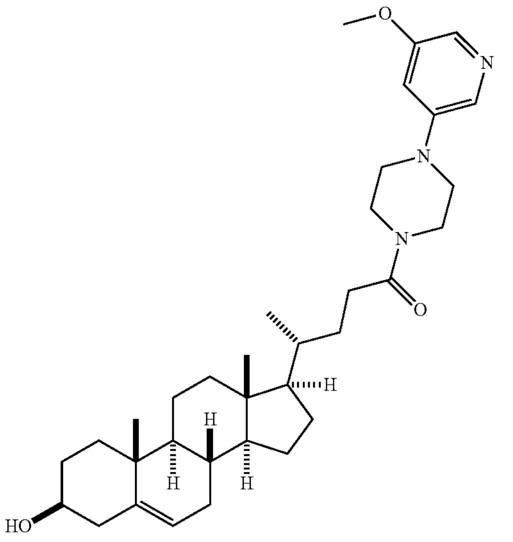

To a solution of compound A (500 mg, 2.66 mmol) in toluene (20 mL), was added compound B (594 mg, 3.19 mmol), $Pd_2(dba)_3$ (122 mg, 133 μmol), BINAP (166 mg, 266 μmol) and t-BuOK (597 mg, 5.32 mmol). The reaction was stirred at 100° C. for 16 h. The reaction was quenched with water (50 mL) and extracted with EtOAc (150 mL). The organic layers were washed by brine (100 mL), dried over sodium sulfate, filtered, and concentrated under reduced pressure. The residue was purified by silica gel chromatography to afford compound C (500 mg, 64%) as a yellow solid.

To a solution of compound C (110 mg, 375 μmol) in Dichloromethane (5 mL) was added TFA (1 mL). The reaction was stirred at room temperature for 3 h. The reaction was concentrated under reduced pressure to afford compound D (150 mg) as the TFA salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (109 mg, 290 μmol) and 1-(5-methoxypyridin-3-yl)piperazine 2,2,2-trifluoroacetate (150 mg, 375 μmol) were reacted according to the method of Example 353 to give the title compound 660 (97.0 mg, 49%) as a white solid. LCMS: [M+1]=550.60 [M+1]. $^1H$ NMR (400 MHz, $CDCl_3$): 7.96 (d, J=2.4 hz, 1H), 7.86 (d, J=2.4 hz, 1H), 6.70 (t, J=2.4 hz, 1H), 5.35 (d, J=5.2 hz, 1H), 3.85 (s, 3H), 3.78 (t, J=5.2 hz, 2H), 3.64 (t, J=5.2 hz, 2H), 3.52 (d, J=5.2 hz, 1H), 3.20 (dt, J=17.2, 5.2 hz, 4H), 2.42 (ddd, J=15.6, 11.2, 5.2 hz, 1H), 2.26-1.77 (m, 9H), 1.58-1.43 (m, 7H), 1.42-1.24 (m, 3H), 1.22-1.02 (m, 5H), 1.01 (s, 3H), 0.98-0.86 (m, 4H), 0.69 (s, 3H).

Example 661: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(5-methylpyridin-3-yl)piperazin-1-yl)pentan-1-one

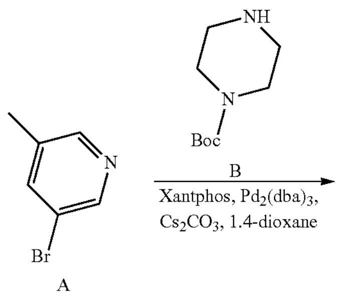

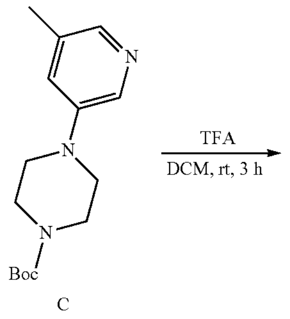

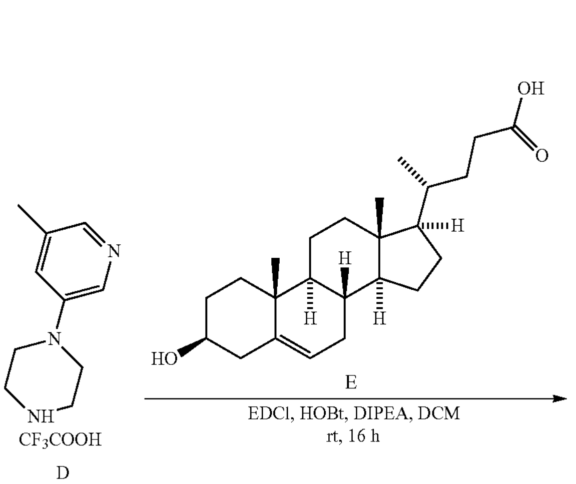

-continued

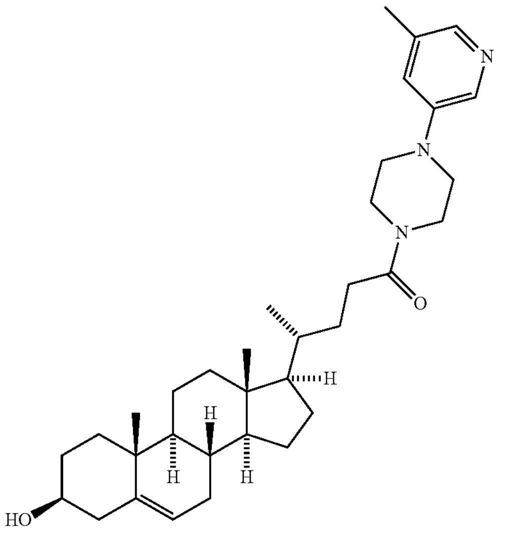

To a solution of compound A (500 mg, 2.91 mmol) in 1,4-dioxane (20 mL) was added compound B (704 mg, 3.78 mmol), $Pd_2(dba)_3$ (133 mg, 145 μmol), Xantphos (168 mg, 291 μmol) and $Cs_2CO_3$ (1.89 g, 5.81 mmol). The reaction was stirred at 110° C. for 16 h. The reaction was quenched with water (50 mL) and extracted with EtOAc (150 mL). The organic layer was washed by brine (100 mL), dried over sodium sulfate, filtered, and concentrated under reduced pressure. The residue was purified by silica gel chromatography to afford compound C (540 mg, 67%) as a yellow solid.

To a solution of compound C (140 mg, 505 μmol) in Dichloromethane (5 mL) was added TFA (1 mL). The reaction was stirred at room temperature for 3 h. The reaction was concentrated under reduced pressure to afford compound D as the TFA salt (180 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (228 mg, 609 μmol) and 1-(5-methylpyridin-3-yl)piperazine 2,2,2-trifluoroacetate (180 mg, 505 μmol) were reacted according to the method of Example 353 give the title compound 661 (188.0 mg, 70%) as a white solid. LCMS: [M+1]=534.50. $^1$H NMR (400 MHz, $CDCl_3$): 8.11 (d, J=2.8 hz, 1H), 7.98 (d, J=1.6 hz, 1H), 7.00 (t, J=2.0 hz, 1H), 5.34 (d, J=5.2 hz, 1H), 3.77 (t, J=5.2 hz, 2H), 3.63 (t, J=5.2 hz, 2H), 3.56-3.46 (m, 1H), 3.17-3.10 (m, 4H), 2.39 (dd, J=10.8, 4.8 hz, 1H), 2.31-2.21 (m, 6H), 2.05-1.75 (m, 9H), 1.63-1.52 (m, 2H), 1.45 (dd, J=11.2, 4.4 hz, 2H), 1.41-1.24 (m, 3H), 1.10-1.00 (m, 4H), 0.96 (d, J=6.4 hz, 3H), 0.94-0.88 (m, 1H), 0.68 (s, 3H).

Example 662: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(6-methoxypyrazin-2-yl)piperazin-1-yl)pentan-1-one

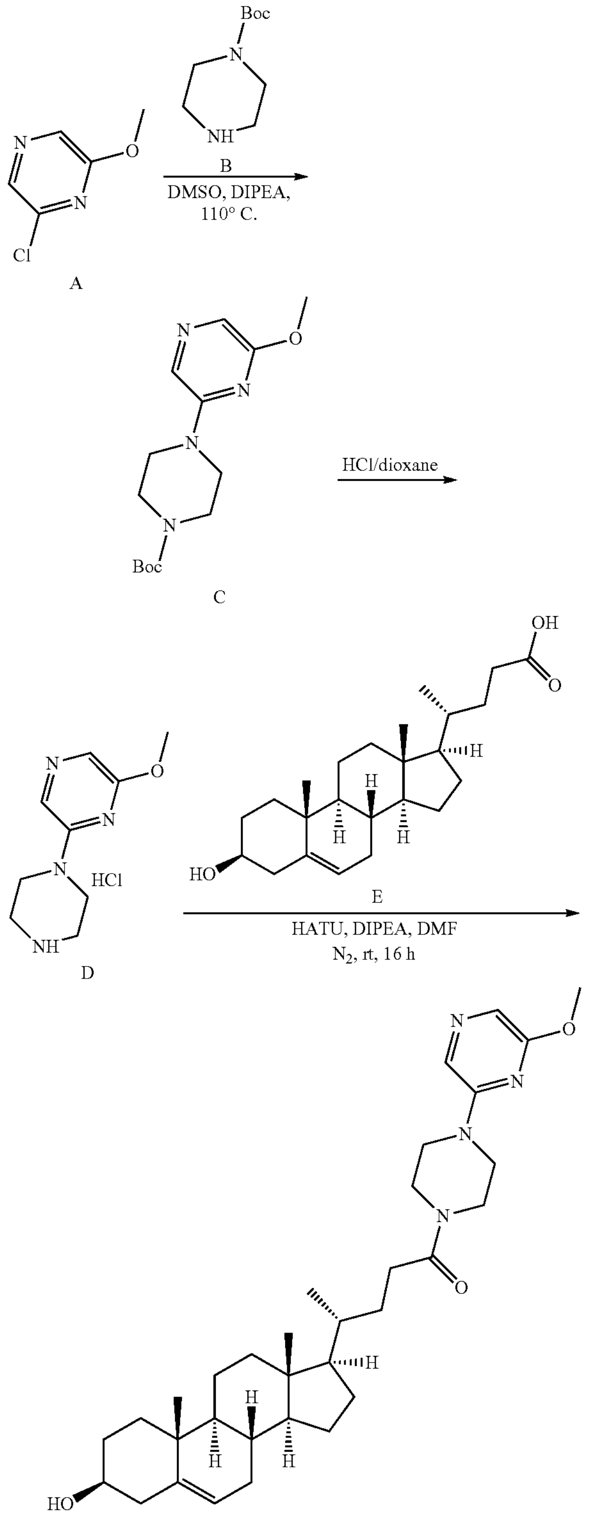

To a solution of compound A (0.5 g, 3.46 mmol) in DMSO (10 mL) was added compound B (644 mg, 3.46 mmol) and DIPEA (536 mg, 4.15 mmol). The reaction was stirred at 110° C. under $N_2$ for 16 h. The reaction was quenched with water (20 mL) and extracted with EtOAc (50 mL). The organic layer was washed with brine (10 mL), dried over sodium sulfate, filtered, and concentrated. The residue was purified by silica gel chromatography to afford the compound C (630 mg, 61.76%) as a white solid.

To a solution of compound C (300 mg, 1.02 mmol) in DCM (10 mL) was added 4NhCl/dioxane (1 mL) The reaction was stirred at room temperature for 1 h. The reaction was concentrated to afford compound D (235 mg) as an HCl salt.

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (154 mg, 412 μmol) and 2-methoxy-6-(piperazin-1-yl)pyrazinehydrochloride (100 mg, 515 μmol) were reacted according to the method of Example 353 to give the title compound 662 (102 mg, 36%) as a white solid. LCMS: $[M+1]^+$=551.40. $^1$H NMR (400 MHz, Chloroform-d) δ 7.64 (s, 1H), 7.58 (s, 1H), 5.35 (d, J=5.2 hz, 1H), 3.90 (s, 3H), 3.75 (bs, 2H), 3.61-3.48 (m, 7H), 2.50-2.39 (m, 1H), 2.27-2.15 (m, 3H), 2.05-1.77 (m, 7H), 1.55-1.28 (m, 11H), 1.22-1.03 (m, 5H), 1.03-0.88 (m, 8H), 0.69 (s, 3H).

Example 663: (R)-1-(4-(6-(dimethylamino)pyrimidin-4-yl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

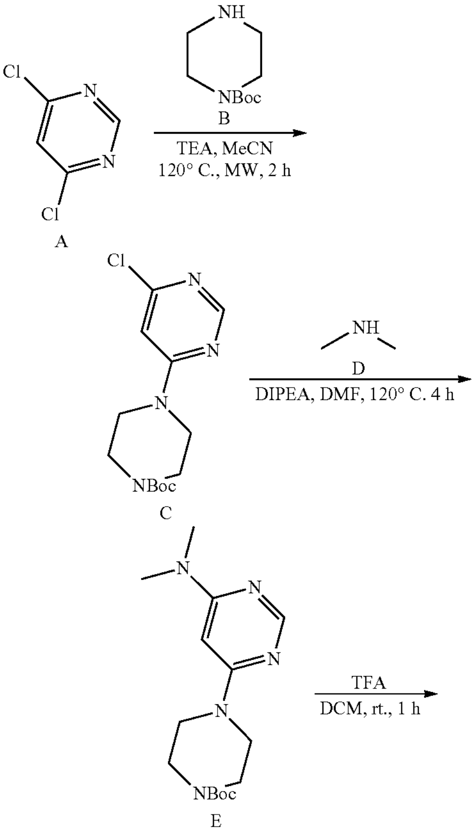

-continued

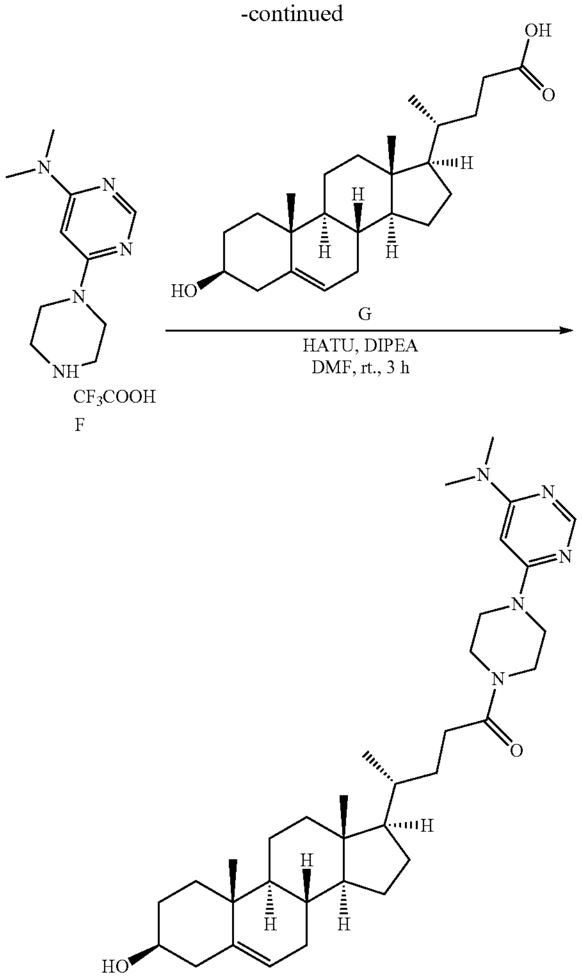

To a solution of compound A (200 mg, 1.34 mmol) in acetonitrile (4 mL) was added compound B (250 mg, 1.34 mmol) and triethylamine (401 mg, 2.69 mmol). The reaction was heated in a microwave vial at 120° C. for 2 h. Water (15 mL) was added to the reaction and extracted with EtOAc (50 mL). The organic phase was washed with brine (10 mL), dried over sodium sulfate, and concentrated under reduced pressure. The crude was purified by silica gel chromatography to afford compound C (310 mg, 76.5%) as yellow oil.

To a solution of compound C (150 mg, 502 μmol) in DMF (3 mL) was added compound D (67.9 mg, 1.51 mmol) and DIEPA (324 mg, 2.51 mmol). The reaction was stirred at 120° C. for 4 h. Water (10 mL) was added to the reaction and extracted with EtOAc (20 mL). The organic layer was washed with brine (5 mL), dried over sodium sulfate, and concentrated under reduced pressure. The crude was purified by silica gel chromatography to afford compound E (100 mg, 64.7%) as yellow oil.

To a solution of compound E (100 mg, 325 μmol) in DCM (1 mL) was added TFA (0.3 mL). The reaction was stirred at room temperature for 1 h. The reaction was concentrated under reduced pressure to afford compound F as the TFA salt (57.6 mg).

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (80 mg, 404 μmol) and 1N,N-dimethyl-6-(piperazin-1-yl)pyrimidin-4-amine 2,2,2-trifluoroacetate (57.6 mg, 178 μmol) were combined according to the method of Example 353 to give the title compound 663 (100 mg, 66.4%) as a white solid. LCMS: $[M+1]^+=564.50$. $^1$HNMR (400 MHz, Chloroform-d) δ 8.24 (s, 1H), 5.45 (s, 1H), 5.35 (d, J=5.2 hz, 1H), 3.71 (s, 4H), 3.53-3.07 (m, 11H), 2.41-2.18 (m, 5H), 2.04-1.75 (m, 7H), 1.58-1.25 (m, 12H), 1.24-1.02 (m, 5H), 1.01 (s, 3H), 0.96 (d, J=6.4 hz, 3H), 0.94-0.86 (m, 1H), 0.69 (s, 3H).

Example 664: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-(3-methylazetidine-1-carbonyl)piperazin-1-yl)pentan-1-one

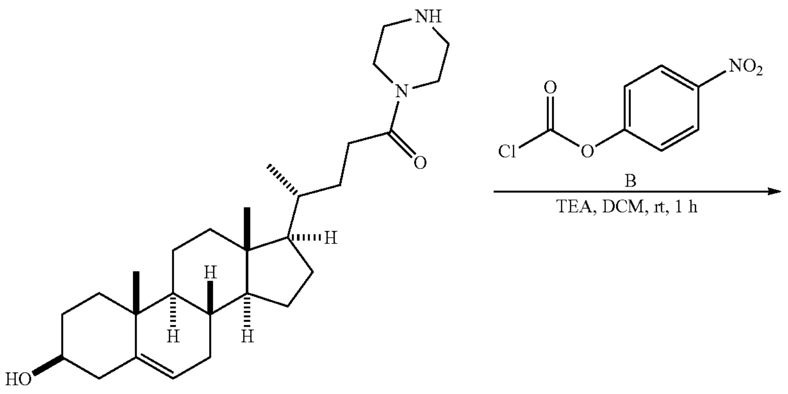

A

-continued

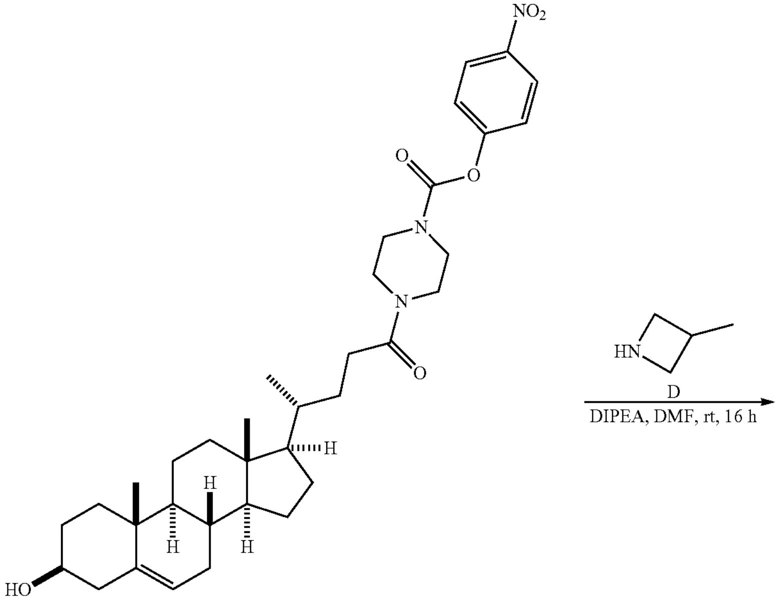

C

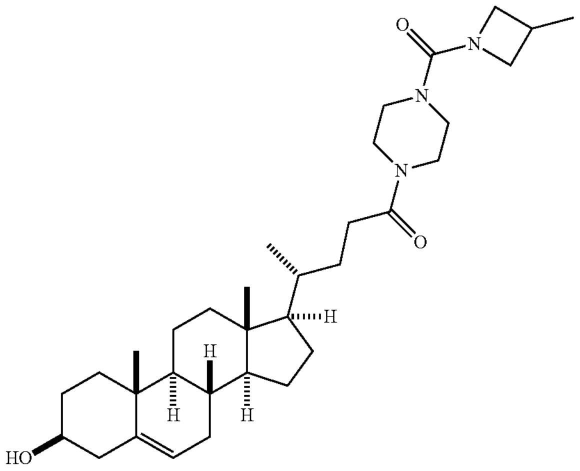

To a solution of compound A (200 mg, 452 umol) in dichloromethane (5 mL) was added compound B (91.1 mg, 452 umol) and TEA (68.6 mg, 678 μmol). The reaction was stirred at room temperature for 1 h. The reaction was quenched with water (20 mL) and extracted with EtOAc (60 mL). The organic layer was washed by brine (50 mL), dried over sodium sulfate, filtered, and concentrated under reduced pressure. The residue was purified by silica gel chromatography to afford compound C (200 mg, 73%) as a yellow solid.

To a solution of compound C (100 mg, 165 μmol) in DMF (2 mL) was added compound D (14 mg, 197 μmol) and DIPEA (63.8 mg, 494 μmol). The reaction was stirred at room temperature for 16 h. The reaction was quenched with water (20 mL) and extracted with EtOAc (60 mL). The organic layer was washed by brine (50 mL), dried over sodium sulfate, filtered, and concentrated under reduced pressure. The residue was purified by silica gel chromatography to give the title compound 664 (40.3 mg, 45%) as a light yellow solid. LCMS: [M+1]=540.45. $^1$H NMR (400 MHz, $CDCl_3$): δ 5.35 (d, J=5.2 hz, 1H), 4.10 (t, J=8.4 hz, 2H), 3.57-3.53 (m, 4H), 3.51 (dd, J=11.2, 6.4 hz, 1H), 3.44-3.37 (m, 4H), 3.27 (t, J=5.2 hz, 2H), 2.67 (h, J=7.2 hz, 1H), 2.44-2.16 (m, 4H), 2.05-1.72 (m, 6H), 1.60-1.39 (m, 8H), 1.38-1.25 (m, 3H), 1.23 (d, J=6.8 hz, 3H), 1.20-1.02 (m, 4H), 1.00 (s, 3H), 0.97-0.86 (m, 4H), 0.68 (s, 3H).

Example 665: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-((S)-2-methylazetidine-1-carbonyl)piperazin-1-yl)pentan-1-one

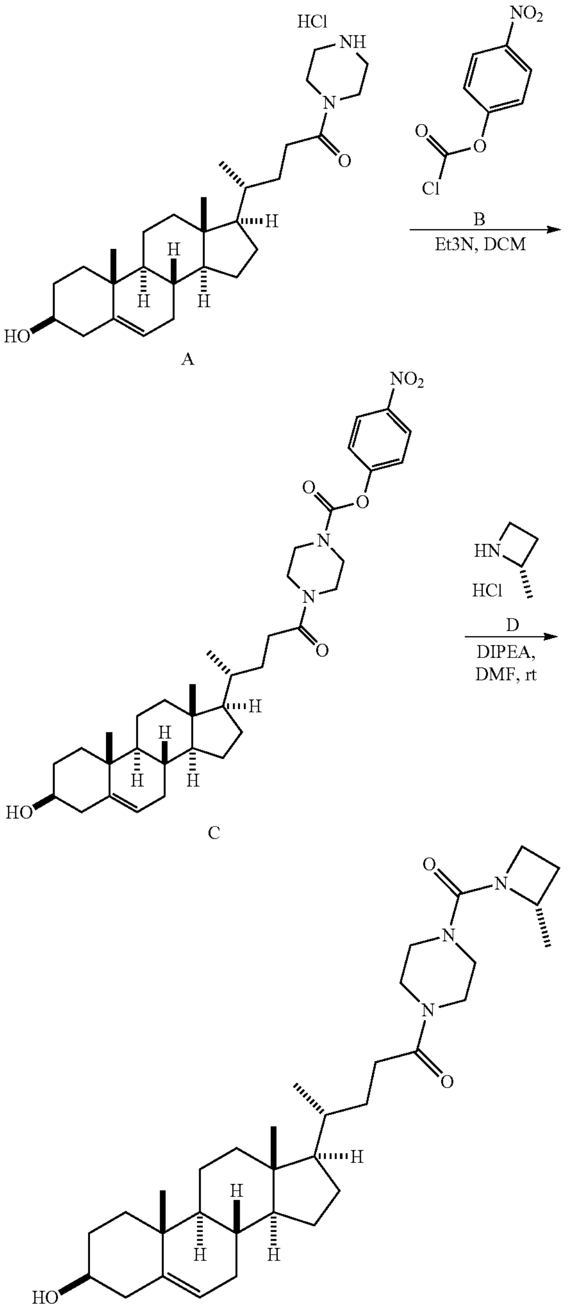

To a 0° C. solution of compound A (3.0 g, 6.26 mmol) and TEA (1.9 g, 18.8 mmol) in DCM (50 mL) was added compound B (1.26 g, 6.26 mmol) under $N_2$. The reaction stirred at room temperature for 1 h. The reaction was quenched with water (200 mL) and extracted with DCM (100 mL*2). The combined organic layers were washed by brine, dried over sodium sulfate, filtered, and concentrated. The residue was purified by silica gel chromatography to afford compound C (3.5 g, 92%) as a white solid.

To a 0° C. solution of compound C (200 mg, 329 μmol) and DIPEA (128 mg, 987 μmol) in DMF (10 mL) was added compound D (42.5 mg, 395 μmol) under $N_2$. The reaction was heated to 50° C. for 16 h. The reaction was quenched with water (20 mL) and extracted with EtOAc (10 mL*3). The combined organic layers were washed by brine (10 mL), dried over sodium sulfate, filtered, and concentrated. The residue was purified by silica gel chromatography to give the title compound 665 (15 mg, 8%) as a white solid. LCMS: $[M+1]^+$=540.45. $^1H$ NMR (400 MHz, $CDCl_3$) δ 5.39-5.30 (m, 1H), 4.53-4.40 (m, 1H), 4.06-3.94 (m, 1H), 3.80-3.68 (m, 1H), 3.68-3.37 (m, 6H), 3.37-3.18 (m, 3H), 2.43-2.17 (m, 5H), 2.06-1.92 (m, 2H), 1.91-1.71 (m, 5H), 1.60-1.39 (m, 7H), 1.39-1.27 (m, 6H), 1.21-1.02 (m, 5H), 1.00 (s, 3H), 0.95 (d, J=6.4 hz, 3H), 0.92-0.79 (m, 1H), 0.68 (s, 3H).

Example 666: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-((S)-2-methylpyrrolidine-1-carbonyl)piperazin-1-yl)pentan-1-one

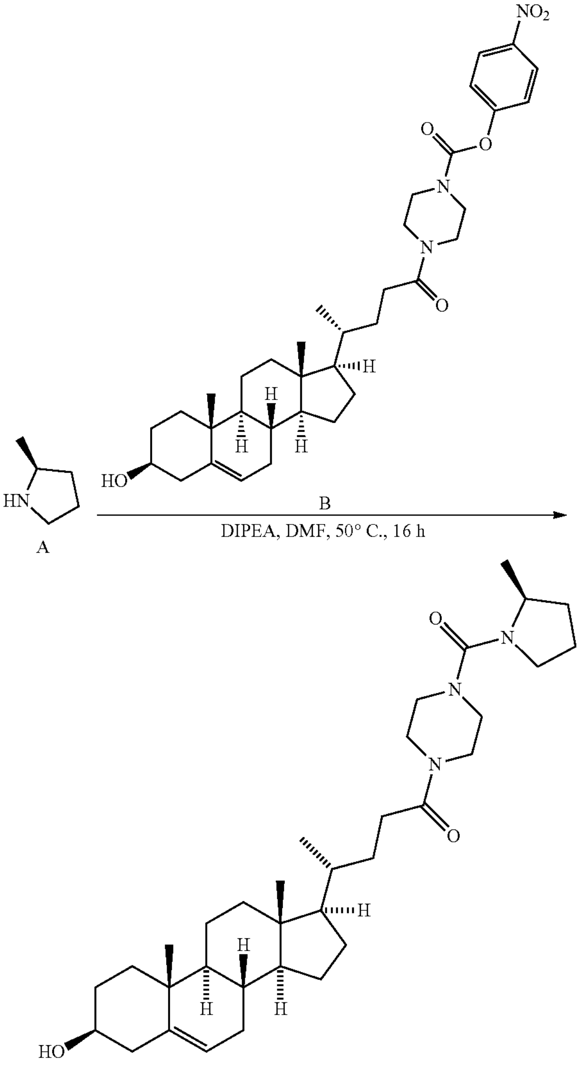

To a solution of compound A (300 mg, 494 μmol) in DMF (6 mL) was added compound B (14 mg, 197 μmol) and DIPEA (84.1 mg, 987 μmol). The reaction was heated to 50° C. for 16 h. The reaction was quenched with water (30 mL) and extracted with EtOAc (120 mL). The organic layer was washed by brine (100 mL), dried over sodium sulfate, filtered, and concentrated under reduced pressure.

The residue was purified by silica gel chromatography to give the title compound 666 (98.1 mg, 36%) as a light yellow solid. LCMS: [M+1]=554.40. $^1$H NMR (400 MHz, $CDCl_3$): δ 5.34 (dt, J=5.6, 2.0 hz, 1H), 4.03-3.97 (m, 1H), 3.64-3.46 (m, 4H), 3.42-3.29 (m, 4H), 3.19-3.15 (m, 2H), 2.43-2.19 (m, 4H), 2.09 (dq, J=10.4, 4.4 hz, 1H), 2.04-1.93 (m, 2H), 1.85-1.73 (m, 6H), 1.61-1.42 (m, 8H), 1.41-1.24 (m, 4H), 1.18 (d, J=6.0 hz, 3H), 1.16-1.02 (m, 4H), 1.00 (s, 3H), 0.97-0.82 (m, 5H), 0.68 (s, 3H).

Example 667: (R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)-1-(4-((R)-3-methylpyrrolidine-1-carbonyl)piperazin-1-yl)pentan-1-one

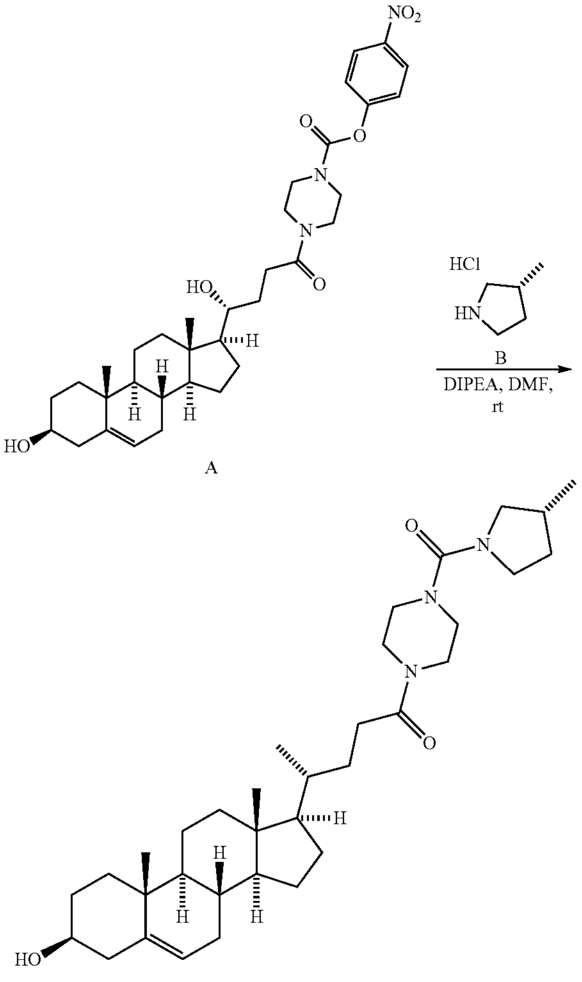

To a solution of compound A (200 mg, 329 μmol) and DIPEA (128 mg, 987 μmol) in DMF (10 mL) was added compound B (48.0 mg, 395 μmol) at 0° C. under $N_2$. The reaction stirred at 50° C. for 16 h. The reaction was quenched with water (20 mL) and extracted with EtOAc (10 mL*3). The combined organic layers were washed by brine (10 mL), dried over sodium sulfate, filtered, and concentrated. The residue was purified by silica gel chromatography to give the title compound 667 (20.0 mg, 11%) as a white solid. LCMS: $[M+1]^+$=554.45. $^1$H NMR (400 MHz, Chloroform-d) δ 5.38-5.32 (m, 1H), 3.61 (t, J=5.2 hz, 2H), 3.57-3.39 (m, 6H), 3.36-3.15 (m, 4H), 3.01-2.92 (m, 1H), 2.43-2.33 (m, 1H), 2.33-2.14 (m, 5H), 2.04-1.93 (m, 3H), 1.92-1.72 (m, 4H), 1.58-1.39 (m, 8H), 1.39-1.28 (m, 3H), 1.22-1.09 (m, 3H), 1.06-1.02 (m, 4H), 1.00 (s, 3H), 0.95 (d, J=6.4 hz, 3H), 0.92-0.81 (m, 1H), 0.68 (s, 3H).

CIS AB Examples (C #)

Example C1: (R)-4-((3S,5S,6R,8S,9S,10R,13R,14S,17R)-3,6-dihydroxy-10,13-dimethylhexadecahydro-1H-cyclopenta[a]phenanthren-17-yl)-N,N-dimethyl-pentanamide

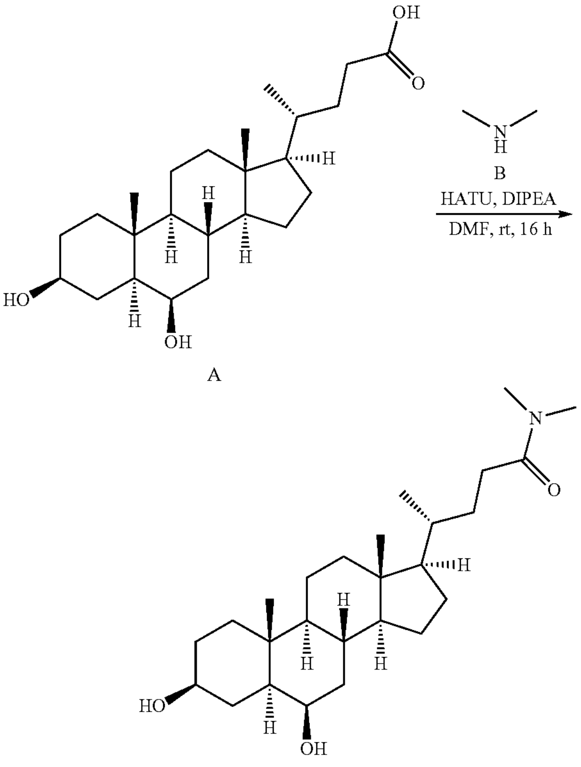

C1

To a solution of compound A (100 mg, 255 μmol) in DMF (3 mL) were added HATU (242 mg, 637 μmol), DIEA (165 mg, 1.27 mmol), and compound B (28.7 mg, 637 μmol) at room temperature. The mixture was stirred for 16 h. After completion, the reaction was quenched by the addition of water and extracted with ethyl acetate. The organic layer was washed by brine, dried over sodium sulfate, filtered, and concentrated to afford the crude product that was purified by column chromatography to give the title compound C1 (11.7 mg, 11%) as a white solid. H NMR (400 MHz, $CDCl_3$) δ 4.09 (t, J=3.0 Hz, 1H), 3.70 (d, J=3.2 Hz, 1H), 2.98 (s, 6H), 2.45-2.32 (m, 1H), 2.24 (q, J=14.5, 11.5 Hz, 1H), 1.99 (dd, J=12.4, 3.8 Hz, 1H), 1.95-1.19 (m, 29H), 1.14 (s, 3H), 1.13-1.01 (m, 3H), 0.95 (d, J=6.5 Hz, 3H), 0.69 (s, 3H).

Example C2: (R)-4-((3S,5S,6R,8S,9S,10R,13R,14S,17R)-3,6-dihydroxy-10,13-dimethylhexadecahydro-1H-cyclopenta[a]phenanthren-17-yl)-1-(4-methylpiperidin-1-yl)pentan-1-one

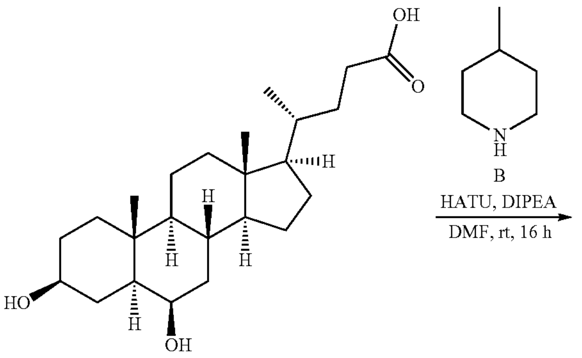

A

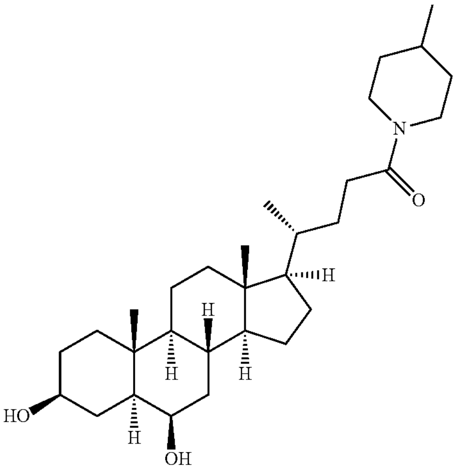

C2

To a solution of compound A (100 mg, 255 μmol) in DMF (5 mL) were added HATU (194 mg, 509 μmol), DIEA (132 mg, 1.02 mmol), and compound B (50.5 mg, 509 μmol) at room temperature. The mixture was stirred for 16 h. After completion, the solution was quenched by the addition of water and extracted with ethyl acetate. The organic layer was washed by brine, dried over sodium sulfate, filtered, and concentrated to afford the crude product that was purified by column chromatography to give the title compound C2 (18.8 mg, 16%) as a white solid. $^1$H NMR (400 MHz, $CDCl_3$) δ 4.56 (s, 1H), 4.09 (t, J=3.0 Hz, 1H), 3.80 (s, 1H), 3.70 (q, J=2.8 Hz, 1H), 3.00 (d, J=17.0 Hz, 1H), 2.51 (d, J=16.5 Hz, 1H), 2.37 (ddd, J=15.7, 11.1, 5.0 Hz, 1H), 2.21 (ddd, J=14.8, 10.7, 5.3 Hz, 1H), 1.99 (dd, J=12.8, 3.6 Hz, 1H), 1.94-1.22 (m, 31H), 1.19-1.04 (m, 9H), 0.95 (dd, J=6.5, 2.3 Hz, 6H), 0.69 (s, 3H). LCMS: $[M+H]^+$=474.30.

Trans-AB Examples (T #)

Example T1: (4R)-4-[(1R,3aS,3bS,5aS,7R,9S,9aS,9bS,11aR)-7,9-dihydroxy-9a,11a-dimethyl-hexadecahydro-1H-cyclopenta[a]phenanthren-1-yl]-N,N-dimethylpentanamide

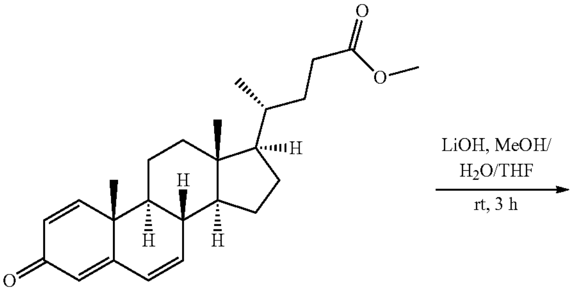

A

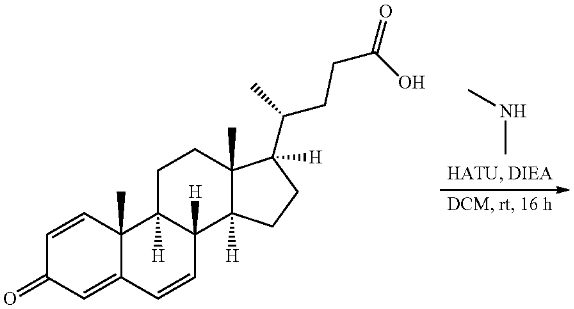

B

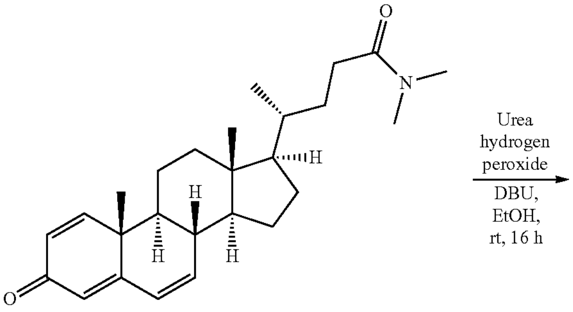

C

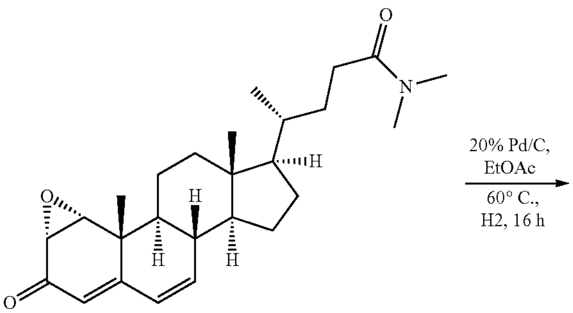

D

-continued

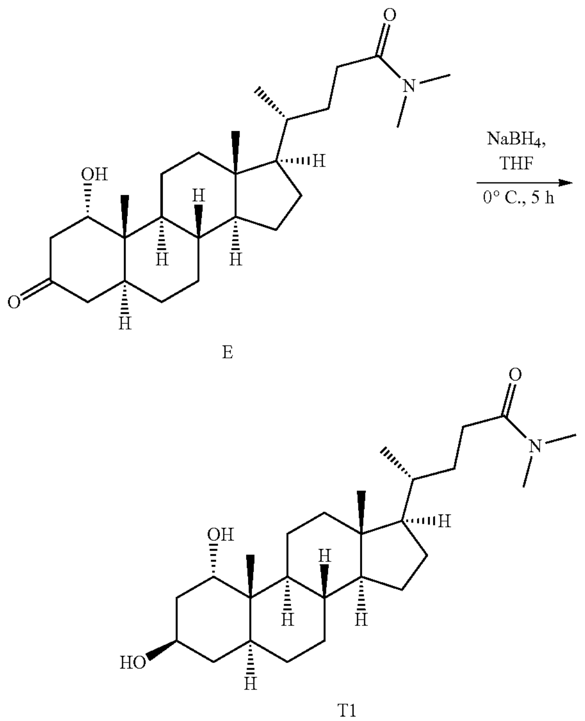

E

T1

To a solution of compound A (6.0 g, 15.7 mmol) in THE (18 mL), methanol (18 mL) and water (18 mL) was added LiOH (3.01 g, 4 eq, 71.6 mmol) at room temperature. The mixture was stirred for 3 h. After completion, the mixture was adjusted to pH 2-3 with 1N HCl and filtered. The filter cake was washed with water and dried under vacuum to give compound B (5.4 g, 93%).

To a solution of compound B (2.0 g, 5.43 mmol) in DCM (8 mL) were added HATU (4.13 g, 2 eq, 10.9 mmol), dimethylamine (489 mg, 2 eq, 10.9 mmol), and DIEA (2.81 g, 4 eq, 21.7 mmol). The mixture was stirred at room temperature for 16 h. After completion, the mixture was diluted with water and extracted with ethyl acetate. The organic layer was washed with brine, dried over sodium sulfate, filtered, and concentrated to give the crude product that was purified by column chromatography to yield compound C (1.86 g, 86%).

To a solution of compound C (1.0 g, 2.61 mmol) in ethanol (104 mL) were added DBU (1.15 g, 2.9 eq, 7.58 mmol) and urea hydrogen peroxide (369 mg, 1.5 eq, 3.92 mmol). The mixture was stirred at room temperature for 16 h. After completion, the mixture was quenched with saturated $Na_2SO_3$ solution and extracted with ethyl acetate. The organic layer was washed with brine, dried over sodium sulfate and concentrated to give the crude which was purified by column chromatography to afford compound D (550 mg, 52%).

A solution of compound D (400 mg, 972 μmol) and Pd/C (80 mg, 20% weight) in ethyl acetate was stirred at 60° C. for 16 h under 1 atm of $H_2$. After completion, the mixture was filtered and concentrated. The residue was purified by column chromatography to afford compound E (70 mg, 17%).

To a solution of compound E (70 mg, 168 μmol) in THF (2 mL) at 0° C. was added $NaBH_4$ (1.9 mg, 0.3 eq, 50.3 μmol). The reaction mixture was stirred for 5 h. After completion, the reaction mixture was quenched with methanol/water and extracted with ethyl acetate. The organic layer was concentrated in vacuo and the residue was purified by silica gel chromatograph to afford the title compound T1 (19 mg, 27%). $^1H$ NMR (400 MHz, $CDCl_3$) δ 4.00 (tt, J=11.0, 4.9 Hz, 1H), 3.80 (d, J=3.0 Hz, 1H), 2.96 (d, J=28.6 Hz, 6H), 2.34 (ddd, J=15.7, 11.0, 5.1 Hz, 1H), 2.19 (ddd, J=15.3, 10.6, 5.6 Hz, 1H), 1.96 (dt, J=11.7, 3.5 Hz, 2H), 1.92-1.71 (m, 3H), 1.62 (dq, J=13.8, 2.9 Hz, 6H), 1.44 (ddt, J=12.8, 9.2, 5.2 Hz, 2H), 1.38-1.22 (m, 7H), 1.22-0.98 (m, 5H), 0.96-0.83 (m, 4H), 0.80 (s, 3H), 0.65 (s, 3H).

Example T2: (R)-4-((1S,3R,5S,8S,9S,10S,13R,14S,17R)-1,3-dihydroxy-10,13-dimethylhexadecahydro-1H-cyclopenta[a]phenanthren-17-yl)-N-methoxy-N-methylpentanamide

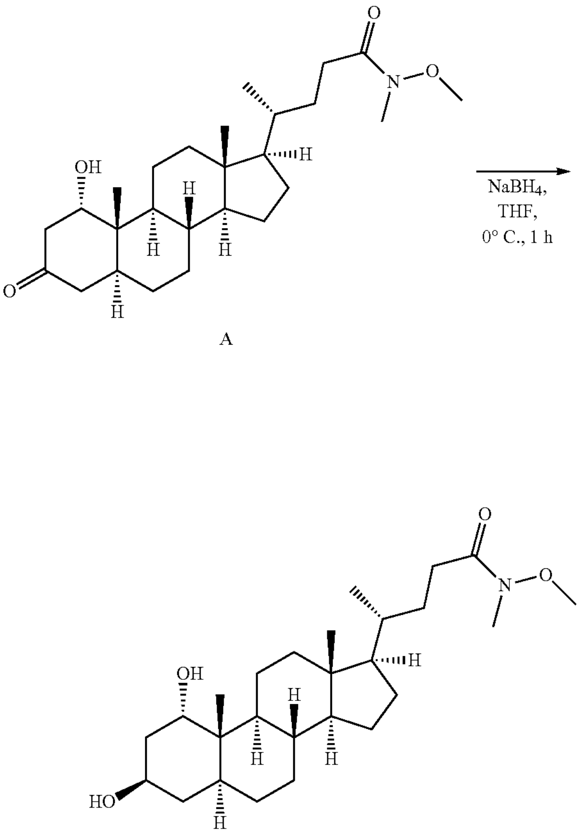

A

T2

To a solution of compound A (70 mg, 161 μmol) in THE (2 mL) was added $NaBH_4$ (1.83 mg, 48.4 μmol) at 0° C. The mixture was stirred at 0° C. for 1 h. After completion, the mixture was quenched with water and extracted with DCM. The organic layer was concentrated to give crude which was purified by column chromatography to afford the title compound T2 (27 mg, 62 μmol). $^1H$ NMR (400 MHz, $CDCl_3$) δ 4.01 (dt, J=11.3, 6.3 Hz, 1H), 3.81 (s, 1H), 3.69 (s, 3H), 3.17 (s, 3H), 2.42 (dd, J=10.6, 5.2 Hz, 1H), 2.37-2.28 (m, 1H), 2.00-1.94 (m, 2H), 1.89-1.75 (m, 2H), 1.66-1.60 (m, 3H), 1.48-1.39 (m, 3H), 1.36-1.30 (m, 6H), 1.25 (s, 3H), 1.21-1.10 (m, 3H), 1.07 (d, J=10.0 Hz, 2H), 0.93 (d, J=6.4 Hz, 3H), 0.81 (s, 3H), 0.66 (s, 3H).

Example T3: (R)-4-((1S,3R,5S,8S,9S,10S,13R,14S,17R)-1,3-dihydroxy-10,13-dimethylhexadecahydro-1H-cyclopenta[a]phenanthren-17-yl)-1-(4-ethyl-4-hydroxypiperidin-1-yl)pentan-1-one

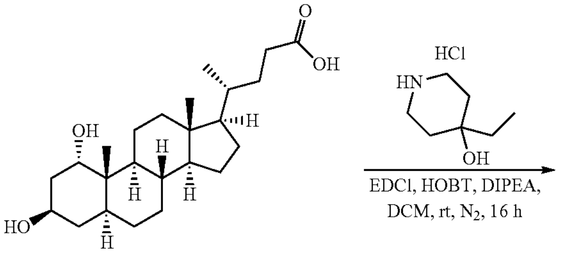

A

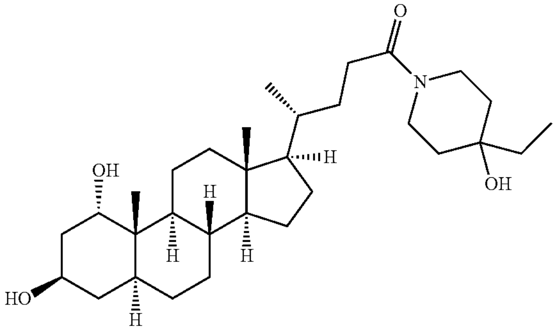

T3

A solution of compound A (20 mg, 50.9 μmol), 4-ethylpiperidin-4-ol hydrochloride (16.9 mg, 2 eq, 102 μmol), ethylbis(propan-2-yl)amine (32.9 mg, 5 eq, 255 μmol), hydrogen N'-[3-(dimethylamino)propyl]propanimidamide chloride (19.7 mg, 2 eq, 102 μmol), and 1H-1,2,3-benzotriazol-1-ol amine (15.5 mg, 2 eq, 102 μmol) in dichloromethane (4 mL) was stirred at room temperature under $N_2$ atmosphere for 16 h. After completion, the mixture was diluted with water (20 mL) and extracted with DCM (30 mL×3). The combined organic layers were washed with brine, dried over sodium sulfate, and concentrated under vacuum to give the crude which was purified by column chromatography (DCM/MeOH=0~10%, v/v) to give the title compound T3 (17 mg, 33.7 μmol, 66%).1H NMR (400 MHz, DMSO-d6) δ 4.21 (dd, J=10.2, 4.7 Hz, 2H), 4.14 (s, 1H), 4.02 (d, J=13.0 Hz, 1H), 3.70 (dt, J=11.2, 5.6 Hz, 1H), 3.55 (d, J=16.6 Hz, 2H), 3.26 (d, J=13.0 Hz, 1H), 2.96-2.82 (m, 1H), 2.29 (dd, J=11.6, 7.0 Hz, 1H), 2.22-2.11 (m, 1H), 1.94-0.93 (m, 33H), 0.88 (d, J=6.4 Hz, 3H), 0.82 (t, J=7.4 Hz, 3H), 0.69 (s, 3H), 0.61 (s, 3H).

Example T4: (R)-4-((3S,5S,6S,8S,9S,10R,13R,14S,17R)-3,6-dihydroxy-10,13-dimethylhexadecahydro-1H-cyclopenta[a]phenanthren-17-yl)-1-(4-ethyl-4-hydroxypiperidin-1-yl)pentan-1-one

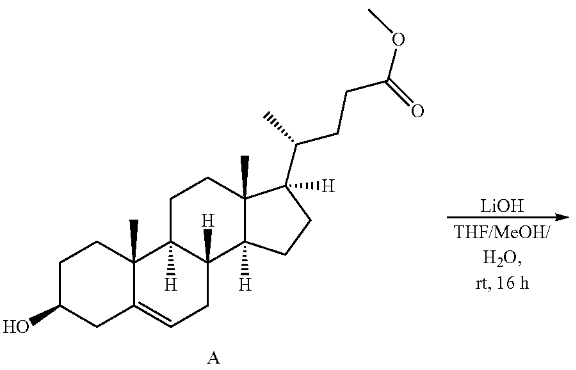

A

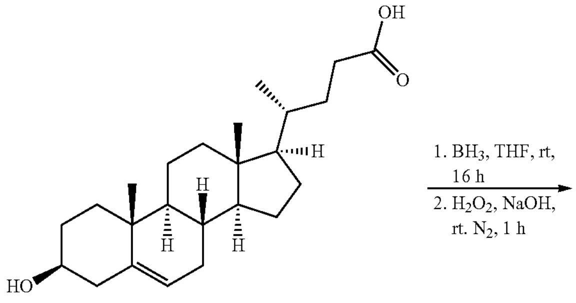

B

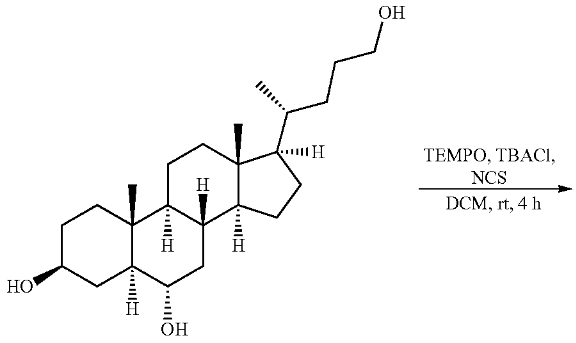

C

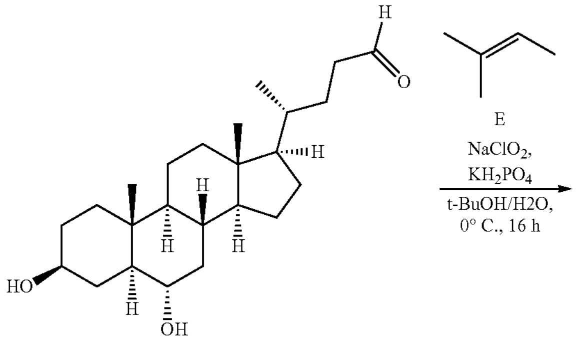

D

-continued

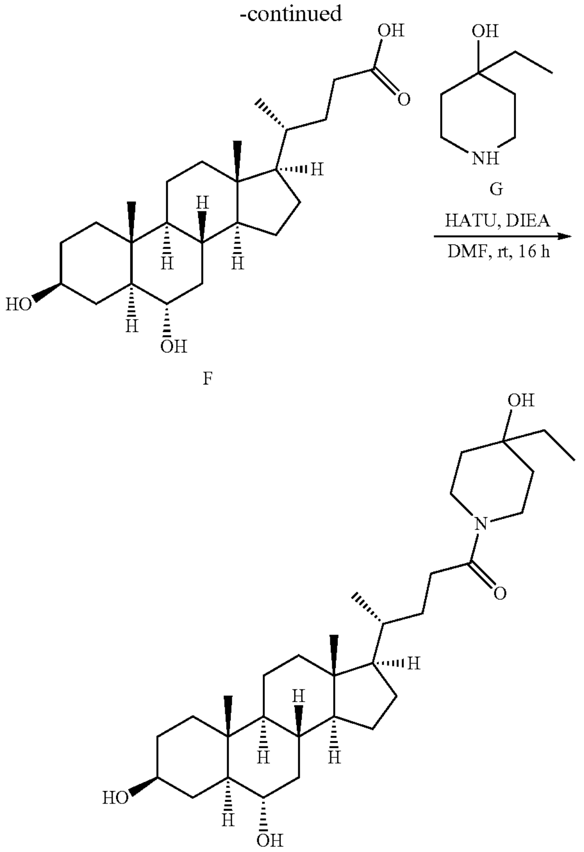

F G T4

To a solution of compound A (16.0 g, 14.1 mmol) in THE (100 mL) and methanol (100 mL) was added the solution of LiOH (1.35 g, 56.3 mmol) in water (100 mL) at room temperature and stirred for 16 h. After completion, the reaction was diluted with water, adjusted to pH 3 with HCl (1M) and extracted with DCM. The organic layer was washed by brine, dried over sodium sulfate, filtered, and concentrated to afford the crude which was purified by column chromatography to give compound B (12.0 g, 76%) as a white solid.

To a solution of compound B (5.0 g, 13.3 mmol) in THE (200 mL) was added $BH_3$ (4.59 g, 53.4 mmol) and it was stirred at 0° C. for 16 h. NaOH (10% w/w) (140 mL) and $H_2O_2$ (42 mL) were added. The mixture was stirred at room temperature for 1 h under $N_2$. After completion, the mixture was extracted with DCM. The combined organic layers were dried over sodium sulfate and concentrated to give the crude product that was purified by column chromatography to give compound C (2.6 g, 51%) as a white solid.

To a solution of compound C (500 mg, 1.32 mmol) were added TEMPO (20.6 mg, 132 μmol), NCS (353 mg, 2.64 mmol), and TBACl (73.4 mg, 264 μmol) in the pH 7 buffer solution (10 mL) and DCM (10 mL) at room temperature. The mixture was stirred for 4 h. After completion, the mixture was extracted with DCM. The combined organic layers were dried over sodium sulfate and concentrated to give the crude that was purified by column chromatography to give compound D (300 mg, 60%) as a white solid.

To a solution of compound D (300 mg, 797 μmol) in tBuOH (4.5 mL) and water (1.5 mL) were added $KH_2PO_4$ (130 mg, 956 μmol), compound E (169 μL, 1.59 mmol), and $NaClO_2$ (86.5 mg, 956 μmol) at 0° C. and stirred for 16 h. After completion, the solution was extracted with DCM. The combined organic layers were dried over sodium sulfate and concentrated to give the crude product that was purified by column chromatography to give compound F (170 mg, 54%) as a white solid.

To a solution of compound F (170 mg, 255 μmol) in DMF (5 mL) were added HATU (153 mg, 650 μmol), DIEA (224 mg, 1.73 mmol) and compound G (215 mg, 1.3 mmol) at room temperature. The mixture was stirred for 16 h. After completion, the reaction was quenched by the addition of water and extracted with DCM. The organic layer was washed by brine, dried over sodium sulfate, filtered, and concentrated to the afford the crude product that was purified by column chromatography to give the title compound T4 (55 mg, 25%) as a white solid. $^1H$ NMR (400 MHz, $CDCl_3$) δ 4.33 (d, J=13.4 Hz, 1H), 3.58 (d, J=5.0 Hz, 2H), 3.48-3.34 (m, 2H), 3.03 (s, 1H), 2.37 (s, 1H), 2.19 (d, J=13.4 Hz, 2H), 2.02-1.66 (m, 7H), 1.65-1.39 (m, 16H), 1.38-1.18 (m, 7H), 1.18-0.83 (m, 15H), 0.81 (s, 3H), 0.65 (s, 4H). LCMS: $[M+H]^+$=504.35

Example T5: (R)-4-((3S,5S,8S,9S,10S,11S,13R,14S,17R)-3,11-dihydroxy-10,13-dimethylhexadecahydro-1H-cyclopenta[a]phenanthren-17-yl)-N,N-dimethylpentanamide See Example 157.

Example T6: (R)-4-((3S,5S,8S,9S,10S,11S,13R,14S,17R)-3,11-dihydroxy-10,13-dimethylhexadecahydro-1H-cyclopenta[a]phenanthren-17-yl)-1-(4-methylpiperidin-1-yl)pentan-1-one

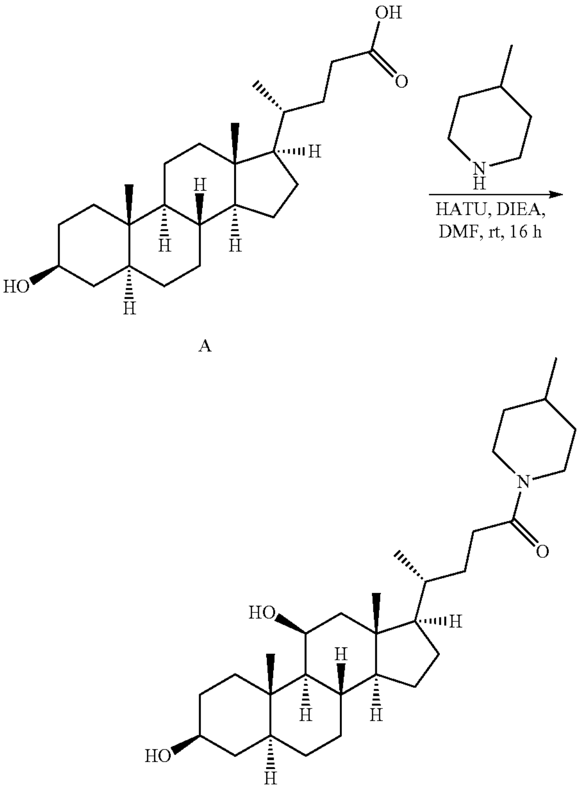

A T6

A solution of compound A (200 mg, 512 μmol), 4-methylpiperidine (60.9 mg, 614 μmol), HATU (292 mg, 768 μmol) and DIPEA (199 mg, 1.54 mmol) in DMF (4 mL) was stirred at room temperature for 16 h. The mixture was purified by Prep-HPLC to give the title compound T6 (47.4 mg, 19%) as a white solid. $^1$H NMR (400 MHz, $CDCl_3$) δ 4.57 (d, J=13.1 Hz, 1H), 4.26 (q, J=3.2 Hz, 1H), 3.79 (d, J=13.5 Hz, 1H), 3.58 (dt, J=11.3, 6.1 Hz, 1H), 3.04-2.92 (m, 1H), 2.57-2.46 (m, 1H), 2.39-2.28 (m, 1H), 2.24-2.10 (m, 2H), 1.88-1.70 (m, 6H), 1.67-1.38 (m, 11H), 1.36-1.24 (m, 6H), 1.10 (dd, J=12.9, 8.9 Hz, 4H), 1.04 (s, 3H), 0.94 (d, J=6.5 Hz, 6H), 0.88 (s, 3H), 0.68 (dd, J=11.0, 3.3 Hz, 1H).

Example T7: (R)-4-((3S,5S,8S,9S,10S,11S,13R,14S,17R)-3,11-dihydroxy-10,13-dimethylhexadecahydro-1H-cyclopenta[a]phenanthren-17-yl)-1-(4-ethyl-4-hydroxypiperidin-1-yl)pentan-1-one See Example 158.

Example T8: (4R)-4-[(1R,3aS,3bR,7S,9aS,9bS,11aR)-7-hydroxy-9a,11a-dimethyl-hexadecahydro-1H-cyclopenta[a]phenanthren-1-yl]-N,N,2-trimethylpentanamide

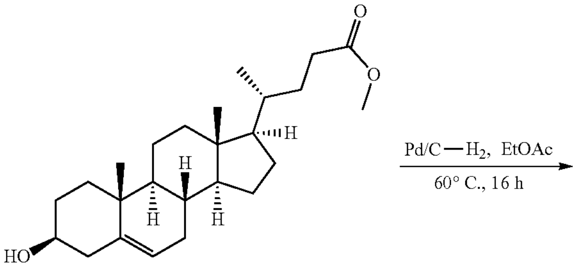

A

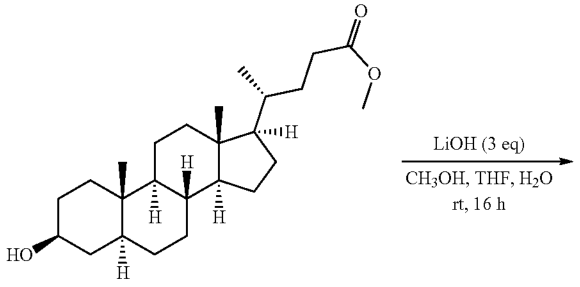

B

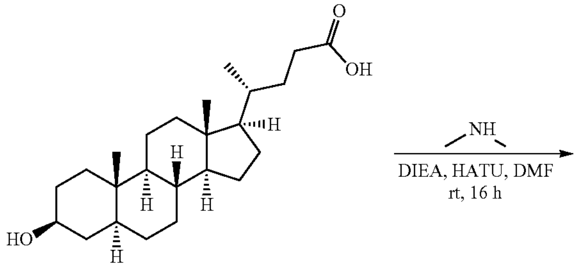

C

-continued

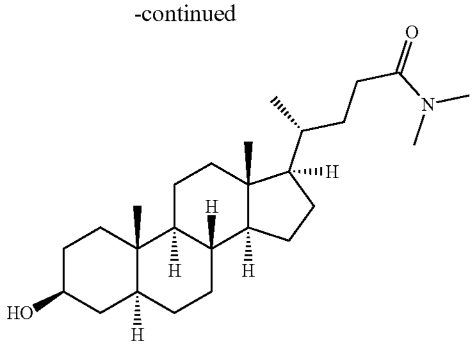

T8

To a solution of compound A (1.5 g, 3.86 mmol) in ethyl acetate (50 mL) at room temperature was added Pd/C (150 mg, 10% weight). The mixture was warmed to 60° C. and stirred for 16 h under 1 atm of $H_2$. The mixture was filtered and concentrated to afford compound B (1.4 g, 93%) as a white solid.

To the solution of compound B (1.4 g, 3.58 mmol) in a mixture of MeOH (15 mL), THF and water was added LiOH (257 mg, 3 eq, 10.74 mmol) at room temperature. The mixture stirred for 16 h. After completion, the solvent was removed in vacuo. The residue was diluted with water, acidified with 1N HCl to pH~3 and extracted with ethyl acetate (100 mL×3). The organic layer was washed by brine, dried over sodium sulfate, filtered, and concentrated to afford compound C (1.35 g, 100%) as a white solid.

To a solution of compound C (200 mg, 531 μmol) in DMF (5 mL) were added dimethylamine (46.2 mg, 1.02 mmol), DIEA (275 mg, 2.12 mmol) and HATU (303 mg, 797 μmol). The reaction was stirred at room temperature for 16 h. After completion, the reaction was quenched with water and extracted with ethyl acetate (10 mL×3). The combined organic layer was washed with brine, dried over sodium sulfate, filtered, and concentrated. The residue was purified by column chromatography to yield the title compound T8 (170 mg, 80%) as a white solid. $^1$H NMR (400 MHz, $CDCl_3$) δ 3.61 (dp, J=11.0, 4.8 Hz, 1H), 3.02 (s, 3H), 2.97 (s, 3H), 2.38 (td, J=13.3, 11.1, 5.1 Hz, 1H), 2.23 (ddd, J=15.6, 10.9, 5.6 Hz, 1H), 1.98 (d, J=12.5 Hz, 1H), 1.93-1.01 (m, 26H), 0.96 (d, J=6.3 Hz, 3H), 0.89 (t, J=9.1 Hz, 1H), 0.85-0.79 (m, 3H), 0.68 (s, 3H).

Example T9: (R)-4-((3S,5S,8R,9S,10S,13R,14S,17R)-3-hydroxy-10,13-dimethylhexadecahydro-1H-cyclopenta[a]phenanthren-17-yl)-1-(4-methylpiperidin-1-yl)pentan-1-one

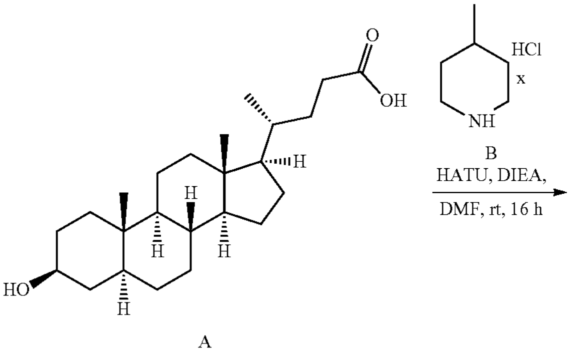

A

-continued

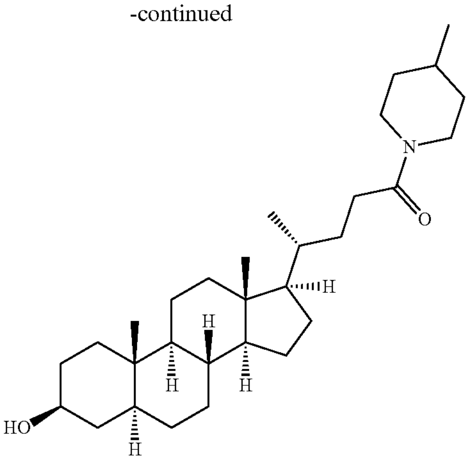

T9

To a solution of compound A (100 mg, 266 μmol) in DMF (4 mL) were added compound B (71.5 mg, 531 μmol), DIEA (172 mg, 1.33 mmol) and HATU (202 mg, 531 μmol). The reaction was stirred at room temperature for 16 h then diluted with water and extracted with ethyl acetate. The organic layer was concentrated, and the residue was purified by column chromatography to give the title compound T9 (50 mg, 41%). $^1H$ NMR (400 MHz, $CDCl_3$) δ 4.56 (d, J=13.1 Hz, 1H), 3.80 (d, J=13.6 Hz, 1H), 3.77-3.66 (m, 2H), 3.58 (tt, J=10.6, 4.7 Hz, 1H), 3.17 (qd, J=7.4, 4.2 Hz, 2H), 3.07-2.90 (m, 3H), 2.54 (t, J=12.7 Hz, 1H), 2.48-2.30 (m, 1H), 2.21 (td, J=14.4, 12.4, 5.1 Hz, 1H), 1.89-1.77 (m, 3H), 1.62-1.52 (m, 4H), 1.51-1.40 (m, 15H), 1.35-1.28 (m, 4H), 1.14-1.04 (m, 5H), 0.80 (s, 3H), 0.65 (s, 3H).

Example T10: (R)-1-(4-ethyl-4-hydroxypiperidin-1-yl)-4-((3S,5S,8R,9S,10S,13R,14S,17R)-3-hydroxy-10,13-dimethylhexadecahydro-1H-cyclopenta[a]phenanthren-17-yl)pentan-1-one

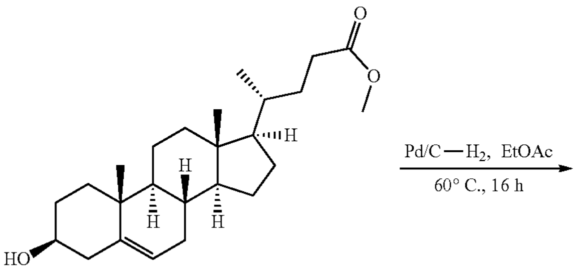

A

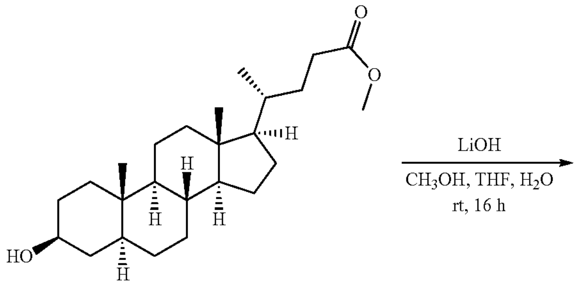

B

-continued

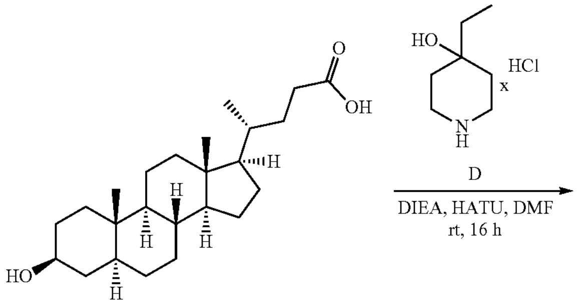

C

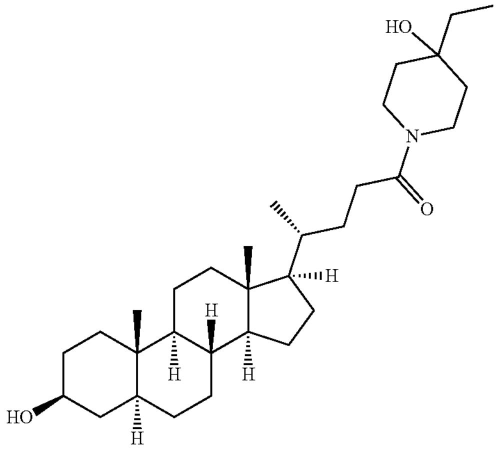

T10

A mixture of compound A (1.5 g, 3.86 mmol) and Pd/C (150 mg, 10% weight) in ethyl acetate (50 mL) was purged with $H_2$ 3 times, warmed to 60° C., and stirred for 16 h under 1 atm of $H_2$. After completion, the mixture was filtered through Celite, and the solvent was concentrated under vacuum to afford compound B (1.4 g, 93%) as a white solid.

To a solution of compound B (1.4 g, 3.58 mmol) in MeOH (10 mL) and THF (10 mL) was added LiOH (343.0 mg, 14.3 mmol) in water (10 mL) at room temperature. The mixture was stirred for 16 h. The solvent was removed in vacuo. The residue was diluted with water, acidified with 1N HCl to pH~2, and extracted with ethyl acetate (100 mL×3). The organic layer was washed by brine, dried over sodium sulfate, filtered, concentrated to afford compound C (1.35 g, 100%) as a white solid.

To the solution of compound C (200 mg, 531 μmol) in DMF (5 mL) were added compound D (176 mg, 1.06 mmol), DIEA (275 mg, 2.12 mmol) and HATU (303 mg, 797 μmol). The mixture was stirred at room temperature for 16 h. After completion, the mixture was diluted with water and extracted with ethyl acetate (10 mL×3). The organic layer was washed with brine, dried over sodium sulfate, filtered, and concentrated to give the crude product that was purified by column chromatography to yield the title compound T10 (115 mg, 45%). $^1H$ NMR (400 MHz, $CDCl_3$) δ 4.32 (d, J=13.2 Hz, 1H), 3.59 (td, J=11.2, 5.4 Hz, 2H), 3.41 (t, J=12.6 Hz, 1H), 3.02 (t, J=11.3 Hz, 1H), 2.46-2.12 (m, 2H), 1.95 (d, J=12.5 Hz, 1H), 1.90-1.61 (m, 6H), 1.55-1.43 (m, 10H), 1.36-1.21 (m, 8H), 1.16-1.03 (m, 4H), 1.00 (q, J=3.6 Hz, 1H), 0.97-0.88 (m, 8H), 0.79 (s, 3H), 0.65 (s, 3H). LCMS: $[M+H]^+$=488.35.

Example T11: (R)-4-((3S,5S,8R,9S,10S,13R,14S,17R)-3-hydroxy-10,13-dimethylhexadecahydro-1H-cyclopenta[a]phenanthren-17-yl)-1-(4-(pyrimidin-4-yl)piperazin-1-yl)pentan-1-one

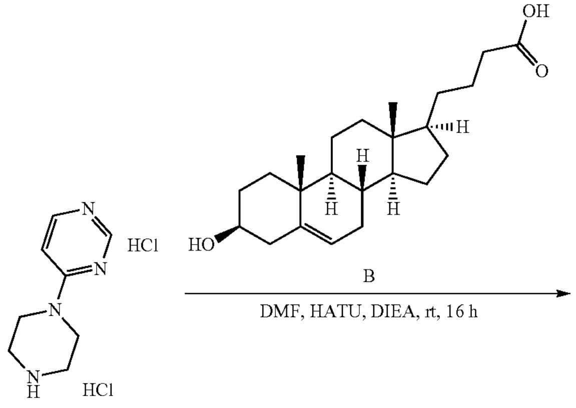

A

-continued

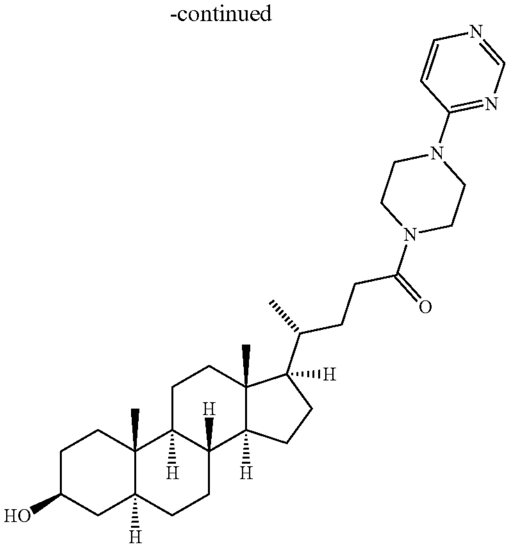

T11

To a solution of compound A (50 mg, 211 μmol) in DMF (3 mL) was added DIEA (164 mg, 1.27 mmol), compound B (71.5 mg, 190 μmol) and HATU (241 mg, 633 μmol). The mixture was stirred at room temperature for 16 hours after which it was quenched by adding saturated ammonium chloride solution (30 mL) and extracted with ethyl acetate (20 mL×3). The organic layer was washed with brine, dried over sodium sulfate, filtered, and concentrated to give a crude which was purified by column chromatography on silica gel to give the title compound T11 (30 mg, 27.2%) as a white solid. $^1H$ NMR (400 MHz, DMSO-d6) δ 8.51 (s, 1H), 8.20 (d, J=6.2 Hz, 1H), 6.83 (dd, J=7.6, 1H), 4.40 (d, J=4.8 Hz, 1H), 3.68-3.49 (m, 8H), 3.38-3.33 (m, 1H), 2.40-2.20 (m, 2H), 2.03-1.33 (m, 11H), 1.32-0.93 (m, 13H), 0.92-0.83 (m, 5H), 0.74 (s, 3H), 0.62 (s, 3H), 0.58 (dd, J=11.1, 2.8 Hz, 1H). LCMS: [M+1]+=523.25.

Example T12: 2-hydroxy-N-((1-((R)-4-((3S,5S,8R,9S,10S,13R,14S,17R)-3-hydroxy-10,13-dimethylhexadecahydro-1H-cyclopenta[a]phenanthren-17-yl)pentanoyl)-4-methylpiperidin-4-yl)methyl)-2-methylpropanamide

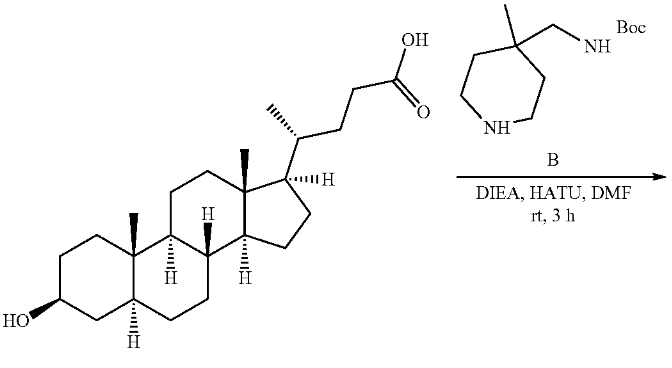

A

-continued

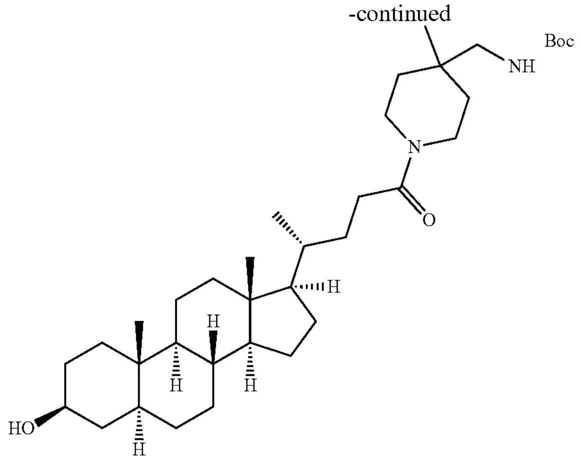

C

HCl-dioxane, rt, 1 h

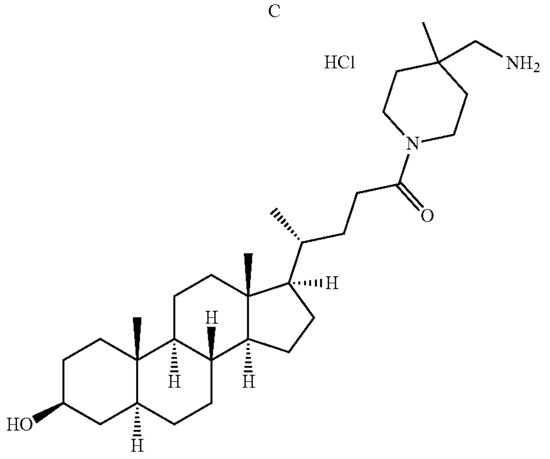

D

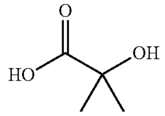

E

DIEA, HATU, DMF
rt, 3 h

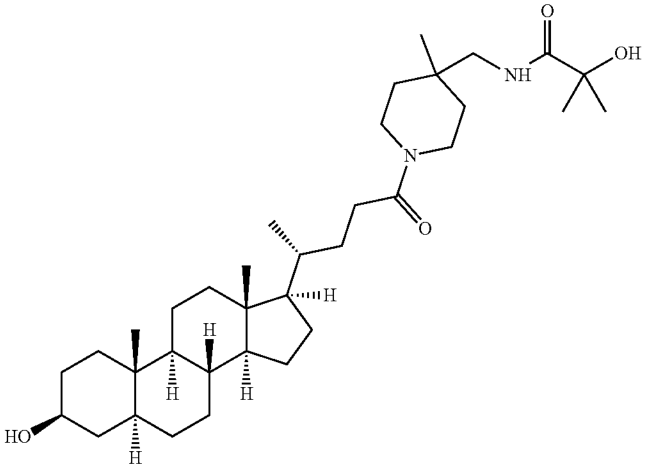

T12

To a solution of compound A (300 mg, 798 μmol) and compound B (200 mg, 876 μmol) in DMF (10 mL) was added HATU (600 mg, 1.58 mmol) and DIEA (600 mg, 4.64 mmol). The mixture was stirred at room temperature for 3 hours after which it was quenched by adding saturated ammonium chloride solution (100 mL) and extracted with ethyl acetate (100 mL×3). The organic layer was washed with brine, dried over sodium sulfate, filtered, and concentrated to give a crude which was purified by column chromatography on silica gel to yield compound C (450 mg, 96%) as a white solid.

To a solution of HCl (1 mL, 4 mmol, 4 M in dioxane) was added slowly compound C (200 mg, 341 μmol) in DCM (4 mL) at room temperature and the mixture was stirred for 1 hour. After completion, the reaction was concentrated to give compound D (160 mg, 96%) as a solid.

To a solution of compound D (150 mg, 287 μmol) and compound E (32.1 mg, 308 μmol) in DMF (5 mL) was added HATU (145 mg, 616 μmol) and DIEA (300 mg, 2.32 mmol). The mixture was stirred at room temperature for 3 hours after which it was quenched by adding a saturated ammonium chloride solution (50 mL) and the reaction was extracted with ethyl acetate (50 mL×3). The organic layer was washed with brine, dried over sodium sulfate, filtered, and concentrated to give a crude which was purified by column chromatography on silica gel to yield compound T12 (78 mg, 44%) as a white solid. LCMS: $[M+H]^+$=573.3. $^1$H NMR (400 MHz, Chloroform-d) δ 6.90 (d, J=7.4 Hz, 1H), 3.86 (bs, 1H), 3.63-3.54 (m, 2H), 3.32 (t, J=11.6 Hz, 3H), 3.08 (bs, 1H), 2.41-2.29 (m, 1H), 2.25-2.13 (m, 1H), 1.98-1.51 (m, 13H), 1.41-1.20 (m, 14H), 1.15-1.03 (m, 4H), 0.99 (s, 3H), 0.92 (d, J=6.4 Hz, 3H), 0.80 (s, 3H), 0.65 (s, 3H), 0.63-0.57 (m, 1H).

Example T13: (4R)-4-((3S,8R,9S,10S,13R,14S,17R)-3-hydroxy-10,13-dimethylhexadecahydro-1H-cyclopenta[a]phenanthren-17-yl)-1-(4-(1-iminoethyl)piperazin-1-yl)pentan-1-one

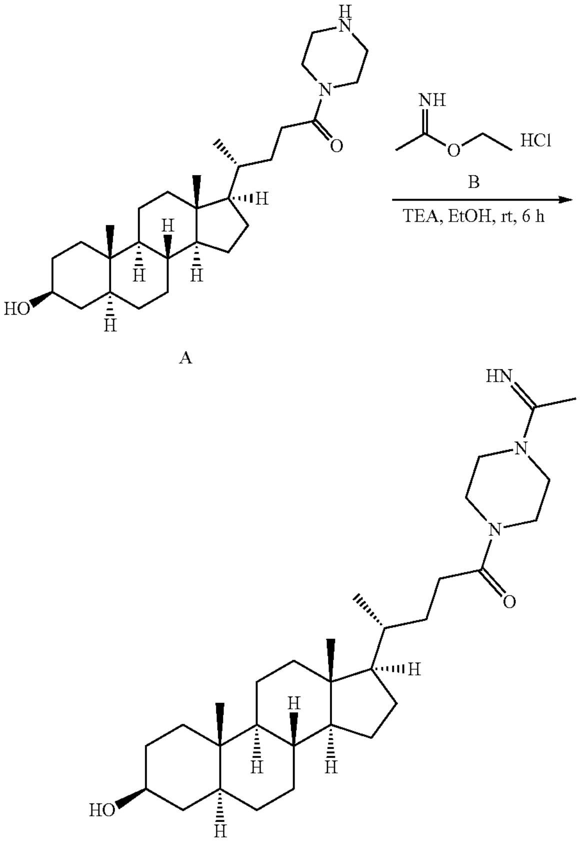

A

B

T13

To a solution of compound A (300 mg, 678 μmol) and compound B (83.7 mg, 678 μmol) in ethanol (5 mL, 85.6 mmol) was added TEA (206 mg, 2.03 mmol). The mixture was stirred at room temperature for 6 hours after which it was diluted with water and extracted with ethyl acetate. The organic layer was concentrated to give a crude which was purified by silica gel chromatography to give the title compound T13 (75 mg, 22.9%). $^1$H NMR (400 MHz, Methanol-$d_4$) δ 3.82-3.57 (m, 8H), 3.55-3.45 (m, 1H), 2.47 (s, 1H), 2.36 (s, 4H), 2.04-1.96 (m, 1H), 1.94-1.83 (m, 1H), 1.81-1.66 (m, 4H), 1.62-1.25 (m, 13H), 1.20-1.04 (m, 5H), 1.03-0.88 (m, 5H), 0.84 (s, 3H), 0.70 (s, 3H),), 0.69-0.61 (m, 1H). LCMS: $[M+1]^+$=486.25.

Example T14: 4—((R)-4-((3S,5S,8R,9S,10S,13R,14S,17R)-3-hydroxy-10,13-dimethylhexadecahydro-1H-cyclopenta[a]phenanthren-17-yl)pentanoyl)piperazine-1-carboxamide

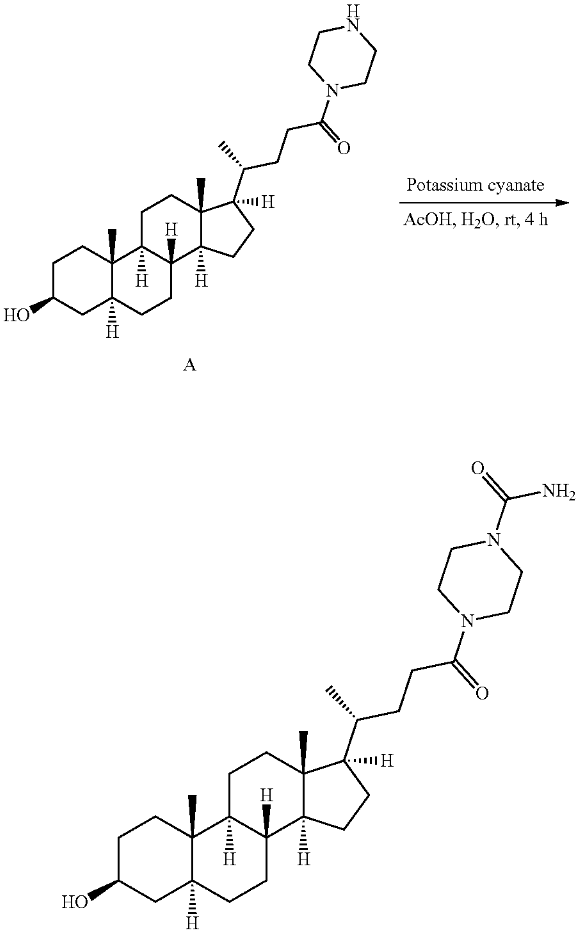

A

T14

To a solution of compound A (50 mg, 112 μmol) in water (2 mL) and acetic acid (1 mL) was added potassium cyanate (45.6 mg, 562 μmol). The mixture was stirred at room temperature for 4 hours after which it was diluted with water and extracted with ethyl acetate. The organic layer was concentrated, and the residue was purified by silica gel chromatography to give compound T14 (15 mg, 27.3%). $^1$H NMR (400 MHz, Methanol-$d_4$) δ 3.63-3.44 (m, 7H), 3.41-3.38 (m, 2H), 2.50-2.42 (m, 1H), 2.35-2.27 (m, 1H), 2.06-1.82 (m, 2H), 1.80-1.66 (m, 4H), 1.64-1.44 (m, 4H), 1.41-1.29 (m, 7H), 1.28-1.02 (m, 7H), 0.98-0.95 (m, 3H), 0.97-0.88 (m, 2H), 0.84 (s, 3H), 0.70 (s, 3H), 0.67-0.59 (m, 1H). LCMS: $[M+1]^+$=488.25.

Example T15: 4R)-4-[(1R,3aS,3bR,5aS,7S,9aS,9bS, 11aR)-7-hydroxy-9a,11a-dimethyl-hexadecahydro-1H-cyclopenta[a]phenanthren-1-yl]-1-(4-acetylpiperazin-1-yl)pentan-1-one

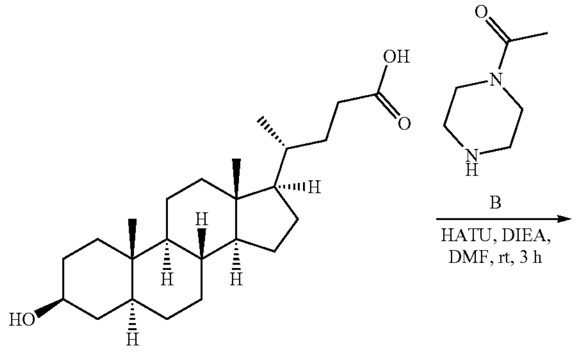

A

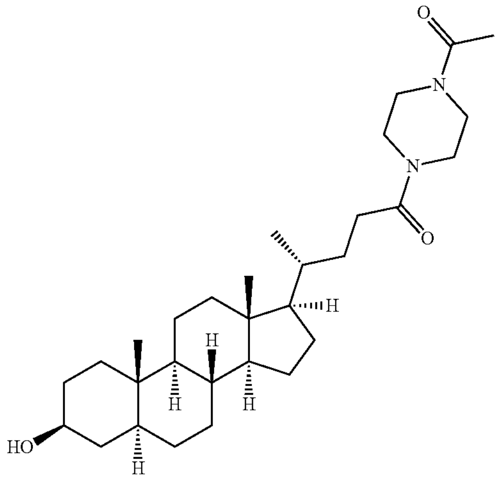

T15

To a solution of compound A (300 mg, 797 μmol) and compound B (128 mg, 996 μmol) in DMF (8 mL) was added HATU (757 mg, 1.99 mmol) and DIEA (772 mg, 5.97 mmol). The mixture was stirred at room temperature for 3 hours after which it was quenched by adding a saturated ammonium chloride solution (30 mL) and then extracted with ethyl acetate (10 mL×3). The organic layer was washed with brine, dried over sodium sulfate, filtered, and concentrated to give a crude which was purified by column chromatography on silica gel to yield the title compound T15 (300 mg, 62%) as a white solid. LCMS: $[M+1]^+$=457.4. $^1H$ NMR (400 MHz, Chloroform-d) δ 3.68-3.39 (m, 9H), 2.37 (td, J=10.5, 5.4 Hz, 1H), 2.23 (td, J=10.7, 9.8, 5.1 Hz, 1H), 2.12 (s, 3H), 1.99-1.75 (m, 4H), 1.74-1.66 (m, 2H), 1.59-1.40 (m, 6H), 1.39-1.27 (m, 5H), 1.23 (d, J=3.9 Hz, 1H), 1.15-0.98 (m, 5H), 0.94 (d, J=6.4 Hz, 3H), 0.89-0.83 (m, 1H), 0.80 (s, 3H), 0.65 (s, 3H), 0.60 (dd, J=11.7, 4.2 Hz, 1H).

Example T16: (4R)-4-[(1R,3aS,3bR,5aS,7S,9aS, 9bS,11aR)-7-hydroxy-9a,11a-dimethyl-hexadecahydro-1H-cyclopenta[a]phenanthren-1-yl]-1-[(3S)-3-methoxypiperidin-1-yl]pentan-1-one

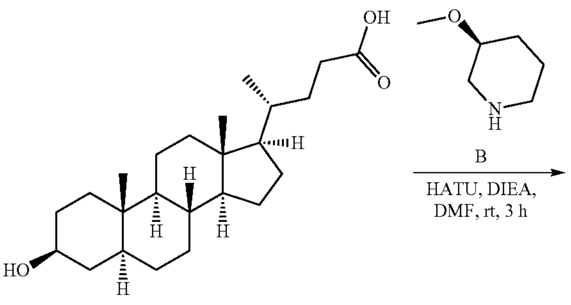

A

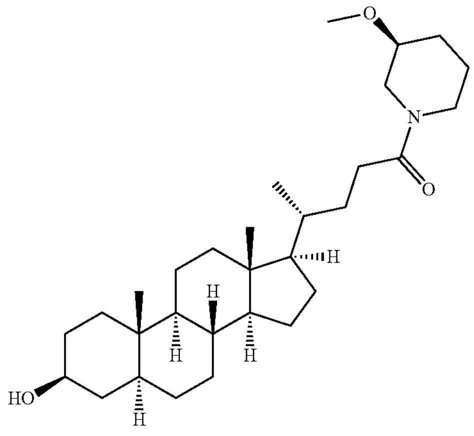

T16

To a solution of compound A (150 mg, 398 μmol) and compound B (45.9 mg, 398 μmol) in DMF (5 mL) was added HATU (303 mg, 797 mmol) and DIEA (309 mg, 2.39 μmol). The mixture was stirred at room temperature for 3 hours after which it was quenched by adding a saturated ammonium chloride solution (30 mL) and then extracted with ethyl acetate (10 mL×3). The organic layer was washed with brine, dried over sodium sulfate, filtered, and concentrated to give a crude which was purified by column chromatography on silica gel to yield compound T16 (100 mg, 53%) as a white solid. LCMS: $[M+1]^+$=474.25. $^1H$ NMR (400 MHz, Chloroform-d) δ 4.10-3.42 (m, 3H), 3.37 (s, 3H), 3.26-3.09 (m, 3H), 2.37 (ddd, J=15.6, 10.9, 5.1 Hz, 1H), 2.21 (ddt, J=15.1, 10.7, 5.4 Hz, 1H), 2.00-1.75 (m, 6H), 1.73-1.61 (m, 3H), 1.47-1.22 (m, 12H), 1.14-0.95 (m, 6H), 0.93 (d, J=6.4 Hz, 3H), 0.91-0.82 (m, 1H), 0.80 (s, 3H), 0.65 (s, 3H), 0.63-0.56 (m, 1H).

Example T17: Methyl-4-[(4R)-4-[(1R,3aS,3bR,5aS,7S,9aS,9bS,11aR)-7-hydroxy-7,9a,11a-trimethyl-hexadecahydro-1H-cyclopenta[a]phenanthren-1-yl]pentanoyl]piperazine-1-carboxylate

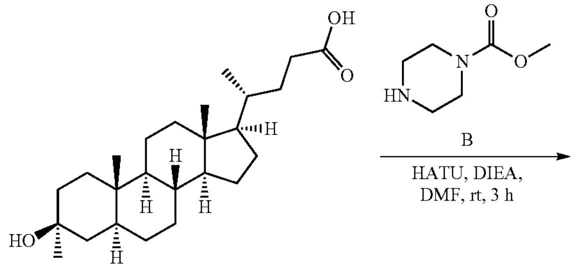

A

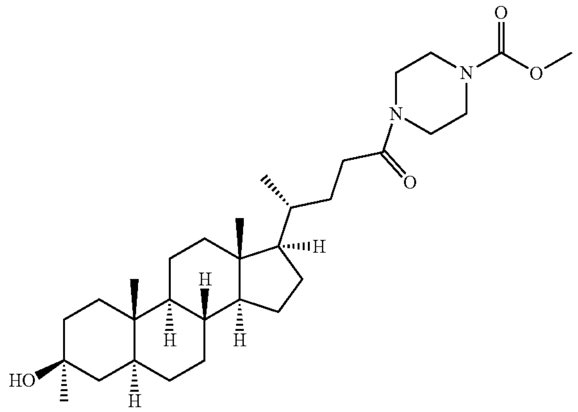

T17

To a solution of compound A (200 mg, 512 μmol) and compound B (92 mg, 640 μmol) in DMF (8 mL) was added HATU (487 mg, 1.28 mmol) and DIEA (496 mg, 3.8 mmol). The mixture was stirred at room temperature for 3 hours after which it was quenched by adding a saturated ammonium chloride solution (30 mL) and then extracted with ethyl acetate (10 mL×3). The organic layer was washed with brine, dried over sodium sulfate, filtered, and concentrated to give a crude which was purified by column chromatography on silica gel to yield the title compound T17 (250 mg, 76%) as a white solid. LCMS: [M+1]+=499.20. $^1$H NMR (400 MHz, Chloroform-d) δ 3.72 (s, 3H), 3.59 (t, J=5.2 Hz, 2H), 3.49 (bs, 2H), 3.45 (bs, 4H), 2.37 (ddd, J=15.7, 11.0, 5.1 Hz, 1H), 2.22 (ddd, J=14.9, 10.5, 5.6 Hz, 1H), 1.95 (dt, J=12.5, 3.4 Hz, 1H), 1.89-1.72 (m, 2H), 1.63-1.27 (m, 13H), 1.27-0.97 (m, 15H), 0.93 (d, J=6.5 Hz, 3H), 0.90-0.82 (m, 1H), 0.80 (s, 3H), 0.68-0.59 (m, 4H).

Example T18: methyl 4-[(4R)-4-[(1R,3aS,3bR,5aS,7S,9aS,9bS,11aR)-7-hydroxy-9a,11a-dimethyl-hexadecahydro-1H-cyclopenta[a]phenanthren-1-yl]pentanoyl]piperazine-1-carboxylate

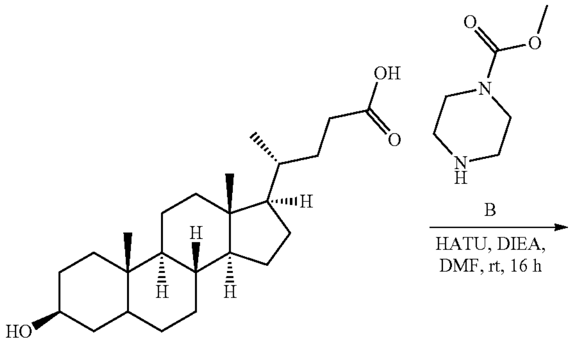

A

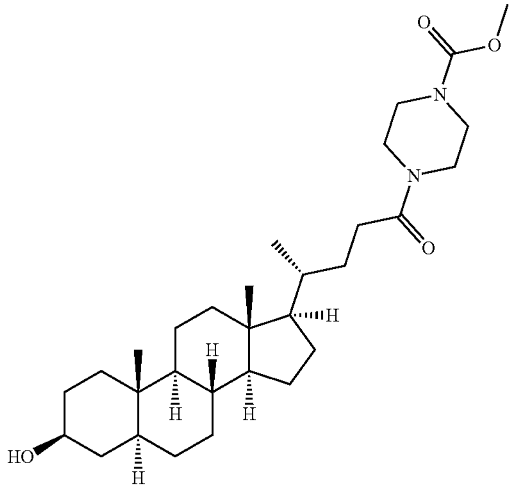

T18

To a solution of compound A (300 mg, 797 μmol) in DMF (3 mL) was added compound B (144 mg, 996 μmol), DIEA(129 mg, 996 μmol) and HATU (469 mg, 1.99 mmol). The mixture was stirred at room temperature for 16 hours after which it was quenched with water and extracted with ethyl acetate (15 mL×4). The combined organic layer was concentrated to give a crude which was purified by silica gel chromatography to yield the title compound T18 (105 mg, 20%). LCMS:$[M+Na]^+$=525.25. $^1$H NMR (400 MHz, Chloroform-d) δ 3.72 (s, 3H), 3.64-3.53 (m, 3H), 3.52-3.38 (m, 6H), 2.43-2.14 (m, 2H), 2.05-1.91 (m, 1H), 1.88-1.71 (m, 4H), 1.70-1.60 (m, 3H), 1.59-1.52 (m, 2H), 1.51-1.40 (m, 3H), 1.38-1.31 (m, 3H), 1.30-1.21 (m, 6H), 1.15-1.04 (m, 4H), 1.02-0.98 (m, 1H), 0.97-0.90 (m, 4H), 0.90-0.83 (m, 1H), 0.80 (s, 3H), 0.68-0.56 (m, 4H).

Example T19: (R)-4-((3S,5S,8S,9S,10S,11S,13R,14S,17R)-3,11-dihydroxy-10,13-dimethylhexadecahydro-1H-cyclopenta[a]phenanthren-17-yl)-1-morpholinopentan-1-one

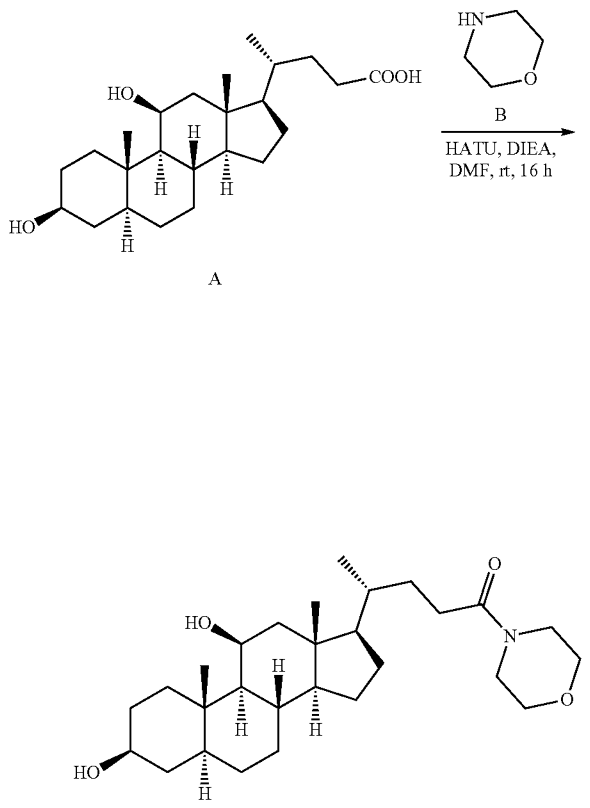

T19

To a stirring solution of compound A (20 mg, 43.3 μmol), morpholine (7.6 mg, 86.6 μmol) and DIPEA (16.8 mg, 129.9 μmol) in DMF (1 mL) was added HATU (24.7 mg, 65.0 μmol) under $N_2$ atmosphere and the mixture was stirred for 16 h. The reaction was then diluted with HCl (1M, 20 mL) and extracted with ethyl acetate (30 mL), then washed with $NaHCO_3$ (10 mL) and water (20 mL×2). The combined organic layers were washed with brine (10 mL), dried over sodium sulfate, and concentrated under vacuum to give a crude which was purified by silica gel chromatography (DCM/MeOH=0~10%, v/v) to afford the title compound T19 (16.0 mg, 68%). LCMS:[M+H$^+$]=461.30; [M+Na$^+$]=484.30. $^1$H NMR (400 MHz, Chloroform-d) δ 4.30 (q, J=3.3 Hz, 1H), 3.78-3.38 (m, 9H), 2.39 (ddd, J=15.6, 10.8, 5.1 Hz, 1H), 2.31-2.12 (m, 2H), 1.98-1.73 (m, 6H), 1.72-1.54 (m, 4H), 1.53-1.23 (m, 12H), 1.23-1.10 (m, 4H), 1.08 (s, 3H), 0.98 (d, J=6.5 Hz, 3H), 0.92 (s, 3H), 0.72 (dd, J=11.1, 3.4 Hz, 1H).

Example T20: (R)-1-(4-acetylpiperazin-1-yl)-4-((3S,5S,8S,9S,10S,11S,13R,14S,17R)-3,11-dihydroxy-10,13-dimethylhexadecahydro-1H-cyclopenta[a]phenanthren-17-yl)pentan-1-one

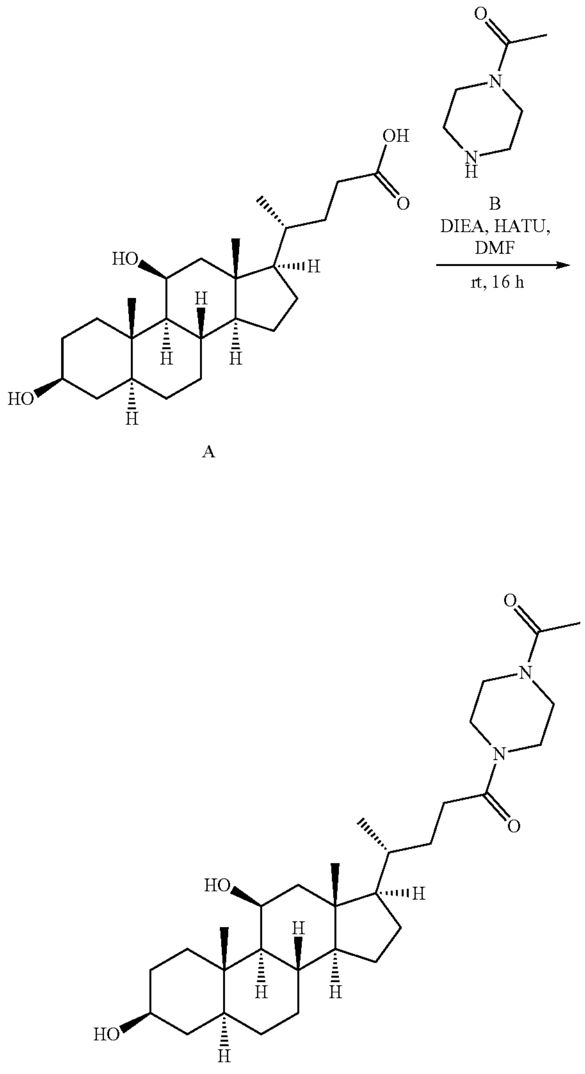

T20

To a solution of compound A (30 mg, 76.4 μmol) and compound B (14.7 mg, 115 μmol) in dry-DMF (1 mL) was added HATU (14.8 mg, 115 μmol)) and DIEA (49.4 mg, 382 μmol) at room temperature and the mixture was stirred for 16 h. To the reaction was then added $H_2O$ and it was extracted with ethyl acetate. The combined organic layers were dried over sodium sulfate and concentrated under reduced pressure. The residue was purified by silica gel chromatography to give the title compound T20 (10 mg, 26%) as a white solid. $^1$H NMR (400 MHz, Chloroform-d) δ 4.26 (d, J=3.4 Hz, 1H), 3.69-3.55 (m, 5H), 3.50-3.42 (m, 4H), 2.42-1.92 (m, 2H), 2.15-2.09 (m, 4H), 1.88-1.72 (m, 6H), 1.51-1.38 (m, 4H), 1.36-1.29 (m, 4H), 1.28-1.24 (m, 5H), 1.14-1.06 (m, 4H), 1.04 (s, 3H), 1.03-0.97 (m, 2H), 0.95 (d, J=6.4 Hz, 3H), 0.89 (s, 3H), 0.68 (dd, J=11.2, 3.4 Hz, 1H).

Example T21: (R)-4-((3S,5S,8S,9S,10S,11S,13R,14S,17R)-3,11-dihydroxy-10,13-dimethylhexadecahydro-1H-cyclopenta[a]phenanthren-17-yl)-1-(4-ethynyl-4-methylpiperidin-1-yl)pentan-1-one

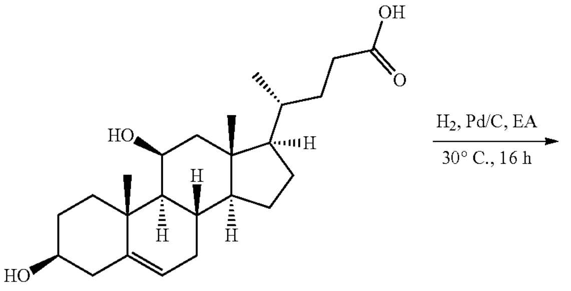

A

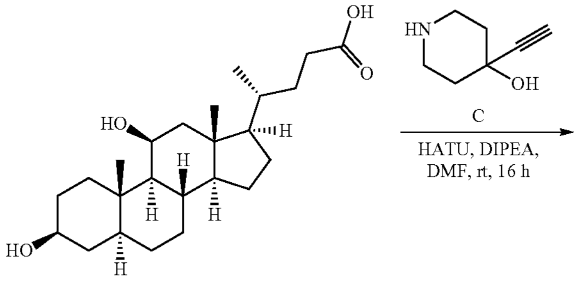

B

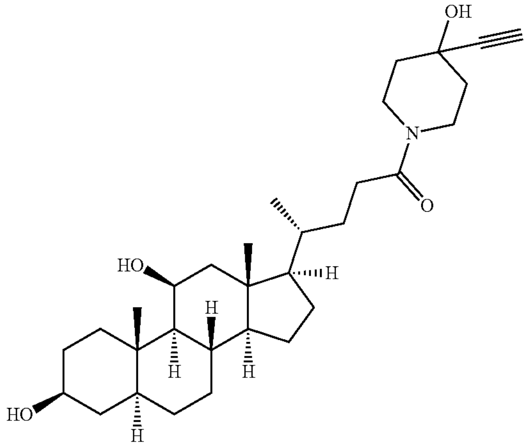

T21

To a stirring solution of compound A (142 mg, 364 μmol) in ethyl acetate (5 mL) was added 10% Pd/C (20 mg). The mixture was stirred under 1 atm of $H_2$ for 16 h at 30° C. After filtration, the solvent was removed to afford compound B (138 mg) as a white solid.

The mixture of compound B (20 mg, 50.9 μmol), compound C (6.38 mg, 50.9 μmol), DIPEA (19.8 mg, 153 μmol) and HATU (29.1 mg, 76.4 μmol) in DMF (1 mL) was stirred at room temperature under $N_2$ atmosphere for 16 h after which it was diluted with HCl (1M, 10 mL) and extracted with ethyl acetate (20 mL×2), then washed with $NaHCO_3$ (30 mL) and water (20 mL×2). The combined organic layers were washed with brine (10 mL), dried over sodium sulfate and concentrated in vacuum to give a crude which was purified by silica gel chromatography (DCM:MeOH=0/100~2/100) to give the title compound T21 (12 mg, 47%). LCMS: $[M+H^+]$=500.35; $[M+Na^+]$=522.35. $^1$H NMR (400 MHz, DMSO-$d_6$) δ 5.63 (s, 1H), 4.38 (d, J=4.0 Hz, 1H), 4.07 (bs, 1H), 3.89 (bs, 1H), 3.71-3.55 (m, 2H), 3.38 (s, 1H), 3.27-3.22 (m, 2H), 2.32-2.04 (m, 3H), 1.90-1.39 (m, 12H), 1.38-1.06 (m, 11H), 1.05-0.98 (m, 3H), 0.95 (s, 3H), 0.90 (d, J=6.0 Hz, 5H), 0.82 (s, 3H), 0.54 (d, J=12.0 Hz, 1H).

Example T22: (R)-4-((3S,5S,8R,9S,10S,13R,14S,17R)-3-hydroxy-10,13-dimethylhexadecahydro-1H-cyclopenta[a]phenanthren-17-yl)-1-(4-hydroxypiperidin-1-yl)pentan-1-one

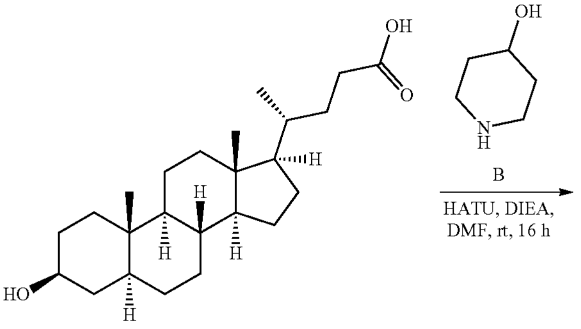

A

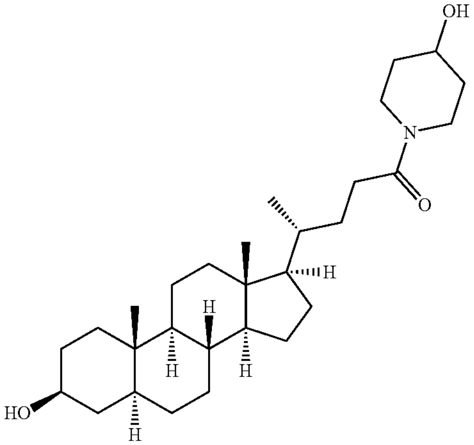

T22

To a solution of compound A (200 mg, 531 μmol) and compound B (64.5 mg, 637 μmol) in DMF (3 mL) was added HATU (404 mg, 1.06 mmol) and DIEA (343 mg, 2.66 mmol). The mixture was stirred at room temperature for 16 hours after which it was quenched by adding a saturated ammonium chloride solution (20 mL) and then extracted with ethyl acetate (20 mL×3). The organic layer was washed with brine, dried over sodium sulfate, filtered, and concentrated to give a crude which was purified by column chromatography on silica gel to yield the title compound T22 (65 mg, 26.6%) as a white solid. LCMS: $[M+H]^+$=460.30. $^1$H NMR (400 MHz, Chloroform-d) δ 4.21-3.53 (m, 4H), 3.22 (t, J=11.6 Hz, 2H), 2.41 (ddd, J=15.6, 11.1, 5.1 Hz, 1H), 2.25 (ddd, J=15.1, 10.7, 5.5 Hz, 1H), 2.02-1.68 (m, 8H), 1.63-1.22 (m, 15H), 1.21-0.99 (m, 6H), 0.97 (d, J=6.4 Hz, 3H), 0.95-0.85 (m, 1H), 0.83 (s, 3H), 0.68 (s, 3H), 0.67-0.60 (m, 1H).

Example T23: (R)-1-(4-ethynyl-4-hydroxypiperidin-1-yl)-4-((3S,5S,8R,9S,10S,13R,14S,17R)-3-hydroxy-10,13-dimethylhexadecahydro-1H-cyclopenta[a]phenanthren-17-yl)pentan-1-one

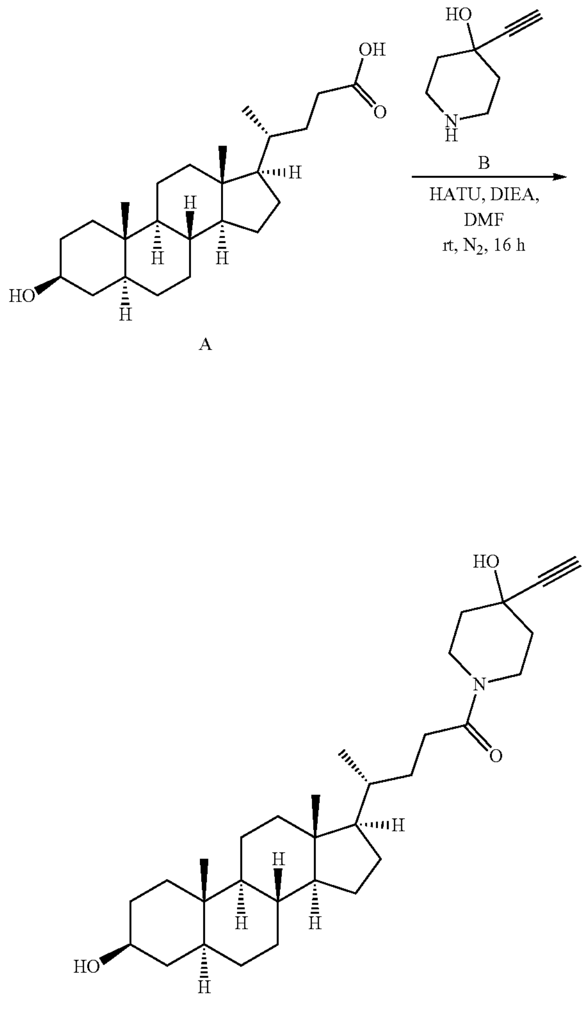

A

T23

To a solution of compound A (200 mg, 0.53 mmol) in DMF (5 mL) was added compound B (66.5 mg, 0.53 mmol), HATU (404 mg, 1.06 mmol) and DIEA (406 mg, 3.14 mmol). The mixture was stirred at room temperature under $N_2$ for 16 h after which it was quenched with saturated $NH_4Cl$ and extracted with ethyl acetate. The organic layer was washed with brine, dried over sodium sulfate, filtered, and concentrated. The mixture was purified by column chromatography on silica gel to afford the title compound T23 (60 mg) as a white solid. $^1H$ NMR (400 MHz, Chloroform-d) δ 4.08-3.97 (m, 1H), 3.72-3.64 (m, 1H), 3.58 (dq, J=10.8, 5.3,4.8 Hz, 1H), 3.39 (t, J=11.6 Hz, 2H), 2.55 (s, 1H), 2.43-2.33 (m, 1H), 2.27-2.15 (m, 2H), 2.00-1.21 (m, 29H), 1.17-0.97 (m, 6H), 0.93 (d, J=6.4 Hz, 3H), 0.90-0.83 (m, 1H), 0.80 (s, 3H), 0.65 (s, 3H), 0.61 (d, J=10.0 Hz, 1H). LCMS: $[M+H]^+$=484.30.

Example T24: (3S,5S,8R,9S,10S,13R,14S,17R)-17-((2R,5S)-5-cyclopropyl-6,6,6-trifluoro-5-hydroxyhexan-2-yl)-3,10,13-trimethylhexadecahydro-1H-cyclopenta[a]phenanthren-3-ol

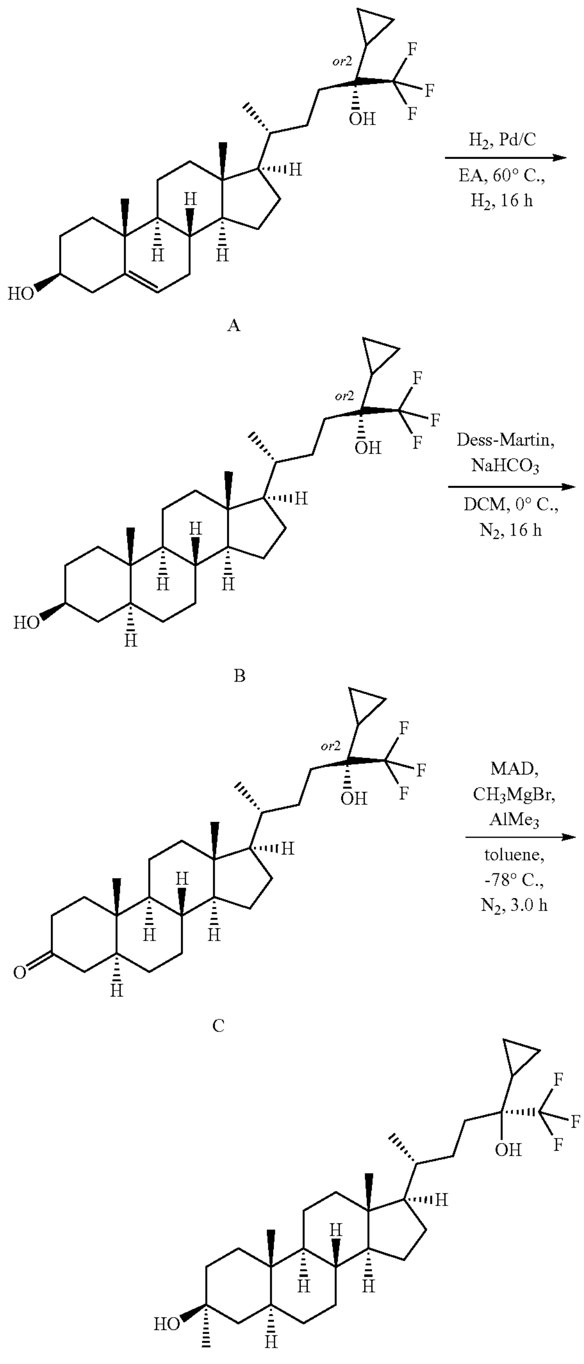

A

B

C $T_{24}$

To a solution of compound A (1.1 g, 2.35 mmol) in ethyl acetate (30 mL) was added 10% Pd/C (300 mg). The mixture was stirred at 60° C. under 1 atm of $H_2$ for 16 h after which it was concentrated to afford the compound B (980 mg, 89%) as a white solid.

To a solution of compound B (500 mg, 1.06 mmol) in DCM (20 mL) was added DMP (901 mg, 2.12 mmol) and sodium hydrogen carbonate (446 mg, 5.31 mmol). The mixture was stirred at 0° C. under $N_2$ for 16 h. The reaction was quenched with saturated $NH_4Cl$. and extracted with ethyl acetate. The organic layer was washed by brine, dried over sodium sulfate. The mixture was purified by column chromatography on silica gel to afford compound C (280 mg) as a white solid.

To a solution of 2,6-di-tert-butyl-4-methylphenol (306 mg, 1.39 mmol) and $AlMe_3$ (0.64 mL, 640 μmol, 1M in toluene) in toluene (22 mL) under $N_2$ at 0° C., compound C (100 mg, 0.21 mmol) was added and the mixture was stirred for 30 mins after which it was cooled to −78° C., and MeMgBr (0.6 mL, 1M in THF, 0.6 mmol) was added to the solution. The mixture was stirred at −78° C. under $N_2$ for 3 h. The reaction was quenched with saturated $NH_4Cl$. and extracted with ethyl acetate. The organic layer was washed with brine, dried over sodium sulfate, filtered, and concentrated. The residue was purified by column chromatography on silica gel to afford the title compound T24 (40 mg) as a white solid. $^1H$ NMR (400 MHz, Chloroform-d): δ 1.99-1.91 (m, 1H), 1.91-1.75 (m, 2H), 1.71-0.84 (m, 37H), 0.81 (s, 3H), 0.70-0.61 (m, 4H), 0.60-0.41 (m, 4H).

Example T25: (3S,5S,8R,9S,10S,13R,14S,17R)-10,13-dimethyl-17-((R)-4-(pyridin-2-yl)butan-2-yl)hexadecahydro-1H-cyclopenta[a]phenanthren-3-ol

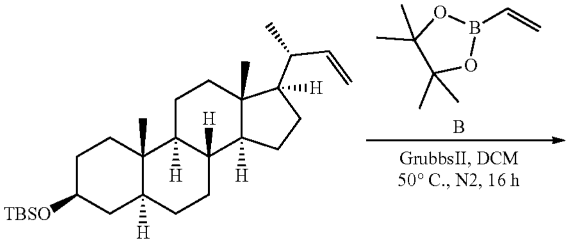

A

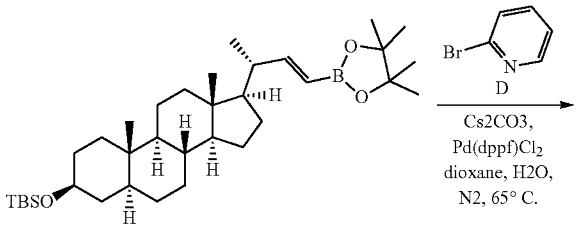

C

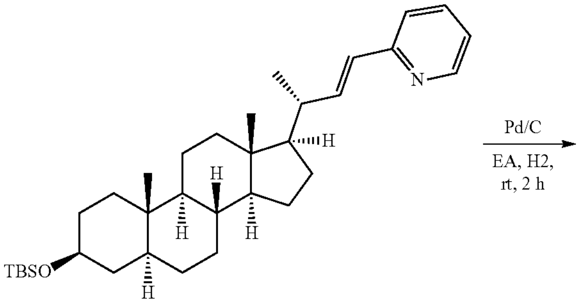

E

-continued

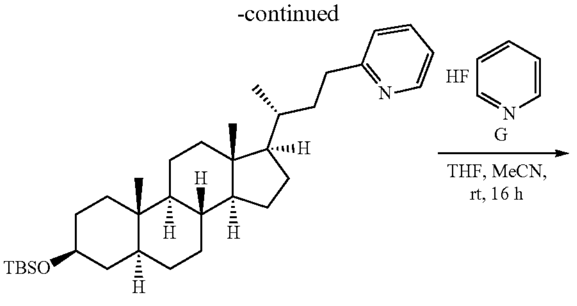

F

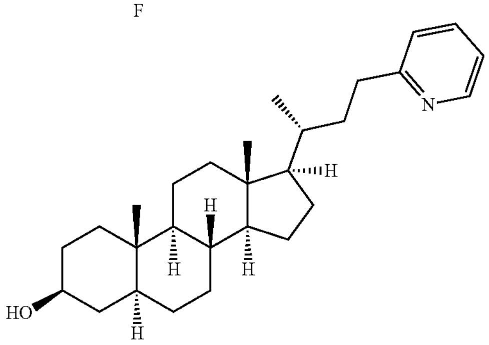

T25

To a solution of compound A (800 mg, 1.8 mmol) in dichloromethane (30 mL) was added compound B (277 mg, 1.8 mmol) and the Grubbs II catalyst (225 mg, 0.36 mmol). The mixture was stirred at 50° C. under $N_2$ for 16 h after which it was quenched with water and extracted with DCM. The organic layer was washed with brine, dried over sodium sulfate, filtered, and concentrated. The mixture was purified by column chromatography on silica gel to afford compound C (550 mg).

To a solution of compound C (550 mg, 0.96 mmol) in 1,4-dioxane (14 mL) and water (2 mL) was added compound D (304 mg, 1.93 mmol), cesium carbonate (1.1 g, 3.37 mmol) and $Pd(dppf)Cl_2$ (69.9 mg, 0.094 mmol). The mixture was stirred at 65° C. under $N_2$ for 16 h after which it was diluted with water and extracted with ethyl acetate. The organic layer was washed by brine, dried over sodium sulfate, filtered, and concentrated. The mixture was purified by column chromatography on silica gel to afford compound E (150 mg) as a solid.

To a solution of compound E (150 mg, 0.28 mmol) in ethyl acetate (10 mL) was added 10% Pd/C (20 mg). The mixture was stirred under 1 atm of $H_2$ at room temperature for 2 h after which it was filtered and concentrated to afford compound F (100 mg) as a white solid.

To a solution of compound F (100 mg, 0.19 mmol) in tetrahydrofuran (2.5 mL) and acetonitrile (2.5 mL) was added pyridine hydrofluoride (1 mL). The mixture was stirred at room temperature for 16 h after which it was diluted with water and extracted with ethyl acetate. The organic layer was washed with brine, dried over sodium sulfate, filtered, and concentrated. The mixture was purified by column chromatography on silica gel to afford the title compound T25 (30 mg) as a white solid. $^1H$ NMR (400 MHz, Chloroform-d) δ 8.57-8.45 (m, 1H), 7.60 (t, J=7.5 Hz, 1H), 7.15 (d, J=7.8 Hz, 1H), 7.13-7.07 (m, 1H), 3.59 (dt, J=11.1, 5.9 Hz, 1H), 2.88 (ddd, J=15.2, 11.4, 4.3 Hz, 1H), 2.68 (dd, J=16.1, 8.3 Hz, 1H), 1.97 (dt, J=12.5, 3.5 Hz, 1H), 1.91-1.62 (m, 8H), 1.60-1.28 (m, 11H), 1.23-1.08 (m, 4H), 1.02 (d, J=6.1 Hz, 3H), 1.00-0.84 (m, 4H), 0.80 (s, 3H), 0.65 (s, 3H), 0.64-0.56 (m, 1H). LCMS: $[M+H]^+$=410.25.

Example T26: (4R)-4-[(1R,3aS,3bR,5aS,7S,9aS,9bS,11aR)-7-hydroxy-7,9a,11a-trimethyl-hexadecahydro-1H-cyclopenta[a]phenanthren-1-yl]-1-(4-ethyl-4-hydroxypiperidin-1-yl)pentan-1-one

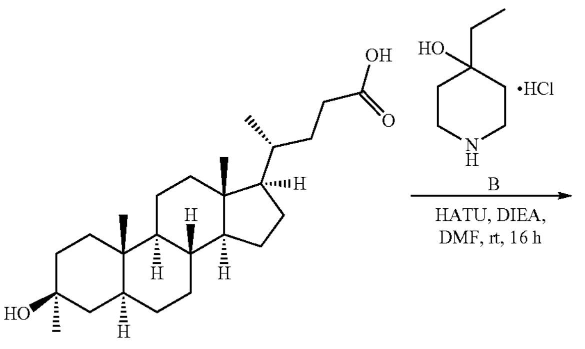

A

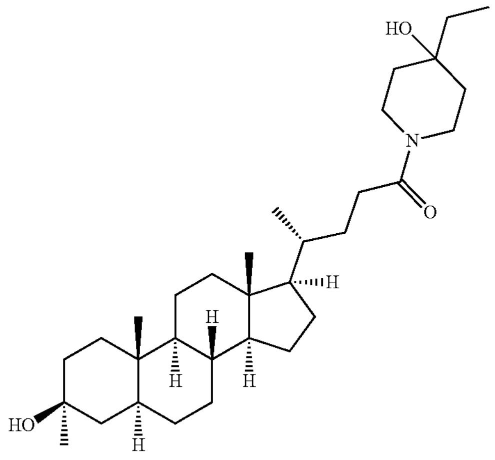

T26

To a solution of compound A (100 mg, 256 μmol) in DMF (2 mL) was added compound B (33.1 mg, 256 μmol), DIEA (132 mg, 1.02 mmol) and HATU (90.3 mg, 384 μmol). The mixture was stirred at room temperature for 16 hours after which it was quenched with water and extracted with ethyl acetate (10 mL×4). The combined organic layer was concentrated to give a crude which was purified by silica gel chromatography to yield the title compound T26 (17 mg, 13%). LCMS:$[M+1]^+$=502.35. $^1$H NMR (400 MHz, Chloroform-d) δ 4.33 (d, J=13.2 Hz, 1H), 3.60 (d, J=13.3 Hz, 1H), 3.41 (t, J=12.3 Hz, 1H), 3.02 (t, J=12.5 Hz, 1H), 2.37 (t, J=14.0 Hz, 1H), 2.26-2.16 (m, 1H), 1.95 (d, J=12.4 Hz, 1H), 1.89-1.71 (m, 2H), 1.69-1.55 (m, 7H), 1.52-1.40 (m, 9H), 1.36-1.28 (m, 4H), 1.26-1.21 (m, 6H), 1.15-0.98 (m, 5H), 0.95-0.90 (m, 7H), 0.80 (s, 3H), 0.69-0.61 (m, 4H).

Example T27: (R)-4-((3S,5S,8R,9S,10S,13R,14S,17R)-3-hydroxy-10,13-dimethylhexadecahydro-1H-cyclopenta[a]phenanthren-17-yl)-N-(pyridin-4-yl)pentanamide

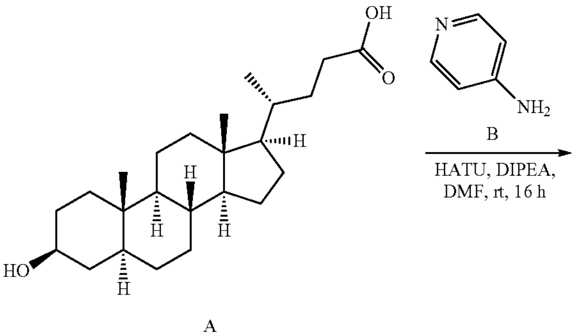

A

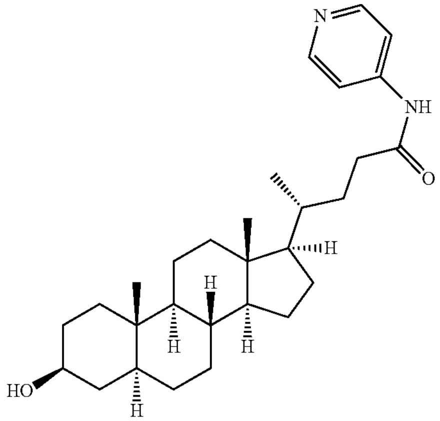

To a solution of (R)-4-((3S,5S,8R,9S,10S,13R,14S,17R)-3-hydroxy-10,13-dimethylhexadecahydro-1H-cyclopenta[a]phenanthren-17-yl)pentanoic acid (200 mg, 531 μmol) and pyridin-4-amine (50 mg, 531 μmol) in DMF (3 mL) was added HATU (404 mg, 1.06 mmol) and DIPEA (343 mg, 2.66 mmol). Upon completion. water (10 mL) was added, and the reaction was extracted with EtOAc (10 mL*3). The combined organic phase was washed with water (10 mL*2), brine (10 mL), dried over sodium sulfate, concentrated under reduced pressure, and purified by silica gel chromatography to afford compound T27 (17.4 mg, 7.2%) as a white solid. LCMS: $[M+H]^+$=453.40. $^1$H NMR (400 MHz, DMSO-$d_6$) δ 10.23 (s, 1H), 8.45-8.33 (m, 2H), 7.59-7.47 (m, 2H), 4.41 (d, J=4.7 Hz, 1H), 2.41-2.33 (m, 1H), 2.28-2.20 (m, 1H), 1.96 (d, J=10.1 Hz, 2H), 1.85-1.70 (m, 2H), 1.58 (d, J=3.4 Hz, 1H), 1.54-1.37 (m, 4H), 1.25 (d, J=10.3 Hz, 6H), 1.23-1.08 (m, 6H), 1.07-0.95 (m, 4H), 0.91 (d, J=6.4 Hz, 3H), 0.89-0.81 (m, 2H), 0.74 (s, 3H), 0.62 (s, 4H).

Example T28: (R)-1-((S)-4-(cyclopropanecarbonyl)-3-methylpiperazin-1-yl)-4-((3S,5S,8R,9S,10S,13R,14S,17R)-3-hydroxy-10,13-dimethylhexadecahydro-1H-cyclopenta[a]phenanthren-17-yl)pentan-1-one

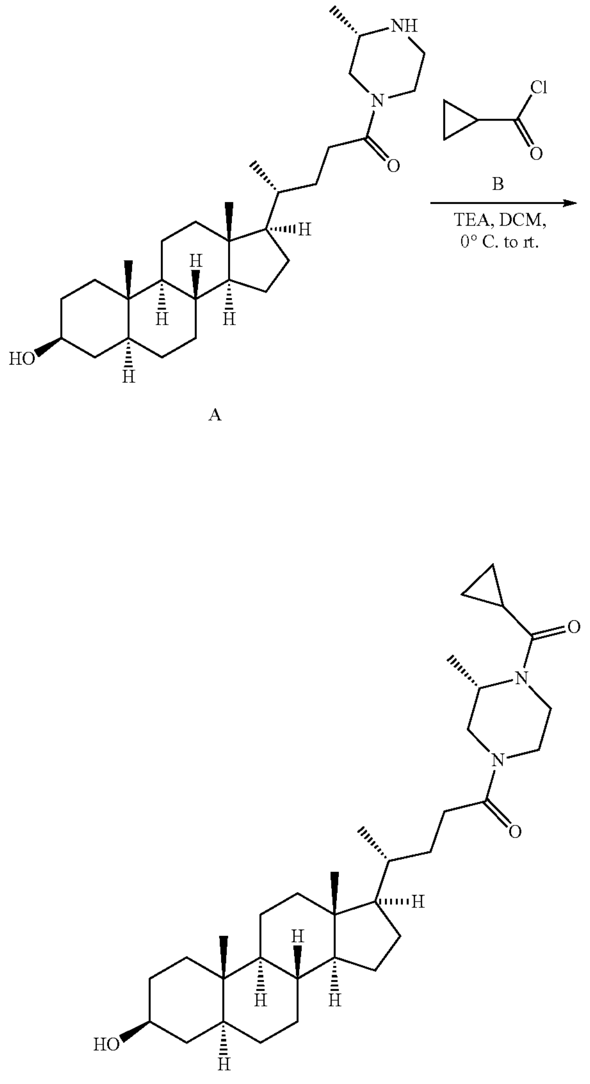

To a 0° C. solution of compound A (50 mg, 109 μmol) and TEA (66.2 mg, 654 μmol) in DCM (2 mL) was added compound B (22.8 mg, 218 μmol) and the reaction was warmed to room temperature under $N_2$ for 2 hours. The reaction was quenched with water (20 mL) and extracted with EtOAc (30 mL*2). The combined organic phase was washed with brine (20 mL), dried over sodium sulfate, and concentrated under reduced pressure. The crude product was purified by silica gel chromatography to afford compound T28 (26 mg, 23%) as white solid. LCMS: $[M+1]^+$=527.20. $^1H$ NMR (400 MHz, Chloroform-d) δ 4.97-4.23 (m, 2H), 4.23-3.72 (m, 1H), 3.70-3.51 (m, 2H), 3.48-2.62 (m, 3H), 2.47-2.16 (m, 2H), 1.95 (d, J=12.0 Hz, 1H), 1.87-1.78 (m, 3H), 1.73-1.61 (m, 5H), 1.58-1.52 (m, 2H), 1.50-1.41 (m, 3H), 1.39-1.28 (m, 5H), 1.25-1.18 (m, 3H), 1.16-1.05 (m, 4H), 1.02-0.98 (m, 3H), 0.94 (t, J=6.4 Hz, 4H), 0.89-0.77 (m, 6H), 0.69-0.58 (m, 4H).

Example T29: (R)-4-((3S,5S,8R,9S,10S,13R,14S,17R)-3-hydroxy-10,13-dimethylhexadecahydro-1H-cyclopenta[a]phenanthren-17-yl)-1-(4-(pyridin-3-yloxy)piperidin-1-yl)pentan-1-one

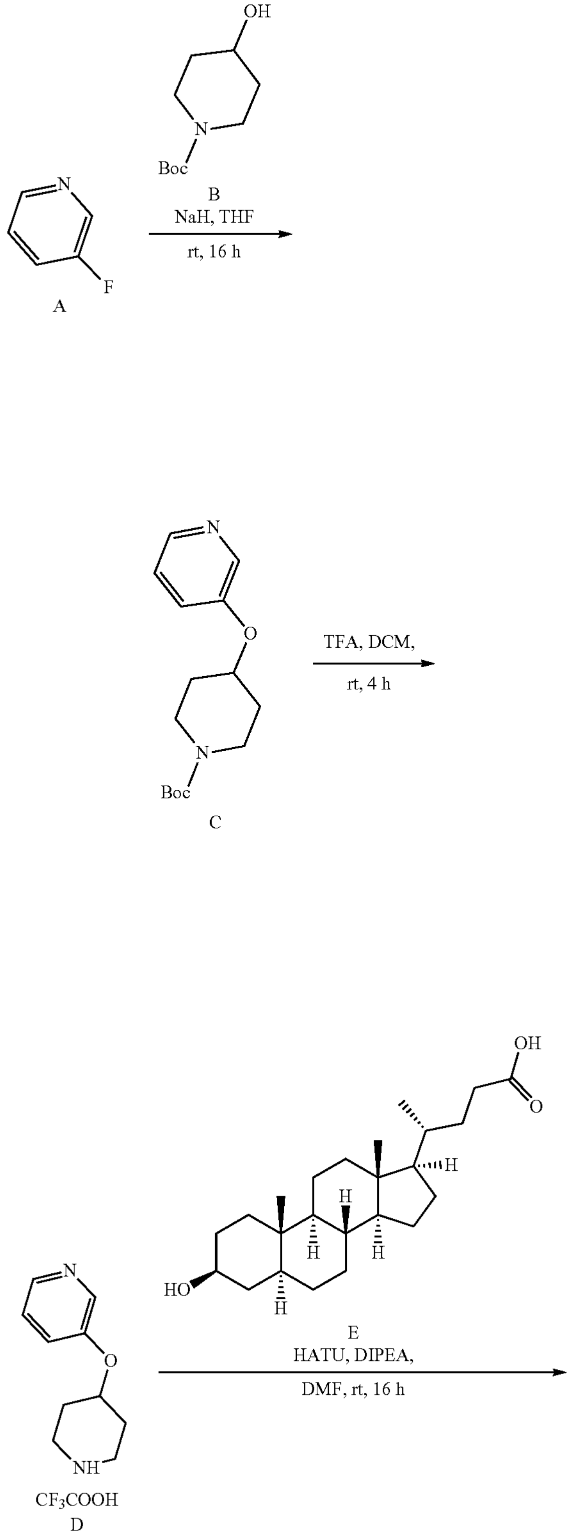

-continued

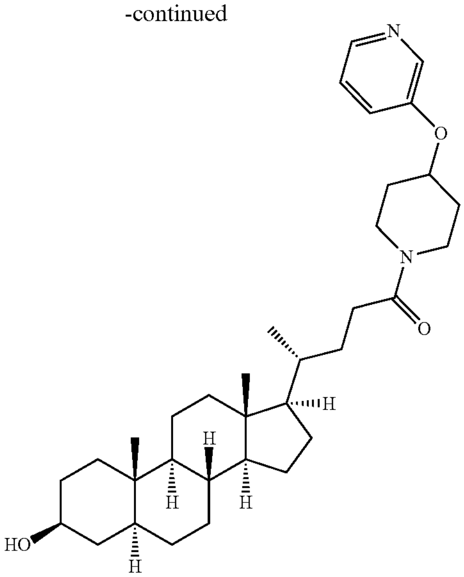

To a solution of compound A (100 mg, 1.03 mmol) in THE (10 mL), was added compound B (207 mg, 1.03 mmol) and NaH (74 mg, 1.85 mmol, 60% dispersion in mineral oil) and the reaction was heated to 25° C. under $N_2$ for 16 h. The reaction was diluted with saturated aqueous $NH_4Cl$ (10 mL) and extracted with EtOAc (10 mL*2). The combined organic layers were washed with saturated aqueous $NaHCO_3$ (20 mL), water (20 mL) and brine (20 mL), dried over sodium sulfate and concentrated under reduced pressure. The residue was purified by silica gel chromatography to afford compound C (100 mg, 35%) as a yellow oil.

To a solution of compound C (100 mg, 359 μmol) in DCM (6 mL) was added TFA (2 mL) at room temperature and the reaction was stirred for 2 h. The reaction was concentrated under reduced pressure to give compound D as the TFA salt (102 mg).

(R)-4-((3S,5S,8R,9S,10S,13R,14S,17R)-3-hydroxy-10,13-dimethylhexadecahydro-1H-cyclopenta[a]phenanthren-17-yl)pentanoic acid (135 mg, 359 μmol) and 3-(piperidin-4-yloxy)pyridine 2,2,2-trifluoroacetate (102 mg, 359 μmol) were reacted according to the method of Example T27 to afford the title compound T29 (75 mg, 39%) as a white solid. LCMS: $[M+1]^+$=537.50. $^1$H NMR (400 MHz, Chloroform-d) δ 8.34-8.30 (m, 1H), 8.24-8.22 (m, 1H), 7.24-7.19 (m, 2H), 4.59-4.54 (m, 1H), 3.84-3.53 (m, 4H), 3.44-3.38 (m, 1H), 2.45-2.17 (m, 2H), 2.01-1.66 (m, 10H), 1.59-1.20 (m, 14H), 1.17-0.78 (m, 14H), 0.58 (s, 4H).

Example T30: (4R)-4-[(1R,3aS,3bR,5aS,7S,9aS,9bS,11aR)-7-hydroxy-9a,11a-dimethyl-hexadecahydro-1H-cyclopenta[a]phenanthren-1-yl]-1-[4-(6-methoxypyrimidin-4-yl)piperazin-1-yl]pentan-1-one

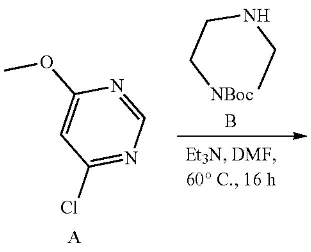

-continued

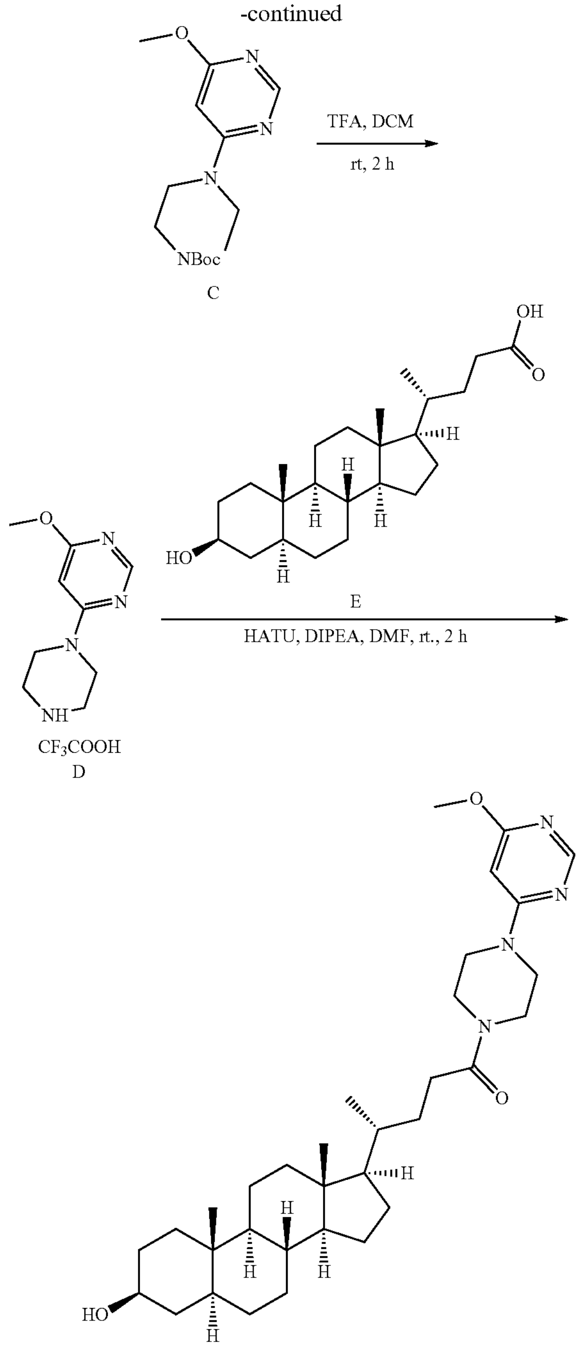

To a solution of compound A (300 mg, 2.08 mmol) in DMF (1.5 mL) was added compound B (387 mg, 2.08 mmol) and triethylamine (0.6 mL, 4.15 mmol). The reaction was warmed to 60° C. for 16 h. Upon completion, water (6 mL) was added, and the reaction was extracted with EtOAc (6 mL*3). The combined organic layers were washed with brine (20 ml*3), dried over sodium sulfate, and concentrated under reduced pressure. The residue was purified by silica gel chromatography to afford compound C (150 mg, 73%) as a yellow oil.

To a solution of compound C (200 mg, 679 μmol) in DCM (2 mL) was added TFA (0.5 mL). The reaction was warmed to room temperature for 2 h. The reaction was concentrated under reduced pressure to afford compound D as the TFA salt (209 mg).

(R)-4-((3S,5S,8R,9S,10S,13R,14S,17R)-3-hydroxy-10,13-dimethylhexadecahydro-1H-cyclopenta[a]phenanthren-17-yl)pentanoic acid (170 mg, 359 µmol) and 4-methoxy-6-(piperazin-1-yl)pyrimidine (209 mg, 679 µmol) were reacted according to the method of Example T27 to afford the title compound T30 (119.6 mg, 65%) as a white solid. LCMS: [M+1]+=553.50. $^1$H NMR (400 MHz, Chloroform-d) δ 8.33 (d, J=0.8 Hz, 1H), 5.82 (d, J=0.8 Hz, 1H), 3.92 (s, 3H), 3.70 (t, J=12.8 Hz, 4H), 3.61-3.50 (m, 5H), 2.36-2.44 (m, 1H), 2.30-2.20 (m, 2H), 2.03-1.63 (m, 8H), 1.51-1.28 (m, 13H), 1.23 (d, J=3.6 Hz, 2H), 1.17-1.06 (m, 4H), 1.01 (td, J=10.8, 6.0 Hz, 2H), 0.95 (d, J=6.4 Hz, 4H), 0.90-0.84 (m, 2H), 0.80 (s, 3H), 0.69-0.60 (m, 4H).

Example T31: (R)-4-((3S,5S,8R,9S,10S,13R,14S,17R)-3-hydroxy-10,13-dimethylhexadecahydro-1H-cyclopenta[a]phenanthren-17-yl)-1-(4-(pyrrolidine-1-carbonyl)piperazin-1-yl)pentan-1-one

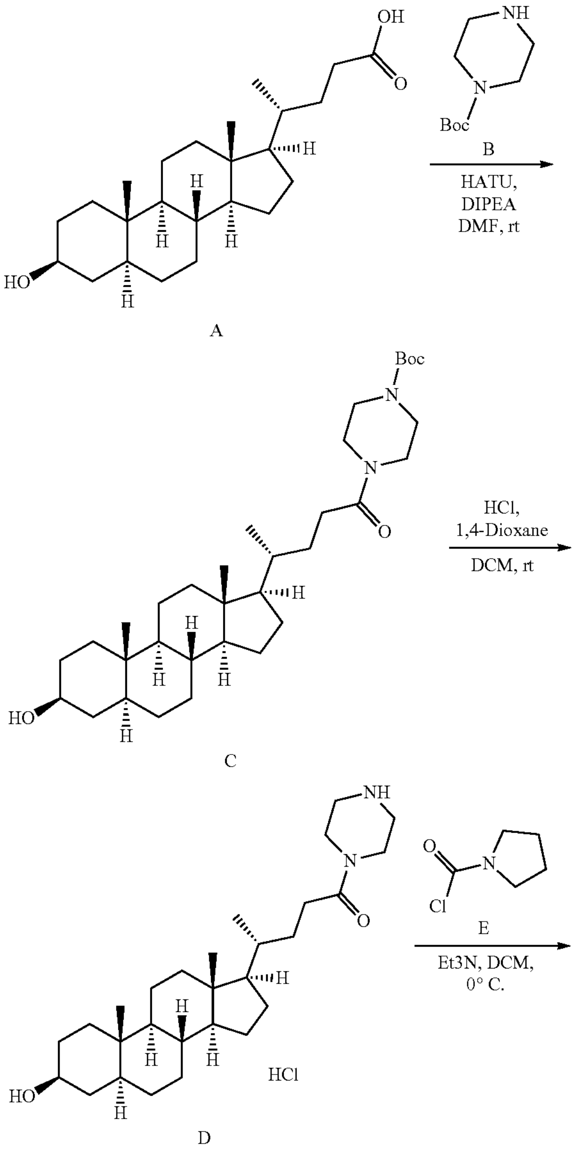

-continued

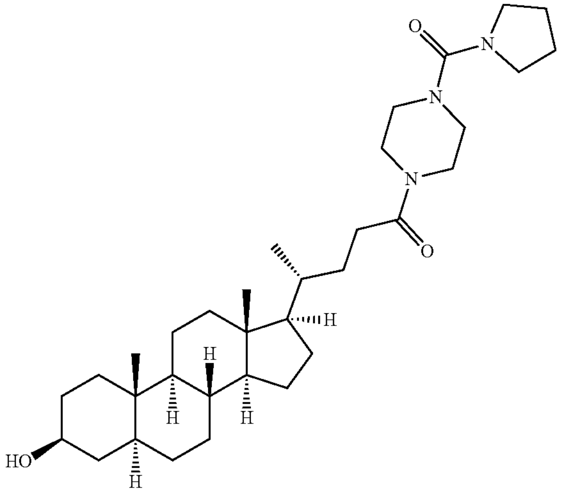

To a solution of compound A (500 mg, 1.33 mmol), compound B (309 mg, 1.66 mmol) and DIPEA (1.29 g, 9.96 mmol) in DMF (10 mL) was added HATU (781 mg, 3.32 mmol) at room temperature under $N_2$ and stirred for 16 h. Upon completion, the reaction was diluted with water (30 mL) and extracted with EtOAc (20 mL*2). The combined organic layers were washed with water (50 mL) and brine (20 mL), dried over sodium sulfate, and concentrated under reduced pressure. The residue was purified by silica gel chromatography to afford compound C (407 mg, 45%) as a white solid.

To a solution of compound C (407 mg, 747 µmol) in DCM (3 mL) was added 4N HCl in 1,4-dioxane (1 mL) at room temperature and the reaction was stirred for 2 h. The reaction was concentrated under reduced pressure to give compound D as the HCl salt (350 mg).

To a solution of compound D (195 mg, 405 µmol) and triethylamine (205 mg, 2.02 mmol) in DCM (5 mL) was added compound E (43.3 mg, 324 µmol) at 0° C. under $N_2$ and stirred for 1 h.

The reaction was quenched with water (20 mL) and extracted with DCM (10 mL*2). The organic layer was washed by brine, dried over sodium sulfate, filtered, and concentrated. The residue was purified by silica gel chromatography to afford the title compound T31 (51 mg, 23%) as a white solid. LCMS: $[M+1]^+$=542.40. $^1$H NMR (400 MHz, $CDCl_3$) δ 3.65-3.53 (m, 3H), 3.48 (t, J=4.8 Hz, 2H), 3.40-3.34 (m, 4H), 3.32-3.22 (m, 4H), 2.43-2.32 (m, 1H), 2.27-2.17 (m, 1H), 1.95 (dt, J=12.4, 3.2 Hz, 1H), 1.87-1.66 (m, 9H), 1.58-1.28 (m, 13H), 1.24-0.83 (m, 13H), 0.80 (s, 3H), 0.70-0.58 (m, 4H).

Example T32: (R)-1-((S)-4-(cyclopropanecarbonyl)-2-methylpiperazin-1-yl)-4-((3S,5S,8R,9S,10S,13R,14S,17R)-3-hydroxy-10,13-dimethylhexadecahydro-1H-cyclopenta[a]phenanthren-17-yl)pentan-1-one

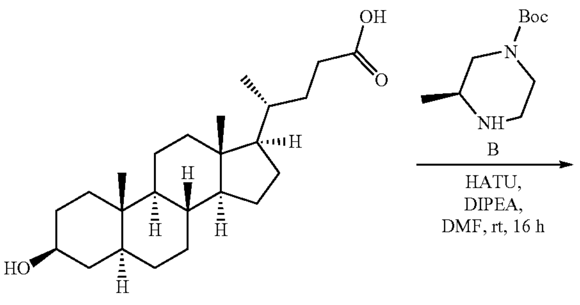

A

-continued

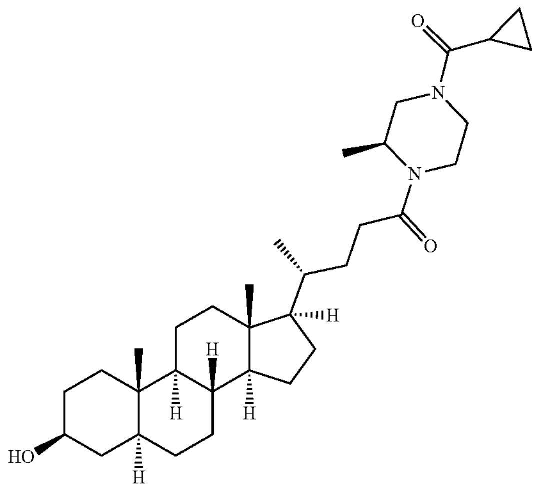

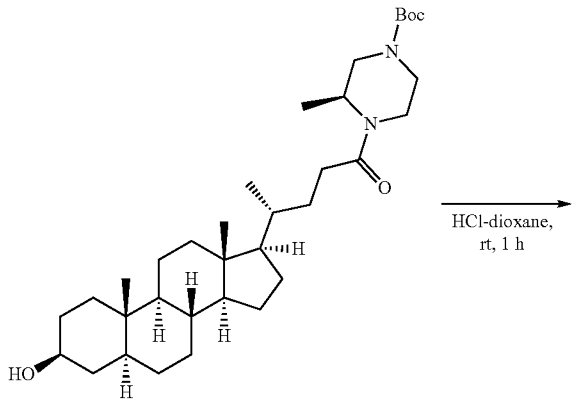

C

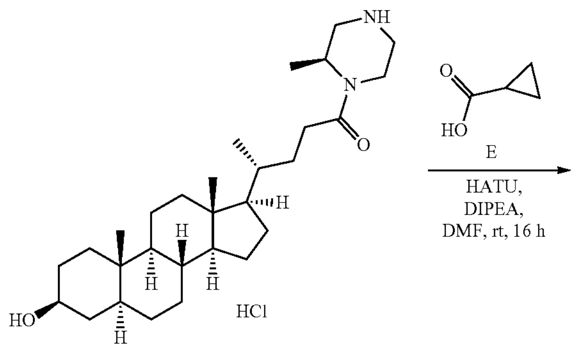

D

To a solution of compound A (2.0 g, 5.31 mmol) and compound B (1.6 g, 7.97 mmol) in DMF (20 mL) was added HATU (4.04 g, 10.6 mmol), DIPEA (3.43 g, 26.6 mmol) and the reaction was stirred at room temperature for 16 hours. Upon completion, the reaction was quenched with saturated aqueous ammonium chloride (50 mL) and extracted with ethyl acetate (50 mL*3). The combined organic layers were washed with brine, dried over sodium sulfate, filtered, and concentrated under reduced pressure. The crude product was purified by silica gel chromatography to afford the title compound C (2.3 g, 77.5%) as a white solid.

4N HCl in 1,4-dioxane (10 mL) was added slowly to the compound C (2.3 g, 4.12 mmol) in a single-neck flask at room temperature and stirred for 1 hour. Upon completion, dichloromethane (15 mL) was added, and the reaction was concentrated under reduced pressure three times to afford the title compound D as the HCl salt (2.0 g).

To a solution of compound D (200 mg, 403 μmol) and compound E (37.5 mg, 436 μmol) in DMF (3 mL) was added HATU (332 mg, 872 μmol), DIPEA (282 mg, 2.18 mmol) and the reaction was warmed to room temperature for 3 hours. The reaction was quenched with saturated aqueous ammonium chloride (10 mL) and extracted with ethyl acetate (10 mL*3). The combined organic layers were washed with brine, dried over sodium sulfate, filtered, and concentrated under reduced pressure. The crude product was purified by silica gel chromatography to afford the title compound T32 (62 mg, 27%) as a white solid. LCMS: $[M+1]^+$=527.55. $^1$H NMR (400 MHz, Chloroform-d) δ 4.86 (s, 1H), 4.62-4.29 (m, 2H), 4.04 (d, J=50.6 Hz, 2H), 3.58 (tt, J=10.8, 4.8 Hz, 2H), 3.44-3.17 (m, 2H), 2.95-2.73 (m, 2H), 2.48-2.16 (m, 2H), 1.95 (d, J=12.4 Hz, 1H), 1.89-1.77 (m, 3H), 1.68 (dt, J=16.6, 3.6 Hz, 4H), 1.53 (d, J=2.4 Hz, 1H), 1.51-1.39 (m, 3H), 1.38-1.31 (m, 3H), 1.30-1.25 (m, 5H), 1.23 (d, J=3.6 Hz, 1H), 1.20-1.10 (m, 4H), 1.09-0.96 (m, 6H), 0.94 (d, J=6.6 Hz, 3H), 0.90-0.84 (m, 1H), 0.80 (s, 4H), 0.65 (s, 4H).

Example T33: (R)-4-((3S,5S,8R,9S,10S,13R,14S,17R)-3-hydroxy-10,13-dimethylhexadecahydro-1H-cyclopenta[a]phenanthren-17-yl)-1-((S)-2-methyl-4-(5-methylpyrimidin-4-yl)piperazin-1-yl)pentan-1-one

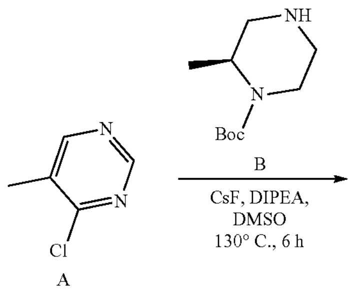

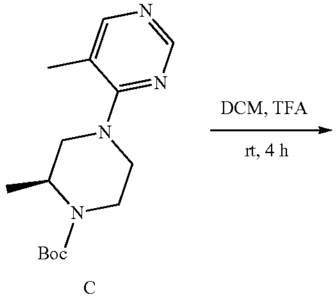

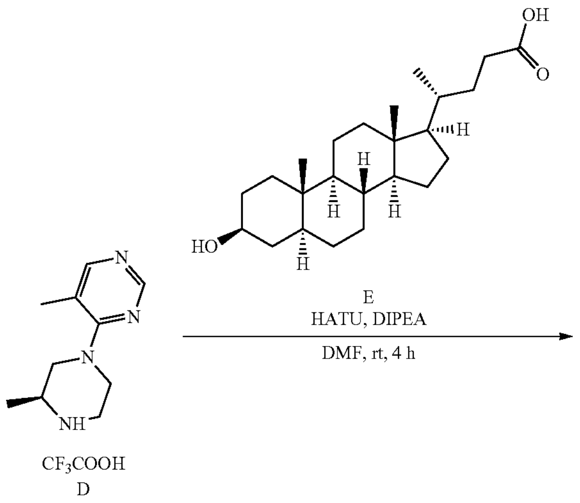

-continued

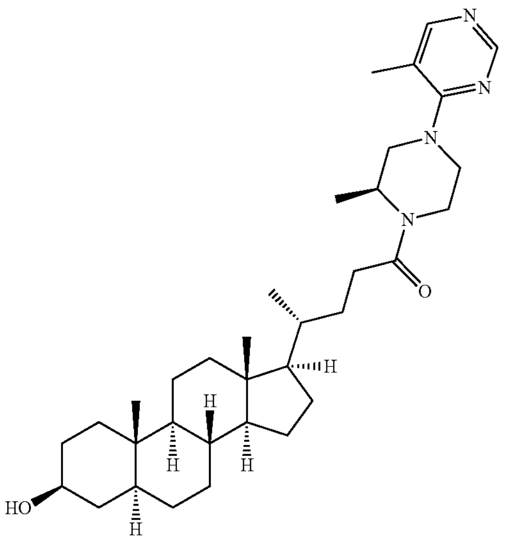

To a solution of compound A (100 mg, 778 μmol) in DMSO (6 mL) was added compound B (156 mg, 778 μmol), CsF (236 mg, 1.56 mmol) and DIPEA (503 mg, 3.89 mmol). The reaction was warmed to 130° C. for 6 hours under $N_2$. Upon completion, the reaction was diluted with water (10 mL) and extracted with ethyl acetate (10 mL). The organic layer was concentrated. The crude product was purified by silica gel chromatography to afford compound C (220 mg, 97%) as white solid.

To a solution of compound C (220 mg, 753 μmol) in DCM (4 mL) was added TFA (2 ml), stirred at room temperature for 4 hours. The reaction was concentrated to give compound D (190 mg) as the TFA salt.

(R)-4-((3S,5S,8R,9S,10S,13R,14S,17R)-3-hydroxy-10,13-dimethylhexadecahydro-1H-cyclopenta[a]phenanthren-17-yl)pentanoic acid (372 mg, 988 μmol) and (S)-5-methyl-4-(3-methylpiperazin-1-yl)pyrimidine 2,2,2-trifluoroacetate (190 mg, 621 μmol) were reacted according to the method of Example T27 to afford the title compound T33 (70 mg, 54%) as white solid. LCMS: $[M+1]^+$=551.50. $^1$H NMR (400 MHz, Chloroform-d) δ 8.61 (s, 1H), 8.17 (s, 1H), 4.06-3.87 (m, 1H), 3.73 (s, 1H), 3.58 (d, J=5.2 Hz, 1H), 3.23-2.83 (m, 2H), 2.36 (s, 1H), 2.26 (s, 3H), 1.96 (d, J=12.4 Hz, 1H), 1.81 (s, 1H), 1.78 (s, 1H), 1.72 (s, 1H), 1.68 (d, J=4.4 Hz, 2H), 1.62 (s, 5H), 1.57 (s, 1H), 1.54 (s, 1H), 1.50 (s, 1H), 1.48-1.42 (m, 2H), 1.38 (s, 1H), 1.33 (s, 2H), 1.30 (s, 2H), 1.26 (s, 4H), 1.24 (s, 1H), 1.10 (d, J=9.2 Hz, 3H), 0.95 (d, J=6.4 Hz, 3H), 0.87 (d, J=8.8 Hz, 2H), 0.80 (s, 3H), 0.66 (s, 3H).

Example T34: (R)-4-((3S,5S,8R,9S,10S,13R,14S,17R)-3-hydroxy-10,13-dimethylhexadecahydro-1H-cyclopenta[a]phenanthren-17-yl)-1-((S)-4-(5-methoxypyrimidin-4-yl)-2-methylpiperazin-1-yl)pentan-1-one

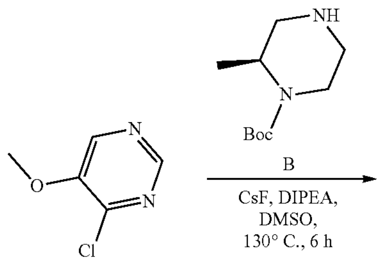

B

A

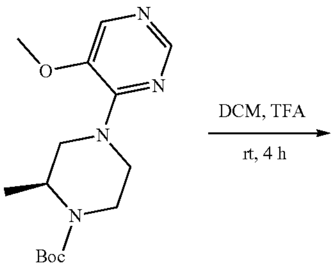

C

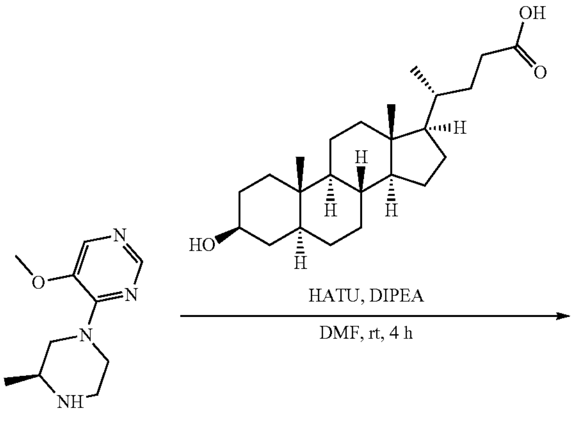

TFA
D

-continued

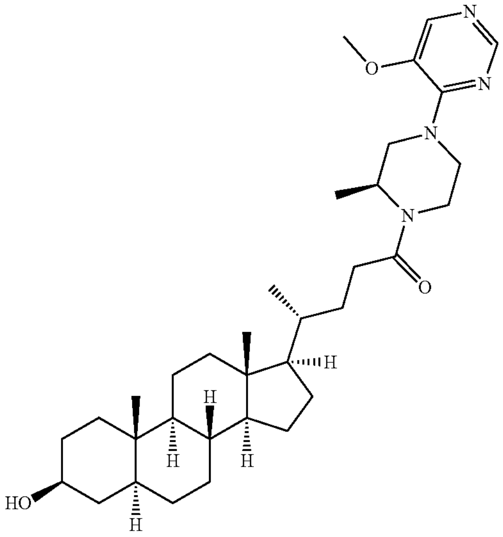

To a solution of compound A (1.0 g, 6.92 mmol) in DMSO (20 mL) was added compound B (1.39 g, 6.92 mmol), CsF (2.1 g, 13.8 mmol) and DIPEA (4.47 g, 34.6 mmol). The reaction was warmed to 130° C. for 6 hours under $N_2$. Upon completion, the reaction was diluted with water (10 mL) and extracted with ethyl acetate (30 mL). The organic layer was concentrated. The crude product was purified by silica gel chromatography to afford compound C (1.58 g, 74%) as white solid.

To a solution of compound C (150 mg, 486 μmol) in DCM was added TFA (2 ml) and stirred at room temperature for 4 hours. The reaction was concentrated to give compound D (100 mg).

(R)-4-((3S,5S,8R,9S,10S,13R,14S,17R)-3-hydroxy-10,13-dimethylhexadecahydro-1H-cyclopenta[a]phenanthren-17-yl)pentanoic acid (181 mg, 480 μmol) and (S)-5-methoxy-4-(3-methylpiperazin-1-yl)pyrimidine TFA salt (100 mg, 311 μmol) were reacted according to the method of Example T27 to afford the title compound T34 (120 mg, 44%). LCMS: $[M+1]^+$=567.50. $^1$H NMR (400 MHz, Chloroform-d) δ 8.32 (s, 1H), 7.91 (s, 1H), 4.59-4.51 (m, 1H), 4.46 (s, 1H), 3.88 (s, 3H), 3.73-3.45 (m, 2H), 3.14 (d, J=13.6 Hz, 1H), 2.98 (d, J=19.2 Hz, 1H), 2.35 (s, 1H), 2.27-2.18 (m, 1H), 1.95 (dd, J=12.4, 3.4 Hz, 1H), 1.82 (dd, J=18.0, 9.6 Hz, 3H), 1.70 (dt, J=18.4, 3.6 Hz, 2H), 1.59-1.52 (m, 3H), 1.51-1.46 (m, 2H), 1.45-1.40 (m, 2H), 1.39-1.33 (m, 2H), 1.33-1.28 (m, 4H), 1.26 (d, J=4.4 Hz, 4H), 1.16 (d, J=6.8 Hz, 2H), 1.12 (d, J=4.0 Hz, 2H), 1.05 (d, J=6.0 Hz, 1H), 1.02-0.99 (m, 1H), 0.95 (d, J=6.4 Hz, 3H), 0.85 (d, J=6.0 Hz, 1H), 0.80 (s, 3H), 0.66 (s, 3H), 0.62 (dd, J=4.0, 1.6 Hz, 1H).

Example T35: cyclopropyl(S)-4-((R)-4-((3S,5S,8R,9S,10S,13R,14S,17R)-3-hydroxy-10,13-dimethylhexadecahydro-1H-cyclopenta[a]phenanthren-17-yl)pentanoyl)-2-methylpiperazine-1-carboxylate
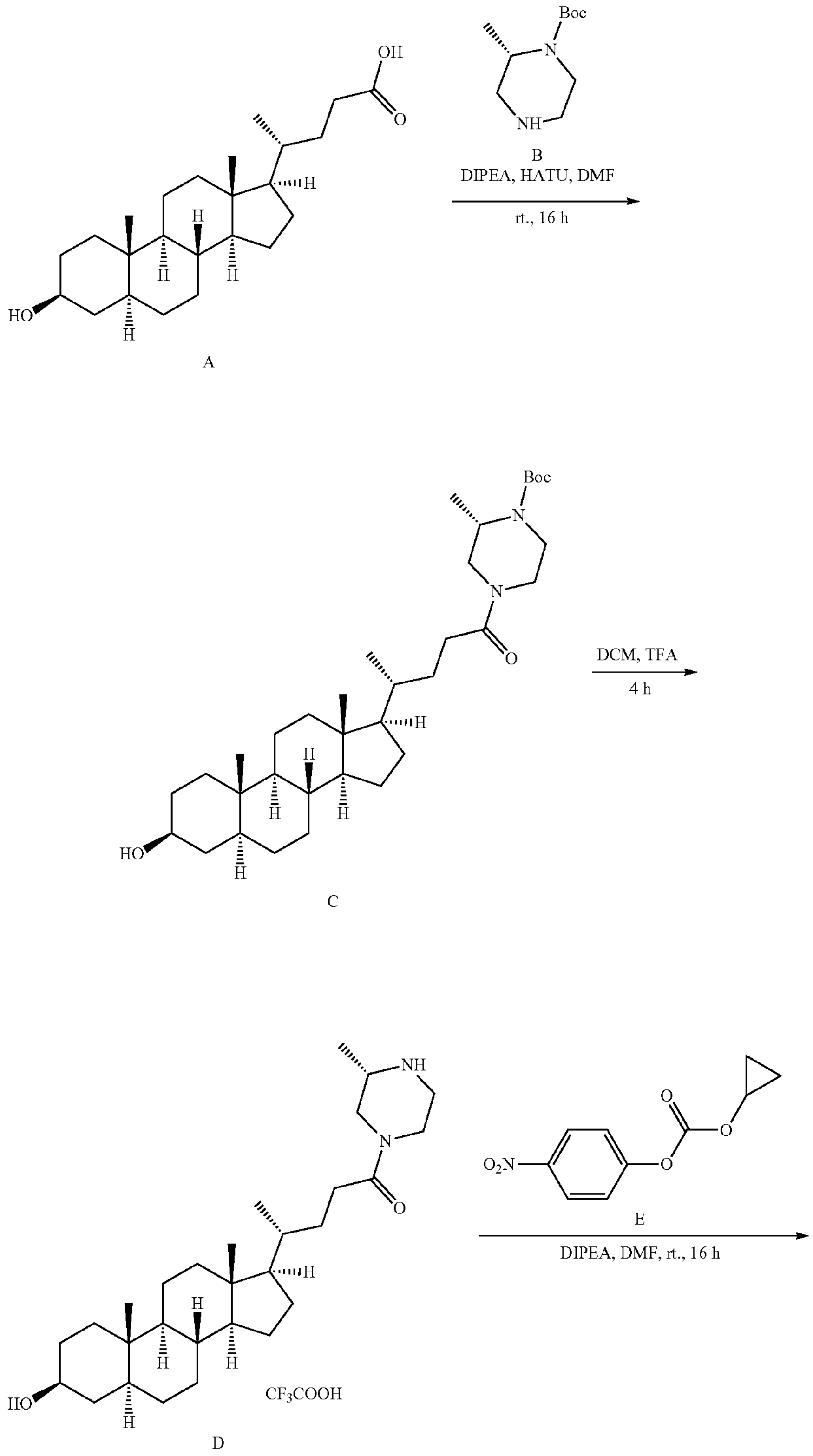

-continued

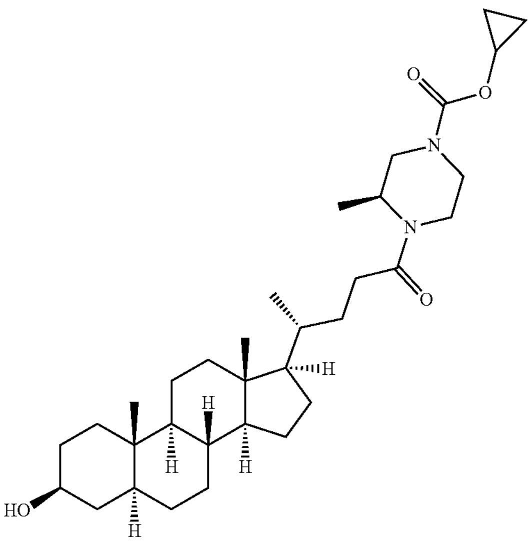

To a solution of compound A (376 mg, 999 μmol), compound B (200 mg, 999 μmol) in DMF(5 mL) was added DIPEA (387 mg, 3 mmol), HATU (570 mg, 1.5 mmol) and the reaction was stirred at room temperature for 16 h under $N_2$. The reaction was diluted with EtOAc (50 mL) and washed with saturated aqueous $NaHCO_3$ (20 mL) and water (20 ml*3), brine (20 mL), dried over sodium sulfate and concentrated under reduced pressure. The residue was purified by silica gel chromatography to afford compound C (358 mg, 64.2%) as white solid.

To a solution of compound C (358 mg, 641 μmol) in dichloromethane (5 mL) was added TFA (2 mL). The reaction was warmed to room temperature under $N_2$ for 16 h. The reaction was concentrated under reduced pressure to afford compound D as the TFA salt (398 mg).

To a solution of compound D (100 mg, 175 μmol) in DMF (3 mL) was added compound E (46.8 mg, 210 μmol), DIPEA (113 mg, 873 μmol) and the reaction was stirred at room temperature under $N_2$ for 4 hours. The reaction was diluted with EtOAc (50 mL), washed with saturated aqueous $NaHCO_3$ (20 mL) and water (20 ml*3). The combined organic layer was washed with brine (20 mL), dried over sodium sulfate, and concentrated under reduced pressure. The residue was purified by silica gel chromatography to afford the title compound T35 (80 mg, 68%) as white solid. LCMS: $[M+1]^+$=543.30. $^1H$ NMR (400 MHz, Chloroform-d) δ 4.52-4.22 (m, 2H), 4.14-4.02 (m, 1H), 3.96-3.69 (m, 1H), 3.61-3.54 (m, 1H), 3.34-2.59 (m, 3H), 2.40-2.15 (m, 2H), 1.94 (d, J=12.4 Hz, 1H), 1.88-1.28 (m, 18H), 1.19-0.85 (m, 14H), 0.79 (s, 3H), 0.74-0.66 (m, 4H), 0.65 (s, 3H).

Example T36: cyclopropyl (S)-4-((R)-4-((3S,5S,8R,9S,10S,13R,14S,17R)-3-hydroxy-10,13-dimethyl-hexadecahydro-1H-cyclopenta[a]phenanthren-17-yl)pentanoyl)-3-methylpiperazine-1-carboxylate

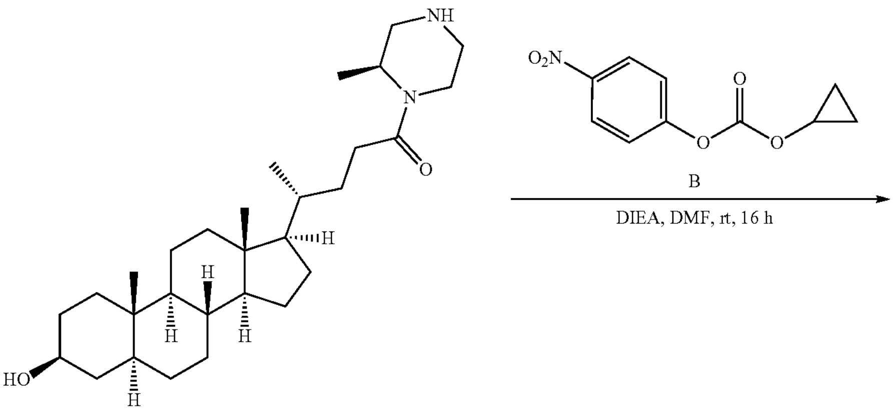

A

-continued

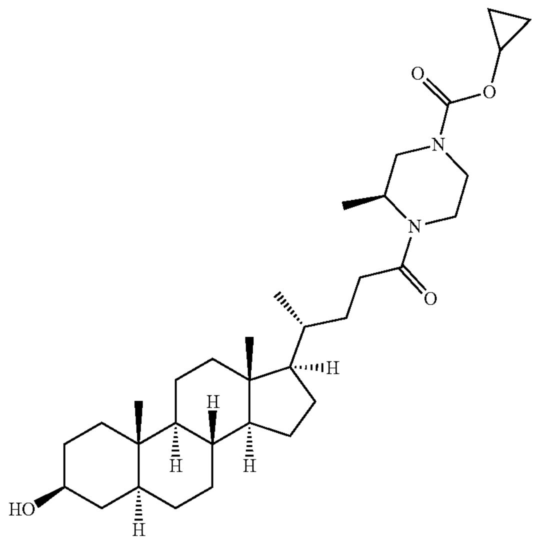

A solution of compound A (100 mg, 218 μmol), compound B (48.7 mg, 218 μmol) and DIEA (84.5 mg, 654 μmol) in DMF (2 mL) was warmed to room temperature for 16 h. Water (20 mL) was added and extracted with EtOAc (20 mL*3). The combined organic layers were concentrated, and the crude product was purified by silica gel chromatography to give the title compound T36 (18 mg, 15.2%). LCMS: $[M+1]^+$=543.50. $^1$H NMR (400 MHz, Chloroform-d) δ 4.91-3.48 (m, 6H), 3.42-2.73 (m, 3H), 2.48-2.11 (m, 2H), 1.94 (dd, J=9.6, 6.4 Hz, 1H), 1.90-1.62 (m, 4H), 1.59-0.82 (m, 28H), 0.80 (s, 3H), 0.75-0.57 (m, 8H).

Example T37: N-(cyclopropylmethyl)-4-((R)-4-((3S,5S,8R,9S,10S,13R,14S,17R)-3-hydroxy-10,13-dimethylhexadecahydro-1H-cyclopenta[a]phenanthren-17-yl)pentanoyl)-N-methylpiperazine-1-carboxamide

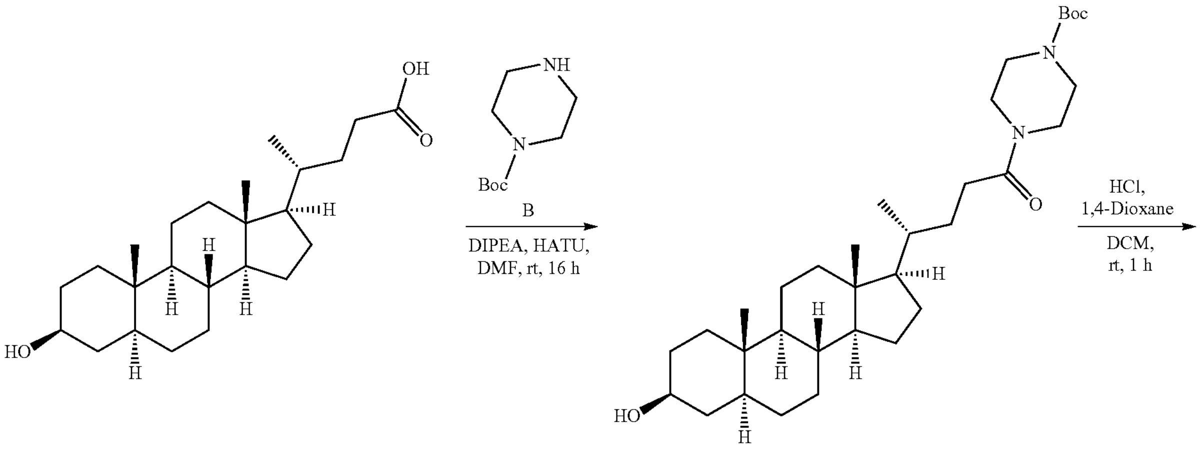

A

C

-continued

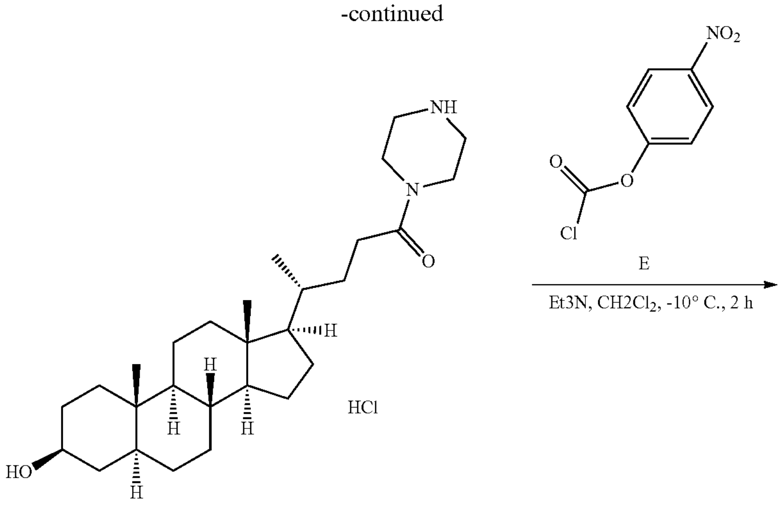

D

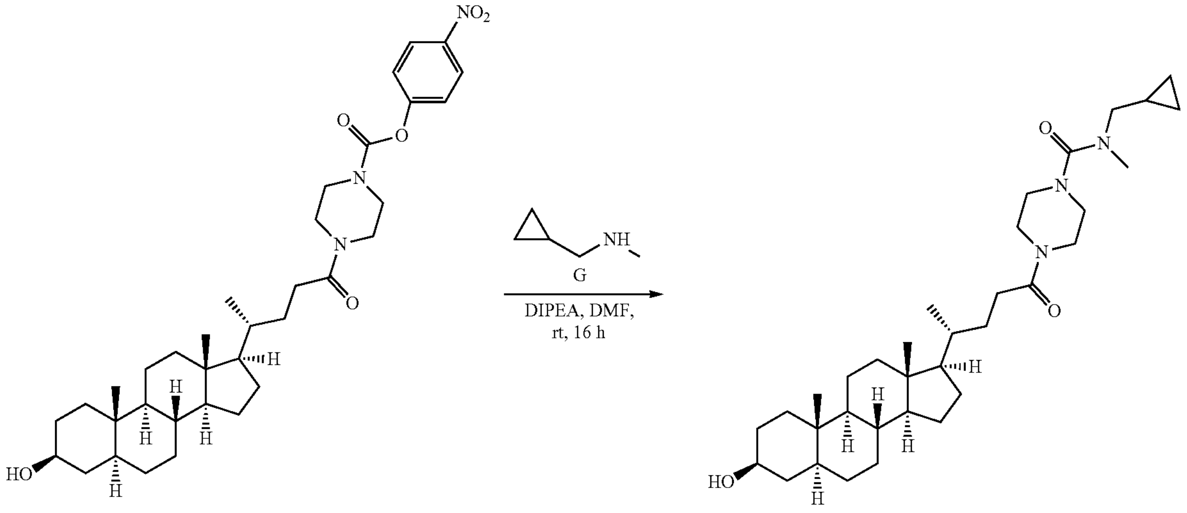

F

To a solution of compound A (1.0 g, 2.66 mmol), compound B (594 mg, 3.19 mmol) and DIPEA (1.7 g, 13.30 mmol) in DMF (5 mL) was added HATU (1.5 g, 3.98 mmol) at room temperature under $N_2$ and stirred for 16 h. The reaction was diluted with saturated aqueous $NH_4Cl$ (30 mL) and extracted with EtOAc (10 mL*2). The combined organic layers were washed with saturated aqueous $NaHCO_3$ (20 mL), water (20 mL) and brine (20 mL), dried over sodium sulfate and concentrated under reduced pressure. The residue was purified by silica gel chromatography to afford C (1.4 g, 97%) as a white solid.

To a solution of compound C (800 mg, 1.47 mmol) in DCM (8 mL) was added 4N HCl in 1,4-dioxane (2 mL, 8 mmol, 4M in 1, 4-dioxane) at room temperature and the reaction was stirred for 1 h. The reaction was concentrated under reduced pressure to afford compound D as the HCl salt (708 mg).

To a solution of compound D (600 mg, 1.35 mmol) and $Et_3N$ (1.4 g, 13.5 mmol) in DCM (12 mL) was added compound E (245 mg, 1.2 mmol) at −10° C. and the reaction was stirred for 2 h. The reaction was concentrated under reduced pressure and the residue was purified by silica gel chromatography to afford compound F (380 mg, 47%) as a white solid.

To a solution of compound F (150 mg, 246 µmol) and compound G (209 mg, 2.46 mmol) in DMF (4 mL) was added DIPEA (96 mg, 738 µmol) at room temperature under $N_2$ and stirred for 16 h.

The reaction was diluted with saturated aqueous $NH_4Cl$ (30 mL) and extracted with EtOAc (10 mL*2). The combined organic layers were washed with saturated aqueous $NaHCO_3$ (20 mL), water (20 mL) and brine (20 mL), dried over sodium sulfate and concentrated under reduced pressure. The residue was purified by silica gel chromatography to afford the title compound T37 (13.6 mg, 10%) as a white solid. LCMS: $[M+H]^+$=556.40. $^1H$ NMR (400 MHz, Chloroform-d) δ 3.62-3.55 (m, 3H), 3.48 (s, 2H), 3.21 (d, J=18.4 Hz, 4H), 3.07 (d, J=6.8 Hz, 2H), 2.93 (s, 3H), 2.42-2.30 (m, 1H), 2.26-2.15 (m, 1H), 2.08-1.92 (m, 2H), 1.90-1.70 (m, 4H), 1.42-1.19 (m, 18H), 1.10 (t, J=7.2 Hz, 4H), 0.94 (d, J=6.4 Hz, 3H), 0.80 (s, 3H), 0.65 (s, 3H), 0.61-0.47 (m, 2H), 0.19 (q, J=5.2 Hz, 2H).

Example T38: (4R)-4-((3S,8R,9S,10S,13R,14S,17R)-3-hydroxy-10,13-dimethylhexadecahydro-1H-cyclopenta[a]phenanthren-17-yl)-1-(4-(5-methyl-1,3,4-oxadiazol-2-yl)piperazin-1-yl)pentan-1-one

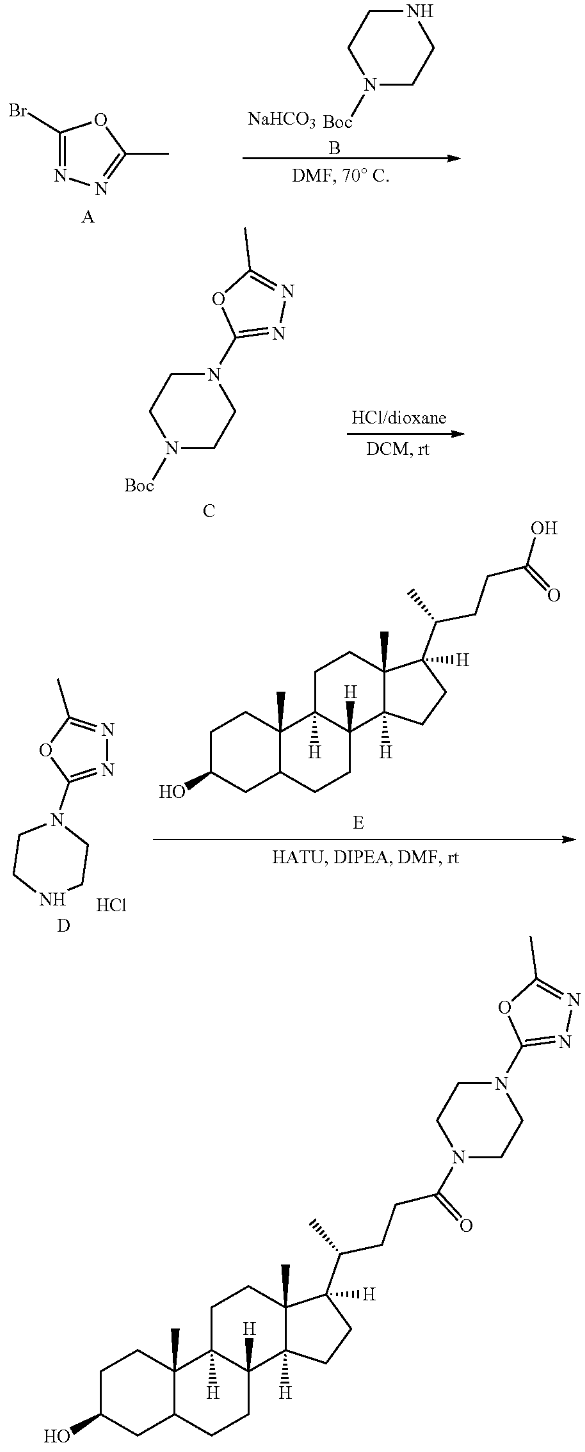

To a solution of compound A (150 mg, 920 μmol) in DMF (5 mL) was added compound B (171 mg, 920 μmol) and saturated aqueous $NaHCO_3$ (155 mg, 1.84 mmol). The reaction was warmed to 70° C. under $N_2$ for 16 h. The reaction was quenched with water (20 mL) and extracted with EtOAc (10 mL*2). The combined organic layers were washed by brine, dried over sodium sulfate, filtered, and concentrated. The residue was purified by silica gel chromatography to afford compound C (151 mg, 61%) as a white solid.

To a solution of compound C (100 mg, 373 μmol) in DCM (2 mL) was added 4N HCl in 1,4-dioxane (1 mL) at room temperature and the reaction was stirred for 2 h. The reaction was concentrated under reduced pressure to afford compound D as the HCl salt (75.0 mg).

(R)-4-((3S,5S,8R,9S,10S,13R,14S,17R)-3-hydroxy-10,13-dimethylhexadecahydro-1H-cyclopenta[a]phenanthren-17-yl)pentanoic acid (112 mg, 298 μmol) and 2-methyl-5-(piperazin-1-yl)-1,3,4-oxadiazole hydrochloride (76.3 mg, 373 μmol) were reacted according to the method of Example T27 to afford the title compound T38 (160 mg, 81%) as a white solid. LCMS: $[M+1]^+=527.35$. $^1H$ NMR (400 MHz, $CDCl_3$) δ 3.77-3.55 (m, 5H), 3.54-3.41 (m, 4H), 2.45-2.34 (m, 4H), 2.30-2.19 (m, 1H), 1.95 (dt, J=12.4, 3.2 Hz, 1H), 1.90-1.70 (m, 4H), 1.70-1.66 (m, 1H), 1.59-1.40 (m, 6H), 1.39-1.26 (m, 7H), 1.17-0.91 (m, 10H), 0.80 (s, 3H), 0.70-0.57 (m, 4H).

Example T39: (4R)-4-[(1R,3aS,3bR,5aS,7S,9aS,9bS,11aR)-7-hydroxy-9a,11a-dimethyl-hexadecahydro-1H-cyclopenta[a]phenanthren-1-yl]-1-[4-(5-cyclopropoxypyrimidin-4-yl)piperazin-1-yl]pentan-1-one

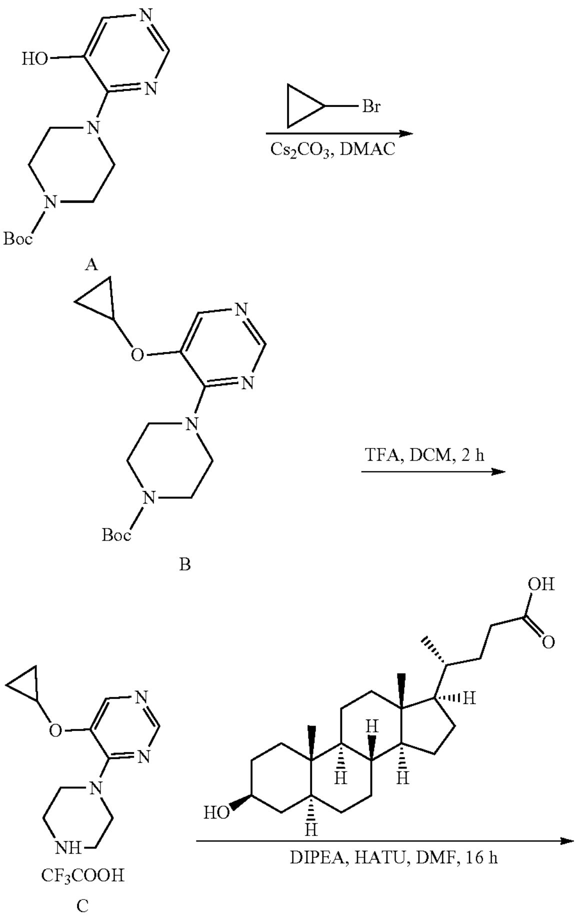

-continued

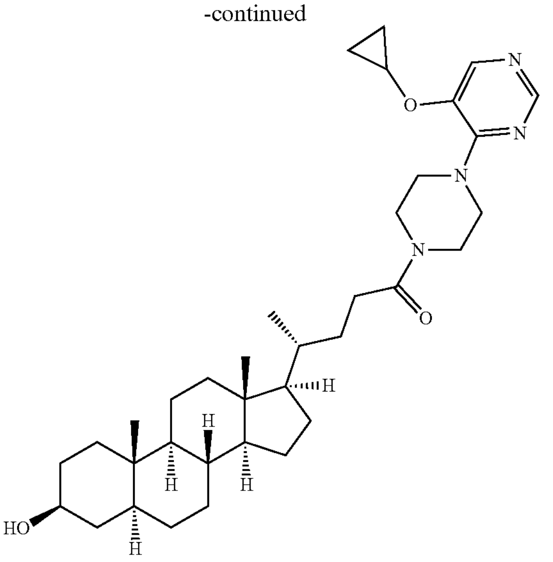

To a solution of compound A (150 mg, 535 μmol) in DMF (5 mL) was added $Cs_2CO_3$ (872 mg, 2.68 mmol) and bromocyclopropane (647 mg, 5.35 mmol). The reaction was heated at 130° C. for 16 h under nitrogen in a sealed tube. The reaction was diluted with water and extracted with ethyl acetate (20 mL). The organic layer was washed with water (5 mL) and brine (5 mL), dried over sodium sulfate, and concentrated under reduced pressure. The crude product was purified by silica gel chromatography to afford compound B (80 mg, 46.6%) as white solid.

To a solution of compound B (80 mg, 250 μmol) in DCM (3 mL) was added TFA (0.5 mL) at room temperature. The reaction was warmed to room temperature for 2 h. The reaction was concentrated under reduced pressure to afford compound C as the TFA salt (84 mg).

(R)-4-((3S,5S,8R,9S,10S,13R,14S,17R)-3-hydroxy-10,13-dimethylhexadecahydro-1H-cyclopenta[a]phenanthren-17-yl)pentanoic acid (75.7 mg, 201 μmol) and 5-cyclopropoxy-4-(piperazin-1-yl)pyrimidine 2,2,2-trifluoroacetate (84 mg, 251 μmol) were reacted according to the method of Example T27 to afford the title compound T39 (38.0 mg, 26.1%) as a white solid. LCMS: $[M+1]^+$=579.50. $^1H$ NMR (400 MHz, $CDCl_3$) δ 8.36 (s, 1H), 8.29 (s, 1H), 3.81-3.52 (m, 10H), 2.43-2.35 (m, 1H), 2.27-2.19 (m, 1H), 1.97-1.92 (m, 1H), 1.87-1.76 (m, 3H), 1.72-1.62 (m, 4H), 1.58-1.53 (m, 2H), 1.50-1.43 (m, 3H), 1.39-1.31 (m, 3H), 1.30-1.24 (m, 6H), 1.18-1.03 (m, 4H), 1.02-0.99 (m, 1H), 0.94 (d, J=6.6 Hz, 3H), 0.88-0.82 (m, 3H), 0.80 (s, 3H), 0.65 (s, 4H).

Example T40: (R)-4-((3S,5S,8R,9S,10S,13R,14S,17R)-3-hydroxy-10,13-dimethylhexadecahydro-1H-cyclopenta[a]phenanthren-17-yl)-1-(4-(5-methoxypyrimidin-4-yl)piperazin-1-yl) pentan-1-one

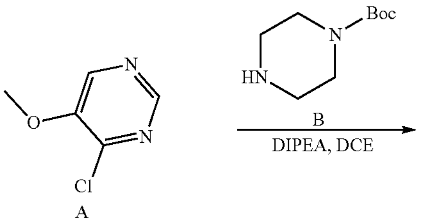

A

-continued

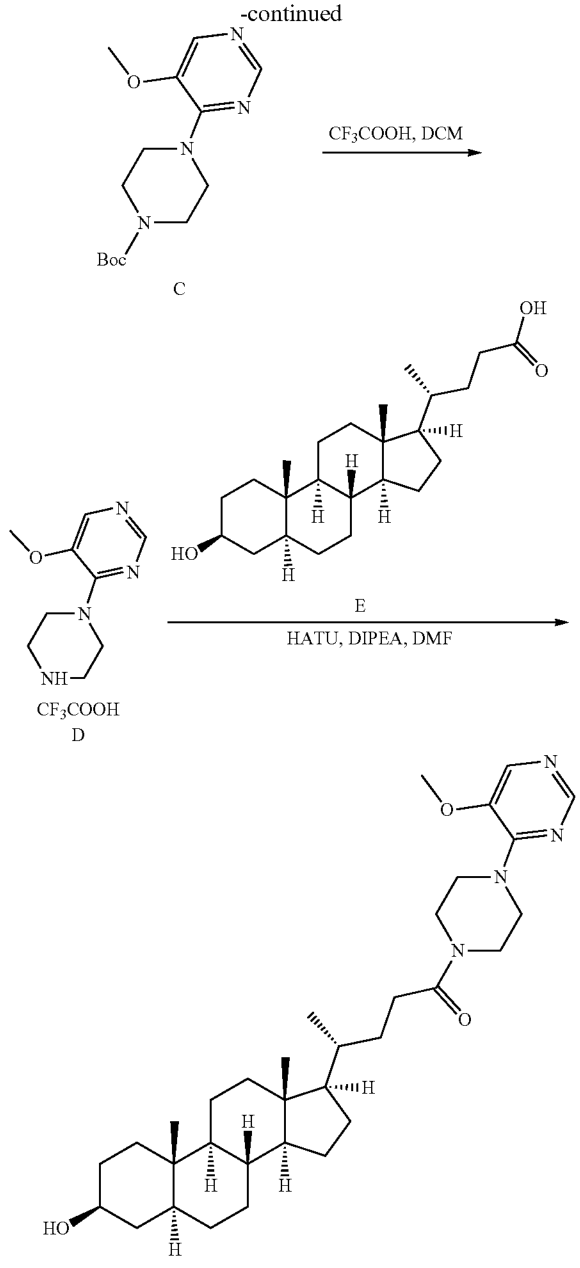

To a solution of compound A (200 mg, 1.38 mmol) in 1,2-dichloroethane (8 mL) was added DIPEA (745 mg, 5.76 mmol) and compound B (745 mg, 5.76 mmol) at room temperature and stirred at 80° C. under nitrogen for 16 hours. Upon completion, the reaction was quenched by water (20 mL) and extracted with ethyl acetate (20 mL*3). The combined organic layers were washed with brine, dried over sodium sulfate, filtered, and concentrated. The crude product was purified by silica gel chromatography to afford compound C (150 mg, 44%) as a white solid.

To a solution of compound C (150 mg, 510 μmol) in dichloromethane (3 mL) was added TFA (1 mL) at room temperature and was stirred for 1 hour. Upon completion, the reaction mixture was added dichloromethane (10 mL) and concentrated three times to afford compound D (140 mg, 94%) as the TFA salt.

(R)-4-((3S,5S,8R,9S,10S,13R,14S,17R)-3-hydroxy-10,13-dimethylhexadecahydro-1H-cyclopenta[a]phenanthren- 17-yl)pentanoic acid (138 mg, 366 μmol) and 5-methoxy-4-(piperazin-1-yl)pyrimidine 2,2,2-trifluoroacetate (140 mg, 455 μmol) were reacted according to the method of Example T27 to afford the title compound T40 (120 mg, 59%) as a white solid. LCMS: $[M+1]^+$=553.53. $^1$H NMR (400 MHz, Chloroform-d) δ 8.35 (s, 1H), 7.94 (s, 1H), 3.88 (s, 3H), 3.81-3.66 (m, 6H), 3.61-3.55 (m, 3H), 2.43-2.37 (m, 1H), 2.25 (m, 1H), 1.95 (dt, J=12.4, 3.2 Hz, 1H), 1.86 (dd, J=8.8, 4.8 Hz, 1H), 1.83-1.75 (m, 2H), 1.72 (t, J=3.6 Hz, 1H), 1.67 (d, J=9.2 Hz, 4H), 1.55 (dt, J=10.0, 3.6 Hz, 2H), 1.50-1.41 (m, 2H), 1.38-1.32 (m, 2H), 1.29 (s, 2H), 1.26 (d, J=4.2 Hz, 3H), 1.23 (d, J=4.2 Hz, 1H), 1.13-1.08 (m, 2H), 1.00 (p, J=6.0 Hz, 2H), 0.95 (d, J=6.6 Hz, 3H), 0.89-0.83 (m, 1H), 0.80 (s, 3H), 0.66 (s, 4H).

Example T41: (R)-4-((3S,5S,8R,9S,10S,13R,14S,17R)-3-hydroxy-10,13-dimethylhexadecahydro-1H-cyclopenta[a]phenanthren-17-yl)-1-(4-(1-methyl-1H-pyrazol-5-yl)piperazin-1-yl)pentan-1-one

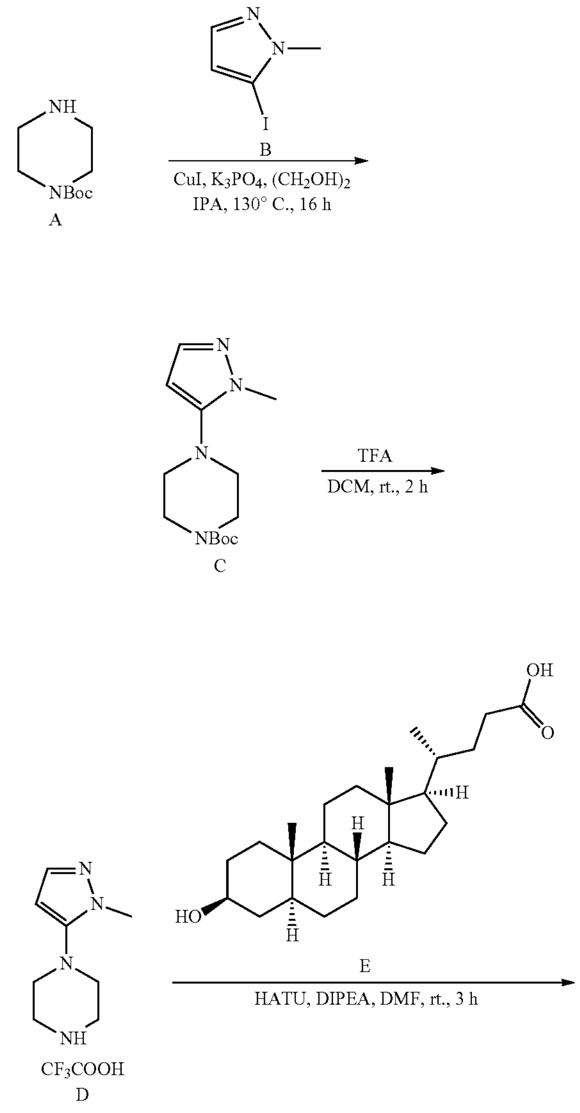

-continued

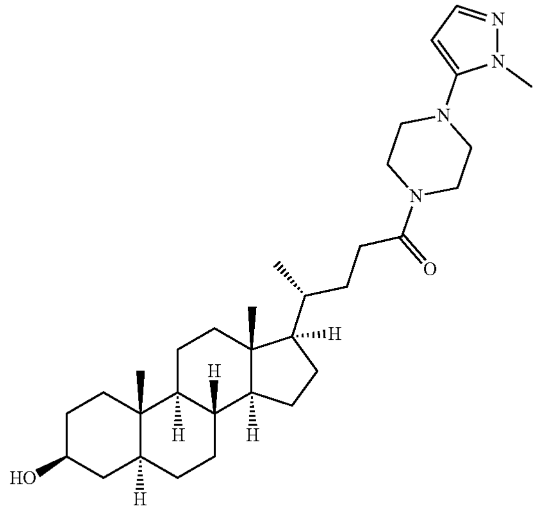

To a solution of compound A (200 mg, 1.07 mmol) in isopropanol (3 mL) was added compound B (447 mg, 2.15 mmol), CuI (40.9 mg, 215 μmol), $K_3PO_4$ (912 mg, 4.3 mmol) and $(CH_2OH)_2$ (133 mg, 2.15 mmol). The reaction was warmed to 130° C. for 16 h. The reaction was added water (5 mL) and extracted with EtOAc (15 mL). The organic layer was dried over sodium sulfate and concentrated under reduced pressure. The crude was purified by silica gel chromatography to afford compound C (70 mg, 24.5%) as a yellow oil.

To a solution of compound C (70 mg, 263 μmol) in DCM (2 mL) was added TFA (0.5 mL). The reaction was warmed to room temperature for 2 h. The reaction was concentrated under reduced pressure to afford compound D as the TFA salt (68 mg).

(R)-4-((3S,5S,8R,9S,10S,13R,14S,17R)-3-hydroxy-10,13-dimethylhexadecahydro-1H-cyclopenta[a]phenanthren-17-yl)pentanoic acid (80 mg, 359 μmol) and 1-(1-methyl-1H-pyrazol-5-yl)piperazine (42.4 mg, 155 μmol) were reacted according to the method of Example T27 to afford the title compound T41 (53.1 mg, 47.4%) as a white solid. LCMS: $[M+1]^+$=525.50. $^1$H NMR (400 MHz, Chloroform-d) δ 7.16 (d, J=2.0 Hz, 1H), 5.64 (d, J=2.4 Hz, 1H), 3.75-3.71 (m, 5H), 3.62-3.54 (m, 3H), 3.19-3.17 (m, 4H), 2.44-2.36 (m, 1H), 2.28-2.20 (m, 1H), 1.95 (dt, J=12.6, 3.2 Hz, 1H), 1.88-1.70 (m, 4H), 1.70-1.54 (m, 10H), 1.50-1.40 (m, 3H), 1.38-1.26 (m, 6H), 1.24 (d, J=3.6 Hz, 1H), 1.14-1.08 (m, 4H), 1.02-0.96 (m, 2H), 0.94 (d, J=6.4 Hz, 3H), 0.92-0.82 (m, 2H), 0.80 (s, 3H), 0.66 (s, 3H), 0.64-0.58 (m, 1H).

Example T42: (S)-2-((3S,5S,8R,9S,10S,13S,14S,17R)-3-hydroxy-10,13-dimethylhexadecahydro-1H-cyclopenta[a]phenanthren-17-yl)propyl 4-(pyridin-4-yl)piperazine-1-carboxylate

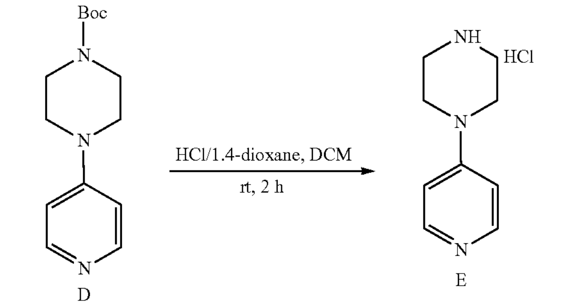

D

E

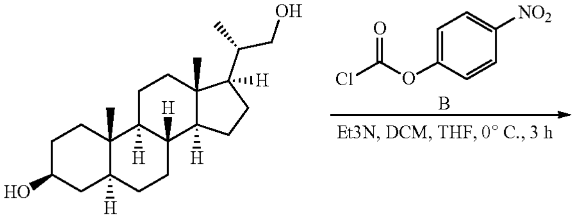

A

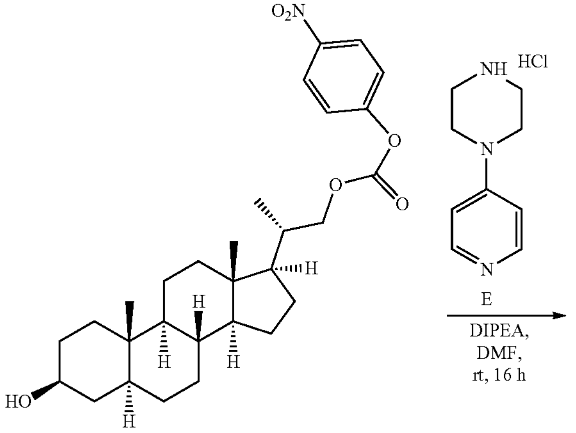

C

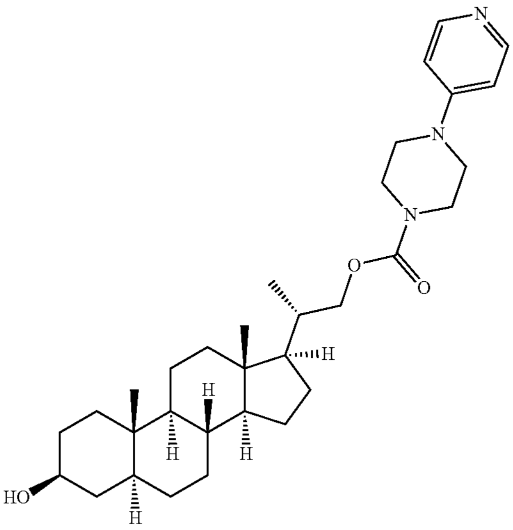

To a 0° C. solution of compound A (100 mg, 299 μmol) in DCM (5 mL), was added $Et_3N$ (90.7 mg, 897 μmol), compound B (48.2 mg, 239 μmol) and the reaction stirred to 0° C. under $N_2$ for 3 h. The reaction was diluted with saturated aqueous $NH_4Cl$ (10 mL) and extracted with EtOAc (10 mL*2). The combined organic layers were washed with saturated aqueous $NaHCO_3$ (20 mL), water (20 mL) and brine (20 mL), dried over sodium sulfate and concentrated under reduced pressure. The residue was purified by silica gel chromatography to afford compound C (60 mg, 40%) as a yellow oil.

To a solution of compound D (50 mg, 190 μmol) in DCM (2 mL) was added 4 M HCl in 1,4-dioxane (1 mL) at room temperature and the reaction was stirred for 2 h. The reaction was concentrated under reduced pressure to afford compound E as the HCl salt (38 mg).

To a solution of compound E (38 mg, 190 μmol) and DIPEA (62.1 mg, 480 μmol) in DMF (5 mL) was added compound C (60 mg, 120 μmol) at room temperature under $N_2$ and stirred for 16 h.

The reaction was diluted with saturated aqueous $NH_4Cl$ (30 mL) and extracted with EtOAc (10 mL*2). The combined organic layers were washed with saturated aqueous $NaHCO_3$ (20 mL), water (20 mL) and brine (20 mL), dried over sodium sulfate and concentrated under reduced pressure. The residue was purified by silica gel chromatography to afford the title compound T42 (20 mg, 32%) as a white solid. LCMS: $[M+1]^+$=524.35. $^1H$ NMR (400 MHz, Chloroform-d) δ 8.10-8.04 (m, 2H), 6.50-6.44 (m, 2H), 3.94 (dd, J=10.4, 3.6 Hz, 1H), 3.60 (dd, J=10.4, 7.2 Hz, 1H), 3.46-3.33 (m, 5H), 3.18 (t, J=5.2 Hz, 4H), 1.75 (d, J=12.4 Hz, 1H), 1.64-1.02 (m, 16H), 0.99-0.58 (m, 14H), 0.47-0.39 (m, 4H).

Example T43: 1-(2S)-2-[(1R,3aS,3bR,5aS,7S,9aS,9bS,11aS)-7-hydroxy-9a,11a-dimethyl-hexadecahydro-1H-cyclopenta[a]phenanthren-1-yl]propyl 4-methyl piperazine-1,4-dicarboxylate; methane

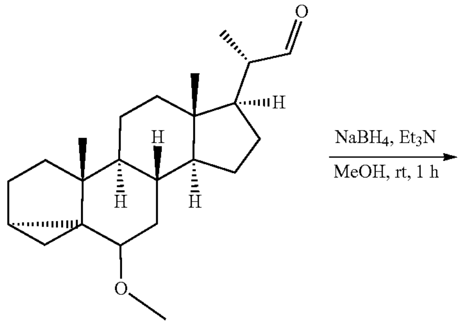

A

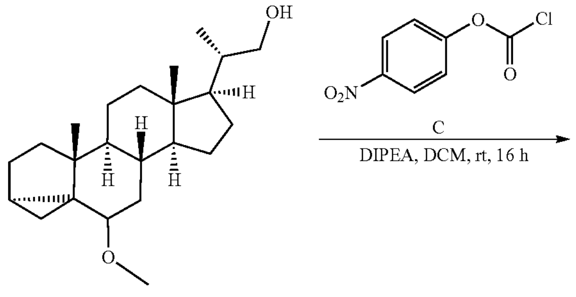

B

-continued

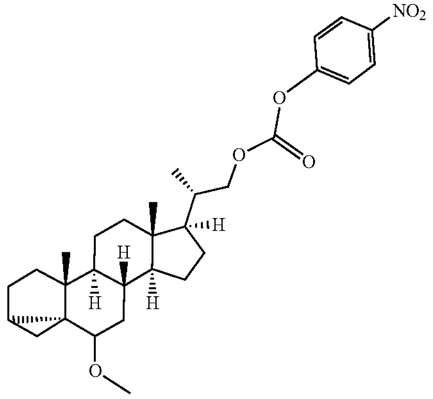

D

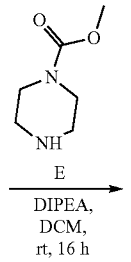

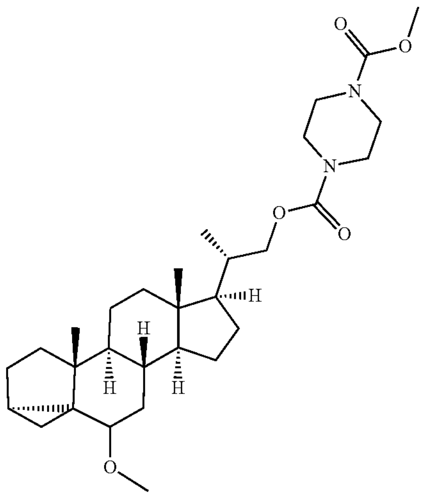

F

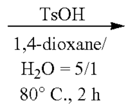

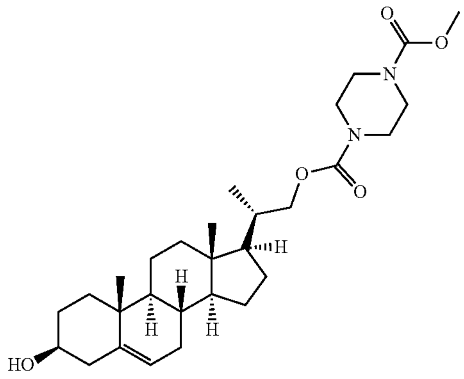

G

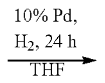

-continued

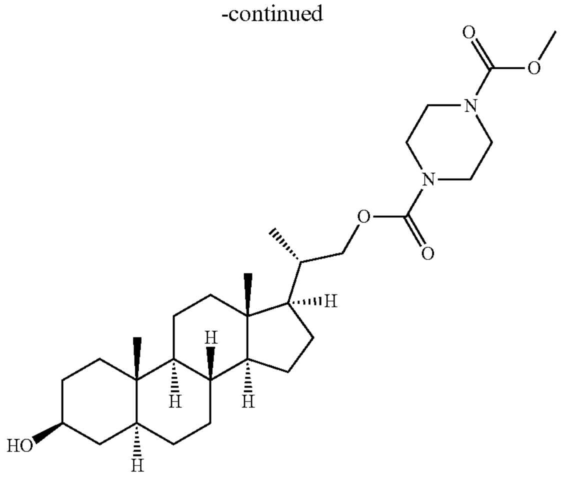

To a solution of compound A (30 mg, 871 μmol) in methanol (5 mL) was added $Et_3N$ (352 mg, 3.48 mmol) and $NaBH_4$ (66 mg, 1.74 mmol) at 0° C. The reaction was warmed to room temperature for 1 hour. The reaction was quenched with water (30 mL) and the reaction was extracted with ethyl acetate (30 mL*3). The combined organic phase was washed with brine (30 mL), dried over sodium sulfate, concentrated under reduced pressure and purified by silica gel chromatography to afford compound B (300 mg, 99%) as white solid.

To a solution of compound B (400 mg, 1.15 mmol) in DCM (10 mL) was added compound C (465 mg, 2.31 mmol), DIPEA (597 mg, 4.62 mmol) and the reaction was warmed to room temperature for 16 hours. Water (30 mL) was added, and the reaction was extracted with DCM (30 mL*3). The combined organic phase was washed with brine (30 mL), dried over sodium sulfate, concentrated under reduced pressure and the residue was purified by silica gel chromatography to afford compound D (250 mg, 43%) as yellow solid.

To a solution of compound D (50 mg, 0.10 mmol) and compound E (14.4 mg, 0.1 mmol) in DMF (2 mL) was added DIPEA (52 mg, 0.4 mmol). The reaction was warmed to room temperature for 16 hours. Water (20 mL) was added, and the reaction was extracted with EtOAc (20 mL*3). The combined organic phase was washed with water (20 mL*2), dried over sodium sulfate, and concentrated under reduced pressure. The residue was purified by silica gel chromatography to afford compound F (50 mg, 96%) as yellow solid.

To a solution of compound F (50 mg, 96.8 μmol) in water (0.4 mL) and 1, 4-dioxane (2 mL) at room temperature was added TsOH (9 mg, 48.4 μmol). The reaction was warmed to 80° C. for 2 hours. The reaction was cooled to room temperature. Water (20 mL) was added. The reaction was extracted with EtOAc (20 mL*3). The combined organic phase was washed with brine (20 mL), dried over sodium sulfate, and concentrated under reduced pressure. The residue was purified by silica gel chromatography to afford compound G (35 mg, 72%) as a yellow oil.

To a solution of compound G (40 mg, 79.6 μmol) in THE (4 mL) was added 10% Pd/C (20 mg). The reaction was warmed to room temperature under an $H_2$ atmosphere for 24 h. The reaction was filtered and concentrated under reduced pressure. The crude was purified by silica gel chromatography to afford the title compound T43 (18 mg, 43%) as white solid. $^1H$ NMR (400 MHz, Chloroform-d) δ 4.12 (dd, J=10.4, 3.6 Hz, 1H), 3.78 (dd, J=10.4, 7.6 Hz, 1H), 3.72 (s, 3H), 3.63-3.55 (m, 1H), 3.46 (s, 8H), 2.04-1.92 (m, 2H), 2.04-1.93 (m, 2H), 1.83-1.76 (m, 2H), 1.73-1.67 (m, 2H), 1.53-1.47 (m, 2H), 1.45-1.41 (m, 1H), 1.33-1.23 (m, 9H), 1.17-1.07 (m, 3H), 1.00 (d, J=6.4 Hz, 4H), 0.88 (t, J=5.2 Hz, 1H), 0.80 (s, 3H), 0.71-0.61 (m, 4H).

Example T44: (4R)-4-[(1R,3aS,3bR,5aS,7S,9aS,9bS,11aR)-7-hydroxy-9a,11a-dimethyl-hexadecahydro-1H-cyclopenta[a]phenanthren-1-yl]-1-[4-(pyrimidin-2-yl)piperazin-1-yl]pentan-1-one

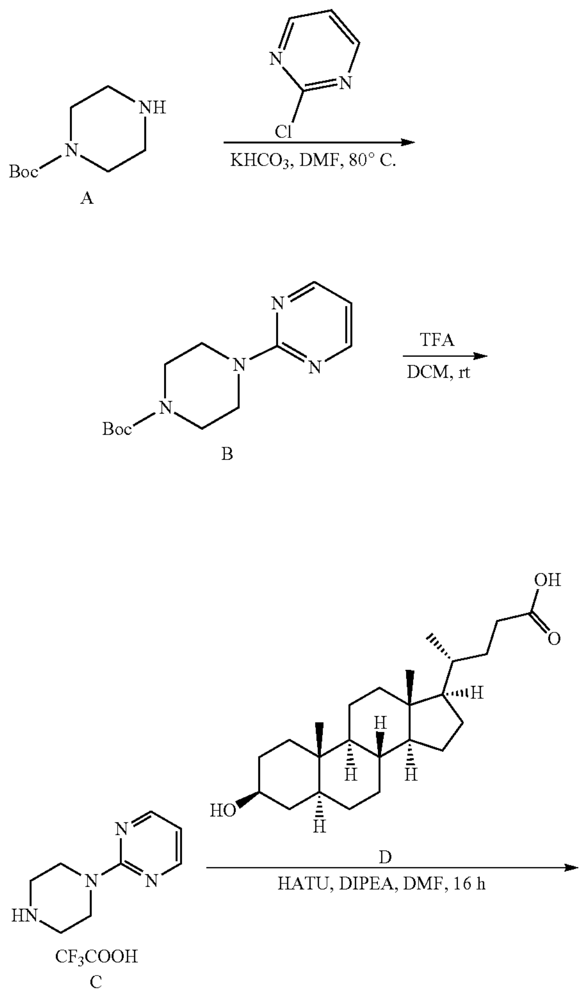

-continued

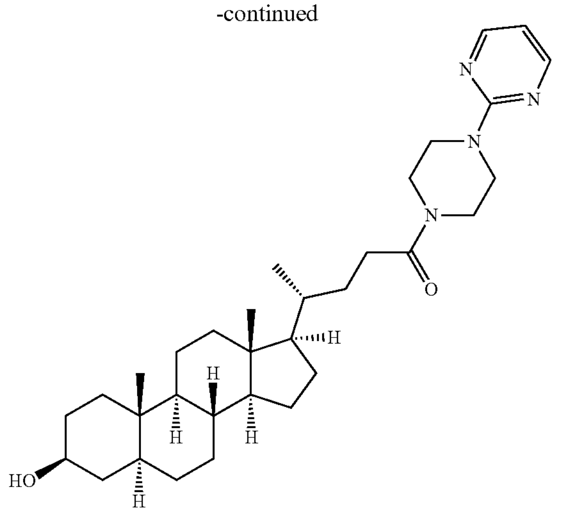

To a room temperature solution of compound A (200 mg, 1.07 mmol) in DMF (8 mL) was added KHCO3 (161 mg, 1.61 mmol) and 2-chloropyrimidine (135 mg, 1.18 mmol). The reaction was heated at 80° C. for 16 h under nitrogen. The reaction was diluted with water and extracted with ethyl acetate. The organic layer was washed with water (10 mL) and brine (5 mL), dried over sodium sulfate, and concentrated under reduced pressure. The crude product was purified by silica gel chromatography to afford compound B (100 mg, 35.2%) as yellow solid.

To a solution of compound B (100 mg, 378 μmol) in dichloromethane (5 mL) was added trifluoroacetic acid (1 mL) dropwise at room temperature and stirred for 2 h. The reaction was concentrated under reduced pressure to give compound C as the TFA salt (105 mg).

(R)-4-((3S,5S,8R,9S,10S,13R,14S,17R)-3-hydroxy-10,13-dimethylhexadecahydro-1H-cyclopenta[a]phenanthren-17-yl)pentanoic acid (142 mg, 377 μmol) and 2-(piperazin-1-yl)pyrimidine 2,2,2-trifluoroacetate (105 mg, 377 μmol) were reacted according to the method of Example T27 to afford the title compound T44 (100.9 mg, 51.1%) as a white solid. LCMS: $[M+1]^+$=523.40. $^1$H NMR (400 MHz, $CDCl_3$) δ 8.32 (d, J=4.4 Hz, 2H), 6.53 (t, J=4.8 Hz, 1H), 3.86-3.79 (m, 4H), 3.69 (t, J=5.2 Hz, 2H), 3.62-3.51 (m, 3H), 2.45-2.37 (m, 1H), 2.30-2.22 (m, 1H), 1.97-1.93 (m, 1H), 1.88-1.76 (m, 3H), 1.74-1.65 (m, 2H), 1.63-1.53 (m, 5H), 1.52-1.40 (m, 3H), 1.39-1.22 (m, 9H), 1.15-1.07 (m, 3H), 0.95 (d, J=6.4 Hz, 3H), 0.89-0.83 (m, 1H), 0.80 (s, 3H), 0.66 (s, 4H).

Example T45: Propan-2-yl 4-[(4R)-4-[(1R,3aS,3bR,5aS,7S,9aS,9bS,11aR)-7-hydroxy-9a,11a-dimethyl-hexadecahydro-1H-cyclopenta[a]phenanthren-1-yl]pentanoyl]piperazine-1-carboxylate

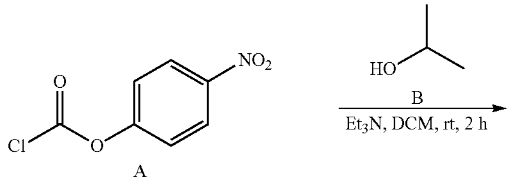

-continued

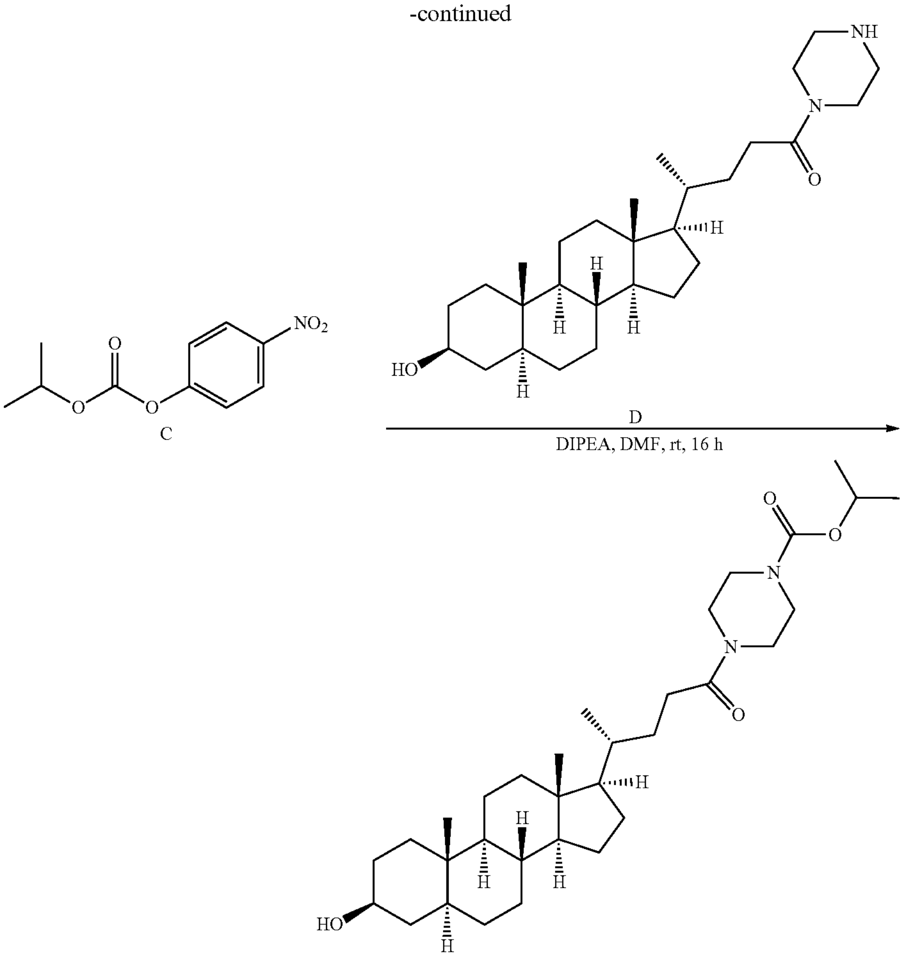

31

To a room temperature solution of compound A (300 mg, 1.49 mmol) and compound B (89 mg, 1.49 mmol) in DCM (3 mL) was added $Et_3N$ (602 mg, 5.95 mmol) and the reaction stirred for 16 hours. The reaction was diluted with water (30 mL) and the reaction was extracted with DCM (30 mL*2). The combined organic phase was washed with water (30 mL), dried over sodium sulfate, concentrated under reduced pressure and the residue was purified by silica gel chromatography to afford compound C (200 mg, 60%) as yellow solid.

To a solution of compound C (100 mg, 478 μmol) and compound D (170 mg, 382 μmol) in DMF (3 mL) was added DIPEA (247 mg, 1.91 mmol) and the reaction stirred for 16 hours. The reaction was quenched by water (30 mL) and extracted with ethyl acetate (30 mL*3). The combined organic phase was washed with water (30 mL*2), brine (30 mL), dried over sodium sulfate and concentrated under reduced pressure. The residue was purified by silica gel chromatography to afford the title compound T45 (18 mg, 7%) as white solid. LCMS: [M+1]+=531.40. $^1H$ NMR (400 MHz, Chloroform-d) δ 4.97-4.91 (m, 1H), 3.61-3.56 (m, 3H), 3.51-3.41 (m, 6H), 2.44-2.32 (m, 1H), 2.26-2.18 (m, 1H), 1.94 (dd, J=12.4, 3.6 Hz, 1H), 1.84-1.75 (m, 3H), 1.73-1.70 (m, 3H), 1.67-1.61 (m, 2H), 1.58-1.53 (m, 2H), 1.48-1.44 (m, 2H), 1.40-1.31 (m, 4H), 1.25 (d, J=6.4 Hz, 10H), 1.14-1.06 (m, 3H), 0.97-0.91 (m, 5H), 0.80 (s, 3H), 0.65 (s, 5H).

Example T46: (R)-4-((3S,5S,8R,9S,10S,13R,14S,17R)-3-hydroxy-10,13-dimethylhexadecahydro-1H-cyclopenta[a]phenanthren-17-yl)-1-(4-(2-methyl-2H-tetrazole-5-carbonyl)piperazin-1-yl)pentan-1-one

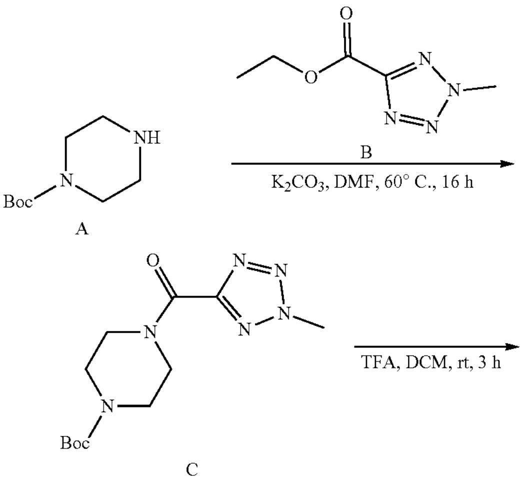

-continued

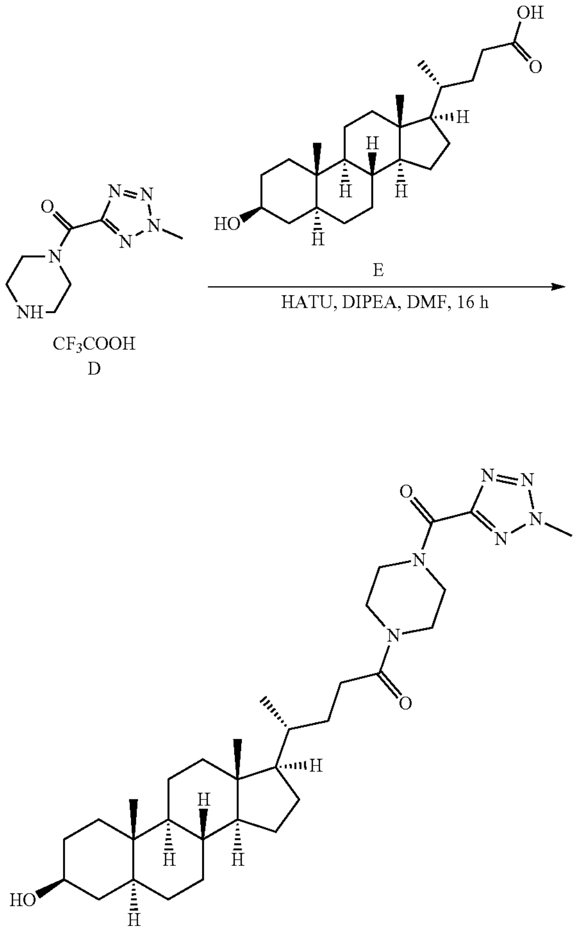

To a room temperature solution of compound A (100 mg, 537 μmol) in DMF (5 mL) was added compound B (83.8 mg, 537 μmol), $K_2CO_3$ (223 mg, 1.61 mmol) and the reaction was heated to 60° C. under $N_2$ for 16 h. The reaction was cooled to room temperature and the reaction was diluted with water (10 mL) and extracted with EtOAc (10 mL*2). The combined organic layers were washed with saturated aqueous $NaHCO_3$ (20 mL), water (20 mL) and brine (20 mL), dried over sodium sulfate and concentrated under reduced pressure. The residue was purified by silica gel chromatography to afford compound C (50 mg, 31%) as a yellow oil.

To a solution of compound C (50 mg, 169 μmol) in DCM (2 mL) was added TFA (1 mL) at room temperature and the reaction was stirred for 2 h. The reaction was concentrated under reduced pressure to afford compound D as the TFA salt (52 mg).

(R)-4-((3S,5S,8R,9S,10S,13R,14S,17R)-3-hydroxy-10,13-dimethylhexadecahydro-1H-cyclopenta[a]phenanthren-17-yl)pentanoic acid (63 mg, 169 μmol) and (2-methyl-2H-tetrazol-5-yl)(piperazin-1-yl)methanone 2,2,2-trifluoroacetate (52 mg, 169 μmol) were reacted according to the method of Example T27 to afford the title compound T46 (40 mg, 42%) as a white solid. LCMS: $[M+1]^+$=555.40. $^1H$ NMR (400 MHz, Chloroform-d) δ: 4.44 (s, 3H), 3.98-3.53 (m, 10H), 2.46-2.20 (m, 2H), 2.00-1.63 (m, 8H), 1.53-1.28 (m, 11H), 1.19-0.77 (m, 18H), 0.66-0.57 (m, 4H).

Example T47: Methyl (S)-4-((R)-4-((3S,5S,8R,9S,10S,13R,14S,17R)-3-hydroxy-10,13-dimethylhexadecahydro-1H-cyclopenta[a]phenanthren-17-yl)pentanoyl)-3-methylpiperazine-1-carboxylate

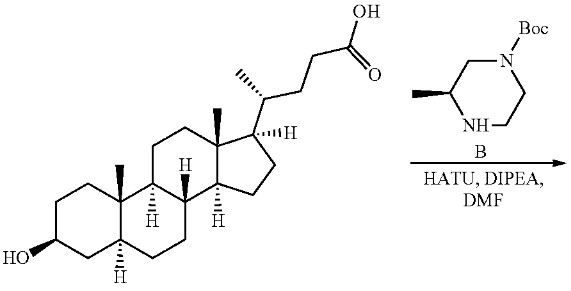

A

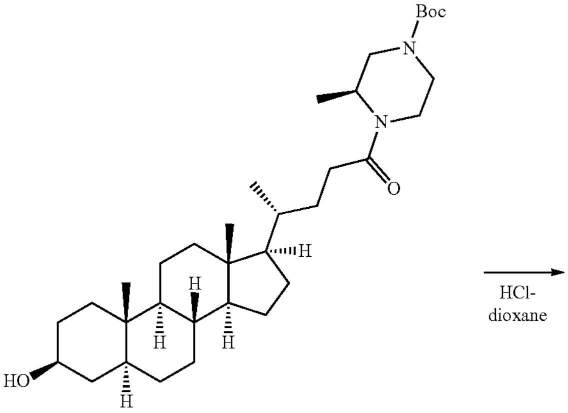

C

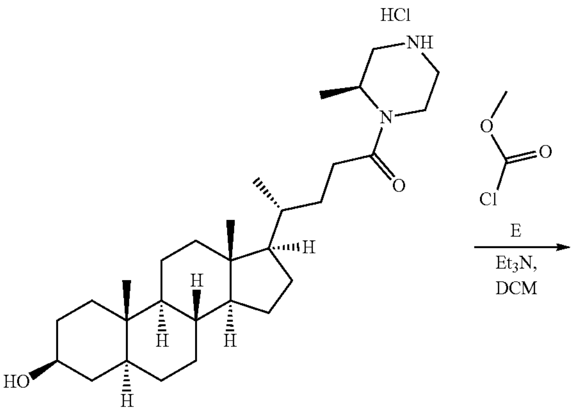

D

-continued

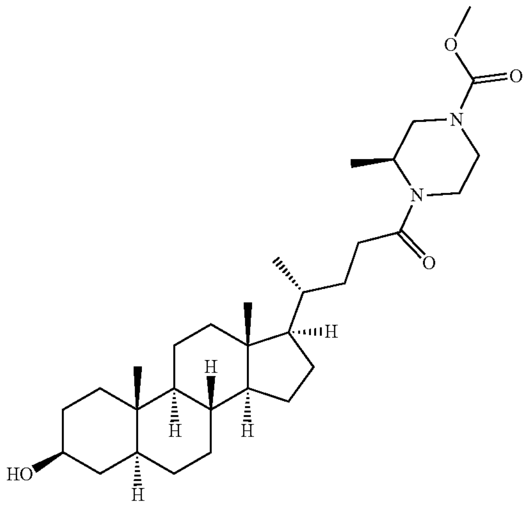

To a solution of compound A (200 mg, 531 μmol) and compound B (160 mg, 797 μmol) in DMF (5 mL) was added HATU (250 mg, 1.06 mmol), DIPEA (343 mg, 2.66 mmol) and the reaction was stirred at room temperature for 3 hours. Upon completion, the reaction was quenched by saturated aqueous ammonium chloride (50 mL) and extracted with ethyl acetate (50 mL*3). The organic layer was washed with brine, dried over sodium sulfate, filtered, and concentrated. The crude product was purified by silica gel chromatography to afford compound C (250 mg, 84%) as a white solid.

4N HCl in 1,4-dioxane (3 mL) was added slowly to the compound C (250 mg, 447 μmol) in a single-neck flask at room temperature and stirred for 1 hour. Upon completion, the reaction mixture was added dichloromethane (10 mL) and concentrated three times to afford compound D (210 mg, 95%) as the HCl salt.

To a solution of compound D (108 mg, 219 μmol) in dichloromethane (5 mL) was added $Et_3N$ (88.6 mg, 876 μmol) and methyl carbonochloridate (18.6 mg, 197 μmol) at 0° C. slowly. The reaction mixture was stirred for 1 hour. Upon completion, the reaction was quenched with water (10 mL) and extracted with ethyl acetate (10 mL*3). The organic layer was washed with brine, dried over sodium sulfate, filtered, and concentrated. The crude product was purified by silica gel chromatography to afford the title compound T47 (40 mg, 34%) as a white solid. LCMS: $[M+1]^+=517.30$. $^1H$ NMR (400 MHz, Chloroform-d) δ 4.08-4.06 (m, 3H), 3.72 (s, 3H), 3.58 (tt, J=10.8, 4.8 Hz, 2H), 3.32 (s, 1H), 3.02 (d, J=13.2 Hz, 1H), 2.86 (s, 1H), 2.47-2.26 (m, 1H), 2.25-2.14 (m, 1H), 1.95 (dt, J=12.4, 3.6 Hz, 1H), 1.82-1.79 (m, 3H), 1.73-1.61 (m, 3H), 1.56-1.51 (m, 2H), 1.51-1.46 (m, 1H), 1.42 (dt, J=8.4, 3.0 Hz, 1H), 1.38 (d, J=2.8 Hz, 1H), 1.36-1.31 (m, 2H), 1.30-1.28 (m, 2H), 1.27-1.25 (m, 3H), 1.23 (d, J=4.2 Hz, 1H), 1.16-1.05 (m, 5H), 1.00 (dd, J=6.6, 3.6 Hz, 1H), 0.93 (d, J=6.6 Hz, 4H), 0.89-0.84 (m, 1H), 0.80 (s, 3H), 0.65 (s, 4H).

Example T48: Methyl (S)-4-((R)-4-((3S,5S,8R,9S,10S,13R,14S,17R)-3-hydroxy-10,13-dimethylhexadecahydro-1H-cyclopenta[a]phenanthren-17-yl)pentanoyl)-2-methylpiperazine-1-carboxylate

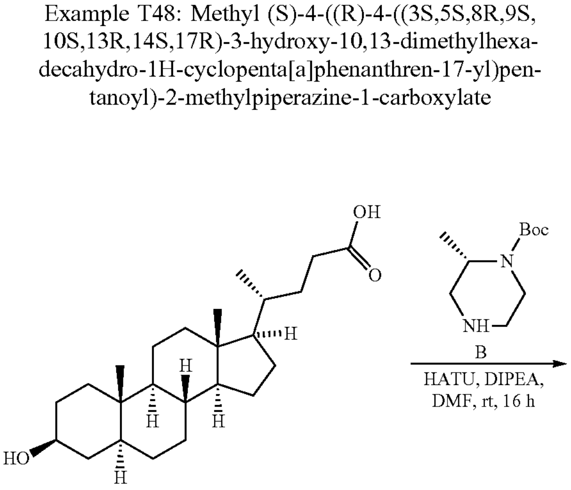

A

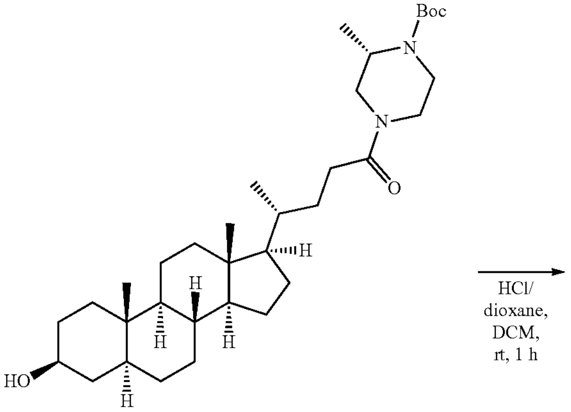

C

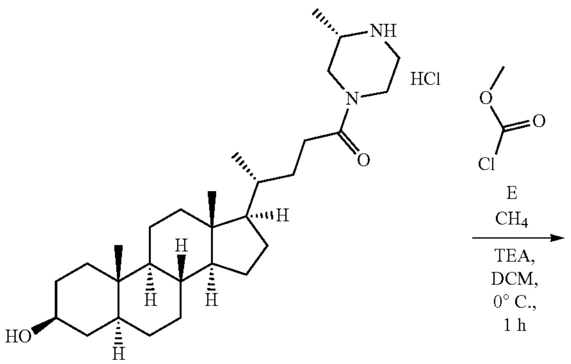

D

-continued

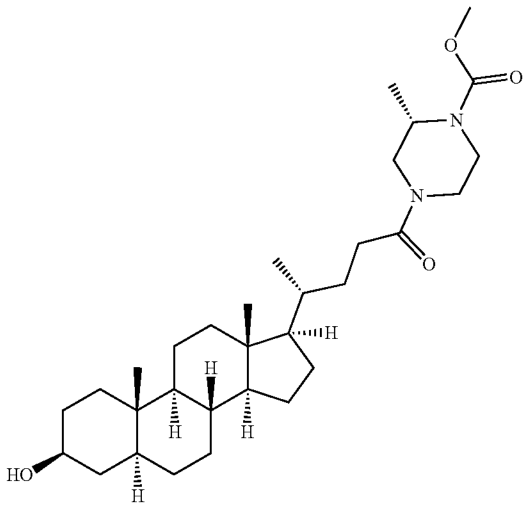

To a solution of compound A (5.0 g, 13.3 mmol) in DMF (70 mL), was added compound B (2.66 g, 13.3 mmol), DIPEA (5.15 g, 39.8 mmol), HATU (10.1 g, 26.6 mmol) at room temperature under $N_2$ and stirred for 16 h. The reaction was diluted with saturated aqueous $NH_4Cl$ (50 mL) and extracted with EtOAc (50 mL*2). The combined organic layers were washed with saturated aqueous $NaHCO_3$ (50 mL), water (50 mL) and brine (50 mL), dried over sodium sulfate and concentrated under reduced pressure. The residue was purified by silica gel chromatography to afford compound C (6.5 g, 88%) as a yellow oil.

To a solution of compound C (6.5 g, 11.6 mmol) in DCM (60 mL) was added 4 M HCl in 1,4-dioxane (20 mL) at room temperature and the reaction was stirred for 2 h. The reaction was concentrated under reduced pressure to afford compound D as the HCl salt (5.7 g).

To a 0° C. solution of compound D (5.7 g, 11.6 mmol) in DCM (50 mL) was added TEA (4.6 g, 46 mmol), compound E (1.09 g, 11.6 mmol) and stirred for 1 h. The reaction was diluted with saturated aqueous $NH_4Cl$ (30 mL) and extracted with EtOAc (10 mL*2). The combined organic layer was washed with saturated aqueous $NaHCO_3$ (20 mL), water (20 mL) and brine (20 mL), dried over sodium sulfate and concentrated under reduced pressure. The residue was purified by silica gel chromatography to afford the title compound T48 (4.5 g, 75%) as a white solid. LCMS: $[M+1]^+$ =517.30. $^1H$ NMR (400 MHz, Chloroform-d) δ 4.32 (d, J=12.8 Hz, 1H), 3.96-3.87 (m, 1H), 3.72 (s, 3H), 3.62-3.52 (m, 1.5H), 3.30-3.28 (m, 0.5H), 3.20-3.01 (m, 1.5H), 2.92-2.84 (m, 0.5H), 2.70-2.63 (m, 0.5H), 2.42-2.13 (m, 2H), 1.95 (d, J=12.6 Hz, 1H), 1.87-1.66 (m, 4H), 1.59-0.77 (m, 31H), 0.65-0.58 (m, 4H).

Example T49: N—((S)-1-((R)-4-((3S,5S,8R,9S,10S,13R,14S,17R)-3-hydroxy-10,13-dimethylhexadecahydro-1H-cyclopenta[a]phenanthren-17-yl)pentanoyl)pyrrolidin-3-yl)acetamide

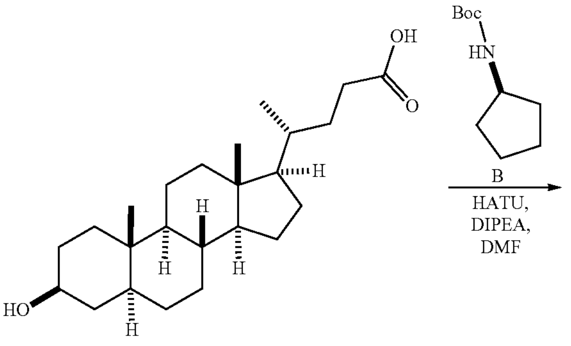

A

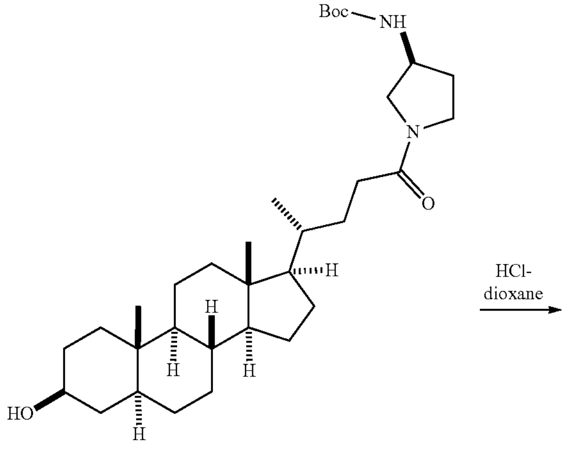

C

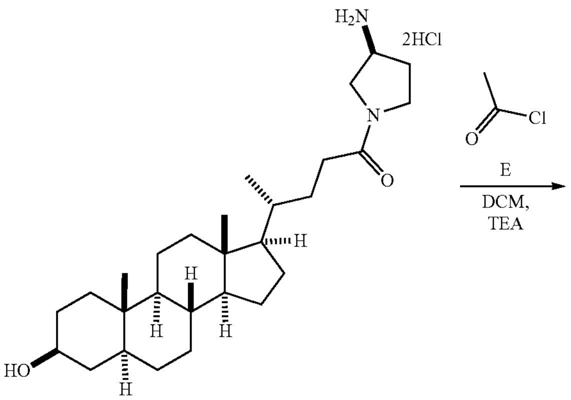

D

-continued

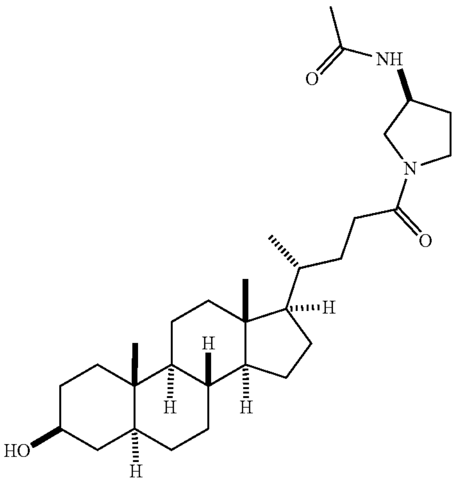

To a room temperature solution of compound A (500 mg, 1.33 mmol) and compound B (371 mg, 1.99 mmol) in DMF (5 mL) was added HATU (625 mg, 2.66 mmol), DIPEA (1.03 g, 7.97 mmol) and the reaction was stirred for 3 hours. Upon completion, the reaction was quenched by saturated aqueous ammonium chloride (50 mL) and extracted with ethyl acetate (50 mL*3). The combined organic layers were washed with brine, dried over sodium sulfate, filtered, and concentrated. The crude product was purified by silica gel chromatography to afford compound C (520 mg, 72%) as a white solid.

4N HCl in 1,4-dioxane (5 mL, 4N) was added slowly to compound C (300 mg, 551 μmol) in a single-neck flask at room temperature and stirred for 1 hour. Upon completion, the reaction mixture was added dichloromethane (10 mL) and concentrated to afford compound D (260 mg, 98%) as the HCl salt.

To a solution of compound D (235 mg, 450 μmol) in dichloromethane (5 mL) was added TEA (6 mL, 93.7 mmol) and acetyl chloride (31.8 mg, 405 μmol) at 0° C. slowly. The reaction mixture was stirred for 1 hour. Upon completion, the reaction was quenched with water (10 mL) and extracted with ethyl acetate (10 mL*3). The organic layer was washed with brine, dried over sodium sulfate, filtered, and concentrated. The crude product was purified by silica gel chromatography to afford the title compound T49 (120 mg, 55%) as a white solid. LCMS: $[M+1]^+$=487.35. $^1$H NMR (400 MHz, Chloroform-d) δ 6.12-5.98 (m, 1H), 4.46-4.40 (m, 1H), 3.78-3.27 (m, 6H), 2.27 (dd, J=11.0, 5.2 Hz, 1H), 2.12 (dd, J=13.6, 7.0 Hz, 1H), 1.99 (d, J=4.2 Hz, 4H), 1.79 (d, J=14.0 Hz, 3H), 1.69 (s, 5H), 1.59-1.52 (m, 2H), 1.48 (dd, J=13.8, 3.4 Hz, 1H), 1.44-1.37 (m, 2H), 1.34 (d, J=3.2 Hz, 1H), 1.31 (d, J=11.8 Hz, 2H), 1.25 (q, J=7.0, 6.0 Hz, 4H), 1.10 (t, J=4.76 Hz, 2H), 1.08-1.06 (m, 1H), 1.00 (t, J=4.8 Hz, 1H), 0.96 (t, J=3.0 Hz, 1H), 0.92 (t, J=6.0 Hz, 3H), 0.89-0.83 (m, 1H), 0.79 (s, 3H), 0.64 (d, J=2.8 Hz, 4H).

Example T50: (R)-4-((3S,5S,8R,9S,10S,13R,14S,17R)-3-hydroxy-10,13-dimethylhexadecahydro-1H-cyclopenta[a]phenanthren-17-yl)-1-(4-(pyridazin-4-yl)piperazin-1-yl) pentan-1-one

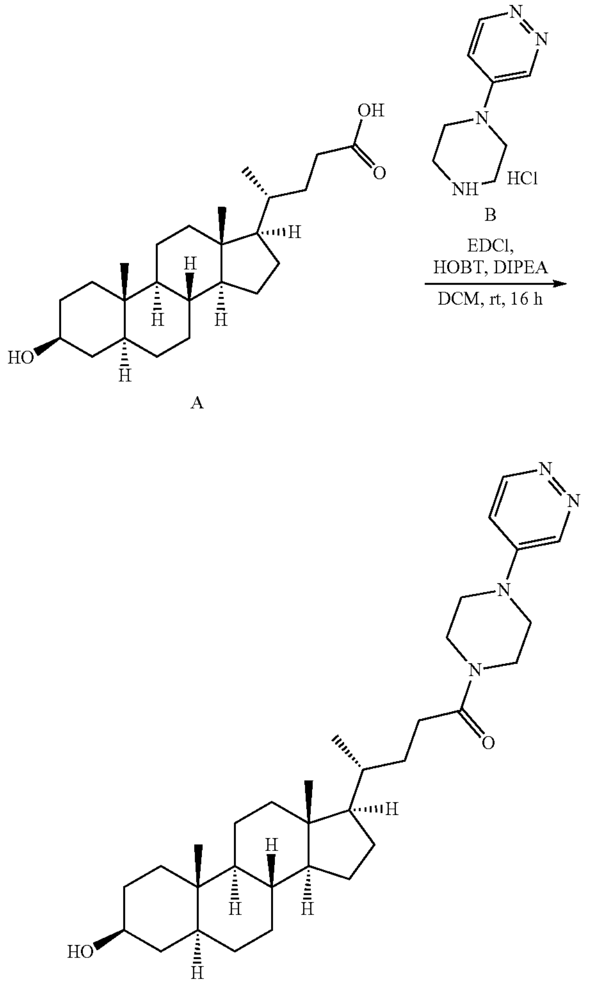

To a room temperature solution of compound A (100 mg, 266 μmol) in DCM (3 mL) was added compound B (64 mg, 319 μmol), HOBT (80.8 mg, 531 μmol), EDCI (103 mg, 531 μmol), DIPEA (206 mg, 1.59 mmol) and the reaction stirred under $N_2$ for 16 h. Saturated aqueous $NH_4Cl$ (30 mL) was added, and the reaction was extracted with DCM (10 mL*2). The combined organic layers were washed with water (20 mL) and brine (20 mL), dried over sodium sulfate, and concentrated under reduced pressure. The residue was purified by silica gel chromatography to afford the title compound T50 (70 mg, 50%) as a white solid. LCMS: $[M+H]^+$=523.30. $^1$H NMR (400 MHz, Chloroform-d) δ 8.86 (d, J=3.2 Hz, 1H), 8.74 (d, J=6.4 Hz, 1H), 6.68-6.66 (m, 1H), 3.80-3.78 (m, 2H), 3.68-3.64 (m, 2H), 3.62-3.54 (m, 1H), 3.49-3.36 (m, 4H), 2.44-2.37 (m, 1H), 2.29-2.21 (m, 1H), 1.95 (dt, J=12.4, 3.6 Hz, 1H), 1.90-1.78 (m, 3H), 1.73-1.62 (m, 6H), 1.60-1.53 (m, 2H), 1.51-1.47 (m, 2H), 1.40-1.31 (m, 3H), 1.30-1.22 (m, 6H), 1.15-1.07 (m, 3H), 1.03-0.99 (m, 1H), 0.95 (d, J=6.4 Hz, 3H), 0.89-0.83 (m, 1H), 0.80 (s, 3H), 0.66-0.58 (m, 4H).

Example T51: (R)-1-(4-(1-cyclopropyl-1H-pyrrol-3-yl)piperazin-1-yl)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentan-1-one

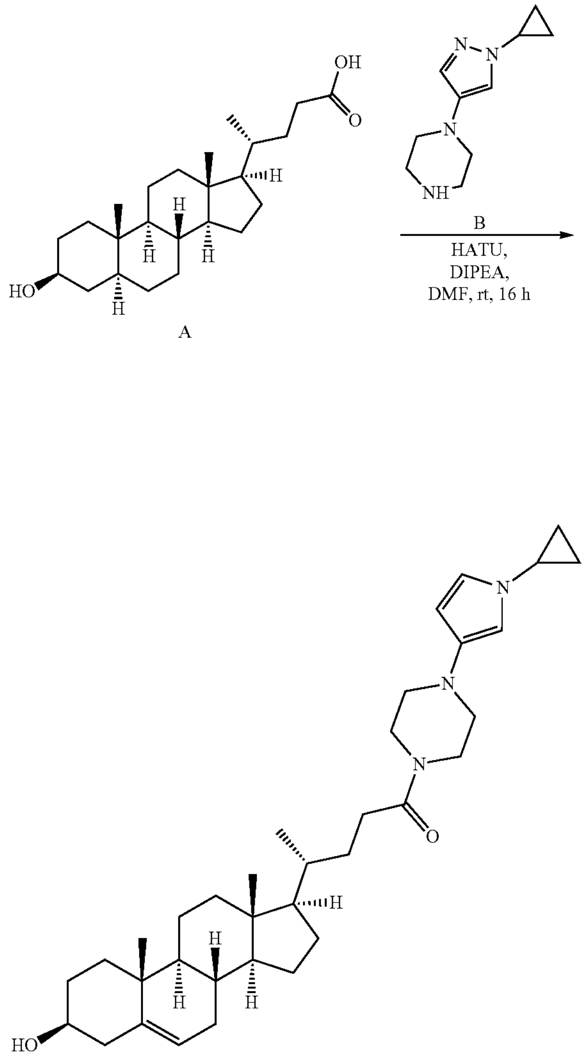

(R)-4-((3S,5S,8R,9S,10S,13R,14S,17R)-3-hydroxy-10,13-dimethylhexadecahydro-1H-cyclopenta[a]phenanthren-17-yl)pentanoic acid (100 mg, 266 μmol) and 1-(1-cyclopropyl-1H-pyrazol-4-yl) piperazine (102 mg, 359 μmol) were reacted according to the method of Example T27 to afford the title compound T51 (60.4 mg, 41.29%) as a white solid. LCMS: $[M+1]^+$=551.35. $^1$H NMR (400 MHz, Chloroform-d) δ 7.20 (d, J=0.8 Hz, 1H), 7.05 (s, 1H), 3.74 (t, J=4.8 Hz, 2H), 3.64-3.48 (m, 4H), 2.90 (dt, J=16.4, 5.2 Hz, 3H), 2.33-2.44 (m, 1H), 2.18-2.28 (m, 1H), 1.95 (d, J=12.8 Hz, 1H), 1.89-1.76 (m, 3H), 1.72 (t, J=3.6 Hz, 1H), 1.68 (d, J=4.4 Hz, 1H), 1.65-1.61 (m, 3H), 1.54 (d, J=3.2 Hz, 1H), 1.51-1.46 (m, 2H), 1.44 (d, J=6.6 Hz, 1H), 1.39-1.31 (m, 3H), 1.29-1.23 (m, 5H), 1.11 (d, J=4.0 Hz, 2H), 1.10-1.06 (m, 3H), 1.00-0.95 (m, 3H), 0.94 (d, J=6.4 Hz, 3H), 0.89-0.83 (m, 1H), 0.80 (s, 3H), 0.65 (s, 4H).

Example T52: (R)-4-((3S,5S,8R,9S,10S,13R,14S,17R)-3-hydroxy-10,13-dimethylhexadecahydro-1H-cyclopenta[a]phenanthren-17-yl)-1-(4-(1-methyl-1H-pyrazol-4-yl)piperazin-1-yl) pentan-1-one

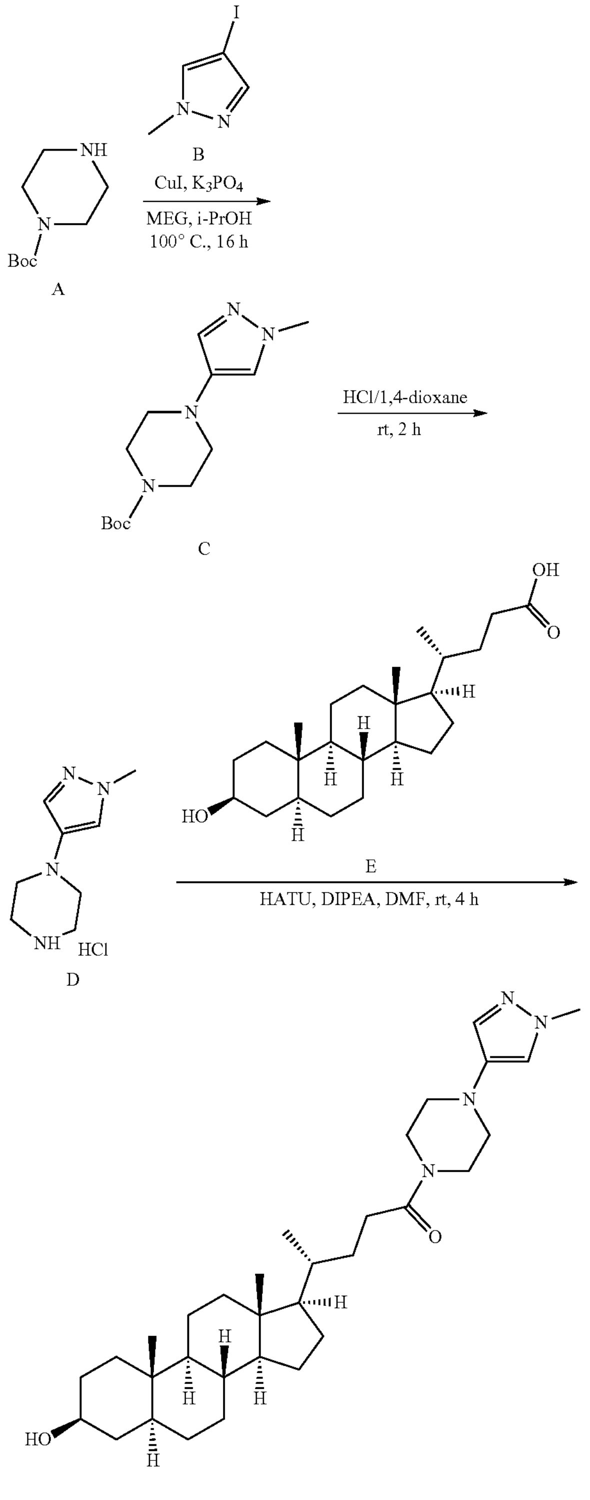

To a solution of compound A (200 mg, 1.07 mmol) in i-PrOH (4 mL) was added compound B (223 mg, 1.07 mmol), CuI (40.9 mg, 215 μmol), $K_3PO_4$ (912 mg, 4.3 mmol) and ethane-1.2-diol (66.6 mg, 1.07 mmol). The reaction was warmed to 100° C. for 6 hours under $N_2$.

The reaction was diluted with water (5 mL) and extracted with ethyl acetate (10 mL). The organic layer was concentrated. The crude product was purified by silica gel chromatography to afford compound C (100 mg, 35%) as yellow solid.

To a solution of compound C (100 mg, 375 μmol) in DCM (2 mL) was added 4N HCl in 1,4-dioxane (1 mL) and stirred at room temperature for 2 hours. The reaction was concentrated to afford compound D (63 mg).

(R)-4-((3S,5S,8R,9S,10S,13R,14S,17R)-3-hydroxy-10,13-dimethylhexadecahydro-1H-cyclopenta[a]phenanthren-17-yl)pentanoic acid (141 mg, 375 μmol) and 1-(1-methyl-1H-pyrazol-4-yl)piperazine hydrochloride (63 mg, 375 μmol) were reacted according to the method of Example T27 to afford the title compound T52 (90 mg, 46%) as white solid. LCMS: [M+1]+=525.35. $^1H$ NMR (400 MHz, Chloroform-d) δ 7.22 (s, 1H), 7.00 (s, 1H), 3.83 (s, 3H), 3.76 (s, 2H), 3.60 (d, J=5.6 Hz, 2H), 2.92 (d, J=14.4 Hz, 4H), 2.39 (td, J=11.0, 5.2 Hz, 1H), 2.23 (td, J=9.6, 5.2 Hz, 1H), 1.95 (d, J=12.4 Hz, 1H), 1.82-1.77 (m, 2H), 1.68 (d, J=4.2 Hz, 2H), 1.64 (d, J=3.2 Hz, 3H), 1.58-1.54 (m, 3H), 1.52-1.49 (m, 1H), 1.46 (d, J=6.4 Hz, 2H), 1.38 (s, 1H), 1.35 (s, 1H), 1.33-1.28 (m, 4H), 1.27-1.25 (m, 4H), 1.24 (s, 1H), 1.12-1.07 (m, 3H), 0.94 (d, J=6.4 Hz, 3H), 0.80 (s, 3H), 0.65 (s, 3H).

Example T53: Cyclopentyl4-[(4R)-4-[(1R,3aS,3bR,5aS,7S,9aS,9bS,11aR)-7-hydroxy-9a,11a-dimethyl-hexadecahydro-1H-cyclopenta[a]phenanthren-1-yl]pentanoyl]piperazine-1-carboxylate

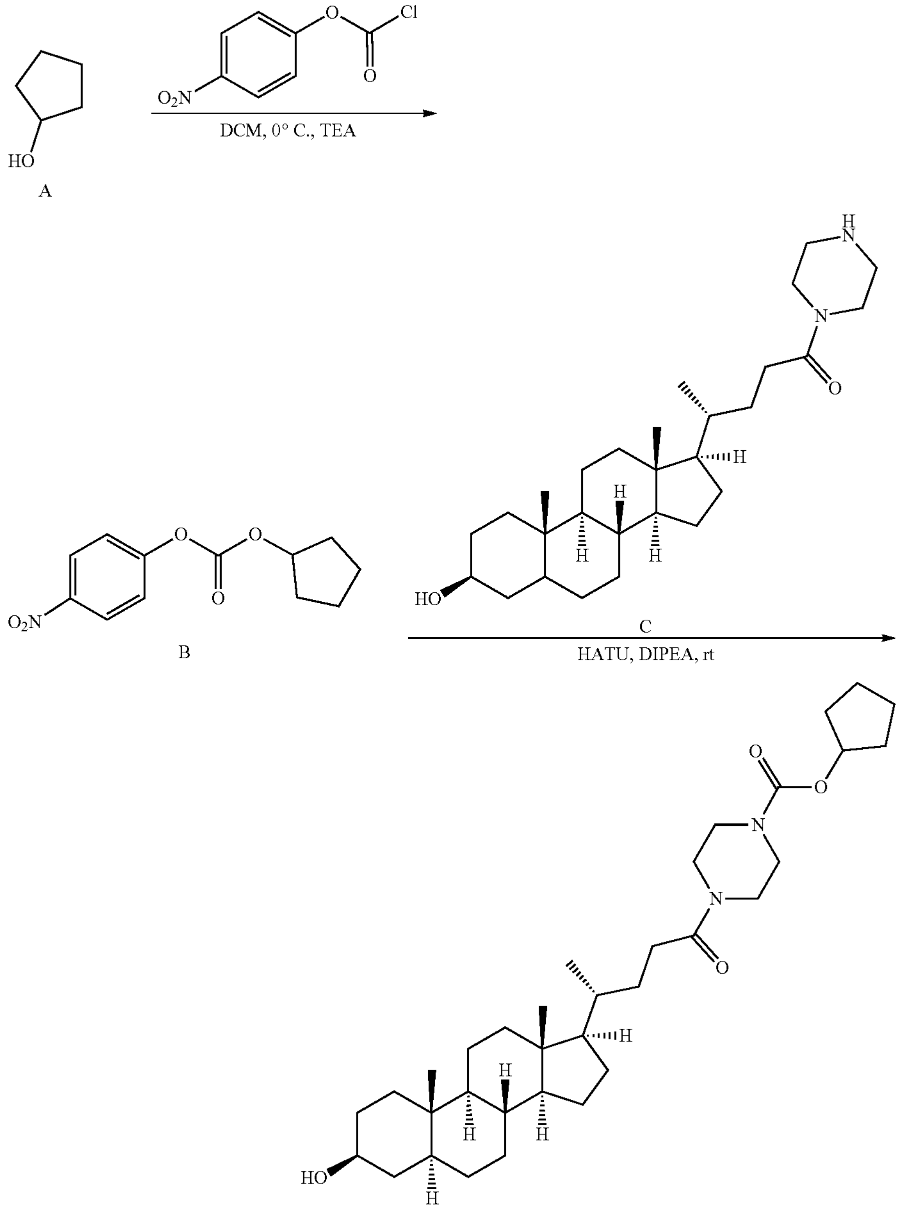

To a solution of compound A (513 mg, 5.95 mmol) in dichloromethane (15 mL) was added triethylamine (1.24 mL, 8.93 mmol) dropwise at room temperature. After addition, the solution was cooled to 0° C. for 10 min. A solution of 4-nitrophenyl carbonochloridate (600 mg, 2.98 mmol) in dichloromethane (15 mL) was added at 0° C. The reaction was warmed to room temperature for 3 h. The reaction was concentrated under reduced pressure and purified by silica gel chromatography to afford compound B (500 mg, 66.8%) as yellow solid.

To a solution of compound C (531 mg, 1.19 mmol) in dichloromethane (10 mL) was added DIPEA (693 μL, 3.98 mmol), compound B (200 mg, 796 μmol) and the reaction stirred for 16 h. The reaction was diluted with ethyl acetate (15 mL), washed with water (5 mL) and brine (5 mL), dried over sodium sulfate, and concentrated under reduced pressure. The crude product was purified by silica gel chromatography to afford the title compound T53 (38.8 mg, 8.7%) as white solid. LCMS: $[M+1]^+$=557.35. $^1$H NMR (400 MHz, $CDCl_3$) δ 5.16-5.09 (m, 1H), 3.62-3.54 (m, 3H), 3.44-3.42 (m, 6H), 2.40-2.33 (m, 1H), 2.33-2.09 (m, 2H), 1.95 (d, J=12.4 Hz, 1H), 1.89-1.75 (m, 6H), 1.72-1.66 (m, 6H), 1.52-1.39 (m, 4H), 1.39-1.28 (m, 6H), 1.26 (d, J=3.6 Hz, 3H), 1.23 (d, J=4.0 Hz, 1H), 1.16-1.03 (m, 5H), 1.01 (q, J=4.8 Hz, 2H), 0.93 (d, J=6.4 Hz, 3H), 0.80 (s, 3H), 0.65 (s, 3H).

Example T54: (R)-4-((3S,5S,8R,9S,10S,13R,14S,17R)-3-hydroxy-10,13-dimethylhexadecahydro-1H-cyclopenta[a]phenanthren-17-yl)-1-(4-(pyridin-4-yl)piperazin-1-yl)pentan-1-one

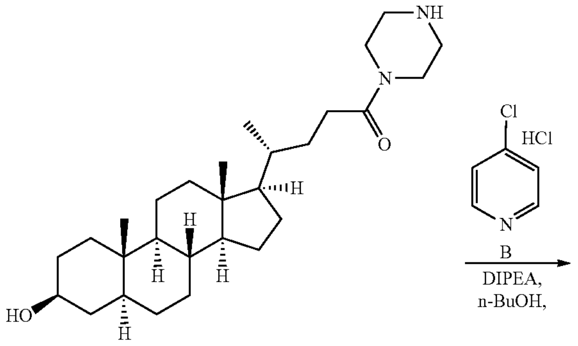

A

-continued

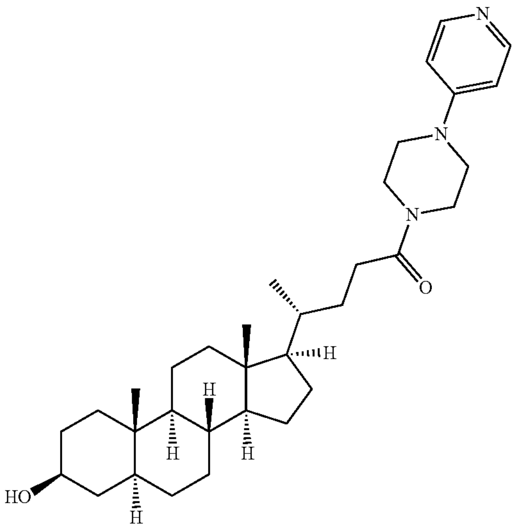

To a solution of compound A (300 mg, 675 μmol) and compound B (101 mg, 675 μmol) in DIPEA (3 mL, 17.2 mmol) was added n-butanol (1.5 mL, 16.4 mmol) at 120° C. under $N_2$ for 16 h. The reaction was concentrated under reduced pressure and purified by silica gel chromatography to afford the title compound T54 (80 mg, 23%) as off-white solid. LCMS: $[M+1]^+$=522.50. $^1$H NMR (400 MHz, Chloroform-d) δ 8.47-8.01 (m, 2H), 6.69-6.46 (m, 2H), 3.81-3.55 (m, 5H), 3.37 (s, 4H), 2.44-2.36 (m, 1H), 2.30-2.23 (m, 1H), 2.00-1.94 (m, 1H), 1.90-1.77 (m, 3H), 1.75-1.63 (m, 3H), 1.46-1.22 (m, 11H), 1.19-1.06 (m, 4H), 1.03-0.94 (m, 5H), 0.91-0.86 (m, 1H), 0.81 (s, 3H), 0.70-0.60 (m, 4H).

Example T55: (R)-4-((3S,5S,8R,9S,10S,13R,14S,17R)-3-hydroxy-10,13-dimethylhexadecahydro-1H-cyclopenta[a]phenanthren-17-yl)-1-(4-(1-methyl-1H-pyrazole-4-carbonyl)piperazin-1-yl)pentan-1-one

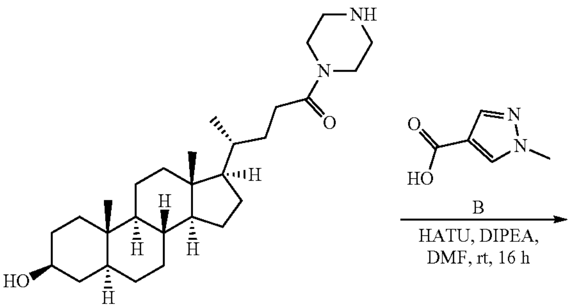

A

-continued

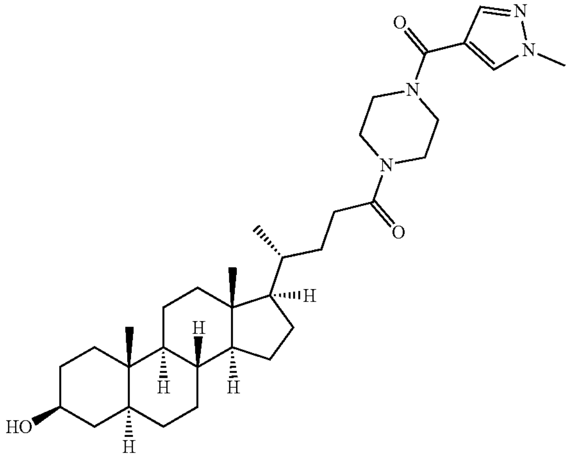

To a solution of compound A (200 mg, 450 μmol) and compound B (56.7 mg, 450 μmol) in DMF (3 mL) was added HATU (257 mg, 675 μmol), DIPEA (174 mg, 1.35 mmol) and the reaction stirred for 3 hours. Upon completion, the reaction was quenched by saturated aqueous ammonium chloride (10 mL) and extracted with ethyl acetate (10 mL*3). The combined organic layers were washed with brine (5 mL), dried over sodium sulfate, filtered, and concentrated under reduced pressure. The crude product was purified by silica gel chromatography to afford the title T55 (92 mg, 37%) as a white solid. LCMS: $[M+1]^+$=553.30. $^1$H NMR (400 MHz, Chloroform-d) δ 7.72 (s, 1H), 7.60 (s, 1H), 3.93 (s, 3H), 3.76-3.62 (m, 6H), 3.62-3.49 (m, 3H), 2.43-2.34 (m, 1H), 2.28-2.19 (m, 1H), 2.04-1.90 (m, 2H), 1.88-1.75 (m, 4H), 1.67 (ddt, J=16.6, 12.8, 3.6 Hz, 3H), 1.53 (q, J=2.4 Hz, 1H), 1.51-1.38 (m, 3H), 1.38-1.28 (m, 4H), 1.26 (q, J=3.2, 2.8 Hz, 3H), 1.23 (d, J=3.6 Hz, 1H), 1.15-0.98 (m, 5H), 0.94 (d, J=6.6 Hz, 3H), 0.90-0.82 (m, 1H), 0.79 (s, 3H), 0.65 (s, 3H), 0.63-0.57 (m, 1H).

Example T56: Cyclopropyl4-[(4R)-4-[(1R,3aS,3bR,5aS,7S,9aS,9bS,11aR)-7-hydroxy-9a,11a-dimethyl-hexadecahydro-1H-cyclopenta[a]phenanthren-1-yl]pentanoyl]piperazine-1-carboxylate

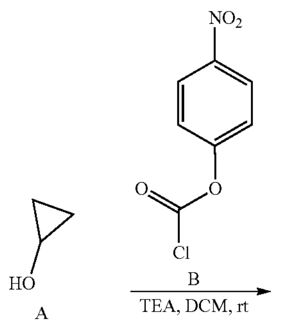

-continued

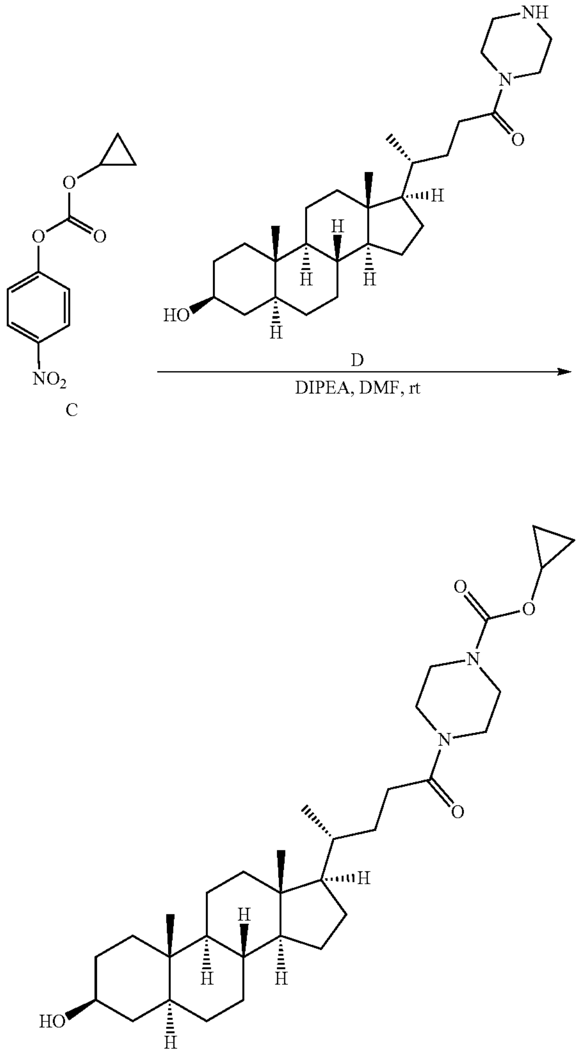

To a solution of compound A (207 mg, 3.57 mmol) in dichloromethane (6 mL) was added TEA (361 mg, 3.57 mmol) at room temperature. After addition, the solution was cooled to 0° C. for 10 min. A solution of compound B (600 mg, 2.98 mmol) in dichloromethane (6 mL) was added at 0° C. The reaction was warmed to room temperature for 3 h. The reaction was concentrated to afford compound C (796 mg, 100%) and was used directly to the next step.

To a solution of compound D (299 mg, 672 μmol) in dichloromethane (3 mL) was added DIEA (174 mg, 1.34 mmol) and compound C (100 mg, 448 μmol) at room temperature and the reaction stirred for 16 h. The reaction was diluted with ethyl acetate (15 mL), washed with water (5 mL) and brine (5 mL), dried with sodium sulfate, and concentrated under reduced pressure. The crude product was purified by silica gel chromatography to afford the title compound T56 (77.4 mg, 32.6%) as white solid. LCMS: $[M+1]^+$=529.35. $^1$H NMR (400 MHz, $CDCl_3$) δ 4.13-4.08 (m, 1H), 3.65-3.35 (m, 9H), 2.40-2.32 (m, 1H), 2.26-2.18 (m, 1H), 1.96 (dt, J=12.4, 3.2 Hz, 1H), 1.90-1.75 (m, 3H), 1.74-1.64 (m, 2H), 1.52-1.41 (m, 5H), 1.39-1.24 (m, 9H), 1.18-1.04 (m, 4H), 1.00 (dt, J=14.4, 5.2 Hz, 2H), 0.94 (d, J=6.4 Hz, 3H), 0.81 (s, 3H), 0.73-0.60 (m, 8H).

Example T57: (R)-4-((3S,5S,8R,9S,10S,13R,14S,17R)-3-hydroxy-10,13-dimethylhexadecahydro-1H-cyclopenta[a]phenanthren-17-yl)-1-(4-(1-methyl-1H-1,2,3-triazol-4-yl)piperazin-1-yl)pentan-1-one

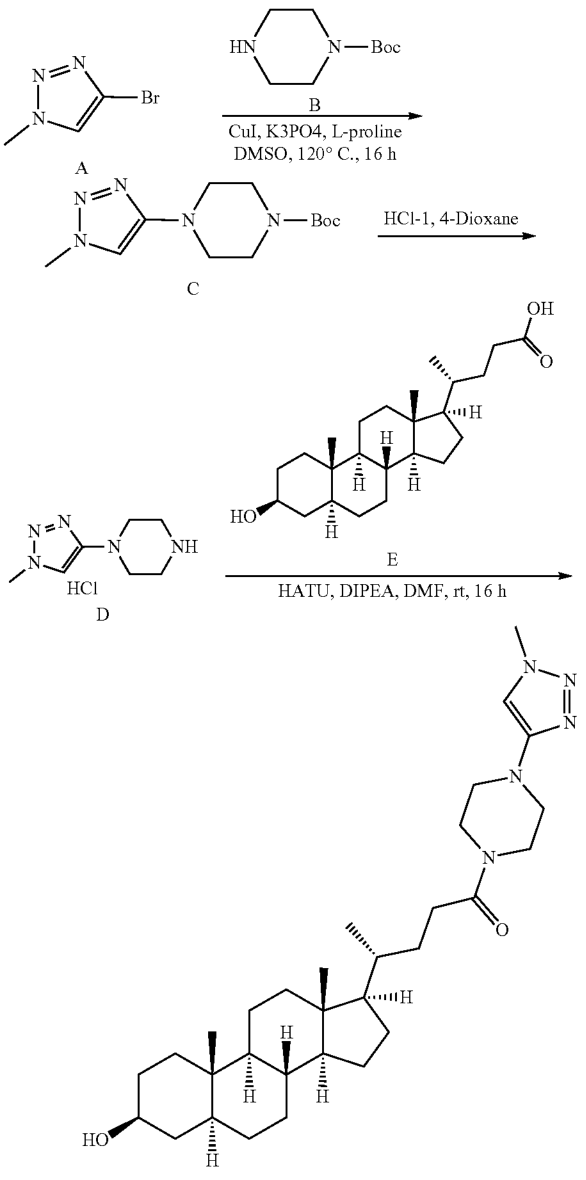

To a solution of compound A (2.5 g, 15.4 mmol) in DMSO (40 mL) was added compound B (3.45 g, 18.5 mmol), CuI (882 mg, 4.63 mmol), $K_3PO_4$ (9.83 g, 46.3 mmol) and pyrrolidine-2-carboxylic acid (1.07 g, 9.26 mmol). The reaction was heated to 120° C. for 16 hours under nitrogen. The reaction was diluted with water (5 mL) and extracted with ethyl acetate (15 mL). The organic layer was dried over sodium sulfate, filtered, and concentrated under reduced pressure. The crude product was purified by silica gel chromatography to afford compound C (150 mg, 3.6%).

4N HCl in 1,4-dioxane (3 mL) was added slowly to the compound C (150 mg, 561 μmol) in a single-neck flask at room temperature and stirred for 1 hour. Upon completion, the reaction mixture was added dichloromethane (10 mL) and concentrated under reduced pressure to afford compound D as the HCl salt (114 mg).

(R)-4-((3S,5S,8R,9S,10S,13R,14S,17R)-3-hydroxy-10,13-dimethylhexadecahydro-1H-cyclopenta[a]phenanthren-17-yl)pentanoic acid (300 mg, 797 μmol) and 1-(1-methyl-1H-1,2,3-triazol-4-yl) piperazine hydrochloride (114 mg, 559 μmol) were reacted according to the method of Example T27 to afford to afford the title compound T57 (51 mg, 11.9%) as a white solid. LCMS: $[M+1]^+$=526.40. $^1$H NMR (400 MHz, Chloroform-d) δ 6.87 (s, 1H), 4.01 (s, 3H), 3.75 (t, J=5.2 Hz, 2H), 3.62-3.54 (m, 3H), 3.28 (t, J=5.2 Hz, 2H), 3.09 (t, J=5.2 Hz, 2H), 2.35-2.44 (m, 1H), 2.20-2.28 (m, 1H), 1.95 (dt, J=12.4, 3.2 Hz, 1H), 1.86-1.76 (m, 3H), 1.72-1.63 (m, 5H), 1.39-1.52 (m, 3H), 1.39-1.30 (m, 3H), 1.30-1.22 (m, 5H), 1.16-1.02 (m, 4H), 1.02-0.96 (m, 2H), 0.94 (d, J=6.5 Hz, 3H), 0.80 (s, 3H), 0.65 (s, 4H).

Example T58: (R)-4-((3S,5S,8R,9S,10S,13R,14S,17R)-3-hydroxy-10,13-dimethylhexadecahydro-1H-cyclopenta[a]phenanthren-17-yl)-1-(4-(pyrimidin-4-yl)piperazin-1-yl)pentan-1-one

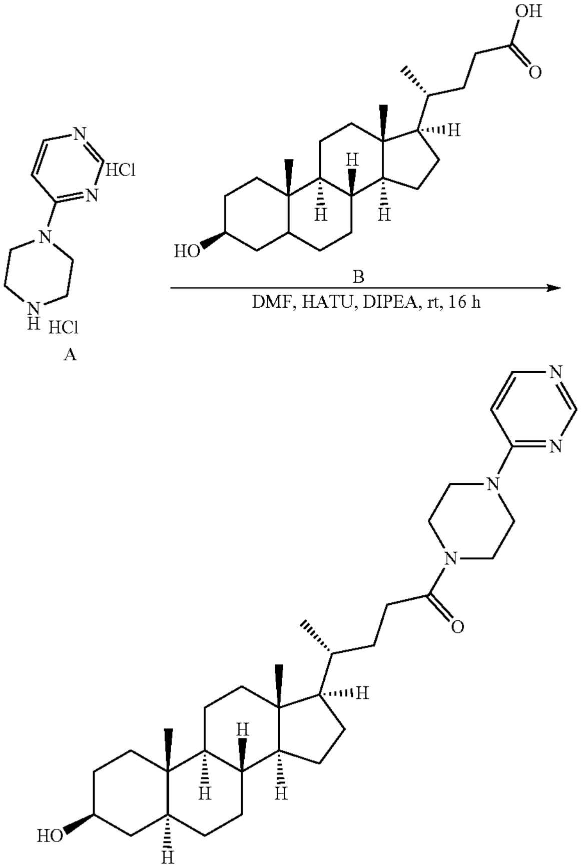

(R)-4-((3S,8S,9S,10R,13R,14S,17R)-3-hydroxy-10,13-dimethyl-2,3,4,7,8,9,10,11,12,13,14,15,16,17-tetradecahydro-1H-cyclopenta[a]phenanthren-17-yl)pentanoic acid (71.5 mg, 190 μmol) and 4-(piperazin-1-yl)pyrimidine dihydrochloride (50 mg, 211 μmol) to afford the title compound T58 (30 mg, 27.2%) as a white solid. LCMS: [M+1]+ =523.25. $^1$H NMR (400 MHz, DMSO-$d_6$) δ 8.51 (s, 1H), 8.20 (d, J=6.2 Hz, 1H), 6.83 (d, J=7.6, 1H), 4.40 (d, J=4.8 Hz, 1H), 3.68-3.49 (m, 8H), 3.38-3.33 (m, 1H), 2.40-2.20

(m, 2H), 2.03-1.33 (m, 11H), 1.32-0.93 (m, 13H), 0.92-0.83 (m, 5H), 0.74 (s, 3H), 0.62 (s, 3H), 0.58 (dd, J=11.0, 2.8 Hz, 1H).

Example T59: (R)-4-((3S,5S,8R,9S,10S,13R,14S,17R)-3-hydroxy-10,13-dimethylhexadecahydro-1H-cyclopenta[a]phenanthren-17-yl)-1-(4-(1-methyl-1H-1,2,3-triazole-4-carbonyl)piperazin-1-yl)pentan-1-one

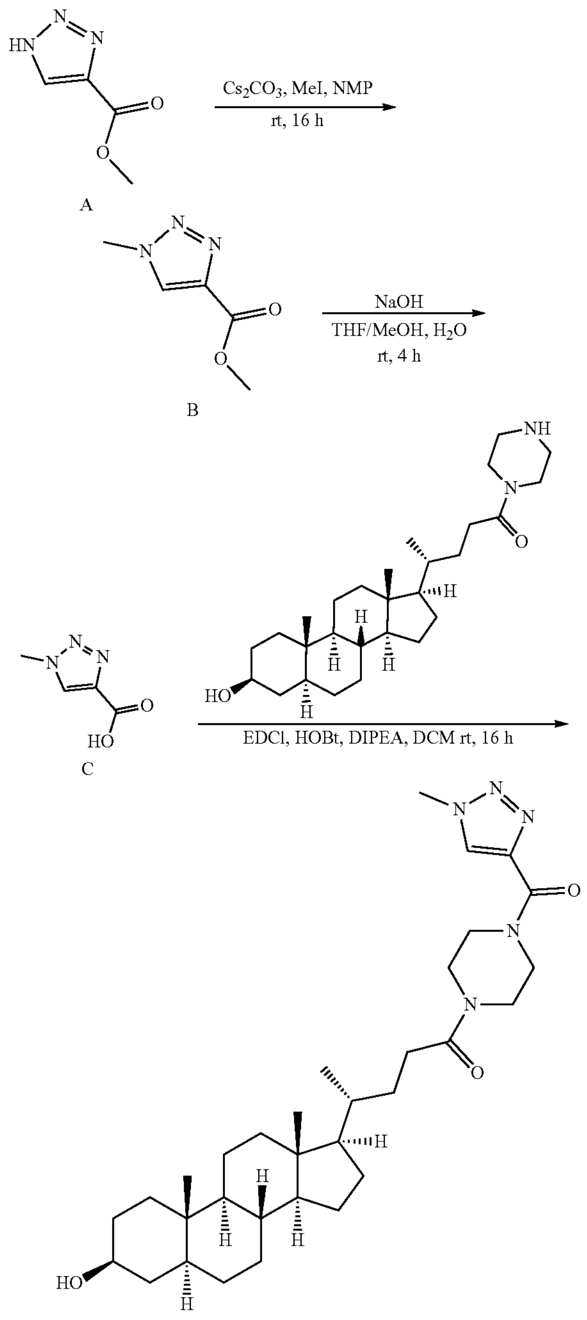

To a solution of compound A (500 mg, 3.93 mmol) in NMP (5 mL), was added $Cs_2CO_3$ (2.56 g, 7.87 mmol), MeI (2 mL) and the reaction stirred for 16 h. The reaction was quenched with water (20 mL) and extracted with EtOAc (60 mL). The organic layer was washed by brine (50 mL), dried over sodium sulfate, filtered, and concentrated under reduced pressure. The residue was purified by silica gel chromatography to afford compound B (140 mg, 11%) as a white solid.

To a solution of compound B (100 mg, 709 μmol) in THF (1 mL, 12.3 mmol), water (1 mL, 55.5 mmol) and methanol (1 mL, 24.7 mmol) was added sodium hydroxide (56.7 mg, 1.42 mmol) and the reaction stirred for 4 h. The reaction was quenched with 1M HCl (10 mL) and extracted with EtOAc (30 mL). The organic layer was washed by brine (20 mL), dried over sodium sulfate, filtrated, and concentrated under reduced pressure to afford compound C (80 mg, 89%) as a white solid.

To a solution of compound C (80 mg, 629 μmol) in dichloromethane (5 mL) was added compound D (280 mg, 629 μmol), EDCI (244 mg, 1.26 mmol), HOBt (192 mg, 1.26 mmol), DIPEA (488 mg, 3.78 mmol) and the reaction stirred for 16 h. The reaction was quenched with saturated aqueous $NaHCO_3$ (20 mL) and extracted with EtOAc (60 mL). The organic layer was washed with brine, saturated aqueous $NaHCO_3$ (50 mL), dried over sodium sulfate, filtered, and concentrated under reduced pressure. The residue was purified by silica gel chromatography to afford the title compound T59 (140 mg, 17%) as a white solid. LCMS: [M+1]=554.25. $^1H$ NMR (400 MHz, $CDCl_3$): 8.08 (d, J=10.4 Hz, 1H), 4.30-4.26 (m, 2H), 4.13 (s, 3H), 3.80-3.50 (m, 7H), 2.31-2.28 (m, 2H), 2.00-1.26 (m, 21H), 1.16-0.96 (m, 6H), 0.78 (s, 3H), 0.64 (s, 4H)

Example T60: 2-hydroxy-N-((1-((R)-4-((3S,5S,8R,9S,10S,13R,14S,17R)-3-hydroxy-10,13-dimethyl-hexadecahydro-1H-cyclopenta[a]phenanthren-17-yl)pentanoyl)-4-methylpiperidin-4-yl)methyl)-2-methylpropanamide

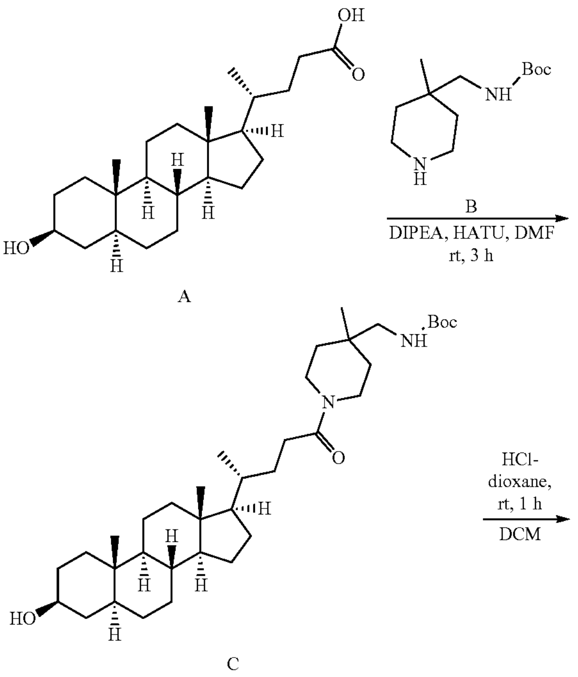

-continued

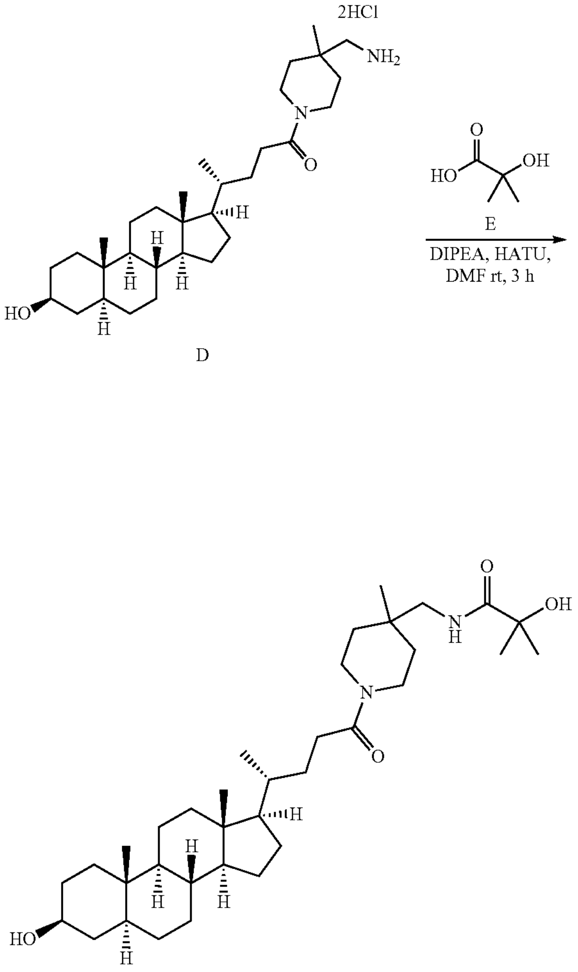

D

To a solution of compound A (300 mg, 798 μmol) and compound B (200 mg, 876 μmol) in DMF (10 mL) was added HATU (600 mg, 1.58 mmol), DIPEA (600 mg, 4.64 mmol) and the reaction stirred for 3 hours. Upon completion, the reaction was quenched with saturated aqueous ammonium chloride (100 mL) and extracted with ethyl acetate (100 mL*3). The combined organic layers were washed with brine, dried over sodium sulfate, filtered, and concentrated. The crude product was purified by silica gel chromatography to afford compound C (450 mg, 96%) as a white solid.

To a solution of 4N HCl in 1,4-dioxane (1 mL, 4 mmol) was added slowly a solution of compound C (200 mg, 341 μmol) in DCM (4 mL) at room temperature and stirred for 1 hour. Upon completion, the reaction mixture was concentrated to afford compound D (160 mg, 96%) as the HCl salt.

To a solution of compound D (150 mg, 308 μmol) and compound E (32.1 mg, 308 μmol) in DMF (5 mL) was added HATU (145 mg, 616 μmol), DIPEA (300 mg, 2.32 mmol). And the reaction stirred for 3 hours. Upon completion, the reaction was quenched by saturated aqueous ammonium chloride (50 mL) and extracted with ethyl acetate (50 mL*3). The organic layer was washed with brine, dried over sodium sulfate, filtered, and concentrated. The crude product was purified by silica gel chromatography to afford the title compound T60 (78 mg, 44%) as a white solid. LCMS: $[M+1]^+$=573.30. $^1$H NMR (400 MHz, Chloroform-d) δ 6.90 (d, J=7.2 Hz, 1H), 3.89-3.86 (m, 1H), 3.63-3.54 (m, 2H), 3.32 (t, J=11.6 Hz, 3H), 3.09-3.02 (m, 1H), 2.41-2.29 (m, 1H), 2.25-2.13 (m, 1H), 1.98-1.51 (m, 13H), 1.41-1.20 (m, 14H), 1.15-1.03 (m, 4H), 0.99 (s, 3H), 0.92 (d, J=6.4 Hz, 3H), 0.80 (s, 3H), 0.65 (s, 3H), 0.63-0.57 (m, 1H).

Example T61: 4—((R)-4-((3S,5S,8R,9S,10S,13R,14S,17R)-3-hydroxy-10,13-dimethylhexadecahydro-1H-cyclopenta[a]phenanthren-17-yl)pentanoyl)-N-methylpiperazine-1-carboximidamide

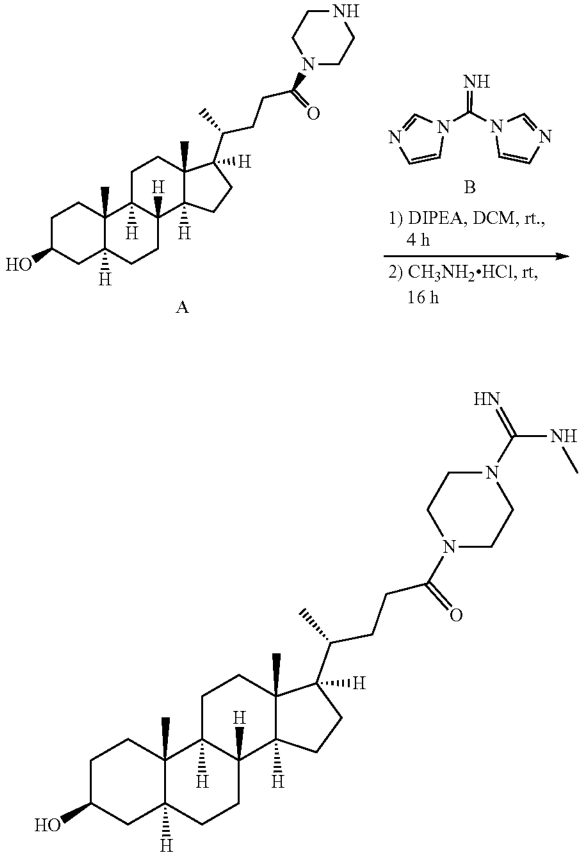

To a solution of compound A (100 mg, 225 μmol) in DCM (2 mL) was added compound B (36.2 mg, 225 μmol), DIPEA (87.2 mg, 675 μmol) and the reaction stirred for 4 h. $CH_3NH_2$·HCl (113 mg, 1.67 mmol) was added, and the reaction stirred at room temperature for 16 h. The reaction was concentrated under reduced pressure. The crude product was purified by Prep-HPLC to afford the title compound T61 (34.7 mg, 30.8%) as a white solid. LCMS: $[M+1]^+$=501.25. $^1$H NMR (400 MHz, DMSO-$d_6$) δ 7.76 (s, 1H), 7.68 (s, 2H), 4.45-4.34 (m, 1H), 3.52 (dt, J=11.8, 5.2 Hz, 4H), 3.45-3.36 (m, 4H), 2.78 (d, J=4.4 Hz, 3H), 2.28-2.25 (m, 2H), 1.95-1.88 (m, 1H), 1.77 (m, 1H), 1.65-1.56 (m, 4H), 1.54-1.37 (m, 4H), 1.35-0.94 (m, 16H), 0.89-0.86 (m, 5H), 0.74 (s, 3H), 0.62 (s, 4H).

Example T62: (4R)-4-((3S,8R,9S,10S,13R,14S,17R)-3-hydroxy-10,13-dimethylhexadecahydro-1H-cyclopenta[a]phenanthren-17-yl)-1-(4-(1-iminoethyl)piperazin-1-yl)pentan-1-one

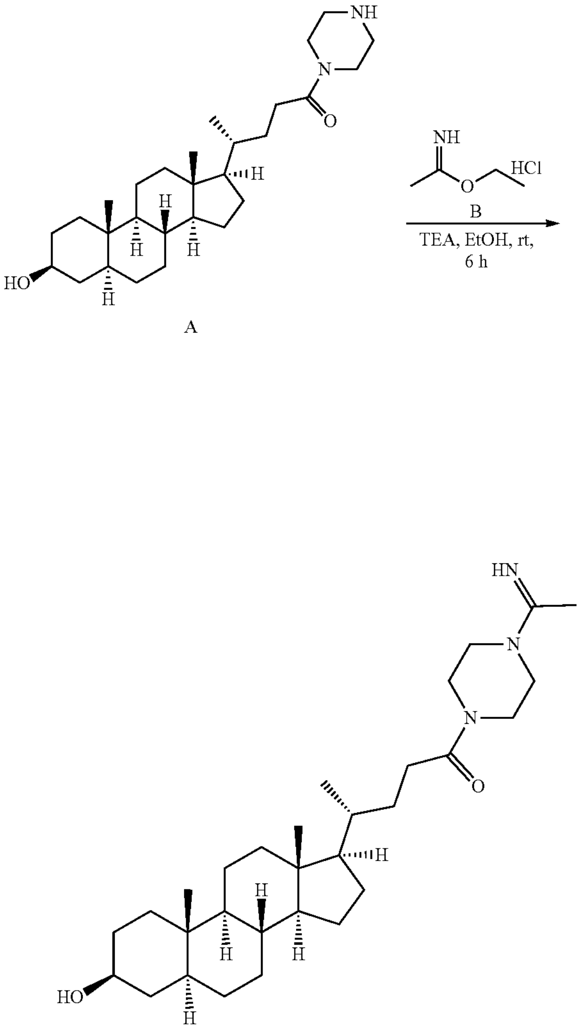

A

To a solution of compound A (300 mg, 678 μmol) and compound B (83.7 mg, 678 μmol) in ethanol (5 mL, 85.6 mmol) was added TEA (206 mg, 2.03 mmol) and the reaction was warmed to room temperature for 6 hours. The reaction mixture was diluted with water (20 mL) and extracted with ethyl acetate (20 mL*2). The combined organic layers were concentrated. The crude product was purified by silica gel chromatography to afford the title compound T62 (75 mg, 22.9%) as white solid. LCMS: $[M+1]^+$=486.25. $^1$H NMR (400 MHz, Methanol-$d_4$) δ 3.82-3.57 (m, 8H), 3.55-3.45 (m, 1H), 2.47 (s, 1H), 2.36 (s, 4H), 2.04-1.96 (m, 1H), 1.94-1.83 (m, 1H), 1.81-1.66 (m, 4H), 1.62-1.25 (m, 13H), 1.20-1.04 (m, 5H), 1.03-0.88 (m, 5H), 0.84 (s, 3H), 0.70 (s, 3H), 0.69-0.61 (m, 1H).

Example T63: 4—((R)-4-((3S,5S,8R,9S,10S,13R,14S,17R)-3-hydroxy-10,13-dimethylhexadecahydro-1H-cyclopenta[a]phenanthren-17-yl)pentanoyl)piperazine-1-carboxamide

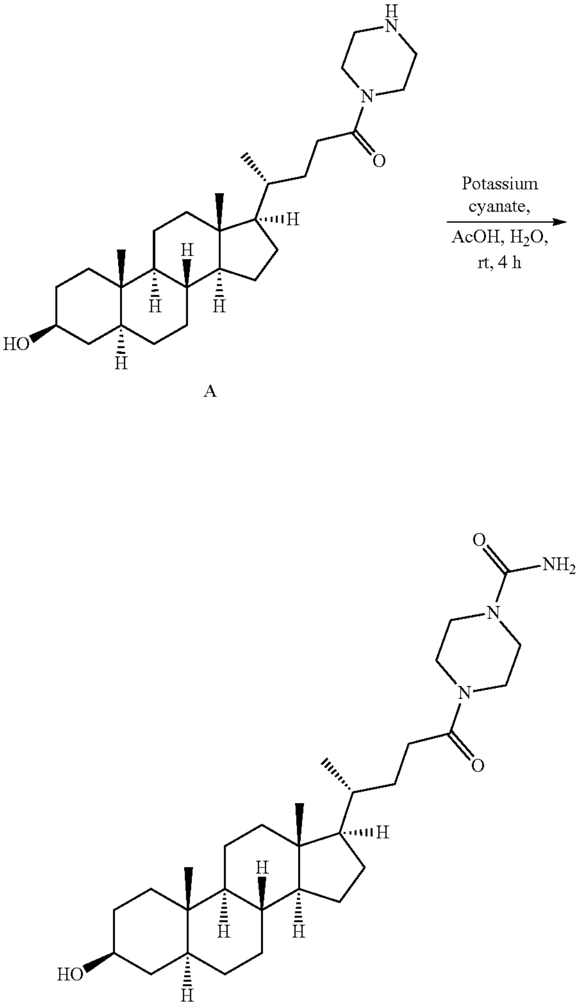

A

To a solution of compound A (50 mg, 112 μmol) in water (2 mL) and acetic acid (1 mL) was added potassium cyanate (45.6 mg, 562 μmol) and the reaction stirred for 4 hours. The reaction mixture was diluted with water (20 mL) and extracted with ethyl acetate (10 mL*2). The combined organic layers were washed with water (20 mL), brine (20 mL), dried over sodium sulfate and concentrated under reduced pressure. The residue was purified by silica gel chromatography to afford the title compound T63 (15 mg, 26.7%) as white solid. LCMS: $[M+1]^+$=488.25. $^1$H NMR (400 MHz, Methanol-$d_4$) δ 3.63-3.44 (m, 7H), 3.40-3.38 (m, 2H), 2.49-2.42 (m, 1H), 2.34-2.79 (m, 1H), 2.06-1.82 (m, 2H), 1.80-1.66 (m, 4H), 1.64-1.44 (m, 4H), 1.41-1.29 (m, 7H), 1.28-1.02 (m, 7H), 0.98-0.88 (m, 5H), 0.84 (s, 3H), 0.70 (s, 3H), 0.67-0.59 (m, 1H).

Example T64: 4R)-4-[(1R,3aS,3bR,5aS,7S,9aS,9bS,11aR)-7-hydroxy-9a,11a-dimethyl-hexadecahydro-1H-cyclopenta[a]phenanthren-1-yl]-1-(4-acetylpiperazin-1-yl)pentan-1-one

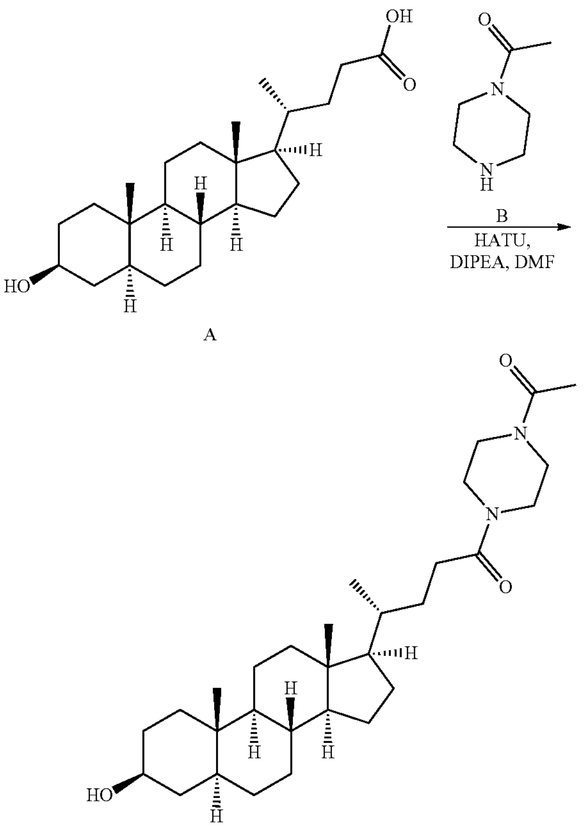

(R)-4-((3S,5S,8R,9S,10S,13R,14S,17R)-3-hydroxy-10,13-dimethylhexadecahydro-1H-cyclopenta[a]phenanthren-17-yl)pentanoic acid (300 mg, 797 μmol) and 1-(piperazin-1-yl)ethan-1-one (128 mg, 996 μmol) were reacted according to the method of Example T27 to afford the title compound T64 (300 mg, 62%) as a white solid. LCMS: [M+23]$^+$=509.20. $^1$H NMR (400 MHz, Chloroform-d) δ 3.68-3.39 (m, 9H), 2.37-2.35 (m, 1H), 2.23-2.19 (m, 1H), 2.12 (s, 3H), 1.95-1.92 (m, 1H), 1.90-1.75 (m, 3H), 1.70-1.65 (m, 2H), 1.59-1.40 (m, 6H), 1.39-1.27 (m, 5H), 1.23-1.18 (m, 1H), 1.16-1.04 (m, 4H), 1.00-0,98 (m, 1H), 0.94-0.92 (m, 4H), 0.89-0.83 (m, 1H), 0.80 (s, 3H), 0.65 (s, 4H).

Example T65: (4R)-4-[(1R,3aS,3bR,5aS,7S,9aS,9bS,11aR)-7-hydroxy-9a,11a-dimethyl-hexadecahydro-1H-cyclopenta[a]phenanthren-1-yl]-1-[(3S)-3-methoxypiperidin-1-yl]pentan-1-one

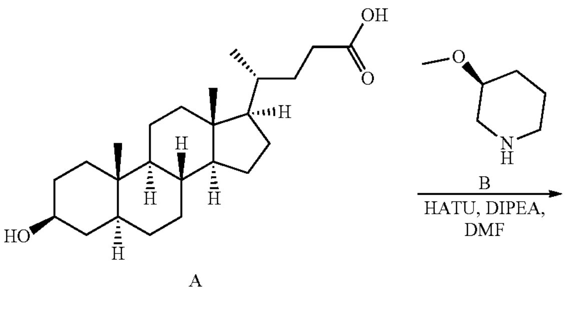

-continued

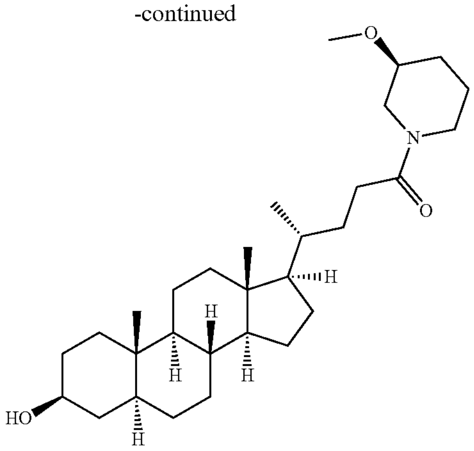

(R)-4-((3S,5S,8R,9S,10S,13R,14S,17R)-3-hydroxy-10,13-dimethylhexadecahydro-1H-cyclopenta[a]phenanthren-17-yl)pentanoic acid (150 mg, 398 μmol) and 3-(piperidin-4-yloxy)pyridine 2,2,2-trifluoroacetate (45.9 mg, 398 μmol) were reacted according to the method of Example T27 to afford the title compound T65 (100 mg, 53%) as a white solid. LCMS: [M+1]$^+$=474.25. $^1$H NMR (400 MHz, Chloroform-d) δ 4.06-4.04 (m, 1H), 3.87-3.83 (m, 0.45H), 3.69-3.65 (m, 0.45H), 3.62-3.54 (m, 1H), 3.52-3.44 (m, 1H), 3.37 (s, 3H), 3.26-3.09 (m, 3H), 2.41-2.33 (m, 1H), 2.26-2.15 (m, 1H), 2.01-1.91 (m, 2H), 1.89-1.74 (m, 4H), 1.73-1.62 (m, 3H), 1.50-1.47 (m, 3H), 1.47-1.37 (m, 4H), 1.36-1.28 (m, 4H), 1.26-1.22 (m, 1H), 1.14-1.10 (m, 4H), 1.04-0.98 (m, 2H), 0.97-0.9 (m, 5H), 0.90-0.81 (m, 1H), 0.80 (s, 3H), 0.69-0.57 (m, 4H).

Example T66: Methyl-4-[(4R)-4-[(1R,3aS,3bR,5aS,7S,9aS,9bS,11aR)-7-hydroxy-7,9a,11a-trimethyl-hexadecahydro-1H-cyclopenta[a]phenanthren-1-yl]pentanoyl]piperazine-1-carboxylate

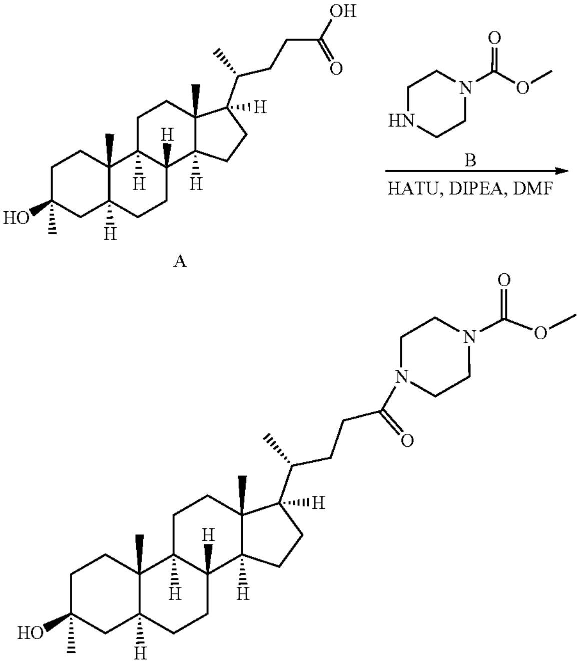

(R)-4-((3S,5S,8R,9S,10S,13R,14S,17R)-3-hydroxy-10,13-dimethylhexadecahydro-1H-cyclopenta[a]phenanthren-17-yl)pentanoic acid (200 mg, 512 μmol), methyl piperazine-1-carboxylate (92 mg, 640 μmol) to afford the title compound T66 (250 mg, 75%) as a white solid. LCMS: $[M+1]^+$=517.30. $^1$H NMR (400 MHz, Chloroform-d) δ 3.72 (s, 3H), 3.60-3.57 (m, 2H), 3.48-3.44 (m, 6H), 2.40-2.33 (m, 1H), 2.22-2.17 (m, 1H), 1.97-1.92 (m, 1H), 1.89-1.72 (m, 2H), 1.66-1.59 (m, 6H), 1.57-1.52 (m, 2H), 1.46-1.42 (m, 4H), 1.38-1.28 (m, 4H), 1.22-1.18 (m, 2H), 1.21-1.1.9 (m, 2H), 1.08-0.97 (m, 4H), 0.94 (d, J=6.4, 3H), 0.90-0.82 (m, 1H), 0.80 (s, 3H), 0.65 (s, 4H).

Example T67: Methyl 4-[(4R)-4-[(1R,3aS,3bR,5aS,7S,9aS,9bS,11aR)-7-hydroxy-9a,11a-dimethyl-hexadecahydro-1H-cyclopenta[a]phenanthren-1-yl]pentanoyl]piperazine-1-carboxylate

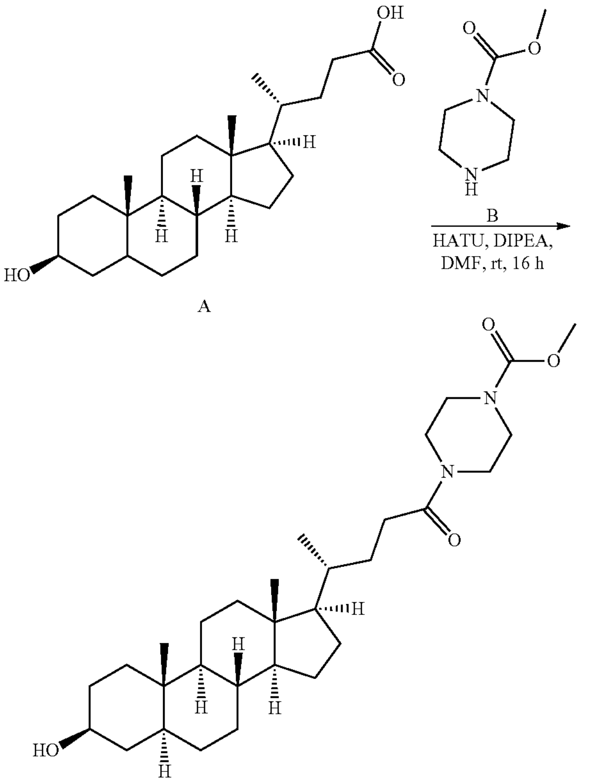

(R)-4-((3S,5S,8R,9S,10S,13R,14S,17R)-3-hydroxy-10,13-dimethylhexadecahydro-1H-cyclopenta[a]phenanthren-17-yl)pentanoic acid (300 mg, 797 μmol) and methyl piperazine-1-carboxylate (144 mg, 996 μmol) were reacted according to the method of Example T27 to afford the title compound T67 (105 mg, 20%) as a white solid. LCMS: [M+1]+=525.25. $^1$H NMR (400 MHz, Chloroform-d) δ 3.72 (s, 3H), 3.64-3.53 (m, 3H), 3.52-3.38 (m, 6H), 2.43-2.31 (m, 1H), 2.28-2.17 (m, 1H), 2.05-1.91 (m, 1H), 1.88-1.75 (m, 3H), 1.72 (s, 1H), 1.70-1.60 (m, 3H), 1.59-1.52 (m, 2H), 1.51-1.40 (m, 3H), 1.38-1.31 (m, 3H), 1.30-1.21 (m, 6H), 1.15-1.04 (m, 4H), 1.02-0.98 (m, 1H), 0.97-0.90 (m, 4H), 0.90-0.83 (m, 1H), 0.80 (s, 3H), 0.65 (s, 4H).

Utility

Multiple SREBP-2-mediated pathways are attractive potential targets for cancer therapy. SREBP-2 reportedly binds to the sterol regulatory elements (SREs) in the promoters of its target genes and activates the transcription of mevalonate pathway genes, such as 3-hydroxy-3-methylglutaryl-CoA (HMG-CoA) reductase (HMGCR), mevalonate kinase (MVK), and other key enzymes. The mevalonate pathway and its metabolites are essential for cancer growth and malignant progression in a series of cancers. Moreover, multiple key pathways, such as the p53 and phosphatidylinositol-3-kinase (PI3K)/Akt signaling pathways, lead to the activation of SREBP-2 to promote tumorigenesis. Accordingly, targeting SREBP-2 and its pathways is an encouraging strategy for identifying and developing useful cancer therapies.

GBM is the most common and aggressive malignant primary brain tumor occurring in humans. GBM involves glial cells and accounts for 52% of all functional tissue brain tumor cases and 20% of all intracranial tumors. The treatment of GBM is extremely difficult due to several factors: (1) the tumor cells are very resistant to conventional therapies; (2) the brain is susceptible to damage using conventional therapy; (3) the brain has a very limited capacity for self-repair; and (4) many therapeutic drugs cannot cross the blood-brain barrier to act on the tumor.

GBM has an extremely poor prognosis, despite various treatment methods. The median survival time from the time of diagnosis without any treatment is 3 months, but with treatment survival of 1-2 years is common. Increasing age (>60 years of age) carries a worse prognostic risk. Death is usually due to cerebral edema or increased intracranial pressure. Common symptoms of GBM include seizures, nausea, vomiting, headache, and hemiparesis. However, the single most prevalent symptom of GBM is progressive memory, personality, or neurological deficit due to involvement of the temporal or frontal lobe of the brain. The kind of symptoms produced by GBM depends highly on the location of the tumor and less on its exact pathology. The tumor can start producing symptoms quickly, but occasionally is asymptomatic until it reaches an extremely large size.

GBM has been linked to aberrant fatty acid metabolism and overexpression of sterol regulatory element-binding protein 1 (SREBP-1), a key lipid transcription factor. SREBPs are a family of basic-helix-loop-helix leucine zipper transcription factors that regulate de novo synthesis of fatty acids and cholesterol as well as cholesterol uptake. Mammalian cells express three SREBP proteins, SREBP-1a, -1c and -2, which are encoded by two genes, SREBF1 and SREBF2. SREBP-1a can activate all target genes. SREBP-1c primarily regulates fatty acid metabolism, such as regulation of the fatty acid synthase (FASN) gene. SREBP-2 is mainly responsible for cholesterol-related genes. Since cholesterol and fatty acid synthesis decreases following the inhibition of SREBP expression, regulation of SREBP should have an anti-tumor effect on GBM tumor cells, including the reduction of cell viability, proliferation, size, and migration rate.

For example, the oncogenic signaling EGFR-PI3K-Akt pathway is involved in boosting lipid levels and their uptake into glioblastoma cells by the upregulation of the sterol regulatory element-binding protein SREBP-1. The inhibition of EGFR-PI3K-Akt signaling by the EGFR inhibitor lapatinib, suppresses SREBP-1 nuclear translocation sensitized glioblastoma xenografts, resulting in cell death. SREBP-1 and its pathways can therefore serve as novel targets for the treatment of GBM and alleviation of one or more of its symptoms.

Melanoma is a skin cancer known to have a lipogenic component. Melanoma includes both wild type melanoma and BRAF mutant melanoma (BRAF+). Activation of the SREBP pathway has been linked to sustained growth of melanoma tumor cells. Specifically, it has been shown that the restoration of downregulated SREBP-1 leads to therapy-resistant melanoma cells. It has also been reported that SREBP-2 contributes to melanoma drug resistance and metastasis. SREBP-1 and SREBP-2 and their pathways can therefore serve as novel targets for the treatment of melanoma and alleviation of one or more of its symptoms.

For prostate cancer, SREBP-1a, -1c, and -2 are all upregulated during prostate cancer progression to androgen independence. SREBP-2 has been shown to promote prostate cancer tumorigenicity and metastasis by activating cMyc. SREBP-1 and SREBP-2 and their pathways can therefore serve as novel targets for the treatment of prostate cancer and alleviation of one or more of its symptoms.

For breast cancer, elevated SREBP-1 and elevated SREBP-2 expression each is associated with breast tumor metastasis and predicts poor prognosis in patients. SREBP-1 and SREBP-2 and their pathways can therefore serve as novel targets for the treatment of breast cancer and alleviation of one or more of its symptoms.

For colon (or colorectal) cancer it is known that down-regulation of SREBP inhibits tumor growth and initiation by altering cellular metabolism. Chemoresistant colon cancer samples have been shown to express high levels of SREBP-1. Also, SREBP-1 overexpression has been correlated with chemoresistance and poor prognosis in patients. SREBP and its pathways can therefore serve as novel targets for the treatment of breast cancer and alleviation of one or more of its symptoms.

For lung cancer, specifically non-small cell lung cancer (NSCLC), inhibition of SREBP-1 has been found to sensitize EGFR-mutant therapy resistant NSCLC to EGFR therapy. So at least SREBP-1 and its pathways can therefore serve as novel targets for the treatment of lung cancer and alleviation of one or more of its symptoms.

For hepatocellular carcinoma (HCC), high levels of SREBP-1 are found in HCC tumors and correlate to poor survival in patients. Inhibition of SREBP-1 displays anti-tumor activity against HCC and facilitates the anti-tumor activity of sorafenib. Therefore, SREBP inhibition constitutes a novel target for the treatment of HCC.

For ovarian cancer, altered expression of key SREBP-1 pathway molecules involved in lipid metabolism are linked to lipid-driven oncogenic progression and omental dissemination in ovarian cancer. Inhibition of SREBP-1 and key lipogenic target genes demonstrates inhibition of ovarian cancer growth and metastasis. Pharmaceutical targeting of SREBP either alone or in combination with standard chemotherapeutic drug represents a novel therapeutic strategy.

Lipogenic cancers have also been linked to LXR receptors, with the agonism of these receptors leading alleviation of one or more symptoms of these cancers. So, steroidal compounds of the invention that function as dual modulators of SREBP (antagonism) and LXR (agonism) would be useful for the treatment of lipogenic cancers.

Assays

In Vitro Assay-SREBP-2

10,000 cells/well of the PathHunter U2OS SREBP-2 Nuclear Translocation Cell Line are plated in quadruplicate on 384 well plates in 20 μL of AssayComplete cell plating 5 reagent (CP5-high serum) overnight at 37° C./5% $CO_2$. A dilution series of test compound is added to cells, incubated for 1 hour at 37° C./5% $CO_2$, and U18666A (a known SREBP agonist) is added to a final concentration of 10 μM. The plate is incubated overnight (16 hours) at 37° C./5% $CO_2$. PathHunter Flash detection mix is added to the wells, incubated one hour in the dark, and the plate read on an Envision luminometer.

In Vitro Assay-LXRβ

PathHunter NHR CHO cells stably transfected with tagged full-length human LXRβ and a nuclear fusion protein containing Steroid Receptor Co-activator Peptide (SRCP). The full-length human LXRβ was tagged with the Pro-Link™ component of the DiscoverX Enzyme Fragment Complementation (EFC) system and the SRCP domain is fused to the enzyme acceptor component (EA) expressed in the nucleus. Cells were seeded in a total volume of 20 μL into white walled, 384-well microplates and incubated at 37° C. overnight prior to testing. Assay media contained charcoal-dextran filtered serum to reduce the level of hormones present. Final assay vehicle concentration was 1%. Assay signal was generated through a single addition of 12.5 or 15 μL (50% v/v) of PathHunter Detection reagent cocktail, followed by a one-hour incubation at room temperature. Microplates were read following signal generation with a PerkinElmer Envision instrument for chemiluminescent signal detection.

In Vivo Assay

Syngeneic models involve GBM tumor cells that are murine in origin and can be transplanted back into mice of a similar genetic background. Syngeneic tumor lines can be generated from spontaneously occurring murine tumors but are frequently generated using mutagenic chemicals or transposons. Syngeneic models are well suited for preclinical studies evaluating treatments involving the immune system, such as checkpoint inhibitors, as the immune system is intact in these models. Syngeneic models have multiple advantages, including that tumor cells can be easily maintained and expanded in vitro before their implantation into a mouse, resulting in the formation of consistent, reproducible tumors with reliable rates of growth and impact on murine survival. The ability to be implanted into immunocompetent animals provides a complete tumor microenvironment, as the host immune system is intact and able to be interrogated. Syngeneic cells are typically more desirable over other model types in studies where a fully functional immune system is required, such as preclinical investigations into immunotherapies.

Cell Culture

The tumor cell lines LN18-luc, T98G-luc or DBTG-05MG-luc are maintained in vitro as monolayer culture in EMEM supplemented with 10% fetal bovine serum and 8000 ng/ml puromycin at 37° C. in an atmosphere of 5% $CO_2$ in air. The tumor cells are routinely subcultured weekly by trypsin-EDTA treatment, not to exceed 4-5 passages. The cells growing in an exponential growth phase are harvested and counted for tumor inoculation.

Method for Tumor Inoculation and Randomization

Animals are anesthetized by i.m. injection of Zoletil™ 50 (Virbac S.A) and xylazine hydrochloride. The skin over the coronal and sagittal sutures of anesthetized mice is sterilized with iodine followed by alcohol. An incision of 0.5 cm is made along the skin over the midline to expose coronal and sagittal suture junctions. Animals are placed on the stereotaxic instrument (Stoelting, USA) for intracranial injection. $2\times10^5$ luciferase-expressing tumor cells suspended in 2 μL EMEM media are injected into the right forebrain by positioning the needle at 2.0 mm lateral to the sagittal suture, 0.5-1.0 mm anterior to coronal suture with the injection depth precisely controlled at 3.0 mm. The injection is slowly proceeded over a one-minute period. Upon completing injection, the needle is retained for another minute. After the needle removal, the hole is sealed with bone wax and the incision is closed. The tumor growth is monitored by image analysis. Mice are then randomized into each group based on bioluminescent signal of tumor and body weight around day 21 post tumor cells inoculation. The treatments will be administrated to the tumor-bearing mice accordingly to the study design shown below wherein typical doses would are 30, 100 and 300 mg/kg, dosed QDx28d.

Group and Treatments

| Group | Treatment | N | Dose (mg/kg) | Vol (mL/kg) | Route | Regimen |
|---|---|---|---|---|---|---|
| 1 | Vehicle Control | 10 | — | 10 | p.o. | qd × 3-4 weeks |
| 2 | ASTX-XXX | 10 | 10 | 10 | p.o. | qd × 3-4 weeks |
| 3 | ASTX-XXX | 10 | 30 | 10 | p.o. | qd × 3-4 weeks |
| 4 | ASTX-XXX | 10 | 100 | 10 | p.o. | qd × 3-4 weeks |

Measurement Parameters

For routine monitoring, all study animals are monitored not only for tumor growth but also behavior such as mobility, food, and water consumption (by cage side checking only, everyday), body weight (BW), eye/hair matting and any other abnormal effect. Any mortality and/or abnormal clinical signs will be recorded.

Body Weight

Body weights of all animals will be measured 2 times per week throughout the study. Body weight change, expressed in %, will be calculated using the following formula:

BW change (%)=($BW_{Dayx}$/$BW_{Day\ 0}$)×100, where $BW_{Dayx}$ is BW on a given day, and $BW_{Day\ 0}$ is BW on Day 0 (initiation of treatment).

Imaging Analysis of Tumor Development

Mice will be injected intraperitoneally with 15 mg/mL (at 5 μL/g BW) of D-luciferin (Perkin Elmer) and anesthetized with 1-2% isoflurane inhalation. At 10 minutes after the luciferin injection, the mice will be imaged using IVIS Lumina III (Perkin Elmer) once per week. Living Image software (Perkin Elmer) is used to compute regions of interest (ROI) and integrate the total bioluminescence signal in each ROI from whole body. Bioluminescent signals (photons/s) from ROI will be quantified and used as an indicator of tumor growth and antitumor activity. BLI Decrease (%)=(1−$BLI_{treatment}$/$BLI_{control}$)×100%, where $BLI_{treatment}$ and $BLI_{control}$ will be the mean BLI in the treated and the control groups, respectively, on a given day after tumor inoculation. Imaging will be terminated once animal is found dead.

Representative compounds were tested for SREBP-2 activity and LXRβ activity (see the in vitro assays described above) with values provided as shown in the table below.

| Activity | SREBP-2 IC50 | LXRβ PPI |
|---|---|---|
| A | <1 nM to 250 nM | <1 nM to 250 nM |
| B | 250 nM-1000 nM | 250 nM-1000 nM |
| C | 1000-10000 nM | 1000-10000 nM |
| D | >10000 nM | >10000 nM |

Table 1 shows cholenic acid derivative examples of the compounds of the invention. Each example in each table represents an individual species of the invention.

TABLE 1

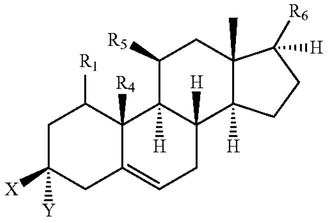

| Ex. # | SREBP-2 IC50 | LXRβ PPI |
|---|---|---|
| 1. | A | B |
| 2. | B | C |
| 3. | A | D |
| 4. | A | D |
| 5. | A | C |
| 6. | A | B |
| 7. | A | C |
| 8. | A | B |
| 9. | A | D |
| 10. | A | A |
| 11. | N/A | B |
| 12. | N/A | B |
| 13. | A | B |
| 14. | B | B |
| 15. | N/A | C |
| 16. | N/A | C |
| 17. | N/A | C |
| 18. | A | D |
| 19. | A | C |
| 20. | A | D |
| 21. | A | N/A |
| 22. | B | N/A |
| 23. | A | N/A |
| 24. | B | N/A |
| 25. | B | N/A |
| 26. | B | N/A |
| 27. | N/A | C |
| 28. | B | D |
| 29. | A | D |
| 30. | N/A | C |
| 31. | N/A | C |
| 32. | B | D |
| 33. | N/A | B |
| 34. | A | B |
| 35. | B | B |
| 36. | B | A |
| 37. | B | B |
| 38. | N/A | C |
| 39. | N/A | B |
| 40. | N/A | C |
| 41. | N/A | C |
| 42. | B | B |
| 43. | B | D |
| 44. | B | D |
| 45. | B | D |
| 46. | B | D |
| 47. | B | C |
| 48. | B | D |
| 49. | B | B |
| 50. | N/A | C |
| 51. | A | C |
| 52 | N/A | C |
| 53. | A | C |
| 54. | N/A | D |
| 55. | N/A | D |
| 56. | N/A | B |
| 57 | N/A | B |
| 58. | N/A | B |
| 59. | N/A | B |
| 60. | N/A | B |
| 61. | N/A | C |
| 62. | B | B |
| 63. | D | B |
| 64. | B | A |
| 65. | A | C |
| 66. | B | B |

TABLE 1-continued

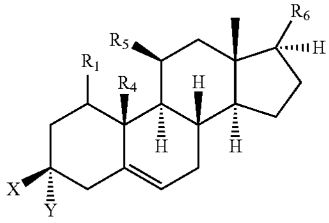

| Ex. # | SREBP-2 IC50 | LXRβ PPI |
|---|---|---|
| 67. | N/A | C |
| 68. | N/A | N/A |
| 69. | A | B |
| 70. | B | B |
| 71. | B | B |
| 72. | B | B |
| 73. | N/A | N/A |
| 74. | A | N/A |
| 75. | N/A | B |
| 76. | A | C |
| 77. | A | C |
| 78. | A | C |
| 79. | A | C |
| 80. | A | C |
| 81. | A | B |
| 82. | A | D |
| 83. | B | D |
| 84. | B | D |
| 85. | A | D |
| 86. | B | D |
| 87. | B | D |
| 88. | A | D |
| 89. | A | D |
| 90. | A | B |
| 91. | A | D |
| 92. | A | B |
| 93. | A | A |
| 94. | A | B |
| 95. | N/A | N/A |
| 96. | N/A | N/A |
| 97. | A | D |
| 98. | A | D |
| 99. | A | D |
| 100. | A | D |
| 101. | A | D |
| 102. | A | D |
| 103. | A | B |
| 104. | A | B |
| 105. | A | C |
| 106. | A | B |
| 107. | D | N/A |
| 108. | D | N/A |
| 109. | D | N/A |
| 110. | A | C |
| 111. | A | B |
| 112. | A | B |
| 113. | A | B |
| 114. | A | B |
| 115. | A | B |
| 116. | A | D |
| 117. | A | D |
| 118. | D | D |
| 119. | D | D |
| 120. | C | D |
| 121. | D | C |
| 122. | D | N/A |
| 123. | D | C |
| 124. | A | B |
| 125. | N/A | N/A |
| 126. | D | D |
| 127. | D | D |
| 128. | A | A |
| 129. | A | A |
| 130. | A | A |
| 131. | B | D |
| 132. | B | C |

TABLE 1-continued

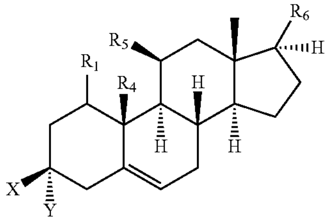

| Ex. # | SREBP-2 IC50 | LXRβ PPI |
|---|---|---|
| 133. | B | B |
| 134. | D | B |
| 135. | A | C |
| 136. | A | B |
| 137. | B | C |
| 138. | N/A | B |
| 139. | B | D |
| 140. | B | D |
| 141. | N/A | D |
| 142. | C | C |
| 143. | N/A | D |
| 144. | N/A | D |
| 145. | N/A | D |
| 146. | A | A |
| 147. | A | A |
| 148. | A | A |
| 149. | A | B |
| 150. | A | A |
| 151. | A | A |
| 152. | A | A |
| 153. | A | B |
| 154. | A | A |
| 155. | C | D |
| 156. | D | A |
| 157. | B | B |
| 158. | B | A |
| 159. | A | D |
| 160. | B | D |
| 161. | A | C |
| 162. | A | C |
| 163. | A | C |
| 164. | B | B |
| 165. | B | D |
| 166. | B | D |
| 167. | B | D |
| 168. | B | D |
| 169. | B | A |
| 170. | N/A | D |
| 171. | A | D |
| 172. | B | C |
| 173. | B | D |
| 174. | B | B |
| 175. | A | C |
| 176. | B | D |
| 177. | B | C |
| 178. | B | D |
| 179. | A | D |
| 180. | A | D |
| 181. | B | D |
| 182. | B | D |
| 183. | B | D |
| 184. | A | C |
| 185. | B | C |
| 186. | A | A |
| 187. | A | B |
| 188. | A | C |
| 189. | A | C |
| 190. | B | C |
| 191. | A | B |
| 192. | A | D |
| 193. | A | A |
| 193A | A | B |
| 194. | A | C |
| 195. | A | C |
| 196. | A | C |
| 197. | A | B |

TABLE 1-continued

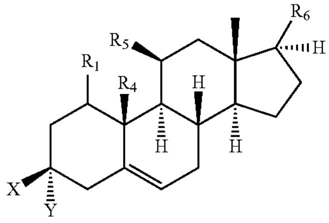

| Ex. # | SREBP-2 IC50 | LXRβ PPI |
|---|---|---|
| 198. | A | C |
| 199. | A | B |
| 200. | A | C |
| 201. | A | C |
| 202. | A | D |
| 203. | A | D |
| 204. | A | D |
| 205. | A | D |
| 206. | A | D |
| 207. | A | D |
| 208. | A | D |
| 209. | A | D |
| 210. | A | D |
| 211. | A | D |
| 212. | A | D |
| 213. | A | D |
| 214. | A | D |
| 215. | B | N/A |
| 216. | A | D |
| 217. | A | D |
| 218. | A | B |
| 219. | A | D |
| 220. | A | C |
| 221. | A | C |
| 222. | A | D |
| 223. | A | D |
| 224. | A | D |
| 225. | A | D |
| 226. | A | D |
| 227. | A | D |
| 228. | A | D |
| 229. | A | D |
| 230. | A | D |
| 231. | A | D |
| 232. | A | D |
| 233. | A | N/A |
| 234. | A | N/A |
| 235. | N/A | N/A |
| 236. | A | D |
| 237. | A | N/A |
| 238. | A | D |
| 239. | B | N/A |
| 240. | B | N/A |
| 241. | A | N/A |
| 242. | B | N/A |
| 243. | A | N/A |
| 244. | A | N/A |
| 245. | B | D |
| 246. | A | B |
| 247. | A | B |
| 248. | A | A |
| 249. | A | A |
| 250. | A | A |
| 251. | A | D |
| 252. | A | D |
| 253. | A | D |
| 254. | A | N/A |
| 255. | A | D |
| 256. | B | N/A |
| 257. | A | D |
| 258. | A | D |
| 259. | B | N/A |
| 260. | A | D |
| 261. | A | D |
| 262. | A | N/A |
| 263. | B | N/A |

TABLE 1-continued

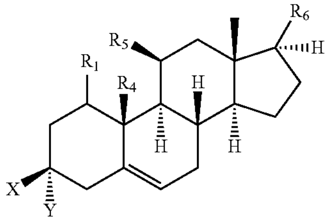

| Ex. # | SREBP-2 IC50 | LXRβ PPI |
|---|---|---|
| 264. | B | D |
| 265. | C | N/A |
| 266. | B | N/A |
| 267. | B | N/A |
| 268. | B | N/A |
| 269. | B | N/A |
| 270. | B | N/A |
| 271. | B | N/A |
| 272. | A | N/A |
| 273. | A | N/A |
| 274. | B | D |
| 275. | A | D |
| 276. | A | D |
| 277. | A | D |
| 278. | A | D |
| 279. | A | D |
| 280. | A | D |
| 281. | A | D |
| 282. | A | D |
| 283. | A | D |
| 284. | C | D |
| 285. | C | D |
| 286. | A | D |
| 287. | A | D |
| 288. | B | D |
| 289. | B | D |
| 290. | A | D |
| 291. | A | D |
| 292. | A | D |
| 293. | A | B |
| 294. | B | N/A |
| 295. | A | N/A |
| 296. | A | D |
| 297. | A | D |
| 298. | A | D |
| 299. | A | D |
| 300. | A | B |
| 301. | A | D |
| 302. | A | D |
| 303. | A | D |
| 304. | A | D |
| 305. | A | D |
| 306. | A | D |
| 307. | A | D |
| 308. | A | D |
| 309. | A | D |
| 310. | A | D |
| 311. | A | D |
| 312. | A | D |
| 313. | A | D |
| 314. | A | D |
| 315. | A | D |
| 316. | A | D |
| 317. | A | D |
| 318. | B | D |
| 319. | A | D |
| 320. | A | D |
| 321. | A | D |
| 322. | A | D |
| 323. | B | D |
| 324. | B | D |
| 325. | B | N/A |
| 326. | B | N/A |
| 327. | B | N/A |
| 328. | B | N/A |
| 329. | A | C |

TABLE 1-continued

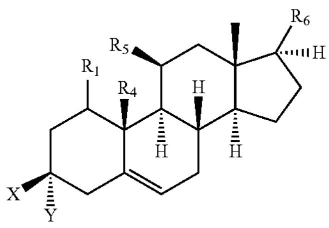

| Ex. # | SREBP-2 IC50 | LXRβ PPI |
|---|---|---|
| 330. | A | B |
| 331. | A | D |
| 332. | A | D |
| 333. | A | D |
| 334. | A | D |
| 335. | A | D |
| 336. | A | D |
| 337. | A | D |
| 338. | A | D |
| 339. | A | D |
| 340. | A | D |
| 341. | A | D |
| 342. | A | D |
| 343. | C | N/A |
| 344. | A | D |
| 345. | B | N/A |
| 346. | A | A |
| 347. | B | N/A |
| 348. | A | D |
| 349. | A | D |
| 350. | B | D |
| 351. | A | D |
| 352. | A | C |
| 353. | A | D |
| 354. | A | D |
| 355. | B | D |
| 356. | A | D |
| 357. | A | D |
| 358. | A | D |
| 359. | A | D |
| 360. | A | D |
| 361. | B | D |
| 362. | B | D |
| 363. | A | D |
| 364. | A | D |
| 365. | A | D |
| 366. | B | N/A |
| 367. | A | D |
| 368. | B | N/A |
| 369. | B | C |
| 370. | B | N/A |
| 371. | B | A |
| 372. | A | D |
| 373. | B | D |
| 374. | A | B |
| 375. | A | D |
| 376. | A | B |
| 377. | A | B |
| 378. | A | D |
| 379. | B | D |
| 380. | A | D |
| 381. | C | N/A |
| 382. | A | D |
| 383. | A | D |
| 384. | A | A |
| 385. | A | D |
| 386. | A | D |
| 387. | A | D |
| 388. | A | D |
| 389. | A | D |
| 390. | A | D |
| 391. | A | D |
| 392. | A | D |
| 393. | A | D |
| 394. | A | D |
| 395. | A | D |

TABLE 1-continued

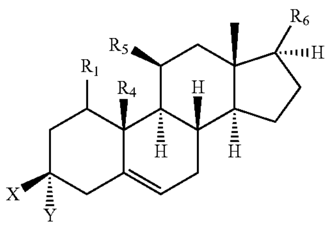

| Ex. # | SREBP-2 IC50 | LXRβ PPI |
|---|---|---|
| 396. | A | D |
| 397. | A | D |
| 398. | A | D |
| 399. | A | D |
| 400. | A | D |
| 401. | A | D |
| 402. | A | B |
| 403. | A | D |
| 404. | A | D |
| 405. | A | D |
| 406. | A | D |
| 407. | A | D |
| 408. | B | N/A |
| 409. | A | B |
| 410. | C | D |
| 411. | A | D |
| 412. | A | D |
| 413. | B | D |
| 414. | B | D |
| 415. | B | D |
| 416. | A | D |
| 417. | A | D |
| 418. | C | N/A |
| 419. | C | N/A |
| 420. | A | D |
| 421. | A | D |
| 422. | A | D |
| 423. | A | D |
| 424. | A | D |
| 425. | A | D |
| 426. | A | D |
| 427. | A | D |
| 428. | A | D |
| 429. | A | D |
| 430. | B | D |
| 431. | A | N/A |
| 432. | A | N/A |
| 433. | B | N/A |
| 434. | B | N/A |
| 435. | B | N/A |
| 436. | B | N/A |
| 437. | B | N/A |
| 438. | B | N/A |
| 439. | B | N/A |
| 440. | B | D |
| 441. | B | N/A |
| 442. | A | N/A |
| 443. | A | D |
| 444. | A | D |
| 445. | B | N/A |
| 446. | A | D |
| 447. | A | D |
| 448. | B | N/A |
| 449. | A | D |
| 450. | A | N/A |
| 451. | A | D |
| 452. | A | D |
| 453. | A | D |
| 454. | A | A |
| 455. | A | A |
| 456. | A | A |
| 457. | A | B |
| 458. | A | B |
| 459. | B | N/A |
| 460. | A | D |
| 461. | B | N/A |

TABLE 1-continued

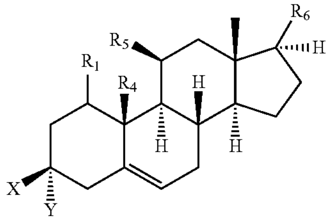

| Ex. # | SREBP-2 IC50 | LXRβ PPI |
|---|---|---|
| 462. | A | N/A |
| 463. | B | N/A |
| 464. | B | N/A |
| 465. | A | D |
| 466. | B | N/A |
| 467. | A | D |
| 468. | A | N/A |
| 469. | A | B |
| 470. | A | N/A |
| 471. | A | N/A |
| 472. | A | D |
| 473. | A | D |
| 474. | A | D |
| 475. | A | D |
| 476. | A | N/A |
| 477. | A | N/A |
| 478. | A | N/A |
| 479. | A | N/A |
| 480. | A | D |
| 481. | A | D |
| 482. | A | D |
| 483. | A | D |
| 484. | A | D |
| 485. | A | D |
| 486. | A | D |
| 487. | A | D |
| 488. | A | C |
| 489. | A | C |
| 490. | A | D |
| 491. | A | B |
| 492. | A | D |
| 493. | A | D |
| 494. | B | N/A |
| 495. | A | D |
| 496. | A | D |
| 497. | A | D |
| 498. | A | D |
| 499. | A | D |
| 500. | A | D |
| 501. | A | D |
| 502. | A | D |
| 503. | A | D |
| 504. | A | D |
| 505. | A | N/A |
| 506. | A | N/A |
| 507. | A | N/A |
| 508. | A | D |
| 509. | A | D |
| 510. | A | D |
| 511. | A | D |
| 512. | A | D |
| 513. | A | D |
| 514. | A | D |
| 515. | A | D |
| 516. | A | D |
| 517. | A | N/A |
| 518. | A | N/A |
| 519. | A | C |
| 520. | A | N/A |
| 521. | A | N/A |
| 522. | A | N/A |
| 523. | A | B |
| 524. | B | N/A |
| 525. | A | N/A |
| 526. | A | N/A |
| 527. | A | N/A |

TABLE 1-continued

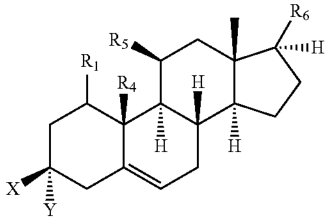

| Ex. # | SREBP-2 IC50 | LXRβ PPI |
|---|---|---|
| 528. | A | N/A |
| 529. | A | N/A |
| 530. | B | N/A |
| 531. | A | N/A |
| 532. | A | N/A |
| 533. | A | N/A |
| 534. | A | N/A |
| 535. | B | N/A |
| 536. | B | N/A |
| 537. | B | N/A |
| 538. | A | D |
| 539. | A | D |
| 540. | A | D |
| 541. | A | N/A |
| 542. | B | N/A |
| 543. | A | B |
| 544. | A | N/A |
| 545. | B | B |
| 546. | A | D |
| 547. | A | N/A |
| 548. | A | B |
| 549. | A | N/A |
| 550. | A | D |
| 551. | A | D |
| 552. | C | D |
| 553. | B | D |
| 554. | A | D |
| 555. | A | D |
| 556. | A | N/A |
| 557. | B | D |
| 558. | A | N/A |
| 559. | A | D |
| 560. | A | D |
| 561. | A | D |
| 562. | A | D |
| 563. | A | D |
| 564. | A | D |
| 565. | A | D |
| 566. | A | D |
| 567. | A | D |
| 568. | A | D |
| 569. | A | D |
| 570. | A | D |
| 571. | A | D |
| 572. | A | D |
| 573. | A | D |
| 574. | A | D |
| 575. | A | D |
| 576. | A | D |
| 577. | A | D |
| 578. | A | D |
| 579. | A | D |
| 580. | A | D |
| 581. | A | D |
| 582. | A | D |
| 583. | A | D |
| 584. | A | D |
| 585. | A | B |
| 586. | A | N/A |
| 587. | A | D |
| 588. | A | D |
| 589. | A | D |
| 590. | A | D |
| 591. | A | D |
| 592. | A | N/A |
| 593. | C | D |

TABLE 1-continued

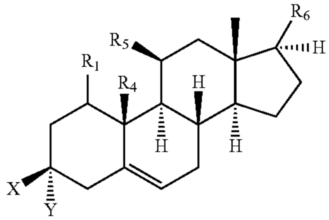

| Ex. # | SREBP-2 IC50 | LXRβ PPI |
|---|---|---|
| 594. | C | D |
| 595. | C | D |
| 596. | A | D |
| 597. | A | D |
| 598. | C | D |
| 599. | C | D |
| 600. | C | D |
| 601. | B | C |
| 602. | A | B |
| 603. | A | D |
| 604. | A | D |
| 605. | A | D |
| 606. | A | D |
| 607. | A | D |
| 608. | A | D |
| 609. | A | D |
| 610. | A | D |
| 611. | A | D |
| 612. | A | D |
| 613. | A | D |
| 614. | A | D |
| 615. | A | D |
| 616. | A | D |
| 617. | A | D |
| 618. | A | D |
| 619. | A | D |
| 620. | A | D |
| 621. | A | D |
| 622. | A | D |
| 623. | A | C |
| 624. | A | D |
| 625. | A | D |
| 626. | A | C |
| 627. | A | D |
| 628. | A | D |
| 629. | A | D |
| 630. | A | D |
| 631. | A | D |
| 632. | A | D |
| 633. | A | D |
| 634. | A | D |
| 635. | A | D |
| 636. | A | D |
| 637. | A | D |
| 638. | A | B |
| 639. | B | D |
| 640. | A | D |
| 641. | A | D |
| 642. | A | D |
| 643. | A | D |
| 644. | A | D |
| 645. | A | D |
| 646. | A | D |
| 647. | A | D |
| 648. | A | D |
| 649. | A | D |
| 650. | A | D |
| 651. | A | D |
| 652. | A | D |
| 653. | A | D |
| 654. | A | D |
| 655. | A | D |
| 656. | A | D |
| 657. | A | D |
| 658. | A | D |
| 659. | A | D |

TABLE 1-continued

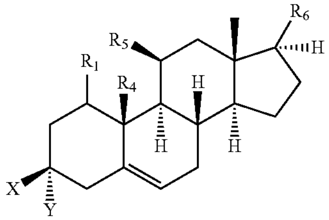

| Ex. # | SREBP-2 IC50 | LXRβ PPI |
|---|---|---|
| 660. | A | D |
| 661. | A | D |
| 662. | A | D |
| 663. | A | D |
| 664. | A | D |
| 665. | A | D |
| 666. | A | D |
| 667. | A | D |

Table 2 shows cis-AB examples of the compounds of the invention. Each example in each table represents an individual species of the invention.

TABLE 2

(Examples C1-C2)

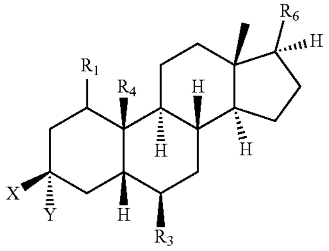

| Ex. # | SREBP-2 IC50 | LXRβ PPI |
|---|---|---|
| 1. | D | D |
| 2. | D | D |

Table 3 shows trans-AB examples of the compounds of the invention. Each example in each table represents an individual species of the invention.

TABLE 3

(Examples T1-T12)

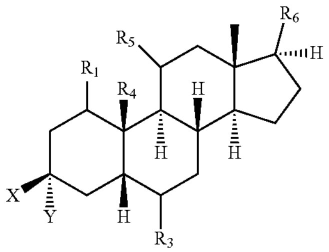

| Ex. # | SREBP-2 IC50 | LXRβ PPI |
|---|---|---|
| 1. | C | C |
| 2. | C | C |
| 3. | C | B |
| 4. | C | C |
| 5. | B | N/A |

TABLE 3-continued (Examples T1-T12)

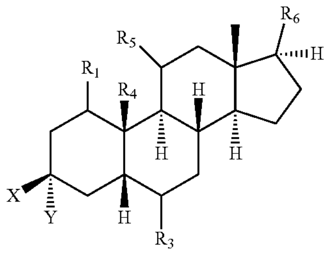

| Ex. # | SREBP-2 IC50 | LXRβ PPI |
|---|---|---|
| 6. | A | N/A |
| 7. | B | N/A |
| 8. | B | D |
| 9. | A | C |
| 10. | A | B |
| 11. | A | D |
| 12. | A | D |
| 13. | A | D |
| 14. | A | D |
| 15. | A | D |
| 16. | A | B |
| 17. | A | D |
| 18. | A | D |
| 19. | A | D |
| 20. | A | D |
| 21. | A | C |
| 22. | A | B |
| 23. | A | A |
| 24. | B | N/A |
| 25. | B | C |
| 26. | B | B |
| 27. | A | D |
| 28. | A | D |
| 29. | A | D |
| 30. | A | D |
| 31. | A | D |
| 32. | A | D |
| 33. | A | D |
| 34. | A | D |
| 35. | A | D |
| 36. | A | D |
| 37. | A | D |
| 38. | A | D |
| 39. | A | D |
| 40. | A | D |
| 41. | A | D |
| 42. | A | D |
| 43. | A | D |
| 44. | A | D |
| 45. | A | D |
| 46. | A | D |
| 47. | A | D |
| 48. | A | D |
| 49. | A | N/A |
| 50. | A | D |
| 51. | A | D |
| 52. | A | D |
| 53. | A | D |
| 54. | A | D |
| 55. | A | D |
| 56. | A | D |
| 57. | A | D |
| 58. | A | D |
| 59. | A | D |
| 60. | A | D |
| 61. | B | N/A |
| 62. | A | D |
| 63. | A | D |
| 64. | A | D |
| 65. | A | B |
| 66. | A | D |
| 67. | A | D |

All references listed herein are individually incorporated herein in their entirety by reference.

Numerous modifications and variations of the invention are possible considering the above teachings. It is therefore to be understood that within the scope of the appended claims, the invention may be practiced otherwise than as specifically described herein.

The invention claimed is:

1. A compound of Formula IIa or a stereoisomer or pharmaceutically acceptable salt thereof:

IIa

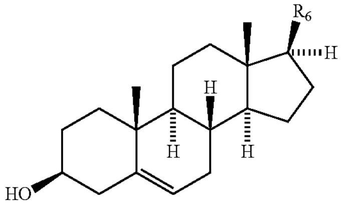

wherein:

$R_6$ is $R_{6C}$ (wherein * is the point of attachment to formula I):

$R_{6C}$

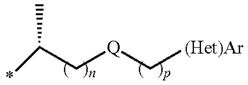

Q is absent or is O;

n is selected from 0, 1, 2, and 3;

p is selected from 0, 1, 2, and 3, provided that in $R_{6C}$, when Q is absent, then n+p total at least 2;

Het(Ar) is selected from the group pyridyl, pyrimidinyl, pyridazinyl, pyrazinyl, 1,2-thiazolyl, 1,3-thiazolyl, 1,2,5-thiadiazolyl, and 1,3-oxazolyl, (a) the Het(Ar) ring is optionally substituted with 1-2 groups selected from —NC, $C_{1-6}$ alkyl, —$C_{0-4}$ alkylene-$C_{3-6}$ cycloalkyl, halo, $CH_2CF_3$, $CHF_2$, $CF_3$, $CH_2CHF_2$, $C(OR)(CF_3)_2$, $C_{2-6}$ alkenyl, $C_{2-6}$ alkynyl, —$C_{0-4}$ alkylene-OR, —O—$C_{2-4}$ alkylene-OR, —$C_{0-4}$ alkylene-C(O)R, —$C_{0-4}$ alkylene-C(O)OR, —$C_{0-4}$ alkylene-C(O)$NR^aR^b$, —$C_{0-4}$ alkylene-$S(O)_2NR^aR^b$, —$C_{0-4}$ alkylene-$NR^aC(O)$—$C_{1-4}$ alkyl, —$C_{0-4}$ alkylene-$NR^aS(O)_2$—$C_{1-4}$ alkyl, and —$C_{0-4}$ alkylene-$S(O)_2$—$C_{1-4}$ alkyl; and, (b) R is $C_{1-4}$ alkyl.

2. The compound of claim 1 or a stereoisomer or pharmaceutically acceptable salt thereof, wherein:

$R_6$ is $R_{6C1}$ wherein * is the point of attachment to formula I:

$R_{6C1}$

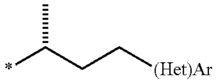

Het (Ar) is selected from the group, pyridyl, pyrimidinyl, quinolinyl, 1,2-thiazolyl, 1,3-thiazolyl, and 1,3-oxazolyl, wherein the Het (Ar) ring is optionally substituted with 1-2 groups selected from $C_{1-6}$ alkyl, OR, Cl, F, and $CF_3$; and, R is $C_{1-4}$ alkyl.
3. A pharmaceutical composition, comprising: a pharmaceutically acceptable carrier and a therapeutically effective amount of a compound of claim 1 or a stereoisomer or pharmaceutically acceptable salt thereof.
4. The compound of claim 1, wherein the compound is selected from the group consisting of:
| Ex # | $R_6$ is |
|---|---|
| 124 | 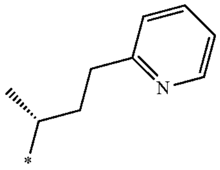 [SMILES: *[C@H](C)CCc1ccccn1] |
| 130 | 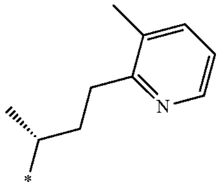 [SMILES: *[C@H](C)CCc1ncccc1C] |
| 131 | 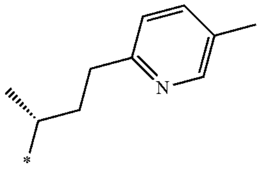 [SMILES: *[C@H](C)CCc1ccc(C)cn1] |
| 132 | 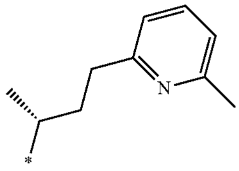 [SMILES: *[C@H](C)CCc1cccc(C)n1] |
| 133 | 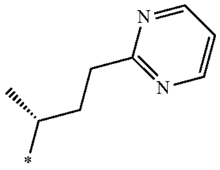 [SMILES: *[C@H](C)CCc1ncccn1] |
| 134 | 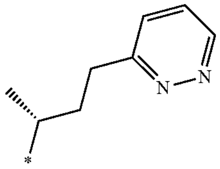 [SMILES: *[C@H](C)CCc1cccnn1] |
| 135 | 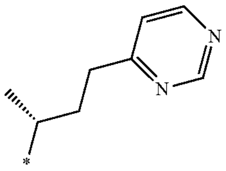 [SMILES: *[C@H](C)CCc1ccncn1] |
-continued
| Ex # | $R_6$ is |
|---|---|
| 136 | 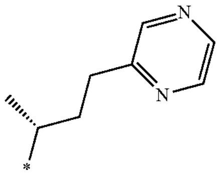 [SMILES: *[C@H](C)CCc1cnccn1] |
| 137 | 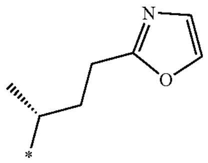 [SMILES: *[C@H](C)CCc1ncco1] |
| 159 | 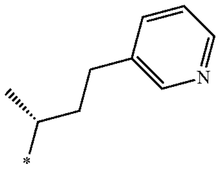 [SMILES: *[C@H](C)CCc1cccnc1] |
| 160 | 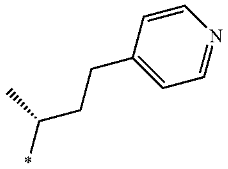 [SMILES: *[C@H](C)CCc1ccncc1] |
| 161 | 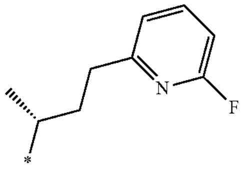 [SMILES: *[C@H](C)CCc1cccc(F)n1] |
| 162 | 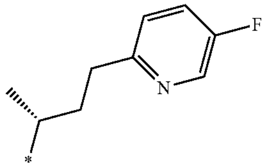 [SMILES: *[C@H](C)CCc1ccc(F)cn1] |
| 163 | 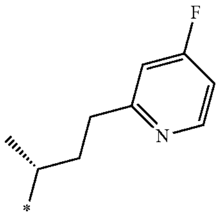 [SMILES: *[C@H](C)CCc1cc(F)ccn1] |
| 164 | 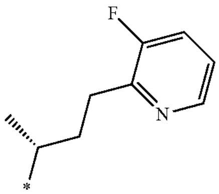 [SMILES: *[C@H](C)CCc1ncccc1F] |

-continued
| Ex # | $R_6$ is |
| --- | --- |
| 165 | 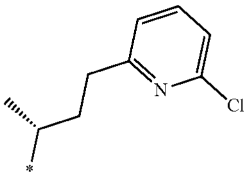 [SMILES: *[C@H](C)CCc1cccc(Cl)n1] |
| 166 | 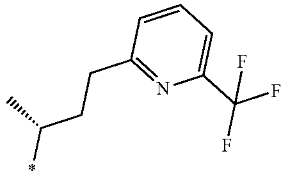 [SMILES: *[C@H](C)CCc1cccc(C(F)(F)F)n1] |
| 167 | 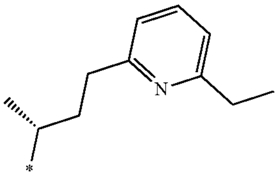 |
| 168 | 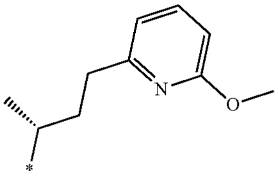 [SMILES: *[C@H](C)CCc1cccc(OC)n1] |
| 170 | 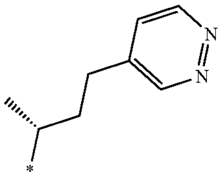 [SMILES: *[C@H](C)CCc1ccnnc1] |
| 171 | 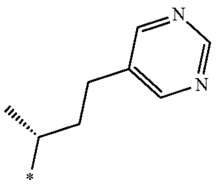 [SMILES: *[C@H](C)CCc1cncnc1] |
| 172 | 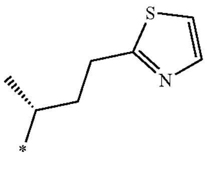 [SMILES: *[C@H](C)CCc1nccs1] |
| 173 | 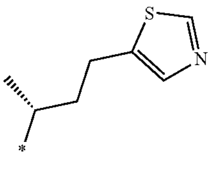 [SMILES: *[C@H](C)CCc1cncs1] |
-continued
| Ex # | $R_6$ is |
| --- | --- |
| 174 | 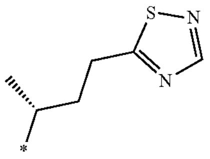 [SMILES: *[C@H](C)CCc1ncns1] |
| 175 | 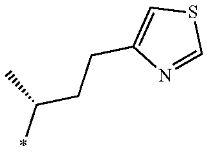 [SMILES: *[C@H](C)CCc1cscn1] |
| 176 | 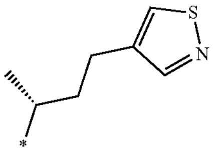 [SMILES: *[C@H](C)CCc1cnsc1] |
| 177 | 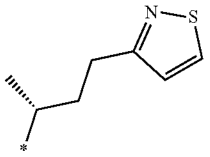 [SMILES: *[C@H](C)CCc1ccsn1] |
| 179 | 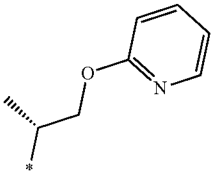 [SMILES: *[C@H](C)COc1ccccn1] |
| 180 | 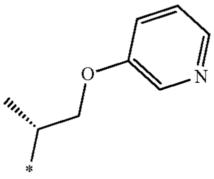 [SMILES: *[C@H](C)COc1cccnc1] |
| 181 | 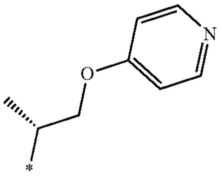 [SMILES: *[C@H](C)COc1ccncc1] |
| 183 | 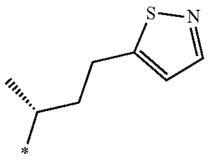 [SMILES: *[C@H](C)CCc1ccns1] |
| 184 | 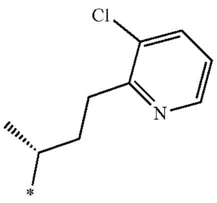 [SMILES: *[C@H](C)CCc1ncccc1Cl] |

-continued
| Ex # | $R_6$ is |
| --- | --- |
| 185 | 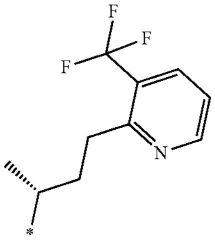 [SMILES: *[C@H](C)CCc1ncccc1C(F)(F)F] |
| 186 | 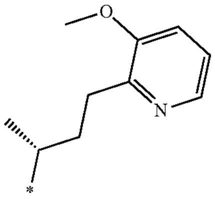 [SMILES: *[C@H](C)CCc1ncccc1OC] |
| 187 | 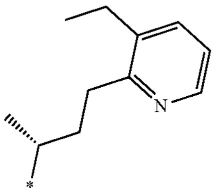 [SMILES: *[C@H](C)CCc1ncccc1CC] |
| 188 | 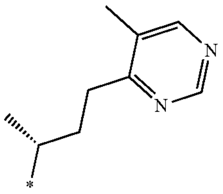 [SMILES: *[C@H](C)CCc1ncncc1C] |
| 189 | 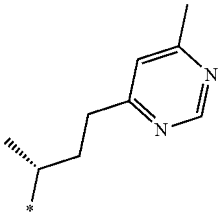 [SMILES: *[C@H](C)CCc1cc(C)ncn1] |
| 190 | 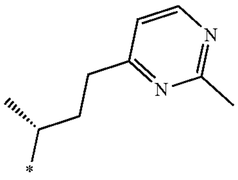 [SMILES: *[C@H](C)CCc1ccnc(C)n1] |
| 191 | 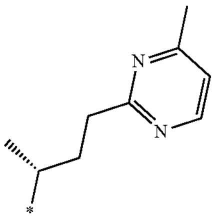 [SMILES: *[C@H](C)CCc1nccc(C)n1] |
-continued
| Ex # | $R_6$ is |
| --- | --- |
| 192 | 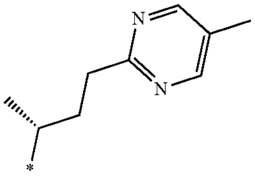 [SMILES: *[C@H](C)CCc1ncc(C)cn1] |
| 246 | 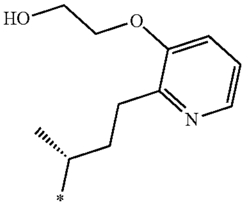 [SMILES: *[C@H](C)CCc1ncccc1OCCO] |
| 247 | 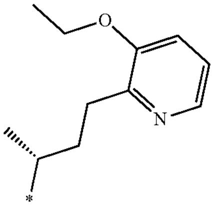 [SMILES: *[C@H](C)CCc1ncccc1OCC] |
| 248 | 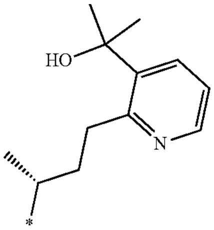 [SMILES: *[C@H](C)CCc1ncccc1C(C)(C)O] |
| 249 | 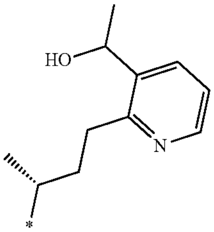 [SMILES: *[C@H](C)CCc1ncccc1C(C)O] |
| 250 | 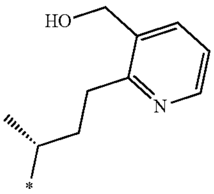 [SMILES: *[C@H](C)CCc1ncccc1CO] |
| 253 | 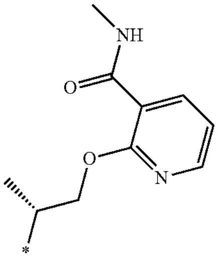 [SMILES: *[C@H](C)COc1ncccc1C(=O)NC] |

-continued
| Ex # | R$_6$ is |
|---|---|
| 254 | 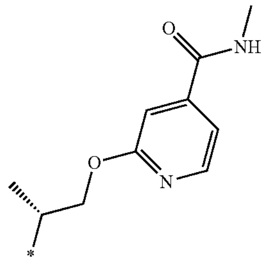 [SMILES: *[C@H](C)COc1cc(C(=O)NC)ccn1] |
| 255 | 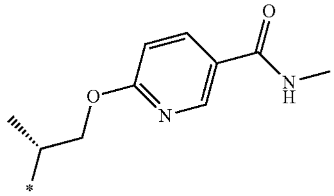 [SMILES: *[C@H](C)COc1ccc(C(=O)NC)cn1] |
| 256 | 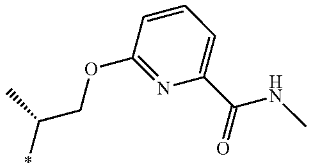 [SMILES: *[C@H](C)COc1cccc(C(=O)NC)n1] |
| 257 | 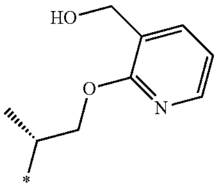 [SMILES: *[C@H](C)COc1ncccc1CO] |
| 258 | 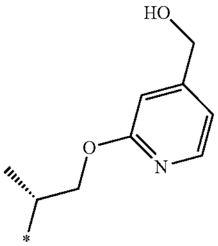 [SMILES: *[C@H](C)COc1cc(CO)ccn1] |
| 259 | 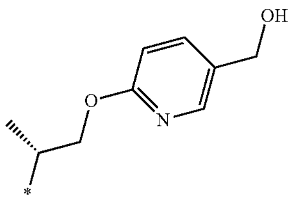 [SMILES: *[C@H](C)COc1ccc(CO)cn1] |
| 260 | 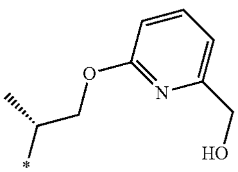 [SMILES: *[C@H](C)COc1cccc(CO)n1] |
-continued
| Ex # | R$_6$ is |
|---|---|
| 261 | 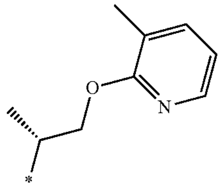 [SMILES: *[C@H](C)COc1ncccc1C] |
| 262 | 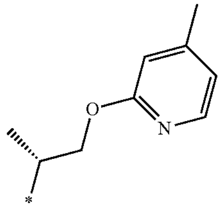 [SMILES: *[C@H](C)COc1cc(C)ccn1] |
| 263 | 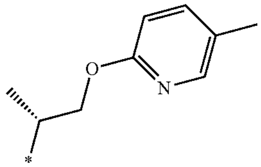 [SMILES: *[C@H](C)COc1ccc(C)cn1] |
| 264 | 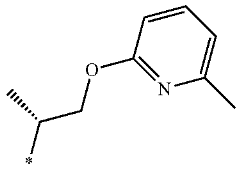 [SMILES: *[C@H](C)COc1cccc(C)n1] |
| 265 | 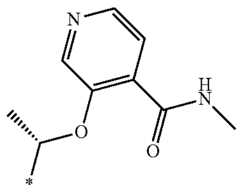 [SMILES: *[C@H](C)Oc1cnccc1C(=O)NC] |
| 266 | 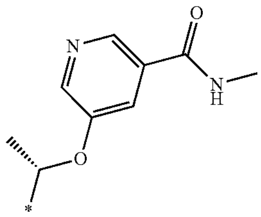 [SMILES: *[C@H](C)Oc1cncc(C(=O)NC)c1] |
| 267 | 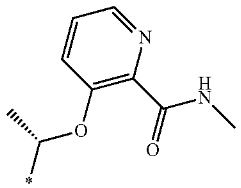 [SMILES: *[C@H](C)Oc1cccnc1C(=O)NC] |
| 268 | 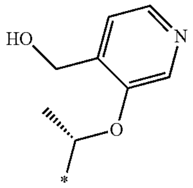 [SMILES: *[C@H](C)Oc1cnccc1CO] |

-continued
| Ex # | $R_6$ is |
|---|---|
| 269 | 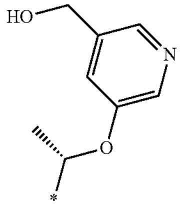 [SMILES: *[C@H](C)Oc1cncc(CO)c1] |
| 270 | 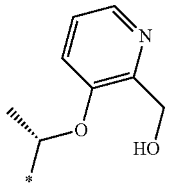 [SMILES: *[C@H](C)Oc1cccnc1CO] |
| 271 | 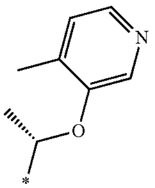 [SMILES: *[C@H](C)Oc1cnccc1C] |
| 272 | 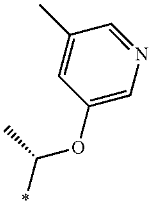 [SMILES: *[C@H](C)Oc1cncc(C)c1] |
| 273 | 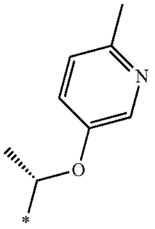 [SMILES: *[C@H](C)Oc1ccc(C)nc1] |
| 274 | 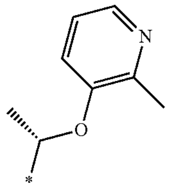 [SMILES: *[C@H](C)Oc1cccnc1C] |
| 379 | 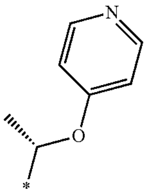 [SMILES: *[C@H](C)Oc1ccncc1] |
-continued
| Ex # | $R_6$ is |
|---|---|
| 380 | 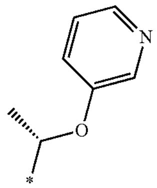 [SMILES: *[C@H](C)Oc1cccnc1] |
| 381 | 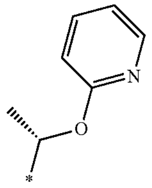 [SMILES: *[C@H](C)Oc1ccccn1] |
| 435 | 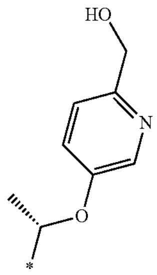 [SMILES: *[C@H](C)Oc1ccc(CO)nc1] |
| 438 | 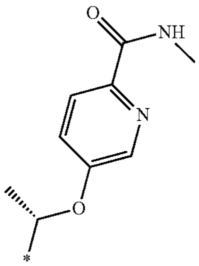 [SMILES: *[C@H](C)Oc1ccc(C(=O)NC)nc1] |
| 601 | 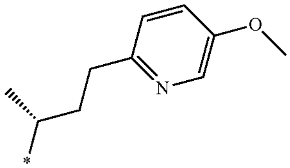 [SMILES: *[C@H](C)CCc1ccc(OC)cn1] |
| 602 | 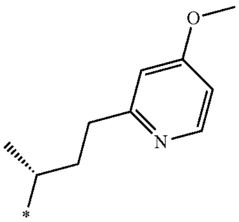 and |

-continued

| Ex # | $R_6$ is |
|---|---|
| | and |
| 638 | 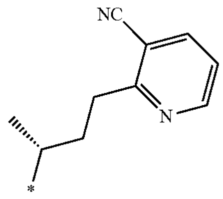 [SMILES: *[C@H](C)CCc1ncccc1C#N] |

or a stereoisomer or pharmaceutically acceptable salt thereof.

5. A pharmaceutical composition, comprising: a pharmaceutically acceptable carrier and a therapeutically effective amount of a compound of claim 2 or a stereoisomer or pharmaceutically acceptable salt thereof.

6. A pharmaceutical composition, comprising: a pharmaceutically acceptable carrier and a therapeutically effective amount of a compound of claim 4 or a stereoisomer or pharmaceutically acceptable salt thereof.

* * * * *